United States Patent
Dipietro et al.

(10) Patent No.: US 12,219,327 B2
(45) Date of Patent: Feb. 4, 2025

(54) SUBSTITUTED ISOINDOLINES AS PI3K-ALPHA INHIBITORS

(71) Applicants: Relay Therapeutics, Inc., Cambridge, MA (US); D.E. Shaw Research, LLC, New York, NY (US)

(72) Inventors: Lucian V. Dipietro, Cambridge, MA (US); Kelley C. Shortsleeves, Cambridge, MA (US); Thomas H. McLean, Cambridge, MA (US); Alexandre Larivee, Montreal (CA); Fabrizio Giordanetto, New York, NY (US); André Lescarbeau, Cambridge, MA (US); Alessandro Boezio, Cambridge, MA (US); Hanmo Zhang, Cambridge, MA (US)

(73) Assignees: Relay Therapeutics, Inc., Cambridge, MA (US); D. E. Shaw Research, LLC, New York, NY (US)

( * ) Notice: Subject to any disclaimer, the term of this patent is extended or adjusted under 35 U.S.C. 154(b) by 23 days.

(21) Appl. No.: 18/208,023

(22) Filed: Jun. 9, 2023

(65) Prior Publication Data

US 2023/0353959 A1     Nov. 2, 2023

Related U.S. Application Data

(63) Continuation of application No. 17/921,580, filed as application No. PCT/US2021/029882 on Apr. 29, 2021.

(60) Provisional application No. 63/066,489, filed on Aug. 17, 2020, provisional application No. 63/017,571, filed on Apr. 29, 2020.

(51) Int. Cl.
| | | |
|---|---|---|
| *A61K 31/4035* | (2006.01) | |
| *A61B 5/00* | (2006.01) | |
| *C07D 209/46* | (2006.01) | |
| *C07D 487/04* | (2006.01) | |
| *H04R 25/00* | (2006.01) | |

(52) U.S. Cl.
CPC ......... *H04R 25/554* (2013.01); *A61B 5/0026* (2013.01); *A61B 5/746* (2013.01); *C07D 487/04* (2013.01); *H04R 2225/55* (2013.01)

(58) Field of Classification Search
CPC .......................... A61K 31/4035; C07D 209/46
USPC ........................................... 514/416; 548/482
See application file for complete search history.

(56) References Cited

U.S. PATENT DOCUMENTS

| | | |
|---|---|---|
| 2011/0237608 A1 | 9/2011 | Baik et al. |
| 2014/0005172 A1 | 1/2014 | Rice |
| 2014/0038936 A1 | 2/2014 | Aronov et al. |
| 2014/0134133 A1 | 5/2014 | Xi |
| 2016/0115169 A1 | 4/2016 | Alonso-De Diego et al. |
| 2017/0226132 A1 | 8/2017 | Ray et al. |
| 2018/0169072 A1 | 6/2018 | Morriello et al. |
| 2019/0016708 A1 | 1/2019 | Chessari et al. |
| 2020/0345729 A1 | 11/2020 | Ikuma et al. |
| 2021/0094960 A1 | 4/2021 | Svenstrup et al. |

FOREIGN PATENT DOCUMENTS

| | | |
|---|---|---|
| CN | 102140087 A | 8/2011 |
| WO | WO-1998027975 A1 | 7/1998 |
| WO | WO-2011067365 A1 | 6/2011 |
| WO | WO-2017120591 A1 | 7/2017 |
| WO | WO-2020173935 A1 | 9/2020 |
| WO | WO-2020257790 A1 | 12/2020 |
| WO | WO-2021222556 A1 | 11/2021 |
| WO | WO-2023288242 A1 | 1/2023 |
| WO | WO-2023039532 A1 | 3/2023 |
| WO | WO-2023060262 A1 | 4/2023 |
| WO | WO-2023081757 A1 | 5/2023 |
| WO | WO-2023081759 A1 | 5/2023 |

OTHER PUBLICATIONS

Aware et al., "Cyclopentyl-pyrimidine based analogues as novel and potent IGF-1R inhibitor," Eur J Med Chem. 2015;92:246-56.
Brown, "A study of Hydrocarbon Reactions over Supported Metal Catalysts : Support and Metal Dependence," The University of Edinburgh Doctoral Thesis or Dissertation. 1990.
PCT International Search Report and Written Opinion for PCT/US2022/073672, dated Dec. 8, 2022.
PCT International Search Report and Written Opinion from PCT/US2021/029882, dated Sep. 24, 2021.
PCT International Search Report and Written Opinion from PCT/US2021/182715, dated Sep. 24, 2021.
PCT International Search Report and Written Opinion from PCT/US2022/076213, dated Jan. 17, 2023.
PCT International Search Report and Written Opinion from PCT/US2022/077801, dated Dec. 1, 2022.
PCT International Search Report and Written Opinion from PCT/US2022/079221, dated Feb. 14, 2023.
PCT International Search Report and Written Opinion from PCT/US2022/079223, dated Feb. 21, 2023.
Pubchem CID 101963520, NIH National Library of Medicine/National Center for Biotechnology Information, 1-8, Web. 2015, p. 2.
Pubchem CID 136794731 Compound Summary: 2-Phenyl-7-(4-methylphenyl)quinazoline-4(3H)-one, PubMed. Created Jan. 25, 2019: https://pubchem.ncbi.nlm.nih.gov/compound/136794731.
Pubchem CID 141207212, NIH National Library of Medicine/National Center for Biotechnology Information, 1-9, Web. 2019, p. 2.
Pubchem CID 141854888, NIH National Library of Medicine/National Center for Biotechnology Information, 1-9, Web. 2019, p. 2.

(Continued)

*Primary Examiner* — Douglas M Willis
(74) *Attorney, Agent, or Firm* — Dechert LLP; John P. Rearick; Gang Wang

(57) ABSTRACT

The present disclosure relates to novel compounds and pharmaceutical compositions thereof, and methods for inhibiting the activity of PI3K-α enzymes with the compounds and compositions of the disclosure. The present disclosure further relates to, but is not limited to, methods for treating disorders associated with PI3K-α signaling with the compounds and compositions of the disclosure.

6 Claims, No Drawings

(56) References Cited

OTHER PUBLICATIONS

Pubchem CID 57034493 Compound Summary: 7-Phenylchromen-4-one, PubChem. Created Jun. 13, 2012: https://pubchem.ncbi.nlm.nih.gov/compound/57034493.
Pubchem CID 83672716, NIH National Library of Medicine/National Center for Biotechnology Information,, 1-8, Web. 2014, p. 2.
Pubchem SID 368778762, Deposit Date: May 25, 2018; pp. 1-5.
Pubchem SID 381053983, Deposit Date: Jan. 30, 2019, pp. 1-6.
Timmins, "Deuterated drugs: where are we now?" Expert Opin Ther Pat. 2014;24(10):1067-75.
U.S. Appl. No. 17/921,580, filed Oct. 26, 2022.
Yu et al., "Cyclopentadione-aniline conjugate suppresses proliferation and induces apoptosis in liver cancer cells via up-regulation of p38 phosphorylation," Trop J Pharm Res. 2019;18(3):505-11.
Yu et al., "Targeting Protein Kinases Degradation by PROTACs," Front Chem. 2021;9:679120.

SUBSTITUTED ISOINDOLINES AS PI3K-ALPHA INHIBITORS

CROSS-REFERENCE TO RELATED APPLICATIONS

This application is a continuation of U.S. application Ser. No. 17/921,580, filed on Oct. 26, 2022, which is a national stage of International (PCT) Patent Application No. PCT/US2021/029882, filed Apr. 29, 2021, which claims the benefit of U.S. Provisional Application No. 63/017,571, filed on Apr. 29, 2020, and U.S. Provisional Application No. 63/066,489, filed on Aug. 17, 2020; the entirety of each of which is hereby incorporated by reference.

JOINT RESEARCH AGREEMENT

The present disclosure was made by or on behalf of the below listed parties to a joint research agreement. The joint research agreement was in effect on or before the date the present disclosure was made, and the present disclosure was made as a result of activities undertaken within the scope of the joint research agreement. The parties to the joint research agreement are 1) RELAY THERAPEUTICS, INC. and 2) D.E. SHAW RESEARCH, LLC.

BACKGROUND

Phosphatidylinositol 3-kinases (PI3Ks) comprise a family of lipid kinases that catalyze the transfer of phosphate to the D-3' position of inositol lipids to produce phosphoinositol-3-phosphate (PIP), phosphoinositol-3,4-diphosphate ($PIP_2$) and phosphoinositol-3,4,5-triphosphate ($PIP_3$), which, in turn, act as second messengers in signaling cascades by docking proteins containing pleckstrin-homology, FYVE, Phox and other phospholipid-binding domains into a variety of signaling complexes often at the plasma membrane (Vanhaesebroeck et al., Annu. Rev. Biochem 70:535 (2001); Katso et al., Annu. Rev. Cell Dev. Biol. 17:615 (2001)). Of the two Class 1 PI3K sub-classes, Class 1 A PI3Ks are heterodimers composed of a catalytic p110 subunit (alpha, beta, or delta isoforms) constitutively associated with a regulatory subunit that can be p85 alpha, p55 alpha, p50 alpha, p85 beta, or p55 gamma. The Class 1B sub-class has one family member, a heterodimer composed of a catalytic p110 gamma subunit associated with one of two regulatory subunits, p101 or p84 (Fruman et al., Annu Rev. Biochem. 67:481 (1998); Suire et al., Curr. Biol. 15:566 (2005)). The modular domains of the p85/55/50 subunits include Src Homology (SH2) domains that bind phosphotyrosine residues in a specific sequence context on activated receptor and cytoplasmic tyrosine kinases, resulting in activation and localization of Class 1A PI3Ks. Class 1B PI3K is activated directly by G protein-coupled receptors that bind a diverse repertoire of peptide and non-peptide ligands (Stephens et al., Cell 89:105 (1997); Katso et al., Annu. Rev. Cell Dev. Biol. 17:615-675 (2001)).

Consequently, the resultant phospholipid products of Class I PI3Ks link upstream receptors with downstream cellular activities including proliferation, survival, chemotaxis, cellular trafficking, motility, metabolism, inflammatory and allergic responses, transcription and translation (Cantley et al., Cell 64:281 (1991); Escobedo and Williams, Nature 335:85 (1988); Fantl et al., Cell 69:413 (1992)). In many cases, $PIP_2$ and $PIP_3$ recruit Aid, the product of the human homologue of the viral oncogene v-Akt, to the plasma membrane where it acts as a nodal point for many intracellular signaling pathways important for growth and survival (Fantl et al., Cell 69:413-423 (1992); Bader et al., Nature Rev. Cancer 5:921 (2005); Vivanco and Sawyer, Nature Rev. Cancer 2:489 (2002)).

Aberrant regulation of PI3K, which often increases survival through Aid activation, is one of the most prevalent events in human cancer and has been shown to occur at multiple levels. The tumor suppressor gene PTEN, which dephosphorylates phosphoinositides at the 3' position of the inositol ring, and in so doing antagonizes PI3K activity, is functionally deleted in a variety of tumors. In other tumors, the genes for the p110 alpha isoform, PIK3CA, and for Akt are amplified, and increased protein expression of their gene products has been demonstrated in several human cancers. Furthermore, mutations and translocation of p85 alpha that serve to up-regulate the p85-p110 complex have been described in human cancers. Finally, somatic missense mutations in PIK3CA that activate downstream signaling pathways have been described at significant frequencies in a wide diversity of human cancers (Kang et el., Proc. Natl. Acad. Sci. USA 102:802 (2005); Samuels et al., Science 304:554 (2004); Samuels et al., Cancer Cell 7:561-573 (2005)). These observations show that deregulation of phosphoinositol-3 kinase, and the upstream and downstream components of this signaling pathway, is one of the most common deregulations associated with human cancers and proliferative diseases (Parsons et al., Nature 436:792 (2005); Hennessey at el., Nature Rev. Drug Disc. 4:988-1004 (2005)).

In view of the above, inhibitors of PI3Kα would be of particular value in the treatment of proliferative disease and other disorders. While multiple inhibitors of PI3Ks have been developed (for example, taselisib, alpelisib, buparlisib and others), these molecules inhibit multiple Class 1A PI3K isoforms. Inhibitors that are active against multiple Class 1A PI3K isoforms are known as "pan-PI3K" inhibitors. A major hurdle for the clinical development of existing PI3K inhibitors has been the inability to achieve the required level of target inhibition in tumors while avoiding toxicity in cancer patients. Pan-PI3K inhibitors share certain target-related toxicities including diarrhea, rash, fatigue, and hyperglycemia. The toxicity of PI3K inhibitors is dependent on their isoform selectivity profile. Inhibition of PI3Kα is associated with hyperglycemia and rash, whereas inhibition of PI3Kδ or PI3Kγ is associated with diarrhea, myelosuppression, and transaminitis (Hanker et al., Cancer Discovery (2019) PMID: 30837161. Therefore, selective inhibitors of PI3Kα may increase the therapeutic window, enabling sufficient target inhibition in the tumor while avoiding dose-limiting toxicity in cancer patients.

SUMMARY

In some embodiments, the present disclosure provides a compound of formula I-1:

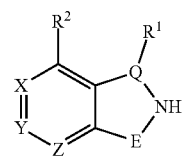

I-1 or a pharmaceutically acceptable salt thereof, wherein each of $R^1$, $R^2$, Q, E, X, Y, and Z is as defined in embodiments and classes and subclasses herein.

In some embodiments, the present disclosure provides a compound of formula I:

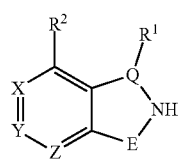

I or a pharmaceutically acceptable salt thereof, wherein each of $R^1$, $R^2$, Q, E, X, Y, and Z is as defined in embodiments and classes and subclasses herein.

In some embodiments, the present invention provides a pharmaceutical composition comprising a compound of formula I, or a pharmaceutically acceptable salt thereof, and a pharmaceutically acceptable carrier, adjuvant, or diluent.

In some embodiments, the present invention provides a method of treating a PI3Kα-mediated disorder comprising administering to a patient in need thereof a compound of formula 1, or composition comprising said compound.

In some embodiments, the present invention provides a process for providing a compound of formula 1, or synthetic intermediates thereof.

In some embodiments, the present invention provides a process for providing pharmaceutical compositions comprising compounds of formula I.

DETAILED DESCRIPTION

1. General Description of Certain Embodiments of the Invention

Compounds of the present invention, and pharmaceutical compositions thereof, are useful as inhibitors of PI3Kα. In some embodiments, the present invention provides a compound of formula I:

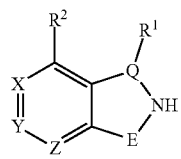

I or a pharmaceutically acceptable salt thereof, wherein:
E is —C(O)—, —C($R^E$)$_2$—, —C($R^E$)$_2$C($R^E$)$_2$—, —C(S)—, —S(O)$_2$—, —OC(O)—, —N($R^E$)C(O)—, —C(O)N($R^E$)—, or —C($R^E$)$_2$C(O)—;
Q is CH, C($R^Q$), or N;
X is CH, C($R^X$), or N;
Y is CH, C($R^Y$), or N;
Z is CH, C($R^Z$), or N;
$R^1$ is -$L^1$-$R^{1A}$;
$R^2$ is -$L^2$-$R^{2A}$;
each instance of $R^E$ is independently H or -$L^E$-$R^{EA}$.
$R^Q$ is -$L^Q$-$R^{QA}$;
$R^X$ is -$L^X$-$R^{XA}$;
$R^Y$ is -$L^Y$-$R^{YA}$;
$R^Z$ is -$L^Z$-$R^{ZA}$; or two instances of $R^E$ are taken together with their intervening atoms to form a 3-8 membered saturated or partially unsaturated monocyclic ring having 0-4 heteroatoms independently selected from nitrogen, oxygen, and sulfur; or an 8-12 membered saturated or partially unsaturated bicyclic ring having 0-4 heteroatoms independently selected from nitrogen, oxygen, and sulfur; wherein each ring is substituted with n instances of $R^{EEC}$;

$R^Q$ and $R^1$ are taken together with their intervening atoms to form a 4-8 membered saturated or partially unsaturated monocyclic ring having 0-4 heteroatoms independently selected from nitrogen, oxygen, and sulfur; or an 8-12 membered saturated or partially unsaturated bicyclic ring having 0-4 heteroatoms independently selected from nitrogen, oxygen, and sulfur; wherein each ring is substituted with p instances of $R^{Q1C}$;

$R^Y$ and $R^Z$ are taken together with their intervening atoms to form a 4-7 membered partially unsaturated or aromatic ring having 0-4 heteroatoms independently selected from nitrogen, oxygen, and sulfur; wherein said ring is substituted with q instances of $R^{YZC}$;

each of $L^1$, $L^2$, $L^E$, $L^Q$, $L^X$, $L^Y$, and $L^Z$ is independently a covalent bond, or a $C_{1-4}$ bivalent saturated or unsaturated, straight or branched hydrocarbon chain wherein one or two methylene units of the chain are optionally and independently replaced by —CH($R^L$)—, —C($R^L$)$_2$—, $C_{3-6}$ cycloalkylene, $C_{3-6}$ heterocycloalkylene, —N(R)—, —N(R)C(O)—, —N(R)C(NR)—, —N(R)C(NOR)—, —N(R)C(NCN)—, —C(O)N(R)—, —N(R)S(O)$_2$—, —S(O)$_2$N(R)—, —O—, —C(O)—, —OC(O)—, —C(O)O—, —S—, —S(O)—, or —S(O)$_2$—;

$R^{1A}$ is $R^A$ or $R^B$ substituted by $r^1$ instances of $R^{1C}$;
$R^{2A}$ is $R^A$ or $R^B$ substituted by $r^2$ instances of $R^{2C}$;
$R^{EA}$ is $R^A$ or $R^B$ substituted by $r^3$ instances of $R^{EC}$;
$R^{QA}$ is $R^A$ or $R^B$ substituted by $r^4$ instances of $R^{QC}$;
$R^{XA}$ is $R^A$ or $R^B$ substituted by instances of $R^{XC}$;
$R^{YA}$ is $R^A$ or $R^B$ substituted by $r^6$ instances of $R^{YC}$;
$R^{ZA}$ is $R^A$ or $R^B$ substituted by $r^7$ instances of $R^{ZC}$;
$R^L$ is $R^A$ or $R^B$ substituted by $r^8$ instances of $R^{LC}$;

each instance of $R^A$ is independently oxo, deuterium, halogen, —CN, —NO$_2$, —OR, —SF$_5$, —SR, —NR$_2$, —S(O)$_2$R, —S(O)$_2$NR$_2$, —S(O)$_2$F, —S(O)R, —S(O)NR$_2$, —S(O)(NR)R, —C(O)R, —C(O)OR, —C(O)NR$_2$, —C(O)N(R)OR, —OC(O)R, —OC(O)NR$_2$, —N(R)C(O)OR, —N(R)C(O)R, —N(R)C(O)NR$_2$, —N(R)C(NR)NR$_2$, —N(R)S(O)$_2$NR$_2$, —N(R)S(O)$_2$R, —P(O)R$_2$, —P(O)(R)OR, or —B(OR)$_2$;

each instance of $R^B$ is independently a $C_{1-6}$ aliphatic chain; phenyl; naphthyl; cubanyl; adamantyl; a 5-6 membered monocyclic heteroaryl ring having 1-4 heteroatoms independently selected from nitrogen, oxygen, and sulfur; an 8-10 membered bicyclic heteroaryl ring having 1-4 heteroatoms independently selected from nitrogen, oxygen, and sulfur; a 3-7 membered saturated or partially unsaturated monocyclic carbocyclic ring; a 5-12 membered saturated or partially unsaturated bicyclic carbocyclic ring; a 3-7 membered saturated or partially unsaturated monocyclic heterocyclic ring having 1-2 heteroatoms independently selected from nitrogen, oxygen, and sulfur; or a 7-12 membered saturated or partially unsaturated bicyclic heterocyclic ring having 1-4 heteroatoms independently selected from nitrogen, oxygen, and sulfur;

each instance of $R^{1C}$, $R^{2C}$, $R^{EC}$, $R^{QC}$, $R^{XC}$, $R^{YC}$, $R^{ZC}$, $R^{LC}$, $R^{EEC}$, $R^{Q1C}$, and $R^{YZC}$ is independently oxo, deuterium, halogen, —CN, —NO$_2$, —OR, —SF$_5$, —SR, —NR$_2$, —S(O)$_2$R, —S(O)$_2$NR$_2$, —S(O)$_2$F, —S(O)R, —S(O)NR$_2$, —S(O)(NR)R, —C(O)R, —C(O)OR, —C(O)NR$_2$, —C(O)N(R)OR, —OC(O)R, —OC(O)NR$_2$, —N(R)C(O)OR, —N(R)C(O)R, —N(R)C(O)NR$_2$, —N(R)C(NR)NR$_2$, —N(R)S(O)$_2$NR$_2$, —N(R)S(O)$_2$R, —P(O)R$_2$, —P(O)(R)OR, —B(OR)$_2$, or an optionally substituted group selected from C$_{1-6}$ aliphatic, phenyl, a 3-7 membered saturated or partially unsaturated monocyclic heterocyclic ring having 1-2 heteroatoms independently selected from nitrogen, oxygen, and sulfur, and a 5-6 membered monocyclic heteroaryl ring having 1-4 heteroatoms independently selected from nitrogen, oxygen, and sulfur;

each instance of R is independently hydrogen, or an optionally substituted group selected from C$_{1-6}$ aliphatic, phenyl, a 3-7 membered saturated or partially unsaturated monocyclic heterocyclic ring having 1-2 heteroatoms independently selected from nitrogen, oxygen, and sulfur, and a 5-6 membered monocyclic heteroaryl ring having 1-4 heteroatoms independently selected from nitrogen, oxygen, and sulfur; or two R groups on the same nitrogen are taken together with their intervening atoms to form a 4-7 membered saturated, partially unsaturated, or heteroaryl ring having 0-3 heteroatoms, in addition to the nitrogen, independently selected from nitrogen, oxygen, and sulfur; and each of n, p, q, $r^1$, $r^2$, $r^3$, $r^4$, $r^5$, $r^6$, $r^7$, and $r^8$ is independently 0, 1, 2, 3, or 4.

2. Compounds and Definitions

Compounds of the present invention include those described generally herein, and are further illustrated by the classes, subclasses, and species disclosed herein. As used herein, the following definitions shall apply unless otherwise indicated. For purposes of this invention, the chemical elements are identified in accordance with the Periodic Table of the Elements, CAS version, Handbook of Chemistry and Physics, 75$^{th}$ Ed. Additionally, general principles of organic chemistry are described in "Organic Chemistry", Thomas Sorrell, University Science Books, Sausalito: 1999, and "March's Advanced Organic Chemistry", 5$^{th}$ Ed., Ed.: Smith, M. B. and March, J., John Wiley & Sons, New York: 2001, the entire contents of which are hereby incorporated by reference.

The term "aliphatic" or "aliphatic group", as used herein, means a straight-chain (i.e., unbranched) or branched, substituted or unsubstituted hydrocarbon chain that is completely saturated or that contains one or more units of unsaturation, or a monocyclic hydrocarbon or bicyclic hydrocarbon that is completely saturated or that contains one or more units of unsaturation, but which is not aromatic (also referred to herein as "carbocycle" or "cycloaliphatic"), that has a single point of attachment to the rest of the molecule. Unless otherwise specified, aliphatic groups contain 1-6 aliphatic carbon atoms. In some embodiments, aliphatic groups contain 1-5 aliphatic carbon atoms. In other embodiments, aliphatic groups contain 1-4 aliphatic carbon atoms. In still other embodiments, aliphatic groups contain 1-3 aliphatic carbon atoms, and in yet other embodiments, aliphatic groups contain 1-2 aliphatic carbon atoms. In some embodiments, "cycloaliphatic" (or "carbocycle") refers to a monocyclic C$_3$-C$_6$ hydrocarbon that is completely saturated or that contains one or more units of unsaturation, but which is not aromatic, that has a single point of attachment to the rest of the molecule. Suitable aliphatic groups include, but are not limited to, linear or branched, substituted or unsubstituted alkyl, alkenyl, alkynyl groups and hybrids thereof such as (cycloalkyl)alkyl, (cycloalkenyl)alkyl or (cycloalkyl)alkenyl.

The term "alkyl", unless otherwise indicated, as used herein, refers to a monovalent aliphatic hydrocarbon radical having a straight chain, branched chain, monocyclic moiety, or polycyclic moiety or combinations thereof, wherein the radical is optionally substituted at one or more carbons of the straight chain, branched chain, monocyclic moiety, or polycyclic moiety or combinations thereof with one or more substituents at each carbon, wherein the one or more substituents are independently C$_1$-C$_{10}$ alkyl. Examples of "alkyl" groups include methyl, ethyl, propyl, isopropyl, butyl, iso-butyl, sec-butyl, tert-butyl, pentyl, hexyl, heptyl, cyclopropyl, cyclobutyl, cyclopentyl, cyclohexyl, cycloheptyl, norbornyl, and the like.

The term "lower alkyl" refers to a C$_{1-4}$ straight or branched alkyl group. Exemplary lower alkyl groups are methyl, ethyl, propyl, isopropyl, butyl, isobutyl, and tert-butyl.

The term "lower haloalkyl" refers to a C$_{1-4}$ straight or branched alkyl group that is substituted with one or more halogen atoms.

The term "heteroatom" means one or more of oxygen, sulfur, nitrogen, phosphorus, or silicon (including, any oxidized form of nitrogen, sulfur, phosphorus, or silicon; the quaternized form of any basic nitrogen or; a substitutable nitrogen of a heterocyclic ring, for example N (as in 3,4-dihydro-2H-pyrrolyl), NH (as in pyrrolidinyl) or NR (as in N-substituted pyrrolidinyl)).

The term "unsaturated," as used herein, means that a moiety has one or more units of unsaturation.

As used herein, the term "C$_{1-8}$ (or C$_{1-6}$, or C$_{1-4}$) bivalent saturated or unsaturated, straight or branched, hydrocarbon chain", refers to bivalent alkylene, alkenylene, and alkynylene chains that are straight or branched as defined herein.

The term "alkylene" refers to a bivalent alkyl group. An "alkylene chain" is a polymethylene group, i.e., —(CH$_2$)$_n$—, wherein n is a positive integer, preferably from 1 to 6, from 1 to 4, from 1 to 3, from 1 to 2, or from 2 to 3. A substituted alkylene chain is a polymethylene group in which one or more methylene hydrogen atoms are replaced with a substituent. Suitable substituents include those described below for a substituted aliphatic group.

The term "alkenylene" refers to a bivalent alkenyl group. A substituted alkenylene chain is a polymethylene group containing at least one double bond in which one or more hydrogen atoms are replaced with a substituent. Suitable substituents include those described below for a substituted aliphatic group.

The term "halogen" means F, Cl, Br, or I.

The term "aryl," used alone or as part of a larger moiety as in "aralkyl," "aralkoxy," or "aryloxyalkyl," refers to monocyclic or bicyclic ring systems having a total of five to fourteen ring members, wherein at least one ring in the system is aromatic and wherein each ring in the system contains 3 to 7 ring members. The term "aryl" may be used interchangeably with the term "aryl ring." In certain embodiments of the present invention, "aryl" refers to an aromatic ring system which includes, but is not limited to, phenyl, biphenyl, naphthyl, anthracyl and the like, which may bear one or more substituents.

The terms "heteroaryl" or "heteroaromatic", unless otherwise defined, as used herein refers to a monocyclic aromatic 5-6 membered ring containing one or more heteroatoms, for example one to three heteroatoms, such as nitrogen, oxygen, and sulfur, or an 8-10 membered polycyclic ring system containing one or more heteroatoms, wherein at least one ring in the polycyclic ring system is aromatic, and the point of attachment of the polycyclic ring system is through a ring atom on an aromatic ring. A heteroaryl ring may be linked to adjacent radicals though carbon or nitrogen. Examples of heteroaryl rings include but are not limited to furan, thiophene, pyrrole, thiazole, oxazole, isothiazole, isoxazole, imidazole, pyrazole, triazole, pyridine, pyrimidine, indole, etc. For example, unless otherwise defined, 1,2,3,4-tetrahydroquinoline is a heteroaryl ring if its point of attachment is through the benzo ring, e.g.:

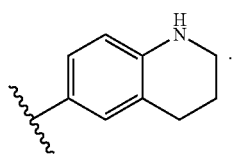 [SMILES: *c1ccc2c(c1)CCCN2]

The terms "heterocyclyl" or "heterocyclic group", unless otherwise defined, refer to a saturated or partially unsaturated 3-10 membered monocyclic or 7-14 membered polycyclic ring system, including bridged or fused rings, and whose ring system includes one to four heteroatoms, such as nitrogen, oxygen, and sulfur. A heterocyclyl ring may be linked to adjacent radicals through carbon or nitrogen.

The term "partially unsaturated" in the context of rings, unless otherwise defined, refers to a monocyclic ring, or a component ring within a polycyclic (e.g. bicyclic, tricyclic, etc.) ring system, wherein the component ring contains at least one degree of unsaturation in addition to those provided by the ring itself, but is not aromatic. Examples of partially unsaturated rings include, but are not limited to, 3,4-dihydro-2H-pyran, 3-pyrroline, 2-thiazoline, etc. Where a partially unsaturated ring is part of a polycyclic ring system, the other component rings in the polycyclic ring system may be saturated, partially unsaturated, or aromatic, but the point of attachment of the polycyclic ring system is on a partially unsaturated component ring. For example, unless otherwise defined, 1,2,3,4-tetrahydroquinoline is a partially unsaturated ring if its point of attachment is through the piperidino ring, e.g.:

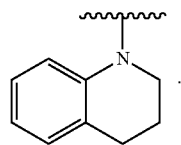 [SMILES: *N1CCCc2ccccc21]

The term "saturated" in the context of rings, unless otherwise defined, refers to a 3-10 membered monocyclic ring, or a 7-14 membered polycyclic (e.g. bicyclic, tricyclic, etc.) ring system, wherein the monocyclic ring or the component ring that is the point of attachment for the polycyclic ring system contains no additional degrees of unsaturation in addition to that provided by the ring itself. Examples of monocyclic saturated rings include, but are not limited to, azetidine, oxetane, cyclohexane, etc. Where a saturated ring is part of a polycyclic ring system, the other component rings in the polycyclic ring system may be saturated, partially unsaturated, or aromatic, but the point of attachment of the polycyclic ring system is on a saturated component ring. For example, unless otherwise defined, 2-azaspiro[3.4]oct-6-ene is a saturated ring if its point of attachment is through the azetidino ring, e.g.:

The terms "alkylene", "arylene", "cycloalkylene", "heteroarylene", "heterocycloalkylene", and the other similar terms with the suffix "-ylene" as used herein refers to a divalently bonded version of the group that the suffix modifies. For example, "alkylene" is a divalent alkyl group connecting the groups to which it is attached.

As used herein, the term "bridged bicyclic" refers to any bicyclic ring system, i.e. carbocyclic or heterocyclic, saturated or partially unsaturated, having at least one bridge. As defined by IUPAC, a "bridge" is an unbranched chain of atoms or an atom or a valence bond connecting two bridgeheads, where a "bridgehead" is any skeletal atom of the ring system which is bonded to three or more skeletal atoms (excluding hydrogen). In some embodiments, a bridged bicyclic group has 7-12 ring members and 0-4 heteroatoms independently selected from nitrogen, oxygen, or sulfur. Such bridged bicyclic groups are well known in the art and include those groups set forth below where each group is attached to the rest of the molecule at any substitutable carbon or nitrogen atom. Unless otherwise specified, a bridged bicyclic group is optionally substituted with one or more substituents as set forth for aliphatic groups. Additionally or alternatively, any substitutable nitrogen of a bridged bicyclic group is optionally substituted. Exemplary bridged bicyclics include:

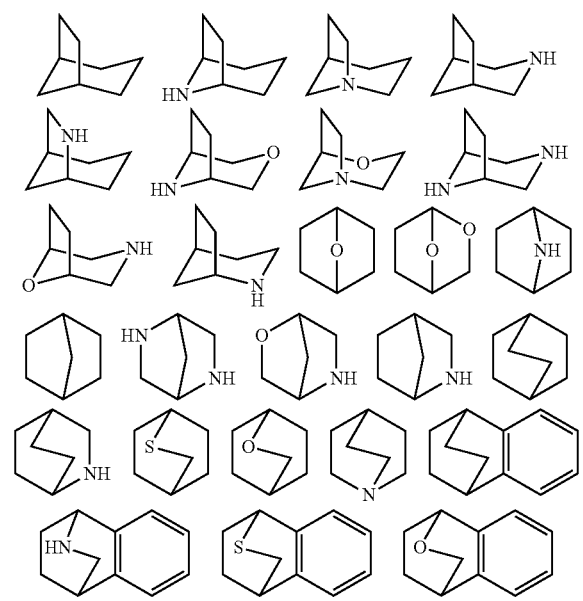

As described herein, compounds of the invention may contain "optionally substituted" moieties. In general, the term "substituted," whether preceded by the term "optionally" or not, means that one or more hydrogens of the designated moiety are replaced with a suitable substituent. Unless otherwise indicated, an "optionally substituted" group may have a suitable substituent at each substitutable position of the group, and when more than one position in any given structure may be substituted with more than one substituent selected from a specified group, the substituent may be either the same or different at every position.

Combinations of substituents envisioned by this invention are preferably those that result in the formation of stable or chemically feasible compounds. The term "stable," as used herein, refers to compounds that are not substantially altered when subjected to conditions to allow for their production, detection, and, in certain embodiments, their recovery, purification, and use for one or more of the purposes disclosed herein.

Suitable monovalent substituents on a substitutable carbon atom of an "optionally substituted" group are independently halogen; —$(CH_2)_{0-4}R°$; —$(CH_2)_{0-4}OR°$; —$O(CH_2)_{0-4}R°$, —O—$(CH_2)_{0-4}C(O)OR°$; —$(CH_2)_{0-4}CH(OR°)_2$; —$(CH_2)_{0-4}SR°$; —$(CH_2)_{0-4}Ph$, which may be substituted with $R°$; —$(CH_2)_{0-4}O(CH_2)_{0-1}Ph$ which may be substituted with $R°$; —CH=CHPh, which may be substituted with $R°$; —$(CH_2)_{0-4}O(CH_2)_{0-1}$-pyridyl which may be substituted with $R°$; —$NO_2$; —CN; —$N_3$; —$(CH_2)_{0-4}N(R°)_2$; —$(CH_2)_{0-4}N(R°)C(O)R°$; —$N(R°)C(S)R°$; —$(CH_2)_{0-4}N(R°)C(O)NR°_2$; —$N(R°)C(S)NR°_2$; —$(CH_2)_{0-4}N(R°)C(O)OR°$; —$N(R°)N(R°)C(O)R°$; —$N(R°)N(R°)C(O)NR°_2$; —$N(R°)N(R°)C(O)OR°$; —$(CH_2)_{0-4}C(O)R°$; —C(S)R°; —$(CH_2)_{0-4}C(O)OR°$; —$(CH_2)_{0-4}C(O)SR°$; —$(CH_2)_{0-4}C(O)OSiR°_3$; —$(CH_2)_{0-4}OC(O)R°$; —$OC(O)(CH_2)_{0-4}SR°$; —SC(S)SR°; —$(CH_2)_{0-4}SC(O)R°$; —$(CH_2)_{0-4}C(O)NR°_2$; —$C(S)NR°_2$; —$C(S)SR°$; —$SC(S)SR°$, —$(CH_2)_{0-4}OC(O)NR°_2$; —$C(O)N(OR°)R°$; —$C(O)C(O)R°$; —$C(O)CH_2C(O)R°$; —$C(NOR°)R°$; —$(CH_2)_{0-4}SSR°$; —$(CH_2)_{0-4}S(O)_2R°$; —$(CH_2)_{0-4}S(O)_2OR°$; —$(CH_2)_{0-4}OS(O)_2R°$; —$S(O)_2NR°_2$; —$(CH_2)_{0-4}S(O)R°$; —$N(R°)S(O)_2NR°_2$; —$N(R°)S(O)_2R°$; —$N(OR°)R°$; —$C(NH)NR°_2$; —$P(O)(OR°)R°$; —$P(O)R°_2$; —$OP(O)R°_2$; —$OP(O)(OR°)_2$; —$SiR°_3$; —$(C_{1-4}$ straight or branched alkylene)O—$N(R°)_2$; or —$(C_{1-4}$ straight or branched alkylene)C(O)O—$N(R°)_2$, wherein each $R°$ may be substituted as defined below and is independently hydrogen, $C_{1-6}$ aliphatic, —$CH_2Ph$, —$O(CH_2)_{0-1}Ph$, —$CH_2$-(5-6 membered heteroaryl ring), or a 5-6-membered saturated, partially unsaturated, or aryl ring having 0-4 heteroatoms independently selected from nitrogen, oxygen, or sulfur, or, notwithstanding the definition above, two independent occurrences of $R°$, taken together with their intervening atom(s), form a 3-12-membered saturated, partially unsaturated, or aryl mono- or bicyclic ring having 0-4 heteroatoms independently selected from nitrogen, oxygen, or sulfur, which may be substituted as defined below.

Suitable monovalent substituents on $R°$ (or the ring formed by taking two independent occurrences of $R°$ together with their intervening atoms), are independently halogen, —$(CH_2)_{0-2}R^•$, -(haloR$^•$), —$(CH_2)_{0-2}OH$, —$(CH_2)_{0-2}OR^•$, —$(CH_2)_{0-2}CH(OR^•)_2$; —O(haloR$^•$), —CN, —$N_3$, —$(CH_2)_{0-2}C(O)R^•$, —$(CH_2)_{0-2}C(O)OH$, —$(CH_2)_{0-2}C(O)OR^*$, —$(CH_2)_{0-2}SR^•$, —$(CH_2)_{0-2}SH$, —$(CH_2)_{0-2}NH_2$, —$(CH_2)_{0-2}NHR^•$, —$(CH_2)_{0-2}NR^•_2$, —$NO_2$, —$SiR^•_3$, —$OSiR^•_3$, —$C(O)SR^•$, —$(C_{1-4}$ straight or branched alkylene)C(O)OR$^•$, or —SSR$^•$ wherein each $R^•$ is unsubstituted or where preceded by "halo" is substituted only with one or more halogens, and is independently selected from $C_{1-4}$ aliphatic, —$CH_2Ph$, —$O(CH_2)_{0-1}Ph$, or a 5-6-membered saturated, partially unsaturated, or aryl ring having 0-4 heteroatoms independently selected from nitrogen, oxygen, or sulfur. Suitable divalent substituents on a saturated carbon atom of $R°$ include =O and =S.

Suitable divalent substituents on a saturated carbon atom of an "optionally substituted" group include the following: =O, =S, =$NNR^*_2$, =NNHC(O)R*, =NNHC(O)OR*, =$NNHS(O)_2R^*$, =NR*, =NOR*, —$O(C(R^*_2))_{2-3}O$—, or —$S(C(R^*_2))_{2-3}S$—, wherein each independent occurrence of R* is selected from hydrogen, $C_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur. Suitable divalent substituents that are bound to vicinal substitutable carbons of an "optionally substituted" group include: —$O(CR^*_2)_{2-3}O$—, wherein each independent occurrence of R* is selected from hydrogen, $C_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur.

Suitable substituents on the aliphatic group of R* include halogen, —R$^•$, -(haloR$^•$), —OH, —OR$^•$, —O(haloR$^•$), —CN, —C(O)OH, —C(O)OR$^•$, —$NH_2$, —NHR$^•$, —NR$^•_2$, or —$NO_2$, wherein each R$^•$ is unsubstituted or where preceded by "halo" is substituted only with one or more halogens, and is independently $C_{1-4}$ aliphatic, —$CH_2Ph$, —$O(CH_2)_{0-1}Ph$, or a 5-6-membered saturated, partially unsaturated, or aryl ring having 0-4 heteroatoms independently selected from nitrogen, oxygen, or sulfur.

Suitable substituents on a substitutable nitrogen of an "optionally substituted" group include —R$^†$, —NR$^†_2$, —C(O)R$^†$, —C(O)OR$^†$, —C(O)C(O)R$^†$, —C(O)$CH_2$C(O)R$^†$, —$S(O)_2R^†$, —$S(O)_2NR^†_2$, —C(S)NR$^†_2$, —C(NH)NR$^†_2$, or —$N(R^T)S(O)_2R^†$; wherein each R$^†$ is independently hydrogen, $C_{1-6}$ aliphatic which may be substituted as defined below, unsubstituted —OPh, or an unsubstituted 5-6-membered saturated, partially unsaturated, or aryl ring having 0-4 heteroatoms independently selected from nitrogen, oxygen, or sulfur, or, notwithstanding the definition above, two independent occurrences of R$^†$, taken together with their intervening atom(s) form an unsubstituted 3-12-membered saturated, partially unsaturated, or aryl mono- or bicyclic ring having 0-4 heteroatoms independently selected from nitrogen, oxygen, or sulfur.

Suitable substituents on the aliphatic group of R$^†$ are independently halogen, —R$^•$, -(haloR$^•$), —OH, —OR$^•$, —O(haloR$^•$), —CN, —C(O)OH, —C(O)OR$^•$, —$NH_2$, —NHR$^•$, —NR$^•_2$, or —$NO_2$, wherein each R$^•$ is unsubstituted or where preceded by "halo" is substituted only with one or more halogens, and is independently $C_{1-4}$ aliphatic, —$CH_2Ph$, —$O(CH_2)_{0-1}Ph$, or a 5-6-membered saturated, partially unsaturated, or aryl ring having 0-4 heteroatoms independently selected from nitrogen, oxygen, or sulfur.

The term "isomer" as used herein refers to a compound having the identical chemical formula but different structural or optical configurations. The term "stereoisomer" as used herein refers to and includes isomeric molecules that have the same molecular formula but differ in positioning of atoms and/or functional groups in the space. All stereoisomers of the present compounds (e.g., those which may exist due to asymmetric carbons on various substituents), including enantiomeric forms and diastereomeric forms, are contemplated within the scope of this disclosure. Therefore, unless otherwise stated, single stereochemical isomers as well as mixtures of enantiomeric, diastereomeric, and geometric (or conformational) isomers of the present compounds are within the scope of the invention.

The term "tautomer" as used herein refers to one of two or more structural isomers which exist in equilibrium and which are readily converted from one isomeric form to another. It is understood that tautomers encompass valence tautomers and proton tautomers (also known as prototropic tautomers). Valence tautomers include interconversions by reorganization of some of the bonding electrons. Proton tautomers include interconversions via migration of a proton, such as keto-enol and imine-enamine isomerizations. Unless otherwise stated, all tautomers of the compounds of the invention are within the scope of the invention.

The term "isotopic substitution" as used herein refers to the substitution of an atom with its isotope. The term "isotope" as used herein refers to an atom having the same atomic number as that of atoms dominant in nature but having a mass number (neutron number) different from the mass number of the atoms dominant in nature. It is understood that a compound with an isotopic substitution refers to a compound in which at least one atom contained therein is substituted with its isotope. Atoms that can be substituted with its isotope include, but are not limited to, hydrogen, carbon, and oxygen. Examples of the isotope of a hydrogen atom include $^2$H (also represented as D) and $^3$H. Examples of the isotope of a carbon atom include $^{13}$C and $^{14}$C. Examples of the isotope of an oxygen atom include $^{18}$O. Unless otherwise stated, all isotopic substitution of the compounds of the invention are within the scope of the invention. Such compounds are useful, for example, as analytical tools, as probes in biological assays, or as therapeutic agents in accordance with the present invention. In certain embodiments, for example, a warhead moiety, $R^W$, of a provided compound comprises one or more deuterium atoms.

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Exemplary pharmaceutically acceptable salts are found, e.g., in Berge, et al. (*J. Pharm. Sci.* 1977, 66(1), 1; and Gould, P. L., *Int. J. Pharmaceutics* 1986, 33, 201-217; (each hereby incorporated by reference in its entirety).

Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, pivalate, propionate, stearate, succinate, sulfate, tartrate, thiocyanate, p-toluenesulfonate, undecanoate, valerate salts, and the like.

Salts derived from appropriate bases include alkali metal, alkaline earth metal, ammonium and $N^+(C_{1-4}alkyl)_4$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, loweralkyl sulfonate and aryl sulfonate.

Pharmaceutically acceptable salts are also intended to encompass hemi-salts, wherein the ratio of compound:acid is respectively 2:1. Exemplary hemi-salts are those salts derived from acids comprising two carboxylic acid groups, such as malic acid, fumaric acid, maleic acid, succinic acid, tartaric acid, glutaric acid, oxalic acid, adipic acid and citric acid. Other exemplary hemi-salts are those salts derived from diprotic mineral acids such as sulfuric acid. Exemplary preferred hemi-salts include, but are not limited to, hemimaleate, hemifumarate, and hemisuccinate.

As used herein the term "about" is used herein to mean approximately, roughly, around, or in the region of. When the term "about" is used in conjunction with a numerical range, it modifies that range by extending the boundaries above and below the numerical values set forth. In general, the term "about" is used herein to modify a numerical value above and below the stated value by a variance of 20 percent up or down (higher or lower).

An "effective amount", "sufficient amount" or "therapeutically effective amount" as used herein is an amount of a compound that is sufficient to effect beneficial or desired results, including clinical results. As such, the effective amount may be sufficient, e.g., to reduce or ameliorate the severity and/or duration of afflictions related to PI3Kα signaling, or one or more symptoms thereof, prevent the advancement of conditions or symptoms related to afflictions related to PI3Kα signaling, or enhance or otherwise improve the prophylactic or therapeutic effect(s) of another therapy. An effective amount also includes the amount of the compound that avoids or substantially attenuates undesirable side effects.

As used herein and as well understood in the art, "treatment" is an approach for obtaining beneficial or desired results, including clinical results. Beneficial or desired clinical results may include, but are not limited to, alleviation or amelioration of one or more symptoms or conditions, diminution of extent of disease or affliction, a stabilized (i.e., not worsening) state of disease or affliction, preventing spread of disease or affliction, delay or slowing of disease or affliction progression, amelioration or palliation of the disease or affliction state and remission (whether partial or total), whether detectable or undetectable. "Treatment" can also mean prolonging survival as compared to expected survival if not receiving treatment. In some embodiments, treatment may be administered after one or more symptoms have developed. In other embodiments, treatment may be administered in the absence of symptoms. For example, treatment may be administered to a susceptible individual prior to the onset of symptoms (e.g., in light of a history of symptoms and/or in light of genetic or other susceptibility factors). Treatment may also be continued after symptoms have resolved, for example to prevent or delay their recurrence.

The phrase "in need thereof" refers to the need for symptomatic or asymptomatic relief from conditions related to PI3Kα signaling activity or that may otherwise be relieved by the compounds and/or compositions of the disclosure.

3. Description of Exemplary Embodiments

As described above, in some embodiments, the present invention provides a compound of formula I-1:

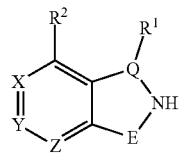

I-1 or a pharmaceutically acceptable salt thereof, wherein:

E is —C(O)—, —C($R^E$)$_2$—, —C($R^E$)$_2$C($R^E$)$_2$—, —C(S)—, —S(O)$_2$—, —OC(O)—, —N($R^E$)C(O)—, —C(O)N($R^E$)—, or —C($R^E$)$_2$C(O)—;

Q is CH, C($R^Q$), or N;
X is CH, C($R^X$), or N;
Y is CH, C($R^Y$), or N;
Z is CH, C($R^Z$), or N;
$R^1$ is -$L^1$-$R^{1A}$;
$R^2$ is -$L^2$-$R^{2A}$;
each instance of $R^E$ is independently H or -$L^E$-$R^{EA}$.
$R^Q$ is -$L^Q$-$R^{QA}$;
$R^X$ is -$L^X$-$R^{XA}$;
$R^Y$ is -$L^Y$-$R^{YA}$;
$R^Z$ is -$L^Z$-$R^{ZA}$; or two instances of $R^E$ are taken together with their intervening atoms to form a 3-8 membered saturated or partially unsaturated monocyclic ring having 0-4 heteroatoms independently selected from nitrogen, oxygen, and sulfur; or an 8-12 membered saturated or partially unsaturated bicyclic ring having 0-4 heteroatoms independently selected from nitrogen, oxygen, and sulfur; wherein each ring is substituted with n instances of $R^{EEC}$;

$R^Q$ and $R^1$ are taken together with their intervening atoms to form a 4-8 membered saturated or partially unsaturated monocyclic ring having 0-4 heteroatoms independently selected from nitrogen, oxygen, and sulfur; or an 8-12 membered saturated or partially unsaturated bicyclic ring having 0-4 heteroatoms independently selected from nitrogen, oxygen, and sulfur; wherein each ring is substituted with p instances of $R^{Q1C}$;

$R^Y$ and $R^Z$ are taken together with their intervening atoms to form a 4-7 membered partially unsaturated or aromatic ring having 0-4 heteroatoms independently selected from nitrogen, oxygen, and sulfur; wherein said ring is substituted with q instances of $R^{YZC}$;

each of $L^1$, $L^2$, $L^E$, $L^Q$, $L^X$, $L^Y$, and $L^Z$ is independently a covalent bond, or a $C_{1-4}$ bivalent saturated or unsaturated, straight or branched hydrocarbon chain wherein one or two methylene units of the chain are optionally and independently replaced by —CH($R^L$)—, —C($R^L$)$_2$—, $C_{3-6}$ cycloalkylene, $C_{3-6}$ heterocycloalkylene, —N(R)—, —N(R)C(O)—, —N(R)C(NR)—, —N(R)C(NOR)—, —N(R)C(NCN)—, —C(O)N(R)—, —N(R)S(O)$_2$—, —S(O)$_2$N(R)—, —O—, —C(O)—, —OC(O)—, —C(O)O—, —S—, —S(O)—, or —S(O)$_2$—;

$R^{1A}$ is $R^A$ or $R^B$ substituted by r instances of $R^{1C}$;
$R^{2A}$ is $R^A$ or $R^B$ substituted by $r^2$ instances of $R^{2C}$;
$R^{EA}$ is $R^A$ or $R^B$ substituted by $r^3$ instances of $R^{EC}$;
$R^{QA}$ is $R^A$ or $R^B$ substituted by $r^4$ instances of $R^{QC}$;
$R^{XA}$ is $R^A$ or $R^B$ substituted by $r^5$ instances of $R^{XC}$;
$R^{YA}$ is $R^A$ or $R^B$ substituted by $r^6$ instances of $R^{YC}$;
$R^{ZA}$ is $R^A$ or $R^B$ substituted by r instances of $R^{ZC}$;
$R^L$ is $R^A$ or $R^B$ substituted by $r^8$ instances of $R^{LC}$;

each instance of $R^A$ is independently oxo, deuterium, halogen, —CN, —NO$_2$, —OR, —SF$_5$, —SR, —NR$_2$, —S(O)$_2$R, —S(O)$_2$NR$_2$, —S(O)$_2$F, —S(O)R, —S(O)NR$_2$, —S(O)(NR)R, —S(O)(NCN)R, —S(NCN)R, —C(O)R, —C(O)OR, —C(O)NR$_2$, —C(O)N(R)OR, —OC(O)R, —OC(O)NR$_2$, —N(R)C(O)OR, —N(R)C(O)R, —N(R)C(O)NR$_2$, —N(R)C(NR)NR$_2$, —N(R)S(O)$_2$NR$_2$, —N(R)S(O)$_2$R, —P(O)R$_2$, —P(O)(R)OR, or —B(OR)$_2$;

each instance of $R^B$ is independently a $C_{1-6}$ aliphatic chain; phenyl; naphthyl; cubanyl; adamantyl; a 5-6 membered monocyclic heteroaryl ring having 1-4 heteroatoms independently selected from nitrogen, oxygen, and sulfur; an 8-10 membered bicyclic heteroaryl ring having 1-4 heteroatoms independently selected from nitrogen, oxygen, and sulfur; a 3-7 membered saturated or partially unsaturated monocyclic carbocyclic ring; a 5-12 membered saturated or partially unsaturated bicyclic carbocyclic ring; a 3-7 membered saturated or partially unsaturated monocyclic heterocyclic ring having 1-2 heteroatoms independently selected from nitrogen, oxygen, and sulfur; or a 7-12 membered saturated or partially unsaturated bicyclic heterocyclic ring having 1-4 heteroatoms independently selected from nitrogen, oxygen, and sulfur;

each instance of $R^{1C}$, $R^{2C}$, $R^{EC}$, $R^{QC}$, $R^{XC}$, $R^{YC}$, $R^{ZC}$, $R^{LC}$, $R^{EEC}$, $R^{Q1C}$ and $R^{YZC}$ is independently oxo, deuterium, halogen, —CN, —NO$_2$, —OR, —SF$_5$, —SR, —NR$_2$, —S(O)$_2$R, —S(O)$_2$NR$_2$, —S(O)$_2$F, —S(O)R, —S(O)NR$_2$, —S(O)(NR)R, —C(O)R, —C(O)OR, —C(O)NR$_2$, —C(O)N(R)OR, —OC(O)R, —OC(O)NR$_2$, —N(R)C(O)OR, —N(R)C(O)R, —N(R)C(O)NR$_2$, —N(R)C(NR)NR$_2$, —N(R)S(O)$_2$NR$_2$, —N(R)S(O)$_2$R, —P(O)R$_2$, —P(O)(R)OR, —B(OR)$_2$, or an optionally substituted group selected from $C_{1-6}$ aliphatic, phenyl, a 3-7 membered saturated or partially unsaturated monocyclic heterocyclic ring having 1-2 heteroatoms independently selected from nitrogen, oxygen, and sulfur, and a 5-6 membered monocyclic heteroaryl ring having 1-4 heteroatoms independently selected from nitrogen, oxygen, and sulfur; each instance of R is independently hydrogen, or an optionally substituted group selected from $C_{1-6}$ aliphatic, phenyl, a 3-7 membered saturated or partially unsaturated monocyclic heterocyclic ring having 1-2 heteroatoms independently selected from nitrogen, oxygen, and sulfur, and a 5-6 membered monocyclic heteroaryl ring having 1-4 heteroatoms independently selected from nitrogen, oxygen, and sulfur; or two R groups on the same nitrogen are taken together with their intervening atoms to form a 4-7 membered saturated, partially unsaturated, or heteroaryl ring having 0-3 heteroatoms, in addition to the nitrogen, independently selected from nitrogen, oxygen, and sulfur; and each of n, p, q, $r^1$, $r^2$, $r^3$, $r^4$, $r^5$, $r^6$, $r^7$, and $r^8$ is independently 0, 1, 2, 3, 4, or 5.

In some embodiments, the present invention provides a compound of Formula I-1, wherein each of E, Q, X Y, Z, $R^1$, $R^2$, $R^E$, $R^Q$, $R^X$, $R^Y$, $R^Z$, $R^{1A}$, $R^{2A}$, $R^{EA}$, $R^{QA}$, $R^{XA}$, $R^{YA}$, $R^{ZA}$ $R^L$, $R^A$, $R^B$, $R^{1C}$, $R^{2C}$, $R^{EC}$, $R^{QC}$, $R^{XC}$, $R^{YC}$, $R^{ZC}$, $R^{LC}$, $R^{EEC}$, $R^{Q1C}$, $R^{YZC}$, R, n, p q $r^1$, $r^2$, $r^3$, $r^4$, $r^5$, $r^6$, $r^7$, and $r^8$ is as defined below, and described in embodiments herein, both singly and in combination.

In certain embodiments, $R^{YA}$ is —S(O)$_2$R, —S(O)$_2$NR$_2$, —S(O)$_2$F, —S(O)R, —S(O)NR$_2$, —S(O)(NR)R, —S(O)(NCN)R, or —S(NCN)R. In certain embodiments, $R^{YA}$ is —S(O)(NR)R, —S(O)(NCN)R, or —S(NCN)R. In certain embodiments, $R^{YA}$ is —S(O)(NCN)R or —S(NCN)R. In certain embodiments, $R^{YA}$ is —S(O)(NCN)R. In certain embodiments, $R^{YA}$ is —S(NCN)R. In some embodiments, $R^{YA}$ is selected from the groups depicted in the compounds in Table 1.

In certain embodiments, $R^A$ is —S(O)$_2$R, —S(O)$_2$NR$_2$, —S(O)$_2$F, —S(O)R, —S(O)NR$_2$, —S(O)(NR)R, —S(O)(NCN)R, or —S(NCN)R. In certain embodiments, $R^A$ is —S(O)(NR)R, —S(O)(NCN)R, or —S(NCN)R. In certain embodiments, $R^A$ is —S(O)(NCN)R or —S(NCN)R. In certain embodiments, $R^A$ is —S(O)(NCN)R. In certain embodiments, $R^A$ is —S(NCN)R. In some embodiments, $R^A$ is selected from the groups depicted in the compounds in Table 1.

In certain embodiments, n is 1, 2, 3, 4, or 5. In certain embodiments, n is 2, 3, 4, or 5. In certain embodiments, n is 3, 4, or 5. In certain embodiments, n is 4 or 5. In certain embodiments, n is 5. In certain embodiments, n is selected from the values represented in the compounds in Table 1.

In certain embodiments, p is 1, 2, 3, 4, or 5. In certain embodiments, p is 2, 3, 4, or 5. In certain embodiments, p is 3, 4, or 5. In certain embodiments, p is 4 or 5. In certain embodiments, p is 5. In certain embodiments, p is selected from the values represented in the compounds in Table 1.

In certain embodiments, q is 1, 2, 3, 4, or 5. In certain embodiments, q is 2, 3, 4, or 5. In certain embodiments, q is 3, 4, or 5. In certain embodiments, q is 4 or 5. In certain embodiments, q is 5. In certain embodiments, q is selected from the values represented in the compounds in Table 1.

In certain embodiments, $r^1$ is 1, 2, 3, 4, or 5. In certain embodiments, $r^1$ is 2, 3, 4, or 5. In certain embodiments, $r^1$ is 3, 4, or 5. In certain embodiments, $r^1$ is 4 or 5. In certain embodiments, $r^1$ is 5. In certain embodiments, $r^1$ is selected from the values represented in the compounds in Table 1.

In certain embodiments, $r^2$ is 1, 2, 3, 4, or 5. In certain embodiments, $r^2$ is 2, 3, 4, or 5. In certain embodiments, $r^2$ is 3, 4, or 5. In certain embodiments, $r^2$ is 4 or 5. In certain embodiments, $r^2$ is 5. In certain embodiments, $r^2$ is selected from the values represented in the compounds in Table 1.

In certain embodiments, $r^3$ is 1, 2, 3, 4, or 5. In certain embodiments, $r^3$ is 2, 3, 4, or 5. In certain embodiments, $r^3$ is 3, 4, or 5. In certain embodiments, $r^3$ is 4 or 5. In certain embodiments, $r^3$ is 5. In certain embodiments, $r^3$ is selected from the values represented in the compounds in Table 1.

In certain embodiments, $r^4$ is 1, 2, 3, 4, or 5. In certain embodiments, $r^4$ is 2, 3, 4, or 5. In certain embodiments, $r^4$ is 3, 4, or 5. In certain embodiments, $r^4$ is 4 or 5. In certain embodiments, $r^4$ is 5. In certain embodiments, $r^4$ is selected from the values represented in the compounds in Table 1.

In certain embodiments, $r^5$ is 1, 2, 3, 4, or 5. In certain embodiments, $r^5$ is 2, 3, 4, or 5. In certain embodiments, $r^5$ is 3, 4, or 5. In certain embodiments, $r^5$ is 4 or 5. In certain embodiments, $r^5$ is 5. In certain embodiments, $r^5$ is selected from the values represented in the compounds in Table 1.

In certain embodiments, $r^6$ is 1, 2, 3, 4, or 5. In certain embodiments, $r^6$ is 2, 3, 4, or 5. In certain embodiments, $r^6$ is 3, 4, or 5. In certain embodiments, $r^6$ is 4 or 5. In certain embodiments, $r^6$ is 5. In certain embodiments, $r^6$ is selected from the values represented in the compounds in Table 1.

In certain embodiments, $r^7$ is 1, 2, 3, 4, or 5. In certain embodiments, $r^7$ is 2, 3, 4, or 5. In certain embodiments, $r^7$ is 3, 4, or 5. In certain embodiments, $r^7$ is 4 or 5. In certain embodiments, $r^7$ is 5. In certain embodiments, $r^7$ is selected from the values represented in the compounds in Table 1.

In certain embodiments, $r^8$ is 1, 2, 3, 4, or 5. In certain embodiments, $r^8$ is 2, 3, 4, or 5. In certain embodiments, $r^8$ is 3, 4, or 5. In certain embodiments, $r^8$ is 4 or 5. In certain embodiments, $r^8$ is 5. In certain embodiments, $r^8$ is selected from the values represented in the compounds in Table 1.

As described above, in some embodiments, the present invention provides a compound of formula I:

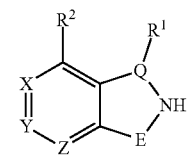

or a pharmaceutically acceptable salt thereof, wherein:
E is —C(O)—, —C($R^E$)$_2$—, —C($R^E$)$_2$C($R^E$)$_2$—, —C(S)—, —S(O)$_2$—, —OC(O)—, —N($R^E$)C(O)—, —C(O)N($R^E$)—, or —C($R^E$)$_2$C(O)—;
Q is CH, C($R^Q$), or N;
X is CH, C($R^X$), or N;
Y is CH, C($R^Y$), or N;
Z is CH, C($R^Z$), or N;
$R^1$ is -$L^1$-$R^{1A}$;
$R^2$ is -$L^2$-$R^{2A}$;
each instance of $R^E$ is independently H or -$L^E$-$R^{EA}$.
$R^Q$ is -$L^Q$-$R^{QA}$;
$R^X$ is -$L^X$-$R^{XA}$;
$R^Y$ is -$L^Y$-$R^{YA}$
$R^Z$ is -$L^Z$-$R^{ZA}$; or
  two instances of $R^E$ are taken together with their intervening atoms to form a 3-8 membered saturated or partially unsaturated monocyclic ring having 0-4 heteroatoms independently selected from nitrogen, oxygen, and sulfur; or an 8-12 membered saturated or partially unsaturated bicyclic ring having 0-4 heteroatoms independently selected from nitrogen, oxygen, and sulfur; wherein each ring is substituted with n instances of $R^{EEC}$;
  $R^Q$ and $R^1$ are taken together with their intervening atoms to form a 4-8 membered saturated or partially unsaturated monocyclic ring having 0-4 heteroatoms independently selected from nitrogen, oxygen, and sulfur; or an 8-12 membered saturated or partially unsaturated bicyclic ring having 0-4 heteroatoms independently selected from nitrogen, oxygen, and sulfur; wherein each ring is substituted with p instances of $R^{Q1C}$;
  $R^Y$ and $R^Z$ are taken together with their intervening atoms to form a 4-7 membered partially unsaturated or aromatic ring having 0-4 heteroatoms independently selected from nitrogen, oxygen, and sulfur; wherein said ring is substituted with q instances of $R^{YZC}$;
each of $L^1$, $L^2$, $L^E$, $L^Q$, $L^X$, $L^Y$, and $L^Z$ is independently a covalent bond, or a $C_{1-4}$ bivalent saturated or unsaturated, straight or branched hydrocarbon chain wherein one or two methylene units of the chain are optionally and independently replaced by —CH($R^L$)—, —C($R^E$)$_2$—, $C_{3-6}$ cycloalkylene, $C_{3-6}$ heterocycloalkylene, —N(R)—, —N(R)C(O)—, —N(R)C(NR)—, —N(R)C(NOR)—, —N(R)C(NCN)—, —C(O)N(R)—, —N(R)S(O)$_2$—, —S(O)$_2$N(R)—, —O—, —C(O)—, —OC(O)—, —C(O)O—, —S—, —S(O)—, or —S(O)$_2$—;

$R^{1A}$ is $R^A$ or $R^B$ substituted by $r^1$ instances of $R^{1C}$;
$R^{2A}$ is $R^A$ or $R^B$ substituted by $r^2$ instances of $R^{2C}$;
$R^{EA}$ is $R^A$ or $R^B$ substituted by $r^3$ instances of $R^{EC}$;
$R^{QA}$ is $R^A$ or $R^B$ substituted by $r^4$ instances of $R^{QC}$;
$R^{XA}$ is $R^A$ or $R^B$ substituted by instances of $R^{XC}$;
$R^{YA}$ is $R^A$ or $R^B$ substituted by $r^6$ instances of $R^{YC}$;
$R^{ZA}$ is $R^A$ or $R^B$ substituted by r instances of $R^{ZC}$;
$R^L$ is $R^A$ or $R^B$ substituted by $r^8$ instances of $R^{LC}$;

each instance of $R^A$ is independently oxo, deuterium, halogen, —CN, —NO$_2$, —OR, —SF$_5$, —SR, —NR$_2$, —S(O)$_2$R, —S(O)$_2$NR$_2$, —S(O)$_2$F, —S(O)R, —S(O)NR$_2$, —S(O)(NR)R, —C(O)R, —C(O)OR, —C(O)NR$_2$, —C(O)N(R)OR, —OC(O)R, —OC(O)NR$_2$, —N(R)C(O)OR, —N(R)C(O)R, —N(R)C(O)NR$_2$, —N(R)C(NR)NR$_2$, —N(R)S(O)$_2$NR$_2$, —N(R)S(O)$_2$R, —P(O)R$_2$, —P(O)(R)OR, or —B(OR)$_2$;

each instance of $R^B$ is independently a $C_{1-6}$ aliphatic chain; phenyl; naphthyl; cubanyl; adamantyl; a 5-6 membered monocyclic heteroaryl ring having 1-4 heteroatoms independently selected from nitrogen, oxygen, and sulfur; an 8-10 membered bicyclic heteroaryl ring having 1-4 heteroatoms independently selected from nitrogen, oxygen, and sulfur; a 3-7 membered saturated or partially unsaturated monocyclic carbocyclic ring; a 5-12 membered saturated or partially unsaturated bicyclic carbocyclic ring; a 3-7 membered saturated or partially unsaturated monocyclic heterocyclic ring having 1-2 heteroatoms independently selected from nitrogen, oxygen, and sulfur; or a 7-12 membered saturated or partially unsaturated bicyclic heterocyclic ring having 1-4 heteroatoms independently selected from nitrogen, oxygen, and sulfur;

each instance of $R^{1C}$, $R^{2C}$, $R^{EC}$, $R^{QC}$, $R^{XC}$, $R^{YC}$, $R^{ZC}$, $R^{LC}$, $R^{EEC}$, $R^{Q1C}$, and $R^{YZC}$ is independently oxo, deuterium, halogen, —CN, —NO$_2$, —OR, —SF$_5$, —SR, —NR$_2$, —S(O)$_2$R, —S(O)$_2$NR$_2$, —S(O)$_2$F, —S(O)R, —S(O)NR$_2$, —S(O)(NR)R, —C(O)R, —C(O)OR, —C(O)NR$_2$, —C(O)N(R)OR, —OC(O)R, —OC(O)NR$_2$, —N(R)C(O)OR, —N(R)C(O)R, —N(R)C(O)NR$_2$, —N(R)C(NR)NR$_2$, —N(R)S(O)$_2$NR$_2$, —N(R)S(O)$_2$R, —P(O)R$_2$, —P(O)(R)OR, —B(OR)$_2$, or an optionally substituted group selected from $C_{1-6}$ aliphatic, phenyl, a 3-7 membered saturated or partially unsaturated monocyclic heterocyclic ring having 1-2 heteroatoms independently selected from nitrogen, oxygen, and sulfur, and a 5-6 membered monocyclic heteroaryl ring having 1-4 heteroatoms independently selected from nitrogen, oxygen, and sulfur;

each instance of R is independently hydrogen, or an optionally substituted group selected from $C_{1-6}$ aliphatic, phenyl, a 3-7 membered saturated or partially unsaturated monocyclic heterocyclic ring having 1-2 heteroatoms independently selected from nitrogen, oxygen, and sulfur, and a 5-6 membered monocyclic heteroaryl ring having 1-4 heteroatoms independently selected from nitrogen, oxygen, and sulfur; or two R groups on the same nitrogen are taken together with their intervening atoms to form a 4-7 membered saturated, partially unsaturated, or heteroaryl ring having 0-3 heteroatoms, in addition to the nitrogen, independently selected from nitrogen, oxygen, and sulfur; and each of n, p, q, $r^1$, $r^2$, $r^3$, $r^4$, $r^5$, $r^6$, $r^7$, and $r^8$ is independently 0, 1, 2, 3, or 4.

As defined generally above, E is —C(O)—, —C(R$^E$)$_2$—, —C(R$^E$)$_2$C(R$^E$)$_2$—, $C_{3-6}$ cycloalkylene, $C_{3-6}$ heterocycloalkylene, —C(S)—, —S(O)$_2$—, —OC(O)—, —N(R$^E$)C(O)—, —C(O)N(R$^E$)—, or —C(R$^E$)$_2$C(O)—. In some embodiments, E is —C(O)—. In some embodiments, E is —OC(O)— or —N(R$^E$)C(O)—. In some embodiments, E is —C(R$^E$)$_2$—, $C_{3-6}$ cycloalkylene, or $C_{3-6}$ heterocycloalkylene.

In some embodiments, E is —C(O)—, —OC(O)—, —N(R$^E$)C(O)—, or —C(R$^E$)$_2$C(O)—. In some embodiments, E is —OC(O)—, —N(R$^E$)C(O)—, or —C(R$^E$)$_2$C(O)—. In some embodiments, E is —C(O)— or —N(R$^E$)C(O)—.

In some embodiments, E is —C(O)—, —C(R$^E$)$_2$—, —C(S)—, or —S(O)$_2$—. In some embodiments, E is —C(O)—, —C(R$^E$)$_2$—, or —C(S)—. In some embodiments, E is —C(O)— or —C(S)—.

In some embodiments, E is —C(R$^E$)$_2$C(R$^E$)$_2$—, $C_{3-6}$ cycloalkylene, $C_{3-6}$ heterocycloalkylene, —OC(O)—, —N(R$^E$)C(O)—, —C(O)N(R$^E$)—, or —C(R$^E$)$_2$C(O)—. In some embodiments, E is $C_{3-6}$ cycloalkylene or $C_{3-6}$ heterocycloalkylene. In some embodiments, E is —C(R$^E$)$_2$C(R$^E$)$_2$—, —OC(O)—, —N(R$^E$)C(O)—, —C(O)N(R$^E$)—, or —C(R$^E$)$_2$C(O)—. In some embodiments, E is —OC(O)—, —N(R$^E$)C(O)—, —C(O)N(R$^E$)—, or —C(R$^E$)$_2$C(O)—. In some embodiments, E is —OC(O)—, —N(R$^E$)C(O)—, or —C(O)N(R$^E$)—. In some embodiments, E is —N(R$^E$)C(O)— or —C(O)N(R$^E$)—. In some embodiments, E is —N(H)C(O)— or —C(O)N(H)—. In some embodiments, E is —N(CH$_3$)C(O)— or —C(O)N(CH$_3$)—.

In some embodiments, E is —S(O)$_2$—, —OC(O)—, —N(R$^E$)C(O)—, or —C(O)N(R$^E$)—. In some embodiments, E is —C(O)—, —C(R$^E$)$_2$—, —C(R$^E$)$_2$C(R$^E$)$_2$—, $C_{3-6}$ cycloalkylene, $C_{3-6}$ heterocycloalkylene, —C(S)—, or —C(R$^E$)$_2$C(O)—. In some embodiments, E is —C(O)—, —C(R$^E$)$_2$—, —C(R$^E$)$_2$C(R$^E$)$_2$—, —C(S)—, or —C(R$^E$)$_2$C(O)—. In some embodiments, E is —C(O)—, —C(S)—, or —C(R$^E$)$_2$C(O)—. In some embodiments, E is —C(R$^E$)$_2$—, —C(R$^E$)$_2$C(R$^E$)$_2$—, or —C(R$^E$)$_2$C(O)—. In some embodiments, E is —C(R$^E$)$_2$— or —C(R$^E$)$_2$C(R$^E$)$_2$—.

In some embodiments, E is —C(R$^E$)$_2$—. In some embodiments, E is —C(R$^E$)$_2$C(R$^E$)$_2$—. In some embodiments, E is $C_{3-6}$ cycloalkylene. In some embodiments, E is $C_{3-6}$ heterocycloalkylene. In some embodiments, E is —C(S)—. In some embodiments, E is —S(O)$_2$—. In some embodiments, E is —OC(O)—. In some embodiments, E is —N(R$^E$)C(O)—. In some embodiments, E is —N(H)C(O)—. In some embodiments, E is —N(CH$_3$)C(O)—. In some embodiments, E is —C(O)N(R$^E$)—. In some embodiments, E is —C(O)N(H)—. In some embodiments, E is —C(O)N(CH$_3$)—. In some embodiments, E is —C(R$^E$)$_2$C(O)—.

In some embodiments, E is selected from the groups depicted in the compounds in Table 1.

As defined generally above, Q is CH, C(R$^Q$), or N. In some embodiments, Q is CH. In some embodiments, Q is C(R$^Q$). In some embodiments, Q is N. In some embodiments, Q is CH or C(R$^Q$). In some embodiments, Q is CH or N. In some embodiments, Q is C(R$^Q$) or N. In some embodiments, Q is selected from the groups depicted in the compounds in Table 1.

As defined generally above, X is CH, C(R$^X$), or N. In some embodiments, X is CH. In some embodiments, X is C($R^X$). In some embodiments, X is N. In some embodiments, X is CH or C($R^X$). In some embodiments, X is CH or N. In some embodiments, X is C($R^X$) or N. In some embodiments, X is selected from the groups depicted in the compounds in Table 1.

As defined generally above, Y is CH, C($R^Y$), or N. In some embodiments, Y is CH. In some embodiments, Y is C($R^Y$). In some embodiments, Y is N. In some embodiments, Y is CH or C($R^Y$). In some embodiments, Y is CH or N. In some embodiments, Y is C($R^Y$) or N. In some embodiments, Y is selected from the groups depicted in the compounds in Table 1.

As defined generally above, Z is CH, C($R^Z$), or N. In some embodiments, Z is CH. In some embodiments, Z is C($R^Z$). In some embodiments, Z is N. In some embodiments, Z is CH or C($R^Z$). In some embodiments, Z is CH or N. In some embodiments, Z is C($R^Z$) or N. In some embodiments, Z is selected from the groups depicted in the compounds in Table 1.

As defined generally above, $R^1$ is -$L^1$-$R^{1A}$ or $R^Q$ and $R^1$ are taken together with their intervening atoms to form a 4-8 membered saturated or partially unsaturated monocyclic ring having 0-4 heteroatoms independently selected from nitrogen, oxygen, and sulfur; or an 8-12 membered saturated or partially unsaturated bicyclic ring having 0-4 heteroatoms independently selected from nitrogen, oxygen, and sulfur; wherein each ring is substituted with p instances of $R^{Q1C}$. In some embodiments, $R^1$ is -$L^1$-$R^{1A}$. In some embodiments, $R^1$ is —$R^{1A}$.

In some embodiments, $R^Q$ and $R^1$ are taken together with their intervening atoms to form a 4-8 membered saturated or partially unsaturated monocyclic ring having 0-4 heteroatoms independently selected from nitrogen, oxygen, and sulfur; or an 8-12 membered saturated or partially unsaturated bicyclic ring having 0-4 heteroatoms independently selected from nitrogen, oxygen, and sulfur; wherein each ring is substituted with p instances of $R^{Q1C}$ In some embodiments, $R^Q$ and $R^1$ are taken together with their intervening atoms to form a 4-8 membered saturated or partially unsaturated monocyclic ring having 0-4 heteroatoms independently selected from nitrogen, oxygen, and sulfur; wherein said ring is substituted with p instances of $R^{Q1C}$. In some embodiments, $R^Q$ and $R^1$ are taken together with their intervening atoms to form an 8-12 membered saturated or partially unsaturated bicyclic ring having 0-4 heteroatoms independently selected from nitrogen, oxygen, and sulfur; wherein said ring is substituted with p instances of $R^{Q1C}$.

In some embodiments, $R^1$ (i.e. -$L^1$-$R^{1A}$ taken together) is

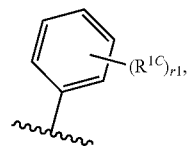

wherein $R^{1C}$ embodiments, $R^1$ (i.e. -$L^1$-$R^{1A}$ taken together) is

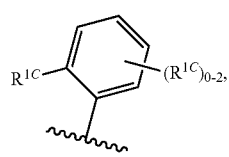

wherein $R^{1C}$ is as defined in the embodiments and classes and subclasses herein. In some embodiments, $R^1$ (i.e. -$L^1$-$R^{1A}$ taken together) is

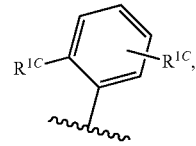

wherein $R^{1C}$ is as defined in the embodiments and classes and subclasses herein. In some embodiments, $R^1$ (i.e. -$L^1$-$R^{1A}$ taken together) is

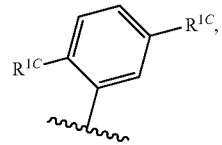

wherein $R^{1C}$ is as defined in the embodiments and classes and subclasses herein. In some embodiments, $R^1$ (i.e. -$L^1$-$R^{1A}$ taken together) is

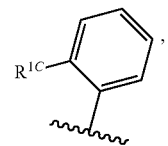

wherein $R^{1C}$ is as defined in the embodiments and classes and subclasses herein.

In some embodiments, $R^1$ (i.e. -$L^1$-$R^{1A}$ taken together) is

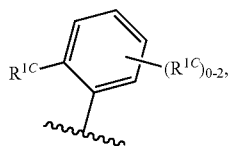

wherein each instance of $R^{1C}$ is independently halogen, —CN, —O-(optionally substituted $C_{1-6}$ aliphatic), or an optionally substituted $C_{1-6}$ aliphatic. In some embodiments, $R^1$ (i.e. -$L^1$-$R^{1A}$ taken together) is

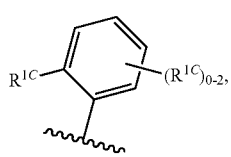

wherein each instance of $R^{1C}$ is independently halogen or $C_{1-3}$ aliphatic optionally substituted with 1-3 halogen. In some embodiments, $R^1$ (i.e. -$L^1$-$R^{1A}$ taken together) is

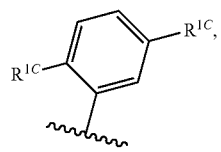

wherein each instance of $R^{1C}$ is independently halogen or $C_{1-3}$ aliphatic optionally substituted with 1-3 halogen. In some embodiments, $R^1$ (i.e. -$L^1$-$R^{1A}$ taken together) is

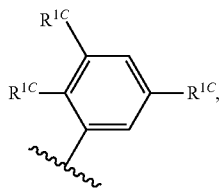

wherein each instance of $R^{1C}$ is independently halogen or $C_{1-3}$ aliphatic optionally substituted with 1-3 halogen. In some embodiments, $R^1$ (i.e. -$L^1$-$R^{1A}$ taken together) is

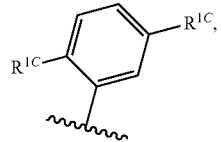

wherein each instance of $R^{1C}$ is independently fluorine, chlorine, —$CH_3$, —$CHF_2$, or —$CF_3$. In some embodiments, $R^1$ (i.e. -$L^1$-$R^{1A}$ taken together) is

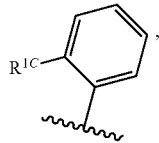

wherein $R^{1C}$ is halogen or $C_{1-3}$ aliphatic optionally substituted with 1-3 halogen.

In some embodiments, $R^1$ (i.e. -$L^1$-$R^{1A}$ taken together) is

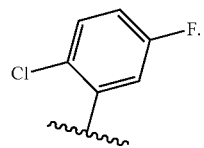 [SMILES: *c1cc(F)ccc1Cl]

In some embodiments, $R^1$ (i.e. -$L^1$-$R^{1A}$ taken together) is

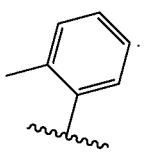

In some embodiments, $R^1$ (i.e. -$L^1$-$R^{1A}$ taken together) is

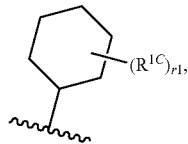

wherein $R^{1C}$ and $r^1$ are as defined in the embodiments and classes and subclasses herein. In some embodiments, $R^1$ (i.e. -$L^1$-$R^{1A}$ taken together) is

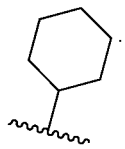 [SMILES: *C1CCCCC1]

In some embodiments, $R^1$ (i.e. -$L^1$-$R^{1A}$ taken together) is

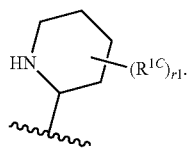

In some embodiments, $R^1$ (i.e. -L-$R^{1A}$ taken together) is

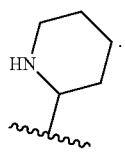

In some embodiments, $R^1$ is selected from the groups depicted in the compounds in Table 1.

As defined generally above, $R^2$ is -$L^2$-$R^{2A}$. In some embodiments, $R^2$ (i.e. -$L^2$-$R^{2A}$ taken together) is —N(R)C(O)—$R^{2A}$ or —$R^{2A}$, wherein R and $R^{2A}$ are as defined in the embodiments and classes and subclasses herein. In some embodiments, $R^2$ (i.e. -$L^2$-$R^{2A}$ taken together) is —N(R)C(O)—$R^{2A}$, wherein R and $R^{2A}$ are as defined in the embodiments and classes and subclasses herein. In some embodiments, $R^2$ (i.e. -$L^2$-$R^{2A}$ taken together) is —N(H)C(O)—$R^{2A}$, wherein $R^{2A}$ is as defined in the embodiments and classes and subclasses herein. In some embodiments, $R^2$ (i.e. -$L^2$-$R^{2A}$ taken together) is —N(H)C(O)—$R^{2A}$, wherein $R^{2A}$ is $R^B$ substituted by $r^2$ instances of $R^{2C}$. In some embodiments, $R^2$ is -$R^{2A}$.

In some embodiments, $R^2$ is —N(H)C(O)—$R^{2A}$, —N(H)C(O)N(H)—$R^{2A}$, —C(O)N(H)—$R^{2A}$, —N(H)—$R^{2A}$, —S(O)$_2$CH$_2$—$R^{2A}$, —CH$_2$S(O)$_2$—$R^{2A}$, or —C(H)(CH$_3$)OH. In some embodiments, $R^2$ is —N(H)C(O)—$R^{2A}$, —N(H)C(O)N(H)—$R^{2A}$, or —N(H)—$R^{2A}$. In some embodiments, $R^2$ is —C(O)N(H)—$R^{2A}$, —CH$_2$S(O)$_2$—$R^{2A}$, or —C(H)(CH$_3$)OH. In some embodiments, $R^2$ is —S(O)$_2$CH$_2$—$R^{2A}$ or —CH$_2$S(O)$_2$—$R^{2A}$.

In some embodiments, $R^2$ is —N(H)C(O)N(H)—$R^{2A}$. In some embodiments, $R^2$ is —C(O)N(H)—$R^{2A}$. In some embodiments, $R^2$ is —N(H)—$R^{2A}$. In some embodiments, $R^2$ is —S(O)$_2$CH$_2$—$R^{2A}$. In some embodiments, $R^2$ is —CH$_2$S(O)$_2$—$R^{2A}$. In some embodiments, $R^2$ is —C(H)(CH$_3$)OH.

In some embodiments, $R^2$ (i.e. -L$^2$-R$^{2A}$ taken together) is

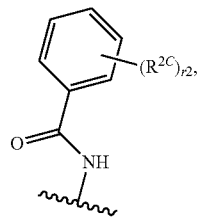

wherein $R^{2C}$ and $r^2$ are as defined in the embodiments and classes and subclasses herein. In some embodiments, $R^2$ (i.e. -L$^2$-R$^{2A}$ taken together) is

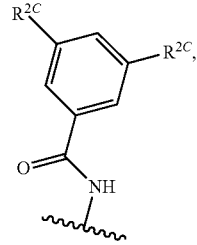

wherein $R^{2C}$ is as defined in the embodiments and classes and subclasses herein.

In some embodiments, $R^2$ (i.e. -L$^2$-R$^{2A}$ taken together) is

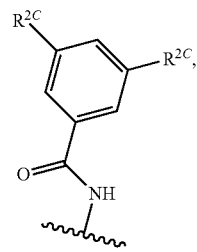

wherein each instance of $R^{2C}$ is independently halogen, —CN, —O-(optionally substituted C$_{1-6}$ aliphatic), or an optionally substituted C$_{1-6}$ aliphatic. In some embodiments, $R^2$ (i.e. -L$^2$-R$^{2A}$ taken together) is

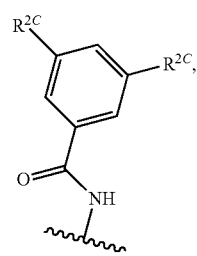

wherein each instance of $R^{2C}$ is independently halogen or C$_{1-3}$ aliphatic optionally substituted with 1-3 halogen. In some embodiments, $R^2$ (i.e. -L$^2$-R$^{2A}$ taken together) is

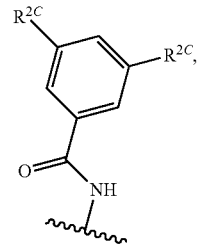

wherein each instance of $R^{2C}$ is independently fluorine, chlorine, —CH$_3$, —CHF$_2$, or —CF$_3$. In some embodiments, $R^2$ (i.e. -L$^2$-R$^{2A}$ taken together) is

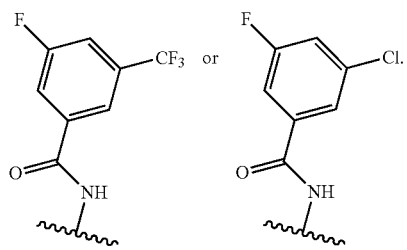 [SMILES: *NC(=O)c1cc(F)cc(C(F)(F)F)c1 ; *NC(=O)c1cc(F)cc(Cl)c1]

In some embodiments, $R^2$ (i.e. -L$^2$-R$^{2A}$ taken together) is

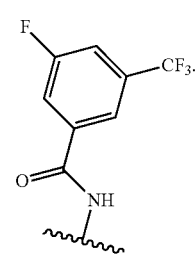 [SMILES: *NC(=O)c1cc(F)cc(C(F)(F)F)c1]

In some embodiments, $R^2$ (i.e. -L$^2$-R$^{2A}$ taken together) is

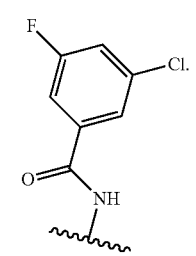 [SMILES: *NC(=O)c1cc(F)cc(Cl)c1]

In some embodiments, $R^2$ (i.e. -$L^2$-$R^{2A}$ taken together) is

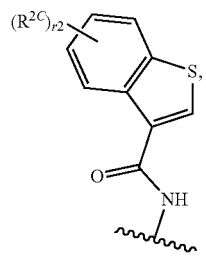

wherein $R^{2C}$ and $r^2$ are as defined in the embodiments and classes and subclasses herein. In some embodiments, $R^2$ (i.e. -$L^2$-$R^{2A}$ taken together) is

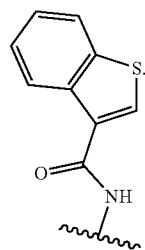 [SMILES: *NC(=O)c1csc2ccccc12]

In some embodiments, $R^2$ (i.e. -$L^2$-$R^{2A}$ taken together) is

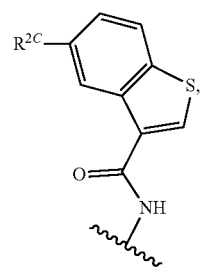

wherein $R^{2C}$ is as defined in the embodiments and classes and subclasses herein.

In some embodiments, $R^2$ (i.e. -$L^2$-$R^{2A}$ taken together) is

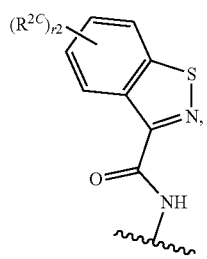

wherein $R^{2C}$ and $r^2$ are as defined in the embodiments and classes and subclasses herein. In some embodiments, $R^2$ (i.e. -$L^2$-$R^{2A}$ taken together) is

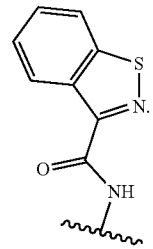 [SMILES: *NC(=O)c1nsc2ccccc12]

In some embodiments, $R^2$ (i.e. -$L^2$-$R^{2A}$ taken together) is

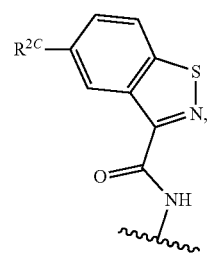

wherein $R^{2C}$ is as defined in the embodiments and classes and subclasses herein.

In some embodiments, $R^2$ (i.e. -$L^2$-$R^{2A}$ taken together) is

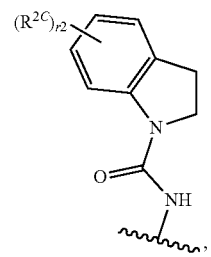

wherein embodiments, $R^2$ (i.e. -$L^2$-$R^{2A}$ taken together) is

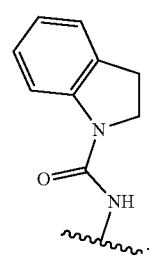 [SMILES: *NC(=O)N1CCc2ccccc21]

In some embodiments, $R^2$ (i.e. -$L^2$-$R^{2A}$ taken together) is

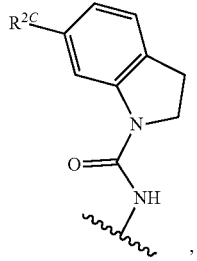, wherein $R^{2C}$ is as defined in the embodiments and classes and subclasses herein.

In some embodiments, $R^2$ (i.e. -$L^2$-$R^{2A}$ taken together) is

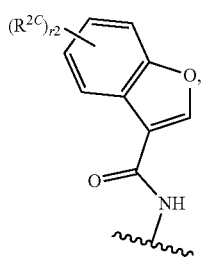, wherein $R^{2C}$ and $r^2$ are as defined in the embodiments and classes and subclasses herein. In some embodiments, $R^2$ (i.e. -$L^2$-$R^{2A}$ taken together) is

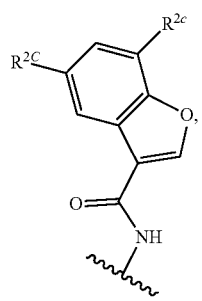, wherein $R^{2C}$ is as defined in the embodiments and classes and subclasses herein.

In some embodiments, $R^2$ (i.e. -$L^2$-$R^{2A}$ taken together) is

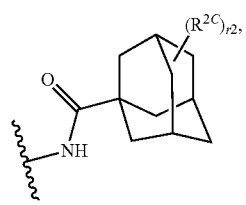

wherein $R^{2C}$ and $r^2$ are as defined in the embodiments and classes and subclasses herein. In some embodiments, $R^2$ (i.e. -$L^2$-$R^{2A}$ taken together) is

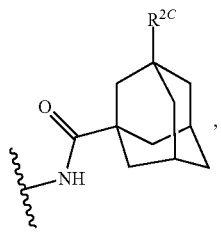, wherein $R^{2C}$ is as defined in the embodiments and classes and subclasses herein.

In some embodiments, $R^2$ (i.e. -$L^2$-$R^{2A}$ taken together) is

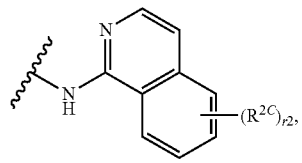, wherein $R^{2C}$ and $r^2$ are as defined in the embodiments and classes and subclasses herein. In some embodiments, $R^2$ (i.e. -$L^2$-$R^{2A}$ taken together) is

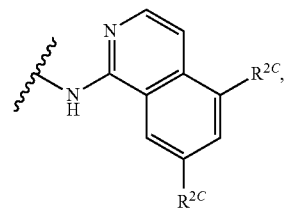, wherein $R^{2C}$ is as defined in the embodiments and classes and subclasses herein.

In some embodiments, $R^2$ (i.e. -$L^2$-$R^{2A}$ taken together) is

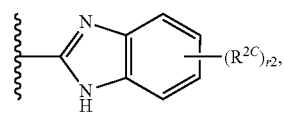, wherein $R^{2C}$ and $r^2$ are as defined in the embodiments and classes and subclasses herein. In some embodiments, $R^2$ (i.e. -$L^2$-$R^{2A}$ taken together) is

, wherein $R^{2C}$ is as defined in the embodiments and classes and subclasses herein.

In some embodiments, R² is
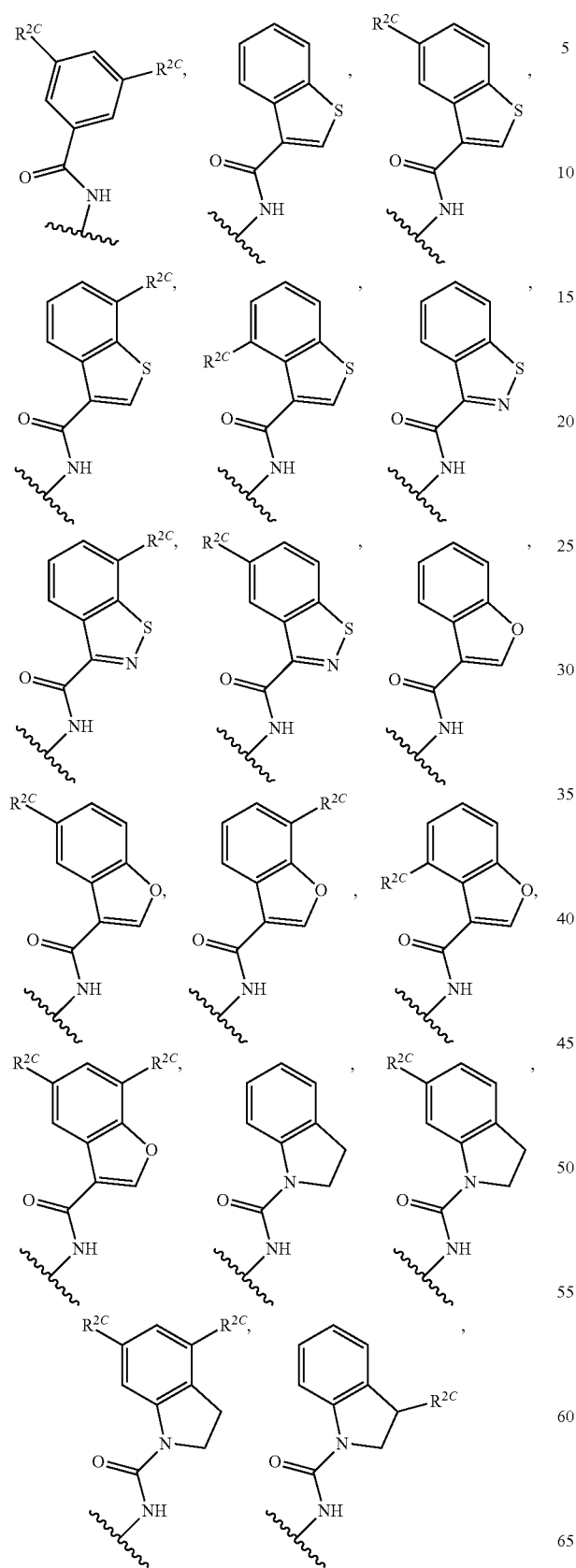
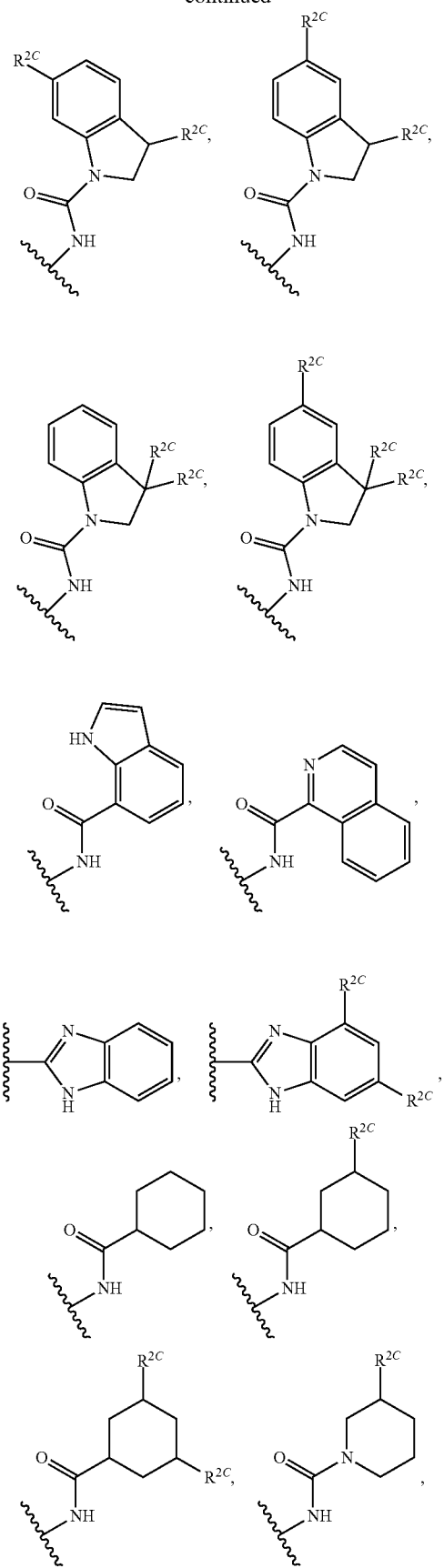

-continued
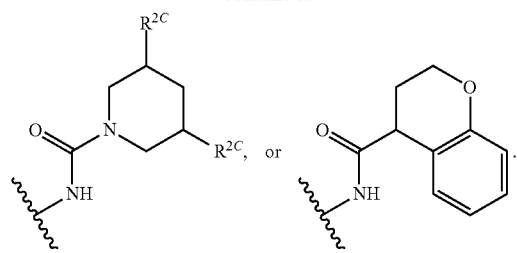
In some embodiments, $R^2$ is
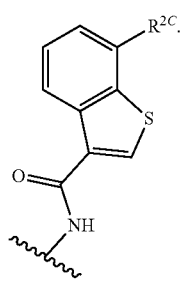
In some embodiments, $R^2$ is
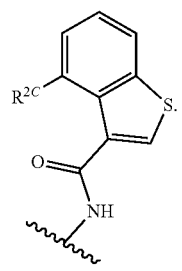
In some embodiments, $R^2$ is
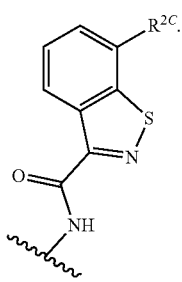
In some embodiments, $R^2$ is
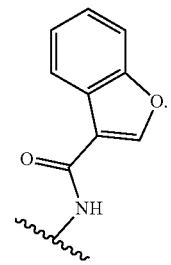 [SMILES: *NC(=O)c1coc2ccccc12]
In some embodiments, $R^2$ is
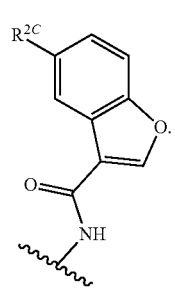
In some embodiments, $R^2$ is
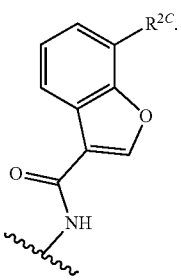
In some embodiments, $R^2$ is
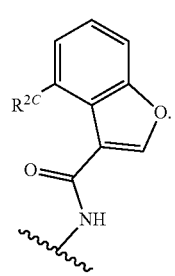

In some embodiments, R² is
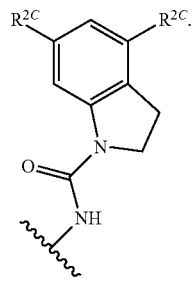
In some embodiments, R² is
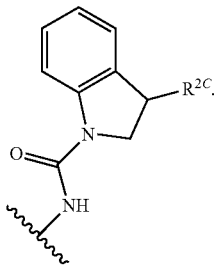
In some embodiments, R² is
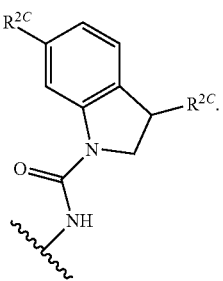
In some embodiments, R² is
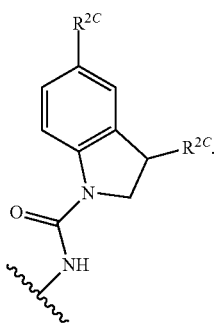
In some embodiments, R² is
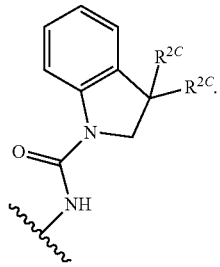
In some embodiments, R² is
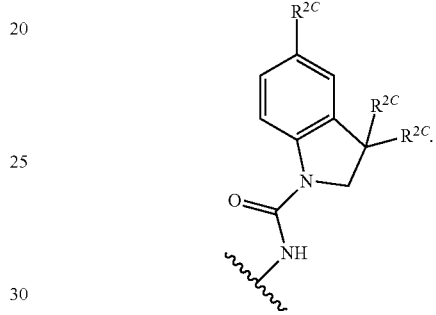
In some embodiments, R² is
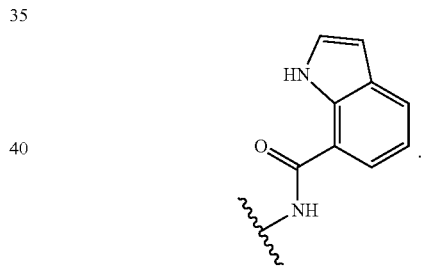
In some embodiments, R² is
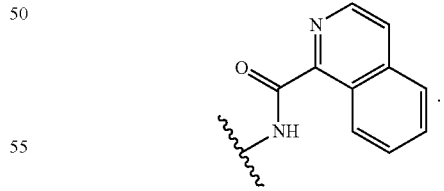
In some embodiments, R² is
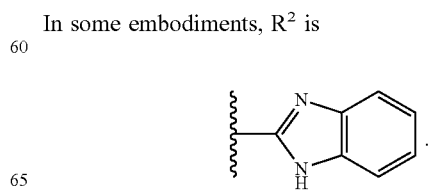

In some embodiments, R² is

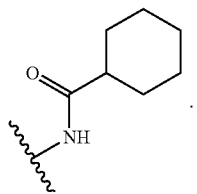 [SMILES: *NC(=O)C1CCCCC1]

In some embodiments, R² is

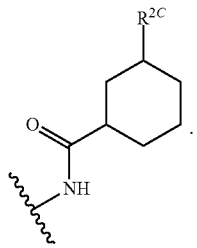

In some embodiments, R² is

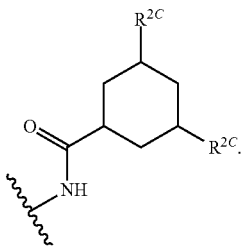

In some embodiments, R² is

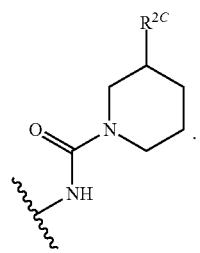

In some embodiments, R² is

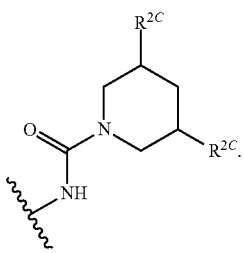

In some embodiments, R² is

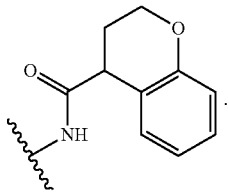 [SMILES: *NC(=O)C1CCOc2ccccc21]

In some embodiments, R² is selected from the groups depicted in the compounds in Table 1.

As defined generally above, each instance of $R^E$ is independently H or -$L^E$-$R^{EA}$; or two instances of $R^E$ are taken together with their intervening atoms to form a 3-8 membered saturated or partially unsaturated monocyclic ring having 0-4 heteroatoms independently selected from nitrogen, oxygen, and sulfur; or an 8-12 membered saturated or partially unsaturated bicyclic ring having 0-4 heteroatoms independently selected from nitrogen, oxygen, and sulfur; wherein each ring is substituted with n instances of $R^{EE}C$.

In some embodiments, each instance of $R^E$ is independently H or -$L^E$-$R^{EA}$. In some embodiments, $R^E$ is H. In some embodiments, each instance of $R^E$ is independently -$L^E$-$R^{EA}$.

In some embodiments, each instance of $R^E$ is independently $R^{EA}$. In some embodiments, each instance of $R^E$ is independently $R^A$. In some embodiments, each instance of $R^E$ is independently $R°$ substituted by $r^3$ instances of $R^{EC}$.

In some embodiments, each instance of $R^E$ is independently H or $C_{1-6}$ aliphatic substituted by $r^3$ instances of $R^{EC}$. In some embodiments, each instance of $R^E$ is independently H or $C_{1-3}$ aliphatic substituted by $r^3$ instances of $R^{EC}$. In some embodiments, each instance of $R^E$ is independently H or $C_{1-3}$ aliphatic substituted by $r^3$ instances of halogen.

In some embodiments, each instance of $R^E$ is independently H or $C_{1-3}$ aliphatic. In some embodiments, each instance of $R^E$ is independently H, —$CH_3$, —$CH_2F$, —$CHF_2$—, or —$CF_3$. In some embodiments, each instance of $R^E$ is independently H or —$CH_3$.

In some embodiments, each instance of $R^E$ is independently $C_{1-6}$ aliphatic substituted by $r^3$ instances of $R^{EC}$. In some embodiments, each instance of $R^E$ is independently $C_{1-3}$ aliphatic substituted by $r^3$ instances of $R^{EC}$. In some embodiments, each instance of $R^E$ is independently $C_{1-3}$ aliphatic substituted by $r^3$ instances of halogen. In some embodiments, each instance of $R^E$ is independently $C_{1-3}$ aliphatic. In some embodiments, each instance of $R^E$ is independently —$CH_3$, —$CH_2F$, —$CHF_2$—, or —$CF_3$. In some embodiments, $R^E$ is —$CH_3$.

In some embodiments, two instances of $R^E$ are taken together with their intervening atoms to form a 3-8 membered saturated or partially unsaturated monocyclic ring having 0-4 heteroatoms independently selected from nitrogen, oxygen, and sulfur; or an 8-12 membered saturated or partially unsaturated bicyclic ring having 0-4 heteroatoms independently selected from nitrogen, oxygen, and sulfur; wherein each ring is substituted with n instances of $R^{EC}$.

In some embodiments, two instances of $R^E$ are taken together with their intervening atoms to form a 3-8 membered saturated or partially unsaturated monocyclic ring having 0-4 heteroatoms independently selected from nitrogen, oxygen, and sulfur; wherein said ring is substituted with n instances of $R^EEC$. In some embodiments, two instances of $R^E$ are taken together with their intervening atoms to form an 8-12 membered saturated or partially unsaturated bicyclic ring having 0-4 heteroatoms independently selected from nitrogen, oxygen, and sulfur; wherein said ring is substituted with n instances of $R^{EC}$.

In some embodiments, $R^E$ is selected from the groups depicted in the compounds in Table 1.

As defined generally above, $R^Q$ is -$L^Q$-$R^{QA}$ or $R^Q$ and $R^1$ are taken together with their intervening atoms to form a 4-8 membered saturated or partially unsaturated monocyclic ring having 0-4 heteroatoms independently selected from nitrogen, oxygen, and sulfur; or an 8-12 membered saturated or partially unsaturated bicyclic ring having 0-4 heteroatoms independently selected from nitrogen, oxygen, and sulfur; wherein said ring is substituted with p instances of $R^{Q1C}$. In some embodiments, $R^Q$ is -$L^Q$-$R^{QA}$. In some embodiments, $R^Q$ is -$R^{QA}$;

In some embodiments, $R^Q$ and $R^1$ are taken together with their intervening atoms to form a 4-8 membered saturated or partially unsaturated monocyclic ring having 0-4 heteroatoms independently selected from nitrogen, oxygen, and sulfur; or an 8-12 membered saturated or partially unsaturated bicyclic ring having 0-4 heteroatoms independently selected from nitrogen, oxygen, and sulfur; wherein said ring is substituted with p instances of $R^{Q1C}$.

In some embodiments, $R^Q$ and $R^1$ are taken together with their intervening atoms to form a 4-8 membered saturated or partially unsaturated monocyclic ring having 0-4 heteroatoms independently selected from nitrogen, oxygen, and sulfur; wherein said ring is substituted with p instances of $R^{Q1C}$. In some embodiments, $R^Q$ and $R^1$ are taken together with their intervening atoms to form an 8-12 membered saturated or partially unsaturated bicyclic ring having 0-4 heteroatoms independently selected from nitrogen, oxygen, and sulfur; wherein said ring is substituted with p instances of $R^{Q1C}$.

In some embodiments, $R^Q$ is halogen, —CN, —NO$_2$, —OR, —SR, —NR$_2$, —S(O)$_2$R, —S(O)$_2$NR$_2$, —S(O)$_2$F, —S(O)R, —S(O)NR$_2$, —S(O)(NR)R, —C(O)R, —C(O)OR, —C(O)NR$_2$, —C(O)N(R)OR, —OC(O)R, —OC(O)NR$_2$, —N(R)C(O)OR, —N(R)C(O)R, —N(R)C(O)NR$_2$, —N(R)C(NR)NR$_2$, —N(R)S(O)$_2$NR$_2$, —N(R)S(O)$_2$R, —P(O)R$_2$, —P(O)(R)OR, or —B(OR)$_2$.

In some embodiments, $R^Q$ is halogen, —CN, —OH, —O-(optionally substituted C$_{1-6}$ aliphatic), or an optionally substituted C$_{1-6}$ aliphatic. In some embodiments, $R^Q$ is halogen, —OH, or C$_{1-3}$ aliphatic optionally substituted with 1-3 halogen. In some embodiments, $R^Q$ is fluorine, chlorine, —OH, or —CH$_3$. In some embodiments, $R^Q$ is deuterium. In some embodiments, $R^Q$ is selected from the groups depicted in the compounds in Table 1.

As defined generally above, $R^X$ is -$L^X$-$R^{XA}$. In some embodiments, $R^X$ is -$R^{XA}$. In some embodiments, $R^X$ is oxo, halogen, —CN, —NO$_2$, —OR, —SR, —NR$_2$, —S(O)$_2$R, —S(O)$_2$NR$_2$, —S(O)$_2$F, —S(O)R, —S(O)NR$_2$, —S(O)(NR)R, —C(O)R, —C(O)OR, —C(O)NR$_2$, —C(O)N(R)OR, —OC(O)R, —OC(O)NR$_2$, —N(R)C(O)OR, —N(R)C(O)R, —N(R)C(O)NR$_2$, —N(R)C(NR)NR$_2$, —N(R)S(O)$_2$NR$_2$, —N(R)S(O)$_2$R, —P(O)R$_2$, —P(O)(R)OR, or —B(OR)$_2$.

In some embodiments, $R^X$ is halogen, —CN, —OH, —O-(optionally substituted C$_{1-6}$ aliphatic), or an optionally substituted C$_{1-6}$ aliphatic. In some embodiments, $R^X$ is halogen, —OH, —O—(C$_{1-3}$ aliphatic), or C$_{1-3}$ aliphatic, wherein each C$_{1-3}$ aliphatic is optionally substituted with 1-3 halogen. In some embodiments, $R^X$ is fluorine, chlorine, —OCH$_3$, or —CH$_3$. In some embodiments, $R^X$ is selected from the groups depicted in the compounds in Table 1.

As defined generally above, $R^Y$ is -$L^Y$-$R^{YA}$ or $R^Y$ and $R^Z$ are taken together with their intervening atoms to form a 4-7 membered partially unsaturated or aromatic ring having 0-4 heteroatoms independently selected from nitrogen, oxygen, and sulfur; wherein said ring is substituted with q instances of $R^{YZC}$. In some embodiments, $R^1$ is -$L^Y$-$R^{YA}$. In some embodiments, $R^Y$ and $R^Z$ are taken together with their intervening atoms to form a 4-7 membered partially unsaturated or aromatic ring having 0-4 heteroatoms independently selected from nitrogen, oxygen, and sulfur; wherein said ring is substituted with q instances of $R^{YZC}$. In some embodiments, $R^Y$ is selected from the groups depicted in the compounds in Table 1.

As defined generally above, $R^Z$ is -$L^Z$-$R^{ZA}$ or $R^Y$ and $R^Z$ are taken together with their intervening atoms to form a 4-7 membered partially unsaturated or aromatic ring having 0-4 heteroatoms independently selected from nitrogen, oxygen, and sulfur; wherein said ring is substituted with q instances of $R^{YZC}$. In some embodiments, $R^Z$ is -$L^Z$-$R^{ZA}$. In some embodiments, $R^Y$ and $R^Z$ are taken together with their intervening atoms to form a 4-7 membered partially unsaturated or aromatic ring having 0-4 heteroatoms independently selected from nitrogen, oxygen, and sulfur; wherein said ring is substituted with q instances of $R^{YZC}$. In some embodiments, $R^Z$ is selected from the groups depicted in the compounds in Table 1.

As defined generally above, $L^1$ is a covalent bond, or a C$_{1-4}$ bivalent saturated or unsaturated, straight or branched hydrocarbon chain wherein one or two methylene units of the chain are optionally and independently replaced by —CH(R')—, —C(R')$_2$—, C$_{3-6}$ cycloalkylene, C$_{3-6}$ heterocycloalkylene, —N(R)—, —N(R)C(O)—, —C(O)N(R)—, —N(R)S(O)$_2$—, —S(O)$_2$N(R)—, —O—, —C(O)—, —OC(O)—, —C(O)O—, —S—, —S(O)—, or —S(O)$_2$—. In some embodiments, $L^1$ is a covalent bond. In some embodiments, $L^1$ is a C$_{1-4}$ bivalent saturated or unsaturated, straight or branched hydrocarbon chain wherein one or two methylene units of the chain are optionally and independently replaced by —CH(R$^L$)—, —C(R$^L$)$_2$—, C$_{3-6}$ cycloalkylene, C$_{3-6}$ heterocycloalkylene, —N(R)—, —N(R)C(O)—, —C(O)N(R)—, —N(R)S(O)$_2$—, —S(O)$_2$N(R)—, —O—, —C(O)—, —OC(O)—, —C(O)O—, —S—, —S(O)—, or —S(O)$_2$—. In some embodiments, $L^1$ is a C$_{1-4}$ bivalent saturated or unsaturated, straight or branched hydrocarbon chain.

In some embodiments, $L^1$ is a C$_{1-2}$ bivalent saturated or unsaturated hydrocarbon chain wherein one or two methylene units of the chain are optionally and independently replaced by —CH(R$^L$)—, —C(R$^L$)$_2$—, C$_{3-6}$ cycloalkylene, C$_{3-6}$ heterocycloalkylene, —N(R)—, —N(R)C(O)—, —C(O)N(R)—, —N(R)S(O)$_2$—, —S(O)$_2$N(R)—, —O—, —C(O)—, —OC(O)—, —C(O)O—, —S—, —S(O)—, or —S(O)$_2$—. In some embodiments, $L^1$ is a C$_{1-2}$ bivalent saturated or unsaturated hydrocarbon chain wherein one or two methylene units of the chain are optionally and independently replaced by —CH(R$^L$)—, —C(R$^L$)$_2$—, —N(R)—, —N(R)C(O)—, —C(O)N(R)—, —N(R)S(O)$_2$—, —S(O)$_2$N(R)—, or —O—. In some embodiments, $L^1$ is a C$_{1-2}$ bivalent saturated or unsaturated hydrocarbon chain. In some embodiments, $L^1$ is selected from the groups depicted in the compounds in Table 1.

As defined generally above, $L^2$ is a covalent bond, or a C$_{1-4}$ bivalent saturated or unsaturated, straight or branched hydrocarbon chain wherein one or two methylene units of the chain are optionally and independently replaced by —CH(R$^L$)—, —C(R$^L$)$_2$—, C$_{3-6}$ cycloalkylene, C$_{3-6}$ heterocycloalkylene, —N(R)—, —N(R)C(O)—, —C(O)N(R)—, —N(R)S(O)$_2$—, —S(O)$_2$N(R)—, —O—, —C(O)—, —OC(O)—, —C(O)O—, —S—, —S(O)—, or —S(O)$_2$—. In some embodiments, L$^2$ is a covalent bond. In some embodiments, L$^2$ is a C$_{1-4}$ bivalent saturated or unsaturated, straight or branched hydrocarbon chain wherein one or two methylene units of the chain are optionally and independently replaced by —CH(R$^L$)—, —C(R$^L$)$_2$—, C$_{3-6}$ cycloalkylene, C$_{3-6}$ heterocycloalkylene, —N(R)—, —N(R)C(O)—, —C(O)N(R)—, —N(R)S(O)$_2$—, —S(O)$_2$N(R)—, —O—, —C(O)—, —OC(O)—, —C(O)O—, —S—, —S(O)—, or —S(O)$_2$—. In some embodiments, L$^2$ is a C$_{1-4}$ bivalent saturated or unsaturated, straight or branched hydrocarbon chain.

In some embodiments, L$^2$ is a C$_{1-2}$ bivalent saturated or unsaturated hydrocarbon chain wherein one or two methylene units of the chain are optionally and independently replaced by —CH(R$^L$)—, —C(R$^L$)$_2$—, C$_{3-6}$ cycloalkylene, C$_{3-6}$ heterocycloalkylene, —N(R)—, —N(R)C(O)—, —C(O)N(R)—, —N(R)S(O)$_2$—, —S(O)$_2$N(R)—, —O—, —C(O)—, —OC(O)—, —C(O)O—, —S—, —S(O)—, or —S(O)$_2$—. In some embodiments, L$^2$ is a C$_{1-2}$ bivalent saturated or unsaturated hydrocarbon chain wherein one or two methylene units of the chain are optionally and independently replaced by —CH(R$^L$)—, —C(R$^L$)$_2$—, —N(R)—, —N(R)C(O)—, —C(O)N(R)—, —N(R)S(O)$_2$—, —S(O)$_2$N(R)—, or —O—. In some embodiments, L$^2$ is a C$_{1-2}$ bivalent saturated or unsaturated hydrocarbon chain.

In some embodiments, L$^2$ is —N(R)C(O)— or —N(R)C(O)N(R)—. In some embodiments, L$^2$ is —N(H)C(O)— or —N(H)C(O)N(H)—. In some embodiments, L$^2$ is —N(R)C(O)—. In some embodiments, L$^2$ is —N(H)C(O)—. In some embodiments, L$^2$ is —N(R)C(O)N(R)—. In some embodiments, L$^2$ is —N(H)C(O)N(H)—. In some embodiments, L$^2$ is —N(R)—. In some embodiments, L$^2$ is —N(H)—. In some embodiments, L$^2$ is a covalent bond. In some embodiments, L$^2$ is selected from the groups depicted in the compounds in Table 1.

As defined generally above, L$^E$ is a covalent bond, or a C$_{1-4}$ bivalent saturated or unsaturated, straight or branched hydrocarbon chain wherein one or two methylene units of the chain are optionally and independently replaced by —CH(R$^L$)—, —C(R$^L$)$_2$—, C$_{3-6}$ cycloalkylene, C$_{3-6}$ heterocycloalkylene, —N(R)—, —N(R)C(O)—, —C(O)N(R)—, —N(R)S(O)$_2$—, —S(O)$_2$N(R)—, —O—, —C(O)—, —OC(O)—, —C(O)O—, —S—, —S(O)—, or —S(O)$_2$—. In some embodiments, L$^E$ is a covalent bond. In some embodiments, L$^L$ is a C$_{1-4}$ bivalent saturated or unsaturated, straight or branched hydrocarbon chain wherein one or two methylene units of the chain are optionally and independently replaced by —CH(R$^L$)—, —C(R$^L$)$_2$—, C$_{3-6}$ cycloalkylene, C$_{3-6}$ heterocycloalkylene, —N(R)—, —N(R)C(O)—, —C(O)N(R)—, —N(R)S(O)$_2$—, —S(O)$_2$N(R)—, —O—, —C(O)—, —OC(O)—, —C(O)O—, —S—, —S(O)—, or —S(O)$_2$—. In some embodiments, L$^E$ is a bivalent saturated or unsaturated, straight or branched hydrocarbon chain.

In some embodiments, L$^E$ is a C$_{1-2}$ bivalent saturated or unsaturated hydrocarbon chain wherein one or two methylene units of the chain are optionally and independently replaced by —CH(R$^L$)—, —C(R$^L$)$_2$—, C$_{3-6}$ cycloalkylene, C$_{3-6}$ heterocycloalkylene, —N(R)—, —N(R)C(O)—, —C(O)N(R)—, —N(R)S(O)$_2$—, —S(O)$_2$N(R)—, —O—, —C(O)—, —OC(O)—, —C(O)O—, —S—, —S(O)—, or —S(O)$_2$—. In some embodiments, L$^E$ is a C$_{1-2}$ bivalent saturated or unsaturated hydrocarbon chain wherein one or two methylene units of the chain are optionally and independently replaced by —CH(R$^L$)—, —C(R$^L$)$_2$—, —N(R)—, —N(R)C(O)—, —C(O)N(R)—, —N(R)S(O)$_2$—, —S(O)$_2$N(R)—, or —O—. In some embodiments, L$^E$ is a C$_{1-2}$ bivalent saturated or unsaturated hydrocarbon chain. In some embodiments, L$^E$ is selected from the groups depicted in the compounds in Table 1.

As defined generally above, L$^Q$ is a covalent bond, or a C$_{1-4}$ bivalent saturated or unsaturated, straight or branched hydrocarbon chain wherein one or two methylene units of the chain are optionally and independently replaced by —CH(R$^L$)—, —C(R$^L$)$_2$—, C$_{3-6}$ cycloalkylene, C$_{3-6}$ heterocycloalkylene, —N(R)—, —N(R)C(O)—, —C(O)N(R)—, —N(R)S(O)$_2$—, —S(O)$_2$N(R)—, —O—, —C(O)—, —OC(O)—, —C(O)O—, —S—, —S(O)—, or —S(O)$_2$—. In some embodiments, L$^Q$ is a covalent bond. In some embodiments, L$^Q$ is a C$_{1-4}$ bivalent saturated or unsaturated, straight or branched hydrocarbon chain wherein one or two methylene units of the chain are optionally and independently replaced by —CH(R$^L$)—, —C(R$^L$)$_2$—, C$_{3-6}$ cycloalkylene, C$_{3-6}$ heterocycloalkylene, —N(R)—, —N(R)C(O)—, —C(O)N(R)—, —N(R)S(O)$_2$—, —S(O)$_2$N(R)—, —O—, —C(O)—, —OC(O)—, —C(O)O—, —S—, —S(O)—, or —S(O)$_2$—. In some embodiments, L$^Q$ is a C$_{1-4}$ bivalent saturated or unsaturated, straight or branched hydrocarbon chain.

In some embodiments, L$^Q$ is a C$_{1-2}$ bivalent saturated or unsaturated hydrocarbon chain wherein one or two methylene units of the chain are optionally and independently replaced by —CH(R$^L$)—, —C(R$^L$)$_2$—, C$_{3-6}$ cycloalkylene, C$_{3-6}$ heterocycloalkylene, —N(R)—, —N(R)C(O)—, —C(O)N(R)—, —N(R)S(O)$_2$—, —S(O)$_2$N(R)—, —O—, —C(O)—, —OC(O)—, —C(O)O—, —S—, —S(O)—, or —S(O)$_2$—. In some embodiments, L$^Q$ is a C$_{1-2}$ bivalent saturated or unsaturated hydrocarbon chain wherein one or two methylene units of the chain are optionally and independently replaced by —CH(R$^L$)—, —C(R$^L$)$_2$—, —N(R)—, —N(R)C(O)—, —C(O)N(R)—, —N(R)S(O)$_2$—, —S(O)$_2$N(R)—, or —O—. In some embodiments, L$^Q$ is a C$_{1-2}$ bivalent saturated or unsaturated hydrocarbon chain. In some embodiments, L$^Q$ is selected from the groups depicted in the compounds in Table 1.

As defined generally above, L$^X$ is a covalent bond, or a C$_{1-4}$ bivalent saturated or unsaturated, straight or branched hydrocarbon chain wherein one or two methylene units of the chain are optionally and independently replaced by —CH(R$^L$)—, —C(R$^L$)$_2$—, C$_{3-6}$ cycloalkylene, C$_{3-6}$ heterocycloalkylene, —N(R)—, —N(R)C(O)—, —C(O)N(R)—, —N(R)S(O)$_2$—, —S(O)$_2$N(R)—, —O—, —C(O)—, —OC(O)—, —C(O)O—, —S—, —S(O)—, or —S(O)$_2$—. In some embodiments, L$^X$ is a covalent bond. In some embodiments, L$^X$ is a C$_{1-4}$ bivalent saturated or unsaturated, straight or branched hydrocarbon chain wherein one or two methylene units of the chain are optionally and independently replaced by —CH(R$^L$)—, —C(R$^L$)$_2$—, C$_{3-6}$ cycloalkylene, C$_{3-6}$ heterocycloalkylene, —N(R)—, —N(R)C(O)—, —C(O)N(R)—, —N(R)S(O)$_2$—, —S(O)$_2$N(R)—, —O—, —C(O)—, —OC(O)—, —C(O)O—, —S—, —S(O)—, or —S(O)$_2$—. In some embodiments, L$^X$ is a C$_{1-4}$ bivalent saturated or unsaturated, straight or branched hydrocarbon chain.

In some embodiments, L$^X$ is a C$_{1-2}$ bivalent saturated or unsaturated hydrocarbon chain wherein one or two methylene units of the chain are optionally and independently replaced by —CH(R$^L$)—, —C(R$^L$)$_2$—, C$_{3-6}$ cycloalkylene, C$_{3-6}$ heterocycloalkylene, —N(R)—, —N(R)C(O)—, —C(O)N(R)—, —N(R)S(O)$_2$—, —S(O)$_2$N(R)—, —O—, —C(O)—, —OC(O)—, —C(O)O—, —S—, —S(O)—, or —S(O)$_2$—. In some embodiments, L$^X$ is a C$_{1-2}$ bivalent saturated or unsaturated hydrocarbon chain wherein one or two methylene units of the chain are optionally and independently replaced by —CH($R^L$)—, —C($R^L$)$_2$—, —N(R)—, —N(R)C(O)—, —C(O)N(R)—, —N(R)S(O)$_2$—, —S(O)$_2$N(R)—, or —O—. In some embodiments, $L^X$ is a $C_{1-2}$ bivalent saturated or unsaturated hydrocarbon chain. In some embodiments, $L^X$ is selected from the groups depicted in the compounds in Table 1.

As defined generally above, $L^Y$ is a covalent bond, or a $C_{1-4}$ bivalent saturated or unsaturated, straight or branched hydrocarbon chain wherein one or two methylene units of the chain are optionally and independently replaced by —CH($R^L$)—, —C($R^L$)$_2$—, $C_{3-6}$ cycloalkylene, $C_{3-6}$ heterocycloalkylene, —N(R)—, —N(R)C(O)—, —C(O)N(R)—, —N(R)S(O)$_2$—, —S(O)$_2$N(R)—, —O—, —C(O)—, —OC(O)—, —C(O)O—, —S—, —S(O)—, or —S(O)$_2$—. In some embodiments, $L^Y$ is a covalent bond. In some embodiments, $L^Y$ is a $C_{1-4}$ bivalent saturated or unsaturated, straight or branched hydrocarbon chain wherein one or two methylene units of the chain are optionally and independently replaced by —CH($R^L$)—, —C($R^L$)$_2$—, $C_{3-6}$ cycloalkylene, $C_{3-6}$ heterocycloalkylene, —N(R)—, —N(R)C(O)—, —C(O)N(R)—, —N(R)S(O)$_2$—, —S(O)$_2$N(R)—, —O—, —C(O)—, —OC(O)—, —C(O)O—, —S—, —S(O)—, or —S(O)$_2$—. In some embodiments, $L^Y$ is a $C_{1-4}$ bivalent saturated or unsaturated, straight or branched hydrocarbon chain.

In some embodiments, $L^Y$ is a $C_{1-2}$ bivalent saturated or unsaturated hydrocarbon chain wherein one or two methylene units of the chain are optionally and independently replaced by —CH($R^L$)—, —C($R^L$)$_2$—, $C_{3-6}$ cycloalkylene, $C_{3-6}$ heterocycloalkylene, —N(R)—, —N(R)C(O)—, —C(O)N(R)—, —N(R)S(O)$_2$—, —S(O)$_2$N(R)—, —O—, —C(O)—, —OC(O)—, —C(O)O—, —S—, —S(O)—, or —S(O)$_2$—. In some embodiments, $L^Y$ is a $C_{1-2}$ bivalent saturated or unsaturated hydrocarbon chain wherein one or two methylene units of the chain are optionally and independently replaced by —CH($R^L$)—, —C($R^L$)$_2$—, —N(R)—, —N(R)C(O)—, —C(O)N(R)—, —N(R)S(O)$_2$—, —S(O)$_2$N(R)—, or —O—. In some embodiments, $L^Y$ is a $C_{1-2}$ bivalent saturated or unsaturated hydrocarbon chain.

In some embodiments, $L^Y$ is —C(H)$_2$—, —CH($R^L$)—, —C($R^L$)$_2$—, $C_{3-6}$ cycloalkylene, $C_{3-6}$ heterocycloalkylene, —N(R)—, —N(R)C(O)—, —C(O)N(R)—, —N(R)S(O)$_2$—, —S(O)$_2$N(R)—, —O—, —C(O)—, —OC(O)—, —C(O)O—, —S—, —S(O)—, or —S(O)$_2$—. In some embodiments, $L^Y$ is —C(H)$_2$—, —CH($R^L$)—, —C($R^L$)$_2$—, —N(R)—, —N(R)C(O)—, —C(O)N(R)—, —N(R)S(O)$_2$—, —S(O)$_2$N(R)—, or —O—. In some embodiments, $L^Y$ is —C(H)$_2$—, —N(R)—, —N(R)C(O)—, or —C(O)N(R)—. In some embodiments, $L^Y$ is —C(H)$_2$—, —N(H)—, —N(H)C(O)—, or —C(O)N(H)—. In some embodiments, $L^Y$ is selected from the groups depicted in the compounds in Table 1.

As defined generally above, $L^Z$ is a covalent bond, or a $C_{1-4}$ bivalent saturated or unsaturated, straight or branched hydrocarbon chain wherein one or two methylene units of the chain are optionally and independently replaced by —CH($R^L$)—, —C($R^L$)$_2$—, $C_{3-6}$ cycloalkylene, $C_{3-6}$ heterocycloalkylene, —N(R)—, —N(R)C(O)—, —C(O)N(R)—, —N(R)S(O)$_2$—, —S(O)$_2$N(R)—, —O—, —C(O)—, —OC(O)—, —C(O)O—, —S—, —S(O)—, or —S(O)$_2$—. In some embodiments, $L^Z$ is a covalent bond. In some embodiments, $L^Z$ is a $C_{1-4}$ bivalent saturated or unsaturated, straight or branched hydrocarbon chain wherein one or two methylene units of the chain are optionally and independently replaced by —CH($R^L$)—, —C($R^L$)$_2$—, $C_{3-6}$ cycloalkylene, $C_{3-6}$ heterocycloalkylene, —N(R)—, —N(R)C(O)—, —C(O)N(R)—, —N(R)S(O)$_2$—, —S(O)$_2$N(R)—, —O—, —C(O)—, —OC(O)—, —C(O)O—, —S—, —S(O)—, or —S(O)$_2$—. In some embodiments, $L^Z$ is a $C_{1-4}$ bivalent saturated or unsaturated, straight or branched hydrocarbon chain.

In some embodiments, $L^Z$ is a $C_{1-2}$ bivalent saturated or unsaturated hydrocarbon chain wherein one or two methylene units of the chain are optionally and independently replaced by —CH($R^L$)—, —C($R^L$)$_2$—, $C_{3-6}$ cycloalkylene, $C_{3-6}$ heterocycloalkylene, —N(R)—, —N(R)C(O)—, —C(O)N(R)—, —N(R)S(O)$_2$—, —S(O)$_2$N(R)—, —O—, —C(O)—, —OC(O)—, —C(O)O—, —S—, —S(O)—, or —S(O)$_2$—. In some embodiments, $L^Z$ is a $C_{1-2}$ bivalent saturated or unsaturated hydrocarbon chain wherein one or two methylene units of the chain are optionally and independently replaced by —CH($R^L$)—, —C($R^L$)$_2$—, —N(R)—, —N(R)C(O)—, —C(O)N(R)—, —N(R)S(O)$_2$—, —S(O)$_2$N(R)—, or —O—. In some embodiments, $L^Z$ is a $C_{1-2}$ bivalent saturated or unsaturated hydrocarbon chain.

In some embodiments, $L^Z$ is —C(H)$_2$—, —CH($R^L$)—, —C($R^L$)$_2$—, $C_{3-6}$ cycloalkylene, $C_{3-6}$ heterocycloalkylene, —N(R)—, —N(R)C(O)—, —C(O)N(R)—, —N(R)S(O)$_2$—, —S(O)$_2$N(R)—, —O—, —C(O)—, —OC(O)—, —C(O)O—, —S—, —S(O)—, or —S(O)$_2$—. In some embodiments, $L^Z$ is —C(H)$_2$—, —CH($R^L$)—, —C($R^L$)$_2$—, —N(R)—, —N(R)C(O)—, —C(O)N(R)—, —N(R)S(O)$_2$—, —S(O)$_2$N(R)—, or —O—. In some embodiments, $L^Z$ is —C(H)$_2$—, —N(R)—, —N(R)C(O)—, or —C(O)N(R)—. In some embodiments, $L^Z$ is —C(H)$_2$—, —N(H)—, —N(H)C(O)—, or —C(O)N(H)—. In some embodiments, $L^Z$ is selected from the groups depicted in the compounds in Table 1.

As defined generally above, $R^{1A}$ is $R^A$ or $R^B$ substituted by $r^1$ instances of $R^{1C}$. In some embodiments, $R^{1A}$, $R^A$. In some embodiments, $R^{1A}$ is $R^B$ substituted by $r^1$ instances of $R^{1C}$.

In some embodiments, $R^{1A}$ is phenyl; naphthyl; a 5-6 membered monocyclic heteroaryl ring having 1-4 heteroatoms independently selected from nitrogen, oxygen, and sulfur; an 8-10 membered bicyclic heteroaryl ring having 1-4 heteroatoms independently selected from nitrogen, oxygen, and sulfur; a 3-7 membered saturated or partially unsaturated monocyclic carbocyclic ring; a 5-12 membered saturated or partially unsaturated bicyclic carbocyclic ring; a 3-7 membered saturated or partially unsaturated monocyclic heterocyclic ring having 1-2 heteroatoms independently selected from nitrogen, oxygen, and sulfur; or a 7-12 membered saturated or partially unsaturated bicyclic heterocyclic ring having 1-4 heteroatoms independently selected from nitrogen, oxygen, and sulfur; wherein $R^{1A}$ is substituted by $r^1$ instances of $R^{1C}$.

In some embodiments, $R^{1A}$ is phenyl substituted by $r^1$ instances of $R^{1C}$. In some embodiments, $R^{1A}$ is an 8-10 membered bicyclic heteroaryl ring having 1-4 heteroatoms independently selected from nitrogen, oxygen, and sulfur, wherein $R^{1A}$ is substituted by $r^1$ instances of $R^{1C}$. In some embodiments, $R^{1A}$ is phenyl or an 8-10 membered bicyclic heteroaryl ring having 1-4 heteroatoms independently selected from nitrogen, oxygen, and sulfur, wherein $R^{1A}$ is substituted by $r^1$ instances of $R^{1C}$.

In some embodiments, $R^{1A}$ is phenyl; naphthyl; a 5-6 membered monocyclic heteroaryl ring having 1-4 heteroatoms independently selected from nitrogen, oxygen, and sulfur; an 8-10 membered bicyclic heteroaryl ring having 1-4 heteroatoms independently selected from nitrogen, oxygen, and sulfur; or a 3-7 membered saturated or partially unsaturated monocyclic carbocyclic ring; wherein $R^{1A}$ is substituted by $r^1$ instances of $R^{1C}$.

In some embodiments, $R^{1A}$ is phenyl substituted by $r^1$ instances of a group independently selected from oxo, halogen, —CN, —NO$_2$, —OR, —SR, —NR$_2$, —S(O)$_2$R, —S(O)$_2$NR$_2$, —S(O)$_2$F, —S(O)R, —S(O)NR$_2$, —S(O)(NR)R, —C(O)R, —C(O)OR, —C(O)NR$_2$, —C(O)N(R)OR, —OC(O)R, —OC(O)NR$_2$, —N(R)C(O)OR, —N(R)C(O)R, —N(R)C(O)NR$_2$, —N(R)C(NR)NR$_2$, —N(R)S(O)$_2$NR$_2$, —N(R)S(O)$_2$R, —P(O)R$_2$, —P(O)(R)OR, —B(OR)$_2$, and optionally substituted $C_{1-6}$ aliphatic. In some embodiments, $R^{1A}$ is an 8-10 membered bicyclic heteroaryl ring having 1-4 heteroatoms independently selected from nitrogen, oxygen, and sulfur, wherein $R^{1A}$ is substituted by $r^1$ instances of a group independently selected from oxo, halogen, —CN, —NO$_2$, —OR, —SR, —NR$_2$, —S(O)$_2$R, —S(O)$_2$NR$_2$, —S(O)$_2$F, —S(O)R, —S(O)NR$_2$, —S(O)(NR)R, —C(O)R, —C(O)OR, —C(O)NR$_2$, —C(O)N(R)OR, —OC(O)R, —OC(O)NR$_2$, —N(R)C(O)OR, —N(R)C(O)R, —N(R)C(O)NR$_2$, —N(R)C(NR)NR$_2$, —N(R)S(O)$_2$NR$_2$, —N(R)S(O)$_2$R, —P(O)R$_2$, —P(O)(R)OR, —B(OR)$_2$, and optionally substituted $C_{1-6}$ aliphatic. In some embodiments, $R^{1A}$ is phenyl or an 8-10 membered bicyclic heteroaryl ring having 1-4 heteroatoms independently selected from nitrogen, oxygen, and sulfur, wherein $R^{1A}$ is substituted by $r^1$ instances of a group independently selected from oxo, halogen, —CN, —NO$_2$, —OR, —SR, —NR$_2$, —S(O)$_2$R, —S(O)$_2$NR$_2$, —S(O)$_2$F, —S(O)R, —S(O)NR$_2$, —S(O)(NR)R, —C(O)R, —C(O)OR, —C(O)NR$_2$, —C(O)N(R)OR, —OC(O)R, —OC(O)NR$_2$, —N(R)C(O)OR, —N(R)C(O)R, —N(R)C(O)NR$_2$, —N(R)C(NR)NR$_2$, —N(R)S(O)$_2$NR$_2$, —N(R)S(O)$_2$R, —P(O)R$_2$, —P(O)(R)OR, —B(OR)$_2$, and optionally substituted $C_{1-6}$ aliphatic.

In some embodiments, $R^{1A}$ is phenyl substituted by 1-3 instances of $R^{1C}$. In some embodiments, $R^{1A}$ is phenyl substituted by 2 instances of $R^{1C}$. In some embodiments, $R^{1A}$ is phenyl substituted by 1 instance of $R^{1C}$.

In some embodiments, $R^{1A}$ is phenyl substituted by 1-3 instances of a group independently selected from halogen, —CN, —O-(optionally substituted $C_{1-6}$ aliphatic), and an optionally substituted $C_{1-6}$ aliphatic. In some embodiments, $R^{1A}$ is phenyl substituted by 1-3 instances of a group independently selected from halogen and $C_{1-3}$ aliphatic optionally substituted with 1-3 halogen. In some embodiments, $R^{1A}$ is phenyl substituted by 1-3 instances of a group independently selected from fluorine, chlorine, —CH$_3$, —CHF$_2$, and —CF$_3$.

In some embodiments, $R^{1A}$ is phenyl substituted by 2 instances of a group independently selected from halogen, —CN, —O-(optionally substituted $C_{1-6}$ aliphatic), and an optionally substituted $C_{1-6}$ aliphatic. In some embodiments, $R^{1A}$ is phenyl substituted by 2 instances of a group independently selected from halogen and $C_{1-3}$ aliphatic optionally substituted with 1-3 halogen. In some embodiments, $R^{1A}$ is phenyl substituted by 2 instances of a group independently selected from fluorine, chlorine, —CH$_3$, —CHF$_2$, and —CF$_3$.

In some embodiments, $R^{1A}$ is phenyl substituted by one group selected from halogen, —CN, —O-(optionally substituted $C_6$ aliphatic), and an optionally substituted $C_6$ aliphatic. In some embodiments, $R^{1A}$ is phenyl substituted by one halogen or $C_{1-3}$ aliphatic group optionally substituted with 1-3 halogen. In some embodiments, $R^{1A}$ is phenyl substituted by one fluorine, chlorine, —CH$_3$, —CHF$_2$, or —CF$_3$.

In some embodiments, $R^{1A}$ is

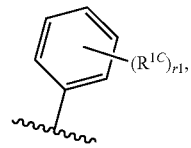

wherein $R^{1C}$ and $r^1$ are as defined in the embodiments and classes and subclasses herein. In some embodiments, $R^{1A}$ is

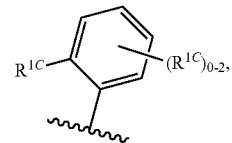

wherein $R^{1C}$ is as defined in the embodiments and classes and subclasses herein. In some embodiments, $R^{1A}$ is

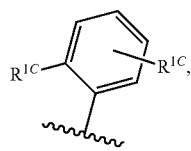

wherein $R^{1C}$ is as defined in the embodiments and classes and subclasses herein. In some embodiments, $R^{1A}$ is

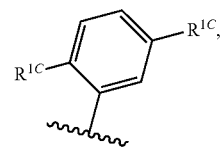

wherein $R^{1C}$ is as defined in the embodiments and classes and subclasses herein. In some embodiments, $R^{1A}$ is

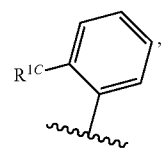

wherein $R^{1C}$ is as defined in the embodiments and classes and subclasses herein.

In some embodiments, $R^{1A}$ is

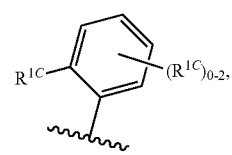

wherein each instance of $R^{1C}$ is independently halogen, —CN, —O-(optionally substituted $C_{1-6}$ aliphatic), or an optionally substituted $C_{1-6}$ aliphatic. In some embodiments, $R^{1A}$ is

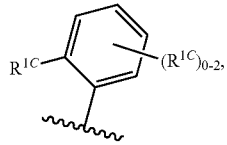

wherein each instance of $R^{1C}$ is independently halogen or $C_{1-3}$ aliphatic optionally substituted with 1-3 halogen. In some embodiments, $R^{1A}$ is

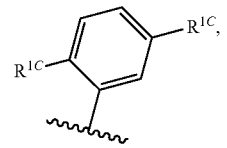

wherein each instance of $R^{1C}$ is independently halogen or $C_{1-3}$ aliphatic optionally substituted with 1-3 halogen. In some embodiments, $R^{1A}$ is

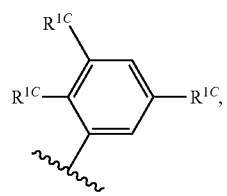

wherein each instance of $R^{1C}$ is independently halogen or $C_{1-3}$ aliphatic optionally substituted with 1-3 halogen. In some embodiments, $R^{1A}$ is

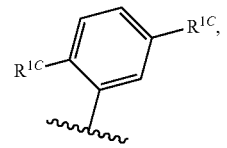

wherein each instance of $R^{1C}$ is independently fluorine, chlorine, —CH$_3$, —CHF$_2$, or —CF$_3$. In some embodiments, $R^{1A}$ is

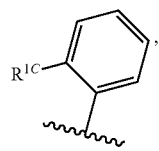

wherein $R^{1C}$ is halogen or $C_{1-3}$ aliphatic optionally substituted with 1-3 halogen.

In some embodiments, $R^{1A}$ is

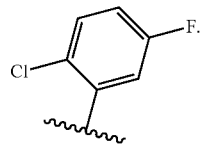 [SMILES: *c1cc(F)ccc1Cl]

In some embodiments, $R^{1A}$ is

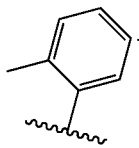

In some embodiments, $R^{1A}$ is

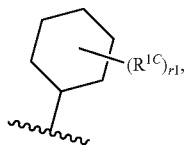

wherein $R^{1C}$ and $r^1$ are as defined in the embodiments and classes and subclasses herein. In some embodiments, $R^{1A}$ is

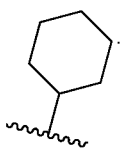 [SMILES: *C1CCCCC1]

In some embodiments, $R^{1A}$ is

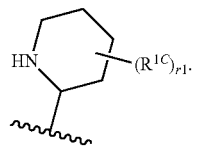

In some embodiments, $R^{1A}$ is

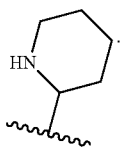

In some embodiments, $R^{1A}$ is oxo, halogen, —CN, —NO$_2$, —OR, —SR, —NR$_2$, —S(O)$_2$R, —S(O)$_2$NR$_2$, —S(O)$_2$F, —S(O)R, —S(O)NR$_2$, —S(O)(NR)R, —C(O)R, —C(O)OR, —C(O)NR$_2$, —C(O)N(R)OR, —OC(O)R, —OC(O)NR$_2$, —N(R)C(O)OR, —N(R)C(O)R, —N(R)C(O)NR$_2$, —N(R)C(NR)NR$_2$, —N(R)S(O)$_2$NR$_2$, —N(R)S(O)$_2$R, —P(O)R$_2$, —P(O)(R)OR, —B(OR)$_2$, or deuterium.

In some embodiments, $R^{1A}$ is oxo, halogen, —CN, —NO$_2$, —OR, —SR, —NR$_2$, —S(O)$_2$R, —S(O)$_2$NR$_2$, —S(O)$_2$F, —S(O)R, —S(O)NR$_2$, —S(O)(NR)R, —C(O)R, —C(O)OR, —C(O)NR$_2$, —C(O)N(R)OR, —OC(O)R, —OC(O)NR$_2$, —N(R)C(O)OR, —N(R)C(O)R, —N(R)C(O)NR$_2$, —N(R)C(NR)NR$_2$, —N(R)S(O)$_2$NR$_2$, —N(R)S(O)$_2$R, —P(O)R$_2$, —P(O)(R)OR, or —B(OR)$_2$.

In some embodiments, $R^{1A}$ is oxo. In some embodiments, $R^{1A}$ is halogen. In some embodiments, $R^{1A}$ is —CN. In some embodiments, $R^{1A}$ is —NO$_2$. In some embodiments, $R^{1A}$ is —OR. In some embodiments, $R^{1A}$ is —SR. In some embodiments, $R^{1A}$ is —NR$_2$. In some embodiments, $R^{1A}$ is —S(O)$_2$R. In some embodiments, $R^A$ is —S(O)$_2$NR$_2$. In some embodiments, $R^{1A}$ is —S(O)$_2$F. In some embodiments, $R^{1A}$ is —S(O)R. In some embodiments, $R^{1A}$ is —S(O)NR$_2$. In some embodiments, $R^{1A}$ is —S(O)(NR)R. In some embodiments, $R^{1A}$ is —C(O)R. In some embodiments, $R^{1A}$ is —C(O)OR. In some embodiments, $R^{1A}$ is —C(O)NR$_2$.

In some embodiments, $R^{1A}$ is —C(O)N(R)OR. In some embodiments, $R^{1A}$ is —OC(O)R. In some embodiments, $R^{1A}$ is —OC(O)NR$_2$. In some embodiments, $R^{1A}$ is —N(R)C(O)OR. In some embodiments, $R^{1A}$ is —N(R)C(O)R. In some embodiments, $R^{1A}$ is —N(R)C(O)NR$_2$. In some embodiments, $R^{1A}$ is —N(R)C(NR)NR$_2$.

In some embodiments, $R^{1A}$ is —N(R)S(O)$_2$R. In some embodiments, $R^{1A}$ is —P(O)R$_2$. In some embodiments, $R^{1A}$ is —P(O)(R)OR. In some embodiments, $R^{1A}$ is —B(OR)$_2$. In some embodiments, $R^{1A}$ is deuterium.

In some embodiments, $R^{1A}$ is halogen, —CN, —NO$_2$, —OR, —SR, —NR$_2$, —S(O)$_2$R, —S(O)$_2$NR$_2$, —S(O)$_2$F, —S(O)R, —S(O)NR$_2$, —S(O)(NR)R, —C(O)R, —C(O)OR, —C(O)NR$_2$, —C(O)N(R)OR, —OC(O)R, —OC(O)NR$_2$, —N(R)C(O)OR, —N(R)C(O)R, —N(R)C(O)NR$_2$, —N(R)C(NR)NR$_2$, —N(R)S(O)$_2$NR$_2$, —N(R)S(O)$_2$R, —P(O)R$_2$, —P(O)(R)OR, or —B(OR)$_2$.

In some embodiments, $R^{1A}$ is halogen, —CN, or —NO$_2$. In some embodiments, $R^{1A}$ is —OR, —SR, or —NR$_2$. In some embodiments, $R^{1A}$ is —S(O)$_2$R, —S(O)$_2$NR$_2$, —S(O)$_2$F, —S(O)R, —S(O)NR$_2$, or —S(O)(NR)R. In some embodiments, $R^{1A}$ is —C(O)R, —C(O)OR, —C(O)NR$_2$, or —C(O)N(R)OR. In some embodiments, $R^{1A}$ is —OC(O)R or —OC(O)NR$_2$. In some embodiments, $R^{1A}$ is —N(R)C(O)OR, —N(R)C(O)R, —N(R)C(O)NR$_2$, —N(R)C(NR)NR$_2$, —N(R)S(O)$_2$NR$_2$, or —N(R)S(O)$_2$R. In some embodiments, $R^{1A}$ is —P(O)R$_2$ or —P(O)(R)OR.

In some embodiments, $R^{1A}$ is —OR, —OC(O)R, or —OC(O)NR$_2$. In some embodiments, $R^{1A}$ is —SR, —S(O)$_2$R, —S(O)$_2$NR$_2$, —S(O)$_2$F, —S(O)R, —S(O)NR$_2$, or —S(O)(NR)R. In some embodiments, $R^{1A}$ is —NR$_2$, —N(R)C(O)OR, —N(R)C(O)R, —N(R)C(O)NR$_2$, —N(R)C(NR)NR$_2$, —N(R)S(O)$_2$NR$_2$, or —N(R)S(O)$_2$R.

In some embodiments, $R^{1A}$ is —S(O)$_2$R, —S(O)$_2$NR$_2$, or —S(O)$_2$F. In some embodiments, $R^{1A}$ is —S(O)R, —S(O)NR$_2$, or —S(O)(NR)R. In some embodiments, $R^{1A}$ is —SR, —S(O)$_2$R, or —S(O)R. In some embodiments, $R^{1A}$ is —S(O)$_2$NR$_2$, —S(O)NR$_2$, or —S(O)(NR)R. In some embodiments, $R^{1A}$ is —S(O)$_2$NR$_2$ or —S(O)NR$_2$. In some embodiments, $R^{1A}$ is —SR, —S(O)$_2$R, —S(O)$_2$NR$_2$, or —S(O)R.

In some embodiments, $R^{1A}$ is —N(R)C(O)OR, —N(R)C(O)R, or —N(R)C(O)NR$_2$. In some embodiments, $R^{1A}$ is —N(R)S(O)$_2$NR$_2$ or —N(R)S(O)$_2$R. In some embodiments, $R^{1A}$ is —N(R)C(O)OR or —N(R)C(O)R. In some embodiments, $R^{1A}$ is —N(R)C(O)NR$_2$ or —N(R)S(O)$_2$NR$_2$. In some embodiments, $R^{1A}$ is —N(R)C(O)OR, —N(R)C(O)R, or —N(R)S(O)$_2$R.

In some embodiments, $R^{1A}$ is —NR$_2$, —N(R)C(O)OR, —N(R)C(O)R, or —N(R)C(O)NR$_2$. In some embodiments, $R^{1A}$ is —NR$_2$, —N(R)C(O)OR, or —N(R)C(O)R. In some embodiments, $R^{1A}$ is —NR$_2$, —N(R)C(O)OR, —N(R)C(O)R, or —N(R)S(O)$_2$R.

In some embodiments, $R^{1A}$ is a $C_{1-6}$ aliphatic chain; phenyl; naphthyl; a 5-6 membered monocyclic heteroaryl ring having 1-4 heteroatoms independently selected from nitrogen, oxygen, and sulfur; an 8-10 membered bicyclic heteroaryl ring having 1-4 heteroatoms independently selected from nitrogen, oxygen, and sulfur; a 3-7 membered saturated or partially unsaturated monocyclic carbocyclic ring; a 5-12 membered saturated or partially unsaturated bicyclic carbocyclic ring; a 3-7 membered saturated or partially unsaturated monocyclic heterocyclic ring having 1-2 heteroatoms independently selected from nitrogen, oxygen, and sulfur; or a 7-12 membered saturated or partially unsaturated bicyclic heterocyclic ring having 1-4 heteroatoms independently selected from nitrogen, oxygen, and sulfur; each of which is substituted by $r^1$ instances of $R^{1C}$.

In some embodiments, $R^{1A}$ is a $C_{1-6}$ aliphatic chain substituted by $r^1$ instances of $R^{YC}$.

In some embodiments, $R^{1A}$ is phenyl substituted by $r^1$ instances of $R^1$. In some embodiments, $R^{1A}$ is naphthyl substituted by $r^1$ instances of $R^{1C}$. In some embodiments, $R^{1A}$ is a 5-6 membered monocyclic heteroaryl ring having 1-4 heteroatoms independently selected from nitrogen, oxygen, and sulfur; wherein said ring is substituted by $r^1$ instances of $R^{1C}$. In some embodiments, $R^{1A}$ is an 8-10 membered bicyclic heteroaryl ring having 1-4 heteroatoms independently selected from nitrogen, oxygen, and sulfur; wherein said ring is substituted by $r^1$ instances of $R^{1C}$. In some embodiments, $R^{1A}$ is a 3-7 membered saturated or partially unsaturated monocyclic carbocyclic ring substituted by r instances of $R^{1C}$. In some embodiments, $R^{1A}$ is a 5-12 membered saturated or partially unsaturated bicyclic carbocyclic ring substituted by $r^1$ instances of $R^{1C}$. In some embodiments, $R^{1A}$ is a 3-7 membered saturated or partially unsaturated monocyclic heterocyclic ring having 1-2 heteroatoms independently selected from nitrogen, oxygen, and sulfur; wherein said ring is substituted by $r^1$ instances of $R^{1C}$. In some embodiments, $R^{1A}$ is a 7-12 membered saturated or partially unsaturated bicyclic heterocyclic ring having 1-4 heteroatoms independently selected from nitrogen, oxygen, and sulfur; wherein said ring is substituted by $r^1$ instances of $R^{1C}$.

In some embodiments, $R^{1A}$ is phenyl; naphthyl; a 5-6 membered monocyclic heteroaryl ring having 1-4 heteroatoms independently selected from nitrogen, oxygen, and sulfur; or an 8-10 membered bicyclic heteroaryl ring having 1-4 heteroatoms independently selected from nitrogen, oxygen, and sulfur; each of which is substituted by $r^1$ instances of $R^{1C}$. In some embodiments, $R^{1A}$ is a 3-7 membered saturated or partially unsaturated monocyclic carbocyclic ring; a 5-12 membered saturated or partially unsaturated bicyclic carbocyclic ring; a 3-7 membered saturated or partially unsaturated monocyclic heterocyclic ring having 1-2 heteroatoms independently selected from nitrogen, oxygen, and sulfur; or a 7-12 membered saturated or partially unsaturated bicyclic heterocyclic ring having 1-4 heteroatoms independently selected from nitrogen, oxygen, and sulfur; each of which is substituted by $r^1$ instances of $R^{1C}$.

In some embodiments, $R^{1A}$ is phenyl; naphthyl; a 3-7 membered saturated or partially unsaturated monocyclic carbocyclic ring; or a 5-12 membered saturated or partially unsaturated bicyclic carbocyclic ring; each of which is substituted by $r^1$ instances of $R^{1C}$. In some embodiments, $R^{1A}$ is a 5-6 membered monocyclic heteroaryl ring having 1-4 heteroatoms independently selected from nitrogen, oxygen, and sulfur; an 8-10 membered bicyclic heteroaryl ring having 1-4 heteroatoms independently selected from nitrogen, oxygen, and sulfur; a 3-7 membered saturated or partially unsaturated monocyclic heterocyclic ring having 1-2 heteroatoms independently selected from nitrogen, oxygen, and sulfur; or a 7-12 membered saturated or partially unsaturated bicyclic heterocyclic ring having 1-4 heteroatoms independently selected from nitrogen, oxygen, and sulfur; each of which is substituted by $r^1$ instances of $R^{1C}$.

In some embodiments, $R^{1A}$ is phenyl; a 5-6 membered monocyclic heteroaryl ring having 1-4 heteroatoms independently selected from nitrogen, oxygen, and sulfur; a 3-7 membered saturated or partially unsaturated monocyclic carbocyclic ring; or a 3-7 membered saturated or partially unsaturated monocyclic heterocyclic ring having 1-2 heteroatoms independently selected from nitrogen, oxygen, and sulfur; each of which is substituted by $r^1$ instances of $R^{1C}$. In some embodiments, $R^{1A}$ is naphthyl; an 8-10 membered bicyclic heteroaryl ring having 1-4 heteroatoms independently selected from nitrogen, oxygen, and sulfur; a 5-12 membered saturated or partially unsaturated bicyclic carbocyclic ring; or a 7-12 membered saturated or partially unsaturated bicyclic heterocyclic ring having 1-4 heteroatoms independently selected from nitrogen, oxygen, and sulfur; each of which is substituted by $r^1$ instances of $R^{1C}$.

In some embodiments, $R^{1A}$ is phenyl or naphthyl; each of which is substituted by $r^1$ instances of $R^{1C}$. In some embodiments, $R^{1A}$ is a 5-6 membered monocyclic heteroaryl ring having 1-4 heteroatoms independently selected from nitrogen, oxygen, and sulfur; or an 8-10 membered bicyclic heteroaryl ring having 1-4 heteroatoms independently selected from nitrogen, oxygen, and sulfur; each of which is substituted by $r^1$ instances of $R^{1C}$. In some embodiments, $R^{1A}$ is a 3-7 membered saturated or partially unsaturated monocyclic carbocyclic ring or a 5-12 membered saturated or partially unsaturated bicyclic carbocyclic ring; each of which is substituted by $r^1$ instances of $R^{1C}$. In some embodiments, $R^{1A}$ is a 3-7 membered saturated or partially unsaturated monocyclic heterocyclic ring having 1-2 heteroatoms independently selected from nitrogen, oxygen, and sulfur; or a 7-12 membered saturated or partially unsaturated bicyclic heterocyclic ring having 1-4 heteroatoms independently selected from nitrogen, oxygen, and sulfur; each of which is substituted by $r^1$ instances of $R^{1C}$.

In some embodiments, $R^{1A}$ is phenyl or a 5-6 membered monocyclic heteroaryl ring having 1-4 heteroatoms independently selected from nitrogen, oxygen, and sulfur; each of which is substituted by $r^1$ instances of $R^{1C}$. In some embodiments, $R^{1A}$ is a 3-7 membered saturated or partially unsaturated monocyclic carbocyclic ring or a 3-7 membered saturated or partially unsaturated monocyclic heterocyclic ring having 1-2 heteroatoms independently selected from nitrogen, oxygen, and sulfur; each of which is substituted by $r^1$ instances of $R^{1C}$. In some embodiments, $R^{1A}$ is naphthyl or an 8-10 membered bicyclic heteroaryl ring having 1-4 heteroatoms independently selected from nitrogen, oxygen, and sulfur; each of which is substituted by $r^1$ instances of $R^{1C}$. In some embodiments, $R^{1A}$ is a 5-12 membered saturated or partially unsaturated bicyclic carbocyclic ring or a 7-12 membered saturated or partially unsaturated bicyclic heterocyclic ring having 1-4 heteroatoms independently selected from nitrogen, oxygen, and sulfur; each of which is substituted by $r^1$ instances of $R^{1C}$.

In some embodiments, $R^{1A}$ is phenyl or a 3-7 membered saturated or partially unsaturated monocyclic carbocyclic ring; each of which is substituted by $r^1$ instances of $R^{1C}$ In some embodiments, $R^{1A}$ is naphthyl or a 5-12 membered saturated or partially unsaturated bicyclic carbocyclic ring; each of which is substituted by $r^1$ instances of $R^{1C}$. In some embodiments, $R^{1A}$ is a 5-6 membered monocyclic heteroaryl ring having 1-4 heteroatoms independently selected from nitrogen, oxygen, and sulfur; or a 3-7 membered saturated or partially unsaturated monocyclic heterocyclic ring having 1-2 heteroatoms independently selected from nitrogen, oxygen, and sulfur; each of which is substituted by $r^1$ instances of $R^{1C}$. In some embodiments, $R^{1A}$ is an 8-10 membered bicyclic heteroaryl ring having 1-4 heteroatoms independently selected from nitrogen, oxygen, and sulfur; or a 7-12 membered saturated or partially unsaturated bicyclic heterocyclic ring having 1-4 heteroatoms independently selected from nitrogen, oxygen, and sulfur; each of which is substituted by $r^1$ instances of $R^{1C}$.

In some embodiments, $R^{1A}$ is a $C_{1-6}$ aliphatic chain; a 3-7 membered saturated or partially unsaturated monocyclic carbocyclic ring; a 5-12 membered saturated or partially unsaturated bicyclic carbocyclic ring; a 3-7 membered saturated or partially unsaturated monocyclic heterocyclic ring having 1-2 heteroatoms independently selected from nitrogen, oxygen, and sulfur; or a 7-12 membered saturated or partially unsaturated bicyclic heterocyclic ring having 1-4 heteroatoms independently selected from nitrogen, oxygen, and sulfur; each of which is substituted by $r^1$ instances of $R^{1C}$. In some embodiments, $R^{1A}$ is a $C_{1-6}$ aliphatic chain; phenyl; naphthyl; a 3-7 membered saturated or partially unsaturated monocyclic carbocyclic ring; or a 5-12 membered saturated or partially unsaturated bicyclic carbocyclic ring; each of which is substituted by $r^1$ instances of $R^{1C}$. In some embodiments, $R^{1A}$ is a $C_{1-6}$ aliphatic chain; phenyl; a 5-6 membered monocyclic heteroaryl ring having 1-4 heteroatoms independently selected from nitrogen, oxygen, and sulfur; a 3-7 membered saturated or partially unsaturated monocyclic carbocyclic ring; or a 3-7 membered saturated or partially unsaturated monocyclic heterocyclic ring having 1-2 heteroatoms independently selected from nitrogen, oxygen, and sulfur; each of which is substituted by $r^1$ instances of $R^{1C}$.

In some embodiments, $R^{1A}$ is a $C_{1-6}$ aliphatic chain, a 3-7 membered saturated or partially unsaturated monocyclic carbocyclic ring, or a 5-12 membered saturated or partially unsaturated bicyclic carbocyclic ring; each of which is substituted by $r^1$ instances of $R^{1C}$. In some embodiments, $R^{1A}$ is a $C_{1-6}$ aliphatic chain, a 3-7 membered saturated or partially unsaturated monocyclic carbocyclic ring, or a 3-7 membered saturated or partially unsaturated monocyclic heterocyclic ring having 1-2 heteroatoms independently selected from nitrogen, oxygen, and sulfur; each of which is substituted by $r^1$ instances of $R^{YC}$. In some embodiments, $R^{1A}$ is a $C_{1-6}$ aliphatic chain, phenyl, or a 3-7 membered saturated or partially unsaturated monocyclic carbocyclic ring; each of which is substituted by $r^1$ instances of $R^{1C}$.

In some embodiments, $R^{1A}$ is selected from the groups depicted in the compounds in Table 1.

As defined generally above, $R^{2A}$ is $R^A$ or $R^B$ substituted by $r^2$ instances of $R^{2C}$. In some embodiments, $R^{2A}$ is $R^A$. In some embodiments, $R^{2A}$ is $R^B$ substituted by $r^2$ instances of $R^{2C}$.

In some embodiments, $R^{2A}$ is phenyl; naphthyl; cubanyl; adamantyl; a 5-6 membered monocyclic heteroaryl ring having 1-4 heteroatoms independently selected from nitrogen, oxygen, and sulfur; an 8-10 membered bicyclic heteroaryl ring having 1-4 heteroatoms independently selected from nitrogen, oxygen, and sulfur; a 3-7 membered saturated or partially unsaturated monocyclic carbocyclic ring; a 5-12 membered saturated or partially unsaturated bicyclic carbocyclic ring; a 3-7 membered saturated or partially unsaturated monocyclic heterocyclic ring having 1-2 heteroatoms independently selected from nitrogen, oxygen, and sulfur; or a 7-12 membered saturated or partially unsaturated bicyclic heterocyclic ring having 1-4 heteroatoms independently selected from nitrogen, oxygen, and sulfur; wherein $R^{2A}$ is substituted by $r^2$ instances of $R^{2C}$.

In some embodiments, $R^{2A}$ is phenyl; naphthyl; an 8-10 membered bicyclic heteroaryl ring having 1-4 heteroatoms independently selected from nitrogen, oxygen, and sulfur; or a 7-12 membered saturated or partially unsaturated bicyclic heterocyclic ring having 1-4 heteroatoms independently selected from nitrogen, oxygen, and sulfur; wherein $R^{2A}$ is substituted by $r^2$ instances of $R^{2C}$. In some embodiments, $R^{2A}$ is phenyl; an 8-10 membered bicyclic heteroaryl ring having 1-4 heteroatoms independently selected from nitrogen, oxygen, and sulfur; or a 7-12 membered saturated or partially unsaturated bicyclic heterocyclic ring having 1-4 heteroatoms independently selected from nitrogen, oxygen, and sulfur; wherein $R^{2A}$ is substituted by $r^2$ instances of $R^{2C}$. In some embodiments, $R^{2A}$ is phenyl or an 8-10 membered bicyclic heteroaryl ring having 1-4 heteroatoms independently selected from nitrogen, oxygen, and sulfur; wherein $R^{2A}$ is substituted by $r^2$ instances of $R^{2C}$.

In some embodiments, $R^{2A}$ is phenyl; naphthyl; an 8-10 membered bicyclic heteroaryl ring having 1-4 heteroatoms independently selected from nitrogen, oxygen, and sulfur; or a 7-12 membered saturated or partially unsaturated bicyclic heterocyclic ring having 1-4 heteroatoms independently selected from nitrogen, oxygen, and sulfur; wherein $R^{2A}$ is substituted by $r^2$ instances of a group independently selected from oxo, halogen, —CN, —NO$_2$, —OR, —SR, —NR$_2$, —S(O)$_2$R, —S(O)$_2$NR$_2$, —S(O)$_2$F, —S(O)R, —S(O)NR$_2$, —S(O)(NR)R, —C(O)R, —C(O)OR, —C(O)NR$_2$, —C(O)N(R)OR, —OC(O)R, —OC(O)NR$_2$, —N(R)C(O)O R, —N(R)C(O)R, —N(R)C(O)NR$_2$, —N(R)C(NR)NR$_2$, —N(R)S(O)$_2$NR$_2$, —N(R)S(O)$_2$R, —P(O)R$_2$, —P(O)(R)OR, —B(OR)$_2$, and optionally substituted C$_{1-6}$ aliphatic. In some embodiments, $R^{2A}$ is phenyl; an 8-10 membered bicyclic heteroaryl ring having 1-4 heteroatoms independently selected from nitrogen, oxygen, and sulfur; or a 7-12 membered saturated or partially unsaturated bicyclic heterocyclic ring having 1-4 heteroatoms independently selected from nitrogen, oxygen, and sulfur; wherein $R^{2A}$ is substituted by $r^2$ instances of a group independently selected from oxo, halogen, —CN, —NO$_2$, —OR, —SR, —NR$_2$, —S(O)$_2$R, —S(O)$_2$NR$_2$, —S(O)$_2$F, —S(O)R, —S(O)NR$_2$, —S(O)(NR)R, —C(O)R, —C(O)OR, —C(O)NR$_2$, —C(O)N(R)OR, —OC(O)R, —OC(O)NR$_2$, —N(R)C(O)OR, —N(R)C(O)R, —N(R)C(O)NR$_2$, —N(R)C(NR)NR$_2$, —N(R)S(O)$_2$NR$_2$, —N(R)S(O)$_2$R, —P(O)R$_2$, —P(O)(R)OR, —B(OR)$_2$, and optionally substituted C$_{1-6}$ aliphatic. In some embodiments, $R^{2A}$ is phenyl or an 8-10 membered bicyclic heteroaryl ring having 1-4 heteroatoms independently selected from nitrogen, oxygen, and sulfur; wherein $R^{2A}$ is substituted by $r^2$ instances of a group independently selected from oxo, halogen, —CN, —NO$_2$, —OR, —SR, —NR$_2$, —S(O)$_2$R, —S(O)$_2$NR$_2$, —S(O)$_2$F, —S(O)R, —S(O)NR$_2$, —S(O)(NR)R, —C(O)R, —C(O)OR, —C(O)NR$_2$, —C(O)N(R)OR, —OC(O)R, —OC(O)NR$_2$, —N(R)C(O)OR, —N(R)C(O)R, —N(R)C(O)NR$_2$, —N(R)C(NR)NR$_2$, —N(R)S(O)$_2$NR$_2$, —N(R)S(O)$_2$R, —P(O)R$_2$, —P(O)(R)OR, —B(OR)$_2$, and optionally substituted C$_{1-6}$ aliphatic.

In some embodiments, $R^{2A}$ is phenyl substituted by $r^2$ instances of $R^{2C}$. In some embodiments, $R^{2A}$ is phenyl substituted by $r^2$ instances of a group independently selected from oxo, halogen, —CN, —NO$_2$, —OR, —SR, —NR$_2$, —S(O)$_2$R, —S(O)$_2$NR$_2$, —S(O)$_2$F, —S(O)R, —S(O)NR$_2$, —S(O)(NR)R, —C(O)R, —C(O)OR, —C(O)NR$_2$, —C(O)N(R)OR, —OC(O)R, —OC(O)NR$_2$, —N(R)C(O)OR, —N(R)C(O)R, —N(R)C(O)NR$_2$, —N(R)C(NR)NR$_2$, —N(R)S(O)$_2$NR$_2$, —N(R)S(O)$_2$R, —P(O)R$_2$, —P(O)(R)OR, —B(OR)$_2$, and optionally substituted C$_{1-6}$ aliphatic.

In some embodiments, $R^{2A}$ is phenyl substituted by 1-3 instances of a group independently selected from halogen, —CN, —O-(optionally substituted C$_{1-6}$ aliphatic), and an optionally substituted C$_{1-6}$ aliphatic. In some embodiments, $R^{2A}$ is phenyl substituted by 1-3 instances of a group independently selected from halogen and C$_{1-3}$ aliphatic optionally substituted with 1-3 halogen. In some embodiments, $R^{2A}$ is phenyl substituted by 1-3 instances of a group independently selected from fluorine, chlorine, —CH$_3$, —CHF$_2$, and —CF$_3$.

In some embodiments, $R^{2A}$ is phenyl substituted by 2 instances of a group independently selected from halogen, —CN, —O-(optionally substituted C$_{1-6}$ aliphatic), and an optionally substituted C$_{1-6}$ aliphatic. In some embodiments, $R^{2A}$ is phenyl substituted by 2 instances of a group independently selected from halogen and C$_{1-3}$ aliphatic optionally substituted with 1-3 halogen. In some embodiments, $R^{2A}$ is phenyl substituted by 2 instances of a group independently selected from fluorine, chlorine, —CH$_3$, —CHF$_2$, and —CF$_3$.

In some embodiments, $R^{2A}$ is an 8-10 membered bicyclic heteroaryl ring having 1-4 heteroatoms independently selected from nitrogen, oxygen, and sulfur; wherein $R^{2A}$ is substituted by $r^2$ instances of $R^{2C}$. In some embodiments, $R^{2A}$ is an 8-10 membered bicyclic heteroaryl ring having 1-4 heteroatoms independently selected from nitrogen, oxygen, and sulfur; wherein $R^{2A}$ is substituted by $r^2$ instances of a group independently selected from oxo, halogen, —CN, —NO$_2$, —OR, —SR, —NR$_2$, —S(O)$_2$R, —S(O)$_2$NR$_2$, —S(O)$_2$F, —S(O)R, —S(O)NR$_2$, —S(O)(NR)R, —C(O)R, —C(O)OR, —C(O)NR$_2$, —C(O)N(R)OR, —OC(O)R, —OC(O)NR$_2$, —N(R)C(O)OR, —N(R)C(O)R, —N(R)C(O)NR$_2$, —N(R)C(NR)NR$_2$, —N(R)S(O)$_2$NR$_2$, —N(R)S(O)$_2$R, —P(O)R$_2$, —P(O)(R)OR, —B(OR)$_2$, and optionally substituted C$_{1-6}$ aliphatic.

In some embodiments, $R^{2A}$ is an 8-10 membered bicyclic heteroaryl ring having 1-2 heteroatoms independently selected from nitrogen, oxygen, and sulfur; wherein $R^{2A}$ is substituted by $r^2$ instances of $R^2$. In some embodiments, $R^{2A}$ is an 8-10 membered bicyclic heteroaryl ring having 1-2 heteroatoms independently selected from nitrogen, oxygen, and sulfur; wherein $R^{2A}$ is substituted by $r^2$ instances of a group independently selected from oxo, halogen, —CN, —NO$_2$, —OR, —SR, —NR$_2$, —S(O)$_2$R, —S(O)$_2$NR$_2$, —S(O)$_2$F, —S(O)R, —S(O)NR$_2$, —S(O)(NR)R, —C(O)R, —C(O)OR, —C(O)NR$_2$, —C(O)N(R)OR, —OC(O)R, —OC(O)NR$_2$, —N(R)C(O)OR, —N(R)C(O)R, —N(R)C(O)NR$_2$, —N(R)C(NR)NR$_2$, —N(R)S(O)$_2$NR$_2$, —N(R)S(O)$_2$R, —P(O)R$_2$, —P(O)(R)OR, or —B(OR)$_2$, and optionally substituted C$_{1-6}$ aliphatic.

In some embodiments, $R^{2A}$ is an 8-10 membered bicyclic heteroaryl ring having 1-2 heteroatoms independently selected from nitrogen, oxygen, and sulfur; wherein $R^{2A}$ is substituted by 0-2 instances of a group independently selected from halogen, —CN, —O-(optionally substituted C$_{1-6}$ aliphatic), and an optionally substituted C$_{1-6}$ aliphatic. In some embodiments, $R^{2A}$ is an 8-10 membered bicyclic heteroaryl ring having 1-2 heteroatoms independently selected from nitrogen, oxygen, and sulfur; wherein $R^{2A}$ is substituted by 0-2 instances of a group independently selected from halogen and C$_{1-3}$ aliphatic optionally substituted with 1-3 halogen. In some embodiments, $R^{2A}$ is an 8-10 membered bicyclic heteroaryl ring having 1-2 heteroatoms independently selected from nitrogen, oxygen, and sulfur; wherein $R^{2A}$ is substituted by 0-2 instances of a group independently selected from fluorine, chlorine, —$CH_3$, —$CHF_2$, and —$CF_3$.

In some embodiments, $R^{2A}$ is:

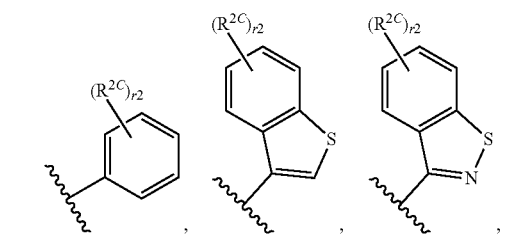

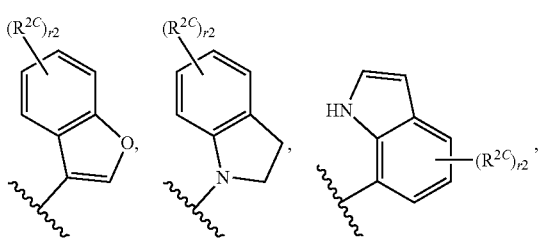

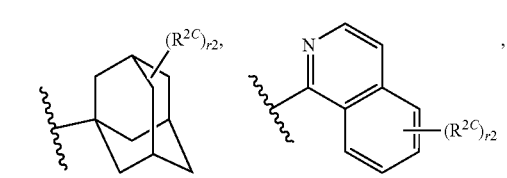

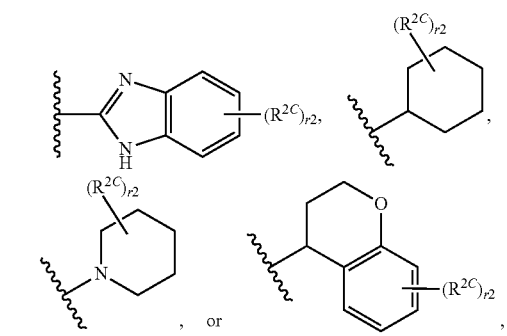

wherein $R^{2C}$ and $r^2$ are as defined in the embodiments and classes and subclasses herein. In some embodiments, $R^{2A}$ is

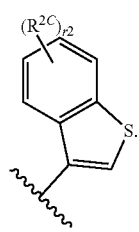

In some embodiments, $R^{2A}$ is

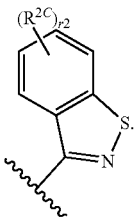

In some embodiments, $R^{2A}$ is

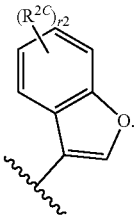

In some embodiments, $R^{2A}$ is

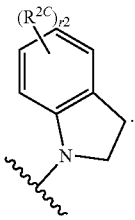

In some embodiments, $R^{2A}$ is

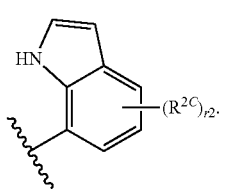

In some embodiments, $R^{2A}$ is

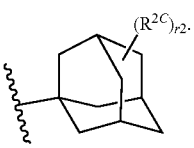

In some embodiments, $R^{2A}$ is

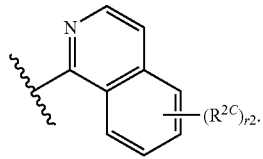

In some embodiments, $R^{2A}$ is

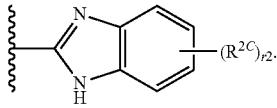

In some embodiments, $R^{2A}$ is

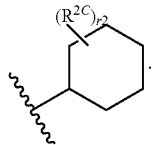

In some embodiments, $R^{2A}$ is

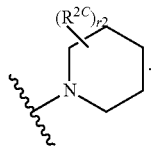

In some embodiments, $R^{2A}$ is

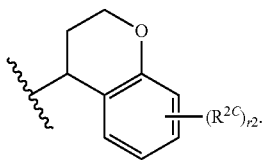

In some embodiments. $R^{2A}$ is oxo, halogen, —CN, —NO$_2$, —OR, —SR, —NR$_2$, —S(O)$_2$R, —S(O)$_2$NR$_2$, —S(O)$_2$F, —S(O)R, —S(O)NR$_2$, —S(O)(NR)R, —C(O)R, —C(O)OR, —C(O)NR$_2$, —C(O)N(R)OR, —OC(O)R, —OC(O)NR$_2$, —N(R)C(O)OR, —N(R)C(O)R, —N(R)C(O)NR$_2$, —N(R)C(NR)NR$_2$, —N(R)S(O)$_2$NR$_2$, —N(R)S(O)$_2$R, —P(O)R$_2$, —P(O)(R)OR, —B(OR)$_2$, or deuterium.

In some embodiments, $R^{2A}$ is oxo, halogen, —CN, —NO$_2$, —OR, —SR, —NR$_2$, —S(O)$_2$R, —S(O)$_2$NR$_2$, —S(O)$_2$F, —S(O)R, —S(O)NR$_2$, —S(O)(NR)R, —C(O)R, —C(O)OR, —C(O)NR$_2$, —C(O)N(R)OR, —OC(O)R, —OC(O)NR$_2$, —N(R)C(O)OR, —N(R)C(O)R, —N(R)C(O)NR$_2$, —N(R)C(NR)NR$_2$, —N(R)S(O)$_2$NR$_2$, —N(R)S(O)$_2$R, —P(O)R$_2$, —P(O)(R)OR, or —B(OR)$_2$.

In some embodiments, $R^{2A}$ is oxo. In some embodiments, $R^{2A}$ is halogen. In some embodiments, $R^{2A}$ is —CN. In some embodiments, $R^{2A}$ is —NO$_2$. In some embodiments, $R^{2A}$ is —OR. In some embodiments, $R^{2A}$ is —SR. In some embodiments, $R^{2A}$ is —NR$_2$. In some embodiments, $R^{2A}$ is —S(O)$_2$R. In some embodiments, $R^{2A}$ is —S(O)$_2$NR$_2$. In some embodiments, $R^{2A}$ is —S(O)$_2$F. In some embodiments, $R^{2A}$ is —S(O)R. In some embodiments, $R^{2A}$ is —S(O)NR$_2$. In some embodiments, $R^{2A}$ is —S(O)(NR)R. In some embodiments, $R^{2A}$ is —C(O)R. In some embodiments, $R^{2A}$ is —C(O)OR. In some embodiments, $R^{2A}$ is —C(O)NR$_2$.

In some embodiments, $R^{2A}$ is —C(O)N(R)OR. In some embodiments, $R^{2A}$ is —OC(O)R. In some embodiments, $R^{2A}$ is —OC(O)NR$_2$. In some embodiments, $R^{2A}$ is —N(R)C(O)OR. In some embodiments, $R^{2A}$ is —N(R)C(O)R. In some embodiments, $R^{2A}$ is —N(R)C(O)NR$_2$. In some embodiments, $R^{2A}$ is —N(R)C(NR)NR$_2$. In some embodiments, $R^{2A}$ is —N(R)S(O)$_2$NR$_2$.

In some embodiments, $R^{2A}$ is —N(R)S(O)$_2$R. In some embodiments, $R^{2A}$ is —P(O)R$_2$. In some embodiments, $R^{2A}$ is —P(O)(R)OR. In some embodiments, $R^{2A}$ is —B(OR)$_2$. In some embodiments, $R^{2A}$ is deuterium.

In some embodiments, $R^{2A}$ is halogen, —CN, —NO$_2$, —OR, —SR, —NR$_2$, —S(O)$_2$R, —S(O)$_2$NR$_2$, —S(O)$_2$F, —S(O)R, —S(O)NR$_2$, —S(O)(NR)R, —C(O)R, —C(O)OR, —C(O)NR$_2$, —C(O)N(R)OR, —OC(O)R, —OC(O)NR$_2$, —N(R)C(O)OR, —N(R)C(O)R, —N(R)C(O)NR$_2$, —N(R)C(NR)NR$_2$, —N(R)S(O)$_2$NR$_2$, —N(R)S(O)$_2$R, —P(O)R$_2$, —P(O)(R)OR, or —B(OR)$_2$.

In some embodiments, $R^{2A}$ is halogen, —CN, or —NO$_2$. In some embodiments, $R^{2A}$ is —OR, —SR, or —NR$_2$. In some embodiments, $R^{2A}$ is —S(O)$_2$R, —S(O)$_2$NR$_2$, —S(O)$_2$F, —S(O)R, —S(O)NR$_2$, or —S(O)(NR)R. In some embodiments, $R^{2A}$ is —C(O)R, —C(O)OR, —C(O)NR$_2$, or —C(O)N(R)OR. In some embodiments, $R^{2A}$ is —OC(O)R or —OC(O)NR$_2$. In some embodiments, $R^{2A}$ is —N(R)C(O)OR, —N(R)C(O)R, —N(R)C(O)NR$_2$, —N(R)C(NR)NR$_2$, —N(R)S(O)$_2$NR$_2$, or —N(R)S(O)$_2$R. In some embodiments, $R^{2A}$ is —P(O)R$_2$ or —P(O)(R)OR.

In some embodiments, $R^{2A}$ is —OR, —OC(O)R, or —OC(O)NR$_2$. In some embodiments, $R^{2A}$ is —SR, —S(O)$_2$R, —S(O)$_2$NR$_2$, —S(O)$_2$F, —S(O)R, —S(O)NR$_2$, or —S(O)(NR)R. In some embodiments, $R^{2A}$ is —NR$_2$, —N(R)C(O)OR, —N(R)C(O)R, —N(R)C(O)NR$_2$, —N(R)C(NR)NR$_2$, —N(R)S(O)$_2$NR$_2$, or —N(R)S(O)$_2$R.

In some embodiments, $R^{2A}$ is —S(O)$_2$R, —S(O)$_2$NR$_2$, or —S(O)$_2$F. In some embodiments, $R^{2A}$ is —S(O)R, —S(O)NR$_2$, or —S(O)(NR)R. In some embodiments, $R^{2A}$ is —SR, —S(O)$_2$R, or —S(O)R. In some embodiments, $R^{2A}$ is —S(O)$_2$NR$_2$, —S(O)NR$_2$, or —S(O)(NR)R. In some embodiments, $R^{2A}$ is —S(O)$_2$NR$_2$ or —S(O)NR$_2$. In some embodiments, $R^{2A}$ is —SR, —S(O)$_2$R, —S(O)$_2$NR$_2$, or —S(O)R.

In some embodiments, $R^{2A}$ is —N(R)C(O)OR, —N(R)C(O)R, or —N(R)C(O)NR$_2$. In some embodiments, $R^{2A}$ is —N(R)S(O)$_2$NR$_2$ or —N(R)S(O)$_2$R. In some embodiments, $R^{2A}$ is —N(R)C(O)OR or —N(R)C(O)R. In some embodiments, $R^{2A}$ is —N(R)C(O)NR$_2$ or —N(R)S(O)$_2$NR$_2$. In some embodiments, $R^{2A}$ is —N(R)C(O)OR, —N(R)C(O)R, or —N(R)S(O)$_2$R.

In some embodiments, $R^{2A}$ is —NR$_2$, —N(R)C(O)OR, —N(R)C(O)R, or —N(R)C(O)NR$_2$. In some embodiments, $R^{2A}$ is —NR$_2$, —N(R)C(O)OR, or —N(R)C(O)R. In some embodiments, $R^{2A}$ is —NR$_2$, —N(R)C(O)OR, —N(R)C(O)R, or —N(R)S(O)$_2$R.

In some embodiments, $R^{2A}$ is a $C_{1-6}$ aliphatic chain; phenyl; naphthyl; cubanyl; adamantyl; a 5-6 membered monocyclic heteroaryl ring having 1-4 heteroatoms independently selected from nitrogen, oxygen, and sulfur; an 8-10 membered bicyclic heteroaryl ring having 1-4 heteroatoms independently selected from nitrogen, oxygen, and sulfur; a 3-7 membered saturated or partially unsaturated monocyclic carbocyclic ring; a 5-12 membered saturated or partially unsaturated bicyclic carbocyclic ring; a 3-7 membered saturated or partially unsaturated monocyclic heterocyclic ring having 1-2 heteroatoms independently selected from nitrogen, oxygen, and sulfur; or a 7-12 membered saturated or partially unsaturated bicyclic heterocyclic ring having 1-4 heteroatoms independently selected from nitrogen, oxygen, and sulfur; each of which is substituted by $r^2$ instances of $R^{2C}$.

In some embodiments, $R^{2A}$ is a $C_{1-6}$ aliphatic chain substituted by $r^2$ instances of $R^{2C}$. In some embodiments, $R^{2A}$ is phenyl substituted by $r^2$ instances of $R^{2C}$. In some embodiments, $R^{2A}$ is naphthyl substituted by $r^2$ instances of $R^{2C}$. In some embodiments, $R^{2A}$ is cubanyl substituted by $r^2$ instances of $R^{2C}$. In some embodiments, $R^{2A}$ is adamantyl substituted by $r^2$ instances of $R^{2C}$. In some embodiments, $R^{2A}$ is a 5-6 membered monocyclic heteroaryl ring having 1-4 heteroatoms independently selected from nitrogen, oxygen, and sulfur; wherein said ring is substituted by $r^2$ instances of $R^{2C}$. In some embodiments, $R^{2A}$ is an 8-10 membered bicyclic heteroaryl ring having 1-4 heteroatoms independently selected from nitrogen, oxygen, and sulfur; wherein said ring is substituted by $r^2$ instances of $R^{2C}$. In some embodiments, $R^{2A}$ is a 3-7 membered saturated or partially unsaturated monocyclic carbocyclic ring substituted by $r^2$ instances of $R^{2C}$. In some embodiments, $R^{2A}$ is a 5-12 membered saturated or partially unsaturated bicyclic carbocyclic ring substituted by $r^2$ instances of $R^{2C}$. In some embodiments, $R^{2A}$ is a 3-7 membered saturated or partially unsaturated monocyclic heterocyclic ring having 1-2 heteroatoms independently selected from nitrogen, oxygen, and sulfur; wherein said ring is substituted by $r^2$ instances of $R^{2C}$. In some embodiments, $R^{2A}$ is a 7-12 membered saturated or partially unsaturated bicyclic heterocyclic ring having 1-4 heteroatoms independently selected from nitrogen, oxygen, and sulfur; wherein said ring is substituted by $r^2$ instances of $R^{2C}$.

In some embodiments, $R^{2A}$ is phenyl; naphthyl; a 5-6 membered monocyclic heteroaryl ring having 1-4 heteroatoms independently selected from nitrogen, oxygen, and sulfur; or an 8-10 membered bicyclic heteroaryl ring having 1-4 heteroatoms independently selected from nitrogen, oxygen, and sulfur; each of which is substituted by $r^2$ instances of $R^{2C}$. In some embodiments, $R^{2A}$ is cubanyl; adamantyl; a 3-7 membered saturated or partially unsaturated monocyclic carbocyclic ring; a 5-12 membered saturated or partially unsaturated bicyclic carbocyclic ring; a 3-7 membered saturated or partially unsaturated monocyclic heterocyclic ring having 1-2 heteroatoms independently selected from nitrogen, oxygen, and sulfur; or a 7-12 membered saturated or partially unsaturated bicyclic heterocyclic ring having 1-4 heteroatoms independently selected from nitrogen, oxygen, and sulfur; each of which is substituted by $r^2$ instances of $R^{2C}$.

In some embodiments, $R^{2A}$ is phenyl; naphthyl; cubanyl; adamantyl; a 3-7 membered saturated or partially unsaturated monocyclic carbocyclic ring; or a 5-12 membered saturated or partially unsaturated bicyclic carbocyclic ring; each of which is substituted by $r^2$ instances of $R^{2C}$. In some embodiments, $R^{2A}$ is a 5-6 membered monocyclic heteroaryl ring having 1-4 heteroatoms independently selected from nitrogen, oxygen, and sulfur; an 8-10 membered bicyclic heteroaryl ring having 1-4 heteroatoms independently selected from nitrogen, oxygen, and sulfur; a 3-7 membered saturated or partially unsaturated monocyclic heterocyclic ring having 1-2 heteroatoms independently selected from nitrogen, oxygen, and sulfur; or a 7-12 membered saturated or partially unsaturated bicyclic heterocyclic ring having 1-4 heteroatoms independently selected from nitrogen, oxygen, and sulfur; each of which is substituted by $r^2$ instances of $R^{2C}$.

In some embodiments, $R^{2A}$ is phenyl; a 5-6 membered monocyclic heteroaryl ring having 1-4 heteroatoms independently selected from nitrogen, oxygen, and sulfur; a 3-7 membered saturated or partially unsaturated monocyclic carbocyclic ring; or a 3-7 membered saturated or partially unsaturated monocyclic heterocyclic ring having 1-2 heteroatoms independently selected from nitrogen, oxygen, and sulfur; each of which is substituted by $r^2$ instances of $R^{2C}$. In some embodiments, $R^{2A}$ is naphthyl; cubanyl; adamantyl; an 8-10 membered bicyclic heteroaryl ring having 1-4 heteroatoms independently selected from nitrogen, oxygen, and sulfur; a 5-12 membered saturated or partially unsaturated bicyclic carbocyclic ring; or a 7-12 membered saturated or partially unsaturated bicyclic heterocyclic ring having 1-4 heteroatoms independently selected from nitrogen, oxygen, and sulfur; each of which is substituted by $r^2$ instances of $R^{2C}$.

In some embodiments, $R^{2A}$ is phenyl or naphthyl; each of which is substituted by $r^2$ instances of $R^{2C}$. In some embodiments, $R^{2A}$ is a 5-6 membered monocyclic heteroaryl ring having 1-4 heteroatoms independently selected from nitrogen, oxygen, and sulfur; or an 8-10 membered bicyclic heteroaryl ring having 1-4 heteroatoms independently selected from nitrogen, oxygen, and sulfur; each of which is substituted by $r^2$ instances of $R^{2C}$. In some embodiments, $R^{2A}$ is a 3-7 membered saturated or partially unsaturated monocyclic carbocyclic ring or a 5-12 membered saturated or partially unsaturated bicyclic carbocyclic ring; each of which is substituted by $r^2$ instances of $R^{2C}$. In some embodiments, $R^{2A}$ is a 3-7 membered saturated or partially unsaturated monocyclic heterocyclic ring having 1-2 heteroatoms independently selected from nitrogen, oxygen, and sulfur; or a 7-12 membered saturated or partially unsaturated bicyclic heterocyclic ring having 1-4 heteroatoms independently selected from nitrogen, oxygen, and sulfur; each of which is substituted by $r^2$ instances of $R^{2C}$.

In some embodiments, $R^{2A}$ is phenyl or a 5-6 membered monocyclic heteroaryl ring having 1-4 heteroatoms independently selected from nitrogen, oxygen, and sulfur; each of which is substituted by $r^2$ instances of $R^{2C}$. In some embodiments, $R^{2A}$ is a 3-7 membered saturated or partially unsaturated monocyclic carbocyclic ring or a 3-7 membered saturated or partially unsaturated monocyclic heterocyclic ring having 1-2 heteroatoms independently selected from nitrogen, oxygen, and sulfur; each of which is substituted by $r^2$ instances of $R^{2C}$. In some embodiments, $R^{2A}$ is naphthyl or an 8-10 membered bicyclic heteroaryl ring having 1-4 heteroatoms independently selected from nitrogen, oxygen, and sulfur; each of which is substituted by $r^2$ instances of $R^{2C}$. In some embodiments, $R^{2A}$ is cubanyl; adamantyl; a 5-12 membered saturated or partially unsaturated bicyclic carbocyclic ring; or a 7-12 membered saturated or partially unsaturated bicyclic heterocyclic ring having 1-4 heteroatoms independently selected from nitrogen, oxygen, and sulfur; each of which is substituted by $r^2$ instances of $R^{2C}$.

In some embodiments, $R^{2A}$ is phenyl or a 3-7 membered saturated or partially unsaturated monocyclic carbocyclic ring; each of which is substituted by $r^2$ instances of $R^{2C}$.

In some embodiments, $R^{2A}$ is naphthyl; cubanyl; adamantyl; or a 5-12 membered saturated or partially unsaturated bicyclic carbocyclic ring; each of which is substituted by $r^2$ instances of $R^{2C}$. In some embodiments, $R^{2A}$ is a 5-6 membered monocyclic heteroaryl ring having 1-4 heteroatoms independently selected from nitrogen, oxygen, and sulfur; or a 3-7 membered saturated or partially unsaturated monocyclic heterocyclic ring having 1-2 heteroatoms independently selected from nitrogen, oxygen, and sulfur; each of which is substituted by $r^2$ instances of $R^{2C}$. In some embodiments, $R^{2A}$ is an 8-10 membered bicyclic heteroaryl ring having 1-4 heteroatoms independently selected from nitrogen, oxygen, and sulfur; or a 7-12 membered saturated or partially unsaturated bicyclic heterocyclic ring having 1-4 heteroatoms independently selected from nitrogen, oxygen, and sulfur; each of which is substituted by $r^2$ instances of $R^{2C}$.

In some embodiments, $R^{2A}$ is a $C_{1-6}$ aliphatic chain; cubanyl; adamantyl; a 3-7 membered saturated or partially unsaturated monocyclic carbocyclic ring; a 5-12 membered saturated or partially unsaturated bicyclic carbocyclic ring; a 3-7 membered saturated or partially unsaturated monocyclic heterocyclic ring having 1-2 heteroatoms independently selected from nitrogen, oxygen, and sulfur; or a 7-12 membered saturated or partially unsaturated bicyclic heterocyclic ring having 1-4 heteroatoms independently selected from nitrogen, oxygen, and sulfur; each of which is substituted by r instances of $R^{2C}$. In some embodiments, $R^{2A}$ is a $C_{1-6}$ aliphatic chain; phenyl; naphthyl; cubanyl; adamantyl; a 3-7 membered saturated or partially unsaturated monocyclic carbocyclic ring; or a 5-12 membered saturated or partially unsaturated bicyclic carbocyclic ring; each of which is substituted by $r^2$ instances of $R^{2C}$. In some embodiments, $R^{2A}$ is a $C_{1-6}$ aliphatic chain; phenyl; a 5-6 membered monocyclic heteroaryl ring having 1-4 heteroatoms independently selected from nitrogen, oxygen, and sulfur; a 3-7 membered saturated or partially unsaturated monocyclic carbocyclic ring; or a 3-7 membered saturated or partially unsaturated monocyclic heterocyclic ring having 1-2 heteroatoms independently selected from nitrogen, oxygen, and sulfur; each of which is substituted by $r^2$ instances of $R^{2C}$.

In some embodiments, $R^{2A}$ is a $C_{1-6}$ aliphatic chain, cubanyl, adamantyl, a 3-7 membered saturated or partially unsaturated monocyclic carbocyclic ring, or a 5-12 membered saturated or partially unsaturated bicyclic carbocyclic ring; each of which is substituted by $r^2$ instances of $R^{2C}$. In some embodiments, $R^{2A}$ is a $C_{1-6}$ aliphatic chain, a 3-7 membered saturated or partially unsaturated monocyclic carbocyclic ring, or a 3-7 membered saturated or partially unsaturated monocyclic heterocyclic ring having 1-2 heteroatoms independently selected from nitrogen, oxygen, and sulfur; each of which is substituted by $r^2$ instances of $R^{2C}$. In some embodiments, $R^{2A}$ is a $C_{1-6}$ aliphatic chain, phenyl, or a 3-7 membered saturated or partially unsaturated monocyclic carbocyclic ring; each of which is substituted by $r^2$ instances of $R^{2C}$.

In some embodiments, $R^{2A}$ is selected from the groups depicted in the compounds in Table 1.

As defined generally above, $R^{EA}$ is $R^A$ or $R^B$ substituted by 3 instances of $R^{EC}$. In some embodiments, $R^{EA}$ is $R^A$. In some embodiments, $R^{EA}$ is $R^B$ substituted by 3 instances of $R^{EC}$.

In some embodiments, each instance of $R^{EA}$ is independently $C_{1-6}$ aliphatic substituted by $r^3$ instances of $R^{EQ}$. In some embodiments, each instance of $R^{EA}$ is independently $C_{1-3}$ aliphatic substituted by $r^3$ instances of $R^{EC}$. In some embodiments, each instance of $R^{EA}$ is independently $C_{1-3}$ aliphatic substituted by $r^3$ instances of halogen. In some embodiments, each instance of $R^{EA}$ is independently $C_{1-3}$ aliphatic. In some embodiments, each instance of $R^{EA}$ is independently —$CH_3$, —$CH_2F$, —$CHF_2$—, or —$CF_3$. In some embodiments, $R^{EA}$ is —$CH_3$.

In some embodiments, $R^{EA}$ is selected from the groups depicted in the compounds in Table 1.

As defined generally above, $R^{QA}$ is $R^A$ or $R^B$ substituted by $r^4$ instances of $R^{QC}$. In some embodiments, $R^{QA}$ is $R^A$. In some embodiments, $R^{QA}$ is $R^B$ substituted by $r^4$ instances of $R^{QC}$.

In some embodiments, $R^{QA}$ is oxo, halogen, —CN, —$NO_2$, —OR, —SR, —$NR_2$, —$S(O)_2R$, —$S(O)_2NR_2$, —$S(O)_2F$, —S(O)R, —$S(O)NR_2$, —S(O)(NR)R, —C(O)R, —C(O)OR, —$C(O)NR_2$, —C(O)N(R)OR, —OC(O)R, —$OC(O)NR_2$, —N(R)C(O)OR, —N(R)C(O)R, —N(R)C(O)$NR_2$, —N(R)C(NR)$NR_2$, —N(R)$S(O)_2NR_2$, —N(R)S(O)$_2$R, —$P(O)R_2$, —P(O)(R)OR, —$B(OR)_2$, or deuterium.

In some embodiments, $R^{QA}$ is oxo, halogen, —CN, —$NO_2$, —OR, —SR, —$NR_2$, —$S(O)_2R$, —$S(O)_2NR_2$, —$S(O)_2F$, —S(O)R, —$S(O)NR_2$, —S(O)(NR)R, —C(O)R, —C(O)OR, —$C(O)NR_2$, —C(O)N(R)OR, —OC(O)R, —$OC(O)NR_2$, —N(R)C(O)OR, —N(R)C(O)R, —N(R)C(O)$NR_2$, —N(R)C(NR)$NR_2$, —N(R)$S(O)_2NR_2$, —N(R)S(O)$_2$R, —$P(O)R_2$, —P(O)(R)OR, or —$B(OR)_2$.

In some embodiments, $R^{QA}$ is oxo. In some embodiments, $R^{QA}$ is halogen. In some embodiments, $R^{QA}$ is —CN. In some embodiments, $R^{QA}$ is —$NO_2$. In some embodiments, $R^{QA}$ is —OR. In some embodiments, $R^{QA}$ is —SR. In some embodiments, $R^{QA}$ is —$NR_2$. In some embodiments, $R^{QA}$ is —$S(O)_2R$. In some embodiments, $R^{QA}$ is —$S(O)_2NR_2$. In some embodiments, $R^{QA}$ is —$S(O)_2F$. In some embodiments, $R^{QA}$ is —S(O)R. In some embodiments, $R^{QA}$ is —$S(O)NR_2$. In some embodiments, $R^{QA}$ is —S(O)(NR)R. In some embodiments, $R^{QA}$ is —C(O)R. In some embodiments, $R^{QA}$ is —C(O)OR. In some embodiments, $R^{QA}$ is —$C(O)NR_2$. In some embodiments, $R^{QA}$ is —C(O)N(R)OR. In some embodiments, $R^{QA}$ is —OC(O)R. In some embodiments, $R^{QA}$ is —$OC(O)NR_2$. In some embodiments, $R^{QA}$ is —N(R)C(O)OR. In some embodiments, $R^{QA}$ is —N(R)C(O)R. In some embodiments, $R^{QA}$ is —N(R)C(O)$NR_2$. In some embodiments, $R^{QA}$ is —N(R)C(NR)$NR_2$. In some embodiments, $R^{QA}$ is —N(R)$S(O)_2NR_2$. In some embodiments, $R^{QA}$ is —N(R)S(O)$_2$R. In some embodiments, $R^{QA}$ is —$P(O)R^2$. In some embodiments, $R^{QA}$ is —P(O)(R)OR. In some embodiments, $R^{QA}$ is —$B(OR)_2$. In some embodiments, $R^{QA}$ is deuterium.

In some embodiments, $R^{QA}$ is halogen, —CN, —$NO_2$, —OR, —SR, —$NR_2$, —$S(O)_2R$, —$S(O)_2NR_2$, —$S(O)_2F$, —S(O)R, —$S(O)NR_2$, —S(O)(NR)R, —C(O)R, —C(O)OR, —$C(O)NR_2$, —C(O)N(R)OR, —OC(O)R, —$OC(O)NR_2$, —N(R)C(O)OR, —N(R)C(O)R, —N(R)C(O)$NR_2$, —N(R)C(NR)$NR_2$, —N(R)$S(O)_2NR_2$, —N(R)S(O)$_2$R, —$P(O)R_2$, —P(O)(R)OR, or —$B(OR)_2$.

In some embodiments, $R^{QA}$ is halogen, —CN, or —$NO_2$. In some embodiments, $R^{QA}$ is —OR, —SR, or —$NR_2$. In some embodiments, $R^{QA}$ is —$S(O)_2R$, —$S(O)_2NR_2$, —$S(O)_2F$, —S(O)R, —$S(O)NR_2$, or —S(O)(NR)R. In some embodiments, $R^{QA}$ is —C(O)R, —C(O)OR, —$C(O)NR_2$, or —C(O)N(R)OR. In some embodiments, $R^{QA}$ is —OC(O)R or —$OC(O)NR_2$. In some embodiments, $R^{QA}$ is —N(R)C(O)OR, —N(R)C(O)R, —N(R)C(O)$NR_2$, —N(R)C(NR)$NR_2$, —N(R)$S(O)_2NR_2$, or —N(R)S(O)$_2$R. In some embodiments, $R^{QA}$ is —$P(O)R_2$ or —P(O)(R)OR.

In some embodiments, $R^{QA}$ is —OR, —OC(O)R, or —$OC(O)NR_2$. In some embodiments, $R^{QA}$ is —SR, —$S(O)_2R$, —$S(O)_2NR_2$, —$S(O)_2F$, —S(O)R, —$S(O)NR_2$, or —S(O)(NR)R. In some embodiments, $R^{QA}$ is —$NR_2$, —N(R)C(O)OR, —N(R)C(O)R, —N(R)C(O)$NR_2$, —N(R)C(NR)$NR_2$, —N(R)$S(O)_2NR_2$, or —N(R)S(O)$_2$R.

In some embodiments, $R^{QA}$ is —$S(O)_2R$, —$S(O)_2NR_2$, or —$S(O)_2F$. In some embodiments, $R^{QA}$ is —S(O)R, —S(O)

NR$_2$, or —S(O)(NR)R. In some embodiments, R$^{QA}$ is —SR, —S(O)$_2$R, or —S(O)R. In some embodiments, R$^{QA}$ is —S(O)$_2$NR$_2$, —S(O)NR$_2$, or —S(O)(NR)R.

In some embodiments, R$^{QA}$ is —S(O)$_2$NR$_2$ or —S(O)NR$_2$. In some embodiments, R$^{QA}$ is —SR, —S(O)$_2$R, —S(O)$_2$NR$_2$, or —S(O)R.

In some embodiments, R$^{QA}$ is —N(R)C(O)OR, —N(R)C(O)R, or —N(R)C(O)NR$_2$. In some embodiments, R$^{QA}$ is —N(R)S(O)$_2$NR$_2$ or —N(R)S(O)$_2$R. In some embodiments, R$^{QA}$ is —N(R)C(O)OR or —N(R)C(O)R. In some embodiments, R$^{QA}$ is —N(R)C(O)NR$_2$ or —N(R)S(O)$_2$NR$_2$. In some embodiments, R$^{QA}$ is —N(R)C(O)OR, —N(R)C(O)R, or —N(R)S(O)$_2$R.

In some embodiments, R$^{QA}$ is —NR$_2$, —N(R)C(O)OR, —N(R)C(O)R, or —N(R)C(O)NR$_2$. In some embodiments, R$^{QA}$ is —NR$_2$, —N(R)C(O)OR, or —N(R)C(O)R. In some embodiments, R$^{QA}$ is —NR$_2$, —N(R)C(O)OR, —N(R)C(O)R, or —N(R)S(O)$_2$R.

In some embodiments, R$^{QA}$ is a C$_{1-6}$ aliphatic chain; phenyl; naphthyl; a 5-6 membered monocyclic heteroaryl ring having 1-4 heteroatoms independently selected from nitrogen, oxygen, and sulfur; an 8-10 membered bicyclic heteroaryl ring having 1-4 heteroatoms independently selected from nitrogen, oxygen, and sulfur; a 3-7 membered saturated or partially unsaturated monocyclic carbocyclic ring; a 5-12 membered saturated or partially unsaturated bicyclic carbocyclic ring; a 3-7 membered saturated or partially unsaturated monocyclic heterocyclic ring having 1-2 heteroatoms independently selected from nitrogen, oxygen, and sulfur; or a 7-12 membered saturated or partially unsaturated bicyclic heterocyclic ring having 1-4 heteroatoms independently selected from nitrogen, oxygen, and sulfur; each of which is substituted by r$^4$ instances of R$^Q$.

In some embodiments, R$^{QA}$ is a C$_{1-6}$ aliphatic chain substituted by r$^4$ instances of R$^{QC}$. In some embodiments, R$^{QA}$ is phenyl substituted by r$^4$ instances of R$^{QC}$. In some embodiments, R$^{QA}$ is naphthyl substituted by r$^4$ instances of R$^{QC}$. In some embodiments, R$^{QA}$ is a 5-6 membered monocyclic heteroaryl ring having 1-4 heteroatoms independently selected from nitrogen, oxygen, and sulfur; wherein said ring is substituted by r$^4$ instances of R$^{QC}$. In some embodiments, R$^{QA}$ is an 8-10 membered bicyclic heteroaryl ring having 1-4 heteroatoms independently selected from nitrogen, oxygen, and sulfur; wherein said ring is substituted by r$^4$ instances of R$^{QC}$. In some embodiments, R$^{QA}$ is a 3-7 membered saturated or partially unsaturated monocyclic carbocyclic ring substituted by r$^4$ instances of R$^{QC}$. In some embodiments, R$^{QA}$ is a 5-12 membered saturated or partially unsaturated bicyclic carbocyclic ring substituted by r$^4$ instances of R$^{QC}$. In some embodiments, R$^{QA}$ is a 3-7 membered saturated or partially unsaturated monocyclic heterocyclic ring having 1-2 heteroatoms independently selected from nitrogen, oxygen, and sulfur; wherein said ring is substituted by r$^4$ instances of R$^{QC}$. In some embodiments, R$^{QA}$ is a 7-12 membered saturated or partially unsaturated bicyclic heterocyclic ring having 1-4 heteroatoms independently selected from nitrogen, oxygen, and sulfur; wherein said ring is substituted by r$^4$ instances of R$^{QC}$.

In some embodiments, R$^{QA}$ is phenyl; naphthyl; a 5-6 membered monocyclic heteroaryl ring having 1-4 heteroatoms independently selected from nitrogen, oxygen, and sulfur; an 8-10 membered bicyclic heteroaryl ring having 1-4 heteroatoms independently selected from nitrogen, oxygen, and sulfur; a 3-7 membered saturated or partially unsaturated monocyclic carbocyclic ring; a 5-12 membered saturated or partially unsaturated bicyclic carbocyclic ring; a 3-7 membered saturated or partially unsaturated monocyclic heterocyclic ring having 1-2 heteroatoms independently selected from nitrogen, oxygen, and sulfur; or a 7-12 membered saturated or partially unsaturated bicyclic heterocyclic ring having 1-4 heteroatoms independently selected from nitrogen, oxygen, and sulfur; each of which is substituted by r$^4$ instances of R$^{QC}$.

In some embodiments, R$^{QA}$ is phenyl; naphthyl; a 5-6 membered monocyclic heteroaryl ring having 1-4 heteroatoms independently selected from nitrogen, oxygen, and sulfur; or an 8-10 membered bicyclic heteroaryl ring having 1-4 heteroatoms independently selected from nitrogen, oxygen, and sulfur; each of which is substituted by r$^4$ instances of R$^{QC}$. In some embodiments, R$^{QA}$ is a 3-7 membered saturated or partially unsaturated monocyclic carbocyclic ring; a 5-12 membered saturated or partially unsaturated bicyclic carbocyclic ring; a 3-7 membered saturated or partially unsaturated monocyclic heterocyclic ring having 1-2 heteroatoms independently selected from nitrogen, oxygen, and sulfur; or a 7-12 membered saturated or partially unsaturated bicyclic heterocyclic ring having 1-4 heteroatoms independently selected from nitrogen, oxygen, and sulfur; each of which is substituted by r$^4$ instances of R$^{QC}$.

In some embodiments, R$^{QA}$ is phenyl; naphthyl; a 3-7 membered saturated or partially unsaturated monocyclic carbocyclic ring; or a 5-12 membered saturated or partially unsaturated bicyclic carbocyclic ring; each of which is substituted by r$^4$ instances of R$^{QC}$. In some embodiments, R$^{QA}$ is a 5-6 membered monocyclic heteroaryl ring having 1-4 heteroatoms independently selected from nitrogen, oxygen, and sulfur; an 8-10 membered bicyclic heteroaryl ring having 1-4 heteroatoms independently selected from nitrogen, oxygen, and sulfur; a 3-7 membered saturated or partially unsaturated monocyclic heterocyclic ring having 1-2 heteroatoms independently selected from nitrogen, oxygen, and sulfur; or a 7-12 membered saturated or partially unsaturated bicyclic heterocyclic ring having 1-4 heteroatoms independently selected from nitrogen, oxygen, and sulfur; each of which is substituted by r$^4$ instances of R$^{QC}$.

In some embodiments, R$^{QA}$ is phenyl; a 5-6 membered monocyclic heteroaryl ring having 1-4 heteroatoms independently selected from nitrogen, oxygen, and sulfur; a 3-7 membered saturated or partially unsaturated monocyclic carbocyclic ring; or a 3-7 membered saturated or partially unsaturated monocyclic heterocyclic ring having 1-2 heteroatoms independently selected from nitrogen, oxygen, and sulfur; each of which is substituted by r$^4$ instances of R$^{QC}$. In some embodiments, R$^{QA}$ is naphthyl; an 8-10 membered bicyclic heteroaryl ring having 1-4 heteroatoms independently selected from nitrogen, oxygen, and sulfur; a 5-12 membered saturated or partially unsaturated bicyclic carbocyclic ring; or a 7-12 membered saturated or partially unsaturated bicyclic heterocyclic ring having 1-4 heteroatoms independently selected from nitrogen, oxygen, and sulfur; each of which is substituted by r$^4$ instances of R$^{QC}$.

In some embodiments, R$^{QA}$ is phenyl or naphthyl; each of which is substituted by r$^4$ instances of R$^{QC}$. In some embodiments, R$^{QA}$ is a 5-6 membered monocyclic heteroaryl ring having 1-4 heteroatoms independently selected from nitrogen, oxygen, and sulfur; or an 8-10 membered bicyclic heteroaryl ring having 1-4 heteroatoms independently selected from nitrogen, oxygen, and sulfur; each of which is substituted by r$^4$ instances of R$^{QC}$. In some embodiments, R$^{QA}$ is a 3-7 membered saturated or partially unsaturated monocyclic carbocyclic ring or a 5-12 membered saturated or partially unsaturated bicyclic carbocyclic ring; each of which is substituted by r$^4$ instances of R$^{QC}$. In some embodiments, R$^{QA}$ is a 3-7 membered saturated or partially unsaturated monocyclic heterocyclic ring having 1-2 heteroatoms independently selected from nitrogen, oxygen, and sulfur; or a 7-12 membered saturated or partially unsaturated bicyclic heterocyclic ring having 1-4 heteroatoms independently selected from nitrogen, oxygen, and sulfur; each of which is substituted by $r^4$ instances of $R^Q$.

In some embodiments, $R^{QA}$ is phenyl or a 5-6 membered monocyclic heteroaryl ring having 1-4 heteroatoms independently selected from nitrogen, oxygen, and sulfur; each of which is substituted by $r^4$ instances of $R^{QC}$. In some embodiments, $R^{QA}$ is a 3-7 membered saturated or partially unsaturated monocyclic carbocyclic ring or a 3-7 membered saturated or partially unsaturated monocyclic heterocyclic ring having 1-2 heteroatoms independently selected from nitrogen, oxygen, and sulfur; each of which is substituted by $r^4$ instances of $R^{QC}$. In some embodiments, $R^{QA}$ is naphthyl or an 8-10 membered bicyclic heteroaryl ring having 1-4 heteroatoms independently selected from nitrogen, oxygen, and sulfur; each of which is substituted by $r^4$ instances of $R^{QC}$. In some embodiments, $R^{QA}$ is a 5-12 membered saturated or partially unsaturated bicyclic carbocyclic ring or a 7-12 membered saturated or partially unsaturated bicyclic heterocyclic ring having 1-4 heteroatoms independently selected from nitrogen, oxygen, and sulfur; each of which is substituted by $r^4$ instances of $R^{QC}$.

In some embodiments, $R^{QA}$ is phenyl or a 3-7 membered saturated or partially unsaturated monocyclic carbocyclic ring; each of which is substituted by $r^4$ instances of $R^{QC}$. In some embodiments, $R^{QA}$ is naphthyl or a 5-12 membered saturated or partially unsaturated bicyclic carbocyclic ring; each of which is substituted by $r^4$ instances of $R^{QC}$. In some embodiments, $R^{QA}$ is a 5-6 membered monocyclic heteroaryl ring having 1-4 heteroatoms independently selected from nitrogen, oxygen, and sulfur; or a 3-7 membered saturated or partially unsaturated monocyclic heterocyclic ring having 1-2 heteroatoms independently selected from nitrogen, oxygen, and sulfur; each of which is substituted by $r^4$ instances of $R^{QC}$. In some embodiments, $R^{QA}$ is an 8-10 membered bicyclic heteroaryl ring having 1-4 heteroatoms independently selected from nitrogen, oxygen, and sulfur; or a 7-12 membered saturated or partially unsaturated bicyclic heterocyclic ring having 1-4 heteroatoms independently selected from nitrogen, oxygen, and sulfur; each of which is substituted by $r^4$ instances of $R^{QC}$.

In some embodiments, $R^{QA}$ is a $C_{1-6}$ aliphatic chain; a 3-7 membered saturated or partially unsaturated monocyclic carbocyclic ring; a 5-12 membered saturated or partially unsaturated bicyclic carbocyclic ring; a 3-7 membered saturated or partially unsaturated monocyclic heterocyclic ring having 1-2 heteroatoms independently selected from nitrogen, oxygen, and sulfur; or a 7-12 membered saturated or partially unsaturated bicyclic heterocyclic ring having 1-4 heteroatoms independently selected from nitrogen, oxygen, and sulfur; each of which is substituted by $r^4$ instances of $R^{QC}$. In some embodiments, $R^{QA}$ is a $C_{1-6}$ aliphatic chain; phenyl; naphthyl; a 3-7 membered saturated or partially unsaturated monocyclic carbocyclic ring; or a 5-12 membered saturated or partially unsaturated bicyclic carbocyclic ring; each of which is substituted by $r^4$ instances of $R^{QC}$. In some embodiments, $R^{QA}$ is a $C_{1-6}$ aliphatic chain; phenyl; a 5-6 membered monocyclic heteroaryl ring having 1-4 heteroatoms independently selected from nitrogen, oxygen, and sulfur; a 3-7 membered saturated or partially unsaturated monocyclic carbocyclic ring; or a 3-7 membered saturated or partially unsaturated monocyclic heterocyclic ring having 1-2 heteroatoms independently selected from nitrogen, oxygen, and sulfur; each of which is substituted by $r^4$ instances of $R^{QC}$.

In some embodiments, $R^{QA}$ is a $C_{1-6}$ aliphatic chain, a 3-7 membered saturated or partially unsaturated monocyclic carbocyclic ring, or a 5-12 membered saturated or partially unsaturated bicyclic carbocyclic ring; each of which is substituted by $r^4$ instances of $R^{QC}$. In some embodiments, $R^{QA}$ is a $C_{1-6}$ aliphatic chain, a 3-7 membered saturated or partially unsaturated monocyclic carbocyclic ring, or a 3-7 membered saturated or partially unsaturated monocyclic heterocyclic ring having 1-2 heteroatoms independently selected from nitrogen, oxygen, and sulfur; each of which is substituted by $r^4$ instances of $R^{QC}$. In some embodiments, $R^{QA}$ is a $C_{1-6}$ aliphatic chain, phenyl, or a 3-7 membered saturated or partially unsaturated monocyclic carbocyclic ring; each of which is substituted by $r^4$ instances of $R^{QC}$.

In some embodiments, $R^{QA}$ is selected from the groups depicted in the compounds in Table 1.

As defined generally above, $R^{XA}$ is $R^A$ or $R^B$ substituted by $r^5$ instances of $R^{XC}$. In some embodiments, $R^{XA}$ is $R^A$. In some embodiments, $R^{XA}$ is $R^B$ substituted by $r^5$ instances of $R^{XC}$.

In some embodiments, $R^{XA}$ is oxo, halogen, —CN, —NO$_2$, —OR, —SR, —NR$_2$, —S(O)$_2$R, —S(O)$_2$NR$_2$, —S(O)$_2$F, —S(O)R, —S(O)NR$_2$, —S(O)(NR)R, —C(O)R, —C(O)OR, —C(O)NR$_2$, —C(O)N(R)OR, —OC(O)R, —OC(O)NR$_2$, —N(R)C(O)OR, —N(R)C(O)R, —N(R)C(O)NR$_2$, —N(R)C(NR)NR$_2$, —N(R)S(O)$_2$NR$_2$, —N(R)S(O)$_2$R, —P(O)R$_2$, —P(O)(R)OR, —B(OR)$_2$, or deuterium.

In some embodiments, $R^{XA}$ is oxo, halogen, —CN, —NO$_2$, —OR, —SR, —NR$_2$, —S(O)$_2$R, —S(O)$_2$NR$_2$, —S(O)$_2$F, —S(O)R, —S(O)NR$_2$, —S(O)(NR)R, —C(O)R, —C(O)OR, —C(O)NR$_2$, —C(O)N(R)OR, —OC(O)R, —OC(O)NR$_2$, —N(R)C(O)OR, —N(R)C(O)R, —N(R)C(O)NR$_2$, —N(R)C(NR)NR$_2$, —N(R)S(O)$_2$NR$_2$, —N(R)S(O)$_2$R, —P(O)R$_2$, —P(O)(R)OR, or —B(OR)$_2$.

In some embodiments, $R^{XA}$ is oxo. In some embodiments, $R^{XA}$ is halogen. In some embodiments, $R^{XA}$ is —CN. In some embodiments, $R^{XA}$ is —NO$_2$. In some embodiments, $R^{XA}$ is —OR. In some embodiments, $R^{XA}$ is —SR. In some embodiments, $R^{XA}$ is —NR$_2$. In some embodiments, $R^{XA}$ is —S(O)$_2$R. In some embodiments, $R^{XA}$ is —S(O)$_2$NR$_2$. In some embodiments, $R^{XA}$ is —S(O)$_2$F. In some embodiments, $R^{XA}$ is —S(O)R. In some embodiments, $R^{XA}$ is —S(O)NR$_2$. In some embodiments, $R^{XA}$ is —S(O)(NR)R. In some embodiments, $R^{XA}$ is —C(O)R. In some embodiments, $R^{XA}$ is —C(O)OR. In some embodiments, $R^{XA}$ is —C(O)NR$_2$. In some embodiments, $R^{XA}$ is —C(O)N(R)OR. In some embodiments, $R^{XA}$ is —OC(O)R. In some embodiments, $R^{XA}$ is —OC(O)NR$_2$. In some embodiments, $R^{XA}$ is —N(R)C(O)OR. In some embodiments, $R^{XA}$ is —N(R)C(O)R. In some embodiments, $R^{XA}$ is —N(R)C(O)NR$_2$. In some embodiments, $R^{XA}$ is —N(R)C(NR)NR$_2$. In some embodiments, $R^{XA}$ is —N(R)S(O)$_2$NR$_2$. In some embodiments, $R^{XA}$ is —N(R)S(O)$_2$R. In some embodiments, $R^{XA}$ is —P(O)R$_2$. In some embodiments, $R^{XA}$ is —P(O)(R)OR. In some embodiments, $R^{XA}$ is —B(OR)$_2$. In some embodiments, $R^{XA}$ is deuterium.

In some embodiments, $R^{XA}$ is halogen, —CN, —NO$_2$, —OR, —SR, —NR$_2$, —S(O)$_2$R, —S(O)$_2$NR$_2$, —S(O)$_2$F, —S(O)R, —S(O)NR$_2$, —S(O)(NR)R, —C(O)R, —C(O)OR, —C(O)NR$_2$, —C(O)N(R)OR, —OC(O)R, —OC(O)NR$_2$, —N(R)C(O)OR, —N(R)C(O)R, —N(R)C(O)NR$_2$, —N(R)C(NR)NR$_2$, —N(R)S(O)$_2$NR$_2$, —N(R)S(O)$_2$R, —P(O)R$_2$, —P(O)(R)OR, or —B(OR)$_2$.

In some embodiments, $R^{XA}$ is halogen, —CN, or —NO$_2$. In some embodiments, $R^{XA}$ is —OR, —SR, or —NR$_2$. In some embodiments, $R^{XA}$ is —S(O)$_2$R, —S(O)$_2$NR$_2$, —S(O)$_2$F, —S(O)R, —S(O)NR$_2$, or —S(O)(NR)R. In some embodiments, $R^X$ is —C(O)R, —C(O)OR, —C(O)NR$_2$, or —C(O)N(R)OR. In some embodiments, $R^{XA}$ is —OC(O)R or —OC(O)NR$_2$. In some embodiments, $R^{XA}$ is —N(R)C(O)OR, —N(R)C(O)R, —N(R)C(O)NR$_2$, —N(R)C(NR)NR$_2$, —N(R)S(O)$_2$NR$_2$, or —N(R)S(O)$_2$R. In some embodiments, $R^{XA}$ is —P(O)R$_2$ or —P(O)(R)OR.

In some embodiments, $R^{XA}$ is —OR, —OC(O)R, or —OC(O)NR$_2$. In some embodiments, $R^{XA}$ is —SR, —S(O)$_2$R, —S(O)$_2$NR$_2$, —S(O)$_2$F, —S(O)R, —S(O)NR$_2$, or —S(O)(NR)R. In some embodiments, $R^{XA}$ is —NR$_2$, —N(R)C(O)OR, —N(R)C(O)R, —N(R)C(O)NR$_2$, —N(R)C(NR)NR$_2$, —N(R)S(O)$_2$NR$_2$, or —N(R)S(O)$_2$R.

In some embodiments, $R^{XA}$ is —S(O)$_2$R, —S(O)$_2$NR$_2$, or —S(O)$_2$F. In some embodiments, $R^{XA}$ is —S(O)R, —S(O)NR$_2$, or —S(O)(NR)R. In some embodiments, $R^{XA}$ is —SR, —S(O)$_2$R, or —S(O)R. In some embodiments, $R^{XA}$ is —S(O)$_2$NR$_2$, —S(O)NR$_2$, or —S(O)(NR)R.

In some embodiments, $R^{XA}$ is —S(O)$_2$NR$_2$ or —S(O)NR$_2$. In some embodiments, $R^{XA}$ is —SR, —S(O)$_2$R, —S(O)$_2$NR$_2$, or —S(O)R.

In some embodiments, $R^{XA}$ is —N(R)C(O)OR, —N(R)C(O)R, or —N(R)C(O)NR$_2$. In some embodiments, $R^{XA}$ is —N(R)S(O)$_2$NR$_2$ or —N(R)S(O)$_2$R. In some embodiments, $R^{XA}$ is —N(R)C(O)OR or —N(R)C(O)R. In some embodiments, $R^{XA}$ is —N(R)C(O)NR$_2$ or —N(R)S(O)$_2$NR$_2$. In some embodiments, $R^{XA}$ is —N(R)C(O)OR, —N(R)C(O)R, or —N(R)S(O)$_2$R.

In some embodiments, $R^{XA}$ is —NR$_2$, —N(R)C(O)OR, —N(R)C(O)R, or —N(R)C(O)NR$_2$. In some embodiments, $R^{XA}$ is —NR$_2$, —N(R)C(O)OR, or —N(R)C(O)R. In some embodiments, $R^{XA}$ is —NR$_2$, —N(R)C(O)OR, —N(R)C(O)R, or —N(R)S(O)$_2$R.

In some embodiments, $R^{XA}$ is a $C_{1-6}$ aliphatic chain; phenyl; naphthyl; a 5-6 membered monocyclic heteroaryl ring having 1-4 heteroatoms independently selected from nitrogen, oxygen, and sulfur; an 8-10 membered bicyclic heteroaryl ring having 1-4 heteroatoms independently selected from nitrogen, oxygen, and sulfur; a 3-7 membered saturated or partially unsaturated monocyclic carbocyclic ring; a 5-12 membered saturated or partially unsaturated bicyclic carbocyclic ring; a 3-7 membered saturated or partially unsaturated monocyclic heterocyclic ring having 1-2 heteroatoms independently selected from nitrogen, oxygen, and sulfur; or a 7-12 membered saturated or partially unsaturated bicyclic heterocyclic ring having 1-4 heteroatoms independently selected from nitrogen, oxygen, and sulfur; each of which is substituted by $r^5$ instances of $R^{XC}$.

In some embodiments, $R^{XA}$ is a $C_{1-6}$ aliphatic chain substituted by $r^5$ instances of $R^{XC}$. In some embodiments, $R^{XA}$ is phenyl substituted by $r^5$ instances of $R^{XC}$. In some embodiments, $R^{XA}$ is naphthyl substituted by $r^5$ instances of $R^{XC}$. In some embodiments, $R^{X}A$ is a 5-6 membered monocyclic heteroaryl ring having 1-4 heteroatoms independently selected from nitrogen, oxygen, and sulfur; wherein said ring is substituted by $r^5$ instances of $R^X$. In some embodiments, $R^{XA}$ is an 8-10 membered bicyclic heteroaryl ring having 1-4 heteroatoms independently selected from nitrogen, oxygen, and sulfur; wherein said ring is substituted by $r^5$ instances of $R^{XC}$. In some embodiments, $R^{XA}$ is a 3-7 membered saturated or partially unsaturated monocyclic carbocyclic ring substituted by $r^5$ instances of $R^{XC}$. In some embodiments, $R^{XA}$ is a 5-12 membered saturated or partially unsaturated bicyclic carbocyclic ring substituted by $r^5$ instances of $R^{XC}$. In some embodiments, $R^{XA}$ is a 3-7 membered saturated or partially unsaturated monocyclic heterocyclic ring having 1-2 heteroatoms independently selected from nitrogen, oxygen, and sulfur; wherein said ring is substituted by $r^5$ instances of $R^{XC}$. In some embodiments, $R^{XA}$ is a 7-12 membered saturated or partially unsaturated bicyclic heterocyclic ring having 1-4 heteroatoms independently selected from nitrogen, oxygen, and sulfur; wherein said ring is substituted by $r^5$ instances of $R^{XC}$.

In some embodiments, $R^{XA}$ is phenyl; naphthyl; a 5-6 membered monocyclic heteroaryl ring having 1-4 heteroatoms independently selected from nitrogen, oxygen, and sulfur; an 8-10 membered bicyclic heteroaryl ring having 1-4 heteroatoms independently selected from nitrogen, oxygen, and sulfur; a 3-7 membered saturated or partially unsaturated monocyclic carbocyclic ring; a 5-12 membered saturated or partially unsaturated bicyclic carbocyclic ring; a 3-7 membered saturated or partially unsaturated monocyclic heterocyclic ring having 1-2 heteroatoms independently selected from nitrogen, oxygen, and sulfur; or a 7-12 membered saturated or partially unsaturated bicyclic heterocyclic ring having 1-4 heteroatoms independently selected from nitrogen, oxygen, and sulfur; each of which is substituted by $r^5$ instances of $R^{XC}$.

In some embodiments, $R^{XA}$ is phenyl; naphthyl; a 5-6 membered monocyclic heteroaryl ring having 1-4 heteroatoms independently selected from nitrogen, oxygen, and sulfur; or an 8-10 membered bicyclic heteroaryl ring having 1-4 heteroatoms independently selected from nitrogen, oxygen, and sulfur; each of which is substituted by $r^5$ instances of $R^{XC}$. In some embodiments, $R^{XA}$ is a 3-7 membered saturated or partially unsaturated monocyclic carbocyclic ring; a 5-12 membered saturated or partially unsaturated bicyclic carbocyclic ring; a 3-7 membered saturated or partially unsaturated monocyclic heterocyclic ring having 1-2 heteroatoms independently selected from nitrogen, oxygen, and sulfur; or a 7-12 membered saturated or partially unsaturated bicyclic heterocyclic ring having 1-4 heteroatoms independently selected from nitrogen, oxygen, and sulfur; each of which is substituted by $r^5$ instances of $R^{XC}$.

In some embodiments, $R^{XA}$ is phenyl; naphthyl; a 3-7 membered saturated or partially unsaturated monocyclic carbocyclic ring; or a 5-12 membered saturated or partially unsaturated bicyclic carbocyclic ring; each of which is substituted by $r^5$ instances of $R^{XC}$. In some embodiments, $R^{XA}$ is a 5-6 membered monocyclic heteroaryl ring having 1-4 heteroatoms independently selected from nitrogen, oxygen, and sulfur; an 8-10 membered bicyclic heteroaryl ring having 1-4 heteroatoms independently selected from nitrogen, oxygen, and sulfur; a 3-7 membered saturated or partially unsaturated monocyclic heterocyclic ring having 1-2 heteroatoms independently selected from nitrogen, oxygen, and sulfur; or a 7-12 membered saturated or partially unsaturated bicyclic heterocyclic ring having 1-4 heteroatoms independently selected from nitrogen, oxygen, and sulfur; each of which is substituted by $r^5$ instances of $R^{XC}$.

In some embodiments, $R^{XA}$ is phenyl; a 5-6 membered monocyclic heteroaryl ring having 1-4 heteroatoms independently selected from nitrogen, oxygen, and sulfur; a 3-7 membered saturated or partially unsaturated monocyclic carbocyclic ring; or a 3-7 membered saturated or partially unsaturated monocyclic heterocyclic ring having 1-2 heteroatoms independently selected from nitrogen, oxygen, and sulfur; each of which is substituted by $r^5$ instances of $R^{XC}$. In some embodiments, $R^{XA}$ is naphthyl; an 8-10 membered bicyclic heteroaryl ring having 1-4 heteroatoms independently selected from nitrogen, oxygen, and sulfur; a 5-12 membered saturated or partially unsaturated bicyclic carbocyclic ring; or a 7-12 membered saturated or partially unsaturated bicyclic heterocyclic ring having 1-4 heteroatoms independently selected from nitrogen, oxygen, and sulfur; each of which is substituted by $r^5$ instances of $R^{XC}$.

In some embodiments, $R^{XA}$ is phenyl or naphthyl; each of which is substituted by $r^5$ instances of $R^{XC}$. In some embodiments, $R^{XA}$ is a 5-6 membered monocyclic heteroaryl ring having 1-4 heteroatoms independently selected from nitrogen, oxygen, and sulfur; or an 8-10 membered bicyclic heteroaryl ring having 1-4 heteroatoms independently selected from nitrogen, oxygen, and sulfur; each of which is substituted by $r^1$ instances of $R^{XC}$. In some embodiments, $R^{XA}$ is a 3-7 membered saturated or partially unsaturated monocyclic carbocyclic ring or a 5-12 membered saturated or partially unsaturated bicyclic carbocyclic ring; each of which is substituted by $r^1$ instances of $R^{XC}$. In some embodiments, $R^{XA}$ is a 3-7 membered saturated or partially unsaturated monocyclic heterocyclic ring having 1-2 heteroatoms independently selected from nitrogen, oxygen, and sulfur; or a 7-12 membered saturated or partially unsaturated bicyclic heterocyclic ring having 1-4 heteroatoms independently selected from nitrogen, oxygen, and sulfur; each of which is substituted by $r^5$ instances of $R^{XC}$.

In some embodiments, $R^{XA}$ is phenyl or a 5-6 membered monocyclic heteroaryl ring having 1-4 heteroatoms independently selected from nitrogen, oxygen, and sulfur; each of which is substituted by $r^5$ instances of $R^{XC}$. In some embodiments, $R^{XA}$ is a 3-7 membered saturated or partially unsaturated monocyclic carbocyclic ring or a 3-7 membered saturated or partially unsaturated monocyclic heterocyclic ring having 1-2 heteroatoms independently selected from nitrogen, oxygen, and sulfur; each of which is substituted by $r^5$ instances of $R^{XC}$. In some embodiments, $R^{XA}$ is naphthyl or an 8-10 membered bicyclic heteroaryl ring having 1-4 heteroatoms independently selected from nitrogen, oxygen, and sulfur; each of which is substituted by $r^5$ instances of $R^{XC}$. In some embodiments, $R^{XA}$ is a 5-12 membered saturated or partially unsaturated bicyclic carbocyclic ring or a 7-12 membered saturated or partially unsaturated bicyclic heterocyclic ring having 1-4 heteroatoms independently selected from nitrogen, oxygen, and sulfur; each of which is substituted by $r^5$ instances of $R^{XC}$.

In some embodiments, $R^{XA}$ is phenyl or a 3-7 membered saturated or partially unsaturated monocyclic carbocyclic ring; each of which is substituted by $r^5$ instances of $R^{XC}$ In some embodiments, $R^{XA}$ is naphthyl or a 5-12 membered saturated or partially unsaturated bicyclic carbocyclic ring; each of which is substituted by $r^1$ instances of $R^{XC}$. In some embodiments, $R^A$ is a 5-6 membered monocyclic heteroaryl ring having 1-4 heteroatoms independently selected from nitrogen, oxygen, and sulfur; or a 3-7 membered saturated or partially unsaturated monocyclic heterocyclic ring having 1-2 heteroatoms independently selected from nitrogen, oxygen, and sulfur; each of which is substituted by $r^5$ instances of $R^{XC}$. In some embodiments, $R^{XA}$ is an 8-10 membered bicyclic heteroaryl ring having 1-4 heteroatoms independently selected from nitrogen, oxygen, and sulfur; or a 7-12 membered saturated or partially unsaturated bicyclic heterocyclic ring having 1-4 heteroatoms independently selected from nitrogen, oxygen, and sulfur; each of which is substituted by $r^5$ instances of $R^{XC}$.

In some embodiments, $R^{XA}$ is a $C_{1-6}$ aliphatic chain; a 3-7 membered saturated or partially unsaturated monocyclic carbocyclic ring; a 5-12 membered saturated or partially unsaturated bicyclic carbocyclic ring; a 3-7 membered saturated or partially unsaturated monocyclic heterocyclic ring having 1-2 heteroatoms independently selected from nitrogen, oxygen, and sulfur; or a 7-12 membered saturated or partially unsaturated bicyclic heterocyclic ring having 1-4 heteroatoms independently selected from nitrogen, oxygen, and sulfur; each of which is substituted by $r^5$ instances of $R^{XC}$. In some embodiments, $R^{XA}$ is a $C_{1-6}$ aliphatic chain; phenyl; naphthyl; a 3-7 membered saturated or partially unsaturated monocyclic carbocyclic ring; or a 5-12 membered saturated or partially unsaturated bicyclic carbocyclic ring; each of which is substituted by $r^5$ instances of $R^{XC}$. In some embodiments, $R^{XA}$ is a $C_{1-6}$ aliphatic chain; phenyl; a 5-6 membered monocyclic heteroaryl ring having 1-4 heteroatoms independently selected from nitrogen, oxygen, and sulfur; a 3-7 membered saturated or partially unsaturated monocyclic carbocyclic ring; or a 3-7 membered saturated or partially unsaturated monocyclic heterocyclic ring having 1-2 heteroatoms independently selected from nitrogen, oxygen, and sulfur; each of which is substituted by $r^5$ instances of $R^{XC}$.

In some embodiments, $R^{XA}$ is a $C_{1-6}$ aliphatic chain, a 3-7 membered saturated or partially unsaturated monocyclic carbocyclic ring, or a 5-12 membered saturated or partially unsaturated bicyclic carbocyclic ring; each of which is substituted by $r^5$ instances of $R^{XC}$. In some embodiments, $R^{XA}$ is a $C_{1-6}$ aliphatic chain, a 3-7 membered saturated or partially unsaturated monocyclic carbocyclic ring, or a 3-7 membered saturated or partially unsaturated monocyclic heterocyclic ring having 1-2 heteroatoms independently selected from nitrogen, oxygen, and sulfur; each of which is substituted by $r^5$ instances of $R^{XC}$. In some embodiments, $R^{XA}$ is a $C_{1-6}$ aliphatic chain, phenyl, or a 3-7 membered saturated or partially unsaturated monocyclic carbocyclic ring; each of which is substituted by $r^5$ instances of $R^{XC}$.

In some embodiments, $R^{XA}$ is selected from the groups depicted in the compounds in Table 1.

As defined generally above, $R^{YA}$ is $R^A$ or $R^B$ substituted by $r^6$ instances of $R^{YC}$. In some embodiments, $R^{YA}$ is $R^A$. In some embodiments, $R^{YA}$ is $R^B$ substituted by $r^6$ instances of $R^{YC}$.

In some embodiments, $R^{YA}$ is oxo, halogen, —CN, —NO$_2$, —OR, —SR, —NR$_2$, —S(O)$_2$R, —S(O)$_2$NR$_2$, —S(O)$_2$F, —S(O)R, —S(O)NR$_2$, —S(O)(NR)R, —C(O)R, —C(O)OR, —C(O)NR$_2$, —C(O)N(R)OR, —OC(O)R, —OC(O)NR$_2$, —N(R)C(O)OR, —N(R)C(O)R, —N(R)C(O)NR$_2$, —N(R)C(NR)NR$_2$, —N(R)S(O)$_2$NR$_2$, —N(R)S(O)$_2$R, —P(O)R$_2$, —P(O)(R)OR, —B(OR)$_2$, or $R^B$ selected from a $C_{1-6}$ aliphatic chain; phenyl; a 5-6 membered monocyclic heteroaryl ring having 1-4 heteroatoms independently selected from nitrogen, oxygen, and sulfur; a 3-7 membered saturated or partially unsaturated monocyclic carbocyclic ring; and a 3-7 membered saturated or partially unsaturated monocyclic heterocyclic ring having 1-2 heteroatoms independently selected from nitrogen, oxygen, and sulfur; wherein said $R^B$ is substituted by $r^6$ instances of $R^{YC}$.

In some embodiments, $R^{YA}$ is halogen, —CN, —OR, —NR$_2$, —C(O)R, —C(O)OR, —C(O)NR$_2$, —N(R)C(O)R, or $R^B$ selected from a $C_{1-6}$ aliphatic chain; phenyl; a 5-6 membered monocyclic heteroaryl ring having 1-4 heteroatoms independently selected from nitrogen, oxygen, and sulfur; a 3-7 membered saturated or partially unsaturated monocyclic carbocyclic ring; and a 3-7 membered saturated or partially unsaturated monocyclic heterocyclic ring having 1-2 heteroatoms independently selected from nitrogen, oxygen, and sulfur; wherein said $R^B$ is substituted by $r^6$ instances of $R^{YC}$.

In some embodiments, $R^{YA}$ is halogen, —CN, —OR, —NR$_2$, —C(O)R, —C(O)OR, —C(O)NR$_2$, —N(R)C(O)R, or $R^B$ selected from a $C_{1-6}$ aliphatic chain; a 5-6 membered monocyclic heteroaryl ring having 1-4 heteroatoms independently selected from nitrogen, oxygen, and sulfur; a 3-7 membered saturated or partially unsaturated monocyclic carbocyclic ring; and a 3-7 membered saturated or partially unsaturated monocyclic heterocyclic ring having 1-2 heteroatoms independently selected from nitrogen, oxygen, and sulfur; wherein said $R^B$ is substituted by $r^6$ instances of $R^{YC}$. In some embodiments, $R^{YA}$ is halogen or $R^B$ selected from a $C_{1-6}$ aliphatic chain; a 5-6 membered monocyclic heteroaryl ring having 1-4 heteroatoms independently selected from nitrogen, oxygen, and sulfur; a 3-7 membered saturated or partially unsaturated monocyclic carbocyclic ring; and a 3-7 membered saturated or partially unsaturated monocyclic heterocyclic ring having 1-2 heteroatoms independently selected from nitrogen, oxygen, and sulfur; wherein said $R^B$ is substituted by $r^6$ instances of $R^{YC}$.

In some embodiments, $R^{YA}$ is halogen or $R^B$ selected from a $C_{1-4}$ aliphatic chain; a 5-6 membered monocyclic heteroaryl ring having 1-4 heteroatoms independently selected from nitrogen, oxygen, and sulfur; a 3-5 membered saturated or partially unsaturated monocyclic carbocyclic ring; and a 3-5 membered saturated or partially unsaturated monocyclic heterocyclic ring having 1-2 heteroatoms independently selected from nitrogen, oxygen, and sulfur; wherein said $R^B$ is substituted by $r^6$ instances of $R^{YC}$. In some embodiments, $R^{YA}$ is halogen or $R^B$ selected from a $C_{1-4}$ aliphatic chain; a 5-6 membered monocyclic heteroaryl ring having 1-4 heteroatoms independently selected from nitrogen, oxygen, and sulfur; a 3-5 membered saturated or partially unsaturated monocyclic carbocyclic ring; and a 3-5 membered saturated or partially unsaturated monocyclic heterocyclic ring having 1-2 heteroatoms independently selected from nitrogen, oxygen, and sulfur; wherein said $R^B$ is substituted by $r^6$ instances of a group independently selected from oxo, halogen, —CN, —NO$_2$, —OR, —SR, —NR$_2$, —S(O)$_2$R, —S(O)$_2$NR$_2$, —S(O)$_2$F, —S(O)R, —S(O)NR$_2$, —S(O)(NR)R, —C(O)R, —C(O)OR, —C(O)NR$_2$, —C(O)N(R)OR, —OC(O)R, —OC(O)NR$_2$, —N(R)C(O)OR, —N(R)C(O)R, —N(R)C(O)NR$_2$, —N(R)C(NR)NR$_2$, —N(R)S(O)$_2$NR$_2$, —N(R)S(O)$_2$R, —P(O)R$_2$, —P(O)(R)OR, —B(OR)$_2$, and optionally substituted $C_{1-6}$ aliphatic.

In some embodiments, $R^{YA}$ is halogen or $R^B$ selected from a $C_{1-4}$ aliphatic chain; a 5-6 membered monocyclic heteroaryl ring having 1-4 heteroatoms independently selected from nitrogen, oxygen, and sulfur; a 3-5 membered saturated or partially unsaturated monocyclic carbocyclic ring; and a 3-5 membered saturated or partially unsaturated monocyclic heterocyclic ring having 1-2 heteroatoms independently selected from nitrogen, oxygen, and sulfur; wherein said $R^B$ is substituted by $r^6$ instances of a group independently selected from halogen, —CN, —OH, —O-(optionally substituted $C_{1-6}$ aliphatic), and an optionally substituted $C_{1-3}$ aliphatic. In some embodiments, $R^{YA}$ is halogen or $R^B$ selected from a $C_{1-4}$ aliphatic chain; a 5-6 membered monocyclic heteroaryl ring having 1-4 heteroatoms independently selected from nitrogen, oxygen, and sulfur; a 3-5 membered saturated or partially unsaturated monocyclic carbocyclic ring; and a 3-5 membered saturated or partially unsaturated monocyclic heterocyclic ring having 1-2 heteroatoms independently selected from nitrogen, oxygen, and sulfur; wherein said $R^B$ is substituted by $r^6$ instances of a group independently selected from halogen, —OH, —O—($C_{1-3}$ aliphatic), and $C_{1-3}$ aliphatic, wherein each $C_{1-3}$ aliphatic is optionally substituted with 1-3 halogen. In some embodiments, $R^{YA}$ is halogen or $R^B$ selected from a $C_{1-4}$ aliphatic chain; a 5-6 membered monocyclic heteroaryl ring having 1-4 heteroatoms independently selected from nitrogen, oxygen, and sulfur; a 3-5 membered saturated or partially unsaturated monocyclic carbocyclic ring; and a 3-5 membered saturated or partially unsaturated monocyclic heterocyclic ring having 1-2 heteroatoms independently selected from nitrogen, oxygen, and sulfur; wherein said $R^B$ is substituted by $r^6$ instances of a group independently selected from fluorine, chlorine, —OH, —OCH$_3$, —OCF$_3$, —CH$_3$, —CHF$_2$, and —CF$_3$.

In some embodiments, $R^{YA}$ is halogen or $R^B$ selected from a $C_{1-4}$ aliphatic chain and a 3-5 membered saturated or partially unsaturated monocyclic heterocyclic ring having 1-2 heteroatoms independently selected from nitrogen, oxygen, and sulfur; wherein said $R^B$ is substituted by $r^6$ instances of a group independently selected from halogen, —OH, —O—($C_{1-3}$ aliphatic), and $C_{1-3}$ aliphatic, wherein each $C_{1-3}$ aliphatic is optionally substituted with 1-3 halogen. In some embodiments, $R^{YA}$ is halogen or $R^B$ selected from a $C_{1-4}$ aliphatic chain and a 3-5 membered saturated or partially unsaturated monocyclic heterocyclic ring having 1-2 heteroatoms independently selected from nitrogen and oxygen; wherein said $R^B$ is substituted by $r^6$ instances of a group independently selected from fluorine, chlorine, —OH, —OCH$_3$, —OCF$_3$, —CH$_3$, —CHF$_2$, and —CF$_3$.

In some embodiments, $R^{YA}$ is halogen or a $C_{1-4}$ aliphatic chain substituted by —OH and 0-3 fluorine.

In some embodiments, $R^{YA}$ is halogen, —CN, —OR, —NR$_2$, —C(O)R, —C(O)OR, —C(O)NR$_2$, or —N(R)C(O)R. In some embodiments, $R^A$ is halogen.

In some embodiments, $R^{YA}$ is a $C_{1-6}$ aliphatic chain; phenyl; a 5-6 membered monocyclic heteroaryl ring having 1-4 heteroatoms independently selected from nitrogen, oxygen, and sulfur; a 3-7 membered saturated or partially unsaturated monocyclic carbocyclic ring; or a 3-7 membered saturated or partially unsaturated monocyclic heterocyclic ring having 1-2 heteroatoms independently selected from nitrogen, oxygen, and sulfur; wherein $R^{YA}$ is substituted by $r^6$ instances of $R^{YC}$. In some embodiments, $R^{YA}$ is a $C_{1-6}$ aliphatic chain; a 5-6 membered monocyclic heteroaryl ring having 1-4 heteroatoms independently selected from nitrogen, oxygen, and sulfur; a 3-7 membered saturated or partially unsaturated monocyclic carbocyclic ring; or a 3-7 membered saturated or partially unsaturated monocyclic heterocyclic ring having 1-2 heteroatoms independently selected from nitrogen, oxygen, and sulfur; wherein $R^{YA}$ is substituted by $r^6$ instances of $R^{YC}$.

In some embodiments, $R^{YA}$ is a $C_{1-4}$ aliphatic chain; a 5-6 membered monocyclic heteroaryl ring having 1-4 heteroatoms independently selected from nitrogen, oxygen, and sulfur; a 3-5 membered saturated or partially unsaturated monocyclic carbocyclic ring; or a 3-5 membered saturated or partially unsaturated monocyclic heterocyclic ring having 1-2 heteroatoms independently selected from nitrogen, oxygen, and sulfur; wherein $R^{YA}$ is substituted by $r^6$ instances of $R^{YC}$. In some embodiments, $R^{YA}$ is a $C_{1-4}$ aliphatic chain; a 5-6 membered monocyclic heteroaryl ring having 1-4 heteroatoms independently selected from nitrogen, oxygen, and sulfur; a 3-5 membered saturated or partially unsaturated monocyclic carbocyclic ring; or a 3-5 membered saturated or partially unsaturated monocyclic heterocyclic ring having 1-2 heteroatoms independently selected from nitrogen, oxygen, and sulfur; wherein $R^{YA}$ is substituted by $r^6$ instances of a group independently selected from oxo, halogen, —CN, —NO$_2$, —OR, —SR, —NR$_2$, —S(O)$_2$R, —S(O)$_2$NR$_2$, —S(O)$_2$F, —S(O)R, —S(O)NR$_2$, —S(O)(NR)R, —C(O)R, —C(O)OR, —C(O)NR$_2$, —C(O)N(R)OR, —OC(O)R, —OC(O)NR$_2$, —N(R)C(O)OR, —N(R)C(O)R, —N(R)C (O)NR$_2$, —N(R)C(NR)NR$_2$, —N(R)S(O)$_2$NR$_2$, —N(R)S(O)$_2$R, —P(O)R$_2$, —P(O)(R)OR, —B(OR)$_2$, and optionally substituted C$_{1-6}$ aliphatic.

In some embodiments, R$^{YA}$ is a C$_{1-4}$ aliphatic chain; a 5-6 membered monocyclic heteroaryl ring having 1-4 heteroatoms independently selected from nitrogen, oxygen, and sulfur; a 3-5 membered saturated or partially unsaturated monocyclic carbocyclic ring; or a 3-5 membered saturated or partially unsaturated monocyclic heterocyclic ring having 1-2 heteroatoms independently selected from nitrogen, oxygen, and sulfur; wherein R$^{YA}$ is substituted by r$^6$ instances of a group independently selected from halogen, —CN, —OH, —O-(optionally substituted C$_{1-3}$ aliphatic), and an optionally substituted C$_{1-3}$ aliphatic. In some embodiments, R$^{YA}$ is a C$_{1-4}$ aliphatic chain; a 5-6 membered monocyclic heteroaryl ring having 1-4 heteroatoms independently selected from nitrogen, oxygen, and sulfur; a 3-5 membered saturated or partially unsaturated monocyclic carbocyclic ring; or a 3-5 membered saturated or partially unsaturated monocyclic heterocyclic ring having 1-2 heteroatoms independently selected from nitrogen, oxygen, and sulfur; wherein R$^{YA}$ is substituted by r$^6$ instances of a group independently selected from halogen, —OH, —O—(C$_{1-3}$ aliphatic), and C$_{1-3}$ aliphatic, wherein each C$_{1-3}$ aliphatic is optionally substituted with 1-3 halogen. In some embodiments, R$^{YA}$ is a C$_{1-4}$ aliphatic chain; a 5-6 membered monocyclic heteroaryl ring having 1-4 heteroatoms independently selected from nitrogen, oxygen, and sulfur; a 3-5 membered saturated or partially unsaturated monocyclic carbocyclic ring; or a 3-5 membered saturated or partially unsaturated monocyclic heterocyclic ring having 1-2 heteroatoms independently selected from nitrogen, oxygen, and sulfur; wherein R$^{YA}$ is substituted by r$^6$ instances of a group independently selected from fluorine, chlorine, —OH, —OCH$_3$, —OCF$_3$, —CH$_3$, —CHF$_2$, and —CF$_3$.

In some embodiments, R$^{YA}$ is a C$_{1-4}$ aliphatic chain or a 3-5 membered saturated or partially unsaturated monocyclic heterocyclic ring having 1-2 heteroatoms independently selected from nitrogen, oxygen, and sulfur; wherein R$^{YA}$ is substituted by r$^6$ instances of a group independently selected from halogen, —OH, —O—(C$_{1-3}$ aliphatic), and C$_{1-3}$ aliphatic, wherein each C$_{1-3}$ aliphatic is optionally substituted with 1-3 halogen. In some embodiments, R$^{YA}$ is a C$_{1-4}$ aliphatic chain or a 3-5 membered saturated or partially unsaturated monocyclic heterocyclic ring having 1-2 heteroatoms independently selected from nitrogen and oxygen; wherein R$^{YA}$ is substituted by r$^6$ instances of a group independently selected from fluorine, chlorine, —OH, —OCH$_3$, —OCF$_3$, —CH$_3$, —CHF$_2$, and —CF$_3$. In some embodiments, R$^{YA}$ is a C$_{1-4}$ aliphatic chain substituted by —OH and 0-3 fluorine.

In some embodiments, R$^{YA}$ is oxo, halogen, —CN, —NO$_2$, —OR, —SR, —NR$_2$, —S(O)$_2$R, —S(O)$_2$NR$_2$, —S(O)$_2$F, —S(O)R, —S(O)NR$_2$, —S(O)(NR)R, —C(O)R, —C(O)OR, —C(O)NR$_2$, —C(O)N(R)OR, —OC(O)R, —OC(O)NR$_2$, —N(R)C(O)OR, —N(R)C(O)R, —N(R)C(O)NR$_2$, —N(R)C(NR)NR$_2$, —N(R)S(O)$_2$NR$_2$, —N(R)S(O)$_2$R, —P(O)R$_2$, —P(O)(R)OR, —B(OR)$_2$, or deuterium.

In some embodiments, R$^{YA}$ is oxo, halogen, —CN, —NO$_2$, —OR, —SR, —NR$_2$, —S(O)$_2$R, —S(O)$_2$NR$_2$, —S(O)$_2$F, —S(O)R, —S(O)NR$_2$, —S(O)(NR)R, —C(O)R, —C(O)OR, —C(O)NR$_2$, —C(O)N(R)OR, —OC(O)R, —OC(O)NR$_2$, —N(R)C(O)OR, —N(R)C(O)R, —N(R)C(O)NR$_2$, —N(R)C(NR)NR$_2$, —N(R)S(O)$_2$NR$_2$, —N(R)S(O)$_2$R, —P(O)R$_2$, —P(O)(R)OR, or —B(OR)$_2$.

In some embodiments, R$^{YA}$ is oxo. In some embodiments, R$^{YA}$ is halogen. In some embodiments, R$^{YA}$ is —CN. In some embodiments, R$^{YA}$ is —NO$_2$. In some embodiments, R$^{YA}$ is —OR. In some embodiments, R$^{YA}$ is —SR. In some embodiments, R$^{YA}$ is —NR$_2$. In some embodiments, R$^{YA}$ is —S(O)$_2$R. In some embodiments, R$^{YA}$ is —S(O)$_2$NR$_2$. In some embodiments, R$^{YA}$ is —S(O)$_2$F. In some embodiments, R$^{YA}$ is —S(O)R. In some embodiments, R$^{YA}$ is —S(O)NR$_2$. In some embodiments, R$^{YA}$ is —S(O)(NR)R. In some embodiments, R$^{YA}$ is —C(O)R. In some embodiments, R$^{YA}$ is —C(O)OR. In some embodiments, R$^{YA}$ is —C(O)NR$_2$. In some embodiments, R$^{YA}$ is —C(O)N(R)OR. In some embodiments, R$^{YA}$ is —OC(O)R. In some embodiments, R$^{YA}$ is —OC(O)NR$_2$. In some embodiments, R$^{YA}$ is —N(R)C(O)OR. In some embodiments, R$^{YA}$ is —N(R)C(O)R. In some embodiments, R$^{YA}$ is —N(R)C(O)NR$_2$. In some embodiments, R$^{YA}$ is —N(R)C(NR)NR$_2$. In some embodiments, R$^{YA}$ is —N(R)S(O)$_2$NR$_2$. In some embodiments, R$^{YA}$ is —N(R)S(O)$_2$R. In some embodiments, R$^{YA}$ is —P(O)R$^2$. In some embodiments, R$^{YA}$ is —P(O)(R)OR. In some embodiments, R$^{YA}$ is —B(OR)$_2$. In some embodiments, R$^{YA}$ is deuterium.

In some embodiments, R$^{YA}$ is halogen, —CN, —NO$_2$, —OR, —SR, —NR$_2$, —S(O)$_2$R, —S(O)$_2$NR$_2$, —S(O)$_2$F, —S(O)R, —S(O)NR$_2$, —S(O)(NR)R, —C(O)R, —C(O)OR, —C(O)NR$_2$, —C(O)N(R)OR, —OC(O)R, —OC(O)NR$_2$, —N(R)C(O)OR, —N(R)C(O)R, —N(R)C(O)NR$_2$, —N(R)C(NR)NR$_2$, —N(R)S(O)$_2$NR$_2$, —N(R)S(O)$_2$R, —P(O)R$_2$, —P(O)(R)OR, or —B(OR)$_2$.

In some embodiments, R$^{YA}$ is halogen, —CN, or —NO$_2$. In some embodiments, R$^{YA}$ is —OR, —SR, or —NR$_2$. In some embodiments, R$^{YA}$ is —S(O)$_2$R, —S(O)$_2$NR$_2$, —S(O)$_2$F, —S(O)R, —S(O)NR$_2$, or —S(O)(NR)R. In some embodiments, R$^{YA}$ is —C(O)R, —C(O)OR, —C(O)NR$_2$, or —C(O)N(R)OR. In some embodiments, R$^{YA}$ is —OC(O)R or —OC(O)NR$_2$. In some embodiments, R$^{YA}$ is —N(R)C(O)OR, —N(R)C(O)R, —N(R)C(O)NR$_2$, —N(R)C(NR)NR$_2$, —N(R)S(O)$_2$NR$_2$, or —N(R)S(O)$_2$R. In some embodiments, R$^{YA}$ is —P(O)R$_2$ or —P(O)(R)OR.

In some embodiments, R$^{YA}$ is —OR, —OC(O)R, or —OC(O)NR$_2$. In some embodiments, R$^{YA}$ is —SR, —S(O)$_2$R, —S(O)$_2$NR$_2$, —S(O)$_2$F, —S(O)R, —S(O)NR$_2$, or —S(O)(NR)R. In some embodiments, R$^{YA}$ is —NR$_2$, —N(R)C(O)OR, —N(R)C(O)R, —N(R)C(O)NR$_2$, —N(R)C(NR)NR$_2$, —N(R)S(O)$_2$NR$_2$, or —N(R)S(O)$_2$R.

In some embodiments, R$^{YA}$ is —S(O)$_2$R, —S(O)$_2$NR$_2$, or —S(O)$_2$F. In some embodiments, R$^{YA}$ is —S(O)R, —S(O)NR$_2$, or —S(O)(NR)R. In some embodiments, R$^{YA}$ is —SR, —S(O)$_2$R, or —S(O)R. In some embodiments, R$^{Y*}$ is —S(O)$_2$NR$_2$, —S(O)NR$_2$, or —S(O)(NR)R.

In some embodiments, R$^{YA}$ is —S(O)$_2$NR$_2$ or —S(O)NR$_2$. In some embodiments, R$^{YA}$ is —SR, —S(O)$_2$R, —S(O)$_2$NR$_2$, or —S(O)R.

In some embodiments, R$^{YA}$ is —N(R)C(O)OR, —N(R)C(O)R, or —N(R)C(O)NR$_2$. In some embodiments, R$^{YA}$ is —N(R)S(O)$_2$NR$_2$ or —N(R)S(O)$_2$R. In some embodiments, R$^{YA}$ is —N(R)C(O)OR or —N(R)C(O)R. In some embodiments, R$^{YA}$ is —N(R)C(O)NR$_2$ or —N(R)S(O)$_2$NR$_2$. In some embodiments, R$^{YA}$ is —N(R)C(O)OR, —N(R)C(O)R, or —N(R)S(O)$_2$R.

In some embodiments, R$^{YA}$ is —NR$_2$, —N(R)C(O)OR, —N(R)C(O)R, or —N(R)C(O)NR$_2$. In some embodiments, R$^{YA}$ is —NR$_2$, —N(R)C(O)OR, or —N(R)C(O)R. In some embodiments, R$^{YA}$ is —NR$_2$, —N(R)C(O)OR, —N(R)C(O)R, or —N(R)S(O)$_2$R.

In some embodiments, R$^{YA}$ is a C$_{1-6}$ aliphatic chain; phenyl; naphthyl; a 5-6 membered monocyclic heteroaryl ring having 1-4 heteroatoms independently selected from nitrogen, oxygen, and sulfur; an 8-10 membered bicyclic heteroaryl ring having 1-4 heteroatoms independently selected from nitrogen, oxygen, and sulfur; a 3-7 membered saturated or partially unsaturated monocyclic carbocyclic ring; a 5-12 membered saturated or partially unsaturated bicyclic carbocyclic ring; a 3-7 membered saturated or partially unsaturated monocyclic heterocyclic ring having 1-2 heteroatoms independently selected from nitrogen, oxygen, and sulfur; or a 7-12 membered saturated or partially unsaturated bicyclic heterocyclic ring having 1-4 heteroatoms independently selected from nitrogen, oxygen, and sulfur; each of which is substituted by $r^6$ instances of $R^{YC}$.

In some embodiments, $R^{YA}$ is a $C_{1-6}$ aliphatic chain substituted by $r^6$ instances of $R^{YC}$.

In some embodiments, $R^{YA}$ is phenyl substituted by $r^6$ instances of $R^{YC}$. In some embodiments, $R^{YA}$ is naphthyl substituted by $r^6$ instances of $R^{YC}$. In some embodiments, $R^{YA}$ is a 5-6 membered monocyclic heteroaryl ring having 1-4 heteroatoms independently selected from nitrogen, oxygen, and sulfur; wherein said ring is substituted by $r^6$ instances of $R^{YC}$. In some embodiments, $R^{YA}$ is an 8-10 membered bicyclic heteroaryl ring having 1-4 heteroatoms independently selected from nitrogen, oxygen, and sulfur; wherein said ring is substituted by $r^6$ instances of $R^{YC}$. In some embodiments, $R^{YA}$ is a 3-7 membered saturated or partially unsaturated monocyclic carbocyclic ring substituted by $r^6$ instances of $R^{YC}$. In some embodiments, $R^{YA}$ is a 5-12 membered saturated or partially unsaturated bicyclic carbocyclic ring substituted by $r^6$ instances of $R^{YC}$. In some embodiments, $R^{YA}$ is a 3-7 membered saturated or partially unsaturated monocyclic heterocyclic ring having 1-2 heteroatoms independently selected from nitrogen, oxygen, and sulfur; wherein said ring is substituted by $r^6$ instances of $R^{YC}$. In some embodiments, $R^{YA}$ is a 7-12 membered saturated or partially unsaturated bicyclic heterocyclic ring having 1-4 heteroatoms independently selected from nitrogen, oxygen, and sulfur; wherein said ring is substituted by $r^6$ instances of $R^{YC}$.

In some embodiments, $R^{YA}$ is phenyl; naphthyl; a 5-6 membered monocyclic heteroaryl ring having 1-4 heteroatoms independently selected from nitrogen, oxygen, and sulfur; an 8-10 membered bicyclic heteroaryl ring having 1-4 heteroatoms independently selected from nitrogen, oxygen, and sulfur; a 3-7 membered saturated or partially unsaturated monocyclic carbocyclic ring; a 5-12 membered saturated or partially unsaturated bicyclic carbocyclic ring; a 3-7 membered saturated or partially unsaturated monocyclic heterocyclic ring having 1-2 heteroatoms independently selected from nitrogen, oxygen, and sulfur; or a 7-12 membered saturated or partially unsaturated bicyclic heterocyclic ring having 1-4 heteroatoms independently selected from nitrogen, oxygen, and sulfur; each of which is substituted by $r^6$ instances of $R^{YC}$.

In some embodiments, $R^{YA}$ is phenyl; naphthyl; a 5-6 membered monocyclic heteroaryl ring having 1-4 heteroatoms independently selected from nitrogen, oxygen, and sulfur; or an 8-10 membered bicyclic heteroaryl ring having 1-4 heteroatoms independently selected from nitrogen, oxygen, and sulfur; each of which is substituted by $r^6$ instances of $R^{YC}$. In some embodiments, $R^{YA}$ is a 3-7 membered saturated or partially unsaturated monocyclic carbocyclic ring; a 5-12 membered saturated or partially unsaturated bicyclic carbocyclic ring; a 3-7 membered saturated or partially unsaturated monocyclic heterocyclic ring having 1-2 heteroatoms independently selected from nitrogen, oxygen, and sulfur; or a 7-12 membered saturated or partially unsaturated bicyclic heterocyclic ring having 1-4 heteroatoms independently selected from nitrogen, oxygen, and sulfur; each of which is substituted by $r^6$ instances of $R^{YC}$.

In some embodiments, $R^{YA}$ is phenyl; naphthyl; a 3-7 membered saturated or partially unsaturated monocyclic carbocyclic ring; or a 5-12 membered saturated or partially unsaturated bicyclic carbocyclic ring; each of which is substituted by $r^6$ instances of $R^{YC}$. In some embodiments, $R^{YA}$ is a 5-6 membered monocyclic heteroaryl ring having 1-4 heteroatoms independently selected from nitrogen, oxygen, and sulfur; an 8-10 membered bicyclic heteroaryl ring having 1-4 heteroatoms independently selected from nitrogen, oxygen, and sulfur; a 3-7 membered saturated or partially unsaturated monocyclic heterocyclic ring having 1-2 heteroatoms independently selected from nitrogen, oxygen, and sulfur; or a 7-12 membered saturated or partially unsaturated bicyclic heterocyclic ring having 1-4 heteroatoms independently selected from nitrogen, oxygen, and sulfur; each of which is substituted by $r^6$ instances of $R^{YC}$.

In some embodiments, $R^{YA}$ is phenyl; a 5-6 membered monocyclic heteroaryl ring having 1-4 heteroatoms independently selected from nitrogen, oxygen, and sulfur; a 3-7 membered saturated or partially unsaturated monocyclic carbocyclic ring; or a 3-7 membered saturated or partially unsaturated monocyclic heterocyclic ring having 1-2 heteroatoms independently selected from nitrogen, oxygen, and sulfur; each of which is substituted by $r^6$ instances of $R^{YC}$. In some embodiments, $R^{YA}$ is naphthyl; an 8-10 membered bicyclic heteroaryl ring having 1-4 heteroatoms independently selected from nitrogen, oxygen, and sulfur; a 5-12 membered saturated or partially unsaturated bicyclic carbocyclic ring; or a 7-12 membered saturated or partially unsaturated bicyclic heterocyclic ring having 1-4 heteroatoms independently selected from nitrogen, oxygen, and sulfur; each of which is substituted by $r^6$ instances of $R^{YC}$.

In some embodiments, $R^{YA}$ is phenyl or naphthyl; each of which is substituted by $r^6$ instances of $R^{YC}$. In some embodiments, $R^{YA}$ is a 5-6 membered monocyclic heteroaryl ring having 1-4 heteroatoms independently selected from nitrogen, oxygen, and sulfur; or an 8-10 membered bicyclic heteroaryl ring having 1-4 heteroatoms independently selected from nitrogen, oxygen, and sulfur; each of which is substituted by $r^6$ instances of $R^{YC}$. In some embodiments, $R^{YA}$ is a 3-7 membered saturated or partially unsaturated monocyclic carbocyclic ring or a 5-12 membered saturated or partially unsaturated bicyclic carbocyclic ring; each of which is substituted by $r^6$ instances of $R^{YC}$. In some embodiments, $R^{YA}$ is a 3-7 membered saturated or partially unsaturated monocyclic heterocyclic ring having 1-2 heteroatoms independently selected from nitrogen, oxygen, and sulfur; or a 7-12 membered saturated or partially unsaturated bicyclic heterocyclic ring having 1-4 heteroatoms independently selected from nitrogen, oxygen, and sulfur; each of which is substituted by $r^6$ instances of $R^{YC}$.

In some embodiments, $R^{YA}$ is phenyl or a 5-6 membered monocyclic heteroaryl ring having 1-4 heteroatoms independently selected from nitrogen, oxygen, and sulfur; each of which is substituted by $r^6$ instances of $R^{YC}$. In some embodiments, $R^{YA}$ is a 3-7 membered saturated or partially unsaturated monocyclic carbocyclic ring or a 3-7 membered saturated or partially unsaturated monocyclic heterocyclic ring having 1-2 heteroatoms independently selected from nitrogen, oxygen, and sulfur; each of which is substituted by $r^6$ instances of $R^{YC}$. In some embodiments, $R^{YA}$ is naphthyl or an 8-10 membered bicyclic heteroaryl ring having 1-4 heteroatoms independently selected from nitrogen, oxygen, and sulfur; each of which is substituted by $r^6$ instances of $R^{YC}$. In some embodiments, $R^{YA}$ is a 5-12 membered saturated or partially unsaturated bicyclic carbocyclic ring or a 7-12 membered saturated or partially unsaturated bicyclic heterocyclic ring having 1-4 heteroatoms independently selected from nitrogen, oxygen, and sulfur; each of which is substituted by $r^6$ instances of $R^{YC}$.

In some embodiments, $R^{YA}$ is phenyl or a 3-7 membered saturated or partially unsaturated monocyclic carbocyclic ring; each of which is substituted by $r^6$ instances of $R^{YC}$. In some embodiments, $R^A$ is naphthyl or a 5-12 membered saturated or partially unsaturated bicyclic carbocyclic ring; each of which is substituted by $r^6$ instances of $R^{YC}$. In some embodiments, $R^{YA}$ is a 5-6 membered monocyclic heteroaryl ring having 1-4 heteroatoms independently selected from nitrogen, oxygen, and sulfur; or a 3-7 membered saturated or partially unsaturated monocyclic heterocyclic ring having 1-2 heteroatoms independently selected from nitrogen, oxygen, and sulfur; each of which is substituted by $r^6$ instances of $R^{YC}$. In some embodiments, $R^{YA}$ is an 8-10 membered bicyclic heteroaryl ring having 1-4 heteroatoms independently selected from nitrogen, oxygen, and sulfur; or a 7-12 membered saturated or partially unsaturated bicyclic heterocyclic ring having 1-4 heteroatoms independently selected from nitrogen, oxygen, and sulfur; each of which is substituted by $r^6$ instances of $R^{YC}$.

In some embodiments, $R^{YA}$ is a $C_{1-6}$ aliphatic chain; a 3-7 membered saturated or partially unsaturated monocyclic carbocyclic ring; a 5-12 membered saturated or partially unsaturated bicyclic carbocyclic ring; a 3-7 membered saturated or partially unsaturated monocyclic heterocyclic ring having 1-2 heteroatoms independently selected from nitrogen, oxygen, and sulfur; or a 7-12 membered saturated or partially unsaturated bicyclic heterocyclic ring having 1-4 heteroatoms independently selected from nitrogen, oxygen, and sulfur; each of which is substituted by $r^6$ instances of $R^{YC}$. In some embodiments, $R^{YA}$ is a $C_{1-6}$ aliphatic chain; phenyl; naphthyl; a 3-7 membered saturated or partially unsaturated monocyclic carbocyclic ring; or a 5-12 membered saturated or partially unsaturated bicyclic carbocyclic ring; each of which is substituted by $r^6$ instances of $R^{YC}$. In some embodiments, $R^{YA}$ is a $C_{1-6}$ aliphatic chain; phenyl; a 5-6 membered monocyclic heteroaryl ring having 1-4 heteroatoms independently selected from nitrogen, oxygen, and sulfur; a 3-7 membered saturated or partially unsaturated monocyclic carbocyclic ring; or a 3-7 membered saturated or partially unsaturated monocyclic heterocyclic ring having 1-2 heteroatoms independently selected from nitrogen, oxygen, and sulfur; each of which is substituted by $r^6$ instances of $R^{YC}$.

In some embodiments, $R^{YA}$ is a $C_{1-6}$ aliphatic chain, a 3-7 membered saturated or partially unsaturated monocyclic carbocyclic ring, or a 5-12 membered saturated or partially unsaturated bicyclic carbocyclic ring; each of which is substituted by $r^6$ instances of $R^{YC}$. In some embodiments, $R^{YA}$ is a $C_{1-6}$ aliphatic chain, a 3-7 membered saturated or partially unsaturated monocyclic carbocyclic ring, or a 3-7 membered saturated or partially unsaturated monocyclic heterocyclic ring having 1-2 heteroatoms independently selected from nitrogen, oxygen, and sulfur; each of which is substituted by $r^6$ instances of $R^{YC}$. In some embodiments, $R^{YA}$ is a $C_{1-6}$ aliphatic chain, phenyl, or a 3-7 membered saturated or partially unsaturated monocyclic carbocyclic ring; each of which is substituted by $r^6$ instances of $R^{YC}$.

In some embodiments, $R^{YA}$ is an 8-10 membered bicyclic heteroaryl ring having 1, 2, or 3 heteroatoms independently selected from nitrogen, oxygen, and sulfur; wherein said ring is substituted by $r^6$ instances of $R^{YC}$. In some embodiments, $R^{YA}$ is an 8-10 membered bicyclic heteroaryl ring having 2 or 3 heteroatoms independently selected from nitrogen, oxygen, and sulfur; wherein said ring is substituted by $r^6$ instances of $R^Y$. In some embodiments, $R^{YA}$ is an 8-10 membered bicyclic heteroaryl ring having 1, 2, or 3 nitrogen atoms; wherein said ring is substituted by $r^6$ instances of $R^{YC}$. In some embodiments, $R^{YA}$ is an 8-10 membered bicyclic heteroaryl ring having 2 or 3 nitrogen atoms; wherein said ring is substituted by $r^6$ instances of $R^{YC}$.

In certain embodiments, $R^{YA}$ is imidazo[1,2-a]pyrazinyl, [1,2,4]triazolo[1,5-a]pyridinyl, or pyrazolo[1,5-a]pyrimidinyl; each of which is substituted by $r^6$ instances of $R^{YC}$. In certain embodiments, $R^{YA}$ is imidazo[1,2-a]pyrazinyl substituted by $r^6$ instances of $R^{YC}$. In certain embodiments, $R^{YA}$ is [1,2,4]triazolo[1,5-a]pyridinyl substituted by $r^6$ instances of $R^{YC}$. In certain embodiments, $R^{YA}$ is pyrazolo[1,5-a]pyrimidinyl substituted by $r^6$ instances of $R^{YC}$.

In certain embodiments, $R^{YA}$ is imidazo[1,2-a]pyrazin-6-yl, [1,2,4]triazolo[1,5-a]pyridin-6-yl, or pyrazolo[1,5-a]pyrimidin-5-yl; each of which is substituted by $r^6$ instances of $R^{YC}$. In certain embodiments, $R^{YA}$ is imidazo[1,2-a]pyrazin-6-yl substituted by $r^6$ instances of $R^{YC}$. In certain embodiments, $R^{YA}$ is [1,2,4]triazolo[1,5-a]pyridin-6-yl substituted by $r^6$ instances of $R^{YC}$. In certain embodiments, $R^{YA}$ is pyrazolo[1,5-a]pyrimidin-5-yl substituted by $r^6$ instances of $R^{YC}$.

In certain embodiments, $R^{YA}$ is imidazo[1,2-a]pyrazin-6-yl, [1,2,4]triazolo[1,5-a]pyridin-6-yl, or pyrazolo[1,5-a]pyrimidin-5-yl. In certain embodiments, $R^{YA}$ is imidazo[1,2-a]pyrazin-6-yl. In certain embodiments, $R^{YA}$ is [1,2,4]triazolo[1,5-a]pyridin-6-yl. In certain embodiments, $R^A$ is pyrazolo[1,5-a]pyrimidin-5-yl.

In some embodiments, $R^{YA}$ is a 5-6 membered monocyclic heteroaryl ring having 1, 2, or 3 heteroatoms independently selected from nitrogen, oxygen, and sulfur; or a 5-7 membered saturated or partially unsaturated monocyclic heterocyclic ring having 1 or 2 heteroatoms independently selected from nitrogen, oxygen, and sulfur; each of which is substituted by $r^6$ instances of $R^{YC}$.

In some embodiments, $R^{YA}$ is a 5-6 membered monocyclic heteroaryl ring having 1, 2, or 3 heteroatoms independently selected from nitrogen, oxygen, and sulfur; wherein said ring is substituted by $r^6$ instances of $R^{YC}$. In some embodiments, $R^{YA}$ is a 5-membered monocyclic heteroaryl ring having 1, 2, or 3 heteroatoms independently selected from nitrogen, oxygen, and sulfur; wherein said ring is substituted by $r^6$ instances of $R^{YC}$. In some embodiments, $R^{YA}$ is a 5-membered monocyclic heteroaryl ring having 1 or 2 heteroatoms independently selected from nitrogen and oxygen; wherein said ring is substituted by $r^6$ instances of $R^{YC}$. In some embodiments, $R^{YA}$ is a 6-membered monocyclic heteroaryl ring having 1 or 2 nitrogen atoms; wherein said ring is substituted by $r^6$ instances of $R^{YC}$.

In certain embodiments, $R^{YA}$ is pyrazolyl or imidazolyl, each of which is substituted by $r^6$ instances of $R^{YC}$. In certain embodiments, $R^{YA}$ is pyrazolyl substituted by $r^6$ instances of $R^{YC}$. In certain embodiments, $R^{YA}$ is imidazolyl substituted by $r^6$ instances of $R^{YC}$. In certain embodiments, $R^YA$ is pyrazol-4-yl or imidazol-4-yl, each of which is substituted by $r^6$ instances of $R^{YC}$. In certain embodiments, $R^{YA}$ is pyrazol-4-yl substituted by $r^6$ instances of $R^{YC}$. In certain embodiments, $R^{YA}$ is imidazol-4-yl substituted by $r^6$ instances of $R^{YC}$.

In some embodiments, $R^{YA}$ is a 3-7 membered partially unsaturated monocyclic heterocyclic ring having 1 or 2 heteroatoms independently selected from nitrogen, oxygen, and sulfur; wherein said ring is substituted by $r^6$ instances of $R^{YC}$. In some embodiments, $R^{YA}$ is a 3-7 membered saturated monocyclic heterocyclic ring having 1 or 2 heteroatoms independently selected from nitrogen, oxygen, and sulfur; wherein said ring is substituted by $r^6$ instances of $R^{YC}$.

In some embodiments, $R^{YA}$ is a 5-7 membered saturated or partially unsaturated monocyclic heterocyclic ring having 1 or 2 heteroatoms independently selected from nitrogen, oxygen, and sulfur; wherein said ring is substituted by $r^6$ instances of RC. In some embodiments, $R^{YA}$ is a 5-7 membered saturated monocyclic heterocyclic ring having 1 or 2 heteroatoms independently selected from nitrogen, oxygen, and sulfur; wherein said ring is substituted by $r^6$ instances of $R^{YC}$. In some embodiments, $R^{YA}$ is a 5-7 membered partially unsaturated monocyclic heterocyclic ring having 1 or 2 heteroatoms independently selected from nitrogen, oxygen, and sulfur; wherein said ring is substituted by $r^6$ instances of $R^{YC}$.

In some embodiments, $R^{YA}$ is a 6-membered saturated or partially unsaturated monocyclic heterocyclic ring having 1 or 2 heteroatoms independently selected from nitrogen and oxygen; wherein said ring is substituted by $r^6$ instances of $R^{YC}$. In some embodiments, $R^{YA}$ is a 6-membered saturated monocyclic heterocyclic ring having 1 or 2 heteroatoms independently selected from nitrogen and oxygen; wherein said ring is substituted by $r^6$ instances of $R^{YC}$. In some embodiments, $R^{YA}$ is a 6-membered partially unsaturated monocyclic heterocyclic ring having 1 or 2 heteroatoms independently selected from nitrogen and oxygen; wherein said ring is substituted by $r^6$ instances of $R^{YC}$. In some embodiments, $R^{YA}$ is pyridin-2(1H)-onyl substituted by 0, 1, 2, or 3 instances of $R^{YC}$. In some embodiments, $R^{YA}$ is pyridin-2(1H)-on-5-yl substituted by 0, 1, 2, or 3 instances of $R^Y$.

In some embodiments, $R^{YA}$ is

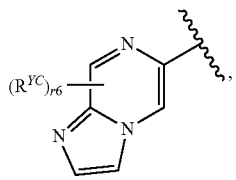 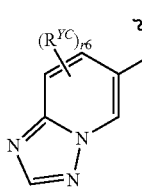 or

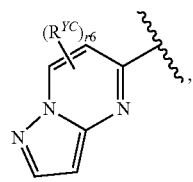

wherein $R^{YC}$ and $r^6$ are as defined in the embodiments and classes and subclasses herein. In some embodiments, $R^{YA}$ is

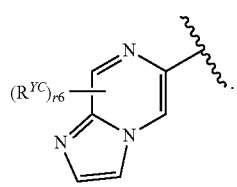

In some embodiments, $R^{YA}$ is

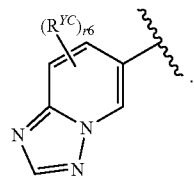

In some embodiments, $R^{YA}$ is

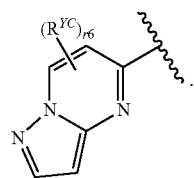

In some embodiments, $R^{YA}$ is

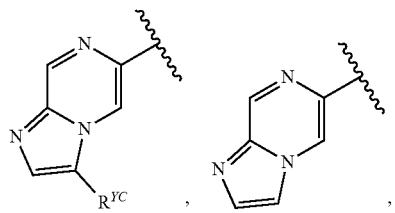

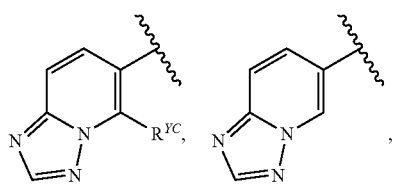

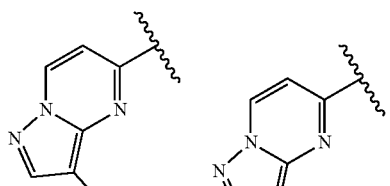

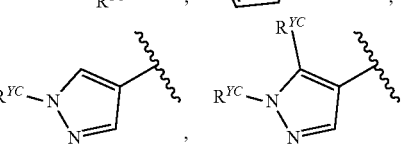

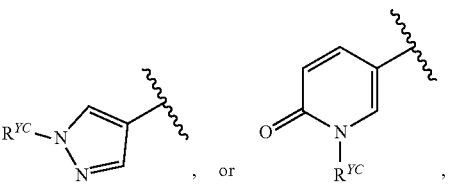 or 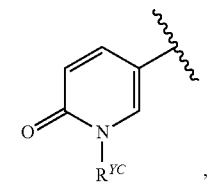

wherein $R^{YC}$ is as defined in the embodiments and classes and subclasses herein. In some embodiments, $R^{YA}$ is

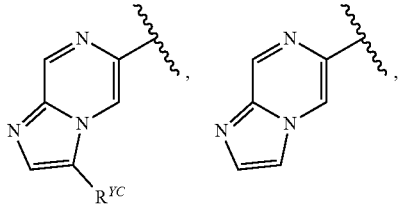

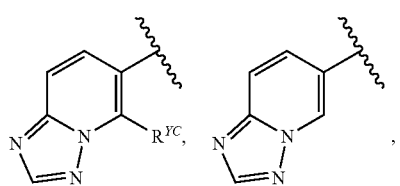

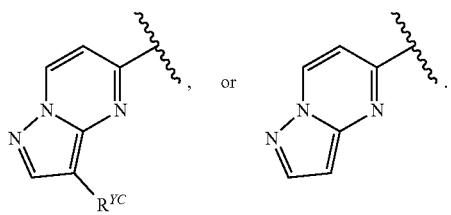

In some embodiments, $R^{YA}$ is

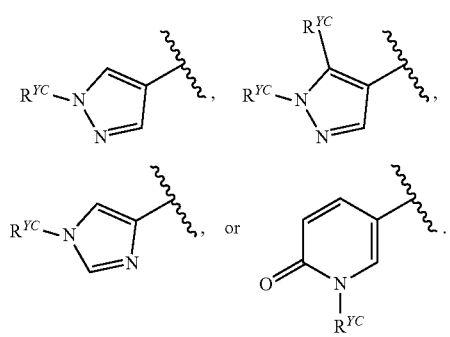

In some embodiments, $R^{YA}$ is

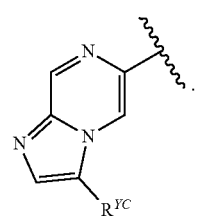

In some embodiments, $R^{YA}$ is

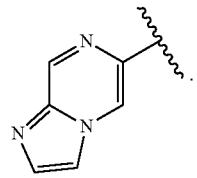

In some embodiments, $R^{YA}$ is

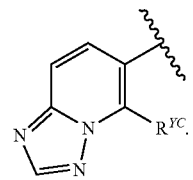

In some embodiments, $R^{YA}$ is

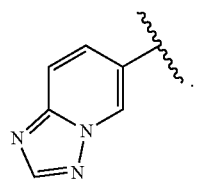 [SMILES: *c1ccc2ncnn2c1]

In some embodiments, $R^{YA}$ is

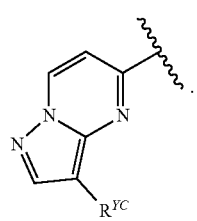

In some embodiments, $R^{YA}$ is

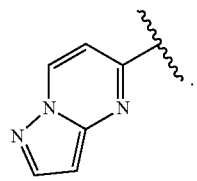 [SMILES: *c1ccn2nccc2n1]

In some embodiments, $R^{YA}$ is

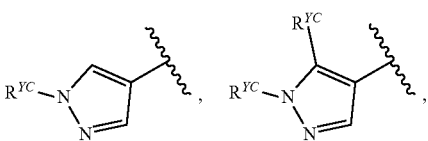

In some embodiments, $R^{YA}$ is

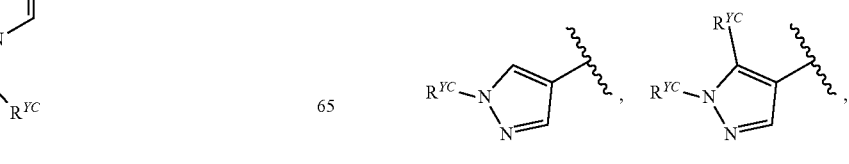

-continued

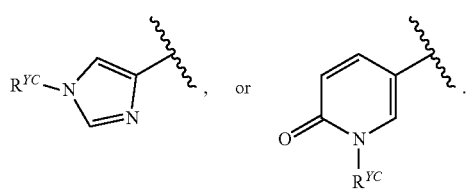

In some embodiments, $R^{YA}$ is

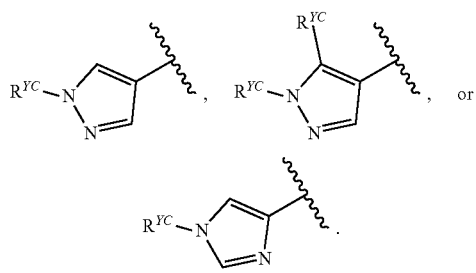

In some embodiments, $R^{YA}$ is

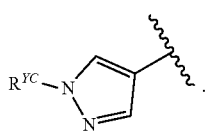

In some embodiments, $R^{YA}$ is

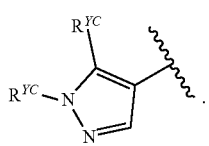

In some embodiments, $R^{YA}$ is

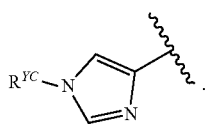

In some embodiments, $R^{YA}$ is

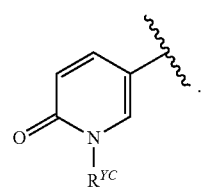

In some embodiments, $R^{YA}$ is selected from the groups depicted in the compounds in Table 1.

As defined generally above, $R^{ZA}$ is $R^A$ or $R^B$ substituted by $r^7$ instances of $R^{ZC}$. In some embodiments, $R^{ZA}$ is $R^A$. In some embodiments, $R^{ZA}$ is $R^B$ substituted by $r^7$ instances of $R^{ZC}$.

In some embodiments, $R^{ZA}$ is oxo, halogen, —CN, —NO$_2$, —OR, —SR, —NR$_2$, —S(O)$_2$R, —S(O)$_2$NR$_2$, —S(O)$_2$F, —S(O)R, —S(O)NR$_2$, —S(O)(NR)R, —C(O)R, —C(O)OR, —C(O)NR$_2$, —C(O)N(R)OR, —OC(O)R, —OC(O)NR$_2$, —N(R)C(O)OR, —N(R)C(O)R, —N(R)C(O)NR$_2$, —N(R)C(NR)NR$_2$, —N(R)S(O)$_2$NR$_2$, —N(R)S(O)$_2$R, —P(O)R$_2$, —P(O)(R)OR, —B(OR)$_2$, or $R^B$ selected from a $C_{1-6}$ aliphatic chain; phenyl; a 5-6 membered monocyclic heteroaryl ring having 1-4 heteroatoms independently selected from nitrogen, oxygen, and sulfur; a 3-7 membered saturated or partially unsaturated monocyclic carbocyclic ring; and a 3-7 membered saturated or partially unsaturated monocyclic heterocyclic ring having 1-2 heteroatoms independently selected from nitrogen, oxygen, and sulfur; wherein said $R^B$ is substituted by $r^1$ instances of $R^{ZC}$.

In some embodiments, $R^{ZA}$ is halogen, —CN, —OR, —NR$_2$, —C(O)R, —C(O)OR, —C(O)NR$_2$, —N(R)C(O)R, or $R^B$ selected from a $C_{1-6}$ aliphatic chain; a 3-7 membered saturated or partially unsaturated monocyclic carbocyclic ring; and a 3-7 membered saturated or partially unsaturated monocyclic heterocyclic ring having 1-2 heteroatoms independently selected from nitrogen, oxygen, and sulfur; wherein said $R^B$ is substituted by r instances of $R^{ZC}$. In some embodiments, $R^{ZA}$ is halogen or $R^B$ selected from a $C_{1-4}$ aliphatic chain; a 3-5 membered saturated or partially unsaturated monocyclic carbocyclic ring; and a 3-5 membered saturated or partially unsaturated monocyclic heterocyclic ring having 1-2 heteroatoms independently selected from nitrogen, oxygen, and sulfur; wherein said $R^B$ is substituted by $r^7$ instances of a group independently selected from oxo, halogen, —CN, —NO$_2$, —OR, —SR, —NR$_2$, —S(O)$_2$R, —S(O)$_2$NR$_2$, —S(O)$_2$F, —S(O)R, —S(O)NR$_2$, —S(O)(NR)R, —C(O)R, —C(O)OR, —C(O)NR$_2$, —C(O)N(R)OR, —OC(O)R, —OC(O)NR$_2$, —N(R)C(O)OR, —N(R)C(O)R, —N(R)C(O)NR$_2$, —N(R)C(NR)NR$_2$, —N(R)S(O)$_2$NR$_2$, —N(R)S(O)$_2$R, —P(O)R$_2$, —P(O)(R)OR, or —B(OR)$_2$, and optionally substituted $C_{1-6}$ aliphatic.

In some embodiments, $R^{ZA}$ is halogen or $R^B$ selected from a $C_{1-4}$ aliphatic chain; a 3-5 membered saturated or partially unsaturated monocyclic carbocyclic ring; and a 3-5 membered saturated or partially unsaturated monocyclic heterocyclic ring having 1-2 heteroatoms independently selected from nitrogen, oxygen, and sulfur; wherein said $R^B$ is substituted by $r^7$ instances of a group independently selected from halogen, —OH, —O—($C_{1-3}$ aliphatic), and $C_{1-3}$ aliphatic, wherein each $C_{1-3}$ aliphatic is optionally substituted with 1-3 halogen. In some embodiments, $R^{ZA}$ is halogen or $R^B$ selected from a $C_{1-4}$ aliphatic chain; a 3-5 membered saturated or partially unsaturated monocyclic carbocyclic ring; and a 3-5 membered saturated or partially unsaturated monocyclic heterocyclic ring having 1-2 heteroatoms independently selected from nitrogen, oxygen, and sulfur; wherein said $R^B$ is substituted by $r^7$ instances of a group independently selected from fluorine, chlorine, —OH, —OCH$_3$, —OCF$_3$, —CH$_3$, —CHF$_2$, and —CF$_3$.

In some embodiments, $R^{ZA}$ is halogen, —CN, —OR, —NR$_2$, —C(O)R, —C(O)OR, —C(O)NR$_2$, or —N(R)C(O)R. In some embodiments, $R^{ZA}$ is halogen.

In some embodiments, $R^{ZA}$ is a $C_{1-6}$ aliphatic chain; a 3-7 membered saturated or partially unsaturated monocyclic carbocyclic ring; or a 3-7 membered saturated or partially unsaturated monocyclic heterocyclic ring having 1-2 heteroatoms independently selected from nitrogen, oxygen, and sulfur; wherein $R^{ZA}$ is substituted by r instances of $R^{ZC}$. In some embodiments, $R^{ZA}$ is a $C_{1-4}$ aliphatic chain; a 3-5 membered saturated or partially unsaturated monocyclic carbocyclic ring; or a 3-5 membered saturated or partially unsaturated monocyclic heterocyclic ring having 1-2 heteroatoms independently selected from nitrogen, oxygen, and sulfur; wherein $R^{ZA}$ is substituted by $r^1$ instances of a group independently selected from oxo, halogen, —CN, —NO$_2$, —OR, —SR, —NR$_2$, —S(O)$_2$R, —S(O)$_2$NR$_2$, —S(O)$_2$F, —S(O)R, —S(O)NR$_2$, —S(O)(NR)R, —C(O)R, —C(O)OR, —C(O)NR$_2$, —C(O)N(R)OR, —OC(O)R, —OC(O)NR$_2$, —N(R)C(O)OR, —N(R)C(O)R, —N(R)C(O)NR$_2$, —N(R)C(NR)NR$_2$, —N(R)S(O)$_2$NR$_2$, —N(R)S(O)$_2$R, —P(O)R$_2$, —P(O)(R)OR, —B(OR)$_2$, and optionally substituted C$_{1-6}$ aliphatic.

In some embodiments, $R^{ZA}$ is a C$_{1-4}$ aliphatic chain; a 3-5 membered saturated or partially unsaturated monocyclic carbocyclic ring; or a 3-5 membered saturated or partially unsaturated monocyclic heterocyclic ring having 1-2 heteroatoms independently selected from nitrogen, oxygen, and sulfur; wherein $R^{ZA}$ is substituted by $r^7$ instances of a group independently selected from halogen, —OH, —O—(C$_{1-3}$ aliphatic), and C$_{1-3}$ aliphatic, wherein each C$_{1-3}$ aliphatic is optionally substituted with 1-3 halogen. In some embodiments, $R^{ZA}$ is a C$_{1-4}$ aliphatic chain; a 3-5 membered saturated or partially unsaturated monocyclic carbocyclic ring; or a 3-5 membered saturated or partially unsaturated monocyclic heterocyclic ring having 1-2 heteroatoms independently selected from nitrogen, oxygen, and sulfur; wherein $R^{ZA}$ is substituted by $r^7$ instances of a group independently selected from fluorine, chlorine, —OH, —OCH$_3$, —OCF$_3$, —CH$_3$, —CHF$_2$, and —CF$_3$.

In some embodiments, $R^{ZA}$ is oxo, halogen, —CN, —NO$_2$, —OR, —SR, —NR$_2$, —S(O)$_2$R, —S(O)$_2$NR$_2$, —S(O)$_2$F, —S(O)R, —S(O)NR$_2$, —S(O)(NR)R, —C(O)R, —C(O)OR, —C(O)NR$_2$, —C(O)N(R)OR, —OC(O)R, —OC(O)NR$_2$, —N(R)C(O)OR, —N(R)C(O)R, —N(R)C(O)NR$_2$, —N(R)C(NR)NR$_2$, —N(R)S(O)$_2$NR$_2$, —N(R)S(O)$_2$R, —P(O)R$_2$, —P(O)(R)OR, —B(OR)$_2$, or deuterium.

In some embodiments, $R^{ZA}$ is oxo, halogen, —CN, —NO$_2$, —OR, —SR, —NR$_2$, —S(O)$_2$R, —S(O)$_2$NR$_2$, —S(O)$_2$F, —S(O)R, —S(O)NR$_2$, —S(O)(NR)R, —C(O)R, —C(O)OR, —C(O)NR$_2$, —C(O)N(R)OR, —OC(O)R, —OC(O)NR$_2$, —N(R)C(O)OR, —N(R)C(O)R, —N(R)C(O)NR$_2$, —N(R)C(NR)NR$_2$, —N(R)S(O)$_2$NR$_2$, —N(R)S(O)$_2$R, —P(O)R$_2$, —P(O)(R)OR, or —B(OR)$_2$.

In some embodiments, $R^{ZA}$ is oxo. In some embodiments, $R^{ZA}$ is halogen. In some embodiments, $R^{ZA}$ is —CN. In some embodiments, $R^{ZA}$ is —NO$_2$. In some embodiments, $R^{ZA}$ is —OR. In some embodiments, $R^{ZA}$ is —SR. In some embodiments, $R^{ZA}$ is —NR$_2$. In some embodiments, $R^{ZA}$ is —S(O)$_2$R. In some embodiments, $R^{ZA}$ is —S(O)$_2$NR$_2$. In some embodiments, $R^{ZA}$ is —S(O)$_2$F. In some embodiments, $R^{ZA}$ is —S(O)R. In some embodiments, $R^{ZA}$ is —S(O)NR$_2$. In some embodiments, $R^{ZA}$ is —S(O)(NR)R. In some embodiments, $R^{ZA}$ is —C(O)R. In some embodiments, $R^{ZA}$ is —C(O)OR. In some embodiments, $R^{ZA}$ is —C(O)NR$_2$. In some embodiments, $R^{ZA}$ is —C(O)N(R)OR. In some embodiments, $R^{ZA}$ is —OC(O)R. In some embodiments, $R^{ZA}$ is —OC(O)NR$_2$. In some embodiments, $R^{ZA}$ is —N(R)C(O)OR. In some embodiments, $R^{ZA}$ is —N(R)C(O)R. In some embodiments, $R^{ZA}$ is —N(R)C(O)NR$_2$. In some embodiments, $R^{ZA}$ is —N(R)C(NR)NR$_2$. In some embodiments, $R^{ZA}$ is —N(R)S(O)$_2$NR$_2$. In some embodiments, $R^{ZA}$ is —N(R)S(O)$_2$R. In some embodiments, $R^{ZA}$ is —P(O)R$_2$. In some embodiments, $R^{ZA}$ is —P(O)(R)OR. In some embodiments, $R^{ZA}$ is —B(OR)$_2$. In some embodiments, $R^{ZA}$ is deuterium.

In some embodiments, $R^{ZA}$ is halogen, —CN, —NO$_2$, —OR, —SR, —NR$_2$, —S(O)$_2$R, —S(O)$_2$NR$_2$, —S(O)$_2$F, —S(O)R, —S(O)NR$_2$, —S(O)(NR)R, —C(O)R, —C(O)OR, —C(O)NR$_2$, —C(O)N(R)OR, —OC(O)R, —OC(O)NR$_2$, —N(R)C(O)OR, —N(R)C(O)R, —N(R)C(O)NR$_2$, —N(R)C(NR)NR$_2$, —N(R)S(O)$_2$NR$_2$, —N(R)S(O)$_2$R, —P(O)R$_2$, —P(O)(R)OR, or —B(OR)$_2$.

In some embodiments, $R^{ZA}$ is halogen, —CN, or —NO$_2$. In some embodiments, $R^{ZA}$ is —OR, —SR, or —NR$_2$. In some embodiments, $R^{ZA}$ is —S(O)$_2$R, —S(O)$_2$NR$_2$, —S(O)$_2$F, —S(O)R, —S(O)NR$_2$, or —S(O)(NR)R. In some embodiments, $R^{ZA}$ is —C(O)R, —C(O)OR, —C(O)NR$_2$, or —C(O)N(R)OR. In some embodiments, $R^{ZA}$ is —OC(O)R or —OC(O)NR$_2$. In some embodiments, $R^{ZA}$ is —N(R)C(O)OR, —N(R)C(O)R, —N(R)C(O)NR$_2$, —N(R)C(NR)NR$_2$, —N(R)S(O)$_2$NR$_2$, or —N(R)S(O)$_2$R. In some embodiments, $R^{ZA}$ is —P(O)R$_2$ or —P(O)(R)OR.

In some embodiments, $R^{ZA}$ is —OR, —OC(O)R, or —OC(O)NR$_2$. In some embodiments, $R^{ZA}$ is —SR, —S(O)$_2$R, —S(O)$_2$NR$_2$, —S(O)$_2$F, —S(O)R, —S(O)NR$_2$, or —S(O)(NR)R. In some embodiments, $R^{ZA}$ is —NR$_2$, —N(R)C(O)OR, —N(R)C(O)R, —N(R)C(O)NR$_2$, —N(R)C(NR)NR$_2$, —N(R)S(O)$_2$NR$_2$, or —N(R)S(O)$_2$R.

In some embodiments, $R^{ZA}$ is —S(O)$_2$R, —S(O)$_2$NR$_2$, or —S(O)$_2$F. In some embodiments, $R^{ZA}$ is —S(O)R, —S(O)NR$_2$, or —S(O)(NR)R. In some embodiments, $R^{ZA}$ is —SR, —S(O)$_2$R, or —S(O)R. In some embodiments, $R^{ZA}$ is —S(O)$_2$NR$_2$, —S(O)NR$_2$, or —S(O)(NR)R. In some embodiments, $R^{ZA}$ is —S(O)$_2$NR$_2$ or —S(O)NR$_2$. In some embodiments, $R^{ZA}$ is —SR, —S(O)$_2$R, —S(O)$_2$NR$_2$, or —S(O)R.

In some embodiments, $R^{ZA}$ is —N(R)C(O)OR, —N(R)C(O)R, or —N(R)C(O)NR$_2$. In some embodiments, $R^{ZA}$ is —N(R)S(O)$_2$NR$_2$ or —N(R)S(O)$_2$R. In some embodiments, $R^{ZA}$ is —N(R)C(O)OR or —N(R)C(O)R. In some embodiments, $R^{ZA}$ is —N(R)C(O)NR$_2$ or —N(R)S(O)$_2$NR$_2$. In some embodiments, $R^{ZA}$ is —N(R)C(O)OR, —N(R)C(O)R, or —N(R)S(O)$_2$R.

In some embodiments, $R^{ZA}$ is —NR$_2$, —N(R)C(O)OR, —N(R)C(O)R, or —N(R)C(O)NR$_2$. In some embodiments, $R^{ZA}$ is —NR$_2$, —N(R)C(O)OR, or —N(R)C(O)R. In some embodiments, $R^{ZA}$ is —NR$_2$, —N(R)C(O)OR, —N(R)C(O)R, or —N(R)S(O)$_2$R.

In some embodiments, $R^{ZA}$ is a C$_{1-6}$ aliphatic chain; phenyl; naphthyl; a 5-6 membered monocyclic heteroaryl ring having 1-4 heteroatoms independently selected from nitrogen, oxygen, and sulfur; an 8-10 membered bicyclic heteroaryl ring having 1-4 heteroatoms independently selected from nitrogen, oxygen, and sulfur; a 3-7 membered saturated or partially unsaturated monocyclic carbocyclic ring; a 5-12 membered saturated or partially unsaturated bicyclic carbocyclic ring; a 3-7 membered saturated or partially unsaturated monocyclic heterocyclic ring having 1-2 heteroatoms independently selected from nitrogen, oxygen, and sulfur; or a 7-12 membered saturated or partially unsaturated bicyclic heterocyclic ring having 1-4 heteroatoms independently selected from nitrogen, oxygen, and sulfur; each of which is substituted by $r^1$ instances of $R^{ZC}$.

In some embodiments, $R^{ZA}$ is a C$_{1-6}$ aliphatic chain substituted by $r^7$ instances of $R^{ZC}$. In some embodiments, $R^{ZA}$ is phenyl substituted by $r^1$ instances of $R^{ZC}$. In some embodiments, $R^{ZA}$ is naphthyl substituted by $r^7$ instances of $R^{ZC}$. In some embodiments, $R^{ZA}$ is a 5-6 membered monocyclic heteroaryl ring having 1-4 heteroatoms independently selected from nitrogen, oxygen, and sulfur; wherein said ring is substituted by $r^7$ instances of $R^{ZC}$. In some embodiments, $R^{ZA}$ is an 8-10 membered bicyclic heteroaryl ring having 1-4 heteroatoms independently selected from nitrogen, oxygen, and sulfur; wherein said ring is substituted by $r^7$ instances of $R^{ZC}$. In some embodiments, $R^{ZA}$ is a 3-7 membered saturated or partially unsaturated monocyclic carbocyclic ring substituted by $r^7$ instances of $R^{ZC}$. In some embodiments, $R^{ZA}$ is a 5-12 membered saturated or partially unsaturated bicyclic carbocyclic ring substituted by r instances of $R^{ZC}$. In some embodiments, $R^{ZA}$ is a 3-7 membered saturated or partially unsaturated monocyclic heterocyclic ring having 1-2 heteroatoms independently selected from nitrogen, oxygen, and sulfur; wherein said ring is substituted by $r^7$ instances of $R^{ZC}$. In some embodiments, $R^{ZA}$ is a 7-12 membered saturated or partially unsaturated bicyclic heterocyclic ring having 1-4 heteroatoms independently selected from nitrogen, oxygen, and sulfur; wherein said ring is substituted by $r^7$ instances of $R^{ZC}$.

In some embodiments, $R^{ZA}$ is phenyl; naphthyl; a 5-6 membered monocyclic heteroaryl ring having 1-4 heteroatoms independently selected from nitrogen, oxygen, and sulfur; an 8-10 membered bicyclic heteroaryl ring having 1-4 heteroatoms independently selected from nitrogen, oxygen, and sulfur; a 3-7 membered saturated or partially unsaturated monocyclic carbocyclic ring; a 5-12 membered saturated or partially unsaturated bicyclic carbocyclic ring; a 3-7 membered saturated or partially unsaturated monocyclic heterocyclic ring having 1-2 heteroatoms independently selected from nitrogen, oxygen, and sulfur; or a 7-12 membered saturated or partially unsaturated bicyclic heterocyclic ring having 1-4 heteroatoms independently selected from nitrogen, oxygen, and sulfur; each of which is substituted by $r^7$ instances of $R^{ZC}$.

In some embodiments, $R^{ZA}$ is phenyl; naphthyl; a 5-6 membered monocyclic heteroaryl ring having 1-4 heteroatoms independently selected from nitrogen, oxygen, and sulfur; or an 8-10 membered bicyclic heteroaryl ring having 1-4 heteroatoms independently selected from nitrogen, oxygen, and sulfur; each of which is substituted by $r^7$ instances of $R^{ZC}$. In some embodiments, $R^{ZA}$ is a 3-7 membered saturated or partially unsaturated monocyclic carbocyclic ring; a 5-12 membered saturated or partially unsaturated bicyclic carbocyclic ring; a 3-7 membered saturated or partially unsaturated monocyclic heterocyclic ring having 1-2 heteroatoms independently selected from nitrogen, oxygen, and sulfur; or a 7-12 membered saturated or partially unsaturated bicyclic heterocyclic ring having 1-4 heteroatoms independently selected from nitrogen, oxygen, and sulfur; each of which is substituted by $r^7$ instances of $R^{ZC}$.

In some embodiments, $R^{ZA}$ is phenyl; naphthyl; a 3-7 membered saturated or partially unsaturated monocyclic carbocyclic ring; or a 5-12 membered saturated or partially unsaturated bicyclic carbocyclic ring; each of which is substituted by $r^1$ instances of $R^{ZC}$. In some embodiments, $R^{ZA}$ is a 5-6 membered monocyclic heteroaryl ring having 1-4 heteroatoms independently selected from nitrogen, oxygen, and sulfur; an 8-10 membered bicyclic heteroaryl ring having 1-4 heteroatoms independently selected from nitrogen, oxygen, and sulfur; a 3-7 membered saturated or partially unsaturated monocyclic heterocyclic ring having 1-2 heteroatoms independently selected from nitrogen, oxygen, and sulfur; or a 7-12 membered saturated or partially unsaturated bicyclic heterocyclic ring having 1-4 heteroatoms independently selected from nitrogen, oxygen, and sulfur; each of which is substituted by $r^1$ instances of $R^{ZC}$.

In some embodiments, $R^{ZA}$ is phenyl; a 5-6 membered monocyclic heteroaryl ring having 1-4 heteroatoms independently selected from nitrogen, oxygen, and sulfur; a 3-7 membered saturated or partially unsaturated monocyclic carbocyclic ring; or a 3-7 membered saturated or partially unsaturated monocyclic heterocyclic ring having 1-2 heteroatoms independently selected from nitrogen, oxygen, and sulfur; each of which is substituted by $r^7$ instances of $R^{ZC}$. In some embodiments, $R^{ZA}$ is naphthyl; an 8-10 membered bicyclic heteroaryl ring having 1-4 heteroatoms independently selected from nitrogen, oxygen, and sulfur; a 5-12 membered saturated or partially unsaturated bicyclic carbocyclic ring; or a 7-12 membered saturated or partially unsaturated bicyclic heterocyclic ring having 1-4 heteroatoms independently selected from nitrogen, oxygen, and sulfur; each of which is substituted by $r^7$ instances of $R^{ZC}$.

In some embodiments, $R^{ZA}$ is phenyl or naphthyl; each of which is substituted by $r^7$ instances of $R^{ZC}$. In some embodiments, $R^{ZA}$ is a 5-6 membered monocyclic heteroaryl ring having 1-4 heteroatoms independently selected from nitrogen, oxygen, and sulfur; or an 8-10 membered bicyclic heteroaryl ring having 1-4 heteroatoms independently selected from nitrogen, oxygen, and sulfur; each of which is substituted by $r^7$ instances of $R^{ZC}$. In some embodiments, $R^{ZA}$ is a 3-7 membered saturated or partially unsaturated monocyclic carbocyclic ring or a 5-12 membered saturated or partially unsaturated bicyclic carbocyclic ring; each of which is substituted by $r^1$ instances of $R^{ZC}$. In some embodiments, $R^{ZA}$ is a 3-7 membered saturated or partially unsaturated monocyclic heterocyclic ring having 1-2 heteroatoms independently selected from nitrogen, oxygen, and sulfur; or a 7-12 membered saturated or partially unsaturated bicyclic heterocyclic ring having 1-4 heteroatoms independently selected from nitrogen, oxygen, and sulfur; each of which is substituted by $r^7$ instances of $R^{ZC}$.

In some embodiments, $R^{ZA}$ is phenyl or a 5-6 membered monocyclic heteroaryl ring having 1-4 heteroatoms independently selected from nitrogen, oxygen, and sulfur; each of which is substituted by $r^1$ instances of $R^{ZC}$. In some embodiments, $R^{ZA}$ is a 3-7 membered saturated or partially unsaturated monocyclic carbocyclic ring or a 3-7 membered saturated or partially unsaturated monocyclic heterocyclic ring having 1-2 heteroatoms independently selected from nitrogen, oxygen, and sulfur; each of which is substituted by $r^1$ instances of $R^{ZC}$. In some embodiments, $R^{ZA}$ is naphthyl or an 8-10 membered bicyclic heteroaryl ring having 1-4 heteroatoms independently selected from nitrogen, oxygen, and sulfur; each of which is substituted by $r^1$ instances of $R^{ZC}$. In some embodiments, $R^{ZA}$ is a 5-12 membered saturated or partially unsaturated bicyclic carbocyclic ring or a 7-12 membered saturated or partially unsaturated bicyclic heterocyclic ring having 1-4 heteroatoms independently selected from nitrogen, oxygen, and sulfur; each of which is substituted by $r^1$ instances of $R^{ZC}$.

In some embodiments, $R^{ZA}$ is phenyl or a 3-7 membered saturated or partially unsaturated monocyclic carbocyclic ring; each of which is substituted by $r^1$ instances of $R^{ZC}$ In some embodiments, $R^{ZA}$ is naphthyl or a 5-12 membered saturated or partially unsaturated bicyclic carbocyclic ring; each of which is substituted by $r^7$ instances of $R^{ZC}$. In some embodiments, $R^{ZA}$ is a 5-6 membered monocyclic heteroaryl ring having 1-4 heteroatoms independently selected from nitrogen, oxygen, and sulfur; or a 3-7 membered saturated or partially unsaturated monocyclic heterocyclic ring having 1-2 heteroatoms independently selected from nitrogen, oxygen, and sulfur; each of which is substituted by $r^7$ instances of $R^{ZC}$. In some embodiments, $R^{ZA}$ is an 8-10 membered bicyclic heteroaryl ring having 1-4 heteroatoms independently selected from nitrogen, oxygen, and sulfur; or a 7-12 membered saturated or partially unsaturated bicyclic heterocyclic ring having 1-4 heteroatoms independently selected from nitrogen, oxygen, and sulfur; each of which is substituted by $r^7$ instances of $R^{ZC}$.

In some embodiments, $R^{ZA}$ is a $C_{1-6}$ aliphatic chain; a 3-7 membered saturated or partially unsaturated monocyclic carbocyclic ring; a 5-12 membered saturated or partially unsaturated bicyclic carbocyclic ring; a 3-7 membered saturated or partially unsaturated monocyclic heterocyclic ring having 1-2 heteroatoms independently selected from nitrogen, oxygen, and sulfur; or a 7-12 membered saturated or partially unsaturated bicyclic heterocyclic ring having 1-4 heteroatoms independently selected from nitrogen, oxygen, and sulfur; each of which is substituted by $r^7$ instances of $R^{ZC}$. In some embodiments, $R^{ZA}$ is a $C_{1-6}$ aliphatic chain; naphthyl; a 3-7 membered saturated or partially unsaturated monocyclic carbocyclic ring; or a 5-12 membered saturated or partially unsaturated bicyclic carbocyclic ring; each of which is substituted by $r^2$ instances of $R^{ZC}$. In some embodiments, $R^{ZA}$ is a $C_{1-6}$ aliphatic chain; phenyl; a 5-6 membered monocyclic heteroaryl ring having 1-4 heteroatoms independently selected from nitrogen, oxygen, and sulfur; a 3-7 membered saturated or partially unsaturated monocyclic carbocyclic ring; or a 3-7 membered saturated or partially unsaturated monocyclic heterocyclic ring having 1-2 heteroatoms independently selected from nitrogen, oxygen, and sulfur; each of which is substituted by $r^7$ instances of $R^{ZC}$.

In some embodiments, $R^{ZA}$ is a $C_{1-6}$ aliphatic chain, a 3-7 membered saturated or partially unsaturated monocyclic carbocyclic ring, or a 5-12 membered saturated or partially unsaturated bicyclic carbocyclic ring; each of which is substituted by $r^1$ instances of $R^{ZC}$. In some embodiments, $R^{ZA}$ is a $C_{1-6}$ aliphatic chain, a 3-7 membered saturated or partially unsaturated monocyclic carbocyclic ring, or a 3-7 membered saturated or partially unsaturated monocyclic heterocyclic ring having 1-2 heteroatoms independently selected from nitrogen, oxygen, and sulfur; each of which is substituted by $r^1$ instances of $R^{ZC}$. In some embodiments, $R^{ZA}$ is a $C_{1-6}$ aliphatic chain, phenyl, or a 3-7 membered saturated or partially unsaturated monocyclic carbocyclic ring; each of which is substituted by $r^7$ instances of $R^{ZC}$.

In some embodiments, $R^{ZA}$ is selected from the groups depicted in the compounds in Table 1.

As defined generally above, $R^L$ is $R^A$ or $R^B$ substituted by r instances of $R^{LC}$. In some embodiments, $R^L$ is $R^A$. In some embodiments, $R^L$ is $R^B$ substituted by $r^8$ instances of $R^{1C}$.

In some embodiments, $R^L$ is oxo, halogen, —CN, —NO$_2$, —OR, —SR, —NR$_2$, —S(O)$_2$R, —S(O)$_2$NR$_2$, —S(O)$_2$F, —S(O)R, —S(O)NR$_2$, —S(O)(NR)R, —C(O)R, —C(O)OR, —C(O)NR$_2$, —C(O)N(R)OR, —OC(O)R, —OC(O)NR$_2$, —N(R)C(O)OR, —N(R)C(O)R, —N(R)C(O)NR$_2$, —N(R)C(NR)NR$_2$, —N(R)S(O)$_2$NR$_2$, —N(R)S(O)$_2$R, —P(O)R$_2$, —P(O)(R)OR, —B(OR)$_2$, or deuterium.

In some embodiments, $R^L$ is oxo, halogen, —CN, —NO$_2$, —OR, —SR, —NR$_2$, —S(O)$_2$R, —S(O)$_2$NR$_2$, —S(O)$_2$F, —S(O)R, —S(O)NR$_2$, —S(O)(NR)R, —C(O)R, —C(O)OR, —C(O)NR$_2$, —C(O)N(R)OR, —OC(O)R, —OC(O)NR$_2$, —N(R)C(O)OR, —N(R)C(O)R, —N(R)C(O)NR$_2$, —N(R)C(NR)NR$_2$, —N(R)S(O)$_2$NR$_2$, —N(R)S(O)$_2$R, —P(O)R$_2$, —P(O)(R)OR, or —B(OR)$_2$.

In some embodiments, $R^L$ is oxo. In some embodiments, $R^L$ is halogen. In some embodiments, $R^L$ is —CN. In some embodiments, $R^L$ is —NO$_2$. In some embodiments, $R^L$ is —OR. In some embodiments, $R^L$ is —SR. In some embodiments, $R^L$ is —NR$_2$. In some embodiments, $R^L$ is —S(O)$_2$R. In some embodiments, $R^L$ is —S(O)$_2$NR$_2$. In some embodiments, $R^L$ is —S(O)$_2$F. In some embodiments, $R^L$ is —S(O)R. In some embodiments, $R^L$ is —S(O)NR$_2$. In some embodiments, $R^L$ is —S(O)(NR)R. In some embodiments, $R^L$ is —C(O)R. In some embodiments, $R^L$ is —C(O)OR. In some embodiments, $R^L$ is —C(O)NR$_2$. In some embodiments, $R^L$ is —C(O)N(R)OR. In some embodiments, $R^L$ is —OC(O)R. In some embodiments, $R^L$ is —OC(O)NR$_2$. In some embodiments, $R^L$ is —N(R)C(O)OR. In some embodiments, $R^L$ is —N(R)C(O)R. In some embodiments, $R^L$ is —N(R)C(O)NR$_2$. In some embodiments, $R^L$ is —N(R)C(NR)NR$_2$. In some embodiments, $R^L$ is —N(R)S(O)$_2$NR$_2$. In some embodiments, $R^L$ is —N(R)S(O)$_2$R. In some embodiments, $R^L$ is —P(O)R$_2$. In some embodiments, $R^L$ is —P(O)(R)OR. In some embodiments, $R^L$ is —B(OR)$_2$. In some embodiments, $R^L$ is deuterium.

In some embodiments, $R^L$ is halogen, —CN, —NO$_2$, —OR, —SR, —NR$_2$, —S(O)$_2$R, —S(O)$_2$NR$_2$, —S(O)$_2$F, —S(O)R, —S(O)NR$_2$, —S(O)(NR)R, —C(O)R, —C(O)OR, —C(O)NR$_2$, —C(O)N(R)OR, —OC(O)R, —OC(O)NR$_2$, —N(R)C(O)OR, —N(R)C(O)R, —N(R)C(O)NR$_2$, —N(R)C(NR)NR$_2$, —N(R)S(O)$_2$NR$_2$, —N(R)S(O)$_2$R, —P(O)R$_2$, —P(O)(R)OR, or —B(OR)$_2$.

In some embodiments, $R^L$ is halogen, —CN, or —NO$_2$. In some embodiments, $R^L$ is —OR, —SR, or —NR$_2$. In some embodiments, $R^L$ is —S(O)$_2$R, —S(O)$_2$NR$_2$, —S(O)$_2$F, —S(O)R, —S(O)NR$_2$, or —S(O)(NR)R. In some embodiments, $R^L$ is —C(O)R, —C(O)OR, —C(O)NR$_2$, or —C(O)N(R)OR. In some embodiments, $R^L$ is —OC(O)R or —OC(O)NR$_2$. In some embodiments, $R^L$ is —N(R)C(O)OR, —N(R)C(O)R, —N(R)C(O)NR$_2$, —N(R)C(NR)NR$_2$, —N(R)S(O)$_2$NR$_2$, or —N(R)S(O)$_2$R. In some embodiments, $R^L$ is —P(O)R$_2$ or —P(O)(R)OR.

In some embodiments, $R^L$ is —OR, —OC(O)R, or —OC(O)NR$_2$. In some embodiments, $R^L$ is —SR, —S(O)$_2$R, —S(O)$_2$NR$_2$, —S(O)$_2$F, —S(O)R, —S(O)NR$_2$, or —S(O)(NR)R. In some embodiments, $R^L$ is —NR$_2$, —N(R)C(O)OR, —N(R)C(O)R, —N(R)C(O)NR$_2$, —N(R)C(NR)NR$_2$, —N(R)S(O)$_2$NR$_2$, or —N(R)S(O)$_2$R.

In some embodiments, $R^L$ is —S(O)$_2$R, —S(O)$_2$NR$_2$, or —S(O)$_2$F. In some embodiments, $R^L$ is —S(O)R, —S(O)NR$_2$, or —S(O)(NR)R. In some embodiments, $R^L$ is —SR, —S(O)$_2$R, or —S(O)R. In some embodiments, $R^L$ is —S(O)$_2$NR$_2$, —S(O)NR$_2$, or —S(O)(NR)R. In some embodiments, $R^L$ is —S(O)$_2$NR$_2$ or —S(O)NR$_2$. In some embodiments, $R^L$ is —SR, —S(O)$_2$R, —S(O)$_2$NR$_2$, or —S(O)R.

In some embodiments, $R^L$ is —N(R)C(O)OR, —N(R)C(O)R, or —N(R)C(O)NR$_2$. In some embodiments, $R^L$ is —N(R)S(O)$_2$NR$_2$ or —N(R)S(O)$_2$R. In some embodiments, $R^L$ is —N(R)C(O)OR or —N(R)C(O)R. In some embodiments, $R^L$ is —N(R)C(O)NR$_2$ or —N(R)S(O)$_2$NR$_2$. In some embodiments, $R^L$ is —N(R)C(O)OR, —N(R)C(O)R, or —N(R)S(O)$_2$R.

In some embodiments, $R^L$ is —NR$_2$, —N(R)C(O)OR, —N(R)C(O)R, or —N(R)C(O)NR$_2$. In some embodiments, $R^L$ is —NR$_2$, —N(R)C(O)OR, or —N(R)C(O)R. In some embodiments, $R^L$ is —NR$_2$, —N(R)C(O)OR, —N(R)C(O)R, or —N(R)S(O)$_2$R.

In some embodiments, $R^L$ is a $C_{1-6}$ aliphatic chain; phenyl; naphthyl; a 5-6 membered monocyclic heteroaryl ring having 1-4 heteroatoms independently selected from nitrogen, oxygen, and sulfur; an 8-10 membered bicyclic heteroaryl ring having 1-4 heteroatoms independently selected from nitrogen, oxygen, and sulfur; a 3-7 membered saturated or partially unsaturated monocyclic carbocyclic ring; a 5-12 membered saturated or partially unsaturated bicyclic carbocyclic ring; a 3-7 membered saturated or partially unsaturated monocyclic heterocyclic ring having 1-2 heteroatoms independently selected from nitrogen, oxygen, and sulfur; or a 7-12 membered saturated or partially unsaturated bicyclic heterocyclic ring having 1-4 heteroatoms independently selected from nitrogen, oxygen, and sulfur; each of which is substituted by $r^8$ instances of $R^{LC}$.

In some embodiments, $R^L$ is a $C_{1-6}$ aliphatic chain substituted by $r^1$ instances of $R^{LC}$.

In some embodiments, $R^L$ is phenyl substituted by $r^8$ instances of $R^L$. In some embodiments, $R^L$ is naphthyl substituted by $r^7$ instances of $R^{LC}$. In some embodiments, $R^L$ is a 5-6 membered monocyclic heteroaryl ring having 1-4 heteroatoms independently selected from nitrogen, oxygen, and sulfur; wherein said ring is substituted by r¹ instances of $R^{LC}$ In some embodiments, $R^L$ is an 8-10 membered bicyclic heteroaryl ring having 1-4 heteroatoms independently selected from nitrogen, oxygen, and sulfur; wherein said ring is substituted by r⁸ instances of $R^{LC}$. In some embodiments, $R^L$ is a 3-7 membered saturated or partially unsaturated monocyclic carbocyclic ring substituted by r instances of $R^{LC}$. In some embodiments, $R^L$ is a 5-12 membered saturated or partially unsaturated bicyclic carbocyclic ring substituted by r⁵ instances of $R^{LC}$. In some embodiments, $R^L$ is a 3-7 membered saturated or partially unsaturated monocyclic heterocyclic ring having 1-2 heteroatoms independently selected from nitrogen, oxygen, and sulfur; wherein said ring is substituted by r⁸ instances of $R^{LC}$. In some embodiments, $R^L$ is a 7-12 membered saturated or partially unsaturated bicyclic heterocyclic ring having 1-4 heteroatoms independently selected from nitrogen, oxygen, and sulfur; wherein said ring is substituted by r⁵ instances of $R^{LC}$.

In some embodiments, $R^L$ is phenyl; naphthyl; a 5-6 membered monocyclic heteroaryl ring having 1-4 heteroatoms independently selected from nitrogen, oxygen, and sulfur; an 8-10 membered bicyclic heteroaryl ring having 1-4 heteroatoms independently selected from nitrogen, oxygen, and sulfur; a 3-7 membered saturated or partially unsaturated monocyclic carbocyclic ring; a 5-12 membered saturated or partially unsaturated bicyclic carbocyclic ring; a 3-7 membered saturated or partially unsaturated monocyclic heterocyclic ring having 1-2 heteroatoms independently selected from nitrogen, oxygen, and sulfur; or a 7-12 membered saturated or partially unsaturated bicyclic heterocyclic ring having 1-4 heteroatoms independently selected from nitrogen, oxygen, and sulfur; each of which is substituted by r⁸ instances of $R^{LC}$.

In some embodiments, $R^L$ is phenyl; naphthyl; a 5-6 membered monocyclic heteroaryl ring having 1-4 heteroatoms independently selected from nitrogen, oxygen, and sulfur; or an 8-10 membered bicyclic heteroaryl ring having 1-4 heteroatoms independently selected from nitrogen, oxygen, and sulfur; each of which is substituted by r⁸ instances of $R^{LC}$. In some embodiments, $R^L$ is a 3-7 membered saturated or partially unsaturated monocyclic carbocyclic ring; a 5-12 membered saturated or partially unsaturated bicyclic carbocyclic ring; a 3-7 membered saturated or partially unsaturated monocyclic heterocyclic ring having 1-2 heteroatoms independently selected from nitrogen, oxygen, and sulfur; or a 7-12 membered saturated or partially unsaturated bicyclic heterocyclic ring having 1-4 heteroatoms independently selected from nitrogen, oxygen, and sulfur; each of which is substituted by r⁵ instances of $R^{LC}$.

In some embodiments, $R^L$ is phenyl; naphthyl; a 3-7 membered saturated or partially unsaturated monocyclic carbocyclic ring; or a 5-12 membered saturated or partially unsaturated bicyclic carbocyclic ring; each of which is substituted by r⁸ instances of $R^{LC}$. In some embodiments, $R^L$ is a 5-6 membered monocyclic heteroaryl ring having 1-4 heteroatoms independently selected from nitrogen, oxygen, and sulfur; an 8-10 membered bicyclic heteroaryl ring having 1-4 heteroatoms independently selected from nitrogen, oxygen, and sulfur; a 3-7 membered saturated or partially unsaturated monocyclic heterocyclic ring having 1-2 heteroatoms independently selected from nitrogen, oxygen, and sulfur; or a 7-12 membered saturated or partially unsaturated bicyclic heterocyclic ring having 1-4 heteroatoms independently selected from nitrogen, oxygen, and sulfur; each of which is substituted by r⁸ instances of $R^{LC}$.

In some embodiments, $R^L$ is phenyl; a 5-6 membered monocyclic heteroaryl ring having 1-4 heteroatoms independently selected from nitrogen, oxygen, and sulfur; a 3-7 membered saturated or partially unsaturated monocyclic carbocyclic ring; or a 3-7 membered saturated or partially unsaturated monocyclic heterocyclic ring having 1-2 heteroatoms independently selected from nitrogen, oxygen, and sulfur; each of which is substituted by r⁸ instances of $R^{LC}$. In some embodiments, $R^L$ is naphthyl; an 8-10 membered bicyclic heteroaryl ring having 1-4 heteroatoms independently selected from nitrogen, oxygen, and sulfur; a 5-12 membered saturated or partially unsaturated bicyclic carbocyclic ring; or a 7-12 membered saturated or partially unsaturated bicyclic heterocyclic ring having 1-4 heteroatoms independently selected from nitrogen, oxygen, and sulfur; each of which is substituted by r⁸ instances of $R^{LC}$.

In some embodiments, $R^L$ is phenyl or naphthyl; each of which is substituted by r⁸ instances of $R^{LC}$. In some embodiments, $R^L$ is a 5-6 membered monocyclic heteroaryl ring having 1-4 heteroatoms independently selected from nitrogen, oxygen, and sulfur; or an 8-10 membered bicyclic heteroaryl ring having 1-4 heteroatoms independently selected from nitrogen, oxygen, and sulfur; each of which is substituted by r¹ instances of $R^{LC}$. In some embodiments, $R^L$ is a 3-7 membered saturated or partially unsaturated monocyclic carbocyclic ring or a 5-12 membered saturated or partially unsaturated bicyclic carbocyclic ring; each of which is substituted by r⁸ instances of $R^{LC}$. In some embodiments, $R^L$ is a 3-7 membered saturated or partially unsaturated monocyclic heterocyclic ring having 1-2 heteroatoms independently selected from nitrogen, oxygen, and sulfur; or a 7-12 membered saturated or partially unsaturated bicyclic heterocyclic ring having 1-4 heteroatoms independently selected from nitrogen, oxygen, and sulfur; each of which is substituted by r⁸ instances of $R^{LC}$.

In some embodiments, $R^L$ is phenyl or a 5-6 membered monocyclic heteroaryl ring having 1-4 heteroatoms independently selected from nitrogen, oxygen, and sulfur; each of which is substituted by r⁵ instances of $R^{LC}$. In some embodiments, $R^L$ is a 3-7 membered saturated or partially unsaturated monocyclic carbocyclic ring or a 3-7 membered saturated or partially unsaturated monocyclic heterocyclic ring having 1-2 heteroatoms independently selected from nitrogen, oxygen, and sulfur; each of which is substituted by r¹ instances of $R^{LC}$. In some embodiments, $R^L$ is naphthyl or an 8-10 membered bicyclic heteroaryl ring having 1-4 heteroatoms independently selected from nitrogen, oxygen, and sulfur; each of which is substituted by r⁵ instances of $R^{LC}$. In some embodiments, $R^L$ is a 5-12 membered saturated or partially unsaturated bicyclic carbocyclic ring or a 7-12 membered saturated or partially unsaturated bicyclic heterocyclic ring having 1-4 heteroatoms independently selected from nitrogen, oxygen, and sulfur; each of which is substituted by r¹ instances of $R^{LC}$.

In some embodiments, $R^L$ is phenyl or a 3-7 membered saturated or partially unsaturated monocyclic carbocyclic ring; each of which is substituted by r⁵ instances of $R^{LC}$ In some embodiments, $R^L$ is naphthyl or a 5-12 membered saturated or partially unsaturated bicyclic carbocyclic ring; each of which is substituted by r⁵ instances of $R^{LC}$. In some embodiments, $R^L$ is a 5-6 membered monocyclic heteroaryl ring having 1-4 heteroatoms independently selected from nitrogen, oxygen, and sulfur; or a 3-7 membered saturated or partially unsaturated monocyclic heterocyclic ring having 1-2 heteroatoms independently selected from nitrogen, oxygen, and sulfur; each of which is substituted by r⁸ instances of $R^{LC}$. In some embodiments, $R^L$ is an 8-10 membered bicyclic heteroaryl ring having 1-4 heteroatoms independently selected from nitrogen, oxygen, and sulfur; or a 7-12 membered saturated or partially unsaturated bicyclic heterocyclic ring having 1-4 heteroatoms independently selected from nitrogen, oxygen, and sulfur; each of which is substituted by $r^8$ instances of $R^{LC}$.

In some embodiments, $R^L$ is a $C_{1-6}$ aliphatic chain; a 3-7 membered saturated or partially unsaturated monocyclic carbocyclic ring; a 5-12 membered saturated or partially unsaturated bicyclic carbocyclic ring; a 3-7 membered saturated or partially unsaturated monocyclic heterocyclic ring having 1-2 heteroatoms independently selected from nitrogen, oxygen, and sulfur; or a 7-12 membered saturated or partially unsaturated bicyclic heterocyclic ring having 1-4 heteroatoms independently selected from nitrogen, oxygen, and sulfur; each of which is substituted by $r^8$ instances of $R^{LC}$. In some embodiments, $R^L$ is a $C_{1-6}$ aliphatic chain; phenyl; naphthyl; a 3-7 membered saturated or partially unsaturated monocyclic carbocyclic ring; or a 5-12 membered saturated or partially unsaturated bicyclic carbocyclic ring; each of which is substituted by $r^8$ instances of $R^{LC}$. In some embodiments, $R^L$ is a $C_{1-6}$ aliphatic chain; phenyl; a 5-6 membered monocyclic heteroaryl ring having 1-4 heteroatoms independently selected from nitrogen, oxygen, and sulfur; a 3-7 membered saturated or partially unsaturated monocyclic carbocyclic ring; or a 3-7 membered saturated or partially unsaturated monocyclic heterocyclic ring having 1-2 heteroatoms independently selected from nitrogen, oxygen, and sulfur; each of which is substituted by $r^8$ instances of $R^{LC}$.

In some embodiments, $R^L$ is a $C_{1-6}$ aliphatic chain, a 3-7 membered saturated or partially unsaturated monocyclic carbocyclic ring, or a 5-12 membered saturated or partially unsaturated bicyclic carbocyclic ring; each of which is substituted by $r^8$ instances of $R^{LC}$ In some embodiments, $R^L$ is a $C_{1-6}$ aliphatic chain, a 3-7 membered saturated or partially unsaturated monocyclic carbocyclic ring, or a 3-7 membered saturated or partially unsaturated monocyclic heterocyclic ring having 1-2 heteroatoms independently selected from nitrogen, oxygen, and sulfur; each of which is substituted by $r^8$ instances of $R^{LC}$ In some embodiments, $R^L$ is a $C_{1-6}$ aliphatic chain, phenyl, or a 3-7 membered saturated or partially unsaturated monocyclic carbocyclic ring; each of which is substituted by $r^8$ instances of $R^{LC}$.

In some embodiments, $R^L$ is selected from the groups depicted in the compounds in Table 1.

As defined generally above, each instance of $R^A$ is independently oxo, deuterium, halogen, —CN, —NO$_2$, —OR, —SF$_5$, —SR, —NR$_2$, —S(O)$_2$R, —S(O)$_2$NR$_2$, —S(O)$_2$F, —S(O)R, —S(O)NR$_2$, —S(O)(NR)R, —C(O)R, —C(O)OR, —C(O)NR$_2$, —C(O)N(R)OR, —OC(O)R, —OC(O)NR$_2$, —N(R)C(O)OR, —N(R)C(O)R, —N(R)C(O)NR$_2$, —N(R)C(NR)NR$_2$, —N(R)S(O)$_2$NR$_2$, —N(R)S(O)$_2$R, —P(O)R$_2$, —P(O)(R)OR, or —B(OR)$_2$.

In some embodiments, each instance of $R^A$ is independently oxo, halogen, —CN, —NO$_2$, —OR, —SF$_5$, —SR, —NR$_2$, —S(O)$_2$R, —S(O)$_2$NR$_2$, —S(O)$_2$F, —S(O)R, —S(O)NR$_2$, —S(O)(NR)R, —C(O)R, —C(O)OR, —C(O)NR$_2$, —C(O)N(R)OR, —OC(O)R, —OC(O)NR$_2$, —N(R)C(O)OR, —N(R)C(O)R, —N(R)C(O)NR$_2$, —N(R)C(NR)NR$_2$, —N(R)S(O)$_2$NR$_2$, —N(R)S(O)$_2$R, —P(O)R$_2$, —P(O)(R)OR, or —B(OR)$_2$.

In some embodiments, $R^A$ is oxo. In some embodiments, $R^A$ is halogen. In some embodiments, $R^A$ is —CN. In some embodiments, $R^A$ is —NO$_2$. In some embodiments, $R^A$ is —OR. In some embodiments, $R^A$ is —SF$_5$. In some embodiments, $R^A$ is —SR. In some embodiments, $R^A$ is —NR$_2$. In some embodiments, $R^A$ is —S(O)$_2$R. In some embodiments, $R^A$ is —S(O)$_2$NR$_2$. In some embodiments, $R^A$ is —S(O)$_2$F. In some embodiments, $R^A$ is —S(O)R. In some embodiments, $R^A$ is —S(O)NR$_2$. In some embodiments, $R^A$ is —S(O)(NR)R. In some embodiments, $R^A$ is —C(O)R. In some embodiments, $R^A$ is —C(O)OR. In some embodiments, $R^A$ is —C(O)NR$_2$. In some embodiments, $R^A$ is —C(O)N(R)OR. In some embodiments, $R^A$ is —OC(O)R. In some embodiments, $R^A$ is —OC(O)NR$_2$. In some embodiments, $R^A$ is —N(R)C(O)OR. In some embodiments, $R^A$ is —N(R)C(O)R. In some embodiments, $R^A$ is —N(R)C(O)NR$_2$. In some embodiments, $R^A$ is —N(R)C(NR)NR$_2$. In some embodiments, $R^A$ is —N(R)S(O)$_2$NR$_2$. In some embodiments, $R^A$ is —N(R)S(O)$_2$R. In some embodiments, $R^A$ is —P(O)R$_2$. In some embodiments, $R^A$ is —P(O)(R)OR. In some embodiments, $R^A$ is —B(OR)$_2$. In some embodiments, $R^A$ is deuterium.

In some embodiments, $R^A$ is halogen, —CN, —NO$_2$, —OR, —SR, —NR$_2$, —S(O)$_2$R, —S(O)$_2$NR$_2$, —S(O)$_2$F, —S(O)R, —S(O)NR$_2$, —S(O)(NR)R, —C(O)R, —C(O)OR, —C(O)NR$_2$, —C(O)N(R)OR, —OC(O)R, —OC(O)NR$_2$, —N(R)C(O)OR, —N(R)C(O)R, —N(R)C(O)NR$_2$, —N(R)C(NR)NR$_2$, —N(R)S(O)$_2$NR$_2$, —N(R)S(O)$_2$R, —P(O)R$_2$, —P(O)(R)OR, or —B(OR)$_2$.

In some embodiments, $R^A$ is halogen, —CN, or —NO$_2$. In some embodiments, $R^A$ is —OR, —SR, or —NR$_2$. In some embodiments, $R^A$ is —S(O)$_2$R, —S(O)$_2$NR$_2$, —S(O)$_2$F, —S(O)R, —S(O)NR$_2$, or —S(O)(NR)R. In some embodiments, $R^A$ is —C(O)R, —C(O)OR, —C(O)NR$_2$, or —C(O)N(R)OR. In some embodiments, $R^A$ is —OC(O)R or —OC(O)NR$_2$. In some embodiments, $R^A$ is —N(R)C(O)OR, —N(R)C(O)R, —N(R)C(O)NR$_2$, —N(R)C(NR)NR$_2$, —N(R)S(O)$_2$NR$_2$, or —N(R)S(O)$_2$R. In some embodiments, $R^A$ is —P(O)R$_2$ or —P(O)(R)OR.

In some embodiments, $R^A$ is —OR, —OC(O)R, or —OC(O)NR$_2$. In some embodiments, $R^A$ is —SR, —S(O)$_2$R, —S(O)$_2$NR$_2$, —S(O)$_2$F, —S(O)R, —S(O)NR$_2$, or —S(O)(NR)R. In some embodiments, $R^A$ is —NR$_2$, —N(R)C(O)OR, —N(R)C(O)R, —N(R)C(O)NR$_2$, —N(R)C(NR)NR$_2$, —N(R)S(O)$_2$NR$_2$, or —N(R)S(O)$_2$R.

In some embodiments, $R^A$ is —S(O)$_2$R, —S(O)$_2$NR$_2$, or —S(O)$_2$F. In some embodiments, $R^A$ is —S(O)R, —S(O)NR$_2$, or —S(O)(NR)R. In some embodiments, $R^A$ is —SR, —S(O)$_2$R, or —S(O)R. In some embodiments, $R^A$ is —S(O)$_2$NR$_2$, —S(O)NR$_2$, or —S(O)(NR)R. In some embodiments, $R^A$ is —S(O)$_2$NR$_2$ or —S(O)NR$_2$. In some embodiments, $R^A$ is —SR, —S(O)$_2$R, —S(O)$_2$NR$_2$, or —S(O)R.

In some embodiments, $R^A$ is —N(R)C(O)OR, —N(R)C(O)R, or —N(R)C(O)NR$_2$. In some embodiments, $R^A$ is —N(R)S(O)$_2$NR$_2$ or —N(R)S(O)$_2$R. In some embodiments, $R^A$ is —N(R)C(O)OR or —N(R)C(O)R. In some embodiments, $R^A$ is —N(R)C(O)NR$_2$ or —N(R)S(O)$_2$NR$_2$. In some embodiments, $R^A$ is —N(R)C(O)OR, —N(R)C(O)R, or —N(R)S(O)$_2$R.

In some embodiments, $R^A$ is —NR$_2$, —N(R)C(O)OR, —N(R)C(O)R, or —N(R)C(O)NR$_2$. In some embodiments, $R^A$ is —NR$_2$, —N(R)C(O)OR, or —N(R)C(O)R. In some embodiments, $R^A$ is —NR$_2$, —N(R)C(O)OR, —N(R)C(O)R, or —N(R)S(O)$_2$R.

In some embodiments, $R^A$ is selected from the groups depicted in the compounds in Table 1.

As defined generally above, each instance of $R^B$ is independently a $C_{1-6}$ aliphatic chain; phenyl; naphthyl; cubanyl; adamantyl; a 5-6 membered monocyclic heteroaryl ring having 1-4 heteroatoms independently selected from nitrogen, oxygen, and sulfur; an 8-10 membered bicyclic heteroaryl ring having 1-4 heteroatoms independently selected from nitrogen, oxygen, and sulfur; a 3-7 membered saturated or partially unsaturated monocyclic carbocyclic ring; a 5-12 membered saturated or partially unsaturated bicyclic carbocyclic ring; a 3-7 membered saturated or partially unsaturated monocyclic heterocyclic ring having 1-2 heteroatoms independently selected from nitrogen, oxygen, and sulfur; or a 7-12 membered saturated or partially unsaturated bicyclic heterocyclic ring having 1-4 heteroatoms independently selected from nitrogen, oxygen, and sulfur.

In some embodiments, $R^B$ is a $C_{1-6}$ aliphatic chain. In some embodiments, $R^B$ is phenyl. In some embodiments, $R^B$ is naphthyl. In some embodiments, $R^B$ is cubanyl. In some embodiments, $R^B$ is adamantyl. In some embodiments, $R^B$ is a 5-6 membered monocyclic heteroaryl ring having 1-4 heteroatoms independently selected from nitrogen, oxygen, and sulfur. In some embodiments, $R^B$ is an 8-10 membered bicyclic heteroaryl ring having 1-4 heteroatoms independently selected from nitrogen, oxygen, and sulfur. In some embodiments, $R^B$ is a 3-7 membered saturated or partially unsaturated monocyclic carbocyclic ring. In some embodiments, $R^B$ is a 5-12 membered saturated or partially unsaturated bicyclic carbocyclic ring. In some embodiments, $R^B$ is a 3-7 membered saturated or partially unsaturated monocyclic heterocyclic ring having 1-2 heteroatoms independently selected from nitrogen, oxygen, and sulfur. In some embodiments, $R^B$ is a 7-12 membered saturated or partially unsaturated bicyclic heterocyclic ring having 1-4 heteroatoms independently selected from nitrogen, oxygen, and sulfur.

In some embodiments, $R^B$ is phenyl; naphthyl; a 5-6 membered monocyclic heteroaryl ring having 1-4 heteroatoms independently selected from nitrogen, oxygen, and sulfur; an 8-10 membered bicyclic heteroaryl ring having 1-4 heteroatoms independently selected from nitrogen, oxygen, and sulfur; a 3-7 membered saturated or partially unsaturated monocyclic carbocyclic ring; a 5-12 membered saturated or partially unsaturated bicyclic carbocyclic ring; a 3-7 membered saturated or partially unsaturated monocyclic heterocyclic ring having 1-2 heteroatoms independently selected from nitrogen, oxygen, and sulfur; or a 7-12 membered saturated or partially unsaturated bicyclic heterocyclic ring having 1-4 heteroatoms independently selected from nitrogen, oxygen, and sulfur.

In some embodiments, $R^B$ is phenyl; naphthyl; a 5-6 membered monocyclic heteroaryl ring having 1-4 heteroatoms independently selected from nitrogen, oxygen, and sulfur; or an 8-10 membered bicyclic heteroaryl ring having 1-4 heteroatoms independently selected from nitrogen, oxygen, and sulfur. In some embodiments, $R^B$ is a 3-7 membered saturated or partially unsaturated monocyclic carbocyclic ring; a 5-12 membered saturated or partially unsaturated bicyclic carbocyclic ring; a 3-7 membered saturated or partially unsaturated monocyclic heterocyclic ring having 1-2 heteroatoms independently selected from nitrogen, oxygen, and sulfur; or a 7-12 membered saturated or partially unsaturated bicyclic heterocyclic ring having 1-4 heteroatoms independently selected from nitrogen, oxygen, and sulfur.

In some embodiments, $R^B$ is phenyl; naphthyl; a 3-7 membered saturated or partially unsaturated monocyclic carbocyclic ring; or a 5-12 membered saturated or partially unsaturated bicyclic carbocyclic ring. In some embodiments, $R^B$ is a 5-6 membered monocyclic heteroaryl ring having 1-4 heteroatoms independently selected from nitrogen, oxygen, and sulfur; an 8-10 membered bicyclic heteroaryl ring having 1-4 heteroatoms independently selected from nitrogen, oxygen, and sulfur; a 3-7 membered saturated or partially unsaturated monocyclic heterocyclic ring having 1-2 heteroatoms independently selected from nitrogen, oxygen, and sulfur; or a 7-12 membered saturated or partially unsaturated bicyclic heterocyclic ring having 1-4 heteroatoms independently selected from nitrogen, oxygen, and sulfur.

In some embodiments, $R^B$ is phenyl; a 5-6 membered monocyclic heteroaryl ring having 1-4 heteroatoms independently selected from nitrogen, oxygen, and sulfur; a 3-7 membered saturated or partially unsaturated monocyclic carbocyclic ring; or a 3-7 membered saturated or partially unsaturated monocyclic heterocyclic ring having 1-2 heteroatoms independently selected from nitrogen, oxygen, and sulfur. In some embodiments, $R^B$ is naphthyl; an 8-10 membered bicyclic heteroaryl ring having 1-4 heteroatoms independently selected from nitrogen, oxygen, and sulfur; a 5-12 membered saturated or partially unsaturated bicyclic carbocyclic ring; or a 7-12 membered saturated or partially unsaturated bicyclic heterocyclic ring having 1-4 heteroatoms independently selected from nitrogen, oxygen, and sulfur.

In some embodiments, $R^B$ is phenyl or naphthyl. In some embodiments, $R^B$ is a 5-6 membered monocyclic heteroaryl ring having 1-4 heteroatoms independently selected from nitrogen, oxygen, and sulfur; or an 8-10 membered bicyclic heteroaryl ring having 1-4 heteroatoms independently selected from nitrogen, oxygen, and sulfur. In some embodiments, $R^B$ is a 3-7 membered saturated or partially unsaturated monocyclic carbocyclic ring or a 5-12 membered saturated or partially unsaturated bicyclic carbocyclic ring. In some embodiments, $R^B$ is a 3-7 membered saturated or partially unsaturated monocyclic heterocyclic ring having 1-2 heteroatoms independently selected from nitrogen, oxygen, and sulfur; or a 7-12 membered saturated or partially unsaturated bicyclic heterocyclic ring having 1-4 heteroatoms independently selected from nitrogen, oxygen, and sulfur.

In some embodiments, $R^B$ is phenyl or a 5-6 membered monocyclic heteroaryl ring having 1-4 heteroatoms independently selected from nitrogen, oxygen, and sulfur. In some embodiments, $R^B$ is a 3-7 membered saturated or partially unsaturated monocyclic carbocyclic ring or a 3-7 membered saturated or partially unsaturated monocyclic heterocyclic ring having 1-2 heteroatoms independently selected from nitrogen, oxygen, and sulfur. In some embodiments, $R^B$ is naphthyl or an 8-10 membered bicyclic heteroaryl ring having 1-4 heteroatoms independently selected from nitrogen, oxygen, and sulfur. In some embodiments, $R^B$ is a 5-12 membered saturated or partially unsaturated bicyclic carbocyclic ring or a 7-12 membered saturated or partially unsaturated bicyclic heterocyclic ring having 1-4 heteroatoms independently selected from nitrogen, oxygen, and sulfur.

In some embodiments, $R^B$ is phenyl or a 3-7 membered saturated or partially unsaturated monocyclic carbocyclic ring. In some embodiments, $R^B$ is naphthyl or a 5-12 membered saturated or partially unsaturated bicyclic carbocyclic ring. In some embodiments, $R^B$ is a 5-6 membered monocyclic heteroaryl ring having 1-4 heteroatoms independently selected from nitrogen, oxygen, and sulfur; or a 3-7 membered saturated or partially unsaturated monocyclic heterocyclic ring having 1-2 heteroatoms independently selected from nitrogen, oxygen, and sulfur. In some embodiments, $R^B$ is an 8-10 membered bicyclic heteroaryl ring having 1-4 heteroatoms independently selected from nitrogen, oxygen, and sulfur; or a 7-12 membered saturated or partially unsaturated bicyclic heterocyclic ring having 1-4 heteroatoms independently selected from nitrogen, oxygen, and sulfur.

In some embodiments, $R^B$ is a $C_{1-6}$ aliphatic chain; a 3-7 membered saturated or partially unsaturated monocyclic carbocyclic ring; a 5-12 membered saturated or partially unsaturated bicyclic carbocyclic ring; a 3-7 membered saturated or partially unsaturated monocyclic heterocyclic ring having 1-2 heteroatoms independently selected from nitrogen, oxygen, and sulfur; or a 7-12 membered saturated or partially unsaturated bicyclic heterocyclic ring having 1-4 heteroatoms independently selected from nitrogen, oxygen, and sulfur. In some embodiments, $R^B$ is a $C_{1-6}$ aliphatic chain; phenyl; naphthyl; a 3-7 membered saturated or partially unsaturated monocyclic carbocyclic ring; or a 5-12 membered saturated or partially unsaturated bicyclic carbocyclic ring. In some embodiments, $R^B$ is a $C_{1-6}$ aliphatic chain; phenyl; a 5-6 membered monocyclic heteroaryl ring having 1-4 heteroatoms independently selected from nitrogen, oxygen, and sulfur; a 3-7 membered saturated or partially unsaturated monocyclic carbocyclic ring; or a 3-7 membered saturated or partially unsaturated monocyclic heterocyclic ring having 1-2 heteroatoms independently selected from nitrogen, oxygen, and sulfur.

In some embodiments, $R^B$ is a $C_{1-6}$ aliphatic chain, a 3-7 membered saturated or partially unsaturated monocyclic carbocyclic ring, or a 5-12 membered saturated or partially unsaturated bicyclic carbocyclic ring. In some embodiments, $R^B$ is a $C_{1-6}$ aliphatic chain, a 3-7 membered saturated or partially unsaturated monocyclic carbocyclic ring, or a 3-7 membered saturated or partially unsaturated monocyclic heterocyclic ring having 1-2 heteroatoms independently selected from nitrogen, oxygen, and sulfur. In some embodiments, $R^B$ is a $C_{1-6}$ aliphatic chain, phenyl, or a 3-7 membered saturated or partially unsaturated monocyclic carbocyclic ring.

In some embodiments, $R^B$ is selected from the groups depicted in the compounds in Table 1.

As defined generally above, each instance of $R^{1C}$ is independently oxo, deuterium, halogen, —CN, —NO$_2$, —OR, —SR, —NR$_2$, —S(O)$_2$R, —S(O)$_2$NR$_2$, —S(O)$_2$F, —S(O)R, —S(O)NR$_2$, —S(O)(NR)R, —C(O)R, —C(O)OR, —C(O)NR$_2$, —C(O)N(R)OR, —OC(O)R, —OC(O)NR$_2$, —N(R)C(O)OR, —N(R)C(O)R, —N(R)C(O)NR$_2$, —N(R)C(NR)NR$_2$, —N(R)S(O)$_2$NR$_2$, —N(R)S(O)$_2$R, —P(O)R$_2$, —P(O)(R)OR, —B(OR)$_2$, or an optionally substituted group selected from $C_{1-6}$ aliphatic, phenyl, a 3-7 membered saturated or partially unsaturated monocyclic heterocyclic ring having 1-2 heteroatoms independently selected from nitrogen, oxygen, and sulfur, and a 5-6 membered monocyclic heteroaryl ring having 1-4 heteroatoms independently selected from nitrogen, oxygen, and sulfur.

In some embodiments, each instance of $R^{1C}$ is independently oxo, halogen, —CN, —NO$_2$, —OR, —SR, —NR$_2$, —S(O)$_2$R, —S(O)$_2$NR$_2$, —S(O)$_2$F, —S(O)R, —S(O)NR$_2$, —S(O)(NR)R, —C(O)R, —C(O)OR, —C(O)NR$_2$, —C(O)N(R)OR, —OC(O)R, —OC(O)NR$_2$, —N(R)C(O)OR, —N(R)C(O)R, —N(R)C(O)NR$_2$, —N(R)C(NR)NR$_2$, —N(R)S(O)$_2$NR$_2$, —N(R)S(O)$_2$R, —P(O)R$_2$, —P(O)(R) OR, —B(OR)$_2$, or an optionally substituted group selected from $C_{1-6}$ aliphatic, phenyl, a 3-7 membered saturated or partially unsaturated monocyclic heterocyclic ring having 1-2 heteroatoms independently selected from nitrogen, oxygen, and sulfur, and a 5-6 membered monocyclic heteroaryl ring having 1-4 heteroatoms independently selected from nitrogen, oxygen, and sulfur.

In some embodiments, each instance of $R^{1C}$ is independently oxo, halogen, —CN, —NO$_2$, —OR, —SR, —NR$_2$, —S(O)$_2$R, —S(O)$_2$NR$_2$, —S(O)$_2$F, —S(O)R, —S(O)NR$_2$, —S(O)(NR)R, —C(O)R, —C(O)OR, —C(O)NR$_2$, —C(O) N(R)OR, —OC(O)R, —OC(O)NR$_2$, —N(R)C(O)OR, —N(R)C(O)R, —N(R)C(O)NR$_2$, —N(R)C(NR)NR$_2$, —N(R)S(O)$_2$NR$_2$, —N(R)S(O)$_2$R, —P(O)R$_2$, —P(O)(R) OR, or —B(OR)$_2$. In some embodiments, each instance of $R^{1C}$ is independently an optionally substituted group selected from $C_{1-6}$ aliphatic, phenyl, a 3-7 membered saturated or partially unsaturated monocyclic heterocyclic ring having 1-2 heteroatoms independently selected from nitrogen, oxygen, and sulfur, and a 5-6 membered monocyclic heteroaryl ring having 1-4 heteroatoms independently selected from nitrogen, oxygen, and sulfur.

In some embodiments, $R^{1C}$ is oxo. In some embodiments, $R^{1C}$ is deuterium. In some embodiments, each instance of $R^{1C}$ is independently halogen. In some embodiments, $R^{1C}$ is —CN. In some embodiments, $R^{1C}$ is —NO$_2$. In some embodiments, $R^{1C}$ is —OR. In some embodiments, $R^{1C}$ is —SR. In some embodiments, $R^{1C}$ is —NR$_2$. In some embodiments, $R^{1C}$ is —S(O)$_2$R. In some embodiments, $R^{1C}$ is —S(O)$_2$NR$_2$. In some embodiments, $R^{1C}$ is —S(O)$_2$F. In some embodiments, $R^{1C}$ is —S(O)R. In some embodiments, $R^{1C}$ is —S(O)NR$_2$. In some embodiments, $R^{1C}$ is —S(O) (NR)R. In some embodiments, $R^{1C}$ is —C(O)R. In some embodiments, $R^{1C}$ is —C(O)OR. In some embodiments, $R^{1C}$ is —C(O)NR$_2$. In some embodiments, $R^{1C}$ is —C(O) N(R)OR. In some embodiments, $R^{1C}$ is —OC(O)R. In some embodiments, $R^{1C}$ is —OC(O)NR$_2$. In some embodiments, $R^{1C}$ is —N(R)C(O)OR. In some embodiments, $R^{1C}$ is —N(R)C(O)R. In some embodiments, $R^{1C}$ is —N(R)C(O) NR$_2$. In some embodiments, $R^{1C}$ is —N(R)C(NR)NR$_2$. In some embodiments, $R^{1C}$ is —N(R)S(O)$_2$NR$_2$. In some embodiments, $R^{1C}$ is —N(R)S(O)$_2$R. In some embodiments, $R^{1C}$ is —P(O)R$_2$. In some embodiments, $R^{1C}$ is —P(O)(R) OR. In some embodiments, $R^{1C}$ is —B(OR)$_2$.

In some embodiments, each instance of $R^{1C}$ is independently halogen, —CN, —NO$_2$, —OR, —SR, —NR$_2$, —S(O)$_2$R, —S(O)$_2$NR$_2$, —S(O)$_2$F, —S(O)R, —S(O)NR$_2$, —S(O)(NR)R, —C(O)R, —C(O)OR, —C(O)NR$_2$, —C(O) N(R)OR, —OC(O)R, —OC(O)NR$_2$, —N(R)C(O)OR, —N(R)C(O)R, —N(R)C(O)NR$_2$, —N(R)C(NR)NR$_2$, —N(R)S(O)$_2$NR$_2$, —N(R)S(O)$_2$R, —P(O)R$_2$, —P(O)(R) OR, or —B(OR)$_2$.

In some embodiments, each instance of $R^{1C}$ is independently halogen, —CN, or —NO$_2$. In some embodiments, each instance of $R^{1C}$ is independently —OR, —SR, or —NR$_2$. In some embodiments, each instance of $R^{1C}$ is independently —S(O)$_2$R, —S(O)$_2$NR$_2$, —S(O)$_2$F, —S(O)R, —S(O)NR$_2$, or —S(O)(NR)R. In some embodiments, each instance of $R^{1C}$ is independently —C(O)R, —C(O)OR, —C(O)NR$_2$, or —C(O)N(R)OR. In some embodiments, each instance of $R^{1C}$ is independently —OC(O)R or —OC (O)NR$_2$. In some embodiments, each instance of $R^{1C}$ is independently —N(R)C(O)OR, —N(R)C(O)R, —N(R)C (O)NR$_2$, —N(R)C(NR)NR$_2$, —N(R)S(O)$_2$NR$_2$, or —N(R) S(O)$_2$R. In some embodiments, each instance of $R^{1C}$ is independently —P(O)R$_2$ or —P(O)(R)OR.

In some embodiments, each instance of $R^{1C}$ is independently —OR, —OC(O)R, or —OC(O)NR$_2$. In some embodiments, each instance of $R^{1C}$ is independently —SR, —S(O)$_2$R, —S(O)$_2$NR$_2$, —S(O)$_2$F, —S(O)R, —S(O)NR$_2$, or —S(O)(NR)R. In some embodiments, each instance of $R^{1C}$ is independently —NR$_2$, —N(R)C(O)OR, —N(R)C(O) R, —N(R)C(O)NR$_2$, —N(R)C(NR)NR$_2$, —N(R)S(O)$_2$NR$_2$, or —N(R)S(O)$_2$R.

In some embodiments, each instance of $R^{1C}$ is independently —S(O)$_2$R, —S(O)$_2$NR$_2$, or —S(O)$_2$F. In some embodiments, each instance of $R^{1C}$ is independently —S(O)R, —S(O)NR$_2$, or —S(O)(NR)R. In some embodiments, each instance of $R^{1C}$ is independently —SR, —S(O)$_2$R, or —S(O)R. In some embodiments, each instance of $R^{1C}$ is independently —S(O)$_2$NR$_2$, —S(O)NR$_2$, or —S(O)(NR)R. In some embodiments, each instance of $R^{1C}$ is independently —S(O)$_2$NR$_2$ or —S(O)NR$_2$. In some embodiments, each instance of $R^{1C}$ is independently —SR, —S(O)$_2$R, —S(O)$_2$NR$_2$, or —S(O)R.

In some embodiments, each instance of $R^{1C}$ is independently —N(R)C(O)OR, —N(R)C(O)R, or —N(R)C(O)NR$_2$. In some embodiments, each instance of $R^{1C}$ is independently —N(R)S(O)$_2$NR$_2$ or —N(R)S(O)$_2$R. In some embodiments, each instance of $R^{1C}$ is independently —N(R)C(O)OR or —N(R)C(O)R. In some embodiments, each instance of $R^{1C}$ is independently —N(R)C(O)NR$_2$ or —N(R)S(O)$_2$NR$_2$. In some embodiments, each instance of $R^{1C}$ is independently —N(R)C(O)OR, —N(R)C(O)R, or —N(R)S(O)$_2$R.

In some embodiments, each instance of $R^{1C}$ is independently —NR$_2$, —N(R)C(O)OR, —N(R)C(O)R, or —N(R)C(O)NR$_2$. In some embodiments, each instance of $R^{1C}$ is independently —NR$_2$, —N(R)C(O)OR, or —N(R)C(O)R. In some embodiments, each instance of $R^{1C}$ is independently —NR$_2$, —N(R)C(O)OR, —N(R)C(O)R, or —N(R)S(O)$_2$R.

In some embodiments, each instance of $R^{1C}$ is independently an optionally substituted $C_{1-6}$ aliphatic. In some embodiments, each instance of $R^{1C}$ is independently an optionally substituted phenyl. In some embodiments, each instance of $R^{1C}$ is independently an optionally substituted 3-7 membered saturated or partially unsaturated monocyclic heterocyclic ring having 1-2 heteroatoms independently selected from nitrogen, oxygen, and sulfur. In some embodiments, each instance of $R^{1C}$ is independently an optionally substituted 5-6 membered monocyclic heteroaryl ring having 1-4 heteroatoms independently selected from nitrogen, oxygen, and sulfur.

In some embodiments, each instance of $R^{1C}$ is independently an optionally substituted $C_{1-6}$ aliphatic or an optionally substituted 3-7 membered saturated or partially unsaturated monocyclic heterocyclic ring having 1-2 heteroatoms independently selected from nitrogen, oxygen, and sulfur. In some embodiments, each instance of $R^{1C}$ is independently an optionally substituted phenyl or an optionally substituted 5-6 membered monocyclic heteroaryl ring having 1-4 heteroatoms independently selected from nitrogen, oxygen, and sulfur.

In some embodiments, each instance of $R^{1C}$ is independently an optionally substituted $C_{1-6}$ aliphatic or an optionally substituted phenyl. In some embodiments, each instance of $R^{1C}$ is independently an optionally substituted 3-7 membered saturated or partially unsaturated monocyclic heterocyclic ring having 1-2 heteroatoms independently selected from nitrogen, oxygen, and sulfur, or an optionally substituted 5-6 membered monocyclic heteroaryl ring having 1-4 heteroatoms independently selected from nitrogen, oxygen, and sulfur.

In some embodiments, each instance of $R^{1C}$ is independently an optionally substituted group selected from phenyl, a 3-7 membered saturated or partially unsaturated monocyclic heterocyclic ring having 1-2 heteroatoms independently selected from nitrogen, oxygen, and sulfur, and a 5-6 membered monocyclic heteroaryl ring having 1-4 heteroatoms independently selected from nitrogen, oxygen, and sulfur.

In some embodiments, each instance of $R^{1C}$ is independently a $C_{1-6}$ aliphatic. In some embodiments, $R^{1C}$ is phenyl. In some embodiments, each instance of $R^{1C}$ is independently a 3-7 membered saturated or partially unsaturated monocyclic heterocyclic ring having 1-2 heteroatoms independently selected from nitrogen, oxygen, and sulfur. In some embodiments, each instance of $R^{1C}$ is independently a 5-6 membered monocyclic heteroaryl ring having 1-4 heteroatoms independently selected from nitrogen, oxygen, and sulfur.

In some embodiments, each instance of $R^{1C}$ is independently a $C_{1-6}$ aliphatic or a 3-7 membered saturated or partially unsaturated monocyclic heterocyclic ring having 1-2 heteroatoms independently selected from nitrogen, oxygen, and sulfur. In some embodiments, each instance of $R^{1C}$ is independently phenyl or a 5-6 membered monocyclic heteroaryl ring having 1-4 heteroatoms independently selected from nitrogen, oxygen, and sulfur.

In some embodiments, each instance of $R^{1C}$ is independently a $C_{1-6}$ aliphatic or phenyl. In some embodiments, each instance of $R^{1C}$ is independently a 3-7 membered saturated or partially unsaturated monocyclic heterocyclic ring having 1-2 heteroatoms independently selected from nitrogen, oxygen, and sulfur, or a 5-6 membered monocyclic heteroaryl ring having 1-4 heteroatoms independently selected from nitrogen, oxygen, and sulfur.

In some embodiments, each instance of $R^{1C}$ is independently phenyl, a 3-7 membered saturated or partially unsaturated monocyclic heterocyclic ring having 1-2 heteroatoms independently selected from nitrogen, oxygen, and sulfur, or a 5-6 membered monocyclic heteroaryl ring having 1-4 heteroatoms independently selected from nitrogen, oxygen, and sulfur.

In some embodiments, each instance of $R^{1C}$ is independently halogen, —CN, —O-(optionally substituted $C_{1-6}$ aliphatic), or an optionally substituted $C_{1-6}$ aliphatic. In some embodiments, each instance of $R^{1C}$ is independently halogen, —CN, —O—($C_{1-6}$ aliphatic), or $C_{1-6}$ aliphatic; wherein each $C_{1-6}$ aliphatic is optionally substituted with one or more halogen atoms. In some embodiments, each instance of $R^{1C}$ is independently halogen or $C_{1-3}$ aliphatic optionally substituted with 1-3 halogen. In some embodiments, each instance of $R^{1C}$ is independently fluorine, chlorine, —CH$_3$, —CHF$_2$, or —CF$_3$.

In some embodiments, each instance of $R^{1C}$ is independently oxo, halogen, —CN, —NO$_2$, —OR, —SR, —NR$_2$, —S(O)$_2$R, —S(O)$_2$NR$_2$, —S(O)$_2$F, —S(O)R, —S(O)NR$_2$, —S(O)(NR)R, —C(O)R, —C(O)OR, —C(O)NR$_2$, —C(O)N(R)OR, —OC(O)R, —OC(O)NR$_2$, —N(R)C(O)OR, —N(R)C(O)R, —N(R)C(O)NR$_2$, —N(R)C(NR)NR$_2$, —N(R)S(O)$_2$NR$_2$, —N(R)S(O)$_2$R, —P(O)R$_2$, —P(O)(R)OR, —B(OR)$_2$, or optionally substituted $C_{1-6}$ aliphatic.

In some embodiments, each instance of $R^{1C}$ is independently selected from the groups depicted in the compounds in Table 1.

As defined generally above, each instance of $R^{2C}$ is independently oxo, deuterium, halogen, —CN, —NO$_2$, —OR, —SR, —NR$_2$, —S(O)$_2$R, —S(O)$_2$NR$_2$, —S(O)$_2$F, —S(O)R, —S(O)NR$_2$, —S(O)(NR)R, —C(O)R, —C(O)OR, —C(O)NR$_2$, —C(O)N(R)OR, —OC(O)R, —OC(O)NR$_2$, —N(R)C(O)OR, —N(R)C(O)R, —N(R)C(O)NR$_2$, —N(R)C(NR)NR$_2$, —N(R)S(O)$_2$NR$_2$, —N(R)S(O)$_2$R, —P(O)R$_2$, —P(O)(R)OR, —B(OR)$_2$, or an optionally substituted group selected from $C_{1-6}$ aliphatic, phenyl, a 3-7 membered saturated or partially unsaturated monocyclic heterocyclic ring having 1-2 heteroatoms independently selected from nitrogen, oxygen, and sulfur, and a 5-6 membered monocyclic heteroaryl ring having 1-4 heteroatoms independently selected from nitrogen, oxygen, and sulfur.

In some embodiments, each instance of $R^{2C}$ is independently oxo, halogen, —CN, —NO$_2$, —OR, —SR, —NR$_2$, —S(O)$_2$R, —S(O)$_2$NR$_2$, —S(O)$_2$F, —S(O)R, —S(O)NR$_2$, —S(O)(NR)R, —C(O)R, —C(O)OR, —C(O)NR$_2$, —C(O)N(R)OR, —OC(O)R, —OC(O)NR$_2$, —N(R)C(O)OR, —N(R)C(O)R, —N(R)C(O)NR$_2$, —N(R)C(NR)NR$_2$, —N(R)S(O)$_2$NR$_2$, —N(R)S(O)$_2$R, —P(O)R$_2$, —P(O)(R)OR, —B(OR)$_2$, or an optionally substituted group selected from C$_{1-6}$ aliphatic, phenyl, a 3-7 membered saturated or partially unsaturated monocyclic heterocyclic ring having 1-2 heteroatoms independently selected from nitrogen, oxygen, and sulfur, and a 5-6 membered monocyclic heteroaryl ring having 1-4 heteroatoms independently selected from nitrogen, oxygen, and sulfur.

In some embodiments, each instance of $R^{2C}$ is independently oxo, halogen, —CN, —NO$_2$, —OR, —SR, —NR$_2$, —S(O)$_2$R, —S(O)$_2$NR$_2$, —S(O)$_2$F, —S(O)R, —S(O)NR$_2$, —S(O)(NR)R, —C(O)R, —C(O)OR, —C(O)NR$_2$, —C(O)N(R)OR, —OC(O)R, —OC(O)NR$_2$, —N(R)C(O)OR, —N(R)C(O)R, —N(R)C(O)NR$_2$, —N(R)C(NR)NR$_2$, —N(R)S(O)$_2$NR$_2$, —N(R)S(O)$_2$R, —P(O)R$_2$, —P(O)(R)OR, or —B(OR)$_2$. In some embodiments, each instance of $R^{2C}$ is independently an optionally substituted group selected from C$_{1-6}$ aliphatic, phenyl, a 3-7 membered saturated or partially unsaturated monocyclic heterocyclic ring having 1-2 heteroatoms independently selected from nitrogen, oxygen, and sulfur, and a 5-6 membered monocyclic heteroaryl ring having 1-4 heteroatoms independently selected from nitrogen, oxygen, and sulfur.

In some embodiments, $R^{2C}$ is oxo. In some embodiments, $R^{2C}$ is deuterium. In some embodiments, each instance of $R^{2C}$ is independently halogen. In some embodiments, $R^{2C}$ is —CN. In some embodiments, $R^{2C}$ is —NO$_2$. In some embodiments, $R^{2C}$ is —OR. In some embodiments, $R^{2C}$ is —SR. In some embodiments, $R^{2C}$ is —NR$_2$. In some embodiments, $R^{2C}$ is —S(O)$_2$R. In some embodiments, $R^{2C}$ is —S(O)$_2$NR$_2$. In some embodiments, $R^{2C}$ is —S(O)$_2$F.

In some embodiments, $R^{2C}$ is —S(O)R. In some embodiments, $R^{2C}$ is —S(O)NR$_2$. In some embodiments, $R^{2C}$ is —S(O)(NR)R. In some embodiments, $R^{2C}$ is —C(O)R. In some embodiments, $R^{2C}$ is —C(O)OR. In some embodiments, $R^{2C}$ is —C(O)NR$_2$. In some embodiments, $R^{2C}$ is —C(O)N(R)OR. In some embodiments, $R^{2C}$ is —OC(O)R. In some embodiments, $R^{2C}$ is —OC(O)NR$_2$. In some embodiments, $R^{2C}$ is —N(R)C(O)OR. In some embodiments, $R^{2C}$ is —N(R)C(O)R. In some embodiments, $R^{2C}$ is —N(R)C(O)NR$_2$. In some embodiments, $R^{2C}$ is —N(R)C(NR)NR$_2$. In some embodiments, $R^{2C}$ is —N(R)S(O)$_2$NR$_2$. In some embodiments, $R^{2C}$ is —N(R)S(O)$_2$R. In some embodiments, $R^{2C}$ is —P(O)R$_2$. In some embodiments, $R^{2C}$ is —P(O)(R)OR. In some embodiments, $R^{2C}$ is —B(OR)$_2$.

In some embodiments, each instance of $R^{2C}$ is independently halogen, —CN, —NO$_2$, —OR, —SR, —NR$_2$, —S(O)$_2$R, —S(O)$_2$NR$_2$, —S(O)$_2$F, —S(O)R, —S(O)NR$_2$, —S(O)(NR)R, —C(O)R, —C(O)OR, —C(O)NR$_2$, —C(O)N(R)OR, —OC(O)R, —OC(O)NR$_2$, —N(R)C(O)OR, —N(R)C(O)R, —N(R)C(O)NR$_2$, —N(R)C(NR)NR$_2$, —N(R)S(O)$_2$NR$_2$, —N(R)S(O)$_2$R, —P(O)R$_2$, —P(O)(R)OR, or —B(OR)$_2$.

In some embodiments, each instance of $R^{2C}$ is independently halogen, —CN, or —NO$_2$. In some embodiments, each instance of $R^{2C}$ is independently —OR, —SR, or —NR$_2$. In some embodiments, each instance of $R^{2C}$ is independently —S(O)$_2$R, —S(O)$_2$NR$_2$, —S(O)$_2$F, —S(O)R, —S(O)NR$_2$, or —S(O)(NR)R. In some embodiments, each instance of $R^{2C}$ is independently —C(O)R, —C(O)OR, —C(O)NR$_2$, or —C(O)N(R)OR. In some embodiments, each instance of $R^{2C}$ is independently —OC(O)R or —OC(O)NR$_2$. In some embodiments, each instance of $R^{2C}$ is independently —N(R)C(O)OR, —N(R)C(O)R, —N(R)C(O)NR$_2$, —N(R)C(NR)NR$_2$, —N(R)S(O)$_2$NR$_2$, or —N(R)S(O)$_2$R. In some embodiments, each instance of $R^{2C}$ is independently —P(O)R$_2$ or —P(O)(R)OR.

In some embodiments, each instance of $R^{2C}$ is independently —OR, —OC(O)R, or —OC(O)NR$_2$. In some embodiments, each instance of $R^{2C}$ is independently —SR, —S(O)$_2$R, —S(O)$_2$NR$_2$, —S(O)$_2$F, —S(O)R, —S(O)NR$_2$, or —S(O)(NR)R. In some embodiments, each instance of $R^{2C}$ is independently —NR$_2$, —N(R)C(O)OR, —N(R)C(O)R, —N(R)C(O)NR$_2$, —N(R)C(NR)NR$_2$, —N(R)S(O)$_2$NR$_2$, or —N(R)S(O)$_2$R.

In some embodiments, each instance of $R^{2C}$ is independently —S(O)$_2$R, —S(O)$_2$NR$_2$, or —S(O)$_2$F. In some embodiments, each instance of $R^{2C}$ is independently —S(O)R, —S(O)NR$_2$, or —S(O)(NR)R. In some embodiments, each instance of $R^{2C}$ is independently —SR, —S(O)$_2$R, or —S(O)R. In some embodiments, each instance of $R^{2C}$ is independently —S(O)$_2$NR$_2$, —S(O)NR$_2$, or —S(O)(NR)R. In some embodiments, each instance of $R^{2C}$ is independently —S(O)$_2$NR$_2$ or —S(O)NR$_2$. In some embodiments, each instance of $R^{2C}$ is independently —SR, —S(O)$_2$R, —S(O)$_2$NR$_2$, or —S(O)R.

In some embodiments, each instance of $R^{2C}$ is independently —N(R)C(O)OR, —N(R)C(O)R, or —N(R)C(O)NR$_2$. In some embodiments, each instance of $R^{2C}$ is independently —N(R)S(O)$_2$NR$_2$ or —N(R)S(O)$_2$R. In some embodiments, each instance of $R^{2C}$ is independently —N(R)C(O)OR or —N(R)C(O)R. In some embodiments, each instance of $R^{2C}$ is independently —N(R)C(O)NR$_2$ or —N(R)S(O)$_2$NR$_2$. In some embodiments, each instance of $R^{2C}$ is independently —N(R)C(O)OR, —N(R)C(O)R, or —N(R)S(O)$_2$R.

In some embodiments, each instance of $R^{2C}$ is independently —NR$_2$, —N(R)C(O)OR, —N(R)C(O)R, or —N(R)C(O)NR$_2$. In some embodiments, each instance of $R^{2C}$ is independently —NR$_2$, —N(R)C(O)OR, or —N(R)C(O)R. In some embodiments, each instance of $R^{2C}$ is independently —NR$_2$, —N(R)C(O)OR, —N(R)C(O)R, or —N(R)S(O)$_2$R.

In some embodiments, each instance of $R^{2C}$ is independently an optionally substituted C$_{1-6}$ aliphatic. In some embodiments, each instance of $R^{21}$ is independently an optionally substituted phenyl. In some embodiments, each instance of $R^{2C}$ is independently an optionally substituted 3-7 membered saturated or partially unsaturated monocyclic heterocyclic ring having 1-2 heteroatoms independently selected from nitrogen, oxygen, and sulfur. In some embodiments, each instance of $R^{2C}$ is independently an optionally substituted 5-6 membered monocyclic heteroaryl ring having 1-4 heteroatoms independently selected from nitrogen, oxygen, and sulfur.

In some embodiments, each instance of $R^{2C}$ is independently an optionally substituted C$_{1-6}$ aliphatic or an optionally substituted 3-7 membered saturated or partially unsaturated monocyclic heterocyclic ring having 1-2 heteroatoms independently selected from nitrogen, oxygen, and sulfur. In some embodiments, each instance of $R^{2C}$ is independently an optionally substituted phenyl or an optionally substituted 5-6 membered monocyclic heteroaryl ring having 1-4 heteroatoms independently selected from nitrogen, oxygen, and sulfur.

In some embodiments, each instance of $R^{2C}$ is independently an optionally substituted C$_{1-6}$ aliphatic or an optionally substituted phenyl. In some embodiments, each instance of $R^{2C}$ is independently an optionally substituted 3-7 membered saturated or partially unsaturated monocyclic heterocyclic ring having 1-2 heteroatoms independently selected from nitrogen, oxygen, and sulfur, or an optionally substituted 5-6 membered monocyclic heteroaryl ring having 1-4 heteroatoms independently selected from nitrogen, oxygen, and sulfur.

In some embodiments, each instance of $R^{2C}$ is independently an optionally substituted group selected from phenyl, a 3-7 membered saturated or partially unsaturated monocyclic heterocyclic ring having 1-2 heteroatoms independently selected from nitrogen, oxygen, and sulfur, and a 5-6 membered monocyclic heteroaryl ring having 1-4 heteroatoms independently selected from nitrogen, oxygen, and sulfur.

In some embodiments, each instance of $R^{2C}$ is independently a $C_{1-6}$ aliphatic. In some embodiments, $R^{2C}$ is phenyl. In some embodiments, each instance of $R^{2C}$ is independently a 3-7 membered saturated or partially unsaturated monocyclic heterocyclic ring having 1-2 heteroatoms independently selected from nitrogen, oxygen, and sulfur. In some embodiments, each instance of $R^{2C}$ is independently a 5-6 membered monocyclic heteroaryl ring having 1-4 heteroatoms independently selected from nitrogen, oxygen, and sulfur.

In some embodiments, each instance of $R^{2C}$ is independently a $C_{1-6}$ aliphatic or a 3-7 membered saturated or partially unsaturated monocyclic heterocyclic ring having 1-2 heteroatoms independently selected from nitrogen, oxygen, and sulfur. In some embodiments, each instance of $R^{2C}$ is independently phenyl or a 5-6 membered monocyclic heteroaryl ring having 1-4 heteroatoms independently selected from nitrogen, oxygen, and sulfur.

In some embodiments, each instance of $R^{2C}$ is independently a $C_{1-6}$ aliphatic or phenyl. In some embodiments, each instance of $R^{2C}$ is independently a 3-7 membered saturated or partially unsaturated monocyclic heterocyclic ring having 1-2 heteroatoms independently selected from nitrogen, oxygen, and sulfur, or a 5-6 membered monocyclic heteroaryl ring having 1-4 heteroatoms independently selected from nitrogen, oxygen, and sulfur.

In some embodiments, each instance of $R^{2C}$ is independently phenyl, a 3-7 membered saturated or partially unsaturated monocyclic heterocyclic ring having 1-2 heteroatoms independently selected from nitrogen, oxygen, and sulfur, or a 5-6 membered monocyclic heteroaryl ring having 1-4 heteroatoms independently selected from nitrogen, oxygen, and sulfur.

In some embodiments, each instance of $R^{2C}$ is independently halogen, —CN, —O-(optionally substituted $C_{1-6}$ aliphatic), or an optionally substituted $C_{1-6}$ aliphatic. In some embodiments, each instance of $R^{2C}$ is independently halogen, —CN, —O—($C_{1-6}$ aliphatic), or $C_{1-6}$ aliphatic; wherein each $C_{1-6}$ aliphatic is optionally substituted with one or more halogen atoms. In some embodiments, each instance of $R^{2C}$ is independently halogen or $C_{1-3}$ aliphatic optionally substituted with 1-3 halogen. In some embodiments, each instance of $R^{2C}$ is independently fluorine, chlorine, —CH$_3$, —CHF$_2$, or —CF$_3$.

In some embodiments, each instance of $R^{YC}$ is independently oxo, halogen, —CN, —NO$_2$, —OR, —SR, —NR$_2$, —S(O)$_2$R, —S(O)$_2$NR$_2$, —S(O)$_2$F, —S(O)R, —S(O)NR$_2$, —S(O)(NR)R, —C(O)R, —C(O)OR, —C(O)NR$_2$, —C(O)N(R)OR, —OC(O)R, —OC(O)NR$_2$, —N(R)C(O)OR, —N(R)C(O)R, —N(R)C(O)NR$_2$, —N(R)C(NR)NR$_2$, —N(R)S(O)$_2$NR$_2$, —N(R)S(O)$_2$R, —P(O)R$_2$, —P(O)(R)OR, —B(OR)$_2$, or optionally substituted $C_{1-6}$ aliphatic.

In some embodiments, each instance of $R^{2C}$ is independently selected from the groups depicted in the compounds in Table 1.

As defined generally above, each instance of $R^{EC}$ is independently oxo, deuterium, halogen, —CN, —NO$_2$, —OR, —SR, —NR$_2$, —S(O)$_2$R, —S(O)$_2$NR$_2$, —S(O)$_2$F, —S(O)R, —S(O)NR$_2$, —S(O)(NR)R, —C(O)R, —C(O)OR, —C(O)NR$_2$, —C(O)N(R)OR, —OC(O)R, —OC(O)NR$_2$, —N(R)C(O)OR, —N(R)C(O)R, —N(R)C(O)NR$_2$, —N(R)C(NR)NR$_2$, —N(R)S(O)$_2$NR$_2$, —N(R)S(O)$_2$R, —P(O)R$_2$, —P(O)(R)OR, —B(OR)$_2$, or an optionally substituted group selected from $C_{1-6}$ aliphatic, phenyl, a 3-7 membered saturated or partially unsaturated monocyclic heterocyclic ring having 1-2 heteroatoms independently selected from nitrogen, oxygen, and sulfur, and a 5-6 membered monocyclic heteroaryl ring having 1-4 heteroatoms independently selected from nitrogen, oxygen, and sulfur.

In some embodiments, each instance of $R^{EC}$ is independently oxo, deuterium, halogen, —CN, —NO$_2$, —OR, —SR, —NR$_2$, —S(O)$_2$R, —S(O)$_2$NR$_2$, —S(O)$_2$F, —S(O)R, —S(O)NR$_2$, —S(O)(NR)R, —C(O)R, —C(O)OR, —C(O)NR$_2$, —C(O)N(R)OR, —OC(O)R, —OC(O)NR$_2$, —N(R)C(O)OR, —N(R) C(O)R, —N(R)C(O)NR$_2$, —N(R)C(NR)NR$_2$, —N(R)S(O)$_2$NR$_2$, —N(R)S(O)$_2$R, —P(O)R$_2$, —P(O)(R) OR, or —B(OR)$_2$. In some embodiments, each instance of $R^{EC}$ is independently oxo, deuterium, halogen, —CN, —NO$_2$, —OR, —NR$_2$, —C(O)R, —C(O)OR, —C(O)NR$_2$, —OC(O)R, —N(R)C(O)R, or —N(R)S(O)$_2$R. In some embodiments, each instance of $R^{EC}$ is independently deuterium, halogen, —CN, —OR, or —NR$_2$. In some embodiments, each instance of $R^{EC}$ is independently deuterium or halogen. In some embodiments, each instance of $R^{EC}$ is independently halogen.

In some embodiments, each instance of $R^{EC}$ is independently an optionally substituted group selected from $C_{1-6}$ aliphatic, phenyl, a 3-7 membered saturated or partially unsaturated monocyclic heterocyclic ring having 1-2 heteroatoms independently selected from nitrogen, oxygen, and sulfur, and a 5-6 membered monocyclic heteroaryl ring having 1-4 heteroatoms independently selected from nitrogen, oxygen, and sulfur.

In some embodiments, each instance of $R^{EC}$ is independently selected from the groups depicted in the compounds in Table 1.

As defined generally above, each instance of $R^{QC}$ is independently oxo, deuterium, halogen, —CN, —NO$_2$, —OR, —SR, —NR$_2$, —S(O)$_2$R, —S(O)$_2$NR$_2$, —S(O)$_2$F, —S(O)R, —S(O)NR$_2$, —S(O)(NR)R, —C(O)R, —C(O)OR, —C(O)NR$_2$, —C(O)N(R)OR, —OC(O)R, —OC(O)NR$_2$, —N(R)C(O)OR, —N(R)C(O)R, —N(R)C(O)NR$_2$, —N(R)C(NR)NR$_2$, —N(R)S(O)$_2$NR$_2$, —N(R)S(O)$_2$R, —P(O)R$_2$, —P(O)(R)OR, —B(OR)$_2$, or an optionally substituted group selected from $C_{1-6}$ aliphatic, phenyl, a 3-7 membered saturated or partially unsaturated monocyclic heterocyclic ring having 1-2 heteroatoms independently selected from nitrogen, oxygen, and sulfur, and a 5-6 membered monocyclic heteroaryl ring having 1-4 heteroatoms independently selected from nitrogen, oxygen, and sulfur.

In some embodiments, each instance of $R^{QC}$ is independently oxo, halogen, —CN, —NO$_2$, —OR, —SR, —NR$_2$, —S(O)$_2$R, —S(O)$_2$NR$_2$, —S(O)$_2$F, —S(O)R, —S(O)NR$_2$, —S(O)(NR)R, —C(O)R, —C(O)OR, —C(O)NR$_2$, —C(O)N(R)OR, —OC(O)R, —OC(O)NR$_2$, —N(R)C(O)OR, —N(R)C(O)R, —N(R)C(O)NR$_2$, —N(R)C(NR)NR$_2$, —N(R)S(O)$_2$NR$_2$, —N(R)S(O)$_2$R, —P(O)R$_2$, —P(O)(R) OR, —B(OR)$_2$, or an optionally substituted group selected from $C_{1-6}$ aliphatic, phenyl, a 3-7 membered saturated or partially unsaturated monocyclic heterocyclic ring having 1-2 heteroatoms independently selected from nitrogen, oxygen, and sulfur, and a 5-6 membered monocyclic heteroaryl ring having 1-4 heteroatoms independently selected from nitrogen, oxygen, and sulfur.

In some embodiments, each instance of $R^{QC}$ is independently oxo, halogen, —CN, —NO$_2$, —OR, —SR, —NR$_2$, —S(O)$_2$R, —S(O)$_2$NR$_2$, —S(O)$_2$F, —S(O)R, —S(O)NR$_2$, —S(O)(NR)R, —C(O)R, —C(O)OR, —C(O)NR$_2$, —C(O)N(R)OR, —OC(O)R, —OC(O)NR$_2$, —N(R)C(O)OR, —N(R)C(O)R, —N(R)C(O)NR$_2$, —N(R)C(NR)NR$_2$, —N(R)S(O)$_2$NR$_2$, —N(R)S(O)$_2$R, —P(O)R$_2$, —P(O)(R)OR, or —B(OR)$_2$. In some embodiments, each instance of $R^{QC}$ is independently an optionally substituted group selected from $C_{1-6}$ aliphatic, phenyl, a 3-7 membered saturated or partially unsaturated monocyclic heterocyclic ring having 1-2 heteroatoms independently selected from nitrogen, oxygen, and sulfur, and a 5-6 membered monocyclic heteroaryl ring having 1-4 heteroatoms independently selected from nitrogen, oxygen, and sulfur.

In some embodiments, $R^{QC}$ is oxo. In some embodiments, $R^{QC}$ is deuterium. In some embodiments, each instance of $R^{QC}$ is independently halogen. In some embodiments, $R^{QC}$ is —CN. In some embodiments, $R^{QC}$ is —NO$_2$. In some embodiments, $R^{QC}$ is —OR. In some embodiments, $R^{QC}$ is —SR. In some embodiments, $R^{QC}$ is —NR$_2$. In some embodiments, $R^{QC}$ is —S(O)$_2$R. In some embodiments, $R^{QC}$ is —S(O)$_2$NR$_2$. In some embodiments, $R^{QC}$ is —S(O)$_2$F. In some embodiments, $R^{QC}$ is —S(O)R. In some embodiments, $R^{QC}$ is —S(O)NR$_2$.

In some embodiments, $R^{QC}$ is —S(O)(NR)R. In some embodiments, $R^{QC}$ is —C(O)R. In some embodiments, $R^{QC}$ is —C(O)OR. In some embodiments, $R^{QC}$ is —C(O)NR$_2$. In some embodiments, $R^{QC}$ is —C(O)N(R)OR. In some embodiments, $R^{QC}$ is —OC(O)R. In some embodiments, $R^{QC}$ is —OC(O)NR$_2$. In some embodiments, $R^{QC}$ is —N(R)C(O)OR. In some embodiments, $R^{QC}$ is —N(R)C(O)R. In some embodiments, $R^{QC}$ is —N(R)C(O)NR$_2$. In some embodiments, $R^{QC}$ is —N(R)C(NR)NR$_2$. In some embodiments, $R^{QC}$ is —N(R)S(O)$_2$NR$_2$. In some embodiments, $R^{QC}$ is —N(R)S(O)$_2$R. In some embodiments, $R^{QC}$ is —P(O)R$_2$. In some embodiments, $R^{QC}$ is —P(O)(R)OR. In some embodiments, $R^Q$ is —B(OR)$_2$.

In some embodiments, each instance of $R^{QC}$ is independently halogen, —CN, —NO$_2$, —OR, —SR, —NR$_2$, —S(O)$_2$R, —S(O)$_2$NR$_2$, —S(O)$_2$F, —S(O)R, —S(O)NR$_2$, —S(O)(NR)R, —C(O)R, —C(O)OR, —C(O)NR$_2$, —C(O)N(R)OR, —OC(O)R, —OC(O)NR$_2$, —N(R)C(O)OR, —N(R)C(O)R, —N(R)C(O)NR$_2$, —N(R)C(NR)NR$_2$, —N(R)S(O)$_2$NR$_2$, —N(R)S(O)$_2$R, —P(O)R$_2$, —P(O)(R)OR, or —B(OR)$_2$.

In some embodiments, each instance of $R^{QC}$ is independently halogen, —CN, or —NO$_2$. In some embodiments, each instance of $R^{QC}$ is independently —OR, —SR, or —NR$_2$. In some embodiments, each instance of $R^{QC}$ is independently —S(O)$_2$R, —S(O)$_2$NR$_2$, —S(O)$_2$F, —S(O)R, —S(O)NR$_2$, or —S(O)(NR)R. In some embodiments, each instance of $R^{QC}$ is independently —C(O)R, —C(O)OR, —C(O)NR$_2$, or —C(O)N(R)OR. In some embodiments, each instance of $R^{QC}$ is independently —OC(O)R or —OC(O)NR$_2$. In some embodiments, each instance of $R^{QC}$ is independently —N(R)C(O)OR, —N(R)C(O)R, —N(R)C(O)NR$_2$, —N(R)C(NR)NR$_2$, —N(R)S(O)$_2$NR$_2$, or —N(R)S(O)$_2$R. In some embodiments, each instance of $R^{QC}$ is independently —P(O)R$^2$ or —P(O)(R)OR.

In some embodiments, each instance of $R^{QC}$ is independently —OR, —OC(O)R, or —OC(O)NR$_2$. In some embodiments, each instance of $R^{QC}$ is independently —SR, —S(O)$_2$R, —S(O)$_2$NR$_2$, —S(O)$_2$F, —S(O)R, —S(O)NR$_2$, or —S(O)(NR)R. In some embodiments, each instance of $R^{QC}$ is independently —NR$_2$, —N(R)C(O)OR, —N(R)C(O)R, —N(R)C(O)NR$_2$, —N(R)C(NR)NR$_2$, —N(R)S(O)$_2$NR$_2$, or —N(R)S(O)$_2$R.

In some embodiments, each instance of $R^{QC}$ is independently —S(O)$_2$R, —S(O)$_2$NR$_2$, or —S(O)$_2$F. In some embodiments, each instance of $R^{QC}$ is independently —S(O)R, —S(O)NR$_2$, or —S(O)(NR)R. In some embodiments, each instance of $R^{QC}$ is independently —SR, —S(O)$_2$R, or —S(O)R. In some embodiments, each instance of $R^{QC}$ is independently —S(O)$_2$NR$_2$, —S(O)NR$_2$, or —S(O)(NR)R. In some embodiments, each instance of $R^{QC}$ is independently —S(O)$_2$NR$_2$ or —S(O)NR$_2$. In some embodiments, each instance of $R^{QC}$ is independently —SR, —S(O)$_2$R, —S(O)$_2$NR$_2$, or —S(O)R.

In some embodiments, each instance of $R^{QC}$ is independently —N(R)C(O)OR, —N(R)C(O)R, or —N(R)C(O)NR$_2$. In some embodiments, each instance of $R^{QC}$ is independently —N(R)S(O)$_2$NR$_2$ or —N(R)S(O)$_2$R. In some embodiments, each instance of $R^{QC}$ is independently —N(R)C(O)OR or —N(R)C(O)R. In some embodiments, each instance of $R^{QC}$ is independently —N(R)C(O)NR$_2$ or —N(R)S(O)$_2$NR$_2$. In some embodiments, each instance of $R^{QC}$ is independently —N(R)C(O)OR, —N(R)C(O)R, or —N(R)S(O)$_2$R.

In some embodiments, each instance of $R^{QC}$ is independently —NR$_2$, —N(R)C(O)OR, —N(R)C(O)R, or —N(R)C(O)NR$_2$. In some embodiments, each instance of $R^{QC}$ is independently —NR$_2$, —N(R)C(O)OR, or —N(R)C(O)R. In some embodiments, each instance of $R^{QC}$ is independently —NR$_2$, —N(R)C(O)OR, —N(R)C(O)R, or —N(R)S(O)$_2$R.

In some embodiments, each instance of $R^{QC}$ is independently an optionally substituted $C_{1-6}$ aliphatic. In some embodiments, each instance of $R^{QC}$ is independently an optionally substituted phenyl. In some embodiments, each instance of $R^{QC}$ is independently an optionally substituted 3-7 membered saturated or partially unsaturated monocyclic heterocyclic ring having 1-2 heteroatoms independently selected from nitrogen, oxygen, and sulfur. In some embodiments, each instance of $R^{QC}$ is independently an optionally substituted 5-6 membered monocyclic heteroaryl ring having 1-4 heteroatoms independently selected from nitrogen, oxygen, and sulfur.

In some embodiments, each instance of $R^{QC}$ is independently an optionally substituted $C_{1-6}$ aliphatic or an optionally substituted 3-7 membered saturated or partially unsaturated monocyclic heterocyclic ring having 1-2 heteroatoms independently selected from nitrogen, oxygen, and sulfur. In some embodiments, each instance of $R^{QC}$ is independently an optionally substituted phenyl or an optionally substituted 5-6 membered monocyclic heteroaryl ring having 1-4 heteroatoms independently selected from nitrogen, oxygen, and sulfur.

In some embodiments, each instance of $R^{QC}$ is independently an optionally substituted $C_{1-6}$ aliphatic or an optionally substituted phenyl. In some embodiments, each instance of $R^{QC}$ is independently an optionally substituted 3-7 membered saturated or partially unsaturated monocyclic heterocyclic ring having 1-2 heteroatoms independently selected from nitrogen, oxygen, and sulfur, or an optionally substituted 5-6 membered monocyclic heteroaryl ring having 1-4 heteroatoms independently selected from nitrogen, oxygen, and sulfur.

In some embodiments, each instance of $R^{QC}$ is independently an optionally substituted group selected from phenyl, a 3-7 membered saturated or partially unsaturated monocyclic heterocyclic ring having 1-2 heteroatoms independently selected from nitrogen, oxygen, and sulfur, and a 5-6 membered monocyclic heteroaryl ring having 1-4 heteroatoms independently selected from nitrogen, oxygen, and sulfur.

In some embodiments, each instance of $R^{QC}$ is independently a $C_{1-6}$ aliphatic. In some embodiments, $R^{QC}$ is phenyl. In some embodiments, each instance of $R^{QC}$ is independently a 3-7 membered saturated or partially unsaturated monocyclic heterocyclic ring having 1-2 heteroatoms independently selected from nitrogen, oxygen, and sulfur. In some embodiments, each instance of $R^{QC}$ is independently a 5-6 membered monocyclic heteroaryl ring having 1-4 heteroatoms independently selected from nitrogen, oxygen, and sulfur.

In some embodiments, each instance of $R^{QC}$ is independently a $C_{1-6}$ aliphatic or a 3-7 membered saturated or partially unsaturated monocyclic heterocyclic ring having 1-2 heteroatoms independently selected from nitrogen, oxygen, and sulfur. In some embodiments, each instance of $R^{QC}$ is independently phenyl or a 5-6 membered monocyclic heteroaryl ring having 1-4 heteroatoms independently selected from nitrogen, oxygen, and sulfur.

In some embodiments, each instance of $R^{QC}$ is independently a $C_{1-6}$ aliphatic or phenyl. In some embodiments, each instance of $R^{QC}$ is independently a 3-7 membered saturated or partially unsaturated monocyclic heterocyclic ring having 1-2 heteroatoms independently selected from nitrogen, oxygen, and sulfur, or a 5-6 membered monocyclic heteroaryl ring having 1-4 heteroatoms independently selected from nitrogen, oxygen, and sulfur.

In some embodiments, each instance of $R^{QC}$ is independently phenyl, a 3-7 membered saturated or partially unsaturated monocyclic heterocyclic ring having 1-2 heteroatoms independently selected from nitrogen, oxygen, and sulfur, or a 5-6 membered monocyclic heteroaryl ring having 1-4 heteroatoms independently selected from nitrogen, oxygen, and sulfur.

In some embodiments, each instance of $R^{QC}$ is independently selected from the groups depicted in the compounds in Table 1.

As defined generally above, each instance of $R^{XC}$ is independently oxo, deuterium, halogen, —CN, —NO$_2$, —OR, —SR, —NR$_2$, —S(O)$_2$R, —S(O)$_2$NR$_2$, —S(O)$_2$F, —S(O)R, —S(O)NR$_2$, —S(O)(NR)R, —C(O)R, —C(O)OR, —C(O)NR$_2$, —C(O)N(R)OR, —OC(O)R, —OC(O)NR$_2$, —N(R)C(O)OR, —N(R)C(O)R, —N(R)C(O)NR$_2$, —N(R)C(NR)NR$_2$, —N(R)S(O)$_2$NR$_2$, —N(R)S(O)$_2$R, —P(O)R$_2$, —P(O)(R)OR, —B(OR)$_2$, or an optionally substituted group selected from $C_{1-6}$ aliphatic, phenyl, a 3-7 membered saturated or partially unsaturated monocyclic heterocyclic ring having 1-2 heteroatoms independently selected from nitrogen, oxygen, and sulfur, and a 5-6 membered monocyclic heteroaryl ring having 1-4 heteroatoms independently selected from nitrogen, oxygen, and sulfur.

In some embodiments, each instance of $R^{XC}$ is independently oxo, halogen, —CN, —NO$_2$, —OR, —SR, —NR$_2$, —S(O)$_2$R, —S(O)$_2$NR$_2$, —S(O)$_2$F, —S(O)R, —S(O)NR$_2$, —S(O)(NR)R, —C(O)R, —C(O)OR, —C(O)NR$_2$, —C(O)N(R)OR, —OC(O)R, —OC(O)NR$_2$, —N(R)C(O)OR, —N(R)C(O)R, —N(R)C(O)NR$_2$, —N(R)C(NR)NR$_2$, —N(R)S(O)$_2$NR$_2$, —N(R)S(O)$_2$R, —P(O)R$_2$, —P(O)(R)OR, —B(OR)$_2$, or an optionally substituted group selected from $C_{1-6}$ aliphatic, phenyl, a 3-7 membered saturated or partially unsaturated monocyclic heterocyclic ring having 1-2 heteroatoms independently selected from nitrogen, oxygen, and sulfur, and a 5-6 membered monocyclic heteroaryl ring having 1-4 heteroatoms independently selected from nitrogen, oxygen, and sulfur.

In some embodiments, each instance of $R^{XC}$ is independently oxo, halogen, —CN, —NO$_2$, —OR, —SR, —NR$_2$, —S(O)$_2$R, —S(O)$_2$NR$_2$, —S(O)$_2$F, —S(O)R, —S(O)NR$_2$, —S(O)(NR)R, —C(O)R, —C(O)OR, —C(O)NR$_2$, —C(O)N(R)OR, —OC(O)R, —OC(O)NR$_2$, —N(R)C(O)OR, —N(R)C(O)R, —N(R)C(O)NR$_2$, —N(R)C(NR)NR$_2$, —N(R)S(O)$_2$NR$_2$, —N(R)S(O)$_2$R, —P(O)R$_2$, —P(O)(R)OR, or —B(OR)$_2$. In some embodiments, each instance of $R^{XC}$ is independently an optionally substituted group selected from $C_{1-6}$ aliphatic, phenyl, a 3-7 membered saturated or partially unsaturated monocyclic heterocyclic ring having 1-2 heteroatoms independently selected from nitrogen, oxygen, and sulfur, and a 5-6 membered monocyclic heteroaryl ring having 1-4 heteroatoms independently selected from nitrogen, oxygen, and sulfur.

In some embodiments, $R^{XC}$ is oxo. In some embodiments, $R^{XC}$ is deuterium. In some embodiments, each instance of $R^{XC}$ is independently halogen. In some embodiments, $R^{XC}$ is —CN. In some embodiments, $R^{XC}$ is —NO$_2$. In some embodiments, $R^{XC}$ is —OR. In some embodiments, $R^{XC}$ is —SR. In some embodiments, $R^{XC}$ is —NR$_2$. In some embodiments, $R^{XC}$ is —S(O)$_2$R. In some embodiments, $R^{XC}$ is —S(O)$_2$NR$_2$. In some embodiments, $R^{XC}$ is —S(O)$_2$F. In some embodiments, $R^{XC}$ is —S(O)R. In some embodiments, $R^{XC}$ is —S(O)NR$_2$.

In some embodiments, $R^{XC}$ is —S(O)(NR)R. In some embodiments, $R^{XC}$ is —C(O)R. In some embodiments, $R^{XC}$ is —C(O)OR. In some embodiments, $R^{XC}$ is —C(O)NR$_2$. In some embodiments, $R^{XC}$ is —C(O)N(R)OR. In some embodiments, $R^{XC}$ is —OC(O)R. In some embodiments, $R^{XC}$ is —OC(O)NR$_2$. In some embodiments, $R^{XC}$ is —N(R)C(O)OR. In some embodiments, $R^{XC}$ is —N(R)C(O)R. In some embodiments, $R^{XC}$ is —N(R)C(O)NR$_2$. In some embodiments, $R^{XC}$ is —N(R)C(NR)NR$_2$. In some embodiments, $R^{XC}$ is —N(R)S(O)$_2$NR$_2$. In some embodiments, $R^{XC}$ is —N(R)S(O)$_2$R. In some embodiments, $R^{XC}$ is —P(O)R$_2$. In some embodiments, $R^{XC}$ is —P(O)(R)OR. In some embodiments, $R^{XC}$ is —B(OR)$_2$.

In some embodiments, each instance of $R^{XC}$ is independently halogen, —CN, —NO$_2$, —OR, —SR, —NR$_2$, —S(O)$_2$R, —S(O)$_2$NR$_2$, —S(O)$_2$F, —S(O)R, —S(O)NR$_2$, —S(O)(NR)R, —C(O)R, —C(O)OR, —C(O)NR$_2$, —C(O)N(R)OR, —OC(O)R, —OC(O)NR$_2$, —N(R)C(O)OR, —N(R)C(O)R, —N(R)C(O)NR$_2$, —N(R)C(NR)NR$_2$, —N(R)S(O)$_2$NR$_2$, —N(R)S(O)$_2$R, —P(O)R$_2$, —P(O)(R)OR, or —B(OR)$_2$.

In some embodiments, each instance of $R^{XC}$ is independently halogen, —CN, or —NO$_2$. In some embodiments, each instance of $R^{XC}$ is independently —OR, —SR, or —NR$_2$. In some embodiments, each instance of $R^{XC}$ is independently —S(O)$_2$R, —S(O)$_2$NR$_2$, —S(O)$_2$F, —S(O)R, —S(O)NR$_2$, or —S(O)(NR)R. In some embodiments, each instance of $R^{XC}$ is independently —C(O)R, —C(O)OR, —C(O)NR$_2$, or —C(O)N(R)OR. In some embodiments, each instance of $R^{XC}$ is independently —OC(O)R or —OC(O)NR$_2$. In some embodiments, each instance of $R^{XC}$ is independently —N(R)C(O)OR, —N(R)C(O)R, —N(R)C(O)NR$_2$, —N(R)C(NR)NR$_2$, —N(R)S(O)$_2$NR$_2$, or —N(R)S(O)$_2$R. In some embodiments, each instance of $R^{XC}$ is independently —P(O)R$_2$ or —P(O)(R)OR.

In some embodiments, each instance of $R^{XC}$ is independently —OR, —OC(O)R, or —OC(O)NR$_2$. In some embodiments, each instance of $R^{XC}$ is independently —SR, —S(O)₂R, —S(O)₂NR₂, —S(O)₂F, —S(O)R, —S(O)NR₂, or —S(O)(NR)R. In some embodiments, each instance of $R^{XC}$ is independently —NR₂, —N(R)C(O)OR, —N(R)C(O)R, —N(R)C(O)NR₂, —N(R)C(NR)NR₂, —N(R)S(O)₂NR₂, or —N(R)S(O)₂R.

In some embodiments, each instance of $R^{XC}$ is independently —S(O)₂R, —S(O)₂NR₂, or —S(O)₂F. In some embodiments, each instance of $R^{XC}$ is independently —S(O)R, —S(O)NR₂, or —S(O)(NR)R. In some embodiments, each instance of $R^{XC}$ is independently —SR, —S(O)₂R, or —S(O)R. In some embodiments, each instance of $R^{XC}$ is independently —S(O)₂NR₂, —S(O)NR₂, or —S(O)(NR)R. In some embodiments, each instance of $R^{XC}$ is independently —S(O)₂NR₂ or —S(O)NR₂. In some embodiments, each instance of $R^{XC}$ is independently —SR, —S(O)₂R, —S(O)₂NR₂, or —S(O)R.

In some embodiments, each instance of $R^{XC}$ is independently —N(R)C(O)OR, —N(R)C(O)R, or —N(R)C(O)NR₂. In some embodiments, each instance of $R^{XC}$ is independently —N(R)S(O)₂NR₂ or —N(R)S(O)₂R. In some embodiments, each instance of $R^{XC}$ is independently —N(R)C(O)OR or —N(R)C(O)R. In some embodiments, each instance of $R^{XC}$ is independently —N(R)C(O)NR₂ or —N(R)S(O)₂NR₂. In some embodiments, each instance of $R^{XC}$ is independently —N(R)C(O)OR, —N(R)C(O)R, or —N(R)S(O)₂R.

In some embodiments, each instance of $R^{XC}$ is independently —NR₂, —N(R)C(O)OR, —N(R)C(O)R, or —N(R)C(O)NR₂. In some embodiments, each instance of $R^{XC}$ is independently —NR₂, —N(R)C(O)OR, or —N(R)C(O)R. In some embodiments, each instance of $R^{XC}$ is independently —NR₂, —N(R)C(O)OR, —N(R)C(O)R, or —N(R)S(O)₂R.

In some embodiments, each instance of $R^{XC}$ is independently an optionally substituted $C_{1-6}$ aliphatic. In some embodiments, each instance of $R^{XC}$ is independently an optionally substituted phenyl. In some embodiments, each instance of $R^{XC}$ is independently an optionally substituted 3-7 membered saturated or partially unsaturated monocyclic heterocyclic ring having 1-2 heteroatoms independently selected from nitrogen, oxygen, and sulfur. In some embodiments, each instance of RC is independently an optionally substituted 5-6 membered monocyclic heteroaryl ring having 1-4 heteroatoms independently selected from nitrogen, oxygen, and sulfur.

In some embodiments, each instance of $R^{XC}$ is independently an optionally substituted $C_{1-6}$ aliphatic or an optionally substituted 3-7 membered saturated or partially unsaturated monocyclic heterocyclic ring having 1-2 heteroatoms independently selected from nitrogen, oxygen, and sulfur. In some embodiments, each instance of $R^{XC}$ is independently an optionally substituted phenyl or an optionally substituted 5-6 membered monocyclic heteroaryl ring having 1-4 heteroatoms independently selected from nitrogen, oxygen, and sulfur.

In some embodiments, each instance of $R^{XC}$ is independently an optionally substituted $C_{1-6}$ aliphatic or an optionally substituted phenyl. In some embodiments, each instance of $R^{XC}$ is independently an optionally substituted 3-7 membered saturated or partially unsaturated monocyclic heterocyclic ring having 1-2 heteroatoms independently selected from nitrogen, oxygen, and sulfur, or an optionally substituted 5-6 membered monocyclic heteroaryl ring having 1-4 heteroatoms independently selected from nitrogen, oxygen, and sulfur.

In some embodiments, each instance of $R^{XC}$ is independently an optionally substituted group selected from phenyl, a 3-7 membered saturated or partially unsaturated monocyclic heterocyclic ring having 1-2 heteroatoms independently selected from nitrogen, oxygen, and sulfur, and a 5-6 membered monocyclic heteroaryl ring having 1-4 heteroatoms independently selected from nitrogen, oxygen, and sulfur.

In some embodiments, each instance of $R^{XC}$ is independently a $C_{1-6}$ aliphatic. In some embodiments, $R^{XC}$ is phenyl. In some embodiments, each instance of $R^{XC}$ is independently a 3-7 membered saturated or partially unsaturated monocyclic heterocyclic ring having 1-2 heteroatoms independently selected from nitrogen, oxygen, and sulfur. In some embodiments, each instance of $R^{XC}$ is independently a 5-6 membered monocyclic heteroaryl ring having 1-4 heteroatoms independently selected from nitrogen, oxygen, and sulfur.

In some embodiments, each instance of $R^{XC}$ is independently a $C_{1-6}$ aliphatic or a 3-7 membered saturated or partially unsaturated monocyclic heterocyclic ring having 1-2 heteroatoms independently selected from nitrogen, oxygen, and sulfur. In some embodiments, each instance of R is independently phenyl or a 5-6 membered monocyclic heteroaryl ring having 1-4 heteroatoms independently selected from nitrogen, oxygen, and sulfur.

In some embodiments, each instance of $R^{XC}$ is independently a $C_{1-6}$ aliphatic or phenyl. In some embodiments, each instance of $R^{XC}$ is independently a 3-7 membered saturated or partially unsaturated monocyclic heterocyclic ring having 1-2 heteroatoms independently selected from nitrogen, oxygen, and sulfur, or a 5-6 membered monocyclic heteroaryl ring having 1-4 heteroatoms independently selected from nitrogen, oxygen, and sulfur.

In some embodiments, each instance of $R^{XC}$ is independently phenyl, a 3-7 membered saturated or partially unsaturated monocyclic heterocyclic ring having 1-2 heteroatoms independently selected from nitrogen, oxygen, and sulfur, or a 5-6 membered monocyclic heteroaryl ring having 1-4 heteroatoms independently selected from nitrogen, oxygen, and sulfur.

In some embodiments, each instance of $R^{XC}$ is independently selected from the groups depicted in the compounds in Table 1.

As defined generally above, each instance of $R^{YC}$ is independently oxo, deuterium, halogen, —CN, —NO₂, —OR, —SR, —NR₂, —S(O)₂R, —S(O)₂NR₂, —S(O)₂F, —S(O)R, —S(O)NR₂, —S(O)(NR)R, —C(O)R, —C(O)OR, —C(O)NR₂, —C(O)N(R)OR, —OC(O)R, —OC(O)NR₂, —N(R)C(O)OR, —N(R)C(O)R, —N(R)C(O)NR₂, —N(R)C(NR)NR₂, —N(R)S(O)₂NR₂, —N(R)S(O)₂R, —P(O)R₂, —P(O)(R)OR, —B(OR)₂, or an optionally substituted group selected from $C_{1-6}$ aliphatic, phenyl, a 3-7 membered saturated or partially unsaturated monocyclic heterocyclic ring having 1-2 heteroatoms independently selected from nitrogen, oxygen, and sulfur, and a 5-6 membered monocyclic heteroaryl ring having 1-4 heteroatoms independently selected from nitrogen, oxygen, and sulfur.

In some embodiments, each instance of $R^{YC}$ is independently oxo, halogen, —CN, —NO₂, —OR, —SR, —NR₂, —S(O)₂R, —S(O)₂NR₂, —S(O)₂F, —S(O)R, —S(O)NR₂, —S(O)(NR)R, —C(O)R, —C(O)OR, —C(O)NR₂, —C(O)N(R)OR, —OC(O)R, —OC(O)NR₂, —N(R)C(O)OR, —N(R)C(O)R, —N(R)C(O)NR₂, —N(R)C(NR)NR₂, —N(R)S(O)₂NR₂, —N(R)S(O)₂R, —P(O)R₂, —P(O)(R)OR, —B(OR)₂, or an optionally substituted group selected from $C_{1-6}$ aliphatic, phenyl, a 3-7 membered saturated or partially unsaturated monocyclic heterocyclic ring having 1-2 heteroatoms independently selected from nitrogen, oxygen, and sulfur, and a 5-6 membered monocyclic heteroaryl ring having 1-4 heteroatoms independently selected from nitrogen, oxygen, and sulfur.

In some embodiments, each instance of $R^{YC}$ is independently oxo, halogen, —CN, —NO$_2$, —OR, —SR, —NR$_2$, —S(O)$_2$R, —S(O)$_2$NR$_2$, —S(O)$_2$F, —S(O)R, —S(O)NR$_2$, —S(O)(NR)R, —C(O)R, —C(O)OR, —C(O)NR$_2$, —C(O)N(R)OR, —OC(O)R, —OC(O)NR$_2$, —N(R)C(O)OR, —N(R)C(O)R, —N(R)C(O)NR$_2$, —N(R)C(NR)NR$_2$, —N(R)S(O)$_2$NR$_2$, —N(R)S(O)$_2$R, —P(O)R$_2$, —P(O)(R)OR, or —B(OR)$_2$. In some embodiments, each instance of $R^{YC}$ is independently an optionally substituted group selected from C$_{1-6}$ aliphatic, phenyl, a 3-7 membered saturated or partially unsaturated monocyclic heterocyclic ring having 1-2 heteroatoms independently selected from nitrogen, oxygen, and sulfur, and a 5-6 membered monocyclic heteroaryl ring having 1-4 heteroatoms independently selected from nitrogen, oxygen, and sulfur.

In some embodiments, $R^{YC}$ is oxo. In some embodiments, $R^{YC}$ is deuterium. In some embodiments, each instance of $R^{YC}$ is independently halogen. In some embodiments, $R^{YC}$ is —CN. In some embodiments, $R^{YC}$ is —NO$_2$. In some embodiments, $R^{YC}$ is —OR. In some embodiments, $R^{YC}$ is —SR. In some embodiments, $R^{YC}$ is —NR$_2$. In some embodiments, $R^{YC}$ is —S(O)$_2$R. In some embodiments, $R^{YC}$ is —S(O)$_2$NR$_2$. In some embodiments, $R^{YC}$ is —S(O)$_2$F. In some embodiments, $R^{YC}$ is —S(O)R. In some embodiments, $R^{YC}$ is —S(O)NR$_2$.

In some embodiments, $R^{YC}$ is —S(O)(NR)R. In some embodiments, $R^{YC}$ is —C(O)R. In some embodiments, $R^{YC}$ is —C(O)OR. In some embodiments, $R^{YC}$ is —C(O)NR$_2$. In some embodiments, $R^{YC}$ is —C(O)N(R)OR. In some embodiments, $R^{YC}$ is —OC(O)R. In some embodiments, $R^{YC}$ is —OC(O)NR$_2$. In some embodiments, $R^{YC}$ is —N(R)C(O)OR. In some embodiments, $R^{YC}$ is —N(R)C(O)R. In some embodiments, $R^{YC}$ is —N(R)C(O)NR$_2$. In some embodiments, $R^{YC}$ is —N(R)C(NR)NR$_2$. In some embodiments, $R^{YC}$ is —N(R)S(O)$_2$NR$_2$. In some embodiments, $R^{YC}$ is —N(R)S(O)$_2$R. In some embodiments, $R^{YC}$ is —P(O)R$_2$. In some embodiments, $R^{YC}$ is —P(O)(R)OR. In some embodiments, $R^{YC}$ is —B(OR)$_2$.

In some embodiments, each instance of $R^{YC}$ is independently halogen, —CN, —NO$_2$, —OR, —SR, —NR$_2$, —S(O)$_2$R, —S(O)$_2$NR$_2$, —S(O)$_2$F, —S(O)R, —S(O)NR$_2$, —S(O)(NR)R, —C(O)R, —C(O)OR, —C(O)NR$_2$, —C(O)N(R)OR, —OC(O)R, —OC(O)NR$_2$, —N(R)C(O)OR, —N(R)C(O)R, —N(R)C(O)NR$_2$, —N(R)C(NR)NR$_2$, —N(R)S(O)$_2$NR$_2$, —N(R)S(O)$_2$R, —P(O)R$_2$, —P(O)(R)OR, or —B(OR)$_2$.

In some embodiments, each instance of $R^{YC}$ is independently halogen, —CN, or —NO$_2$. In some embodiments, each instance of $R^{YC}$ is independently —OR, —SR, or —NR$_2$. In some embodiments, each instance of $R^{YC}$ is independently —S(O)$_2$R, —S(O)$_2$NR$_2$, —S(O)$_2$F, —S(O)R, —S(O)NR$_2$, or —S(O)(NR)R. In some embodiments, each instance of $R^{YC}$ is independently —C(O)R, —C(O)OR, —C(O)NR$_2$, or —C(O)N(R)OR. In some embodiments, each instance of $R^{YC}$ is independently —OC(O)R or —OC(O)NR$_2$. In some embodiments, each instance of $R^{YC}$ is independently —N(R)C(O)OR, —N(R)C(O)R, —N(R)C(O)NR$_2$, —N(R)C(NR)NR$_2$, —N(R)S(O)$_2$NR$_2$, or —N(R)S(O)$_2$R. In some embodiments, each instance of RC is independently —P(O)R$_2$ or —P(O)(R)OR.

In some embodiments, each instance of $R^{YC}$ is independently —OR, —OC(O)R, or —OC(O)NR$_2$. In some embodiments, each instance of $R^{YC}$ is independently —SR, —S(O)$_2$R, —S(O)$_2$NR$_2$, —S(O)$_2$F, —S(O)R, —S(O)NR$_2$, or —S(O)(NR)R. In some embodiments, each instance of $R^{YC}$ is independently —NR$_2$, —N(R)C(O)OR, —N(R)C(O)R, —N(R)C(O)NR$_2$, —N(R)C(NR)NR$_2$, —N(R)S(O)$_2$NR$_2$, or —N(R)S(O)$_2$R.

In some embodiments, each instance of $R^{YC}$ is independently —S(O)$_2$R, —S(O)$_2$NR$_2$, or —S(O)$_2$F. In some embodiments, each instance of $R^{YC}$ is independently —S(O)R, —S(O)NR$_2$, or —S(O)(NR)R. In some embodiments, each instance of R C is independently —SR, —S(O)$_2$R, or —S(O)R. In some embodiments, each instance of $R^{YC}$ is independently —S(O)$_2$NR$_2$, —S(O)NR$_2$, or —S(O)(NR)R. In some embodiments, each instance of $R^{YC}$ is independently —S(O)$_2$NR$_2$ or —S(O)NR$_2$. In some embodiments, each instance of $R^{YC}$ is independently —SR, —S(O)$_2$R, —S(O)$_2$NR$_2$, or —S(O)R.

In some embodiments, each instance of $R^{YC}$ is independently —N(R)C(O)OR, —N(R)C(O)R, or —N(R)C(O)NR$_2$. In some embodiments, each instance of $R^{YC}$ is independently —N(R)S(O)$_2$NR$_2$ or —N(R)S(O)$_2$R. In some embodiments, each instance of $R^{YC}$ is independently —N(R)C(O)OR or —N(R)C(O)R. In some embodiments, each instance of $R^{Y}$ is independently —N(R)C(O)NR$_2$ or —N(R)S(O)$_2$NR$_2$. In some embodiments, each instance of $R^{YC}$ is independently —N(R)C(O)OR, —N(R)C(O)R, or —N(R)S(O)$_2$R.

In some embodiments, each instance of $R^{YC}$ is independently —NR$_2$, —N(R)C(O)OR, —N(R)C(O)R, or —N(R)C(O)NR$_2$. In some embodiments, each instance of $R^{YC}$ is independently —NR$_2$, —N(R)C(O)OR, or —N(R)C(O)R. In some embodiments, each instance of $R^{YC}$ is independently —NR$_2$, —N(R)C(O)OR, —N(R)C(O)R, or —N(R)S(O)$_2$R.

In some embodiments, each instance of $R^{YC}$ is independently an optionally substituted C$_{1-6}$ aliphatic. In some embodiments, each instance of $R^{YC}$ is independently an optionally substituted phenyl. In some embodiments, each instance of $R^{YC}$ is independently an optionally substituted 3-7 membered saturated or partially unsaturated monocyclic heterocyclic ring having 1-2 heteroatoms independently selected from nitrogen, oxygen, and sulfur. In some embodiments, each instance of $R^{YC}$ is independently an optionally substituted 5-6 membered monocyclic heteroaryl ring having 1-4 heteroatoms independently selected from nitrogen, oxygen, and sulfur.

In some embodiments, each instance of $R^{YC}$ is independently an optionally substituted C$_{1-6}$ aliphatic or an optionally substituted 3-7 membered saturated or partially unsaturated monocyclic heterocyclic ring having 1-2 heteroatoms independently selected from nitrogen, oxygen, and sulfur. In some embodiments, each instance of RC is independently an optionally substituted phenyl or an optionally substituted 5-6 membered monocyclic heteroaryl ring having 1-4 heteroatoms independently selected from nitrogen, oxygen, and sulfur.

In some embodiments, each instance of $R^{YC}$ is independently an optionally substituted C$_{1-6}$ aliphatic or an optionally substituted phenyl. In some embodiments, each instance of $R^{YC}$ is independently an optionally substituted 3-7 membered saturated or partially unsaturated monocyclic heterocyclic ring having 1-2 heteroatoms independently selected from nitrogen, oxygen, and sulfur, or an optionally substituted 5-6 membered monocyclic heteroaryl ring having 1-4 heteroatoms independently selected from nitrogen, oxygen, and sulfur.

In some embodiments, each instance of $R^{YC}$ is independently an optionally substituted group selected from phenyl, a 3-7 membered saturated or partially unsaturated monocyclic heterocyclic ring having 1-2 heteroatoms independently selected from nitrogen, oxygen, and sulfur, and a 5-6 membered monocyclic heteroaryl ring having 1-4 heteroatoms independently selected from nitrogen, oxygen, and sulfur.

In some embodiments, each instance of $R^{YC}$ is independently a $C_{1-6}$ aliphatic. In some embodiments, $R^{YC}$ is phenyl. In some embodiments, each instance of $R^{YC}$ is independently a 3-7 membered saturated or partially unsaturated monocyclic heterocyclic ring having 1-2 heteroatoms independently selected from nitrogen, oxygen, and sulfur. In some embodiments, each instance of $R^{YC}$ is independently a 5-6 membered monocyclic heteroaryl ring having 1-4 heteroatoms independently selected from nitrogen, oxygen, and sulfur.

In some embodiments, each instance of $R^{YC}$ is independently a $C_{1-6}$ aliphatic or a 3-7 membered saturated or partially unsaturated monocyclic heterocyclic ring having 1-2 heteroatoms independently selected from nitrogen, oxygen, and sulfur. In some embodiments, each instance of $R^{YC}$ is independently phenyl or a 5-6 membered monocyclic heteroaryl ring having 1-4 heteroatoms independently selected from nitrogen, oxygen, and sulfur.

In some embodiments, each instance of $R^{YC}$ is independently a $C_{1-6}$ aliphatic or phenyl. In some embodiments, each instance of $R^{YC}$ is independently a 3-7 membered saturated or partially unsaturated monocyclic heterocyclic ring having 1-2 heteroatoms independently selected from nitrogen, oxygen, and sulfur, or a 5-6 membered monocyclic heteroaryl ring having 1-4 heteroatoms independently selected from nitrogen, oxygen, and sulfur.

In some embodiments, each instance of $R^{YC}$ is independently phenyl, a 3-7 membered saturated or partially unsaturated monocyclic heterocyclic ring having 1-2 heteroatoms independently selected from nitrogen, oxygen, and sulfur, or a 5-6 membered monocyclic heteroaryl ring having 1-4 heteroatoms independently selected from nitrogen, oxygen, and sulfur.

In some embodiments, each instance of $R^{YC}$ is independently oxo, halogen, —CN, —$NO_2$, —OR, —SR, —$NR_2$, —$S(O)_2R$, —$S(O)_2NR_2$, —$S(O)_2F$, —S(O)R, —$S(O)NR_2$, —S(O)(NR)R, —C(O)R, —C(O)OR, —$C(O)NR_2$, —C(O)N(R)OR, —OC(O)R, —$OC(O)NR_2$, —N(R)C(O)OR, —N(R)C(O)R, —$N(R)C(O)NR_2$, —$N(R)C(NR)NR_2$, —$N(R)S(O)_2NR_2$, —$N(R)S(O)_2R$, —$P(O)R_2$, —P(O)(R)OR, —$B(OR)_2$, or optionally substituted $C_{1-6}$ aliphatic.

In some embodiments, each instance of $R^{YC}$ is independently halogen, —CN, —OH, —O-(optionally substituted $C_{1-3}$ aliphatic), or an optionally substituted $C_{1-3}$ aliphatic. In some embodiments, each instance of $R^{YC}$ is independently halogen, —OH, —O—($C_{1-3}$ aliphatic), or $C_{1-3}$ aliphatic, wherein each $C_{1-3}$ aliphatic is optionally substituted with 1-3 halogen. In some embodiments, each instance of $R^{YC}$ is independently fluorine, chlorine, —OH, —$OCH_3$, —$OCF_3$, —$CH_3$, —$CHF_2$, or —$CF_3$. In some embodiments, each instance of $R^{YC}$ is independently fluorine or —OH.

In some embodiments, each instance of $R^{YC}$ is independently oxo, halogen, —CN, —OH, —O-(optionally substituted $C_{1-3}$ aliphatic), or an optionally substituted $C_{1-3}$ aliphatic. In some embodiments, each instance of $R^{YC}$ is independently oxo, halogen, —CN, —OH, —O—($C_{1-3}$ aliphatic), or $C_{1-3}$ aliphatic, wherein each $C_{1-3}$ aliphatic is optionally substituted with one or more halogen atoms. In some embodiments, each instance of $R^{YC}$ is independently oxo, halogen, —CN, —OH, —O—($C_{1-3}$ aliphatic), or $C_{1-3}$ aliphatic, wherein each $C_{1-3}$ aliphatic is optionally substituted with 1-3 halogen. In some embodiments, each instance of $R^{YC}$ is independently oxo, fluorine, chlorine, —CN, —OH, —$OCH_3$, —$OCF_3$, —$CH_3$, —$CHF_2$, or —$CF_3$. In some embodiments, each instance of $R^{YC}$ is independently oxo, —CN, fluorine, or —OH. In some embodiments, each instance of $R^{YC}$ is independently oxo, —CN, —$CH_3$, or —$CHF_2$. In some embodiments, each instance of $R^{YC}$ is independently —CN, —$CH_3$, or —$CHF_2$.

In some embodiments, each instance of $R^{YC}$ is independently selected from the groups depicted in the compounds in Table 1.

As defined generally above, each instance of $R^{ZC}$ is independently oxo, deuterium, halogen, —CN, —$NO_2$, —OR, —SR, —$NR_2$, —$S(O)_2R$, —$S(O)_2NR_2$, —$S(O)_2F$, —S(O)R, —$S(O)NR_2$, —S(O)(NR)R, —C(O)R, —C(O)OR, —$C(O)NR_2$, —C(O)N(R)OR, —OC(O)R, —$OC(O)NR_2$, —N(R)C(O)OR, —N(R)C(O)R, —$N(R)C(O)NR_2$, —$N(R)C(NR)NR_2$, —$N(R)S(O)_2NR_2$, —$N(R)S(O)_2R$, —$P(O)R_2$, —P(O)(R)OR, —$B(OR)_2$, or an optionally substituted group selected from $C_{1-6}$ aliphatic, phenyl, a 3-7 membered saturated or partially unsaturated monocyclic heterocyclic ring having 1-2 heteroatoms independently selected from nitrogen, oxygen, and sulfur, and a 5-6 membered monocyclic heteroaryl ring having 1-4 heteroatoms independently selected from nitrogen, oxygen, and sulfur.

In some embodiments, each instance of $R^{ZC}$ is independently oxo, halogen, —CN, —$NO_2$, —OR, —SR, —$NR_2$, —$S(O)_2R$, —$S(O)_2NR_2$, —$S(O)_2F$, —S(O)R, —$S(O)NR_2$, —S(O)(NR)R, —C(O)R, —C(O)OR, —$C(O)NR_2$, —C(O)N(R)OR, —OC(O)R, —$OC(O)NR_2$, —N(R)C(O)OR, —N(R)C(O)R, —$N(R)C(O)NR_2$, —$N(R)C(NR)NR_2$, —$N(R)S(O)_2NR_2$, —$N(R)S(O)_2R$, —$P(O)R_2$, —P(O)(R)OR, —$B(OR)_2$, or an optionally substituted group selected from $C_{1-6}$ aliphatic, phenyl, a 3-7 membered saturated or partially unsaturated monocyclic heterocyclic ring having 1-2 heteroatoms independently selected from nitrogen, oxygen, and sulfur, and a 5-6 membered monocyclic heteroaryl ring having 1-4 heteroatoms independently selected from nitrogen, oxygen, and sulfur.

In some embodiments, each instance of $R^{ZC}$ is independently oxo, halogen, —CN, —$NO_2$, —OR, —SR, —$NR_2$, —$S(O)_2R$, —$S(O)_2NR_2$, —$S(O)_2F$, —S(O)R, —$S(O)NR_2$, —S(O)(NR)R, —C(O)R, —C(O)OR, —$C(O)NR_2$, —C(O)N(R)OR, —OC(O)R, —$OC(O)NR_2$, —N(R)C(O)OR, —N(R)C(O)R, —$N(R)C(O)NR_2$, —$N(R)C(NR)NR_2$, —$N(R)S(O)_2NR_2$, —$N(R)S(O)_2R$, —$P(O)R_2$, —P(O)(R)OR, or —$B(OR)_2$. In some embodiments, each instance of $R^{ZC}$ is independently an optionally substituted group selected from $C_{1-6}$ aliphatic, phenyl, a 3-7 membered saturated or partially unsaturated monocyclic heterocyclic ring having 1-2 heteroatoms independently selected from nitrogen, oxygen, and sulfur, and a 5-6 membered monocyclic heteroaryl ring having 1-4 heteroatoms independently selected from nitrogen, oxygen, and sulfur.

In some embodiments, $R^{ZC}$ is oxo. In some embodiments, $R^{ZC}$ is deuterium. In some embodiments, each instance of $R^{ZC}$ is independently halogen. In some embodiments, $R^{ZC}$ is —CN. In some embodiments, $R^{ZC}$ is —$NO_2$. In some embodiments, $R^{ZC}$ is —OR. In some embodiments, $R^{ZC}$ is —SR. In some embodiments, $R^{ZC}$ is —$NR_2$. In some embodiments, $R^{ZC}$ is —$S(O)_2R$. In some embodiments, $R^{ZC}$ is —$S(O)_2NR_2$. In some embodiments, $R^{ZC}$ is —$S(O)_2F$.

In some embodiments, $R^{ZC}$ is —S(O)R. In some embodiments, $R^{ZC}$ is —$S(O)NR_2$. In some embodiments, $R^{ZC}$ is —S(O)(NR)R. In some embodiments, $R^{ZC}$ is —C(O)R. In some embodiments, $R^{ZC}$ is —C(O)OR. In some embodiments, $R^{ZC}$ is —$C(O)NR_2$. In some embodiments, $R^{ZC}$ is —C(O)N(R)OR. In some embodiments, $R^{ZC}$ is —OC(O)R. In some embodiments, $R^{ZC}$ is —$OC(O)NR_2$. In some embodiments, $R^{ZC}$ is —N(R)C(O)OR. In some embodiments, $R^{ZC}$ is —N(R)C(O)R. In some embodiments, $R^{ZC}$ is —N(R)C(O)NR$_2$. In some embodiments, $R^{ZC}$ is —N(R)C(NR)NR$_2$. In some embodiments, $R^{ZC}$ is —N(R)S(O)$_2$NR$_2$. In some embodiments, $R^{ZC}$ is —N(R)S(O)$_2$R. In some embodiments, $R^{ZC}$ is —P(O)R$_2$. In some embodiments, $R^{ZC}$ is —P(O)(R)OR. In some embodiments, $R^{ZC}$ is —B(OR)$_2$.

In some embodiments, each instance of $R^{ZC}$ is independently halogen, —CN, —NO$_2$, —OR, —SR, —NR$_2$, —S(O)$_2$R, —S(O)$_2$NR$_2$, —S(O)$_2$F, —S(O)R, —S(O)NR$_2$, —S(O)(NR)R, —C(O)R, —C(O)OR, —C(O)NR$_2$, —C(O)N(R)OR, —OC(O)R, —OC(O)NR$_2$, —N(R)C(O)OR, —N(R)C(O)R, —N(R)C(O)NR$_2$, —N(R)C(NR)NR$_2$, —N(R)S(O)$_2$NR$_2$, —N(R)S(O)$_2$R, —P(O)R$_2$, —P(O)(R)OR, or —B(OR)$_2$.

In some embodiments, each instance of $R^{ZC}$ is independently halogen, —CN, or —NO$_2$. In some embodiments, each instance of $R^{ZC}$ is independently —OR, —SR, or —NR$_2$. In some embodiments, each instance of $R^{ZC}$ is independently —S(O)$_2$R, —S(O)$_2$NR$_2$, —S(O)$_2$F, —S(O)R, —S(O)NR$_2$, or —S(O)(NR)R. In some embodiments, each instance of $R^{ZC}$ is independently —C(O)R, —C(O)OR, —C(O)NR$_2$, or —C(O)N(R)OR. In some embodiments, each instance of $R^{ZC}$ is independently —OC(O)R or —OC(O)NR$_2$. In some embodiments, each instance of $R^{ZC}$ is independently —N(R)C(O)OR, —N(R)C(O)R, —N(R)C(O)NR$_2$, —N(R)C(NR)NR$_2$, —N(R)S(O)$_2$NR$_2$, or —N(R)S(O)$_2$R. In some embodiments, each instance of $R^{ZC}$ is independently —P(O)R$_2$ or —P(O)(R)OR.

In some embodiments, each instance of $R^{ZC}$ is independently —OR, —OC(O)R, or —OC(O)NR$_2$. In some embodiments, each instance of $R^{ZC}$ is independently —SR, —S(O)$_2$R, —S(O)$_2$NR$_2$, —S(O)$_2$F, —S(O)R, —S(O)NR$_2$, or —S(O)(NR)R. In some embodiments, each instance of $R^{ZC}$ is independently —NR$_2$, —N(R)C(O)OR, —N(R)C(O)R, —N(R)C(O)NR$_2$, —N(R)C(NR)NR$_2$, —N(R)S(O)$_2$NR$_2$, or —N(R)S(O)$_2$R.

In some embodiments, each instance of $R^{ZC}$ is independently —S(O)$_2$R, —S(O)$_2$NR$_2$, or —S(O)$_2$F. In some embodiments, each instance of $R^{ZC}$ is independently —S(O)R, —S(O)NR$_2$, or —S(O)(NR)R. In some embodiments, each instance of $R^{ZC}$ is independently —SR, —S(O)$_2$R, or —S(O)R. In some embodiments, each instance of $R^{ZC}$ is independently —S(O)$_2$NR$_2$, —S(O)NR$_2$, or —S(O)(NR)R. In some embodiments, each instance of $R^{ZC}$ is independently —S(O)$_2$NR$_2$ or —S(O)NR$_2$. In some embodiments, each instance of $R^{ZC}$ is independently —SR, —S(O)$_2$R, —S(O)$_2$NR$_2$, or —S(O)R.

In some embodiments, each instance of $R^{ZC}$ is independently —N(R)C(O)OR, —N(R)C(O)R, or —N(R)C(O)NR$_2$. In some embodiments, each instance of $R^{ZC}$ is independently —N(R)S(O)$_2$NR$_2$ or —N(R)S(O)$_2$R. In some embodiments, each instance of $R^{ZC}$ is independently —N(R)C(O)OR or —N(R)C(O)R. In some embodiments, each instance of $R^{ZC}$ is independently —N(R)C(O)NR$_2$ or —N(R)S(O)$_2$NR$_2$. In some embodiments, each instance of $R^{ZC}$ is independently —N(R)C(O)OR, —N(R)C(O)R, or —N(R)S(O)$_2$R.

In some embodiments, each instance of $R^{ZC}$ is independently —NR$_2$, —N(R)C(O)OR, —N(R)C(O)R, or —N(R)C(O)NR$_2$. In some embodiments, each instance of $R^{ZC}$ is independently —NR$_2$, —N(R)C(O)OR, or —N(R)C(O)R. In some embodiments, each instance of $R^{ZC}$ is independently —NR$_2$, —N(R)C(O)OR, —N(R)C(O)R, or —N(R)S(O)$_2$R.

In some embodiments, each instance of $R^{ZC}$ is independently an optionally substituted $C_{1-6}$ aliphatic. In some embodiments, each instance of $R^{ZC}$ is independently an optionally substituted phenyl. In some embodiments, each instance of $R^{ZC}$ is independently an optionally substituted 3-7 membered saturated or partially unsaturated monocyclic heterocyclic ring having 1-2 heteroatoms independently selected from nitrogen, oxygen, and sulfur. In some embodiments, each instance of $R^{ZC}$ is independently an optionally substituted 5-6 membered monocyclic heteroaryl ring having 1-4 heteroatoms independently selected from nitrogen, oxygen, and sulfur.

In some embodiments, each instance of $R^{ZC}$ is independently an optionally substituted $C_{1-6}$ aliphatic or an optionally substituted 3-7 membered saturated or partially unsaturated monocyclic heterocyclic ring having 1-2 heteroatoms independently selected from nitrogen, oxygen, and sulfur. In some embodiments, each instance of $R^{ZC}$ is independently an optionally substituted phenyl or an optionally substituted 5-6 membered monocyclic heteroaryl ring having 1-4 heteroatoms independently selected from nitrogen, oxygen, and sulfur.

In some embodiments, each instance of $R^{ZC}$ is independently an optionally substituted $C_{1-6}$ aliphatic or an optionally substituted phenyl. In some embodiments, each instance of $R^{ZC}$ is independently an optionally substituted 3-7 membered saturated or partially unsaturated monocyclic heterocyclic ring having 1-2 heteroatoms independently selected from nitrogen, oxygen, and sulfur, or an optionally substituted 5-6 membered monocyclic heteroaryl ring having 1-4 heteroatoms independently selected from nitrogen, oxygen, and sulfur.

In some embodiments, each instance of $R^{ZC}$ is independently an optionally substituted group selected from phenyl, a 3-7 membered saturated or partially unsaturated monocyclic heterocyclic ring having 1-2 heteroatoms independently selected from nitrogen, oxygen, and sulfur, and a 5-6 membered monocyclic heteroaryl ring having 1-4 heteroatoms independently selected from nitrogen, oxygen, and sulfur.

In some embodiments, each instance of $R^{ZC}$ is independently a $C_{1-6}$ aliphatic. In some embodiments, $R^{ZC}$ is phenyl. In some embodiments, each instance of RC is independently a 3-7 membered saturated or partially unsaturated monocyclic heterocyclic ring having 1-2 heteroatoms independently selected from nitrogen, oxygen, and sulfur. In some embodiments, each instance of $R^{ZC}$ is independently a 5-6 membered monocyclic heteroaryl ring having 1-4 heteroatoms independently selected from nitrogen, oxygen, and sulfur.

In some embodiments, each instance of $R^{ZC}$ is independently a $C_{1-6}$ aliphatic or a 3-7 membered saturated or partially unsaturated monocyclic heterocyclic ring having 1-2 heteroatoms independently selected from nitrogen, oxygen, and sulfur. In some embodiments, each instance of $R^{ZC}$ is independently phenyl or a 5-6 membered monocyclic heteroaryl ring having 1-4 heteroatoms independently selected from nitrogen, oxygen, and sulfur.

In some embodiments, each instance of $R^{ZC}$ is independently a $C_{1-6}$ aliphatic or phenyl. In some embodiments, each instance of $R^{ZC}$ is independently a 3-7 membered saturated or partially unsaturated monocyclic heterocyclic ring having 1-2 heteroatoms independently selected from nitrogen, oxygen, and sulfur, or a 5-6 membered monocyclic heteroaryl ring having 1-4 heteroatoms independently selected from nitrogen, oxygen, and sulfur.

In some embodiments, each instance of $R^{ZC}$ is independently phenyl, a 3-7 membered saturated or partially unsaturated monocyclic heterocyclic ring having 1-2 heteroatoms independently selected from nitrogen, oxygen, and sulfur, or a 5-6 membered monocyclic heteroaryl ring having 1-4 heteroatoms independently selected from nitrogen, oxygen, and sulfur.

In some embodiments, each instance of $R^{ZC}$ is independently oxo, halogen, —CN, —NO$_2$, —OR, —SR, —NR$_2$, —S(O)$_2$R, —S(O)$_2$NR$_2$, —S(O)$_2$F, —S(O)R, —S(O)NR$_2$, —S(O)(NR)R, —C(O)R, —C(O)OR, —C(O)NR$_2$, —C(O)N(R)OR, —OC(O)R, —OC(O)NR$_2$, —N(R)C(O)OR, —N(R)C(O)R, —N(R)C(O)NR$_2$, —N(R)C(NR)NR$_2$, —N(R)S(O)$_2$NR$_2$, —N(R)S(O)$_2$R, —P(O)R$_2$, —P(O)(R)OR, —B(OR)$_2$, or optionally substituted C$_{1-6}$ aliphatic.

In some embodiments, each instance of $R^{ZC}$ is independently halogen, —CN, —OH, —O-(optionally substituted C$_{1-3}$ aliphatic), or an optionally substituted C$_{1-3}$ aliphatic. In some embodiments, each instance of $R^{ZC}$ is independently halogen, —OH, —O—(C$_{1-3}$ aliphatic), or C$_{1-3}$ aliphatic, wherein each C$_{1-3}$ aliphatic is optionally substituted with 1-3 halogen. In some embodiments, each instance of RC is independently fluorine, chlorine, —OH, —OCH$_3$, —OCF$_3$, —CH$_3$, —CHF$_2$, or —CF$_3$. In some embodiments, each instance of $R^{YC}$ is independently fluorine or —OH.

In some embodiments, each instance of $R^Z$ is independently selected from the groups depicted in the compounds in Table 1.

As defined generally above, each instance of $R^1$- is independently oxo, deuterium, halogen, —CN, —NO$_2$, —OR, —SR, —NR$_2$, —S(O)$_2$R, —S(O)$_2$NR$_2$, —S(O)$_2$F, —S(O)R, —S(O)NR$_2$, —S(O)(NR)R, —C(O)R, —C(O)OR, —C(O)NR$_2$, —C(O)N(R)OR, —OC(O)R, —OC(O)NR$_2$, —N(R)C(O)OR, —N(R)C(O)R, —N(R)C(O)NR$_2$, —N(R)C(NR)NR$_2$, —N(R)S(O)$_2$NR$_2$, —N(R)S(O)$_2$R, —P(O)R$_2$, —P(O)(R)OR, —B(OR)$_2$, or an optionally substituted group selected from C$_{1-6}$ aliphatic, phenyl, a 3-7 membered saturated or partially unsaturated monocyclic heterocyclic ring having 1-2 heteroatoms independently selected from nitrogen, oxygen, and sulfur, and a 5-6 membered monocyclic heteroaryl ring having 1-4 heteroatoms independently selected from nitrogen, oxygen, and sulfur.

In some embodiments, each instance of $R^{LC}$ is independently oxo, halogen, —CN, —NO$_2$, —OR, —SR, —NR$_2$, —S(O)$_2$R, —S(O)$_2$NR$_2$, —S(O)$_2$F, —S(O)R, —S(O)NR$_2$, —S(O)(NR)R, —C(O)R, —C(O)OR, —C(O)NR$_2$, —C(O)N(R)OR, —OC(O)R, —OC(O)NR$_2$, —N(R)C(O)OR, —N(R)C(O)R, —N(R)C(O)NR$_2$, —N(R)C(NR)NR$_2$, —N(R)S(O)$_2$NR$_2$, —N(R)S(O)$_2$R, —P(O)R$_2$, —P(O)(R)OR, —B(OR)$_2$, or an optionally substituted group selected from C$_{1-6}$ aliphatic, phenyl, a 3-7 membered saturated or partially unsaturated monocyclic heterocyclic ring having 1-2 heteroatoms independently selected from nitrogen, oxygen, and sulfur, and a 5-6 membered monocyclic heteroaryl ring having 1-4 heteroatoms independently selected from nitrogen, oxygen, and sulfur.

In some embodiments, each instance of $R^{LC}$ is independently oxo, halogen, —CN, —NO$_2$, —OR, —SR, —NR$_2$, —S(O)$_2$R, —S(O)$_2$NR$_2$, —S(O)$_2$F, —S(O)R, —S(O)NR$_2$, —S(O)(NR)R, —C(O)R, —C(O)OR, —C(O)NR$_2$, —C(O)N(R)OR, —OC(O)R, —OC(O)NR$_2$, —N(R)C(O)OR, —N(R)C(O)R, —N(R)C(O)NR$_2$, —N(R)C(NR)NR$_2$, —N(R)S(O)$_2$NR$_2$, —N(R)S(O)$_2$R, —P(O)R$_2$, —P(O)(R)OR, or —B(OR)$_2$. In some embodiments, each instance of $R^{LC}$ is independently an optionally substituted group selected from C$_{1-6}$ aliphatic, phenyl, a 3-7 membered saturated or partially unsaturated monocyclic heterocyclic ring having 1-2 heteroatoms independently selected from nitrogen, oxygen, and sulfur, and a 5-6 membered monocyclic heteroaryl ring having 1-4 heteroatoms independently selected from nitrogen, oxygen, and sulfur.

In some embodiments, $R^{LC}$ is oxo. In some embodiments, $R^{LC}$ is deuterium. In some embodiments, each instance of $R^{LC}$ is independently halogen. In some embodiments, $R^{LC}$ is —CN. In some embodiments, $R^{LC}$ is —NO$_2$. In some embodiments, $R^{LC}$ is —OR. In some embodiments, $R^{LC}$ is —SR. In some embodiments, $R^{LC}$ is —NR$_2$. In some embodiments, $R^{LC}$ is —S(O)$_2$R. In some embodiments, $R^{LC}$ is —S(O)$_2$NR$_2$. In some embodiments, $R^{LC}$ is —S(O)$_2$F.

In some embodiments, $R^{LC}$ is —S(O)R. In some embodiments, $R^{LC}$ is —S(O)NR$_2$. In some embodiments, $R^{LC}$ is —S(O)(NR)R. In some embodiments, $R^{LC}$ is —C(O)R. In some embodiments, $R^{LC}$ is —C(O)OR. In some embodiments, $R^{LC}$ is —C(O)NR$_2$. In some embodiments, $R^{LC}$ is —C(O)N(R)OR. In some embodiments, $R^{LC}$ is —OC(O)R. In some embodiments, $R^{LC}$ is —OC(O)NR$_2$. In some embodiments, $R^{LC}$ is —N(R)C(O)OR. In some embodiments, $R^{LC}$ is —N(R)C(O)R. In some embodiments, $R^{LC}$ is —N(R)C(O)NR$_2$. In some embodiments, $R^{LC}$ is —N(R)C(NR)NR$_2$. In some embodiments, $R^{LC}$ is —N(R)S(O)$_2$NR$_2$. In some embodiments, $R^{LC}$ is —N(R)S(O)$_2$R. In some embodiments, $R^{LC}$ is —P(O)R$_2$. In some embodiments, $R^{LC}$ is —P(O)(R)OR. In some embodiments, $R^{LC}$ is —B(OR)$_2$.

In some embodiments, each instance of $R^{LC}$ is independently halogen, —CN, —NO$_2$, —OR, —SR, —NR$_2$, —S(O)$_2$R, —S(O)$_2$NR$_2$, —S(O)$_2$F, —S(O)R, —S(O)NR$_2$, —S(O)(NR)R, —C(O)R, —C(O)OR, —C(O)NR$_2$, —C(O)N(R)OR, —OC(O)R, —OC(O)NR$_2$, —N(R)C(O)OR, —N(R)C(O)R, —N(R)C(O)NR$_2$, —N(R)C(NR)NR$_2$, —N(R)S(O)$_2$NR$_2$, —N(R)S(O)$_2$R, —P(O)R$_2$, —P(O)(R)OR, or —B(OR)$_2$.

In some embodiments, each instance of $R^{LC}$ is independently halogen, —CN, or —NO$_2$. In some embodiments, each instance of $R^{LC}$ is independently —OR, —SR, or —NR$_2$. In some embodiments, each instance of $R^{LC}$ is independently —S(O)$_2$R, —S(O)$_2$NR$_2$, —S(O)$_2$F, —S(O)R, —S(O)NR$_2$, or —S(O)(NR)R. In some embodiments, each instance of $R^{LC}$ is independently —C(O)R, —C(O)OR, —C(O)NR$_2$, or —C(O)N(R)OR. In some embodiments, each instance of $R^{LC}$ is independently —OC(O)R or —OC(O)NR$_2$. In some embodiments, each instance of $R^{LC}$ is independently —N(R)C(O)OR, —N(R)C(O)R, —N(R)C(O)NR$_2$, —N(R)C(NR)NR$_2$, —N(R)S(O)$_2$NR$_2$, or —N(R)S(O)$_2$R. In some embodiments, each instance of $R^{LC}$ is independently —P(O)R$_2$ or —P(O)(R)OR.

In some embodiments, each instance of $R^{LC}$ is independently —OR, —OC(O)R, or —OC(O)NR$_2$. In some embodiments, each instance of $R^{LC}$ is independently —SR, —S(O)$_2$R, —S(O)$_2$NR$_2$, —S(O)$_2$F, —S(O)R, —S(O)NR$_2$, or —S(O)(NR)R. In some embodiments, each instance of $R^{LC}$ is independently —NR$_2$, —N(R)C(O)OR, —N(R)C(O)R, —N(R)C(O)NR$_2$, —N(R)C(NR)NR$_2$, —N(R)S(O)$_2$NR$_2$, or —N(R)S(O)$_2$R.

In some embodiments, each instance of $R^{LC}$ is independently —S(O)$_2$R, —S(O)$_2$NR$_2$, or —S(O)$_2$F. In some embodiments, each instance of $R^{LC}$ is independently —S(O)R, —S(O)NR$_2$, or —S(O)(NR)R. In some embodiments, each instance of $R^{LC}$ is independently —SR, —S(O)$_2$R, or —S(O)R. In some embodiments, each instance of $R^{LC}$ is independently —S(O)$_2$NR$_2$, —S(O)NR$_2$, or —S(O)(NR)R. In some embodiments, each instance of $R^{LC}$ is independently —S(O)$_2$NR$_2$ or —S(O)NR$_2$. In some embodiments, each instance of $R^{LC}$ is independently —SR, —S(O)$_2$R, —S(O)$_2$NR$_2$, or —S(O)R.

In some embodiments, each instance of $R^{LC}$ is independently —N(R)C(O)OR, —N(R)C(O)R, or —N(R)C(O)NR$_2$. In some embodiments, each instance of $R^{LC}$ is independently —N(R)S(O)$_2$NR$_2$ or —N(R)S(O)$_2$R. In some embodiments, each instance of $R^{LC}$ is independently —N(R)C(O)OR or —N(R)C(O)R. In some embodiments, each instance of $R^{LC}$ is independently —N(R)C(O)NR$_2$ or —N(R)S(O)$_2$NR$_2$. In some embodiments, each instance of $R^{LC}$ is independently —N(R)C(O)OR, —N(R)C(O)R, or —N(R)S(O)$_2$R.

In some embodiments, each instance of $R^{LC}$ is independently —NR$_2$, —N(R)C(O)OR, —N(R)C(O)R, or —N(R)C(O)NR$_2$. In some embodiments, each instance of $R^{LC}$ is independently —NR$_2$, —N(R)C(O)OR, or —N(R)C(O)R. In some embodiments, each instance of $R^{LC}$ is independently —NR$_2$, —N(R)C(O)OR, —N(R)C(O)R, or —N(R)S(O)$_2$R.

In some embodiments, each instance of $R^{LC}$ is independently an optionally substituted $C_{1-6}$ aliphatic. In some embodiments, each instance of $R^{LC}$ is independently an optionally substituted phenyl. In some embodiments, each instance of $R^{LC}$ is independently an optionally substituted 3-7 membered saturated or partially unsaturated monocyclic heterocyclic ring having 1-2 heteroatoms independently selected from nitrogen, oxygen, and sulfur. In some embodiments, each instance of $R^{LC}$ is independently an optionally substituted 5-6 membered monocyclic heteroaryl ring having 1-4 heteroatoms independently selected from nitrogen, oxygen, and sulfur.

In some embodiments, each instance of $R^{LC}$ is independently an optionally substituted $C_{1-6}$ aliphatic or an optionally substituted 3-7 membered saturated or partially unsaturated monocyclic heterocyclic ring having 1-2 heteroatoms independently selected from nitrogen, oxygen, and sulfur. In some embodiments, each instance of $R^{LC}$ is independently an optionally substituted phenyl or an optionally substituted 5-6 membered monocyclic heteroaryl ring having 1-4 heteroatoms independently selected from nitrogen, oxygen, and sulfur.

In some embodiments, each instance of $R^{LC}$ is independently an optionally substituted $C_{1-6}$ aliphatic or an optionally substituted phenyl. In some embodiments, each instance of $R^{LC}$ is independently an optionally substituted 3-7 membered saturated or partially unsaturated monocyclic heterocyclic ring having 1-2 heteroatoms independently selected from nitrogen, oxygen, and sulfur, or an optionally substituted 5-6 membered monocyclic heteroaryl ring having 1-4 heteroatoms independently selected from nitrogen, oxygen, and sulfur.

In some embodiments, each instance of $R^{LC}$ is independently an optionally substituted group selected from phenyl, a 3-7 membered saturated or partially unsaturated monocyclic heterocyclic ring having 1-2 heteroatoms independently selected from nitrogen, oxygen, and sulfur, and a 5-6 membered monocyclic heteroaryl ring having 1-4 heteroatoms independently selected from nitrogen, oxygen, and sulfur.

In some embodiments, each instance of $R^{LC}$ is independently a $C_{1-6}$ aliphatic. In some embodiments, $R^{LC}$ is phenyl. In some embodiments, each instance of $R^{LC}$ is independently a 3-7 membered saturated or partially unsaturated monocyclic heterocyclic ring having 1-2 heteroatoms independently selected from nitrogen, oxygen, and sulfur. In some embodiments, each instance of $R^{LC}$ is independently a 5-6 membered monocyclic heteroaryl ring having 1-4 heteroatoms independently selected from nitrogen, oxygen, and sulfur.

In some embodiments, each instance of $R^{LC}$ is independently a $C_{1-6}$ aliphatic or a 3-7 membered saturated or partially unsaturated monocyclic heterocyclic ring having 1-2 heteroatoms independently selected from nitrogen, oxygen, and sulfur. In some embodiments, each instance of $R^{LC}$ is independently phenyl or a 5-6 membered monocyclic heteroaryl ring having 1-4 heteroatoms independently selected from nitrogen, oxygen, and sulfur.

In some embodiments, each instance of $R^{LC}$ is independently a $C_{1-6}$ aliphatic or phenyl. In some embodiments, each instance of $R^{LC}$ is independently a 3-7 membered saturated or partially unsaturated monocyclic heterocyclic ring having 1-2 heteroatoms independently selected from nitrogen, oxygen, and sulfur, or a 5-6 membered monocyclic heteroaryl ring having 1-4 heteroatoms independently selected from nitrogen, oxygen, and sulfur.

In some embodiments, each instance of $R^{LC}$ is independently phenyl, a 3-7 membered saturated or partially unsaturated monocyclic heterocyclic ring having 1-2 heteroatoms independently selected from nitrogen, oxygen, and sulfur, or a 5-6 membered monocyclic heteroaryl ring having 1-4 heteroatoms independently selected from nitrogen, oxygen, and sulfur.

In some embodiments, each instance of $R^{LC}$ is independently selected from the groups depicted in the compounds in Table 1.

As defined generally above, each instance of $R^{LC}$ is independently oxo, deuterium, halogen, —CN, —NO$_2$, —OR, —SR, —NR$_2$, —S(O)$_2$R, —S(O)$_2$NR$_2$, —S(O)$_2$F, —S(O)R, —S(O)NR$_2$, —S(O)(NR)R, —C(O)R, —C(O)OR, —C(O)NR$_2$, —C(O)N(R)OR, —OC(O)R, —OC(O)NR$_2$, —N(R)C(O)OR, —N(R)C(O)R, —N(R)C(O)NR$_2$, —N(R)C(NR)NR$_2$, —N(R)S(O)$_2$NR$_2$, —N(R)S(O)$_2$R, —P(O)R$_2$, —P(O)(R)OR, —B(OR)$_2$, or an optionally substituted group selected from $C_{1-6}$ aliphatic, phenyl, a 3-7 membered saturated or partially unsaturated monocyclic heterocyclic ring having 1-2 heteroatoms independently selected from nitrogen, oxygen, and sulfur, and a 5-6 membered monocyclic heteroaryl ring having 1-4 heteroatoms independently selected from nitrogen, oxygen, and sulfur.

In some embodiments, each instance of $R^{EEC}$ is independently oxo, deuterium, halogen, —CN, —NO$_2$, —OR, —SR, —NR$_2$, —S(O)$_2$R, —S(O)$_2$NR$_2$, —S(O)$_2$F, —S(O)R, —S(O)NR$_2$, —S(O)(NR)R, —C(O)R, —C(O)OR, —C(O)NR$_2$, —C(O)N(R)OR, —OC(O)R, —OC(O)NR$_2$, —N(R)C(O)OR, —N(R)C(O)R, —N(R)C(O)NR$_2$, —N(R)C(NR)NR$_2$, —N(R)S(O)$_2$NR$_2$, —N(R)S(O)$_2$R, —P(O)R$_2$, —P(O)(R)OR, or —B(OR)$_2$. In some embodiments, each instance of $R^{EEC}$ is independently oxo, deuterium, halogen, —CN, —NO$_2$, —OR, —NR$_2$, —C(O)R, —C(O)OR, —C(O)NR$_2$, —OC(O)R, —N(R)C(O)R, or —N(R)S(O)$_2$R. In some embodiments, each instance of $R^{EEC}$ is independently deuterium, halogen, —CN, —OR, or —NR$_2$. In some embodiments, each instance of $R^{EEC}$ is independently deuterium or halogen. In some embodiments, each instance of $R^{EEC}$ is independently halogen.

In some embodiments, each instance of $R^{EEC}$ is independently an optionally substituted group selected from $C_{1-6}$ aliphatic, phenyl, a 3-7 membered saturated or partially unsaturated monocyclic heterocyclic ring having 1-2 heteroatoms independently selected from nitrogen, oxygen, and sulfur, and a 5-6 membered monocyclic heteroaryl ring having 1-4 heteroatoms independently selected from nitrogen, oxygen, and sulfur.

In some embodiments, each instance of $R^{EEC}$ is independently selected from the groups depicted in the compounds in Table 1.

As defined generally above, each instance of $R^{Q1C}$ is independently oxo, deuterium, halogen, —CN, —NO$_2$, —OR, —SR, —NR$_2$, —S(O)$_2$R, —S(O)$_2$NR$_2$, —S(O)$_2$F, —S(O)R, —S(O)NR$_2$, —S(O)(NR)R, —C(O)R, —C(O)OR, —C(O)NR$_2$, —C(O)N(R)OR, —OC(O)R, —OC(O)

$NR_2$, $-N(R)C(O)OR$, $-N(R)C(O)R$, $-N(R)C(O)NR_2$, $-N(R)C(NR)NR_2$, $-N(R)S(O)_2NR_2$, $-N(R)S(O)_2R$, $-P(O)R_2$, $-P(O)(R)OR$, $-B(OR)_2$, or an optionally substituted group selected from $C_{1-6}$ aliphatic, phenyl, a 3-7 membered saturated or partially unsaturated monocyclic heterocyclic ring having 1-2 heteroatoms independently selected from nitrogen, oxygen, and sulfur, and a 5-6 membered monocyclic heteroaryl ring having 1-4 heteroatoms independently selected from nitrogen, oxygen, and sulfur.

In some embodiments, each instance of $R^{Q1C}$ is independently oxo, halogen, $-CN$, $-NO_2$, $-OR$, $-SR$, $-NR_2$, $-S(O)_2R$, $-S(O)_2NR_2$, $-S(O)_2F$, $-S(O)R$, $-S(O)NR_2$, $-S(O)(NR)R$, $-C(O)R$, $-C(O)OR$, $-C(O)NR_2$, $-C(O)N(R)OR$, $-OC(O)R$, $-OC(O)NR_2$, $-N(R)C(O)OR$, $-N(R)C(O)R$, $-N(R)C(O)NR_2$, $-N(R)C(NR)NR_2$, $-N(R)S(O)_2NR_2$, $-N(R)S(O)_2R$, $-P(O)R_2$, $-P(O)(R)OR$, $-B(OR)_2$, or an optionally substituted group selected from $C_{1-6}$ aliphatic, phenyl, a 3-7 membered saturated or partially unsaturated monocyclic heterocyclic ring having 1-2 heteroatoms independently selected from nitrogen, oxygen, and sulfur, and a 5-6 membered monocyclic heteroaryl ring having 1-4 heteroatoms independently selected from nitrogen, oxygen, and sulfur.

In some embodiments, each instance of $R^{QC}$ is independently oxo, halogen, $-CN$, $-NO_2$, $-OR$, $-SR$, $-NR_2$, $-S(O)_2R$, $-S(O)_2NR_2$, $-S(O)_2F$, $-S(O)R$, $-S(O)NR_2$, $-S(O)(NR)R$, $-C(O)R$, $-C(O)OR$, $-C(O)NR_2$, $-C(O)N(R)OR$, $-OC(O)R$, $-OC(O)NR_2$, $-N(R)C(O)OR$, $-N(R)C(O)R$, $-N(R)C(O)NR_2$, $-N(R)C(NR)NR_2$, $-N(R)S(O)_2NR_2$, $-N(R)S(O)_2R$, $-P(O)R_2$, $-P(O)(R)OR$, or $-B(OR)_2$. In some embodiments, each instance of $R^{Q1C}$ is independently an optionally substituted group selected from $C_{1-6}$ aliphatic, phenyl, a 3-7 membered saturated or partially unsaturated monocyclic heterocyclic ring having 1-2 heteroatoms independently selected from nitrogen, oxygen, and sulfur, and a 5-6 membered monocyclic heteroaryl ring having 1-4 heteroatoms independently selected from nitrogen, oxygen, and sulfur.

In some embodiments, $R^{Q1C}$ is oxo. In some embodiments, $R^{Q1C}$ is deuterium. In some embodiments, each instance of $R^{Q1C}$ is independently halogen. In some embodiments, $R^{Q1C}$ is $-CN$. In some embodiments, $R^{Q1C}$ is $-NO_2$. In some embodiments, $R^{Q1C}$ is $-OR$. In some embodiments, $R^{Q1C}$ is $-SR$. In some embodiments, $R^{Q1C}$ is $-NR_2$. In some embodiments, $R^{Q1C}$ is $-S(O)_2R$. In some embodiments, $R^{Q1C}$ is $-S(O)_2NR_2$. In some embodiments, $R^{Q1C}$ is $-S(O)_2F$. In some embodiments, $R^{Q1C}$ is $-S(O)R$. In some embodiments, $R^{Q1C}$ is $-S(O)NR_2$. In some embodiments, $R^{Q1C}$ is $-S(O)(NR)R$. In some embodiments, $R^{Q1C}$ is $-C(O)R$. In some embodiments, $R^{Q1C}$ is $-C(O)OR$. In some embodiments, $R^{Q1C}$ is $-C(O)NR_2$. In some embodiments, $R^{Q1C}$ is $-C(O)N(R)OR$. In some embodiments, $R^{Q1C}$ is $-OC(O)R$. In some embodiments, $R^{Q1C}$ is $-OC(O)NR_2$. In some embodiments, $R^{Q1C}$ is $-N(R)C(O)OR$. In some embodiments, $R^{Q1C}$ is $-N(R)C(O)R$. In some embodiments, $R^{Q1C}$ is $-N(R)C(O)NR_2$. In some embodiments, $R^{Q1C}$ is $-N(R)C(NR)NR_2$. In some embodiments, $R^{Q1C}$ is $-N(R)S(O)_2NR_2$. In some embodiments, $R^{Q1C}$ is $-N(R)S(O)_2R$. In some embodiments, $R^{Q1C}$ is $-P(O)R_2$. In some embodiments, $R^{Q1C}$ is $-P(O)(R)OR$. In some embodiments, $R^{Q1C}$ c is $-B(OR)_2$.

In some embodiments, each instance of $R^{Q1C}$ is independently halogen, $-CN$, $-NO_2$, $-OR$, $-SR$, $-NR_2$, $-S(O)_2R$, $-S(O)_2NR_2$, $-S(O)_2F$, $-S(O)R$, $-S(O)NR_2$, $-S(O)(NR)R$, $-C(O)R$, $-C(O)OR$, $-C(O)NR_2$, $-C(O)N(R)OR$, $-OC(O)R$, $-OC(O)NR_2$, $-N(R)C(O)OR$, $-N(R)C(O)R$, $-N(R)C(O)NR_2$, $-N(R)C(NR)NR_2$, $-N(R)S(O)_2NR_2$, $-N(R)S(O)_2R$, $-P(O)R_2$, $-P(O)(R)OR$, or $-B(OR)_2$.

In some embodiments, each instance of $R^{Q1C}$ is independently halogen, $-CN$, or $-NO_2$. In some embodiments, each instance of $R^{Q1C}$ is independently $-OR$, $-SR$, or $-NR_2$. In some embodiments, each instance of $R^{Q1C}$ is independently $-S(O)_2R$, $-S(O)_2NR_2$, $-S(O)_2F$, $-S(O)R$, $-S(O)NR_2$, or $-S(O)(NR)R$. In some embodiments, each instance of $R^{QC}$ is independently $-C(O)R$, $-C(O)OR$, $-C(O)NR_2$, or $-C(O)N(R)OR$. In some embodiments, each instance of $R^{Q1C}$ is independently $-OC(O)R$ or $-OC(O)NR_2$. In some embodiments, each instance of $R^{Q1C}$ is independently $-N(R)C(O)OR$, $-N(R)C(O)R$, $-N(R)C(O)NR_2$, $-N(R)C(NR)NR_2$, $-N(R)S(O)_2NR_2$, or $-N(R)S(O)_2R$. In some embodiments, each instance of $R^{Q1C}$ is independently $-P(O)R_2$ or $-P(O)(R)OR$.

In some embodiments, each instance of $R^{Q1C}$ is independently $-OR$, $-OC(O)R$, or $-OC(O)NR_2$. In some embodiments, each instance of $R^{Q1C}$ is independently $-SR$, $-S(O)_2R$, $-S(O)_2NR_2$, $-S(O)_2F$, $-S(O)R$, $-S(O)NR_2$, or $-S(O)(NR)R$. In some embodiments, each instance of $R^{Q1C}$ is independently $-NR_2$, $-N(R)C(O)OR$, $-N(R)C(O)R$, $-N(R)C(O)NR_2$, $-N(R)C(NR)NR_2$, $-N(R)S(O)_2NR_2$, or $-N(R)S(O)_2R$.

In some embodiments, each instance of $R^{Q1C}$ is independently $-S(O)_2R$, $-S(O)_2NR_2$, or $-S(O)_2F$. In some embodiments, each instance of $R^{Q1C}$ is independently $-S(O)R$, $-S(O)NR_2$, or $-S(O)(NR)R$. In some embodiments, each instance of $R^{Q1C}$ is independently $-SR$, $-S(O)_2R$, or $-S(O)R$. In some embodiments, each instance of $R^{Q1C}$ is independently $-S(O)_2NR_2$, $-S(O)NR_2$, or $-S(O)(NR)R$. In some embodiments, each instance of $R^{Q1C}$ is independently $-S(O)_2NR_2$ or $-S(O)NR_2$. In some embodiments, each instance of $R^{Q1C}$ is independently $-SR$, $-S(O)_2R$, $-S(O)_2NR_2$, or $-S(O)R$.

In some embodiments, each instance of $R^{Q1C}$ is independently $-N(R)C(O)OR$, $-N(R)C(O)R$, or $-N(R)C(O)NR_2$. In some embodiments, each instance of $R^{Q1C}$ is independently $-N(R)S(O)_2NR_2$ or $-N(R)S(O)_2R$. In some embodiments, each instance of $R^{Q1C}$ is independently $-N(R)C(O)OR$ or $-N(R)C(O)R$. In some embodiments, each instance of $R^{Q1C}$ is independently $-N(R)C(O)NR_2$ or $-N(R)S(O)_2NR_2$. In some embodiments, each instance of $R^{Q1C}$ is independently $-N(R)C(O)OR$, $-N(R)C(O)R$, or $-N(R)S(O)_2R$.

In some embodiments, each instance of $R^{Q1C}$ is independently $-NR_2$, $-N(R)C(O)OR$, $-N(R)C(O)R$, or $-N(R)C(O)NR_2$. In some embodiments, each instance of $R^{Q1C}$ is independently $-NR_2$, $-N(R)C(O)OR$, or $-N(R)C(O)R$. In some embodiments, each instance of $R^{Q1C}$ is independently $-NR_2$, $-N(R)C(O)OR$, $-N(R)C(O)R$, or $-N(R)S(O)_2R$.

In some embodiments, each instance of $R^{Q1C}$ is independently an optionally substituted $C_{1-6}$ aliphatic. In some embodiments, each instance of $R^{Q1C}$ is independently an optionally substituted phenyl. In some embodiments, each instance of $R^{Q1C}$ is independently an optionally substituted 3-7 membered saturated or partially unsaturated monocyclic heterocyclic ring having 1-2 heteroatoms independently selected from nitrogen, oxygen, and sulfur. In some embodiments, each instance of $R^{Q1C}$ is independently an optionally substituted 5-6 membered monocyclic heteroaryl ring having 1-4 heteroatoms independently selected from nitrogen, oxygen, and sulfur.

In some embodiments, each instance of $R^{Q1C}$ is independently an optionally substituted $C_{1-6}$ aliphatic or an optionally substituted 3-7 membered saturated or partially unsaturated monocyclic heterocyclic ring having 1-2 heteroatoms independently selected from nitrogen, oxygen, and sulfur. In some embodiments, each instance of $R^{Q1C}$ is independently an optionally substituted phenyl or an optionally substituted 5-6 membered monocyclic heteroaryl ring having 1-4 heteroatoms independently selected from nitrogen, oxygen, and sulfur.

In some embodiments, each instance of $R^{Q1C}$ is independently an optionally substituted $C_{1-6}$ aliphatic or an optionally substituted phenyl. In some embodiments, each instance of $R^{Q1C}$ is independently an optionally substituted 3-7 membered saturated or partially unsaturated monocyclic heterocyclic ring having 1-2 heteroatoms independently selected from nitrogen, oxygen, and sulfur, or an optionally substituted 5-6 membered monocyclic heteroaryl ring having 1-4 heteroatoms independently selected from nitrogen, oxygen, and sulfur.

In some embodiments, each instance of $R^{Q1C}$ is independently an optionally substituted group selected from phenyl, a 3-7 membered saturated or partially unsaturated monocyclic heterocyclic ring having 1-2 heteroatoms independently selected from nitrogen, oxygen, and sulfur, and a 5-6 membered monocyclic heteroaryl ring having 1-4 heteroatoms independently selected from nitrogen, oxygen, and sulfur.

In some embodiments, each instance of $R^{Q1C}$ is independently a $C_{1-6}$ aliphatic. In some embodiments, $R^{Q1C}$ is phenyl. In some embodiments, each instance of $R^{Q1C}$ is independently a 3-7 membered saturated or partially unsaturated monocyclic heterocyclic ring having 1-2 heteroatoms independently selected from nitrogen, oxygen, and sulfur. In some embodiments, each instance of $R^{Q1C}$ is independently a 5-6 membered monocyclic heteroaryl ring having 1-4 heteroatoms independently selected from nitrogen, oxygen, and sulfur.

In some embodiments, each instance of $R^{Q1C}$ is independently a $C_{1-6}$ aliphatic or a 3-7 membered saturated or partially unsaturated monocyclic heterocyclic ring having 1-2 heteroatoms independently selected from nitrogen, oxygen, and sulfur. In some embodiments, each instance of $R^{1C}$ is independently phenyl or a 5-6 membered monocyclic heteroaryl ring having 1-4 heteroatoms independently selected from nitrogen, oxygen, and sulfur.

In some embodiments, each instance of $R^{Q1C}$ is independently a $C_{1-6}$ aliphatic or phenyl. In some embodiments, each instance of $R^{Q1C}$ is independently a 3-7 membered saturated or partially unsaturated monocyclic heterocyclic ring having 1-2 heteroatoms independently selected from nitrogen, oxygen, and sulfur, or a 5-6 membered monocyclic heteroaryl ring having 1-4 heteroatoms independently selected from nitrogen, oxygen, and sulfur.

In some embodiments, each instance of $R^{Q1C}$ is independently phenyl, a 3-7 membered saturated or partially unsaturated monocyclic heterocyclic ring having 1-2 heteroatoms independently selected from nitrogen, oxygen, and sulfur, or a 5-6 membered monocyclic heteroaryl ring having 1-4 heteroatoms independently selected from nitrogen, oxygen, and sulfur.

In some embodiments, each instance of $R^{Q1C}$ is independently selected from the groups depicted in the compounds in Table 1.

As defined generally above, each instance of $R^{YZC}$ is independently oxo, deuterium, halogen, —CN, —NO₂, —OR, —SR, —NR₂, —S(O)₂R, —S(O)₂NR₂, —S(O)₂F, —S(O)R, —S(O)NR₂, —S(O)(NR)R, —C(O)R, —C(O)OR, —C(O)NR₂, —C(O)N(R)OR, —OC(O)R, —OC(O)NR₂, —N(R)C(O)OR, —N(R)C(O)R, —N(R)C(O)NR₂, —N(R)C(NR)NR₂, —N(R)S(O)₂NR₂, —N(R)S(O)₂R, —P(O)R₂, —P(O)(R)OR, —B(OR)₂, or an optionally substituted group selected from $C_{1-6}$ aliphatic, phenyl, a 3-7 membered saturated or partially unsaturated monocyclic heterocyclic ring having 1-2 heteroatoms independently selected from nitrogen, oxygen, and sulfur, and a 5-6 membered monocyclic heteroaryl ring having 1-4 heteroatoms independently selected from nitrogen, oxygen, and sulfur.

In some embodiments, each instance of $R^{YZC}$ is independently oxo, halogen, —CN, —NO₂, —OR, —SR, —NR₂, —S(O)₂R, —S(O)₂NR₂, —S(O)₂F, —S(O)R, —S(O)NR₂, —S(O)(NR)R, —C(O)R, —C(O)OR, —C(O)NR₂, —C(O)N(R)OR, —OC(O)R, —OC(O)NR₂, —N(R)C(O)OR, —N(R)C(O)R, —N(R)C(O)NR₂, —N(R)C(NR)NR₂, —N(R)S(O)₂NR₂, —N(R)S(O)₂R, —P(O)R₂, —P(O)(R)OR, —B(OR)₂, or an optionally substituted group selected from $C_{1-6}$ aliphatic, phenyl, a 3-7 membered saturated or partially unsaturated monocyclic heterocyclic ring having 1-2 heteroatoms independently selected from nitrogen, oxygen, and sulfur, and a 5-6 membered monocyclic heteroaryl ring having 1-4 heteroatoms independently selected from nitrogen, oxygen, and sulfur.

In some embodiments, each instance of $R^{YZC}$ is independently oxo, halogen, —CN, —NO₂, —OR, —SR, —NR₂, —S(O)₂R, —S(O)₂NR₂, —S(O)₂F, —S(O)R, —S(O)NR₂, —S(O)(NR)R, —C(O)R, —C(O)OR, —C(O)NR₂, —C(O)N(R)OR, —OC(O)R, —OC(O)NR₂, —N(R)C(O)OR, —N(R)C(O)R, —N(R)C(O)NR₂, —N(R)C(NR)NR₂, —N(R)S(O)₂NR₂, —N(R)S(O)₂R, —P(O)R₂, —P(O)(R)OR, or —B(OR)₂. In some embodiments, each instance of $R^{YZC}$ is independently an optionally substituted group selected from $C_{1-6}$ aliphatic, phenyl, a 3-7 membered saturated or partially unsaturated monocyclic heterocyclic ring having 1-2 heteroatoms independently selected from nitrogen, oxygen, and sulfur, and a 5-6 membered monocyclic heteroaryl ring having 1-4 heteroatoms independently selected from nitrogen, oxygen, and sulfur.

In some embodiments, $R^{YZC}$ is oxo. In some embodiments, $R^{YZC}$ is deuterium. In some embodiments, each instance of $R^{YZC}$ is independently halogen. In some embodiments, $R^{YZC}$ is —CN. In some embodiments, $R^{YZC}$ is —NO₂. In some embodiments, $R^{YZC}$ is —OR. In some embodiments, $R^{YZC}$ is —SR. In some embodiments, $R^{YZC}$ is —NR₂. In some embodiments, $R^{YZC}$ is —S(O)₂R. In some embodiments, $R^{YZC}$ is —S(O)₂NR₂. In some embodiments, $R^{YZC}$ is —S(O)₂F. In some embodiments, $R^{YZC}$ is —S(O)R. In some embodiments, $R^{YZC}$ is —S(O)NR₂. In some embodiments, $R^{YZC}$ is —S(O)(NR)R. In some embodiments, $R^{YZC}$ is —C(O)R. In some embodiments, $R^{YZC}$ is —C(O)OR. In some embodiments, $R^{YZC}$ is —C(O)NR₂. In some embodiments, $R^{YZC}$ is —C(O)N(R)OR. In some embodiments, $R^{YZC}$ is —OC(O)R. In some embodiments, $R^{YZC}$ is —OC(O)NR₂. In some embodiments, $R^{YZC}$ is —N(R)C(O)OR. In some embodiments, $R^{YZC}$ is —N(R)C(O)R. In some embodiments, $R^{YZC}$ is —N(R)C(O)NR₂. In some embodiments, $R^{YZC}$ is —N(R)C(NR)NR₂. In some embodiments, $R^{YZC}$ is —N(R)S(O)₂NR₂. In some embodiments, $R^{YZC}$ is —N(R)S(O)₂R. In some embodiments, $R^{YZC}$ is —P(O)R₂. In some embodiments, $R^{YZC}$ is —P(O)(R)OR. In some embodiments, $R^{YZC}$ is —B(OR)₂.

In some embodiments, each instance of $R^{YZC}$ is independently halogen, —CN, —NO₂, —OR, —SR, —NR₂, —S(O)₂R, —S(O)₂NR₂, —S(O)₂F, —S(O)R, —S(O)NR₂, —S(O)(NR)R, —C(O)R, —C(O)OR, —C(O)NR₂, —C(O)N(R)OR, —OC(O)R, —OC(O)NR₂, —N(R)C(O)OR, —N(R)C(O)R, —N(R)C(O)NR$_2$, —N(R)C(NR)NR$_2$, —N(R)S(O)$_2$NR$_2$, —N(R)S(O)$_2$R, —P(O)R$_2$, —P(O)(R)OR, or —B(OR)$_2$.

In some embodiments, each instance of R$^{YZC}$ is independently halogen, —CN, or —NO$_2$. In some embodiments, each instance of R$^{YZC}$ is independently —OR, —SR, or —NR$_2$. In some embodiments, each instance of R$^{YZC}$ is independently —S(O)$_2$R, —S(O)$_2$NR$_2$, —S(O)$_2$F, —S(O)R, —S(O)NR$_2$, or —S(O)(NR)R. In some embodiments, each instance of R$^{YZC}$ is independently —C(O)R, —C(O)OR, —C(O)NR$_2$, or —C(O)N(R)OR. In some embodiments, each instance of R$^{YZC}$ is independently —OC(O)R or —OC(O)NR$_2$. In some embodiments, each instance of R$^{YZC}$ is independently —N(R)C(O)OR, —N(R)C(O)R, —N(R)C(O)NR$_2$, —N(R)C(NR)NR$_2$, —N(R)S(O)$_2$NR$_2$, or —N(R)S(O)$_2$R. In some embodiments, each instance of R$^{YZC}$ is independently —P(O)R$_2$ or —P(O)(R)OR.

In some embodiments, each instance of R$^{YZC}$ is independently —OR, —OC(O)R, or —OC(O)NR$_2$. In some embodiments, each instance of R$^{YZC}$ is independently —SR, —S(O)$_2$R, —S(O)$_2$NR$_2$, —S(O)$_2$F, —S(O)R, —S(O)NR$_2$, or —S(O)(NR)R. In some embodiments, each instance of R$^{YZC}$ is independently —NR$_2$, —N(R)C(O)OR, —N(R)C(O)R, —N(R)C(O)NR$_2$, —N(R)C(NR)NR$_2$, —N(R)S(O)$_2$NR$_2$, or —N(R)S(O)$_2$R.

In some embodiments, each instance of R$^{YZC}$ is independently —S(O)$_2$R, —S(O)$_2$NR$_2$, or —S(O)$_2$F. In some embodiments, each instance of R$^{YZC}$ is independently —S(O)R, —S(O)NR$_2$, or —S(O)(NR)R. In some embodiments, each instance of R$^{YZC}$ is independently —SR, —S(O)$_2$R, or —S(O)R. In some embodiments, each instance of R$^{YZC}$ is independently —S(O)$_2$NR$_2$, —S(O)NR$_2$, or —S(O)(NR)R. In some embodiments, each instance of R$^{YZC}$ is independently —S(O)$_2$NR$_2$ or —S(O)NR$_2$. In some embodiments, each instance of R$^{YZC}$ is independently —SR, —S(O)$_2$R, —S(O)$_2$NR$_2$, or —S(O)R.

In some embodiments, each instance of R$^{YZC}$ is independently —N(R)C(O)OR, —N(R)C(O)R, or —N(R)C(O)NR$_2$. In some embodiments, each instance of R$^{YZC}$ is independently —N(R)S(O)$_2$NR$_2$ or —N(R)S(O)$_2$R. In some embodiments, each instance of R$^{YZC}$ is independently —N(R)C(O)OR or —N(R)C(O)R. In some embodiments, each instance of R$^{YZC}$ is independently —N(R)C(O)NR$_2$ or —N(R)S(O)$_2$NR$_2$. In some embodiments, each instance of R$^{YZC}$ is independently —N(R)C(O)OR, —N(R)C(O)R, or —N(R)S(O)$_2$R.

In some embodiments, each instance of R$^{YZC}$ is independently —NR$_2$, —N(R)C(O)OR, —N(R)C(O)R, or —N(R)C(O)NR$_2$. In some embodiments, each instance of R$^{YZC}$ is independently —NR$_2$, —N(R)C(O)OR, or —N(R)C(O)R. In some embodiments, each instance of R$^{YZC}$ is independently —NR$_2$, —N(R)C(O)OR, —N(R)C(O)R, or —N(R)S(O)$_2$R.

In some embodiments, each instance of R$^{YZC}$ is independently an optionally substituted C$_{1-6}$ aliphatic. In some embodiments, each instance of R$^{YZC}$ is independently an optionally substituted phenyl. In some embodiments, each instance of R$^{YZC}$ is independently an optionally substituted 3-7 membered saturated or partially unsaturated monocyclic heterocyclic ring having 1-2 heteroatoms independently selected from nitrogen, oxygen, and sulfur. In some embodiments, each instance of R$^{YZC}$ is independently an optionally substituted 5-6 membered monocyclic heteroaryl ring having 1-4 heteroatoms independently selected from nitrogen, oxygen, and sulfur. In some embodiments, each instance of R$^{YZC}$ is independently an optionally substituted C$_{1-6}$ aliphatic or an optionally substituted 3-7 membered saturated or partially unsaturated monocyclic heterocyclic ring having 1-2 heteroatoms independently selected from nitrogen, oxygen, and sulfur. In some embodiments, each instance of R$^{YZC}$ is independently an optionally substituted phenyl or an optionally substituted 5-6 membered monocyclic heteroaryl ring having 1-4 heteroatoms independently selected from nitrogen, oxygen, and sulfur.

In some embodiments, each instance of R$^{YZC}$ is independently an optionally substituted C$_{1-6}$ aliphatic or an optionally substituted phenyl. In some embodiments, each instance of R$^{YZC}$ is independently an optionally substituted 3-7 membered saturated or partially unsaturated monocyclic heterocyclic ring having 1-2 heteroatoms independently selected from nitrogen, oxygen, and sulfur, or an optionally substituted 5-6 membered monocyclic heteroaryl ring having 1-4 heteroatoms independently selected from nitrogen, oxygen, and sulfur.

In some embodiments, each instance of R$^{YZC}$ is independently an optionally substituted group selected from phenyl, a 3-7 membered saturated or partially unsaturated monocyclic heterocyclic ring having 1-2 heteroatoms independently selected from nitrogen, oxygen, and sulfur, and a 5-6 membered monocyclic heteroaryl ring having 1-4 heteroatoms independently selected from nitrogen, oxygen, and sulfur.

In some embodiments, each instance of R$^{YZC}$ is independently a C$_{1-6}$ aliphatic. In some embodiments, R$^{YZC}$ is phenyl. In some embodiments, each instance of R$^{YZC}$ is independently a 3-7 membered saturated or partially unsaturated monocyclic heterocyclic ring having 1-2 heteroatoms independently selected from nitrogen, oxygen, and sulfur. In some embodiments, each instance of R$^{YZC}$ is independently a 5-6 membered monocyclic heteroaryl ring having 1-4 heteroatoms independently selected from nitrogen, oxygen, and sulfur.

In some embodiments, each instance of R$^{YZC}$ is independently a C$_{1-6}$ aliphatic or a 3-7 membered saturated or partially unsaturated monocyclic heterocyclic ring having 1-2 heteroatoms independently selected from nitrogen, oxygen, and sulfur. In some embodiments, each instance of R$^{YZC}$ is independently phenyl or a 5-6 membered monocyclic heteroaryl ring having 1-4 heteroatoms independently selected from nitrogen, oxygen, and sulfur.

In some embodiments, each instance of R$^{YZC}$ is independently a C$_{1-6}$ aliphatic or phenyl. In some embodiments, each instance of R$^{YZC}$ is independently a 3-7 membered saturated or partially unsaturated monocyclic heterocyclic ring having 1-2 heteroatoms independently selected from nitrogen, oxygen, and sulfur, or a 5-6 membered monocyclic heteroaryl ring having 1-4 heteroatoms independently selected from nitrogen, oxygen, and sulfur.

In some embodiments, each instance of R$^{YZC}$ is independently phenyl, a 3-7 membered saturated or partially unsaturated monocyclic heterocyclic ring having 1-2 heteroatoms independently selected from nitrogen, oxygen, and sulfur, or a 5-6 membered monocyclic heteroaryl ring having 1-4 heteroatoms independently selected from nitrogen, oxygen, and sulfur.

In some embodiments, each instance of R$^{YZC}$ is independently selected from the groups depicted in the compounds in Table 1.

As defined generally above, each instance of R is independently hydrogen, or an optionally substituted group selected from C$_{1-6}$ aliphatic, phenyl, a 3-7 membered saturated or partially unsaturated monocyclic heterocyclic ring having 1-2 heteroatoms independently selected from nitrogen, oxygen, and sulfur, and a 5-6 membered monocyclic heteroaryl ring having 1-4 heteroatoms independently selected from nitrogen, oxygen, and sulfur; or two R groups on the same nitrogen are taken together with their intervening atoms to form a 4-7 membered saturated, partially unsaturated, or heteroaryl ring having 0-3 heteroatoms, in addition to the nitrogen, independently selected from nitrogen, oxygen, and sulfur.

In some embodiments, R is hydrogen or an optionally substituted group selected from $C_{1-6}$ aliphatic, phenyl, a 3-7 membered saturated or partially unsaturated monocyclic heterocyclic ring having 1-2 heteroatoms independently selected from nitrogen, oxygen, and sulfur, and a 5-6 membered monocyclic heteroaryl ring having 1-4 heteroatoms independently selected from nitrogen, oxygen, and sulfur. In some embodiments, two R groups on the same nitrogen are taken together with their intervening atoms to form a 4-7 membered saturated, partially unsaturated, or heteroaryl ring having 0-3 heteroatoms, in addition to the nitrogen, independently selected from nitrogen, oxygen, and sulfur.

In some embodiments, R is hydrogen. In some embodiments, R is an optionally substituted group selected from $C_{1-6}$ aliphatic, phenyl, a 3-7 membered saturated or partially unsaturated monocyclic heterocyclic ring having 1-2 heteroatoms independently selected from nitrogen, oxygen, and sulfur, and a 5-6 membered monocyclic heteroaryl ring having 1-4 heteroatoms independently selected from nitrogen, oxygen, and sulfur. In some embodiments, R is hydrogen, $C_{1-6}$ aliphatic, phenyl, a 3-7 membered saturated or partially unsaturated monocyclic heterocyclic ring having 1-2 heteroatoms independently selected from nitrogen, oxygen, and sulfur, or a 5-6 membered monocyclic heteroaryl ring having 1-4 heteroatoms independently selected from nitrogen, oxygen, and sulfur.

In some embodiments, R is an optionally substituted $C_{1-6}$ aliphatic. In some embodiments, R is an optionally substituted phenyl. In some embodiments, R is an optionally substituted 3-7 membered saturated or partially unsaturated monocyclic heterocyclic ring having 1-2 heteroatoms independently selected from nitrogen, oxygen, and sulfur. In some embodiments, R is an optionally substituted 5-6 membered monocyclic heteroaryl ring having 1-4 heteroatoms independently selected from nitrogen, oxygen, and sulfur.

In some embodiments, R is an optionally substituted $C_{1-6}$ aliphatic or an optionally substituted 3-7 membered saturated or partially unsaturated monocyclic heterocyclic ring having 1-2 heteroatoms independently selected from nitrogen, oxygen, and sulfur. In some embodiments, R is an optionally substituted phenyl or an optionally substituted 5-6 membered monocyclic heteroaryl ring having 1-4 heteroatoms independently selected from nitrogen, oxygen, and sulfur.

In some embodiments, R is an optionally substituted $C_{1-6}$ aliphatic or an optionally substituted phenyl. In some embodiments, R is an optionally substituted 3-7 membered saturated or partially unsaturated monocyclic heterocyclic ring having 1-2 heteroatoms independently selected from nitrogen, oxygen, and sulfur, or an optionally substituted 5-6 membered monocyclic heteroaryl ring having 1-4 heteroatoms independently selected from nitrogen, oxygen, and sulfur.

In some embodiments, R is an optionally substituted group selected from phenyl, a 3-7 membered saturated or partially unsaturated monocyclic heterocyclic ring having 1-2 heteroatoms independently selected from nitrogen, oxygen, and sulfur, and a 5-6 membered monocyclic heteroaryl ring having 1-4 heteroatoms independently selected from nitrogen, oxygen, and sulfur.

In some embodiments, R is a $C_{1-6}$ aliphatic. In some embodiments, R is phenyl. In some embodiments, R is a 3-7 membered saturated or partially unsaturated monocyclic heterocyclic ring having 1-2 heteroatoms independently selected from nitrogen, oxygen, and sulfur. In some embodiments, R is a 5-6 membered monocyclic heteroaryl ring having 1-4 heteroatoms independently selected from nitrogen, oxygen, and sulfur.

In some embodiments, R is a $C_{1-6}$ aliphatic or a 3-7 membered saturated or partially unsaturated monocyclic heterocyclic ring having 1-2 heteroatoms independently selected from nitrogen, oxygen, and sulfur. In some embodiments, R is phenyl or a 5-6 membered monocyclic heteroaryl ring having 1-4 heteroatoms independently selected from nitrogen, oxygen, and sulfur.

In some embodiments, R is a $C_{1-6}$ aliphatic or phenyl. In some embodiments, R is a 3-7 membered saturated or partially unsaturated monocyclic heterocyclic ring having 1-2 heteroatoms independently selected from nitrogen, oxygen, and sulfur, or a 5-6 membered monocyclic heteroaryl ring having 1-4 heteroatoms independently selected from nitrogen, oxygen, and sulfur.

In some embodiments, R is phenyl, a 3-7 membered saturated or partially unsaturated monocyclic heterocyclic ring having 1-2 heteroatoms independently selected from nitrogen, oxygen, and sulfur, or a 5-6 membered monocyclic heteroaryl ring having 1-4 heteroatoms independently selected from nitrogen, oxygen, and sulfur.

In some embodiments, two R groups on the same nitrogen are taken together with their intervening atoms to form a 4-7 membered saturated, partially unsaturated, or heteroaryl ring having 1-3 heteroatoms, in addition to the nitrogen, independently selected from nitrogen, oxygen, and sulfur. In some embodiments, two R groups on the same nitrogen are taken together with their intervening atoms to form a 4-7 membered saturated, partially unsaturated, or heteroaryl ring having no additional heteroatoms other than said nitrogen.

In some embodiments, two R groups on the same nitrogen are taken together with their intervening atoms to form a 4-7 membered saturated ring having 0-3 heteroatoms, in addition to the nitrogen, independently selected from nitrogen, oxygen, and sulfur. In some embodiments, two R groups on the same nitrogen are taken together with their intervening atoms to form a 4-7 membered partially unsaturated ring having 0-3 heteroatoms, in addition to the nitrogen, independently selected from nitrogen, oxygen, and sulfur. In some embodiments, two R groups on the same nitrogen are taken together with their intervening atoms to form a 4-7 membered heteroaryl ring having 0-3 heteroatoms, in addition to the nitrogen, independently selected from nitrogen, oxygen, and sulfur.

In some embodiments, two R groups on the same nitrogen are taken together with their intervening atoms to form a 4-7 membered saturated ring having 1-3 heteroatoms, in addition to the nitrogen, independently selected from nitrogen, oxygen, and sulfur. In some embodiments, two R groups on the same nitrogen are taken together with their intervening atoms to form a 4-7 membered partially unsaturated ring having 1-3 heteroatoms, in addition to the nitrogen, independently selected from nitrogen, oxygen, and sulfur. In some embodiments, two R groups on the same nitrogen are taken together with their intervening atoms to form a 4-7 membered heteroaryl ring having 1-3 heteroatoms, in addition to the nitrogen, independently selected from nitrogen, oxygen, and sulfur.

In some embodiments, two R groups on the same nitrogen are taken together with their intervening atoms to form a 4-7 membered saturated ring having no additional heteroatoms other than said nitrogen. In some embodiments, two R groups on the same nitrogen are taken together with their intervening atoms to form a 4-7 membered partially unsaturated ring having no additional heteroatoms other than said nitrogen. In some embodiments, two R groups on the same nitrogen are taken together with their intervening atoms to form a 4-7 membered heteroaryl ring having no additional heteroatoms other than said nitrogen.

In some embodiments, R is selected from the groups depicted in the compounds in Table 1.

As defined generally above, n is 0, 1, 2, 3, or 4. In some embodiments, n is 0. In some embodiments, n is 1. In some embodiments, n is 2. In some embodiments, n is 3. In some embodiments, n is 4. In some embodiments, n is 0 or 1. In some embodiments, n is 0, 1, or 2. In some embodiments, n is 0, 1, 2, or 3. In some embodiments, n is 1 or 2. In some embodiments, n is 1, 2, or 3. In some embodiments, n is 1, 2, 3, or 4. In some embodiments, n is 2 or 3. In some embodiments, n is 2, 3, or 4. In some embodiments, n is 3 or 4. In some embodiments, n is selected from the values represented in the compounds in Table 1.

As defined generally above, p is 0, 1, 2, 3, or 4. In some embodiments, p is 0. In some embodiments, p is 1. In some embodiments, p is 2. In some embodiments, p is 3. In some embodiments, p is 4. In some embodiments, p is 0 or 1. In some embodiments, p is 0, 1, or 2. In some embodiments, p is 0, 1, 2, or 3. In some embodiments, p is 1 or 2. In some embodiments, p is 1, 2, or 3. In some embodiments, p is 1, 2, 3, or 4. In some embodiments, p is 2 or 3. In some embodiments, p is 2, 3, or 4. In some embodiments, p is 3 or 4. In some embodiments, p is selected from the values represented in the compounds in Table 1.

As defined generally above, q is 0, 1, 2, 3, or 4. In some embodiments, q is 0. In some embodiments, q is 1. In some embodiments, q is 2. In some embodiments, q is 3. In some embodiments, q is 4. In some embodiments, q is 0 or 1. In some embodiments, q is 0, 1, or 2. In some embodiments, q is 0, 1, 2, or 3. In some embodiments, q is 1 or 2. In some embodiments, q is 1, 2, or 3. In some embodiments, q is 1, 2, 3, or 4. In some embodiments, q is 2 or 3. In some embodiments, q is 2, 3, or 4. In some embodiments, q is 3 or 4. In some embodiments, q is selected from the values represented in the compounds in Table 1.

As defined generally above, $r^1$ is 0, 1, 2, 3, or 4. In some embodiments, $r^1$ is 0. In some embodiments, $r^1$ is 1. In some embodiments, $r^1$ is 2. In some embodiments, $r^1$ is 3. In some embodiments, $r^1$ is 4. In some embodiments, $r^1$ is 0 or 1. In some embodiments, $r^1$ is 0, 1, or 2. In some embodiments, $r^1$ is 0, 1, 2, or 3. In some embodiments, $r^1$ is 1 or 2. In some embodiments, $r^1$ is 1, 2, or 3. In some embodiments, $r^1$ is 1, 2, 3, or 4. In some embodiments, $r^1$ is 2 or 3. In some embodiments, $r^1$ is 2, 3, or 4. In some embodiments, $r^1$ is 3 or 4. In some embodiments, $r^1$ is selected from the values represented in the compounds in Table 1.

As defined generally above, $r^2$ is 0, 1, 2, 3, or 4. In some embodiments, $r^2$ is 0. In some embodiments, $r^2$ is 1. In some embodiments, $r^2$ is 2. In some embodiments, $r^2$ is 3. In some embodiments, $r^2$ is 4. In some embodiments, $r^2$ is 0 or 1. In some embodiments, $r^2$ is 0, 1, or 2. In some embodiments, $r^2$ is 0, 1, 2, or 3. In some embodiments, $r^2$ is 1 or 2. In some embodiments, $r^2$ is 1, 2, or 3. In some embodiments, $r^2$ is 1, 2, 3, or 4. In some embodiments, $r^2$ is 2 or 3. In some embodiments, $r^2$ is 2, 3, or 4. In some embodiments, $r^2$ is 3 or 4. In some embodiments, $r^2$ is selected from the values represented in the compounds in Table 1.

As defined generally above, $r^3$ is 0, 1, 2, 3, or 4. In some embodiments, $r^3$ is 0. In some embodiments, $r^3$ is 1. In some embodiments, $r^3$ is 2. In some embodiments, $r^3$ is 3. In some embodiments, $r^3$ is 4. In some embodiments, $r^3$ is 0 or 1. In some embodiments, $r^3$ is 0, 1, or 2. In some embodiments, $r^3$ is 0, 1, 2, or 3. In some embodiments, $r^3$ is 1 or 2. In some embodiments, $r^3$ is 1, 2, or 3. In some embodiments, $r^3$ is 1, 2, 3, or 4. In some embodiments, $r^3$ is 2 or 3. In some embodiments, $r^3$ is 2, 3, or 4. In some embodiments, $r^3$ is 3 or 4. In some embodiments, $r^3$ is selected from the values represented in the compounds in Table 1.

As defined generally above, $r^4$ is 0, 1, 2, 3, or 4. In some embodiments, $r^4$ is 0. In some embodiments, $r^4$ is 1. In some embodiments, $r^4$ is 2. In some embodiments, $r^4$ is 3. In some embodiments, $r^4$ is 4. In some embodiments, $r^4$ is 0 or 1. In some embodiments, $r^4$ is 0, 1, or 2. In some embodiments, $r^4$ is 0, 1, 2, or 3. In some embodiments, $r^4$ is 1 or 2. In some embodiments, $r^4$ is 1, 2, or 3. In some embodiments, $r^4$ is 1, 2, 3, or 4. In some embodiments, $r^4$ is 2 or 3. In some embodiments, $r^4$ is 2, 3, or 4. In some embodiments, $r^4$ is 3 or 4. In some embodiments, $r^4$ is selected from the values represented in the compounds in Table 1.

As defined generally above, $r^1$ is 0, 1, 2, 3, or 4. In some embodiments, $r^1$ is 0. In some embodiments, $r^5$ is 1. In some embodiments, $r^5$ is 2. In some embodiments, $r^5$ is 3. In some embodiments, $r^5$ is 4. In some embodiments, $r^5$ is 0 or 1. In some embodiments, $r^5$ is 0, 1, or 2. In some embodiments, $r^5$ is 0, 1, 2, or 3. In some embodiments, $r^5$ is 1 or 2. In some embodiments, $r^5$ is 1, 2, or 3. In some embodiments, $r^5$ is 1, 2, 3, or 4. In some embodiments, $r^5$ is 2 or 3. In some embodiments, $r^1$ is 2, 3, or 4. In some embodiments, $r^5$ is 3 or 4. In some embodiments, $r^5$ is selected from the values represented in the compounds in Table 1.

As defined generally above, $r^6$ is 0, 1, 2, 3, or 4. In some embodiments, $r^6$ is 0. In some embodiments, $r^6$ is 1. In some embodiments, $r^6$ is 2. In some embodiments, $r^6$ is 3. In some embodiments, $r^6$ is 4. In some embodiments, $r^6$ is 0 or 1. In some embodiments, $r^6$ is 0, 1, or 2. In some embodiments, $r^6$ is 0, 1, 2, or 3. In some embodiments, $r^6$ is 1 or 2. In some embodiments, $r^6$ is 1, 2, or 3. In some embodiments, $r^6$ is 1, 2, 3, or 4. In some embodiments, $r^6$ is 2 or 3. In some embodiments, $r^6$ is 2, 3, or 4. In some embodiments, $r^6$ is 3 or 4. In some embodiments, $r^6$ is selected from the values represented in the compounds in Table 1.

As defined generally above, $r^7$ is 0, 1, 2, 3, or 4. In some embodiments, $r^7$ is 0. In some embodiments, $r^7$ is 1. In some embodiments, $r^7$ is 2. In some embodiments, $r^7$ is 3. In some embodiments, $r^7$ is 4. In some embodiments, $r^7$ is 0 or 1. In some embodiments, $r^7$ is 0, 1, or 2. In some embodiments, $r^7$ is 0, 1, 2, or 3. In some embodiments, $r^7$ is 1 or 2. In some embodiments, $r^7$ is 1, 2, or 3. In some embodiments, $r^7$ is 1, 2, 3, or 4. In some embodiments, $r^7$ is 2 or 3. In some embodiments, $r^7$ is 2, 3, or 4. In some embodiments, $r^7$ is 3 or 4. In some embodiments, $r^7$ is selected from the values represented in the compounds in Table 1.

As defined generally above, $r^5$ is 0, 1, 2, 3, or 4. In some embodiments, $r^5$ is 0. In some embodiments, $r^8$ is 1. In some embodiments, $r^8$ is 2. In some embodiments, $r^8$ is 3. In some embodiments, $r^8$ is 4. In some embodiments, $r^8$ is 0 or 1. In some embodiments, $r^8$ is 0, 1, or 2. In some embodiments, $r^0$ is 0, 1, 2, or 3. In some embodiments, $r^8$ is 1 or 2. In some embodiments, $r^8$ is 1, 2, or 3. In some embodiments, $r^8$ is 1, 2, 3, or 4. In some embodiments, $r^8$ is 2 or 3. In some embodiments, $r^8$ is 2, 3, or 4. In some embodiments, $r^8$ is 3 or 4. In some embodiments, $r^8$ is selected from the values represented in the compounds in Table 1.

In some embodiments, the present invention provides a compound of formula I wherein E is —C(O)—, thereby forming a compound of formula II:

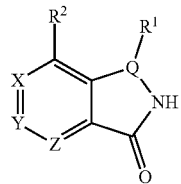

II or a pharmaceutically acceptable salt thereof, wherein each of Q, R¹, R², X, Y, and Z is as defined in embodiments and classes and subclasses herein.

In some embodiments, the present invention provides a compound of formula II wherein Q is CH, thereby forming a compound of formula III:

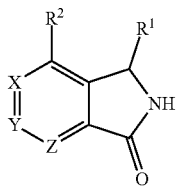

III or a pharmaceutically acceptable salt thereof, wherein each of R¹, R², X, Y, and Z is as defined in embodiments and classes and subclasses herein.

In some embodiments, the present invention provides a compound of formula II wherein Q is N, thereby forming a compound of formula IV:

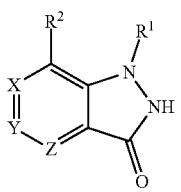

IV or a pharmaceutically acceptable salt thereof, wherein each of R¹, R², X, Y, and Z is as defined in embodiments and classes and subclasses herein.

In some embodiments, the present invention provides a compound of formula II wherein X, Y, or Z is CH, thereby forming a compound of formula V, VI, or VII:

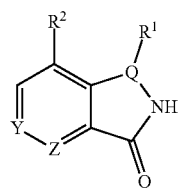

V

-continued

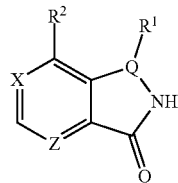

VI

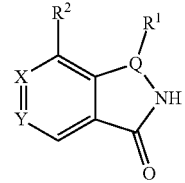

VII or a pharmaceutically acceptable salt thereof, wherein each of R¹, R², Q, X, Y, and Z is as defined in embodiments and classes and subclasses herein.

In some embodiments, the present invention provides a compound of formula II wherein X, Y, or Z is N, thereby forming a compound of formula VIII, IX, or X:

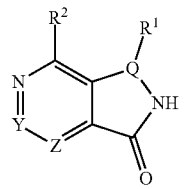

VIII

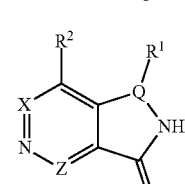

IX

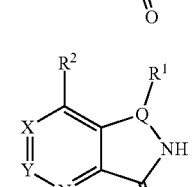

X or a pharmaceutically acceptable salt thereof, wherein each of R¹, R², Q, X, Y, and Z is as defined in embodiments and classes and subclasses herein.

In some embodiments, the present invention provides a compound of formula III wherein X, Y, or Z is CH, thereby forming a compound of formula XI, XII, or XIII:

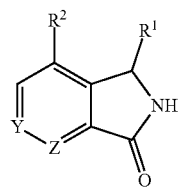

XI

XII

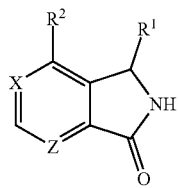

XIII

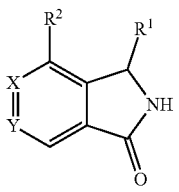

or a pharmaceutically acceptable salt thereof, wherein each of $R^1$, $R^2$, X, Y, and Z is as defined in embodiments and classes and subclasses herein.

In some embodiments, the present invention provides a compound of formula III wherein X, Y, or Z is N, thereby forming a compound of formula XIV, XV, or XVI:

XIV

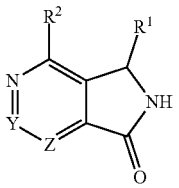

XV

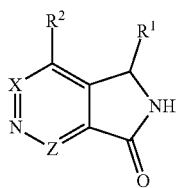

XVI

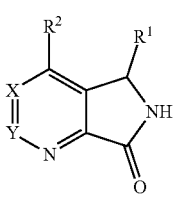

or a pharmaceutically acceptable salt thereof, wherein each of $R^1$, $R^2$, X, Y, and Z is as defined in embodiments and classes and subclasses herein.

In some embodiments, the present invention provides a compound of formulas III, XIII, XV, and XVI wherein X is CH, thereby forming a compound of formula XVII, XVIII, XIX, or XX:

XVII

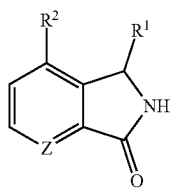

XVIII

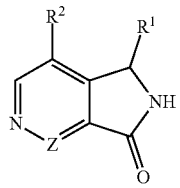

XIX

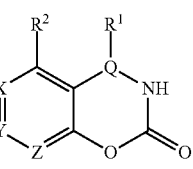

XX

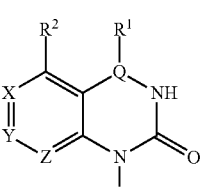

or a pharmaceutically acceptable salt thereof, wherein each of $R^1$, $R^2$, X, Y, and Z is as defined in embodiments and classes and subclasses herein.

In some embodiments, the present invention provides a compound of formula I wherein E is —OC(O)—, —N($R^E$)C(O)—, or —C($R^E$)$_2$C(O)—, thereby forming a compound of formula XXI, XXII, or XXIII, respectively:

XXI

XXII

XXIII or a pharmaceutically acceptable salt thereof, wherein each of Q, R¹, R², $R^E$, X, Y, and Z is as defined in embodiments and classes and subclasses herein.

In some embodiments, the present invention provides a compound of formula XXI, XXII, or XXIII wherein Q is CH, thereby forming a compound of formula XXIV, XXV, or XXVI respectively:

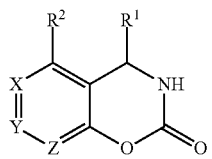

XXIV

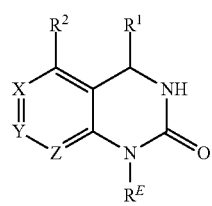

XXV

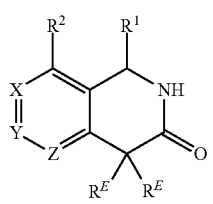

XXVI or a pharmaceutically acceptable salt thereof, wherein each of R¹, R², $R^E$, X, Y, and Z is as defined in embodiments and classes and subclasses herein.

In some embodiments, the present invention provides a compound of formula III, XI, XII, XIII, XIV, XV, XVI, XVII, XVIII, XIX, XX, XXIV, XXV, or XXVI, having the depicted stereochemistry at Q when Q is CH, thereby forming a compound of formula XXVII, XXVIII, XXIX, XXX, XXXI, XXXII, XXXIII, XXXIV, XXXV, XXXVI, XXXVII, XXXVIII, XXXIX, or XXXX respectively:

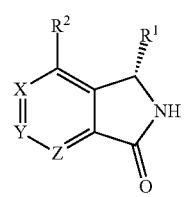

XXVII

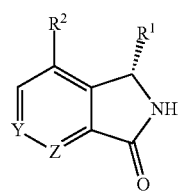

XXVIII

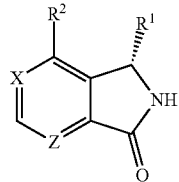

XXIX

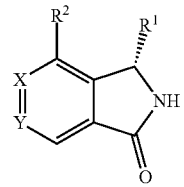

XXX

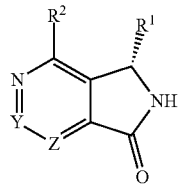

XXXI

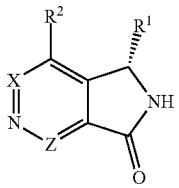

XXXII

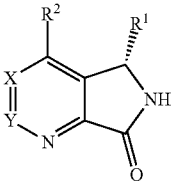

XXXIII

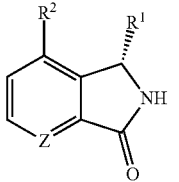

XXXIV

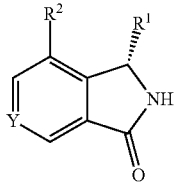

XXXV

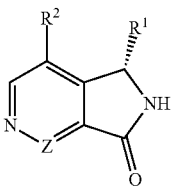

XXXVI

-continued

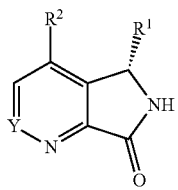

XXXVII

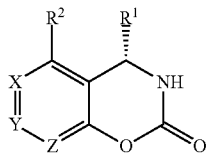

XXXVIII

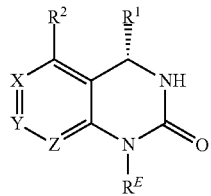

XXXIX

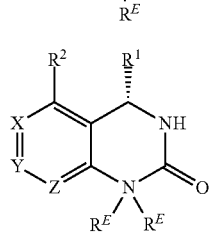

XXXX or a pharmaceutically acceptable salt thereof, wherein each of $R^1$, $R^2$, $R^E$, X, Y, and Z is as defined in embodiments and classes and subclasses herein.

In some embodiments, the present invention provides a compound of formula XXVIII:

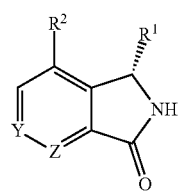

XXVIII or a pharmaceutically acceptable salt thereof, wherein each of $R^1$, $R^2$, Y, and Z is as defined in embodiments and classes and subclasses herein.

In some embodiments, the present invention provides a compound of formula XXXV:

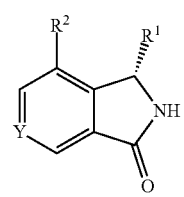

XXXV or a pharmaceutically acceptable salt thereof, wherein each of $R^1$, $R^2$, and Y is as defined in embodiments and classes and subclasses herein.

In some embodiments, the present invention provides a compound of formula XXXVII:

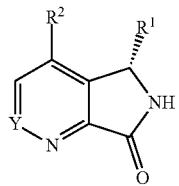

XXXVII or a pharmaceutically acceptable salt thereof, wherein each of $R^1$, $R^2$, and Y is as defined in embodiments and classes and subclasses herein.

In some embodiments, the present invention provides a compound of formula I, II, III, IV, V, VI, VII, VIII, IX, X, XI, XII, XIII, XIV, XV, XVI, XVII, XVIII, XIX, XX, XXI, XXII, XXIII, XXIV, XXV, XXVI, XXVII, XXVIII, XXIX, XXX, XXXI, XXXII, XXXIII, XXXIV, XXXV, XXXVI, XXXVII, XXXVIII, XXXIX, or XXXX, wherein $L^1$ is a covalent bond, and $R^2$ is —N(R)C(O)—$R^{2A}$, —N(R)—$R^{2A}$, or —$R^{2A}$.

In some embodiments, the present invention provides a compound of formula I, II, III, IV, V, VI, VII, VIII, IX, X, XI, XII, XIII, XIV, XV, XVI, XVII, XVIII, XIX, XX, XXI, XXII, XXIII, XXIV, XXV, XXVI, XXVII, XXVIII, XXIX, XXX, XXXI, XXXII, XXXIII, XXXIV, XXXV, XXXVI, XXXVII, XXXVIII, XXXIX, or XXXX, wherein $L^1$ is a covalent bond, and $R^2$ is —N(R)C(O)—$R^{2A}$. In some embodiments, the present invention provides a compound of formula I, II, III, IV, V, VI, VII, VIII, IX, X, XI, XII, XIII, XIV, XV, XVI, XVII, XVIII, XIX, XX, XXI, XXII, XXIII, XXIV, XXV, XXVI, XXVII, XXVIII, XXIX, XXX, XXXI, XXXII, XXXIII, XXXIV, XXXV, XXXVI, XXXVII, XXXVIII, XXXIX, or XXXX, wherein $L^1$ is a covalent bond, and $R^2$ is —N(R)—$R^{2A}$. In some embodiments, the present invention provides a compound of formula I, II, III, IV, V, VI, VII, VIII, IX, X, XI, XII, XIII, XIV, XV, XVI, XVII, XVIII, XIX, XX, XXI, XXII, XXIII, XXIV, XXV, XXVI, XXVII, XXVIII, XXIX, XXX, XXXI, XXXII, XXXIII, XXXIV, XXXV, XXXVI, XXXVII, XXXVIII, XXXIX, or XXXX, wherein $L^1$ is a covalent bond, and $R^2$ is -$R^{2A}$.

In some embodiments, the present invention provides a compound of formula I, II, III, IV, V, VI, VII, VIII, IX, X, XI, XII, XIII, XIV, XV, XVI, XVII, XVIII, XIX, XX, XXI, XXII, XXIII, XXIV, XXV, XXVI, XXVII, XXVIII, XXIX, XXX, XXXI, XXXII, XXXIII, XXXIV, XXXV, XXXVI, XXXVII, XXXVIII, XXXIX, or XXXX, wherein $L^1$ is a covalent bond, and $R^2$ is —N(H)C(O)—$R^{2A}$, —N(H)—$R^{2A}$, or —$R^{2A}$. In some embodiments, the present invention provides a compound of formula I, II, III, IV, V, VI, VII, VIII, IX, X, XI, XII, XIII, XIV, XV, XVI, XVII, XVIII, XIX, XX, XXI, XXII, XXIII, XXIV, XXV, XXVI, XXVII, XXVIII, XXIX, XXX, XXXI, XXXII, XXXIII, XXXIV, XXXV, XXXVI, XXXVII, XXXVIII, XXXIX, or XXXX, wherein $L^1$ is a covalent bond, and $R^2$ is —N(I)C(O)—$R^{2A}$. In some embodiments, the present invention provides a compound of formula I, II, III, IV, V, VI, VII, VIII, IX, X, XI, XII, XIII, XIV, XV, XVI, XVII, XVIII, XIX, XX, XXI, XXII, XXIII, XXIV, XXV, XXVI, XXVII, XXVIII, XXIX, XXX, XXXI, XXXII, XXXIII, XXXIV, XXXV, XXXVI, XXXVII, XXXVIII, XXXIX, or XXXX, wherein $L^1$ is a covalent bond, and $R^2$ is —N(H)—$R^{2A}$.

In some embodiments, the present invention provides a compound of formula I, II, III, IV, V, VI, VII, VIII, IX, X, XI, XII, XIII, XIV, XV, XVI, XVII, XVIII, XIX, XX, XXI, XXII, XXIII, XXIV, XXV, XXVI, XXVII, XXVIII, XXIX, XXX, XXXI, XXXII, XXXIII, XXXIV, XXXV, XXXVI, XXXVII, XXXVIII, XXXIX, or XXXX, wherein Y is $C(R^{Y4})$, $L^1$ is a covalent bond, and $R^2$ is —N(R)C(O)—$R^{2A}$. In some embodiments, the present invention provides a compound of formula I, II, III, IV, V, VI, VII, VIII, IX, X, XI, XII, XIII, XIV, XV, XVI, XVII, XVIII, XIX, XX, XXI, XXII, XXIII, XXIV, XXV, XXVI, XXVII, XXVIII, XXIX, XXX, XXXI, XXXII, XXXIII, XXXIV, XXXV, XXXVI, XXXVII, XXXVIII, XXXIX, or XXXX, wherein Y is $C(R^{Y})$, $L^1$ is a covalent bond, and $R^2$ is —N(R)—$R^{2A}$. In some embodiments, the present invention provides a compound of formula I, II, III, IV, V, VI, VII, VIII, IX, X, XI, XII, XIII, XIV, XV, XVI, XVII, XVIII, XIX, XX, XXI, XXII, XXIII, XXIV, XXV, XXVI, XXVII, XXVIII, XXIX, XXX, XXXI, XXXII, XXXIII, XXXIV, XXXV, XXXVI, XXXVII, XXXVII, XXXIX, or XXXX, wherein Y is $C(R^{Y4})$, $L^1$ is a covalent bond, and $R^2$ is -$R^{2A}$.

In some embodiments, the present invention provides a compound of formula I, II, III, IV, V, VI, VII, VIII, IX, X, XI, XII, XIII, XIV, XV, XVI, XVII, XVIII, XIX, XX, XXI, XXII, XXIII, XXIV, XXV, XXVI, XXVII, XXVIII, XXIX, XXX, XXXI, XXXII, XXXIII, XXXIV, XXXV, XXXVI, XXXVII, XXXVIII, XXXIX, or XXXX, wherein Y is $C(R^4)$, $L^1$ is a covalent bond, and $R^2$ is —N(H)C(O)—$R^{2A}$, —N(H)—$R^{2A}$, or —$R^{2A}$. In some embodiments, the present invention provides a compound of formula I, II, III, IV, V, VI, VII, VIII, IX, X, XI, XII, XIII, XIV, XV, XVI, XVII, XVIII, XIX, XX, XXI, XXII, XXIII, XXIV, XXV, XXVI, XXVII, XXVIII, XXIX, XXX, XXXI, XXXII, XXXIII, XXXIV, XXXV, XXXVI, XXXVII, XXXVIII, XXXIX, or XXXX, wherein Y is $C(R^{Y4})$, $L^1$ is a covalent bond, and $R^2$ is —N(H)C(O)—$R^{2A}$. In some embodiments, the present invention provides a compound of formula I, II, III, IV, V, VI, VII, VIII, IX, X, XI, XII, XIII, XIV, XV, XVI, XVII, XVIII, XIX, XX, XXI, XXII, XXIII, XXIV, XXV, XXVI, XXVII, XXVIII, XXIX, XXX, XXXI, XXXII, XXXIII, XXXIV, XXXV, XXXVI, XXXVII, XXXVIII, XXXIX, or XXXX, wherein Y is $C(R^{Y4})$, $L^1$ is a covalent bond, and $R^2$ is —N(H)—$R^{1A}$.

In some embodiments, the present invention provides a compound of formula I, II, III, IV, V, VI, VII, VIII, IX, X, XI, XII, XIII, XIV, XV, XVI, XVII, XVIII, XIX, XX, XXI, XXII, XXIII, XXIV, XXV, XXVI, XXVII, XXVIII, XXIX, XXX, XXXI, XXXII, XXXIII, XXXIV, XXXV, XXXVI, XXXVII, XXXVIII, XXXIX, or XXXX, wherein Y is $C(R^{Y4})$.

In some embodiments, the present invention provides a compound of formula I, II, III, IV, V, VI, VII, VIII, IX, X, XI, XII, XIII, XIV, XV, XVI, XVII, XVIII, XIX, XX, XXI, XXII, XXIII, XXIV, XXV, XXVI, XXVII, XXVIII, XXIX, XXX, XXXI, XXXII, XXXIII, XXXIV, XXXV, XXXVI, XXXVII, XXXVIII, XXXIX, or XXXX, wherein $L^1$ is a covalent bond (i.e. $R^1$ is -$R^{1A}$).

In some embodiments, the present invention provides a compound of formula I, II, III, IV, V, VI, VII, VIII, IX, X, XI, XII, XIII, XIV, XV, XVI, XVII, XVIII, XIX, XX, XXI, XXII, XXIII, XXIV, XXV, XXVI, XXVII, XXVIII, XXIX, XXX, XXXI, XXXII, XXXIII, XXXIV, XXXV, XXXVI, XXXVII, XXXVIII, XXXIX, or XXXX, wherein $R^2$ is —N(R)C(O)—$R^{2A}$, —N(R)—$R^{2A}$, or —$R^{2A}$. In some embodiments, the present invention provides a compound of formula I, II, III, IV, V, VI, VII, VIII, IX, X, XI, XII, XIII, XIV, XV, XVI, XVII, XVIII, XIX, XX, XXI, XXII, XXIII, XXIV, XXV, XXVI, XXVII, XXVIII, XXIX, XXX, XXXI, XXXII, XXXIII, XXXIV, XXXV, XXXVI, XXXVII, XXXVIII, XXXIX, or XXXX, wherein $R^2$ is —N(R)C(O)—$R^{2A}$. In some embodiments, the present invention provides a compound of formula I, II, III, IV, V, VI, VII, VIII, IX, X, XI, XII, XIII, XIV, XV, XVI, XVII, XVIII, XIX, XX, XXI, XXII, XXIII, XXIV, XXV, XXVI, XXVII, XXVIII, XXIX, XXX, XXXI, XXXII, XXXIII, XXXIV, XXXV, XXXVI, XXXVII, XXXVIII, XXXIX, or XXXX, wherein $R^2$ is —N(R)—$R^{2A}$. In some embodiments, the present invention provides a compound of formula I, II, III, IV, V, VI, VII, VII, IX, X, XI, XII, XIII, XIV, XV, XVI, XVII, XVII, XIX, XX, XXI, XXII, XXII, XXIV, XXV, XXVI, XXVII, XXVIII, XXIX, XXX, XXXI, XXXII, XXXIII, XXXIV, XXXV, XXXVI, XXXVII, XXXVIII, XXXIX, or XXXX, wherein $R^2$ is -$R^{2A}$.

In some embodiments, the present invention provides a compound of formula I, II, III, IV, V, VI, VII, VIII, IX, X, XI, XII, XIII, XIV, XV, XVI, XVII, XVIII, XIX, XX, XXI, XXII, XXIII, XXIV, XXV, XXVI, XXVII, XXVIII, XXIX, XXX, XXXI, XXXII, XXXIII, XXXIV, XXXV, XXXVI, XXXVII, XXXVIII, XXXIX, or XXXX, wherein $R^2$ is —N(H)C(O)—$R^{2A}$, —N(H)—$R^{2A}$, or —$R^{2A}$. In some embodiments, the present invention provides a compound of formula I, II, III, IV, V, VI, VII, VIII, IX, X, XI, XII, XIII, XIV, XV, XVI, XVII, XVIII, XIX, XX, XXI, XXII, XXIII, XXIV, XXV, XXVI, XXVII, XXVIII, XXIX, XXX, XXXI, XXXII, XXXIII, XXXIV, XXXV, XXXVI, XXXVII, XXXVIII, XXXIX, or XXXX, wherein $R^2$ is —N(H)C(O)—$R^{2A}$. In some embodiments, the present invention provides a compound of formula I, II, III, IV, V, VI, VII, VIII, IX, X, XI, XII, XIII, XIV, XV, XVI, XVII, XVIII, XIX, XX, XXI, XXII, XXIII, XXIV, XXV, XXVI, XXVII, XXVIII, XXIX, XXX, XXXI, XXXII, XXXIII, XXXIV, XXXV, XXXVI, XXXVII, XXXVIII, XXXIX, or XXXX, wherein $R^2$ is —N(H)—$R^{2A}$.

In some embodiments, the present invention provides a compound of formula I, II, III, IV, V, VI, VII, VIII, IX, X, XI, XII, XIII, XIV, XV, XVI, XVII, XVIII, XIX, XX, XXI, XXII, XXIII, XXIV, XXV, XXVI, XXVII, XXVIII, XXIX, XXX, XXXI, XXXII, XXXIII, XXXIV, XXXV, XXXVI, XXXVII, XXXVIII, XXXIX, or XXXX, wherein Y is $C(R^{Y4})$.

Examples of compounds of the present invention include those listed in the Tables and exemplification herein, or a pharmaceutically acceptable salt, stereoisomer, or mixture of stereoisomers thereof. In some embodiments, the present invention comprises a compound selected from those depicted in Table 1, below, or a pharmaceutically acceptable salt, stereoisomer, or mixture of stereoisomers thereof. In some embodiments, the present invention provides a compound set forth in Table 1, below, or a pharmaceutically acceptable salt thereof. In some embodiments, the present invention provides a compound set forth in Table 1, below.

TABLE 2

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-1 | 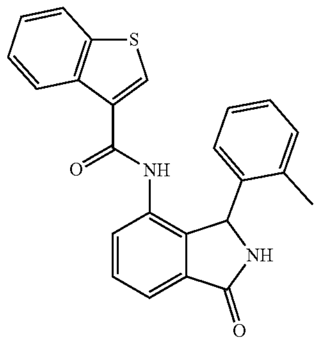 [SMILES: Cc1ccccc1C1NC(=O)c2cccc(NC(=O)c3csc4ccccc34)c21] | Cc1ccccc1C1NC(=O)c2cccc(NC(=O)c3csc4cccc c34)c12 | 1H NMR (400 MHz, DMSO-d6) 10.09 (s, 1H), 9.02 (s, 1H), 7.94-8.07 (m, 2H), 7.52-7.72 (m, 4H), 7.32-7.46 (m, 2H), 7.04-7.15 (m, 1H), 6.91-7.00 (m, 2H), 6.62 (br s, 1H), 6.02 (s, 1H), 2.07-2.30 (m, 3 H) | 399.2 | B | B |
| I-2 | 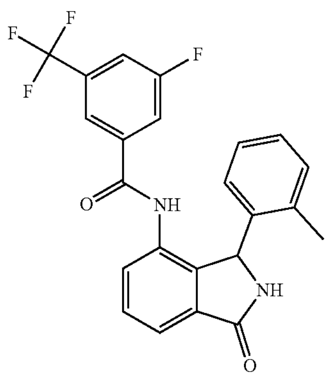 [SMILES: Cc1ccccc1C1NC(=O)c2cccc(NC(=O)c3cc(F)cc(C(F)(F)F)c3)c21] | Cc1ccccc1C1NC(=O)c2cccc(NC(=O)c3cc(F)cc(c3)C(F)(F)F)c12 | 1H NMR (400 MHz, DMSO-d6) 10.37 (s, 1 H) 9.06 (s, 1H) 7.88 (br d, 8.59 Hz., 1 H) 7.65-7.69 (m, 1 H) 7.61 (t, 7.58 Hz, 1 H) 7.51 (d, 7.58 Hz, 1 H) 7.47 (br d, 8.84 Hz, 1 H) 7.33 (br d, 1.26 Hz, 1 H) 7.02-7.08 (m, 1 H) 6.91-7.00 (m, 2H) 5.89 (br s, 1 H) 1.93-2.35 (m, 3H) | 429.3 | B | |
| I-3 | 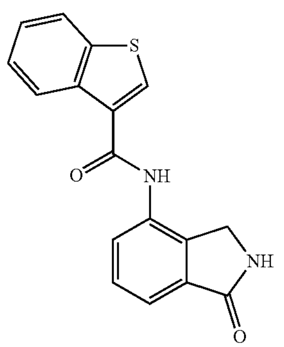 [SMILES: O=C1NCc2c(NC(=O)c3csc4ccccc34)cccc21] | O=C(Nc1cccc2C(=O)NCc12)c1csc2ccccc12 | 1H NMR (400 MHz, DMSO-d6) 10.33 (s, 1 H) 8.53-8.67 (m, 2 H) 8.31-8.47 (m, 1 H) 8.09 (br d, 6.57 Hz, 1 H) 7.79 (br dd, 3.54, 2.53 Hz, 1 H) 7.36-7.63 (m, 4 H) 4.43 (s, 2 H) | 309.17 | E | |
| I-4 | 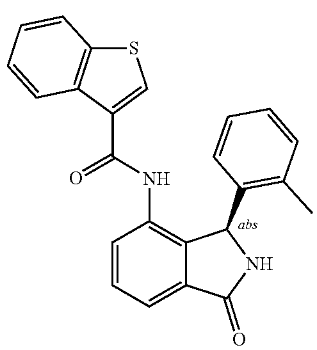 [SMILES: Cc1ccccc1[C@H]1NC(=O)c2cccc(NC(=O)c3csc4ccccc34)c21] | Cc1ccccc1[C@H]1NC(=O)c2cccc(NC(=O)c3csc4cccc c34)c12 | 1H NMR (400 MHz, DMSO-d6) 10.10 (s, 1 H) 9.04 (s, 1 H) 7.96-8.14 (m, 2 H) 7.54-7.74 (m, 4 H) 7.31-7.53 (m, 2 H) 6.89-7.16 (m, 3H) 6.46-6.83 (m, 1 H) 6.04 (s, 1 H) 2.19 (br s, 2 H) | 399.23 | C | |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-5 | 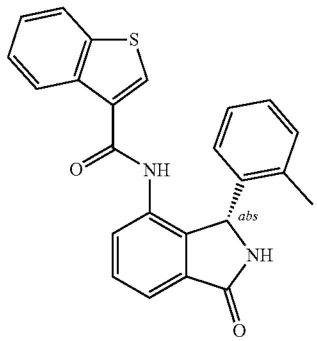 [SMILES: Cc1ccccc1[C@@H]1NC(=O)c2cccc(NC(=O)c3csc4ccccc34)c21] | Cc1ccccc1[C@@H]1NC(=O)c2cccc(NC(=O)c3csc4ccccc34)c12 | 1H NMR (400 MHz, DMSO-d6) 10.10 (s, 1 H) 9.04 (s, 1 H) 7.99-8.09 (m, 2 H) 7.57-7.69 (m, 4 H) 7.37-7.45 (m, 2 H) 7.0-7.13 (m, 1H) 7.02 (d, 7.33 Hz, 1 H) 6.95-7.01 (m, 1 H) 6.53-6.72 (m, 1 H) 6.04 (s, 1 H) 2.05-2.32 (m, 3 H) | 399.23 | A | B |
| I-6 | 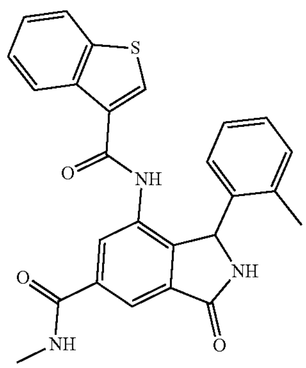 [SMILES: CNC(=O)c1cc(NC(=O)c2csc3ccccc23)c2c(c1)C(=O)NC2c1ccccc1C] | CNC(=O)c1cc2C(=O)NC(c2c(NC(=O)c2csc3ccccc23)c1)c1ccccc1C | 1H NMR (400 MHz, DMSO-d6) 10.15-10.31 (m, 1H), 9.11-9.22 (m, 1H), 8.63-8.81 (m, 1H), 8.12-8.15 (m, 1H), 8.08-8.18 (m, 2H), 8.04-8.10 (m, 2H), 8.04-8.09 (m, 2H), 7.97-8.03 (m, 1H), 7.70 (s, 1H), 7.33-7.49 (m, 2H), 6.91-7.17 (m, 5H), 5.96-6.18 (m, 1H), 2.73-3.00 (m, 4H), 2.11-2.26 (m, 3H) | 456 | A | A |
| I-7 | 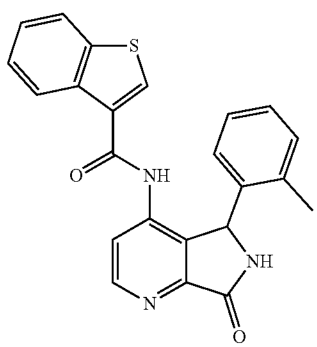 [SMILES: Cc1ccccc1C1NC(=O)c2nccc(NC(=O)c3csc4ccccc34)c21] | Cc1ccccc1C1NC(=O)c2nccc(NC(=O)c3csc4ccccc34)c12 | ¹H NMR (400 MHz, DMSO-d$_6$) δ 10.41 (s, 1H), 9.43 (s, 1H), 8.77 (d, J = 5.3 Hz, 1H), 8.01-8.06 (m, 1H), 7.98 (br d, J = 7.1 Hz, 1H), 7.75 (s, 1H), 7.64 (d, J = 5.3 Hz, 1H), 7.36-7.45 (m, 2H), 6.98-7.16 (m, 4H), 6.09 (s, 1H), 2.26 (br s, 3H). | 400.3 | B | |
| I-8 | 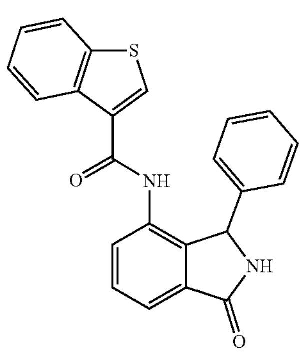 [SMILES: O=C1NC(c2ccccc2)c2c(NC(=O)c3csc4ccccc34)cccc21] | O=C(Nc1cccc2C(=O)NC(c12)c1ccccc1)c1csc2ccccc12 | 1H NMR (400 MHz, DMSO-d6) 10.13 (s, 1 H), 9.06 (s, 1 H), 8.16-8.25 (m, 1 H), 8.03-8.11 (m, 1 H), 7.94 (s, 1 H), 7.55-7.71 (m, 3 H), 7.40-7.51 (m, 2 H), 7.12-7.26 (m, 3 H), 6.98-7.10 (m, 2 H), 5.86 (s, 1 H) | 385.3 | B | |

TABLE 2-continued

Representative Compounds of the Invention with Bioactivity Data.

| Ex. No. | Structure | SMILES | $^1$H NMR | MS | ADP-Glo IC$_{50}$ | MCF 10A IC$_{50}$ |
|---|---|---|---|---|---|---|
| I-9 | 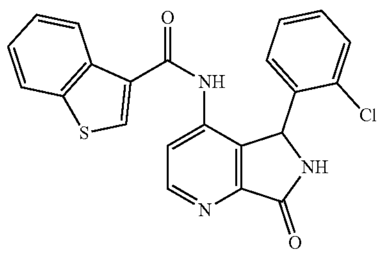 [SMILES: O=C1NC(c2ccccc2Cl)c2c(NC(=O)c3csc4ccccc34)ccnc21] | Clc1cccc c1C1NC (=O)c2ncc c(NC(=O) c3csc4cc ccc34)c1 2 | $^1$H NMR (400 MHz, DMSO-d$_6$) δ 10.50 (s, 1H), 9.46 (br s, 1H), 8.76 (d, J = 5.3 Hz, 1H), 8.08-8.14 (m, 1H), 8.02-8.07 (m, 1H), 7.95 (s, 1H), 7.58 (d, J = 5.3 Hz, 1H), 7.39-7.47 (m, 2H), 7.29-7.33 (m, 1H), 7.24 (td, J = 7.6, 1.6 Hz, 1H), 7.10-7.17 (m, 1H), 6.16-6.27 (m, 1H), 5.75 (s, 1H). | 420.2 | B | |
| I-10 | 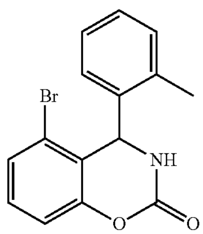 [SMILES: Cc1ccccc1C1NC(=O)Oc2cccc(Br)c21] | Cc1cccc c1C1NC(=O) Oc2cc cc(Br)c1 2 | | 318.2 | E | |
| I-11 | 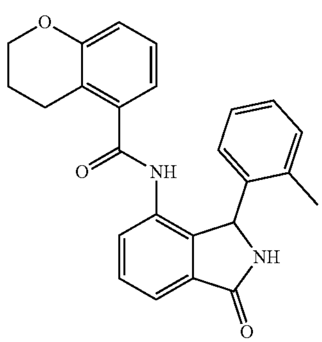 [SMILES: Cc1ccccc1C1NC(=O)c2cccc(NC(=O)c3cccc4c3CCCO4)c21] | Cc1cccc c1C1NC(=O) c2cccc (NC(=O) c3cccc4O CCCc34) c12 | 1H NMR (400 MHz, DMSO-d6) 9.94 (s, 1H), 9.03 (s, 1H), 7.63-7.54 (m, 3H), 7.24-7.16 (m, 2H), 7.05 (td, 7.3, 1.4 Hz, 1H), 6.94 (t, 7.8 Hz, 1H), 6.76 (dd, 8.2, 1.2 Hz, 1H), 6.53 (br. s, 1H), 6.10 (dd, 7.5, 1.1 Hz, 1H), 6.05 (br. s, 1H), 4.14-3.99 (m, 2H), 2.30 (br. s, 3H), 2.17 (t, 5.9 Hz, 1H), 2.13 (t, 5.7 Hz, 1H), 1.80-1.62 (m, 2H). | 399.3 | E | |
| I-12 | 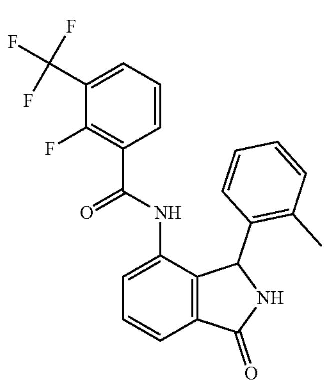 [SMILES: Cc1ccccc1C1NC(=O)c2cccc(NC(=O)c3cccc(C(F)(F)F)c3F)c21] | Cc1cccc c1C1NC(= O)c2cccc (NC(=O) c3cccc(c 3F)C(F) (F)F)c12 | 1H NMR (400 MHz, DMSO-d6) 10.32 (s, 1H), 9.07 (s, 1H), 7.87 (t, 6.8 Hz, 1H), 7.68 (dd, 7.5, 1.1 Hz, 1H), 7.61 (t, 7.6 Hz, 1H), 7.52 (dd, 7.7, 0.8 Hz, 1H), 7.35 (t, 7.8 Hz, 1H), 7.19 (td, 7.4, 1.3 Hz, 1H), 7.13 (d, 6.9 Hz, 1H), 7.08-6.96 (m, 2H), 6.59 (br s, 1H), 5.96 (s, 1H), 2.43-2.08 (br s, 3H). | 429.3 | E | |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-13 | 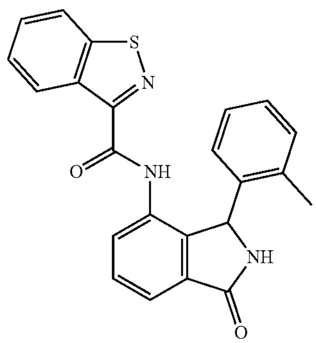 [SMILES: Cc1ccccc1C1NC(=O)c2cccc(NC(=O)c3nsc4ccccc34)c21] | Cc1ccccc1C1NC(=O)c2cccc(NC(=O)c3nsc4ccccc34)c12 | 1H NMR (400 MHz, DMSO-d6) 10.15 (s, 1H), 9.05 (s, 1H), 8.58 (d, 8.2 Hz, 1H), 8.29 (d, 8.2 Hz, 1H), 7.80 (dd, 7.6, 1.2 Hz, 1H), 7.74-7.55 (m, 4H), 7.06-6.93 (m, 2H), 6.89 (t, 13.3 Hz, 1H), 6.68 (br s, 1H), 6.12 (s, 1H), 2.40-2.10 (br s, 3H). | 400.3 | B | B |
| I-14 | 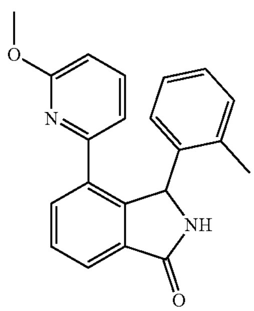 [SMILES: COc1cccc(-c2cccc3c2C(c2ccccc2C)NC3=O)n1] | COc1cccc(n1)-c1cccc2C(=O)NC(c12)c1ccccc1C | | 331.4 | E | |
| I-15 | 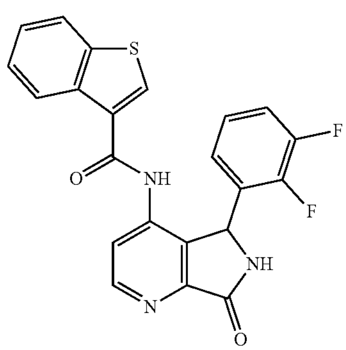 [SMILES: O=C1NC(c2cccc(F)c2F)c2c(NC(=O)c3csc4ccccc34)ccnc21] | Fc1cccc(C2NC(=O)c3nccc(NC(=O)c4csc5ccccc45)c23)c1F | ¹H NMR (400 MHz, DMSO-d$_6$) δ 10.61 (s, 1H), 9.49 (s, 1H), 8.76 (d, J = 5.1 Hz, 1H), 8.11-8.17 (m, 1H), 8.05-8.09 (m, 1H), 8.05 (s, 1H), 7.61 (d, J = 5.3 Hz, 1H), 7.41-7.48 (m, 2H), 7.25-7.34 (m, 1H), 6.98-7.05 (m, 1H), 6.82 (br t, J = 7.1 Hz, 1H), 6.11 (s, 1H). | 422.5 | B | |
| I-16 | 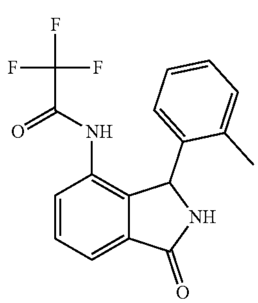 [SMILES: Cc1ccccc1C1NC(=O)c2cccc(NC(=O)C(F)(F)F)c21] | Cc1ccccc1C1NC(=O)c2cccc(NC(=O)C(F)(F)F)c12 | 1H NMR (400 MHz, DMSO-d6) 11.05 (s, 1H), 9.08 (s, 1H), 7.71 (d, 7.3 Hz, 1H), 7.61 (t, 7.6 Hz, 1H), 7.48 (dd, 7.8, 0.8 Hz, 1H), 7.24-7.08 (m, 2H), 7.10-6.95 (m, 1H), 6.53 (br. s, 1H), 5.86 (s, 1H), 2.27 (br. s, 3H). | 335 | E | |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-17 | 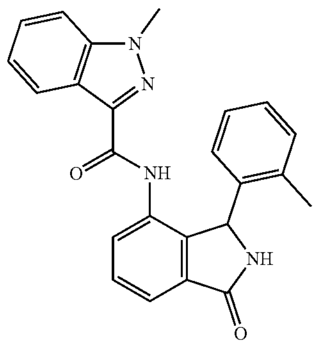 [SMILES: Cc1ccccc1C1NC(=O)c2cccc(NC(=O)c3nn(C)c4ccccc34)c21] | Cc1ccccc1C1NC(=O)c2cccc(NC(=O)c3nn(C)c4cccc34)c12 | 1H NMR (400 MHz, DMSO-d6) 9.35 (s, 2H), 9.02 (s, 2H), 8.07 (d, 8.3 Hz, 2H), 7.98 (p, 3.8 Hz, 2H), 7.72 (d, 8.6 Hz, 2H), 7.60-7.52 (m, 4H), 7.45 (dd, 11.4, 4.0 Hz, 2H), 7.31-7.25 (m, 2H), 7.13-7.01 (m, 4H), 6.98 (t, 7.3 Hz, 2H), 6.87-6.49 (m, 2H), 6.12 (s, 2H), 4.08 (s, 6H), 2.30 (br s, 3H) | 397 | E | |
| I-18 | 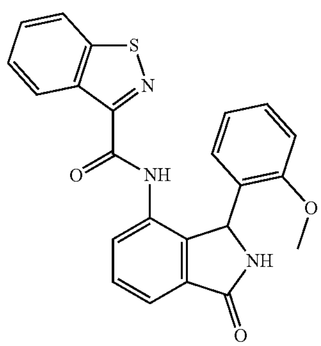 [SMILES: COc1ccccc1C1NC(=O)c2cccc(NC(=O)c3nsc4ccccc34)c21] | COc1cccc1C1NC(=O)c2cccc(NC(=O)c3csc4ccccc34)c12 | 1H NMR (400 MHz, DMSO-d6) 10.00 (br s, 1H), 8.86 (s, 1H), 8.38 (br s, 1H), 8.18 (dd, 6.1, 3.0 Hz, 1H), 8.01-8.07 (m, 1H), 7.98 (s, 1H), 7.59-7.65 (m, 2H), 7.50-7.58 (m, 1H), 7.35-7.44 (m, 2H), 7.07-7.21 (m, 1H), 6.80 (d, 8.3 Hz, 1H), 6.63-6.76 (m, 2H), 6.15 (s, 1H), 3.20-3.50 (m, 3H) | 415.4 | D | |
| I-19 | 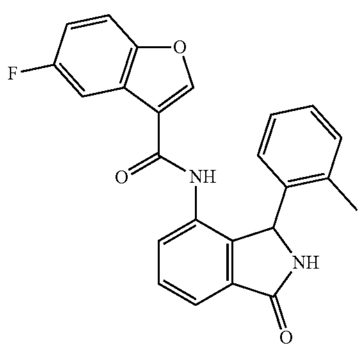 | Cc1ccccc1C1NC(=O)c2cccc(NC(=O)c3coc4cc(F)cc34)c12 | | 401.4 | C | B |
| I-20 | 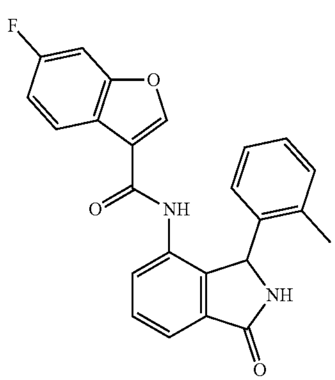 [SMILES: Cc1ccccc1C1NC(=O)c2cccc(NC(=O)c3coc4cc(F)ccc34)c21] | Cc1ccccc1C1NC(=O)c2cccc(NC(=O)c3coc4cc(F)ccc34)c12 | | 401.5 | C | |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-21 | 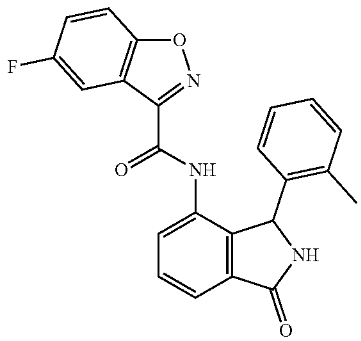 [SMILES: Cc1ccccc1C1NC(=O)c2cccc(NC(=O)c3noc4ccc(F)cc34)c21] | Cc1ccccc1C1NC(=O)c2cccc(NC(=O)c3noc4ccc(F)cc34)c12 | | 402.5 | D | |
| I-22 | 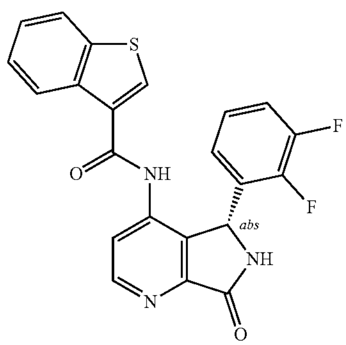 [SMILES: O=C1N[C@@H](c2cccc(F)c2F)c2c(NC(=O)c3csc4ccccc34)ccnc21] | Fc1cccc([C@@H]2NC(=O)c3nccc(NC(=O)c4csc5cccc45)c23)c1F | ¹H NMR (400 MHz, DMSO-d$_6$) δ 10.60 (s, 1H), 9.49 (s, 1H), 8.77 (d, J = 5.4 Hz., 1H), 8.11-8.16 (m, 1H), 8.05-8.09 (m, 1H), 8.05 (s, 1H), 7.60 (d, J = 5.4 Hz, 1H), 7.41-7.48 (m, 2H), 7.25-7.34 (m, 1H), 6.98-7.05 (m, 1H), 6.82 (br t, J = 7.0 Hz, 1H), 6.12 (s, 1H). | 422.4 | C | B |
| I-23 | 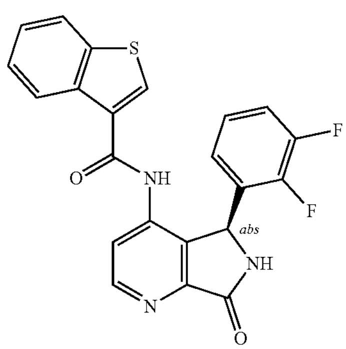 [SMILES: O=C1N[C@H](c2cccc(F)c2F)c2c(NC(=O)c3csc4ccccc34)ccnc21] | Fc1cccc([C@H]2NC(=O)c3nccc(NC(=O)c4csc5cccc45)c23)c1F | ¹H NMR (400 MHz, DMSO-d$_6$) δ 10.60 (br s, 1H), 9.49 (s, 1H), 8.76 (br d, J = 5.4 Hz, 1H), 8.10-8.18 (m, 1H), 8.07 (br d, J = 3.9 Hz, 1H), 8.05 (s, 1H), 7.61 (br d, J = 5.1 Hz, 1H), 7.44 (dt, J = 4.6, 2.3 Hz, 2H), 7.24-7.35 (m, 1H), 6.97-7.06 (m, 1H), 6.82 (br t, J = 6.8 Hz, 1H), 6.12 (s, 1H). | 422.4 | D | |
| I-24 | 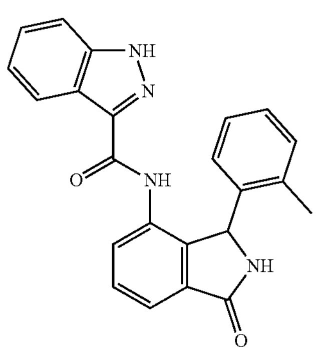 | Cc1ccccc1C1NC(=O)c2cccc(NC(=O)c3n[nH]c4cccc34)c12 | 1H NMR (400 MHz, DMSO-d6) 13.65 (s, 1H), 9.62 (s, 1H), 9.00 (s, 1H), 8.07 (d, 8.2 Hz, 1H), 7.87 (dd, 6.7, 2.2 Hz, 1H), 7.62-7.52 (m, 3H), 7.44-7.37 (m, 1H), 7.28-7.20 (m, 1H), 7.02-6.96 (m, 2H), 6.96-6.88 (br s, 1H), 6.66 (br s, 1H), 6.15 (s, 1H), 2.30 (br s, 3H) (formate salt) | 383.3 | E | |

TABLE 2-continued

Representative Compounds of the Invention with Bioactivity Data.

| Ex. No. | Structure | SMILES | $^1$H NMR | MS | ADP-Glo IC$_{50}$ | MCF 10A IC$_{50}$ |
|---|---|---|---|---|---|---|
| I-25 | 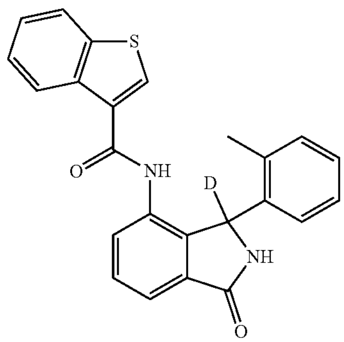 [SMILES: [2H]C1(c2ccccc2C)NC(=O)c2cccc(NC(=O)c3csc4ccccc34)c21] | [2H]C1(NC(=O)c2cccc(NC(=O)c3csc4cccc c34)c12)c1ccccc1C | 1H NMR (400 MHz, DMSO-d6) 10.09 (s, 1H), 9.01 (s, 1H), 8.03-7.95 (m, 2H), 7.66-7.51 (m, 4H), 7.43-7.32 (m, 2H), 7.07 (td, 7.4, 1.4 Hz, 1H), 7.02-6.88 (m, 2H), 6.55 (br s, 1H), 2.16 (br s, 3H). | 400.4 | A | B |
| I-26 | 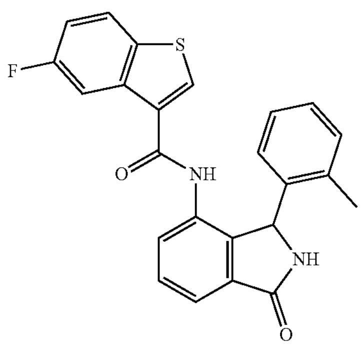 [SMILES: Cc1ccccc1C1NC(=O)c2cccc(NC(=O)c3csc4ccc(F)cc34)c21] | Cc1ccccc1C1NC(=O)c2cccc(NC(=O)c3csc4ccc(F)cc34)c12 | | 417.5 | B | B |
| I-27 | 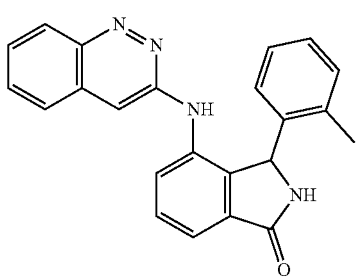 [SMILES: Cc1ccccc1C1NC(=O)c2cccc(Nc3cc4ccccc4nn3)c21] | Cc1ccccc1C1NC(=O)c2cccc(Nc3cc4ccccc4nn3)c12 | | 367.4 | E | |
| I-28 | 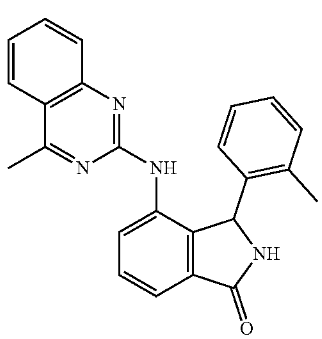 [SMILES: Cc1ccccc1C1NC(=O)c2cccc(Nc3nc(C)c4ccccc4n3)c21] | Cc1ccccc1C1NC(=O)c2cccc(Nc3nc(C)c4ccccc4n3)c12 | | 381.4 | E | |

TABLE 2-continued

Representative Compounds of the Invention with Bioactivity Data.

| Ex. No. | Structure | SMILES | $^1$H NMR | MS | ADP-Glo IC$_{50}$ | MCF 10A IC$_{50}$ |
|---|---|---|---|---|---|---|
| I-29 | 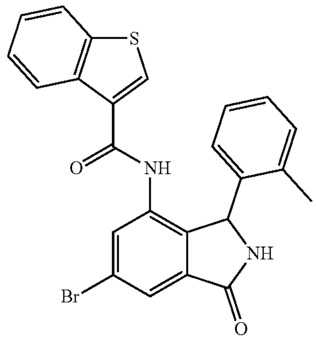 [SMILES: Cc1ccccc1C1NC(=O)c2cc(Br)cc(NC(=O)c3csc4ccccc34)c21] | Cc1ccccc1C1NC(=O)c2cc(Br)cc(NC(=O)c3csc4cccc34)c12 | 1H NMR (400 MHz, DMSO-d6) 10.12-10.35 (m, 1H), 9.13-9.35 (m, 1H), 7.96-8.08 (m, 2H), 7.80-7.87 (m, 1H), 7.71-7.78 (m, 1H), 7.56-7.68 (m, 1H), 7.32-7.49 (m, 2H), 7.05-7.14 (m, 1H), 6.88-7.05 (m, 2H), 6.44-6.82 (m, 1H), 5.91-6.11 (m, 1H), 1.82-2.38 (m, 3H) | 477 | A | A |
| I-30 | 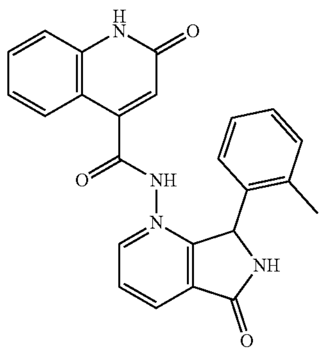 | Cc1ccccc1C1NC(=O)c2cccc(NC(=O)c3cc(=O)[nH]c4cccc34)c12 | 1H NMR (400 MHz, DMSO-d6) 11.91 (s, 1H), 10.54 (s, 1H), 9.10 (s, 1H), 7.69 (dd, 7.5, 1.1 Hz, 1H), 7.62 (t, 7.6 Hz, 1H), 7.55-7.46 (m, 2H), 7.30 (d, 7.7 Hz, 1H), 7.27-7.15 (m, 3H), 7.12-7.02 (m, 2H), 6.55 (br. s, 1H), 6.06 (s, 1H), 5.63 (d, 2.0 Hz, 1H), 2.33 (br. s, 3H). | 410 | E | |
| I-31 | 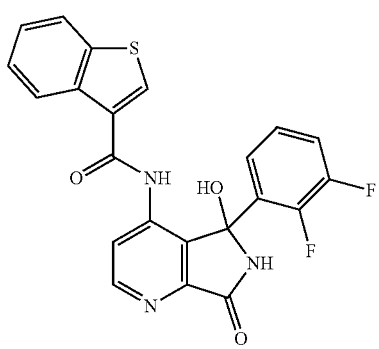 [SMILES: O=C1NC(O)(c2cccc(F)c2F)c2c(NC(=O)c3csc4ccccc34)ccnc21] | OC1(NC(=O)c2nccc(NC(=O)c3csc4cccc34)c12)c1cccc(F)c1F | | 438.5 | E | |
| I-32 | 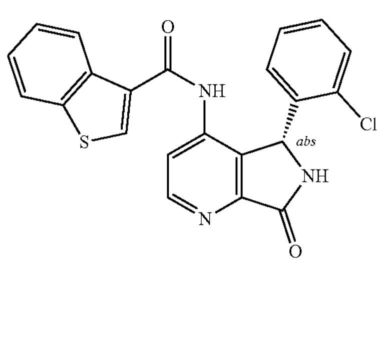 [SMILES: O=C1N[C@@H](c2ccccc2Cl)c2c(NC(=O)c3csc4ccccc34)ccnc21] | Clc1ccccc1[C@H]1NC(=O)c2nccc(NC(=O)c3csc4cccc34)c12 | $^1$H NMR (400 MHz, DMSO-d$_6$) δ 10.50 (s, 1H), 9.46 (br s, 1H), 8.76 (d, J = 5.3 Hz, 1H), 8.08-8.14 (m, 1H), 8.02-8.07 (m, 1H), 7.95 (s, 1H), 7.58 (d, J = 5.3 Hz, 1H), 7.39-7.47 (m, 2H), 7.29-7.33 (m, 1H), 7.24 (td, J = 7.6, 1.6 Hz, 1H), 7.10-7.17 (m, 1H), 6.16-6.27 (m, 1H), 5.75 (s, 1H). | 420.5 | D | |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-33 | 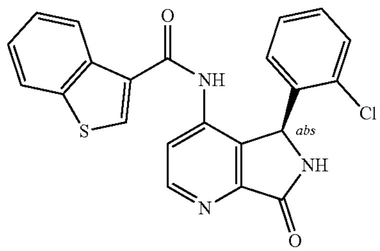 [SMILES: O=C1N[C@H](c2ccccc2Cl)c2c(NC(=O)c3csc4ccccc34)ccnc21] | C1c1cccc c1[C@@H]1NC(=O)c2nccc(NC(=O)c3csc4ccccc34)c12 | ¹H NMR (400 MHz, DMSO-d$_6$) δ 10.50 (s, 1H), 9.46 (br s, 1H), 8.76 (d, J = 5.3 Hz, 1H), 8.08-8.14 (m, 1H), 8.02-8.07 (m, 1H), 7.95 (s, 1H), 7.58 (d, J = 5.3 Hz, 1H), 7.39-7.47 (m, 2H), 7.29-7.33 (m, 1H), 7.24 (td, J = 7.6, 1.6 Hz, 1H), 7.10-7.17 (m, 1H), 6.16-6.27 (m, 1H), 5.75 (s, 1H). | 420.4 | B | B |
| I-34 | 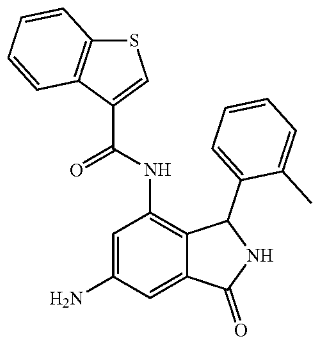 [SMILES: Cc1ccccc1C1NC(=O)c2cc(N)cc(NC(=O)c3csc4ccccc34)c21] | Cc1ccccc1C1NC(=O)c2cc(N)cc(NC(=O)c3csc4ccccc34)c12 | 1H NMR (400 MHz, DMSO-d6) 9.70-9.85 (m, 1H), 8.68-8.80 (m, 1H), 8.42-8.56 (m, 1H), 7.93-8.08 (m, 2H), 7.55 (s, 1H), 7.31-7.45 (m, 2H), 6.87-7.11 (m, 3H), 6.73-6.85 (m, 2H), 6.56-6.73 (m, 1H), 5.76-5.90 (m, 1H), 5.38-5.61 (m, 2H), 2.03-2.24 (m, 2H) | 414 | A | B |
| I-35 | 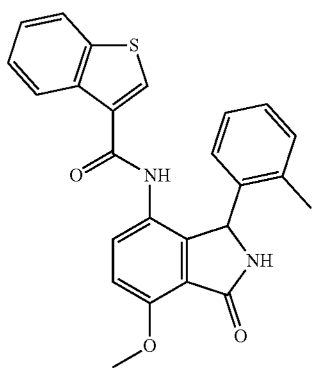 [SMILES: COc1ccc(NC(=O)c2csc3ccccc23)c2c1C(=O)NC2c1ccccc1C] | COc1ccc(NC(=O)c2csc3ccccc23)c2C(NC(=O)c12)c1ccccc1C | | 429.4 | A | B |
| I-36 | 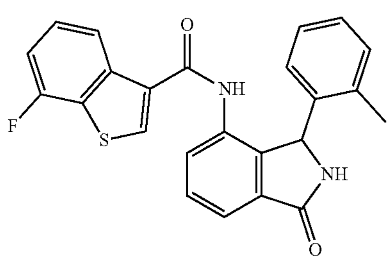 [SMILES: Cc1ccccc1C1NC(=O)c2cccc(NC(=O)c3csc4c(F)cccc34)c21] | Cc1ccccc1C1NC(=O)c2cccc(NC(=O)c3csc4c(F)cccc34)c12 | 1H NMR (400 MHz, DMSO-d6) 10.20 (s, 1H), 9.02 (s, 1H), 7.85 (br d, 8.34 Hz, 1H), 7.76 (s, 1H), 7.64-7.67 (m, 1H), 7.60 (t, 7.45 Hz, 1H), 7.53-7.57 (m, 1H), 7.43 (dt, 5.43, 8.02 Hz, 1H), 7.30 (dd, 7.83, 10.10 Hz, 1H), 7.05-7.10 (m, 1H), 6.94-7.01 (m, 2H), 6.55-6.67 (m, 1H), 6.00 (s, 1H) | 417.303 | B | |

TABLE 2-continued

Representative Compounds of the Invention with Bioactivity Data.

| Ex. No. | Structure | SMILES | $^1$H NMR | MS | ADP-Glo IC$_{50}$ | MCF 10A IC$_{50}$ |
|---|---|---|---|---|---|---|
| I-37 | 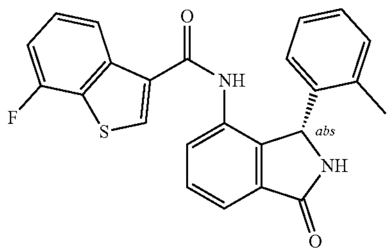 [SMILES: Cc1ccccc1[C@@H]1NC(=O)c2cccc(NC(=O)c3csc4c(F)cccc34)c21] | Cc1ccccc1[C@H]1NC(=O)c2cccc(NC(=O)c3csc4c(F)cccc34)c12 | 1H NMR (400 MHz, DMSO-d6) 10.20 (s, 1H), 9.02 (s, 1H), 7.85 (br d, 8.34 Hz, 1H), 7.76 (s, 1H), 7.63-7.68 (m, 1H), 7.59-7.62 (m, 1H), 7.51-7.57 (m, 1H), 7.43 (dt, 5.43, 8.02 Hz, 1H), 7.28-7.34 (m, 1H), 7.04-7.11 (m, 1H), 6.93-7.02 (m, 2H), 6.55-6.66 (m, 1H), 6.00 (s, 1H), 2.07-2.25 (m, 3H) | 417.25 | E | |
| I-38 | 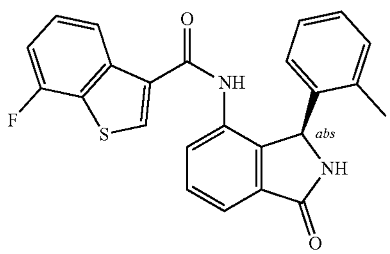 [SMILES: Cc1ccccc1[C@H]1NC(=O)c2cccc(NC(=O)c3csc4c(F)cccc34)c21] | Cc1ccccc1[C@@H]1NC(=O)c2cccc(NC(=O)c3csc4c(F)cccc34)c12 | 1H NMR (400 MHz, DMSO-d6) 10.20 (s, 1H), 9.02 (s, 1H), 7.85 (br d, 8.34 Hz., 1H), 7.76 (s, 1H), 7.63-7.68 (m, 1H), 7.59-7.62 (m, 1H), 7.51-7.57 (m, 1H), 7.43 (dt, 5.43, 8.02 Hz, 1H), 7.28-7.34 (m, 1H), 7.04-7.11 (m, 1H), 6.93-7.02 (m, 2H), 6.55-6.66 (m, 1H), 6.00 (s, 1H), 2.07-2.25 (m, 3H) | 417.25 | B | B |
| I-39 | 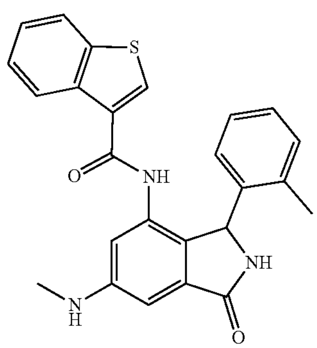 [SMILES: CNc1cc(NC(=O)c2csc3ccccc23)c2c(c1)C(=O)NC2c1ccccc1C] | CNc1cc2C(=O)NC(c2c(NC(=O)c2csc3cccc23)c1)c1ccccc1C | 1H NMR (400 MHz, DMSO-d6) 9.76-9.94 (m, 1H), 8.71-8.85 (m, 1H), 8.39-8.52 (m, 1H), 7.93-8.08 (m, 2H), 7.52-7.66 (m, 1H), 7.26-7.46 (m, 3H), 6.90-7.16 (m, 4H), 6.59-6.85 (m, 4H), 6.00-6.18 (m, 2H), 5.77-5.90 (m, 1H), 2.70-2.85 (m, 3H), 2.03-2.29 (m, 3H) | 428 | A | B |
| I-40 | 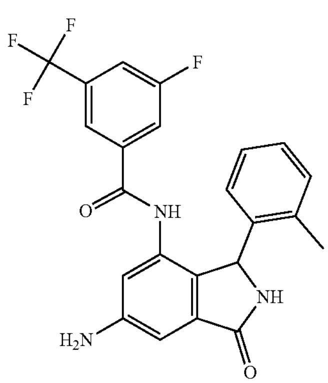 [SMILES: Cc1ccccc1C1NC(=O)c2cc(N)cc(NC(=O)c3cc(F)cc(C(F)(F)F)c3)c21] | Cc1ccccc1C1NC(=O)c2cc(N)cc(NC(=O)c3cc(F)cc(c3)C(F)(F)F)c12 | 1H NMR (400 MHz, DMSO-d6) 9.98-10.14 (m, 1H), 8.68-8.84 (m, 1H), 8.44-8.59 (m, 1H), 7.75-7.93 (m, 1H), 7.36-7.51 (m, 1H), 7.22-7.36 (m, 1H), 6.98-7.08 (m, 1H), 6.85-6.97 (m, 1H), 6.68-6.85 (m, 2H), 6.43-6.68 (m, 2H), 5.62-5.79 (m, 1H), 5.42-5.60 (m, 1H), 2.01-2.26 (m, 3H) | 444 | A | B |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-41 | 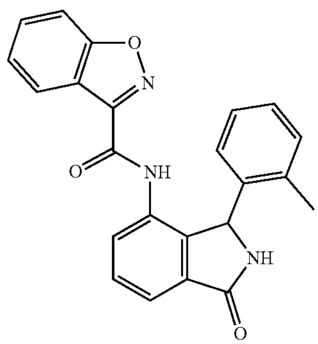 [SMILES: Cc1ccccc1C1NC(=O)c2cccc(NC(=O)c3noc4ccccc34)c21] | Cc1ccccc1C1NC(=O)c2cccc(NC(=O)c3noc4ccccc34)c12 | 1H NMR (400 MHz, DMSO-d6) 9.07 (s, 1H), 7.86 (d, 8.8 Hz, 2H), 7.77-7.67 (m, 2H), 7.63 (d, 4.3 Hz, 2H), 7.49 (t, 7.8 Hz, 1H), 7.03-6.84 (m, 3H), 6.61 (br s, 1H), 6.05 (s, 1H), 2.42-1.87 (m, 3H). | 384.3 | E | |
| I-42 | 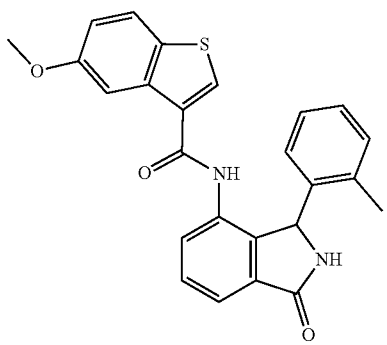 | COc1ccc2scc(C(=O)Nc3cccc4C(=O)NC(c34)c3ccccc3C)c2c1 | 1H NMR (400 MHz, DMSO-d6) 10.08 (s, 1H), 9.04 (s, 1H), 7.89 (d, 8.9 Hz, 1H), 7.78 (d, 2.5 Hz, 1H), 7.66 (dd, 7.1, 1.5 Hz, 1H)., 7.62 (s, 1H), 7.60 (d, 7.2 Hz., 1H), 7.57 (dd, 7.7, 1.5 Hz, 1H), 7.12-7.03 (m, 2H), 7.03-6.90 (m, 2H), 6.61 (s, 1H), 6.03 (s, 1H), 3.79 (s, 3H), 2.18 (br s, 3H). | 429.3 | D | |
| I-43 | 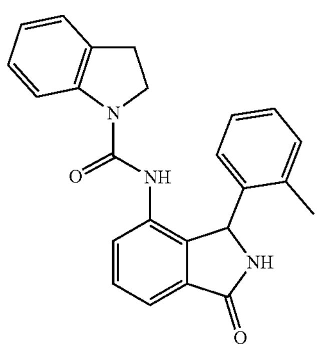 [SMILES: Cc1ccccc1C1NC(=O)c2cccc(NC(=O)N3CCc4ccccc43)c21] | Cc1ccccc1C1NC(=O)c2cccc(NC(=O)N3CCc4ccccc34)c12 | 1H NMR (400 MHz, DMSO-d6) 8.95 (s, 1H), 8.37 (s, 1H), 7.68 (d, 8.0 Hz, 1H), 7.60-7.50 (m, 2H), 7.47-7.35 (m, 1H), 7.19-7.06 (m, 3H), 7.02 (d, 7.3 Hz, 1H), 6.95 (t, 7.1 Hz, 1H), 6.88 (td, 7.4, 1.0 Hz, 1H), 6.54 (s, 1H), 5.88 (s, 1H), 3.68-3.50 (m, 1H), 3.01-2.80 (m, 3H), 2.07 (s, 3H). | 384.3 | A | B |
| I-44 | 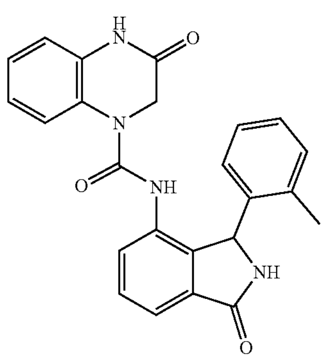 [SMILES: Cc1ccccc1C1NC(=O)c2cccc(NC(=O)N3CC(=O)Nc4ccccc43)c21] | Cc1ccccc1C1NC(=O)c2cccc(NC(=O)N3CC(=O)Nc4ccccc34)c12 | 1H NMR (400 MHz, DMSO-d6) 10.63 (s, 1H), 8.87 (s, 1H), 7.52 (dd, 7.4, 1.2 Hz, 1H), 7.47 (t, 7.5 Hz, 1H), 7.32 (dd, 7.6, 1.0 Hz, 1H), 7.19-7.06 (m, 3H), 7.01-6.94 (m, 1H), 6.90 (dd, 8.0, 1.4 Hz, 1H), 6.60 (t, 7.8 Hz, 1H), 5.91 (s, 1H), 5.84 (d, 7.3 Hz, 1H), 4.30 (d, 16.3 Hz, 1H), 3.75 (t, 12.4 Hz, 1H), 2.42-2.10 (m, 3H) | 411.4 | E | |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-45 | 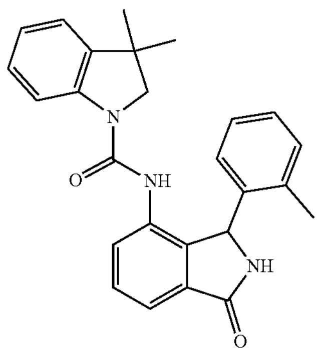 [SMILES: Cc1ccccc1C1NC(=O)c2cccc(NC(=O)N3CC(C)(C)c4ccccc43)c21] | Cc1ccccc1C1NC(=O)c2cccc(NC(=O)N3CC(C)(C)c4cccc34)c12 | 1H NMR (400 MHz, DMSO-d6) 8.96 (s, 1H), 8.31 (s, 1H), 7.71 (d, 8.1 Hz, 1H), 7.56-7.51 (m, 2H), 7.50-7.44 (m, 1H), 7.19-7.07 (m, 3H), 7.03 (d, 7.4 Hz, 1H), 6.99-6.89 (m, 2H), 6.56 (br. s, 1H), 5.93 (s, 1H), 3.36 (d, 9.9 Hz, 1H), 2.78 (d, 9.8 Hz, 1H), 2.19 (br. s, 3H), 1.17 (s, 3H), 1.13 (s, 3H) | 412.3 | D | D |
| I-46 | 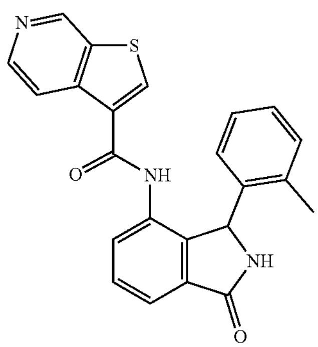 [SMILES: Cc1ccccc1C1NC(=O)c2cccc(NC(=O)c3csc4cnccc34)c21] | Cc1ccccc1C1NC(=O)c2cccc(NC(=O)c3csc4cnccc34)c12 | | 400 | B | D |
| I-47 | 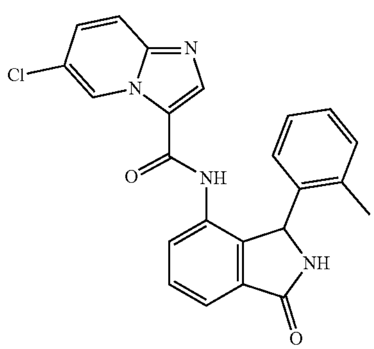 [SMILES: Cc1ccccc1C1NC(=O)c2cccc(NC(=O)c3cnc4ccc(Cl)cn34)c21] | Cc1ccccc1C1NC(=O)c2cccc(NC(=O)c3cnc4ccc(Cl)cn34)c12 | | 417.2 | E | |
| I-48 | 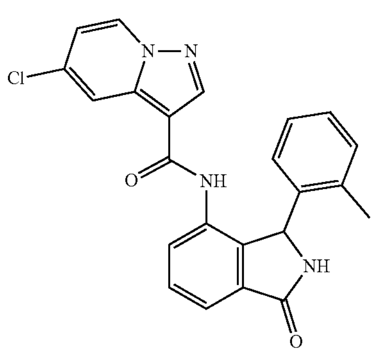 [SMILES: Cc1ccccc1C1NC(=O)c2cccc(NC(=O)c3cnn4ccc(Cl)cc34)c21] | Cc1ccccc1C1NC(=O)c2cccc(NC(=O)c3cnn4ccc(Cl)cc34c12 | | 417.2 | D | |

TABLE 2-continued

Representative Compounds of the Invention with Bioactivity Data.

| Ex. No. | Structure | SMILES | $^1$H NMR | MS | ADP-Glo IC$_{50}$ | MCF 10A IC$_{50}$ |
|---|---|---|---|---|---|---|
| I-49 | 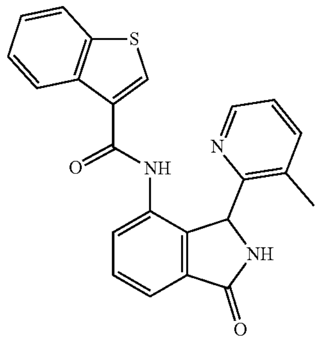 [SMILES: Cc1cccnc1C1NC(=O)c2cccc(NC(=O)c3csc4ccccc34)c21] | Cc1cccnc1C1NC(=O)c2cccc(NC(=O)c3csc4ccccc34)c12 | $^1$H NMR (400 MHz, DMSO-d$_6$) δ 10.13 (s, 1H), 9.03 (s, 1H), 8.18 (dd, J = 4.7, 1.4 Hz, 1H), 8.11-8.16 (m, 1H), 8.01-8.07 (m, 1H), 7.89 (s, 1H), 7.78-7.85 (m, 3H), 7.60-7.65 (m, 1H), 7.51-7.59 (m, 2H), 7.13 (dd, J = 7.7, 4.7 Hz, 1H), 6.18 (s, 1H), 2.17-2.26 (m, 3H) | 400.4 | D | |
| I-50 | 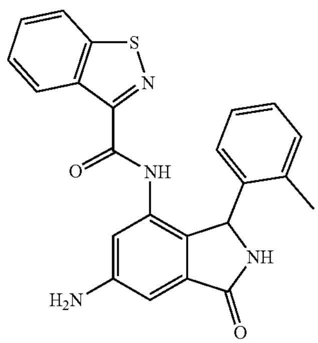 [SMILES: Cc1ccccc1C1NC(=O)c2cc(N)cc(NC(=O)c3nsc4ccccc34)c21] | Cc1ccccc1C1NC(=O)c2cc(N)cc(NC(=O)c3nsc4ccccc34)c12 | 1H NMR (400 MHz, DMSO-d6) 9.6-9.9 (m, 1H), 8.7-8.9 (m, 1H), 8.4-8.6 (m, 1H), 8.2-8.3 (m, 1H), 7.6-7.8 (m, 1H), 7.5-7.6 (m, 1H), 7.1-7.2 (m, 1H), 6.9-7.0 (m, 3H), 6.7-6.8 (m, 1H), 6.5-6.7 (m, 1H), 5.8-6.0 (m, 1H), 5.4-5.6 (m, 2H), 2.1-2.4 (m, 3H) | 415 | A | A |
| I-51 | 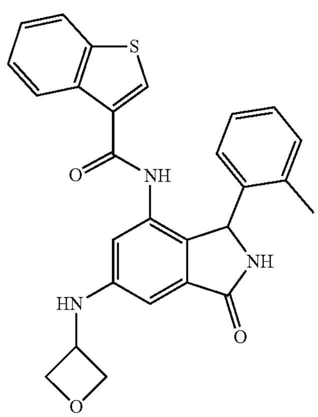 [SMILES: Cc1ccccc1C1NC(=O)c2cc(NC3COC3)cc(NC(=O)c3csc4ccccc34)c21] | Cc1ccccc1C1NC(=O)c2cc(NC3COC3)cc(NC(=O)c3csc4ccccc34)c12 | 1H NMR (400 MHz, DMSO-d6) 9.8-9.9 (m, 1H), 8.8-9.0 (m, 1H), 7.9-8.1 (m, 2H), 7.6-7.7 (m, 1H), 7.3-7.5 (m, 2H), 6.9-7.1 (m, 2H), 6.7-6.9 (m, 2H), 6.5-6.7 (m, 2H), 5.8-5.9 (m, 1H), 4.8-5.0 (m, 2H), 4.6-4.7 (m, 1H), 4.4-4.5 (m, 1H), 3.9-4.3 (m, 2H), 2.1-2.3 (m, 3H) | 470 | A | A |
| I-52 | 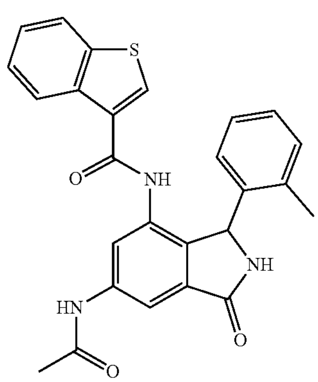 [SMILES: CC(=O)Nc1cc(NC(=O)c2csc3ccccc23)c2c(c1)C(=O)NC2c1ccccc1C] | CC(=O)Nc1cc2C(=O)NC(c2c(NC(=O)c2csc3cccc23)c1)c1ccccc1C | 1H NMR (400 MHz, DMSO-d6) 10.2-10.4 (m, 1H), 10.0-10.2 (m, 1H), 8.9-9.1 (m, 1H), 8.0-8.1 (m, 1H), 7.9-8.0 (m, 1H), 7.8-7.9 (m, 1H), 7.5-7.7 (m, 2H), 7.3-7.5 (m, 1H), 6.9-7.2 (m, 1H), 6.5-6.8 (m, 1H), 5.9-6.0 (m, 1H), 2.3-2.4 (m, 1H), 2.1-2.2 (m, 1H), 2.1-2.1 (m, 1H), 2.1-2.2 (m, 6H) | 456 | A | A |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-53 | 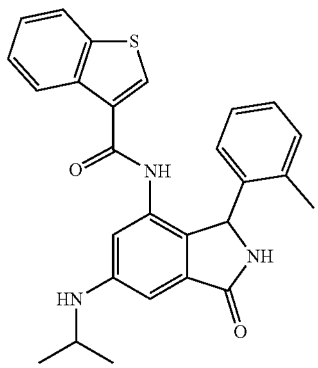 [SMILES: Cc1ccccc1C1NC(=O)c2cc(NC(C)C)cc(NC(=O)c3csc4ccccc34)c21] | CC(C)Nc1cc2C(=O)NC(c2c(NC(=O)c2csc3ccccc23)c1)c1ccccc1C | 1H NMR (400 MHz, DMSO-d6) 9.8-9.9 (m, 1H), 8.7-8.8 (m, 1H), 8.2-8.4 (m, 1H), 7.9-8.1 (m, 3H), 7.6-7.8 (m, 3H), 7.3-7.5 (m, 2H), 6.9-7.2 (m, 2H), 6.5-6.7 (m, 1H), 5.7-6.0 (m, 2H), 2.1-2.3 (m, 3H), 1.0-1.2 (m, 6H) | 456 | A | A |
| I-54 | 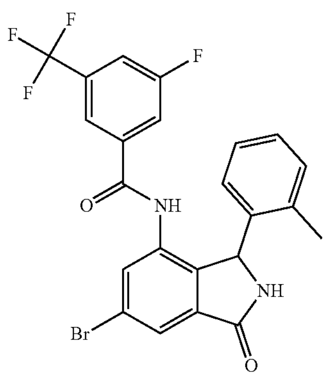 [SMILES: Cc1ccccc1C1NC(=O)c2cc(Br)cc(NC(=O)c3cc(F)cc(C(F)(F)F)c3)c21] | Cc1ccccc1C1NC(=O)c2cc(Br)cc(NC(=O)c3cc(F)cc(c3)C(F)(F)F)c12 | 1H NMR (400 MHz, DMSO-d6) 10.0-10.1 (m, 1H), 8.6-8.8 (m, 1H), 7.7-7.9 (m, 1H), 7.4-7.5 (m, 1H), 7.2-7.3 (m, 1H), 6.9-7.1 (m, 3H), 6.8-6.8 (m, 1H), 6.7-6.8 (m, 1H), 6.5-6.6 (m, 1H), 5.6-5.8 (m, 1H), 1.8-2.3 (m, 3H) | 507 | B | B |
| I-55 | 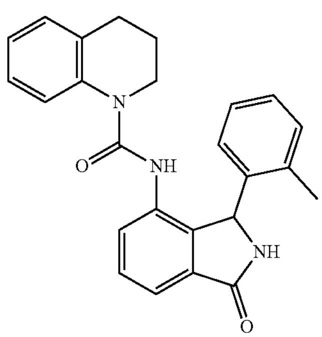 [SMILES: Cc1ccccc1C1NC(=O)c2cccc(NC(=O)N3CCCc4ccccc43)c21] | Cc1ccccc1C1NC(=O)c2cccc(NC(=O)N3CCCc4ccccc34)c12 | 1H NMR (400 MHz, DMSO-d6) 8.92 (s, 1H), 8.57 (s, 1H), 7.52-7.41 (m, 2H), 7.41-7.32 (m, 1H), 7.22-6.99 (m, 4H), 6.86 (td, 7.4, 1.2 Hz, 1H), 6.78 (t, 7.7 Hz, 1H), 6.47 (br s, 1H), 6.32 (d, 8.0 Hz, 1H), 5.90 (s, 1H), 3.44-3.35 (m, 1H), 3.15-3.06 (m, 1H), 2.67-2.49 (m, 2H), 2.40-2.07 (br s, 3H), 1.74-1.47 (m, 2H). | 397.9 | D | |
| I-56 | 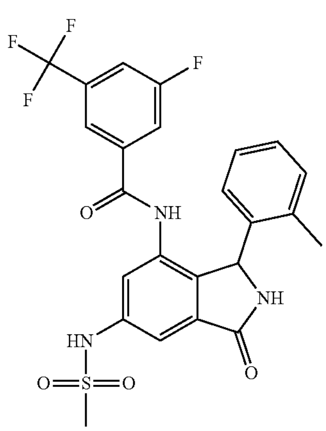 [SMILES: Cc1ccccc1C1NC(=O)c2cc(NS(C)(=O)=O)cc(NC(=O)c3cc(F)cc(C(F)(F)F)c3)c21] | Cc1ccccc1C1NC(=O)c2cc(NS(C)(=O)=O)cc(NC(=O)c3cc(F)cc(c3)C(F)(F)F)c12 | 1H NMR (400 MHz, DMSO-d6) 10.2-10.5 (m, 1H), 8.8-9.1 (m, 1H), 8.3-8.5 (m, 1H), 7.7-7.9 (m, 1H), 7.4-7.5 (m, 1H), 7.3-7.4 (m, 1H), 7.2-7.3 (m, 1H), 7.0-7.1 (m, 1H), 6.9-7.0 (m, 2H), 6.6-6.7 (m, 2H), 5.7-5.9 (m, 1H), 2.8-3.1 (m, 3H), 2.1-2.3 (m, 3H) | 522 | B | |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-57 | 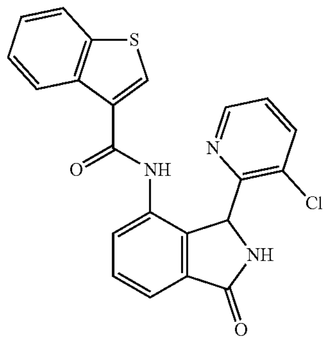 [SMILES: O=C1NC(c2ncccc2Cl)c2c(NC(=O)c3csc4ccccc34)cccc21] | Clc1cccnc1C1NC(=O)c2cccc(NC(=O)c3csc4ccccc34)c12 | ¹H NMR (400 MHz, DMSO-d$_6$) δ 10.14 (s, 1H), 9.08 (s, 1H), 8.28 (dd, J = 1.52, 4.55 Hz, 1H), 8.17-8.24 (m, 1H), 7.98-8.06 (m, 2H), 7.72 (dd, J = 1.39, 8.21 Hz, 1H), 7.60-7.66 (m, 1H), 7.56 (t, J = 7.58 Hz, 1H), 7.47 (dd, J = 1.01, 7.58 Hz, 1H), 7.38-7.44 (m, 2H), 7.25 (dd, J = 4.55, 8.08 Hz, 1H), 6.30-6.57 (m, 1H). | 420.3 | D | |
| I-58 | 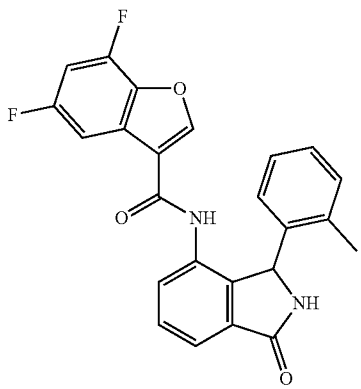 [SMILES: Cc1ccccc1C1NC(=O)c2cccc(NC(=O)c3coc4c(F)cc(F)cc34)c21] | Cc1ccccc1C1NC(=O)c2cccc(NC(=O)c3coc4c(F)cc(F)cc34)c12 | | 419.4 | B | |
| I-59 | 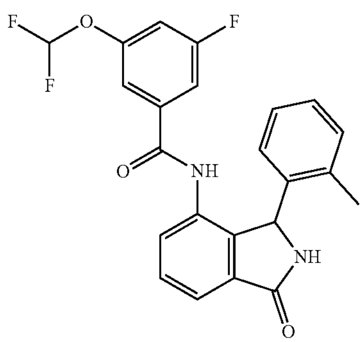 [SMILES: Cc1ccccc1C1NC(=O)c2cccc(NC(=O)c3cc(F)cc(OC(F)F)c3)c21] | Cc1ccccc1C1NC(=O)c2cccc(NC(=O)c3cc(F)cc(OC(F)F)c3)c12 | | 427.4 | D | |
| I-60 | 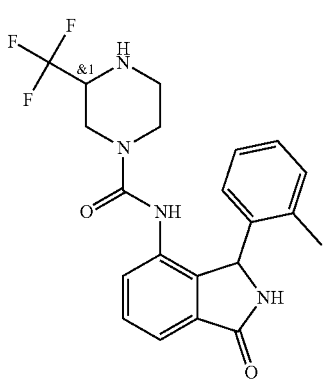 [SMILES: Cc1ccccc1C1NC(=O)c2cccc(NC(=O)N3CCNC(C(F)(F)F)C3)c21] | Cc1ccccc1C1NC(=O)c2cccc(NC(=O)N3CCNC(C3)C(F)(F)F)c12 | 1H NMR (400 MHz, DMSO-d6) 8.93 (d, 3.3 Hz, 1H), 8.56 (s, 1H), 8.47 (s, 1H), 7.52-7.45 (m, 2H), 7.32-7.24 (m, 1H), 7.21-7.11 (m, 2H), 7.07-6.97 (m, 1H), 6.47 (br s, 1H), 5.89 (s, 1H), 3.72-3.59 (m, 1H), 3.53 (d, 10.8 Hz, 1H), 3.20-3.40 (m., 2 H), 2.85-2.70 (m, 1H), 2.70-2.62 (m, 1H), 2.62-2.52 (m, 1H), 2.40-2.25 (m, 3H). | 418.9 | E | |

TABLE 2-continued

Representative Compounds of the Invention with Bioactivity Data.

| Ex. No. | Structure | SMILES | $^1$H NMR | MS | ADP-Glo IC$_{50}$ | MCF 10A IC$_{50}$ |
|---|---|---|---|---|---|---|
| I-61 | 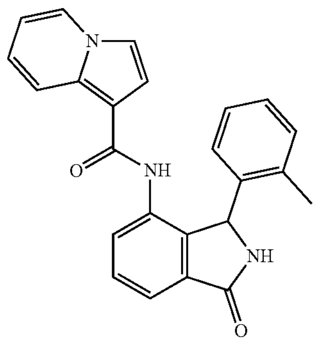 [SMILES: Cc1ccccc1C1NC(=O)c2cccc(NC(=O)c3ccn4ccccc34)c21] | Cc1ccccc1C1NC(=O)c2cccc(NC(=O)c3ccn4ccccc34)c12 | 1H NMR (400 MHz, DMSO-d6) 9.24 (s, 1H), 8.97 (s, 1H), 8.36 (dt, 6.9, 1.1 Hz, 1H), 8.04 (d, 9.1 Hz, 1H), 7.68 (dd, 6.2, 2.7 Hz, 1H), 7.56 (s, 1H), 7.58-7.53 (m, 1H), 7.45 (d, 3.0 Hz, 1H), 7.05-7.00 (m, 2H), 6.99-6.96 (m, 1H), 6.92 (td, 7.4, 1.4 Hz, 1H), 6.89 (d, 3.1 Hz, 1H), 6.77 (td, 6.8, 1.3 Hz, 1H), 6.61 (br s, 1H), 6.15 (s, 1H), 2.22 (br s, 3H) | 382.3 | B | |
| I-62 | 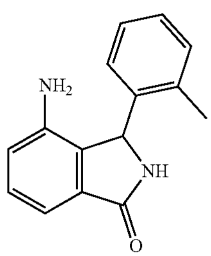 [SMILES: Cc1ccccc1C1NC(=O)c2cccc(N)c21] | Cc1ccccc1C1NC(=O)c2cccc(N)c12 | 1H NMR (400 MHz, DMSO-d6) 8.79 (s, 1H), 7.23 (t, 7.6 Hz, 1H), 7.21-7.19 (m, 2H), 7.09 (dt, 8.5, 4.3 Hz, 1H), 6.96 (dd, 7.4, 0.8 Hz, 1H), 6.79 (dd, 7.9, 0.8 Hz, 1H), 6.78 (br s, 1H), 5.68 (s, 1H), 4.62 (s, 2H), 2.35 (br s, 3H). | 239.2 | E | |
| I-63 | 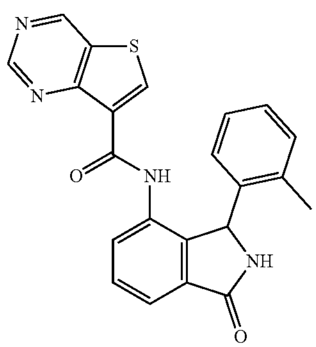 [SMILES: Cc1ccccc1C1NC(=O)c2cccc(NC(=O)c3csc4cncnc34)c21] | Cc1ccccc1C1NC(=O)c2cccc(NC(=O)c3csc4cncnc34)c12 | 1H NMR (400 MHz, DMSO-d6) 10.53 (s, 1H), 9.63 (s, 1H), 9.19 (s, 1H), 9.13 (s, 1H), 8.91 (s, 1H), 8.25 (d, 5.8 Hz, 1H), 7.76-7.58 (m, 2H), 7.13 (d, 7.5 Hz, 1H), 7.04 (t, 7.5 Hz, 1H), 6.90 (t, 7.2 Hz, 1H), 6.54 (br s, 1H), 6.12 (s, 1H), 2.49-2.24 (br s, 3H). | 400.46 | E | |
| I-64 | 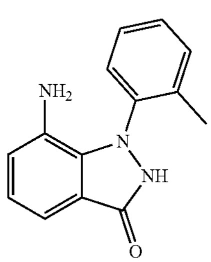 [SMILES: Cc1ccccc1-n1[nH]c(=O)c2cccc(N)c21] | Cc1ccccc1-n1[nH]c(=O)c2cccc(N)c12 | 1H NMR (400 MHz, CDCl3) 8.03 (s, 1H), 7.43-7.37 (m, 1H), 7.36-7.33 (m, 1H), 7.29 (d, 3.5 Hz, 2H), 7.21 (dd, 7.9, 0.7 Hz, 1H), 6.96 (t, 7.5 Hz, 1H), 6.62 (dd, 7.4, 0.7 Hz, 1H), 2.19 (s, 3H). | 239.9 | D | |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-65 | 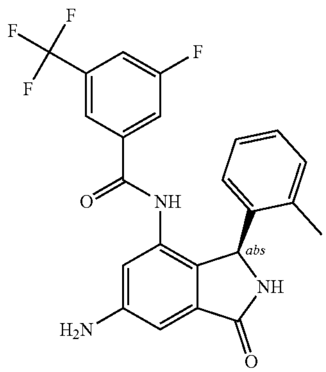 [SMILES: Cc1ccccc1[C@H]1NC(=O)c2cc(N)cc(NC(=O)c3cc(F)cc(C(F)(F)F)c3)c21] | Cc1ccccc1[C@H]1NC(=O)c2cc(N)cc(NC(=O)c3cc(F)cc(c3)C(F)(F)F)c12 | 1H NMR (400 MHz, DMSO-d6) 10.0-10.1 (m, 1H), 8.7-8.9 (m, 1H), 8.3-8.6 (m, 1H), 7.7-8.0 (m, 2H), 7.2-7.5 (m, 2H), 7.0-7.1 (m, 1H), 6.9-7.0 (m, 1H), 6.81 (s, 1H), 6.72 (br s, 1H), 6.6-6.7 (m, 1H), 5.6-5.7 (m, 1H), 5.4-5.6 (m, 1H), 2.1-2.3 (m, 3H) | 444 | D | |
| I-66 | 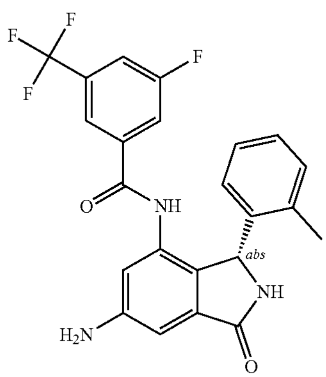 [SMILES: Cc1ccccc1[C@@H]1NC(=O)c2cc(N)cc(NC(=O)c3cc(F)cc(C(F)(F)F)c3)c21] | Cc1ccccc1[C@@H]1NC(=O)c2cc(N)cc(NC(=O)c3cc(F)cc(c3)C(F)(F)F)c12 | 1H NMR (400 MHz, DMSO-d6) 10.0-10.1 (m, 1H), 8.7-8.9 (m, 1H), 8.3-8.6 (m, 1H), 7.7-8.0 (m, 2H), 7.2-7.5 (m, 2H), 7.0-7.1 (m, 1H), 6.9-7.0 (m, 1H), 6.81 (s, 1H), 6.72 (br s, 1H), 6.6-6.7 (m, 1H), 5.6-5.7 (m, 1H), 5.4-5.6 (m, 1H), 2.1-2.3 (m, 3H) | 444 | A | |
| I-67 | 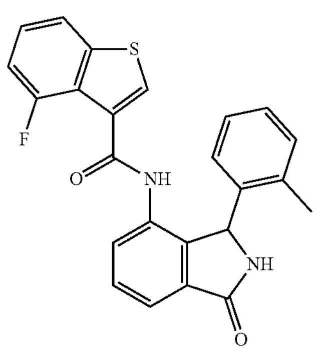 [SMILES: Cc1ccccc1C1NC(=O)c2cccc(NC(=O)c3csc4cccc(F)c34)c21] | Cc1ccccc1C1NC(=O)c2cccc(NC(=O)c3csc4cccc(F)c34)c12 | 1H NMR (400 MHz, DMSO-d6) 10.22 (s, 1H), 9.05 (s, 1H), 7.87 (d, 8.1 Hz, 1H), 7.64 (t, 7.4 Hz, 1H), 7.60 (d, 7.4 Hz, 1H), 7.54 (d, 7.4 Hz, 1H), 7.44 (td, 8.0, 4.8 Hz, 1H), 7.23 (dd, 9.3, 6.3 Hz, 2H), 7.18 (t, 6.0 Hz, 1H), 7.08 (t, 7.5 Hz, 1H), 6.70 (br s, 1H), 6.65 (br s, 1H), 6.00 (s, 1H), 2.22 (br s, 3H). | 417.2 | D | |
| I-68 | 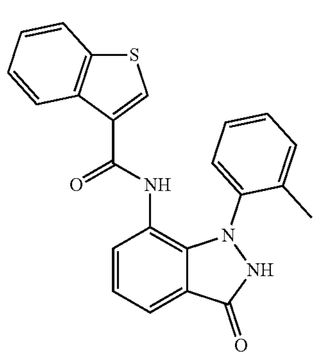 [SMILES: Cc1ccccc1-n1[nH]c(=O)c2cccc(NC(=O)c3csc4ccccc34)c21] | Cc1ccccc1-n1[nH]c(=O)c2cccc(NC(=O)c3csc4ccccc34)c12 | 1H NMR (400 MHz, DMSO-d6) 11.01 (s, 1H), 9.70 (s, 1H), 8.23-8.12 (m, 1H), 8.02-7.93 (m, 1H), 7.70 (dd, 8.0, 0.9 Hz, 1H), 7.59 (s, 1H), 7.44-7.34 (m, 2H), 7.31 (d, 7.1 Hz, 1H), 7.18-7.11 (m, 2H), 7.09-7.04 (m, 1H), 7.03-6.93 (m, 2H), 2.06 (s, 3H). | 400.2 | C | |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-69 | 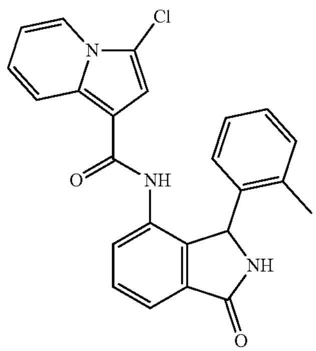 [SMILES: Cc1ccccc1C1NC(=O)c2cccc(NC(=O)c3cc(Cl)n4ccccc34)c21] | Cc1ccccc1C1NC(=O)c2cccc(NC(=O)c3cc(C1)n4cccc34)c12 | 1H NMR (400 MHz, DMSO-d6) 9.43 (s, 1H), 8.98 (s, 1H), 8.24 (d, 6.9 Hz, 1H), 8.14 (d, 8.9 Hz, 1H), 7.64-7.54 (m, 3H), 7.15 (dd, 9.0, 6.6 Hz, 1H), 7.05-6.89 (m, 5H), 6.60 (br s, 1H), 6.11 (s, 1H), 2.20 (br s, 3H). | 416.2 | B | |
| I-70 | 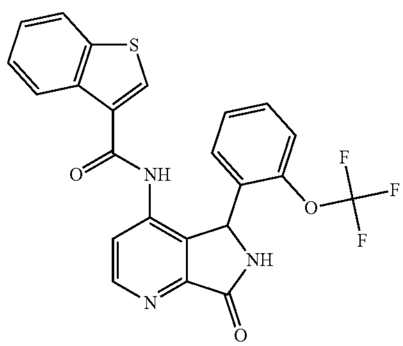 [SMILES: O=C1NC(c2ccccc2OC(F)(F)F)c2c(NC(=O)c3csc4ccccc34)ccnc21] | FC(F)(F)Oc1ccccc1C1NC(=O)c2nccc(NC(=O)c3csc4ccccc34)c12 | 1H NMR(400 MHz, CD3CN) 8.75 (d, 5.3 Hz, 1H), 8.53 (s, 1H), 8.27-8.21 (m, 1H), 7.99-7.93 (m, 1H), 7.72 (d, 5.4 Hz, 1H), 7.66 (s, 1H), 7.50-7.42 (m, 3H), 7.38-7.32 (m, 1H), 7.27-7.18 (m, 2H), 7.15 (td, 7.6, 1.2 Hz, 1H), 6.11 (s, 1H). | 470.2 | D | |
| I-71 | 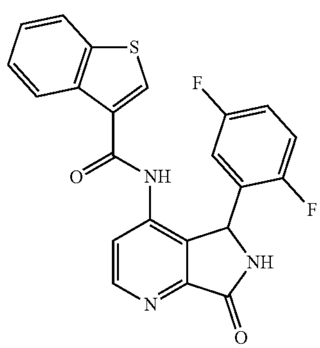 [SMILES: O=C1NC(c2cc(F)ccc2F)c2c(NC(=O)c3csc4ccccc34)ccnc21] | Fc1ccc(F)c(c1)C1NC(=O)c2nccc(NC(=O)c3csc4cccc34)c12 | 1H NMR (400 MHz, CD3CN) 8.76 (dd, 5.2, 0.5 Hz, 1H), 8.70 (s, 1H), 8.29-8.26 (m, 1H), 7.99-7.96 (m, 1H), 7.81 (s, 1H), 7.64 (d, 5.3 Hz, 1H), 7.51-7.45 (m, 3H), 7.01-6.96 (m, 2H), 6.85-6.79 (m, 1H), 6.09 (s, 1H). | 422.2 | C | |
| I-72 | 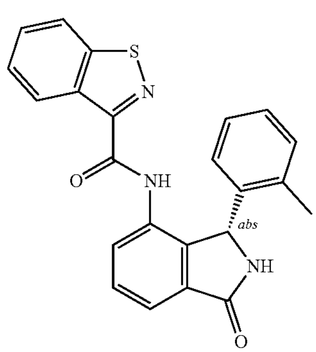 [SMILES: Cc1ccccc1[C@@H]1NC(=O)c2cccc(NC(=O)c3nsc4ccccc34)c21] | Cc1ccccc1[C@@H]1NC(=O)c2cccc(NC(=O)c3nsc4cccc34)c12 | 1H NMR (400 MHz, DMSO-d6) 10.15 (s, 1H), 9.05 (s, 1H), 8.58 (d, 8.2 Hz, 1H), 8.29 (d, 8.2 Hz, 1H), 7.80 (dd, 7.6, 1.2 Hz, 1H), 7.74-7.55 (m, 4H), 7.06-6.93 (m, 2H), 6.89 (t, 13.3 Hz, 1H), 6.68 (br s, 1H), 6.12 (s, 1H), 2.40-2.10 (br s, 3H). | 400.2 | A | |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-73 | 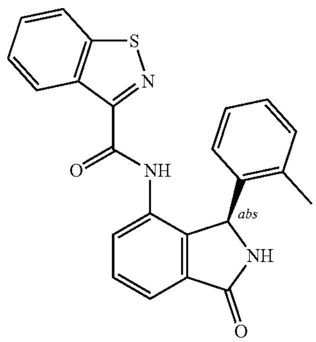 [SMILES: Cc1ccccc1[C@H]1NC(=O)c2cccc(NC(=O)c3nsc4ccccc34)c21] | Cc1ccccc1[C@H]1NC(=O)c2cccc(NC(=O)c3nsc4cccc34)c12 | 1H NMR (400 MHz, DMSO-d6) 10.15 (s, 1H), 9.05 (s, 1H), 8.58 (d, 8.2 Hz, 1H), 8.29 (d, 8.2 Hz, 1H), 7.80 (dd, 7.6, 1.2 Hz, 1H), 7.74-7.55 (m, 4H), 7.06-6.93 (m, 2H), 6.89 (t, 13.3 Hz, 1H), 6.68 (br s, 1H), 6.12 (s, 1H), 2.40-2.10 (br s, 3H). | 400.2 | C | |
| I-74 | 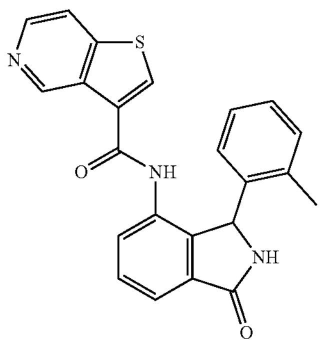 [SMILES: Cc1ccccc1C1NC(=O)c2cccc(NC(=O)c3csc4ccncc34)c21] | Cc1ccccc1C1NC(=O)c2cccc(NC(=O)c3csc4ccncc34)c12 | 1H NMR (400 MHz, DMSO-d6) 10.27 (s, 1H), 9.29 (d, 0.7 Hz, 1H), 9.04 (s, 1H), 8.46 (d, 5.6 Hz, 1H), 8.10 (dd, 5.6, 1.0 Hz, 1H), 7.85 (s, 1H), 7.68 (dd, 7.4, 1.2 Hz, 1H), 7.62 (t, 7.5 Hz, 1H), 7.54 (dd, 7.7, 1.2 Hz, 1H), 7.07-7.00 (m, 1H), 6.95 (dt, 11.5, 5.2 Hz, 2H), 6.62 (br s, 1H), 6.01 (s, 1H), 2.06 (m, 3H) + 89% pure by LC | 400.3 | D | |
| I-75 | 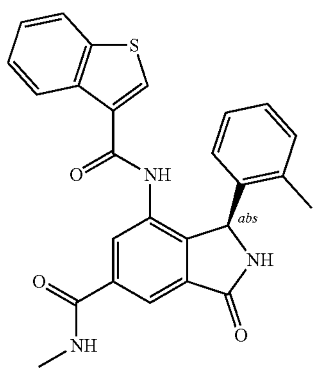 [SMILES: CNC(=O)c1cc(NC(=O)c2csc3ccccc23)c2c(c1)C(=O)N[C@@H]2c1ccccc1C] | CNC(=O)c1cc2C(=O)N[C@@H](c2c(NC(=O)c2csc3ccccc23)c1)c1ccccc1C | 1H NMR (400 MHz, DMSO-d6) δ 10.24 (s, 1H) 9.17 (s, 1H) 8.76 (q, J = 4.21 Hz, 1H) 8.15 (d, J = 1.52 Hz, 1H) 8.06-8.10 (m, 2H) 8.01-8.05 (m, 1H) 7.71 (s, 1H) 7.36-7.48 (m, 2H) 7.08-7.13 (m, 1H) 6.96-7.05 (m, 2H) 6.08 (s, 1H) 2.84 (d, J = 4.55 Hz, 3H) 1.99-2.34 (m, 2H) | 456.1 | D | |
| I-76 | 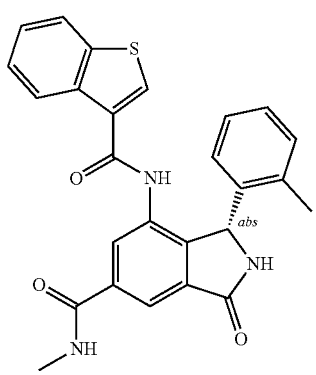 [SMILES: CNC(=O)c1cc(NC(=O)c2csc3ccccc23)c2c(c1)C(=O)N[C@H]2c1ccccc1C] | CNC(=O)c1cc2C(=O)N[C@H](c2c(NC(=O)c2csc3ccccc23)c1)c1ccccc1C | 1H NMR (400 MHz, DMSO-d6) δ 10.24 (s, 1H) 9.17 (s, 1H) 8.76 (q, J = 4.21 Hz, 1H) 8.15 (d, J = 1.52 Hz, 1H) 8.06-8.10 (m, 2H) 8.01-8.05 (m, 1H) 7.71 (s, 1H) 7.36-7.48 (m, 2H) 7.08-7.13 (m, 1H) 6.96-7.05 (m, 2H) 6.08 (s, 1H) 2.84 (d, J = 4.55 Hz, 3H) 1.99-2.34 (m, 2H) | 456.1 | A | A |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-77 | 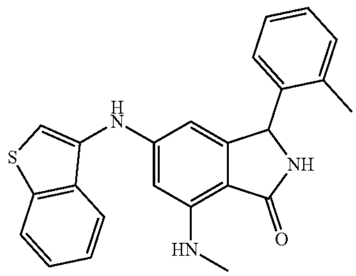 [SMILES: CNc1cc(Nc2csc3ccccc23)cc2c1C(=O)NC2c1ccccc1C] | CNc1cc(Nc2csc3ccccc23)cc2C(NC(=O)c12)c1ccccc1C | 1H NMR(400 MHz, DMSO-d6) 8.35 (s, 1H), 8.15 (s, 1H), 7.93-7.85 (m, 1H), 7.82-7.76 (m, 1H), 7.37-7.29 (m, 2H), 7.19 (s, 1H), 7.16-7.07 (m, 3H), 6.97 (d, 7.0 Hz, 1H), 6.51 (q, 5.1 Hz, 1H), 6.17 (d, 1.5 Hz, 1H), 6.02 (s, 1H), 5.64 (s, 1H), 2.74 (d, 5.1 Hz, 3H), 2.33 (s, 3H). | 400.3 | D | |
| I-78 | 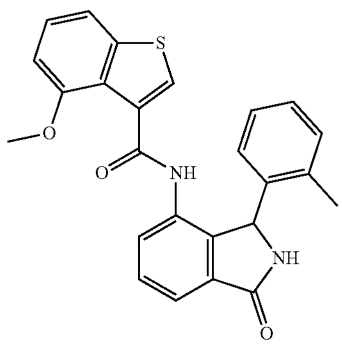 | COc1cccc2scc(C(=O)Nc3cccc4C(=O)NC(c34)c3ccccc3C)c12 | 1H NMR (400 MHz, DMSO-d6) 9.96 (s, 1H), 9.04 (s, 1H), 7.66-7.58 (m, 2H), 7.55 (ddd, 5.2, 4.5, 1.1 Hz, 2H), 7.36 (t, 8.0 Hz, 1H), 7.28-7.18 (m, 2H), 7.10 (t, 7.1 Hz, 1H), 6.94 (d, 7.6 Hz, 1H), 6.67 (s, 1H), 6.44 (s, 1H), 6.04 (s, 1H), 3.81 (s, 3H), 2.41-2.00 (m, 3H). | 429.3 | E | |
| I-79 | 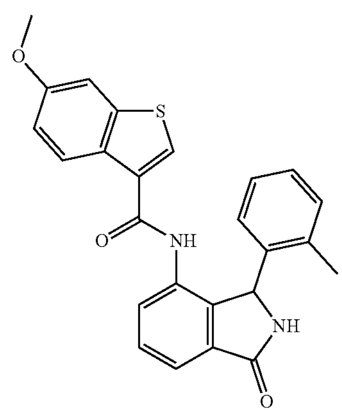 [SMILES: COc1ccc2c(C(=O)Nc3cccc4c3C(c3ccccc3C)NC4=O)csc2c1] | COc1ccc2c(csc2c1)C(=O)Nc1cccc2C(=O)NC(c12)c1ccccc1C | 1H NMR (400 MHz, DMSO-d6) 10.04 (s, 1H), 9.03 (s, 1H), 7.92 (d, 8.9 Hz, 1H), 7.65 (dd, 6.5, 2.2 Hz, 1H), 7.61 (d, 7.7 Hz, 1H), 7.57 (m,2H), 7.48 (s, 1H), 7.09 (td, 7.4, 1.3 Hz, 1H), 6.98 (m, 3H), 6.60 (br s, 1H), 6.03 (s, 1H), 3.82 (s, 3H), 2.34-1.92 (m, 3H). | 429.3 | E | |
| I-80 | 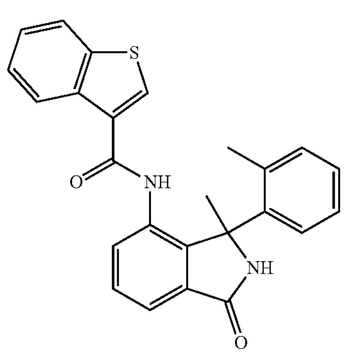 [SMILES: Cc1ccccc1C1(C)NC(=O)c2cccc(NC(=O)c3csc4ccccc34)c21] | Cc1ccccc1C1(C)NC(=O)c2cccc(NC(=O)c3csc4ccccc34)c12 | 1H NMR (400 MHz, DMSO-d6) 8.96 (s, 1H), 8.88 (s, 1H), 8.11-8.05 (m, 1H), 8.05-7.99 (m, 1H), 7.73 (dd, 7.8, 0.7 Hz, 1H), 7.71-7.65 (m, 3H), 7.58 (t, 7.6 Hz, 1H), 7.43-7.37 (m, 2H), 7.12-7.05 (m, 2H), 7.05-7.00 (m, 1H), 1.98 (s, 3H), 1.63 (s, 3H). | 413.3 | E | |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-81 | 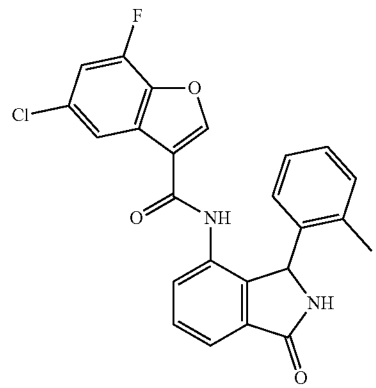 [SMILES: Cc1ccccc1C1NC(=O)c2cccc(NC(=O)c3coc4c(F)cc(Cl)cc34)c21] | Cc1ccccc1C1NC(=O)c2cccc(NC(=O)c3coc4c(F)cc(Cl)cc34)c12 | 1H NMR (400 MHz, DMSO-d6) 10.20 (s, 1H), 9.05 (s, 1H), 8.28 (s, 1H), 7.68 (dd, 7.5, 1.1 Hz, 1H), 7.62 (t, 7.6 Hz, 1H), 7.57 (dd, 10.6, 1.9 Hz, 1H), 7.49 (m, 2H), 7.04 (td, 7.5, 1.3 Hz, 1H), 6.94 (dd, 12.8, 6.9 Hz, 2H), 6.60 (br s, 1H), 5.96 (s, 1H), 2.16 (br s, 3H). | 435.2 | A | |
| I-82 | 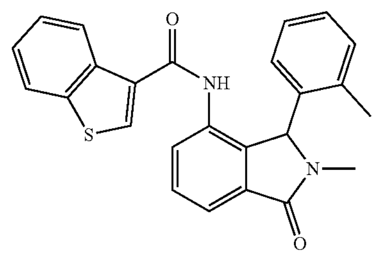 [SMILES: Cc1ccccc1C1c2c(NC(=O)c3csc4ccccc34)cccc2C(=O)N1C] | CN1C(c2c(cccc2NC(=O)c2csc3cccc23)C1=O)c1ccccc1C | 1H NMR (400 MHz, DMSO-d6) 10.18 (s, 1H), 10.10 (s, 0.62H), 8.31-8.16 (m, 0.65H), 8.13-7.97 (m, 13.1, 7.0, 2.5 Hz, 3H), 7.78 (s, 0.64 H), 7.76 (s, 1H), 7.68 (td, 7.2, 0.9 Hz, 1.78H), 7.64-7.55 (m, 1.8H), 7.51 (d, 7.0 Hz, 0.67H), 7.49-7.35 (m, 5H), 7.21-6.94 (m, 5H), 6.83 (t, 7.5, 0.65 H), 6.29 (dd, 7.7, 1.2 Hz, 1H), 6.00 (s, 1H), 5.78 (s, 0.65H), 2.77 (s, 1.84H), 2.74 (s, 3H), 2.32 (s, 3H), 1.39 (s, 1.87H). | 413.3 | E | |
| I-83 | 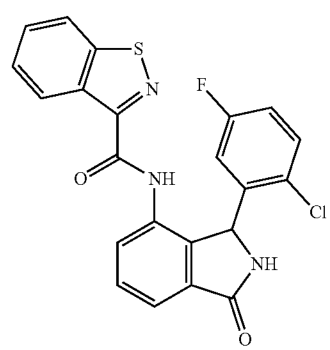 [SMILES: O=C1NC(c2cc(F)ccc2Cl)c2c(NC(=O)c3nsc4ccccc34)cccc21] | Fc1ccc(Cl)c(c1)C1NC(=O)c2cccc(NC(=O)c3nsc4cccc34)c12 | ¹H NMR (400 MHz, DMSO-d$_6$) δ 10.38 (br s, 1H), 9.12 (br s, 1H), 8.63 (d, J = 8.08 Hz, 1H), 8.30 (d, J = 8.34 Hz, 1H), 7.53-7.82 (m, 6H), 7.16-7.31 (m, 1H), 6.92-7.06 (m, 1H), 6.07-6.29 (m, 1H). | 438.3 | A | A |
| I-84 | 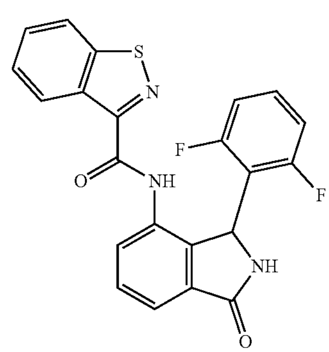 [SMILES: O=C1NC(c2c(F)cccc2F)c2c(NC(=O)c3nsc4ccccc34)cccc21] | Fc1cccc(F)c1C1NC(=O)c2cccc(NC(=O)c3nsc4cccc34)c12 | ¹H NMR (400 MHz, DMSO-d$_6$) δ 10.49 (s, 1H), 9.01 (s, 1H), 8.64 (d, J = 8.1 Hz, 1H), 8.30 (d, J = 8.3 Hz, 1H), 7.50-7.76 (m, 5H), 7.18 (tt, J = 8.3, 6.6 Hz, 1H), 6.78 (br t, J = 7.8 Hz, 2H), 6.21 (s, 1H). | 422.3 | D | |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-85 | 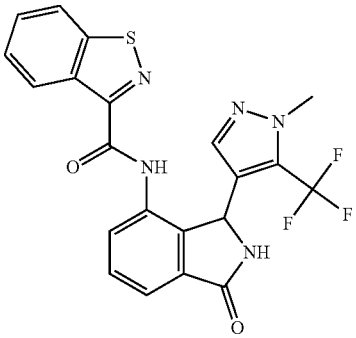 [SMILES: Cn1ncc(C2NC(=O)c3cccc(NC(=O)c4nsc5ccccc45)c32)c1C(F)(F)F] | Cn1ncc(C2NC(=O)c3cccc(NC(=O)c4nsc5ccccc45)c23)c1C(F)(F)F | ¹H NMR (400 MHz, DMSO-d$_6$) δ 10.45 (s, 1H), 9.08 (s, 1H), 8.61 (d, J = 8.1 Hz, 1H), 8.16-8.39 (m, 1H), 7.47-7.81 (m, 5H), 7.01 (s, 1H), 6.07 (s, 1H), 3.69 (d, J = 0.8 Hz, 3H). | 458.4 | D | |
| I-86 | 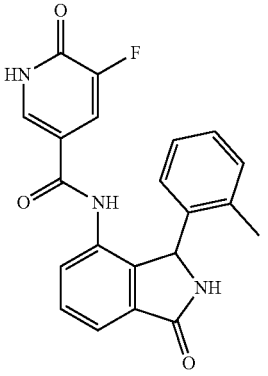 [SMILES: Cc1ccccc1C1NC(=O)c2cccc(NC(=O)c3c[nH]c(=O)c(F)c3)c21] | Cc1ccccc1C1NC(=O)c2cccc(NC(=O)c3c[nH]c(=O)c(F)c3)c12 | 1H NMR (400 MHz, DMSO-d6) 12.48 (br s, 1H), 9.85 (s, 1H), 9.00 (s, 1H), 7.50-7.70 (m, 2H), 7.26-7.47 (m, 3H), 6.88-7.14 (m, 3H), 6.53 (br d, 3.90 Hz, 1H), 5.84 (br s, 1H), 1.86-2.35 (m, 3H) | 378.28 | E | |
| I-87 | 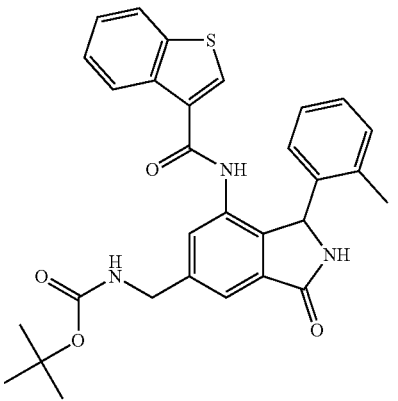 [SMILES: Cc1ccccc1C1NC(=O)c2cc(CNC(=O)OC(C)(C)C)cc(NC(=O)c3csc4ccccc34)c21] | Cc1ccccc1C1NC(=O)c2cc(CNC(=O)OC(C)(C)C)cc(NC(=O)c3csc4ccccc34)c12 | | 528 | A | B |
| I-88 | 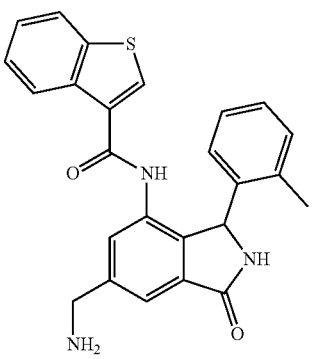 [SMILES: Cc1ccccc1C1NC(=O)c2cc(CN)cc(NC(=O)c3csc4ccccc34)c21] | Cc1ccccc1C1NC(=O)c2cc(CN)cc(NC(=O)c3csc4ccccc34)c12 | | 428 | A | |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-89 | 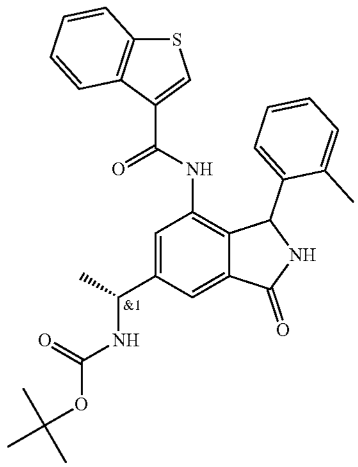 [SMILES: Cc1ccccc1C1NC(=O)c2cc([C@@H](C)NC(=O)OC(C)(C)C)cc(NC(=O)c3csc4ccccc34)c21] | C[C@@H](NC(=O)OC(C)(C)C)c1cc2C(=O)NC(c2c(NC(=O)c2csc3cccc23)c1)c1ccccc1C | | 542 | B | |
| I-90 | 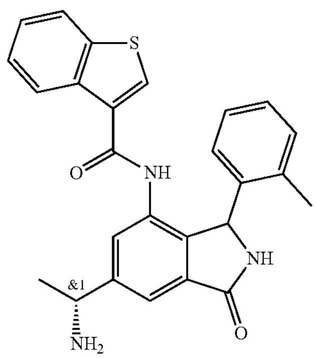 [SMILES: Cc1ccccc1C1NC(=O)c2cc([C@@H](C)N)cc(NC(=O)c3csc4ccccc34)c21] | C[C@@H](N)c1cc2C(=O)NC(c2c(NC(=O)c2csc3cccc23)c1)c1ccccc1C | | 442 | A | |
| I-91 | 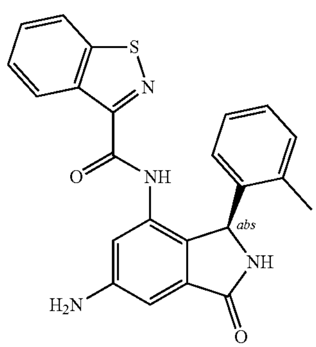 [SMILES: Cc1ccccc1[C@H]1NC(=O)c2cc(N)cc(NC(=O)c3nsc4ccccc34)c21] | Cc1ccccc1[C@H]1NC(=O)c2cc(N)cc(NC(=O)c3nsc4ccccc34)c12 | 1H NMR (400 MHz, DMSO-d6) 9.6-9.9 (m, 1H), 8.7-8.9 (m, 1H), 8.4-8.6 (m, 1H), 8.2-8.3 (m, 1H), 7.6-7.8 (m, 1H), 7.5-7.6 (m, 1H), 7.1-7.2 (m, 1H), 6.9-7.0 (m, 3H), 6.7-6.8 (m, 1H), 6.5-6.7 (m, 1H), 5.8-6.0 (m, 1H), 5.4-5.6 (m, 2H), 2.1-2.4 (m, 3H) | 415 | C | |
| I-92 | 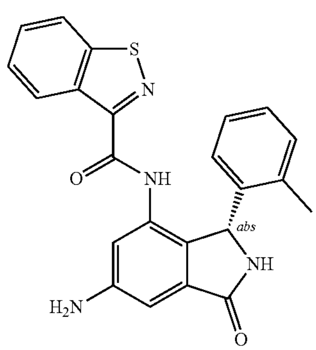 [SMILES: Cc1ccccc1[C@@H]1NC(=O)c2cc(N)cc(NC(=O)c3nsc4ccccc34)c21] | Cc1ccccc1[C@@H]1NC(=O)c2cc(N)cc(NC(=O)c3nsc4ccccc34)c12 | 1H NMR (400 MHz, DMSO-d6) 9.6-9.9 (m, 1H), 8.7-8.9 (m, 1H), 8.4-8.6 (m, 1H), 8.2-8.3 (m, 1H), 7.6-7.8 (m, 1H), 7.5-7.6 (m, 1H), 7.1-7.2 (m, 1H), 6.9-7.0 (m, 3H), 6.7-6.8 (m, 1H), 6.5-6.7 (m, 1H), 5.8-6.0 (m, 1H), 5.4-5.6 (m, 2H), 2.1-2.4 (m, 3H) | 415 | A | A |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-93 | 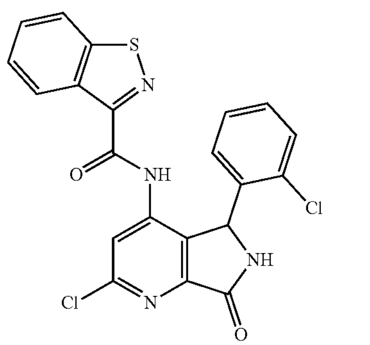 [SMILES: O=C1NC(c2ccccc2Cl)c2c(NC(=O)c3nsc4ccccc34)cc(Cl)nc21] | Clc1cc(NC(=O)c2nsc3ccccc23)c2C(NC(=O)c2n1)c1ccccc1Cl | ¹H NMR (400 MHz, DMSO-d$_6$) δ 10.53 (s, 1H), 9.65 (s, 1H), 8.67 (d, 1H), 8.32 (d, 1H), 7.98 (s, 1H), 7.69 (t, 1H), 7.62 (t, 1H), 7.33 (d, 1H), 7.22 (t, 1H), 7.14 (t, 1H). | 455.26 | A | |
| I-94 | 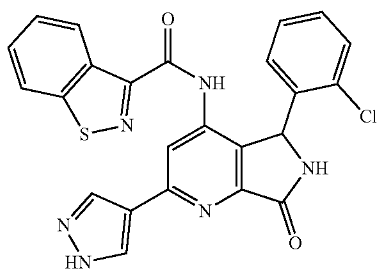 [SMILES: O=C1NC(c2ccccc2Cl)c2c(NC(=O)c3nsc4ccccc34)cc(-c3cn[nH]c3)nc21] | Clc1ccccc1C1NC(=O)c2nc(cc(NC(=O)c3nsc4ccccc34)c12)-c1cn[nH]c1 | ¹H NMR (400 MHz, DMSO-d$_6$) δ 13.20 (br s, 1H), 10.48 (s, 1H), 9.46 (s, 1H), 8.69 (d, J = 8.1 Hz, 1H), 8.41 (br s, 1H), 8.33 (d, J = 8.1 Hz, 1H), 8.10 (br s, 1H), 8.07 (s, 1H), 7.60-7.73 (m, 3H), 7.30 (d, J = 7.8 Hz, 1H), 7.15-7.21 (m, 1H), 7.09-7.14 (m, 1H), 6.29 ppm (br s, 1H). | 487.33 | B | |
| I-95 | 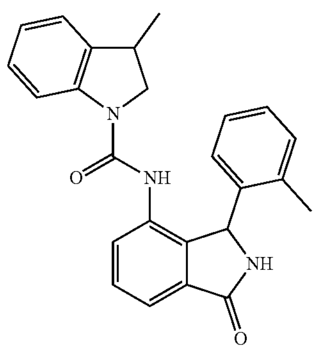 [SMILES: Cc1ccccc1C1NC(=O)c2cccc(NC(=O)N3CC(C)c4ccccc43)c21] | CC1CN(C(=O)Nc2cccc3C(=O)NC(c23)c2cccc2C)c2ccccc12 | 1H NMR (400 MHz, DMSO-d6) 8.92 (s, 1H), 8.39 (s, 1H), 8.33 (s, 1H), 8.27 (s, 1H), 7.70 (d, 8.1 Hz, 1H), 7.62 (m, 1H), 7.53-7.48 (m, 2H), 7.46-7.32 (m, 2H), 7.22 (t, 7.4 Hz, 1H), 7.15-7.03 (m, 3H), 6.99 (d, 7.4 Hz, 1H), 6.96-6.84 (m, 2H), 6.79 (d, 8.7 Hz, 1), 6.54 (br s, 1H), 6.25 (t, 12.4 Hz, 1H), 6.17 (s, 0.24H), 5.87 (s, 1H), 3.79 (t, 9.8 Hz, 1H), 3.74 (s, 1H), 3.66 (s, 1H), 3.22-3.01 (m, 2H), 2.04 (s, 3H), 1.33 (d, 6.8 Hz, 1H), 1.18 (d, 6.2 Hz, 1H), 1.11 (d, 6.4 Hz, 2H), 1.07 (d, 6.7 Hz, 1H). | 398.3 | B | |
| I-96 | 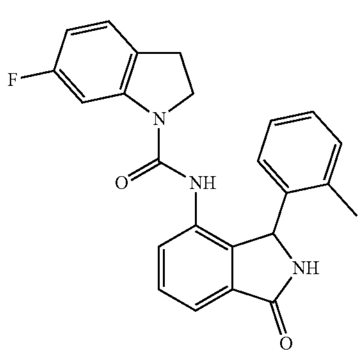 [SMILES: Cc1ccccc1C1NC(=O)c2cccc(NC(=O)N3CCc4ccc(F)cc43)c21] | Cc1ccccc1C1NC(=O)c2cccc(NC(=O)N3CCc4cc(F)cc34)c12 | 1H NMR (400 MHz, DMSO-d6) 8.97 (s, 1H), 8.49 (s, 1H), 7.60-7.51 (m, 2H), 7.43 (dd, 11.1, 2.1 Hz, 1H), 7.39 (dd, 7.1, 1.7 Hz, 1H), 7.13 (ddd, 7.4, 6.7, 3.5 Hz, 2H), 7.02 (d, 7.4 Hz, 1H), 6.95 (t, 7.3 Hz, 1H), 6.69 (ddd, 9.2, 8.3, 2.5 Hz, 1H), 6.57 (br s, 1H), 5.86 (s, 1H), 3.83-3.55 (m, 1H), 3.01-2.78 (m, 3H), 2.15 (m, 3H). | 402.3 | B | |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-97 | 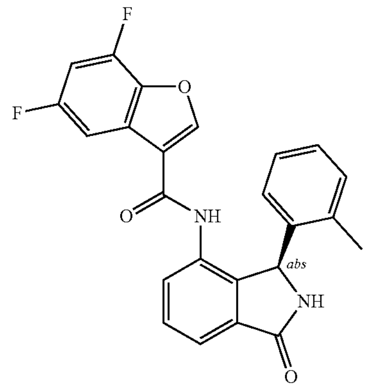 [SMILES: Cc1ccccc1[C@H]1NC(=O)c2cccc(NC(=O)c3coc4c(F)cc(F)cc34)c21] | Cc1ccccc1[C@H]1NC(=O)c2cccc(NC(=O)c3coc4c(F)cc(F)cc34)c12 | 1H NMR (400 MHz, DMSO-d6) 10.08 (s, 1H), 8.98 (s, 1H), 8.18 (s, 1H), 7.61 (d, 7.6 Hz, 1H), 7.55 (t, 7.6 Hz, 1H), 7.45 (d, 7.6 Hz, 1H), 7.37 (t, 7.6 Hz, 1H), 7.25 (d, 7.6 Hz, 1H), 6.99-6.87 (m, 3H), 5.90 (s, 1H), 2.10 (s, 3H) | 417.3 | E | |
| I-98 | 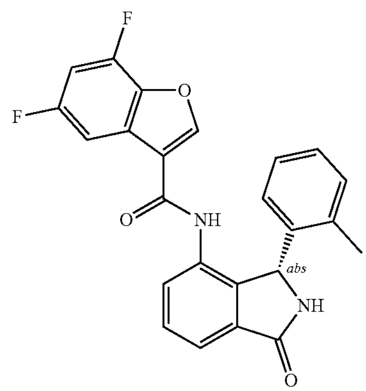 [SMILES: Cc1ccccc1[C@@H]1NC(=O)c2cccc(NC(=O)c3coc4c(F)cc(F)cc34)c21] | Cc1ccccc1[C@@H]1NC(=O)c2cccc(NC(=O)c3coc4c(F)cc(F)cc34)c12 | 1H NMR (400 MHz, DMSO-d6) 10.08 (s, 1H), 8.98 (s, 1H), 8.18 (s, 1H), 7.61 (d, 7.6 Hz, 1H), 7.55 (t, 7.6 Hz, 1H), 7.45 (d, 7.6 Hz, 1H), 7.37 (t, 7.6 Hz, 1H), 7.25 (d, 7.6 Hz, 1H), 6.99-6.87 (m, 3H), 5.90 (s, 1H), 2.10 (s, 3H) | 417.3 | B | |
| I-99 | 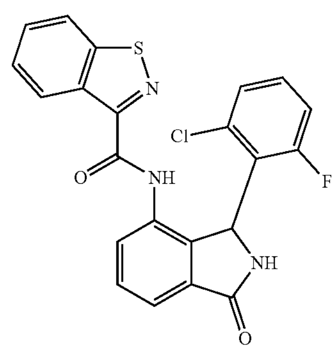 [SMILES: O=C1NC(c2c(F)cccc2Cl)c2c(NC(=O)c3nsc4ccccc34)cccc21] | Fc1cccc(C1)c1C1NC(=O)c2cccc(NC(=O)c3nsc4cccc34)c12 | ¹H NMR (400 MHz, DMSO-d$_6$) δ 10.25-10.42 (m, 1H), 8.82-9.15 (m, 1H), 8.22-8.71 (m, 2H), 7.47-7.73 (m, 4H), 6.77-7.24 (m, 3H), 6.25-6.42 (m, 1H), 3.97-4.18 (m, 1H). | 438.2 | C | |
| I-100 | 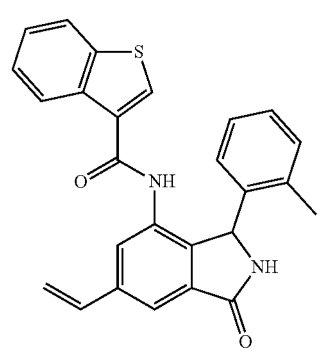 [SMILES: C=Cc1cc(NC(=O)c2csc3ccccc23)c2c(c1)C(=O)NC2c1ccccc1C] | Cc1ccccc1C1NC(=O)c2cc(C=C)cc(NC(=O)c3csc4cccc34)c12 | 1H NMR (400 MHz, CD3CN) 8.27 (brs, 1H), 8.23-8.14 (m, 1H), 8.00-7.91 (m, 1H), 7.83-7.76 (m, 2H), 7.49-7.40 (m, 2H), 7.34 (s, 1H), 7.28 (s, 1H), 7.16 (m, 1H), 7.05 (m, 2H), 6.91 (dd, 17.6, 11.0 Hz, 1H), 6.04 (s, 1H), 5.97 (d, 17.6 Hz, 1H), 5.41 (d, 10.9 Hz, 1H), 2.18 (s, 3H). | 425.3 | A | C |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-101 | 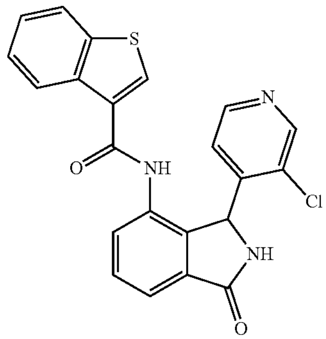 [SMILES: O=C1NC(c2ccncc2Cl)c2c(NC(=O)c3csc4ccccc34)cccc21] | Clc1cncc c1C1NC (=O)c2ccc c(NC(=O) c3csc4cc ccc34)c1 2 | 1H NMR (400 MHz, DMSO-d6) 10.23 (s, 1H), 9.13 (s, 1H), 8.40 (s, 1H), 8.24 (d, 4.9 Hz, 1H), 8.18-8.13 (m, 1H), 8.04-7.99 (m, 1H), 7.97 (s, 1H), 7.67 (dd, 7.5, 1.2 Hz, 1H), 7.61 (t, 7.6 Hz, 1H), 7.49 (dd, 7.7, 1.1 Hz, 1H), 7.42-7.37 (m, 2H), 6.86 (br s, 1H), 6.09 (s, 1H). | 420.2 | D | |
| I-102 | 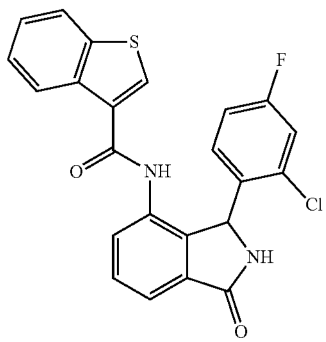 [SMILES: O=C1NC(c2ccc(F)cc2Cl)c2c(NC(=O)c3csc4ccccc34)cccc21] | Fc1ccc(C 2NC(=O) c3cccc(N C(=O)c4 csc5cccc c45)c23) c(Cl)c1 | 1H NMR (400 MHz, DMSO-d6) 10.19 (s, 1H), 9.06 (s, 1H), 8.36 (s, 1H), 8.12-8.06 (m, 1H), 8.03-7.98 (m, 1H), 7.96 (s, 1H), 7.66-7.55 (m, 2H), 7.49 (dd, 7.8, 1.0 Hz, 1H), 7.42-7.34 (m, 2H), 7.22 (dd, 8.9, 2.7 Hz, 1H), 6.97 (s, 1H), 6.11 (s, 1H). | 437.2 | A | |
| I-103 | 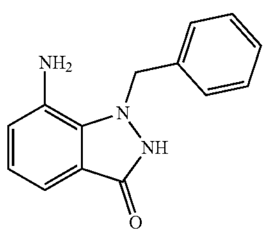 [SMILES: Nc1cccc2c(=O)[nH]n(Cc3ccccc3)c12] | Nc1cccc2 c1n(Cc1c cccc1)[n H]c2=O | 1H NMR (400 MHz, DMSO-d6) 10.57 (s, 1H), 7.26-7.14 (m, 3H), 7.14-7.09 (m, 2H), 6.85 (dd, 7.9, 0.9 Hz, 1H), 6.77 (t, 7.6 Hz, 1H), 6.61 (d, 7.5 Hz, 1H), 5.32 (s, 2H), 5.16 (s, 2H) | 240.2 | E | |
| I-104 | 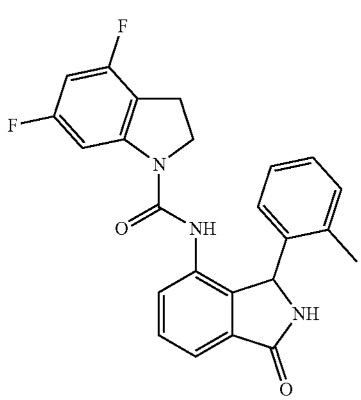 [SMILES: Cc1ccccc1C1NC(=O)c2cccc(NC(=O)N3CCc4c(F)cc(F)cc43)c21] | Cc1ccccc 1C1NC(= O)c2cccc (NC(=O) N3CCc4c 3cc(F)cc 4F)c12 | 1H NMR (400 MHz, DMSO-d6) 8.94 (s, 1H), 8.58 (s, 1H), 7.54 (dd, 7.5, 1.5 Hz, 1H), 7.51 (t, 7.4 Hz, 1H), 7.34 (dd, 7.4, 1.5 Hz, 1H), 7.27 (d, 10.5 , 1.8 Hz, 1H), 7.10 (td, 8.3, 4.1 Hz, 1H), 7.01 (d, 7.3 Hz, 1H), 6.93 (t, 7.8 Hz, 1H), 6.70 (td, 9.5, 2.2 Hz, 1H), 6.61-6.38 (m, 1H), 5.80 (s, 1H), 3.75-3.62 (m, 1H), 2.97-2.78 (m, 3H), 2.34-1.80 (m, 3H). | 420.3 | B | |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-105 | 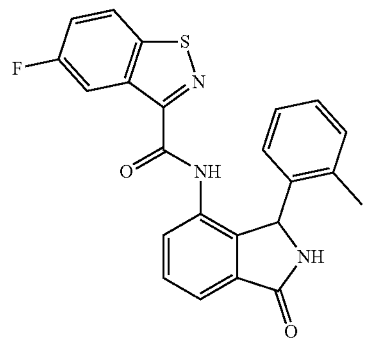 [SMILES: Cc1ccccc1C1NC(=O)c2cccc(NC(=O)c3nsc4ccc(F)cc34)c21] | Cc1ccccc1C1NC(=O)c2cccc(NC(=O)c3nsc4ccc(F)cc34)c12 | | 418 | B | |
| I-106 | 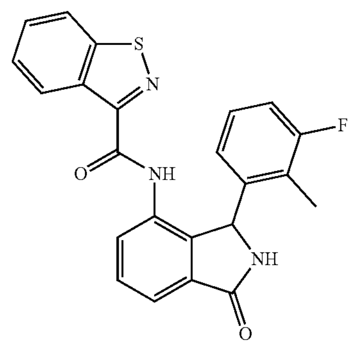 [SMILES: Cc1c(F)cccc1C1NC(=O)c2cccc(NC(=O)c3nsc4ccccc34)c21] | Cc1c(F)cccc1C1NC(=O)c2cccc(NC(=O)c3nsc4ccccc34)c12 | ¹H NMR (400 MHz, DMSO-d$_6$) δ 10.17 (s, 1H), 9.07 (s, 1H), 8.56 (br d, J =8.1 Hz, 1H), 8.29 (d, J =8.3 Hz, 1H), 7.78 (br d, J =7.3 Hz, 1H), 7.50-7.70 (m, 4H), 6.76-7.01 (m, 2H), 6.30-6.65 (m, 1H), 6.02-6.25 (m, 1H), 1.67-2.42 (m, 3H). | 418.3 | B | |
| I-107 | 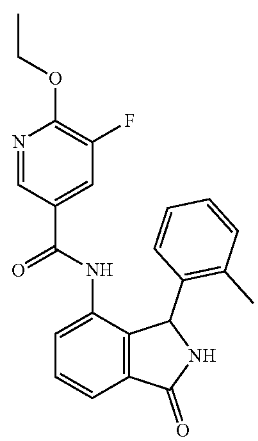 [SMILES: CCOc1ncc(C(=O)Nc2cccc3c2C(c2ccccc2C)NC3=O)cc1F] | CCOc1ncc(cc1F)C(=O)Nc1cccc2C(=O)NC(c12)c1ccccc1C | 1H NMR (400 MHz, DMSO-d6) 10.10 (s, 1H), 9.02 (s, 1H), 7.96 (s, 1H), 7.45-7.70 (m, 4H), 7.03-7.10 (m, 1H), 6.91-7.02 (m, 2H), 6.47-6.67 (m, 1H), 5.89 (br s, 1H), 4.42 (q, 6.91 Hz, 2H), 1.98-2.31 (m, 3H), 1.34 (1, 7.08 Hz, 3H) | 406.39 | E | |
| I-108 | 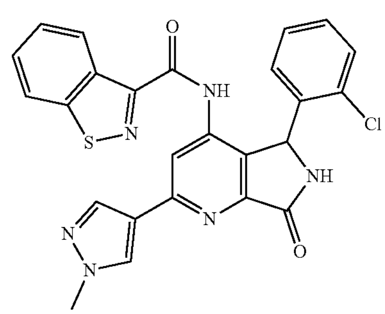 [SMILES: Cn1cc(-c2cc(NC(=O)c3nsc4ccccc34)c3c(n2)C(=O)NC3c2ccccc2Cl)cn1] | Cn1cc(cn1)-c1cc(NC(=O)c2nsc3ccccc23)c2C(NC(=O)c2n1)c1ccccc1Cl | ¹H NMR (400 MHz, DMSO-d$_6$) δ 10.44 (s, 1H), 9.46 (br s, 1H), 8.68 (br d, J = 8.1 Hz, 1H), 8.40 (s, 1H), 8.33 (br d, J = 8.5 Hz, 1H), 8.04 (d, J = 7.3 Hz, 2H), 7.35-7.75 (m, 3H), 7.31 (br d, J = 7.8 Hz, 1H), 7.19 (br t, J = 8.3 Hz, 1H), 7.08-7.15 (m, 1H), 6.30 (br s, 1H), 3.94 (s, 3H). | 501.4 | B | |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-109 | 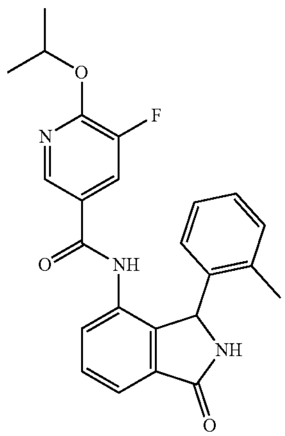 [SMILES: Cc1ccccc1C1NC(=O)c2cccc(NC(=O)c3cnc(OC(C)C)c(F)c3)c21] | CC(C)Oc1ncc(cc1F)C(=O)Nc1cccc2C(=O)NC(c12)c1ccccc1C | 1H NMR (400 MHz, DMSO-d6) 10.09 (s, 1H), 9.02 (s, 1H), 7.95 (s, 1H), 7.63-7.68 (m, 1H), 7.59 (t, 7.57 Hz, 1H), 7.46-7.55 (m, 2H), 7.03-7.10 (m, 1H), 6.90-7.02 (m, 2H), 6.45-6.68 (m, 1H), 5.89 (br s, 1H), 5.34 (td, 6.13, 12.39 Hz, 1H), 1.94-2.28 (m, 3H), 1.33 (d, 6.10 Hz, 6H) | 420.45 | E | |
| I-110 | 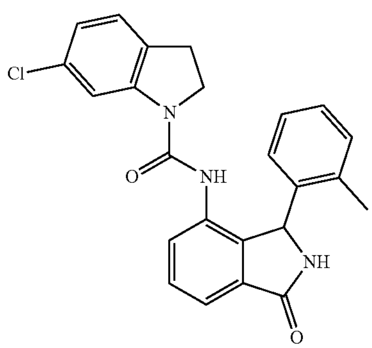 [SMILES: Cc1ccccc1C1NC(=O)c2cccc(NC(=O)N3CCc4ccc(Cl)cc43)c21] | Cc1ccccc1C1NC(=O)c2cccc(NC(=O)N3CCc4cc(Cl)cc34)c12 | 1H NMR (400 MHz, DMSO-d6) 8.93 (s, 1H), 8.48 (s, 1H), 7.63 (d, 1.5 Hz, 1H), 7.55-7.47 (m, 2H), 7.35 (dd, 7.2, 1.7 Hz, 1H), 7.14-7.06 (m, 2H), 6.98 (d, 7.4 Hz, 1H), 6.95-6.86 (m, 2H), 6.60 (br s, 1H), 5.82 (s, 1H), 3.71-3.56 (m, 1H), 2.96-2.76 (m, 3H), 2.11 (s, 3H). | 418.3 | B | |
| I-111 | 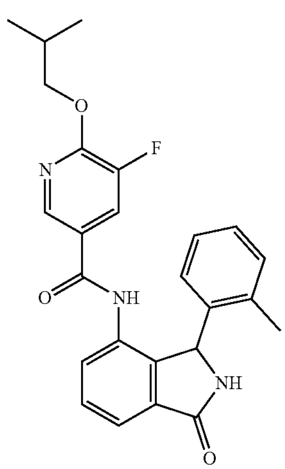 [SMILES: Cc1ccccc1C1NC(=O)c2cccc(NC(=O)c3cnc(OCC(C)C)c(F)c3)c21] | CC(C)COc1ncc(c1F)C(=O)Nc1cccc2C(=O)NC(c12)c1ccccc1C | 1H NMR (400 MHz, DMSO-d6) 10.10 (s, 1H), 9.02 (s, 1H), 7.96 (s, 1H), 7.62-7.67 (m, 1H), 7.47-7.62 (m, 3H), 7.04-7.12 (m, 1H), 6.89-7.02 (m, 2H), 6.42-6.68 (m, 1H), 5.89 (br s, 1H), 4.16 (d, 6.83 Hz, 2H), 1.93-2.29 (m, 4H), 0.97 (d, 6.59 Hz, 6H) | 434.45 | E | |

TABLE 2-continued

Representative Compounds of the Invention with Bioactivity Data.

| Ex. No. | Structure | SMILES | $^1$H NMR | MS | ADP-Glo IC$_{50}$ | MCF 10A IC$_{50}$ |
|---|---|---|---|---|---|---|
| I-112 | 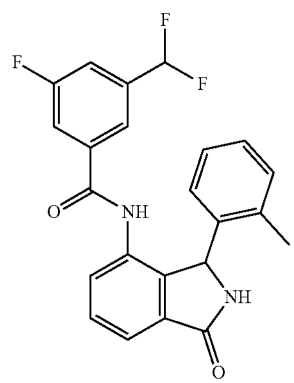 [SMILES: Cc1ccccc1C1NC(=O)c2cccc(NC(=O)c3cc(F)cc(C(F)F)c3)c21] | Cc1ccccc1C1NC(=O)c2cccc(NC(=O)c3cc(F)cc(c3)C(F)F)c12 | 1H NMR (400 MHz, DMSO-d6) 10.25 (s, 1H), 9.04 (s, 1H), 7.64-7.69 (m, 1H), 7.55-7.62 (m, 2H), 7.52 (d, 7.57 Hz, 1H), 7.39 (s, 1H), 7.15-7.26 (m, 1H), 6.86-7.10 (m, 4H), 6.59 (br d, 7.08 Hz, 1H), 5.91 (br s, 1H), 3.31 (s, 1H), 1.94-2.35 (m, 3H) | 411.39 | | D |
| I-113 | 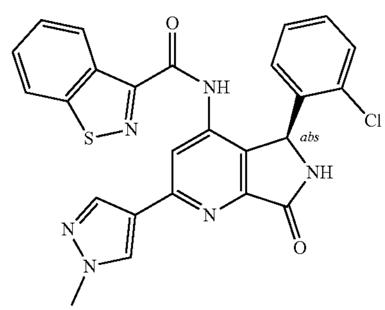 [SMILES: Cn1cc(-c2cc(NC(=O)c3nsc4ccccc34)c3c(n2)C(=O)N[C@@H]3c2ccccc2Cl)cn1] | Cn1cc(cn1)-c1cc(NC(=O)c2nsc3ccccc23)c2[C@@H](NC(=O)c2n1)c1ccccc1C1 | $^1$H NMR (400 MHz, DMSO-d$_6$) δ 10.43 (br s, 1H), 9.45 (br s, 1H), 8.67 (br d, J = 5.9 Hz, 1H), 8.39 (s, 1H), 8.32 (br d, J = 8.1 Hz, 1H), 8.04 (d, J = 11.5 Hz, 2H), 7.66-7.74 (m, 1H), 7.62 (br d, J = 7.1 Hz, 1H), 7.31 (br d, J = 7.8 Hz, 1H), 7.16-7.23 (m, 1H), 7.13 (br t, J = 7.1 Hz, 1H), 6.29 (br s, 1H), 3.94 (s, 3H). | 501.3 | | B |
| I-114 | 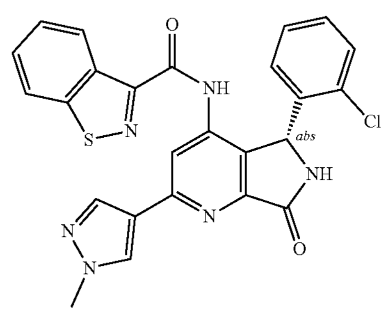 [SMILES: Cn1cc(-c2cc(NC(=O)c3nsc4ccccc34)c3c(n2)C(=O)N[C@H]3c2ccccc2Cl)cn1] | Cn1cc(cn1)-c1cc(NC(=O)c2nsc3ccccc23)c2[C@H](NC(=O)c2n1)c1ccccc1C1 | $^1$H NMR (400 MHz, DMSO-d$_6$) δ 10.44 (br s, 1H), 9.46 (br s, 1H), 8.68 (br d, J = 7.6 Hz, 1H), 8.39 (s, 1H), 8.32 (br d, J = 8.3 Hz, 1H), 8.04 (d, J = 9.0 Hz, 2H), 7.66-7.74 (m, 1H), 7.57-7.66 (m, 1H), 7.31 (br d, J = 7.8 Hz, 1H), 7.16-7.23 (m, 1H), 7.13 (br t, J = 7.3 Hz, 1H), 6.30 (br s, 1H), 3.94 (s, 3H) | 501.4 | | D |
| I-115 | 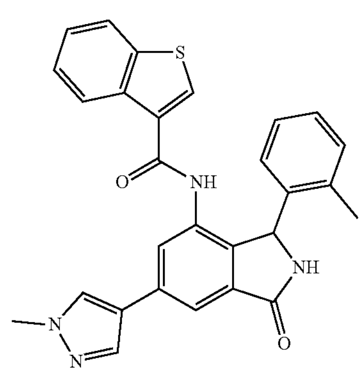 | Cc1ccccc1C1NC(=O)c2cc(c(NC(=O)c3csc4ccccc34)c12)-c1cnn(C)c1 | 1H NMR (400 MHz, CDCl3) 8.46 (br s, 1H), 8.26 (br s, 1H), 7.88 (s, 1H), 7.86 (d, 1.4 Hz, 1H), 7.76 (s, 1H), 7.49-7.40 (m, 3H), 7.36 (d, 7.3 Hz, 1H), 7.24-7.21 (m, 1H), 6.85 (s, 1H), 6.35 (s, 1H), 5.87 (s, 1H), 3.97 (s, 3H), 1.55 (s, 3H) | 479.6 | | A |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-116 | 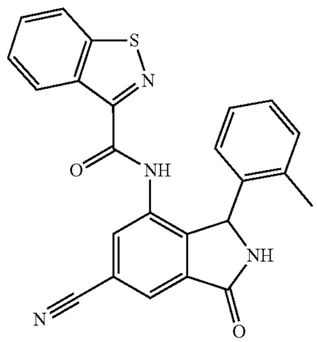 [SMILES: Cc1ccccc1C1NC(=O)c2cc(C#N)cc(NC(=O)c3nsc4ccccc34)c21] | Cc1ccccc1C1NC(=O)c2cc(cc(NC(=O)c3nsc4ccccc34)c12)C#N | 1H NMR (400 MHz, DMSO-d6) 10.37 (s, 1H), 9.38 (s, 1H), 8.61 (d, 8.2 Hz, 1H), 8.31 (d, 8.2 Hz, 1H), 8.22 (d, 1.4 Hz, 1H), 8.11 (d, 1.3 Hz, 1H), 7.73-7.64 (m, 1H), 7.63-7.57 (m, 1H), 7.02-6.95 (m, 2H), 6.91 (t, 7.0 Hz, 1H), 6.63 (br s, 1H), 6.23 (s, 1H), 2.27 (br s, 3H). | 425.2 | A | |
| I-117 | 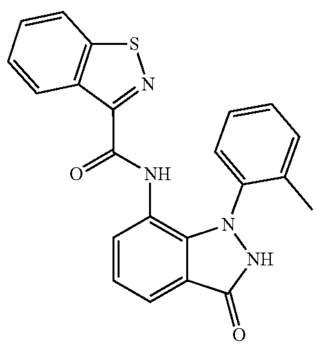 [SMILES: Cc1ccccc1-n1[nH]c(=O)c2cccc(NC(=O)c3nsc4ccccc34)c21] | Cc1ccccc1-n1[nH]c(=O)c2ccc(NC(=O)c3nsc4ccccc34)c12 | 1H NMR (400 MHz, DMSO-d6) 11.71-11.31 (m, 1H), 9.89 (s, 1H), 8.57-8.50 (m, 1H), 8.24 (dt, 8.3, 0.8 Hz, 1H), 7.70 (dd, 8.0, 0.7 Hz, 1H), 7.63 (ddd, 8.2, 7.0, 1.2 Hz, 1H), 7.55 (ddd, 7.0, 4.7, 1.1 Hz, 2H), 7.18 (dd, 7.7, 1.4 Hz, 1H), 7.13 (t, 7.7 Hz, 1H), 6.98 (d, 7.4 Hz, 1H), 6.88 (dt, 7.6, 3.9 Hz, 1H), 6.83 (td, 7.4, 1.4 Hz, 1H), 2.06 (s, 3H). | 401.2 | D | |
| I-118 | 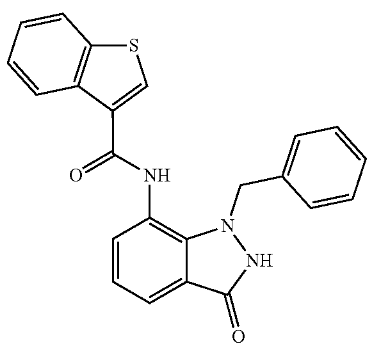 [SMILES: O=C(Nc1cccc2c(=O)[nH]n(Cc3ccccc3)c12)c1csc2ccccc12] | O=C(Nc1cccc2c1n(Cc1ccccc1)[nH]c2=O)c1csc2ccccc12 | 1H NMR (400 MHz, DMSO-d6) 11.05 (br s, 1H), 10.48 (s, 1H), 8.54 (s, 1H), 8.42-8.33 (m, 1H), 8.11-8.03 (m, 1H), 7.60 (dd, 8.0, 1.0 Hz, 1H), 7.48-7.42 (m, 2H), 7.28 (d, 7.0 Hz, 1H), 7.19-7.11 (m, 3H), 7.10-7.03 (m, 1H), 7.01-6.94 (m, 2H), 5.34 (s, 2H). | 400.3 | E | |
| I-119 | 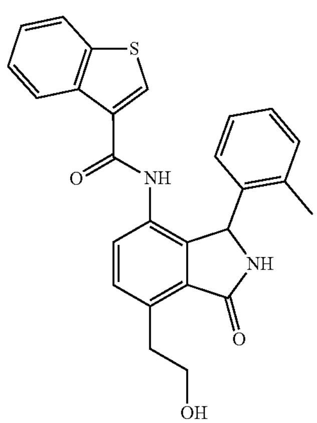 [SMILES: Cc1ccccc1C1NC(=O)c2c(CCO)ccc(NC(=O)c3csc4ccccc34)c21] | Cc1ccccc1C1NC(=O)c2c1c(NC(=O)c1csc3ccccc13)ccc2CCO | 1H NMR (400 MHz, DMSO-d6) 9.97 (s, 1H), 8.96 (s, 1H), 8.06-7.98 (m, 2H), 7.60 (s, 1H), 7.45 (d, 8.0 Hz, 1H), 7.43-7.35 (m, 3H), 7.09 (td, 7.5, 1.3 Hz, 1H), 6.99 (dd, 16.6, 7.3 Hz, 2H), 6.62 (s, 1H), 5.94 (s, 1H), 4.68 (t, 5.3 Hz, 1H), 3.75-3.63 (m, 2H), 3.39 (dt, 13.3, 6.8 Hz, 1H), 3.30-3.21 (m, 1H), 2.18 (s, 2H). | 443.3 | A | |

TABLE 2-continued

Representative Compounds of the Invention with Bioactivity Data.

| Ex. No. | Structure | SMILES | $^1$H NMR | MS | ADP-Glo IC$_{50}$ | MCF 10A IC$_{50}$ |
|---|---|---|---|---|---|---|
| I-120 | 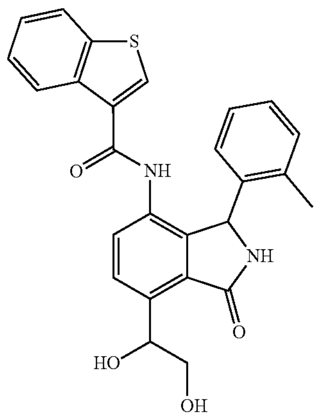 [SMILES: Cc1ccccc1C1NC(=O)c2c(C(O)CO)ccc(NC(=O)c3csc4ccccc34)c21] | Cc1ccccc1C1NC(=O)c2c1c(NC(=O)c1csc3cccccc13)ccc2C(O)CO | 1H NMR (400 MHz, DMSO-d6) 10.04 (s, 0.8 H), 10.03 (s, 1H), 9.21 (s, 1H), 9.16 (s, 0.8H), 8.02 (dd, 6.5, 2.5 Hz, 4H), 7.68-7.57 (m, 4H), 7.52 (dd, 8.1, 4.3 Hz, 2H), 7.45-7.35 (m, 4H), 7.16-7.06 (m, 2H), 6.99 (dd, 16.2, 7.3 Hz, 4H), 6.61 (br s, 1H), 6.00 (d, 6.7 Hz, 2H), 5.77 (d, 5.9 Hz, 1H), 5.68 (d, 6.3 Hz, 0.8H), 5.56 (td, 6.6, 4.6 Hz, 0.8H), 5.47 (td, 6.7, 4.9 Hz, 1H), 4.77 (dd, 9.8, 5.6 Hz, 2H), 4.57 (s, 1H), 3.66-3.56 (m, 2H), 3.56-3.42 (m, 2H), 2.19 (br s, 5H).. | 459.2 | B | |
| I-121 | 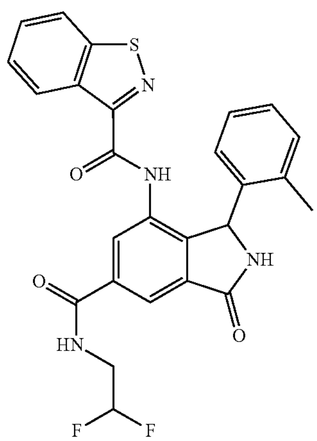 [SMILES: Cc1ccccc1C1NC(=O)c2cc(C(=O)NCC(F)F)cc(NC(=O)c3nsc4ccccc34)c21] | Cc1ccccc1C1NC(=O)c2cc(cc(NC(=O)c3nsc4ccccc34)c12)C(=O)NCC(F)F | 1H NMR (400 MHz, DMSO-d6) 10.25 (s, 1H), 9.16 (s, 1H), 8.69-8.81 (m, 1H), 8.54-8.62 (m, 1H), 8.24-8.34 (m, 2H), 8.13 (d, 1.22 Hz, 1H), 7.63-7.71 (m, 1H), 7.53-7.62 (m, 1H), 6.85-7.02 (m, 3H), 6.60-6.79 (m, 1H), 6.15 (br s, 1H), 2.82 (d, 4.39 Hz, 3H), 2.10-2.41 (m, 3H) | 507.38 | A | A |
| I-122 | 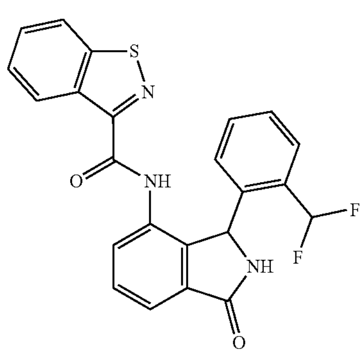 [SMILES: O=C1NC(c2ccccc2C(F)F)c2c(NC(=O)c3nsc4ccccc34)cccc21] | FC(F)c1ccccc1C1NC(=O)c2cccc(NC(=O)c3nsc4cccc34)c12 | $^1$H NMR (400 MHz, DMSO-d$_6$) δ 10.14 (s, 1H), 9.16 (s, 1H), 8.56 (d, J = 8.08 Hz, 1H), 8.22-8.33 (m, 1H), 7.82 (dd, J = 1.14, 7.71 Hz, 1H), 7.59-7.72 (m, 3H), 7.56 (ddd, J = 0.88, 7.07, 8.21 Hz, 1H), 7.39-7.59 (m, 1H), 7.35 (d, J = 7.83 Hz, 1H), 7.21-7.32 (m, 2H), 6.75 (br s, 1H), 6.18 (s, 1H). | 436.3 | A | B |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-123 | 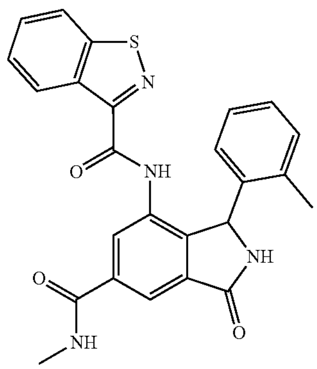 [SMILES: CNC(=O)c1cc(NC(=O)c2nsc3ccccc23)c2c(c1)C(=O)NC2c1ccccc1C] | CNC(=O)c1cc2C(=O)NC(c2c(NC(=O)c2nsc3ccccc23)c1ccccc1C | 1H NMR (400 MHz, DMSO-d6) 10.28 (s, 1H), 9.13-9.25 (m, 2H), 8.52-8.64 (m, 1H), 8.26-8.36 (m, 2H), 8.20 (s, 1H), 7.67 (br t, 7.57 Hz, 1H), 7.54-7.61 (m, 1H), 6.86-7.01 (m, 3H), 6.66-6.78 (m, 1H), 6.10-6.24 (m, 2H), 3.72 (tt, 4.76, 15.38 Hz, 2H), 2.10-2.40 (m, 3H) | 457.41 | A | |
| I-124 | 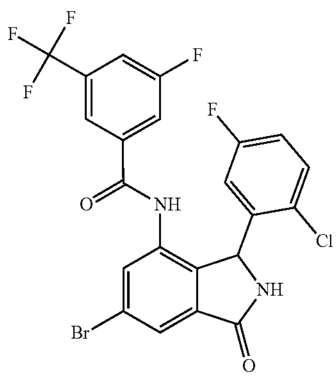 [SMILES: O=C(Nc1cc(Br)cc2c1C(c1cc(F)ccc1Cl)NC2=O)c1cc(F)cc(C(F)(F)F)c1] | Fc1ccc(C1)c(c1)C1NC(=O)c2cc(Br)cc(NC(=O)c3cc(F)cc(c3)C(F)(F)F)c12 | 1H NMR (400 MHz, DMSO-d6) 10.3-11.0 (m, 1H), 9.0-9.4 (m, 1H), 8.3-8.6 (m, 1H), 7.5-8.1 (m, 3H), 7.2-7.4 (m, 1H), 7.0-7.2 (m, 1H), 6.5-6.9 (m, 2H), 5.7-6.1 (m, 1H) | 545 | A | B |
| I-125 | 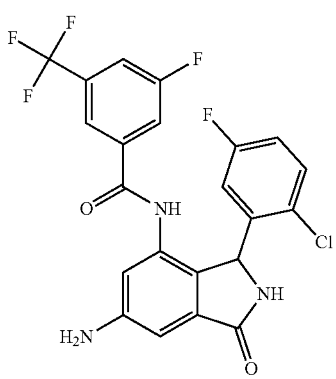 [SMILES: Nc1cc(NC(=O)c2cc(F)cc(C(F)(F)F)c2)c2c(c1)C(=O)NC2c1cc(F)ccc1Cl] | Nc1cc2C(=O)NC(c2c(NC(=O)c2cc(F)cc(c2)C(F)(F)F)c1ccc(F)ccc1Cl | 1H NMR (500 MHz, DMSO-d6) 10.1-10.3 (m, 1H), 8.8-8.9 (m, 1H), 7.9-8.0 (m, 1H), 7.6-7.8 (m, 1H), 7.6-7.6 (m, 1H), 7.2-7.4 (m, 2H), 7.0-7.1 (m, 1H), 6.8-6.9 (m, 1H), 6.66 (s, 1H), 5.7-5.9 (m, 1H), 5.5-5.7 (m, 2H) | 482 | A | A |
| I-126 | 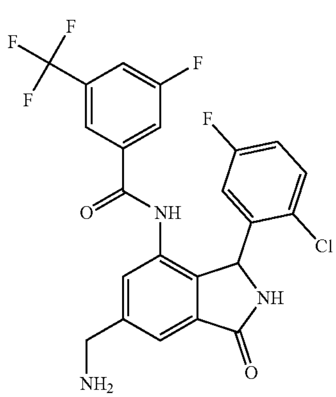 [SMILES: NCc1cc(NC(=O)c2cc(F)cc(C(F)(F)F)c2)c2c(c1)C(=O)NC2c1cc(F)ccc1Cl] | NCc1cc2C(=O)NC(c2c(NC(=O)c2cc(F)cc(c2)C(F)(F)F)c1cc(F)ccc1Cl | 1H NMR (400 MHz, DMSO-d6) 10.3-10.6 (m, 1H), 9.0-9.3 (m, 1H), 7.9-8.0 (m, 1H), 7.7-7.8 (m, 1H), 7.6-7.7 (m, 2H), 7.4-7.5 (m, 1H), 7.2-7.3 (m, 2H), 7.0-7.1 (m, 1H), 6.6-6.8 (m, 1H), 5.8-6.1 (m, 1H), 5.3-5.6 (m, 1H), 4.4-4.8 (m, 2H) | 496 | A | |

TABLE 2-continued

Representative Compounds of the Invention with Bioactivity Data.

| Ex. No. | Structure | SMILES | $^1$H NMR | MS | ADP-Glo IC$_{50}$ | MCF 10A IC$_{50}$ |
|---|---|---|---|---|---|---|
| I-127 | 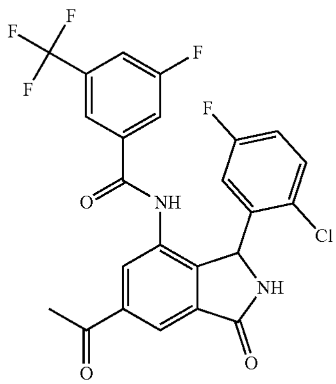 [SMILES: CC(=O)c1cc(NC(=O)c2cc(F)cc(C(F)(F)F)c2)c2c(c1)C(=O)NC2c1cc(F)ccc1Cl] | CC(=O)c1cc2C(=O)NC(c2c(NC(=O)c2cc(F)cc(c2)C(F)(F)F)c1)c1cc(F)ccc1Cl | 1H NMR (400 MHz, DMSO-d6) 10.5-10.8 (m, 1H), 9.2-9.5 (m, 1H), 8.4-8.6 (m, 1H), 8.2-8.3 (m, 1H), 7.93 (br d, 1H, 8.1 Hz), 7.6-7.8 (m, 2H), 7.2-7.5 (m, 1H), 6.9-7.2 (m, 1H), 6.6-6.9 (m, 1H), 5.9-6.2 (m, 1H), 2.7-2.8 (m, 3H) | 509 | A | |
| I-128 | 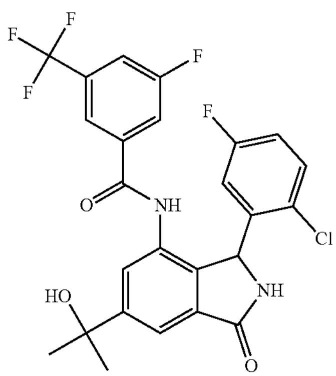 [SMILES: CC(C)(O)c1cc(NC(=O)c2cc(F)cc(C(F)(F)F)c2)c2c(c1)C(=O)NC2c1cc(F)ccc1Cl] | CC(C)(O)c1cc2C(=O)NC(c2c(NC(=O)c2cc(F)cc(c2)C(F)(F)F)c1)c1cc(F)cc1Cl | 1H NMR (400 MHz, DMSO-d6) 10.4-10.6 (m, 1H), 8.9-9.2 (m, 1H), 7.9-8.0 (m, 1H), 7.7-7.8 (m, 2H), 7.6-7.7 (m, 1H), 7.5-7.6 (m, 1H), 7.2-7.4 (m, 1H), 6.9-7.1 (m, 1H), 6.3-6.9 (m, 1H), 5.9-6.1 (m, 1H), 5.2-5.4 (m, 1H), 1.4-1.6 (m, 6H) | 525 | A | |
| I-129 | 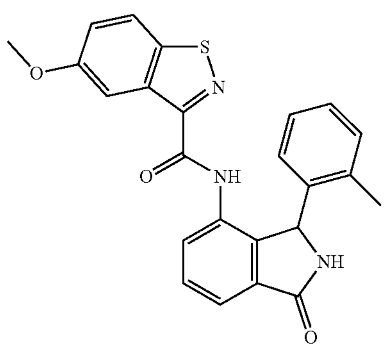 | COc1ccc2snc(C(=O)Nc3cccc4C(=O)NC(c34)c3ccccc3C)c2c1 | 1H NMR (400 MHz, DMSO-d6) 10.07 (s, 1H), 9.05 (s, 1H), 8.17 (d, 9.0 Hz, 1H), 8.10 (d, 2.4 Hz, 1H), 7.83 (dd, 7.6, 1.1 Hz, 1H), 7.68-7.55 (m, 2H), 7.32 (dd, 9.0, 2.5 Hz, 1H), 7.02-6.83 (m, 3H), 6.69 (br s, 1H), 6.13 (s, 1H), 3.86 (s, 3H), 2.42-2.02 (m, 3H). | 430.2 | E | |
| I-130 | 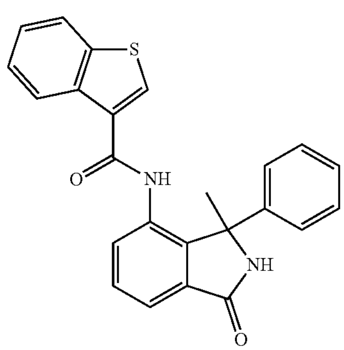 [SMILES: CC1(c2ccccc2)NC(=O)c2cccc(NC(=O)c3csc4ccccc34)c21] | CC1(NC(=O)c2ccc(NC(=O)c3csc4ccccc34)c12)c1ccccc1 | 1H NMR (400 MHz, DMSO-d6) 9.23 (s, 1H), 9.13 (s, 1H), 8.14-8.09 (m, 2H), 8.07-8.02 (m, 1H), 7.68 (dd, 7.0, 1.6 Hz, 1H), 7.64-7.56 (m, 2H), 7.43-7.39 (m, 2H), 7.28-7.18 (m, 5H), 1.97 (s, 3H). | 399.3 | E | |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-131 | 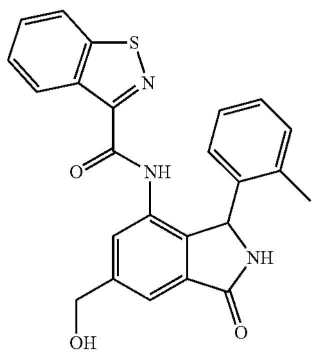 [SMILES: Cc1ccccc1C1NC(=O)c2cc(CO)cc(NC(=O)c3nsc4ccccc34)c21] | Cc1ccccc1C1NC(=O)c2cc(CO)cc(NC(=O)c3nsc4ccccc34)c12 | 1H NMR (400 MHz, DMSO-d6) 10.11 (s, 1H), 9.02 (s, 1H), 8.57 (d, 8.2 Hz, 1H), 8.29 (d, 8.2 Hz., 1H), 7.78 (s, 1H), 7.67 (ddd, 8.2, 7.1, 1.1 Hz, 1H), 7.61 (s, 1H), 7.58 (t, 7.6 Hz, 1H), 7.02-6.95 (m, 2H), 6.91 (t, 7.1 Hz, 1H), 6.68 (br s, 1H), 6.09 (s, 1H), 5.45 (s, 1H), 2.25 (br s, 3H). | 430.2 | A | |
| I-132 | 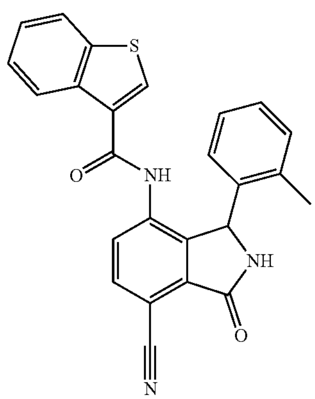 [SMILES: Cc1ccccc1C1NC(=O)c2c(C#N)ccc(NC(=O)c3csc4ccccc34)c21] | Cc1ccccc1C1NC(=O)c2c1c(NC(=O)c1csc3cccc13)ccc2C#N | 1H NMR (400 MHz, DMSO-d6) 10.45 (br s, 1H), 9.48 (s, 1H), 8.08 (d, 8.2 Hz, 1H), 8.02 (dd, 12.5, 5.5 Hz, 2H), 7.81 (d, 8.2 Hz, 1H), 7.65 (s, 1H), 7.46 7.33 (m, 2H), 7.12 (dd, 13.8, 6.8 Hz, 1H), 7.01 (dd, 15.2, 7.3 Hz, 1H), 6.58 (br s, 1H), 6.10 (s, 1H), 2.23 (br s, 3H). | 424.2 | A | |
| I-133 | 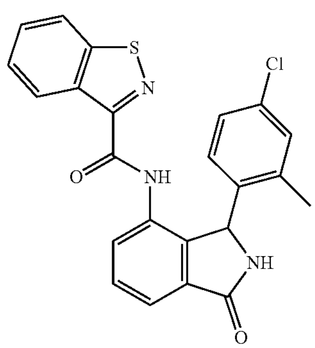 [SMILES: Cc1cc(Cl)ccc1C1NC(=O)c2cccc(NC(=O)c3nsc4ccccc34)c21] | Cc1cc(Cl)ccc1C1NC(=O)c2cccc(NC(=O)c3nsc4ccccc34)c12 | 1H NMR (400 MHz, DMSO-d6) 10.27 (s, 1H), 9.06 (s, 1H), 8.55 (d, 8.2 Hz, 1H), 8.31 (d, 8.3 Hz, 1H), 7.75 (dd, 7.6, 1.1 Hz, 1H), 7.73-7.55 (m, 4H), 7.01 (d, 2.0 Hz, 1H), 6.95 (d, 7.3 Hz, 1H), 6.65 (br s, 1H), 6.07 (s, 1H), 2.22 (br s, 3H). | 433.7 | D | |
| I-134 | 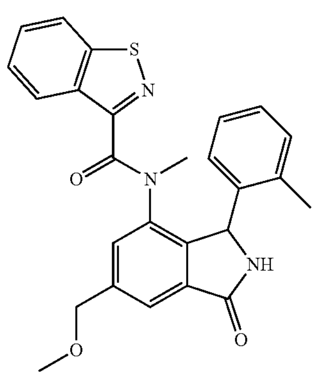 [SMILES: COCc1cc2c(c(N(C)C(=O)c3nsc4ccccc34)c1)C(c1ccccc1C)NC2=O] | COCc1cc2C(=O)NC(c2c(c1)N(C)C(=O)c1nsc2ccccc12)c1ccccc1C | 1H NMR (400 MHz, CD3OD) (s, 1H), 8.13 (d, 7.8 Hz, 0.40H), 7.98 (d, 7.9 Hz, 1H), 7.90 (s, 0.33H), 7.66 (s, 1H), 7.64-7.47 (m, 2H), 7.44-7.01 (m, 4H), 6.73 (br s, 0.55H), 6.37 (br s, 0.53H), 6.03 (br s, 0.31H), 4.67 (s, 0.35H), 4.58-4.48 (m, 0.34H), 4.36 (s, 1.37H), 3.50 (d, 8.6 Hz, 1H), 3.08 (br s, 2H), 2.94 (br s, 0.56H), 2.64 (br s, 2H), 1.29 (s, 1.12H). | 458.3 | E | |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-135 | 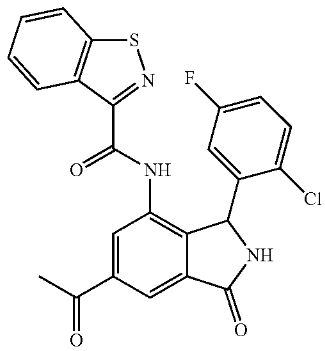 [SMILES: CC(=O)c1cc(NC(=O)c2nsc3ccccc23)c2c(c1)C(=O)NC2c1cc(F)ccc1Cl] | CC(=O)c1cc2C(=O)NC(c2c(NC(=O)c2nsc3ccccc23)c1)c1cc(F)ccc1Cl | 1H NMR (400 MHz, DMSO-d6) 10.1-10.5 (m, 1H), 8.9-9.2 (m, 1H), 8.5-8.7 (m, 1H), 8.2-8.3 (m, 1H), 7.8-7.9 (m, 1H), 7.7-7.8 (m, 1H), 7.6-7.7 (m, 1H), 7.5-7.6 (m, 1H), 7.1-7.3 (m, 1H), 6.9-7.0 (m, 1H), 6.0-6.3 (m, 1H), 5.6-5.8 (m, 1H), 2.5 (m, 3H) | 480 | C | |
| I-136 | 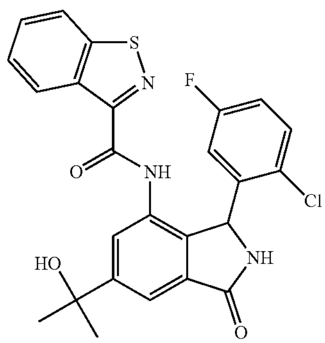 [SMILES: CC(C)(O)c1cc(NC(=O)c2nsc3ccccc23)c2c(c1)C(=O)NC2c1cc(F)ccc1Cl] | CC(C)(O)c1cc2C(=O)NC(c2c(NC(=O)c2nsc3ccccc23)c1)c1cc(F)ccc1Cl | ¹H NMR (400 MHz, DMSO-d$_6$) δ 10.1-10.5 (m, 1H), 8.9-9.2 (m, 1H), 8.5-8.7 (m, 1H), 8.2-8.3 (m, 1H), 7.8-7.8 (m, 1H), 7.6-7.7 (m, 1H), 7.5-7.6 (m, 1H), 7.2-7.3 (m, 1H), 6.9-7.0 (m, 1H), 6.4-6.9 (m, 1H), 6.0-6.2 (m, 1H), 5.6-5.7 (m, 1H), 5.1-5.3 (m, 1H), 1.3-1.6 (m, 6H). | 496 | A | |
| I-137 | 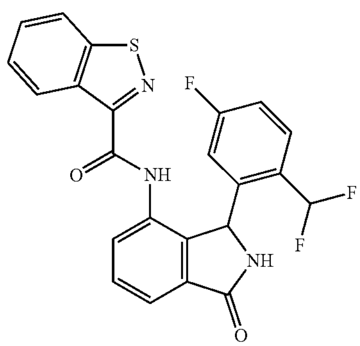 [SMILES: O=C1NC(c2cc(F)ccc2C(F)F)c2c(NC(=O)c3nsc4ccccc34)cccc21] | FC(F)c1cc(F)cc1C1NC(=O)c2cccc(NC(=O)c3nsc4ccccc34)c1 2 | ¹H NMR (400 MHz, DMSO-d$_6$) δ 10.25 (s, 1H), 9.17 (s, 1H), 8.54 (d, J = 8.05 Hz, 1H), 8.26 (d, J = 8.30 Hz, 1H), 7.11-8.09 (m, 7H), 7.05 (dt, J = 2.44, 8.42 Hz, 1H), 6.35-6.65 (m, 1H), 6.13 (s, 1H). | 454.4 | A | |
| I-138 | 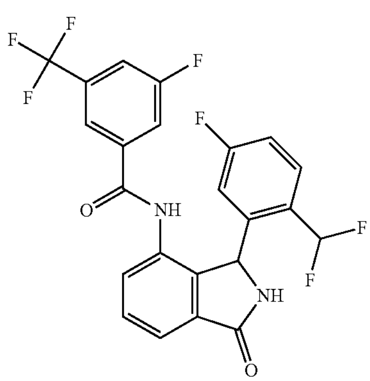 [SMILES: O=C(Nc1cccc2c1C(c1cc(F)ccc1C(F)F)NC2=O)c1cc(F)cc(C(F)(F)F)c1] | FC(F)c1cc(F)cc1C1NC(=O)c2cccc(NC(=O)c3cc(F)cc(c3)C(F)(F)F)c12 | ¹H NMR (400 MHz, DMSO-d$_6$) δ 10.44 (s, 1H), 9.14 (s, 1H), 7.90-8.00 (m, 1H), 7.83-7.90 (m, 1H), 7.67-7.74 (m, 1H), 7.58-7.67 (m, 2H), 7.52-7.57 (m, 1H), 7.47-7.52 (m, 1H), 7.40-7.47 (m, 1H), 7.16 (dt, J = 2.44, 8.42 Hz, 1H), 6.24-6.62 (m, 1H), 5.77-6.15 (m, 1H). | 483.4 | A | |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-139 | 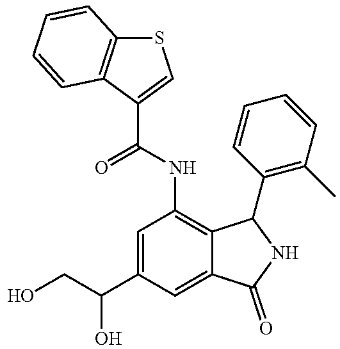 [SMILES: Cc1ccccc1C1NC(=O)c2cc(C(O)CO)cc(NC(=O)c3csc4ccccc34)c21] | Cc1ccccc1C1NC(=O)c2cc(cc(NC(=O)c3csc4ccccc34)c12)C(O)CO | 1H NMR (400 MHz, DMSO-d6) 10.09 (s, 0.5H), 10.07 (s, 0.5H), 8.95 (s, 1H), 7.98 (m, 2H), 7.64 (s, 0.5H), 7.62 (s, 0.5H), 7.55 (d, 14.9 Hz, 2H), 7.36 (m, 2H), 7.05 (d, 7.5 Hz, 1H), 6.96 (m, 12.5, 5.3 Hz, 2H), 6.56 (br s, 1H), 5.97 (s, 1H), 5.46 (d, 4.4 Hz, 1H), 4.80 (sets of d, 5.8 Hz, 1H), 4.65 (m, 1H), 3.50 (m, 2H), 2.15 (s, 3H). | 458.7 | A | |
| I-140 | 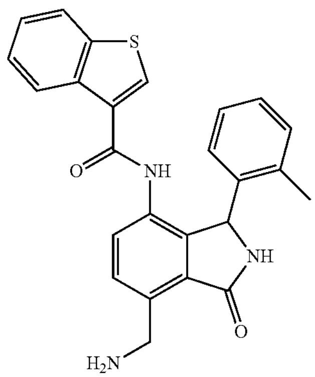 [SMILES: Cc1ccccc1C1NC(=O)c2c(CN)ccc(NC(=O)c3csc4ccccc34)c21] | Cc1ccccc1C1NC(=O)c2c1c(NC(=O)c1csc3ccccc13)ccc2CN | 1H NMR (400 MHz, DMSO-d6) 10.25-10.10 (m, 1H), 9.38 (s, 1H), 8.02 (d, 7.2 Hz, 2H), 7.62 (d, J = 16.0 Hz, 3H), 7.46-7.35 (m, 2H), 7.11 (1, 7.2 Hz, 1H), 7.06-6.95 (m, 2H), 6.61 (s, 1H), 6.07 (s, 1H), 4.47 (s, 2H), 2.23 (s, 3H). | 429.3 | A | |
| I-141 | 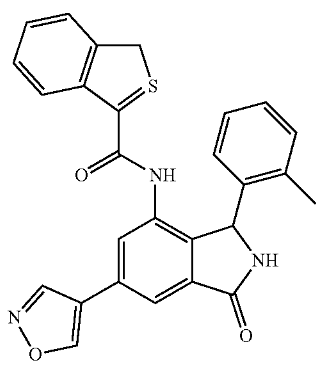 | Cc1ccccc1C1NC(=O)c2cc(cc(NC(=O)c3csc4ccccc34)c12)-c1cnoc1 | 1H NMR (400 MHz, DMSO-d6) 10.19 (s, 1H), 9.61 (s, 1H), 9.29 (s, 1H), 9.08 (s, 1H), 8.09-8.03 (m, 1H), 8.02-7.97 (m, 2H), 7.84 (d, 1.5 Hz, 1H), 7.66 (s, 1H), 7.42-7.34 (m, 2H), 7.05 (td, 7.4, 1.3 Hz, 1H), 7.01-6.91 (m, 2H), 6.00 (s, 1H), 1.20 (s, 3H). | 465.8 | A | |
| I-142 | 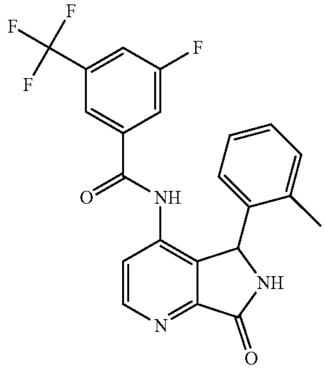 | Cc1ccccc1C1NC(=O)c2nccc(NC(=O)c3cc(F)cc(c3)C(F)(F)F)c12 | | 430.4 | B | |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-143 | 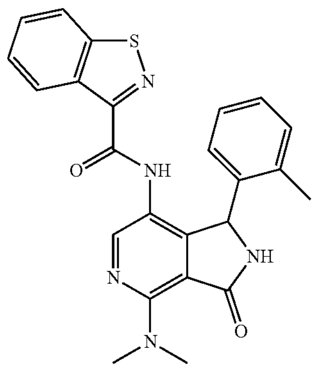 [SMILES: Cc1ccccc1C1NC(=O)c2c(N(C)C)ncc(NC(=O)c3nsc4ccccc34)c21] | CN(C)c1ncc(NC(=O)c2nsc3cccc23)c2C(NC(=O)c12)c1ccccc1C | | 444.45 | B | |
| I-144 | 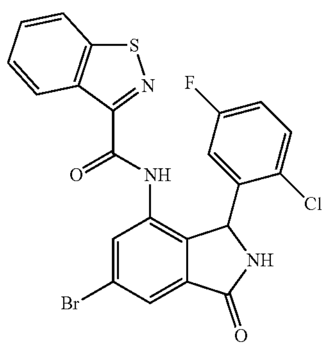 [SMILES: O=C1NC(c2cc(F)ccc2Cl)c2c(NC(=O)c3nsc4ccccc34)cc(Br)cc21] | Fc1ccc(C1)c(c1)C1NC(=O)c2cc(Br)cc(NC(=O)c3nsc4ccccc34)c12 | 1H NMR (400 MHz, DMSO-d6) 10.3-10.6 (m, 1H), 9.2-9.4 (m, 1H), 8.5-8.7 (m, 1H), 8.2-8.3 (m, 1H), 7.9-8.0 (m, 1H), 7.75 (s, 1H), 7.6-7.7 (m, 1H), 7.5-7.6 (m, 1H), 7.2-7.3 (m, 1H), 6.9-7.0 (m, 1H), 6.5-6.9 (m, 1H), 6.0-6.2 (m, 1H) | 518.29 | A | C |
| I-145 | 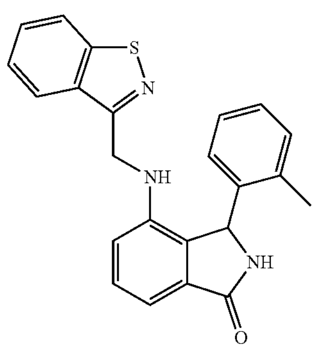 [SMILES: Cc1ccccc1C1NC(=O)c2cccc(NCc3nsc4ccccc34)c21] | Cc1ccccc1C1NC(=O)c2cccc(NCc3nsc4ccccc34)c12 | 1H NMR (400 MHz, DMSO-d6) 8.87 (s, 1H), 8.13 (d, 8.2 Hz, 1H), 7.83 (d, 8.2 Hz, 1H), 7.55 (t, 7.7 Hz, 1H), 7.31 (t, 7.7 Hz, 2H), 7.23 (d, 4.2 Hz, 2H), 7.04-7.02 (m, 2 Hz, 2H), 6.89 (d, 8.2 Hz, 1H), 6.74 (m, 1H), 6.82-6.60 (m, 1H), 5.80 (s, 1H), 5.30 (s, 1H), 4.71 (ddd, 21.1, 16.1, 5.4 Hz, 2H), 2.40 (br s, 3H) | 386.3 | E | |
| I-146 | 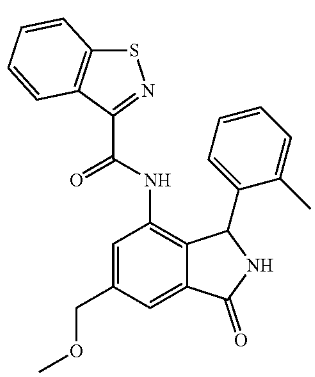 [SMILES: COCc1cc(NC(=O)c2nsc3ccccc23)c2c(c1)C(=O)NC2c1ccccc1C] | COCc1cc2C(=O)NC(c2c(NC(=O)c2nsc3cccc23)c1)c1ccccc1C | 1H NMR (400 MHz, CDCl3) 8.93 (d, 7.5 Hz, 1H), 8.81 (s, 1H), 8.45 (s, 1H), 7.95 (d, 7.8 Hz, 1H), 7.77 (s, 1H), 7.56 (dtd, 16.2, 7.0, 1.2 Hz, 2H), 7.23 (s, 1H), 7.15 (s, 1H), 6.52 (s, 1H), 5.98 (br s, 1H), 4.62 (s, 2H), 3.47 (s, 3H), 1.78 (br s, 3H). | 444.2 | A | C |

TABLE 2-continued

Representative Compounds of the Invention with Bioactivity Data.

| Ex. No. | Structure | SMILES | $^1$H NMR | MS | ADP-Glo IC$_{50}$ | MCF 10A IC$_{50}$ |
|---|---|---|---|---|---|---|
| I-147 | 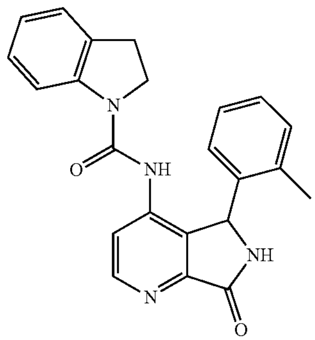 | Cc1ccccc1C1NC(=O)c2nccc(NC(=O)N3CCc4ccccc34)c12 | 1H NMR (400 MHz, DMSO-d6) 9.34 (s, 1H), 8.83 (br s, 1H), 8.64 (d, 5.3 Hz, 1H), 7.64 (d, 7.8 Hz, 1H), 7.42 (d, 5.4 Hz, 1H), 7.18-7.07 (m, 3H), 7.04-6.95 (m, 2H), 6.92 (t, 7.1 Hz, 1H), 6.55 (br s, 1H), 5.90 (s, 1H), 3.62-3.52 (m, 1H), 3.01-2.78 (m, 3H), 2.11 (br s, 3H) | 385.4 | B | |
| I-148 | 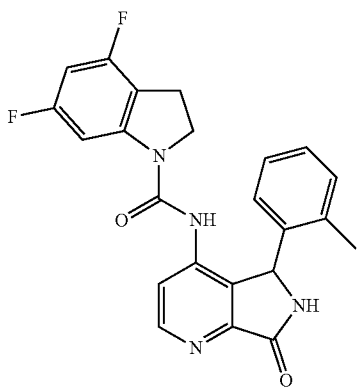 [SMILES: Cc1ccccc1C1NC(=O)c2nccc(NC(=O)N3CCc4c(F)cc(F)cc43)c21] | Cc1ccccc1C1NC(=O)c2nccc(NC(=O)N3CCc4cc(F)cc4F)c12 | 1H NMR (400 MHz, DMSO-d6) 9.33 (s, 1H), 9.06 (br s, 1H), 8.63 (d, 5.3 Hz, 1H), 7.33 (d, 5.3 Hz, 1H), 7.26 (d, 10.3 Hz, 1H), 7.12 (td, 7.4, 1.0 Hz, 1H), 6.96 (dd, 17.5, 7.5 Hz, 2H), 6.75 (td, 9.5, 2.2 Hz, 1H), 6.63-6.40 (m, 1H), 5.82 (s, 1H), 3.74-3.57 (m, 1H), 3.02-2.82 (m, 2H), 2.76 (m, 1H), 2.13 (m, 3H). | 421.2 | C | |
| I-149 | 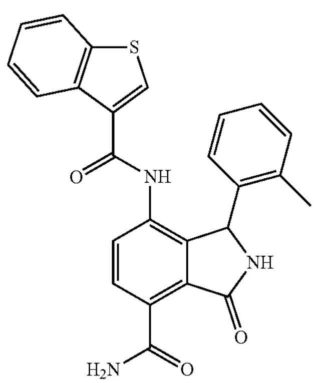 [SMILES: Cc1ccccc1C1NC(=O)c2c(C(N)=O)ccc(NC(=O)c3csc4ccccc34)c21] | Cc1ccccc1C1NC(=O)c2c1c(NC(=O)c1csc3cccc13)ccc2C(N)=O | 1H NMR (400 MHz, DMSO-d6) 10.78 (s, 1H), 10.25 (Br s, 1H), 9.80 (s, 1H), 8.33 (d, 8.3 Hz, 1H), 8.06-8.01 (m, 2H), 7.78 (d, 8.4 Hz, 1H), 7.73 (s, 1H), 7.68-7.58 (m, 1H), 7.45-7.36 (m, 2H), 7.12 (td, 7.7, 0.9 Hz, 1H), 7.07-6.97 (m, 2H), 6.60 (Br s, 1H), 6.12 (s, 1H), 2.23 (Br s, 3H). | 442.3 | A | |
| I-150 | 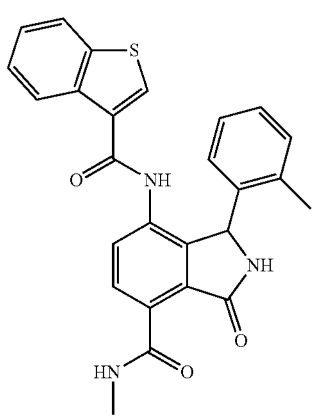 [SMILES: CNC(=O)c1ccc(NC(=O)c2csc3ccccc23)c2c1C(=O)NC2c1ccccc1C] | CNC(=O)c1ccc(NC(=O)c2csc3cccc23)c2C(NC(=O)c12)c1cccc1C | 1H NMR (400 MHz, DMSO-d6) 11.20 (s, 1H), 10.22 (s, 1H), 9.82 (s, 1H), 8.33 (d, 7.9 Hz, 1H), 8.03 (d, 6.2 Hz, 2H), 7.77 (d, 8.1 Hz, 1H), 7.62 (s, 1H), 7.41 (s, 2H), 7.11 (d, 7.1 Hz, 1H), 7.07-6.93 (m, 2H), 6.61 (Br s, 1H), 6.13 (s, 1H), 2.91 (s, 3H), 2.23 (br s, 3H). | 456.3 | A | |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-151 | 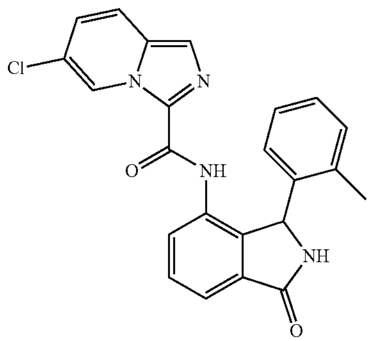 [SMILES: Cc1ccccc1C1NC(=O)c2cccc(NC(=O)c3ncc4ccc(Cl)cn34)c21] | Cc1ccccc1C1NC(=O)c2cccc(NC(=O)c3ncc4ccc(Cl)cn34)c12 | 1H NMR (400 MHz, DMSO-d6) 9.90 (s, 1H), 9.31 (dt, 1.7, 0.8 Hz, 1H), 9.03 (s, 1H), 7.87 (dd, 9.6, 0.9 Hz, 1H), 7.82 (dd, 7.5, 1.3 Hz, 1H), 7.64-7.56 (m, 3H), 7.19 (dd, 9.5, 1.8 Hz, 1H), 6.99-6.93 (m, 2H), 6.91-6.86 (m, 1H), 6.67 (br s, 1H), 6.11 (s, 1H), 2.26 (br. s, 3H). | 417.2 | E | |
| I-152 | 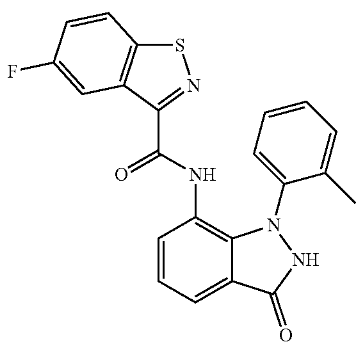 [SMILES: Cc1ccccc1-n1[nH]c(=O)c2cccc(NC(=O)c3nsc4ccc(F)cc34)c21] | Cc1ccccc1-n1[nH]c(=O)c2cccc(NC(=O)c3nsc4ccc(F)cc34)c12 | 1H NMR (400 MHz, DMSO-d6) 11.12 (br s, 1H), 9.98 (s, 1H), 8.28 (dd, 9.1, 4.8 Hz, 1H), 8.11 (dd, 9.7, 2.5 Hz, 1H), 7.66 (dd, 8.0, 0.7 Hz, 1H), 7.55 (td, 8.8, 2.6 Hz, 1H), 7.45 (d, 7.2 Hz, 1H), 7.15-7.08 (m, 2H), 6.92 (d, 7.5 Hz, 1H), 6.81 (td, 7.5, 1.3 Hz, 1H), 6.74 (td, 7.5, 1.3 Hz, 1H), 2.04 (s, 3H). | 419.2 | D | |
| I-153 | 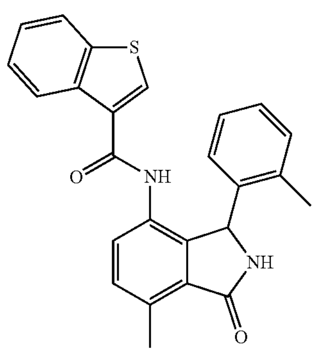 [SMILES: Cc1ccccc1C1NC(=O)c2c(C)ccc(NC(=O)c3csc4ccccc34)c21] | Cc1ccc(NC(=O)c2csc3cccccc23)c2C(NC(=O)c12)c1ccccc1C | 1H NMR (400 MHz, DMSO-d6) 9.98 (s, 1H), 8.93 (s, 1H), 8.06-7.99 (m, 2H), 7.61 (s, 1H), 7.45-7.35 (m, 3H), 7.34 (d, 8.0 Hz, 1H), 7.08 (td, 7.5, 1.3 Hz, 1H), 6.98 (m, 2H), 6.62 (br s, 1H), 5.95 (s, 1H), 2.69 (s, 3H), 2.19 (br s, 3H). | 413.3 | B | |
| I-154 | 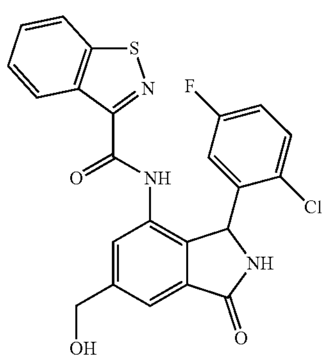 [SMILES: O=C1NC(c2cc(F)ccc2Cl)c2c(NC(=O)c3nsc4ccccc34)cc(CO)cc21] | OCc1cc2C(=O)NC(c2c(NC(=O)c2nsc3cccc23)c1)c1cc(F)ccc1Cl | 1H NMR (400 MHz, DMSO-d6) 10.2-10.6 (m, 1H), 8.9-9.3 (m, 1H), 8.5-8.8 (m, 1H), 8.2-8.3 (m, 1H), 8.1-8.4 (m, 1H), 7.5-7.8 (m, 4H), 7.2-7.4 (m, 1H), 6.9-7.1 (m, 1H), 5.9-6.3 (m, 1H), 5.4-5.6 (m, 1H), 4.5-4.8 (m, 2H) | 468 | A | |

TABLE 2-continued

Representative Compounds of the Invention with Bioactivity Data.

| Ex. No. | Structure | SMILES | $^1$H NMR | MS | ADP-Glo IC$_{50}$ | MCF 10A IC$_{50}$ |
|---|---|---|---|---|---|---|
| I-155 | 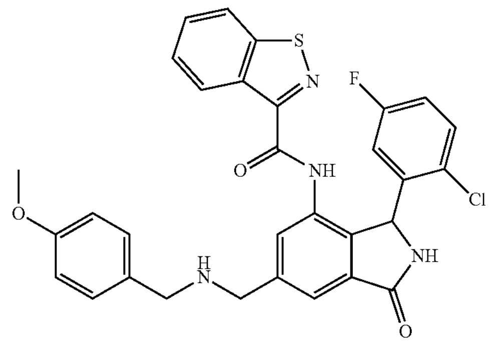 [SMILES: COc1ccc(CNCc2cc(NC(=O)c3nsc4ccccc34)c3c(c2)C(=O)NC3c2cc(F)ccc2Cl)cc1] | COc1ccc(CNCc2cc3C(=O)NC(c3c(NC(=O)c3nsc4cccc34)c2)c2cc(F)ccc2Cl)cc1 | 1H NMR (500 MHz, DMSO-d6) 3.64-3.77 (m, 2H), 3.79-3.91 (m, 1H), 5.98-6.24 (m, 1H), 6.78-6.95 (m, 1H), 6.95-7.06 (m, 1H), 7.17-7.33 (m, 1H), 7.48-7.63 (m, 1H), 7.63-7.81 (m, 1H), 8.05-8.19 (m, 1H), 8.23-8.37 (m, 1H), 8.53-8.74 (m, 1H), 8.93-9.22 (m, 1H) 10.21-10.57 (m, 1H) | 587 | A | B |
| I-156 | 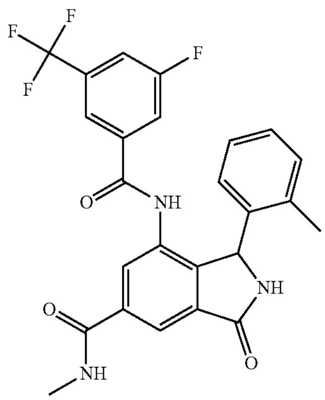 [SMILES: CNC(=O)c1cc(NC(=O)c2cc(F)cc(C(F)(F)F)c2)c2c(c1)C(=O)NC2c1ccccc1C] | CNC(=O)c1cc2C(=O)NC(c2c(NC(=O)c2cc(F)cc(c2)C(F)(F)F)c1)c1ccccc1C | 1H NMR (400 MHz, CDCl3) 8.60 (s, 1H), 8.15 (d, 1.4 Hz, 1H), 7.51-7.42 (m, 2H), 7.34 (d, 7.5 Hz, 1H), 7.22 (d, 8.3 Hz, 5H), 6.43 (s, 1H), 6.33 (s, 1H), 5.93 (s, 1H), 3.06 (d, 4.8 Hz, 3H) | 486.37 | A | |
| I-157 | 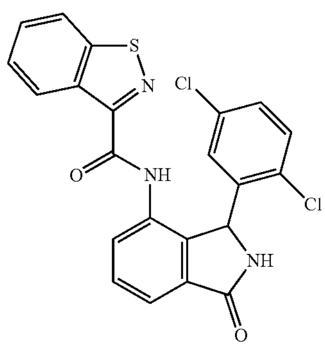 [SMILES: O=C1NC(c2cc(Cl)ccc2Cl)c2c(NC(=O)c3nsc4ccccc34)cccc21] | C1c1ccc(C1)c(c1)C1NC(=O)c2cccc(NC(=O)c3nsc4ccccc34)c12 | $^1$H NMR (400 MHz, DMSO-d$_6$) δ 10.17-10.60 (m, 1H), 8.89-9.28 (m, 1H), 8.65 (br d, J = 8.05 Hz, 1H), 8.30 (d, J = 8.05 Hz, 1H), 6.82-8.02 (m, 7H), 5.74-6.69 (m, 2H). | 454.3 | A | |
| I-158 | 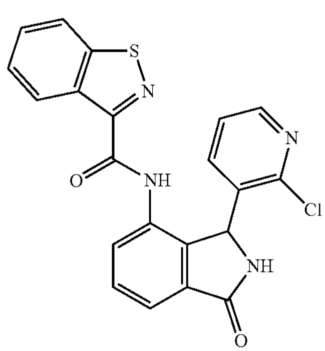 [SMILES: O=C1NC(c2cccnc2Cl)c2c(NC(=O)c3nsc4ccccc34)cccc21] | C1c1ncccc1C1NC(=O)c2cccc(NC(=O)c3nsc4ccccc34)c12 | $^1$H NMR (400 MHz, DMSO-d$_6$) δ 10.32-10.59 (m, 1H), 8.97-9.31 (m, 1H), 8.62 (br d, J = 8.30 Hz, 1H), 8.22-8.37 (m, 1H), 8.04-8.22 (m, 1H), 6.82-7.88 (m, 7H), 5.87-6.53 (m, 1H). | 421.3 | D | |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-159 | 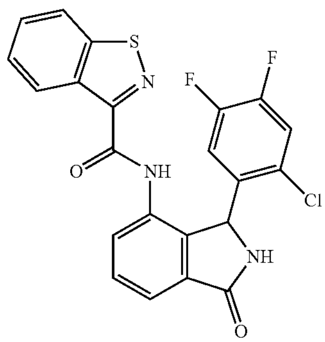 [SMILES: O=C1NC(c2cc(F)c(F)cc2Cl)c2c(NC(=O)c3nsc4ccccc34)cccc21] | Fc1cc(Cl)c(cc1F)C1NC(=O)c2cccc(NC(=O)c3nsc4ccccc34)c12 | ¹H NMR (400 MHz, DMSO-d$_6$) δ 10.21-10.54 (m, 1H), 8.95-9.30 (m, 1H), 8.62 (d, J = 8.05 Hz, 1H), 8.31 (d, J = 8.30 Hz, 1H), 6.86-7.83 (m, 7H), 6.00-6.27 (m, 1H). | 456.4 | A | |
| I-160 | 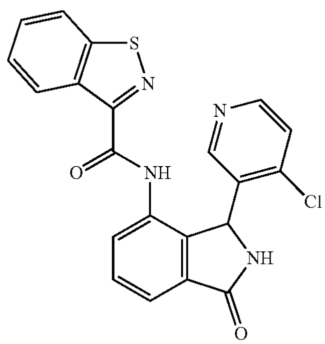 [SMILES: O=C1NC(c2cnccc2Cl)c2c(NC(=O)c3nsc4ccccc34)cccc21] | C1c1ccncc1C1NC(=O)c2cccc(NC(=O)c3nsc4ccccc34)c12 | ¹H NMR (400 MHz, DMSO-d$_6$) δ 10.53 (s, 1H), 9.10 (br s, 1H), 8.63 (d, J = 8.30 Hz, 1H), 7.91-8.40 (m, 3H), 7.44-7.78 (m, 5H), 7.30 (d, J = 5.13 Hz, 1H), 6.01-6.31 (m, 1H). | 421.3 | C | |
| I-161 | 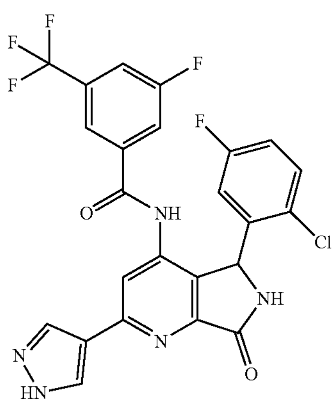 [SMILES: O=C(Nc1cc(-c2cn[nH]c2)nc2c1C(c1cc(F)ccc1Cl)NC2=O)c1cc(F)cc(C(F)(F)F)c1] | Fc1ccc(Cl)c(cc1)C1NC(=O)c2nc(cc(NC(=O)c3cc(F)cc(c3)C(F)(F)F)c12)-c1cn[nH]c1 | ¹H NMR (400 MHz, DMSO-d$_6$) δ 13.21 (br s, 1H), 10.85 (br s, 1H), 9.44 (br s, 1H), 8.43 (br s, 1H), 8.12 (br s, 1H), 7.97 (br d, J = 4.1 Hz, 1H), 7.63-7.87 (m, 3H), 7.34 (br dd, J = 8.8, 5.1 Hz, 1H), 7.09 (td, J = 8.4, 2.9 Hz, 1H), 6.75-6.96 (m, 1H), 5.98 (br s, 1H). | 534.4 | A | B |
| I-162 | 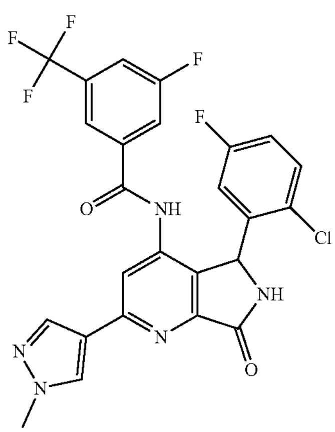 [SMILES: Cn1cc(-c2cc(NC(=O)c3cc(F)cc(C(F)(F)F)c3)c3c(n2)C(=O)NC3c2cc(F)ccc2Cl)cn1] | Cn1cc(cn1)-c1cc(NC(=O)c2cc(F)cc(c2)C(F)(F)F)c2C(NC(=O)c2n1)c1cc(F)ccc1Cl | ¹H NMR (400 MHz, DMSO-d$_6$) δ 10.84 (br s, 1H), 9.44 (br s, 1H), 8.40 (s, 1H), 8.05 (s, 1H), 7.97 (br d, J = 6.6 Hz, 1H), 7.62-7.79 (m, 3H), 7.34 (br dd, J = 8.8, 5.1 Hz, 1H), 7.09 (td, J = 8.4, 2.9 Hz, 1H), 6.81-6.97 (m, 1H), 5.98 (br s, 1H), 3.93 (s, 3H) | 548.4 | A | |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-163 | 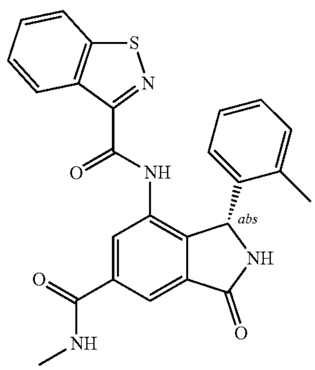 [SMILES: CNC(=O)c1cc(NC(=O)c2nsc3ccccc23)c2c(c1)C(=O)N[C@H]2c1ccccc1C] | CNC(=O)c1cc2C(=O)N[C@H](c2c(NC(=O)c2nsc3ccccc23)c1)c1ccccc1C | 1H NMR (400 MHz, DMSO-d6) 10.28 (s, 1H), 9.13-9.25 (m, 2H), 8.52-8.64 (m, 1H), 8.26-8.36 (m, 2H), 8.20 (s, 1H), 7.67 (br t, 7.57 Hz, 1H), 7.54-7.61 (m, 1H), 6.86-7.01 (m, 3H), 6.66-6.78 (m, 1H), 6.10-6.24 (m, 2H), 3.72 (tt, 4.76, 15.38 Hz, 2H), 2.10-2.40 (m, 3H) | 457.41 | A | |
| I-164 | 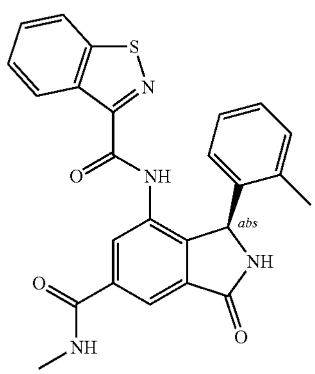 [SMILES: CNC(=O)c1cc(NC(=O)c2nsc3ccccc23)c2c(c1)C(=O)N[C@@H]2c1ccccc1C] | CNC(=O)c1cc2C(=O)N[C@@H](c2c(NC(=O)c2nsc3ccccc23)c1)c1ccccc1C | 1H NMR (400 MHz, DMSO-d6) 10.28 (s, 1H), 9.13-9.25 (m, 2H), 8.52-8.64 (m, 1H), 8.26-8.36 (m, 2H), 8.20 (s, 1H), 7.67 (br t, 7.57 Hz, 1H), 7.54-7.61 (m, 1H), 6.86-7.01 (m, 3H), 6.66-6.78 (m, 1H), 6.10-6.24 (m, 2H), 3.72 (tt, 4.76, 15.38 Hz, 2H), 2.10-2.40 (m, 3H) | 457.41 | D | D |
| I-165 | 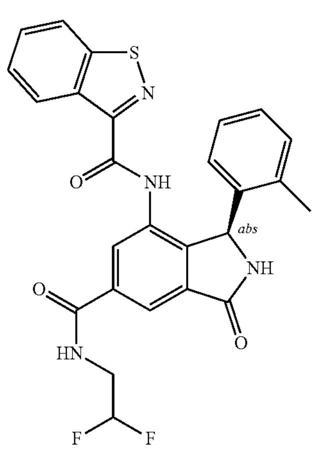 [SMILES: Cc1ccccc1[C@H]1NC(=O)c2cc(C(=O)NCC(F)F)cc(NC(=O)c3nsc4ccccc34)c21] | Cc1ccccc1[C@H]1NC(=O)c2cc(cc(NC(=O)c3nsc4ccccc34)c12)C(=O)NCC(F)F | | 507.38 | B | |

TABLE 2-continued

Representative Compounds of the Invention with Bioactivity Data.

| Ex. No. | Structure | SMILES | $^1$H NMR | MS | ADP-Glo IC$_{50}$ | MCF 10A IC$_{50}$ |
|---|---|---|---|---|---|---|
| I-166 | 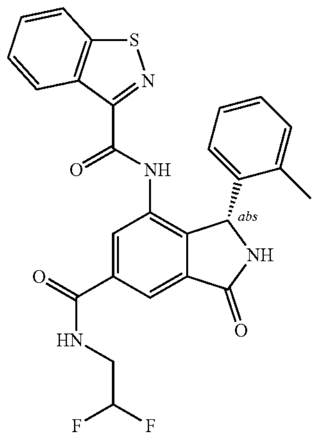 [SMILES: Cc1ccccc1[C@@H]1NC(=O)c2cc(C(=O)NCC(F)F)cc(NC(=O)c3nsc4ccccc34)c21] | Cc1ccccc1[C@@H]1NC(=O)c2cc(c(NC(=O)c3nsc4ccccc34)c12)C(=O)NCC(F)F | | 507.38 | A | A |
| I-167 | 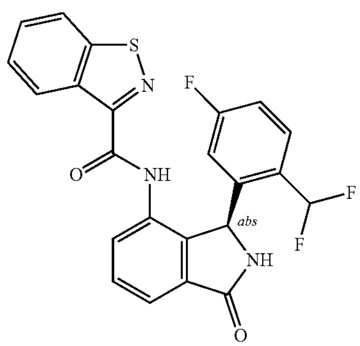 [SMILES: O=C1N[C@H](c2cc(F)ccc2C(F)F)c2c(NC(=O)c3nsc4ccccc34)cccc21] | FC(F)c1ccc(F)cc1[C@H]1NC(=O)c2cccc(NC(=O)c3nsc4cccc34)c12 | 1H NMR (400 MHz, DMSO-d6) 10.25 (s, 1H), 9.17 (s, 1H), 8.54 (d, 8.05 Hz, 1H), 8.26 (d, 8.30 Hz, 1H), 7.74 (d, 7.32 Hz, 1H), 7.65 (td, 7.38, 15.01 Hz, 2H), 7.47-7.56 (m, 1H), 7.35 (br dd, 5.61, 8.54 Hz, 1H), 7.05 (dt, 2.44, 8.42 Hz, 1H), 6.34-6.62 (m, 1H), 6.13 (s, 1H) | 452 | A | B |
| I-168 | 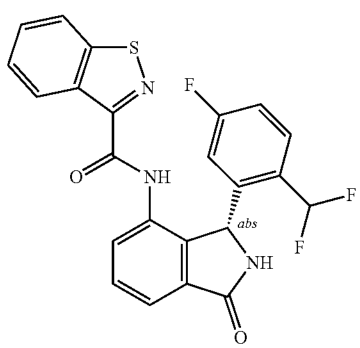 [SMILES: O=C1N[C@@H](c2cc(F)ccc2C(F)F)c2c(NC(=O)c3nsc4ccccc34)cccc21] | FC(F)c1ccc(F)cc1[c@@H]1NC(=O)c2cccc(NC(=O)c3nsc4cccc34)c12 | 1H NMR (400 MHz, DMSO-d6) 10.25 (s, 1H), 9.17 (s, 1H), 8.54 (d, 8.05 Hz, 1H), 8.26 (d, 8.30 Hz, 1H), 7.74 (d, 7.32 Hz, 1H), 7.65 (td, 7.38, 15.01 Hz, 2H), 7.47-7.56 (m, 1H), 7.35 (br dd, 5.61, 8.54 Hz, 1H), 7.05 (dt, 2.44, 8.42 Hz, 1H), 6.34-6.62 (m, 1H), 6.13 (s, 1H) | 452 | A | |
| I-169 | 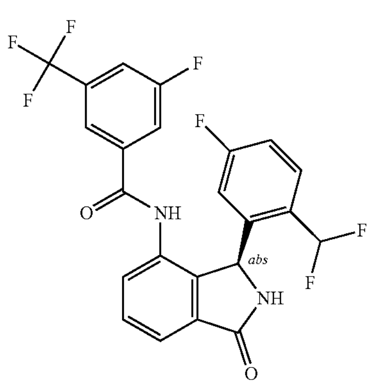 [SMILES: O=C(Nc1cccc2c1[C@@H](c1cc(F)ccc1C(F)F)NC2=O)c1cc(F)cc(C(F)(F)F)c1] | FC(F)c1ccc(F)cc1[C@H]1NC(=O)c2cccc(NC(=O)c3cc(F)cc(c3)C(F)(F)F)c12 | 1H NMR (400 MHz, DMSO-d6) 10.44 (s, 1H), 9.14 (s, 1H), 7.90-8.00 (m, 1H), 7.83-7.90 (m, 1H), 7.67-7.74 (m, 1H), 7.58-7.67 (m, 2H), 7.52-7.57 (m, 1H), 7.47-7.52 (m, 1H), 7.40-7.47 (m, 1H), 7.16 (dt, 2.44, 8.42 Hz, 1H), 6.24-6.62 (m, 1H), 5.77-6.15 (m, 1H) | 483 | D | |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-170 | 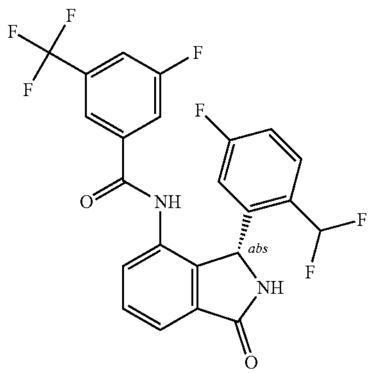 [SMILES: O=C(Nc1cccc2c1[C@H](c1cc(F)ccc1C(F)F)NC2=O)c1cc(F)cc(C(F)(F)F)c1] | FC(F)c1cc(F)cc1[C@@H]1NC(=O)c2cccc(NC(=O)c3cc(F)cc(c3)C(F)(F)F)c12 | 1H NMR (400 MHz, DMSO-d6) 10.44 (s, 1H), 9.14 (s, 1H), 7.90-8.00 (m, 1H), 7.83-7.90 (m, 1H), 7.67-7.74 (m, 1H), 7.58-7.67 (m, 2H), 7.52-7.57 (m, 1H), 7.47-7.52 (m, 1H), 7.40-7.47 (m, 1H), 7.16 (dt, 2.44, 8.42 Hz, 1H), 6.24-6.62 (m, 1H), 5.77-6.15 (m, 1H) | 483 | A | |
| I-171 | 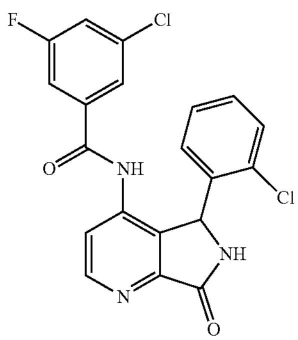 [SMILES: O=C(Nc1ccnc2c1C(c1ccccc1Cl)NC2=O)c1cc(F)cc(Cl)c1] | Fc1cc(Cl)cc(c1)C(=O)Nc1ccnc2C(=O)NC(c12)c1ccccc1Cl | | 416.2 | D | |
| I-172 | 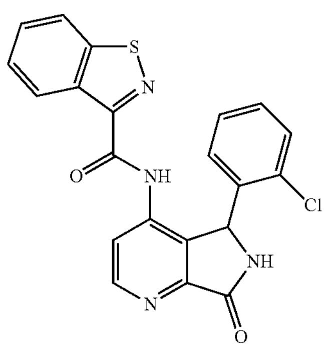 [SMILES: O=C1NC(c2ccccc2Cl)c2c(NC(=O)c3nsc4ccccc34)ccnc21] | C1c1cccc1C1NC(=O)c2nccc(NC(=O)c3nsc4cccc34)c12 | | 421 | B | |
| I-173 | 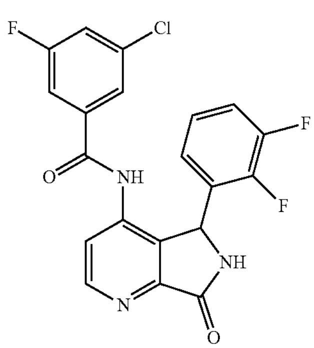 [SMILES: O=C(Nc1ccnc2c1C(c1cccc(F)c1F)NC2=O)c1cc(F)cc(Cl)c1] | Fc1cc(Cl)cc(c1)C(=O)Nc1ccnc2C(=O)NC(c12)c1cccc(F)c1F | | 418 | D | |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-174 | 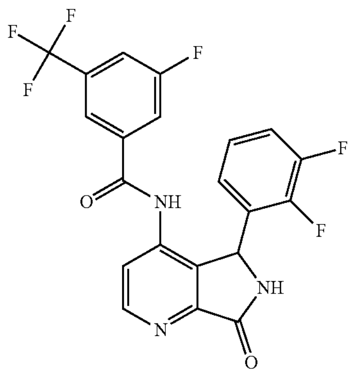 [SMILES: O=C(Nc1ccnc2c1C(c1cccc(F)c1F)NC2=O)c1cc(F)cc(C(F)(F)F)c1] | Fc1cc(cc(c1)C(F)(F)F)C(=O)Nc1ccnc2C(=O)NC(c12)c1cccc(F)c1F | | 452.2 | D | |
| I-175 | 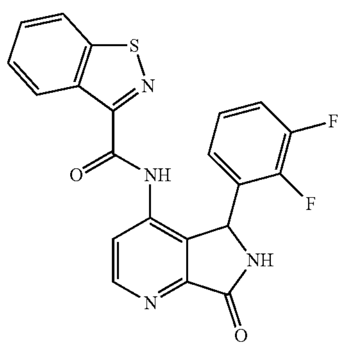 [SMILES: O=C1NC(c2cccc(F)c2F)c2c(NC(=O)c3nsc4ccccc34)ccnc21] | Fc1cccc(C2NC(=O)c3nccc(NC(=O)c4nsc5ccccc45)c23)c1F | | 421 | C | |
| I-176 | 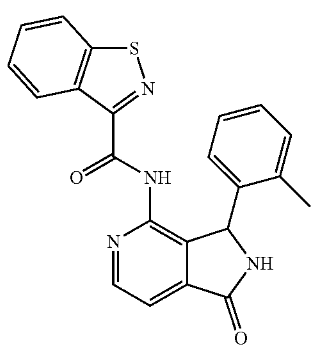 [SMILES: Cc1ccccc1C1NC(=O)c2ccnc(NC(=O)c3nsc4ccccc34)c21] | Cc1ccccc1C1NC(=O)c2ccnc(NC(=O)c3nsc4ccccc34)c12 | 1H NMR (400 MHz, DMSO-d6) 9.45 (s, 1H), 8.70 (d, 4.9 Hz, 1H), 8.42 (d, 8.4 Hz, 1H), 8.37 (s, 1H), 8.30 (d, 8.2 Hz, 1H), 7.72 (d, 4.9 Hz, 1H), 7.67 (t, 7.0 Hz, 1H), 7.58 (t, 7.7 Hz, 1H), 7.04-6.92 (m, 2H), 6.92-6.83 (m, 1H), 6.60 (br s, 1H), 6.23 (s, 1H), 2.22 (br s, 3H). | 401.2 | D | |
| I-177 | 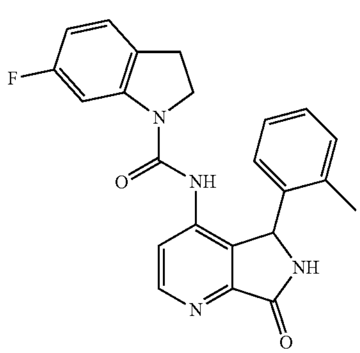 [SMILES: Cc1ccccc1C1NC(=O)c2nccc(NC(=O)N3CCc4ccc(F)cc43)c21] | Cc1ccccc1C1NC(=O)c2nccc(NC(=O)N3CCc4cc(F)cc34)c12 | 1H NMR (400 MHz, DMSO-d6) 9.35 (s, 1H), 8.95 (br s, 1H), 8.66 (d, 5.3 Hz, 1H), 7.43-7.38 (m, 2H), 7.20-7.09 (m, 2H), 7.01-6.96 (m, 2H), 6.79-6.70 (m, 1H), 6.55 (br s, 1H), 5.88 (s, 1H), 3.68-3.61 (m, 1H), 3.03-2.75 (m, 3H), 2.29-2.00 (m, 3H). | 403.3 | C | |

TABLE 2-continued

Representative Compounds of the Invention with Bioactivity Data.

| Ex. No. | Structure | SMILES | $^1$H NMR | MS | ADP-Glo IC$_{50}$ | MCF 10A IC$_{50}$ |
|---|---|---|---|---|---|---|
| I-178 | 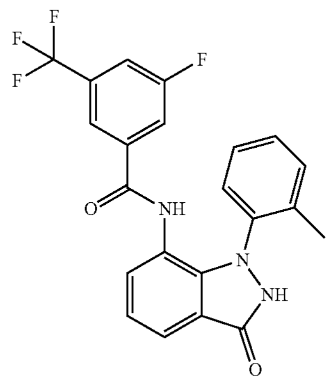 [SMILES: Cc1ccccc1-n1[nH]c(=O)c2cccc(NC(=O)c3cc(F)cc(C(F)(F)F)c3)c21] | Cc1ccccc 1-n1[nH]c (=O)c2ccc c(NC(=O) c3cc(F)c c(c3)C(F) (F)F)c12 | 1H NMR (400 MHz, DMSO-d6) 11.08 (s, 1H), 10.13 (s, 1H), 7.84 (d, 8.5 Hz, 1H), 7.72 (dd, 8.0, 0.9 Hz, 1H), 7.48 (s, 1H), 7.44 (d, 9.1 Hz, 1H), 7.25 (dd, 7.3, 0.8 Hz, 1H), 7.14 (t, 7.8 Hz, 1H), 7.11-7.06 (m, 2H), 7.01-6.92 (m, 2H), 2.03 (s, 3H). | 428.3 | C | |
| I-179 | 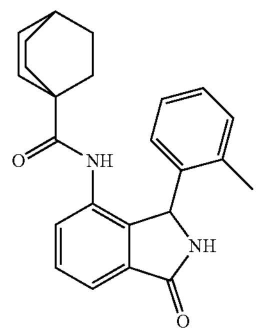 [SMILES: Cc1ccccc1C1NC(=O)c2cccc(NC(=O)C34CCC(CC3)CC4)c21] | Cc1ccccc 1C1NC(= O)c2cccc (NC(=O) C34CCC (CC3)CC 4)c12 | 1H NMR (400 MHz, DMSO-d6) 8.97 (s, 1H), 8.75 (s, 1H), 7.57-7.54 (m, 1H), 7.53-7.49 (m, 1H), 7.45 (dd, 7.5, 1.4 Hz, 1H), 7.18 (d, 4.0 Hz, 2H), 7.06-6.98 (m, 1H), 6.47 (br. s, 1H), 5.94 (s, 1H), 2.32 (br. s, 3H), 1.50-1.45 (m, 1H), 1.42-1.33 (m, 6H), 1.32-1.21 (m, 6H). | 375.3 | D | |
| I-180 | 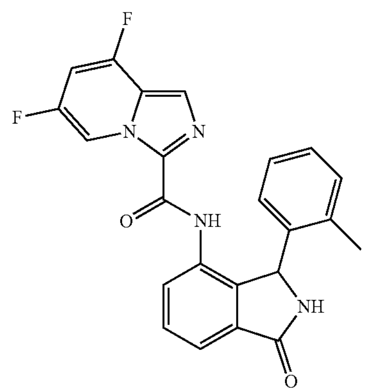 [SMILES: Cc1ccccc1C1NC(=O)c2cccc(NC(=O)c3ncc4c(F)cc(F)cn34)c21] | Cc1ccccc 1C1NC(= O)c2cccc (NC(=O) c3ncc4c( F)cc(F)cn 34)c12 | 1H NMR (400 MHz, DMSO-d6) 10.02 (br s, 1H), 9.14 (d, 4.0 Hz, 1H), 9.03 (s, 1H), 7.84 (d, 0.8 Hz, 1H), 7.78 (dd, 7.6, 1.2 Hz, 1H), 7.65-7.62 (m, 1H), 7.62-7.57 (m, 1H), 7.44 (ddd, 10.6, 8.8, 1.8 Hz, 1H), 6.99-6.92 (m, 2H), 6.90-6.85 (m, 1H), 6.68 (br s, 1H), 6.10 (s, 1H), 2.23 (br s, 3H). | 419.3 | E | |
| I-181 | 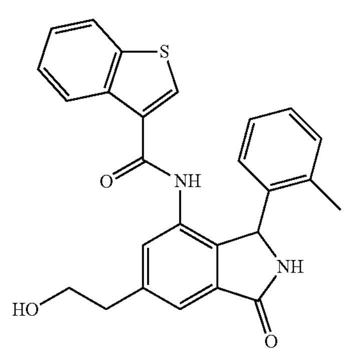 [SMILES: Cc1ccccc1C1NC(=O)c2cc(CCO)cc(NC(=O)c3csc4ccccc34)c21] | Cc1ccccc 1C1NC(= O)c2cc(C CO)cc(N C(=O)c3 csc4cccc c34)c12 | 1H NMR (400 MHz, DMSO-d6) 10.06 (s, 1H), 8.93 (s, 1H), 8.62-8.38 (m, 2H), 8.03-7.95 (m, 2H), 7.62 (s, 1H), 7.47 (s, 1H), 7.41-7.32 (m, 3H), 7.05 (t, 7.8 Hz, 1H), 6.99-6.90 (m, 1H), 6.57 (br s, 1H), 5.95 (s, 1H), 4.71 (br s, 1H), 3.71-3.61 (m, 2H), 2.92-2.77 (m, 2H), 2.14 (s, 3H). | 442.8 | A | |

TABLE 2-continued

Representative Compounds of the Invention with Bioactivity Data.

| Ex. No. | Structure | SMILES | $^1$H NMR | MS | ADP-Glo IC$_{50}$ | MCF 10A IC$_{50}$ |
|---|---|---|---|---|---|---|
| I-182 | 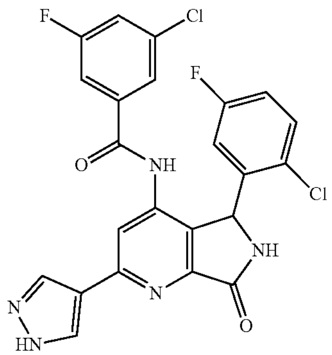 [SMILES: O=C(Nc1cc(-c2cn[nH]c2)nc2c1C(c1cc(F)ccc1Cl)NC2=O)c1cc(F)cc(Cl)c1] | Fc1ccc(C1)c(c1)C1NC(=O)c2nc(cc(NC(=O)c3cc(F)cc(C1)c3)c12)-c1cn[nH]c1 | $^1$H NMR (500 MHz., DMSO-d$_6$) δ 13.20 (br s, 1H), 10.69 (br s, 1H), 9.44 (br s, 1H), 8.42 (br s, 1H), 8.11 (br s, 1H), 7.88 (br s, 1H), 7.57-7.83 (m, 3H), 7.36-7.43 (m, 2H), 7.14 (td, J = 8.4, 3.1 Hz, 1H), 5.99 (br s, 1H). | 500.4 | B | |
| I-183 | 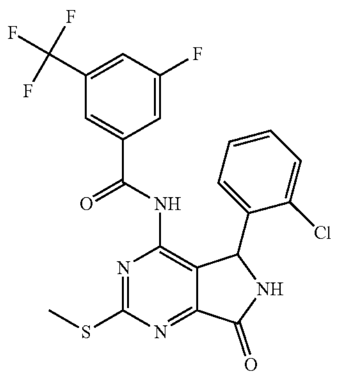 [SMILES: CSc1nc(NC(=O)c2cc(F)cc(C(F)(F)F)c2)c2c(n1)C(=O)NC2c1ccccc1Cl] | CSc1nc2C(=O)NC(c2c(NC(=O)c2cc(F)cc(c2)C(F)(F)F)n1)c1ccccc1Cl | 1H NMR (400 MHz, DMSO-d6) 9.63 (br s, 1H), 7.84 (br d, 7.58 Hz, 1H), 7.64 (br d, 9.09 Hz, 1H), 7.59 (s, 1H), 7.15-7.23 (m, 1H), 7.07-7.15 (m, 1H), 7.03 (br t, 6.95 Hz, 1H), 6.83-6.97 (m, 1H), 6.51 (s, 1H), 5.98 (br s, 1H), 2.60 (s, 3H) | 497.3 | D | |
| I-184 | 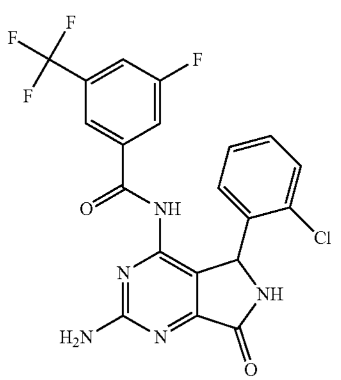 [SMILES: Nc1nc(NC(=O)c2cc(F)cc(C(F)(F)F)c2)c2c(n1)C(=O)NC2c1ccccc1Cl] | Nc1nc2C(=O)NC(c2c(NC(=O)c2cc(F)cc(c2)C(F)(F)F)n1)c1ccccc1Cl | | 466.4 | C | |
| I-185 | 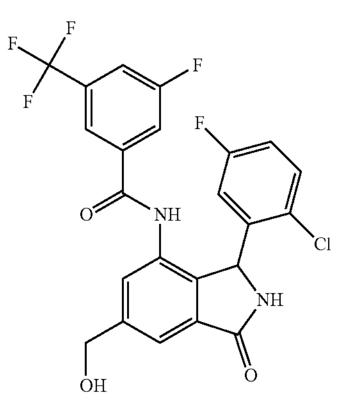 [SMILES: O=C(Nc1cc(CO)cc2c1C(c1cc(F)ccc1Cl)NC2=O)c1cc(F)cc(C(F)(F)F)c1] | OCc1cc2C(=O)NC(c2c(NC(=O)c2cc(F)cc(c2)C(F)(F)F)c1)c1cc(F)ccc1Cl | 1H NMR (DMSO-d6, 400 MHz) 10.4-10.6 (m, 1H), 9.0-9.2 (m, 1H), 7.9-8.0 (m, 1H), 7.7-7.8 (m, 1H), 7.5-7.7 (m, 2H), 7.4-7.5 (m, 1H), 7.2-7.4 (m, 1H), 7.0-7.1 (m, 1H), 6.5-6.8 (m, 1H), 5.9-6.2 (m, 1H), 5.3-5.6 (m, 1H), 4.4-4.9 (m, 2H) | 497 | A | |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-186 | 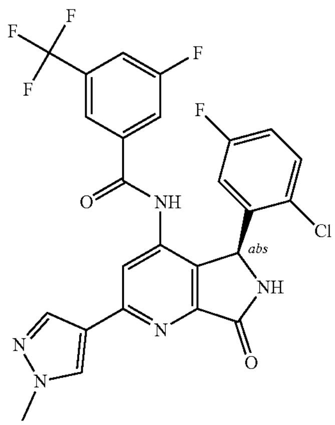 [SMILES: Cn1cc(-c2cc(NC(=O)c3cc(F)cc(C(F)(F)F)c3)c3c(n2)C(=O)N[C@@H]3c2cc(F)ccc2Cl)cn1] | Cn1cc(cn1)-c1cc(NC(=O)c2cc(F)cc(c2)C(F)(F)F)c2[C@H](NC(=O)c2n1)c1cc(F)ccc1Cl | ¹H NMR (400 MHz, DMSO-d$_6$) δ 10.84 (br s, 1H), 9.44 (br s, 1H), 8.40 (s, 1H), 8.05 (s, 1H), 7.97 (br d, J = 6.6 Hz, 1H), 7.62-7.79 (m, 3H), 7.34 (br dd, J = 8.8, 5.1 Hz, 1H), 7.09 (td, J = 8.4, 2.9 Hz, 1H), 6.81-6.97 (m, 1H), 5.98 (br s, 1H), 3.93 (s, 3H). | 548.3 | C | |
| I-187 | 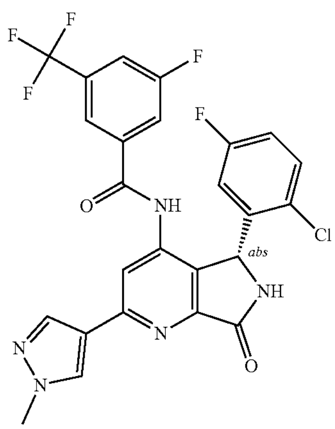 [SMILES: Cn1cc(-c2cc(NC(=O)c3cc(F)cc(C(F)(F)F)c3)c3c(n2)C(=O)N[C@H]3c2cc(F)ccc2Cl)cn1] | Cn1cc(cn1)-c1cc(NC(=O)c2cc(F)cc(c2)C(F)(F)F)c2[C@@H](NC(=O)c2n1)c1cc(F)cc1Cl | ¹H NMR (400 MHz, DMSO-d$_6$) δ 10.84 (br s, 1H), 9.44 (br s, 1H), 8.40 (s, 1H), 8.05 (s, 1H), 7.97 (br d, J = 6.6 Hz, 1H), 7.62-7.79 (m, 3H), 7.34 (br dd, J = 8.8, 5.1 Hz, 1H), 7.09 (td, J = 8.4, 2.9 Hz, 1H), 6.81-6.97 (m, 1H), 5.98 (br s, 1H), 3.93 (s, 3H). | 548.4 | A | |
| I-188 | 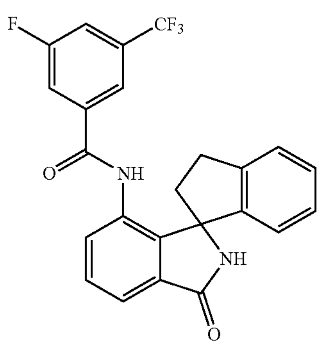 [SMILES: O=C(Nc1cccc2c1C1(CCc3ccccc31)NC2=O)c1cc(F)cc(C(F)(F)F)c1] | Fc1cc(cc(c1)C(F)(F)F)C(=O)Nc1ccc2C(=O)NC3(CCc4ccccc34)c12 | 1H NMR (500 MHz, DMSO-d6) 11.55 (s, 1H), 9.47 (s, 1H), 8.34 (d, 8.24 Hz, 1H), 8.12 (s, 1H), 8.06 (br dd, 6.71, 7.93 Hz, 2H), 7.57 (t, 7.93 Hz, 1H), 7.40 (d, 7.63 Hz, 1H), 7.26-7.33 (m, 1H), 7.15 (t, 7.32 Hz, 1H), 7.01 (d, 7.32 Hz, 1H), 6.79 (d, 7.32 Hz, 1H), 3.12-3.27 (m, 2H), 2.51-2.57 (m, 1H), 2.39-2.46 (m, 1H) | 441.07 | E | |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-189 | 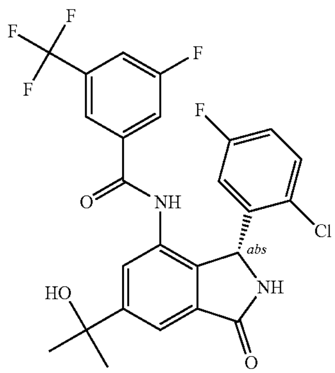 [SMILES: CC(C)(O)c1cc(NC(=O)c2cc(F)cc(C(F)(F)F)c2)c2c(c1)C(=O)N[C@H]2c1cc(F)ccc1Cl] | CC(C)(O)c1cc2C(=O)N[C@H](c2c(NC(=O)c2cc(F)cc(c2)C(F)(F)F)c1)c1cc(F)ccc1Cl | 1H NMR (400 MHz, DMSO-d6) 10.4-10.6 (m, 1H), 8.9-9.2 (m, 1H), 7.9-8.0 (m, 1H), 7.7-7.8 (m, 2H), 7.6-7.7 (m, 1H), 7.5-7.6 (m, 1H), 7.2-7.4 (m, 1H), 6.9-7.1 (m, 1H), 6.3-6.9 (m, 1H), 5.9-6.1 (m, 1H), 5.2-5.4 (m, 1H), 1.4-1.6 (m, 6H) | 525 | A | A |
| I-190 | 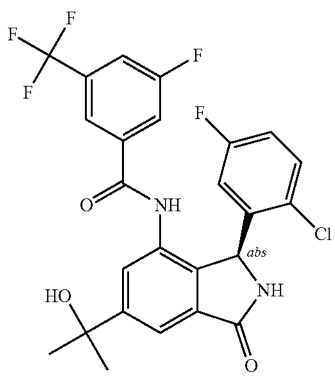 [SMILES: CC(C)(O)c1cc(NC(=O)c2cc(F)cc(C(F)(F)F)c2)c2c(c1)C(=O)N[C@@H]2c1cc(F)ccc1Cl] | CC(C)(O)c1cc2C(=O)N[C@@H](c2c(NC(=O)c2cc(F)cc(c2)C(F)(F)F)c1cc(F)ccc1Cl | 1H NMR (400 MHz, DMSO-d6) 10.4-10.6 (m, 1H), 8.9-9.2 (m, 1H), 7.9-8.0 (m, 1H), 7.7-7.8 (m, 2H), 7.6-7.7 (m, 1H), 7.5-7.6 (m, 1H), 7.2-7.4 (m, 1H), 6.9-7.1 (m, 1H), 6.3-6.9 (m, 1H), 5.9-6.1 (m, 1H), 5.2-5.4 (m, 1H), 1.4-1.6 (m, 6H) | 525 | D | |
| I-191 | 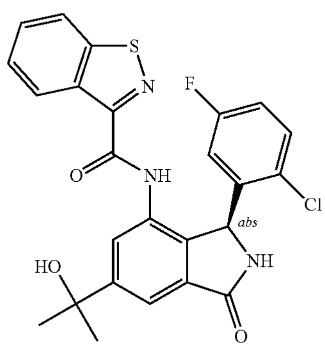 [SMILES: CC(C)(O)c1cc(NC(=O)c2nsc3ccccc23)c2c(c1)C(=O)N[C@@H]2c1cc(F)ccc1Cl] | CC(C)(O)c1cc2C(=O)N[C@@H](c2c(NC(=O)c2nsc3ccccc23)c1)c1cc(F)ccc1Cl | ¹H NMR (400 MHz, DMSO-d$_6$) δ 10.1-10.5 (m, 1H), 8.9-9.2 (m, 1H), 8.5-8.7 (m, 1H), 8.2-8.3 (m, 1H), 7.8-7.8 (m, 1H), 7.6-7.7 (m, 1H), 7.5-7.6 (m, 1H), 7.2-7.3 (m, 1H), 6.9-7.0 (m, 1H), 6.4-6.9 (m, 1H), 6.0-6.2 (m, 1H), 5.6-5.7 (m, 1H), 5.1-5.3 (m, 1H), 1.3-1.6 (m, 6H | 496 | C | |
| I-192 | 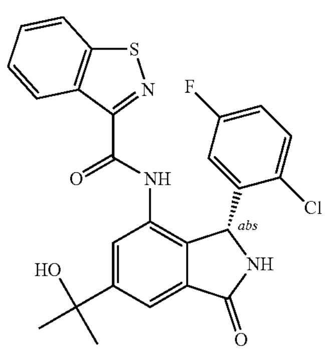 [SMILES: CC(C)(O)c1cc(NC(=O)c2nsc3ccccc23)c2c(c1)C(=O)N[C@H]2c1cc(F)ccc1Cl] | CC(C)(O)c1cc2C(=O)N[C@H](c2c(NC(=O)c2nsc3ccccc23)c1)c1cc(1F)ccc1Cl | 1H NMR (400 MHz, DMSO-d6) 10.1-10.5 (m, 1H), 8.9-9.2 (m, 1H), 8.5-8.7 (m, 1H), 8.2-8.3 (m, 1H), 7.8-7.8 (m, 1H), 7.6-7.7 (m, 1H), 7.5-7.6 (m, 1H), 7.2-7.3 (m, 1H), 6.9-7.0 (m, 1H), 6.4-6.9 (m, 1H), 6.0-6.2 (m, 1H), 5.6-5.7 (m, 1H), 5.1-5.3 (m, 1H), 1.3-1.6 (m, 6H) | 496 | A | A |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-193 | 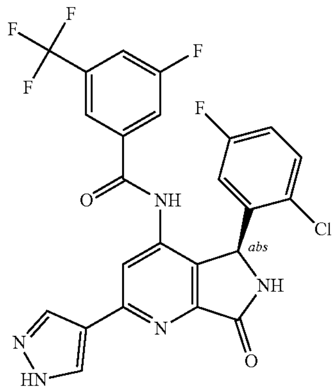 [SMILES: O=C(Nc1cc(-c2cn[nH]c2)nc2c1[C@@H](c1cc(F)ccc1Cl)NC2=O)c1cc(F)cc(C(F)(F)F)c1] | Fc1ccc(C1)c(c1)[C@H]1NC(=O)c2nc(cc(NC(=O)c3cc(F)cc(c3)C(F)(F)F)c12)-c1cn[nH]c1 | ¹H NMR (400 MHz, DMSO-d$_6$) δ 13.21 (br s, 1H), 10.85 (br s, 1H), 9.44 (br s, 1H), 8.43 (br s, 1H), 8.12 (br s, 1H), 7.97 (br d, J = 4.1 Hz, 1H), 7.63-7.87 (m, 3H), 7.34 (br dd, J = 8.8, 5.1 Hz, 1H), 7.09 (td, J = 8.4, 2.9 Hz, 1H), 6.75-6.96 (m, 1H), 5.98 (br s, 1H). | 534.4 | D | |
| I-194 | 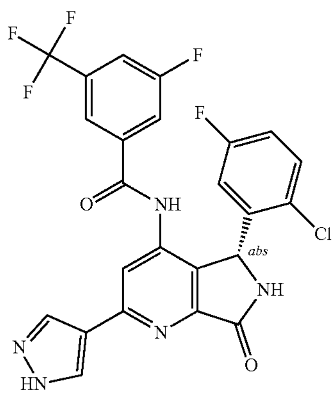 [SMILES: O=C(Nc1cc(-c2cn[nH]c2)nc2c1[C@H](c1cc(F)ccc1Cl)NC2=O)c1cc(F)cc(C(F)(F)F)c1] | Fc1ccc(C1)c(c1)[C@@H]1NC(=O)c2nc(cc(NC(=O)c3cc(F)cc(c3)C(F)(F)F)c12)-c1cn[nH]c1 | ¹H NMR (400 MHz, DMSO-d$_6$) δ 13.21 (br s, 1H), 10.85 (br s, 1H), 9.44 (br s, 1H), 8.43 (br s, 1H), 8.12 (br s, 1H), 7.97 (br d, J = 4.1 Hz, 1H), 7.63-7.87 (m, 3H), 7.34 (br dd, J = 8.8, 5.1 Hz, 1H), 7.09 (td, J = 8.4, 2.9 Hz, 1H), 6.75-6.96 (m, 1H), 5.98 (br s, 1H). | 534.4 | A | |
| I-195 | 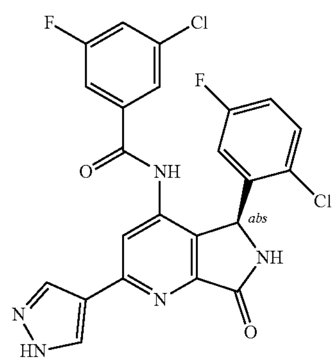 [SMILES: O=C(Nc1cc(-c2cn[nH]c2)nc2c1[C@@H](c1cc(F)ccc1Cl)NC2=O)c1cc(F)cc(Cl)c1] | Fc1ccc(C1)c(c1)[C@H]1NC(=O)c2nc(cc(NC(=O)c3cc(F)cc(C1)c3)c12)-c1cn[nH]c1 | ¹H NMR (400 MHz, DMSO-d$_6$) δ 13.20 (br s, 1H), 10.69 (br s, 1H), 9.44 (br s, 1H), 8.42 (br s, 1H), 8.11 (br s, 1H), 7.88 (br s, 1H), 7.57-7.83 (m, 3H), 7.36-7.43 (m, 2H), 7.14 (td, J = 8.4, 3.1 Hz, 1H), 5.99 (br s, 1H). | 500.4 | D | |
| I-196 | 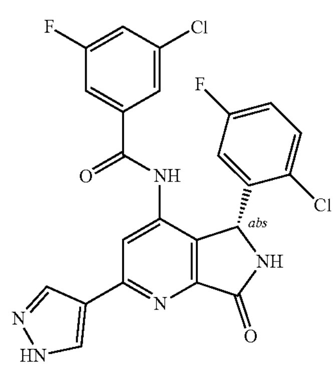 [SMILES: O=C(Nc1cc(-c2cn[nH]c2)nc2c1[C@H](c1cc(F)ccc1Cl)NC2=O)c1cc(F)cc(Cl)c1] | Fc1ccc(C1)c(c1)[C@@H]1NC(=O)c2nc(cc(NC(=O)c3cc(F)cc(C1)c3)c12)-c1cn[nH]c1 | ¹H NMR (400 MHz, DMSO-d$_6$) δ 13.20 (br s, 1H), 10.69 (br s, 1H), 9.44 (br s, 1H), 8.42 (br s, 1H), 8.11 (br s, 1H), 7.88 (br s, 1H), 7.57-7.83 (m, 3H), 7.36-7.43 (m, 2H), 7.14 (td, J = 8.4, 3.1 Hz, 1H), 5.99 (br s, 1H). | 500.4 | A | |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-197 | 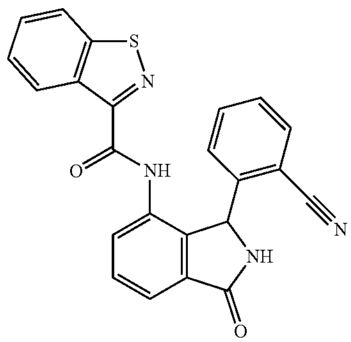 [SMILES: N#Cc1ccccc1C1NC(=O)c2cccc(NC(=O)c3nsc4ccccc34)c21] | O=C(Nc1cccc2C(=O)NC(c12)c1cccc c1C#N)c1nsc2ccc cc12 | 1H NMR (400 MHz, DMSO-d6) 10.46 (s, 1H), 9.21 (s, 1H), 8.65 (dt, 8.1, 0.9 Hz, 1H), 8.31 (dt, 8.2, 0.9 Hz, 1H), 7.72-7.62 (m, 4H), 7.62-7.56 (m, 2H), 7.35 (td, 7.6, 1.2 Hz, 1H), 7.27 (td, 7.6, 1.3 Hz, 1H), 7.23-7.12 (br s), 6.15 (s). | 411.2 | D | |
| I-198 | 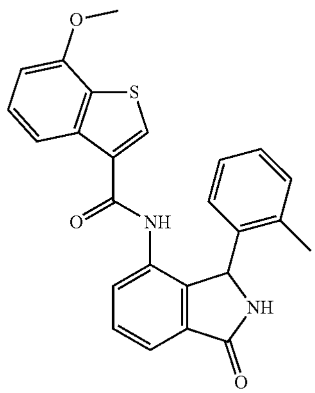 [SMILES: COc1cccc2c(C(=O)Nc3cccc4c3C(c3ccccc3C)NC4=O)csc12] | COc1cccc2c(csc1 2)C(=O)Nc1cccc2 C(=O)NC(c12)c1 ccccc1C | 1H NMR (400 MHz, DMSO-d6) 10.10 (s, 1H), 9.03 (s, 1H), 7.70-7.52 (m, 5H), 7.35 (t, 8.0 Hz, 1H), 7.09 (td, 7.4, 1.0, 1H), 7.01-6.95 (m, 3H), 6.55 (br s, 1H), 6.00 (s, 1H), 3.96 (s, 3H), 2.12 (br s, 3H). | 429.3 | E | |
| I-199 | 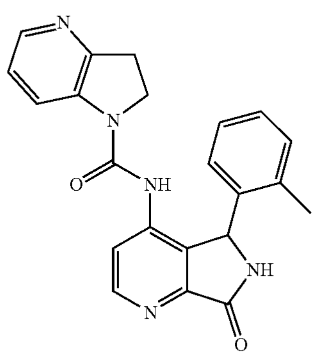 [SMILES: Cc1ccccc1C1NC(=O)c2nccc(NC(=O)N3CCc4ncccc43)c21] | Cc1ccccc1C1NC(=O)c2nccc(NC(=O)N3CCc4ncccc34)c12 | 1H NMR (400 MHz, DMSO-d6) 9.35 (s, 1H), 9.00 (br s, 1H), 8.66 (d, 5.3 Hz, 1H), 8.04 (dd, 4.9, 1.4 Hz, 1H), 7.85 (d, 7.8 Hz, 1H), 7.39 (d, 5.3 Hz, 1H), 7.22-7.07 (m, 2H), 6.98 (d, 7.5 Hz, 2H), 6.54 (br s, 1H), 5.87 (s, 1H), 3.71-3.60 (m, 1H), 3.10-2.81 (m, 3H), 2.29-1.94 (m, 3H). | 386.3 | E | |
| I-200 | 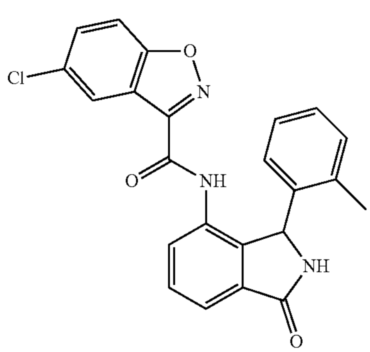 [SMILES: Cc1ccccc1C1NC(=O)c2cccc(NC(=O)c3noc4ccc(Cl)cc34)c21] | Cc1ccccc1C1NC(=O)c2cccc(NC(=O)c3noc4ccc(Cl)cc34)c12 | 1H NMR (400 MHz, DMSO-d6) 10.72 (br s, 1H), 9.07 (s, 1H), 7.94 (dd, 9.0, 0.4 Hz, 1H), 7.79 (dd, 9.0, 2.1 Hz, 1H), 7.73 (br s, 1H), 7.71 (dd, 7.2, 1.3 Hz, 1H), 7.63 (t, 7.5 Hz, 1H), 7.59 (dd, 7.8, 1.2 Hz, 1H), 7.02-6.93 (m, 2H), 6.93-6.85 (m, 1H), 6.64 (br s, 1H), 6.02 (s, 1H), 2.20 (br s, 3H) | 835.3 | D | |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-201 | 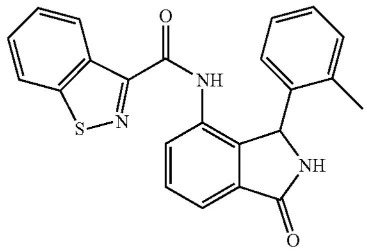 [SMILES: Cc1ccccc1C1NC(=O)c2cccc(NC(=O)c3nsc4ccccc34)c21] | Cc1ccccc1C1NCc2cccc(NC(=O)c3nsc4cccc34)c12 | 1H NMR (400 MHz, DMSO-d6) 8.85-8.80 (m, 1H), 8.77 (s, 1H), 8.10 (dt, 8.2, 0.8 Hz, 1H), 7.90 (d, 8.2 Hz, 1H), 7.62 (ddd, 8.2, 7.0, 1.2 Hz, 1H), 7.56 (ddd, 8.2, 7.0, 1.2 Hz, 1H), 7.40 (t, 7.5 Hz, 1H), 7.23 (dd, 7.5, 0.8 Hz, 1H), 7.14-7.02 (m, 3 H), 6.96 (dd, 7.5, 1.2 Hz, 1H), 5.91 (s, 1H), 4.42 (d, 14.0 Hz, 1H), 4.32 (d, 14.0 Hz, 1H), 2.42 (s, 3H).. | 386.2 | D | |
| I-202 | 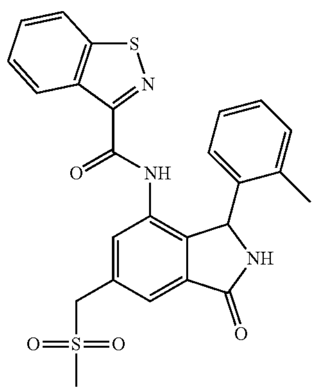 [SMILES: Cc1ccccc1C1NC(=O)c2cc(CS(C)(=O)=O)cc(NC(=O)c3nsc4ccccc34)c21] | Cc1ccccc1C1NC(=O)c2cc(CS(C)(=O)=O)cc(NC(=O)c3nsc4cccc34)c12 | 1H NMR (400 MHz, CDCl3) 8.90 (d, 7.7 Hz, 1H), 8.87 (s, 1H), 8.59 (s, 1H), 7.94 (d, 7.8 Hz, 1H), 7.79 (d, 1.2 Hz, 1H), 7.72-7.62 (m, 1H), 7.60-7.50 (m, 3H), 7.46 (td, 7.4, 3.0 Hz, 1H), 7.17 (br s, 1H), 6.65 (s, 1H), 6.00 (br s, 1H), 4.41 (s, 2H), 2.89 (s, 3H), 2.16 (s, 1H), 1.24 (br s, 3H). | 492.3 | A | A |
| I-203 | 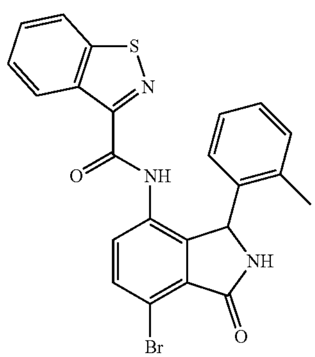 [SMILES: Cc1ccccc1C1NC(=O)c2c(Br)ccc(NC(=O)c3nsc4ccccc34)c21] | Cc1ccccc1C1NC(=O)c2c1c(NC(=O)c1nsc3cccc13)ccc2Br | 1H NMR (400 MHz, DMSO-d6) 10.10 (s, 1H), 9.22 (s, 1H), 8.58 (d, 8.2 Hz, 1H), 8.30 (d, 8.2 Hz, 1H), 7.76 (dd, 21.4, 8.4 Hz, 2H), 7.70-7.64 (m, 1H), 7.61-7.54 (m, 1 H), 7.01-6.94 (m, 2H), 6.91 (m, 1 H), 6.69 (br s, 1H), 6.08 (s, 1H), 2.24 (br s, 3H). | 480.1 | A | |
| I-204 | 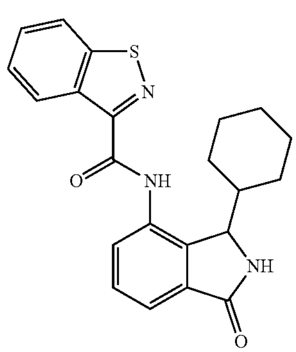 [SMILES: O=C1NC(C2CCCCC2)c2c(NC(=O)c3nsc4ccccc34)cccc21] | O=C(Nc1cccc2C(=O)NC(C3CCCCC3)c12)c1nsc2ccccc12 | 1H NMR (400 MHz, DMSO-d6) 10.90 (s, 1H), 8.72 (s, 1H), 8.70 (d, 8.3 Hz, 1H), 8.37 (d, 8.2 Hz, 1H), 7.75-7.69 (m, 2H), 7.64 (t, 7.6 Hz, 1H), 7.57-7.50 (m, 2H), 4.89 (s, 1H), 2.09-1.97 (m, 1H), 1.62 (m, 2H), 1.48 (d, 8.6 Hz, 2H), 1.34 (qd, 12.2, 9.4 Hz, 1H), 0.91 (t, 8.6 Hz, 2H), 0.87 (m, 1H), 0.71 (t, 8.7 Hz, 2H). | 392.2 | B | |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-205 | 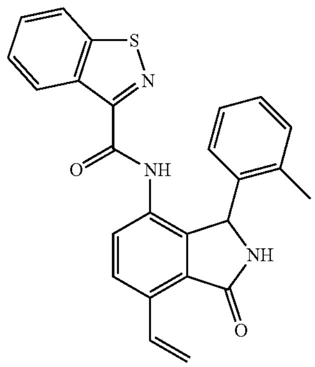 [SMILES: C=Cc1ccc(NC(=O)c2nsc3ccccc23)c2c1C(=O)NC2c1ccccc1C] | Cc1ccccc1C1NC(=O)c2c1c(NC(=O)c1nsc3ccccc13)ccc2C=C | 1H NMR (400 MHz, DMSO-d6) 10.03 (br s, 1H), 9.06 (s, 1H), 8.59 (d, 8.1 Hz, 1H), 8.29 (d, 8.2 Hz, 1H), 8.11 (dd, 17.9, 11.2 Hz, 1H), 7.90 (d, 8.4 Hz, 1H), 7.79 (d, 8.3 Hz, 1H), 7.67 (t, 7.2 Hz, 1H), 7.58 (t, 7.4 Hz, 1 H), 7.06-6.94 (m, 2H), 6.93-6.90 (m, 1H), 6.71 (br s, 1H), 6.14-5.98 (m, 2H), 5.45 (d, 11.9 Hz, 1H), 2.25 (br s, 3H). | 426.3 | B | |
| I-206 | 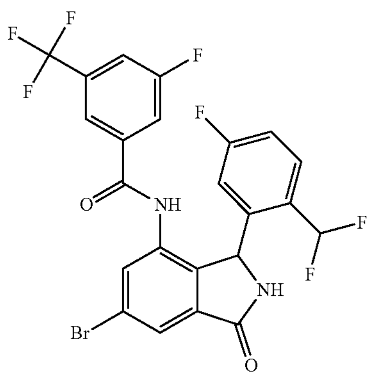 [SMILES: O=C(Nc1cc(Br)cc2c1C(c1cc(F)ccc1C(F)F)NC2=O)c1cc(F)cc(C(F)(F)F)c1] | FC(F)c1ccc(F)cc1C1NC(=O)c2cc(Br)cc(NC(=O)c3cc(F)cc(c3)C(F)(F)F)c12 | 1H NMR (400 MHz, DMSO-d6) 10.55 (s, 1H), 9.33 (s, 1H), 7.94 (d, 8.2 Hz, 1H), 7.87 (d, 1.7 Hz, 1H), 7.78 (d, 1.7 Hz, 1H), 7.67 (d, 8.9 Hz, 1H), 7.58 (s, 1H), 7.50 (dd, 8.8, 5.6 Hz, 1H), 7.22 (td, 8.4, 2.7 Hz, 1H), 7.11 (s, 1H), 6.57 (s, 1H), 6.02 (s, 1H). | 561.05 | A | |
| I-207 | 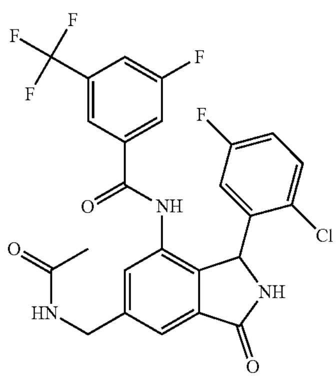 [SMILES: CC(=O)NCc1cc(NC(=O)c2cc(F)cc(C(F)(F)F)c2)c2c(c1)C(=O)NC2c1cc(F)ccc1Cl] | CC(=O)NCc1cc2C(=O)NC(c2c(NC(=O)c2cc(F)cc(c2)C(F)F)c1cc(F)ccc1C1 | 1H NMR (400 MHz, DMSO-d6) 10.3-10.7 (m, 1H), 8.8-9.3 (m, 1H), 7.9-8.0 (m, 1H), 7.7-7.8 (m, 1H), 7.6-7.7 (m, 2H), 7.4-7.5 (m, 2H), 7.3-7.3 (m, 1H), 7.0-7.1 (m, 1H), 5.8-6.1 (m, 1H), 5.2-5.6 (m. 1H), 4.4-4.8 (m, 2H), 2.0-2.1 (m, 3H) | 538 | B | |
| I-208 | 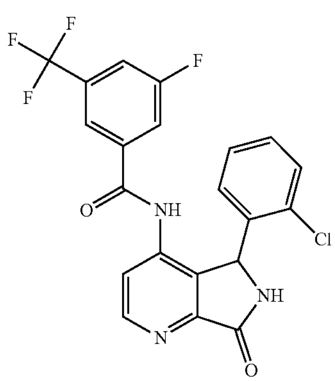 [SMILES: O=C(Nc1ccnc2c1C(c1ccccc1Cl)NC2=O)c1cc(F)cc(C(F)(F)F)c1] | Fc1cc(cc(c1)C(F)(F)F)C(=O)Nc1ccnc2C(=O)NC(c12)c1ccccc1C1 | 1H NMR (400 MHz, DMSO-d6) 10.75 (br s, 1H), 9.48 (br s, 1H), 8.78 (d, 5.13 Hz, 1H), 7.94 (br d, 8.54 Hz, 1H), 7.63 (br d, 8.79 Hz, 1H), 7.48-7.57 (m, 2H), 7.26-7.33 (m, 1H), 7.18-7.25 (m, 1H), 7.11 (br t, 7.20 Hz, 1H), 6.70-6.99 (m, 1H), 6.06 (br s, 1H) | 450.36 | C | |

TABLE 2-continued

Representative Compounds of the Invention with Bioactivity Data.

| Ex. No. | Structure | SMILES | $^1$H NMR | MS | ADP-Glo IC$_{50}$ | MCF 10A IC$_{50}$ |
|---|---|---|---|---|---|---|
| I-209 | 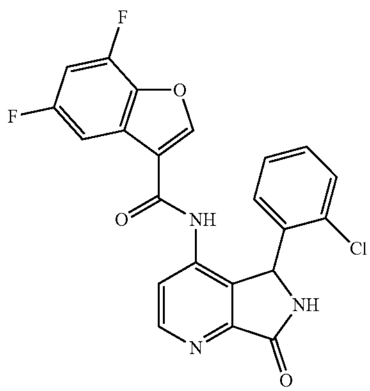 [SMILES: O=C1NC(c2ccccc2Cl)c2c(NC(=O)c3coc4c(F)cc(F)cc34)ccnc21] | Fc1cc(F)c2occ(C(=O)Nc3cnc4C(=O)NC(c34)c3ccccc3Cl)c2c1 | 1H NMR (400 MHz, DMSO-d6) 10.55 (s, 1H), 9.46 (br s, 1H), 8.72-8.85 (m, 1H), 8.45 (s, 1H), 7.38-7.56 (m, 4H), 7.22-7.29 (m, 1H), 7.15-7.21 (m, 1H), 7.09 (br t, 7.20 Hz, 1H), 6.15 (br s, 1H) | 440.35 | C | |
| I-210 | 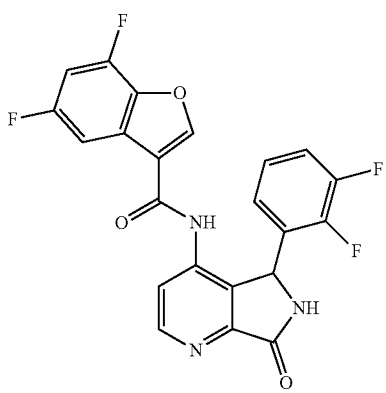 [SMILES: O=C1NC(c2cccc(F)c2F)c2c(NC(=O)c3coc4c(F)cc(F)cc34)ccnc21] | Fc1cc(F)c2occ(C(=O)Nc3cnc4C(=O)NC(c34)c3cccc(F)c3F)c2c1 | 1H NMR (400 MHz, DMSO-d6) 10.62 (br s, 1H), 9.49 (s, 1H), 8.77 (d, 5.37 Hz, 1H), 8.53 (s, 1H), 7.54 (d, 5.37 Hz, 1H), 7.39-7.50 (m, 2H), 7.19-7.30 (m, 1H), 6.93-7.01 (m, 1H), 6.82 (br t, 6.96 Hz, 1H), 6.06 (s, 1H) | 442.4 | D | |
| I-211 | 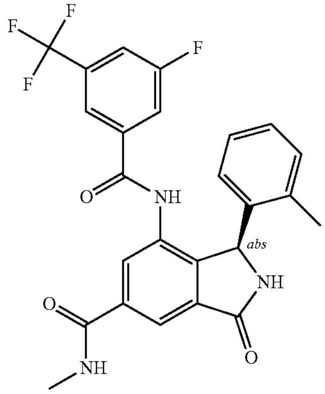 [SMILES: CNC(=O)c1cc(NC(=O)c2cc(F)cc(C(F)(F)F)c2)c2c(c1)C(=O)N[C@@H]2c1ccccc1C] | CNC(=O)c1cc2C(=O)N[C@@H](c2c(NC(=O)c2cc(F)cc(c2)C(F)(F)F)c1)c1ccccc1C | | 486.37 | E | |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-212 | 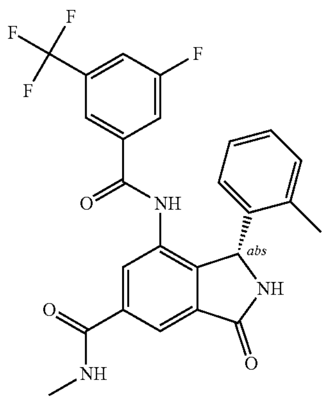 [SMILES: CNC(=O)c1cc(NC(=O)c2cc(F)cc(C(F)(F)F)c2)c2c(c1)C(=O)N[C@H]2c1ccccc1C] | CNC(=O)c1cc2C(=O)N[C@H](c2c(NC(=O)c2cc(F)cc(c2)C(F)(F)F)c1)c1ccccc1C | | 486.37 | A | |
| I-213 | 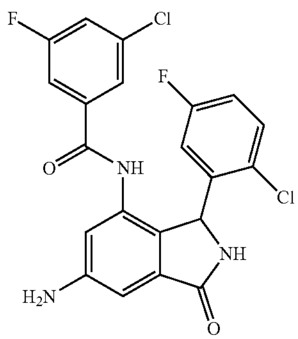 [SMILES: Nc1cc(NC(=O)c2cc(F)cc(Cl)c2)c2c(c1)C(=O)NC2c1cc(F)ccc1Cl] | Nc1cc2C(=O)NC(c2c(NC(=O)c2cc(F)cc(C1)c2)c1)c1cc(F)ccc1Cl | 1H NMR (400 MHz, DMSO-d6) 5.43-5.68 (m, 2H), 5.74-5.91 (m, 1H), 6.37-6.60 (m, 1H), 6.63-6.72 (m, 1H), 6.76-6.87 (m, 1H), 6.93-7.17 (m, 1H), 7.21-7.44 (m, 3H), 7.51-7.79 (m, 1H), 8.70-8.97 (m, 1H), 9.84-10.17 (m, 1H) | 448 | A | A |
| I-214 | 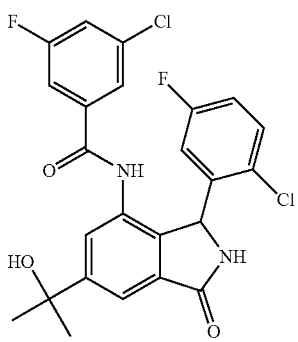 [SMILES: CC(C)(O)c1cc(NC(=O)c2cc(F)cc(Cl)c2)c2c(c1)C(=O)NC2c1cc(F)ccc1Cl] | CC(C)(O)c1cc2C(=O)NC(c2c(NC(=O)c2cc(F)cc(C1)c2)c1)c1cc(F)ccc1Cl | 1H NMR (400 MHz, DMSO-d6) 10.2-10.4 (m, 1H), 9.0-9.2 (m, 1H), 7.7-7.8 (m, 1H), 7.66 (br d, 8.3 Hz, 2H), 7.5-7.6 (m, 1H), 7.3-7.5 (m, 2H), 7.0-7.2 (m, 1H), 6.6-6.7 (m, 1H), 5.8-6.1 (m, 1H), 5.2-5.4 (m, 1H), 1.4-1.6 (m, 6H) | 491 | A | |
| I-215 | 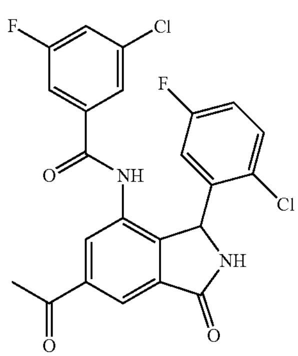 [SMILES: CC(=O)c1cc(NC(=O)c2cc(F)cc(Cl)c2)c2c(c1)C(=O)NC2c1cc(F)ccc1Cl] | CC(=O)c1cc2C(=O)NC(c2c(NC(=O)c2cc(F)cc(C1)c2)c1)c1cc(F)ccc1Cl | 1H NMR (400 MHz, DMSO-d6) 10.3-10.7 (m, 1H), 9.1-9.4 (m, 1H), 8.4-8.6 (m, 1H), 8.0-8.3 (m, 1H), 7.6-7.8 (m, 1H), 7.3-7.5 (m, 3H), 7.0-7.2 (m, 1H), 6.5-6.9 (m, 1H), 5.8-6.2 (m, 1H), 3.8-4.3 (m, 3H) | 475 | B | |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-216 | 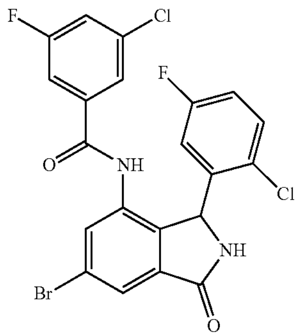 [SMILES: O=C(Nc1cc(Br)cc2c1C(c1cc(F)ccc1Cl)NC2=O)c1cc(F)cc(Cl)c1] | Fc1ccc(C1)c(c1)C1NC(=O)c2cc(Br)cc(NC(=O)c3cc(F)cc(C1)c3)c12 | 1H NMR (400 MHz, DMSO-d6) 10.2-10.7 (m, 1H), 9.1-9.5 (m, 1H), 8.3-8.5 (m, 1H), 7.6-8.0 (m, 2H), 7.3-7.4 (m, 2H), 7.0-7.2 (m, 1H), 6.5-6.8 (m, 1H), 5.5-6.3 (m, 2H) | 513 | A | |
| I-217 | 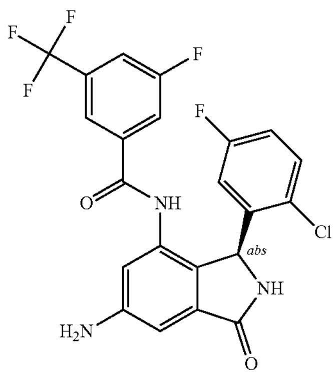 [SMILES: Nc1cc(NC(=O)c2cc(F)cc(C(F)(F)F)c2)c2c(c1)C(=O)N[C@@H]2c1cc(F)ccc1Cl] | Nc1cc2C(=O)N[C@@H](c2c(NC(=O)c2cc(F)cc(c2)C(F)(F)F)c1)c1cc(F)ccc1C1 | 1H NMR (500 MHz, DMSO-d6) 10.1-10.3 (m, 1H), 8.8-8.9 (m, 1H), 7.9-8.0 (m, 1H), 7.6-7.8 (m, 1H), 7.6-7.6 (m, 1H), 7.2-7.4 (m, 2H), 7.0-7.1 (m, 1H), 6.8-6.9 (m, 1H), 6.66 (s, 1H), 5.7-5.9 (m, 1H), 5.5-5.7 (m, 2H) | 482 | D | |
| I-218 | 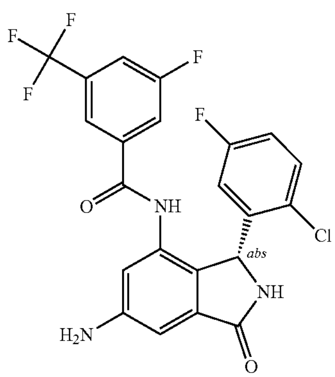 [SMILES: Nc1cc(NC(=O)c2cc(F)cc(C(F)(F)F)c2)c2c(c1)C(=O)N[C@H]2c1cc(F)ccc1Cl] | Nc1cc2C(=O)N[C@H](c2c(NC(=O)c2cc(F)cc(c2)C(F)(F)F)c1)c1cc(F)ccc1C1 | 1H NMR (500 MHz, DMSO-d6) 10.1-10.3 (m, 1H), 8.8-8.9 (m, 1H), 7.9-8.0 (m, 1H), 7.6-7.8 (m, 1H), 7.6-7.6 (m, 1H), 7.2-7.4 (m, 2H), 7.0-7.1 (m, 1H), 6.8-6.9 (m, 1H), 6.66 (s, 1H), 5.7-5.9 (m, 1H), 5.5-5.7 (m, 2H) | 482 | A | A |
| I-219 | 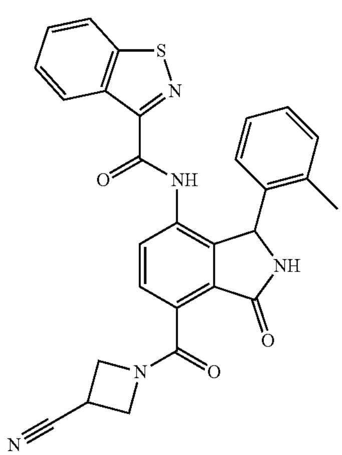 [SMILES: Cc1ccccc1C1NC(=O)c2c(C(=O)N3CC(C#N)C3)ccc(NC(=O)c3nsc4ccccc34)c21] | Cc1ccccc1C1NC(=O)c2c1c(NC(=O)c1nsc3ccccc13)ccc2C(=O)N1CC(C1)C#N | 1H NMR (400 MHz, DMSO-d6) 10.20 (br s, 1H), 9.25 (s, 1H), 8.59 (d, 8.3 Hz, 1H), 8.30 (d, 8.2 Hz, 1H), 7.88 (dd, 8.1, 2.2 Hz, 1H), 7.71-7.64 (m, 1H), 7.59 (t, 7.5 Hz, 1H), 7.53 (d, 8.1 Hz, 1H), 7.03-6.95 (m, 2H), 6.92 (s, 1H), 6.68 (br s, 1H), 6.15 (s, 1H), 4.37 (t, 9.4 Hz, 1H), 4.23 (dd, 9.6, 6.2 Hz, 1H), 4.20-4.07 (m, 2H), 3.91-3.81 (m, 1H), 2.27 (br s, 3H) | 508.2 | C | |

TABLE 2-continued

Representative Compounds of the Invention with Bioactivity Data.

| Ex. No. | Structure | SMILES | $^1$H NMR | MS | ADP-Glo IC$_{50}$ | MCF 10A IC$_{50}$ |
|---|---|---|---|---|---|---|
| I-220 | 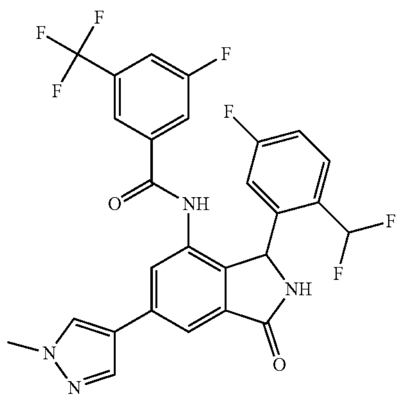 [SMILES: Cn1cc(-c2cc(NC(=O)c3cc(F)cc(C(F)(F)F)c3)c3c(c2)C(=O)NC3c2cc(F)ccc2C(F)F)cn1] | Cn1cc(cn1)-c1cc2C(=O)NC(c2c(NC(=O)c2cc(F)cc(c2)C(F)(F)F)c1)cc(F)ccc1C(F)F | 1H NMR (400 MHz, DMSO-d6) δ 10.53 (br s, 1H) 9.14 (s, 1H) 8.33 (s, 1H) 8.00 (s, 1H) 7.85-7.94 (m, 2H) 7.65-7.74 (m, 2H) 7.62 (s, 1H) 7.47 (dd, J = 8.72, 5.68 Hz, 1H) 7.19 (td, J = 8.46, 2.53 Hz, 1H) 6.46-6.61 (m, 1H) 5.98 (s, 1H) 3.74-4.02 (m, 1H) 3.88 (s, 2H) | 563.1 | A | A |
| I-221 | 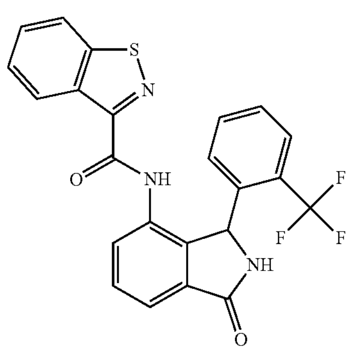 [SMILES: O=C1NC(c2ccccc2C(F)(F)F)c2c(NC(=O)c3nsc4ccccc34)cccc21] | FC(F)(F)c1ccccc1C1NC(=O)c2cccc(NC(=O)c3nsc4ccccc34)c12 | 1H NMR (400 MHz, DMSO-d6) 11.10 (s, 1H), 9.24 (s, 1H), 8.77 (d, 8.1 Hz, 1H), 8.39 (t, 4.4 Hz, 1H), 8.36 (d, 8.2 Hz, 1H), 7.99 (dt, 15.6, 7.8 Hz, 1H), 7.83 (d, 7.9 Hz, 1H), 7.76-7.68 (m, 1H), 7.67-7.63 (m, 1H), 7.61 (dd, 11.0, 4.2 Hz, 1H), 7.53 (t, 7.4 Hz, 1H), 7.18 (d, 8.2 Hz, 1H), 7.09 (d, 7.7 Hz, 1H), 5.91 (s, 1H). | 454.2 | E | |
| I-222 | 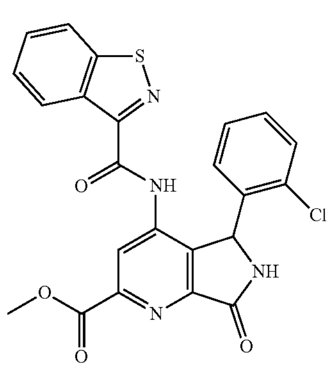 [SMILES: COC(=O)c1cc(NC(=O)c2nsc3ccccc23)c2c(n1)C(=O)NC2c1ccccc1Cl] | COC(=O)c1cc(NC(=O)c2nsc3ccccc23)c2C(NC(=O)c2n1)c1cccc1Cl | 1H NMR (400 MHz, DMSO-d6) 10.61 (br s, 1H), 9.70 (br s, 1H), 8.70 (d, 7.9 Hz, 1H), 8.60 (s, 1H), 8.33 (d, 8.2 Hz, 1H), 7.70 (ddd, 8.3, 7.0, 1.2 Hz, 1H), 7.67-7.52 (m, 1H), 7.33 (d, 7.7 Hz, 1H), 7.23 (td, 7.9, 1.6 Hz, 1H), 7.15 (td, 7.4, 1.1 Hz, 1H), 6.40 (br s, 1H), 3.97 (s, 3H). | 479.2 | B | |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-223 | 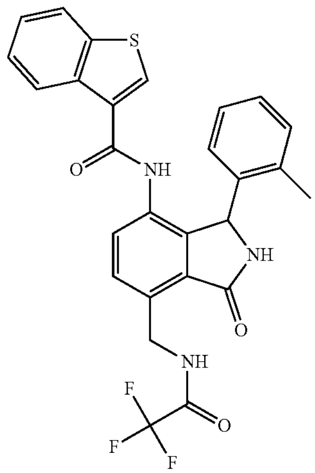 [SMILES: Cc1ccccc1C1NC(=O)c2c(CNC(=O)C(F)(F)F)ccc(NC(=O)c3csc4ccccc34)c21] | Cc1ccccc 1C1NC(= O)c2c1c (NC(=O)c 1csc3ccc cc13)ccc 2CNC(= O)C(F)(F) F | 1H NMR (400 MHz, DMSO-d6) 10.11-10.04 (m, 2H), 9.17 (s, 1H), 8.05-7.97 (m, 2H), 7.62 (s, 1H), 7.55 (d, 8.1 Hz, 1H), 7.42-7.37 (m, 3 H), 7.10 (td, 7.6, 1.1 Hz, 1H), 7.05-6.95 (m, 2H), 6.62 (br s, 1H), 6.02 (s, 1H), 5.02 (d, 5.8 Hz, 2H), 2.20 (br s, 3H). | 524.2 | B | |
| I-224 | 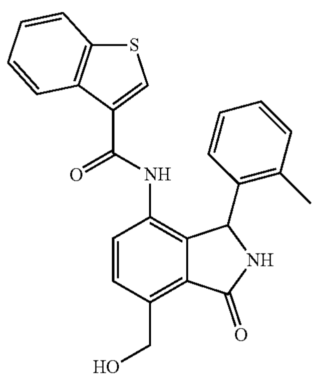 [SMILES: Cc1ccccc1C1NC(=O)c2c(CO)ccc(NC(=O)c3csc4ccccc34)c21] | Cc1ccccc 1C1NC(= O)c2c1c (NC(=O)c 1csc3ccc cc13)ccc 2CO | 1H NMR (400 MHz, DMSO-d6) 10.07 (s, 1H), 9.11 (s, 1H), 8.08-7.99 (m, 2H), 7.63 (d, 8.0 Hz, 2H), 7.53 (d, 8.1 Hz, 1H), 7.43-7.35 (m, 2H), 7.09 (t, 7.4 Hz, 1H), 7.03-6.94 (m, 2H), 6.62 (br s, 1H), 6.02 (s, 1H), 5.04 (s, 2H), 2.19 (br s, 3H). | 429.3 | A | |
| I-225 | 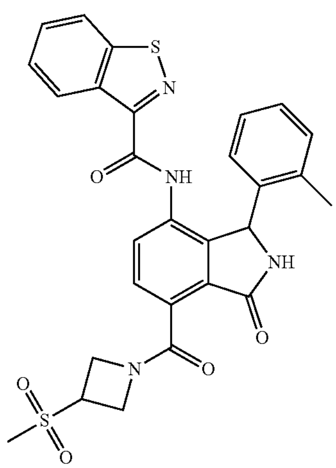 | Cc1ccccc 1C1NC(= O)c2c1c (NC(=O)c 1nsc3ccc cc13)ccc 2C(=O)N 1CC(C1) S(C)(=O)=O | 1H NMR (400 MHz, DMSO-d6) 10.22 (br s, 1H), 9.26 (d, 5.2 Hz, 1H), 8.59 (d, 8.1 Hz, 1H), 8.30 (d, 8.2 Hz, 1H), 7.89 (t, 8.1 Hz, 1H), 7.71-7.64 (m, 1H), 7.59 (t, 7.6 Hz, 1H), 7.52 (dd, 8.1, 4.1 Hz, 1H), 7.06-6.95 (m, 2H), 6.92 (br s, 1H), 6.67 (br s, 1H), 6.15 (s, 1H), 4.43-4.32 (m, 2H), 4.23-4.19 (m, 2H), 4.06 (ddd, 13.1, 9.2, 3.5 Hz, 1H), 3.08 (d, 6.8 Hz, 3H), 2.27 (br s, 3H). | 561.3 | B | |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-226 | 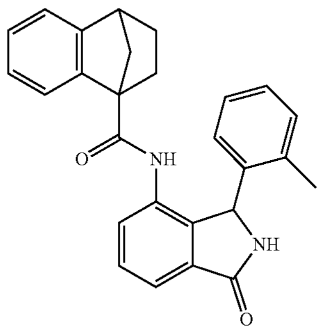 [SMILES: Cc1ccccc1C1NC(=O)c2cccc(NC(=O)C34CCC(C3)c3ccccc34)c21] | Cc1ccccc1C1NC(=O)c2cccc(NC(=O)C34CCC(C3)c3ccccc43)c12 | 1H NMR (400 MHz, DMSO-d6) 9.02 (br s, 1H), 8.99 (br s, 1H), 8.80 (br s, 2H), 7.67-7.53 (m, 6H), 7.23-7.10 (m, 6H), 7.09-6.91 (m, 6H), 6.85 (d, 7.2 Hz, 1H), 6.66-6.58 (m, 3H), 6.07 (s, 2H), 3.31 (dd, 11.4, 3.4 Hz, 2H), 2.29 (br. s, 6H), 1.93-1.84 (m, 2H), 1.81-1.76 (m, 1H), 1.76-1.64 (m, 3H), 1.44 (d, 8.7 Hz, 1H), 1.36 (d, 8.7 Hz, 1H), 1.22-1.14 (m, 1H), 1.14-1.08 (m, 1H), 1.08-0.99 (m, 2H). Spectrum recorded at 70° C. (343K). | 409.4 | D | |
| I-227 | 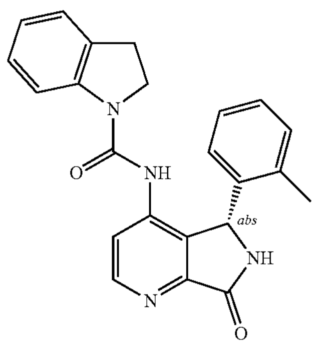 [SMILES: Cc1ccccc1[C@@H]1NC(=O)c2nccc(NC(=O)N3CCc4ccccc43)c21] | Cc1ccccc1[C@@H]1NC(=O)c2nccc(NC(=O)N3CCc4ccccc34)c12 | 1H NMR (400 MHz, DMSO-d6) 9.34 (s, 1H), 8.83 (br s, 1H), 8.64 (d, 5.3 Hz, 1H), 7.64 (d, 7.8 Hz, 1H), 7.42 (d, 5.4 Hz, 1H), 7.18-7.07 (m, 3H), 7.04-6.95 (m, 2H), 6.92 (t, 7.1 Hz, 1H), 6.55 (br s, 1H), 5.90 (s, 1H), 3.62-3.52 (m, 1H), 3.01-2.78 (m, 3H), 2.11 (br s, 3H) | 385.2 | B | |
| I-228 | 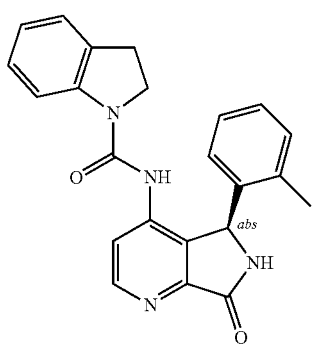 [SMILES: Cc1ccccc1[C@H]1NC(=O)c2nccc(NC(=O)N3CCc4ccccc43)c21] | Cc1ccccc1[C@H]1NC(=O)c2nccc(NC(=O)N3CCc4ccccc34)c12 | 1H NMR (400 MHz, DMSO-d6) 9.34 (s, 1H), 8.83 (br s, 1H), 8.64 (d, 5.3 Hz, 1H), 7.64 (d, 7.8 Hz, 1H), 7.42 (d, 5.4 Hz, 1H), 7.18-7.07 (m, 3H), 7.04-6.95 (m, 2H), 6.92 (t, 7.1 Hz, 1H), 6.55 (br s, 1H), 5.90 (s, 1H), 3.62-3.52 (m, 1H), 3.01-2.78 (m, 3H), 2.11 (br s, 3H) | 385.4 | E | |
| I-229 | 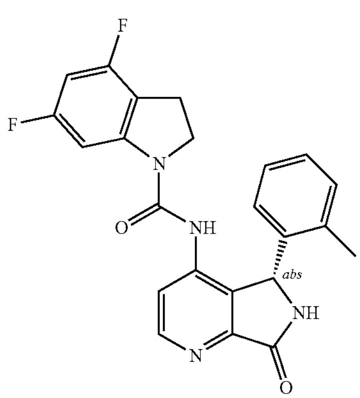 [SMILES: Cc1ccccc1[C@@H]1NC(=O)c2nccc(NC(=O)N3CCc4c(F)cc(F)cc43)c21] | Cc1ccccc1[C@@H]1NC(=O)c2nccc(NC(=O)N3CCc4c3cc(F)cc4F)c12 | 1H NMR (400 MHz, DMSO-d6) 9.33 (s, 1H), 9.06 (br s, 1H), 8.63 (d, 5.3 Hz, 1H), 7.33 (d, 5.3 Hz, 1H), 7.26 (d, 10.3 Hz, 1H), 7.12 (td, 7.4, 1.0 Hz, 1H), 6.96 (dd, 17.5, 7.5 Hz, 2H), 6.75 (td, 9.5, 2.2 Hz, 1H), 6.63-6.40 (m, 1H), 5.82 (s, 1H), 3.74-3.57 (m, 1H), 3.02-2.82 (m, 2H), 2.76 (ddd, 25.2, 16.0, 11.6 Hz, 1H), 2.13 (m, 3H). | 421.2 | C | |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-230 | 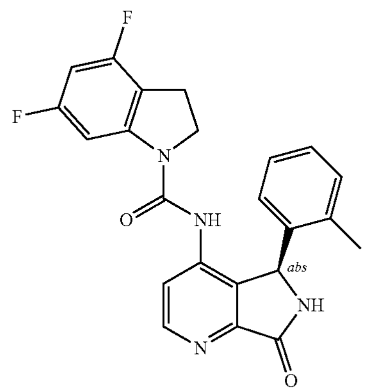 [SMILES: Cc1ccccc1[C@H]1NC(=O)c2nccc(NC(=O)N3CCc4c(F)cc(F)cc43)c21] | Cc1ccccc1[C@H]1NC(=O)c2nccc(NC(=O)N3CCc4c3c(F)cc4F)c12 | 1H NMR (400 MHz, DMSO-d6) 9.33 (s, 1H), 9.06 (br s, 1H), 8.63 (d, 5.3 Hz., 1H), 7.33 (d, 5.3 Hz, 1H), 7.26 (d, 10.3 Hz, 1H), 7.12 (td, 7.4, 1.0 Hz, 1H), 6.96 (dd, 17.5, 7.5 Hz, 2H), 6.75 (td, 9.5, 2.2 Hz, 1H), 6.63-6.40 (m, 1H), 5.82 (s, 1H), 3.74-3.57 (m, 1H), 3.02-2.82 (m, 2H), 2.76 (ddd, 25.2, 16.0, 11.6 Hz, 1H), 2.13 (m, 3H). | 421.3 | E | |
| I-231 | 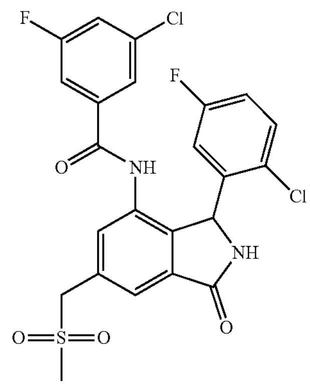 [SMILES: CS(=O)(=O)Cc1cc(NC(=O)c2cc(F)cc(Cl)c2)c2c(c1)C(=O)NC2c1cc(F)ccc1Cl] | CS(=O)(=O)Cc1cc2C(=O)NC(c2c(NC(=O)c2cc(F)cc(Cl)c2)c1)c1cc(F)ccc1Cl | 1H NMR (400 MHz, DMSO-d6) 2.84-3.03 (m, 3H), 3.97-4.15 (m, 1 H), 4.59-4.78 (m, 2H), 5.81-6.08 (m, 1H), 6.54-6.76 (m, 1H), 7.05-7.17 (m, 1H), 7.31-7.36 (m, 1H), 7.36-7.40 (m, 2H), 7.49-7.69 (m, 5H), 7.71-7.79 (m, 1H), 8.99-9.36 (m, 1 H), 10.24-10.55 (m, 1H) | 525 | A | |
| I-232 | 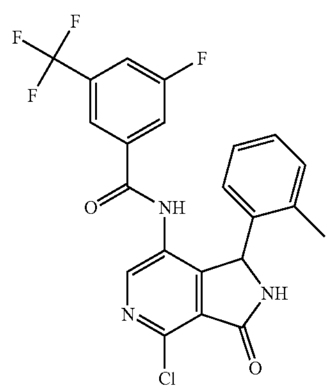 [SMILES: Cc1ccccc1C1NC(=O)c2c(Cl)ncc(NC(=O)c3cc(F)cc(C(F)(F)F)c3)c21] | Cc1ccccc1C1NC(=O)c2c1c(NC(=O)c1cc(F)cc(c1)C(F)(F)F)cnc2Cl | | 464.36 | B | |
| I-233 | 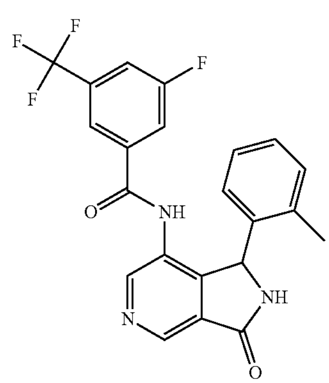 [SMILES: Cc1ccccc1C1NC(=O)c2cncc(NC(=O)c3cc(F)cc(C(F)(F)F)c3)c21] | Cc1ccccc1C1NC(=O)c2cncc(NC(=O)c3cc(F)cc(c3)C(F)(F)F)c12 | 1H NMR (400 MHz, DMSO-d6) 10.65 (s, 1H), 9.28 (s, 1H), 8.88 (s, 1H), 8.69 (s, 1H), 7.91 (br d, 8.54 Hz, 1H), 7.53 (br d, 8.54 Hz, 1H), 7.40 (br s, 1H), 7.03-7.11 (m, 1H), 6.93-7.02 (m, 2H), 6.50-6.64 (m, 1H), 5.95 (br s, 1H), 2.01-2.33 (m, 3H) | 430.45 | B | |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-234 | 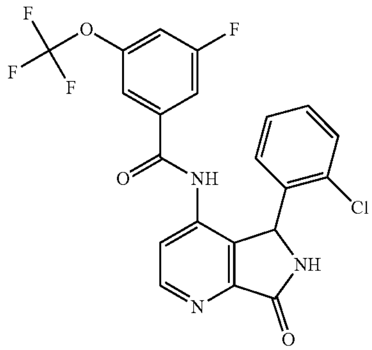 [SMILES: O=C(Nc1ccnc2c1C(c1ccccc1Cl)NC2=O)c1cc(F)cc(OC(F)(F)F)c1] | Fc1cc(OC(F)(F)F)cc(c1)C(=O)Nc1cnc2C(=O)NC(c12)c1cccc c1Cl | ¹H NMR (400 MHz, DMSO-d$_6$) δ 10.48-10.87 (m, 1H), 9.35-9.58 (m, 1H), 8.77 (d, J = 5.13 Hz, 1H), 7.65 (br d, J = 8.79 Hz, 1H), 7.54 (d, J = 5.37 Hz, 1H), 6.57-7.42 (m, 6H), 5.91-6.20 (m, 1H). | 466.3 | | D |
| I-235 | 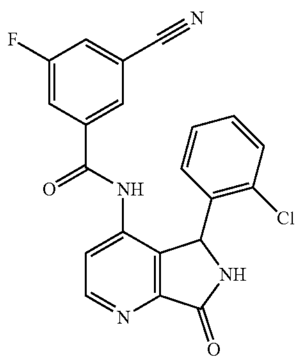 [SMILES: N#Cc1cc(F)cc(C(=O)Nc2ccnc3c2C(c2ccccc2Cl)NC3=O)c1] | Fc1cc(cc(c1)C(=O)Nc1ccnc2C(=O)NC(c12)c1ccccc1Cl)C#N | ¹H NMR (400 MHz, DMSO-d$_6$) δ 10.49-10.99 (m, 1H), 9.46 (br s, 1H), 8.75 (d, J = 5.13 Hz, 1H), 8.08 (br d, J = 7.81 Hz, 1H), 7.46-7.75 (m, 3H), 6.63-7.39 (m, 4H), 5.86-6.20 (m, 1H). | 407.3 | | E |
| I-236 | 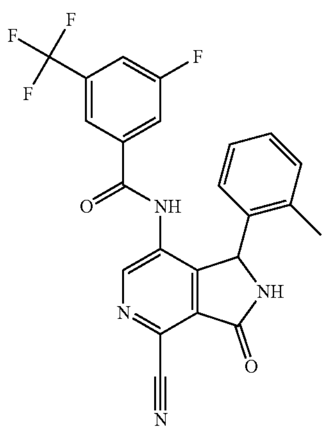 [SMILES: Cc1ccccc1C1NC(=O)c2c(C#N)ncc(NC(=O)c3cc(F)cc(C(F)(F)F)c3)c21] | Cc1ccccc1C1NC(=O)c2c1c(NC(=O)c1cc(F)cc(c1)C(F)(F)F)cnc2C#N | 1H NMR (400 MHz, DMSO-d6) 10.99 (br s, 1H), 9.67 (s, 1H), 8.84 (s, 1H), 7.93 (br d, 8.30 Hz, 1H), 7.51 (br d, 8.79 Hz, 1H), 7.35 (br s, 1H), 7.05-7.12 (m, 1H), 6.93-7.03 (m, 2H), 6.61 (br s, 1H), 6.01 (s, 1H), 2.07-2.37 (m, 3H) | 455.41 | | D |
| I-237 | 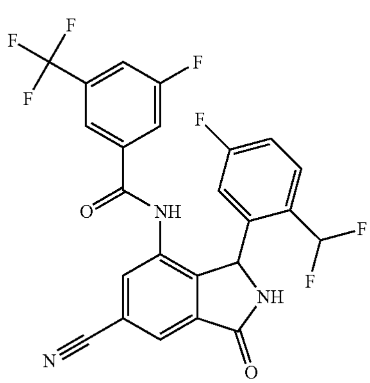 [SMILES: N#Cc1cc(NC(=O)c2cc(F)cc(C(F)(F)F)c2)c2c(c1)C(=O)NC2c1cc(F)ccc1C(F)F] | FC(F)c1ccc(F)cc1C1NC(=O)c2cc(c(NC(=O)c3cc(F)cc(c3)C(F)(F)F)c12)C#N | | | | A |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-238 | 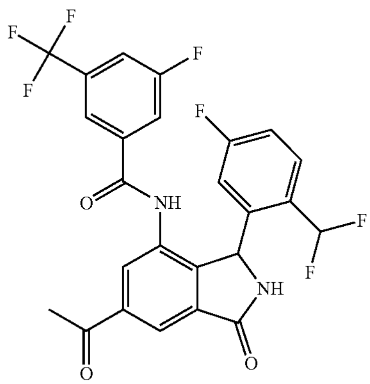 [SMILES: CC(=O)c1cc(NC(=O)c2cc(F)cc(C(F)(F)F)c2)c2c(c1)C(=O)NC2c1cc(F)ccc1C(F)F] | CC(=O)c1cc2C(=O)NC(c2c(NC(=O)c2cc(F)cc(c2)C(F)(F)F)c1)cc(F)ccc1C(F)F | ¹H NMR (400 MHz, DMSO-d$_6$) δ 10.61 (s, 1 H) 9.33 (s, 1 H) 8.24 (d, J = 1.52 Hz, 1 H) 8.07 (d, J = 1.52 Hz, 1 H) 7.92 (br d, J = 8.34 Hz, 1 H) 7.69 (br d, J = 9.09 Hz, 1 H) 7.60 (s, 1 H) 7.49 (dd, J = 8.84, 5.56 Hz, 1 H) 7.21 (td, J = 8.40, 2.65 Hz, 2 H) 6.50 (br s, 1 H) 6.10 (s, 1 H) 2.71 (s, 3 H). | | A | |
| I-239 | 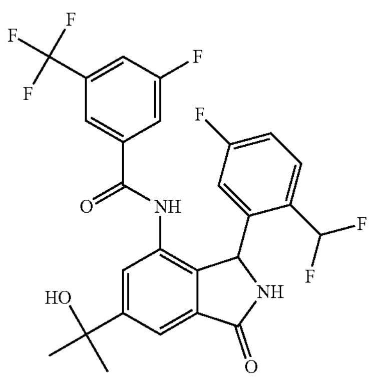 [SMILES: CC(C)(O)c1cc(NC(=O)c2cc(F)cc(C(F)(F)F)c2)c2c(c1)C(=O)NC2c1cc(F)ccc1C(F)F] | CC(C)(O)c1cc2C(=O)NC(c2c(NC(=O)c2cc(F)cc(c2)C(F)(F)F)c1)cc(F)ccc1C(F)F | ¹H NMR (400 MHz, DMSO-d$_6$) δ 10.47 (s, 1 H) 9.10 (s, 1 H) 7.89 (br d, J = 8.08 Hz, 1 H) 7.80 (s, 1 H) 7.68 (br d, J = 9.09 Hz, 1 H) 7.55-7.63 (m, 2 H) 7.47 (dd, J = 8.59, 5.56 Hz, 1 H) 7.19 (td, J = 8.46, 2.53 Hz, 1 H) 6.44 (br d, J = 2.53 Hz, 1 H) 5.95 (s, 1 H) 5.31 (s, 1 H) 1.51 (s, 6 H). | | A | |
| I-240 | 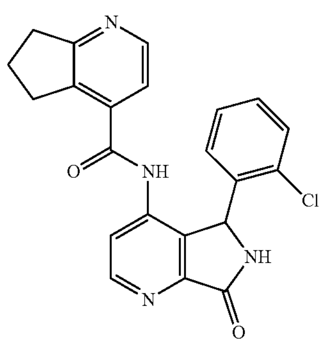 [SMILES: O=C(Nc1ccnc2c1C(c1ccccc1Cl)NC2=O)c1ccnc2c1CCC2] | C1c1ccccc1C1NC(=O)c2ncc(NC(=O)c3ccnc4CCCc34)c12 | ¹H NMR (400 MHz, DMSO-d$_6$) δ 10.36-10.57 (m, 1H), 8.66-8.87 (m, 1H), 8.30-8.47 (m, 1H), 7.44-7.54 (m, 1H), 7.24-7.39 (m, 2H), 6.79-7.09 (m, 2H), 6.38-6.57 (m, 2H), 5.67-5.83 (m, 1H), 4.68-4.91 (m, 1H), 2.74-3.00 (m, 3H), 2.25-2.44 (m, 1H), 1.78-2.07 (m, 2H). | 405.3 | E | |
| I-241 | 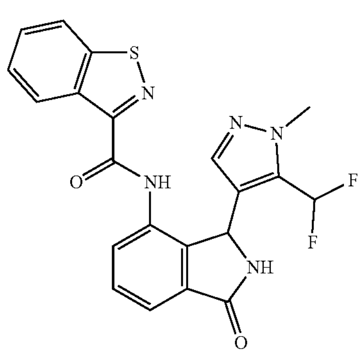 [SMILES: Cn1ncc(C2NC(=O)c3cccc(NC(=O)c4nsc5ccccc45)c32)c1C(F)F] | Cn1ncc(C2NC(=O)c3cccc(NC(=O)c4nsc5ccccc45)c23)c1C(F)F | ¹H NMR (400 MHz, DMSO-d$_6$) δ 10.23-10.40 (m, 1H), 8.83-9.08 (m, 1H), 8.61 (d, J = 8.30 Hz, 1H), 8.31 (d, J = 8.30 Hz, 1H), 7.80 (dd, J = 1.22, 7.08 Hz, 1H), 7.49-7.73 (m, 4H), 6.90-7.32 (m, 2H), 6.08 (s, 1H), 3.67 (s, 3H). | 440.4 | E | |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-242 | 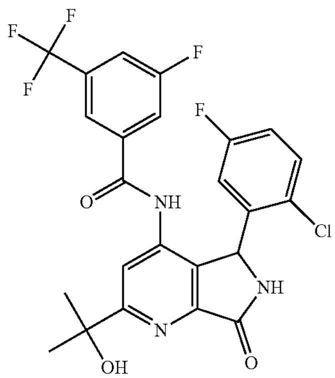 [SMILES: CC(C)(O)c1cc(NC(=O)c2cc(F)cc(C(F)(F)F)c2)c2c(n1)C(=O)NC2c1cc(F)ccc1Cl] | CC(C)(O)c1cc(NC(=O)c2cc(F)cc(c2)C(F)(F)F)c2C(NC(=O)c2n1)c1cc(F)ccc1Cl | 1H NMR (400 MHz, DMSO-d6) 10.86 (s, 1H), 9.46 (s, 1H), 7.97 (d, 7.4 Hz, 1H), 7.80 (s, 1H), 7.75 (d, 8.8 Hz, 1H), 7.64 (s, 1H), 7.33 (dd, 8.9, 5.2 Hz, 1H), 7.17-7.02 (m, 1H), 6.77 (br s, 1H), 5.99 (br s, 1H), 5.47 (s, 1H), 1.56 (s, 3H), 1.51 (s, 3H). | 526.4 | B | |
| I-243 | 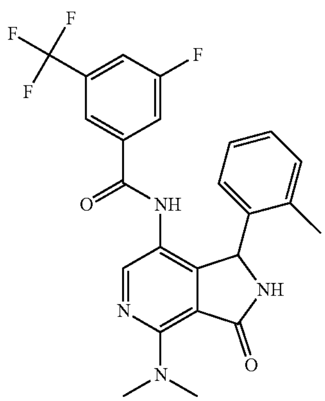 [SMILES: Cc1ccccc1C1NC(=O)c2c(N(C)C)ncc(NC(=O)c3cc(F)cc(C(F)(F)F)c3)c21] | CN(C)c1ncc(NC(=O)c2cc(F)cc(c2)C(F)(F)F)c2C(NC(=O)c12)c1ccccc1C | 1H NMR (400 MHz, DMSO-d6) 10.12 (s, 1H), 8.82 (s, 1H), 8.43 (br s, 1H), 8.13 (s, 1H), 7.86 (br d, 8.54 Hz, 1H), 7.48 (br d, 9.27 Hz, 1H), 7.37 (s, 1H), 7.00-7.08 (m, 1H), 6.89-6.98 (m, 1H), 6.66 (br s, 1H), 6.61 (br s, 1H), 5.74 (s, 1H), 3.19 (s, 3H), 2.11 (br s, 3H) | 473.52 | C | |
| I-244 | 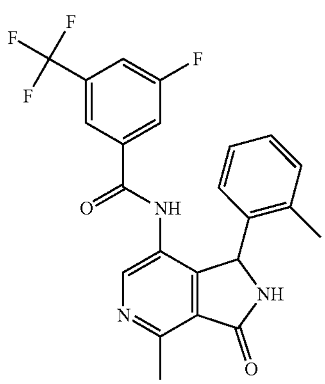 [SMILES: Cc1ccccc1C1NC(=O)c2c(C)ncc(NC(=O)c3cc(F)cc(C(F)(F)F)c3)c21] | Cc1ccccc1C1NC(=O)c2c1c(NC(=O)c1cc(F)cc(c1)C(F)(F)F)cnc2C | 1H NMR (400 MHz, DMSO-d6) 10.50 (br s, 1H), 9.16 (br s, 1H), 8.48-8.54 (m, 1H), 7.89 (br d, 8.30 Hz, 1H), 7.51 (br d, 8.54 Hz, 1H), 7.39 (br s, 1H), 7.03-7.10 (m, 1H), 6.91-7.02 (m, 2H), 6.58 (br s, 1H), 5.86 (br s, 1H), 3.29 (s, 3H), 2.83 (s, 3H) | 444.45 | B | |
| I-245 | 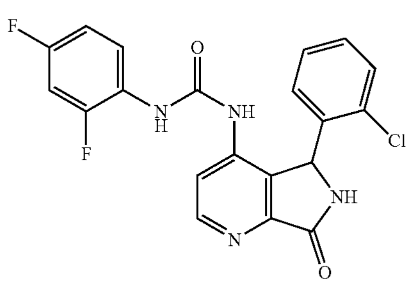 [SMILES: O=C(Nc1ccc(F)cc1F)Nc1ccnc2c1C(c1ccccc1Cl)NC2=O] | Fc1ccc(NC(=O)Nc2ccnc3C(=O)NC(c23)c2cccc2Cl)c(F)c1 | 1H NMR (400 MHz, DMSO-d$_6$) δ 9.39 (br s, 1H), 8.79 (br s, 2H), 8.63 (br d, J = 5.4 Hz, 1H), 7.79-7.87 (m, 1H), 7.76 (br d, J = 3.9 Hz, 1H), 7.46 (br d, J = 7.6 Hz, 1H), 7.32-7.37 (m, 1H), 7.20-7.31 (m, 2H), 7.04 (br t, J = 8.2 Hz, 1H), 6.76-6.91 (m, 1H), 6.10 ppm (br s, 1H). | 415.3 | D | |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-246 | 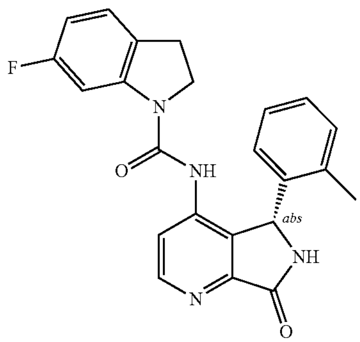 [SMILES: Cc1ccccc1[C@@H]1NC(=O)c2nccc(NC(=O)N3CCc4ccc(F)cc43)c21] | Cc1ccccc1[C@@H]1NC(=O)c2nccc(NC(=O)N3CCc4ccc(F)cc34)c12 | 1H NMR (400 MHz, DMSO-d6) 9.35 (s, 1H), 8.95 (br s, 1H), 8.66 (d, 5.3 Hz, 1H), 7.43-7.38 (m, 2H), 7.20-7.09 (m, 2H), 7.01-6.96 (m, 2H), 6.79-6.70 (m, 1H), 6.55(br s, 1H), 5.88 (s, 1H), 3.68-3.61 (m, 1H), 3.03-2.75 (m, 3H), 2.29-2.00 (br s, 3H). | 403.3 | B | |
| I-247 | 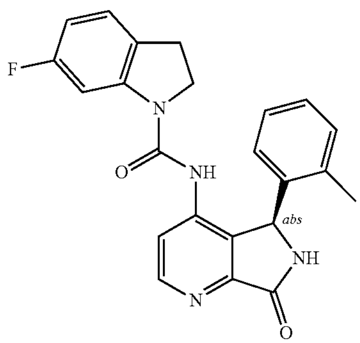 [SMILES: Cc1ccccc1[C@H]1NC(=O)c2nccc(NC(=O)N3CCc4ccc(F)cc43)c21] | Cc1ccccc1[C@H]1NC(=O)c2nccc(NC(=O)N3CCc4ccc(F)cc34)c12 | 1H NMR (400 MHz, DMSO-d6) 9.35 (s, 1H), 8.95 (br s, 1H), 8.66 (d, 5.3 Hz, 1H), 7.43-7.38 (m, 2H), 7.20-7.09 (m, 2H), 7.01-6.96 (m, 2H), 6.79-6.70 (m, 1H), 6.55(br s, 1H), 5.88 (s, 1H), 3.68-3.61 (m, 1H), 3.03-2.75 (m, 3H), 2.29-2.00 (br s, 3H). | 403.3 | E | |
| I-248 | 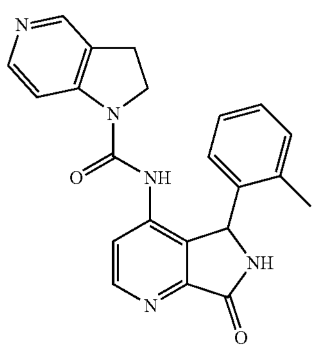 [SMILES: Cc1ccccc1C1NC(=O)c2nccc(NC(=O)N3CCc4cnccc43)c21] | Cc1ccccc1C1NC(=O)c2nccc(NC(=O)N3CCc4nccc34)c12 | 1H NMR (400 MHz, DMSO-d6) 9.36 (s, 1H), 9.10 (br s, 1H), 8.67 (d, 5.3 Hz, 1H), 8.27 (s, 1H), 8.24 (d, 5.4 Hz, 1H), 7.50 (d, 5.4 Hz, 1H), 7.41 (d, 5.3 Hz, 1H), 7.14 (td, 7.5, 1.1 Hz, 1H), 7.01 (d, 7.7 Hz, 1H), 6.97 (t, 7.4 H, 1Hz), 6.55 (br s, 1H), 5.86 (s,1H), 370-3.63 (m, 1H), 3.11-2.79 (m, 3H), 2.16 (br s, 3H). | 386.3 | E | |
| I-249 | 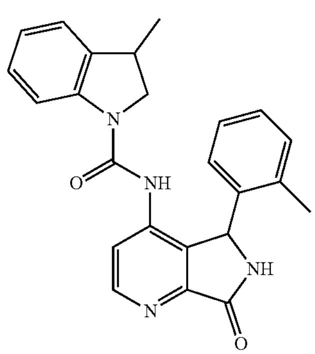 [SMILES: Cc1ccccc1C1NC(=O)c2nccc(NC(=O)N3CC(C)c4ccccc43)c21] | CC1CN(C(=O)Nc2ccnc3C(=O)NC(c23)c2cccc2C)c2ccccc12 | 1H NMR (400 MHz, DMSO-d6) 9.31 (s, 2H), 8.78 (br s, 1H), 8.67 (br s, 1H), 8.61 (s, 1H), 8.60 (s, 1H), 7.64 (d, 8.0 Hz, 1H), 7.59 (d, 8.1 Hz, 1H), 7.46 (d, 5.4 Hz, 1H), 7.40 (d, 5.3 Hz, 1H), 7.17-7.05 (m, 6H), 7.03-6.87 (m, 6H), 6.49 (br s, 2H), 5.89 (s, 1H), 5.88 (s, 1H), 3.79-3.65 (m, 2H), 3.25-3.08 (m, 2H), 2.99 (dd, 8.9, 5.9 Hz, 1H), 2.51 (dd, 10.0, 6.7 Hz, 1H), 2.15 (br s, 6H), 1.09 (d, 7.6 Hz, 3H), 1.04 (d, 6.8 Hz, 3H). | 397.4 | B | |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-250 | 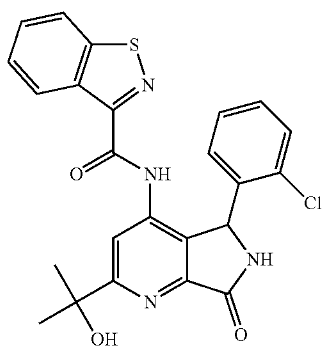 [SMILES: CC(C)(O)c1cc(NC(=O)c2nsc3ccccc23)c2c(n1)C(=O)NC2c1ccccc1Cl] | CC(C)(O)c1cc(NC(=O)c2nsc3ccccc23)c2C(NC(=O)c2n1)c1ccccc1Cl | 1H NMR (400 MHz, DMSO-d6) 10.40 (s, 1H), 9.47 (s, 1H), 8.65 (d, 8.1 Hz, 1H), 8.32 (d, 8.2 Hz, 1H), 8.23 (s, 1H), 7.72-7.66 (m, 1H), 7.65-7.59 (m, 1H), 7.58-7.54 (m, 1H), 7.33 (d, 7.7 Hz., 1H), 7.22 (td, 7.7, 1.8 Hz, 1H), 7.15 (td, 7.6, 1.2 Hz, 1H), 6.31 (br s, 1H), 5.44 (s, 1H), 1.56 (s, 3H), 1.52 (s, 3H). | 479.2 | A | |
| I-251 | 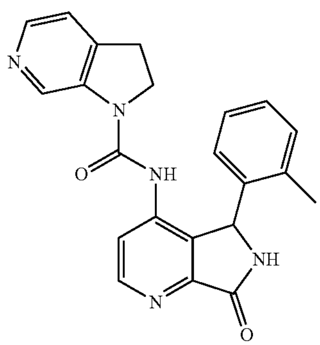 [SMILES: Cc1ccccc1C1NC(=O)c2nccc(NC(=O)N3CCc4ccncc43)c21] | Cc1ccccc1C1NC(=O)c2nccc(NC(=O)N3CCc4cncc34)c12 | 1H NMR (400 MHz, DMSO-d6) 9.36 (s, 1H), 9.02 (s, 1H), 8.84 (s, 1H), 8.67 (d, 5.3 Hz, 1H), 8.15 (d, 4.9 Hz, 1H), 7.39 (d, 5.4 Hz, 1H), 7.24 (d, 4.7 Hz, 1H), 7.13 (td, 7.5, 1.2 Hz, 1H), 6.97 (m, 2H), 6.54 (br s, 1H), 5.88 (s, 1H), 3.71-3.55 (m, 1H), 3.09-2.77 (m, 3H), 2.11 (br s, 3H). | 386.4 | E | |
| I-252 | 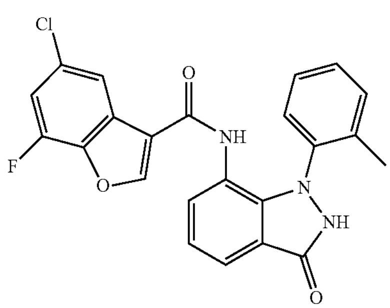 [SMILES: Cc1ccccc1-n1[nH]c(=O)c2cccc(NC(=O)c3coc4c(F)cc(Cl)cc34)c21] | Cc1ccccc1-n1[nH]c(=O)c2ccc(NC(=O)c3coc4c(F)cc(Cl)cc34)c12 | 1H NMR (400 MHz, DMSO-d6) 11.15 (br s, 1H), 9.85 (s, 1H), 8.17 (s, 1H), 7.72 (dd, 8.0, 3.9 Hz, 1H), 7.59 (d, 1.8 Hz, 1H), 7.53 (dd, 10.7, 1.9 Hz, 1H), 7.26 (d, 7.0 Hz, 1H), 7.14 (dd, 7.9, 7.4 Hz, 1H), 7.07 (dd, 7.7, 1.1 Hz, 1H), 6.97-6.92 (m, 2H), 6.87 (td, 7.5, 1.1 Hz., 1H), 2.06 (s, 3H). | 436.1 | B | |
| I-253 | 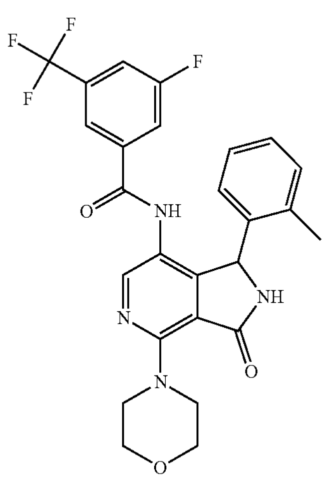 [SMILES: Cc1ccccc1C1NC(=O)c2c(N3CCOCC3)ncc(NC(=O)c3cc(F)cc(C(F)(F)F)c3)c21] | Cc1ccccc1C1NC(=O)c2c1c(NC(=O)c1cc(F)cc(C(F)(F)F)cnc2N1CCOCC1 | 1H NMR (400 MHz, DMSO-d6) 10.19 (s, 1H), 8.98 (s, 1H), 8.17 (s, 1H), 7.85 (d, 8.4 Hz, 1H), 7.45 (d, 8.8 Hz, 1H), 7.33 (s, 1H), 7.06-6.83 (m, 3H), 6.60 (s, J, 1H), 5.75 (s), 3.80-3.66 (m, 6H), 3.63-3.51 (m, 2H), 2.15 (s, 3H). | 515.3 | D | |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-254 | 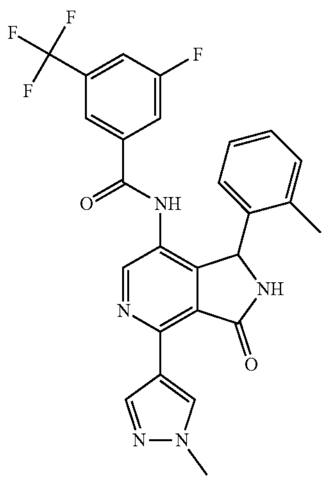 [SMILES: Cc1ccccc1C1NC(=O)c2c(-c3cnn(C)c3)ncc(NC(=O)c3cc(F)cc(C(F)(F)F)c3)c21] | Cc1ccccc1C1NC(=O)c2c1c(NC(=O)c(1cc(F)cc1)C(F)(F)F)cnc2-c1cnn(C)c1 | 1H NMR (400 MHz, DMSO-d6) 9.24 (s, 1H), 8.90 (s, 1H), 8.59 (s, 1H), 8.38 (s, 1H), 7.87 (d, 8.7 Hz, 1H), 7.49 (d, 8.8 Hz, 1H), 7.36 (s, 1H), 7.08-7.01 (m, 1H), 7.0-6.90 (m, 2H), 6.64 (s, 1H), 5.88 (s, 1H), 3.91 (s, 3H), 2.33-2.00 (m, 60.5 Hz, 3H). | 510.2 | B | |
| I-255 | 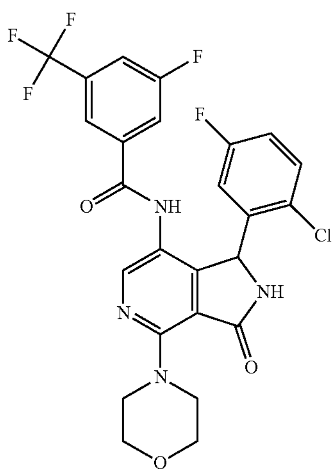 [SMILES: O=C(Nc1cnc(N2CCOCC2)c2c1C(c1cc(F)ccc1Cl)NC2=O)c1cc(F)cc(C(F)(F)F)c1] | Fc1ccc(C1)c(c1)C1NC(=O)c2c1c(NC(=O)c1cc(F)cc(c1)C(F)(F)F)cnc2N1CCOCC1 | 1H NMR (400 MHz, CD3OD) 8.16 (s, 1H), 7.74-7.55 (m, 3H), 7.24 (dd, 8.9, 5.0 Hz, 1H), 7.10-6.91 (m, 1H), 6.80-6.61 (bs, 1H), 6.03 (bs, 1H), 3.93-3.71 (m, 6H), 3.71-3.57 (m, 2H), | 553.3 | D | |
| I-256 | 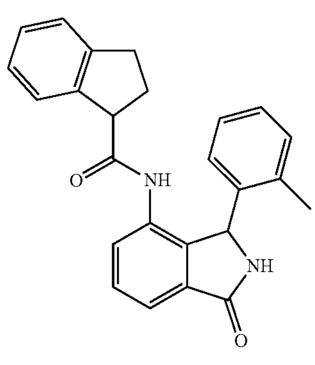 [SMILES: Cc1ccccc1C1NC(=O)c2cccc(NC(=O)C3CCc4ccccc43)c21] | Cc1ccccc1C1NC(=O)c2cccc(NC(=O)C3CCc4ccccc34)c12 | 1H NMR (400 MHz, DMSO-d6) 9.87 (s, 0.6H), 9.85 (s, 0.4H), 9.01 (s, 0.4H), 8.98 (s, 0.6H), 7.65-7.53 (m, 2.4H), 7.47 (d, 1.2 Hz, 0.6H), 7.28-7.16 (m, 2.4H), 7.16-7.09 (m, 1.7H), 7.08-6.91 (m, 2H), 6.61 (d, 7.5 Hz, 0.4H), 6.45 (br s, 1.3H), 6.02 (s, 1H), 3.79-3.68 (m, 1H), 2.95-2.82 (m, 1H), 2.81-2.66 (m, 1H), 2.33 (br s, 1H), 2.16 (s, 2H), 2.06-1.94 (m, 1H), 1.94-1.82 (m, 1H). | 383.3 | D | |

TABLE 2-continued

Representative Compounds of the Invention with Bioactivity Data.

| Ex. No. | Structure | SMILES | $^1$H NMR | MS | ADP-Glo IC$_{50}$ | MCF 10A IC$_{50}$ |
|---|---|---|---|---|---|---|
| I-257 | 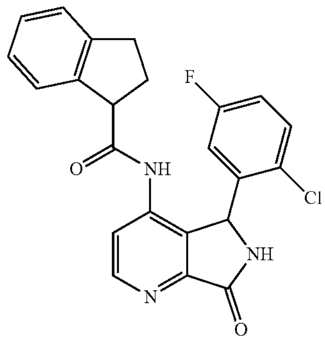 [SMILES: O=C1NC(c2cc(F)ccc2Cl)c2c(NC(=O)C3CCc4ccccc43)ccnc21] | Fc1ccc(C1)c(c1)C1NC(=O)c2nccc(NC(=O)N3CCc4cccc34)c12 | 1H NMR (400 MHz, DMSO-d6) 9.37 (s, 1H), 9.11 (s, 1H), 8.64 (s, 1H), 8.50 (s, 1H), 7.67 (d, 7.7 Hz, 1H), 7.41 (s, 1H), 7.35 (dd, 8.8, 5.2 Hz, 1H), 7.21-7.14 (m, 2H), 7.14-7.07 (m, 1H), 6.92 (t, 7.1 Hz, 1H), 6.72 (br s, 1H), 5.97 (br s, 1H), 3.89-3.75 (m, 1H), 3.25-3.16 (m, 1H), 3.08-2.87 (m, 2H) | 423.6 | C | |
| I-258 | 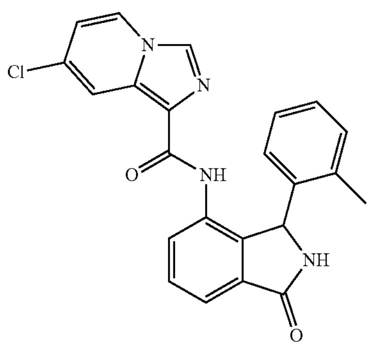 [SMILES: Cc1ccccc1C1NC(=O)c2cccc(NC(=O)c3ncn4ccc(Cl)cc34)c21] | Cc1ccccc1C1NC(=O)c2cccc(NC(=O)c3ncn4ccc(Cl)cc34)c12 | 1H NMR (400 MHz, DMSO-d6) 9.29 (s, 1H), 9.02 (s, 1H), 8.52 (dd, 7.4, 0.8 Hz, 1H), 8.42 (s, 1H), 8.03-7.98 (m, 2H), 7.56 (d, 1.7 Hz, 1H), 7.55 (s, 1H), 7.09-7.02 (m, 2H), 7.01-6.94 (m, 2H), 6.69 (br. s, 1H), 6.15 (s, 1H), 2.35 (br. s, 3H). | 417.2 | D | |
| I-259 | 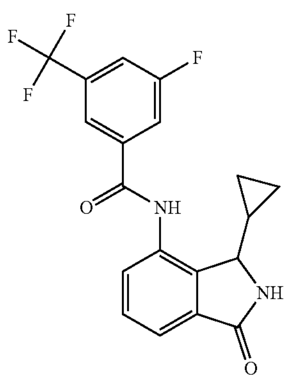 [SMILES: O=C(Nc1cccc2c1C(C1CC1)NC2=O)c1cc(F)cc(C(F)(F)F)c1] | Fc1cc(cc(c1)C(F)(F)F)C(=O)Nc1ccc2C(=O)NC(C3CC3)c12 | 1H NMR (400 MHz, DMSO-d6) 10.68 (s, 1H), 8.70 (s, 1H), 8.23 (s, 1H), 8.16 (d, 9.2 Hz, 1H), 8.04 (d, 8.5 Hz, 1H), 7.62 (dd, 6.9, 2.1 Hz, 1H), 7.58-7.54 (m, 2H), 4.37 (d, 7.4 Hz, 1H), 0.84-0.74 (m, 1H), 0.42-0.24 (m, 3H), 0.16 (m, 1H). | 379.2 | E | |
| I-260 | 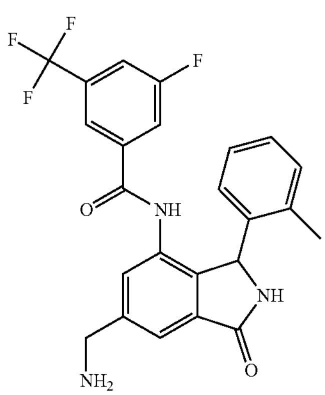 [SMILES: Cc1ccccc1C1NC(=O)c2cc(CN)cc(NC(=O)c3cc(F)cc(C(F)(F)F)c3)c21] | Cc1ccccc1C1NC(=O)c2cc(CN)cc(NC(=O)c3cc(F)cc(c3)C(F)(F)F)c12 | 1H NMR (400 MHz, CD3OD) 7.89 (s, 1H), 7.67-7.65 (m, 2H), 7.40-7.37 (m, 2H), 7.13 (td, 1.2, 7.7 Hz, 1H), 7.04 (d, 7.5 Hz, 1H), 6.99 (br t, 6.0 Hz, 1H), 6.60 (br s, 1H), 6.05 (s, 1H), 4.29 (br s, 2H), 2.30 (br s, 3H). | 458.3 | B | |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-261 | 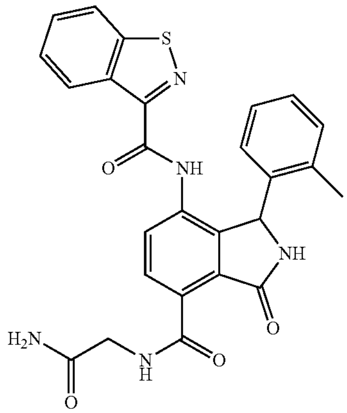 [SMILES: Cc1ccccc1C1NC(=O)c2c(C(=O)NCC(N)=O)ccc(NC(=O)c3nsc4ccccc34)c21] | Cc1ccccc1C1NC(=O)c2c1c(NC(=O)c1nsc3cccc13)ccc2C(=O)NCC(N)=O | 1H NMR (400 MHz, DMSO-d6) 10.59 (t, 5.8 Hz, 1H), 10.14 (br s, 1H), 9.66 (s, 1 H), 8.60 (d, 8.1 Hz, 1H), 8.31 (d, 8.2 Hz, 1H), 8.05 (d, 8.3 Hz, 1H), 7.96 (d, 8.3 Hz, 1H), 7.91 (s, 1H), 7.68 (ddd, 8.2, 7.0, 1.2 Hz, 1H), 7.59 (ddd, 8.0, 7.0, 0.9 Hz, 1H), 7.18 (s, 1 H), 7.04-6.97 (m, 2H), 6.97-6.90 (m, 1 H), 6.70 (br s, 1H), 6.22 (s, 1H), 3.90 (d, 6.2 Hz, 2H), 2.35 (br s, 3H). | 500.3 | A | |
| I-262 | 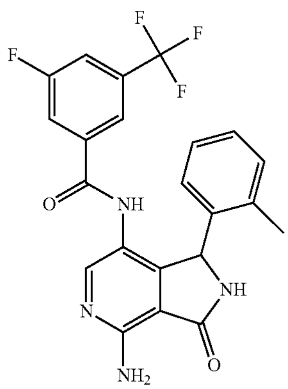 [SMILES: Cc1ccccc1C1NC(=O)c2c(N)ncc(NC(=O)c3cc(F)cc(C(F)(F)F)c3)c21] | Cc1ccccc1C1NC(=O)c2c1c(NC(=O)c1cc(F)cc(c1)C(F)(F)F)cnc2N | 1H NMR (400 MHz, DMSO-d6) 10.03 (s, 1H), 8.83 (s, 1H), 7.90-8.00 (m, 1H), 7.79 (br d, 8.34 Hz, 1H), 7.41-7.52 (m, 1H), 7.36 (s, 1H), 6.97-7.04 (m, 1H), 6.84-6.95 (m, 2H), 6.58-6.75 (m, 3H), 5.73 (s, 1H), 1.97-2.19 (m, 3H) | 445.35 | B | |
| I-263 | 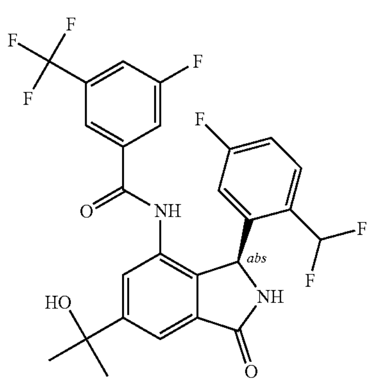 [SMILES: CC(C)(O)c1cc(NC(=O)c2cc(F)cc(C(F)(F)F)c2)c2c(c1)C(=O)N[C@@H]2c1cc(F)ccc1C(F)F] | CC(C)(O)c1cc2C(=O)N[C@@H](c2c(NC(=O)c2cc(F)cc(c2)C(F)(F)F)c1)c1cc(F)ccc1C(F)F | ¹H NMR (400 MHz, DMSO-d$_6$) δ 10.47 (s, 1 H) 9.10 (s, 1 H) 7.89 (br d, J = 8.08 Hz, 1 H) 7.80 (s, 1 H) 7.68 (br d, J = 9.09 Hz, 1 H) 7.55-7.63 (m, 2 H) 7.47 (dd, J = 8.59, 5.56 Hz, 1 H) 7.19 (td, J = 8.46, 2.53 Hz, 1 H) 6.44 (br d, J = 2.53 Hz, 1 H) 5.95 (s, 1 H) 5.31 (s, 1 H) 1.51 (s, 6 H). | | E | |

TABLE 2-continued

Representative Compounds of the Invention with Bioactivity Data.

| Ex. No. | Structure | SMILES | ¹H NMR | MS | ADP-Glo IC₅₀ | MCF 10A IC₅₀ |
|---|---|---|---|---|---|---|
| I-264 | 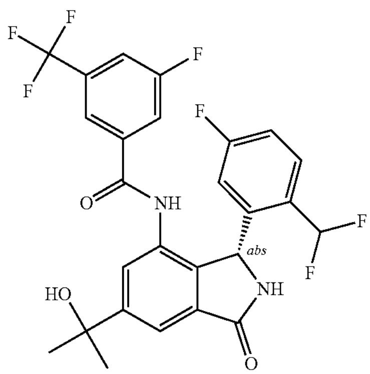 | CC(C)(O)c1cc2C(=O)N[C@H](c2c(NC(=O)c2cc(F)cc(c2)C(F)(F)F)c1)c1cc(F)ccc1C(F)F | ¹H NMR (400 MHz, DMSO-d₆) δ 10.47 (s, 1 H) 9.10 (s, 1 H) 7.89 (br d, J = 8.08 Hz, 1 H) 7.80 (s, 1 H) 7.68 (br d, J = 9.09 Hz, 1 H) 7.55-7.63 (m, 2 H) 7.47 (dd, J = 8.59, 5.56 Hz, 1 H) 7.19 (td, J = 8.46, 2.53 Hz, 1 H) 6.44 (br d, J = 2.53 Hz, 1 H) 5.95 (s, 1 H) 5.31 (s, 1 H) 1.51 (s, 6 H) | | A | B |
| I-265 | 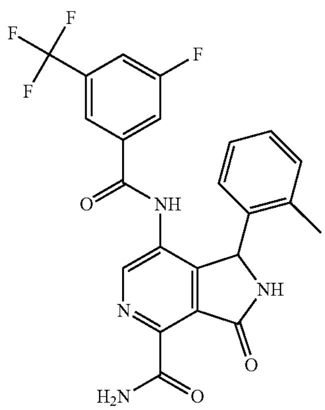 [SMILES: Cc1ccccc1C1NC(=O)c2c(C(N)=O)ncc(NC(=O)c3cc(F)cc(C(F)(F)F)c3)c21] | Cc1ccccc1C1NC(=O)c2c1c(NC(=O)c1cc(F)cc(c1)C(F)(F)F)cnc2C(N)=O | 1H NMR (400 MHz, DMSO-d6) 10.68 (br s, 1H), 9.47 (s, 1H), 8.79-8.91 (m, 1H), 8.71 (br s, 1H), 7.90 (br d, 6.83 Hz, 1H), 7.70 (br s, 1H), 7.53 (br d, 9.03 Hz, 1H), 7.39 (br s, 1H), 6.94-7.12 (m, 2H), 6.52-6.65 (m, 1H), 5.95 (br s, 1H), 2.07-2.35 (m, 3H) | 473.4 | B | |
| I-266 | 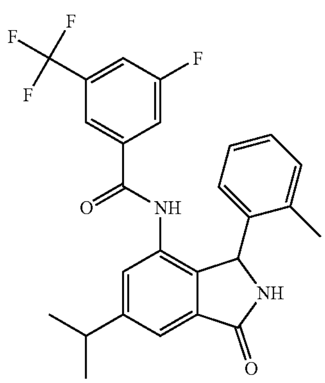 [SMILES: Cc1ccccc1C1NC(=O)c2cc(C(C)C)cc(NC(=O)c3cc(F)cc(C(F)(F)F)c3)c21] | CC(C)c1cc2C(=O)NC(c2c(NC(=O)c2cc(F)cc(c2)C(F)(F)F)c1)c1ccccc1C | 1H NMR (400 MHz, DMSO-d6) 1.29 (d, 6.82 Hz, 6H), 2.17 (br d, 1.26 Hz, 3H), 3.02-3.14 (m, 1H), 5.85 (s, 1H), 6.60 (s, 1H), 6.87-6.99 (m, 2H), 7.01-7.09 (m, 1H), 7.33-7.41 (m, 2H), 7.49 (br d, 8.84 Hz, 1H), 7.55 (d, 1.26 Hz, 1H), 7.87 (br d, 8.59 Hz, 1H), 8.99 (s, 1H), 10.33 (s, 1H) | 471.4 | B | |
| I-267 | 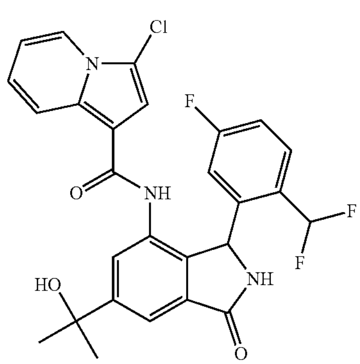 [SMILES: CC(C)(O)c1cc(NC(=O)c2cc(Cl)n3ccccc23)c2c(c1)C(=O)NC2c1cc(F)ccc1C(F)F] | CC(C)(O)c1cc2C(=O)NC(c2c(NC(=O)c2cc(C1)n3cccc23)c1)c1cc(F)ccc1C(F)F | ¹H NMR (400 MHz, DMSO-d₆) δ 9.67 (s, 1 H) 9.05 (s, 1 H) 8.15-8.28 (m, 2 H) 7.72 (d, J = 1.52 Hz, 1 H) 7.62 (d, J = 1.52 Hz, 1 H) 7.38 (dd, J = 8.72, 5.68 Hz, 1 H) 7.07-7.24 (m, 4 H) 7.00 (td, J = 6.95, 1.26 Hz, 1 H) 6.39 (br d, J = 9.35 Hz, 1 H) 6.08 (s, 1 H) 5.27 (s, 1 H) 1.51 (s, 6 H). | | A | |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-268 | 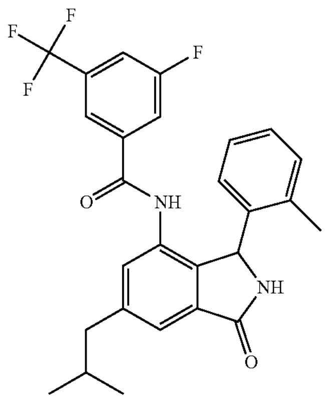 [SMILES: Cc1ccccc1C1NC(=O)c2cc(CC(C)C)cc(NC(=O)c3cc(F)cc(C(F)(F)F)c3)c21] | CC(C)Cc1cc2C(=O)NC(c2c(NC(=O)c2cc(F)cc(c2)C(F)(F)F)c1)c1ccccc1C | 1H NMR (400 MHz, DMSO-d6) 0.91 (dd, 6.57, 1.26 Hz, 6H), 1.91 (tt, 13.45, 6.63 Hz, 1H), 2.04-2.24 (m, 2H), 2.51-2.70 (m, 3H), 5.85 (br s, 1H), 6.62 (s, 1H), 6.90-7.07 (m, 3H), 7.30 (s, 1H), 7.36 (br s, 1H), 7.42-7.50 (m, 2H), 7.86 (br d, 8.59 Hz, 1H), 8.98 (s, 1H), 10.30 (s, 1H) | 485.4 | A | |
| I-269 | 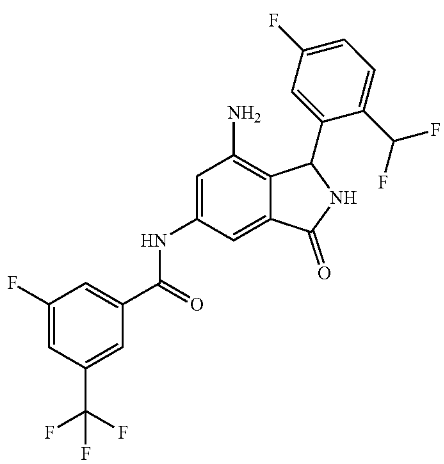 [SMILES: Nc1cc(NC(=O)c2cc(F)cc(C(F)(F)F)c2)cc2c1C(c1cc(F)ccc1C(F)F)NC2=O] | Nc1cc(NC(=O)c2cc(F)cc(c2)C(F)(F)F)cc2C(=O)NC(c12)c1cc(F)ccc1C(F)F | | | | E |
| I-270 | 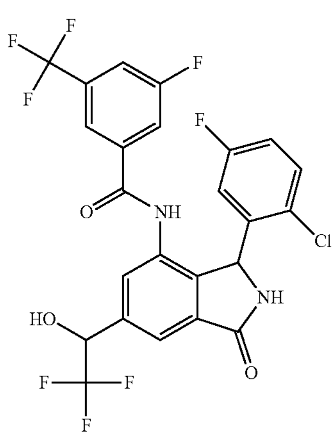 [SMILES: O=C(Nc1cc(C(O)C(F)(F)F)cc2c1C(c1cc(F)ccc1Cl)NC2=O)c1cc(F)cc(C(F)(F)F)c1] | OC(c1cc2C(=O)NC(c2c(NC(=O)c2cc(F)cc(c2)C(F)(F)F)c1)c1cc(F)ccc1Cl)C(F)(F)F | 1H NMR (400 MHz, DMSO-d6) 5.44 (dt, 13.07, 6.47 Hz, 1H), 5.97 (br s, 1H), 7.05-7.15 (m, 2H), 7.30 (dd, 8.84, 5.31 Hz, 1H), 7.60-7.68 (m, 2H), 7.74 (br d, 8.59 Hz, 1H), 7.82 (br d, 4.29 Hz, 1H), 7.93 (br d, 8.34 Hz, 1H), 9.19 (br s, 1H), 10.57 (br d, 8.34 Hz, 1H) | 565 | A | |

TABLE 2-continued

Representative Compounds of the Invention with Bioactivity Data.

| Ex. No. | Structure | SMILES | $^1$H NMR | MS | ADP-Glo IC$_{50}$ | MCF 10A IC$_{50}$ |
|---|---|---|---|---|---|---|
| I-271 | 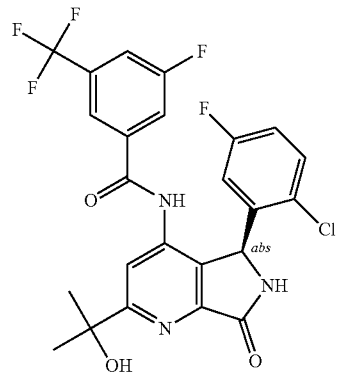 [SMILES: CC(C)(O)c1cc(NC(=O)c2cc(F)cc(C(F)(F)F)c2)c2c(n1)C(=O)N[C@@H]2c1cc(F)ccc1Cl] | CC(C)(O)c1cc(NC(=O)c2cc(F)cc(c2)C(F)(F)F)c2[C@H](NC(=O)c2n1)c1cc(F)ccc1Cl | $^1$H NMR (400 MHz, DMSO-d$_6$) δ 10.86 (s, 1H), 9.46 (s, 1H), 7.97 (d, J = 7.4 Hz, 1H), 7.80 (s, 1H), 7.75 (d, J = 8.8 Hz, 1H), 7.64 (s, 1H), 7.33 (dd, J = 8.9, 5.2 Hz, 1H), 7.17-7.02 (m, 1H), 6.77 (br s, 1H), 5.99 (br s, 1H), 5.47 (s, 1H), 1.56 (s, 3H), 1.51 (s, 3H). | 526.4 | D | |
| I-272 | 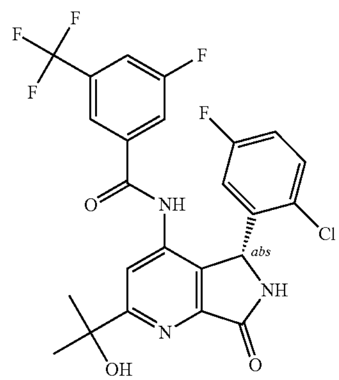 [SMILES: CC(C)(O)c1cc(NC(=O)c2cc(F)cc(C(F)(F)F)c2)c2c(n1)C(=O)N[C@H]2c1cc(F)ccc1Cl] | CC(C)(O)c1cc(NC(=O)c2cc(F)cc(c2)C(F)(F)F)c2[C@@H](NC(=O)c2n1)c1cc(F)ccc1Cl | $^1$H NMR (400 MHz, DMSO-d$_6$) δ 10.86 (s, 1H), 9.46 (s, 1H), 7.97 (d, J = 7.4 Hz, 1H), 7.80 (s, 1H), 7.75 (d, J = 8.8 Hz, 1H), 7.64 (s, 1H), 7.33 (dd, J = 8.9, 5.2 Hz, 1H), 7.17-7.02 (m, 1H), 6.77 (br s, 1H), 5.99 (br s, 1H), 5.47 (s, 1H), 1.56 (s, 3H), 1.51 (s, 3H). | 526.4 | B | |
| I-273 | 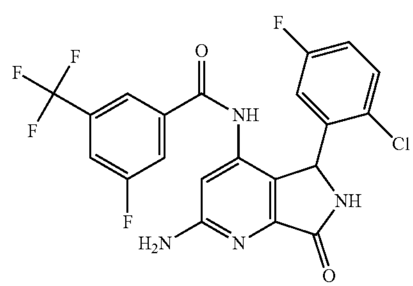 [SMILES: Nc1cc(NC(=O)c2cc(F)cc(C(F)(F)F)c2)c2c(n1)C(=O)NC2c1cc(F)ccc1Cl] | Nc1cc(NC(=O)c2cc(F)cc(c2)C(F)(F)F)c2C(NC(=O)c2n1)c1cc(F)ccc1Cl | $^1$H NMR (400 MHz, DMSO-d$_6$) δ 10.47 (s, 1H), 9.14 (br s, 1H), 7.94 (br d, J = 8.3 Hz, 1H), 7.67 (br d, J = 8.8 Hz, 1H), 7.56 (s, 1H), 7.31 (dd, J = 8.8, 5.1 Hz, 1H), 7.07 (td, J = 8.1, 2.4 Hz, 1H), 6.76-6.89 (m, 1H), 6.41-6.67 (m, 3H), 5.83 (br s, 1H). | 483.4 | B | |
| I-274 | 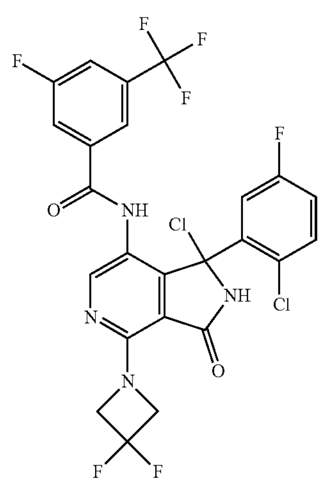 [SMILES: O=C(Nc1cnc(N2CC(F)(F)C2)c2c1C(Cl)(c1cc(F)ccc1Cl)NC2=O)c1cc(F)cc(C(F)(F)F)c1] | Fc1ccc(C1)c(c1)C1(C1)NC(=O)c2c1c(NC(=O)c1cc(F)cc(c1)C(F)F)cnc2N1CC(F)(F)C1 | 1H NMR (400 MHz, CD3OD) 8.71 (s, 1H), 7.87 (s, 1H), 7.77 (d, 8.6 Hz, 1H), 7.68-7.58 (m, 2H), 7.49-7.32 (m, 1H), 7.14-6.97 (m, 1H), 3.82-3.56 (m, 4H). | 593.1 | D | |

TABLE 2-continued

Representative Compounds of the Invention with Bioactivity Data.

| Ex. No. | Structure | SMILES | $^1$H NMR | MS | ADP-Glo IC$_{50}$ | MCF 10A IC$_{50}$ |
|---|---|---|---|---|---|---|
| I-275 | 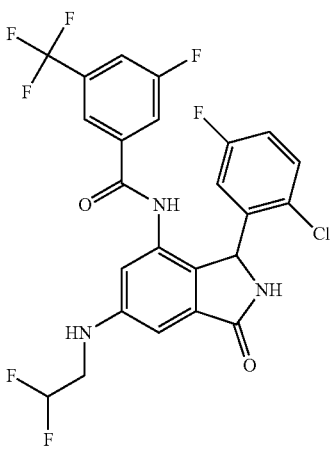 [SMILES: O=C(Nc1cc(NCC(F)F)cc2c1C(c1cc(F)ccc1Cl)NC2=O)c1cc(F)cc(C(F)(F)F)c1] | FC(F)CNc1cc2C(=O)NC(c2c(NC(=O)c2cc(F)cc(c2)C(F)(F)F)c1)c1cc(F)ccc1Cl | 1H NMR (400 MHz, DMSO-d6) 3.49-3.66 (m, 2H), 5.82 (br s, 1H), 5.98-6.31 (m, 2H), 6.52 (br t, 6.35 Hz, 1H), 6.80 (s, 1H), 6.94 (d, 1.71 Hz, 1H), 7.05 (td, 8.36, 3.05 Hz, 1H), 7.27 (dd, 8.79, 5.13 Hz, 1H), 7.61 (s, 1H), 7.69 (br d, 8.79 Hz, 1H), 7.90 (br d, 8.30 Hz, 1H), 8.92 (br s, 1H), 10.29 (s, 1H) | 546.26 | A | |
| I-276 | 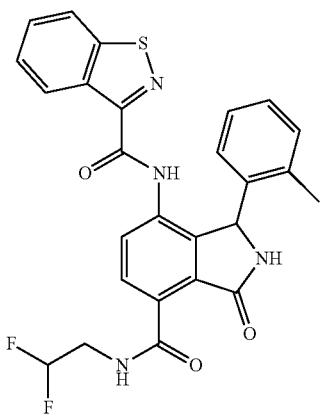 [SMILES: Cc1ccccc1C1NC(=O)c2c(C(=O)NCC(F)F)ccc(NC(=O)c3nsc4ccccc34)c21] | Cc1ccccc1C1NC(=O)c2c1c(NC(=O)c1nsc3cccc13)ccc2C(=O)NCC(F)F | 1H NMR (400 MHz, DMSO-d6) 11.78 (t, 5.5 Hz, 1H), 10.09 (s, 1H), 9.91 (s, 1H), 8.60 (d, 8.3 Hz, 1H), 8.38 (d, 8.4 Hz, 1H), 8.33-8.29 (m, 1H), 8.08 (d, 8.5 Hz, 1H), 7.68 (ddd, 8.2, 7.0, 1.2 Hz, 1H), 7.59 (ddd, 8.0, 7.0, 0.9 Hz, 1H), 7.05-7.00 (m, 2H), 6.98-6.90 (m, 1H), 6.64 (br s, 1H), 6.26 (s, 1H), 6.23 (tt, 55.7, 3.7 Hz, 1H), 3.85 (tdd, 16.4, 5.5, 4.0 Hz, 2H), 2.29 (br s, 3H). | 507.2 | A | |
| I-277 | 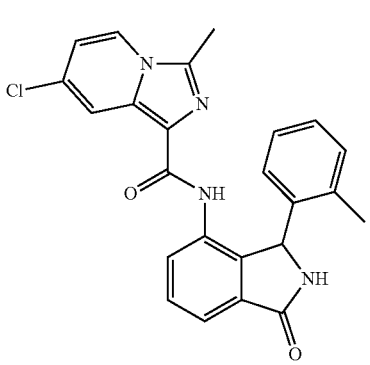 [SMILES: Cc1ccccc1C1NC(=O)c2cccc(NC(=O)c3nc(C)n4ccc(Cl)cc34)c21] | Cc1nc(C(=O)Nc2cccc3C(=O)NC(c23)c2cccc2C)c2cc(Cl)ccn12 | 1H NMR (400 MHz, DMSO-d6) 9.05 (s, 1H), 9.04 (s, 1H), 8.33 (dd, 7.6, 0.5 Hz, 1H), 8.17 (dd, 7.4, 1.3 Hz, 1H), 7.98 (dd, 2.1, 0.7 Hz), 7.59-7.50 (m, 2H), 7.17 (br. d, 7.4 Hz, 1H), 7.14-7.08 (m, 1H), 7.03 (br. t, 7.2 Hz, 1H), 6.97 (dd, 7.5, 2.1 Hz, 1H), 6.72 (br. s, 1H), 6.12 (s, 1H), 2.61 (s, 3H), 2.45 (br. s, 3H). | 431.3 | E | |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-278 | 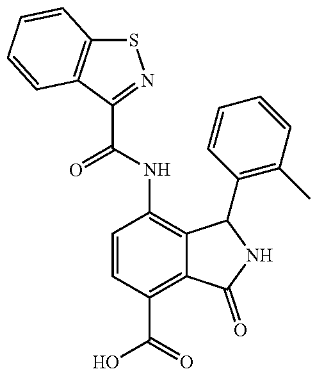 [SMILES: Cc1ccccc1C1NC(=O)c2c(C(=O)O)ccc(NC(=O)c3nsc4ccccc34)c21] | Cc1ccccc1C1NC(=O)c2c1c(NC(=O)c1nsc3cccc c13)ccc2C(O)=O | 1H NMR (400 MHz, DMSO-d6) 10.31 (br s, 1H), 8.61 (d, 8.1 Hz, 1 H), 8.31 (d, 8.2 Hz, 1H), 8.28 (d, 8.2 Hz, 1H), 8.10 (d, 8.3 Hz, 1H), 7.68 (ddd, 8.2, 7.0, 1.1 Hz, 1H), 7.63-7.57 (m, 1H), 7.43-7.27 (m), 7.11-7.02 (m, 2 H), 6.96 (d, 6.1 Hz, 1H), 6.85 (br s, 1H), 6.38 (s, 1H), 2.39 (br s, 3H). | 444.2 | C | |
| I-279 | 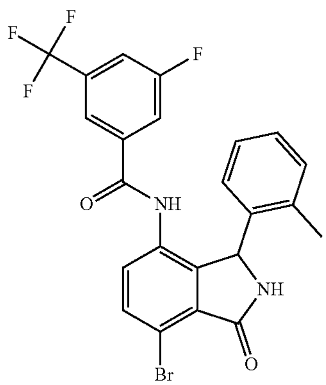 [SMILES: Cc1ccccc1C1NC(=O)c2c(Br)ccc(NC(=O)c3cc(F)cc(C(F)(F)F)c3)c21] | Cc1ccccc1C1NC(=O)c2c1c(NC(=O)c1cc(F)cc(c1)C(F)(F)F)ccc2Br | 1H NMR (400 MHz, DMSO-d6) 10.37 (s, 1H), 9.25 (s, 1H), 7.89 (d, 8.5 Hz, 1H), 7.79 (d, 8.3 Hz, 1 H), 7.46 (8.4 Hz, 1H), 7.31 (s, 1H), 7.07 (td, 7.5, 1.2 Hz, 1H), 7.03-6.91 (m, 2H), 6.53 (br s, 1H), 5.87 (s, 1H), 2.22 (br s, 3H). | 507.2 | B | |
| I-280 | 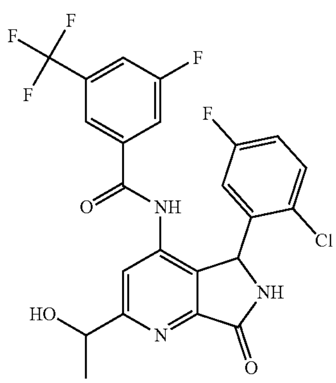 [SMILES: CC(O)c1cc(NC(=O)c2cc(F)cc(C(F)(F)F)c2)c2c(n1)C(=O)NC2c1cc(F)ccc1Cl] | CC(O)c1cc(NC(=O)c2cc(F)cc(c2)C(F)(F)F)c2C(NC(=O)c2n1)c1cc(F)ccc1Cl | 1H NMR (400 MHz, DMSO-d6) 10.84 (br s, 1H), 9.41 (s, 1H), 8.08-7.84 (m, 1H), 7.85-7.70 (m, 2H), 7.67 (s, 1H), 7.34 (dd, 8.8, 5.2 Hz, 1H), 7.09 (td, 8.3, 3.0 Hz, 1H), 6.78 (br s, 1H), 5.98 (s, 1H), 5.61 (br s, 1H), 4.96-4.76 (m, 1H), 1.46 (d, 6.5 Hz, 1.5H), 1.42 (d, 6.6 Hz, 1.5H). | 512.2 | B | |
| I-281 | 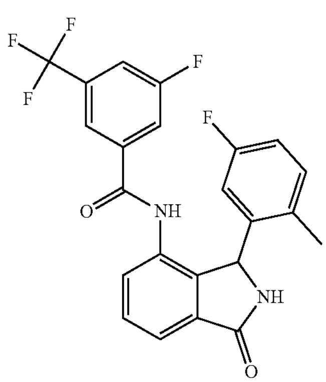 [SMILES: Cc1ccc(F)cc1C1NC(=O)c2cccc(NC(=O)c3cc(F)cc(C(F)(F)F)c3)c21] | Cc1ccc(F)cc1C1NC(=O)c2cccc(NC(=O)c3cc(F)cc(c3)C(F)(F)F)c12 | 1H NMR (400 MHz, DMSO-d6) 10.47 (s, 1H), 9.11 (s, 1H), 7.92 (d, 8.5 Hz, 1H), 7.70 (m, 1H), 7.65 (1, 7.6 Hz, 1H), 7.60 (d, 8.8 Hz, 1H), 7.52 (dd, 7.7, 1.1 Hz, 1H), 7.45 (s, 1H), 7.02 (dd, 8.5, 6.0 Hz, 1H), 6.89 (td, 8.5, 2.8 Hz, 1H), 6.35 (br s, 1H), 5.85 (s, 1H), 2.01 (br s, 3H). | 445.3 | B | |

TABLE 2-continued

Representative Compounds of the Invention with Bioactivity Data.

| Ex. No. | Structure | SMILES | $^1$H NMR | MS | ADP-Glo IC$_{50}$ | MCF 10A IC$_{50}$ |
|---|---|---|---|---|---|---|
| I-282 | 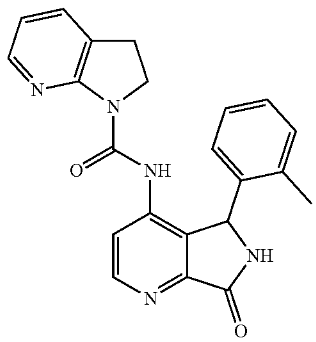 [SMILES: Cc1ccccc1C1NC(=O)c2nccc(NC(=O)N3CCc4cccnc43)c21] | Cc1ccccc1C1NC(=O)c2nccc(NC(=O)N3CCc4cccnc34)c12 | 1H NMR (400 MHz, DMSO-d6) 11.04 (s, 1H), 9.47 (s, 1H), 8.68 (d, 5.9 Hz, 1H), 8.41 (d, 5.6 Hz, 1H), 7.59 (d, 6.4 Hz, 1H), 7.46 (br s, 1H), 7.32 (d, 10.7,1H), 7.17 (t, 7.2 Hz, 1H), 7.01 (t, 7.5 Hz, 1H), 6.88 (dd, 7.1, 5.7 Hz, 1H), 6.56 (br s, 1H), 6.10 (s, 1H), 3.96 (t, 8.6 Hz, 2H), 3.02 (t, 8.6 Hz, 2H), 2.64 (br s, 3H). | 386.3 | D | |
| I-283 | 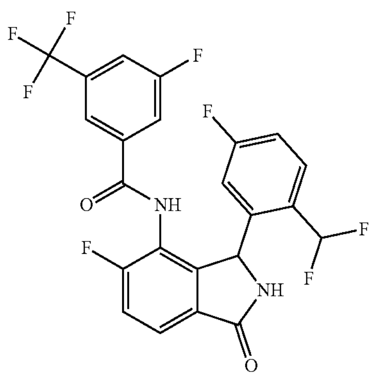 [SMILES: O=C(Nc1c(F)ccc2c1C(c1cc(F)ccc1C(F)F)NC2=O)c1cc(F)cc(C(F)(F)F)c1] | FC(F)c1cc(F)cc1C1NC(=O)c2ccc(F)c(NC(=O)c3cc(F)cc(c3)C(F)(F)F)c12 | 1H NMR (400 MHz, CD3CN) 8.53 (s, 1H), 7.83 (dd, 8.4, 4.6 Hz, 1H), 7.64 (d, 8.7 Hz, 1H), 7.59-7.40 (m, 4H), 7.24 (s, 1H), 7.10 (td, 8.9, 2.8 Hz, 1H), 6.62 (s, 1H), 6.02 (s, 1H). | 499.2 | C | |
| I-284 | 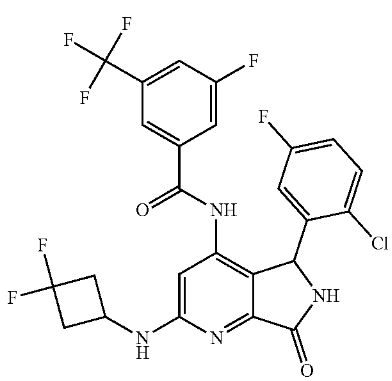 [SMILES: O=C(Nc1cc(NC2CC(F)(F)C2)nc2c1C(c1cc(F)ccc1Cl)NC2=O)c1cc(F)cc(C(F)(F)F)c1] | Fc1ccc(C1)c(c1)C1NC(=O)c2nc(NC3CC(F)(F)C3)cc(NC(=O)c3cc(F)cc(c3)C(F)(F)F)c12 | 1H NMR (400 MHz, DMSO-d6) 10.49 (br s, 1H), 9.15 (br s, 1H), 7.93 (br s, 1H), 7.68 (d, 8.9 Hz, 1H), 7.58 (br s, 1H), 7.33 (dd, 8.9, 5.1 Hz, 1H), 7.07 (td, 8.4, 3.1 Hz, 1H), 6.85-6.45 (m, 2H), 5.84 (br s, 1H), 4.38-4.15 (m, 1H), 3.13-2.88 (m, 2H), 2.65-2.52 (m, 2H). | 573.2 | A | |
| I-285 | 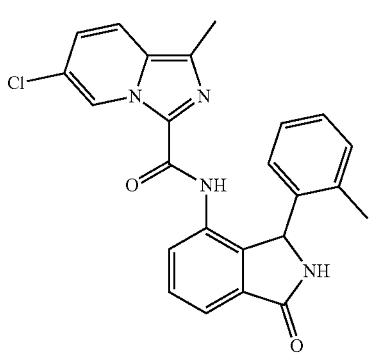 [SMILES: Cc1ccccc1C1NC(=O)c2cccc(NC(=O)c3nc(C)c4ccc(Cl)cn34)c21] | Cc1nc(C(=O)Nc2cccc3C(=O)NC(c23)c2ccccc2C)n2cc(Cl)ccc12 | 1H NMR (400 MHz, DMSO-d6) 9.60 (s, 1H), 9.24 (dd, 1.7, 0.9 Hz, 1H), 9.04 (s, 1H), 7.94 (dd, 6.1, 2.8 Hz, 1H), 7.86 (dd, 9.5, 0.9 Hz, 1H), 7.61-7.57 (m, 2H), 7.10 (dd, 9.6, 1.7 Hz, 1H), 7.07-7.00 (m, 2H), 6.98-6.92 (m, 1H), 6.69 (br s, 1H), 6.11 (s, 1H), 2.47 (s, 3H), 2.34 (br s, 3H). | 431.2 | E | |

TABLE 2-continued

Representative Compounds of the Invention with Bioactivity Data.

| Ex. No. | Structure | SMILES | $^1$H NMR | MS | ADP-Glo IC$_{50}$ | MCF 10A IC$_{50}$ |
|---|---|---|---|---|---|---|
| I-286 | 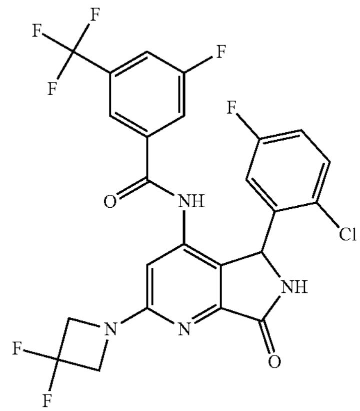 [SMILES: O=C(Nc1cc(N2CC(F)(F)C2)nc2c1C(c1cc(F)ccc1Cl)NC2=O)c1cc(F)cc(C(F)(F)F)c1] | Fc1ccc(C1)c(c1)C1NC(=O)c2nc(cc(NC(=O)c3cc(F)cc(c3)C(F)(F)F)c12)N1CC(F)(F)C1 | 1H NMR (400 MHz, DMSO-d6) 10.72 (br s, 1H), 9.30 (br s, 1H), 7.94 (d, 6.5 Hz, 1H), 7.71 (d, 9.0 Hz, 1H), 7.62 (s, 1H), 7.34 (dd, 8.9, 5.2 Hz, 1H), 7.17-6.97 (m, 1H), 6.94-6.56 (m, 2H), 5.91 (br s, 1H), 4.65-4.33 (m, 4H). | 559.3 | A | |
| I-287 | 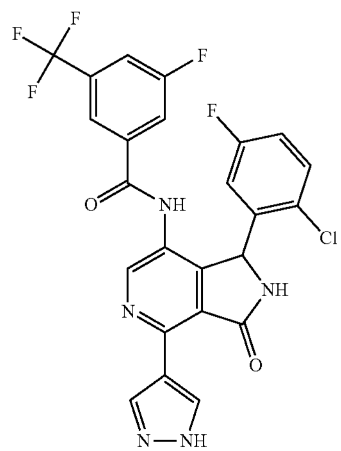 [SMILES: O=C(Nc1cnc(-c2cn[nH]c2)c2c1C(c1cc(F)ccc1Cl)NC2=O)c1cc(F)cc(C(F)(F)F)c1] | Fc1ccc(C1)c(c1)C1NC(=O)c2c1c(NC(=O)c1cc(F)cc(c1)C(F)(F)F)cnc2-c1cn[nH]c1 | 1H NMR (400 MHz, CD3OD) 8.80 (s, 1H), 8.92-8.44 (bs, 2H), 8.57 (s, 1H), 7.71-7.62 (m, 3H), 7.27 (dd, 8.9, 5.1 Hz, 1H), 6.99 (td, 7.9, 3.0 Hz, 1H), 6.83-6.65 (bs, 1H), 6.30-6.02 (bs, 1H). | 534.2 | B | |
| I-288 | 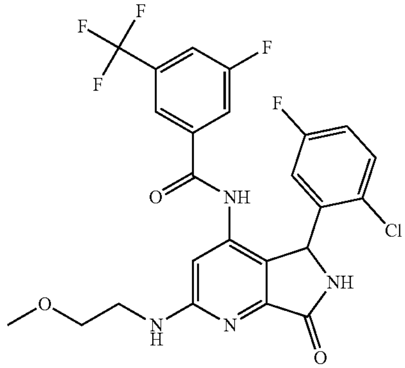 [SMILES: COCCNc1cc(NC(=O)c2cc(F)cc(C(F)(F)F)c2)c2c(n1)C(=O)NC2c1cc(F)ccc1Cl] | COCCNc1cc(NC(=O)c2cc(F)cc(c2)C(F)(F)F)c2C(NC(=O)c2n1)c1cc(F)ccc1Cl | 1H NMR (400 MHz, DMSO-d$_6$) δ 10.49 (s, 1H), 9.14 (s, 1H), 7.95 (d, J = 8.6 Hz, 1H), 7.67 (d, J = 8.7 Hz, 1H), 7.55 (s, 1H), 7.31 (dd, J = 8.9, 5.2 Hz, 1H), 7.21 (br s, 1H), 7.07 (td, J = 8.4, 3.1 Hz, 1H), 6.82 (br s, 1H), 6.65 (s, 1H), 5.82 (br s, 1H), 3.60-3.44 (m, 4H), 3.30 (s, 3H). | 541.2 | B | |

TABLE 2-continued

Representative Compounds of the Invention with Bioactivity Data.

| Ex. No. | Structure | SMILES | $^1$H NMR | MS | ADP-Glo IC$_{50}$ | MCF 10A IC$_{50}$ |
|---|---|---|---|---|---|---|
| I-289 | 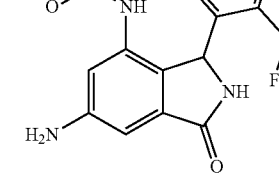 | Nc1cc2C(=O)NC(c2c(NC(=O)c2cc(F)cc(c2)C(F)(F)F)c1)cc(F)ccc1C(F)F | $^1$H NMR (400 MHz, DMSO-d$_6$) δ 10.21 (s, 1H) 8.89 (s, 1H) 7.88 (br d, J = 8.24 Hz, 1H) 7.61 (br d, J = 8.85 Hz, 1H) 7.38-7.58 (m, 2H) 7.15 (td, J = 8.31, 2.29 Hz, 1H) 6.86 (d, J = 1.83 Hz, 1H) 6.69 (d, J = 1.22 Hz, 1H) 6.50 (br s, 1H) 5.77 (br s, 1H) 5.66 (s, 2H) | 498.1 | A | A |
| I-290 | 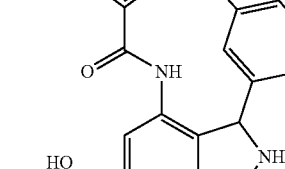 | CC(C)(O)c1cc2C(=O)NC(c2c(NC(=O)c2coc3c(F)cc(F)cc23)c1)cc(F)ccc1C(F)F | $^1$H NMR (400 MHz, DMSO-d$_6$) δ 10.28 (s, 1 H) 9.11 (s, 1 H) 8.46 (s, 1 H) 7.78 (s, 1 H) 7.60 (d, J = 1.22 Hz, 1 H) 7.36-7.49 (m, 2 H) 7.16 (td, J = 8.31, 2.29 Hz, 1 H) 6.42 (br s, 1 H) 6.03 (s, 1 H) 5.31 (s, 1 H) 1.51 (s, 6 H). | | A | |
| I-291 | 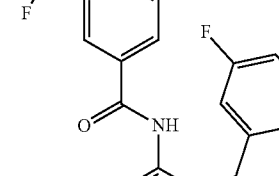 | CN1CCN(CC1)c1cc(NC(=O)c2cc(F)cc(c2)C(F)(F)c2C(NC(=O)c2n1)c1cc(F)ccc1Cl | $^1$H NMR (400 MHz, DMSO-d$_6$) δ 10.63 (br s, 1H), 9.22 (br s, 1H), 8.34 (br s, 1H), 7.93 (br d, J = 8.1 Hz, 1H), 7.71 (br d, J = 8.8 Hz, 1H), 7.63 (s, 1H), 7.31 (br dd, J = 8.8, 5.1 Hz, 1H), 7.06 (td, J = 8.3, 2.9 Hz, 1H), 6.92 (br s, 1H), 6.63-6.79 (m, 1H), 5.87 (br s, 1H), 3.47-3.66 (m, 4H), 2.32-2.47 (m, J = 4.6 Hz, 3H), 2.24 (s, 3H). | 566.5 | B | |
| I-292 | 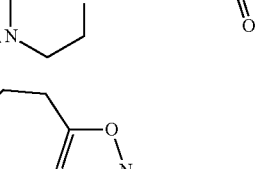 | Cc1ccccc1C1NC(=O)c2cccc(NC(=O)c3noc4CCCCc34)c12 | | 402.4 | E | |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-293 | 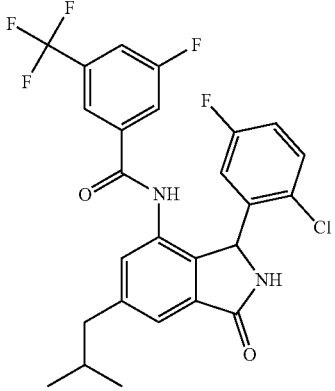 [SMILES: CC(C)Cc1cc(NC(=O)c2cc(F)cc(C(F)(F)F)c2)c2c(c1)C(=O)NC2c1cc(F)ccc1Cl] | CC(C)Cc1cc2C(=O)NC(c2c(NC(=O)c2cc(F)cc(c2)C(F)(F)F)c1)c1cc(F)ccc1Cl | 1H NMR (400 MHz, DMSO-d$_6$) 0.71-1.13 (m, 6H), 1.91 (dt, 13.36, 6.62 Hz, 1H), 2.55-2.67 (m, 2H), 5.92 (br s, 1H), 7.07 (td, 8.36, 3.05 Hz, 1H), 7.18-7.37 (m, 2H), 7.47 (s, 1H), 7.65 (s, 1H), 7.72 (br d, 9.03 Hz, 1H), 7.92 (br d, 8.54 Hz, 1H), 9.06 (br s, 1H), 10.44 (s, 1H) | 523.4 | A | |
| I-294 | 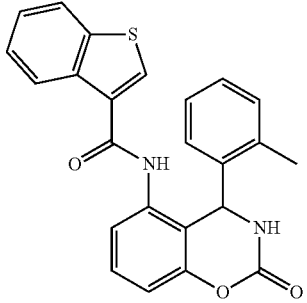 [SMILES: Cc1ccccc1C1NC(=O)Oc2cccc(NC(=O)c3csc4ccccc34)c21] | Cc1ccccc1C1NC(=O)Oc2ccccc(NC(=O)c3csc4ccccc34)c12 | | | | B |
| I-295 | 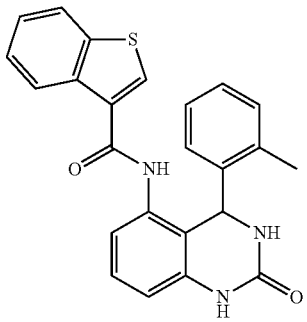 [SMILES: Cc1ccccc1C1NC(=O)Nc2cccc(NC(=O)c3csc4ccccc34)c21] | Cc1ccccc1C1NC(=O)Nc2ccccc(OC(=O)c3csc4ccccc34)c12 | | | | D |
| I-296 | 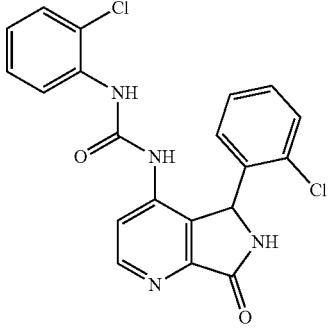 [SMILES: O=C(Nc1ccccc1Cl)Nc1ccnc2c1C(c1ccccc1Cl)NC2=O] | Clc1ccccc1NC(=O)Nc1ccnc2C(=O)NC(c12)c1ccccc1Cl | 1H NMR (400 MHz, DMSO-d$_6$) δ 9.40 (br s, 1H), 9.25 (br s, 1H), 8.65 (br d, J = 5.4 Hz, 1H), 8.47 (br s, 1H), 7.87 (br d, J = 7.8 Hz, 1H), 7.66 (br d, J = 5.1 Hz, 1H), 7.44 (br d, J = 8.1 Hz, 2H), 7.27-7.36 (m, 2H), 7.22 (br t, J = 7.4 Hz, 1H), 7.04-7.11 (m, 1H), 6.81-6.95 (m, 1H), 6.15 (br s, 1H). | 413.3 | | D |

TABLE 2-continued

Representative Compounds of the Invention with Bioactivity Data.

| Ex. No. | Structure | SMILES | $^1$H NMR | MS | ADP-Glo IC$_{50}$ | MCF 10A IC$_{50}$ |
|---|---|---|---|---|---|---|
| I-297 | 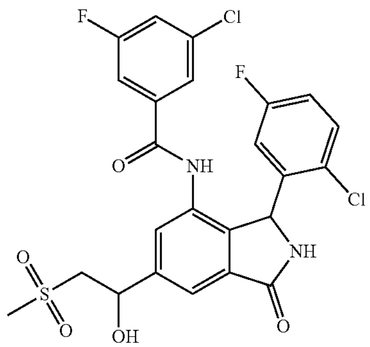 [SMILES: CS(=O)(=O)CC(O)c1cc(NC(=O)c2cc(F)cc(Cl)c2)c2c(c1)C(=O)NC2c1cc(F)ccc1Cl] | CS(=O)(=O)CC(O)c1cc2C(=O)NC(c2c(NC(=O)c2cc(F)cc(Cl)c2)c1)c1cc(F)ccc1Cl | 1H NMR (500 MHz, DMSO-d6) 2.89-3.11 (m, 3H), 3.56-3.86 (m, 1H), 5.06-5.29 (m, 1H), 5.79-6.06 (m, 1H), 6.12-6.28 (m, 1H), 6.54-6.72 (m, 1H), 7.00-7.21 (m, 1H), 7.26-7.44 (m, 2H), 7.48-7.96 (m, 4H), 8.93-9.42 (m, 2H), 10.18-10.55 (m, 1H) | 555 | B | |
| I-298 | 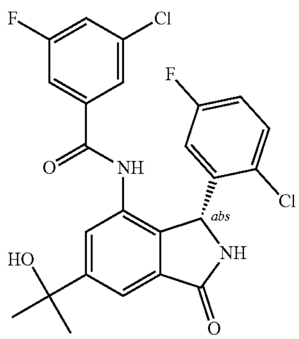 [SMILES: CC(C)(O)c1cc(NC(=O)c2cc(F)cc(Cl)c2)c2c(c1)C(=O)N[C@H]2c1cc(F)ccc1Cl] | CC(C)(O)c1cc2C(=O)N[C@H](c2c(NC(=O)c2cc(F)cc(Cl)c2)c1)c1cc(F)ccc1Cl | 1H NMR (500 MHz, DMSO-d6) 10.3-10.4 (m, 1H), 8.9-9.2 (m, 1H), 7.7-7.8 (m, 1H), 7.6-7.7 (m, 1H), 7.5-7.6 (m, 1H), 7.3-7.5 (m, 3H), 7.1-7.2 (m, 1H), 6.3-6.9 (m, 1H), 5.6-6.2 (m, 1H), 5.2-5.4 (m, 1H), 1.4-1.6 (m, 6H) | 492 | A | A |
| I-299 | 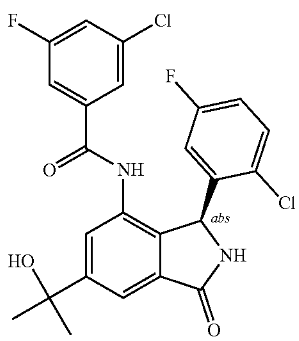 [SMILES: CC(C)(O)c1cc(NC(=O)c2cc(F)cc(Cl)c2)c2c(c1)C(=O)N[C@@H]2c1cc(F)ccc1Cl] | CC(C)(O)c1cc2C(=O)N[C@@H](c2c(NC(=O)c2cc(F)cc(Cl)c2)c1)c1cc(F)ccc1Cl | 1H NMR (500 MHz DMSO-d6) 10.3-10.4 (m, 1H), 8.9-9.2 (m, 1H), 7.7-7.8 (m, 1H), 7.6-7.7 (m, 1H), 7.5-7.6 (m, 1H), 7.3-7.5 (m, 3H), 7.1-7.2 (m, 1H), 6.3-6.9 (m, 1H), 5.6-6.2 (m, 1H), 5.2-5.4 (m, 1H), 1.4-1.6 (m, 6H) | 492 | E | |
| I-300 | 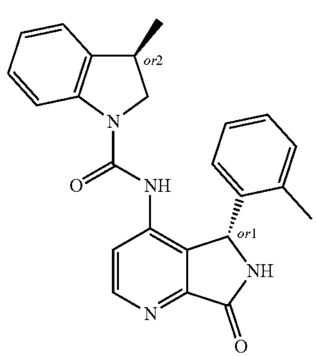 [SMILES: Cc1ccccc1[C@@H]1NC(=O)c2nccc(NC(=O)N3C[C@H](C)c4ccccc43)c21] | C[C@H]1CN(C(=O)Nc2ccnc3C(=O)N[C@H](c23)c2ccccc2C)c2ccccc12 | 1H NMR (400 MHz, DMSO-d6) 9.31 (s, 2H), 8.78 (br s, 1H), 8.67 (br s, 1H), 8.61 (s, 1H), 8.60 (s, 1H), 7.64 (d, 8.0 Hz, 1H), 7.59 (d, 8.1 Hz, 1H), 7.46 (d, 5.4 Hz, 1H), 7.40 (d, 5.3 Hz, 1H), 7.17-7.05 (m, 6H), 7.03-6.87 (m, 6H), 6.49 (br s, 2H), 5.89 (s, 1H), 5.88 (s, 1H), 3.79-3.65 (m, 2H), 3.25-3.08 (m, 2H), 2.99 (dd, 8.9, 5.9 Hz, 1H), 2.51 (dd, 10.0, 6.7 Hz, 1H), 2.15 (br s, 6H), 1.09 (d, 7.6 Hz, 3H), 1.04 (d, 6.8 Hz, 3H) | 398.5 | B | |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-301 | 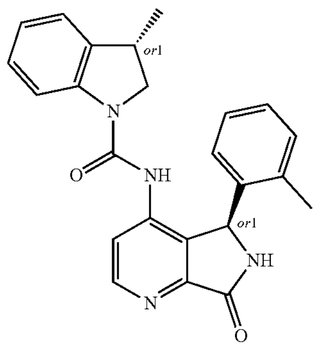 [SMILES: Cc1ccccc1[C@H]1NC(=O)c2nccc(NC(=O)N3C[C@@H](C)c4ccccc43)c21] | C[C@@H]1CN(C(=O)Nc2cncc3C(=O)N[C@@H](c23)c2ccccc2C)c2ccccc12 | 1H NMR (400 MHz, DMSO-d6) 9.31 (s, 2H), 8.78 (br s, 1H), 8.67 (br s, 1H), 8.61 (s, 1H), 8.60 (s, 1H), 7.64 (d, 8.0 Hz, 1H), 7.59 (d, 8.1 Hz, 1H), 7.46 (d, 5.4 Hz, 1H), 7.40 (d, 5.3 Hz, 1H), 7.17-7.05 (m, 6H), 7.03-6.87 (m, 6H), 6.49 (br s, 2H), 5.89 (s, 1H), 5.88 (s, 1H), 3.79-3.65 (m, 2H), 3.25-3.08 (m, 2H), 2.99 (dd, 8.9, 5.9 Hz, 1H), 2.51 (dd, 10.0, 6.7 Hz, 1H), 2.15 (br s, 6H), 1.09 (d, 7.6 Hz, 3H), 1.04 (d, 6.8 Hz, 3H) | 398.5 | C | |
| I-302 | 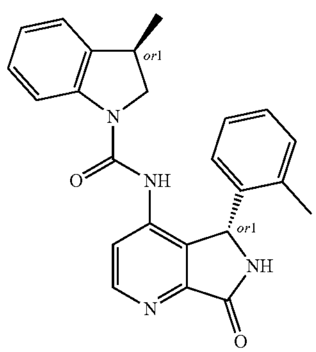 [SMILES: Cc1ccccc1[C@@H]1NC(=O)c2nccc(NC(=O)N3C[C@H](C)c4ccccc43)c21] | C[C@H]1CN(C(=O)Nc2ccnc3C(=O)N[C@H](c23)c2ccccc2C)c2ccccc12 | 1H NMR (400 MHz, DMSO-d6) 9.31 (s, 2H), 8.78 (br s, 1H), 8.67 (br s, 1H), 8.61 (s, 1H), 8.60 (s, 1H), 7.64 (d, 8.0 Hz, 1H), 7.59 (d, 8.1 Hz, 1H), 7.46 (d, 5.4 Hz, 1H), 7.40 (d, 5.3 Hz, 1H), 7.17-7.05 (m, 6H), 7.03-6.87 (m, 6H), 6.49 (br s, 2H), 5.89 (s, 1H), 5.88 (s, 1H), 3.79-3.65 (m, 2H), 3.25-3.08 (m, 2H), 2.99 (dd, 8.9, 5.9 Hz, 1H), 2.51 (dd, 10.0, 6.7 Hz, 1H), 2.15 (br s, 6H), 1.09 (d, 7.6 Hz, 3H), 1.04 (d, 6.8 Hz, 3H) | 398.5 | C | |
| I-303 | 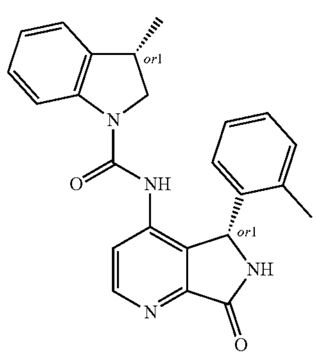 [SMILES: Cc1ccccc1[C@@H]1NC(=O)c2nccc(NC(=O)N3C[C@@H](C)c4ccccc43)c21] | C[C@@H]1CN(C(=O)Nc2ccnc3C(=O)N[C@H](c23)c2ccccc2C)c2ccccc12 | 1H NMR (400 MHz, DMSO-d6) 9.31 (s, 2H), 8.78 (br s, 1H), 8.67 (br s, 1H), 8.61 (s, 1H), 8.60 (s, 1H), 7.64 (d, 8.0 Hz, 1H), 7.59 (d, 8.1 Hz, 1H), 7.46 (d, 5.4 Hz, 1H), 7.40 (d, 5.3 Hz, 1H), 7.17-7.05 (m, 6H), 7.03-6.87 (m, 6H), 6.49 (br s, 2H), 5.89 (s, 1H), 5.88 (s, 1H), 3.79-3.65 (m, 2H), 3.25-3.08 (m, 2H), 2.99 (dd, 8.9, 5.9 Hz, 1H), 2.51 (dd, 10.0, 6.7 Hz, 1H), 2.15 (br s, 6H), 1.09 (d, 7.6 Hz, 3H), 1.04 (d, 6.8 Hz, 3H) | 398.5 | E | |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-304 | 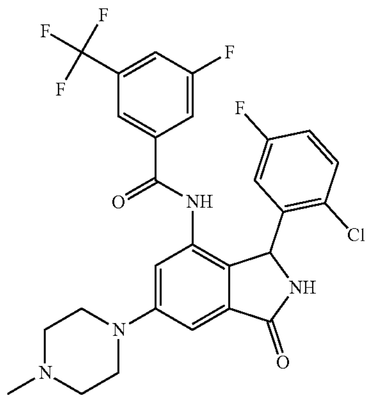 [SMILES: CN1CCN(c2cc(NC(=O)c3cc(F)cc(C(F)(F)F)c3)c3c(c2)C(=O)NC3c2cc(F)ccc2Cl)CC1] | CNCCN(CC1)c1c c2C(=O) NC(c2c (NC(=O)c 2cc(F)cc (c2)C(F) (F)F)c1)c 1cc(F)ccc 1Cl | 1H NMR (400 MHz, DMSO-d6) 2.87 (br s, 2 H), 3.02-3.25 (m, 3H), 3.53 (br s, 2H), 3.98 (br d, 4.15 Hz, 2H), 5.73-6.03 (m, 2H) 6.53 (br s, 1H), 7.00-7.19 (m, 2H), 7.22-7.40 (m, 2H), 7.60-7.80 (m, 2H) 7.95 (br d, 8.30 Hz, 1H) 9.07 (br s, 1H) 9.69 (br s, 1H) 10.41 (s, 1H) | 565.36 | A | |
| I-305 | 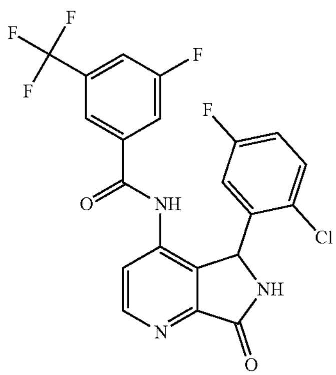 [SMILES: O=C(Nc1ccnc2c1C(c1cc(F)ccc1Cl)NC2=O)c1cc(F)cc(C(F)(F)F)c1] | Fc1ccc(C 1)c(c1)C1 NC(=O)c 2nccc(N C(=O)c3 cc(F)cc(c 3)C(F)(F) F)c12 | 1H NMR (400 MHz, DMSO-d6) 10.75 (br s, 1H), 9.46 (s, 1H), 8.75 (d, 4.4 Hz, 1H), 7.94 (d, 7.0 Hz, 1H), 7.73 (d, 9.1 Hz, 1H), 7.64 (s, 1H), 7.58 (s, 1H), 7.35 (dd, 8.9, 5.2 Hz, 1H), 7.10 (ddd, 8.8, 8.0, 3.1 Hz, 1H), 7.02-6.55 (br s, 1H), 6.06-5.92 (br s, 1H) | 468.2 | B | |
| I-306 | 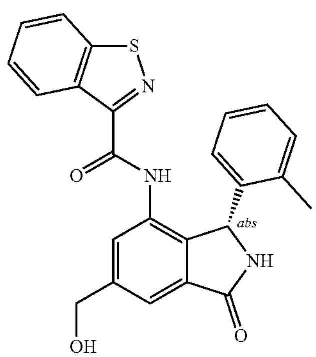 [SMILES: Cc1ccccc1[C@@H]1NC(=O)c2cc(CO)cc(NC(=O)c3nsc4ccccc34)c21] | Cc1ccccc 1[C@@ H]1NC(= O)c2cc(C O)cc(NC (=O)c3ns c4ccccc3 4)c12 | 1H NMR (400 MHz, DMSO-d6) 10.12 (s, 1H), 9.01 (s, 1H), 8.55 (d, 7.8 Hz, 1H), 8.29 (d, 8.3 Hz, 1H), 7.78 (s, 1H), 7.66 (t, 7.2 Hz, 1H), 7.59 (s, 1H), 7.55 (m, 1H), 7.02-6.95 (m, 2H), 6.91 (t, 6.5 Hz, 1H), 6.68 (br s, 1H), 6.09 (s, 1H), 5.45 (s, 1H), 4.65 (s, 2H), 2.25 (br s, 3H). | 430.3 | A | |
| I-307 | 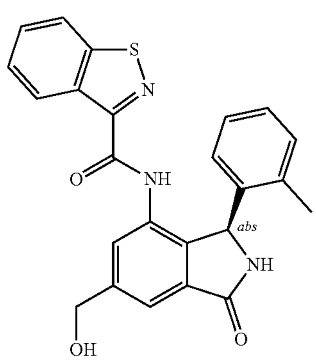 [SMILES: Cc1ccccc1[C@H]1NC(=O)c2cc(CO)cc(NC(=O)c3nsc4ccccc34)c21] | Cc1ccccc 1[C@H] 1NC(=O) c2cc(CO) cc(NC(= O)c3nsc4 ccccc34) c12 | 1H NMR (400 MHz, DMSO-d6) 10.12 (s, 1H), 9.02 (s, 1H), 8.56 (d, 8.2 Hz, 1H), 8.29 (d, 8.2 Hz, 1H), 7.78 (d, 0.9 Hz, 1H), 7.67 (ddd, 8.2, 7.0, 1.1 Hz, 1H), 7.60 (s, 1H), 7.57 (t, 7.6 Hz, 1H), 7.02-6.95 (m, 2H), 6.91 (t, 6.6 Hz, 1H), 6.69 (br s, 1H), 6.09 (s, 1H), 5.46 (t, 5.7 Hz, 1H), 4.65 (d, 5.1 Hz, 2H), 2.26 (br s, 3H). | 430.3 | D | |

TABLE 2-continued

Representative Compounds of the Invention with Bioactivity Data.

| Ex. No. | Structure | SMILES | $^1$H NMR | MS | ADP-Glo IC$_{50}$ | MCF 10A IC$_{50}$ |
|---|---|---|---|---|---|---|
| I-308 | 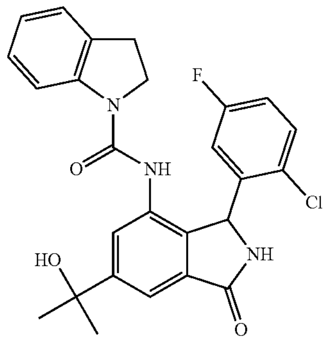 [SMILES: CC(C)(O)c1cc(NC(=O)N2CCc3ccccc32)c2c(c1)C(=O)NC2c1cc(F)ccc1Cl] | CC(C)(O)c1cc2C(=O)NC(c2c(NC(=O)N2CCc3ccccc23)c1)c1cc(F)ccc1Cl | 1H NMR (400 MHz, DMSO-d6) 8.99 (s, 1H), 8.55 (s, 1H), 7.71 (d, 7.9 Hz, 1H), 7.65 (d, 1.4 Hz, 1H), 7.49 (d, 1.4 Hz, 1H), 7.36 (dd, 8.9, 5.2 Hz, 1H), 7.20-7.11 (m, 2H), 7.09 (t, 7.7 Hz, 1H), 6.88 (td, 7.4, 1.0 Hz, 1H), 6.54 (br s, 1H), 5.97 (br s, 1H), 5.25 (br s, 1H), 3.93-3.83 (m, 1H), 3.09-2.93 (m, 3H), 1.49 (s, 6H). | 480.5 | A | |
| I-309 | 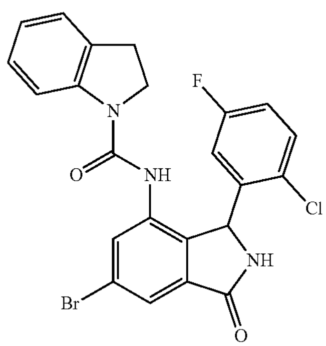 [SMILES: O=C1NC(c2cc(F)ccc2Cl)c2c(NC(=O)N3CCc4ccccc43)cc(Br)cc21] | Fc1ccc(C1)c(c1)C1NC(=O)c2cc(Br)cc(NC(=O)N3CCc4ccccc34)c12 | 1H NMR (400 MHz, DMSO-d6) 9.20 (s, 1H), 8.66 (s, 1H), 7.74-7.64 (m, 2H), 7.59 (s, 1H), 7.37 (dd, 8.8, 5.3 Hz, 1H), 7.22-7.05 (m, 3H), 6.90 (t, 7.4 Hz, 1H), 6.64 (br s, 1H), 5.99 (br s, 1H), 3.80 (dd, 17.2, 9.7 Hz, 1H), 3.27-3.13 (m, 1H), 3.10-2.92 (m, 2H) | 500.1 | A | |
| I-310 | 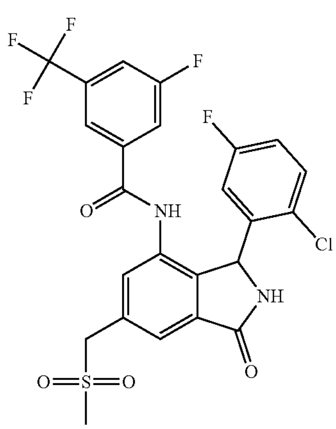 | CS(=O)(=O)Cc1cc2C(=O)NC(c2c(NC(=O)c2cc(F)cc(c2)C(F)(F)F)c1)c1cc(F)ccc1Cl | 1H NMR (400 MHz, DMSO-d6) 10.62 (s, 1H), 9.22 (s, 1H), 7.95 (d, 8.5 Hz, 1H), 7.77 (s, 1H), 7.74 (d, 8.9 Hz, 1H), 7.64 (s, 1H), 7.52 (s, 1H), 7.32 (dd, 8.9, 5.2 Hz, 1H), 7.10 (td, 8.4, 3.0 Hz, 1H), 6.65 (br s, 1H), 5.98 (br s, 1H), 4.72 (s, 2H), 2.98 (s, 3H). | 559 | A | |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-311 | 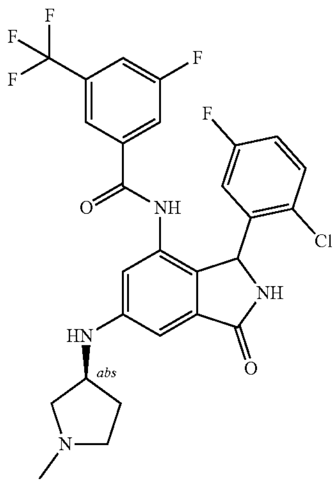 [SMILES: CN1CC[C@H](Nc2cc(NC(=O)c3cc(F)cc(C(F)(F)F)c3)c3c(c2)C(=O)NC3c2cc(F)ccc2Cl)C1] | CN1CC[C@@H](C1)Nc1cc2C(=O)NC(c2c(NC(=O)c2cc(F)cc(c2)C(F)(F)F)c1)c1cc(F)ccc1Cl | 1H NMR (400 MHz, DMSO-d6) 10.28 (s, 1H), 8.91 (br. s, 1H), 7.92 (dt, 8.4 and 1.6 Hz, 1H), 7.69 (d, 9.4 Hz, 1H), 7.60 (s, 1H), 7.28 (dd, 8.9, 5.2 Hz, 1H), 7.06 (td, 8.3, 3.1 Hz, 1H), 6.77 (t, 1.7 Hz, 1H), 6.68-6.64 (m, 1H), 6.36 (d, 6.6 Hz, 1H), 5.82 (br. s, 1H), 3.96-3.89 (m, 1H), 2.76-2.72 (m, 1H), 2.64-2.59 (m, 1H), 2.43-2.36 (m, 2H), 2.27 (s, 3H), 2.27-2.20 (m, 1H), 1.67-1.58 (m, 1H). | 565.4 | A | |
| I-312 | 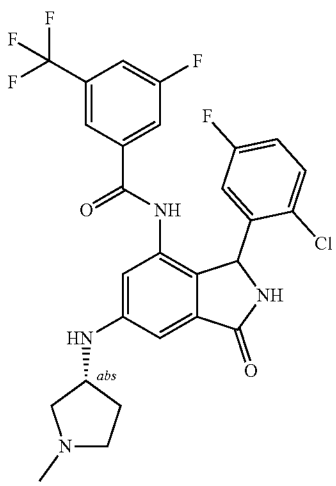 [SMILES: CN1CC[C@@H](Nc2cc(NC(=O)c3cc(F)cc(C(F)(F)F)c3)c3c(c2)C(=O)NC3c2cc(F)ccc2Cl)C1] | CN1CC[C@H](C1)Nc1cc2C(=O)NC(c2c(NC(=O)c2cc(F)cc(c2)C(F)(F)F)c1)c1cc(F)ccc1Cl | 1H NMR (400 MHz, DMSO-d6) 10.27 (s, 1H), 8.91 (br s, 1H), 8.22 (s, 1H), 7.92 (dt, 8.4 and 1.6 Hz, 1H), 7.69 (d, 9.2 Hz, 1H), 7.60 (s, 1H), 7.28 (dd, 8.9, 5.2 Hz, 1H), 7.06 (td, 8.4, 3.0 Hz, 1H), 6.77 (t, 1.7 Hz, 1H), 6.71-6.59 (m, 1H), 6.57 (br. s, 1H), 6.37 (d, 6.6 Hz, 1H), 5.82 (br. s, 1H), 3.98-3.90 (m, 1H), 2.77 (ddd, 9.1, 6.7, 2.4 Hz, 1H), 2.69-2.57 (m, 1H), 2.47-2.39 (m, 2H), 2.28 (s, 3H), 2.27-2.20 (m, 1H), 1.68-1.59 (m, 1H). | 565.3 | A | |
| I-313 | 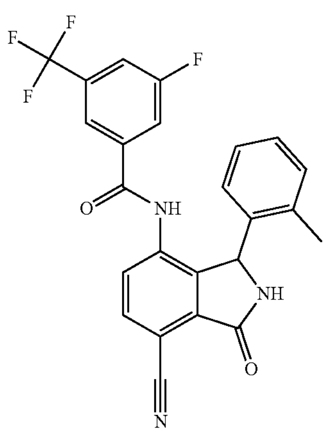 [SMILES: Cc1ccccc1C1NC(=O)c2c(C#N)ccc(NC(=O)c3cc(F)cc(C(F)(F)F)c3)c21] | Cc1ccccc1C1NC(=O)c2c1c(NC(=O)c1cc(F)cc(c1)C(F)(F)F)ccc2C#N | 1H NMR (400 MHz, DMSO-d6) 10.64 (br s, 1H), 9.48 (s, 1H), 8.08 (d, 8.1 Hz, 1H), 7.90 (d, 8.3 Hz, 1H), 7.77 (d, 8.0 Hz., 1H), 7.49-7.43 (m, 1H), 7.30 (br s, 1H), 7.08 (td, 7.5, 1.2 Hz, 1H), 7.01 (d, 7.2 Hz, 1H), 6.97 (t, 7.3 Hz, 1H), 6.52 (br s, 1H), 5.96 (s, 1H), 2.28 (s, 3 H). | 454.2 | B | |

TABLE 2-continued

Representative Compounds of the Invention with Bioactivity Data.

| Ex. No. | Structure | SMILES | $^1$H NMR | MS | ADP-Glo IC$_{50}$ | MCF 10A IC$_{50}$ |
|---|---|---|---|---|---|---|
| I-314 | 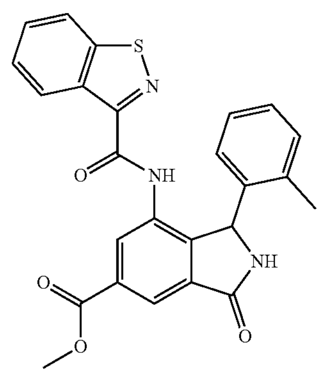 [SMILES: COC(=O)c1cc(NC(=O)c2nsc3ccccc23)c2c(c1)C(=O)NC2c1ccccc1C] | COC(=O) c1cc2C (=O)NC(c 2c(NC(= O)c2nsc3 ccccc23) c1)c1ccc cc1C | 1H NMR (400 MHz, DMSO-d6) 10.28 (s, 1H), 9.29 (s, 1H), 8.62 (d, 8.2 Hz, 1H), 8.45 (d, 1.4 Hz, 1H), 8.31 (dt, 8.2, 0.8 Hz, 1H), 8.13 (d, 1.4 Hz, 1H), 7.68 (ddd, 8.2, 7.0, 1.2 Hz, 1H), 7.59 (ddd, 8.1, 7.0, 1.0 Hz, 1H), 7.02-6.98 (m, 2H), 6.96-6.87 (m, 2H), 6.22 (br s, 1H), 3.94 (s, 3H), 2.26 (br s, 3H). | 458.3 | C | |
| I-315 | 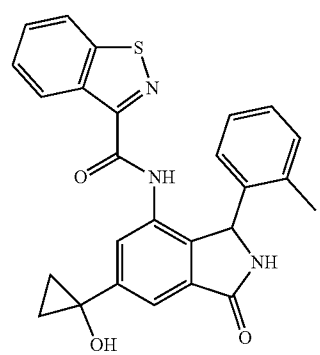 [SMILES: Cc1ccccc1C1NC(=O)c2cc(C3(O)CC3)cc(NC(=O)c3nsc4ccccc34)c21] | Cc1cccc c1C1NC(= O)c2cc(c c(NC(=O) c3nsc4c cccc34)c 12)C1(O) CC1 | 1H NMR (400 MHz, DMSO-d6) 10.13 (s, 1H), 9.00 (s, 1H), 8.56 (d, 8.1 Hz, 1H), 8.28 (dd, 5.0, 4.1 Hz, 1H), 7.66 (ddd, 8.2, 7.0, 1.2 Hz, 1H), 7.64 (d, 1.5 Hz, 1H), 7.57 (ddd, 8.1, 7.0, 1.0 Hz, 1H), 7.49 (d, 1.6 Hz, 1H), 7.01-6.85 (m, 3H), 6.67 (brs, 1H), 6.18 (s, 1H), 6.07 (br s, 1H), 2.23 (br s, 3H), 1.24-1.16 (m, 2H), 1.09-1.03 (m, 2H). | 456.3 | A | |
| I-316 | 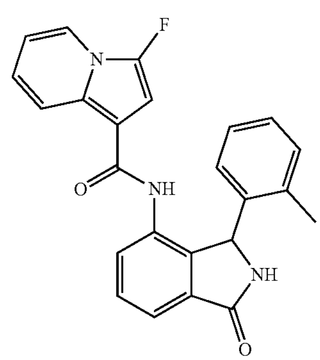 [SMILES: Cc1ccccc1C1NC(=O)c2cccc(NC(=O)c3cc(F)n4ccccc34)c21] | Cc1cccc c1C1NC(= O)c2cccc (NC(=O) c3cc(F)n 4ccccc34) c12 | 1H NMR (400 MHz, CD3CN) 8.09 (d, 9.2 Hz, 1H), 7.93 (d, 7.0 Hz, 1H), 7.88 (d, 7.9 Hz, 1H), 7.66-7.54 (m, 3H), 7.19-7.08 (m, 3H), 7.05 (t, 7.6 Hz, 1H), 6.99 (ddd, 9.3, 6.6, 1.0 Hz, 1H), 6.83 (td, 6.9, 1.2 Hz, 1H), 6.06 (br s, 1H), 5.94 (d, 3.1 Hz, 1H), 2.15 (br s, 3H) | 400.1 | C | |
| I-317 | 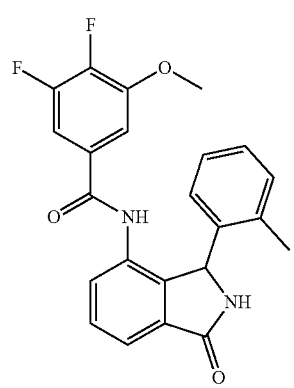 [SMILES: COc1cc(C(=O)Nc2cccc3c2C(c2ccccc2C)NC3=O)cc(F)c1F] | COc1cc (cc(F)c1F) C(=O)Nc 1cccc2C (=O)NC(c 12)c1ccc cc1C | 1H NMR (400 MHz, DMSO-d6) 10.14 (s, 1H), 9.05 (s, 1H), 7.67 (dd, 7.4, 1.2 Hz, 1H), 7.61 (t, 7.5 Hz, 1H), 7.53 (dd, 7.7, 1.1 Hz, 1H), 7.10 (td, 7.4, 1.3 Hz, 1H), 7.03 (d, 7.1 Hz, 1H), 7.00-6.96 (m, 2H), 6.94-6.89 (mt, 1H), 6.57 (br. s, 1H), 5.92 (s, 1H), 3.84 (s, 3H), 2.19 (br. s, 3H). | 409.2 | C | |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-318 | 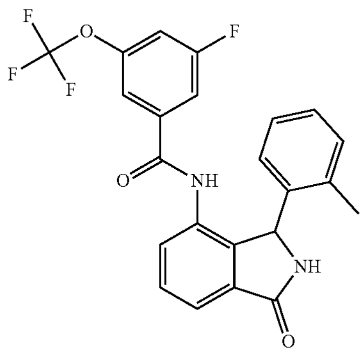 [SMILES: Cc1ccccc1C1NC(=O)c2cccc(NC(=O)c3cc(F)cc(OC(F)(F)F)c3)c21] | Cc1ccccc1C1NC(=O)c2cccc(NC(=O)c3cc(F)cc(OC(F)(F)F)c3)c12 | 1H NMR (400 MHz, DMSO-d6) 10.29 (s, 1H), 9.06 (s, 1H), 7.68 (dd, 7.5, 1.1 Hz, 1H), 7.61 (t, 7.5 Hz, 1H), 7.61 (mt, 1H, 1H), 7.53 (dd, 7.6, 0.7 Hz, 1H), 7.19 (br. d, 8.6 Hz, 1H), 7.11 (br. s, 1H), 7.07 (td, 7.5, 1.3 Hz, 1H), 7.00 (d, 7.0 Hz, 1H), 6.95 (br. t, 7.2 Hz, 1H), 6.55 (br. s, 1H), 5.90 (s, 1H), 2.19 (br. s, 3H). | 445.2 | C | |
| I-319 | 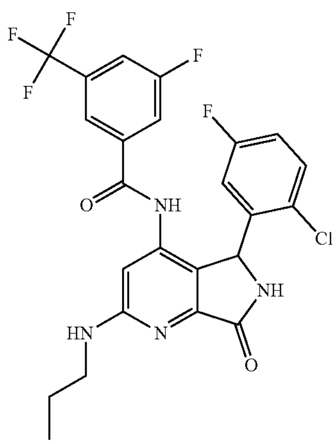 [SMILES: CCCNc1cc(NC(=O)c2cc(F)cc(C(F)(F)F)c2)c2c(n1)C(=O)NC2c1cc(F)ccc1Cl] | CCCNc1cc(NC(=O)c2cc(F)cc(c2)C(F)(F)F)c2C(NC(=O)c2n1)c1cc(F)ccc1Cl | 1H NMR (400 MHz, DMSO-d6) 10.45 (br s, 1H), 9.12 (br s, 1H), 7.93 (d, 8.4 Hz, 1H), 7.67 (d, 9.4 Hz, 1H), 7.57 (s, 1H), 7.30 (dd, 8.9, 5.2 Hz, 1H), 7.11 (br s, 1H), 7.06 (ddd, 8.8, 8.1, 3.1 Hz, 1H), 6.74 (br s, 1H), 6.62 (s, 1H), 5.82 (br s, 1H), 3.28-3.25 (m, 2H), 1.59 (sx, 7.4 Hz, 2H), 0.95 (t, 7.4 Hz, 3H). | 525.2 | A | |
| I-320 | 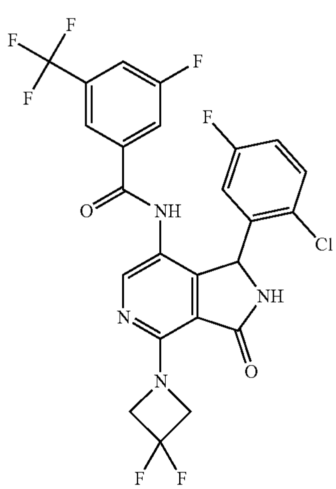 [SMILES: O=C(Nc1cnc(N2CC(F)(F)C2)c2c1C(c1cc(F)ccc1Cl)NC2=O)c1cc(F)cc(C(F)(F)F)c1] | Fc1ccc(C1)c(c1)C1NC(=O)c2c1c(NC(=O)c1cc(F)cc(c1)C(F)(F)F)cnc2N1CC(F)(F)C1 | 1H NMR (400 MHz, CD3CN) 8.46 (br s, 1H), 8.20 (s, 1H), 7.66-7.58 (m, 3H), 7.23 (dd, 8.9, 5.1 Hz, 1H), 7.05 (br s, 1H), 6.98 (ddd, 8.8, 8.0, 3.1 Hz, 1H), 6.76 (br s, 1H), 6.05 (br s, 1H), 4.80-4.31 (m, 4H). | 559.2 | B | |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-321 | 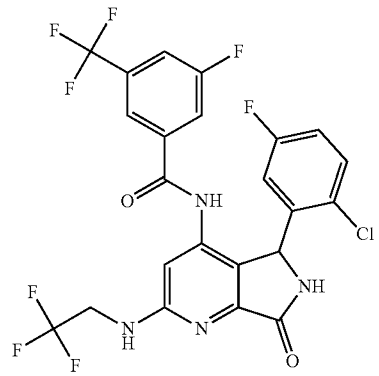 [SMILES: O=C(Nc1cc(NCC(F)(F)F)nc2c1C(c1cc(F)ccc1Cl)NC2=O)c1cc(F)cc(C(F)(F)F)c1] | Fc1ccc(C1)c(c1)C1NC(=O)c2nc(NCC(F)(F)F)cc(NC(=O)c3cc(F)cc(c3)C(F)(F)F)c12 | 1H NMR (400 MHz, DMSO-d6) 10.38 (br s, 1H), 9.22 (s, 1H), 7.93 (d, 8.3 Hz, 1H), 7.73-7.66 (m, 2H), 7.57 (s, 1H), 7.32 (dd, 8.9, 5.2 Hz, 1H), 7.07 (ddd, 8.7, 8.0, 3.1 Hz, 1H), 6.83 (s, 1H), 6.75 (br s, 1H), 5.85 (br s, 1H), 4.43-4.16 (m, 2H). | 565.1 | A | |
| I-322 | 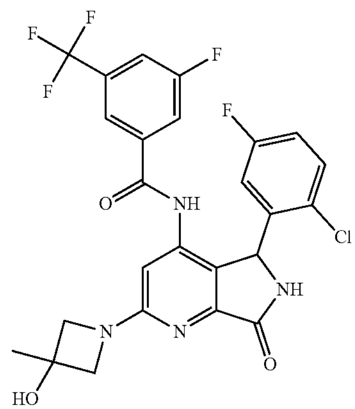 [SMILES: CC1(O)CN(c2cc(NC(=O)c3cc(F)cc(C(F)(F)F)c3)c3c(n2)C(=O)NC3c2cc(F)ccc2Cl)C1] | CC1(O)CN(C1)c1cc(NC(=O)c2cc(F)cc(c2)C(F)(F)c2C(NC(=O)c2n1)c1cc(F)ccc1C1 | 1H NMR (400 MHz, DMSO-d6) 10.59 (s, 1H), 9.22 (s, 1H), 8.10-7.84 (m, 1H), 7.70 (d, 9.6 Hz, 1H), 7.61 (s, 1H), 7.45-7.22 (m, 1H), 7.07 (t, 7.9 Hz, 1H), 6.71 (br s, 1H), 6.61-6.30 (m, 1H), 5.87 (br s, 1H), 5.66 (s, 1H), 3.94-3.85 (m, 4H), 1.47 (s, 3H). | 553.2 | B | |
| I-323 | 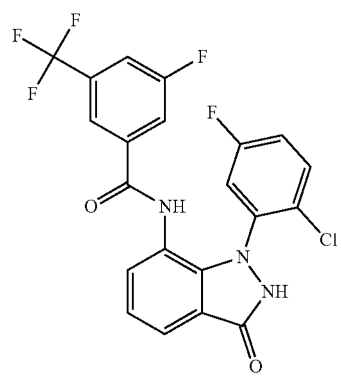 [SMILES: O=C(Nc1cccc2c(=O)[nH]n(-c3cc(F)ccc3Cl)c12)c1cc(F)cc(C(F)(F)F)c1] | Fc1ccc(C1)c(c1)-n1[nH]c(=O)c2ccc(NC(=O)c3cc(F)cc(c3)C(F)(F)F)c12 | 1H NMR (400 MHz, DMSO-d6) 11.43 (br s, 1H), 10.42 (s, 1H), 7.92 (d, 8.1 Hz, 1H), 7.73 (d, 8.0 Hz, 1H), 7.70-7.62 (m, 2H), 7.37 (dd, 8.8, 5.6 Hz, 1H), 7.30 (d, 7.3 Hz, 1H), 7.25 (dd, 9.0, 2.9 Hz, 1H), 7.20 (t, 7.6 Hz, 1H), 6.97 (td, 8.4, 3.0 Hz, 1H). | 466.2 | D | |
| I-324 | 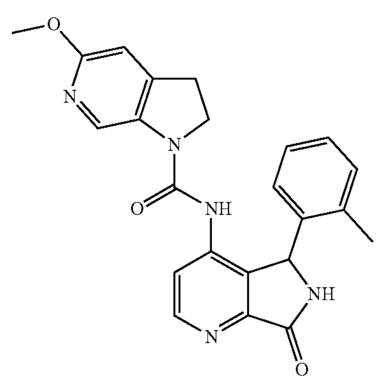 | COc1cc2CCN(C(=O)Nc3ccnc4C(=O)NC(c34)c3ccccc3C)c2cn1 | 1H NMR (400 MHz, DMSO-d6) 9.37 (s, 1H), 8.94 (s, 1H), 8.65 (d, 5.4 Hz, 1H), 8.36 (s, 1H), 7.39 (d, 5.4 Hz, 1H), 7.14 (td, 7.6, 1.2 Hz, 1H), 7.03-6.94 (m, 2H), 6.68 (s, 1H), 6.54 (br s, 1H), 5.89 (s, 1H), 3.80 (s, 3H), 3.65-3.55 (m, 1H), 3.02-2.78 (m, 3H), 2.13 (br s, 3H) | 416.3 | E | |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-325 | 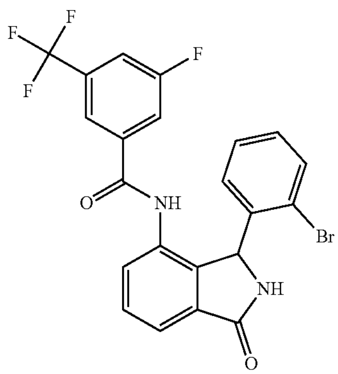 [SMILES: O=C(Nc1cccc2c1C(c1ccccc1Br)NC2=O)c1cc(F)cc(C(F)(F)F)c1] | Fc1cc(cc(c1)C(F)(F)F)C(=O)Nc1ccc c2C(=O)NC(c12)c1ccccc1Br | 1H NMR (400 MHz, DMSO-d6) 10.43 (s, 1H), 9.19 (br s, 1H), 7.92 (d, 8.6 Hz, 1H), 7.74-7.59 (m, 3H), 7.54 (s, 1H), 7.48 (d, 6.7 Hz, 1H), 7.42 (d, 8.6 Hz, 1H), 7.24-7.08 (m, 2H, 6.56 (br s, 1H), 6.15 (br s, 1H). | 493.3 | B | |
| I-326 | 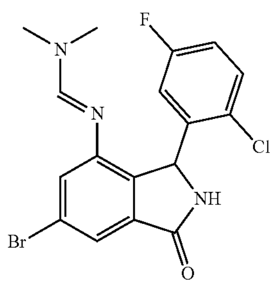 [SMILES: CN(C)/C=N/c1cc(Br)cc2c1C(c1cc(F)ccc1Cl)NC2=O] | CN(C)\C=N\c1cc(Br)cc2C(=O)NC(c12)c1cc(F)ccc1Cl | | | | E |
| I-327 | 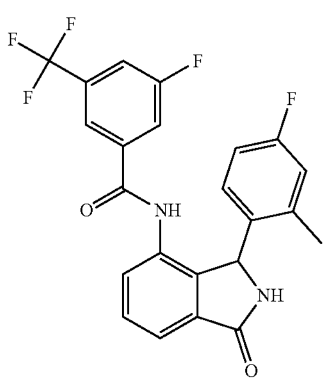 [SMILES: Cc1cc(F)ccc1C1NC(=O)c2cccc(NC(=O)c3cc(F)cc(C(F)(F)F)c3)c21] | Cc1cc(F)ccc1C1NC(=O)c2cccc(NC(=O)c3cc(F)cc(c3)C(F)(F)F)c12 | 1H NMR (400 MHz, CD3CN) 8.52 (s, 1H), 7.74 (dd, 7.5, 1.2 Hz, 1H), 7.64-7.62 (m, 3H), 7.57 (dd, 7.5, 1.2 Hz, 1H), 7.47 (d, 9.1 Hz, 1H), 7.37 (s, 1H), 7.16 (s, 1H), 6.78 (dd, 9.9, 2.1 Hz, 1H), 6.73 (s, 1H), 5.94 (s, 1H), 2.22 (s, 3H). | 445.3 | C | |
| I-328 | 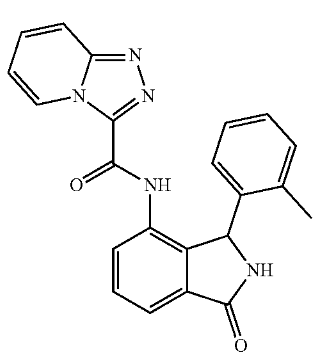 [SMILES: Cc1ccccc1C1NC(=O)c2cccc(NC(=O)c3nnc4ccccn34)c21] | Cc1ccccc1C1NC(=O)c2cccc(NC(=O)c3nnc4ccccn34)c12 | 1H NMR (400 MHz, DMSO-d6)-10.61 (br. s, 1H), 9.07 (dt, 7.0, 1.1 Hz, 1H), 9.05 (s, 1H), 7.98 (dt, 9.3, 1.1 Hz, 1H), 7.69 (dd, 2.7, 1.2 Hz, 1H), 7.67 (dd, 3.0, 1.2 Hz, 1H), 7.64-7.58 (m, 2H), 7.24 (td, 6.9, 1.1 Hz, 1H), 6.93-6.86 (m, 2H), 6.82 (br. s, 1H), 6.66 (br. s, 1H), 6.09 (s, 1H), 2.19 (br. s, 3H) | 384.3 | E | |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-329 | 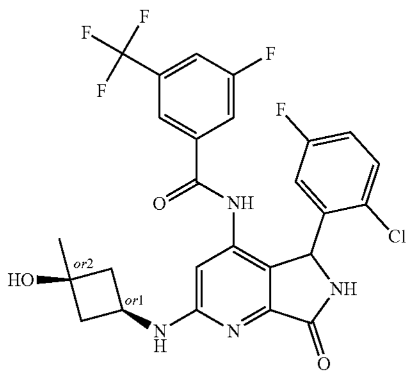 [SMILES: C[C@]1(O)C[C@@H](Nc2cc(NC(=O)c3cc(F)cc(C(F)(F)F)c3)c3c(n2)C(=O)NC3c2cc(F)ccc2Cl)C1] | C[C@@]1(O)C[C@@H](C1)Nc1cc(NC(=O)c2cc(F)cc(c2)C(F)(F)F)c2C(NC(=O)c2n1)c1cc(F)ccc1Cl | 1H NMR (400 MHz, DMSO-d6) 10.49 (s, 1H), 9.14 (s, 1H), 7.94 (d, 8.5 Hz, 1H), 7.67 (d, 8.9 Hz, 1H), 7.56 (s, 1H), 7.34 (br s, 1H), 7.31 (dd, 8.9, 5.2 Hz, 1H), 7.06 (td, 8.4, 3.1 Hz, 1H), 6.68 (br s, 1H), 6.55 (s, 1H), 5.82 (br s, 1H), 5.01 (s, 1H), 4.04-3.77 (m, 1H), 2.40 (dd, 11.0, 7.2 Hz, 2H), 2.03-1.87 (m, 2H), 1.30 (s, 3H). | 567.3 | B | |
| I-330 | 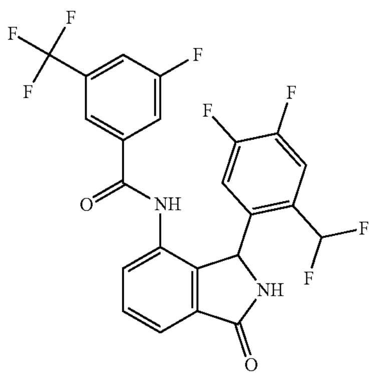 [SMILES: O=C(Nc1cccc2c1C(c1cc(F)c(F)cc1C(F)F)NC2=O)c1cc(F)cc(C(F)(F)F)c1] | FC(F)c1cc(F)c(F)cc1C1NC(=O)c2ccc(NC(=O)c3cc(F)c(c3)C(F)(F)F)c12 | ¹H NMR (400 MHz, DMSO-d$_6$) δ 10.47 (s, 1H), 9.16 (s, 1H), 7.87-8.05 (m, 3H), 7.64-7.77 (m, 2H), 7.42-7.58 (m, 2H), 6.64-7.38 (m, 2H), 5.96 (s, 1H). | 501.4 | A | |
| I-331 | 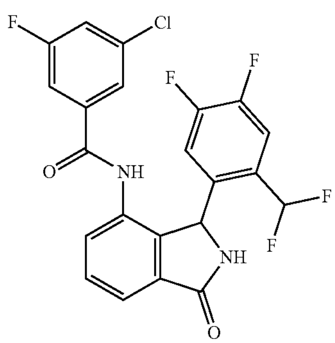 [SMILES: O=C(Nc1cccc2c1C(c1cc(F)c(F)cc1C(F)F)NC2=O)c1cc(F)cc(Cl)c1] | FC(F)c1cc(F)c(F)cc1C1NC(=O)c2ccc(NC(=O)c3cc(F)c(Cl)c3)c12 | ¹H NMR (400 MHz, DMSO-d$_6$) δ 10.31 (s, 1H), 9.15 (s, 1H), 7.61-7.79 (m, 3H), 7.47-7.58 (m, 2H), 7.29-7.38 (m, 2H), 6.59-7.24 (m, 2H), 5.90-6.01 (m, 1H). | 467.4 | B | |
| I-332 | 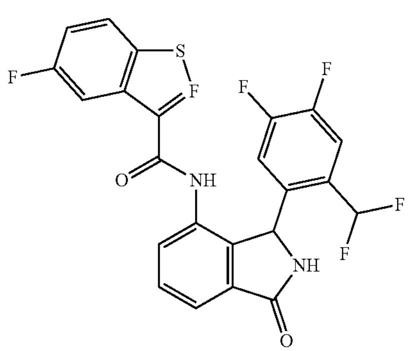 | FC(F)c1cc(F)c(F)cc1C1NC(=O)c2ccc(NC(=O)c3nsc4cc(F)cc34)c12 | ¹H NMR (400 MHz, DMSO-d$_6$) δ 10.36 (s, 1H), 9.20 (s, 1H), 8.37 (br dd, J = 4.88, 9.03 Hz, 1H), 8.20 (br dd, J = 2.20, 9.52 Hz, 1H), 6.95-7.98 (m, 6H), 6.65-6.91 (m, 1H), 5.97-6.17 (m, 1H). | 490.4 | A | |

TABLE 2-continued

Representative Compounds of the Invention with Bioactivity Data.

| Ex. No. | Structure | SMILES | $^1$H NMR | MS | ADP-Glo IC$_{50}$ | MCF 10A IC$_{50}$ |
|---|---|---|---|---|---|---|
| I-333 | 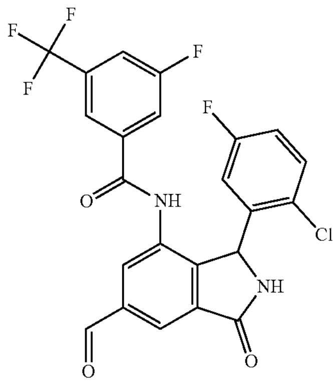 [SMILES: O=Cc1cc(NC(=O)c2cc(F)cc(C(F)(F)F)c2)c2c(c1)C(=O)NC2c1cc(F)ccc1Cl] | Fc1ccc(C1)c(c1)C1NC(=O)cc2cc(C=O)cc(NC(=O)c3cc(F)cc(c3)C(F)(F)F)c12 | $^1$H NMR (400 MHz, DMSO-d$_6$) δ 10.67 (s, 1H), 10.08-10.21 (m, 1H), 9.26-9.52 (m, 1H), 8.18-8.32 (m, 1H), 7.88-7.89 (m, 1H), 7.84-8.09 (m, 1H), 7.63-7.79 (m, 1H), 7.56-7.82 (m, 1H), 7.25-7.38 (m, 1H), 6.98-7.15 (m, 1H), 5.90-6.23 (m, 2H). | 495.3 | A | |
| I-334 | 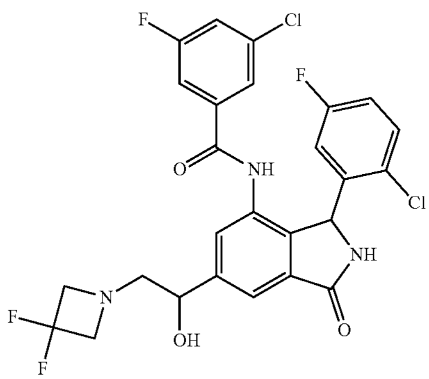 [SMILES: O=C(Nc1cc(C(O)CN2CC(F)(F)C2)cc2c1C(c1cc(F)ccc1Cl)NC2=O)c1cc(F)cc(Cl)c1] | OC(CN1CC(F)(F)C1)c1cc2C(=O)NC(c2c(NC(=O)c2cc(F)cc(Cl)c2)c1)c1cc(F)ccc1Cl | 1H NMR (DMSO-d6, 500 MHz) 10.3-10.5 (m, 1H), 8.9-9.3 (m, 1H), 8.3-8.5 (m, 1H), 7.6-7.8 (m, 1H), 7.2-7.6 (m, 3H), 7.0-7.2 (m, 1H), 6.5-6.8 (m, 1H), 5.8-6.2 (m, 2H), 5.4-5.6 (m, 1H), 4.4-4.9 (m, 2H), 3.5-3.8 (m, 3H), 2.7-3.0 (m, 2H) | 568 | B | |
| I-335 | 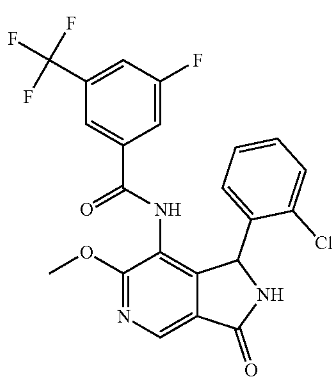 [SMILES: COc1ncc2c(c1NC(=O)c1cc(F)cc(C(F)(F)F)c1)C(c1ccccc1Cl)NC2=O] | COc1ncc2C(=O)NC(c2c1NC(=O)c1cc(F)cc(c1)C(F)(F)F)c1ccccc1Cl | 1H NMR (400 MHz, DMSO-d6) 10.24 (s, 1H), 9.05 (br s, 1H), 8.54 (s, 1H), 7.91 (br d, 8.30 Hz, 1H), 7.63 (br d, 8.79 Hz, 1H), 7.58 (br s, 1H), 7.19-7.31 (m, 2H), 7.03-7.17 (m, 1H), 6.60 (br s, 1H), 5.87-6.02 (m, 1H), 3.97 (s, 3H) | 480.42 | E | |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-336 | 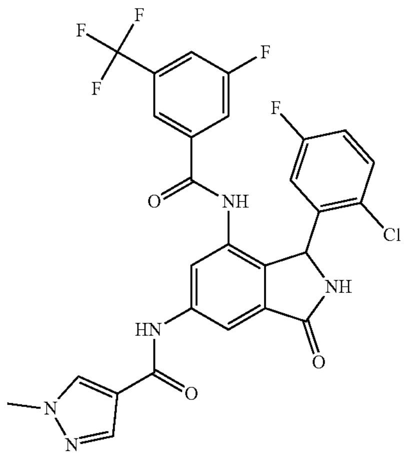 [SMILES: Cn1cc(C(=O)Nc2cc(NC(=O)c3cc(F)cc(C(F)(F)F)c3)c3c(c2)C(=O)NC3c2cc(F)ccc2Cl)cn1] | Cn1cc(cn 1)C(=O) Nc1cc2C (=O)NC (c2c(NC (=O)c2cc (F)cc(c2) C(F)(F)F) c1)c1cc (F)ccc1Cl | 1H NMR (400 MHz, DMSO-d6) 3.91 (s, 3H), 5.81-6.04 (m, 2H), 7.08 (td, 8.36, 3.05 Hz, 1H), 7.31 (dd, 8.91, 5.25 Hz, 1H), 7.64 (s, 1H), 7.73 (br d, 8.79 Hz, 1H), 7.91-7.99 (m, 2H), 8.03-8.10 (m, 2H), 8.36 (s, 1H), 9.13 (br s, 1H), 10.16 (s, 1H), 10.52 (s, 1H) | 590.28 | A | |
| I-337 | 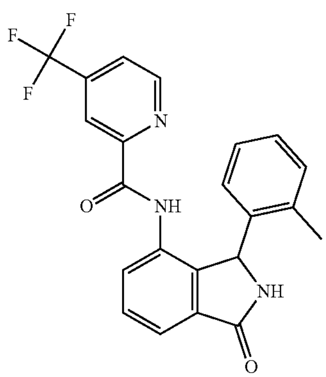 [SMILES: Cc1ccccc1C1NC(=O)c2cccc(NC(=O)c3cc(C(F)(F)F)ccn3)c21] | Cc1ccccc 1C1NC(= O)c2cccc (NC(=O) c3cc(ccn 3)C(F)(F) F)c12 | 1H NMR (400 MHz, DMSO-d6) 10.07 (s, 1H), 9.08 (s, 1H), 8.83 (d, 7.1 Hz, 1H), 8.14 (s, 1H), 8.06-8.00 (m, 2H), 7.67-7.58 (m, 2H), 7.13-7.02 (m, 2H), 7.01-6.95 (m, 1H), 6.69 (br s, 1H), 6.08 (s, 1H), 2.26 (br s, 3H). | 412.3 | E | |
| I-338 | 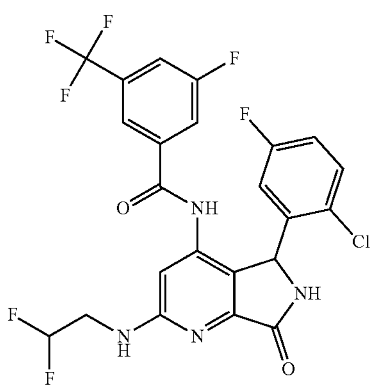 [SMILES: O=C(Nc1cc(NCC(F)F)nc2c1C(c1cc(F)ccc1Cl)NC2=O)c1cc(F)cc(C(F)(F)F)c1] | FC(F)CN c1cc(NC (=O)c2cc (F)cc(c2) C(F)(F)F) c2C(NC (=O)c2n1) c1cc(F)c cc1Cl | 1H NMR (400 MHz, DMSO-d6) 10.55 (s, 1H), 9.21 (s, 1H), 7.96 (d, 8.1 Hz, 1H), 7.67 (d, 8.9 Hz, 1H), 7.55 (br s,2H), 7.32 (dd, 8.8, 5.2 Hz, 1H), 7.07 (td, 8.5, 3.0 Hz, 1H), 6.75 (s, 1H), 6.72 (br s, 1H), 6.18 (tt, 56.5, 4.0 Hz, 1H), 5.86 (br s, 1H), 4.09-3.55 (m, 2H). | 547.2 | A | |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-339 | 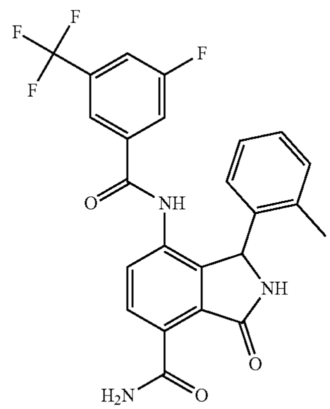 [SMILES: Cc1ccccc1C1NC(=O)c2c(C(N)=O)ccc(NC(=O)c3cc(F)cc(C(F)(F)F)c3)c21] | Cc1cccc1C1NC(=O)c2c1c(NC(=O)c1cc(F)cc(c1)C(F)(F)F)ccc2C(N)=O | 1H NMR (400 MHz, DMSO-d6) 10.73 (s, 1H), 10.48 (br s, 1H), 9.80 (s, 1H), 8.33 (d, 8.3 Hz, 1H), 7.90 (d, 8.5 Hz, 1H), 7.75 (s, 1H), 7.71 (d, 8.3 Hz, 1H), 7.47 (d, 8.6 Hz, 1H), 7.31 (br s, 1H), 7.09 (td, 7.6, 0.9 Hz, 1H), 7.01 (d, 7.3 Hz, 1H), 6.99-6.93 (m, 1H), 6.47 (br s, 1H), 6.00 (br s, 1H), 2.30 (br s, 3H). | 472.3 | B | |
| I-340 | 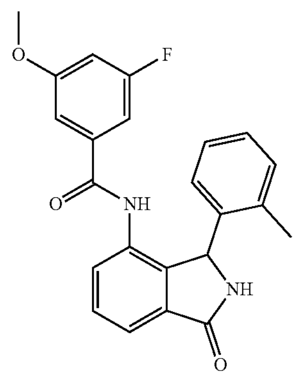 [SMILES: COc1cc(F)cc(C(=O)Nc2cccc3c2C(c2ccccc2C)NC3=O)c1] | COc1cc(F)cc(c1)C(=O)Nc1cccc2C(=O)NC(c12)c1cccc1C | 1H NMR (400 MHz, DMSO-d6) 10.07 (s, 1H), 9.04 (s, 1H), 7.65 (dd, 7.4, 1.2 Hz, 1H), 7.60 (t, 7.5 Hz, 1), 7.53 (dd, 7.7, 1.1 Hz, 1H), 7.10 (td, 7.4, 1.4 Hz, 1H), 7.04 (br. d, 7.0 Hz, 1H), 6.99 (t, 2.3 Hz, 1H), 6.98-6.94 (m, 1H), 6.76 (s, 1H), 6.68 (br. d, 8.4 Hz, 1H), 6.56 (br s, 1H), 5.94 (s, 1H), 3.75 (s, 3H), 2.20 (br s, 3H) | 391.3 | D | |
| I-341 | 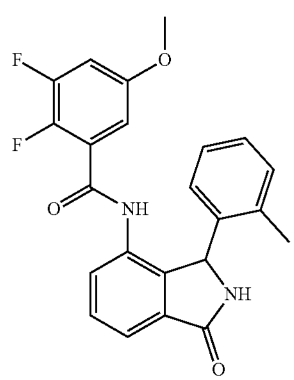 [SMILES: COc1cc(F)c(F)c(C(=O)Nc2cccc3c2C(c2ccccc2C)NC3=O)c1] | COc1cc(F)c(F)c(c1)C(=O)Nc1cccc2C(=O)NC(c12)c1ccccc1C | 1H NMR (400 MHz, DMSO-d6) 10.26 (s, 1H), 9.07 (s, 1H), 7.67 (dd, 7.5, 1.0 Hz, 1H), 7.60 (t, 7.6 Hz, 1H), 7.49 (dd, 7.7, 0.5 Hz, 1H), 7.21-7.14 (m, 3H), 7.03 (td, 7.6, 1.6 Hz, 1H), 6.55 (br. s, 1H), 6.02 (s, 1H), 5.97 (s, 1H), 3.69 (s, 3H), 2.26 (br s, 3H) | 409.3 | E | |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-342 | 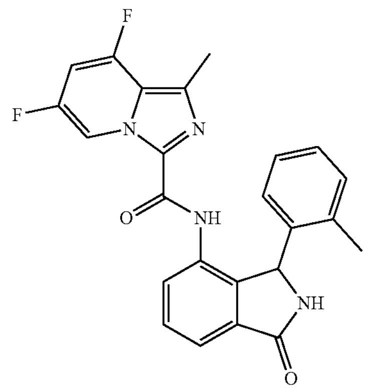 [SMILES: Cc1ccccc1C1NC(=O)c2cccc(NC(=O)c3nc(C)c4c(F)cc(F)cn34)c21] | Cc1nc(C(=O)Nc2cccc3C(=O)NC(c23)c2ccccc2C)n2cc(F)cc(F)c12 | 1H NMR (400 MHz, DMSO-d6) 9.69 (s, 1H), 9.06 (dd, 5.1, 1.7 Hz, 1H), 9.05 (s, 1H), 7.91 (dd, 7.0, 1.7 Hz, 1H), 7.62-7.56 (m, 2H), 7.30 (ddd, 10.7, 8.8, 1.6 Hz, 1H), 7.07-7.01 (m, 2H), 6.97-6.92 (m, 1H), 6.69 (br s, 1H), 6.10 (s, 1H), 2.55 (s, 3H), 2.32 (br. s, 3H). | 433.3 | E | |
| I-343 | 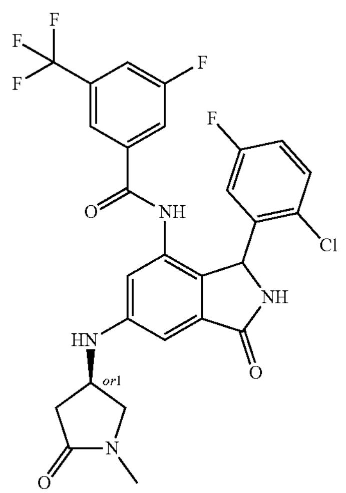 [SMILES: CN1C[C@H](Nc2cc(NC(=O)c3cc(F)cc(C(F)(F)F)c3)c3c(c2)C(=O)NC3c2cc(F)ccc2Cl)CC1=O] | CN1C[C@@H](CC1=O)Nc1cc2C(=O)NC(c2c(NC(=O)c2cc(F)cc(c2)C(F)(F)F)c1)c1cc(F)ccc1Cl | 1H NMR (400 MHz, DMSO-d6) 10.29 (d, 4.0 Hz, 1H), 8.95 (s, 1H), 7.92 (d, 8.6 Hz, 1H), 7.69 (d, 9.3 Hz, 1H), 7.60 (s, 1H), 7.28 (dd, 8.9, 5.2 Hz, 1H), 7.06 (td, 8.5, 3.1 Hz, 1H), 6.80 (d, 1.9 Hz, 1H), 6.69 (s, 1H), 6.62 (br. s, 1H), 6.58 (d, 6.2 Hz, IH), 5.84 (br. s, 1H), 4.19-4.08 (m, 1H), 3.79-3.74 (m, 1H), 3.24-3.16 (m, 1H), 2.79-2.73 (m, 1H), 2.75 (s, 3H), 2.22-2.15 (m, 1H) | 579.3 | A | |
| I-344 | 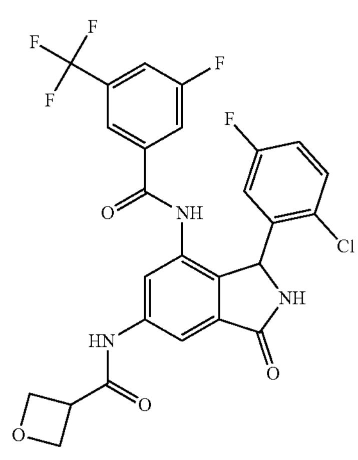 [SMILES: O=C(Nc1cc(NC(=O)C2COC2)cc2c1C(c1cc(F)ccc1Cl)NC2=O)c1cc(F)cc(C(F)(F)F)c1] | Fc1ccc(C1)c(c1)C1NC(=O)c2cc(NC(=O)C3COC3)cc(NC(=O)c3cc(F)cc(c3)C(F)(F)F)c12 | 1H NMR (400 MHz, DMSO-d6) 2.87 (br s, 1H), 3.99 (dt, 14.89, 7.44 Hz, 2H), 4.68-4.81 (m, 2H), 5.84-6.04 (m, 2H), 6.51 (br s, 1H), 7.03-7.13 (m, 1H), 7.30 (br dd, 8.79, 5.13 Hz, 1H), 7.62 (br s, 1H), 7.67-7.76 (m, 1H), 7.82 (br s, 1H), 7.93 (br d, 11.71 Hz, 1H), 9.13 (s, 1H), 10.32 (br s, 1H), 10.50 (br s, 1H) | 566.31 | A | |

TABLE 2-continued

Representative Compounds of the Invention with Bioactivity Data.

| Ex. No. | Structure | SMILES | $^1$H NMR | MS | ADP-Glo IC$_{50}$ | MCF 10A IC$_{50}$ |
|---|---|---|---|---|---|---|
| I-345 | 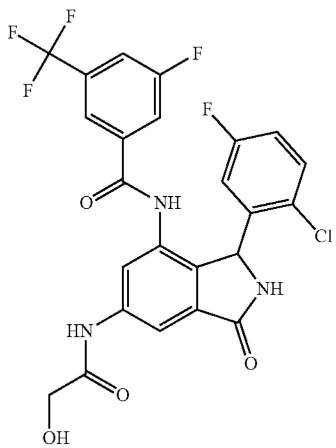 [SMILES: O=C(CO)Nc1cc(NC(=O)c2cc(F)cc(C(F)(F)F)c2)c2c(c1)C(=O)NC2c1cc(F)ccc1Cl] | OCC(=O)Nc1cc2C(=O)NC(c2c(NC(=O)c2cc(F)cc(c2)C(F)(F)F)c1c1cc(F)ccc1Cl | 1H NMR (400 MHz, DMSO-d6) 4.04 (br d, 4.39 Hz, 2H), 5.73 (br s, 1H), 5.79-6.03 (m, 2H), 6.63 (br s, 1H), 7.07 (td, 8.24, 2.81 Hz, 1H), 7.29 (br dd, 8.91, 5.25 Hz, 1H), 7.62 (s, 1H), 7.71 (br d, 9.03 Hz, 1H), 7.83-8.00 (m, 2H), 8.06 (s, 1H), 8.47 (s, 1H), 9.10 (br s, 1H), 10.13(br s, 1H), 10.52 (s, 1H) | 540.25 | A | |
| I-346 | 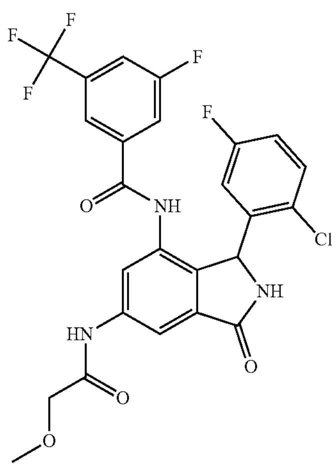 [SMILES: COCC(=O)Nc1cc(NC(=O)c2cc(F)cc(C(F)(F)F)c2)c2c(c1)C(=O)NC2c1cc(F)ccc1Cl] | COCC(=O)Nc1cc2C(=O)NC(c2c(NC(=O)c2cc(F)cc(c2)C(F)(F)F)c1c1cc(F)ccc1Cl | 1H NMR (400 MHz, DMSO-d6) 2.53 (s, 3H), 4.06 (s, 2H), 5.85-5.96 (m, 1H), 7.07 (br d, 2.68 Hz, 2H), 7.29 (br dd, 8.79, 5.13 Hz, 1 H)7.62 (s, 1H) 7.71 (br d, 9.27 Hz, 1 H), 7.88-7.93 (m, 1H) 8.02 (s, 1 H) 9.01-9.21 (m, 2 ) 10.20 (s, 1 H) 10.51 (s, 1 H) | 554.31 | A | |
| I-347 | 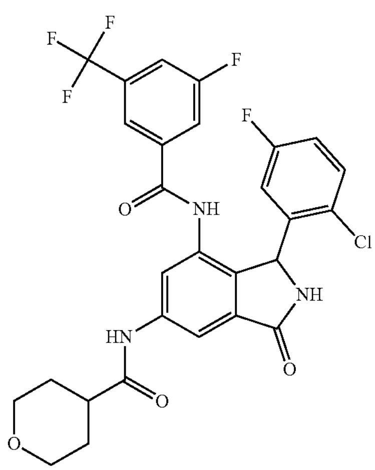 [SMILES: O=C(Nc1cc(NC(=O)C2CCOCC2)cc2c1C(c1cc(F)ccc1Cl)NC2=O)c1cc(F)cc(C(F)(F)F)c1] | Fc1ccc(C1)c(c1)C1NC(=O)c2cc(NC(=O)C3COCC3)cc(NC(=O)c3cc(F)cc(c3)C(F)(F)F)c12 | 1H NMR (400 MHz, DMSO-d6) 1.54-1.91 (m, 4H) 2.56-2.71 (m, 2H) 3.91 (br d, 11.23 Hz, 2 H) 5.84-5.99 (m, 1H) 7.07 (td, 8.30, 2.93 Hz, 1H) 7.29 (br dd, 8.79, 5.13 Hz, 1H) 7.62 (s, 1H) 7.68-7.78 (m, 1H) 7.82 (s, 1H) 7.89-7.94 (m, 1H) 9.10 (br s, 2H) 10.27 (s, 1H) 10.48 (s, 1H) | 594.28 | A | |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-348 | 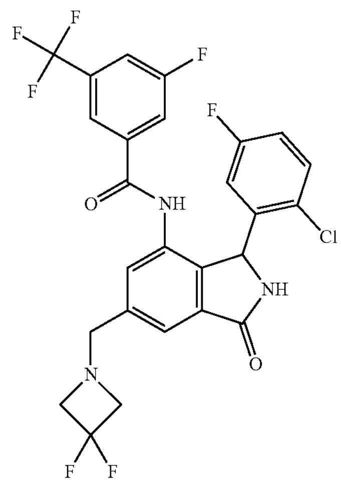 [SMILES: O=C(Nc1cc(CN2CC(F)(F)C2)cc2c1C(c1cc(F)ccc1Cl)NC2=O)c1cc(F)cc(C(F)(F)F)c1] | Fc1ccc(C1)c(c1)C1NC(=O)c2cc(CN3CC(F)(F)C3)cc(NC(=O)c3cc(F)cc(c3)C(F)(F)F)c12 | ¹H NMR (400 MHz, DMSO-d$_6$) δ 10.33-10.66 (m, 1H), 9.11 (br s, 1H), 8.43 (br s, 1H), 6.17-8.11 (m, 7H), 5.80-6.08 (m, 1H), 3.76-3.99 (m, 1H), 3.58-3.72 (m, 1H), 3.13-3.31 (m, 4H). | 572.2 | A | |
| I-349 | 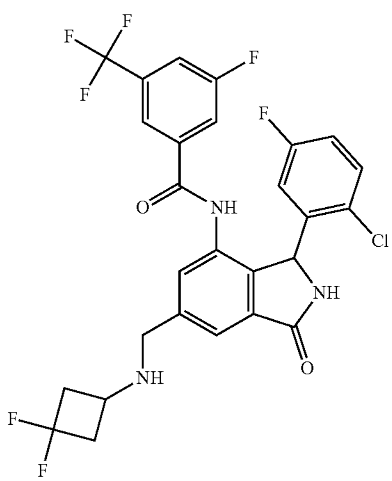 [SMILES: O=C(Nc1cc(CNC2CC(F)(F)C2)cc2c1C(c1cc(F)ccc1Cl)NC2=O)c1cc(F)cc(C(F)(F)F)c1] | Fc1ccc(C1)c(c1)C1NC(=O)c2cc(CNC3CC(F)(F)C3)cc(NC(=O)c3cc(F)cc(c3)C(F)(F)F)c12 | ¹H NMR (400 MHz, DMSO-d$_6$) δ 10.48 (s, 1H), 9.09 (br s, 1H), 8.33 (s, 1H), 7.40-7.97 (m, 3H), 7.25-7.35 (m, 1H), 7.07 (dt, J = 3.05, 8.36 Hz, 1H), 6.24-6.89 (m, 2H), 5.79-6.10 (m, 1H), 3.77 (s, 1H), 3.01-3.23 (m, 2H), 2.61-2.93 (m, 2H), 2.15-2.44 (m, 2H). | 586.2 | A | |
| I-350 | 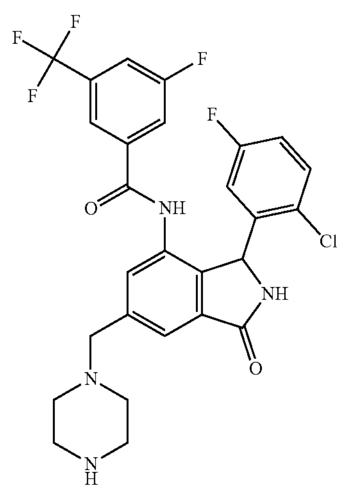 [SMILES: O=C(Nc1cc(CN2CCNCC2)cc2c1C(c1cc(F)ccc1Cl)NC2=O)c1cc(F)cc(C(F)(F)F)c1] | Fc1ccc(C1)c(c1)C1NC(=O)c2cc(CN3CCNCC3)cc(NC(=O)c3cc(F)cc(c3)C(F)(F)F)c12 | ¹H NMR (400 MHz, DMSO-d$_6$) δ 10.49 (br s, 1H), 9.10 (br s, 1H), 8.34 (s, 1H), 6.11-8.09 (m, 6H), 5.68-6.05 (m, 1H), 3.33-3.74 (m, 10H), 2.60-2.85 (m, 1H), 2.24-2.44 (m, 1H). | 565.2 | A | |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-351 | 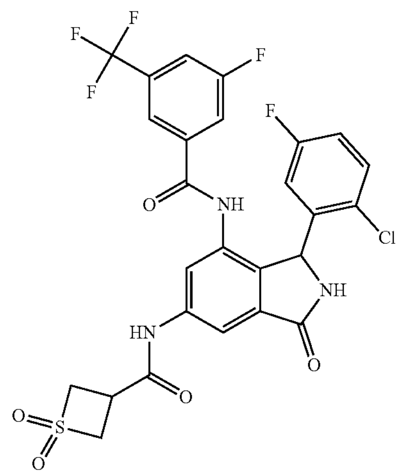 [SMILES: O=C(Nc1cc(NC(=O)C2CS(=O)(=O)C2)cc2c1C(c1cc(F)ccc1Cl)NC2=O)c1cc(F)cc(C(F)(F)F)c1] | Fc1ccc(C1)c(c1)C1NC(=O)c2cc(NC(=O)C3CS(=O)(=O)C3)cc(NC(=O)c3cc(F)cc(c3)C(F)(F)F)c12 | 1H NMR (400 MHz, DMSO-d6) 3.48-3.62 (m, 2H), 4.35-4.49 (m, 3H), 5.92 (br d, 6.35 Hz, 1H), 7.07 (td, 8.30, 2.93 Hz, 1H), 7.30 (br dd, 8.79, 5.13 Hz, 1H), 7.61 (s, 1H), 7.71 (br d, 8.79 Hz, 1H), 7.79 (s, 1H), 7.93 (s, lH), 9.14 (br s, 3H), 10.51 (s, 1H), 10.64 (s, 1H) | 614.34 | A | |
| I-352 | 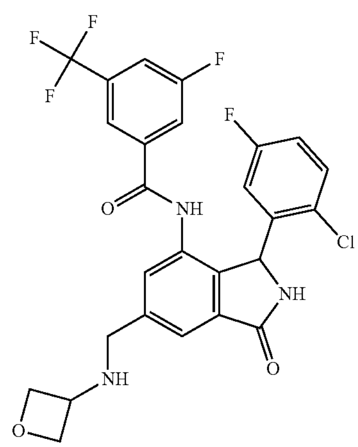 [SMILES: O=C(Nc1cc(CNC2COC2)cc2c1C(c1cc(F)ccc1Cl)NC2=O)c1cc(F)cc(C(F)(F)F)c1] | Fc1ccc(C1)c(c1)C1NC(=O)c2cc(CNC3COC3)cc(NC(=O)c3cc(F)cc(c3)C(F)(F)F)c12 | ¹H NMR (400 MHz, DMSO-d$_6$) δ 10.47 (br s, 1H), 9.08 (br s, 1H), 8.36 (br d, J = 4.88 Hz, 1H), 6.19-8.08 (m, 7H), 5.74-6.11 (m, 1H), 4.45-4.63 (m, 1H), 4.16-4.38 (m, 1H), 3.82-3.99 (m, 1H), 3.66-3.82 (m, 1H), 2.83-3.30 (m, 3H). | 552.1 | A | |
| I-353 | 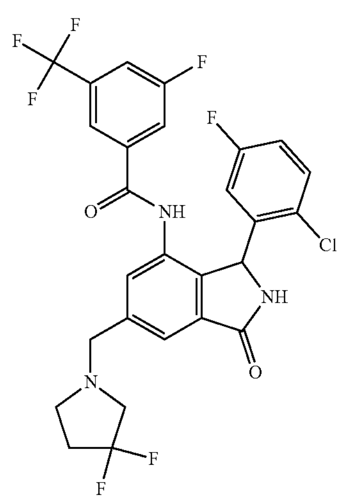 [SMILES: O=C(Nc1cc(CN2CCC(F)(F)C2)cc2c1C(c1cc(F)ccc1Cl)NC2=O)c1cc(F)cc(C(F)(F)F)c1] | Fc1ccc(C1)c(c1)C1NC(=O)c2cc(CN3CCC(F)(F)C3)cc(NC(=O)c3cc(F)cc(c3)C(F)(F)F)c12 | ¹H NMR (400 MHz, DMSO-d$_6$) δ 10.33-10.72 (m, 1H), 8.96-9.33 (m, 1H), 8.27-8.55 (m, lH), 6.32-8.09 (m, 6H), 5.62-6.23 (m, 2H), 3.66-3.90 (m, 1H), 3.12-3.30 (m, 2H), 2.81-3.02 (m, 1H), 2.62-2.81 (m, 1H), 2.13-2.37 (m, 1H), 1.18-1.61 (m, 2H). | 586.2 | A | |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-354 | 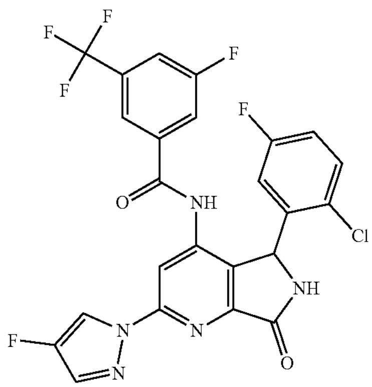 [SMILES: O=C(Nc1cc(-n2cc(F)cn2)nc2c1C(c1cc(F)ccc1Cl)NC2=O)c1cc(F)cc(C(F)(F)F)c1] | Fc1cnn(c1)-c1cc(NC(=O)c2cc(F)cc(c2)C(F)(F)F)c2C(NC(=O)c2n1)c1cc(F)ccc1Cl | ¹H NMR (400 MHz, DMSO-d$_6$) δ 9.34 (br s, 1H), 8.68 (br d, J = 3.9 Hz, 1H), 8.59 (br s, 1H), 8.25 (br s, 1H), 7.92 (br d, J = 3.7 Hz, 1H), 7.65-7.84 (m, 3H), 7.41 (br dd, J = 8.7, 5.0 Hz, 1H), 7.12 (td, J = 8.4, 2.9 Hz, 1H), 6.77-6.93 (m, 1H), 6.00 (br s, 1H). | 552.4 | B | |
| I-355 | 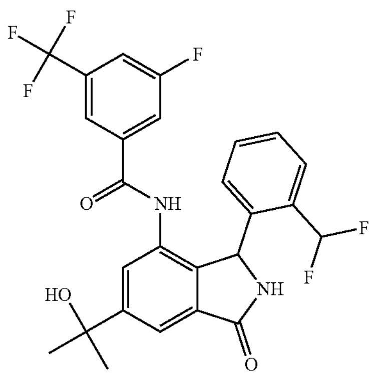 [SMILES: CC(C)(O)c1cc(NC(=O)c2cc(F)cc(C(F)(F)F)c2)c2c(c1)C(=O)NC2c1ccccc1C(F)F] | CC(C)(O)c1cc2C(=O)NC(c2c(NC(=O)c2cc(F)cc(c2)C(F)(F)F)c1)c1ccccc1C(F)F | 1H NMR (DMSO-d6, 400 MHz) Shift 10.4-10.5 (m, 1H), 9.0-9.2 (m, 1H), 7.88 (br d, 1H, 8.3 Hz), 7.78 (d, 1H, 1.2 Hz), 7.5-7.7 (m, 2H), 7.4-7.5 (m, 1H), 7.3-7.4 (m, 2H), 6.5-6.8 (m, 2H), 5.9-6.1 (m, 1H), 5.2-5.4 (m, 1H), 1.4-1.7 (m, 6H) | 523 | A | |
| I-356 | 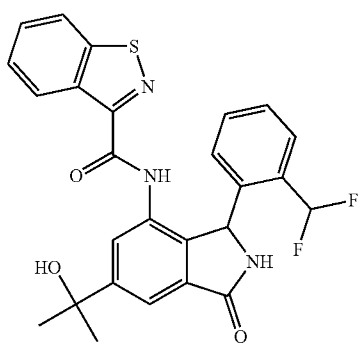 [SMILES: CC(C)(O)c1cc(NC(=O)c2nsc3ccccc23)c2c(c1)C(=O)NC2c1ccccc1C(F)F] | CC(C)(O)c1cc2C(=O)NC(c2c(NC(=O)c2nsc3ccccc23)c1)c1ccccc1C(F)F | ¹H NMR (400 MHz, DMSO-d$_6$) δ 10.0-10.3 (m, 1H), 9.1-9.2 (m, 1H), 9.0-9.2 (m, 1H), 8.5-8.7 (m, 1H), 8.2-8.4 (m, 1H), 8.1-8.1 (m, 1H), 7.94 (s, 1H), 7.7-7.8 (m, 1H), 7.7-7.7 (m, 1H), 7.6-7.7 (m, 1H), 7.5-7.4 (m, 1H), 7.2-7.3 (m, 1H), 6.7-6.8 (m, 1H), 6.1-6.2 (m, 1H), 5.2-5.4 (m, 1H), 1.4-1.6 (m, 6H). | 494 | A | |
| I-357 | 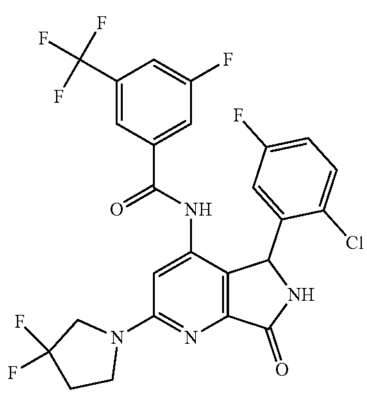 [SMILES: O=C(Nc1cc(N2CCC(F)(F)C2)nc2c1C(c1cc(F)ccc1Cl)NC2=O)c1cc(F)cc(C(F)(F)F)c1] | Fc1ccc(C1)c(c1)C1NC(=O)c2nc(cc(NC(=O)c3cc(F)cc(c3)C(F)(F)F)c12)N1CCC(F)(F)C1 | ¹H NMR (400 MHz, DMSO-d$_6$) δ 10.61-10.73 (m, 1H), 9.08-9.25 (m, 1H), 8.42 (s, 1H), 7.82-7.98 (m, 1H), 7.72 (br d, J = 9.0 Hz, 1H), 7.65 (s, 1H), 7.33 (br dd, J = 8.5, 5.1 Hz, 1H), 7.07 (td, J = 8.3, 2.9 Hz, 1H), 6.62-6.73 (m, 1H), 5.88 (s, 1H), 3.82-4.02 (m, 2H), 3.60-3.77 (m, 2H), 2.54-2.63 (m, 2H). | 573.5 | A | |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-358 | 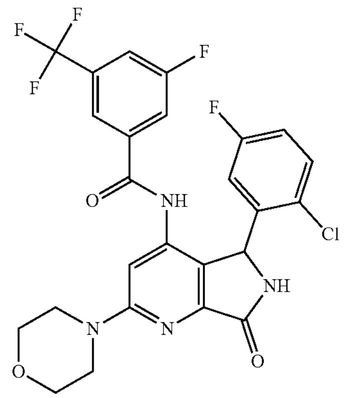 [SMILES: O=C(Nc1cc(N2CCOCC2)nc2c1C(c1cc(F)ccc1Cl)NC2=O)c1cc(F)cc(C(F)(F)F)c1] | Fc1ccc(C1)c(c1)C1NC(=O)c2nc(cc(NC(=O)c3cc(F)cc(c3)C(F)(F)F)c12)N1CCOCC1 | 1H NMR (400 MHz, DMSO-d6) δ 10.57-10.72 (m, 1H), 9.16-9.28 (m, 1H), 8.42 (br s, 1H), 7.85-8.00 (m, 1H), 7.71 (br d, J = 8.5 Hz, 1H), 7.65 (br s, 1H), 7.32 (br dd, J = 8.9, 5.2 Hz, 1H), 7.07 (td, J = 8.4, 3.1 Hz, 1H), 6.88-6.99 (m, 1H), 5.88 (br s, 1H), 3.65-3.79 (m, 4H), 3.54 (br s, 4H). | 553.5 | A | |
| I-359 | 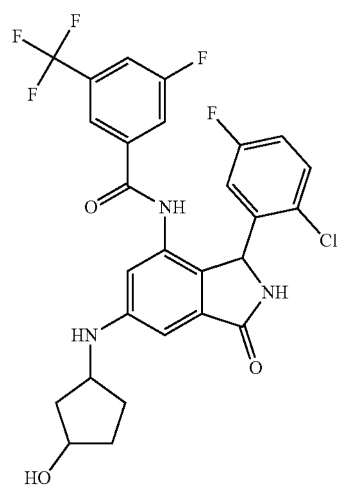 [SMILES: O=C(Nc1cc(NC2CCC(O)C2)cc2c1C(c1cc(F)ccc1Cl)NC2=O)c1cc(F)cc(C(F)(F)F)c1] | OC1CCC(C1)Nc1cc2C(=O)NC(c2c(NC(=O)c2cc(F)cc(c2)C(F)(F)F)c1)c1cc(F)ccc1Cl | 1H NMR (400 MHz, DMSO-d6) 1.23 (br s, 1 H) 1.39 (td, 12.45, 5.86 Hz, 1 H) 1.62 (br dd, 14.64, 7.08 Hz, 1 H) 1.73 (br d, 3.66 Hz, 1H) 1.96 (br d, 6.35 Hz, 1 H) 2.28 (br d, 6.59 Hz, 1 H) 3.64-3.76 (m, 1 H) 4.12 (br d, 4.88 Hz, 1 H) 4.63 (br d, 2.68 Hz, 1 H) 5.76-5.90 (m, 1 H) 6.19 (br d, 6.83 Hz, 1 H) 6.47-6.59 (m, 1 H) 6.65 (br s, 1 H) 6.77 (br d, 1.71 Hz, 1 H) 7.05 (td, 8.42, 2.93 Hz, 1 H) 7.26 (br dd, 8.79, 5.13 Hz, 1 H) 7.60 (br s, 1 H) 7.68 (br d, 9.27 Hz, 1 H) 7.90 (br d, 8.05 Hz, 1 H) 8.87 (br s, 1 H) 10.23 (s, 1 H) | | A | |
| I-360 | 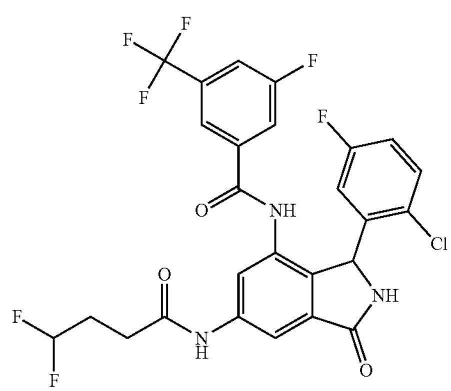 [SMILES: O=C(CCC(F)F)Nc1cc(NC(=O)c2cc(F)cc(C(F)(F)F)c2)c2c(c1)C(=O)NC2c1cc(F)ccc1Cl] | FC(F)CCC(=O)Nc1cc2C(=O)NC(c2c(NC(=O)c2cc(F)cc(c2)C(F)(F)F)c1)c1cc(F)ccc1Cl | 1H NMR (400 MHz, DMSO-d6) 2.06-2.25 (m, 3H) 2.52-2.57 (m, 2 H) 5.91 (br d, 9.27 Hz, 2H) 7.07 (td, 8.36, 2.81 Hz, 1H) 7.29 (br dd, 8.91, 5.25 Hz, 1H) 7.61 (s, 1H) 7.71 (br d, 8.79 Hz, 1 H) 7.78 (s, 1H) 7.86-7.96 (m, 2 H) 9.11 (br s, 1H) 10.40 (s, 1H) 10.49 (s, 1H) | 588.22 | A | |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-361 | 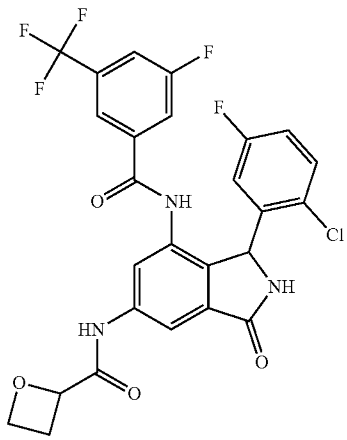 [SMILES: O=C(Nc1cc(NC(=O)C2CCO2)cc2c1C(c1cc(F)ccc1Cl)NC2=O)c1cc(F)cc(C(F)(F)F)c1] | Fc1ccc(C1)c(c1)C1NC(=O)c2cc(NC(=O)C3CCO3)cc(NC(=O)c3cc(F)cc(c3)C(F)(F)F)c12 | 1H NMR (400 MHz, DMSO-d6) 2.92-3.05 (m, 2 H) 4.66 (br t, 7.81 Hz, 2H) 5.13 (ddd, 9.09, 6.41, 2.81 Hz, 1H) 5.86-5.97 (m, 1H) 7.08 (br d, 2.68 Hz, 1H) 7.30 (dd, 8.79, 5.13 Hz, 1 H) 7.63 (s, 1H) 7.71 (br d, 9.03 Hz, 1H) 7.91-8.00 (m, 2H) 8.09 (br d, 5.12 Hz, 1H) 9.13 (br s, 1H) 10.32 (s, 1H) 10.52 (s, 1H) | 566.16 | A | |
| I-362 | 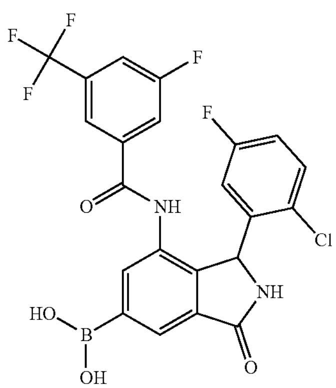 [SMILES: O=C(Nc1cc(B(O)O)cc2c1C(c1cc(F)ccc1Cl)NC2=O)c1cc(F)cc(C(F)(F)F)c1] | OB(O)c1cc2C(=O)NC(c2c(NC(=O)c2cc(F)cc(c2)C(F)(F)F)c1)c1cc(F)ccc1Cl | 1H NMR (400 MHz, DMSO-d6) 5.81-6.14 (m, 2H) 6.45-6.63 (m, 1H) 6.90-7.13 (m, 2H) 7.20-7.37 (m, 1 H) 7.57-7.78 (m, 2H) 7.84 (s, 1 H) 7.88-7.98 (m, 1H) 8.10-8.23 (m, 1H) 8.37-8.54 (m, 2H) 8.99-9.19 (m, 1H) 10.41-10.54 (m, 1H) | 511 | A | |
| I-363 | 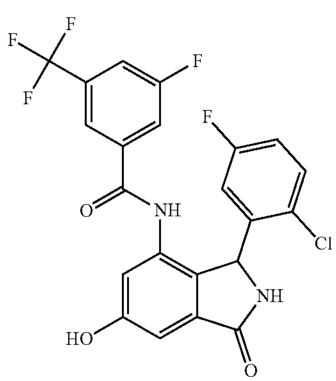 | Oc1cc2C(=O)NC(c2c(NC(=O)c2cc(F)cc(c2)C(F)(F)F)c1)c1cc(F)ccc1Cl | 1H NMR (DMSO-d6, 400 MHz) 10.3-10.5 (m, 1H), 10.0-10.2 (m, 1H), 8.9-9.1 (m, 1H), 7.9-8.0 (m, 1H), 7.6-7.8 (m, 1H), 7.5-7.6 (m, 1H), 7.2-7.4 (m, 1H), 7.0-7.1 (m, 1H), 6.8-6.9 (m, 1H), 6.4-6.7 (m, 1H), 6.3-6.8 (m, 1H), 5.5-6.0 (m, 1H) | 483 | A | |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-364 | 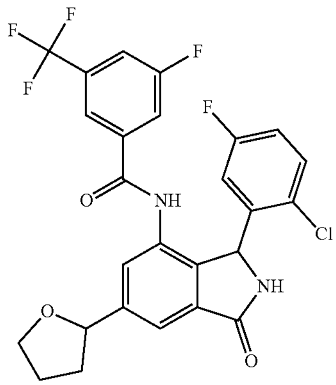 [SMILES: O=C(Nc1cc(C2CCCO2)cc2c1C(c1cc(F)ccc1Cl)NC2=O)c1cc(F)cc(C(F)(F)F)c1] | Fc1ccc(C1)c(c1)C1NC(=O)c2cc(cc(NC(=O)c3cc(F)cc(c3)C(F)(F)F)c12)C1CCCO1 | 1H NMR (400 MHz, CD3CN) 8.63 (s, 1H), 7.69 (dd, 8.3, 0.8 Hz, 1H), 7.64 (dd, 8.4, 1.6 Hz, IH), 7.61-7.52 (m, 3H), 7.25 (ddd, 8.9, 5.1, 1.2 Hz, 2H), 7.01-6.92 (m, 1H), 6.62 (br s, 1H), 6.11 (br s, 1H), 5.00 (q, 7.4 Hz, 1H), 4.12-4.04 (m, 1H), 3.95-3.86 (m, 1H), 2.48-2.38 (m, 1H), 2.06-1.97 (m, 2H), 1.84-1.72 (m, 1H). | 537.2 | A | |
| I-365 | 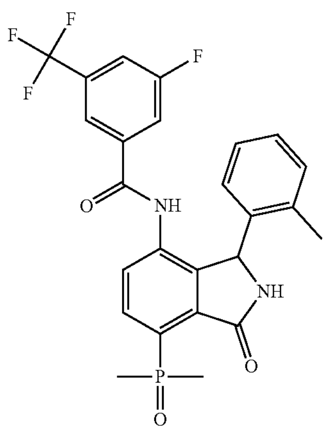 [SMILES: Cc1ccccc1C1NC(=O)c2c(P(C)(C)=O)ccc(NC(=O)c3cc(F)cc(C(F)(F)F)c3)c21] | Cc1ccccc1C1NC(=O)c2c1c(NC(=O)c1cc(F)cc(c1)C(F)(F)F)ccc2P(C)(C)=O | 1H NMR (400 MHz, DMSO-d6) 10.48 (br s, 1 H), 9.38 (s, 1 H), 8.17 (dd, 11.6, 8.1 Hz, 1 H), 7.88 (d, 8.5 Hz, 1 H), 7.70 (d, 8.0 Hz, 1 H), 7.44 (d, 8.2 Hz, 1 H), 7.28 (s, 1 H), 7.06 (td, 7.5, 1.2 Hz, 1 H), 7.00-6.90 (m, 2 H), 6.47 (br s, 1H), 5.94 (s, 1 H), 2.25 (br s, 3 H), 1.91 (d, 6.9 Hz, 3 H), 1.87 (d, 6.9 Hz, 3 H). | 503.3 | D | |
| I-366 | 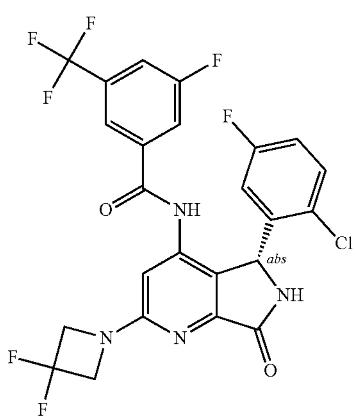 | Fc1ccc(C1)c(c1)[C@@H]1NC(=O)c2nc(cc(NC(=O)c3cc(F)cc(c3)C(F)(F)F)c12)N1CC(F)(F)C1 | ¹H NMR (400 MHz, DMSO-d$_6$) δ 10.72 (br s, 1H), 9.30 (br s, 1H), 7.94 (d, J = 6.5 Hz, 1H), 7.71 (d, J = 9.0 Hz, 1H), 7.62 (s, 1H), 7.34 (dd, J = 8.9, 5.2 Hz, 1H), 7.17-6.97 (m, 1H), 6.94-6.56 (m, 2H), 5.91 (br s, 1H), 4.65-4.33 (m, 4H). | 559.3 | A | |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-367 | 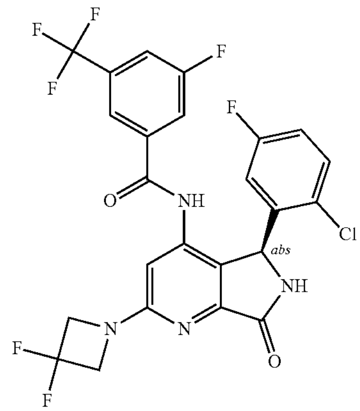 [SMILES: O=C(Nc1cc(N2CC(F)(F)C2)nc2c1[C@@H](c1cc(F)ccc1Cl)NC2=O)c1cc(F)cc(C(F)(F)F)c1] | Fc1ccc(C1)c(c1)[C@H]1NC(=O)c2nc(cc(NC(=O)c3cc(F)cc(c3)C(F)(F)F)c12)N1CC(F)(F)C1 | ¹H NMR (400 MHz, DMSO-d$_6$) δ 10.72 (br s, 1H), 9.30 (br s, 1H), 7.94 (d, J = 6.5 Hz, 1H), 7.71 (d, J = 9.0 Hz, 1H), 7.62 (s, 1H), 7.34 (dd, J = 8.9, 5.2 Hz, 1H), 7.17-6.97 (m, 1H), 6.94-6.56 (m, 2H), 5.91 (br s, 1H), 4.65-4.33 (m, 4H). | 559.2 | D | |
| I-368 | 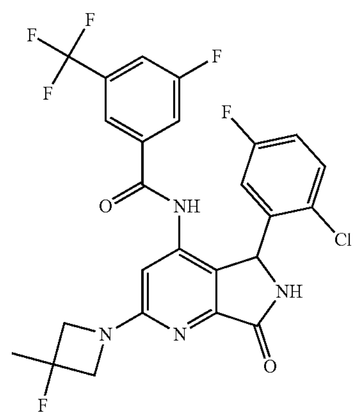 [SMILES: CC1(F)CN(c2cc(NC(=O)c3cc(F)cc(C(F)(F)F)c3)c3c(n2)C(=O)NC3c2cc(F)ccc2Cl)C1] | CC1(F)CN(C1)c1cc(NC(=O)c2cc(F)cc(c2)C(F)(F)c2C(NC(=O)c2n1)c1cc(F)ccc1Cl | 1H NMR (400 MHz, DMSO-d6) 10.64 (s, 1H), 9.27 (s, 1H), 7.96 (d, 8.1 Hz, 1H), 7.70 (d, 8.9 Hz, 1H), 7.60 (s, 1H), 7.32 (dd, 8.9, 5.2 Hz, 1H), 7.13-7.00 (m, 1H), 6.75 (br s, 1H), 6.53 (s, 1H), 5.89 (s, 1H), 4.27-4.01 (m, 4H), 1.67 (d, 22.2 Hz, 3H). | 555.3 | B | |
| I-369 | 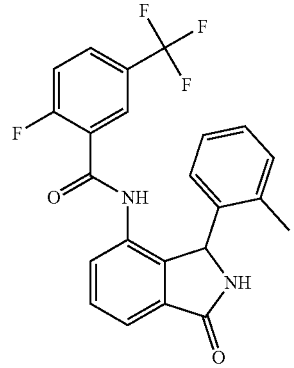 [SMILES: Cc1ccccc1C1NC(=O)c2cccc(NC(=O)c3cc(C(F)(F)F)ccc3F)c21] | Cc1ccccc1C1NC(=O)c2cccc(NC(=O)c3cc(ccc3F)C(F)(F)F)c12 | 1H NMR (400 MHz, DMSO-d6) 10.42 (s, 1H), 9.09 (s, 1H), 7.90 (mt, 1H), 7.68 (dd, 7.5, 1.0 Hz, 1H), 7.62 (t, 7.6 Hz, 1H), 7.58-7.45 (m, 2H), 7.17 (td, 7.2, 0.8 Hz, 1H), 7.12 (d, 6.8 Hz, 1H), 7.03 (td, 7.6, 1.2 Hz, 1H), 6.76 (s, 1H), 6.56 (br. s, 1H), 5.95 (s, 1H), 2.26 (br. s, 3H) | 429.3 | D | |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-370 | 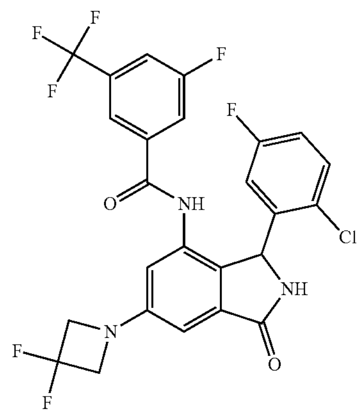 [SMILES: O=C(Nc1cc(N2CC(F)(F)C2)cc2c1C(c1cc(F)ccc1Cl)NC2=O)c1cc(F)cc(C(F)(F)F)c1] | Fc1ccc(C1)c(c1)C1 NC(=O)c 2cc(cc(N C(=O)c3 cc(F)cc(c 3)C(F)(F) F)c12)N1 CC(F)(F) C1 | 1H NMR (400 MHz, CD3CN) 8.55 (s, 1H), 7.66 (d, 8.9 Hz, 1H), 7.60 (d, 8.9 Hz, 1H), 7.57 (s, 1H), 7.27 (dd, 8.9, 5.1 Hz, 1H), 7.18 (s, 1H), 7.01-6.94 (m, 1H), 6.92 (d, 2.2 Hz, 1H), 6.78 (d, 2.2 Hz, 1H), 6.66 (br s, 1H), 6.05 (br s, 1H), 4.37 (t, 12.1 Hz, 4H). | 558.3 | A | |
| I-371 | 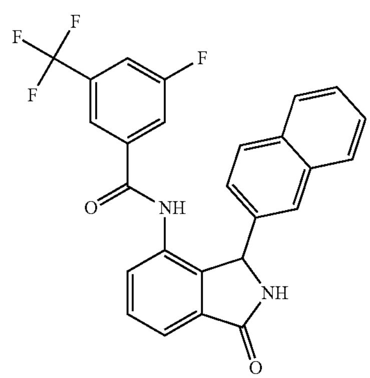 [SMILES: O=C(Nc1cccc2c1C(c1ccc3ccccc3c1)NC2=O)c1cc(F)cc(C(F)(F)F)c1] | Fc1cc(cc (c1)C(F) (F)F)C(= O)Nc1cc cc2C(=O) NC(c12) c1ccc2cc ccc2c1 | 1H NMR (400 MHz, DMSO-d6) 10.35 (s, 1H), 9.18 (s, 1H), 7.84 (d, 8.1 Hz, 1H), 7.78 (d, 8.0 Hz, 1H), 7.72 (dd, 7.2, 0.4 Hz, 1H), 7.70 (d, 8.4 Hz, 1H), 7.66-7.55 (m, 3H), 7.52 (s, 1H), 7.49-7.39 (m, 3H), 7.35 (m, 1H), 6.87 (dd, 8.6, 1.4 Hz, 1H), 5.88 (s, 1H) | 465.2 | E | |
| I-372 | 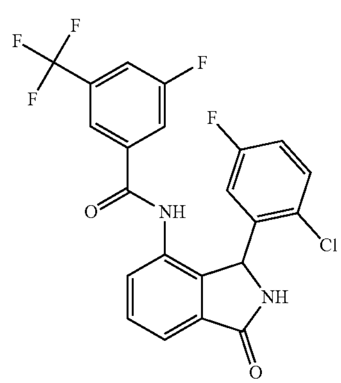 [SMILES: O=C(Nc1cccc2c1C(c1cc(F)ccc1Cl)NC2=O)c1cc(F)cc(C(F)(F)F)c1] | Fc1ccc(C1)c(c1)C1 NC(=O)c 2cccc(N C(=O)c3 cc(F)cc(c 3)C(F)(F) F)c12 | 1H NMR (400 MHz, CD3CN) 8.63 (s, 1H), 7.77 (dd, 7.5, 0.9 Hz, 1H), 7.67-7.52 (m, 5H), 7.25 (dd, 8.9, 5.1 Hz, 2H), 6.97 (ddd, 8.9, 8.0, 3.1 Hz, 1H), 6.62 (br s, 1H), 6.13 (br s, 1H). | 467 | A | |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-373 | 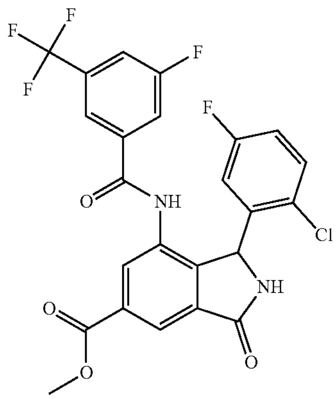 [SMILES: COC(=O)c1cc(NC(=O)c2cc(F)cc(C(F)(F)F)c2)c2c(c1)C(=O)NC2c1cc(F)ccc1Cl] | COC(=O)c1cc2C(=O)NC(c2c(NC(=O)c2cc(F)cc(c2)C(F)(F)F)c1)c1cc(F)ccc1Cl | 1H NMR (400 MHz, d6-DMSO) 10.66 (s, 1H), 9.35 (br s, 1H), 8.13 (dd, 16.4, 1.2 Hz, 2H), 7.96 (d, 8.3 Hz, 1H), 7.76 (d, 8.8 Hz, 1H), 7.68 (s, 1H), 7.33 (dd, 8.9, 5.2 Hz, 1H), 7.10 (td, 8.5, 3.1 Hz, 1H), 6.04 (br s, 1H), 3.93 (s, 3H). | 525.3 | A | |
| I-374 | 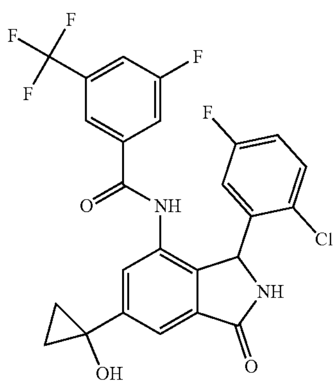 [SMILES: O=C(Nc1cc(C2(O)CC2)cc2c1C(c1cc(F)ccc1Cl)NC2=O)c1cc(F)cc(C(F)(F)F)c1] | OC1(CC1)c1cc2C(=O)NC(c2c(NC(=O)c2cc(F)cc(c2)C(F)(F)F)c1)c1cc(F)ccc1Cl | 1H NMR (400 MHz, CD3CN) 8.61 (s, 1H), 7.67-7.56 (m, 4H), 7.55 (d, 1.6 Hz, 1H), 7.51 (d, 1.3 Hz, 1H), 7.25 (dd, 8.9, 5.1 Hz, 1H), 7.20 (br s, 1H), 6.96 (ddd, 8.9, 8.0, 3.1 Hz, 1H), 6.63 (br s, 1H), 6.09 (s, 1H), 1.30-1.26 (m, 2H), 1.14-1.10 (m, 2H). | 523.4 | A | |
| I-375 | 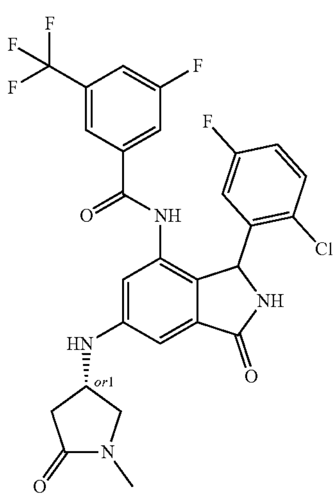 [SMILES: CN1C[C@@H](Nc2cc(NC(=O)c3cc(F)cc(C(F)(F)F)c3)c3c(c2)C(=O)NC3c2cc(F)ccc2Cl)CC1=O] | CN1C[C@H](CC1=O)Nc1cc2C(=O)NC(c2c(NC(=O)c2cc(F)cc(c2)C(F)(F)F)c1)c1cc(F)ccc1Cl | NMR (400 MHz, ) 10.30 (br. s, 1H), 8.95 (br. s, 1H), 7.93 (d, 8.5 Hz, 1H), 7.69 (d, 9.0 Hz, 1H), 7.60 (s, 1H), 7.28 (dd, 8.7, 5.1 Hz, 1H), 7.07 (td, 8.1, 2.8 Hz, 1H), 6.80 (d, 1.3 Hz, 1H), 6.69 (s, 1H), 6.58 (d, 6.2 Hz, 1H), 5.84 (br. s, 1H), 4.17-4.12 (m, 1H), 3.79-3.74 (m, 1H), 3.21 (m, 1H), 2.79-2.73 (m, 1H), 2.75 (s, 3H), 2.25-2.13 (m, 1H) | 579.4 | A | |

TABLE 2-continued

Representative Compounds of the Invention with Bioactivity Data.

| Ex. No. | Structure | SMILES | $^1$H NMR | MS | ADP-Glo IC$_{50}$ | MCF 10A IC$_{50}$ |
|---|---|---|---|---|---|---|
| I-376 | 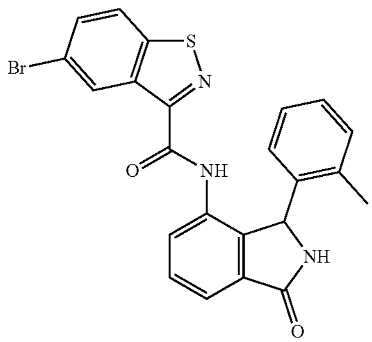 [SMILES: Cc1ccccc1C1NC(=O)c2cccc(NC(=O)c3nsc4ccc(Br)cc34)c21] | Cc1ccccc1C1NC(=O)c2cccc(NC(=O)c3nsc4ccc(Br)cc34)c12 | | 478.3 | C | |
| I-377 | 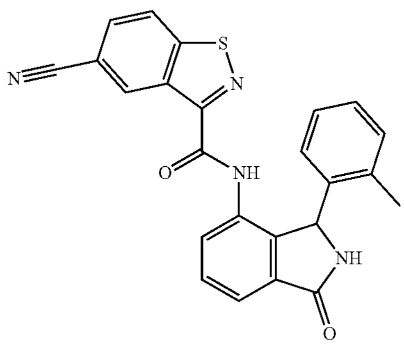 [SMILES: Cc1ccccc1C1NC(=O)c2cccc(NC(=O)c3nsc4ccc(C#N)cc34)c21] | Cc1ccccc1C1NC(=O)c2cccc(NC(=O)c3nsc4ccc(cc34)C#N)c12 | | 425.4 | D | |
| I-378 | 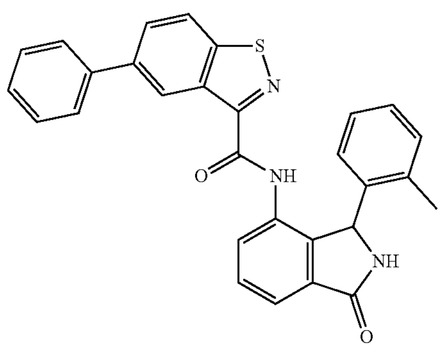 [SMILES: Cc1ccccc1C1NC(=O)c2cccc(NC(=O)c3nsc4ccc(-c5ccccc5)cc34)c21] | Cc1ccccc1C1NC(=O)c2cccc(NC(=O)c3nsc4ccc(cc34)-c3ccccc3)c12 | | 476.5 | D | |
| I-379 | 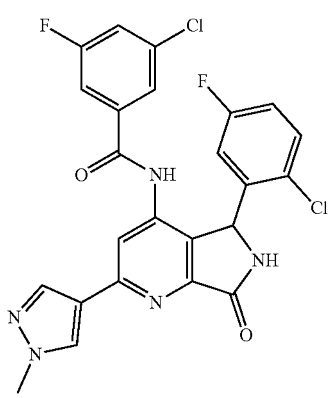 [SMILES: Cn1cc(-c2cc(NC(=O)c3cc(F)cc(Cl)c3)c3c(n2)C(=O)NC3c2cc(F)ccc2Cl)cn1] | Cn1cc(cn1)-c1cc(NC(=O)c2cc(F)cc(Cl)c2)c2C(N C(=O)c2n1)c1cc(F)ccc1Cl | 1H NMR (400 MHz, DMSO-d6) 10.67 (s, 1H), 9.43 (br s, 1H), 8.38 (s, 1H), 8.03 (s, 1H), 7.63-7.76 (m, 2H), 7.27-7.43 (m, 3H), 7.13 (td, 8.4, 3.1 Hz, 1H), 6.79-6.95 (m, 1H), 5.98 (br s, 1H), 3.92 (s, 3H) | 514.4 | B | |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-380 | 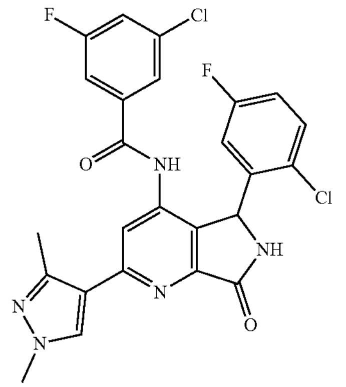 [SMILES: Cc1nn(C)cc1-c1cc(NC(=O)c2cc(F)cc(Cl)c2)c2c(n1)C(=O)NC2c1cc(F)ccc1Cl] | Cc1nn(C)cc1-c1cc(NC(=O)c2cc(F)cc(C1)c2)c2C(NC(=O)c2n1)c1cc(F)ccc1Cl | 1H NMR (DMSO-d6, 400 MHz) 10.65 (br s, 1H), 9.43 (br s, 1H), 8.26 (s, 1H), 7.61-7.75 (m, 2H), 7.29-7.44 (m, 3H), 7.15 (td, 8.4, 3.1 Hz, 1H), 6.81-6.97 (m, 1H), 6.00 (br s, 1H), 3.84 (s, 3H), 3.30 (br s, 3H) | 528.4 | B | |
| I-381 | 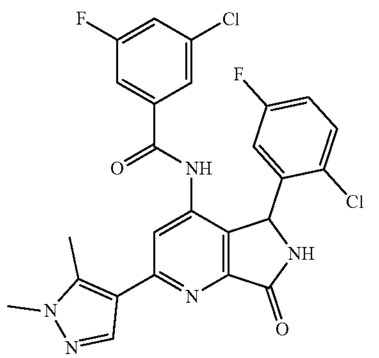 [SMILES: Cc1c(-c2cc(NC(=O)c3cc(F)cc(Cl)c3)c3c(n2)C(=O)NC3c2cc(F)ccc2Cl)cnn1C] | Cc1c(cnn1C)-c1cc(NC(=O)c2cc(F)cc(C1)c2)c2C(NC(=O)c2n1)c1cc(F)ccc1Cl | 1H NMR (DMSO-d6, 400 MHz) 10.66 (br s, 1H), 9.33-9.45 (m, 1H), 7.90 (br s, 1H), 7.57-7.76 (m, 2H), 7.38 (br d, 8.8 Hz, 3H), 7.13 (td, 8.4, 3.1 Hz, 1H), 6.80-6.90 (m, 1H), 5.98 (s, 1H), 3.81 (s, 3H), 2.70 (s, 3H) | 528.4 | B | |
| I-382 | 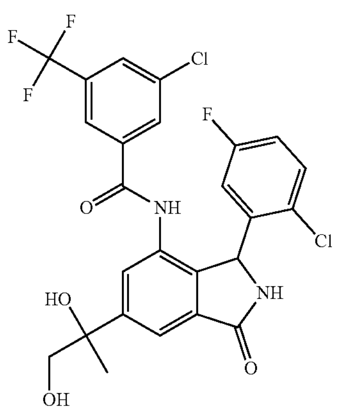 [SMILES: CC(O)(CO)c1cc(NC(=O)c2cc(Cl)cc(C(F)(F)F)c2)c2c(c1)C(=O)NC2c1cc(F)ccc1Cl] | CC(O)(CO)c1cc2C(=O)NC(c2c(NC(=O)c2cc(F)cc(c2)C(F)(F)F)c1)c1cc(F)ccc1Cl | 1H NMR (DMSO-d6, 400 MHz) Shift 10.4-10.7 (m, 1H), 8.9-9.2 (m, 1H), 7.8-8.0 (m, 1H), 7.7-7.8 (m, 1H), 7.66 (s, 1H), 7.5-7.6 (m, 1H), 7.2-7.4 (m, 1H), 6.9-7.2 (m, 1H), 6.5-6.7 (m, 1H), 5.8-6.1 (m, 2H), 5.1-5.3 (m, 1H), 4.7-5.0 (m, 1H), 3.4-3.7 (m, 2H), 1.3-1.6 (m, 3H) | 541 | B | |
| I-383 | 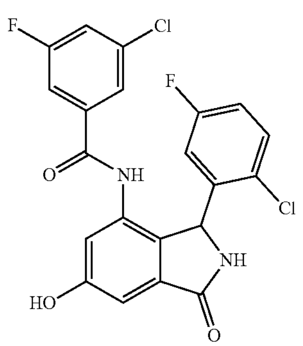 [SMILES: O=C(Nc1cc(O)cc2c1C(c1cc(F)ccc1Cl)NC2=O)c1cc(F)cc(Cl)c1] | Oc1cc2C(=O)NC(c2c(NC(=O)c2cc(F)cc(C1)c2)c1)c1cc(F)ccc1Cl | 1H NMR (400 MHz, DMSO-d6) 5.43-6.14 (m, 2H), 6.82-6.95 (m, 1H), 7.00 (d, 1.95 Hz, 1H), 7.10 (td, 8.36, 3.05 Hz, 1H), 7.25-7.47 (m, 2H), 7.53-7.88 (m, 1H), 8.82-9.39 (m, 2H), 10.00-10.41 (m, 2H) | 450 | A | |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-384 | 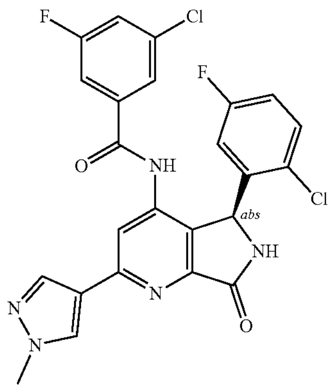 [SMILES: Cn1cc(-c2cc(NC(=O)c3cc(F)cc(Cl)c3)c3c(n2)C(=O)N[C@@H]3c2cc(F)ccc2Cl)cn1] | Cn1cc(cn1)-c1cc(NC(=O)c2cc(F)cc(Cl)c2)c2[C@H](NC(=O)c2n1)c1cc(F)ccc1Cl | ¹H NMR (400 MHz, DMSO-d$_6$) δ 10.67 (s, 1H), 9.43 (br s, 1H), 8.38 (s, 1H), 8.03 (s, 1H), 7.63-7.76 (m, 2H), 7.27-7.43 (m, 3H), 7.13 (td, J = 8.4, 3.1 Hz, 1H), 6.79-6.95 (m, 1H), 5.98 (br s, 1H), 3.92 (s, 3H). | 514.4 | D | |
| I-385 | 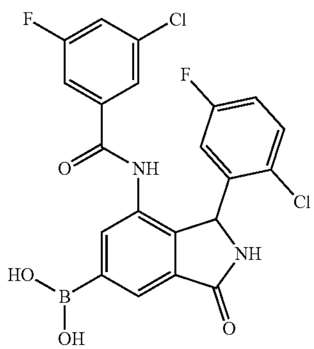 [SMILES: O=C(Nc1cc(B(O)O)cc2c1C(c1cc(F)ccc1Cl)NC2=O)c1cc(F)cc(Cl)c1] | OB(O)c1cc2C(=O)NC(c2c(NC(=O)c2cc(F)cc(Cl)c2)c1)c1cc(F)ccc1Cl | 1H NMR (400 MHz, DMSO-d6) 5.78-6.22 (m, 1H), 6.46-6.65 (m, 1H), 6.93-7.22 (m, 1H), 7.25-7.49 (m, 1H), 7.55-7.71 (m, 1H), 7.81-7.91 (m, 1H), 8.11-8.23 (m, 1H), 8.36-8.58 (m, 1H), 8.88-9.35 (m, 1H), 10.16-10.67 (m, 1H) | 478 | A | |
| I-386 | 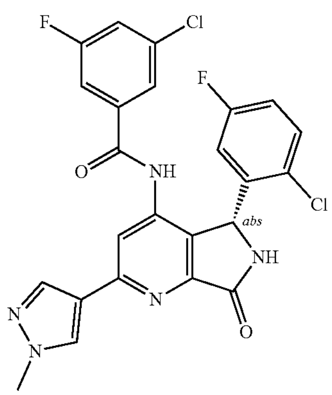 [SMILES: Cn1cc(-c2cc(NC(=O)c3cc(F)cc(Cl)c3)c3c(n2)C(=O)N[C@H]3c2cc(F)ccc2Cl)cn1] | Cn1cc(cn1)-c1cc(NC(=O)c2cc(F)cc(Cl)c2)c2[C@@H](NC(=O)c2n1)c1cc(F)ccc1Cl | ¹H NMR (400 MHz, DMSO-d$_6$) δ 10.67 (s, 1H), 9.43 (br s, 1H), 8.38 (s, 1H), 8.03 (s, 1H), 7.63-7.76 (m, 2H), 7.27-7.43 (m, 3H), 7.13 (td, J = 8.4, 3.1 Hz, 1H), 6.79-6.95 (m, 1H), 5.98 (br s, 1H), 3.92 (s, 3H). | 514.4 | A | |
| I-387 | 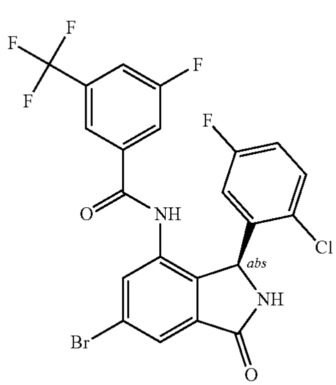 [SMILES: O=C(Nc1cc(Br)cc2c1[C@@H](c1cc(F)ccc1Cl)NC2=O)c1cc(F)cc(C(F)(F)F)c1] | Fc1ccc(Cl)c(c1)[C@H]1NC(=O)c2cc(Br)cc(NC(=O)c3cc(F)cc(c3)C(F)(F)F)c12 | 1H NMR (DMSO-d6, 500 MHz) 10.4-10.7 (m, 1H), 9.1-9.4 (m, 1H), 7.9-8.0 (m, 1H), 7.8-7.9 (m, 1H), 7.7-7.8 (m, 2H), 7.6-7.7 (m, 1H), 7.2-7.4 (m, 1H), 7.0-7.1 (m, 1H), 6.3-6.8 (m, 1H), 5.8-6.1 (m, 1H) | 546 | D | |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-388 | 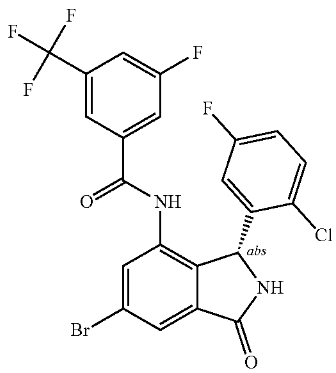 [SMILES: O=C(Nc1cc(Br)cc2c1[C@H](c1cc(F)ccc1Cl)NC2=O)c1cc(F)cc(C(F)(F)F)c1] | Fc1ccc(C 1)c(c1)[C @@H]1 NC(=O)c 2cc(Br)cc (NC(=O) c3cc(F)cc (c3)C(F) (F)F)c12 | 1H NMR (DMSO-d6, 500 MHz) 10.4-10.7 (m, 1H), 9.1-9.4 (m, 1H), 7.9-8.0 (m, 1H), 7.8-7.9 (m, 1H), 7.7-7.8 (m, 2H), 7.6-7.7 (m, 1H), 7.2-7.4 (m, 1H), 7.0-7.1 (m, 1H), 6.3-6.8 (m, 1H), 5.8-6.1 (m, 1H) | 546 | A | A |
| I-389 | 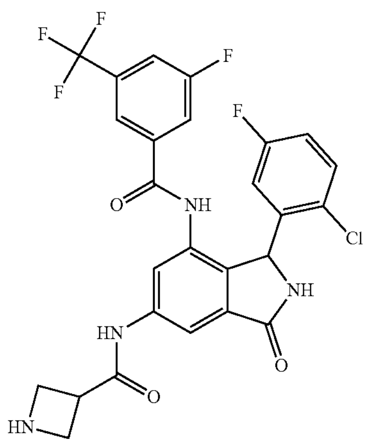 [SMILES: O=C(Nc1cc(NC(=O)C2CNC2)cc2c1C(c1cc(F)ccc1Cl)NC2=O)c1cc(F)cc(C(F)(F)F)c1] | Fc1ccc(C 1)c(c1)C1 NC(=O)c 2cc(NC (=O)C3C NC3)cc (NC(=O)c 3cc(F)cc (c3)C(F) (F)F)c12 | 1H NMR (400 MHz, DMSO-d6) 3.73-3.81 (m, 1H), 3.94-4.21 (m, 4H), 5.80-6.02 (m, 2H) 6.52 (s, 1H), 7.08 (td,8.36, 2.81 Hz, 1 H), 7.31 (br dd, 8.79, 5.13 Hz, 1 H), 7.61 (s, 1H), 7.67-7.80 (m, 2H), 7.90-8.03 (m, 2H), 8.46-8.56 (m, 1H), 9.15 (br s, 1H), 10.49 (br d, 3.17 Hz, 1H) | 565.5 | B | |
| I-390 | 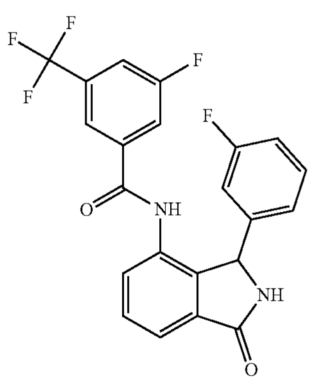 [SMILES: O=C(Nc1cccc2c1C(c1cccc(F)c1)NC2=O)c1cc(F)cc(C(F)(F)F)c1] | Fc1cccc (c1)C1NC (=O)c2cc cc(NC(= O)c3cc(F) cc(c3)C (F)(F)F)c1 2 | 1H NMR (400 MHz, DMSO-d6) 10.44 (s, 1H), 9.12 (s, 1H), 8.01-7.93(m, 1H), 7.77-7.72(m, 1H), 7.69 (dd, 7.5, 1.0 Hz, 1H), 7.66 (br s, 1H), 7.61 (t, 7.6 Hz, 1H), 7.54-7.49 (m, 1H), 7.19 (td, 8.0, 6.0 Hz, 1H), 7.07-6.98 (m, 1H), 6.83-6.74 (m, 2H), 5.74 (s, 1H). | 431.3 | D | |
| I-391 | 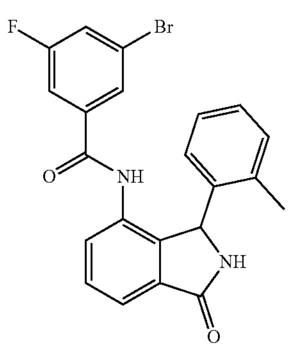 [SMILES: Cc1ccccc1C1NC(=O)c2cccc(NC(=O)c3cc(F)cc(Br)c3)c21] | Cc1ccccc 1C1NC(= O)c2cccc (NC(=O) c3cc(F)cc (Br)c3)c1 2 | 1H NMR (400 MHz, DMSO-d6) 10.22 (s, 1H), 9.06 (s, 1H), 7.74 (td, 8.3, 2.0 Hz, 1H), 7.67 (dd, 7.4, 1.1 Hz, 1H), 7.61 (t, 7.5 Hz, 1H), 7.53 (dd, 7.7, 0.9 Hz, 1H), 7.21-7.14 (m, 2H), 7.10 (dd, 7.4, 1.2 Hz, 1H), 7.04 (d, 7.1 Hz, 1H), 6.98 (t, 7.2 Hz, 1H), 6.54 (br s, 1H), 5.90 (s, 1H), 2.20 (br s, 3H). | 439.2 | C | |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-392 | 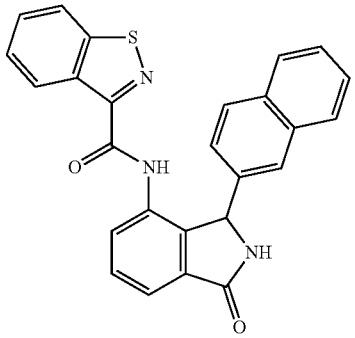 [SMILES: O=C1NC(c2ccc3ccccc3c2)c2c(NC(=O)c3nsc4ccccc34)cccc21] | O=C(Nc1 cccc2C(= O)NC(c1 2)c1ccc2 ccccc2c1) c1nsc2c cccc12 | 1H NMR (400 MHz, DMSO-d6) 10.22 (s, 1H), 9.18 (s, 1H), 8.56 (dt, 8.2, 1.0 Hz, 1H), 8.25 (dt, 8.3, 0.9 Hz, 1H), 7.85 (s, 1H), 7.77 (dd, 7.8, 0.9 Hz, 1H), 7.69 (d, 8.0 Hz, 1H), 7.66-7.60 (m, 3H), 7.57 (t, 7.7 Hz, 1H), 7.50 (ddd, 8.0, 7.0, 1.0 Hz, 1H), 7.39 (d, 8.1 Hz., 1H), 7.33 (ddd, 8.2, 6.9, 1.4 Hz, 1H), 7.26 (ddd, 8.1, 6.9, 1.2 Hz, 1H), 6.93 (dd, 8.5, 1.7 Hz, 1H), 6.09 (s, 1H) | 436.3 | E | |
| I-393 | 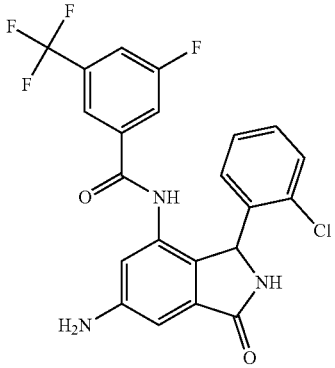 [SMILES: Nc1cc(NC(=O)c2cc(F)cc(C(F)(F)F)c2)c2c(c1)C(=O)NC2c1ccccc1Cl] | Nc1cc2C (=O)NC (c2c(NC (=O)c2cc (F)cc(c2) C(F)(F)F) c1)c1ccc cc1Cl | 1H NMR (400 MHz, CD3CN) 8.34 (s, 1H), 7.61 (d, 8.5 Hz, 1H), 7.52-7.44 (m, 3H), 7.28-7.23 (m, 2H), 7.19 (td, 7.6, 1.7 Hz, 1H), 7.12 (t, 7.4 Hz, 1H), 7.06 (s, 1H), 6.99-6.87 (m, 3H), 6.03 (s, 1H). | 464 | A | |
| I-394 | 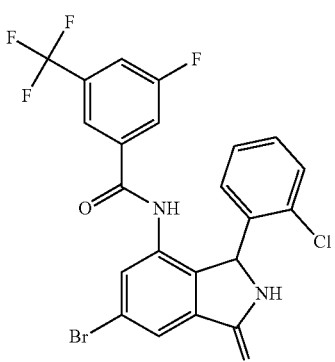 | Fc1cc(cc (c1)C(F) (F)F)C(= O)Nc1cc (Br)cc2C (=O)NC(c 12)c1ccc cc1Cl | 1H NMR (400 MHz, CD3CN) 8.62 (br s, 1H), 7.88 (d, 1.7 Hz, 1H), 7.80 (br s, 1H), 7.67-7.61 (m, 1H), 7.53-7.46 (m, 2H), 7.32 (br s, 1H), 7.28 (dd, 8.0, 1.6 Hz, 1H), 7.24-7.19 (m, 1H), 7.12 (br t, 7.0 Hz, 1H), 6.90 (br s, 1H), 6.13 (br s, 1H). | 527 | B | |
| I-395 | 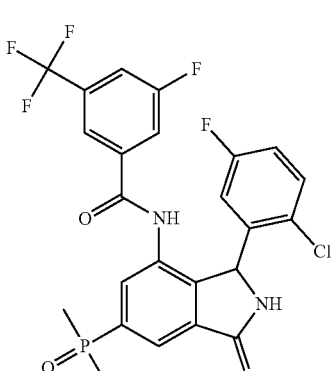 | CP(C)(= O)c1cc2 C(=O)N C(c2c(N C(=O)c2 cc(F)cc(c 2)C(F)(F) F)c1)c1c c(F)ccc1 Cl | 1H NMR (400 MHz, DMSO-d6) 9.29 (br s, 1 H), 8.34 (br s, 1 H), 8.08 (d, 10.5 Hz, 1 H), 7.96 (d, 8.6 Hz, 1 H), 7.91 (d, 11.5 Hz, 1 H), 7.76 (d, 8.8 Hz, 1 H), 7.69 (s, 1 H), 7.32 (dd, 8.9, 5.1 Hz, 1 H), 7.10 (td, 8.5, 3.0 Hz, 1 H), 6.67 (br s, 1H), 6.04 (br s, 1 H), 1.80-1.70 (m, 6H). | 543.3 | A | |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-396 | 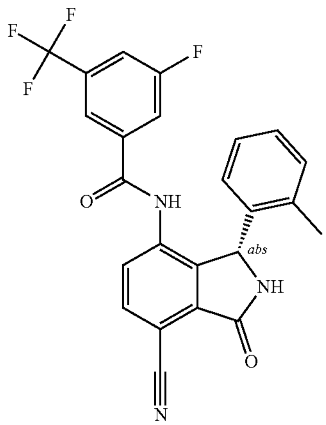 | Cc1ccccc1[C@@H]1NC(=O)c2c1c(NC(=O)c1cc(F)cc(c1)C(F)(F)F)ccc2C#N | 1H NMR (400 MHz, DMSO-d6) 10.64 (br s, 1 H), 9.48 (s, 1 H), 8.08 (d, 8.1 Hz, 1 H), 7.90 (d, 8.3 Hz, 1 H), 7.77 (d, 8.0 Hz, 1 H), 7.49-7.43 (m, 1H), 7.30 (br s, 1 H), 7.08 (td, 7.5, 1.2 Hz, 1 H), 7.01 (d, 7.2 Hz, 1 H), 6.97 (1, 7.3 Hz, 1 H), 6.52 (br s, 1 H), 5.96 (s, 1 H), 2.28 (s, 3 H). | 454.3 | | |
| I-397 | 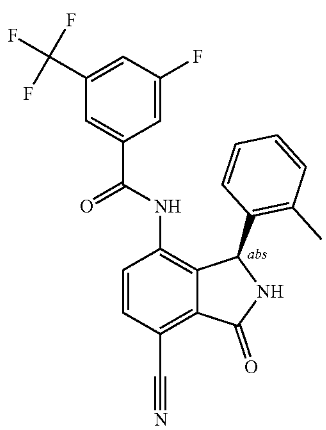 [SMILES: Cc1ccccc1[C@H]1NC(=O)c2c(C#N)ccc(NC(=O)c3cc(F)cc(C(F)(F)F)c3)c21] | Cc1ccccc1[C@H]1NC(=O)c2c1c(NC(=O)c1cc(F)cc(c1)C(F)(F)F)ccc2C#N | (400 MHz, DMSO-D6) 10.64 (br s, 1 H), 9.48 (s, 1 H), 8.08 (d, 8.1 Hz, 1 H), 7.90 (d, 8.3 Hz, 1 H), 7.77 (d, 8.0 Hz, 1 H), 7.49-7.43 (m, 1 H), 7.30 (br s, 1 H), 7.08 (td, 7.5, 1.2 Hz, 1 H), 7.01 (d, 7.2 Hz, 1 H), 6.97 (t, 7.3 Hz, 1 H), 6.52 (br s, 1 H), 5.96 (s, 1 H), 2.28 (s, 3 H). | 454.3 | B | |
| I-398 | 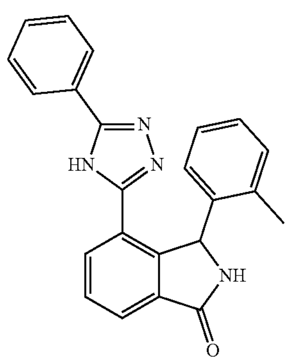 [SMILES: Cc1ccccc1C1NC(=O)c2cccc(-c3nnc(-c4ccccc4)[nH]3)c21] | Cc1ccccc1C1NC(=O)c2cccc(-c3nnc([nH]3)-c3ccccc3)c12 | NMR (400 MHz, DMSO-d6) 8.29 (br. s, 1H), 8.02-8.01 (m, 2H), 7.82-7.81 (m, 2H), 7.58 (br. s, 1H), 7.28-7.24 (m, 4H), 7.21-7.15 (m, 4H), 6.67 (br. s, 1H), 2.10 (br. s, 3H)-0.88-0.82 | 366.2 | E | |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-399 | 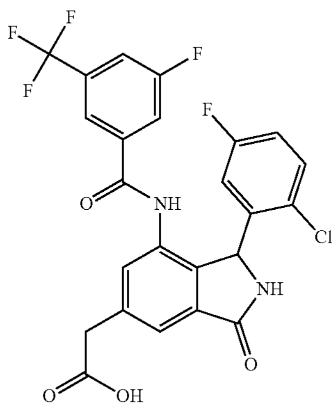 [SMILES: O=C(O)Cc1cc(NC(=O)c2cc(F)cc(C(F)(F)F)c2)c2c(c1)C(=O)NC2c1cc(F)ccc1Cl] | OC(=O) Cc1cc2C (=O)NC (c2c(NC (=O)c2cc (F)cc(c2) C(F)(F)F) c1cc (F)ccc1Cl | 1H-NMR (400 MHz, DMSO-d6) 10.51 (br. s, 1H), 9.11 (s, 1H), 7.93 (dt, 8.5, 1.7 Hz, 1H), 7.73 (br. d, 8.8 Hz, 1H), 7.66 (s, 1H), 7.58 (s, 1H), 7.37 (s, 1H), 7.31 (dd, 8.9, 5.2 Hz, 1H), 7.09 (td, 8.5, 3.1 Hz, 1H), 6.58 (br. s, 1H), 5.95 (br. s, 1H), 3.71 (d, A of AB, JAB = 15.9 Hz, 1H), 3.66 (d, B of AB, JAB = 15.6 Hz, 1H). | 525.3 | A | |
| I-400 | 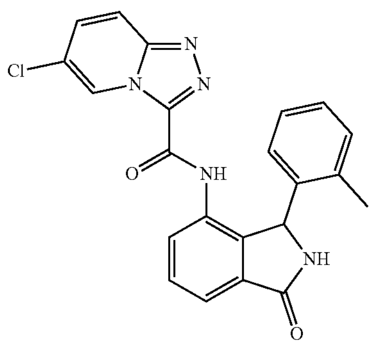 [SMILES: Cc1ccccc1C1NC(=O)c2cccc(NC(=O)c3nnc4ccc(Cl)cn34)c21] | Cc1ccccc 1C1NC(= O)c2cccc (NC(=O) c3nnc4cc c(Cl)cn3 4)c12 | 1H-NMR (400 MHz, DMSO-d6) 10.70 (s, 1H), 9.08 (dd, 1.9, 0.9 Hz, 1H), 9.05 (s, 1H), 8.06 (dd, 9.7, 1.0 Hz, 1H), 7.71-7.66 (m, 3H), 7.65-7.59 (m, 1H), 6.94-6.86 (m, 2H), 6.85-6.79 (m, 1H), 6.67 (br. s, 1H), 6.07 (s, 1H), 2.18 (br. s, 3H). | 418.3 | E | |
| I-401 | 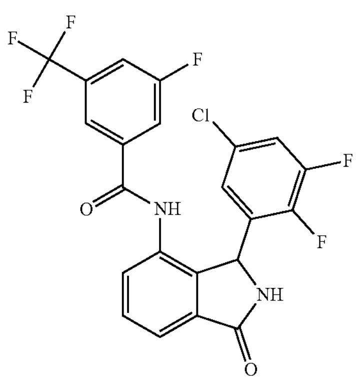 [SMILES: O=C(Nc1cccc2c1C(c1cc(Cl)cc(F)c1F)NC2=O)c1cc(F)cc(C(F)(F)F)c1] | Fc1cc(cc (c1)C(F) (F)F)C(= O)Nc1cc cc2C(=O) NC(c12) c1cc(Cl)c c(F)c1F | 1H NMR (400 MHz, CD3CN) 8.84 (s, 1H), 7.77 (d, 7.5 Hz, 1H), 7.74-7.66 (m, 3H), 7.63 (t, 7.7 Hz, 1H), 7.50 (d, 7.7 Hz, 1H). 7.26-7.15 (m, 2H), 6.89-6.79 (m, 1H), 5.93 (s, 1H). | 485.2 | B | |
| I-402 | 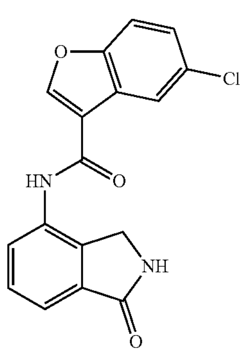 [SMILES: O=C1NCc2c(NC(=O)c3coc4ccc(Cl)cc34)cccc21] | C1c1ccc2 occ(C(= O)Nc3cc cc4C(=O) NCc34)c 2c1 | | | E | |

TABLE 2-continued

Representative Compounds of the Invention with Bioactivity Data.

| Ex. No. | Structure | SMILES | $^1$H NMR | MS | ADP-Glo IC$_{50}$ | MCF 10A IC$_{50}$ |
|---|---|---|---|---|---|---|
| I-403 | 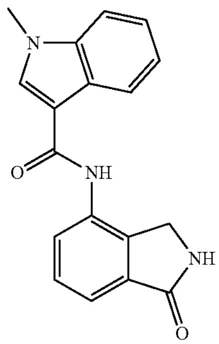 [SMILES: Cn1cc(C(=O)Nc2cccc3c2CNC3=O)c2ccccc21] | Cn1cc(C(=O)Nc2cccc3C(=O)NCc23)c2ccccc12 | | | | E |
| I-404 | 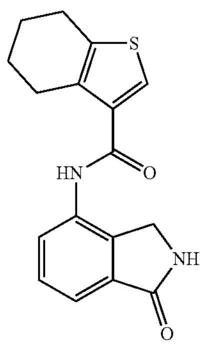 [SMILES: O=C1NCc2c(NC(=O)c3csc4c3CCCC4)cccc21] | O=C(Nc1cccc2C(=O)NCc12)c1csc2CCCCc12 | | | | E |
| I-405 | 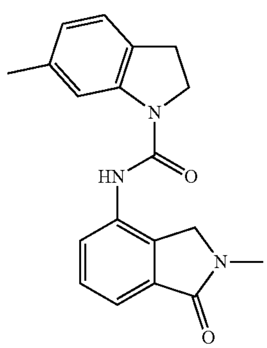 | CN1Cc2c(cccc2NC(=O)N2CCc3ccc(C)cc23)C1=O | | | | E |
| I-406 | 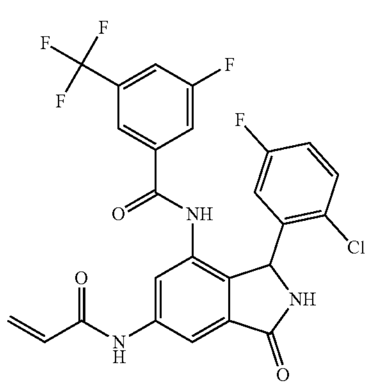 [SMILES: C=CC(=O)Nc1cc(NC(=O)c2cc(F)cc(C(F)(F)F)c2)c2c(c1)C(=O)NC2c1cc(F)ccc1Cl] | Fc1ccc(C1)c(c1)C1NC(=O)c2cc(NC(=O)C=C)cc(NC(=O)c3cc(F)cc(c3)C(F)(F)F)c12 | | 536.25 | A | |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-407 | 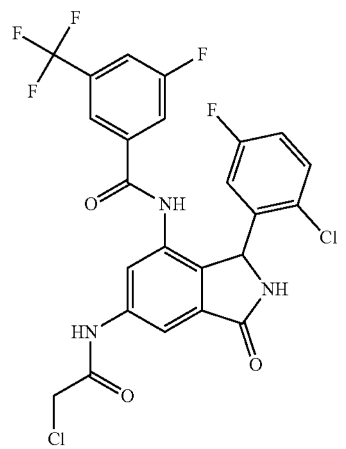 [SMILES: O=C(CCl)Nc1cc(NC(=O)c2cc(F)cc(C(F)(F)F)c2)c2c(c1)C(=O)NC2c1cc(F)ccc1Cl] | Fc1ccc(C1)c(c1)C1NC(=O)c2cc(NC(=O)CC1)cc(NC(=O)c3cc(F)cc(c3)C(F)(F)F)c12 | | 558.26 | A | |
| I-408 | 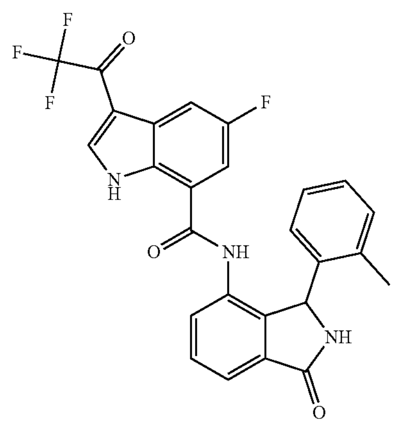 [SMILES: Cc1ccccc1C1NC(=O)c2cccc(NC(=O)c3cc(F)cc4c(C(=O)C(F)(F)F)c[nH]c34)c21] | Cc1ccccc1C1NC(=O)c2cccc(NC(=O)c3cc(F)cc4c(c[nH]c34)C(=O)C(F)(F)F)c12 | 1H NMR (400 MHz, DMSO-d6) Shift 12.68 (br s, 1H), 10.36 (br s, 1H), 9.06 (s, 1H), 8.28 (br s, 1H), 8.01 (br d, 5.86 Hz, 1H), 7.47-7.72 (m, 3H), 6.84-7.06 (m, 3H), 6.44-6.73 (m, 2H), 6.00 (br s, 1H), 1.94-2.28 (m, 3H) | 496.28 | E | |
| I-409 | 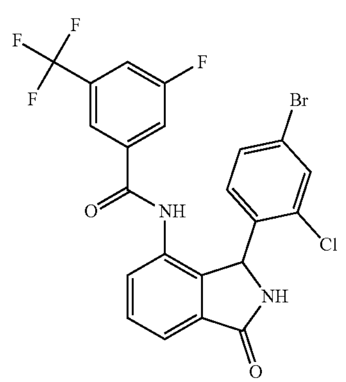 [SMILES: O=C(Nc1cccc2c1C(c1ccc(Br)cc1Cl)NC2=O)c1cc(F)cc(C(F)(F)F)c1] | Fc1cc(cc(c1)C(F)(F)F)C(=O)Nc1ccc2C(=O)NC(c12)c1ccc(Br)cc1Cl | | | D | |

| Ex. No. | Structure | SMILES | ¹H NMR | MS | ADP-Glo IC$_{50}$ | MCF 10A IC$_{50}$ |
|---|---|---|---|---|---|---|
| I-410 | 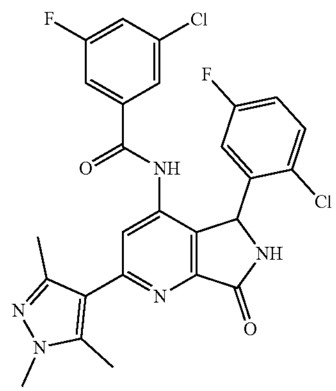 [SMILES: Cc1nn(C)c(C)c1-c1cc(NC(=O)c2cc(F)cc(Cl)c2)c2c(n1)C(=O)NC2c1cc(F)ccc1Cl] | Cc1nn(C)c(C)c1-c1cc(NC(=O)c2cc(F)cc(C1)c2)c2C(NC(=O)c2n1)c1cc(F)ccc1C1 | | 542.4 | C | |
| I-411 | 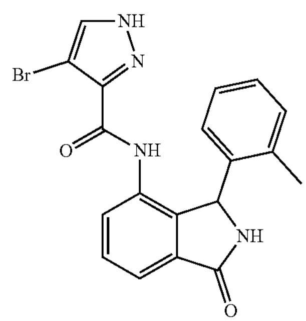 [SMILES: Cc1ccccc1C1NC(=O)c2cccc(NC(=O)c3n[nH]cc3Br)c21] | Cc1ccccc1C1NC(=O)c2cccc(NC(=O)c3n[nH]c c3Br)c12 | 1H NMR (400 MHz, DMSO-d6) 13.52-13.93 (m, 1H), 9.42 (br s, 1H), 8.98 (s, 1H), 8.03 (s, 1H), 7.79 (dd, 7.20, 1.10 Hz, 1H), 7.50-7.60 (m, 2H), 7.02-7.13 (m, 2H), 6.96 (dt, 7.87, 4.24 Hz, 1H), 6.54-6.73 (m, 1H), 6.06 (s, 1H), 2.14-2.40 (m, 3H) | 411.19 | E | |
| I-412 | 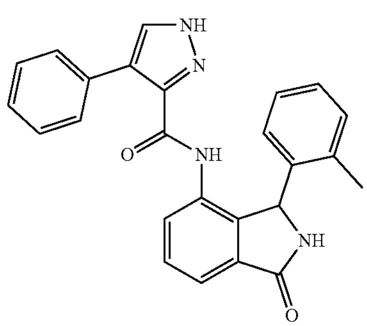 [SMILES: Cc1ccccc1C1NC(=O)c2cccc(NC(=O)c3n[nH]cc3-c3ccccc3)c21] | Cc1ccccc1C1NC(=O)c2cccc(NC(=O)c3n[nH]c c3-c3ccccc3)c12 | 1H NMR (400 MHz, DMSO-d6) 13.43 (br s, 1 H), 9.37 (br s, 1H), 8.97 (s, 1H) 7.99 (s, 1H) 7.85 (br d, 5.37 Hz., 1H) 7.48-7.61 (m, 2 H), 7.43 (br s, 2H) 7.26-7.35 (m, 2H) 7.19-7.26 (m, 1H) 7.06-7.16 (m, 2H) 6.95-7.05 (m, 1H) 6.57-6.77 (m, 1H) 6.07 (s, 1H) 2.14-2.42 (m, 3H) | 409.39 | E | |
| I-413 | 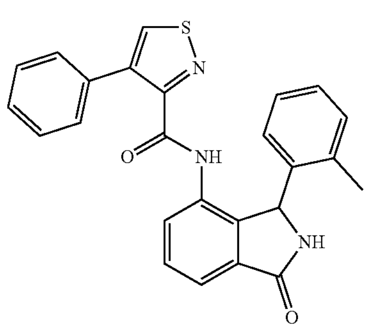 [SMILES: Cc1ccccc1C1NC(=O)c2cccc(NC(=O)c3nscc3-c3ccccc3)c21] | Cc1ccccc1C1NC(=O)c2cccc(NC(=O)c3nscc3-c3ccccc3)c12 | 1H NMR (400 MHz, DMSO-d6) 9.99 (s, 1 H), 9.05 (s, 1 H), 8.98 (s, 1 H), 7.68 (d, 7.32 Hz, 1 H) 7.50-7.62 (m, 2 H) 7.29-7.38 (m, 3 H), 7.17-7.27 (m, 2 H) 7.07-7.13 (m, 2 H) 6.97-7.04 (m, 1 H) 6.64 (br d, 3.17 Hz, 1 H), 6.03 (s, 1 H), 2.13-2.30 (m, 3 H) | 426.3 | D | |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-414 | 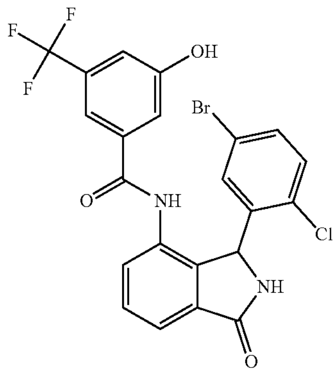 [SMILES: O=C(Nc1cccc2c1C(c1cc(Br)ccc1Cl)NC2=O)c1cc(O)cc(C(F)(F)F)c1] | Oc1cc(cc(c1)C(F)(F)F)C(=O)Nc1ccc c2C(=O)NC(c12)c1cc(Br)ccc1Cl | | 525 | B | |
| I-415 | 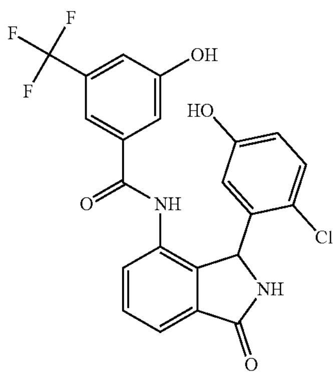 [SMILES: O=C(Nc1cccc2c1C(c1cc(O)ccc1Cl)NC2=O)c1cc(O)cc(C(F)(F)F)c1] | Oc1ccc(C1)c(c1)C1NC(=O)c2cccc(NC(=O)c3cc(O)cc(c3)C(F)(F)F)c12 | 1H NMR (400 MHz, DMSO-d6) 5.81-6.28 (m, 2 H), 6.47-6.72 (m, 1 H), 6.90-7.06 (m, 1 H), 7.17 (s, 1 H), 7.25-7.35 (m, 1 H), 7.38-7.52 (m, 1 H), 7.54-7.90 (m, 1 H), 8.90-9.20 (m, 1 H), 9.29-9.81 (m, 1 H), 10.09-10.38 (m, 1 H) | 463 | E | |
| I-416 | 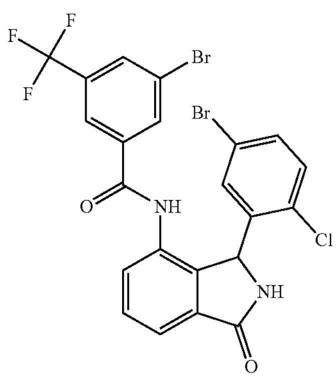 [SMILES: O=C(Nc1cccc2c1C(c1cc(Br)ccc1Cl)NC2=O)c1cc(Br)cc(C(F)(F)F)c1] | FC(F)(F)c1cc(Br)cc(c1)C(=O)Nc1ccc c2C(=O)NC(c12)c1cc(Br)ccc1Cl | 1H NMR (400 MHz, DMSO-d6) 5.59-6.12 (m, 1 H), 6.47-6.69 (m, 1 H), 7.16-7.29 (m, 1 H), 7.31-7.52 (m, 1 H), 7.53-7.73 (m, 1 H), 7.75-7.86 (m, 1 H), 7.89-8.03 (m, 1 H), 8.14-8.32 (m, 1 H), 8.79-9.36 (m, 1 H), 10.34-10.85 (m, 1 H) | 589 | | |
| I-417 | 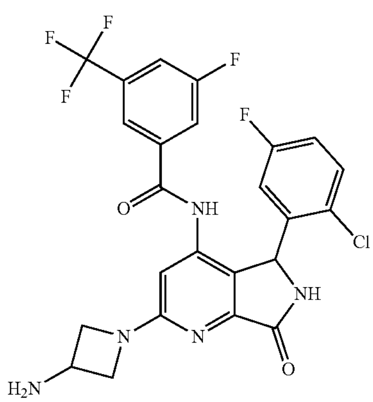 [SMILES: NC1CN(c2cc(NC(=O)c3cc(F)cc(C(F)(F)F)c3)c3c(n2)C(=O)NC3c2cc(F)ccc2Cl)C1] | NC1CN(C1)c1cc(NC(=O)c2cc(F)cc(c2)C(F)(F)F)c2C(NC(=O)c2nl)c1cc(F)ccc1Cl | 1H NMR (400 MHz, DMSO-d6) 10.62 (br s, 1H), 9.23 (s, 1H), 8.25 (s, 1H), 7.95 (d, 8.2 Hz, 1H), 7.71 (d, 8.9 Hz, 1H), 7.61 (s, 1H), 7.32 (dd, 8.8, 5.1 Hz, 1H), 7.07 (td, 8.5, 3.0 Hz, 1H), 6.70 (br s, 1H), 6.46 (s, 1H), 5.88 (s, 1H), 4.22 (d, 8.1 Hz, 2H), 3.95-3.85 (m, 1H), 3.69 (dd, 14.1, 8.4 Hz, 2H). | 538.3 | B | |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-418 | 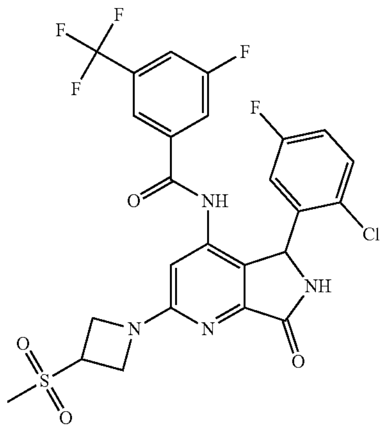 [SMILES: CS(=O)(=O)C1CN(c2cc(NC(=O)c3cc(F)cc(C(F)(F)F)c3)c3c(n2)C(=O)NC3c2cc(F)ccc2Cl)C1] | CS(=O)(=O)C1CN(C1)c1cc(NC(=O)c2cc(F)cc(c2)C(F)(F)F)c2C(NC(=O)c2n1)c1cc(F)ccc1C1 | 1H NMR (400 MHz, DMSO-d6) 10.51 (br s, 1H), 9.26 (s, 1H), 8.34 (s, 1H), 7.92 (d, 14.2 Hz, 1H), 7.71 (d, 9.0 Hz, 1H), 7.62 (s, 1H), 7.33 (dd, 8.8, 5.2 Hz, 1H), 7.08 (td, 8.3, 3.0 Hz, 1H), 6.75 (br s, 1H), 6.63 (s, 1H), 5.89 (s, 1H), 4.53-4.41 (m, 1H), 4.36 (q, 8.4 Hz, 2H), 4.24 (td, 8.9, 5.2 Hz, 2H), 3.10 (s, 1H). | 601.1 | B | |
| I-419 | 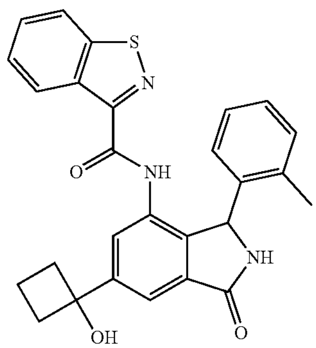 [SMILES: Cc1ccccc1C1NC(=O)c2cc(C3(O)CCC3)cc(NC(=O)c3nsc4ccccc34)c21] | Cc1ccccc1C1NC(=O)c2cc(c(NC(=O)c3nsc4ccccc34)c12)C1(O)CCC1 | 1H NMR (400 MHz, CD3CN) 8.93 (s, 1H), 8.85 (d, 8.1 Hz, 1H), 8.26 (t, 1.5 Hz, 1H), 8.13 (dt, 8.2, 1.0 Hz, 1H), 8.10 (s, 2.8 Hz, 1H), 7.65 (ddd, 7.1, 6.4, 1.3 Hz, 2H), 7.59 (ddd, 8.1, 7.0, 1.1 Hz, 1H), 7.23-7.10 (m, 4H), 7.05 (td, 8.2, 3.5 Hz, 1H), 6.05 (brs, 1H), 1.01 (t, 6.1 Hz, 1H), 0.90 (t, 7.3 Hz, 1H), 0.82 (dd, 6.4, 1.6 Hz, 4H) | 470.3 | A | |
| I-420 | 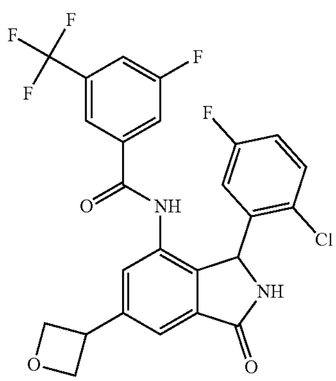 [SMILES: O=C(Nc1cc(C2COC2)cc2c1C(c1cc(F)ccc1Cl)NC2=O)c1cc(F)cc(C(F)(F)F)c1] | Fc1ccc(C1)c(c1)C1NC(=O)c2cc(cc(NC(=O)c3cc(F)cc(c3)C(F)(F)F)c12)C1COC1 | 1H NMR (400 MHz, DMSO-d6) 2.07 (s, 3 H) 4.43 (dt, 15.13, 7.32 Hz, 1 H) 4.59-4.76 (m, 2 H) 4.98-5.04 (m, 1 H) 5.98 (br d, 4.39 Hz, 1 H) 7.09 (td, 8.36, 3.05 Hz, 1 H) 7.31 (br dd, 8.79, 5.13 Hz, 1 H) 7.56 (s, 1 H) 7.65-7.78 (m, 2 H) 7.94 (br d, 8.30 Hz, 1 H) 9.15 (br s, 1 H) 10.52 (s, 1 H) | 523.25 | A | |
| I-421 | 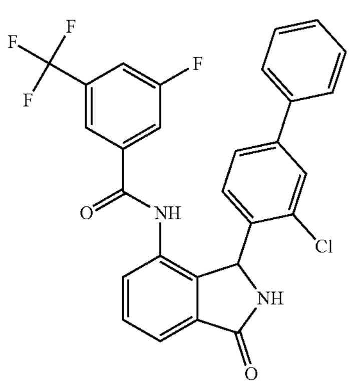 [SMILES: O=C(Nc1cccc2c1C(c1ccc(-c3ccccc3)cc1Cl)NC2=O)c1cc(F)cc(C(F)(F)F)c1] | Fc1cc(cc(c1)C(F)(F)F)C(=O)Nc1ccc2C(=O)NC(c12)c1ccc(cc1Cl)-c1ccccc1 | | | D | |

TABLE 2-continued

Representative Compounds of the Invention with Bioactivity Data.

| Ex. No. | Structure | SMILES | $^1$H NMR | MS | ADP-Glo IC$_{50}$ | MCF 10A IC$_{50}$ |
|---|---|---|---|---|---|---|
| I-422 | 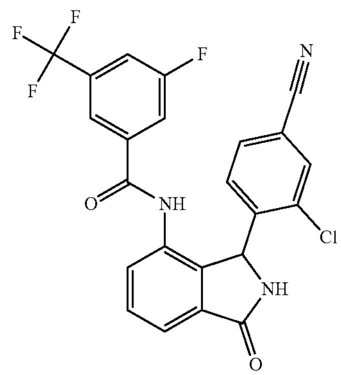 [SMILES: N#Cc1ccc(C2NC(=O)c3cccc(NC(=O)c4cc(F)cc(C(F)(F)F)c4)c32)c(Cl)c1] | Fc1cc(cc(c1)C(F)(F)F)C(=O)Nc1cccc2C(=O)NC(c12)c1ccc(cc1Cl)C#N | | | | E |
| I-423 | 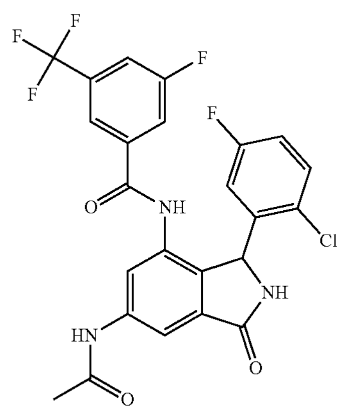 [SMILES: CC(=O)Nc1cc(NC(=O)c2cc(F)cc(C(F)(F)F)c2)c2c(c1)C(=O)NC2c1cc(F)ccc1Cl] | CC(=O)Nc1cc2C(=O)NC(c2c(NC(=O)c2cc(F)cc(c2)C(F)(F)F)c1)c1cc(F)ccc1Cl | | 524.25 | | A |
| I-424 | 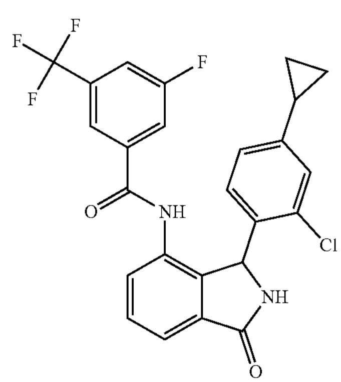 [SMILES: O=C(Nc1cccc2c1C(c1ccc(C3CC3)cc1Cl)NC2=O)c1cc(F)cc(C(F)(F)F)c1] | Fc1cc(cc(c1)C(F)(F)F)C(=O)Nc1ccccc2C(=O)NC(c12)c1ccc(cc1Cl)C1CC1 | | | | D |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-425 | 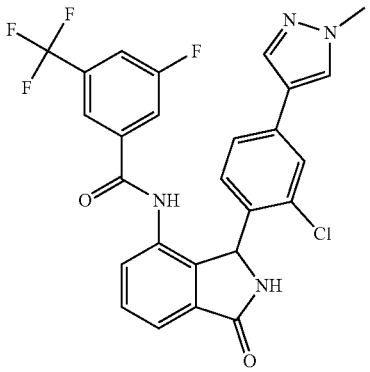 [SMILES: Cn1cc(-c2ccc(C3NC(=O)c4cccc(NC(=O)c5cc(F)cc(C(F)(F)F)c5)c43)c(Cl)c2)cn1] | Cn1cc(cn1)-c1ccc(C2NC(=O)c3cccc(NC(=O)c4cc(F)cc(c4)C(F)(F)F)c23)c(Cl)c1 | | | | E |
| I-426 | 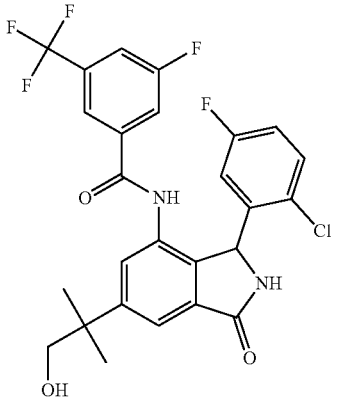 [SMILES: CC(C)(CO)c1cc(NC(=O)c2cc(F)cc(C(F)(F)F)c2)c2c(c1)C(=O)NC2c1cc(F)ccc1Cl] | CC(C)(CO)c1cc2C(=O)NCc2c(NC(=O)c2cc(F)cc(c2)C(F)(F)F)c1c c(F)ccc1Cl | 1H NMR (400 MHz, DMSO-d6) 1.13-1.41 (m, 6 H), 4.66-4.88 (m, 1 H), 5.79-6.13 (m, 1 H), 6.61-6.80 (m, 1 H), 6.99-7.15 (m, 1 H), 7.18-7.35 (m, 1 H), 7.44-7.52 (m, 1 H), 7.58-7.81 (m, 4 H), 7.87-8.01 (m, 1 H), 8.41-8.54 (m, 1 H), 8.99-9.23 (m, 1 H), 10.39-10.63 (m, 1 H) | 563 | | A |
| I-427 | 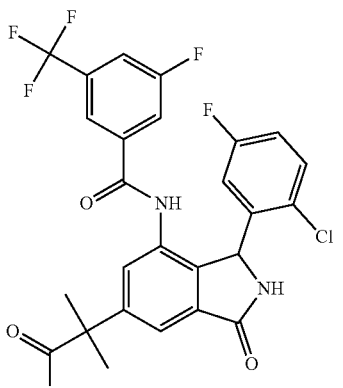 | CC(C)(C(O)=O)c1cc2C(=O)NC(c2c(NC(=O)c2cc(F)cc(c2)C(F)(F)F)c1cc(F)ccc1Cl | 1H NMR (400 MHz, DMSO-d6) 1.41-1.64 (m, 6 H), 5.82-6.07 (m, 1 H), 7.02-7.14 (m, 1 H), 7.24-7.34 (m, 1 H), 7.41-7.48 (m, 1 H), 7.60-7.67 (m, 2 H), 7.70-7.80 (m, 1 H), 7.88-7.98 (m, 1 H), 8.32-8.45 (m, 1 H), 9.03-9.25 (m, 1 H), 10.42-10.65 (m, 1 H) | 553 | | B |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-428 | 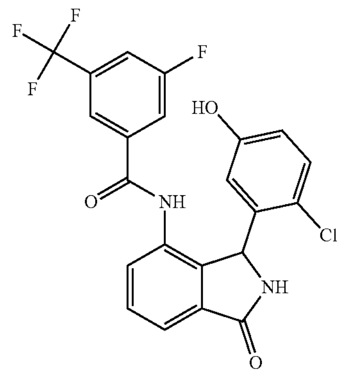 [SMILES: O=C(Nc1cccc2c1C(c1cc(O)ccc1Cl)NC2=O)c1cc(F)cc(C(F)(F)F)c1] | Oc1ccc(C1)c(c1)C1NC(=O)c2cccc(NC(=O)c3cc(F)cc(c3)C(F)(F)F)c12 | | 465 | D | |
| I-429 | 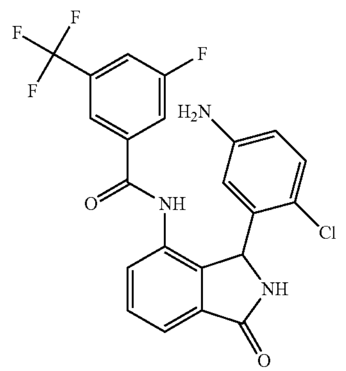 [SMILES: Nc1ccc(Cl)c(C2NC(=O)c3cccc(NC(=O)c4cc(F)cc(C(F)(F)F)c4)c32)c1] | Nc1ccc(C1)c(c1)C1NC(=O)c2cccc(NC(=O)c3cc(F)cc(c3)C(F)(F)F)c12 | | 464 | D | |
| I-430 | 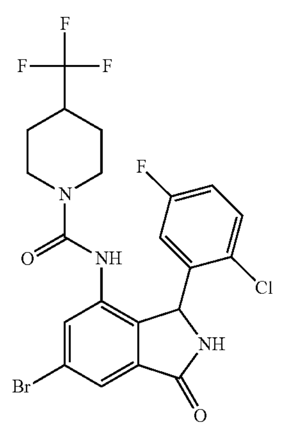 [SMILES: O=C1NC(c2cc(F)ccc2Cl)c2c(NC(=O)N3CCC(C(F)(F)F)CC3)cc(Br)cc21] | Fc1ccc(C1)c(c1)C1NC(=O)c2cc(Br)cc(NC(=O)N3CCC(CC3)C(F)(F)F)c12 | 1H NMR (400 MHz, DMSO-d6) 9.19 (s, 1H), 8.68 (s, 1H), 7.59 (d, 1.4 Hz, 1H), 7.50 (d, 1.4 Hz, 1H), 7.48-7.40 (m, 1H), 7.22 (td, 8.4, 3.0 Hz, 1H), 6.55 (br s, 1H), 6.03 (br s, 1H), 3.93 (d, 13.4 Hz, 1H), 3.78 (d, 13.6 Hz, 1H), 2.70 (d, 12.7 Hz, 1H), 2.55-2.38 (m, 2H), 1.72 (d, 12.3 Hz, 1H), 1.64 (d, 12.3 Hz, 1H), 1.25-1.09 (m, 1H), 0.89-0.65 (m, 1H). | 534.2 | D | |
| I-431 | 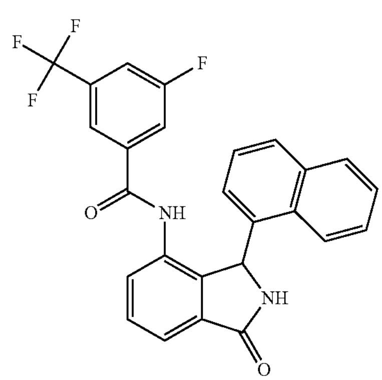 [SMILES: O=C(Nc1cccc2c1C(c1cccc3ccccc13)NC2=O)c1cc(F)cc(C(F)(F)F)c1] | Fc1cc(cc(c1)C(F)(F)F)C(=O)Nc1ccc2C(=O)NC(c12)c1cccc2ccccc12 | 1H NMR (400 MHz, DMSO-d6) 10.03 (s, 1H), 8.99 (s, 1H), 8.01 (s, 1H), 7.92 (d, 7.9 Hz, 1H), 7.83-7.77 (m, 2H), 7.75 (d, 8.3 Hz, 2H), 7.68 (m, 1H), 7.63 (t, 7.6 Hz, 1H), 7.48 (d, 7.6 H, 1Hz), 7.39-7.19 (m, 4H), 6.48 (br s, 1H). | 463.3 | D | |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-432 | 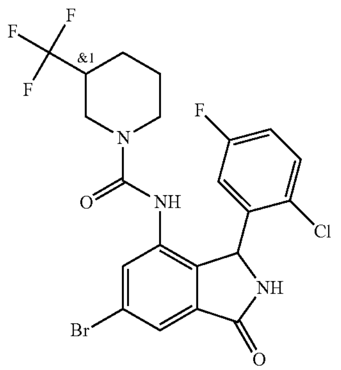 [SMILES: O=C1NC(c2cc(F)ccc2Cl)c2c(NC(=O)N3CCCC(C(F)(F)F)C3)cc(Br)cc21] | Fc1ccc(C1)c(c1)C1NC(=O)c2cc(Br)cc(NC(=O)N3CCCC(C3)C(F)(F)F)c12 | 1H NMR (400 MHz, DMSO-d6) 9.20 (s, 2H), 8.80 (s, 1H), 8.77 (s, 1H), 7.57 (s, 1H), 7.57 (s, 1H), 7.54-7.42 (m, 4H), 7.25-7.15 (m, 2H), 6.52 (br s, 2H), 5.98 (br s, 2H), 4.03-3.87 (m, 2H), 3.71 (d, 13.0 Hz, 1H), 3.57 (d, 13.2 Hz, 1H), 2.70-2.54 (m, 2H), 2.36 (t, 12.3 Hz, 1H), 2.10 (br s, 1H), 1.83-1.70 (m, 2H), 1.68-1.11 (m, 7H), 0.6 (br s, 1H). [1:1 mixture of diastereomers] | 534.2 | C | |
| I-433 | 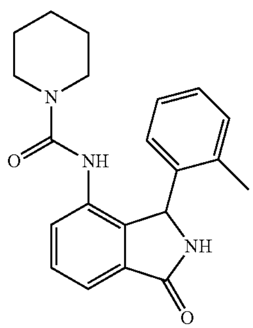 [SMILES: Cc1ccccc1C1NC(=O)c2cccc(NC(=O)N3CCCCC3)c21] | Cc1ccccc1C1NC(=O)c2cccc(NC(=O)N3CCCCC3)c12 | DMSO-d6) 8.90 (s, 1H), 8.24 (s, 1H), 7.46-7.42 (m, 2H), 7.31 (dd, 6.2, 2.7 Hz, 1H), 7.19-7.12 (m, 2H), 7.07-6.98 (m, 1H), 6.53 (br s, 1H), 5.94 (s, 1H), 3.11-3.00 (m, 2H), 2.97-2.85 (m, 2H), 2.33 (br s, 3H), 1.43-1.32 (m, 2H), 1.28-1.14 (m, 2H), 1.13-0.98 (m, 2H). | 350.3 | E | |
| I-434 | 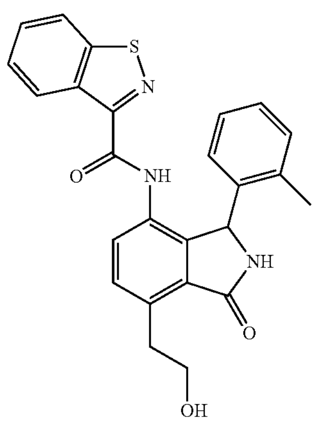 [SMILES: Cc1ccccc1C1NC(=O)c2c(CCO)ccc(NC(=O)c3nsc4ccccc34)c21] | Cc1ccccc1C1NC(=O)c2c1c(NC(=O)c1nsc3cccc13)ccc2CCO | 1H NMR (400 MHz, DMSO-d6) 10.03 (s, 1 H), 8.96 (s, 1 H), 8.56 (d, 8.1 Hz, 1 H), 8.29 (d, 8.2 Hz, 1 H), 7.69-7.63 (m, 2 H), 7.57 (t, 7.6 Hz, 1 H), 7.39 (d, 8.1 Hz, 1 H), 6.99-6.84 (m, 3 H), 6.68 (br s, 1 H), 6.02 (s, 1 H), 4.69 (s, 1 H), 3.75-3.65 (m, 2 H), 3.43-3.22 (m, 2 H), 2.23 (s, 3 H). | 444.3 | A | |
| I-435 | 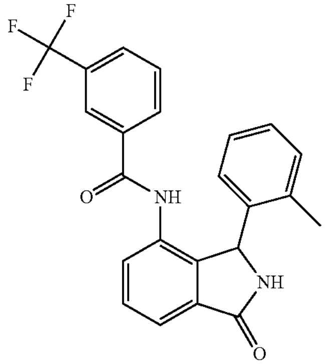 [SMILES: Cc1ccccc1C1NC(=O)c2cccc(NC(=O)c3cccc(C(F)(F)F)c3)c21] | Cc1ccccc1C1NC(=O)c2cccc(NC(=O)c3cccc(c3)C(F)(F)F)c12 | NMR (400 MHz, DMSO-d6) 10.29 (s, 1H), 9.05 (s, 1H), 7.87 (d, 7.6 Hz, 1H), 7.74 (d, 8.0 Hz, 1H), 7.69-7.58 (m, 3H), 7.53 (d, 7.8 Hz, 1H), 7.45 (s, 1H), 7.06 (td, 7.2 and 0.8 Hz, 1H), 6.99-6.93 (m, 2H), 6.55 (br. s, 1H), 5.94 (s, 1H), 2.18 (br. s, 3H). | 411.3 | D | |

TABLE 2-continued

Representative Compounds of the Invention with Bioactivity Data.

| Ex. No. | Structure | SMILES | $^1$H NMR | MS | ADP-Glo IC$_{50}$ | MCF 10A IC$_{50}$ |
|---|---|---|---|---|---|---|
| I-436 | 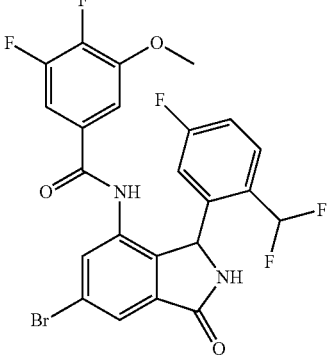 | COc1cc(cc(F)c1F)C(=O)Nc1cc(Br)cc2C(=O)NC(c12)c1cc(F)ccc1C(F)F | 1H NMR (400 MHz, DMSO-d6) 10.33 (br. s, 1H), 9.32 (s, 1H), 7.84 (d, 1.7 Hz, 1H), 7.76 (d, 1.7 Hz, 1H), 7.53 (dd, 8.7, 5.7 Hz, 1H), 7.24 (td, 8.5, 2.6 Hz, 1H), 7.45-7.00 (1 H submerged), 7.16-7.10 (m, 2H), 6.55 (br. s, 1H), 6.01 (s, 1H), 3.86 (s, 3H). | 539.2 | B | |
| I-437 | 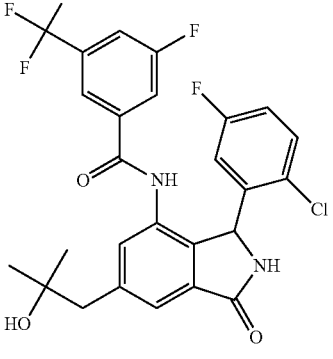 | CC(C)(O)Cc1cc2C(=O)NC(c2c(NC(=O)c2cc(F)cc(c2)C(F)(F)F)c1)c1cc(F)ccc1Cl | 1H-NMR (400 MHz, DMSO-d6) as a ca. 9:1 mixture of rotamers; assignment for major rotamer-' 10.49 (s, 1H), 9.07 (br. s, 1H), 7.93 (d, 8.6 Hz, 1H), 7.73 (d, 8.9 Hz, 1H), 7.65 (s, 1H), 7.56 (s, 1H), 7.34-7.31 (m, 1H), 7.31-7.28 (m, 1H), 7.09 (td, 8.4, 3.0 Hz, 1H), 6.60 (br. s, 1H), 5.94 (br. s, 1H), 4.47 (br. s, 1H), 2.83 (d, A of AB, JAB = 13.2 Hz, 1H), 2.78 (d, B of AB, JAB = 12.9 Hz), 1.12 (s, 3H), 1.10 (s, 3H). | 539.4 | A | |
| I-438 | 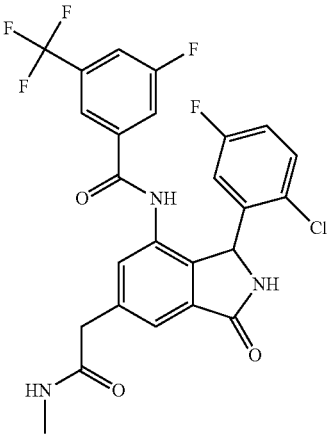 [SMILES: CNC(=O)Cc1cc(NC(=O)c2cc(F)cc(C(F)(F)F)c2)c2c(c1)C(=O)NC2c1cc(F)ccc1Cl] | CNC(=O)Cc1cc2C(=O)NC(c2c(NC(=O)c2cc(F)cc(c2)C(F)(F)F)c1)c1cc(F)ccc1Cl | 1H-NMR (400 MHz, DMSO-d6) 10.52 (br. s, 1H), 9.13 (s, 1H), 8.10 (q, 4.0 Hz, 1H), 7.94 (d, 8.5 Hz, 1H), 7.73 (d, 9.1 Hz, 1H), 7.65 (s, 1H), 7.59 (s, 1H), 7.37 (s, 1H), 7.31 (dd, 8.9, 5.2 Hz, IH), 7.09 (td, 8.4, 3.1 Hz, 1H), 6.58 (br. s, 1H), 5.95 (br. s, 1H), 3.59 (d, A of AB, JAB = 14.3 Hz, 1H), 3.55 (d, B of AB, JAB = 14.3 Hz, 1H), 2.60 (d, 4.6 Hz, 3H).. | 538.3 | A | |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-439 | 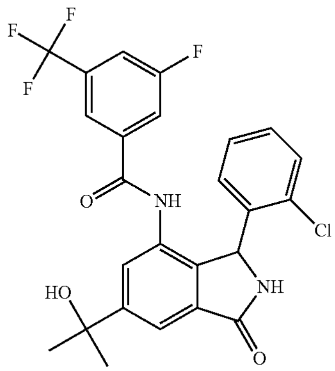 [SMILES: CC(C)(O)c1cc(NC(=O)c2cc(F)cc(C(F)(F)F)c2)c2c(c1)C(=O)NC2c1ccccc1Cl] | CC(C)(O)c1cc2C(=O)NC(c2c(NC(=O)c2cc(F)cc(c2)C(F)(F)F)c1)c1ccccc1Cl | NMR (400 MHz, CD3CN) 8.57 (br s, 1H), 7.81 (d, 1.5 Hz, 1H), 7.75 (br s, 1H), 7.67-7.63 (m, 1H), 7.62-7.58 (m, 1H), 7.54 (s, 1H), 7.51 (m, 2H), 7.26 (dd, 8.0, 1.4 Hz, 1H), 7.20 (td, 7.6, 1.7 Hz., 1H) overlapped with (s, 1H), 7.12 (t, 7.0 Hz, 1H), 6.87 (s, 1H), 6.15 (s, 1H), 1.57 (s, 3H), 1.56 (s, 3H). | 507 | B | |
| I-440 | 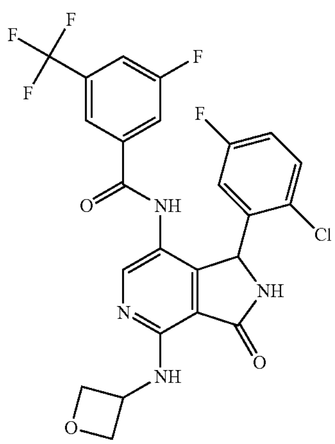 [SMILES: O=C(Nc1cnc(NC2COC2)c2c1C(c1cc(F)ccc1Cl)NC2=O)c1cc(F)cc(C(F)(F)F)c1] | Fc1ccc(C1)c(c1)C1NC(=O)c2c1c(NC(=O)c1cc(F)cc(c1)C(F)(F)F)cnc2NC1COC1 | NMR (400 MHz, MeOD4) 8.55 (s, 1H), 8.06 (s, 1H), 7.74-7.58 (m, 3H), 7.28 (dd, 8.9, 5.1 Hz, 1H), 7.01 (ddd, 8.9, 5.1 and 3.0 Hz, 1H), 6.74 (br. s, 1H), 6.12 (br. s, 1H), 5.49 (s, 1H), 5.32-5.18 (m, 1H), 5.02 (td, 6.9, 2.0 Hz, 2H), 4.72 (q, 6.6 Hz, 2H). | 539.3 | D | |
| I-441 | 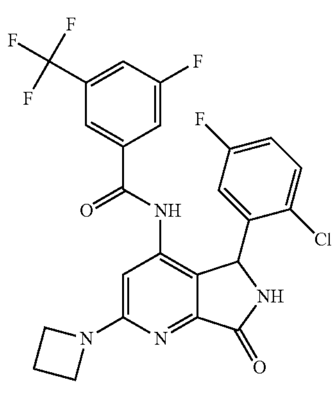 [SMILES: O=C(Nc1cc(N2CCC2)nc2c1C(c1cc(F)ccc1Cl)NC2=O)c1cc(F)cc(C(F)(F)F)c1] | Fc1ccc(C1)c(c1)C1NC(=O)c2nc(cc(NC(=O)c3cc(F)cc(c3)C(F)(F)F)c12)N1CCC1 | NMR (400 MHz, DMSO-d6) 10.57 (br. s, 1H), 9.22 (br. s, 1H), 7.95 (d, 8.6 Hz, 1H), 7.70 (d, 9.0 Hz, 1H), 7.60 (s, 1H), 7.32 (dd, 8.9, 5.2 Hz 1H), 7.10-7.05 (m, 1H), 6.67 (br. s, 1H), 6.45 (br. s, 1H), 5.88 (br. s, 1H), 4.13-3.97 (m, 4H), 2.38 (qt, 8.9, 7.6 Hz, 2H). | 523.2 | A | |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-442 | 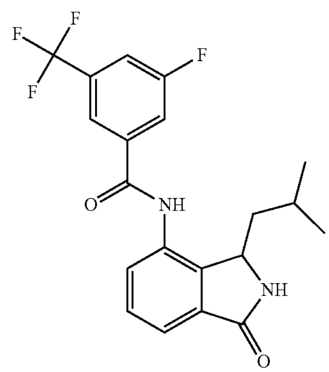 [SMILES: CC(C)CC1NC(=O)c2cccc(NC(=O)c3cc(F)cc(C(F)(F)F)c3)c21] | CC(C)CC1NC(=O)c2cccc(NC(=O)c3cc(F)cc(c3)C(F)(F)F)c12 | NMR (400 MHz, DMSO-d6) 10.78 (s, 1H), 8.93 (s, 1H), 8.18 (s, 1H), 8.12 (d, 8.9 Hz, 1H), 8.04 (d, 8.4 Hz, 1H), 7.62-7.50 (m, 3H), 4.81 (d, 9.0 Hz, 1H), 1.73 (m, 1H), 1.68-1.58 (ddd, 13.1, 10.4, 2.1Hz, 1H), 1.10 (ddd, 13.2, 6.4, 2.2 Hz, 1H), 0.78 (d, 6.3 Hz, 3H), 0.72 (d, 6.5 Hz, 3H). | 395.3 | D | |
| I-443 | 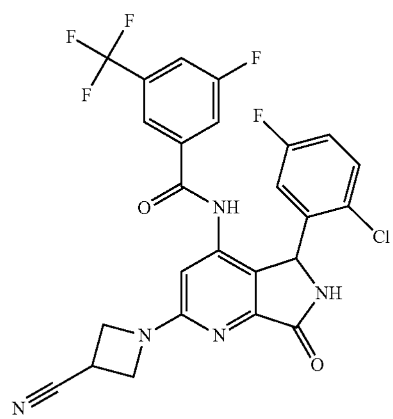 [SMILES: N#CC1CN(c2cc(NC(=O)c3cc(F)cc(C(F)(F)F)c3)c3c(n2)C(=O)NC3c2cc(F)ccc2Cl)C1] | Fc1ccc(C1)c(c1)C1NC(=O)c2nc(cc(NC(=O)c3cc(F)cc(c3)C(F)(F)F)c12)N1CC(C1)C#N | 1H NMR (400 MHz, ACN-d3) 8.62 (s, 1H), 7.66 (d, 8.4 Hz, 1H), 7.55 (d, 8.9 Hz, 1H), 7.52 (s, 1H), 7.42 (s, 1H), 7.31 (dd, 8.9, 5.1 Hz, 1H), 6.99 (td, 8.4, 3.0 Hz, 1H), 6.72 (s, 2H), 6.04 (s, 1H), 4.37 (td, 8.4, 3.9 Hz, 2H), 4.26 (ddd, 8.3, 5.9, 2.7 Hz., 2H), 3.75 (tt, 8.8, 5.9 Hz, 1H). contains grease at 1.2 and 0.8 and trace impurities at 3.4 to 3.5 | 548.3 | A | |
| I-444 | 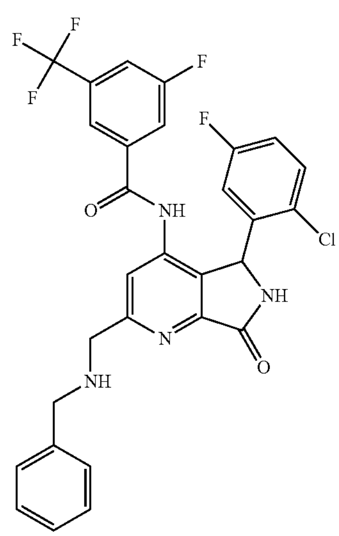 [SMILES: O=C(Nc1cc(CNCc2ccccc2)nc2c1C(c1cc(F)ccc1Cl)NC2=O)c1cc(F)cc(C(F)(F)F)c1] | Fc1ccc(C1)c(c1)C1NC(=O)c2nc(CNCc3ccccc3)cc(NC(=O)c3cc(F)cc(c3)C(F)(F)F)c12 | (400 MHz, CD3CN) 8.10 (s, 1H), 7.76 (s, 1H), 7.66 (d, 8.3 Hz, 1H), 7.59 (d, 13.5 Hz, 3H), 7.41 (d, 7.3 Hz, 2H), 7.36-7.25 (m, 4H), 6.99 (td, 8.3, 2.8 Hz, 1H), 6.78-6.70 (m, 1 H), 6.15 (s, 1H), 4.08 (s, 2H), 3.89 (s, 2H). | 587.3 | B | |

TABLE 2-continued

Representative Compounds of the Invention with Bioactivity Data.

| Ex. No. | Structure | SMILES | $^1$H NMR | MS | ADP-Glo IC$_{50}$ | MCF 10A IC$_{50}$ |
|---|---|---|---|---|---|---|
| I-445 | 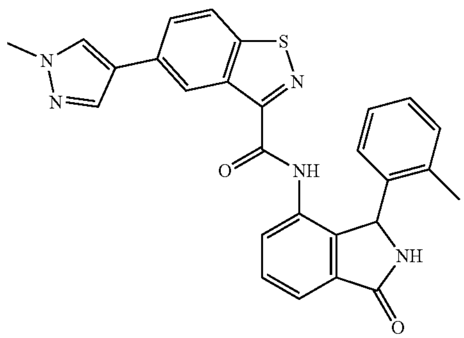 | Cc1ccccc1C1NC(=O)c2cccc(NC(=O)c3nsc4ccc(cc34)-c3cnn(C)c3)c12 | | 480.5 | D | |
| I-446 | 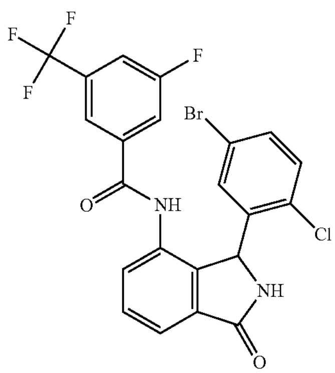 [SMILES: O=C(Nc1cccc2c1C(c1cc(Br)ccc1Cl)NC2=O)c1cc(F)cc(C(F)(F)F)c1] | Fc1cc(cc(c1)C(F)(F)F)C(=O)Nc1ccc2C(=O)NC(c12)c1cc(Br)ccc1Cl | | 527 | A | |
| I-447 | 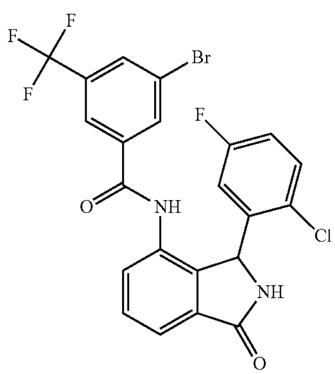 [SMILES: O=C(Nc1cccc2c1C(c1cc(F)ccc1Cl)NC2=O)c1cc(Br)cc(C(F)(F)F)c1] | Fc1ccc(C1)c(c1)C1NC(=O)c2cccc(NC(=O)c3cc(Br)cc(c3)C(F)(F)F)c12 | | 527 | D | |
| I-448 | 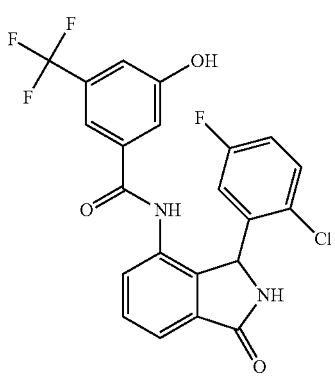 [SMILES: O=C(Nc1cccc2c1C(c1cc(F)ccc1Cl)NC2=O)c1cc(O)cc(C(F)(F)F)c1] | Oc1cc(cc(c1)C(F)(F)F)C(=O)Nc1ccc2C(=O)NC(c12)c1cc(F)ccc1Cl | | 465 | C | |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-449 | 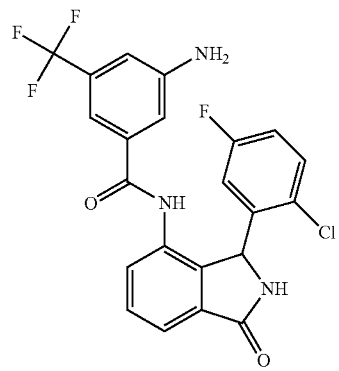 [SMILES: Nc1cc(C(=O)Nc2cccc3c2C(c2cc(F)ccc2Cl)NC3=O)cc(C(F)(F)F)c1] | Nc1cc(cc(c1)C(F)(F)F)C(=O)Nc1cccc2C(=O)NC(c12)c1cc(F)ccc1Cl | | 464 | D | |
| I-450 | 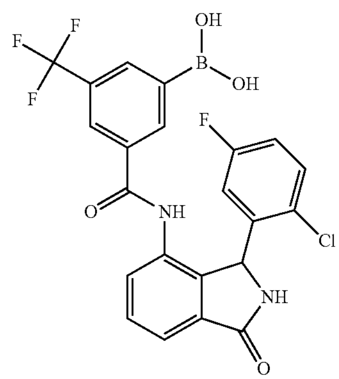 [SMILES: O=C(Nc1cccc2c1C(c1cc(F)ccc1Cl)NC2=O)c1cc(B(O)O)cc(C(F)(F)F)c1] | OB(O)c1cc(cc(c1)C(F)(F)F)C(=O)Nc1cccc2C(=O)NC(c12)c1cc(F)ccc1Cl | | 493 | D | |
| I-451 | 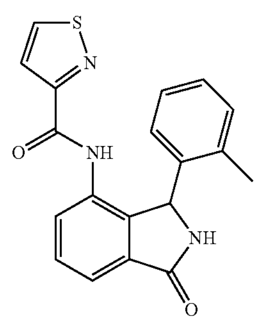 [SMILES: Cc1ccccc1C1NC(=O)c2cccc(NC(=O)c3ccsn3)c21] | Cc1ccccc1C1NC(=O)c2cccc(NC(=O)c3ccsn3)c12 | 1H NMR (400 MHz, DMSO-d6) Shift 9.87 (s, 1H), 9.11 (d, 4.64 Hz, 1H), 9.01 (s, 1H), 7.76 (d, 7.32 Hz, 1H), 7.67 (d, 4.64 Hz, 1H), 7.54-7.64 (m, 2H), 6.99-7.07 (m, 2H), 6.89-6.96 (m, 1H), 6.57-6.79 (m, 1H), 6.05 (br s, 1H), 2.10-2.39 (m, 3H) | 350.31 | E | |
| I-452 | 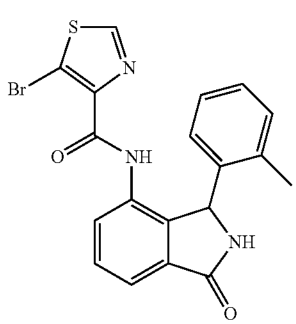 [SMILES: Cc1ccccc1C1NC(=O)c2cccc(NC(=O)c3ncsc3Br)c21] | Cc1ccccc1C1NC(=O)c2cccc(NC(=O)c3ncsc3Br)c12 | 1H NMR (400 MHz, DMSO-d6) Shift 9.69 (s, 1H), 9.07 (s, 1H), 9.01 (s, 1H), 7.84 (d, 7.08 Hz, 1H), 7.49-7.64 (m, 2H), 7.07 (br d, 4.39 Hz, 2H), 6.92-7.02 (m, 1H), 6.57-6.79 (m, 1H), 6.03 (br s, 1H), 2.03-2.40 (m, 3H) | 428.2 | D | |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-453 | 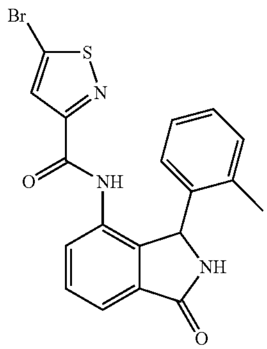 [SMILES: Cc1ccccc1C1NC(=O)c2cccc(NC(=O)c3cc(Br)sn3)c21] | Cc1ccccc1C1NC(=O)c2cccc(NC(=O)c3cc(Br)sn3)c12 | 1H NMR (400 MHz, DMSO-d6) Shift 9.97 (s, 1H), 9.01 (s, 1H), 7.79 (s, 1H), 7.69 (d, 7.57 Hz, 1H), 7.61-7.66 (m, IH), 7.54-7.61 (m, 1H), 6.99-7.08 (m, 2H), 6.94 (br t, 7.32 Hz, 1H), 6.50-6.80 (m, 1H), 6.01 (br s, 1H), 2.02-2.40 (m, 3H) | 428.25 | E | |
| I-454 | 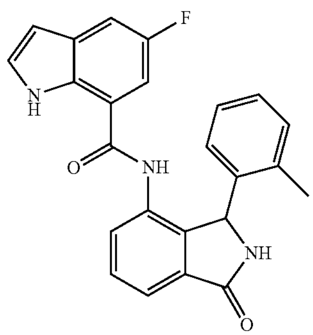 [SMILES: Cc1ccccc1C1NC(=O)c2cccc(NC(=O)c3cc(F)cc4cc[nH]c34)c21] | Cc1ccccc1C1NC(=O)c2cccc(NC(=O)c3cc(F)cc4cc[nH]c34)c12 | 1H NMR (400 MHz, DMSO-d6) Shift 11.17 (br s, 1H), 10.06 (s, 1H), 9.03 (s, 1H), 7.64-7.70 (m, 1H), 7.60 (d, 4.39 Hz, 1H), 7.50 (dd, 2.07, 9.40 Hz, 1H), 7.40 (br t, 2.68 Hz, 1H), 7.02-7.09 (m, 1H), 6.97 (br d, 7.32 Hz, 1H), 6.91 (br t, 7.20 Hz, 1H), 6.75 (br d, 9.52 Hz, 1H), 6.57-6.71 (m, 1H), 6.41-6.54 (m, 1H), 6.04 (s, 1H), 1.99-2.25 (m, 3H) | 400.33 | B | |
| I-455 | 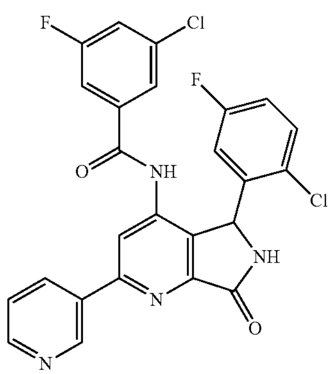 [SMILES: O=C(Nc1cc(-c2cccnc2)nc2c1C(c1cc(F)ccc1Cl)NC2=O)c1cc(F)cc(Cl)c1] | Fc1ccc(C1)c(c1)C1NC(=O)c2nc(cc(NC(=O)c3cc(F)cc(C1)c3)c12)-c1cccnc1 | | 511.4 | B | |
| I-456 | 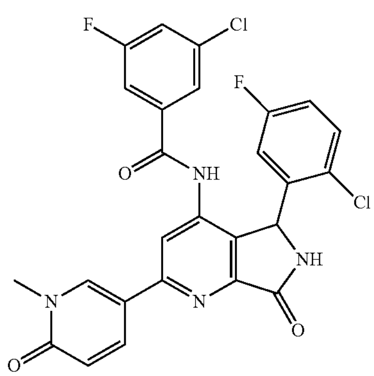 [SMILES: Cn1cc(-c2cc(NC(=O)c3cc(F)cc(Cl)c3)c3c(n2)C(=O)NC3c2cc(F)ccc2Cl)ccc1=O] | Cn1cc(ccc1=O)-c1cc(NC(=O)c2cc(F)cc(Cl)c2)c2C(NC(=O)c2n1)c1cc(F)ccc1C1 | | 541.4 | A | |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-457 | 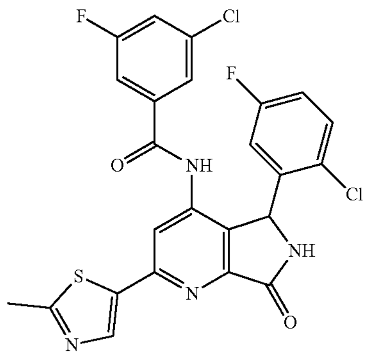 [SMILES: Cc1ncc(-c2cc(NC(=O)c3cc(F)cc(Cl)c3)c3c(n2)C(=O)NC3c2cc(F)ccc2Cl)s1] | Cc1ncc(s1)-c1cc(NC(=O)c2cc(F)cc(Cl)c2)c2C(NC(=O)c2n1)c1cc(F)ccc1Cl | | 531.3 | A | |
| I-458 | 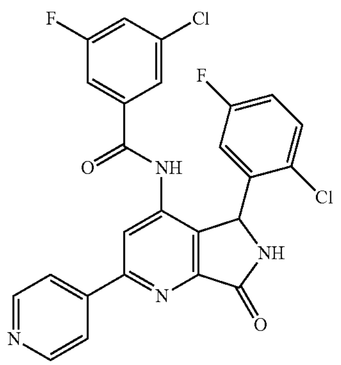 [SMILES: O=C(Nc1cc(-c2ccncc2)nc2c1C(c1cc(F)ccc1Cl)NC2=O)c1cc(F)cc(Cl)c1] | Fc1ccc(Cl)c(c1)C1NC(=O)c2nc(cc(NC(=O)c3cc(F)cc(Cl)c3)c12)-c1ccncc1 | | 511.4 | B | |
| I-459 | 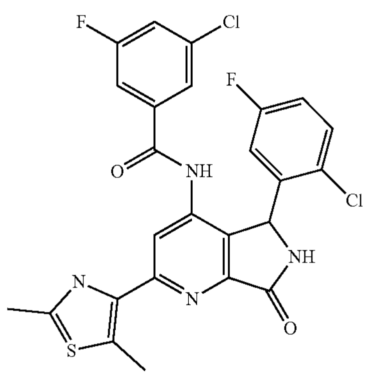 | Cc1nc(C)c(s1)-c1cc(NC(=O)c2cc(F)cc(Cl)c2)c2C(NC(=O)c2n1)c1cc(F)ccc1Cl | | 545.3 | A | |
| I-460 | 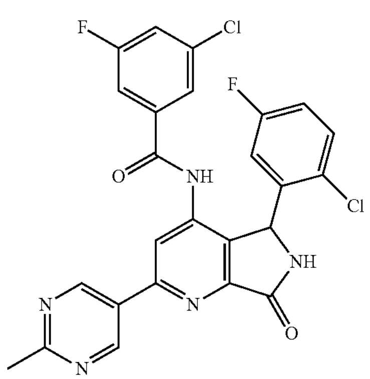 [SMILES: Cc1ncc(-c2cc(NC(=O)c3cc(F)cc(Cl)c3)c3c(n2)C(=O)NC3c2cc(F)ccc2Cl)cn1] | Cc1ncc(cn1)-c1cc(NC(=O)c2cc(F)cc(Cl)c2)c2C(NC(=O)c2n1)c1cc(F)ccc1Cl | | 526.4 | B | |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-461 | 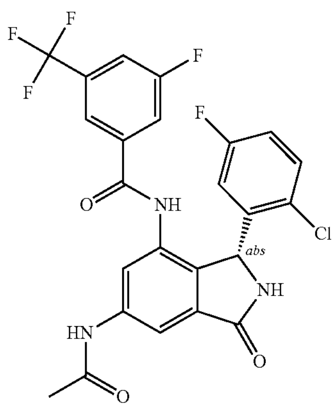 [SMILES: CC(=O)Nc1cc(NC(=O)c2cc(F)cc(C(F)(F)F)c2)c2c(c1)C(=O)N[C@H]2c1cc(F)ccc1Cl] | CC(=O)Nc1cc2C(=O)N[C@H](c2c(NC(=O)c2cc(F)cc(c2)C(F)(F)F)c1)c1cc(F)ccc1Cl | | 524.2 | A | |
| I-462 | 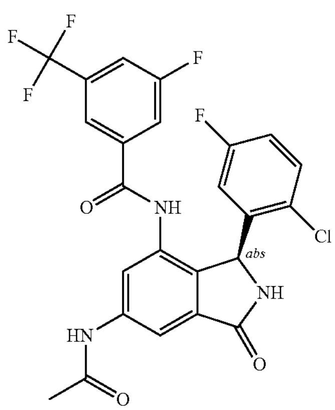 [SMILES: CC(=O)Nc1cc(NC(=O)c2cc(F)cc(C(F)(F)F)c2)c2c(c1)C(=O)N[C@@H]2c1cc(F)ccc1Cl] | CC(=O)Nc1cc2C(=O)N[C@@H](c2c(NC(=O)c2cc(F)cc(c2)C(F)(F)F)c1)c1cc(F)ccc1Cl | | 524.2 | D | |
| I-463 | 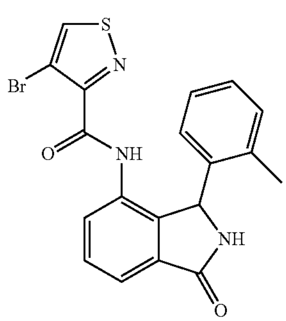 [SMILES: Cc1ccccc1C1NC(=O)c2cccc(NC(=O)c3nscc3Br)c21] | Cc1ccccc1C1NC(=O)c2cccc(NC(=O)c3nscc3Br)c12 | 1H NMR (400 MHz, DMSO-d6) 10.05 (s, 1 H) 9.22 (s, 1 H) 9.01 (s, 1 H) 7.52-7.71 (m, 3 H) 7.02-7.10 (m, 2 H) 6.91-6.98 (m, 1 H) 6.58-6.78 (m, 1 H) 6.03 (s, 1 H) 2.03-2.35 (m, 3 H) | 428.2 | D | |
| I-464 | 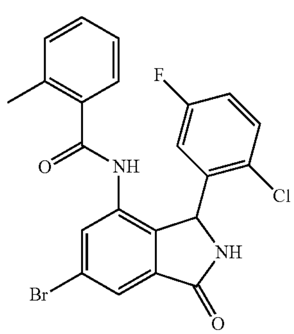 [SMILES: Cc1ccccc1C(=O)Nc1cc(Br)cc2c1C(c1cc(F)ccc1Cl)NC2=O] | Cc1ccccc1C(=O)Nc1cc(Br)cc2C(=O)NC(c12)c1cc(F)ccc1Cl | 1H NMR (400 MHz, Methanol-d4) 7.93 (d, 1.7 Hz, 1H), 7.80 (s, 1H), 7.47 (dd, 8.8, 5.0 Hz, 1H), 7.35 (td, 7.5, 1.4 Hz, 1H), 7.25 (d, 7.6 Hz, 1H), 7.22-7.09 (m, 2H), 6.74 (d, 7.7 Hz, 2H), 6.26 (s, 1H), 2.27 (s, 3H). | 475.15 | E | |

| Ex. No. | Structure | SMILES | ¹H NMR | MS | ADP-Glo IC$_{50}$ | MCF 10A IC$_{50}$ |
|---|---|---|---|---|---|---|
| I-465 | 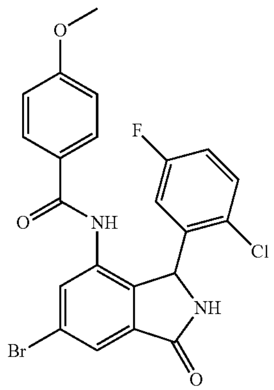 [SMILES: COc1ccc(C(=O)Nc2cc(Br)cc3c2C(c2cc(F)ccc2Cl)NC3=O)cc1] | COc1ccc(cc1)C(=O)Nc1cc(Br)cc2C(=O)NC(c(12)c1ccF)ccc1Cl | 1H NMR (400 MHz, Methanol-d4) 7.92 (d, 1.7 Hz, 1H), 7.74 (d, 1.7 Hz, 1H), 7.62-7.54 (m, 2H), 7.29 (dd, 8.9, 5.1 Hz, 1H), 7.00 (ddd, 8.9, 7.8, 3.1 Hz, 1H), 6.99-6.91 (m, 2H), 6.66 (s, 1H), 6.18 (s, 1H), 3.87 (s, 3H). | 491 | E | |
| I-466 | 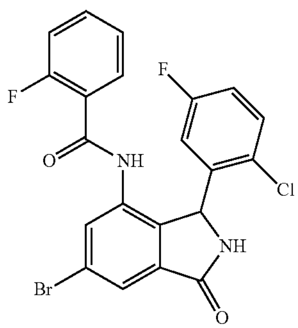 [SMILES: O=C(Nc1cc(Br)cc2c1C(c1cc(F)ccc1Cl)NC2=O)c1ccccc1F] | Fc1ccc(C1)c(c1)C1NC(=O)c2cc(Br)cc(NC(=O)c3ccccc3F)c12 | 1H NMR (400 MHz, Methanol-d4) 7.94 (d, 1.7 Hz, 1H), 7.83-7.78 (m, 1H), 7.56 (dddd, 8.3, 7.2, 5.1, 1.9 Hz, 1H), 7.46 (td, 7.5, 1.9 Hz, 1H), 7.38 (dd, 8.9, 5.1 Hz, 1H), 7.25 (td, 7.6, 1.1 Hz, 1H), 7.17 (ddd, 11.0, 8.4, 1.1 Hz, 1H), 7.08 (ddd, 8.9, 7.8, 3.1 Hz, 1H), 6.71 (s, 1H), 6.22 (s, 1H). | 478.95 | E | |
| I-467 | 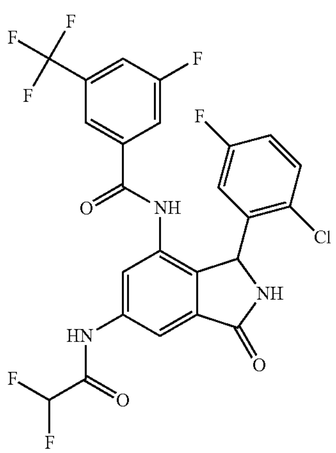 [SMILES: O=C(Nc1cc(NC(=O)C(F)F)cc2c1C(c1cc(F)ccc1Cl)NC2=O)c1cc(F)cc(C(F)(F)F)c1] | FC(F)C(=O)Nc1cc2C(=O)NC(c2c(NC(=O)c2cc(F)cc(c2)C(F)(F)F)c1)c1cc(F)ccc1Cl | 1H NMR (400 MHz, DMSO-d6) 5.93 (br s, 1 H) 6.29-6.51 (m, 2 H) 7.08 (td, 8.42, 2.93 Hz, 1 H) 7.30 (br dd, 8.79, 5.13 Hz, 1 H) 7.61 (s, 1 H) 7.71 (br d, 9.03 Hz, 1 H) 7.87 (s, 1 H) 7.93 (br d, 6.35 Hz, 1 H) 8.00 (s, 1 H) 9.19 (br s, 1 H) 10.56 (s, 1 H) 11.11 (s, 1 H) | 560.26 | A | |
| I-468 | 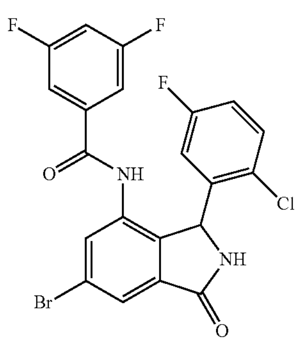 [SMILES: O=C(Nc1cc(Br)cc2c1C(c1cc(F)ccc1Cl)NC2=O)c1cc(F)cc(F)c1] | Fc1ccc(C1)c(c1)C1NC(=O)c2cc(Br)cc(NC(=O)c3cc(F)cc(F)c3)c12 | 1H NMR (400 MHz, DMSO-d6) 10.39 (s, 1H), 9.29 (s, 1H), 7.82 (d, 1.7 Hz, 1H), 7.74 (t, 2.0 Hz, 1H), 7.52 (tt, 9.1, 2.4 Hz, 1H), 7.36 (dd, 8.9, 5.2 Hz, 1H), 7.24 (h, 4.8 Hz, 2H), 7.14 (td, 8.4, 3.1 Hz, 1H), 6.80 (s, 1H), 5.98 (s, 1H). | 495 | B | |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-469 | 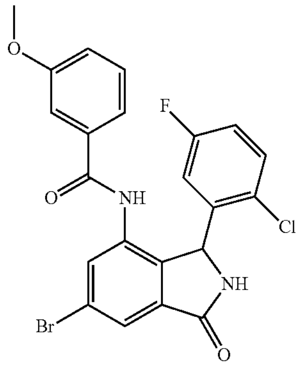 [SMILES: COc1cccc(C(=O)Nc2cc(Br)cc3c2C(c2cc(F)ccc2Cl)NC3=O)c1] | COc1ccc c(c1)C(= O)Nc1cc (Br)cc2C (=O)NC(c (12)c1cc F)ccc1Cl | 1H NMR (400 MHz, DMSO-d6) 9.79 (s, 1H), 9.27 (s, 1H), 7.87 (s, 1H), 7.75 (d, 1.8 Hz, 1H), 7.53-7.45 (m, 1H), 7.45-7.35 (m, 2H), 7.18 (td, 8.4, 3.1 Hz, 1H), 7.10 (d, 8.4 Hz, 1H), 6.99 (t, 7.5 Hz, 1H), 6.74 (s, 1H), 6.11 (s, 1H), 3.74 (s, 3H) | 489 | E | |
| I-470 | 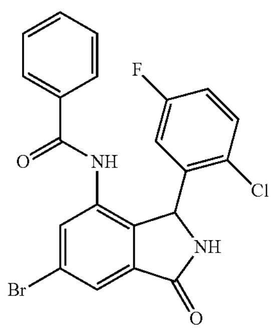 [SMILES: O=C(Nc1cc(Br)cc2c1C(c1cc(F)ccc1Cl)NC2=O)c1ccccc1] | Fc1ccc(C 1)c(c1)Cl NC(=O)c 2cc(Br)cc (NC(=O) c3ccccc3) c12 | 1H NMR (400 MHz, DMSO-d6) 10.22 (s, 1H), 9.27 (s, 1H), 7.80-7.73 (m, 2H), 7.55 (d, 8.0 Hz, 3H), 7.44 (t, 7.6 Hz, 2H), 7.35 (dd, 8.9, 5.2 Hz, 1H), 7.12 (td, 8.4, 3.1 Hz, 1H), 7.00-6.55 (br, 1H), 6.04 (s, 1H). | 459.1 | E | |
| I-471 | 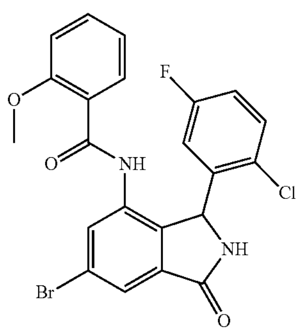 [SMILES: COc1ccccc1C(=O)Nc1cc(Br)cc2c1C(c1cc(F)ccc1Cl)NC2=O] | COc1ccc cc1C(=O) Nc1cc(B r)cc2C(= O)NC(c1 2)c1cc(F) ccc1Cl | 1H NMR (400 MHz, DMSO-d6) 9.79 (s, 1H), 9.26 (s, 1H), 7.88 (t, 3.0 Hz, 1H), 7.75 (d, 1.8 Hz, 1H), 7.48 (ddd, 8.6, 7.3, 1.8 Hz, 1H), 7.45-7.34 (m, 2H), 7.18 (td, 8.4, 3.1 Hz, 1H), 7.10 (d, 8.3 Hz, 1H), 6.98 (t, 7.5 Hz, 1H), 6.74 (s, 1H), 6.11 (s, 1H), 3.73 (s, 3H). | 489 | E | |
| I-472 | 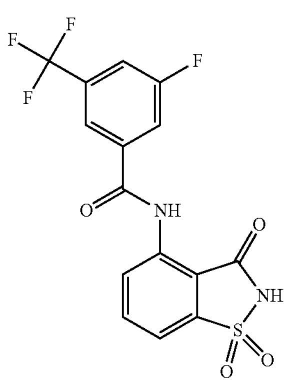 [SMILES: O=C(Nc1cccc2c1C(=O)NS2(=O)=O)c1cc(F)cc(C(F)(F)F)c1] | Fc1cc(cc (c1)C(F) (F)F)C(= O)Nc1cc cc2c1C(= O)NS2(= O)=O | NMR (400 MHz, DMSO) 12.14 (s, 1H), 8.57 (d, 8.2 Hz, 1H), 8.10-7.98 (m, 3H), 7.76 (t, 7.9 Hz, 1H), 7.58 (d, 7.5 Hz, 1H), 6.44 (br s, 1H). | 387.3 | E | |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-473 | 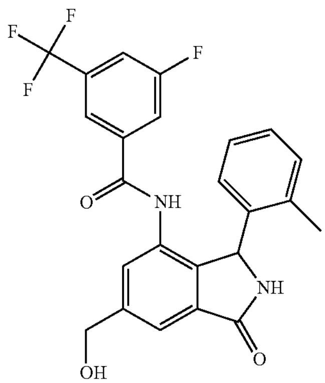 [SMILES: Cc1ccccc1C1NC(=O)c2cc(CO)cc(NC(=O)c3cc(F)cc(C(F)(F)F)c3)c21] | Cc1ccccc1C1NC(=O)c2cc(CO)cc(NC(=O)c3cc(F)cc(c3)C(F)(F)F)c12 | NMR (400 MHz, DMSO) 10.33 (s, 1H), 9.00 (s, 1H), 7.84 (d, 8.3 Hz, 1H), 7.58 (s, 1H), 7.45 (t, 4.1 Hz, 2H), 7.32 (s, 1H), 7.01 (t, 7.7 Hz, 1H), 6.97-6.86 (m, 2H), 6.51 (br s, 1H), 5.84 (s, 1H), 5.41 (s, 1H), 4.62 (d, 2.4 Hz, 2H), 2.15 (br s, 3H). | 459.1 | A | |
| I-474 | 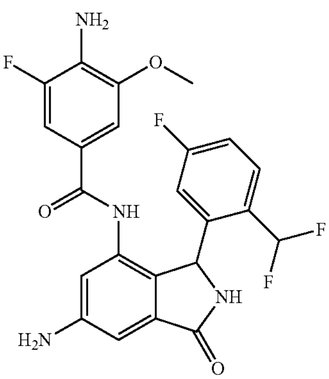 [SMILES: COc1cc(C(=O)Nc2cc(N)cc3c2C(c2cc(F)ccc2C(F)F)NC3=O)cc(F)c1N] | COc1cc(cc(F)c1N)C(=O)Nc1cc(N)cc2C(=O)NC(c12)c1cc(F)ccc1C(F)F | 1H NMR (400 MHz, DMSO-d6) 8.08 (br. d, 7.4 Hz, 1H), 7.96 (ddd, 8.4, 7.0, 1.9 Hz, 1H), 7.85 (dd, 8.7, 5.4 Hz, 1H), 7.74 (s, 1H), 7.46 (td, 8.2, 2.3 Hz, 1H), 7.12 (d, 2.1 Hz, 1H), 7.09 (s, 2H), 7.06 (d, 2.5 Hz, 1H), 7.05 (t, 54.4 Hz, 1H), 6.99 (d, 2.2 Hz, 1H), 7.20-6.8 (2 submerged H), 6.72 (br. s, 2H), 3.97 (s, 3H). | 475.3 | E | |
| I-475 | 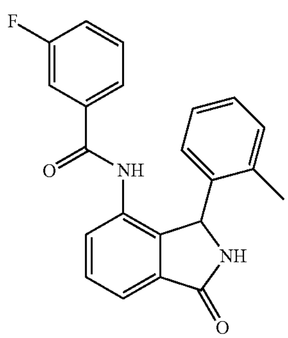 [SMILES: Cc1ccccc1C1NC(=O)c2cccc(NC(=O)c3cccc(F)c3)c21] | Cc1ccccc1C1NC(=O)c2cccc(NC(=O)c3cccc(F)c3)c12 | 1H NMR (400 MHz, DMSO-d6) 10.09 (s, 1H), 9.04 (s, 1H), 7.66 (dd, 7.3, 1.3 Hz, 1H), 7.60 (t, 7.5 Hz, 1H), 7.54 (dd, 7.7, 1.3 Hz, 1H), 7.44 (td, 8.0, 5.9 Hz, 1H), 7.35 (tdd, 8.7, 2.6, 1.0 Hz, 1H), 7.25 (d, 7.6 Hz, 1H), 7.09 (td, 7.4, 1.3 Hz, 1H), 7.03-6.99 (m, 2H), 6.97 (t, 7.5 Hz, 1H), 6.58 (br. s, 1H), 5.95 (s, 1H), 2.18 (br. s, 3H). | 361.3 | D | |
| I-476 | 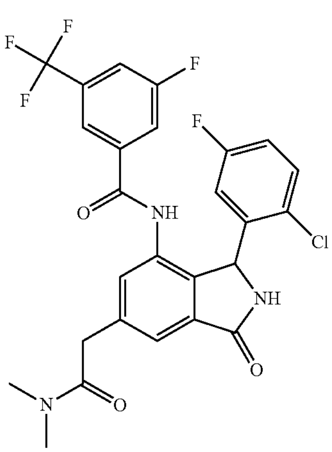 [SMILES: CN(C)C(=O)Cc1cc(NC(=O)c2cc(F)cc(C(F)(F)F)c2)c2c(c1)C(=O)NC2c1cc(F)ccc1Cl] | CN(C)C(=O)Cc1cc2C(=O)NC(c2c(NC(=O)c2cc(F)cc(c2)C(F)F)c1)c1cc(F)ccc1Cl | 1H-NMR (400 MHz, DMSO-d6)-10.51 (br. s, 1H), 9.12 (s, 1H), 7.94 (d, 8.5 Hz, 1H), 7.73 (d, 9.1 Hz, 1H), 7.65 (s, 1H), 7.56 (s, 1H), 7.33 (s, 1H), 7.31 (dd, 8.9, 5.2 Hz, 1H), 7.09 (td, 8.4, 3.1 Hz, 1H), 6.58 (br. s, 1H), 5.95 (br. s, 1H), 3.91 (d, A of AB, JAB = 15.6 Hz, 1H), 3.86 (d, B of AB, JAB = 15.6 Hz., 1H), 3.06 (s, 3H), 2.86 (s, 3H). Contains traces of n-hexane (1.27 and 0.86) and grease (1.54 and 1.03). | 552.3 | A | |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-477 | 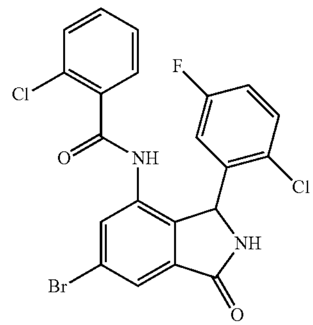 [SMILES: O=C(Nc1cc(Br)cc2c1C(c1cc(F)ccc1Cl)NC2=O)c1ccccc1Cl] | Fc1ccc(C1)c(c1)C1NC(=O)c2cc(Br)cc(NC(=O)c3ccccc3C1)c12 | 1H NMR (400 MHz, DMSO-d6) 10.42 (s, 1H), 9.30 (s, 1H), 7.8-7.75 (m, 2H), 7.55-7.43 (m, 3H), 7.38-7.24 (m, 2H), 6.82 (m, 2H), 6.11 (s, 1H). | 493 | E | |
| I-478 | 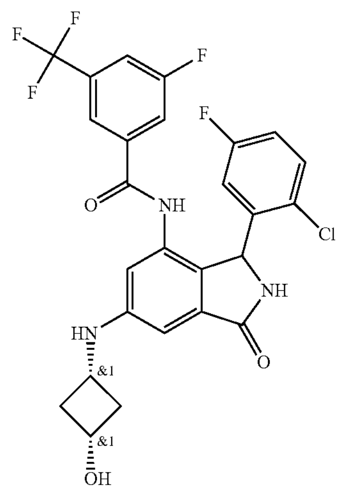 [SMILES: O=C(Nc1cc(N[C@H]2C[C@@H](O)C2)cc2c1C(c1cc(F)ccc1Cl)NC2=O)c1cc(F)cc(C(F)(F)F)c1] | O[C@H]1C[C@H](C1)Nc1cc2C(=O)NC(c2c(NC(=O)c2cc(F)cc(c2)C(F)(F)F)c1)c1cc(F)ccc1Cl | 1H NMR (400 MHz, DMSO-d6) 10.26 (br s, 1H), 8.90 (br s, 1H), 7.92 (d, 7.6 Hz, 1H), 7.69 (d, 8.0 Hz, 1H), 7.61 (s, 1H), 7.27 (dd, 8.7, 5.3 Hz, 1H), 7.06 (td, 8.3, 2.8 Hz, 1H), 6.73 (d, 1.7 Hz, 1H), 6.60 (s, 1H), 6.58 (br. s, 1H), 6.43 (d, 6.0 Hz, 1H), 5.82 (br s, 1H), 5.12 (d, 6.2 Hz, 1H), 3.95-3.86 (m, 1H), 3.39-3.30 (m, 1H), 2.75-2.67 (m, 2H), 1.75-1.66 (m, 2H); DMSO satellites at 2.67 and 2.33; multiplet at 3.39-3.30 overlaps with water peak at 3.30. | 552.3 | A | |
| I-479 | 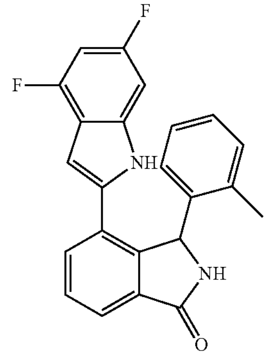 [SMILES: Cc1ccccc1C1NC(=O)c2cccc(-c3cc4c(F)cc(F)cc4[nH]3)c21] | Cc1ccccc1C1NC(=O)c2cccc(-c3cc4c(F)cc(F)cc4[nH]3)c12 | 1H NMR (400 MHz, DMSO-d6) 11.87 (br. s, 1H), 9.15 (br. s, 1H), 7.87 (d, 7.6 Hz, 1H), 7.79 (d, 7.5 Hz, 1H), 7.71 (t, 7.5 Hz, 1H), 7.02-6.93 (m, 3H), 6.83 (t, 7.4 Hz, 1H), 6.74 (td, 10.2, 1.6 Hz, 1H), 6.46 (s, 1H), 6.43 (s, 1H), 2.36 (br. s, 3H); DMSO satellites at 2.67 and 2.33; residual acetonitrile at 2.07; sample contains 18% of formate salt (peak at 8.51). | 375.3 | D | |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-480 | 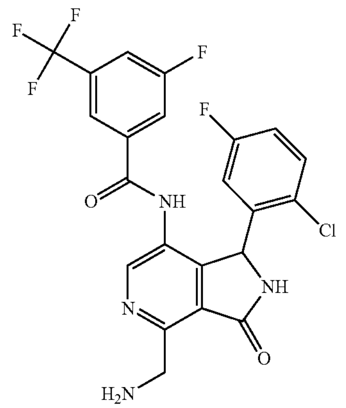 [SMILES: NCc1ncc(NC(=O)c2cc(F)cc(C(F)(F)F)c2)c2c1C(=O)NC2c1cc(F)ccc1Cl] | NCc1ncc(NC(=O)c2cc(F)cc(c2)C(F)(F)F)c2C(NC(=O)c12)c1cc(F)ccc1Cl | 1H NMR (400 MHz, MeOD4) 8.68 (s, 1H), 8.54 (br. s, 1H), 7.76-7.65 (m, 3H), 7.31 (dd, 9.0, 5.0 Hz, 1H), 7.04 (ddd, 8.9, 7.9, 3.0 Hz, 1H), 6.76 (br. s, 1H), 6.25 (br. s, 1H), 4.82-4.69 (m, 2H) | 497.1 | C | |
| I-481 | 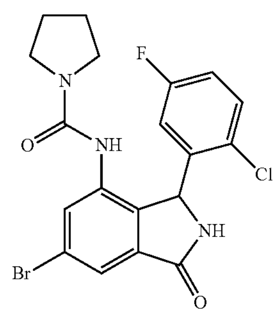 [SMILES: O=C1NC(c2cc(F)ccc2Cl)c2c(NC(=O)N3CCCC3)cc(Br)cc21] | Fc1ccc(C1)c(c1)C1NC(=O)c2cc(Br)cc(NC(=O)N3CCCC3)c12 | (400 MHz, DMSO-d6) 9.16 (br. s, 1H), 8.20 (s, 1H), 7.58 (d, 1.6 Hz, 1H), 7.49 (d, 1.6 Hz, 1H), 7.47 (br. s, 1H), 7.24 (td, 8.4, 3.0 Hz, 1H), 5.95 (br. s, 1H), 3.18 (m, 2H), 2.77 (m, 2H), 1.78-1.59 (m, 4H). | 452.2 | E | |
| I-482 | 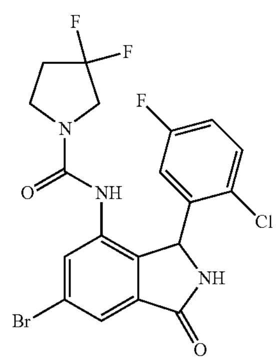 [SMILES: O=C1NC(c2cc(F)ccc2Cl)c2c(NC(=O)N3CCC(F)(F)C3)cc(Br)cc21] | Fc1ccc(C1)c(c1)C1NC(=O)c2cc(Br)cc(NC(=O)N3CCC(F)(F)C3)c12 | (400 MHz, CD3CN) 7.73 (d, 1.5 Hz, 1H), 7.60 (s, 1H), 7.44 (dd, 8.5, 5.2 Hz, 1H), 7.24 (s, 1H), 7.10 (td, 8.5, 3.1 Hz, 1H), 6.76 (s, 1H), 6.08 (s, 1H), 3.59 (q, 13.4 Hz, 1H), 3.46-3.28 (m, 2H), 3.13 (s, 1H), 2.36-2.23 (m, 2H). | 488.2 | D | |
| I-483 | 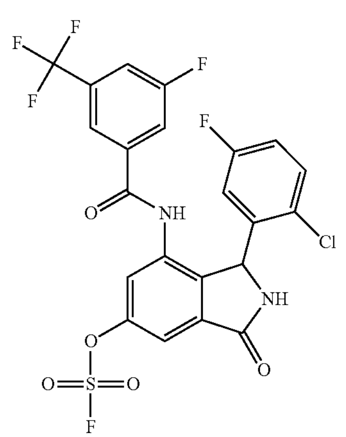 [SMILES: O=C(Nc1cc(OS(=O)(=O)F)cc2c1C(c1cc(F)ccc1Cl)NC2=O)c1cc(F)cc(C(F)(F)F)c1] | Fc1ccc(C1)c(c1)C1NC(=O)c2cc(OS(F)(=O)=O)cc(NC(=O)c3cc(F)cc(c3)C(F)(F)F)c12 | 1H NMR (400 MHz, DMSO-d6) 5.73-6.32 (m, 1 H), 6.40-7.00 (m, 1 H), 7.04-7.16 (m, 1 H), 7.27-7.40 (m, 1 H), 7.59-7.66 (m, 1 H), 7.67-7.76 (m, 1 H), 7.77-7.85 (m, 1 H), 7.89-8.03 (m, 2 H), 9.05-9.62 (m, 1 H), 10.50-11.01 (m, 1 H) | 565 | A | |

TABLE 2-continued

Representative Compounds of the Invention with Bioactivity Data.

| Ex. No. | Structure | SMILES | $^1$H NMR | MS | ADP-Glo IC$_{50}$ | MCF 10A IC$_{50}$ |
|---|---|---|---|---|---|---|
| I-484 | 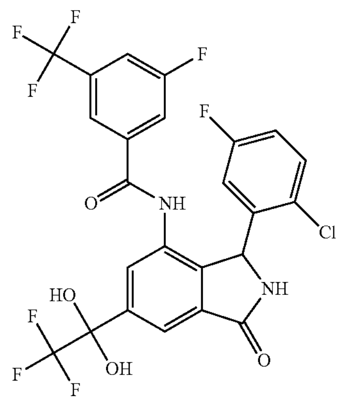 [SMILES: O=C(Nc1cc(C(O)(O)C(F)(F)F)cc2c1C(c1cc(F)ccc1Cl)NC2=O)c1cc(F)cc(C(F)(F)F)c1] | OC(O)(c1cc2C(=O)NC(c2c(NC(=O)c2cc(F)cc(c2)C(F)(F)F)c1)c1cc(F)ccc1Cl)C(F)(F)F | 1H NMR (400 MHz, DMSO-d6) 5.77-6.12 (m, 2 H), 6.41-6.62 (m, 1 H), 6.99-7.20 (m, 1 H), 7.25-7.46 (m, 2 H), 7.54-7.71 (m, 1 H), 7.79-7.92 (m, 1 H), 8.05-8.22 (m, 1 H), 8.30-8.54 (m, 2 H), 8.93-9.14 (m, 1 H), 10.28-10.43 (m, 1 H) | 581 | B | |
| I-485 | 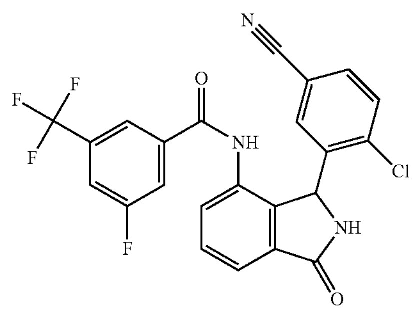 [SMILES: N#Cc1ccc(Cl)c(C2NC(=O)c3cccc(NC(=O)c4cc(F)cc(C(F)(F)F)c4)c32)c1] | Fc1cc(cc(c1)C(F)(F)F)C(=O)Nc1ccc2C(=O)NC(c12)c1cc(ccc1Cl)C#N | | 474.3 | E | |
| I-486 | 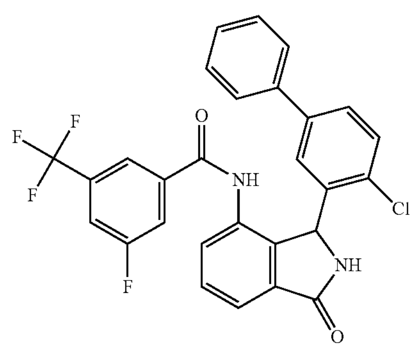 [SMILES: O=C(Nc1cccc2c1C(c1cc(-c3ccccc3)ccc1Cl)NC2=O)c1cc(F)cc(C(F)(F)F)c1] | Fc1cc(cc(c1)C(F)(F)F)C(=O)Nc1ccc2C(=O)NC(c12)c1cc(ccc1Cl)-c1ccccc1 | | 525.4 | D | |
| I-487 | 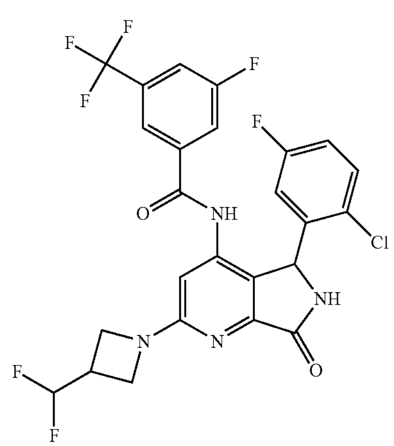 [SMILES: O=C(Nc1cc(N2CC(C(F)F)C2)nc2c1C(c1cc(F)ccc1Cl)NC2=O)c1cc(F)cc(C(F)(F)F)c1] | FC(F)C1CN(C1)c1cc(NC(=O)c2cc(F)cc(c2)C(F)(F)F)c2C(NC(=O)c2n1)c1cc(F)ccc1Cl | 1H NMR (400 MHz, DMSO-d6) 10.62 (br s, 1H), 9.26 (br s, 1H), 7.96 (d, 7.9 Hz, 1H), 7.70 (d, 8.9 Hz, 1H), 7.60 (s, 1H), 7.32 (dd, 8.5, 5.1 Hz, 1H), 7.11-7.04 (m, 1H), 6.76 (br s, 1H), 6.50 (s, 1H), 6.42 (td, 56.3, 3.4 Hz, 1H), 5.88 (br s, 1H), 4.17 (q, 8.8 Hz, 1H), 4.00-3.95 (m, 2H), 3.56-3.37 (m, 1H). | 573.3 | A | |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-488 | 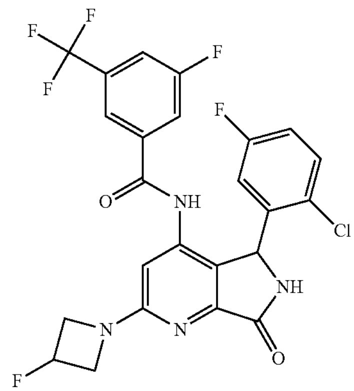 [SMILES: O=C(Nc1cc(N2CC(F)C2)nc2c1C(c1cc(F)ccc1Cl)NC2=O)c1cc(F)cc(C(F)(F)F)c1] | FC1CN(C1)c1cc(NC(=O)c2cc(F)cc(c2)C(F)(F)F)c2C(NC(=O)c2n1)c1cc(F)ccc1Cl | 1H NMR (400 MHz, DMSO-d6) 10.64 (s, 1H), 9.27 (s, 1H), 7.97 (d, 8.2 Hz, 1H), 7.70 (d, 8.8 Hz, 1H), 7.60 (s, 1H), 7.32 (dd, 8.8, 5.1 Hz, 1H), 7.08 (td, 8.5, 3.0 Hz, 1H), 6.75 (br s, 1H), 6.54 (s, 1H), 5.89 (br s, 1H), 5.73-5.34 (m, 1H), 4.55-4.27 (m, 2H), 4.25-3.96 (m, 2H). | 541.1 | A | |
| I-489 | 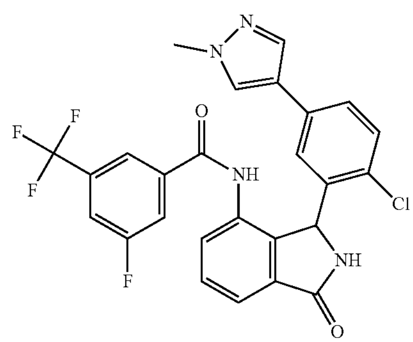 [SMILES: Cn1cc(-c2ccc(Cl)c(C3NC(=O)c4cccc(NC(=O)c5cc(F)cc(C(F)(F)F)c5)c43)c2)cn1] | Cn1cc(cn1)-c1ccc(Cl)c(c1)C1NC(=O)c2cccc(NC(=O)c3cc(F)cc(c3)C(F)(F)F)c12 | | 529.4 | E | |
| I-490 | 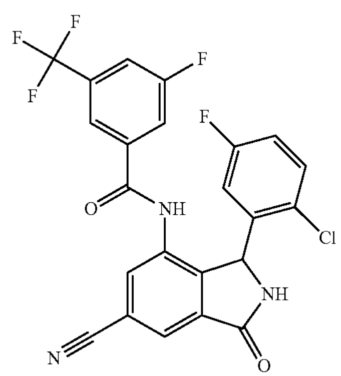 [SMILES: N#Cc1cc(NC(=O)c2cc(F)cc(C(F)(F)F)c2)c2c(c1)C(=O)NC2c1cc(F)ccc1Cl] | Fc1ccc(Cl)c(c1)C1NC(=O)c2cc(cc(NC(=O)c3cc(F)cc(c3)C(F)(F)F)c12)C#N | (400 MHz, CD3CN) 8.76 (br s, 1 H), 8.10 (d, 1.2 Hz, 1H), 7.90 (s, 1H), 7.67 (d, 8.4 Hz, 1H), 7.59 (d, 9.0 Hz, 1H), 7.55 (s, 1H), 7.45 (br s, 1H), 7.27 (dd, 8.9, 5.1 Hz, 1H), 6.99 (ddd, 8.8, 8.1, 3.1 Hz, 1H), 6.64 (br s, 1H), 6.18 (br s, 1H). | 490.3 | A | |
| I-491 | 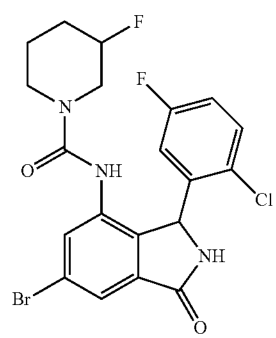 [SMILES: O=C1NC(c2cc(F)ccc2Cl)c2c(NC(=O)N3CCCC(F)C3)cc(Br)cc21] | FC1CCCN(C1)C(=O)Nc1cc(Br)cc2C(=O)NC(c12)c1cc(F)ccc1Cl | NMR (400 MHz, CD3CN) 7.69 (d, 1.6 Hz, 1H), 7.64-7.54 (m, 1H), 7.44 (dd, 8.2, 5.0 Hz, 1H), 7.23 (d, 1.3 Hz, 1H), 7.15-7.04 (m, 1H), 7.04-6.90 (m, 1H), 6.69 (br s, 1H), 6.06 (s, 1H), 4.72-4.05 (m, 1H), 3.52-2.79 (m, 4H), 1.89-1.68 (m, 2H), 1.67-1.16 (m, 2H). | 484.1 | E | |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-492 | 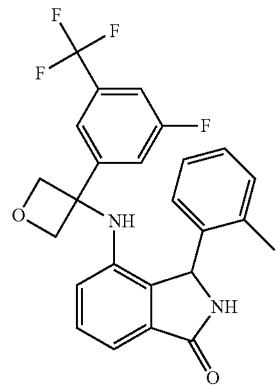 [SMILES: Cc1ccccc1C1NC(=O)c2cccc(NC3(c4cc(F)cc(C(F)(F)F)c4)COC3)c21] | Cc1ccccc1C1NC(=O)c2cccc(NC3(COC3)c3cc(F)cc(c3)C(F)(F)F)c12 | NMR (400 MHz, DMSO-d6) 8.92 (s, 1H), 7.69-7.62 (m, 1H), 7.48-7.45 (m, 2H), 7.26-7.23 (m, 2H), 7.20 (d, 7.7 Hz, 1H), 7.16-7.08 (m, 1H), 7.06 (d, 7.3 Hz, 1H), 6.72 (br s, 1H), 6.13 (d, 7.9 Hz, 1H), 5.90 (s, 1H), 5.38 (s, 1H), 5.18 (d, 6.8 Hz, 1H), 4.87 (d, 6.5 Hz, 1H), 4.67 (d, 6.2 Hz, 1H), 4.50 (d, 7.0 Hz, 1H), 2.40-2.27 (br s, 3H). | 457.2 | D | |
| I-493 | 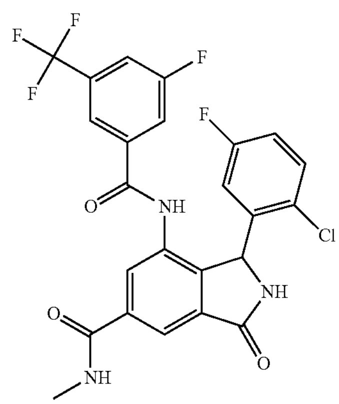 [SMILES: CNC(=O)c1cc(NC(=O)c2cc(F)cc(C(F)(F)F)c2)c2c(c1)C(=O)NC2c1cc(F)ccc1Cl] | CNC(=O)c1cc2C(=O)NC(c2c(NC(=O)c2cc(F)cc(c2)C(F)(F)F)c1)c1cc(F)ccc1Cl | (400 MHz, CD3CN) 8.82 (s, 1H), 8.09 (d, 1.4 Hz, 1H), 8.02 (s, 1H), 7.69 (d, 8.4 Hz, 1H), 7.60 (d, 8.9 Hz 1H), 7.58 (s, 1H) 7.37 (s, 1H), 7.26 (dd, 8.9, 5.1 Hz, 1H), 7.26 (br s, 1H), 6.97 (ddd, 8.8, 8.0, 3.1 Hz, 1H), 6.67 (br s, 1H), 6.16 (br s, 1H), 2.90 (d, 4.7 Hz, 3H) | 524.3 | A | A |
| I-494 | 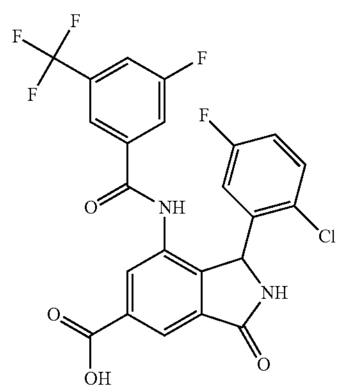 [SMILES: O=C(O)c1cc(NC(=O)c2cc(F)cc(C(F)(F)F)c2)c2c(c1)C(=O)NC2c1cc(F)ccc1Cl] | OC(=O)c1cc2C(=O)NC(c2c(NC(=O)c2cc(F)cc(c2)C(F)(F)c1)c1cc(F)ccc1Cl | (400 MHz, d6-DMSO) 10.64 (br s, 1H), 9.24 (br s, 1H), 8.31 (br s, 1H), 8.13 (s, 1H), 8.03 (d, 10.0 Hz, 1H), 7.95 (d, 8.3 Hz, 1H), 7.76 (d, 8.9 Hz, 1H), 7.68 (s, 1H), 7.32 (dd, 8.9, 5.2 Hz, 1H), 7.09 (td, 8.0, 2.7 Hz, 1H), 6.04 (br s, 1H). | 509.2 | A | |
| I-495 | 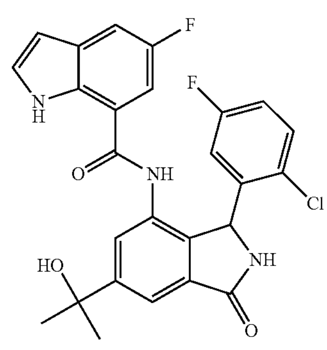 [SMILES: CC(C)(O)c1cc(NC(=O)c2cc(F)cc3cc[nH]c23)c2c(c1)C(=O)NC2c1cc(F)ccc1Cl] | CC(C)(O)c1cc2C(=O)NC(c2c(NC(=O)c2cc(F)cc3cc[nH]c23)c1)c1cc(F)ccc1Cl | 1H NMR (400 MHz, DMSO-d6) 11.21 (br s, 1H), 10.21 (s, 1H), 9.06 (br s, 1H), 7.75 (s, 1H), 7.67 (s, 1H), 7.53 (br dd, 2.20, 9.27 Hz, 1H), 7.43 (br t, 2.56 Hz, 1H), 7.27 (br dd, 5.25, 8.91 Hz, 1H), 7.13 (br dd, 2.20, 10.25 Hz, 1H), 7.04 (dt, 2.93, 8.30 Hz, 1H), 6.58-6.76 (m, 1H), 6.45-6.51 (m, 1H), 6.10 (br s, 1H), 5.28 (s, 1H), 1.50 (d, 1.95 Hz, 3H), 0.75-1.19 (m, 3H) | 496.38 | A | |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-496 | 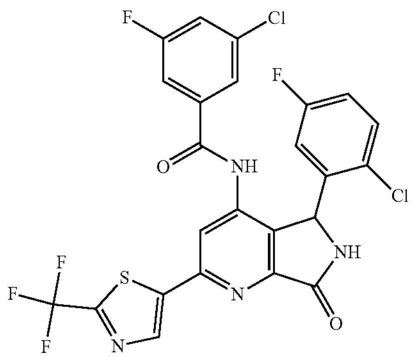 [SMILES: O=C(Nc1cc(-c2cnc(C(F)(F)F)s2)nc2c1C(c1cc(F)ccc1Cl)NC2=O)c1cc(F)cc(Cl)c1] | Fc1ccc(C1)c(c1)C1NC(=O)c2nc(cc(NC(=O)c3cc(F)cc(Cl)c3)c12)-c1cnc(s1)C(F)(F)F | | 585.4 | A | |
| I-497 | 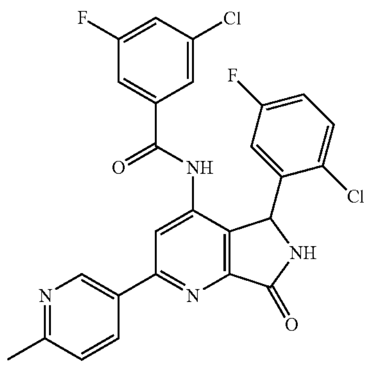 [SMILES: Cc1ccc(-c2cc(NC(=O)c3cc(F)cc(Cl)c3)c3c(n2)C(=O)NC3c2cc(F)ccc2Cl)cn1] | Cc1ccc(cn1)-c1cc(NC(=O)c2cc(F)cc(Cl)c2)c2C(NC(=O)c2n1)c1cc(F)ccc1Cl | | 525.4 | B | |
| I-499 | 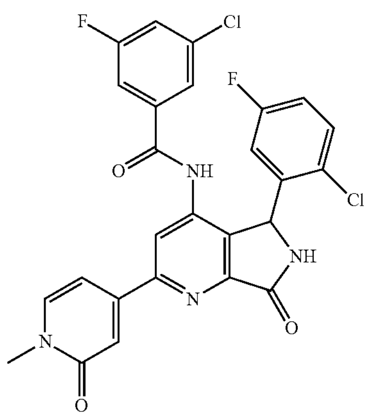 [SMILES: Cn1ccc(-c2cc(NC(=O)c3cc(F)cc(Cl)c3)c3c(n2)C(=O)NC3c2cc(F)ccc2Cl)cc1=O] | Cn1ccc(cc1=O)-c1cc(NC(=O)c2cc(F)cc(Cl)c2)c2C(NC(=O)c2n1)c1cc(F)ccc1Cl | | 541.4 | B | |
| I-500 | 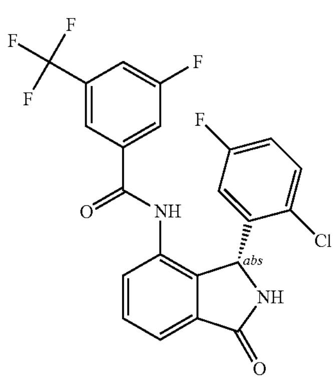 [SMILES: O=C(Nc1cccc2c1[C@H](c1cc(F)ccc1Cl)NC2=O)c1cc(F)cc(C(F)(F)F)c1] | Fc1ccc(C1)c(c1)[C@@H]1NC(=O)c2cccc(NC(=O)c3cc(F)cc(c3)C(F)(F)F)c12 | 1H NMR (DMSO-d6, 400 MHz) Shift 10.3-10.7 (m, 1H), 8.9-9.3 (m, 1H), 7.93 (br d, 1H, 8.5 Hz), 7.6-7.8 (m, 4H), 7.4-7.5 (m, 1H), 7.2-7.4 (m, 1H), 7.0-7.2 (m, 1H), 6.4-6.8 (m, 1H), 5.7-6.2 (m, 1H) | 467.1 | A | A |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-501 | 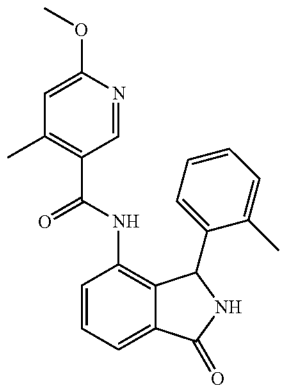 | COc1cc(C)c(cn1)C(=O)Nc1cccc2C(=O)NC(c12)c1ccccc1C | | 388 | | E |
| I-502 | 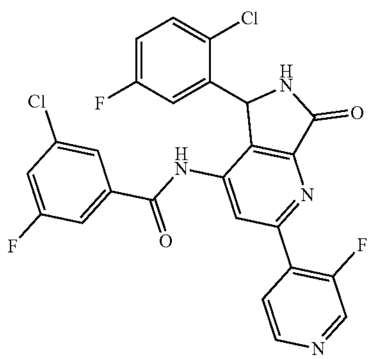 [SMILES: O=C(Nc1cc(-c2ccncc2F)nc2c1C(c1cc(F)ccc1Cl)NC2=O)c1cc(F)cc(Cl)c1] | Fc1ccc(C1)c(c1)C1NC(=O)c2nc(cc(NC(=O)c3cc(F)cc(C1)c3)c12)-c1ccncc1F | | 529.4 | | A |
| I-503 | 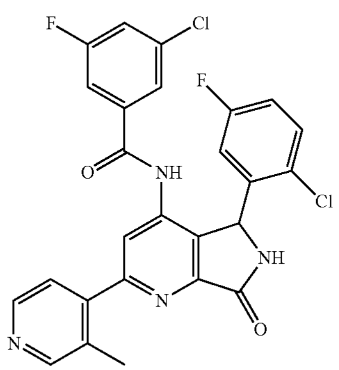 [SMILES: Cc1cnccc1-c1cc(NC(=O)c2cc(F)cc(Cl)c2)c2c(n1)C(=O)NC2c1cc(F)ccc1Cl] | Cc1cnccc1-c1cc(NC(=O)c2cc(F)cc(Cl)c2)c2C(NC(=O)c2n1)c1ccc(F)ccc1Cl | | 525.4 | | A |
| I-504 | 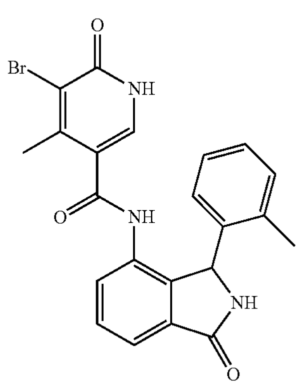 [SMILES: Cc1ccccc1C1NC(=O)c2cccc(NC(=O)c3c[nH]c(=O)c(Br)c3C)c21] | Cc1ccccc1C1NC(=O)c2cccc(NC(=O)c3c[nH]c(=O)c(Br)c3C)c12 | | 452 | | E |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-505 | 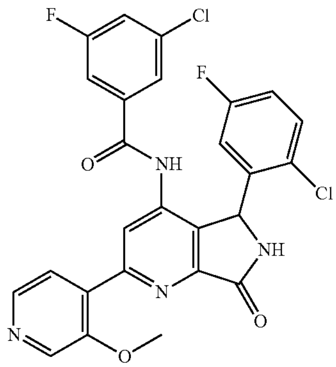 [SMILES: COc1cnccc1-c1cc(NC(=O)c2cc(F)cc(Cl)c2)c2c(n1)C(=O)NC2c1cc(F)ccc1Cl] | COc1cnccc1-c1cc(NC(=O)c2cc(F)cc(Cl)c2)c2C(NC(=O)c2n1)c1cc(F)ccc1Cl | | 541.4 | B | |
| I-506 | 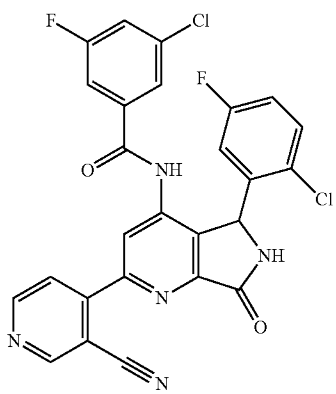 [SMILES: N#Cc1cnccc1-c1cc(NC(=O)c2cc(F)cc(Cl)c2)c2c(n1)C(=O)NC2c1cc(F)ccc1Cl] | Fc1ccc(Cl)c(c1)C1NC(=O)c2nc(cc(NC(=O)c3cc(F)cc(Cl)c3)c12)-c1ccncc1C#N | | 536.4 | A | |
| I-507 | 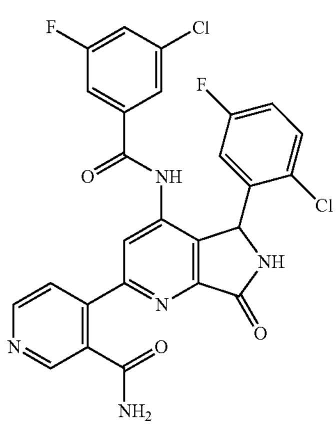 [SMILES: NC(=O)c1cnccc1-c1cc(NC(=O)c2cc(F)cc(Cl)c2)c2c(n1)C(=O)NC2c1cc(F)ccc1Cl] | NC(=O)c1cnccc1-c1cc(NC(=O)c2cc(F)cc(Cl)c2)c2C(NC(=O)c2n1)c1cc(F)ccc1Cl | | 554.4 | D | |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-508 | 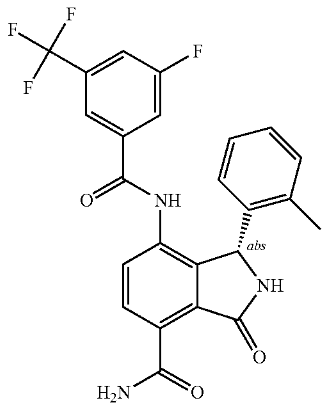 [SMILES: Cc1ccccc1[C@@H]1NC(=O)c2c(C(N)=O)ccc(NC(=O)c3cc(F)cc(C(F)(F)F)c3)c21] | Cc1ccccc1[C@@H]1NC(=O)c2c1c(NC(=O)c1cc(F)cc(c1)C(F)(F)F)ccc2C(N)=O | (400 MHz, DMSO-D6) 10.73 (s, 1 H), 10.48 (br s, 1 H), 9.80 (s, 1 H), 8.33 (d, 8.3 Hz, 1 H), 7.90 (d, 8.5 Hz, 1 H), 7.75 (s, 1 H), 7.71 (d, 8.3 Hz,1 H), 7.47 (d, 8.6 Hz, 1 H), 7.31 (br s, 1 H), 7.09 (td, 7.6, 0.9 Hz, 1 H), 7.01 (d, 7.3 Hz, 1 H), 6.99-6.93 (m, 1 H), 6.47 (br s, 1 H), 6.00 (br s, 1 H), 2.30 (br s, 3 H). | 472.3 | A | |
| I-509 | 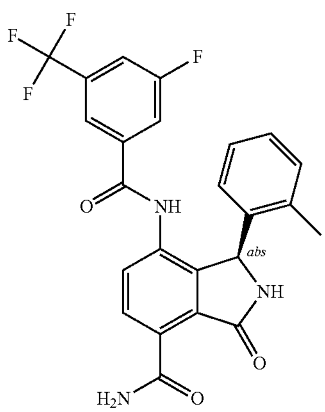 [SMILES: Cc1ccccc1[C@H]1NC(=O)c2c(C(N)=O)ccc(NC(=O)c3cc(F)cc(C(F)(F)F)c3)c21] | Cc1ccccc1[C@H]1NC(=O)c2c1c(NC(=O)c1cc(F)cc(c1)C(F)(F)F)ccc2C(N)=O | (400 MHz, DMSO-D6) 10.73 (s, 1 H), 10.48 (br s, 1 H), 9.80 (s, 1 H), 8.33 (d, 8.3 Hz, 1 H), 7.90 (d, 8.5 Hz, 1 H), 7.75 (s, 1 H), 7.71 (d, 8.3 Hz,1 H), 7.47 (d, 8.6 Hz, 1 H), 7.31 (br s, 1 H), 7.09 (td, 7.6, 0.9 Hz, 1 H), 7.01 (d, 7.3 Hz, 1 H), 6.99-6.93 (m, 1 H), 6.47 (br s, 1 H), 6.00 (br s, 1 H), 2.30 (br s, 3 H). | 472.3 | B | |
| I-510 | 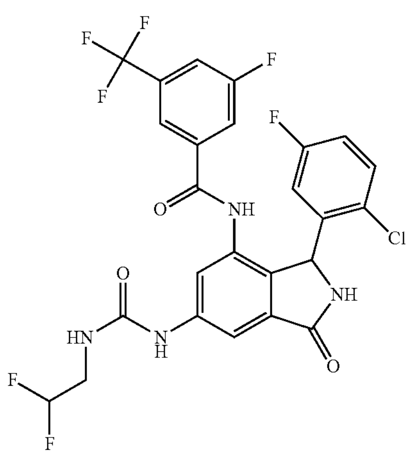 [SMILES: O=C(NCC(F)F)Nc1cc(NC(=O)c2cc(F)cc(C(F)(F)F)c2)c2c(c1)C(=O)NC2c1cc(F)ccc1Cl] | FC(F)CNC(=O)Nc1cc2C(=O)NC(c2c(NC(=O)c2cc(F)cc(c2)C(F)(F)F)c1)c1cc(F)ccc1Cl | 1H NMR (400 MHz, DMSO-d6) 3.48-3.62 (m, 2 H) 5.92-6.26 (m, 3 H) 6.70 (br t, 5.86 Hz, 1 H) 7.08 (td, 8.30, 2.93 Hz, 1 H) 7.30 (br dd, 8.79, 5.13 Hz, 1 H) 7.61 (br d, 15.62 Hz, 2 H) 7.68-7.79 (m, 2 H) 7.93 (br d, 8.30 Hz, 1 H) 9.07 (br s, 1 H) 9.21 (s, 1 H) 10.46 (s, 1 H) | 589.28 | A | |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-511 | 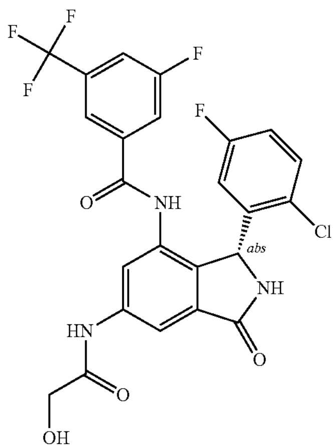 [SMILES: O=C(CO)Nc1cc(NC(=O)c2cc(F)cc(C(F)(F)F)c2)c2c(c1)C(=O)N[C@H]2c1cc(F)ccc1Cl] | OCC(=O)Nc1cc2C(=O)N[C@H](c2cc(NC(=O)c2cc(F)cc(c2)C(F)(F)F)c1)cc1cc(F)ccc1Cl | | 540.3 | A | |
| I-512 | 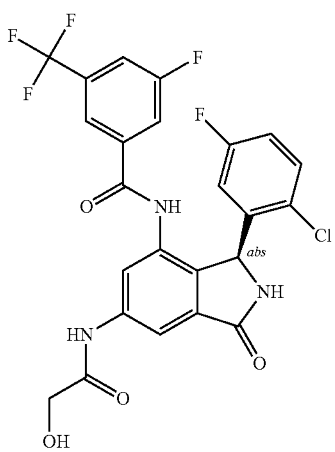 [SMILES: O=C(CO)Nc1cc(NC(=O)c2cc(F)cc(C(F)(F)F)c2)c2c(c1)C(=O)N[C@@H]2c1cc(F)ccc1Cl] | OCC(=O)Nc1cc2C(=O)N[C@@H](c2c(NC(=O)c2cc(F)cc(c2)C(F)(F)F)c1cc(F)ccc1Cl | | 540.3 | B | |
| I-513 | 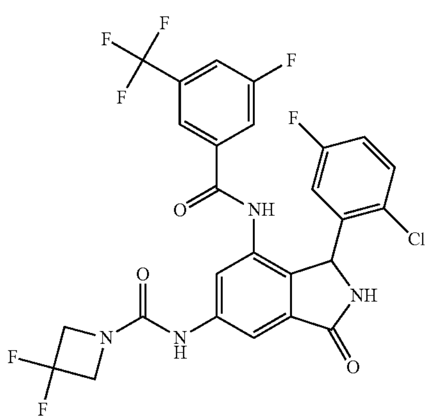 [SMILES: O=C(Nc1cc(NC(=O)N2CC(F)(F)C2)cc2c1C(c1cc(F)ccc1Cl)NC2=O)c1cc(F)cc(C(F)(F)F)c1] | Fc1ccc(C1)c(c1)C1NC(=O)c2cc(NC(=O)N3CC(F)(F)C3)cc(NC(=O)c3cc(F)cc(c3)C(F)(F)F)c12 | 1H NMR (400 MHz, DMSO-d6) 4.41 (br t, 12.69 Hz, 4 H) 5.90 (br s, 1 H) 6.75 (br s, 1 H) 7.07 (td, 8.36, 3.05 Hz, 1 H) 7.29 (br dd, 8.91, 5.25 Hz, 1 H) 7.62 (br s, 1 H) 7.70 (br s, 1 H) 7.86 (br s, 1 H) 7.92 (br d, 7.57 Hz, 1 H) 8.50 (br s, 1 H) 9.07 (br s, 1 H) 9.26 (br s, 1 H) 10.48 (s, 1 H) | 601.33 | A | |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-514 | 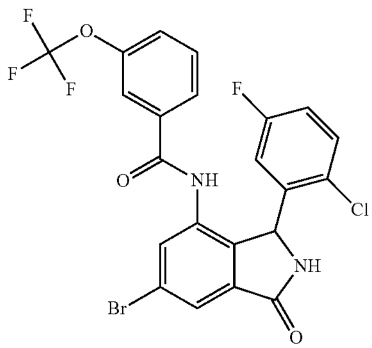 [SMILES: O=C(Nc1cc(Br)cc2c1C(c1cc(F)ccc1Cl)NC2=O)c1cccc(OC(F)(F)F)c1] | Fc1ccc(C1)c(c1)C1NC(=O)c2cc(Br)cc(NC(=O)c3cccc(OC(F)(F)F)c3)c12 | 1H NMR (400 MHz, Methanol-d4) 7.96 (d, 1.7 Hz, 1H), 7.77-7.72 (m, 1H), 7.61 (dt, 7.7, 1.5 Hz, 1H), 7.56 (dd, 8.7, 7.7 Hz, 1H), 7.52-7.46 (m, 2H), 7.29 (dd, 8.9, 5.1 Hz, 1H), 7.01 (ddd, 8.9, 7.8, 3.1 Hz, 1H), 6.63 (s, 1H), 6.18 (s, 1H). | 541 | C | |
| I-515 | 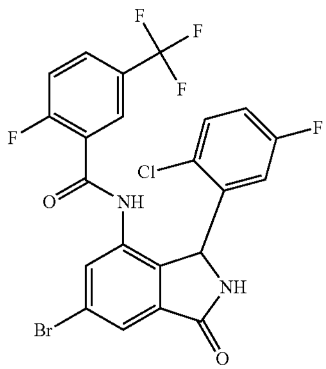 [SMILES: O=C(Nc1cc(Br)cc2c1C(c1cc(F)ccc1Cl)NC2=O)c1cc(C(F)(F)F)ccc1F] | Fc1ccc(C1)c(c1)C1NC(=O)c2cc(Br)cc(NC(=O)c3cc(ccc3F)C(F)(F)F)c12 | 1H NMR (400 MHz, DMSO-d6) 10.55 (s, 1H), 9.31 (s, 1H), 8.0 (s, 1H), 7.82 (d, 1.7 Hz, 1H), 7.73 (s, 1H), 7.56 (t, 9.2 Hz, 1H), 7.45 (dd, 8.9, 5.1 Hz, 1H), 7.38 (d, 5.8 Hz, 1H), 7.21 (td, 8.4, 3.1 Hz, 1H), 6.67 (s, 1H), 6.01 (s, 1H). | 545 | D | |
| I-516 | 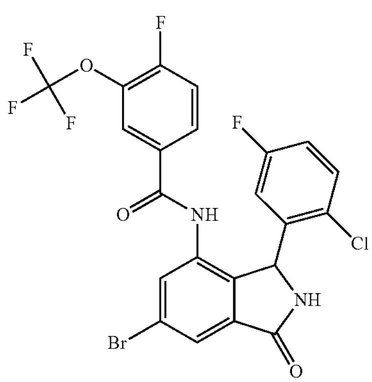 [SMILES: O=C(Nc1cc(Br)cc2c1C(c1cc(F)ccc1Cl)NC2=O)c1ccc(F)c(OC(F)(F)F)c1] | Fc1ccc(C1)c(c1)C1NC(=O)c2cc(Br)cc(NC(=O)c3ccc(F)c(OC(F)(F)F)c3)c12 | 1H NMR (400 MHz, DMSO-d6) 10.44 (s, 1H), 9.28 (s, 1H), 7.82 (d, 1.8 Hz, 1H), 7.79-7.70 (m, 2H), 7.70 (d, 7.4 Hz, 1H), 7.70-7.61 (m, 1H), 7.31 (dd, 8.9, 5.1 Hz, 1H), 7.09 (td, 8.4, 3.0 Hz, 1H), 6.73 (s, 1H), 5.97 (s, 1H). | 561 | B | |
| I-517 | 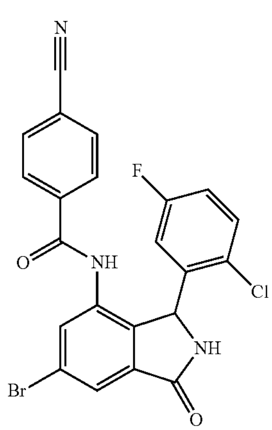 [SMILES: N#Cc1ccc(C(=O)Nc2cc(Br)cc3c2C(c2cc(F)ccc2Cl)NC3=O)cc1] | Fc1ccc(C1)c(c1)C1NC(=O)c2cc(Br)cc(NC(=O)c3ccc(cc3)C#N)c12 | 1H NMR (400 MHz, DMSO-d6) 10.45 (s, 1H), 9.29 (s, 1H), 7.88-7.79 (m, 2H), 7.73 (d, 1.8 Hz, 1H), 7.49 (d, 1.9 Hz, 3H), 7.37 (dd, 8.9, 5.2 Hz, 1H), 7.15 (td, 8.5, 3.1 Hz, 1H), 6.77 (s, 1H), 5.97 (s, 1H). | 484 | E | |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-518 | 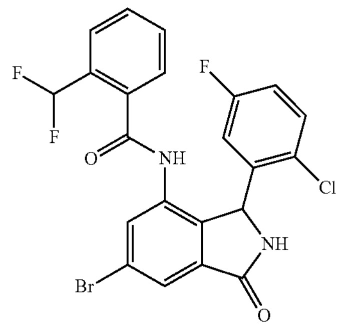 [SMILES: O=C(Nc1cc(Br)cc2c1C(c1cc(F)ccc1Cl)NC2=O)c1ccccc1C(F)F] | FC(F)c1c cccc1C(= O)Nc1cc (Br)cc2C (=O)NC(c 12)c1cc (F)ccc1Cl | 1H NMR (400 MHz, DMSO-d6) 10.50 (s, 1H), 9.30 (s, 1H), 7.81 (d, 9.4 Hz, 2H), 7.73 (d, 7.8 Hz, 1H), 7.66 (t, 7.6 Hz, 1H), 7.51 (q, 6.5, 5.6 Hz, 2H), 7.27 (td, 8.5, 3.2 Hz, 1H), 7.14 (s, 1H), 6.79 (d, 7.2 Hz, 2H), 6.04 (s, 1H). | 509 | E | |
| I-519 | 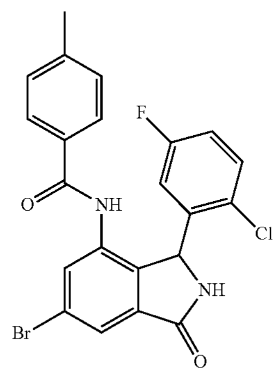 [SMILES: Cc1ccc(C(=O)Nc2cc(Br)cc3c2C(c2cc(F)ccc2Cl)NC3=O)cc1] | Cc1ccc(c c1)C(=O) Nc1cc(Br) cc2C(= O)NC(c1 2)c1cc(F) ccc1Cl | 1H NMR (400 MHz, Methanol-d4) 7.93 (d, 1.7 Hz, 1H), 7.75 (d, 1.7 Hz, 1H), 7.53-7.45 (m, 2H), 7.33-7.21 (m, 3H), 7.00 (ddd, 8.8, 7.7, 3.1 Hz, 1H), 6.66 (s, 1H), 6.18 (s, 1H), 2.41 (s, 3H). | 473 | E | |
| I-520 | 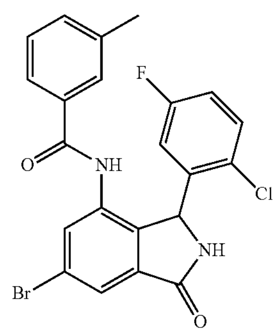 [SMILES: Cc1cccc(C(=O)Nc2cc(Br)cc3c2C(c2cc(F)ccc2Cl)NC3=O)c1] | Cc1cccc (c1)C(=O) Nc1cc(Br) cc2C(= O)NC(c1 2)c1cc(F) ccc1Cl | 1H NMR (400 MHz, Chloroform-d) 8.53 (s, 1H), 7.92 (d, 1.7 Hz, 1H), 7.47-7.25 (m, 6H), 7.07 (ddd, 8.9, 7.3, 3.0 Hz, 1H), 6.72 (s, 1H), 6.56 (s, 1H), 6.18 (s, 1H), 2.40 (s, 3H). | 473 | D | |
| I-521 | 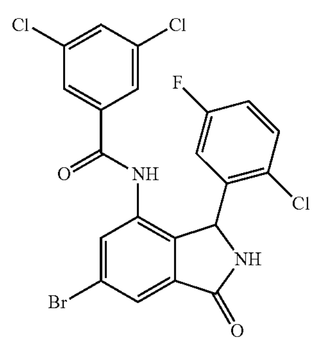 [SMILES: O=C(Nc1cc(Br)cc2c1C(c1cc(F)ccc1Cl)NC2=O)c1cc(Cl)cc(Cl)c1] | Fc1ccc(C 1)c(c1)C1 NC(=O)c 2cc(Br)cc (NC(=O) c3cc(Cl)c c(Cl)c3)c 12 | 1H NMR (400 MHz, DMSO-d6) 10.49 (s, 1H), 9.28 (s, 1H), 7.96 (d, 8.2 Hz, 2H), 7.81 (d, 1.8 Hz, 1H), 7.71 (d, 8.3 Hz, 3H), 7.34 (dd, 8.9, 5.1 Hz, 1H), 7.12 (td, 8.4, 3.1 Hz, 1H), 6.00 (s, 1H). | 527 | A | |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-522 | 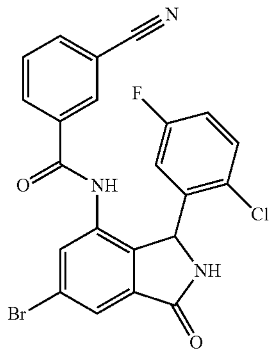 [SMILES: N#Cc1cccc(C(=O)Nc2cc(Br)cc3c2C(c2cc(F)ccc2Cl)NC3=O)c1] | Fc1ccc(C1)c(c1)CNC(=O)c2cc(Br)cc(NC(=O)c3cccc(c3)C#N)c12 | 1H NMR (400 MHz, Chloroform-d) 8.52 (s, 1H), 7.97 (d, 1.7 Hz, 1H), 7.93-7.83 (m, 2H), 7.63 (t, 7.8 Hz, 1H), 7.58-7.50 (m, 2H), 7.37 (s, 1H), 7.15 (ddd, 8.9, 7.3, 3.0 Hz, 1H), 6.74 (s, 1H), 6.41 (s, 1H), 6.19 (s, 1H), 0.87 (s, 0H) | 486 | D | |
| I-523 | 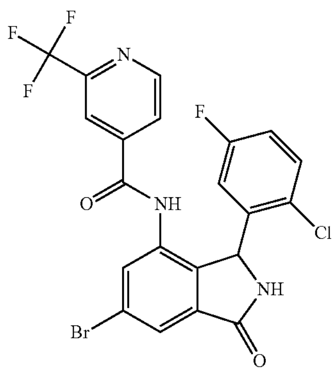 [SMILES: O=C(Nc1cc(Br)cc2c1C(c1cc(F)ccc1Cl)NC2=O)c1ccnc(C(F)(F)F)c1] | Fc1ccc(C1)c(c1)CNC(=O)c2cc(Br)cc(NC(=O)c3ccnc(c3)C(F)(F)F)c12 | 1H NMR (400 MHz, Methanol-d4) 8.86 (d, 4.9 Hz, 1H), 7.99 (d, 1.7 Hz, 1H), 7.90-7.78 (m, 2H), 7.75 (s, 1H), 7.31 (dd, 8.9, 5.1 Hz, 1H), 7.03 (ddd, 8.9, 7.7, 3.1 Hz, 1H), 6.66 (s, 1H), 6.12 (s, 1H). | 528 | E | |
| I-524 | 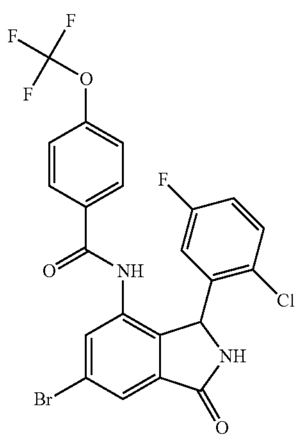 [SMILES: O=C(Nc1cc(Br)cc2c1C(c1cc(F)ccc1Cl)NC2=O)c1ccc(OC(F)(F)F)cc1] | Fc1ccc(C1)c(c1)CNC(=O)c2cc(Br)cc(NC(=O)c3ccc(OC(F)(F)F)cc3)c12 | 1H NMR (400 MHz, Methanol-d4) 7.95 (d, 1.7 Hz, 1H), 7.76-7.66 (m, 3H), 7.38-7.26 (m, 3H), 7.02 (ddd, 8.9, 7.8, 3.0 Hz, 1H), 6.79 (s, 1H), 6.17 (s, 1H). | 541 | D | |
| I-525 | 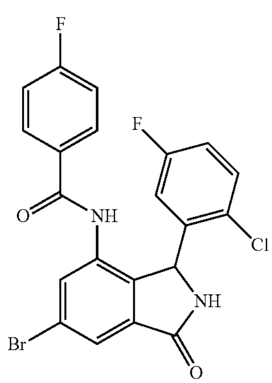 [SMILES: O=C(Nc1cc(Br)cc2c1C(c1cc(F)ccc1Cl)NC2=O)c1ccc(F)cc1] | Fc1ccc(cc1)C(=O)Nc1cc(Br)cc2C(=O)NC(c12)c1cc(F)ccc1Cl | 1H NMR (400 MHz, Methanol-d4) 7.94 (d, 1.7 Hz, 1H), 7.73 (d, 1.7 Hz, 1H), 7.70-7.61 (m, 2H), 7.30 (dd, 8.9, 5.1 Hz, 1H), 7.22-7.12 (m, 2H), 7.01 (ddd, 8.9, 7.7, 3.0 Hz, 1H), 6.65 (s, 1H), 6.17 (s, 1H). | 477 | E | |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-526 | 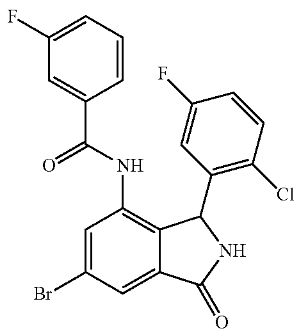 [SMILES: O=C(Nc1cc(Br)cc2c1C(c1cc(F)ccc1Cl)NC2=O)c1cccc(F)c1] | Fc1cccc(c1)C(=O)Nc1cc(Br)cc2C(=O)NC(c12)c1cc(F)ccc1Cl | 1H NMR (400 MHz, DMSO-d6) 10.31 (s, 1H), 9.27 (s, 1H), 7.80 (d, 1.8 Hz, 1H), 7.74 (d, 1.9 Hz, 1H), 7.56-7.46 (m, 1H), 7.46-7.38 (m, 2H), 7.38-7.27 (m, 2H), 7.13 (td, 8.4, 3.1 Hz, 1H), 6.95-6.40 (br, 1H), 6.01 (s, 1H). | 476.9 | D | |
| I-527 | 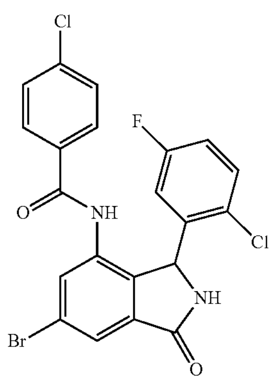 [SMILES: O=C(Nc1cc(Br)cc2c1C(c1cc(F)ccc1Cl)NC2=O)c1ccc(Cl)cc1] | Fc1ccc(C1)c(c1)C1NC(=O)c2cc(Br)cc(NC(=O)c3ccc(C1)cc3)c12 | 1H NMR (400 MHz, Methanol-d4) 7.95 (d, 1.7 Hz, 1H), 7.73 (d, 1.7 Hz, 1H), 7.62-7.54 (m, 2H), 7.50-7.43 (m, 2H), 7.31 (dd, 8.9, 5.1 Hz, 1H), 7.02 (ddd, 8.8, 7.7, 3.0 Hz, 1H), 6.65 (s, 1H), 6.18 (s, 1H). | 492.9 | D | |
| I-528 | 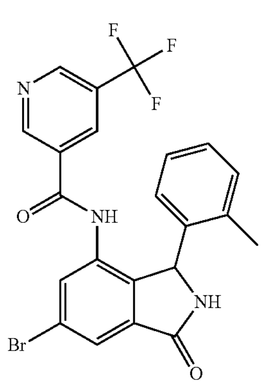 [SMILES: Cc1ccccc1C1NC(=O)c2cc(Br)cc(NC(=O)c3cncc(C(F)(F)F)c3)c21] | Cc1ccccc1C1NC(=O)c2cc(Br)cc(NC(=O)c3cncc(c3)C(F)(F)F)c12 | 1H NMR (400 MHz, DMSO-d6) 10.22 (br. s, 1H), 9.26 (s, 1H), 9.10 (s, 1H), 8.78 (s, 1H), 7.83 (overlap s, 1H), 7.80 (d, 1.7 Hz, 1H), 7.78 (d, 1.7 Hz, 1H), 7.07 (td, 7.5, 1.3 Hz, 1H), 7.00 (d, 6.8 Hz, 1H), 6.96 (br. t, 7.2 Hz, 1H), 6.57 (br. s, 1H), 5.89 (s, 1H), 2.23 (br. s, 3H), 10% of impurities at 1.98, 1.23 and 0.85 | 488.3 | D | |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-529 | 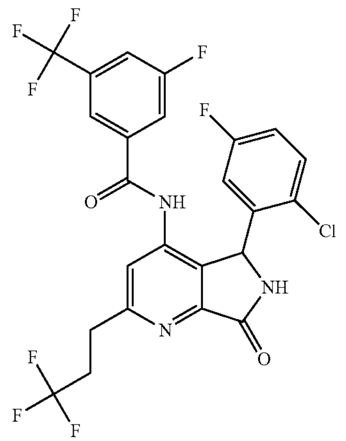 [SMILES: O=C(Nc1cc(CCC(F)(F)F)nc2c1C(c1cc(F)ccc1Cl)NC2=O)c1cc(F)cc(C(F)(F)F)c1] | Fc1ccc(C1)c(c1)C1NC(=O)c2nc(CCC(F)(F)F)cc(NC(=O)c3cc(F)cc(c3)C(F)(F)F)c12 | 1H NMR (400 MHz, DMSO-d6) 10.61 (br s, 1H), 9.47 (s, 1H), 7.96 (d, 7.8 Hz, 1H), 7.73 (d, 8.5 Hz, 1H), 7.62 (s, 1H), 7.51 (s, 1H), 7.34 (dd, 8.9, 5.2 Hz, 1H), 7.10 (td, 8.4, 3.1 Hz, 1H), 6.81 (br s, 1H), 5.97 (br s, 1H), 3.22-3.09 (m, 2H), 2.94-2.70 (m, 2H). contains 5%-10% | 564.3 | A | |
| I-530 | 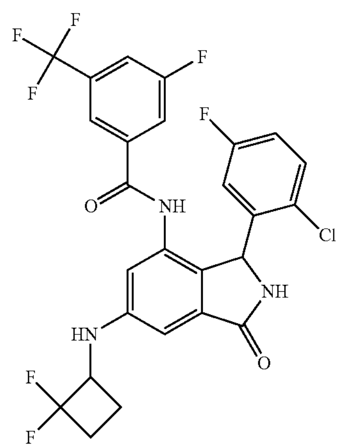 [SMILES: O=C(Nc1cc(NC2CCC2(F)F)cc2c1C(c1cc(F)ccc1Cl)NC2=O)c1cc(F)cc(C(F)(F)F)c1] | Fc1ccc(C1)c(c1)C1NC(=O)c2cc(NC3CCC3(F)F)cc(NC(=O)c3cc(F)cc(c3)C(F)(F)F)c12 | 1H NMR (400 MHz, DMSO-d6) 10.32 (d, 4.5 Hz, 1H), 8.96 (s, 1H), 7.92 (d, 8.4 Hz, 1H), 7.69 (d, 9.2 Hz, 1H), 7.60 (s, 1H), 7.28 (ddd, 8.8, 5.2, 1.7 Hz, 1H), 7.14-7.00 (m, 1H), 6.90 (d, 1.8 Hz, 1H), 6.77 (s, 1H), 6.74 (d, 7.3 Hz, 1H), 6.57 (br s, 1H), 5.82 (br s, 1H), 4.57-4.22 (m, 1H), 2.47-2.32 (m, 2H), 2.31-2.17 (m, 1H), 1.71 (p, 9.9 Hz, 1H). | 572.5 | A | |
| I-531 | 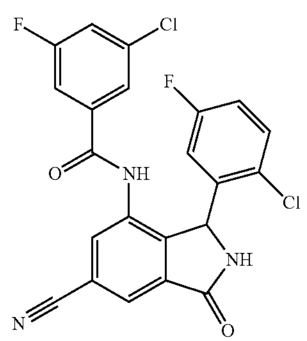 [SMILES: N#Cc1cc(NC(=O)c2cc(F)cc(Cl)c2)c2c(c1)C(=O)NC2c1cc(F)ccc1Cl] | Fc1ccc(C1)c(c1)C1NC(=O)c2cc(cc(NC(=O)c3cc(F)cc(Cl)c3)c12)C#N | NMR (400 MHz, DMSO-d6i) 9.42 (s, 1H), 8.10 (s, 1H), 8.03 (s, 1H), 7.69 (d, 8.5 Hz, 1H), 7.44-7.33 (m, 4H), 7.16 (td, 8.3, 2.8 Hz, 1H), 6.77 (br s, 1H), 6.06 (s, 1H). | 458 | A | |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-532 | 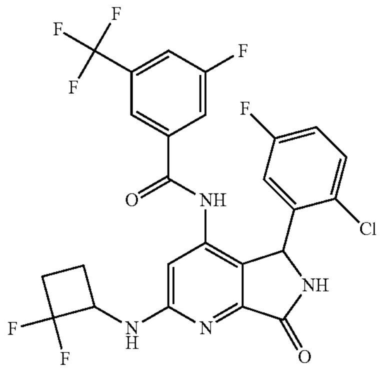 [SMILES: O=C(Nc1cc(NC2CCC2(F)F)nc2c1C(c1cc(F)ccc1Cl)NC2=O)c1cc(F)cc(C(F)(F)F)c1] | Fc1ccc(C1)c(c1)C1NC(=O)c2nc(NC3CCC3(F)F)cc(NC(=O)c3cc(F)cc(c3)C(F)(F)F)c12 | 1H NMR (400 MHz, DMSO-d6) 10.55 (s, 1H), 9.21 (s, 1H), 7.96 (d, 8.3 Hz, 1H), 7.66 (d, 7.8 Hz, 2H), 7.54 (s, 1H), 7.31 (ddd, 8.7, 5.2, 1.9 Hz, 1H), 7.07 (td, 8.4, 3.0 Hz, 1H), 6.77 (br s, 1H), 6.73 (d, 1.9 Hz, 1H), 5.85 (br s, 1H), 5.09 (br s, 1H), 2.54-2.30 (m, 2H), 2.30-2.18 (m, 1H), 1.82-1.57 (m, 1H). | 573.4 | A | |
| I-533 | 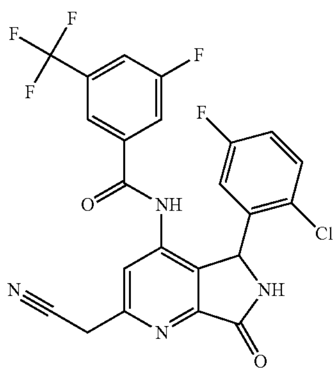 [SMILES: N#CCc1cc(NC(=O)c2cc(F)cc(C(F)(F)F)c2)c2c(n1)C(=O)NC2c1cc(F)ccc1Cl] | Fc1ccc(C1)c(c1)C1NC(=O)c2cc(CC#N)cc(NC(=O)c3cc(F)cc(c3)C(F)(F)F)c12 | 1H-NMR (400 MHz, DMSO-d6) 10.61 (br. s, 1H), 9.22 (br. s, 1H), 7.95 (d, 7.7 Hz, 1H), 7.74 (d, 8.8 Hz, 1H), 7.70-7.63 (m, 2H), 7.51 (, 1Hs), 7.32 (dd, 8.9, 5.2 Hz, 1H), 7.09 (td, 8.5, 3.1 Hz, 1H), 6.63 (br. s, 1H), 5.98 (br. s, 1H), 4.26 (s, 2H). Partial formate salt (peak at 8.47). | 504.3 | A | |
| I-534 | 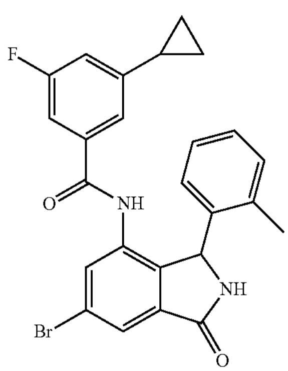 [SMILES: Cc1ccccc1C1NC(=O)c2cc(Br)cc(NC(=O)c3cc(F)cc(C4CC4)c3)c21] | Cc1ccccc1C1NC(=O)c2cc(Br)cc(NC(=O)c3cc(F)cc(c3)C3CC3)c12 | 10.11 (s, 1H), 9.23 (s, 1H), 7.81 (d, 1.7 Hz, 1H), 7.76 (d, 1.7 Hz, 1H), 7.14-7.06 (m, 3H), 6.99 (td, 7.5, 1.3 Hz, 1H), 6.86 (br. d, 9.5 Hz, 1H), 6.74 (s, 1H), 6.55 (br. s, 1H), 5.95 (s, 1H), 2.28 (br. s, 3H), 1.95-1.85 (m, 1H), 1.03-0.95 (m, 2H), 0.71-0.62 (m, 2H), traces of impurities 1.98, 1.23 and 0.85. | 479.3 | D | |
| I-535 | 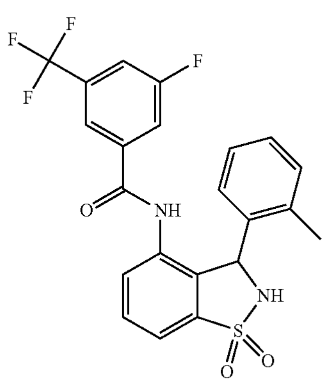 [SMILES: Cc1ccccc1C1NS(=O)(=O)c2cccc(NC(=O)c3cc(F)cc(C(F)(F)F)c3)c21] | Cc1ccccc1C1NS(=O)(=O)c2cccc(NC(=O)c3cc(F)cc(c3)C(F)(F)F)c12 | NMR (400 MHz, DMSO) 10.41 (s, 1H), 8.45 (d, 4.5 Hz, 1H), 7.85 (dt, 8.3 and 1.6 Hz, 1H), 7.81 (d, 7.6 Hz, 1H), 7.72 (t, 7.7 Hz, 1H), 7.59 (d, 7.4 Hz, 1H), 7.39 (d, 8.8 Hz, 1H), 7.22 (s, 1H), 7.03 (t, 7.3 Hz, 1H), 6.90-6.99 (m, 2H), 6.55 (br s, 1H), 5.97 (s, 1H), 2.16 (br. s, 3H). | 465.1 | D | |

TABLE 2-continued

Representative Compounds of the Invention with Bioactivity Data.

| Ex. No. | Structure | SMILES | $^1$H NMR | MS | ADP-Glo IC$_{50}$ | MCF 10A IC$_{50}$ |
|---|---|---|---|---|---|---|
| I-536 | 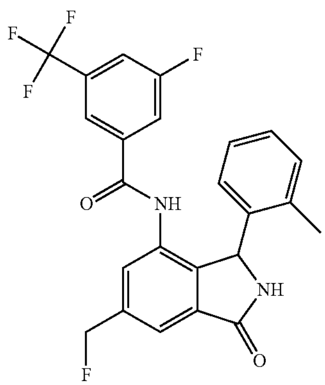 [SMILES: Cc1ccccc1C1NC(=O)c2cc(CF)cc(NC(=O)c3cc(F)cc(C(F)(F)F)c3)c21] | Cc1ccccc1C1NC(=O)c2cc(CF)cc(NC(=O)c3cc(F)cc(c3)C(F)(F)F)c12 | NMR (400 MHz, DMSO) 10.44 (s, 1H), 9.15 (s, 1H), 7.90 (d, 8.5 Hz, 1H), 7.72 (s, 1H), 7.60 (s, 1H), 7.49 (d, 9.0 Hz, 1H), 7.36 (s, 1H), 7.07 (t, 7.5 Hz, 1H), 7.00 (d, 7.3 Hz, 1H), 6.95 (t, 7.0 Hz, 1H), 6.59 (br s, 1H), 5.93 (s, 1H), 5.61 (d, 47.4 Hz, 2H), 2.21 (br s, 3H). | 461.2 | A | |
| I-537 | 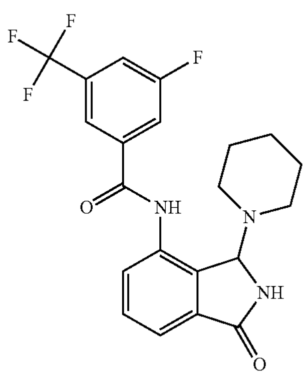 [SMILES: O=C(Nc1cccc2c1C(N1CCCCC1)NC2=O)c1cc(F)cc(C(F)(F)F)c1] | Fc1cc(cc(c1)C(F)(F)F)C(=O)Nc1ccc2C(=O)NC(N3CCCCC3)c12 | NMR (400 MHz, DMSO-d6) 10.48 (s, 1H), 8.96 (s, 1H), 8.26 (dd, 8.0, 0.7 Hz, 1H), 8.12 (s, 1H), 8.11-8.04 (m, 2H), 7.57 (t, 7.7 Hz, 1H), 7.47 (dd, 7.5, 0.9 Hz, 1H), 5.68 (s, 1H), 2.53 (m, 2H), 2.33-2.24 (m, 2H), 1.38 (m, 4H), 1.35-1.27 (m, 2H) | 422.3 | E | |
| I-538 | 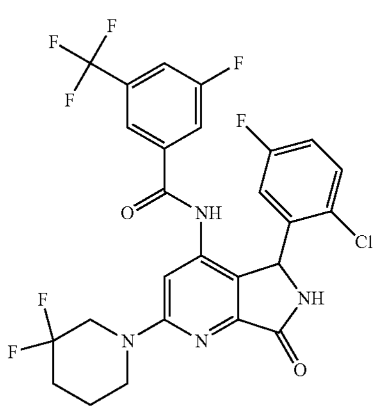 [SMILES: O=C(Nc1cc(N2CCCC(F)(F)C2)nc2c1C(c1cc(F)ccc1Cl)NC2=O)c1cc(F)cc(C(F)(F)F)c1] | Fc1ccc(C1)c(c1)C1NC(=O)c2nc(cc(NC(=O)c3cc(F)cc(c3)C(F)(F)F)c12)N1CCCC(F)(F)C1 | (400 MHz, CD3CN) 8.63 (s, 1H), 7.66 (d, 8.9 Hz, 1H), 7.57 (d, 8.5 Hz, 1H), 7.55 (br. s, 1H), 7.39 (br. s, 1H), 7.33-7.27 (m, 1H), 7.10 (s, 1H), 6.98 (td, 8.4, 3.1 Hz, 1H), 6.75 (br. s, 1H), 6.04 (s, 1H), 4.06-3.94 (m, 2H), 3.73-3.65 (m, 2H), 1.91-1.81 (m, 4H). | 587.3 | A | |

TABLE 2-continued

Representative Compounds of the Invention with Bioactivity Data.

| Ex. No. | Structure | SMILES | $^1$H NMR | MS | ADP-Glo IC$_{50}$ | MCF 10A IC$_{50}$ |
|---|---|---|---|---|---|---|
| I-539 | 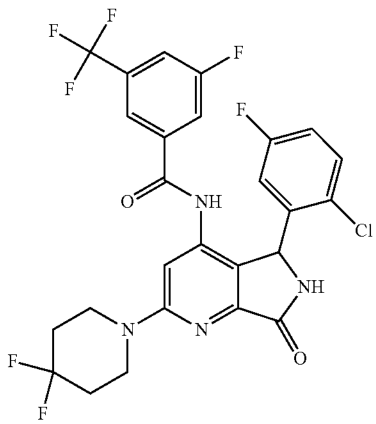 [SMILES: O=C(Nc1cc(N2CCC(F)(F)CC2)nc2c1C(c1cc(F)ccc1Cl)NC2=O)c1cc(F)cc(C(F)(F)F)c1] | Fc1ccc(C1)c(c1)C1NC(=O)c2nc(cc(NC(=O)c3cc(F)cc(c3)C(F)(F)F)c12)N1CCC(F)(F)CC1 | (400 MHz, CD3CN) 8.64 (br. s, 1H), 7.66 (d, 8.4 Hz, 1H), 7.61-7.50 (m, 2H), 7.39 (s, 1H), 7.30 (dd, 8.9, 5.1 Hz, 1H), 7.13 (s, 1H), 6.98 (ddd, 8.9, 8.0, 3.0 Hz, 1H), 6.75 (br. s, 1H), 6.05 (s, 1H), 3.84-3.81 (m, 4 H), 2.10-2.03 (m, 4H). | 587.3 | A | |
| I-540 | 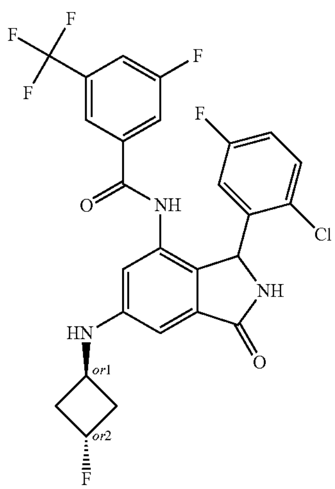 [SMILES: O=C(Nc1cc(N[C@H]2C[C@H](F)C2)cc2c1C(c1cc(F)ccc1Cl)NC2=O)c1cc(F)cc(C(F)(F)F)c1] | F[C@H]1C[c@@H](C1)Nc1cc2C(=O)NC(c2c(NC(=O)c2cc(F)cc(c2)C(F)(F)F)c1)c1cc(F)ccc1Cl | 1H NMR (400 MHz, DMSO-d6) 10.28 br. (s, 1H), 8.94 (br. s, 1H), 7.92 (d, 8.5 Hz, 1H), 7.69 (d, 9.0 Hz, 1H), 7.60 (s, 1H), 7.28 (dd, 8.9, 5.2 Hz, 1H), 7.06 (td, 8.4, 3.1 Hz, 1H), 6.70 (d, 2.0 Hz, 1H), 6.61 (s, 1H), 6.58 (d, 4.3 Hz, 1H), 6.74-6.42 (1H submerged), 5.83 (br. s, 1H), 5.38-5.18 (m, 1H), 4.07-4.03 (m, 1H), 2.64-2.54 (m, 2H), 2.37-2.26 (m, 2H) | 554.3 | A | |
| I-541 | 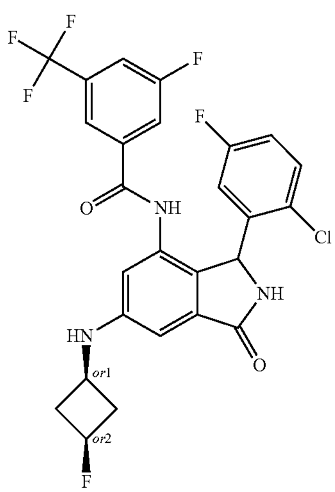 [SMILES: O=C(Nc1cc(N[C@H]2C[C@@H](F)C2)cc2c1C(c1cc(F)ccc1Cl)NC2=O)c1cc(F)cc(C(F)(F)F)c1] | F[C@H]1C[C@H](C1)Nc1cc2C(=O)NC(c2c(NC(=O)c2cc(F)cc(c2)C(F)(F)F)c1)c1cc(F)ccc1Cl | 1H NMR (400 MHz, ) 10.28 (br. s, 1H), 8.93 (br. s, 1H), 7.92 (d, 8.5 Hz, 1H), 7.69 (d, 9.2 Hz, 1H), 7.61 (s, 1H), 7.28 (dd, 8.9, 5.2 Hz, 1H), 7.06 (td, 8.4, 3.1 Hz, 1H), 6.75 (d, 2.0 Hz, 1H), 6.63 (d, 1.4 Hz, 1H), 6.55 (d, 6.8 Hz, 1H), 6.74-6.42 (1H submerged), 5.82 (br. s, 1H), 4.92 (dp, 56.2, 6.8 Hz, 1H), 3.53-3.43 (m, 1H), 2.94-2.86 (m, 2H), 2.12-1.96 (m, 2H); | 554.2 | A | |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-542 | 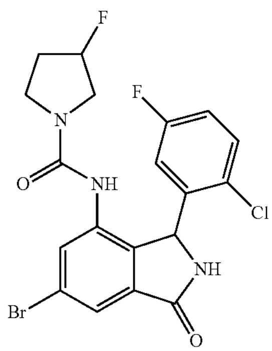 [SMILES: O=C1NC(c2cc(F)ccc2Cl)c2c(NC(=O)N3CCC(F)C3)cc(Br)cc21] | FC1CCN(C1)C(=O)Nc1cc(Br)cc2C(=O)NC(c12)c1cc(F)ccc1Cl | NMR (400 MHz, CD3CN) 7.74-7.60 (m, 2H), 7.47-7.37 (m, 1H), 7.25 (s, 1H), 7.13-7.03 (m, 1H), 6.68 (s, 1H), 6.10 (s, 1H), 5.31-5.08 (m, 1H), 3.65-2.89 (m, 5H), 2.09-2.02 (m, 1H), 1.90-1.80 (m, 1H): possible mixture of rotamers and diastereomers + grease | 470.1 | E | |
| I-543 | 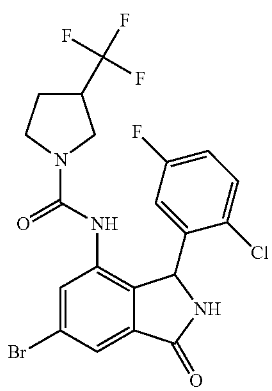 [SMILES: O=C1NC(c2cc(F)ccc2Cl)c2c(NC(=O)N3CCC(C(F)(F)F)C3)cc(Br)cc21] | Fc1ccc(Cl)c(c1)C1NC(=O)c2cc(Br)cc(NC(=O)N3CCC(C3)C(F)(F)F)c12 | NMR (400 MHz, CD3CN) 7.73-7.69 (m, 1H), 7.66 (d, 7.3 Hz, 1H), 7.44 (dd, 8.7, 5.1 Hz, 1H), 7.25 (s, 1H), 7.15-7.03 (m, 1H), 6.72 (br s, 1H), 6.67 (d, 14.4 Hz, 1H), 6.20-5.95 (m, 1H), 3.71-3.37 (m, 2H), 3.31-3.14 (m, 1H), 3.12-2.86 (m, 2H), 2.14-2.05 (m, 1H), 2.02-1.96 (m, 1H). | 518.2 | D | |
| I-544 | 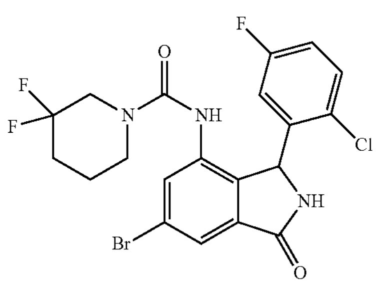 [SMILES: O=C1NC(c2cc(F)ccc2Cl)c2c(NC(=O)N3CCCC(F)(F)C3)cc(Br)cc21] | Fc1ccc(Cl)c(c1)C1NC(=O)c2cc(Br)cc(NC(=O)N3CCCC(F)(F)C3)c12 | NMR (400 MHz, CD3CN) 7.71 (d, 1.7 Hz, 1H), 7.58 (d, 1.6 Hz, 1H), 7.42 (dd, 17.2, 8.7 Hz, 1H), 7.23 (d, 1.6 Hz, 1H), 7.08 (ddd, 8.9, 8.0, 3.1 Hz 1H), 7.03 (s, 1H), 6.71 (br s, 1H), 6.06 (br s, 1H), 3.60-3.46 (m, 1H), 3.46-3.31 (m, 1H), 3.22-3.10 (m, 1H), 3.05-2.91 (m, 1H), 2.13-2.09 (m, 1H), 2.02-1.97 (m, 1H), 1.66-1.45 (m, 2H). approx 10% impurity by NMR | 502.1 | D | |
| I-545 | 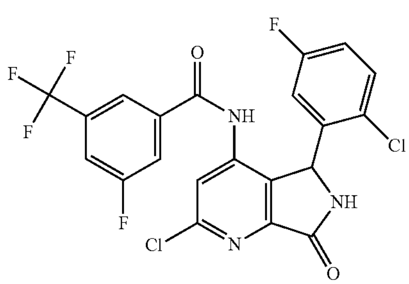 [SMILES: O=C(Nc1cc(Cl)nc2c1C(c1cc(F)ccc1Cl)NC2=O)c1cc(F)cc(C(F)(F)F)c1] | Fc1ccc(Cl)c(c1)C1NC(=O)c2nc(Cl)cc(NC(=O)c3cc(F)cc(c3)C(F)(F)F)c12 | | 502.3 | A | |

TABLE 2-continued

Representative Compounds of the Invention with Bioactivity Data.

| Ex. No. | Structure | SMILES | $^1$H NMR | MS | ADP-Glo IC$_{50}$ | MCF 10A IC$_{50}$ |
|---|---|---|---|---|---|---|
| I-546 | 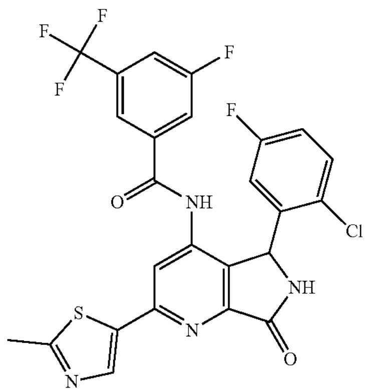 [SMILES: Cc1ncc(-c2cc(NC(=O)c3cc(F)cc(C(F)(F)F)c3)c3c(n2)C(=O)NC3c2cc(F)ccc2Cl)s1] | Cc1ncc(s1)-c1cc(NC(=O)c2cc(F)cc(c2)C(F)(F)F)c2C(NC(=O)c2n1)c1cc(F)ccc1Cl | | 565.4 | A | |
| I-547 | 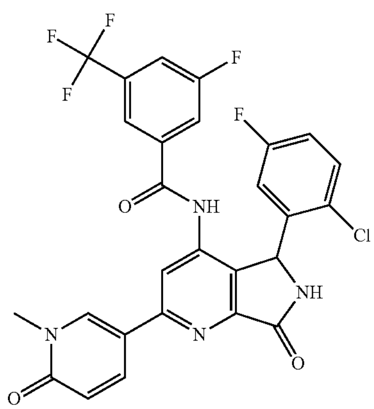 [SMILES: Cn1cc(-c2cc(NC(=O)c3cc(F)cc(C(F)(F)F)c3)c3c(n2)C(=O)NC3c2cc(F)ccc2Cl)ccc1=O] | Cn1cc(ccc1=O)-c1cc(NC(=O)c2cc(F)cc(c2)C(F)(F)F)c2C(NC(=O)c2n1)c1cc(F)ccc1Cl | | 575.5 | A | |
| I-548 | 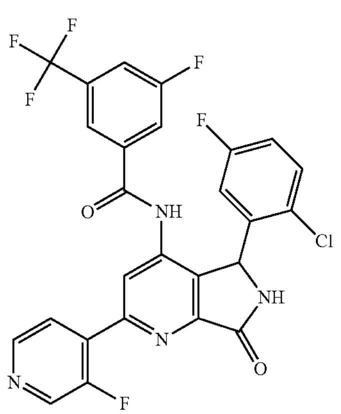 [SMILES: O=C(Nc1cc(-c2ccncc2F)nc2c1C(c1cc(F)ccc1Cl)NC2=O)c1cc(F)cc(C(F)(F)F)c1] | Fc1ccc(C1)c(c1)C1NC(=O)c2nc(cc(NC(=O)c3cc(F)cc(c3)C(F)(F)F)c12)-c1ccncc1F | | 563.4 | A | |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-549 | 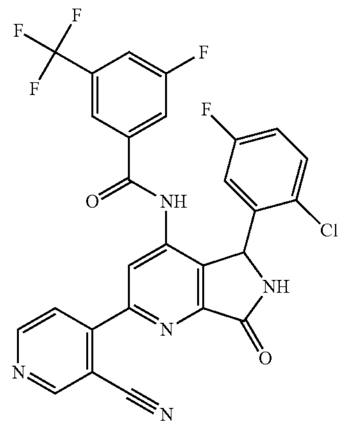 [SMILES: N#Cc1cnccc1-c1cc(NC(=O)c2cc(F)cc(C(F)(F)F)c2)c2c(n1)C(=O)NC2c1cc(F)ccc1Cl] | Fc1ccc(C1)c(c1)CNC(=O)c2nc(cc(NC(=O)c3cc(F)cc(c3)C(F)(F)F)c12)-c1ccncc1C#N | | 570.4 | A | |
| I-550 | 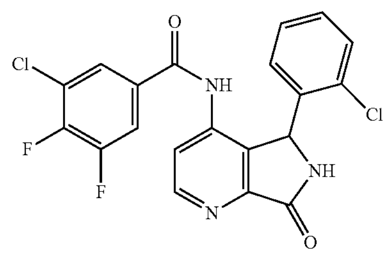 [SMILES: O=C(Nc1ccnc2c1C(c1ccccc1Cl)NC2=O)c1cc(F)c(F)c(Cl)c1] | Fc1cc(cc(Cl)c1F)C(=O)Nc1ccnc2C(=O)NC(c12)c1ccccc1Cl | | 434.3 | C | |
| I-551 | 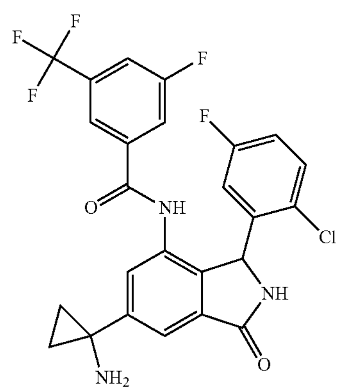 [SMILES: NC1(c2cc(NC(=O)c3cc(F)cc(C(F)(F)F)c3)c3c(c2)C(=O)NC3c2cc(F)ccc2Cl)CC1] | NC1(CC1)c1cc2C(=O)NC(c2c(NC(=O)c2cc(F)cc(c2)C(F)(F)F)c1)c1ccc(F)ccc1Cl | NMR (400 MHz, CD3CN) 8.73 (s, 1H), 8.27 (d, 1.4 Hz, 1H), 8.12 (s, 1H), 7.66 (dd, 6.8, 1.8 Hz, 1H), 7.64-7.57 (m, 2H), 7.35 (s, 1H), 7.27 (dd, 8.9, 5.1 Hz, 1H), 6.98 (ddd, 8.9, 8.0, 3.1 Hz, 1H), 6.66 (br s, 1H), 6.17 (br s, 1H), 3.15 (qd, 7.1, 0.9 Hz, 2H), 1.19 (t, 7.2 Hz, 4H). | 523.1 | A | |
| I-552 | 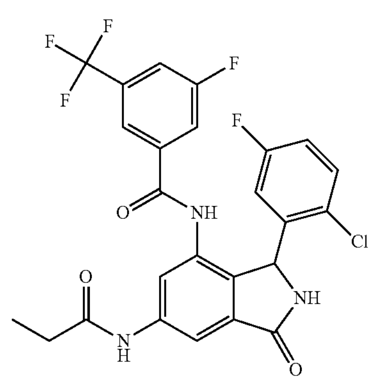 [SMILES: CCC(=O)Nc1cc(NC(=O)c2cc(F)cc(C(F)(F)F)c2)c2c(c1)C(=O)NC2c1cc(F)ccc1Cl] | CCC(=O)Nc1cc2C(=O)NC(c2c(NC(=O)c2cc(F)cc(c2)C(F)(F)F)c1)c1ccc(F)ccc1Cl | 1H NMR (400 MHz, DMSO-d6) 1.12 (t, 7.44 Hz, 3 H) 2.29-2.45 (m, 2 H) 5.91 (br s, 1 H) 6.83 (br s, 1 H) 7.08 (td, 8.30, 2.93 Hz, 1 H) 7.31 (br dd, 8.91, 5.25 Hz, 1 H) 7.58-7.97 (m, 4 H) 8.50 (s, 1 H) 9.10 (br s, 1 H) 10.28 (br s, 1 H) 10.52 (br s, 1 H) | 538.25 | A | |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-553 | 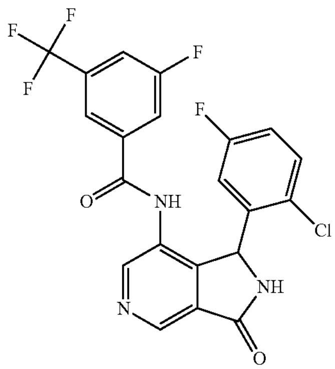 [SMILES: O=C(Nc1cncc2c1C(c1cc(F)ccc1Cl)NC2=O)c1cc(F)cc(C(F)(F)F)c1] | Fc1ccc(C1)c(c1)C1NC(=O)c2cncc(NC(=O)c3cc(F)cc(c3)C(F)(F)F)c12 | NMR (400 MHz, DMSO-d6) 10.70 (br. s, 1H), 9.33 (s, 1H), 8.89 (s, 1H), 8.69 (s, 1H), 7.97 (d, 8.7 Hz, 1H), 7.76 (d, 9.1 Hz, 1H), 7.68 (s, 1H), 7.34 (dd, 8.9, 5.2 Hz, 1H), 7.16-7.05 (m, 1H), 6.85 (br. s, 1H), 6.02 (br. s, 1H). | 468 | A | |
| I-554 | 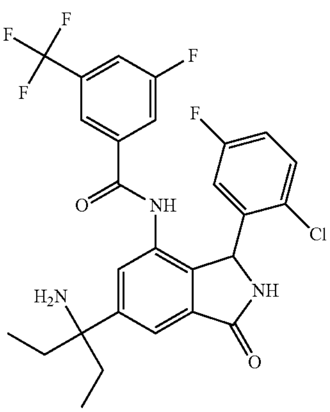 [SMILES: CCC(N)(CC)c1cc(NC(=O)c2cc(F)cc(C(F)(F)F)c2)c2c(c1)C(=O)NC2c1cc(F)ccc1Cl] | CCC(N)(CC)c1cc2C(=O)NC(c2c(NC(=O)c2cc(F)cc(c2)C(F)(F)F)c1)c1cc(F)ccc1C1 | (400 MHz, CD3CN) 8.65 (br s, 1H), 8.10 (s, 1H), 7.82 (d, 1.6 Hz, 1H), 7.64 (s, 1H), 7.64-7.59 (m, 1H), 7.57 (s, 1H), 7.25 (dd, 8.8, 5.1 Hz, 1H), 7.19 (s, 1H), 6.96 (ddd, 8.8, 7.9, 3.0 Hz., 1H), 6.61 (br s, 1H), 6.09 (br s, 1H), 3.93 (t, 6.0 Hz, 1H), 3.28 (t, 5.9 Hz, 1H), 1.87 (br q, 7.0 Hz, 2H), 1.71 (br q, 7.3 Hz, 2H), 0.73 (td, 7.4, 2.0 Hz, 6H). | 550.4 | A | |
| I-555 | 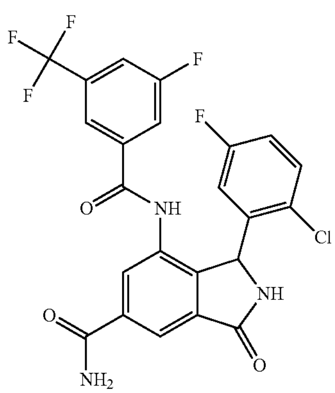 [SMILES: NC(=O)c1cc(NC(=O)c2cc(F)cc(C(F)(F)F)c2)c2c(c1)C(=O)NC2c1cc(F)ccc1Cl] | NC(=O)c1cc2C(=O)NC(c2c(NC(=O)c2cc(F)cc(c2)C(F)(F)F)c1)c1cc(F)ccc1Cl | (400 MHz, d6-DMSO) 10.63 (s, 1H), 9.26 (s, 1H), 8.30 (s, 1H), 8.25 (s, 1H), 8.01 (d, 0.9 Hz, 1H), 7.96 (d, 8.5 Hz, 1H), 7.75 (d, 9.1 Hz, 1H), 7.68 (s, 1H), 7.59 (s, 1H), 7.32 (dd, 8.9, 5.2 Hz, 1H), 7.10 (ddd, 8.8, 3.2, 3.2 Hz, 1H), 6.02 (br s, 1H). | 510.2 | A | |
| I-556 | 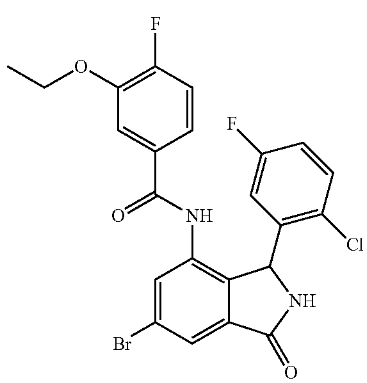 [SMILES: CCOc1cc(C(=O)Nc2cc(Br)cc3c2C(c2cc(F)ccc2Cl)NC3=O)ccc1F] | CCOc1cc(ccc1F)C(=O)Nc1cc(Br)cc2C(=O)NC(c12)c1cc(F)ccc1Cl | 1H NMR (400 MHz, Methanol-d4)7.94 (d, 1.7 Hz, 1H), 7.73 (s, 1H), 7.32 (ddd, 10.1, 7.5, 3.5 Hz, 2H), 7.21-7.10 (m, 2H), 7.02 (ddd, 8.8, 7.7, 3.1 Hz, 1H), 6.42 (d, 201.1 Hz, 2H), 4.13 (qd, 7.0, 4.9 Hz, 2H), 1.46 (t, 7.0 Hz, 3H). | 520.95 | D | |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-557 | 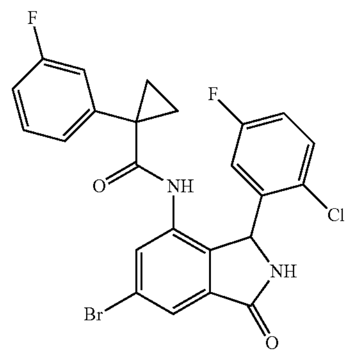 [SMILES: O=C1NC(c2cc(F)ccc2Cl)c2c(NC(=O)C3(c4cccc(F)c4)CC3)cc(Br)cc21] | Fc1cccc(c1)C1(CC1)C(=O)Nc1cc(Br)cc2C(=O)NC(c12)c1cc(F)ccc1Cl | 1H NMR (400 MHz, Methanol-d4) 7.85 (d, 1.8 Hz, 1H), 7.68 (s, 1H), 7.59 (s, 1H), 7.35-7.20 (m, 2H), 7.02 (td, 8.3, 2.6 Hz, 1H), 6.87 (dt, 7.7, 1.3 Hz, 1H), 6.76 (dt, 9.9, 2.1 Hz, 1H), 6.44 (s, 1H), 6.08 (s, 1H), 1.62 (s, 1H), 1.34 (ddd, 10.1, 7.0, 4.0 Hz, 1H), 1.20-1.11 (m, 1H), 0.98 (ddd, 9.6, 7.0, 3.8 Hz, 1H). | 516.9 | D | |
| I-558 | 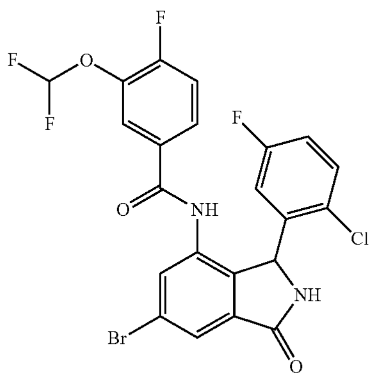 [SMILES: O=C(Nc1cc(Br)cc2c1C(c1cc(F)ccc1Cl)NC2=O)c1ccc(F)c(OC(F)F)c1] | FC(F)Oc1cc(ccc1F)C(=O)Nc1cc(Br)cc2C(=O)NC(c12)c1cc(F)ccc1Cl | 1H NMR (400 MHz, Methanol-d4) 7.95 (d, 1.7 Hz, 1H), 7.72 (s, 1H), 7.61-7.48 (m, 2H), 7.41-7.24 (m, 2H), 7.11-6.50 (m, 3H), 6.16 (s, 1H). | 542.85 | D | |
| I-559 | 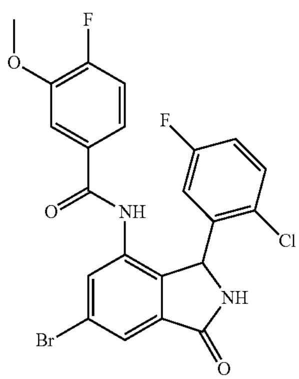 [SMILES: COc1cc(C(=O)Nc2cc(Br)cc3c2C(c2cc(F)ccc2Cl)NC3=O)ccc1F] | COc1cc(ccc1F)C(=O)Nc1cc(Br)cc2C(=O)NC(c12)c1cc(F)ccc1Cl | 1H NMR (400 MHz, Chloroform-d) 8.41 (s, 1H), 7.95 (d, 1.6 Hz, 1H), 7.44-7.33 (m, 3H), 7.13-7.01 (m, 2H), 6.83 (s, 1H), 6.71 (s, 1H), 6.49 (s, 1H), 6.18 (s, 1H), 3.94 (s, 3H), 2.03 (s, 0H). | 508.9 | D | |
| I-560 | 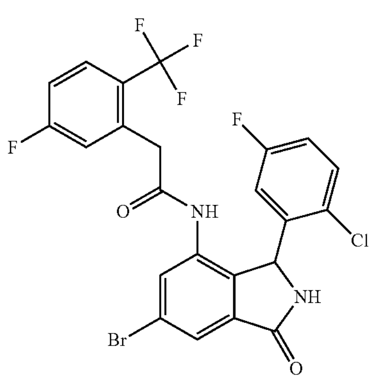 [SMILES: O=C(Cc1cc(F)ccc1C(F)(F)F)Nc1cc(Br)cc2c1C(c1cc(F)ccc1Cl)NC2=O] | Fc1ccc(c(CC(=O)Nc2cc(Br)cc3C(=O)NC(c23)c2cc(F)ccc2Cl)c1)C(F)(F)F | 1H NMR (400 MHz, Chloroform-d) 8.38 (s, 1H), 7.90 (d, 1.7 Hz, 1H), 7.64 (dd, 8.8, 5.4 Hz, 1H), 7.45 (dd, 8.9, 4.9 Hz, 1H), 7.15-7.01 (m, 3H), 6.85 (s, 1H), 6.53 (d, 8.3 Hz, 1H), 6.38 (s, 1H), 6.02 (s, 1H), 3.76-3.65 (m, 2H), 3.50 (d, 16.0 Hz, 1H). | 561 | D | |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-561 | 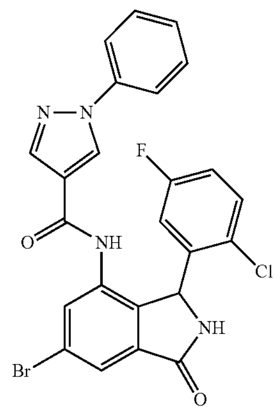 [SMILES: O=C(Nc1cc(Br)cc2c1C(c1cc(F)ccc1Cl)NC2=O)c1cnn(-c2ccccc2)c1] | Fc1ccc(C1)c(c1)C1NC(=O)c2cc(Br)cc(NC(=O)c3cnn(c3)-c3ccccc3)c12 | 1H NMR (400 MHz, Chloroform-d) 8.52 (s, 1H), 8.36 (s, 1H), 7.93 (d, 1.7 Hz, IH), 7.75-7.68 (m, 2H), 7.65 (s, 1H), 7.58-7.47 (m, 3H), 7.42 (t, 7.4 Hz, 1H), 7.09 (ddd, 12.2, 6.8, 3.1 Hz, 2H), 6.72 (s, 1H), 6.42 (s, 1H), 6.22 (s, 1H). | 527 | E | |
| I-562 | 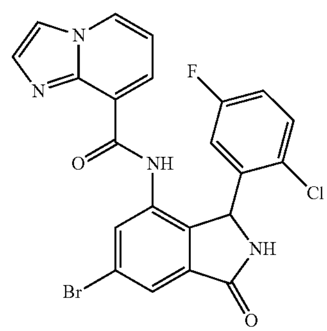 [SMILES: O=C1NC(c2cc(F)ccc2Cl)c2c(NC(=O)c3cccn4ccnc34)cc(Br)cc21] | Fc1ccc(C1)c(c1)C1NC(=O)c2cc(Br)cc(NC(=O)c3cccn4ccnc34)c12 | 1H NMR (400 MHz, DMSO-d6) 11.99 (s, 1H), 9.41 (s, 1H), 8.83-8.77 (m, 2H), 8.12-8.05 (m, 2H), 7.73 (d, 1.8 Hz, 1H), 7.53 (s, 2H), 7.13 (t, 7.0 Hz, 1H), 7.12 (s, 1H), 6.54 (s, 1H), 6.19 (s, 1H). | 499 | E | |
| I-563 | 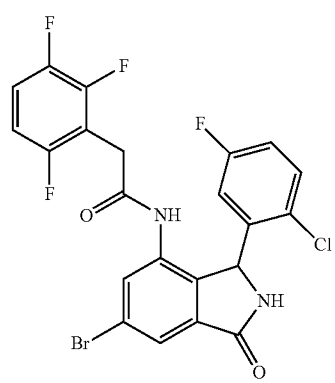 [SMILES: O=C(Cc1c(F)ccc(F)c1F)Nc1cc(Br)cc2c1C(c1cc(F)ccc1Cl)NC2=O] | Fc1ccc(C1)c(c1)C1NC(=O)c2cc(Br)cc(NC(=O)Cc3c(F)ccc(F)c3F)c12 | 1H NMR (400 MHz, Methanol-d4) 7.90 (d, 1.7 Hz, 1H), 7.68 (d, 1.6 Hz, 1H), 7.48-7.40 (m, 1H), 7.25 (qd, 9.4, 5.1 Hz, 1H), 7.13 (ddd, 8.9, 7.8, 3.1 Hz, 1H), 6.96 (ddt, 9.6, 6.6, 3.4 Hz, 1H), 6.14 (s, 1H), 3.64-3.51 (m, 2H). | 527 | E | |
| I-564 | 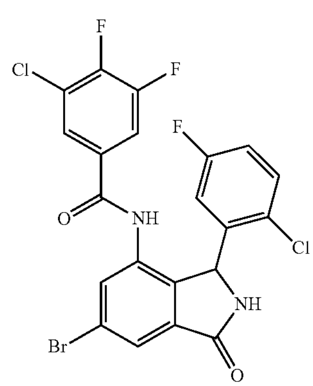 [SMILES: O=C(Nc1cc(Br)cc2c1C(c1cc(F)ccc1Cl)NC2=O)c1cc(F)c(F)c(Cl)c1] | Fc1ccc(C1)c(c1)C1NC(=O)c2cc(Br)cc(NC(=O)c3cc(F)c(F)c(Cl)c3)c12 | 1H NMR (400 MHz, Methanol-d4) 7.96 (d, 1.7 Hz, 2H), 7.73 (s, 2H), 7.58-7.47 (m, 4H), 7.34 (dd, 8.9, 5.0 Hz, 2H), 7.06 (ddd, 8.9, 7.7, 3.1 Hz, 2H), 6.65 (s, 3H), 6.14 (s, 2H), 4.63 (s, 2H). | 530.9 | A | |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-565 | 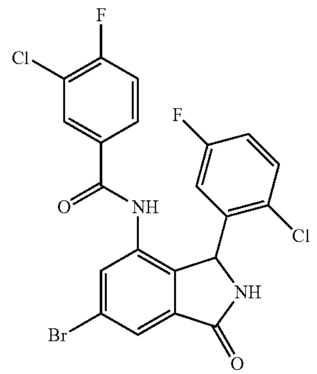 [SMILES: O=C(Nc1cc(Br)cc2c1C(c1cc(F)ccc1Cl)NC2=O)c1ccc(F)c(Cl)c1] | Fc1ccc(C1)c(c1)C1NC(=O)c2cc(Br)cc(NC(=O)c3ccc(F)c(Cl)c3)c12 | 1H NMR (400 MHz, Chloroform-d) 8.45 (s, 1H), 7.94 (d, 1.6 Hz, 1H), 7.55-7.43 (m, 3H), 7.34 (s, 1H), 7.23 (t, 8.4 Hz, 1H), 7.10 (ddd, 8.9, 7.3, 3.0 Hz, 1H), 6.72 (s, 1H), 6.60 (s, 1H), 6.18 (s, 1H). | 510.95 | C | |
| I-566 | 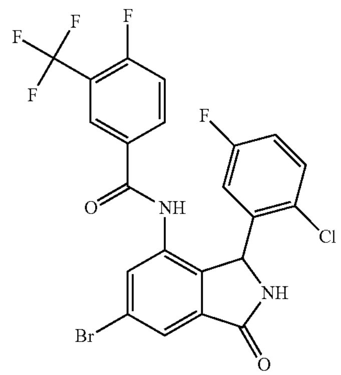 [SMILES: O=C(Nc1cc(Br)cc2c1C(c1cc(F)ccc1Cl)NC2=O)c1ccc(F)c(C(F)(F)F)c1] | Fc1ccc(C1)c(c1)C1NC(=O)c2cc(Br)cc(NC(=O)c3ccc(F)c(c3)C(F)(F)F)c12 | 1H NMR (400 MHz, Chloroform-d) 8.39 (s, 1H), 7.95 (s, 1H), 7.87 (s, 1H), 7.68 (d, 6.3 Hz, 1H), 7.40 (s, 2H), 7.31 (d, 8.8 Hz, 1H), 7.07 (s, 1H), 6.70 (s, 2H), 6.21 (s, 1H). | 545 | C | |
| I-567 | 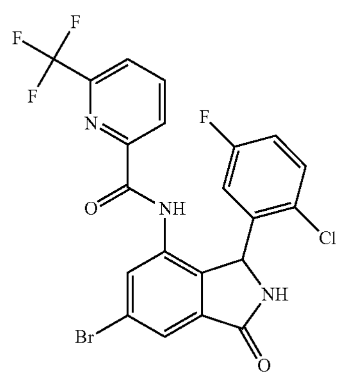 [SMILES: O=C(Nc1cc(Br)cc2c1C(c1cc(F)ccc1Cl)NC2=O)c1cccc(C(F)(F)F)n1] | Fc1ccc(C1)c(c1)C1NC(=O)c2cc(Br)cc(NC(=O)c3cccc(n3)C(F)(F)F)c12 | 1H NMR (400 MHz, Chloroform-d) 9.30 (s, 1H), 8.74 (s, 1H), 8.45 (d, 7.9 Hz, 1H), 8.13 (t, 7.8 Hz, 1H), 7.96 (d, 1.7 Hz, 1H), 7.87 (d, 7.8 Hz, 1H), 7.48 (dd, 8.8, 4.8 Hz, 1H), 7.03 (s, 1H), 6.60 (s, 1H), 6.47 (s, 1H), 6.22 (s, 1H) | 529.9 | D | |
| I-568 | 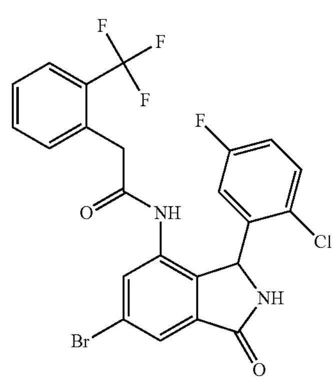 [SMILES: O=C(Cc1ccccc1C(F)(F)F)Nc1cc(Br)cc2c1C(c1cc(F)ccc1Cl)NC2=O] | Fc1ccc(C1)c(c1)C1NC(=O)c2cc(Br)cc(NC(=O)Cc3ccccc3C(F)(F)F)c12 | 1H NMR (400 MHz, DMSO-d6) 10.01 (s, 1H), 9.22 (s, 1H), 7.75-(m, 2H), 7.69-7.59 (m, 1H), 7.59 (d, 7.6 Hz, 1H), 7.47 (t, 7.5 Hz, 2H), 7.30-7.21 (m, 2H), 7.23-6.08 (m, 1H), 5.98 (s, 1H), 3.65-3.49 (m, 2H). | 541.05 | D | |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-569 | 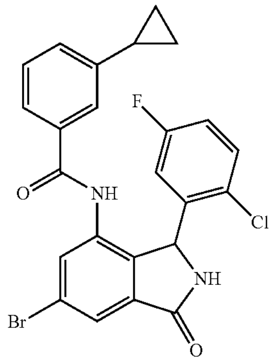 [SMILES: O=C(Nc1cc(Br)cc2c1C(c1cc(F)ccc1Cl)NC2=O)c1cccc(C2CC2)c1] | Fc1ccc(C1)c(c1)C1NC(=O)c2cc(Br)cc(NC(=O)c3cccc(c3)C3CC3)c12 | 1H NMR (400 MHz, DMSO-d6) 10.16 (s, 1H), 9.27 (s, 1H), 7.82-7.73 (m, 2H), 7.37 (dd, 8.9, 5.2 Hz, 1H), 7.36-7.26 (m, 2H), 7.28 (s, 1H), 7.18-7.08 (m, 2H), 6.78 (s, 1H), 6.04 (s, 1H), 1.98-1.87 (m, 1H), 0.99 (dq, 8.3, 1.5 Hz, 2H), 0.73-0.60 (m, 2H). | 499.05 | D | |
| I-570 | 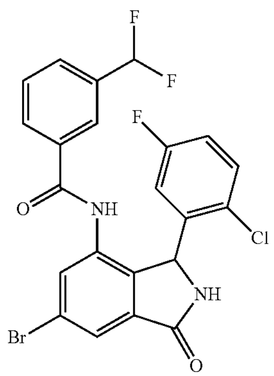 [SMILES: O=C(Nc1cc(Br)cc2c1C(c1cc(F)ccc1Cl)NC2=O)c1cccc(C(F)F)c1] | FC(F)c1cccc(c1)C(=O)Nc1cc(Br)cc2C(=O)NC(c12)c1cc(F)ccc1Cl | 1H NMR (400 MHz, DMSO-d6) 10.42 (s, 1H), 9.28 (s, 1H), 7.80 (d, 1.7 Hz, 1H), 7.78-7.69 (m, 4H), 7.60 (t, 7.8 Hz, 1H), 7.33 (dd, 8.8, 5.1 Hz, 1H), 7.15-7.05 (m, 2H), 6.71 (s, 1H), 6.02 (s, 1H). | 509 | D | |
| I-571 | 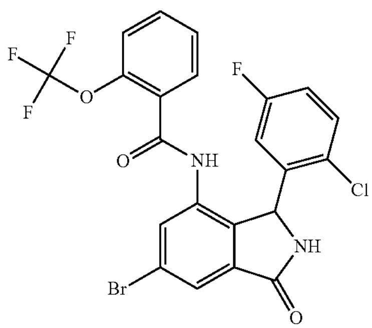 [SMILES: O=C(Nc1cc(Br)cc2c1C(c1cc(F)ccc1Cl)NC2=O)c1ccccc1OC(F)(F)F] | Fc1ccc(C1)c(c1)C1NC(=O)c2cc(Br)cc(NC(=O)c3ccccc3OC(F)(F)F)c12 | 1H NMR (400 MHz, DMSO-d6) 10.40 (s, 1H), 9.29 (s, 1H), 7.79 (d, 1.7 Hz, 1H), 7.69 (d, 1.9 Hz, 1H), 7.67-7.59 (m, 1H), 7.48 (t, 8.4 Hz, 2H), 7.39 (td, 7.6, 1.1 Hz, 1H), 7.27 (td, 8.4, 3.1 Hz, 1H), 6.83 (dt, 7.7, 2.2 Hz, 2H), 6.05 (s, 1H). | 542.92 | D | |
| I-572 | 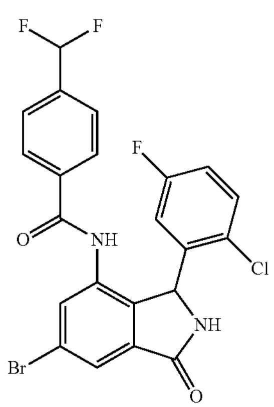 [SMILES: O=C(Nc1cc(Br)cc2c1C(c1cc(F)ccc1Cl)NC2=O)c1ccc(C(F)F)cc1] | FC(F)c1ccc(cc1)C(=O)Nc1cc(Br)cc2C(=O)NC(c12)c1cc(F)ccc1Cl | 1H NMR (400 MHz, Chloroform-d) 7.96 (d, 1.7 Hz, 1H), 6.72 (t, 56.1 Hz, 2H), 8.46 (s, 1H), 7.60 (s, 4H), 7.41 (dd, 8.1, 4.3 Hz, 2H), 7.12-7.03 (m, 1H), 6.45 (s, 1H), 6.20 (s, 1H) | 509 | D | |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-573 | 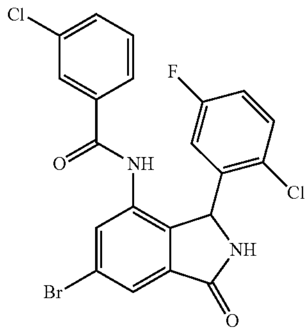 [SMILES: O=C(Nc1cc(Br)cc2c1C(c1cc(F)ccc1Cl)NC2=O)c1cccc(Cl)c1] | Fc1ccc(C1)c(c1)C1NC(=O)c2cc(Br)cc(NC(=O)c3cccc(C1)c3)c12 | 1H NMR (400 MHz, DMSO-d6) 10.36 (s, 1H), 9.29 (s, 1H), 7.80 (d, 1.8 Hz, 1H), 7.74 (d, 1.8 Hz, 1H), 7.64 (dt, 7.8, 1.6 Hz, 1H), 7.55 (dt, 7.9, 1.5 Hz, 1H), 7.52-7.45 (m, 2H), 7.36 (dd, 8.9, 5.2 Hz, 1H), 7.14 (td, 8.4, 3.1 Hz, 1H), 7.11-6.25 (br, 1H), 6.00 (s, 1H). | 492.85 | C | |
| I-574 | 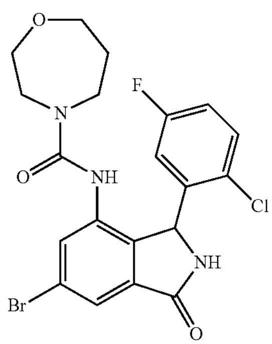 [SMILES: O=C1NC(c2cc(F)ccc2Cl)c2c(NC(=O)N3CCCOCC3)cc(Br)cc21] | Fc1ccc(C1)c(c1)C1NC(=O)c2cc(Br)cc(NC(=O)N3CCCOCC3)c12 | (400 MHz, CDCl3) 8.14 (s, 1H), 7.81 (dd, 1.6, 0.4 Hz, 1H), 7.45 (dd, 8.9, 4.9 Hz, 1H), 7.06 (ddd, 8.9, 7.4, 3.0 Hz 1H), 6.62 (br s, 1H), 6.45 (dd, 20.1, 8.5 Hz, 1H), 6.11 (s, 1H), 5.89 (s, 1H), 3.69-3.52 (m, 4H), 3.44-3.36 (m, 2H), 3.32 (t, 5.2 Hz, 2H), 1.83-1.67 (m, 2H) | 482.2 | E | |
| I-575 | 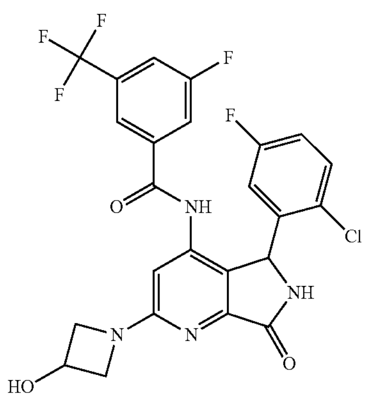 [SMILES: O=C(Nc1cc(N2CC(O)C2)nc2c1C(c1cc(F)ccc1Cl)NC2=O)c1cc(F)cc(C(F)(F)F)c1] | OC1CN(C1)c1cc(NC(=O)c2cc(F)cc(c2)C(F)(F)F)c2C(NC(=O)c2n1)c1cc(F)ccc1C1 | 1H NMR (400 MHz, DMSO-d6) 10.68 (br s, 1H), 9.16 (s, 1H), 8.45 (s, 1H), 7.88 (s, 1H), 7.72 (d, 9.2 Hz, 1H), 7.66 (s, 1H), 7.33 (dd, 8.8, 5.2 Hz, 1H), 7.07 (td, 8.5, 2.9 Hz, 1H), 6.60 (br s, 1H), 5.86 (s, 1H), 5.65 (br s, 1H), 4.69-4.58 (m, 1H), 4.23 (dd, 15.5, 8.3 Hz, 2H), 3.77-3074 (m, 2H). | 539.5 | A | |
| I-576 | 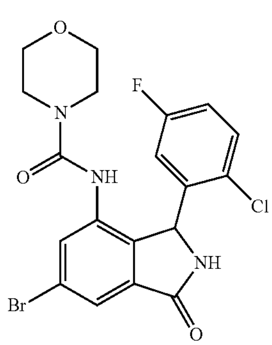 [SMILES: O=C1NC(c2cc(F)ccc2Cl)c2c(NC(=O)N3CCOCC3)cc(Br)cc21] | Fc1ccc(C1)c(c1)C1NC(=O)c2cc(Br)cc(NC(=O)N3CCOCC3)c12 | NMR (400 MHz, CD3CN) 7.70 (d, 1.7 Hz, 1H), 7.52 (d, 1.6 Hz, 1H), 7.46 (dd, 7.8, 5.5 Hz, 1H), 7.24 (s, 1H), 7.11 (ddd, 8.9, 8.0, 3.1 Hz, 1H), 7.00 (s 1H), 6.69 (br s, 1H), 6.08 (s, 1H), 3.48 (ddd, 11.3, 6.5, 3.2 Hz, 2H), 3.42-3.34 (m, 2H), 3.19 (ddd, 13.1, 6.5, 3.3 Hz, 2H), 2.99 (ddd, 13.2, 6.5, 3.2 Hz, 2H). | 466.3 | E | |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-577 | 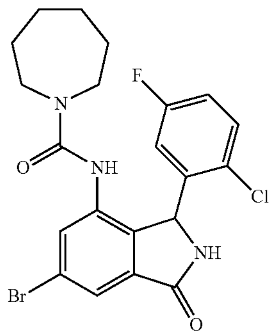 [SMILES: O=C1NC(c2cc(F)ccc2Cl)c2c(NC(=O)N3CCCCCC3)cc(Br)cc21] | Fc1ccc(C1)c(c1)C1NC(=O)c2cc(Br)cc(NC(=O)N3CCCCCC3)c12 | NMR (400 MHz, CD3CN) 7.68 (s, 2H), 7.44 (dd, 8.9, 5.2 Hz, 1H), 7.23 (s, 1H), 7.09 (ddd, 8.8, 8.0, 3.1 Hz, 1H), 6.74 (s, 1H), 6.64 (br s, 1H), 6.16 (s, 1H), 3.33-2.98 (m, 4H), 1.54-1.44 (m, 4H), 1.43-1.36 (m, 2H), 1.33-1.22 (m, 2H). | 480.2 | E | |
| I-578 | 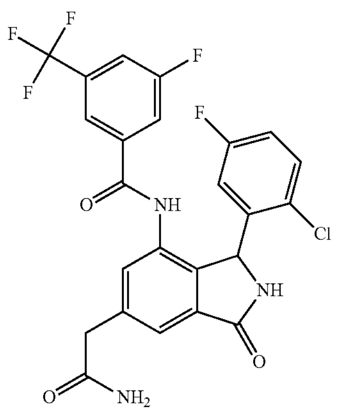 [SMILES: NC(=O)Cc1cc(NC(=O)c2cc(F)cc(C(F)(F)F)c2)c2c(c1)C(=O)NC2c1cc(F)ccc1Cl] | NC(=O)Cc1cc2C(=O)NC(c2c(NC(=O)c2cc(F)cc(c2)C(F)(F)F)c1)c1cc(F)ccc1C1 | 1H-NMR (400 MHz, DMSO-d6) 10.52 (s, 1H), 9.12 (br. s, 1H), 7.94 (d, 8.5 Hz, 1H), 7.73 (d, 9.0 Hz., 1H), 7.65 (s, 1H), 7.61 (s, 2H), 7.38 (s, 1H), 7.31 (dd, 8.9, 5.2 Hz, 1H), 7.09 (td, 8.4, 3.0 Hz, 1H), 7.01 (br. s, 1H), 6.59 (br. s, 1H), 5.95 (br. s, 1H), 3.62-3.51 (m, 2H). | 524.2 | A | |
| I-579 | 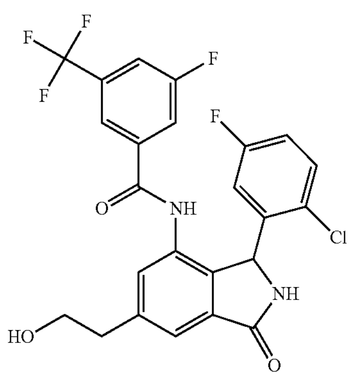 [SMILES: O=C(Nc1cc(CCO)cc2c1C(c1cc(F)ccc1Cl)NC2=O)c1cc(F)cc(C(F)(F)F)c1] | OCCc1cc2C(=O)NC(c2c(NC(=O)c2cc(F)cc(c2)C(F)(F)F)c1)c1cc(F)ccc1C1 | NMR (400 MHz, DMSO-d6) 10.49 (br. s, 1H), 9.09 (br. s, 1H), 7.94 (d, 8.5 Hz, 1H), 7.73 (d, 9.1 Hz, 1H), 7.65 (s, 1H), 7.56 (s, 1H), 7.34 (s, 1H), 7.30 (dd, 8.9, 5.2 Hz, 1H), 7.09 (td, 8.4, 3.1 Hz, 1H), 6.58 (br. s, 1H), 5.94 (br. s, 1H), 4.74 (br. s, 1H), 3.70 (t, 6.4 Hz, 2H), 2.95-2.82 (m, 2H). | 511.2 | A | |
| I-580 | 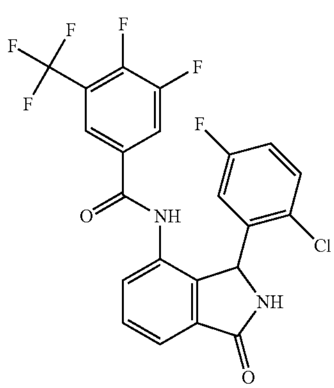 [SMILES: O=C(Nc1cccc2c1C(c1cc(F)ccc1Cl)NC2=O)c1cc(F)c(F)c(C(F)(F)F)c1] | Fc1ccc(C1)c(c1)C1NC(=O)c2cccc(NC(=O)c3cc(F)c(F)c(c3)C(F)(F)F)c12 | | 485.1 | A | |

TABLE 2-continued

Representative Compounds of the Invention with Bioactivity Data.

| Ex. No. | Structure | SMILES | $^1$H NMR | MS | ADP-Glo IC$_{50}$ | MCF 10A IC$_{50}$ |
|---|---|---|---|---|---|---|
| I-581 | 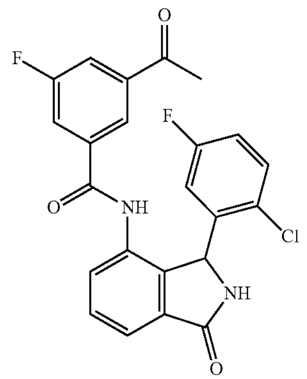 [SMILES: CC(=O)c1cc(F)cc(C(=O)Nc2cccc3c2C(c2cc(F)ccc2Cl)NC3=O)c1] | CC(=O)c1cc(F)cc(c1)C(=O)Nc1cccc2C(=O)NC(c12)c1cc(F)ccc1Cl | | 441.4 | D | |
| I-582 | 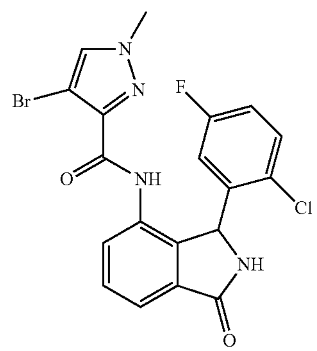 [SMILES: Cn1cc(Br)c(C(=O)Nc2cccc3c2C(c2cc(F)ccc2Cl)NC3=O)n1] | Cn1cc(Br)c(n1)C(=O)Nc1cccc2C(=O)NC(c12)c1cc(F)ccc1Cl | | 463.22 | E | |
| I-583 | 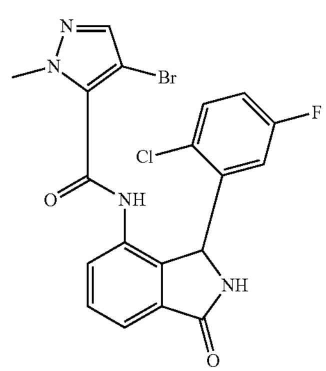 [SMILES: Cn1ncc(Br)c1C(=O)Nc1cccc2c1C(c1cc(F)ccc1Cl)NC2=O] | Cn1ncc(Br)c1C(=O)Nc1cccc2C(=O)NC(c12)c1cc(F)ccc1Cl | | 463.22 | E | |
| I-584 | 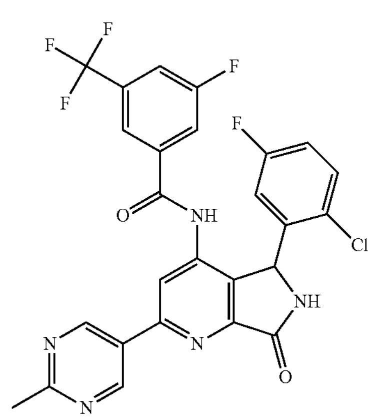 [SMILES: Cc1ncc(-c2cc(NC(=O)c3cc(F)cc(C(F)(F)F)c3)c3c(n2)C(=O)NC3c2cc(F)ccc2Cl)cn1] | Cc1ncc(cn1)-c1cc(NC(=O)c2cc(F)cc(c2)C(F)(F)F)c2C(NC(=O)c2n1)c1cc(F)ccc1Cl | 1H NMR (DMSO-d6, 400 MHz) 11.04 (br s, 1H), 9.63 (br s, 1H), 9.38 (s, 2H), 8.14 (s, 1H), 8.00 (br d, 8.1 Hz, 1H), 7.76 (br d, 8.8 Hz, 1H), 7.67 (s, 1H), 7.35 (dd, 8.9, 5.2 Hz, 1H), 7.10 (td, 8.4, 2.9 Hz, 1H), 6.83-7.02 (m, 1H), 6.08 (br s, 1H), 2.74 (s, 3H) | 560.5 | A | |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-585 | 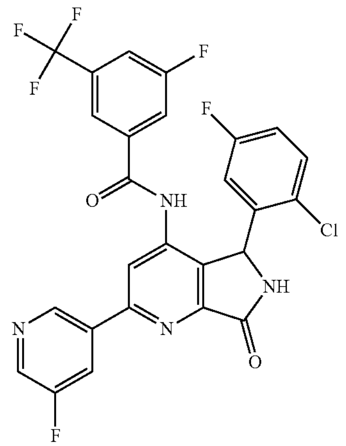 [SMILES: O=C(Nc1cc(-c2cncc(F)c2)nc2c1C(c1cc(F)ccc1Cl)NC2=O)c1cc(F)cc(C(F)(F)F)c1] | Fc1ccc(C1)c(c1)C1NC(=O)c2nc(cc(NC(=O)c3cc(F)cc(c3)C(F)(F)F)c12)-c1cncc(F)c1 | 1H NMR (DMSO-d6, 400 MHz) 11.03 (s, 1H), 9.63 (br s, 1H), 9.21 (s, 1H), 8.74 (br d, 2.4 Hz, 1H), 8.39 (br d, 9.8 Hz, 1H), 8.19 (br s, 1H), 8.00 (br d, 7.6 Hz, 1H), 7.77 (br d, 9.0 Hz, 1H), 7.68 (br s, 1H), 7.36 (br dd, 8.8, 5.1 Hz, 1H), 7.11 (td, 8.4, 3.1 Hz, 1H), 6.83-7.03 (m, 1H), 6.08 (br s, 1H) | 563.5 | A | |
| I-586 | 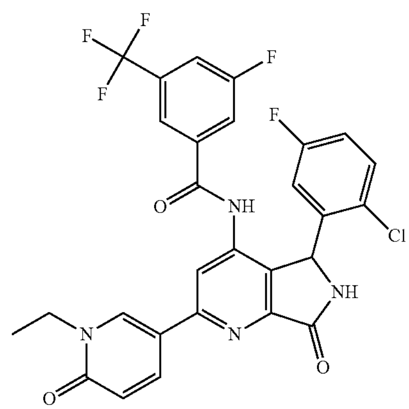 [SMILES: CCn1cc(-c2cc(NC(=O)c3cc(F)cc(C(F)(F)F)c3)c3c(n2)C(=O)NC3c2cc(F)ccc2Cl)ccc1=O] | CCn1cc(ccc1=O)-c1cc(NC(=O)c2cc(F)cc(c2)C(F)(F)F)c2C(NC(=O)c2n1)c1cc(F)ccc1Cl | 1H NMR (DMSO-d6, 400 MHz) 10.91 (s, 1H), 9.52 (br s, 1H), 8.62 (d, 2.2 Hz, 1H), 8.20 (dd, 9.5, 2.4 Hz, 1H), 7.99 (br d, 8.1 Hz, 1H), 7.90 (s, 1H), 7.76 (br d, 9.0 Hz, 1H), 7.68 (s, 1H), 7.34 (dd, 9.0, 5.1 Hz, 1H), 7.10 (td, 8.4, 2.9 Hz, 1H), 6.79-6.98 (m, 1H), 6.57 (d, 9.5 Hz, 1H), 6.02 (br s, 1H), 4.07 (q, 7.1 Hz, 2H), 1.30 (t, 7.1 Hz, 3H) | 589.5 | A | |
| I-587 | 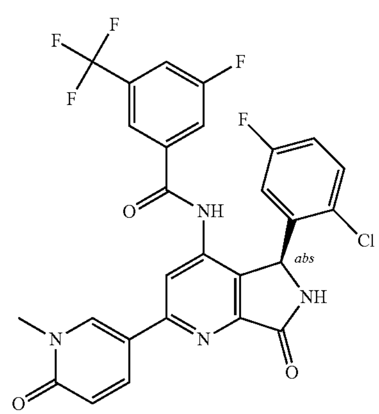 [SMILES: Cn1cc(-c2cc(NC(=O)c3cc(F)cc(C(F)(F)F)c3)c3c(n2)C(=O)N[C@@H]3c2cc(F)ccc2Cl)ccc1=O] | Cn1cc(ccc1=O)-c1cc(NC(=O)c2cc(F)cc(c2)C(F)(F)F)c2[C@H](NC(=O)c2n1)c1cc(F)ccc1Cl | | 575.2 | D | |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-588 | 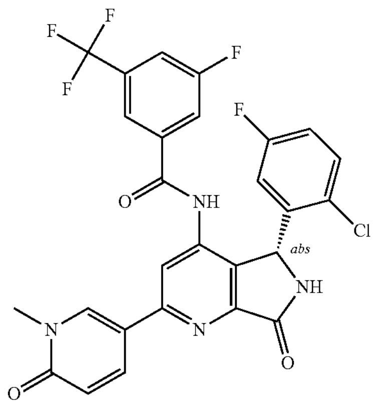 [SMILES: Cn1cc(-c2cc(NC(=O)c3cc(F)cc(C(F)(F)F)c3)c3c(n2)C(=O)N[C@H]3c2cc(F)ccc2Cl)ccc1=O] | Cn1cc(ccc1=O)-c1cc(NC(=O)c2cc(F)cc(c2)C(F)(F)F)c2[C@@H](NC(=O)c2n1)c1cc(F)ccc1Cl | | 575.2 | A | |
| I-589 | 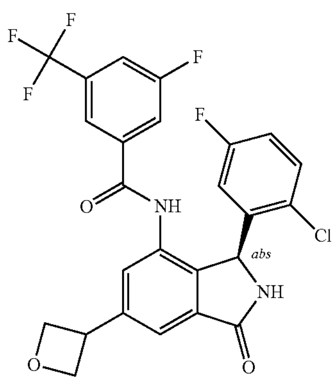 [SMILES: O=C(Nc1cc(C2COC2)cc2c1[C@@H](c1cc(F)ccc1Cl)NC2=O)c1cc(F)cc(C(F)(F)F)c1] | Fc1ccc(C1)c(c1)[C@H]1NC(=O)c2cc(cc(NC(=O)c3cc(F)cc(c3)C(F)(F)F)c12)C1COC1 | | 523.4 | A | |
| I-590 | 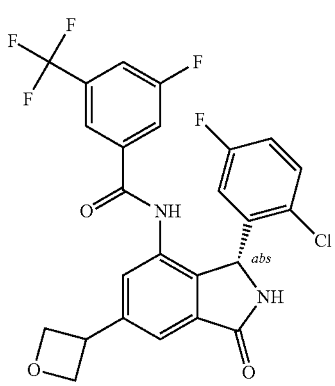 [SMILES: O=C(Nc1cc(C2COC2)cc2c1[C@H](c1cc(F)ccc1Cl)NC2=O)c1cc(F)cc(C(F)(F)F)c1] | Fc1ccc(C1)c(c1)[C@@H]1NC(=O)c2cc(cc(NC(=O)c3cc(F)cc(c3)C(F)(F)F)c12)C1COC1 | | 523.4 | A | |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-591 | 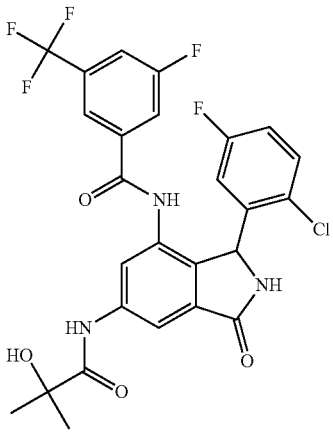 [SMILES: CC(C)(O)C(=O)Nc1cc(NC(=O)c2cc(F)cc(C(F)(F)F)c2)c2c(c1)C(=O)NC2c1cc(F)ccc1Cl] | CC(C)(O)C(=O)Nc1cc2C(=O)NCc(c2c(NC(=O)c2cc(F)cc(c2)C(F)(F)F)c1)c1cc(F)ccc1Cl | | 568.27 | A | |
| I-592 | 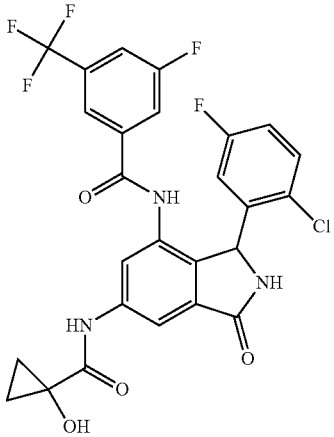 [SMILES: O=C(Nc1cc(NC(=O)C2(O)CC2)cc2c1C(c1cc(F)ccc1Cl)NC2=O)c1cc(F)cc(C(F)(F)F)c1] | OC1(CC1)C(=O)Nc1cc2C(=O)NC(c2c(NC(=O)c2cc(F)cc(c2)C(F)(F)F)c1)c1cc(F)ccc1Cl | | 566.21 | A | |
| I-593 | 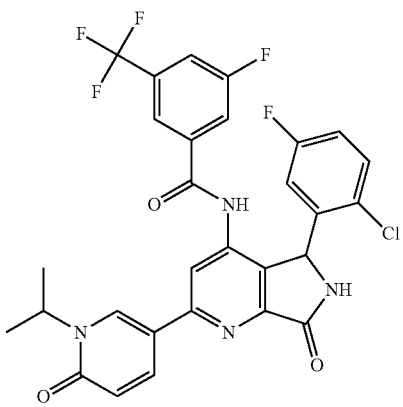 [SMILES: CC(C)n1cc(-c2cc(NC(=O)c3cc(F)cc(C(F)(F)F)c3)c3c(n2)C(=O)NC3c2cc(F)ccc2Cl)ccc1=O] | CC(C)n1cc(ccc1=O)-c1cc(NC(=O)c2cc(F)cc(c2)C(F)(F)F)c2C(NC(=O)c2n1)c1cc(F)ccc1Cl | 1H NMR (DMSO-d6, 400 MHz) 10.94 (br s, 1H), 9.51 (br s, 1H), 8.48 (br d, 2.2 Hz, 1H), 8.20 (br dd, 9.6, 2.3 Hz, 1H), 7.98 (br s, 2H), 7.76 (br d, 8.8 Hz, 1H), 7.69 (s, 1H), 7.34 (dd, 8.9, 5.2 Hz, 1H), 7.09 (td, 8.4, 2.9 Hz, 1H), 6.77-6.96 (m, 1H), 6.58 (d, 9.5 Hz, 1H), 6.01 (br s, 1H), 5.13 (dt, 13.6, 6.7 Hz, 1H), 1.41 (dd, 6.6, 4.9 Hz, 6H) | 603.6 | A | |

TABLE 2-continued

Representative Compounds of the Invention with Bioactivity Data.

| Ex. No. | Structure | SMILES | $^1$H NMR | MS | ADP-Glo IC$_{50}$ | MCF 10A IC$_{50}$ |
|---|---|---|---|---|---|---|
| I-594 | 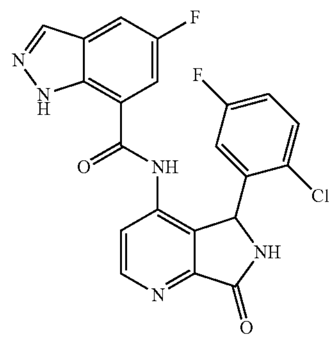 [SMILES: O=C1NC(c2cc(F)ccc2Cl)c2c(NC(=O)c3cc(F)cc4cn[nH]c34)ccnc21] | Fc1ccc(C1)c(c1)C1NC(=O)c2cccc(NC(=O)c3cc(F)cc4cn[nH]c34)c12 | | 439.33 | C | |
| I-595 | 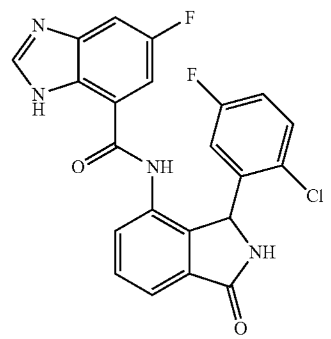 [SMILES: O=C1NC(c2cc(F)ccc2Cl)c2c(NC(=O)c3cc(F)cc4nc[nH]c34)cccc21] | Fc1ccc(C1)c(c1)C1NC(=O)c2cccc(NC(=O)c3cc(F)cc4nc[nH]c34)c12 | | 439.38 | D | |
| I-596 | 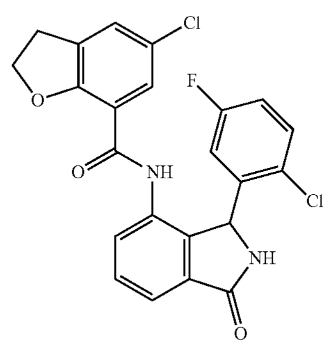 [SMILES: O=C(Nc1cccc2c1C(c1cc(F)ccc1Cl)NC2=O)c1cc(Cl)cc2c1OCC2] | Fc1ccc(C1)c(c1)C1NC(=O)c2cccc(NC(=O)c3cc(Cl)cc4CCOc34)c12 | | 457.4 | D | |
| I-597 | 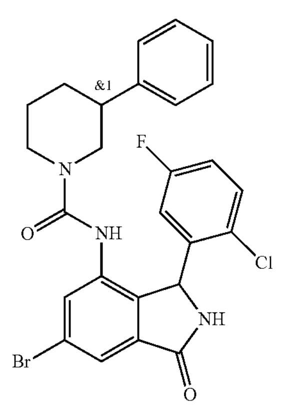 [SMILES: O=C1NC(c2cc(F)ccc2Cl)c2c(NC(=O)N3CCCC(c4ccccc4)C3)cc(Br)cc21] | Fc1ccc(C1)c(c1)C1NC(=O)c2cc(Br)cc(NC(=O)N3CCCC(C3)c3ccccc3)c12 | (400 MHz, DMSO-d6) 9.19 (s, 1H), 8.71 (s, 0.5H), 8.67 (s, 0.5H), 7.61-7.57 (m, 1H), 7.56-7.50 (m, 1H), 7.47 (d, 1.6 Hz, 0.5H), 7.46 (d, 1.6 Hz, 0.5H) 7.38-7.28 (m, 3H), 7.28-7.19 (m, 3H), 7.12 (d, 7.1 Hz, 1H), 6.60 (br s, 1H), 6.07 (br s, 1H), 3.96 (d, 12.1 Hz, 0.5H), 3.86 (d, 7.6 Hz, 0.5H), 3.76 (t, 14.4 Hz, 1H), 2.75-2.57 (m, 1H), 2.48-2.40 (m, 1H), 1.99-1.82 (m, 0.5H), 1.82-1.68 (m, 1H), 1.68-1.43 (m, 2H), 1.43-1.27 (m, 0.5H) | 542.3 | D | |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-598 | 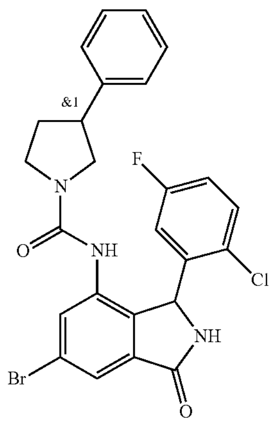 [SMILES: O=C1NC(c2cc(F)ccc2Cl)c2c(NC(=O)N3CCC(c4ccccc4)C3)cc(Br)cc21] | Fc1ccc(C 1)c(c1)C1 NC(=O)c 2cc(Br)cc (NC(=O) N3CCC (C3)c3ccc cc3)c12 | (400 MHz, DMSO-d6) 9.15 (s, 1H), 8.28 (s, 0.5H), 8.19 (s, 0.5H), 7.56 (dd, 2.7, 1.8 Hz, 1H), 7.51 (d, (t, 1.7 Hz, 1H), 7.46 (d, (1, 1.7 Hz, 1H), 7.31 (1, 7.7 Hz, 2H), 7.28-7.13 (m, 5H), 5.94 (br s, 1H), 3.79-3.57 (m, 0.5H), 3.56-3.37 (m, 1H), 3.25-3.11 (m, 2.5H), 3.10-2.99 (m, 1H), 2.17-2.04 (m, 1H), 1.89-1.65 (m, 1H) | 528.3 | D | |
| I-599 | 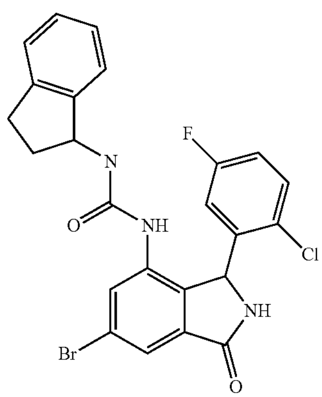 [SMILES: O=C(Nc1cc(Br)cc2c1C(c1cc(F)ccc1Cl)NC2=O)NC1CCc2ccccc21] | Fc1ccc(C 1)c(c1)C1 NC(=O)c 2cc(Br)cc (NC(=O) CC3CCc 4cccc34) c12 | 1H NMR (400 MHz, Chloroform-d) 8.46 (s, 1H), 7.89 (t, 1.9 Hz, 1H), 7.42 (ddd, 22.3, 8.9, 4.9 Hz, 1H), 7.26 (d, 8.7 Hz, 1H), 7.22 (d, 6.6 Hz, 1H), 7.19-6.97 (m, 3H), 6.88 (s, 1H), 6.66 (dd, 8.5, 3.0 Hz, 1H), 6.42 (d, 5.1 Hz, 1H), 6.06 (s, 1H), 3.59-3.51 (m, 1H), 2.72-2.57 (m, 2H), 2.40-2.30 (m, 1H), 2.34-2.23 (m, 2H), 1.69 (dt, 13.3, 7.4 Hz, 1H). | 515 | E | |
| I-600 | 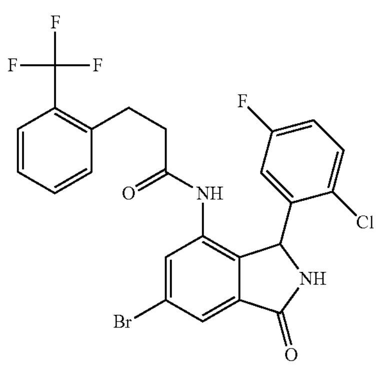 [SMILES: O=C(CCc1ccccc1C(F)(F)F)Nc1cc(Br)cc2c1C(c1cc(F)ccc1Cl)NC2=O] | Fc1ccc(C 1)c(c1)C1 NC(=O)c 2cc(Br)cc (NC(=O) CCc3ccc cc3C(F) (F)F)c12 | 1H NMR (400 MHz, DMSO-d6) 9.87 (s, 1H), 9.25 (s, 1H), 7.75-7.57 (m, 4H), 7.44 (q, 7.7 Hz, 2H), 7.37 (d, 7.7 Hz, 1H), 7.22 (ddd, 8.9, 7.9, 3.1 Hz, 1H), 6.71 (s, 1H), 6.00 (s, 1H), 2.81 (dd, 20.3, 10.4 Hz, 2H), 2.34-2.19 (m, 2H). | 555 | D | |
| I-601 | 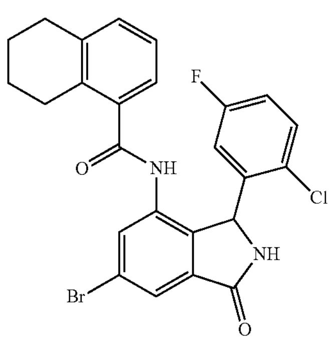 [SMILES: O=C(Nc1cc(Br)cc2c1C(c1cc(F)ccc1Cl)NC2=O)c1cccc2c1CCCC2] | Fc1ccc(C 1)c(c1)C1 NC(=O)c 2cc(Br)cc (NC(=O) c3cccc4C CCOc34) c12 | 1H NMR (400 MHz, DMSO-d6) 9.73 (s, 1H), 9.27 (s, 1H), 7.89 (d, 16.6 Hz, 1H), 7.74 (d, 1.8 Hz, 1H), 7.44 (s, 1H), 7.27-7.15 (m, 3H), 6.85 (t, 7.6 Hz, 2H), 6.11 (s, 1H), 4.18-4.10 (m, 1H), 4.04 (dt, 10.6, 5.2 Hz, 1H), 2.76 (t, 6.5 Hz, 2H), 1.90 (q, 5.9 Hz, 2H). | 515.05 | E | |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-602 | 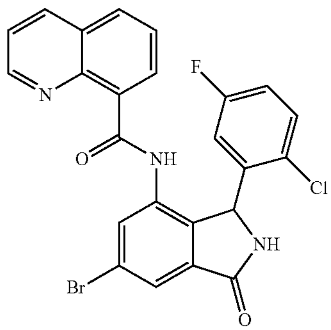 [SMILES: O=C1NC(c2cc(F)ccc2Cl)c2c(NC(=O)c3cccc4cccnc34)cc(Br)cc21] | Fc1ccc(C1)c(c1)C1NC(=O)c2cc(Br)cc(NC(=O)c3cccc4cccnc34)c12 | 1H NMR (400 MHz, DMSO-d6) 12.91 (s, 1H), 9.34 (s, 1H), 8.93 (s, 1H), 8.58 (ddd, 14.9, 7.9, 1.7 Hz, 2H), 8.39 (s, 1H), 8.26 (dd, 8.1, 1.6 Hz, 1H), 7.82-7.68 (m, 3H), 7.29 (dd, 8.8, 5.1 Hz, 1H), 6.98 (d, 8.9 Hz, 1H), 6.80 (s, 1H), 6.26 (s, 1H). | 510 | D | |
| I-603 | 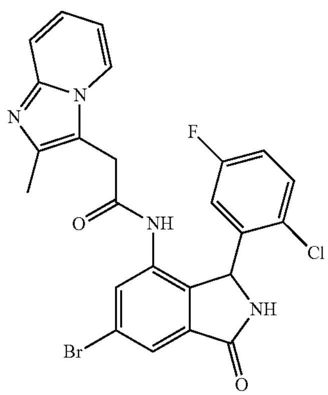 [SMILES: Cc1nc2ccccn2c1CC(=O)Nc1cc(Br)cc2c1C(c1cc(F)ccc1Cl)NC2=O] | Cc1nc2ccccn2c1CC(=O)Nc1cc(Br)cc2C(=O)NC(c12)c1cc(F)ccc1C1 | 1H NMR (400 MHz, DMSO-d6) 10.12 (s, 1H), 9.21 (s, 1H), 8.06 (d, 6.9 Hz, 1H), 7.71 (dd, 13.5, 1.8 Hz, 2H), 7.44 (d, 9.0 Hz, 1H), 7.34 (dd, 8.8, 5.1 Hz, 1H), 7.23-7.14 (m, 1H), 7.15 (s, 1H), 6.83 (td, 6.8, 1.2 Hz, 1H), 6.54 (s, 1H), 5.98 (s, 1H), 3.72 (s, 2H), 2.17 (s, 3H). | 527 | E | |
| I-604 | 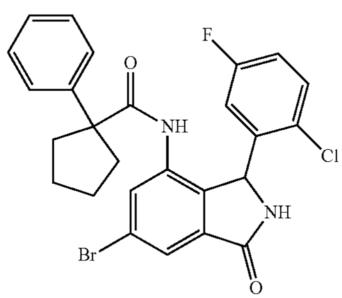 [SMILES: O=C1NC(c2cc(F)ccc2Cl)c2c(NC(=O)C3(c4ccccc4)CCCC3)cc(Br)cc21] | Fc1ccc(C1)c(c1)C1NC(=O)c2cc(Br)cc(NC(=O)C3(CCCC3)c3ccccc3)c12 | 1H NMR (400 MHz, DMSO-d6) 9.23 (s, 1H), 9.16 (s, 1H), 7.69 (d, 1.8 Hz, 1H), 7.53 (d, 1.8 Hz, 2H), 7.30-7.13 (m, 6H), 6.17 (s, 1H), 2.14 (s, 2H), 1.89 (d, 23.1 Hz, 1H), 1.68 (dt, 13.1, 7.1 Hz, 1H), 1.48 (s, 2H), 1.26 (s, 2H). | 527.05 | D | |
| I-605 | 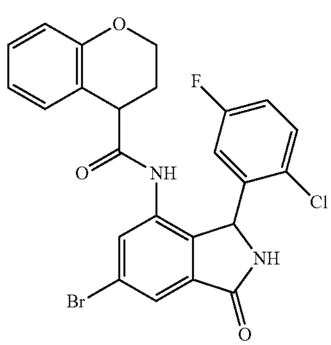 [SMILES: O=C1NC(c2cc(F)ccc2Cl)c2c(NC(=O)C3CCOc4ccccc43)cc(Br)cc21] | Fc1ccc(C1)c(c1)C1NC(=O)c2cc(Br)cc(NC(=O)C3CCOc4ccccc34)c12 | 1H NMR (400 MHz, DMSO-d6) 10.21-10.11 (m, 1H), 9.26 (d, 15.1 Hz, 1H), 7.82-7.69 (m, 2H), 7.60 (s, 1H), 7.46-7.33 (m, 1H), 7.21-7.05 (m, 1H), 6.78-6.67 (m, 3H), 6.56 (s, 1H), 6.08 (s, 1H), 4.23-3.97 (m, 2H), 3.65-3.58 (m, 1H), 1.86-1.79 (m, 1H), 1.71-1.63 (m, 1H). | 515 | E | |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-606 | 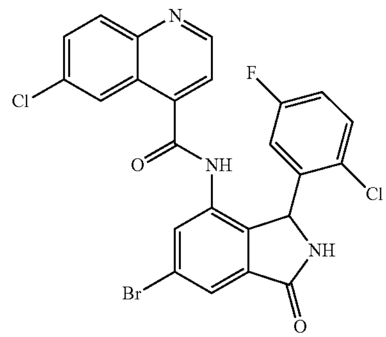 [SMILES: O=C1NC(c2cc(F)ccc2Cl)c2c(NC(=O)c3ccnc4ccc(Cl)cc34)cc(Br)cc21] | Fc1ccc(C1)c(c1)C1NC(=O)c2cc(Br)cc(NC(=O)c3ccnc4ccc(Cl)cc34)c12 | 1H NMR (400 MHz, DMSO-d6) 10.30 (s, 1H), 9.34 (s, 1H), 8.99 (d, 4.3 Hz, 1H), 8.13 (d, 9.0 Hz, 1H), 7.92 (d, 2.3 Hz, 1H), 7.86 (ddd, 8.3, 3.4, 2.0 Hz, 3H), 7.49 (dd, 8.9, 5.1 Hz, 1H), 7.24 (td, 8.4, 3.1 Hz, 1H), 7.14 (s, 1H), 6.70 (s, 1H), 6.13 (s, 1H). | 543.95 | E | |
| I-607 | 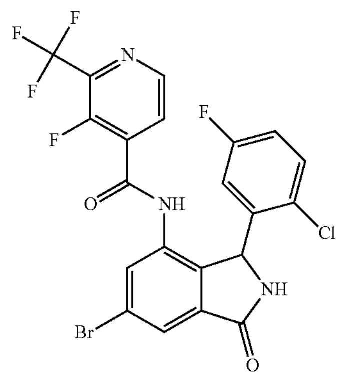 [SMILES: O=C(Nc1cc(Br)cc2c1C(c1cc(F)ccc1Cl)NC2=O)c1ccnc(C(F)(F)F)c1F] | Fc1ccc(C1)c(c1)C1NC(=O)c2cc(Br)cc(NC(=O)c3ccnc(c3F)C(F)(F)F)c12 | 1H NMR (400 MHz, Chloroform-d) 8.70 (d, 4.8 Hz, 1H), 8.45-8.40 (m, 1H), 8.10 (t, 5.0 Hz, 1H), 7.98 (d, 1.6 Hz, 1H), 7.86 (d, 11.0 Hz, 1H), 7.42 (dd, 8.9, 4.9 Hz, 1H), 7.08 (ddd, 8.9, 7.4, 3.0 Hz, 1H), 6.94 (s, 1H), 6.65 (s, 1H), 6.17 (s, 1H). | 545.95 | E | |
| I-608 | 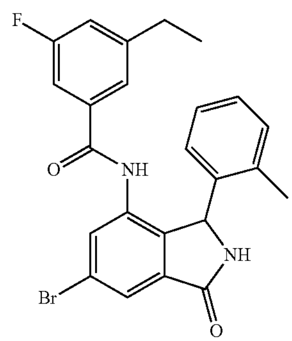 [SMILES: CCc1cc(F)cc(C(=O)Nc2cc(Br)cc3c2C(c2ccccc2C)NC3=O)c1] | CCc1cc(F)cc(c1)C(=O)Nc1cc(Br)cc2C(=O)NC(c12)c1ccccc1C | NMR (400 MHz, DMSO-d6) 10.12 (br. s, 1H), 9.23 (s, 1H), 7.85 (d, 1.7 Hz, 1H), 7.76 (d, 1.7 Hz, 1H), 7.25-7.21 (m, 1H), 7.12 (td, 7.6, 1.2 Hz, 1H), 7.07-7.06 (m, 1H), 6.99 (td, 7.6, 1.2 Hz, 1H), 6.91-6.88 (m, 2H), 6.58 (br. s, 1H), 5.96 (s, 1H), 2.58 (q, 7.5 Hz, 2H), 2.26 (br. s, 3H), 1.15 (t, 7.6 Hz, 3H), traces of impurities at 3.63, 1.99, 1.22, 0.86. | 465.3 | C | |
| I-609 | 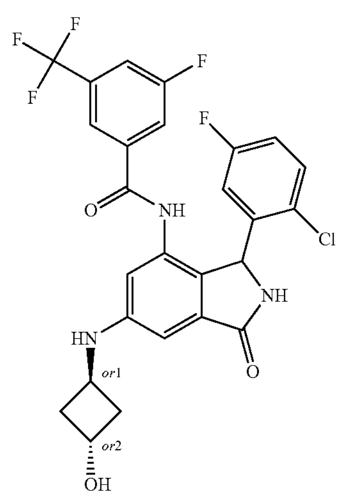 [SMILES: O=C(Nc1cc(N[C@H]2C[C@H](O)C2)cc2c1C(c1cc(F)ccc1Cl)NC2=O)c1cc(F)cc(C(F)(F)F)c1] | O[C@H]1C[C@@H](C1)Nc1cc2C(=O)NC(c2c(NC(=O)c2cc(F)cc(c2)C(F)(F)F)c1)c1cc(F)ccc1Cl | NMR (400 MHz, DMSO-d6) 10.25 (br. s, 1H), 8.88 (br. s, 1H), 8.43 (br. s, 1H), 7.88 (d, 8.4 Hz, 1H), 7.65 (d, 8.6 Hz, 1H), 7.56 (s, 1H), 7.24 (dd, 8.9, 5.2 Hz, 1H), 7.02 (td, 8.5, 2.4 Hz, 1H), 6.63 (d, 1.9 Hz, 1H), 6.54 (s, 1H), 6.44 (d, 5.1 Hz, 1H), 5.79 (br. s, 1H), 5.07 (br. s, 1H), 4.37-4.20 (m, 1H), 3.84 (ddd, 11.5, 7.6, 4.3 Hz, 1H), 2.24-2.01 (m, 3H). | 552.2 | A | |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-610 | 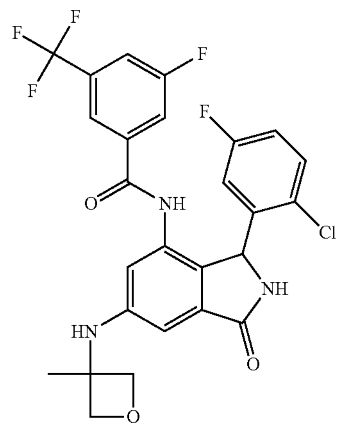 [SMILES: CC1(Nc2cc(NC(=O)c3cc(F)cc(C(F)(F)F)c3)c3c(c2)C(=O)NC3c2cc(F)ccc2Cl)COC1] | CC1(COC1)Nc1cc2C(=O)NC(c2c(NC(=O)c2cc(F)cc(c2)C(F)(F)F)c1)c1cc(F)ccc1Cl | NMR (400 MHz, DMSO-d6) 10.24 (s, 1H), 8.91 (br. s, 1H), 7.88 (td, 8.4, 1.6 Hz, 1H), 7.64 (d, 9.0 Hz, 1H), 7.55 (s, 1H), 7.25 (dd, 8.9, 5.2 Hz, 1H), 7.03 (td, 8.4, 3.1 Hz, 1H), 6.64 (s, 1H), 6.57 (br. s, 1.6 Hz, 1H), 6.52 (d, 2.1 Hz, 1H), 6.47 (br. d, 1H), 5.80 (s, 1H), 4.63 (d, 5.7 Hz, 2H), 4.48 (d, 5.8 Hz, 2H), 1.57 (s, 3H). 6% as formate salt at 8.32 | 552.2 | A | |
| I-611 | 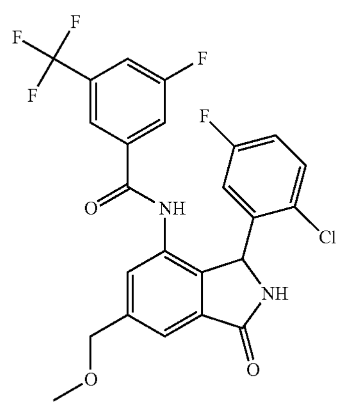 [SMILES: COCc1cc(NC(=O)c2cc(F)cc(C(F)(F)F)c2)c2c(c1)C(=O)NC2c1cc(F)ccc1Cl] | COCc1cc2C(=O)NC(c2c(NC(=O)c2cc(F)cc(c2)C(F)(F)F)c1)c1cc(F)ccc1Cl | NMR (400 MHz, ACN) 8.61 (s, 1H), 7.69 (s, 1H), 7.65 (d, 8.5 Hz, 1H), 7.61-7.55 (m, 2H), 7.53 (s, 1H), 7.25 (dd, 8.9, 5.1 Hz, 1H), 7.22 (br s, 1H), 6.97 (ddd, 8.8, 8.0, 3.1 Hz, 1H), 6.64 (br s, 1H), 6.11 (br s, 1H), 4.59 (s, 2H), 3.41 (s, 3H) | 511.1 | A | |
| I-612 | 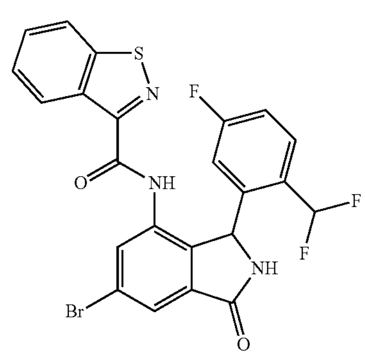 [SMILES: O=C1NC(c2cc(F)ccc2C(F)F)c2c(NC(=O)c3nsc4ccccc34)cc(Br)cc21] | FC(F)c1ccc(F)cc1C1NC(=O)c2cc(Br)cc(NC(=O)c3nsc4ccccc34)c12 | NMR (400 MHz, DMSO) 10.31 (br s, 1H), 9.38 (s, 1H), 8.60 (d, 8.2 Hz, 1H), 8.31 (dt, 8.3, 0.9 Hz, 1H), 8.01 (d, 1.7 Hz, 1H), 7.83 (d, 1.7 Hz, 1H), 7.67 (ddd, 8.2, 7.0, 1.2 Hz, 1H), 7.59 (ddd, 8.1, 7.0, 1.0 Hz, 1H), 7.42 (dd, 8.6, 5.7 Hz, 1H), 7.11 (td, 8.5, 2.6 Hz, 1H), 6.63 (br s, 1H), 6.16 (s, 1H). contains 9% formate salt (8.34) and residual acetone from NMR tube (2.05). | 532.1 | A | |

TABLE 2-continued

Representative Compounds of the Invention with Bioactivity Data.

| Ex. No. | Structure | SMILES | $^1$H NMR | MS | ADP-Glo IC$_{50}$ | MCF 10A IC$_{50}$ |
|---|---|---|---|---|---|---|
| I-613 | 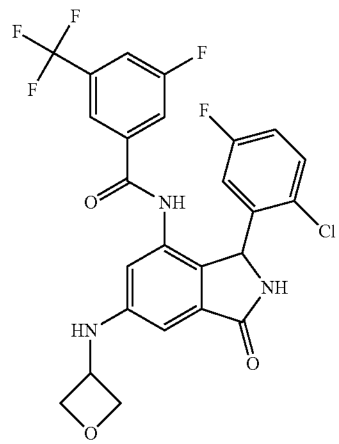 [SMILES: O=C(Nc1cc(NC2COC2)cc2c1C(c1cc(F)ccc1Cl)NC2=O)c1cc(F)cc(C(F)(F)F)c1] | Fc1ccc(C1)c(c1)C1NC(=O)c2cc(NC3COC3)cc(NC(=O)c3cc(F)cc(c3)C(F)(F)F)c12 | NMR (400 MHz, DMSO-d6) 10.30 (s, 1H), 8.95 (br. s, 1H), 7.92 (d, 8.6 Hz, 1H), 7.69 (d, 8.9 Hz, 1H), 7.60 (s, 1H), 7.28 (dd, 8.9, 5.2 Hz, 1H), 7.06 (td, 8.4, 3.1 Hz, 1H), 6.94 (d, 6.3 Hz, 1H), 6.69 (d, 2.0 Hz, 1H), 6.62 (s, 1H), 6.57 (br. s, 1H), 5.82 (br. s, 1H), 4.89 (t, 6.5 Hz, 2H), 4.62 (dd, 12.7, 6.4 Hz, 1H), 4.45 (q, 6.1 Hz, 2H). 6% of formate salt at 8.36 | 538.2 | A | |
| I-614 | 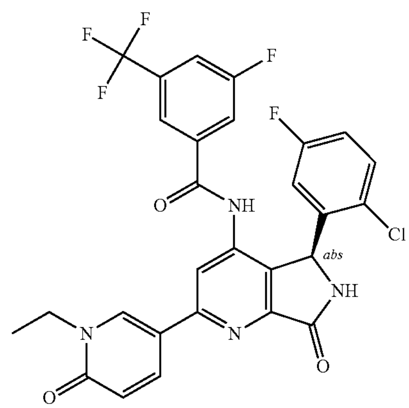 [SMILES: CCn1cc(-c2cc(NC(=O)c3cc(F)cc(C(F)(F)F)c3)c3c(n2)C(=O)N[C@@H]3c2cc(F)ccc2Cl)ccc1=O] | CCn1cc(ccc1=O)-c1cc(NC(=O)c2cc(F)cc(c2)C(F)(F)F)c2[C@H](NC(=O)c2n1)c1cc(F)ccc1Cl | | 589.3 | D | |
| I-615 | 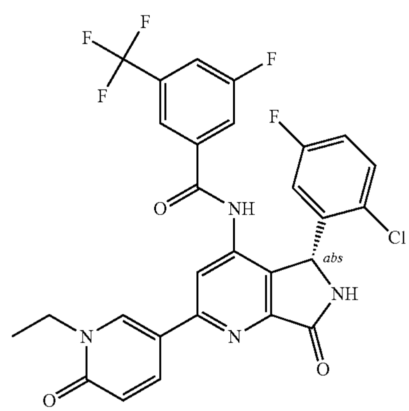 [SMILES: CCn1cc(-c2cc(NC(=O)c3cc(F)cc(C(F)(F)F)c3)c3c(n2)C(=O)N[C@H]3c2cc(F)ccc2Cl)ccc1=O] | CCn1cc(ccc1=O)-c1cc(NC(=O)c2cc(F)cc(c2)C(F)(F)F)c2[C@@H](NC(=O)c2n1)c1cc(F)ccc1Cl | | 589.3 | A | |
| I-616 | 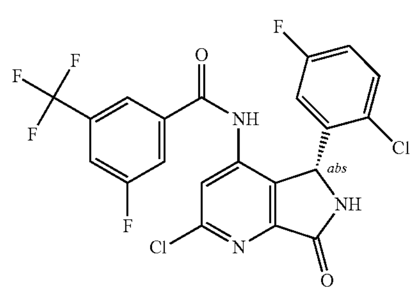 [SMILES: O=C(Nc1cc(Cl)nc2c1[C@H](c1cc(F)ccc1Cl)NC2=O)c1cc(F)cc(C(F)(F)F)c1] | Fc1ccc(C1)c(c1)[C@H]1NC(=O)c2nc(C1)cc(NC(=O)c3cc(F)cc(c3)C(F)(F)F)c12 | | 502.2 | B | |

TABLE 2-continued

Representative Compounds of the Invention with Bioactivity Data.

| Ex. No. | Structure | SMILES | $^1$H NMR | MS | ADP-Glo IC$_{50}$ | MCF 10A IC$_{50}$ |
|---|---|---|---|---|---|---|
| I-617 | 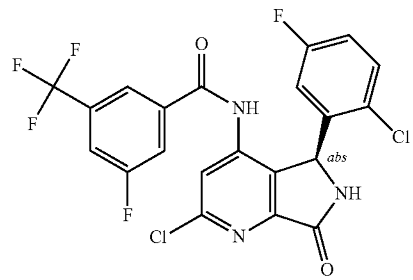 [SMILES: O=C(Nc1cc(Cl)nc2c1[C@@H](c1cc(F)ccc1Cl)NC2=O)c1cc(F)cc(C(F)(F)F)c1] | Fc1ccc(C1)c(c1)[C@@H]1NC(=O)c2nc(Cl)cc(NC(=O)c3cc(F)cc(c3)C(F)(F)F)c12 | | 502.2 | A | |
| I-618 | 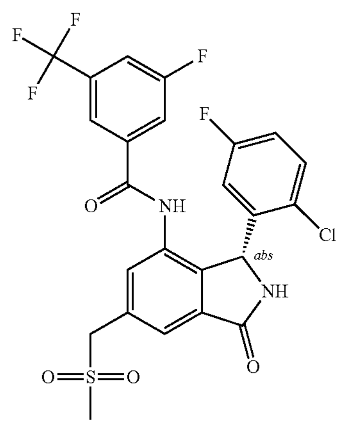 [SMILES: CS(=O)(=O)Cc1cc(NC(=O)c2cc(F)cc(C(F)(F)F)c2)c2c(c1)C(=O)N[C@H]2c1cc(F)ccc1Cl] | CS(=O)(=O)Cc1cc2C(=O)N[C@H](c2c(NC(=O)c2cc(F)cc(c2)C(F)(F)F)c1)c1cc(F)ccc1Cl | 1H NMR (DMSO-d6, 500 MHz) 10.5-10.7 (m, 1H), 9.0-9.3 (m, 1H), 7.9-8.0 (m, 1H), 7.7-7.8 (m, 2H), 7.6-7.7 (m, 1H), 7.4-7.6 (m, 1H), 7.2-7.4 (m, 1H), 6.9-7.2 (m, 1H), 6.5-7.0 (m, 2H), 5.7-6.2 (m, 1H), 4.5-4.9 (m, 2H), 2.9-3.1 (m, 3H) | 559 | A | |
| I-619 | 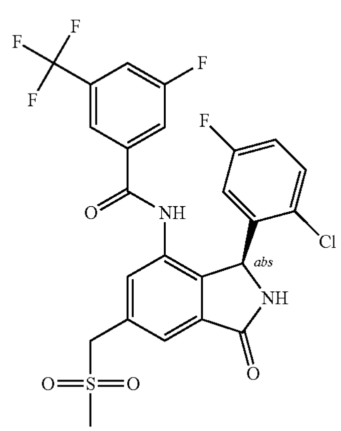 [SMILES: CS(=O)(=O)Cc1cc(NC(=O)c2cc(F)cc(C(F)(F)F)c2)c2c(c1)C(=O)N[C@@H]2c1cc(F)ccc1Cl] | CS(=O)(=O)Cc1cc2C(=O)N[C@@H](c2c(NC(=O)c2cc(F)cc(c2)C(F)(F)F)c1)c1cc(F)ccc1Cl | 1H NMR (DMSO-d6, 500 MHz) 10.5-10.7 (m, 1H), 9.1-9.4 (m, 1H), 7.92 (br d, 1H, 8.2 Hz), 7.7-7.8 (m, 2H), 7.6-7.7 (m, 1H), 7.5-7.6 (m, 1H), 7.2-7.4 (m, 1H), 7.0-7.2 (m, 1H), 6.2-7.0 (m, 1H), 5.7-6.2 (m, 1H), 4.5-4.8 (m, 2H), 2.9-3.1 (m, 3H) | 559 | D | |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-620 | 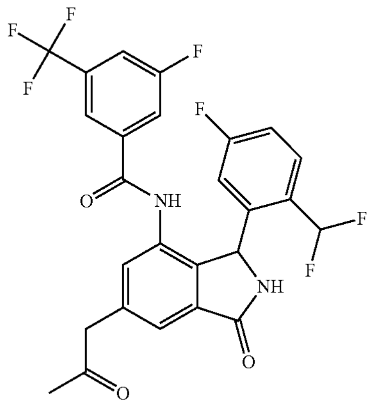 [SMILES: CC(=O)Cc1cc(NC(=O)c2cc(F)cc(C(F)(F)F)c2)c2c(c1)C(=O)NC2c1cc(F)ccc1C(F)F] | CC(=O)Cc1cc2C(=O)NC(c2c(NC(=O)c2cc(F)cc(c2)C(F)(F)F)c1)c1cc(F)ccc1C(F)F | | 539 | A | |
| I-621 | 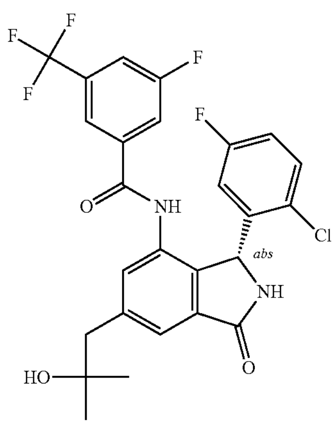 [SMILES: CC(C)(O)Cc1cc(NC(=O)c2cc(F)cc(C(F)(F)F)c2)c2c(c1)C(=O)N[C@H]2c1cc(F)ccc1Cl] | CC(C)(O)Cc1cc2C(=O)N[C@H](c2c(NC(=O)c2cc(F)cc(c2)C(F)(F)F)c1)c1cc(F)ccc1Cl | | 539 | A | |
| I-622 | 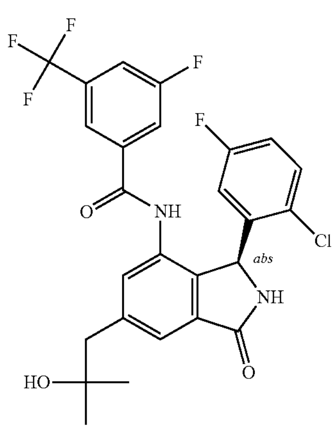 [SMILES: CC(C)(O)Cc1cc(NC(=O)c2cc(F)cc(C(F)(F)F)c2)c2c(c1)C(=O)N[C@@H]2c1cc(F)ccc1Cl] | CC(C)(O)Cc1cc2C(=O)N[C@@H](c2c(NC(=O)c2cc(F)cc(c2)C(F)(F)F)c1)c1cc(F)ccc1Cl | | 539 | B | |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-623 | 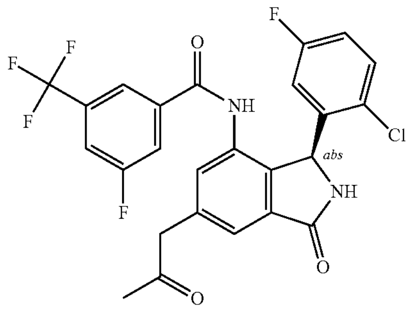 [SMILES: CC(=O)Cc1cc(NC(=O)c2cc(F)cc(C(F)(F)F)c2)c2c(c1)C(=O)N[C@@H]2c1cc(F)ccc1Cl] | CC(=O)Cc1cc2C(=O)N[C@H](c2c(NC(=O)c2cc(F)cc(c2)C(F)(F)F)c1)c1cc(F)ccc1Cl | | 523 | A | |
| I-624 | 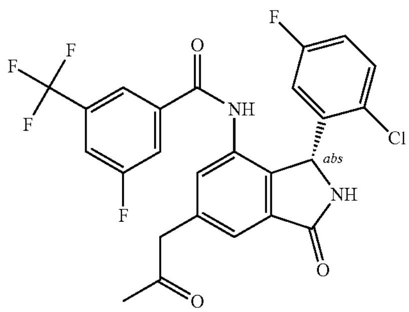 [SMILES: CC(=O)Cc1cc(NC(=O)c2cc(F)cc(C(F)(F)F)c2)c2c(c1)C(=O)N[C@H]2c1cc(F)ccc1Cl] | CC(=O)Cc1cc2C(=O)N[C@@H](c2c(NC(=O)c2cc(F)cc(c2)C(F)(F)F)c1)c1cc(F)ccc1Cl | | 523 | B | |
| I-625 | 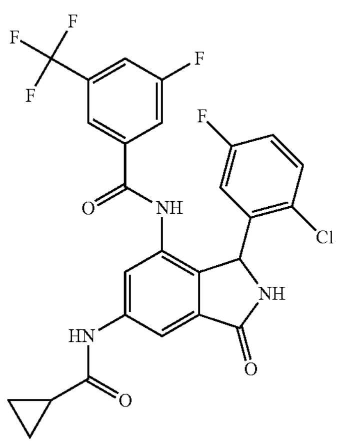 [SMILES: O=C(Nc1cc(NC(=O)C2CC2)cc2c1C(c1cc(F)ccc1Cl)NC2=O)c1cc(F)cc(C(F)(F)F)c1] | Fc1ccc(C1)c(c1)C1NC(=O)c2cc(NC(=O)C3CC3)cc(NC(=O)c3cc(F)cc(c3)C(F)(F)F)c12 | 1H NMR (500 MHz, DMSO-d6) 0.81-0.87 (m, 4 H) 1.81 (dt, 12.53, 6.19 Hz, 1 H) 5.85-5.95 (m, 1 H) 6.56 (br s, 1 H) 7.06 (td, 8.35, 3.15 Hz, 1 H) 7.29 (dd, 8.83, 5.04 Hz, 1 H) 7.62 (s, 1 H) 7.70 (br d, 9.14 Hz, 1 H) 7.80 (s, 1 H) 7.88-7.96 (m, 2 H) 9.08 (br s, 1 H) 10.47 (s, 1 H) 10.56 (s, 1 H) | 550.4 | A | |
| I-626 | 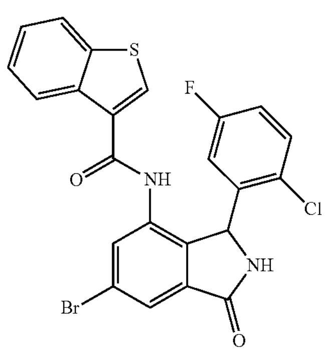 [SMILES: O=C1NC(c2cc(F)ccc2Cl)c2c(NC(=O)c3csc4ccccc34)cc(Br)cc21] | Fc1ccc(C1)c(c1)C1NC(=O)c2cc(Br)cc(NC(=O)c3csc4ccccc34)c12 | | 517.3 | A | |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-627 | 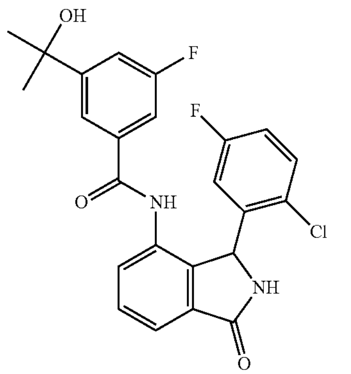 [SMILES: CC(C)(O)c1cc(F)cc(C(=O)Nc2cccc3c2C(c2cc(F)ccc2Cl)NC3=O)c1] | CC(C)(O)c1cc(F)cc(c1)C(=O)Nc1ccc c2C(=O)NC(c12)c1cc(F)ccc1Cl | | 457.4 | E | |
| I-628 | 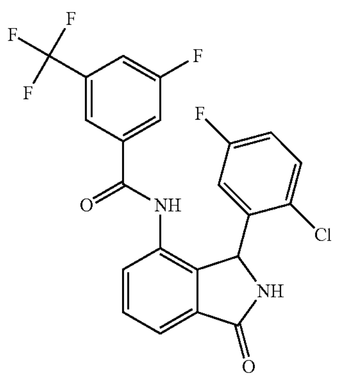 [SMILES: O=C(Nc1cccc2c1C(c1cc(F)ccc1Cl)NC2=O)c1cc(F)cc(C(F)(F)F)c1] | Fc1ccc(Br)c(c1)C1NC(=O)c2cccc(NC(=O)c3cc(F)cc(c3)C(F)(F)F)c12 | (400 MHz, DMSO-d6) 10.34 (s, 1H), 8.99 (s, 1H), 7.86 (d, 8.5 Hz, 1H), 7.75-7.68 (m, 3H), 7.65 (t, 7.6 Hz, 1H), 7.51 (d, 7.5 Hz, 1H), 7.46 (dd, 8.9, 5.4 Hz, 1H), 7.00 (dt, 8.5, 3.1 Hz, 1H), 6.55 (br s, 1H), 6.01 (s, 1H) [T = 60° C.]. | 509.3 | A | |
| I-629 | 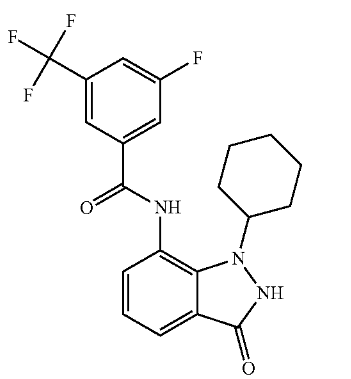 [SMILES: O=C(Nc1cccc2c(=O)[nH]n(C3CCCCC3)c12)c1cc(F)cc(C(F)(F)F)c1] | Fc1cc(cc(c1)C(F)(F)F)C(=O)Nc1ccc c2c1n([nH]c2=O)C1CCCCC1 | NMR (400 MHz, DMSO-d6) 10.61 (s, 2H), 8.26 (s, 1H), 8.15 (d, 8.7 Hz, 1H), 8.05 (d, 8.6 Hz, 1H), 7.59 (d, 7.9, 0.7 Hz, 1H), 7.23 (d, 7.2 Hz, 1H), 7.01 (t, 17.2, 9.5 Hz, 1H), 4.40 (m, 1H), 1.88-1.77 (m, 2H), 1.77-1.64 (m, 4H), 1.56-1.43 (m, 1H), 1.15-1.00 (m, 1H), 1.00-0.81 (m, 2H). | 422.5 | D | |
| I-630 | 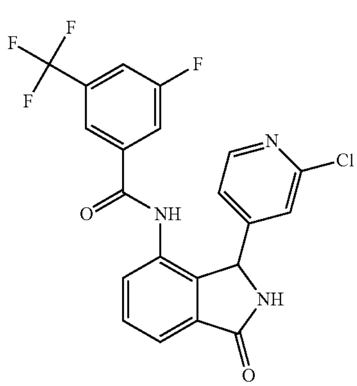 [SMILES: O=C(Nc1cccc2c1C(c1ccnc(Cl)c1)NC2=O)c1cc(F)cc(C(F)(F)F)c1] | Fc1cc(cc(c1)C(F)(F)F)C(=O)Nc1ccc c2C(=O)NC(c12)c1ccnc(Cl)c1 | (400 MHz, d6-DMSO) 10.52 (s, 1H), 9.17 (s, 1H), 8.19 (d, 5.1 Hz, 1H), 8.01 (d, 8.5 Hz, 1H), 7.86 (d, 8.5 Hz, 1H), 7.84 (s 1H), 7.72 (dd, 7.5, 1.0 Hz, 1H), 7.64 (t, 7.6 Hz, 1H), 7.51 (dd, 7.8, 1.0 Hz, 1H), 7.18 (s, 1H), 6.93 (dd, 5.2, 1.4 Hz, 1H), 5.75 (s, 1H). With traces of aliphatic impurity. | 448.3 | E | |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-631 | 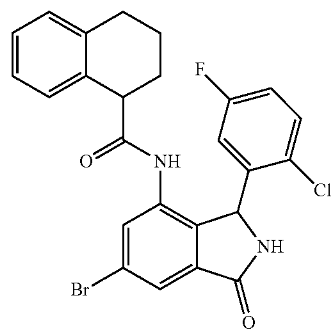 [SMILES: O=C1NC(c2cc(F)ccc2Cl)c2c(NC(=O)C3CCCc4ccccc43)cc(Br)cc21] | Fc1ccc(C1)c(c1)C1NC(=O)c2cc(Br)cc(NC(=O)C3CCCc4cccc34)c12 | 1H NMR (400 MHz, DMSO-d6) 9.99 (d, 52.3 Hz, 1H), 9.25 (s, 1H), 7.79 (d, 12.1 Hz, 1H), 7.72 (s, 1H), 7.65-7.24 (m, 2H), 7.16-6.93 (m, 3H), 6.59 (d, 59.8 Hz, 1H), 6.10 (s, 1H), 3.59 (s, 1H), 2.66 (d, 6.3 Hz, 2H), 1.95-1.67 (m, 2H), 1.64 (s, 2H), . | 512.95 | D | |
| I-632 | 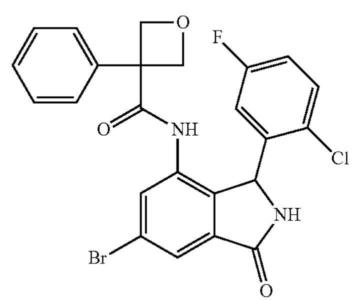 [SMILES: O=C1NC(c2cc(F)ccc2Cl)c2c(NC(=O)C3(c4ccccc4)COC3)cc(Br)cc21] | Fc1ccc(C1)c(c1)C1NC(=O)c2cc(Br)cc(NC(=O)C3(COC3)c3cccc3)c12 | 1H NMR (400 MHz, DMSO-d6) 9.89 (s, 1H), 9.29 (s, 1H), 7.76 (d, 1.7 Hz, 1H), 7.51 (s, 2H), 7.39-7.18 (m, 6H), 6.11 (s, 1H), 4.87 (d, 6.4 Hz, 1H), 4.69 (d, 6.3 Hz, 1H), 4.62 (d, 6.4 Hz, 1H), 4.51 (s, 1H). | 514.95 | E | |
| I-633 | 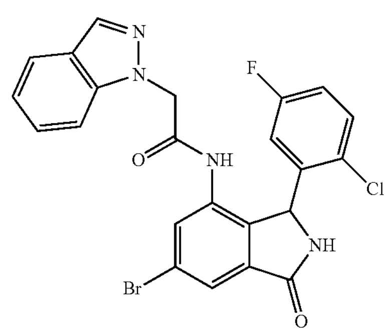 [SMILES: O=C(Cn1ncc2ccccc21)Nc1cc(Br)cc2c1C(c1cc(F)ccc1Cl)NC2=O] | Fc1ccc(C1)c(c1)C1NC(=O)c2cc(Br)cc(NC(=O)Cn3ncc4ccccc34)c12 | 1H NMR (400 MHz, DMSO-d6) 10.19 (s, 1H), 9.22 (s, 1H), 8.06 (s, 1H), 7.75 (dd, 18.4, 8.9 Hz, 3H), 7.54 (s, 1H), 7.41-7.23 (m, 3H), 7.16 (t, 7.4 Hz, 1H), 5.95 (s, 1H), 4.99 (s, 2H). | 512.95 | E | |
| I-634 | 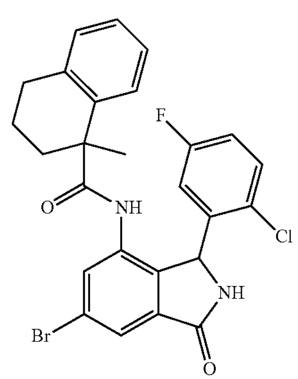 [SMILES: CC1(C(=O)Nc2cc(Br)cc3c2C(c2cc(F)ccc2Cl)NC3=O)CCCc2ccccc21] | CC1(CCCc2ccccc12)C(=O)Nc1cc(Br)cc2C(=O)NC(c12)c1cc(F)ccc1C1 | 1H NMR (400 MHz, Chloroform-d) 855-8.25 (d, 111.5 Hz, 1H), 7.84 (dd, 9.8, 1.7 Hz, 1H), 7.44 (dt, 9.2, 4.9 Hz, 1H), 7.23-6.95 (m, 4H), 6.92-6.81 (m, 1H), 6.57 (d, 8.1 Hz, 1H), 6.41 (d, 7.0 Hz, 1H), 6.33-6.23 (m, 1H), 5.82-5.46 (m, 1H), 2.72 (ddt, 22.0, 10.5, 5.9 Hz, 2H), 2.24-2.05 (m, 1H), 1.89-1.72 (m, 1H), 1.71-1.61 (m, 1H), 1.51 (d, 6.8 Hz, 4H). | 527.1 | D | |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-635 | 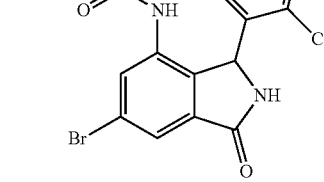 | Cc1cc2cc cc(C(=O) Nc3cc(Br) cc4C(= O)NC(c3 4)c3cc(F) ccc3Cl)c 2o1 | 1H NMR (400 MHz, DMSO-d6) 10.14 (s, 1H), 9.27 (s, 1H), 7.77 (dd, 17.9, 1.8 Hz, 2H), 7.69 (dd, 6.8, 2.3 Hz, 1H), 7.33 (dd, 8.9, 5.1 Hz, 1H), 7.28-7.18 (m, 2H), 7.11 (td, 8.4, 3.1 Hz, 1H), 6.65 (d, 1.3 Hz, 2H), 6.06 (s, 1H), 2.41 (s, 3H). | 513 | D | |
| I-636 | 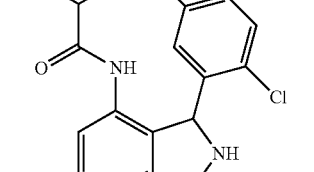 | Cn1ccc2c (ccnc12) C(=O)Nc 1cc(Br)cc 2C(=O)N C(c12)c1 cc(F)ccc1 Cl | 1H NMR (400 MHz, DMSO-d6) 10.40 (s, 1H), 9.29 (s, 1H), 8.32 (d, 4.9 Hz, 1H), 7.80 (s, 2H), 7.63 (d, 3.5 Hz, 1H), 7.37 (dd, 8.8, 5.1 Hz, 1H), 7.14 (td, 8.5, 3.1 Hz, 1H), 7.01 (d, 4.9 Hz, 1H), 6.72 (s, 1H), 6.45 (d, 3.5 Hz, 1H), 6.10 (s, 1H), 3.85 (s, 3H). | 513 | E | |
| I-637 | 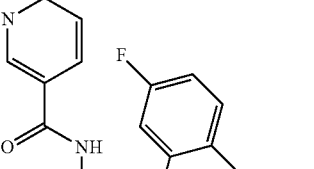 | Fc1ccc(C 1)c(c1)C1 NC(=O)c 2cc(Br)cc (NC(=O) c3ccc4nn cn4c3)c1 2 | 1H NMR (400 MHz, DMSO-d6) 10.46 (s, 1H), 9.42 (d, 0.8 Hz, 1H), 9.29 (s, 1H), 8.94 (t, 1.4 Hz, 1H), 7.88-7.80 (m, 2H), 7.71 (d, 1.7 Hz, 1H), 7.46 (dd, 9.6, 1.7 Hz, 1H), 7.34 (dd, 8.9, 5.2 Hz, 1H), 7.11 (td, 8.4, 3.0 Hz, 1H), 6.70 (s, 1H), 6.00 (s, 1H). | 500 | E | |
| I-638 | 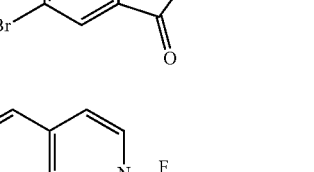 | Fc1ccc(C 1)c(c1)C1 NC(=O)c 2cc(Br)cc (NC(=O) c3nccc4c cccc34)c 12 | 1H NMR (400 MHz, DMSO-d6) 10.51 (s, 1H), 9.34 (s, 1H), 9.05 (d, 8.8 Hz, 1H), 8.50 (d, 5.5 Hz, 1H), 8.28 (d, 6.4 Hz, 1H), 8.12 (dd, 13.7, 6.9 Hz, 2H), 7.82 (dt, 40.5, 7.6 Hz, 3H), 7.45 (s, 1H), 7.15 (t, 8.5 Hz., 1H), 6.24 (s, 1H). | 510 | E | |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-639 | 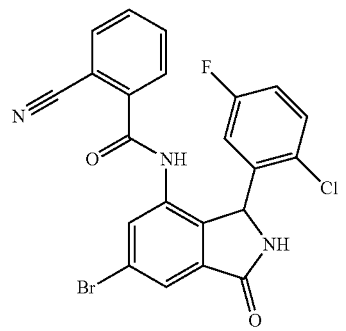 [SMILES: N#Cc1ccccc1C(=O)Nc1cc(Br)cc2c1C(c1cc(F)ccc1Cl)NC2=O] | Fc1ccc(C1)c(c1)C1 NC(=O)c 2cc(Br)cc (NC(=O) c3ccccc3 C#N)c12 | 1H NMR (400 MHz, Chloroform-d) 8.20 (s, 1H), 7.93 (s, 1H), 7.73 (s, 4H), 6.96 (s, 1H), 6.73 (t, 8.3 Hz, 1H), 6.61 (s, 1H), 6.55 (s, 1H), 6.17 (s, 1H). | 484 | E | |
| I-640 | 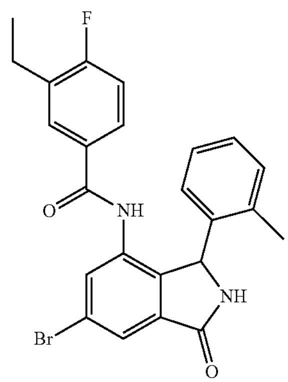 [SMILES: CCc1cc(C(=O)Nc2cc(Br)cc3c2C(c2ccccc2C)NC3=O)ccc1F] | CCc1cc(c cc1F)C(= O)Nc1cc (Br)cc2C (=O)NC(c 12)c1ccc cc1C | NMR (400 MHz, DMSO-d6) 10.04 (s, 1H), 9.22 (s, 1H), 7.84 (d, 1.6 Hz, 1H), 7.75 (d, 1.6 Hz, 1H), 7.30 (ddd, 7.6, 5.0, 2.2 Hz, 1H), 7.16 (dd, 9.6, 8.4, Hz, 1H), 7.13-7.09 (m, 2H), 7.06 (br. d, 6.9 Hz, 1H), 6.99 (td, 7.3, 1.2 Hz, 1H), 6.57 (br. s, 1H), 5.96 (s, 1H), 2.57 (q, 7.6 Hz, 2H), 2.25 (br. s, 3H), 1.14 (t, 7.5 Hz, 3H), impurities at 3.7, 1.2 and 0.9 | 467.4 | D | |
| I-641 | 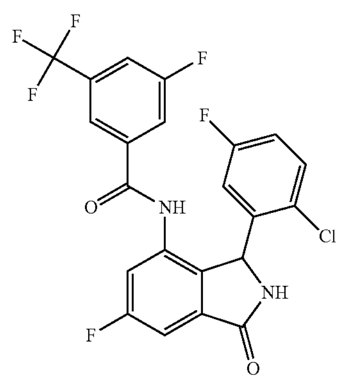 [SMILES: O=C(Nc1cc(F)cc2c1C(c1cc(F)ccc1Cl)NC2=O)c1cc(F)cc(C(F)(F)F)c1] | Fc1ccc(C1)c(c1)C1 NC(=O)c 2cc(F)cc (NC(=O)c 3cc(F)cc (c3)C(F) (F)F)c12 | NMR (400 MHz, DMSO-d6) 10.59 (br. s, 1H), 9.30 (s, 1H), 7.96 (d, 7.6 Hz, 1H), 7.72 (d, 8.9 Hz, 1H), 7.63 (s, 1H), 7.49 (d, 6.5 Hz, 1H), 7.44 (d, 10.0 Hz, 1H), 7.33 (dd, 8.9, 5.2 Hz, 1H), 7.10 (td, 8.5, 2.5 Hz, 1H), 6.65 (br. s, 1H), 5.98 (br. s, 1H). 9% of formate salt at 8.36. | 485.1 | A | |
| I-642 | 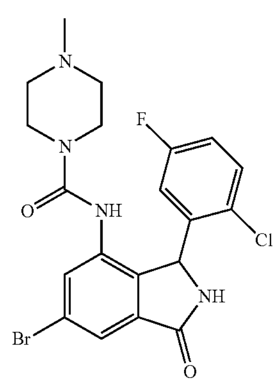 [SMILES: CN1CCN(C(=O)Nc2cc(Br)cc3c2C(c2cc(F)ccc2Cl)NC3=O)CC1] | CN1CCN (CC1)C (=O)Nc1c c(Br)cc2 C(=O)N C(c12)c1 cc(F)ccc1 C1 | 1H-NMR (400 MHz, DMSO-d6) 9.17 (br. s, 1H), 8.64 (s, 1H), 7.58 (d, 1.7 Hz, 1H), 7.54-7.48 (m, 1H), 7.47 (d, 1.7 Hz, 1H), 7.25 (ddd, 8.7, 8.1, 3.1 Hz, 1H), 6.57 (br. s, 1H), 5.97 (br. s, 1H), 3.22-3.11 (m, 2H), 3.03-2.93 (m, 2H), 2.18-2.09 (m, 2H), 2.12 (s, 3H), 2.05-1.95 (m, 2H). Compound is a partial salt (peak at 8.22). | 473.2 | E | |

TABLE 2-continued

Representative Compounds of the Invention with Bioactivity Data.

| Ex. No. | Structure | SMILES | $^1$H NMR | MS | ADP-Glo IC$_{50}$ | MCF 10A IC$_{50}$ |
|---|---|---|---|---|---|---|
| I-643 | 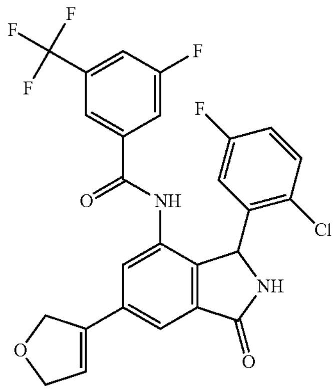 [SMILES: O=C(Nc1cc(C2=CCOC2)cc2c1C(c1cc(F)ccc1Cl)NC2=O)c1cc(F)cc(C(F)(F)F)c1] | Fc1ccc(C1)c(c1)C1NC(=O)c2cc(cc(NC(=O)c3cc(F)cc(c3)C(F)(F)F)c12)C1=CCOC1 | NMR (400 MHz, MeCN-d3) 8.64 (s, 1H), 7.74 (s, 1H), 7.63 (d, 8.7 Hz, 1H), 7.58 (d, 8.7 Hz, 1H), 7.58-7.53 (m, 2H), 7.26 (dd, 8.9, 5.2 Hz, 2H), 6.97 (td, 8.5, 2.9 Hz, 1H), 6.66 (br. s, 1H), 6.54 (s, 1H), 6.13 (br. s, 1H), 5.04-4.99 (m, 2H), 4.81 (t, 4.1 Hz, 2H). | 535.2 | A | |
| I-644 | 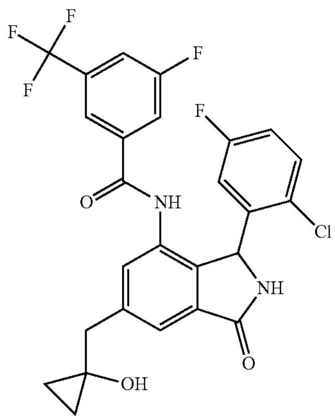 [SMILES: O=C(Nc1cc(CC2(O)CC2)cc2c1C(c1cc(F)ccc1Cl)NC2=O)c1cc(F)cc(C(F)(F)F)c1] | OC1(Cc2cc3C(=O)NC(c3c(NC(=O)c3cc(F)cc(c3)C(F)(F)F)c2)c2cc(F)ccc2C1)CC1 | NMR (400 MHz, DMSO-d6) 10.51 (s, 1H), 9.09 (br. s, 1H), 7.94 (d, 8.5 Hz, 1H), 7.74 (d, 9.0 Hz, 1H), 7.66 (s, 1H), 7.64 (s, 1H), 7.40 (s, 1H), 7.32 (dd, 8.9, 5.2 Hz, 1H), 7.10 (td, 8.3, 3.0 Hz, 1H), 6.58 (br. s, 1H), 5.96 (br. s, 1H), 5.29 (s, 1H), 2.93 (s, 2H), 0.66-0.62 (m, 2H), 0.60-0.56 (m, 2H). | 537.2 | A | |
| I-645 | 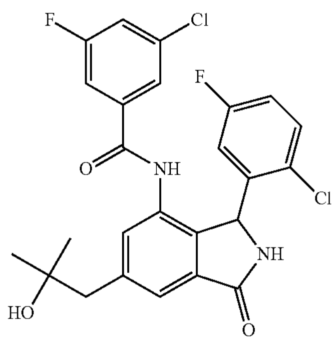 [SMILES: CC(C)(O)Cc1cc(NC(=O)c2cc(F)cc(Cl)c2)c2c(c1)C(=O)NC2c1cc(F)ccc1Cl] | CC(C)(O)Cc1cc2C(=O)NC(c2c(NC(=O)c2cc(F)cc(Cl)c2)c1)c1cc(F)ccc1Cl | NMR (400 MHz, CD3CN) 8.46 (s, 1H), 7.60 (s, 1H), 7.42 (s, 1H), 7.39 (m, 1H), 7.32-7.27 (m, 3H), 7.24 (dd, 9.0, 1.8 Hz, 1H), 7.00 (ddd, 11.5, 5.7, 2.8 Hz, 1H), 6.63 (br s, 1H), 6.10 (br s, 1H), 2.92-2.82 (m, 2H), 1.19 (s, 3H), 1.17 (s, 3H). | 505 | A | |
| I-646 | 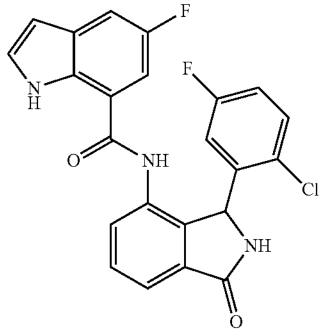 [SMILES: O=C1NC(c2cc(F)ccc2Cl)c2c(NC(=O)c3cc(F)cc4cc[nH]c34)cccc21] | Fc1ccc(C1)c(c1)C1NC(=O)c2cccc(NC(=O)c3cc(F)cc4c[nH]c34)c12 | | 438.46 | A | |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-647 | 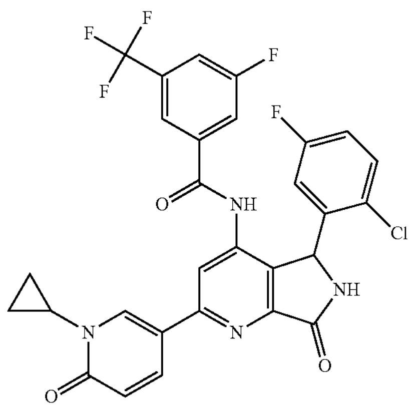 [SMILES: O=C(Nc1cc(-c2ccc(=O)n(C3CC3)c2)nc2c1C(c1cc(F)ccc1Cl)NC2=O)c1cc(F)cc(C(F)(F)F)c1] | Fc1ccc(C1)c(c1)C1NC(=O)c2nc(cc(NC(=O)c3cc(F)cc(c3)C(F)(F)F)c12)-c1ccc(=O)n(c1)C1CC1 | 1H NMR (DMSO-d6, 500 MHz) 10.90 (br s, 1H), 9.50 (br s, 1H), 8.32 (d, 2.2 Hz, 1H), 8.18 (dd, 9.6, 2.7 Hz, 1H), 7.85-8.03 (m, 2H), 7.76 (br d, 9.1 Hz, 1H), 7.68 (s, 1H), 7.34 (dd, 8.8, 5.0 Hz, 1H), 7.09 (td, 8.4, 3.2 Hz, 1H), 6.76-6.99 (m, 1H), 6.55 (d, 9.5 Hz, 1H), 6.01 (br s, 1H), 3.39-3.45 (m, 1H), 1.04-1.12 (m, 2H), 0.90-1.01 (m, 2H) | 601.6 | A | |
| I-648 | 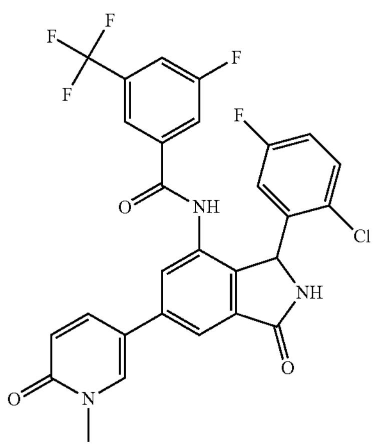 [SMILES: Cn1cc(-c2cc(NC(=O)c3cc(F)cc(C(F)(F)F)c3)c3c(c2)C(=O)NC3c2cc(F)ccc2Cl)ccc1=O] | Cn1cc(ccc1=O)-c1cc2C(=O)NC(c2c(NC(=O)c2cc(F)cc(c2)C(F)(F)F)c1)c1cc(F)ccc1Cl | | 574.5 | A | |
| I-649 | 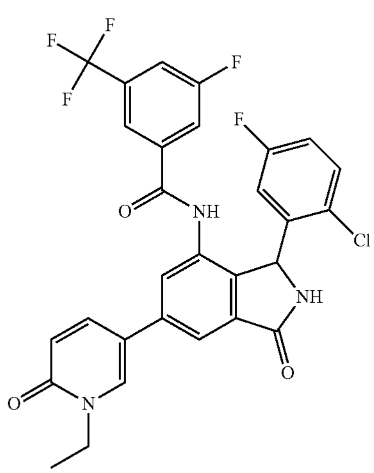 [SMILES: CCn1cc(-c2cc(NC(=O)c3cc(F)cc(C(F)(F)F)c3)c3c(c2)C(=O)NC3c2cc(F)ccc2Cl)ccc1=O] | CCn1cc(ccc1=O)-c1cc2C(=O)NC(c2c(NC(=O)c2cc(F)cc(c2)C(F)(F)F)c1)c1cc(F)ccc1Cl | | 588.5 | A | |

TABLE 2-continued

Representative Compounds of the Invention with Bioactivity Data.

| Ex. No. | Structure | SMILES | $^1$H NMR | MS | ADP-Glo IC$_{50}$ | MCF 10A IC$_{50}$ |
|---|---|---|---|---|---|---|
| I-650 | 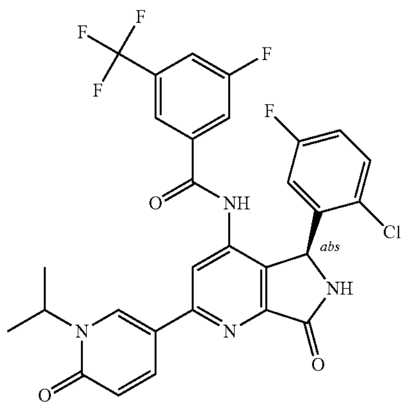 [SMILES: CC(C)n1cc(-c2cc(NC(=O)c3cc(F)cc(C(F)(F)F)c3)c3c(n2)C(=O)N[C@@H]3c2cc(F)ccc2Cl)ccc1=O] | CC(C)n1cc(ccc1=O)-c1cc(NC(=O)c2cc(F)cc(c2)C(F)(F)F)c2[C@H](NC(=O)c2n1)c1cc(F)ccc1Cl | | 603.4 | | C |
| I-651 | 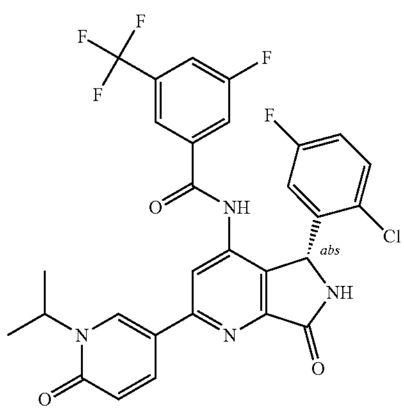 [SMILES: CC(C)n1cc(-c2cc(NC(=O)c3cc(F)cc(C(F)(F)F)c3)c3c(n2)C(=O)N[C@H]3c2cc(F)ccc2Cl)ccc1=O] | CC(C)n1cc(ccc1=O)-c1cc(NC(=O)c2cc(F)cc(c2)C(F)(F)F)c2[C@@H](NC(=O)c2n1)c1cc(F)ccc1Cl | | 603.4 | | A |
| I-652 | 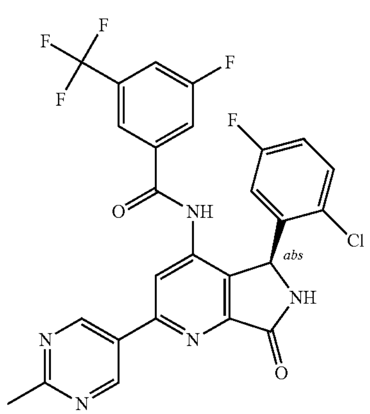 [SMILES: Cc1ncc(-c2cc(NC(=O)c3cc(F)cc(C(F)(F)F)c3)c3c(n2)C(=O)N[C@@H]3c2cc(F)ccc2Cl)cn1] | Cc1ncc(cn1)-c1cc(NC(=O)c2cc(F)cc(c2)C(F)(F)F)c2[C@H](NC(=O)c2n1)c1cc(F)ccc1Cl | | 560.2 | | C |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-653 | 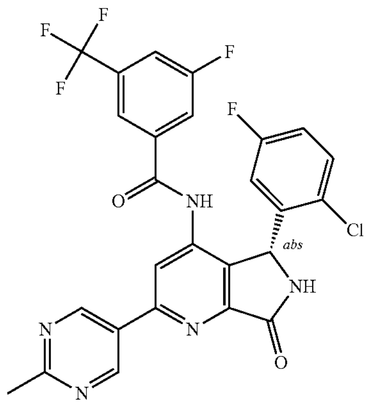 [SMILES: Cc1ncc(-c2cc(NC(=O)c3cc(F)cc(C(F)(F)F)c3)c3c(n2)C(=O)N[C@H]3c2cc(F)ccc2Cl)cn1] | Cc1ncc(cn1)-c1cc(NC(=O)c2cc(F)cc(c2)C(F)(F)F)c2[C@@H](NC(=O)c2n1)c1cc(F)ccc1Cl | | 560.2 | A | |
| I-654 | 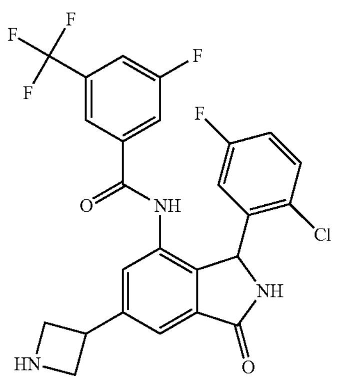 [SMILES: O=C(Nc1cc(C2CNC2)cc2c1C(c1cc(F)ccc1Cl)NC2=O)c1cc(F)cc(C(F)(F)F)c1] | Fc1ccc(C1)c(c1)C1NC(=O)c2cc(cc(NC(=O)c3cc(F)cc(c3)C(F)(F)F)c12)C1CNC1 | | 522.4 | A | |
| I-655 | 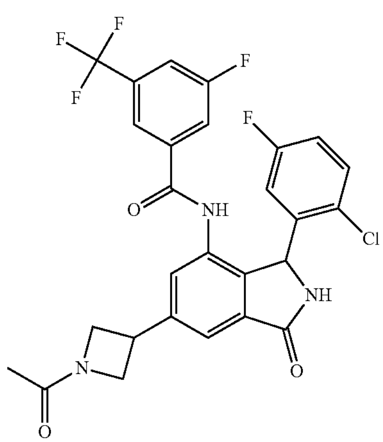 [SMILES: CC(=O)N1CC(c2cc(NC(=O)c3cc(F)cc(C(F)(F)F)c3)c3c(c2)C(=O)NC3c2cc(F)ccc2Cl)C1] | CC(=O)N1CC(C1)c1cc2C(=O)NC(c2c(NC(=O)c2cc(F)cc(c2)C(F)(F)F)c1)c1cc(F)ccc1Cl | | 564.51 | A | |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-656 | 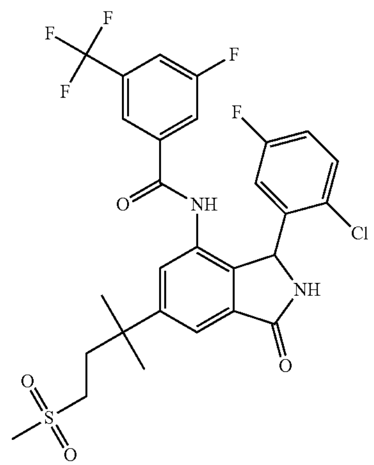 [SMILES: CC(C)(CCS(C)(=O)=O)c1cc(NC(=O)c2cc(F)cc(C(F)(F)F)c2)c2c(c1)C(=O)NC2c1cc(F)ccc1Cl] | CC(C)(COS(C)(=O)=O)c1cc2C(=O)NC(c2c(NC(=O)c2cc(F)cc(c2)C(F)(F)F)c1)c1cc(F)ccc1Cl | | 617 | A | |
| I-657 | 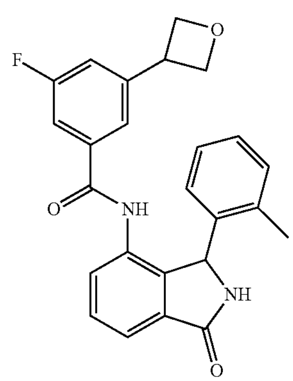 [SMILES: Cc1ccccc1C1NC(=O)c2cccc(NC(=O)c3cc(F)cc(C4COC4)c3)c21] | Cc1ccccc1C1NC(=O)c2cccc(NC(=O)c3cc(F)cc(c3)C3COC3)c12 | | 417.45 | D | |
| I-658 | 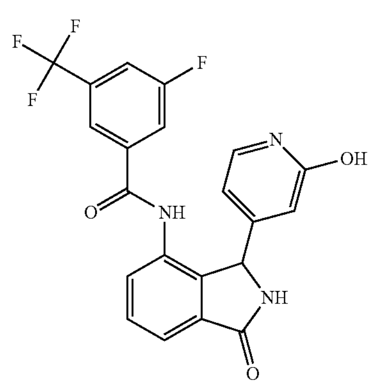 [SMILES: O=C(Nc1cccc2c1C(c1ccnc(O)c1)NC2=O)c1cc(F)cc(C(F)(F)F)c1] | Oc1cc(ccn1)C1NC(=O)c2cccc(NC(=O)c3cc(F)cc(c3)C(F)(F)F)c12 | (400 MHz, d6-DMSO) 11.39 (br s, 1H), 10.58 (br s, 1H), 9.07 (s, 1H), 7.99 (d, 8.2 Hz, 1H), 7.91 (s, 1H), 7.87 (d, 9.1 Hz, 1H), 7.68 (dd, 7.4, 0.9 Hz, 1H), 7.62 (app t, 7.6 Hz, 1H), 7.53 (d, 6.8 Hz, 1H), 7.15 (d, 6.8 Hz, 1H), 6.06 (s, 1H), 5.52 (s, 1H), 5.45 (d, 6.6 Hz, 1H). | 430.4 | E | |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-659 | 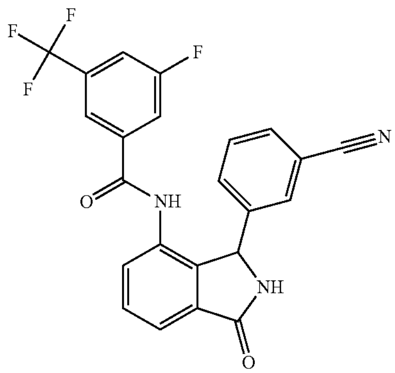 [SMILES: N#Cc1cccc(C2NC(=O)c3cccc(NC(=O)c4cc(F)cc(C(F)(F)F)c4)c32)c1] | Fc1cc(cc (c1)C(F) (F)F)C(= O)Nc1cc cc2C(=O) NC(c12) c1cccc(c 1)C#N | (400 MHz, d6-DMSO) 10.44 (br s, 1H), 9.13 (s, 1H), 7.98 (d, 8.5 Hz, 1H), 7.77 (d, 8.9 Hz, 1H), 7.71 (dd, 7.5, 1.0 Hz, 1H), 7.67 (s, 1H), 7.66 (d, 7.2 Hz, 1H), 7.63 (app t, 6.6 Hz, 1H), 7.49 (dd, 7.7, 1.0 Hz, 1H), 7.45 (app t, 1.5 Hz, 1H), 7.38 (app t, 7.8 Hz, 1H), 7.22 (br d, 8.0 Hz, 1H), 5.77 (s, 1H). | 438.4 | E | |
| I-660 | 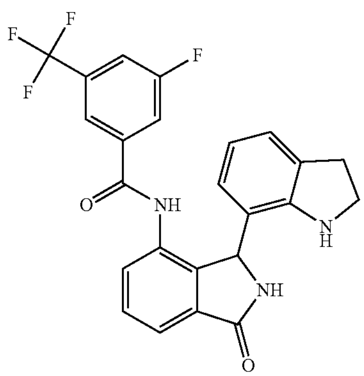 [SMILES: O=C(Nc1cccc2c1C(c1cccc3c1NCC3)NC2=O)c1cc(F)cc(C(F)(F)F)c1] | Fc1cc(cc (c1)C(F) (F)F)C(= O)Nc1cc cc2C(=O) NC(c12) c1cccc2C CNc12 | 1H NMR (400 MHz, CD3CN) 8.93 (br. s, 1H), 7.90 (d, 7.8 Hz, 1H), 7.69-7.65 (m, 3H), 7.59-7.54 (m, 2H), 7.08 (br. s, 1H), 6.95 (dd, 7.2, 0.9 Hz, 1H), 6.62 (br. d, 7.3 Hz, 1H), 6.54 (t, 7.5 Hz, 1H), 5.74 (s, 1H), 4.21 (br. s, 1H), 3.30-3.22 (m, 1H), 2.93-2.79 (m, 2H), 2.54-2.44 (m, 1H); acetonitrile satellites at 2.11 and 1.77. | 456.2 | E | |
| I-661 | 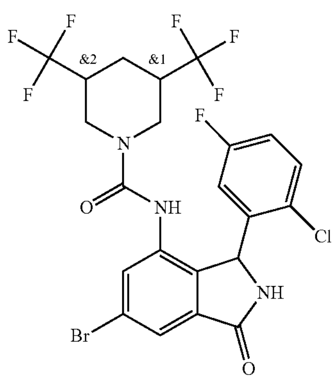 [SMILES: O=C1NC(c2cc(F)ccc2Cl)c2c(NC(=O)N3CC(C(F)(F)F)CC(C(F)(F)F)C3)cc(Br)cc21] | Fc1ccc(C 1)c(c1)C1 NC(=O)c 2cc(Br)cc (NC(=O) N3CC(C C(C3)C (F)(F)F)C (F)(F)F)c 12 | (400 MHz, DMSO-d6) 9.18 (br s, 1H), 8.82 (s, 0.3 H), 8.65 (s, 0.6 H), 7.69-7.58 (m, 2H), 7.53-7.42 (m, 1H), 7.27-7.17 (m, 1H), 6.67 (br s, 1H), 5.98 (s, 1H), 3.45-3.34 (m, 4H), 2.65-2.53 (m, 2H), 1.92 (t, 6.5 Hz, 2H) | 602.2 | D | |
| I-662 | 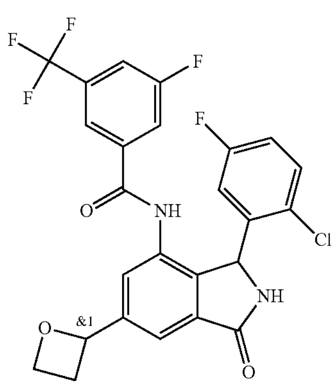 [SMILES: O=C(Nc1cc(C2CCO2)cc2c1C(c1cc(F)ccc1Cl)NC2=O)c1cc(F)cc(C(F)(F)F)c1] | Fc1ccc(C 1)c(c1)C1 NC(=O)c 2cc(cc(N C(=O)c3 cc(F)cc(c 3)C(F)(F) F)c12)C1 CCO1 | (400 MHz, DMSO-d6) 10.53 (s, 1H), 9.09 (s, 1H), 7.94 (d, 8.4 Hz, 1H), 7.90 (d, 8.1 Hz, 1H), 7.73 (d, 8.4 Hz, 1H), 7.66 (s, 1H), 7.55 (d, 8.0 Hz, 1H), 7.30 (ddd, 7.7, 5.1, 2.8 Hz, 1H), 7.13-7.05 (m, 1H), 6.62 (t, 7.4 Hz, 0.3H), 6.57 (t, 7.4 Hz, 0.7H), 6.00 (br s, 1H), 4.74 (dd, 13.7, 7.9 Hz, 1H), 4.65-4.55 (m, 1H), 3.52-3.46 (m, 1H), 3.24-3.11 (m, 1H). | 523.4 | B | |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-663 | 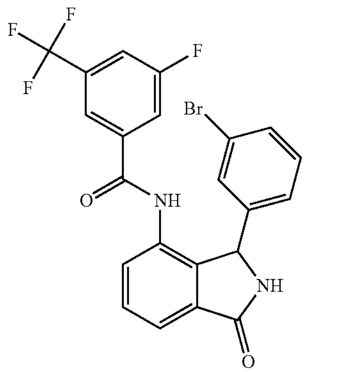 [SMILES: O=C(Nc1cccc2c1C(c1cccc(Br)c1)NC2=O)c1cc(F)cc(C(F)(F)F)c1] | Fc1cc(cc(c1)C(F)(F)F)C(=O)Nc1ccc c2C(=O)NC(c12)c1cccc(Br)c1 | (400 MHz, d6-DMSO) 10.47 (s, 1H), 9.10 (s, 1H), 7.98 (d, 8.5 Hz, 1H), 7.77 (d, 8.9 Hz, 1H), 7.72 (s, 1H), 7.69 (d, 7.3 Hz, 1H), 7.61 (app t, 7.6 Hz, 1H), 7.48 (d, 7.6 Hz, 1H), 7.38 (d, 7.9 Hz, 1H), 7.15 (d, 1.3 Hz, 1H), 7.13 (app t, 9.2 Hz, 1H), 6.89 (d, 7.8 Hz, 1H), 5.69 (s, 1H). | 493.3 | E | |
| I-664 | 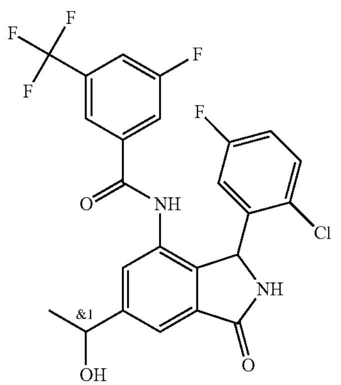 [SMILES: CC(O)c1cc(NC(=O)c2cc(F)cc(C(F)(F)F)c2)c2c(c1)C(=O)NC2c1cc(F)ccc1Cl] | CC(O)c1cc2C(=O)NC(c2c(NC(=O)c2cc(F)cc(c2)C(F)(F)F)c1)c1cc(F)ccc1Cl | NMR (400 MHz, DMSO-d6) 10.50 (2xs, 1H), 9.11 (s, 1H), 7.94 (d, 8.5 Hz, 1H), 7.74 (d, 8.6 Hz, 1H), 7.69-7.64 (m, 2H), 7.47 (2xs, 1H), 7.31 (dd, 8.9, 5.1 Hz, 1H), 7.09 (td, 8.4, 3.0 Hz, 1H), 6.60 (br. s, 1H), 5.96 (br. s, 1H), 5.44 (2xs, 1H), 4.94-4.83 (m, 1H), 1.40 (2xd, 2.1 Hz, 3H). | 511.1 | A | |
| I-665 | 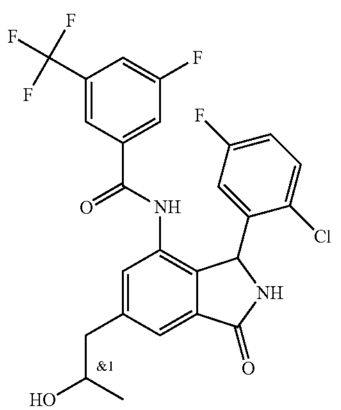 [SMILES: CC(O)Cc1cc(NC(=O)c2cc(F)cc(C(F)(F)F)c2)c2c(c1)C(=O)NC2c1cc(F)ccc1Cl] | CC(O)Cc1cc2C(=O)NC(c2c(NC(=O)c2cc(F)cc(c2)C(F)(F)F)c1)c1cc(F)ccc1Cl | NMR (400 MHz, DMSO-d6) 10.47 (s, 1H), 9.08 (s, 1H), 7.93 (d, 8.3 Hz, 1H), 7.73 (d, 8.9 Hz, 1H), 7.65 (s, 1H), 7.54 (s, 1H), 7.36-7.26 (m, 2H), 7.09 (td, 8.4, 3.0 Hz, 1H), 6.61 (br. s, 1H), 5.94 (br. s, 1H), 4.68 (2xd, 1.2 Hz, 1H), 3.95-3.85 (m, 1H), 2.86-2.72 (m, 2H), 1.09 (2xd, 2.9 Hz, 3H). | 525.1 | A | |
| I-666 | 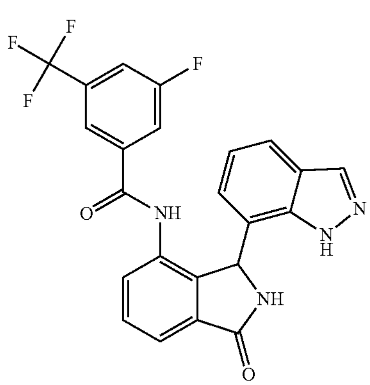 [SMILES: O=C(Nc1cccc2c1C(c1cccc3cn[nH]c13)NC2=O)c1cc(F)cc(C(F)(F)F)c1] | Fc1cc(cc(c1)C(F)(F)F)C(=O)Nc1ccc c2C(=O)NC(c12)c1cccc2cn[nH]c12 | 1H NMR (400 MHz, DMSO-d6) 13.02 (s, 1H), 10.28 (s, 1H), 9.16 (s, 1H), 7.86 (s, 1H), 7.78 (d, 8.5 Hz, 1H), 7.72 (d, 7.4 Hz, 1H), 7.63 (t, 7.7 Hz, 1H), 7.57 (d, 7.9 Hz, 1H), 7.45 (d, 7.7 Hz, 1H), 7.20 (d, 8.8 Hz, 1H), 7.14 (s, 1H), 6.89 (t, 7.6 Hz, 1H), 6.64 (d, 7.2 Hz, 1H), 6.31 (s, 1H) | 455.3 | E | |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-667 | 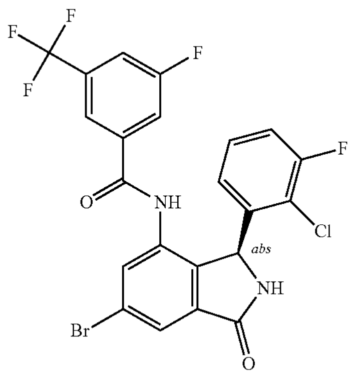 | Fc1cc(cc(c1)C(F)(F)F)C(=O)Nc1cc(Br)cc2C(=O)N[C@@H](c12)c1ccc(F)c1Cl | 1H NMR (400 MHz, DMSO-d6) 10.55 (s, 1H), 9.33 (s, 1H), 7.96 (d, 8.4 Hz, 1H), 7.84 (d, 1.7 Hz, 1H), 7.76 (s, 1H), 7.69 (d, 9.0 Hz, 1H), 7.56 (s, 1H), 7.26 (t, 8.7 Hz, 1H), 7.17 (s. 1H), 6.67 (s, 1H), 6.07 (s, 1H). | 545 | D | |
| I-668 | 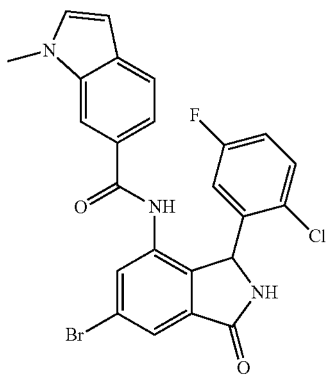 [SMILES: Cn1ccc2ccc(C(=O)Nc3cc(Br)cc4c3C(c3cc(F)ccc3Cl)NC4=O)cc21] | Cn1ccc2cc(cc12)C(=O)Nc1cc(Br)cc2C(=O)NC(c12)c1cc(F)ccc1Cl | 1H NMR (400 MHz, Chloroform-d) 7.80 (s, 1H), 7.64 (d, 8.3 Hz, 1H), 7.48 (d, 1.6 Hz, 1H), 7.46 (s, 1H), 7.28 (s, 1H), 7.25-7.16 (m, 1H), 7.09-6.97 (m, 2H), 6.87 (d, 15.2 Hz, 2H), 6.66-6.26 (m, 1H), 3.85 (s, 3H). | 512.05 | D | |
| I-669 | 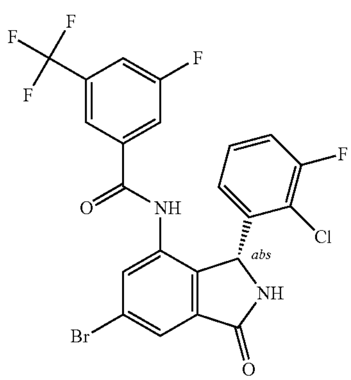 | Fc1cc(cc(c1)C(F)(F)F)C(=O)Nc1cc(Br)cc2C(=O)N[C@H](c12)c1cccc(F)c1Cl | 1H NMR (400 MHz, DMSO-d6) 10.55 (s, 1H), 9.33 (s, 1H), 7.96 (d, 8.4 Hz, 1H), 7.84 (d, 1.7 Hz, 1H), 7.76 (s, 1H), 7.69 (d, 9.0 Hz, 1H), 7.56 (s, 1H), 7.26 (t, 8.7 Hz, 1H), 7.17 (s, 1H), 6.67 (s, 1H), 6.07 (s, 1H). | 545 | A | |
| I-670 | 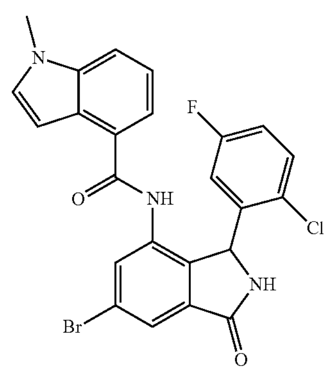 [SMILES: Cn1ccc2c(C(=O)Nc3cc(Br)cc4c3C(c3cc(F)ccc3Cl)NC4=O)cccc21] | Cn1ccc2c(cccc12)C(=O)Nc1cc(Br)cc2C(=O)NC(c12)c1cc(F)ccc1Cl | 1H NMR (400 MHz, Methanol-d4) 7.61 (dt, 8.2, 0.9 Hz, 1H), 7.56-7.35 (m, 2H), 7.35-7.16 (m, 3H), 7.18-6.50 (m, 5H), 3.86 (s, 3H). | 512.05 | E | |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-671 | 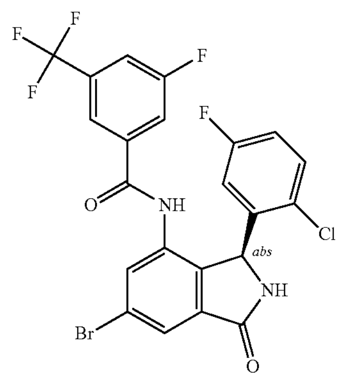 [SMILES: O=C(Nc1cc(Br)cc2c1[C@@H](c1cc(F)ccc1Cl)NC2=O)c1cc(F)cc(C(F)(F)F)c1] | Fc1ccc(F)c(c1)[C@H]1NC(=O)c2cc(Br)cc(NC(=O)c3cc(F)cc(c3)C(F)(F)F)c12 | 1H NMR (400 MHz, DMSO-d6) 10.59 (s, 1H), 9.27 (s, 1H), 7.98 (d, 8.6 Hz, 1H), 7.82 (d, 1.8 Hz, 1H), 7.78-7.70 (m, 2H), 7.68 (s, 1H), 7.09 (dt, 9.7, 4.0 Hz, 2H), 6.88 (dd, 8.1, 4.7 Hz, 1H), 5.85 (s, 1H). | 529 | D | |
| I-672 | 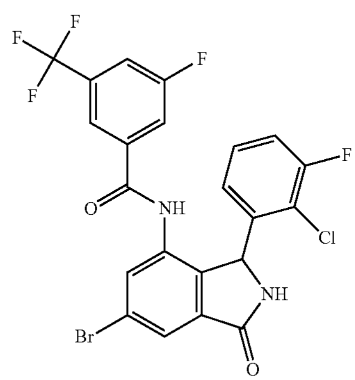 [SMILES: O=C(Nc1cc(Br)cc2c1C(c1cccc(F)c1Cl)NC2=O)c1cc(F)cc(C(F)(F)F)c1] | Fc1cc(cc(c1)C(F)(F)F)C(=O)Nc1cc(Br)cc2C(=O)NC(c12)c1ccc(F)c1Cl | 1H NMR (400 MHz, DMSO-d6) 10.55 (s, 1H), 9.33 (s, 1H), 7.96 (d, 8.4 Hz, 1H), 7.84 (d, 1.7 Hz, 1H), 7.76 (s, 1H), 7.69 (d, 9.0 Hz, 1H), 7.56 (s, 1H), 7.26 (t, 8.7 Hz, 1H), 7.17 (s, 1H), 6.67 (s, 1H), 6.07 (s, 1H). | 545 | A | |
| I-673 | 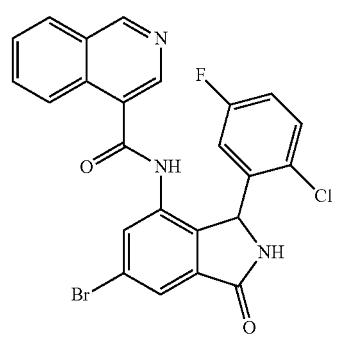 [SMILES: O=C1NC(c2cc(F)ccc2Cl)c2c(NC(=O)c3cncc4ccccc34)cc(Br)cc21] | Fc1ccc(C1)c(c1)C1NC(=O)c2cc(Br)cc(NC(=O)c3cncc4ccccc34)c12 | 1H NMR (400 MHz, Methanol-d4) 9.35 (d, 0.8 Hz, 1H), 8.20 (dd, 7.7, 1.4 Hz, 1H), 8.10 (d, 8.5 Hz, 1H), 7.98 (d, 1.7 Hz, 2H), 7.82 (dddd, 26.6, 8.1, 6.9, 1.3 Hz, 3H), 7.45 (dd, 8.9, 5.0 Hz, 1H), 7.17 (ddd, 8.9, 7.7, 3.0 Hz, 1H), 6.69 (s, 1H), 6.30 (s, 1H). | 510 | D | |
| I-674 | 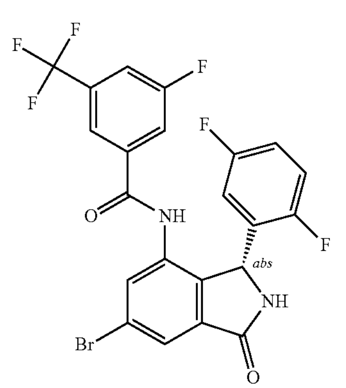 [SMILES: O=C(Nc1cc(Br)cc2c1[C@H](c1cc(F)ccc1F)NC2=O)c1cc(F)cc(C(F)(F)F)c1] | Fc1ccc(F)c(c1)[C@@H]1NC(=O)c2cc(Br)cc(NC(=O)c3cc(F)cc(c3)C(F)(F)F)c12 | 1H NMR (400 MHz, DMSO-d6) 10.59 (s, 1H), 9.27 (s, 1H), 7.98 (d, 8.5 Hz, 1H), 7.82 (d, 1.7 Hz, 1H), 7.78-7.70 (m, 2H), 7.68 (s, 1H), 7.14-7.02 (m, 2H), 6.92-6.84 (m, 1H), 5.85 (s, 1H). | 531 | B | |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-675 | 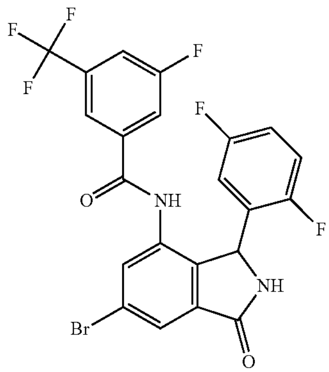 [SMILES: O=C(Nc1cc(Br)cc2c1C(c1cc(F)ccc1F)NC2=O)c1cc(F)cc(C(F)(F)F)c1] | Fc1ccc(F)c(c1)C1NC(=O)c2cc(Br)cc(NC(=O)c3cc(F)cc(c3)C(F)(F)F)c12 | 1H NMR (400 MHz, DMSO-d6) 10.58 (s, 1H), 9.27 (s, 1H), 7.98 (d, 8.5 Hz, 1H), 7.82 (d, 1.8 Hz, 1H), 7.78-7.71 (m, 2H), 7.68 (s, 1H), 7.09 (dq, 8.0, 3.0 Hz, 2H), 6.88 (s, 1H), 5.85 (s, 1H). | 529 | A | |
| I-676 | 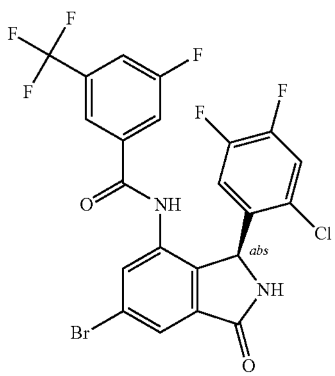 [SMILES: O=C(Nc1cc(Br)cc2c1[C@@H](c1cc(F)c(F)cc1Cl)NC2=O)c1cc(F)cc(C(F)(F)F)c1] | Fc1cc(cc(c1)C(F)(F)F)C(=O)Nc1cc(Br)cc2C(=O)N[C@@H](c12)c1cc(F)c(F)cc1Cl | 1H NMR (400 MHz, DMSO-d6) 10.58 (s, 1H), 9.29 (s, 1H), 7.99 (d, 8.5 Hz, 1H), 7.83 (d, 1.7 Hz, 1H), 7.81-7.71 (m, 2H), 7.63 (s, 1H), 7.57 (dd, 10.4, 7.3 Hz, 1H), 6.98 (s, 1H), 5.94 (s, 1H). | 562.9 | D | |
| I-677 | 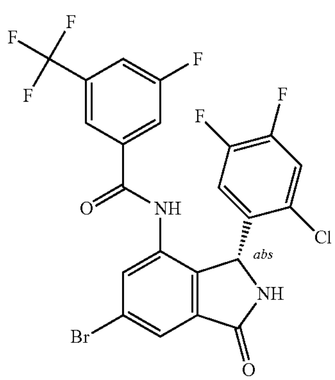 [SMILES: O=C(Nc1cc(Br)cc2c1[C@H](c1cc(F)c(F)cc1Cl)NC2=O)c1cc(F)cc(C(F)(F)F)c1] | Fc1cc(cc(c1)C(F)(F)F)C(=O)Nc1cc(Br)cc2C(=O)N[C@H](c12)c1cc(F)c(F)cc1Cl | 1H NMR (400 MHz, DMSO-d6) 10.58 (s, 1H), 9.32-9.27 (m, 1H), 7.98 (d, 8.8 Hz, 1H), 7.83 (d, 1.7 Hz, 1H), 7.81-7.71 (m, 2H), 7.63 (s, 1H), 7.57 (dd, 10.4, 7.2 Hz, 1H), 6.91 (s, 1H), 5.94 (s, 1H). | 562.9 | A | |
| I-678 | 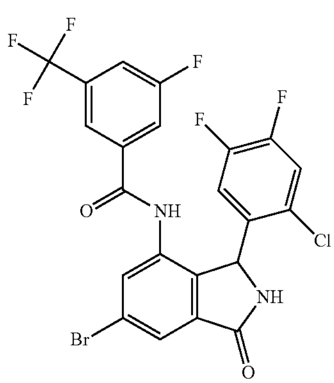 [SMILES: O=C(Nc1cc(Br)cc2c1C(c1cc(F)c(F)cc1Cl)NC2=O)c1cc(F)cc(C(F)(F)F)c1] | Fc1cc(cc(c1)C(F)(F)F)C(=O)Nc1cc(Br)cc2C(=O)NC(c12)c1cc(F)c(F)cc1Cl | 1H NMR (400 MHz, DMSO-d6) 10.58 (s, 1H), 9.29 (s, 1H), 7.99 (d, 8.4 Hz, 1H), 7.86-7.81 (m, 1H), 7.81-7.72 (m, 2H), 7.63 (s, 1H), 7.57 (dd, 10.4, 7.3 Hz, 1H), 6.91 (s, 1H), 5.93 (s, 1H). | 562.95 | A | |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-679 | 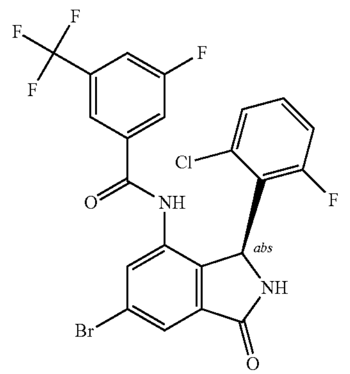 [SMILES: O=C(Nc1cc(Br)cc2c1[C@@H](c1c(F)cccc1Cl)NC2=O)c1cc(F)cc(C(F)(F)F)c1] | Fc1cc(cc(c1)C(F)(F)F)C(=O)Nc1cc(Br)cc2C(=O)N[C@@H](c12)c1c(F)cccc1Cl | 1H NMR (400 MHz, DMSO-d6) 10.61 (d, 15.9 Hz, 1H), 9.24 (d, 57.4 Hz, 1H), 8.00-7.93 (m, 1H), 7.83 (dd, 5.3, 1.7 Hz, 1H), 7.74-7.60 (m, 3H), 7.27 (qd, 8.2, 5.9 Hz, 1H), 7.20-6.91 (m, 2H), 6.16 (d, 1.9 Hz, 1H). | 544.9 | D | |
| I-680 | 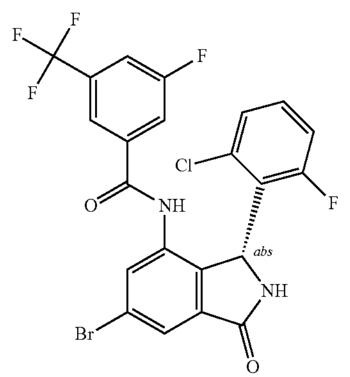 [SMILES: O=C(Nc1cc(Br)cc2c1[C@H](c1c(F)cccc1Cl)NC2=O)c1cc(F)cc(C(F)(F)F)c1] | Fc1cc(cc(c1)C(F)(F)F)C(=O)Nc1cc(Br)cc2C(=O)N[C@H](c12)c1c(F)cccc1Cl | 1H NMR (400 MHz, DMSO-d6) 10.61 (d, 15.9 Hz, 1H), 9.24 (d, 57.5 Hz, 1H), 7.97 (d, 8.4 Hz, 1H), 7.83 (dd, 5.3, 1.7 Hz, 1H), 7.74-7.60 (m, 3H), 7.27 (qd, 8.1, 5.9 Hz, 1H), 7.20-6.92 (m, 2H), 6.16 (d, 2.0 Hz, 1H). | 544.9 | A | |
| I-681 | 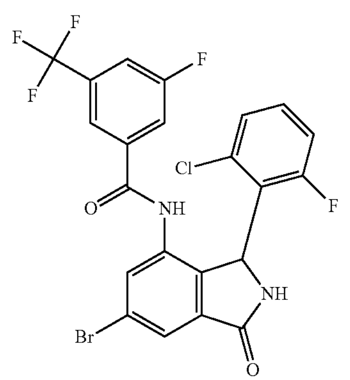 [SMILES: O=C(Nc1cc(Br)cc2c1C(c1c(F)cccc1Cl)NC2=O)c1cc(F)cc(C(F)(F)F)c1] | Fc1cc(cc(c1)C(F)(F)F)C(=O)Nc1cc(Br)cc2C(=O)NC(c12)c1c(F)cccc1Cl | 1H NMR (400 MHz, DMSO-d6) 10.62 (d, 15.8 Hz, 1H), 9.25 (d, 57.4 Hz, 1H), 7.96 (d, 8.5 Hz, 1H), 7.83 (dd, 5.4, 1.8 Hz, 1H), 7.75-7.59 (m, 3H), 7.28 (td, 8.4, 6.1 Hz, 1H), 7.20-6.91 (m, 2H), 6.16 (s, 1H). | 544.95 | D | |
| I-682 | 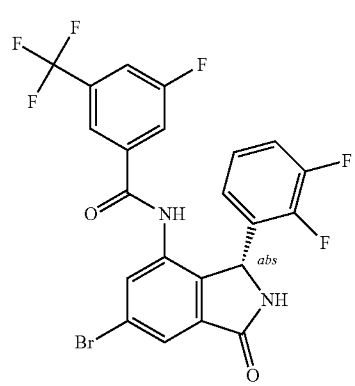 [SMILES: O=C(Nc1cc(Br)cc2c1[C@H](c1cccc(F)c1F)NC2=O)c1cc(F)cc(C(F)(F)F)c1] | Fc1cc(cc(c1)C(F)(F)F)C(=O)Nc1cc(Br)cc2C(=O)N[C@H](c12)c1cccc(F)c1F | 1H NMR (400 MHz, DMSO-d6) 10.58 (s, 1H), 9.30 (s, 1H), 7.98 (d, 8.4 Hz, 1H), 7.84 (d, 1.7 Hz, 1H), 7.79 (d, 1.8 Hz, 1H), 7.73 (d, 9.0 Hz, 1H), 7.63 (s, 1H), 7.35-7.24 (m, 1H), 7.05-6.95 (m, 1H), 6.80 (t, 7.0 Hz, 1H), 5.95 (s, 1H). | 528.95 | B | |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-683 | 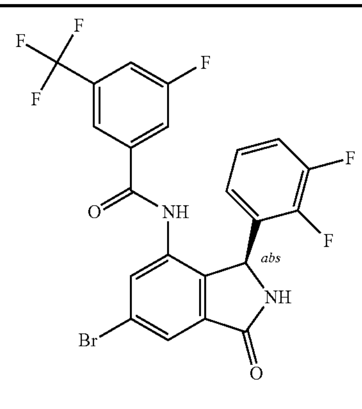 | Fc1cc(cc (c1)C(F) (F)F)C(= O)Nc1cc (Br)cc2C (=O)N[C @@H](c 12)cccc(F)c1F | 1H NMR (400 MHz, DMSO-d6) 10.58 (s, 1H), 9.30 (s, 1H), 8.02-7.95 (m, 1H), 7.84 (d, 1.8 Hz, 1H), 7.79 (d, 1.8 Hz, 1H), 7.73 (d, 8.8 Hz, 1H), 7.63 (s, 1H), 7.29 (q, 8.9 Hz, 1H), 7.00 (q, 7.9 Hz, 1H), 6.80 (t, 7.0 Hz, 1H), 5.95 (s, 1H). | 528.95 | D | |
| I-684 | 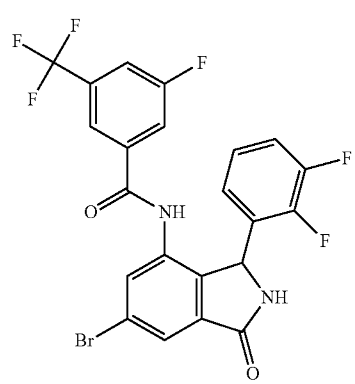 [SMILES: O=C(Nc1cc(Br)cc2c1C(c1cccc(F)c1F)NC2=O)c1cc(F)cc(C(F)(F)F)c1] | Fc1cc(cc (c1)C(F) (F)F)C(= O)Nc1cc (Br)cc2C (=O)NC(c 12)cccc(F)c1F | 1H NMR (400 MHz, DMSO-d6) 10.58 (s, 1H), 9.31 (s, 1H), 7.99 (d, 8.5 Hz, 1H), 7.84 (d, 1.7 Hz, 1H), 7.79 (t, 2.2 Hz, 1H), 7.73 (d, 9.0 Hz, 1H), 7.62 (s, 1H), 7.29 (q, 8.8 Hz, 1H), 7.03-6.95 (m, 1H), 6.84-6.76 (m, 1H), 5.95 (s, 1H). | 528.95 | D | |
| I-685 | 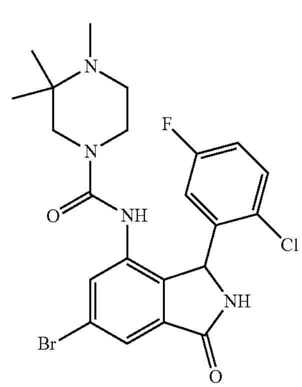 [SMILES: CN1CCN(C(=O)Nc2cc(Br)cc3c2C(c2cc(F)ccc2Cl)NC3=O)CC1(C)C] | CN1CCN (CC1(C) C)C(=O) Nc1cc(Br) cc2C(= O)NC(c1 2)cc(F) ccc1Cl | 1H-NMR (400 MHz, DMSO-d6) 9.16 (s, 1H), 8.49 (s, 1H), 7.59 (d, 1.4 Hz, 1H), 7.53 (d, 1.5 Hz, 1H), 7.51-7.44 (m, 1H), 7.23 (td, 8.4, 3.0 Hz, 1H), 6.61 (br. s, 1H), 6.01 (br. s, 1H), 3.23-3.16 (m, 1H), 3.02-2.96 (m, 1H), 2.92 (d, 13.4 Hz, 1H), 2.76 (d, 12.6 Hz, 1H), 2.32-2.20 (m, 2H), 2.06 (s, 3H), 0.84 (s, 3H), 0.69 (s, 3H). Partial formate salt. Presence of racemic impurity derived from piperazine (possibly the carbamic acid), includes-' 4.01 (t, 6.2 Hz, 2H), 3.66 (t, 6.4 Hz, 2H), 2.10 (s, 3H), 0.90 (s, 3H). | 511.3 | E | |

TABLE 2-continued

Representative Compounds of the Invention with Bioactivity Data.

| Ex. No. | Structure | SMILES | $^1$H NMR | MS | ADP-Glo IC$_{50}$ | MCF 10A IC$_{50}$ |
|---|---|---|---|---|---|---|
| I-686 | 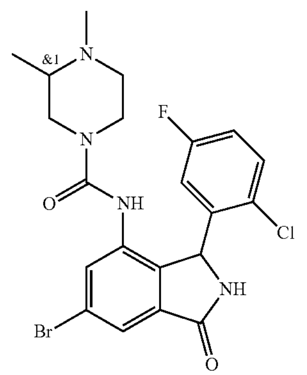 [SMILES: CC1CN(C(=O)Nc2cc(Br)cc3c2C(c2cc(F)ccc2Cl)NC3=O)CCN1C] | CC1CN(CCN1C)C(=O)Nc1cc(Br)cc2C(=O)NC(c12)c1cc(F)ccc1Cl | 1H-NMR (400 MHz, DMSO-d6) as a ca. 1:1 mixture of diastereomers, 9.16 (br. s, 2H), 8.63 (br. s, 1H), 8.61 (br. s, 1H), 7.58 (d, 1.4 Hz, 2H), 7.49 (br. d, 1.5 Hz, 2H), 7.48 (br. d, 1.3 Hz, 2H), 7.25 (td, 8.5, 3.0 Hz, 2H), 6.56 (br. s, 2H), 5.97 (br. s, 2H), 3.69-3.64 (m, 1H), 3.64-3.43 (m, 4H), 2.79-2.70 (m, 1H), 2.62-2.52 (m, 1H), 2.34 (dd, 12.9, 10.6 Hz, 1H), 2.18-2.12 (m, 1H), 2.11 (s, 6H), 1.90-1.82 (m, 1H), 1.80-1.72 (m, 1H), 1.72-1.65 (m, 1H), 1.62-1.52 (m, 1H), 1.49-1.36 (m, 1H), 0.89 (d, 6.2 Hz, 3H), 0.87 (d, 6.3 Hz, 3H). | 497.3 | E | |
| I-687 | 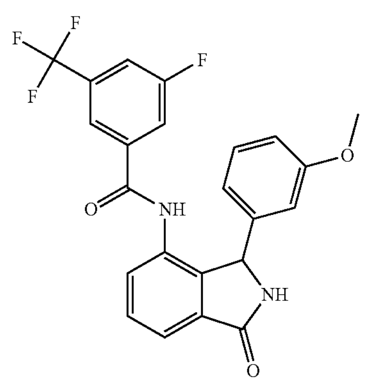 [SMILES: COc1cccc(C2NC(=O)c3cccc(NC(=O)c4cc(F)cc(C(F)(F)F)c4)c32)c1] | COc1cccc(c1)C1NC(=O)c2cccc(NC(=O)c3cc(F)cc(c3)C(F)(F)F)c12 | NMR (400 MHz, DMSOd6) 10.42 (s, 1H), 9.07 (s, 1H), 7.96 (d, 8.5 Hz, 1H), 7.70 (d, 8.2 Hz, 1H), 7.67 (m, 2H), 7.59 (1, 7.6 Hz, 1H), 7.49 (d, 7.7 Hz, 1 H), 7.08 (t, 7.9 Hz, 1H), 6.75 (dd, 8.2, 2.4 Hz, 1H), 6.53 (bs, 1H), 6.48 (d, 7.7 Hz, 1H), 5.68 (s, 1H), 3.48 (s, 3H). | 445.2 | E | |
| I-688 | 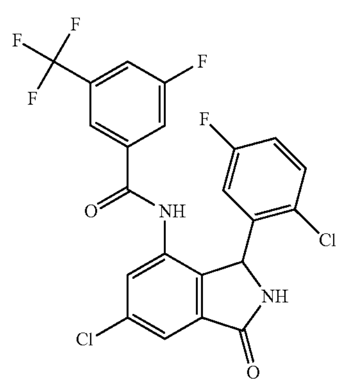 [SMILES: O=C(Nc1cc(Cl)cc2c1C(c1cc(F)ccc1Cl)NC2=O)c1cc(F)cc(C(F)(F)F)c1] | Fc1ccc(C1)c(c1)C1NC(=O)c2cc(Cl)cc(NC(=O)c3cc(F)cc(c3)C(F)(F)F)c12 | NMR (400 MHz, CD3CN) 8.64 (br s, 1H), 7.74 (d, 1.8 Hz, 1H), 7.63 (d, 6.0 Hz, 1H), 7.60 (s, 1H), 7.56 (d, 6.0 Hz, 1H), 7.53 (s, 1H), 7.30 (br s, 1H), 7.25 (dd, 8.8, 5.2 Hz, 1H), 6.96 (td, 8.4, 3.1 Hz, 1H), 6.66 (br s, 1H), 6.09 (br s, 1H). | 542.3 | A | |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-689 | 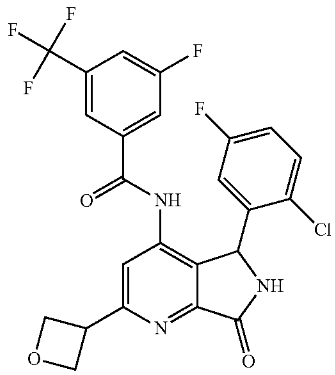 [SMILES: O=C(Nc1cc(C2COC2)nc2c1C(c1cc(F)ccc1Cl)NC2=O)c1cc(F)cc(C(F)(F)F)c1] | Fc1ccc(C1)c(c1)C1NC(=O)c2nc(cc(NC(=O)c3cc(F)cc(c3)C(F)(F)F)c12)C1COC1 | 1H NMR (400 MHz, DMSO-d6) 9.29 (s, 1H), 8.40 (s, 1H), 7.89-7.64 (m, 4H), 7.37 (dd, 8.9, 5.2 Hz, 1H), 7.09 (td, 8.4, 3.1 Hz, 1H), 6.75 (br s, 1H), 5.96 (s, 1H), 4.94 (dd, 8.5, 5.5 Hz, 2H), 4.89 (dd, 6.7, 5.7 Hz, 1H), 4.83 (dd, 6.7, 5.7 Hz, 1H), 4.53-4.40 (m, 1H). | 524.1 | B | |
| I-690 | 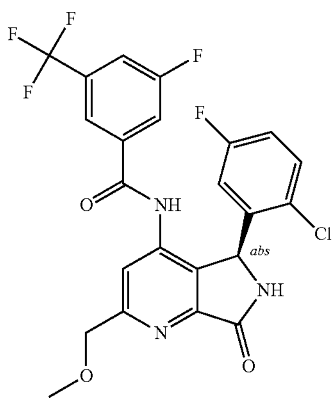 [SMILES: COCc1cc(NC(=O)c2cc(F)cc(C(F)(F)F)c2)c2c(n1)C(=O)N[C@@H]2c1cc(F)ccc1Cl] | COCc1cc2C(=O)N[C@@H](c2c(NC(=O)c2cc(F)cc(c2)C(F)(F)F)c1)c1cc(F)ccc1Cl | NMR (400 MHz, ACN) 8.61 (s, 1H), 7.69 (s, 1H), 7.65 (d, 8.5 Hz, 1H), 7.61-7.55 (m, 2H), 7.53 (s, 1H), 7.25 (dd, 8.9, 5.1 Hz, 1H), 7.22 (br s, 1H), 6.97 (ddd, 8.8, 8.0, 3.1 Hz, 1H), 6.64 (br s, 1H), 6.11 (br s, 1H), 4.59 (s, 2H), 3.41 (s, 3H) | 511.2 | B | |
| I-691 | 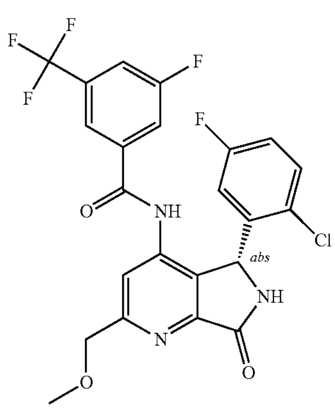 [SMILES: COCc1cc(NC(=O)c2cc(F)cc(C(F)(F)F)c2)c2c(n1)C(=O)N[C@H]2c1cc(F)ccc1Cl] | COCc1cc2C(=O)N[C@H](c2c(NC(=O)c2cc(F)cc(c2)C(F)(F)F)c1)c1cc(F)ccc1Cl | NMR (400 MHz, ACN) 8.61 (s, 1H), 7.69 (s, 1H), 7.65 (d, 8.5 Hz, 1H), 7.61-7.55 (m, 2H), 7.53 (s, 1H), 7.25 (dd, 8.9, 5.1 Hz, 1H), 7.22 (br s, 1H), 6.97 (ddd, 8.8, 8.0, 3.1 Hz, 1H), 6.64 (br s, 1H), 6.11 (br s, 1H), 4.59 (s, 2H), 3.41 (s, 3H) | 511.2 | A | A |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-692 | 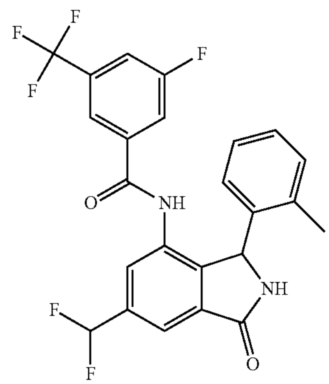 [SMILES: Cc1ccccc1C1NC(=O)c2cc(C(F)F)cc(NC(=O)c3cc(F)cc(C(F)(F)F)c3)c21] | Cc1cccc c1NC(= O)c2cc(c c(NC(=O) c3cc(F)c c(c3)C(F) (F)F)c12) C(F)F | NMR (400 MHz, DMSO) 10.49 (s, 1H), 9.24 (s, 1H), 7.87 (d, 8.6 Hz, 1H), 7.82 (d, 0.8 Hz, 1H), 7.73 (s, 1H), 7.46 (d, 8.5 Hz, 1H), 7.31 (s, 1H), 7.21 (t, 55.6 Hz, 1H), 7.04 (td, 7.5, 1.3 Hz, 1H), 6.97 (d, 6.7 Hz, 1H), 6.92 (t, 7.6 Hz, 1H), 6.48 (br s, 1H), 5.94 (s, 1H), 2.20 (br s, 3H). | 479.2 | B | |
| I-693 | 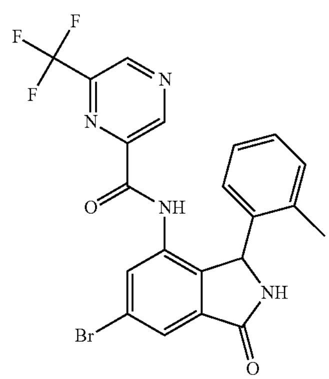 [SMILES: Cc1ccccc1C1NC(=O)c2cc(Br)cc(NC(=O)c3cncc(C(F)(F)F)n3)c21] | Cc1cccc c1NC(= O)c2cc(B r)cc(NC (=O)c3cnc c(n3)C(F) (F)F)c12 | NMR (400 MHz, CDCl3) 9.65 (s, 1H), 9.15 (s, 1H), 8.92 (s, 1H), 8.37 (br. d, 7.7 Hz, 1H), 7.86 (dd, 7.6, 0.8 Hz, 1H), 7.69 (t, 7.8 Hz, 1H), 7.42 (dd, 8.8, 4.9 Hz, 1H), 7.00 (ddd, 8.9, 7.5, 3.0 Hz, 1H), 6.68 (s, 1H), 6.59 (br. s, 1H), 6.26 (s, 1H), 1.63 (br. s, 3H). | 492.3 | E | |
| I-694 | 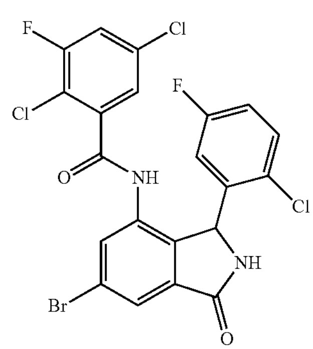 [SMILES: O=C(Nc1cc(Br)cc2c1C(c1cc(F)ccc1Cl)NC2=O)c1cc(Cl)cc(F)c1Cl] | Fc1ccc(C 1)c(c1)C1 NC(=O)c 2cc(Br)cc (NC(=O) c3cc(Cl)c c(F)c3Cl) c12 | NMR (400 MHz, DMSO-d6) 10.46 (br. s, 1H), 9.31 (br. s, 1H), 7.84 (d, 9.6 Hz, 1H), 7.80 (d, 1.6 Hz, 1H), 7.72 (d, 1.4 Hz, 1H), 7.46 (dd, 8.3, 5.3 Hz, 1H), 7.30 (d, 6.7 Hz, 1H), 7.24 (ddd, 8.8, 8.0, 3.1 Hz, 1H), 6.67 (br. s, 1H), 5.98 (br. s, 1H), | 547 | D | |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-695 | 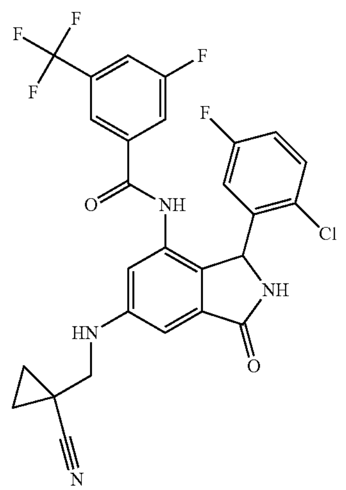 [SMILES: N#CC1(CNc2cc(NC(=O)c3cc(F)cc(C(F)(F)F)c3)c3c(c2)C(=O)NC3c2cc(F)ccc2Cl)CC1] | Fc1ccc(C1)c(c1)C1NC(=O)c2cc(NCC3(CC3)C#N)cc(NC(=O)c3cc(F)cc(c3)C(F)(F)F)c12 | 1H NMR (400 MHz, DMSO-d6) 10.32 (s, 1H), 8.94 (s, 1H), 7.92 (d, 8.3 Hz, 1H), 7.70 (d, 8.9 Hz, 1H), 7.62 (s, 1H), 7.28 (dd, 8.8, 5.2 Hz, 1H), 7.06 (td, 8.5, 2.9 Hz, 1H), 6.92 (d, 1.6 Hz, 1H), 6.79 (s, 1H), 6.62 (br s, 1H), 6.57 (br t, 5.6 Hz, 1H), 5.84 (br s, 1H), 3.30 (m, 2H), 1.33-1.17 (m, 2H), 1.14-0.98 (m, 2H). | 559.5 | A | |
| I-696 | 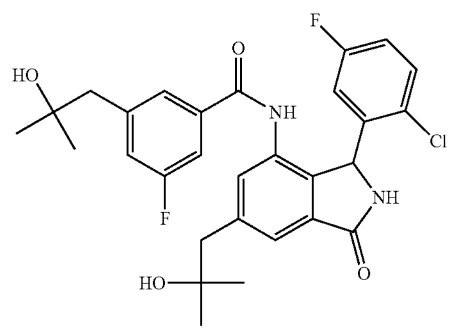 [SMILES: CC(C)(O)Cc1cc(F)cc(C(=O)Nc2cc(CC(C)(C)O)cc3c2C(c2cc(F)ccc2Cl)NC3=O)c1] | CC(C)(O)Cc1cc2C(=O)NC(c2c(NC(=O)c2cc(F)cc(CC(C)(C)O)c2)c1)c1cc(F)ccc1Cl | NMR (400 MHz, DMSO) 10.13 (s, 1H), 9.03 (s, 1H), 7.52 (s, 1H), 7.37-7.28 (m, 3H), 7.22 (d, 9.7 Hz, 1H), 7.11 (m, 2H), 6.61 (s, 1H), 6.00 (s, 1H), 4.45 (s, 1H), 4.42 (s, 1H), 2.82 (d, 12.7 Hz, 1H), 2.77 (d, 13.4 Hz, 1H)., 2.67 (s, 2H), 1.12 (s, 3H), 1.09 (s, 3H), 1.05 (s, 3H), 1.04 (s, 3H). | 543 | E | |
| I-697 | 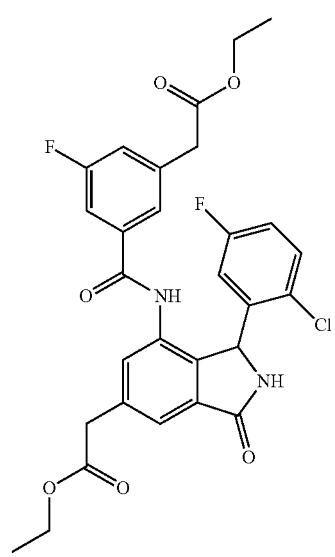 [SMILES: CCOC(=O)Cc1cc(F)cc(C(=O)Nc2cc(CC(=O)OCC)cc3c2C(c2cc(F)ccc2Cl)NC3=O)c1] | CCOC(=O)Cc1cc2C(=O)NC(c2c(NC(=O)c2cc(F)cc(CC(=O)OCC)c2)c1)c1cc(F)ccc1Cl | NMR (400 MHz, DMSO) 10.23 (s, 1H), 9.12 (s, 1H), 7.59 (s, 1H), 7.41 (s, 1H), 7.36-7.32 (m, 3H), 7.18 (m, 1H), 7.12 (td, 8.5, 3.2 Hz, 1H), 6.58 (br s, 1H), 5.99 (br s, 1H), 4.12 (q, 7.1, 2H), 4.11 (q, 7.1, 2H), 3.90 (d, A of AB, 16 Hz, 1H), 3.85 (d, B of AB, 16 Hz, 1H), 3.74 (s, 2H), 1.21 (t, 7.1, 3H), 1.20 (tt, 7.1, 3H). | 571 | D | |

TABLE 2-continued

Representative Compounds of the Invention with Bioactivity Data.

| Ex. No. | Structure | SMILES | $^1$H NMR | MS | ADP-Glo IC$_{50}$ | MCF 10A IC$_{50}$ |
|---|---|---|---|---|---|---|
| I-698 | 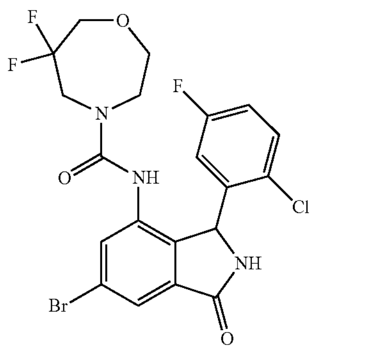 [SMILES: O=C1NC(c2cc(F)ccc2Cl)c2c(NC(=O)N3CCOCC(F)(F)C3)cc(Br)cc21] | Fc1ccc(C1)c(c1)C1NC(=O)c2cc(Br)cc(NC(=O)N3CCOCC(F)(F)C3)c12 | 1H-NMR (400 MHz, DMSO-d6)-9.22 (s, 1H), 8.66 (s, 1H), 7.66 (d, 1.6 Hz, 1H), 7.55 (d, 1.7 Hz, 1H), 7.53-7.47 (m, 1H), 7.23 (td, 8.4, 3.1 Hz, 1H), 6.57 (br. s, 1H), 6.04 (br s, 1H), 4.17 (dt, 15.4, 11.2 Hz, 1H), 3.77-3.53 (m, 4H), 3.52-3.41 (m, 2H), 3.19 (ddd, 14.6, 8.0, 3.6 Hz, 1H). | 518.2 | | E |
| I-699 | 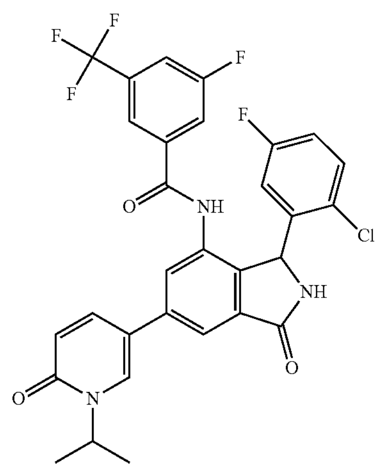 [SMILES: CC(C)n1cc(-c2cc(NC(=O)c3cc(F)cc(C(F)(F)F)c3)c3c(c2)C(=O)NC3c2cc(F)ccc2Cl)ccc1=O] | CC(C)n1cc(ccc1=O)-c1cc2C(=O)NC(c2cc(NC(=O)c2cc(F)cc(c2)C(F)(F)F)c1)c1cc(F)ccc1Cl | 1H NMR (DMSO-d6, 500 MHz):-' = 10.54 (s, 1H), 9.17 (br s, 1H), 8.17 (d, 2.7 Hz, 1H), 7.94-7.98 (m, 2H), 7.88 (dd, 9.5, 2.6 Hz, 1H), 7.68-7.78 (m, 3H), 7.32 (dd, 8.9, 5.2 Hz, 1H), 7.10 (td, 8.4, 3.1 Hz, 1H), 6.55-6.84 (m, 1H), 6.52 (d, 9.5 Hz, 1H), 6.00 (br s, 1H), 5.12 (quin, 6.8 Hz, 1H), 1.40 (dd, 6.9, 2.9 Hz, 6H) | 602.1 | | A |
| I-700 | 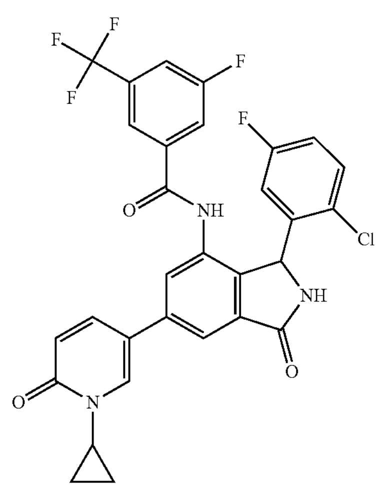 [SMILES: O=C(Nc1cc(-c2ccc(=O)n(C3CC3)c2)cc2c1C(c1cc(F)ccc1Cl)NC2=O)c1cc(F)cc(C(F)(F)F)c1] | Fc1ccc(C1)c(c1)C1NC(=O)c2cc(cc(NC(=O)c3cc(F)cc(c3)C(F)(F)F)c12)-c1ccc(=O)n(c1)C1CC1 | 1H NMR (DMSO-d6, 500 MHz) 10.53 (s, 1H), 9.16 (br s, 1H), 7.93-7.98 (m, 2H), 7.91 (d, 1.2 Hz, 1H), 7.88 (dd, 9.5, 2.7 Hz, 1H), 7.76 (br d, 8.2 Hz, 1H), 7.70 (s, 2H), 7.32 (dd, 8.9, 5.1 Hz, 1H), 7.10 (td, 8.4, 3.1 Hz, 1H), 6.54-6.76 (m, 1H), 6.51 (d, 9.3 Hz, 1H), 6.01 (br s, 1H), 3.38-3.43 (m, 1H), 0.99-1.05 (m, 4H) | 600.1 | | A |

TABLE 2-continued

Representative Compounds of the Invention with Bioactivity Data.

| Ex. No. | Structure | SMILES | $^1$H NMR | MS | ADP-Glo IC$_{50}$ | MCF 10A IC$_{50}$ |
|---|---|---|---|---|---|---|
| I-701 | 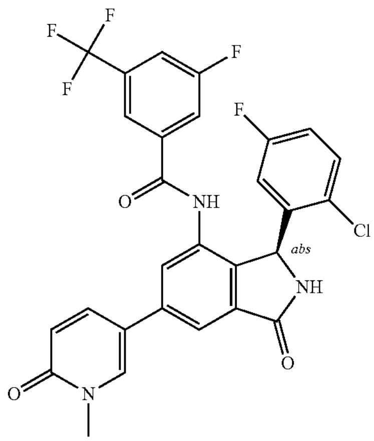 [SMILES: Cn1cc(-c2cc(NC(=O)c3cc(F)cc(C(F)(F)F)c3)c3c(c2)C(=O)N[C@@H]3c2cc(F)ccc2Cl)ccc1=O] | Cn1cc(ccc1=O)-c1cc2C(=O)N[C@@H](c2c(NC(=O)c2cc(F)cc(c2)C(F)(F)F)c1)c1cc(F)ccc1Cl | $^1$H NMR (400 MHz, DMSO-d$_6$) δ 10.90 (s, 1H), 9.52 (s, 1H), 8.62 (d, J = 1.5 Hz, 1H), 8.18 (dd, J = 8.6, 1.6 Hz, 1H), 7.98 (d, J = 8.7, 1H), 7.87 (s, 1H), 7.75 (d, J = 8.5, 1H), 7.67 (s, 1H), 7.35 (m, 1H), 7.10 (td, 8.6, 1.6 Hz, 1H), 6.57 (d, J = 8.8 Hz, 1H), 6.02 (s, 1H), 3.59 (s, 3H). | 574.3 | C | |
| I-702 | 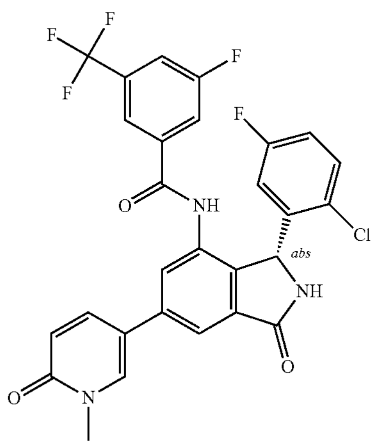 [SMILES: Cn1cc(-c2cc(NC(=O)c3cc(F)cc(C(F)(F)F)c3)c3c(c2)C(=O)N[C@H]3c2cc(F)ccc2Cl)ccc1=O] | Cn1cc(ccc1=O)-c1cc2C(=O)N[C@H](c2c(NC(=O)c2cc(F)cc(c2)C(F)(F)F)c1)c1cc(F)ccc1Cl | $^1$H NMR (400 MHz, DMSO-d$_6$) δ 10.90 (s, 1H), 9.52 (s, 1H), 8.62 (d, J = 1.5 Hz, 1H), 8.18 (dd, J = 8.6, 1.6 Hz, 1H), 7.98 (d, J = 8.7, 1H), 7.87 (s, 1H), 7.75 (d, J = 8.5, 1H), 7.67 (s, 1H), 7.35 (m, 1H), 7.10 (td, 8.6, 1.6 Hz, 1H), 6.57 (d, J = 8.8 Hz, 1H), 6.02 (s, 1H), 3.59 (s, 3H). | 574.2 | A | |
| I-703 | 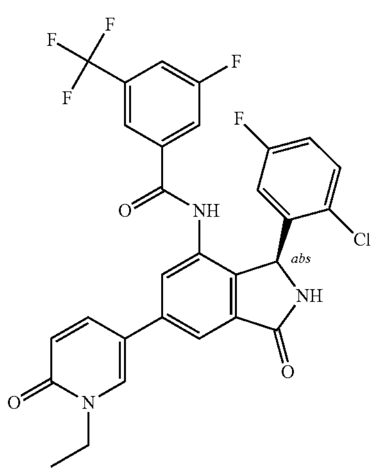 [SMILES: CCn1cc(-c2cc(NC(=O)c3cc(F)cc(C(F)(F)F)c3)c3c(c2)C(=O)N[C@@H]3c2cc(F)ccc2Cl)ccc1=O] | CCn1cc(ccc1=O)-c1cc2C(=O)N[C@@H](c2c(NC(=O)c2cc(F)cc(c2)C(F)(F)F)c1)c1cc(F)ccc1Cl | | 588.2 | E | |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-704 | 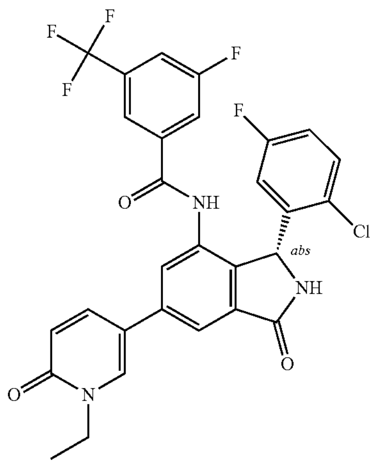 [SMILES: CCn1cc(-c2cc(NC(=O)c3cc(F)cc(C(F)(F)F)c3)c3c(c2)C(=O)N[C@H]3c2cc(F)ccc2Cl)ccc1=O] | CCn1cc(ccc1=O)-c1cc2C(=O)N[C@H](c2c(NC(=O)c2cc(F)cc(c2)C(F)(F)F)c1c(F)ccc1Cl | | 588.4 | A | |
| I-705 | 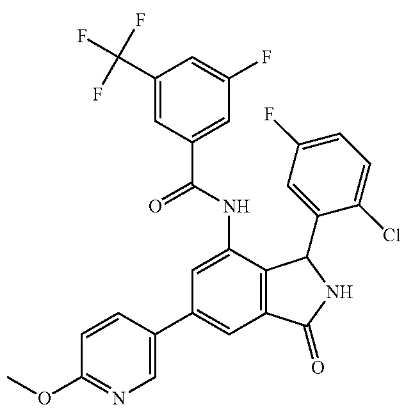 [SMILES: COc1ccc(-c2cc(NC(=O)c3cc(F)cc(C(F)(F)F)c3)c3c(c2)C(=O)NC3c2cc(F)ccc2Cl)cn1] | COc1ccc(cn1)-c1cc2C(=O)NC(c2c(NC(=O)c2cc(F)cc(c2)C(F)(F)F)c1c1cc(F)ccc1Cl | | 574 | A | |
| I-706 | 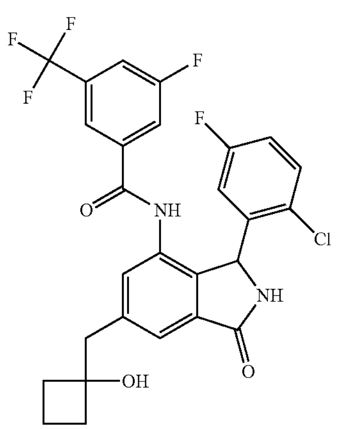 [SMILES: O=C(Nc1cc(CC2(O)CCC2)cc2c1C(c1cc(F)ccc1Cl)NC2=O)c1cc(F)cc(C(F)(F)F)c1] | OC1(Cc2cc3C(=O)NC(c3c(NC(=O)c3cc(F)cc(c3)C(F)(F)F)c2cc(F)ccc2Cl)CCC1 | 1H NMR (500 MHz., DMSO-d6) 1.48-1.67 (m, 2H), 1.88-2.03 (m, 4H), 2.94 (d, 15.26 Hz, 2H), 5.10 (s, 1H), 5.79-6.05 (m, 1H), 7.07 (td, 8.32, 3.05 Hz, 1H), 7.29 (dd, 8.85, 5.19 Hz, 1H), 7.38 (s, 1H), 7.63 (d, 17.85 Hz, 2H), 7.72 (br d, 8.85 Hz, 1H), 7.91 (br d, 8.39 Hz, 1H), 9.04 (br s, 1H), 10.44 (s, 1H) | 551.41 | A | |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-707 | 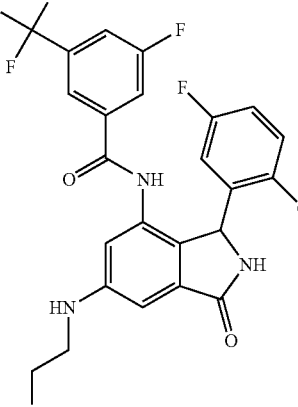 | OCCNc1cc2C(=O)NC(c2c(NC(=O)c2cc(F)cc(c2)C(F)(F)F)c1)c1cc(F)ccc1Cl | 1H NMR (500 MHz, DMSO-d6) 3.16 (q, 5.80 Hz, 2 H) 3.55-3.63 (m, 2 H) 4.75 (br t, 4.43 Hz, 1 H) 6.13-6.18 (m, 1 H) 6.69 (s, 1 H) 6.75 (br s, 1 H) 6.82 (d, 1.83 Hz, 1 H) 7.04 (td, 8.28, 2.98 Hz, 1 H) 7.26 (dd, 8.85, 5.19 Hz, 1 H) 7.61 (s, 1 H) 7.66-7.71 (m, 1 H) 7.89 (br d, 8.09 Hz, 1 H) 8.50 (s, 1 H) 8.87 (br s, 1 H) 10.26 (s, 1 H) | 526.4 | A | |
| I-708 | 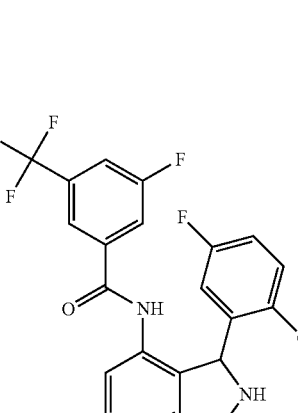 | CC(=O)COc1cc2C(=O)NC(c2c(NC(=O)c2cc(F)cc(c2)C(F)(F)F)c1)c1cc(F)ccc1Cl | 1H NMR (DMSO-d6, 500 MHz) 10.3-10.6 (m, 1H), 9.0-9.2 (m, 1H), 7.8-8.0 (m, 1H), 7.63 (s, 2H), 7.2-7.4 (m, 1H), 7.1-7.2 (m, 1H), 7.0-7.1 (m, 2H), 5.8-6.1 (m, 1H), 4.9-5.2 (m, 2H), 2.1-2.3 (m, 3H), 1.0-1.3 (m, 3H) | 539 | A | |
| I-709 | 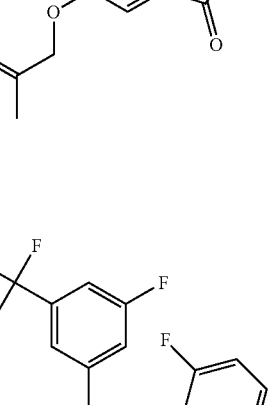 | CC(C)(O)COc1cc2C(=O)NC(c2c(NC(=O)c2cc(F)cc(c2)C(F)(F)F)c1)c1cc(F)ccc1Cl | 1H NMR (DMSO-d6, 500 MHz) 10.3-10.5 (m, 1H), 9.0-9.2 (m, 1H), 7.9-8.1 (m, 1H), 7.7-7.8 (m, 1H), 7.6-7.7 (m, 1H), 7.3-7.4 (m, 1H), 7.1-7.2 (m, 1H), 7.0-7.1 (m, 2H), 6.3-6.8 (m, 1H), 5.7-6.1 (m, 1H), 4.5-4.8 (m, 1H), 3.7-3.9 (m, 2H), 1.1-1.4 (m, 6H) | 555 | A | |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-710 | 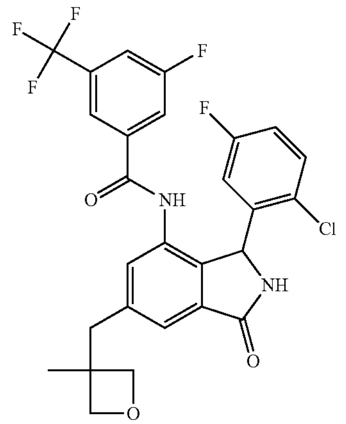 [SMILES: CC1(Cc2cc(NC(=O)c3cc(F)cc(C(F)(F)F)c3)c3c(c2)C(=O)NC3c2cc(F)ccc2Cl)COC1] | CC1(Cc2cc3C(=O)NC(c3c(NC(=O)c3cc(F)cc(c3)C(F)(F)F)c2)c2ccc(F)ccc2Cl)COC1 | 1H NMR (400 MHz, DMSO-d6) 1.24 (s, 2 H) 1.25-1.25 (m, 1 H) 2.83-3.16 (m, 3 H) 4.23 (d, 5.56 Hz, 2 H) 4.58 (t, 5.68 Hz, 2 H) 5.76-6.07 (m, 1 H) 7.09 (td, 8.46, 3.03 Hz, 1 H) 7.28-7.33 (m, 2 H) 7.51 (s, 1 H) 7.65 (s, 1 H) 7.73 (br d, 8.59 Hz, 1 H) 7.94 (br d, 8.59 Hz, 1 H) 9.10 (br s, 1 H) 10.45 (s, 1 H) | 551.41 | A | |
| I-711 | 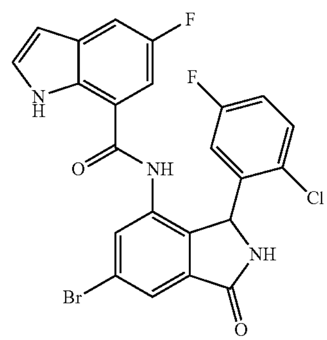 [SMILES: O=C1NC(c2cc(F)ccc2Cl)c2c(NC(=O)c3cc(F)cc4cc[nH]c34)cc(Br)cc21] | Fc1ccc(C1)c(c1)C1NC(=O)c2cc(Br)cc(NC(=O)c3cc(F)cc4cc[nH]c34)c12 | | | A | |
| I-712 | 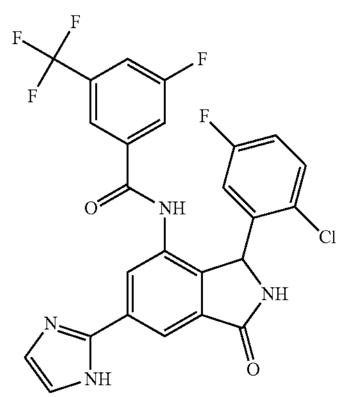 [SMILES: O=C(Nc1cc(-c2ncc[nH]2)cc2c1C(c1cc(F)ccc1Cl)NC2=O)c1cc(F)cc(C(F)(F)F)c1] | Fc1ccc(C1)c(c1)C1NC(=O)c2cc(cc(NC(=O)c3cc(F)cc(c3)C(F)(F)F)c12)-c1ncc[nH]1 | 1H NMR (400 MHz, DMSO-d6) 12.83 (br. s, 1H), 10.65 (s, 1H), 9.22 (s, 1H), 8.37 (s, 1H), 8.27 (d, 0.7 Hz, 1H), 8.14 (d, 1.0 Hz, 1H), 7.96 (d, 8.3 Hz, 1H), 7.77 (d, 8.6 Hz), 7.69 (s, 1H), 7.32 (dd, 8.9, 5.2 Hz, 1H), 7.34-7.07 (m, 1H), 7.09 (td, 8.5, 3.0 Hz, 1H), 6.66 (br. s, 1H), 6.02 (br. s, 1H) | 533.2 | A | |
| I-713 | 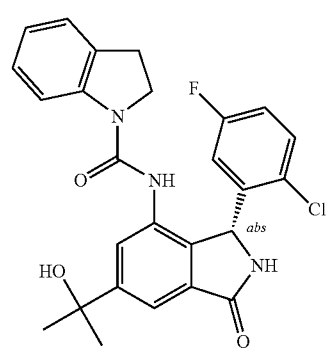 [SMILES: CC(C)(O)c1cc(NC(=O)N2CCc3ccccc32)c2c(c1)C(=O)N[C@H]2c1cc(F)ccc1Cl] | CC(C)(O)c1cc2C(=O)N[C@H](c2c(NC(=O)N2CCc3ccccc23)c1)c1cc(F)ccc1Cl | (400 MHz, DMSO-d6) 8.99 (s, 1H), 8.55 (s, 1H), 7.71 (d, 7.9 Hz, 1H), 7.65 (d, 1.4 Hz, 1H), 7.49 (d, 1.4 Hz, 1H), 7.36 (dd, 8.9, 5.2 Hz, 1H), 7.20-7.11 (m, 2H), 7.09 (t, 7.7 Hz, 1H), 6.88 (td, 7.4, 1.0 Hz, 1H), 6.54 (br s, 1H), 5.97 (br s, 1H), 5.25 (br s, 1H), 3.93-3.83 (m, 1H), 3.09-2.93 (m, 3H), 1.49 (s, 6H). | 480.2 | A | |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-714 | 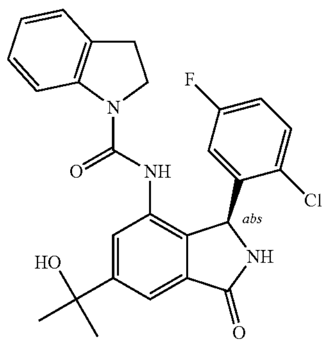 [SMILES: CC(C)(O)c1cc(NC(=O)N2CCc3ccccc32)c2c(c1)C(=O)N[C@@H]2c1cc(F)ccc1Cl] | CC(C)(O)c1cc2C(=O)N[C@@H](c2c(NC(=O)N2CCc3ccccc23)c1)c1cc(F)ccc1Cl | (400 MHz, DMSO-d6) 8.99 (s, 1H), 8.55 (s, 1H), 7.71 (d, 7.9 Hz, 1H), 7.65 (d, 1.4 Hz, 1H), 7.49 (d, 1.4 Hz, 1H), 7.36 (dd, 8.9, 5.2 Hz, 1H), 7.20-7.11 (m, 2H), 7.09 (t, 7.7 Hz, 1H), 6.88 (td, 7.4, 1.0 Hz, 1H), 6.54 (br s, 1H), 5.97 (br s, 1H), 5.25 (br s, 1H), 3.93-3.83 (m, 1H), 3.09-2.93 (m, 3H), 1.49 (s, 6H) | 480.2 | E | |
| I-715 | 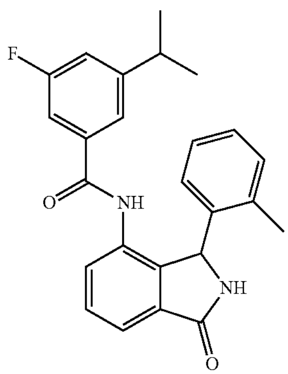 [SMILES: Cc1ccccc1C1NC(=O)c2cccc(NC(=O)c3cc(F)cc(C(C)C)c3)c21] | CC(C)c1cc(F)cc(c1)C(=O)Nc1cccc2C(=O)NC(c12)c1ccccc1C | 1H NMR (400 MHz, DMSO-d6) 10.03 (s, 1H), 9.05 (s, 1H), 7.65 (dd, 6.8, 1.8 Hz, 1H), 7.62-7.55 (m, 2H), 7.24 (dt, 9.9, 2.0 Hz, 1H), 7.09 (td, 7.3, 1.2 Hz, 1H), 7.03 (d, 7.1 Hz, 1H), 7.00-6.94 (m, 2H), 6.92 (d, 9.1 Hz, 1H), 6.55 (br s, 1H), 5.96 (s, 1H), 2.86 (sept, 6.8 Hz, 1H), 2.21 (br s, 3H), 1.18 (d, 1.7 Hz, 3H), 1.16 (d, 1.7 Hz, 3H). | 403.3 | D | |
| I-716 | 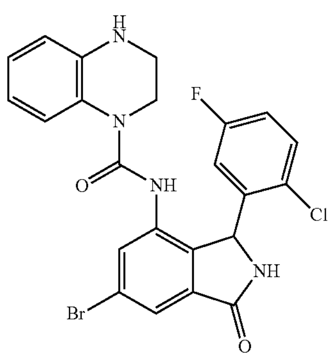 [SMILES: O=C1NC(c2cc(F)ccc2Cl)c2c(NC(=O)N3CCNc4ccccc43)cc(Br)cc21] | Fc1ccc(C1)c(c1)C1NC(=O)c2cc(Br)cc(NC(=O)N3CCNc4ccccc34)c12 | (400 MHz, DMSO-d6) 9.20 (br s, 1H), 8.70 (s, 1H), 7.66-7.57 (m, 2H), 7.48 (dd, 8.7, 5.0 Hz, 1H), 7.22 (td, 8.4, 2.9 Hz, 1H), 6.76 (ddd, 8.1, 7.3, 1.4 Hz, 1H), 6.54 (dd, 8.1, 1.3 Hz, 1H), 6.19 (ddd, 8.4, 7.4, 1.4 Hz, 1H), 6.12-5.97 (m, 3H), 4.07-3.95 (m, 1H), 3.31-3.24 (m, 2H), 3.03 (t, 9.0 Hz, 1H), 2.91 (t, 9.0 Hz, 1H). | 515.1 | D | |
| I-717 | 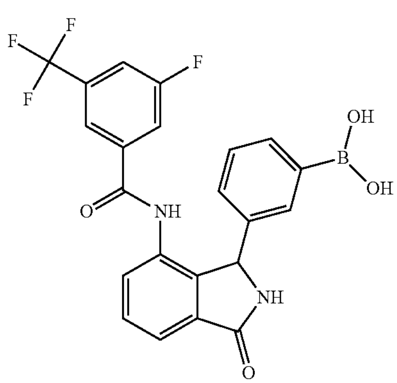 [SMILES: O=C(Nc1cccc2c1C(c1cccc(B(O)O)c1)NC2=O)c1cc(F)cc(C(F)(F)F)c1] | OB(O)c1cccc(c1)C1NC(=O)c2cccc(NC(=O)c3cc(F)cc(c3)C(F)(F)F)c12 | 1H NMR (400 MHz, d6-DMSO) 10.35 (s, 1H), 9.05 (s, 1H), 7.92 (s, 1H), 7.90 (s, 2H), 7.68 (dd, 7.4, 0.9 Hz, 1H), 7.66-7.61 (m, 3H), 7.58 (t, 7.6 Hz, 1H), 7.47 (d, 7.7 Hz, 1H), 7.44 (s, 1H), 7.07 (t, 7.5 Hz, 1H), 6.99 (m, 1H), 5.71 (s, 1H). | 457.4 | E | |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-718 | 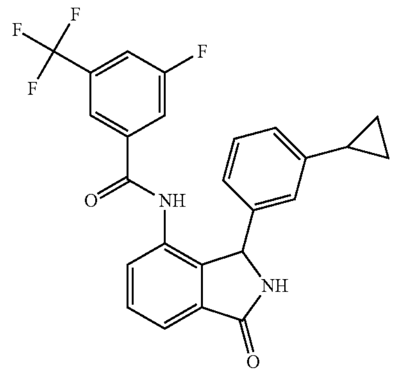 [SMILES: O=C(Nc1cccc2c1C(c1cccc(C3CC3)c1)NC2=O)c1cc(F)cc(C(F)(F)F)c1] | Fc1cc(cc (c1)C(F) (F)F)C(= O)Nc1cc cc2C(=O) NC(c12) c1cccc(c 1)C1CC1 | (400 MHz, d6-DMSO) 10.40 (s, 1H), 9.03 (s, 1H), 7.97 (d, 8.3 Hz, 1H), 7.70 (s, 1H), 7.69-7.64 (m, 2H), 7.59 (app t, 7.6 Hz, 1H), 7.45 (d, 7.1 Hz, 1H), 7.03 (app t, 7.7 Hz, 1H), 6.85 (d, 7.7 Hz, 1H), 6.71 (s, 1H), 6.61 (d, 7.6 Hz, 1H), 5.65 (s, 1H), 1.63-1.52 (m, 1H), 0.75-0.60 (m, 2H), 0.40-0.30 (m, 1H), 0.23-0.13 (m, 1H). | 455.2 | E | |
| I-719 | 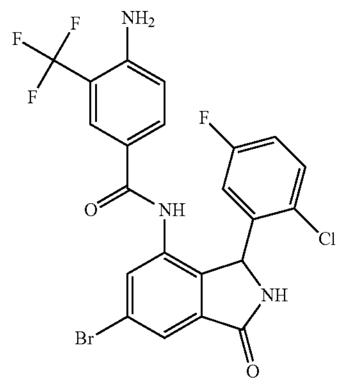 [SMILES: Nc1ccc(C(=O)Nc2cc(Br)cc3c2C(c2cc(F)ccc2Cl)NC3=O)cc1C(F)(F)F] | Nc1ccc(c c1C(F)(F) F)C(=O) Nc1cc(Br) cc2C(= O)NC(c1 2)c1cc(F) ccc1Cl | 1H NMR (400 MHz, DMSO-d6) 9.99 (s, 1H), 9.22 (s, 1H), 7.76-7.67 (m, 2H), 7.59-7.51 (m, 2H), 7.31 (dd, 8.9, 5.2 Hz, 1H), 7.08 (td, 8.4, 3.1 Hz, 1H), 6.78 (d, 8.6 Hz, 2H), 6.27 (s, 2H), 5.99 (s, 1H). | 542 | D | |
| I-720 | 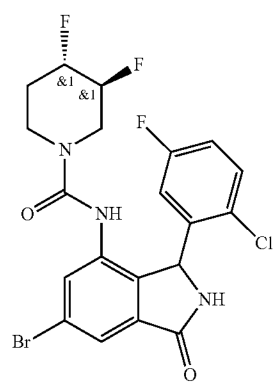 [SMILES: O=C1NC(c2cc(F)ccc2Cl)c2c(NC(=O)N3CC[C@H](F)[C@@H](F)C3)cc(Br)cc21] | F[C@H] 1CCN(C [C@@H] 1F)C(=O) Nc1cc(B r)cc2C(= O)NC(c1 2)c1cc(F) ccc1Cl | 1H-NMR (400 MHz, DMSO-d6) as a ca. 1:1 mixture of diastereomers-' 9.18 (br. s, 2H), 8.74 (s, 1H), 8.70 (s, 1H), 7.62-7.59 (m, 2H), 7.55 (d, 1.7 Hz, 1H), 7.48 (d, 1.7 Hz, 1H), 7.51-7.43 (m, 2H), 7.27-7.18 (m, 2H), 6.64 (br. s, 2H), 5.96 (br. s, 2H), 4.98-4.86 (m, 1H), 4.85-4.61 (m, 2H), 4.60-4.39 (m, 1H), 3.67-3.57 (m, 1H), 3.57-3.47 (m, 1H), 3.28-3.18 (m, 2H), 3.12-3.02 (m, 1H), 2.96-2.88 (m, 1H), 1.85-1.66 (m, 3H), 1.63-1.50 (m, 1H). | 504.2 | E | |

TABLE 2-continued

Representative Compounds of the Invention with Bioactivity Data.

| Ex. No. | Structure | SMILES | $^1$H NMR | MS | ADP-Glo IC$_{50}$ | MCF 10A IC$_{50}$ |
|---|---|---|---|---|---|---|
| I-721 | 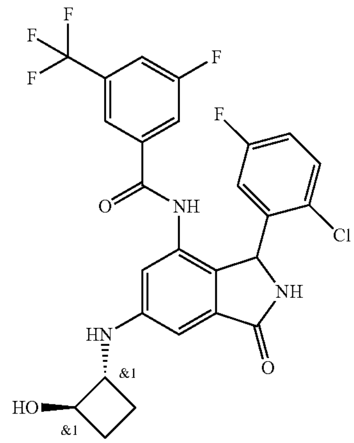 [SMILES: O=C(Nc1cc(N[C@@H]2CC[C@H]2O)cc2c1C(c1cc(F)ccc1Cl)NC2=O)c1cc(F)cc(C(F)(F)F)c1] | O[C@@H]1CC[C@H]1Nc1cc2C(=O)NC(c2c(NC(=O)c2cc(F)cc(c2)C(F)(F)F)c1)cc(F)ccc1Cl | 1H NMR (400 MHz, CD3CN) 8.49 (d, 11.1 Hz, 1H), 7.63 (d, 8.6 Hz, 1H), 7.56 (m, 3H), 7.23 (dd, 8.8, 5.1 Hz, 1H), 7.08 (s, 1H), 7.00 (t, 1.9 Hz, 1H), 6.97-6.92 (m, 1H), 6.85 (s, 1H), 6.64 (s, 1H), 5.96 (s, 1H), 5.19 (d, 6.1 Hz, 1H), 3.90 (dd, 15.2, 7.9 Hz, 1H), 3.67 (m, 1H), 1.62-1.44 (m 1H), 1.35-1.18 (m, 3H). | 552.2 | A | |
| I-722 | 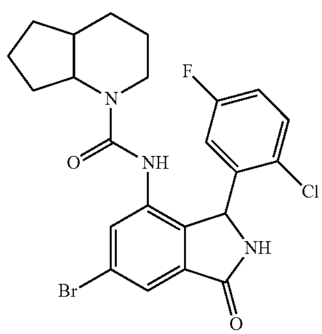 [SMILES: O=C1NC(c2cc(F)ccc2Cl)c2c(NC(=O)N3CCCC4CCCC43)cc(Br)cc21] | Fc1ccc(C1)c(c1)C1NC(=O)c2cc(Br)cc(NC(=O)N3CCCC4CCCC34)c12 | 1H NMR (400 MHz, CDCl3) 8.15 (d, 7.2 Hz, 1H), 7.78 (d, 1.3 Hz, 1H), 7.44 (dd, 8.7, 5.1 Hz, 1H), 7.08-7.04 (m, 1H), 6.64 (s, 1H), 6.42 (s, 1H), 6.09 (s, 1H), 5.99-5.96 (m, 1H), 3.81-3.61 (m, 2H), 2.72-2.58 (m, 1H), 1.86-1.71 (m, 3H), 1.69-1.52 (m, 11H), 1.51-1.39 (m, 4H), 1.37-1.24 (m, 3H), 1.21-1.12 (m, 1H). | 508 | B | |
| I-723 | 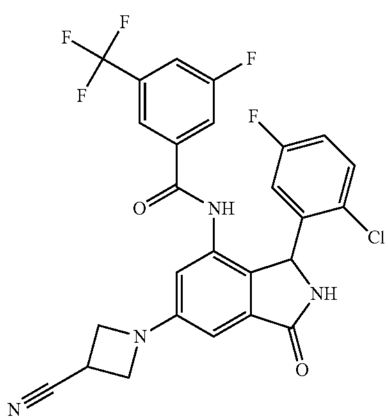 | Fc1ccc(C1)c(c1)C1NC(=O)c2cc(cc(NC(=O)c3cc(F)cc(c3)C(F)(F)F)c12)N1CC(C1)C#N | NMR (400 MHz, CD3CN) 8.49 (s, 1H), 7.62 (d, 8.5 Hz, 1H), 7.55 (d, 8.9 Hz, 1H), 7.52 (s, 1H), 7.22 (dd, 8.9, 5.1 Hz, 1H), 7.12 (br s, 1H), 6.97-6.90 (m), 6.79 (d, 2.0 Hz, 1H), 6.65 (s, 1H), 6.59 (br s, 1H), 5.99 (br s, 1H), 4.24-4.17 (m, 2H), 4.13-4.07 (m, 2H), 3.68 (m, 1H). | 547.3 | A | |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-724 | 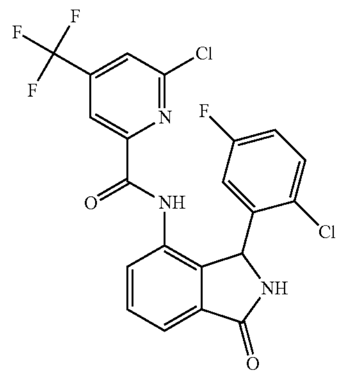 [SMILES: O=C(Nc1cccc2c1C(c1cc(F)ccc1Cl)NC2=O)c1cc(C(F)(F)F)cc(Cl)n1] | Fc1ccc(C1)c(c1)C1NC(=O)c2cccc(NC(=O)c3cc(cc(Cl)n3)C(F)(F)F)c12 | 1H-NMR (400 MHz, DMSO-d6) 10.29 (br. s, 1H), 9.14 (br. s, 1H), 8.33 (s, 1H), 8.15 (s, 1H), 7.75 (dd, 7.5, 0.9 Hz, 1H), 7.70-7.60 (m, 1H), 7.32 (dd, 8.8, 5.0 Hz, 1H), 7.07 (td, 8.5, 2.9 Hz, 1H), 6.58 (br. s, 1H), 6.11 (br. s, 1H). | 484.2 | D | |
| I-725 | 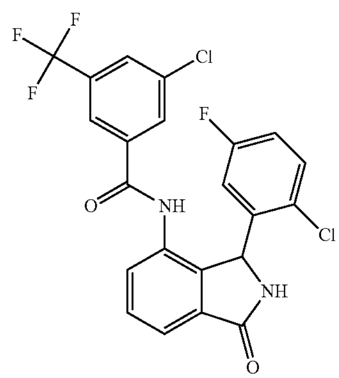 [SMILES: O=C(Nc1cccc2c1C(c1cc(F)ccc1Cl)NC2=O)c1cc(Cl)cc(C(F)(F)F)c1] | Fc1ccc(C1)c(c1)C1NC(=O)c2cccc(NC(=O)c3cc(Cl)cc(c3)C(F)(F)F)c12 | 1H NMR (400 MHz, DMSO-d6) 10.52 (br. s, 1H), 9.15 (br. s, 1H), 8.11 (s, 1H), 7.87 (s, 1H), 7.76 (s, 1H), 7.71 (d, 7.1 Hz, 1H), 7.64 (t, 7.6 Hz, 1H), 7.49 (d, 7.5 Hz, 1H), 7.32 (dd, 8.9, 5.2 Hz, 1H), 7.10 (td, 8.4, 3.0 Hz, 1H), 6.52 (br. s, 1H), 5.98 (br. s, 1H). | 483.1 | C | |
| I-726 | 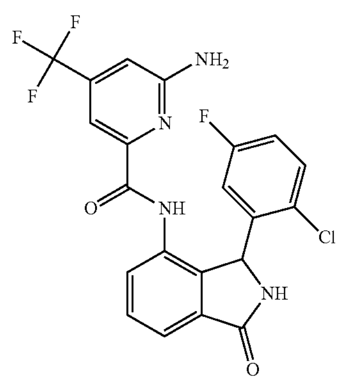 [SMILES: Nc1cc(C(F)(F)F)cc(C(=O)Nc2cccc3c2C(c2cc(F)ccc2Cl)NC3=O)n1] | Nc1cc(cc(n1)C(=O)Nc1cccc2C(=O)NC(c12)c1cc(F)ccc1Cl)C(F)(F)F | 1H NMR (400 MHz, DMSO-d6) 9.86 (s, 1H), 9.14 (s, 1H), 7.86 (dd, 6.7, 2.2 Hz, 1H), 7.64-7.60 (m, 2H), 7.41-7.32 (m, 1H), 7.22 (s, 1H), 7.11 (td, 8.4, 3.0 Hz, 1H), 6.97-6.95 (m, 1H), 6.63 (br. s, 2H), 6.63 (br. s, 1H), 6.12 (br. s, 1H). | 465.2 | D | |
| I-727 | 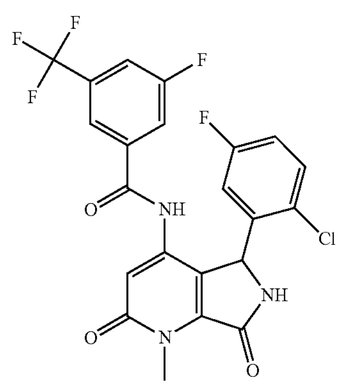 [SMILES: Cn1c2c(c(NC(=O)c3cc(F)cc(C(F)(F)F)c3)cc1=O)C(c1cc(F)ccc1Cl)NC2=O] | Cn1c2C(=O)NC(c2c(NC(=O)c2cc(F)cc(c2)C(F)(F)F)cc1=O)c1cc(F)ccc1Cl | (400 MHz, DMSO-d6) 8.35 (s, 1H), 8.12-8.01 (m, 1H), 7.95 (d, 8.7 Hz, 1H), 7.83 (br. s, 2H), 7.57 (br. s, 1H), 7.27 (ddd, 8.8, 8.0, 3.1 Hz, 1H), 6.42 (br. s, 1H), 5.68 (s, 1H), 3.56 (s, 3H) | 498.3 | E | |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-728 | 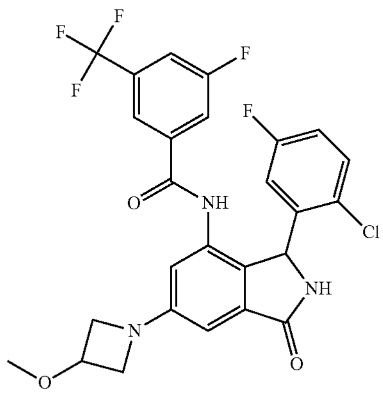 [SMILES: COC1CN(c2cc(NC(=O)c3cc(F)cc(C(F)(F)F)c3)c3c(c2)C(=O)NC3c2cc(F)ccc2Cl)C1] | COC1CN(C1)c1cc2C(=O)NC(c2c(NC(=O)c2cc(F)cc(c2)C(F)(F)F)c1c1c(F)ccc1Cl | NMR (400 MHz, CD3CN) 8.49 (s, 1H), 7.63 (d, 8.6 Hz, 1H), 7.57 (d, 9.2 Hz, 1H), 7.55 (s, 1H), 7.24 (dd, 8.8, 5.2 Hz, 1H), 7.11 (br s, 1H), 6.99-6.89 (m, 1H), 6.76 (d, 2.0 Hz, 1H), 6.63 (br s, 2H), 6.01 (br s, 1H), 4.39-4.33 (m, 1H), 4.27-4.07 (m, 2H), 3.95-3.65 (m, 2H), 3.31 (s, 3H). | 552.3 | B | |
| I-729 | 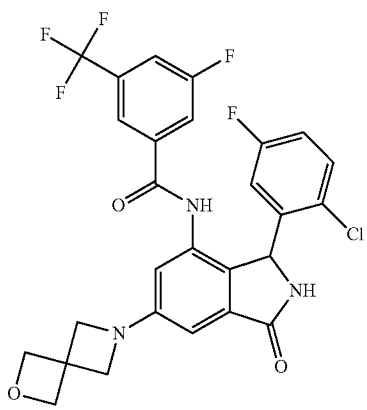 [SMILES: O=C(Nc1cc(N2CC3(COC3)C2)cc2c1C(c1cc(F)ccc1Cl)NC2=O)c1cc(F)cc(C(F)(F)F)c1] | Fc1ccc(C1)c(c1)C1NC(=O)c2cc(cc(NC(=O)c3cc(F)cc(c3)C(F)(F)F)c12)N1CC2(COC2)C1 | NMR (400 MHz, DMSO-d6) 10.35 (s, 1H), 9.00 (br. s, 1H), 7.93 (d, 8.4 Hz, 1H), 7.71 (d, 8.9 Hz, 1H), 7.64 (s, 1H), 7.29 (dd, 8.9, 5.2 Hz, 1H), 7.06 (td, 8.3, 3.1 Hz, 1H), 6.67 (d, 2.0 Hz, 1H), 6.52 (d, 1.5 Hz, 1H), 6.63-6.44 (br. s, 1H) 5.87 (br. s, 1H), 4.77-4.71 (m, 4H), 4.12-4.03 (m, 4H). | 564.3 | A | |
| I-730 | 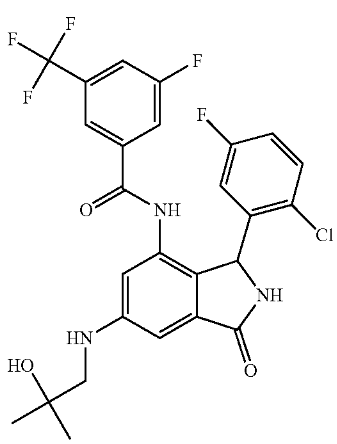 [SMILES: CC(C)(O)CNc1cc(NC(=O)c2cc(F)cc(C(F)(F)F)c2)c2c(c1)C(=O)NC2c1cc(F)ccc1Cl] | CC(C)(O)CNc1cc2C(=O)NC(c2c(NC(=O)c2cc(F)cc(c2)C(F)(F)F)c1c1c(F)ccc1Cl | 1H NMR (500 MHz, DMSO-d6) 1.19 (s, 6 H) 3.02 (dd, 5.72, 1.30 Hz, 2 H) 5.82 (br s, 1 H) 5.96 (br t, 5.19 Hz, 1 H) 6.78 (d, 1.37 Hz, 1 H) 6.90 (d, 1.98 Hz, 1 H) 7.05 (td, 8.39, 3.05 Hz, 1 H) 7.27 (dd, 8.85, 5.19 Hz, 1 H) 7.63 (s, 1 H) 7.69 (br d, 9.77 Hz, 1 H) 7.90 (br d, 8.39 Hz, 1 H) 8.86 (br s, 1 H) 10.18-10.31 (m, 1 H) | 554.36 | A | |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-731 | 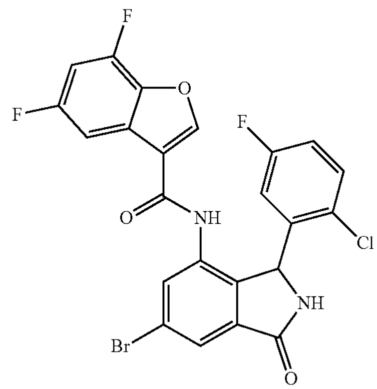 [SMILES: O=C1NC(c2cc(F)ccc2Cl)c2c(NC(=O)c3coc4c(F)cc(F)cc34)cc(Br)cc21] | Fc1ccc(C1)c(c1)C1NC(=O)c2cc(Br)cc(NC(=O)c3coc4c(F)cc(F)cc34)c12 | 1H NMR (500 MHz, DMSO-d6) 6.03 (br s, 1 H) 7.05 (td, 8.35, 3.13 Hz, 1 H) 7.29 (dd, 8.85, 5.19 Hz, 1 H) 7.38-7.55 (m, 2 H) 7.70 (s, 1 H) 7.80 (d, 1.53 Hz, 1 H) 8.48 (s, 1 H) 9.26 (br s, 1 H) 10.32 (br s, 1 H) | 537.25 | A | |
| I-732 | 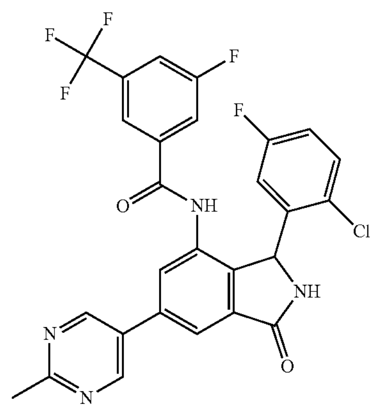 [SMILES: Cc1ncc(-c2cc(NC(=O)c3cc(F)cc(C(F)(F)F)c3)c3c(c2)C(=O)NC3c2cc(F)ccc2Cl)cn1] | Cc1ncc(cn1)-c1cc2C(=O)NC(c2c(NC(=O)c2cc(F)cc(c2)C(F)(F)F)c1)c1cc(F)ccc1Cl | | 559 | A | |
| I-733 | 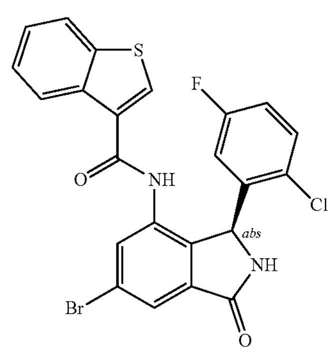 [SMILES: O=C1N[C@H](c2cc(F)ccc2Cl)c2c(NC(=O)c3csc4ccccc34)cc(Br)cc21] | Fc1ccc(C1)c(c1)[C@H]1NC(=O)c2cc(Br)cc(NC(=O)c3csc4cccc34)c12 | | 517.3 | D | |
| I-734 | 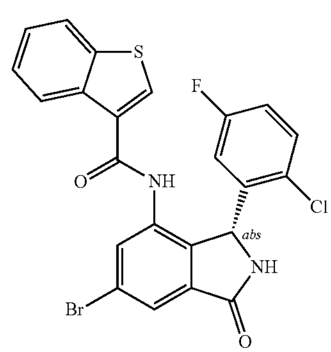 [SMILES: O=C1N[C@@H](c2cc(F)ccc2Cl)c2c(NC(=O)c3csc4ccccc34)cc(Br)cc21] | Fc1ccc(C1)c(c1)[C@@H]1NC(=O)c2cc(Br)cc(NC(=O)c3csc4cccc34)c12 | | 517.3 | A | |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-735 | 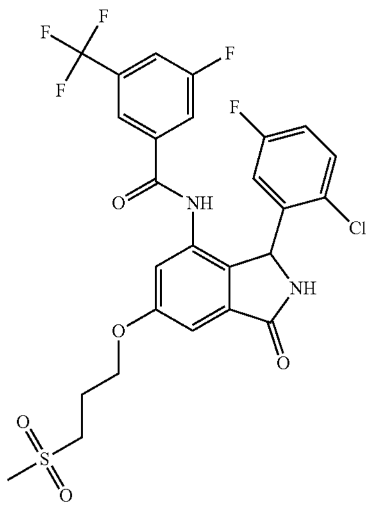 [SMILES: CS(=O)(=O)CCCOc1cc(NC(=O)c2cc(F)cc(C(F)(F)F)c2)c2c(c1)C(=O)NC2c1cc(F)ccc1Cl] | CS(=O)(=O)CCC Oc1cc2C(=O)NC(c2c(NC(=O)c2cc(F)cc(c2)C(F)(F)F)c1)c1cc(F)ccc1Cl | 1H NMR (DMSO-d6, 400 MHz) 10.3-10.4 (m, 1H), 10.0-10.1 (m, 1H), 7.8-8.0 (m, 1H), 7.6-7.7 (m, 1H), 7.5-7.6 (m, 1H), 7.2-7.3 (m, 1H), 7.1-7.1 (m, 1H), 7.0-7.0 (m, 1H), 6.9-7.0 (m, 1H), 6.8-6.9 (m, 1H), 6.2-6.6 (m, 1H), 5.8-6.1 (m, 1H), 4.3-4.5 (m, 2H), 3.2-3.5 (m, 2H) 3.0-3.0 (m, 3H), 2.1-2.3 (m, 2H) | 603 | B | |
| I-736 | 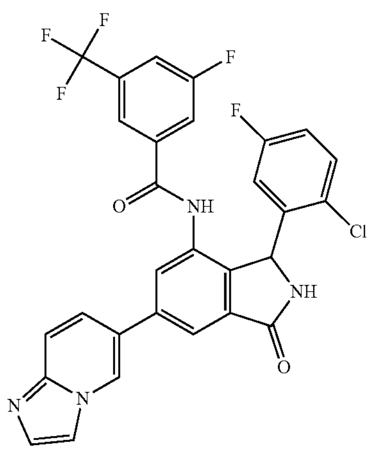 [SMILES: O=C(Nc1cc(-c2ccc3nccn3c2)cc2c1C(c1cc(F)ccc1Cl)NC2=O)c1cc(F)cc(C(F)(F)F)c1] | Fc1ccc(C1)c(c1)C1NC(=O)c2cc(cc(NC(=O)c3cc(F)cc(c3)C(F)(F)F)c12)-c1ccc2ncn2c1 | | 583 | A | |
| I-737 | 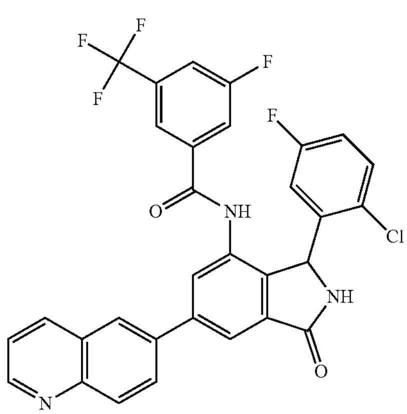 [SMILES: O=C(Nc1cc(-c2ccc3ncccc3c2)cc2c1C(c1cc(F)ccc1Cl)NC2=O)c1cc(F)cc(C(F)(F)F)c1] | Fc1ccc(C1)c(c1)C1NC(=O)c2cc(cc(NC(=O)c3cc(F)cc(c3)C(F)(F)F)c12)-c1ccc2nccccc2c1 | | 594 | A | |

TABLE 2-continued

Representative Compounds of the Invention with Bioactivity Data.

| Ex. No. | Structure | SMILES | $^1$H NMR | MS | ADP-Glo IC$_{50}$ | MCF 10A IC$_{50}$ |
|---|---|---|---|---|---|---|
| I-738 | 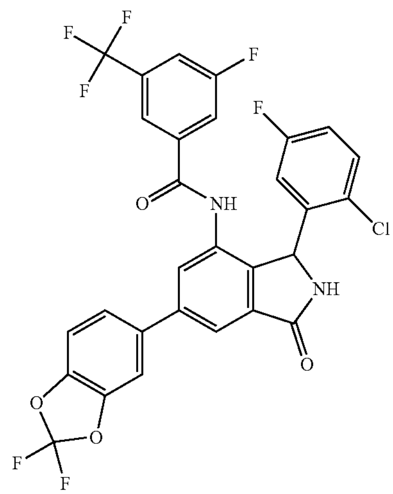 [SMILES: O=C(Nc1cc(-c2ccc3c(c2)OC(F)(F)O3)cc2c1C(c1cc(F)ccc1Cl)NC2=O)c1cc(F)cc(C(F)(F)F)c1] | Fc1ccc(C1)c(c1)C1NC(=O)c2cc(cc(NC(=O)c3cc(F)cc(c3)C(F)(F)F)c12)-c1ccc2OC(F)(F)Oc2c1 | | 623 | B | |
| I-739 | 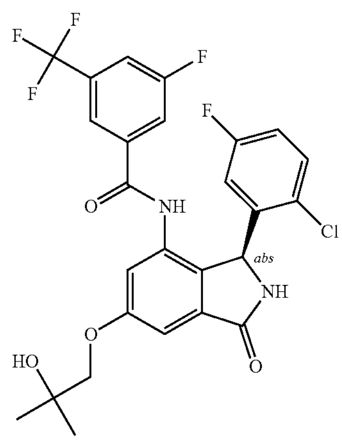 [SMILES: CC(C)(O)COc1cc(NC(=O)c2cc(F)cc(C(F)(F)F)c2)c2c(c1)C(=O)N[C@@H]2c1cc(F)ccc1Cl] | CC(C)(O)COc1cc2C(=O)N[C@@H](c2c(NC(=O)c2cc(F)cc(c2)C(F)(F)F)c1cc(F)ccc1Cl | 1H NMR (DMSO-d6, 400 MHz) 10.3-10.5 (m, 1H), 8.9-9.2 (m, 1H), 7.8-8.1 (m, 1H), 7.7-7.8 (m, 1H), 7.6-7.7 (m, 1H), 7.2-7.3 (m, 1H), 7.1-7.2 (m, 1H), 7.0-7.1 (m, 2H), 6.2-6.9 (m, 1H), 5.7-6.1 (m, 1H), 4.6-4.7 (m, 1H), 4.0-4.1 (m, 2H), 1.1-1.3 (m, 6H) | 555 | D | |
| I-740 | 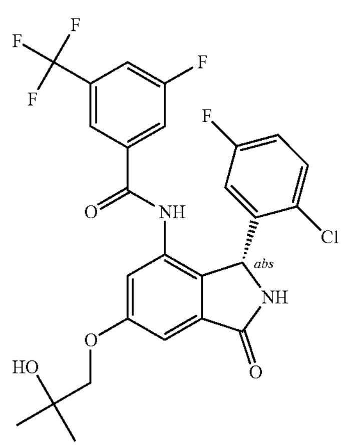 [SMILES: CC(C)(O)COc1cc(NC(=O)c2cc(F)cc(C(F)(F)F)c2)c2c(c1)C(=O)N[C@H]2c1cc(F)ccc1Cl] | CC(C)(O)COc1cc2C(=O)N[C@H](c2c(NC(=O)c2cc(F)cc(c2)C(F)(F)F)c1cc(F)ccc1Cl | 1H NMR (DMSO-d6, 400 MHz) 10.3-10.6 (m, 1H), 8.9-9.3 (m, 1H), 7.9-8.0 (m, 1H), 7.7-7.8 (m, 1H), 7.6-7.7 (m, 1H), 7.2-7.4 (m, 1H), 7.1-7.2 (m, 1H), 7.0-7.1 (m, 2H), 6.2-6.9 (m, 1H), 5.7-6.1 (m, 1H), 4.6-4.8 (m, 1H), 4.0-4.2 (m, 2H), 1.1-1.3 (m, 6H) | 555 | A | |

TABLE 2-continued

Representative Compounds of the Invention with Bioactivity Data.

| Ex. No. | Structure | SMILES | $^1$H NMR | MS | ADP-Glo IC$_{50}$ | MCF 10A IC$_{50}$ |
|---|---|---|---|---|---|---|
| I-741 | 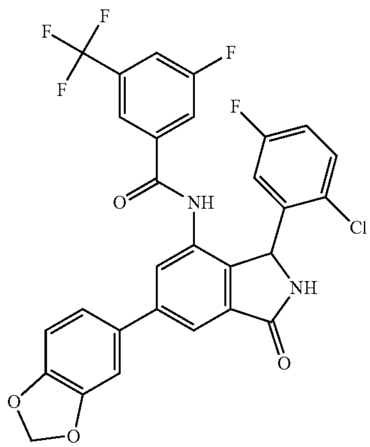 [SMILES: O=C(Nc1cc(-c2ccc3c(c2)OCO3)cc2c1C(c1cc(F)ccc1Cl)NC2=O)c1cc(F)cc(C(F)(F)F)c1] | Fc1ccc(C1)c(c1)C1NC(=O)c2cc(cc(NC(=O)c3cc(F)cc(c3)C(F)(F)F)c12)-c1ccc2OCOc2c1 | | 587 | A | |
| I-742 | 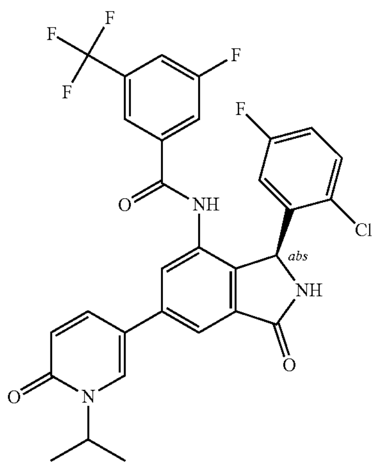 [SMILES: CC(C)n1cc(-c2cc(NC(=O)c3cc(F)cc(C(F)(F)F)c3)c3c(c2)C(=O)N[C@@H]3c2cc(F)ccc2Cl)ccc1=O] | CC(C)n1cc(ccc1=O)-c1cc2C(=O)N[C@@H](c2c(NC(=O)c2cc(F)cc(c2)C(F)(F)F)c1)c1cc(F)ccc1Cl | | 602.4 | D | |
| I-743 | 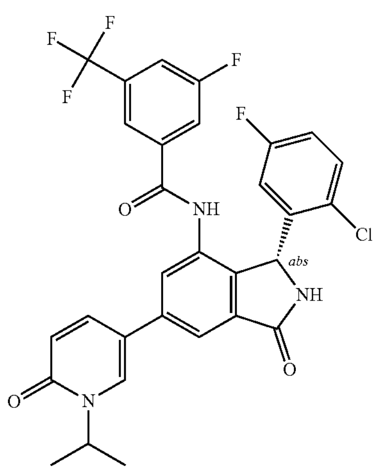 [SMILES: CC(C)n1cc(-c2cc(NC(=O)c3cc(F)cc(C(F)(F)F)c3)c3c(c2)C(=O)N[C@H]3c2cc(F)ccc2Cl)ccc1=O] | CC(C)n1cc(ccc1=O)-c1cc2C(=O)N[C@H](c2c(NC(=O)c2cc(F)cc(c2)C(F)(F)F)c1)c1cc(F)ccc1Cl | | 602.3 | A | |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-744 | 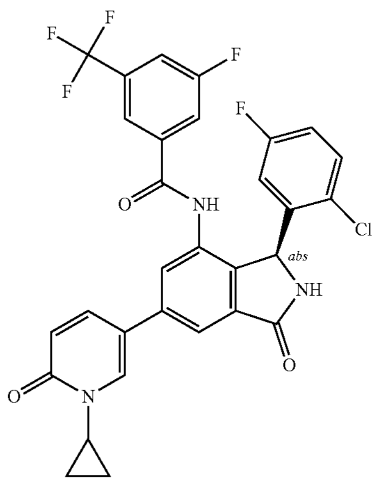 [SMILES: O=C(Nc1cc(-c2ccc(=O)n(C3CC3)c2)cc2c1[C@@H](c1cc(F)ccc1Cl)NC2=O)c1cc(F)cc(C(F)(F)F)c1] | Fc1ccc(C1)c(c1)[C@H]1NC(=O)c2cc(cc(NC(=O)c3cc(F)cc(c3)C(F)(F)F)c12)-c1ccc(=O)n(c1)C1CC1 | | 600.4 | D | |
| I-745 | 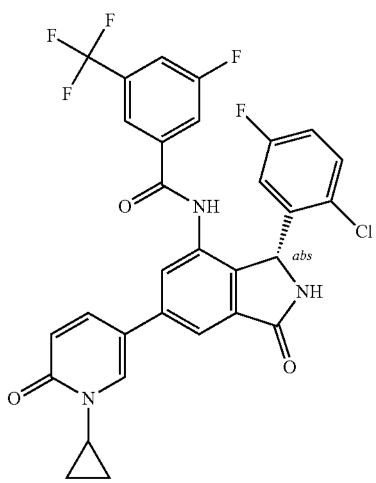 [SMILES: O=C(Nc1cc(-c2ccc(=O)n(C3CC3)c2)cc2c1[C@H](c1cc(F)ccc1Cl)NC2=O)c1cc(F)cc(C(F)(F)F)c1] | Fc1ccc(C1)c(c1)[C@@H]1NC(=O)c2cc(cc(NC(=O)c3cc(F)cc(c3)C(F)(F)F)c12)-c1ccc(=O)n(c1)C1CC1 | | 600.4 | A | |
| I-746 | 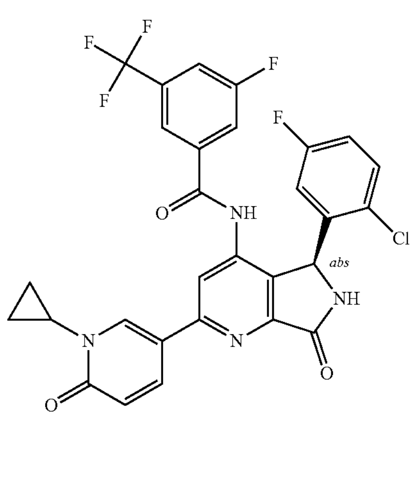 [SMILES: O=C(Nc1cc(-c2ccc(=O)n(C3CC3)c2)nc2c1[C@@H](c1cc(F)ccc1Cl)NC2=O)c1cc(F)cc(C(F)(F)F)c1] | Fc1ccc(C1)c(c1)[C@H]1NC(=O)c2nc(cc(NC(=O)c3cc(F)cc(c3)C(F)(F)F)c12)-c1ccc(=O)n(c1)C1CC1 | | 601.3 | D | |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-747 | 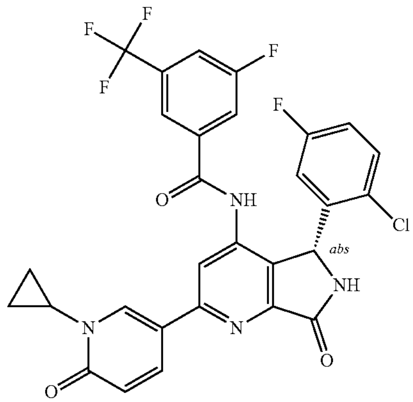 [SMILES: O=C(Nc1cc(-c2ccc(=O)n(C3CC3)c2)nc2c1[C@H](c1cc(F)ccc1Cl)NC2=O)c1cc(F)cc(C(F)(F)F)c1] | Fc1ccc(C1)c(c1)[C@@H]1NC(=O)c2nc(cc(NC(=O)c3cc(F)cc(c3)C(F)(F)F)c12)-c1ccc(=O)n(c1)C1CC1 | | 601.3 | A | A |
| I-748 | 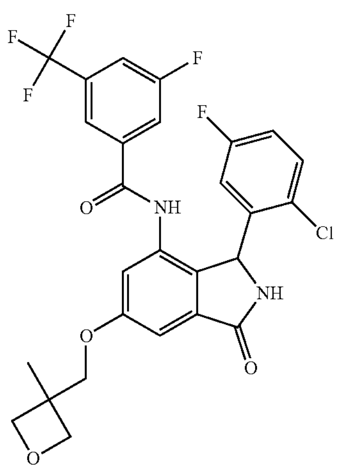 [SMILES: CC1(COc2cc(NC(=O)c3cc(F)cc(C(F)(F)F)c3)c3c(c2)C(=O)NC3c2cc(F)ccc2Cl)COC1] | CC1(COc2cc3C(=O)NC(c3c(NC(=O)c3cc(F)cc(c3)C(F)(F)F)c2)c2cc(F)ccc2Cl)COC1 | | 567 | A | |
| I-749 | 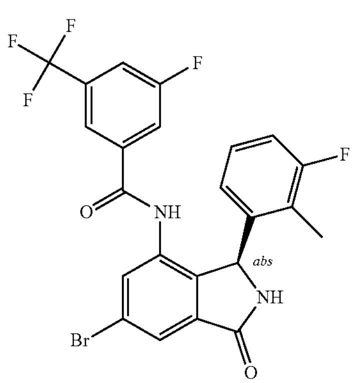 [SMILES: Cc1c(F)cccc1[C@H]1NC(=O)c2cc(Br)cc(NC(=O)c3cc(F)cc(C(F)(F)F)c3)c21] | Cc1c(F)cccc1[C@H]1NC(=O)c2cc(Br)cc(NC(=O)c3cc(F)cc(c3)C(F)(F)F)c12 | 1H NMR (400 MHz, DMSO-d6) 10.51 (s, 1H), 9.28 (s, 1H), 7.97-7.90 (m, 1H), 7.84-7.78 (m, 2H), 7.55 (d, 9.0 Hz, 1H), 7.34 (s, 1H), 7.02-6.93 (m, 2H), 6.36 (s, 1H), 5.93 (s, 1H), 2.19 (s, 3H). | 527 | D | |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-750 | 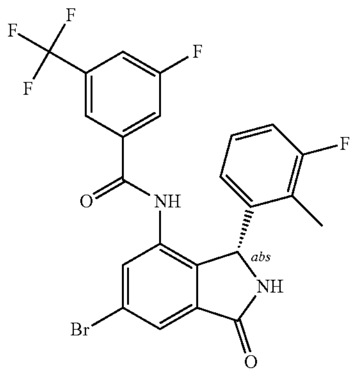 | Cc1c(F)cccc1[C@@H]1NC(=O)c2cc(Br)cc(NC(=O)c3cc(F)cc(c3)C(F)(F)F)c12 | 1H NMR (400 MHz, DMSO-d6) 10.50 (s, 1H), 9.28 (s, 1H), 7.93 (dt, 8.7, 2.0 Hz, 1H), 7.84-7.77 (m, 2H), 7.55 (d, 8.8 Hz, 1H), 7.35 (s, 1H), 7.03-6.92 (m, 2H), 6.38 (s, 1H), 5.93 (s, 1H), 2.17 (s, 3H). | 527 | B | |
| I-751 | 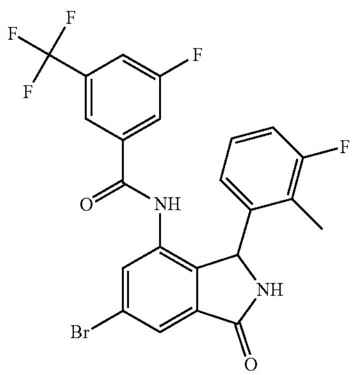 [SMILES: Cc1c(F)cccc1C1NC(=O)c2cc(Br)cc(NC(=O)c3cc(F)cc(C(F)(F)F)c3)c21] | Cc1c(F)cccc1C1NC(=O)c2cc(Br)cc(NC(=O)c3cc(F)cc(c3)C(F)(F)F)c12 | 1H NMR (400 MHz, DMSO-d6) 10.50 (s, 1H), 9.28 (s, 1H), 7.93 (d, 8.4 Hz, 1H), 7.87-7.75 (m, 2H), 7.55 (d, 8.9 Hz, 1H), 7.35 (s, 1H), 7.08-6.90 (m, 2H), 6.38 (s, 1H), 5.94 (s, 1H), 2.17 (s, 3H). | 525.15 | B | |
| I-752 | 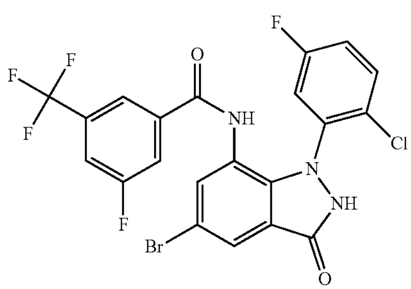 [SMILES: O=C(Nc1cc(Br)cc2c(=O)[nH]n(-c3cc(F)ccc3Cl)c12)c1cc(F)cc(C(F)(F)F)c1] | Fc1ccc(C1)c(c1)-n1[nH]c(=O)c2cc(Br)cc(NC(=O)c3cc(F)cc(c3)C(F)(F)F)c12 | 1H NMR (400 MHz, CD3CN) 8.65 (s, 1H), 7.92 (d, 1.7 Hz, 1H), 7.68-7.61 (m, 1H), 7.54 7.50 (m, 3H), 7.31 (dd, 9.0, 5.5 Hz, 1H), 7.25 (dd, 8.8, 3.0 Hz, 1H), 6.92 (ddd, 9.0, 8.0, 3.0 Hz, 1H) | 544.3 | D | |
| I-753 | 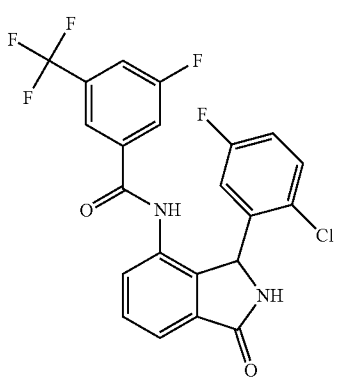 [SMILES: O=C(Nc1cccc2c1C(c1cc(F)ccc1Cl)NC2=O)c1cc(F)cc(C(F)(F)F)c1] | Fc1ccc(C1)c(c1)C1NC(=O)c2cccc(NC(=S)c3cc(F)cc(c3)C(F)(F)F)c12 | (400 MHz, DMSO-d6) 7.86 (d, 7.1 Hz, 1H), 7.69 (t, 7.7 Hz, 1H), 7.60 (app d, 8.2 Hz, 1H), 7.55 (app d, 8.3 Hz, 2H), 7.38 (s, 1H), 7.33 (dd, 8.9, 5.1 Hz, 1H), 7.28-7.19 (m, 1H), 7.06 (ddd, 8.8, 8.1, 3.1 Hz, 1H), 6.69 (br s, 1H), 6.15 (br s, 1H). | 481.3 | C | |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-754 | 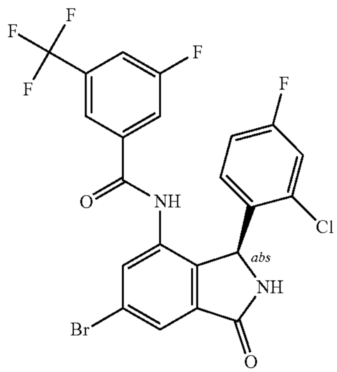 [SMILES: O=C(Nc1cc(Br)cc2c1[C@@H](c1ccc(F)cc1Cl)NC2=O)c1cc(F)cc(C(F)(F)F)c1] | Fc1ccc([C@H]2NC(=O)c3cc(Br)cc(NC(=O)c4cc(F)cc(c4)C(F)(F)F)c23)c(Cl)c1 | 1H NMR (400 MHz, Chloroform-d) 8.46 (s, 1H), 7.93 (d, 1.6 Hz, 1H), 7.58-7.49 (m, 2H), 7.47 (s, 1H), 7.38 (s, 1H), 7.25-7.18 (m, 1H), 7.00 (s, 2H), 6.70 (s, 1H), 6.19 (s, 1H). | 547 | D | |
| I-755 | 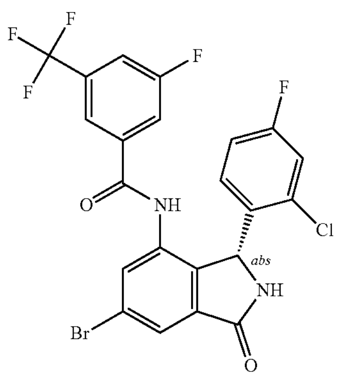 [SMILES: O=C(Nc1cc(Br)cc2c1[C@H](c1ccc(F)cc1Cl)NC2=O)c1cc(F)cc(C(F)(F)F)c1] | Fc1ccc([C@@H]2NC(=O)c3cc(Br)cc(NC(=O)c4cc(F)cc(c4)C(F)(F)F)c23)c(Cl)c1 | 1H NMR (400 MHz, Chloroform-d) 8.46 (s, 1H), 7.93 (d, 1.7 Hz, 1H), 7.58-7.49 (m, 2H), 7.45 (s, 1H), 7.38 (s, 1H), 7.21 (dd, 7.9, 1.9 Hz, 1H), 7.01 (s, 2H), 6.69 (s, 1H), 6.19 (s, 1H). | 547 | B | |
| I-756 | 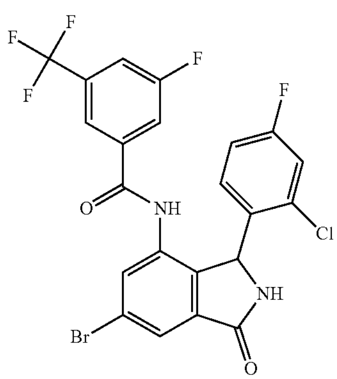 [SMILES: O=C(Nc1cc(Br)cc2c1C(c1ccc(F)cc1Cl)NC2=O)c1cc(F)cc(C(F)(F)F)c1] | Fc1ccc(C2NC(=O)c3cc(Br)cc(NC(=O)c4cc(F)cc(c4)C(F)(F)F)c23)c(Cl)c1 | 1H NMR (400 MHz, Methanol-d4) 7.96 (d, 1.7 Hz, 1H), 7.81-7.68 (m, 2H), 7.69-7.50 (m, 2H), 7.11 (dd, 8.7, 2.5 Hz, 1H), 6.93 (s, 2H), 6.22 (s, 1H). | 547 | B | |
| I-757 | 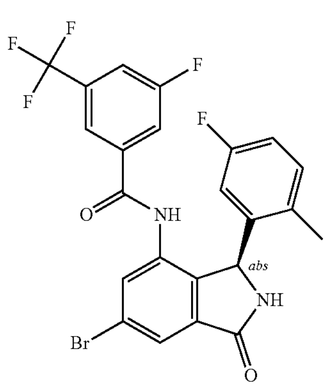 [SMILES: Cc1ccc(F)cc1[C@H]1NC(=O)c2cc(Br)cc(NC(=O)c3cc(F)cc(C(F)(F)F)c3)c21] | Cc1ccc(F)cc1[C@H]1NC(=O)c2cc(Br)cc(NC(=O)c3cc(F)cc(c3)C(F)(F)F)c12 | 1H NMR (400 MHz, DMSO-d6) 10.53 (s, 1H), 9.26 (s, 1H), 7.97-7.90 (m, 1H), 7.82 (d, 1.7 Hz, 1H), 7.77 (t, 2.0 Hz, 1H), 7.59 (d, 9.0 Hz, 1H), 7.46 (s, 1H), 7.04 (dd, 8.5, 5.9 Hz, 1H), 6.90 (td, 8.4, 2.8 Hz, 1H), 6.40 (s, 1H), 5.86 (s, 1H), 2.33 (s, 3H) | 525 | D | |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-758 | 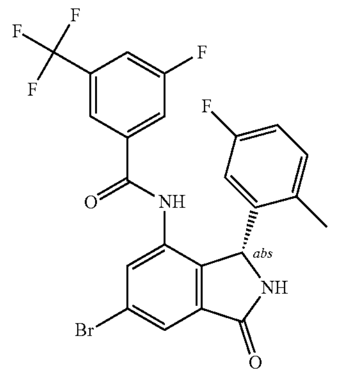 [SMILES: Cc1ccc(F)cc1[C@@H]1NC(=O)c2cc(Br)cc(NC(=O)c3cc(F)cc(C(F)(F)F)c3)c21] | Cc1ccc(F)cc1[C@@H]1NC(=O)c2cc(Br)cc(NC(=O)c3cc(F)cc(c3)C(F)(F)F)c12 | 1H NMR (400 MHz, DMSO-d6) 10.53 (s, 1H), 9.26 (s, 1H), 7.97-7.90 (m, 1H), 7.82 (d, 1.7 Hz, 1H), 7.77 (t, 2.0 Hz, 1H), 7.59 (d, 9.0 Hz, 1H), 7.46 (s, 1H), 7.04 (dd, 8.5, 5.9 Hz, 1H), 6.90 (td, 8.4, 2.8 Hz, 1H), 6.40 (s, 1H), 5.86 (s, 1H), 2.33 (s, 3H). | 525 | A | |
| I-759 | 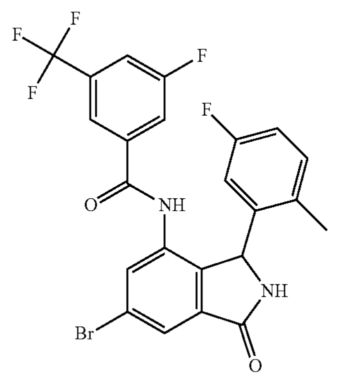 [SMILES: Cc1ccc(F)cc1C1NC(=O)c2cc(Br)cc(NC(=O)c3cc(F)cc(C(F)(F)F)c3)c21] | Cc1ccc(F)cc1C1NC(=O)c2cc(Br)cc(NC(=O)c3cc(F)cc(c3)C(F)(F)F)c12 | 1H NMR (400 MHz, DMSO-d6) 10.53 (s, 1H), 9.26 (s, 1H), 7.97-7.90 (m, 1H), 7.82 (d, 1.7 Hz, 1H), 7.77 (t, 2.0 Hz, 1H), 7.59 (d, 9.0 Hz, 1H), 7.46 (s, 1H), 7.04 (dd, 8.5, 5.9 Hz, 1H), 6.90 (td, 8.4, 2.8 Hz, 1H), 6.40 (s, 1H), 5.86 (s, 1H), 2.33 (s, 3H). | 525 | A | |
| I-760 | 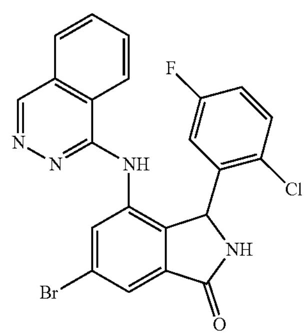 [SMILES: O=C1NC(c2cc(F)ccc2Cl)c2c(Nc3nncc4ccccc34)cc(Br)cc21] | Fc1ccc(C1)c(c1)C1NC(=O)c2cc(Br)cc(Nc3nncc4ccccc34)c12 | 1H NMR (400 MHz, DMSO-d6) 11.16-9.18 (d, 750.6 Hz, 1H), 9.13 (d, 29.5 Hz, 1H), 8.02 (d, 8.5 Hz, 1H), 7.98-7.80 (m, 2H), 7.80-7.60 (m, 3H), 7.55-7.13 (m, 1H), 6.95 (s, 2H), 6.73-6.19 (m, 1H), 5.81 (s, 1H). | 483 | E | |
| I-761 | 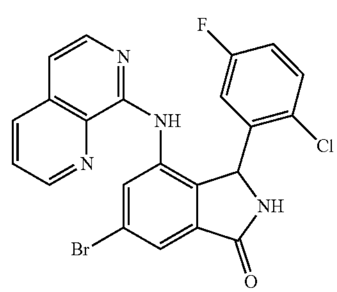 [SMILES: O=C1NC(c2cc(F)ccc2Cl)c2c(Nc3nccc4cccnc34)cc(Br)cc21] | Fc1ccc(C1)c(c1)C1NC(=O)c2cc(Br)cc(Nc3nccc4cccnc34)c12 | 1H NMR (400 MHz, DMSO-d6) 9.30 (s, 1H), 9.04 (s, 1H), 8.89 (s, 1H), 8.76 (dd, 4.2, 1.6 Hz, 1H), 8.31 (dd, 8.3, 1.7 Hz, 1H), 8.13 (dd, 5.8, 1.7 Hz, 1H), 7.78 (dd, 8.3, 4.2 Hz, 1H), 7.58 (d, 1.8 Hz, 1H), 7.47 (s, 1H), 7.27 (d, 5.8 Hz, 1H), 7.16 (td, 8.3, 3.0 Hz, 1H), 6.73 (s, 1H), 6.22 (s, 1H) | 483 | E | |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-762 | 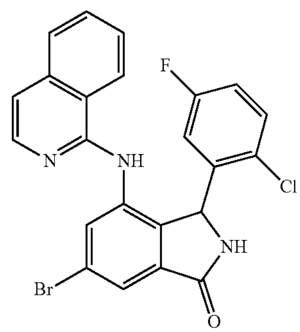 [SMILES: O=C1NC(c2cc(F)ccc2Cl)c2c(Nc3nccc4ccccc34)cc(Br)cc21] | Fc1ccc(C1)c(c1)C1NC(=O)c2cc(Br)cc(Nc3nccc4ccccc34)c12 | 1H NMR (400 MHz, Chloroform-d) 8.40 (s, 1H), 8.10 (s, 1H), 7.85 (d, 1.7 Hz, 1H), 7.77 (d, 8.3 Hz, 1H), 7.66 (ddd, 8.1, 6.8, 1.1 Hz, 1H), 7.45 (ddd, 8.3, 6.9, 1.3 Hz, 2H), 7.28 (s, 3H), 6.97-6.87 (m, 1H), 6.67 (dd, 8.7, 3.0 Hz, 1H), 6.49 (s, 1H), 6.17 (s, 1H). | 482 | D | |
| I-763 | 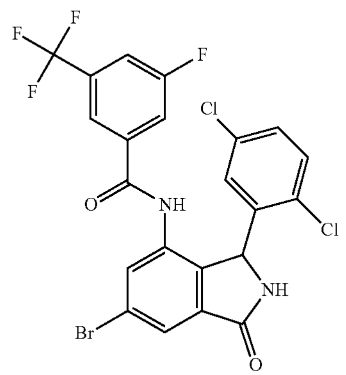 [SMILES: O=C(Nc1cc(Br)cc2c1C(c1cc(Cl)ccc1Cl)NC2=O)c1cc(F)cc(C(F)(F)F)c1] | Fc1cc(cc(c1)C(F)(F)F)C(=O)Nc1cc(Br)cc2C(=O)NC(c12)c1cc(Cl)ccc1Cl | 1H NMR (400 MHz, Methanol-d4) 7.97 (d, 1.7 Hz, 1H), 7.83-7.58 (m, 4H), 7.39-7.18 (m, 2H), 7.00 (s, 1H), 6.07 (s, 1H). | 562.85 | A | |
| I-764 | 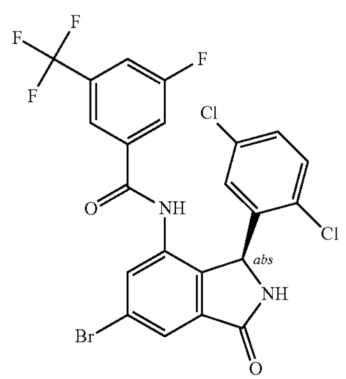 [SMILES: O=C(Nc1cc(Br)cc2c1[C@@H](c1cc(Cl)ccc1Cl)NC2=O)c1cc(F)cc(C(F)(F)F)c1] | Fc1cc(cc(c1)C(F)(F)F)C(=O)Nc1cc(Br)cc2C(=O)N[C@@H](c12)c1cc(Cl)ccc1Cl | 1H NMR (400 MHz, Chloroform-d) 8.40 (s, 1H), 7.98 (d, 1.7 Hz, 1H), 7.59-7.50 (m, 2H), 7.43 (s, 2H), 7.39 (d, 8.6 Hz, 1H), 7.33 (dd, 8.6, 2.4 Hz, 1H), 6.98 (s, 1H), 6.52 (s, 1H), 6.17 (s, 1H). | 563.05 | D | |
| I-765 | 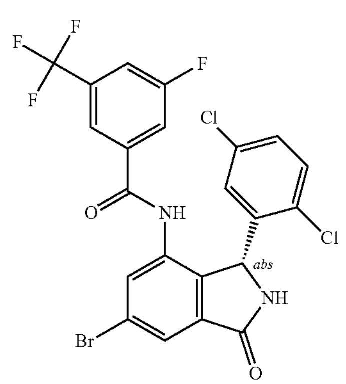 | Fc1cc(cc(c1)C(F)(F)F)C(=O)Nc1cc(Br)cc2C(=O)N[C@H](c12)c1cc(Cl)ccc1Cl | 1H NMR (400 MHz, Chloroform-d) 8.40 (s, 1H), 7.98 (d, 1.7 Hz, 1H), 7.55 (td, 8.4, 7.2, 4.1 Hz, 2H), 7.43 (s, 2H), 7.39 (d, 8.6 Hz, 1H), 7.33 (dd, 8.6, 2.4 Hz, 1H), 6.98 (s, 1H), 6.49 (s, 1H), 6.17 (s, 1H). | 563 | A | |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-766 | 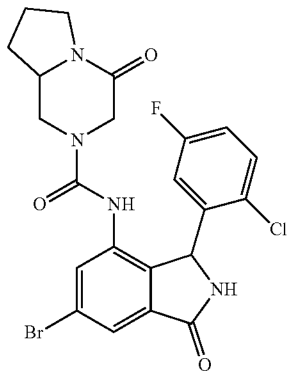 [SMILES: O=C1NC(c2cc(F)ccc2Cl)c2c(NC(=O)N3CC(=O)N4CCCC4C3)cc(Br)cc21] | Fc1ccc(C1)c(c1)C1NC(=O)c2cc(Br)cc(NC(=O)N3CC4CCCN4C(=O)C3)c12 | NMR (400 MHz, DMSO-d6) 9.19 (s, 1H), 8.75-8.71 (m, 1H), 7.63 (dd, 6.6, 1.6 Hz, 1H), 7.46 (d, 1.6 Hz, 1H), 7.24 (ddd, 8.9, 8.1, 3.1 Hz, 1H), 7.18 (ddd, 8.9, 8.1, 3.1 Hz, 1H), 6.59 (br. s, 1H), 5.96-5.91 (m, 1H), 4.20-3.98 (m, 2H), 3.46-3.25 (m, 5H under water peak), 2.04-1.95 (m, 1H), 1.95-1.86 (m, 2H), 1.81-1.66 (m, 1H), 1.42-1.30 (m, 1H) | 521.3 | E | |
| I-767 | 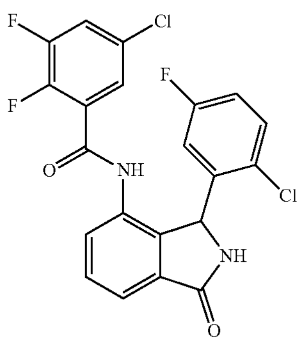 [SMILES: O=C(Nc1cccc2c1C(c1cc(F)ccc1Cl)NC2=O)c1cc(Cl)cc(F)c1F] | Fc1ccc(C1)c(c1)C1NC(=O)c2cccc(NC(=O)c3cc(Cl)cc(F)c3F)c12 | NMR (400 MHz, DMSO-d6) 10.49 (br. s, 1H), 9.16 (s, 1H), 7.91 (ddd, 10.0, 6.6, 2.6 Hz, 1H), 7.70 (dd, 7.6, 0.8 Hz, 1H), 7.64 (t, 8.0 Hz, 1H), 7.50-7.46 (m, 2H), 7.25 (ddd, 8.8, 8.1, 3.1 Hz, 1H), 6.88 (dt, 4.8, 2.0 Hz, 1H), 6.56 (br. s, 1H), 6.02 (br. s, 1H) | 451.2 | B | |
| I-768 | 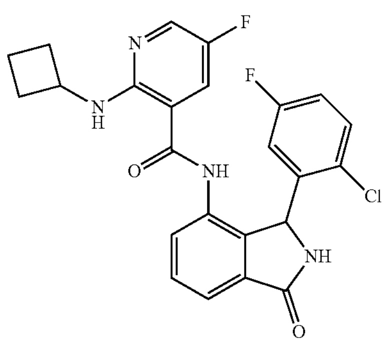 | Fc1ccc(C1)c(c1)C1NC(=O)c2cccc(NC(=O)c3cc(F)cnc3NC3CCC3)c12 | NMR (400 MHz, DMSO-d6) 10.16 (s, 1H), 9.14 (s, 1H), 8.20 (d, 2.9 Hz, 1H), 8.04 (d, 7.0 Hz, 1H), 7.69 (d. 6.9 Hz, 1H), 7.63 (t, 7.6 Hz, 1H), 7.46 (d, 7.7 Hz, 1H), 7.40 (br. d, 8.9 Hz, 1H), 7.34 (dd, 8.9, 5.2 Hz, 1H), 7.12 (ddd, 8.8, 8.1, 3.1 Hz, 1H), 6.59 (br. s submerged, 1H), 6.01 (br. s, 1H), 4.47-4.36 (sx, 7.6 Hz, 1H), 2.36-2.25 (m, 2H), 1.91-1.77 (m, 2H), 1.77-1.62 (m, 2H). | 469.4 | D | |
| I-769 | 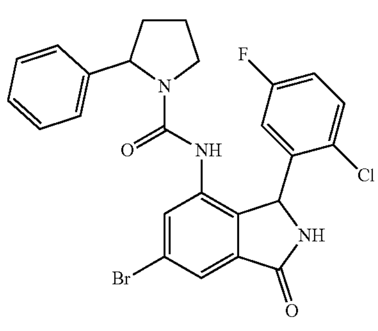 [SMILES: O=C1NC(c2cc(F)ccc2Cl)c2c(NC(=O)N3CCCC3c3ccccc3)cc(Br)cc21] | Fc1ccc(C1)c(c1)C1NC(=O)c2cc(Br)cc(NC(=O)N3CCCC3c3ccccc3)c12 | NMR (400 MHz, DMSO) 9.37 (s, 1H), 9.24-9.16 (m, 1H), 7.81 (s, 1H), 7.67 (d, 1.6 Hz, 1H), 7.60 (d, 1.5 Hz, 1H), 7.58 (d, 1.6 Hz, 1H), 7.54-48 (m, 1H), 7.33-7.27 (m, 2H), 7.26-7.16 (m, 1H), 7.09-7.03 (m, 1H), 6.57 (s, 1H), 6.04 (s, 1H), 4.74 (s, 1H), 3.98 (t, 6.0 Hz, 1H), 3.62 (t, 6.3 Hz, 1H), 3.46-3.38 (m, 1H), 2.11-2.01 (m, 1H), 1.77-1.54 (m, 3H). | 528 | D | |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-770 | 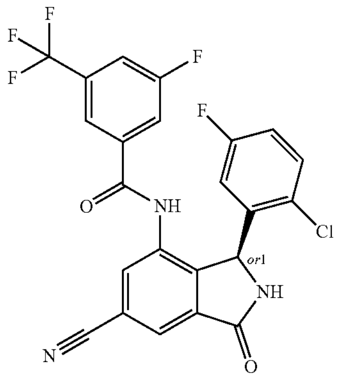 [SMILES: N#Cc1cc(NC(=O)c2cc(F)cc(C(F)(F)F)c2)c2c(c1)C(=O)N[C@@H]2c1cc(F)ccc1Cl] | Fc1ccc(C1)c(c1)[C@H]1NC(=O)c2cc(cc(NC(=O)c3cc(F)cc(c3)C(F)(F)F)c12)C#N | | 490.3 | A | |
| I-771 | 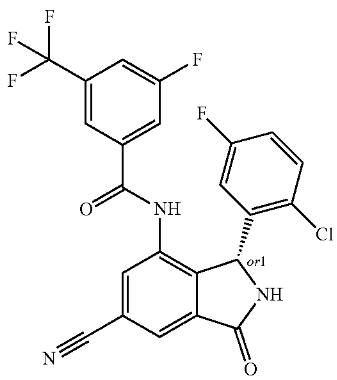 [SMILES: N#Cc1cc(NC(=O)c2cc(F)cc(C(F)(F)F)c2)c2c(c1)C(=O)N[C@H]2c1cc(F)ccc1Cl] | Fc1ccc(C1)c(c1)[C@@H]1NC(=O)c2cc(cc(NC(=O)c3cc(F)cc(c3)C(F)(F)F)c12)C#N | | 490.3 | A | |
| I-772 | 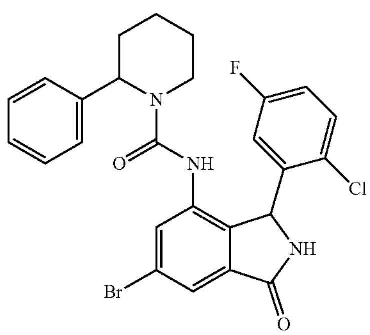 [SMILES: O=C1NC(c2cc(F)ccc2Cl)c2c(NC(=O)N3CCCCC3c3ccccc3)cc(Br)cc21] | Fc1ccc(C1)c(c1)C1NC(=O)c2cc(Br)cc(NC(=O)N3CCCCC3c3ccccc3)c12 | NMR (400 MHz, DMSO) 9.19 (s, 2H), 8.67 (s, 1H), 8.59 (s, 1H), 7.68-7.64 (m, 1H), 7.60 (dt, 3.5, 1.8 Hz, 3H), 7.55 (br s, 1H), 7.40-7.31 (m, 4H), 7.30-7.19 (m, 4H), 7.13-7.05 (m, 4H), 6.12 (s, 1H), 5.46 (s, 1H), 5.07 (s, 1H), 3.77 (d, 12.9 Hz, 1H), 3.50 (d, 12.4 Hz, 1H), 2.71-2.58 (m, 1H), 2.46-2.42 (m, 1H), 2.32 (dd, 7.6, 5.8 Hz, 1H), 2.22 (dd, 9.9, 1.7 Hz, 1H), 1.77-1.55 (m, 2H), 1.51-1.13 (m, 8H), 0.95-0.77 (m, 1H). | 544 | D | |
| I-773 | 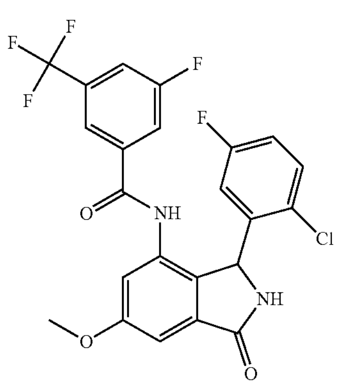 [SMILES: COc1cc(NC(=O)c2cc(F)cc(C(F)(F)F)c2)c2c(c1)C(=O)NC2c1cc(F)ccc1Cl] | COc1cc2C(=O)NC(c2c(NC(=O)c2cc(F)cc(c2)C(F)(F)F)c1)c1cc(F)ccc1Cl | NMR (400 MHz, DMSO-d6) 10.48 (br. s, 1H), 9.13 (s, 1H), 7.94 (d, 8.5 Hz, 1H), 7.72 (d, 9.0 Hz, 1H), 7.64 (s, 1H), 7.30 (dd, 8.8, 5.2 Hz, 1H), 7.21 (d, 2.1 Hz, 1H), 7.12-7.04 (m, 2H), 6.59 (br. s, 1H), 5.93 (br. s, 1H), 3.88 (s, 3H) | 497.2 | A | |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-774 | | Fc1ccc(C1)c(c1)C1NC(=O)c2cc(Br)cc(NC(=O)c3cc(F)cc(c3)S(F)(F)(F)(F)F)c12 | NMR (400 MHz, DMSO D6) 10.64 (s, broad, 1H), 9.30 (s, broad, 1H, ), 8.21 (dd, 8.7, 1.9 Hz, 1H), 7.83 (s, 2H), 7.76 (d, 8.5 Hz, 1H), 7.73 (s, 1H), 7.31 (dd, 8.9, 5.2 Hz, 1H), 7.09 (td, 8.5, 3.0 Hz, 1H), 7.25-6.25 (m, broad, 1H), 6.20-5.60 (m, broad, 1H). | 603.1 | A | |
| I-775 | 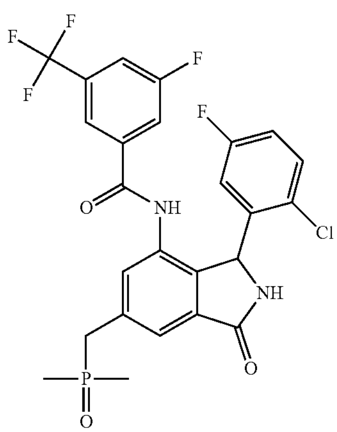 [SMILES: CP(C)(=O)Cc1cc(NC(=O)c2cc(F)cc(C(F)(F)F)c2)c2c(c1)C(=O)NC2c1cc(F)ccc1Cl] | CP(C)(=O)Cc1cc2C(=O)NC(c2c(NC(=O)c2cc(F)cc(c2)C(F)(F)F)c1c(F)ccc1Cl | NMR (400 MHz, DMSO-d6) 10.55 (br. s, 1H), 9.14 (s, 1H), 7.94 (d, 8.6 Hz, 1H), 7.73 (d, 9.0 Hz, 1H), 7.63 (s, 1H), 7.60 (br. t, 2.0 Hz 1H), 7.37 (s, 1H), 7.31 (dd, 8.9, 5.2 Hz, 1H), 7.09 (td, 8.4, 3.0 Hz, 1H), 6.66 (br. s, 1H), 5.95 (br. s, 1H), 3.45-3.23 (s, 2H), 1.40 (d, 7.7 Hz, 1H), 1.37 (d, 7.7 Hz, 1H). | 557.2 | A | |
| I-776 | 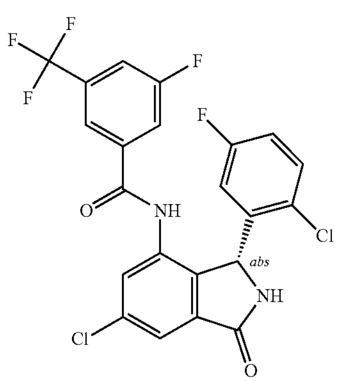 [SMILES: O=C(Nc1cc(Cl)cc2c1[C@H](c1cc(F)ccc1Cl)NC2=O)c1cc(F)cc(C(F)(F)F)c1] | Fc1ccc(C1)c(c1)[C@@H]1NC(=O)c2cc(Cl)cc(NC(=O)c3cc(F)cc(c3)C(F)(F)F)c12 | NMR (400 MHz, CD3CN) 8.64 (br s,1H), 7.74 (d, 1.8 Hz, 1H), 7.63 (d, 6.0 Hz, 1H), 7.60 (s, 1H), 7.56 (d, 6.0 Hz, 1H), 7.53 (s, 1H), 7.30 (br s, 1H), 7.25 (dd, 8.8, 5.2 Hz, 1H), 6.96 (td, 8.4, 3.1 Hz, 1H), 6.66 (br s, 1H), 6.09 (br s, 1H). | 542.3 | A | A |

TABLE 2-continued

Representative Compounds of the Invention with Bioactivity Data.

| Ex. No. | Structure | SMILES | $^1$H NMR | MS | ADP-Glo IC$_{50}$ | MCF 10A IC$_{50}$ |
|---|---|---|---|---|---|---|
| I-777 | 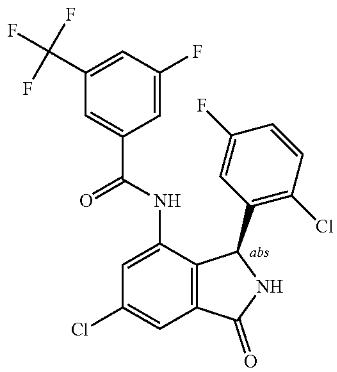 [SMILES: O=C(Nc1cc(Cl)cc2c1[C@@H](c1cc(F)ccc1Cl)NC2=O)c1cc(F)cc(C(F)(F)F)c1] | Fc1ccc(C1)c(c1)[C@H]1NC(=O)c2cc(Cl)cc(NC(=O)c3cc(F)cc(c3)C(F)(F)F)c12 | NMR (400 MHz, CD3CN) 8.64 (br s, 1H), 7.74 (d, 1.8 Hz, 1H), 7.63 (d, 6.0 Hz, 1H), 7.60 (s, 1H), 7.56 (d, 6.0 Hz, 1H), 7.53 (s, 1H), 7.30 (br s, 1H), 7.25 (dd, 8.8, 5.2 Hz, 1H), 6.96 (td, 8.4, 3.1 Hz, 1H), 6.66 (br s, 1H), 6.09 (br s, 1H). | 542.3 | D | |
| I-778 | 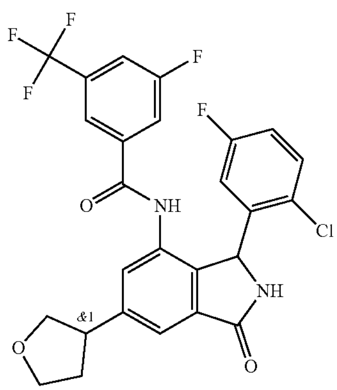 [SMILES: O=C(Nc1cc(C2CCOC2)cc2c1C(c1cc(F)ccc1Cl)NC2=O)c1cc(F)cc(C(F)(F)F)c1] | Fc1ccc(C1)c(c1)C1NC(=O)c2cc(cc(NC(=O)c3cc(F)cc(c3)C(F)(F)F)c12)C1CCOC1 | NMR (400 MHz, CD3CN) 8.58 (s, 1H), 7.63-7.50 (m, 4H), 7.42 (s, 1H), 7.20 (dd, 8.9, 5.1 Hz, 1H), 7.16 (br s, 1H), 6.93 (ddd, 11.9, 8.9, 5.1 Hz, 1H), 6.56 (br s, 1H), 6.04 (br s, 1H), 4.10-4.03 (m, 1H), 3.99 (td, 8.5, 4.7 Hz, 1H), 3.82 (q, 7.5 Hz, 1H), 3.67 (dd, 14.9, 7.8 Hz, 1H), 3.58-3.49 (m, 1H), 2.39 (ddd, 12.4, 10.1, 6.1 Hz, 1H), 2.01-1.94 (m, 1H). | 537.3 | A | |
| I-779 | 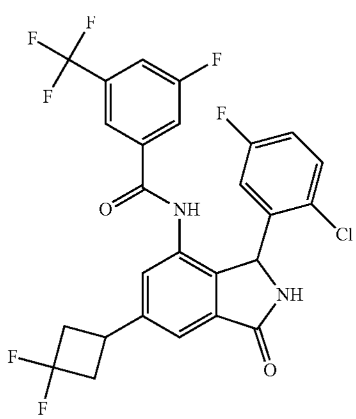 [SMILES: O=C(Nc1cc(C2CC(F)(F)C2)cc2c1C(c1cc(F)ccc1Cl)NC2=O)c1cc(F)cc(C(F)(F)F)c1] | Fc1ccc(C1)c(c1)C1NC(=O)c2cc(cc(NC(=O)c3cc(F)cc(c3)C(F)(F)F)c12)C1CC(F)(F)C1 | NMR (400 MHz, CD3CN) 8.62 (s, 1H), 7.71-7.54 (m, 4H), 7.47 (s, 1H), 7.25 (dd, 8.9, 5.1 Hz, 2H), 6.96 (ddd, 8.9, 8.0, 3.1 Hz, 1H), 6.59 (br s, 1H), 6.10 (br s, 1H), 3.66-3.54 (m, 1H), 3.15-3.02 (m, 2H), 2.85-2.67 (m, 2H). | 598.3 | A | |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-780 | 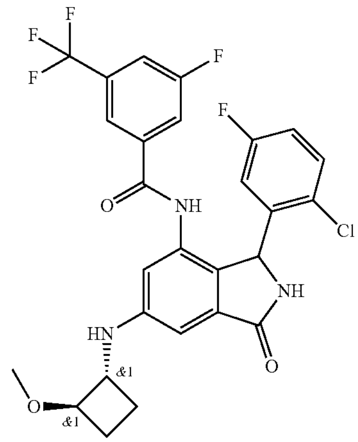 [SMILES: CO[C@@H]1CC[C@H]1Nc1cc(NC(=O)c2cc(F)cc(C(F)(F)F)c2)c2c(c1)C(=O)NC2c1cc(F)ccc1Cl] | CO[c@@H]1CC[C@H]1Nc1cc2C(=O)NC(c2c(NC(=O)c2cc(F)cc(c2)C(F)(F)F)c1)c1cc(F)ccc1Cl | NMR (400 MHz, DMSO-d6) 10.28 (s, 1H), 8.96 (s, 1H), 7.92 (d, 8.6 Hz, 1H), 7.67 (d, 16.1Hz, 1H), 7.61 (s, 1H), 7.28 (dd, 8.9, 5.2 Hz, 1H), 7.06 (td, 8.4, 3.1 Hz, 1H), 6.69 (d, 2.0 Hz, 1H), 6.60 (s, 1H), 6.54 (d, 5.3 Hz, 1H), 5.88 (s, 1H), 4.10-3.99 (m, 1H), 3.95-3.87 (m, 1H), 3.16 (s, 3H), 2.31 (ddd, 12.5, 7.6, 4.8 Hz, 2H), 2.18-2.09 (m, 2H). | 566.3 | A | |
| I-781 | 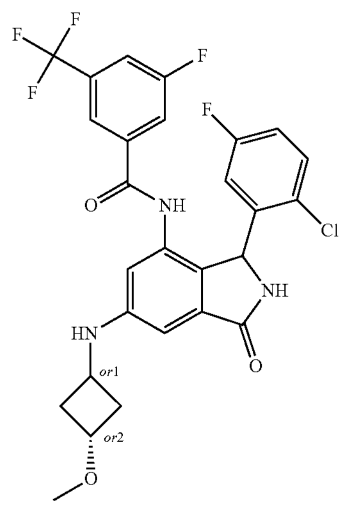 | CO[c@H]1CC(C1)Nc1cc2C(=O)NC(c2c(NC(=O)c2cc(F)cc(c2)C(F)F)c1)c1cc(F)ccc1Cl | NMR (400 MHz, CD3CN) 8.46 (s, 1H), 7.63 (d, 8.5 Hz, 2.0 Hz, 1H), 7.59-7.53 (m, 2H), 7.23 (dd, 8.9, 5.1 Hz, 1H), 7.09 (s, 1H), 6.95 (ddd, 8.8 Hz, 8.1 Hz, 3.1 Hz, 1H), 6.84 (d, 2.1 Hz, 1H), 6.76 (s, 1H), 6.63 (br, s, 1H), 5.98 (s, 1H), 5.09 (d, 6.9 Hz, 1H), 3.69 (p, 7.3 Hz, 1H), 3.62-3.53 (m, 1H), 3.20 (s, 3H), 2.86-2.79 (m, 2H), 1.77-1.69 (m, 2H). | 566.3 | A | |
| I-782 | 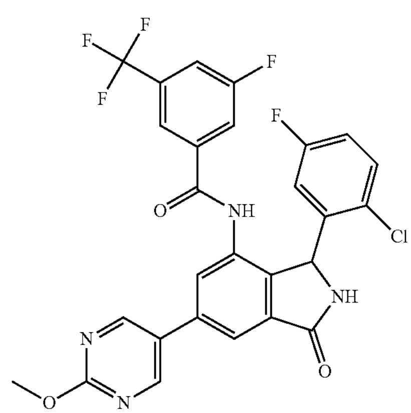 [SMILES: COc1ncc(-c2cc(NC(=O)c3cc(F)cc(C(F)(F)F)c3)c3c(c2)C(=O)NC3c2cc(F)ccc2Cl)cn1] | COc1ncc(cn1)-c1cc2C(=O)NC(c2c(NC(=O)c2cc(F)cc(c2)C(F)(F)F)c1)c1cc(F)ccc1Cl | 1H NMR (DMSO-d6, 400 MHz) 10.63 (s, 1H), 9.24 (br s, 1H), 9.05 (s, 2H), 8.06 (d, 1.5 Hz, 1H), 7.96 (br d, 8.3 Hz, 1H), 7.84 (d, 1.3 Hz, 1H), 7.76 (br d, 8.8 Hz, 1H), 7.70 (s, 1H), 7.33 (dd, 8.8, 5.3 Hz, 1H), 7.11 (td, 8.5, 3.0 Hz, 1H), 6.43-6.91 (m, 1H), 6.04 (br s, 1H), 4.00 (s, 3H) | 575 | A | |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-783 | 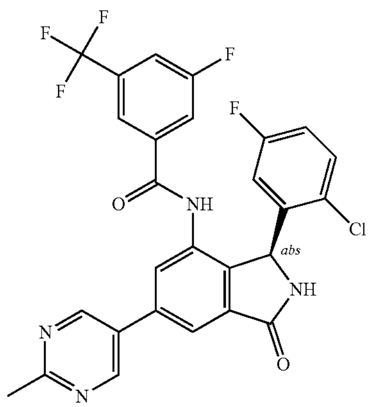 [SMILES: Cc1ncc(-c2cc(NC(=O)c3cc(F)cc(C(F)(F)F)c3)c3c(c2)C(=O)N[C@@H]3c2cc(F)ccc2Cl)cn1] | Cc1ncc(cn1)-c1cc2C(=O)N[C@@H](c2c(NC(=O)c2cc(F)cc(c2)C(F)(F)F)c1)c1cc(F)ccc1Cl | | 559.2 | D | |
| I-784 | 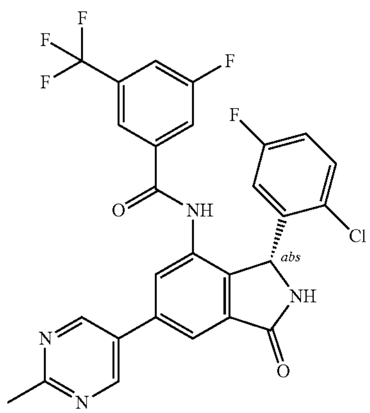 [SMILES: Cc1ncc(-c2cc(NC(=O)c3cc(F)cc(C(F)(F)F)c3)c3c(c2)C(=O)N[C@H]3c2cc(F)ccc2Cl)cn1] | Cc1ncc(cn1)-c1cc2C(=O)N[C@H](c2c(NC(=O)c2cc(F)cc(c2)C(F)(F)F)c1)c1cc(F)ccc1Cl | | 559.2 | A | |
| I-785 | 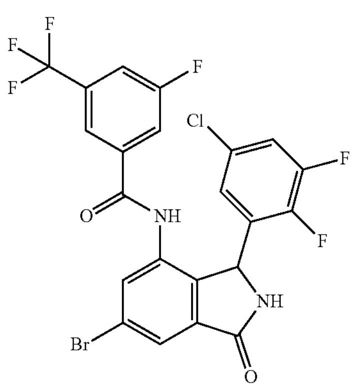 [SMILES: O=C(Nc1cc(Br)cc2c1C(c1cc(Cl)cc(F)c1F)NC2=O)c1cc(F)cc(C(F)(F)F)c1] | Fc1cc(cc(c1)C(F)(F)F)C(=O)Nc1cc(Br)cc2C(=O)NC(c12)c1cc(Cl)cc(F)c1F | 1H NMR (400 MHz, DMSO-d6) 10.61 (s, 1H), 9.28 (s, 1H), 8.01 (d, 8.5 Hz, 1H), 7.87-7.73 (m, 4H), 7.59 (ddd, 9.7, 6.7, 2.6 Hz, 1H), 6.99 (s, 1H), 5.86 (s, 1H). | 563 | A | |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-786 | 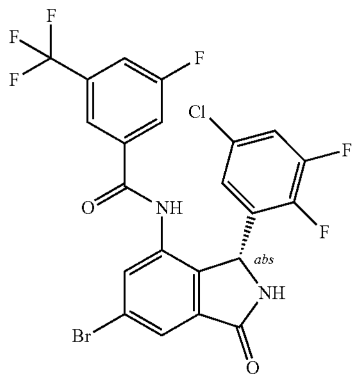 [SMILES: O=C(Nc1cc(Br)cc2c1[C@H](c1cc(Cl)cc(F)c1F)NC2=O)c1cc(F)cc(C(F)(F)F)c1] | Fc1cc(cc (c1)C(F) (F)F)C(= O)Nc1cc (Br)cc2C (=O)N[C @H](c12) c1cc(Cl) cc(F)c1F | 1H NMR (400 MHz, DMSO-d6) 10.61 (s, 1H), 9.28 (s, 1H), 8.00 (d, 8.5 Hz, 1H), 7.87-7.78 (m, 2H), 7.78-7.73 (m, 2H), 7.59 (ddd, 9.7, 6.6, 2.6 Hz, 1H), 6.99 (s, 1H), 5.86 (s, 1H). | 563 | A | |
| I-787 | 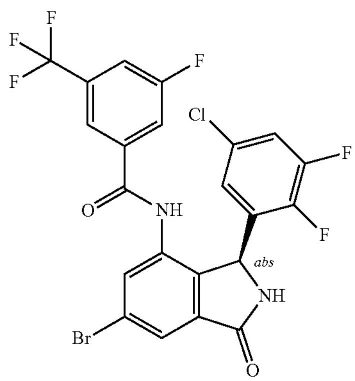 [SMILES: O=C(Nc1cc(Br)cc2c1[C@@H](c1cc(Cl)cc(F)c1F)NC2=O)c1cc(F)cc(C(F)(F)F)c1] | Fc1cc(cc (c1)C(F) (F)F)C(= O)Nc1cc (Br)cc2C (=O)N[C @@H](c 12)c1cc (Cl)cc(F)c 1F | 1H NMR (400 MHz, DMSO-d6) 10.61 (s, 1H), 9.28 (s, 1H), 8.01 (d, 8.4 Hz, 1H), 7.87-7.79 (m, 2H), 7.79-7.73 (m, 2H), 7.59 (ddd, 9.5, 6.7, 2.6 Hz, 1H), 6.99 (s, 1H), 5.86 (s, 1H). | 563 | D | |
| I-788 | 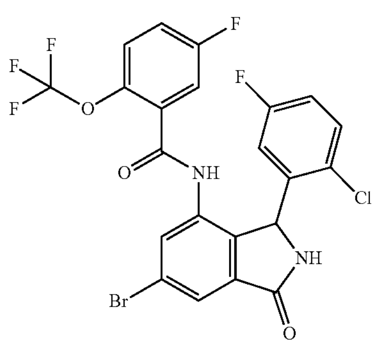 [SMILES: O=C(Nc1cc(Br)cc2c1C(c1cc(F)ccc1Cl)NC2=O)c1cc(F)ccc1OC(F)(F)F] | Fc1ccc(C 1)c(c1)C1 NC(=O)c 2cc(Br)cc (NC(=O) c3cc(F)cc c3OC(F) (F)F)c12 | 1H NMR (400 MHz, DMSO-d6) 10.50 (s, 1H), 9.33-9.29 (m, 1H), 7.81 (d, 1.7 Hz, 1H), 7.72 (d, 1.8 Hz, 1H), 7.60-7.47 (m, 3H), 7.29 (td, 8.4, 3.1 Hz, 1H), 6.78 (s, 1H), 6.58 (dd, 8.2, 3.0 Hz, 1H), 6.03 (s, 1H). | 563 | D | |
| I-789 | 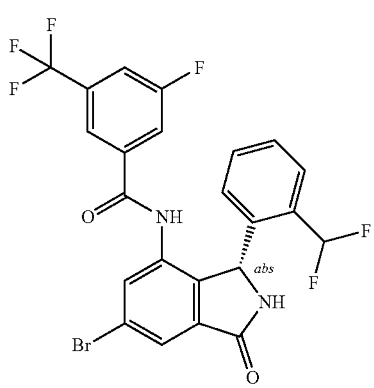 [SMILES: O=C(Nc1cc(Br)cc2c1[C@H](c1ccccc1C(F)F)NC2=O)c1cc(F)cc(C(F)(F)F)c1] | FC(F)c1c cccc1[C @@H]1 NC(=O)c 2cc(Br)cc (NC(=O) c3cc(F)cc (c3)C(F) (F)F)c12 | 1H NMR (400 MHz, DMSO-d6) 10.50 (s, 1H), 9.29 (s, 1H), 7.92 (d, 8.7 Hz, 1H), 7.85 (d, 1.8 Hz, 1H), 7.78 (d, 1.8 Hz, 1H), 7.67-7.00 (m, 6H), 6.72 (s, 1H), 6.02 (s, 1H). | 545.15 | A | |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-790 | 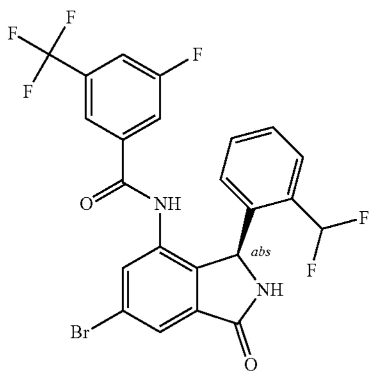 [SMILES: O=C(Nc1cc(Br)cc2c1[C@@H](c1ccccc1C(F)F)NC2=O)c1cc(F)cc(C(F)(F)F)c1] | FC(F)c1c cccc1[C @H]1NC (=O)c2cc (Br)cc(N C(=O)c3 cc(F)cc(c 3)C(F)(F) F)c12 | 1H NMR (400 MHz, DMSO-d6) 10.50 (s, 1H), 9.29 (s, 1H), 7.92 (dt, 8.6, 1.9 Hz, 1H), 7.85 (d, 1.7 Hz, 1H), 7.78 (d, 1.8 Hz, 1H), 7.63-7.09 (m, 6H), 6.72 (s, 1H), 6.02 (s, 1H). | 545.15 | D | |
| I-791 | 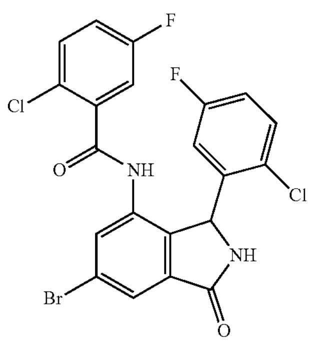 [SMILES: O=C(Nc1cc(Br)cc2c1C(c1cc(F)ccc1Cl)NC2=O)c1cc(F)ccc1Cl] | Fc1ccc(C 1)c(c1)C1 NC(=O)c 2cc(Br)cc (NC(=O) c3cc(F)cc c3Cl)c12 | 1H NMR (400 MHz, Methanol-d4) 7.95 (d, 1.7 Hz, 1H), 7.88-7.73 (m, 1H), 7.66-7.36 (m, 2H), 7.21 (dddd, 20.0, 8.8, 7.9, 3.0 Hz, 2H), 6.63 (d, 3.1 Hz, 1H), 6.61 (d, 3.1 Hz, 1H), 6.27 (s, 1H). | 512.95 | E | |
| I-792 | 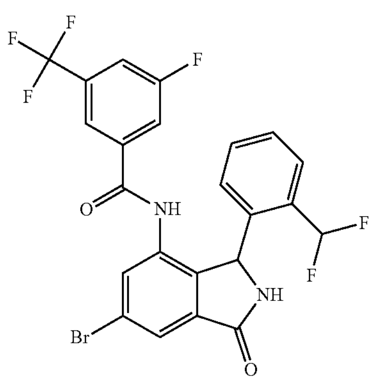 [SMILES: O=C(Nc1cc(Br)cc2c1C(c1ccccc1C(F)F)NC2=O)c1cc(F)cc(C(F)(F)F)c1] | FC(F)c1c cccc1C1 NC(=O)c 2cc(Br)cc (NC(=O) c3cc(F)cc (c3)C(F) (F)F)c12 | 1H NMR (400 MHz, DMSO-d6) 10.50 (s, 1H), 9.29 (s, 1H), 7.92 (d, 8.4 Hz, 1H), 7.85 (d, 1.8 Hz, 1H), 7.78 (d, 1.9 Hz, 1H), 7.62-7.04 (m, 6H), 6.72 (s, 1H), 6.02 (s, 1H). | 545.15 | A | |
| I-793 | 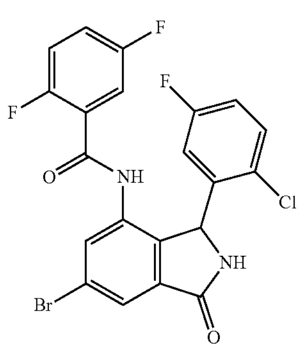 [SMILES: O=C(Nc1cc(Br)cc2c1C(c1cc(F)ccc1Cl)NC2=O)c1cc(F)ccc1F] | Fc1ccc(C 1)c(c1)C1 NC(=O)c 2cc(Br)cc (NC(=O) c3cc(F)cc c3F)c12 | 1H NMR (400 MHz, DMSO-d6) 10.36 (s, 1H), 9.30 (s, 1H), 7.80 (d, 1.7 Hz, 1H), 7.74 (d, 1.8 Hz, 1H), 7.45 (ddt, 11.9, 7.4, 3.1 Hz, 2H), 7.36 (td, 9.3, 4.3 Hz, 1H), 7.28-7.19 (m, 1H), 6.98 (ddd, 8.5, 5.4, 3.2 Hz, 1H), 6.74 (s, 1H), 6.02 (s, 1H). | 496.9 | D | |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-794 | 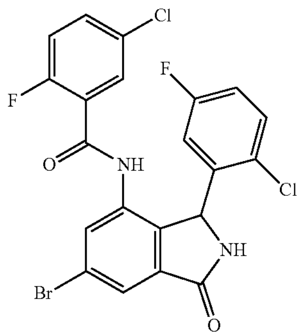 [SMILES: O=C(Nc1cc(Br)cc2c1C(c1cc(F)ccc1Cl)NC2=O)c1cc(Cl)ccc1F] | Fc1ccc(C1)c(c1)C1NC(=O)c2cc(Br)cc(NC(=O)c3cc(Cl)ccc3F)c12 | 1H NMR (400 MHz, DMSO-d6) 10.43 (s, 1H), 9.30 (s, 1H), 7.80 (d, 1.7 Hz, 1H), 7.76-7.71 (m, 1H), 7.63 (ddd, 8.9, 4.3, 2.8 Hz, 1H), 7.51-7.43 (m, 1H), 7.36 (t, 9.3 Hz, 1H), 7.25 (td, 8.4, 3.0 Hz, 1H), 7.06 (dd, 6.0, 2.8 Hz, 1H), 6.71 (s, 1H), 6.00 (s, 1H). | 512.95 | D | |
| I-795 | 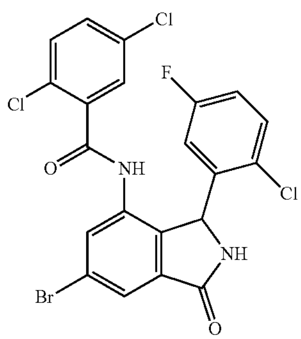 [SMILES: O=C(Nc1cc(Br)cc2c1C(c1cc(F)ccc1Cl)NC2=O)c1cc(Cl)ccc1Cl] | Fc1ccc(C1)c(c1)C1NC(=O)c2cc(Br)cc(NC(=O)c3cc(Cl)ccc3Cl)c12 | 1H NMR (400 MHz, Chloroform-d) 8.45 (s, 1H), 7.95 (d, 1.6 Hz, 1H), 7.64 (s, 1H), 7.45-7.32 (m, 4H), 7.08 (td, 8.9, 8.2, 3.0 Hz, 1H), 6.66-6.59 (m, 2H), 6.16 (s, 1H). | 528.85 | D | |
| I-796 | 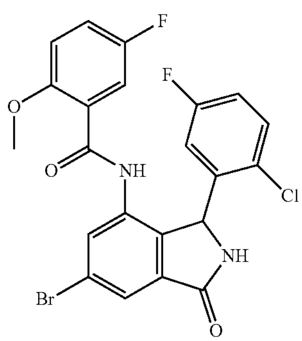 [SMILES: COc1ccc(F)cc1C(=O)Nc1cc(Br)cc2c1C(c1cc(F)ccc1Cl)NC2=O] | COc1ccc(F)cc1C(=O)Nc1cc(Br)cc2C(=O)NC(c12)c1cc(F)ccc1Cl | 1H NMR (400 MHz, DMSO-d6) 9.89 (s, 1H), 9.28 (s, 1H), 7.83 (d, 1.7 Hz, 1H), 7.77 (d, 1.8 Hz, 1H), 7.42 (dd, 8.8, 5.1 Hz, 1H), 7.35 (ddd, 9.1, 7.9, 3.3 Hz, 1H), 7.23-7.05 (m, 3H), 6.73 (s, 1H), 6.07 (s, 1H), 3.73 (s, 3H). | 509 | D | |
| I-797 | 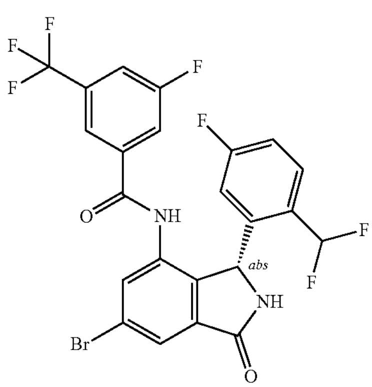 [SMILES: O=C(Nc1cc(Br)cc2c1[C@H](c1cc(F)ccc1C(F)F)NC2=O)c1cc(F)cc(C(F)(F)F)c1] | FC(F)c1cc(F)cc1[C@@H]1NC(=O)c2cc(Br)cc(NC(=O)c3cc(F)cc(c3)C(F)(F)F)c12 | 1H NMR (400 MHz, DMSO-d6) 10.55 (s, 1H), 9.33 (s, 1H), 7.94 (d, 8.2 Hz, 1H), 7.87 (d, 1.7 Hz, 1H), 7.78 (d, 1.7 Hz, 1H), 7.67 (d, 8.9 Hz, 1H), 7.58 (s, 1H), 7.50 (dd, 8.8, 5.6 Hz, 1H), 7.22 (td, 8.4, 2.7 Hz, 1H), 7.11 (s, 1H), 6.57 (s, 1H), 6.02 (s, 1H). | 561.05 | A | |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-798 | 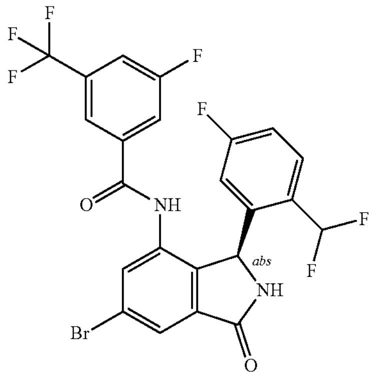 [SMILES: O=C(Nc1cc(Br)cc2c1[C@@H](c1cc(F)ccc1C(F)F)NC2=O)c1cc(F)cc(C(F)(F)F)c1] | FC(F)c1cc(F)cc1[C@H]1NC(=O)c2cc(Br)cc(NC(=O)c3cc(F)cc(c3)C(F)(F)F)c12 | 1H NMR (400 MHz, DMSO-d6) 10.55 (s, 1H), 9.33 (s, 1H), 7.94 (d, 8.2 Hz, 1H), 7.87 (d, 1.7 Hz, 1H), 7.78 (d, 1.7 Hz, 1H), 7.67 (d, 8.9 Hz, 1H), 7.58 (s, 1H), 7.50 (dd, 8.8, 5.6 Hz, 1H), 7.22 (td, 8.4, 2.7 Hz, 1H), 7.11 (s, 1H), 6.57 (s, 1H), 6.02 (s, 1H). | 561.05 | D | |
| I-799 | 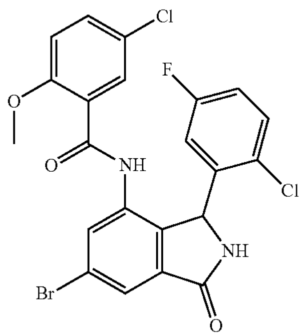 [SMILES: COc1ccc(Cl)cc1C(=O)Nc1cc(Br)cc2c1C(c1cc(F)ccc1Cl)NC2=O] | COc1ccc(Cl)cc1C(=O)Nc1cc(Br)cc2C(=O)NC(c12)c1cc(F)ccc1Cl | 1H NMR (400 MHz, DMSO-d6) 9.95 (s, 1H), 9.28 (s, 1H), 7.82-7.74 (m, 2H), 7.52 (dd, 8.9, 2.8 Hz, 1H), 7.44 (dd, 8.8, 5.1 Hz, 1H), 7.21 (ddd, 8.9, 8.0, 3.1 Hz, 1H), 7.16-7.10 (m, 2H), 6.74 (s, 1H), 6.06 (s, 1H), 3.74 (s, 3H). | 522.95 | D | |
| I-800 | 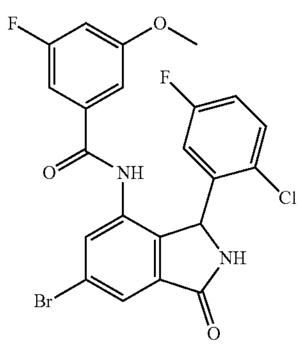 [SMILES: COc1cc(F)cc(C(=O)Nc2cc(Br)cc3c2C(c2cc(F)ccc2Cl)NC3=O)c1] | COc1cc(F)cc(c1)C(=O)Nc1cc(Br)cc2C(=O)NC(c12)c1cc(F)ccc1Cl | 1H NMR (400 MHz, DMSO-d6) 10.29 (s, 1H), 9.31-9.26 (m, 1H), 7.82-7.77 (m, 1H), 7.74 (d, 2.0 Hz, 1H), 7.37 (dd, 8.8, 5.1 Hz, 1H), 7.14 (td, 8.4, 3.0 Hz, 1H), 7.05 (dt, 10.7, 2.5 Hz, 1H), 6.97 (s, 1H), 6.92 (d, 9.0 Hz, 1H), 6.70 (s, 1H), 6.01 (s, 1H), 3.80 (s, 3H). | 506.9 | C | |
| I-801 | 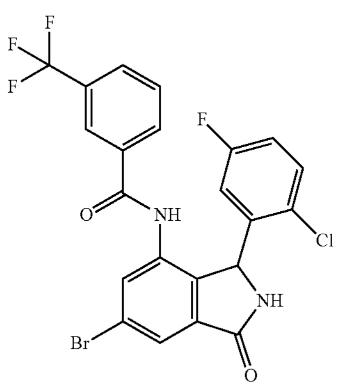 [SMILES: O=C(Nc1cc(Br)cc2c1C(c1cc(F)ccc1Cl)NC2=O)c1cccc(C(F)(F)F)c1] | Fc1ccc(C1)c(c1)C1NC(=O)c2cc(Br)cc(NC(=O)c3cccc(c3)C(F)(F)F)c12 | 1H NMR (400 MHz, DMSO-d6) 10.51 (s, 1H), 9.29 (s, 1H), 7.93 (t, 9.0 Hz, 2H), 7.81 (d, 1.7 Hz, 1H), 7.78-7.67 (m, 3H), 7.32 (dd, 8.8, 5.1 Hz, 1H), 7.09 (td, 8.3, 3.0 Hz, 1H), 6.91-6.24 (m, 1H), 5.99 (s, 1H). | 526.9 | B | |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-802 | 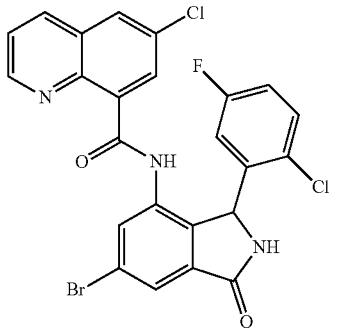 [SMILES: O=C1NC(c2cc(F)ccc2Cl)c2c(NC(=O)c3cc(Cl)cc4cccnc34)cc(Br)cc21] | Fc1ccc(C1)c(c1)C1NC(=O)c2cc(Br)cc(NC(=O)c3cc(Cl)cc4cccnc34)c12 | 1H NMR (400 MHz, Chloroform-d) 13.17 (s, 1H), 8.82 (d, 2.5 Hz, 2H), 8.61 (dd, 4.4, 1.8 Hz., 1H), 8.22 (dd, 8.4, 1.8 Hz, 1H), 8.00 (d, 2.5 Hz, 1H), 7.95 (d, 1.7 Hz, 1H), 7.51 (dd, 8.4, 4.3 Hz, 1H), 7.34 (dd, 8.8, 4.9 Hz, 1H), 6.89-6.80 (m, 1H), 6.64 (s, 1H), 6.59 (dd, 8.8, 2.9 Hz, 1H), 6.27 (s, 1H). | 543.95 | E | |
| I-803 | 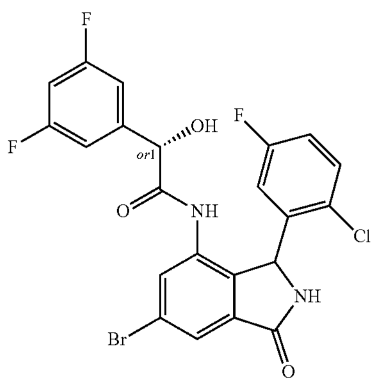 [SMILES: O=C1NC(c2cc(F)ccc2Cl)c2c(NC(=O)[C@@H](O)c3cc(F)cc(F)c3)cc(Br)cc21] | O[C@H](C(=O)Nc1cc(Br)cc2C(=O)NC(c12)c1cc(F)ccc1Cl)c1cc(F)cc(F)c1 | 1H NMR (400 MHz, DMSO-d6) 9.54 (s, 1H), 9.25 (s, 1H), 8.01 (s, 1H), 7.70 (d, 1.7 Hz, 1H), 7.41 (s, 1H), 7.16-7.04 (m, 2H), 6.84 (s, 1H), 6.81-6.74 (m, 2H), 6.56 (s, 1H), 6.18 (s, 1H), 5.04 (d, 3.1 Hz, 1H) | 525.15 | E | |
| I-804 | 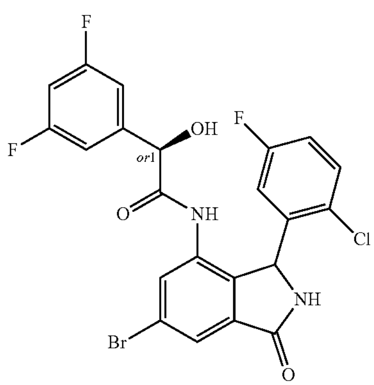 [SMILES: O=C1NC(c2cc(F)ccc2Cl)c2c(NC(=O)[C@H](O)c3cc(F)cc(F)c3)cc(Br)cc21] | O[C@@H](C(=O)Nc1cc(Br)cc2C(=O)NC(c12)c1cc(F)ccc1Cl)c1cc(F)cc(F)c1 | 1H NMR (400 MHz, DMSO-d6) 9.72 (s, 1H), 9.20 (s, 1H), 7.91 (s, 1H), 7.71 (d, 1.7 Hz, 1H), 7.31 (dd, 8.8, 5.1 Hz, 1H), 7.13 (ddt, 10.9, 8.5, 4.2 Hz, 2H), 6.92 (d, 7.6 Hz, 2H), 6.75 (d, 4.5 Hz, 1H), 6.51 (s, 1H), 6.06 (s, 1H), 4.97 (d, 4.2 Hz, 1H). | 525.15 | E | |
| I-805 | 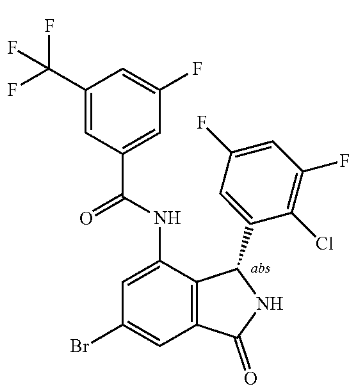 [SMILES: O=C(Nc1cc(Br)cc2c1[C@H](c1cc(F)cc(F)c1Cl)NC2=O)c1cc(F)cc(C(F)(F)F)c1] | Fc1cc(F)c(Cl)c(c1)[C@@H]1NC(=O)c2cc(Br)cc(NC(=O)c3cc(F)cc(c3)C(F)(F)F)c12 | 1H NMR (400 MHz, DMSO-d6) 10.60 (s, 1H), 9.33 (s, 1H), 7.99 (dt, 8.6, 2.1 Hz, 1H), 7.85 (d, 1.7 Hz, 1H), 7.81-7.74 (m, 2H), 7.68 (s, 1H), 7.41 (td, 8.9, 2.9 Hz, 1H), 6.63 (s, 1H), 6.02 (s, 1H). | 563 | A | |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-806 | 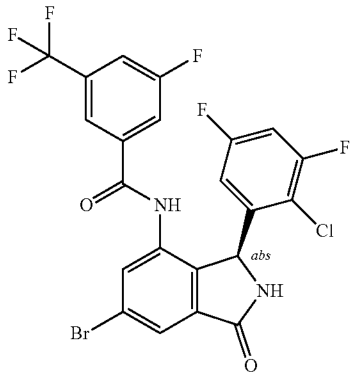 [SMILES: O=C(Nc1cc(Br)cc2c1[C@@H](c1cc(F)cc(F)c1Cl)NC2=O)c1cc(F)cc(C(F)(F)F)c1] | Fc1cc(F)c(Cl)c(c1)[C@H]1NC(=O)c2cc(Br)cc(NC(=O)c3cc(F)cc(c3)C(F)(F)F)c12 | 1H NMR (400 MHz, DMSO-d6) 10.58 (s, 1H), 9.32 (s, 1H), 7.98 (dd, 8.5, 2.4 Hz, 1H), 7.85 (d, 1.7 Hz, 1H), 7.81-7.74 (m, 2H), 7.68 (s, 1H), 7.41 (td, 9.0, 2.9 Hz, 1H), 6.66 (s, 1H), 6.01 (s, 1H). | 562.85 | C | |
| I-807 | 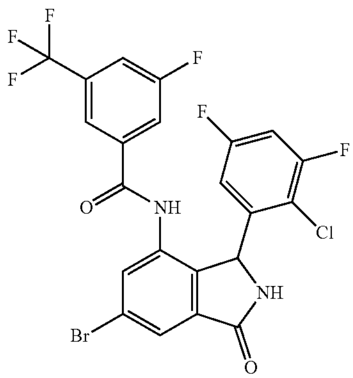 [SMILES: O=C(Nc1cc(Br)cc2c1C(c1cc(F)cc(F)c1Cl)NC2=O)c1cc(F)cc(C(F)(F)F)c1] | Fc1cc(F)c(Cl)c(c1)C1NC(=O)c2cc(Br)cc(NC(=O)c3cc(F)cc(c3)C(F)(F)F)c12 | 1H NMR (400 MHz, DMSO-d6) 10.58 (s, 1H), 9.32 (s, 1H), 7.98 (d, 8.4 Hz, 1H), 7.85 (d, 1.7 Hz, 1H), 7.81-7.74 (m, 2H), 7.68 (s, 1H), 7.40 (td, 8.9, 2.9 Hz, 1H), 6.65 (s, 1H), 6.01 (s, 1H). | 562.9 | A | |
| I-808 | 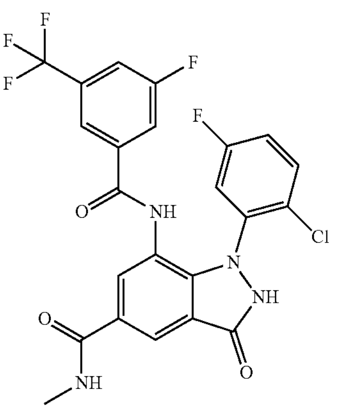 [SMILES: CNC(=O)c1cc(NC(=O)c2cc(F)cc(C(F)(F)F)c2)c2c(c1)c(=O)[nH]n2-c1cc(F)ccc1Cl] | CNC(=O)c1cc(NC(=O)c2cc(F)cc(c2)C(F)(F)F)c2n[nH]c(=O)c2c1)-c1cc(F)ccc1Cl | NMR (400 MHz, CD3CN) 8.78 (s, 1H), 8.38 (s, 1H), 7.81 (s, 1H), 7.63 (d, 8.3 Hz, 1H), 7.58-7.49 (m, 2H), 7.37 (br s, 1H), 7.33-7.18 (m, 2H), 6.89 (td, 9.2, 3.7 Hz, 1H), 2.87 (d, 4.5 Hz, 3H). | 523.3 | D | |
| I-809 | 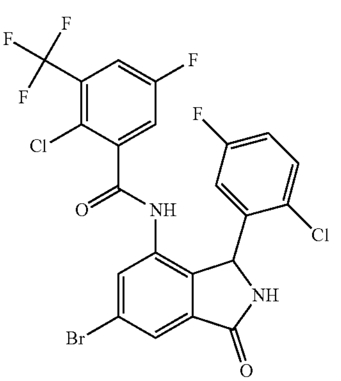 [SMILES: O=C(Nc1cc(Br)cc2c1C(c1cc(F)ccc1Cl)NC2=O)c1cc(F)cc(C(F)(F)F)c1Cl] | Fc1ccc(C1)c(c1)C1NC(=O)c2cc(Br)cc(NC(=O)c3cc(F)cc(c3Cl)C(F)(F)F)c12 | (400 MHz, DMSO-d6) 10.65 (br s, 1H), 9.33 (s, 1H), 7.97 (dd, 8.5, 3.0 Hz, 1H), 7.86 (d, 1.7 Hz, 1H), 7.81 (d, 1.5 Hz, 1H), 7.60-7.48 (m, 1H), 7.30 (td, 8.4, 3.0 Hz, 1H), 7.16 (d, 5.8 Hz, 1H), 6.67 (br s, 1H), 6.09 (br s, 1H) | 577.3 | D | |

TABLE 2-continued

Representative Compounds of the Invention with Bioactivity Data.

| Ex. No. | Structure | SMILES | $^1$H NMR | MS | ADP-Glo IC$_{50}$ | MCF 10A IC$_{50}$ |
|---|---|---|---|---|---|---|
| I-810 | 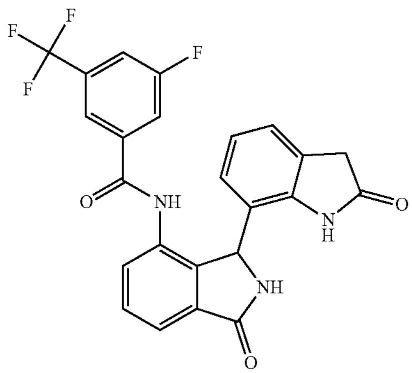 | Fc1cc(cc(c1)C(F)(F)F)C(=O)Nc1ccc2C(=O)NC(c12)c1cccc2CC(=O)Nc12 | 1H NMR (400 MHz, DMSO-d6) 10.53 (br. s, 1H), 10.37 (br. s, 1H), 9.00 (s, 1H), 7.91 (d, 8.5 Hz, 1H), 7.67 (dd, 7.5, 1.0 Hz, 1H), 7.61 (t, 7.6 Hz, 1H), 7.52-7.46 (m, 2H), 7.43 (s, 1H), 6.99 (d, 6.6 Hz, 1H), 6.76 (t, 7.6 Hz, 1H), 6.31 (d, 7.5 Hz, 1H), 5.94 (br. s, 1H), 3.38 (d, 22.7 Hz, 1H), 2.70 (d, 22.7 Hz, 1H). | 470.2 | E | |
| I-811 | 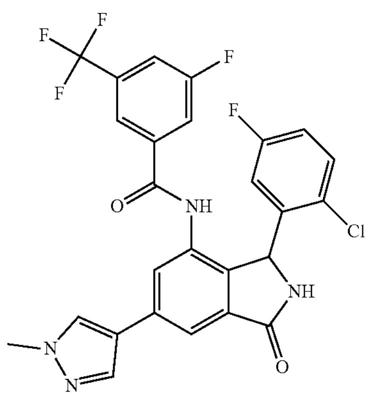 [SMILES: Cn1cc(-c2cc(NC(=O)c3cc(F)cc(C(F)(F)F)c3)c3c(c2)C(=O)NC3c2cc(F)ccc2Cl)cn1] | Cn1cc(cn1)-c1cc2C(=O)NC(c2c(NC(=O)c2cc(F)cc(c2)C(F)(F)F)c1)c1cc(F)ccc1Cl | 1h NMR (400 MHz, DMSO-d6) 10.52 (s, 1H), 9.14 (br. s, 1H), 8.34 (s, 1H), 8.01 (s, 1H), 7.95 (dt, 9.9, 1.5 Hz, 1H), 7.88 (d, 1.0 Hz, 1H), 7.75 (d, 8.0 Hz, 1H), 7.71-7.66 (m, 8.8 Hz, 2H), 7.31 (dd, 8.9, 5.1 Hz, 1H), 7.09 (td, 8.5, 3.0 Hz, 1H), 6.61 (br. s, 1H), 5.96 (br. s, 1H), 3.89 (s, 3H) | 547.2 | A | A |
| I-812 | 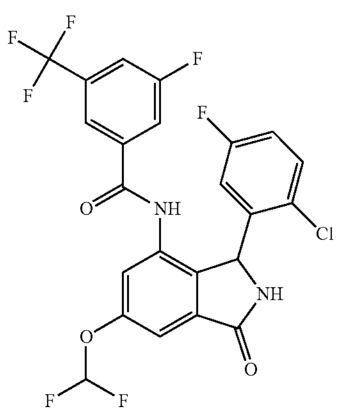 [SMILES: O=C(Nc1cc(OC(F)F)cc2c1C(c1cc(F)ccc1Cl)NC2=O)c1cc(F)cc(C(F)(F)F)c1] | FC(F)Oc1cc2C(=O)NC(c2c(NC(=O)c2cc(F)cc(c2)C(F)(F)F)c1)c1cc(F)ccc1Cl | NMR (400 MHz, MeCN-d3) 8.70 (br. s, 1H), 7.68-7.63 (m, 1H), 7.61-7.57 (m, 1H), 7.56 (s, 1H), 7.49 (d, 2.1 Hz, 1H), 7.40 (d, 1.4 Hz, 1H), 7.34 (s, 1H), 7.27 (dd, 8.9, 5.1 Hz, 1H), 6.98 (ddd, 8.8, 8.1, 3.1 Hz, 1H), 6.91 (t, 73.6 Hz, 1H), 6.66 (br.s, 1H), 6.12 (br. s, 1H). Contains 4% of formate salt at 8.17 | 531.4 | A | |

TABLE 2-continued

Representative Compounds of the Invention with Bioactivity Data.

| Ex. No. | Structure | SMILES | $^1$H NMR | MS | ADP-Glo IC$_{50}$ | MCF 10A IC$_{50}$ |
|---|---|---|---|---|---|---|
| I-813 | 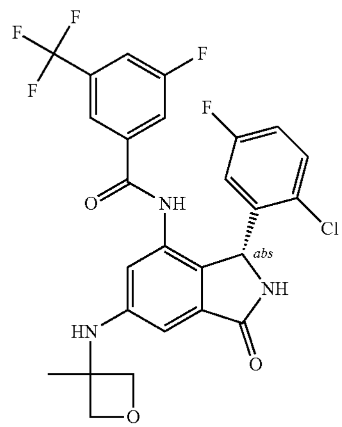 [SMILES: CC1(Nc2cc(NC(=O)c3cc(F)cc(C(F)(F)F)c3)c3c(c2)C(=O)N[C@H]3c2cc(F)ccc2Cl)COC1] | CC1(COC1)Nc1cc2C(=O)N[C@H](c2c(NC(=O)c2cc(F)cc(c2)C(F)(F)F)c1)c1cc(F)ccc1Cl | NMR (400 MHz, DMSO-d6) 10.24 (s, 1H), 8.91 (br. s, 1H), 7.88 (td, 8.4, 1.6 Hz, 1H), 7.64 (d, 9.0 Hz, 1H), 7.55 (s, 1H), 7.25 (dd, 8.9, 5.2 Hz, 1H), 7.03 (td, 8.4, 3.1 Hz, 1H), 6.64 (s, 1H), 6.57 (br. s, 1.6 Hz, 1H), 6.52 (d, 2.1 Hz, 1H), 6.47 (br. d, 1H), 5.80 (s, 1H), 4.63 (d, 5.7 Hz, 2H), 4.48 (d, 5.8 Hz, 2H), 1.57 (s, 3H). | 552.1 | A | |
| I-814 | 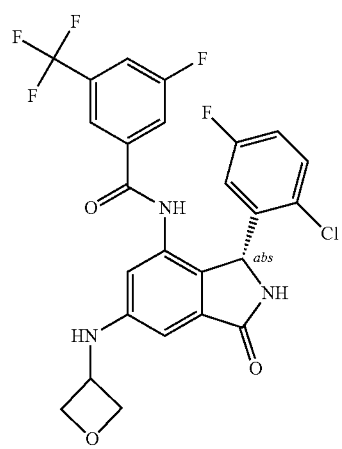 [SMILES: O=C(Nc1cc(NC2COC2)cc2c1[C@H](c1cc(F)ccc1Cl)NC2=O)c1cc(F)cc(C(F)(F)F)c1] | Fc1ccc(C1)c(c1)[C@@H]1NC(=O)c2cc(NC3COC3)cc(NC(=O)c3cc(F)cc(c3)C(F)(F)F)c12 | NMR (400 MHz, DMSO-d6) 10.30 (s, 1H), 8.95 (br. s, 1H), 7.92 (d, 8.6 Hz, 1H), 7.69 (d, 8.9 Hz, 1H), 7.60 (s, 1H), 7.28 (dd, 8.9, 5.2 Hz, 1H), 7.06 (td, 8.4, 3.1 Hz, 1H), 6.94 (d, 6.3 Hz, 1H), 6.69 (d, 2.0 Hz, 1H), 6.62 (s, 1H), 6.57 (br. s, 1H), 5.82 (br. s, 1H), 4.89 (t, 6.5 Hz, 2H), 4.62 (dd, 12.7, 6.4 Hz, 1H), 4.45 (q, 6.1 Hz, 2H). | 538.3 | A | A |
| I-815 | 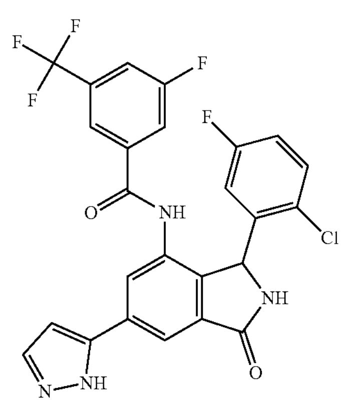 [SMILES: O=C(Nc1cc(-c2ccn[nH]2)cc2c1C(c1cc(F)ccc1Cl)NC2=O)c1cc(F)cc(C(F)(F)F)c1] | Fc1ccc(C1)c(c1)C1NC(=O)c2cc(cc(NC(=O)c3cc(F)cc(c3)C(F)(F)F)c12)-c1ccn[nH]1 | NMR (400 MHz, CD3CN) 8.67 (br s, 1H), 8.10 (d, 1.3 Hz, 1H), 8.05 (s, 1H), 7.68 (d, 2.4 Hz, 1H), 7.63 (d, 8.5 Hz, 1H), 7.59 (d, 9.0 Hz, 1H), 7.57 (s, 1H), 7.24 (dd, 8.9, 5.1 Hz, 2H), 6.99-6.91 (m, 1H), 6.79 (d, 2.4 Hz, 1H), 6.68 (br s, 1H), 6.14 (br s, 1H). | 533.3 | A | |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-816 | 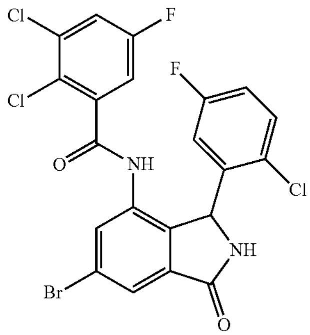 [SMILES: O=C(Nc1cc(Br)cc2c1C(c1cc(F)ccc1Cl)NC2=O)c1cc(F)cc(Cl)c1Cl] | Fc1ccc(C1)c(c1)CNC(=O)c2cc(Br)cc(NC(=O)c3cc(F)cc(Cl)c3Cl)c12 | NMR (400 MHz, DMSO) 9.29 (s, 1H), 7.81 (d, 1.6 Hz, 1H), 7.75 (d, 1.6 Hz, 1H), 7.60 (m, 3H), 7.36 (dd, 8.7, 5.2 Hz, 1H), 7.17-7.11 (m, 1H), 5.96 (br s, 1H). | 545 | B | |
| I-817 | 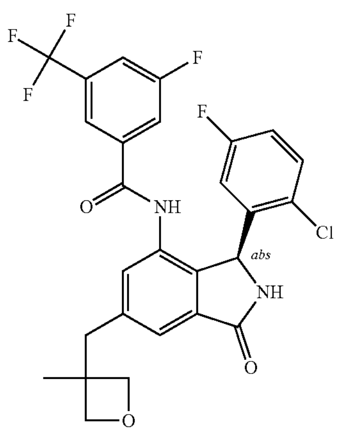 [SMILES: CC1(Cc2cc(NC(=O)c3cc(F)cc(C(F)(F)F)c3)c3c(c2)C(=O)N[C@@H]3c2cc(F)ccc2Cl)COC1] | CC1(Cc2cc3C(=O)N[C@@H](c3c(NC(=O)c3cc(F)cc(c3)C(F)(F)F)c2)c2cc(F)ccc2Cl)COC1 | | 551.31 | D | |
| I-818 | 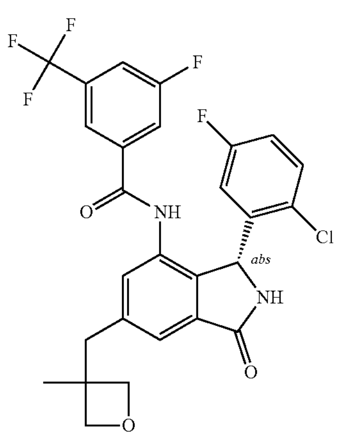 [SMILES: CC1(Cc2cc(NC(=O)c3cc(F)cc(C(F)(F)F)c3)c3c(c2)C(=O)N[C@H]3c2cc(F)ccc2Cl)COC1] | CC1(Cc2cc3C(=O)N[C@H](c3c(NC(=O)c3cc(F)cc(c3)C(F)(F)F)c2)c2cc(F)ccc2Cl)COC1 | | 551.31 | A | |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-819 | 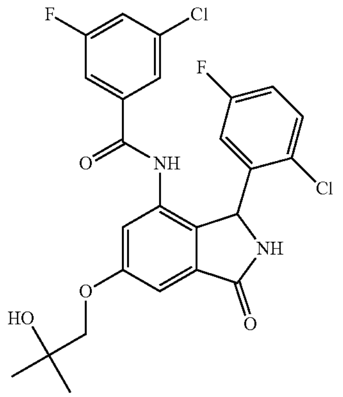 [SMILES: CC(C)(O)COc1cc(NC(=O)c2cc(F)cc(Cl)c2)c2c(c1)C(=O)NC2c1cc(F)ccc1Cl] | CC(C)(O)COc1cc2C(=O)NC(c2c(NC(=O)c2cc(F)cc(Cl)c2)c1)c1cc(F)ccc1Cl | | 521 | A | |
| I-820 | 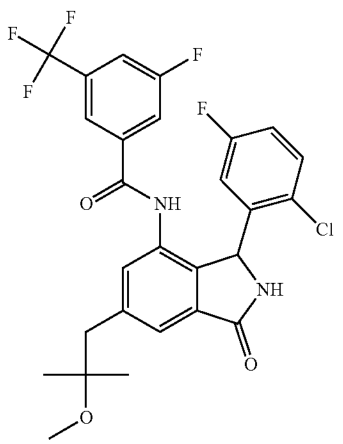 [SMILES: COC(C)(C)Cc1cc(NC(=O)c2cc(F)cc(C(F)(F)F)c2)c2c(c1)C(=O)NC2c1cc(F)ccc1Cl] | COC(C)(C)Cc1cc2C(=O)NC(c2c(NC(=O)c2cc(F)cc(c2)C(F)(F)F)c1)c1cc(F)ccc1Cl | | 553.31 | A | |
| I-821 | 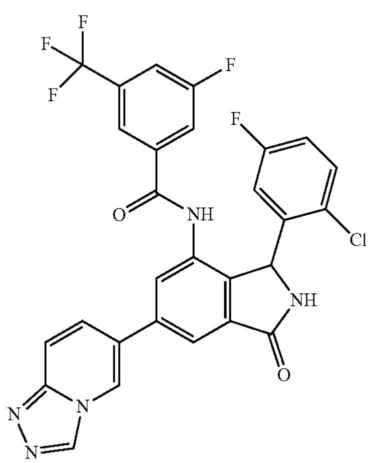 [SMILES: O=C(Nc1cc(-c2ccc3nncn3c2)cc2c1C(c1cc(F)ccc1Cl)NC2=O)c1cc(F)cc(C(F)(F)F)c1] | Fc1ccc(C1)c(c1)C1NC(=O)c2cc(cc(NC(=O)c3cc(F)cc(c3)C(F)(F)F)c12)-c1ccc2nncn2c1 | 1H NMR (DMSO-d6, 400 MHz):-' = 10.64 (s, 1H), 9.28 (d, 0.8 Hz, 1H), 9.22-9.27 (m, 1H), 9.14 (s, 1H), 8.05 (s, 1H), 7.97 (br d, 8.1 Hz, 1H), 7.88-7.94 (m, 2H), 7.83-7.88 (m, 1H), 7.78 (br d, 8.8 Hz, 1H), 7.73 (s, 1H), 7.35 (dd, 8.8, 5.3 Hz, 1H), 7.12 (td, 8.3, 3.0 Hz, 1H), 6.50-7.03 (m, 1H), 6.07 (br s, 1H) | 584 | A | |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-822 | 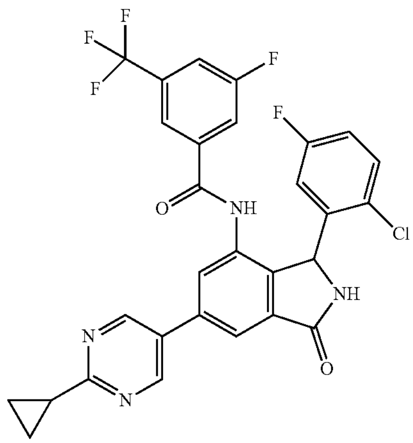 [SMILES: O=C(Nc1cc(-c2cnc(C3CC3)nc2)cc2c1C(c1cc(F)ccc1Cl)NC2=O)c1cc(F)cc(C(F)(F)F)c1] | Fc1ccc(C1)c(c1)C1NC(=O)c2cc(cc(NC(=O)c3cc(F)cc(c3)C(F)(F)F)c12)-c1cnc(nc1)C1CC1 | | 585 | A | |
| I-823 | 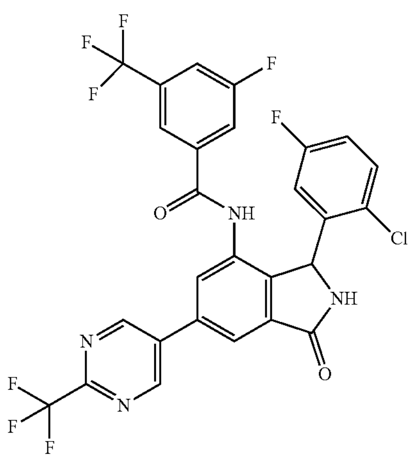 [SMILES: O=C(Nc1cc(-c2cnc(C(F)(F)F)nc2)cc2c1C(c1cc(F)ccc1Cl)NC2=O)c1cc(F)cc(C(F)(F)F)c1] | Fc1ccc(C1)c(c1)C1NC(=O)c2cc(cc(NC(=O)c3cc(F)cc(c3)C(F)(F)F)c12)-c1cnc(nc1)C(F)(F)F | | 613.1 | A | |
| I-824 | 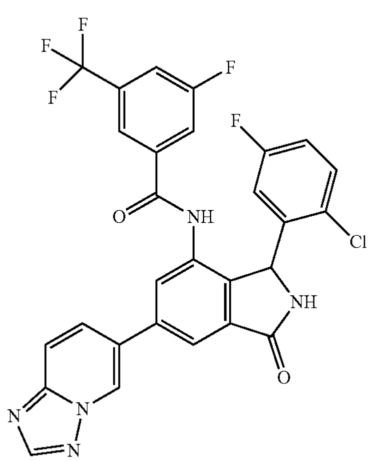 [SMILES: O=C(Nc1cc(-c2ccc3ncnn3c2)cc2c1C(c1cc(F)ccc1Cl)NC2=O)c1cc(F)cc(C(F)(F)F)c1] | Fc1ccc(C1)c(c1)C1NC(=O)c2cc(cc(NC(=O)c3cc(F)cc(c3)C(F)(F)F)c12)-c1ccc2ncnn2c1 | | 584 | A | |

TABLE 2-continued

Representative Compounds of the Invention with Bioactivity Data.

| Ex. No. | Structure | SMILES | $^1$H NMR | MS | ADP-Glo IC$_{50}$ | MCF 10A IC$_{50}$ |
|---|---|---|---|---|---|---|
| I-825 | 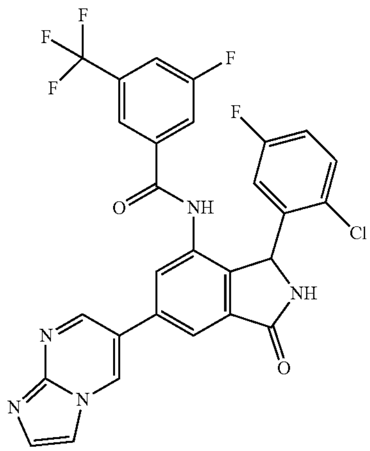 [SMILES: O=C(Nc1cc(-c2cnc3nccn3c2)cc2c1C(c1cc(F)ccc1Cl)NC2=O)c1cc(F)cc(C(F)(F)F)c1] | Fc1ccc(C1)c(c1)C1NC(=O)c2cc(cc(NC(=O)c3cc(F)cc(c3)C(F)(F)F)c12)-c1cnc2nccn2c1 | | 584 | A | |
| I-826 | 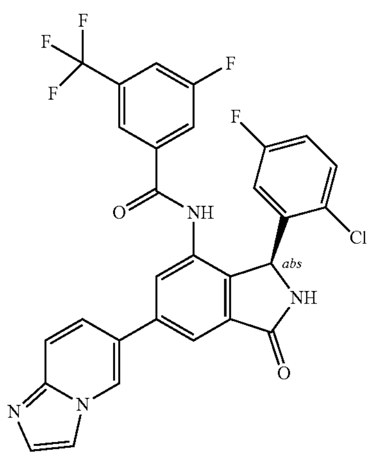 [SMILES: O=C(Nc1cc(-c2ccc3nccn3c2)cc2c1[C@@H](c1cc(F)ccc1Cl)NC2=O)c1cc(F)cc(C(F)(F)F)c1] | Fc1ccc(C1)c(c1)[C@H]1NC(=O)c2cc(cc(NC(=O)c3cc(F)cc(c3)C(F)(F)F)c12)-c1ccc2nccn2c1 | | | | C |
| I-827 | 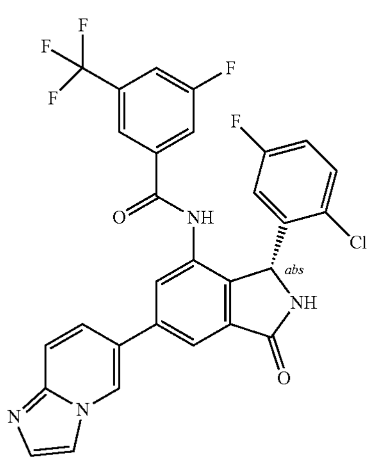 [SMILES: O=C(Nc1cc(-c2ccc3nccn3c2)cc2c1[C@H](c1cc(F)ccc1Cl)NC2=O)c1cc(F)cc(C(F)(F)F)c1] | Fc1ccc(C1)c(c1)[C@@H]1NC(=O)c2cc(cc(NC(=O)c3cc(F)cc(c3)C(F)(F)F)c12)-c1ccc2nccn2c1 | | 583.3 | A | |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-828 | 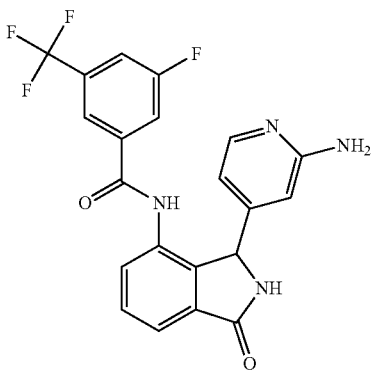 [SMILES: Nc1cc(C2NC(=O)c3cccc(NC(=O)c4cc(F)cc(C(F)(F)F)c4)c32)ccn1] | Nc1cc(ccn1)C1NC(=O)c2ccc(NC(=O)c3cc(F)cc(c3)C(F)(F)F)c12 | (400 MHz, d6-DMSO) 10.51 (s, 1H), 9.06 (s, 1H), 8.35 (s, 1H), 7.97 (d, 8.3 Hz, 1H), 7.83 (br s, 1H), 7.79 (br d, 8.7 Hz, 1H), 7.66 (dd, 7.4, 1.0 Hz, 1H), 7.62 (dd, 5.7, 0.8 Hz, 1H) 7.58 (t, 7.5 Hz, 1H), 7.50 (dd, 7.7, 0.9 Hz, 1H), 6.06 (dd, 5.2, 1.4 Hz, 1H), 6.05 (s, 1H) 5.78 (br s, 2H), 5.54 (s, 1H). | 431.2 | E | |
| I-829 | 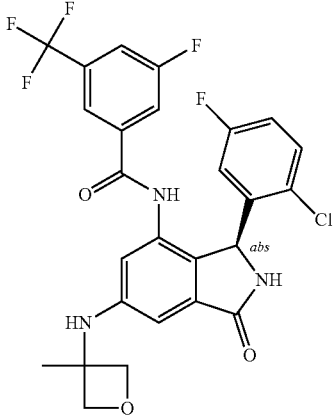 [SMILES: CC1(Nc2cc(NC(=O)c3cc(F)cc(C(F)(F)F)c3)c3c(c2)C(=O)N[C@@H]3c2cc(F)ccc2Cl)COC1] | CC1(COC1)Nc1cc2C(=O)N[C@@H](c2c(NC(=O)c2cc(F)cc(c2)C(F)(F)F)c1c(F)ccc1Cl | NMR (400 MHz, DMSO-d6) 10.24 (s, 1H), 8.91 (br. s, 1H), 7.88 (td, 8.4, 1.6 Hz, 1H), 7.64 (d, 9.0 Hz, 1H), 7.55 (s, 1H), 7.25 (dd, 8.9, 5.2 Hz, 1H), 7.03 (td, 8.4, 3.1 Hz, 1H), 6.64 (s, 1H), 6.57 (br. s, 1.6 Hz, 1H), 6.52 (d, 2.1 Hz, 1H), 6.47 (br. d, 1H), 5.80 (s, 1H), 4.63 (d, 5.7 Hz, 2H), 4.48 (d, 5.8 Hz, 2H), 1.57 (s, 3H). | 552.1 | C | |
| I-830 | 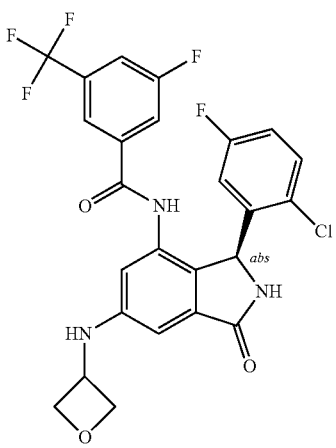 [SMILES: O=C(Nc1cc(NC2COC2)cc2c1[C@@H](c1cc(F)ccc1Cl)NC2=O)c1cc(F)cc(C(F)(F)F)c1] | Fc1ccc(C1)c(c1)[C@H]1NC(=O)c2cc(NC3COC3)cc(NC(=O)c3cc(F)cc(c3)C(F)(F)F)c12 | NMR (400 MHz, DMSO-d6) 10.30 (s, 1H), 8.95 (br. s, 1H), 7.92 (d, 8.6 Hz, 1H), 7.69 (d, 8.9 Hz., 1H), 7.60 (s, 1H), 7.28 (dd, 8.9, 5.2 Hz, 1H), 7.06 (td, 8.4, 3.1 Hz, 1H), 6.94 (d, 6.3 Hz, 1H), 6.69 (d, 2.0 Hz, 1H), 6.62 (s, 1H), 6.57 (br. s, 1H), 5.82 (br. s, 1H), 4.89 (t, 6.5 Hz, 2H), 4.62 (dd, 12.7, 6.4 Hz, 1H), 4.45 (q, 6.1 Hz, 2H). | 538.3 | D | |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-831 | 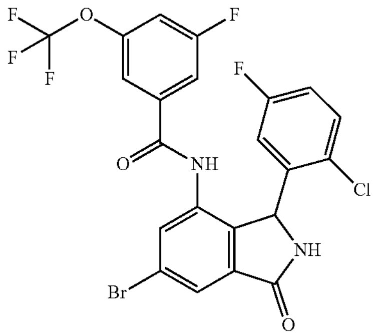 [SMILES: O=C(Nc1cc(Br)cc2c1C(c1cc(F)ccc1Cl)NC2=O)c1cc(F)cc(OC(F)(F)F)c1] | Fc1ccc(C1)c(c1)C1NC(=O)c2cc(Br)cc(NC(=O)c3cc(F)cc(OC(F)(F)F)c3)c12 | 1H NMR (400 MHz, Chloroform-d) 8.40 (s, 1H), 7.94 (d, 1.6 Hz, 1H), 7.54-7.40 (m, 2H), 7.22-7.15 (m, 2H), 7.14-7.04 (m, 2H), 6.73 (d, 14.7 Hz, 2H), 6.18 (s, 1H). | 563.1 | B | |
| I-832 | 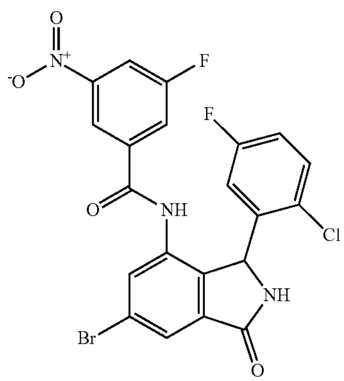 | [O-][N+](=O)c1cc(F)cc(c1)C(=O)Nc1cc(Br)cc2C(=O)NC(c12)c1cc(F)ccc1Cl | 1H NMR (400 MHz, CDCl3) 8.47 (s, 1H), 8.16 (dt, 7.7, 2.2 Hz, 1H), 8.03-7.97 (m, 2H), 7.82-7.75 (m, 1H), 7.51 (dd, 8.7, 4.3 Hz, 2H), 7.14 (ddd, 8.9, 7.3, 3.0 Hz, 1H), 6.74 (s, 1H), 6.46 (s, 1H), 6.21 (s, 1H). | 524 | A | |
| I-833 | 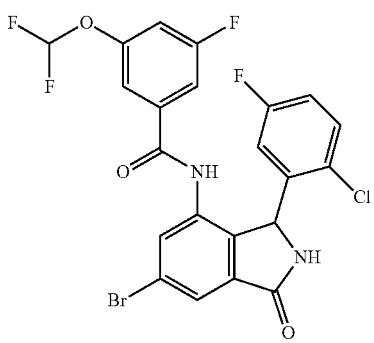 [SMILES: O=C(Nc1cc(Br)cc2c1C(c1cc(F)ccc1Cl)NC2=O)c1cc(F)cc(OC(F)F)c1] | FC(F)Oc1cc(F)cc(c1)C(=O)Nc1cc(Br)cc2C(=O)NC(c12)c1cc(F)ccc1Cl | 1H NMR (400 MHz, Chloroform-d) 8.45 (s, 1H), 7.96 (d, 1.6 Hz, 1H), 7.45 (dd, 8.9, 4.9 Hz, 1H), 7.34 (s, 1H), 7.08 (dddd, 20.4, 10.1, 7.8, 2.5 Hz, 4H), 6.72 (s, 1H), 6.58-6.43 (m, 2H), 6.18 (s, 1H). | 545 | B | |
| I-834 | 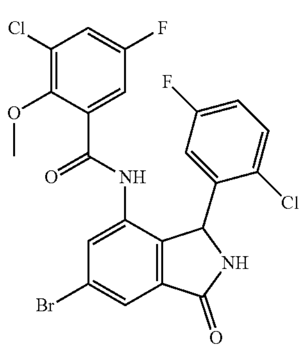 [SMILES: COc1c(Cl)cc(F)cc1C(=O)Nc1cc(Br)cc2c1C(c1cc(F)ccc1Cl)NC2=O] | COc1c(C1)cc(F)cc1C(=O)Nc1cc(Br)cc2C(=O)NC(c12)c1cc(F)ccc1Cl | 1H NMR (400 MHz, DMSO-d6) 10.29 (s, 1H), 9.31 (s, 1H), 7.84 (d, 1.8 Hz, 1H), 7.80 (d, 1.7 Hz, 1H), 7.70 (dd, 8.1, 3.1 Hz, 1H), 7.50 (t, 6.3 Hz., 1H), 7.27 (ddd, 8.9, 7.9, 3.1 Hz, 1H), 6.60 (dd, 8.3, 3.2 Hz, 2H), 6.07 (s, 1H), 3.64 (s, 3H), 1.59 (s, 1H). | 540.95 | D | |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-835 | 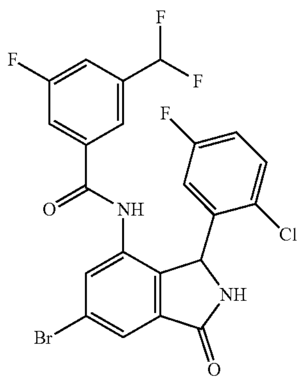 [SMILES: O=C(Nc1cc(Br)cc2c1C(c1cc(F)ccc1Cl)NC2=O)c1cc(F)cc(C(F)F)c1] | FC(F)c1cc(F)cc(c1)C(=O)Nc1cc(Br)cc2C(=O)NC(c12)c1cc(F)ccc1Cl | 1H NMR (400 MHz, Methanol-d4) 7.96 (d, 1.6 Hz, 1H), 7.74 (s, 1H), 7.61-7.45 (m, 3H), 7.31 (dd, 8.9, 5.0 Hz, 1H), 7.08-6.95 (m, 1H), 6.84 (s, 1H), 6.71 (s, 1H), 6.19 (s, 1H). | 526.85 | B | |
| I-836 | 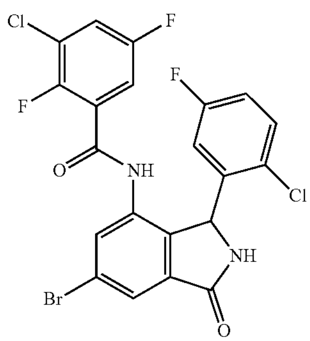 [SMILES: O=C(Nc1cc(Br)cc2c1C(c1cc(F)ccc1Cl)NC2=O)c1cc(F)cc(Cl)c1F] | Fc1ccc(C1)c(c1)C1NC(=O)c2cc(Br)cc(NC(=O)c3cc(F)cc(Cl)c3F)c12 | 1H NMR (400 MHz, DMSO-d6) 10.51 (s, 1H), 9.31 (s, 1H), 7.86 (ddd, 8.4, 5.5, 3.2 Hz, 1H), 7.81 (d, 1.7 Hz, 1H), 7.74 (d, 1.8 Hz, 1H), 7.47 (t, 7.0 Hz, 1H), 7.25 (ddd, 8.8, 7.9, 3.1 Hz, 1H), 7.03 (ddd, 7.9, 4.5, 2.9 Hz, 1H), 6.84 (s, 1H), 6.00 (s, 1H). | 528.9 | C | |
| I-837 | 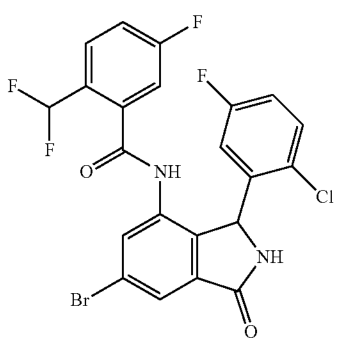 [SMILES: O=C(Nc1cc(Br)cc2c1C(c1cc(F)ccc1Cl)NC2=O)c1cc(F)ccc1C(F)F] | FC(F)c1ccc(F)cc1C(=O)Nc1cc(Br)cc2C(=O)NC(c12)c1cc(F)ccc1Cl | 1H NMR (400 MHz, Methanol-d4) 7.95 (d, 1.7 Hz, 1H), 7.84-7.72 (m, 2H), 7.47 (dd, 8.9, 5.0 Hz, 1H), 7.39 (td, 8.4, 2.7 Hz, 1H), 7.26-6.93 (m, 2H), 6.54 (s, 2H), 6.19 (s, 1H). | 526.9 | D | |
| I-838 | 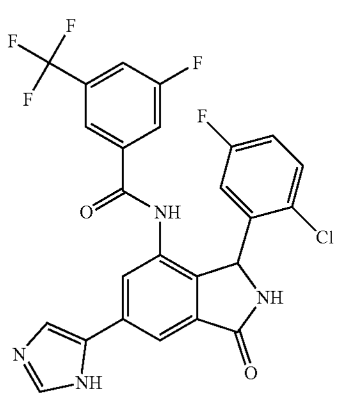 [SMILES: O=C(Nc1cc(-c2cnc[nH]2)cc2c1C(c1cc(F)ccc1Cl)NC2=O)c1cc(F)cc(C(F)(F)F)c1] | Fc1ccc(C1)c(c1)C1NC(=O)c2cc(cc(NC(=O)c3cc(F)cc(c3)C(F)(F)F)c12)-c1cnc[nH]1 | NMR (400 MHz, DMSO-d6): Presence of the 2 tautomeric forms of the imidazole (4 and 5 substituted imidazoles) in a 3:1 ratio. Major tautomer:-' 12.32 (br. s, 1H), 10.55 (s, 1H), 9.12 (s, 1H), 8.07 (d, 0.8 Hz, 1H), 7.96 (s, 1H), 7.93 (s, 1H), 7.84 (br. s, 1H), 7.79-7.74 (m, 2H), 7.70 (s, 1H), 7.31 (dd, 8.9, 5.2 Hz, 1H), 7.11-7.06 (m, 1H), 6.63 (br. s, 1H), 5.97 (br. s, 1H). 24% of formate salt at 8.24. | 533.2 | A | |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-839 | 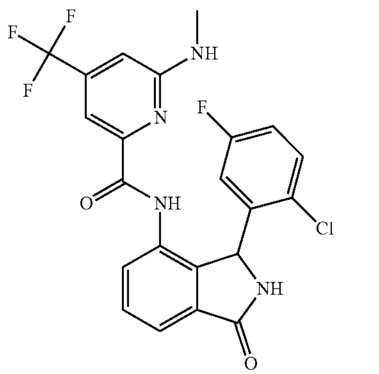 [SMILES: CNc1cc(C(F)(F)F)cc(C(=O)Nc2cccc3c2C(c2cc(F)ccc2Cl)NC3=O)n1] | CNc1cc(cc(n1)C(=O)Nc1cccc2C(=O)NC(c12)c1cc(F)ccc1Cl)C(F)(F)F | 1H-NMR (400 MHz, DMSO-d6) 9.90 (s, 1H), 9.13 (s, 1H), 7.80 (d, 6.2 Hz, 1H), 7.69-7.60 (m, 2H), 7.36-7.27 (m, 2H), 7.18 (d, 1.0 Hz, 1H), 7.07 (td, 8.4, 3.1 Hz, 1H), 6.93-6.91 (m, 1H), 6.62 (br. s, 1H), 6.17 (br. s, 1H), 2.84 (d, 4.4 Hz, 3H). | 479.3 | E | |
| I-840 | 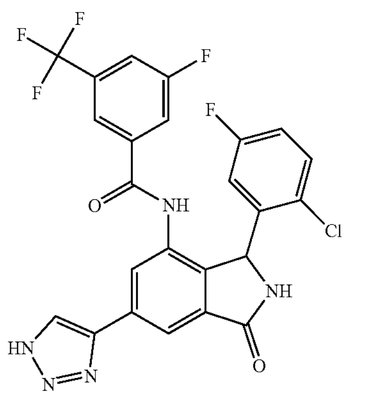 [SMILES: O=C(Nc1cc(-c2c[nH]nn2)cc2c1C(c1cc(F)ccc1Cl)NC2=O)c1cc(F)cc(C(F)(F)F)c1] | Fc1ccc(C1)c(c1)C1NC(=O)c2cc(cc(NC(=O)c3cc(F)cc(c3)C(F)(F)F)c12)-c1c[nH]nn1 | NMR (400 MHz, DMSO-d6) 10.63 (br. s, 1H), 9.21 (br. s, 1H), 8.59 (br. s, 1H), 8.17 (s, 1H), 8.05 (s, 1H), 7.96 (d, 8.5 Hz, 1H), 7.77 (d, 9.0 Hz, 1H), 7.70 (s, 1H), 7.32 (dd, 8.8, 5.1 Hz, 1H), 7.09 (td, 9.16, 9.02, 3.04 Hz, 1H), 6.69 (br. s, 1H), 6.02 (br. s, 1H). | 534.2 | A | A |
| I-841 | 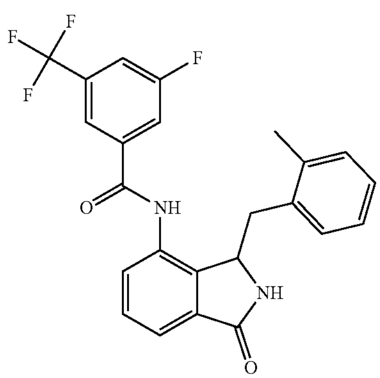 [SMILES: Cc1ccccc1CC1NC(=O)c2cccc(NC(=O)c3cc(F)cc(C(F)(F)F)c3)c21] | Cc1ccccc1CC1NC(=O)c2ccccc(NC(=O)c3cc(F)cc(c3)C(F)(F)F)c12 | NMR (400 MHz, DMSOd6) 10.75 (s, 1H), 8.57 (s, 1H), 8.21 (s, 1H), 8.14 (d, 9.0 Hz, 1H), 8.03 (d, 8.4 Hz, 1H), 7.62 (m, 1H), 7.55 (d, 2.8 Hz, 1H), 7.54 (s, 1H), 7.01-6.92 (m, 4H), 5.14-5.06 (m, 1H), 3.16 (dd, 14.0, 4.4 Hz, 1H), 2.56 (dd, 14.0, 7.8 Hz, 1H), 2.12 (s, 3H). | 443.4 | D | |
| I-842 | 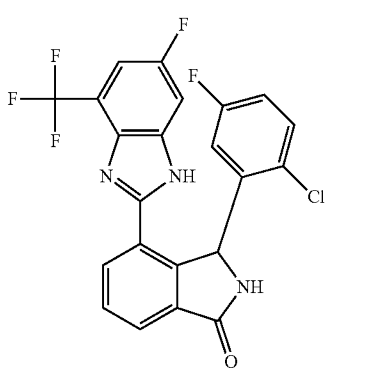 [SMILES: O=C1NC(c2cc(F)ccc2Cl)c2c1cccc2-c1nc2c(C(F)(F)F)cc(F)cc2[nH]1] | Fc1ccc(C1)c(c1)C1NC(=O)c2cccc-c3nc4c(cc(F)cc4[nH]3)C(F)(F)Fc12 | NMR (400 MHz, DMSO-D6) 9.23 (br s, 1 H), 8.39-8.15 (m, 2 H), 7.92 (dd, 7.5, 0.7 Hz, 1 H), 7.82 (t, 7.6 Hz, 1 H), 7.61 (dd, 8.8, 2.1 Hz, 1 H), 7.43-7.12 (m, 2 H), 6.95 (ddd, 8.7, 8.2, 3.1 Hz, 1 H), 6.60 (br s, 1 H), 6.29 (br s, 1 H). | 464.2 | B | |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-843 | 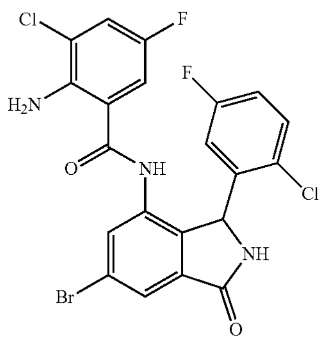 [SMILES: Nc1c(Cl)cc(F)cc1C(=O)Nc1cc(Br)cc2c1C(c1cc(F)ccc1Cl)NC2=O] | Nc1c(Cl)cc(F)cc1C(=O)Nc1cc(Br)cc2C(=O)NC(c12)c1cc(F)ccc1Cl | (400 MHz, DMSO-d6) 10.20 (br s, 1H), 9.29 (s, 1H), 7.78 (d, 1.4 Hz, 1H), 7.73 (d, 1.4 Hz, 1H), 7.48 (dd, 8.1, 2.9 Hz, 1H), 7.39 (dd, 8.8, 5.2 Hz, 1H), 7.16 (td, 8.4, 3.1 Hz, 1H), 6.97-6.47 (m, 1H), 6.71 (dd, 9.3, 2.1 Hz, 1H), 6.31 (s, 2H), 5.97 (br s, 1H) | 524.3 | B | |
| I-844 | 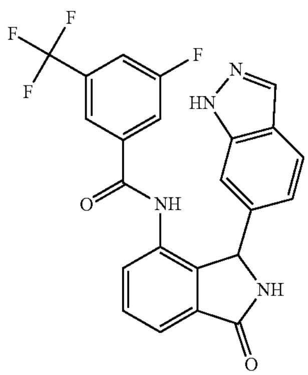 [SMILES: O=C(Nc1cccc2c1C(c1ccc3cn[nH]c3c1)NC2=O)c1cc(F)cc(C(F)(F)F)c1] | Fc1cc(cc(c1)C(F)(F)F)C(=O)Nc1ccc2C(=O)NC(c12)c1ccc2cn[nH]c2c1 | 1H NMR (400 MHz, DMSO-d6) 12.76 (s, 1H), 10.35 (s, 1H), 9.13 (s, 1H), 7.95 (s, 1H), 7.88 (d, 8.3 Hz, 1H), 7.70 (dd, 7.5, 0.9 Hz, 1H), 7.60 (1, 7.6 Hz, 1H), 7.53 (d, 8.4 Hz, 1H), 7.51-7.45 (m, 8.1 Hz, 2H), 7.42 (s, 1H), 7.15 (s, 1H), 6.56 (d, 8.4 Hz, 1H), 5.82 (s, 1H). DMSO satellites at 2.67 and 2.33. | 455.3 | E | |
| I-845 | 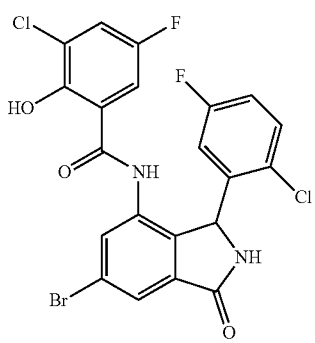 [SMILES: O=C(Nc1cc(Br)cc2c1C(c1cc(F)ccc1Cl)NC2=O)c1cc(F)cc(Cl)c1O] | Oc1c(Cl)cc(F)cc1C(=O)Nc1cc(Br)cc2C(=O)NC(c12)c1cc(F)ccc1Cl | (400 MHz, DMSO-d6) 12.35 (br s, 1H), 9.25 (s, 1H), 8.04 (s, 1H), 7.72 (s, 1H), 7.48 (d, 4.8 Hz, 1H), 7.38-7.26 (m, 2H), 7.10 (td, 8.4, 3.1 Hz, 1H), 6.90 (br s, 1H), 5.98 (s, 1H) | 525.2 | C | |
| I-846 | 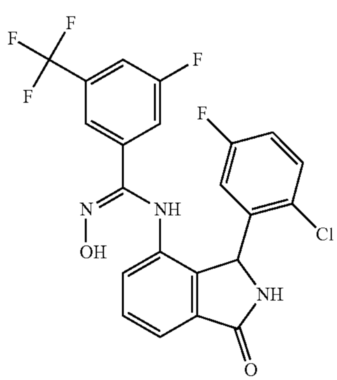 [SMILES: O=C1NC(c2cc(F)ccc2Cl)c2c(N/C(=N\O)c3cc(F)cc(C(F)(F)F)c3)cccc21] | O\N=C(/Nc1cccc2C(=S)NC(c12)c1cc(F)ccc1Cl)c1cc(F)cc(c1)C(F)(F)F | | 498 | C | |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-847 | 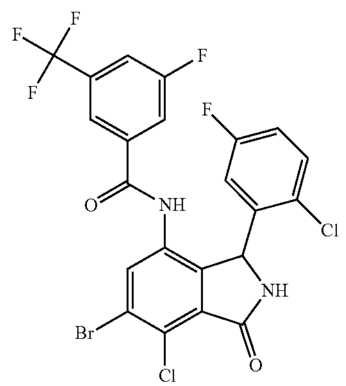 [SMILES: O=C(Nc1cc(Br)c(Cl)c2c1C(c1cc(F)ccc1Cl)NC2=O)c1cc(F)cc(C(F)(F)F)c1] | Fc1ccc(C1)c(c1)CNC(=O)c2c1c(NC(=O)c1cc(F)cc(c1)C(F)(F)F)cc(Br)c2Cl | | | A | |
| I-848 | 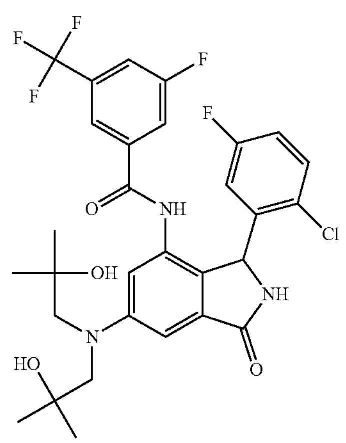 [SMILES: CC(C)(O)CN(CC(C)(C)O)c1cc(NC(=O)c2cc(F)cc(C(F)(F)F)c2)c2c(c1)C(=O)NC2c1cc(F)ccc1Cl] | CC(C)(O)CN(CC(C)(C)O)c1cc2C(=O)NC(c2c(NC(=O)c2cc(F)cc(c2)C(F)(F)F)c1)c1cc(F)ccc1Cl | | 626.39 | D | |
| I-849 | 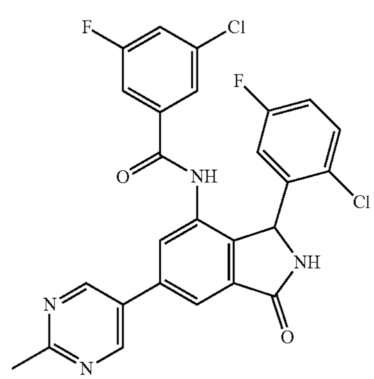 [SMILES: Cc1ncc(-c2cc(NC(=O)c3cc(F)cc(Cl)c3)c3c(c2)C(=O)NC3c2cc(F)ccc2Cl)cn1] | Cc1ncc(cn1)-c1cc2C(=O)NC(c2c(NC(=O)c2cc(F)cc(c2)C(Cl)c2)c1)c1cc(F)ccc1Cl | | 525 | A | |

TABLE 2-continued

Representative Compounds of the Invention with Bioactivity Data.

| Ex. No. | Structure | SMILES | $^1$H NMR | MS | ADP-Glo IC$_{50}$ | MCF 10A IC$_{50}$ |
|---|---|---|---|---|---|---|
| I-850 | 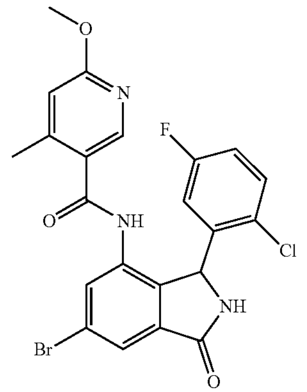 [SMILES: COc1cc(C)c(C(=O)Nc2cc(Br)cc3c2C(c2cc(F)ccc2Cl)NC3=O)cn1] | COc1cc(C)c(cn1)C(=O)Nc1cc(Br)cc2C(=O)NC(c12)c1cc(F)ccc1Cl | 1H NMR (400 MHz, DMSO-d6) 2.17 (s, 3 H) 3.83 (s, 3 H) 6.03 (br d, 4.80 Hz, 1 H) 6.64-6.74 (m, 2 H) 7.20-7.32 (m, 1 H) 7.43-7.52 (m, 1 H) 7.57 (s, 1 H) 7.71-7.79 (m, 2 H) 9.27 (br s, 1 H) 10.25 (s, 1 H) | 506.29 | E | |
| I-851 | 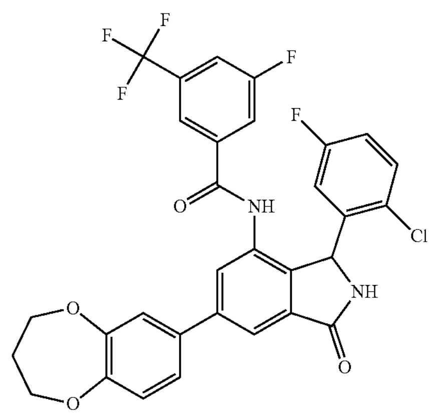 [SMILES: O=C(Nc1cc(-c2ccc3c(c2)OCCCO3)cc2c1C(c1cc(F)ccc1Cl)NC2=O)c1cc(F)cc(C(F)(F)F)c1] | Fc1ccc(C1)c(c1)C1NC(=O)c2cc(cc(NC(=O)c3cc(F)cc(c3)C(F)(F)F)c12)-c1ccc2OCCCOc2c1 | | 615.39 | A | |
| I-852 | 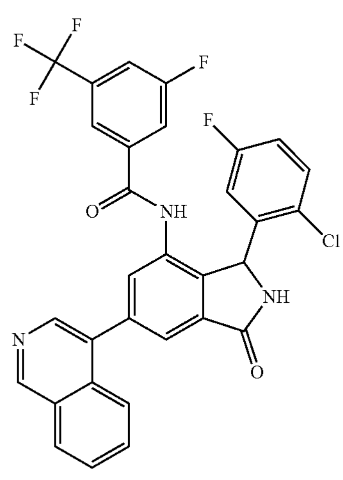 [SMILES: O=C(Nc1cc(-c2cncc3ccccc23)cc2c1C(c1cc(F)ccc1Cl)NC2=O)c1cc(F)cc(C(F)(F)F)c1] | Fc1ccc(C1)c(c1)C1NC(=O)c2cc(cc(NC(=O)c3cc(F)cc(c3)C(F)(F)F)c12)-c1cncc2ccccc12 | | 594.33 | A | |

TABLE 2-continued

Representative Compounds of the Invention with Bioactivity Data.

| Ex. No. | Structure | SMILES | $^1$H NMR | MS | ADP-Glo IC$_{50}$ | MCF 10A IC$_{50}$ |
|---|---|---|---|---|---|---|
| I-853 | 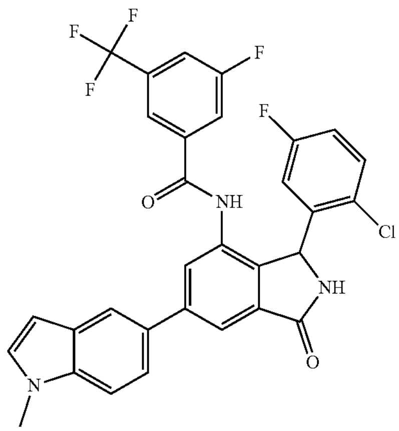 [SMILES: Cn1ccc2cc(-c3cc(NC(=O)c4cc(F)cc(C(F)(F)F)c4)c4c(c3)C(=O)NC4c3cc(F)ccc3Cl)ccc21] | Cn1ccc2c c(ccc12)- c1cc2C(= O)NC(c2 c(NC(=O) c2cc(F)c c(c2)C(F) (F)F)c1)c 1cc(F)ccc 1Cl | | 596.33 | B | |
| I-854 | 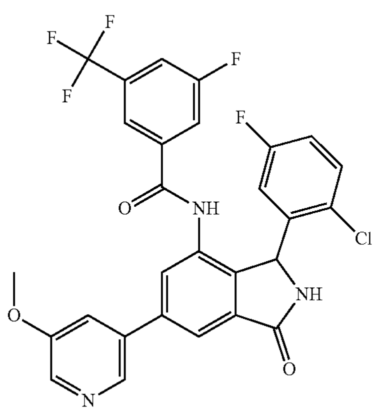 [SMILES: COc1cncc(-c2cc(NC(=O)c3cc(F)cc(C(F)(F)F)c3)c3c(c2)C(=O)NC3c2cc(F)ccc2Cl)c1] | COc1cnc c(c1)- c1cc2C(= O)NC(c2 c(NC(=O) c2cc(F)c c(c2)C(F) (F)F)c1)c 1cc(F)ccc 1Cl | | 574.32 | A | |
| I-855 | 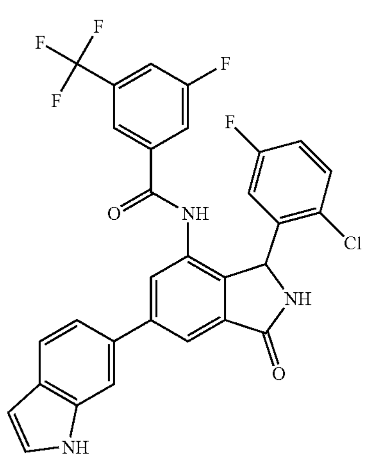 [SMILES: O=C(Nc1cc(-c2ccc3cc[nH]c3c2)cc2c1C(c1cc(F)ccc1Cl)NC2=O)c1cc(F)cc(C(F)(F)F)c1] | Fc1ccc(C 1)c(c1)C1 NC(=O)c 2cc(cc(N C(=O)c3 cc(F)cc(c 3)C(F)(F) F)c12)- c1ccc2cc [nH]c2c1 | | 582.27 | B | |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-856 | 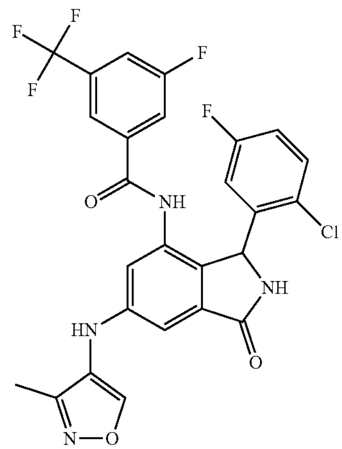 [SMILES: Cc1nocc1Nc1cc(NC(=O)c2cc(F)cc(C(F)(F)F)c2)c2c(c1)C(=O)NC2c1cc(F)ccc1Cl] | Cc1nocc1Nc1cc2C(=O)NC(c2c(NC(=O)c2cc(F)cc(c2)C(F)(F)F)c1c1cc(F)ccc1Cl | (400 MHz, DMSO-d6) 10.36 (s, 1H), 9.02 (s, 1H), 9.01 (s, 1H), 7.96 (s, 1H), 7.93 (d, 8.4 Hz, 1H), 7.70 (d, 9.2 Hz, 1H), 7.60 (s, 1H), 7.30 (dd, 8.9, 5.2 Hz, 1H), 7.07 (td, 8.4, 3.1 Hz, 1H), 6.99 (d, 2.0 Hz, 1H), 6.90 (d, 1.5 Hz, 1H), 6.63 (br s, 1H), 5.88 (br s, 1H), 2.20 (s, 3H). | 561.4 | A | A |
| I-857 | 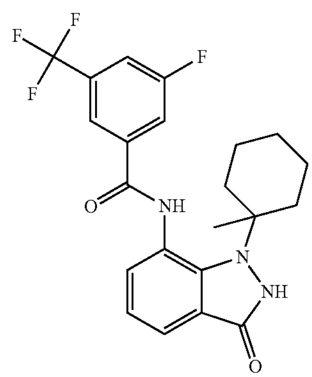 [SMILES: CC1(n2[nH]c(=O)c3cccc(NC(=O)c4cc(F)cc(C(F)(F)F)c4)c32)CCCCC1] | CC1(CCCCC1)n1[nH]c(=O)c2cccc(NC(=O)c3cc(F)cc(c3)C(F)(F)F)c12 | 1H NMR (400 MHz, DSMO-d6) 10.66 (s, 1H), 10.52 (br s, 1H), 8.21 (s, 1H), 8.11 (d, 9.2 Hz, 1H), 8.03 (d, 8.6 Hz, 1H), 7.66 (d, 7.9 Hz, 1H), 7.24 (d, 7.2 Hz, 1H), 7.08 (t, 7.6 Hz, 1H), 2.45-2.34 (m, 2H), 1.81-1.70 (m, 1H), 1.55-1.21 (m, 6H), 1.40 (s, 3H). | 434.5 | D | |
| I-858 | 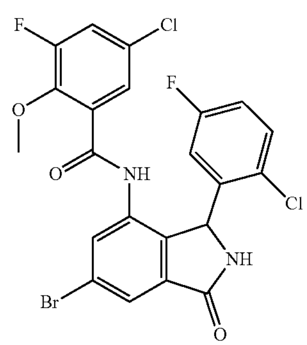 [SMILES: COc1c(F)cc(Cl)cc1C(=O)Nc1cc(Br)cc2c1C(c1cc(F)ccc1Cl)NC2=O] | COc1c(F)cc(Cl)cc1C(=O)Nc1cc(Br)cc2C(=O)NC(c12)c1cc(F)ccc1Cl | 1H NMR (400 MHz, Chloroform-d) 9.16 (s, 1H), 8.35 (s, 1H), 7.97 (d, 1.7 Hz, 1H), 7.85 (dd, 2.7, 1.7 Hz, 1H), 7.42 (dd, 8.9, 5.0 Hz, 1H), 7.31 (d, 2.7 Hz, 1H), 7.02 (ddd, 8.8, 7.4, 3.0 Hz, 1H), 6.58 (d, 11.2 Hz, 2H), 6.15 (s, 1H), 3.75 (d, 2.3 Hz, 3H). | 541 | D | |
| I-859 | 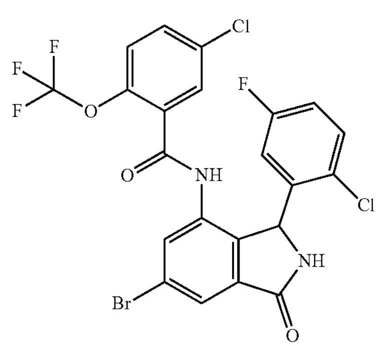 [SMILES: O=C(Nc1cc(Br)cc2c1C(c1cc(F)ccc1Cl)NC2=O)c1cc(Cl)ccc1OC(F)(F)F] | Fc1ccc(C1)c(c1)C1NC(=O)c2cc(Br)cc(NC(=O)c3cc(Cl)ccc3OC(F)(F)F)c12 | 1H NMR (400 MHz, Chloroform-d) 8.28 (s, 1H), 7.98 (d, 1.7 Hz, 1H), 7.72 (s, 1H), 7.67 (d, 2.7 Hz, 1H), 7.55 (dd, 8.8, 2.7 Hz, 1H), 7.35 (dd, 8.9, 4.9 Hz, 1H), 7.27 (dt, 8.8, 1.5 Hz, 1H), 7.03 (ddd, 8.9, 7.4, 3.0 Hz, 1H), 6.66 (s, 1H), 6.55 (s, 1H), 6.17 (s, 1H). | 578.95 | D | |

TABLE 2-continued

Representative Compounds of the Invention with Bioactivity Data.

| Ex. No. | Structure | SMILES | $^1$H NMR | MS | ADP-Glo IC$_{50}$ | MCF 10A IC$_{50}$ |
|---|---|---|---|---|---|---|
| I-860 | 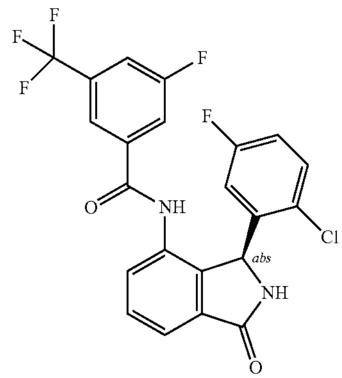 [SMILES: O=C(Nc1cccc2c1[C@@H](c1cc(F)ccc1Cl)NC2=O)c1cc(F)cc(C(F)(F)F)c1] | Fc1ccc(C1)c(c1)[C@H]1NC(=O)c2cccc(NC(=O)c3cc(F)cc(c3)C(F)(F)F)c12 | 1H NMR (400 MHz, DMSO-d6) 10.49 (s, 1H), 9.14 (s, 1H), 7.99-7.91 (m, 1H), 7.77-7.69 (m, 2H), 7.69-7.61 (m, 2H), 7.50 (d, 7.8 Hz, 1H), 7.32 (dd, 8.9, 5.2 Hz, 1H), 7.10 (td, 8.4, 3.1 Hz, 1H), 6.60 (s, 1H), 5.99 (s, 1H). | 467.37 | D | |
| I-861 | 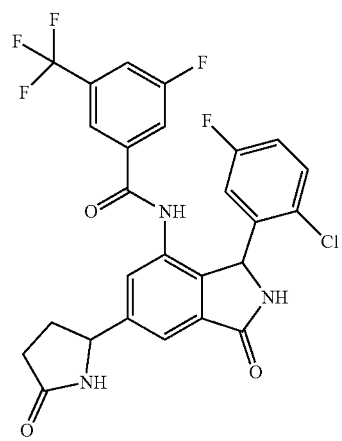 [SMILES: O=C1CCC(c2cc(NC(=O)c3cc(F)cc(C(F)(F)F)c3)c3c(c2)C(=O)NC3c2cc(F)ccc2Cl)N1] | Fc1ccc(C1)c(c1)C1NC(=O)c2cc(cc(NC(=O)c3cc(F)cc(c3)C(F)(F)F)c12)C1CCC(=O)N1 | 1H NMR (400 MHz, DMSO-d6) 10.55 (d, 5.1 Hz, 1H), 9.17 (s, 1H), 8.23 (d, 7.5 Hz, 1H), 7.95 (d, 8.5 Hz, 1H), 7.75 (d, 9.2 Hz, 1H), 7.70-7.62 (m, 2H), 7.45 (s, 1H), 7.32 (dd, 8.9, 5.1 Hz, 1H), 7.10 (td, 8.4, 2.9 Hz, 1H), 5.99 (s, 1H), 4.87 (q, 6.4 Hz, 1H), 2.59 (dd, 12.7, 7.4 Hz, 1H), 2.54 (s, 1H), 2.28 (dd, 10.6, 5.7 Hz, 2H), 1.88-1.80 (m, 1H). | 550.25 | A | |
| I-862 | 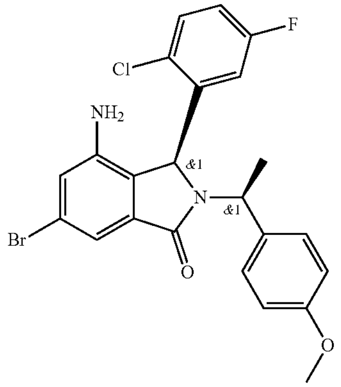 [SMILES: COc1ccc([C@H](C)N2C(=O)c3cc(Br)cc(N)c3[C@H]2c2cc(F)ccc2Cl)cc1] | COc1ccc(cc1)[C@H](C)N1[C@H](c2cc(cc(Br)cc2N)C1=O)c1cc(F)ccc1Cl | 1H NMR (400 MHz, DMSO-d6) 7.59 (dd, 8.9, 5.1 Hz, 1H), 7.35-7.20 (m, 2H), 7.15-7.02 (m, 3H), 7.01-6.84 (m, 3H), 6.62 (dd, 9.3, 3.1 Hz, 1H), 5.64-5.24 (m, 2H), 5.02 (d, 8.2 Hz, 1H), 4.77 (d, 13.1 Hz, 1H), 3.75 (d, 15.2 Hz, 3H), 1.18 (dd, 16.3, 7.3 Hz, 3H). | 491.05 | D | |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-863 | 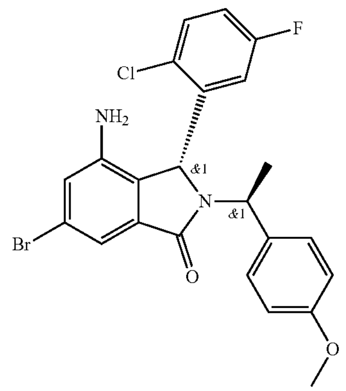 [SMILES: COc1ccc([C@H](C)N2C(=O)c3cc(Br)cc(N)c3[C@@H]2c2cc(F)ccc2Cl)cc1] | COc1ccc(cc1)[C@H](C)N1[C@H](c2c(cc(Br)cc2NC1=O)c1cc(F)ccc1Cl | 1H NMR (400 MHz, DMSO-d6) 7.66-7.43 (m, 1H), 7.15-6.95 (m, 4H), 6.91 (d, 1.7 Hz, 1H), 6.68-6.59 (m, 2H), 6.05 (dd, 9.3, 3.1 Hz, 1H), 5.97-5.70 (m, 1H), 5.26 (q, 7.2 Hz, 1H), 5.11 (q, 7.2 Hz, 1H), 4.95-4.78 (m, 1H), 3.66 (d, 3.7 Hz, 3H), 1.65 (dd, 9.2, 7.2 Hz, 3H). | 491 | D | |
| I-864 | 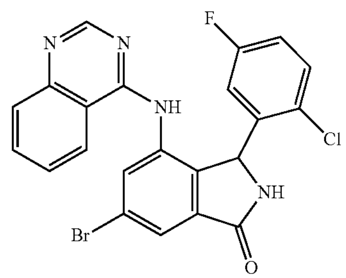 [SMILES: O=C1NC(c2cc(F)ccc2Cl)c2c(Nc3ncnc4ccccc34)cc(Br)cc21] | Fc1ccc(C1)c(c1)C1NC(=O)c2cc(Br)cc(Nc3ncnc4ccccc34)c12 | 1H NMR (400 MHz, DMSO-d6) 9.84 (s, 1H), 9.21 (d, 35.3 Hz, 1H), 8.52 (s, 1H), 7.96 (d, 8.3 Hz, 1H), 7.89-7.67 (m, 4H), 7.52 (td, 7.4, 6.7, 1.4 Hz, 1H), 7.24-6.86 (m, 2H), 6.77-6.39 (m, 1H), 6.03 (s, 1H). | 483 | E | |
| I-865 | 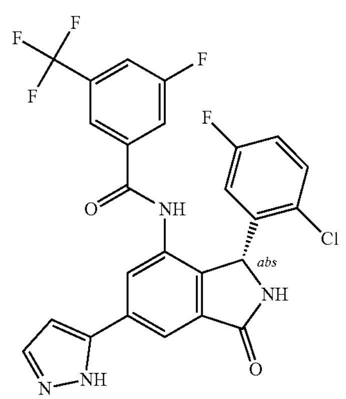 [SMILES: O=C(Nc1cc(-c2ccn[nH]2)cc2c1[C@H](c1cc(F)ccc1Cl)NC2=O)c1cc(F)cc(C(F)(F)F)c1] | Fc1ccc(C1)c(c1)[C@@H]1NC(=O)c2cc(cc(NC(=O)c3cc(F)cc(c3)C(F)(F)F)c12)-c1ccn[nH]1 | NMR (400 MHz, CD3CN) 8.67 (br s, 1H), 8.10 (d, 1.3 Hz, 1H), 8.05 (s, 1H), 7.68 (d, 2.4 Hz, 1H), 7.63 (d, 8.5 Hz, 1H), 7.59 (d, 9.0 Hz, 1H), 7.57 (s, 1H), 7.24 (dd, 8.9, 5.1 Hz, 2H), 6.99-6.91 (m, 1H), 6.79 (d, 2.4 Hz, 1H), 6.68 (br s, 1H), 6.14 (br s, 1H). | 533.3 | A | A |
| I-866 | 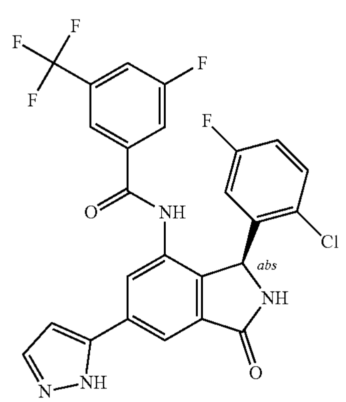 [SMILES: O=C(Nc1cc(-c2ccn[nH]2)cc2c1[C@@H](c1cc(F)ccc1Cl)NC2=O)c1cc(F)cc(C(F)(F)F)c1] | Fc1ccc(C1)c(c1)[C@H]1NC(=O)c2cc(cc(NC(=O)c3cc(F)cc(c3)C(F)(F)F)c12)-c1ccn[nH]1 | 1H NMR (400 MHz, CD3CN) 8.67 (br s, 1H), 8.10 (d, 1.3 Hz, 1H), 8.05 (s, 1H), 7.68 (d, 2.4 Hz, 1H), 7.63 (d, 8.5 Hz, 1H), 7.59 (d, 9.0 Hz, 1H), 7.57 (s, 1H), 7.24 (dd, 8.9, 5.1 Hz, 2H), 6.99-6.91 (m, 1H), 6.79 (d, 2.4 Hz, 1H), 6.68 (br s, 1H), 6.14 (br s, 1H). | 533.3 | D | |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-867 | 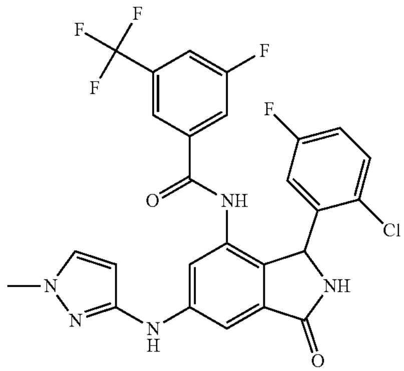 | Cn1ccc(Nc2cc3C(=O)NC(c3c(NC(=O)c3cc(F)cc(c3)C(F)(F)F)c2)c2cc(F)ccc2Cl)n1 | NMR (400 MHz, DMSO-d6) 10.41 (s, 1H), 8.98 (br. s, 1H), 8.92 (s, 1H), 7.92 (d, 8.4 Hz, 1H), 7.72 (d, 1.9 Hz, 1H), 7.70 (d, 8.6 Hz, 1H), 7.61 (s, 1H), 7.56 (d, 2.2 Hz, 1H), 7.39 (d, 1.5 Hz, 1H), 7.29 (dd, 8.9, 5.2 Hz, 1H), 7.07 (td, 8.4, 3.0 Hz, 1H), 6.59 (br. s, 1H), 5.85 (br. s, 1H), 5.82 (d, 2.2 Hz, 1H), 3.77 (s, 3H). | 562.3 | A | |
| I-868 | 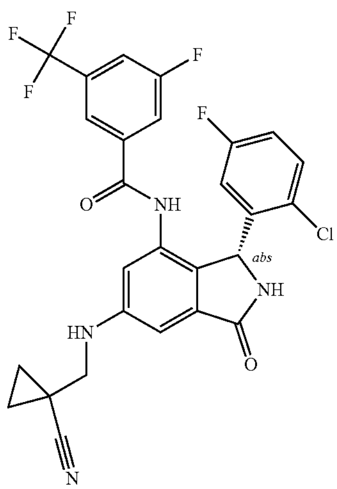 [SMILES: N#CC1(CNc2cc(NC(=O)c3cc(F)cc(C(F)(F)F)c3)c3c(c2)C(=O)N[C@H]3c2cc(F)ccc2Cl)CC1] | Fc1ccc(C1)c(c1)[C@@H]1NC(=O)c2cc(NCC3(CC3)C#N)cc(NC(=O)c3cc(F)cc(c3)C(F)(F)F)c12 | (400 MHz, DMSO-d6) 10.32 (s, 1H), 8.94 (s, 1H), 7.92 (d, 8.3 Hz, 1H), 7.70 (d, 8.9 Hz, 1H), 7.62 (s, 1H), 7.28 (dd, 8.8, 5.2 Hz, 1H), 7.06 (td, 8.5, 2.9 Hz, 1H), 6.92 (d, 1.6 Hz, 1H), 6.79 (s, 1H), 6.62 (br s, 1H), 6.57 (br t, 5.6 Hz, 1H), 5.84 (br s, 1H), 3.30 (m, 2H), 1.33-1.17 (m, 2H), 1.14-0.98 (m, 2H). | 561.4 | A | A |
| I-869 | 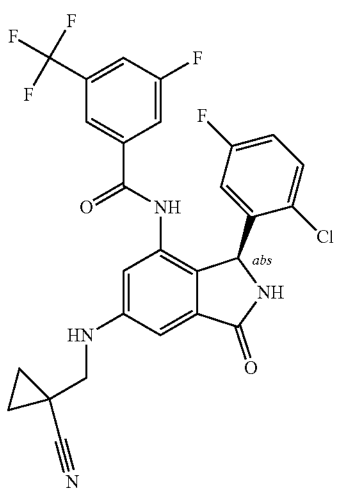 [SMILES: N#CC1(CNc2cc(NC(=O)c3cc(F)cc(C(F)(F)F)c3)c3c(c2)C(=O)N[C@@H]3c2cc(F)ccc2Cl)CC1] | Fc1ccc(C1)c(c1)[C@H]1NC(=O)c2cc(NCC3(CC3)C#N)cc(NC(=O)c3cc(F)cc(c3)C(F)(F)F)c12 | (400 MHz, DMSO-d6) 10.32 (s, 1H), 8.94 (s, 1H), 7.92 (d, 8.3 Hz, 1H), 7.70 (d, 8.9 Hz, 1H), 7.62 (s, 1H), 7.28 (dd, 8.8, 5.2 Hz, 1H), 7.06 (td, 8.5, 2.9 Hz, 1H), 6.92 (d, 1.6 Hz, 1H), 6.79 (s, 1H), 6.62 (br s, 1H), 6.57 (br t, 5.6 Hz, 1H), 5.84 (br s, 1H), 3.30 (m, 2H), 1.33-1.17 (m, 2H), 1.14-0.98 (m, 2H). | 561.4 | B | |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-870 | 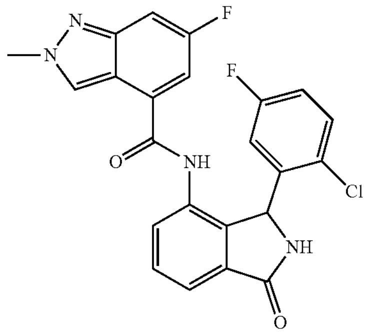 [SMILES: Cn1cc2c(C(=O)Nc3cccc4c3C(c3cc(F)ccc3Cl)NC4=O)cc(F)cc2n1] | Cn1cc2c(cc(F)cc2n1)C(=O)Nc1cccc2C(=O)NC(c12)c1cc(F)ccc1Cl | NMR (400 MHz, CD3CN) 8.51 (s, 1H), 8.25 (s, 1H), 7.76 (dd, 7.2, 1.3 Hz, 1H), 7.65 (t, 7.4 Hz, 1H), 7.60 (dd, 7.7, 1.0 Hz, 1H), 7.46 (ddd, 9.8, 2.1, 1.0 Hz, 1H), 7.22 (dd, 8.9, 5.1 Hz, 1H), 7.24-7.20 (m, 1H), 6.98-6.91 (m, 2H), 6.64 (br. s, 1H), 6.18 (br. s, 1H), 4.15 (s, 3H). | 453.5 | E | |
| I-871 | 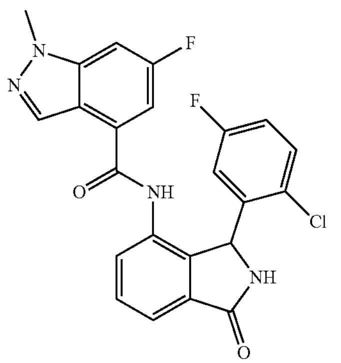 [SMILES: Cn1ncc2c(C(=O)Nc3cccc4c3C(c3cc(F)ccc3Cl)NC4=O)cc(F)cc21] | Cn1ncc2c(cc(F)cc12)C(=O)Nc1cccc2C(=O)NC(c12)c1cc(F)ccc1Cl | NMR (400 MHz, CD3CN) 8.54 (s, 1H), 8.06 (s, 1H), 7.76 (dd, 7.1, 1.3 Hz, 1H), 7.65 (t, 7.5 Hz, 1H), 7.61 (dd, 7.9, 1.4 Hz, 1H), 7.43 (ddd, 9.2, 2.0, 1.0 Hz, 1H), 7.24 (dd, 8.9, 5.2 Hz, 1H), 7.25-7.22 (submerged signal, 1H), 6.99-6.92 (m, 2H), 6.66 (br. s, 1H), 6.20 (br. s, 1H), 4.02 (s, 3H) | 453.3 | E | |
| I-872 | 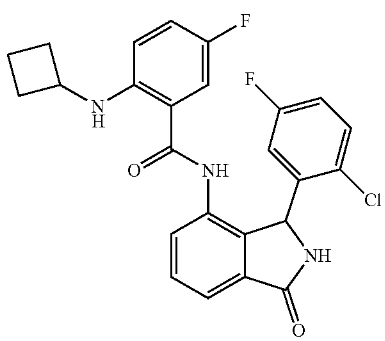 | Fc1ccc(C1)c(c1)C1NC(=O)c2cccc(NC(=O)c3cc(F)ccc3NC3CCC3)c12 | NMR (400 MHz, DMSO-d6) 10.02 (s, 1H), 9.11 (s, 1H), 7.66 (dd, 7.3, 0.7 Hz, 1H), 7.61 (t, 7.5 Hz, 1H), 7.47 (dd, 7.6, 0.9 Hz, 1H), 7.39 (d, 6.1 Hz, 1H), 7.36 (dd, 8.9, 5.2 Hz, 1H), 7.16-7.13 m, 2H), 6.82 (dd, 9.9, 2.2 Hz, 1H), 6.54 (dd, 9.3, 4.7 Hz, 1H), 6.70-6.40 (m, 1H), 6.01 (s, 1H), 3.94-3.81 (m, 1H), 2.44-2.29 (m, 2H), 1.82-1.68 (m, 4H) | 468.4 | D | |
| I-873 | 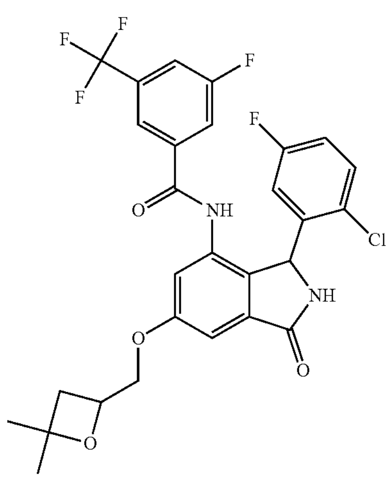 [SMILES: CC1(C)CC(COc2cc(NC(=O)c3cc(F)cc(C(F)(F)F)c3)c3c(c2)C(=O)NC3c2cc(F)ccc2Cl)O1] | CC1(C)COc2cc3C(=O)NC(c3cc(NC(=O)c3cc(F)cc(c3)C(F)(F)F)c2)c2cc(F)ccc2Cl)O1 | 1H NMR (400 MHz, DMSO-d6) 10.44 (s, 1H), 9.10 (s, 1H), 7.92 (d, 7.6 Hz, 1H), 7.72 (d, 8.8 Hz, 1H), 7.65 (s, 1H), 7.35-7.28 (m, 1H), 7.23 (s, 1H), 7.14 (s, 1H), 7.11-7.03 (m, 1H), 6.63 (s (br), 1H), 5.92 (s (br), 1H), 4.90-4.77 (m, 1H), 4.27-4.12 (m, 2H), 2.47-2.32 (m, 2H), 1.42 (s, 3H), 1.40-1.37 (m, 3H). | 581.2 | B | |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-874 | 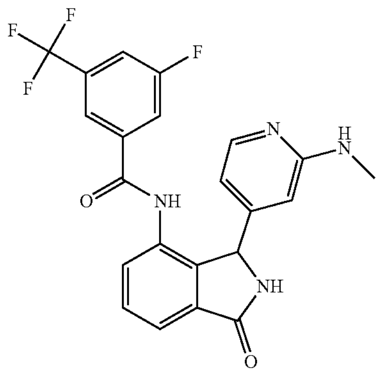 | CNc1cc(ccn1)C1NC(=O)c2cccc(NC(=O)c3cc(F)cc(c3)C(F)(F)F)c12 | (400 MHz, d6-DMSO) 9.05 (br s, 2H), 7.86 (s, 1H), 7.83 (d, 8.3 Hz, 1H), 7.79 (br d, 9.4 Hz, 1H), 7.71 (d, 5.2 Hz, 1H), 7.63-7.56 (m, 1H), 7.49 (s, 1H), 7.48 (d, 5.0 Hz, 1H), 6.28-6.21 (m, 1H), 6.09 (s, 1H), 6.04 (dd, 5.3, 1.0 Hz, 1H), 5.50 (s, 1H), 2.54 (d, 4.8 Hz, 3H). | 445.4 | E | |
| I-875 | 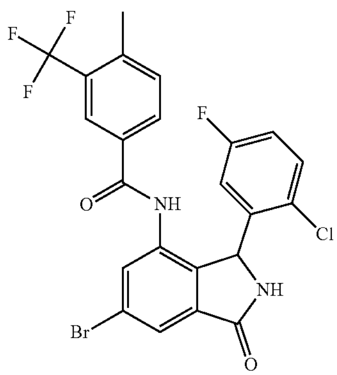 [SMILES: Cc1ccc(C(=O)Nc2cc(Br)cc3c2C(c2cc(F)ccc2Cl)NC3=O)cc1C(F)(F)F] | Cc1ccc(c1C(F)(F)F)C(=O)Nc1cc(Br)cc2C(=O)NC(c12)c1cc(F)ccc1Cl | NMR (400 MHz, CD3CN) 8.57 (s, 1H), 7.87 (d, 1.7 Hz, 1H), 7.75 (s, 1H), 7.72-7.66 (m, 2H), 7.44 (d, 7.9 Hz, 1H), 7.30 (br s, 1H), 7.25 (dd, 8.9, 5.1 Hz, 1H), 6.97 (ddd, 8.8, 8.0, 3.1 Hz, 1H), 6.67 (br s, 1H), 6.09 (s, 1H), 2.52 (d, 1.6 Hz, 3H). | 541 | B | |
| I-876 | 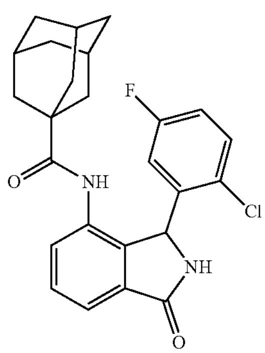 [SMILES: O=C1NC(c2cc(F)ccc2Cl)c2c(NC(=O)C34CC5CC(CC(C5)C3)C4)cccc21] | Fc1ccc(C1)c(c1)C1NC(=O)c2cccc(NC(=O)C34CC5CC(CC(C5)C3)C4)c12 | 1H NMR (400 MHz, DMSO-d6) 9.09 (s, 1H), 9.06 (br. s, 1H), 7.60-7.53 (m, 2H), 7.52-7.46 (m, 1H), 7.40 (dd, 7.4, 1.5 Hz, 1H), 7.24 (ddd, 8.7, 8.2, 3.1 Hz, 1H), 6.45 (br. s, 1H), 6.04 (br. s, 1H), 1.92-1.85 (m, 3H), 1.66-1.60 (m, 3H), 1.58-1.47 (m, 9H). | 439.4 | B | |
| I-877 | 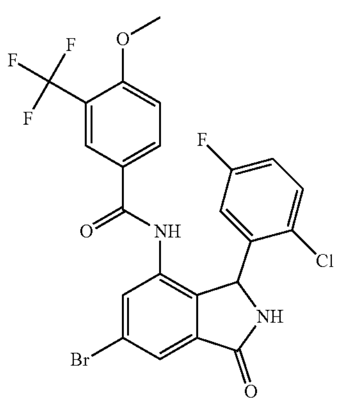 [SMILES: COc1ccc(C(=O)Nc2cc(Br)cc3c2C(c2cc(F)ccc2Cl)NC3=O)cc1C(F)(F)F] | COc1ccc(cc1C(F)(F)F)C(=O)Nc1cc(Br)cc2C(=O)NC(c12)c1cc(F)ccc1Cl | NMR (400 MHz, DMSO-d6) 10.34 (s, 1H), 9.27 (br s, 1H), 7.93 (dd, 8.8, 1.9 Hz, 1H), 7.78 (d, 1.6 Hz, 1H), 7.74 (d, 2.0 Hz, 1H), 7.70 (d, 1.5 Hz, 1H), 7.34 (d, 8.9 Hz, 1H), 7.30 (dd, 8.9, 5.2 Hz, 1H), 7.13-7.02 (m, 1H), 5.98 (s, 1H), 3.96 (s, 3H). | 555 | C | |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-878 | 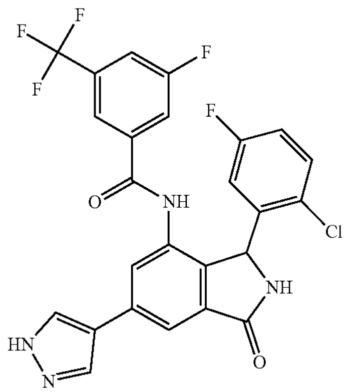 [SMILES: O=C(Nc1cc(-c2cn[nH]c2)cc2c1C(c1cc(F)ccc1Cl)NC2=O)c1cc(F)cc(C(F)(F)F)c1] | Fc1ccc(C1)c(c1)C1NC(=O)c2cc(cc(NC(=O)c3cc(F)cc(c3)C(F)(F)F)c12)-c1cn[nH]c1 | NMR (400 MHz, DMSO-d6) 13.07 (br.s, 1H), 10.56 (br. s, 1H), 9.12 (br. s, 1H), 8.41-8.11 (m, 2H), 7.95 (br. d, 6.5 Hz, 1H), 7.94 (s, 1H), 7.76 (br.d, 9.8 Hz, 1H), 7.73 (s, 1H), 7.71 (s, 1H), 7.31 (dd, 8.9, 5.2 Hz, 1H), 7.09 (td, 8.5, 3.1 Hz, 1H), 6.65 (br. s, 1H), 5.97 (br. s, 1H). | 533.2 | A | A |
| I-879 | 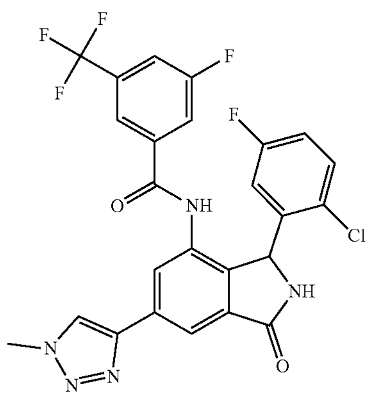 [SMILES: Cn1cc(-c2cc(NC(=O)c3cc(F)cc(C(F)(F)F)c3)c3c(c2)C(=O)NC3c2cc(F)ccc2Cl)nn1] | Cn1cc(nn1)-c1cc2C(=O)NC(c2c(NC(=O)c2cc(F)cc(c2)C(F)(F)F)c1)c1cc(F)ccc1Cl | NMR (400 MHz, MeCN-D3) Major rotamer: 8.72 (s, 1H), 8.23 (s, 1H), 8.12 (d, 1.3 Hz, 1H), 8.10 (d, 1.3 Hz, 1H), 7.67-7.60 (m, 2H), 7.59 (s, 1H), 7.28-7.25 (m, 1H), 7.26 (dd, 8.9, 5.1 Hz, 1H), 6.98 (ddd, 8.9, 8.0, 3.1 Hz, 1H), 6.71 (br. s, 1H), 6.16 (br. s, 1H), 4.11 (s, 3H). | 548.1 | A | |
| I-880 | 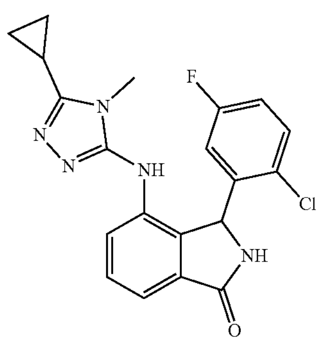 [SMILES: Cn1c(Nc2cccc3c2C(c2cc(F)ccc2Cl)NC3=O)nnc1C1CC1] | Cn1c(Nc2cccc3C(=O)NC(c23)c2cc(F)ccc2Cl)nnc1C1CC1 | 1H-NMR (400 MHz, DMSO-d6) 8.95 (br. s, 1H), 8.47 (br. s, 1H), 7.50 (t, 7.4 Hz, 1H), 7.44-7.38 (m, 2H), 7.32 (d, 7.7 Hz, 1H), 7.20 (td, 8.5, 3.1 Hz, 1H), 6.30-6.24 (m, 1H), 5.76 (br. s, 1H), 2.94 (s, 3H), 1.83-1.74 (m, 1H), 0.98-0.86 (m, 4H). Peak at 8.38 suspected to be due to presence of formate salt. Multiplet at 0.83-0.75 may be due to grease. | 398.4 | E | |
| I-881 | 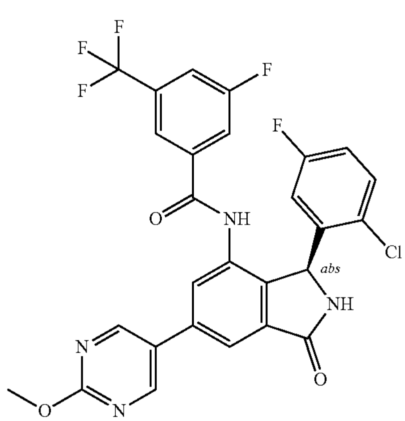 [SMILES: COc1ncc(-c2cc(NC(=O)c3cc(F)cc(C(F)(F)F)c3)c3c(c2)C(=O)N[C@@H]3c2cc(F)ccc2Cl)cn1] | COc1ncc(cn1)-c1cc2C(=O)N[C@@H](c2c(NC(=O)c2cc(F)cc(c2)C(F)(F)F)c1)c1cc(F)ccc1Cl | | 575.2 | D | |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-882 | 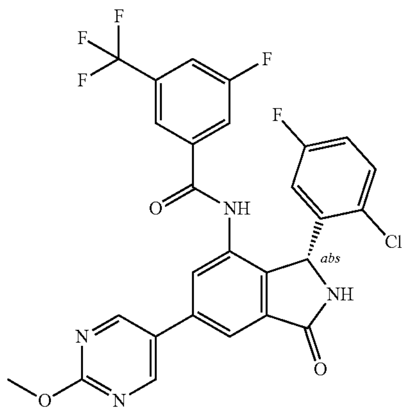 [SMILES: COc1ncc(-c2cc(NC(=O)c3cc(F)cc(C(F)(F)F)c3)c3c(c2)C(=O)N[C@H]3c2cc(F)ccc2Cl)cn1] | COc1ncc(cn1)-c1cc2C(=O)N[C@H](c2c(NC(=O)c2cc(F)cc(c2)C(F)(F)F)c1)c1cc(F)ccc1Cl | | 575.2 | A | A |
| I-883 | 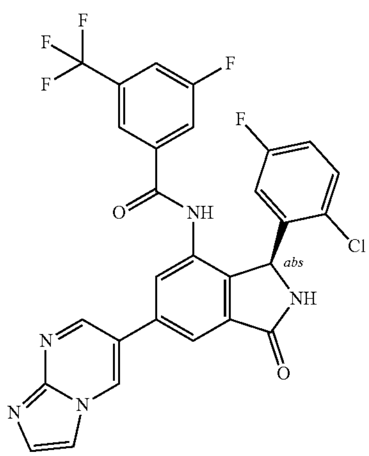 [SMILES: O=C(Nc1cc(-c2cnc3nccn3c2)cc2c1[C@@H](c1cc(F)ccc1Cl)NC2=O)c1cc(F)cc(C(F)(F)F)c1] | Fc1ccc(C1)c(c1)[C@H]1NC(=O)c2cc(cc(NC(=O)c3cc(F)cc(c3)C(F)(F)F)c12)-c1cnc2nccn2c1 | | 584.2 | D | |
| I-884 | 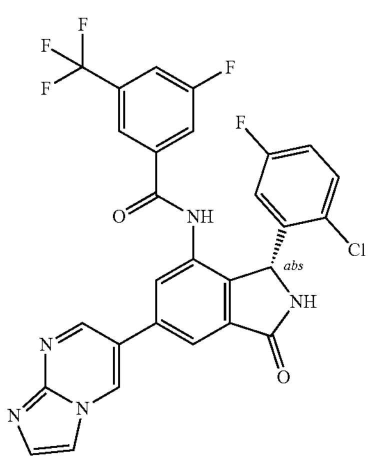 [SMILES: O=C(Nc1cc(-c2cnc3nccn3c2)cc2c1[C@H](c1cc(F)ccc1Cl)NC2=O)c1cc(F)cc(C(F)(F)F)c1] | Fc1ccc(C1)c(c1)[C@@H]1NC(=O)c2cc(cc(NC(=O)c3cc(F)cc(c3)C(F)(F)F)c12)-c1cnc2nccn2c1 | | 584.3 | A | A |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-885 | 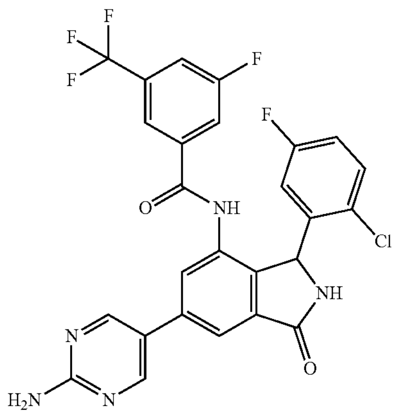 [SMILES: Nc1ncc(-c2cc(NC(=O)c3cc(F)cc(C(F)(F)F)c3)c3c(c2)C(=O)NC3c2cc(F)ccc2Cl)cn1] | Nc1ncc(cn1)-c1cc2C(=O)NC(c2cc(F)cc(c2)C(F)(F)F)c1c1cc(F)ccc1Cl | 1H NMR (400 MHz, DMSO-d6) 10.50-10.59 (m, 1H), 9.13-9.21 (m, 1H), 8.66-8.71 (m, 2H), 7.90-7.96 (m, 2H), 7.71-7.80 (m, 2H), 7.69 (s, 1H), 7.31 (dd, 5.18, 8.97 Hz, 1H), 7.09 (dt, 3.03, 8.34 Hz, 1H), 6.90 (s, 2H), 2.92-3.04 (m, 2H) | 560.31 | A | |
| I-886 | 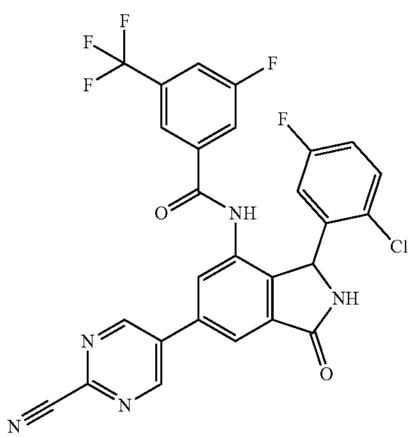 [SMILES: N#Cc1ncc(-c2cc(NC(=O)c3cc(F)cc(C(F)(F)F)c3)c3c(c2)C(=O)NC3c2cc(F)ccc2Cl)cn1] | Fc1ccc(Cl)c(c1)C1NC(=O)c2cc(cc(NC(=O)c3cc(F)cc(c3)C(F)(F)F)c12)-c1cnc(nc1)C#N | 1H NMR (400 MHz, DMSO-d6) Shift 10.72 (br s, 1H), 9.44-9.55 (m, 2H), 9.30 (br s, 1H), 8.24 (s, 1H), 8.04 (s, 1H), 7.95 (br d, 8.08 Hz, 1H), 7.76 (br d, 8.84 Hz, 1H), 7.70 (s, 1H). 7.33 (dd, 5.31, 8.84 Hz, 1H), 7.10 (dt, 3.16, 8.40 Hz, 1H), 5.97-6.15 (m, 1H) | 570.31 | A | |
| I-887 | 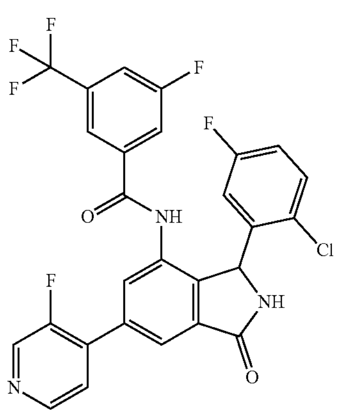 [SMILES: O=C(Nc1cc(-c2ccncc2F)cc2c1C(c1cc(F)ccc1Cl)NC2=O)c1cc(F)cc(C(F)(F)F)c1] | Fc1ccc(Cl)c(c1)C1NC(=O)c2cc(cc(NC(=O)c3cc(F)cc(c3)C(F)(F)F)c12)-c1ccncc1F | 1H NMR (400 MHz, DMSO-d6) Shift 10.66 (br s, 1H), 9.29 (br s, 1H), 8.73 (d, 2.78 Hz, 1H), 8.56 (dd, 0.76, 5.05 Hz, 1H), 7.90-8.02 (m, 2H), 7.73-7.86 (m, 3H), 7.68 (s, 1H), 7.33 (dd, 5.18, 8.97 Hz, 1H), 7.11 (dt, 3.16, 8.40 Hz, 1H), 5.96-6.14 (m, 1H) | 562.41 | A | A |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-888 | 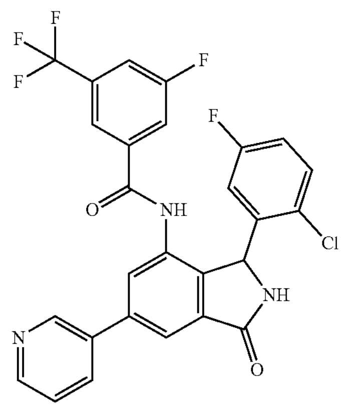 [SMILES: O=C(Nc1cc(-c2cccnc2)cc2c1C(c1cc(F)ccc1Cl)NC2=O)c1cc(F)cc(C(F)(F)F)c1] | Fc1ccc(C1)c(c1)C1NC(=O)c2cc(cc(NC(=O)c3cc(F)cc(c3)C(F)(F)F)c12)-c1cccnc1 | 1H NMR (400 MHz, DMSO-d6) Shift 10.62 (s, 1H), 9.24 (br s, 1H), 8.99 (d, 2.02 Hz, 1H), 8.63 (dd, 1.52, 4.80 Hz, 1H), 8.17-8.25 (m, 1H), 8.01 (d, 1.52 Hz, 1H), 7.95 (br d, 8.59 Hz, 1H), 7.86 (s, 1H), 7.76 (br d, 8.84 Hz, 1H), 7.69 (s, 1H), 7.57-7.67 (m, 2H), 7.49-7.57 (m, 3H), 7.33 (dd, 5.05, 8.84 Hz, 1H), 7.10 (dt, 3.16, 8.40 Hz, 1H), 5.95-6.15 (m, 1H) | 544.45 | A | |
| I-889 | 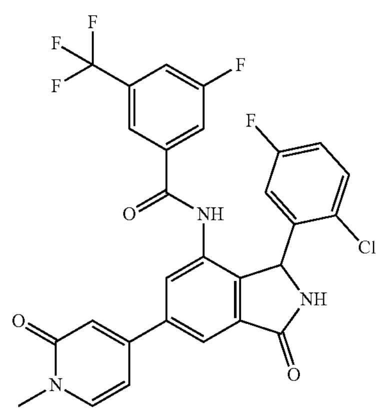 [SMILES: Cn1ccc(-c2cc(NC(=O)c3cc(F)cc(C(F)(F)F)c3)c3c(c2)C(=O)NC3c2cc(F)ccc2Cl)cc1=O] | Cn1ccc(cc1=O)-c1cc2C(=O)NC(c2c(NC(=O)c2cc(F)cc(c2)C(F)(F)F)c1)c1cc(F)ccc1Cl | 1H NMR (400 MHz, DMSO-d6) 10.59 (br s, 1H), 9.24 (br s, 1H), 7.92-7.97 (m, 2H), 7.84 (s, 1H), 7.82 (s, 1H), 7.75 (br d, 8.84 Hz, 1H), 7.69 (s, 1H), 7.32 (dd, 5.18, 8.97 Hz, 1H), 7.09 (dt, 3.03, 8.34 Hz, 1H), 6.75 (d, 2.02 Hz, 1H), 6.68 (dd, 2.02, 7.07 Hz, 1H), 5.97-6.10 (m, 1H), 3.47 (s, 3H) | 574.36 | A | |
| I-890 | 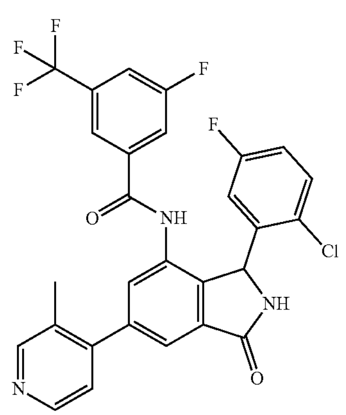 | Cc1cnccc1-c1cc2C(=O)NC(c2c(NC(=O)c2cc(F)cc(c2)C(F)(F)F)c1)c1cc(F)ccc1Cl | 1H NMR (400 MHz, DMSO-d6) 10.59 (s, 1H), 9.25 (br s, 1H), 8.56 (s, 1H), 8.50 (d, 4.80 Hz, 1H), 8.26 (s, 1H), 7.94 (br d, 8.34 Hz, 1H), 7.73 (br d, 9.09 Hz, 1H), 7.62-7.69 (m, 2H), 7.52 (s, 1H), 7.28-7.38 (m, 2H), 7.10 (dt, 3.03, 8.34 Hz, 1H), 5.96-6.14 (m, 1H), 2.31 (s, 3H) | 558.41 | A | |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-891 | 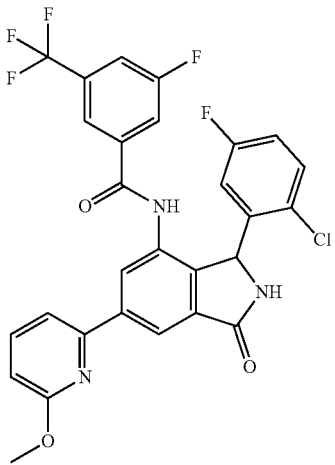 [SMILES: COc1cccc(-c2cc(NC(=O)c3cc(F)cc(C(F)(F)F)c3)c3c(c2)C(=O)NC3c2cc(F)ccc2Cl)n1] | COc1ccc(n1)-c1cc2C(=O)NC(c2c(NC(=O)c2cc(F)cc(c2)C(F)(F)F)c1)c1cc(F)ccc1Cl | 1H NMR (400 MHz, DMSO-d6) 10.58 (s, 1H), 9.23 (br s, 1H), 8.53 (s, 1H), 8.33 (d, 4.80 Hz, 1H), 7.94 (br d, 8.34 Hz, 1H), 7.86 (d, 1.01 Hz, 1H), 7.70-7.80 (m, 2H), 7.67 (s, 1H), 7.46 (d, 4.80 Hz, 1H), 7.33 (dd, 5.18, 8.97 Hz, 1H), 7.10 (dt, 3.03, 8.46 Hz, 1H), 5.98-6.13 (m, 1H), 3.95 (s, 3H) | 574.41 | A | |
| I-892 | 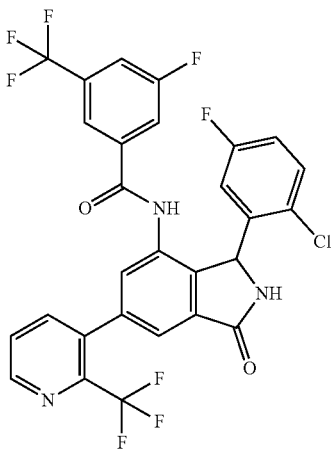 [SMILES: O=C(Nc1cc(-c2cccnc2C(F)(F)F)cc2c1C(c1cc(F)ccc1Cl)NC2=O)c1cc(F)cc(C(F)(F)F)c1] | Fc1ccc(C1)c(c1)C1NC(=O)c2cc(cc(NC(=O)c3cc(F)cc(c3)C(F)(F)F)c12)-c1cccnc1C(F)(F)F | 1H NMR (400 MHz, DMSO-d6) Shift 10.62 (s, 1H), 9.21-9.35 (m, 1H), 8.83 (dd, 1.14, 4.67 Hz, 1H), 8.04 (d, 7.58 Hz, 1H), 7.93 (br d, 8.59 Hz, 1H), 7.83 (dd, 4.67, 7.96 Hz, 1H), 7.73 (br d, 8.84 Hz, 1H), 7.64 (br d, 6.06 Hz, 2H), 7.48 (br s, 1H), 7.34 (dd, 5.18, 8.97 Hz, 1H), 7.11 (dt, 3.16, 8.40 Hz, 1H), 5.94-6.12 (m, 1H) | 612.38 | A | |
| I-893 | 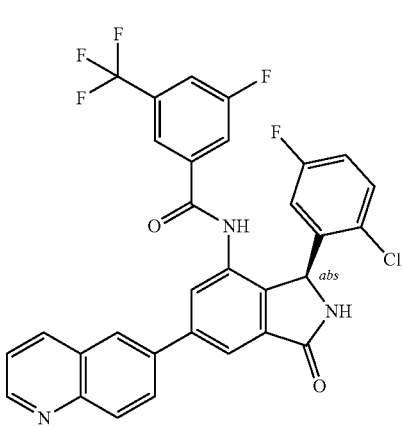 [SMILES: O=C(Nc1cc(-c2ccc3ncccc3c2)cc2c1[C@@H](c1cc(F)ccc1Cl)NC2=O)c1cc(F)cc(C(F)(F)F)c1] | Fc1ccc(C1)c(c1)[C@H]1NC(=O)c2cc(cc(NC(=O)c3cc(F)cc(c3)C(F)(F)F)c12)-c1ccc2ncccc2c1 | | 594.3 | D | |

TABLE 2-continued
Representative Compounds of the Invention with Bioactivity Data.
| Ex. No. | Structure | SMILES | ¹H NMR | MS | ADP-Glo IC$_{50}$ | MCF 10A IC$_{50}$ |
|---|---|---|---|---|---|---|
| I-894 | 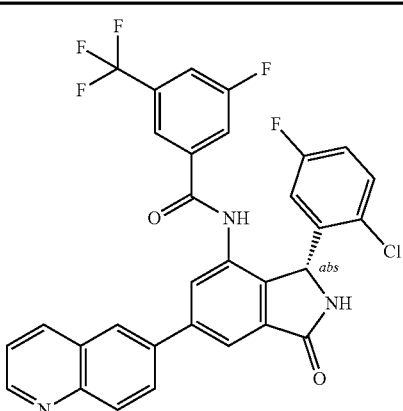 | Fc1ccc(C1)c(c1)[C@@H]1NC(=O)c2cc(cc(NC(=O)c3cc(F)cc(c3)C(F)(F)F)c12)-c1ccc2ncccc2c1 | | 594.3 | A | A |
| I-895 | 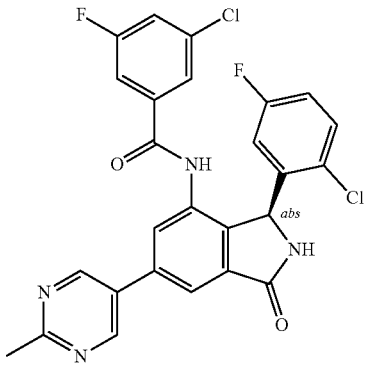 [SMILES: Cc1ncc(-c2cc(NC(=O)c3cc(F)cc(Cl)c3)c3c(c2)C(=O)N[C@@H]3c2cc(F)ccc2Cl)cn1] | Cc1ncc(cn1)-c1cc2C(=O)N[C@@H](c2c(NC(=O)c2cc(F)cc(Cl)c2)c1)c1cc(F)ccc1Cl | | 525.2 | E | |
| I-896 | 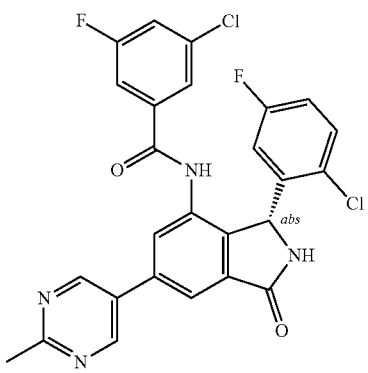 [SMILES: Cc1ncc(-c2cc(NC(=O)c3cc(F)cc(Cl)c3)c3c(c2)C(=O)N[C@H]3c2cc(F)ccc2Cl)cn1] | Cc1ncc(cn1)-c1cc2C(=O)N[C@H](c2c(NC(=O)c2cc(F)cc(Cl)c2)c1)c1cc(F)ccc1Cl | | 525.2 | A | |
| I-897 | 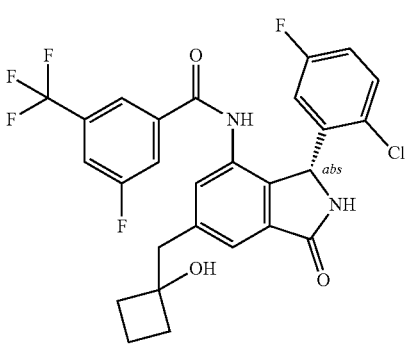 [SMILES: O=C(Nc1cc(CC2(O)CCC2)cc2c1[C@H](c1cc(F)ccc1Cl)NC2=O)c1cc(F)cc(C(F)(F)F)c1] | OC1(Cc2cc3C(=O)N[C@@H](c3c(NC(=O)c3cc(F)cc(c3)C(F)(F)F)c2)c2cc(F)ccc2Cl)CCC1 | | 549.2 | D | |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-898 | 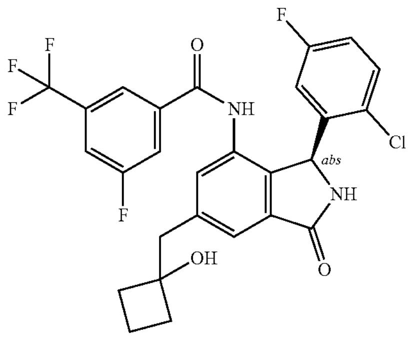 [SMILES: O=C(Nc1cc(CC2(O)CCC2)cc2c1[C@@H](c1cc(F)ccc1Cl)NC2=O)c1cc(F)cc(C(F)(F)F)c1] | OC1(Cc2cc3C(=O)N[C@H](c3c(NC(=O)c3cc(F)cc(c3)C(F)(F)F)c2)c2cc(F)ccc2Cl)CCC1 | | 549.2 | A | |
| I-899 | 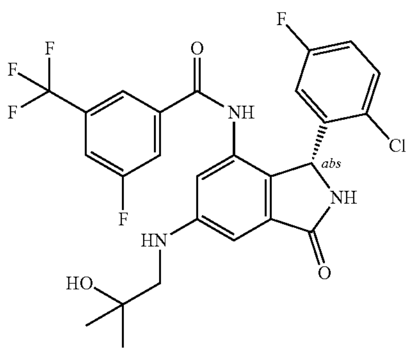 [SMILES: CC(C)(O)CNc1cc(NC(=O)c2cc(F)cc(C(F)(F)F)c2)c2c(c1)C(=O)N[C@H]2c1cc(F)ccc1Cl] | CC(C)(O)CNc1cc2C(=O)N[C@@H](c2c(NC(=O)c2cc(F)cc(c2)C(F)(F)F)c1)c1cc(F)ccc1Cl | | 554.3 | E | |
| I-900 | 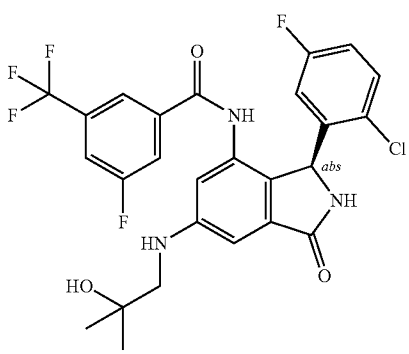 [SMILES: CC(C)(O)CNc1cc(NC(=O)c2cc(F)cc(C(F)(F)F)c2)c2c(c1)C(=O)N[C@@H]2c1cc(F)ccc1Cl] | CC(C)(O)CNc1cc2C(=O)N[C@H](c2c(NC(=O)c2cc(F)cc(c2)C(F)(F)F)c1)c1cc(F)ccc1Cl | | 554.3 | A | A |
| I-901 | 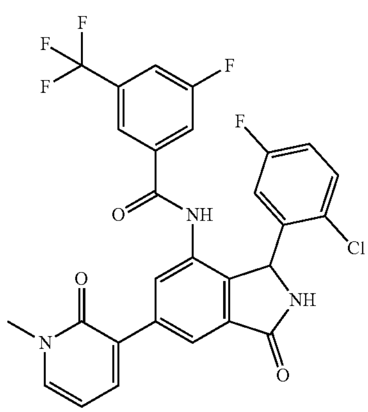 [SMILES: Cn1cccc(-c2cc(NC(=O)c3cc(F)cc(C(F)(F)F)c3)c3c(c2)C(=O)NC3c2cc(F)ccc2Cl)c1=O] | Cn1cccc(-c2cc3C(=O)NC(c3c(NC(=O)c3cc(F)cc(c3)C(F)(F)F)c2)c2cc(F)ccc2Cl)c1=O | 1H NMR (500 MHz, DMSO-d6) 10.57 (s, 1H), 9.10-9.18 (m, 1H), 8.04 (s, 1H), 7.89-7.99 (m, 2H), 7.83 (dt, 2.29, 4.65 Hz, 2H), 7.76 (br d, 8.85 Hz, 1H), 7.70 (s, 1H), 7.34 (dd, 5.19, 8.85 Hz, 1H), 7.08-7.14 (m, 1H), 6.40 (t, 6.87 Hz, 1H), 5.93-6.09 (m, 1H), 3.56 (s, 3H) | 574.32 | B | B |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-902 | 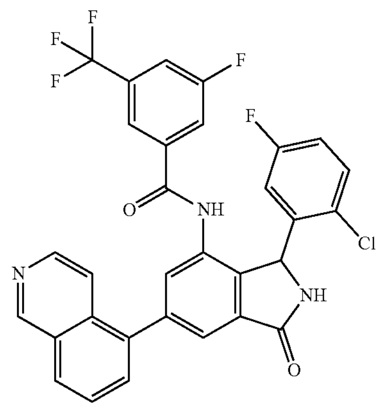 [SMILES: O=C(Nc1cc(-c2cccc3cnccc23)cc2c1C(c1cc(F)ccc1Cl)NC2=O)c1cc(F)cc(C(F)(F)F)c1] | Fc1ccc(C1)c(c1)C1NC(=O)c2cc(cc(NC(=O)c3cc(F)cc(c3)C(F)(F)F)c12)-c1cccc2cnccc12 | 1H NMR (500 MHz, DMSO-d6) 10.63 (s, 1H), 9.45 (s, 1H), 9.25-9.32 (m, 1H), 8.58 (d, 6.10 Hz, 1H), 8.25 (d, 8.24 Hz, 1H), 7.93-7.98 (m, 1H), 7.87-7.90 (m, 1H), 7.84 (d, 7.93 Hz, 1H), 7.73-7.80 (m, 3H), 7.63-7.71 (m, 2H), 7.38 (dd, 5.19, 8.85 Hz, 1H), 7.11-7.17 (m, 1H), 6.08-6.18 (m, 1H) | 594.32 | A | A |
| I-903 | 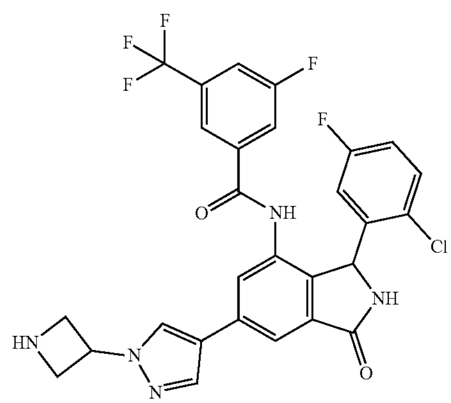 [SMILES: O=C(Nc1cc(-c2cnn(C3CNC3)c2)cc2c1C(c1cc(F)ccc1Cl)NC2=O)c1cc(F)cc(C(F)(F)F)c1] | Fc1ccc(C1)c(c1)C1NC(=O)c2cc(cc(NC(=O)c3cc(F)cc(c3)C(F)(F)F)c12)-c1cnn(c1)C1CNC1 | 1H NMR (500 MHz, DMSO) 10.51 (s, 1H), 9.14 (s, 1H), 8.95 (d, 89.5 Hz, 2H), 8.54 (s, 1H), 8.28 (s, 1H), 7.98-7.89 (m, 2H), 7.76-7.68 (m, 3H), 7.31 (dd, 8.8, 5.2 Hz, 1H), 7.09 (td, 8.4, 3.1 Hz, 1H), 5.97 (s, 1H), 5.46-5.36 (m, 1H), 4.47-4.34 (m, 4H). | 588.375 | A | D |
| I-904 | 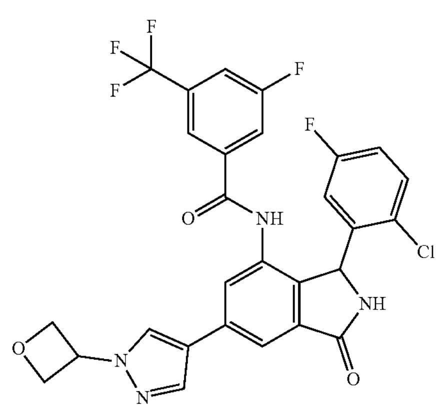 [SMILES: O=C(Nc1cc(-c2cnn(C3COC3)c2)cc2c1C(c1cc(F)ccc1Cl)NC2=O)c1cc(F)cc(C(F)(F)F)c1] | Fc1ccc(C1)c(c1)C1NC(=O)c2cc(cc(NC(=O)c3cc(F)cc(c3)C(F)(F)F)c12)-c1cnn(c1)C1COC1 | 1H NMR (500 MHz, DMSO) 10.51 (s, 1H), 9.12 (s, 1H), 8.60 (s, 1H), 8.17 (s, 1H), 7.98-7.90 (m, 2H), 7.79-7.67 (m, 3H), 7.30 (dd, 8.9, 5.2 Hz, 1H), 7.09 (qd, 8.4, 2.0 Hz, 1H), 5.96 (s, 1H), 5.63-5.55 (m, 1H), 4.98-4.89 (m, 4H). | 589.38 | A | A |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-905 | 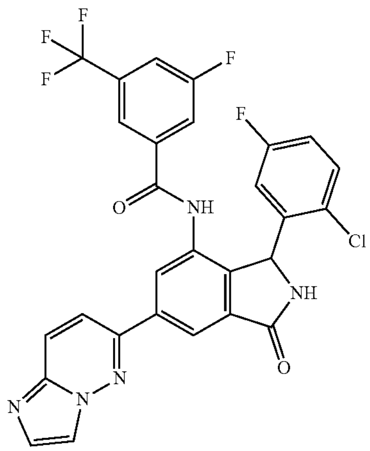 [SMILES: O=C(Nc1cc(-c2ccc3nccn3n2)cc2c1C(c1cc(F)ccc1Cl)NC2=O)c1cc(F)cc(C(F)(F)F)c1] | Fc1ccc(C1)c(c1)C1NC(=O)c2cc(cc(NC(=O)c3cc(F)cc(c3)C(F)(F)F)c12)-c1ccc2nccn2n1 | 1H NMR (500 MHz, DMSO) 10.68 (s, 1H), 9.28 (s, 1H), 8.40-8.32 (m, 2H), 8.29-8.21 (m, 2H), 8.00-7.94 (m, 2H), 7.86 (d, 1.2 Hz, 1H), 7.78 (dd, 9.2, 2.5 Hz, 1H), 7.72 (s, 1H), 7.33 (dd, 8.9, 5.1 Hz, 1H), 7.10 (td, 8.4, 3.0 Hz, 1H), 6.08 (s, 1H). | 584.37 | A | A |
| I-906 | 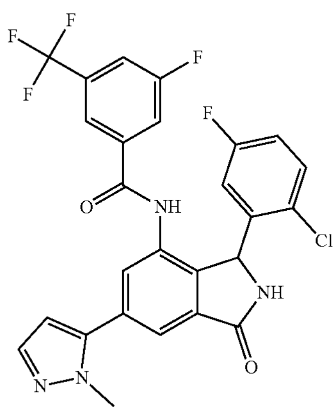 [SMILES: Cn1nccc1-c1cc(NC(=O)c2cc(F)cc(C(F)(F)F)c2)c2c(c1)C(=O)NC2c1cc(F)ccc1Cl] | Cn1nccc1-c1cc2C(=O)NC(c2c(NC(=O)c2cc(F)cc(c2)C(F)(F)F)c1)c1cc(F)ccc1Cl | NMR (400 MHz, CD3CN) 8.76 (br. s, 1H), 7.84 (d, 1.5 Hz, 1H), 7.68-7.64 (m, 2H), 7.64-7.57 (m, 2H), 7.49 (d, 1.9 Hz, 1H), 7.36 (br. s, 1H), 7.27 (dd, 8.9, 5.1 Hz, 1H), 6.99 (ddd, 8.9, 8.0, 3.1 Hz, 1H), 6.70 (br. s, 1H), 6.47 (d, 1.9 Hz, 1H), 6.19 (br. s, 1H), 3.93 (s, 3H). | 547.4 | A | A |
| I-907 | 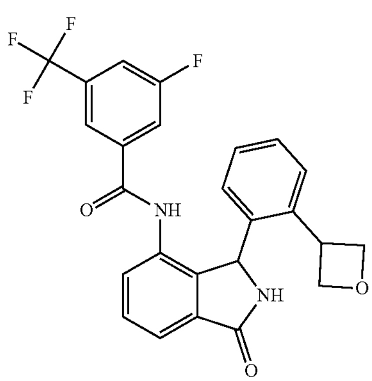 [SMILES: O=C(Nc1cccc2c1C(c1ccccc1C1COC1)NC2=O)c1cc(F)cc(C(F)(F)F)c1] | Fc1cc(cc(c1)C(F)(F)F)C(=O)Nc1ccccc2C(=O)NC(c12)c1ccccc1C1COC1 | 1H NMR (400 MHz, DMSO-d6) 10.44 (br. s, 1H), 9.06 (s, 1H), 7.90 (d, 8.4 Hz, 1H), 7.71 (d, 5.2 Hz, 1H), 7.63 (t, 7.6 Hz, 1H), 7.53-7.22 (m, 5H), 7.09 (br. s, 1H), 6.41 (br. s, 1H), 5.74 (s, 1H), 5.03-4.43 (m, 4H), 4.16 (m, 1H); DMSO satellites at 2.67 and 2.33; TMS containing minor impurities in 0.08-0.03 region. | 471.2 | E | |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-908 | 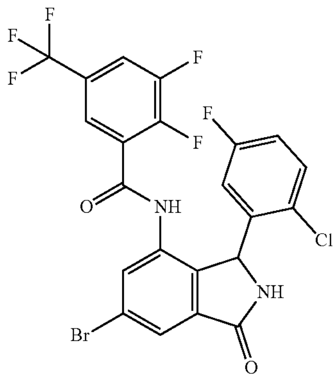 [SMILES: O=C(Nc1cc(Br)cc2c1C(c1cc(F)ccc1Cl)NC2=O)c1cc(C(F)(F)F)cc(F)c1F] | Fc1ccc(C1)c(c1)C1NC(=O)c2cc(Br)cc(NC(=O)c3cc(cc(F)c3F)C(F)(F)F)c12 | 1H NMR (400 MHz, Methanol-d4) 7.97 (d, 1.7 Hz, 1H), 7.90 (ddd, 9.5, 6.8, 2.3 Hz, 1H), 7.76 (s, 1H), 7.41 (dt, 8.2, 4.1 Hz, 2H), 7.11 (ddd, 8.9, 7.8, 3.1 Hz, 1H), 6.69 (s, 1H), 6.20 (s, 1H). | 565 | D | |
| I-909 | 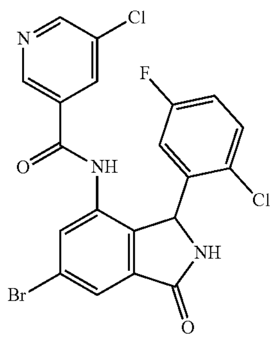 [SMILES: O=C(Nc1cc(Br)cc2c1C(c1cc(F)ccc1Cl)NC2=O)c1cncc(Cl)c1] | Fc1ccc(C1)c(c1)C1NC(=O)c2cc(Br)cc(NC(=O)c3cncc(C1)c3)c12 | 1H NMR (400 MHz, Chloroform-d) 8.76 (s, 1H), 8.55 (s, 1H), 8.43 (s,1H), 7.97 (d, 1.6 Hz, 1H), 7.88 (s, 1H), 7.47 (dd, 8.4, 4.3 Hz, 2H), 7.11 (m, 1H), 6.72 (s, 1H), 6.53 (s, 1H), 6.20 (s, 1H). | 495.95 | D | |
| I-910 | 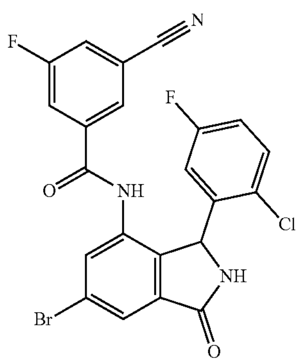 [SMILES: N#Cc1cc(F)cc(C(=O)Nc2cc(Br)cc3c2C(c2cc(F)ccc2Cl)NC3=O)c1] | Fc1ccc(C1)c(c1)C1NC(=O)c2cc(Br)cc(NC(=O)c3cc(F)cc(c3)C#N)c12 | 1H NMR (400 MHz, Chloroform-d) 8.50 (s, 1H), 7.97 (d, 1.6 Hz, 1H), 7.57 (td, 10.5, 9.9, 6.3 Hz, 3H), 7.42-7.38 (m, 2H), 7.22-7.12 (m, 1H), 6.74 (s, 1H), 6.52 (s, 1H), 6.19 (s, 1H). | | D | |
| I-911 | 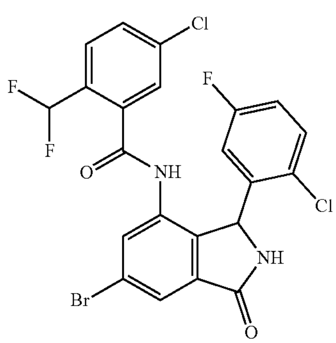 [SMILES: O=C(Nc1cc(Br)cc2c1C(c1cc(F)ccc1Cl)NC2=O)c1cc(Cl)ccc1C(F)F] | FC(F)c1ccc(Cl)cc1C(=O)Nc1cc(Br)cc2C(=O)NC(c12)c1cc(F)ccc1Cl | 1H NMR (400 MHz, Chloroform-d) 8.45 (s, 1H), 7.96 (q, 1.8 Hz, 1H), 7.73 (d, 8.4 Hz, 1H), 7.61 (dd, 8.4, 2.0 Hz, 1H), 7.45-7.22 (m, 2H), 7.18-7.06 (m, 2H), 6.95 (d, 4.1 Hz, 1H), 6.72 (d, 8.5 Hz, 1H), 6.58 (s, 1H), 6.17 (s, 1H) | 544.95 | D | |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-912 | 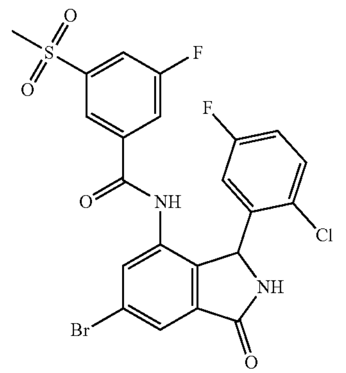 [SMILES: CS(=O)(=O)c1cc(F)cc(C(=O)Nc2cc(Br)cc3c2C(c2cc(F)ccc2Cl)NC3=O)c1] | CS(=O)(=O)c1cc(F)cc(c1)C(=O)Nc1cc(Br)cc2C(=O)NC(c12)c1cc(F)ccc1Cl | 1H NMR (400 MHz, Chloroform-d) 8.34 (s, 1H), 7.94 (d, 1.6 Hz, 1H), 7.87-7.81 (m, 3H), 7.67 (ddd, 8.3, 2.4, 1.5 Hz, 1H), 7.46 (dd, 8.9, 4.9 Hz, 1H), 7.07 (ddd, 8.9, 7.4, 3.0 Hz, 1H), 6.73-6.64 (m, 2H), 6.21 (s, 1H), 3.12 (s, 3H). | 557 | E | |
| I-913 | 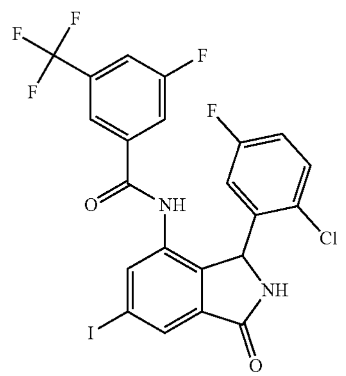 [SMILES: O=C(Nc1cc(I)cc2c1C(c1cc(F)ccc1Cl)NC2=O)c1cc(F)cc(C(F)(F)F)c1] | Fc1ccc(C1)c(c1)C1NC(=O)c2cc(I)cc(NC(=O)c3cc(F)cc(c3)C(F)(F)F)c12 | (400 MHz, DMSO-d6) 10.54 (s, 1 H), 9.22 (s, 1 H), 8.03-7.80 (m, 3 H), 7.72 (d, 9.0 Hz, 1 H), 7.66 (s, 1 H), 7.32 (dd, 8.9, 5.2 Hz, 1 H), 7.09 (td, 8.5, 3.0 Hz, 1 H), 6.66 (br s, 1 H), 5.93 (br s, 1 H). | 591.3 | A | A |
| I-914 | 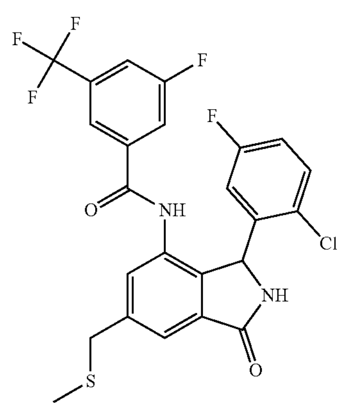 [SMILES: CSCc1cc(NC(=O)c2cc(F)cc(C(F)(F)F)c2)c2c(c1)C(=O)NC2c1cc(F)ccc1Cl] | CSCc1cc2C(=O)NC(c2c(NC(=O)c2cc(F)cc(c2)C(F)(F)F)c1)c1cc(F)ccc1Cl | NMR (400 MHz, DMSO-d6) 10.52 (s, 1H), 9.14 (s, 1H), 7.93 (t, 8.7 Hz, 1H), 7.74 (d, 9.2 Hz, 1H), 7.64 (d, 6.4 Hz, 2H), 7.44 (s, 1H), 7.31 (dd, 8.9, 5.2 Hz, 1H), 7.09 (td, 8.4, 3.0 Hz, 1H), 5.97 (br, s, 1H), 4.00-3.75 (m, 2H), 1.99 (s,3H). | 527.3 | A | A |
| I-915 | 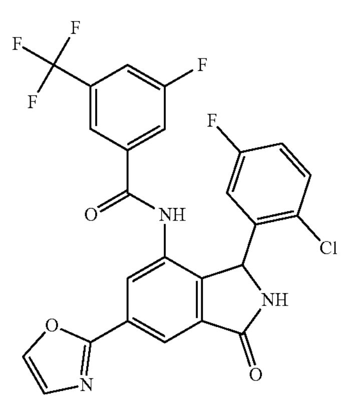 [SMILES: O=C(Nc1cc(-c2ncco2)cc2c1C(c1cc(F)ccc1Cl)NC2=O)c1cc(F)cc(C(F)(F)F)c1] | Fc1ccc(C1)c(c1)C1NC(=O)c2cc(cc(NC(=O)c3cc(F)cc(c3)C(F)(F)F)c12)-c1ncco1 | NMR (400 MHz, DMSO) 10.69 (s, 1H), 9.33 (s, 1H), 8.33 (s, 1H), 8.16 (s, 2H), 7.96 (d, 8.3 Hz, 1H), 7.77 (d, 8.9 Hz, 1H), 7.68 (s, 1H), 7.48 (s, 1H), 7.34 (dd, 8.8, 5.2 Hz, 1H), 7.10 (td, 8.5, 3.1 Hz, 1H), 6.08 (s, 1H). Ortho proton of the B-ring is missing | 534 | A | A |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-916 | 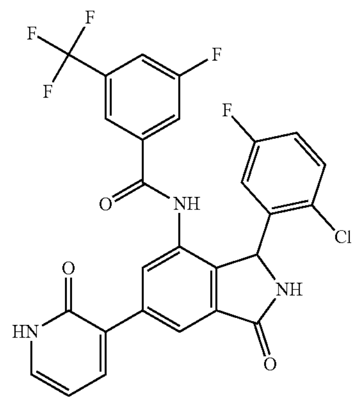 [SMILES: O=C(Nc1cc(-c2ccc[nH]c2=O)cc2c1C(c1cc(F)ccc1Cl)NC2=O)c1cc(F)cc(C(F)(F)F)c1] | Fc1ccc(C1)c(c1)C1NC(=O)c2cc(cc(NC(=O)c3cc(F)cc(c3)C(F)(F)F)c12)-c1ccc[nH]c1=O | NMR (400 MHz, DMSO) 12.00 (s, 1H), 10.59 (s, 1H), 9.15 (s, 1H), 8.07 (m, 1H), 7.94 (m, 2H), 7.85 (dd, 7.0, 2.0 Hz, 1H), 7.75 (d, 8.7 Hz, 1H), 7.68 (s, 1H), 7.47 (dd, 6.3, 1.4 Hz, 1H), 7.33 (dd, 8.9, 5.2 Hz, 1H), 7.10 (td, 8.4, 3.1 Hz, 1H), 6.36 (t, 6.7 Hz, 1H), 5.99 (s, 1H). Ortho proton of B-ring is missing | 560 | A | A |
| I-917 | 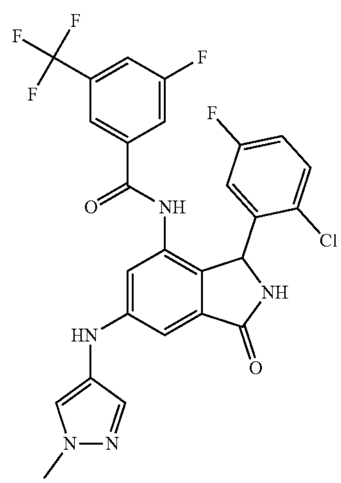 [SMILES: Cn1cc(Nc2cc(NC(=O)c3cc(F)cc(C(F)(F)F)c3)c3c(c2)C(=O)NC3c2cc(F)ccc2Cl)cn1] | Cn1cc(Nc2cc3C(=O)NC(c3c(NC(=O)c3cc(F)cc(c3)C(F)(F)F)c2)c2cc(F)ccc2Cl)cn1 | NMR (400 MHz, DMSO-d6) 10.30 (s, 1H), 8.96 (bs, 1H), 7.95 (s, 1H), 7.92 (d, 8.5 Hz, 1H), 7.74 (s, 1H), 7.69 (d, 9.1 Hz, 1H), 7.60 (s, 1H), 7.38 (s, 1H), 7.28 (dd, 8.8, 5.1 Hz, 1H), 7.06 (td, 8.3, 2.9 Hz, 1H), 6.96 (d, 1.6 Hz, 1H), 6.84 (d, 1.5 Hz, 1H), 6.69 (bs, 1H), 5.85 (bs, 1H), 3.83 (s, 3H). | 262.4 | A | A |
| I-918 | 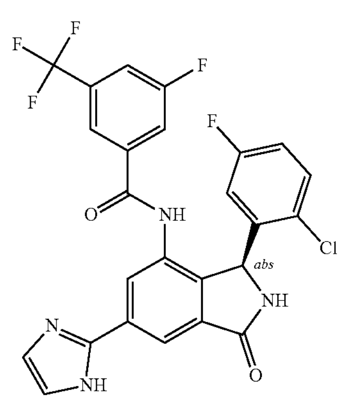 [SMILES: O=C(Nc1cc(-c2ncc[nH]2)cc2c1[C@@H](c1cc(F)ccc1Cl)NC2=O)c1cc(F)cc(C(F)(F)F)c1] | Fc1ccc(C1)c(c1)[C@H]1NC(=O)c2cc(cc(NC(=O)c3cc(F)cc(c3)C(F)(F)F)c12)-c1ncc[nH]1 | NMR (400 MHz, DMSO-d6) 12.83 (br. s, 1H), 10.65 (s, 1H), 9.22 (s, 1H), 8.37 (s, 1H), 8.27 (d, 0.7 Hz, 1H), 8.14 (d, 1.0 Hz, 1H), 7.96 (d, 8.3 Hz, 1H), 7.77 (d, 8.6 Hz), 7.69 (s, 1H), 7.32 (dd, 8.9, 5.2 Hz, 1H), 7.34-7.07 (m, sumerged 1H), 7.09 (td, 8.5, 3.0 Hz, 1H), 6.66 (br. s, 1H), 6.02 (br. s, 1H). | 533.2 | C | |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-919 | 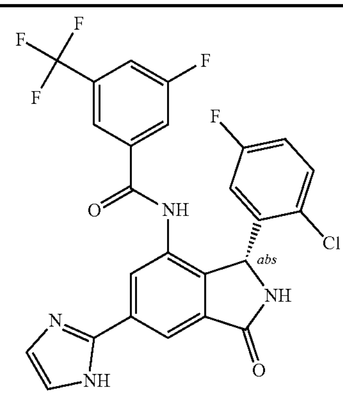 | Fc1ccc(C1)c(c1)[C@@H]1NC(=O)c2cc(cc(NC(=O)c3cc(F)cc(c3)C(F)(F)F)c12)-c1ncc[nH]1 | NMR (400 MHz, DMSO-d6) 12.83 (br. s, 1H), 10.65 (s, 1H), 9.22 (s, 1H), 8.37 (s, 1H), 8.27 (d, 0.7 Hz, 1H), 8.14 (d, 1.0 Hz, 1H), 7.96 (d, 8.3 Hz, 1H), 7.77 (d, 8.6 Hz), 7.69 (s, 1H), 7.32 (dd, 8.9, 5.2 Hz, 1H), 7.34-7.07 (m, sumerged 1H), 7.09 (td, 8.5, 3.0 Hz, 1H), 6.66 (br. s, 1H), 6.02 (br. s, 1H). | 533.2 | A | A |
| I-920 | 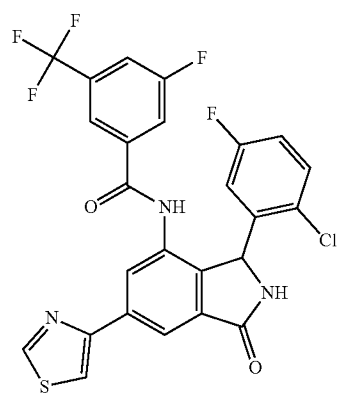 [SMILES: O=C(Nc1cc(-c2cscn2)cc2c1C(c1cc(F)ccc1Cl)NC2=O)c1cc(F)cc(C(F)(F)F)c1] | Fc1ccc(C1)c(c1)C1NC(=O)c2cc(cc(NC(=O)c3cc(F)cc(c3)C(F)(F)F)c12)-c1cscn1 | NMR (400 MHz, CD3CN) 9.01 (d, 1.9 Hz, 1H), 8.76 (br s, 1H), 8.29 (d, 1.4 Hz, 1H), 8.25 (s, 1H), 8.02 (d, 1.9 Hz, 1H), 7.70-7.59 (m, 3H), 7.32 (br s, 1H), 7.27 (dd, 8.9, 5.1 Hz, 1H), 6.98 (ddd, 8.8, 8.0, 3.1 Hz, 1H), 6.72 (br s, 1H), 6.18 (br s, 1H). | 550.3 | A | A |
| I-921 | 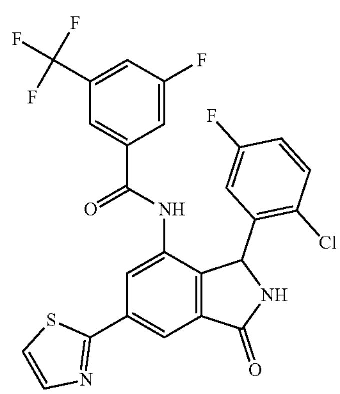 [SMILES: O=C(Nc1cc(-c2nccs2)cc2c1C(c1cc(F)ccc1Cl)NC2=O)c1cc(F)cc(C(F)(F)F)c1] | Fc1ccc(C1)c(c1)C1NC(=O)c2cc(cc(NC(=O)c3cc(F)cc(c3)C(F)(F)F)c12)-c1nccs1 | NMR (400 MHz, CD3CN) 8.76 (s, 1H), 8.20 (m, 2H), 7.93 (d, 3.6, 1H), 7.65-7.55 (m, 4H), 7.35 (br s, 1H), 7.25 (dd, 8.9, 5.1 Hz, 1H), 6.99 (ddd, 8.8, 8.0, 3.1 Hz, 1H), 6.69 (br s, 1H), 6.16 (br s, 1H). | 550.3 | A | A |
| I-922 | 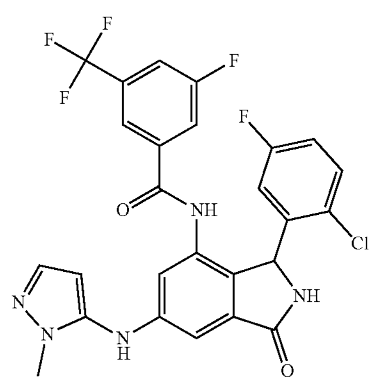 | Cn1nccc1Nc1cc2C(=O)NC(c2c(NC(=O)c2cc(F)cc(c2)C(F)(F)F)c1)c1cc(F)ccc1Cl | NMR (400 MHz, DMSOd6) 10.37 (s, 1H), 9.04 (s, 1H), 8.45 (s, 1H), 7.93 (d, 8.5 Hz, 1H), 7.69 (d, 9.2 Hz, 1H), 7.59 (s, 1H), 7.42 (d, 1.9 Hz, 1H), 7.30 (dd, 8.9, 5.2 Hz, 1H), 7.07 (td, 8.3, 3.1 Hz, 1H), 7.02 (d, 2.0 Hz, 1H), 6.93 (d, 1.64 Hz, 1H), 6.63 (bs, not well resolved, 1H), 6.12 (d, 1.9 Hz, 1H), 5.90 (bs, 1H), 3.68 (s, 3H). | 562.3 | A | A |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-923 | 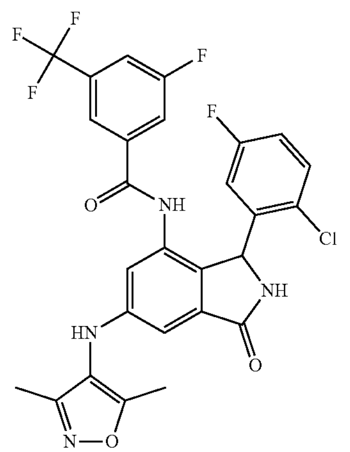 [SMILES: Cc1noc(C)c1Nc1cc(NC(=O)c2cc(F)cc(C(F)(F)F)c2)c2c(c1)C(=O)NC2c1cc(F)ccc1Cl] | Cc1noc(C)c1Nc1cc2C(=O)NC(c2c(NC(=O)c2cc(F)cc(c2)C(F)(F)F)c1)c1cc(F)ccc1Cl | NMR (400 MHz, CD3CN) 8.47 (br s, 1H), 7.60 (br d, 1H), 7.55 (d, 12.2 Hz, 1H), 7.51 (s, 1H), 7.22 (dd, 8.9, 5.1 Hz, 1H), 7.15 (br s, 1H), 6.93 (ddd, 11.1, 7.0, 3.1 Hz, 1H), 6.86 (d, 2.1 Hz, 1H), 6.76 (d, 1.8 Hz, 1H), 6.62 (br s, 1H), 6.17 (s, 1H), 5.99 (br s, 1H), 2.26 (s, 3H), 2.08 (s, 3H). | 577.5 | A | A |
| I-924 | 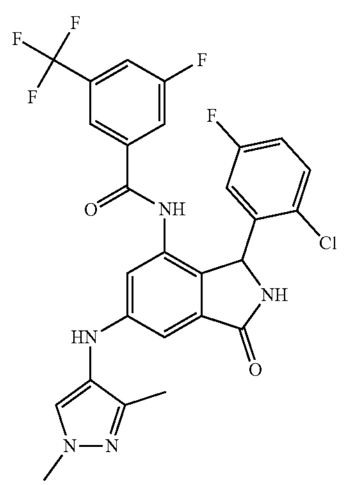 [SMILES: Cc1nn(C)cc1Nc1cc(NC(=O)c2cc(F)cc(C(F)(F)F)c2)c2c(c1)C(=O)NC2c1cc(F)ccc1Cl] | Cc1nn(C)cc1Nc1cc2C(=O)NC(c2c(NC(=O)c2cc(F)cc(c2)C(F)(F)F)c1)c1cc(F)ccc1Cl | NMR (400 MHz, DMSOd6) 10.29 (s, 1H), 8.94 (s, 1H), 7.91 (d, 8.7 Hz, 1H), 7.68 (submerged br. d, 1H), 7.67 (s, 1H), 7.60-7.58 (m, 1H), 7.28 (dd, 8.9, 5.2 Hz, 1H), 7.06 (td, 8.3, 3.1 Hz, 1H), 6.82 (d, 2.0 Hz, 1H), 6.72 (d, 1.8 Hz, 1H), 6.60 (bs, not well resolved, 1H), 5.83 (bs, 1H), 3.76 (s, 3H), 2.02 (s, 3H). Presence of 20% formate salt (8.38). | 576.3 | A | A |
| I-925 | 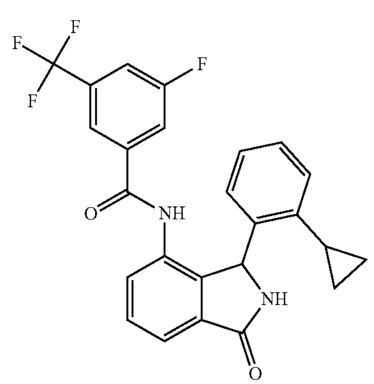 [SMILES: O=C(Nc1cccc2c1C(c1ccccc1C1CC1)NC2=O)c1cc(F)cc(C(F)(F)F)c1] | Fc1cc(cc(c1)C(F)(F)F)C(=O)Nc1cccc2C(=O)NC(c12)c1ccccc1C1CC1 | 1H NMR (400 MHz, DMSO-d6) 10.15 (br. s, 1H), 8.85 (s, 1H), 7.79 (d, 8.4 Hz, 1H), 7.69 (d, 7.5 Hz, 1H), 7.61 (t, 7.6 Hz, 1H), 7.54-7.47 (m, 3H), 7.08 (t, 7.8 Hz, 1H), 6.95 (t, 7.7 Hz, 1H), 6.85 (d, 7.6 Hz, 1H), 6.66 (br. s, 1H), 6.21 (br. s, 1H), 1.88 (s), 0.74-0.47 (m, 1H), 0.70-0.50 (m, 3H), 0.47-0.39 (m, 1H); DMSO satellites at 2.68 and 2.33 | 455.3 | B | |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-926 | 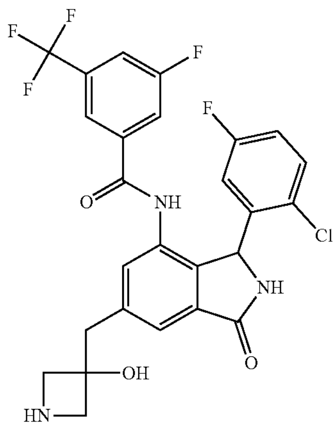 [SMILES: O=C(Nc1cc(CC2(O)CNC2)cc2c1C(c1cc(F)ccc1Cl)NC2=O)c1cc(F)cc(C(F)(F)F)c1] | OC1(Cc2cc3C(=O)NC(c3c(NC(=O)c3cc(F)cc(c3)C(F)(F)F)c2)c2cc(F)ccc2Cl)CNC1 | NMR (400 MHz, DMSO-d6) 10.54 (s, 1H), 9.07 (s, 1H), 8.34 (s, 1H), 7.90 (d, 8.6 Hz, 1H), 7.69 (d, 8.7 Hz, 1H), 7.59 (d, 4.4 Hz, 2H), 7.36 (s, 1H), 7.27 (dd, 8.9, 5.2 Hz, 1H), 7.05 (td, 8.4, 3.1 Hz, 1H), 6.58 (br., 1H), 6.21 (br, 1H), 5.90 (s, 1H), 3.65 (d, 9.6 Hz, 2H), 3.58 (d, 9.8 Hz, 2H)3.13 (dd, 13.9 Hz, 9.6Hz, 2H). | 552.3 | A | D |
| I-927 | 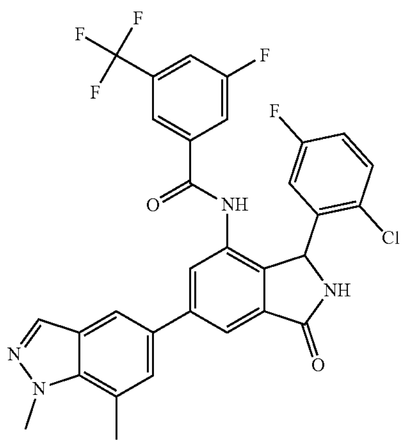 [SMILES: Cc1cc(-c2cc(NC(=O)c3cc(F)cc(C(F)(F)F)c3)c3c(c2)C(=O)NC3c2cc(F)ccc2Cl)cc2cnn(C)c12] | Cc1cc(cc2cnn(C)c12)-c1cc2C(=O)NC(c2c(NC(=O)c2cc(F)cc(c2)C(F)(F)F)c1)c1cc(F)ccc1Cl | | | B | C |
| I-928 | 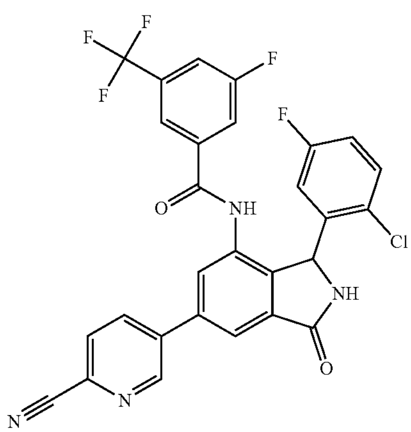 [SMILES: N#Cc1ccc(-c2cc(NC(=O)c3cc(F)cc(C(F)(F)F)c3)c3c(c2)C(=O)NC3c2cc(F)ccc2Cl)cn1] | Fc1ccc(C1)c(c1)C1NC(=O)c2cc(cc(NC(=O)c3cc(F)cc(c3)C(F)(F)F)c12)-c1ccc(nc1)C#N | | | A | A |

TABLE 2-continued

Representative Compounds of the Invention with Bioactivity Data.

| Ex. No. | Structure | SMILES | $^1$H NMR | MS | ADP-Glo IC$_{50}$ | MCF 10A IC$_{50}$ |
|---|---|---|---|---|---|---|
| I-929 | 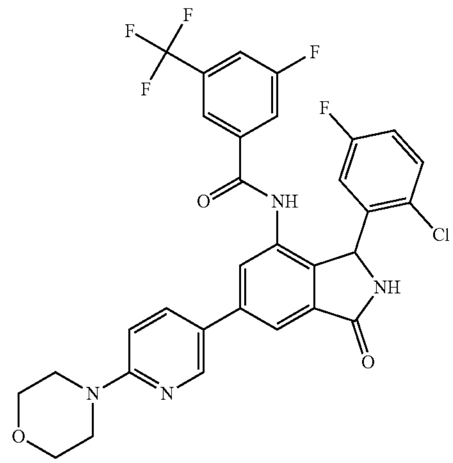 [SMILES: O=C(Nc1cc(-c2ccc(N3CCOCC3)nc2)cc2c1C(c1cc(F)ccc1Cl)NC2=O)c1cc(F)cc(C(F)(F)F)c1] | Fc1ccc(C1)c(c1)C1NC(=O)c2cc(cc(NC(=O)c3cc(F)cc(c3)C(F)(F)F)c12)-c1ccc(nc1)N1CCOCC1 | | | A | A |
| I-930 | 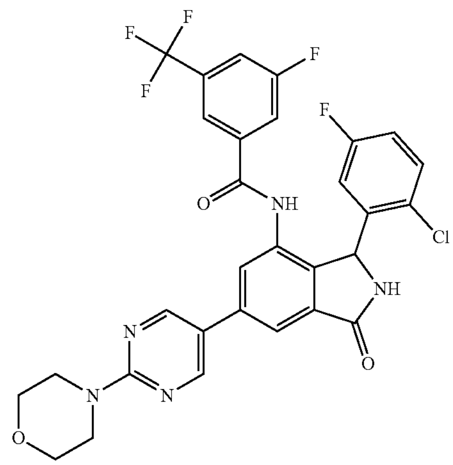 [SMILES: O=C(Nc1cc(-c2cnc(N3CCOCC3)nc2)cc2c1C(c1cc(F)ccc1Cl)NC2=O)c1cc(F)cc(C(F)(F)F)c1] | Fc1ccc(C1)c(c1)C1NC(=O)c2cc(cc(NC(=O)c3cc(F)cc(c3)C(F)(F)F)c12)-c1cnc(nc1)N1CCOCC1 | | | A | B |
| I-931 | 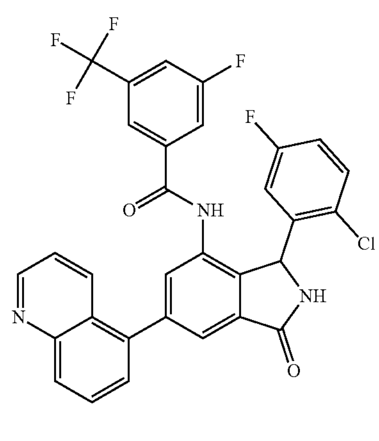 [SMILES: O=C(Nc1cc(-c2cccc3ncccc23)cc2c1C(c1cc(F)ccc1Cl)NC2=O)c1cc(F)cc(C(F)(F)F)c1] | Fc1ccc(C1)c(c1)C1NC(=O)c2cc(cc(NC(=O)c3cc(F)cc(c3)C(F)(F)F)c12)-c1cccc2ncccc12 | | | A | A |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-932 | 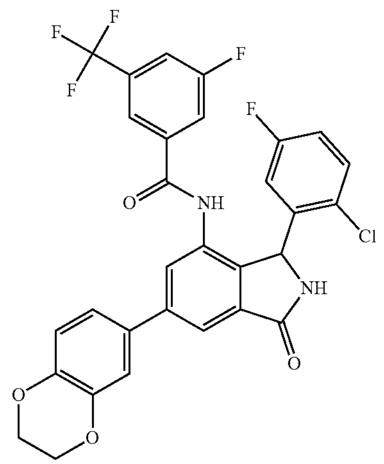 [SMILES: O=C(Nc1cc(-c2ccc3c(c2)OCCO3)cc2c1C(c1cc(F)ccc1Cl)NC2=O)c1cc(F)cc(C(F)(F)F)c1] | Fc1ccc(C1)c(c1)C1NC(=O)c2cc(cc(NC(=O)c3cc(F)cc(c3)C(F)(F)F)c12)-c1ccc2OCCOc2c1 | | | B | B |
| I-933 | 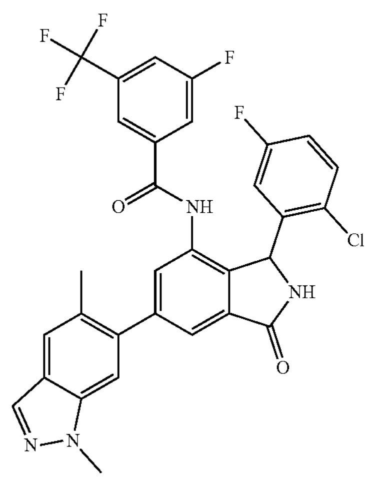 [SMILES: Cc1cc2cnn(C)c2cc1-c1cc(NC(=O)c2cc(F)cc(C(F)(F)F)c2)c2c(c1)C(=O)NC2c1cc(F)ccc1Cl] | Cc1cc2cnn(C)c2cc1-c1cc2C(=O)NC(c2c(NC(=O)c2cc(F)cc(c2)C(F)(F)F)c1)c1cc(F)ccc1Cl | | | B | C |
| I-934 | 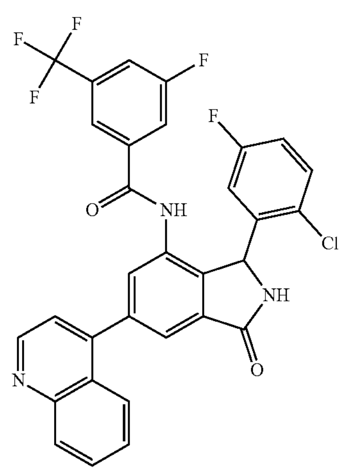 [SMILES: O=C(Nc1cc(-c2ccnc3ccccc23)cc2c1C(c1cc(F)ccc1Cl)NC2=O)c1cc(F)cc(C(F)(F)F)c1] | Fc1ccc(C1)c(c1)C1NC(=O)c2cc(cc(NC(=O)c3cc(F)cc(c3)C(F)(F)F)c12)-c1ccnc2ccccc12 | | | A | A |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-935 | 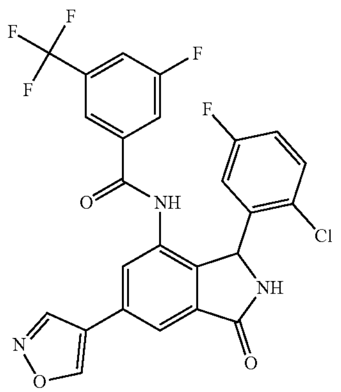 [SMILES: O=C(Nc1cc(-c2cnoc2)cc2c1C(c1cc(F)ccc1Cl)NC2=O)c1cc(F)cc(C(F)(F)F)c1] | Fc1ccc(C1)c(c1)C1NC(=O)c2cc(cc(NC(=O)c3cc(F)cc(c3)C(F)(F)F)c12)-c1cnoc1 | | | A | A |
| I-936 | 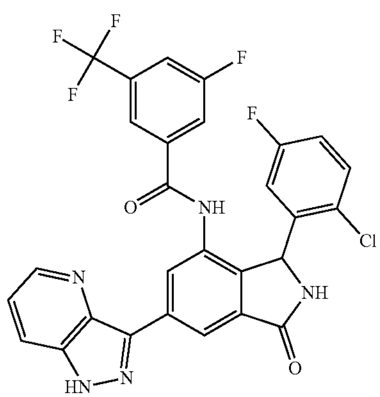 [SMILES: O=C(Nc1cc(-c2n[nH]c3cccnc23)cc2c1C(c1cc(F)ccc1Cl)NC2=O)c1cc(F)cc(C(F)(F)F)c1] | Fc1ccc(C1)c(c1)C1NC(=O)c2cc(cc(NC(=O)c3cc(F)cc(c3)C(F)(F)F)c12)-c1n[nH]c2cccnc12 | | | A | A |
| I-937 | 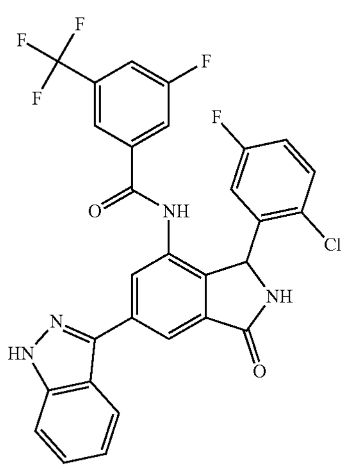 [SMILES: O=C(Nc1cc(-c2n[nH]c3ccccc23)cc2c1C(c1cc(F)ccc1Cl)NC2=O)c1cc(F)cc(C(F)(F)F)c1] | Fc1ccc(C1)c(c1)C1NC(=O)c2cc(cc(NC(=O)c3cc(F)cc(c3)C(F)(F)F)c12)-c1n[nH]c2ccccc12 | | | B | B |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-938 | 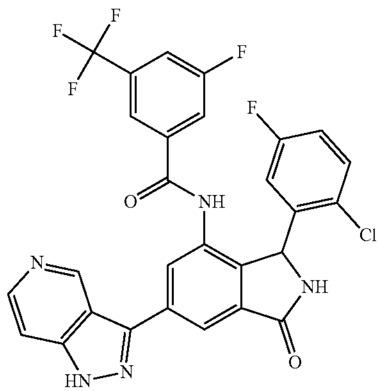 [SMILES: O=C(Nc1cc(-c2n[nH]c3ccncc23)cc2c1C(c1cc(F)ccc1Cl)NC2=O)c1cc(F)cc(C(F)(F)F)c1] | Fc1ccc(C1)c(c1)C1NC(=O)c2cc(cc(NC(=O)c3cc(F)cc(c3)C(F)(F)F)c12)-c1n[nH]c2ccncc12 | | | B | |
| I-939 | 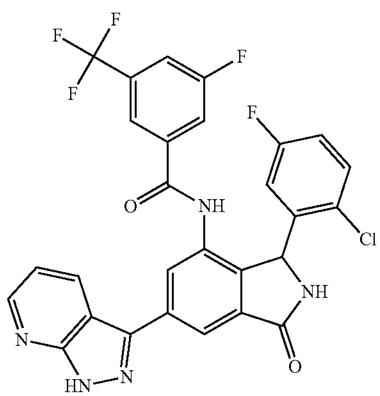 [SMILES: O=C(Nc1cc(-c2n[nH]c3ncccc23)cc2c1C(c1cc(F)ccc1Cl)NC2=O)c1cc(F)cc(C(F)(F)F)c1] | Fc1ccc(C1)c(c1)C1NC(=O)c2cc(cc(NC(=O)c3cc(F)cc(c3)C(F)(F)F)c12)-c1n[nH]c2ncccc12 | | | A | A |
| I-940 | 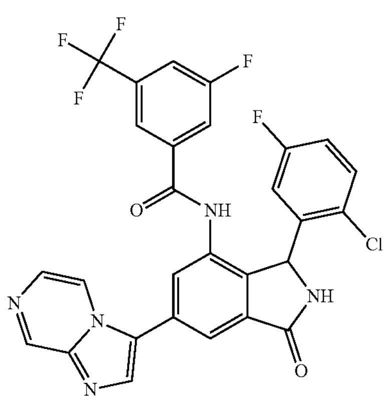 [SMILES: O=C(Nc1cc(-c2cnc3cnccn23)cc2c1C(c1cc(F)ccc1Cl)NC2=O)c1cc(F)cc(C(F)(F)F)c1] | Fc1ccc(C1)c(c1)C1NC(=O)c2cc(cc(NC(=O)c3cc(F)cc(c3)C(F)(F)F)c12)-c1cnc2cnccn12 | | | A | A |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-941 | 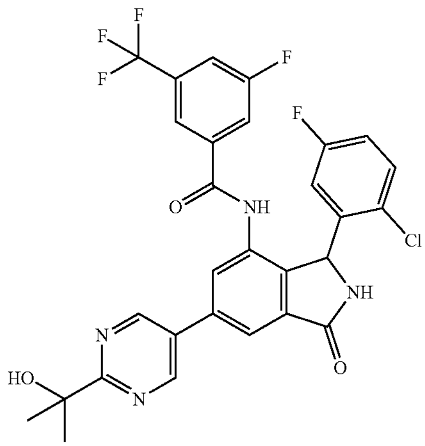 [SMILES: CC(C)(O)c1ncc(-c2cc(NC(=O)c3cc(F)cc(C(F)(F)F)c3)c3c(c2)C(=O)NC3c2cc(F)ccc2Cl)cn1] | CC(C)(O)c1ncc(cn1)-c1cc2C(=O)NC(c2c(NC(=O)c2cc(F)cc(c2)C(F)(F)F)c1)c1cc(F)ccc1Cl | | 603.5 | B | A |
| I-942 | 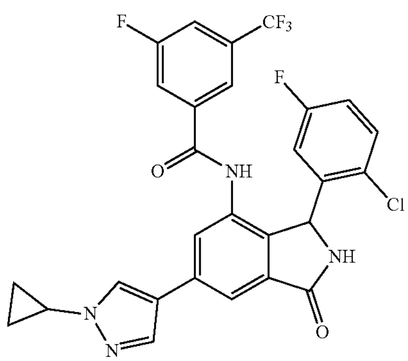 [SMILES: O=C(Nc1cc(-c2cnn(C3CC3)c2)cc2c1C(c1cc(F)ccc1Cl)NC2=O)c1cc(F)cc(C(F)(F)F)c1] | Fc1ccc(C1)c(c1)C1NC(=O)c2cc(cc(NC(=O)c3cc(F)cc(c3)C(F)(F)F)c12)-c1cnn(c1)C1CC1 | | 573.4 | A | A |
| I-943 | 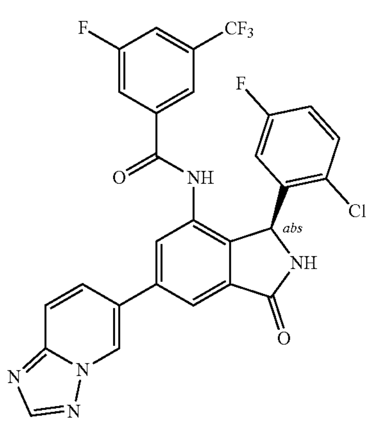 [SMILES: O=C(Nc1cc(-c2ccc3ncnn3c2)cc2c1[C@@H](c1cc(F)ccc1Cl)NC2=O)c1cc(F)cc(C(F)(F)F)c1] | Fc1ccc(C1)c(c1)[C@H]1NC(=O)c2cc(cc(NC(=O)c3cc(F)cc(c3)C(F)(F)F)c12)-c1ccc2ncnn2c1 | ¹H NMR (DMSO-d$_6$, 400 MHz): δ = 10.64 (s, 1H), 9.48 (s, 1H), 9.26 (br s, 1H), 8.58 (s, 1H), 8.10-8.19 (m, 2H), 7.99 (br d, J = 9.9 Hz, 3H), 7.75-7.83 (m, 1H), 7.73 (s, 1H), 7.35 (dd, J = 8.8, 5.3 Hz, 1H), 7.12 (td, J = 8.3, 3.0 Hz, 1H), 6.51-6.97 (m, 1H), 6.07 (br s, 1H). | 584.3 | C | |

TABLE 2-continued

Representative Compounds of the Invention with Bioactivity Data.

| Ex. No. | Structure | SMILES | $^1$H NMR | MS | ADP-Glo IC$_{50}$ | MCF 10A IC$_{50}$ |
|---|---|---|---|---|---|---|
| I-944 | 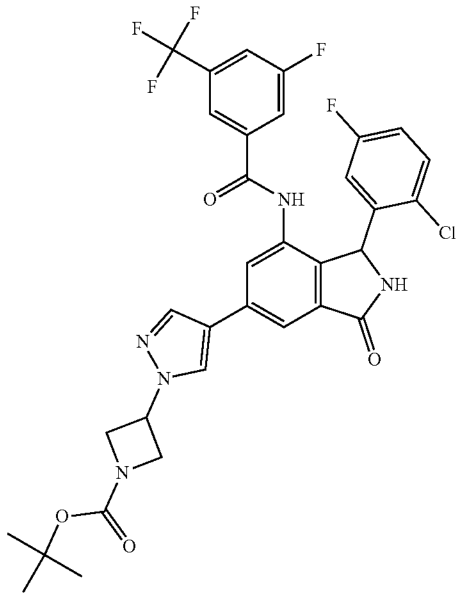 [SMILES: CC(C)(C)OC(=O)N1CC(n2cc(-c3cc(NC(=O)c4cc(F)cc(C(F)(F)F)c4)c4c(c3)C(=O)NC4c3cc(F)ccc3Cl)cn2)C1] | CC(C)(C)OC(=O)N1CC(C1)n1cc(cn1)-c1cc2C(=O)NC(c2c(NC(=O)c2cc(F)cc(c2)C(F)(F)F)c1)c1cc(F)ccc1Cl | | 588.37 | A | C |
| I-945 | 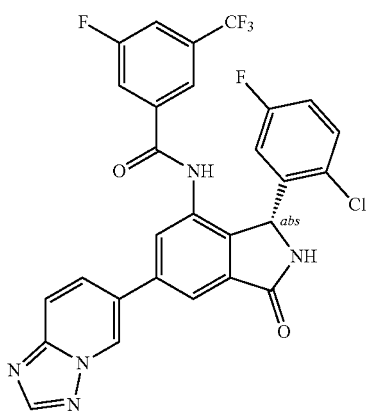 [SMILES: O=C(Nc1cc(-c2ccc3ncnn3c2)cc2c1[C@H](c1cc(F)ccc1Cl)NC2=O)c1cc(F)cc(C(F)(F)F)c1] | Fc1ccc(C1)c(c1)[C@@H]1NC(=O)c2cc(cc(NC(=O)c3cc(F)cc(c3)C(F)(F)F)c12)-c1ccc2ncnn2c1 | $^1$H NMR (DMSO-d$_6$, 400 MHz): δ = 10.64 (s, 1H), 9.48 (s, 1H), 9.26 (br s, 1H), 8.58 (s, 1H), 8.10-8.19 (m, 2H), 7.99 (br d, J = 9.9 Hz, 3H), 7.75-7.83 (m, 1H), 7.73 (s, 1H), 7.35 (dd, J = 8.8, 5.3 Hz, 1H), 7.12 (td, J = 8.3, 3.0 Hz, 1H), 6.51-6.97 (m, 1H), 6.07 ppm (br s, 1H). | 584.3 | A | A |
| I-946 | 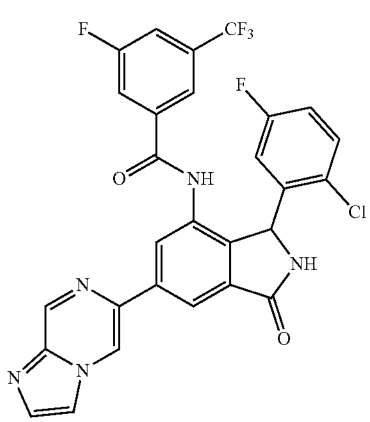 [SMILES: O=C(Nc1cc(-c2cn3ccnc3cn2)cc2c1C(c1cc(F)ccc1Cl)NC2=O)c1cc(F)cc(C(F)(F)F)c1] | Fc1ccc(C1)c(c1)C1NC(=O)c2cc(cc(NC(=O)c3cc(F)cc(c3)C(F)(F)F)c12)-c1cn2ccnc2cn1 | 1H NMR (500 MHz, DMSO) 10.64 (s, 1H), 9.51 (d, 1.5 Hz, 1H), 9.27-9.12 (m, 2H), 8.29 (d, 26.2 Hz, 2H), 8.15 (t, 0.9 Hz, 1H), 7.94 (d, 8.4 Hz, 1H), 7.91-7.84 (m, 1H), 7.78 (d, 9.0 Hz, 1H), 7.72 (s, 1H), 7.33 (dd, 8.9, 5.2 Hz, 1H), 7.09 (td, 8.3, 3.1 Hz, 1H), 6.06 (s, 1H). | 584.37 | A | A |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-947 | 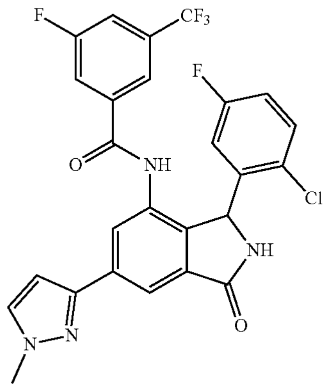 [SMILES: Cn1ccc(-c2cc(NC(=O)c3cc(F)cc(C(F)(F)F)c3)c3c(c2)C(=O)NC3c2cc(F)ccc2Cl)n1] | Cn1ccc(n1)-c1cc2C(=O)NC(c2c(NC(=O)c2cc(F)cc(c2)C(F)(F)F)c1)c1cc(F)ccc1Cl | 1H NMR (500 MHz, DMSO) 10.52 (s, 1H), 9.13 (s, 1H), 8.04 (d, 1.5 Hz, 1H), 7.98-7.88 (m, 2H), 7.83-7.66 (m, 3H), 7.31 (dd, 8.9, 5.1 Hz, 1H), 7.08 (td, 8.4, 3.2 Hz, 1H), 6.86 (d, 2.3 Hz, 1H), 5.99 (s, 1H), 3.91 (s, 3H). | 547.41 | A | A |
| I-948 | 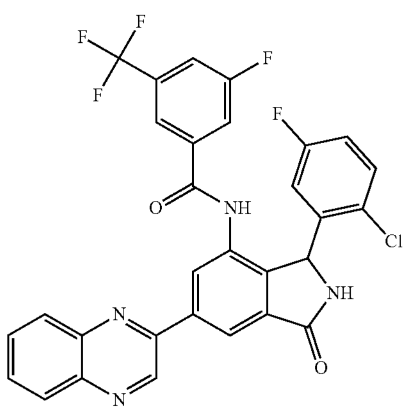 [SMILES: O=C(Nc1cc(-c2cnc3ccccc3n2)cc2c1C(c1cc(F)ccc1Cl)NC2=O)c1cc(F)cc(C(F)(F)F)c1] | Fc1ccc(C1)c(c1)C1NC(=O)c2cc(cc(NC(=O)c3cc(F)cc(c3)C(F)(F)F)c12)-c1cnc2ccccc2n1 | 1H NMR (500 MHz, DMSO-d6) 6.04-6.18 (m, 1 H) 6.52 (br d, 1.53 Hz, 1 H) 7.12 (td, 8.32, 2.90 Hz, 1 H) 7.36 (dd, 9.00, 5.04 Hz, 1 H) 7.73-7.78 (m, 1 H) 7.82 (br d, 8.85 Hz, 1 H) 7.89-8.03 (m, 3 H) 8.19 (td, 7.55, 1.68 Hz, 2 H) 8.52 (s, 1 H) 8.67 (s, 1 H) 9.31 (br d, 3.05 Hz, 1 H) 9.77 (s, 1 H) 10.76 (s, 1 H) | 595.33 | A | A |
| I-949 | 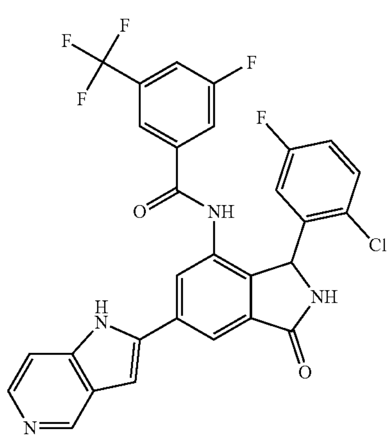 | Fc1ccc(C1)c(c1)C1NC(=O)c2cc(cc(NC(=O)c3cc(F)cc(c3)C(F)(F)F)c12)-c1cc2cnccc2[nH]1 | 1H NMR (500 MHz, DMSO-d6) 7.09-7.14 (m, 1 H) 7.33-7.37 (m, 1 H) 7.66 (s, 1 H) 7.73 (s, 1 H) 7.78 (br d, 9.16 Hz, 1 H) 7.93-8.04 (m, 3 H) 8.18 (s, 1 H) 8.38 (s, 1 H) 8.45 (d, 6.71 Hz, 1 H) 9.27-9.38 (m, 2 H) 10.69 (s, 1 H) 13.57 (s, 1 H) 14.65-14.98 (m, 1 H) | 583.32 | A | B |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-950 | 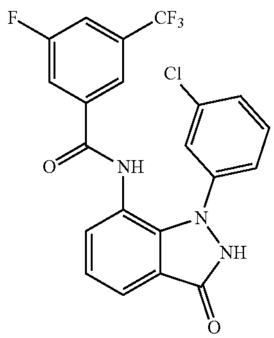 [SMILES: O=C(Nc1cccc2c(=O)[nH]n(-c3cccc(Cl)c3)c12)c1cc(F)cc(C(F)(F)F)c1] | Fc1cc(cc(c1)C(F)(F)F)C(=O)Nc1ccccc2c1n([nH]c2=O)-c1cccc(Cl)c1 | 1H NMR (400 MHz, DMSO-d6) 11.50 (br s, 1H), 10.65 (s, 1H), 7.94 (d, 12.7 Hz. 1H), 7.74 (m, 3H), 7.38 (d, 7.4 Hz., 1H), 7.33 (d, 8.2 Hz, 1H), 7.23(m, 3H), 7.05 (d, 8.0 Hz, 1H). | 450.3 | D | |
| I-951 | 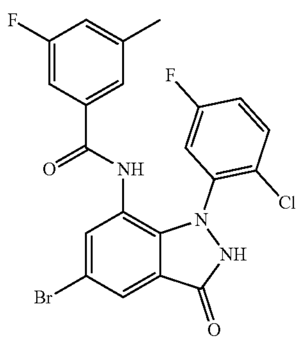 [SMILES: Cc1cc(F)cc(C(=O)Nc2cc(Br)cc3c(=O)[nH]n(-c4cc(F)ccc4Cl)c23)c1] | Cc1cc(F)cc(c1)C(=O)Nc1cc(Br)cc2C(=O)NC(c12)c1cc(F)ccc1Cl | 1H NMR (400 MHz, Chloroform-d) 8.52 (s, 1H), 7.94 (d, 1.7 Hz, 1H), 7.46 (dd, 8.9, 4.9 Hz, 1H), 7.32 (s, 1H), 7.15-7.04 (m, 3H), 6.97 (d, 8.7 Hz, 1H), 6.73 (s, 1H), 6.49 (s, 1H), 6.18 (s, 1H), 2.41 (d, 0.8 Hz, 3H). | 493 | D | |
| I-952 | 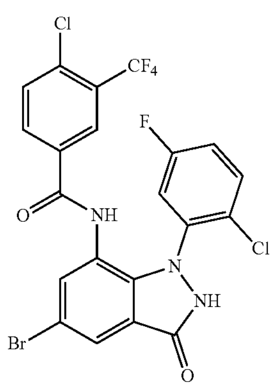 | Fc1ccc(C1)c(c1)C1NC(=O)c2cc(Br)cc(NC(=O)c3ccc(Cl)c(c3)C(F)(F)F)c12 | 1H NMR (400 MHz, Chloroform-d) 8.41 (s, 1H), 7.98 (d, 1.7 Hz, 1H), 7.74 (d, 5.3 Hz, 2H), 7.63 (d, 8.9 Hz, 1H), 7.45-7.36 (m, 2H), 7.13-7.03 (m, 1H), 6.71 (s, 1H), 6.44 (s, 1H), 6.18 (s, 1H). | 560.85 | B | |
| I-953 | 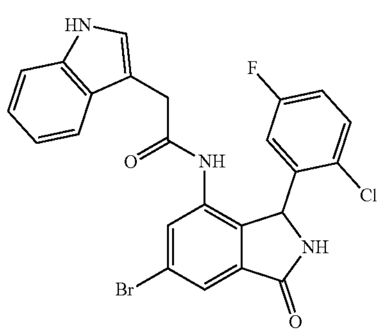 [SMILES: O=C(Cc1c[nH]c2ccccc12)Nc1cc(Br)cc2c1C(c1cc(F)ccc1Cl)NC2=O] | Fc1ccc(C1)c(c1)C1NC(=O)c2cc(Br)cc(NC(=O)Cc3c[nH]c4ccccc34)c12 | 1H NMR (400 MHz, DMSO-d6) 10.87 (s, 1H), 9.71 (s, 1H), 9.20 (s, 1H), 7.71 (dd, 16.6, 1.7 Hz, 2H), 7.40 (dd, 8.9, 5.2 Hz, 1H), 7.36-7.30 (m, 1H), 7.35-7.25 (m, 1H), 7.15 (td, 8.5, 2.9 Hz, 1H), 7.11-7.03 (m, 1H), 7.01 (d, 2.4 Hz, 1H), 6.94 (ddd, 7.9, 6.9, 1.1 Hz, 1H), 6.65 (s, 1H), 6.02 (s, 1H), 3.46 (s, 2H). | 512 | E | |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-954 | 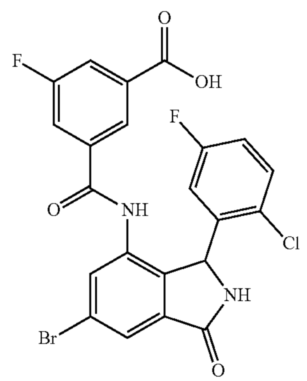 [SMILES: O=C(O)c1cc(F)cc(C(=O)Nc2cc(Br)cc3c2C(c2cc(F)ccc2Cl)NC3=O)c1] | OC(=O)c1cc(F)cc(c1)C(=O)Nc1cc(Br)cc2C(=O)NC(c12)c1cc(F)ccc1Cl | 1H NMR (400 MHz, DMSO-d6) 13.51 (s, 1H), 10.53 (s, 1H), 9.28 (s, 1H), 8.00 (d, 1.5 Hz, 1H), 7.89-7.79 (m, 2H), 7.72 (d, 1.9 Hz, 1H), 7.60 (dt, 9.2, 2.0 Hz, 1H), 7.33 (dd, 8.9, 5.2 Hz, 1H), 7.09 (td, 8.4, 3.1 Hz, 1H), 6.73 (s, 1H), 5.99 (s, 1H). | 523 | E | |
| I-955 | 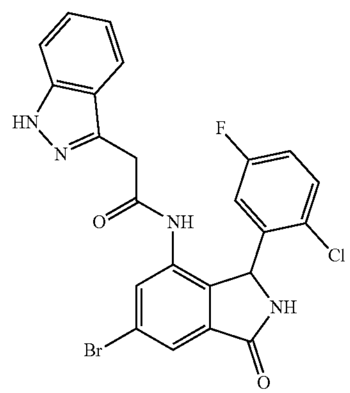 [SMILES: O=C(Cc1n[nH]c2ccccc12)Nc1cc(Br)cc2c1C(c1cc(F)ccc1Cl)NC2=O] | Fc1ccc(C1)c(c1)C1NC(=O)c2cc(Br)cc(NC(=O)Cc3n[nH]c4cccc34)c12 | 1H NMR (400 MHz, DMSO-d6) 12.78 (s, 1H), 10.04 (s, 1H), 9.20 (s, 1H), 7.76-7.69 (m, 2H), 7.53-7.44 (m, 2H), 7.42-7.29 (m, 2H), 7.16 (t, 7.2 Hz, 1H), 7.10-6.30 (m, 2H), 6.00 (s, 1H), 3.70 (s, 2H),. | 513.05 | E | |
| I-956 | 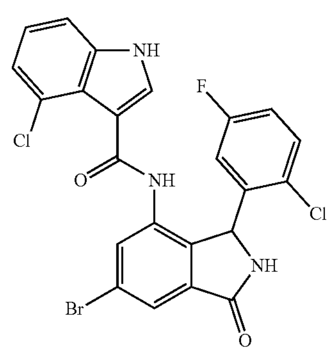 [SMILES: O=C1NC(c2cc(F)ccc2Cl)c2c(NC(=O)c3c[nH]c4cccc(Cl)c34)cc(Br)cc21] | Fc1ccc(C1)c(c1)C1NC(=O)c2cc(Br)cc(NC(=O)c3c[nH]c4cccc(Cl)c34)c12 | 1H NMR (400 MHz, DMSO-d6) 11.89 (s, 1H), 9.93 (s, 1H), 9.23 (s, 1H), 7.80 (d, 1.9 Hz, 1H), 7.72 (d, 1.7 Hz, 1H), 7.49-7.40 (m, 2H), 7.27-7.10 (m, 4H), 6.78 (s, 1H), 6.11 (s, 1H). | 532 | D | |
| I-957 | 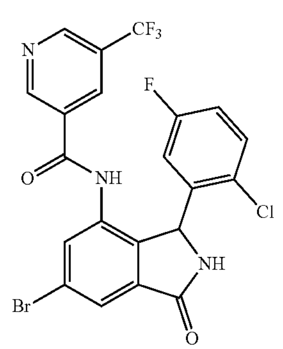 | Fc1ccc(C1)c(c1)C1NC(=O)c2cc(Br)cc(NC(=O)c3cncc(c3)C(F)(F)F)c12 | 1H NMR (400 MHz, DMSO-d6) 10.68 (s, 1H), 9.31 (s, 1H), 9.18 (s, 1H), 9.02 (s, 1H), 8.18 (s, 1H), 7.85 (s, 1H), 7.75 (s, 1H), 7.33 (dd, 8.9, 5.0 Hz, 1H), 7.10 (dd, 8.7, 3.0 Hz, 1H), 6.82 (t, 9.0 Hz, 1H), 5.97 (s, 1H). | 530.1 | D | |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-958 | 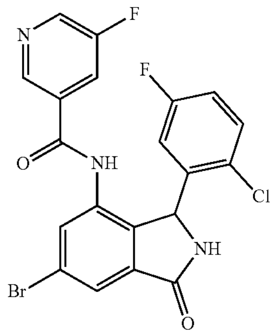 [SMILES: O=C(Nc1cc(Br)cc2c1C(c1cc(F)ccc1Cl)NC2=O)c1cncc(F)c1] | Fc1ccc(C 1)c(c1)C1 NC(=O)c 2cc(Br)cc (NC(=O) c3cncc(F) c3)c12 | 1H NMR (400 MHz, DMSO-d6) 10.52 (s, 1H), 9.30 (s, 1H), 8.78 (d, 2.8 Hz, 1H), 8.56 (d, 1.8 Hz, 1H), 7.87-7.79 (m, 2H), 7.75 (d, 1.8 Hz, 1H), 7.36 (dd, 8.8, 5.2 Hz, 1H), 7.19-7.09 (m, 1H), 6.76 (s, 1H), 5.99 (s, 1H). | 479.95 | E | |
| I-959 | 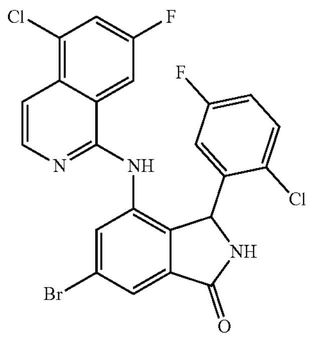 [SMILES: O=C1NC(c2cc(F)ccc2Cl)c2c(Nc3nccc4c(Cl)cc(F)cc34)cc(Br)cc21] | Fc1ccc(C 1)c(c1)C1 NC(=O)c 2cc(Br)cc (Nc3nccc 4c(Cl)cc (F)cc34)c 12 | 1H NMR (400 MHz, DMSO-d6) 9.27 (s, 1H), 9.14 (s, 1H), 8.09 (d, 6.0 Hz, 1H), 7.98 (dd, 8.6, 2.4 Hz, 1H), 7.73-7.66 (m, 2H), 7.65 (d, 9.8 Hz, 1H), 7.39 (d, 6.0 Hz, 1H), 7.06 (s, 1H), 6.93-6.84 (m, 1H), 6.30 (s, 1H), 5.80 (s, 1H) | 533.95 | B | A |
| I-960 | 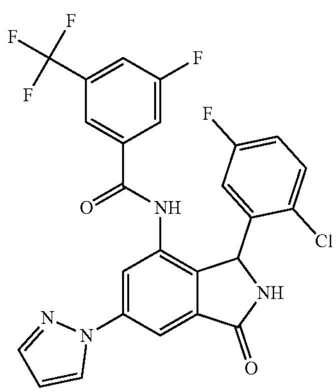 [SMILES: O=C(Nc1cc(-n2cccn2)cc2c1C(c1cc(F)ccc1Cl)NC2=O)c1cc(F)cc(C(F)(F)F)c1] | Fc1ccc(C 1)c(c1)C1 NC(=O)c 2cc(cc(N C(=O)c3 cc(F)cc(c 3)C(F)(F) F)c12)-n1cccn1 | (400 MHz, DMSO-D6) 10.67 (s, 1 H), 9.29 (s, 1 H), 8.76 (d, 2.5 Hz, 1 H), 8.14 (d, 1.6 Hz, 1 H), 8.09 (d, 1.6 Hz, 1 H), 7.96 (d, 8.4 Hz, 1 H), 7.82 (d, 1.6 Hz, 1 H), 7.76 (d, 8.9 Hz, 1 H), 7.69 (s, 1 H), 7.33 (dd, 8.9, 5.2 Hz, 1 H), 7.10 (td, 8.5, 3.0 Hz, 1 H), 6.66-6.58 (m, 1 H), 6.03 (br s, 1 H). Ortho-proton of the B-ring is missing/submerged. | 533.3 | A | A |
| I-961 | 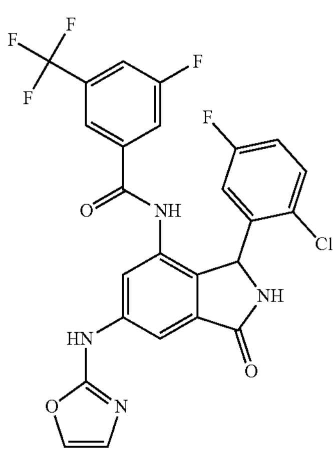 [SMILES: O=C(Nc1cc(Nc2ncco2)cc2c1C(c1cc(F)ccc1Cl)NC2=O)c1cc(F)cc(C(F)(F)F)c1] | Fc1ccc(C 1)c(c1)C1 NC(=O)c 2cc(Nc3n cco3)cc (NC(=O)c 3cc(F)cc (c3)C(F) (F)F)c12 | NMR (400 MHz, DMSOd6) 10.58 (s, 1H), 10.53 (s, 1H), 9.08 (Presence of Formate salt), 7.98 (s, 1H), 7.94 (d, 8.6 Hz, 1H), 7.76 (s, 1H), 7.69 (m, 2H including d, 1.01 Hz, 1H), 7.62 (s, 1H), 7.30 (dd, 8.9, 5.2 Hz, 1H), 7.08 (submerged td, 8.38, 3.04 Hz, 1H), 7.05 (submerged s, 1H), 6.60 (bs, 1H), 5.90 (bs, 1H). | 549.3 | A | A |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-962 | 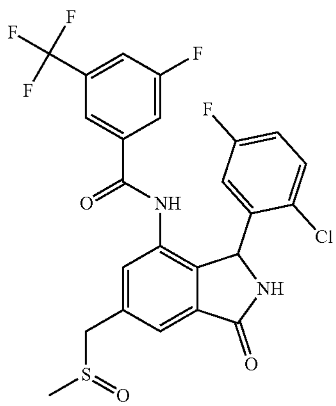 [SMILES: CS(=O)Cc1cc(NC(=O)c2cc(F)cc(C(F)(F)F)c2)c2c(c1)C(=O)NC2c1cc(F)ccc1Cl] | CS(=O)C c1cc2C(=O)NC(c2(NC(=O)c2cc(F)cc(c2)C(F)(F)F)c1)cc(F)ccc1Cl | NMR (400 MHz, Cd3CN) 8.75 (s, 1H), 7.67 (s, 1H), 7.65 (d, 8.5 Hz, 1H), 7.61-7.55 (m, 2H), 7.51 (s, 1H), 7.32 (s, 1H), 7.25 (dd, 8.9, 5.1 Hz, 1H), 6.97 (td, 8.4, 3.0 Hz, 1H), 6.65 (br, s, 1H), 6.11 (s, 1H), 4.21 (dd, 13.0, 1.2 Hz, 1H), 4.01 (dd, 13.1, 1.1 Hz, 1H), 2.49 (d, 3.6 Hz, 3H). | 543.2 | A | A |
| I-963 | 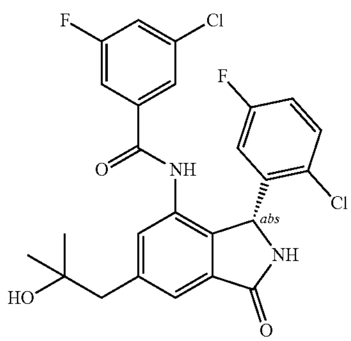 [SMILES: CC(C)(O)Cc1cc(NC(=O)c2cc(F)cc(Cl)c2)c2c(c1)C(=O)N[C@H]2c1cc(F)ccc1Cl] | CC(C)(O)Cc1cc2C(=O)N[C@H](c2c(NC(=O)c2cc(F)cc(Cl)c2)c1)cc(F)ccc1Cl | | 505 | C | |
| I-964 | 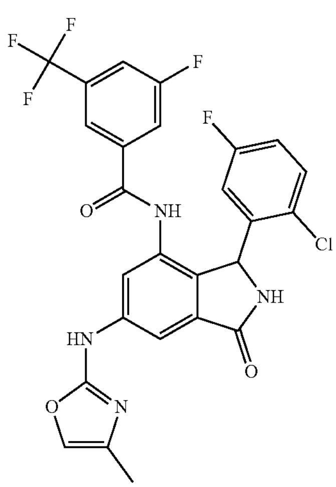 [SMILES: Cc1coc(Nc2cc(NC(=O)c3cc(F)cc(C(F)(F)F)c3)c3c(c2)C(=O)NC3c2cc(F)ccc2Cl)n1] | Cc1coc(Nc2cc3C(=O)NC(c3c(NC(=O)c3cc(F)cc(c3)C(F)(F)F)c2)c2cc(F)ccc2Cl)n1 | NMR (400 MHz, DMSOd6) 10.53 (s, 1H), 10.47 (s, 1H), 9.10 (br s, 1H), 8.02 (d, 1.8 Hz, 1H), 7.94 (d, 8.2 Hz, 1H), 7.71 (d, 9.6 Hz, 1H), 7.68 (s, 1H), 7.61 (s, 1H), 7.40 (d, 1.4 Hz, 1H), 7.30 (dd, 8.9, 5.2 Hz, 1H), 7.08 (td, 8.5, 3.0 Hz, 1H), 6.61 (br s, 1H), 5.87 (br s, 1H), 2.07 (d, 1.3 Hz, 3H). | 563.4 | A | A |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-965 | 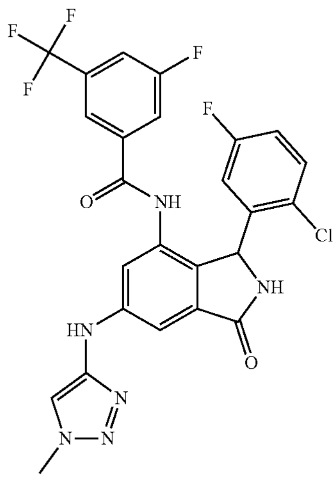 [SMILES: Cn1cc(Nc2cc(NC(=O)c3cc(F)cc(C(F)(F)F)c3)c3c(c2)C(=O)NC3c2cc(F)ccc2Cl)nn1] | Cn1cc(N c2cc3C(= O)NC(c3 c(NC(=O) c3cc(F)c c(c3)C(F) (F)F)c2)c 2cc(F)ccc 2Cl)nn1 | 1H-NMR (400 MHz, DMSO-d6) 10.42 (s, 1H), 9.01 (br. s, 1H), 8.98 (s, 1H), 7.93 (br. d, 8.4 Hz, 1H), 7.84 (s, 1H), 7.71 (br. d, 8.8 Hz, 1H), 7.62 (s, 1H), 7.39 (d, 2.0 Hz, 1H), 7.29 (dd, 8.9, 5.2 Hz, 1H), 7.24 (d, 1.8 Hz, 1H), 7.07 (app. td, 8.4, 3.1 Hz, 1H), 6.60 (br. s, 1H), 5.87 (br. s, 1H), 4.04 (s, 3H). | 563.4 | A | A |
| I-966 | 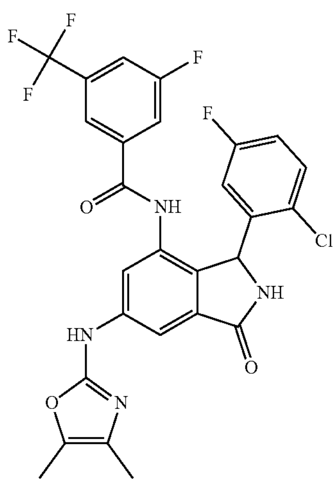 [SMILES: Cc1nc(Nc2cc(NC(=O)c3cc(F)cc(C(F)(F)F)c3)c3c(c2)C(=O)NC3c2cc(F)ccc2Cl)oc1C] | Cc1nc(N c2cc3C(= O)NC(c3 c(NC(=O) c3cc(F)c c(c3)C(F) (F)F)c2)c 2cc(F)ccc 2Cl)oc1C | NMR (400 MHz, DMSOd6) 10.52 (s, 1H), 10.33 (s, 1H), 9.08 (br s, 1H), 7.99 (d, 1.8 Hz, 1H), 7.93 (d, 8.2 Hz, 1H), 7.71 (d, 8.8 Hz, 1H), 7.66 (s, 1H), 7.61 (s, 1H), 7.29 (dd, 8.8, 5.2 Hz, 1H), 7.07 (td, 8.5, 3.1 Hz, 1H), 6.68 (br s, 1H), 5.88 (br s, 1H), 2.19 (d, 0.9 Hz, 3H), 2.00 (d, 0.9 Hz, 3H). | 577.4 | A | A |
| I-967 | 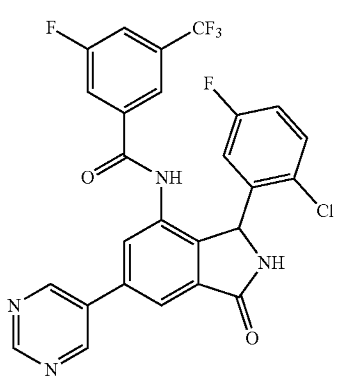 [SMILES: O=C(Nc1cc(-c2cncnc2)cc2c1C(c1cc(F)ccc1Cl)NC2=O)c1cc(F)cc(C(F)(F)F)c1] | Fc1ccc(C 1)c(c1)C1 NC(=O)c 2cc(cc(N C(=O)c3 cc(F)cc(c 3)C(F)(F) F)c12)- c1cncnc1 | | 545.4 | A | A |

TABLE 2-continued

Representative Compounds of the Invention with Bioactivity Data.

| Ex. No. | Structure | SMILES | $^1$H NMR | MS | ADP-Glo IC$_{50}$ | MCF 10A IC$_{50}$ |
|---|---|---|---|---|---|---|
| I-968 | 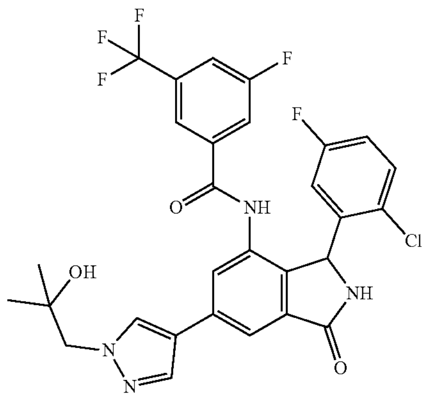 [SMILES: CC(C)(O)Cn1cc(-c2cc(NC(=O)c3cc(F)cc(C(F)(F)F)c3)c3c(c2)C(=O)NC3c2cc(F)ccc2Cl)cn1] | CC(C)(O)Cn1cc(cn1)-c1cc2C(=O)NC(c2c(NC(=O)c2cc(F)cc(c2)C(F)(F)F)c1)c1cc(F)ccc1Cl | | 605.6 | A | A |
| I-969 | 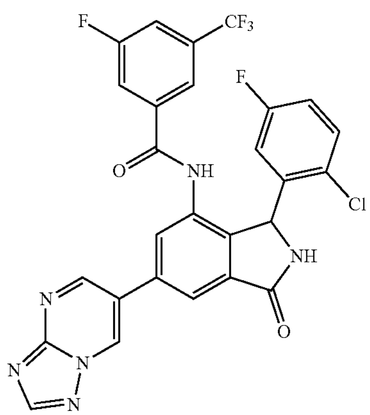 [SMILES: O=C(Nc1cc(-c2cnc3ncnn3c2)cc2c1C(c1cc(F)ccc1Cl)NC2=O)c1cc(F)cc(C(F)(F)F)c1] | Fc1ccc(Cl)c(c1)C1NC(=O)c2cc(cc(NC(=O)c3cc(F)cc(c3)C(F)(F)F)c12)-c1cnc2ncnn2c1 | | 585.4 | A | A |
| I-970 | 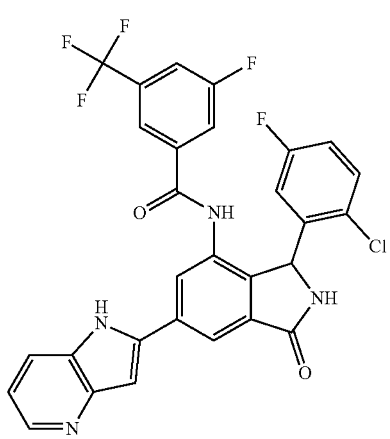 | Fc1ccc(Cl)c(c1)C1NC(=O)c2cc(cc(NC(=O)c3cc(F)cc(c3)C(F)(F)F)c12)-c1cc2nccccc2[nH]1 | | 582.27 | A | A |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-971 | 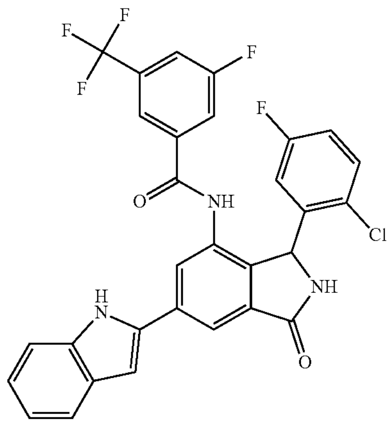 | Fc1ccc(C 1)c(c1)C1 NC(=O)c 2cc(cc(N C(=O)c3 cc(F)cc(c 3)C(F)(F) F)c12)- c1cc2ccc cc2[nH]1 | 1H NMR (400 MHz, DMSO-d6) 6.01 (br s, 1 H) 6.37-6.91 (m, 1 H) 6.99-7.15 (m, 4 H) 7.32 (dd, 8.84, 5.05 Hz, 1 H) 7.41 (dd, 8.08, 0.76 Hz, 1 H) 7.56 (d, 7.83 Hz, 1 H) 7.69-7.80 (m, 2 H) 7.92-8.02 (m, 2 H) 8.21 (s, 1 H) 9.20 (br s, 1 H) 10.60 (s, 1 H) 11.81 (s, 1 H) | 582.27 | A | A |
| I-972 | 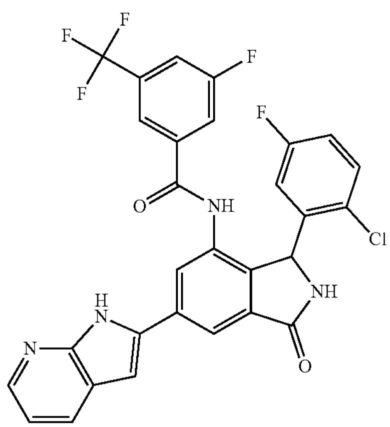 | Fc1ccc(C 1)c(c1)C1 NC(=O)c 2cc(cc(N C(=O)c3 cc(F)cc(c 3)C(F)(F) F)c12)- c1cc2ccc nc2[nH]1 | 1H NMR (400 MHz, DMSO-d6) 5.90-6.12 (m, 1 H) 6.86-6.98 (m, 1 H) 7.05-7.13 (m, 3 H) 7.32 (dd, 8.84, 5.05 Hz, 1 H) 7.72 (s, 1 H) 7.77 (br d, 9.35 Hz, 1 H) 7.91-7.99 (m, 2 H) 8.08 (br s, 1 H) 8.24 (dd, 4.55, 1.52 Hz, 1 H) 8.29 (br s, 1 H) 8.47 (s, 1 H) 9.10-9.32 (m, 1 H) 10.68 (br s, 1 H) 12.24-12.42 (m, 1 H) | 583.27 | A | A |
| I-974 | 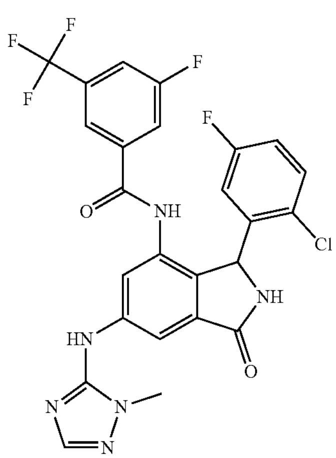 [SMILES: Cn1ncnc1Nc1cc(NC(=O)c2cc(F)cc(C(F)(F)F)c2)c2c(c1)C(=O)NC2c1cc(F)ccc1Cl] | Cn1ncnc 1Nc1cc2 C(=O)N C(c2c(N C(=O)c2 cc(F)cc(c 2)C(F)(F) F)c1)c1c c(F)ccc1 Cl | 1H NMR (400 MHz, DMSO-d6) 10.50 (br. s, 1H), 9.39 (s, 1H), 9.09 (br. s, 1H), 8.00 (d, 1.8 Hz, 1H), 7.94 (d, 8.5 Hz, 1H), 7.82 (d, 1.6 Hz, 1H), 7.72 (d, 9.1 Hz, 1H), 7.69 (s, 1H), 7.63 (s, 1H), 7.31 (dd, 8.9, 5.2 Hz, 1H), 7.08 (td, 8.5, 3.0 Hz, 1H), 6.61 (br. s, 1H), 5.91 (br. s, 1H), 3.37 (s, 3H) | 563.3 | A | A |

TABLE 2-continued

Representative Compounds of the Invention with Bioactivity Data.

| Ex. No. | Structure | SMILES | $^1$H NMR | MS | ADP-Glo IC$_{50}$ | MCF 10A IC$_{50}$ |
|---|---|---|---|---|---|---|
| I-975 | 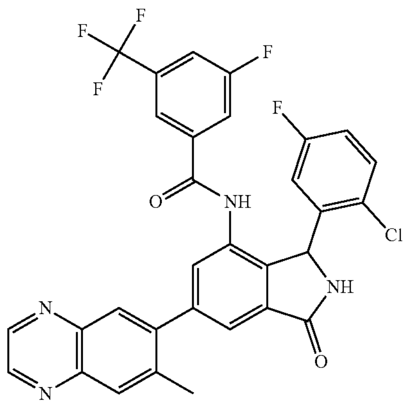 [SMILES: Cc1cc2nccnc2cc1-c1cc(NC(=O)c2cc(F)cc(C(F)(F)F)c2)c2c(c1)C(=O)NC2c1cc(F)ccc1Cl] | Cc1cc2ncnc2cc1-c1cc2C(=O)NC(c2c(NC(=O)c2cc(F)cc(c2)C(F)(F)F)c1)c1cc(F)ccc1Cl | | 609.3 | B | |
| I-976 | 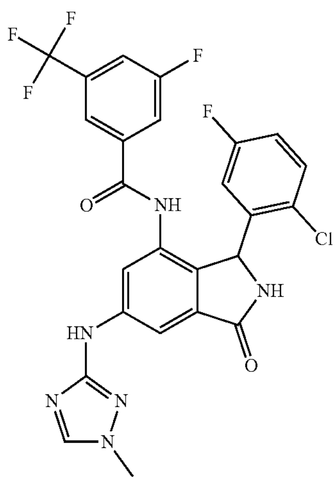 [SMILES: Cn1cnc(Nc2cc(NC(=O)c3cc(F)cc(C(F)(F)F)c3)c3c(c2)C(=O)NC3c2cc(F)ccc2Cl)n1] | Cn1cnc(Nc2cc3C(=O)NC(c3c(NC(=O)c3cc(F)cc(c3)C(F)(F)F)c2)c2cc(F)ccc2Cl)n1 | 1H NMR (400 MHz, DMSO-d6) 10.47 (s, 1H), 9.67 (s, 1H), 9.02 (br. s, 1H), 8.26 (s, 1H), 7.96 (d, 1.9 Hz, 1H), 7.93 (dt, 8.5 Hz, 1H), 7.71 (d, 8.7 Hz, 1H), 7.61 (s, 1H), 7.58 (d, 1.5 Hz, 1H), 7.28 (dd, 8.8, 5.2 Hz, 1H), 7.07 (td, 8.6, 3.0 Hz, 1H), 6.54 (br. s, 1H), 5.86 (br. s, 1H), 3.81 (s, 3H); | 563.3 | A | A |
| I-977 | 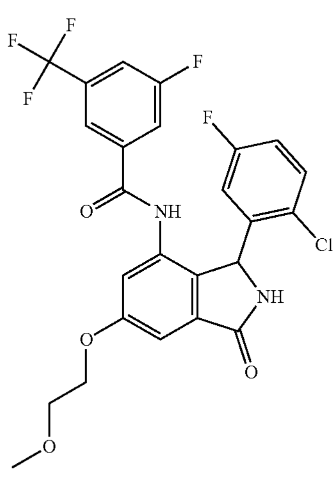 [SMILES: COCCOc1cc(NC(=O)c2cc(F)cc(C(F)(F)F)c2)c2c(c1)C(=O)NC2c1cc(F)ccc1Cl] | COCCOc1cc2C(=O)NC(c2c(NC(=O)c2cc(F)cc(c2)C(F)(F)F)c1)c1cc(F)ccc1Cl | (400 MHz, DMSO-d6) 10.50 (br s, 1H), 9.13 (s, 1H), 7.94 (d, 8.5 Hz, 1H), 7.71 (d, 8.7 Hz, 1H), 7.63 (s, 1H), 7.31 (dd, 8.9, 5.2 Hz, 1H), 7.25-7.16 (m, 1H), 7.08 (td, 8.9, 3.1 Hz, 2H), 5.92 (br s, 1H), 4.28-4.17 (m, 2H), 3.70 (t, 4.4 Hz, 2H), 3.33 (s, 3H) | 541.3 | B | |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-978 | 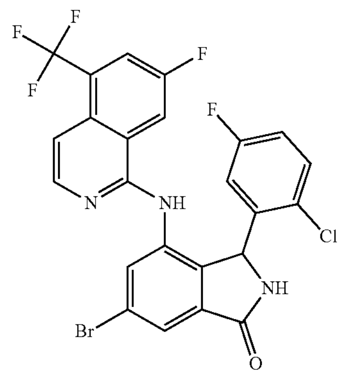 [SMILES: O=C1NC(c2cc(F)ccc2Cl)c2c(Nc3nccc4c(C(F)(F)F)cc(F)cc34)cc(Br)cc21] | Fc1ccc(C1)c(c1)C1NC(=O)c2cc(Br)cc(Nc3nccc4c(cc(F)cc34)C(F)(F)F)c12 | 1H NMR (400 MHz, DMSO-d6) 9.40 (s, 1H), 9.15 (s, 1H), 8.20-8.10 (m, 2H), 7.95 (d, 9.9 Hz, 1H), 7.70 (dd, 14.7, 1.7 Hz, 2H), 7.28 (s, 1H), 7.03 (s, 1H), 6.91-6.82 (m, 1H), 6.29 (s, 1H), 5.76 (s, 1H). | 568.15 | A | A |
| I-979 | 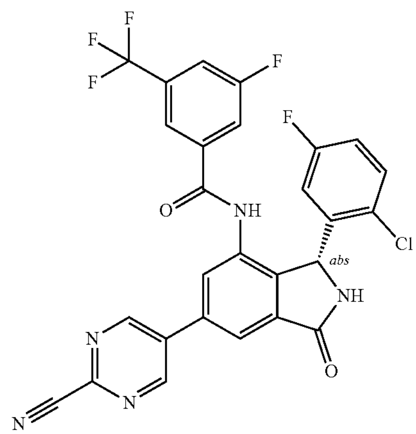 [SMILES: N#Cc1ncc(-c2cc(NC(=O)c3cc(F)cc(C(F)(F)F)c3)c3c(c2)C(=O)N[C@H]3c2cc(F)ccc2Cl)cn1] | Fc1ccc(C1)c(c1)[C@@H]1NC(=O)c2cc(cc(NC(=O)c3cc(F)cc(c3)C(F)(F)F)c12)-c1cnc(nc1)C#N | | 570.1 | B | |
| I-980 | 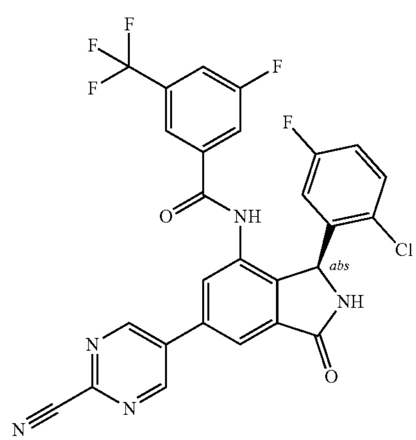 [SMILES: N#Cc1ncc(-c2cc(NC(=O)c3cc(F)cc(C(F)(F)F)c3)c3c(c2)C(=O)N[C@@H]3c2cc(F)ccc2Cl)cn1] | Fc1ccc(C1)c(c1)[C@H]1NC(=O)c2cc(cc(NC(=O)c3cc(F)cc(c3)C(F)(F)F)c12)-c1cnc(nc1)C#N | | 570.1 | A | A |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-981 | 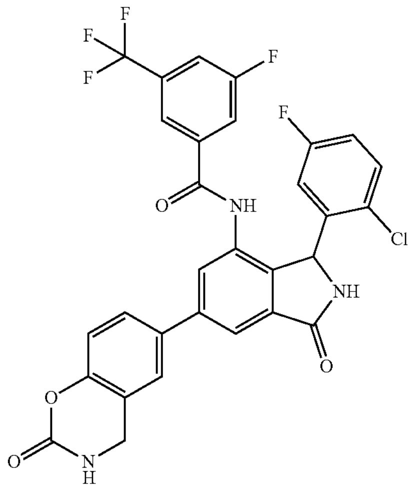 | Fc1ccc(C1)c(c1)C1NC(=O)c2cc(cc(NC(=O)c3cc(F)cc(c3)C(F)(F)F)c12)-c1ccc2OC(=O)NCc2c1 | 1H NMR (400 MHz, DMSO-d6) 4.49 (s, 2 H) 5.93-6.10 (m, 1 H) 7.05-7.17 (m, 2 H) 7.32 (dd, 8.84, 5.05 Hz, 1 H) 7.66-7.82 (m, 6 H) 7.89-7.98 (m, 2 H) 8.03 (s, 1 H) 9.19 (br s, 1 H) 10.57 (s, 1 H) | 614.3 | A | A |
| I-982 | 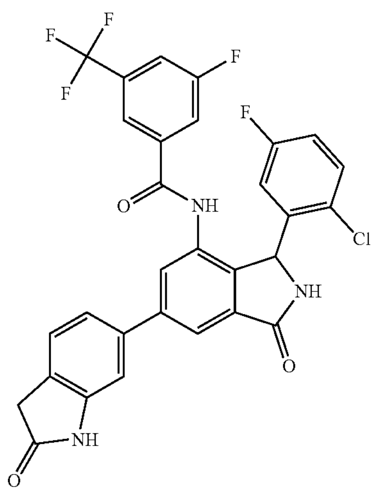 [SMILES: O=C1Cc2ccc(-c3cc(NC(=O)c4cc(F)cc(C(F)(F)F)c4)c4c(c3)C(=O)NC4c3cc(F)ccc3Cl)cc2N1] | Fc1ccc(C1)c(c1)C1NC(=O)c2cc(cc(NC(=O)c3cc(F)cc(c3)C(F)(F)F)c12)-c1ccc2CC(=O)Nc2c1 | | 598.2 | A | A |
| I-983 | 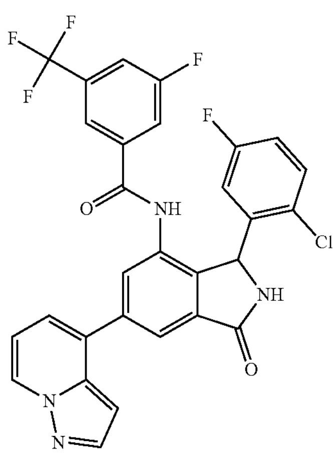 [SMILES: O=C(Nc1cc(-c2cccn3nccc23)cc2c1C(c1cc(F)ccc1Cl)NC2=O)c1cc(F)cc(C(F)(F)F)c1] | Fc1ccc(C1)c(c1)C1NC(=O)c2cc(cc(NC(=O)c3cc(F)cc(c3)C(F)(F)F)c12)-c1cccn2nccc12 | 1H NMR (400 MHz, DMSO-d6) 4.08 (q, 5.14 Hz, 1 H) 6.01-6.17 (m, 1 H) 6.83 (d, 1.52 Hz, 1 H) 7.04 (t, 6.95 Hz, 1 H) 7.11 (td, 8.46, 3.03 Hz, 1 H) 7.35 (dd, 8.84, 5.31 Hz, 1 H) 7.48 (dd, 6.82, 0.76 Hz, 1 H) 7.67 (s, 1 H) 7.75 (br d, 8.59 Hz, 1 H) 7.87-8.00 (m, 3 H) 8.12 (d, 2.27 Hz, 1 H) 8.76 (d, 7.07 Hz, 1 H) 9.26 (br s, 1 H) 10.60 (s, 1 H) | 583.2 | A | A |

TABLE 2-continued

Representative Compounds of the Invention with Bioactivity Data.

| Ex. No. | Structure | SMILES | $^1$H NMR | MS | ADP-Glo IC$_{50}$ | MCF 10A IC$_{50}$ |
|---|---|---|---|---|---|---|
| I-984 | 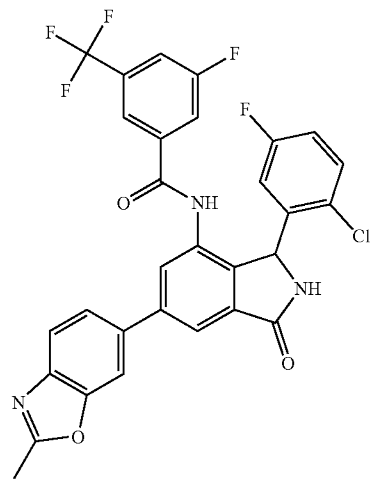 [SMILES: Cc1nc2ccc(-c3cc(NC(=O)c4cc(F)cc(C(F)(F)F)c4)c4c(c3)C(=O)NC4c3cc(F)ccc3Cl)cc2o1] | Cc1nc2cc c(cc2ol)- c1cc2C(= O)NC(c2 c(NC(=O) c2cc(F)c c(c2)C(F) (F)F)c1)c 1cc(F)ccc 1Cl | 1H NMR (400 MHz, DMSO-d6) 2.65 (s, 3 H) 5.84-6.18 (m, 1 H) 6.50-6.94 (m, 1 H) 7.10 (td, 8.34, 3.03 Hz, 1 H) 7.33 (dd, 8.84, 5.05 Hz, 1 H) 7.70 (s, 1 H) 7.73-7.78 (m, 3 H) 7.86 (s, 1 H) 7.95 (br d, 8.34 Hz, 1 H) 7.99 (s, 1 H) 8.11 (s, 1 H) 9.15-9.25 (m, 1 H) 10.59 (s, 1 H) | 598.2 | A | A |
| I-985 | 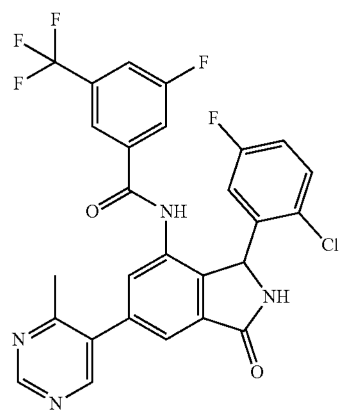 [SMILES: Cc1ncncc1-c1cc(NC(=O)c2cc(F)cc(C(F)(F)F)c2)c2c(c1)C(=O)NC2c1cc(F)ccc1Cl] | Cc1ncncc 1- c1cc2C(= O)NC(c2 c(NC(=O) c2cc(F)c c(c2)C(F) (F)F)c1)c 1cc(F)ccc 1Cl | | 559.4 | A | A |
| I-986 | 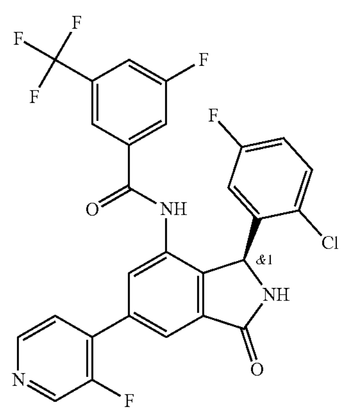 [SMILES: O=C(Nc1cc(-c2ccncc2F)cc2c1[C@@H](c1cc(F)ccc1Cl)NC2=O)c1cc(F)cc(C(F)(F)F)c1] | Fc1ccc(C 1)c(c1)[C @H]1NC (=O)c2cc (cc(NC(= O)c3cc(F) cc(c3)C (F)(F)F)c1 2)- c1ccncc1 F | | 562.1 | A | A |

TABLE 2-continued

Representative Compounds of the Invention with Bioactivity Data.

| Ex. No. | Structure | SMILES | $^1$H NMR | MS | ADP-Glo IC$_{50}$ | MCF 10A IC$_{50}$ |
|---|---|---|---|---|---|---|
| I-987 | 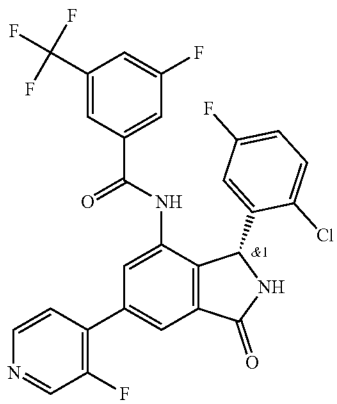 [SMILES: O=C(Nc1cc(-c2ccncc2F)cc2c1[C@H](c1cc(F)ccc1Cl)NC2=O)c1cc(F)cc(C(F)(F)F)c1] | Fc1ccc(C1)c(c1)[C@@H]1NC(=O)c2cc(cc(NC(=O)c3cc(F)cc(c3)C(F)(F)F)c12)-c1ccncc1F | | 562.15 | D | |
| I-988 | 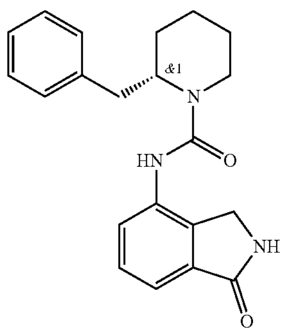 [SMILES: O=C1NCc2c(NC(=O)N3CCCC[C@H]3Cc3ccccc3)cccc21] | O=C(Nc1cccc2C(=O)NCc12)N1CCCC[C@H]1Cc1cccc1 | 1H NMR (400 MHz, DMSO-d6) 8.39 (d, 26.3 Hz, 2H), 7.37-7.31 (m, 3H), 7.27 (d, 6.2 Hz, 4H), 7.19 (tt, 5.4, 2.4 Hz, 1H), 4.53 (p, 4.1 Hz, 1H), 4.26-3.81 (m, 3H), 3.09 (td, 13.3, 2.7 Hz, 1H), 2.92 (qd, 13.3, 7.7 Hz, 2H), 1.86-1.61 (m, 2H), 1.60 (s, 2H), 1.57-1.51 (m, 3H), 1.40 (qt, 12.5, 3.9 Hz, 1H). | 350.15 | E | |
| I-989 | 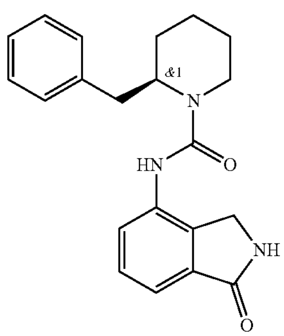 [SMILES: O=C1NCc2c(NC(=O)N3CCCC[C@@H]3Cc3ccccc3)cccc21] | O=C(Nc1cccc2C(=O)NCc12)N1CCCC[C@@H]1Cc1cccc1 | 1H NMR (400 MHz, DMSO-d6) 8.39 (d, 26.3 Hz, 2H), 7.37-7.31 (m, 3H), 7.27 (d, 6.2 Hz, 4H), 7.19 (tt, 5.4, 2.4 Hz, 1H), 4.53 (p, 4.1 Hz, 1H), 4.26-3.81 (m, 3H), 3.09 (td, 13.3, 2.7 Hz, 1H), 2.92 (qd, 13.3, 7.7 Hz, 2H), 1.86-1.61 (m, 2H), 1.60 (s, 2H), 1.57-1.51 (m, 3H), 1.40 (qt, 12.5, 3.9 Hz, 1H). | 350.2 | E | |
| I-990 | 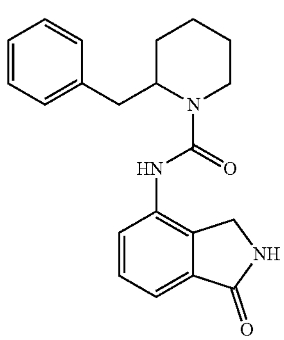 [SMILES: O=C1NCc2c(NC(=O)N3CCCCC3Cc3ccccc3)cccc21] | O=C(Nc1cccc2C(=O)NCc12)N1CCCCC1Cc1cccc1 | 1H NMR (400 MHz, DMSO-d6) 8.39 (d, 26.3 Hz, 2H), 7.37-7.31 (m, 3H), 7.27 (d, 6.2 Hz, 4H), 7.19 (tt, 5.4, 2.4 Hz, 1H), 4.53 (p, 4.1 Hz, 1H), 4.26-3.81 (m, 3H), 3.09 (td, 13.3, 2.7 Hz, 1H), 2.92 (qd, 13.3, 7.7 Hz, 2H), 1.86-1.61 (m, 2H), 1.60 (s, 2H), 1.57-1.51 (m, 3H), 1.40 (qt, 12.5, 3.9 Hz, 1H). | 350.15 | E | |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-991 | 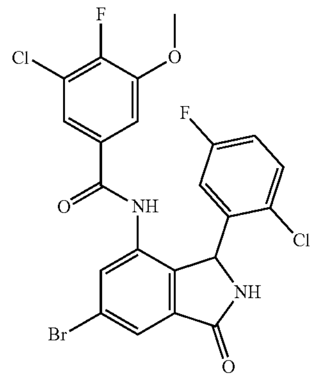 [SMILES: COc1cc(C(=O)Nc2cc(Br)cc3c2C(c2cc(F)ccc2Cl)NC3=O)cc(Cl)c1F] | COc1cc(cc(Cl)c1F)C(=O)Nc1cc(Br)cc2C(=O)NC(c12)c1cc(F)ccc1Cl | 1H NMR (400 MHz, DMSO-d6) 10.34 (s, 1H), 9.29 (s, 1H), 7.81 (d, 1.7 Hz, 1H), 7.74 (d, 1.8 Hz, 1H), 7.37 (td, 9.2, 5.9 Hz, 2H), 7.24 (dd, 6.1, 2.0 Hz, 1H), 7.15 (ddd, 8.9, 7.9, 3.1 Hz, 1H), 6.66 (s, 1H), 5.98 (s, 1H), 3.90 (s, 3H). | 541 | B | |
| I-992 | 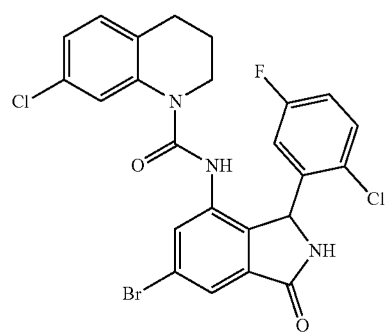 [SMILES: O=C1NC(c2cc(F)ccc2Cl)c2c(NC(=O)N3CCCc4ccc(Cl)cc43)cc(Br)cc21] | Fc1ccc(C1)c(c1)C1NC(=O)c2cc(Br)cc(NC(=O)N3CCCc4ccc(Cl)cc34)c12 | 1H NMR (400 MHz, DMSO-d6) 11.59 (s, 1H), 10.32 (s, 1H), 8.11 (s, 1H), 8.03 (d, 9.1 Hz, 1H), 7.95 (d, 8.4 Hz, 1H), 7.75 (dd, 7.5, 1.8 Hz, 1H), 7.67 (dd, 7.8, 1.5 Hz, 1H), 7.50-7.39 (m, 3H), 7.16 (d, 7.3 Hz, 1H), 7.00 (t, 7.8 Hz, 1H), 6.75 (d, 2.0 Hz, 1H). | 550 | D | |
| I-993 | 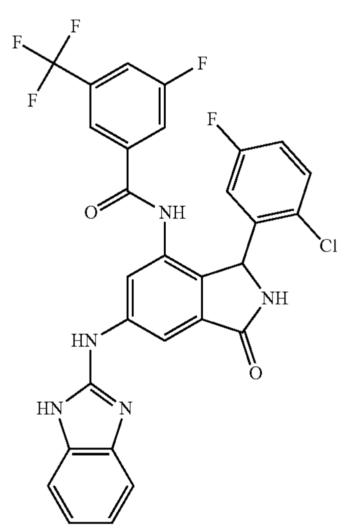 [SMILES: O=C(Nc1cc(Nc2nc3ccccc3[nH]2)cc2c1C(c1cc(F)ccc1Cl)NC2=O)c1cc(F)cc(C(F)(F)F)c1] | Fc1ccc(C1)c(c1)C1NC(=O)c2cc(Nc3nc4ccccc4[nH]3)cc(NC(=O)c3cc(F)cc(c3)C(F)(F)F)c12 | 1H-NMR (400 MHz, DMSO-d6)-11.36 (br. s, 1H), 10.55 (s, 1H), 10.10 (br. s, 1H), 9.09 (br. s, 1H), 8.19 (d, 1.8 Hz, 1H), 7.97-7.95 (m, 1H), 7.95-7.92 (m, 1H), 7.73 (br. d, 8.9 Hz, 1H), 7.64 (s, 1H), 7.40 (br. s, 1H), 7.32 (d, 5.2 Hz, 1H), 7.30 (d, 5.2 Hz, 1H), 7.09 (app. td, 8.5, 3.1 Hz, 1H), 7.04-7.00 (m, 2H), 6.61 (br. s, 1H), 5.91 (br. s, 1H). | 598.4 | A | B |

TABLE 2-continued

Representative Compounds of the Invention with Bioactivity Data.

| Ex. No. | Structure | SMILES | $^1$H NMR | MS | ADP-Glo IC$_{50}$ | MCF 10A IC$_{50}$ |
|---|---|---|---|---|---|---|
| I-994 | 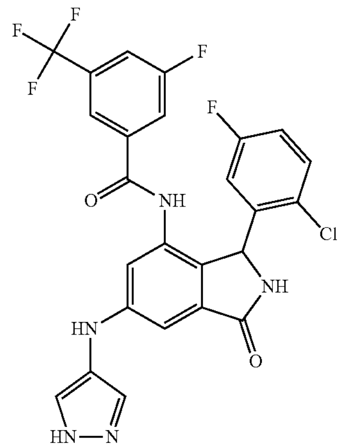 [SMILES: O=C(Nc1cc(Nc2cn[nH]c2)cc2c1C(c1cc(F)ccc1Cl)NC2=O)c1cc(F)cc(C(F)(F)F)c1] | Fc1ccc(C1)c(c1)C1NC(=O)c2cc(Nc3cn[nH]c3)cc(NC(=O)c3cc(F)cc(c3)C(F)(F)F)c12 | 1H-NMR (400 MHz, DMSO-d6) 12.73 (br. s, 1H), 10.30 (br. s, 1H), 8.95 (s, 1H), 7.94-7.89 (m, 2H), 7.69 (br. d, 8.7 Hz, 1H), 7.73-7.52 (m, 2H), 7.59 (s, 1H), 7.28 (dd, 8.9, 5.2 Hz, 1H), 7.06 (app. td, 8.4, 3.1 Hz, 1H), 6.95 (d, 2.1 Hz, 1H), 6.84 (d, 2.0 Hz, 1H), 6.58 (br. s, 1H), 5.85 (br. s, 1H). | 548.3 | A | A |
| I-995 | 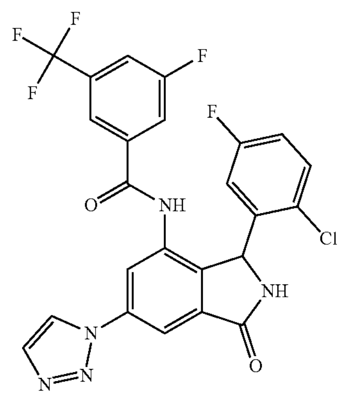 [SMILES: O=C(Nc1cc(-n2ccnn2)cc2c1C(c1cc(F)ccc1Cl)NC2=O)c1cc(F)cc(C(F)(F)F)c1] | Fc1ccc(C1)c(c1)C1NC(=O)c2cc(cc(NC(=O)c3cc(F)cc(c3)C(F)(F)F)c12)-n1ccnn1 | (400 MHz, DMSO-D6) 10.77 (br s, 1 H), 9.37 (s, 1 H), 8.26 (d, 1.5 Hz, 1 H), 8.23 (s, 2 H), 8.20 (d, 1.7 Hz, 1 H), 7.96 (d, 8.4 Hz, 1 H), 7.77 (d, 8.9 Hz, 1 H), 7.69 (s, 1 H), 7.34 (dd, 8.9, 5.2 Hz, 1 H), 7.10 (td, 8.5, 3.0 Hz, 1 H), 6.71 (br s, 1 H), 6.08 (br s, 1 H). | 532.4 | A | A |
| I-996 | 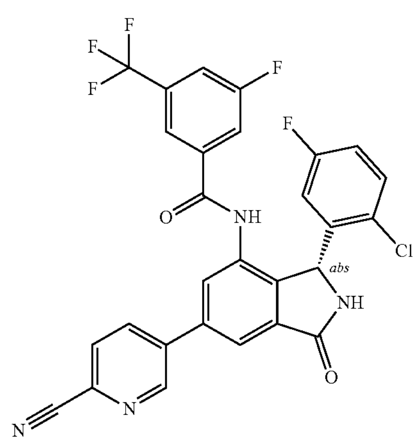 [SMILES: N#Cc1ccc(-c2cc(NC(=O)c3cc(F)cc(C(F)(F)F)c3)c3c(c2)C(=O)N[C@H]3c2cc(F)ccc2Cl)cn1] | Fc1ccc(C1)c(c1)[C@@H]1NC(=O)c2cc(cc(NC(=O)c3cc(F)cc(c3)C(F)(F)F)c12)-c1ccc(nc1)C#N | | 569.3 | C | |

TABLE 2-continued

Representative Compounds of the Invention with Bioactivity Data.

| Ex. No. | Structure | SMILES | $^1$H NMR | MS | ADP-Glo IC$_{50}$ | MCF 10A IC$_{50}$ |
|---|---|---|---|---|---|---|
| I-997 | 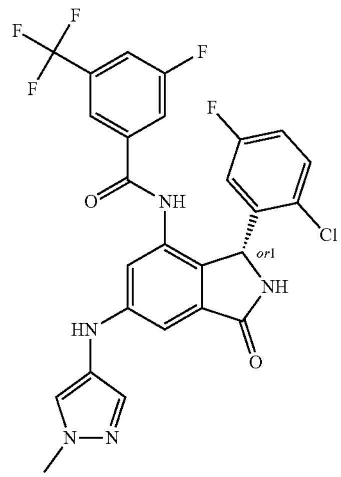 [SMILES: Cn1cc(Nc2cc(NC(=O)c3cc(F)cc(C(F)(F)F)c3)c3c(c2)C(=O)N[C@H]3c2cc(F)ccc2Cl)cn1] | Cn1cc(Nc2cc3C(=O)N[C@H](c3c(NC(=O)c3cc(F)cc(c3)C(F)(F)F)c2)c2cc(F)ccc2Cl)cn1 | 1H NMR (400 MHz, DMSO-d6) 11.02 (br s, 1H), 10.44 (s, 1H), 9.19 (br s, 1H), 9.00 (s, 1H), 7.92 (d, 8.5 Hz, 1H), 7.75 (s, 1H), 7.71 (d, 9.2 Hz, 1H), 7.63 (s, 1H), 7.58 (s, 1H), 7.29 (dd, 8.8, 5.2 Hz, 1H), 7.07 (td, 8.4, 2.9 Hz, 1H), 6.81 (s, 1H), 6.68 (s, 1H), 5.87 (br s, 1H). | 562.4 | A | A |
| I-998 | 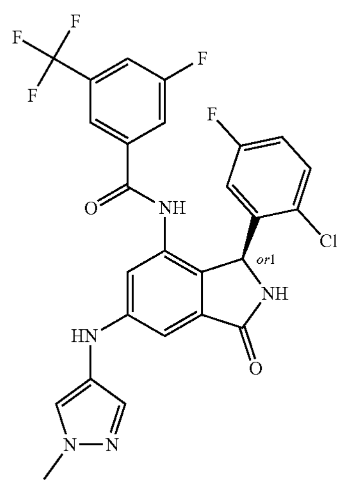 [SMILES: Cn1cc(Nc2cc(NC(=O)c3cc(F)cc(C(F)(F)F)c3)c3c(c2)C(=O)N[C@@H]3c2cc(F)ccc2Cl)cn1] | Cn1cc(Nc2cc3C(=O)N[C@@H](c3c(NC(=O)c3cc(F)cc(c3)C(F)(F)F)c2)c2cc(F)ccc2Cl)cn1 | 1H NMR (400 MHz, DMSOD6) 10.33 (br s, 1H), 8.95 (br s, 1H), 8.54 (s, residual salt), 7.94 (submerged s, 1H), 7.91 (submerged d, 8.03 Hz, 1H), 7.73 (s, 1H), 7.69 (d, 9.3 Hz, 1H), 7.61 (s, 1H), 7.38 (s, 1H), 7.29 (dd, 8.9, 5.2 Hz, 1H), 7.06 (td, 8.4, 3.2 Hz, 1H), 6.94 (br s, 1H), 6.86 (br s, 1H), 6.57 (br s, 1H), 5.85 (br s, 1H), 3.83 (s, 3H). | 562.4 | C | |
| I-999 | 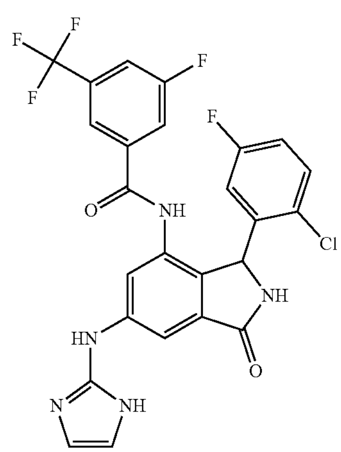 [SMILES: O=C(Nc1cc(Nc2ncc[nH]2)cc2c1C(c1cc(F)ccc1Cl)NC2=O)c1cc(F)cc(C(F)(F)F)c1] | Fc1ccc(C1)c(c1)C1NC(=O)c2cc(Nc3ncc[nH]3)cc(NC(=O)c3cc(F)cc(c3)C(F)(F)F)c12 | NMR (400 MHz, DMSOD6) 11.02 (br s, 1H), 10.44 (s, 1H), 9.19 (br s, 1H), 9.00 (s, 1H), 7.92 (d, 8.5 Hz, 1H), 7.75 (s, 1H), 7.71 (d, 9.2 Hz, 1H), 7.63 (s, 1H), 7.58 (s, 1H), 7.29 (dd, 8.8, 5.2 Hz, 1H), 7.07 (td, 8.4, 2.9 Hz, 1H), 6.81 (s, 1H), 6.68 (s, 1H), 5.87 (br s, 1H). | 548.4 | A | B |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-1000 | 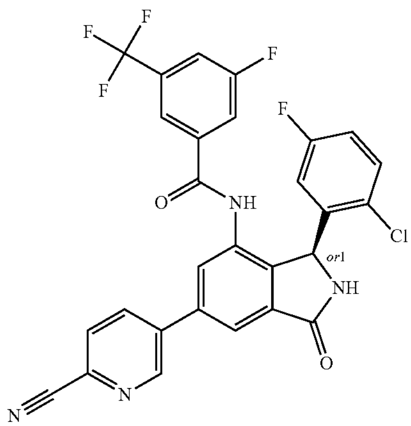 [SMILES: N#Cc1ccc(-c2cc(NC(=O)c3cc(F)cc(C(F)(F)F)c3)c3c(c2)C(=O)N[C@@H]3c2cc(F)ccc2Cl)cn1] | Fc1ccc(C1)c(c1)[C@H]1NC(=O)c2cc(cc(NC(=O)c3cc(F)cc(c3)C(F)(F)F)c12)-c1ccc(nc1)C#N | | 569.3 | A | A |
| I-1001 | 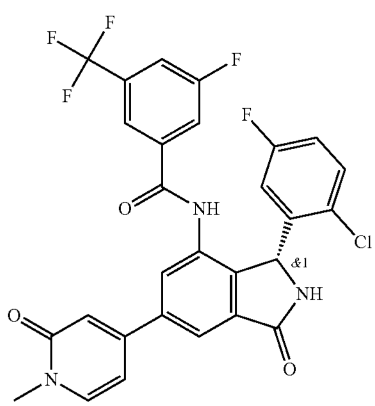 [SMILES: Cn1ccc(-c2cc(NC(=O)c3cc(F)cc(C(F)(F)F)c3)c3c(c2)C(=O)N[C@H]3c2cc(F)ccc2Cl)cc1=O] | Cn1ccc(cc1=O)-c1cc2C(=O)N[C@H](c2c(NC(=O)c2cc(F)cc(c2)C(F)(F)F)c1)c1cc(F)ccc1Cl | | 574.1 | D | |
| I-1002 | 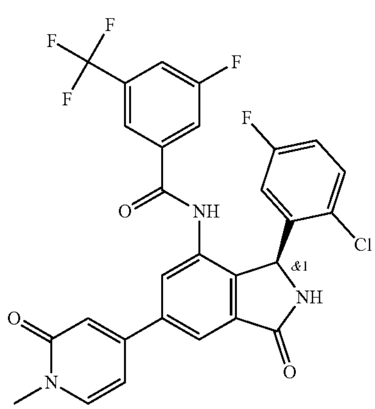 [SMILES: Cn1ccc(-c2cc(NC(=O)c3cc(F)cc(C(F)(F)F)c3)c3c(c2)C(=O)N[C@@H]3c2cc(F)ccc2Cl)cc1=O] | Cn1ccc(cc1=O)-c1cc2C(=O)N[C@@H](c2c(NC(=O)c2cc(F)cc(c2)C(F)(F)F)c1)c1cc(F)ccc1Cl | | 574.15 | A | A |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-1003 | 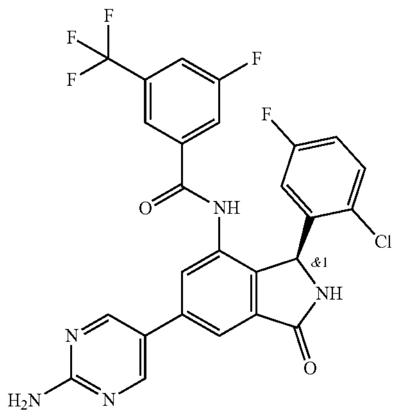 [SMILES: Nc1ncc(-c2cc(NC(=O)c3cc(F)cc(C(F)(F)F)c3)c3c(c2)C(=O)N[C@@H]3c2cc(F)ccc2Cl)cn1] | Nc1ncc(cn1)-c1cc2C(=O)N[C@@H](c2c(NC(=O)c2cc(F)cc(c2)C(F)(F)F)c1)c1cc(F)ccc1Cl | | 560.15 | A | A |
| I-1004 | 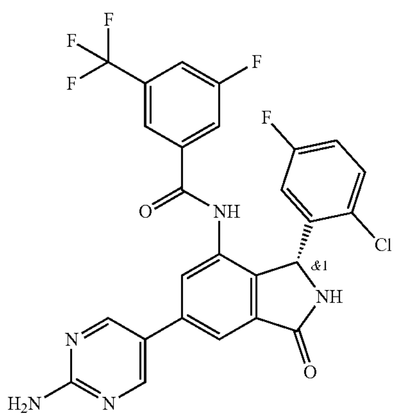 | Nc1ncc(cn1)-c1cc2C(=O)N[C@H](c2c(NC(=O)c2cc(F)cc(c2)C(F)(F)F)c1)c1cc(F)ccc1Cl | | 560.15 | D | |
| I-1005 | 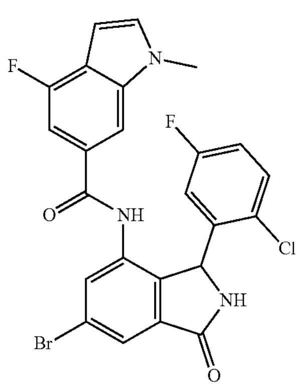 [SMILES: Cn1ccc2c(F)cc(C(=O)Nc3cc(Br)cc4c3C(c3cc(F)ccc3Cl)NC4=O)cc21] | Cn1ccc2c(F)cc(cc12)C(=O)Nc1cc(Br)cc2C(=O)NC(c12)c1cc(F)ccc1Cl | 1H NMR (400 MHz, DMSO-d6) 10.19 (s, 1H), 9.27 (s, 1H), 7.79 (dt, 4.5, 2.1 Hz, 2H), 7.59 (d, 2.9 Hz, 2H), 7.34 (dd, 8.9, 5.1 Hz, 1H), 7.10 (td, 8.4, 3.1 Hz, 1H), 7.02 (d, 11.4 Hz, 1H), 6.78-6.56 (s, 2H), , 6.08 (s, 1H), 3.85 (s, 3H). | 529.9 | D | |

TABLE 2-continued

Representative Compounds of the Invention with Bioactivity Data.

| Ex. No. | Structure | SMILES | $^1$H NMR | MS | ADP-Glo IC$_{50}$ | MCF 10A IC$_{50}$ |
|---|---|---|---|---|---|---|
| I-1006 | 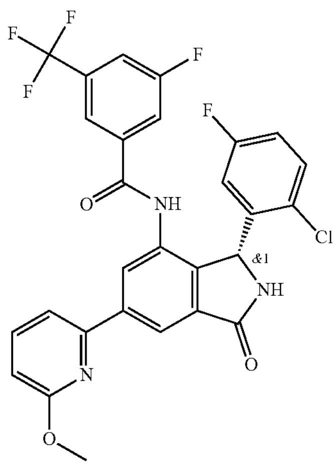 [SMILES: COc1cccc(-c2cc(NC(=O)c3cc(F)cc(C(F)(F)F)c3)c3c(c2)C(=O)N[C@H]3c2cc(F)ccc2Cl)n1] | COc1ccc c(n1)-c1cc2C(=O)N[C@H](c2c(NC(=O)c2cc(F)cc(c2)C(F)(F)F)c1)c1cc(F)ccc1Cl | | 574.05 | A | A |
| I-1007 | 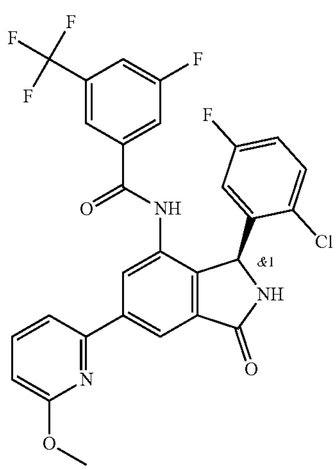 [SMILES: COc1cccc(-c2cc(NC(=O)c3cc(F)cc(C(F)(F)F)c3)c3c(c2)C(=O)N[C@@H]3c2cc(F)ccc2Cl)n1] | COc1ccc c(n1)-c1cc2C(=O)N[C@@H](c2c(NC(=O)c2cc(F)cc(c2)C(F)(F)F)c1)c1cc(F)ccc1Cl | | 574.05 | D | |
| I-1008 | 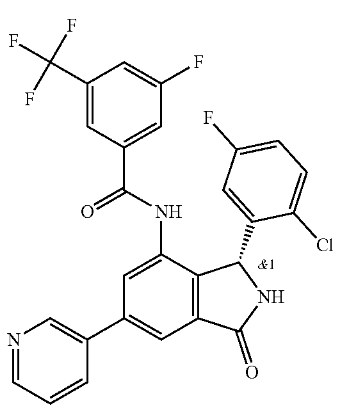 [SMILES: O=C(Nc1cc(-c2cccnc2)cc2c1[C@H](c1cc(F)ccc1Cl)NC2=O)c1cc(F)cc(C(F)(F)F)c1] | Fc1ccc(C1)c(c1)[C@@H]1NC(=O)c2cc(cc(NC(=O)c3cc(F)cc(c3)C(F)(F)F)c12)-c1cccnc1 | | 544.1 | D | |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-1009 | 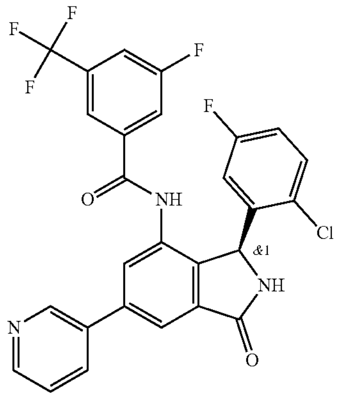 [SMILES: O=C(Nc1cc(-c2cccnc2)cc2c1[C@@H](c1cc(F)ccc1Cl)NC2=O)c1cc(F)cc(C(F)(F)F)c1] | Fc1ccc(C1)c(c1)[C@H]1NC(=O)c2cc(cc(NC(=O)c3cc(F)cc(c3)C(F)(F)F)c12)-c1cccnc1 | | 544.1 | A | A |
| I-1010 | 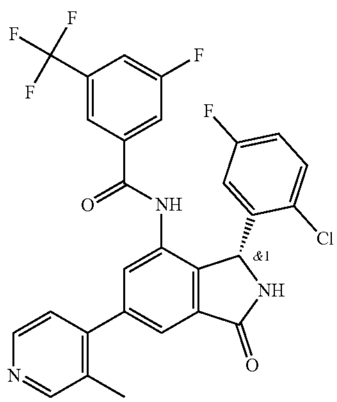 [SMILES: Cc1cnccc1-c1cc(NC(=O)c2cc(F)cc(C(F)(F)F)c2)c2c(c1)C(=O)N[C@H]2c1cc(F)ccc1Cl] | Cc1cnccc1-c1cc2C(=O)N[C@H](c2c(NC(=O)c2cc(F)cc(c2)C(F)(F)F)c1)c1cc(F)ccc1Cl | | 558.15 | A | A |
| I-1011 | 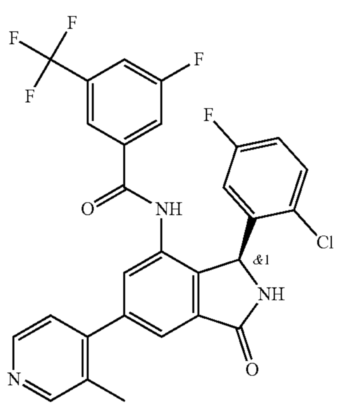 [SMILES: Cc1cnccc1-c1cc(NC(=O)c2cc(F)cc(C(F)(F)F)c2)c2c(c1)C(=O)N[C@@H]2c1cc(F)ccc1Cl] | Cc1cnccc1-c1cc2C(=O)N[C@@H](c2c(NC(=O)c2cc(F)cc(c2)C(F)(F)F)c1)c1cc(F)ccc1Cl | | 558.15 | D | |

TABLE 2-continued

Representative Compounds of the Invention with Bioactivity Data.

| Ex. No. | Structure | SMILES | $^1$H NMR | MS | ADP-Glo IC$_{50}$ | MCF 10A IC$_{50}$ |
|---|---|---|---|---|---|---|
| I-1012 | 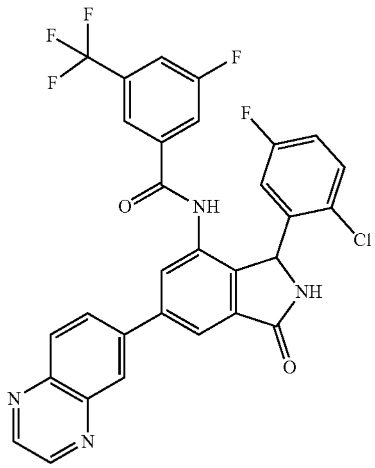 [SMILES: O=C(Nc1cc(-c2ccc3nccnc3c2)cc2c1C(c1cc(F)ccc1Cl)NC2=O)c1cc(F)cc(C(F)(F)F)c1] | Fc1ccc(C1)c(c1)C1NC(=O)c2cc(cc(NC(=O)c3cc(F)cc(c3)C(F)(F)F)c12)-c1ccc2nccnc2c1 | | 595.4 | A | A |
| I-1013 | 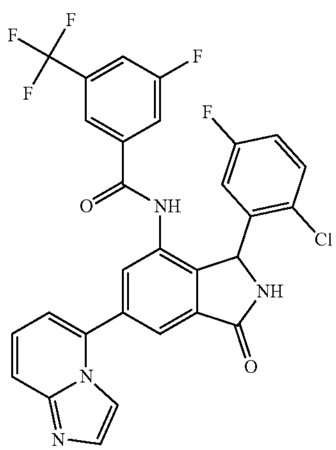 [SMILES: O=C(Nc1cc(-c2cccc3nccn23)cc2c1C(c1cc(F)ccc1Cl)NC2=O)c1cc(F)cc(C(F)(F)F)c1] | Fc1ccc(C1)c(c1)C1NC(=O)c2cc(cc(NC(=O)c3cc(F)cc(c3)C(F)(F)F)c12)-c1cccc2nccn12 | 1H NMR (400 MHz, DMSO-d6) 5.94-6.19 (m, 1 H) 6.96-7.17 (m, 2 H) 7.30-7.43 (m, 2 H) 7.62-7.82 (m, 5 H) 7.85-8.02 (m, 4 H) 8.68 (br d, 6.57 Hz, 1 H) 9.16-9.40 (m, 1 H) 10.68 (br s, 1 H) | 583.27 | A | A |
| I-1014 | 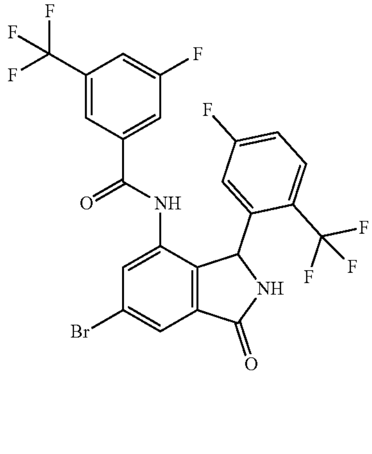 [SMILES: O=C(Nc1cc(Br)cc2c1C(c1cc(F)ccc1C(F)(F)F)NC2=O)c1cc(F)cc(C(F)(F)F)c1] | Fc1ccc(c(c1)C1NC(=O)c2cc(Br)cc(NC(=O)c3cc(F)cc(c3)C(F)(F)F)c12)C(F)(F)F | 1H NMR (400 MHz,Chloroform-d) 8.63 (d, 1.7 Hz, 1H), 7.98 (d, 1.6 Hz, 1H), 7.85 (dd, 8.9, 5.1 Hz, 1H), 7.50 (dd, 13.0, 8.2 Hz, 2H), 7.26 (d, 22.8 Hz, 2H), 7.14 (s, 1H), 6.71 (dd, 8.8, 2.6 Hz, 1H), 6.58 (s, 1H), 6.05 (s, 1H). | 581.05 | A | A |

TABLE 2-continued

Representative Compounds of the Invention with Bioactivity Data.

| Ex. No. | Structure | SMILES | $^1$H NMR | MS | ADP-Glo IC$_{50}$ | MCF 10A IC$_{50}$ |
|---|---|---|---|---|---|---|
| I-1015 | 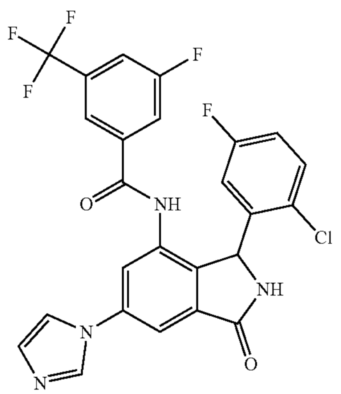 [SMILES: O=C(Nc1cc(-n2ccnc2)cc2c1C(c1cc(F)ccc1Cl)NC2=O)c1cc(F)cc(C(F)(F)F)c1] | Fc1ccc(C1)c(c1)C1NC(=O)c2cc(cc(NC(=O)c3cc(F)cc(c3)C(F)(F)F)c12)-n1ccnc1 | (400 MHz, DMSO-D6) 10.71 (br s, 1 H), 9.31 (s, 1 H), 8.45 (s, 1 H), 8.03-7.90 (m, 3 H), 7.84 (s, 1 H), 7.76 (d, 8.8 Hz, 1 H), 7.69 (s, 1 H), 7.33 (dd, 8.9, 5.1 Hz, 1 H), 7.16 (s, 1 H), 7.10 (td, 8.4, 2.9 Hz, 1 H), 6.67 (br s, 1 H), 6.02 (br s, 1 H). | 531.4 | A | A |
| I-1016 | 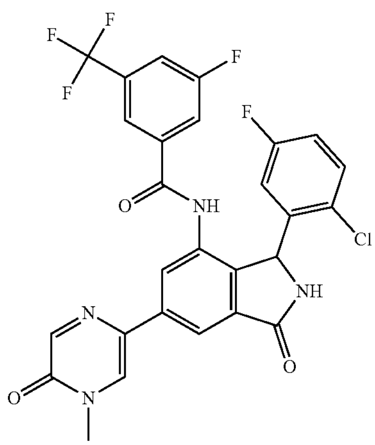 [SMILES: Cn1cc(-c2cc(NC(=O)c3cc(F)cc(C(F)(F)F)c3)c3c(c2)C(=O)NC3c2cc(F)ccc2Cl)ncc1=O] | Cn1cc(ncc1=O)-c1cc2C(=O)NC(c2c(NC(=O)c2cc(F)cc(c2)C(F)(F)F)c1)c1cc(F)ccc1Cl | NMR (400 MHz, DMSO) 10.59 (s, 1H), 9.19 (s, 1H), 8.67 (s, 1H), 8.16 (s, 1H), 8.14 (s, 1H), 8.06 (s, 1H), 7.95 (d, 8.3 Hz, 1H), 7.77 (d, 8.5 Hz, 1H), 7.70 (s, 1H), 7.32 (dd, 8.9, 5.1 Hz, 1H), 7.09 (td, 8.6, 2.9 Hz, 1H), 6.01 (s, 1H), 3.55 (s, 3H) | 573 | A | A |
| I-1017 | 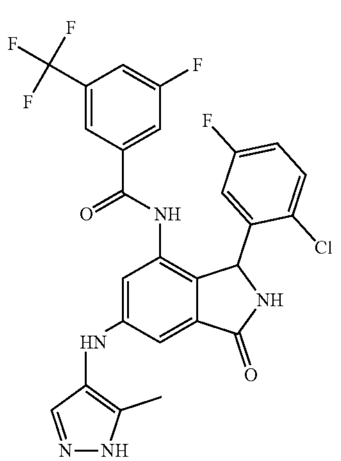 [SMILES: Cc1[nH]ncc1Nc1cc(NC(=O)c2cc(F)cc(C(F)(F)F)c2)c2c(c1)C(=O)NC2c1cc(F)ccc1Cl] | Cc1[nH]ncc1Nc1cc2C(=O)NC(c2c(NC(=O)c2cc(F)cc(c2)C(F)(F)F)c1)c1cc(F)ccc1Cl | NMR (400 MHz, DMSO-d6) 10.27 (s, 1H), 8.94 (s, 1H), 7.91 (d, 8.4 Hz, 1H), 7.68 (d, 8.8 Hz, 1H), 7.58 (d, 5.8 Hz, 2H), 7.32-7.24 (m, 1H), 7.06 (td, 8.4, 3.2 Hz, 1H), 6.81 (d, 1.9 Hz, 1H), 6.70 (s, 1H), 5.84 (s, 1H), 2.08 (s, 3H). | 562.3 | A | A |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-1018 | 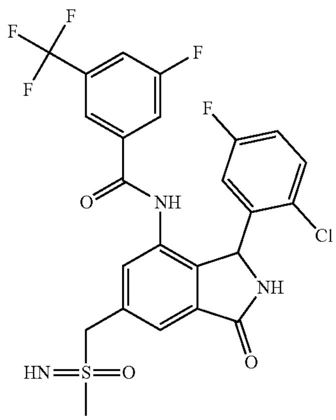 [SMILES: CS(=N)(=O)Cc1cc(NC(=O)c2cc(F)cc(C(F)(F)F)c2)c2c(c1)C(=O)NC2c1cc(F)ccc1Cl] | CS(=N)(=O)Cc1cc2C(=O)NC(c2c(NC(=O)c2cc(F)cc(c2)C(F)(F)F)c1)c1cc(F)ccc1Cl | NMR (400 MHz, DMSO-d6) 10.60 (s, 1H), 9.19 (br. s, 1H), 7.94 (d, 8.5 Hz, 1H), 7.81 (d, 0.5 Hz, 1H), 7.73 (d, 9.1 Hz, 1H), 7.64 (d, 3.3 Hz, 1H), 7.54 (d, 2.1 Hz, 1H), 7.32 (dd, 8.9, 5.2 Hz, 1H), 7.14-7.06 (m, 1H), 6.65 (br. s, 1H), 5.98 (br. s, 1H), 4.66-4.47 (m, 2H), 3.77 (d, 4.4 Hz, 1H), 2.84 (s, 3H). | 558.2 | A | A |
| I-1019 | 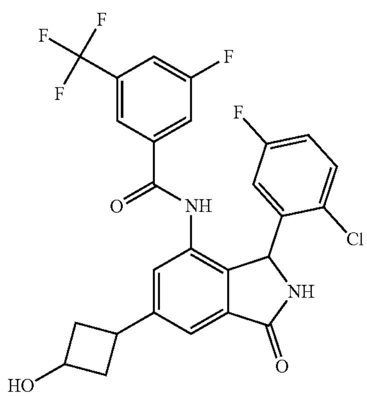 [SMILES: O=C(Nc1cc(C2CC(O)C2)cc2c1C(c1cc(F)ccc1Cl)NC2=O)c1cc(F)cc(C(F)(F)F)c1] | OC1CC(C1)c1cc2C(=O)NC(c2c(NC(=O)c2cc(F)cc(c2)C(F)(F)F)c1c(F)ccc1Cl | 1H NMR (400 MHz, DMSO-d6) 10.42 (s, 1H), 9.07 (br. s, 1H), 7.90 (d, 8.5 Hz, 1H), 7.70 (d, 8.9 Hz, 1H), 7.62 (s, 1H), 7.54 (s, 1H), 7.31 (s, 1H), 7.26 (dd, 8.9, 5.2 Hz, 1H), 7.04 (td, 8.4, 3.1 Hz, 1H), 6.61 (br. s, 1H), 5.91 (br. s, 1H), 5.12 (d, 7.5 Hz, 1H), 4.11-3.94 (m, 1H), 3.07-2.95 (m, 1H), 2.65 (ddd, 14.5, 7.2, 3.8 Hz, 2H), 1.93 (ddd, 21.2, 7.3, 2.2 Hz, 2H). | 537.1 | A | A |
| I-1020 | 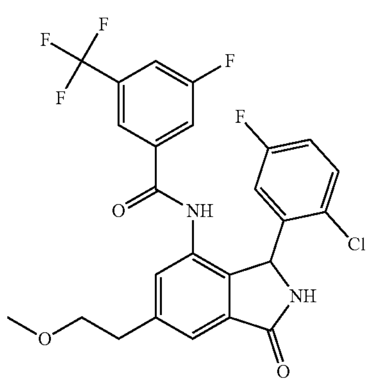 [SMILES: COCCc1cc(NC(=O)c2cc(F)cc(C(F)(F)F)c2)c2c(c1)C(=O)NC2c1cc(F)ccc1Cl] | COCCc1cc2C(=O)NC(c2c(NC(=O)c2cc(F)cc(c2)C(F)(F)F)c1)c1cc(F)ccc1Cl | NMR (400 MHz, CD3CN) 8.58 (br s, 1H), 7.64-7.52 (m, 4H), 7.39 (s, 1H), 7.21 (m, 2H), 6.94 (td, 8.4, 3.1 Hz, 1H), 6.58 (br s, 1H), 6.04 (br s, 1H), 3.63 (1, 6.5 Hz, 2H), 3.28 (s, 3H), 2.98 (td, 6.7, 1.7 Hz, 2H). | 525.4 | A | A |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-1021 | 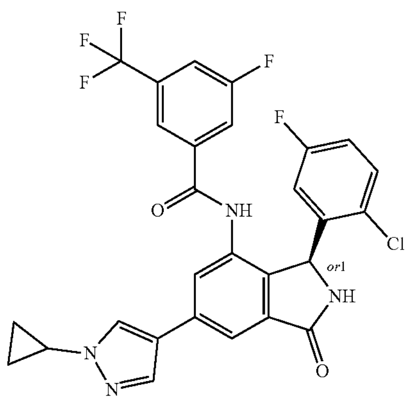 [SMILES: O=C(Nc1cc(-c2cnn(C3CC3)c2)cc2c1[C@@H](c1cc(F)ccc1Cl)NC2=O)c1cc(F)cc(C(F)(F)F)c1] | Fc1ccc(C1)c(c1)[C@H]1NC(=O)c2cc(cc(NC(=O)c3cc(F)cc(c3)C(F)(F)F)c12)-c1cnn(c1)C1CC1 | | 573.2 | E | |
| I-1022 | 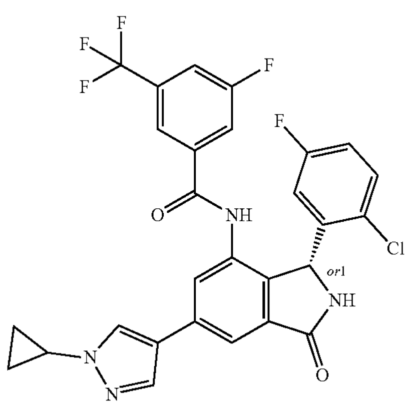 [SMILES: O=C(Nc1cc(-c2cnn(C3CC3)c2)cc2c1[C@H](c1cc(F)ccc1Cl)NC2=O)c1cc(F)cc(C(F)(F)F)c1] | Fc1ccc(C1)c(c1)[C@@H]1NC(=O)c2cc(cc(NC(=O)c3cc(F)cc(c3)C(F)(F)F)c12)-c1cnn(c1)C1CC1 | | 573.3 | A | A |
| I-1023 | 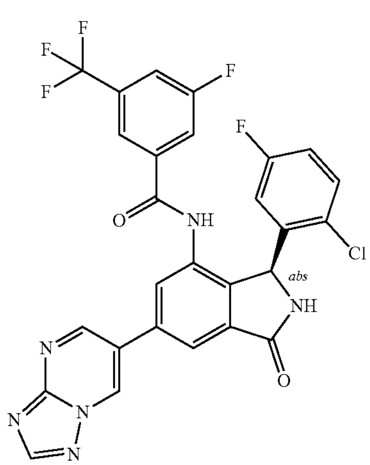 [SMILES: O=C(Nc1cc(-c2cnc3ncnn3c2)cc2c1[C@@H](c1cc(F)ccc1Cl)NC2=O)c1cc(F)cc(C(F)(F)F)c1] | Fc1ccc(C1)c(c1)[C@H]1NC(=O)c2cc(cc(NC(=O)c3cc(F)cc(c3)C(F)(F)F)c12)-c1cnc2ncnn2c1 | | 585.4 | C | |

TABLE 2-continued

Representative Compounds of the Invention with Bioactivity Data.

| Ex. No. | Structure | SMILES | $^1$H NMR | MS | ADP-Glo IC$_{50}$ | MCF 10A IC$_{50}$ |
|---|---|---|---|---|---|---|
| I-1024 | 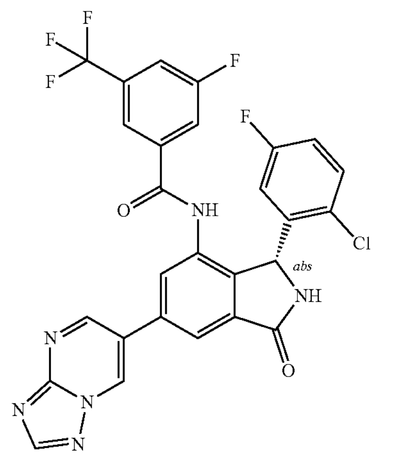 [SMILES: O=C(Nc1cc(-c2cnc3ncnn3c2)cc2c1[C@H](c1cc(F)ccc1Cl)NC2=O)c1cc(F)cc(C(F)(F)F)c1] | Fc1ccc(C1)c(c1)[C@@H]1NC(=O)c2cc(cc(NC(=O)c3cc(F)cc(c3)C(F)(F)F)c12)-c1cnc2ncnn2c1 | | 585.2 | A | A |
| I-1025 | 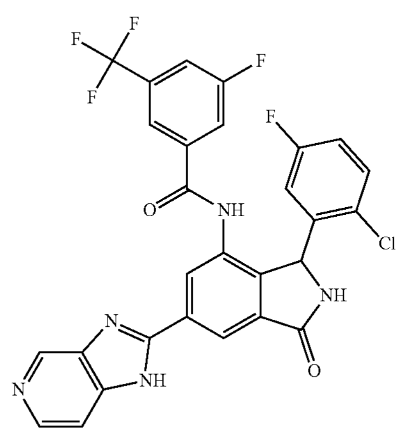 [SMILES: O=C(Nc1cc(-c2nc3cnccc3[nH]2)cc2c1C(c1cc(F)ccc1Cl)NC2=O)c1cc(F)cc(C(F)(F)F)c1] | Fc1ccc(C1)c(c1)C1NC(=O)c2cc(cc(NC(=O)c3cc(F)cc(c3)C(F)(F)F)c12)-c1nc2cnccc2[nH]1 | | 584.32 | A | B |
| I-1026 | 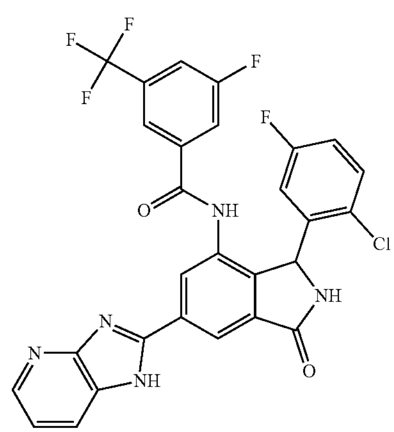 [SMILES: O=C(Nc1cc(-c2nc3ncccc3[nH]2)cc2c1C(c1cc(F)ccc1Cl)NC2=O)c1cc(F)cc(C(F)(F)F)c1] | Fc1ccc(C1)c(c1)C1NC(=O)c2cc(cc(NC(=O)c3cc(F)cc(c3)C(F)(F)F)c12)-c1nc2nccc2[nH]1 | | 584.32 | A | A |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-1027 | 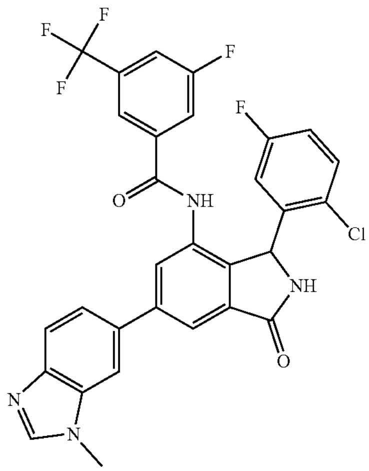 [SMILES: Cn1cnc2ccc(-c3cc(NC(=O)c4cc(F)cc(C(F)(F)F)c4)c4c(c3)C(=O)NC4c3cc(F)ccc3Cl)cc21] | Cn1cnc2ccc(cc12)-c1cc2C(=O)NC(c2c(NC(=O)c2cc(F)cc(c2)C(F)(F)F)c1)c1cc(F)ccc1Cl | | 597.38 | A | |
| I-1028 | 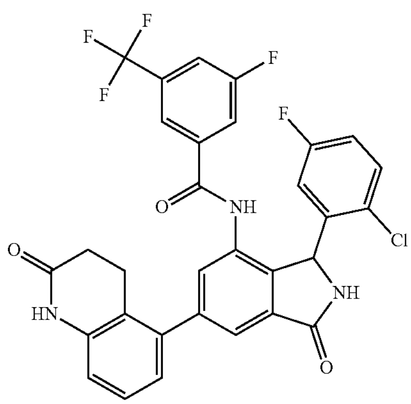 [SMILES: O=C1CCc2c(cccc2-c2cc(NC(=O)c3cc(F)cc(C(F)(F)F)c3)c3c(c2)C(=O)NC3c2cc(F)ccc2Cl)N1] | Fc1ccc(C1)c(c1)C1NC(=O)c2cc(cc(NC(=O)c3cc(F)cc(c3)C(F)(F)F)c12)-c1cccc2NC(=O)CCc12 | | 612.34 | A | A |
| I-1029 | 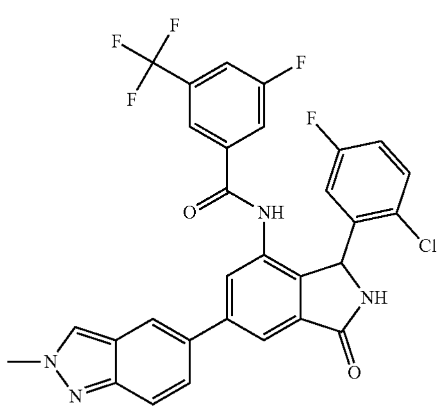 [SMILES: Cn1cc2cc(-c3cc(NC(=O)c4cc(F)cc(C(F)(F)F)c4)c4c(c3)C(=O)NC4c3cc(F)ccc3Cl)ccc2n1] | Cn1cc2cc(ccc2n1)-c1cc2C(=O)NC(c2c(NC(=O)c2cc(F)cc(c2)C(F)(F)F)c1)c1cc(F)ccc1Cl | | 597.33 | A | A |

TABLE 2-continued

Representative Compounds of the Invention with Bioactivity Data.

| Ex. No. | Structure | SMILES | $^1$H NMR | MS | ADP-Glo IC$_{50}$ | MCF 10A IC$_{50}$ |
| --- | --- | --- | --- | --- | --- | --- |
| I-1030 | 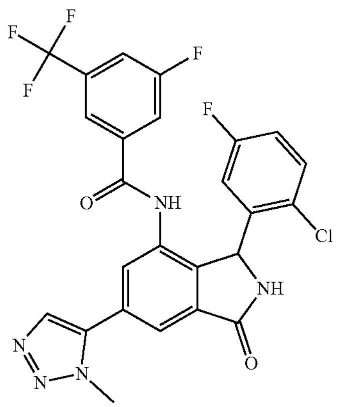 [SMILES: Cn1nncc1-c1cc(NC(=O)c2cc(F)cc(C(F)(F)F)c2)c2c(c1)C(=O)NC2c1cc(F)ccc1Cl] | Cn1nncc 1-c1cc2C(= O)NC(c2 c(NC(=O) c2cc(F)c c(c2)C(F) (F)F)c1)c 1cc(F)ccc 1Cl | | 548.31 | A | A |
| I-1031 | 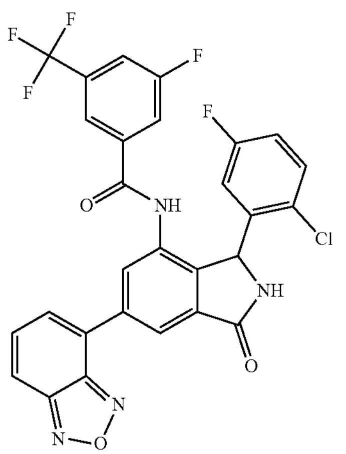 [SMILES: O=C(Nc1cc(-c2cccc3nonc23)cc2c1C(c1cc(F)ccc1Cl)NC2=O)c1cc(F)cc(C(F)(F)F)c1] | Fc1ccc(C 1)c(c1)C1 NC(=O)c 2cc(cc(N C(=O)c3 cc(F)cc(c 3)C(F)(F) F)c12)- c1cccc2n onc12 | | 585.27 | A | A |
| I-1032 | 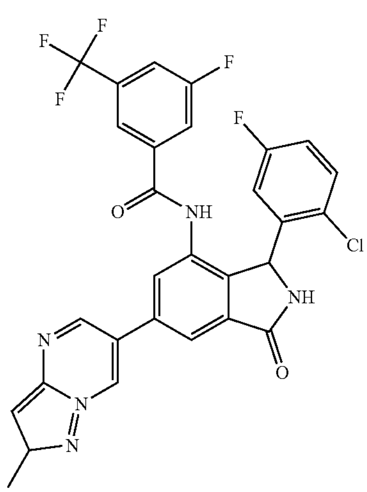 | Cc1cc2nc c(cn2n1)- c1cc2C(= O)NC(c2 c(NC(=O) c2cc(F)c c(c2)C(F) (F)F)c1)c 1cc(F)ccc 1Cl | | 598.38 | A | A |

TABLE 2-continued
Representative Compounds of the Invention with Bioactivity Data.
| Ex. No. | Structure | SMILES | $^1$H NMR | MS | ADP-Glo IC$_{50}$ | MCF 10A IC$_{50}$ |
|---|---|---|---|---|---|---|
| I-1033 | 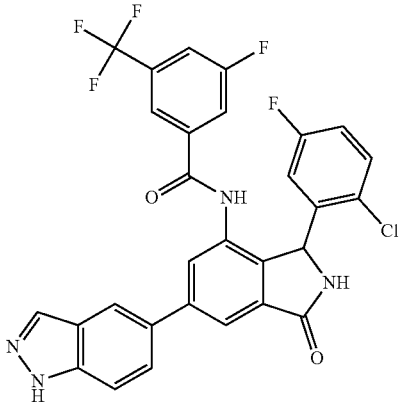 [SMILES: O=C(Nc1cc(-c2ccc3[nH]ncc3c2)cc2c1C(c1cc(F)ccc1Cl)NC2=O)c1cc(F)cc(C(F)(F)F)c1] | Fc1ccc(C1)c(c1)C1NC(=O)c2cc(cc(NC(=O)c3cc(F)cc(c3)C(F)(F)F)c12)-c1ccc2[nH]ncc2c1 | | 583.37 | A | A |
| I-1034 | 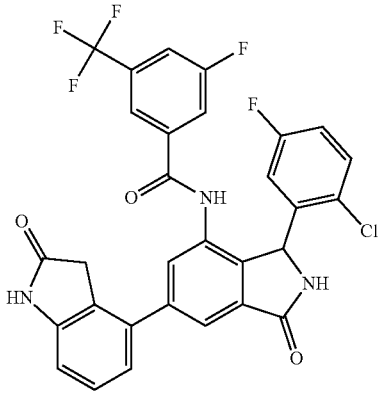 [SMILES: O=C1Cc2c(cccc2-c2cc(NC(=O)c3cc(F)cc(C(F)(F)F)c3)c3c(c2)C(=O)NC3c2cc(F)ccc2Cl)N1] | Fc1ccc(C1)c(c1)C1NC(=O)c2cc(cc(NC(=O)c3cc(F)cc(c3)C(F)(F)F)c12)-c1cccc2NC(=O)Cc12 | | 598.38 | A | |
| I-1035 | 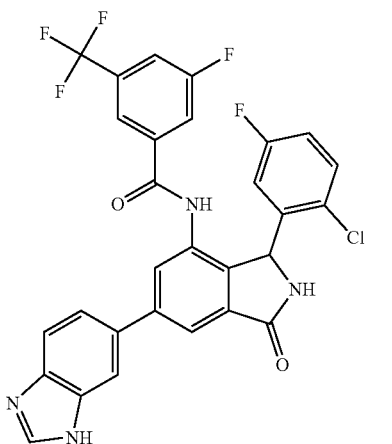 [SMILES: O=C(Nc1cc(-c2ccc3nc[nH]c3c2)cc2c1C(c1cc(F)ccc1Cl)NC2=O)c1cc(F)cc(C(F)(F)F)c1] | Fc1ccc(C1)c(c1)C1NC(=O)c2cc(cc(NC(=O)c3cc(F)cc(c3)C(F)(F)F)c12)-c1ccc2nc[nH]c2c1 | | 583.32 | A | |

TABLE 2-continued
Representative Compounds of the Invention with Bioactivity Data.
| Ex. No. | Structure | SMILES | ¹H NMR | MS | ADP-Glo IC$_{50}$ | MCF 10A IC$_{50}$ |
|---|---|---|---|---|---|---|
| I-1036 | 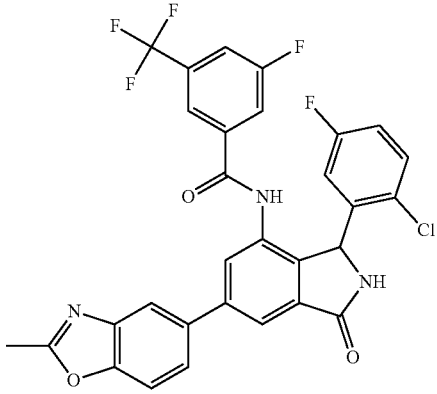 [SMILES: Cc1nc2cc(-c3cc(NC(=O)c4cc(F)cc(C(F)(F)F)c4)c4c(c3)C(=O)NC4c3cc(F)ccc3Cl)ccc2o1] | Cc1nc2cc(ccc2o1)-c1cc2C(=O)NC(c2c(NC(=O)c2cc(F)cc(c2)C(F)(F)F)c1)c1cc(F)ccc1Cl | | 598.33 | A | |
| I-1037 | 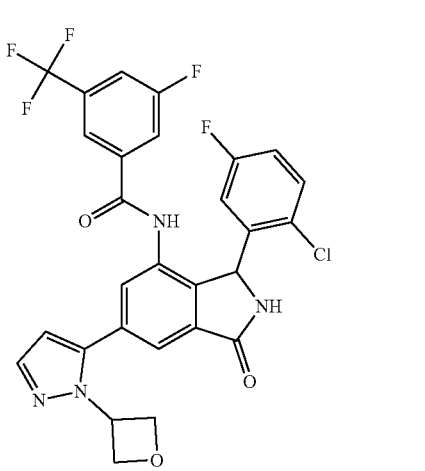 [SMILES: O=C(Nc1cc(-c2ccnn2C2COC2)cc2c1C(c1cc(F)ccc1Cl)NC2=O)c1cc(F)cc(C(F)(F)F)c1] | Fc1ccc(C1)c(c1)C1NC(=O)c2cc(cc(NC(=O)c3cc(F)cc(c3)C(F)(F)F)c12)-c1ccnn1C1COC1 | | 589.33 | A | |
| I-1038 | 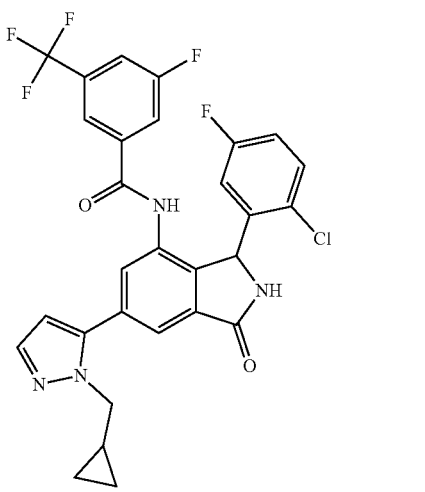 [SMILES: O=C(Nc1cc(-c2ccnn2CC2CC2)cc2c1C(c1cc(F)ccc1Cl)NC2=O)c1cc(F)cc(C(F)(F)F)c1] | Fc1ccc(C1)c(c1)C1NC(=O)c2cc(cc(NC(=O)c3cc(F)cc(c3)C(F)(F)F)c12)-c1ccnn1CC1CC1 | | 587.32 | A | A |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-1039 | 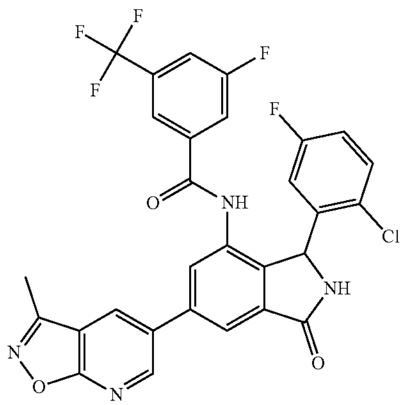 [SMILES: Cc1noc2ncc(-c3cc(NC(=O)c4cc(F)cc(C(F)(F)F)c4)c4c(c3)C(=O)NC4c3cc(F)ccc3Cl)cc12] | Cc1noc2ncc(cc12)-c1cc2C(=O)NC(c2c(NC(=O)c2cc(F)cc(c2)C(F)(F)F)c1)c1cc(F)ccc1Cl | | 599.33 | A | A |
| I-1040 | 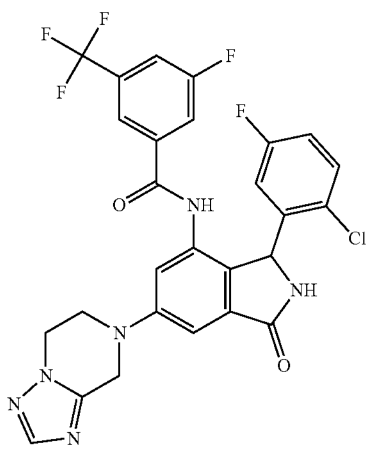 [SMILES: O=C(Nc1cc(N2CCn3ncnc3C2)cc2c1C(c1cc(F)ccc1Cl)NC2=O)c1cc(F)cc(C(F)(F)F)c1] | Fc1ccc(C1)c(c1)C1NC(=O)c2cc(cc(NC(=O)c3cc(F)cc(c3)C(F)(F)F)c12)N1CCn2ncnc2C1 | | 589.33 | A | B |
| I-1041 | 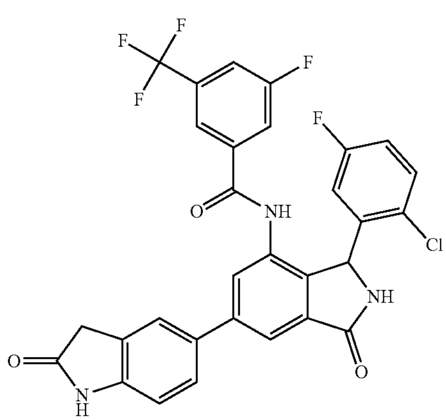 [SMILES: O=C1Cc2cc(-c3cc(NC(=O)c4cc(F)cc(C(F)(F)F)c4)c4c(c3)C(=O)NC4c3cc(F)ccc3Cl)ccc2N1] | Fc1ccc(C1)c(c1)C1NC(=O)c2cc(cc(NC(=O)c3cc(F)cc(c3)C(F)(F)F)c12)-c1ccc2NC(=O)Cc2c1 | | 598.23 | A | |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-1042 | 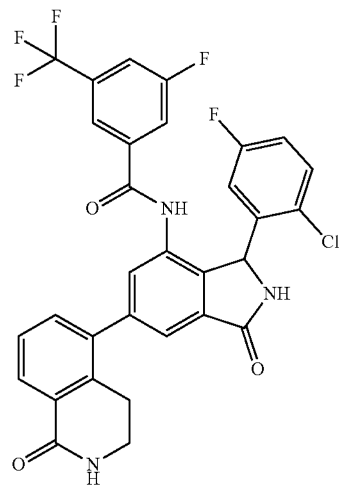 [SMILES: O=C(Nc1cc(-c2cccc3c2CCNC3=O)cc2c1C(c1cc(F)ccc1Cl)NC2=O)c1cc(F)cc(C(F)(F)F)c1] | Fc1ccc(C1)c(c1)C1NC(=O)c2cc(cc(NC(=O)c3cc(F)cc(c3)C(F)(F)F)c12)-c1cccc2C(=O)NCCc12 | | 612.39 | A | A |
| I-1043 | 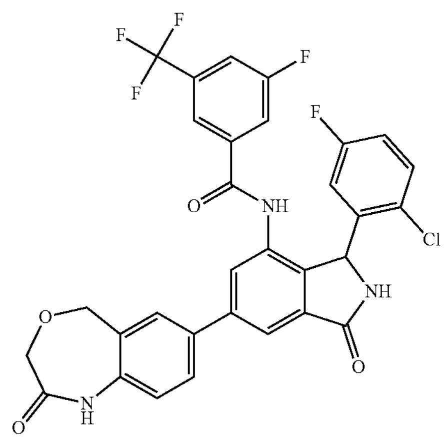 [SMILES: O=C1COCc2cc(-c3cc(NC(=O)c4cc(F)cc(C(F)(F)F)c4)c4c(c3)C(=O)NC4c3cc(F)ccc3Cl)ccc2N1] | Fc1ccc(C1)c(c1)C1NC(=O)c2cc(cc(NC(=O)c3cc(F)cc(c3)C(F)(F)F)c12)-c1ccc2NC(=O)COCc2c1 | | 628.34 | A | A |
| I-1044 | 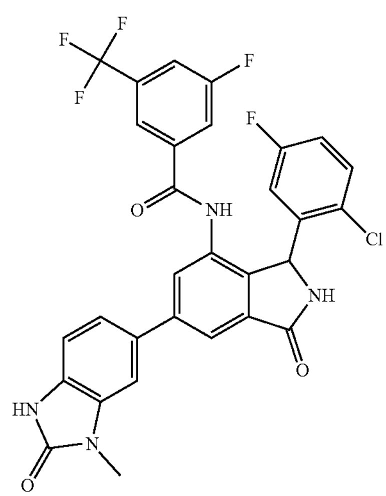 [SMILES: Cn1c(=O)[nH]c2ccc(-c3cc(NC(=O)c4cc(F)cc(C(F)(F)F)c4)c4c(c3)C(=O)NC4c3cc(F)ccc3Cl)cc21] | Cn1c2cc(ccc2[nH]c1=O)-c1cc2C(=O)NC(c2c(NC(=O)c2cc(F)cc(c2)C(F)(F)c1)c1cc(F)ccc1Cl | | 613.34 | A | |

TABLE 2-continued

Representative Compounds of the Invention with Bioactivity Data.

| Ex. No. | Structure | SMILES | $^1$H NMR | MS | ADP-Glo IC$_{50}$ | MCF 10A IC$_{50}$ |
|---|---|---|---|---|---|---|
| I-1045 | 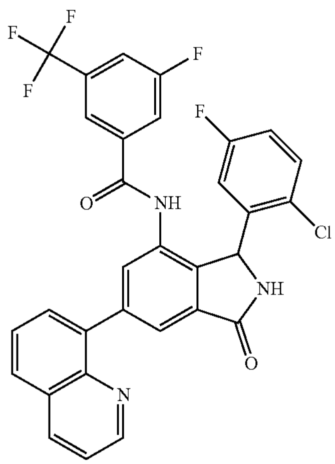 [SMILES: O=C(Nc1cc(-c2cccc3cccnc23)cc2c1C(c1cc(F)ccc1Cl)NC2=O)c1cc(F)cc(C(F)(F)F)c1] | Fc1ccc(C1)c(c1)C1NC(=O)c2cc(cc(NC(=O)c3cc(F)cc(c3)C(F)(F)F)c12)-c1cccc2cccnc12 | | 594.33 | A | |
| I-1046 | 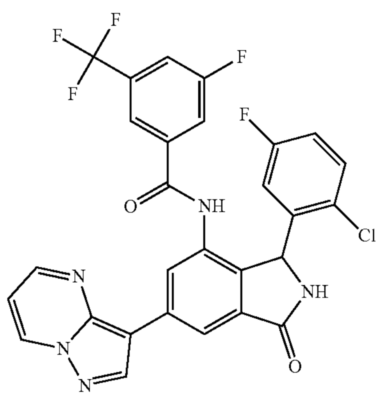 [SMILES: O=C(Nc1cc(-c2cnn3cccnc23)cc2c1C(c1cc(F)ccc1Cl)NC2=O)c1cc(F)cc(C(F)(F)F)c1] | Fc1ccc(C1)c(c1)C1NC(=O)c2cc(cc(NC(=O)c3cc(F)cc(c3)C(F)(F)F)c12)-c1cnn2cccnc12 | | 584.32 | A | A |
| I-1047 | 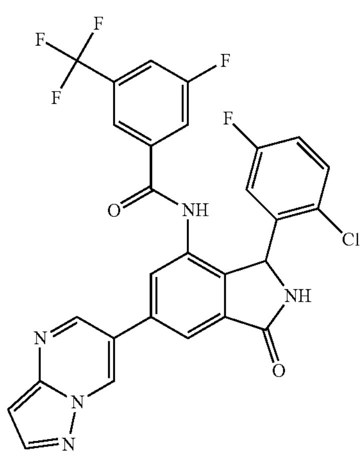 [SMILES: O=C(Nc1cc(-c2cnc3ccnn3c2)cc2c1C(c1cc(F)ccc1Cl)NC2=O)c1cc(F)cc(C(F)(F)F)c1] | Fc1ccc(C1)c(c1)C1NC(=O)c2cc(cc(NC(=O)c3cc(F)cc(c3)C(F)(F)F)c12)-c1cnc2ccnn2c1 | | 584.32 | A | A |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-1048 | 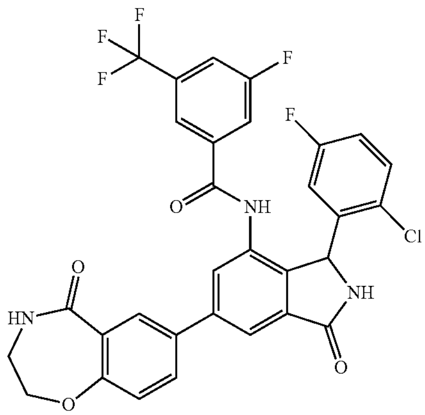 [SMILES: O=C(Nc1cc(-c2ccc3c(c2)C(=O)NCCO3)cc2c1C(c1cc(F)ccc1Cl)NC2=O)c1cc(F)cc(C(F)(F)F)c1] | Fc1ccc(C1)c(c1)C1NC(=O)c2cc(cc(NC(=O)c3cc(F)cc(c3)C(F)(F)F)c12)-c1ccc2OCCNC(=O)c2c1 | | 628.34 | A | A |
| I-1049 | 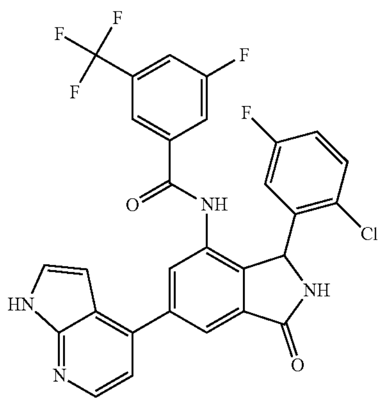 [SMILES: O=C(Nc1cc(-c2ccnc3[nH]ccc23)cc2c1C(c1cc(F)ccc1Cl)NC2=O)c1cc(F)cc(C(F)(F)F)c1] | Fc1ccc(C1)c(c1)C1NC(=O)c2cc(cc(NC(=O)c3cc(F)cc(c3)C(F)(F)F)c12)-c1ccnc2[nH]ccc12 | | 583.32 | A | A |
| I-1050 | 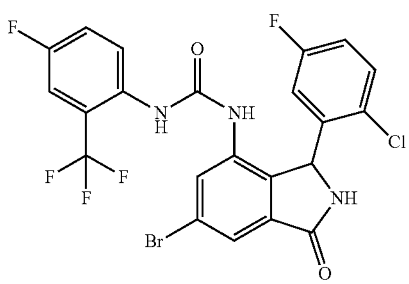 [SMILES: O=C(Nc1ccc(F)cc1C(F)(F)F)Nc1cc(Br)cc2c1C(c1cc(F)ccc1Cl)NC2=O] | Fc1ccc(C1)c(c1)C1NC(=O)c2cc(Br)cc(NC(=O)Nc3ccc(F)cc3C(F)(F)F)c12 | (400 MHz, DMSO-d6) 9.31 (br s, 1H), 9.21 (s, 1H), 8.56 (br s, 1H), 7.80 (d, 1.3 Hz, 1H), 7.62 (d, 1.3 Hz, 1H), 7.61-7.42 (m, 4H), 7.22 (td, 8.5, 3.0 Hz, 1H), 6.82 (br s, 1H), 6.06 (s, 1H) | 558.3 | B | |
| I-1051 | 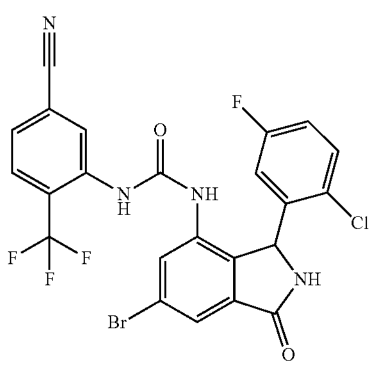 [SMILES: N#Cc1ccc(C(F)(F)F)c(NC(=O)Nc2cc(Br)cc3c2C(c2cc(F)ccc2Cl)NC3=O)c1] | Fc1ccc(C1)c(c1)C1NC(=O)c2cc(Br)cc(NC(=O)Nc3cc(cc3C(F)(F)F)C#N)c12 | 1H NMR (400 MHz, DMSO-d6, 60 Å ° C.) 9.06 (br s, 1H), 8.39 (s, 1H), 8.24 (s, 1H), 7.81 (d. 7.4 Hz, 2H), 7.64 (s, 2H), 7.44 (dd, 8.8, 5.1 Hz, 1H), 7.18 (td, 8.4, 3.1 Hz, 1H), 6.78 (br s, 1H), 6.05 (s, 1H) | 565.3 | D | |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-1052 | 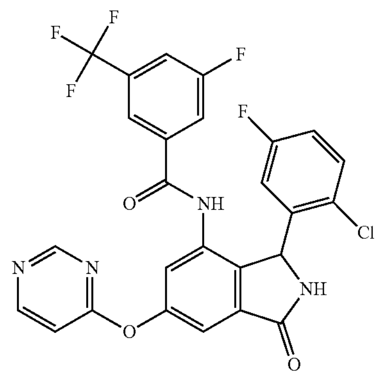 [SMILES: O=C(Nc1cc(Oc2ccncn2)cc2c1C(c1cc(F)ccc1Cl)NC2=O)c1cc(F)cc(C(F)(F)F)c1] | Fc1ccc(C1)c(c1)C1NC(=O)c2cc(Oc3cncn3)cc(NC(=O)c3cc(F)cc(c3)C(F)(F)F)c12 | (400 MHz, DMSO-d6) 10.52 (br s, 1H), 9.29 (s, 1H), 8.82 (s, 1H), 8.75 (d, 6.0 Hz, 1H), 7.95 (d, 8.4 Hz, 1H), 7.72 (d, 8.9 Hz, 1H), 7.64 (s, 1H), 7.54 (d, 1.9 Hz., 1H), 7.41 (s, 1H), 7.34 (dd, 8.9, 5.2 Hz, 1H), 7.28 (dd, 5.7, 0.7 Hz, 1H), 7.12 (td, 8.5, 3.0 Hz, 1H), 6.70 (br s, 1H), 6.01 (br s, 1H) | 559.4 | B | |
| I-1053 | 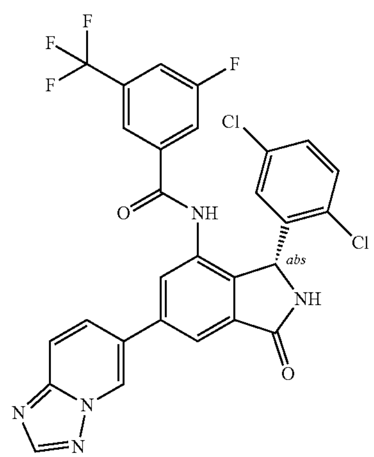 [SMILES: O=C(Nc1cc(-c2ccc3ncnn3c2)cc2c1[C@H](c1cc(Cl)ccc1Cl)NC2=O)c1cc(F)cc(C(F)(F)F)c1] | Fc1cc(cc(c1)C(F)(F)F)C(=O)Nc1cc(cc2C(=O)N[C@H](c12)c1cc(Cl)ccc1Cl)-c1ccc2ncnn2c1 | 1H NMR (400 MHz, Chloroform-d) 8.96 (s, 1H), 8.56 (s, 1H), 8.45 (s, 1H), 8.09 (d, 1.6 Hz, 1H), 7.97-7.87 (m, 2H), 7.58-7.51(m, 4H), 7.43 (d, 8.6 Hz, 1H), 7.36 (dd, 8.6, 2.4 Hz, 1H), 7.06 (s, 1H), 6.50 (s, 1H), 6.30 (s, 1H) | 600.05 | C | |
| I-1054 | 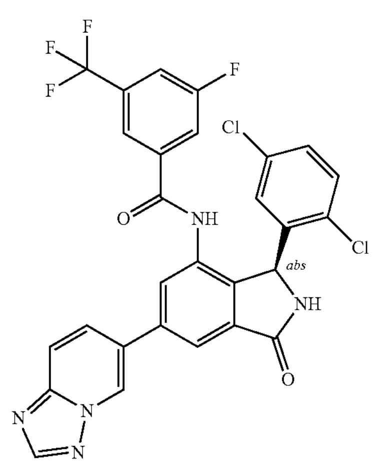 [SMILES: O=C(Nc1cc(-c2ccc3ncnn3c2)cc2c1[C@@H](c1cc(Cl)ccc1Cl)NC2=O)c1cc(F)cc(C(F)(F)F)c1] | Fc1cc(cc(c1)C(F)(F)F)C(=O)Nc1cc(cc2C(=O)N[C@@H](c12)c1cc(Cl)ccc1Cl)-c1ccc2ncnn2c1 | 1H NMR (400 MHz, Chloroform-d) 8.96 (s, 1H), 8.56 (s, 1H), 8.45 (s, 1H), 8.09 (d, 1.5 Hz, 1H), 7.97-7.87 (m, 2H), 7.58-7.53 (m,3H), 7.49 (s, 1H), 7.43 (d, 8.6 Hz, 1H), 7.36 (dd, 8.7, 2.4 Hz, 1H), 7.06 (s, 1H), 6.51 (s, 1H), 6.30 (s, 1H). | 600.05 | A | A |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-1055 | 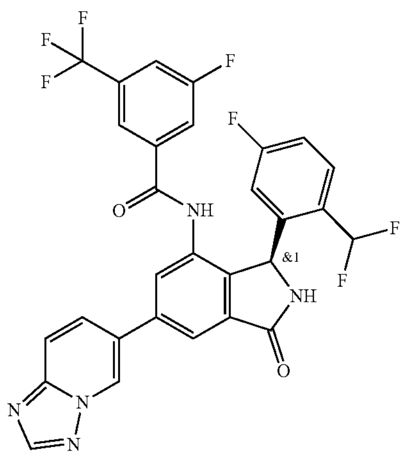 [SMILES: O=C(Nc1cc(-c2ccc3ncnn3c2)cc2c1[C@@H](c1cc(F)ccc1C(F)F)NC2=O)c1cc(F)cc(C(F)(F)F)c1] | FC(F)c1cc(F)cc1[C@H]1NC(=O)c2cc(cc(NC(=O)c3cc(F)cc(c3)C(F)(F)F)c12)-c1ccc2ncnn2c1 | 1H NMR (400 MHz, DMSO-d6) 10.62 (s, 1H), 9.50 (s, 1H), 9.30 (s, 1H), 8.59 (s, 1H), 8.16 (dd, 11.3, 1.8 Hz, 2H), 8.00 (dd, 5.5, 3.8 Hz, 2H), 7.95 (d, 8.5 Hz, 1H), 7.72 (d, 8.9 Hz, 1H), 7.65 (s, 1H), 7.52 (dd, 8.9, 5.6 Hz, 1H), 7.23 (td, 8.4, 2.7 Hz, 1H), 6.57 (s, 1H), 6.11 (s, 1H). | 600.2 | D | |
| I-1056 | 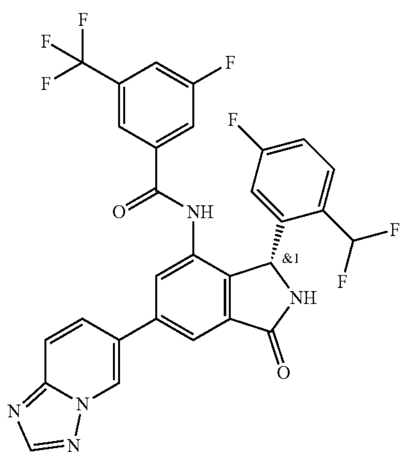 [SMILES: O=C(Nc1cc(-c2ccc3ncnn3c2)cc2c1[C@H](c1cc(F)ccc1C(F)F)NC2=O)c1cc(F)cc(C(F)(F)F)c1] | FC(F)c1cc(F)cc1[C@@H]1NC(=O)c2cc(cc(NC(=O)c3cc(F)cc(c3)C(F)(F)F)c12)-c1ccc2ncnn2c1 | 1H NMR (400 MHz, DMSO-d6) 10.62 (s, 1H), 9.50 (s, 1H), 9.30 (s, 1H), 8.59 (s, 1H), 8.16 (dd, 11.3, 1.8 Hz, 2H), 8.00 (dd, 5.5, 3.8 Hz, 2H), 7.95 (d, 8.5 Hz, 1H), 7.72 (d, 8.9 Hz, 1H), 7.65 (s, 1H), 7.52 (dd, 8.9, 5.6 Hz, 1H), 7.23 (td, 8.4, 2.7 Hz, 1H), 6.57 (s, 1H), 6.11 (s, 1H). | 600.2 | A | A |
| I-1057 | 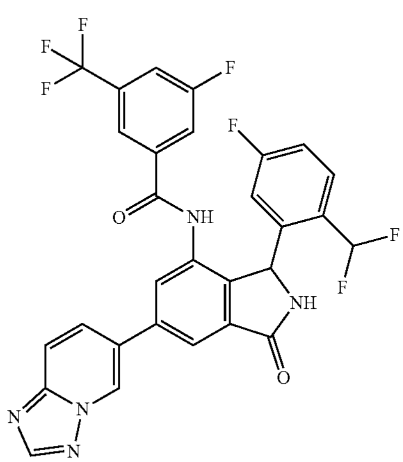 [SMILES: O=C(Nc1cc(-c2ccc3ncnn3c2)cc2c1C(c1cc(F)ccc1C(F)F)NC2=O)c1cc(F)cc(C(F)(F)F)c1] | FC(F)c1cc(F)cc1C1NC(=O)c2cc(cc(NC(=O)c3cc(F)cc(c3)C(F)(F)F)c12)-c1ccc2ncnn2c1 | 1H NMR (400 MHz, DMSO-d6) 10.62 (s, 1H), 9.50 (s, 1H), 9.30 (s, 1H), 8.59 (s, 1H), 8.16 (dd, 11.3, 1.8 Hz, 2H), 8.00 (dd, 5.5, 3.8 Hz, 2H), 7.95 (d, 8.5 Hz, 1H), 7.72 (d, 8.9 Hz, 1H), 7.65 (s, 1H), 7.52 (dd, 8.9, 5.6 Hz, 1H), 7.23 (td, 8.4, 2.7 Hz, 1H), 6.57 (s, 1H), 6.11 (s, 1H). | 600.2 | A | A |

TABLE 2-continued

Representative Compounds of the Invention with Bioactivity Data.

| Ex. No. | Structure | SMILES | $^1$H NMR | MS | ADP-Glo IC$_{50}$ | MCF 10A IC$_{50}$ |
|---|---|---|---|---|---|---|
| I-1058 | 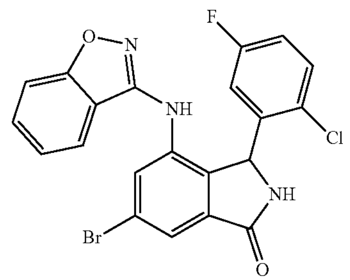 [SMILES: O=C1NC(c2cc(F)ccc2Cl)c2c(Nc3noc4ccccc34)cc(Br)cc21] | Fc1ccc(C 1)c(c1)C1 NC(=O)c 2cc(Br)cc (Nc3noc4 ccccc34) c12 | 1H NMR (400 MHz, DMSO-d6) 9.24 (s, 1H), 9.12 (s, 1H), 7.98 (d, 1.8 Hz, 1H), 7.65 (d, 1.7 Hz, 1H), 7.63-7.55 (m, 3H), 7.35-7.21 (m, 2H), 7.02 (td, 8.4, 3.0 Hz, 1H), 6.81 (s, 1H), 6.16 (s, 1H). | 472.05 | E | |
| I-1059 | 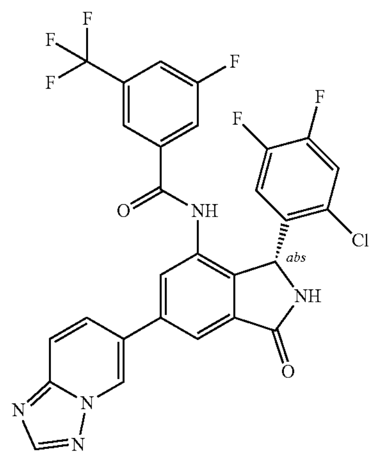 [SMILES: O=C(Nc1cc(-c2ccc3ncnn3c2)cc2c1[C@H](c1cc(F)c(F)cc1Cl)NC2=O)c1cc(F)cc(C(F)(F)F)c1] | Fc1cc(cc (c1)C(F) (F)F)C(= O)Nc1cc (cc2C(=O) N[C@H] (c12)c1c c(F)c(F)c c1Cl)-c1ccc2nc nn2c1 | 1H NMR (400 MHz, DMSO-d6) 10.65 (s, 1H), 9.48 (t, 1.4 Hz, 1H), 9.26 (s, 1H), 8.58 (s, 1H), 8.18-8.11 (m, 2H), 8.03-7.95 (m, 3H), 7.84 (d, 9.0 Hz, 1H), 7.72 (s, 1H), 7.59 (dd, 10.4, 7.3 Hz, 1H), 7.00 (s, 1H), 6.04 (s, 1H). | 602.1 | D | |
| I-1060 | 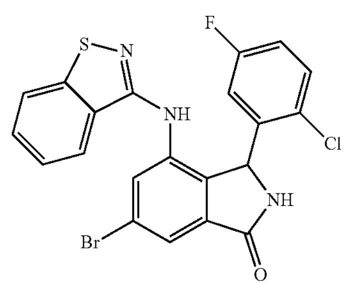 [SMILES: O=C1NC(c2cc(F)ccc2Cl)c2c(Nc3nsc4ccccc34)cc(Br)cc21] | Fc1ccc(C 1)c(c1)C1 NC(=O)c 2cc(Br)cc (Nc3nsc4 ccccc34) c12 | 1H NMR (400 MHz, DMSO-d6) 9.29 (s, 1H), 9.17 (s, 1H), 8.07-7.97 (m, 2H), 7.81 (d, 8.1 Hz, 1H), 7.65 (d, 1.7 Hz, 1H), 7.61-7.52 (m, 1H), 7.40 (dd, 8.2, 6.9 Hz, 1H), 7.21 (dd, 8.9, 5.1 Hz, 1H), 6.97 (td, 8.4, 3.1 Hz, 1H), 6.57 (s, 1H), 6.11-6.07 (m, 1H). | 488 | E | |
| I-1061 | 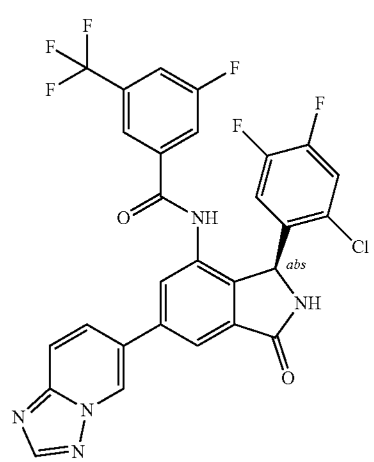 [SMILES: O=C(Nc1cc(-c2ccc3ncnn3c2)cc2c1[C@@H](c1cc(F)c(F)cc1Cl)NC2=O)c1cc(F)cc(C(F)(F)F)c1] | Fc1cc(cc (c1)C(F) (F)F)C(= O)Nc1cc (cc2C(=O) N[C@@ H](c12)c 1cc(F)c(F) cc1Cl)-c1ccc2nc nn2c1 | 1H NMR (400 MHz, DMSO-d6) 10.64 (s, 1H), 9.48 (t, 1.4 Hz, 1H), 9.26 (s, 1H), 8.58 (s, 1H), 8.18-8.11 (m, 2H), 8.03-7.95 (m, 3H), 7.83 (d, 8.9 Hz, 1H), 7.71 (s, 1H), 7.59 (dd, 10.4, 7.2 Hz, 1H), 7.00 (s, 1H), 6.04 (s, 1H). | 602.1 | A | A |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-1062 | 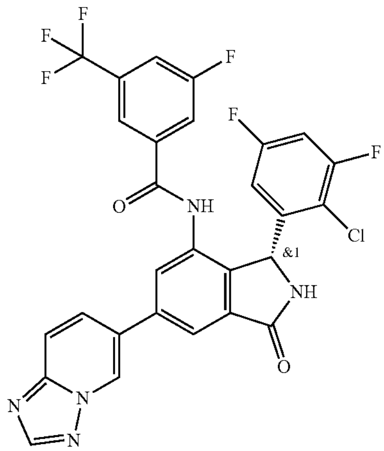 [SMILES: O=C(Nc1cc(-c2ccc3ncnn3c2)cc2c1[C@H](c1cc(F)cc(F)c1Cl)NC2=O)c1cc(F)cc(C(F)(F)F)c1] | Fc1cc(cc (c1)C(F) (F)F)C(= O)Nc1cc (cc2C(=O) N[C@H] (c12)c1c c(F)cc(F) c1Cl)- c1ccc2nc nn2c1 | 1H NMR (400 MHz, Chloroform-d) 8.95 (s, 1H), 8.45 (s, 1H), 8.39 (s, 1H), 8.11 (d, 1.6 Hz, 1H), 7.97-7.86 (m, 2H), 7.58 (d, 8.1 Hz, 2H), 7.51 (d, 9.0 Hz, 2H), 6.99 (dd, 8.1, 2.9 Hz, 1H), 6.65 (s, 1H), 6.47 (s, 1H), 6.35 (s, 1H). | 602.1 | A | A |
| I-1063 | 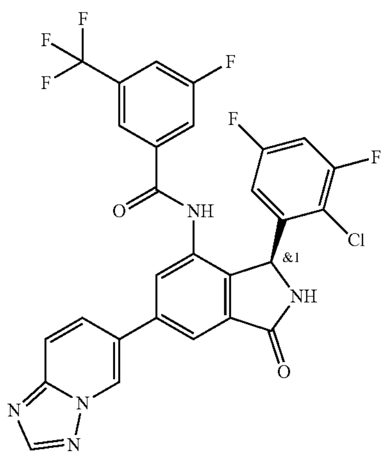 [SMILES: O=C(Nc1cc(-c2ccc3ncnn3c2)cc2c1[C@@H](c1cc(F)cc(F)c1Cl)NC2=O)c1cc(F)cc(C(F)(F)F)c1] | Fc1cc(cc (c1)C(F) (F)F)C(= O)Nc1cc (cc2C(=O) N[C@@ H](c12)c 1cc(F)cc (F)c1Cl)- c1ccc2nc nn2c1 | 1H NMR (400 MHz, Chloroform-d) 8.96 (s, 1H), 8.45 (s, 1H), 8.38 (s, 1H), 8.11 (s, 1H), 7.91 (q, 9.1 Hz, 2H), 7.61-7.52 (m, 3H), 7.50 (s, 1H), 6.99 (d, 8.0 Hz, 1H), 6.64 (s, 1H), 6.51 (s, 1H), 6.34 (s, 1H). | 602.1 | E | |
| I-1064 | 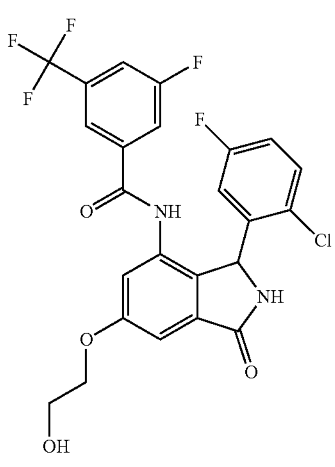 [SMILES: O=C(Nc1cc(OCCO)cc2c1C(c1cc(F)ccc1Cl)NC2=O)c1cc(F)cc(C(F)(F)F)c1] | OCCOc1 cc2C(=O) NC(c2c (NC(=O)c 2cc(F)cc (c2)C(F) (F)F)c1)c 1cc(F)ccc 1Cl | NMR (400 MHz, DMSO-d6) 10.49-10.36 (s, 1H), 9.13 (s, 1H), 7.94 (d, 8.3 Hz, 1H), 7.71 (d, 8.7 Hz, 1H), 7.63 (s, 1H), 7.31 (dd, 8.9, 5.2 Hz, 1H), 7.20 (s), 7.12-7.05 (m, 2H), 5.90 (br, s, 1H), 4.94 (t, 5.5 Hz, 1H), 4.15-4.08 (m, 2H), 3.76 (q, 5.0 Hz, 2H). | 527.2 | A | A |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-1065 | 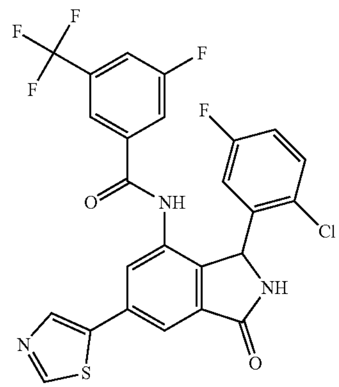 [SMILES: O=C(Nc1cc(-c2cncs2)cc2c1C(c1cc(F)ccc1Cl)NC2=O)c1cc(F)cc(C(F)(F)F)c1] | Fc1ccc(C1)c(c1)C1NC(=O)c2cc(cc(NC(=O)c3cc(F)cc(c3)C(F)(F)F)c12)-c1cncs1 | NMR (400 MHz, CD3CN) 8.88 (s, 1H), 8.73 (br s, 1H), 8.25 (d, 5.4 Hz, 1H), 7.95 (br s, 1H), 7.80 (s, 1H), 7.68-7.52 (m, 3H), 7.31 (m, 1H), 7.26-7.19 (m, 1H), 6.95 (td, 8.8, 2.7 Hz, 1H), 6.67 (br s, 1H), 6.13 (br s, 1H). | 550 | A | A |
| I-1066 | 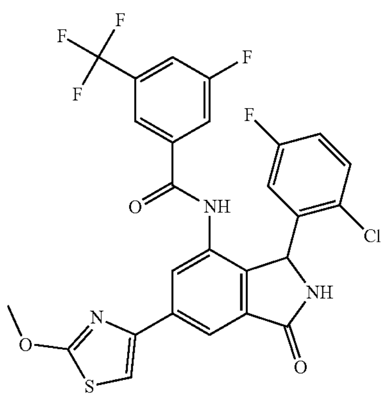 [SMILES: COc1nc(-c2cc(NC(=O)c3cc(F)cc(C(F)(F)F)c3)c3c(c2)C(=O)NC3c2cc(F)ccc2Cl)cs1] | COc1nc(cs1)-c1cc2C(=O)NC(c2c(NC(=O)c2cc(F)cc(c2)C(F)(F)F)c1)c1cc(F)ccc1Cl | NMR (400 MHz, CD3CN) 8.67 (br s, 1H), 8.16 (s, 1H), 8.03 (s, 1H), 7.61 (dd, 18.1, 9.7 Hz, 3H), 7.29 (d, 1.3 Hz, 1H), 7.23 (dd, 8.9, 5.0 Hz, 2H), 6.94 (td, 8.5, 3.4 Hz, 1H), 6.67 (br s, 1H), 6.12 (br s, 1H), 4.12 (s, 3H). | 580 | A | B |
| I-1067 | 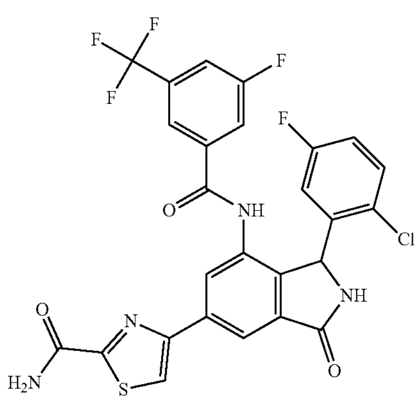 [SMILES: NC(=O)c1nc(-c2cc(NC(=O)c3cc(F)cc(C(F)(F)F)c3)c3c(c2)C(=O)NC3c2cc(F)ccc2Cl)cs1] | NC(=O)c1nc(cs1)-c1cc2C(=O)NC(c2c(NC(=O)c2cc(F)cc(c2)C(F)(F)F)c1)c1cc(F)ccc1Cl | NMR (400 MHz, CD3CN/DMSO) 10.49 (br s, 1H), 8.88 (br s, 1H), 8.43 (br s, 1H), 8.36 (d, 14.5 Hz, 2H), 8.15 (br s, 1H), 7.97 (br s, 1H), 7.78-7.64 (m, 3H), 7.59 (m, 1H), 7.20 (dd, 8.7, 5.2 Hz, 1H), 6.94 (td, 8.4, 3.0 Hz, 1H), 6.06 (br s, 1H). | 591 | A | A |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-1068 | 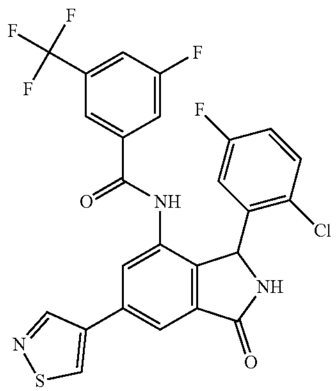 [SMILES: O=C(Nc1cc(-c2cnsc2)cc2c1C(c1cc(F)ccc1Cl)NC2=O)c1cc(F)cc(C(F)(F)F)c1] | Fc1ccc(C1)c(c1)C1NC(=O)c2cc(cc(NC(=O)c3cc(F)cc(c3)C(F)(F)F)c12)-c1cnsc1 | NMR (400 MHz, CD3CN) 9.14 (s, 1H), 8.94 (s, 1H), 8.77 (br s, 1H), 8.08 (s, 1H), 7.89 (s, 1H), 7.66 (br d, 8.2 Hz, 1H), 7.61 (submerged br d, 8.3 Hz, 1H), 7.61-7.58 (m, 1H), 7.25 (dd, 8.2, 4.8 Hz, 1H), 7.29-7.26 (submerged m, 1H), 7.01-6.95 (m, 1H), 6.69 (br s, 1H), 6.16 (br s, 1H). | 548 | A | A |
| I-1069 | 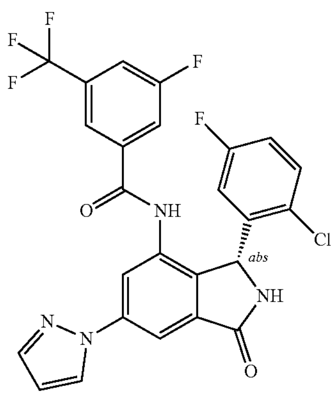 [SMILES: O=C(Nc1cc(-n2cccn2)cc2c1[C@H](c1cc(F)ccc1Cl)NC2=O)c1cc(F)cc(C(F)(F)F)c1] | Fc1ccc(C1)c(c1)[C@@H]1NC(=O)c2cc(cc(NC(=O)c3cc(F)cc(c3)C(F)(F)F)c12)-n1cccn1 | (400 MHz, DMSO-D6) 10.67 (s, 1 H), 9.29 (s, 1 H), 8.76 (d, 2.5 Hz, 1 H), 8.14 (d, 1.6 Hz, 1 H), 8.09 (d, 1.6 Hz, 1 H), 7.96 (d, 8.4 Hz, 1 H), 7.82 (d, 1.6 Hz, 1 H), 7.76 (d, 8.9 Hz, 1 H), 7.69 (s, 1 H), 7.33 (dd, 8.9, 5.2 Hz, 1 H), 7.10 (td, 8.5, 3.0 Hz, 1 H), 6.66-6.58 (m, 1 H), 6.03 (br s, 1 H). \. | 533.3 | A | A |
| I-1070 | 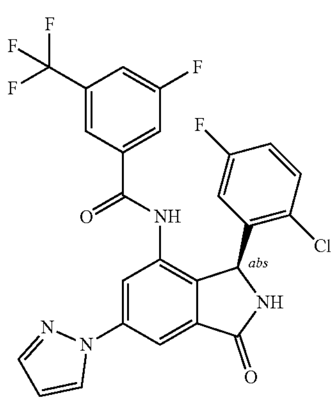 [SMILES: O=C(Nc1cc(-n2cccn2)cc2c1[C@@H](c1cc(F)ccc1Cl)NC2=O)c1cc(F)cc(C(F)(F)F)c1] | Fc1ccc(C1)c(c1)[C@H]1NC(=O)c2cc(cc(NC(=O)c3cc(F)cc(c3)C(F)(F)F)c12)-n1cccn1 | (400 MHz, DMSO-D6) 10.67 (s, 1 H), 9.29 (s, 1 H), 8.76 (d, 2.5 Hz, 1 H), 8.14 (d, 1.6 Hz, 1 H), 8.09 (d, 1.6 Hz, 1 H), 7.96 (d, 8.4 Hz, 1 H), 7.82 (d, 1.6 Hz, 1 H), 7.76 (d, 8.9 Hz, 1 H), 7.69 (s, 1 H), 7.33 (dd, 8.9, 5.2 Hz, 1 H), 7.10 (td, 8.5, 3.0 Hz, 1 H), 6.66-6.58 (m, 1 H), 6.03 (br s, 1 H). | 533.3 | D | |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-1071 | 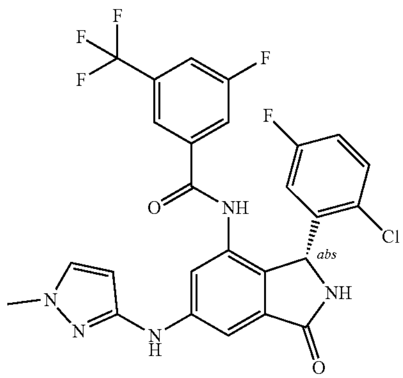 [SMILES: Cn1ccc(Nc2cc(NC(=O)c3cc(F)cc(C(F)(F)F)c3)c3c(c2)C(=O)N[C@H]3c2cc(F)ccc2Cl)n1] | Cn1ccc(Nc2cc3C(=O)N[C@H](c3c(NC(=O)c3cc(F)cc(c3)C(F)(F)F)c2)c2cc(F)ccc2Cl)n1 | 1H-NMR (400 MHz, DMSO-d6) 10.41 (s, 1H), 8.96 (br. s, 1H), 8.90 (br. s, 1H), 7.91 (br. s, 1H), 7.73-7.68 (m, 2H), 7.62 (br. s, 1H), 7.56 (d, 2.1 Hz, 1H), 7.40 (br. s, 1H), 7.29 (dd, 8.9, 5.2 Hz, 1H), 7.07 (app. td, 8.6, 3.0 Hz, 1H), 6.60 (br. s, 1H), 5.85 (br. s, 1H), 5.82 (d, 2.3 Hz, 1H), 3.77 (s, 3H). | 562.4 | A | A |
| I-1072 | 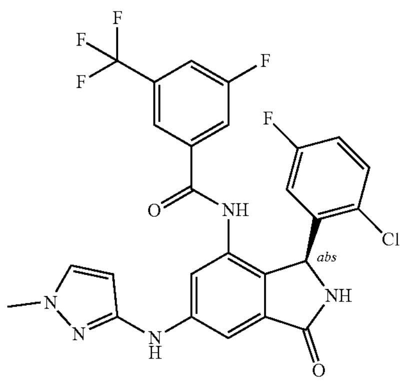 [SMILES: Cn1ccc(Nc2cc(NC(=O)c3cc(F)cc(C(F)(F)F)c3)c3c(c2)C(=O)N[C@@H]3c2cc(F)ccc2Cl)n1] | Cn1ccc(Nc2cc3C(=O)N1C@@H](c3c(NC(=O)c3cc(F)cc(c3)C(F)(F)F)c2)c2cc(F)cc2Cl)n1 | 1H-NMR (400 MHz, DMSO-d6) 10.43 (br. s, 1H), 8.97 (br. s, 1H), 8.90 (br. s, 1H), 7.91 (br. d, 6.5 Hz, 1H), 7.73-7.68 (m, 2H), 7.62 (br. s, 1H), 7.56 (d, 2.2 Hz, 1H), 7.41 (br. s, 1H), 7.29 (dd, 8.9, 5.2 Hz, 1H), 7.07 (app. td, 8.5, 3.0 Hz, 1H), 6.58 (br. s, 1H), 5.85 (s, 1H), 5.82 (d, 2.3 Hz, 1H), 3.77 (s, 3H) | 562.4 | C | |
| I-1073 | 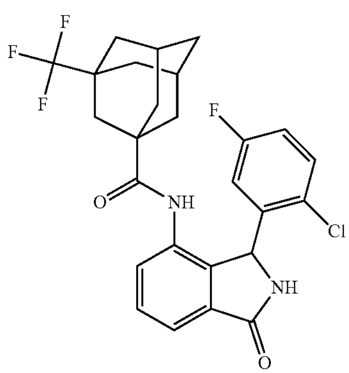 [SMILES: O=C1NC(c2cc(F)ccc2Cl)c2c(NC(=O)C34CC5CC(C3)CC(C(F)(F)F)(C5)C4)cccc21] | Fc1ccc(C1)c(c1)C1NC(=O)c2cccc(NC(=O)C34CC5CC(C3)CC(C5)(C4)C(F)(F)F)c12 | 1H-NMR (400 MHz, DMSO-d6) 9.37 (s, 1H), 9.09 (br. s, 1H), 7.61 (dd, 7.4, 1.1 Hz, 1H), 7.57 (t, 7.5 Hz, 1H), 7.52-7.45 (m, 1H), 7.36 (dd, 7.4, 1.0 Hz, 1H), 7.21 (app. td, 8.4, 3.1 Hz, 1H), 6.39 (br. s, 1H), 6.01 (br. s, 1H), 2.11-2.04 (m, 2H), 1.69-1.44 (m, 11H), 1.37-1.31 (m, 1H). | 507.4 | A | A |
| I-1074 | 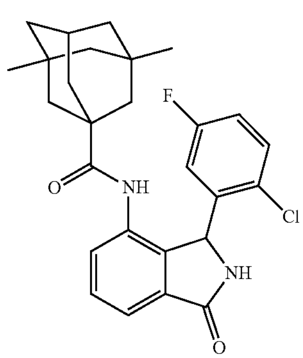 [SMILES: CC12CC3CC(C)(C1)CC(C(=O)Nc1cccc4c1C(c1cc(F)ccc1Cl)NC4=O)(C3)C2] | CC12CC3CC(C)(C1)CC(C3)(C2)C(=O)Nc1cccc2C(=O)NC(c12)c1cc(F)ccc1Cl | 1H-NMR (400 MHz, DMSO-d6) 9.09 (s, 1H), 9.07 (br. s, 1H), 7.61-7.53 (m, 2H), 7.53-7.47 (m, 1H), 7.41 (dd, 7.3, 1.5 Hz, 1H), 7.24 (ddd, 8.8, 8.1, 3.1 Hz, 1H), 6.41 (br. s, 1H), 6.03 (br. s, 1H), 1.98 (dt, 6.0, 3.0 Hz, 1H), 1.44-1.35 (m, 2H), 1.35-1.18 (m, 5H), 1.16-0.95 (m, 5H), 0.75 (s, 3H), 0.75 (s, 3H). | 467.4 | B | |

TABLE 2-continued

Representative Compounds of the Invention with Bioactivity Data.

| Ex. No. | Structure | SMILES | $^1$H NMR | MS | ADP-Glo IC$_{50}$ | MCF 10A IC$_{50}$ |
|---|---|---|---|---|---|---|
| I-1075 | 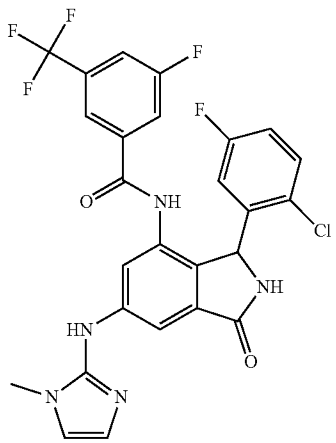 [SMILES: Cn1ccnc1Nc1cc(NC(=O)c2cc(F)cc(C(F)(F)F)c2)c2c(c1)C(=O)NC2c1cc(F)ccc1Cl] | Cn1ccnc1Nc1cc2C(=O)NC(c2c(NC(=O)c2cc(F)cc(c2)C(F)(F)F)c1)c1cc(F)ccc1Cl | 1H NMR (400 MHz, DMSO-d6) 10.42 (s, 1H), 9.01 (br. s, 1H), 8.75 (s, 1H), 8.15 (s, 1H), 7.93 (br. d, 8.9 Hz, 1H), 7.72 (d, 1.9 Hz, 1H), 7.71 (br. d, 8.9 Hz, 1H), 7.62 (s, 1H), 7.58 (d, 1.6 Hz), 1H, 7.30 (dd, 8.9, 5.2 Hz, 1H), 7.06 (td, 8.1, 3.1 Hz, 1H), 6.91 (d, 1.4 Hz, 1H), 6.70 (d, 1.4 Hz, 1H), 5.88 (br. s, 1H), 3.54 (s, 3H) | 562.3 | A | A |
| I-1076 | 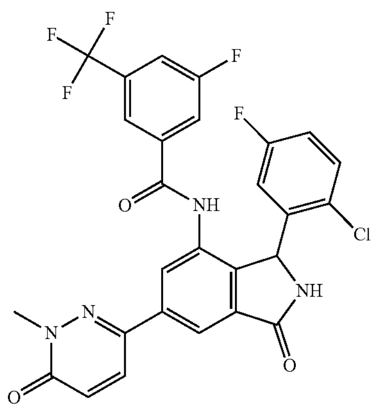 [SMILES: Cn1nc(-c2cc(NC(=O)c3cc(F)cc(C(F)(F)F)c3)c3c(c2)C(=O)NC3c2cc(F)ccc2Cl)ccc1=O] | Cn1nc(ccc1=O)-c1cc2C(=O)NC(c2c(NC(=O)c2cc(F)cc(c2)C(F)(F)F)c1)c1cc(F)ccc1Cl | NMR (400 MHz, DMSO) 10.65 (s, 1H), 9.26 (br s, 1H), 8.23 (d, 9.8 Hz, 1H), 8.18 (d, 1.0 Hz, 1H), 8.04 (s, 1H), 7.96 (d, 8.2 Hz, 1H), 7.77 (d, 9.4 Hz, 1H), 7.70 (s, 1H), 7.33 (dd, 8.9, 5.2 Hz, 1H), 7.14-7.06 (m, 2H), 6.04 (br s, 1H), 3.78 (s, 3H) | 573 | A | A |
| I-1077 | 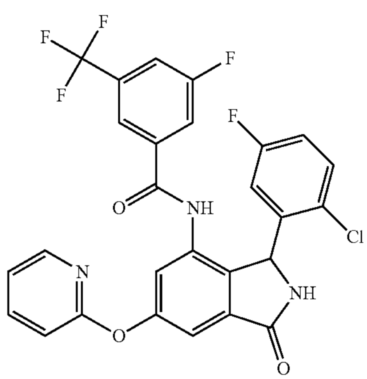 [SMILES: O=C(Nc1cc(Oc2ccccn2)cc2c1C(c1cc(F)ccc1Cl)NC2=O)c1cc(F)cc(C(F)(F)F)c1] | Fc1ccc(C1)c(c1)C1NC(=O)c2cc(Oc3ccccn3)cc(NC(=O)c3cc(F)cc(c3)C(F)(F)F)c12 | NMR (400 MHz, CD3CN) 8.62 (s, 1H), 8.17 (ddd, 5.0, 2.0, 0.8 Hz, 1H), 7.85 (ddd, 8.3, 7.2, 2.0 Hz, 1H), 7.67-7.62 (m, 1H), 7.60-7.54 (m, 2H), 7.49 (d, 2.1 Hz, 1H), 7.38-7.34 (m, 1H), 7.32-7.29 (m overlapped with dd, 1H), 7.28 (dd, 8.9, 5.1 Hz, 1H), 7.15 (ddd, 7.2, 5.0, 0.9 Hz, 1H), 7.09 (dt, 8.3, 0.8 Hz, 1H), 6.99 (ddd, 8.8, 8.0, 3.1 Hz, 1H), 6.71 (br s, 1H), 6.14 (br s, 1H) | 558 | B | |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-1078 | 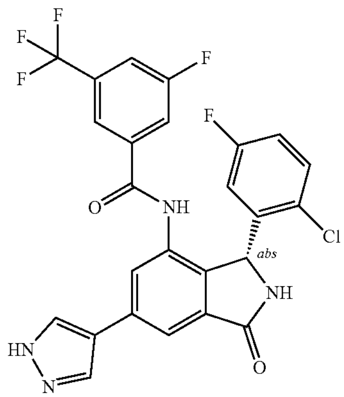 [SMILES: O=C(Nc1cc(-c2cn[nH]c2)cc2c1[C@H](c1cc(F)ccc1Cl)NC2=O)c1cc(F)cc(C(F)(F)F)c1] | Fc1ccc(C1)c(c1)[C@@H]1NC(=O)c2cc(cc(NC(=O)c3cc(F)cc(c3)C(F)(F)F)c12)-c1cn[nH]c1 | | 533 | A | A |
| I-1079 | 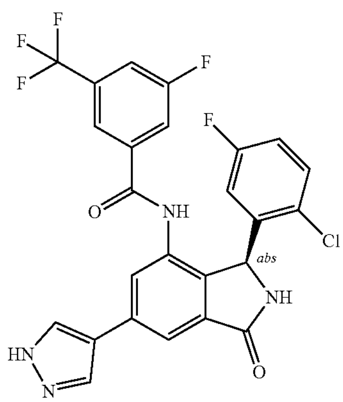 [SMILES: O=C(Nc1cc(-c2cn[nH]c2)cc2c1[C@@H](c1cc(F)ccc1Cl)NC2=O)c1cc(F)cc(C(F)(F)F)c1] | Fc1ccc(C1)c(c1)[C@H]1NC(=O)c2cc(cc(NC(=O)c3cc(F)cc(c3)C(F)(F)F)c12)-c1cn[nH]c1 | | 531 | A | |
| I-1080 | 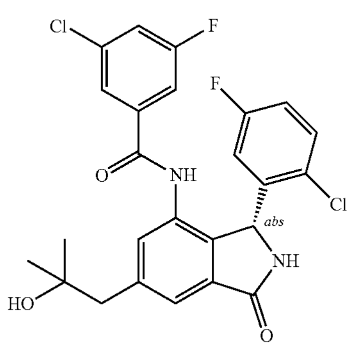 [SMILES: CC(C)(O)Cc1cc(NC(=O)c2cc(F)cc(Cl)c2)c2c(c1)C(=O)N[C@H]2c1cc(F)ccc1Cl] | CC(C)(O)Cc1cc2C(=O)N[C@H](c2c(NC(=O)c2cc(F)cc(Cl)c2)c1)c1cc(F)ccc1Cl | | 505 | A | A |

TABLE 2-continued

Representative Compounds of the Invention with Bioactivity Data.

| Ex. No. | Structure | SMILES | $^1$H NMR | MS | ADP-Glo IC$_{50}$ | MCF 10A IC$_{50}$ |
|---|---|---|---|---|---|---|
| I-1081 | 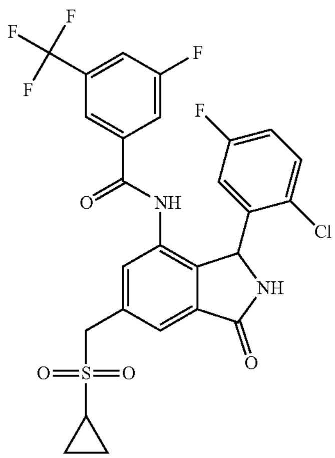 [SMILES: O=C(Nc1cc(CS(=O)(=O)C2CC2)cc2c1C(c1cc(F)ccc1Cl)NC2=O)c1cc(F)cc(C(F)(F)F)c1] | Fc1ccc(C1)c(c1)C1NC(=O)c2cc(CS(=O)(=O)C3CC3)cc(NC(=O)c3cc(F)cc(c3)C(F)(F)F)c12 | NMR (400 MHz, DMSO-d6) 10.61 (br. s, 1H), 9.21 (br. s, 1H), 7.95 (br. d, 8.3 Hz, 1H), 7.79 (d, 0.5 Hz, 1H), 7.74 (br. d, 9.0 Hz, 1H), 7.65 (s, 1H), 7.54 (s, 1H), 7.32 (dd, 8.9, 5.2 Hz, 1H), 7.10 (td, 8.5, 3.0 Hz, 1H), 6.59 (br. s, 1H), 5.98 (br. s, 1H), 4.77 (s, 2H), 2.71-2.61 (m, 1H), 1.02-0.91 (m, 2H), 0.89-0.79 (m, 2H). Presence of 2w% of OPPh3 (signals between 7.55 and 7.64). Partial formate salt at 8.41. | 585.2 | A | A |
| I-1082 | 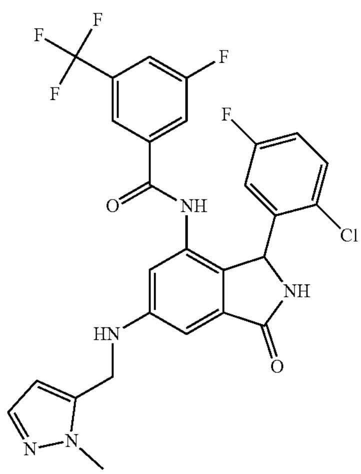 [SMILES: Cn1nccc1CNc1cc(NC(=O)c2cc(F)cc(C(F)(F)F)c2)c2c(c1)C(=O)NC2c1cc(F)ccc1Cl] | Cn1nccc1CNc1cc2C(=O)NC(c2c(NC(=O)c2cc(F)cc(c2)C(F)(F)F)c1)c1cc(F)ccc1Cl | NMR (400 MHz, DMSO-d6) 10.31 (s, 1H), 8.93 (br. s, 1H), 7.92 (br. d, 8.5 Hz, 1H), 7.69 (br. d, 9.0 Hz, 1H), 7.61 (s, 1H), 7.32 (d, 1.8 Hz, 1H), 7.28 (dd, 8.9, 5.2 Hz, 1H), 7.06 (td, 8.4, 3.1 Hz, 1H), 6.91 (d, 2.0 Hz, 1H), 6.79 (d, 1.6 Hz, 1H), 6.66 (br. t, 5.4 Hz, 1H), 6.59 (br. s, 1H), 6.22 (d, 1.7 Hz, 1H), 5.82 (br. s, 1H), 4.40 (d, 5.6 Hz, 2H), 3.83 (s, 3H). | 576.2 | A | A |
| I-1083 | 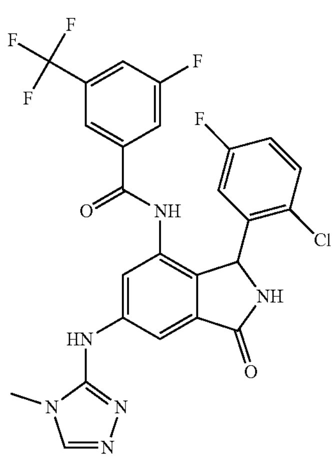 [SMILES: Cn1cnnc1Nc1cc(NC(=O)c2cc(F)cc(C(F)(F)F)c2)c2c(c1)C(=O)NC2c1cc(F)ccc1Cl] | Cn1cnnc1Nc1cc2C(=O)NC(c2c(NC(=O)c2cc(F)cc(c2)C(F)(F)F)c1)c1cc(F)ccc1Cl | 1H NMR (400 MHz, DMSO-d6) 10.50 (s, 1H), 9.12 (s, 1H), 9.08 (br. s, 1H), 8.22 (s, 1H), 7.93 (br. d, 9.5 Hz, 1H), 7.92 (d, 1.9 Hz, 1H), 7.84 (d, 1.8 Hz, 1H), 7.72 (br. d, 9.5 Hz, 1H), 7.63 (s, 1H), 7.31 (dd, 8.9, 5.2 Hz, 1H), 7.08 (td, 8.5, 3.0 Hz, 1H), 6.59 (br. s, 1H), 5.91 (br. s, 1H), 3.59 (s, 3H). | 563.3 | A | B |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-1084 | 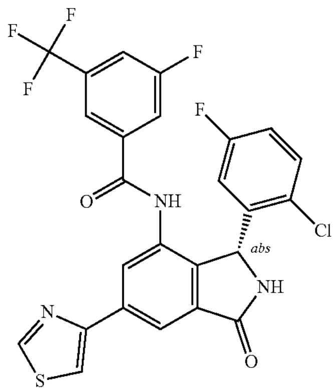 [SMILES: O=C(Nc1cc(-c2cscn2)cc2c1[C@H](c1cc(F)ccc1Cl)NC2=O)c1cc(F)cc(C(F)(F)F)c1] | Fc1ccc(C1)c(c1)[C@@H]1NC(=O)c2cc(cc(NC(=O)c3cc(F)cc(c3)C(F)(F)F)c12)-c1cscn1 | NMR (400 MHz, CD3CN) 9.01 (d, 1.9 Hz, 1H), 8.76 (br s, 1H), 8.29 (d, 1.4 Hz, 1H), 8.25 (s, 1H), 8.02 (d, 1.9 Hz, 1H), 7.70-7.59 (m, 3H), 7.32 (br s, 1H), 7.27 (dd, 8.9, 5.1 Hz, 1H), 6.98 (ddd, 8.8, 8.0, 3.1 Hz, 1H), 6.72 (br s, 1H), 6.18 (br s, 1H). | 550.3 | A | A |
| I-1085 | 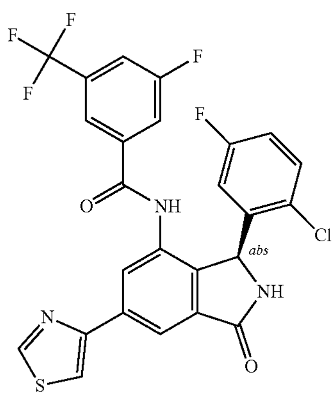 [SMILES: O=C(Nc1cc(-c2cscn2)cc2c1[C@@H](c1cc(F)ccc1Cl)NC2=O)c1cc(F)cc(C(F)(F)F)c1] | Fc1ccc(C1)c(c1)[C@H]1NC(=O)c2cc(cc(NC(=O)c3cc(F)cc(c3)C(F)(F)F)c12)-c1cscn1 | NMR (400 MHz, CD3CN) 9.01 (d, 1.9 Hz, 1H), 8.76 (br s, 1H), 8.29 (d, 1.4 Hz, 1H), 8.25 (s, 1H), 8.02 (d, 1.9 Hz, 1H), 7.70-7.59 (m, 3H), 7.32 (br s, 1H), 7.27 (dd, 8.9, 5.1 Hz, 1H), 6.98 (ddd, 8.8, 8.0, 3.1 Hz, 1H), 6.72 (br s, 1H), 6.18 (br s, 1H). | 550.3 | D | |
| I-1086 | 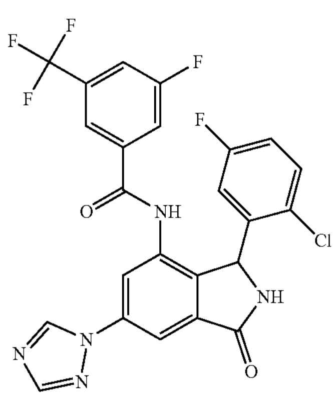 [SMILES: O=C(Nc1cc(-n2cncn2)cc2c1C(c1cc(F)ccc1Cl)NC2=O)c1cc(F)cc(C(F)(F)F)c1] | Fc1ccc(C1)c(c1)C1NC(=O)c2cc(cc(NC(=O)c3cc(F)cc(c3)C(F)(F)F)c12)-n1cncn1 | (400 MHz, DMSO-D6) 10.73 (s, 1 H), 9.55 (s, 1 H), 9.35 (s, 1 H), 8.32 (s, 1 H), 8.24 (d, 1.1 Hz, 1 H), 8.09 (s, 1 H), 7.96 (d, 8.5 Hz, 1 H), 7.76 (d, 8.9 Hz, 1 H), 7.68 (s, 1 H), 7.34 (dd, 8.9, 5.2 Hz, 1 H), 7.11 (td, 8.4, 3.1 Hz, 1 H), 6.65 (br s, 1 H), 6.05 (br s, 1 H). | 532.3 | A | A |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-1087 | 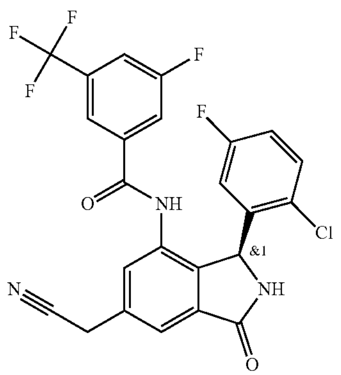 [SMILES: N#CCc1cc(NC(=O)c2cc(F)cc(C(F)(F)F)c2)c2c(c1)C(=O)N[C@@H]2c1cc(F)ccc1Cl] | Fc1ccc(C1)c(c1)[C@H]1NC(=O)c2cc(CC#N)cc(NC(=O)c3cc(F)cc(c3)C(F)(F)F)c12 | | 504.2 | B | |
| I-1088 | 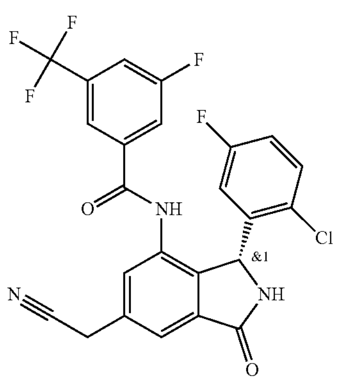 [SMILES: N#CCc1cc(NC(=O)c2cc(F)cc(C(F)(F)F)c2)c2c(c1)C(=O)N[C@H]2c1cc(F)ccc1Cl] | Fc1ccc(C1)c(c1)[C@@H]1NC(=O)c2cc(CC#N)cc(NC(=O)c3cc(F)cc(c3)C(F)(F)F)c12 | | 506.2 | A | A |
| I-1089 | 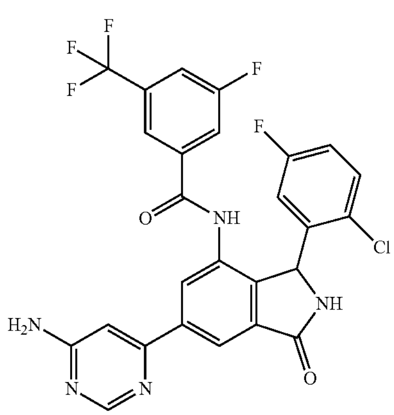 [SMILES: Nc1cc(-c2cc(NC(=O)c3cc(F)cc(C(F)(F)F)c3)c3c(c2)C(=O)NC3c2cc(F)ccc2Cl)ncn1] | Nc1cc(ncn1)-c1cc2C(=O)NC(c2c(NC(=O)c2cc(F)cc(c2)C(F)(F)F)c1)c1cc(F)ccc1Cl | 1H NMR (400 MHz, DMSO) 10.64 (s, 1H), 9.24 (s, 1H), 8.48 (d, 1.1 Hz, 1H), 8.19 (s, 2H), 7.94 (d, 8.4 Hz, 1H), 7.76 (d, 9.0 Hz, 1H), 7.70 (s, 1H), 7.65-7.51 (m, 1H), 7.32 (dd, 8.9, 5.2 Hz, 1H), 7.09 (td, 8.3, 3.1 Hz, 1H), 7.06-6.99 (m, 3H), 6.65 (s, 1H), 6.05 (s, 1H). | 560.36 | A | |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-1090 | 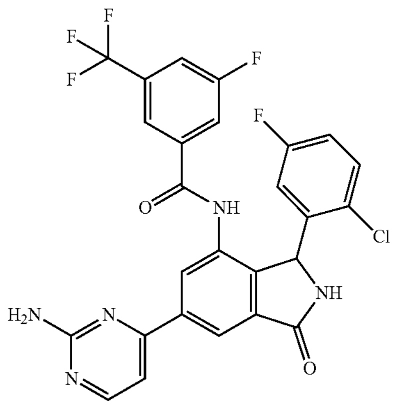 [SMILES: Nc1nccc(-c2cc(NC(=O)c3cc(F)cc(C(F)(F)F)c3)c3c(c2)C(=O)NC3c2cc(F)ccc2Cl)n1] | Nc1nccc(n1)-c1cc2C(=O)NC(c2c(NC(=O)c2cc(F)cc(c2)C(F)(F)F)c1)c1cc(F)ccc1Cl | 1H NMR (400 MHz, DMSO) 10.67 (s, 1H), 9.23 (s, 1H), 8.42-8.31 (m, 2H), 8.22 (s, 1H), 7.94 (d, 8.5 Hz, 1H), 7.77 (d, 9.2 Hz, 1H), 7.71 (s, 1H), 7.31 (dd, 8.9, 5.2 Hz, 1H), 7.27 (d, 5.2 Hz, 1H), 7.09 (td, 8.4, 3.1 Hz, 1H), 6.77 (s, 3H). | 560.31 | A | |
| I-1091 | 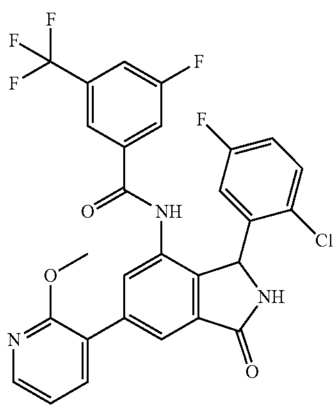 [SMILES: COc1ncccc1-c1cc(NC(=O)c2cc(F)cc(C(F)(F)F)c2)c2c(c1)C(=O)NC2c1cc(F)ccc1Cl] | COc1nccccc1-c1cc2C(=O)NC(c2c(NC(=O)c2cc(F)cc(c2)C(F)(F)F)c1)c1cc(F)ccc1Cl | 1H NMR (400 MHz, DMSO) 10.62 (s, 1H), 9.23 (s, 1H), 8.28 (d, 5.3 Hz, 1H), 8.01 (d, 1.6 Hz, 1H), 7.94 (d, 5.5 Hz, 2H), 7.75 (dd, 8.8, 2.4 Hz, 1H), 7.70 (s, 1H), 7.41 (dd, 5.4, 1.6 Hz, 1H), 7.33 (dd, 8.9, 5.2 Hz, 1H), 7.20 (d, 1.8 Hz, 1H), 7.09 (ddd, 8.8, 7.9, 3.1 Hz, 1H), 6.63 (s, 1H), 6.04 (s, 1H), 3.91 (s, 3H). | 574.32 | A | A |
| I-1092 | 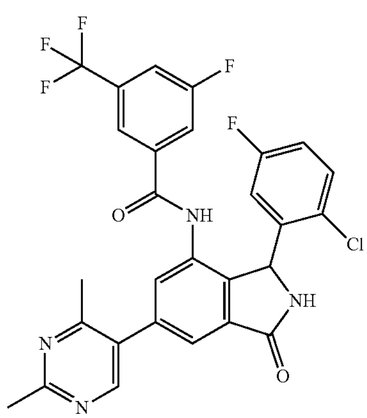 [SMILES: Cc1ncc(-c2cc(NC(=O)c3cc(F)cc(C(F)(F)F)c3)c3c(c2)C(=O)NC3c2cc(F)ccc2Cl)c(C)n1] | Cc1ncc(c(C)n1)-c1cc2C(=O)NC(c2c(NC(=O)c2cc(F)cc(c2)C(F)(F)F)c1)c1cc(F)ccc1Cl | | 573 | B | |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-1093 | 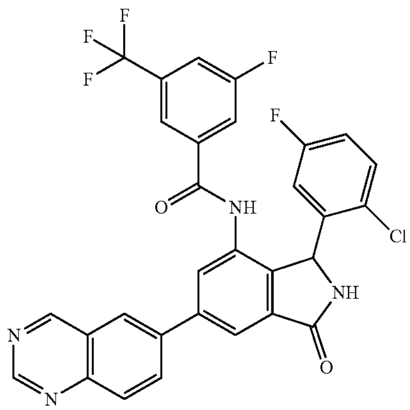 [SMILES: O=C(Nc1cc(-c2ccc3ncncc3c2)cc2c1C(c1cc(F)ccc1Cl)NC2=O)c1cc(F)cc(C(F)(F)F)c1] | Fc1ccc(C1)c(c1)CNC(=O)c2cc(cc(NC(=O)c3cc(F)cc(c3)C(F)(F)F)c12)-c1ccc2ncncc2c1 | | 595.5 | A | A |
| I-1094 | 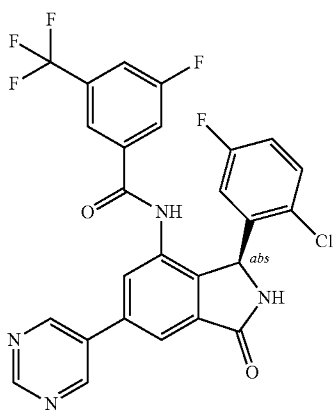 [SMILES: O=C(Nc1cc(-c2cncnc2)cc2c1[C@@H](c1cc(F)ccc1Cl)NC2=O)c1cc(F)cc(C(F)(F)F)c1] | Fc1ccc(C1)c(c1)[C@H]1NC(=O)c2cc(cc(NC(=O)c3cc(F)cc(c3)C(F)(F)F)c12)-c1cncnc1 | | 545.2 | C | |
| I-1095 | 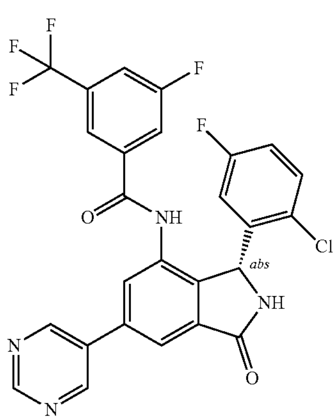 [SMILES: O=C(Nc1cc(-c2cncnc2)cc2c1[C@H](c1cc(F)ccc1Cl)NC2=O)c1cc(F)cc(C(F)(F)F)c1] | Fc1ccc(C1)c(c1)[C@@H]1NC(=O)c2cc(cc(NC(=O)c3cc(F)cc(c3)C(F)(F)F)c12)-c1cncnc1 | | 545.2 | A | A |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-1096 | 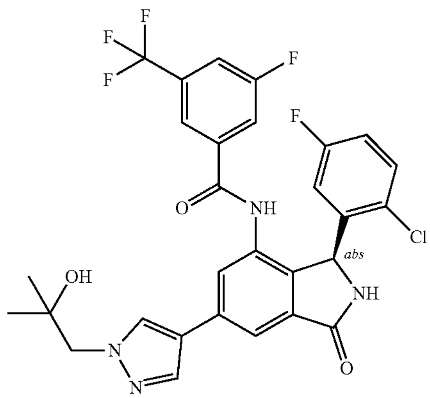 [SMILES: CC(C)(O)Cn1cc(-c2cc(NC(=O)c3cc(F)cc(C(F)(F)F)c3)c3c(c2)C(=O)N[C@@H]3c2cc(F)ccc2Cl)cn1] | CC(C)(O)Cn1cc(cn1)-c1cc2C(=O)N[C@@H](c2c(NC(=O)c2cc(F)cc(c2)C(F)(F)F)c1)c1cc(F)ccc1Cl | | 605.4 | E | |
| I-1097 | 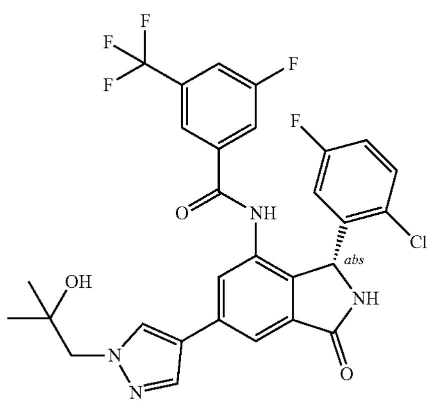 [SMILES: CC(C)(O)Cn1cc(-c2cc(NC(=O)c3cc(F)cc(C(F)(F)F)c3)c3c(c2)C(=O)N[C@H]3c2cc(F)ccc2Cl)cn1] | CC(C)(O)Cn1cc(cn1)-c1cc2C(=O)N[C@H](c2c(NC(=O)c2cc(F)cc(c2)C(F)(F)F)c1)c1cc(F)ccc1Cl | | 605.4 | A | A |
| I-1098 | 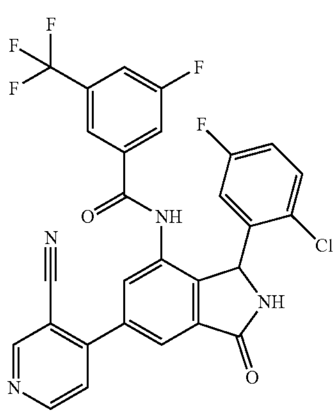 [SMILES: N#Cc1cnccc1-c1cc(NC(=O)c2cc(F)cc(C(F)(F)F)c2)c2c(c1)C(=O)NC2c1cc(F)ccc1Cl] | Fc1ccc(C1)c(c1)C1NC(=O)c2cc(cc(NC(=O)c3cc(F)cc(c3)C(F)(F)F)c12)-c1ccncc1C#N | | 569.26 | A | A |

TABLE 2-continued

Representative Compounds of the Invention with Bioactivity Data.

| Ex. No. | Structure | SMILES | $^1$H NMR | MS | ADP-Glo IC$_{50}$ | MCF 10A IC$_{50}$ |
|---|---|---|---|---|---|---|
| I-1099 | 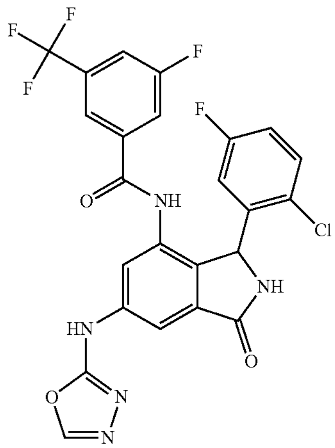 [SMILES: O=C(Nc1cc(Nc2nnco2)cc2c1C(c1cc(F)ccc1Cl)NC2=O)c1cc(F)cc(C(F)(F)F)c1] | Fc1ccc(C1)c(c1)C1NC(=O)c2cc(Nc3nnco3)cc(NC(=O)c3cc(F)cc(c3)C(F)(F)F)c12 | 1H-NMR (400 MHz, DMSO-d6) 11.00 (br. s, 1H), 10.59 (br. s, 1H), 9.15 (br. s, 1H), 8.82 (s, 1H), 7.94 (br. d, 8.7 Hz, 1H), 7.92 (d, 1.5 Hz, 1H), 7.77 (s, 1H), 7.73 (br. d, 9.0 Hz, 1H), 7.62 (s, 1H), 7.31 (dd, 8.9, 5.2 Hz, 1H), 7.09 (app. td, 8.4, 3.0 Hz, 1H), 6.62 (br. s, 1H), 5.93 (br. s, 1H). | 550.3 | A | A |
| I-1100 | 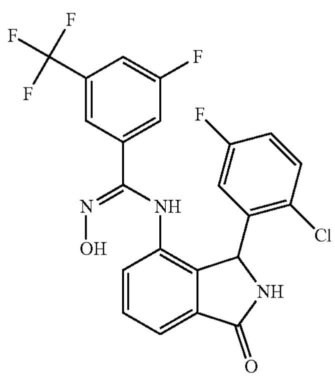 [SMILES: O=C1NC(c2cc(F)ccc2Cl)c2c(N/C(=N\O)c3cc(F)cc(C(F)(F)F)c3)cccc21] | O\N=C(/Nc1cccc2C(=O)NC(c12)c1cc(F)ccc1Cl)c1cc(F)cc(c1)C(F)(F)F | | 482.4 | A | |
| I-1101 | 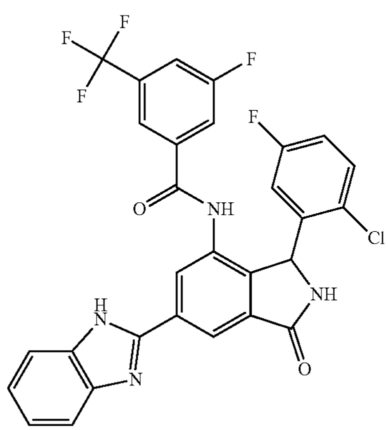 [SMILES: O=C(Nc1cc(-c2nc3ccccc3[nH]2)cc2c1C(c1cc(F)ccc1Cl)NC2=O)c1cc(F)cc(C(F)(F)F)c1] | Fc1ccc(C1)c(c1)C1NC(=O)c2cc(cc(NC(=O)c3cc(F)cc(c3)C(F)(F)F)c12)-c1nc2cccc2[nH]1 | 1H NMR (500 MHz, DMSO) 13.23 (s, 1H), 10.68 (s, 1H), 9.28 (s, 1H), 8.52-8.38 (m, 2H), 7.95 (d, 8.5 Hz, 1H), 7.79 (d, 8.8 Hz, 1H), 7.75-7.52 (m, 4H), 7.34-7.30 (m, 1H), 7.23 (s, 2H), 7.10 (dt, 8.7, 4.4 Hz, 1H), 6.64 (s, 1H), 6.08 (s, 1H). | 583.27 | A | A |

TABLE 2-continued

Representative Compounds of the Invention with Bioactivity Data.

| Ex. No. | Structure | SMILES | $^1$H NMR | MS | ADP-Glo IC$_{50}$ | MCF 10A IC$_{50}$ |
|---|---|---|---|---|---|---|
| I-1102 | 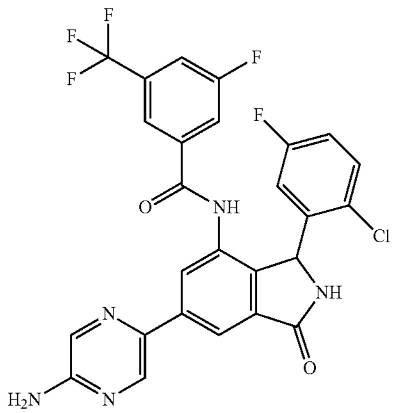 [SMILES: Nc1cnc(-c2cc(NC(=O)c3cc(F)cc(C(F)(F)F)c3)c3c(c2)C(=O)NC3c2cc(F)ccc2Cl)cn1] | Nc1cnc(cn1)-c1cc2C(=O)NC(c2c(NC(=O)c2cc(F)cc(c2)C(F)(F)F)c1)c1cc(F)ccc1Cl | 1H NMR (500 MHz, DMSO) 10.55 (s, 1H), 9.14 (s, 1H), 8.66 (d, 1.5 Hz, 1H), 8.19 (d, 1.6 Hz, 1H), 8.08 (d, 1.6 Hz, 1H), 7.98 (d, 1.5 Hz, 1H), 7.93 (d, 8.6 Hz, 1H), 7.76 (d, 9.2 Hz, 1H), 7.70 (s, 1H), 7.31 (dd, 8.9, 5.2 Hz, 1H), 7.08 (td, 8.4, 3.1 Hz, 1H), 6.70 (s, 2H), 6.01 (s, 1H). | 560.36 | A | A |
| I-1103 | 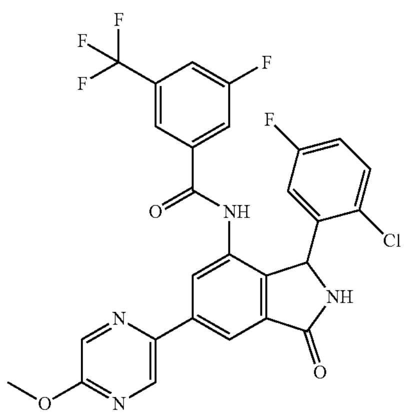 [SMILES: COc1cnc(-c2cc(NC(=O)c3cc(F)cc(C(F)(F)F)c3)c3c(c2)C(=O)NC3c2cc(F)ccc2Cl)cn1] | COc1cnc(cn1)-c1cc2C(=O)NC(c2c(NC(=O)c2cc(F)cc(c2)C(F)(F)F)c1)c1cc(F)ccc1Cl | 1H NMR (500 MHz, DMSO) 10.64 (s, 1H), 9.21 (s, 1H), 8.98 (d, 1.5 Hz, 1H), 8.44 (d, 1.4 Hz, 1H), 8.32 (d, 1.6 Hz, 1H), 8.20 (s, 1H), 7.94 (d, 8.5 Hz, 1H), 7.76 (d, 9.1 Hz, 1H), 7.70 (s, 1H), 7.32 (dd, 8.9, 5.1 Hz, 1H), 7.09 (td, 8.4, 3.1 Hz, 1H), 6.68 (s, 1H), 6.04 (s, 1H), 3.99 (s, 3H). | 575.31 | A | |
| I-1104 | 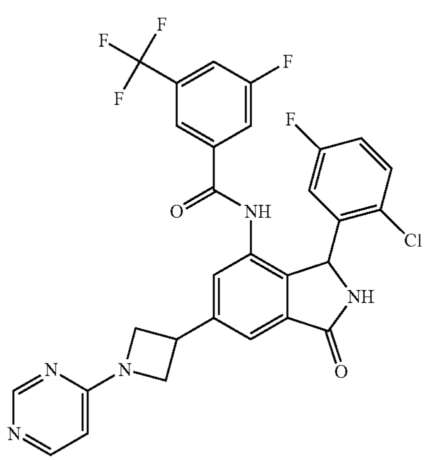 [SMILES: O=C(Nc1cc(C2CN(c3ccncn3)C2)cc2c1C(c1cc(F)ccc1Cl)NC2=O)c1cc(F)cc(C(F)(F)F)c1] | Fc1ccc(C1)c(c1)C1NC(=O)c2cc(cc(NC(=O)c3cc(F)cc(c3)C(F)(F)F)c12)C1CN(C1)c1ccncn1 | | 600.33 | A | A |

TABLE 2-continued

Representative Compounds of the Invention with Bioactivity Data.

| Ex. No. | Structure | SMILES | $^1$H NMR | MS | ADP-Glo IC$_{50}$ | MCF 10A IC$_{50}$ |
|---|---|---|---|---|---|---|
| I-1105 | 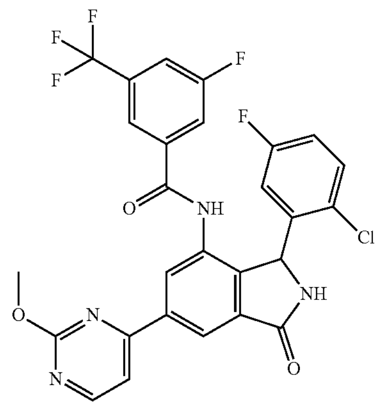 [SMILES: COc1nccc(-c2cc(NC(=O)c3cc(F)cc(C(F)(F)F)c3)c3c(c2)C(=O)NC3c2cc(F)ccc2Cl)n1] | COc1ncc c(n1)- c1cc2C(= O)NC(c2 c(NC(=O) c2cc(F)c c(c2)C(F) (F)F)c1)c 1cc(F)ccc 1Cl | 1H NMR (500 MHz, DMSO) 10.68 (s, 1H), 9.27 (s, 1H), 8.73 (d, 5.2 Hz, 1H), 8.47-8.31 (m, 2H), 7.92 (dd, 23.2, 6.7 H2, 2H), 7.80-7.65 (m, 2H), 7.32 (dd, 8.9, 5.2 Hz, 1H), 7.09 (td, 8.4, 3.0 Hz, 1H), 6.59 (s, 1H), 6.05 (s, 1H), 4.02 (s, 3H) | 575.31 | A | A |
| I-1106 | 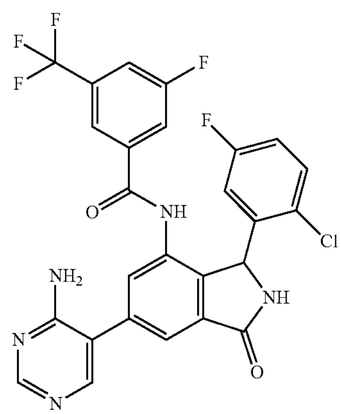 [SMILES: Nc1ncncc1-c1cc(NC(=O)c2cc(F)cc(C(F)(F)F)c2)c2c(c1)C(=O)NC2c1cc(F)ccc1Cl] | Nc1ncnc c1- c1cc2C(= O)NC(c2 c(NC(=O) c2cc(F)c c(c2)C(F) (F)F)c1)c 1cc(F)ccc 1Cl | | 560.5 | A | |
| I-1107 | 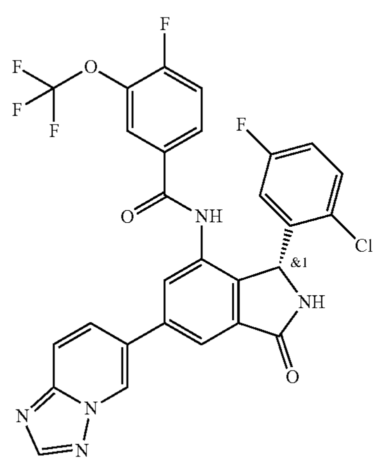 [SMILES: O=C(Nc1cc(-c2ccc3ncnn3c2)cc2c1[C@H](c1cc(F)ccc1Cl)NC2=O)c1ccc(F)c(OC(F)(F)F)c1] | Fc1ccc(C 1)c(c1)[C @@H]1 NC(=O)c 2cc(cc(N C(=O)c3 ccc(F)c (OC(F)(F) F)c3)c12)- c1ccc2nc nn2c1 | 1H NMR (400 MHz, DMSO-d6) 10.50 (s, 1H), 9.48 (t, 1.4 Hz, 1H), 9.25 (s, 1H), 8.58 (s, 1H), 8.18-8.10 (m, 2H), 8.02-7.92 (m, 2H), 7.85-7.74 (m, 2H), 7.67 (dd, 10.1, 8.7 Hz, 1H), 7.34 (dd, 8.9, 5.1 Hz, 1H), 7.11 (td, 8.4, 3.1 Hz, 1H), 6.68 (s, 1H), 6.08 (s, 1H). | 600.1 | B | |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-1108 | 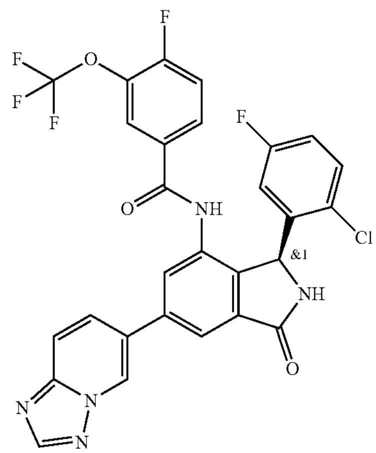 [SMILES: O=C(Nc1cc(-c2ccc3ncnn3c2)cc2c1[C@@H](c1cc(F)ccc1Cl)NC2=O)c1ccc(F)c(OC(F)(F)F)c1] | Fc1ccc(C1)c(c1)[C@H]1NC(=O)c2cc(cc(NC(=O)c3ccc(F)c(OC(F)(F)F)c3)c12)-c1ccc2ncnn2c1 | 1H NMR (400 MHz, DMSO-d6) 10.50 (s, 1H), 9.48 (t, 1.4 Hz, 1H), 9.25 (s, 1H), 8.58 (s, 1H), 8.18-8.10 (m, 2H), 8.02-7.92 (m, 2H), 7.85-7.74 (m, 2H), 7.67 (dd, 10.1, 8.7 Hz, 1H), 7.34 (dd, 8.9, 5.1 Hz, 1H), 7.11 (td, 8.4, 3.1 Hz, 1H), 6.68 (s, 1H), 6.08 (s, 1H). | 600.05 | | D |
| I-1109 | 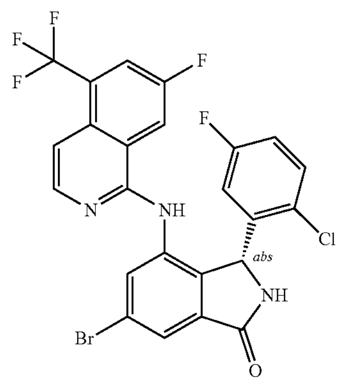 [SMILES: O=C1N[C@@H](c2cc(F)ccc2Cl)c2c(Nc3nccc4c(C(F)(F)F)cc(F)cc34)cc(Br)cc21] | Fc1ccc(C1)c(c1)[C@@H]1NC(=O)c2cc(Br)cc(Nc3nccc4c(cc(F)cc34)C(F)(F)F)c12 | 1H NMR (400 MHz, Chloroform-d) 8.35 (s, 1H), 8.21 (s, 1H), 7.88-7.83 (m, 2H), 7.50 (s, 1H), 7.34 (s, 1H), 7.10 (s, 1H), 6.99 (s, 1H), 6.68 (dd, 8.7, 3.0 Hz, 1H), 6.57-6.44 (m, 2H), 6.14 (s, 1H). | 569.9 | A | A |
| I-1110 | 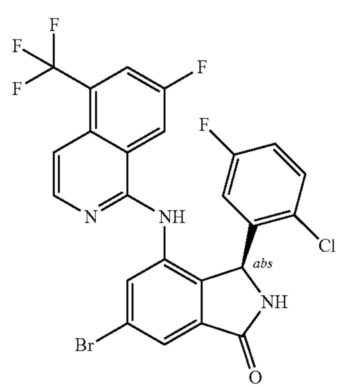 [SMILES: O=C1N[C@H](c2cc(F)ccc2Cl)c2c(Nc3nccc4c(C(F)(F)F)cc(F)cc34)cc(Br)cc21] | Fc1ccc(C1)c(c1)[C@H]1NC(=O)c2cc(Br)cc(Nc3nccc4c(cc(F)cc34)C(F)(F)F)c12 | 1H NMR (400 MHz, Chloroform-d) 8.34 (s, 1H), 8.22 (d, 6.2 Hz, 1H), 7.90-7.85(s,1H),7.80-7.85(s,1H) 7.53-7.46 (m, 1H), 7.32 (dd, 8.9, 4.9 Hz, 1H), 7.14-7.07 (m, 1H), 6.99 (s, 1H), 6.67-6.57 (m, 3H), 6.14 (s, 1H) | 569.9 | | D |

TABLE 2-continued

Representative Compounds of the Invention with Bioactivity Data.

| Ex. No. | Structure | SMILES | $^1$H NMR | MS | ADP-Glo IC$_{50}$ | MCF 10A IC$_{50}$ |
|---|---|---|---|---|---|---|
| I-1111 | 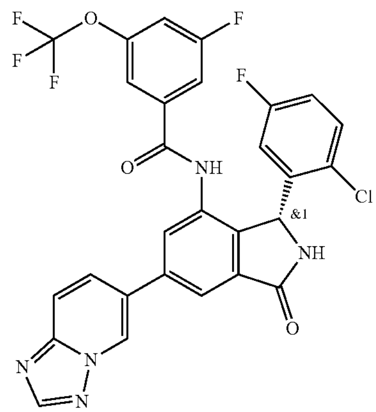 [SMILES: O=C(Nc1cc(-c2ccc3ncnn3c2)cc2c1[C@H](c1cc(F)ccc1Cl)NC2=O)c1cc(F)cc(OC(F)(F)F)c1] | Fc1ccc(C1)c(c1)[C@@H]1NC(=O)c2cc(cc(NC(=O)c3cc(F)cc(OC(F)(F)F)c3)c12)-c1ccc2ncnn2c1 | 1H NMR (400 MHz, DMSO-d6) 10.55 (s, 1H), 9.48 (dd, 1.9, 1.0 Hz, 1H), 9.26 (s, 1H), 8.58 (s, 1H), 8.18-8.03 (m, 2H), 8.03-7.95 (m, 2H), 7.68 (d, 8.8 Hz., 1H), 7.53 (d, 8.8 Hz, 1H), 7.46-7.42 (m, 1H), 7.36 (dd, 8.9, 5.2 Hz, 1H), 7.13 (td, 8.4, 3.1 Hz, 1H), 6.08 (s, 1H). | 600.1 | A | A |
| I-1112 | 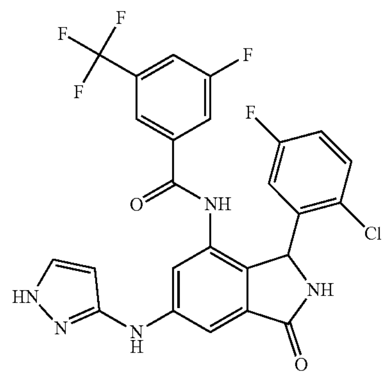 [SMILES: O=C(Nc1cc(Nc2cc[nH]n2)cc2c1C(c1cc(F)ccc1Cl)NC2=O)c1cc(F)cc(C(F)(F)F)c1] | Fc1ccc(C1)c(c1)C1NC(=O)c2cc(Nc3cc[nH]n3)cc(NC(=O)c3cc(F)cc(c3)C(F)(F)F)c12 | 1H NMR (400 MHz, DMSO-d6) 12.12 (s, 1H), 10.39 (s, 1H), 8.96 (br. s, 1H), 8.91 (s, 1H), 7.92 (d, 8.5 Hz, 1H), 7.74 (d, 0.9 Hz, 1H), 7.71 (br. d, 8.5 Hz, 1H), 7.62 (s, 1H), 7.47 (br. s, 1H), 7.29 (dd, 8.9, 5.2 Hz, 1H), 7.07 (td, 8.4, 3.1 Hz, 1H), 6.63 (br. s, 1H), 5.90 (m, 1H) | 548.3 | A | A |
| I-1113 | 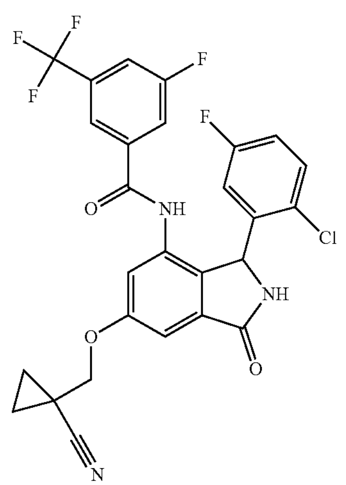 [SMILES: N#CC1(COc2cc(NC(=O)c3cc(F)cc(C(F)(F)F)c3)c3c(c2)C(=O)NC3c2cc(F)ccc2Cl)CC1] | Fc1ccc(C1)c(c1)C1NC(=O)c2cc(OCC3(CC3)C#N)cc(NC(=O)c3cc(F)cc(c3)C(F)(F)F)c12 | (400 MHz, DMSO-D6) 10.51 (br s, 1 H), 9.15 (br s, 1 H), 7.94 (d, 8.5 Hz, 1 H), 7.71 (d, 9.1 Hz, 1 H), 7.64 (s, 1 H), 7.31 (dd, 8.9, 5.2 Hz, 1 H), 7.22 (d, 2.1 Hz, 1 H), 7.13 (s, 1 H), 7.08 (td, 8.4, 3.1 Hz, 1 H), 6.61 (br s, 1 H), 5.93 (br s, 1 H), 4.18 (dd, 28.4, 10.4 Hz, 2 H), 1.40 (dd, 7.3, 4.7 Hz, 2 H), 1.20 (dd, 7.4, 4.9 Hz, 2 H). | 562.4 | A | |

TABLE 2-continued

Representative Compounds of the Invention with Bioactivity Data.

| Ex. No. | Structure | SMILES | $^1$H NMR | MS | ADP-Glo IC$_{50}$ | MCF 10A IC$_{50}$ |
|---|---|---|---|---|---|---|
| I-1114 | 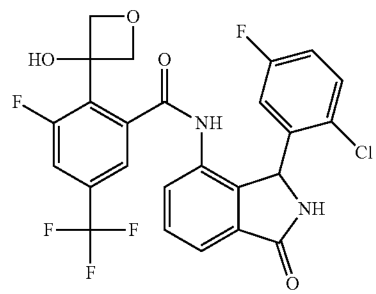 [SMILES: O=C1NC(c2cc(F)ccc2Cl)c2c(NC(=O)c3cc(C(F)(F)F)cc(F)c3C3(O)COC3)cccc21] | OC1(COC1)c1c(F)cc(cc1C(=O)Nc1ccc2C(=O)NC(c12)c1cc(F)ccc1Cl)C(F)(F)F | NMR (400 MHz, DMSO-d6) 10.62 (br. s, 1H), 9.16 (br. s, 1H), 7.90 (d, 10.6 Hz, 1H), 7.70 (d, 7.4 Hz, 1H), 7.65 (t, 7.5 Hz, 1H), 7.55-7.44 (m, 2H), 7.23 (td, 8.4, 2.9 Hz, 1H), 6.51 (s, 1H), 6.33 (br. s, 1H), 6.00 (br. s, 1H), 4.91 (dd, 7.3, 1.8 Hz., 1H), 4.79 (d, 7.5 Hz, 1H), 4.65 (d, 7.4 Hz, 1H), 4.43 (d, 7.5 Hz, 1H) | 539.2 | D | |
| I-1115 | 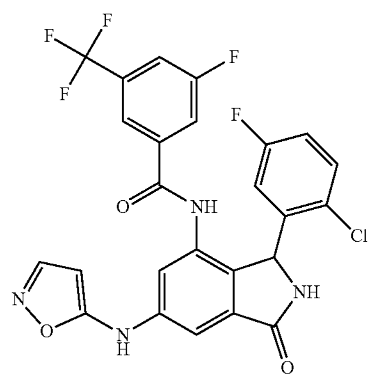 [SMILES: O=C(Nc1cc(Nc2ccno2)cc2c1C(c1cc(F)ccc1Cl)NC2=O)c1cc(F)cc(C(F)(F)F)c1] | Fc1ccc(C1)c(c1)C1NC(=O)c2cc(Nc3ccno3)cc(NC(=O)c3cc(F)cc(c3)C(F)(F)F)c12 | 1H-NMR (400 MHz, DMSO-d6) 10.65 (br. s, 1H), 9.28 (br. s, 1H), 8.00 (br. d, 10.2 Hz, 1H), 7.95 (d, 8.1 Hz, 1H), 7.79 (d, 4.4 Hz, 1H), 7.74 (br. d, 8.3 Hz, 1H), 7.67 (br. s, 1H), 7.64 (s, 1H), 7.58 (s, 1H), 7.32 (dd, 8.7, 5.1 Hz, 1H), 7.10 (app. td, 8.4, 3.0 Hz, 1H), 6.63 (br. s, 1H), 5.99 (br. s, 1H), 5.33 (s, 1H). | 549.2 | A | |
| I-1116 | 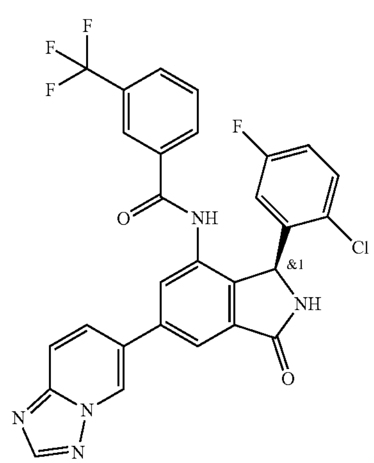 [SMILES: O=C(Nc1cc(-c2ccc3ncnn3c2)cc2c1[C@@H](c1cc(F)ccc1Cl)NC2=O)c1cccc(C(F)(F)F)c1] | Fc1ccc(C1)c(c1)[C@H]1NC(=O)c2cc(cc(NC(=O)c3cccc(c3)C(F)(F)c12)-c1ccc2ncnn2c1 | 1H NMR (400 MHz, DMSO-d6) 10.57 (s, 1H), 9.48 (t, 1.3 Hz, 1H), 9.25 (s, 1H), 8.58 (s, 1H), 8.18-8.04 (m, 2H), 8.03-7.90 (m, 4H), 7.83 (s, 1H), 7.74 (t, 7.8 Hz, 1H), 7.34 (dd, 8.9, 5.1 Hz, 1H), 7.11 (td, 8.4, 3.1 Hz, 1H), 6.11 (s, 1H), 1.24 (s, 1H) | 566.05 | E | |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-1117 | 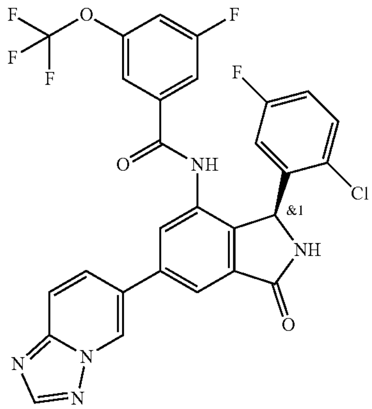 [SMILES: O=C(Nc1cc(-c2ccc3ncnn3c2)cc2c1[C@@H](c1cc(F)ccc1Cl)NC2=O)c1cc(F)cc(OC(F)(F)F)c1] | Fc1ccc(C1)c(c1)[C@H]1NC(=O)c2cc(cc(NC(=O)c3cc(F)cc(OC(F)(F)F)c3)c12)-c1ccc2ncnn2c1 | 1H NMR (400 MHz, DMSO-d6) 10.55 (s, 1H), 9.48 (dd, 1.9, 1.0 Hz, 1H), 9.26 (s, 1H), 8.58 (s, 1H), 8.18-8.03 (m, 2H), 8.03-7.95 (m, 2H), 7.68 (d, 8.8 Hz, 1H), 7.53 (d, 8.8 Hz, 1H), 7.46-7.42 (m, 1H), 7.36 (dd, 8.9, 5.2 Hz, 1H), 7.13 (td, 8.4, 3.1 Hz, 1H), 6.08 (s, 1H). | 600.1 | D | |
| I-1118 | 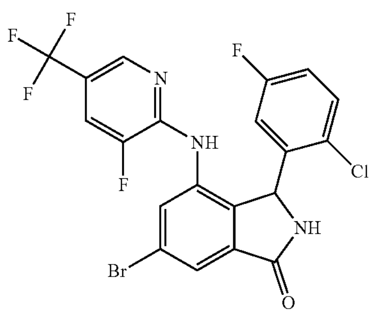 [SMILES: O=C1NC(c2cc(F)ccc2Cl)c2c(Nc3ncc(C(F)(F)F)cc3F)cc(Br)cc21] | Fc1ccc(C1)c(c1)C1NC(=O)c2cc(Br)cc(Nc3ncc(cc3F)C(F)(F)F)c12 | 1H NMR (400 MHz, DMSO-d6) 10.10 (s, 1H), 10.04 (s, 1H), 9.06 (s, 1H), 8.72 (dd, 11.2, 2.1 Hz, 1H), 8.58-8.50 (m, 2H), 8.12 (dd, 8.9, 5.1 Hz, 1H), 7.90 (ddd, 8.8, 7.9, 3.1 Hz, 1H), 7.34 (s, 1H), 6.76 (s, 1H) | 518 | C | |
| I-1119 | 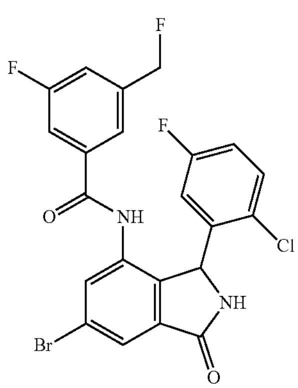 [SMILES: O=C(Nc1cc(Br)cc2c1C(c1cc(F)ccc1Cl)NC2=O)c1cc(F)cc(CF)c1] | FCc1cc(F)cc(c1)C(=O)Nc1cc(Br)cc2C(=O)NC(c12)c1cc(F)ccc1Cl | 1H NMR (400 MHz, Chloroform-d) 8.49 (s, 1H), 7.96 (s, 1H), 7.45 (dd, 8.9, 4.9 Hz, 2H), 7.38 (s, 1H), 7.26-7.18 (m, 2H), 7.14-7.05 (m, 1H), 6.72 (s, 1H), 6.50 (s, 1H), 6.19 (s, 1H), 5.48 (s, 1H), 5.37 (s, 1H). | 509 | C | |

TABLE 2-continued

Representative Compounds of the Invention with Bioactivity Data.

| Ex. No. | Structure | SMILES | $^1$H NMR | MS | ADP-Glo IC$_{50}$ | MCF 10A IC$_{50}$ |
|---|---|---|---|---|---|---|
| I-1120 | 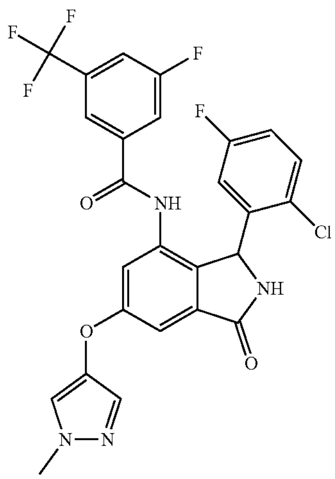 [SMILES: Cn1cc(Oc2cc(NC(=O)c3cc(F)cc(C(F)(F)F)c3)c3c(c2)C(=O)NC3c2cc(F)ccc2Cl)cn1] | Cn1cc(Oc2cc3C(=O)NC(c3c(NC(=O)c3cc(F)cc(c3)C(F)(F)F)c2)c2cc(F)ccc2Cl)cn1 | NMR (400 MHz, DMSO) 10.50 (s, 1H), 8.52 (s, 1H), 7.98 (s, 1H), 7.84 (d, 9.2 Hz, 1H), 7.83 (s, 1H), 7.79 (s, 1H), 7.54 (d, 0.6 Hz, 1H), 7.51 (dd, 9.2, 3.0 Hz, 1H), 7.22 (dd, 8.8, 5.2 Hz, 1H), 7.08 (d, 1.7 Hz, 1H), 7.02 (td, 8.5, 3.1 Hz, 1H), 6.92 (br s, 1H), 6.04 (s, 1H), 3.74 (s, 3H). | 563 | D | |
| I-1121 | 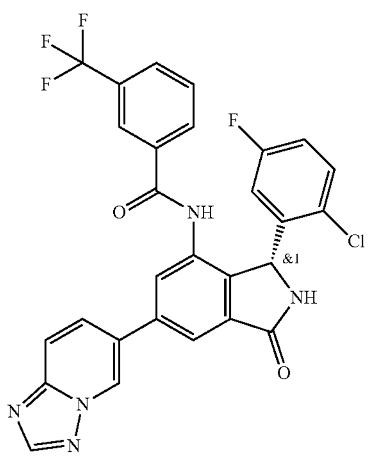 [SMILES: O=C(Nc1cc(-c2ccc3ncnn3c2)cc2c1[C@H](c1cc(F)ccc1Cl)NC2=O)c1cccc(C(F)(F)F)c1] | Fc1ccc(C1)c(c1)[C@@H]1NC(=O)c2cc(cc(NC(=O)c3cccc(c3)C(F)(F)F)c12)-c1ccc2ncnn2c1 | 1H NMR (400 MHz, DMSO-d6)10.57 (s, 1H), 9.48 (t, 1.3 Hz, 1H), 9.25 (s, 1H), 8.58 (s, 1H), 8.18-8.04 (m, 2H), 8.03-7.90 (m, 4H), 7.83 (s, 1H), 7.74 (t, 7.8 Hz, 1H), 7.34 (dd, 8.9, 5.1 Hz, 1H), 7.11 (td, 8.4, 3.1 Hz, 1H), 6.11 (s, 1H), 1.24 (s, 1H). | 566.05 | A | |
| I-1122 | 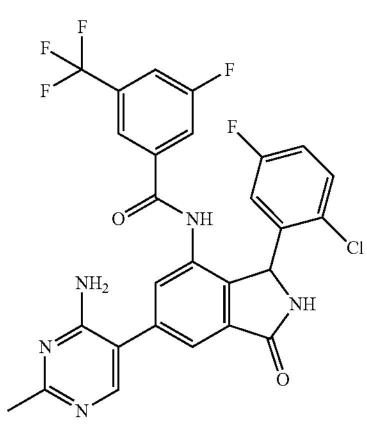 [SMILES: Cc1ncc(-c2cc(NC(=O)c3cc(F)cc(C(F)(F)F)c3)c3c(c2)C(=O)NC3c2cc(F)ccc2Cl)c(N)n1] | Cc1ncc(c(N)n1)-c1cc2C(=O)NC(c2c(NC(=O)c2cc(F)cc(c2)C(F)(F)F)c1)c1cc(F)ccc1Cl | | 574.4 | A | |

TABLE 2-continued

Representative Compounds of the Invention with Bioactivity Data.

| Ex. No. | Structure | SMILES | $^1$H NMR | MS | ADP-Glo IC$_{50}$ | MCF 10A IC$_{50}$ |
|---|---|---|---|---|---|---|
| I-1123 | 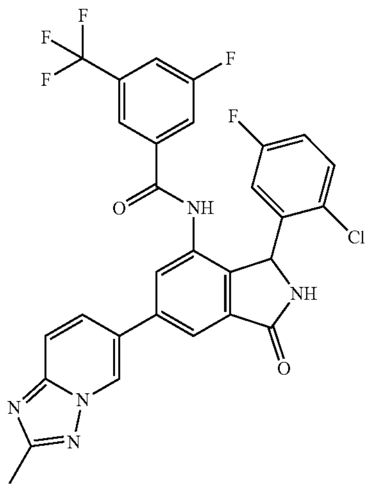 [SMILES: Cc1nc2ccc(-c3cc(NC(=O)c4cc(F)cc(C(F)(F)F)c4)c4c(c3)C(=O)NC4c3cc(F)ccc3Cl)cn2n1] | Cc1nc2cc c(cn2n1)-c1cc2C(= O)NC(c2 c(NC(=O) c2cc(F)c c(c2)C(F) (F)F)c1)c 1cc(F)ccc 1Cl | | 598.6 | A | A |
| I-1124 | 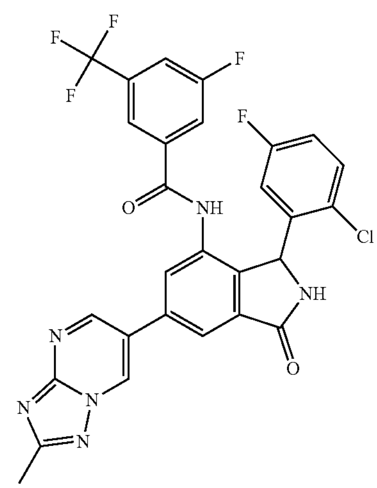 [SMILES: Cc1nc2ncc(-c3cc(NC(=O)c4cc(F)cc(C(F)(F)F)c4)c4c(c3)C(=O)NC4c3cc(F)ccc3Cl)cn2n1] | Cc1nc2n cc(cn2n1)-c1cc2C(= O)NC(c2 c(NC(=O) c2cc(F)c c(c2)C(F) (F)F)c1)c 1cc(F)ccc 1Cl | | 599.5 | A | A |
| I-1125 | 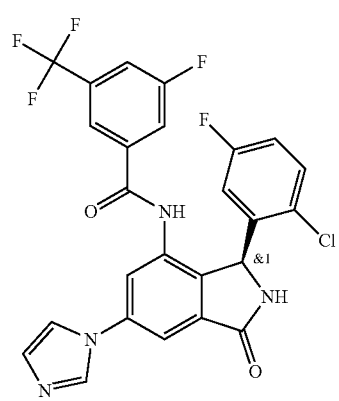 [SMILES: O=C(Nc1cc(-n2ccnc2)cc2c1[C@@H](c1cc(F)ccc1Cl)NC2=O)c1cc(F)cc(C(F)(F)F)c1] | Fc1ccc(C 1)c(c1)[C @H]1NC (=O)c2cc (cc(NC(= O)c3cc(F) cc(c3)C (F)(F)F)c1 2)-n1ccnc1 | (400 MHz, DMSO-D6) 10.71 (br s, 1 H), 9.31 (s, 1 H), 8.45 (s, 1 H), 8.03-7.90 (m, 3 H), 7.84 (s, 1 H), 7.76 (d, 8.8 Hz, 1 H), 7.69 (s, 1 H), 7.33 (dd, 8.9, 5.1 Hz, 1 H), 7.16 (s, 1 H), 7.10 (td, 8.4, 2.9 Hz, 1 H), 6.67 (br s, 1 H), 6.02 (br s, 1 H). | 533.3 | B | |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-1126 | 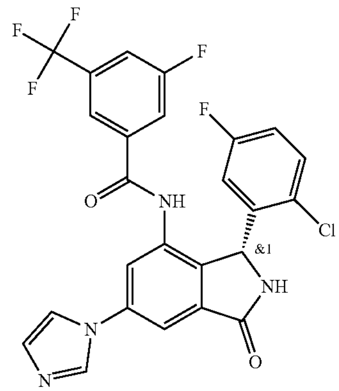 [SMILES: O=C(Nc1cc(-n2ccnc2)cc2c1[C@H](c1cc(F)ccc1Cl)NC2=O)c1cc(F)cc(C(F)(F)F)c1] | Fc1ccc(C1)c(c1)[C@@H]1NC(=O)c2cc(cc(NC(=O)c3cc(F)cc(c3)C(F)(F)F)c12)-n1ccnc1 | (400 MHz, DMSO-D6) 10.71 (br s, 1 H), 9.31 (s, 1 H), 8.45 (s, 1 H), 8.03-7.90 (m, 3 H), 7.84 (s, 1 H), 7.76 (d, 8.8 Hz, 1 H), 7.69 (s, 1 H), 7.33 (dd, 8.9, 5.1 Hz, 1 H), 7.16 (s, 1 H), 7.10 (td, 8.4, 2.9 Hz, 1 H), 6.67 (br s, 1 H), 6.02 (br s, 1 H). | 533.3 | A | |
| I-1127 | 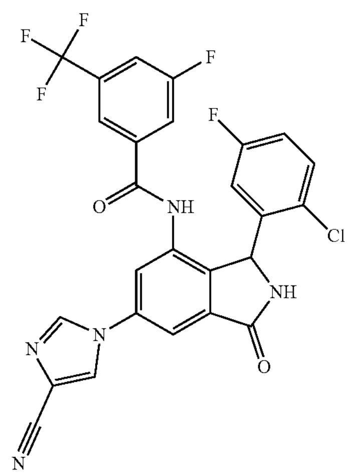 [SMILES: N#Cc1cn(-c2cc(NC(=O)c3cc(F)cc(C(F)(F)F)c3)c3c(c2)C(=O)NC3c2cc(F)ccc2Cl)cn1] | Fc1ccc(C1)c(c1)C1NC(=O)c2cc(cc(NC(=O)c3cc(F)cc(c3)C(F)(F)F)c12)-n1cnc(c1)C#N | (400 MHz, DMSO-D6) 9.36 (s, 1 H), 8.90 (d, 1.1 Hz, 1 H), 8.67 (d, 0.9 Hz, 1 H), 8.06 (s, 1 H), 7.94 (d, 6.7 Hz, 2 H), 7.79-7.62 (m, 3 H), 7.34 (dd, 8.9, 5.2 Hz, 1 H), 7.11 (td, 8.4, 3.0 Hz, 1 H), 6.67 (br s, 1 H), 6.03 (br s, 1 H). | 556.3 | A | |
| I-1128 | 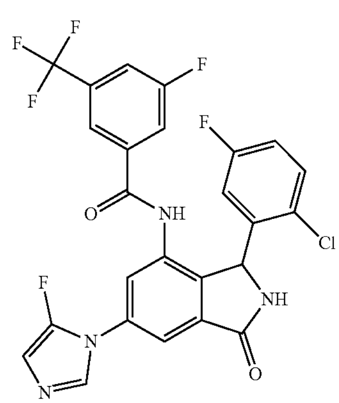 [SMILES: O=C(Nc1cc(-n2cncc2F)cc2c1C(c1cc(F)ccc1Cl)NC2=O)c1cc(F)cc(C(F)(F)F)c1] | Fc1cncn1-c1cc2C(=O)NC(c2c(NC(=O)c2cc(F)cc(c2)C(F)(F)F)c1)cc1cc(F)ccc1Cl | (400 MHz, DMSO-D6) 9.33 (s, 1 H), 8.39 (br s, 1 H), 8.23 (s, 1 H), 8.00 (s, 1 H), 7.96 (d, 8.3 Hz, 1 H), 7.88 (s, 1 H), 7.80-7.73 (m, 2 H), 7.71 (s, 1 H), 7.33 (dd, 8.8, 5.1 Hz, 1 H), 7.10 (td, 8.4, 2.7 Hz, 1 H), 6.71 (br s, 1 H), 6.03 (br s, 1 H). | 551.3 | A | |

TABLE 2-continued

Representative Compounds of the Invention with Bioactivity Data.

| Ex. No. | Structure | SMILES | $^1$H NMR | MS | ADP-Glo IC$_{50}$ | MCF 10A IC$_{50}$ |
|---|---|---|---|---|---|---|
| I-1129 | 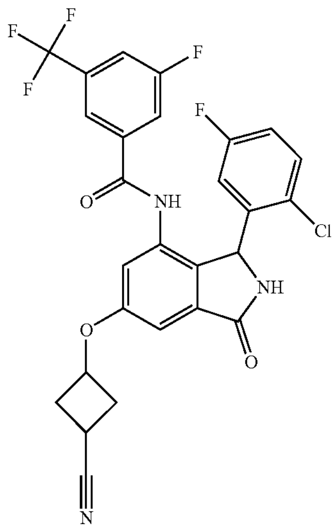 [SMILES: N#CC1CC(Oc2cc(NC(=O)c3cc(F)cc(C(F)(F)F)c3)c3c(c2)C(=O)NC3c2cc(F)ccc2Cl)C1] | Fc1ccc(C1)c(c1)C1NC(=O)c2cc(OC3CC(C3)C#N)cc(NC(=O)c3cc(F)cc(c3)C(F)(F)F)c12 | 1H NMR (400 MHz, DMSO-d6) 10.44 (s, 1H), 9.14 (s, 1H), 7.94 (dt, 8.5, 1.2 Hz, 1H), 7.71 (br. d, 8.9 Hz, 1H), 7.62 (s, 1H), 7.31 (dd, 8.9, 5.2 Hz, 1H), 7.12-7.05 (m, 2H), 7.03 d, 1.6 Hz, 1H), 6.58 (br. s, 1H), 5.92 (br. s, 1H), 5.19-5.08 (m, 1H), 3.53-3.44 (m, 1H), 2.92-2.80 (m, 2H), 2.62-2.52 (m, 2H) | 562.3 | A | |
| I-1130 | 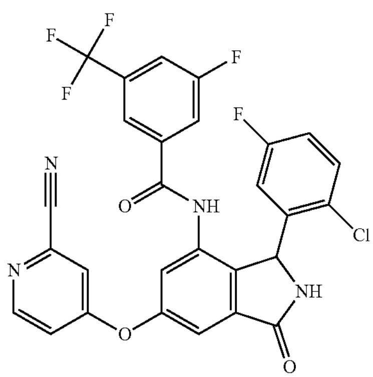 [SMILES: N#Cc1cc(Oc2cc(NC(=O)c3cc(F)cc(C(F)(F)F)c3)c3c(c2)C(=O)NC3c2cc(F)ccc2Cl)ccn1] | Fc1ccc(C1)c(c1)C1NC(=O)c2cc(Oc3cnc(C#N)cc(NC(=O)c3cc(F)cc(c3)C(F)(F)F)c12 | (400 MHz, DMSO-d6) 10.68 (br s, 1H), 9.31 (s, 1H), 8.67 (d, 5.7 Hz, 1H), 7.91 (d, 6.8 Hz, 1H), 7.86 (s, 1H), 7.71 (d, 8.4 Hz, 1H), 7.63 (s, 1H), 7.52-7.43 (m, 2H), 7.40-7.31 (m, 2H), 7.11 (td, 8.5, 3.0 Hz, 1H), 6.87 (br s, 1H), 6.05 (s, 1H). | 583.4 | A | |
| I-1131 | 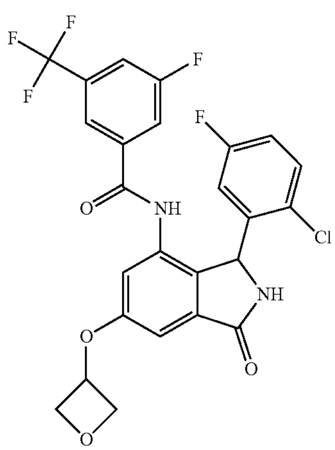 [SMILES: O=C(Nc1cc(OC2COC2)cc2c1C(c1cc(F)ccc1Cl)NC2=O)c1cc(F)cc(C(F)(F)F)c1] | Fc1ccc(C1)c(c1)C1NC(=O)c2cc(OC3COC3)cc(NC(=O)c3cc(F)cc(c3)C(F)(F)F)c12 | (400 MHz, DMSO-d6) 10.52 (br s, 1H), 9.15 (s, 1H), 7.94 (d, 8.4 Hz, 1H), 7.71 (d, 8.9 Hz, 1H), 7.63 (s, 1H), 7.30 (dd, 8.8, 5.2 Hz, 1H), 7.08 (td, 8.5, 3.0 Hz, 1H), 7.00 (s, 1H), 6.97 (d, 2.1 Hz, 1H), 6.65 (br s, 1H), 5.92 (s, 1H), 5.44 (p, 5.2 Hz, 1H), 4.98 (t, 6.6 Hz, 2H), 4.64-4.57 (m, 2H) | 537.3 | A | |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-1132 | 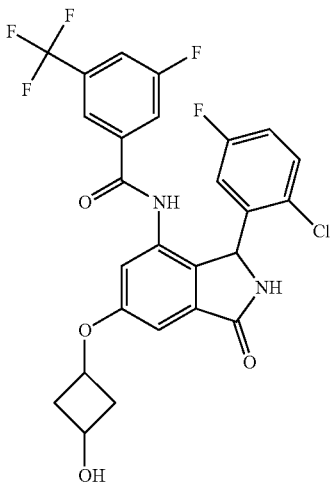 [SMILES: O=C(Nc1cc(OC2CC(O)C2)cc2c1C(c1cc(F)ccc1Cl)NC2=O)c1cc(F)cc(C(F)(F)F)c1] | OC1CC(C1)Oc1cc2C(=O)NC(c2c(NC(=O)c2cc(F)cc(c2)C(F)(F)F)c1)c1cc(F)ccc1Cl | NMR (400 MHz, DMSO-d6) 8.60 (br. d, 7.9 Hz, 1H), 7.67-7.55 (m, 3H), 7.30-7.23 (m, 2H), 7.21 (br. s, 1H), 7.13 (dd, 5.6, 2.1 Hz, 2H), 6.96 (ddd, 8.8, 8.0, 3.1 Hz), 6.64 (br. s, 1H), 6.05 (br. s, 1H), 4.77-4.68 (m, 1H), 3.69-3.62 (m, 1H), 1.36 (dd, 6.0, 5.2 Hz, 2H), 1.28-1.25 (m, 1H), 1.19 (d, 6.2 Hz, 1H) | 555.3 | B | |
| I-1133 | 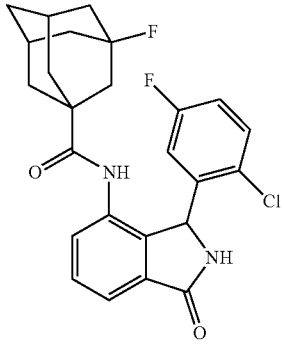 [SMILES: O=C1NC(c2cc(F)ccc2Cl)c2c(NC(=O)C34CC5CC(CC(F)(C5)C3)C4)cccc21] | Fc1ccc(C1)c(c1)C1NC(=O)c2cccc(NC(=O)C34CC5CC(CC(F)(C5)C3)C4)c12 | 1H-NMR (400MHz, DMSO-d6)-9.29 (s, 1H), 9.08 (br. s, 1H), 7.61 (dd, 7.3, 1.1 Hz, 1H), 7.57 (t, 7.5 Hz, 1H), 7.54-7.47 (m, 1H), 7.37 (dd, 7.5, 1.3 Hz, 1H), 7.24 (ddd, 8.8, 8.1, 3.1 Hz, 1H), 6.42 (br. s, 1H), 6.02 (br. s, 1H), 2.24-2.15 (m, 2H), 1.78 (d, 2.8 Hz, 1H), 1.77-1.72 (m, 1H), 1.71-1.64 (m, 3H), 1.62-1.56 (m, 1H), 1.53-1.39 (m, 5H), 1.37-1.31 (m, 1H). | 457.4 | C | |
| I-1134 | 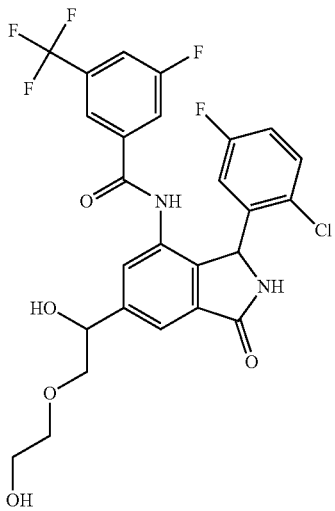 [SMILES: O=C(Nc1cc(C(O)COCCO)cc2c1C(c1cc(F)ccc1Cl)NC2=O)c1cc(F)cc(C(F)(F)F)c1] | OCCOCC(O)c1cc2C(=O)NC(c2c(NC(=O)c2cc(F)cc(c2)C(F)(F)F)c1)c1cc(F)ccc1Cl | NMR (400 MHz, DMSO-d6 ) 10.55 (br s, 1H), 9.19 (br s 1H), 7.91 (d, 7.1 Hz, 1H), 7.79-7.69 (m, 2H), 7.66 (s, 2H), 7.54-7.48 (m, 1H), 7.31 (dd, 8.8, 5.2 Hz, 1H), 7.09 (tt, 8.7, 4.3 Hz, 1H), 5.96 (br s, 1H), 5.62 (d, 8.0 Hz, 1H), 4.88 (ddd, 16.6, 11.5, 5.0 Hz, 1H), 4.60 (dd, 5.0, 3.7 Hz, 1H), 3.62-3.52 (m, 2H), 3.52-3.43 (m, 4H). | 571.3 | B | |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-1135 | 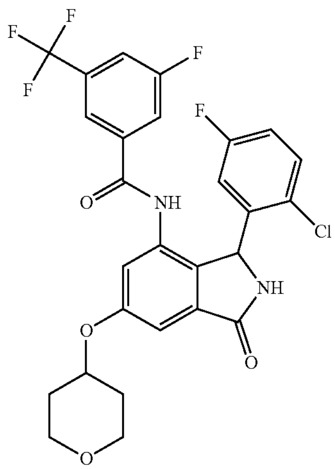 [SMILES: O=C(Nc1cc(OC2CCOCC2)cc2c1C(c1cc(F)ccc1Cl)NC2=O)c1cc(F)cc(C(F)(F)F)c1] | Fc1ccc(C1)c(c1)C1NC(=O)c2cc(OC3CCOCC3)cc(NC(=O)c3cc(F)cc(c3)C(F)(F)F)c12 | NMR (400 MHz, DMSO-d6) 10.41 (br. s, 1H), 9.12 (s, 1H), 7.94 (dt, 8.4, 1.6 Hz, 1H), 7.71 (br. d, 9.2 Hz), 7.63 (s, 1H), 7.30 (dd, 8.9, 5.2 Hz, 1H), 7.26 (d, 2.2 Hz, 1H), 7.11-7.07 (m, 2H), 6.64 (br. s, 1H), 5.92 (br. s, 1H), 4.75 (tt, 8.4, 4.0 Hz, 1H), 3.93-3.81 (m, 2H), 3.57-3.46 (m, 2H), 2.07-1.94 (m, 2H), 1.72-1.54 (m, 2H). | 567.3 | A | |
| I-1136 | 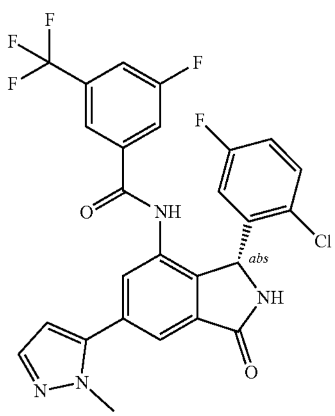 [SMILES: Cn1nccc1-c1cc(NC(=O)c2cc(F)cc(C(F)(F)F)c2)c2c(c1)C(=O)N[C@H]2c1cc(F)ccc1Cl] | Cn1nccc1-c1cc2C(=O)N[C@H](c2c(NC(=O)c2cc(F)cc(c2)C(F)F)c1c(F)ccc1Cl | NMR (400 MHz, DMSO-d6) 10.61 (s, 1H), 9.27 (br. s, 1H), 7.96 (br. d, 7.6 Hz, 1H), 7.79 (s, 1H), 7.74 (br. d, 7.9 Hz, 1H), 7.67 (s, 2H), 7.53 (d, 1.9 Hz, 1H), 7.34 (dd, 8.9, 5.2 Hz, 1H), 7.11 (td, 8.4, 3.1 Hz, 1H), 6.80 (s, 1H), 6.57 (d, 1.9 Hz, 1H), 6.05 (s, 1H), 3.94 (s, 3H). | 547.4 | A | |
| I-1137 | 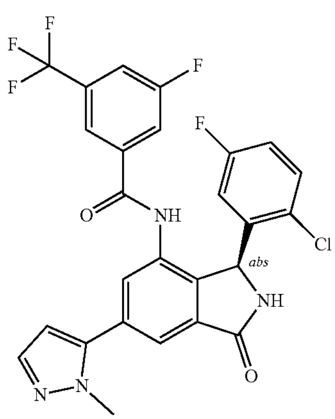 [SMILES: Cn1nccc1-c1cc(NC(=O)c2cc(F)cc(C(F)(F)F)c2)c2c(c1)C(=O)N[C@@H]2c1cc(F)ccc1Cl] | Cn1nccc1-c1cc2C(=O)N[C@@H](c2c(NC(=O)c2cc(F)cc(c2)C(F)(F)F)c1cc(F)ccc1Cl | NMR (400 MHz, DMSO-d6) 10.60 (s, 1H), 9.28 (br. s, 1H), 7.96 (br. d, 8.5 Hz, 1H), 7.80 (d, 1.3 Hz, 1H), 7.74 (br. d, 9.4 Hz, 1H), 7.66-7.65 (m, 2H), 7.53 (d, 1.9 Hz, 1H), 7.34 (dd, 8.9, 5.2 Hz, 1H), 7.11 (td, 8.5, 3.0 Hz, 1H), 6.75 (s, 1H), 6.57 (d, 1.9 Hz, 1H), 6.05 (s, 1H), 3.94 (s, 3H). | 547.4 | D | |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-1138 | 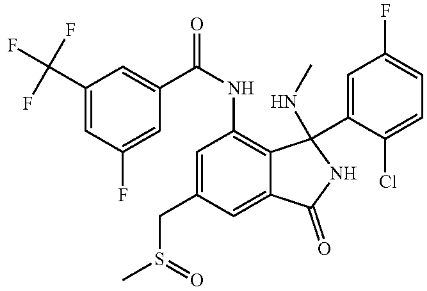 [SMILES: CNC1(c2cc(F)ccc2Cl)NC(=O)c2cc(CS(C)=O)cc(NC(=O)c3cc(F)cc(C(F)(F)F)c3)c21] | CNC1(NC(=O)c2cc(CS(C)=O)cc(NC(=O)c3cc(F)cc(c3)C(F)(F)F)c12)c1cc(F)ccc1Cl | NMR (400 MHz, MeCNd3) 9.81 (br. s, 1H), 8.46 (dd, 1.6, 2.0 Hz, 1H), 7.78 (s, 1H), 7.70 (d, 0.8 Hz, 1H), 7.68 (d, 0.8 Hz, 1H), 7.51 (dd, 1.6, 2.0 Hz, 1H), 7.43 (dd, 8.8, 5.4 Hz, 1H), 7.30 (dt, 10.4, 3.1 Hz, 1H), 7.20 (br. s, 1H), 7.06 (dddd, 10.8, 7.2, 2.8, 0.4 Hz, 1H), 4.20 (dd, 12.9, 1.2 Hz, 1H), 4.03 (d, 12.9 Hz, 1H), 3.31 (br. s, 1H) 2.49 (d, 2.5 Hz, 3H), 2.18 (s, 3H). | 572.2 | D | |
| I-1139 | 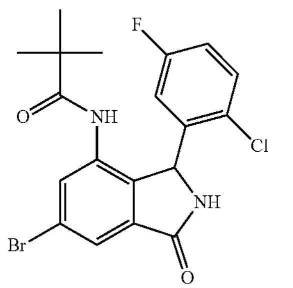 [SMILES: CC(C)(C)C(=O)Nc1cc(Br)cc2c1C(c1cc(F)ccc1Cl)NC2=O] | CC(C)(C)C(=O)Nc1cc(Br)cc2C(=O)NC(c12)c1cc(F)ccc1Cl | 1H-NMR (400 MHz, Solvent) 9.30 (s, 1H), 9.24 (br. s, 1H), 7.71 (d, 1.7 Hz, 1H), 7.58 (d, 1.7 Hz, 1H), 7.54-7.47 (m, 1H), 7.24 (ddd, 8.8, 8.1, 3.1 Hz, 1H), 6.56 (br. s, 1H), 6.03 (s, 1H), 0.89 (s, 9H). | 439.3 | D | |
| I-1140 | 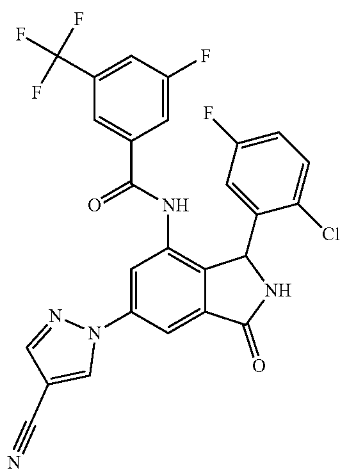 [SMILES: N#Cc1cnn(-c2cc(NC(=O)c3cc(F)cc(C(F)(F)F)c3)c3c(c2)C(=O)NC3c2cc(F)ccc2Cl)c1] | Fc1ccc(C1)c(c1)C1NC(=O)c2cc(cc(NC(=O)c3cc(F)cc(c3)C(F)(F)F)c12)-n1cc(cn1)C#N | (400 MHz, DMSO-D6) 10.71 (br s, 1 H), 9.57 (s, 1 H), 9.36 (s, 1 H), 8.44 (s, 1 H), 8.18 (s, 1 H), 8.12 (s, 1 H), 7.96 (d, 7.8 Hz, 1 H), 7.76 (d, 8.6 Hz, 1 H), 7.68 (s, 1 H), 7.34 (dd, 8.9, 5.2 Hz, 1 H), 7.11 (td, 8.5, 3.1 Hz, 1 H), 6.66 (br s, 1 H), 6.05 (br s, 1 H). | 556.3 | A | |
| I-1141 | 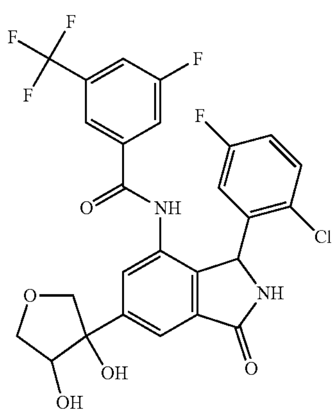 [SMILES: O=C(Nc1cc(C2(O)COCC2O)cc2c1C(c1cc(F)ccc1Cl)NC2=O)c1cc(F)cc(C(F)(F)F)c1] | OC1COCC1(O)c1cc2C(=O)NC(c2c(NC(=O)c2cc(F)cc(c2)C(F)(F)F)c1)c1cc(F)ccc1Cl | NMR (400 MHz, DMSO-d6) 10.65 (br s, 1H), 9.13 (br s, 1H), 7.94 (d, 8.7 Hz, 1H), 7.85 (s, 1H) 7.77 (d, 8.7 Hz, 1H), 7.69 (s, 1H), 7.64-7.62 (m, 1H), 7.30 (dd, 8.9, 5.1 Hz, 1H), 7.11-7.06 (m, 1H), 6.58 (br s, 1H), 5.99 (br s, 1H), 5.51-5.46 (m, 1H), 5.40 (d, 6.0 Hz, 1H), 4.31 (ddd, 20.5, 13.2, 6.7 Hz, 1H), 4.14-4.01 (m, 1H), 3.98 (d, 9.3 Hz, 1H), 3.90 (dd, 9.3, 4.6 Hz, 1H), 3.70-3.59 (m, 1H). | 569.3 | B | |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-1142 | 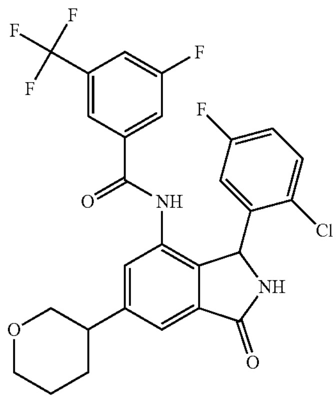 [SMILES: O=C(Nc1cc(C2CCCOC2)cc2c1C(c1cc(F)ccc1Cl)NC2=O)c1cc(F)cc(C(F)(F)F)c1] | Fc1ccc(C1)c(c1)C1NC(=O)c2cc(cc(NC(=O)c3cc(F)cc(c3)C(F)(F)F)c12)C1CCCOC1 | NMR (400 MHz, DMSO-d6) 9.11 (br s, 1H), 8.44 (br s, 1H), 7.94 (d, 8.4 Hz, 1H), 7.74 (d, 9.1 Hz, 1H), 7.67 (s, 1H), 7.61 (s, 1H), 7.40 (s, 1H), 7.30 (dd, 8.9, 5.2 Hz, 1H), 7.08 (td, 8.5, 2.9 Hz, 1H), 6.61 (br s, 1H), 5.95 (br s, 1H), 3.92-3.86 (m, 2H), 3.47-3.3 (m, 2H), 3.10-2.94 (m, 1H), 2.05-1.99 (m, 1H), 1.89-1.74 (m, 1H), 1.77-1.65 (m, 2H). | 551.3 | A | |
| I-1143 | 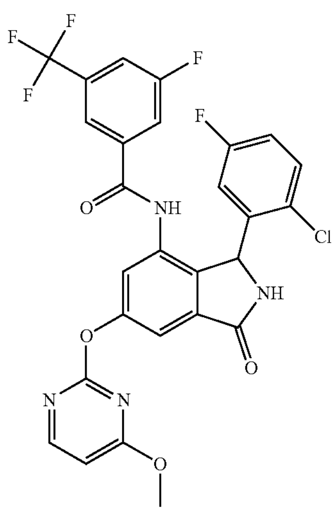 [SMILES: COc1ccnc(Oc2cc(NC(=O)c3cc(F)cc(C(F)(F)F)c3)c3c(c2)C(=O)NC3c2cc(F)ccc2Cl)n1] | COc1ccnc(Oc2cc3C(=O)NC(c3c(NC(=O)c3cc(F)cc(c3)C(F)(F)F)c2)c2cc(F)ccc2Cl)n1 | NMR (400 MHz, CD3CN) 8.76 (br s, 1H), 8.21 (d, 5.7 Hz, 1H), 7.66-7.62 (m, 1H), 7.60-7.53 (m, 3H), 7.42 (d, 1.6 Hz, 1H), 7.40 (br s, 1H), 7.26 (dd, 8.9, 5.1 Hz, 1H), 6.98 (ddd, 8.8, 8.0, 3.1 Hz, 1H), 6.68 (br s, 1H), 6.58 (d, 5.7 Hz, 1H), 6.13 (s, 1H), 3.90 (s, 3H). | 591 | B | |
| I-1144 | 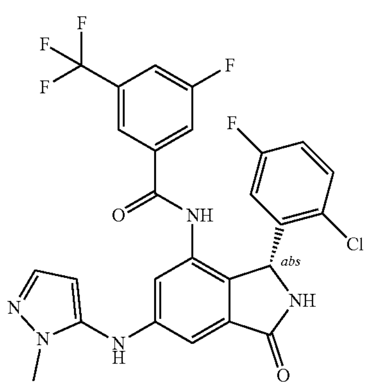 [SMILES: Cn1nccc1Nc1cc(NC(=O)c2cc(F)cc(C(F)(F)F)c2)c2c(c1)C(=O)N[C@H]2c1cc(F)ccc1Cl] | Cn1nccc1Nc1cc2C(=O)N[C@H](c2c(NC(=O)c2cc(F)cc(c2)C(F)(F)F)c1)c1cc(F)ccc1Cl | 1H NMR (400 MHz, DMSO-D6) 10.37 (s, 1H), 9.04 (s, 1H), 8.45 (s, 1H), 7.92 (d, 8.5 Hz, 1H), 7.69 (d, 8.9 Hz, 1H), 7.59 (s, 1H), 7.42 (d, 1.4 Hz, 1H), 7.30 (dd, 8.9, 5.1 Hz, 1H), 7.07 (td, 8.4, 2.9 Hz, 1H), 7.02 (d, 1.6 Hz, 1H), 6.94 (s, 1H), 6.66 (br s, 1H), 6.12 (d, 1.6 Hz, 1H), 5.89 (br s, 1H), 3.68 (s, 3H). | 562.3 | A | |

TABLE 2-continued

Representative Compounds of the Invention with Bioactivity Data.

| Ex. No. | Structure | SMILES | $^1$H NMR | MS | ADP-Glo IC$_{50}$ | MCF 10A IC$_{50}$ |
|---|---|---|---|---|---|---|
| I-1145 | 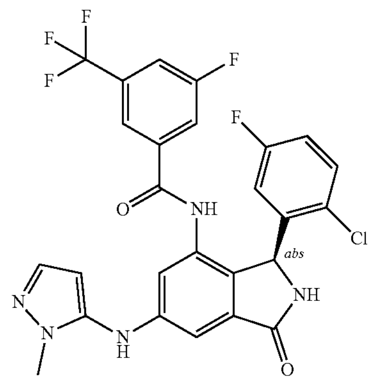 [SMILES: Cn1nccc1Nc1cc(NC(=O)c2cc(F)cc(C(F)(F)F)c2)c2c(c1)C(=O)N[C@@H]2c1cc(F)ccc1Cl] | Cn1nccc 1Nc1cc2 C(=O)N1 c2c(NC (=O)c2cc (F)cc(c2) C(F)(F)F) c1c1cc (F)ccc1Cl | 1H NMR (400 MHz, DMSO-d6) 10.36 (s, 1H), 9.04 (br s, 1H), 8.44 (s, 1H), 7.93 (d, 8.6 Hz, 1H), 7.69 (d, 9.0 Hz, 1H), 7.59 (s, 1H), 7.42 (d, 1.9 Hz, 1H), 7.30 (dd, 8.9, 5.2 Hz, 1H), 7.07 (td, 8.4, 3.1 Hz, 1H), 7.02 (d, 2.0 Hz, 1H), 6.93 (br s, 1H), 6.64 (br s, 1H), 6.12 (d, 1.8 Hz, 1H), 5.89 (br s, 1H), 3.68 (s, 3 H). | 562.3 | D | |
| I-1146 | 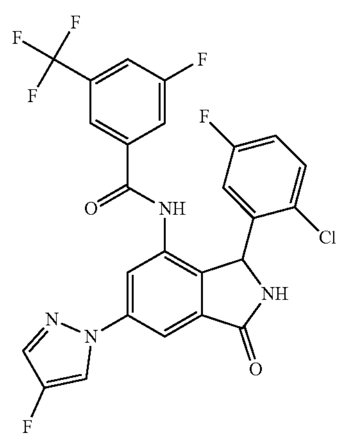 [SMILES: O=C(Nc1cc(-n2cc(F)cn2)cc2c1C(c1cc(F)ccc1Cl)NC2=O)c1cc(F)cc(C(F)(F)F)c1] | Fc1cnn(c 1)-c1cc2C(= O)NC(c2 c(NC(=O) c2cc(F)c c(c2)C(F) (F)F)c1)c 1cc(F)ccc 1Cl | (400 MHz, DMSO-D6) 10.69 (br s, 1 H), 9.30 (br s, 1 H), 8.96 (d, 4.4 Hz, 1 H), 8.12-8.02 (m, 2 H), 7.96 (d, 8.7 Hz, 1 H), 7.93 (d, 4.3 Hz, 1 H), 7.76 (d, 8.9 Hz, 1 H), 7.68 (s, 1 H), 7.33 (dd, 8.9, 5.2 Hz, 1 H), 7.10 (td, 8.5, 3.0 Hz, 1 H), 6.66 (br s, 1 H), 6.02 (br s, 1 H). | 549.3 | A | A |
| I-1147 | 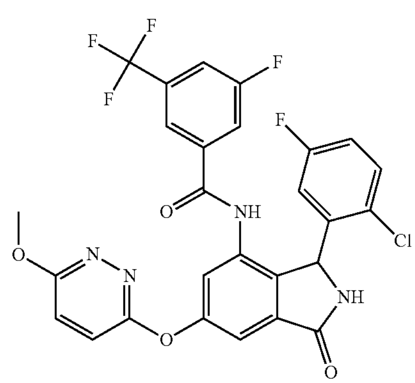 [SMILES: COc1ccc(Oc2cc(NC(=O)c3cc(F)cc(C(F)(F)F)c3)c3c(c2)C(=O)NC3c2cc(F)ccc2Cl)nn1] | COc1ccc (Oc2cc3 C(=O)N C(c3c(N C(=O)c3 cc(F)cc(c 3)C(F)(F) F)c2)c2c c(F)ccc2 Cl)nn1 | NMR (400 MHz, DMSO) 10.66 (br s, 1H), 9.24 (br s, 1H), 8.49 (s, 1H), 7.92 (br d, 7.0 Hz, 1H), 7.73 (br d, 8.9 Hz, 1H), 7.65 (s, 1H), 7.57 (d, 9.4 Hz, 1H), 7.41-7.39 (m, 2H), 7.34 (dd, 8.9, 5.2 Hz, 1H), 7.11 (td, 8.3, 3.0 Hz, 1H), 6.71 (br s, 1H), 6.01 (br s, 1H), 3.97 (s, 3H). | 591 | A | |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-1148 | 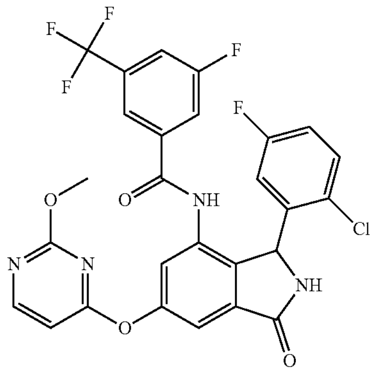 [SMILES: COc1nccc(Oc2cc(NC(=O)c3cc(F)cc(C(F)(F)F)c3)c3c(c2)C(=O)NC3c2cc(F)ccc2Cl)n1] | COcncc c(Oc2cc3 C(=O)N C(c3c(N C(=O)c3 cc(F)cc(c 3)C(F)(F) F)c2)c2c c(F)ccc2 Cl)n1 | NMR (400 MHz, CD3CN) 8.72 (br s, 1H), 8.42 (d, 5.6 Hz, 1H), 7.65 (d, 8.4 Hz, 1H), 7.62-7.54 (m, 3H), 7.42 (d, 1.2 Hz, 1H), 7.35 (s, 1H), 7.28 (dd, 8.9, 5.1 Hz, 1H), 7.02-6.96 (m, 1H), 6.71 (br d, 5.6 Hz, 2H), 6.15 (br s, 1H), 3.86 (s, 3H). | 591 | A | |
| I-1149 | 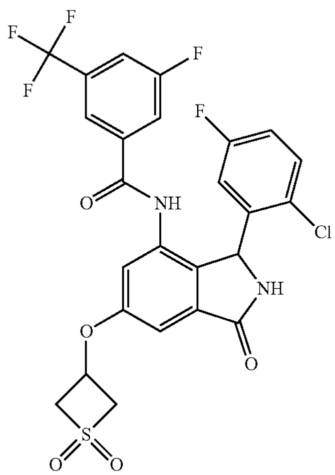 [SMILES: O=C(Nc1cc(OC2CS(=O)(=O)C2)cc2c1C(c1cc(F)ccc1Cl)NC2=O)c1cc(F)cc(C(F)(F)F)c1] | Fc1ccc(C 1)c(c1)C1 NC(=O)c 2cc(OC3 CS(=O) (=O)C3)c c(NC(=O) c3cc(F)c c(c3)C(F) (F)F)c12 | NMR (400 MHz, DMSO-d6) Major rotamer:-' 10.40 (br. s, 1H), 10.32 (br. s, 1H), 7.98 (br. d, 8.2 Hz, 1H), 7.78 (br. d, 8.8 Hz, 1H), 7.69 (s, 1H), 7.36-7.31 (m, 2H), 7.14-7.08 (m, 1H), 7.03 (d, 2.2 Hz, 1H), 6.86 (d, 2.2 Hz, 1H), 5.83 (s, 1H), 4.88-4.81 (m, 1H), 4.81-4.74 (m, 1H), 4.38-4.27 (m, 2H), 4.20-4.11 (m, 1H) | 587.1 | D | |
| I-1150 | 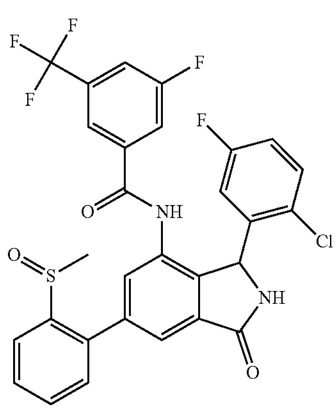 [SMILES: CS(=O)c1ccccc1-c1cc(NC(=O)c2cc(F)cc(C(F)(F)F)c2)c2c(c1)C(=O)NC2c1cc(F)ccc1Cl] | CS(=O)c 1ccccc1-c1cc2C(= O)NC(c2 c(NC(=O) c2cc(F)c c(c2)C(F) (F)F)c1)c 1cc(F)ccc 1Cl | 1H NMR (400 MHz, DMSO-d6) 2.53-2.56 (m, 4 H) 5.98-6.19 (m, 1 H) 7.12-7.20 (m, 1 H) 7.39 (ddd, 8.84, 5.18, 2.15 Hz, 1 H) 7.50-7.62 (m, 2 H) 7.68-7.75 (m, 3 H) 7.76-7.83 (m, 2 H) 7.99 (br d, 8.34 Hz, 1 H) 8.09 (ddd, 7.77, 2.97, 1.14 Hz, 1 H) 9.31 (br s, 1 H) 10.65 (br d, 16.67 Hz, 1 H) | 605.28 | A | |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-1151 | 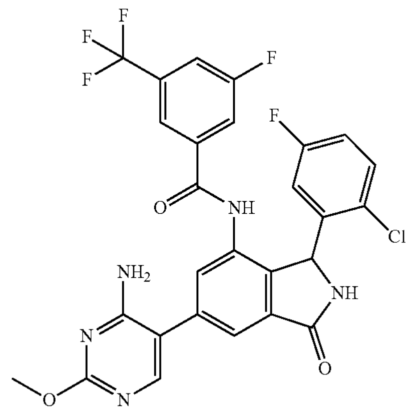 [SMILES: COc1ncc(-c2cc(NC(=O)c3cc(F)cc(C(F)(F)F)c3)c3c(c2)C(=O)NC3c2cc(F)ccc2Cl)c(N)n1] | COc1ncc(c(N)n1)-c1cc2C(=O)NC(c2c(NC(=O)c2cc(F)cc(c2)C(F)(F)F)c1)c1cc(F)ccc1Cl | | 590.5 | B | |
| I-1152 | 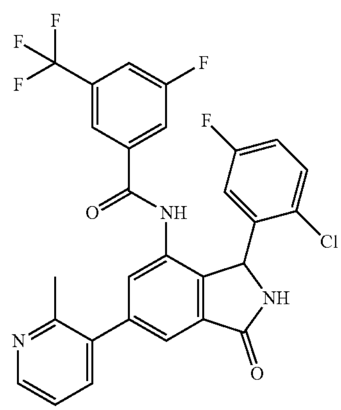 [SMILES: Cc1ncccc1-c1cc(NC(=O)c2cc(F)cc(C(F)(F)F)c2)c2c(c1)C(=O)NC2c1cc(F)ccc1Cl] | Cc1ncccc1-c1cc2C(=O)NC(c2c(NC(=O)c2cc(F)cc(c2)C(F)(F)F)c1)c1cc(F)ccc1Cl | | 558.36 | A | |
| I-1153 | 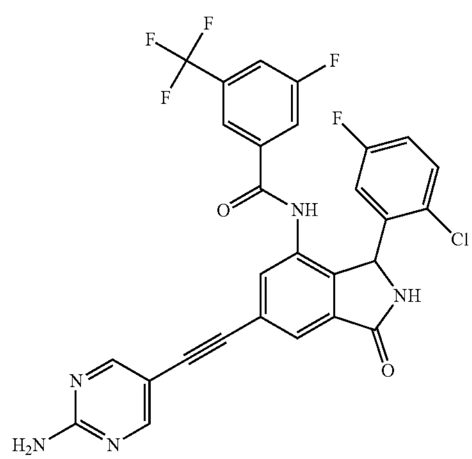 [SMILES: Nc1ncc(C#Cc2cc(NC(=O)c3cc(F)cc(C(F)(F)F)c3)c3c(c2)C(=O)NC3c2cc(F)ccc2Cl)cn1] | Nc1ncc(cn1)C#Cc1cc2C(=O)NC(c2c(NC(=O)c2cc(F)cc(c2)C(F)(F)F)c1)c1cc(F)ccc1Cl | 1H NMR (DMSO-d6, 400 MHz):-' = 10.53 (s, 1H), 9.26 (br s, 1H), 8.49 (s, 2H), 7.96 (br d, 8.3 Hz, 1H), 7.60-7.77 (m, 4H), 7.33 (dd, 8.8, 5.3 Hz, 1H), 7.22 (s, 2H), 7.10 (td, 8.3, 3.0 Hz, 1H), 6.02 (br s, 1H), 2.99 (br s, 1H) | 584.5 | A | |

TABLE 2-continued

Representative Compounds of the Invention with Bioactivity Data.

| Ex. No. | Structure | SMILES | $^1$H NMR | MS | ADP-Glo IC$_{50}$ | MCF 10A IC$_{50}$ |
|---|---|---|---|---|---|---|
| I-1154 | 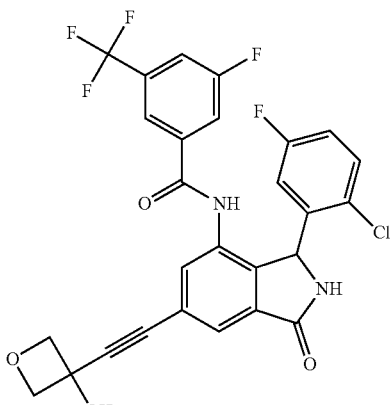 | OC1(COC1)C#Cc1cc2C(=O)NC(c2c(NC(=O)c2cc(F)cc(c2)C(F)(F)F)c1)c1cc(F)ccc1Cl | 1H NMR (DMSO-d6, 400 MHz):-' = 10.52 (s, 1H), 9.28 (br s, 1H), 7.96 (br d, 8.3 Hz, 1H), 7.69-7.76 (m, 2H), 7.66 (s, 1H), 7.61 (d, 1.0 Hz, 1H), 7.33 (dd, 8.8, 5.3 Hz, 1H), 7.10 (td, 8.4, 3.2 Hz, 1H), 6.70 (s, 1H), 6.01 (br s, 1H), 4.80 (d, 6.6 Hz, 2H), 4.63 (d, 6.6 Hz, 2H), 4.31-4.58 (m, 1H), 3.13 (s, 1H) | 563.4 | A | |
| I-1155 | 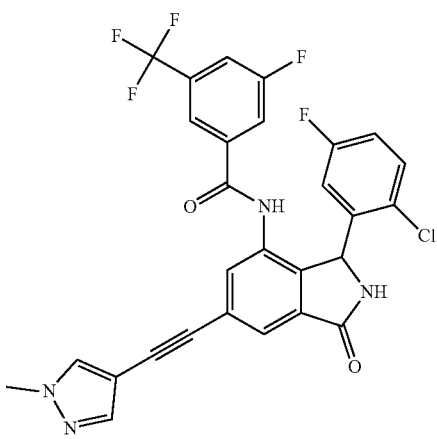 [SMILES: Cn1cc(C#Cc2cc(NC(=O)c3cc(F)cc(C(F)(F)F)c3)c3c(c2)C(=O)NC3c2cc(F)ccc2Cl)cn1] | Cn1cc(cn1)C#Cc1cc2C(=O)NC(c2c(NC(=O)c2cc(F)cc(c2)C(F)(F)F)c1)c1cc(F)ccc1Cl | 1H NMR (DMSO-d6, 400 MHz):-' = 10.51 (s, 1H), 9.26 (br s, 1H), 8.13 (s, 1H), 7.96 (br d, 8.6 Hz, 1H), 7.71-7.77 (m, 2H), 7.69 (d, 1.0 Hz, 1H), 7.66 (s, 1H), 7.60 (s, 1H), 7.33 (dd, 9.0, 5.2 Hz, 1H), 7.10 (td, 8.3, 3.0 Hz, 1H), 6.01 (br s, 1H), 3.87 (s, 3H), 2.98 (br s, 1H) | 571.4 | A | |
| I-1156 | 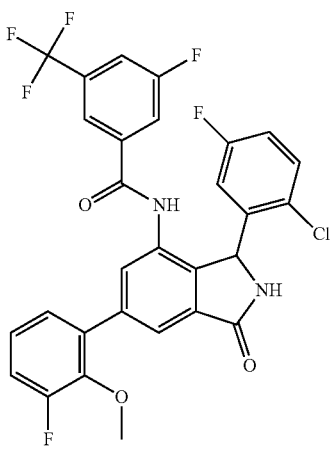 [SMILES: COc1c(F)cccc1-c1cc(NC(=O)c2cc(F)cc(C(F)(F)F)c2)c2c(c1)C(=O)NC2c1cc(F)ccc1Cl] | COc1c(F)cccc1-c1cc2C(=O)NC(c2c(NC(=O)c2cc(F)cc(c2)C(F)(F)F)c1)c1cc(F)ccc1Cl | 1H NMR (500 MHz, DMSO-d6) 3.74 (d, 1.37 Hz, 3 H) 6.06 (br s, 1 H) 6.74 (br d, 3.36 Hz, 1 H) 7.09 (td, 8.39, 3.05 Hz, 1 H) 7.21-7.27 (m, 1 H) 7.28-7.37 (m, 3 H) 7.66 (s, 1 H) 7.69-7.81 (m, 3 H) 7.88 (br d, 8.39 Hz, 1 H) 9.09 (s, 1 H) 10.47 (br s, 1 H) | 591.33 | A | A |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-1157 | 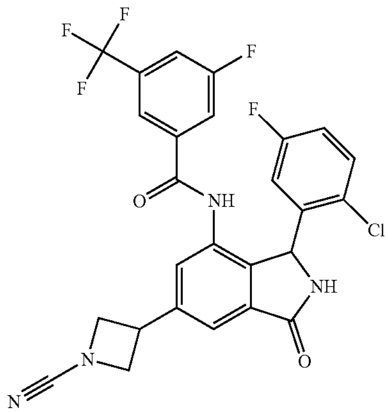 [SMILES: N#CN1CC(c2cc(NC(=O)c3cc(F)cc(C(F)(F)F)c3)c3c(c2)C(=O)NC3c2cc(F)ccc2Cl)C1] | Fc1ccc(C1)c(c1)C1NC(=O)c2cc(cc(NC(=O)c3cc(F)cc(c3)C(F)(F)F)c12)C1CN(C1)C#N | 1H NMR (500 MHz, DMSO-d6) 4.14-4.21 (m, 1 H) 4.23-4.32 (m, 2 H) 4.53-4.62 (m, 2 H) 6.00 (br s, 1 H) 6.56-6.72 (m, 1 H) 7.07 (td, 8.39, 3.05 Hz, 1 H) 7.30 (dd, 8.85, 5.19 Hz, 1 H) 7.54 (d, 1.22 Hz, 1 H) 7.67-7.76 (m, 3 H) 7.89 (br d, 8.39 Hz, 1 H) 9.04 (s, 1 H) 10.42 (s, 1 H) | 547.31 | A | C |
| I-1158 | 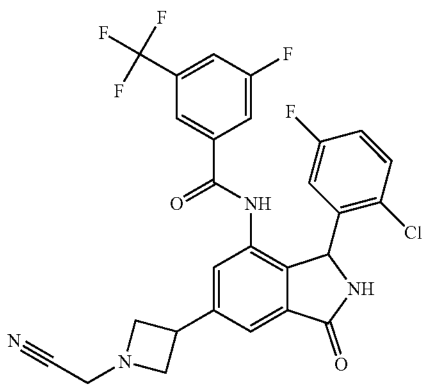 [SMILES: N#CCN1CC(c2cc(NC(=O)c3cc(F)cc(C(F)(F)F)c3)c3c(c2)C(=O)NC3c2cc(F)ccc2Cl)C1] | Fc1ccc(C1)c(c1)C1NC(=O)c2cc(cc(NC(=O)c3cc(F)cc(c3)C(F)(F)F)c12)C1CN(CC#N)C1 | 1H NMR (500 MHz, DMSO-d6) 3.34-3.40 (m, 2 H) 3.70 (s, 2 H) 3.74-3.80 (m, 2 H) 3.80-3.87 (m, 1 H) 5.97 (br s, 1 H) 6.50-6.72 (m, 1 H) 7.06 (td, 8.39, 3.05 Hz, 1 H) 7.28 (dd, 8.85, 5.19 Hz, 1 H) 7.49 (s, 1 H) 7.66-7.75 (m, 3 H) 7.87 (br d, 8.39 Hz, 1 H) 8.99 (s, 1 H) 10.40 (br s, 1 H) | 534.4 | A | A |
| I-1159 | 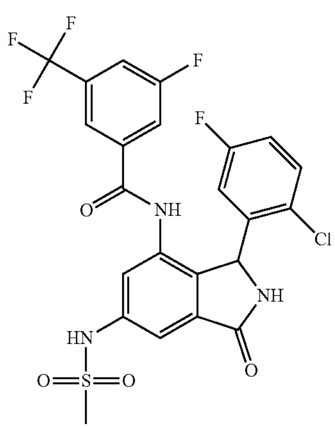 [SMILES: CS(=O)(=O)Nc1cc(NC(=O)c2cc(F)cc(C(F)(F)F)c2)c2c(c1)C(=O)NC2c1cc(F)ccc1Cl] | CS(=O)(=O)Nc1cc2C(=O)NC(c2c(NC(=O)c2cc(F)cc(c2)C(F)(F)F)c1c1cc(F)ccc1Cl | 1H NMR (400 MHz, DMSO-d6) 3.07 (s, 3 H) 5.92 (br s, 1 H) 6.58 (br s, 1 H) 7.08 (td, 8.40, 3.16 Hz, 1 H) 7.27-7.36 (m, 2 H) 7.49 (d, 1.77 Hz, 1 H) 7.60 (s, 1 H) 7.71 (br d, 9.09 Hz, 1 H) 7.94 (br d, 8.34 Hz, 1 H) 9.15 (br s, 1 H) 10.18-10.47 (m, 1 H) 10.54 (br s, 1 H) | 560.31 | A | A |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-1160 | 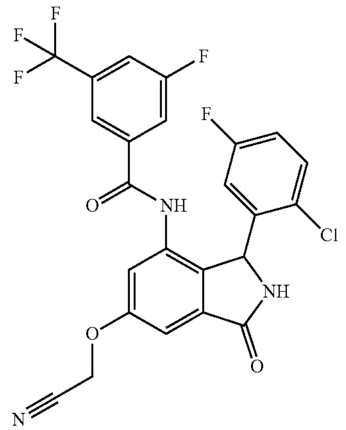 [SMILES: N#CCOc1cc(NC(=O)c2cc(F)cc(C(F)(F)F)c2)c2c(c1)C(=O)NC2c1cc(F)ccc1Cl] | Fc1ccc(C1)c(c1)C1NC(=O)c2cc(OCC#N)cc(NC(=O)c3cc(F)cc(c3)C(F)(F)F)c12 | | 522.4 | A | A |
| I-1161 | 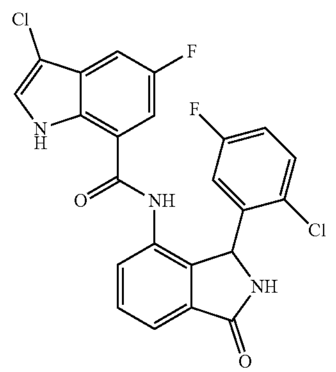 [SMILES: O=C1NC(c2cc(F)ccc2Cl)c2c(NC(=O)c3cc(F)cc4c(Cl)c[nH]c34)cccc21] | Fc1ccc(C1)c(c1)C1NC(=O)c2cccc(NC(=O)c3cc(F)cc4c(C1)c[nH]c34)c12 | | 472 | B | B |
| I-1162 | 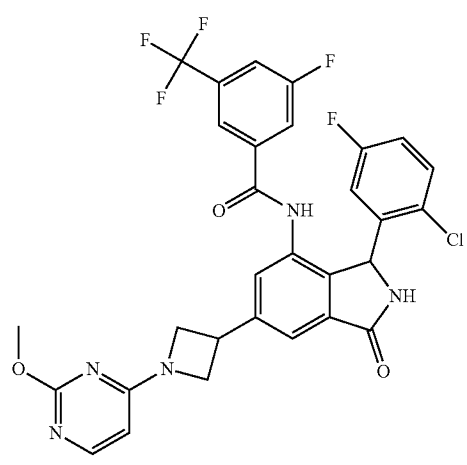 [SMILES: COc1nccc(N2CC(c3cc(NC(=O)c4cc(F)cc(C(F)(F)F)c4)c4c(c3)C(=O)NC4c3cc(F)ccc3Cl)C2)n1] | COc1ncc c(n1)N1 CC(C1)c 1cc2C(= O)NC(c2 c(NC(=O) c2cc(F)c c(c2)C(F) (F)F)c1)c 1cc(F)ccc 1Cl | 1H NMR (400 MHz, DMSO-d6) 3.80 (s, 3 H) 4.08 (ddd, 11.87, 8.72, 5.94 Hz, 2 H) 4.15-4.25 (m, 1 H) 4.45-4.55 (m, 2 H) 6.16 (d, 5.81 Hz, 1 H) 6.70-6.82 (m, 1 H) 7.10 (td, 8.40, 2.91 Hz, 1 H) 7.32 (dd, 8.97, 5.18 Hz, 1 H) 7.56 (s, 1 H) 7.64-7.79 (m, 3 H) 7.94 (br d, 8.08 Hz, 1 H) 8.03 (d, 5.56 Hz, 1 H) 8.47 (s, 1 H) 9.16 (br s, 1 H) 10.53 (br s, 1 H) | 630.39 | A | A |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-1163 | 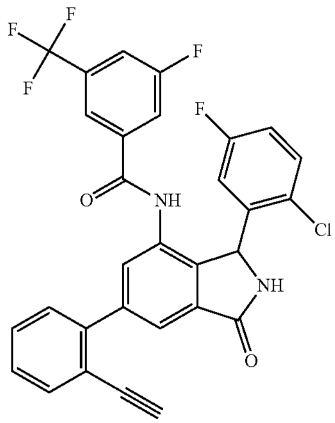 [SMILES: C#Cc1ccccc1-c1cc(NC(=O)c2cc(F)cc(C(F)(F)F)c2)c2c(c1)C(=O)NC2c1cc(F)ccc1Cl] | Fc1ccc(C1)c(c1)C1NC(=O)c2cc(cc(NC(=O)c3cc(F)cc(c3)C(F)(F)F)c12)-c1ccccc1C#C | 1H NMR (400 MHz, DMSO-d6) 4.22 (s, 1 H) 5.99-6.12 (m, 1 H) 7.11 (td, 8.46, 3.03 Hz, 1 H) 7.34 (dd, 8.84, 5.05 Hz, 1 H) 7.43-7.49 (m, 1 H) 7.51-7.59 (m, 2 H) 7.63-7.70 (m, 3 H) 7.75 (br d, 9.09 Hz, 1 H) 7.86 (d, 1.26 Hz, 1 H) 7.95 (br d, 8.34 Hz, 1 H) 9.23 (br s, 1 H) 10.60 (s, 1 H) | 567.32 | A | A |
| I-1164 | 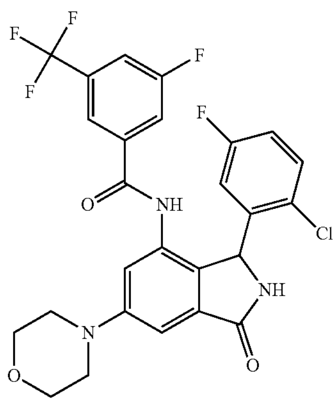 [SMILES: O=C(Nc1cc(N2CCOCC2)cc2c1C(c1cc(F)ccc1Cl)NC2=O)c1cc(F)cc(C(F)(F)F)c1] | Fc1ccc(C1)c(c1)C1NC(=O)c2cc(cc(NC(=O)c3cc(F)cc(c3)C(F)(F)F)c12)N1CCOCC1 | 1H NMR (400 MHz, DMSO-d6) 3.22 (q, 4.46 Hz, 4 H) 3.76 (t, 4.80 Hz, 4 H) 5.83-5.94 (m, 1 H) 7.02-7.10 (m, 2 H) 7.17 (d, 2.02 Hz, 1 H) 7.28 (dd, 8.84, 5.05 Hz, 1 H) 7.65 (s, 1 H) 7.71 (br d, 8.84 Hz, 1 H) 7.92 (br d, 8.59 Hz, 1 H) 9.01 (br s, 1 H) 10.38 (s, 1 H) | 552.36 | A | A |
| I-1165 | 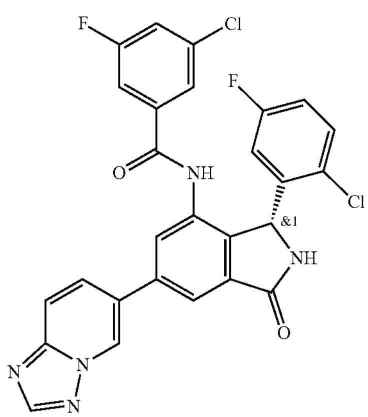 [SMILES: O=C(Nc1cc(-c2ccc3ncnn3c2)cc2c1[C@H](c1cc(F)ccc1Cl)NC2=O)c1cc(F)cc(Cl)c1] | Fc1ccc(C1)c(c1)[C@@H]1NC(=O)c2cc(cc(NC(=O)c3cc(F)cc(Cl)c3)c12)-c1ccc2ncnn2c1 | 1H NMR (400 MHz, DMSO-d6) 10.50 (s, 1H), 9.48 (dd, 1.9, 1.0 Hz, 1H), 9.27 (s, 1H), 8.58 (s, 1H), 8.18-8.10 (m, 2H), 8.03-7.94 (m, 2H), 7.72 (dt, 8.6, 2.2 Hz, 1H), 7.48-7.36 (m, 3H), 7.17 (td, 8.4, 3.1 Hz, 1H), 6.08 (s, 1H). | 550.1 | A | |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-1166 | 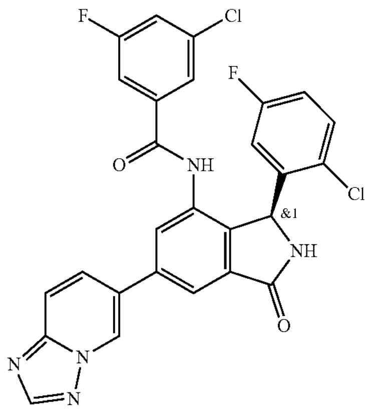 [SMILES: O=C(Nc1cc(-c2ccc3ncnn3c2)cc2c1[C@@H](c1cc(F)ccc1Cl)NC2=O)c1cc(F)cc(Cl)c1] | Fc1ccc(C1)c(c1)[C@H]1NC(=O)c2cc(cc(NC(=O)c3cc(F)cc(Cl)c3)c12)-c1ccc2ncnn2c1 | 1H NMR (400 MHz, DMSO-d6) 10.50 (s, 1H), 9.48 (d, 1.6 Hz, 1H), 9.27 (s, 1H), 8.58 (s, 1H), 8.14 (dd, 9.4, 1.8 Hz, 2H), 8.03-7.94 (m, 2H), 7.75-7.68 (m, 1H), 7.47-7.36 (m, 3H), 7.17 (td, 8.4, 3.1 Hz, 1H), 6.08 (s, 1H), 1.24 (s, 0H). | 550.1 | D | |
| I-1167 | 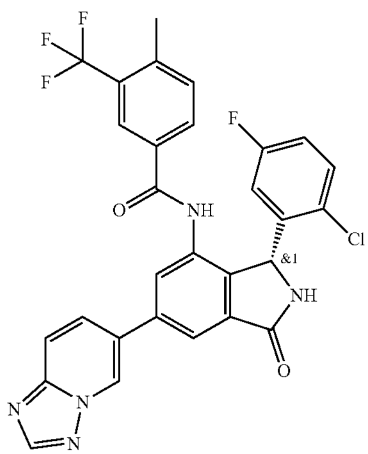 [SMILES: Cc1ccc(C(=O)Nc2cc(-c3ccc4ncnn4c3)cc3c2[C@H](c2cc(F)ccc2Cl)NC3=O)cc1C(F)(F)F] | Cc1ccc(cc1C(F)(F)F)C(=O)Nc1cc(cc2C(=O)N[C@H](c12)c1cc(F)ccc1Cl)-c1ccc2ncnn2c1 | 1H NMR (400 MHz, Chloroform-d) 8.96 (t, 1.4 Hz, 1H), 8.60 (s, 1H), 8.44 (s, 1H), 8.05 (d, 1.6 Hz, 1H), 7.91 (t, 1.3 Hz, 2H), 7.77-7.67 (m, 2H), 7.52 (s, 1H), 7.49-7.40 (m, 2H), 7.10 (ddd, 8.9, 7.3, 3.0 Hz, 1H), 6.79 (d, 8.3 Hz, 1H), 6.56 (s, 1H), 6.31 (s, 1H), 2.60 (d, 1.9 Hz, 3H). | 580.15 | A | |
| I-1168 | 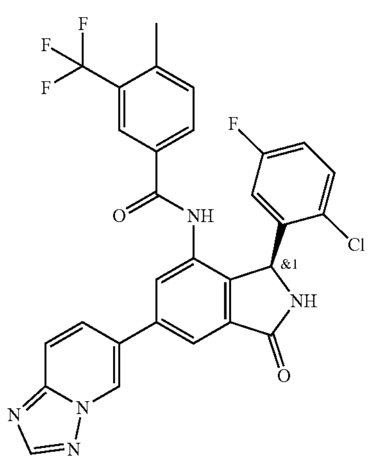 [SMILES: Cc1ccc(C(=O)Nc2cc(-c3ccc4ncnn4c3)cc3c2[C@@H](c2cc(F)ccc2Cl)NC3=O)cc1C(F)(F)F] | Cc1ccc(cc1C(F)(F)F)C(=O)Nc1cc(cc2C(=O)N[C@@H](c12)c1cc(F)ccc1Cl)-c1ccc2ncnn2c1 | 1H NMR (400 MHz, Chloroform-d) 8.97 (s, 1H), 8.60 (s, 1H), 8.44 (s, 1H), 8.05 (d, 1.6 Hz, 1H), 7.92 (s, 2H), 7.76-7.68 (m, 2H), 7.54 (s, 1H), 7.49-7.40 (m, 2H), 7.10 (ddd, 8.9, 7.2, 3.0 Hz, 1H), 6.79 (d, 8.4 Hz, 1H), 6.62 (s, 1H), 6.31 (s, 1H), 2.60 (q, 1.9 Hz, 3H). | 580.05 | E | |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-1169 | 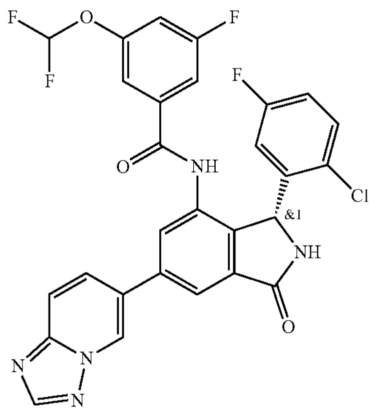 [SMILES: O=C(Nc1cc(-c2ccc3ncnn3c2)cc2c1[C@H](c1cc(F)ccc1Cl)NC2=O)c1cc(F)cc(OC(F)F)c1] | FC(F)Oc1cc(F)cc(c1)C(=O)Nc1cc(cc2C(=O)N[C@H](c12)c1cc(F)ccc1Cl)-c1ccc2ncnn2c1 | 1H NMR (400 MHz, DMSO-d6) 10.45 (s, 1H), 9.47 (t, 1.3 Hz, 1H), 9.25 (s, 1H), 8.58 (s, 1H), 8.17-8.10 (m, 2H), 8.02-7.94 (m, 2H), 7.44-7.27 (m, 5H), 7.14 (td, 8.9, 8.0, 3.1 Hz, 1H), 6.10 (s, 2H). | 582.1 | B | |
| I-1170 | 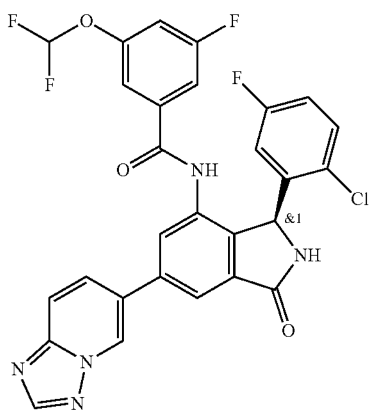 [SMILES: O=C(Nc1cc(-c2ccc3ncnn3c2)cc2c1[C@@H](c1cc(F)ccc1Cl)NC2=O)c1cc(F)cc(OC(F)F)c1] | FC(F)Oc1cc(F)cc(c1)C(=O)Nc1cc(cc2C(=O)N[C@@H](c12)c1cc(F)ccc1Cl)-c1ccc2ncnn2c1 | 1H NMR (400 MHz, DMSO-d6) 10.45 (s, 1H), 9.48 (d, 1.3 Hz, 1H), 9.25 (s, 1H), 8.58 (s, 1H), 8.17-8.10 (m,2H), 8.02-7.94 (m, 2H), 7.42-7.27 (m, 5H), 7.14 (td, 8.8, 8.1, 3.0 Hz, 1H), 6.10 (s, 2H). | 582.05 | E | |
| I-1171 | 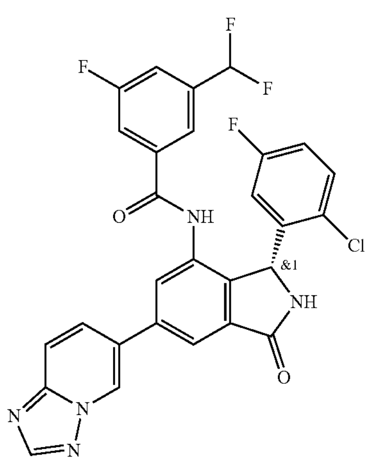 [SMILES: O=C(Nc1cc(-c2ccc3ncnn3c2)cc2c1[C@H](c1cc(F)ccc1Cl)NC2=O)c1cc(F)cc(C(F)F)c1] | FC(F)c1cc(F)cc(c1)C(=O)Nc1cc(cc2C(=O)N[C@H](c12)c1cc(F)ccc1Cl)-c1ccc2ncnn2c1 | 1H NMR (400 MHz, DMSO-d6) 10.55 (s, 1H), 9.48 (s, 2H), 9.26 (s, 1H), 8.58 (d, 1.3 Hz, 1H), 8.14 (d, 10.2 Hz, 2H), 8.02-7.94 (m, 1H), 7.70 (d, 2.1 Hz, 1H), 7.68 (s, 2H), 7.58 (d, 9.3 Hz, 1H), 7.36 (dd, 9.0, 5.1 Hz, 1H), 7.12 (d, 5.7 Hz, 2H), 6.73 (s, 1H), 6.10 (s, 1H) | 566.15 | B | |

TABLE 2-continued

Representative Compounds of the Invention with Bioactivity Data.

| Ex. No. | Structure | SMILES | $^1$H NMR | MS | ADP-Glo IC$_{50}$ | MCF 10A IC$_{50}$ |
|---|---|---|---|---|---|---|
| I-1172 | 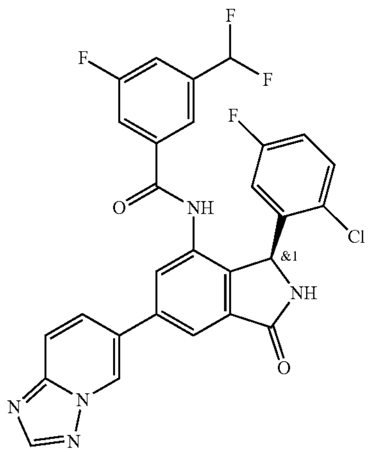 [SMILES: O=C(Nc1cc(-c2ccc3ncnn3c2)cc2c1[C@@H](c1cc(F)ccc1Cl)NC2=O)c1cc(F)cc(C(F)F)c1] | FC(F)c1cc(F)cc(c1)C(=O)Nc1cc(cc2C(=O)N[C@@H](c12)c1cc(F)ccc1Cl)-c1ccc2ncnn2c1 | 1H NMR (400 MHz, DMSO-d6) 10.55 (s, 1H), 9.48 (s, 1H), 9.25 (s, 1H), 8.58 (s, 1H), 8.14 (d, 10.1 Hz, 2H), 8.02-7.94 (m, 2H), 7.69 (d, 9.4 Hz, 2H), 7.58 (d, 9.2 Hz, 1H), 7.36 (dd, 8.9, 5.1 Hz, 1H), 7.12 (d, 8.0 Hz, 2H), 6.73 (s, 1H), 6.09 (s, 1H). | 566.2 | E | |
| I-1173 | 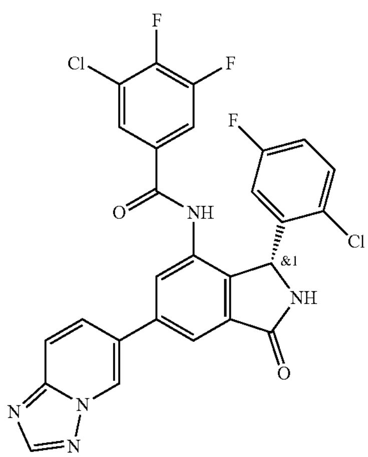 [SMILES: O=C(Nc1cc(-c2ccc3ncnn3c2)cc2c1[C@H](c1cc(F)ccc1Cl)NC2=O)c1cc(F)c(F)c(Cl)c1] | Fc1ccc(C1)c(c1)[C@@H]1NC(=O)c2cc(cc(NC(=O)c3cc(F)c(F)c(Cl)c3)c12)-c1ccc2ncnn2c1 | 1H NMR (400 MHz, DMSO-d6) 10.49 (s, 1H), 9.47 (t, 1.4 Hz, 1H), 9.28-9.23 (m, 1H), 8.58 (s, 1H), 8.17-8.10 (m, 2H), 8.02-7.94 (m, 2H), 7.75-7.66 (m, 1H), 7.63 (dt, 6.1, 1.9 Hz, 1H), 7.39 (dd, 8.9, 5.2 Hz, 1H), 7.16 (td, 8.4, 3.1 Hz, 1H), 6.65 (s, 1H), 6.07 (s, 1H). | 568.1 | A | |
| I-1174 | 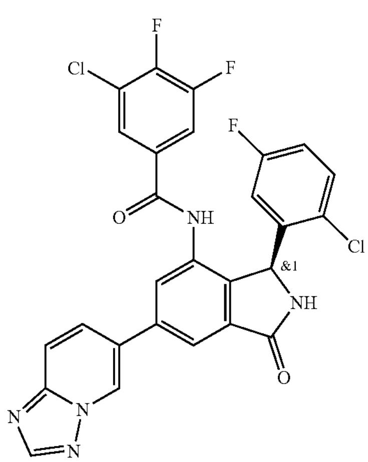 [SMILES: O=C(Nc1cc(-c2ccc3ncnn3c2)cc2c1[C@@H](c1cc(F)ccc1Cl)NC2=O)c1cc(F)c(F)c(Cl)c1] | Fc1ccc(C1)c(c1)[C@H]1NC(=O)c2cc(cc(NC(=O)c3cc(F)c(F)c(Cl)c3)c12)-c1ccc2ncnn2c1 | 1H NMR (400 MHz, DMSO-d6) 10.49 (s, 1H), 9.47 (t, 1.4 Hz, 1H), 9.28-9.23 (m, 1H), 8.58 (s, 1H), 8.17-8.10 (m, 2H), 8.02-7.94 (m, 2H), 7.75-7.66 (m, 1H), 7.63 (dt, 6.1, 1.9 Hz, 1H), 7.39 (dd, 8.9, 5.2 Hz, 1H), 7.16 (td, 8.4, 3.1 Hz, 1H), 6.65 (s, 1H), 6.07 (s, 1H). | 568.1 | D | |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-1175 | 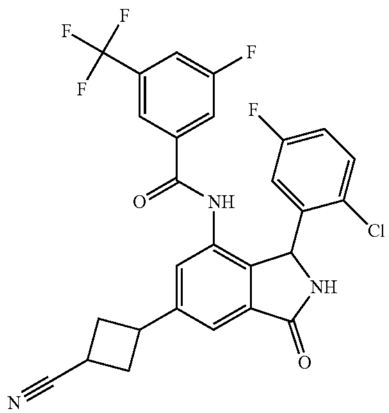 [SMILES: N#CC1CC(c2cc(NC(=O)c3cc(F)cc(C(F)(F)F)c3)c3c(c2)C(=O)NC3c2cc(F)ccc2Cl)C1] | Fc1ccc(C1)c(c1)C1NC(=O)c2cc(cc(NC(=O)c3cc(F)cc(c3)C(F)(F)F)c12)C1CC(C1)C#N | NMR (400 MHz, CD3CN) 8.64 (s,1H), 7.68-7.56 (m, 4H), 7.42 (d, 6.9 Hz,1H), 7.30-7.22 (m, 2H), 7.02-6.92 (m,1H), 6.60 (br, s, 1H), 6.09 (br, s, 1H), 3.78-3.67 (m,1H), 3.31-3.19 (m,1H), 2.88-2.80 (m,1H), 2.78-2.70 (m,1H), 2.69-2.59 (m,1H), 2.56-2.44 (m,1H). | 546.3 | A | |
| I-1176 | 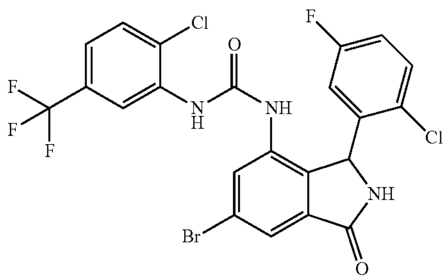 [SMILES: O=C(Nc1cc(C(F)(F)F)ccc1Cl)Nc1cc(Br)cc2c1C(c1cc(F)ccc1Cl)NC2=O] | Fc1ccc(C1)c(c1)C1NC(=O)c2cc(Br)cc(NC(=O)Nc3cc(cc3Cl)C(F)(F)F)c12 | (400 MHz, DMSO-d6) 9.27 (s, 1H), 9.09 (s, 1H), 8.46 (s, 1H), 8.35 (d, 1.9 Hz, 1H), 7.74-7.66 (m, 3H), 7.46-7.36 (m, 2H), 7.17 (dt, 8.6, 2.3 Hz, 1H), 6.71 (br s, 1H), 6.06 (br s, 1H). | 574.2 | B | |
| I-1177 | 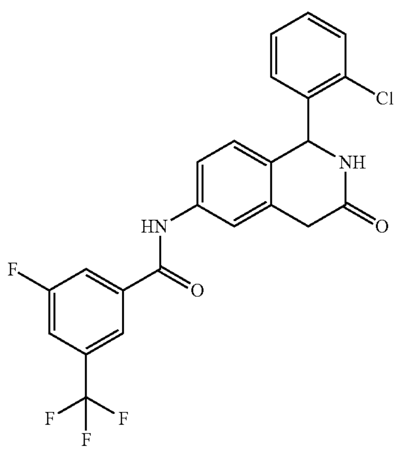 [SMILES: O=C1Cc2cc(NC(=O)c3cc(F)cc(C(F)(F)F)c3)ccc2C(c2ccccc2Cl)N1] | Fc1cc(cc(c1)C(F)(F)F)C(=O)Nc1ccc2C(NC(=O)Cc2c1)c1ccccc1Cl | NMR (400 MHz, DMSO) 10.56 (s, 1H), 8.45 (d, 2.3 Hz, 1H), 8.16 (s, 1H), 8.10 (d, 9.1 Hz, 1H), 7.98 (d, 8.5 Hz, 1H), 7.67 (d, 2.0 Hz, 1H), 7.53 (dd, 8.5, 2.1 Hz, 1H), 7.51-7.47 (m, 1H), 7.36-7.26 (m, 3H), 7.00 (d, 8.6 Hz, 1H), 6.07 (d, 1.7 Hz, 1H), 3.79 (d, 20.4 Hz, 1H), 3.61 (d, 19.6 Hz, 1H). | 463.1 | D | |
| I-1178 | 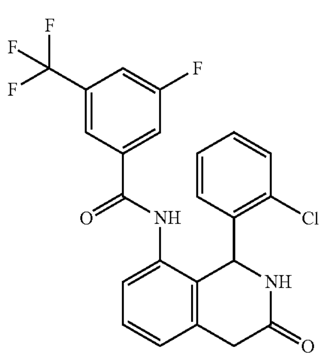 | Fc1cc(cc(c1)C(F)(F)F)C(=O)Nc1ccc2CC(=O)NC(c3ccccc3C1)c12 | NMR (400 MHz, DMSO) 10.18 (s, 1H), 8.59 (d, 3.8 Hz, 1H), 7.98-7.91 (m, 2H), 7.87 (d, 9.0 Hz, 1H), 7.40 (t, 7.7 Hz, 1H), 7.31-7.25 (m, 2H), 7.20 (td, 7.6, 1.7 Hz, 1H), 7.18-7.09 (m, 2H), 6.90 (dd, 7.7, 1.4 Hz., 1H), 6.23 (d, 3.7 Hz, 1H), 3.90 (d, 20.6 Hz, 1H), 3.62 (d, 20.7 Hz, 1H). | 463.1 | D | |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-1179 | 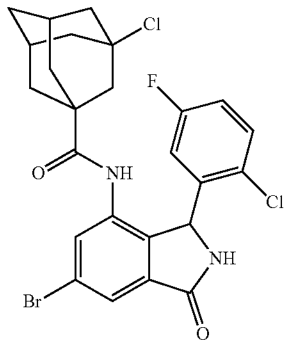 [SMILES: O=C1NC(c2cc(F)ccc2Cl)c2c(NC(=O)C34CC5CC(CC(Cl)(C5)C3)C4)cc(Br)cc21] | Fc1ccc(C1)c(c1)C1NC(=O)c2cc(Br)cc(NC(=O)C34CC5CC(CC(Cl)(C5)C3)C4)c12 | 1H-NMR (400 MHz, DMSO-d6) 9.38 (s, 1H), 9.24 (br. s, 1H), 7.72 (d, 1.7 Hz, 1H), 7.58 (d, 1.7 Hz, 1H), 7.55-7.47 (m, 1H), 7.25 (ddd, 8.8, 8.1, 3.1 Hz, 1H), 6.52 (br. s, 1H), 6.00 (br. s, 1H), 2.15-2.09 (m, 2H), 2.06-1.99 (m, 2H), 1.95-1.85 (m, 3H), 1.81-1.75 (m, 1H), 1.61-1.55 (m, 1H), 1.52-1.40 (m, 5H). | 551.3 | A | |
| I-1180 | 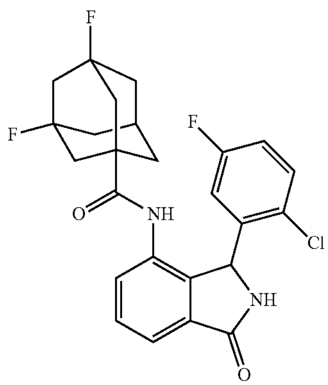 [SMILES: O=C1NC(c2cc(F)ccc2Cl)c2c(NC(=O)C34CC5CC(F)(CC(F)(C5)C3)C4)cccc21] | Fc1ccc(C1)c(c1)C1NC(=O)c2cccc(NC(=O)C34CC5CC(F)(CC(F)(C5)C3)C4)c12 | 1H-NMR (400 MHz, DMSO-d6) 9.45 (s, 1H), 9.11 (br. s, 1H), 7.63 (d, 6.8 Hz, 1H), 7.58 (t, 7.6 Hz, 1H), 7.56-7.49 (m, 1H), 7.39-7.35 (m, 1H), 7.25 (app. td, 8.4, 3.0 Hz, 1H), 6.38 (br. s, 1H), 6.01 (br. s, 1H), 2.42-2.35 (m, 1H), 2.07-1.99 (m, 1H), 1.94-1.87 (m, 1H), 1.81-1.73 (m, 2H), 1.71-1.59 (m, 5H), 1.58-1.52 (m, 1H), 1.42-1.29 (m, 2H). | 473.4 | B | |
| I-1181 | 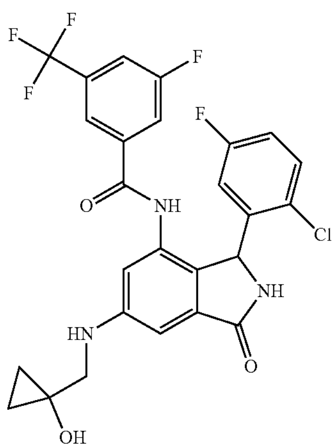 [SMILES: O=C(Nc1cc(NCC2(O)CC2)cc2c1C(c1cc(F)ccc1Cl)NC2=O)c1cc(F)cc(C(F)(F)F)c1] | OC1(CNc2cc3C(=O)NC(c3c(NC(=O)c3cc(F)cc(c3)C(F)(F)F)c2)c2cc(F)ccc2Cl)CC1 | (400 MHz, CD3CN) 8.48 (s, 1 H), 7.63 (d, 8.4 Hz, 1 H), 7.57 (d, 9.0 Hz, 1 H), 7.54 (s, 1 H), 7.23 (dd, 8.9, 5.1 Hz, 1 H), 7.09 (s, 1 H), 6.98-6.91 (m, 2 H), 6.86 (d, 1.9 Hz, 1 H), 6.64 (br s, 1 H), 5.98 (br s, 1 H), 5.08 (t, 5.5 Hz, 1 H), 3.60 (br s, 1 H), 3.28 (d, 5.6 Hz, 2 H), 0.73-0.69 (m, 2 H), 0.63-0.59 (m, 2 H). Contains small grease peaks at 0.86 and 1.27. | 552.4 | A | |
| I-1182 | 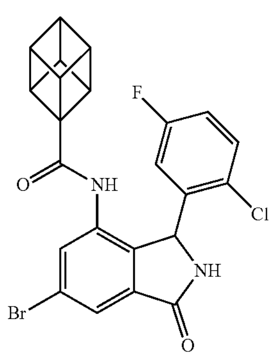 [SMILES: O=C1NC(c2cc(F)ccc2Cl)c2c(NC(=O)C34C5C6C7C5C3C7C64)cc(Br)cc21] | Fc1ccc(C1)c(c1)C1NC(=O)c2cc(Br)cc(NC(=O)C34C5C6C7C5C3C7C46)c12 | 1H-NMR (400MHz, DMSO-d6) 9.44 (s, 1H), 9.22 (br. s, 1H), 7.71 (d, 1.5 Hz, 1H), 7.62 (d, 1.7 Hz, 1H), 7.52-7.43 (m, 1H), 7.24 (app. td, 8.4, 3.1 Hz, 1H), 6.69 (br. s, 1H), 5.97 (br. s, 1H), 3.94-3.90 (m, 4H), 3.89-3.84 (m, 3H). | 485.3 | D | |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-1183 | 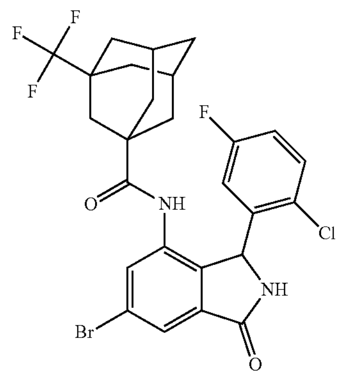 [SMILES: O=C1NC(c2cc(F)ccc2Cl)c2c(NC(=O)C34CC5CC(C3)CC(C(F)(F)F)(C5)C4)cc(Br)cc21] | Fc1ccc(C1)c(c1)C1NC(=O)c2cc(Br)cc(NC(=O)C34CC5CC(C3)CC(C5)(C4)C(F)(F)F)c12 | 1H-NMR (400 MHz, DMSO-d6) 9.44 (s, 1H), 9.25 (br. s, 1H), 7.72 (d, 1.6 Hz, 1H), 7.57 (d, 1.7 Hz, 1H), 7.52-7.44 (m, 1H), 7.22 (app. td, 8.4, 3.1 Hz, 1H), 6.48 (br. s, 1H), 5.99 (br. s, 1H), 2.11-2.04 (m, 2H), 1.69-1.62 (m, 2H), 1.61-1.41 (m, 9H), 1.38-1.32 (m, 1H). | 585.3 | A | |
| I-1184 | 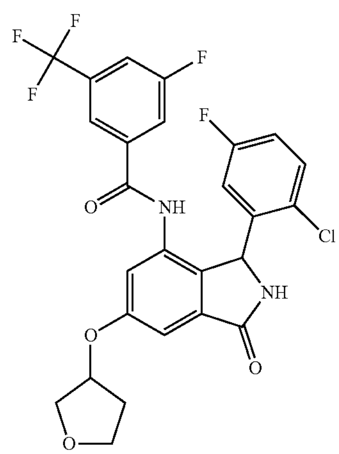 [SMILES: O=C(Nc1cc(OC2CCOC2)cc2c1C(c1cc(F)ccc1Cl)NC2=O)c1cc(F)cc(C(F)(F)F)c1] | Fc1ccc(C1)c(c1)C1NC(=O)c2cc(OC3CCOC3)cc(NC(=O)c3cc(F)cc(c3)C(F)(F)F)c12 | NMR (400 MHz, DMSO) 10.49 (br s, 1H), 9.14 (br s, 1H), 7.94 (d, 8.1 Hz., 1H), 7.71 (d, 9.0 Hz, 1H), 7.63 (s, 1H), 7.31 (dd, 8.9, 5.2 Hz, 1H), 7.18 (s, 1H), 7.09 (td overlapped with s, 8.2, 2.9 Hz, 1H), 7.06 (s overlapped with td, 1H), 6.64 (br s, 1H), 5.93 (br s, 1H), 5.20 (m, 1H), 3.90 (m, 3H), 3.79 (td, 8.4, 4.6 Hz, 1H), 2.34-2.21 (m, 1H), 2.09-1.97 (m, 1H). | 553 | A | |
| I-1185 | 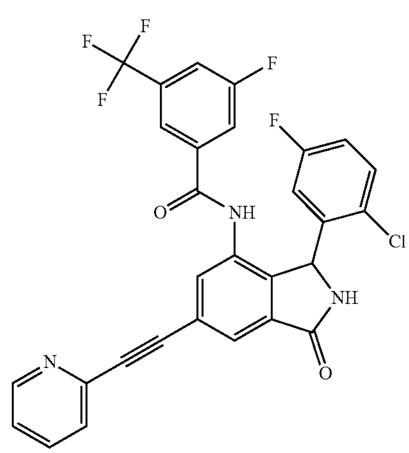 [SMILES: O=C(Nc1cc(C#Cc2ccccn2)cc2c1C(c1cc(F)ccc1Cl)NC2=O)c1cc(F)cc(C(F)(F)F)c1] | Fc1ccc(C1)c(c1)C1NC(=O)c2cc(cc(NC(=O)c3cc(F)cc(c3)C(F)(F)F)c12)C#Cc1ccccn1 | NMR (400 MHz, DMSO-d6) 10.53 (br. s, 1H), 9.31 (s, 1H), 8.65 (ddd, 4.8, 1.7, 0.9 Hz, 1H), 7.96 (br. d, 8.5 Hz, 1H), 7.90 (td, 7.7, 1.8 Hz, 1H), 7.85 (d, 0.9 Hz, 1H), 7.77-7.70 (m, 3H), 7.67 (s, 1H), 7.46 (ddd, 7.6, 4.9, 1.2 Hz, 1H), 7.34 (dd, 8.9, 5.2 Hz, 1H), 7.11 (td, 8.4, 3.0 Hz, 1H), 6.74 (br. s, 1H), 6.03 (br. s, 1H). | 568.3 | A | |

TABLE 2-continued

Representative Compounds of the Invention with Bioactivity Data.

| Ex. No. | Structure | SMILES | $^1$H NMR | MS | ADP-Glo IC$_{50}$ | MCF 10A IC$_{50}$ |
|---|---|---|---|---|---|---|
| I-1186 | 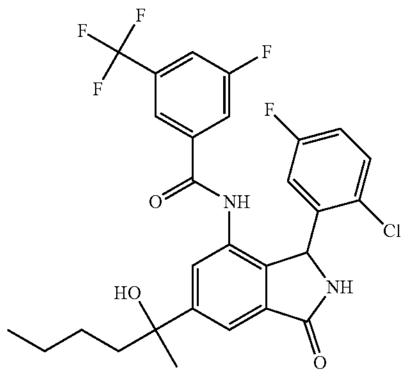 [SMILES: CCCCC(C)(O)c1cc(NC(=O)c2cc(F)cc(C(F)(F)F)c2)c2c(c1)C(=O)NC2c1cc(F)ccc1Cl] | CCCCC(C)(O)c1cc2C(=O)NC(c2c(NC(=O)c2cc(F)cc(c2)C(F)(F)F)c1)c1cc(F)ccc1Cl | NMR (400 MHz, DMSO-d6) 10.53 (s, 1H), 9.09 (s, 1H), 7.93 (br. d, 8.4 Hz, 1H), 7.76 (br. d, 8.9 Hz, 1H), 7.73-7.70 (m, 1H), 7.68 (s, 1H), 7.54 (s, 1H), 7.31 (dd, 8.9, 5.2 Hz, 1H), 7.09 (td, 8.4, 3.0 Hz, 1H), 6.57 (br. s, 1H), 5.93 (br. s, 1H), 5.14 (s, 1H), 1.81-1.64 (m, 2H), 1.50 (s, 3H), 1.33-1.12 (m, 3H), 1.05-0.89 (m, 1H), 0.84-0.76 (m, 3H). | 567.2 | A | |
| I-1187 | 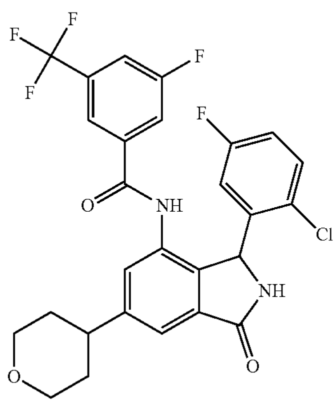 [SMILES: O=C(Nc1cc(C2CCOCC2)cc2c1C(c1cc(F)ccc1Cl)NC2=O)c1cc(F)cc(C(F)(F)F)c1] | Fc1ccc(C1)c(c1)C1NC(=O)c2cc(cc(NC(=O)c3cc(F)cc(c3)C(F)(F)F)c12)C1CCOCC1 | NMR (400 MHz, DMSO-D6) 10.52 (br s, 1H), 9.12 (br s, 1H), 7.94 (d, 9.2 Hz, 1H), 7.74 (d, 8.3 Hz, 1H), 7.66 (s, 1H), 7.57 (s, 1H), 7.38 (s, 1H), 7.30 (dd, 8.8, 5.2 Hz, 1H), 7.08 (td, 8.2, 2.6 Hz, 1H), 6.61 (br s, 1H), 5.97 (br s, 1H), 3.98 (dd, 11.1, 3.6 Hz, 2H), 3.47 (t, 11.5 Hz, 2H), 3.01-2.95 (m, 1H), 1.89-1.56 (m, 4H). | 551.3 | A | |
| I-1188 | 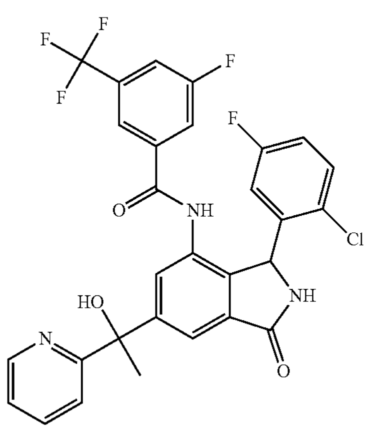 [SMILES: CC(O)(c1cc(NC(=O)c2cc(F)cc(C(F)(F)F)c2)c2c(c1)C(=O)NC2c1cc(F)ccc1Cl)c1ccccn1] | CC(O)(c1cc2C(=O)NC(c2c(NC(=O)c2cc(F)cc(c2)C(F)(F)F)c1)c1cc(F)ccc1Cl)c1ccccn1 | NMR (400 MHz, DMSO-d6) 10.50 (br. s, 1H), 9.10 (s, 1H), 8.55-8.50 (m, 1H), 7.93 (br. d, 8.5 Hz, 1H), 7.82-7.77 (m, 2H), 7.76-7.70 (m, 2H), 7.64 (s, 1H), 7.60 (s, 1H), 7.31-7.22 (m, 2H), 6.55 (br. s, 1H), 6.25 (s, 1H), 5.90 (br. s, 1H), 1.94 (s, 3H). | 588.2 | A | |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-1189 | 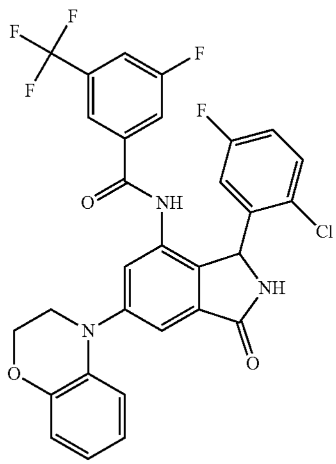 [SMILES: O=C(Nc1cc(N2CCOc3ccccc32)cc2c1C(c1cc(F)ccc1Cl)NC2=O)c1cc(F)cc(C(F)(F)F)c1] | Fc1ccc(C1)c(c1)C1NC(=O)c2cc(cc(NC(=O)c3cc(F)cc(c3)C(F)(F)F)c12)N1CCOc2ccccc12 | | 600.38 | A | |
| I-1190 | 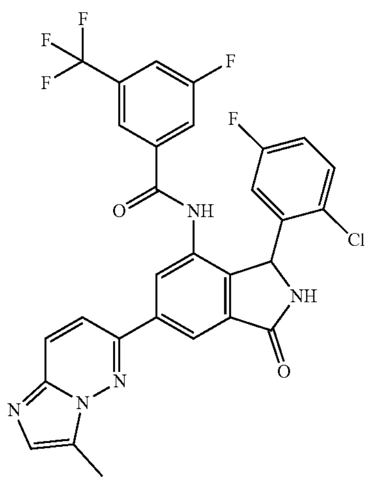 [SMILES: Cc1cnc2ccc(-c3cc(NC(=O)c4cc(F)cc(C(F)(F)F)c4)c4c(c3)C(=O)NC4c3cc(F)ccc3Cl)nn12] | Cc1cnc2ccc(nn12)-c1cc2C(=O)NC(c2c(NC(=O)c2cc(F)cc(c2)C(F)(F)F)c1)c1cc(F)ccc1Cl | | 598.38 | A | |
| I-1191 | 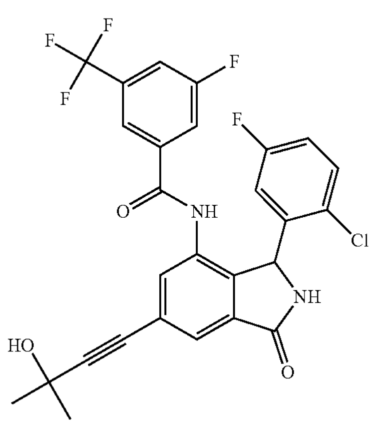 [SMILES: CC(C)(O)C#Cc1cc(NC(=O)c2cc(F)cc(C(F)(F)F)c2)c2c(c1)C(=O)NC2c1cc(F)ccc1Cl] | CC(C)(O)C#Cc1cc2C(=O)NC(c2c(NC(=O)c2cc(F)cc(c2)C(F)(F)F)c1)c1cc(F)ccc1Cl | | 549.4 | A | |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-1192 | 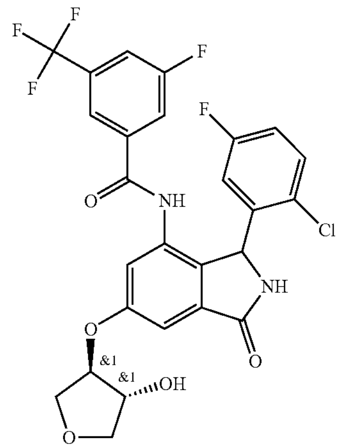 [SMILES: O=C(Nc1cc(O[C@@H]2COC[C@H]2O)cc2c1C(c1cc(F)ccc1Cl)NC2=O)c1cc(F)cc(C(F)(F)F)c1] | O[C@@H]1COC[C@H]1Oc1cc2C(=O)NC(c2c(NC(=O)c2cc(F)cc(c2)C(F)(F)F)c1)c1cc(F)ccc1Cl | | 569.4 | A | |
| I-1193 | 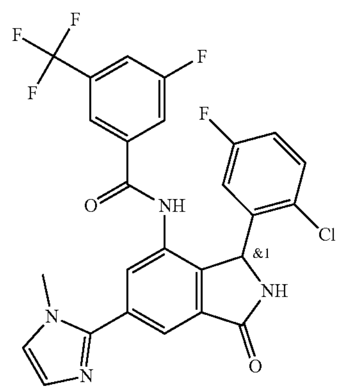 [SMILES: Cn1ccnc1-c1cc(NC(=O)c2cc(F)cc(C(F)(F)F)c2)c2c(c1)C(=O)NC2c1cc(F)ccc1Cl] | Cn1ccnc1-c1cc2C(=O)NC(c2c(NC(=O)c2cc(F)cc(c2)C(F)(F)F)c1)c1cc(F)ccc1Cl | (400 MHz, DMSO-d6) 9.15 (s, 1H), 8.51 (s, 1H), 8.08 (br s, 1H), 7.87-7.70 (m, 4H), 7.35 (dd, 8.8, 5.2 Hz, 1H), 7.31 (s, 1H), 7.09 (td, 8.4, 2.9 Hz, 1H), 7.03 (s, 1H), 6.70 (br s, 1H), 6.04 (s, 1H), 3.85 (s, 3H) | 547.2 | B | |
| I-1194 | 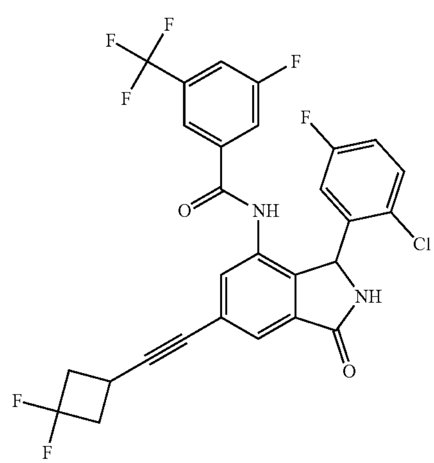 [SMILES: O=C(Nc1cc(C#CC2CC(F)(F)C2)cc2c1C(c1cc(F)ccc1Cl)NC2=O)c1cc(F)cc(C(F)(F)F)c1] | Fc1ccc(C1)c(c1)C1NC(=O)c2cc(cc(NC(=O)c3cc(F)cc(c3)C(F)(F)F)c12)C#CC1CC(F)(F)C1 | | 581.5 | B | |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-1195 | 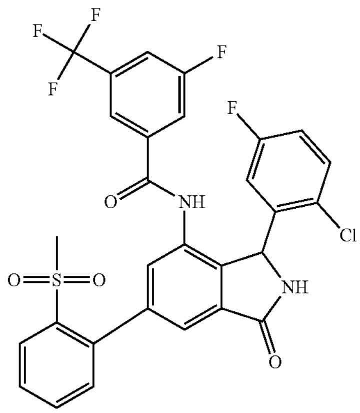 [SMILES: CS(=O)(=O)c1ccccc1-c1cc(NC(=O)c2cc(F)cc(C(F)(F)F)c2)c2c(c1)C(=O)NC2c1cc(F)ccc1Cl] | CS(=O)(=O)c1cccc1-c1cc2C(=O)NC(c2c(NC(=O)c2cc(F)cc(c2)C(F)(F)F)c1)c1cc(F)ccc1Cl | 1H NMR (400 MHz, DMSO-d6) 2.97 (s, 3 H) 6.05 (br s, 1 H) 7.11 (td, 8.34, 3.03 Hz, 1 H) 7.34 (dd, 8.97, 5.18 Hz, 1 H) 7.46-7.54 (m, 2 H) 7.63-7.83 (m, 5 H) 7.93 (br d, 8.34 Hz, 1 H) 8.13 (dd, 7.83, 1.26 Hz, 1 H) 9.25 (br s, 1 H) 10.62 (s, 1 H) | 621.34 | A | |
| I-1196 | 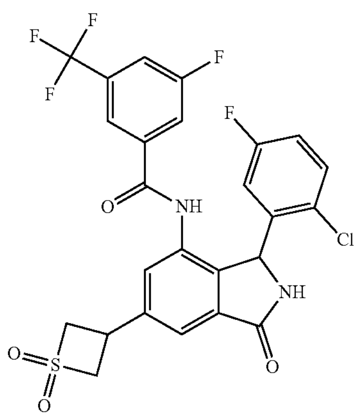 [SMILES: O=C(Nc1cc(C2CS(=O)(=O)C2)cc2c1C(c1cc(F)ccc1Cl)NC2=O)c1cc(F)cc(C(F)(F)F)c1] | Fc1ccc(C1)c(c1)C1NC(=O)c2cc(cc(NC(=O)c3cc(F)cc(c3)C(F)(F)F)c12)C1CS(=O)(=O)C1 | 1H NMR (500 MHz, DMSO-d6) 4.04-4.14 (m, 1 H) 4.32-4.49 (m, 2 H) 4.62-4.73 (m, 2 H) 5.98 (br d, 1.98 Hz, 1 H) 6.73-6.89 (m, 1 H) 7.09 (td, 8.39, 2.90 Hz, 1 H) 7.31 (dd, 8.85, 5.19 Hz, 1 H) 7.51-7.57 (m, 1 H) 7.67 (s, 1 H) 7.71-7.81 (m, 2 H) 7.94 (br d, 8.24 Hz, 1 H) 9.17 (br s, 1 H) 10.59 (br s, 1 H) | 571.32 | A | |
| I-1197 | 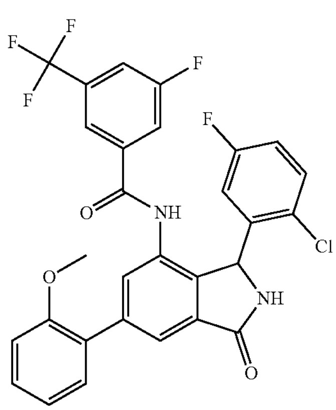 [SMILES: COc1ccccc1-c1cc(NC(=O)c2cc(F)cc(C(F)(F)F)c2)c2c(c1)C(=O)NC2c1cc(F)ccc1Cl] | COc1ccccc1-c1cc2C(=O)NC(c2c(NC(=O)c2cc(F)cc(c2)C(F)(F)F)c1)c1cc(F)ccc1Cl | 1H NMR (500 MHz, DMSO-d6) 3.81 (s, 3 H) 6.02 (br s, 1 H) 7.04-7.14 (m, 2 H) 7.18 (d, 8.24 Hz, 1 H) 7.32 (dd, 8.85, 5.19 Hz, 1 H) 7.36-7.44 (m, 2 H) 7.60 (s, 1 H) 7.67 (s, 1 H) 7.70-7.80 (m, 2 H) 7.93 (br d, 8.24 Hz, 1 H) 9.16 (br s, 1 H) 10.51 (s, 1 H) | 573.37 | B | |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-1198 | 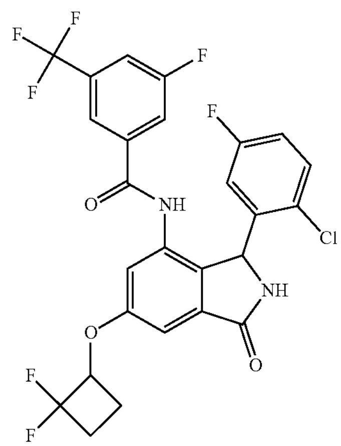 [SMILES: O=C(Nc1cc(OC2CCC2(F)F)cc2c1C(c1cc(F)ccc1Cl)NC2=O)c1cc(F)cc(C(F)(F)F)c1] | Fc1ccc(C1)c(c1)C1NC(=O)c2cc(OC3CCC3(F)F)cc(NC(=O)c3cc(F)cc(c3)C(F)(F)F)c12 | 1H NMR (400 MHz, DMSO) 10.55 (br. s, 1H), 9.24 (s, 1H), 7.95 (d, 8.2 Hz, 1H), 7.72 (d, 9.7 Hz, 1H), 7.64 (s, 1H), 7.43 (s, 1H), 7.37-7.26 (m, 2H), 7.09 (td, 8.5, 3.1 Hz, 1H), 6.61 (submerged br. s, 1H), 6.43 (ddd, 59.9, 16.9, 11.9 Hz, 1H), 5.96 (s, 1H), 1.37-1.14 (m, 2H), 1.15-0.99 (m, 2H) | 573.2 | A | |
| I-1199 | 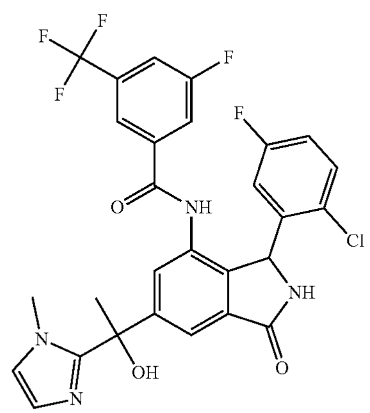 [SMILES: Cn1ccnc1C(C)(O)c1cc(NC(=O)c2cc(F)cc(C(F)(F)F)c2)c2c(c1)C(=O)NC2c1cc(F)ccc1Cl] | Cn1ccnc1C(C)(O)c1cc2C(=O)NC(c2c(NC(=O)c2cc(F)cc(c2)C(F)(F)F)c1)c1cc(F)ccc1Cl | NMR (400 MHz, DMSO-d6) 10.56 (br. s, 1H), 9.13 (br. s, 1H), 8.26 (s, 1H), 7.92 (br. d, 8.3 Hz, 1H), 7.72 (app. t, 8.4 Hz, 1H), 7.64-7.59 (m, 1H), 7.43 (s, 1H), 7.30 (dd, 8.9, 5.2 Hz, 1H), 7.11-7.04 (m, 2H), 6.85-6.82 (m, 1H), 6.43 (br. s, 1H), 5.93 (br. s, 1H), 3.33 (s, 3H), 1.90 (s, 3H). | 591.2 | A | |
| I-1200 | 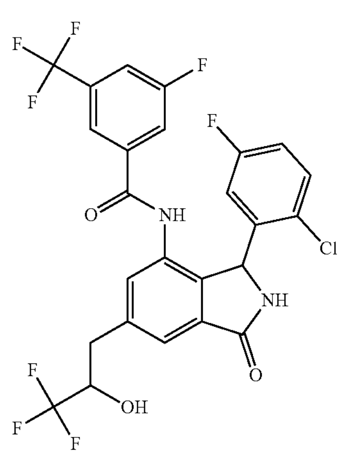 [SMILES: O=C(Nc1cc(CC(O)C(F)(F)F)cc2c1C(c1cc(F)ccc1Cl)NC2=O)c1cc(F)cc(C(F)(F)F)c1] | OC(Cc1cc2C(=O)NC(c2c(NC(=O)c2cc(F)cc(c2)C(F)(F)F)c1)c1cc(F)ccc1Cl)C(F)(F)F | NMR (400 MHz, DMSO-d6) 10.50 (br s, 1H), 9.12 (br s, 1H), 7.94 (d, 8.3 Hz, 1H), 7.74 (d, 8.7 Hz, 1H), 7.70-7.63 (m, 2H), 7.43 (s, 1H), 7.31 (dd, 8.9, 5.1 Hz, 1H), 7.10 (td, 8.9, 2.1 Hz, 1H), 6.65 (submerged br s, 1H), 6.35 (br s, 1H), 5.94 (br s, 1H), 4.28 (br s, 1H), 3.18-3.03 (m, 1H), 2.97-2.79 (m, 1H). | 579.2 | A | |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-1201 | 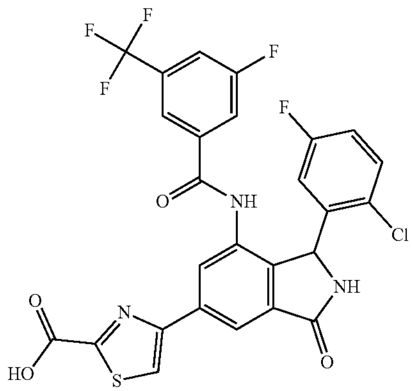 [SMILES: O=C(Nc1cc(-c2csc(C(=O)O)n2)cc2c1C(c1cc(F)ccc1Cl)NC2=O)c1cc(F)cc(C(F)(F)F)c1] | OC(=O)c1nc(cs1)-c1cc2C(=O)NC(c2c(NC(=O)c2cc(F)cc(c2)C(F)(F)F)c1)c1cc(F)ccc1Cl | NMR (400 MHz, DMSO-d6) 10.65 (br s, 1H), 9.20 (br s, 1H), 8.43 (br s, 1H), 8.26 (s, 1H), 8.18 (s, 1H), 7.94 (dd, 9.0, 1.2 Hz, 1H), 7.79 (dd, 9.0, 1.2 Hz, 1H), 7.72 (br s, 1H), 7.32 (dd, 9.0, 5.1 Hz, 1H), 7.17 (br s, 1H), 7.13-7.05 (m, 1H), 6.03 (br s, 1H). | 594.1 | A | |
| I-1202 | 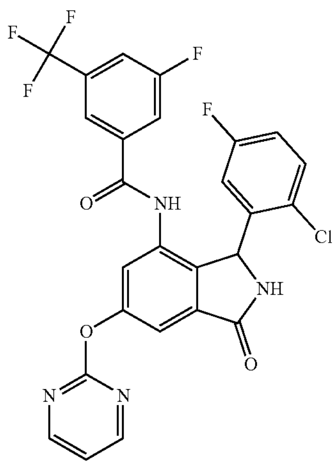 [SMILES: O=C(Nc1cc(Oc2ncccn2)cc2c1C(c1cc(F)ccc1Cl)NC2=O)c1cc(F)cc(C(F)(F)F)c1] | Fc1ccc(C1)c(c1)C1NC(=O)c2cc(Oc3ncccn3)cc(NC(=O)c3cc(F)cc(c3)C(F)(F)F)c12 | NMR (400 MHz, DMSO-d6) 10.56 (s, 1H), 9.27 (s, 1H), 8.71 (d, 4.8 Hz, 2 X 1H), 7.95 (dt, 8.4, 2.0 Hz, 1H), 7.72 (br. d, 9.2 Hz, 1H), 7.64 (s, 1H), 7.52 (d, 1.9 Hz, 1H), 7.37 (s, 1H), 7.36-7.32 (m, 2H), 7.12 (td, 8.5, 3.1 Hz, 1H), 6.69 (br. s, 1H), 6.00 (br. s, 1H). | 561.1 | B | |
| I-1203 | 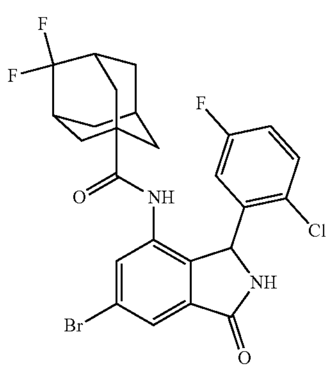 [SMILES: O=C1NC(c2cc(F)ccc2Cl)c2c(NC(=O)C34CC5CC(C3)C(F)(F)C(C5)C4)cc(Br)cc21] | Fc1ccc(C1)c(c1)C1NC(=O)c2cc(Br)cc(NC(=O)C34CC5CC(C3)C(F)(F)C(C5)C4)c12 | 1H-NMR (400 MHz, DMSO-d6) 9.42 (s, 1H), 9.25 (br. s, 1H), 7.72 (d, 1.6 Hz, 1H), 7.59 (d, 1.7 Hz, 1H), 7.55-7.45 (m, 1H), 7.25 (app. td, 8.4, 3.0 Hz, 1H), 6.56 (br. s, 1H), 5.99 (br. s, 1H), 2.18-2.10 (m, 2H), 1.92-1.86 (m, 1H), 1.79-1.66 (m, 3H), 1.65-1.57 (m, 5H), 1.56-1.51 (m, 2H). | 555.2 | B | |
| I-1204 | 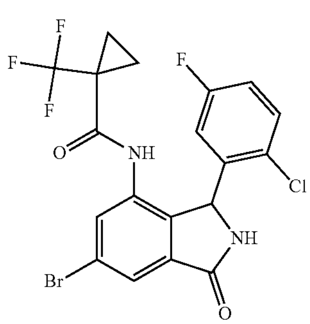 [SMILES: O=C1NC(c2cc(F)ccc2Cl)c2c(NC(=O)C3(C(F)(F)F)CC3)cc(Br)cc21] | Fc1ccc(C1)c(c1)C1NC(=O)c2cc(Br)cc(NC(=O)C3(CC3)C(F)(F)F)c12 | 1H-NMR (400 MHz, DMSO-d6) 9.51 (br. s, 1H), 9.25 (s, 1H), 7.75 (s, 1H), 7.62 (s, 1H), 7.55-7.44 (m, 1H), 7.25 (app. td, 8.5, 3.1 Hz, 1H), 6.55 (br. s, 1H), 5.90 (br. s, 1H), 1.22-1.08 (m, 3H), 0.81-0.73 (m, 1H). | 493.1 | E | |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-1205 | 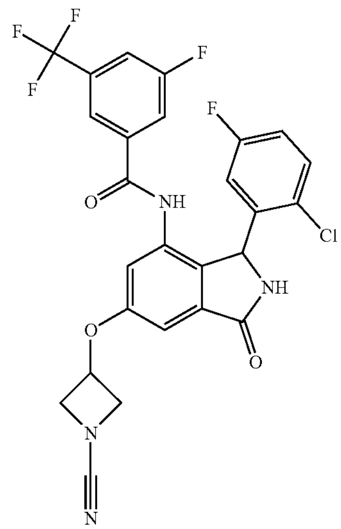 [SMILES: N#CN1CC(Oc2cc(NC(=O)c3cc(F)cc(C(F)(F)F)c3)c3c(c2)C(=O)NC3c2cc(F)ccc2Cl)C1] | Fc1ccc(C1)c(c1)C1NC(=O)c2cc(OC3CN(C3)C#N)cc(NC(=O)c3cc(F)cc(c3)C(F)(F)F)c12 | NMR (400 MHz, DMSO) 10.47 (s, 1H), 9.17 (s, 1H), 7.95 (d, 8.5 Hz, 1H), 7.70 (d, 9.6 Hz, 1H), 7.62 (s, 1H), 7.31 (dd, 8.9, 5.2 Hz, 1H), 7.09 (td, 8.5, 3.3 Hz, 1H), 7.02 (s, 2H), 5.92 (s, 1H), 5.27-5.20 (m, 1H), 4.68-4.64 (m, 2H), 4.24 (m, 2H). B-pocket ortho proton missing. By LC, approx. 12-13% impurity which is oxidized product. | 563 | A | |
| I-1206 | 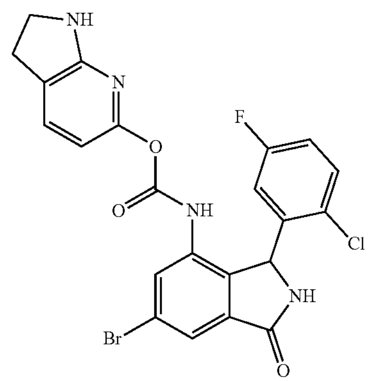 [SMILES: O=C(Nc1cc(Br)cc2c1C(c1cc(F)ccc1Cl)NC2=O)Oc1ccc2c(n1)NCC2] | Fc1ccc(C1)c(c1)C1NC(=O)c2cc(Br)cc(NC(=O)Oc3ccc4CCNc4n3)c12 | 1H NMR (400 MHz, DMSO-d6) 10.65 (s, 1H), 9.26 (s, 1H), 7.89 (s, 1H), 7.71 (s, 1H), 7.47 (d, 8.0 Hz, 1H), 7.29 (dd, 9.0, 5.1 Hz, 1H), 7.04 (1, 8.5 Hz, 1H), 6.18 (d, 8.1 Hz, 2H), 3.92 (q, 9.3 Hz, 1H), 3.80 (q, 10.3, 9.6 Hz, 1H), 2.89 (t, 8.6 Hz, 2H). | 517.1 | E | |
| I-1207 | 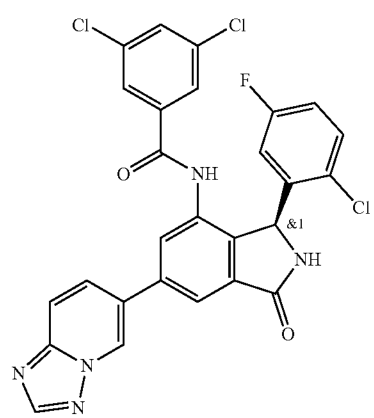 [SMILES: O=C(Nc1cc(-c2ccc3ncnn3c2)cc2c1[C@@H](c1cc(F)ccc1Cl)NC2=O)c1cc(Cl)cc(Cl)c1] | Fc1ccc(C1)c(c1)[C@H]1NC(=O)c2cc(cc(NC(=O)c3cc(C1)cc(Cl)c3)c12)-c1ccc2ncnn2c1 | 1H NMR (400 MHz, DMSO-d6) 10.51 (s, 1H), 9.47 (dd, 1.9, 1.0 Hz, 1H), 9.25 (s, 1H), 8.58 (s, 1H), 8.13 (dd, 9.1, 1.8 Hz, 2H), 8.03-7.93 (m, 2H), 7.86 (t, 1.9 Hz, 1H), 7.57 (d, 1.9 Hz, 2H), 7.40 (dd, 8.9, 5.1 Hz, 1H), 7.17 (td, 8.3, 3.0 Hz, 1H), 6.71 (s, 1H), 6.08 (s, 1H) | 565.8 | D | |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-1208 | 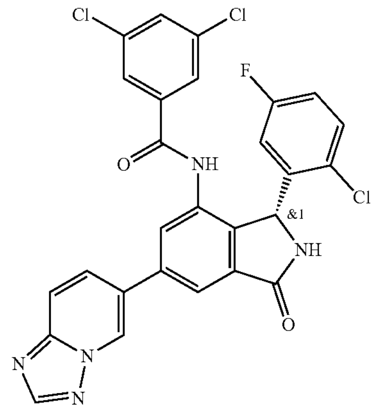 [SMILES: O=C(Nc1cc(-c2ccc3ncnn3c2)cc2c1[C@H](c1cc(F)ccc1Cl)NC2=O)c1cc(Cl)cc(Cl)c1] | Fc1ccc(C1)c(c1)[C@@H]1NC(=O)c2cc(cc(NC(=O)c3cc(Cl)cc(Cl)c3)c1 2)-c1ccc2ncnn2c1 | 1H NMR (400 MHz, DMSO-d6) 10.51 (s, 1H), 9.47 (dd, 1.9, 0.9 Hz, 1H), 9.25 (s, 1H), 8.58 (s, 1H), 8.13 (dd, 9.2, 1.8 Hz, 2H), 8.03-7.93 (m, 2H), 7.86 (t, 1.9 Hz, 1H), 7.57 (d, 1.9 Hz, 2H), 7.40 (dd, 8.9, 5.1 Hz, 1H), 7.17 (td, 8.4, 3.0 Hz, 1H), 6.08 (s, 1H). | 565.95 | A | |
| I-1209 | 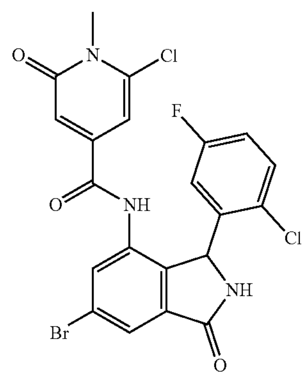 [SMILES: Cn1c(Cl)cc(C(=O)Nc2cc(Br)cc3c2C(c2cc(F)ccc2Cl)NC3=O)cc1=O] | Cn1c(Cl)cc(cc1=O)C(=O)Nc1cc(Br)cc2C(=O)NC(c12)c1cc(F)ccc1Cl | 1H NMR (400 MHz, DMSO-d6) 10.44 (s, 1H), 9.30 (s, 1H), 7.82 (d, 1.7 Hz, 1H), 7.71 (d, 1.6 Hz, 1H), 7.43 (d, 8.2 Hz, 1H), 7.19 (td, 8.5, 8.1, 2.8 Hz, 1H), 6.86 (s, 1H), 6.47 (q, 1.9 Hz, 2H), 5.97 (s, 1H), 3.57 (d, 1.3 Hz, 3H) | 525.85 | E | |
| I-1210 | 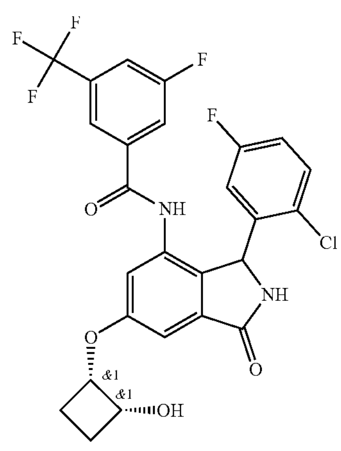 [SMILES: O=C(Nc1cc(O[C@H]2CC[C@H]2O)cc2c1C(c1cc(F)ccc1Cl)NC2=O)c1cc(F)cc(C(F)(F)F)c1] | O[C@@H]1CC[C@@H]1Oc1cc2C(=O)NC(c2c(NC(=O)c2cc(F)cc(c2)C(F)(F)F)c1)c1cc(F)ccc1Cl | 1H NMR (400 MHz, DMSO-d6) 10.45 (s, 1H), 9.11 (s, 1H), 7.94 (d, 8.4 Hz, 1H), 7.71 (d, 8.2 Hz, 1H), 7.62 (s, 1H), 7.31 (dd, 8.5, 5.0 Hz, 1H), 7.11 (d, 2.2 Hz, 1H), 7.07 (td, 8.5, 2.9 Hz, 1H), 7.04 (br. s, 1H), 6.49 (br. s, 1H), 5.92 (br. s, 1H), 5.23 (t, 7.35 Hz, 1H), 4.88-4.72 (m, 1H), 4.44 (br. s, 1H), 2.23-2.02 (m, 3H), 2.01-1.86 (m, 1H); | 553.2 | A | |

TABLE 2-continued

Representative Compounds of the Invention with Bioactivity Data.

| Ex. No. | Structure | SMILES | ¹H NMR | MS | ADP-Glo IC₅₀ | MCF 10A IC₅₀ |
|---|---|---|---|---|---|---|
| I-1211 | 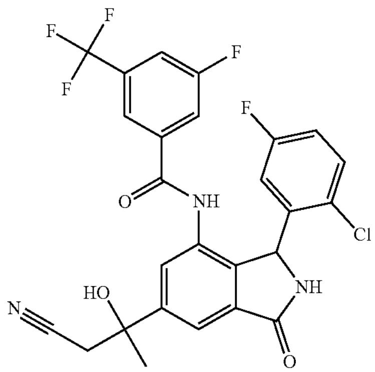 [SMILES: CC(O)(CC#N)c1cc(NC(=O)c2cc(F)cc(C(F)(F)F)c2)c2c(c1)C(=O)NC2c1cc(F)ccc1Cl] | CC(O)(CC#N)c1cc2C(=O)NC(c2c(NC(=O)c2cc(F)cc(c2)C(F)(F)F)c1)cc(F)ccc1Cl | (400 MHz, DMSO-d6) 10.56 (s, 1H), 9.16 (s, 1H), 7.94 (d, 8.4 Hz, 1H), 7.84 (s, 1H), 7.75 (d, 9.0 Hz, 1H), 7.68 (s, 2H), 7.31 (dd, 8.8, 5.2 Hz, 1H), 7.10 (td, 8.4, 3.0 Hz, 1H), 6.58 (br s, 1H), 6.08 (s, 1H), 5.96 (br s, 1H), 3.14-3.07 (m, 2H), 1.63 (s, 3H) | 550.2 | A | |
| I-1212 | 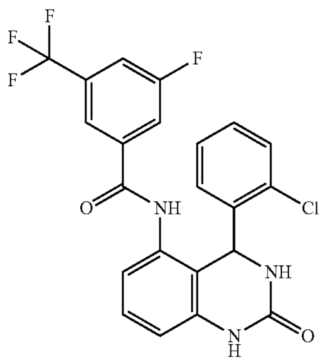 | Fc1cc(cc(c1)C(F)(F)F)C(=O)Nc1ccc2NC(=O)NC(c3ccccc3Cl)c12 | NMR (400 MHz, DMSO) 10.15 (s, 1H), 9.49 (d, 1.7 Hz, 1H), 8.00-7.91 (m, 2H), 7.89 (d, 9.2 Hz, 1H), 7.55-7.49 (m, 2H), 7.31-7.23 (m, 2H), 7.23-7.16 (m, 2H), 7.06 (dd, 5.9, 3.5 Hz, 1H), 6.89 (d, 7.3 Hz, 1H), 6.80 (d, 7.8 Hz, 1H), 6.14 (d, 3.0 Hz, 1H). | 464.1 | D | |
| I-1213 | 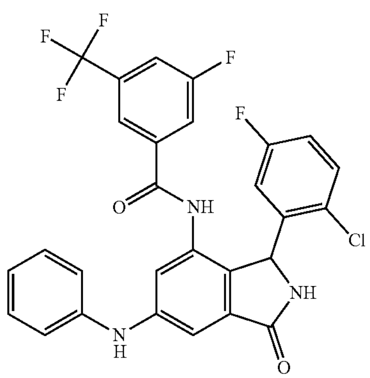 | Fc1ccc(C1)c(c1)C1NC(=O)c2cc(Nc3ccccc3)cc(NC(=O)c3cc(F)cc(c3)C(F)(F)F)c12 | | 558.36 | A | |
| I-1214 | 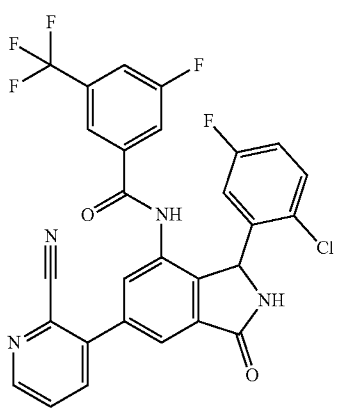 [SMILES: N#Cc1ncccc1-c1cc(NC(=O)c2cc(F)cc(C(F)(F)F)c2)c2c(c1)C(=O)NC2c1cc(F)ccc1Cl] | Fc1ccc(C1)c(c1)C1NC(=O)c2cc(cc(NC(=O)c3cc(F)cc(c3)C(F)(F)F)c12)-c1cccnc1C#N | | 569.31 | A | |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-1215 | 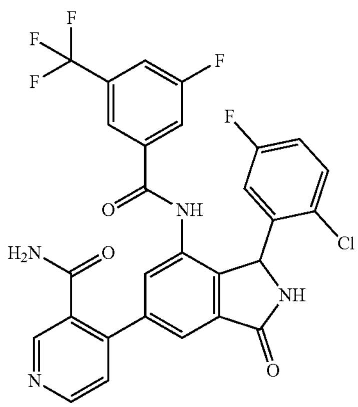 [SMILES: NC(=O)c1cnccc1-c1cc(NC(=O)c2cc(F)cc(C(F)(F)F)c2)c2c(c1)C(=O)NC2c1cc(F)ccc1Cl] | NC(=O)c1cnccc1-c1cc2C(=O)NC(c2c(NC(=O)c2cc(F)cc(c2)C(F)(F)F)c1)c1cc(F)ccc1Cl | | 587.27 | B | |
| I-1216 | 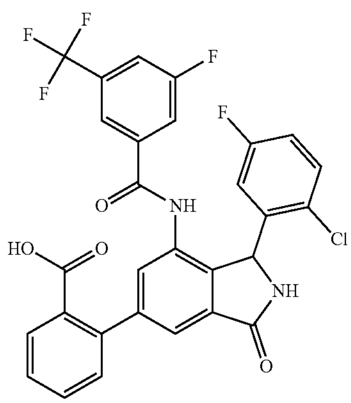 [SMILES: O=C(Nc1cc(-c2ccccc2C(=O)O)cc2c1C(c1cc(F)ccc1Cl)NC2=O)c1cc(F)cc(C(F)(F)F)c1] | OC(=O)c1ccccc1-c1cc2C(=O)NC(c2c(NC(=O)c2cc(F)cc(c2)C(F)(F)F)c1)c1cc(F)ccc1Cl | 1H NMR (500 MHz, DMSO-d6) 5.95-6.11 (m, 1 H) 7.10 (td, 8.32, 2.90 Hz, 1 H) 7.33 (dd, 8.85, 5.04 Hz, 1 H) 7.44-7.53 (m, 3 H) 7.56-7.63 (m, 2 H) 7.66 (s, 1 H) 7.76 (br dd, 15.49, 8.32 Hz, 2 H) 7.93 (br d, 8.39 Hz, 1 H) 9.18 (br s, 1 H) 10.58 (s, 1 H) | 587.37 | B | |
| I-1217 | 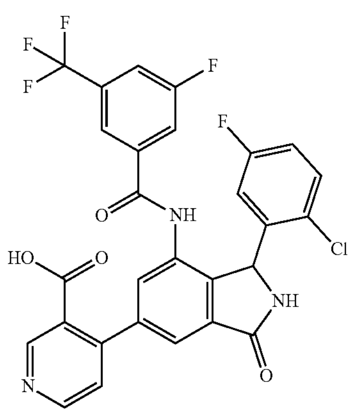 [SMILES: O=C(Nc1cc(-c2ccncc2C(=O)O)cc2c1C(c1cc(F)ccc1Cl)NC2=O)c1cc(F)cc(C(F)(F)F)c1] | OC(=O)c1cnccc1-c1cc2C(=O)NC(c2c(NC(=O)c2cc(F)cc(c2)C(F)(F)F)c1)c1cc(F)ccc1Cl | 1H NMR (500 MHz, DMSO-d6) 5.96-6.12 (m, 1 H) 7.10 (td, 8.32, 2.90 Hz, 1 H) 7.33 (dd, 8.85, 5.19 Hz, 1 H) 7.49-7.57 (m, 5 H) 7.58-7.68 (m, 6 H) 7.74 (br d, 8.39 Hz, 1 H) 7.93 (br d, 8.39 Hz, 1 H) 8.75 (d, 5.04 Hz, 1 H) 8.90-8.95 (m, 1 H) 9.23 (br s, 1 H) 10.62 (s, 1 H) | 588.32 | B | |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-1218 | 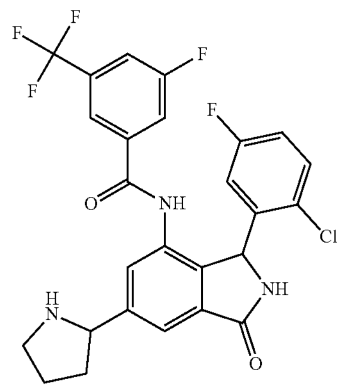 | Fc1ccc(C1)c(c1)C1NC(=O)c2cc(cc(NC(=O)c3cc(F)cc(c3)C(F)(F)F)c12)C1CCCN1 | 1H NMR (500 MHz, DMSO-d6) 1.54-1.65 (m, 1 H) 1.73-1.93 (m, 2 H) 2.25 (quind, 7.78, 7.78, 7.78, 7.78, 4.43 Hz, 1 H) 2.96-3.13 (m, 3 H) 4.25-4.34 (m, 1 H) 5.95 (br s, 1 H) 7.01-7.14 (m, 1 H) 7.29 (ddd, 8.66, 5.23, 1.68 Hz, 1 H) 7.51 (br d, 9.77 Hz, 1 H) 7.61-7.78 (m, 3 H) 7.92 (br d, 7.93 Hz, 1 H) 8.24 (s, 1 H) 9.08 (br s, 1 H) 10.50 (br d, 3.97 Hz, 1 H) | 536.45 | A | |
| I-1219 | 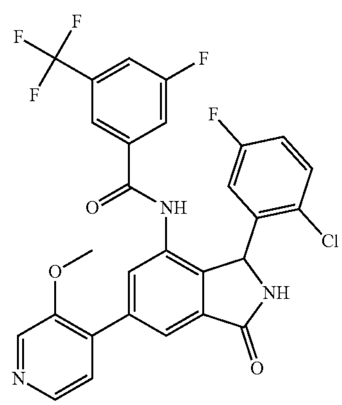 [SMILES: COc1cnccc1-c1cc(NC(=O)c2cc(F)cc(C(F)(F)F)c2)c2c(c1)C(=O)NC2c1cc(F)ccc1Cl] | COc1cnccc1-c1cc2C(=O)NC(c2c(NC(=O)c2cc(F)cc(c2)C(F)(F)F)c1)c1cc(F)ccc1Cl | 1H NMR (500 MHz, DMSO-d6) 3.95 (s, 3 H) 6.04 (br s, 1 H) 7.10 (td, 8.35, 2.98 Hz, 1 H) 7.33 (dd, 8.93, 5.11 Hz, 1 H) 7.47 (d, 4.88 Hz, 1 H) 7.57-7.65 (m, 1 H) 7.65-7.76 (m, 3 H) 7.88 (s, 1 H) 7.94 (br d, 8.39 Hz, 1 H) 8.33 (d, 4.88 Hz, 1 H) 8.54 (s, 1 H) 9.22 (br s, 1 H) 10.57 (s, 1 H) | 574.37 | A | |
| I-1220 | 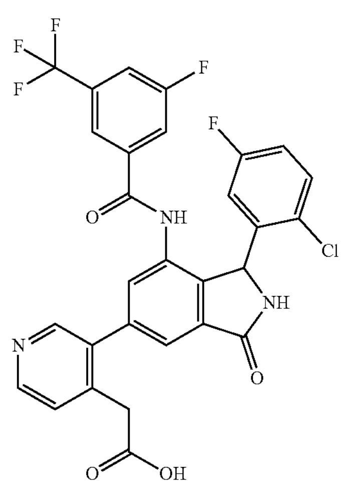 [SMILES: O=C(O)Cc1ccncc1-c1cc(NC(=O)c2cc(F)cc(C(F)(F)F)c2)c2c(c1)C(=O)NC2c1cc(F)ccc1Cl] | OC(=O)Cc1ccncc1-c1cc2C(=O)NC(c2c(NC(=O)c2cc(F)cc(c2)C(F)(F)F)c1)c1cc(F)ccc1Cl | 1H NMR (500 MHz, DMSO-d6) 2.33 (s, 2 H) 5.94-6.13 (m, 1 H) 7.11 (td, 8.35, 2.98 Hz, 1 H) 7.34 (dd, 8.85, 5.34 Hz, 1 H) 7.37-7.40 (m, 1 H) 7.51 (s, 1 H) 7.65-7.69 (m, 2 H) 7.74 (br d, 8.85 Hz, 1 H) 7.94 (br d, 8.39 Hz, 1 H) 8.45-8.51 (m, 2 H) 9.23 (br s, 1 H) 10.56 (s, 1 H) | 602.33 | A | |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-1221 | 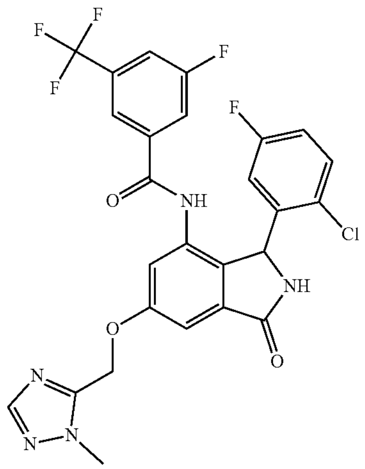 [SMILES: Cn1ncnc1COc1cc(NC(=O)c2cc(F)cc(C(F)(F)F)c2)c2c(c1)C(=O)NC2c1cc(F)ccc1Cl] | Cn1ncnc1COc1cc2C(=O)NC(c2c(NC(=O)c2cc(F)cc(c2)C(F)(F)F)c1)c1cc(F)ccc1Cl | 1H NMR (DMSO-d6, 400 MHz):-' = 10.48 (s, 1H), 9.15 (br s, 1H), 7.97 (s, 1H), 7.92-7.96 (m, 1H), 7.71 (br d, 9.1 Hz, 1H), 7.63 (s, 1H), 7.43 (d, 2.0 Hz, 1H), 7.31 (dd, 8.8, 5.1 Hz, 1H), 7.17 (d, 1.8 Hz, 1H), 7.09 (td, 8.3, 3.0 Hz, 1H), 5.92 (br s, 1H), 5.46 (d, 2.0 Hz, 2H), 3.94 (s, 3H) | 578.1 | A | |
| I-1222 | 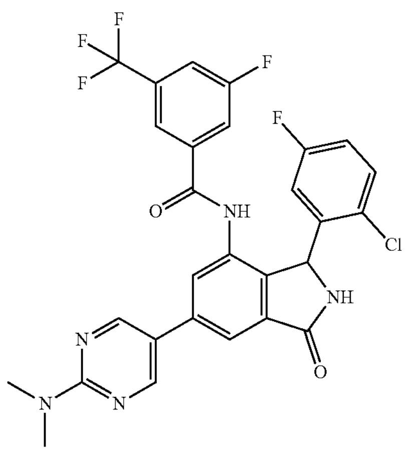 [SMILES: CN(C)c1ncc(-c2cc(NC(=O)c3cc(F)cc(C(F)(F)F)c3)c3c(c2)C(=O)NC3c2cc(F)ccc2Cl)cn1] | CN(C)c1ncc(cn1)-c1cc2C(=O)NC(c2c(NC(=O)c2cc(F)cc(c2)C(F)(F)F)c1)c1cc(F)ccc1Cl | 1H NMR (DMSO-d6, 400 MHz): 10.59 (s, 1H), 9.19 (br s, 1H), 8.80 (s, 2H), 7.91-7.98 (m, 2H), 7.72-7.78 (m, 2H), 7.69 (s, 1H), 7.32 (dd, 8.8, 5.1 Hz, 1H), 7.10 (td, 8.3, 3.3 Hz, 1H), 5.99 (br s, 1H), 3.19 (s, 6H), 2.84-3.07 (m, 1H) | 588.1 | A | |
| I-1223 | 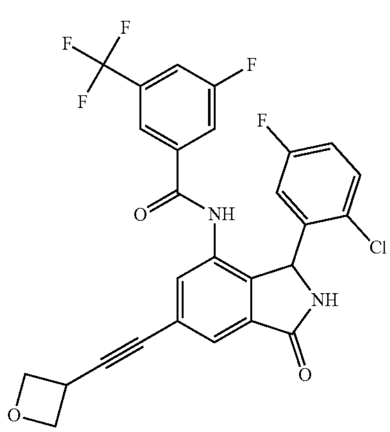 [SMILES: O=C(Nc1cc(C#CC2COC2)cc2c1C(c1cc(F)ccc1Cl)NC2=O)c1cc(F)cc(C(F)(F)F)c1] | Fc1ccc(C1)c(c1)C1NC(=O)c2cc(cc(NC(=O)c3cc(F)cc(c3)C(F)(F)F)c12)C#CC1COC1 | | 547.4 | A | |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-1224 | 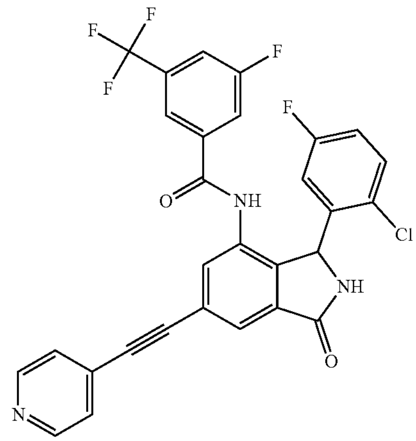 [SMILES: O=C(Nc1cc(C#Cc2ccncc2)cc2c1C(c1cc(F)ccc1Cl)NC2=O)c1cc(F)cc(C(F)(F)F)c1] | Fc1ccc(C1)c(c1)C1NC(=O)c2cc(cc(NC(=O)c3cc(F)cc(c3)C(F)(F)F)c12)C#Cc1ccncc1 | | 568.4 | A | |
| I-1225 | 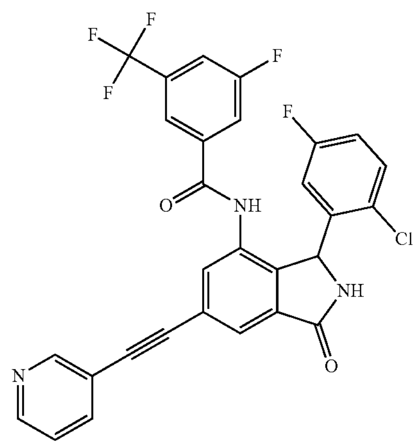 [SMILES: O=C(Nc1cc(C#Cc2cccnc2)cc2c1C(c1cc(F)ccc1Cl)NC2=O)c1cc(F)cc(C(F)(F)F)c1] | Fc1ccc(C1)c(c1)C1NC(=O)c2cc(cc(NC(=O)c3cc(F)cc(c3)C(F)(F)F)c12)C#Cc1cccnc1 | | 568.1 | A | |
| I-1226 | 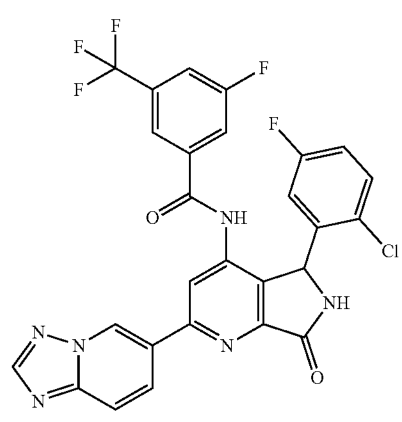 [SMILES: O=C(Nc1cc(-c2ccc3ncnn3c2)nc2c1C(c1cc(F)ccc1Cl)NC2=O)c1cc(F)cc(C(F)(F)F)c1] | Fc1ccc(C1)c(c1)C1NC(=O)c2nc(cc(NC(=O)c3cc(F)cc(c3)C(F)(F)F)c12)-c1ccc2ncnn2c1 | | 585.4 | A | |

TABLE 2-continued

Representative Compounds of the Invention with Bioactivity Data.

| Ex. No. | Structure | SMILES | $^1$H NMR | MS | ADP-Glo IC$_{50}$ | MCF 10A IC$_{50}$ |
|---|---|---|---|---|---|---|
| I-1227 | 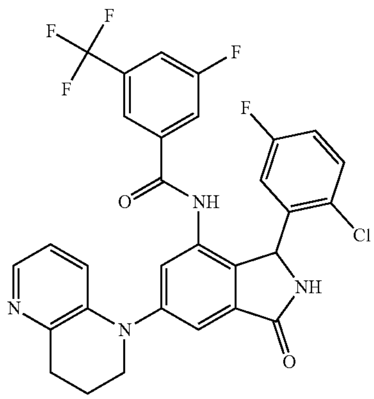 [SMILES: O=C(Nc1cc(N2CCCc3ncccc32)cc2c1C(c1cc(F)ccc1Cl)NC2=O)c1cc(F)cc(C(F)(F)F)c1] | Fc1ccc(C1)c(c1)C1NC(=O)c2cc(cc(NC(=O)c3cc(F)cc(c3)C(F)(F)F)c12)N1CCCc2ncccc12 | 1H NMR (400 MHz, DMSO-d6) 2.06 (quin, 6.13 Hz, 2 H) 2.92 (t, 6.57 Hz, 2 H) 3.63-3.76 (m, 2 H) 5.84-6.14 (m, 1 H) 7.00 (dd, 8.08, 4.55 Hz, 1 H) 7.09 (td, 8.46, 3.03 Hz, 1 H) 7.16 (br d, 7.58 Hz, 1 H) 7.28-7.38 (m, 2 H) 7.46 (d, 1.77 Hz, 1 H) 7.62 (s, 1 H) 7.70 (br d, 9.09 Hz, 1 H) 7.87-7.99 (m, 2 H) 9.15 (br s, 1 H) 10.46 (s, 1 H) | 599.33 | A | |
| I-1228 | 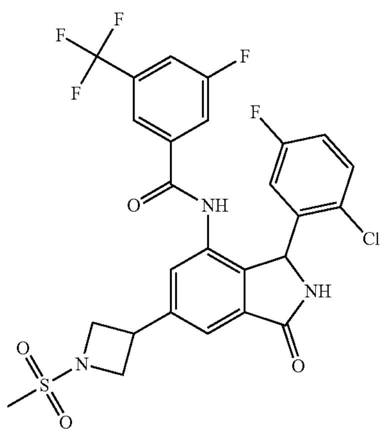 [SMILES: CS(=O)(=O)N1CC(c2cc(NC(=O)c3cc(F)cc(C(F)(F)F)c3)c3c(c2)C(=O)NC3c2cc(F)ccc2Cl)C1] | CS(=O)(=O)N1CC(C1)c1cc2C(=O)NC(c2c(NC(=O)c2cc(F)cc(c2)C(F)(F)F)c1)c1cc(F)ccc1Cl | 1H NMR (400 MHz, DMSO-d6) 3.09 (s, 3 H) 3.92-4.09 (m, 3 H) 4.25-4.33 (m, 2 H) 5.98 (br s, 1 H) 7.09 (td, 8.34, 3.03 Hz, 1 H) 7.31 (dd, 8.97, 5.18 Hz, 1 H) 7.52 (s, 1 H) 7.66 (s, 1 H) 7.70-7.77 (m, 2 H) 7.95 (br d, 8.34 Hz, 1 H) 9.16 (br s, 1 H) 10.55 (s, 1 H) | 600.33 | A | |
| I-1229 | 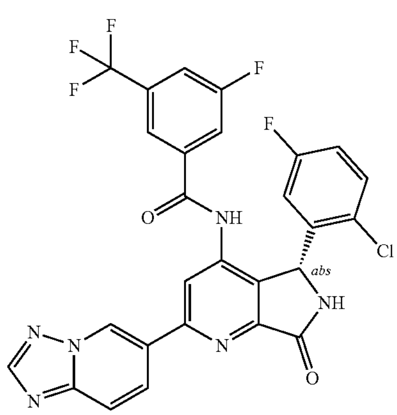 [SMILES: O=C(Nc1cc(-c2ccc3ncnn3c2)nc2c1[C@H](c1cc(F)ccc1Cl)NC2=O)c1cc(F)cc(C(F)(F)F)c1] | Fc1ccc(C1)c(c1)[C@@H]1NC(=O)c2nc(cc(NC(=O)c3cc(F)cc(c3)C(F)(F)F)c12)-c1ccc2ncnn2c1 | | 585.4 | A | |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-1230 | 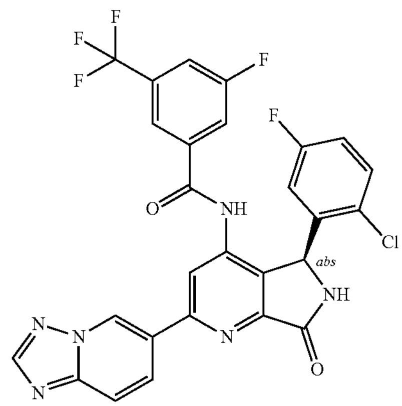 [SMILES: O=C(Nc1cc(-c2ccc3ncnn3c2)nc2c1[C@@H](c1cc(F)ccc1Cl)NC2=O)c1cc(F)cc(C(F)(F)F)c1] | Fc1ccc(C1)c(c1)[C@H]1NC(=O)c2nc(cc(NC(=O)c3cc(F)cc(c3)C(F)(F)F)c12)-c1ccc2ncnn2c1 | | 585.4 | B | |
| I-1231 | 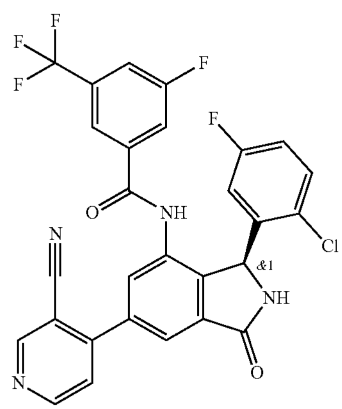 [SMILES: N#Cc1cnccc1-c1cc(NC(=O)c2cc(F)cc(C(F)(F)F)c2)c2c(c1)C(=O)N[C@@H]2c1cc(F)ccc1Cl] | Fc1ccc(C1)c(c1)[C@H]1NC(=O)c2cc(cc(NC(=O)c3cc(F)cc(c3)C(F)(F)F)c12)-c1ccncc1C#N | | | C | |
| I-1232 | 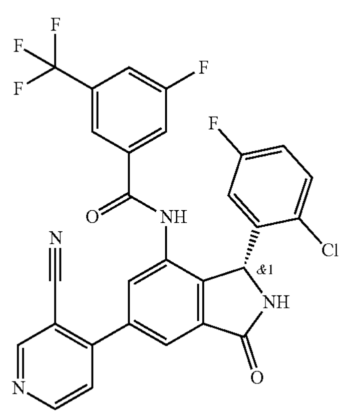 [SMILES: N#Cc1cnccc1-c1cc(NC(=O)c2cc(F)cc(C(F)(F)F)c2)c2c(c1)C(=O)N[C@H]2c1cc(F)ccc1Cl] | Fc1ccc(C1)c(c1)[C@@H]1NC(=O)c2cc(cc(NC(=O)c3cc(F)cc(c3)C(F)(F)F)c12)-c1ccncc1C#N | | 569.08 | A | |

TABLE 2-continued

Representative Compounds of the Invention with Bioactivity Data.

| Ex. No. | Structure | SMILES | $^1$H NMR | MS | ADP-Glo IC$_{50}$ | MCF 10A IC$_{50}$ |
|---|---|---|---|---|---|---|
| I-1233 | 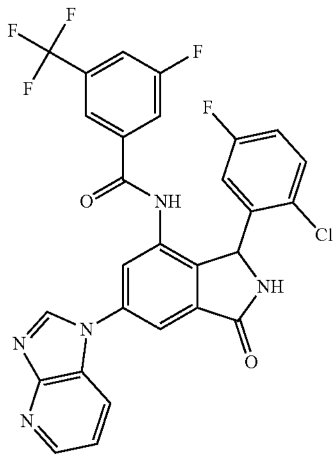 [SMILES: O=C(Nc1cc(-n2cnc3ncccc32)cc2c1C(c1cc(F)ccc1Cl)NC2=O)c1cc(F)cc(C(F)(F)F)c1] | Fc1ccc(C1)c(c1)C1NC(=O)c2cc(cc(NC(=O)c3cc(F)cc(c3)C(F)(F)F)c12)-n1cnc2ncccc12 | | 584.32 | A | |
| I-1234 | 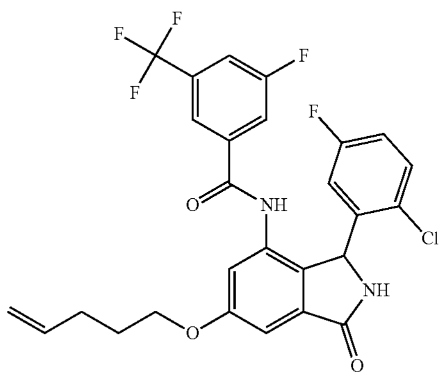 [SMILES: C=CCCCOc1cc(NC(=O)c2cc(F)cc(C(F)(F)F)c2)c2c(c1)C(=O)NC2c1cc(F)ccc1Cl] | Fc1ccc(C1)c(c1)C1NC(=O)c2cc(OCCCC=C)cc(NC(=O)c3cc(F)cc(c3)C(F)(F)F)c12 | 1H NMR (400 MHz, DMSO-d6) 10.43 (s, 1H), 9.12 (br. s, 1H), 7.94 (d, 8.4 Hz, 1H), 7.71 (d, 9.2 Hz, 1H), 7.63 (s, 1H), 7.31 (dd, 8.7, 5.2 Hz, 1H), 7.18 (d, 1.8 Hz, 1H), 7.14-7.01 (m, 2H), 6.63 (br. s, 1H), 5.89 (ddt, 17.0, 10.3, 6.6 Hz, 2H), 5.08 (ddd, 17.3, 3.4, 1.7 Hz, 1H), 5.01 (ddd, 10.3, 3.0, 1.4 Hz, 1H), 4.22-3.98 (m, 2H), 2.21 (dd, 14.5, 6.7 Hz, 2H), 1.92-1.80 (m, 1H). | 551.2 | C | |
| I-1235 | 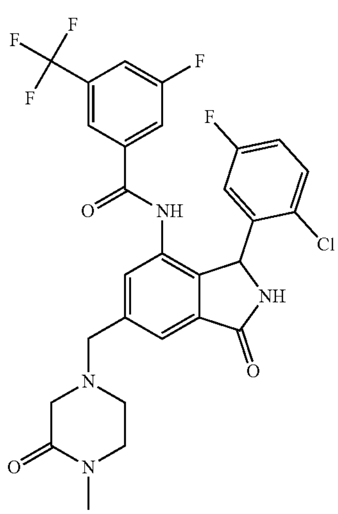 [SMILES: CN1CCN(Cc2cc(NC(=O)c3cc(F)cc(C(F)(F)F)c3)c3c(c2)C(=O)NC3c2cc(F)ccc2Cl)CC1=O] | CN1CCN(Cc2cc3C(=O)NC(c3c(NC(=O)c3cc(F)cc(c3)C(F)(F)F)c2)c2cc(F)ccc2Cl)CC1=O | NMR (400 MHz, CD3CN) 8.73 (s, 1H), 7.72-7.50 (m, 5H), 7.28 (s, 1H), 7.24 (dd, 8.9, 5.1 Hz, 1H), 6.96 (ddd, 8.8, 8.1, 3.1 Hz, 1H), 6.61 (br, s, 1H), 6.11 (br, s, 1H), 3.70 (s, 2H), 3.32-3.27 (m,, 2H), 3.04 (s, 2H), 2.86 (s, 3H), 2.75-2.70 (m, 2H). | 593.3 | B | |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-1236 | 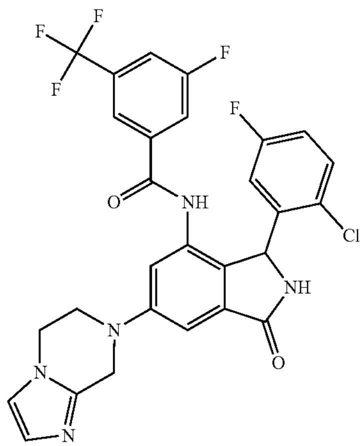 [SMILES: O=C(Nc1cc(N2CCn3ccnc3C2)cc2c1C(c1cc(F)ccc1Cl)NC2=O)c1cc(F)cc(C(F)(F)F)c1] | Fc1ccc(C1)c(c1)CNC(=O)c2cc(cc(NC(=O)c3cc(F)cc(c3)C(F)(F)F)c12)N1CCn2ccnc2C1 | (400 MHz, CD3CN) 8.83 (s, 1 H), 8.08 (s, 1 H), 7.66-7.55 (m, 4 H), 7.37-7.17 (m, 4 H), 6.95 (td, 8.4, 2.9 Hz, 1 H), 6.63 (br s, 1 H), 6.04 (br s, 1 H), 4.55 (app d, 9.3 Hz, 2 H), 4.20-4.12 (m, 2 H), 3.83 (t, 5.1 Hz, 2 H). | 586.3 | A | |
| I-1237 | 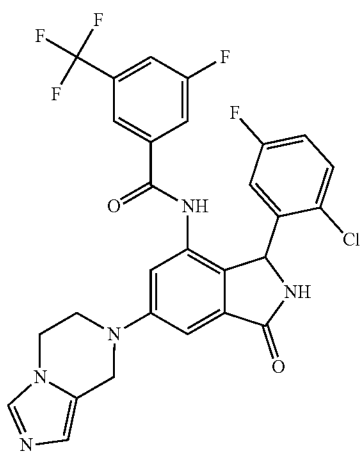 [SMILES: O=C(Nc1cc(N2CCn3cncc3C2)cc2c1C(c1cc(F)ccc1Cl)NC2=O)c1cc(F)cc(C(F)(F)F)c1] | Fc1ccc(C1)c(c1)CNC(=O)c2cc(cc(NC(=O)c3cc(F)cc(c3)C(F)(F)F)c12)N1CCn2cncc2C1 | (400 MHz, CD3CN) 8.66 (s, 1 H), 8.09 (s, 1 H), 7.67-7.56 (m, 4 H), 7.32 (d, 2.0 Hz, 1 H), 7.26-7.17 (m, 3 H), 6.95 (td, 8.4, 3.0 Hz, 1 H), 6.64 (br s, 1 H), 6.04 (br s, 1 H), 4.57 (s, 2 H), 4.19 (t, 5.2 Hz, 2 H), 3.80 (t, 5.3 Hz, 2 H). | 588.3 | A | |
| I-1238 | 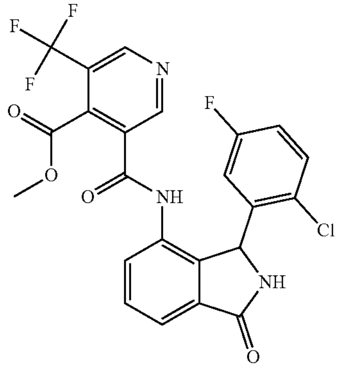 [SMILES: COC(=O)c1c(C(=O)Nc2cccc3c2C(c2cc(F)ccc2Cl)NC3=O)cncc1C(F)(F)F] | COC(=O)c1cc(Nc2cccc3C(=O)NC(c23)c2cc(F)ccc2Cl)ncc1C(F)(F)F | (400 MHz, CD3CN) 8.88 (s, 1 H), 8.61 (s, 1 H), 7.78-7.71 (m, 1 H), 7.49 (br s, 1 H), 7.46 (dd, 5.0, 1.8 Hz, 1 H), 7.37 (t, 7.6 Hz, 1 H), 7.30 (d, 7.3 Hz, 1 H), 7.01 (app t, 7.0 Hz, 1 H), 6.94 (d, 7.8 Hz, 1 H), 6.85 (br s, 1 H), 6.65 (br s, 1 H), 4.19 (s, 1 H), 3.93 (s, 3 H). | 480.3 | D | |

TABLE 2-continued

Representative Compounds of the Invention with Bioactivity Data.

| Ex. No. | Structure | SMILES | $^1$H NMR | MS | ADP-Glo IC$_{50}$ | MCF 10A IC$_{50}$ |
|---|---|---|---|---|---|---|
| I-1239 | 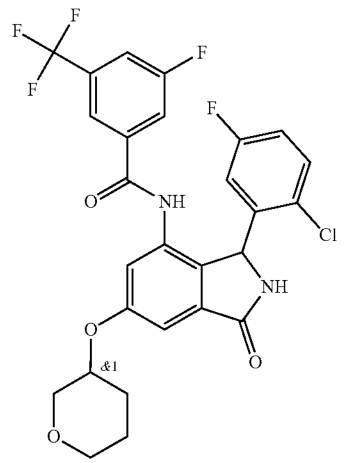 [SMILES: O=C(Nc1cc(OC2CCCOC2)cc2c1C(c1cc(F)ccc1Cl)NC2=O)c1cc(F)cc(C(F)(F)F)c1] | Fc1ccc(C1)c(c1)C1NC(=O)c2cc(OC3CCCOC3)cc(NC(=O)c3cc(F)cc(c3)C(F)(F)F)c12 | 1H NMR (400 MHz, DMSO-d6) 10.43 (br. s, 1H), 9.13 (br. s, 1H), 7.94 (d, 8.5 Hz, 1H), 7.71 (d, 9.1 Hz, 1H), 7.63 (s, 1H), 7.31 (dd, 8.9, 5.2 Hz, 1H), 7.22 (d, 1.2 Hz, 1H), 7.13-7.03 (m, 2H), 6.64 (br. s, 1H), 5.91 (br. s, 1H), 4.64-4.43 (m, 1H), 3.84 (dd, 11.6, 2.4 Hz, 1H), 3.68-3.49 (m, 3H), 2.05 (m, 1H), 1.88-1.68 (m, 2H), 1.64-1.47 (m, 1H) | 567.3 | A | |
| I-1240 | 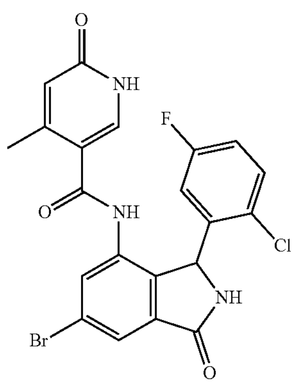 [SMILES: Cc1cc(=O)[nH]cc1C(=O)Nc1cc(Br)cc2c1C(c1cc(F)ccc1Cl)NC2=O] | Cc1cc(=O)[nH]cc1C(=O)Nc1cc(Br)cc2C(=O)NC(c12)c1cc(F)ccc1Cl | 1H NMR (400 MHz, DMSO-d6) 11.75 (s, 1H), 10.06 (s, 1H), 9.26 (s, 1H), 7.75 (d, 1.7 Hz, 1H), 7.64 (s, 1H), 7.46 (dd, 8.8, 5.1 Hz, 1H), 7.21 (ddd, 8.9, 7.9, 3.1 Hz, 1H), 6.89 (s, 1H), 6.65 (s, 1H), 6.16 (s, 1H), 5.96 (s, 1H), 2.13-2.06 (m, 3H). | 489.9 | E | |
| I-1241 | 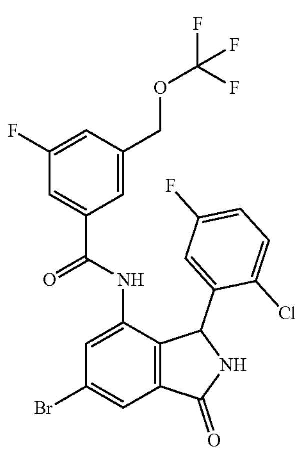 [SMILES: O=C(Nc1cc(Br)cc2c1C(c1cc(F)ccc1Cl)NC2=O)c1cc(F)cc(COC(F)(F)F)c1] | Fc1ccc(C1)c(c1)C1NC(=O)c2cc(Br)cc(NC(=O)c3cc(F)cc(COC(F)(F)F)c3)c12 | 1H NMR (400 MHz, DMSO-d6) 10.40 (s, 1H), 9.28 (s, 1H), 7.81 (d, 1.7 Hz, 1H), 7.74 (d, 1.9 Hz, 1H), 7.57-7.46 (m, 2H), 7.38-7.30 (m, 2H), 7.11 (td, 8.4, 3.1 Hz, 1H), 6.76 (s, 1H), 6.03-5.97 (m, 1H), 5.22 (s, 2H). | 575 | D | |

TABLE 2-continued

Representative Compounds of the Invention with Bioactivity Data.

| Ex. No. | Structure | SMILES | $^1$H NMR | MS | ADP-Glo IC$_{50}$ | MCF 10A IC$_{50}$ |
|---|---|---|---|---|---|---|
| I-1242 | 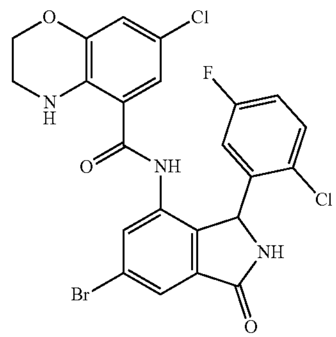 | Fc1ccc(C1)c(c1)C1NC(=O)c2cc(Br)cc(NC(=O)c3cc(Cl)cc4OCCNc34)c12 | 1H NMR (400 MHz, Chloroform-d) 8.46 (s, 1H), 7.92 (d, 1.6 Hz, 1H), 7.55 (dd, 9.0, 4.9 Hz, 1H), 7.4-7.3(S,1H), 7.18 (s, 1H), 7.13 (ddd, 8.9, 7.4, 3.0 Hz, 1H), 6.87 (d, 2.3 Hz., 1H), 6.70 (s, 1H), 6.42 (s, 1H), 6.28 (d, 2.3 Hz, 1H), 6.16 (s, 1H), 4.22 (t, 4.5 Hz, 2H), 3.54-3.47 (m, 2H) | 551.9 | D | |
| I-1243 | 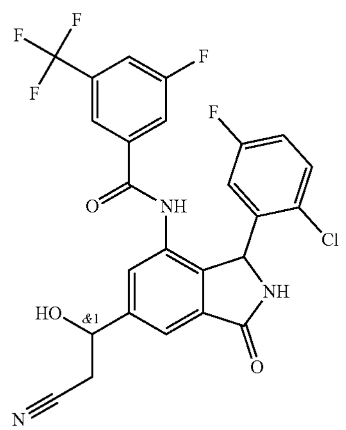 [SMILES: N#CCC(O)c1cc(NC(=O)c2cc(F)cc(C(F)(F)F)c2)c2c(c1)C(=O)NC2c1cc(F)ccc1Cl] | OC(CC#N)c1cc2C(=O)NC(c2c(NC(=O)c2cc(F)cc(c2)C(F)(F)F)c1c(F)ccc1Cl | (400 MHz, DMSO-d6) 10.58 (s, 0.5H), 10.56 (s, 0.5H), 9.16 (s, 1H), 7.96 (s, 0.5H), 7.94 (s, 0.5H), 7.79 (s, 0.5H), 7.77-7.71 (m, 1.5H), 7.66 (s, 1H), 7.59 (s, 0.5H), 7.52 (s, 0.5H), 7.32 (dd, 5.2, 1.4 Hz, 0.5H), 7.30 (dd, 5.2, 1.4 Hz, 0.5H), 7.13-7.06 (m, 1H), 6.55 (br s, 1H), 6.24 (s, 0.5H), 6.22 (s, 0.5H), 5.97 (br s, 1H), 5.12 (q, 5.0 Hz, 0.5H), 5.07 (q, 5.1 Hz, 0.5H), 3.07-2.90 (m, 4H) | 536.2 | A | |
| I-1244 | 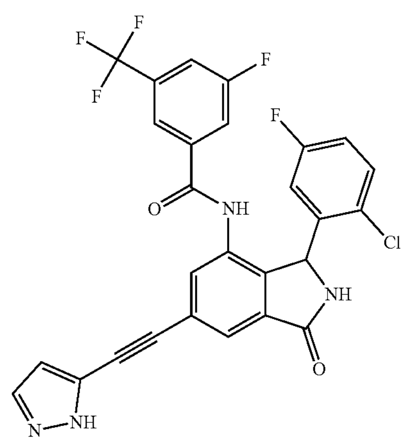 [SMILES: O=C(Nc1cc(C#Cc2ccn[nH]2)cc2c1C(c1cc(F)ccc1Cl)NC2=O)c1cc(F)cc(C(F)(F)F)c1] | Fc1ccc(C1)c(c1)C1NC(=O)c2cc(cc(NC(=O)c3cc(F)cc(c3)C(F)(F)F)c12)C#Cc1ccn[nH]1 | NMR (400 MHz, ACN-d3): 8.79 (br. s, 1H), 7.89 (d, 0.8 Hz, 1H), 7.69 (s, 1H), 7.66-7.64 (m, 2H), 7.59 (mt, 1H), 7.57 (s, 1H), 7.41 (br. s, 1H), 7.26 (dd, 8.8, 5.1 Hz., 1H), 6.98 (td, 8.6, 3.0 Hz, 1H), 6.70 (br. s, 1H), 6.57 (s, 1H), 6.15 (br. s, 1H) | 557.1 | A | |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-1245 | 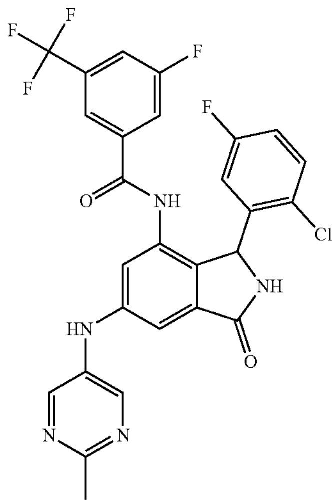 [SMILES: Cc1ncc(Nc2cc(NC(=O)c3cc(F)cc(C(F)(F)F)c3)c3c(c2)C(=O)NC3c2cc(F)ccc2Cl)cn1] | Cc1ncc(Nc2cc3C(=O)NC(c3c(NC(=O)c3cc(F)cc(c3)C(F)(F)F)c2cc(F)ccc2Cl)cn1 | 1H-NMR (400 MHz, DMSO-d6) 10.39 (br. s, 1H), 9.09 (br. s, 1H), 8.78 (s, 1H), 8.60 (s, 2H), 7.94 (br. d, 8.3 Hz, 1H), 7.71 (br. d, 8.9 Hz, 1H), 7.61 (br. s, 1H), 7.31 (dd, 8.9, 5.2 Hz, 1H), 7.23 (d, 2.0 Hz, 1H), 7.19 (d, 1.7 Hz, 1H), 7.11-7.05 (m, 1H), 6.67 (br. s, 1H), 5.93 (br. s, 1H), 2.56 (s, 3H). | 574.4 | A | |
| I-1246 | 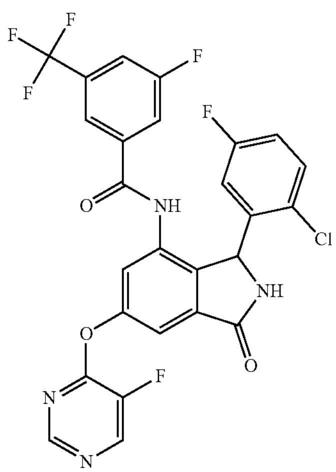 [SMILES: O=C(Nc1cc(Oc2ncncc2F)cc2c1C(c1cc(F)ccc1Cl)NC2=O)c1cc(F)cc(C(F)(F)F)c1] | Fc1ccc(C1)c(c1)C1NC(=O)c2cc(Oc3ncncc3F)c(NC(=O)c3cc(F)cc(c3)C(F)(F)F)c12 | NMR (400 MHz, CD3CN) 8.71 (br. s, 1H), 8.61 (d, 2.9 Hz, 1H), 8.51 (d, 1.4 Hz, 1H), 7.66-7.64 (m, 1H), 7.63 (d, 2.1 Hz, 1H), 7.61-7.58 (m, 1H), 7.57 (s, 1H), 7.51 (d, 1.5 Hz, 1H), 7.36 (br. s, 1H), 7.29 (dd, 8.9, 5.1 Hz, 1H), 7.00 (ddd, 8.6, 8.2, 3.1 Hz, 1H), 6.73 (br. s, 1H), 6.17 (br. s, 1H) | 577.3 | A | |
| I-1247 | 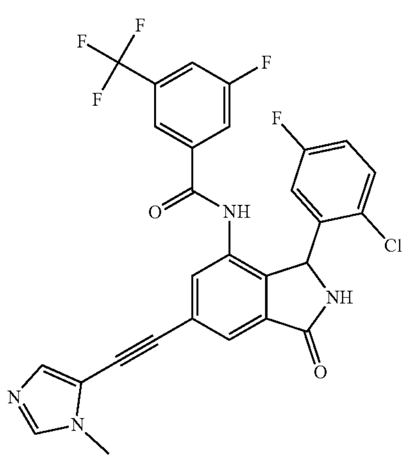 [SMILES: Cn1cncc1C#Cc1cc(NC(=O)c2cc(F)cc(C(F)(F)F)c2)c2c(c1)C(=O)NC2c1cc(F)ccc1Cl] | Cn1cncc1C#Cc1cc2C(=O)NC(c2c(NC(=O)c2cc(F)cc(c2)C(F)(F)F)c1)c1cc(F)ccc1Cl | NMR (400 MHz, ACN-d3): 8.80 (br. s, 1H), 7.89 (s, 1H), 7.69 (s, 1H), 7.66 (dt, 24.4, 8.4 Hz, 1H), 7.61-7.58 (m, 2H), 7.57 (s, 1H), 7.43 (br. s, 1H), 7.34 (br. s, 1H), 7.26 (dd, 9.0, 5.0 Hz, 1H), 6.98 (td, 8.7, 3.0 Hz, 1H), 6.69 (br. s, 1H), 6.14 (br. s, 1H), 3.75 (s, 3H) | 571.4 | A | |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-1248 | 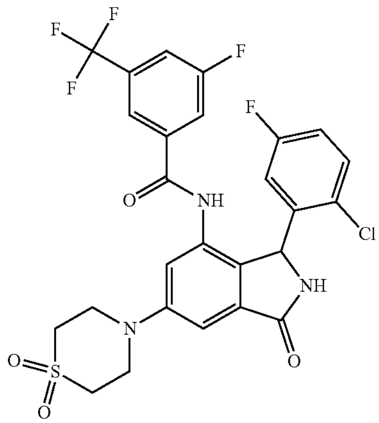 [SMILES: O=C(Nc1cc(N2CCS(=O)(=O)CC2)cc2c1C(c1cc(F)ccc1Cl)NC2=O)c1cc(F)cc(C(F)(F)F)c1] | Fc1ccc(C1)c(c1)C1NC(=O)c2cc(cc(NC(=O)c3cc(F)cc(c3)C(F)(F)F)c12)N1CCS(=O)(=O)CC1 | (400 MHz, CD3CN) 8.59 (br. s, 1H), 7.64 (br. d, 8.0 Hz, 1H), 7.58 (br. d, 8.0 Hz, 1H), 7.57 (br. s, 1H), 7.32 (d, 2.3 Hz, 1H), 7.25 (dd, 8.9, 5.1 Hz, 1H), 7.17 (d, 2.0 Hz, 2H), 6.96 (td, 8.0, 3.1 Hz, 1H), 6.64 (br. s, 1H), 6.06 (br. s, 1H), 3.97-3.88 (m, 4H), 3.14-3.07 (m, 4H). | 600.2 | A | |
| I-1249 | 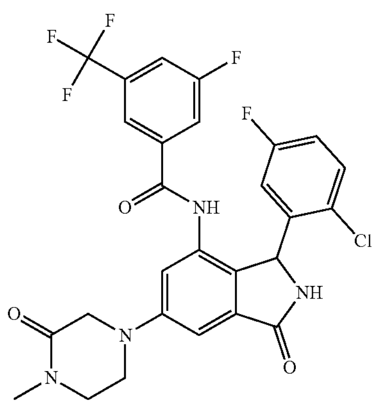 [SMILES: CN1CCN(c2cc(NC(=O)c3cc(F)cc(C(F)(F)F)c3)c3c(c2)C(=O)NC3c2cc(F)ccc2Cl)CC1=O] | CN1CCN(CC1=O)c1cc2C(=O)NC(c2c(NC(=O)c2cc(F)cc(c2)C(F)(F)F)c1)c1cc(F)ccc1Cl | (400 MHz, CD3CN) 8.54 (br. s, 1H), 7.65-7.53 (m, 3H), 7.23-7.19 (m, 2H), 7.13 (s, 1H), 7.05 (d, 2.1 Hz, 1H), 6.93 (ddd, 8.8, 8.0, 3.1 Hz, 1H), 6.60 (br. s, 1H), 6.00 (br. s, 1H), 3.84 (s, 2H), 3.62-3.50 (m, 2H), 3.49-3.39 (m, 2H), 2.93 (s, 3H). | 579.4 | A | |
| I-1250 | 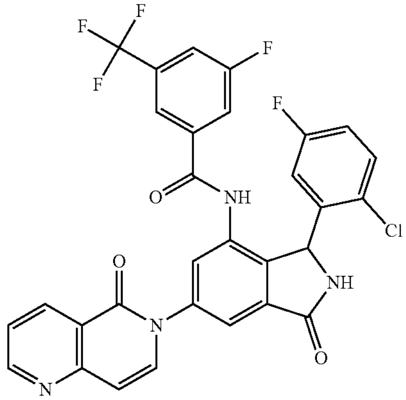 [SMILES: O=C(Nc1cc(-n2ccc3ncccc3c2=O)cc2c1C(c1cc(F)ccc1Cl)NC2=O)c1cc(F)cc(C(F)(F)F)c1] | Fc1ccc(C1)c(c1)C1NC(=O)c2cc(cc(NC(=O)c3cc(F)cc(c3)C(F)(F)F)c12)-n1ccc2ncccc2c1=O | (400 MHz, CD3CN) 8.92 (dd, 4.6, 1.7 Hz, 1H), 8.75 (br. s, 1H), 8.60 (dd, 8.0, 1.3 Hz, 1H), 7.80 (d, 1.8 Hz, 1H), 7.71 (s, 1H), 7.65-7.57 (m, 3H), 7.56-7.53 (m, 1H), 7.49 (dd, 8.1, 4.6 Hz, 1H), 7.34 (s, 1H), 7.26 (dd, 8.9, 5.2 Hz, 1H), 7.00-6.94 (m, 1H), 6.82 (d, 7.6 Hz, 1H), 6.71 (br. s, 1H), 6.18 (br. s, 1H). | 611.3 | A | |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-1251 | 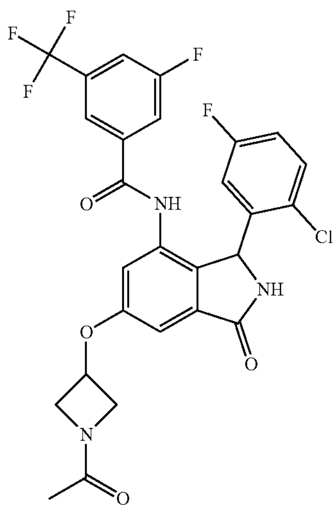 [SMILES: CC(=O)N1CC(Oc2cc(NC(=O)c3cc(F)cc(C(F)(F)F)c3)c3c(c2)C(=O)NC3c2cc(F)ccc2Cl)C1] | CC(=O)N1CC(C1)Oc1cc2C(=O)NC(c2c(NC(=O)c2cc(F)cc(c2)C(F)(F)F)c1c c(F)ccc1Cl | NMR (400 MHz, CD3CN) 8.68 (s, 1H), 7.64 (br d, 8.3 Hz, 1H), 7.58 (d overlapped with m, 8.3 Hz, 1H), 7.56 (s, 1H) 7.31 (s, 1H), 7.25 (dd, 8.9, 5.1 Hz, 1H), 7.08 (s, 2H), 6.96 (ddd, 8.8, 8.0, 3.1 Hz, 1H), 6.64 (br s, 1H), 6.07 (br s, 1H), 5.13-5.06 (m, 1H), 4.61-4.53 (m, 1H), 4.33 (dd, 10.5, 6.6 Hz, 1H), 4.16 (ddd, 6.6, 5.6, 2.7 Hz., 1H), 3.88 (dd, 10.6, 3.5 Hz, 1H), 1.81 (s, 3H). | 580 | B | |
| I-1252 | 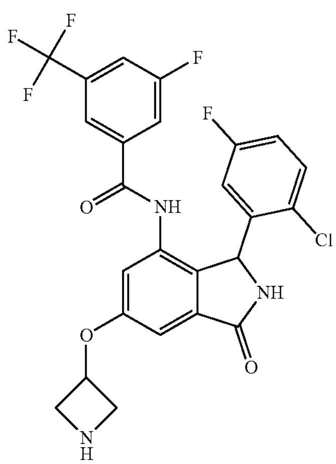 | Fc1ccc(C1)c(c1)C1NC(=O)c2cc(OC3CNC3)cc(NC(=O)c3cc(F)cc(c3)C(F)(F)F)c12 | NMR (400 MHz, CD3CN) 9.04 (s, 1H), 7.72-7.54 (m, 4H), 7.45 (s, 1H), 7.24 (dd, 8.9, 5.1 Hz, 1H), 7.11 (d, 5.8 Hz, 1H), 6.95 (td, 8.4, 3.0 Hz, 1H), 6.65 (br s, 1H), 6.08 (br s, 1H), 5.30-5.18 (m, 1H), 4.64-4.47 (m, 2H), 4.30-4.10 (m, 2H), 3.89 (dd, 11.8, 5.3 Hz). | 538 | B | |
| I-1253 | 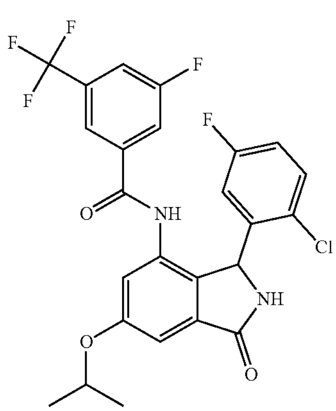 [SMILES: CC(C)Oc1cc(NC(=O)c2cc(F)cc(C(F)(F)F)c2)c2c(c1)C(=O)NC2c1cc(F)ccc1Cl] | CC(C)Oc1cc2C(=O)NC(c2c(NC(=O)c2cc(F)cc(c2)C(F)(F)F)c1)c1cc(F)ccc1Cl | 1H NMR (400 MHz, DMSO-d6) 10.41 (s, 1H), 9.11 (s, 1H), 7.94 (d, 8.0 Hz, 1H), 7.71 (d, 9.6 Hz, 1H), 7.62 (s, 1H), 7.31 (dd, 8.9, 5.2 Hz, 1H), 7.17 (d, 2.1 Hz, 1H), 7.08 (td, 8.5, 3.1 Hz, 1H), 7.02 (s, 1H), 6.59 (br. s, 1H), 5.92 (br. s, 1H), 4.75 (m, 1H), 1.32 (dd, 6.0, 3.5 Hz, 6H) | 525.2 | A | |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-1254 | 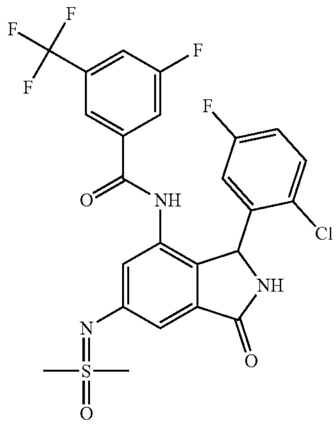 [SMILES: CS(C)(=O)=Nc1cc(NC(=O)c2cc(F)cc(C(F)(F)F)c2)c2c(c1)C(=O)NC2c1cc(F)ccc1Cl] | CS(C)(=O)=Nc1cc2C(=O)NC(c2c(NC(=O)c2cc(F)cc(c2)C(F)(F)F)c1)c1cc(F)ccc1Cl | NMR (400 MHz, DMSO-d6) 10.40 (br. s, 1H), 9.03 (br. s, 1H), 7.93 (br. d, 8.5 Hz, 1H), 7.71 (br. d, 9.0 Hz, 1H), 7.61 (s, 1H), 7.30 (dd, 8.9, 5.2 Hz, 1H), 7.19 (d, 1.8 Hz, 1H), 7.07 (td, 8.4, 3.0 Hz, 1H), 7.02 (d, 1.8 Hz, 1H), 6.62 (br. s, 1H), 5.89 (br. s, 1H), 3.29 (s, 6H). | 558.2 | B | |
| I-1255 | 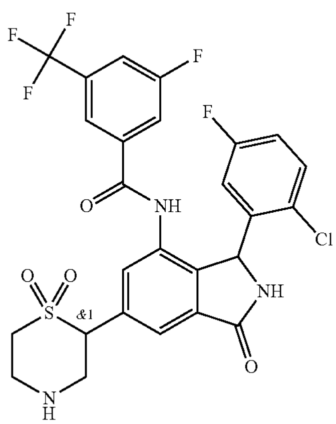 | Fc1ccc(C1)c(c1)C1NC(=O)c2cc(cc(NC(=O)c3cc(F)cc(c3)C(F)(F)F)c12)C1CNCCS1(=O)=O | NMR (400 MHz, CD3CN) 8.71 (br s, 1H), 7.77 (d, 2.6 Hz, 1H), 7.71-7.56 (m, 5H), 7.38-7.29 (m, 1H), 7.25 (dd, 8.9, 5.1 Hz, 1H), 6.97 (td, 8.4, 3.0 Hz, 1H), 6.65 (br s, 1H), 6.14 (br s, 1H), 4.33-4.38 (m, 1H), 3.43-3.51 (m, 3H), 3.24-3.26 (m, 1H), 3.12-3.14 (m, 2H). | 600.2 | A | |
| I-1256 | 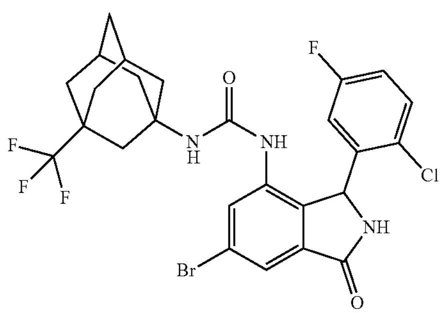 | Fc1ccc(C1)c(c1)C1NC(=O)c2cc(Br)cc(NC(=O)NC34CC5CC(C3)CC(C5)(C4)C(F)(F)F)c12 | 1H-NMR (400 MHz, DMSO-d6) 9.14 (br. s, 1H), 7.99 (s, 1H), 7.66 (br. s, 1H), 7.53 (d, 1.7 Hz, 1H), 7.46 (dd, 8.2, 5.0 Hz, 1H), 7.23 (ddd, 8.8, 8.1, 3.1 Hz, 1H), 6.68 (br. s, 1H), 6.24 (s, 1H), 6.02 (br. s, 1H), 2.18-2.12 (m, 2H), 1.96 (d, 11.9 Hz, 1H), 1.93-1.84 (m, 2H), 1.80 (d, 11.8 Hz, 1H), 1.66-1.54 (m, 8H). | 602.2 | B | |
| I-1257 | 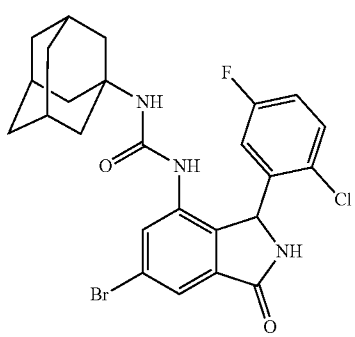 [SMILES: O=C(Nc1cc(Br)cc2c1C(c1cc(F)ccc1Cl)NC2=O)NC12CC3CC(CC(C3)C1)C2] | Fc1ccc(C1)c(c1)C1NC(=O)c2cc(Br)cc(NC(=O)NC34CC5CC(CC(C5)C3)C4)c12 | 1H-NMR (400 MHz, DMSO-d6) 9.12 (br. s, 1H), 8.24 (br. s, 1H), 7.70 (br. s, 1H), 7.49 (d, 1.7 Hz, 1H), 7.46 (dd, 8.2, 5.2 Hz, 1H), 7.23 (ddd, 8.7, 8.4, 3.1 Hz, 1H), 6.76 (br. s, 1H), 6.23 (s, 1H), 6.03 (br. s, 1H), 2.02-1.95 (m, 3H), 1.86-1.77 (m, 6H), 1.64-1.55 (m, 6H). | 534.2 | B | |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-1258 | 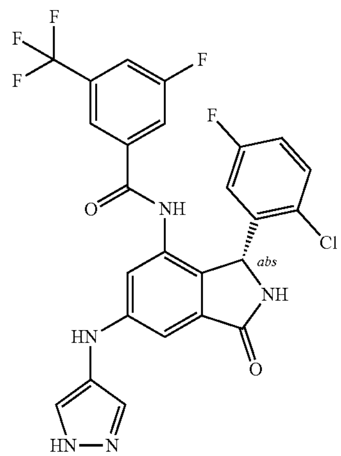 [SMILES: O=C(Nc1cc(Nc2cn[nH]c2)cc2c1[C@H](c1cc(F)ccc1Cl)NC2=O)c1cc(F)cc(C(F)(F)F)c1] | Fc1ccc(C1)c(c1)[C@@H]1NC(=O)c2cc(Nc3cn[nH]c3)cc(NC(=O)c3cc(F)cc(c3)C(F)(F)F)c12 | 1H-NMR (400 MHz, DMSO-d6) 12.73 (br. s, 1H), 10.30 (s, 1H), 8.94 (br. s, 1H), 7.94-7.86 (m, 2H), 7.69 (br. d, 9.0 Hz, 1H), 7.60 (s, 1H), 7.65-7.55 (m, 2H), 7.29 (dd, 8.9, 5.2 Hz, 1H), 7.06 (app. td, 8.4, 3.1 Hz, 1H), 6.93 (br. s, 1H), 6.86 (br. s, 1H), 6.58 (br. s, 1H), 5.85 (br. s, 1H). | 548.3 | A | |
| I-1259 | 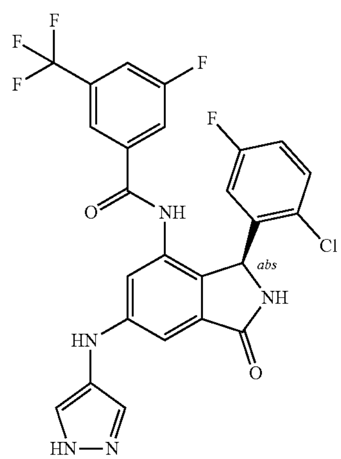 [SMILES: O=C(Nc1cc(Nc2cn[nH]c2)cc2c1[C@@H](c1cc(F)ccc1Cl)NC2=O)c1cc(F)cc(C(F)(F)F)c1] | Fc1ccc(C1)c(c1)[C@H]1NC(=O)c2cc(Nc3cn[nH]c3)cc(NC(=O)c3cc(F)cc(c3)C(F)(F)F)c12 | 1H-NMR (400 MHz, DMSO-d6) 12.73 (br. s, 1H), 10.29 (s, 1H), 8.95 (br. s, 1H), 7.94-7.88 (m, 2H), 7.69 (br. d, 9.3 Hz, 1H), 7.78-7.43 (m, 2H), 7.60 (s, 1H), 7.29 (dd, 8.9, 5.2 Hz, 1H), 7.06 (app. td, 8.4, 3.1 Hz, 1H), 6.94 (s, 1H), 6.85 (br. s, 1H), 6.59 (br. s, 1H), 5.85 (br. s, 1H). | 548.4 | D | |
| I-1260 | 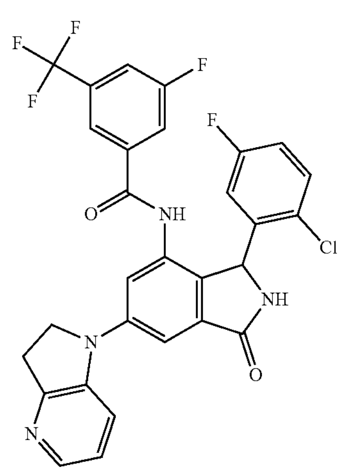 [SMILES: O=C(Nc1cc(N2CCc3ncccc32)cc2c1C(c1cc(F)ccc1Cl)NC2=O)c1cc(F)cc(C(F)(F)F)c1] | Fc1ccc(C1)c(c1)C1NC(=O)c2cc(cc(NC(=O)c3cc(F)cc(c3)C(F)(F)F)c12)N1CCc2nccc12 | | | A | |

TABLE 2-continued

Representative Compounds of the Invention with Bioactivity Data.

| Ex. No. | Structure | SMILES | $^1$H NMR | MS | ADP-Glo IC$_{50}$ | MCF 10A IC$_{50}$ |
|---|---|---|---|---|---|---|
| I-1261 | 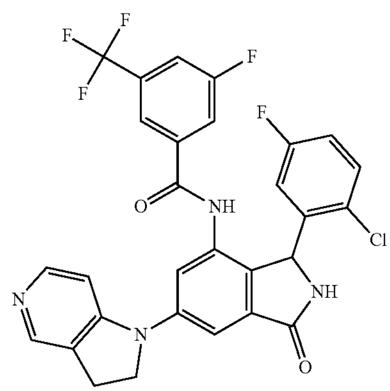 [SMILES: O=C(Nc1cc(N2CCc3cnccc32)cc2c1C(c1cc(F)ccc1Cl)NC2=O)c1cc(F)cc(C(F)(F)F)c1] | Fc1ccc(C1)c(c1)C1NC(=O)c2cc(cc(NC(=O)c3cc(F)cc(c3)C(F)(F)F)c12)N1CCc2cnccc12 | | | | A |
| I-1262 | 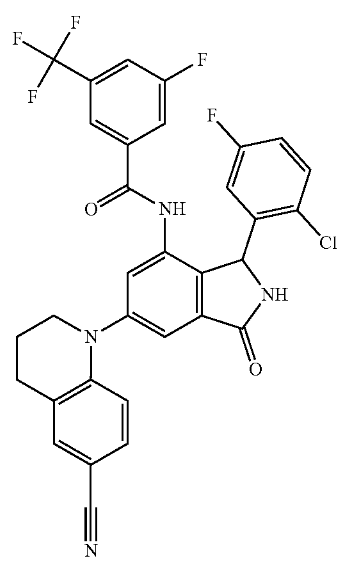 [SMILES: N#Cc1ccc2c(c1)CCCN2c1cc(NC(=O)c2cc(F)cc(C(F)(F)F)c2)c2c(c1)C(=O)NC2c1cc(F)ccc1Cl] | Fc1ccc(C1)c(c1)C1NC(=O)c2cc(cc(NC(=O)c3cc(F)cc(c3)C(F)(F)F)c12)N1CCCc2cc(ccc12)C#N | | | | A |
| I-1263 | 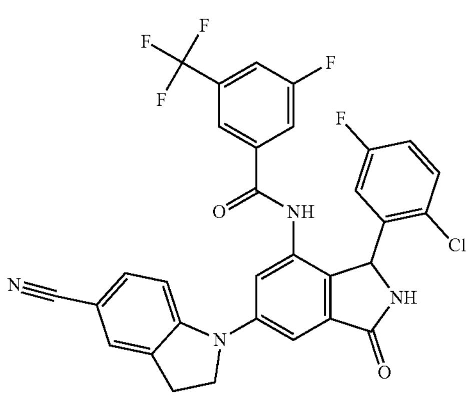 [SMILES: N#Cc1ccc2c(c1)CCN2c1cc(NC(=O)c2cc(F)cc(C(F)(F)F)c2)c2c(c1)C(=O)NC2c1cc(F)ccc1Cl] | Fc1ccc(C1)c(c1)C1NC(=O)c2cc(cc(NC(=O)c3cc(F)cc(c3)C(F)(F)F)c12)N1CCc2cc(ccc12)C#N | | | | A |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-1264 | 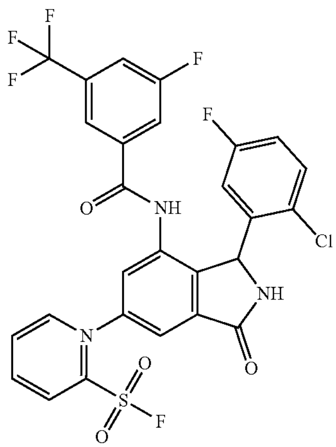 | Fc1ccc(C1)c(c1)C1NC(=O)c2cc(cc(NC(=O)c3cc(F)cc(c3)C(F)(F)F)c12)-c1ccccc1S(F)(=O)=O | 1H NMR (400 MHz, DMSO-d6) 5.96-6.13 (m, 1 H) 7.12 (td, 8.46, 3.03 Hz, 1 H) 7.34 (dd, 8.84, 5.05 Hz, 1 H) 7.48 (s, 1 H) 7.65 (s, 2 H) 7.69-7.76 (m, 2 H) 7.85 (t, 7.71 Hz, 1 H) 7.93 (br d, 8.08 Hz, 1 H) 8.02 (td, 7.58, 1.26 Hz, 1 H) 8.29 (dd, 8.08, 1.01 Hz, 1 H) 9.28 (br s, 1 H) 10.63 (s, 1 H) | 625.29 | A | |
| I-1265 | 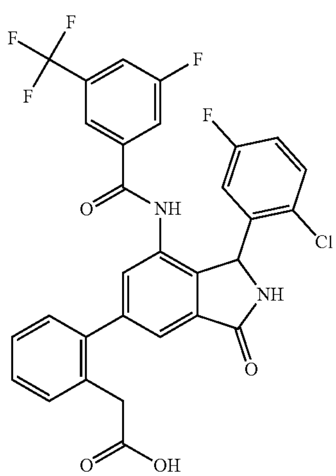 [SMILES: O=C(O)Cc1ccccc1-c1cc(NC(=O)c2cc(F)cc(C(F)(F)F)c2)c2c(c1)C(=O)NC2c1cc(F)ccc1Cl] | OC(=O)Cc1ccccc1-c1cc2C(=O)NC(c2c(NC(=O)c2cc(F)cc(c2)C(F)(F)F)c1)c1cc(F)ccc1Cl | 1H NMR (400 MHz, DMSO-d6) 3.56-3.60 (m, 2 H) 5.93-6.14 (m, 1 H) 7.11 (td, 8.34, 3.03 Hz, 1 H) 7.30-7.45 (m, 7 H) 7.57 (d, 1.26 Hz, 1 H) 7.65 (s, 1 H) 7.73 (br d, 9.09 Hz, 1 H) 7.94 (br d, 8.34 Hz, 1 H) 9.21 (br s, 1 H) 10.57 (s, 1 H) | 601.28 | B | |
| I-1266 | 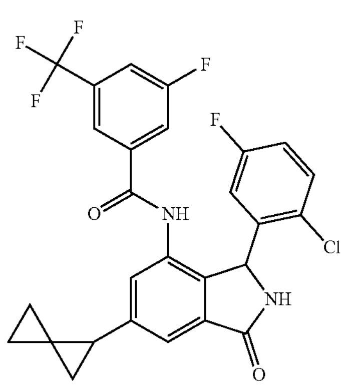 [SMILES: O=C(Nc1cc(C2CC23CC3)cc2c1C(c1cc(F)ccc1Cl)NC2=O)c1cc(F)cc(C(F)(F)F)c1] | Fc1ccc(C1)c(c1)C1NC(=O)c2cc(cc(NC(=O)c3cc(F)cc(c3)C(F)(F)F)c12)C1CC1CC1 | 1H NMR (400 MHz, DMSO-d6) 0.68 (br d, 4.29 Hz, 1 H) 0.95-1.03 (m, 3 H) 1.15 (dt, 15.22, 4.39 Hz, 1 H) 1.61 (dt, 8.08, 4.04 Hz, 1 H) 2.43 (s, 1 H) 5.83-6.05 (m, 1 H) 7.04-7.12 (m, 1 H) 7.24 (br d, 6.82 Hz, 1 H) 7.30 (dt, 8.91, 5.40 Hz, 1 H) 7.42 (dd, 4.29, 1.26 Hz, 1 H) 7.65 (br s, 1 H) 7.72 (br d, 8.84 Hz, 1 H) 7.94 (br d, 8.34 Hz, 1 H) 9.08 (br s, 1 H) 10.42 (br d, 6.82 Hz, 1 H) | 533.35 | A | |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-1267 | 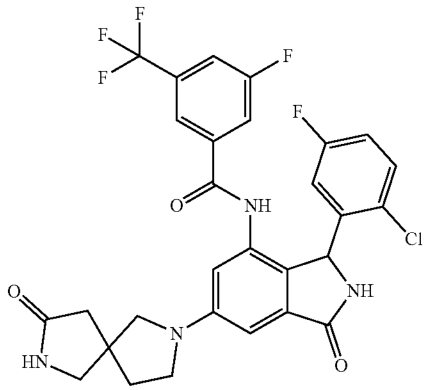 [SMILES: O=C1CC2(CCN(c3cc(NC(=O)c4cc(F)cc(C(F)(F)F)c4)c4c(c3)C(=O)NC4c3cc(F)ccc3Cl)C2)CN1] | Fc1ccc(C1)c(c1)C1NC(=O)c2cc(cc(NC(=O)c3cc(F)cc(c3)C(F)(F)F)c12)N1CCC2(CNC(=O)C2)C1 | (400 MHz, DMSO-d6) 10.37 (s, 1 H), 8.96 (s, 1 H), 7.92 (d, 8.6 Hz, 1 H), 7.72 (d, 8.9 Hz, 1 H) 7.68 (s, 1 H), 7.65 (s, 1 H), 7.29 (dd, 8.9, 5.2 Hz, 1 H), 7.06 ((ddd, 8.8, 8.1, 3.1 Hz), 1 H), 6.74 (d, 1.9 Hz, 1 H), 6.71-6.51 (submerged br. s, 1H), 6.63 (d, 1.3 Hz, 1 H), 5.87 (br s, 1 H), 3.33-3.25 (m, 6 H, submerged under water peak), 3.35-2.20 (m, 2 H), 2.12-1.98 (m, 2 H). Partial formate salt. | 603.4 | A | |
| I-1268 | 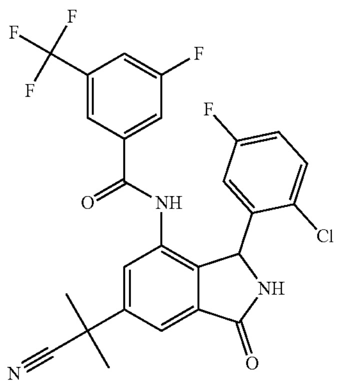 [SMILES: CC(C)(C#N)c1cc(NC(=O)c2cc(F)cc(C(F)(F)F)c2)c2c(c1)C(=O)NC2c1cc(F)ccc1Cl] | CC(C)(C#N)c1cc2C(=O)NC(c2c(NC(=O)c2cc(F)cc(c2)C(F)(F)F)c1c(F)ccc1Cl | (400 MHz, DMSO-d6) 10.64 (s, 1H), 9.22 (s, 1H), 7.93 (d, 7.5 Hz, 1H), 7.84-7.72 (m, 2H), 7.72-7.63 (m, 2H), 7.32 (dd, 8.9, 5.2 Hz, 1H), 7.10 (td, 8.5, 3.1 Hz, 1H), 6.67 (br s, 1H), 5.98 (br s, 1H), 1.79 (s, 3H), 1.78 (s, 3H). | 534.3 | A | |
| I-1269 | 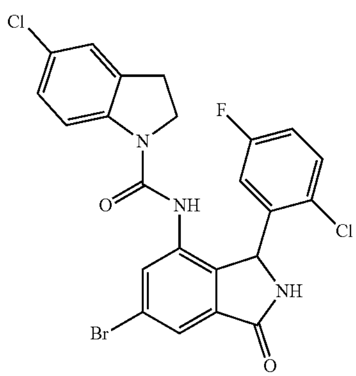 [SMILES: O=C1NC(c2cc(F)ccc2Cl)c2c(NC(=O)N3CCc4cc(Cl)ccc43)cc(Br)cc21] | Fc1ccc(C1)c(c1)C1NC(=O)c2cc(Br)cc(NC(=O)N3CCc4cc(Cl)ccc34)c12 | 1H NMR (400 MHz, DMSO-d6) 9.21 (s, 1H), 8.72 (s, 1H), 7.73-7.67 (m, 2H), 7.57 (d, 1.8 Hz, 1H), 7.39 (dd, 8.9, 5.2 Hz, 1H), 7.24 (d, 2.2 Hz, 1H), 7.22-7.12 (m, 2H), 6.69 (s, 1H), 5.97 (s, 1H), 3.84 (td, 10.1, 7.0 Hz, 2H), 3.03 (dqd, 20.1, 10.0, 4.8 Hz, 2H). | 536 | D | |
| I-1270 | 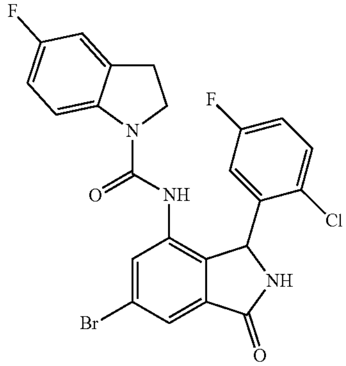 [SMILES: O=C1NC(c2cc(F)ccc2Cl)c2c(NC(=O)N3CCc4cc(F)ccc43)cc(Br)cc21] | Fc1ccc2N(CCc2c1)C(=O)Nc1cc(Br)cc2C(=O)NC(c12)c1cc(F)ccc1Cl | 1H NMR (400 MHz, DMSO-d6) 9.20 (s, 1H), 8.67 (s, 1H), 7.69 (p. 4.4 Hz, 2H), 7.58 (d, 1.8 Hz, 1H), 7.38 (dd, 8.9, 5.1 Hz, 1H), 7.17 (ddd, 8.8, 7.9, 3.1 Hz, 1H), 7.06 (dd, 8.5, 2.7 Hz, 1H), 6.94 (td, 9.0, 2.8 Hz, 1H), 6.70 (s, 1H), 5.97 (s, 1H), 3.84 (td, 10.1, 7.0 Hz, 1H), 3.33 (s, 1H), 3.13-2.89 (m, 2H). | 520.05 | A | |

TABLE 2-continued

Representative Compounds of the Invention with Bioactivity Data.

| Ex. No. | Structure | SMILES | $^1$H NMR | MS | ADP-Glo IC$_{50}$ | MCF 10A IC$_{50}$ |
|---|---|---|---|---|---|---|
| I-1271 | 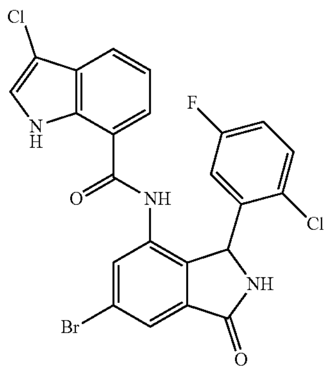 | Fc1ccc(C1)c(c1)C1NC(=O)c2cc(Br)cc(NC(=O)c3cccc4c(Cl)c[nH]c34)c12 | 1H NMR (400 MHz, DMSO-d6) 11.40 (s, 1H), 10.31 (s, 1H), 9.27 (s, 1H), 7.85 (dd, 2.8, 1.8 Hz, 1H), 7.79 (d, 1.8 Hz, 1H), 7.71 (d, 7.9 Hz, 1H), 7.51 (d, 2.6 Hz, 1H), 7.34-7.25 (m, 2H), 7.13 (t, 7.7 Hz, 1H), 7.06 (td, 8.4, 3.0 Hz, 1H), 6.92 (s, 1H), 6.12 (s, 1H). | 533.9 | C | |
| I-1272 | 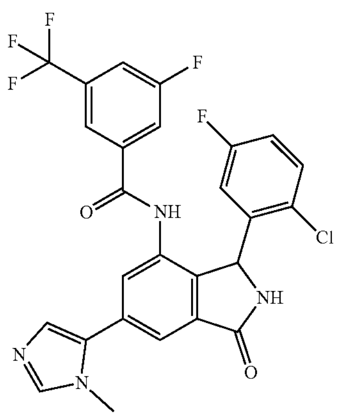 [SMILES: Cn1cncc1-c1cc(NC(=O)c2cc(F)cc(C(F)(F)F)c2)c2c(c1)C(=O)NC2c1cc(F)ccc1Cl] | Cn1cncc1-c1cc2C(=O)NC(c2c(NC(=O)c2cc(F)cc(c2)C(F)(F)F)c1)c1cc(F)ccc1Cl | NMR (400 MHz, DMSO) 10.60 (br s, 1H), 9.23 (br s, 1H), 7.96 (d, 8.3 Hz, 1H), 7.80-7.72 (m, , 3H), 7.67 (s, 1H), 7.62 (s, 1H), 7.33 (dd, 8.8, 5.1 Hz, 1H), 7.23 (s, 1H), 7.10 (td, 8.3, 2.8 Hz, 1H), 6.70 (br s, 1H), 6.03 (br s, 1H), 3.78 (s, 3H). contains 0.48 mol eq. of formate at 8.30. | 547.1 | A | |
| I-1273 | 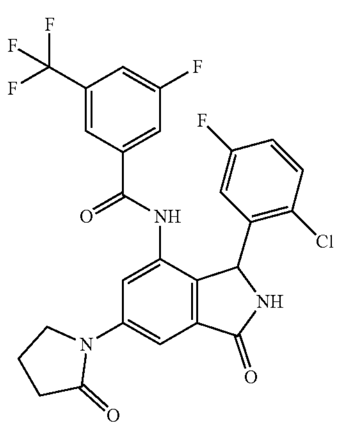 [SMILES: O=C(Nc1cc(N2CCCC2=O)cc2c1C(c1cc(F)ccc1Cl)NC2=O)c1cc(F)cc(C(F)(F)F)c1] | Fc1ccc(C1)c(c1)C1NC(=O)c2cc(cc(NC(=O)c3cc(F)cc(c3)C(F)(F)F)c12)N1CCCC1=O | NMR (400 MHz, ACN) 8.65 (s, 1H), 8.02 (d, 1.9 Hz, 1H), 7.89 (d, 1.9 Hz, 1H), 7.64-7.59 (m, 1H), 7.59-7.53 (m, 2H), 7.26-7.19 (m, 2H), 6.93 (ddd, 8.9, 8.0, 3.1 Hz, 1H), 6.62 (br s, 1H), 6.06 (br s, 1H), 3.95-3.88 (m, 2H), 2.53 (t, 8.0 Hz, 2H), 2.12-2.08 (m, 2H). 2.10 peak shadowed by water signal. | 550 | A | |

TABLE 2-continued

Representative Compounds of the Invention with Bioactivity Data.

| Ex. No. | Structure | SMILES | $^1$H NMR | MS | ADP-Glo IC$_{50}$ | MCF 10A IC$_{50}$ |
|---|---|---|---|---|---|---|
| I-1274 | 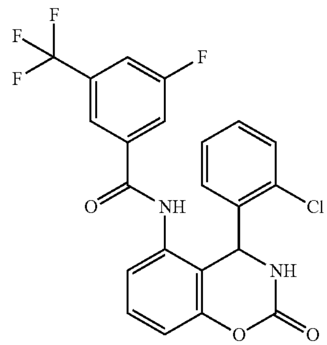 | Fc1cc(cc (c1)C(F) (F)F)C(= O)Nc1cc cc2OC(= O)NC(c3 ccccc3Cl) c12 | NMR (400 MHz, DMSO) 10.26 (s, 1H), 8.70 (d, 2.8 Hz, 1H), 7.97 (br. d, 8.2 Hz, 1H), 7.91 (s, 1H), 7.87 (d, 9.1 Hz, 1H), 7.44 (t, 8.1 Hz, 1H), 7.31 (dd, 8.0, 1.3 Hz, 1H), 7.27-7.23 (m, 1H), 7.18-7.13 (m, 2H), 7.07 (br. d, 7.8 Hz, 1H), 7.02 (dd, 7.7, 1.4 Hz, 1H), 6.15 (d, 2.7 Hz, 1H). | 465.1 | C | |
| I-1275 | 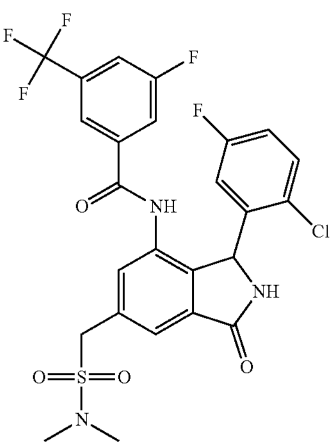 [SMILES: CN(C)S(=O)(=O)Cc1cc(NC(=O)c2cc(F)cc(C(F)(F)F)c2)c2c(c1)C(=O)NC2c1cc(F)ccc1Cl] | CN(C)S (=O)(=O) Cc1cc2C C(=O)NC (c2c(NC (=O)c2cc (F)cc(c2) C(F)(F)F) c1)c1cc (F)ccc1Cl | NMR (400 MHz, DMSO-d6) 10.60 (br. s, 1H), 9.21 (br. s, 1H), 7.95 (dt, 8.5, 2.0 Hz, 1H), 7.77 (s, 1H), 7.75 (br. d, 8.4 Hz, 1H) 7.66 (s, 1H), 7.55 (s, 1H), 7.32 (dd, 8.9, 5.2 Hz, 1H), 7.10 (td, 8.5, 3.1 Hz, 1H), 6.58 (br. s, 1H), 5.97 (br. s, 1H), 4.70-4.58 (m, 2H), 2.76 (s, 6H). | 588.2 | A | |
| I-1276 | 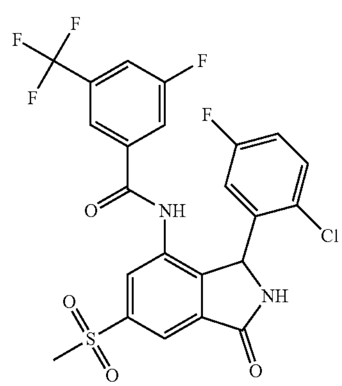 [SMILES: CS(=O)(=O)c1cc(NC(=O)c2cc(F)cc(C(F)(F)F)c2)c2c(c1)C(=O)NC2c1cc(F)ccc1Cl] | CS(=O) (=O)c1cc2 C(=O)N C(c2c(N C(=O)c2 cc(F)cc(c 2)C(F)(F) F)c1)c1c c(F)ccc1 Cl | NMR (400 MHz, CD3CN) 8.81 (br s, 1H), 8.21 (d, 1.5 Hz, 1H), 8.14 (s, 1H), 7.70-7.65 (m, 1H), 7.63-7.58 (m, 1H), 7.55-7.58 (m, 1H), 7.46 (br s, 1H), 7.29 (dd, 8.9, 5.1 Hz, 1H), 7.00 (ddd, 8.9, 8.0, 3.1 Hz, 1H), 6.69 (br s, 1H), 6.23 (br s, 1H), 3.18 (s, 3H). | 543 | A | |

TABLE 2-continued

Representative Compounds of the Invention with Bioactivity Data.

| Ex. No. | Structure | SMILES | $^1$H NMR | MS | ADP-Glo IC$_{50}$ | MCF 10A IC$_{50}$ |
|---|---|---|---|---|---|---|
| I-1277 | 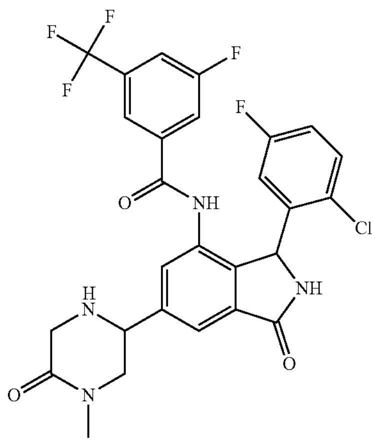 | CN1CC(NCC1=O)c1cc2C(=O)NC(c2c(NC(=O)c2cc(F)cc(c2)C(F)(F)F)c1)c1cc(F)ccc1Cl | NMR (400 MHz, CD3CN) 8.85 (br s, 1H), 7.76 (s,1H), 7.68-7.56 (m, 4H), 7.39 (s, 1H), 7.25 (dd, 8.9, 5.1 Hz, 1H), 6.96 (td, 8.4, 3.0 Hz, 1H), 6.60 (br s, 1H), 6.11 (br s, 1H), 4.27 (dt, 10.2, 4.0 Hz, 1H), 3.55-3.43 (m, 3H), 3.37 (dd, 20.5, 10.7 Hz, 1H), 2.89 (s, 3H). DMSO peak observed @ 2.5 | 579.2 | A | |
| I-1278 | 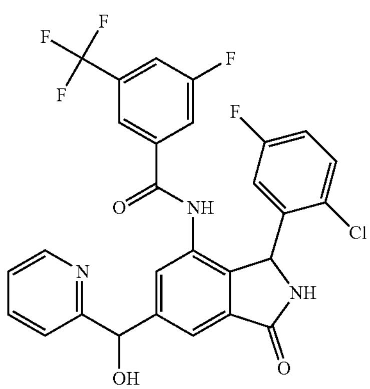 [SMILES: O=C(Nc1cc(C(O)c2ccccn2)cc2c1C(c1cc(F)ccc1Cl)NC2=O)c1cc(F)cc(C(F)(F)F)c1] | OC(c1cc2C(=O)NC(c2c(NC(=O)c2cc(F)cc(c2)C(F)(F)F)c1)c1cc(F)ccc1Cl)c1cccn1 | NMR (400 MHz, DMSO-d6) Description for the major diastereomer.-' 10.49 (br. s, 1Hs), 9.12 (br. s, 1H), 8.50 (ddd, 4.8, 1.7, 0.9 Hz, 1H), 7.93 (br. d, 8.3 Hz, 1H), 7.83 (td, 7.7, 1.8 Hz, 1H), 7.72 (app. d, 9.8 Hz, 2H), 7.66-7.62 (m, 5.9 Hz, 2H), 7.50 (s, 1H), 7.33-7.24 (m, 2H), 7.08 (td, 8.5, 3.1 Hz, 1H), 6.60 (br. s, 1H), 6.40 (br. s, 1H), 5.92 (submerged br. s, 1H), 5.87 (s, 1H). 2:1 mixture in the 2 diastereomers. Presence of grease in the aliphatic region. | 574.2 | A | |
| I-1279 | 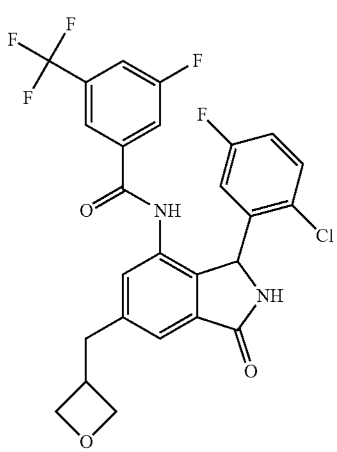 [SMILES: O=C(Nc1cc(CC2COC2)cc2c1C(c1cc(F)ccc1Cl)NC2=O)c1cc(F)cc(C(F)(F)F)c1] | Fc1ccc(C1)c(c1)C1NC(=O)c2cc(CC3COC3)cc(NC(=O)c3cc(F)cc(c3)C(F)(F)F)c12 | 1H NMR (400 MHz, DMSO-d6) 3.12 (dd, 7.71, 4.42 Hz, 2 H) 3.32-3.38 (m, 2 H) 4.38 (td, 6.06, 3.79 Hz, 2 H) 4.65 (ddd, 7.64, 6.00, 1.26 Hz, 2 H) 5.83-5.97 (m, 1 H) 7.07 (td, 8.46, 3.03 Hz, 1 H) 7.26-7.31 (m, 2 H) 7.50 (s, 1 H) 7.63 (s, 1 H) 7.71 (br d, 8.84 Hz, 1 H) 7.93 (br d, 8.59 Hz, 1 H) 9.09 (br s, 1 H) 10.45 (s, 1 H) | 537.35 | A | |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-1280 | 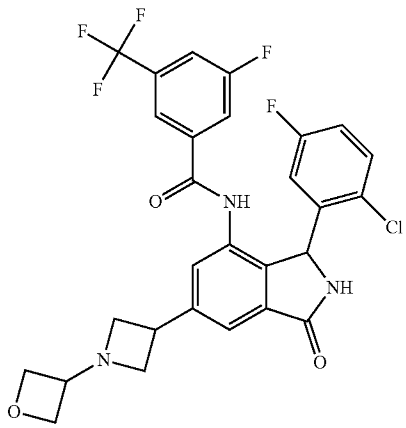 [SMILES: O=C(Nc1cc(C2CN(C3COC3)C2)cc2c1C(c1cc(F)ccc1Cl)NC2=O)c1cc(F)cc(C(F)(F)F)c1] | Fc1ccc(C1)c(c1)C1NC(=O)c2cc(cc(NC(=O)c3cc(F)cc(c3)C(F)(F)F)c12)C1CN(C1)C1COC1 | 1H NMR (400 MHz, DMSO-d6) 2.29 (s, 1 H) 3.56-3.82 (m, 2 H) 3.92-4.31 (m, 4 H) 4.42-4.52 (m, 2 H) 4.67 (br t, 6.57 Hz, 2 H) 5.97 (br s, 1 H) 7.03-7.13 (m, 1 H) 7.30 (dd, 8.84, 5.31 Hz, 1 H) 7.50 (s, 1 H) 7.66 (s, 1 H) 7.69-7.82 (m, 2 H) 7.94 (br d, 8.34 Hz, 1 H) 9.15 (br s, 1 H) 10.53 (s, 1 H) | 578.22 | A | |
| I-1281 | 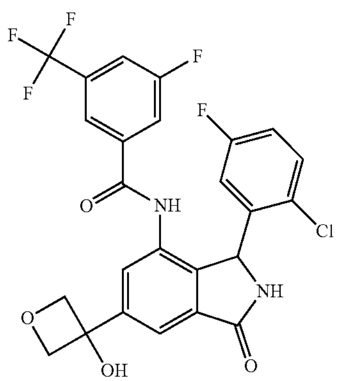 [SMILES: O=C(Nc1cc(C2(O)COC2)cc2c1C(c1cc(F)ccc1Cl)NC2=O)c1cc(F)cc(C(F)(F)F)c1] | OC1(COC1)c1cc2C(=O)NC(c2c(NC(=O)c2cc(F)cc(c2)C(F)(F)F)c1c(F)ccc1Cl | NMR (400 MHz, DMSO-d6) 10.56 (br. s, 1H), 9.15 (s, 1H), 7.93 (submerged br. d, 8.7 Hz, 1H), 7.91 (d, 1.5 Hz, 1H), 7.76 (d, 1.4 Hz, 1H), 7.75 (submerged br. d, 1H), 7.68 (s, 1H), 7.32 (dd, 8.9, 5.2 Hz, 1H), 7.09 (td, 8.4, 3.1 Hz, 1H), 6.82-6.50 (m, 2H), 6.01 (br. s, 1H), 4.86 (d, 6.6 Hz, 2H), 4.76 (d, 6.5 Hz, 1H), 4.71 (d, 6.5 Hz, 1H). | 539.2 | A | |
| I-1282 | 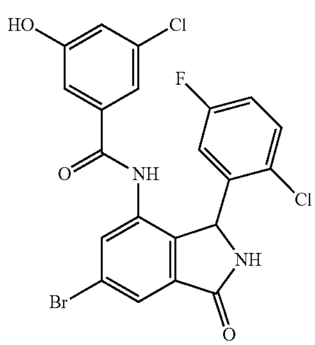 [SMILES: O=C(Nc1cc(Br)cc2c1C(c1cc(F)ccc1Cl)NC2=O)c1cc(O)cc(Cl)c1] | Oc1cc(Cl)cc(c1)C(=O)Nc1cc(Br)cc2C(=O)NC(c12)c1cc(F)ccc1Cl | 1H NMR (400 MHz, DMSO-d6) 10.24 (s,2H), 9.26 (s, 1H), 7.78-7.73 (d, 1.8 Hz, 2H), 7.38 (dd, 8.8, 5.2 Hz, 1H), 7.15 (ddd, 8.8, 7.9, 3.1 Hz, 1H), 6.96 (d, 1.6 Hz, 2H), 6.87 (t, 1.7 Hz, 1H), 6.66 (s, 1H), 6.00 (s, 1H) | 510.09 | B | |
| I-1283 | 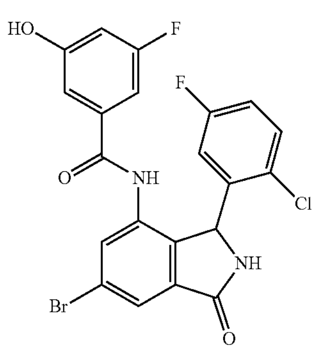 [SMILES: O=C(Nc1cc(Br)cc2c1C(c1cc(F)ccc1Cl)NC2=O)c1cc(O)cc(F)c1] | Oc1cc(F)cc(c1)C(=O)Nc1cc(Br)cc2C(=O)NC(c12)c1cc(F)ccc1Cl | 1H NMR (400 MHz, DMSO-d6) 10.24-10.19 (m, 2H), 9.26 (s, 1H), 7.78-7.72 (m, 2H), 7.38 (dd, 8.9, 5.1 Hz, 1H), 7.14 (ddd, 8.8, 7.9, 3.1 Hz, 1H), 6.90-6.84 (m, 1H), 6.79-6.66 (m, 2H), 6.00 (s, 1H). | 495 | D | |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-1284 | 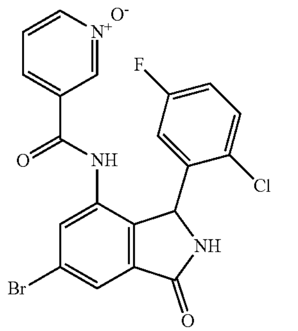 | [O-][n+]1ccc c(c1)C(= O)Nc1cc (Br)cc2C (=O)NC(c 12)c1cc (F)ccc1Cl | 1H NMR (400 MHz, DMSO-d6) 10.51 (s, 1H), 9.29 (s, 1H), 8.40-8.34 (m, 1H), 8.29-8.24 (m, 1H), 7.82 (s, 1H), 7.72 (s, 1H), 7.56-7.43 (m, 2H), 7.38 (dd, 8.9, 5.2 Hz, 1H), 7.20-7.10 (m, 1H), 5.97 (s, 1H). | 477.85 | E | |
| I-1285 | 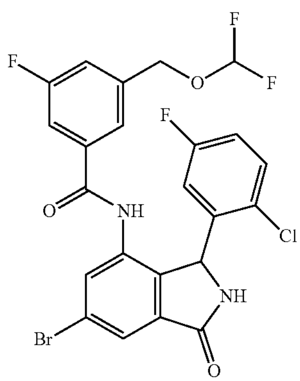 [SMILES: O=C(Nc1cc(Br)cc2c1C(c1cc(F)ccc1Cl)NC2=O)c1cc(F)cc(COC(F)F)c1] | FC(F)OC c1cc(F)cc (c1)C(=O) Nc1cc(Br)cc2C(= O)NC(c1 2)c1cc(F) ccc1Cl | 1H NMR (400 MHz, DMSO-d6) 9.37 (d, 60.3 Hz, 1H), 8.08 (s, 2H), 7.59 (s, 1H), 7.44-7.00 (m, 4H), 6.80 (d, 53.5 Hz, 1H), 6.30 (d, 149.1 Hz., 1H), 5.46 (t, 5.6 Hz, 1H), 4.51 (d, 5.7 Hz, 2H). | 557 | E | |
| I-1286 | 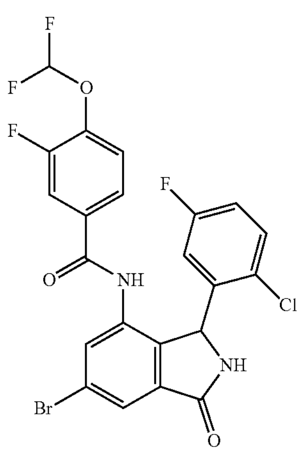 [SMILES: O=C(Nc1cc(Br)cc2c1C(c1cc(F)ccc1Cl)NC2=O)c1ccc(OC(F)F)c(F)c1] | FC(F)Oc 1ccc(cc1 F)C(=O) Nc1cc(Br) cc2C(= O)NC(c1 2)c1cc(F) ccc1Cl | 1H NMR (400 MHz, DMSO-d6) 10.33 (s, 1H), 9.28 (s, 1H), 7.81 (d, 1.7 Hz, 1H), 7.73 (d, 1.7 Hz, 1H), 7.59-7.31 (m, 5H), 7.13 (td, 8.4, 3.1 Hz, 1H), 6.34-6.87(s, 1H), 6.00 (s, 1H). | 544.9 | D | |
| I-1287 | 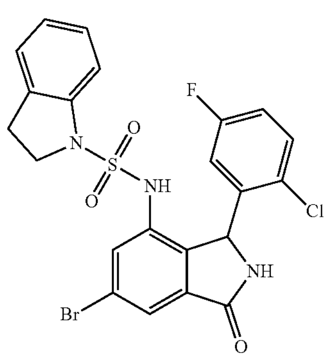 [SMILES: O=C1NC(c2cc(F)ccc2Cl)c2c(NS(=O)(=O)N3CCc4ccccc43)cc(Br)cc21] | Fc1ccc(C 1)c(c1)C1 NC(=O)c 2cc(Br)cc (NS(=O) (=O)N3C Cc4ccccc 34)c12 | 1H NMR (400 MHz, DMSO-d6) 9.93 (s, 1H), 9.24 (s, 1H), 7.61 (s, 1H), 7.48 (s, 1H), 7.27-7.16 (m, 3H), 7.04-6.90 (m, 3H), 6.76 (s, 1H), 6.08 (s, 1H), 3.81-3.72 (m, 1H), 3.65 (td, 10.1, 6.6 Hz, 1H), 3.09-2.88 (m, 2H). | 536 | E | |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-1288 | 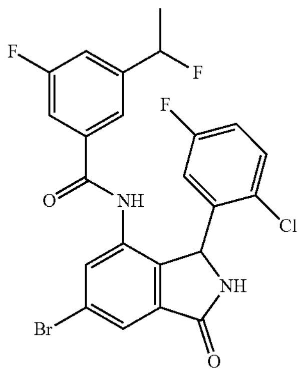 [SMILES: CC(F)c1cc(F)cc(C(=O)Nc2cc(Br)cc3c2C(c2cc(F)ccc2Cl)NC3=O)c1] | CC(F)c1cc(F)cc(c1)C(=O)Nc1cc(Br)cc2C(=O)NC(c12)c1cc(F)ccc1Cl | 1H NMR (400 MHz, DMSO-d6) 10.38 (s, 1H), 9.28 (s, 1H), 7.81 (d, 1.7 Hz, 1H), 7.75 (d, 1.7 Hz, 1H), 7.43 (dd, 19.9, 9.3 Hz, 2H), 7.38-7.27 (m, 2H), 7.12 (tt, 8.7, 3.2 Hz, 1H), 6.72 (s, 2H), 6.00 (s, 1H), 5.85-5.65 (m, 1H), 2.08 (s, OH), 1.59 (ddd, 24.4, 6.4, 1.9 Hz, 3H). | 523 | B | |
| I-1289 | 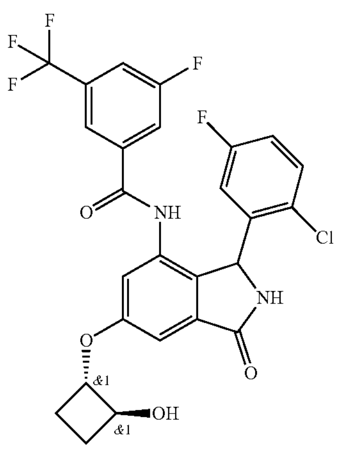 [SMILES: O=C(Nc1cc(O[C@H]2CC[C@@H]2O)cc2c1C(c1cc(F)ccc1Cl)NC2=O)c1cc(F)cc(C(F)(F)F)c1] | O[C@H]1CC[C@@H]1Oc1cc2C(=O)NC(c2c(NC(=O)c2cc(F)cc(c2)C(F)(F)F)c1)c1cc(F)ccc1Cl | 1H NMR (400 MHz, DMSO-d6) 10.46 (br. s, 1H), 9.12 (br. s, 1H), 7.95 (d, 8.4 Hz, 1H), 7.71 (d, 9.1 Hz, 1H), 7.62 (s, 1H), 7.33-7.28 (m, 2H), 7.15-7.01 (m, 2H), 6.58 (br. s, 1H), 5.91 (br. s, 1H), 5.75 (t, 8.0 Hz, 1H), 4.44 (q, 7.5 Hz, 1H), 4.15-3.95 (m, 1H), 2.25-2.19 (m, 1H), 2.12-2.03 (m, 1H), 1.56-1.35 (m, 2H) | 553.2 | B | |
| I-1290 | 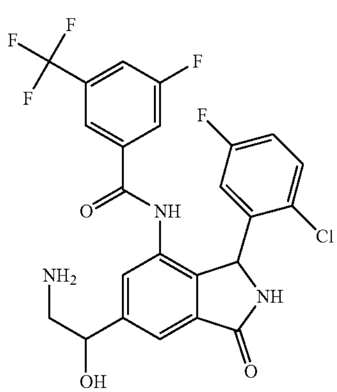 [SMILES: NCC(O)c1cc(NC(=O)c2cc(F)cc(C(F)(F)F)c2)c2c(c1)C(=O)NC2c1cc(F)ccc1Cl] | NCC(O)c1cc2C(=O)NC(c2c(NC(=O)c2cc(F)cc(c2)C(F)(F)F)c1)c1cc(F)ccc1Cl | NMR (400 MHz, DMSO) 10.58 (br s, 1H), 9.13 (br s, 1H), 8.23 (s, 1H), 7.91 (d, 8.3 Hz, 1H), 7.75-7.68 (m, 1 H), 7.64 (d, 7.5 Hz, 1 H), 7.49 (d, 16.8 Hz, 1H), 7.31-7.25 (m, 1 H), 7.35-6.94 (m, 2 H), 7.09-7.02 (m, 1 H), 5.96 (br s, 1H), 4.87 (ddd, 12.6, 8.9, 3.1 Hz, 1H), 3.10-2.99 (m, 1H), 2.88-2.78 (m, 1H). | 526.1 | B | |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-1291 | 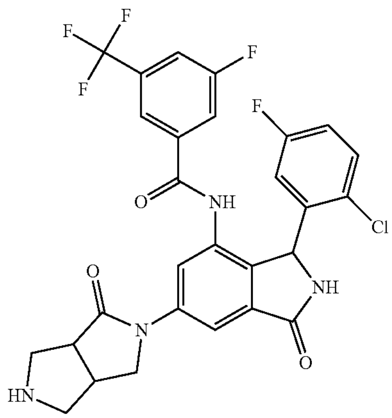 [SMILES: O=C(Nc1cc(N2CC3CNCC3C2=O)cc2c1C(c1cc(F)ccc1Cl)NC2=O)c1cc(F)cc(C(F)(F)F)c1] | Fc1ccc(C1)c(c1)C1NC(=O)c2cc(cc(NC(=O)c3cc(F)cc(c3)C(F)(F)F)c12)N1CC2CNCC2C1=O | (400 MHz, CD3CN) 8.70 (br. s, 1H), 8.14 (s, 1H), 8.11 (dd, 6.0, 1.9 Hz, 1H), 7.93 (dd, 9.9, 1.8 Hz, 1H), 7.65 (d, 7.5 Hz, 1H), 7.59 (d, 7.5 Hz, 1H), 7.58 (s, 1H), 7.27 (br. s, 1H), 7.25 (dd, 9.0, 5.1 Hz, 1H), 6.96 (td, 8.5, 3.0 Hz, 1H), 6.65 (br. s, 1H), 6.09 (br. s, 1H), 4.17 (dd, 17.2, 9.0 Hz, 1H), 3.65 (ddd, 9.8, 6.7, 2.8 Hz, 1H), 3.28 (d, 10.8 Hz, 1H), 3.18 (t, 8.3 Hz, 1H), 3.04-2.91 (m, 4H). | 591.3 | A | |
| I-1292 | 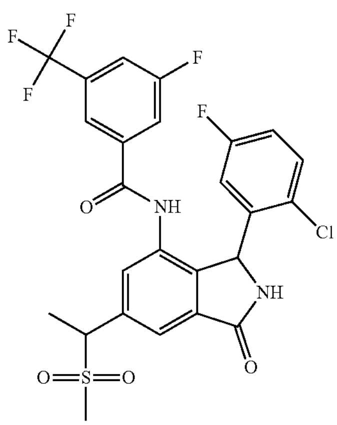 [SMILES: CC(c1cc(NC(=O)c2cc(F)cc(C(F)(F)F)c2)c2c(c1)C(=O)NC2c1cc(F)ccc1Cl)S(C)(=O)=O] | CC(c1cc2C(=O)NC(c2c(NC(=O)c2cc(F)cc(c2)C(F)(F)F)c1)c1cc(F)ccc1Cl)S(C)(=O)=O | NMR (400 MHz, CD3CN) 8.68 (s, 1H), 7.79-7.72 (m, 1H), 7.65 (d, J = 7.9 Hz, 1H), 7.62-7.56 (m, 3H), 7.32-7.22 (m, 2H), 6.97 (td, J = 8.4, 2.6 Hz, 1H), 6.63 (br, s, 1H), 6.11 (br, s, 1H), 5.55-5.46 (m, 1H), 2.68-2.61 (m, 3H), 1.68-1.63 (m, 3H). | 573 | A | |
| I-1293 | 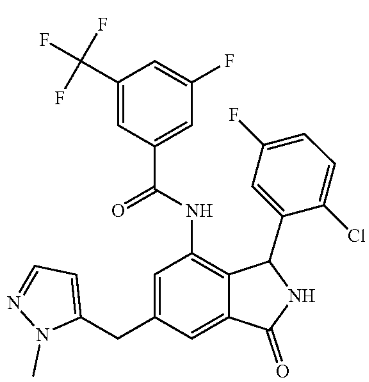 [SMILES: Cn1nccc1Cc1cc(NC(=O)c2cc(F)cc(C(F)(F)F)c2)c2c(c1)C(=O)NC2c1cc(F)ccc1Cl] | Cn1nccc1Cc1cc2C(=O)NC(c2c(NC(=O)c2cc(F)cc(c2)C(F)(F)F)c1)c1cc(F)ccc1Cl | 1H-NMR (400 MHz, DMSO-d6) 10.51 (br. s, 1H), 9.15 (br. s, 1H), 7.94 (br. d, 9.0 Hz, 1H), 7.71 (br. d, 9.7 Hz, 1H), 7.62 (br. s, 1H), 7.53 (br. s, 1H), 7.34 (d, 1.8 Hz, 1H), 7.31 (dd, 8.9, 5.1 Hz, 1H), 7.30-7.28 (m, 1H), 7.08 (app. td, 8.5, 3.1 Hz, 1H), 6.59 (br. s, 1H), 6.09 (s, 1H), 5.94 (br. s, 1H), 4.27-4.18 (m, 2H), 3.71 (s, 3H). | 561.3 | A | |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-1294 | 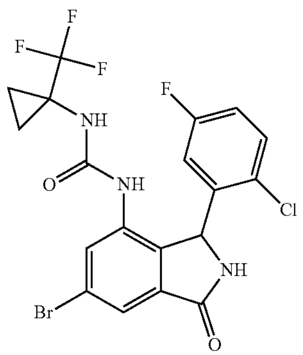 [SMILES: O=C(Nc1cc(Br)cc2c1C(c1cc(F)ccc1Cl)NC2=O)NC1(C(F)(F)F)CC1] | Fc1ccc(C1)c(c1)C1NC(=O)c2cc(Br)cc(NC(=O)NC3(CC3)C(F)(F)F)c12 | 1H-NMR (400 MHz, DMSO-d6) 9.19 (br. s, 1H), 8.11 (s, 1H), 7.72 (br. s, 1H), 7.59 (d, 1.6 Hz, 1H), 7.53-7.43 (m, 1H), 7.36 (s, 1H), 7.23 (app. td, 8.5, 3.1 Hz, 1H), 6.69 (br. s, 1H), 5.97 (br. s, 1H), 1.22-1.17 (m, 1H), 1.16-1.09 (m, 1H), 1.07-0.99 (m, 1H), 0.87-0.78 (m, 1H). | 506.2 | D | |
| I-1295 | 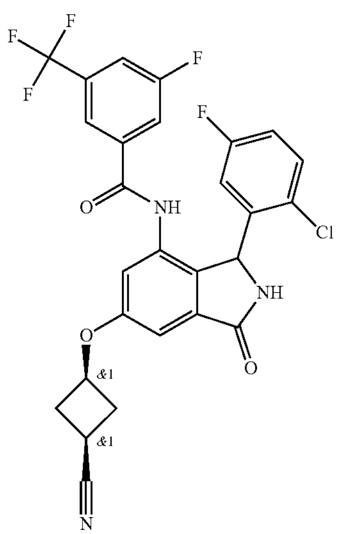 [SMILES: N#C[C@H]1C[C@@H](Oc2cc(NC(=O)c3cc(F)cc(C(F)(F)F)c3)c3c(c2)C(=O)NC3c2cc(F)ccc2Cl)C1] | Fc1ccc(C1)c(c1)C1NC(=O)c2cc(O[C@H]3C[C@H](C3)C#N)cc(NC(=O)c3cc(F)cc(c3)C(F)(F)F)c12 | 1H NMR (400 MHz, DMSO) 10.44 (br. s, 1H), 9.14 (br. s, 1H), 7.94 (br. d, 8.5 Hz, 1H), 7.73-7.68 (m, 1H), 7.62 (s, 1H), 7.31 (dd, 8.9, 5.2 Hz, 1H), 7.13-7.04 (m, 2H), 7.01 (d, 1.9 Hz, 1H), 6.62 (br. s, 1H), 5.91 (s, 1H), 4.90-4.80 (m, 1H), 3.22-3.05 (m, 1H), 3.02-2.89 (m, 2H), 2.48-2.32 (m, 2H) | 562.2 | A | |
| I-1296 | 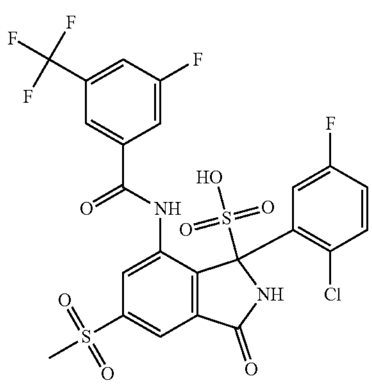 [SMILES: CS(=O)(=O)c1cc(NC(=O)c2cc(F)cc(C(F)(F)F)c2)c2c(c1)C(=O)NC2(c1cc(F)ccc1Cl)S(=O)(=O)O] | CS(=O)(=O)c1cc2C(=O)NC(c2c(NC(=O)c2cc(F)cc(c2)C(F)(F)F)c1)(c1cc(F)ccc1C1)S(O)(=O)=O | (400 MHz, DMSO-d6) 10.93 (s, 1 H), 9.87 (s, 1 H), 8.77 (dd, 11.7, 3.1 Hz, 1 H), 8.66 (d, 1.5 Hz, 1 H), 8.02 (d, 8.5 Hz, 1 H), 8.00 (d, 1.6 Hz, 1 H), 7.79 (s, 1 H), 7.71 (d, 9.0 Hz, 1 H), 7.26 (dd, 8.8, 5.6 Hz, 1 H), 7.24-7.16 (m, 1 H), 7.10 (ddd, 8.8, 7.5, 3.1 Hz, 1 H), 6.95 (br s, 1 H), 3.35 (s, 3 H). | 623.3 | D | |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-1297 | 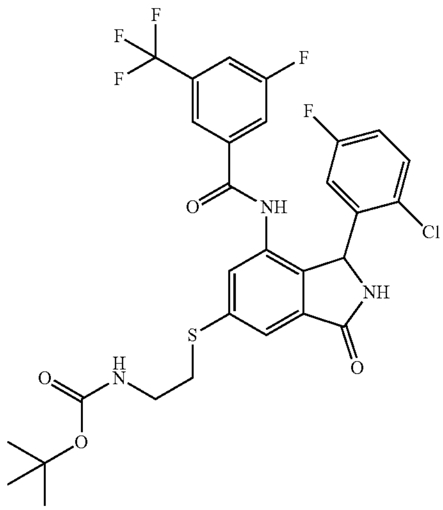 | CC(C)(C)OC(=O)NCCSc1cc2C(=O)NC(c2c(NC(=O)c2cc(F)cc(c2)C(F)(F)F)c1)c1cc(F)ccc1Cl | NMR (400 MHz, CD3CN) 8.70 (brs, 1H), 7.70 (d, 1.4 Hz, 1H), 7.64 (br d, 8.3 Hz, 1H), 7.59 (br d, 8.4 Hz, 1H), 7.58 (s, 1H), 7.27 (br s, 1H), 7.25 (dd, 8.9, 5.1 Hz, 1H), 6.96 (td, 8.4, 3.0 Hz, 1H), 6.67 (brs, 1H), 6.09 (brs, 1H), 5.57 (brs, 1H), 3.30 (q, 6.5 Hz, 2H), 3.18-3.11 (m, 2H), 1.39 (s, 9H). | 642.2 | B | |
| I-1298 | 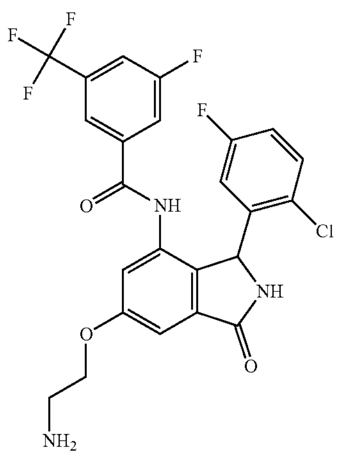 [SMILES: NCCOc1cc(NC(=O)c2cc(F)cc(C(F)(F)F)c2)c2c(c1)C(=O)NC2c1cc(F)ccc1Cl] | NCCOc1cc2C(=O)NC(c2c(NC(=O)c2cc(F)cc(c2)C(F)(F)F)c1)c1cc(F)ccc1Cl | (400 MHz, DMSO-d6) 10.47 (br s, 1H), 9.12 (s, 1H), 7.94 (d, 8.3 Hz, 1H), 7.71 (d, 8.9 Hz, 1H), 7.64 (s, 1H), 7.31 (dd, 8.9, 5.2 Hz, 1H), 7.22 (d, 2.2 Hz, 1H), 7.12-7.03 (m, 2H), 6.57 (br s, 1H), 5.93 (br s, 1H), 4.19-4.06 (m, 2H), 3.35 (br s, 3H), 3.02 (t, 5.3 Hz, 2H) | 526.2 | B | |
| I-1299 | 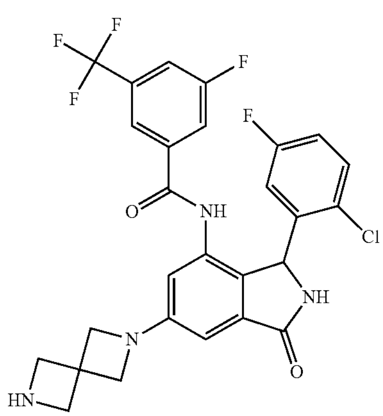 [SMILES: O=C(Nc1cc(N2CC3(CNC3)C2)cc2c1C(c1cc(F)ccc1Cl)NC2=O)c1cc(F)cc(C(F)(F)F)c1] | Fc1ccc(C1)c(c1)C1NC(=O)c2cc(cc(NC(=O)c3cc(F)cc(c3)C(F)(F)F)c12)N1CC2(CNC2)C1 | NMR (400 MHz, DMSO-d6) 10.46 (br. s, 1H), 9.00 (br. s, 1H), 7.92 (br. d, 9.2 Hz, 1H), 7.72 (br. d, 8.3 Hz, 1H), 7.64 (s, 1H), 7.28 (dd, 8.7, 5.1 Hz, 1H), 7.06 (td, 8.3, 3.2 Hz, 1H), 6.66 (d, 1.7 Hz, 1H), 6.52 (d, 1.2 Hz, 1H), 6.75-6.40 (br. s, 1H), 5.87 (br. s, 1H), 4.04-3.99 (m, 4H), 3.94-3.86 (m, 4H) | 561.3 | B | |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-1300 | 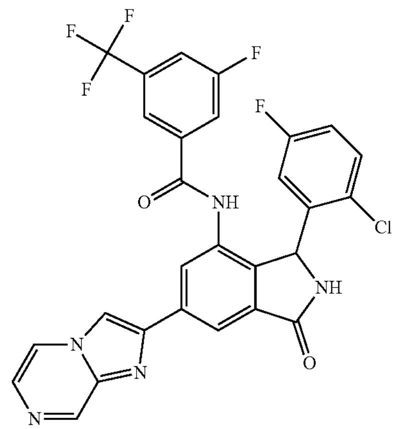 [SMILES: O=C(Nc1cc(-c2cn3ccncc3n2)cc2c1C(c1cc(F)ccc1Cl)NC2=O)c1cc(F)cc(C(F)(F)F)c1] | Fc1ccc(C1)c(c1)C1NC(=O)c2cc(cc(NC(=O)c3cc(F)cc(c3)C(F)(F)F)c12)-c1cn2ccncc2n1 | NMR (400 MHz, ACN-d3) 9.00 (s, 1H), 8.88 (br. s, 1H), 8.41 (s, 1H), 8.32 (dd, 4.5, 1.1 Hz, 1H), 8.29 (m, 2H), 7.86 (d, 4.6 Hz, 1H), 7.68-7.61 (m, 2H), 7.60 (s, 1H), 7.41 (s, 1H), 7.27 (dd, 8.9, 5.1 Hz, 1H), 6.98 (td, 8.5, 3.1 Hz, 1H), 6.73 (br. s, 1H), 6.18 (br. s, 1H) | 582.4 | A | |
| I-1301 | 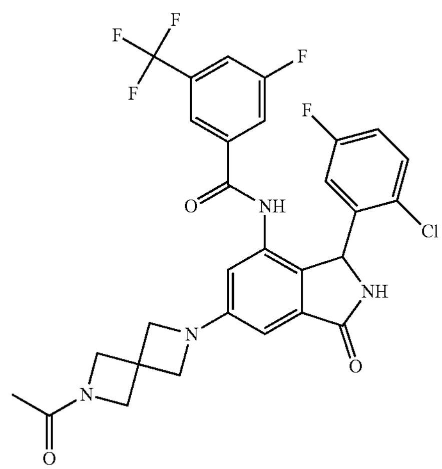 [SMILES: CC(=O)N1CC2(C1)CN(c1cc(NC(=O)c3cc(F)cc(C(F)(F)F)c3)c3c(c1)C(=O)NC3c1cc(F)ccc1Cl)C2] | CC(=O)N1CC2(C1)CN(C2)c1cc2C(=O)NC(c2c(NC(=O)c2cc(F)cc(c2)C(F)(F)F)c1)c1cc(F)ccc1C1 | NMR (400 MHz, DMSO-d6) 10.43 (br. s, 1H), 9.02 (br. s, 1H), 7.93 (br. d, 8.6 Hz, 1H), 7.72 (br. d, 9.2 Hz, 1H), 7.64 (s, 1H), 7.29 (dd, 9.0, 5.1 Hz, 1H), 7.07 (td, 8.3, 3.3 Hz, 1H), 6.67 (d, 1.7 Hz, 1H), 6.54 (br. s, 1H), 6.75-6.40 (br. s, 1H), 5.87 (br. s, 1H), 4.35-4.29 (m, 2H), 4.10-4.01 (m, 6H), 1.76 (s, 3H) | 603.3 | B | |
| I-1302 | 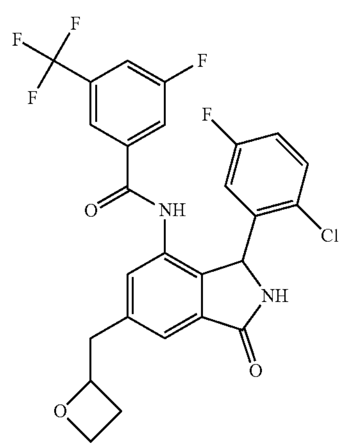 [SMILES: O=C(Nc1cc(CC2CCO2)cc2c1C(c1cc(F)ccc1Cl)NC2=O)c1cc(F)cc(C(F)(F)F)c1] | Fc1ccc(C1)c(c1)C1NC(=O)c2cc(CC3CCO3)cc(NC(=O)c3cc(F)cc(c3)C(F)(F)F)c12 | 1H NMR (400 MHz, DMSO-d6) 2.37-2.45 (m, 1 H) 2.59-2.69 (m, 1 H) 3.04-3.22 (m, 2 H) 4.38 (tt, 9.00, 5.78 Hz, 1 H) 4.45-4.56 (m, 1 H) 4.92-5.04 (m, 1 H) 5.79-6.08 (m, 1 H) 7.09 (td, 8.34, 3.03 Hz, 1 H) 7.26-7.39 (m, 2 H) 7.55-7.79 (m, 3 H) 7.95 (br d, 8.59 Hz, 1 H) 9.12 (br s, 1 H) 10.45-10.56 (m, 1 H) | 537.25 | A | |

TABLE 2-continued

Representative Compounds of the Invention with Bioactivity Data.

| Ex. No. | Structure | SMILES | $^1$H NMR | MS | ADP-Glo IC$_{50}$ | MCF 10A IC$_{50}$ |
|---|---|---|---|---|---|---|
| I-1303 | 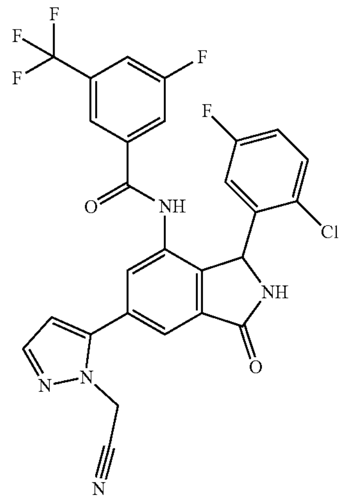 [SMILES: N#CCn1nccc1-c1cc(NC(=O)c2cc(F)cc(C(F)(F)F)c2)c2c(c1)C(=O)NC2c1cc(F)ccc1Cl] | Fc1ccc(C1)c(c1)C1NC(=O)c2cc(cc(NC(=O)c3cc(F)cc(c3)C(F)(F)F)c12)-c1ccnn1CC#N | 1H NMR (400 MHz, DMSO-d6) 5.57 (s, 2 H) 5.91-6.22 (m, 1 H) 6.66 (d, 2.02 Hz, 1 H) 7.11 (td, 8.40, 2.91 Hz, 1 H) 7.33 (dd, 8.84, 5.05 Hz, 1 H) 7.59-7.67 (m, 2 H) 7.70-7.76 (m, 2 H) 7.79 (d, 1.52 Hz, 1 H) 7.96 (br d, 8.34 Hz, 1 H) 9.23-9.40 (m, 1 H) | 572.17 | A | |
| I-1304 | 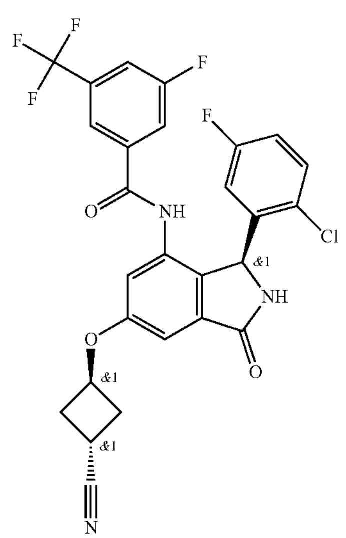 [SMILES: N#C[C@H]1C[C@H](Oc2cc(NC(=O)c3cc(F)cc(C(F)(F)F)c3)c3c(c2)C(=O)N[C@@H]3c2cc(F)ccc2Cl)C1] | Fc1ccc(C1)c(c1)[C@H]1NC(=O)c2cc(O[C@H]3C[C@@H](C3)C#N)cc(NC(=O)c3cc(F)cc(c3)C(F)(F)F)c12 | | | D | |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-1305 | 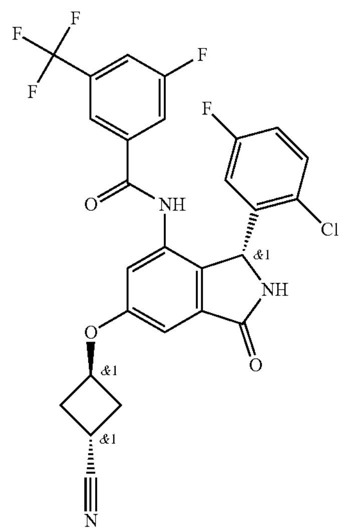 [SMILES: N#C[C@H]1C[C@H](Oc2cc(NC(=O)c3cc(F)cc(C(F)(F)F)c3)c3c(c2)C(=O)N[C@H]3c2cc(F)ccc2Cl)C1] | Fc1ccc(C1)c(c1)[C@@H]1NC(=O)c2cc(O[C@H]3C[C@@H](C3)C#N)cc(NC(=O)c3cc(F)cc(c3)C(F)(F)F)c12 | | | A | |
| I-1306 | 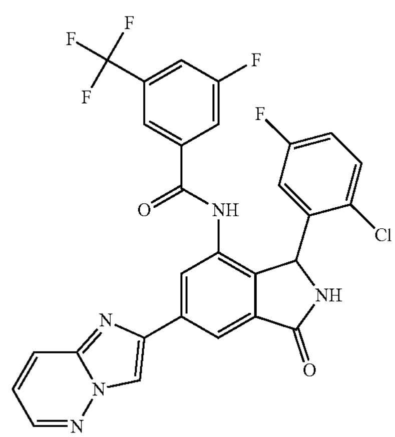 [SMILES: O=C(Nc1cc(-c2cn3ncccc3n2)cc2c1C(c1cc(F)ccc1Cl)NC2=O)c1cc(F)cc(C(F)(F)F)c1] | Fc1ccc(C1)c(c1)C1NC(=O)c2cc(cc(NC(=O)c3cc(F)cc(c3)C(F)(F)F)c12)-c1cn2nccc2n1 | NMR (400 MHz, DMSO-d6) 10.65 (br. s, 1H), 9.22 (br. s, 1H), 9.11 (s, 1H), 8.54 (dd, 4.5, 1.6 Hz, 1H), 8.37 (s, 1H), 8.25 (d, 0.8 Hz, 1H), 8.17 (ddd, 9.6, 1.2, 0.8 Hz, 1H), 7.97 (br. d, 8.3 Hz, 1H), 7.79 (br. d, 9.6 Hz, 1H), 7.72 (s, 1H), 7.33 (dd, 8.9, 5.2 Hz, 1H), 7.28 (dd, 9.2, 4.5 Hz, 1H), 7.10 (td, 8.6, 3.0 Hz, 1H), 6.68 (br. s, 1H), 6.03 (br. s, 1H) | 584.3 | A | |
| I-1307 | 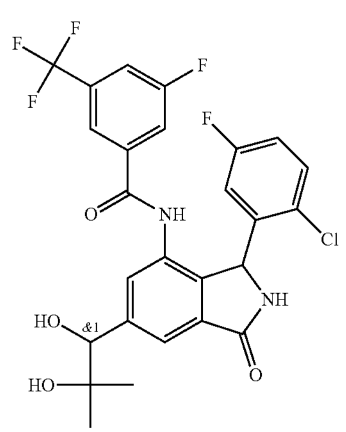 [SMILES: CC(C)(O)C(O)c1cc(NC(=O)c2cc(F)cc(C(F)(F)F)c2)c2c(c1)C(=O)NC2c1cc(F)ccc1Cl] | CC(C)(O)C(O)c1cc2C(=O)NC(c2c(NC(=O)c2cc(F)cc(c2)C(F)(F)F)c1)c1cc(F)ccc1Cl | NMR (400 MHz, DMSO d6) 10.50 (br. s, 1H), 9.09 (br. s, 1H), 7.94 (br. d, 8.2 Hz, 1H), 7.73 (br. d, 7.6 Hz, 1H), 7.70 (s, 1H), 7.64 (s,1H), 7.46 (s, 1H), 7.32-7.28 (m, 1H), 7.09 (td, 8.4, 3.0 Hz, 1H), 6.50 (br s, 1H), 5.97 (br s, 1H), 5.54 (d, 4.5 Hz, 1H), 4.45-4.44 (m, 2H), 1.15 (s, 3H), 0.97 (s, 3H) | 555.3 | B | |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-1308 | 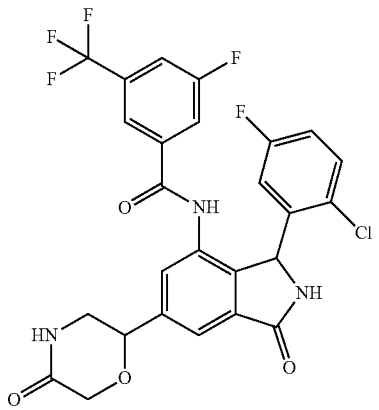 [SMILES: O=C1COC(c2cc(NC(=O)c3cc(F)cc(C(F)(F)F)c3)c3c(c2)C(=O)NC3c2cc(F)ccc2Cl)CN1] | Fc1ccc(C1)c(c1)C1NC(=O)c2cc(cc(NC(=O)c3cc(F)cc(c3)C(F)(F)F)c12)C1CNC(=O)CO1 | NMR (400 MHz, MeOD) 8.54 (s, 1H), 7.90 (d, 3.7 Hz, 1H), 7.73-7.59 (m, 4H), 7.28 (dd, 8.9, 5.1 Hz, 1H), 7.03-6.96 (m, 1H), 6.57 (br s, 1H) 6.19 (br s, 1H), 5.08-5.00 (m, 1H), 4.40 (s, 2H), 3.68-3.62 (m, 1H), 3.52-3.42 (m, 1H). | 566.1 | A | |
| I-1309 | 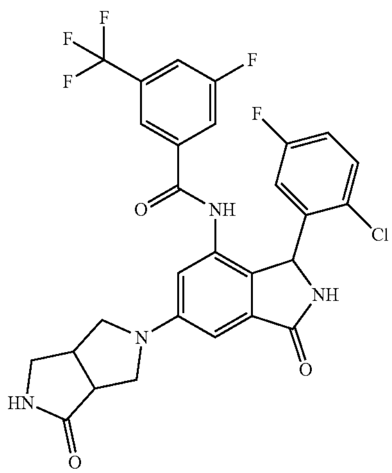 [SMILES: O=C(Nc1cc(N2CC3CNC(=O)C3C2)cc2c1C(c1cc(F)ccc1Cl)NC2=O)c1cc(F)cc(C(F)(F)F)c1] | Fc1ccc(C1)c(c1)C1NC(=O)c2cc(cc(NC(=O)c3cc(F)cc(c3)C(F)(F)F)c12)N1CC2CNC(=O)C2C1 | NMR (400 MHz, CD3CN) 8.53 (br. s, 1H), 7.64 (d, 8.3 Hz, 1H), 7.58 (d, 8.3 Hz, 1H), 7.57 (s, 1H), 7.26-7.21(m, 1H), 7.11 (br. s, 1H), 6.98-6.90 (m, 2H), 6.81 (s, 1H), 6.62 (br. s, 1H), 6.09 (s, 1H), 6.01 (br. s, 1H), 3.68-3.61 (m, 2H), 3.58 (dd, 9.9, 6.6 Hz, 1H), 3.45 (t, 7.8 Hz, 1H), 3.32-3.17 (m, 3H), 3.08 (t, 7.7 Hz, 1H) | 591.3 | A | |
| I-1310 | 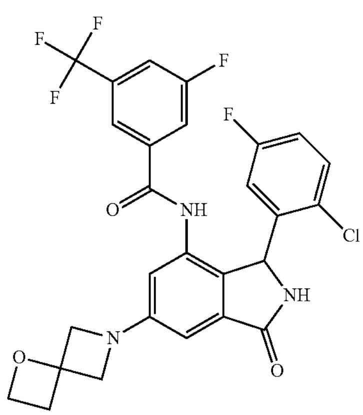 [SMILES: O=C(Nc1cc(N2CC3(CCO3)C2)cc2c1C(c1cc(F)ccc1Cl)NC2=O)c1cc(F)cc(C(F)(F)F)c1] | Fc1ccc(C1)c(c1)C1NC(=O)c2cc(cc(NC(=O)c3cc(F)cc(c3)C(F)(F)F)c12)N1CC2(CCO2)C1 | NMR (400 MHz, DMSO-d6) 10.40 (s, 1H), 9.01 (br. s, 1H), 7.93 (br. d, 8.3 Hz, 1H), 7.71 (br. d, 8.6 Hz, 1H), 7.64 (s, 1H), 7.29 (dd, 8.8, 5.1 Hz, 1H), 7.06 (td, 8.5, 3.0 Hz, 1H), 6.69 (d, 1.6 Hz, 1H), 6.55 (submerged br. s, 1H), 6.53 (s, 1H), 5.86 (br. s, 1H), 4.46 (t, 7.4 Hz, 2H), 4.18 (dd, 14.8, 9.0 Hz, 2), 3.96 (dd, 15.1, 8.9 Hz, 2H), 2.90 (t, 7.5 Hz, 2H). | 564.3 | B | |

TABLE 2-continued

Representative Compounds of the Invention with Bioactivity Data.

| Ex. No. | Structure | SMILES | $^1$H NMR | MS | ADP-Glo IC$_{50}$ | MCF 10A IC$_{50}$ |
|---|---|---|---|---|---|---|
| I-1311 | 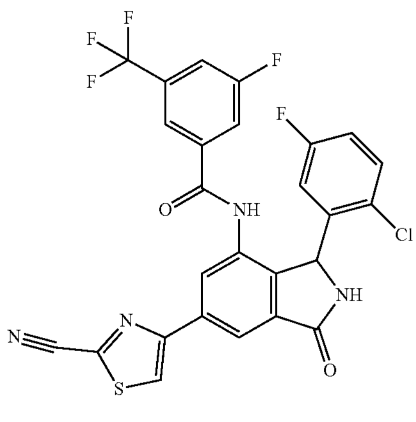 [SMILES: N#Cc1nc(-c2cc(NC(=O)c3cc(F)cc(C(F)(F)F)c3)c3c(c2)C(=O)NC3c2cc(F)ccc2Cl)cs1] | Fc1ccc(C1)c(c1)C1NC(=O)c2cc(cc(NC(=O)c3cc(F)cc(c3)C(F)(F)F)c12)-c1csc(n1)C#N | NMR (400 MHz, CDC3CN/DMSO-d6) 10.27 (br s, 1H), 8.59 (br s, 1H), 8.53 (s, 1H), 8.28 (s, 1H), 8.19 (s, 1H), 7.69-7.77 (m, 2H), 7.67 (br d, 1H), 7.24 (dd, 8.6, 5.3 Hz, 1H), 6.95 (td, 7.9, 3.1 Hz, 1H), 6.66 (br s, 1H), 6.16 (br s, 1H). | 575 | A | |
| I-1312 | 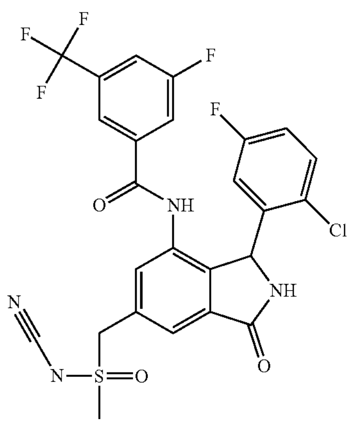 | CS(=O)(Cc1cc2C(=O)NC(c2c(NC(=O)c2cc(F)cc(c2)C(F)(F)F)c1c1cc(F)ccc1C1)=NC#N | NMR (400 MHz, DMSO-d6) 10.68 (br. s, 1H), 9.29 ( s, 1H), 7.95 (br. d, 8.3 Hz, 1H), 7.84 (s, 1H), 7.73 (br. d, 8.9 Hz, 1H), 7.63 (s, 1H), 7.58 (s, 1H), 7.32 (dd, 8.9, 5.2 Hz, 1H), 7.10 (td, 8.4, 2.9 Hz, 1H), 6.65 (br. s, 1H), 6.03 (br. s, 1H), 5.29-5.18 (m, 2H), 3.45 (s, 3H). | 583.1 | A | |
| I-1313 | 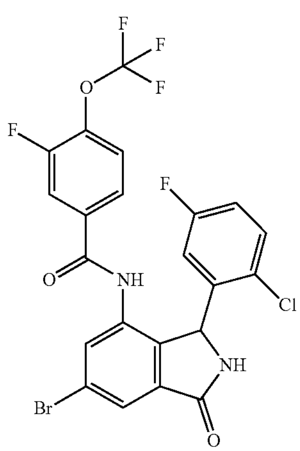 [SMILES: O=C(Nc1cc(Br)cc2c1C(c1cc(F)ccc1Cl)NC2=O)c1ccc(OC(F)(F)F)c(F)c1] | Fc1ccc(C1)c(c1)C1NC(=O)c2cc(Br)cc(NC(=O)c3ccc(OC(F)(F)F)c(F)c3)c12 | 1H NMR (400 MHz, DMSO-d6) 10.41 (s, 1H), 9.27 (s, 1H), 7.81 (d, 1.7 Hz, 1H), 7.75-7.67 (m, 2H), 7.62 (dd, 11.0, 2.1 Hz, 1H), 7.54 (dd, 8.3, 2.0 Hz, 1H), 7.35 (dd, 8.9, 5.2 Hz, 1H), 7.12 (td, 8.4, 3.1 Hz, 1H), 6.75 (s, 1H), 5.97 (s, 1H). | 560.8 | D | |

TABLE 2-continued

Representative Compounds of the Invention with Bioactivity Data.

| Ex. No. | Structure | SMILES | $^1$H NMR | MS | ADP-Glo IC$_{50}$ | MCF 10A IC$_{50}$ |
|---|---|---|---|---|---|---|
| I-1314 | 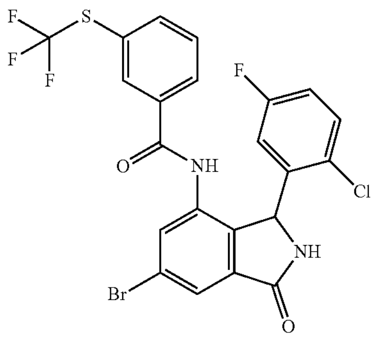 [SMILES: O=C(Nc1cc(Br)cc2c1C(c1cc(F)ccc1Cl)NC2=O)c1cccc(SC(F)(F)F)c1] | Fc1ccc(C1)c(c1)C1NC(=O)c2cc(Br)cc(NC(=O)c3cccc(SC(F)(F)F)c3)c12 | 1H NMR (400 MHz, DMSO-d6) 10.44 (s, 1H), 9.27 (s, 1H), 7.91 (d, 7.6 Hz, 1H), 7.86-7.77 (m, 3H), 7.74 (d, 1.8 Hz, 1H), 7.63 (t, 7.8 Hz, 1H), 7.31 (dd, 8.9, 5.2 Hz, 1H), 7.09 (td, 8.4, 3.1 Hz, 1H), 6.69 (s, 1H), 6.01 (s, 1H). | 558.95 | D | |
| I-1315 | 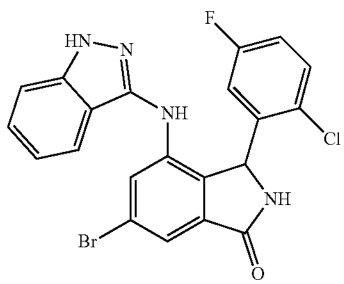 [SMILES: O=C1NC(c2cc(F)ccc2Cl)c2c(Nc3n[nH]c4ccccc34)cc(Br)cc21] | Fc1ccc(C1)c(c1)C1NC(=O)c2cc(Br)cc(Nc3n[nH]c4cccc34)c12 | 1H NMR (400 MHz, DMSO-d6) 12.28 (s, 1H), 9.13 (s, 1H), 8.18 (s, 1H), 8.08-8.03 (m, 1H), 7.42-7.35 (m, 2H), 7.31 (ddt, 7.7, 4.7, 2.1 Hz, 3H), 7.14-7.02 (m, 1H), 6.97 (ddd, 7.9, 6.8, 0.9 Hz, 1H), 6.79 (s, 1H), 6.08 (s, 1H). | 471 | E | |
| I-1316 | 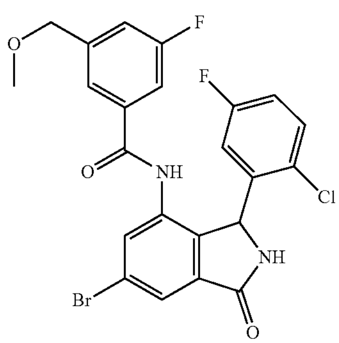 [SMILES: COCc1cc(F)cc(C(=O)Nc2cc(Br)cc3c2C(c2cc(F)ccc2Cl)NC3=O)c1] | COCc1cc(F)cc(c1)C(=O)Nc1cc(Br)cc2C(=O)NC(c12)c1cc(F)ccc1Cl | 1H NMR (400 MHz, DMSO-d6) 10.34 (s, 1H), 9.27 (s, 1H), 7.80 (s, 1H), 7.74 (s, 1H), 7.40-7.31 (m, 3H), 7.23 (d, 9.4 Hz, 1H), 7.14 (td, 8.4, 3.0 Hz, 1H), 6.66 (s, 1H), 6.00 (s, 1H), 4.44 (s, 2H), 3.29-3.32 (m, 3H) | 521 | D | |
| I-1317 | 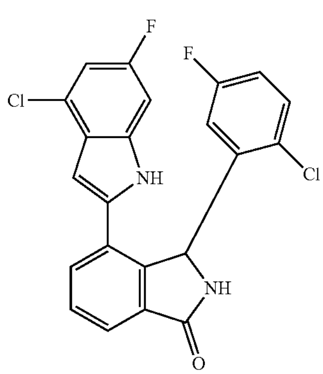 [SMILES: O=C1NC(c2cc(F)ccc2Cl)c2c1cccc2-c1cc2c(Cl)cc(F)cc2[nH]1] | Fc1ccc(C1)c(c1)C1NC(=O)c2cccc(-c3cc4c(C1)cc(F)cc4[nH]3)c12 | 1H NMR (400 MHz, DMSO-d6) 11.85 (s, 1H), 9.28 (s, 1H), 7.90 (d, 7.4 Hz, 1H), 7.82 (dd, 7.6, 1.2 Hz, 1H), 7.75 (t, 7.5 Hz, 1H), 7.31 (s, 1H), 7.09 (ddd, 9.4, 2.2, 0.9 Hz, 1H), 7.05-6.95 (m, 2H), 6.56-6.50 (m, 2H), 6.35 (s, 1H). | 428.95 | B | |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-1318 | 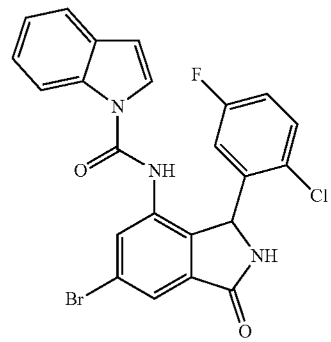 [SMILES: O=C1NC(c2cc(F)ccc2Cl)c2c(NC(=O)n3ccc4ccccc43)cc(Br)cc21] | Fc1ccc(C1)c(c1)C1NC(=O)c2cc(Br)cc(NC(=O)n3ccc4ccccc34)c12 | 1H NMR (400 MHz, DMSO-d6) 10.07 (s, 1H), 9.30 (s, 1H), 8.02 (d, 8.1 Hz, 1H), 7.82 (m, 2H), 7.76 (s, 1H), 7.59 (d, 7.6 Hz, 1H), 7.38-7.06 (m, 5H), 6.65 (d, 3.7 Hz, 1H), 6.05 (s, 1H). | 499.9 | A | |
| I-1319 | 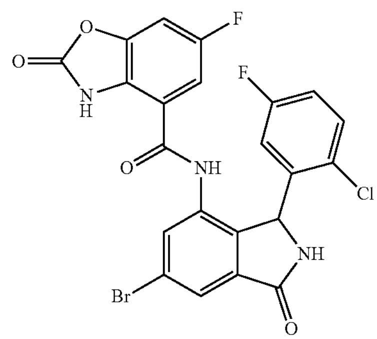 | Fc1ccc(C1)c(c1)C1NC(=O)c2cc(Br)cc(NC(=O)c3cc(F)cc4oc(=O)[nH]c34)c12 | 1H NMR (400 MHz, DMSO-d6) 11.85 (s, 1H), 10.40 (s, 1H), 9.27 (s, 1H), 8.52-7.59 (m, 3H), 7.30 (s, 1H), 7.10-6.90 (m, 3H), 5.98 (s, 1H). | 535.95 | D | |
| I-1320 | 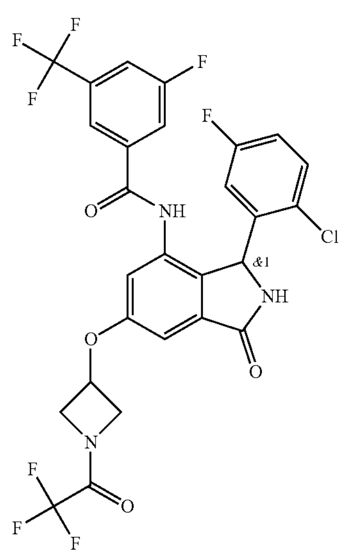 [SMILES: O=C(Nc1cc(OC2CN(C(=O)C(F)(F)F)C2)cc2c1C(c1cc(F)ccc1Cl)NC2=O)c1cc(F)cc(C(F)(F)F)c1] | Fc1ccc(C1)c(c1)C1NC(=O)c2cc(OC3CN(C3)C(=O)C(F)(F)F)cc(NC(=O)c3cc(F)cc(c3)C(F)(F)F)c12 | (400 MHz, DMSO-d6) 10.48 (s, 1H), 9.20 (br s, 1H), 7.96 (d, 8.5 Hz, 1H), 7.71 (d, 8.9 Hz, 1H), 7.61 (s, 1H), 7.32 (dd, 8.9, 5.2 Hz, 1H), 7.12-7.06 (m, 2H), 7.06-7.01 (m, 1H), 6.56 (br s, 1H), 5.94 (br s, 1H), 5.33-5.24 (m, 1H), 5.00-4.90 (m, 1H), 4.62 (dd, 11.3, 6.7 Hz, 1H), 4.52-4.41 (m, 1H), 4.19-4.10 (m, 1H). | 634.2 | B | |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-1321 | 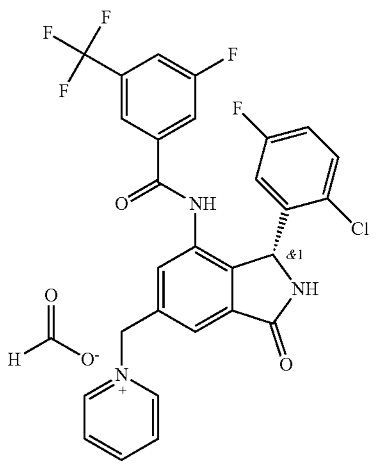 | Fc1ccc(C1)c(c1)CNC(=O)c2cc(C[n+]3ccccc3)cc(NC(=O)c3cc(F)cc(c3)C(F)(F)F)c12 | (400 MHz, CD3CN) 8.95 (d, 6.0 Hz, 2H), 8.52 (t, 7.8 Hz, 1H), 8.39 (s, 2H), 8.05 (t, 6.9 Hz, 2H), 7.85 (s, 1H), 7.80 (s, 1H), 7.76-7.70 (m, 2H), 7.60 (d, 8.4 Hz, 1H), 7.55 (s, 1H), 7.20 (dd, 8.8, 5.1 Hz, 1H), 6.91 (td, 8.4, 2.9 Hz, 1H), 6.67 (br s, 1H), 6.19 (s, 1H), 5.86 (s, 2H). | 558.3 | A | |
| I-1322 | 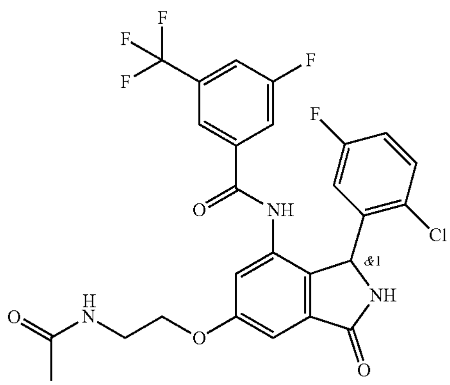 | CC(=O)NCCOc1cc2C(=O)NC(c2c(NC(=O)c2cc(F)cc(c2)C(F)(F)F)c1)c1cc(F)ccc1Cl | (400 MHz, DMSO-d6) 10.47 (s, 1H), 9.14 (s, 1H), 8.16 (t, 5.2 Hz, 1H), 7.95 (d, 8.1 Hz, 1H), 7.71 (d, 8.7 Hz, 1H), 7.63 (s, 1H), 7.31 (dd, 8.8, 5.1 Hz, 1H), 7.20 (s, 1H), 7.08 (d, 8.3 Hz, 2H), 6.54 (br s, 1H), 5.92 (br s, 1H), 4.18-4.04 (m, 2H), 3.45 (dd, 11.0, 5.6 Hz, 2H), 1.83 (s, 3H). | 568.1 | B | |
| I-1323 | 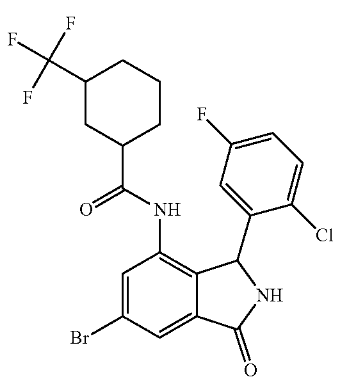 [SMILES: O=C1NC(c2cc(F)ccc2Cl)c2c(NC(=O)C3CCCC(C(F)(F)F)C3)cc(Br)cc21] | Fc1ccc(C1)c(c1)CNC(=O)c2cc(Br)cc(NC(=O)C3CCCC(C3)C(F)(F)F)c12 | 1H-NMR (400 MHz, DMSO-d6) as a ca. 1:1 mixture of diastereomers-' 9.98 (br. s, 1H), 9.91 (br. s, 1H), 9.26 (br. s, 2H), 7.72-7.69 (m, 2H), 7.61 (d, 1.7 Hz, 1H), 7.58 (d, 1.7 Hz, 1H), 7.53-7.41 (m, 2H), 7.25-7.17 (m, 2H), 6.54 (br. s, 2H), 6.01 (br. s, 2H), 2.30-2.20 (m, 2H), 2.19-2.09 (m, 2H), 1.81-1.68 (m, 4H), 1.58 (d, 12.8 Hz, 1H), 1.50 (d, 12.8 Hz, 1H), 1.42-1.31 (m, 2H), 1.27-1.16 (m, 2H), 1.13-0.93 (m, 6H). | 533.2 | B | |

TABLE 2-continued

Representative Compounds of the Invention with Bioactivity Data.

| Ex. No. | Structure | SMILES | $^1$H NMR | MS | ADP-Glo IC$_{50}$ | MCF 10A IC$_{50}$ |
|---|---|---|---|---|---|---|
| I-1324 | 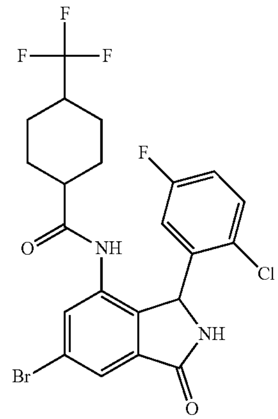 [SMILES: O=C1NC(c2cc(F)ccc2Cl)c2c(NC(=O)C3CCC(C(F)(F)F)CC3)cc(Br)cc21] | Fc1ccc(C1)c(c1)C1NC(=O)c2cc(Br)cc(NC(=O)C3CCC(CC3)C(F)(F)F)c12 | 1H-NMR (400 MHz, DMSO-d6) 9.78 (br. s, 1H), 9.26 (br. s, 1H), 7.75 (d, 1.6 Hz, 1H), 7.69 (d, 1.6 Hz, 1H), 7.53-7.45 (m, 1H), 7.23 (app. td, 8.4, 3.1 Hz, 1H), 6.52 (br. s, 1H), 6.08 (br. s, 1H), 2.38-2.34 (m, 1H), 2.24-2.12 (m, 1H), 1.66-1.58 (m, 1H), 1.57-1.31 (m, 5H), 1.29-1.14 (m, 2H). | 533.2 | D | |
| I-1325 | 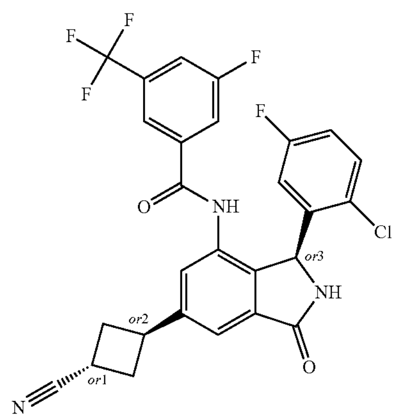 [SMILES: N#C[C@H]1C[C@H](c2cc(NC(=O)c3cc(F)cc(C(F)(F)F)c3)c3c(c2)C(=O)N[C@@H]3c2cc(F)ccc2Cl)C1] | Fc1ccc(C1)c(c1)[C@H]1NC(=O)c2cc(cc(NC(=O)c3cc(F)cc(c3)C(F)(F)F)c12)[C@H]1c[C@@H](C1)C#N | NMR (400 MHz, CD3CN) 8.64 (s, 1H), 7.68-7.56 (m, 4H), 7.42 (d, 6.9 Hz,1H), 7.30-7.22 (m, 2H), 7.02-6.92 (m,1H), 6.60 (br, s, 1H), 6.09 (br, s, 1H), 3.78-3.67 (m,1H), 3.31-3.19 (m,1H), 2.88-2.80 (m,1H), 2.78-2.70 (m,1H), 2.69-2.59 (m,1H), 2.56-2.44 (m,1H) | 546 | B | |
| I-1326 | 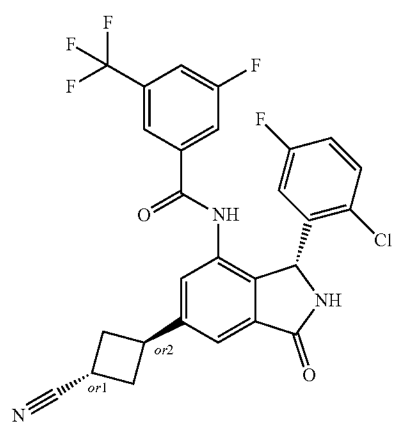 [SMILES: N#C[C@H]1C[C@H](c2cc(NC(=O)c3cc(F)cc(C(F)(F)F)c3)c3c(c2)C(=O)N[C@H]3c2cc(F)ccc2Cl)C1] | Fc1ccc(C1)c(c1)[C@@H]1NC(=O)c2cc(cc(NC(=O)c3cc(F)cc(c3)C(F)(F)F)c12)[C@H]1C[C@@H](C1)C#N | NMR (400 MHz, CD3CN) 8.64 (s,1H), 7.68-7.56 (m, 4H), 7.42 (d, 6.9 Hz,1H), 7.30-7.22 (m, 2H), 7.02-6.92 (m,1H), 6.60 (br, s,1H), 6.09 (br, s, 1H), 3.78-3.67 (m,1H), 3.31-3.19 (m,1H), 2.88-2.80 (m,1H), 2.78-2.70 (m,1H), 2.69-2.59 (m,1H), 2.56-2.44 (m,1H) | 546 | A | |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-1327 | 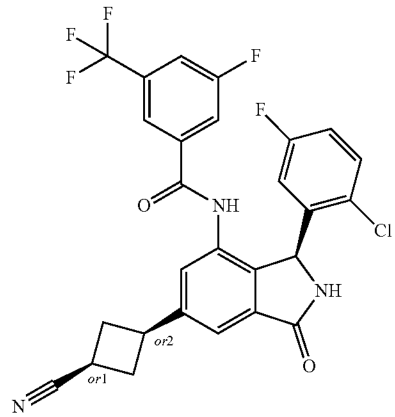 [SMILES: N#C[C@H]1C[C@@H](c2cc(NC(=O)c3cc(F)cc(C(F)(F)F)c3)c3c(c2)C(=O)N[C@@H]3c2cc(F)ccc2Cl)C1] | Fc1ccc(C1)c(c1)[C@H]1NC(=O)c2cc(cc(NC(=O)c3cc(F)cc(c3)C(F)(F)F)c12)[C@@H]1C[C@@H](C1)C#N | NMR (400 MHz, CD3CN) 8.64 (s,1H), 7.68-7.56 (m, 4H), 7.42 (d, 6.9 Hz,1H), 7.30-7.22 (m, 2H), 7.02-6.92 (m,1H), 6.60 (br, s, 1H), 6.09 (br, s, 1H), 3.78-3.67 (m,1H), 3.31-3.19 (m,1H), 2.88-2.80 (m,1H), 2.78-2.70 (m,1H), 2.69-2.59 (m,1H), 2.56-2.44 (m,1H) | 546 | A | |
| I-1328 | 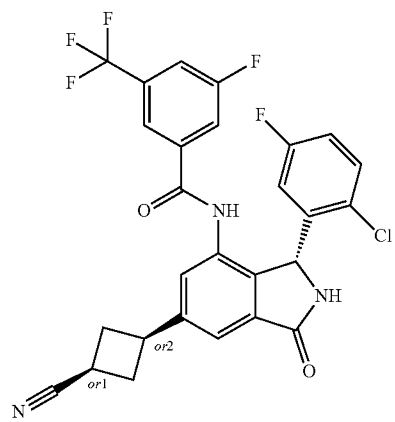 [SMILES: N#C[C@H]1C[C@@H](c2cc(NC(=O)c3cc(F)cc(C(F)(F)F)c3)c3c(c2)C(=O)N[C@H]3c2cc(F)ccc2Cl)C1] | Fc1ccc(C1)c(c1)[C@@H]1NC(=O)c2cc(cc(NC(=O)c3cc(F)cc(c3)C(F)(F)F)c12)[C@@H]1C[C@@H](C1)C#N | NMR (400 MHz, CD3CN) 8.64 (s,1H), 7.68-7.56 (m, 4H), 7.42 (d, 6.9 Hz,1H), 7.30-7.22 (m, 2H), 7.02-6.92 (m,1H), 6.60 (br, s, 1H), 6.09 (br, s, 1H), 3.78-3.67 (m,1H), 3.31-3.19 (m,1H), 2.88-2.80 (m,1H), 2.78-2.70 (m,1H), 2.69-2.59 (m,1H), 2.56-2.44 (m,1H) | 546 | B | |
| I-1329 | 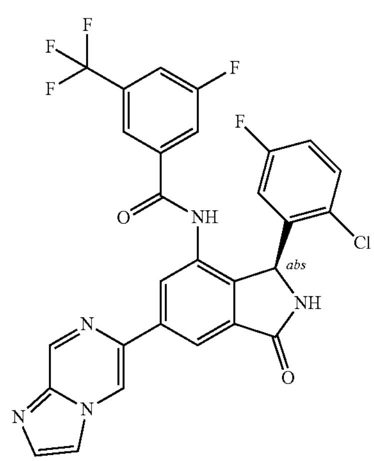 [SMILES: O=C(Nc1cc(-c2cn3ccnc3cn2)cc2c1[C@@H](c1cc(F)ccc1Cl)NC2=O)c1cc(F)cc(C(F)(F)F)c1] | Fc1ccc(C1)c(c1)[C@H]1NC(=O)c2cc(cc(NC(=O)c3cc(F)cc(c3)C(F)(F)F)c12)-c1cn2ccnc2cn1 | | 584.2 | D | |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-1330 | 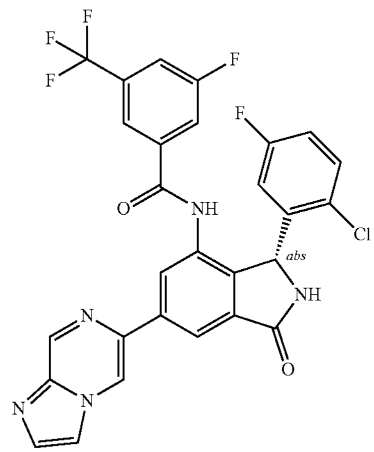 [SMILES: O=C(Nc1cc(-c2cn3ccnc3cn2)cc2c1[C@H](c1cc(F)ccc1Cl)NC2=O)c1cc(F)cc(C(F)(F)F)c1] | Fc1ccc(C1)c(c1)[C@@H]1NC(=O)c2cc(cc(NC(=O)c3cc(F)cc(c3)C(F)(F)F)c12)-c1cn2ccnc2cn1 | | 584.2 | A | |
| I-1331 | 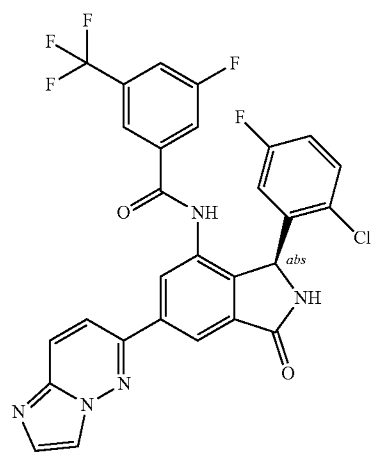 [SMILES: O=C(Nc1cc(-c2ccc3nccn3n2)cc2c1[C@@H](c1cc(F)ccc1Cl)NC2=O)c1cc(F)cc(C(F)(F)F)c1] | Fc1ccc(C1)c(c1)[C@H]1NC(=O)c2cc(cc(NC(=O)c3cc(F)cc(c3)C(F)(F)F)c12)-c1ccc2nccn2n1 | | 584.2 | D | |
| I-1332 | 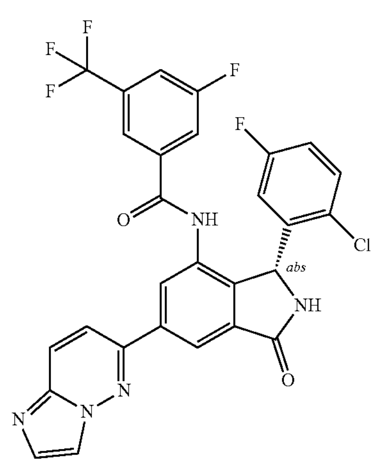 [SMILES: O=C(Nc1cc(-c2ccc3nccn3n2)cc2c1[C@H](c1cc(F)ccc1Cl)NC2=O)c1cc(F)cc(C(F)(F)F)c1] | Fc1ccc(C1)c(c1)[C@@H]1NC(=O)c2cc(cc(NC(=O)c3cc(F)cc(c3)C(F)(F)F)c12)-c1ccc2nccn2n1 | | 584.2 | A | |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-1333 | 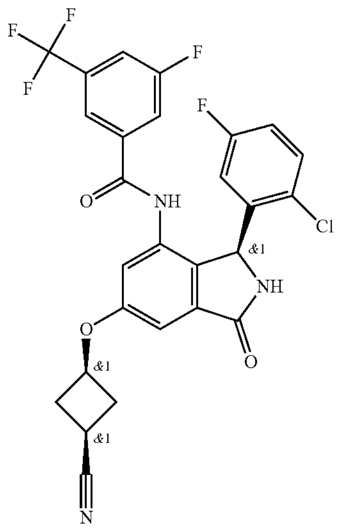 [SMILES: N#C[C@H]1C[C@@H](Oc2cc(NC(=O)c3cc(F)cc(C(F)(F)F)c3)c3c(c2)C(=O)N[C@@H]3c2cc(F)ccc2Cl)C1] | Fc1ccc(C1)c(c1)[C@H]1NC(=O)c2cc(O[C@H]3C[C@H](C3)C#N)cc(NC(=O)c3cc(F)cc(c3)C(F)(F)F)c12 | | 561 | D | |
| I-1334 | 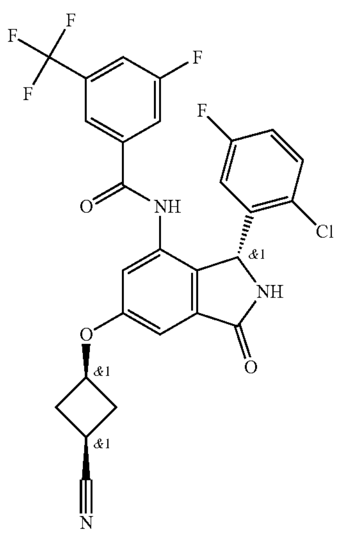 [SMILES: N#C[C@H]1C[C@@H](Oc2cc(NC(=O)c3cc(F)cc(C(F)(F)F)c3)c3c(c2)C(=O)N[C@H]3c2cc(F)ccc2Cl)C1] | Fc1ccc(C1)c(c1)[C@@H]1NC(=O)c2cc(O[C@H]3C[C@H](C3)C#N)cc(NC(=O)c3cc(F)cc(c3)C(F)(F)F)c12 | | 561 | A | |
| I-1335 | 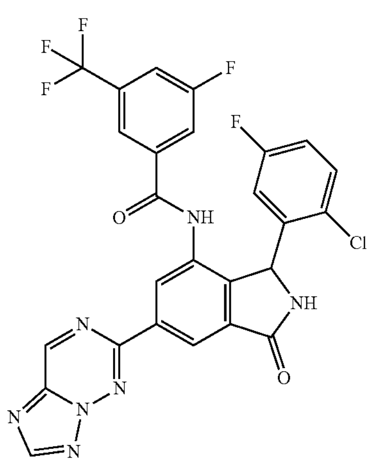 [SMILES: O=C(Nc1cc(-c2ncc3ncnn3n2)cc2c1C(c1cc(F)ccc1Cl)NC2=O)c1cc(F)cc(C(F)(F)F)c1] | Fc1ccc(C1)c(c1)C1NC(=O)c2cc(cc(NC(=O)c3cc(F)cc(c3)C(F)(F)F)c12)-c1cn2ncnc2cn1 | | 585.5 | A | |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-1336 | 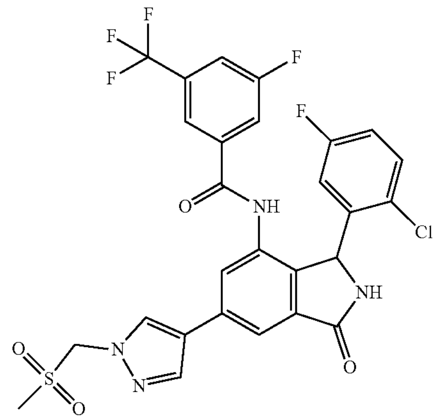 [SMILES: CS(=O)(=O)Cn1cc(-c2cc(NC(=O)c3cc(F)cc(C(F)(F)F)c3)c3c(c2)C(=O)NC3c2cc(F)ccc2Cl)cn1] | CS(=O)(=O)Cn1cc(cn1)-c1cc2C(=O)NC(c2c(NC(=O)c2cc(F)cc(c2)C(F)(F)F)c1)c1cc(F)ccc1Cl | 1H NMR (500 MHz, DMSO-d6) 3.06 (s, 3 H) 5.77 (d, 0.92 Hz, 2 H) 5.89-6.10 (m, 1 H) 7.08 (td, 8.35, 2.98 Hz, 1 H) 7.31 (dd, 8.85, 5.19 Hz., 1 H) 7.69 (s, 1 H) 7.71-7.78 (m, 2 H) 7.94 (br s, 2 H) 8.27 (s, 1 H) 8.47 (s, 1 H) 9.14 (br s, 1 H) 10.53 (s, 1 H) | 625.24 | A | |
| I-1337 | 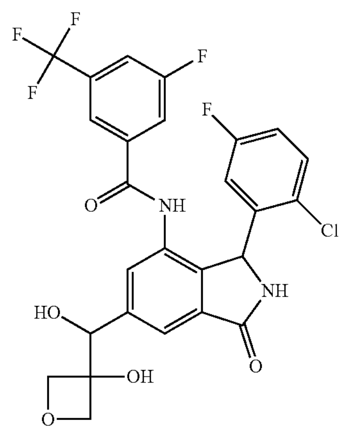 [SMILES: O=C(Nc1cc(C(O)C2(O)COC2)cc2c1C(c1cc(F)ccc1Cl)NC2=O)c1cc(F)cc(C(F)(F)F)c1] | OC(c1cc2C(=O)NC(c2c(NC(=O)c2cc(F)cc(c2)C(F)(F)F)c1)c1cc(F)ccc1Cl)C1(O)COC1 | | 569.22 | B | |
| I-1338 | 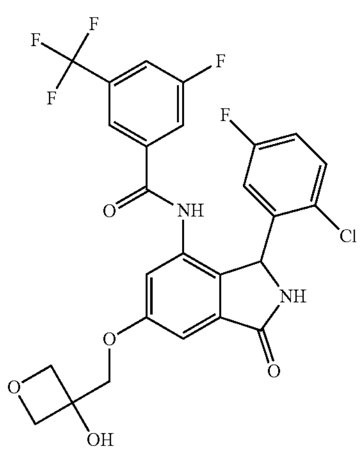 [SMILES: O=C(Nc1cc(OCC2(O)COC2)cc2c1C(c1cc(F)ccc1Cl)NC2=O)c1cc(F)cc(C(F)(F)F)c1] | OC1(COc2cc3C(=O)NC(c3c(NC(=O)c3cc(F)cc(c3)C(F)(F)F)c2)c2cc(F)ccc2Cl)COC1 | | 569.17 | B | |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-1339 | 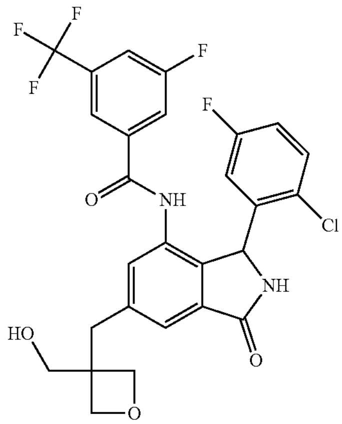 [SMILES: O=C(Nc1cc(CC2(CO)COC2)cc2c1C(c1cc(F)ccc1Cl)NC2=O)c1cc(F)cc(C(F)(F)F)c1] | OCC1(Cc2cc3C(=O)NC(c3c(NC(=O)c3cc(F)cc(c3)C(F)(F)F)c2)cc(F)ccc2Cl)COC1 | 1H NMR (500 MHz, DMSO) 10.45 (s, 1H), 9.08 (s, 1H), 7.92 (dt, 8.6, 2.1 Hz, 1H), 7.72 (d, 9.1 Hz, 1H), 7.64 (s, 1H), 7.54 (d, 1.5 Hz, 1H), 7.35-7.25 (m, 2H), 7.12-6.98 (m, 1H), 6.59 (s, 1H), 5.93 (s, 1H), 5.02 (s, 1H), 4.45 (dd, 12.2, 5.8 Hz, 2H), 4.28 (dd, 20.6, 5.8 Hz, 2H), 3.52 (d, 10.9 Hz, 1H), 3.47 (d, 11.0 Hz, 1H), 3.13 (d, 13.4 Hz, 1H), 3.06 (d, 13.4 Hz, 1H). | 567.22 | A | |
| I-1340 | 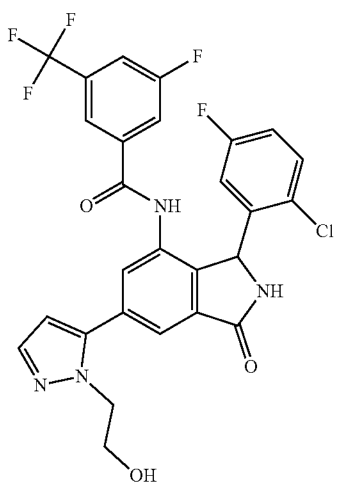 [SMILES: O=C(Nc1cc(-c2ccnn2CCO)cc2c1C(c1cc(F)ccc1Cl)NC2=O)c1cc(F)cc(C(F)(F)F)c1] | OCCn1nccc1-c1cc2C(=O)NC(c2c(NC(=O)c2cc(F)cc(c2)C(F)(F)F)c1)cc1cc(F)ccc1Cl | | 577.22 | A | |
| I-1341 | 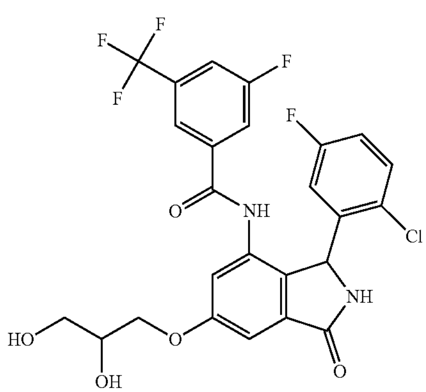 [SMILES: O=C(Nc1cc(OCC(O)CO)cc2c1C(c1cc(F)ccc1Cl)NC2=O)c1cc(F)cc(C(F)(F)F)c1] | OCC(O)COc1cc2C(=O)NC(c2c(NC(=O)c2cc(F)cc(c2)C(F)(F)F)c1)cc1cc(F)ccc1Cl | NMR (400 MHz, DSMO-d6) 10.50 (br s, 1H), 9.17 (s, 1H), 7.95 (d, 9.2 Hz, 1H), 7.71 (d, 8.8 Hz, 1H), 7.63 (s, 1H), 7.31 (dd, 8.8, 5.2 Hz, 1H), 7.19 (d, 1.9 Hz, 1H), 7.13-7.04 (m, 2H), 6.49 (br s, 1H), 5.97 (br s, 1H), 5.05 (d, 5.1 Hz, 1H), 4.74 (t, 5.4 Hz, 1H), 4.13 (td, 9.5, 3.9 Hz, 1H), 4.06-3.90 (m, 1H), 3.90-3.75 (m, 1H), 3.47 (t, 5.5 Hz, 2H). | 557.2 | A | |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-1342 | 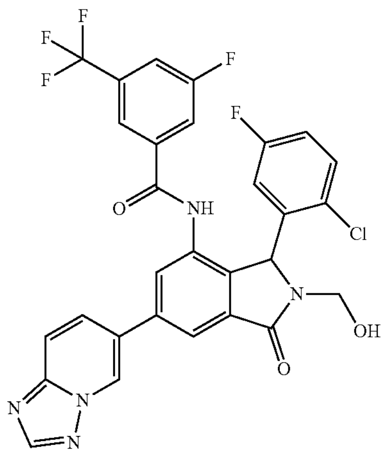 [SMILES: O=C(Nc1cc(-c2ccc3ncnn3c2)cc2c1C(c1cc(F)ccc1Cl)N(CO)C2=O)c1cc(F)cc(C(F)(F)F)c1] | OCN1C(c2c(cc(cc2NC(=O)c2cc(F)cc(c2)C(F)(F)F)-c2ccc3ncnn3c2)C1=O)c1cc(F)ccc1Cl | (400 MHz, DMSO) 10.67 (d, 35.5 Hz, 1H), 9.50 (s, 1H), 8.58 (s, 1H), 8.30-8.11 (m, 2H), 8.07-7.91 (m, 3H), 7.89-7.74 (m, 2H), 7.42-7.27 (m, 1H), 7.19-7.07 (m, 1H), 6.47-6.37 (m, 1H), 6.18 (t, 7.0 Hz, 1H), 6.09-5.98 (m, 1H), 5.30-5.17 (m, 1H), 4.18-4.07 (m, 1H). | 614.4 | B | |
| I-1343 | 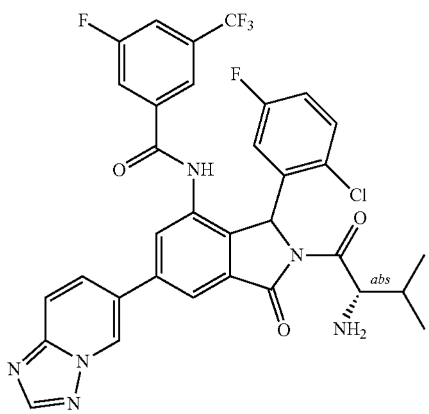 [SMILES: CC(C)[C@H](N)C(=O)N1C(=O)c2cc(-c3ccc4ncnn4c3)cc(NC(=O)c3cc(F)cc(C(F)(F)F)c3)c2C1c1cc(F)ccc1Cl] | CC(C)[C@H](N)C(=O)N1C(c2c(cc(cc2NC(=O)c2cc(F)cc(c2)C(F)(F)F)-c2ccc3ncnn3c2)C1=O)c1cc(F)ccc1Cl | (400 MHz, DMSO-d6, 60 °C.) 9.48-9.40 (m, 1H), 8.57-8.51 (m, 1H), 8.34-8.24 (m, 1H), 8.16-8.07 (m, 2H), 8.00-7.73 (m, 4H), 7.25 (dd, 8.9, 5.2 Hz, 1H), 7.10-7.00 (m, 1H), 6.63-6.41 (m, 1H), 6.14-6.02 (m, 1H), 4.54 (d, 3.7 Hz, 0.5H), 4.44 (d, 4.9 Hz, 0.5H), 2.14-1.93 (m, 1H), 1.01 (d, 6.7 Hz, 1.5H), 0.94 (d, 6.5 Hz, 1.5H), 0.85 (d, 6.6 Hz, 1.5H), 0.42 (br d, 5.5 Hz, 1.5H) | 683.4 | A | |
| I-1344 | 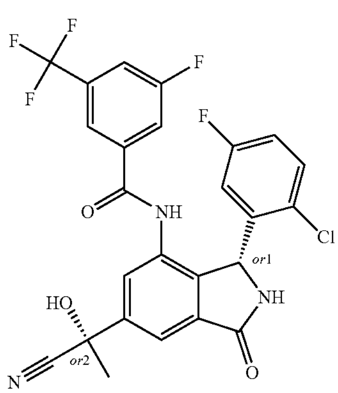 [SMILES: C[C@@](O)(C#N)c1cc(NC(=O)c2cc(F)cc(C(F)(F)F)c2)c2c(c1)C(=O)N[C@H]2c1cc(F)ccc1Cl] | C[C@@](O)(C#N)c1cc2C(=O)N[C@H](c2c(NC(=O)c2cc(F)cc(c2)C(F)(F)F)c1)c1cc(F)ccc1Cl | (400 MHz, DMSO-d6) 10.69 (br s, 1H), 9.10 (br s, 1H), 7.95-7.83 (m, 1H), 7.82-7.66 (m, 4H), 7.32 (dd, 8.8, 5.2 Hz, 1H), 7.09 (td, 8.4, 3.0 Hz, 1H), 6.52 (br s, 1H), 6.07 (br s, 1H), 5.95 (br s, 1H), 3.08 (s, 2H), 1.60 (s, 3H). | 550.3 | C | |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-1345 | 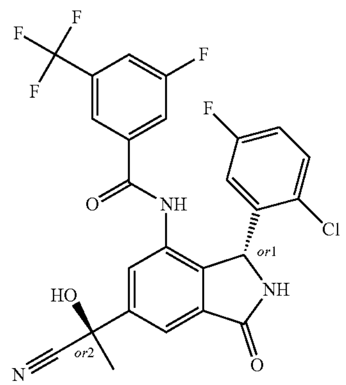 [SMILES: C[C@](O)(C#N)c1cc(NC(=O)c2cc(F)cc(C(F)(F)F)c2)c2c(c1)C(=O)N[C@H]2c1cc(F)ccc1Cl] | C[C@](O)(C#N)c1cc2C(=O)N[C@H](c2c(NC(=O)c2cc(F)cc(c2)C(F)(F)F)c1c c(F)ccc1Cl | (400 MHz, DMSO-d6) 10.66 (br s, 1H), 9.13 (br s, 1H), 8.02-7.88 (m, 1H), 7.88-7.80 (m, 1H), 7.76 (d, 9.1 Hz, 1H), 7.73-7.62 (m, 2H), 7.31 (dd, 8.9, 5.2 Hz, 1H), 7.09 (td, 8.4, 2.9 Hz, 1H), 6.52 (br s, 1H), 6.09 (s, 1H), 5.95 (br s, 1H), 3.09 (s, 2H), 1.60 (s, 3H) [ | 550.2 | A | |
| I-1346 | 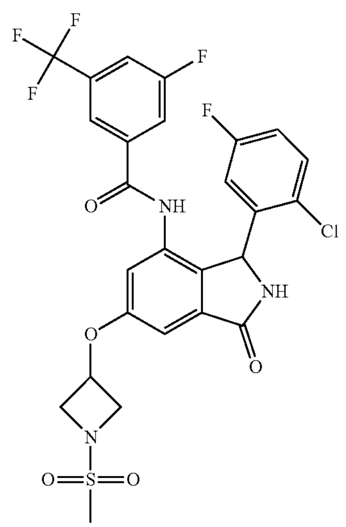 [SMILES: CS(=O)(=O)N1CC(Oc2cc(NC(=O)c3cc(F)cc(C(F)(F)F)c3)c3c(c2)C(=O)NC3c2cc(F)ccc2Cl)C1] | CS(=O)(=O)N1CC(C1)Oc1cc2C(=O)NC(c2c(NC(=O)c2cc(F)cc(c2)C(F)(F)F)c1c1cc(F)ccc1Cl | (400 MHz, ) 10.47 (s, 1H), 9.18 (br s, 1H), 7.95 (d, 7.8 Hz, 1H), 7.71 (d, 8.5 Hz, 1H), 7.62 (s, 1H), 7.31 (dd, 8.8, 5.2 Hz, 1H), 7.14-7.00 (m, 3H), 6.58 (br s, 1H), 5.94 (br s, 1H), 5.21 (p, 5.3 Hz, 1H), 4.37 (t, 6.6 Hz, 2H), 4.00 (td, 9.7, 4.6 Hz, 2H), 3.10 (s, 3H). | 616.3 | A | |
| I-1347 | 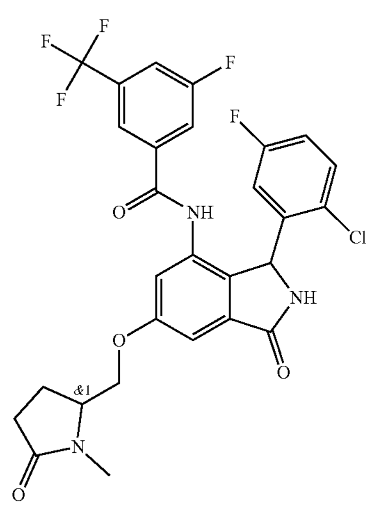 [SMILES: CN1C(=O)CCC1COc1cc(NC(=O)c2cc(F)cc(C(F)(F)F)c2)c2c(c1)C(=O)NC2c1cc(F)ccc1Cl] | CN1C(COc2cc3C(=O)NC(c3c(NC(=O)c3cc(F)cc(c3)C(F)(F)F)c2)c2cc(F)ccc2Cl)CCC1=O | 1H NMR (400 MHz, DMSO-d6) 10.44 (s, 1H), 9.14 (s, 1H), 7.95 (d, 8.3 Hz, 1H), 7.72 (d, 8.6 Hz, 1H), 7.64 (s, 1H), 7.31 (dd, 8.8, 5.1 Hz, 1H), 7.27 (s, 1H), 7.16-7.02 (m, 2H), 6.61 (br. s, 1H), 5.94 (br. s, 1H), 4.35-4.26 (m, 1H), 4.21-4.13 (m, 1H), 3.97-3.85 (m, 1H), 2.79 (s, 3H), 2.46-2.27 (m, 1H), 2.28-2.08 (m, 2H), 1.96-1.77 (m, 1H) | 594.2 | A | |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-1348 | 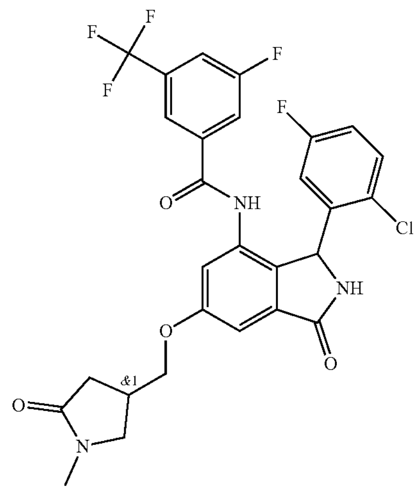 [SMILES: CN1CC(COc2cc(NC(=O)c3cc(F)cc(C(F)(F)F)c3)c3c(c2)C(=O)NC3c2cc(F)ccc2Cl)CC1=O] | CN1CC(COc2cc3C(=O)NC(c3c(NC(=O)c3cc(F)cc(c3)C(F)(F)F)c2)c2ccc(F)ccc2Cl)CC1=O | 1H NMR (400 MHz, DMSO-d6) mixture of diastereomers:-' 10.44 (br. s, 1H), 9.11 (br. s, 1H), 7.92 (br. d, 7.1 Hz, 1H), 7.71 (br. d, 8.9 Hz, 1H), 7.65 (s, 1H), 7.31 (dd, 8.9, 5.2 Hz, 1H), 7.20 (s, 1H), 7.13 (s, 1H), 7.08 (dt, 5.6, 3.0 Hz, 1H), 6.58 (br. s, 1H), 5.92 (br. s, 1H), 4.20-3.98 (m, 2H), 3.54 (dd, 9.7, 8.3 Hz, 1H), 3.24 (dd, 9.6, 5.0 Hz, 1H), 2.90-2.76 (m, 1H), 2.73 (s, 3H), 2.44 (dd, overlapped with solvent peak, 17.0, 9.2 Hz, 1H), 2.17 (dd, 16.8, 6.4 Hz, 1H) | 594.2 | A | |
| I-1349 | 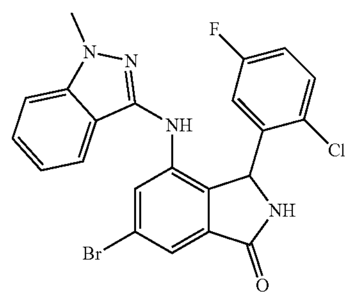 [SMILES: Cn1nc(Nc2cc(Br)cc3c2C(c2cc(F)ccc2Cl)NC3=O)c2ccccc21] | Cn1nc(Nc2cc(Br)cc3C(=O)NC(c23)c2cc(F)ccc2Cl)c2ccccc12 | 1H NMR (400 MHz, DMSO-d6) 9.14 (s, 1H), 8.39 (s, 1H), 7.87 (s, 1H), 7.47 (d, 8.5 Hz, 1H), 7.39 (d, 1.7 Hz, 1H), 7.33 (ddd, 8.3, 6.8, 1.1 Hz, 1H), 7.27 (d, 8.1 Hz, 1H), 7.20 (dd, 8.9, 5.1 Hz, 1H), 7.05-6.91 (m, 2H), 6.67 (s, 1H), 6.01 (s, 1H), 3.91 (s, 3H). | 485 | E | |
| I-1350 | 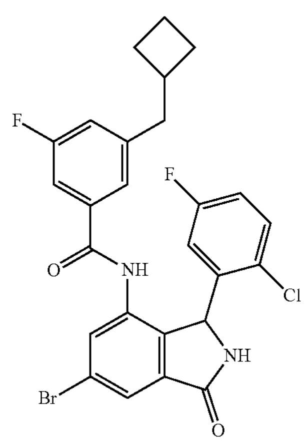 [SMILES: O=C(Nc1cc(Br)cc2c1C(c1cc(F)ccc1Cl)NC2=O)c1cc(F)cc(CC2CCC2)c1] | Fc1ccc(C1)c(c1)C1NC(=O)c2cc(Br)cc(NC(=O)c3cc(F)cc(CC4CCC4)c3)c12 | 1H NMR (400 MHz, DMSO-d6) 10.25 (s, 1H), 9.28 (s, 1H), 7.81-7.74 (m, 2H), 7.36 (dd, 8.9, 5.1 Hz, 1H), 7.22 (dt, 9.7, 1.8 Hz, 1H), 7.13 (ddt, 9.4, 4.7, 2.5 Hz, 3H), 6.71 (s, 1H), 6.01 (s, 1H), 2.69 (d, 7.7 Hz, 2H), 2.02-1.89 (m, 2H), 1.89-1.77 (m, 2H), 1.74-1.61 (m, 2H). | 545 | D | |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-1351 | 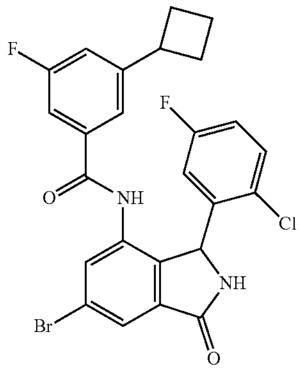 [SMILES: O=C(Nc1cc(Br)cc2c1C(c1cc(F)ccc1Cl)NC2=O)c1cc(F)cc(C2CCC2)c1] | Fc1ccc(C1)c(c1)C1NC(=O)c2cc(Br)cc(NC(=O)c3cc(F)cc(c3)C3CCC3)c12 | 1H NMR (400 MHz, DMSO-d6) 10.30 (s, 1H), 9.28 (s, 1H), 7.79 (d, 1.7 Hz, 1H), 7.74 (d, 1.8 Hz, 1H), 7.36 (dd, 8.8, 5.1 Hz, 1H), 7.26 (dd, 9.8, 2.3 Hz, 1H), 7.20-7.09 (m, 3H), 6.73 (s, 1H), 6.00 (s, 1H), 3.53 (p, 8.6 Hz, 1H), 2.30 (qt, 7.7, 2.5 Hz, 2H), 2.15-2.06 (m, 1H), 2.06 (ddd, 8.4, 6.9, 2.3 Hz, 1H), 2.05-1.89 (m, 1H), 1.88-1.73 (m, 1H). | 531 | D | |
| I-1352 | 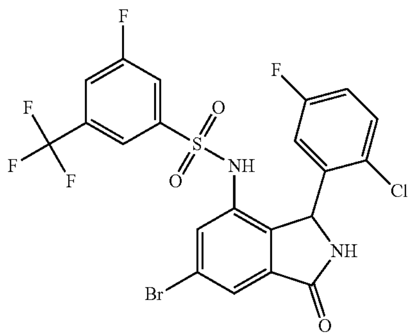 [SMILES: O=C1NC(c2cc(F)ccc2Cl)c2c(NS(=O)(=O)c3cc(F)cc(C(F)(F)F)c3)cc(Br)cc21] | Fc1ccc(C1)c(c1)C1NC(=O)c2cc(Br)cc(NS(=O)(=O)c3cc(F)cc(c3)C(F)(F)F)c12 | 1H NMR (400 MHz, DMSO-d6) 10.42 (s, 1H), 9.21 (s, 1H), 8.13-8.03 (s, 1H), 7.92-7.61 (m, 3H), 7.52-7.34 (s, 1H), 7.31-7.12 (tt, 8.5, 4.9 Hz, 2H), 6.39-6.71 (s, 1H), 6.02 (s, 1H). | 581.15 | E | |
| I-1353 | 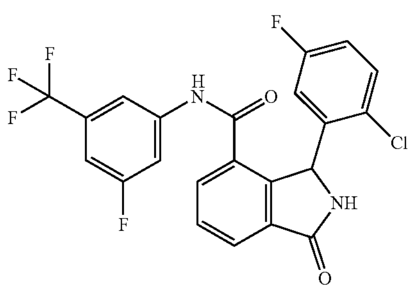 | Fc1ccc(C1)c(c1)C1NC(=O)c2cccc(C(=O)Nc3cc(F)cc(c3)C(F)(F)F)c12 | 1H NMR (400 MHz, DMSO-d6) 10.84 (s, 1H), 9.30 (s, 1H), 8.00-7.90 (m, 2H), 7.77 (t, 7.6 Hz, 1H), 7.63 (s, 1H), 7.57 (d, 11.3 Hz, 1H), 7.38 (d, 8.7 Hz, 2H), 7.10 (td, 8.4, 3.1 Hz, 1H), 6.39 (s, 1H). | 467.05 | D | |
| I-1354 | 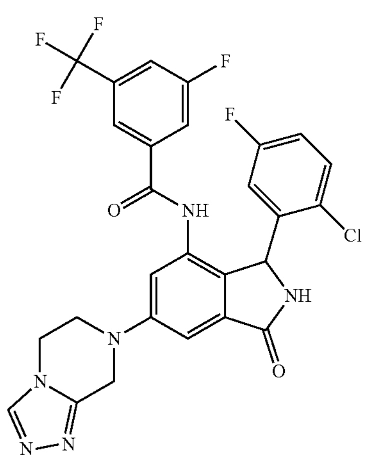 [SMILES: O=C(Nc1cc(N2CCn3cnnc3C2)cc2c1C(c1cc(F)ccc1Cl)NC2=O)c1cc(F)cc(C(F)(F)F)c1] | Fc1ccc(C1)c(c1)C1NC(=O)c2cc(cc(NC(=O)c3cc(F)cc(c3)C(F)(F)F)c12)N1CCn2cnnc2C1 | (400 MHz, DMSO-d6) 10.50 (br s, 1 H), 8.78 (br s, 1 H), 8.51 (d, 13.2 Hz, 1 H), 8.50 (s, 1 H), 7.83 (s, 1 H), 7.75 (d, 9.1 Hz, 1 H), 7.55 (br s, 1 H), 7.36 (dd, 8.8, 5.2 Hz, 1 H), 7.06 (td, 8.4, 3.1 Hz, 1 H), 6.87 (br s, 1 H), 6.51 (br s, 1 H), 5.87 (s, 1 H), 4.57 (s, 2 H), 4.18 (t, 5.2 Hz, 2 H), 3.80-3.72 (m, 2 H). | 589.3 | A | |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-1355 | 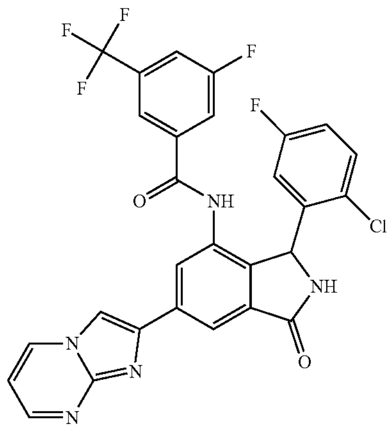 [SMILES: O=C(Nc1cc(-c2cn3cccnc3n2)cc2c1C(c1cc(F)ccc1Cl)NC2=O)c1cc(F)cc(C(F)(F)F)c1] | Fc1ccc(C1)c(c1)C1NC(=O)c2cc(cc(NC(=O)c3cc(F)cc(c3)C(F)(F)F)c12)-c1cn2cccnc2n1 | NMR (400 MHz, DMSO-d6) 10.70 (br. s, 1H), 9.23 (br. s, 1H), 9.00 (dd, 6.8, 1.9 Hz, 1H), 8.61 (s, 1H), 8.57 (dd, 4.1, 2.0 Hz, 1H), 8.27 (s, 1H), 8.21 (s, 1H), 7.96 (br. d, 8.3 Hz, 1H), 7.79 (br. d, 9.1 Hz, 1H), 7.72 (s, 1H), 7.33 (dd, 8.8, 5.1 Hz, 1H), 7.13-7.08 (m, 2H), 6.60 (br. s, 1H), 6.07 (br. s, 1H). | 584.1 | A | |
| I-1356 | 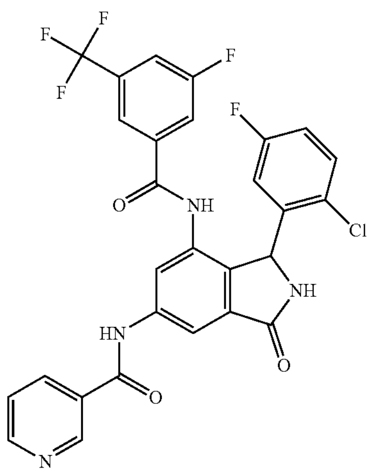 [SMILES: O=C(Nc1cc(NC(=O)c2cc(F)cc(C(F)(F)F)c2)c2c(c1)C(=O)NC2c1cc(F)ccc1Cl)c1cccnc1] | Fc1ccc(C1)c(c1)C1NC(=O)c2cc(NC(=O)c3cccnc3)cc(NC(=O)c3cc(F)cc(c3)C(F)(F)F)c12 1p;2p | NMR (400 MHz, DMSO) 10.86 (s, 1H), 10.63 (s, 1H), 9.19 (s, 1H), 9.15 (d, 2.1 Hz, 1H), 8.79 (dd, 4.8, 1.6 Hz, 1H), 8.37-8.30 (m, 1H), 8.15 (d, 1.4 Hz, 1H), 8.03 (d, 1.1 Hz, 1H), 7.95 (d, 8.0 Hz, 1H), 7.74 (d, 8.6 Hz, 1H), 7.65 (s, , 1H), 7.61 (dd, 8.5, 4.8 Hz, 1H), 7.32 (dd, 8.8, 5.2 Hz, 1H), 7.10 (td, 8.4, 2.9 Hz, 1H), 6.57 (br s, 1H), 5.96 (br s, 1H). | 587.3 | A | |
| I-1357 | 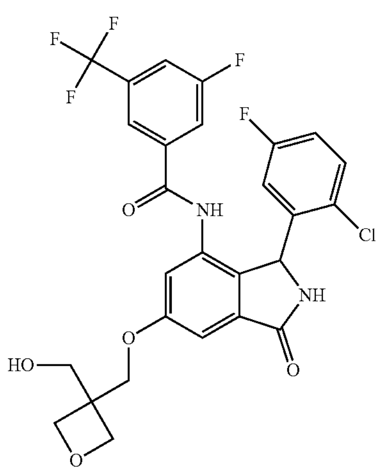 [SMILES: O=C(Nc1cc(OCC2(CO)COC2)cc2c1C(c1cc(F)ccc1Cl)NC2=O)c1cc(F)cc(C(F)(F)F)c1] | OCC1(COc2cc3C(=O)NC(c3c(NC(=O)c3cc(F)cc(c3)C(F)(F)F)c2)c2ccc(F)ccc2Cl)COC1 | NMR (400 MHz, DMSO) 10.45 (br s, 1H), 9.15 (br s, 1H), 7.95 (d, 7.8 Hz, 1H), 7.72 (d, 8.8 Hz, 1H), 7.64 (s, 1H), 7.31 (dd, 8.8, 5.2 Hz, 1H), 7.26 (d, 2.0 Hz, 1H), 7.13 (d, 1.6 Hz, 1H), 7.09 (td, 8.5, 3.1 Hz, 1H), 6.59 (br s, 1H), 5.94 (br s, 1H), 5.04 (s, 1H), 4.50-4.38 (m, 4H), 4.30 (d, 9.5 Hz, 1H), 4.25 (d, 9.5 Hz, 1H), 3.74 (s, 2H). | 583.3 | A | |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-1358 | 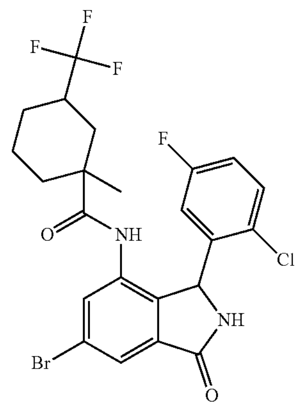 [SMILES: CC1(C(=O)Nc2cc(Br)cc3c2C(c2cc(F)ccc2Cl)NC3=O)CCCC(C(F)(F)F)C1] | CC1(CC CC(C1)C (F)(F)F) C(=O)Nc 1cc(Br)cc 2C(=O)N C(c12)c1 cc(F)ccc1 Cl | 1H-NMR (400 MHz, DMSO-d6) as a mixture of diastereomers-' 9.58 (br. s, 2H), 9.30 (br. s, 2H), 7.74 (br. d, 1.3 Hz, 2H), 7.66 (d, 1.7 Hz, 1H), 7.64 (d, 1.7 Hz, 1H), 7.57-7.48 (m, 2H), 7.27-7.22 (m, 1H), 7.22-7.17 (m, 1H), 6.40 (br. s, 2H), 6.22 (br. s, 1H), 6.15 (br. s, 1H), 2.22-2.13 (m, 2H), 2.10-2.00 (m, 2H), 1.58-1.44 (m, 5H), 1.36-1.29 (m, 1H), 1.10-0.93 (m, 8H), 0.93 (s, 3H), 0.89 (s, 3H). | 547.2 | B | |
| I-1359 | 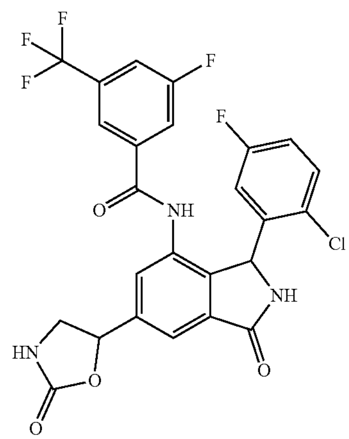 [SMILES: O=C1NCC(c2cc(NC(=O)c3cc(F)cc(C(F)(F)F)c3)c3c(c2)C(=O)NC3c2cc(F)ccc2Cl)O1] | Fc1ccc(C 1)c(c1)C1 NC(=O)c 2cc(cc(N C(=O)c3 cc(F)cc(c 3)C(F)(F) F)c12)C1 CNC(=O) O1 | NMR (400 MHz, DMSO) 10.60 (s, 1H), 9.23 (s, 1H), 7.95 (d, 8.4 Hz, 1H), 7.82 (s, 0.5H), 7.81 (s, 0.5H), 7.74 (d, 9.1 Hz, 1H), 7.71 (s, 1H), 7.65 (s, 1H), 7.54 (s, 0.5H), 7.53 (s, 0.5H), 7.32 (dd, 8.8, 5.1 Hz, 1H), 7.14-7.06 (m, 1H), 6.59 (br s, 1H), 6.00 (br s, 1H), 5.81 (dd, 15.3, 7.8 Hz, 1H), 3.99 (td, 8.8, 6.7 Hz, 1H), 3.45-3.37 (m, 1H) | 552.1 | A | |
| I-1360 | 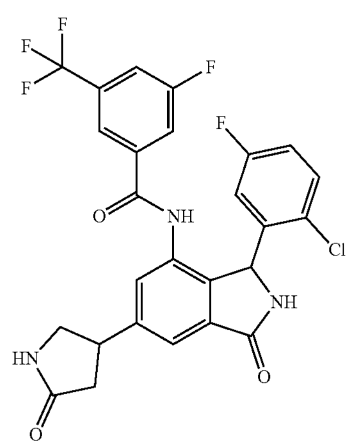 [SMILES: O=C1CC(c2cc(NC(=O)c3cc(F)cc(C(F)(F)F)c3)c3c(c2)C(=O)NC3c2cc(F)ccc2Cl)CN1] | Fc1ccc(C 1)c(c1)C1 NC(=O)c 2cc(cc(N C(=O)c3 cc(F)cc(c 3)C(F)(F) F)c12)C1 CNC(=O) C1 | (400 MHz, CD3CN) 8.65 (br. s, 1H), 7.88-7.55 (m, 5H), 7.48 (s, 1H), 7.32-7.23 (m, 2H), 7.04-6.92 (m, 1H), 6.61 (br. s, 1H), 6.11 (br. s, 1H), 3.91-3.72 (m, 2H), 3.44-3.33 (m, 1H), 2.66 (dtd, 11.2, 8.6, 2.5 Hz, 1H), 2.46-2.33 (m, 1H). | 548.3 | A | |

TABLE 2-continued

Representative Compounds of the Invention with Bioactivity Data.

| Ex. No. | Structure | SMILES | $^1$H NMR | MS | ADP-Glo IC$_{50}$ | MCF 10A IC$_{50}$ |
|---|---|---|---|---|---|---|
| I-1361 | 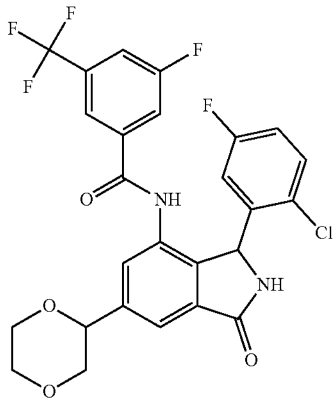 [SMILES: O=C(Nc1cc(C2COCCO2)cc2c1C(c1cc(F)ccc1Cl)NC2=O)c1cc(F)cc(C(F)(F)F)c1] | Fc1ccc(C1)c(c1)C1NC(=O)c2cc(cc(NC(=O)c3cc(F)cc(c3)C(F)(F)F)c12)C1COCCO1 | NMR (400 MHz, CD3CN) 8.60 (br s, 1H), 7.77 (d, 8.0 Hz, 1H), 7.65 (d, 7.9 Hz, 1H), 7.62-7.46 (m, 3H), 7.24 (dd, 9.7, 4.5 Hz, 2H), 7.09-6.92 (m, 1H), 6.63 (br s, 1H), 6.08 (br s, 1H), 5.75 (d, 7.7 Hz, 1H), 4.09 (t, 15.0 Hz, 1H), 3.95 (dd, 11.0, 4.4 Hz, 2H), 3.79 (d, 11.4 Hz, 1H), 3.69 (dt, 12.1, 4.0 Hz, 1H), 3.27 (dt, 16.6, 11.2 Hz, 1H). | 553.3 | B | |
| I-1362 | 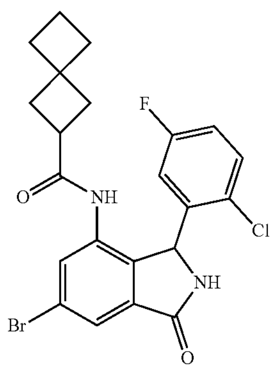 [SMILES: O=C1NC(c2cc(F)ccc2Cl)c2c(NC(=O)C3CC4(CCC4)C3)cc(Br)cc21] | Fc1ccc(C1)c(c1)C1NC(=O)c2cc(Br)cc(NC(=O)C3CC4(CCC4)C3)c12 | 1H-NMR (400 MHz, DMSO-d6) 9.58 (s, 1H), 9.22 (br. s, 1H), 7.68 (d, 1.5 Hz, 1H), 7.58 (d, 1.6 Hz, 1H), 7.52-7.45 (m, 1H), 7.24 (app. td, 8.4, 3.1 Hz, 1H), 6.64 (br. s, 1H), 6.00 (br. s, 1H), 2.74 (p, 8.5 Hz, 1H), 1.96-1.64 (m, 10H). | 477.3 | D | |
| I-1363 | 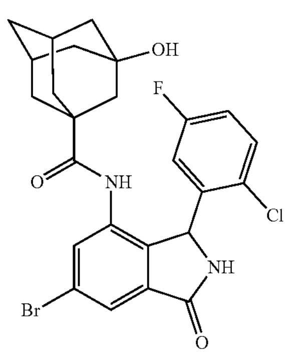 [SMILES: O=C1NC(c2cc(F)ccc2Cl)c2c(NC(=O)C34CC5CC(CC(O)(C5)C3)C4)cc(Br)cc21] | OC12CC3CC(C1)CC(C3)(C2)C(=O)Nc1cc(Br)cc2C(=O)NC(c12)c1cc(F)ccc1Cl | 1H-NMR (400 MHz, DMSO-d6) 9.24 (br. s, 2H), 7.70 (d, 1.6 Hz, 1H), 7.59 (d, 1.7 Hz, 1H), 7.53-7.45 (m, 1H), 7.24 (app. td, 8.5, 3.1 Hz, 1H), 6.51 (br. s, 1H), 6.01 (br. s, 1H), 4.48 (br. s, 1H), 2.07-2.01 (m, 2H), 1.53-1.29 (m, 12H). | 533.3 | D | |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-1364 | 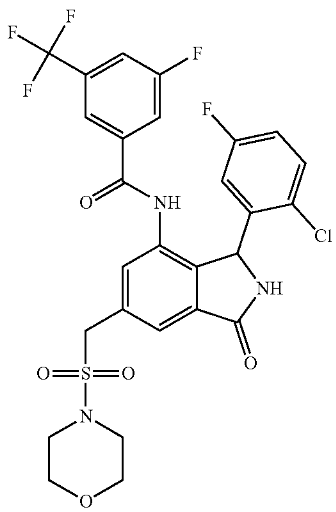 [SMILES: O=C(Nc1cc(CS(=O)(=O)N2CCOCC2)cc2c1C(c1cc(F)ccc1Cl)NC2=O)c1cc(F)cc(C(F)(F)F)c1] | Fc1ccc(C1)c(c1)C1NC(=O)c2cc(CS(=O)(=O)N3CCOCC3)cc(NC(=O)c3cc(F)cc(c3)C(F)(F)F)c12 | NMR (400 MHz, DMSO-d6) 10.61 (s, 1H), 9.23 (br. s, 1H), 7.96 (br. d, 8.3 Hz, 1H), 7.79 (s, 1H), 7.75 (br. d, 9.2 Hz, 1H), 7.65 (s, 1H), 7.55 (s, 1H), 7.33 (dd, 8.9, 5.2 Hz, 1H), 7.11 (td, 8.5, 2.9 Hz, 1H), 6.44 (br. s, 1H), 5.98 (br. s, 1H), 4.71 (d, 13.7 Hz, 1H), 4.67 (d, 13.6 Hz, 1H), 3.64-3.53 (m, 4H), 3.21-3.09 (m, 4H). | 630.2 | A | |
| I-1365 | 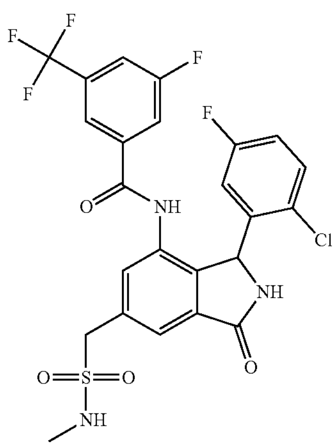 [SMILES: CNS(=O)(=O)Cc1cc(NC(=O)c2cc(F)cc(C(F)(F)F)c2)c2c(c1)C(=O)NC2c1cc(F)ccc1Cl] | CNS(=O)(=O)Cc1cc2C(=O)NC(c2c(NC(=O)c2cc(F)cc(c2)C(F)(F)F)c1)c1cc(F)ccc1Cl | NMR (400 MHz, CD3CN) 8.74 (s, 1H), 7.75 (d, 1.4 Hz, 1H), 7.68-7.53 (m, 1H), 7.62-7.54 (m, 3H) 7.32-7.23 (m, 2H), 6.98 (ddd, 8.9, 8.0, 3.1 Hz, 1H), 6.64 (br, s, 1H), 6.25-6.04 (br, s, 1H), 5.22 (q, 4.8 Hz, 1H), 4.45 (s, 2H), 2.71 (d, 5.0 Hz, 3H). | 574 | A | |
| I-1366 | 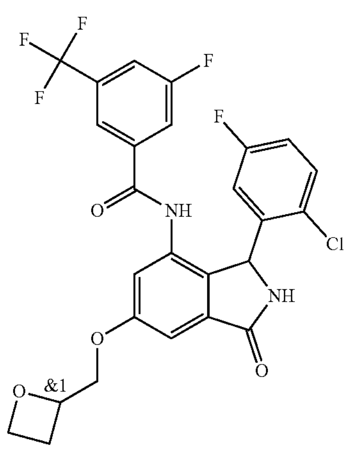 [SMILES: O=C(Nc1cc(OCC2CCO2)cc2c1C(c1cc(F)ccc1Cl)NC2=O)c1cc(F)cc(C(F)(F)F)c1] | Fc1ccc(C1)c(c1)C1NC(=O)c2cc(OCC3CCO3)cc(NC(=O)c3cc(F)cc(c3)C(F)(F)F)c12 | 1H NMR (400 MHz, DMSO-d6) 10.47 (br. s, 1H), 9.14 (br. s, 1H), 7.95 (d, 8.4 Hz, 1H), 7.72 (d, 9.1 Hz, 1H), 7.64 (s, 1H), 7.31 (dd, 8.9, 5.2 Hz, 1H), 7.26 (s, 1H), 7.13 (s, 1H), 7.09 (td, 8.5, 3.0 Hz, 1H), 6.58 (br. s, 1H), 5.93 (br. s, 1H), 5.10-5.00 (m, 1H), 4.61-4.41 (m, 2H), 4.27 m, 2H), 2.79-2.65 (m, 1H), 2.63-2.53 (m, 1H). | 553.1 | A | |

TABLE 2-continued

Representative Compounds of the Invention with Bioactivity Data.

| Ex. No. | Structure | SMILES | $^1$H NMR | MS | ADP-Glo IC$_{50}$ | MCF 10A IC$_{50}$ |
|---|---|---|---|---|---|---|
| I-1367 | 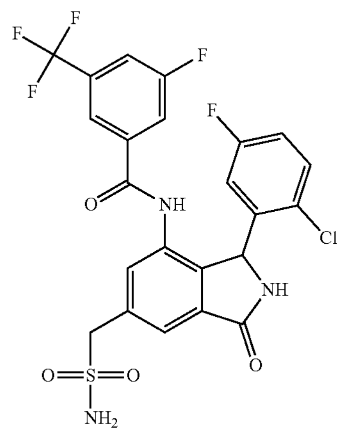 [SMILES: NS(=O)(=O)Cc1cc(NC(=O)c2cc(F)cc(C(F)(F)F)c2)c2c(c1)C(=O)NC2c1cc(F)ccc1Cl] | NS(=O)(=O)Cc1cc2C(=O)NC(c2c(NC(=O)c2cc(F)cc(c2)C(F)(F)F)c1)c1cc(F)ccc1Cl | NMR (400 MHz, DMSO-d6) 10.65 (br. s, 1H), 9.20 (br. s, 1H), 7.94 (br. d, 8.3 Hz, 1H), 7.74 (br. d, 8.9 Hz, 1H), 7.72 (s, 1H), 7.63 (s, 1H), 7.47 (s, 1H), 7.32 (dd, 8.9, 5.2 Hz, 1H), 7.11 (td, 8.6, 3.0 Hz, 1H), 6.97 (s, 2H), 6.60 (br. s, 1H), 6.00 (br. s, 1H), 4.51 (d, 13.7 Hz, 1H), 4.45 (d, 13.6 Hz, 1H). | 560.1 | A | |
| I-1368 | 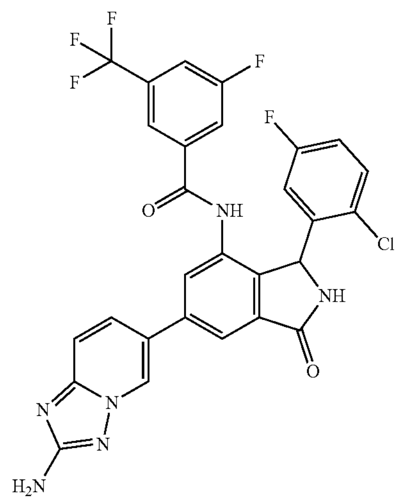 [SMILES: Nc1nc2ccc(-c3cc(NC(=O)c4cc(F)cc(C(F)(F)F)c4)c4c(c3)C(=O)NC4c3cc(F)ccc3Cl)cn2n1] | Nc1nc2ccc(cn2n1)-c1cc2C(=O)NC(c2c(NC(=O)c2cc(F)cc(c2)C(F)(F)F)c1)c1cc(F)ccc1Cl | $^1$H NMR (500 MHz, DMSO) δ 10.79 (s, 1H), 9.21 (s, 1H), 9.03 (dd, J = 2.0, 0.9 Hz, 1H), 8.01 (d, J = 1.7 Hz, 1H), 7.97-7.92 (m, 1H), 7.89 (d, J = 1.7 Hz, 1H), 7.86 (dd, J = 9.2, 1.9 Hz, 1H), 7.83 (s, 1H), 7.75 (s, 1H), 7.48-7.45 (m, 1H), 7.31 (dd, J = 8.9, 5.1 Hz, 1H), 7.08 (td, J = 8.3, 3.0 Hz, 1H), 6.13 (s, 2H), 6.08 (s, 1H). | 599.23 | A | |
| I-1369 | 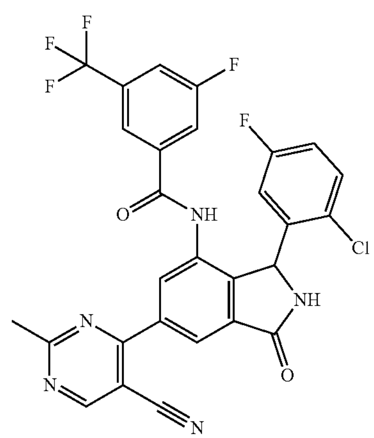 [SMILES: Cc1ncc(C#N)c(-c2cc(NC(=O)c3cc(F)cc(C(F)(F)F)c3)c3c(c2)C(=O)NC3c2cc(F)ccc2Cl)n1] | Cc1ncc(C#N)c(n1)-c1cc2C(=O)NC(c2c(NC(=O)c2cc(F)cc(c2)C(F)(F)F)c1)c1cc(F)ccc1Cl | | | A | |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-1370 | 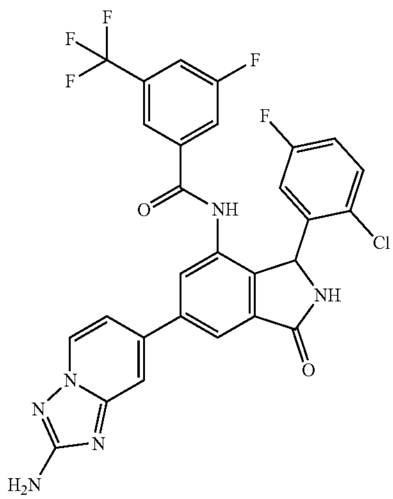 [SMILES: Nc1nc2cc(-c3cc(NC(=O)c4cc(F)cc(C(F)(F)F)c4)c4c(c3)C(=O)NC4c3cc(F)ccc3Cl)ccn2n1] | Nc1nc2c c(ccn2n1)-c1cc2C(=O)NC(c2 c(NC(=O) c2cc(F)c c(c2)C(F) (F)F)c1)c 1cc(F)ccc 1Cl | ¹H NMR (500 MHz, DMSO) δ 10.61 (s, 1H), 9.25 (s, 1H), 8.64 (d, J = 7.0 Hz, 1H), 8.06 (d, J = 1.8 Hz, 1H), 7.98-7.91 (m, 2H), 7.79-7.66 (m, 4H), 7.37-7.27 (m, 2H), 7.10 (td, J = 8.3, 3.2 Hz, 1H), 6.10 (s, 2H). | 599.13 | A | |
| I-1371 | 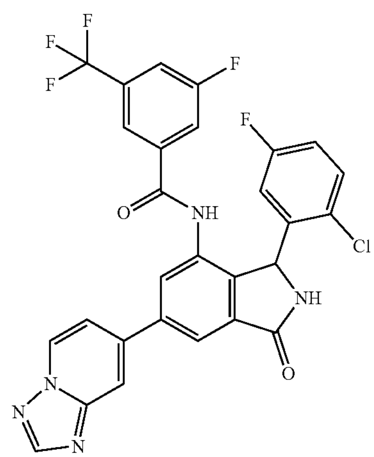 [SMILES: O=C(Nc1cc(-c2ccn3ncnc3c2)cc2c1C(c1cc(F)ccc1Cl)NC2=O)c1cc(F)cc(C(F)(F)F)c1] | Fc1ccc(C 1)c(c1)C1 NC(=O)c 2cc(cc(N C(=O)c3 cc(F)cc(c 3)C(F)(F) F)c12)-c1ccn2nc nc2c1 | | | A | |
| I-1372 | 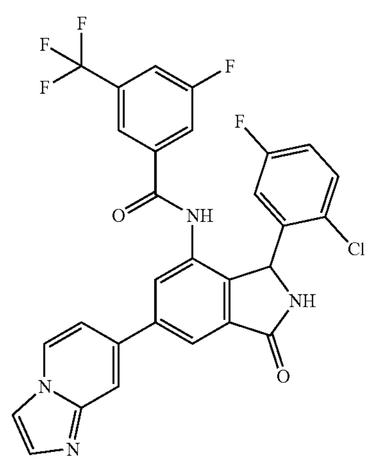 [SMILES: O=C(Nc1cc(-c2ccn3ccnc3c2)cc2c1C(c1cc(F)ccc1Cl)NC2=O)c1cc(F)cc(C(F)(F)F)c1] | Fc1ccc(C 1)c(c1)C1 NC(=O)c 2cc(cc(N C(=O)c3 cc(F)cc(c 3)C(F)(F) F)c12)-c1ccn2cc nc2c1 | | | A | |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-1373 | 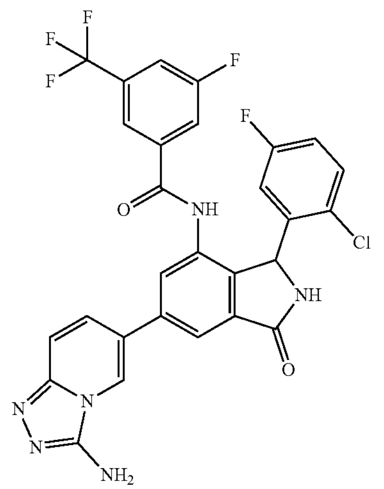 [SMILES: Nc1nnc2ccc(-c3cc(NC(=O)c4cc(F)cc(C(F)(F)F)c4)c4c(c3)C(=O)NC4c3cc(F)ccc3Cl)cn12] | Nc1nnc2ccc(cn12)-c1cc2C(=O)NC(c2c(NC(=O)c2cc(F)cc(c2)C(F)(F)F)c1)c1cc(F)ccc1Cl | | | | A |
| I-1374 | 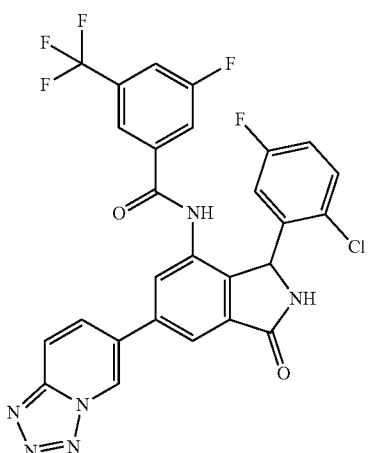 | Fc1ccc(C1)c(c1)C1NC(=O)c2cc(cc(NC(=O)c3cc(F)cc(c3)C(F)(F)F)c12)-c1ccc2nnnn2c1 | | 585.4 | | A |
| I-1375 | 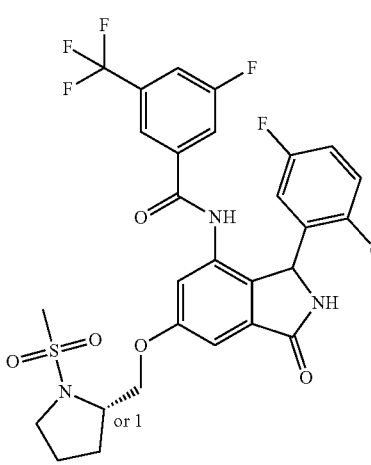 | CS(=O)(=O)N1CCC[C@H]1COc1cc2C(=O)NC(c2c(NC(=O)c2cc(F)cc(c2)C(F)(F)F)c1cc(F)ccc1Cl | NMR (400 MHz, DMSO-d6) 10.45 (s, 1H), 9.14 (br. s, 1H), 7.95 (br. d, 8.5 Hz, 1H), 7.72 (br. d, 8.7 Hz, 1H), 7.64 (s, 1H), 7.31 (dd, 8.9, 5.2 Hz, 1H), 7.21 (d, 1.6 Hz, 1H), 7.11-7.05 (m, 2H), 6.57 (br. s, 1H), 5.94 (br. s, 1H), 4.16-4.00 (m, 3H), 3.32-3.30 (m, 2H), 2.99 (d, 0.8 Hz, 3H), 2.09-1.87 (m, 4H). | 644.2 | | A |

TABLE 2-continued

Representative Compounds of the Invention with Bioactivity Data.

| Ex. No. | Structure | SMILES | $^1$H NMR | MS | ADP-Glo IC$_{50}$ | MCF 10A IC$_{50}$ |
|---|---|---|---|---|---|---|
| I-1376 | 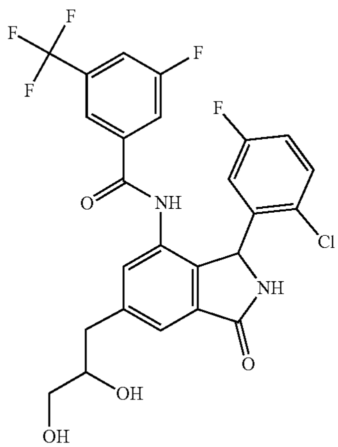 [SMILES: O=C(Nc1cc(CC(O)CO)cc2c1C(c1cc(F)ccc1Cl)NC2=O)c1cc(F)cc(C(F)(F)F)c1] | OCC(O)Cc1cc2C(=O)NC(c2c(NC(=O)c2cc(F)cc(c2)C(F)(F)F)c1c1cc(F)ccc1Cl | NMR (400 MHz, DMSO-d6) 10.48 (br s, 1H), 9.09 (s, 1H), 7.94 (d, 8.3 Hz, 1H), 7.73 (d, 8.9 Hz, 1H), 7.65 (s, 1H), 7.56 (s, 1H), 7.37-7.26 (m, 2H), 7.08 (td, 13.5, 6.7 Hz, 1H), 6.59 (br s, 1H), 5.95 (br s, 1H), 4.73 (d, 4.5 Hz, 1H), 4.67 (br s, 1H), 3.70 (br s, 1H), 3.31-3.25 (m, 2H), 3.01-2.89 (m, 1H), 2.67 (tt, 17.1, 8.5 Hz, 1H). | 541.3 | A | |
| I-1377 | 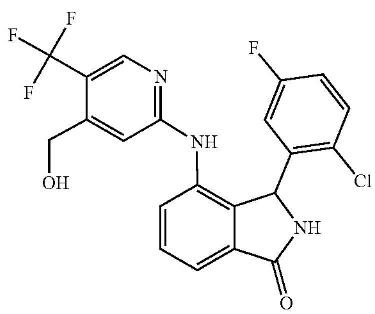 [SMILES: O=C1NC(c2cc(F)ccc2Cl)c2c(Nc3cc(CO)c(C(F)(F)F)cn3)cccc21] | OCc1cc(Nc2cccc3C(=O)NC(c23)c2cc(F)ccc2Cl)ncc1C(F)(F)F | (400 MHz, CD3CN) 8.92 (s, 1 H), 8.41 (s, 1 H), 7.48 (br s, 1 H), 7.35 (app t, 7.6 Hz, 1 H), 7.31-7.26 (m, 1 H), 6.99 (br t, 7.1 Hz, 1 H), 6.92 (d, 7.8 Hz, 1 H), 6.88 (br s, 1 H), 6.75-6.48 (br s, 1 H)), 6.69-6.61 (m, 1 H), 4.80 (d, 16.2 Hz, 1 H), 4.80 (d, 16.2 Hz, 1 H), 4.18 (s, 1 H), 3.68 (s, 1 H). | 452.2 | E | |
| I-1378 | 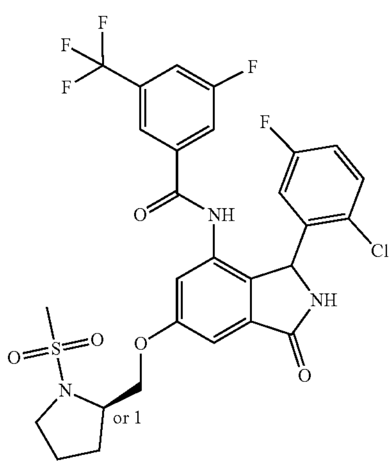 [SMILES: CS(=O)(=O)N1CCC[C@@H]1COc1cc(NC(=O)c2cc(F)cc(C(F)(F)F)c2)c2c(c1)C(=O)NC2c1cc(F)ccc1Cl] | CS(=O)(=O)N1CCC[C@@H]1COc1cc2C(=O)NC(c2c(NC(=O)c2cc(F)cc(c2)C(F)(F)F)c1c1cc(F)ccc1Cl | NMR (400 MHz, DMSO-d6) 10.45 (s, 1H), 9.14 (br. s, 1H), 7.95 (br. d, 8.5 Hz, 1H), 7.72 (br. d, 8.7 Hz, 1H), 7.64 (s, 1H), 7.31 (dd, 8.9, 5.2 Hz, 1H), 7.21 (d, 1.6 Hz, 1H), 7.13-7.03 (m, 2H), 6.58 (br. s, 1H), 5.93 (br. s, 1H), 4.19-3.98 (m, 3H), 3.32-3.30 (m, 2H), 2.99 (d, 0.8 Hz, 3H), 2.10-1.84 (m, 4H). | 644.2 | A | |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-1379 | 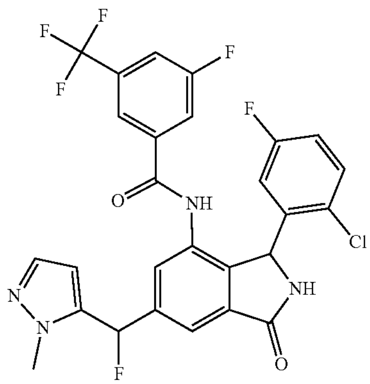 [SMILES: Cn1nccc1C(F)c1cc(NC(=O)c2cc(F)cc(C(F)(F)F)c2)c2c(c1)C(=O)NC2c1cc(F)ccc1Cl] | Cn1nccc1C(F)c1cc2C(=O)NC(c2c(NC(=O)c2cc(F)cc(c2)C(F)(F)F)c1)c1cc(F)ccc1Cl | NMR (400 MHz, DMSO-d6) as a ca. 1.2:1 mixture of diastereomers-' 10.59 (br. s, 2H), 9.27 (br. s, 2H), 7.95 (br. d, 8.2 Hz, 2H), 7.77-7.68 (m, 4H), 7.64 (s, 2H), 7.59 (s, 1H), 7.55 (s, 1H), 7.43 (dd, 6.9, 1.8 Hz, 2H), 7.34 (dd, 5.2, 1.8 Hz, 1H), 7.33-7.29 (m, 2H), 7.22 (d, 7.7 Hz, 1H), 7.13-7.07 (m, 3H), 6.69 (br. s, 2H), 6.12-5.93 (m, 4H), 3.90 (s, 3H), 3.89 (s, 3H). | 579.3 | A | |
| I-1380 | 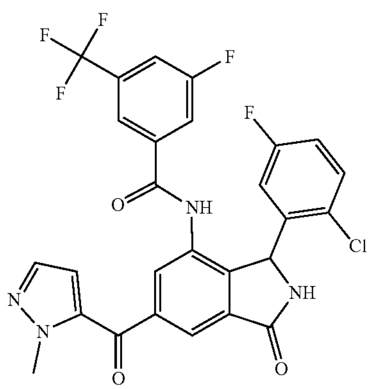 [SMILES: Cn1nccc1C(=O)c1cc(NC(=O)c2cc(F)cc(C(F)(F)F)c2)c2c(c1)C(=O)NC2c1cc(F)ccc1Cl] | Cn1nccc1C(=O)c1cc2C(=O)NC(c2c(NC(=O)c2cc(F)cc(c2)C(F)(F)F)c1)c1cc(F)ccc1Cl | 1H-NMR (400 MHz, DMSO-d6) 10.71 (br. s, 1H), 9.38 (br. s, 1H), 8.03 (s, 1H), 8.00 (s, 1H), 7.97 (br. d, 8.3 Hz, 1H), 7.76 (br. d, 9.1 Hz, 1H), 7.67 (br. s, 1H), 7.66 (d, 2.0 Hz, 1H), 7.35 (dd, 8.9, 5.1 Hz, 1H), 7.12 (td, 8.5, 3.1 Hz, 1H), 6.90 (s, 1H), 6.58 (br. s, 1H), 6.10 (br. s, 1H), 4.14 (s, 3H). | 575.3 | A | |
| I-1381 | 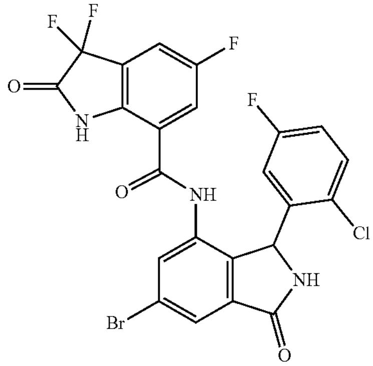 [SMILES: O=C(Nc1cc(Br)cc2c1C(c1cc(F)ccc1Cl)NC2=O)c1cc(F)cc2c1NC(=O)C2(F)F] | Fc1ccc(C1)c(c1)C1NC(=O)c2cc(Br)cc(NC(=O)c3cc(F)cc4c3NC(=O)C4(F)F)c12 | 1H NMR (400 MHz, DMSO-d6) 11.11 (s, 1H), 10.49 (s, 1H), 9.30 (s, 1H), 7.99 (s, 1H), 7.79 (d, 21.8 Hz, 2H), 7.23 (d, 87.9 Hz, 4H), 6.0 (s, 1H) | 570 | B | |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-1382 | 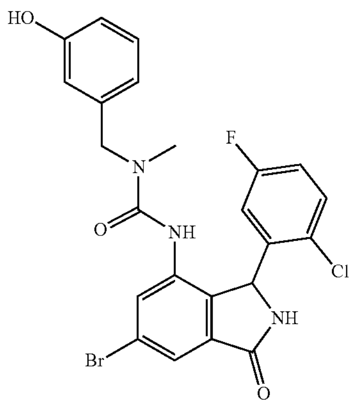 [SMILES: CN(Cc1cccc(O)c1)C(=O)Nc1cc(Br)cc2c1C(c1cc(F)ccc1Cl)NC2=O] | CN(Cc1ccc(O)c1)C(=O)Nc1cc(Br)cc2C(=O)NC(c12)c1cc(F)ccc1Cl | 1H NMR (400 MHz, Chloroform-d) 8.16 (s, 1H), 7.77 (d, 1.6 Hz, 1H), 7.36 (dd, 8.9, 4.9 Hz, 1H), 7.19 (t, 7.8 Hz, 1H), 7.02 (ddd, 8.9, 7.4, 3.1 Hz, 1H), 6.78 (ddd, 8.2, 2.6, 0.9 Hz, 1H), 6.65 (dd, 16.5, 7.1 Hz, 3H), 6.57 (s, 1H), 6.04 (s, 1H), 5.93 (d, 6.8 Hz, 2H), 4.41-4.12 (m, 2H), 2.74 (s, 3H). | 520 | E | |
| I-1383 | 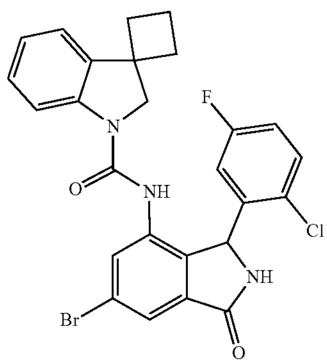 [SMILES: O=C1NC(c2cc(F)ccc2Cl)c2c(NC(=O)N3CC4(CCC4)c4ccccc43)cc(Br)cc21] | Fc1ccc(C1)c(c1)C1NC(=O)c2cc(Br)cc(NC(=O)N3CC4(CCC4)c4ccccc34)c12 | 1H NMR (400 MHz, DMSO-d6) 9.21 (s, 1H), 8.64 (s, 1H), 7.69-7.62 (m, 3H), 7.46 (dd, 7.6, 1.3 Hz, 1H), 7.37 (dd, 8.9, 5.1 Hz, 1H), 7.14 (ddt, 11.0, 6.2, 3.1 Hz, 2H), 7.00 (td, 7.4, 1.1 Hz, 1H), 5.99 (s, 1H), 3.86 (d, 10.5 Hz, 1H), 3.40 (d, 10.4 Hz, 1H), 2.37-2.25 (m, 2H), 2.15-2.01 (m, 1H), 2.04-1.87 (m, 3H). | 540.05 | B | |
| I-1384 | 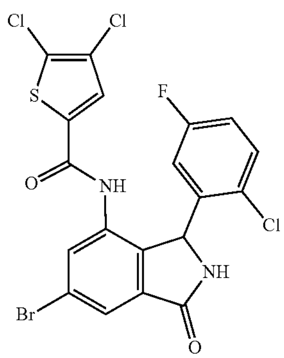 [SMILES: O=C(Nc1cc(Br)cc2c1C(c1cc(F)ccc1Cl)NC2=O)c1cc(Cl)c(Cl)s1] | Fc1ccc(C1)c(c1)C1NC(=O)c2cc(Br)cc(NC(=O)c3cc(Cl)c(Cl)s3)c12 | 1H NMR (400 MHz, DMSO-d6) 10.42 (s, 1H), 9.29 (s, 1H), 7.82 (d, 1.7 Hz, 1H), 7.71 (d, 1.7 Hz, 1H), 7.55 (s, 1H), 7.37 (dd, 8.9, 5.1 Hz, 1H), 7.14 (ddd, 8.8, 7.9, 3.1 Hz, 1H), 7.01-5.62 (m, 2H). | 534.85 | C | |
| I-1385 | 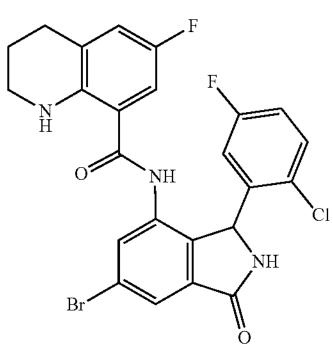 [SMILES: O=C(Nc1cc(Br)cc2c1C(c1cc(F)ccc1Cl)NC2=O)c1cc(F)cc2c1NCCC2] | Fc1ccc(C1)c(c1)C1NC(=O)c2cc(Br)cc(NC(=O)c3cc(F)cc4CCCNc34)c12 | 1H NMR (400 MHz, DMSO-d6) 9.95 (s, 1H), 9.28 (s, 1H), 7.97-7.67 (m, 2H), 7.39 (t, 7.0 Hz, 1H), 7.30 (s, 1H), 7.16 (td, 8.4, 3.1 Hz, 1H), 6.92 (dd, 8.9, 2.9 Hz, 1H), 6.56 (dd, 10.1, 3.0 Hz, 1H), 6.01 (s, 1H), 3.28 (s, 2H), 2.70 (q, 6.2 Hz, 2H), 1.83-1.67 (m, 2H). | 534.05 | C | |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-1386 | 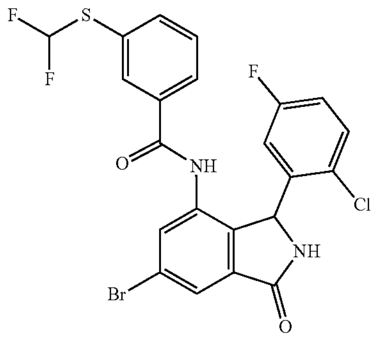 [SMILES: O=C(Nc1cc(Br)cc2c1C(c1cc(F)ccc1Cl)NC2=O)c1cccc(SC(F)F)c1] | FC(F)Sc1cccc(c1)C(=O)Nc1cc(Br)cc2C(=O)NC(c12)c1cc(F)ccc1Cl | 1H NMR (400 MHz, DMSO-d6) 10.37 (s, 1H), 9.27 (s, 1H), 7.85-7.80 (s, 1H), 7.80-7.72 (m, 2H), 7.71-7.69 (s, 1H), 7.67 (s, 1H), 7.54 (s, 1H), 7.49-7.31 (m, 1H), 7.30-7.15 (m, 1H), 7.10 (ddd, 8.8, 7.9, 3.1 Hz, 1H), 6.99-6.23 (s, 1H), 6.16 (s, 1H). | 540.95 | D | |
| I-1387 | 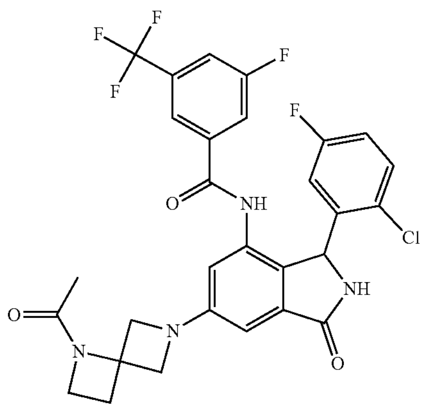 [SMILES: CC(=O)N1CCC12CN(c1cc(NC(=O)c3cc(F)cc(C(F)(F)F)c3)c3c(c1)C(=O)NC3c1cc(F)ccc1Cl)C2] | CC(=O)N1CCC11CN(C1)c1cc2C(=O)NC(c2c(NC(=O)c2cc(F)cc(c2)C(F)(F)F)c1)c1cc(F)ccc1Cl | NMR (400 MHz, DMSO-d6), 10.39 (br. s, 1H), 9.01 (br. s, 1H), 7.93 (br. d, 8.5 Hz, 1H), 7.72 (br. d, 8.8 Hz, 1H), 7.64 (s, 1H), 7.29 (dd, 8.9, 5.2 Hz, 1H), 7.06 (td, 8.4, 3.0 Hz, 1H), 6.67 (d, 2.0 Hz, 1H), 6.51 (d, 1.4 Hz, 1H), 6.9-6.4 (br. s, 1H), 5.87 (br. s, 1H), 4.47 (dd, 7.8, 3.4 Hz, 2H), 4.04-4.00 (m, 4H), 2.54 (t, 7.4 Hz, 2H), 1.76 (s, 3H). | 603.3 | B | |
| I-1388 | 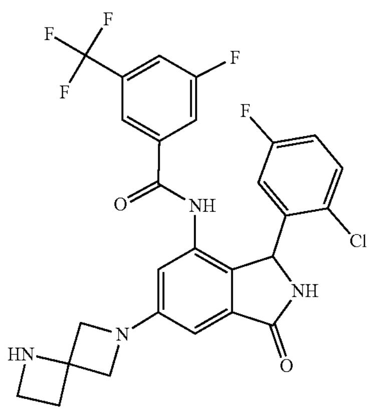 [SMILES: O=C(Nc1cc(N2CC3(CCN3)C2)cc2c1C(c1cc(F)ccc1Cl)NC2=O)c1cc(F)cc(C(F)(F)F)c1] | Fc1ccc(C1)c(c1)C1NC(=O)c2cc(cc(NC(=O)c3cc(F)cc(c3)C(F)(F)F)c12)N1CC2(CCN2)C1 | NMR (400 MHz, DMSO-d6) 10.35 (s, 1H), 8.99 (s, 1H), 7.93 (br. d, 8.4 Hz, 1H), 7.71 (br. d, 8.8 Hz, 1H), 7.63 (s, 1H), 7.28 (dd, 8.9, 5.2 Hz, 1H), 7.06 (td, 8.5, 3.0 Hz, 1H), 6.65 (d, 1.9 Hz, 1H), 6.50 (d, 0.7 Hz, 1H), 6.70-6.40 (submerged br. s, 1H), 5.86 (br. s, 1H), 4.08 (dd, 12.3, 8.0 Hz, 2H), 3.83 (t, 8.3 Hz, 2H), 3.32 (t, 6.9 Hz, 2H), 2.48-2.46 (m, 2H) | 563.2 | B | |
| I-1389 | 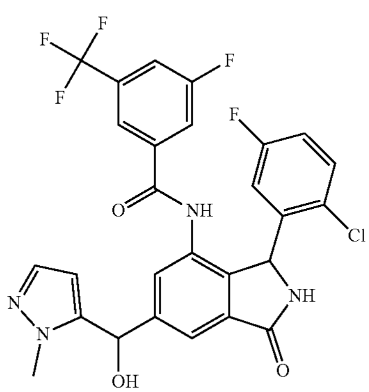 [SMILES: Cn1nccc1C(O)c1cc(NC(=O)c2cc(F)cc(C(F)(F)F)c2)c2c(c1)C(=O)NC2c1cc(F)ccc1Cl] | Cn1nccc1C(O)c1cc2C(=O)NC(c2c(NC(=O)c2cc(F)cc(c2)C(F)(F)F)c1)c1cc(F)ccc1Cl | 1H-NMR (400 MHz, DMSO-d6) 10.53 (br. s, 2H), 9.17 (br. s, 2H), 7.94 (br. d, 8.4 Hz, 2H), 7.73 (d, 9.2 Hz, 2H), 7.72 (s, 2H), 7.65 (d, 10.6 Hz, 2H), 7.64 (s, 2H), 7.50 (s, 12.6 Hz, 1H), 7.47 (br. s, 1H), 7.34-7.28 (m, 4H), 7.13-7.05 (m, 2H), 6.40-6.34 (m, 2H), 6.09 (d, 5.1 Hz, 1H), 6.06 (d, 4.6 Hz, 1H), 5.99 (br. s, 1H), 5.97 (br. s, 2H), 5.95 (br. s, 1H), 3.78 (s, 3H), 3.76 (s, 3H). | 577.3 | A | |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-1390 | 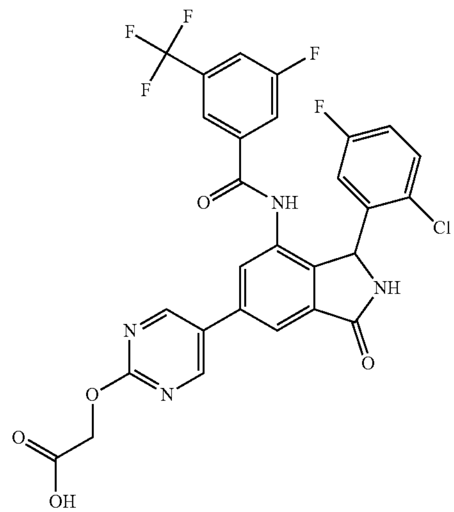 [SMILES: O=C(O)COc1ncc(-c2cc(NC(=O)c3cc(F)cc(C(F)(F)F)c3)c3c(c2)C(=O)NC3c2cc(F)ccc2Cl)cn1] | OC(=O)COc1ncc(cn1)-c1cc2C(=O)NC(c2c(NC(=O)c2cc(F)cc(c2)C(F)(F)F)c1)cc(F)ccc1Cl | (400 MHz, CD3CN) 8.86 (s, 3H), 8.00 (s, 1H), 7.77 (s, 1H), 7.70-7.57 (m, 4H), 7.32 (br. s, 1H), 7.26 (dd, 9.0, 5.0 Hz, 1H), 6.98 (td, 8.3, 2.8 Hz, 1H), 6.66 (br. s, 1H), 6.16 (br. s, 1H), 4.92 (s, 2H). | 619.2 | A | |
| I-1391 | 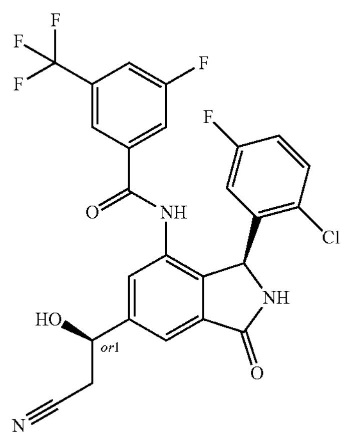 [SMILES: N#CC[C@@H](O)c1cc(NC(=O)c2cc(F)cc(C(F)(F)F)c2)c2c(c1)C(=O)N[C@@H]2c1cc(F)ccc1Cl] | O[C@H](CC#N)c1cc2C(=O)N[C@@H](c2c(NC(=O)c2cc(F)cc(c2)C(F)(F)F)c1)cc(F)ccc1Cl | (400 MHz, DMSO-d6) 10.58 (s, 1H), 9.16 (br s, 1H), 7.94 (d, 7.4 Hz, 1H), 7.81-7.70 (m, 2H), 7.66 (s, 1H), 7.54 (s, 1H), 7.32 (dd, 8.9, 5.2 Hz, 1H), 7.10 (td, 8.5, 3.0 Hz, 1H), 6.52 (br s, 1H), 6.23 (d, 4.0 Hz, 1H), 5.96 (br s, 1H), 5.07 (app q, 4.9 Hz, 1H), 3.03 (dd, 16.8, 4.7 Hz, 1H), 2.95 (dd, 16.8, 6.5 Hz, 1H). | 536.2 | D | |
| I-1392 | 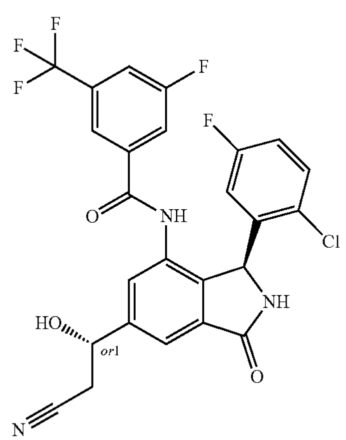 [SMILES: N#CC[C@H](O)c1cc(NC(=O)c2cc(F)cc(C(F)(F)F)c2)c2c(c1)C(=O)N[C@@H]2c1cc(F)ccc1Cl] | O[C@@H](CC#N)c1cc2C(=O)N[C@@H](c2c(NC(=O)c2cc(F)cc(c2)C(F)(F)F)c1cc(F)ccc1Cl | (400 MHz, DMSO-d6) 10.60 (s, 1H), 9.15 (s, 1H), 7.93 (d, 7.8 Hz, 1H), 7.79-7.69 (m, 2H), 7.67 (s, 1H), 7.61 (s, 1H), 7.31 (dd, 8.9, 5.2 Hz, 1H), 7.09 (td, 8.5, 2.9 Hz, 1H), 6.55 (br s, 1H), 6.24 (d, 3.5 Hz, 1H), 5.97 (br s, 1H), 5.12 (app q, 3.6 Hz, 1H), 3.01 (dd, 16.8, 4.9 Hz, 1H), 2.94 (dd, 16.7, 6.4 Hz, 1H). | 536.2 | D | |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-1393 | 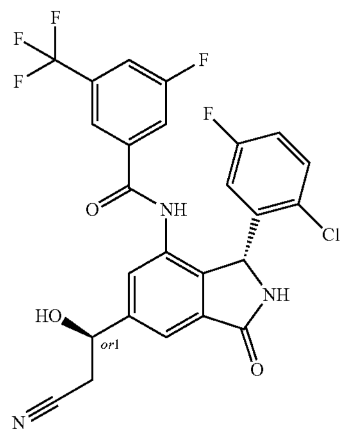 [SMILES: N#CC[C@@H](O)c1cc(NC(=O)c2cc(F)cc(C(F)(F)F)c2)c2c(c1)C(=O)N[C@H]2c1cc(F)ccc1Cl] | O[C@H](CC#N)c1cc2C(=O)N[C@H](c2c(NC(=O)c2cc(F)cc(c2)C(F)(F)F)c1)c1cc(F)ccc1Cl | (400 MHz, DMSO-d6) 10.58 (s, 1H), 9.16 (br s, 1H), 7.94 (d, 7.4 Hz, 1H), 7.83-7.70 (m, 2H), 7.66 (s, 1H), 7.54 (s, 1H), 7.32 (dd, 8.9, 5.2 Hz, 1H), 7.10 (td, 8.5, 3.0 Hz, 1H), 6.54 (br s, 1H), 6.23 (d, 4.0 Hz, 1H), 5.96 (br s, 1H), 5.07 (app q, 5.0 Hz, 1H), 3.02 (dd, 16.8, 4.7 Hz, 1H), 2.95 (dd, 16.8, 6.5 Hz, 1H). | 536.2 | A | |
| I-1394 | 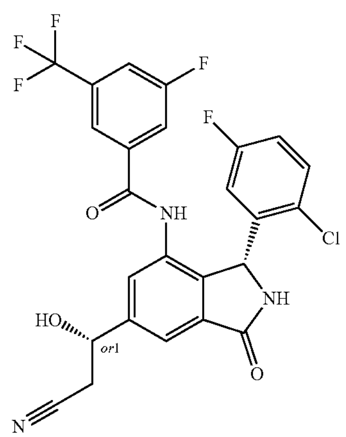 [SMILES: N#CC[C@H](O)c1cc(NC(=O)c2cc(F)cc(C(F)(F)F)c2)c2c(c1)C(=O)N[C@H]2c1cc(F)ccc1Cl] | O[C@@H](CC#N)c1cc2C(=O)N[C@H](c2c(NC(=O)c2cc(F)cc(c2)C(F)(F)F)c1)c1cc(F)ccc1Cl | (400 MHz, DMSO-d6) 10.59 (s, 1H), 9.15 (br s, 1H), 7.93 (d, 7.9 Hz, 1H), 7.78-7.69 (m, 2H), 7.67 (s, 1H), 7.61 (s, 1H), 7.31 (dd, 8.9, 5.2 Hz, 1H), 7.09 (td, 8.5, 3.0 Hz, 1H), 6.51 (br s, 1H), 6.23 (d, 3.3 Hz, 1H), 5.97 (br s, 1H), 5.11 (app q, 4.2 Hz, 1H), 3.00 (dd, 16.7, 4.9 Hz, 1H), 2.93 (dd, 16.7, 6.4 Hz, 1H). | 536.2 | A | |
| I-1395 | 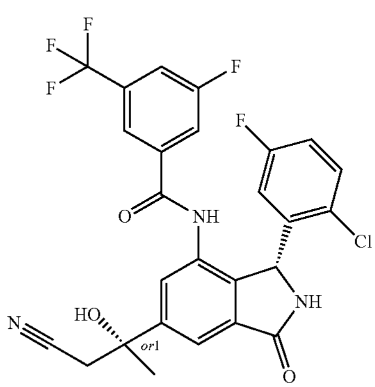 [SMILES: C[C@@](O)(CC#N)c1cc(NC(=O)c2cc(F)cc(C(F)(F)F)c2)c2c(c1)C(=O)N[C@H]2c1cc(F)ccc1Cl] | C[C@@](O)(CC#N)c1cc2C(=O)N1C@H](c2c(NC(=O)c2cc(F)cc(c2)C(F)(F)F)c1)c1cc(F)ccc1Cl | (400 MHz, DMSO-d6) 10.69 (br s, 1H), 9.10 (br s, 1H), 7.95-7.83 (m, 1H), 7.81 (br s, 1H), 7.76-7.66 (m, 3H), 7.32 (dd, 8.8, 5.2 Hz, 1H), 7.09 (td, 8.4, 3.0 Hz, 1H), 6.52 (br s, 1H), 6.07 (br s, 1H), 5.95 (br s, 1H), 3.08 (s, 2H), 1.60 (s, 3H). | 550.3 | A | |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-1396 | 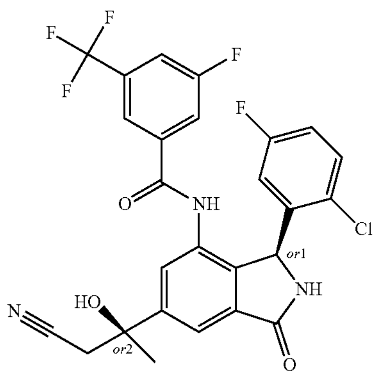 [SMILES: C[C@](O)(CC#N)c1cc(NC(=O)c2cc(F)cc(C(F)(F)F)c2)c2c(c1)C(=O)N[C@@H]2c1cc(F)ccc1Cl] | C[C@](O)(CC#N)c1cc2C(=O)N[C@@H](c2c(NC(=O)c2cc(F)cc(c2)C(F)(F)F)c1)c1cc(F)ccc1Cl | (400 MHz, DMSO-d6) 10.59 (s, 1H), 9.14 (br s, 1H), 7.98-7.87 (m, 1H), 7.81 (s, 1H), 7.78-7.64 (m, 3H), 7.31 (dd, 8.9, 5.2 Hz, 1H), 7.09 (td, 8.6, 2.9 Hz, 1H), 6.53 (br s, 1H), 6.07 (s, 1H), 5.96 (br s, 1H), 3.08 (s, 2H), 1.62 (s, 3H). | 550.3 | D | |
| I-1397 | 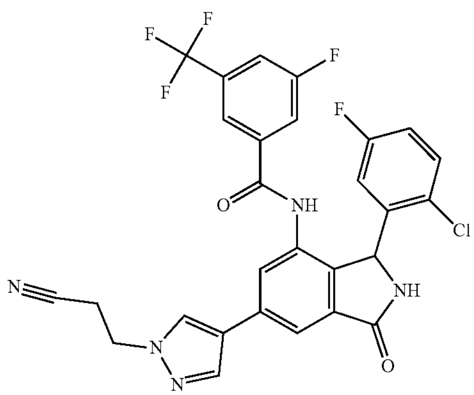 [SMILES: N#CCCn1cc(-c2cc(NC(=O)c3cc(F)cc(C(F)(F)F)c3)c3c(c2)C(=O)NC3c2cc(F)ccc2Cl)cn1] | Fc1ccc(C1)c(c1)C1NC(=O)c2cc(cc(NC(=O)c3cc(F)cc(c3)C(F)(F)F)c12)-c1cnn(CCC#N)c1 | NMR (400 MHz, DMSO-d6) 10.56 (s, 1H), 9.17 (br s, 1H), 8.48 (s, 1H), 8.14 (s, 1H), 7.96 (br d, 8.4 Hz, 1H), 7.91 (s, 1H), 7.76 (br d, 9.1 Hz, 1H), 7.70 (s, 2H), 7.32 (dd, 8.9, 5.2 Hz, 1H), 7.09 (td, 8.5, 2.9 Hz, 1H), 6.65 (br s, 1H), 5.99 (br s, 1H), 4.44 (t, 6.3 Hz, 2H), 3.13 (t, 6.3 Hz, 2H) | 586.3 | A | |
| I-1398 | 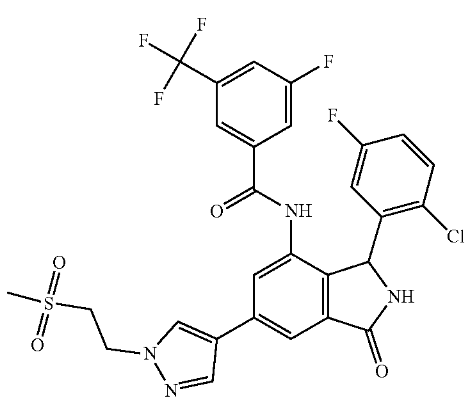 [SMILES: CS(=O)(=O)CCn1cc(-c2cc(NC(=O)c3cc(F)cc(C(F)(F)F)c3)c3c(c2)C(=O)NC3c2cc(F)ccc2Cl)cn1] | CS(=O)(=O)CCn1cc(cn1)-c1cc2C(=O)NC(c2c(NC(=O)c2cc(F)cc(c2)C(F)(F)F)c1c(F)ccc1Cl | NMR (400 MHz, DMSO-d6) 10.58 (br s, 1H), 9.15 (br s, 1H), 8.48 (s, 1H), 8.12 (s, 1H), 7.96 (br d, 8.4 Hz, 1H), 7.90 (s, 1H), 7.76 (br d, 8.9 Hz, 1H), 7.70 (s, 2H), 7.31 (dd, 8.9, 5.2 Hz, 1H), 7.09 (td, 8.5, 3.0 Hz, 1H), 6.68 (br s, 1H), 5.96 (br s, 1H), 4.60 (t, 6.8 Hz, 2H), 3.76 (t, 6.8 Hz, 2H), 2.90 (s, 3H). | 639.2 | A | |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-1399 | 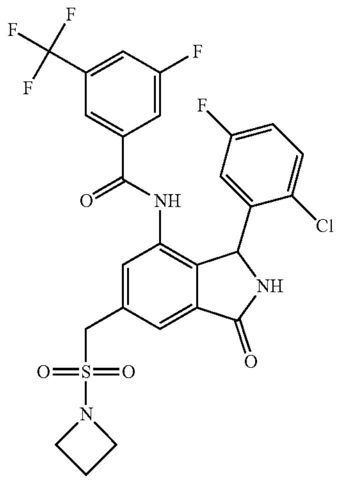 [SMILES: O=C(Nc1cc(CS(=O)(=O)N2CCC2)cc2c1C(c1cc(F)ccc1Cl)NC2=O)c1cc(F)cc(C(F)(F)F)c1] | Fc1ccc(C1)c(c1)C1NC(=O)c2cc(CS(=O)(=O)N3CCC3)cc(NC(=O)c3cc(F)cc(c3)C(F)(F)F)c12 | NMR (400 MHz, DMSOd6) 10.63 (br. s, 1H), 9.22 (br. s, 1H), 7.95 (br. d, 8.3 Hz, 1H), 7.80 (s, 1H), 7.75 (br. d, 8.7 Hz, 1H), 7.66 (s, 1H), 7.56 (s, 1H), 7.32 (dd, 8.8, 5.2 Hz, 1H), 7.10 (td, 8.3, 2.8 Hz, 1H), 6.55 (br. s, 1H), 5.97 (br. s, 1H), 4.81-4.69 (m, 2H), 3.90 (t, 7.7 Hz, 4H), 2.19 (p, 7.8, 2H). | 600.3 | A | |
| I-1400 | 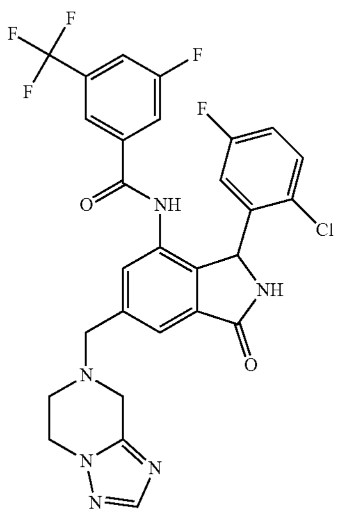 [SMILES: O=C(Nc1cc(CN2CCn3ncnc3C2)cc2c1C(c1cc(F)ccc1Cl)NC2=O)c1cc(F)cc(C(F)(F)F)c1] | Fc1ccc(C1)c(c1)C1NC(=O)c2cc(CN3CCn4ncnc4C3)cc(NC(=O)c3cc(F)cc(c3)C(F)(F)F)c12 | (400 MHz, DMSO-D6) 10.58 (br s, 1 H), 9.16 (s, 1 H), 7.94 (d, 9.7 Hz, 1 H), 7.74 (d, 8.9 Hz, 1 H), 7.69 (s, 1 H), 7.65 (s, 1 H), 7.52 (s, 1 H), 7.31 (dd, 8.9, 5.2 Hz, 1 H), 7.08 (td, 8.5, 3.0 Hz, 1 H), 6.64 (br s, 1 H), 5.98 (br s, 1 H), 4.17 (t, 5.3 Hz, 2 H), 3.99-3.87 (m, 2 H), 3.75 (s, 2 H), 3.10-3.01 (m, 2 H). | 603.4 | A | |
| I-1401 | 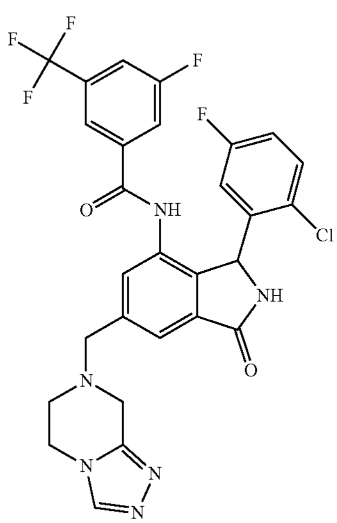 [SMILES: O=C(Nc1cc(CN2CCn3cnnc3C2)cc2c1C(c1cc(F)ccc1Cl)NC2=O)c1cc(F)cc(C(F)(F)F)c1] | Fc1ccc(C1)c(c1)C1NC(=O)c2cc(CN3CCn4cnnc4C3)cc(NC(=O)c3cc(F)cc(c3)C(F)(F)F)c12 | (400 MHz, DMSO-D6) 10.61 (br s, 1 H), 9.17 (s, 1 H), 8.45 (s, 1 H), 7.95-7.91 (m, 1 H), 7.74 (d, 8.9 Hz, 1 H), 7.69 (s, 1 H), 7.65 (s, 1 H), 7.51 (s, 1 H), 7.31 (dd, 8.9, 5.2 Hz, 1 H), 7.09 (td, 8.5, 3.0 Hz, 1 H), 6.67 (br s, 1 H), 5.99 (br s, 1 H), 4.08 (t, 5.4 Hz, 2 H), 3.97-3.86 (m, 2 H), 3.76 (s, 2 H), 2.98-2.89 (m, 2 H).. | 603.4 | A | |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-1402 | 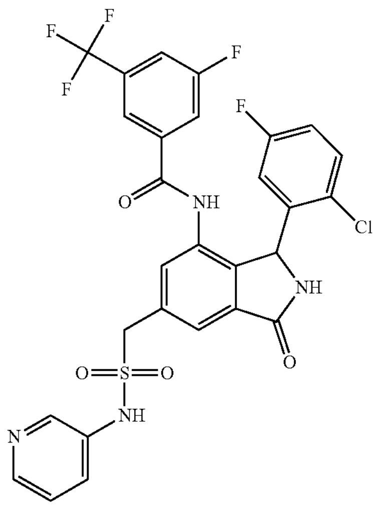 [SMILES: O=C(Nc1cc(CS(=O)(=O)Nc2cccnc2)cc2c1C(c1cc(F)ccc1Cl)NC2=O)c1cc(F)cc(C(F)(F)F)c1] | Fc1ccc(C1)c(c1)C1NC(=O)c2cc(CS(=O)(=O)Nc3cccnc3)cc(NC(=O)c3cc(F)cc(c3)C(F)(F)F)c12 | NMR (400 MHz, DMSO-d6) 10.61 (s, 1H), 10.47 (br. s, 1H), 9.20 (br. s, 1H), 8.37 (d, 2.4 Hz, 1H), 8.24 (dd, 4.6, 1.2 Hz, 1H), 7.95 (br. d, 8.3 Hz, 1H), 7.73 (br. d, 8.7 Hz, 1H), 7.66 (d, 0.8 Hz, 1H), 7.62 (s, 1H), 7.56 (ddd, 8.3, 2.7, 1.4 Hz, 1H), 7.46 (s, 1H), 7.36-7.28 (m, 2H), 7.11 (td, 8.5, 3.0 Hz), 6.48 (br. s, 1H), 5.98 (br. s, 1H), 4.79 (d, 13.9 Hz, 1H), 4.74 (d, 14.1 Hz, 1H). | 637.3 | A | |
| I-1403 | 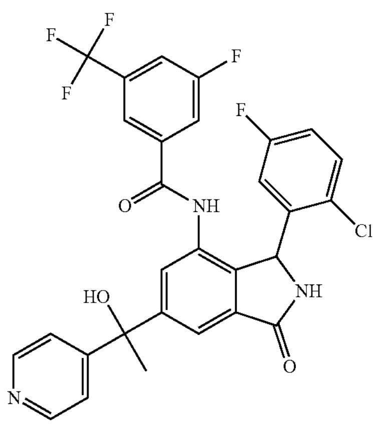 [SMILES: CC(O)(c1ccncc1)c1cc(NC(=O)c2cc(F)cc(C(F)(F)F)c2)c2c(c1)C(=O)NC2c1cc(F)ccc1Cl] | CC(O)(c1ccncc1)c1cc2C(=O)NC(c2c(NC(=O)c2cc(F)cc(c2)C(F)(F)c1)c1cc(F)ccc1Cl | NMR (400 MHz, DMSO-d6) 10.53 (s, 0.5H), 10.51 (s, 0.5H) 9.15 (br. s, 1H), 8.53-8.50 (m, 2H), 7.93 (br. d, 8.5 Hz, 1H), 7.78 (d, 1.3 Hz, 0.5H), 7.74 (d, 1.3 Hz, 0.5H) 7.73 (br. d, 9.0 Hz, 1H), 7.64 (d, 6.4 Hz, 1H), 7.56 (s, 0.5H), 7.52 (s, 0.5H), 7.51 (s, 1H), 7.49 (s, 1H), 7.29 (dd, 8.9, 5.2 Hz, 1H), 7.08 (td, 8.6, 3.0 Hz, 1H), 6.54 (br. s, 1H), 6.29 (br. s, 1H), 5.92 (br. s, 1H), 1.94 (s, 1.5H), 1.93 (s, 1.5H). | 588.2 | A | |
| I-1404 | 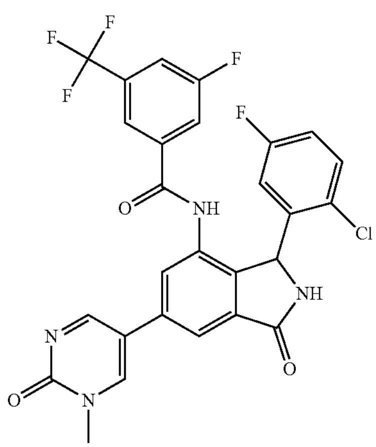 [SMILES: Cn1cc(-c2cc(NC(=O)c3cc(F)cc(C(F)(F)F)c3)c3c(c2)C(=O)NC3c2cc(F)ccc2Cl)cnc1=O] | Cn1cc(cnc1=O)-c1cc2C(=O)NC(c2c(NC(=O)c2cc(F)cc(c2)C(F)(F)c1)c1cc(F)ccc1Cl | 1H NMR (400 MHz, DMSO-d6) 10.61 (s, 1H), 9.22 (br. s, 1H), 9.03 (d, 5.8 Hz, 1H), 8.84 (d, 3.4 Hz, 1H), 7.98 (s, 1H), 7.96 (submerged br.d, 5.8 Hz, 1H), 7.77 (s, 1H), 7.76 (submerged br. d, 5.5 Hz, 1H), 7.70 (s, 1H), 7.33 (dd, 8.9, 5.2 Hz, 1H), 7.10 (td, 8.6, 3.0 Hz, 1H), 6.63 (br. s, 1H), 5.99 (br. s, 1H), 3.54 (s, 3H); | 575.2 | A | |

TABLE 2-continued

Representative Compounds of the Invention with Bioactivity Data.

| Ex. No. | Structure | SMILES | $^1$H NMR | MS | ADP-Glo IC$_{50}$ | MCF 10A IC$_{50}$ |
|---|---|---|---|---|---|---|
| I-1405 | 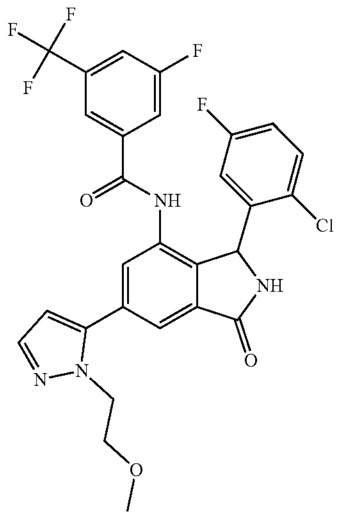 [SMILES: COCCn1nccc1-c1cc(NC(=O)c2cc(F)cc(C(F)(F)F)c2)c2c(c1)C(=O)NC2c1cc(F)ccc1Cl] | COCCn1nccc1-c1cc2C(=O)NC(c2c(NC(=O)c2cc(F)cc(c2)C(F)(F)F)c1)c1cc(F)ccc1Cl | | 606.23 | B | |
| I-1406 | 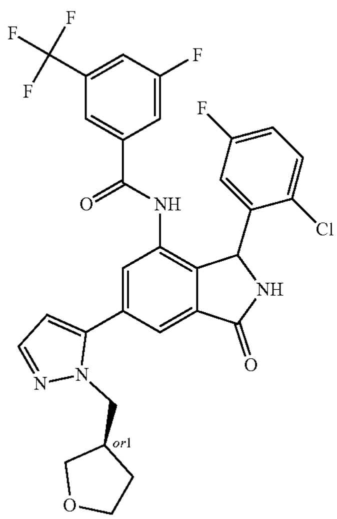 [SMILES: O=C(Nc1cc(-c2ccnn2C[C@H]2CCOC2)cc2c1C(c1cc(F)ccc1Cl)NC2=O)c1cc(F)cc(C(F)(F)F)c1] | Fc1ccc(C1)c(c1)C1NC(=O)c2cc(cc(NC(=O)c3cc(F)cc(c3)C(F)(F)F)c12)-c1ccnn1C[C@H]1CCOC1 | | 617.24 | A | |
| I-1407 | 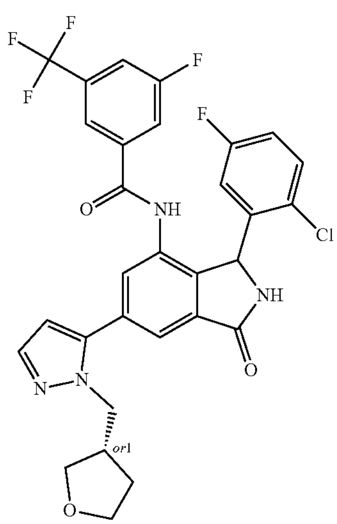 [SMILES: O=C(Nc1cc(-c2ccnn2C[C@@H]2CCOC2)cc2c1C(c1cc(F)ccc1Cl)NC2=O)c1cc(F)cc(C(F)(F)F)c1] | Fc1ccc(C1)c(c1)C1NC(=O)c2cc(cc(NC(=O)c3cc(F)cc(c3)C(F)(F)F)c12)-c1ccnn1C[C@@H]1CCOC1 | | 617.29 | A | |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-1408 | 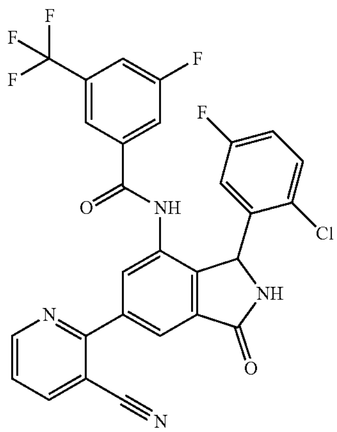 [SMILES: N#Cc1cccnc1-c1cc(NC(=O)c2cc(F)cc(C(F)(F)F)c2)c2c(c1)C(=O)NC2c1cc(F)ccc1Cl] | Fc1ccc(C1)c(c1)C1NC(=O)c2cc(cc(NC(=O)c3cc(F)cc(c3)C(F)(F)F)c12)-c1ncccc1C#N | | 569.27 | A | |
| I-1409 | 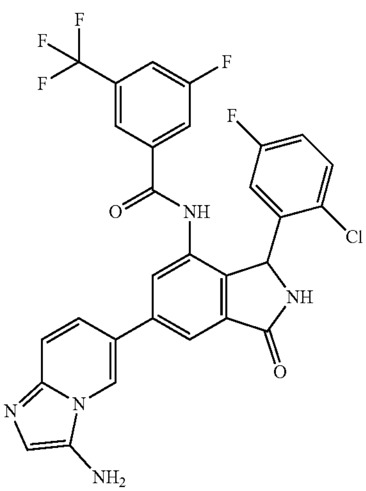 [SMILES: Nc1cnc2ccc(-c3cc(NC(=O)c4cc(F)cc(C(F)(F)F)c4)c4c(c3)C(=O)NC4c3cc(F)ccc3Cl)cn12] | Nc1cnc2ccc(cn12)-c1cc2C(=O)NC(c2c(NC(=O)c2cc(F)cc(c2)C(F)(F)F)c1)c1cc(F)ccc1Cl | | 598.28 | A | |
| I-1410 | 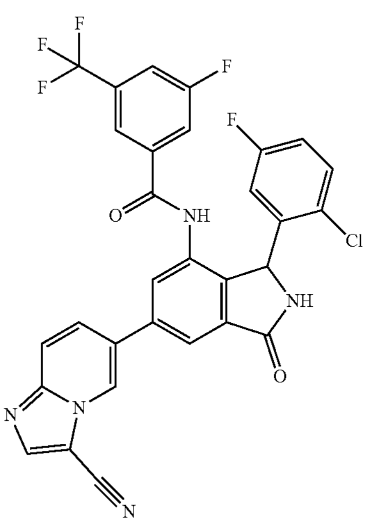 [SMILES: N#Cc1cnc2ccc(-c3cc(NC(=O)c4cc(F)cc(C(F)(F)F)c4)c4c(c3)C(=O)NC4c3cc(F)ccc3Cl)cn12] | Fc1ccc(C1)c(c1)C1NC(=O)c2cc(cc(NC(=O)c3cc(F)cc(c3)C(F)(F)F)c12)-c1ccc2ncc(C#N)n2c1 | | 608.23 | A | |

TABLE 2-continued

Representative Compounds of the Invention with Bioactivity Data.

| Ex. No. | Structure | SMILES | $^1$H NMR | MS | ADP-Glo IC$_{50}$ | MCF 10A IC$_{50}$ |
|---|---|---|---|---|---|---|
| I-1411 | 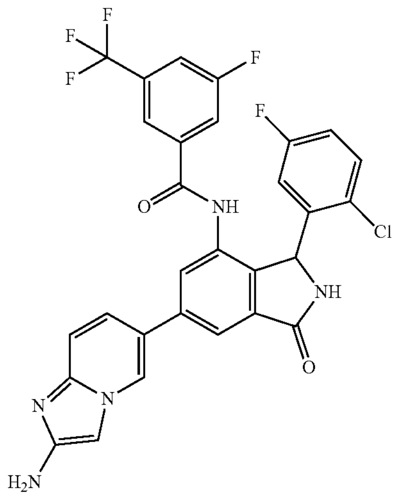 [SMILES: Nc1cn2cc(-c3cc(NC(=O)c4cc(F)cc(C(F)(F)F)c4)c4c(c3)C(=O)NC4c3cc(F)ccc3Cl)ccc2n1] | Nc1cn2cc(ccc2n1)-c1cc2C(=O)NC(c2c(NC(=O)c2cc(F)cc(c2)C(F)(F)F)c1)c1cc(F)ccc1Cl | | 598.28 | A | |
| I-1412 | 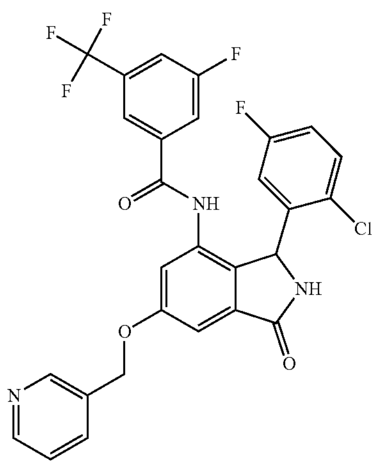 [SMILES: O=C(Nc1cc(OCc2cccnc2)cc2c1C(c1cc(F)ccc1Cl)NC2=O)c1cc(F)cc(C(F)(F)F)c1] | Fc1ccc(C1)c(c1)C1NC(=O)c2cc(OCc3cccnc3)cc(NC(=O)c3cc(F)cc(c3)C(F)(F)F)c12 | | 574.27 | A | |
| I-1413 | 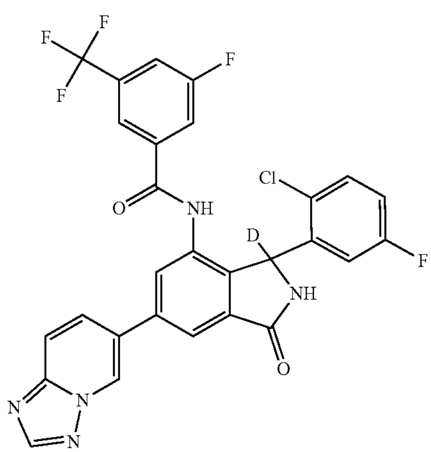 [SMILES: [2H]C1(c2cc(F)ccc2Cl)NC(=O)c2cc(-c3ccc4ncnn4c3)cc(NC(=O)c3cc(F)cc(C(F)(F)F)c3)c21] | [2H]C1(NC(=O)c2cc(cc(NC(=O)c3cc(F)cc(c3)C(F)(F)F)c12)-c1ccc2ncnn2c1)c1cc(F)ccc1Cl | 1H NMR (500 MHz, DMSO-d6) 6.50 (s, 1 H) 7.10 (td, 8.20, 3.13 Hz, 1 H) 7.33 (dd, 8.85, 5.19 Hz, 1 H) 7.70-7.72 (m, 1 H) 7.74-7.79 (m, 1 H) 7.96 (d, 8.70 Hz, 2 H) 7.98 (s, 1 H) 8.11-8.15 (m, 2 H) 8.56 (s, 1 H) 9.46 (d, 0.76 Hz, 1 H) 10.62 (s, 1 H) | 585.23 | A | |

TABLE 2-continued

Representative Compounds of the Invention with Bioactivity Data.

| Ex. No. | Structure | SMILES | $^1$H NMR | MS | ADP-Glo IC$_{50}$ | MCF 10A IC$_{50}$ |
|---|---|---|---|---|---|---|
| I-1414 | 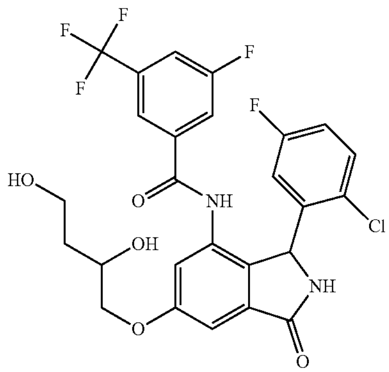 [SMILES: O=C(Nc1cc(OCC(O)CCO)cc2c1C(c1cc(F)ccc1Cl)NC2=O)c1cc(F)cc(C(F)(F)F)c1] | OCCC(O)COc1cc2C(=O)NC(c2c(NC(=O)c2cc(F)cc(c2)C(F)(F)F)c1c c(F)ccc1Cl | 1H NMR (400 MHz, DMSO-d6) 10.48 (br s, 1H), 9.15 (br s, 1H), 7.96 (d, 7.5 Hz, 1H), 7.72 (d, 8.9 Hz, 1H), 7.63 (s, 1H), 7.31 (dd, 8.9, 5.2 Hz, 1H), 7.20 (s, 1H), 7.13-7.03 (m, 2H), 6.57 (br s, 1H), 5.93 (br s, 1H), 4.93 (d, 3.8 Hz, 1H), 4.52-4.43 (m, 1H), 4.07-3.89 (m, 3H), 3.63-3.50 (m, 2H), 1.77-1.50 (m, 2H). | 571.2 | A | |
| I-1415 | 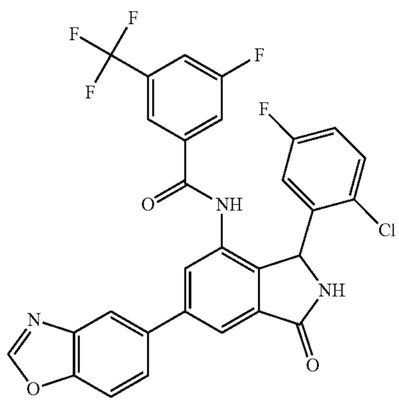 [SMILES: O=C(Nc1cc(-c2ccc3ocnc3c2)cc2c1C(c1cc(F)ccc1Cl)NC2=O)c1cc(F)cc(C(F)(F)F)c1] | Fc1ccc(C1)c(c1)C1NC(=O)c2cc(cc(NC(=O)c3cc(F)cc(c3)C(F)(F)F)c12)-c1ccc2ocnc2c1 | NMR (400 MHz, DMSO-d6) 10.62 (br s, 1H), 9.24 (s, 1H), 8.84 (s, 1H), 8.19 (d, 1.5 Hz, 1H), 8.00 (d, 1.5 Hz, 1H), 7.97 (d, 8.4 Hz, 1H), 7.92 (d, 8.6 Hz, 1H), 7.90-7.84 (m, 1H), 7.78 (d, 9.1 Hz, 1H), 7.71 (s, 1H), 7.34 (dd, 8.9, 5.2 Hz, 1H), 7.11 (td, 8.4, 3.1 Hz, 1H), 6.86-6.56 (br s), 1H, 6.07 (br s, 1H). | 582.2 | A | |
| I-1416 | 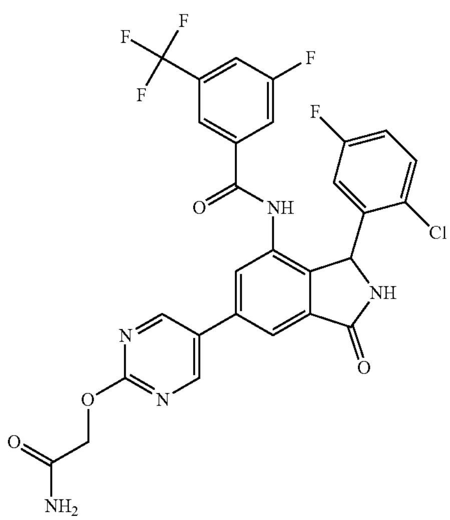 [SMILES: NC(=O)COc1ncc(-c2cc(NC(=O)c3cc(F)cc(C(F)(F)F)c3)c3c(c2)C(=O)NC3c2cc(F)ccc2Cl)cn1] | NC(=O)COc1ncc(cn1)-c1cc2C(=O)NC(c2c(NC(=O)c2cc(F)cc(c2)C(F)(F)F)c1)c1cc(F)ccc1Cl | (400 MHz, DMSO-d6) 10.66 (br s, 1H), 9.25 (br s, 1H), 9.05 (s, 2H), 8.06 (s, 1H), 7.97 (d, 8.5 Hz, 1H), 7.86 (s, 1H), 7.76 (d, 9.0 Hz, 1H), 7.69 (s, 1H), 7.55 (s, 1H), 7.33 (dd, 8.9, 5.2 Hz, 1H), 7.25 (s, 1H), 7.11 (td, 8.4, 3.1 Hz, 1H), 6.67 (br s, 1H), 6.04 (br s, 1H), 4.80 (s, 2H). | 618.1 | A | |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-1417 | 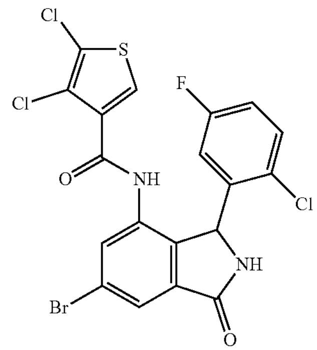 [SMILES: O=C(Nc1cc(Br)cc2c1C(c1cc(F)ccc1Cl)NC2=O)c1csc(Cl)c1Cl] | Fc1ccc(C1)c(c1)C1NC(=O)c2cc(Br)cc(NC(=O)c3csc(Cl)c3Cl)c12 | 1H NMR (400 MHz, DMSO-d6) 10.35 (s, 1H), 9.28 (s, 1H), 7.85-7.79 (s, 1H), 7.78 (d, 1.8 Hz, 1H), 7.70 (s, 1H), 7.56-7.39 (s, 1H), 7.30-7.12 (s, 1H), 7.09-6.20 (s, 1H), 6.00 (s, 1H). | 534.9 | D | |
| I-1418 | 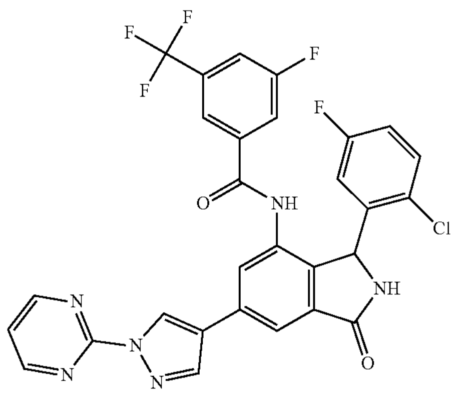 [SMILES: O=C(Nc1cc(-c2cnn(-c3ncccn3)c2)cc2c1C(c1cc(F)ccc1Cl)NC2=O)c1cc(F)cc(C(F)(F)F)c1] | Fc1ccc(C1)c(c1)C1NC(=O)c2cc(cc(NC(=O)c3cc(F)cc(c3)C(F)(F)F)c12)-c1cnn(c1)-c1ncccn1 | NMR (400 MHz, DMSO-d6) 10.57 (br s, 1H), 9.29 (s, 1H), 9.20 (br s, 1H), 8.93 (s, 1H), 8.92 (s, 1H), 8.54 (s, 1H), 8.14 (s, 1H), 7.99 (br d, 7.1 Hz, 1H), 7.96 (s, 1H), 7.78 (br d, 9.6 Hz, 1H), 7.73 (s, 1H), 7.53 (t, 4.8 Hz, 1H), 7.33 (dd, 8.9, 5.2 Hz, 1H), 7.10 (td, 8.5, 3.1 Hz, 1H), 6.65 (br s, 1H), 6.01 (br s, 1H). | 611.2 | A | A |
| I-1419 | 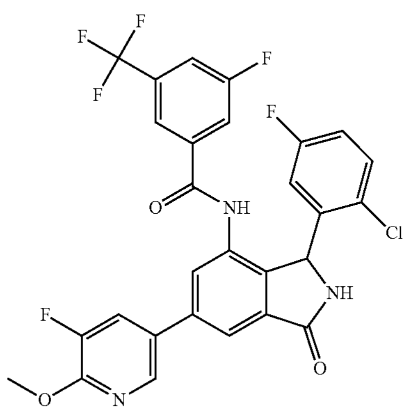 [SMILES: COc1ncc(-c2cc(NC(=O)c3cc(F)cc(C(F)(F)F)c3)c3c(c2)C(=O)NC3c2cc(F)ccc2Cl)cc1F] | COc1ncc(cc1F)-c1cc2C(=O)NC(c2c(NC(=O)c2cc(F)cc(c2)C(F)(F)F)c1)c1cc(F)ccc1Cl | 1H NMR (400 MHz, DMSO-d6) 10.64 (br. s, 1H), 9.25 (s, 1H), 8.45 (d, 1.9 Hz, 1H), 8.22 (dd, 11.8, 1.9 Hz, 1H), 8.01 (s, 1H), 7.97 (d, 8.8 Hz, 1H), 7.84 (s, 1H), 7.76 (d, 9.0 Hz, 1H), 7.70 (s, 1H), 7.33 (dd, 8.9, 5.2 Hz, 1H), 7.11 (td, 8.5, 3.0 Hz, 1H), 6.69 (br. s, 1H), 6.04 (br. s, 1H), 4.01 (s, 3H) | 592.2 | A | |
| I-1420 | 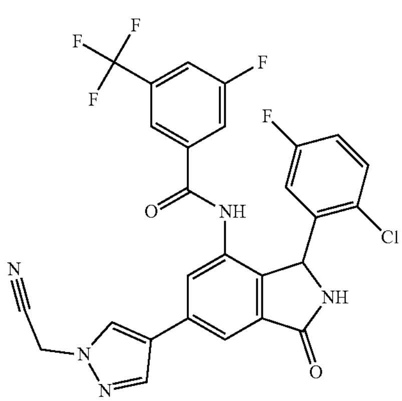 [SMILES: N#CCn1cc(-c2cc(NC(=O)c3cc(F)cc(C(F)(F)F)c3)c3c(c2)C(=O)NC3c2cc(F)ccc2Cl)cn1] | Fc1ccc(C1)c(c1)C1NC(=O)c2cc(cc(NC(=O)c3cc(F)cc(c3)C(F)(F)F)c12)-c1cnn(CC#N)c1 | NMR (400 MHz, DMSO-d6) 10.64 (br s, 1H), 9.18 (br s, 1H), 8.48 (s, 1H), 8.22 (s, 1H), 7.95 (d, 8.5 Hz, 1H), 7.92 (s, 1H), 7.76 (d, 8.0 Hz, 1H), 7.73 (overlapping d, 12.0 Hz, 1H), 7.32 (dd, 8.9, 5.2 Hz, 1H), 7.09 (td, 8.4, 2.9 Hz, 1H), 6.61 (br s, 1H), 5.98 (br s, 1H), 5.55 (s, 2H). | 570.3 | A | |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-1421 | 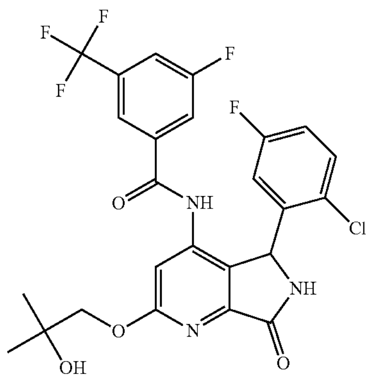 [SMILES: CC(C)(O)COc1cc(NC(=O)c2cc(F)cc(C(F)(F)F)c2)c2c(n1)C(=O)NC2c1cc(F)ccc1Cl] | CC(C)(O)COc1cc(NC(=O)c2cc(F)cc(c2)C(F)(F)F)c2C(NC(=O)c2n1)c1cc(F)ccc1Cl | NMR (400 MHz, DMSOd6) 9.35 (s, 1H), 7.92 (d, 8.3 Hz, 1H), 7.70 (d, 9.0 Hz, 1H), 7.61 (s, H), 7.35 (dd, 8.9, 5.2 Hz, 1H), 7.17-7.00 (td, 1H, 8.3, 3.0 Hz), 7.09 (s, 1H), 6.83 (br s, 1H), 5.95 (s, 1H), 4.73 (br s, 1H), 4.20-4.10 (m, 2H), 1.23 (s, 6H). | 556.3 | B | |
| I-1422 | 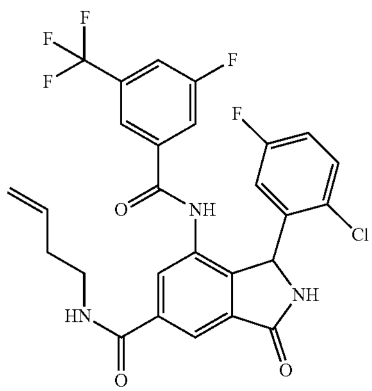 [SMILES: C=CCCNC(=O)c1cc(NC(=O)c2cc(F)cc(C(F)(F)F)c2)c2c(c1)C(=O)NC2c1cc(F)ccc1Cl] | Fc1ccc(C1)c(c1)C1NC(=O)c2cc(cc(NC(=O)c3cc(F)cc(c3)C(F)(F)F)c12)C(=O)NCCC=C | (400 MHz, DMSO-d6) 10.64 (br s, 1 H), 9.27 (s, 1 H), 8.85 (t, 5.6 Hz, 1 H), 8.21 (s, 1 H), 7.99 (d, 0.7 Hz, 1 H), 7.96 (d, 8.4 Hz, 1 H), 7.76 (d, 8.9 Hz, 1 H), 7.68 (s, 1 H), 7.32 (dd, 8.9, 5.2 Hz, 1 H), 7.09 (td, 8.5, 3.0 Hz, 1 H), 6.53 (br s, 1 H), 6.03 (br s, 1 H), 5.85 (ddt, 17.0, 10.3, 6.7 Hz, 1 H), 5.15-5.07 (m, 1 H), 5.06-5.01 (m, 1 H), 3.37 (app dd, 12.9, 6.8 Hz, 2 H), 2.32 (app q, 6.9 Hz, 2 H). | 564.3 | A | |
| I-1423 | 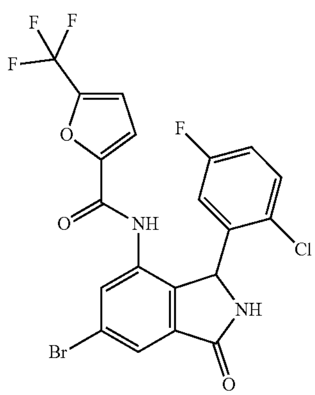 [SMILES: O=C(Nc1cc(Br)cc2c1C(c1cc(F)ccc1Cl)NC2=O)c1ccc(C(F)(F)F)o1] | Fc1ccc(C1)c(c1)C1NC(=O)c2cc(Br)cc(NC(=O)c3ccc(o3)C(F)(F)F)c12 | 1H NMR (400 MHz, Chloroform-d) 8.58 (s, 1H), 7.94 (d, 1.7 Hz, 1H), 7.57 (s, 1H), 7.50 (dd, 9.0, 4.9 Hz, 1H), 7.27 (dd, 3.6, 0.9 Hz, 1H), 7.07 (ddd, 8.9, 7.4, 3.0 Hz, 1H), 6.95 (dt, 3.7, 1.1 Hz, 1H), 6.70-6.65 (m, 2H), 6.23 (s, 1H). | 518.95 | D | |
| I-1424 | 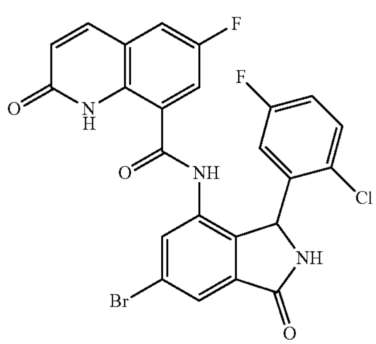 | Fc1ccc(C1)c(c1)C1NC(=O)c2cc(Br)cc(NC(=O)c3cc(F)cc4ccc(=O)[nH]c34)c12 | 1H NMR (400 MHz, DMSO-d6) 11.53 (s, 1H), 10.62 (s, 1H), 9.33 (s, 1H), 7.98 (d, 9.7 Hz, 1H), 7.86 (d, 11.8 Hz, 3H), 7.32 (s, 2H), 7.10 (s, 1H), 6.70 (d, 9.7 Hz, 1H), 6.03 (s, 1H). | 544 | D | |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-1425 | 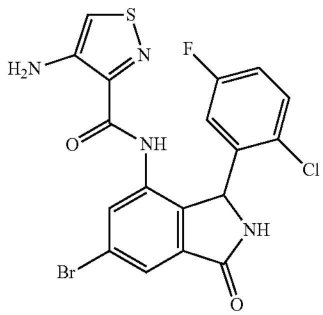 [SMILES: Nc1csnc1C(=O)Nc1cc(Br)cc2c1C(c1cc(F)ccc1Cl)NC2=O] | Nc1csnc1C(=O)Nc1cc(Br)cc2C(=O)NC(c12)c1cc(F)ccc1Cl | 1H NMR (400 MHz, DMSO-d6) 9.98 (s, 1H), 9.27 (s, 1H), 7.97 (s, 1H), 7.70 (d, 16.1 Hz, 2H), 7.35 (s, 1H), 7.12 (dt, 9.4, 4.8 Hz, 1H), 6.12 (s, 1H), 5.75 (s, 2H). | 480.95 | E | |
| I-1426 | 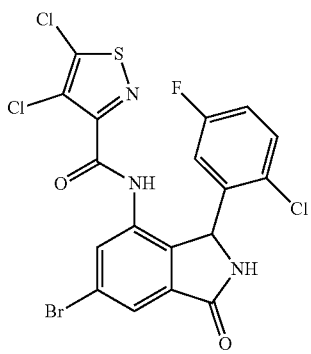 [SMILES: O=C1NC(c2cc(F)ccc2Cl)c2c(NC(=O)c3nsc(Cl)c3Cl)cc(Br)cc21] | Fc1ccc(C1)c(c1)C1NC(=O)c2cc(Br)cc(NC(=O)c3nsc(Cl)c3Cl)c12 | 1H NMR (400 MHz, DMSO-d6) 10.51 (s, 1H), 9.30 (s, 1H), 7.81 (q, 1.8 Hz, 2H), 7.42-7.34 (m, 1H), 7.15 (ddd, 8.9, 7.9, 3.1 Hz, 1H), 6.95-6.20 (s, 1H), 6.05 (s, 1H). | 535.9 | D | |
| I-1427 | 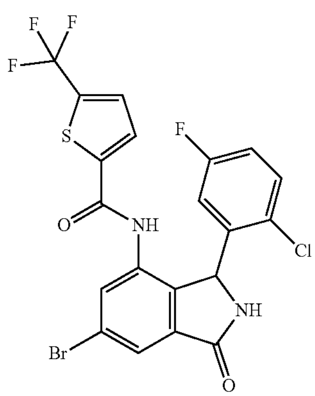 [SMILES: O=C(Nc1cc(Br)cc2c1C(c1cc(F)ccc1Cl)NC2=O)c1ccc(C(F)(F)F)s1] | Fc1ccc(C1)c(c1)C1NC(=O)c2cc(Br)cc(NC(=O)c3ccc(s3)C(F)(F)F)c12 | 1H NMR (400 MHz, DMSO-d6) 10.60 (s, 1H), 9.30 (s, 1H), 7.83 (d, 1.7 Hz., 1H), 7.79-7.70 (m, 2H), 7.60 (dt, 4.0, 1.4 Hz, 1H), 7.33 (dd, 8.9, 5.1 Hz, 1H), 7.10 (ddd, 8.9, 7.9, 3.1 Hz, 1H), 6.82 (s, 1H), 5.99 (s, 1H). | 534.95 | D | |
| I-1428 | 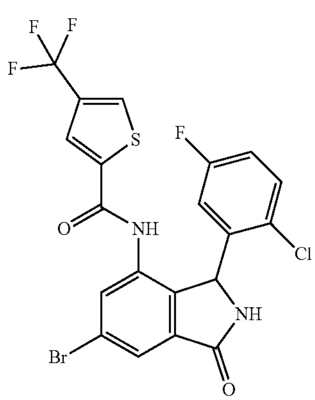 [SMILES: O=C(Nc1cc(Br)cc2c1C(c1cc(F)ccc1Cl)NC2=O)c1cc(C(F)(F)F)cs1] | Fc1ccc(C1)c(c1)C1NC(=O)c2cc(Br)cc(NC(=O)c3cc(cs3)C(F)(F)F)c12 | 1H NMR (400 MHz, DMSO-d6) 10.43 (s, 1H), 9.29 (s, 1H), 8.56-8.51 (m, 1H), 7.81 (d, 1.7 Hz, 1H), 7.73 (dd, 2.7, 1.5 Hz, 2H), 7.31 (dd, 8.9, 5.2 Hz, 1H), 7.13-7.03 (m, 1H), 7.00-6.10 (s, 1H), 5.98 (s, 1H). | 534.9 | D | |

TABLE 2-continued

Representative Compounds of the Invention with Bioactivity Data.

| Ex. No. | Structure | SMILES | $^1$H NMR | MS | ADP-Glo IC$_{50}$ | MCF 10A IC$_{50}$ |
|---|---|---|---|---|---|---|
| I-1429 | 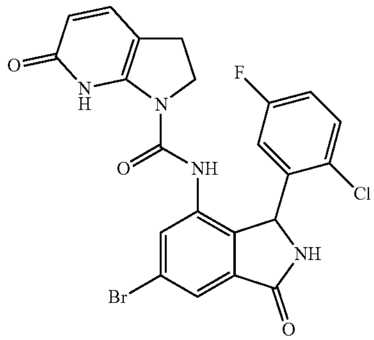 | Fc1ccc(C1)c(c1)C1NC(=O)c2cc(Br)cc(NC(=O)N3CCc4cc(=O)[nH]c34)c12 | 1H NMR (400 MHz, DMSO-d6) 10.66 (s, 2H), 9.27 (s, 1H), 7.89 (s, 1H), 7.76-7.63 (m, 1H), 7.47 (d, 8.0 Hz, 1H), 7.29 (dd, 8.9, 5.1 Hz, 1H), 7.04 (td, 8.4, 3.0 Hz, 1H), 6.18 (d, 8.1 Hz, 2H), 3.92 (q, 9.3 Hz, 1H), 3.80 (q, 10.0, 9.3 Hz, 1H), 3.17 (d, 5.2 Hz, 1H), 2.89 (t, 8.6 Hz, 1H). | 519 | E | |
| I-1430 | 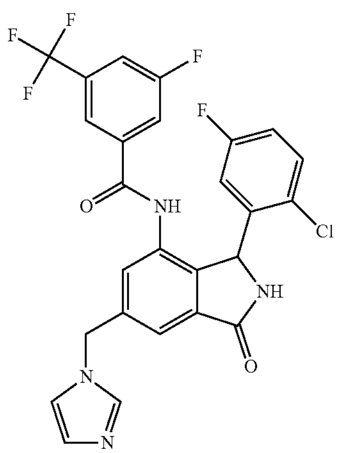 [SMILES: O=C(Nc1cc(Cn2ccnc2)cc2c1C(c1cc(F)ccc1Cl)NC2=O)c1cc(F)cc(C(F)(F)F)c1] | Fc1ccc(C1)c(c1)C1NC(=O)c2cc(Cn3cnc3)cc(NC(=O)c3cc(F)cc(c3)C(F)(F)F)c12 | 1H-NMR (400 MHz, DMSO-d6) 10.55 (br. s, 1H), 9.19 (br. s, 1H), 7.94 (br. d, 8.5 Hz, 1H), 7.84 (s, 1H), 7.71 (br. d, 8.7 Hz, 1H), 7.62 (s, 1H), 7.58 (d, 0.6 Hz, 1H), 7.34 (s, 1H), 7.30 (dd, 8.9, 5.2 Hz, 1H), 7.28 (s, 1H), 7.09 (app. td, 8.4, 3.1 Hz, 1H), 6.95 (s, 1H), 6.57 (br. s, 1H), 5.95 (br. s, 1H), 5.44-5.33 (m, 2H). | 547.3 | A | |
| I-1431 | 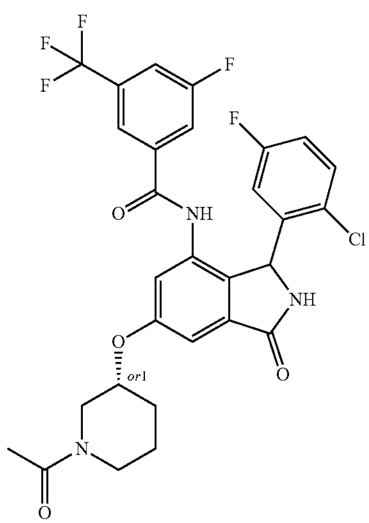 [SMILES: CC(=O)N1CCC[C@@H](Oc2cc(NC(=O)c3cc(F)cc(C(F)(F)F)c3)c3c(c2)C(=O)NC3c2cc(F)ccc2Cl)C1] | CC(=O)N1CCC[C@H](C1)Oc1cc2C(=O)NC(c2c(NC(=O)c2cc(F)cc(c2)C(F)(F)F)c1c(F)ccc1Cl | (400 MHz, DMSO-d6) 10.43 (br s, 1H), 9.14 (s, 1H), 7.95 (d, 8.4 Hz, 1H), 7.71 (d, 8.2 Hz, 1H), 7.64 (s, 1H), 7.31 (dd, 8.8, 5.2 Hz, 1H), 7.25 (ddd, 13.6, 6.3, 2.1 Hz, 1H), 7.13-7.02 (m, 2H), 6.54 (br s, 1H), 5.91 (br s, 1H), 4.79-4.68 (m, 0.5H), 4.54-4.43 (m, 0.5H), 4.00-3.87 (m, 0.5H), 3.83-3.46 (m, 2.5H), 3.24-3.10 (m, 1H), 2.09-1.40 (m, 7H) | 608.3 | A | |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-1432 | 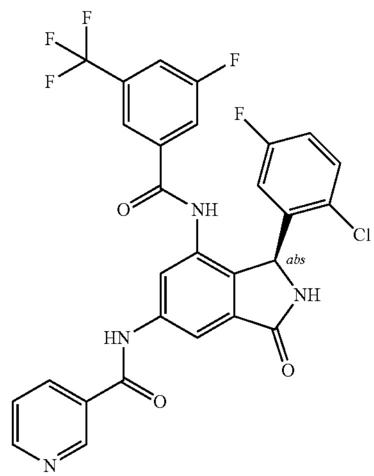 [SMILES: O=C(Nc1cc(NC(=O)c2cc(F)cc(C(F)(F)F)c2)c2c(c1)C(=O)N[C@@H]2c1cc(F)ccc1Cl)c1cccnc1] | Fc1ccc(C1)c(c1)[C@H]1NC(=O)c2cc(NC(=O)c3cccnc3)cc(NC(=O)c3cc(F)cc(c3)C(F)(F)F)c12 | (400 MHz, DMSO-d6) 10.46 (br s, 1H), 9.16 (s, 1H), 7.95 (d, 8.4 Hz, 1H), 7.70 (d, 8.9 Hz, 1H), 7.62 (s, 1H), 7.35-7.28 (m, 1H), 7.26-7.19 (m, 1H), 7.12-7.03 (m, 2H), 6.60 (br s, 1H), 5.93 (br s, 1H), 5.34-5.24 (m, 0.5H), 5.22-5.14 (m, 0.5H), 3.85 (dd, 11.9, 4.4 Hz, 0.5H), 3.69-3.51 (m, 3.5H), 2.29-2.06 (m, 2H), 1.98 (s, 1.8H), 1.96 (s, 0.6H), 1.95 (s, 0.6H) | 594.2 | A | |
| I-1433 | 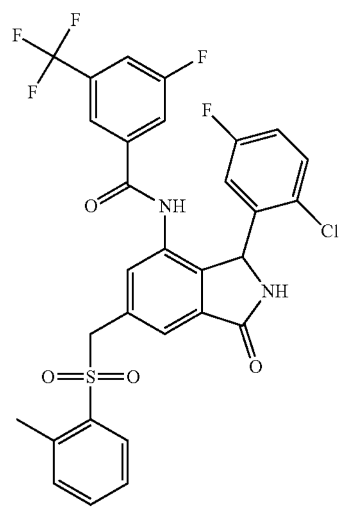 [SMILES: Cc1ccccc1S(=O)(=O)Cc1cc(NC(=O)c2cc(F)cc(C(F)(F)F)c2)c2c(c1)C(=O)NC2c1cc(F)ccc1Cl] | Cc1ccccc1S(=O)(=O)Cc1cc2C(=O)NC(c2c(NC(=O)c2cc(F)cc(c2)C(F)(F)F)c1c1Cl | NMR (400 MHz, CD3CN) 8.64 (s,1H), 7.70 (d, 7.8, 0.9 Hz,1H), 7.65 (dt, 8.8 Hz, 1.5Hz, 1H), 7.61-7.56 (m, 2H), 7.55 (d, 0.8 Hz, 1H), 7.41 (d., 7.0 Hz, 1H), 7.33 (app. t, 7.7 Hz, 1H), 7.26 (dd, 8.9, 5.1 Hz, 1H), 7.25-7.22 (submerged m, 1H), 6.57 (br, s, 1H), 6.13 (br, s, 1H), 4.60 (s, 2H), 2.63 (s,3H). | 635 | A | |
| I-1434 | 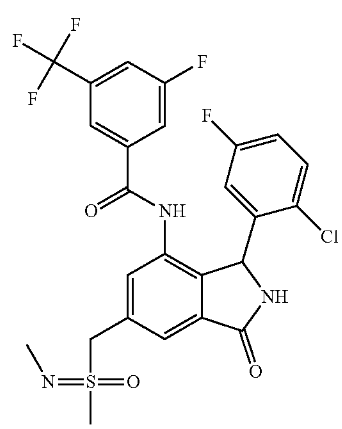 [SMILES: CN=S(C)(=O)Cc1cc(NC(=O)c2cc(F)cc(C(F)(F)F)c2)c2c(c1)C(=O)NC2c1cc(F)ccc1Cl] | CN=S(C)(=O)Cc1cc2C(=O)NC(c2c(NC(=O)c2cc(F)cc(c2)C(F)(F)F)c1ccc1Cl | NMR (400 MHz, DMSO-d6) 10.60 (s, 1H), 9.20 (br. s, 1H), 7.95 (br. d, 8.2 Hz, 1H), 7.79 (s, 1H), 7.74 (br. d, 8.7 Hz, 1H), 7.64 (s, 1H), 7.51 (s, 0.5H), 7.50 (s, 0.5H), 7.32 (dd, 8.7, 5.1 Hz, 1H), 7.13-7.06 (m, 1H), 6.73 (br. s, 1H), 5.98 (br. s, 1H), 4.70 (d, 13.5 Hz, 1H), 4.64 (d, 13.6 Hz, 1H), , 2.83 (s, 1.5H), 2.82 (s, 1.5H), 2.69 (s, 1.5H), 2.67 (s, 1.5H). | 572.1 | A | |

TABLE 2-continued

Representative Compounds of the Invention with Bioactivity Data.

| Ex. No. | Structure | SMILES | ¹H NMR | MS | ADP-Glo $IC_{50}$ | MCF 10A $IC_{50}$ |
|---|---|---|---|---|---|---|
| I-1435 | 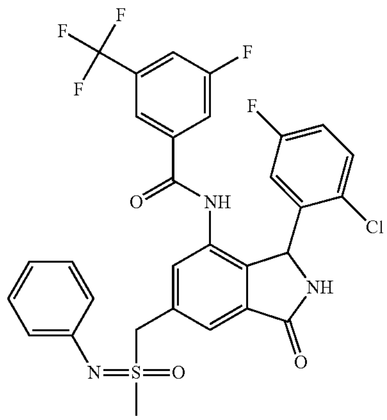 [SMILES: CS(=O)(Cc1cc(NC(=O)c2cc(F)cc(C(F)(F)F)c2)c2c(c1)C(=O)NC2c1cc(F)ccc1Cl)=Nc1ccccc1] | CS(=O)(Cc1cc2C(=O)NC(c2c(NC(=O)c2cc(F)cc(c2)C(F)(F)F)c1cc(F)ccc1C1)=Nc1cccc1 | NMR (400 MHz, DMSO-d6) 10.63 (br. s, 1H), 9.21 (br. s, 1H), 7.96 (br. d, 8.3 Hz, 1H), 7.81 (s, 0.5H), 7.79 (s, 0.5H), 7.73 (br. d, 8.9 Hz, 1H), 7.64 (s, 1H), 7.56 (s, 0.5H), 7.50 (s, 0.5H), 7.32 (dd, 8.3, 5.2 Hz, 2 x 0.5H), 7.21-7.15 (m, 2H), 7.10 (td, 8.2, 2.3 Hz, 1H), 7.01-6.94 (m, 2H), 6.90-6.85 (m, 1H), 6.61 (br. s, 1H), 5.98 (br. s, 1H), 4.99-4.81 (m, 2H), 3.07 (s, 3H).. | 634.2 | A | |
| I-1436 | 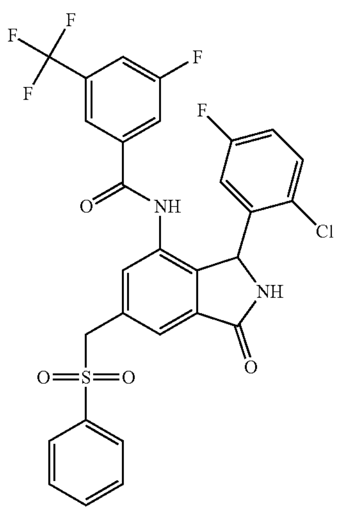 [SMILES: O=C(Nc1cc(CS(=O)(=O)c2ccccc2)cc2c1C(c1cc(F)ccc1Cl)NC2=O)c1cc(F)cc(C(F)(F)F)c1] | Fc1ccc(C1)c(c1)C1NC(=O)c2cc(CS(=O)(=O)c3ccccc3)cc(NC(=O)c3cc(F)cc(c3)C(F)(F)F)c12 | NMR (400 MHz, CD3CN) 8.72 (d, 23.5 Hz, 1H), 7.75-7.71 (m, 2H), 7.69 (dt, 2.5, 1.5Hz, 1H) 7.67-7.63 (m, 1H) 7.61-7.52 (m, 4H), 7.46 (s, 1H), 7.43-7.39 (s, 1H), 7.34-7.29 (m, 1H), 7.26 (dd, 8.9, 5.1 Hz, 1H), 7.01-6.95 (m, 1H), 6.61 (br, s, 1H), 6.15 (br, s, 1H), 4.69-4.33 (m, 2H). | 621 | A | |
| I-1437 | 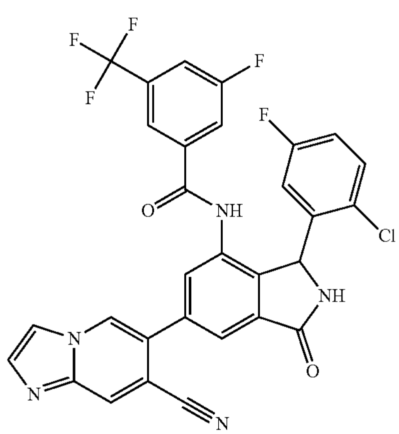 [SMILES: N#Cc1cc2nccn2cc1-c1cc(NC(=O)c2cc(F)cc(C(F)(F)F)c2)c2c(c1)C(=O)NC2c1cc(F)ccc1Cl] | Fc1ccc(C1)c(c1)C1NC(=O)c2cc(cc(NC(=O)c3cc(F)cc(c3)C(F)(F)F)c12)-c1cn2ccnc2cc1C#N | 1H NMR (400 MHz, DMSO-d6) 10.71 (br. s, 1H), 9.33 (br. s, 1H), 8.98 (d, 0.8 Hz, 1H), 8.55 (app.t, 0.8 Hz 1H), 8.19 (s, 1H), 7.98 (d, 8.1 H2, 1H), 7.95-7.92 (submerged m, 1H), 7.93 (d, 1.1 Hz, 1H), 7.81-7.70 (m, 2H), 7.68 (s, 1H), 7.36 (dd, 8.9, 5.2 Hz, 1H), 7.13 (td, 8.1, 2.9 Hz, 1H), 6.68 (br. s, 1H), 6.07 (br. s, 1H) | 608.1 | A | |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-1438 | 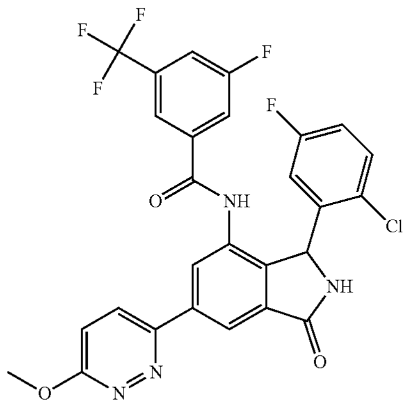 [SMILES: COc1ccc(-c2cc(NC(=O)c3cc(F)cc(C(F)(F)F)c3)c3c(c2)C(=O)NC3c2cc(F)ccc2Cl)nn1] | COc1ccc(nn1)-c1cc2C(=O)NC(c2c(NC(=O)c2cc(F)cc(c2)C(F)(F)F)c1)c1cc(F)ccc1Cl | 1H NMR (400 MHz, DMSO-d6) 10.70 (s, 1H), 9.29 (br. s, 1H), 8.40-8.30 (m, 2H), 8.26 (s, 1H), 7.96 (br. d, 8.2 Hz, 1H), 7.76 (br. d, 8.9 Hz, 1H), 7.68 (s, 1H), 7.38 (d, 9.3 Hz, 1H), 7.33 (dd, 9.0, 5.2 Hz, 1H), 7.10 (td, 8.4, 2.7 Hz, 1H), 6.61 (br. s, 1H), 6.06 (br. s, 1H), 4.10 (s, 3H) | 575.2 | A | |
| I-1439 | 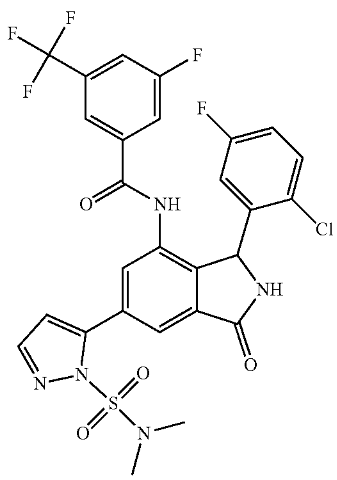 [SMILES: CN(C)S(=O)(=O)n1nccc1-c1cc(NC(=O)c2cc(F)cc(C(F)(F)F)c2)c2c(c1)C(=O)NC2c1cc(F)ccc1Cl] | CN(C)S(=O)(=O)n1nccc1-c1cc2C(=O)NC(c2c(NC(=O)c2cc(F)cc(c2)C(F)(F)F)c1)c1cc(F)ccc1Cl | | 640.24 | A | |
| I-1440 | 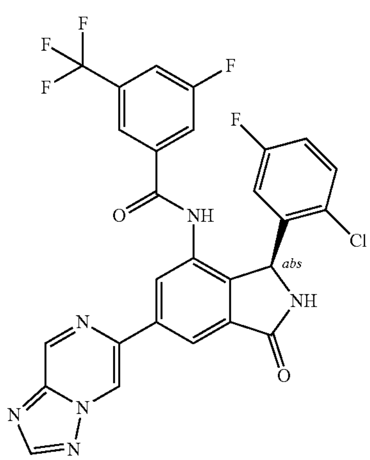 [SMILES: O=C(Nc1cc(-c2cn3ncnc3cn2)cc2c1[C@@H](c1cc(F)ccc1Cl)NC2=O)c1cc(F)cc(C(F)(F)F)c1] | Fc1ccc(C1)c(c1)[C@H]1NC(=O)c2cc(cc(NC(=O)c3cc(F)cc(c3)C(F)(F)F)c12)-c1cn2ncnc2cn1 | | 585.4 | D | |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-1441 | 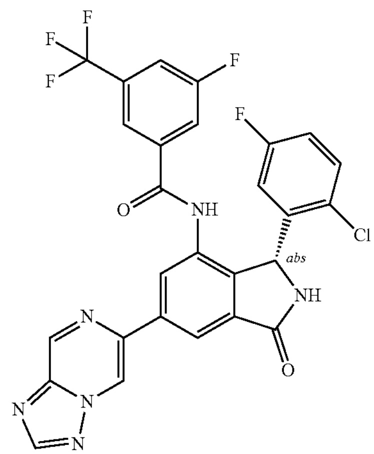 [SMILES: O=C(Nc1cc(-c2cn3ncnc3cn2)cc2c1[C@H](c1cc(F)ccc1Cl)NC2=O)c1cc(F)cc(C(F)(F)F)c1] | Fc1ccc(C1)c(c1)[C@@H]1NC(=O)c2cc(cc(NC(=O)c3cc(F)cc(c3)C(F)(F)F)c12)-c1cn2ncnc2cn1 | | 585.4 | A | A |
| I-1442 | 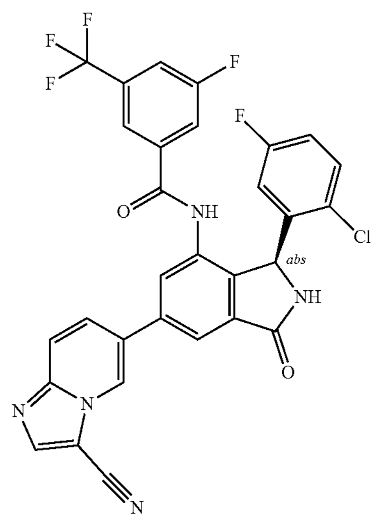 [SMILES: N#Cc1cnc2ccc(-c3cc(NC(=O)c4cc(F)cc(C(F)(F)F)c4)c4c(c3)C(=O)N[C@@H]4c3cc(F)ccc3Cl)cn12] | Fc1ccc(C1)c(c1)[C@H]1NC(=O)c2cc(cc(NC(=O)c3cc(F)cc(c3)C(F)(F)F)c12)-c1ccc2ncc(C#N)n2c1 | | 608.2 | B | |
| I-1443 | 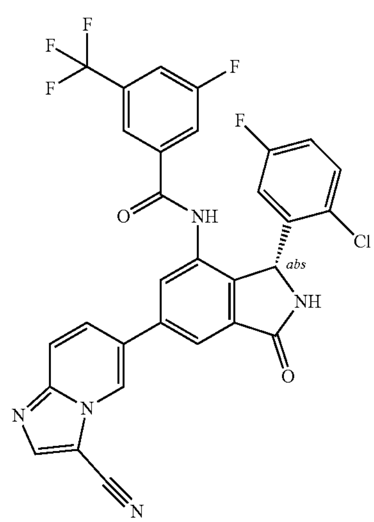 [SMILES: N#Cc1cnc2ccc(-c3cc(NC(=O)c4cc(F)cc(C(F)(F)F)c4)c4c(c3)C(=O)N[C@H]4c3cc(F)ccc3Cl)cn12] | Fc1ccc(C1)c(c1)[C@@H]1NC(=O)c2cc(cc(NC(=O)c3cc(F)cc(c3)C(F)(F)F)c12)-c1ccc2ncc(C#N)n2c1 | | 608.2 | A | |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-1444 | 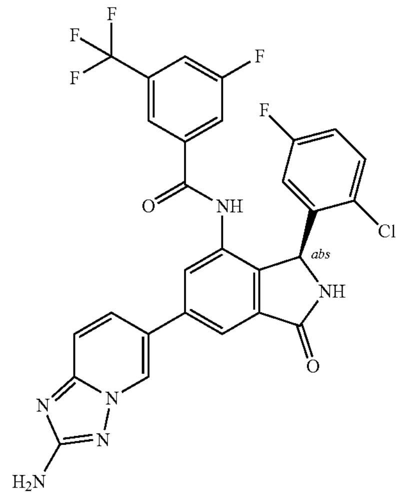 [SMILES: Nc1nc2ccc(-c3cc(NC(=O)c4cc(F)cc(C(F)(F)F)c4)c4c(c3)C(=O)N[C@@H]4c3cc(F)ccc3Cl)cn2n1] | Nc1nc2c cc(cn2n1)- c1cc2C(= O)N[C@ @H](c2c (NC(=O) c2cc(F)cc (c2)C(F) (F)F)c1)c 1cc(F)ccc 1Cl | | 599.2 | A | |
| I-1445 | 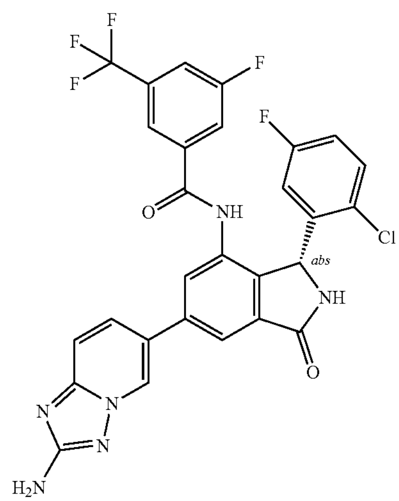 [SMILES: Nc1nc2ccc(-c3cc(NC(=O)c4cc(F)cc(C(F)(F)F)c4)c4c(c3)C(=O)N[C@H]4c3cc(F)ccc3Cl)cn2n1] | Nc1nc2c cc(cn2n1)- c1cc2C(= O)N[C@ H](c2c(N C(=O)c2 cc(F)cc(c 2)C(F)(F) F)c1)c1c c(F)ccc1 Cl | | 599.2 | A | |
| I-1446 | 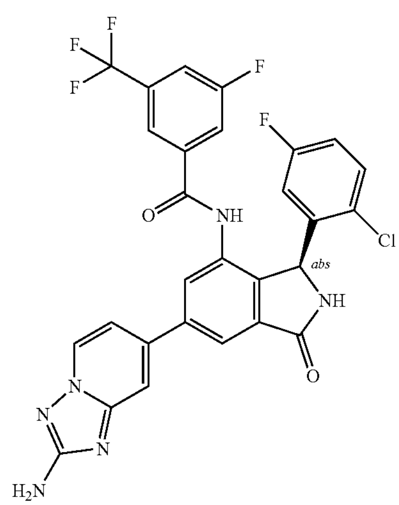 [SMILES: Nc1nc2cc(-c3cc(NC(=O)c4cc(F)cc(C(F)(F)F)c4)c4c(c3)C(=O)N[C@@H]4c3cc(F)ccc3Cl)ccn2n1] | Nc1nc2c c(ccn2n1)- c1cc2C(= O)N[C@ @H](c2c (NC(=O) c2cc(F)cc (c2)C(F) (F)F)c1)c 1cc(F)ccc 1Cl | | 599.2 | A | |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-1447 | 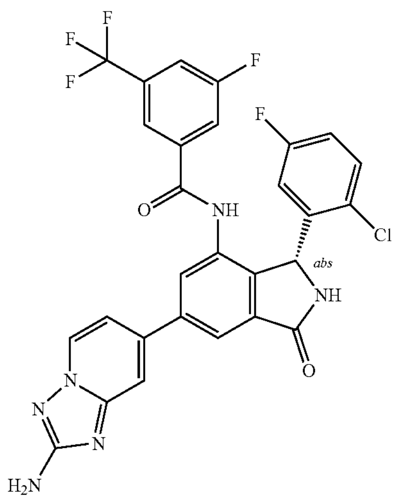 [SMILES: Nc1nc2cc(-c3cc(NC(=O)c4cc(F)cc(C(F)(F)F)c4)c4c(c3)C(=O)N[C@H]4c3cc(F)ccc3Cl)ccn2n1] | Nc1nc2cc(ccn2n1)-c1cc2C(=O)N[C@H](c2c(NC(=O)c2cc(F)cc(c2)C(F)(F)F)c1)c1cc(F)ccc1Cl | | 599.2 | A | |
| I-1448 | 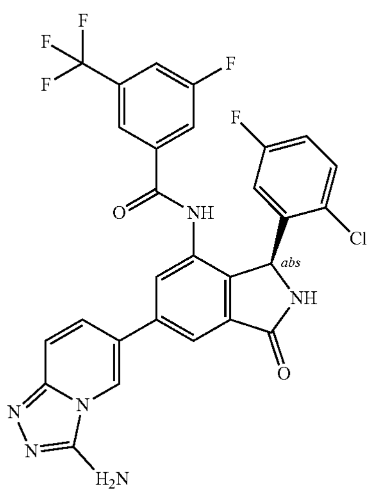 [SMILES: Nc1nnc2ccc(-c3cc(NC(=O)c4cc(F)cc(C(F)(F)F)c4)c4c(c3)C(=O)N[C@@H]4c3cc(F)ccc3Cl)cn12] | Nc1nnc2ccc(cn12)-c1cc2C(=O)N[C@@H](c2c(NC(=O)c2cc(F)cc(c2)C(F)(F)F)c1)c1cc(F)ccc1Cl | | | | C |
| I-1449 | 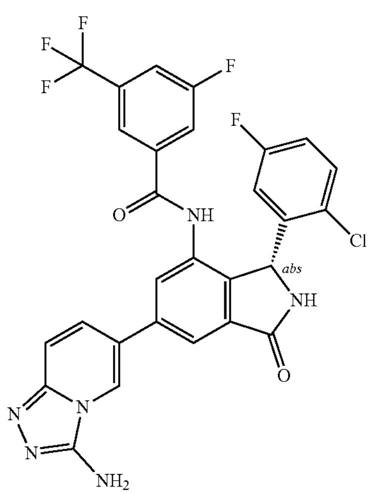 [SMILES: Nc1nnc2ccc(-c3cc(NC(=O)c4cc(F)cc(C(F)(F)F)c4)c4c(c3)C(=O)N[C@H]4c3cc(F)ccc3Cl)cn12] | Nc1nnc2ccc(cn12)-c1cc2C(=O)N[C@H](c2c(NC(=O)c2cc(F)cc(c2)C(F)(F)F)c1)c1cc(F)ccc1Cl | ¹H NMR (500 MHz, DMSO) δ 10.65 (s, 1H), 9.25 (s, 1H), 8.66 (t, J = 1.4 Hz, 1H), 8.04 (d, J = 1.7 Hz, 1H), 7.96 (dt, J = 8.6, 2.0 Hz, 1H), 7.83 (s, 1H), 7.77 (d, J = 9.1 Hz, 1H), 7.70 (s, 1H), 7.55 (qd, J = 9.7, 1.4 Hz, 2H), 7.33 (dd, J = 8.9, 5.2 Hz, 1H), 7.10 (td, J = 8.4, 3.1 Hz, 1H), 6.53 (s, 2H), 6.04 (s, 1H). | 599.19 | A | |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-1450 | 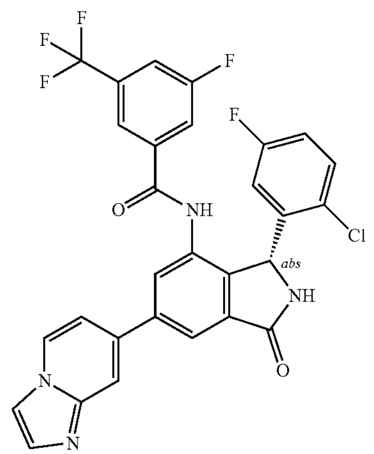 [SMILES: O=C(Nc1cc(-c2ccn3ccnc3c2)cc2c1[C@H](c1cc(F)ccc1Cl)NC2=O)c1cc(F)cc(C(F)(F)F)c1] | Fc1ccc(C1)c(c1)[C@@H]1NC(=O)c2cc(cc(NC(=O)c3cc(F)cc(c3)C(F)(F)F)c12)-c1ccn2ccnc2c1 | | | | A |
| I-1451 | 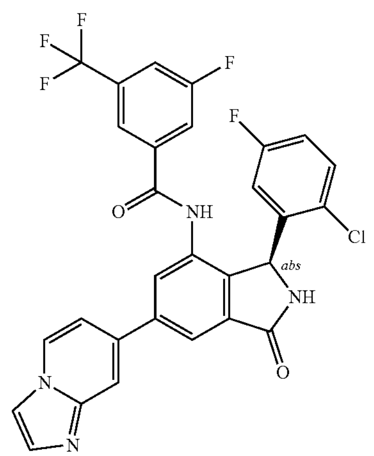 [SMILES: O=C(Nc1cc(-c2ccn3ccnc3c2)cc2c1[C@@H](c1cc(F)ccc1Cl)NC2=O)c1cc(F)cc(C(F)(F)F)c1] | Fc1ccc(C1)c(c1)[C@H]1NC(=O)c2cc(cc(NC(=O)c3cc(F)cc(c3)C(F)(F)F)c12)-c1ccn2ccnc2c1 | | | | B |
| I-1452 | 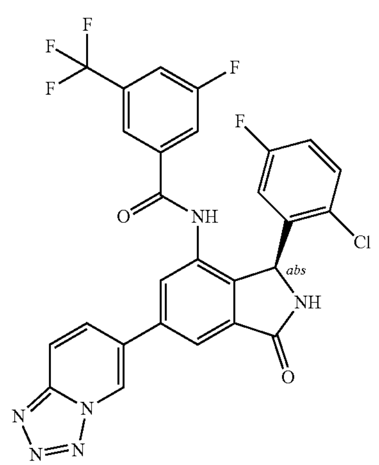 [SMILES: O=C(Nc1cc(-c2ccc3nnnn3c2)cc2c1[C@@H](c1cc(F)ccc1Cl)NC2=O)c1cc(F)cc(C(F)(F)F)c1] | Fc1ccc(C1)c(c1)[C@H]1NC(=O)c2cc(cc(NC(=O)c3cc(F)cc(c3)C(F)(F)F)c12)-c1ccc2nnnn2c1 | | 585.5 | | D |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-1453 | 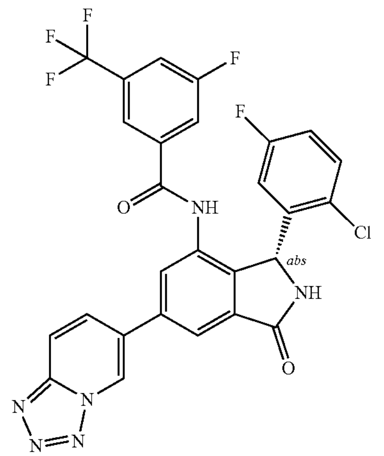 [SMILES: O=C(Nc1cc(-c2ccc3nnnn3c2)cc2c1[C@H](c1cc(F)ccc1Cl)NC2=O)c1cc(F)cc(C(F)(F)F)c1] | Fc1ccc(C1)c(c1)[C@@H]1NC(=O)c2cc(cc(NC(=O)c3cc(F)cc(c3)C(F)(F)F)c12)-c1ccc2nnnn2c1 | | 585.5 | A | |
| I-1454 | 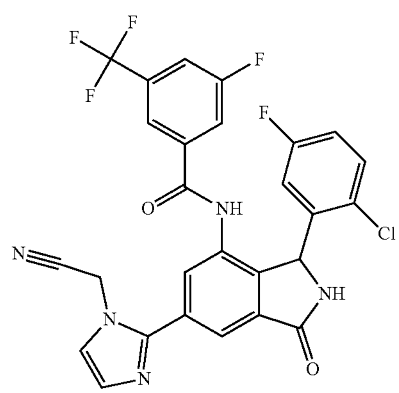 [SMILES: N#CCn1ccnc1-c1cc(NC(=O)c2cc(F)cc(C(F)(F)F)c2)c2c(c1)C(=O)NC2c1cc(F)ccc1Cl] | Fc1ccc(C1)c(c1)C1NC(=O)c2cc(cc(NC(=O)c3cc(F)cc(c3)C(F)(F)F)c12)-c1nccn1CC#N | | 572.22 | B | |
| I-1455 | 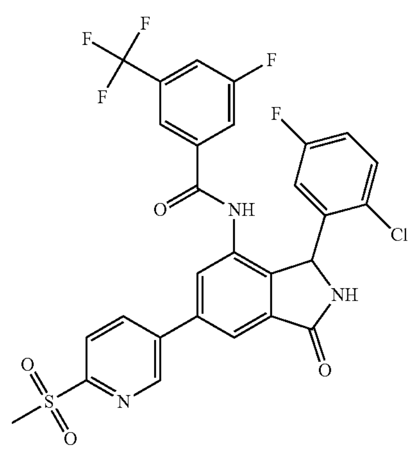 [SMILES: CS(=O)(=O)c1ccc(-c2cc(NC(=O)c3cc(F)cc(C(F)(F)F)c3)c3c(c2)C(=O)NC3c2cc(F)ccc2Cl)cn1] | CS(=O)(=O)c1ccc(cn1)-c1cc2C(=O)NC(c2c(NC(=O)c2cc(F)cc(c2)C(F)(F)F)c1)c1cc(F)ccc1Cl | | 622.19 | A | |

TABLE 2-continued

Representative Compounds of the Invention with Bioactivity Data.

| Ex. No. | Structure | SMILES | $^1$H NMR | MS | ADP-Glo IC$_{50}$ | MCF 10A IC$_{50}$ |
|---|---|---|---|---|---|---|
| I-1456 | 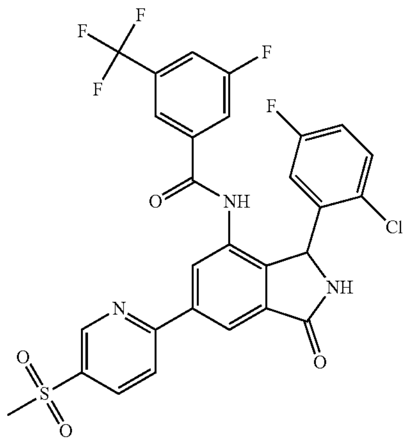 [SMILES: CS(=O)(=O)c1ccc(-c2cc(NC(=O)c3cc(F)cc(C(F)(F)F)c3)c3c(c2)C(=O)NC3c2cc(F)ccc2Cl)nc1] | CS(=O)(=O)c1ccc(nc1)-c1cc2C(=O)NC(c2c(NC(=O)c2cc(F)cc(c2)C(F)(F)F)c1)c1cc(F)ccc1Cl | | 622.14 | A | |
| I-1457 | 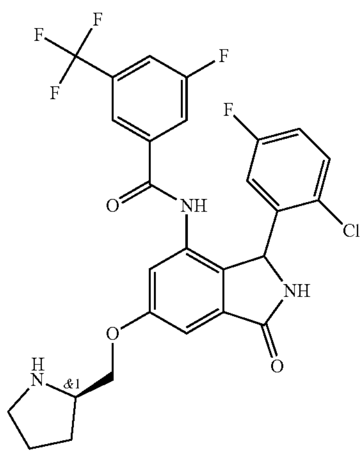 | Fc1ccc(C1)c(c1)C1NC(=O)c2cc(OC[C@H]3CCCN3)cc(NC(=O)c3cc(F)cc(c3)C(F)(F)F)c12 | NMR (400 MHz, DMSO-d6) 10.53 (br. s, 1H), 9.15 (br. s, 1H), 7.95 (br. d, 8.3 Hz, 1H), 7.73 (br. d, 9.1 Hz, 1H), 7.65 (s, 1H), 7.31 (dd, 8.9, 5.2 Hz, 1H), 7.22 (br. t, 2.1 Hz, 1H), 7.11-7.06 (m, 2H), 6.57 (br. s, 1H), 5.93 (br. s, 1H), 4.17-4.03 (m, 2H), 3.65 (m, 1H), 3.06-2.93 (m, 2H), 2.04-1.91 (m, 1H), 1.91-1.69 (m, 2H), 1.65-1.56 (m, 1H) | 566.3 | B | |
| I-1458 | 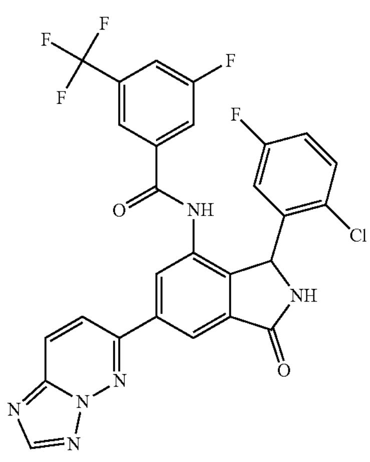 [SMILES: O=C(Nc1cc(-c2ccc3ncnn3n2)cc2c1C(c1cc(F)ccc1Cl)NC2=O)c1cc(F)cc(C(F)(F)F)c1] | Fc1ccc(C1)c(c1)C1NC(=O)c2cc(cc(NC(=O)c3cc(F)cc(c3)C(F)(F)F)c12)-c1ccc2ncnn2n1 | (400 MHz, DMSO-d6) 10.74 (s, 1H), 9.34 (br s, 1H), 8.76 (s, 1H), 8.61 (d, 9.5 Hz, 1H), 8.47 (d, 9.5 Hz, 1H), 8.42 (s, 1H), 8.33 (s, 1H), 7.98 (d, 8.3 Hz, 1H), 7.80 (d, 8.9 Hz, 1H), 7.72 (s, 1H), 7.35 (dd, 8.8, 5.1 Hz, 1H), 7.12 (td, 8.4, 2.9 Hz., 1H), 6.62 (br s, 1H), 6.10 (br s, 1H). | 583.3 | A | |

TABLE 2-continued

Representative Compounds of the Invention with Bioactivity Data.

| Ex. No. | Structure | SMILES | $^1$H NMR | MS | ADP-Glo $IC_{50}$ | MCF 10A $IC_{50}$ |
|---|---|---|---|---|---|---|
| I-1459 | 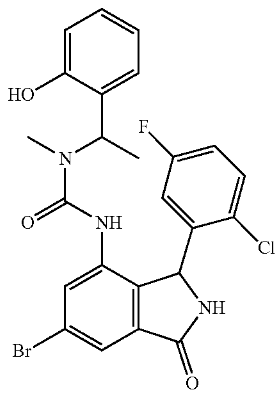 [SMILES: CC(c1ccccc1O)N(C)C(=O)Nc1cc(Br)cc2c1C(c1cc(F)ccc1Cl)NC2=O] | CC(N(C)C(=O)Nc1cc(Br)cc2C(=O)NC(c12)c1cc(F)ccc1Cl)c1cccc c1O | 1H NMR (400 MHz, DMSO-d6) 9.73 (s, 1H), 9.12 (d, 9.4 Hz, 1H), 8.42 (s, 1H), 7.76-7.67 (m, 1H), 7.58 (td, 9.7, 8.9, 5.1 Hz, 1H), 7.50-7.44 (s, 1H), 7.29-7.18 (m, 2H), 7.19-7.08 (s, 1H), 6.92-6.68 (m, 3H), 6.15-5.71 (s, 1H), 5.20 (q, 7.0 Hz, 1H), 2.45 (s, 2H), 2.25 (s, 1H), 1.40-1.15 (m, 3H). | 534 | E | |
| I-1460 | 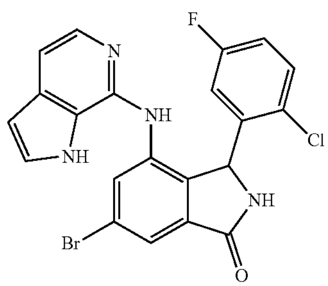 [SMILES: O=C1NC(c2cc(F)ccc2Cl)c2c(Nc3nccc4cc[nH]c34)cc(Br)cc21] | Fc1ccc(C1)c(c1)C1NC(=O)c2cc(Br)cc(Nc3nccc4cc[nH]c34)c12 | 1H NMR (400 MHz, DMSO-d6) 10.78 (s, 1H), 9.09 (s, 1H), 8.42 (s, 1H), 7.78 (d, 1.8 Hz, 1H), 7.67 (d, 5.6 Hz, 1H), 7.55 (d, 1.7 Hz, 1H), 7.39 (t, 2.7 Hz, 1H), 7.18 (dd, 8.8, 5.2 Hz, 1H), 7.08 (d, 5.6 Hz, 1H), 6.95 (td, 8.4, 3.1 Hz, 1H), 6.42-6.36 (m, 1H), 6.28 (d, 9.2 Hz, 1H), 6.02 (s, 1H). | 471 | E | |
| I-1461 | 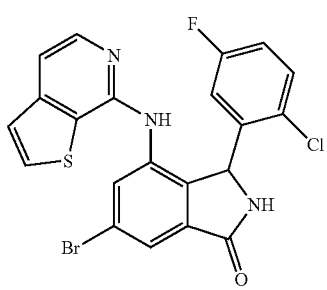 [SMILES: O=C1NC(c2cc(F)ccc2Cl)c2c(Nc3nccc4ccsc34)cc(Br)cc21] | Fc1ccc(C1)c(c1)C1NC(=O)c2cc(Br)cc(Nc3nccc4ccsc34)c12 | 1H NMR (400 MHz, DMSO-d6) 9.10 (s, 1H), 8.88 (s, 1H), 8.03 (d, 5.6 Hz, 1H), 7.92 (d, 5.3 Hz, 1H), 7.72 (d, 1.7 Hz, 1H), 7.60 (d, 1.8 Hz, 1H), 7.43 (d, 5.3 Hz, 1H), 7.36 (d, 5.5 Hz, 1H), 7.12 (dd, 8.8, 5.1 Hz, 1H), 6.94 (td, 8.3, 3.1 Hz, 1H), 6.25 (s, 1H), 5.85 (s, 1H). | 487.95 | E | |
| I-1462 | 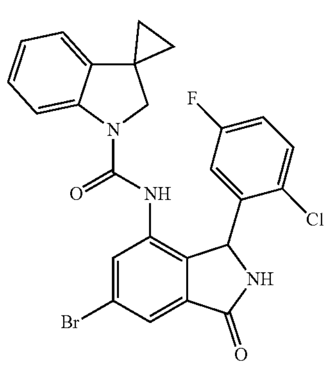 [SMILES: O=C1NC(c2cc(F)ccc2Cl)c2c(NC(=O)N3CC4(CC4)c4ccccc43)cc(Br)cc21] | Fc1ccc(C1)c(c1)C1NC(=O)c2cc(Br)cc(NC(=O)N3CC4(CC4)c4ccccc34)c12 | 1H NMR (400 MHz, DMSO-d6) 9.19 (s, 1H), 8.58 (s, 1H), 7.69-7.60 (m, 3H), 7.37 (dd, 8.9, 5.1 Hz, 1H), 7.17 (td, 8.4, 3.0 Hz, 1H), 7.07 (t, 7.8 Hz, 1H), 6.89-6.42 (m, 3H), 5.96 (s, 1H), 3.78 (d, 9.9 Hz, 1H), 3.22 (s, 1H), 1.09-0.89 (m, 4H) | 526 | B | |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-1463 | 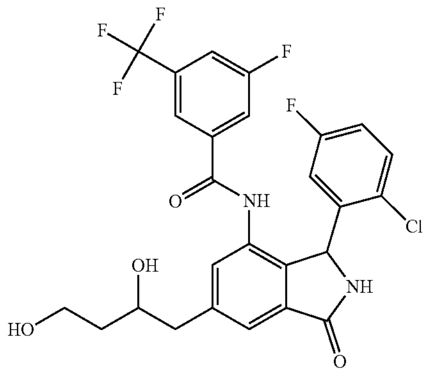 [SMILES: O=C(Nc1cc(CC(O)CCO)cc2c1C(c1cc(F)ccc1Cl)NC2=O)c1cc(F)cc(C(F)(F)F)c1] | OCCC(O)Cc1cc2C(=O)NC(c2c(NC(=O)c2cc(F)cc(c2)C(F)(F)F)c1)c1cc(F)ccc1Cl | NMR (400 MHz, DMSO-d6) 10.48 (br s, 1H), 9.08 (s, 1H), 7.93 (d, 8.4 Hz, 1H), 7.73 (dd, 8.9 Hz, 1H), 7.65 (s, 1H), 7.55 (s, 1H), 7.32 (s, 1H), 7.33 (dd, 8.9, 5.2 Hz, 1H), 7.13-7.05 (m, 1H), 6.61 (br s, 1H), 5.95 (br s, 1H), 4.62 (d, 4.7 Hz, 1H), 4.38 (br t, 4.3 Hz, 1H), 3.92-3.82 (m, 1H), 3.57-3.49 (m, 2H), 2.92-2.71 (m, 2H), 1.65-1.43 (m, 2H). | 555.3 | A | |
| I-1464 | 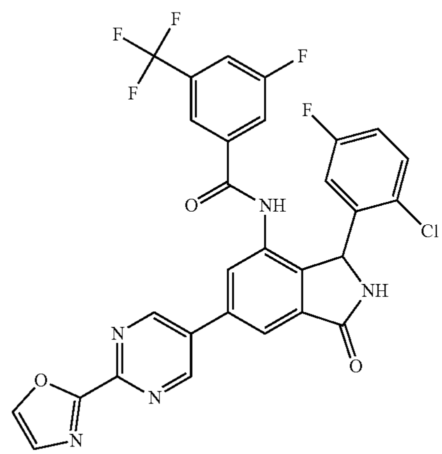 [SMILES: O=C(Nc1cc(-c2cnc(-c3ncco3)nc2)cc2c1C(c1cc(F)ccc1Cl)NC2=O)c1cc(F)cc(C(F)(F)F)c1] | Fc1ccc(C1)c(c1)C1NC(=O)c2cc(cc(NC(=O)c3cc(F)cc(c3)C(F)(F)F)c12)-c1cnc(nc1)-c1nccol | NMR (400 MHz, DMSO-d6) 10.74 (br s, 1H), 9.44 (s, 2H), 9.31 (br s, 1H), 8.43 (s, 1H), 8.25 (d, 0.7 Hz, 1H), 8.03 (s, 1H), 7.98 (d, 8.4 Hz, 1H), 7.78 (d, 9.3 Hz, 1H), 7.71 (s, 1H), 7.59 (s, 1H), 7.34 (dd, 8.9, 5.2 Hz, 1H), 7.12 (td, 8.7, 3.0 Hz, 1H), 6.64 (br s), 6.07 (br s). | 612.2 | A | |
| I-1465 | 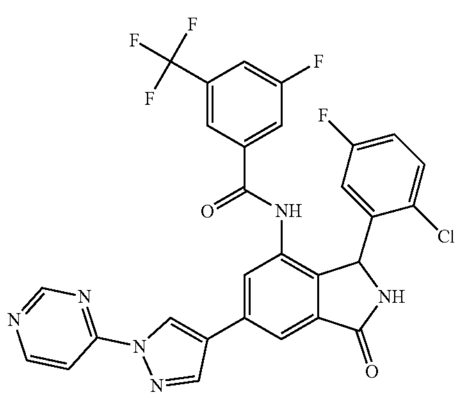 [SMILES: O=C(Nc1cc(-c2cnn(-c3ccncn3)c2)cc2c1C(c1cc(F)ccc1Cl)NC2=O)c1cc(F)cc(C(F)(F)F)c1] | Fc1ccc(C1)c(c1)C1NC(=O)c2cc(cc(NC(=O)c3cc(F)cc(c3)C(F)(F)F)c12)-c1cnn(c1)-c1ccncn1 | NMR (400 MHz, DMSO-d6) 10.59 (br s, 1H), 9.37 (s, 1H), 9.21 (br s, 1H), 9.15 (d, 0.8 Hz, 1H), 8.94 (d, 5.6 Hz, 1H), 8.66 (s, 1H), 8.18 (s, 1H), 8.00 (dd, 5.9, 0.9 Hz, 1H), 8.00-7.95 (m, 2H), 7.78 (d, 8.8 Hz, 1H), 7.73 (s, 1H), 7.33 (dd, 8.9, 5.2 Hz, 1H), 7.10 (td, 8.5, 3.1 Hz, 1H), 6.81 (br s, 1H), 6.01 (br s, 1H). | 611.3 | A | |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-1466 | 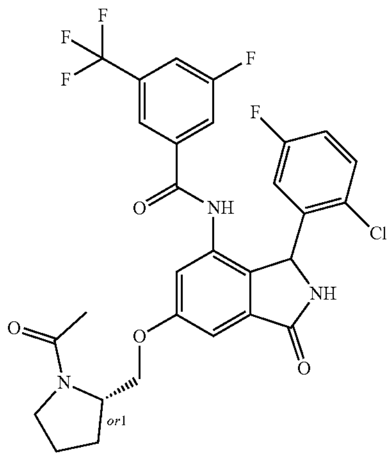 [SMILES: CC(=O)N1CCC[C@H]1COc1cc(NC(=O)c2cc(F)cc(C(F)(F)F)c2)c2c(c1)C(=O)NC2c1cc(F)ccc1Cl] | CC(=O)N1CCC[C@H]1COc1cc2C(=O)NC(c2c(NC(=O)c2cc(F)cc(c2)C(F)(F)F)c1cc(F)ccc1Cl | NMR (400 MHz, CD3CN), ' 8.63 (br. s, 1H), 7.64 (br. d, 8.5 Hz, 1H), 7.58 (br. d, 9.8 Hz, 1H), 7.55 (s, 1H), 7.37 (d, 1.9 Hz, 1H), 7.36 (d, 2.1 Hz, 1H), 7.24 (dd, 8.8, 5.2 Hz, 1H), 7.19-7.11 (m, 1H), 6.96 (td, 8.4, 2.8 Hz, 1H), 6.63 (br. s, 1H), 6.05 (br. s, 1H), 4.34-4.30 (m, 1H), 4.29-4.24 (m, 1H), 4.09-4.00 (m, 2H), 3.55-3.31 (m, 2H), 2.12-2.01(m, 4H), 1.98 (s, 3H) | 608.3 | A | |
| I-1467 | 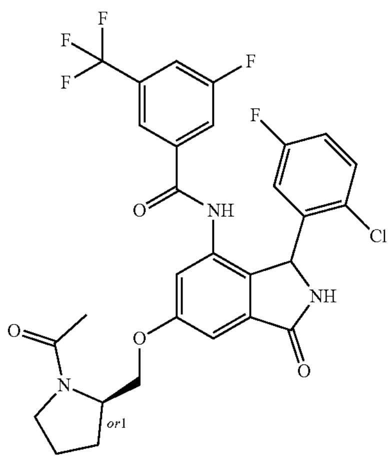 [SMILES: CC(=O)N1CCC[C@@H]1COc1cc(NC(=O)c2cc(F)cc(C(F)(F)F)c2)c2c(c1)C(=O)NC2c1cc(F)ccc1Cl] | CC(=O)N1CCC[C@@H]1COc1cc2C(=O)NC(c2c(NC(=O)c2cc(F)cc(c2)C(F)(F)F)c1cc(F)ccc1Cl | NMR (400 MHz, CD3CN) mixture of rotamers, ' 8.94 (br. s, 1H), 7.63 (br. d, 8.5 Hz, 1H), 7.59-7.56 (m, 2H), 7.36 (d, 1.9 Hz, 1H), 7.35 (d, 2.1 Hz, 1H), 7.24 (dd, 8.8, 5.2 Hz, 1H), 7.19-7.11 (m, 1H), 6.95 (td, 8.4, 2.8 Hz, 1H), 6.63 (br. s, 1H), 6.04 (br. s, 1H), 4.35-4.27 (m, 1H), 4.25 (dd, 9.8, 2.9 Hz, 1H), 4.03 (dd, 9.6, 7.8 Hz, 1H), 3.55-3.31 (m, 2H), 2.14-1.98 (m, 4H), 1.97 (s, 3H) | 608.3 | A | |
| I-1468 | 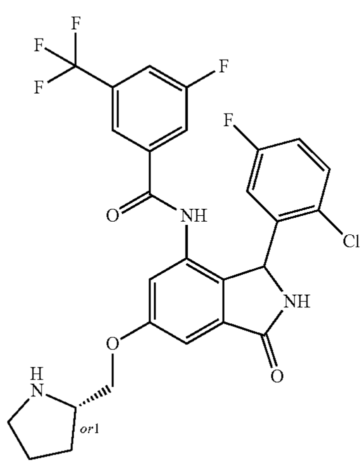 | Fc1ccc(C1)c(c1)C1NC(=O)c2cc(OC[C@@H]3CCCN3)cc(NC(=O)c3cc(F)cc(c3)C(F)(F)F)c12 | NMR (400 MHz, DMSO-d6) 10.58 (br. s, 1H), 9.16 (br. s, 1H), 8.34 (s, 1H), 7.95 (br. d, 8.3 Hz, 1H), 7.73 (br. d, 9.1 Hz, 1H), 7.65 (s, 1H), 7.31 (dd, 8.9, 5.2 Hz, 1H), 7.22 (br. t, 2.1 Hz, 1H), 7.11-7.06 (m, 2H), 6.54 (submerged br. s, 1H), 5.93 (br. s, 1H), 4.20-4.03 (m, 2H), 3.72-3.66 (m, 1H), 3.07-2.96 (m, 2H), 2.04-1.91 (m, 1H), 1.91-1.72 (m, 2H), 1.65-1.56 (m, 1H) | 566.1 | B | |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-1469 | 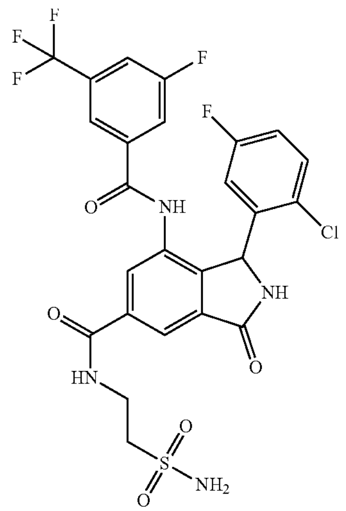 [SMILES: NS(=O)(=O)CCNC(=O)c1cc(NC(=O)c2cc(F)cc(C(F)(F)F)c2)c2c(c1)C(=O)NC2c1cc(F)ccc1Cl] | NS(=O)(=O)CCNC(=O)c1cc2C(=O)NC(c2c(NC(=O)c2cc(F)cc(c2)C(F)(F)F)c1)c1cc(F)ccc1Cl | (400 MHz, DMSO-D6) 10.67 (br s, 1 H), 9.29 (br s, 1 H), 8.99 (t, 5.5 Hz, 1 H), 8.21 (s, 1 H), 7.99 (s, 1 H), 7.96 (br d, 8.6 Hz, 1 H), 7.76 (br d, 8.9 Hz, 1 H), 7.68 (s, 1 H), 7.33 (dd, 8.8, 5.2 Hz, 1 H), 7.10 (td, 8.5, 2.8 Hz, 1 H), 6.98 (s, 2 H), 6.50 (br s, 1 H), 6.03 (br s, 1 H), 3.72-3.65 (m, 2 H), 3.28 (t, 7.2 Hz, 2H). | 615.2 | A | |
| I-1470 | 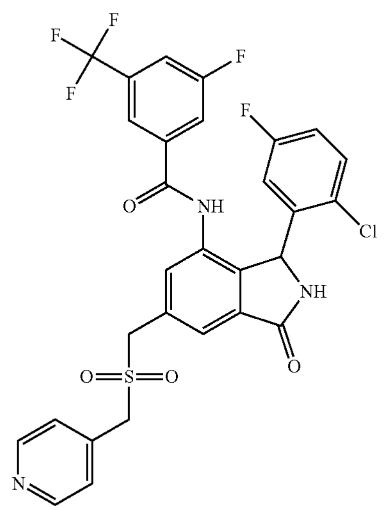 [SMILES: O=C(Nc1cc(CS(=O)(=O)Cc2ccncc2)cc2c1C(c1cc(F)ccc1Cl)NC2=O)c1cc(F)cc(C(F)(F)F)c1] | Fc1ccc(C1)c(c1)C1NC(=O)c2cc(CS(=O)(=O)Cc3ccncc3)cc(NC(=O)c3cc(F)cc(c3)C(F)(F)F)c12 | NMR (400 MHz, DMSO-d6) 10.64 (br s, 1H), 9.24 (br s, 1H), 8.60 (d, 4.6 Hz, 2H), 7.95 (d, 8.3 Hz, 1H), 7.74 (s, 1H), 7.74 (br d, 7.8 Hz, 1H), 7.64 (s, 1H), 7.51 (s, 1H), 7.41 (d, 4.8 Hz, 2H), 7.32 (dd, 8.8, 5.0 Hz, 1H), 7.11 (td, 8.0, 3.6 Hz, 1H), 6.60 (br s, 1H), 5.99 (br s, 1H), 4.79 (s, 2H), 4.64 (s, 2H) | 636 | A | |
| I-1471 | 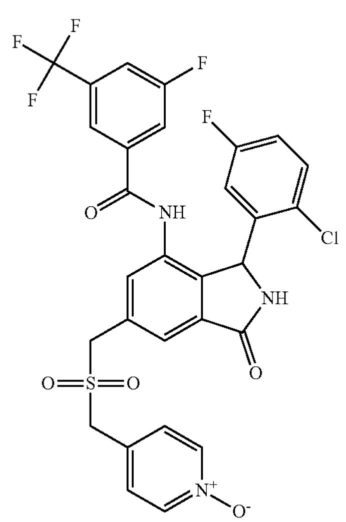 [SMILES: O=C(Nc1cc(CS(=O)(=O)Cc2cc[n+]([O-])cc2)cc2c1C(c1cc(F)ccc1Cl)NC2=O)c1cc(F)cc(C(F)(F)F)c1] | [O-][n+]1ccc(CS(=O)(=O)Cc2cc3C(=O)NC(c3c(NC(=O)c3cc(F)cc(c3)C(F)(F)F)c2)c2cc(F)ccc2Cl)cc1 | NMR (400 MHz, DMSO-d6) 10.62 (br s, 1H), 9.24 (br s, 1H), 8.25 (m, 2H), 7.95 (d, 8.5 Hz, 1H), 7.73 (m, 2H), 7.64 (s, 1H), 7.50 (s, 1H), 7.41 (m, 2H), 7.32 (dd, 8.8, 5.2 Hz, 1H), 7.11 (td, 8.4, 2.9 Hz, 1H), 6.65 (br s, 1H), 6.00 (br s, 1H), 4.81-4.69 (m, 2H), 4.64 (s, 2H). | 652 | A | |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-1472 | 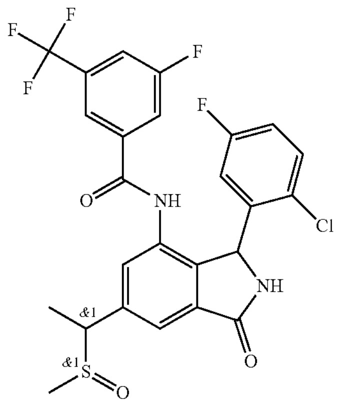 [SMILES: CC(c1cc(NC(=O)c2cc(F)cc(C(F)(F)F)c2)c2c(c1)C(=O)NC2c1cc(F)ccc1Cl)S(C)=O] | CC(c1cc2C(=O)NC(c2c(NC(=O)c2cc(F)cc(c2)C(F)(F)F)c1c(F)ccc1Cl)S(C)=O | NMR (400 MHz, DMSO-d6) 10.67 (br. s, 1H), 9.20 (s, 1H), 7.95 (br. d, 8.3 Hz, 1H), 7.74 (br. d, 9.1 Hz, 1H), 7.70-7.63 (m, 2H), 7.44 (s, 0.5H), 7.41 (s, 0.5H), 7.35-7.28 (m, 1H), 7.14-7.06 (m, 1H), 6.6 (br. s, 1H), 5.98 (br, s, 1H), 4.30-4.23 (m, 0.5H), 4.22-4.15 (m, 0.5H), 2.42-2.37 (m, 1.5H), 2.27-2.21 (m, 1.5H), 1.67-1.63 (m, 1.5H), 1.63-1.58 (m, 1.5H) | 557 | B | |
| I-1473 | 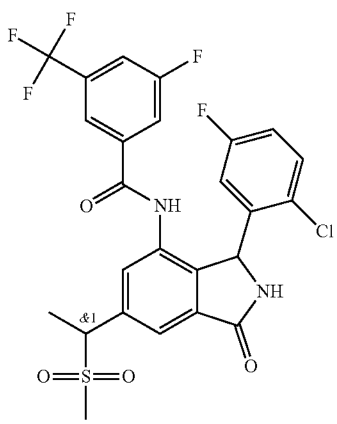 [SMILES: CC(c1cc(NC(=O)c2cc(F)cc(C(F)(F)F)c2)c2c(c1)C(=O)NC2c1cc(F)ccc1Cl)S(C)(=O)=O] | CC(c1cc2C(=O)NC(c2c(NC(=O)c2cc(F)cc(c2)C(F)(F)F)c1c(F)ccc1Cl)S(C)(=O)=O | NMR (400 MHz, DMSO-d6) 10.64 (s, 1H), 9.28 (s, 1H), 7.95 (d. 8.1 Hz, 1H), 7.80 (d, 2.7 Hz, 1H), 7.74 (d, 9.3 Hz, 1H), 7.64 (s, 1H), 7.55 (s, 1H), 7.32 (dd, 8.8, 5.1 Hz, 1H), 7.10 (m, 1H), 6.59 (br, s, 1H), 6.00 (br, s, 1H), 4.87- 4.78 (m, 1H), 2.91 (s, 3H), 1.71 (d, 7.1 Hz, 3H) | 573 | A | |
| I-1474 | 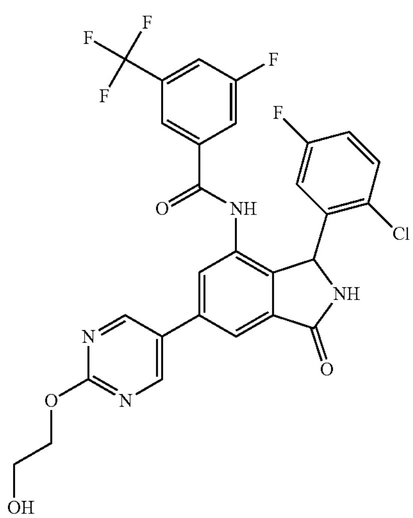 [SMILES: O=C(Nc1cc(-c2cnc(OCCO)nc2)cc2c1C(c1cc(F)ccc1Cl)NC2=O)c1cc(F)cc(C(F)(F)F)c1] | OCCOc1ncc(cn1)-c1cc2C(=O)NC(c2c(NC(=O)c2cc(F)cc(c2)C(F)(F)F)c1cc(F)ccc1Cl | 1H-NMR (400 MHz, DMSO-d6) 10.54 (br. s, 1H), 9.26 (br. s, 1H), 9.04 (s, 2H), 8.05 (d, 0.8 Hz, 1H), 7.96 (br. d, 7.9 Hz, 1H), 7.86 (s, 1H), 7.77 (br. d, 8.8 Hz, 1H), 7.70 (s, 1H), 7.33 (dd, 8.8, 5.2 Hz, 1H), 7.11 (app. td, 8.4, 3.0 Hz, 1H), 6.63 (br. s, 1H), 6.04 (br. s, 1H), 4.96 (br. s, 1H), 4.42-4.38 (t, 5.0 Hz, 2H), 3.76 (t, 5.0 Hz, 2H). | 605.3 | A | |

TABLE 2-continued

Representative Compounds of the Invention with Bioactivity Data.

| Ex. No. | Structure | SMILES | $^1$H NMR | MS | ADP-Glo IC$_{50}$ | MCF 10A IC$_{50}$ |
|---|---|---|---|---|---|---|
| I-1475 | 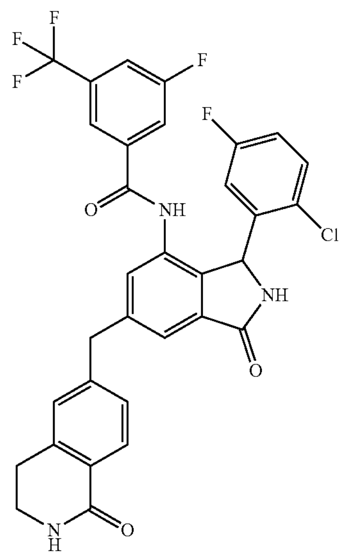 | Fc1ccc(C1)c(c1)C1 NC(=O)c 2cc(Cc3c cc4C(=O) NCCc4c 3)cc(NC (=O)c3cc (F)cc(c3) C(F)(F)F) c12 | 1H-NMR (400 MHz, DMSO-d6) 9.13 (br. s, 1H), 8.36 (br. s, 1H), 7.93 (br. d, 8.4 Hz, 1H), 7.88 (t, 2.5 Hz 1H), 7.79 (d, 7.9 Hz, 1H), 7.72 (br. d, 8.9 Hz, 1H), 7.63 (s, 1H), 7.60 (s, 1H), 7.35 (s, 1H), 7.32-7.27 (m, 2H), 7.25 (s, 1H), 7.08 (app. td, 8.5, 3.1 Hz, 1H), 6.58 (br. s, 1H), 5.92 (br. s, 1H), 4.17 (d, A of AB, JAB = 14.6 Hz, 1H), 4.12 (d, B of AB, JAB = 14.7 Hz, 1H), 3.35 (td, 6.6, 2.7 Hz, 2H), 2.87 (t, 6.5 Hz, 2H). | 626.3 | A | |
| I-1476 | 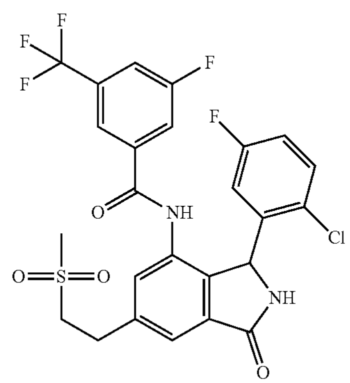 [SMILES: CS(=O)(=O)CCc1cc(NC(=O)c2cc(F)cc(C(F)(F)F)c2)c2c(c1)C(=O)NC2c1cc(F)ccc1Cl] | CS(=O) (=O)CCc1 cc2C(=O) NC(c2c (NC(=O)c 2cc(F)cc (c2)C(F) (F)F)c1)c 1cc(F)ccc 1Cl | NMR (400 MHz, DMSO) 10.53 (br s, 1H), 9.14 (br s, 1H), 7.95 (d, 8.2 Hz, 1H), 7.73 (d, 9.1 Hz, 1H), 7.68 (s, 1H), 7.66 (s, 1H). 7.44 (s, 1H), 7.31 (dt, 9.7, 4.9 Hz, 1H), 7.09 (td, 8.3, 3.0 Hz, 1H), 6.59 (br s, 1H), 5.96 (br s, 1H), 3.54 (t, 7.9 Hz, 2H), 3.22-3.15 (m, 2H), 3.02 (s, 2H). | 573.1 | A | |
| I-1477 | 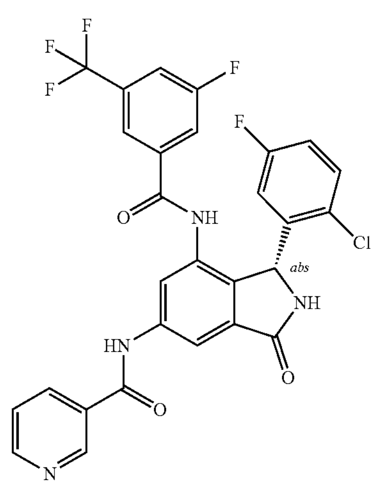 [SMILES: O=C(Nc1cc(NC(=O)c2cc(F)cc(C(F)(F)F)c2)c2c(c1)C(=O)N[C@H]2c1cc(F)ccc1Cl)c1cccnc1] | Fc1ccc(C1)c(c1)[C @@H]1 NC(=O)c 2cc(NC (=O)c3ccc nc3)cc(N C(=O)c3 cc(F)cc(c 3)C(F)(F) F)c12 | NMR (400 MHz, DMSO) 10.86 (s, 1H), 10.63 (s, 1H), 9.19 (s, 1H), 9.15 (d, 2.1 Hz, 1H), 8.79 (dd, 4.8, 1.6 Hz, 1H), 8.37-8.30 (m, 1H), 8.15 (d, 1.4 Hz, 1H), 8.03 (d, 1.1 Hz, 1H), 7.95 (d, 8.0 Hz, 1H), 7.74 (d, 8.6 Hz, 1H), 7.65 (s, , 1H), 7.61 (dd, 8.5, 4.8 Hz, 1H), 7.32 (dd, 8.8, 5.2 Hz, 1H), 7.10 (td, 8.4, 2.9 Hz 1H), 6.57 (br s, 1H), 5.96 (br s, 1H). | 587.2 | A | |

TABLE 2-continued

Representative Compounds of the Invention with Bioactivity Data.

| Ex. No. | Structure | SMILES | $^1$H NMR | MS | ADP-Glo IC$_{50}$ | MCF 10A IC$_{50}$ |
|---|---|---|---|---|---|---|
| I-1478 | 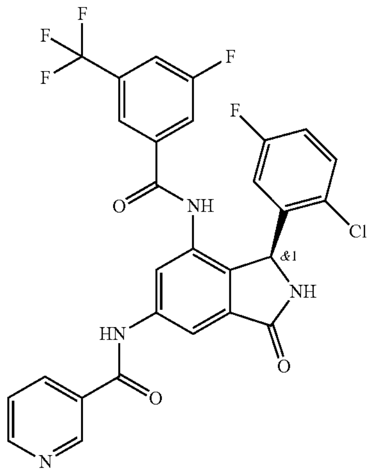 [SMILES: O=C(Nc1cc(NC(=O)c2cc(F)cc(C(F)(F)F)c2)c2c(c1)C(=O)N[C@@H]2c1cc(F)ccc1Cl)c1cccnc1] | Fc1ccc(C1)c(c1)[C@H]1NC(=O)c2cc(NC(=O)c3cccnc3)cc(NC(=O)c3cc(F)cc(c3)C(F)(F)F)c12 | NMR (400 MHz, DMSO) 10.86 (s, 1H), 10.63 (s, 1H), 9.19 (s, 1H), 9.15 (d, 2.1 Hz, 1H), 8.79 (dd, 4.8, 1.6 Hz, 1H), 8.37-8.30 (m, 1H), 8.15 (d, 1.4 Hz, 1H), 8.03 (d, 1.1 Hz, 1H), 7.95 (d, 8.0 Hz, 1H), 7.74 (d, 8.6 Hz, 1H), 7.65 (s, , 1H), 7.61 (dd, 8.5, 4.8 Hz, 1H), 7.32 (dd, 8.8, 5.2 Hz, 1H), 7.10 (td, 8.4, 2.9 Hz. 1H), 6.57 (br s, 1H), 5.96 (br s, 1H). | 587.3 | B | |
| I-1479 | 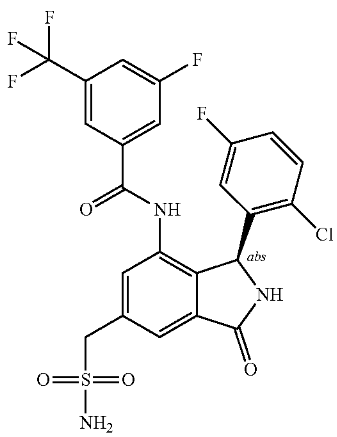 [SMILES: NS(=O)(=O)Cc1cc(NC(=O)c2cc(F)cc(C(F)(F)F)c2)c2c(c1)C(=O)N[C@@H]2c1cc(F)ccc1Cl] | NS(=O)(=O)Cc1cc2C(=O)N[C@@H](c2c(NC(=O)c2cc(F)cc(c2)C(F)(F)F)c1c(F)ccc1Cl | NMR (400 MHz, DMSO-d6) 10.65 (br. s, 1H), 9.20 (br. s, 1H), 7.94 (br. d, 8.3 Hz, 1H), 7.74 (submerged br. d, 8.9 Hz, 1H), 7.72 (s, 1H), 7.63 (s, 1H), 7.47 (s, 1H), 7.32 (dd, 8.9, 5.2 Hz, 1H), 7.11 (td, 8.6, 3.0 Hz, 1H), 6.97 (s, 2H), 6.60 (br. s, 1H), 6.00 (br. s, 1H), 4.48 (app. q, 13.6 Hz, 2H). | 560.1 | D | |
| I-1480 | 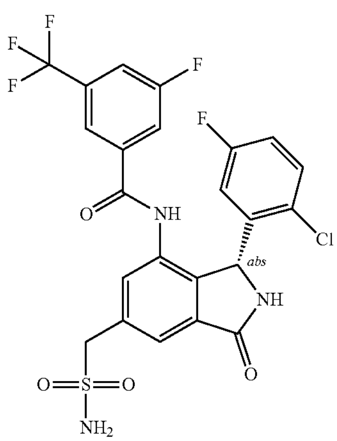 [SMILES: NS(=O)(=O)Cc1cc(NC(=O)c2cc(F)cc(C(F)(F)F)c2)c2c(c1)C(=O)N[C@H]2c1cc(F)ccc1Cl] | NS(=O)(=O)Cc1cc2C(=O)N[C@H](c2c(NC(=O)c2cc(F)cc(c2)C(F)(F)F)c1c1cc(F)ccc1Cl | NMR (400 MHz, DMSO-d6) 10.65 (br. s, 1H), 9.20 (br. s, 1H), 7.94 (br. d, 8.3 Hz, 1H), 7.74 (submerged br. d, 8.9 Hz, 1H), 7.72 (s, 1H), 7.63 (s, 1H), 7.47 (s, 1H), 7.32 (dd, 8.9, 5.2 Hz, 1H), 7.11 (td, 8.6, 3.0 Hz, 1H), 6.97 (s, 2H), 6.60 (br. s, 1H), 6.00 (br. s, 1H), 4.48 (app. q, 13.6 Hz, 2H). | 560.1 | A | |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-1481 | 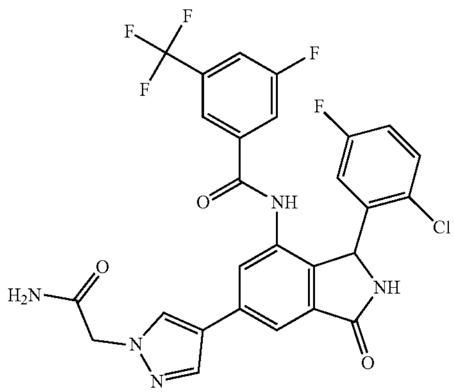 [SMILES: NC(=O)Cn1cc(-c2cc(NC(=O)c3cc(F)cc(C(F)(F)F)c3)c3c(c2)C(=O)NC3c2cc(F)ccc2Cl)cn1] | NC(=O)Cn1cc(cn1)-c1cc2C(=O)NC(c2c(NC(=O)c2cc(F)cc(c2)C(F)(F)F)c1)c1cc(F)ccc1Cl | NMR (400 MHz, DMSO-d6) 10.56 (br s, 1H), 9.15 (br s, 1H), 8.33 (s, 1H), 8.05 (s, 1H), 7.95 (br d, 8.6 Hz, 1H), 7.89 (s, 1H), 7.76 (br d, 9.5 Hz, 1H), 7.70 (s, 1H), 7.66-7.51 (m, 10H), 7.32 (dd, 8.8, 5.2 Hz, 2H), 7.09 (td, 8.7, 3.0 Hz, 1H), 6.61 (br s, 1H), 5.98 (br s, 1H), 4.80 (s, 2H). | 590.2 | A | |
| I-1482 | 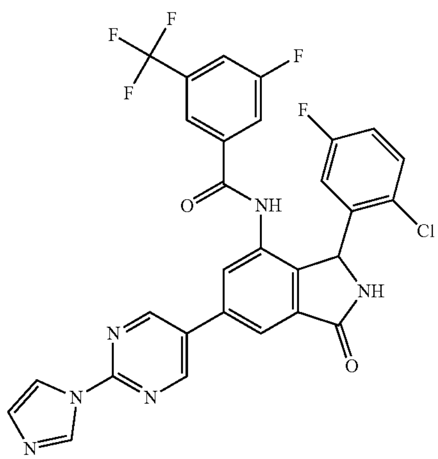 [SMILES: O=C(Nc1cc(-c2cnc(-n3ccnc3)nc2)cc2c1C(c1cc(F)ccc1Cl)NC2=O)c1cc(F)cc(C(F)(F)F)c1] | Fc1ccc(C1)c(c1)C1NC(=O)c2cc(cc(NC(=O)c3cc(F)cc(c3)C(F)(F)F)c12)-c1cnc(nc1)-n1ccnc1 | NMR (400 MHz, DMSO-d6) 10.76 (br s, 1H), 9.32 (s, 2H), 9.29 (submerged br s, 1H), 8.67 (s, 1H), 8.19 (s, 1H), 8.03 (s, 1H), 7.97 (s, 1H), 7.96 (submerged br d, 8.1 Hz, 1H), 7.77 (br d, 8.1 Hz, 1H), 7.71 (s, 1H), 7.34 (dd, 8.9, 5.2 Hz, 1H), 7.20 (s, 1H), 7.11 (td, 8.5, 3.0 Hz., 1H), 6.68 (br s, 1H), 6.04 (br s, 1H) | 611.2 | A | |
| I-1483 | 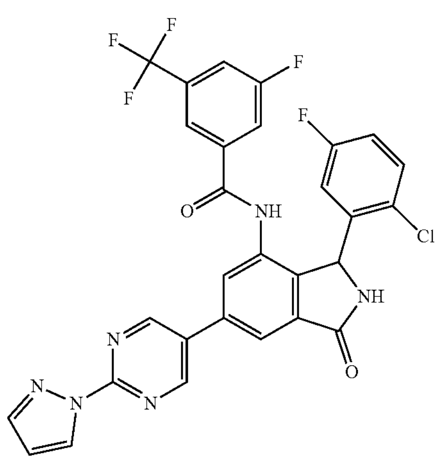 [SMILES: O=C(Nc1cc(-c2cnc(-n3cccn3)nc2)cc2c1C(c1cc(F)ccc1Cl)NC2=O)c1cc(F)cc(C(F)(F)F)c1] | Fc1ccc(C1)c(c1)C1NC(=O)c2cc(cc(NC(=O)c3cc(F)cc(c3)C(F)(F)F)c12)-c1cnc(nc1)-n1cccn1 | NMR (400 MHz, DMSO-d6) 10.73 (br s, 1H), 9.32 (s, 2H), 9.29 (submerged br s, 1H), 8.74 (d, 2.4 Hz, 1H), 8.20 (s, 1H), 7.98 (s, 1H), 7.97 (submerged br d, 7.7 Hz, 1H), 7.92 (d, 0.9 Hz, 1H), 7.78 (br d, 9.0 Hz, 1H), 7.71 (s, 1H), 7.34 (dd, 8.9, 5.2 Hz, 1H), 7.11 (td, 8.6, 3.1 Hz, 1H), 6.75 (submerged br s, 1H), 6.65 (dd, 2.6, 1.6 Hz, 1H), 6.07 (br s, 1H). | 611.2 | A | |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-1484 | 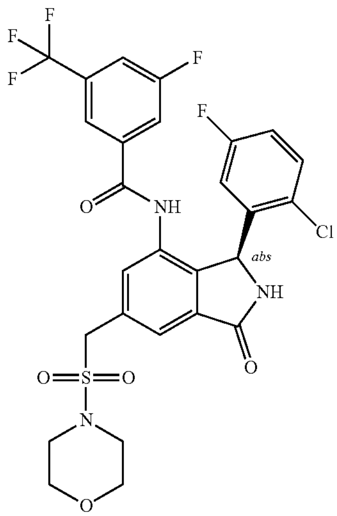 [SMILES: O=C(Nc1cc(CS(=O)(=O)N2CCOCC2)cc2c1[C@@H](c1cc(F)ccc1Cl)NC2=O)c1cc(F)cc(C(F)(F)F)c1] | Fc1ccc(C1)c(c1)[C@H]1NC(=O)c2cc(CS(=O)(=O)N3CCOCC3)cc(NC(=O)c3cc(F)cc(c3)C(F)(F)F)c12 | NMR (400 MHz, DMSO-d6) 10.61 (s, 1H), 9.23 (br. s, 1H), 7.96 (br. d, 8.3 Hz, 1H), 7.79 (s, 1H), 7.75 (br. d, 9.2 Hz, 1H), 7.65 (s, 1H), 7.55 (s, 1H), 7.33 (dd, 8.9, 5.2 Hz, 1H), 7.11 (td, 8.5, 2.9 Hz, 1H), 6.44 (br. s, 1H), 5.98 (br. s, 1H), 4.69 (s, 2H), 3.64-3.53 (m, 4H), 3.21-3.09 (m, 4H). | 630.2 | D | |
| I-1485 | 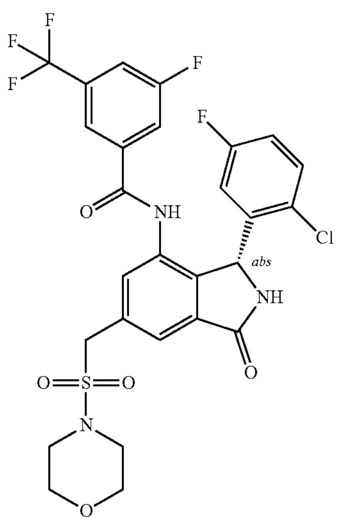 [SMILES: O=C(Nc1cc(CS(=O)(=O)N2CCOCC2)cc2c1[C@H](c1cc(F)ccc1Cl)NC2=O)c1cc(F)cc(C(F)(F)F)c1] | Fc1ccc(C1)c(c1)[C@@H]1NC(=O)c2cc(CS(=O)(=O)N3CCOCC3)cc(NC(=O)c3cc(F)cc(c3)C(F)(F)F)c12 | NMR (400 MHz, DMSO-d6) 10.61 (s, 1H), 9.23 (br. s, 1H), 7.96 (br. d, 8.3 Hz, 1H), 7.79 (s, 1H), 7.75 (br. d, 9.2 Hz, 1H), 7.65 (s, 1H), 7.55 (s, 1H), 7.33 (dd, 8.9, 5.2 Hz, 1H), 7.11 (td, 8.5, 2.9 Hz, 1H), 6.44 (br. s, 1H), 5.98 (br. s, 1H), 4.69 (s, 2H), 3.64-3.53 (m, 4H), 3.21-3.09 (m, 4H). | 630.2 | A | |
| I-1486 | 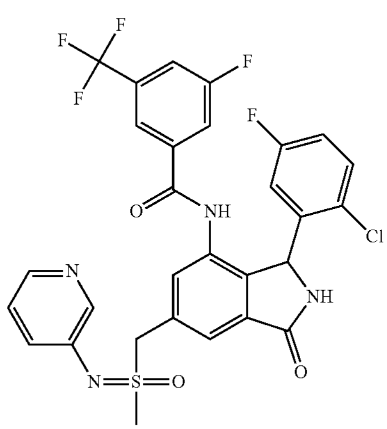 [SMILES: CS(=O)(Cc1cc(NC(=O)c2cc(F)cc(C(F)(F)F)c2)c2c(c1)C(=O)NC2c1cc(F)ccc1Cl)=Nc1cccnc1] | CS(=O)(Cc1cc2C(=O)NC(c2c(NC(=O)c2cc(F)cc(c2)C(F)(F)F)c1cc(F)ccc1Cl)=Nc1cccnc1 | NMR (400 MHz, DMSO-d6) 10.61 (br. s, 1H), 9.21 (br. s, 1H), 8.20 (d, 1.6 Hz, 0.5H), 8.19 (d, 1.7 Hz, 0.5H), 8.07 (app br. t, 4.0 Hz, 1H), 7.96 (br. d, 8.3 Hz, 1H), 7.81 (s, 0.5H), 7.79 (s, 0.5H), 7.73 (br. d, 8.4 Hz, 1H), 7.63 (s, 1H), 7.57 (s, 0.5H), 7.53 (s, 0.5H), 7.36-7.31 (submerged m, 1H), 7.32 (dd, 8.9, 5.2 Hz, 1H), 7.21-7.14 (m, 1H), 7.10 (td, 8.5, 2.7 Hz, 1H), 6.66 (br. s, 1H), 5.97 (br. s, 1H), 5.05-4.90 (m, 2H), 3.16 (s, 3H). | 635.3 | A | |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-1487 | 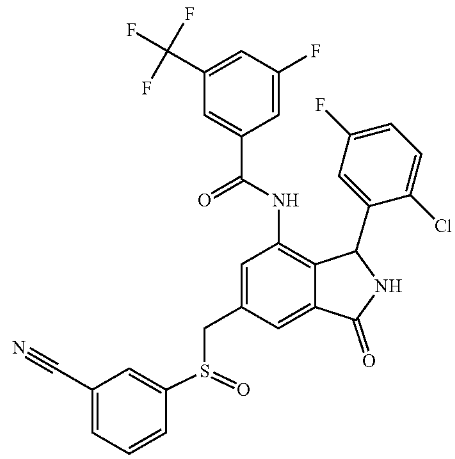 [SMILES: N#Cc1cccc(S(=O)Cc2cc(NC(=O)c3cc(F)cc(C(F)(F)F)c3)c3c(c2)C(=O)NC3c2cc(F)ccc2Cl)c1] | Fc1ccc(C1)c(c1)C1NC(=O)c2cc(CS(=O)c3cccc(c3)C#N)cc(NC(=O)c3cc(F)cc(c3)C(F)(F)F)c12 | NMR (400 MHz, CD3CN) ' 8.63 (br. s 0.5H), 8.58 (br. s, 0.5H), 7.84 (dt, 3.3, 1.5 Hz, 0.5H), 7.82 (dt, 3.2, 1.6 Hz, 0.5H), 7.80 (br. 1, 1.2 Hz, 0.5H), 7.77 (br. t, 1.2 Hz, 0.5H), 7.69-7.61 (m, 3H), 7.61-7.55 (m, 1H), 7.54 (s, 0.5H), 7.53 (s, 0.5H), 7.34 (d, 0.8 Hz, 0.5 H), 7.30-7.20 (m, 3.5H), 6.98 (dt, 8.8, 2.8 Hz, 0.5H), 6.97 (dt, 8.8, 2.8 Hz, 0.5H), 6.61 (br, s, 1H), 6.08 (br, s, 1H), 4.40 (d, 12.8 Hz, 0.5H), 4.37 (d, 12.8 Hz, 0.5H), 4.17 (d, 12.7 Hz, 0.5H), 4.14 (d, 12.9 Hz, 0.5H). | 630 | A | |
| I-1488 | 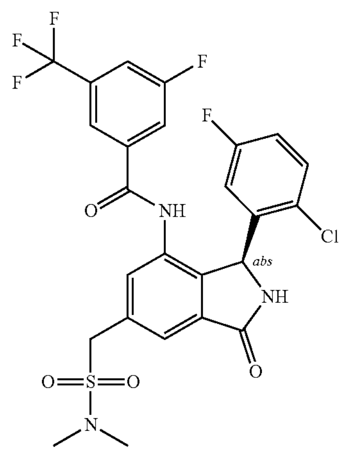 [SMILES: CN(C)S(=O)(=O)Cc1cc(NC(=O)c2cc(F)cc(C(F)(F)F)c2)c2c(c1)C(=O)N[C@@H]2c1cc(F)ccc1Cl] | CN(C)S(=O)(=O)Cc1cc2C(=O)N[C@@H](c2c(NC(=O)c2cc(F)cc(c2)C(F)(F)F)c1)c1cc(F)ccc1Cl | NMR (400 MHz, DMSO-d6) 10.60 (br. s, 1H), 9.21 (br. s, 1H), 7.95 (dt, 8.5, 2.0 Hz, 1H), 7.77 (s, 1H), 7.75 (br. d, 8.4 Hz, 1H) 7.66 (s, 1H), 7.55 (s, 1H), 7.32 (dd, 8.9, 5.2 Hz, 1H), 7.10 (td, 8.5, 3.1 Hz, 1H), 6.58 (br. s, 1H), 5.97 (br. s, 1H), 4.70-4.58 (m, 2H), 2.76 (s, 6H). | 588.2 | D | |
| I-1489 | 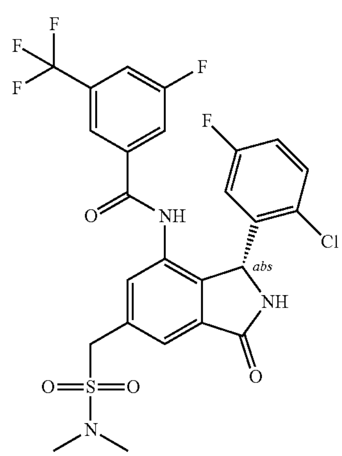 [SMILES: CN(C)S(=O)(=O)Cc1cc(NC(=O)c2cc(F)cc(C(F)(F)F)c2)c2c(c1)C(=O)N[C@H]2c1cc(F)ccc1Cl] | CN(C)S(=O)(=O)Cc1cc2C(=O)N[C@H](c2c(NC(=O)c2cc(F)cc(c2)C(F)(F)F)c1)c1cc(F)ccc1Cl | NMR (400 MHz, DMSO-d6) 10.60 (br. s, 1H), 9.21 (br. s, 1H), 7.95 (dt, 8.5, 2.0 Hz, 1H), 7.77 (s, 1H), 7.75 (submerged br. d, 8.4 Hz, 1H) 7.66 (s, 1H), 7.55 (s, 1H), 7.32 (dd, 8.9, 5.2 Hz, 1H), 7.10 (td, 8.5, 3.1 Hz., 1H), 6.58 (br. s, 1H), 5.97 (br. s, 1H), 4.70-4.58 (m, 2H), 2.76 (s, 6H). | | A | |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-1490 | 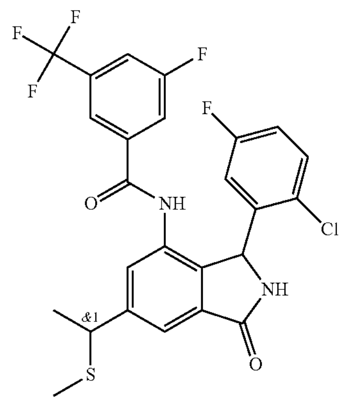 [SMILES: CSC(C)c1cc(NC(=O)c2cc(F)cc(C(F)(F)F)c2)c2c(c1)C(=O)NC2c1cc(F)ccc1Cl] | CSC(C)c1cc2C(=O)NC(c2c(NC(=O)c2cc(F)cc(c2)C(F)(F)F)c1)ccc1Cl | NMR (400 MHz, DMSO-d6) ' 10.51 (br. s, 0.5 H), 10.5 (br. s, 0.5 H), 9.11 (br. s, 1H), 7.90 (br. d, 8.7 Hz, 1H), 7.70 (br. d, 9.2 Hz, 1H), 7.62-7.60 (m, 2H), 7.44 (br. s, 0.5H), 7.42 (br. s, 0.5 H), 7.27 (dd, 8.9, 5.1 Hz, 1H), 7.05 (td, 8.6, 3.1 Hz, 1H), 6.59 (br. s, 1H), 5.90 (br. s, 1H), 4.12 (q, 6.9 Hz, 0.5H), 4.12 (q, 6.9 Hz, 0.5H), 1.88 (s, 1.5H), 1.87 (s, 1.5H), 1.54 (d, 6.9 Hz, 1.5H), 1.53 (d, 6.9 Hz, 1.5H). | 541 | A | |
| I-1491 | 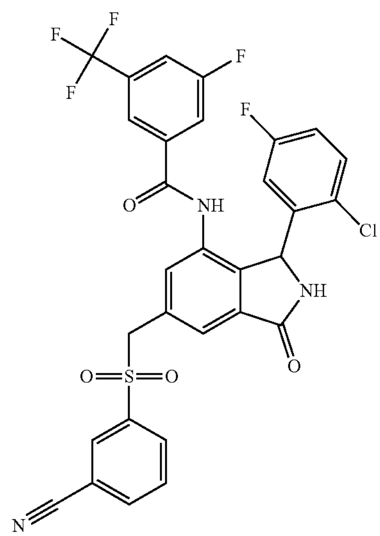 [SMILES: N#Cc1cccc(S(=O)(=O)Cc2cc(NC(=O)c3cc(F)cc(C(F)(F)F)c3)c3c(c2)C(=O)NC3c2cc(F)ccc2Cl)c1] | Fc1ccc(C1)c(c1)C1NC(=O)c2cc(CS(=O)(=O)c3ccccc(c3)C#N)cc(NC(=O)c3cc(F)cc(c3)C(F)(F)F)c12 | NMR (400 MHz, CD3CN) 8.62 (s, 1H), 8.13 (t, 1.1 Hz, 1H), 8.03 (dt, 7.9, 1.2 Hz, 1H), 7.94 (dt, 8.0, 1.3Hz, 1H), 7.70 (1, 7.9 Hz, 1H), 7.66 (br, d, 8.5 Hz, 1H), 7.58 (td, 9.1 Hz, 1.7 Hz, 1H), 7.54 (s, 1H), 7.50 (s, 1H), 7.42 (s, 1H), 7.27 (dd, 8.9, 5.1 Hz, 1H), 7.27 (NH, 1H), 6.98 (td, 8.1, 3.0 Hz, 1H), 6.62 (br, s, 1H), 6.12 (br, s, 1H), 4.66 (s, 2H). | 646 | A | |
| I-1492 | 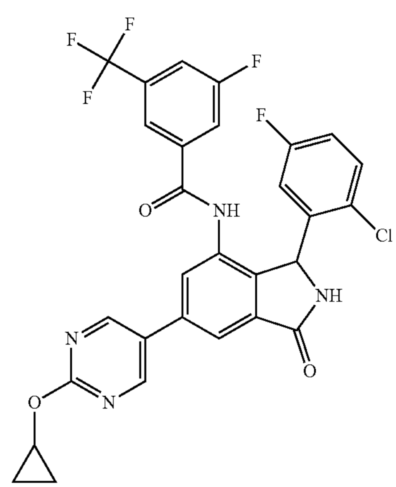 [SMILES: O=C(Nc1cc(-c2cnc(OC3CC3)nc2)cc2c1C(c1cc(F)ccc1Cl)NC2=O)c1cc(F)cc(C(F)(F)F)c1] | Fc1ccc(C1)c(c1)C1NC(=O)c2cc(cc(NC(=O)c3cc(F)cc(c3)C(F)(F)F)c12)-c1cnc(OC2CC2)nc1 | 1H NMR (400 MHz, DMSO-d6) 10.66 (br. s, 1H), 9.26 (br. s, 1H), 9.06 (s, 2H), 8.06 (d, 1.3 Hz, 1H), 7.97 (d, 8.5 Hz, 1H), 7.85 (s, 1H), 7.76 (d, 8.8 Hz, 1H), 7.69 (s, 1H), 7.33 (dd, 8.9, 5.2 Hz, 1H), 7.11 (td, 8.4, 3.0 Hz, 1H), 6.59 (br. s, 1H), 6.02 (br. s, 1H), 4.38 (tt, 6.2, 3.2 Hz, 1H), 0.86-0.80 (m, 2H), 0.80-0.74 (m, 2H). | 601.2 | A | |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-1493 | 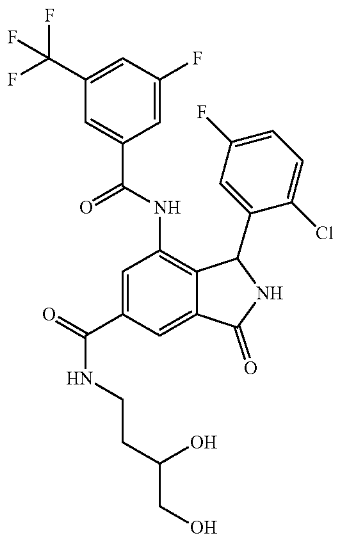 [SMILES: O=C(NCCC(O)CO)c1cc(NC(=O)c2cc(F)cc(C(F)(F)F)c2)c2c(c1)C(=O)NC2c1cc(F)ccc1Cl] | OCC(O)CCNC(=O)c1cc2C(=O)NC(c2c(NC(=O)c2cc(F)cc(c2)C(F)(F)F)c1c1cc(F)ccc1Cl | (400 MHz, DMSO-D6) 10.65 (br s, 1 H), 9.27 (br s, 1 H), 8.79 (t, 5.3 Hz, 1 H), 8.21 (s, 1 H), 7.99 (s, 1 H), 7.96 (d, 8.5 Hz, 1 H), 7.76 (d, 8.8 Hz, 1 H), 7.68 (s, 1 H), 7.32 (dd, 8.9, 5.2 Hz, 1 H), 7.09 (td, 8.5, 2.9 Hz, 1 H), 6.52 (br s, 1 H), 6.03 (br s, 1 H), 4.64-4.50 (m, 2 H), 3.57-3.49 (m, 1 H), 3.47-3.23 (m, 4 H), 1.84-1.72 (m, 1 H), 1.54-1.43 (m, 1 H). | 598.2 | A | |
| I-1494 | 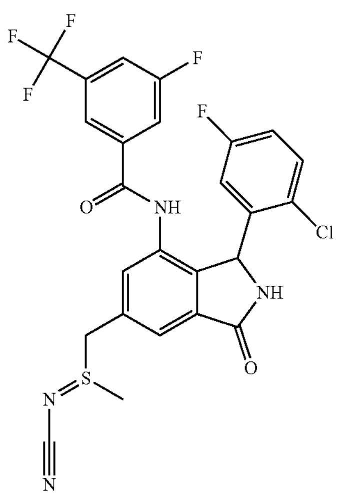 [SMILES: C/S(Cc1cc(NC(=O)c2cc(F)cc(C(F)(F)F)c2)c2c(c1)C(=O)NC2c1cc(F)ccc1Cl)=N\C#N] | C\S(Cc1cc2C(=O)NC(c2c(NC(=O)c2cc(F)cc(c2)C(F)(F)F)c1cc(F)ccc1Cl)=N/C#N | NMR (400 MHz, DMSOO-d6) 10.64 (br. s, 1H), 9.26 (br. s, 1H), 7.95 (br. d, 8.4 Hz, 1H), 7.77 (s, 0.5H), 7.76 (s, 0.5H), 7.73 (br. d, 9.0 Hz, 1H), 7.63 (s, 1H), 7.55 (s, 0.5H), 7.53 (s, 0.5H), 7.33 (dd, 5.3, 2.6 Hz, 0.5H), 7.31 (dd, 5.2, 2.6 Hz, 0.5H), 7.15-7.06 (m, 1H), 6.59 (br. s, 1H), 6.01 (br. s, 1H), 4.71 (d, 12.9 Hz, 0.5H), 4.67 (d, 13.0 Hz, 0.5H), 4.50 (d, 11.9 Hz, 0.5H), 4.47 (d, 12.2 Hz, 0.5H), 2.90 (s, 1.5H), 2.89 (s, 1.5H). | 567.2 | A | |
| I-1495 | 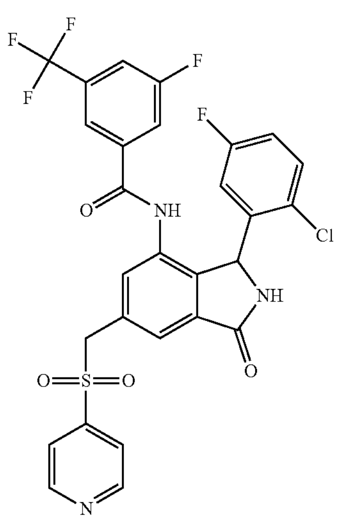 [SMILES: O=C(Nc1cc(CS(=O)(=O)c2ccncc2)cc2c1C(c1cc(F)ccc1Cl)NC2=O)c1cc(F)cc(C(F)(F)F)c1] | Fc1ccc(C1)c(c1)C1NC(=O)c2cc(CS(=O)(=O)c3ccncc3)cc(NC(=O)c3cc(F)cc(c3)C(F)(F)F)c12 | NMR (400 MHz, DMSO-d6) 10.59 (s, 1H), 9.19 (br. s, 1H), 8.89 (dd, 4.5, 1.6 Hz, 2H), 7.95 (br. d, 8.5 Hz, 1H), 7.76 (dd, 5.8, 1.9 Hz, 2H), 7.73 (br. d, 9.1 Hz, 1H), 7.63 (s, 1H), 7.52 (br. s, 1H), 7.44 (s, 1H), 7.33 (dd, 8.9, 5.2 Hz, 1H), 7.11 (td, 8.5, 2.9 Hz, 1H), 6.53 (br. s, 1H), 5.95 (br. s, 1H), 5.08 (s, 2H). | 622.1 | A | |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-1496 | 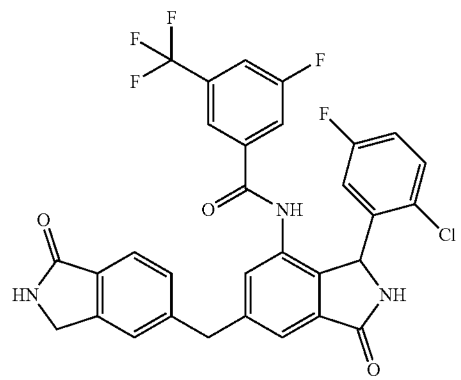 [SMILES: O=C(Nc1cc(Cc2ccc3c(c2)CNC3=O)cc2c1C(c1cc(F)ccc1Cl)NC2=O)c1cc(F)cc(C(F)(F)F)c1] | Fc1ccc(C1)c(c1)C1NC(=O)c2cc(Cc3ccc4C(=O)NCc4c3)cc(NC(=O)c3cc(F)cc(c3)C(F)(F)F)c12 | 1H-NMR (400 MHz, DMSO-d6) 10.48 (br. s, 1H), 9.13 (br. s, 1H), 8.50 (s, 1H), 7.93 (br. d, 8.5 Hz, 1H), 7.71 (br. d, 8.8 Hz, 1H), 7.65-7.61 (m, 3H), 7.52 (s, 1H), 7.44 (d, 7.9 Hz, 1H), 7.36 (s, 1H), 7.30 (dd, 8.9, 5.2 Hz, 1H), 7.08 (app. td, 8.4, 3.0 Hz, 1H), 6.57 (br. s, 1H), 5.93 (br. s, 1H), 4.35 (s, 2H), 4.26 (d, A of AB, JAB = 14.5 Hz, 1H), 4.22 (d, JAB = 14.7 Hz, 1H). | 612.3 | A | |
| I-1497 | 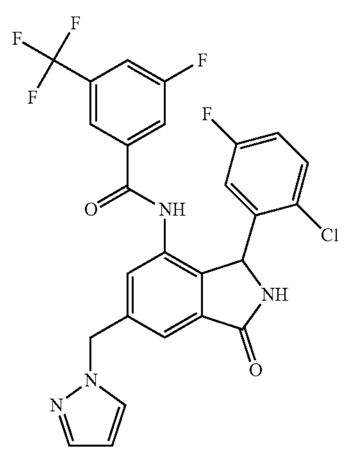 [SMILES: O=C(Nc1cc(Cn2cccn2)cc2c1C(c1cc(F)ccc1Cl)NC2=O)c1cc(F)cc(C(F)(F)F)c1] | Fc1ccc(C1)c(c1)C1NC(=O)c2cc(Cn3cccn3)cc(NC(=O)c3cc(F)cc(c3)C(F)(F)F)c12 | 1H-NMR (400 MHz, DMSO-d6) 10.52 (br. s, 1H), 9.17 (br. s, 1H), 7.97-7.93 (m, 1H), 7.93 (d, 2.0 Hz, 1H), 7.71 (br. d, 8.8 Hz, 1H), 7.62 (s, 1H), 7.52 (d, 1.6 Hz, 1H), 7.50 (s, 1H), 7.32-7.28 (m, 2H), 7.09 (app. td, 8.3, 2.9 Hz, 1H), 6.56 (br. s, 1H), 6.32 (t, 2.0 Hz, 1H), 5.94 (br. s, 1H), 5.57-5.48 (m, 2H). | 547.3 | A | |
| I-1498 | 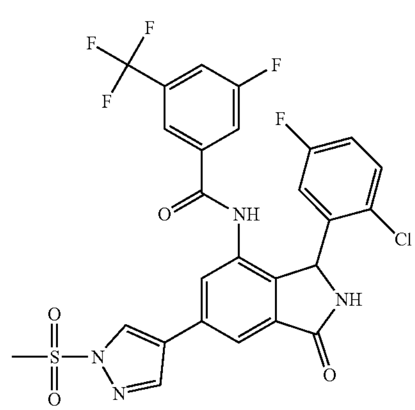 [SMILES: CS(=O)(=O)n1cc(-c2cc(NC(=O)c3cc(F)cc(C(F)(F)F)c3)c3c(c2)C(=O)NC3c2cc(F)ccc2Cl)cn1] | CS(=O)(=O)n1cc(cn1)-c1cc2C(=O)NC(c2c(NC(=O)c2cc(F)cc(c2)C(F)(F)F)c1)c1cc(F)ccc1Cl | | 610.99 | A | |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-1499 | 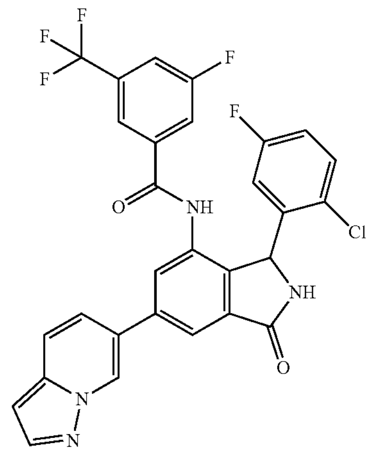 [SMILES: O=C(Nc1cc(-c2ccc3ccnn3c2)cc2c1C(c1cc(F)ccc1Cl)NC2=O)c1cc(F)cc(C(F)(F)F)c1] | Fc1ccc(C1)c(c1)C1NC(=O)c2cc(cc(NC(=O)c3cc(F)cc(c3)C(F)(F)F)c12)-c1ccc2ccnn2c1 | | 583.126 | A | |
| I-1500 | 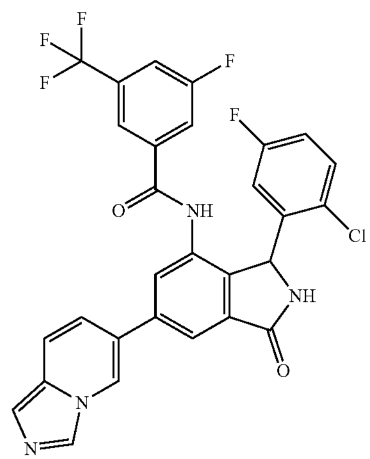 [SMILES: O=C(Nc1cc(-c2ccc3cncn3c2)cc2c1C(c1cc(F)ccc1Cl)NC2=O)c1cc(F)cc(C(F)(F)F)c1] | Fc1ccc(C1)c(c1)C1NC(=O)c2cc(cc(NC(=O)c3cc(F)cc(c3)C(F)(F)F)c12)-c1ccc2cncn2c1 | | 583.12 | A | |
| I-1501 | 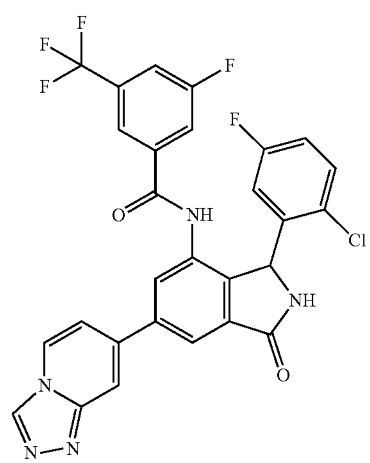 [SMILES: O=C(Nc1cc(-c2ccn3cnnc3c2)cc2c1C(c1cc(F)ccc1Cl)NC2=O)c1cc(F)cc(C(F)(F)F)c1] | Fc1ccc(C1)c(c1)C1NC(=O)c2cc(cc(NC(=O)c3cc(F)cc(c3)C(F)(F)F)c12)-c1ccn2cnnc2c1 | | 584.17 | A | |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-1502 | 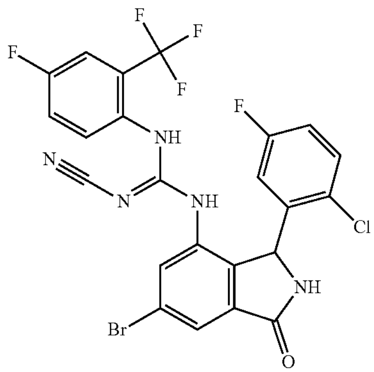 [SMILES: N#C/N=C(\Nc1ccc(F)cc1C(F)(F)F)Nc1cc(Br)cc2c1C(c1cc(F)ccc1Cl)NC2=O] | Fc1ccc(C1)c(c1)C1NC(=O)c2cc(Br)cc(N\C(Nc3ccc(F)cc3C(F)(F)F)=N\C#N)c12 | | 584.3 | D | |
| I-1503 | 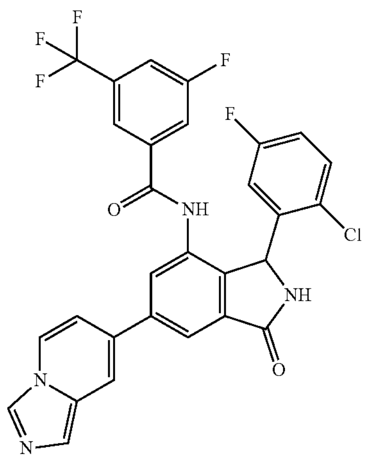 [SMILES: O=C(Nc1cc(-c2ccn3cncc3c2)cc2c1C(c1cc(F)ccc1Cl)NC2=O)c1cc(F)cc(C(F)(F)F)c1] | Fc1ccc(C1)c(c1)C1NC(=O)c2cc(cc(NC(=O)c3cc(F)cc(c3)C(F)(F)F)c12)-c1ccn2cncc2c1 | | 583.12 | A | |
| I-1504 | 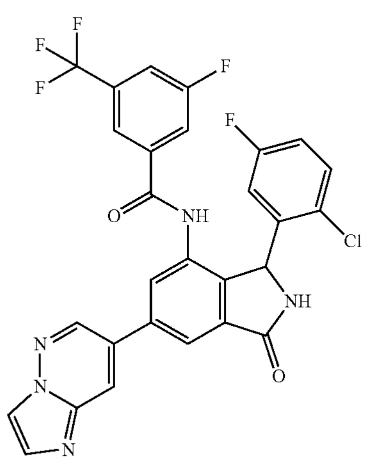 [SMILES: O=C(Nc1cc(-c2cnn3ccnc3c2)cc2c1C(c1cc(F)ccc1Cl)NC2=O)c1cc(F)cc(C(F)(F)F)c1] | Fc1ccc(C1)c(c1)C1NC(=O)c2cc(cc(NC(=O)c3cc(F)cc(c3)C(F)(F)F)c12)-c1cnn2ccnc2c1 | | 584.17 | A | |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-1505 | 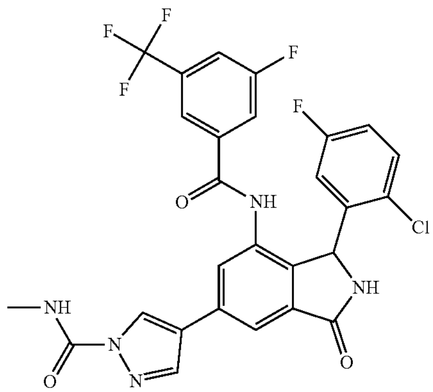 [SMILES: CNC(=O)n1cc(-c2cc(NC(=O)c3cc(F)cc(C(F)(F)F)c3)c3c(c2)C(=O)NC3c2cc(F)ccc2Cl)cn1] | CNC(=O)n1cc(cn1)-c1cc2C(=O)NC(c2c(NC(=O)c2cc(F)cc(c2)C(F)(F)F)c1)c1cc(F)ccc1Cl | | 590.13 | A | |
| I-1506 | 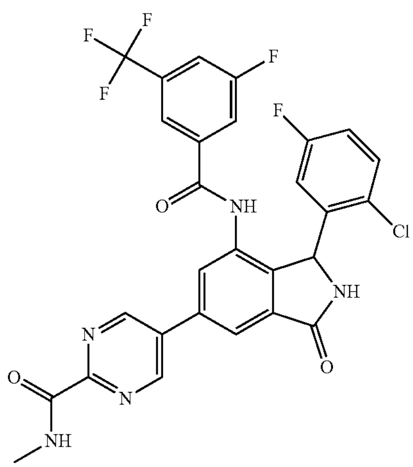 [SMILES: CNC(=O)c1ncc(-c2cc(NC(=O)c3cc(F)cc(C(F)(F)F)c3)c3c(c2)C(=O)NC3c2cc(F)ccc2Cl)cn1] | CNC(=O)c1ncc(cn1)-c1cc2C(=O)NC(c2c(NC(=O)c2cc(F)cc(c2)C(F)(F)F)c1)c1cc(F)ccc1Cl | NMR (400 MHz, DMSO-d6) 10.59 (br s, 1H), 9.39 (s, 2H), 9.31 (br s, 1H), 9.01 (q, 4.6 Hz, 1H), 8.24 (d, 1.1 Hz, 1H), 8.02 (s, 1H), 7.98 (d, 8.5 Hz, 1H), 7.78 (d, 8.3 Hz, 1H), 7.71 (s, 1H), 7.34 (dd, 8.9, 5.2 Hz, 1H), 7.12 (td, 8.5, 2.9 Hz, 1H), 6.65 (br s, 1H), 6.07 (br s, 1H), 2.85 (d, 4.8 Hz, 2H). | 602.2 | B | |
| I-1507 | 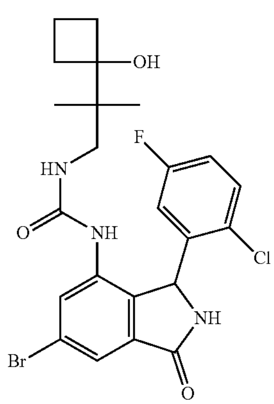 [SMILES: CC(C)(CNC(=O)Nc1cc(Br)cc2c1C(c1cc(F)ccc1Cl)NC2=O)C1(O)CCC1] | CC(C)(CNC(=O)Nc1cc(Br)cc2C(=O)NC(c12)c1cc(F)ccc1Cl)C1(O)CCC1 | 1H NMR (400 MHz, DMSO-d6) 9.16 (s, 1H), 8.13 (s, 1H), 7.83 (s, 1H), 7.52 (d, 1.7 Hz, 1H), 7.50-7.43 (m, 1H), 7.21 (td, 8.4, 3.1 Hz, 1H), 6.70 (s, 1H), 6.20 (t, 6.1 Hz, 1H), 5.99 (s, 1H), 4.86 (s, 1H), 3.03 (d, 8.7 Hz, 1H), 2.82 (dd, 13.5, 5.2 Hz, 1H), 2.16-2.06 (m, 3H), 1.82-1.71 (m, 2H), 1.44-1.34 (m, 1H), 0.69 (d, 10.8 Hz, 6H). | 526.25 | E | |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-1508 | 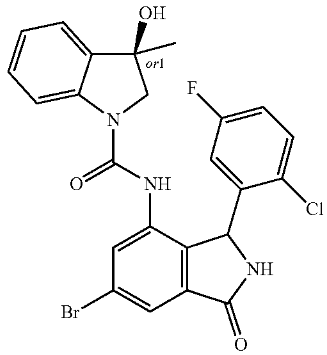 [SMILES: C[C@]1(O)CN(C(=O)Nc2cc(Br)cc3c2C(c2cc(F)ccc2Cl)NC3=O)c2ccccc21] | CC1(O)CN(C(=O)Nc2cc(Br)cc3C(=O)NC(c23)c2cc(F)ccc2Cl)c2ccccc12 | 1H NMR (400 MHz, DMSO-d6) 9.20 (s, 1H), 8.68 (s, 1H), 7.82 (d, 8.1 Hz, 1H), 7.68 (d, 1.8 Hz, 1H), 7.59 (d, 1.8 Hz, 1H), 7.37 (dd, 8.8, 5.1 Hz, 1H), 7.31 (d, 7.4 Hz, 1H), 7.27-7.12 (m, 2H), 7.00 (t, 7.4 Hz, 1H), 6.68 (s, 1H), 5.97 (s, 1H), 5.53 (s, 1H), 3.78 (d, 10.7 Hz, 1H), 2.96 (s, 1H), 1.39 (s, 3H). | 532 | D | |
| I-1509 | 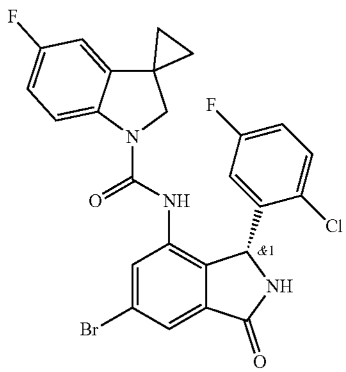 [SMILES: O=C1N[C@@H](c2cc(F)ccc2Cl)c2c(NC(=O)N3CC4(CC4)c4cc(F)ccc43)cc(Br)cc21] | Fc1ccc2N(CC3(CC3)c2c1)C(=O)Nc1cc(Br)cc2C(=O)N[C@H](c12)c1cc(F)ccc1Cl | 1H NMR (400 MHz, DMSO-d6) 9.19 (s, 1H), 8.61 (s, 1H), 7.66 (s, 2H), 7.59 (d, 1.8 Hz, 1H), 7.37 (dd, 8.9, 5.0 Hz, 1H), 7.18 (t, 7.7 Hz, 1H), 6.89 (t, 8.9 Hz, 1H), 6.67 (dd, 8.8, 2.7 Hz, 1H), 5.94 (s, 1H), 3.81 (d, 10.0 Hz, 1H), 3.18 (s, 1H), 1.09 (s, 2H), 0.97 (t, 9.6 Hz, 2H) | 544 | A | |
| I-1510 | 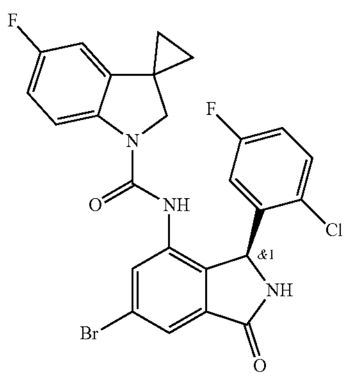 [SMILES: O=C1N[C@H](c2cc(F)ccc2Cl)c2c(NC(=O)N3CC4(CC4)c4cc(F)ccc43)cc(Br)cc21] | Fc1ccc2N(CC3(CC3)c2c1)C(=O)Nc1cc(Br)cc2C(=O)N[C@@H](c12)c1cc(F)ccc1Cl | 1H NMR (400 MHz, DMSO-d6) 9.19 (s, 1H), 8.61 (s, 1H), 7.65 (d, 10.6 Hz, 2H), 7.59 (d, 1.8 Hz, 1H), 7.37 (dd, 9.0, 5.1 Hz, 1H), 7.18 (td, 8.3, 3.0 Hz, 1H), 6.88 (td, 9.1, 2.6 Hz, 1H), 6.67 (dd, 8.7, 2.7 Hz, 1H), 5.93 (s, 1H), 3.81 (d, 10.0 Hz, 1H), 3.18 (s, 1H), 1.09 (d, 3.0 Hz, 2H), 1.02-0.90 (m, 2H). | 544 | D | |
| I-1511 | 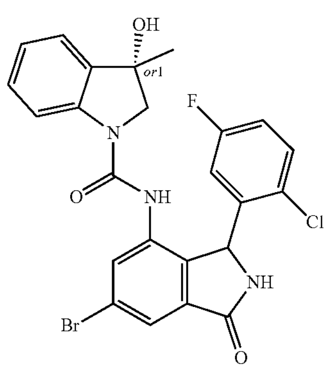 [SMILES: C[C@@]1(O)CN(C(=O)Nc2cc(Br)cc3c2C(c2cc(F)ccc2Cl)NC3=O)c2ccccc21] | C[C@@]1(O)CN(C(=O)Nc2cc(Br)cc3C(=O)NC(c23)c2cc(F)ccc2Cl)c2ccccc12 | 1H NMR (400 MHz, DMSO-d6) 9.20 (s, 1H), 8.68 (s, 1H), 7.82 (d, 8.1 Hz, 1H), 7.68 (d, 1.8 Hz, 1H), 7.59 (d, 1.8 Hz, 1H), 7.37 (dd, 8.8, 5.1 Hz, 1H), 7.31 (d, 7.4 Hz, 1H), 7.27-7.12 (m, 2H), 7.00 (t, 7.4 Hz, 1H), 6.68 (s, 1H), 5.97 (s, 1H), 5.53 (s, 1H), 3.78 (d, 10.7 Hz, 1H), 2.96 (s, 1H), 1.39 (s, 3H). | 514 | A | |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-1512 | 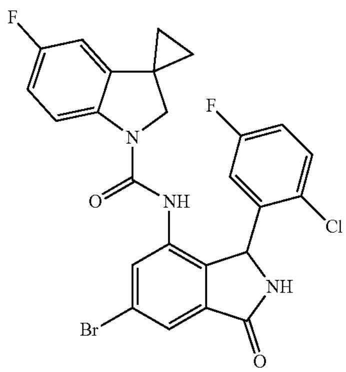 [SMILES: O=C1NC(c2cc(F)ccc2Cl)c2c(NC(=O)N3CC4(CC4)c4cc(F)ccc43)cc(Br)cc21] | Fc1ccc2N(CC3(CC3)c2c1)C(=O)Nc1cc(Br)cc2C(=O)NC(c12)c1cc(F)ccc1Cl | 1H NMR (400 MHz, DMSO-d6) 9.20 (s, 1H), 8.61 (s, 1H), 7.63 (dd, 29.2, 1.7 Hz, 3H), 7.38 (dd, 8.8, 5.1 Hz, 1H), 7.18 (td, 8.4, 3.1 Hz, 1H), 7.06-6.24 (m, 3H), 5.94 (s, 1H), 3.81 (d, 10.0 Hz, 1H), 3.19 (s, 1H), 1.15-1.04 (m, 2H), 1.03-0.91 (m, 2H). | 543.95 | B | |
| I-1513 | 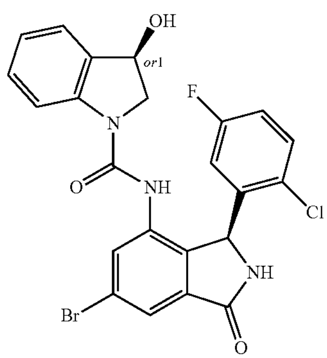 [SMILES: O=C1N[C@H](c2cc(F)ccc2Cl)c2c(NC(=O)N3C[C@H](O)c4ccccc43)cc(Br)cc21] | O[C@H]1CN(C(=O)Nc2cc(Br)cc3C(=O)N[C@@H](c23)c2cc(F)ccc2Cl)c2ccccc12 | 1H NMR (400 MHz, DMSO-d6) 9.20 (s, 1H), 8.72 (s, 1H), 7.82 (d, 8.2 Hz, 1H), 7.71-7.66 (m, 1H), 7.60 (d, 1.8 Hz, 1H), 7.40-7.30 (m, 2H), 7.24 (t, 7.8 Hz, 1H), 7.16 (td, 8.4, 3.1 Hz, 1H), 6.99 (t, 7.4 Hz, 1H), 6.67 (s, 1H), 5.98 (s, 1H), 5.66 (d, 6.0 Hz, 1H), 5.12-5.03 (m, 1H), 3.62 (dd, 11.2, 3.5 Hz, 1H), 3.23 (s, 1H). | 518 | B | |
| I-1514 | 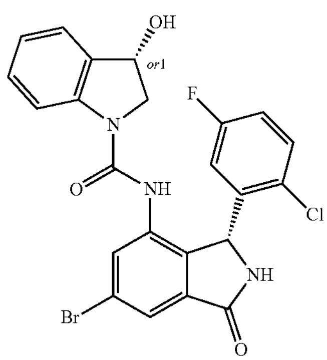 [SMILES: O=C1N[C@@H](c2cc(F)ccc2Cl)c2c(NC(=O)N3C[C@@H](O)c4ccccc43)cc(Br)cc21] | O[C@@H]1CN(C(=O)Nc2cc(Br)cc3C(=O)N[C@H](c23)c2cc(F)ccc2Cl)c2ccccc12 | 1H NMR (400 MHz, DMSO-d6) 9.20 (s, 1H), 8.72 (s, 1H), 7.82 (d, 8.2 Hz, 1H), 7.71-7.66 (m, 1H), 7.60 (d, 1.8 Hz, 1H), 7.40-7.30 (m, 2H), 7.24 (t, 7.8 Hz, 1H), 7.16 (td, 8.4, 3.1 Hz, 1H), 6.99 (t, 7.4 Hz, 1H), 6.67 (s, 1H), 5.98 (s, 1H), 5.66 (d, 6.0 Hz, 1H), 5.12-5.03 (m, 1H), 3.62 (dd, 11.2, 3.5 Hz, 1H), 3.23 (s, 1H) | 518 | A | B |
| I-1515 | 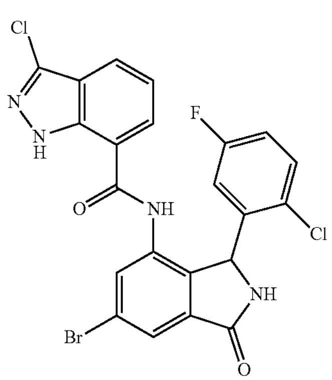 | Fc1ccc(C1)c(c1)C1NC(=O)c2cc(Br)cc(NC(=O)c3cccc4c(Cl)n[nH]c34)c12 | 1H NMR (400 MHz, DMSO-d6) 13.44 (s, 1H), 10.49 (s, 1H), 9.29 (s, 1H), 7.90 (d, 8.1 Hz, 1H), 7.81 (q, 1.8 Hz, 2H), 7.59 (d, 7.3 Hz, 1H), 7.31-7.21 (m, 2H), 7.08-6.99 (m, 1H), 6.08 (s, 1H). | 522.95 | D | |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-1516 | 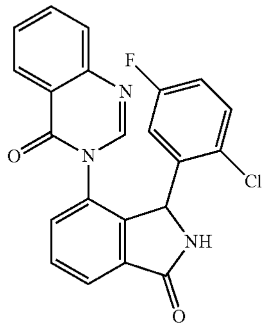 [SMILES: O=C1NC(c2cc(F)ccc2Cl)c2c1cccc2-n1cnc2ccccc2c1=O] | Fc1ccc(C1)c(c1)C1NC(=O)c2cccc(c12)-n1cnc2ccccc2c1=O | 1H NMR (400 MHz, DMSO-d6) 9.30 (s, 1H), 8.60-8.05 (s, 1H), 8.02-7.31 (m, 7H), 7.32-6.80(m, 2H), 6.80-5.39 (m, 2H). | 406.05 | E | |
| I-1517 | 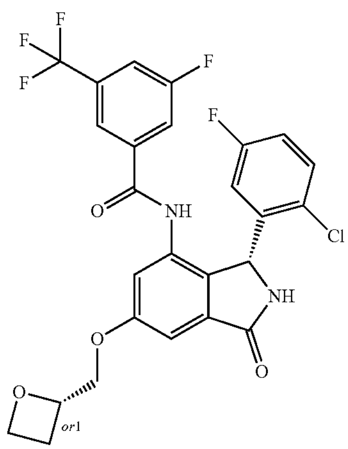 [SMILES: O=C(Nc1cc(OC[C@@H]2CCO2)cc2c1[C@H](c1cc(F)ccc1Cl)NC2=O)c1cc(F)cc(C(F)(F)F)c1] | Fc1ccc(C1)c(c1)[C@@H]1NC(=O)c2cc(OC[C@@H]3CCO3)cc(NC(=O)c3cc(F)cc(c3)C(F)(F)F)c12 | 1H NMR (400 MHz, DMSO-d6) 10.47 (br. s, 1H), 9.14 (br. s, 1H), 7.95 (d, 8.4 Hz, 1H), 7.72 (d, 9.1 Hz, 1H), 7.64 (s, 1H), 7.31 (dd, 8.9, 5.2 Hz, 1H), 7.26 (s, 1H), 7.13 (s, 1H), 7.09 (dt, 8.5, 3.0 Hz, 1H), 6.58 (br. s, 1H), 5.93 (br. s, 1H), 5.10-5.00 (m, 1H), 4.61-4.41 (m, 2H), 4.27 m, 2H), 2.79-2.65 ( m, 1H), 2.63-2.53 (m, 1H). | 553.1 | A | |
| I-1518 | 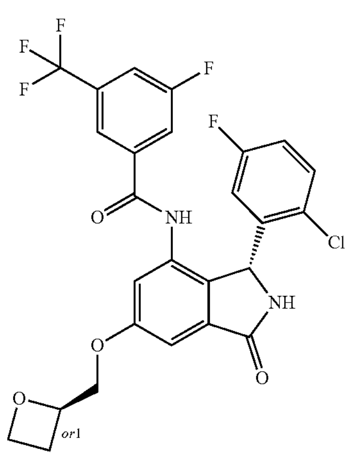 [SMILES: O=C(Nc1cc(OC[C@H]2CCO2)cc2c1[C@H](c1cc(F)ccc1Cl)NC2=O)c1cc(F)cc(C(F)(F)F)c1] | Fc1ccc(C1)c(c1)[C@@H]1NC(=O)c2cc(OC[C@H]3CCO3)cc(NC(=O)c3cc(F)cc(c3)C(F)(F)F)c12 | 1H NMR (400 MHz, DMSO-d6) 10.47 (br. s, 1H), 9.14 (br. s, 1H), 7.95 (d, 8.4 Hz, 1H), 7.72 (d, 9.1 Hz, 1H), 7.64 (s, 1H), 7.31 (dd, 8.9, 5.2 Hz, 1H), 7.26 (s, 1H), 7.13 (s, 1H), 7.09 (dt, 8.5, 3.0 Hz, 1H), 6.58 (br. s, 1H), 5.93 (br. s, 1H), 5.10-5.00 (m, 1H), 4.61-4.41 (m, 2H), 4.27 m, 2H), 2.79-2.65 ( m, 1H), 2.63-2.53 (m, 1H). | 553.1 | A | |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-1519 | 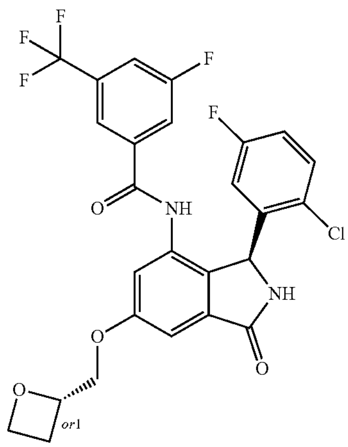 [SMILES: O=C(Nc1cc(OC[C@@H]2CCO2)cc2c1[C@@H](c1cc(F)ccc1Cl)NC2=O)c1cc(F)cc(C(F)(F)F)c1] | Fc1ccc(C1)c(c1)[C@H]1NC(=O)c2cc(OC[C@@H]3CCO3)cc(NC(=O)c3cc(F)cc(c3)C(F)(F)F)c12 | 1H NMR (400 MHz, DMSO-d6) 10.47 (br. s, 1H), 9.14 (br. s, 1H), 7.95 (d, 8.4 Hz, 1H), 7.72 (d, 9.1 Hz, 1H), 7.64 (s, 1H), 7.31 (dd, 8.9, 5.2 Hz, 1H), 7.26 (s, 1H), 7.13 (s, 1H), 7.09 (dt, 8.5, 3.0 Hz, 1H), 6.58 (br. s, 1H), 5.93 (br. s, 1H), 5.10-5.00 (m, 1H), 4.61-4.41 (m, 2H), 4.27 m, 2H), 2.79-2.65 ( m, 1H), 2.63-2.53 (m, 1H). | 553.1 | E | |
| I-1520 | 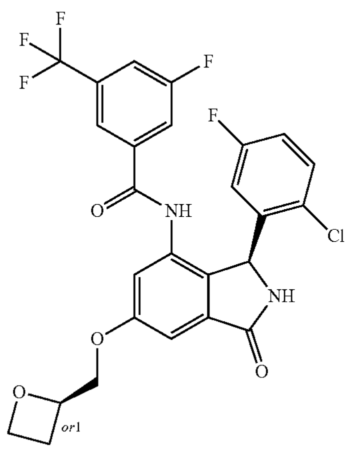 [SMILES: O=C(Nc1cc(OC[C@H]2CCO2)cc2c1[C@@H](c1cc(F)ccc1Cl)NC2=O)c1cc(F)cc(C(F)(F)F)c1] | Fc1ccc(C1)c(c1)[C@H]1NC(=O)c2cc(OC[C@H]3CCO3)cc(NC(=O)c3cc(F)cc(c3)C(F)(F)F)c12 | 1H NMR (400 MHz, DMSO-d6) 10.47 (br. s, 1H), 9.14 (br. s, 1H), 7.95 (d, 8.4 Hz, 1H), 7.72 (d, 9.1 Hz, 1H), 7.64 (s, 1H), 7.31 (dd, 8.9, 5.2 Hz, 1H), 7.26 (s, 1H), 7.13 (s, 1H), 7.09 (dt, 8.5, 3.0 Hz, 1H), 6.58 (br. s, 1H), 5.93 (br. s, 1H), 5.10-5.00 (m, 1H), 4.61-4.41 (m, 2H), 4.27 m, 2H), 2.79-2.65 ( m, 1H), 2.63-2.53 (m, 1H). | 553.1 | E | |
| I-1521 | 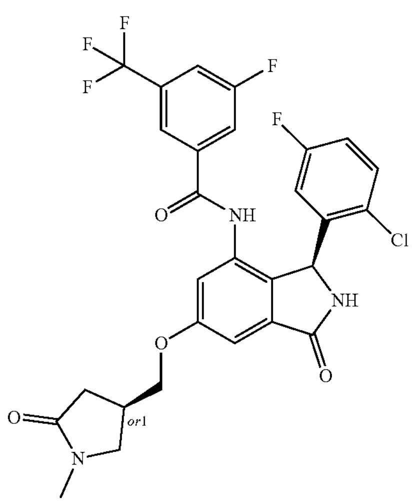 [SMILES: CN1C[C@H](COc2cc(NC(=O)c3cc(F)cc(C(F)(F)F)c3)c3c(c2)C(=O)N[C@@H]3c2cc(F)ccc2Cl)CC1=O] | CN1C[C@H](COc2cc3C(=O)N[C@@H](c3c(NC(=O)c3cc(F)cc(c3)C(F)(F)F)c2)c2cc(F)ccc2Cl)CC1=O | 1H NMR (400 MHz, DMSO-d6) 10.44 (br. s, 1H), 9.11 (br. s, 1H), 7.92 (br. d, 7.1 Hz, 1H), 7.71 (br. d, 8.9 Hz, 1H), 7.65 (s, 1H), 7.31 (dd, 8.9, 5.2 Hz, 1H), 7.20 (s, 1H), 7.13 (s, 1H), 7.08 (dt, 5.6, 3.0 Hz, 1H), 6.58 (br. s, 1H), 5.92 (br. s, 1H), 4.20-3.98 (m, 2H), 3.54 (dd, 9.7, 8.3 Hz, 1H), 3.24 (dd, 9.6, 5.0 Hz, 1H), 2.90-2.76 (m, 1H), 2.73 (s, 3H), 2.44 (dd, 17.0, 9.2 Hz, 1H), 2.17 (dd, 16.8, 6.4 Hz, 1H) | 594.2 | A | |

TABLE 2-continued

Representative Compounds of the Invention with Bioactivity Data.

| Ex. No. | Structure | SMILES | $^1$H NMR | MS | ADP-Glo IC$_{50}$ | MCF 10A IC$_{50}$ |
|---|---|---|---|---|---|---|
| I-1522 | (structure) | CN1C[C@H](COc2cc3C(=O)N[C@H](c3c(NC(=O)c3cc(F)cc(c3)C(F)(F)F)c2)c2cc(F)ccc2Cl)CC1=O | 1H NMR (400 MHz, DMSO-d6) 10.44 (br. s, 1H), 9.11 (br. s, 1H), 7.92 (br. d, 7.1 Hz, 1H), 7.71 (br. d, 8.9 Hz, 1H), 7.65 (s, 1H), 7.31 (dd, 8.9, 5.2 Hz, 1H), 7.20 (s, 1H), 7.13 (s, 1H), 7.08 (dt, 5.6, 3.0 Hz, 1H), 6.58 (br. s, 1H), 5.92 (br. s, 1H), 4.20-3.98 (m, 2H), 3.54 (dd, 9.7, 8.3 Hz, 1H), 3.24 (dd, 9.6, 5.0 Hz, 1H), 2.90-2.76 (m, 1H), 2.73 (s, 3H), 2.44 (dd, overlapped with solvent peak, 17.0, 9.2 Hz, 1H), 2.17 (dd, 16.8, 6.4 Hz, 1H); DMSO satellites at 2.67 and 2.33; signal at 7.13 (s, 1H) is partially overlapped with signal at 7.08 (dt, 5.6, 3.0 Hz, 1H). | 594.2 | A | |
| I-1523 | (structure) | CN1C[C@@H](COc2cc3C(=O)N[C@@H](c3c(NC(=O)c3cc(F)cc(c3)C(F)(F)F)c2)c2cc(F)cc2Cl)CC1=O | 1H NMR (400 MHz, DMSO-d6) 10.44 (br. s, 1H), 9.11 (br. s, 1H), 7.92 (br. d, 7.1 Hz, 1H), 7.71 (br. d, 8.9 Hz, 1H), 7.65 (s, 1H), 7.31 (dd, 8.9, 5.2 Hz, 1H), 7.20 (s, 1H), 7.13 (s, 1H), 7.08 (dt, 5.6, 3.0 Hz, 1H), 6.58 (br. s, 1H), 5.92 (br. s, 1H), 4.20-3.98 (m, 2H), 3.54 (dd, 9.7, 8.3 Hz, 1H), 3.24 (dd, 9.6, 5.0 Hz, 1H), 2.90-2.76 (m, 1H), 2.73 (s, 3H), 2.44 (dd, overlapped with solvent peak, 17.0, 9.2 Hz, 1H), 2.17 (dd, 16.8, 6.4 Hz, 1H); DMSO satellites at 2.67 and 2.33; signal at 7.13 (s, 1H) is partially overlapped with signal at 7.08 (dt, 5.6, 3.0 Hz, 1H). | 594.2 | D | |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-1524 | 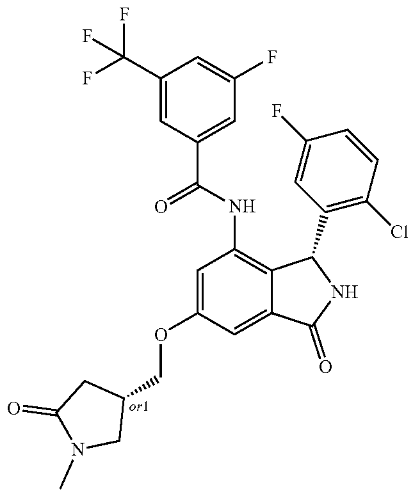 [SMILES: CN1C[C@@H](COc2cc(NC(=O)c3cc(F)cc(C(F)(F)F)c3)c3c(c2)C(=O)N[C@H]3c2cc(F)ccc2Cl)CC1=O] | CN1C[C@@H](COc2cc3C(=O)N[C@H](c3c(NC(=O)c3cc(F)cc(c3)C(F)(F)F)c2)c2cc(F)ccc2Cl)CC1=O | 1H NMR (400 MHz, DMSO-d6) 10.44 (br. s, 1H), 9.11 (br. s, 1H), 7.92 (br. d, 7.1 Hz, 1H), 7.71 (br. d, 8.9 Hz, 1H), 7.65 (s, 1H), 7.31 (dd, 8.9, 5.2 Hz., 1H), 7.20 (s, 1H), 7.13 (s, 1H), 7.08 (dt, 5.6, 3.0 Hz, 1H), 6.58 (br. s, 1H), 5.92 (br. s, 1H), 4.20-3.98 (m, 2H), 3.54 (dd, 9.7, 8.3 Hz, 1H), 3.24 (dd, 9.6, 5.0 Hz, 1H), 2.90-2.76 (m, 1H), 2.73 (s, 3H), 2.44 (dd, 17.0, 9.2 Hz, 1H), 2.17 (dd, 16.8, 6.4 Hz, 1H) | 594.2 | E | |
| I-1525 | 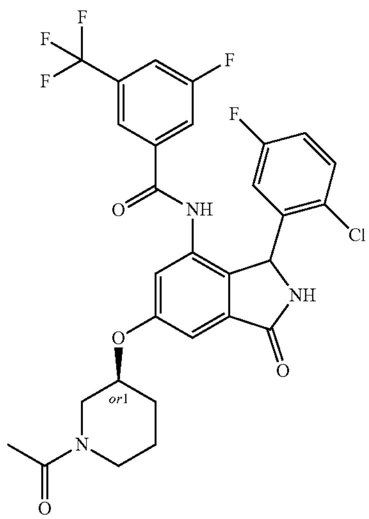 [SMILES: CC(=O)N1CCC[C@H](Oc2cc(NC(=O)c3cc(F)cc(C(F)(F)F)c3)c3c(c2)C(=O)NC3c2cc(F)ccc2Cl)C1] | CC(=O)N1CCC[C@@H](C1)Oc1cc2C(=O)NC(c2c(NC(=O)c2cc(F)cc(c2)C(F)(F)F)c1)c1cc(F)ccc1Cl | (400 MHz, DMSO-D6) 10.44 (s, 1 H), 9.14 (s, 1 H), 7.95 (d, 8.3 Hz, 1 H), 7.71 (d, 8.4 Hz, 1 H), 7.64 (s, 1 H), 7.31 (dd, 8.8, 5.2 Hz, 1 H), 7.26 (ddd, 13.7, 6.3, 2.1 Hz, 1 H), 7.14-7.02 (m, 2 H), 6.60 (br s, 1 H), 5.92 (br s, 1 H), 4.78-4.68 (m, 0.5 H), 4.54-4.43 (m, 0.5 H), 3.93 (ddd, 15.8, 12.7, 2.6 Hz, 0.5 H), 3.84-3.35 (m, 2.5 H), 3.25-3.09 (m, 1 H), 2.10-1.85 (m, 4.5 H), 1.84-1.40 (m, 2.5 H). | 608.3 | B | |
| I-1526 | 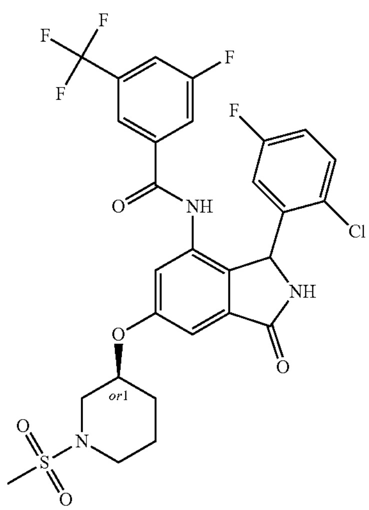 [SMILES: CS(=O)(=O)N1CCC[C@H](Oc2cc(NC(=O)c3cc(F)cc(C(F)(F)F)c3)c3c(c2)C(=O)NC3c2cc(F)ccc2Cl)C1] | CS(=O)(=O)N1CCC[C@@H](C1)Oc1cc2C(=O)NC(c2c(NC(=O)c2cc(F)cc(c2)C(F)(F)F)c1)c1cc(F)ccc1Cl | (400 MHz, DMSO-D6) 10.47 (s, 0.5 H), 10.45 (s, 0.5 H), 9.15 (s, 1 H), 7.95 (br d, 8.5 Hz, 1 H), 7.71 (br d, 8.9 Hz, 1 H), 7.63 (s, 1 H), 7.31 (ddd, 8.8, 5.2, 0.7 Hz, 1 H), 7.27 (dd, 4.6, 2.1 Hz, 1 H), 7.13-7.04 (m, 2 H), 6.56 (br s, 1 H), 5.92 (br s, 1 H), 4.78-4.62 (m, 1 H), 3.54-3.44 (m, 1 H), 3.32-3.10 (m, 3 H), 2.93 (s, 1.5 H), 2.92 (s, 1.5 H), 2.02-1.96 (m, 1 H), 1.92-1.80 (m, 1 H), 1.78-1.68 (m, 1 H), 1.67-1.59 (m, 1 H). | 644.2 | B | |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-1527 | 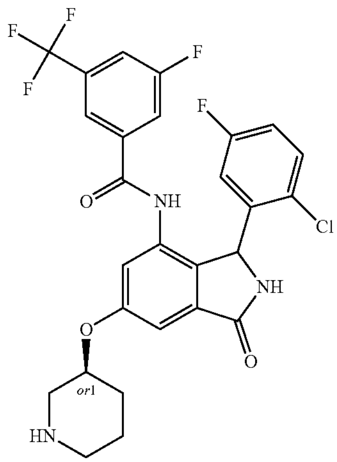 [SMILES: O=C(Nc1cc(O[C@H]2CCCNC2)cc2c1C(c1cc(F)ccc1Cl)NC2=O)c1cc(F)cc(C(F)(F)F)c1] | Fc1ccc(C1)c(c1)C1NC(=O)c2cc(O[C@H]3CCCNC3)cc(NC(=O)c3cc(F)cc(c3)C(F)(F)F)c12 | (400 MHz, DMSO-D6 + D20) 7.92 (d, 8.5 Hz, 1 H), 7.66 (d, 9.1 Hz, 1 H), 7.57 (s, 1 H), 7.35 (app dd, 3.3, 2.3 Hz, 1 H), 7.30 (dd, 8.7, 5.2 Hz, 1 H), 7.17 (dd, 7.0, 1.5 Hz, 1 H), 7.07 (td, 8.3, 2.8 Hz, 1 H), 6.62 (br s, 1 H), 5.90 (br s, 1 H), 4.87 (s, 1 H), 3.37-3.27 (m, 2 H), 3.18-3.09 (m, 1 H), 3.09-2.98 (m, 1 H), 1.98-1.82 (m, 3 H), 1.76-1.61 (m, 1 H). | 566.3 | B | |
| I-1528 | 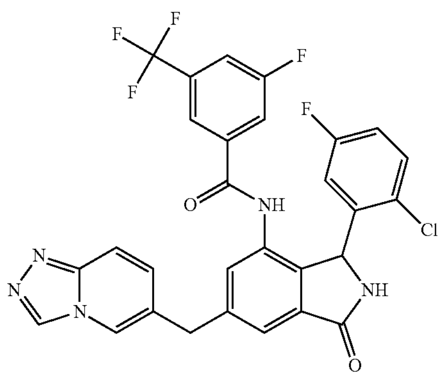 [SMILES: O=C(Nc1cc(Cc2ccc3nncn3c2)cc2c1C(c1cc(F)ccc1Cl)NC2=O)c1cc(F)cc(C(F)(F)F)c1] | Fc1ccc(C1)c(c1)C1NC(=O)c2cc(Cc3cc4nncn4c3)cc(NC(=O)c3cc(F)cc(c3)C(F)(F)F)c12 | 1H-NMR (400 MHz, DMSO-d6) 10.48 (br. s, 1H), 9.24 (s, 1H), 9.14 (br. s, 1H), 8.55 (s, 1H), 7.93 (br. d, 8.6 Hz, 1H), 7.74 (d, 9.5 Hz, 1H), 7.70 (br. d, 8.7 Hz, 1H), 7.68 (s, 1H), 7.65-7.59 (m, 1H), 7.39 (s, 1H), 7.31 (d, 9.6 Hz, 1H), 7.30 (dd, 8.9, 5.3 Hz, 1H), 7.08 (app. td, 8.3, 2.9 Hz, 1H), 6.58 (br. s, 1H), 5.94 (br. s, 1H), 4.17 (d, A of AB, JAB = 16.1 Hz, 1H), 4.12 (d, B of AB, JAB = 15.6 Hz, 1H). | 598.3 | A | |
| I-1529 | 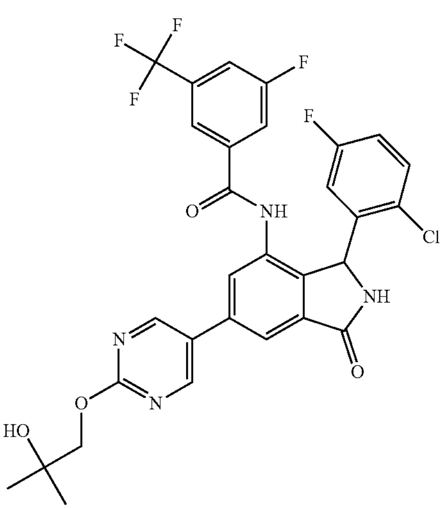 [SMILES: CC(C)(O)COc1ncc(-c2cc(NC(=O)c3cc(F)cc(C(F)(F)F)c3)c3c(c2)C(=O)NC3c2cc(F)ccc2Cl)cn1] | CC(C)(O)COc1ncc(cn1)-c1cc2C(=O)NC(c2c(NC(=O)c2cc(F)cc(c2)C(F)(F)F)c1)c1cc(F)ccc1Cl | 1H-NMR (400 MHz, DMSO-d6) 10.50 (br. s, 1H), 9.26 (br. s, 1H), 9.04 (s, 2H), 8.06 (d, 1.4 Hz, 1H), 7.97 (br. d, 8.4 Hz, 1H), 7.86 (s, 1H), 7.77 (br. d, 8.8 Hz, 1H), 7.70 (s, 1H), 7.33 (dd, 8.9, 5.2 Hz, 1H), 7.11 (app. td, 8.5, 3.1 Hz, 1H), 6.61 (br. s, 1H), 6.04 (br. s, 1H), 4.74 (br. s, 1H), 4.15 (s, 2H), 1.23 (s, 6H). | 633.3 | A | |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-1530 | 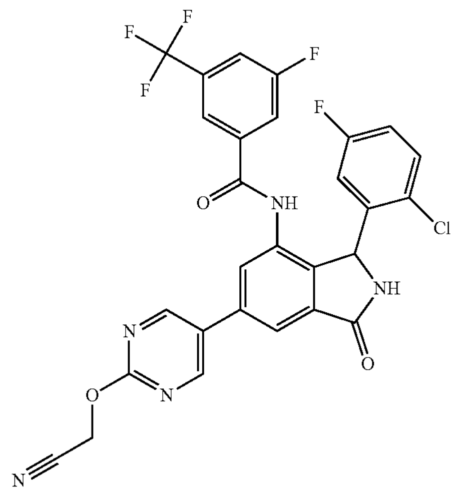 [SMILES: N#CCOc1ncc(-c2cc(NC(=O)c3cc(F)cc(C(F)(F)F)c3)c3c(c2)C(=O)NC3c2cc(F)ccc2Cl)cn1] | Fc1ccc(C1)c(c1)C1NC(=O)c2cc(cc(NC(=O)c3cc(F)cc(c3)C(F)(F)F)c12)-c1cnc(OCC#N)nc1 | (400 MHz, DMSO-d6) 10.75 (br s, 1H), 9.26 (br s, 1H), 9.17 (s, 1H), 9.16 (s, 1H), 8.10 (s, 1H), 7.96 (d, 7.5 Hz, 1H), 7.91 (s, 1H), 7.77 (d, 8.7 Hz, 1H), 7.71 (s, 1H), 7.37-7.29 (m, 1H), 7.11 (t, 8.2 Hz, 1H), 6.68 (br s, 1H), 6.04 (br s, 1H), 5.35 (s, 2H) | 598.3 | A | |
| I-1531 | 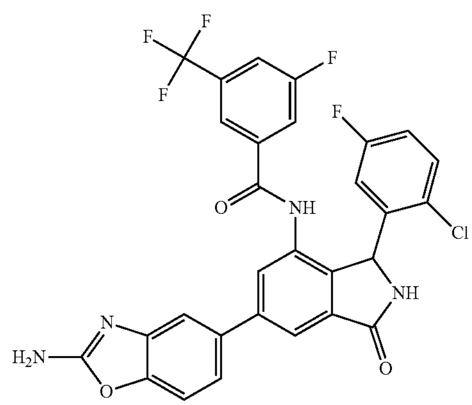 [SMILES: Nc1nc2cc(-c3cc(NC(=O)c4cc(F)cc(C(F)(F)F)c4)c4c(c3)C(=O)NC4c3cc(F)ccc3Cl)ccc2o1] | Nc1nc2cc(ccc2o1)-c1cc2C(=O)NC(c2c(NC(=O)c2cc(F)cc(c2)C(F)(F)F)c1)c1cc(F)ccc1Cl | (400 MHz, CD3CN) 8.73 (s, 1H), 7.99 (d, 1.4 Hz, 1H), 7.80 (s, 1H), 7.69-7.59 (m, 4H), 7.40 (s, 2H), 7.30 (br. s, 1H), 7.27 (dd, 8.9, 5.1 Hz, 1H), 6.98 (ddd, 8.7, 8.1, 3.1 Hz, 1H), 6.68 (br. s, 1H), 6.18 (br. s, 1H), 5.85 (br. s, 2H). | 599.2 | A | |
| I-1532 | 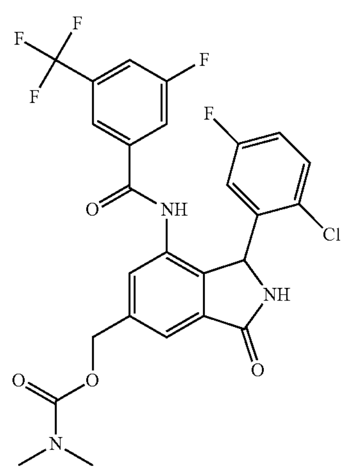 [SMILES: CN(C)C(=O)OCc1cc(NC(=O)c2cc(F)cc(C(F)(F)F)c2)c2c(c1)C(=O)NC2c1cc(F)ccc1Cl] | CN(C)C(=O)OCc1cc2C(=O)NC(c2c(NC(=O)c2cc(F)cc(c2)C(F)(F)F)c1)c1cc(F)ccc1Cl | NMR (400 MHz, DMSO) 10.54 (br s, 1H), 9.19 (br s, 1H), 7.95 (d, 8.6 Hz, 1H), 7.73 (d, 8.9 Hz, 1H), 7.67 (s, 1H), 7.64 (s, 1H), 7.47 (s, 1H), 7.31 (dd, 8.7, 5.2 Hz, 1H), 7.09 (td, 8.5, 2.7 Hz, 1H), 6.61 (br s, 1H), 5.97 (br s, 1H), 5.23 (s, 2H), 2.92 (s, 3H), 2.86 (s, 3H). | 568.1 | A | |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-1533 | 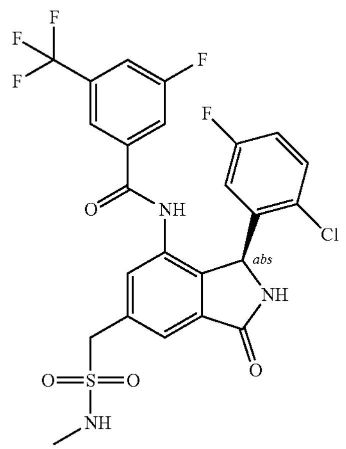 [SMILES: CNS(=O)(=O)Cc1cc(NC(=O)c2cc(F)cc(C(F)(F)F)c2)c2c(c1)C(=O)N[C@@H]2c1cc(F)ccc1Cl] | CNS(=O)(=O)Cc1cc2C(=O)N[C@@H](c2c(NC(=O)c2cc(F)cc(c2)C(F)(F)F)c1c(F)ccc1Cl | NMR (400 MHz, CD3CN) 8.74 (s, 1H), 7.75 (d, 1.4 Hz, 1H), 7.68-7.53 (m, 1H), 7.62-7.54 (m, 3H) 7.32-7.23 (m, 2H), 6.98 (ddd, 8.9, 8.0, 3.1 Hz, 1H), 6.64 (br, s, 1H), 6.25-6.04 (br, s, 1H), 5.22 (q, 4.8 Hz, 1H), 4.45 (s, 2H), 2.71 (d, 5.0 Hz, 3H). | 574 | B | |
| I-1534 | 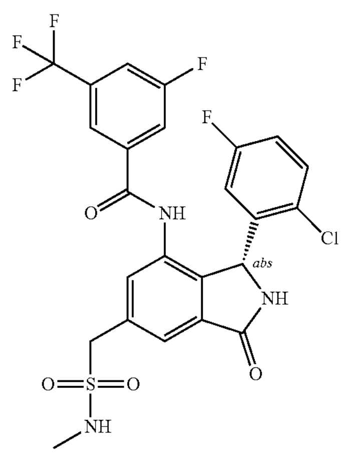 [SMILES: CNS(=O)(=O)Cc1cc(NC(=O)c2cc(F)cc(C(F)(F)F)c2)c2c(c1)C(=O)N[C@H]2c1cc(F)ccc1Cl] | CNS(=O)(=O)Cc1cc2C(=O)N[C@H](c2c(NC(=O)c2cc(F)cc(c2)C(F)(F)F)c1c1cc(F)ccc1Cl | | 574 | A | |
| I-1535 | 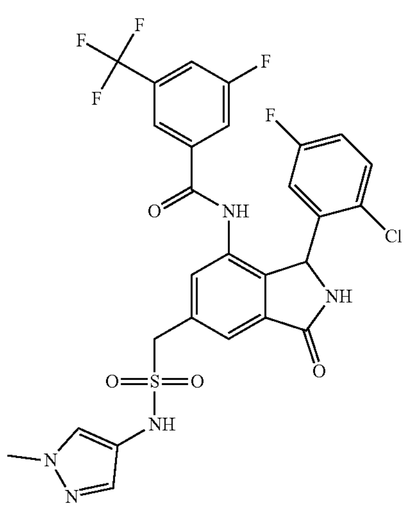 [SMILES: Cn1cc(NS(=O)(=O)Cc2cc(NC(=O)c3cc(F)cc(C(F)(F)F)c3)c3c(c2)C(=O)NC3c2cc(F)ccc2Cl)cn1] | Cn1cc(NS(=O)(=O)Cc2cc3C(=O)NC(c3c(NC(=O)c3cc(F)cc(c3)C(F)(F)F)c2)c2c(F)ccc2Cl)cn1 | NMR (400 MHz, CD3CN) 8.78 (s, 1H), 7.71 (s, 1H), 7.65 (d, 8.4 Hz, 1H), 7.61 (s, 1H), 7.58 (d, 9.0 Hz, 1H), 7.55 (s, 1H) 7.52 (s, 1H), 7.34 (s, 1H), 7.30 (br, s, 1H), 7.27 (dd, 8.9, 5.1 Hz, 1H), 6.98 (td, 8.4, 3.0 Hz, 1H), 6.67 (br, s, 1H), 6.11 (br, s, 1H), 4.49 (d, 14.1 Hz, 1H), 4.45 (d, 14.1 Hz, 1H), 3.82 (s, 3H). | 640 | A | |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-1536 | 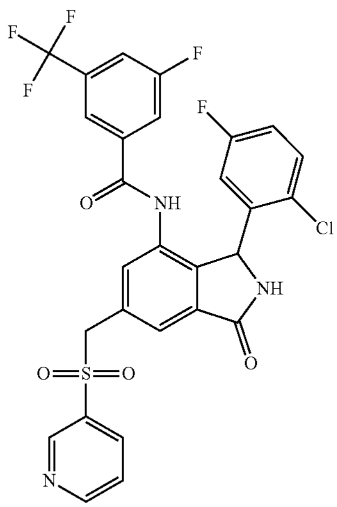 [SMILES: O=C(Nc1cc(CS(=O)(=O)c2cccnc2)cc2c1C(c1cc(F)ccc1Cl)NC2=O)c1cc(F)cc(C(F)(F)F)c1] | Fc1ccc(C1)c(c1)C1NC(=O)c2cc(CS(=O)(=O)c3cccnc3)cc(NC(=O)c3cc(F)cc(c3)C(F)(F)F)c12 | NMR (400 MHz, CD3CN) 8.84 (s, 1H), 8.83 (s, 1H), 8.65 (s, 1H), 8.03 (d, 7.9 Hz, 1H), 7.65 (d, 8.2 Hz, 1H), 7.58 (d, 9.1 Hz, 1H), 7.55-7.50 (m, 2H), 7.48 (s, 2H), 7.27 (dd, 8.8, 5.1 Hz, 1H), 7.27 (NH, s, 1H), 6.98 (td, 8.4, 3.0 Hz, 1H), 6.68 (br, s, 1H), 6.11 (br, s, 1H), 4.68 (s, 2H). | 622 | A | |
| I-1537 | 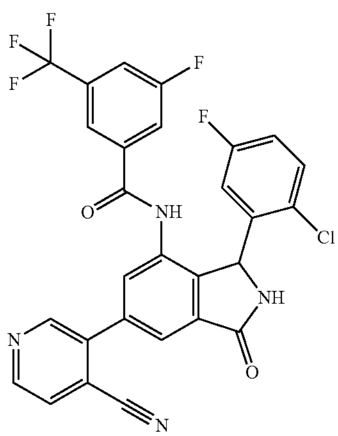 [SMILES: N#Cc1ccncc1-c1cc(NC(=O)c2cc(F)cc(C(F)(F)F)c2)c2c(c1)C(=O)NC2c1cc(F)ccc1Cl] | Fc1ccc(C1)c(c1)C1NC(=O)c2cc(cc(NC(=O)c3cc(F)cc(c3)C(F)(F)F)c12)-c1cnccc1C#N | | | A | |
| I-1538 | 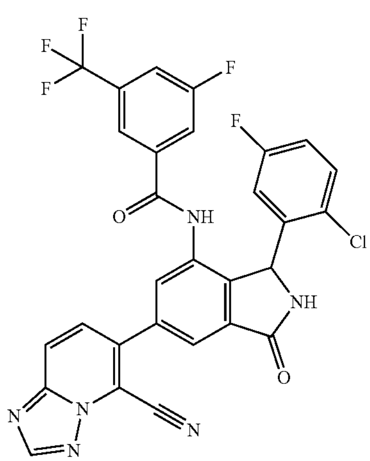 [SMILES: N#Cc1c(-c2cc(NC(=O)c3cc(F)cc(C(F)(F)F)c3)c3c(c2)C(=O)NC3c2cc(F)ccc2Cl)ccc2ncnn12] | Fc1ccc(C1)c(c1)C1NC(=O)c2cc(cc(NC(=O)c3cc(F)cc(c3)C(F)(F)F)c12)-c1ccc2ncnn2c1C#N | | | A | |

TABLE 2-continued

Representative Compounds of the Invention with Bioactivity Data.

| Ex. No. | Structure | SMILES | $^1$H NMR | MS | ADP-Glo IC$_{50}$ | MCF 10A IC$_{50}$ |
|---|---|---|---|---|---|---|
| I-1539 | 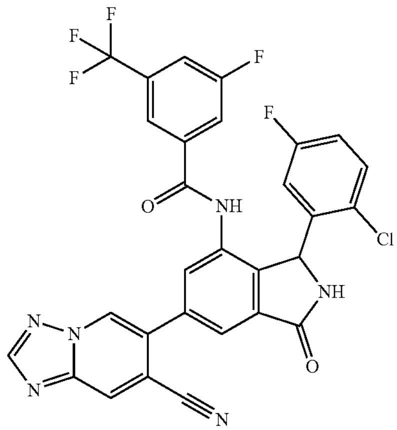 [SMILES: N#Cc1cc2ncnn2cc1-c1cc(NC(=O)c2cc(F)cc(C(F)(F)F)c2)c2c(c1)C(=O)NC2c1cc(F)ccc1Cl] | Fc1ccc(C1)c(c1)C1NC(=O)c2cc(cc(NC(=O)c3cc(F)cc(c3)C(F)(F)F)c12)-c1cn2ncnc2cc1C#N | | | A | |
| I-1540 | 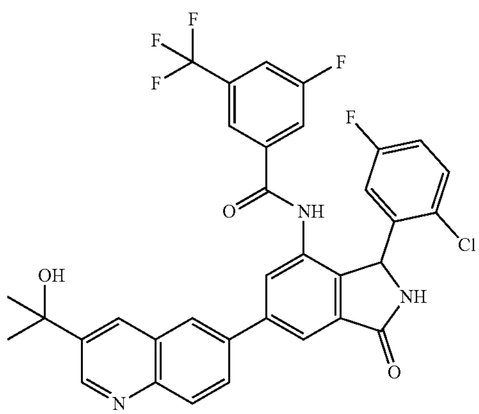 [SMILES: CC(C)(O)c1cnc2ccc(-c3cc(NC(=O)c4cc(F)cc(C(F)(F)F)c4)c4c(c3)C(=O)NC4c3cc(F)ccc3Cl)cc2c1] | CC(C)(O)c1cnc2cc(cc2c1)-c1cc2C(=O)NC(c2c(NC(=O)c2cc(F)cc(c2)C(F)(F)F)c1)c1cc(F)ccc1Cl | | 652.6 | A | |
| I-1541 | 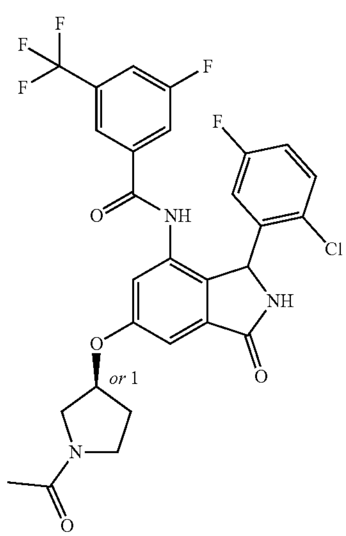 [SMILES: CC(=O)N1CC[C@H](Oc2cc(NC(=O)c3cc(F)cc(C(F)(F)F)c3)c3c(c2)C(=O)NC3c2cc(F)ccc2Cl)C1] | CC(=O)N1CC[C@@H](C1)Oc1cc2C(=O)NC(c2c(NC(=O)c2cc(F)cc(c2)C(F)(F)F)c1)c1cc(F)ccc1Cl | (400 MHz, DMSO-D6) 9.17 (s, 1 H), 7.94 (br d, 8.4 Hz, 1 H), 7.72 (br d, 9.0 Hz, 1 H), 7.64 (s, 1 H), 7.31 (dd, 8.8, 5.2 Hz, 1 H), 7.24 (app t, 2.0 Hz, 0.5 H), 7.22 (d, 2.1 Hz, 0.25 H), 7.21 (d, 2.1 Hz, 0.25 H), 7.12-7.04 (m, 2 H), 6.54 (br s, 1 H), 5.94 (br s, 1 H), 5.27 (s, 0.5 H), 5.18 (s, 0.5 H), 3.85 (dd, 11.8, 4.4 Hz., 0.5 H), 3.69-3.62 (m, 1 H), 3.62-3.51 (m, 2 H), 3.33 (td, 10.4, 2.3 Hz, 0.5 H), 2.34-2.18 (m, 1 H), 2.17-2.01 (m, 1 H), 1.98 (s, 1.5 H), 1.96 (s, 0.75 H), 1.94 (s, 0.75 H). | 594.3 | B | |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-1542 | 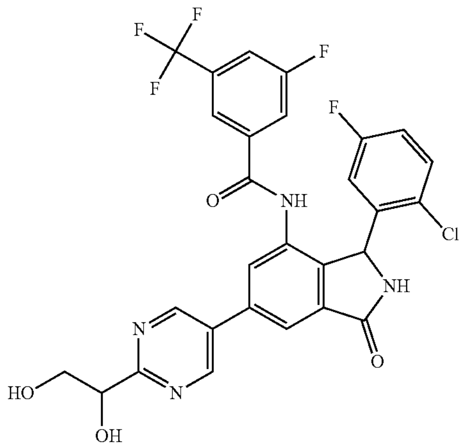 [SMILES: O=C(Nc1cc(-c2cnc(C(O)CO)nc2)cc2c1C(c1cc(F)ccc1Cl)NC2=O)c1cc(F)cc(C(F)(F)F)c1] | OCC(O)c1ncc(cn1)-c1cc2C(=O)NC(c2c(NC(=O)c2cc(F)cc(c2)C(F)(F)F)c1)c1cc(F)ccc1Cl | NMR (400 MHz, DMS-d6) 10.75 (br s, 1H), 9.27 (br s, 1H), 9.24 (s, 2H), 8.14 (s, 1H), 7.97 (d, 8.8 Hz, 1H), 7.94 (s, 1H), 7.77 (d, 8.4 Hz), 7.70 (s, 1H), 7.34 (dd, 8.9, 5.1 Hz, 1H), 7.11 (td, 8.6, 3.0 Hz, 1H), 6.63 (br s, 1H), 6.04 (br s, 1H), 5.36 (d, 6.2 Hz, 1H), 4.75-4.69 (m, 2H), 3.91-3.67 (m, 2H). | 605.2 | A | |
| I-1543 | 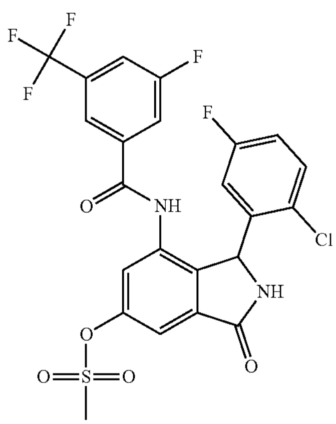 [SMILES: CS(=O)(=O)Oc1cc(NC(=O)c2cc(F)cc(C(F)(F)F)c2)c2c(c1)C(=O)NC2c1cc(F)ccc1Cl] | CS(=O)(=O)Oc1cc2C(=O)NC(c2c(NC(=O)c2cc(F)cc(c2)C(F)(F)F)c1)c1cc(F)ccc1Cl | (400 MHz, DMSO-D6) 10.68 (br s, 1 H), 9.36 (br s, 1 H), 7.96 (br d, 8.4 Hz, 1 H), 7.73 (br d, 9.0 Hz, 1 H), 7.66 (d, 1.8 Hz, 1 H), 7.64 (s, 1 H), 7.52 (s, 1 H), 7.33 (dd, 8.9, 5.2 Hz, 1 H), 7.11 (td, 8.5, 3.0 Hz, 1 H), 6.71 (br s, 1 H), 6.02 (br s, 1 H), 3.50 (s, 3 H). | 559.2 | A | |
| I-1544 | 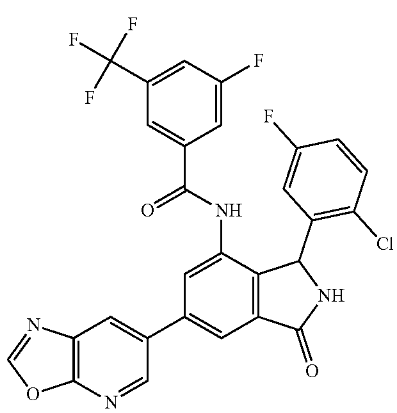 [SMILES: O=C(Nc1cc(-c2cnc3ocnc3c2)cc2c1C(c1cc(F)ccc1Cl)NC2=O)c1cc(F)cc(C(F)(F)F)c1] | Fc1ccc(C1)c(c1)C1NC(=O)c2cc(cc(NC(=O)c3cc(F)cc(c3)C(F)(F)F)c12)-c1cnc2ocnc2c1 | NMR (400 MHz, DMSO-d6) 10.65 (br s, 1H), 9.26 (br s, 1H), 9.00 (s, 1H), 8.84 (d, 2.2 Hz, 1H), 8.72 (d, 2.1 Hz, 1H), 8.09 (d, 1.3 Hz, 1H), 7.97 (d, 8.4 Hz, 1H), 7.93 (s, 1H), 7.77 (d, 9.0 Hz, 1H), 7.71 (s, 1H), 7.34 (dd, 8.9, 5.2 Hz, 1H), 7.11 (td, 8.6, 3.0 Hz, 1H), 6.66 (br s, 1H), 6.06 (br s, 1H). | 583.2 | A | |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-1545 | 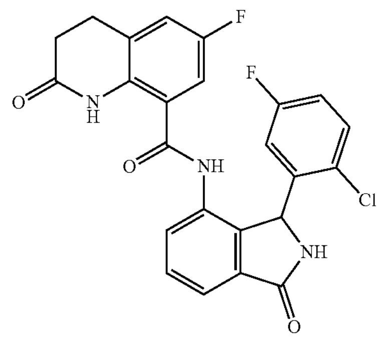 [SMILES: O=C1CCc2cc(F)cc(C(=O)Nc3cccc4c3C(c3cc(F)ccc3Cl)NC4=O)c2N1] | Fc1ccc(C1)c(c1)C1NC(=O)c2cccc(NC(=O)c3cc(F)cc4CCC(=O)Nc34)c12 | 1H NMR (400 MHz, DMSO-d6) 10.35 (s, 1H), 10.16 (s, 1H), 9.15 (s, 1H), 7.72 (d, 7.4 Hz, 1H), 7.65 (t, 7.6 Hz, 1H), 7.51 (d, 7.7 Hz, 1H), 7.40-7.32 (m, 2H), 7.13 (td, 8.4, 3.1 Hz, 1H), 6.97-6.89 (m, 1H), 6.53 (s, 1H), 6.01 (s, 1H), 2.96 (q, 9.6, 8.6 Hz, 2H), 2.52 (s, 2H). | 468.1 | E | |
| I-1546 | 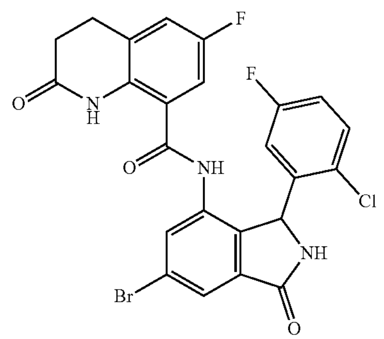 [SMILES: O=C1CCc2cc(F)cc(C(=O)Nc3cc(Br)cc4c3C(c3cc(F)ccc3Cl)NC4=O)c2N1] | Fc1ccc(C1)c(c1)C1NC(=O)c2cc(Br)cc(NC(=O)c3cc(F)cc4CCC(=O)Nc34)c12 | 1H NMR (400 MHz, DMSO-d6) 10.41 (s, 1H), 10.08 (s, 1H), 9.30 (s, 1H), 7.83 (s, 1H), 7.78 (d, 1.7 Hz, 1H), 7.37 (dt, 8.5, 4.3 H7, 2H), 7.15 (td, 8.4, 3.1 Hz, 1H), 6.84 (d, 9.4 Hz, 1H), 6.68 (s, 1H), 5.99 (s, 1H), 2.96 (q, 8.5, 8.0 Hz, 2H), 2.52 (s, 2H). | 546 | E | |
| I-1547 | 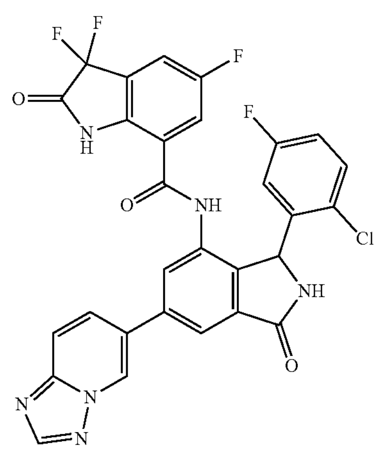 [SMILES: O=C(Nc1cc(-c2ccc3ncnn3c2)cc2c1C(c1cc(F)ccc1Cl)NC2=O)c1cc(F)cc2c1NC(=O)C2(F)F] | Fc1ccc(C1)c(c1)C1NC(=O)c2cc(cc(NC(=O)c3cc(F)cc4c3NC(=O)C4(F)F)c12)-c1ccc2ncnn2c1 | 1H NMR (400 MHz, DMSO-d6) 11.30-10.90 (s, 1H), 10.56 (s, 1H), 9.48 (d, 1.7 Hz, 1H), 9.27 (s, 1H), 8.59 (s, 1H), 8.17-8.10 (m, 2H), 8.00 (d, 9.6 Hz, 3H), 7.38 (d, 9.1 Hz, 2H), 7.14 (s, 1H), 6.20-5.90 (s, 1H). | 607.05 | A | |
| I-1548 | 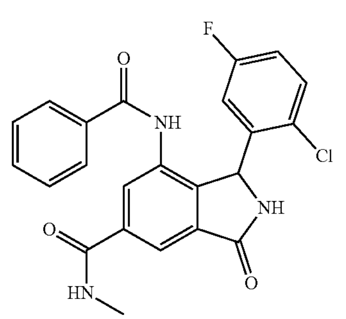 [SMILES: CNC(=O)c1cc(NC(=O)c2ccccc2)c2c(c1)C(=O)NC2c1cc(F)ccc1Cl] | CNC(=O)c1cc2C(=O)NC(c2c(NC(=O)c2cccc2)c1c(F)ccc1Cl | 1H NMR (400 MHz, DMSO-d6) 10.27 (s, 1H), 9.22 (s, 1H), 8.76 (d, 4.8 Hz, 1H), 8.16 (d, 1.5 Hz, 1H), 8.02 (d, 1.6 Hz, 1H), 7.62-7.51 (m, 3H), 7.44 (t, 7.6 Hz, 2H), 7.35 (dd, 8.9, 5.1 Hz, 1H), 7.12 (td, 8.3, 3.0 Hz, 1H), 6.70 (s, 1H), 6.10 (s, 1H), 2.83 (d, 4.4 Hz, 3H). | 438.1 | E | |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-1549 | 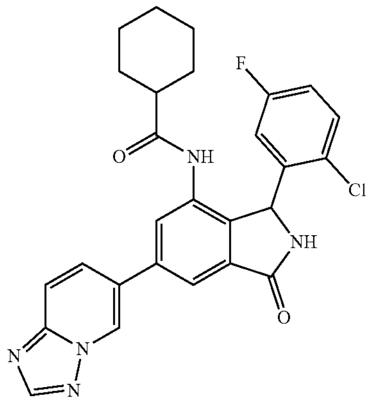 [SMILES: O=C1NC(c2cc(F)ccc2Cl)c2c(NC(=O)C3CCCCC3)cc(-c3ccc4ncnn4c3)cc21] | Fc1ccc(C1)c(c1)C1NC(=O)c2cc(cc(NC(=O)C3CCCCC3)c12)-c1ccc2ncnn2c1 | 1H NMR (400 MHz, DMSO-d6) 9.70 (s, 1H), 9.43 (dd, 1.9, 0.9 Hz, 1H), 9.19 (s, 1H), 8.57 (s, 1H), 8.09 (dd, 9.3, 1.9 Hz, 1H), 8.02-7.94 (m, 2H), 7.81 (d, 1.7 Hz, 1H), 7.51 (s, 1H), 7.25 (td, 8.4, 3.1 Hz, 1H), 6.13 (s, 1H), 2.06 (s, 1H), 1.62 (d, 16.2 Hz, 3H), 1.48 (s, 1H), 1.33 (s, 1H), 1.17 (d, 10.8 Hz, 1H), 1.13 (s, 4H). | 504.2 | D | |
| I-1550 | 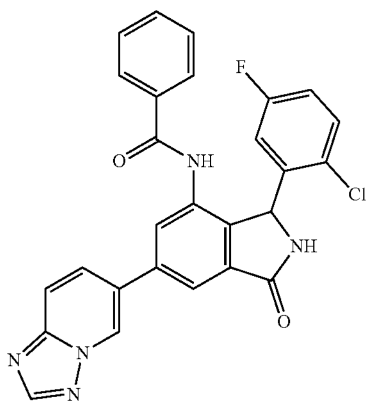 [SMILES: O=C(Nc1cc(-c2ccc3ncnn3c2)cc2c1C(c1cc(F)ccc1Cl)NC2=O)c1ccccc1] | Fc1ccc(C1)c(c1)C1NC(=O)c2cc(cc(NC(=O)c3ccccc3)c12)-c1ccc2ncnn2c1 | 1H NMR (400 MHz, DMSO-d6) 10.28 (s, 1H), 9.47 (d, 1.7 Hz, 1H), 9.23 (s, 1H), 8.58 (s, 1H), 8.14 (dd, 9.3, 2.0 Hz, 1H), 8.09 (d, 1.7 Hz, 1H), 8.02-7.95 (m, 2H), 7.66-7.59 (m, 2H), 7.56 (t, 7.3 Hz, 1H), 7.45 (t, 7.6 Hz, 2H), 7.37 (dd, 8.9, 5.2 Hz, 1H), 7.14 (td, 8.3, 3.1 Hz, 1H), 6.15 (s, 1H). | 498 | D | |
| I-1551 | 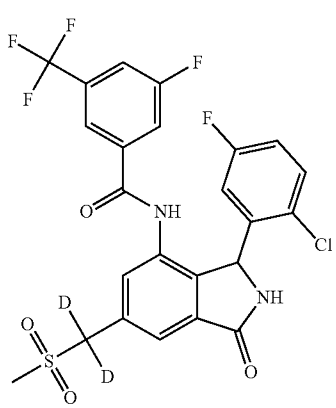 [SMILES: [2H]C([2H])(c1cc(NC(=O)c2cc(F)cc(C(F)(F)F)c2)c2c(c1)C(=O)NC2c1cc(F)ccc1Cl)S(C)(=O)=O] | [2H]C([2H])(c1cc2C(=O)NC(c2c(NC(=O)c2cc(F)cc(c2)C(F)(F)F)c1Cl)c1ccc(F)ccc1Cl)S(C)(=O)=O | NMR (400 MHz, CD3CN) 8.72 (br, s, 1H), 7.78 (d, 1.4 Hz, 1H), 7.65 (br, d, 8.5 Hz, 1H), 7.63 (s, 1H), 7.60 (br, d, 9.1 Hz, 1H), 7.56 (s, 1H), 7.30 (br, s, 1H), 7.26 (dd, 8.9, 5.1 Hz, 1H), 6.98 (ddd, 8.8, 8.1, 3.1 Hz, 1H), 6.66 (br, s, 1H), 6.14 (br, s, 1H), 2.89 (s, 3H). | 561 | A | |

TABLE 2-continued

Representative Compounds of the Invention with Bioactivity Data.

| Ex. No. | Structure | SMILES | $^1$H NMR | MS | ADP-Glo IC$_{50}$ | MCF 10A IC$_{50}$ |
|---|---|---|---|---|---|---|
| I-1552 | 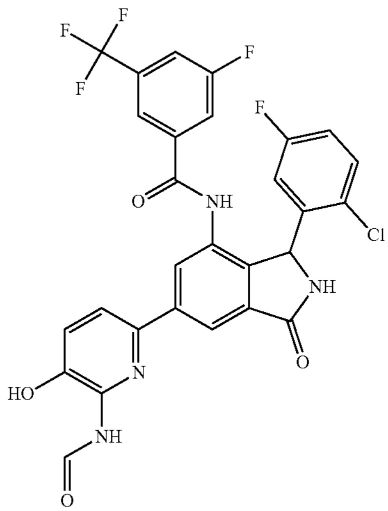 [SMILES: O=CNc1nc(-c2cc(NC(=O)c3cc(F)cc(C(F)(F)F)c3)c3c(c2)C(=O)NC3c2cc(F)ccc2Cl)ccc1O] | Oc1ccc(n c1NC=O)- c1cc2C(= O)NC(c2 c(NC(=O) c2cc(F)c c(c2)C(F) (F)F)c1)c 1cc(F)ccc 1Cl | (400 MHz, DMSO-D6) 10.59 (br s, 1 H), 9.92 (br s, 1 H), 9.40 (s, 1 H), 9.18 (s, 1 H), 8.21 (s, 1 H), 8.15 (s, 1 H), 7.95 (d, 8.4 Hz, 1 H), 7.79-7.73 (m, 2 H), 7.68 (s, 1 H), 7.35-7.30 (m, 1 H), 7.29 (d, 10.0 Hz, 1 H), 7.09 (td, 8.4, 3.0 Hz, 1 H), 6.67 (br s, 1 H), 6.00 (br s, 1 H). | 601.2 | A | |
| I-1553 | 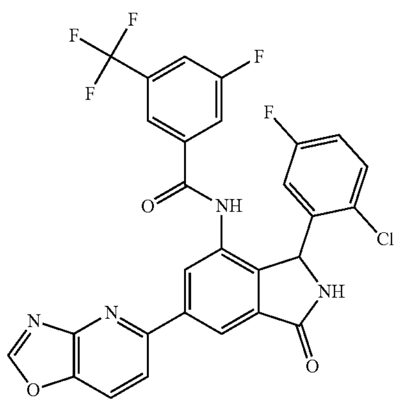 [SMILES: O=C(Nc1cc(-c2ccc3ocnc3n2)cc2c1C(c1cc(F)ccc1Cl)NC2=O)c1cc(F)cc(C(F)(F)F)c1] | Fc1ccc(C 1)c(c1)C1 NC(=O)c 2cc(cc(N C(=O)c3 cc(F)cc(c 3)C(F)(F) F)c12)- c1ccc2oc nc2n1 | (400 MHz, DMSO-D6) 9.26 (br s, 1 H), 9.12 (s, 1 H), 8.70 (br s, 1 H), 8.41 (d, 8.5 Hz, 1 H), 8.40 (s, 1 H), 8.36 (d, 1.2 Hz, 1 H), 8.29 (d, 8.6 Hz, 1 H), 7.96 (d, 8.4 Hz, 1 H), 7.80 (d, 9.1 Hz, 1 H), 7.74 (s, 1 H), 7.34 (dd, 8.9, 5.2 Hz, 1 H), 7.11 (td, 8.5, 3.0 Hz, 1 H), 6.69 (br s, 1 H), 6.07 (br s, 1 H). | 585.2 | A | |
| I-1554 | Isomer 1 | Fc1ccc(C 1)c(c1)C1 NC(=O)c 2cc(cc(N C(=O)c3 cc(F)cc(c 3)C(F)(F) F)c12)- c1cnn(c1)- c1ncccn1 | NMR (400 MHz, DMSO-d6) 10.57 (br s, 1H), 9.29 (s, 1H), 9.20 (br s, 1H), 8.93 (d, 4.8 Hz, 2H), 8.54 (s, 1H), 8.14 (s, 1H), 7.97 (br d, 7.1 Hz, 1H), 7.96 (s, 1H), 7.78 (br d, 9.6 Hz, 1H), 7.73 (s, 1H), 7.53 (t, 4.8 Hz, 1H), 7.33 (dd, 8.9, 5.2 Hz, 1H), 7.10 (td, 8.5, 3.1 Hz, 1H), 6.65 (br s, 1H), 6.01 (br s, 1H). | 611 | D | |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-1555 | 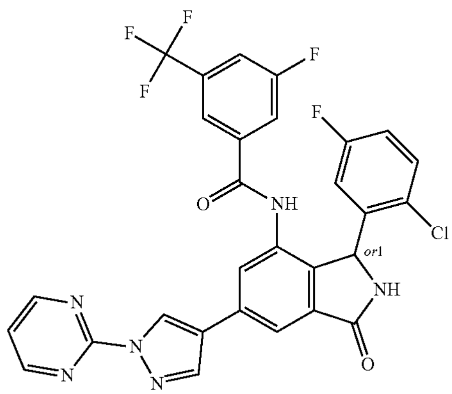 [SMILES: O=C(Nc1cc(-c2cnn(-c3ncccn3)c2)cc2c1C(c1cc(F)ccc1Cl)NC2=O)c1cc(F)cc(C(F)(F)F)c1] | Fc1ccc(C1)c(c1)C1NC(=O)c2cc(cc(NC(=O)c3cc(F)cc(c3)C(F)(F)F)c12)-c1cnn(c1)-c1ncccn1 | NMR (400 MHz, DMSO-d6) 10.57 (br s, 1H), 9.29 (s, 1H), 9.20 (br s, 1H), 8.93 (d, 4.8 Hz, 2H), 8.54 (s, 1H), 8.14 (s, 1H), 7.97 (br d, 7.1 Hz, 1H), 7.96 (s, 1H), 7.78 (br d, 9.6 Hz, 1H), 7.73 (s, 1H), 7.53 (t, 4.8 Hz, 1H), 7.33 (dd, 8.9, 5.2 Hz, 1H), 7.10 (td, 8.5, 3.1 Hz, 1H), 6.65 (br s, 1H), 6.01 (br s, 1H). | 611 | A | |
| I-1556 | 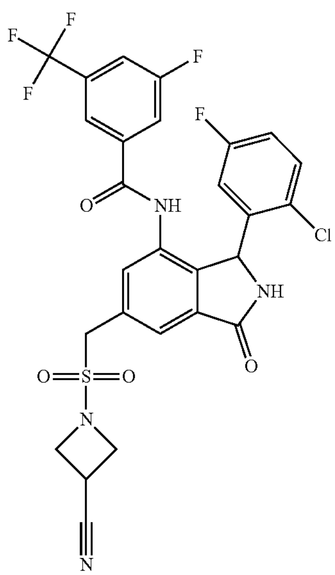 [SMILES: N#CC1CN(S(=O)(=O)Cc2cc(NC(=O)c3cc(F)cc(C(F)(F)F)c3)c3c(c2)C(=O)NC3c2cc(F)ccc2Cl)C1] | Fc1ccc(C1)c(c1)C1NC(=O)c2cc(CS(=O)(=O)N3CC(C3)C#N)cc(NC(=O)c3cc(F)cc(c3)C(F)(F)F)c12 | NMR (400 MHz, DMSO-d6) 10.60 (s, 1H), 9.22 (br. s, 1H), 7.95 (br. d, 8.5 Hz, 1H), 7.79 (s, 1H), 7.74 (br. d, 8.8 Hz, 1H), 7.65 (s, 1H), 7.55 (s, 1H), 7.32 (dd, 8.9, 5.2 Hz, 1H), 7.10 (td, 8.4, 3.0 Hz, 1H), 6.66 (br. s, 1H), 5.97 (br. s, 1H), 4.85 (s, 2H), 4.22-4.11 (m, 3H), 4.10-4.04 (m, 1H), 3.87-3.78 (m, 1H). | 625.2 | A | |
| I-1557 | 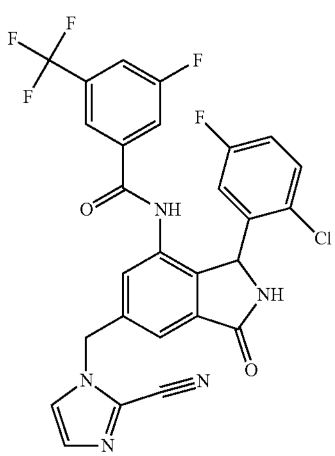 [SMILES: N#Cc1nccn1Cc1cc(NC(=O)c2cc(F)cc(C(F)(F)F)c2)c2c(c1)C(=O)NC2c1cc(F)ccc1Cl] | Fc1ccc(C1)c(c1)C1NC(=O)c2cc(Cn3cnc3C#N)cc(NC(=O)c3cc(F)cc(c3)C(F)(F)F)c12 | 1H-NMR (400 MHz, DMSO-d6) 10.57 (br. s, 1H), 9.24 (br. s, 1H), 7.95 (br. d, 8.5 Hz, 1H), 7.85 (d, 1.0 Hz, 1H), 7.71 (br. d, 8.9 Hz, 1H), 7.62-7.59 (m, 2H), 7.37-7.33 (m, 1H), 7.31 (dd, 8.9, 5.2 Hz, 1H), 7.31 (d, 1.0 Hz, 1H), 7.09 (td, 8.4, 3.1 Hz, 1H), 6.58 (br. s, 1H), 5.97 (br. s, 1H), 5.66-5.58 (m, 2H). | 572.1 | A | |

TABLE 2-continued

Representative Compounds of the Invention with Bioactivity Data.

| Ex. No. | Structure | SMILES | $^1$H NMR | MS | ADP-Glo IC$_{50}$ | MCF 10A IC$_{50}$ |
|---|---|---|---|---|---|---|
| I-1558 | 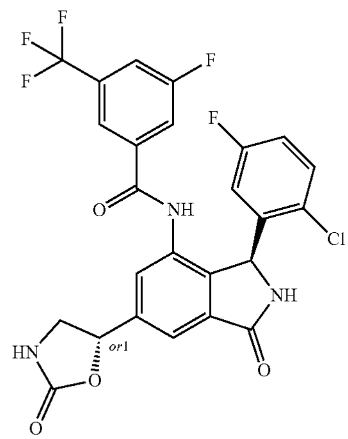 [SMILES: O=C1NC[C@H](c2cc(NC(=O)c3cc(F)cc(C(F)(F)F)c3)c3c(c2)C(=O)N[C@@H]3c2cc(F)ccc2Cl)O1] | Fc1ccc(C1)c(c1)[C@H]1NC(=O)c2cc(cc(NC(=O)c3cc(F)cc(c3)C(F)(F)F)c12)[C@H]1CNC(=O)O1 | NMR (400 MHz, DMSO) 10.60 (s, 1H), 9.23 (s, 1H), 7.95 (d, 8.4 Hz, 1H), 7.82 (s, 0.5H), 7.81 (s, 0.5H), 7.74 (d, 9.1 Hz, 1H), 7.71 (s, 1H), 7.65 (s, 1H), 7.54 (s, 0.5H), 7.53 (s, 0.5H), 7.32 (dd, 8.8, 5.1 Hz, 1H), 7.14-7.06 (m, 1H), 6.59 (br s, 1H), 6.00 (br s, 1H), 5.81 (dd, 15.3, 7.8 Hz, 1H), 3.99 (td, 8.8, 6.7 Hz, 1H), 3.45-3.37 (m, 1H). | 552.1 | B | |
| I-1559 | 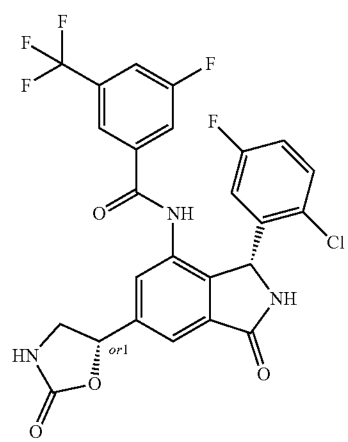 [SMILES: O=C1NC[C@H](c2cc(NC(=O)c3cc(F)cc(C(F)(F)F)c3)c3c(c2)C(=O)N[C@H]3c2cc(F)ccc2Cl)O1] | Fc1ccc(C1)c(c1)[C@@H]1NC(=O)c2cc(cc(NC(=O)c3cc(F)cc(c3)C(F)(F)F)c12)[C@H]1CNC(=O)O1 | NMR (400 MHz, DMSO) 10.60 (s, 1H), 9.23 (s, 1H), 7.95 (d, 8.4 Hz, 1H), 7.82 (s, 0.5H), 7.81 (s, 0.5H), 7.74 (d, 9.1 Hz, 1H), 7.71 (s, 1H), 7.65 (s, 1H), 7.54 (s, 0.5H), 7.53 (s, 0.5H), 7.32 (dd, 8.8, 5.1 Hz, 1H), 7.14-7.06 (m, 1H), 6.59 (br s, 1H), 6.00 (br s, 1H), 5.81 (dd, 15.3, 7.8 Hz, 1H), 3.99 (td, 8.8, 6.7 Hz, 1H), 3.45-3.37 (m, 1H). | 552.1 | A | |
| I-1560 | 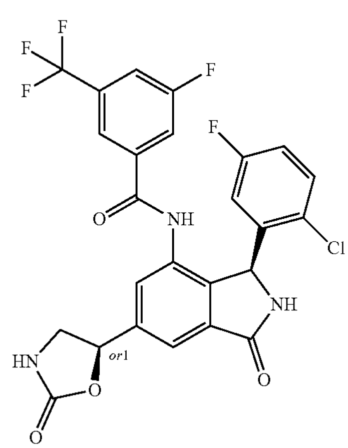 [SMILES: O=C1NC[C@@H](c2cc(NC(=O)c3cc(F)cc(C(F)(F)F)c3)c3c(c2)C(=O)N[C@@H]3c2cc(F)ccc2Cl)O1] | Fc1ccc(C1)c(c1)[C@H]1NC(=O)c2cc(cc(NC(=O)c3cc(F)cc(c3)C(F)(F)F)c12)[C@@H]1CNC(=O)O1 | NMR (400 MHz, DMSO) 10.60 (s, 1H), 9.23 (s, 1H), 7.95 (d, 8.4 Hz, 1H), 7.82 (s, 0.5H), 7.81 (s, 0.5H), 7.74 (d, 9.1 Hz, 1H), 7.71 (s, 1H), 7.65 (s, 1H), 7.54 (s, 0.5H), 7.53 (s, 0.5H), 7.32 (dd, 8.8, 5.1 Hz, 1H), 7.14-7.06 (m, 1H), 6.59 (br s, 1H), 6.00 (br s, 1H), 5.81 (dd, 15.3, 7.8 Hz, 1H), 3.99 (td, 8.8, 6.7 Hz., 1H), 3.45-3.37 (m, 1H). | 552.1 | C | |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-1561 | 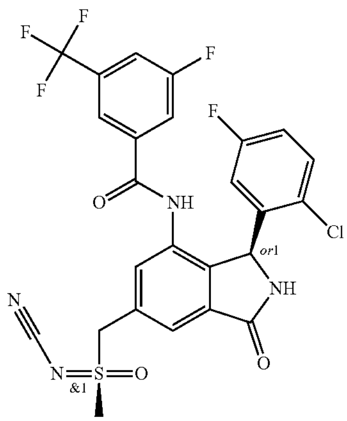 [SMILES: C[S@](=O)(Cc1cc(NC(=O)c2cc(F)cc(C(F)(F)F)c2)c2c(c1)C(=O)N[C@@H]2c1cc(F)ccc1Cl)=NC#N] | CS(=O)(Cc1cc2C(=O)N[C@@H](c2c(NC(=O)c2cc(F)cc(c2)C(F)(F)F)c1)c1cc(F)ccc1Cl)=NC#N | NMR (187) (400 MHz, DMSO-d6) 10.68 (br. s, 1H), 9.29 ( s, 1H), 7.95 (br. d, 8.3 Hz, 1H), 7.84 (s, 1H), 7.73 (br. d, 8.9 Hz, 1H), 7.63 (s, 1H), 7.58 (s, 1H), 7.32 (dd, 8.9, 5.2 Hz, 1H), 7.10 (td, 8.4, 2.9 Hz, 1H), 6.65 (br. s, 1H), 6.03 (br. s, 1H), 5.29-5.18 (m, 2H), 3.45 (s, 3H). | 583.1 | B | |
| I-1562 | 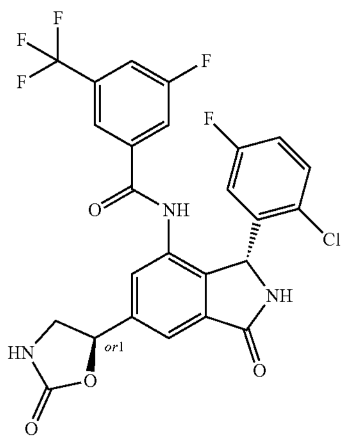 [SMILES: O=C1NC[C@@H](c2cc(NC(=O)c3cc(F)cc(C(F)(F)F)c3)c3c(c2)C(=O)N[C@H]3c2cc(F)ccc2Cl)O1] | Fc1ccc(C1)c(c1)[C@@H]1NC(=O)c2cc(cc(NC(=O)c3cc(F)cc(c3)C(F)(F)F)c12)[C@@H]1CNC(=O)O1 | NMR (400 MHz, DMSO) 10.60 (s, 1H), 9.23 (s, 1H), 7.95 (d, 8.4 Hz, 1H), 7.82 (s, 0.5H), 7.81 (s, 0.5H), 7.74 (d, 9.1 Hz, 1H), 7.71 (s, 1H), 7.65 (s, 1H), 7.54 (s, 0.5H), 7.53 (s, 0.5H), 7.32 (dd, 8.8, 5.1 Hz, 1H), 7.14-7.06 (m, 1H), 6.59 (br s, 1H), 6.00 (br s, 1H), 5.81 (dd, 15.3, 7.8 Hz, 1H), 3.99 (td, 8.8, 6.7 Hz, 1H), 3.45-3.37 (m, 1H). | 552.1 | A | |
| I-1563 | 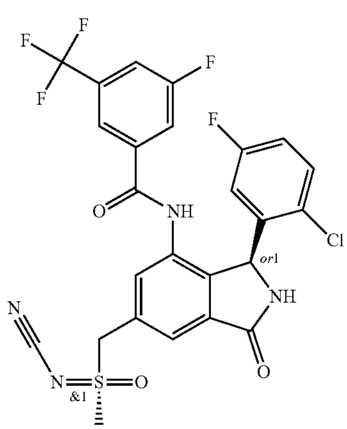 [SMILES: C[S@@](=O)(Cc1cc(NC(=O)c2cc(F)cc(C(F)(F)F)c2)c2c(c1)C(=O)N[C@@H]2c1cc(F)ccc1Cl)=NC#N] | CS(=O)(Cc1cc2C(=O)N[C@@H](c2c(NC(=O)c2cc(F)cc(c2)C(F)(F)F)c1)c1cc(F)ccc1Cl)=NC#N | NMR (187) (400 MHz, DMSO-d6) 10.68 (br. s, 1H), 9.29 ( s, 1H), 7.95 (br. d, 8.3 Hz, 1H), 7.84 (s, 1H), 7.73 (br. d, 8.9 Hz, 1H), 7.63 (s, 1H), 7.58 (s, 1H), 7.32 (dd, 8.9, 5.2 Hz, 1H), 7.10 (td, 8.4, 2.9 Hz, 1H), 6.65 (br. s, 1H), 6.03 (br. s, 1H), 5.29-5.18 (m, 2H), 3.45 (s, 3H). | 583.1 | A | |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-1564 | 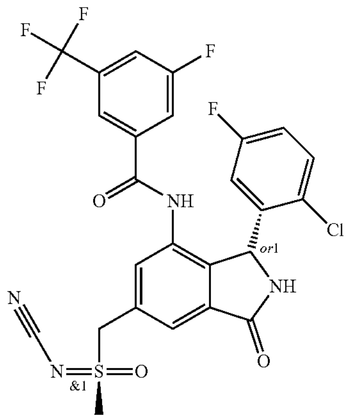 | CS(=O)(Cc1cc2C(=O)N[C@H](c2c(NC(=O)c2cc(F)cc(c2)C(F)(F)F)c1)c1cc(F)ccc1Cl)=NC#N | NMR (187) (400 MHz, DMSO-d6) 10.68 (br. s, 1H), 9.29 ( s, 1H), 7.95 (br. d, 8.3 Hz, 1H), 7.84 (s, 1H), 7.73 (br. d, 8.9 Hz, 1H), 7.63 (s, 1H), 7.58 (s, 1H), 7.32 (dd, 8.9, 5.2 Hz, 1H), 7.10 (td, 8.4, 2.9 Hz, 1H), 6.65 (br. s, 1H), 6.03 (br. s, 1H), 5.29-5.18 (m, 2H), 3.45 (s, 3H). | 583.1 | A | |
| I-1565 | 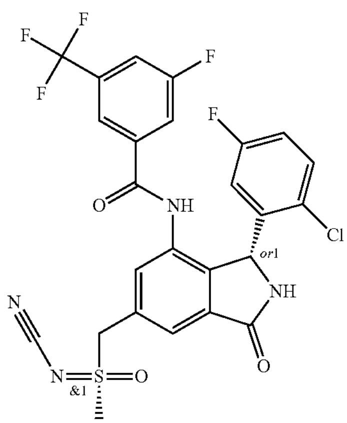 [SMILES: C[S@@](=O)(Cc1cc(NC(=O)c2cc(F)cc(C(F)(F)F)c2)c2c(c1)C(=O)N[C@H]2c1cc(F)ccc1Cl)=NC#N] | CS(=O)(Cccc2C(=O)N[C@H](c2c(NC(=O)c2cc(F)cc(c2)C(F)(F)F)c1)c1cc(F)ccc1Cl)=NC#N | NMR (187) (400 MHz, DMSO-d6) 10.68 (br. s, 1H), 9.29 ( s, 1H), 7.95 (br. d, 8.3 Hz, 1H), 7.84 (s, 1H), 7.73 (br. d, 8.9 Hz, 1H), 7.63 (s, 1H), 7.58 (s, 1H), 7.32 (dd, 8.9, 5.2 Hz, 1H), 7.10 (td, 8.4, 2.9 Hz, 1H), 6.65 (br. s, 1H), 6.03 (br. s, 1H), 5.29-5.18 (m, 2H), 3.45 (s, 3H). | 583.1 | A | |
| I-1566 | 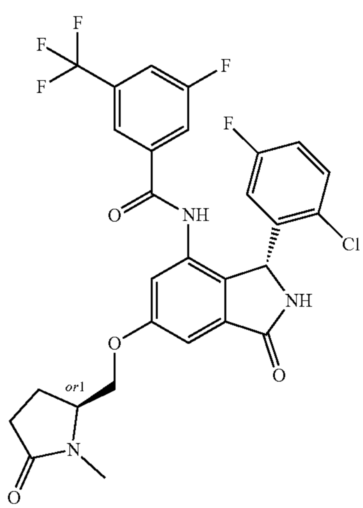 [SMILES: CN1C(=O)CC[C@H]1COc1cc(NC(=O)c2cc(F)cc(C(F)(F)F)c2)c2c(c1)C(=O)N[C@H]2c1cc(F)ccc1Cl] | CN1[C@H](COc2cc3C(=O)N[C@H](c3c(NC(=O)c3cc(F)cc(c3)C(F)(F)F)c2)c2cc(F)ccc2Cl)CCC1=O | 1H NMR (400 MHz, DMSO-d6) 10.44 (s, 1H), 9.14 (s, 1H), 7.95 (d, 8.3 Hz, 1H), 7.72 (d, 8.6 Hz, 1H), 7.64 (s, 1H), 7.31 (dd, 8.8, 5.1 Hz, 1H), 7.27 (s, 1H), 7.16-7.02 (m, 2H), 6.61 (br. s, 1H), 5.94 (br. s, 1H), 4.35-4.26 (m, 1H), 4.21-4.13 (m, 1H), 3.97-3.85 (m, 1H), 2.79 (s, 3H), 2.46-2.27 (m, 1H), 2.28-2.08 (m, 2H), 1.96-1.77 (m, 1H) | 594.2 | A | |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-1567 | 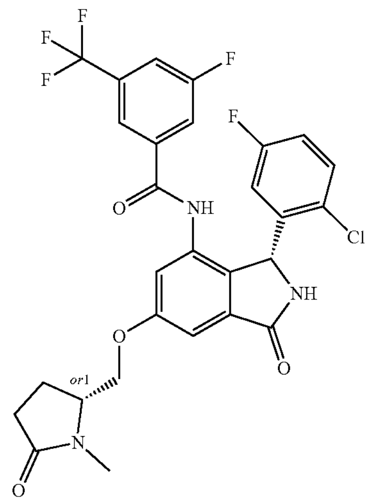 [SMILES: CN1C(=O)CC[C@@H]1COc1cc(NC(=O)c2cc(F)cc(C(F)(F)F)c2)c2c(c1)C(=O)N[C@H]2c1cc(F)ccc1Cl] | CN1[C@@H](COc2cc3C(=O)N[C@H](c3c(NC(=O)c3cc(F)cc(c3)C(F)(F)F)c2)c2cc(F)ccc2Cl)CCC1=O | 1H NMR (400 MHz, DMSO-d6) 10.44 (s, 1H), 9.14 (s, 1H), 7.95 (d, 8.3 Hz, 1H), 7.72 (d, 8.6 Hz, 1H), 7.64 (s, 1H), 7.31 (dd, 8.8, 5.1 Hz, 1H), 7.27 (s, 1H), 7.16-7.02 (m, 2H), 6.61 (br. s, 1H), 5.94 (br. s, 1H), 4.35-4.26 (m, 1H), 4.21-4.13 (m, 1H), 3.97-3.85 (m, 1H), 2.79 (s, 3H), 2.46-2.27 (m, 1H), 2.28-2.08 (m, 2H), 1.96-1.77 (m, 1H) | 594.2 | A | |
| I-1568 | 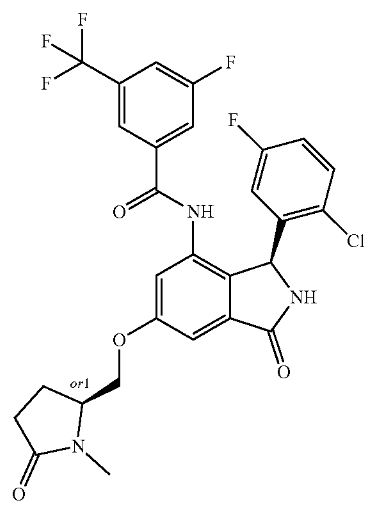 [SMILES: CN1C(=O)CC[C@H]1COc1cc(NC(=O)c2cc(F)cc(C(F)(F)F)c2)c2c(c1)C(=O)N[C@@H]2c1cc(F)ccc1Cl] | CN1[C@H](COc2cc3C(=O)N[C@@H](c3c(NC(=O)c3cc(F)cc(c3)C(F)(F)F)c2)c2cc(F)ccc2Cl)CCC1=O | 1H NMR (400 MHz, DMSO-d6) 10.44 (s, 1H), 9.14 (s, 1H), 7.95 (d, 8.3 Hz, 1H), 7.72 (d, 8.6 Hz, 1H), 7.64 (s, 1H), 7.31 (dd, 8.8, 5.1 Hz, 1H), 7.27 (s, 1H), 7.16-7.02 (m, 2H), 6.61 (br. s, 1H), 5.94 (br. s, 1H), 4.35-4.26 (m, 1H), 4.21-4.13 (m, 1H), 3.97-3.85 (m, 1H), 2.79 (s, 3H), 2.46-2.27 (m, 1H), 2.28-2.08 (m, 2H), 1.96-1.77 (m, 1H) | 594.2 | D | |
| I-1569 | 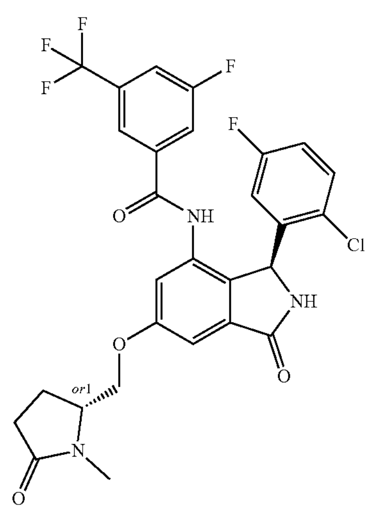 [SMILES: CN1C(=O)CC[C@@H]1COc1cc(NC(=O)c2cc(F)cc(C(F)(F)F)c2)c2c(c1)C(=O)N[C@@H]2c1cc(F)ccc1Cl] | CN1[C@@H](COc2cc3C(=O)N[C@@H](c3c(NC(=O)c3cc(F)cc(c3)C(F)(F)F)c2)c2cc(F)ccc2Cl)CCC1=O | 1H NMR (400 MHz, DMSO-d6) 10.44 (s, 1H), 9.14 (s, 1H), 7.95 (d, 8.3 Hz, 1H), 7.72 (d, 8.6 Hz, 1H), 7.64 (s, 1H), 7.31 (dd, 8.8, 5.1 Hz, 1H), 7.27 (s, 1H), 7.16-7.02 (m, 2H), 6.61 (br. s, 1H), 5.94 (br. s, 1H), 4.35-4.26 (m, 1H), 4.21-4.13 (m, 1H), 3.97-3.85 (m, 1H), 2.79 (s, 3H), 2.46-2.27 (m, 1H), 2.28-2.08 (m, 2H), 1.96-1.77 (m, 1H) | 594.2 | E | |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-1570 | 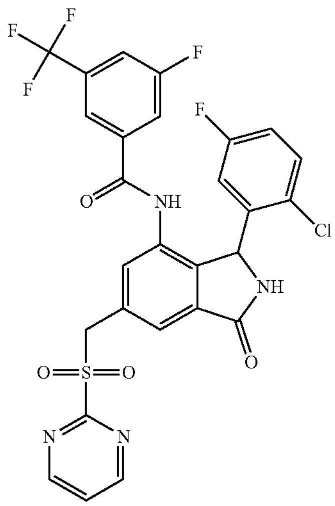 [SMILES: O=C(Nc1cc(CS(=O)(=O)c2ncccn2)cc2c1C(c1cc(F)ccc1Cl)NC2=O)c1cc(F)cc(C(F)(F)F)c1] | Fc1ccc(C1)c(c1)C1NC(=O)c2cc(CS(=O)(=O)c3ncccn3)cc(NC(=O)c3cc(F)cc(c3)C(F)(F)F)c12 | NMR (400 MHz, CD3CN) 8.99 (s, 1H), 8.98 (s, 1H), 8.68 (s, 1H), 7.69 (t, 4.9 Hz, 2H), 7.70 (br, s, 1H), 7.67-7.63 (m, 1H), 7.60 (s, 1H), 7.60-7.56 (m, 1H), 7.55 (m, 1H), 7.32 (s, 1H), 7.24 (dd, 8.9, 5.1 Hz, 1H), 6.97 (ddd, 8.8, 8.0, 3.1 Hz, 1H), 6.54 (br, s, 1H), 6.09 (br, s, 1H), 5.00 (d, 2.1 Hz, 2H). | 623 | A | |
| I-1571 | 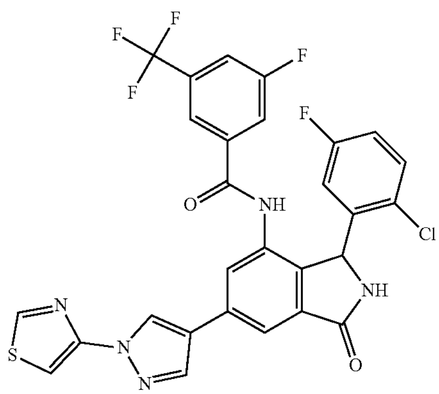 [SMILES: O=C(Nc1cc(-c2cnn(-c3cscn3)c2)cc2c1C(c1cc(F)ccc1Cl)NC2=O)c1cc(F)cc(C(F)(F)F)c1] | Fc1ccc(C1)c(c1)C1NC(=O)c2cc(cc(NC(=O)c3cc(F)cc(c3)C(F)(F)F)c12)-c1cnn(c1)-c1cscn1 | NMR (400 MHz, DMSO-d6) 10.57 (br s, 1H), 9.24 (d, 2.2 Hz, 1H), 9.17 (br s, 1H), 9.04 (s, 1H), 8.44 (s, 1H), 8.10 (s, 1H), 7.96 (br d, 8.4 Hz, 1H), 7.91 (s, 1H), 7.81 (d, 2.2 Hz, 1H), 7.77 (br d, 8.9 Hz, 1H), 7.73 (s, 1H), 7.32 (dd, 8.9, 5.2 Hz, 1H), 7.10 (td, 8.5, 3.0 Hz, 1H), 6.61 (br s, 1H), 6.00 (br s, 1H). | 616 | A | |
| I-1572 | 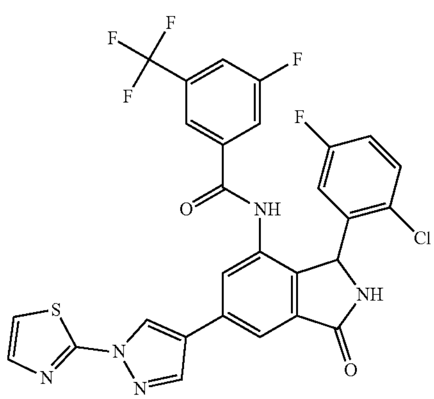 [SMILES: O=C(Nc1cc(-c2cnn(-c3nccs3)c2)cc2c1C(c1cc(F)ccc1Cl)NC2=O)c1cc(F)cc(C(F)(F)F)c1] | Fc1ccc(C1)c(c1)C1NC(=O)c2cc(cc(NC(=O)c3cc(F)cc(c3)C(F)(F)F)c12)-c1cnn(c1)-c1nccs1 | NMR (400 MHz, DMSO-d6) 10.59 (br s, 1H), 9.20 (s, 1H), 9.20 (br s, 1H), 8.55 (s, 1H), 8.16 (s, 1H), 7.97 (br d, 8.6 Hz, 1H), 7.94 (br s, 1H), 7.77 (br d, 9.1 Hz, 1H), 7.72 (br s, 1H), 7.71 (d, 3.5 Hz, 1H), 7.60 (d, 3.5 Hz, 1H), 7.32 (dd, 8.9, 5.2 Hz, 1H), 7.10 (td, 8.5, 3.0 Hz, 1H), 6.62 (br s, 1H), 6.01 (br s, 1H). | 616 | A | |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-1573 | 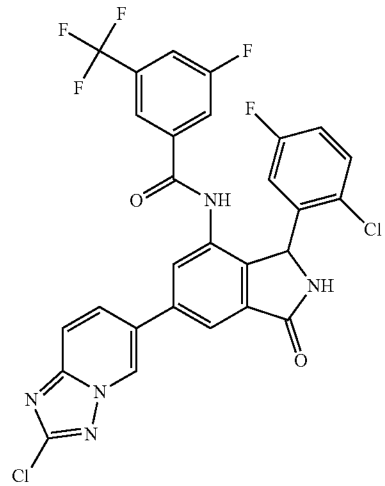 [SMILES: O=C(Nc1cc(-c2ccc3nc(Cl)nn3c2)cc2c1C(c1cc(F)ccc1Cl)NC2=O)c1cc(F)cc(C(F)(F)F)c1] | Fc1ccc(C1)c(c1)C1NC(=O)c2cc(cc(NC(=O)c3cc(F)cc(c3)C(F)(F)F)c12)-c1ccc2nc(Cl)nn2c1 | 1H NMR (500 MHz, DMSO) 10.65 (s, 1H), 9.46 (d, 1.9 Hz, 1H), 9.25 (s, 1H), 8.22 (dd, 9.3, 1.9 Hz, 1H), 8.12 (s, 1H), 7.99-7.91 (m, 3H), 7.76 (d, 9.2 Hz, 1H), 7.71 (s, 1H), 7.33 (dd, 8.8, 5.2 Hz, 1H), 7.10 (td, 8.3, 3.0 Hz, 1H), 6.61 (s, 1H), 6.06 (s, 1H). | 618.18 | A | |
| I-1574 | 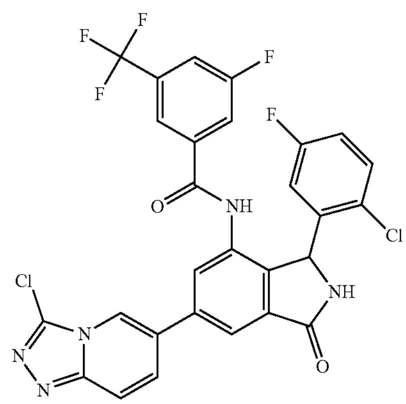 [SMILES: O=C(Nc1cc(-c2ccc3nnc(Cl)n3c2)cc2c1C(c1cc(F)ccc1Cl)NC2=O)c1cc(F)cc(C(F)(F)F)c1] | Fc1ccc(C1)c(c1)C1NC(=O)c2cc(cc(NC(=O)c3cc(F)cc(c3)C(F)(F)F)c12)-c1ccc2nnc(Cl)n2c1 | | 618.04 | A | |
| I-1575 | 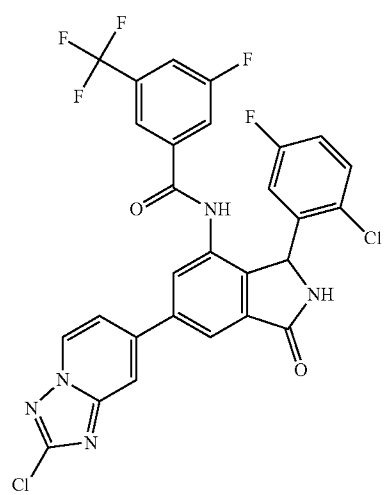 [SMILES: O=C(Nc1cc(-c2ccn3nc(Cl)nc3c2)cc2c1C(c1cc(F)ccc1Cl)NC2=O)c1cc(F)cc(C(F)(F)F)c1] | Fc1ccc(C1)c(c1)C1NC(=O)c2cc(cc(NC(=O)c3cc(F)cc(c3)C(F)(F)F)c12)-c1ccn2nc(Cl)nc2c1 | 1H NMR (500 MHz, DMSO) 10.68 (s, 1H), 9.26 (s, 1H), 9.05 (d, 7.0 Hz, 1H), 8.26 (s, 1H), 8.15 (s, 1H), 8.04 (s, 1H), 7.94 (s, 1H), 7.78-7.71 (m, 3H), 7.34 (dd, 8.9, 5.1 Hz, 1H), 7.10 (td, 8.4, 3.1 Hz, 1H), 6.70 (s, 1H), 6.27 (s, 1H), 6.08 (s, 1H). | 618.13 | A | |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-1576 | 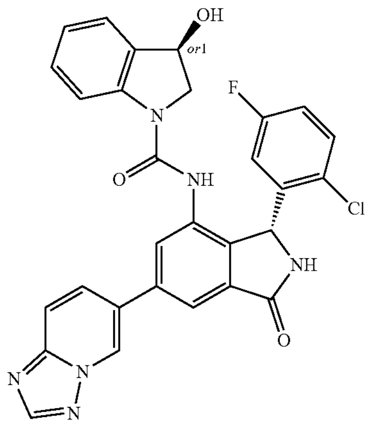 [SMILES: O=C1N[C@@H](c2cc(F)ccc2Cl)c2c(NC(=O)N3C[C@H](O)c4ccccc43)cc(-c3ccc4ncnn4c3)cc21] | O[C@H]1CN(C(=O)Nc2cc(cc3C(=O)N[C@H](c23)c2cc(F)ccc2Cl)-c2ccc3ncnn3c2)ccccc12 | 1H NMR (400 MHz, DMSO-d6) 9.43 (dd, 1.9, 0.9 Hz, 1H), 9.17 (s, 1H), 8.76 (s, 1H), 8.58 (s, 1H), 8.11 (dd, 9.3, 1.9 Hz, 1H), 8.05-7.91 (m, 2H), 7.87 (d, 8.1 Hz, 1H), 7.82 (d, 1.7 Hz, 1H), 7.43-7.31 (m, 2H), 7.30-7.21 (m, 1H), 7.24-7.13 (m, 1H), 7.00 (td, 7.4, 1.0 Hz, 1H), 6.66 (s, 1H), 6.11 (s, 1H), 5.68 (d, 6.0 Hz, 1H), 5.12 (td, 8.3, 7.0, 3.5 Hz, 1H), 3.72 (dd, 11.3, 3.6 Hz, 1H), 3.31 (s, 1H). | 555.35 | B | |
| I-1577 | 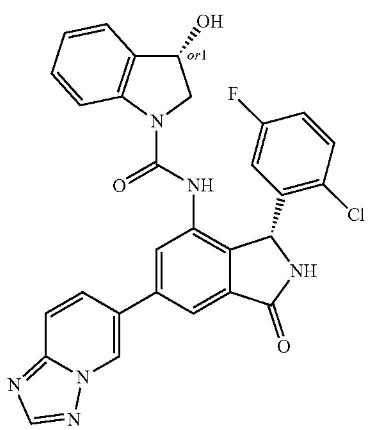 [SMILES: O=C1N[C@@H](c2cc(F)ccc2Cl)c2c(NC(=O)N3C[C@@H](O)c4ccccc43)cc(-c3ccc4ncnn4c3)cc21] | O[C@@H]1CN(C(=O)Nc2cc(cc3C(=O)N[C@H](c23)c2cc(F)ccc2Cl)-c2ccc3ncnn3c2)ccccc12 | 1H NMR (400 MHz, DMSO-d6) 9.43 (dd, 1.9, 0.9 Hz, 1H), 9.17 (s, 1H), 8.76 (s, 1H), 8.58 (s, 1H), 8.11 (dd, 9.3, 1.9 Hz, 1H), 8.05-7.91 (m, 2H), 7.87 (d, 8.1 Hz, 1H), 7.82 (d, 1.7 Hz, 1H), 7.43-7.31 (m, 2H), 7.30-7.21 (m, 1H), 7.24-7.13 (m, 1H), 7.00 (td, 7.4, 1.0 Hz, 1H), 6.66 (s, 1H), 6.11 (s, 1H), 5.68 (d, 6.0 Hz, 1H), 5.12 (td, 8.3, 7.0, 3.5 Hz, 1H), 3.72 (dd, 11.3, 3.6 Hz, 1H), 3.31 (s, 1H). | 555.3 | A | |
| I-1578 | 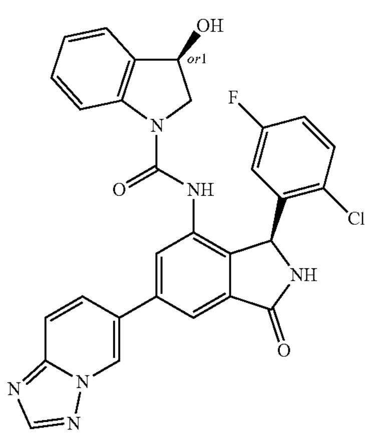 [SMILES: O=C1N[C@H](c2cc(F)ccc2Cl)c2c(NC(=O)N3C[C@H](O)c4ccccc43)cc(-c3ccc4ncnn4c3)cc21] | O[C@H]1CN(C(=O)Nc2cc(cc3C(=O)N[C@@H](c23)c2cc(F)ccc2Cl)-c2ccc3ncnn3c2)ccccc12 | 1H NMR (400 MHz, DMSO-d6) 9.43 (dd, 1.9, 0.9 Hz, 1H), 9.17 (s, 1H), 8.76 (s, 1H), 8.58 (s, 1H), 8.11 (dd, 9.3, 1.9 Hz, 1H), 8.05-7.91 (m, 2H), 7.87 (d, 8.1 Hz, 1H), 7.82 (d, 1.7 Hz, 1H), 7.43-7.31 (m, 2H), 7.30-7.21 (m, 1H), 7.24-7.13 (m, 1H), 7.00 (td, 7.4, 1.0 Hz, 1H), 6.66 (s, 1H), 6.11 (s, 1H), 5.68 (d, 6.0 Hz, 1H), 5.12 (td, 8.3, 7.0, 3.5 Hz, 1H), 3.72 (dd, 11.3, 3.6 Hz, 1H), 3.31 (s, 1H). | 555.1 | E | |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-1579 | 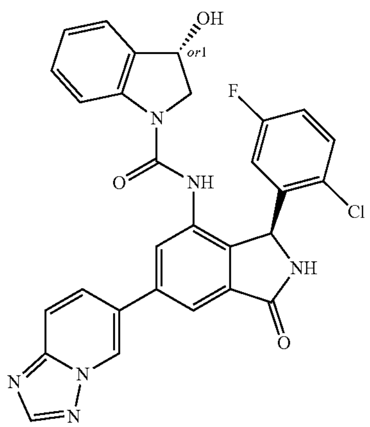 [SMILES: O=C1N[C@H](c2cc(F)ccc2Cl)c2c(NC(=O)N3C[C@@H](O)c4ccccc43)cc(-c3ccc4ncnn4c3)cc21] | O[C@@H]1CN(C(=O)Nc2cc(cc3C(=O)N[C@@H](c23)c2cc(F)ccc2Cl)-c2ccc3ncnn3c2)ccccc12 | 1H NMR (400 MHz, DMSO-d6) 9.43 (dd, 1.9, 0.9 Hz, 1H), 9.17 (s, 1H), 8.76 (s, 1H), 8.58 (s, 1H), 8.11 (dd, 9.3, 1.9 Hz, 1H), 8.05-7.91 (m, 2H), 7.87 (d, 8.1 Hz, 1H), 7.82 (d, 1.7 Hz, 1H), 7.43-7.31 (m, 2H), 7.30-7.21 (m, 1H), 7.24-7.13 (m, 1H), 7.00 (td, 7.4, 1.0 Hz, 1H), 6.66 (s, 1H), 6.11 (s, 1H), 5.68 (d, 6.0 Hz, 1H), 5.12 (td, 8.3, 7.0, 3.5 Hz, 1H), 3.72 (dd, 11.3, 3.6 Hz, 1H), 3.31 (s, 1H). | 555.35 | C | |
| I-1580 | 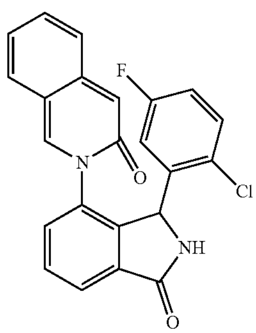 [SMILES: O=C1NC(c2cc(F)ccc2Cl)c2c1cccc2-n1cc2ccccc2cc1=O] | Fc1ccc(C1)c(c1)C1NC(=O)c2cccc(c12)-n1cc2cccc2cc1=O | 1H NMR (400 MHz, Chloroform-d) 8.10 (d, 7.6 Hz, 1H), 7.77-7.53 (m, 3H), 7.39 (s, 1H), 7.23 (s, 1H), 7.01-6.90 (m, 2H), 6.85 (t, 7.4 Hz, 1H), 6.76 (s, 1H), 6.65 (s, 2H), 6.44 (S, 1H), 6.20 (s, 1H). | 405.15 | E | |
| I-1581 | 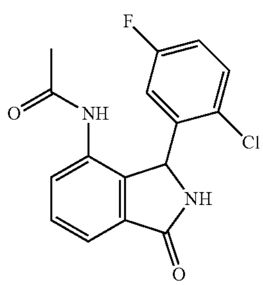 [SMILES: CC(=O)Nc1cccc2c1C(c1cc(F)ccc1Cl)NC2=O] | CC(=O)Nc1cccc2C(=O)NC(c12)c1cc(F)ccc1Cl | 1H NMR (400 MHz, Chloroform-d) 8.10 (d, 7.9 Hz, 1H), 7.76 (d, 7.5 Hz, 1H), 7.58 (t, 7.8 Hz, 1H), 7.48 (dd, 8.9, 4.9 Hz, 1H), 7.06 (ddd, 8.9, 7.3, 3.0 Hz, 1H), 6.99 (s, 1H), 6.69 (d, 8.8 Hz, 1H), 6.63 (s, 1H), 6.19 (s, 1H), 2.03 (s, 3H). | 319 | E | |
| I-1582 | 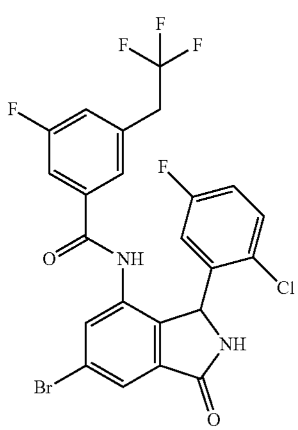 [SMILES: O=C(Nc1cc(Br)cc2c1C(c1cc(F)ccc1Cl)NC2=O)c1cc(F)cc(CC(F)(F)F)c1] | Fc1ccc(C1)c(c1)C1NC(=O)c2cc(Br)cc(NC(=O)c3cc(F)cc(CC(F)(F)F)c3)c12 | 1H NMR (400 MHz, DMSO-d6) 10.35 (s, 1H), 9.28 (s, 1H), 7.81 (d, 1.7 Hz, 1H), 7.75 (d, 1.8 Hz, 1H), 7.47 (s, 2H), 7.34 (dd, 8.9, 5.2 Hz, 1H), 7.28 (d, 9.2 Hz, 1H), 7.12 (td, 8.4, 3.1 Hz, 1H), 5.99 (s, 1H), 3.78-3.72 (d, 2H). | 560.9 | C | |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-1583 | 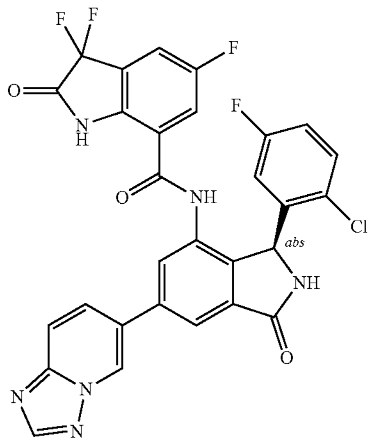 [SMILES: O=C(Nc1cc(-c2ccc3ncnn3c2)cc2c1[C@@H](c1cc(F)ccc1Cl)NC2=O)c1cc(F)cc2c1NC(=O)C2(F)F] | Fc1ccc(C1)c(c1)[C@H]1NC(=O)c2cc(cc(NC(=O)c3cc(F)cc4c3NC(=O)C4(F)F)c12)-c1ccc2ncnn2c1 | 1H NMR (400 MHz, DMSO-d6) 11.08 (s, 1H), 10.55 (s, 1H), 9.47 (dd, 1.9, 1.0 Hz, 1H), 9.26 (s, 1H), 8.58 (s, 1H), 8.17-8.10 (m, 2H), 8.03-7.95 (m, 3H), 7.38 (t, 7.0 Hz, 2H), 7.19-7.10 (m, 1H), 6.07 (s, 1H), 1.29-1.24 (m, 2H), 1.20-1.12 (m, 1H), 1.00-0.70 (s,1H) | 607 | D | |
| I-1584 | 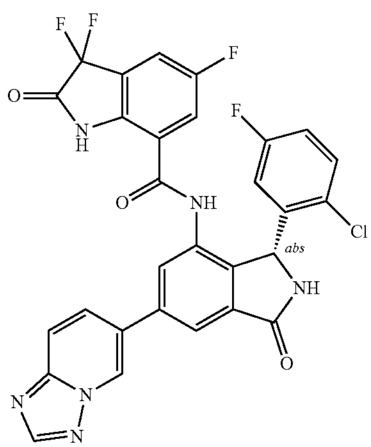 [SMILES: O=C(Nc1cc(-c2ccc3ncnn3c2)cc2c1[C@H](c1cc(F)ccc1Cl)NC2=O)c1cc(F)cc2c1NC(=O)C2(F)F] | Fc1ccc(C1)c(c1)[C@@H]1NC(=O)c2cc(cc(NC(=O)c3cc(F)cc4c3NC(=O)C4(F)F)c12)-c1ccc2ncnn2c1 | 1H NMR (400 MHz, DMSO-d6) 11.08 (s, 1H), 10.57 (s, 1H), 9.47 (t, 1.4 Hz, 1H), 9.26 (s, 1H), 8.58 (s, 1H), 8.17-8.10 (m, 2H), 8.03-7.95 (m, 3H), 7.80-7.50 (m,2H),7.50-7.30 (m,2H),7.30-7.00 (m,2H),6.08 (s, 1H), 1.30-1.22 (s, 3H), 1.20-1.13 (m, 1H),0.90-0.80 (m, 1H). | 607 | B | |
| I-1585 | 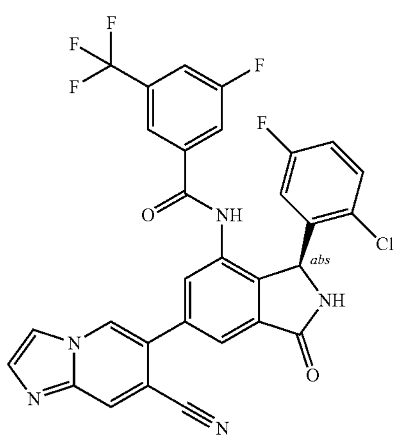 [SMILES: N#Cc1cc2nccn2cc1-c1cc(NC(=O)c2cc(F)cc(C(F)(F)F)c2)c2c(c1)C(=O)N[C@@H]2c1cc(F)ccc1Cl] | Fc1ccc(C1)c(c1)[C@H]1NC(=O)c2cc(cc(NC(=O)c3cc(F)cc(c3)C(F)(F)F)c12)-c1cn2ccnc2cc1C#N | 1H NMR (400 MHz, DMSO-d6) 10.71 (br. s, 1H), 9.33 (br. s, 1H), 8.98 (d, 0.8 Hz, 1H), 8.55 (app.t, 0.8 Hz 1H), 8.19 (s, 1H), 7.98 (d, 8.1 Hz, 1H), 7.95-7.92 (m, 1H), 7.93 (d, 1.1 Hz, 1H), 7.81-7.70 (m, 2H), 7.68 (s, 1H), 7.36 (dd, 8.9, 5.2 Hz, 1H), 7.13 (td, 8.1, 2.9 Hz, 1H), 6.68 (br. s, 1H), 6.07 (br. s, 1H) | 608.1 | C | |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-1586 | 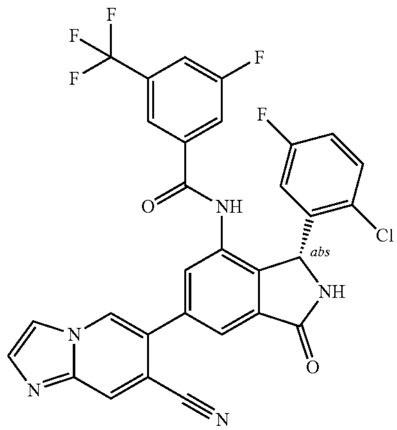 [SMILES: N#Cc1cc2nccn2cc1-c1cc(NC(=O)c2cc(F)cc(C(F)(F)F)c2)c2c(c1)C(=O)N[C@H]2c1cc(F)ccc1Cl] | Fc1ccc(C1)c(c1)[C@@H]1NC(=O)c2cc(cc(NC(=O)c3cc(F)cc(c3)C(F)(F)F)c12)-c1cn2ccnc2cc1C#N | 1H NMR (400 MHz, DMSO-d6) 10.71 (br. s, 1H), 9.33 (br. s, 1H), 8.98 (d, 0.8 Hz, 1H), 8.55 (t, 0.8 Hz 1H), 8.19 (s, 1H), 7.98 (d, 8.1 Hz, 1H), 7.95-7.92 (m, 1H), 7.93 (d, 1.1 Hz, 1H), 7.81-7.70 (m, 2H), 7.68 (s, 1H), 7.36 (dd, 8.9, 5.2 Hz, 1H), 7.13 (td, 8.1, 2.9 Hz, 1H), 6.68 (br. s, 1H), 6.07 (br. s, 1H) | 608.1 | A | |
| I-1587 | 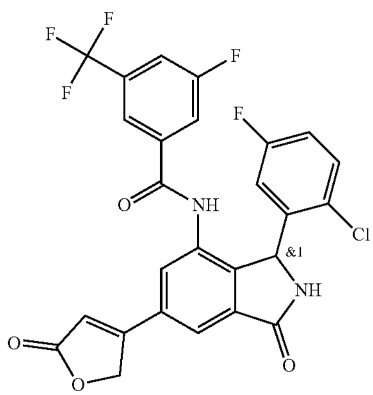 [SMILES: O=C1C=C(c2cc(NC(=O)c3cc(F)cc(C(F)(F)F)c3)c3c(c2)C(=O)NC3c2cc(F)ccc2Cl)CO1] | Fc1ccc(C1)c(c1)C1NC(=O)c2cc(cc(NC(=O)c3cc(F)cc(c3)C(F)(F)F)c12)C1=CC(=O)OC1 | (400 MHz, DMSO-d6) 10.68 (s, 1H), 9.32 (br s, 1H), 8.06 (s, 1H), 7.98 (d, 8.5 Hz., 1H), 7.83 (s, 1H), 7.79-7.71 (m, 1H), 7.69 (s, 1H), 7.33 (dd, 8.9, 5.2 Hz, 1H), 7.11 (td, 8.4, 3.1 Hz, 1H), 6.95 (s, 1H), 6.50 (br s, 1H), 6.04 (br s, 1H), 5.55-5.43 (m, 2H). | 547.2 | A | |
| I-1588 | 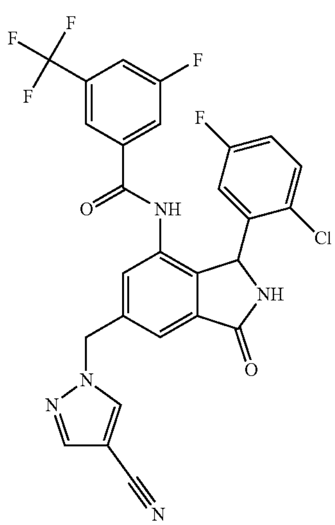 [SMILES: N#Cc1cnn(Cc2cc(NC(=O)c3cc(F)cc(C(F)(F)F)c3)c3c(c2)C(=O)NC3c2cc(F)ccc2Cl)c1] | Fc1ccc(C1)c(c1)C1NC(=O)c2cc(Cn3cc(cn3)C#N)cc(NC(=O)c3cc(F)cc(c3)C(F)(F)F)c12 | 1H-NMR (400 MHz, DMSO-d6) 10.53 (br. s, 1H), 9.21 (br. s, 1H), 8.79 (d, 0.4 Hz, 1H), 8.15 (d, 0.5 Hz, 1H), 7.95 (br. d, 8.3 Hz, 1H), 7.71 (br. d, 8.8 Hz, 1H), 7.62 (s, 1H), 7.61 (s, 1H), 7.37 (br. s, 1H), 7.30 (dd, 8.9, 5.2 Hz, 1H), 7.09 (app. td, 8.4, 3.1 Hz, 1H), 6.57 (br. s, 1H), 5.95 (br. s, 1H), 5.64-5.56 (m, 2H). | 570.2 | A | |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-1589 | 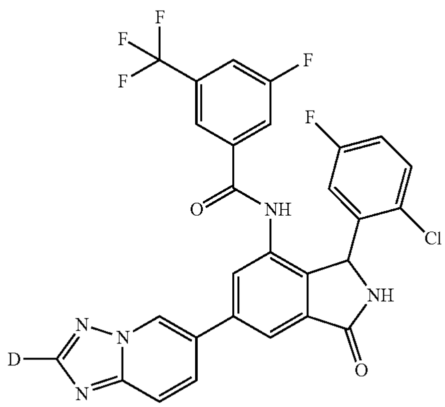 [SMILES: [2H]c1nc2ccc(-c3cc(NC(=O)c4cc(F)cc(C(F)(F)F)c4)c4c(c3)C(=O)NC4c3cc(F)ccc3Cl)cn2n1] | [2H]c1nc2ccc(cn2n1)-c1cc2C(=O)NC(c2c(NC(=O)c2cc(F)cc(c2)C(F)(F)F)c1)cc(F)ccc1Cl | 1H NMR (400 MHz, DMSO-d6) 10.64 (s, 1H), 9.51-9.46 (m, 1H), 9.26 (s, 1H), 8.18-8.07 (m, 2H), 8.03-7.94 (m, 3H), 7.78 (d, 9.3 Hz, 1H), 7.73 (s, 1H), 7.35 (dd, 8.9, 5.2 Hz, 1H), 7.12 (td, 8.4, 3.0 Hz, 1H), 6.67 (s, 1H), 6.08 (s, 1H). | 585.15 | A | |
| I-1590 | 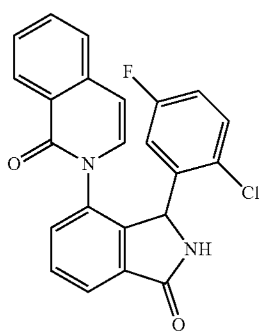 [SMILES: O=C1NC(c2cc(F)ccc2Cl)c2c1cccc2-n1ccc2ccccc2c1=O] | Fc1ccc(C1)c(c1)C1NC(=O)c2cccc(c12)-n1ccc2ccccc2c1=O | 1H NMR (400 MHz, DMSO-d6) 9.21 (s, 1H), 8.26 (d, 8.0 Hz, 1H), 7.90 (d, 7.5 Hz, 1H), 7.76 (dt, 19.1, 7.6 Hz, 2H), 7.62 (dd, 22.6, 7.7 Hz, 2H), 7.55 (d, 7.5 Hz, 1H), 7.14 (s, 1H), 6.99 (s, 1H), 6.83 (d, 7.4 Hz, 1H), 6.66 (s, 1H), 6.49 (s, 1H), 6.34 (d, 7.4 Hz, 1H), 6.01 (s, 1H) | 405.05 | E | |
| I-1591 | 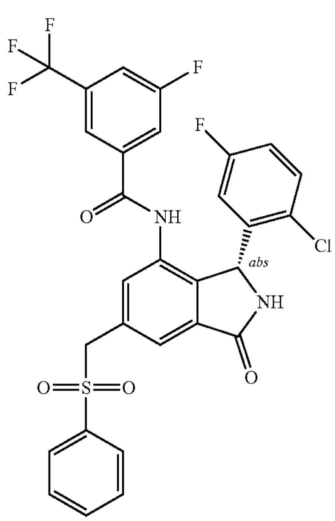 [SMILES: O=C(Nc1cc(CS(=O)(=O)c2ccccc2)cc2c1[C@H](c1cc(F)ccc1Cl)NC2=O)c1cc(F)cc(C(F)(F)F)c1] | Fc1ccc(C1)c(c1)[C@@H]1NC(=O)c2cc(CS(=O)(=O)c3ccccc3)cc(NC(=O)c3cc(F)cc(c3)C(F)(F)F)c12 | NMR (400 MHz, CD3CN) 8.72 (br s, 1H), 7.75-7.71 (m, 2H), 7.69 (dt, 2.5, 1.5 Hz, 1H) 7.67-7.63 (m, 1H) 7.61-7.52 (m, 4H), 7.46 (s, 1H), 7.43-7.39 (s, 1H), 7.34-7.29 (m, 1H), 7.26 (dd, 8.9, 5.1 Hz, 1H), 7.01-6.95 (m, 1H), 6.61 (br, s, 1H), 6.15 (br, s, 1H), 4.69-4.33 (m, 2H). | 621 | A | |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-1592 | 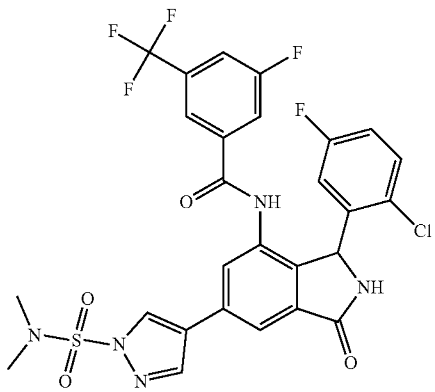 [SMILES: CN(C)S(=O)(=O)n1cc(-c2cc(NC(=O)c3cc(F)cc(C(F)(F)F)c3)c3c(c2)C(=O)NC3c2cc(F)ccc2Cl)cn1] | CN(C)S(=O)(=O)n1cc(cn1)-c1cc2C(=O)NC(c2c(NC(=O)c2cc(F)cc(c2)C(F)(F)F)c1)c1cc(F)ccc1Cl | (400 MHz, DMSO-D6) 10.56 (br s, 1 H), 9.18 (br s, 1 H), 8.97 (s, 1 H), 8.57 (s, 1 H), 8.14 (s, 1 H), 7.97 (br d, 8.4 Hz, 1 H), 7.92 (s, 1 H), 7.77 (br d, 8.7 Hz, 1 H), 7.73 (s, 1 H), 7.32 (dd, 8.9, 5.2 Hz, 1 H), 7.10 (td, 8.5, 2.8 Hz, 1 H), 6.58 (br s, 1 H), 6.00 (br s, 1 H), 2.90 (s, 6 H). | 638.2 | A | |
| I-1593 | 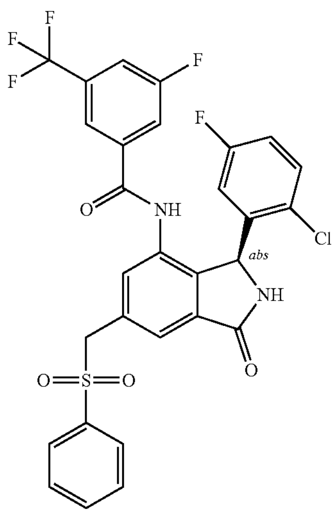 [SMILES: O=C(Nc1cc(CS(=O)(=O)c2ccccc2)cc2c1[C@@H](c1cc(F)ccc1Cl)NC2=O)c1cc(F)cc(C(F)(F)F)c1] | Fc1ccc(C1)c(c1)[C@H]1NC(=O)c2cc(CS(=O)(=O)c3cccc3)cc(NC(=O)c3cc(F)cc(c3)C(F)(F)F)c12 | NMR (400 MHz, CD3CN) 8.72 (d, 23.5 Hz, 1H), 7.75-7.71 (m, 2H), 7.69 (dt, 2.5, 1.5 Hz, 1H) 7.67-7.63 (m, 1H) 7.61-7.52 (m, 4H), 7.46 (s, 1H), 7.43-7.39 (s, 1H), 7.34-7.29 (m, 1H), 7.26 (dd, 8.9, 5.1 Hz, 1H), 7.01-6.95 (m, 1H), 6.61 (br, s, 1H), 6.15 (br, s, 1H), 4.69-4.33 (m, 2H). | 621 | D | |
| I-1594 | 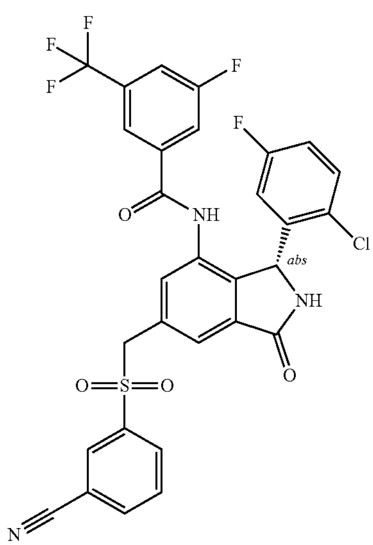 [SMILES: N#Cc1cccc(S(=O)(=O)Cc2cc(NC(=O)c3cc(F)cc(C(F)(F)F)c3)c3c(c2)C(=O)N[C@H]3c2cc(F)ccc2Cl)c1] | Fc1ccc(C1)c(c1)[C@@H]1NC(=O)c2cc(CS(=O)(=O)c3cccc(c3)C#N)cc(NC(=O)c3cc(F)cc(c3)C(F)(F)F)c12 | NMR (400 MHz, CD3CN) 8.62 (s, 1H), 8.13 (t, 1.1 Hz, 1H), 8.03 (dt, 7.9, 1.2 Hz, 1H), 7.94 (dt, 8.0, 1.3 Hz, 1H), 7.70 (t, 7.9 Hz, 1H), 7.66 (br, d, 8.5 Hz, 1H), 7.58 (td, 9.1 Hz, 1.7 Hz, 1H), 7.54 (s, 1H), 7.50 (s, 1H), 7.42 (s, 1H), 7.27 (dd, 8.9, 5.1 Hz, 1H), 7.27 (NH, 1H), 6.98 (td, 8.1, 3.0 Hz, 1H), 6.62 (br, s, 1H), 6.12 (br, s, 1H), 4.66 (s, 2H). | 646 | A | |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-1595 | 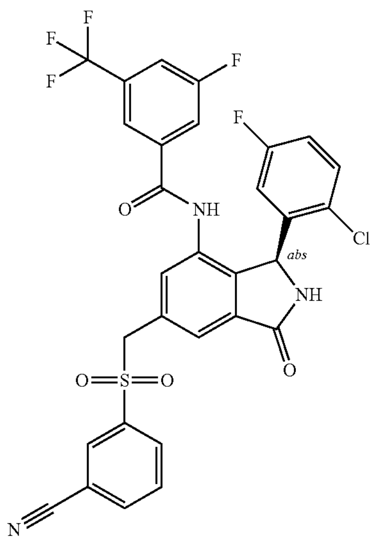 [SMILES: N#Cc1cccc(S(=O)(=O)Cc2cc(NC(=O)c3cc(F)cc(C(F)(F)F)c3)c3c(c2)C(=O)N[C@@H]3c2cc(F)ccc2Cl)c1] | Fc1ccc(C1)c(c1)[C@H]1NC(=O)c2cc(CS(=O)(=O)c3ccc(c3)C#N)cc(NC(=O)c3cc(F)cc(c3)C(F)(F)F)c12 | NMR (400 MHz, CD3CN) 8.62 (s, 1H), 8.13 (t, 1.1 Hz, 1H), 8.03 (dt, 7.9, 1.2 Hz, 1H), 7.94 (dt, 8.0, 1.3 Hz, 1H), 7.70 (1, 7.9 Hz, 1H), 7.66 (br, d, 8.5 Hz, 1H), 7.58 (td, 9.1 Hz, 1.7 Hz, 1H), 7.54 (s, 1H), 7.50 (s, 1H), 7.42 (s, 1H), 7.27 (dd, 8.9, 5.1 Hz, 1H), 7.27 (NH, 1H), 6.98 (td, 8.1, 3.0 Hz, 1H), 6.62 (br, s, 1H), 6.12 (br, s, 1H), 4.66 (s, 2H). | 646 | D | |
| I-1596 | 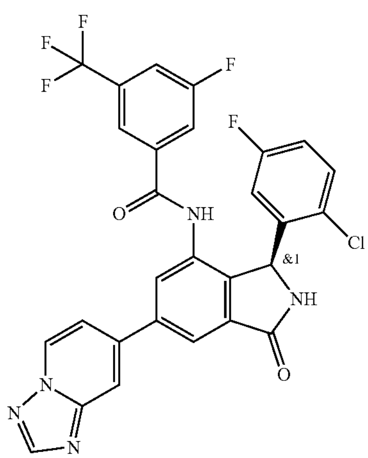 [SMILES: O=C(Nc1cc(-c2ccn3ncnc3c2)cc2c1[C@@H](c1cc(F)ccc1Cl)NC2=O)c1cc(F)cc(C(F)(F)F)c1] | Fc1ccc(C1)c(c1)[C@H]1NC(=O)c2cc(cc(NC(=O)c3cc(F)cc(c3)C(F)(F)F)c12)-c1ccn2ncnc2c1 | | 584.2 | D | |
| I-1597 | 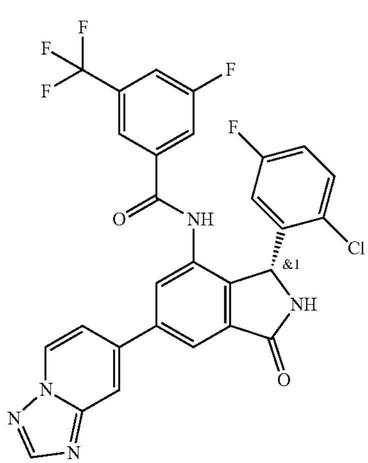 [SMILES: O=C(Nc1cc(-c2ccn3ncnc3c2)cc2c1[C@H](c1cc(F)ccc1Cl)NC2=O)c1cc(F)cc(C(F)(F)F)c1] | Fc1ccc(C1)c(c1)[C@@H]1NC(=O)c2cc(cc(NC(=O)c3cc(F)cc(c3)C(F)(F)F)c12)-c1ccn2ncnc2c1 | | 584.2 | A | |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-1598 | 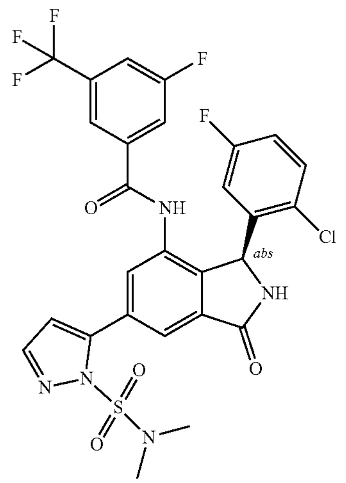 [SMILES: CN(C)S(=O)(=O)n1nccc1-c1cc(NC(=O)c2cc(F)cc(C(F)(F)F)c2)c2c(c1)C(=O)N[C@@H]2c1cc(F)ccc1Cl] | CN(C)S(=O)(=O)n1nccc1-c1cc2C(=O)N[C@@H](c2c(NC(=O)c2cc(F)cc(c2)C(F)(F)F)c1)c1cc(F)ccc1Cl | | 640.14 | C | |
| I-1599 | 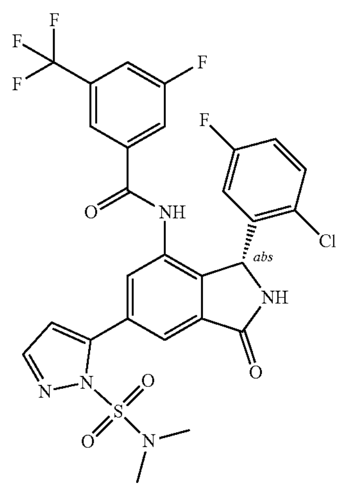 [SMILES: CN(C)S(=O)(=O)n1nccc1-c1cc(NC(=O)c2cc(F)cc(C(F)(F)F)c2)c2c(c1)C(=O)N[C@H]2c1cc(F)ccc1Cl] | CN(C)S(=O)(=O)n1nccc1-c1cc2C(=O)N[C@H](c2c(NC(=O)c2cc(F)cc(c2)C(F)(F)F)c1)c1cc(F)ccc1Cl | | 640.14 | A | |
| I-1600 | 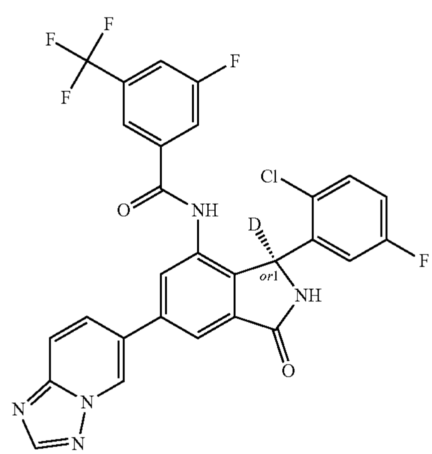 [SMILES: [2H][C@]1(c2cc(F)ccc2Cl)NC(=O)c2cc(-c3ccc4ncnn4c3)cc(NC(=O)c3cc(F)cc(C(F)(F)F)c3)c21] | [2H][C@@]1(NC(=O)c2cc(cc(NC(=O)c3cc(F)cc(c3)C(F)(F)F)c12)-c1ccc2ncnn2c1)c1cc(F)ccc1Cl | | 585.08 | A | |

TABLE 2-continued

Representative Compounds of the Invention with Bioactivity Data.

| Ex. No. | Structure | SMILES | $^1$H NMR | MS | ADP-Glo IC$_{50}$ | MCF 10A IC$_{50}$ |
|---|---|---|---|---|---|---|
| I-1601 | 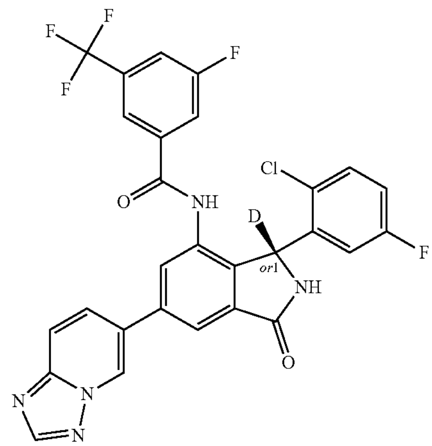 [SMILES: [2H][C@@]1(c2cc(F)ccc2Cl)NC(=O)c2cc(-c3ccc4ncnn4c3)cc(NC(=O)c3cc(F)cc(C(F)(F)F)c3)c21] | [2H][C@]1(NC(=O)c2cc(cc(NC(=O)c3cc(F)cc(c3)C(F)(F)F)c12)-c1ccc2ncnn2c1)c1cc(F)ccc1Cl | | 585.08 | A | |
| I-1602 | 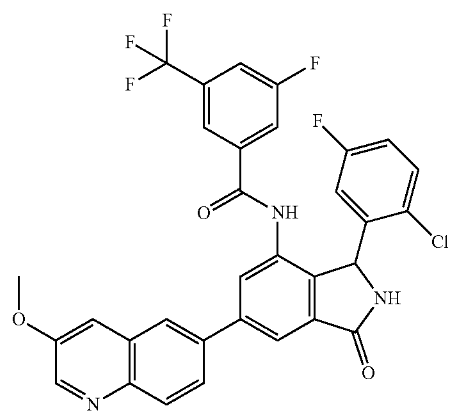 [SMILES: COc1cnc2ccc(-c3cc(NC(=O)c4cc(F)cc(C(F)(F)F)c4)c4c(c3)C(=O)NC4c3cc(F)ccc3Cl)cc2c1] | COc1cnc2ccc(cc2c1)-c1cc2C(=O)NC(c2c(NC(=O)c2cc(F)cc(c2)C(F)(F)F)c1)c1cc(F)ccc1Cl | | 624.5 | A | |
| I-1603 | 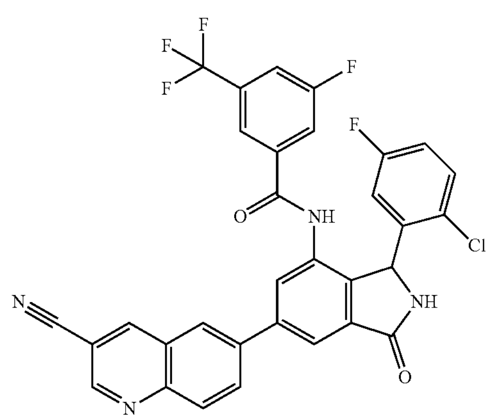 [SMILES: N#Cc1cnc2ccc(-c3cc(NC(=O)c4cc(F)cc(C(F)(F)F)c4)c4c(c3)C(=O)NC4c3cc(F)ccc3Cl)cc2c1] | Fc1ccc(Cl)c(c1)C1NC(=O)c2cc(cc(NC(=O)c3cc(F)cc(c3)C(F)(F)F)c12)-c1ccc2ncc(cc2c1)C#N | 1H NMR (DMSO-d6, 500 MHz) 10.66 (s, 1H), 9.24-9.33 (m, 1H), 9.21 (d, 2.1 Hz, 1H), 9.14 (d, 1.8 Hz, 1H), 8.59 (d, 2.0 Hz, 1H), 8.43 (dd, 8.8, 2.1 Hz, 1H), 8.26 (d, 8.7 Hz, 1H), 8.16 (d, 1.1 Hz, 1H), 8.00 (s, 1H), 7.97 (br d, 8.2 Hz, 1H), 7.78 (br d, 9.0 Hz, 1H), 7.72 (s, 1H), 7.34 (dd, 8.9, 5.2 Hz, 1H), 7.11 (td, 8.4, 3.0 Hz, 1H), 6.42-6.97 (m, 1H), 5.95-6.25 (m, 1H) | 619.5 | A | |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-1604 | 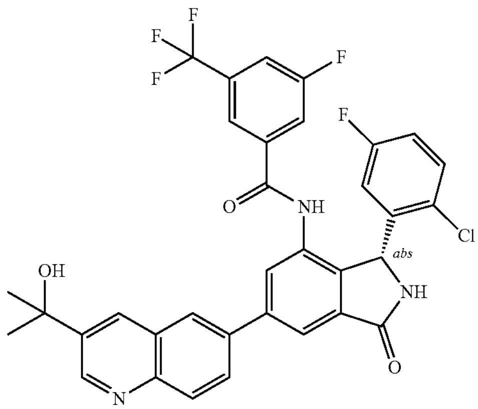 [SMILES: CC(C)(O)c1cnc2ccc(-c3cc(NC(=O)c4cc(F)cc(C(F)(F)F)c4)c4c(c3)C(=O)N[C@H]4c3cc(F)ccc3Cl)cc2c1] | CC(C)(O)c1cnc2cc(cc2c1)-c1cc2C(=O)N[C@H](c2c(NC(=O)c2cc(F)cc(c2)C(F)(F)F)c1)c1cc(F)ccc1Cl | | 652.2 | A | |
| I-1605 | 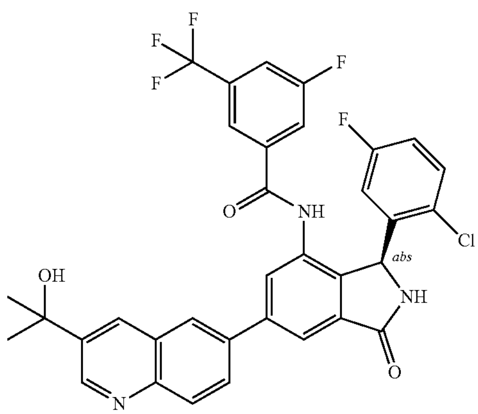 [SMILES: CC(C)(O)c1cnc2ccc(-c3cc(NC(=O)c4cc(F)cc(C(F)(F)F)c4)c4c(c3)C(=O)N[C@@H]4c3cc(F)ccc3Cl)cc2c1] | CC(C)(O)c1cnc2cc(cc2c1)c1cc2C(=O)N[C@@H](c2c(NC(=O)c2cc(F)cc(c2)C(F)(F)F)c1)c1cc(F)ccc1Cl | | 652.2 | E | |
| I-1606 | 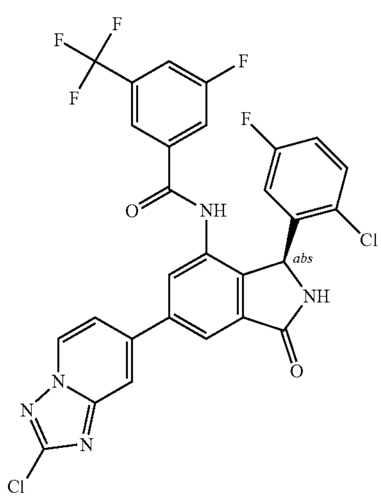 [SMILES: O=C(Nc1cc(-c2ccn3nc(Cl)nc3c2)cc2c1[C@@H](c1cc(F)ccc1Cl)NC2=O)c1cc(F)cc(C(F)(F)F)c1] | Fc1ccc(Cl)c(c1)[C@H]1NC(=O)c2cc(cc(NC(=O)c3cc(F)cc(c3)C(F)(F)F)c12)-c1ccn2nc(Cl)nc2c1 | | 619.2 | B | |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-1607 | 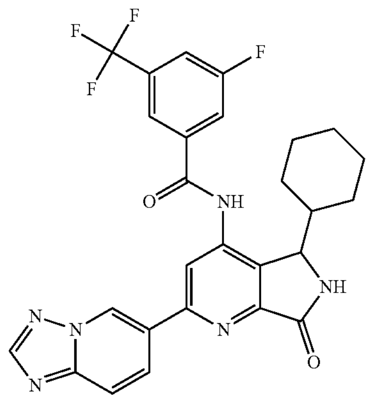 [SMILES: O=C(Nc1cc(-c2ccc3ncnn3c2)nc2c1C(C1CCCCC1)NC2=O)c1cc(F)cc(C(F)(F)F)c1] | Fc1cc(cc(c1)C(F)(F)F)C(=O)Nc1cc(nc2C(=O)NC(C3CCCCC3)c12)-c1ccc2ncnn2c1 | | | | C |
| I-1608 | 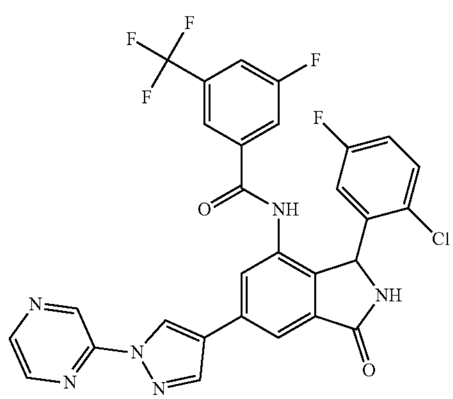 [SMILES: O=C(Nc1cc(-c2cnn(-c3cnccn3)c2)cc2c1C(c1cc(F)ccc1Cl)NC2=O)c1cc(F)cc(C(F)(F)F)c1] | Fc1ccc(C1)c(c1)C1NC(=O)c2cc(cc(NC(=O)c3cc(F)cc(c3)C(F)(F)F)c12)-c1cnn(c1)-c1nccn1 | NMR (400 MHz, DMSO-d6) 10.57 (s, 1H), 9.30 (s, 1H), 9.29 (s, 1H), 9.19 (s, 1H), 8.67 (d, 2.5 Hz, 1H), 8.63-8.60 (m, 2H), 8.17 (s, 1H), 8.00-7.94 (m, 2H), 7.78 (d, 9.3 Hz, 1H), 7.73 (s, 1H), 7.33 (dd, 8.9, 5.2 Hz, 1H), 7.10 (td, 8.4, 2.8 Hz, 1H), 6.58 (br s, 1H), 5.96 (br s, 1H). | 609.1 | A | |
| I-1609 | 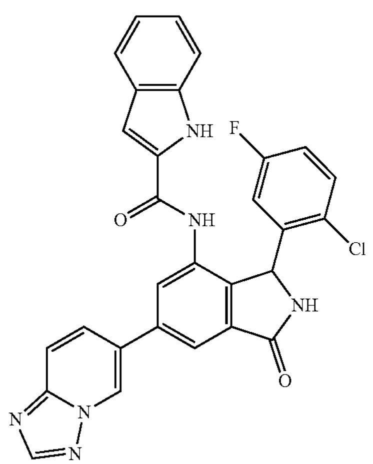 [SMILES: O=C(Nc1cc(-c2ccc3ncnn3c2)cc2c1C(c1cc(F)ccc1Cl)NC2=O)c1cc2ccccc2[nH]1] | Fc1ccc(C1)c(c1)C1NC(=O)c2cc(cc(NC(=O)c3cc4cccc4[nH]3)c12)-c1ccc2ncnn2c1 | NMR (400 MHz, ) 11.72 (s, 1H), 10.29 (s, 1H), 9.49 (s, 1H), 9.25 (s, 1H), 8.58 (s, 1H), 8.15 (dd, 9.3, 1.5 Hz, 1H), 8.09 (d, 0.9 Hz, 1H), 8.02-9.98 (m, 2H), 7.62 (d, 8.0 Hz, 1H), 7.44 (d, 8.2 Hz, 1H), 7.32 (dd, 8.8, 5.2 Hz, 1H), 7.21 (t, 7.5 Hz, 1H), 7.12-6.98 (m, 3H), 6.72 (br s, 1H), 6.26 (br s, 1H). | 535.2 | D | |

TABLE 2-continued

Representative Compounds of the Invention with Bioactivity Data.

| Ex. No. | Structure | SMILES | ¹H NMR | MS | ADP-Glo IC₅₀ | MCF 10A IC₅₀ |
|---|---|---|---|---|---|---|
| I-1610 | 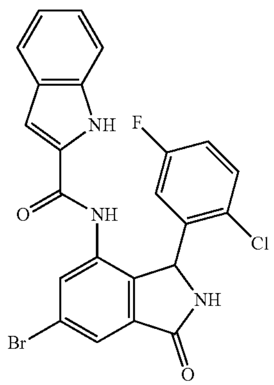 [SMILES: O=C(Nc1cc(Br)cc2c1C(c1cc(F)ccc1Cl)NC2=O)c1cc2ccccc2[nH]1] | Fc1ccc(C1)c(c1)C1NC(=O)c2cc(Br)cc(NC(=O)c3cc4ccc c4[nH]3)c12 | NMR (400 MHz, DMSO-d6) 11.71 (s, 1H), 10.18 (s, 1H), 9.28 (s, 1H), 7.81 (d, 1.5 Hz, 1H), 7.78 (d, 1.4 Hz, 1H), 7.61 (d, 7.9 Hz, 1H), 7.42 (d, 8.2 Hz, 1H), 7.30 (dd, 8.8, 5.2 Hz, 1H), 7.20 (td, 11.7, 4.4 Hz, 1H), 7.09-7.01 (m, 2H), 6.93 (d, 1.4 Hz, 1H), 6.64 (br s, 1H), 6.13 (br s, 1H). | 496.1 | D | |
| I-1611 | 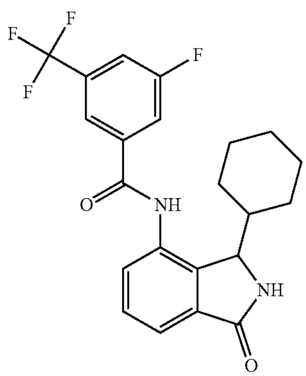 [SMILES: O=C(Nc1cccc2c1C(C1CCCCC1)NC2=O)c1cc(F)cc(C(F)(F)F)c1] | Fc1cc(cc(c1)C(F)(F)F)C(=O)Nc1ccc2C(=O)NC(C3CCCC3)c12 | NMR (400 MHz, DMSO-d6) 10.74 (br. s, 1H), 8.74 (s, 1H), 8.13 (s, 1H), 8.08 (br. d, 9.0 Hz, 1H), 8.04 (br. d, 8.5 Hz, 1H), 7.62-7.49 (m, 3H), 4.73 (d, 1.3 Hz, 1H), 1.90-1.80 (m, 1H), 1.73-1.64 (m, 1H), 1.59-1.50 (m, 3H), 1.39-1.27 (m, 1H), 1.06-0.86 (m, 3H), 0.79-0.61 (m, 2H). | 421.2 | D | |
| I-1612 | 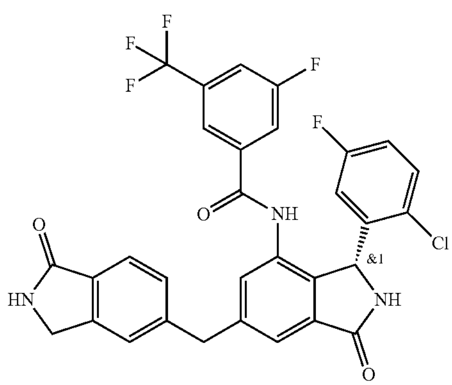 [SMILES: O=C(Nc1cc(Cc2ccc3c(c2)CNC3=O)cc2c1[C@H](c1cc(F)ccc1Cl)NC2=O)c1cc(F)cc(C(F)(F)F)c1] | Fc1ccc(C1)c(c1)[C@@H]1NC(=O)c2cc(Cc3cc4C(=O)NCc4c3)cc(NC(=O)c3cc(F)cc(c3)C(F)(F)F)c12 | 1H-NMR (400 MHz, DMSO-d6) 10.57 (br. s, 1H), 9.07 (br. s, 1H), 8.49 (s, 1H), 7.87 (br. d, 7.9 Hz, 1H), 7.71 (br. d, 8.6 Hz, 1H), 7.66 (s, 1H), 7.62 (d, 7.7 Hz, 1H), 7.56-7.50 (m, 2H), 7.46-7.41 (m, 2H), 7.30 (dd, 8.9, 5.2 Hz, 1H), 7.07 (app. td, 8.4, 3.1 Hz, 1H), 6.62 (br. s, 1H), 5.92 (br. s, 1H), 4.34 (s, 2H), 4.24 (d, A of AB, JAB = 14.9 Hz, 1H), 4.20 (d, B of AB, JAB = 14.7 Hz, 1H). | 612.2 | A | |
| I-1613 | 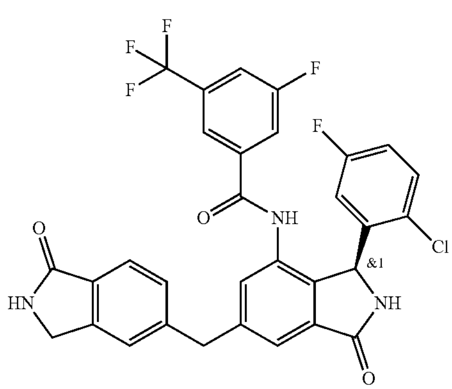 [SMILES: O=C(Nc1cc(Cc2ccc3c(c2)CNC3=O)cc2c1[C@@H](c1cc(F)ccc1Cl)NC2=O)c1cc(F)cc(C(F)(F)F)c1] | Fc1ccc(C1)c(c1)[C@H]1NC(=O)c2cc(Cc3ccc4C(=O)NCc4c3)cc(NC(=O)c3cc(F)cc(c3)C(F)(F)F)c12 | 1H-NMR (400 MHz, DMSO-d6) 10.47 (br. s, 1H), 9.11 (br. s, 1H), 8.48 (s, 1H), 7.92 (br. d, 8.4 Hz, 1H), 7.71 (br. d, 8.8 Hz, 1H), 7.64-7.60 (m, 3H), 7.52 (s, 1H), 7.44 (d, 7.8 Hz, 1H), 7.37 (s, 1H), 7.29 (dd, 8.9, 5.2 Hz, 1H), 7.08 (app. td, 8.4, 3.0 Hz, 1H), 6.60 (br. s, 1H), 5.92 (br. s, 1H), 4.35 (s, 2H), 4.26 (d, A of AB, JAB = 14.5 Hz, 1H), 4.22 (d, B of AB, JAB = 14.4 Hz, 1H). | 612.2 | B | |

TABLE 2-continued

Representative Compounds of the Invention with Bioactivity Data.

| Ex. No. | Structure | SMILES | $^1$H NMR | MS | ADP-Glo IC$_{50}$ | MCF 10A IC$_{50}$ |
|---|---|---|---|---|---|---|
| I-1614 | 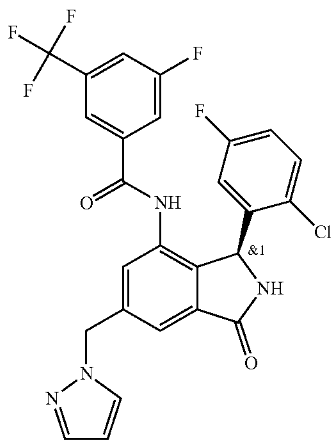 [SMILES: O=C(Nc1cc(Cn2cccn2)cc2c1[C@@H](c1cc(F)ccc1Cl)NC2=O)c1cc(F)cc(C(F)(F)F)c1] | Fc1ccc(C1)c(c1)[C@H]1NC(=O)c2cc(Cn3cccn3)cc(NC(=O)c3cc(F)cc(c3)C(F)(F)F)c12 | 1H-NMR (400 MHz, DMSO-d6) 10.63 (br. s, 1H), 9.09 (br. s, 1H), 7.91 (d, 2.0 Hz, 1H), 7.88-7.82 (m, 1H), 7.72 (br. d, 9.7 Hz, 1H), 7.67 (s, 1H), 7.51 (d, 1.8 Hz, 1H), 7.47-7.35 (m, 2H), 7.31 (dd, 8.8, 5.2 Hz, 1H), 7.08 (app. td, 8.5, 3.0 Hz, 1H), 6.60 (br. s, 1H), 6.31 (t, 2.0 Hz, 1H), 5.93 (br. s, 1H), 5.53-5.45 (m, 2H). | 547.2 | B | |
| I-1615 | 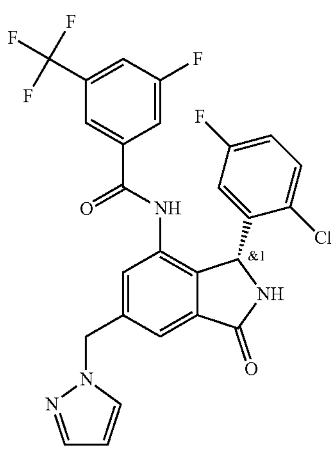 [SMILES: O=C(Nc1cc(Cn2cccn2)cc2c1[C@H](c1cc(F)ccc1Cl)NC2=O)c1cc(F)cc(C(F)(F)F)c1] | Fc1ccc(C1)c(c1)[C@@H]1NC(=O)c2cc(Cn3cccn3)cc(NC(=O)c3cc(F)cc(c3)C(F)(F)F)c12 | 1H-NMR (400 MHz, DMSO-d6) 10.68 (br. s, 1H), 9.08 (br. s, 1H), 7.91 (d, 2.1 Hz, 1H), 7.87-7.81 (m, 1H), 7.72 (br. d, 9.4 Hz, 1H), 7.68 (s, 1H), 7.51 (d, 1.7 Hz, 1H), 7.49-7.43 (m, 1H), 7.37 (br. s, 1H), 7.31 (dd, 8.8, 5.2 Hz, 1H), 7.07 (app. td, 8.5, 3.1 Hz, 1H), 6.62 (br. s, 1H), 6.31 (t, 2.0 Hz, 1H), 5.93 (br. s, 1H), 5.53-5.44 (m, 2H). | 547.2 | A | |
| I-1616 | 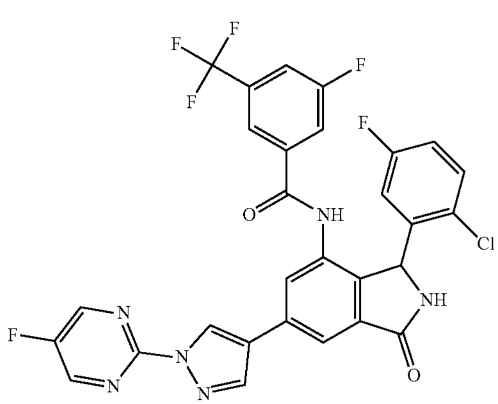 [SMILES: O=C(Nc1cc(-c2cnn(-c3ncc(F)cn3)c2)cc2c1C(c1cc(F)ccc1Cl)NC2=O)c1cc(F)cc(C(F)(F)F)c1] | Fc1cnc(nc1)-n1cc(cn1)-c1cc2C(=O)NC(c2c(NC(=O)c2cc(F)cc(c2)C(F)(F)F)c1)c1cc(F)ccc1Cl | NMR (400 MHz, DMSO-d6) 9.25 (s, 1H), 9.19 (br s, 1H), 9.04-9.01 (m, 2H), 8.54 (s, 1H), 8.36 (br s, 1H), 8.14 (s, 1H), 7.98-7.92 (m, 2H), 7.78 (br d, 8.6 Hz, 1H), 7.73 (s 1H), 7.32 (dd, 8.8, 5.1 Hz, 1H), 7.10 (td, 8.3, 2.7 Hz, 1H), 6.60 (br s, 1H), 6.02 (br s, 1H). | 629 | A | |

TABLE 2-continued

Representative Compounds of the Invention with Bioactivity Data.

| Ex. No. | Structure | SMILES | $^1$H NMR | MS | ADP-Glo IC$_{50}$ | MCF 10A IC$_{50}$ |
|---|---|---|---|---|---|---|
| I-1617 | 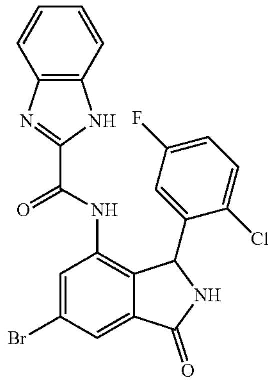 [SMILES: O=C(Nc1cc(Br)cc2c1C(c1cc(F)ccc1Cl)NC2=O)c1nc2ccccc2[nH]1] | Fc1ccc(C1)c(c1)C1NC(=O)c2cc(Br)cc(NC(=O)c3nc4ccc cc4[nH]3)c12 | NMR (400 MHz, DMSO-d6) 9.32 (br s, 1H), 8.38 (s, 1H), 7.99 (br s, 1H), 7.78 (s, 1H), 7.65-7.60 (m, 2H), 7.32 (dd, 6.0, 3.1 Hz, 3H), 7.07 (td, 8.5, 2.9 Hz, 1H), 6.93-6.72 (m, 1H), 6.19 (br s, 1H) | 501 | D | |
| I-1618 | 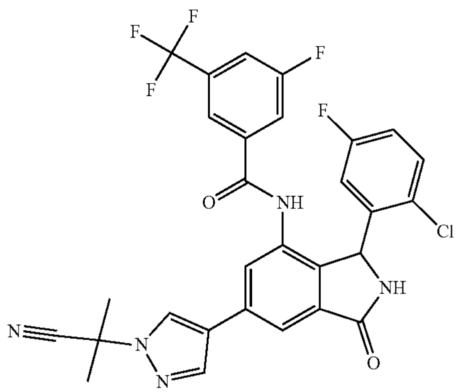 [SMILES: CC(C)(C#N)n1cc(-c2cc(NC(=O)c3cc(F)cc(C(F)(F)F)c3)c3c(c2)C(=O)NC3c2cc(F)ccc2Cl)cn1] | CC(C)(C#N)n1cc(cn1)-c1cc2C(=O)NC(c2c(NC(=O)c2cc(F)cc(c2)C(F)(F)F)c1cc(F)ccc1Cl | (400 MHz, DMSO-D6) 10.56 (br s, 1 H), 9.16 (br s, 1 H), 8.77 (s, 1 H), 8.25 (s, 1 H), 8.04 (s, 1 H), 7.96 (br d, 8.3 Hz, 1 H), 7.79 (s, 1 H), 7.77 (br d, 13.5 Hz, 1 H), 7.72 (s, 1 H), 7.32 (dd, 8.8, 5.2 Hz, 1 H), 7.09 (td, 8.5, 2.8 Hz, 1 H), 6.60 (br s, 1 H), 5.97 (br s, 1 H), 2.03 (s, 6 H). | 598.3 | A | |
| I-1619 | 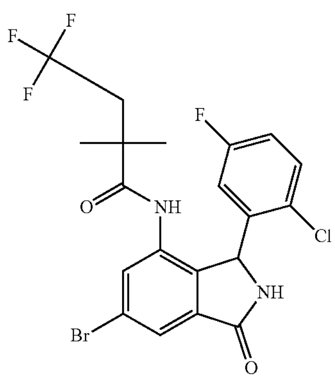 [SMILES: CC(C)(CCC(F)(F)F)C(=O)Nc1cc(Br)cc2c1C(c1cc(F)ccc1Cl)NC2=O] | CC(C)(CC(F)(F)F)C(=O)Nc1cc(Br)cc2C(=O)NC(c12)c1cc(F)ccc1Cl | 1H NMR (400 MHz, DMSO):-' 9.40 (s, 1H), 9.28 (s, 1H), 7.75 (d, 1.2 Hz, 1H), 7.59 (d, 1.5 Hz, 1H), 7.51 (br s, 1H), 7.24 (td, 8.4, 3.0 Hz, 1H), 6.07 (br s, 1H), 2.52-2.47 (m, 2H), 0.98 (s, 3H), 0.90 (s, 3H). | 509.1 | E | |
| I-1620 | 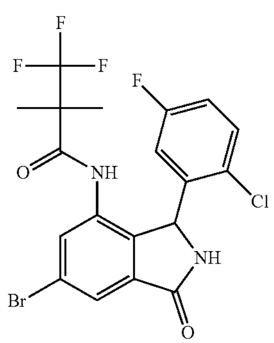 [SMILES: CC(C)(C(=O)Nc1cc(Br)cc2c1C(c1cc(F)ccc1Cl)NC2=O)C(F)(F)F] | CC(C)(C(=O)Nc1cc(Br)cc2C(=O)NC(c12)c1cc(F)ccc1Cl)C(F)(F)F | 1H NMR (400 MHz, DMSO):-' 9.73 (s, 1H), 9.29 (s, 1H), 7.79 (d, 1.6 Hz, 1H), 7.59 (s, 1H), 7.52 (br s, 1H), 7.25 (td, 8.4, 3.0 Hz, 1H), 6.00 (br s, 1H), 1.12 (s, 6H). | 495.1 | E | |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-1621 | 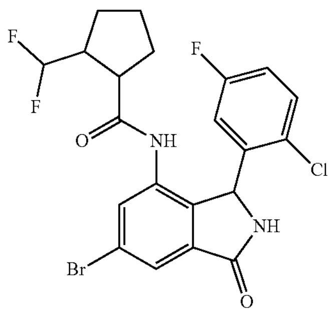 [SMILES: O=C1NC(c2cc(F)ccc2Cl)c2c(NC(=O)C3CCCC3C(F)F)cc(Br)cc21] | FC(F)C1CCCC1C(=O)Nc1cc(Br)cc2C(=O)NC(c12)c1cc(F)ccc1Cl | 1H NMR (400 MHz, DMSO):-' 10.26 (s, 0.5H), 10.16 (s, 0.5H), 9.25 (s, 1H), 7.77 (d, 1.5 Hz, 0.5H), 7.70 (d, 1.4 Hz, 0.5H), 7.68 (d, 1.3 Hz, 0.5H), 7.62 (d, 1.6 Hz, 0.5H), 7.47 (br s, 1H), 7.26-7.19 (m, 1H), 6.14 (s, 0.5H), 6.10 (br s, 0.5H), 5.89 (td, 57.0, 3.9 Hz, 1H), 2.68-2.30 (m, 2H), 1.77-0.92 (m, 6H). | 503 | E | |
| I-1622 | 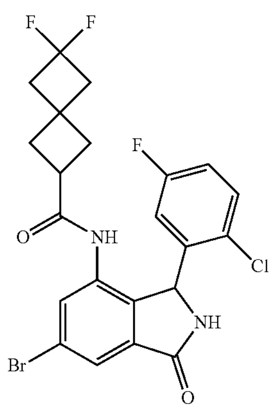 [SMILES: O=C1NC(c2cc(F)ccc2Cl)c2c(NC(=O)C3CC4(C3)CC(F)(F)C4)cc(Br)cc21] | Fc1ccc(C1)c(c1)C1NC(=O)c2cc(Br)cc(NC(=O)C3CC4(C3)CC(F)(F)C4)c12 | 1H NMR (400 MHz, DMSO):-' 9.70 (s, 1H), 9.24 (s, 1H), 7.70 (d, 1.5 Hz, 1H), 7.57 (d, 1.7 Hz, 1H), 7.50 (br s, 1H), 7.24 (td, 8.4, 3.1 Hz, 1H), 6.00 (br s, 1H), 2.84 (pentet, 8.4 Hz, 1H), 2.59 (td, 12.6, 2.0 Hz, 2H), 2.43 (td, 12.5, 1.9 Hz, 2H), 2.10-1.94 (m, 3H), 1.82 (br s, 1H). | 515 | D | |
| I-1623 | 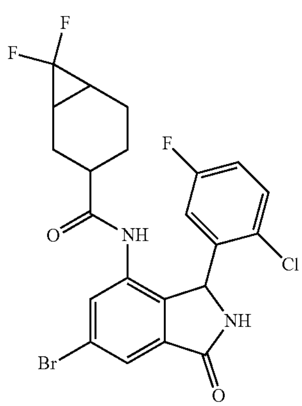 [SMILES: O=C1NC(c2cc(F)ccc2Cl)c2c(NC(=O)C3CCC4C(C3)C4(F)F)cc(Br)cc21] | Fc1ccc(C1)c(c1)C1NC(=O)c2cc(Br)cc(NC(=O)C3CCC4C(C3)C4(F)F)c12 | 1H NMR (400 MHz, DMSO):-' 9.82 (s, 0.5H), 9.77 (d, 5.7 Hz, 0.5H), 9.25 (s, 1H), 7.71-7.68 (m, 1H), 7.66 (d, 1.3 Hz, 0.25H), 7.61 (d, 1.5 Hz, 0.25H), 7.58 (d, 1.7 Hz, 0.25H), 7.57 (d, 1.7 Hz, 0.25H), 7.49 (br s, 1H), 7.29-7.20 (m, 1H), 6.00 (br s, 1H), 2.03-0.72 (m, 9H). | 515.1 | D | |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-1624 | 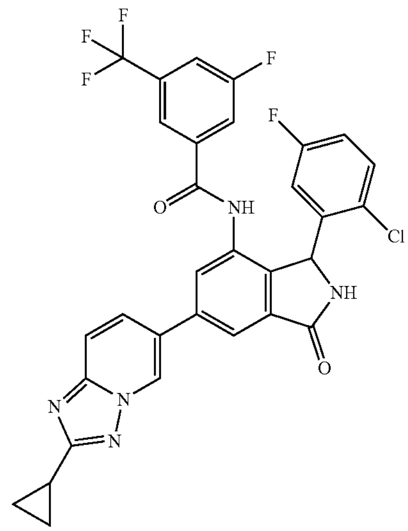 [SMILES: O=C(Nc1cc(-c2ccc3nc(C4CC4)nn3c2)cc2c1C(c1cc(F)ccc1Cl)NC2=O)c1cc(F)cc(C(F)(F)F)c1] | Fc1ccc(C1)c(c1)C1NC(=O)c2cc(cc(NC(=O)c3cc(F)cc(c3)C(F)(F)F)c12)-c1ccc2nc(nn2c1)C1CC1 | | | | A |
| I-1625 | 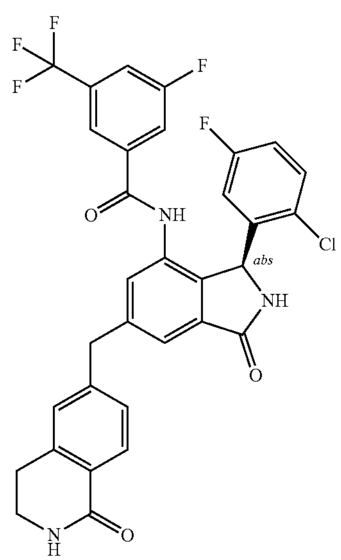 [SMILES: O=C(Nc1cc(Cc2ccc3c(c2)CCNC3=O)cc2c1[C@@H](c1cc(F)ccc1Cl)NC2=O)c1cc(F)cc(C(F)(F)F)c1] | Fc1ccc(C1)c(c1)[C@@H]1NC(=O)c2cc(Cc3cc4C(=O)NCCc4c3)cc(NC(=O)c3cc(F)cc(c3)C(F)(F)F)c12 | 1H-NMR (400 MHz, DMSO-d6) 10.49 (br. s, 1H), 9.12 (br. s, 1H), 7.92 (br. d, 8.1 Hz, 1H), 7.87 (t, 2.7 Hz, 1H), 7.79 (d, 7.9 Hz, 1H), 7.71 (br. d, 9.1 Hz, 1H), 7.63 (s, 1H), 7.58 (s, 1H), 7.36 (s, 1H), 7.32-7.27 (m, 2H), 7.25 (s, 1H), 7.08 (app. td, 8.5, 3.0 Hz, 1H), 6.61 (br. s, 1H), 5.92 (br. s, 1H), 4.17 (d, A of AB, JAB = 14.7 Hz, 1H), 4.12 (d, B of AB, JAB = 14.6 Hz, 1H), 3.36 (td, 6.8, 2.8 Hz, 2H), 2.87 (t, 6.5 Hz, 2H). | 626.3 | | C |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-1626 | 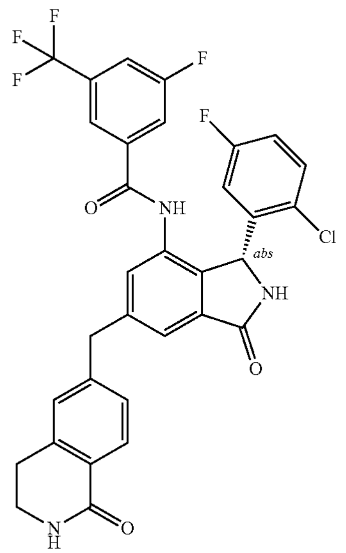 [SMILES: O=C(Nc1cc(Cc2ccc3c(c2)CCNC3=O)cc2c1[C@H](c1cc(F)ccc1Cl)NC2=O)c1cc(F)cc(C(F)(F)F)c1] | Fc1ccc(C1)c(c1)[C@H]1NC(=O)c2cc(Cc3ccc4C(=O)NCCc4c3)cc(NC(=O)c3cc(F)cc(c3)C(F)(F)F)c12 | 1H-NMR (400 MHz, DMSO-d6) 10.48 (s, 1H), 9.13 (br. s, 1H), 7.93 (br. d, 8.5 Hz, 1H), 7.88 (br. t, 2.5 Hz, 1H), 7.79 (d, 7.9 Hz, 1H), 7.71 (br. d, 9.1 Hz, 1H), 7.63 (s, 1H), 7.59 (s, 1H), 7.35 (br. s, 1H), 7.33-7.27 (m, 2H), 7.25 (s, 1H), 7.08 (app. td, 8.4, 3.0 Hz, 1H), 6.57 (br. s, 1H), 5.92 (br. s, 1H), 4.17 (d, A of AB, JAB = 14.6 Hz, 1H), 4.12 (d, B of AB JAB = 14.6 Hz, 1H), 3.35 (td, 6.5, 2.8 Hz, 2H), 2.87 (t, 6.5 Hz, 2H). | 626.2 | A | |
| I-1627 | 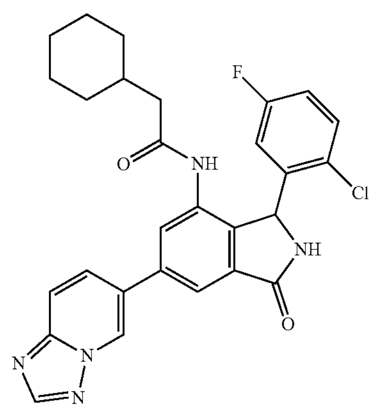 [SMILES: O=C(CC1CCCCC1)Nc1cc(-c2ccc3ncnn3c2)cc2c1C(c1cc(F)ccc1Cl)NC2=O] | Fc1ccc(C1)c(c1)C1NC(=O)c2cc(cc(NC(=O)CC3CCCCC3)c12)-c1ccc2ncnn2c1 | NMR (400 MHz, DMSO-d6) 9.78 (s, 1H), 9.44 (s, 1H), 9.22 (s, 1H), 8.58 (s, 1H), 8.08 (dd, 9.3, 1.6 Hz, 1H), 7.97 (d, 9.3 H7, 1H), 7.87 (d, 1.4 Hz, 1H), 7.58-7.49 (m, 1H), 7.24 (tt, 5.8, 2.9 Hz, 1H), 6.53 (br s, 1H), 6.16 (s, 1H), 1.93 (d, 6.9 Hz, 2H), 1.56 (d, 9.0 Hz, 3H), 1.51-1.44 (m, 1H), 1.38 (t, 13.5 Hz, 2H), 1.16-1.01 (m, 3H), 0.80-0.65 (m, 2H). | 518.2 | D | |
| I-1628 | 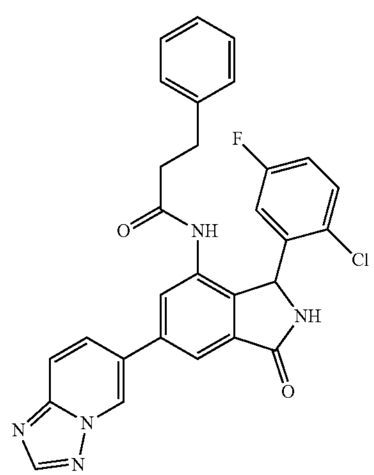 [SMILES: O=C(CCc1ccccc1)Nc1cc(-c2ccc3ncnn3c2)cc2c1C(c1cc(F)ccc1Cl)NC2=O] | Fc1ccc(C1)c(c1)C1NC(=O)c2cc(cc(NC(=O)CCc3ccccc3)c12)-c1ccc2ncnn2c1 | 1H-NMR (400 MHz, DMSO-d6) 9.88 (br. s, 1H), 9.44 (s, 1H), 9.23 (br. s, 1H), 8.57 (s, 1H), 8.08 (d, 9.1 Hz, 1H), 8.02 (s, 1H), 7.97 (d, 9.2 Hz, 1H), 7.78 (s, 1H), 7.58-7.49 (m, 1H), 7.33-7.23 (m, 3H), 7.22-7.09 (m, 3H), 6.65 (br. s, 1H), 6.09 (br. s, 1H), 2.69-2.55 (m, 2H), 2.41-2.19 (m, 2H). | 526.3 | D | |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-1629 | 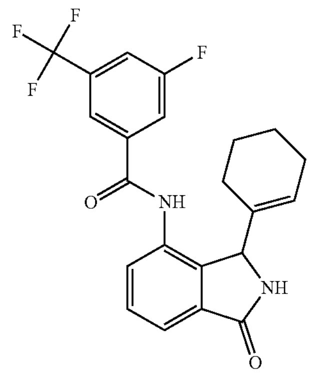 [SMILES: O=C(Nc1cccc2c1C(C1=CCCCC1)NC2=O)c1cc(F)cc(C(F)(F)F)c1] | Fc1cc(cc(c1)C(F)(F)F)C(=O)Nc1ccc2C(=O)NC(c12)C1=CCCCC1 | NMR (400 MHz, DMSO-d6) 10.58 (s, 1H), 8.66 (s, 1H), 8.11 (s, 1H), 8.04 (s, 1H), 8.02 (s, 1H), 7.63-7.50 (m, 3H), 5.69-5.64 (m, 1H), 5.12 (s, 1H), 1.90-1.78 (m, 1H), 1.52-1.27 (m, 5H), 1.26-1.16 (m, 1H), 1.13-1.01 (m, 1H). | 419.2 | D | |
| I-1630 | 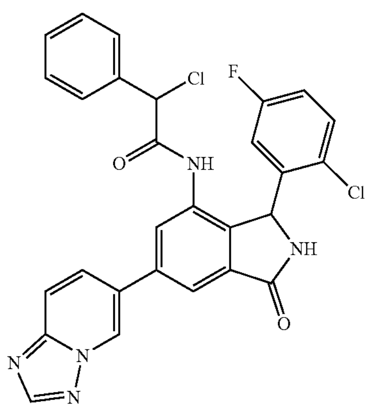 [SMILES: O=C1NC(c2cc(F)ccc2Cl)c2c(NC(=O)C(Cl)c3ccccc3)cc(-c3ccc4ncnn4c3)cc21] | Fc1ccc(C1)c(c1)C1NC(=O)c2cc(cc(NC(=O)C(Cl)c3ccccc3)c12)-c1ccc2ncnn2c1 | NMR (400 MHz, DMSO-d6) 10.43 (br s, 1H), 9.47 (d, 6.0 Hz, 1H), 9.23 (br s, 1H), 8.57 (d, 3.1 Hz, 1H), 8.10 (ddd, 9.2, 7.3, 1.7 Hz, 1H), 8.05 (dd, 5.9, 1.6 Hz, 1H), 7.99-7.94 (m, 1H), 7.93-7.88 (m, 1H), 7.43 (br s, 1H), 7.40-7.29 (m, 6H), 7.16 (dtd, 11.6, 8.6, 3.0 Hz, 1H), 6.49 (br s, 1H), 6.14 (br s, 1H), 5.54 (s, 0.5H), 5.49 (s, 0.5 H). | 546 | D | |
| I-1631 | 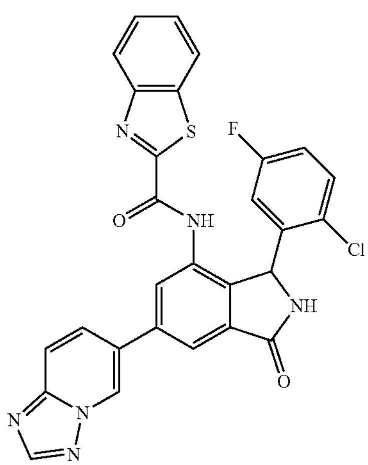 [SMILES: O=C(Nc1cc(-c2ccc3ncnn3c2)cc2c1C(c1cc(F)ccc1Cl)NC2=O)c1nc2ccccc2s1] | Fc1ccc(C1)c(c1)C1NC(=O)c2cc(cc(NC(=O)c3nc4ccccc4s3)c12)-c1ccc2ncnn2c1 | NMR (400 MHz, DMSO-d6) 9.48 (s, 1H), 9.30 (br s, 1H), 8.58 (s, 1H), 8.30-8.23 (m, 2H), 8.21-8.07 (m, 4H), 7.99 (d, 9.2 Hz, 1H), 7.76-7.52 (m, 2H), 7.33 (dd, 8.8, 5.2 Hz, 1H), 7.06 (td, 8.5, 3.0 Hz, 1H), 6.62 (br s, 1H), 6.24 (br s, 1H). | 555 | D | |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-1632 | 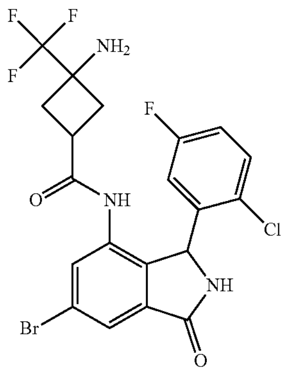 [SMILES: NC1(C(F)(F)F)CC(C(=O)Nc2cc(Br)cc3c2C(c2cc(F)ccc2Cl)NC3=O)C1] | NC1(CC(C1)C(=O)Nc1cc(Br)cc2C(=O)NC(c12)c1cc(F)ccc1Cl)C(F)(F)F | 1H NMR (400 MHz, DMSO):-' 9.79 (s, 0.4H), 9.76 (s, 0.6H), 9.22 (s, 1H), 7.71-7.64 (m, 1H), 7.61 (d, 1.7 Hz, 0.6H), 7.59 (d, 1.7 Hz, 0.4H), 7.51-7.39 (m, 1H), 7.19 (td, 8.3, 3.1 Hz, 1H), 7.09-6.10 (br m, 1H), 5.95 (br s, 1H), 3.13-3.00 (m, 0.4H), 2.69-2.61 (m, 0.6H), 2.32-2.14 (m, 2.4H), 2.10-1.80 (m, 2H), 1.72-1.54 (m, 0.6H). | 520.1 | E | |
| I-1633 | 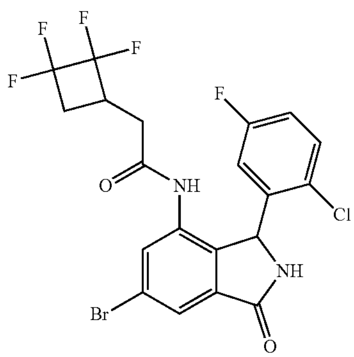 [SMILES: O=C(CC1CC(F)(F)C1(F)F)Nc1cc(Br)cc2c1C(c1cc(F)ccc1Cl)NC2=O] | Fc1ccc(C1)c(c1)C1NC(=O)c2cc(Br)cc(NC(=O)CC3CC(F)(F)C3(F)F)c12 | 1H NMR (400 MHz, DMSO):-' 10.00 (s, 1H), 9.25 (s, 1H), 7.74-7.69 (m, 1H), 7.65 (d, 1.7 Hz, 0.5H), 7.62 (d, 1.4 Hz, 0.5H), 7.56-7.41 (m, 1H), 7.29-7.19 (m, 1H), 7.12-6.14 (br m, 1H), 5.95 (br s, 1H), 2.95 (br s, 1H), 2.80-2.63 (m, 1H), 2.49-2.05 (m, 3H). | 523 | D | |
| I-1634 | 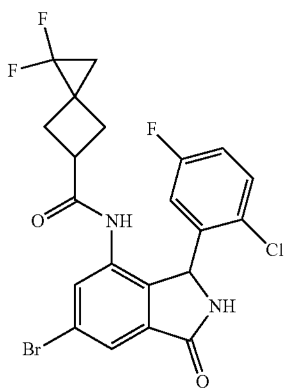 [SMILES: O=C1NC(c2cc(F)ccc2Cl)c2c(NC(=O)C3CC4(C3)CC4(F)F)cc(Br)cc21] | Fc1ccc(C1)c(c1)C1NC(=O)c2cc(Br)cc(NC(=O)C3CC4(CC4(F)F)C3)c12 | 1H NMR (400 MHz, DMSO):-' 9.87 (s, 1H), 9.27 (s, 1H), 7.74-7.68 (m, 1H), 7.62 (d, 1.7 Hz, 0.5H), 7.60 (d, 1.7 Hz, 0.5H), 7.57-7.39 (m, 1H), 7.19 (td, 8.8, 3.1 Hz, 1H), 7.12-6.22 (br m, 1H), 6.03 (br s, 1H), 3.17-2.96 (m, 1H), 2.20-1.77 (m, 4H), 1.38 (t, 8.7 Hz, 1H), 1.29 (td, 8.7, 2.3 Hz, 1H). | 499 | E | |
| I-1635 | 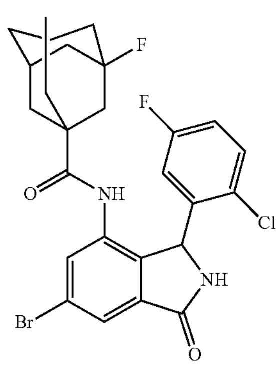 [SMILES: CCC1(C(=O)Nc2cc(Br)cc3c2C(c2cc(F)ccc2Cl)NC3=O)CC2CCCC(F)(C2)C1] | CC12CC3CC(F)(C1)CC(C3)(C2)C(=O)Nc1cc(Br)cc2C(=O)NC(c12)c1cc(F)ccc1Cl | 1H NMR (400 MHz, DMSO):-' 9.38 (s, 0.5H), 9.37 (s, 0.5H), 9.26 (s, 1H), 7.72 (d, 1.6 Hz, 1H), 7.59 (d, 1.7 Hz, 0.5H), 7.58 (d, 1.7 Hz, 0.5H), 7.52 (br s, 1H), 7.26 (td, 8.4, 3.1 Hz, 1H), 7.11-6.18 (br m, 1H), 5.99 (br s, 1H), 2.22 (br s, 1H), 1.72-1.47 (m, 5H), 1.45-0.94 (m, 7H), 0.84 (s, 1.5H), 0.83 (s, 1.5H). | 549.2 | B | |

TABLE 2-continued

Representative Compounds of the Invention with Bioactivity Data.

| Ex. No. | Structure | SMILES | $^1$H NMR | MS | ADP-Glo IC$_{50}$ | MCF 10A IC$_{50}$ |
|---|---|---|---|---|---|---|
| I-1636 | 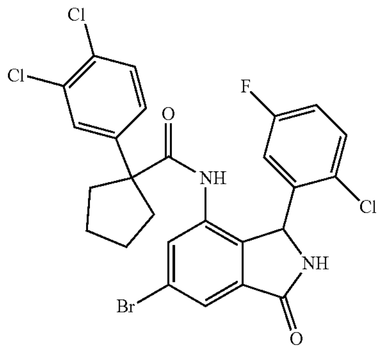 [SMILES: O=C1NC(c2cc(F)ccc2Cl)c2c(NC(=O)C3(c4ccc(Cl)c(Cl)c4)CCCC3)cc(Br)cc21] | Fc1ccc(C1)c(c1)C1NC(=O)c2cc(Br)cc(NC(=O)C3(CCCC3)c3ccc(Cl)c(Cl)c3)c12 | 1H NMR (400 MHz, DMSO):-' 9.37 (s, 1H), 9.25 (s, 1H), 7.71 (d, 1.7 Hz, 1H), 7.55 (d, 1.7 Hz, 1H), 7.49-7.42 (m, 2H), 7.40 (d, 2.2 Hz, 1H), 7.18 (td, 8.4, 3.0 Hz, 1H), 7.07 (dd, 8.5, 2.2 Hz, 1H), 6.70-6.16 (br m, 1H), 6.10 (s, 1H), 2.33-2.12 (m, 2H), 1.84-1.63 (m, 2H), 1.56-1.41 (m, 2H), 1.40-1.22 (m, 2H). | 595.1 | E | |
| I-1637 | 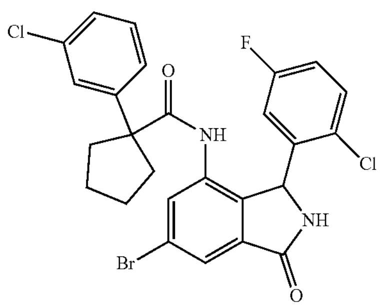 [SMILES: O=C1NC(c2cc(F)ccc2Cl)c2c(NC(=O)C3(c4cccc(Cl)c4)CCCC3)cc(Br)cc21] | Fc1ccc(C1)c(c1)C1NC(=O)c2cc(Br)cc(NC(=O)C3(CCCC3)c3cccc(Cl)c3)c12 | 1H NMR (400 MHz, DMSO):-' 9.30 (s, 1H), 9.25 (s, 1H), 7.70 (d, 1.6 Hz, 1H), 7.51 (d, 1.7 Hz, 1H), 7.51-7.46 (m, 1H), 7.29-7.26 (m, 2H), 7.26-7.24 (m, 1H), 7.21 (dt, 8.3, 2.9 Hz, 1H), 7.10-7.03 (m, 1H), 6.82-6.22 (br m, 1H), 6.11 (br s, 1H), 2.25-2.09 (m, 2H), 1.86-1.75 (m, 1H), 1.74-1.62 (m, 1H), 1.54-1.40 (m, 2H), 1.33-1.19 (m, 2H). | 561.1 | E | |
| I-1638 | 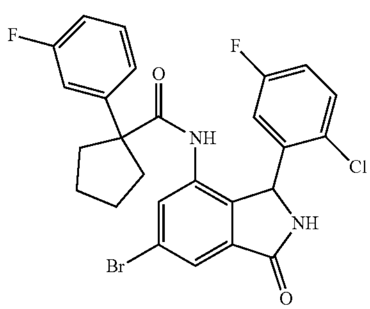 [SMILES: O=C1NC(c2cc(F)ccc2Cl)c2c(NC(=O)C3(c4cccc(F)c4)CCCC3)cc(Br)cc21] | Fc1cccc(c1)C1(CCCC1)C(=O)Nc1cc(Br)cc2C(=O)NC(c12)c1cc(F)ccc1Cl | 1H NMR (400 MHz, DMSO) 9.35-9.19 (m, 2H), 7.69 (d, 1.6 Hz, 1H), 7.52 (d, 1.7 Hz, 1H), 7.52-7.46 (m, 1H), 7.28 (dd, 14.4, 7.9 Hz, 1H), 7.22 (td, 8.5, 3.1 Hz, 1H), 7.07-6.97 (m, 2H), 6.95 (d, 7.9 Hz, 1H), 6.72-6.23 (br m, 1H), 6.14 (br s, 1H), 2.23-2.09 (m, 2H), 1.88-1.77 (m, 1H), 1.73-1.63 (m, 1H), 1.54-1.40 (m, 2H), 1.34-1.20 (m, 2H). | 545 | E | |
| I-1639 | 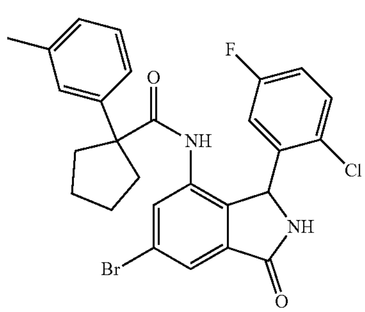 [SMILES: Cc1cccc(C2(C(=O)Nc3cc(Br)cc4c3C(c3cc(F)ccc3Cl)NC4=O)CCCC2)c1] | Cc1cccc(c1)C1(CCCC1)C(=O)Nc1cc(Br)cc2C(=O)NC(c12)c1cc(F)ccc1Cl | 1H NMR (400 MHz, DMSO):-' 9.23 (s, 1H), 9.11 (s, 1H), 7.68 (d, 1.1 Hz, 1H), 7.53 (d, 1.2 Hz, 1H), 7.53-7.46 (m, 1H), 7.23 (td, 8.3, 2.9 Hz, 1H), 7.13 (t, 7.7 Hz, 1H), 7.05 (s, 1H), 7.01 (d, 7.3 Hz, 1H), 6.92 (d, 7.8 Hz, 1H), 6.76-6.24 (br s, 1H), 6.15 (br s, 1H), 2.27 (s, 3H), 2.19-2.08 (m, 2H), 1.87-1.75 (m, 1H), 1.72-1.62 (m, 1H), 1.53-1.38 (m, 2H), 1.31-1.14 (m, 2H). | 541.1 | E | |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-1640 | 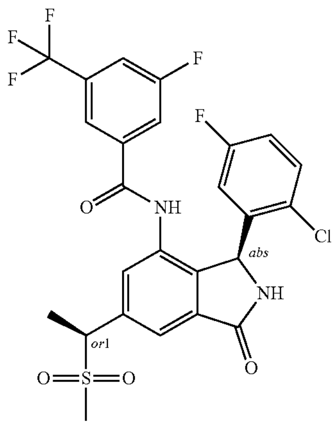 [SMILES: C[C@@H](c1cc(NC(=O)c2cc(F)cc(C(F)(F)F)c2)c2c(c1)C(=O)N[C@@H]2c1cc(F)ccc1Cl)S(C)(=O)=O] | C[C@@H](c1cc2C(=O)N[C@@H](c2c(NC(=O)c2cc(F)cc(c2)C(F)(F)F)c1cc(F)ccc1Cl)S(C)(=O)=O | NMR (400 MHz, DMSO-d6) ' 10.64 (s, 1H), 9.28 (s, 1H), 7.95 (d, 8.1 Hz, 1H), 7.80 (d, 2.7 Hz, 1H), 7.74 (d, 9.3 Hz, 1H), 7.64 (s, 1H), 7.55 (s, 1H), 7.32 (dd, 8.8, 5.1 Hz, 1H), 7.10 (m, 1H), 6.59 (br, s, 1H), 6.00 (br, s, 1H), 4.87-4.78 (m, 1H), 2.91 (s, 3H), 1.71 (d, 7.1 Hz, 3H) | 573 | D | |
| I-1641 | 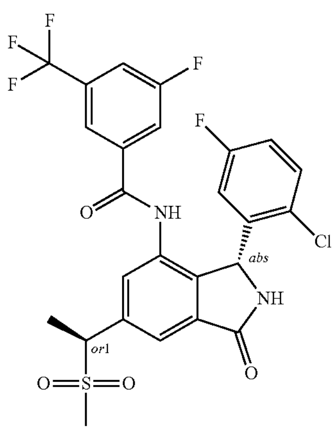 [SMILES: C[C@@H](c1cc(NC(=O)c2cc(F)cc(C(F)(F)F)c2)c2c(c1)C(=O)N[C@H]2c1cc(F)ccc1Cl)S(C)(=O)=O] | C[C@@H](c1cc2C(=O)N[C@H](c2c(NC(=O)c2cc(F)cc(c2)C(F)(F)F)c1cc(F)ccc1Cl)S(C)(=O)=O | NMR (400 MHz, DMSO-d6) 10.64 (s, 1H), 9.28 (s, 1H), 7.95 (d, 8.1 Hz, 1H), 7.80 (d, 2.7 Hz, 1H), 7.74 (d, 9.3 Hz, 1H), 7.64 (s, 1H), 7.55 (s, 1H), 7.32 (dd, 8.8, 5.1 Hz, 1H), 7.10 (m, 1H), 6.59 (br, s, 1H), 6.00 (br, s, 1H), 4.87-4.78 (m, 1H), 2.91 (s, 3H), 1.71 (d, 7.1 Hz, 3H) | 573 | A | |
| I-1642 | 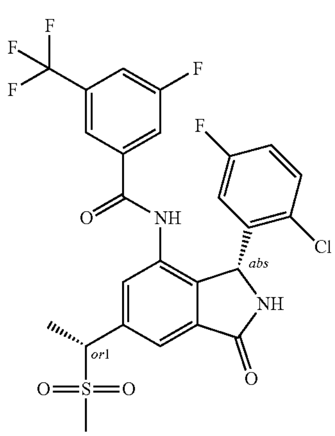 [SMILES: C[C@H](c1cc(NC(=O)c2cc(F)cc(C(F)(F)F)c2)c2c(c1)C(=O)N[C@H]2c1cc(F)ccc1Cl)S(C)(=O)=O] | C[C@H](c1cc2C(=O)N[C@H](c2c(NC(=O)c2cc(F)cc(c2)C(F)(F)F)c1cc(F)ccc1Cl)S(C)(=O)=O | NMR (400 MHz, DMSO-d6) 10.64 (s, 1H), 9.28 (s, 1H), 7.95 (d, 8.1 Hz, 1H), 7.80 (d, 2.7 Hz, 1H), 7.74 (d, 9.3 Hz, 1H), 7.64 (s, 1H), 7.55 (s, 1H), 7.32 (dd, 8.8, 5.1 Hz, 1H), 7.10 (m, 1H), 6.59 (br, s, 1H), 6.00 (br, s, 1H), 4.87-4.78 (m, 1H), 2.91 (s, 3H), 1.71 (d, 7.1 Hz, 3H) | 573 | A | |

TABLE 2-continued

Representative Compounds of the Invention with Bioactivity Data.

| Ex. No. | Structure | SMILES | ¹H NMR | MS | ADP-Glo IC₅₀ | MCF 10A IC₅₀ |
|---|---|---|---|---|---|---|
| I-1643 | 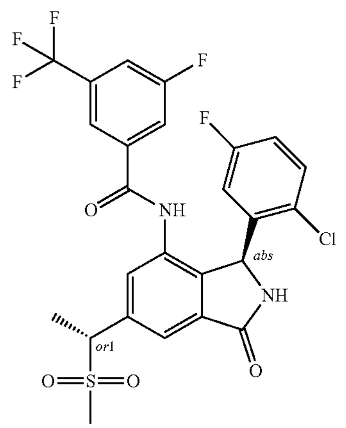 [SMILES: C[C@H](c1cc(NC(=O)c2cc(F)cc(C(F)(F)F)c2)c2c(c1)C(=O)N[C@@H]2c1cc(F)ccc1Cl)S(C)(=O)=O] | C[C@H](c1cc2C(=O)N[C@@H](c2c(NC(=O)c2cc(F)cc(c2)C(F)(F)F)c1)c1cc(F)ccc1Cl)S(C)(=O)=O | NMR (400 MHz, DMSO-d6) 10.64 (s, 1H), 9.28 (s, 1H), 7.95 (d, 8.1 Hz, 1H), 7.80 (d, 2.7 Hz, 1H), 7.74 (d, 9.3 Hz, 1H), 7.64 (s, 1H), 7.55 (s, 1H), 7.32 (dd, 8.8, 5.1 Hz, 1H), 7.10 (m, 1H), 6.59 (br, s, 1H), 6.00 (br, s, 1H), 4.87-4.78 (m, 1H), 2.91 (s, 3H), 1.71 (d, 7.1 Hz, 3H) | 573 | D | |
| I-1644 | 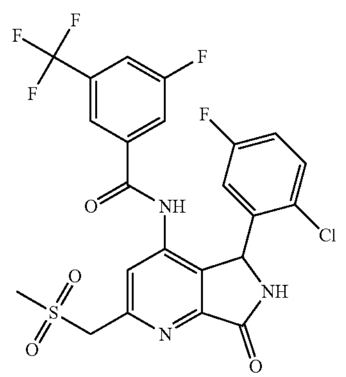 [SMILES: CS(=O)(=O)Cc1cc(NC(=O)c2cc(F)cc(C(F)(F)F)c2)c2c(n1)C(=O)NC2c1cc(F)ccc1Cl] | CS(=O)(=O)Cc1cc(NC(=O)c2cc(F)cc(c2)C(F)(F)F)c2C(NC(=O)c2n1)c1cc(F)ccc1Cl | 1H NMR (400 MHz, DMSO-d6) 10.93 (br. s, 1H), 9.59 (s, 1H), 7.98 (d, 8.2 Hz, 1H), 7.74 (d, 8.9 Hz, 1H), 7.63 (s, 1H), 7.60 (s, 1H), 7.35 (dd, 8.9, 5.2 Hz, 1H), 7.11 (td, 8.1, 3.1 Hz, 1H), 6.86 (br. s, 1H), 6.02 (br. s, 1H), 4.88 (s, 2H), 3.12 (s, 3H) | 560.1 | A | |
| I-1645 | 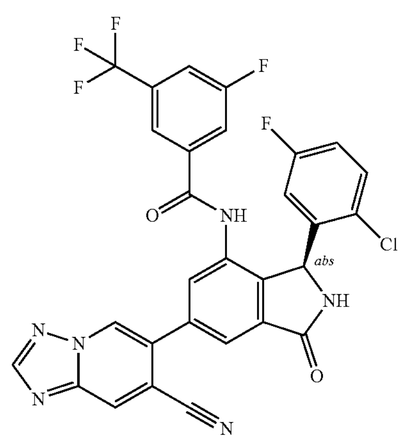 [SMILES: N#Cc1cc2ncnn2cc1-c1cc(NC(=O)c2cc(F)cc(C(F)(F)F)c2)c2c(c1)C(=O)N[C@@H]2c1cc(F)ccc1Cl] | Fc1ccc(C1)c(c1)[C@H]1NC(=O)c2cc(cc(NC(=O)c3cc(F)cc(c3)C(F)(F)F)c12)-c1cn2ncnc2cc1C#N | ¹H NMR (500 MHz, DMSO-d₆) δ 10.69 (s, 1H), 9.41 (d, J = 1.0 Hz, 1H), 9.31 (s, 1H), 8.85 (d, J = 0.9 Hz, 1H), 8.81 (s, 1H), 7.96 (d, J = 20.0 Hz, 2H), 7.76 (s, 2H), 7.68 (s, 1H), 7.35 (dd, J = 8.9, 5.2 Hz, 1H), 7.12 (s, 2H), 6.10 (s, 1H). | 609.2 | D | |

TABLE 2-continued

Representative Compounds of the Invention with Bioactivity Data.

| Ex. No. | Structure | SMILES | $^1$H NMR | MS | ADP-Glo IC$_{50}$ | MCF 10A IC$_{50}$ |
|---|---|---|---|---|---|---|
| I-1646 | 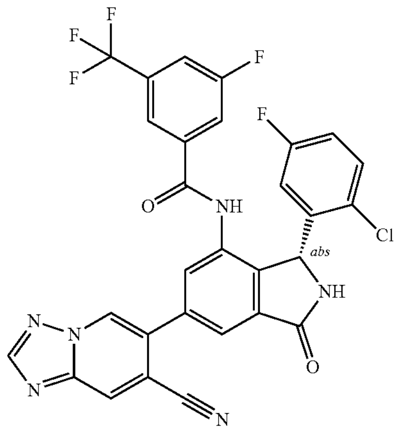 [SMILES: N#Cc1cc2ncnn2cc1-c1cc(NC(=O)c2cc(F)cc(C(F)(F)F)c2)c2c(c1)C(=O)N[C@H]2c1cc(F)ccc1Cl] | Fc1ccc(C1)c(c1)[C@@H]1NC(=O)c2cc(cc(NC(=O)c3cc(F)cc(c3)C(F)(F)F)c12)-c1cn2ncnc2cc1C#N | $^1$H NMR (500 MHz, DMSO-d$_6$) δ 10.69 (s, 1H), 9.41 (d, J = 1.0 Hz, 1H), 9.31 (s, 1H), 8.85 (d, J = 0.9 Hz, 1H), 8.81 (s, 1H), 7.96 (d, J = 20.0 Hz, 2H), 7.76 (s, 2H), 7.68 (s, 1H), 7.35 (dd, J = 8.9, 5.2 Hz, 1H), 7.12 (s, 2H), 6.10 (s, 1H). | 609.2 | A | |
| I-1647 | 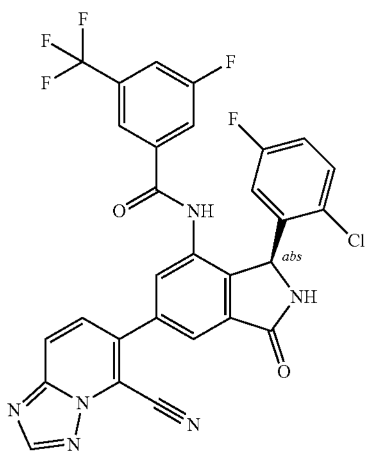 [SMILES: N#Cc1c(-c2cc(NC(=O)c3cc(F)cc(C(F)(F)F)c3)c3c(c2)C(=O)N[C@@H]3c2cc(F)ccc2Cl)ccc2ncnn12] | Fc1ccc(C1)c(c1)[C@H]1NC(=O)c2cc(cc(NC(=O)c3cc(F)cc(c3)C(F)(F)F)c12)-c1ccc2ncnn2c1C#N | $^1$H NMR (500 MHz, DMSO-d$_6$) δ 10.71 (s, 1H), 9.33 (s, 1H), 8.80 (s, 1H), 8.34 (d, J = 9.2 Hz, 1H), 8.07 (s, 1H), 7.97 (t, J = 9.9 Hz, 2H), 7.83 (s, 1H), 7.75 (d, J = 9.2 Hz, 1H), 7.68 (s, 1H), 7.35 (dd, J = 8.8, 5.1 Hz, 1H), 7.13 (d, J = 8.0 Hz, 1H). | 609.1 | B | B |
| I-1648 | 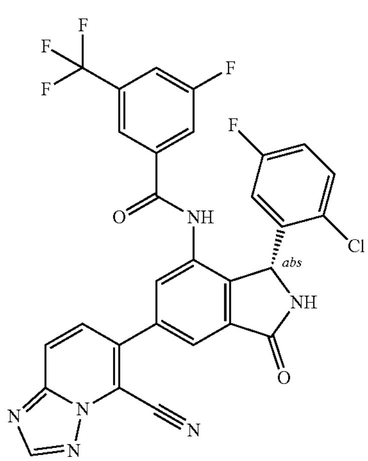 [SMILES: N#Cc1c(-c2cc(NC(=O)c3cc(F)cc(C(F)(F)F)c3)c3c(c2)C(=O)N[C@H]3c2cc(F)ccc2Cl)ccc2ncnn12] | Fc1ccc(C1)c(c1)[C@@H]1NC(=O)c2cc(cc(NC(=O)c3cc(F)cc(c3)C(F)(F)F)c12)-c1ccc2ncnn2c1C#N | $^1$H NMR (500 MHz, DMSO-d$_6$) δ 10.71 (s, 1H), 9.33 (s, 1H), 8.80 (s, 1H), 8.34 (d, J = 9.2 Hz, 1H), 8.07 (s, 1H), 7.97 (t, J = 9.9 Hz, 2H), 7.83 (s, 1H), 7.75 (d, J = 9.2 Hz, 1H), 7.68 (s, 1H), 7.35 (dd, J = 8.8, 5.1 Hz, 1H), 7.13 (d, J = 8.0 Hz, 1H). | 609.1 | A | A |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-1649 | 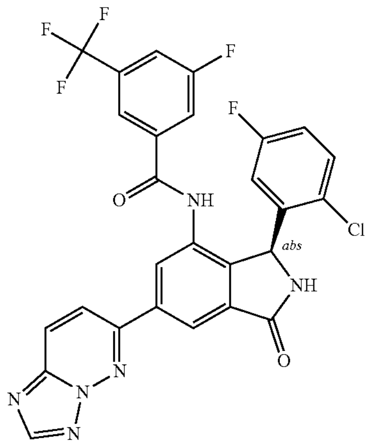 [SMILES: O=C(Nc1cc(-c2ccc3ncnn3n2)cc2c1[C@@H](c1cc(F)ccc1Cl)NC2=O)c1cc(F)cc(C(F)(F)F)c1] | Fc1ccc(C1)c(c1)[C@H]1NC(=O)c2cc(cc(NC(=O)c3cc(F)cc(c3)C(F)(F)F)c12)-c1ccc2ncnn2n1 | 1H NMR (500 MHz, DMSO) δ 10.71 (s, 1H), 9.31 (s, 1H), 8.74 (s, 1H), 8.59 (d, J = 9.5 Hz, 1H), 8.45 (d, J = 9.5 Hz, 1H), 8.41 (d, J = 1.6 Hz, 1H), 8.32 (d, J = 1.6 Hz, 1H), 7.96 (d, J = 8.3 Hz, 1H), 7.79 (d, J = 9.0 Hz, 1H), 7.72 (s, 1H), 7.34 (dd, J = 8.9, 5.2 Hz, 1H), 7.11 (td, J = 8.4, 3.0 Hz, 1H), 6.13 (s, 1H) | 585.2 | D | |
| I-1650 | 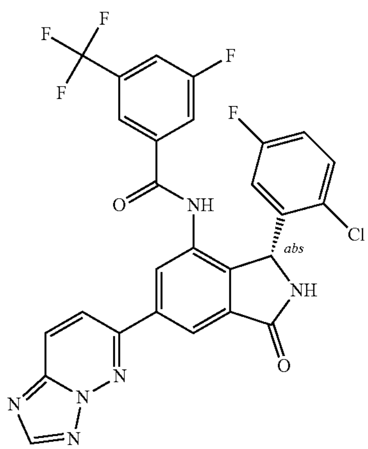 [SMILES: O=C(Nc1cc(-c2ccc3ncnn3n2)cc2c1[C@H](c1cc(F)ccc1Cl)NC2=O)c1cc(F)cc(C(F)(F)F)c1] | Fc1ccc(C1)c(c1)[C@@H]1NC(=O)c2cc(cc(NC(=O)c3cc(F)cc(c3)C(F)(F)F)c12)-c1ccc2ncnn2n1 | 1H NMR (500 MHz, DMSO) δ 10.71 (s, 1H), 9.31 (s, 1H), 8.74 (s, 1H), 8.59 (d, J = 9.5 Hz, 1H), 8.45 (d, J = 9.5 Hz, 1H), 8.41 (d, J = 1.6 Hz, 1H), 8.32 (d, J = 1.7 Hz, 1H), 7.96 (d, J = 8.3 Hz, 1H), 7.79 (d, J = 8.9 Hz, 1H), 7.72 (s, 1H), 7.34 (dd, J = 8.9, 5.1 Hz, 1H), 7.11 (td, J = 8.4, 3.1 Hz, 1H), 6.08 (s, 1H). | 585.2 | A | |
| I-1651 | 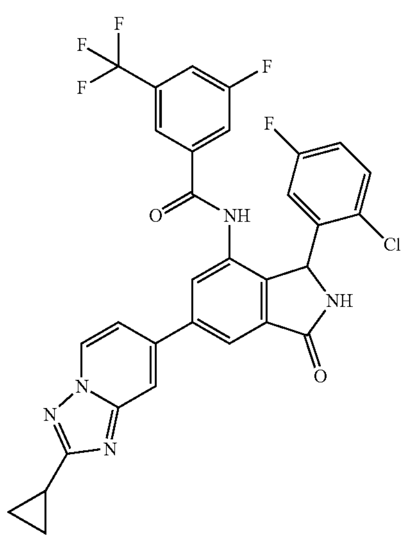 [SMILES: O=C(Nc1cc(-c2ccn3nc(C4CC4)nc3c2)cc2c1C(c1cc(F)ccc1Cl)NC2=O)c1cc(F)cc(C(F)(F)F)c1] | Fc1ccc(C1)c(c1)C1NC(=O)c2cc(cc(NC(=O)c3cc(F)cc(c3)C(F)(F)F)c12)-c1ccn2nc(nc2c1)C1CC1 | | 624.24 | A | |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-1652 | 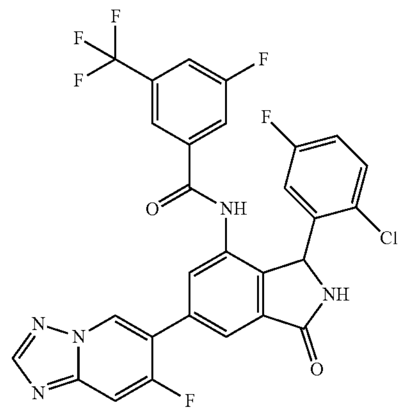 [SMILES: O=C(Nc1cc(-c2cn3ncnc3cc2F)cc2c1C(c1cc(F)ccc1Cl)NC2=O)c1cc(F)cc(C(F)(F)F)c1] | Fc1ccc(C1)c(c1)C1NC(=O)c2cc(cc(NC(=O)c3cc(F)cc(c3)C(F)(F)F)c12)-c1cn2ncnc2cc1F | | 602.18 | A | |
| I-1653 | 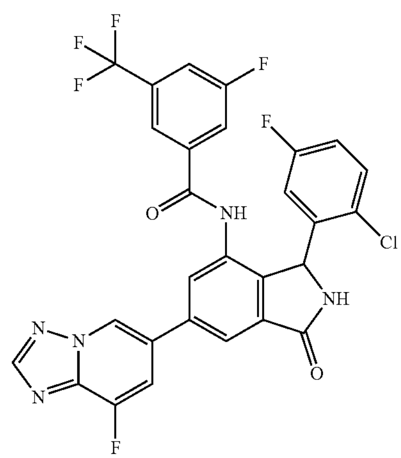 [SMILES: O=C(Nc1cc(-c2cc(F)c3ncnn3c2)cc2c1C(c1cc(F)ccc1Cl)NC2=O)c1cc(F)cc(C(F)(F)F)c1] | Fc1ccc(C1)c(c1)C1NC(=O)c2cc(cc(NC(=O)c3cc(F)cc(c3)C(F)(F)F)c12)-c1cc(F)c2ncnn2c1 | 1H NMR (400 MHz, DMSO) 10.65 (s, 1H), 9.39 (d, 7.1 Hz, 1H), 9.29 (s, 1H), 8.58 (s, 1H), 8.13 (s, 0.5H), 8.00 (s, 0.5H), 7.96 (d, 5.6 Hz, 2H), 7.75 (d, 8.7 Hz, 2H), 7.68 (s, 1H), 7.34 (dd, 8.9, 5.1 Hz, 1H), 7.12 (t, 6.8 Hz, 2H), 6.05 (s, 1H). | 602.13 | A | |
| I-1654 | 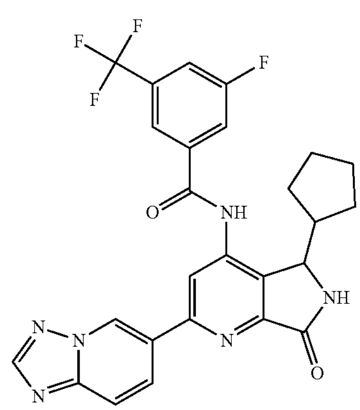 [SMILES: O=C(Nc1cc(-c2ccc3ncnn3c2)nc2c1C(C1CCCC1)NC2=O)c1cc(F)cc(C(F)(F)F)c1] | Fc1cc(cc(c1)C(F)(F)F)C(=O)Nc1cc(nc2C(=O)NC(C3CCCC3)c12)-c1ccc2ncnn2c1 | | 98 | E | |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-1655 | 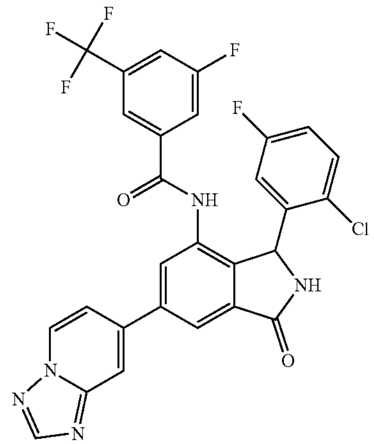 [SMILES: O=C(Nc1cc(-c2ccn3ncnc3c2)cc2c1C(c1cc(F)ccc1Cl)NC2=O)c1cc(F)cc(C(F)(F)F)c1] | Oc1ccc(F)cc1C1NC(=O)c2cc(cc(NC(=O)c3cc(F)cc(c3)C(F)(F)F)c12)-c1ccn2ncnc2c1 | | 566.22 | D | |
| I-1656 | 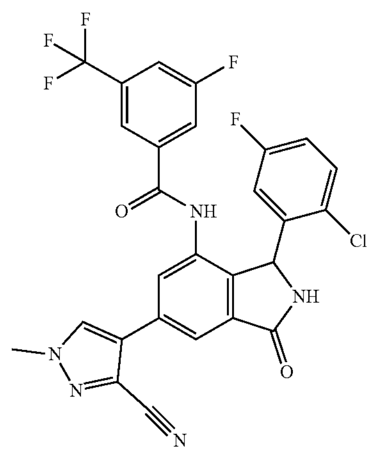 [SMILES: Cn1cc(-c2cc(NC(=O)c3cc(F)cc(C(F)(F)F)c3)c3c(c2)C(=O)NC3c2cc(F)ccc2Cl)c(C#N)n1] | Cn1cc(c(n1)C#N)-c1cc2C(=O)NC(c2c(NC(=O)c2cc(F)cc(c2)C(F)(F)F)c1)c1cc(F)ccc1Cl | | 572.4 | A | |
| I-1657 | 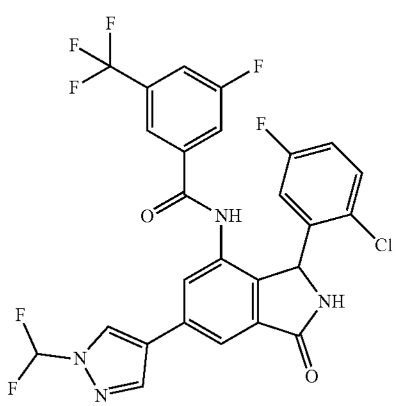 [SMILES: O=C(Nc1cc(-c2cnn(C(F)F)c2)cc2c1C(c1cc(F)ccc1Cl)NC2=O)c1cc(F)cc(C(F)(F)F)c1] | FC(F)n1cc(cn1)-c1cc2C(=O)NC(c2c(NC(=O)c2cc(F)cc(c2)C(F)(F)F)c1)c1cc(F)ccc1Cl | | 583.5 | A | |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-1658 | 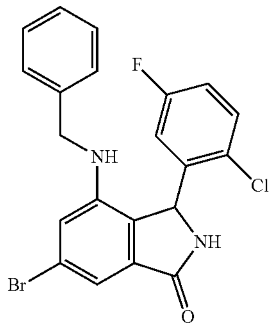 [SMILES: O=C1NC(c2cc(F)ccc2Cl)c2c(NCc3ccccc3)cc(Br)cc21] | Fc1ccc(C1)c(c1)C1NC(=O)c2cc(Br)cc(NCc3ccccc3)c12 | NMR (400 MHz, DMSO-d6) 9.10 (s, 1H), 7.57 (dd, 8.7, 5.1 Hz, 1H), 7.34-7.28 (m, 1H), 7.27-7.19 (m, 3H), 7.08-7.03 (m, 3H), 6.79 (d, 1.4 Hz, 1H), 5.86 (s, 1H), 5.65 (br s, 1H), 4.36-4.21 (m,, 2H). | 445 | E | |
| I-1659 | 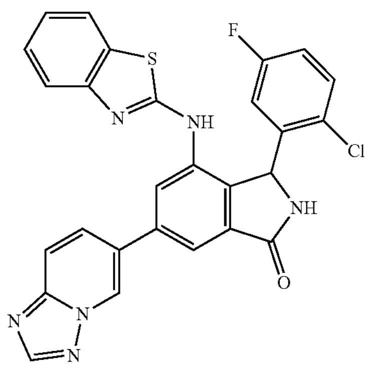 [SMILES: O=C1NC(c2cc(F)ccc2Cl)c2c(Nc3nc4ccccc4s3)cc(-c3ccc4ncnn4c3)cc21] | Fc1ccc(C1)c(c1)C1NC(=O)c2cc(cc(Nc3nc4cccc4s3)c12)-c1ccc2ncnn2c1 | NMR (400 MHz, DMSO-d6) 10.08 (br s, 1H), 9.48 (s, 1H), 9.25 (s, 1H), 8.58 (s, 1H), 8.14 (dd, 9.3, 1.8 Hz, 1H), 8.08 (br s, 1H), 8.00 (s, 1H), 7.98 (d. 9.3 Hz, 1H), 7.71 (br s, 1H), 7.53 (br s, 1H), 7.36 (dd, 8.8, 5.2 Hz, 1H), 7.29 (t, 7.7 Hz, 1H), 7.16-7.06 (m, 2H), 6.53 (br s, 1H), 6.26 (br s, 1H). | 525.2 | B | |
| I-1660 | 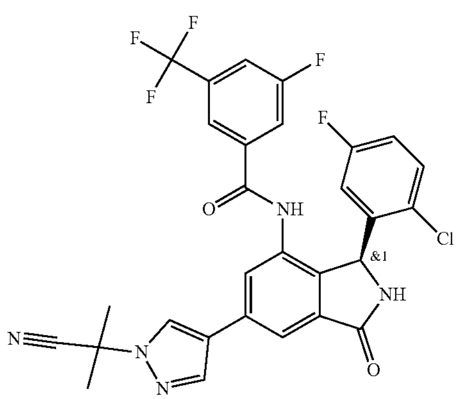 [SMILES: CC(C)(C#N)n1cc(-c2cc(NC(=O)c3cc(F)cc(C(F)(F)F)c3)c3c(c2)C(=O)N[C@@H]3c2cc(F)ccc2Cl)cn1] | CC(C)(C#N)n1cc(cn1)-c1cc2C(=O)N[C@@H](c2c(NC(=O)c2cc(F)cc(c2)C(F)(F)F)c1)c1cc(F)ccc1Cl | (400 MHz, DMSO-D6) 10.57 (s, 1 H), 9.16 (br s, 1 H), 8.77 (s, 1 H), 8.25 (s, 1 H), 8.04 (s, 1 H), 7.96 (d, 8.3 Hz, 1 H), 7.83-7.74 (m, 2 H), 7.72 (s, 1 H), 7.32 (dd, 8.9, 5.2 Hz, 1 H), 7.09 (td, 8.5, 2.8 Hz, 1 H), 6.57 (br s, 1 H), 5.98 (br s, 1 H), 2.03 (s, 6 H). | 598.3 | C | |
| I-1661 | 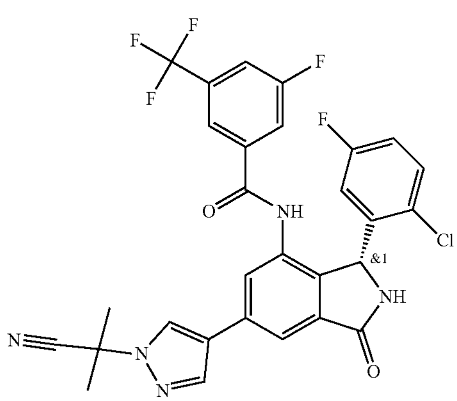 [SMILES: CC(C)(C#N)n1cc(-c2cc(NC(=O)c3cc(F)cc(C(F)(F)F)c3)c3c(c2)C(=O)N[C@H]3c2cc(F)ccc2Cl)cn1] | CC(C)(C#N)n1cc(cn1)-c1cc2C(=O)N[C@H](c2c(NC(=O)c2cc(F)cc(c2)C(F)(F)F)c1)c1cc(F)ccc1Cl | (400 MHz, DMSO-D6) 10.57 (s, 1 H), 9.16 (br s, 1 H), 8.77 (s, 1 H), 8.25 (s, 1 H), 8.04 (s, 1 H), 7.96 (d, 8.3 Hz, 1 H), 7.83-7.74 (m, 2 H), 7.72 (s, 1 H), 7.32 (dd, 8.9, 5.2 Hz, 1 H), 7.09 (td, 8.5, 2.8 Hz, 1 H), 6.57 (br s, 1 H), 5.98 (br s, 1 H), 2.03 (s, 6 H). | 598.3 | A | |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-1662 | 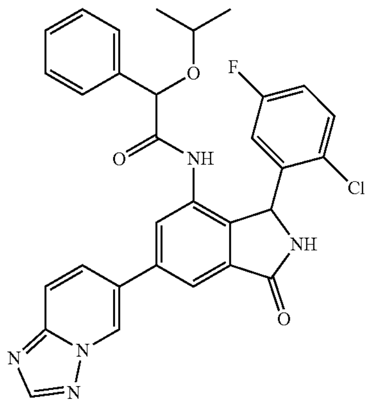 [SMILES: CC(C)OC(C(=O)Nc1cc(-c2ccc3ncnn3c2)cc2c1C(c1cc(F)ccc1Cl)NC2=O)c1ccccc1] | CC(C)OC(C(=O)Nc1cc(cc2C(=O)NC(c12)c1cc(F)ccc1Cl)-c1ccc2ncnn2c1)c1ccccc1 | NMR (400 MHz, DMSO-d6) 9.60-9.53 (m, 1H), 9.45-9.40 (m, 1H), 9.31-9.21 (m, 1H), 8.57 (s, 1H), 8.49 (s, 2H), 8.15 (d, 1.4 Hz, 1H), 8.09-8.03 (m, 1H), 8.02-7.99 (m, 1H), 7.99-7.94 (m, 1H), 7.35-7.26 (m, 4H), 7.25-7.19 (m, 1H), 7.01 (br s, 1H), 6.27 (br s, 1H), 4.87-4.80 (m, 1H), 3.19-3.07 (m, 1H), 1.06-0.99 (m, 6H). | 570 | D | |
| I-1663 | 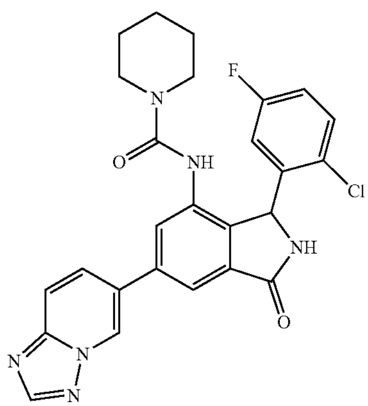 [SMILES: O=C1NC(c2cc(F)ccc2Cl)c2c(NC(=O)N3CCCCC3)cc(-c3ccc4ncnn4c3)cc21] | Fc1ccc(C1)c(c1)C1NC(=O)c2cc(cc(NC(=O)N3CCCCC3)c12)-c1ccc2ncnn2c1 | 1H-NMR (400 MHz, DMSO-d6) 9.39-9.38 (m, 1H), 9.13 (br. s, 1H), 8.58-8.55 (m, 2H), 8.06 (dd, 9.3, 1.7 Hz, 1H), 7.97 (d, 9.3 Hz, 1H), 7.88 (d, 1.5 Hz, 1H), 7.69 (d, 1.4 Hz, 1H), 7.54-7.48 (m, 1H), 7.25 (app. td, 8.3, 3.0 Hz, 1H), 6.63 (br. s, 1H), 6.11 (br. s, 1H), 3.21 (ddd, 11.7, 7.2, 3.1 Hz, 2H), 3.07 (ddd, 12.6, 7.0, 3.3 Hz, 2H), 1.49-1.42 (m, 2H), 1.38-1.28 (m, 2H), 1.21-1.11 (m, 2H). | 505.3 | D | |
| I-1664 | 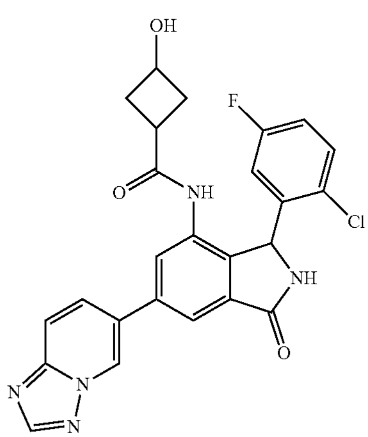 [SMILES: O=C1NC(c2cc(F)ccc2Cl)c2c(NC(=O)C3CC(O)C3)cc(-c3ccc4ncnn4c3)cc21] | OC1CC(C1)C(=O)Nc1cc(c2C(=O)NC(c12)c1cc(F)ccc1Cl)-c1ccc2ncnn2c1 | NMR (400 MHz, DMSO-d6) 9.77 (s, 1H), 9.45-9.43 (m, 1H), 9.22 (br. s, 1H), 8.57 (s, 1H), 8.09-8.07 (m, 1H), 8.01-7.99 (m, 1H), 7.97 (dd, 3.0, 0.7 Hz, 1H), 7.78 (d, 1.6 Hz, 1H), 7.56-7.46 (m, 1H), 7.29-7.20 (m, 1H), 6.61 (br. s, 1H), 6.16 (br. s, 1H), 5.05 (d, 6.3 Hz, 1H), 4.17-4.03 (m, 1H), 2.81-2.74 (m, 1H), 2.39-2.18 (m, 1H), 2.07-2.15 (m, 1H), 1.93-1.82 (m, 2H). | 492 | E | |

TABLE 2-continued

Representative Compounds of the Invention with Bioactivity Data.

| Ex. No. | Structure | SMILES | $^1$H NMR | MS | ADP-Glo IC$_{50}$ | MCF 10A IC$_{50}$ |
|---|---|---|---|---|---|---|
| I-1665 | 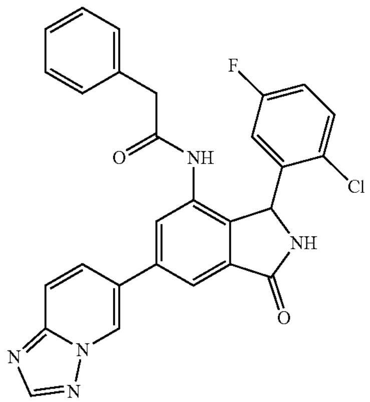 [SMILES: O=C(Cc1ccccc1)Nc1cc(-c2ccc3ncnn3c2)cc2c1C(c1cc(F)ccc1Cl)NC2=O] | Fc1ccc(C1)c(c1)C1NC(=O)c2cc(cc(NC(=O)Cc3ccccc3)c12)-c1ccc2ncnn2c1 | NMR (400 MHz, DMSO-d6) 9.46-9.43 (m, 1H), 8.57 (s, 1H), 8.09 (dd, 9.3, 1.8 Hz, 1H), 8.00 (d, 1.5 Hz, 1H), 7.96 (dd, 9.3, 0.7 Hz, 1H), 7.90 (d, 1.6 Hz, 1H), 7.54-7.43 (m, 1H), 7.34-7.15 (m, 5H), 7.04 (br d, 6.5 Hz, 2H), 6.63 (br s, 1H), 6.12 (br s, 1H), 3.45-3.33 (m, 2H). | 512 | E | |
| I-1666 | 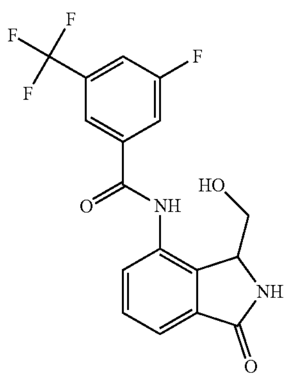 [SMILES: O=C(Nc1cccc2c1C(CO)NC2=O)c1cc(F)cc(C(F)(F)F)c1] | OCC1NC(=O)c2ccc(NC(=O)c3cc(F)cc(c3)C(F)(F)F)c12 | NMR (400 MHz, DMSO-d6) 11.08 (br. s, 1H), 8.71 (s, 1H), 8.13 (s, 1H), 8.08 (dd, 7.6, 1.2 Hz, 1H), 8.07 (br. d, 8.4 Hz, 1H), 8.03 (br. d, 8.5 Hz, 1H), 7.57-7.49 (m, 2H), 6.21 (br. s, 1H), 4.83 (dd, 6.4, 5.7 Hz, 1H), 3.73 (dd, 10.5, 4.9 Hz, 1H), 3.49 (dd, 10.4, 7.2 Hz, 1H). | 369.2 | E | |
| I-1667 | 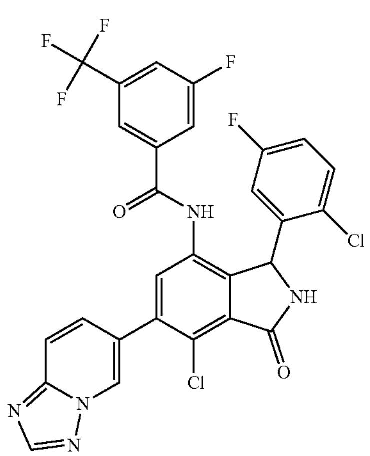 [SMILES: O=C(Nc1cc(-c2ccc3ncnn3c2)c(Cl)c2c1C(c1cc(F)ccc1Cl)NC2=O)c1cc(F)cc(C(F)(F)F)c1] | Fc1ccc(C1)c(c1)C1NC(=O)c2c1c(NC(=O)c1cc(F)cc(c1)C(F)(F)F)cc(c2Cl)-c1ccc2ncnn2c1 | (400 MHz, DMSO-D6) 10.99-10.14 (br s, 1 H), 9.38 (br s, 1 H), 9.18 (s, 1 H), 8.60 (s, 1 H), 7.99 (app d, 9.2 Hz, 1 H), 7.98-7.92 (m, 1 H), 7.83 (dd, 9.2, 1.6 Hz, 1 H), 7.80-7.68 (m, 2 H), 7.66 (s, 1 H), 7.36 (dd, 8.9, 5.1 Hz, 1 H), 7.13 (td, 8.4, 2.9 Hz, 1 H), 6.77 (br s, 1 H), 6.05 (br s, 1 H). | 616.2 | A | |

TABLE 2-continued

Representative Compounds of the Invention with Bioactivity Data.

| Ex. No. | Structure | SMILES | $^1$H NMR | MS | ADP-Glo IC$_{50}$ | MCF 10A IC$_{50}$ |
|---|---|---|---|---|---|---|
| I-1668 | 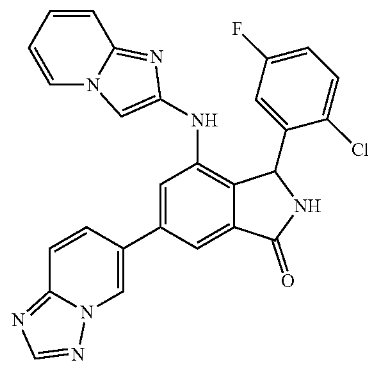 [SMILES: O=C1NC(c2cc(F)ccc2Cl)c2c(Nc3cn4ccccc4n3)cc(-c3ccc4ncnn4c3)cc21] | Fc1ccc(C1)c(c1)CNC(=O)c2cc(cc(Nc3cn4cccc4n3)c12)-c1ccc2ncnn2c1 | 1H NMR (400 MHz, DMSO-d6) 9.40 (s, 1H), 9.12 (s, 1H), 8.57 (s, 1H), 8.37 (d, 6.7 Hz, 1H), 8.11 (br. s, 1H), 8.08 (dd, 9.3, 1.8 Hz, 1H), 8.00 (d, 1.5 Hz, 1H), 7.97 (dd, 9.2, 0.9 Hz, 1H), 7.66 (d, 1.0 Hz, 1H), 7.53 (s, 1H), 7.43 (dd, 8.8, 5.2 Hz, 1H), 7.36 (d, 8.9 Hz, 1H), 7.22-7.10 (m, 2H), 6.82 (t, 6.5 Hz., 1H), 6.69 (br. s, 1H), 6.21 (s, 1H) | 510.2 | D | |
| I-1669 | 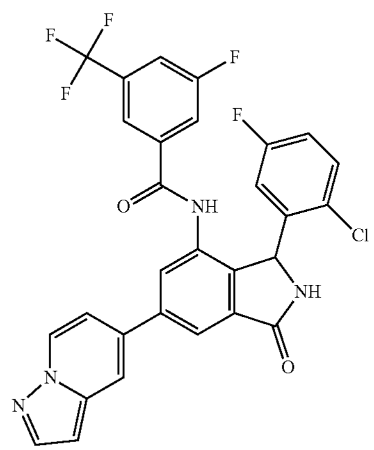 [SMILES: O=C(Nc1cc(-c2ccn3nccc3c2)cc2c1C(c1cc(F)ccc1Cl)NC2=O)c1cc(F)cc(C(F)(F)F)c1] | Fc1ccc(C1)c(c1)CNC(=O)c2cc(cc(NC(=O)c3cc(F)cc(c3)C(F)(F)F)c12)-c1ccn2nccc2c1 | 1H NMR (400 MHz, DMSO) 10.62 (s, 1H), 9.24 (s, 1H), 8.79 (dt, 7.3, 1.0 Hz, 1H), 8.22-8.17 (m, 1H), 8.11-8.04 (m, 2H), 7.95 (d, 9.6 Hz, 2H), 7.77 (d, 9.1 Hz, 1H), 7.71 (s, 1H), 7.36-7.30 (m, 2H), 7.10 (td, 8.4, 3.1 Hz, 1H), 6.70 (dd, 2.3, 0.9 Hz, 1H), 6.06 (s, 1H). | 583.126 | A | |
| I-1670 | 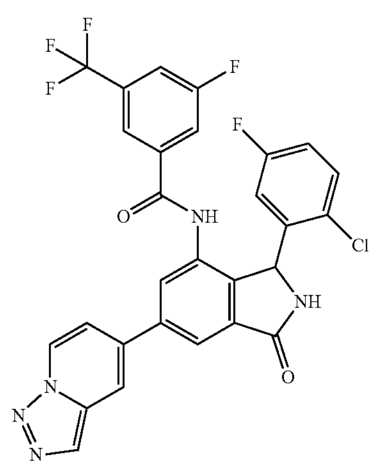 [SMILES: O=C(Nc1cc(-c2ccn3nncc3c2)cc2c1C(c1cc(F)ccc1Cl)NC2=O)c1cc(F)cc(C(F)(F)F)c1] | Fc1ccc(C1)c(c1)CNC(=O)c2cc(cc(NC(=O)c3cc(F)cc(c3)C(F)(F)F)c12)-c1ccn2nncc2c1 | 1H NMR (400 MHz, DMSO) 10.65 (s, 1H), 9.27 (s, 1H), 9.19 (d, 7.4 Hz, 1H), 8.50-8.41 (m, 1H), 8.27 (d, 1.0 Hz, 1H), 8.13 (s, 1H), 7.96 (dd, 13.1, 5.0 Hz, 2H), 7.77 (d, 9.0 Hz, 1H), 7.71 (s, 1H), 7.64 (dd, 7.4, 2.0 Hz, 1H), 7.34 (dd, 8.9, 5.2 Hz, 1H), 7.10 (td, 8.4, 3.0 Hz, 1H), 6.06 (s, 1H). | 584.127 | A | |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-1671 | 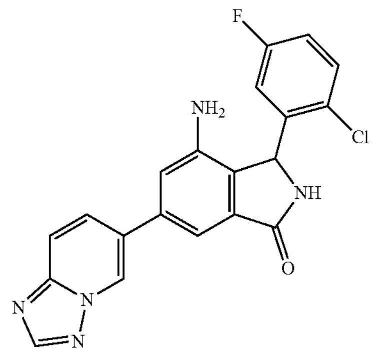 [SMILES: Nc1cc(-c2ccc3ncnn3c2)cc2c1C(c1cc(F)ccc1Cl)NC2=O] | Nc1cc(cc2C(=O)NC(c12)c1cc(F)ccc1Cl)-c1ccc2ncnn2c1 | 1H NMR (500 MHz, DMSO) 9.24 (dd, 1.8, 1.0 Hz, 1H), 8.98 (s, 1H), 8.53 (s, 1H), 7.98 (dd, 9.3, 1.8 Hz, 1H), 7.92 (dd, 9.2, 1.0 Hz, 1H), 7.56 (dd, 8.9, 5.1 Hz, 1H), 7.34 (d, 1.5 Hz, 1H), 7.26 (ddd, 8.8, 7.9, 3.1 Hz, 1H), 7.19 (d, 1.6 Hz, 1H), 6.81 (s, 1H), 5.88 (s, 1H), 5.00 (s, 2H) | 394.26 | E | |
| I-1672 | 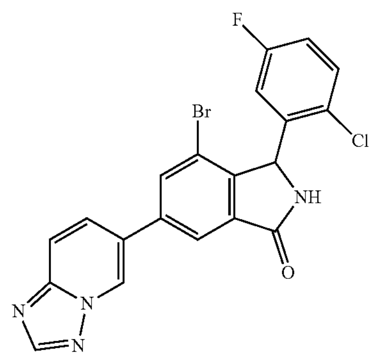 [SMILES: O=C1NC(c2cc(F)ccc2Cl)c2c(Br)cc(-c3ccc4ncnn4c3)cc21] | Fc1ccc(C1)c(c1)C1NC(=O)c2cc(cc(Br)c12)-c1ccc2ncnn2c1 | 1H NMR (500 MHz, DMSO) 9.52 (dd, 1.9, 0.9 Hz, 1H), 9.42 (s, 1H), 8.56 (s, 1H), 8.28 (s, 1H), 8.20-8.13 (m, 2H), 7.94 (dd, 9.2, 0.9 Hz, 1H), 7.62 (s, 1H), 7.28 (td, 8.4, 3.0 Hz, 1H), 6.55 (s, 1H), 6.09 (s, 1H). | 457.12 | E | |
| I-1673 | 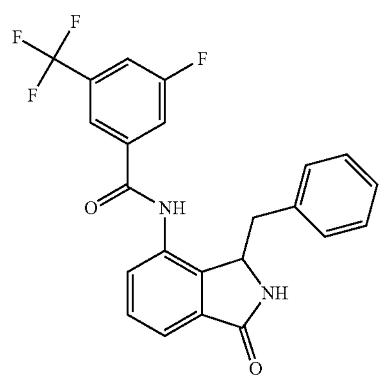 [SMILES: O=C(Nc1cccc2c1C(Cc1ccccc1)NC2=O)c1cc(F)cc(C(F)(F)F)c1] | Fc1cc(cc(c1)C(F)(F)F)C(=O)Nc1ccc2C(=O)NC(Cc3ccccc3)c12 | NMR (400 MHz, DMSO-d6) 10.87 (s, 1H), 8.65 (s, 1H), 8.23 (s), 8.17 (d, 8.9 Hz, 1H), 8.01 (d, 8.2 Hz, 1H), 7.55 (dd, 7.8, 1.0 Hz, 1H), 7.42 (t, 7.6 Hz, 1H), 7.33 (dd, 7.4, 0.9 Hz, 1H), 7.00 (m, 3H), 6.91-6.87 (m, 2H), 5.10 (t, 4.6 Hz, 1H), 3.03 (dd, 13.7, 4.1 Hz, 1H), 2.81 (dd, 13.8, 4.7 Hz, 1H). | 429 | E | |
| I-1674 | 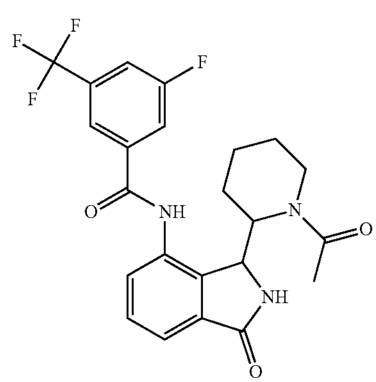 [SMILES: CC(=O)N1CCCCC1C1NC(=O)c2cccc(NC(=O)c3cc(F)cc(C(F)(F)F)c3)c21] | CC(=O)N1CCCCC1C1NC(=O)c2ccc(NC(=O)c3cc(F)cc(c3)C(F)(F)F)c12 | (400 MHz, DMSO-d6) 10.67 (br s, 1H), 8.88 (s, 1H), 8.25 (s, 1H), 8.21 (d, 9.8 Hz, 1H), 7.98 (d, 8.2 Hz, 1H), 7.82 (d, 6.1 Hz, 1H), 7.65-7.52 (m, 2H), 5.11 (s, 1H), 4.79-4.70 (m, 1H), 3.74-3.54 (m, 2H), 1.98 (s, 3H), 1.61-1.36 (m, 4H), 1.29-1.18 (m, 1H), 1.03-0.91 (m, 1H) | 464.3 | E | |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-1675 | 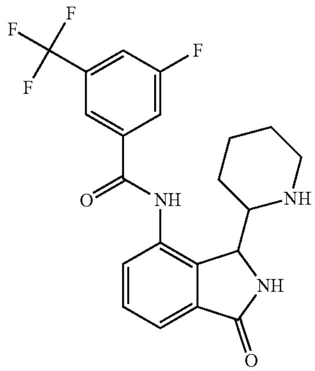 [SMILES: O=C(Nc1cccc2c1C(C1CCCCN1)NC2=O)c1cc(F)cc(C(F)(F)F)c1] | Fc1cc(cc(c1)C(F)(F)F)C(=O)Nc1cccc2C(=O)NC(C3CCCN3)c12 | (400 MHz, DMSO-d6) 8.87 (s, 1H), 8.76 (s, 1H), 8.52 (d, 8.0 Hz, 0.5H), 8.44 (d, 7.2 Hz, 0.5H), 8.06-7.95 (m, 3H), 7.52 (t, 7.7 Hz, 1H), 7.43 (d, 6.7 Hz, 1H), 4.74 (s, 0.5H), 4.53 (d, 7.1 Hz, 0.5H), 3.08-2.98 (m, 0.5H), 2.72 (br. d, 10.9 Hz, 0.5H), 2.65-2.60 (m, 0.5H), 2.59-2.54 (m, 1H), 1.83-1.74 (m, 0.5H), 1.74-1.66 (m, 0.5H), 1.60-1.54 (m, 0.5H), 1.46 (br. d, 9.7 Hz, 1H), 1.40-1.07 (m, 4H) | 422.3 | D | |
| I-1676 | 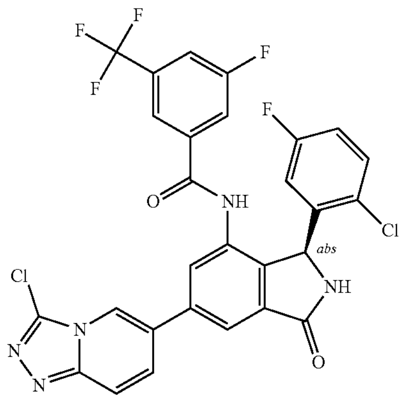 [SMILES: O=C(Nc1cc(-c2ccc3nnc(Cl)n3c2)cc2c1[C@@H](c1cc(F)ccc1Cl)NC2=O)c1cc(F)cc(C(F)(F)F)c1] | Fc1ccc(C1)c(c1)[C@H]1NC(=O)c2cc(cc(NC(=O)c3cc(F)cc(c3)C(F)(F)F)c12)-c1ccc2nnc(Cl)n2c1 | | 618.09 | B | |
| I-1677 | 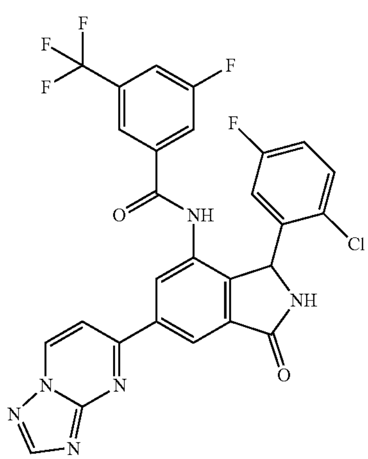 [SMILES: O=C(Nc1cc(-c2ccn3ncnc3n2)cc2c1C(c1cc(F)ccc1Cl)NC2=O)c1cc(F)cc(C(F)(F)F)c1] | Fc1ccc(C1)c(c1)C1NC(=O)c2cc(cc(NC(=O)c3cc(F)cc(c3)C(F)(F)F)c12)-c1ccn2ncnc2n1 | | 585.13 | A | |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-1678 | 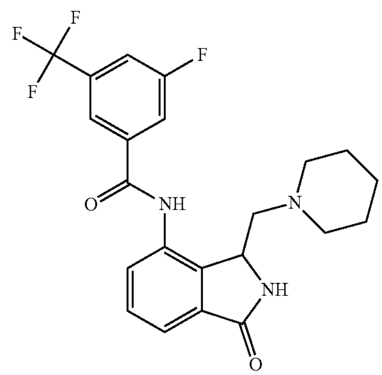 [SMILES: O=C(Nc1cccc2c1C(CN1CCCCC1)NC2=O)c1cc(F)cc(C(F)(F)F)c1] | Fc1cc(cc (c1)C(F) (F)F)C(= O)Nc1cc cc2C(=O) NC(CN3 CCCCC3) c12 | NMR (400 MHz, DMSO-d6) 11.28 (s, 1H), 8.68 (s, 1H), 8.14-8.06 (m, 3H), 8.03 (br. d, 8.6 Hz, 1H), 7.56-7.48 (m, 2H), 4.96 (t, 6.1 Hz, 1H), 2.48 (submerged d, 6.3 Hz, 2H), 2.44-2.24 (m, 4H), 1.21-1.13 (m, 6H). | 436.2 | E | |
| I-1679 | 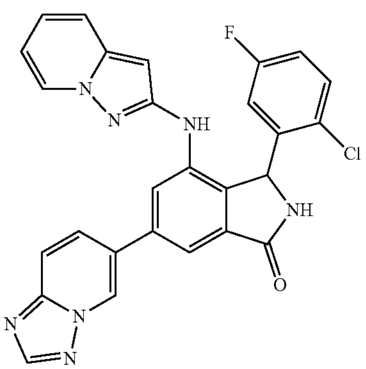 [SMILES: O=C1NC(c2cc(F)ccc2Cl)c2c(Nc3cc4ccccn4n3)cc(-c3ccc4ncnn4c3)cc21] | Fc1ccc(C 1)c(c1)C1 NC(=O)c 2cc(cc(N c3cc4ccc cn4n3)c1 2)-c1ccc2nc nn2c1 | 1H NMR (400 MHz, DMSO-d6) 9.40 (s, 1H), 9.14 (s, 1H), 8.57 (s, 1H), 8.51-8.32 (m, 2H), 8.08 (td, 4.8, 1.8 Hz, 2H), 7.97 (d, 9.2 Hz, 1H), 7.72 (d, 1.5 Hz, 1H), 7.42-7.35 (m, 2H), 7.19-7.08 (m, 2H), 6.67 (td, 6.9, 1.3 Hz, 1H), 6.59 (br. s, 1H), 6.28 (s, 1H), 5.95 (s, 1H) | 510.2 | E | |
| I-1680 | 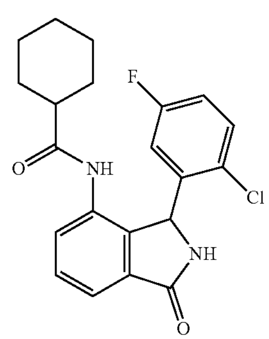 [SMILES: O=C1NC(c2cc(F)ccc2Cl)c2c(NC(=O)C3CCCCC3)cccc21] | Fc1ccc(C 1)c(c1)C1 NC(=O)c 2cccc(N C(=O)C3 CCCCC3) c12 | | 387.2 | D | |
| I-1681 | 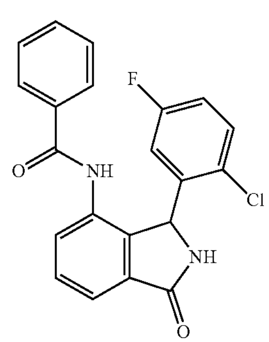 [SMILES: O=C(Nc1cccc2c1C(c1cc(F)ccc1Cl)NC2=O)c1ccccc1] | Fc1ccc(C 1)c(c1)C1 NC(=O)c 2cccc(N C(=O)c3 ccccc3)c 12 | 1H NMR (400 MHz, DMSO-d6) 10.13 (s, 1H), 9.10 (s, 1H), 7.70-7.49 (m, 6H), 7.43 (t, 7.6 Hz, 2H), 7.34 (dd, 8.9, 5.2 Hz, 1H), 7.12 (td, 8.4, 3.1 Hz, 1H), 6.07 (s, 1H). | 381.15 | E | |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-1682 | 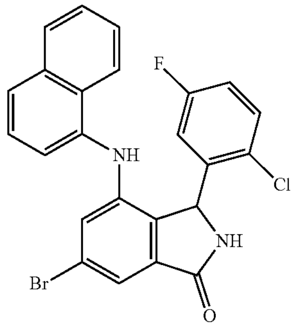 [SMILES: O=C1NC(c2cc(F)ccc2Cl)c2c(Nc3cccc4ccccc34)cc(Br)cc21] | Fc1ccc(C1)c(c1)C1NC(=O)c2cc(Br)cc(Nc3cccc4ccccc34)c12 | NMR (400 MHz, DMSO-d6) 9.09 (br s, 1H), 8.16 (s, 1H), 7.84 (d, 8.2 Hz, 1H), 7.59 (d, 8.2 Hz, 1H), 7.47 (d, 9.1 Hz, 1H), 7.45-7.37 (m, 3H), 7.28 (t, 7.3 Hz, 1H), 7.20 (s, 1H), 7.09-7.02 (m, 1H), 6.97 (d, 7.2 Hz, 1H), 6.93-6.84 (m, 1H), 6.31 (br s, 1H), 5.58 (br s, 1H). | 481.1 | D | |
| I-1683 | 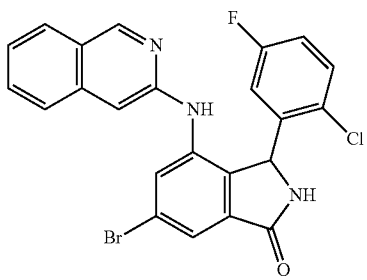 [SMILES: O=C1NC(c2cc(F)ccc2Cl)c2c(Nc3cc4ccccc4cn3)cc(Br)cc21] | Fc1ccc(C1)c(c1)C1NC(=O)c2cc(Br)cc(Nc3cc4ccccc4cn3)c12 | NMR (400 MHz, DMSO-d6) 9.17 (s, 1H), 8.97 (s, 1H), 8.69 (s, 1H), 7.92 (d, 8.2 Hz, 1H), 7.77 (d, 1.0 Hz, 1H), 7.68 (d, 8.4 Hz, 1H), 7.57 (t., 7.1 Hz, 1H), 7.54 (d, 0.9 Hz, 1H), 7.342 (app t, 7.6 Hz, 1H), 7.24 (dd, 8.8, 5.1 Hz, 1H), 7.03 (td, 8.3, 3.0 Hz, 1H), 6.83 (s, 1H), 6.52 (br s, 1H), 6.01 (s, 1H). | 482.1 | E | |
| I-1684 | 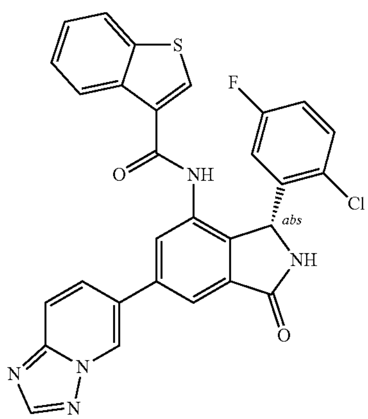 [SMILES: O=C1N[C@@H](c2cc(F)ccc2Cl)c2c(NC(=O)c3csc4ccccc34)cc(-c3ccc4ncnn4c3)cc21] | Fc1ccc(C1)c(c1)[C@@H]1NC(=O)c2cc(cc(NC(=O)c3csc4cccc34)c12)-c1ccc2ncnn2c1 | 1H NMR (400 MHz, DMSO-d6) 10.36 (s, 1H), 9.48 (t, 1.4 Hz, 1H), 9.24 (s, 1H), 8.58 (s, 1H), 8.29-8.22 (m, 1H), 8.15 (dd, 9.3, 1.8 Hz, 1H), 8.10 (d, 1.6 Hz, 1H), 8.06 (q, 3.2, 2.8 Hz, 2H), 8.06-7.96 (m, 2H), 7.49-7.40 (m, 2H), 7.36 (dd, 8.9, 5.2 Hz, 1H), 7.12 (td, 8.4, 3.1 Hz, 1H), 6.72 (s, 1H), 6.21 (s, 1H). | 554.1 | A | A |
| I-1685 | 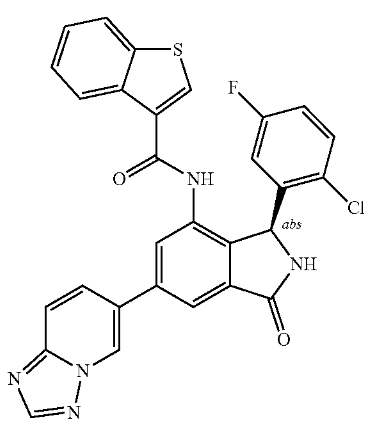 [SMILES: O=C1N[C@H](c2cc(F)ccc2Cl)c2c(NC(=O)c3csc4ccccc34)cc(-c3ccc4ncnn4c3)cc21] | Fc1ccc(C1)c(c1)[C@H]1NC(=O)c2cc(cc(NC(=O)c3csc4ccccc34)c12)-c1ccc2ncnn2c1 | 1H NMR (400 MHz, DMSO-d6) 10.35 (s, 1H), 9.48 (t, 1.4 Hz, 1H), 9.24 (s, 1H), 8.58 (s, 1H), 8.30-8.22 (m, 1H), 8.15 (dd, 9.3, 1.9 Hz, 1H), 8.10 (d, 1.6 Hz, 1H), 8.06 (q, 3.3, 2.7 Hz, 2H), 8.06-7.96 (m, 2H), 7.49-7.40 (m, 2H), 7.36 (dd, 8.9, 5.2 Hz, 1H), 7.12 (td, 8.4, 3.1 Hz, 1H), 6.72 (s, 1H), 6.22 (s, 1H). | 554.1 | D | |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-1686 | 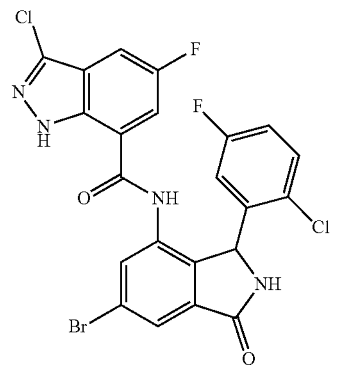 [SMILES: O=C1NC(c2cc(F)ccc2Cl)c2c(NC(=O)c3cc(F)cc4c(Cl)n[nH]c34)cc(Br)cc21] | Fc1ccc(C1)c(c1)C1NC(=O)c2cc(Br)cc(NC(=O)c3cc(F)cc4c(Cl)n[nH]c34)c12 | 1H NMR (400 MHz, DMSO-d6) 11.80 (s, 2H), 10.44 (s, 1H), 9.29 (s, 1H), 7.81 (d, 1.7 Hz, 1H), 7.74 (d, 1.8 Hz, 1H), 7.56 (d, 9.7 Hz, 1H), 7.46 (dd, 8.8, 5.1 Hz, 1H), 7.30 (d, 5.3 Hz, 1H), 7.23 (td, 8.4, 3.1 Hz, 1H), 6.73 (s, 1H), 6.05 (s, 1H). | 550.95 | D | |
| I-1687 | 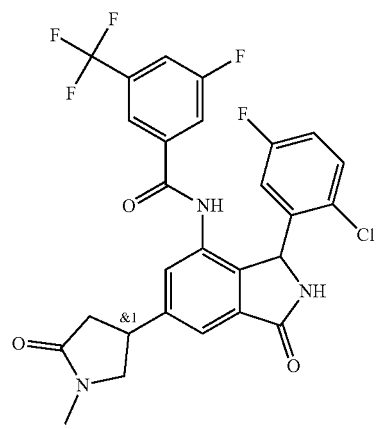 [SMILES: CN1CC(c2cc(NC(=O)c3cc(F)cc(C(F)(F)F)c3)c3c(c2)C(=O)NC3c2cc(F)ccc2Cl)CC1=O] | CN1CC(CC1=O)c1cc2C(=O)NC(c2c(NC(=O)c2cc(F)cc(c2)C(F)(F)F)c1)c1cc(F)ccc1Cl | 1H NMR (400 MHz, DMSO-d6) 10.54 (br s, 1H), 9.15 (s, 1H), 7.95 (d, 8.9 Hz, 1H), 7.73 (d, 8.7 Hz, 1H), 7.65 (s, 1H), 7.62 (s, 1H), 7.42 (s, 1H), 7.31 (dd, 8.8, 5.1 Hz, 1H), 7.09 (td, 8.7, 3.5 Hz, 1H), 5.96 (br s, 1H), 3.83-3.72 (m, 2H), 2.79 (s, 3H), 2.77-2.70 (m, 1H), 2.45-2.37 (m, 2H) | 564.1 | A | |
| I-1688 | 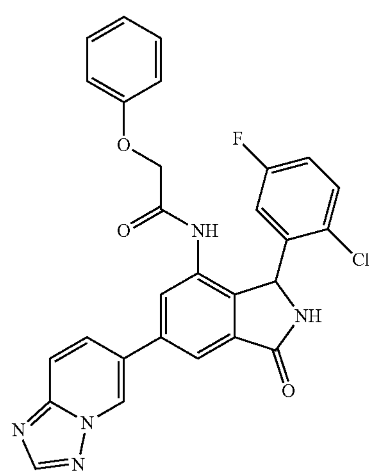 [SMILES: O=C(COc1ccccc1)Nc1cc(-c2ccc3ncnn3c2)cc2c1C(c1cc(F)ccc1Cl)NC2=O] | Fc1ccc(C1)c(c1)C1NC(=O)c2cc(cc(NC(=O)COc3ccccc3)c12)-c1ccc2ncnn2c1 | 1H-NMR (400 MHz, DMSO-d6) 9.90 (s, 1H), 9.45 (dd, 1.7, 0.8 Hz, 1H), 9.24 (br. s, 1H), 8.58 (s, 1H), 8.10 (dd, 9.3, 1.8 Hz, 1H), 8.06 (d, 1.5 Hz, 1H), 8.00-7.96 (m, 2H), 7.50 (dd, 8.3, 5.1 Hz, 1H), 7.32-7.27 (m, 2H), 7.23 (ddd, 8.8, 8.0, 3.1 Hz, 1H), 6.98 (ut, 7.3, 1.0 Hz, 1H), 6.86-6.82 (m, 2H), 6.68 (br. s, 1H), 6.17 (br. s, 1H), 4.42 (s, 2H) | 528.2 | E | |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-1689 | 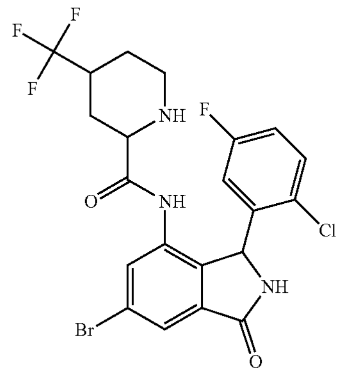 [SMILES: O=C1NC(c2cc(F)ccc2Cl)c2c(NC(=O)C3CC(C(F)(F)F)CCN3)cc(Br)cc21] | Fc1ccc(C1)c(c1)C1NC(=O)c2cc(Br)cc(NC(=O)C3CC(CCN3)C(F)(F)F)c12 | 1H NMR (400 MHz, CD3CN):-' 8.48 (br s, 1H), 8.37 (d, 1.7 Hz, 0.5H), 8.24 (d, 1.7 Hz, 0.5H), 7.73 (d, 1.7 Hz, 0.5H), 7.72 (d, 1.7 Hz, 0.5H), 7.50 (br s, 1H), 7.32 (br s, 1H), 7.13 (td, 8.4, 3.1 Hz, 1H), 6.62 (br s, 1H), 6.09 (br s, 1H), 3.15-2.95 (m, 2H), 2.56 (td, 12.6, 2.9 Hz, 1H), 1.91-1.70 (m, 3H), 1.40-1.29 (m, 1H), 1.21-0.82 (m, 2H). | 534.1 | E | |
| I-1690 | 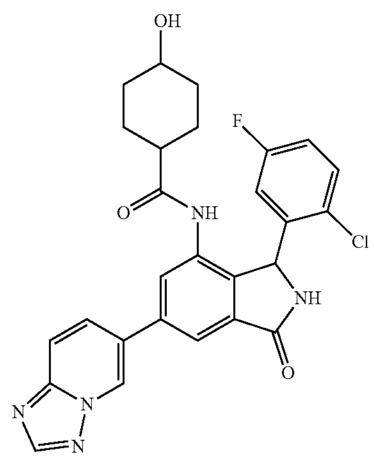 [SMILES: O=C1NC(c2cc(F)ccc2Cl)c2c(NC(=O)C3CCC(O)CC3)cc(-c3ccc4ncnn4c3)cc21] | OC1CCC(CC1)C(=O)Nc1cc(cc2C(=O)NC(c12)c1cc(F)ccc1Cl)-c1ccc2ncnn2c1 | NMR (400 MHz, DMSO-d6) 9.78 (br s, 1H), 9.43 (dd, 1.7, 0.8 Hz, 1H), 9.20 (br s, 1H), 8.57 (s, 1H), 8.09 (dd, 9.3, 1.8 Hz, 1H), 8.01-7.94 (m, 2H), 7.80 (d, 1.6 Hz, , 1H), 7.57-7.45 (m, 1H), 7.32-7.19 (m, 1H), 6.58 (br s, 1H), 6.11 (br s, 1H), 4.57 (br s, 1H), 2.02-1.91 (m, 1H), 1.83-1.68 (m, 2H), 1.54-1.42 (m, 1H), 1.38-1.27 (m, 1H), 1.26-1.10 (m, 2H), 1.10-0.96 (m, 1H). | 520 | E | |
| I-1691 | 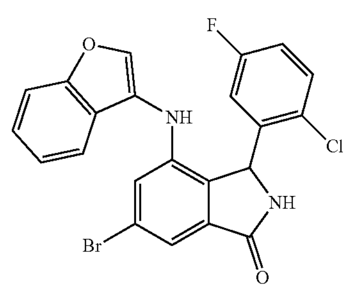 [SMILES: O=C1NC(c2cc(F)ccc2Cl)c2c(Nc3coc4ccccc34)cc(Br)cc21] | Fc1ccc(C1)c(c1)C1NC(=O)c2cc(Br)cc(Nc3coc4ccccc34)c12 | (400 MHz, DMSO-D6) 9.17 (s, 1 H), 7.92 (s, 1 H), 7.65 (br s, 1 H), 7.54 (d, 8.3 Hz, 1 H), 7.37-7.28 (m, 3 H), 7.16 (t, 7.4 Hz, 1 H), 7.10 (td, 8.3, 3.0 Hz, 1 H), 7.08 (d, 8.1 Hz, 1 H), 7.05 (d, 1.2 Hz, 1 H), 6.67 (br s, 1 H), 5.88 (s, 1 H). | 469.2 | D | |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-1692 | 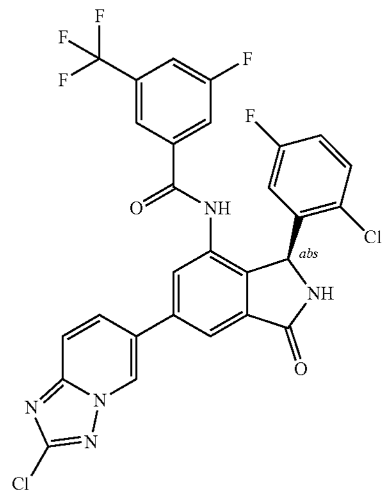 [SMILES: O=C(Nc1cc(-c2ccc3nc(Cl)nn3c2)cc2c1[C@@H](c1cc(F)ccc1Cl)NC2=O)c1cc(F)cc(C(F)(F)F)c1] | Fc1ccc(C1)c(c1)[C@H]1NC(=O)c2cc(cc(NC(=O)c3cc(F)cc(c3)C(F)(F)F)c12)-c1ccc2nc(Cl)nn2c1 | | 618.4 | D | |
| I-1693 | 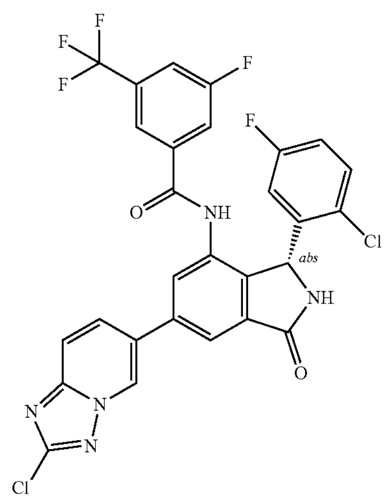 [SMILES: O=C(Nc1cc(-c2ccc3nc(Cl)nn3c2)cc2c1[C@H](c1cc(F)ccc1Cl)NC2=O)c1cc(F)cc(C(F)(F)F)c1] | Fc1ccc(C1)c(c1)[C@@H]1NC(=O)c2cc(cc(NC(=O)c3cc(F)cc(c3)C(F)(F)F)c12)-c1ccc2nc(Cl)nn2c1 | | 618.2 | A | |
| I-1694 | 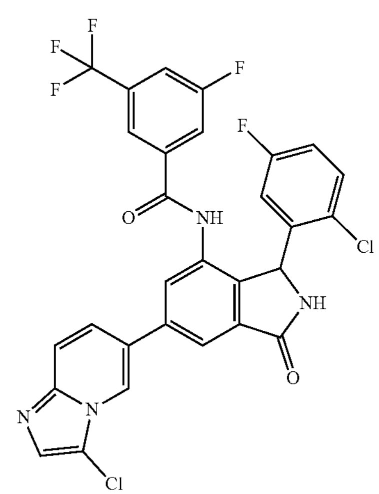 [SMILES: O=C(Nc1cc(-c2ccc3ncc(Cl)n3c2)cc2c1C(c1cc(F)ccc1Cl)NC2=O)c1cc(F)cc(C(F)(F)F)c1] | Fc1ccc(C1)c(c1)C1NC(=O)c2cc(cc(NC(=O)c3cc(F)cc(c3)C(F)(F)F)c12)-c1ccc2ncc(Cl)n2c1 | | 617.13 | A | |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-1695 | 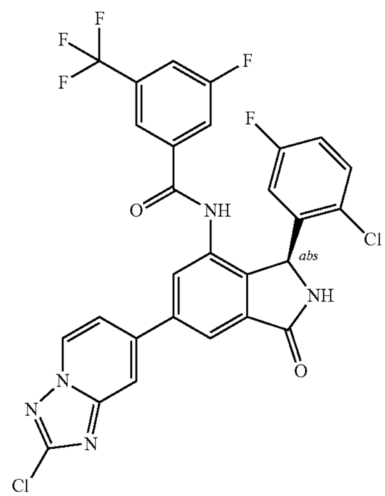 [SMILES: O=C(Nc1cc(-c2ccn3nc(Cl)nc3c2)cc2c1[C@@H](c1cc(F)ccc1Cl)NC2=O)c1cc(F)cc(C(F)(F)F)c1] | Fc1ccc(C1)c(c1)[C@H]1NC(=O)c2cc(cc(NC(=O)c3cc(F)cc(c3)C(F)(F)F)c12)-c1ccn2nc(Cl)nc2c1 | | 618.2 | D | |
| I-1696 | 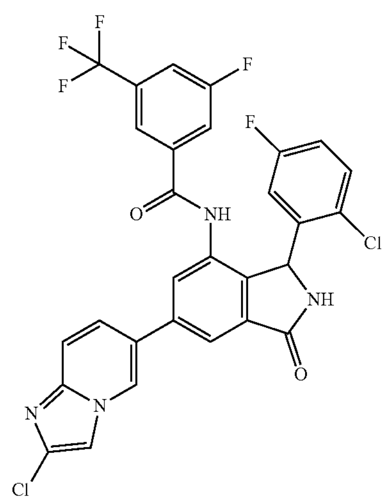 [SMILES: O=C(Nc1cc(-c2ccc3nc(Cl)cn3c2)cc2c1C(c1cc(F)ccc1Cl)NC2=O)c1cc(F)cc(C(F)(F)F)c1] | Fc1ccc(C1)c(c1)C1NC(=O)c2cc(cc(NC(=O)c3cc(F)cc(c3)C(F)(F)F)c12)-c1ccc2nc(Cl)cn2c1 | | 617.08 | A | |
| I-1697 | 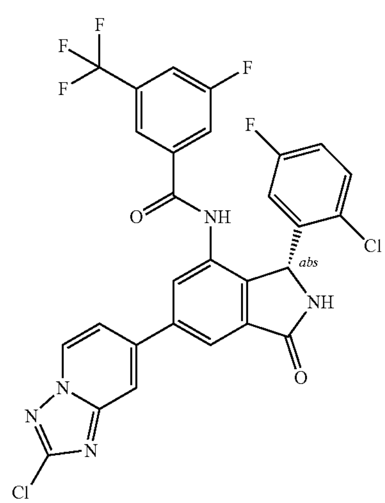 [SMILES: O=C(Nc1cc(-c2ccn3nc(Cl)nc3c2)cc2c1[C@H](c1cc(F)ccc1Cl)NC2=O)c1cc(F)cc(C(F)(F)F)c1] | Fc1ccc(C1)c(c1)[C@@H]1NC(=O)c2cc(cc(NC(=O)c3cc(F)cc(c3)C(F)(F)F)c12)-c1ccn2nc(Cl)nc2c1 | | 618.2 | A | |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-1698 | 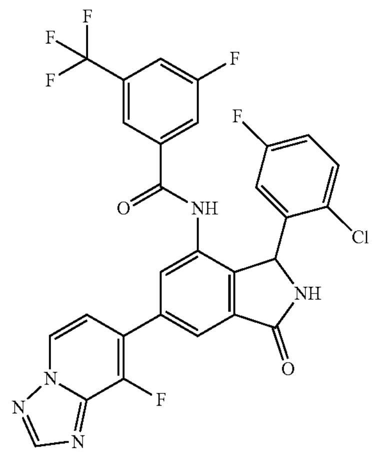 [SMILES: O=C(Nc1cc(-c2ccn3ncnc3c2F)cc2c1C(c1cc(F)ccc1Cl)NC2=O)c1cc(F)cc(C(F)(F)F)c1] | Fc1ccc(C1)c(c1)C1NC(=O)c2cc(cc(NC(=O)c3cc(F)cc(c3)C(F)(F)F)c12)-c1ccn2ncnc2c1F | | 602.18 | A | |
| I-1699 | 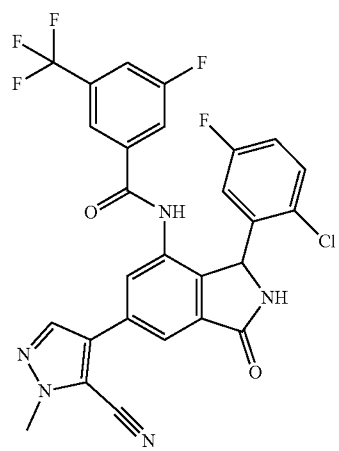 [SMILES: Cn1ncc(-c2cc(NC(=O)c3cc(F)cc(C(F)(F)F)c3)c3c(c2)C(=O)NC3c2cc(F)ccc2Cl)c1C#N] | Cn1ncc(c1C#N)-c1cc2C(=O)NC(c2c(NC(=O)c2cc(F)cc(c2)C(F)(F)F)c1)c1cc(F)ccc1Cl | | 572.4 | A | |
| I-1700 | 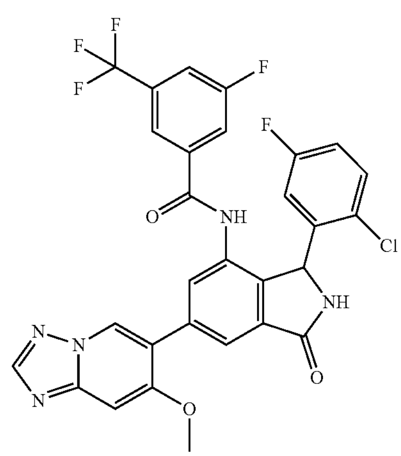 [SMILES: COc1cc2ncnn2cc1-c1cc(NC(=O)c2cc(F)cc(C(F)(F)F)c2)c2c(c1)C(=O)NC2c1cc(F)ccc1Cl] | COc1cc2ncnn2cc1-c1cc2C(=O)NC(c2c(NC(=O)c2cc(F)cc(c2)C(F)(F)F)c1)c1cc(F)ccc1Cl | | 614.08 | A | |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-1701 | 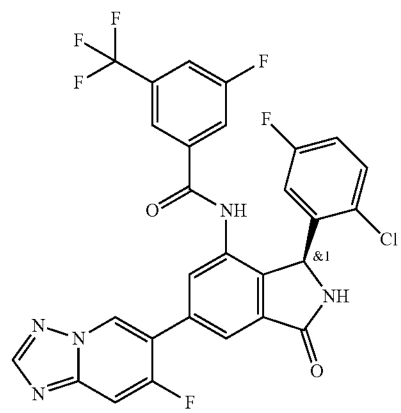 [SMILES: O=C(Nc1cc(-c2cn3ncnc3cc2F)cc2c1[C@@H](c1cc(F)ccc1Cl)NC2=O)c1cc(F)cc(C(F)(F)F)c1] | Fc1ccc(C1)c(c1)[C@H]1NC(=O)c2cc(cc(NC(=O)c3cc(F)cc(c3)C(F)(F)F)c12)-c1cn2ncnc2cc1F | | 602.2 | D | |
| I-1702 | 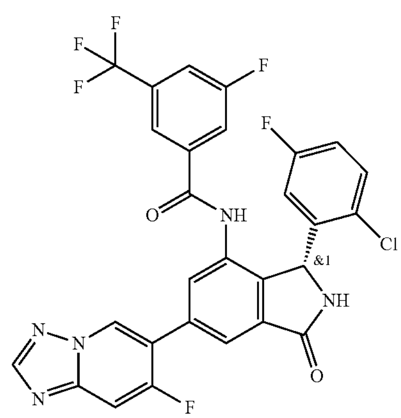 [SMILES: O=C(Nc1cc(-c2cn3ncnc3cc2F)cc2c1[C@H](c1cc(F)ccc1Cl)NC2=O)c1cc(F)cc(C(F)(F)F)c1] | Fc1ccc(C1)c(c1)[C@@H]1NC(=O)c2cc(cc(NC(=O)c3cc(F)cc(c3)C(F)(F)F)c12)-c1cn2ncnc2cc1F | | 602.2 | A | |
| I-1703 | 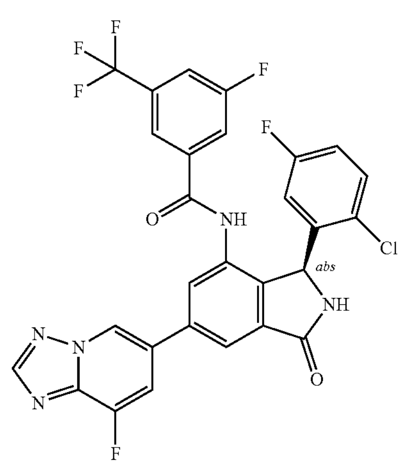 [SMILES: O=C(Nc1cc(-c2cc(F)c3ncnn3c2)cc2c1[C@@H](c1cc(F)ccc1Cl)NC2=O)c1cc(F)cc(C(F)(F)F)c1] | Fc1ccc(C1)c(c1)[C@H]1NC(=O)c2cc(cc(NC(=O)c3cc(F)cc(c3)C(F)(F)F)c12)-c1cc(F)c2ncnn2c1 | | 602.2 | E | |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-1704 | 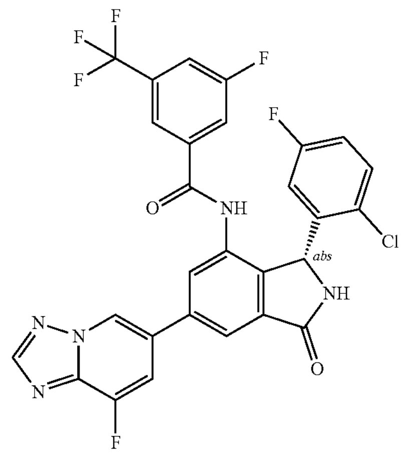 [SMILES: O=C(Nc1cc(-c2cc(F)c3ncnn3c2)cc2c1[C@H](c1cc(F)ccc1Cl)NC2=O)c1cc(F)cc(C(F)(F)F)c1] | Fc1ccc(C1)c(c1)[C@@H]1NC(=O)c2cc(cc(NC(=O)c3cc(F)cc(c3)C(F)(F)F)c12)-c1cc(F)c2ncnn2c1 | | 602.2 | A | |
| I-1705 | 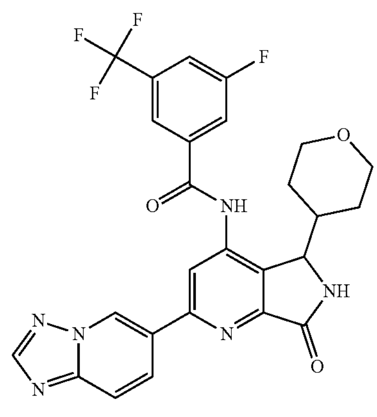 [SMILES: O=C(Nc1cc(-c2ccc3ncnn3c2)nc2c1C(C1CCOCC1)NC2=O)c1cc(F)cc(C(F)(F)F)c1] | Fc1cc(cc(c1)C(F)(F)F)C(=O)Nc1cc(nc2C(=O)NC(C3CCOCC3)c12)-c1ccc2ncnn2c1 | | 541.7 | E | |
| I-1706 | 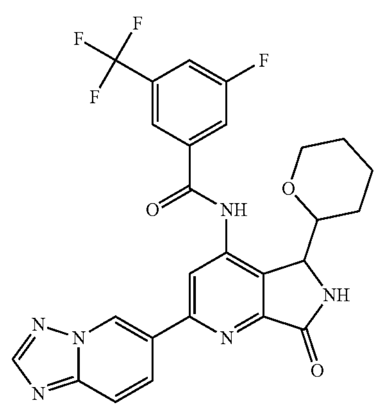 [SMILES: O=C(Nc1cc(-c2ccc3ncnn3c2)nc2c1C(C1CCCCO1)NC2=O)c1cc(F)cc(C(F)(F)F)c1] | Fc1cc(cc(c1)C(F)(F)F)C(=O)Nc1cc(nc2C(=O)NC(C3CCCO3)c12)-c1ccc2ncnn2c1 | | 541.7 | E | |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-1707 | 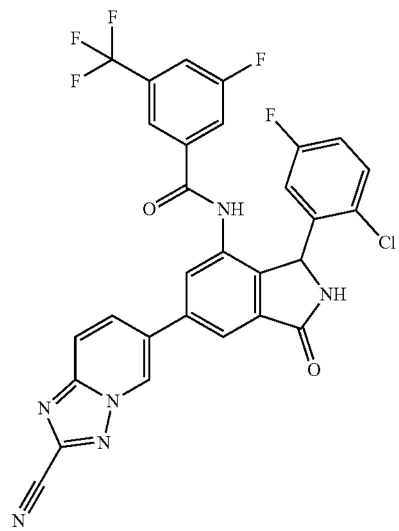 [SMILES: N#Cc1nc2ccc(-c3cc(NC(=O)c4cc(F)cc(C(F)(F)F)c4)c4c(c3)C(=O)NC4c3cc(F)ccc3Cl)cn2n1] | Fc1ccc(C1)c(c1)ClNC(=O)c2cc(cc(NC(=O)c3cc(F)cc(c3)C(F)(F)F)c12)-c1ccc2nc(nn2c1)C#N | | 609.13 | A | |
| I-1708 | 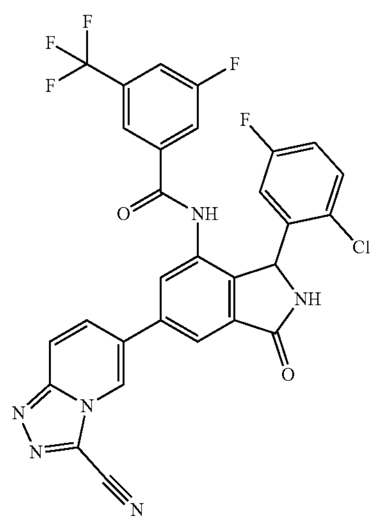 [SMILES: N#Cc1nnc2ccc(-c3cc(NC(=O)c4cc(F)cc(C(F)(F)F)c4)c4c(c3)C(=O)NC4c3cc(F)ccc3Cl)cn12] | Fc1ccc(C1)c(c1)C1NC(=O)c2cc(cc(NC(=O)c3cc(F)cc(c3)C(F)(F)F)c12)-c1ccc2nnc(C#N)n2c1 | | 609.08 | A | |
| I-1709 | 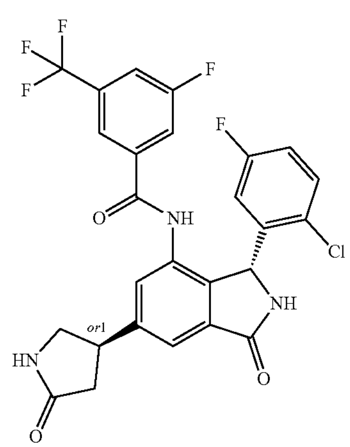 [SMILES: O=C1C[C@H](c2cc(NC(=O)c3cc(F)cc(C(F)(F)F)c3)c3c(c2)C(=O)N[C@H]3c2cc(F)ccc2Cl)CN1] | Fc1ccc(C1)c(c1)[C@@H]1NC(=O)c2cc(cc(NC(=O)c3cc(F)cc(c3)C(F)(F)F)c12)[C@@H]1CNC(=O)C1 | (400 MHz, CD3CN) 8.79 (s, 1H), 7.68 (d, 1.2 Hz, 1H), 7.66-7.62 (m, 1H), 7.62-7.59 (m, 1H), 7.58 (s, 1H), 7.48 (s, 1H), 7.32 (br s, 1H), 7.24 (dd, 8.9, 5.1 Hz, 1H), 6.96 (td, 8.5, 3.2 Hz, 1H), 6.61 (br s, 1H), 6.19 (s, 1H), 6.10 (br s, 1H), 3.89-3.79 (m, 1H), 3.79-3.73 (m, 1H), 3.37 (dd, 9.2, 7.1 Hz, 1H), 2.66 (dd, 16.5, 8.6 Hz, 1H), 2.41 (dd, 16.5, 8.5 Hz, 1H) | 548.2 | A | |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-1710 | 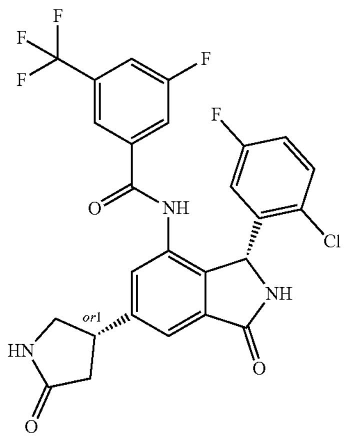 [SMILES: O=C1C[C@@H](c2cc(NC(=O)c3cc(F)cc(C(F)(F)F)c3)c3c(c2)C(=O)N[C@H]3c2cc(F)ccc2Cl)CN1] | Fc1ccc(C1)c(c1)[C@@H]1NC(=O)c2cc(cc(NC(=O)c3cc(F)cc(c3)C(F)(F)F)c12)[C@H]1CNC(=O)C1 | (400 MHz, CD3CN) 8.73 (s, 1H), 7.68 (d, 1.3 Hz, 1H), 7.65 (d, 8.4 Hz, 1H), 7.67-7.58 (m, 1H), 7.57 (s, 1H), 7.48 (s, 1H), 7.28 (s, 1H), 7.24 (dd, 8.9, 5.1 Hz, 1H), 6.96 (td, 8.5, 3.2 Hz, 1H), 6.60 (br s, 1H), 6.15 (s, 1H), 6.11 (s, 1H), 3.90-3.80 (m, 1H), 3.77 (t, 8.4 Hz, 1H), 3.39 (dd, 9.2, 6.9 Hz, 1H), 2.67 (dd, 16.5, 8.6 Hz, 1H), 2.39 (dd, 16.5, 8.3 Hz, 1H). | 548.2 | A | |
| I-1711 | 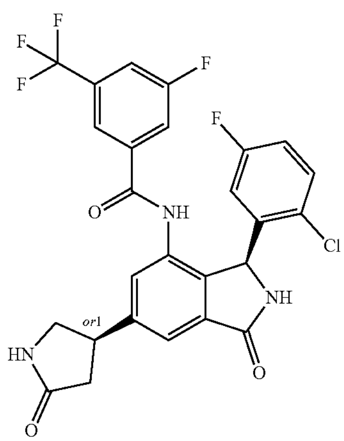 [SMILES: O=C1C[C@H](c2cc(NC(=O)c3cc(F)cc(C(F)(F)F)c3)c3c(c2)C(=O)N[C@@H]3c2cc(F)ccc2Cl)CN1] | Fc1ccc(C1)c(c1)[C@H]1NC(=O)c2cc(cc(NC(=O)c3cc(F)cc(c3)C(F)(F)F)c12)[C@@H]1CNC(=O)C1 | (400 MHz, CD3CN) 8.75 (s, 1H), 7.69 (d, 1.2 Hz, 1H), 7.67-7.63 (m, 1H), 7.63-7.59 (m, 1H), 7.58 (s, 1H), 7.48 (s, 1H), 7.30-7.22 (m, 2H), 6.96 (td, 8.5, 3.1 Hz, 1H), 6.63 (br s, 1H), 6.13 (br s, 2H), 3.90-3.80 (m, 1H), 3.77 (app t, 8.4 Hz, 1H), 3.37 (dd, 9.2, 7.1 Hz, 1H), 2.67 (dd, 16.5, 8.6 Hz, 1H), 2.42 (dd, 16.5, 8.5 Hz, 1H). | 548.2 | D | |
| I-1712 | 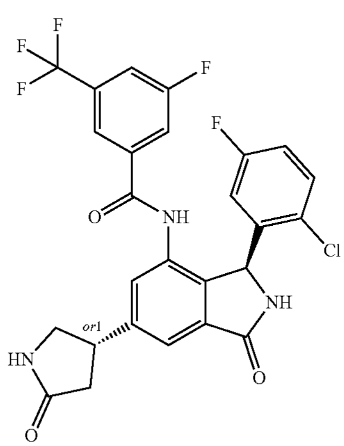 [SMILES: O=C1C[C@@H](c2cc(NC(=O)c3cc(F)cc(C(F)(F)F)c3)c3c(c2)C(=O)N[C@@H]3c2cc(F)ccc2Cl)CN1] | Fc1ccc(C1)c(c1)[C@H]1NC(=O)c2cc(cc(NC(=O)c3cc(F)cc(c3)C(F)(F)F)c12)[C@H]1CNC(=O)C1 | (400 MHz, CD3CN) 8.74 (br s, 1H), 7.68 (d, 1.3 Hz, 1H), 7.67-7.63 (m, 1H), 7.63-7.59 (m, 1H), 7.58 (s, 1H), 7.49 (s, 1H), 7.27-7.22 (m, 2H), 6.96 (td, 8.6, 3.2 Hz, 1H), 6.61 (br s, 1H), 6.12 (br s, 2H), 3.90-3.80 (m, 1H), 3.77 (app t, 8.5 Hz., 1H), 3.39 (dd, 9.2, 6.9 Hz, 1H), 2.67 (dd, 16.5, 8.7 Hz, 1H), 2.39 (dd, 16.5, 8.4 Hz, 1H). | 548.3 | D | |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-1713 | 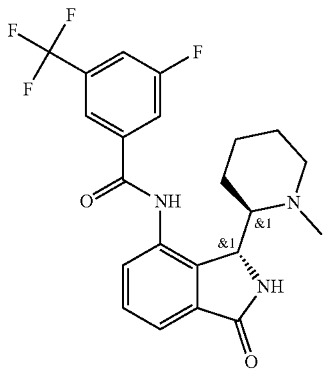 [SMILES: CN1CCCC[C@@H]1[C@@H]1NC(=O)c2cccc(NC(=O)c3cc(F)cc(C(F)(F)F)c3)c21] | CN1CCCC[C@@H]1[C@@H]1NC(=O)c2cccc(NC(=O)c3cc(F)cc(c3)C(F)(F)F)c12 | (400 MHz, DMSO-d6) 8.60 (s, 1H), 8.35 (d, 7.2 Hz, 1H), 8.04 (d, 8.6 Hz, 1H), 7.92 (s, 1H), 7.89 (d, 8.4 Hz, 1H), 7.53 (t, 7.7 Hz, 1H), 7.45 (dd, 7.4, 1.0 Hz, 1H), 5.22 (s, 1H), 2.39-2.34 (m, 1H), 2.21 (s, 3H), 2.13-2.04 (m, 1H), 1.60-1.56 (m, 1H), 1.56-1.50 (m, 1H), 1.45-1.39 (m, 1H), 1.36-1.29 (m, 1H), 1.26-1.21 (m, 1H), 1.13-1.07 (m, 1H), 0.63 (qd, 14.3, 4.7 Hz, 1H) | 436.2 | E | |
| I-1714 | 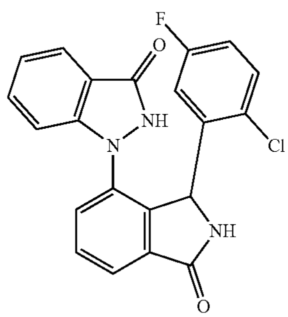 [SMILES: O=C1NC(c2cc(F)ccc2Cl)c2c1cccc2-n1[nH]c(=O)c2ccccc21] | Fc1ccc(C1)c(c1)C1NC(=O)c2cccc(c12)-n1[nH]c(=O)c2ccccc12 | 1H NMR (400 MHz, DMSO-d6) 10.97 (s, 1H), 9.17 (s, 1H), 7.82 (dd, 6.5, 2.5 Hz, 1H), 7.81-7.72 (m, 2H), 7.55 (d, 8.0 Hz, 1H), 7.30 (d, 3.9 Hz, 2H), 7.12 (s, 1H), 7.02 (dt, 7.8, 3.8 Hz, 1H), 6.81 (td, 8.4, 3.1 Hz, 1H), 6.36 (s, 1H), 6.25 (s, 1H). | 394.05 | E | |
| I-1715 | 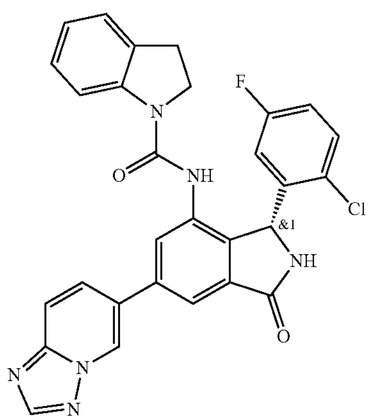 [SMILES: O=C1N[C@@H](c2cc(F)ccc2Cl)c2c(NC(=O)N3CCc4ccccc43)cc(-c3ccc4ncnn4c3)cc21] | Fc1ccc(C1)c(c1)[C@@H]1NC(=O)c2cc(cc(NC(=O)N3CCc4cccc34)c12)-c1ccc2ncnn2c1 | 1H NMR (400 MHz, DMSO-d6) 9.43 (dd, 1.9, 0.9 Hz, 1H), 9.16 (s, 1H), 8.67 (s, 1H), 8.57 (s, 1H), 8.10 (dd, 9.3, 1.9 Hz, 1H), 8.02-7.95 (m, 2H), 7.81 (d, 1.7 Hz, 1H), 7.73 (d, 8.0 Hz, 1H), 7.40 (dd, 8.8, 5.2 Hz, 1H), 7.22-7.14 (m, 2H), 7.17-7.07 (m, 1H), 6.91 (td, 7.4, 1.1 Hz, 1H), 6.69 (s, 1H), 6.10 (s, 1H), 3.88 (td, 10.0, 7.4 Hz, 1H), 3.04 (dt, 16.6, 7.5 Hz, 2H). | 539.3 | A | A |
| I-1716 | 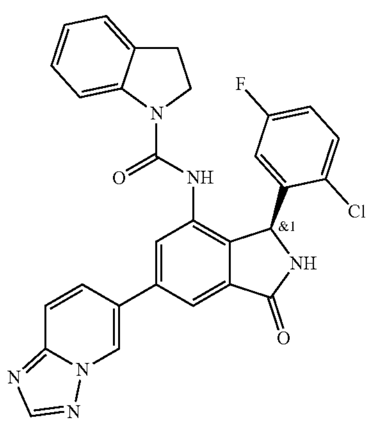 [SMILES: O=C1N[C@H](c2cc(F)ccc2Cl)c2c(NC(=O)N3CCc4ccccc43)cc(-c3ccc4ncnn4c3)cc21] | Fc1ccc(C1)c(c1)[C@H]1NC(=O)c2cc(cc(NC(=O)N3CCc4cccc34)c12)-c1ccc2ncnn2c1 | 1H NMR (400 MHz, DMSO-d6) 9.42 (d, 1.8 Hz, 1H), 9.15 (s, 1H), 8.69 (s, 1H), 8.57 (s, 1H), 8.10 (dd, 9.3, 1.8 Hz, 1H), 8.04-7.95 (m, 2H), 7.82 (d, 2.0 Hz, 1H), 7.73 (d, 8.0 Hz, 1H), 7.40 (dd, 8.9, 5.1 Hz, 1H), 7.30 (d, 9.9 Hz, 1H), 7.28-7.15 (m, 3H), 7.15-7.00 (m, 2H), 6.99-6.85 (m,1H), 6.69 (s, 1H), 6.11 (s, 1H), 3.95-3.84 (m, 1H), 3.35-3.28 (m, 1H), 3.14-2.95 (m, 2H). | 539 | D | |

TABLE 2-continued

Representative Compounds of the Invention with Bioactivity Data.

| Ex. No. | Structure | SMILES | $^1$H NMR | MS | ADP-Glo IC$_{50}$ | MCF 10A IC$_{50}$ |
|---|---|---|---|---|---|---|
| I-1717 | 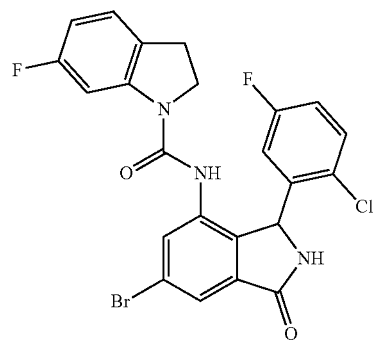 [SMILES: O=C1NC(c2cc(F)ccc2Cl)c2c(NC(=O)N3CCc4ccc(F)cc43)cc(Br)cc21] | Fc1ccc2 CCN(C(= O)Nc3cc (Br)cc4C (=O)NC(c 34)c3cc (F)ccc3Cl) c2c1 | 1H-NMR (400 MHz, DMSO-d6) 9.23 (br. s, 1H), 8.79 (s, 1H), 7.69 (s, 1H), 7.57 (s, 1H), 7.45 (br. d, 10.6 Hz, 1H), 7.38 (dd, 8.8, 5.1 Hz, 1H), 7.19-7.13 (m, 2H), 6.71 (app. td, 9.0, 2.5 Hz, 1H), 6.65 (br. s, 1H), 5.97 (br. s, 1H), 3.87 (td, 10.0, 7.5 Hz, 1H), 3.29-3.17 (m, 1H), 3.07-2.89 (m, 2H). | 520.1 | A | |
| I-1718 | 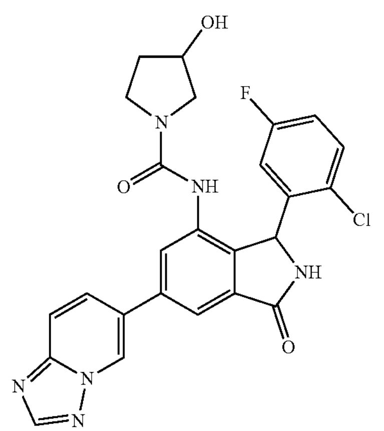 [SMILES: O=C1NC(c2cc(F)ccc2Cl)c2c(NC(=O)N3CCC(O)C3)cc(-c3ccc4ncnn4c3)cc21] | OC1CCN (C1)C(= O)Nc1cc (cc2C(=O) NC(c12) c1cc(F)cc c1Cl)- c1ccc2nc nnn2c1 | 1H-NMR (400 MHz, DMSO-d6) 9.38 (dd, 1.6, 0.9 Hz, 2H), 9.14 (br. s, 2H), 8.57 (s, 2H), 8.23 (br. s, 1H), 8.19 (br. s, 1H), 8.06 (dd, 9.3, 1.8 Hz, 2H), 7.97 (dd, 9.3, 0.5 Hz, 2H), 7.89 (s, 2H), 7.73 (br. s, 1H), 7.71 (br. s, 1H), 7.51-7.44 (m, 2H), 7.27-7.20 (m, 2H), 6.68 (br. s, 2H), 6.07 (br. s, 2H), 4.99 (br. s, 2H), 4.24-4.19 (m, 1H), 4.18-4.13 (m, 1H), 3.39-3.26 (m, 6H), 3.08-3.03 (m, 2H), 1.83-1.75 (m, 1H), 1.75-1.64 (m, 3H). | 507.3 | E | |
| I-1719 | 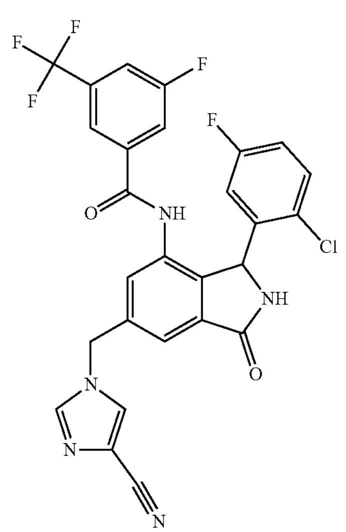 [SMILES: N#Cc1cn(Cc2cc(NC(=O)c3cc(F)cc(C(F)(F)F)c3)c3c(c2)C(=O)NC3c2cc(F)ccc2Cl)cn1] | Fc1ccc(C 1)c(c1)C1 NC(=O)c 2cc(Cn3c nc(c3)C# N)cc(NC (=O)c3cc (F)cc(c3) C(F)(F)F) c12 | 1H-NMR (400 MHz, DMSO-d6) 10.56 (br. s, 1H), 9.16 (br. s, 1H), 8.31(s, 1H), 8.12 (s), 7.93-7.85 (m, 1H), 7.71 (br. d, 8.6 Hz, 1H), 7.65 (s, 1H), 7.61 (br. s, 1H), 7.48 (br. s, 1H), 7.31 (dd, 8.9, 5.3 Hz, 1H), 7.08 (app. id, 8.5, 3.2 Hz, 1H), 6.62 (br. s, 1H), 5.95 (br. s, 1H), 5.47 (d, A of AB, JAB = 15.5 Hz, 1H), 5.42 (d, B of AB, JAB = 15.1 Hz, 1H). | 572.2 | A | |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-1720 | 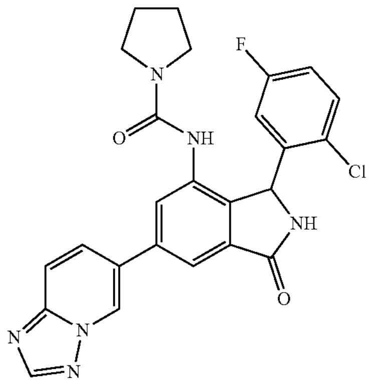 [SMILES: O=C1NC(c2cc(F)ccc2Cl)c2c(NC(=O)N3CCCC3)cc(-c3ccc4ncnn4c3)cc21] | Fc1ccc(C1)c(c1)C1NC(=O)c2cc(cc(NC(=O)N3CCCC3)c12)-c1ccc2ncnn2c1 | 1H-NMR (400 MHz, DMSO-d6) 9.38 (dd, 1.7, 0.9 Hz, 1H), 9.13 (br. s, 1H), 8.57 (s, 1H), 8.25 (br. s, 1H), 8.05 (dd, 9.3, 1.8 Hz, 1H), 7.97 (dd, 9.3, 0.8 Hz, 1H), 7.89 (d, 1.6 Hz, 1H), 7.68 (d, 1.5 Hz, 1H), 7.53-7.46 (m, 1H), 7.25 (ddd, 8.7, 8.2, 3.1 Hz, 1H), 6.67 (br. s, 1H), 6.06 (br. s, 1H), 3.25-3.21 (m, 4H), 1.76-1.71 (m, 4H). | 491.3 | E | |
| I-1721 | 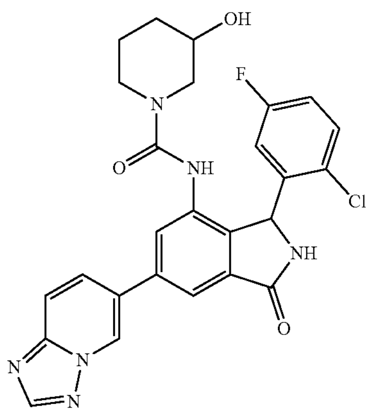 [SMILES: O=C1NC(c2cc(F)ccc2Cl)c2c(NC(=O)N3CCCC(O)C3)cc(-c3ccc4ncnn4c3)cc21] | OC1CCCN(C1)C(=O)Nc1cc(cc2C(=O)NC(c12)c1cc(F)ccc1Cl)-c1ccc2ncnn2c1 | 1H-NMR (400 MHz, DMSO-d6)-9.38 (dd, 1.6, 0.8 Hz, 2H), 9.12 (br. s, 2H), 8.66 (br. s, 1H), 8.61 (br. s, 1H), 8.56 (s, 2H), 8.07 (d, 1.7 Hz, 1H), 8.05 (d, 1.7 Hz, 1H), 7.98 (d, 0.6 Hz, 1H), 7.96 (d, 0.7 Hz, 1H), 7.88 (d, 1.6 Hz, 2H), 7.69 (d, 1.6 Hz, 1H), 7.66 (d, 1.6 Hz, 1H), 7.54-7.47 (m, 2H), 7.28-7.21 (m, 2H), 6.59 (br. s, 1H), 6.08 (br. s, 2H), 4.85 (br. s, 2H), 3.82-3.73 (m, 2H), 3.63 (br. d, 12.8 Hz, 1H), 3.50 (br. d, 12.6 Hz, 1H), 2.99-2.89 (m, 1H), 2.63-2.54 (m, 1H), 2.44-2.34 (m, 2H), 2.27 (dd, 12.2, 9.9 Hz, 1H), 1.84-1.73 (m, 2H), 1.61-1.45 (m, 2H), 1.32-1.10 (m, 4H), 0.92-0.78 (m, 1H). | 521.3 | E | |
| I-1722 | 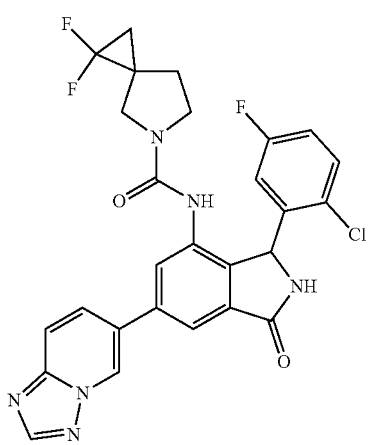 [SMILES: O=C1NC(c2cc(F)ccc2Cl)c2c(NC(=O)N3CCC4(C3)CC4(F)F)cc(-c3ccc4ncnn4c3)cc21] | Fc1ccc(C1)c(c1)C1NC(=O)c2cc(cc(NC(=O)N3CCC4(CC4(F)F)C3)c12)-c1ccc2ncnn2c1 | 1H-NMR (400 MHz, DMSO-d6) ' 9.39-9.38 (m, 1H), 9.16 (br. s, 1H), 8.57 (s, 1H), 8.41 (d, 2.2 Hz, 1H), 8.08-8.04 (m, 1H), 7.97 (dd, 9.3, 0.8 Hz, 1H), 7.92 (d, 1.4 Hz, 1H), 7.68 (dd, 5.4, 1.6 Hz, 1H), 7.53-7.45 (m, 1H), 7.30-7.20 (m, 1H), 6.66 (br. s, 1H), 6.06 (br. s, 1H), 3.54-3.37 (m, 2H), 3.11-3.02 (m, 1H), 3.00-2.86 (m, 1H), 2.02-1.85 (m, 2H), 1.64-1.49 (m, 2H). | 553.3 | D | |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-1723 | 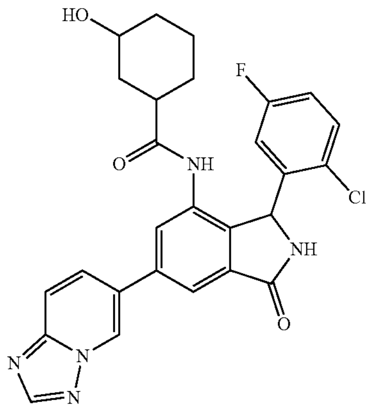 | OC1CCCC(C1)C(=O)Nc1cc(cc2C(=O)NC(c12)c1cc(F)ccc1Cl)-c1ccc2ncnn2c1 | 1H-NMR (400 MHz, DMSO-d6) 9.84 (br. s, 1H), 9.78 (br. s, 1H), 9.45-9.42 (m, 2H), 9.20 (br. s, 2H), 8.57 (s, 2H), 8.10 (dd, 3.8, 1.5 Hz, 1H), 8.07 (dd, 3.6, 1.5 Hz, 1H), 7.99-7.96 (m, 3H), 7.96 (s, 1H), 7.85 (d, 0.8 Hz, 1H), 7.76 (d, 0.6 Hz, 1H), 7.55-7.48 (m, 2H), 7.24 (app. td, 8.3, 2.9 Hz, 2H), 6.56 (br. s, 2H), 6.15 (br. s, 2H), 4.42 (br. s, 2H), 3.90-3.86 (m, 1H), 3.85-3.82 (m, 1H), 1.58-1.44 (m, 5H), 1.43-1.23 (m, 8H), 1.20-1.11 (m, 2H), 1.10-1.01 (m, 1H). | 520.3 | E | |
| I-1724 | 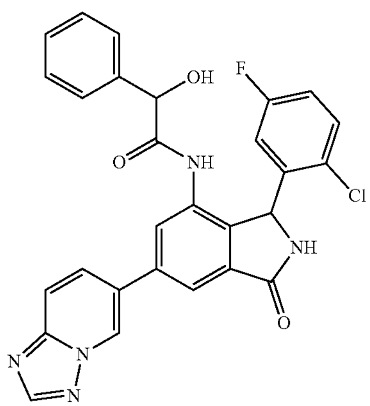 [SMILES: O=C1NC(c2cc(F)ccc2Cl)c2c(NC(=O)C(O)c3ccccc3)cc(-c3ccc4ncnn4c3)cc21] | OC(C(=O)Nc1cc(cc2C(=O)NC(c12)c1cc(F)ccc1Cl)-c1ccc2ncnn2c1)c1ccccc1 | NMR (400 MHz, DMSO-d6) 9.62 (br s, 1H), 9.41 (s, 1Hz), 9.20 (s, 1H), 8.57 (d, 1.7 Hz, 1H), 8.30 (s, 1H), 8.05 (td, 9.2, 1.6 Hz, 1H), 7.98 (d, 3.5 Hz, 1H), 7.62-7.50 (m, 1H), 7.46-7.39 (m, 1H), 7.35-7.17 (m, 5H), 7.06 (d, 2.2 Hz, 1H), 6.63 (br s, 1H), 6.21 (br s, 1H), 4.95 (s, 1H). | 528 | E | |
| I-1725 | 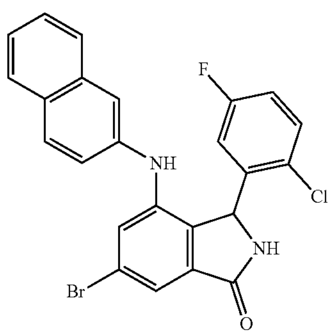 [SMILES: O=C1NC(c2cc(F)ccc2Cl)c2c(Nc3ccc4ccccc4c3)cc(Br)cc21] | Fc1ccc(C1)c(c1)C1NC(=O)c2cc(Br)cc(Nc3ccc4ccccc4c3)c12 | NMR (400 MHz, DMSO-d6) 9.15 (br s, 1H), 8.15 (s, 1H), 7.76 (d, 8.1 Hz, 1H), 7.71 (d, 8.8 Hz, 2H), 7.49-7.46 (m, 2H), 7.39 (t, 7.0 Hz, 1H), 7.32-7.24 (m, 2H), 7.13 (d, 1.7 Hz, 1H), 7.10-7.03 (m, 1H), 6.92 (dd, 8.8, 2.1 Hz, 1H), 6.48 (dd, 9.3, 2.8 Hz, 1H), 5.82 (s, 1H) | 481.1 | D | |
| I-1726 | 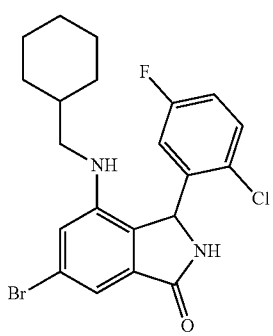 [SMILES: O=C1NC(c2cc(F)ccc2Cl)c2c(NCC3CCCCC3)cc(Br)cc21] | Fc1ccc(C1)c(c1)C1NC(=O)c2cc(Br)cc(NCC3CCCC3)c12 | NMR (400 MHz, DMSO-d6) 9.06 (s, 1H), 7.60-7.49 (m, 1H), 7.26 (td, 8.4, 3.1 Hz, 1H), 7.03 (d, 1.2 Hz, 1H), 6.87 (s, 1H), 6.76 (br s, 1H), 5.82 (s, 1H), 4.65-4.56 (m, 1H), 2.97-2.87 (m, 1H), 2.83-2.74 (m, 1H), 1.55 (d, 6.8 Hz, 3H), 1.45-1.24 (m, 3H), 1.15-0.96 (m, 3H), 0.78-0.58 (m, 2H). | 451.1 | E | |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-1727 | 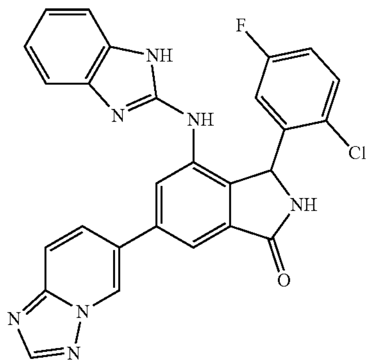 [SMILES: O=C1NC(c2cc(F)ccc2Cl)c2c(Nc3nc4ccccc4[nH]3)cc(-c3ccc4ncnn4c3)cc21] | Fc1ccc(C1)c(c1)C1NC(=O)c2cc(cc(Nc3nc4cccc4[nH]3)c12)-c1ccc2ncnn2c1 | 1H NMR (400 MHz, DMSO-d6) 9.41 (dd, 1.7, 0.9 Hz, 1H), 9.12 (br. s, 1H), 8.57 (s, 1H), 8.40 (d, 1.3 Hz, 1H), 8.35 (br. s, 2H), 8.10 (dd, 9.3, 1.8 Hz, 1H), 7.99 (dd, 9.3, 0.7 Hz, 1H), 7.81 (d, 1.6 Hz., 1H), 7.39 (dd, 8.8, 5.2 Hz, 1H), 7.21 (dd, 5.4, 2.9 Hz, 2H), 7.12 (ddd, 3.1, 8.0, 8.7 Hz, 1H), 7.00-6.87 (m, 2H), 6.61 (br. s, 1H), 6.38 (s, 1H). | 510.3 | D | |
| I-1728 | 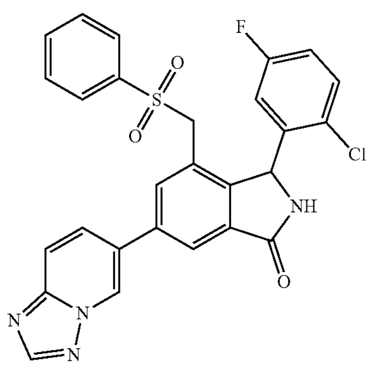 [SMILES: O=C1NC(c2cc(F)ccc2Cl)c2c(CS(=O)(=O)c3ccccc3)cc(-c3ccc4ncnn4c3)cc21] | Fc1ccc(C1)c(c1)C1NC(=O)c2cc(cc(CS(=O)(=O)c3cccc3)c12)-c1ccc2ncnn2c1 | 1H NMR (400 MHz, DMSO-d6) 9.33 (br. s, 1H), 9.23 (dd, 1.7, 0.9 Hz, 1H), 8.58 (s, 1H), 8.21 (s, 1H), 7.99 (d, 9.2 Hz, 1H), 7.83-7.74 (m, 1H), 7.83-7.74 (m, 1H), 7.74-7.60 (m, 5H), 7.45 (br. s, 1H), 7.30 (br. s, 1H), 6.47 (br. s, 1H), 6.07 (br. s, 1H), 4.71 (br. d, 13.4 Hz, 1H), 3.89 (d, 13.8 Hz, 1H) | 533.1 | E | |
| I-1729 | 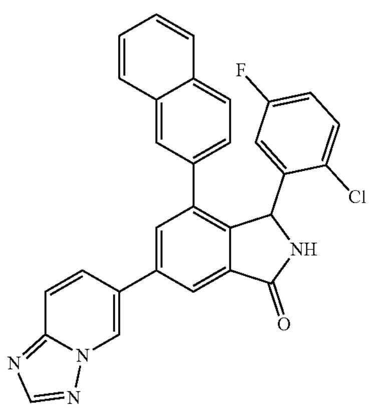 [SMILES: O=C1NC(c2cc(F)ccc2Cl)c2c1cc(-c1ccc3ncnn3c1)cc2-c1ccc2ccccc2c1] | Fc1ccc(C1)c(c1)C1NC(=O)c2cc(cc(c12)-c1ccc2ccccc2c1)-c1ccc2ncnn2c1 | NMR (400 MHz, DMSO-d6) 9.63 (s, 1H), 9.34 (br s, 1H), 8.58 (s, 1H), 8.27 (d, 9.3 Hz, 1H), 8.21 (d, 1.5 Hz, 1H), 8.13 (s, 1H), 8.06 (s, 1H), 7.97 (d, 9.3 Hz, 1H), 7.87 (t, 7.1 Hz, 2H), 7.82 (d, 8.5 Hz, 1H), 7.63 (d, 9.0 Hz, 1H), 7.56-7.44 (m, 2H), 7.07 (dd, 8.8, 5.2 Hz, 1H), 6.84 (td, 8.7, 2.8 Hz, 1H), 6.64 (br s, 1H), 6.39 (br s, 1H). | 505 | D | |
| I-1730 | 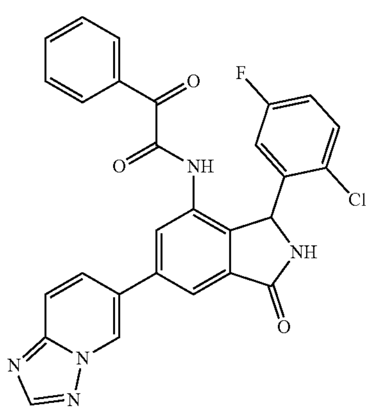 [SMILES: O=C(Nc1cc(-c2ccc3ncnn3c2)cc2c1C(c1cc(F)ccc1Cl)NC2=O)C(=O)c1ccccc1] | Fc1ccc(C1)c(c1)C1NC(=O)c2cc(cc(NC(=O)C(=O)c3ccccc3)c12)-c1ccc2ncnn2c1 | NMR (400 MHz, DMSO-d6) 10.91 (br s, 1H), 9.51 (s, 1H), 9.31 (br s, 1H), 8.58 (s, 1H), 8.15 (dd, 9.3, 1.7 Hz, 1H), 8.12 (d, 1.2 Hz, 1H), 8.06 (d, 1.4 Hz, 1H), 7.99 (d, 9.2 Hz, 1H), 7.82-7.71 (m, 3H), 7.66-7.59 (m, 1H), 7.58-7.49 (m, 3H), 7.24 (td, 8.6, 2.9 Hz, 1H), 6.65 (br s, 1H), 6.21 (br s, 1H). | 526 | D | |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-1731 | 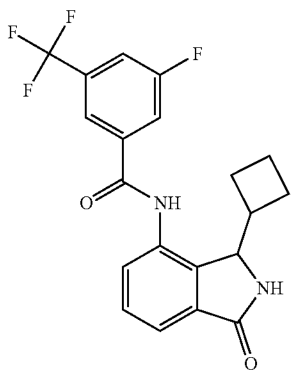 [SMILES: O=C(Nc1cccc2c1C(C1CCC1)NC2=O)c1cc(F)cc(C(F)(F)F)c1] | Fc1cc(cc(c1)C(F)(F)F)C(=O)Nc1ccccc2C(=O)NC(C3CCC3)c12 | NMR (400 MHz, DMSO-d6) 10.68 (s, 1H), 8.92 (s, 1H), 8.21 (s, 1H), 8.16 (d, 9.1 Hz, 1H), 8.04 (d, 8.4 Hz, 1H), 7.58-7.49 (m, 3H), 4.77 (d, 4.5 Hz, 1H), 2.77-2.64 (m, 1H), 2.07-1.95 (m, 1H), 1.90-1.80 (m, 1H), 1.76-1.66 (m, 1H), 1.65-1.53 (m, 1H), 1.39-1.30 (m, 2H). | 393 | E | |
| I-1732 | 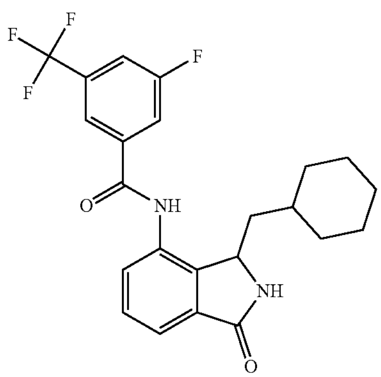 [SMILES: O=C(Nc1cccc2c1C(CC1CCCCC1)NC2=O)c1cc(F)cc(C(F)(F)F)c1] | Fc1cc(cc(c1)C(F)(F)F)C(=O)Nc1ccccc2C(=O)NC(CC3CCCCC3)c12 | NMR (400 MHz, DMSO-d6) 10.78 (s, 1H), 8.91 (s, 1H), 8.17 (s, 1H), 8.12 (d, 9.0 Hz, 1H), 8.05 (d, 8.4 Hz, 1H), 7.60-7.50 (m, 3H), 4.83 (br, d, 8.0 Hz, 1H), 1.83-1.66 (m, 2H), 1.57-1.37 (m, 5H), 1.18-0.90 (m, 4H), 0.81-0.58 (m, 2H). | 435 | D | |
| I-1733 | 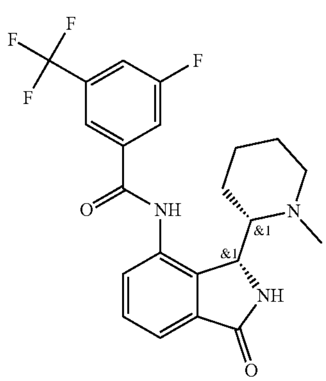 [SMILES: CN1CCCC[C@H]1[C@@H]1NC(=O)c2cccc(NC(=O)c3cc(F)cc(C(F)(F)F)c3)c21] | CN1CCCC[C@H]1[C@@H]1NC(=O)c2cccc(NC(=O)c3cc(F)cc(c3)C(F)(F)F)c12 | (400 MHz, DMSO-d6) 11.17 (br s, 1H), 8.56 (s, 1H), 8.16 (s, 1H), 8.10 (d, 9.4 Hz, 1H), 8.04 (t, 7.8 Hz, 1H), 7.66 (dd, 7.0, 1.8 Hz, 1H), 7.58-7.50 (m, 2H), 5.26 (d, 3.6 Hz, 1H), 2.86-2.77 (app dt, 11.6 Hz, 2.5 H, 1H), 2.29-2.23 (m, 1H), 2.21 (s, 3H), 1.79 (td, 11.5, 2.4 Hz, 1H), 1.56-1.37 (m, 2H), 1.36-1.19 (m, 1H), 1.00-0.89 (m, 2H), 0.69-0.60 (m, 1H) | 436.3 | E | |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-1734 | 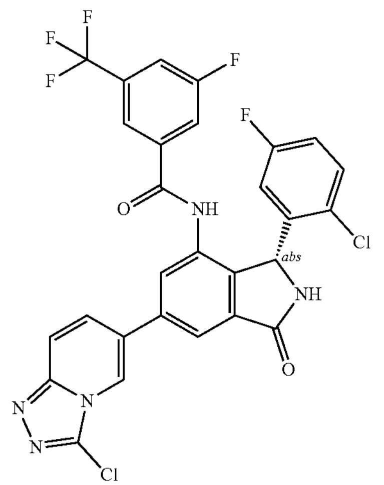 | Fc1ccc(C1)c(c1)[C@@H]1NC(=O)c2cc(cc(NC(=O)c3cc(F)cc(c3)C(F)(F)F)c12)-c1ccc2nnc(Cl)n2c1 | | 618.09 | A | |
| I-1735 | 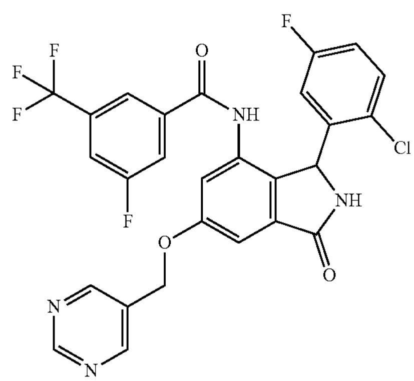 [SMILES: O=C(Nc1cc(OCc2cncnc2)cc2c1C(c1cc(F)ccc1Cl)NC2=O)c1cc(F)cc(C(F)(F)F)c1] | Fc1ccc(C1)c(c1)C1NC(=O)c2cc(OCc3cncnc3)cc(NC(=O)c3cc(F)cc(c3)C(F)(F)F)c12 | | 575.12 | A | |
| I-1736 | 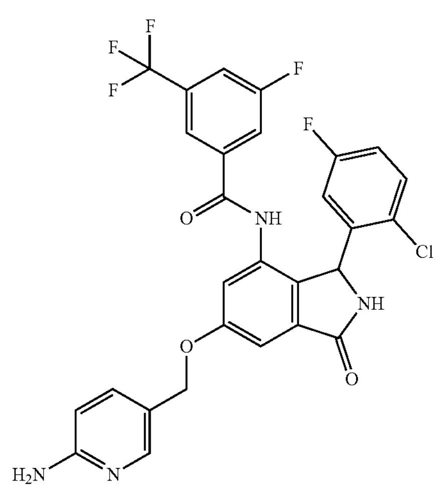 [SMILES: Nc1ccc(COc2cc(NC(=O)c3cc(F)cc(C(F)(F)F)c3)c3c(c2)C(=O)NC3c2cc(F)ccc2Cl)cn1] | Nc1ccc(COc2cc3C(=O)NC(c3c(NC(=O)c3cc(F)cc(c3)C(F)(F)F)c2)c2cc(F)ccc2Cl)cn1 | | 589.13 | A | |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-1737 | 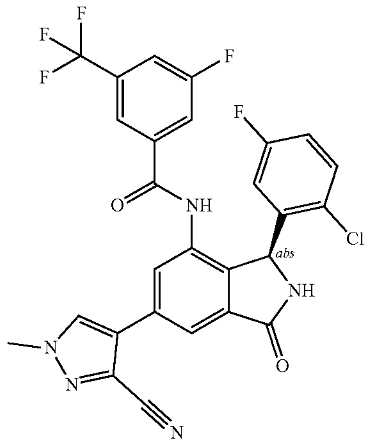 [SMILES: Cn1cc(-c2cc(NC(=O)c3cc(F)cc(C(F)(F)F)c3)c3c(c2)C(=O)N[C@@H]3c2cc(F)ccc2Cl)c(C#N)n1] | Cn1cc(c(n1)C#N)-c1cc2C(=O)N[C@@H](c2c(NC(=O)c2cc(F)cc(c2)C(F)(F)F)c1)c1cc(F)ccc1Cl | | 572.4 | | E |
| I-1738 | 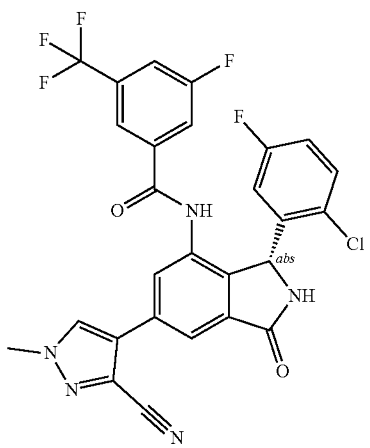 [SMILES: Cn1cc(-c2cc(NC(=O)c3cc(F)cc(C(F)(F)F)c3)c3c(c2)C(=O)N[C@H]3c2cc(F)ccc2Cl)c(C#N)n1] | Cn1cc(c(n1)C#N)-c1cc2C(=O)N[C@H](c2c(NC(=O)c2cc(F)cc(c2)C(F)(F)F)c1)c1cc(F)ccc1Cl | | 572.4 | | A |
| I-1739 | 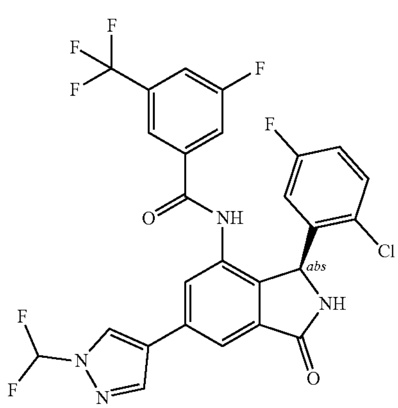 [SMILES: O=C(Nc1cc(-c2cnn(C(F)F)c2)cc2c1[C@@H](c1cc(F)ccc1Cl)NC2=O)c1cc(F)cc(C(F)(F)F)c1] | FC(F)n1cc(cn1)-c1cc2C(=O)N[C@@H](c2c(NC(=O)c2cc(F)cc(c2)C(F)(F)F)c1)c1cc(F)ccc1Cl | ¹H NMR (500 MHz, DMSO-d$_6$) δ 10.55 (s, 1H), 9.17 (s, 1H), 8.94 (s, 1H), 8.44 (s, 1H), 8.06 (d, J = 1.5 Hz, 1H), 7.99-7.69 (m, 5H), 7.32 (dd, J = 8.9, 5.1 Hz, 1H), 7.09 (td, J = 8.4, 3.1 Hz, 1H), 6.92-6.41 (m, 1H), 5.99 (s, 1H). | 583.4 | | D |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-1740 | 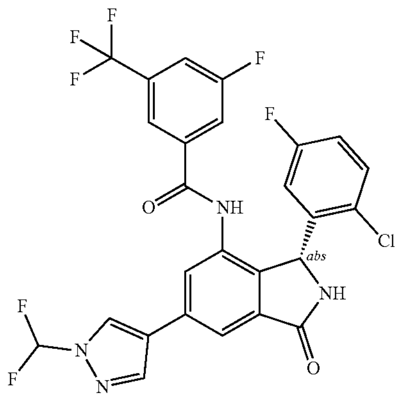 [SMILES: O=C(Nc1cc(-c2cnn(C(F)F)c2)cc2c1[C@H](c1cc(F)ccc1Cl)NC2=O)c1cc(F)cc(C(F)(F)F)c1] | FC(F)n1cc(cn1)-c1cc2C(=O)N[C@H](c2c(NC(=O)c2cc(F)cc(c2)C(F)(F)F)c1)c1ccc(F)ccc1Cl | ¹H NMR (500 MHz, DMSO-d$_6$) δ 10.55 (s, 1H), 9.17 (s, 1H), 8.94 (s, 1H), 8.44 (s, 1H), 8.06 (d, J = 1.5 Hz, 1H), 7.99-7.69 (m, 5H), 7.32 (dd, J = 8.9, 5.1 Hz, 1H), 7.09 (td, J = 8.4, 3.1 Hz, 1H), 6.92-6.41 (m, 1H), 5.99 (s, 1H). | 583.4 | A | A |
| I-1741 | 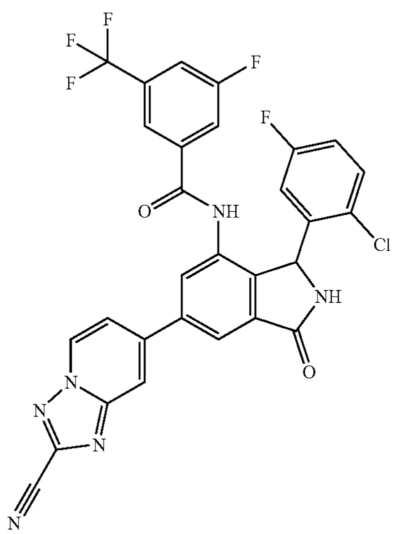 [SMILES: N#Cc1nc2cc(-c3cc(NC(=O)c4cc(F)cc(C(F)(F)F)c4)c4c(c3)C(=O)NC4c3cc(F)ccc3Cl)ccn2n1] | Fc1ccc(C1)c(c1)C1NC(=O)c2cc(cc(NC(=O)c3cc(F)cc(c3)C(F)(F)F)c12)-c1ccn2nc(nc2c1)C#N | | 609.23 | A | |
| I-1742 | 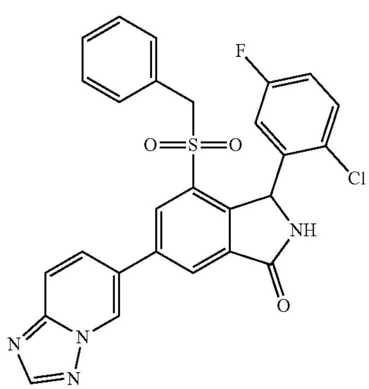 [SMILES: O=C1NC(c2cc(F)ccc2Cl)c2c1cc(-c1ccc3ncnn3c1)cc2S(=O)(=O)Cc1ccccc1] | Fc1ccc(C1)c(c1)C1NC(=O)c2cc(cc(c12)S(=O)(=O)Cc1ccccc1)-c1ccc2ncnn2c1 | 1H NMR (400 MHz, DMSO-d ) 9.59 (br. s, 1H), 9.49 (br. s, 1H), 8.62 (s, 1H), 8.50 (d, 1.5 Hz, 1H), 8.29 (br. s, 1H), 8.16-8.09 (m, 1H), 8.02 (d, 8.5 Hz, 1H), 7.62 (br. s, 1H), 7.40-7.28 (m, 3H), 7.24 (br. s, 1H), 7.02 (d, 6.4 Hz, 2H), 6.42 (br. s, 1H), 6.08 (s, 1H), 4.58 (d, 12.8 Hz, 1H), 4.25 (d, 12.5 Hz, 1H). | 533.1 | D | |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-1743 | 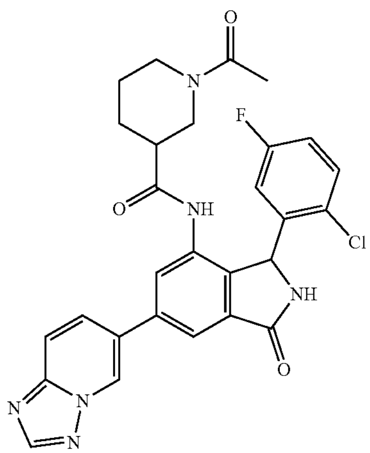 [SMILES: CC(=O)N1CCCC(C(=O)Nc2cc(-c3ccc4ncnn4c3)cc3c2C(c2cc(F)ccc2Cl)NC3=O)C1] | CC(=O)N1CCCC(C1)C(=O)Nc1cc(cc2C(=O)NC(c12)c1cc(F)ccc1Cl)-c1ccc2ncnn2c1 | NMR (400 MHz, DMSO-d6) 10.01 (br s, 1H), 9.45 (s, 1H), 9.23 (br s, 1H), 8.60-8.54 (m, 1H), 8.14-8.08 (m, 1H), 8.05-7.95 (m, 2H), 7.87-7.76 (m, 1H), 7.63-7.46 (m, 1H), 7.33-7.21 (m, 1H), 6.52 (br s, 1H), 6.12 (s, 1H), 4.35-4.07 (m, 1H), 3.79-3.61 (m, 1H), 3.00-2.81 (m, 1H), 2.28-2.07 (m, 1H), 1.95 (s, 3H), 1.74-1.09 (m, 5H) | 547.2 | E | |
| I-1744 | 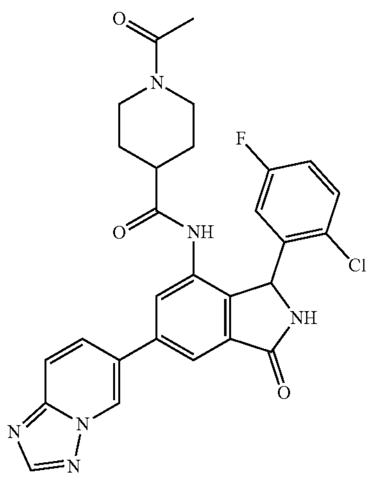 [SMILES: CC(=O)N1CCC(C(=O)Nc2cc(-c3ccc4ncnn4c3)cc3c2C(c2cc(F)ccc2Cl)NC3=O)CC1] | CC(=O)N1CCC(CC1)C(=O)Nc1cc(cc2C(=O)NC(c12)c1cc(F)ccc1Cl)-c1ccc2ncnn2c1 | NMR (400 MHz, DMSO-d6) 9.93 (s, 1H), 9.88 (s, 1H), 9.45 (br s, 2H), 9.23 (br s, 2H), 8.57 (s, 2H), 8.25 (s, 1H), 8.10 (dd, 9.3, 1.8 Hz, 2H), 8.02-8.01 (m, 2H), 7.98 (d, 9.3 Hz, 2H), 7.81 (dd, 12.1, 1.5 Hz, 2H), 7.58-7.49 (m, 2H), 7.31-7.20 (m, 2H), 6.61 (br s, 2H), 6.13 (br s, 2H), 4.30-4.13 (m, 2H), 3.81-3.65 (m, 2H), 3.05-2.88 (m, 2H), 2.37-2.26 (m, 2H), 2.46 (m, 1H), 1.98(s, 6H), 1.60-1.06 (m, 9H). | 547.1 | E | |
| I-1745 | 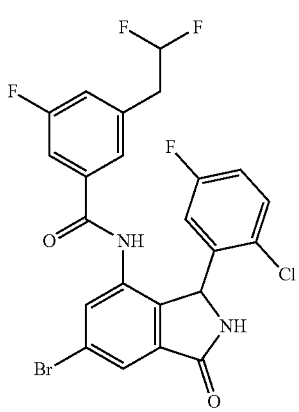 [SMILES: O=C(Nc1cc(Br)cc2c1C(c1cc(F)ccc1Cl)NC2=O)c1cc(F)cc(CC(F)F)c1] | FC(F)Cc1cc(F)cc(c1)C(=O)Nc1cc(Br)cc2C(=O)NC(c12)c1cc(F)ccc1Cl | 1H NMR (400 MHz, DMSO-d6) 10.31 (s, 1H), 9.29 (s, 1H),7.90-7.67 (m, 2H), 7.62-7.27 (m, 3H), 7.25-7.11 (m, 2H), 7.00-7.45 (m,1H), 7.45-6.10 (m,1H), 6.10-5.65 (m,1H), 3.26-3.13 (m, 2H). | 540.95 | D | |

TABLE 2-continued

Representative Compounds of the Invention with Bioactivity Data.

| Ex. No. | Structure | SMILES | $^1$H NMR | MS | ADP-Glo IC$_{50}$ | MCF 10A IC$_{50}$ |
|---|---|---|---|---|---|---|
| I-1746 | 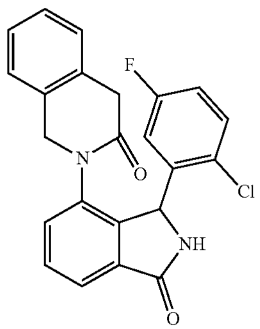 [SMILES: O=C1NC(c2cc(F)ccc2Cl)c2c1cccc2N1Cc2ccccc2CC1=O] | Fc1ccc(C1)c(c1)CNC(=O)c2cccc(N3Cc4cccc4CC3=O)c12 | 1H NMR (400 MHz, DMSO-d6) 9.08 (s, 1H), 7.77-7.65 (m, 2H), 7.59 (d, 7.5 Hz, 1H), 7.21 (t, 7.4 Hz, 1H), 7.18-7.07 (m, 2H), 6.88 (s, 2H), 6.49 (d, 173.5 Hz, 2H), 5.91-5.84 (m, 1H), 4.98 (d, 14.9 Hz, 1H), 3.86-3.59 (m, 2H), 3.45 (d, 18.3 Hz, 1H). | 407.25 | E | |
| I-1747 | 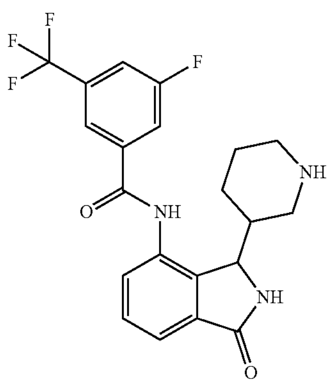 [SMILES: O=C(Nc1cccc2c1C(C1CCCNC1)NC2=O)c1cc(F)cc(C(F)(F)F)c1] | Fc1cc(cc(c1)C(F)(F)F)C(=O)Nc1ccc2C(=O)NC(C3CCCNC3)c12 | (400 MHz, DMSO-d6) 10.79 (br s, 1H), 8.81 (s, 1H), 8.15 (s, 1H), 8.12 (d, 8.5 Hz, 1H), 8.04 (d, 8.4 Hz, 1H), 7.66 (dd, 6.5, 2.3 Hz, 1H), 7.61-7.50 (m, 2H), 4.78 (s, 1H), 2.78 (br d, 10.9 Hz, 1H), 2.25 (t, 11.3 Hz, 1H), 2.05-1.91 (m, 2H), 1.66 (br d, 12.7 Hz, 1H), 1.57 (br d, 12.1 Hz, 1H), 1.52-1.37 (m, 1H), 1.28-1.07 (m, 1H), 0.88-0.67 (m, 1H) | 422.3 | E | |
| I-1748 | 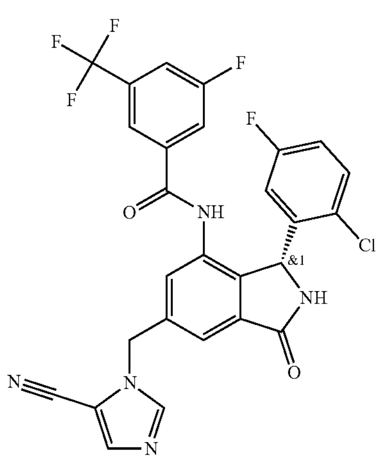 [SMILES: N#Cc1cncn1Cc1cc(NC(=O)c2cc(F)cc(C(F)(F)F)c2)c2c(c1)C(=O)N[C@H]2c1cc(F)ccc1Cl] | Fc1ccc(C1)c(c1)[C@@H]1NC(=O)c2cc(Cn3cncc3C#N)cc(NC(=O)c3cc(F)cc(c3)C(F)(F)F)c12 | 1H-NMR (400 MHz, DMSO-d6) 10.63 (br. s, 1H), 9.17 (br. s, 1H), 8.32 (d, 0.5 Hz, 1H), 7.93 (d, 0.8 Hz, 1H), 7.90-7.83 (m, 1H), 7.72 (br. d, 8.8 Hz, 1H), 7.65 (s, 1H), 7.53-7.40 (m, 2H), 7.32 (dd, 8.8, 5.2 Hz, 1H), 7.08 (app. td, 8.4, 3.0 Hz, 1H), 6.59 (br. s, 1H), 5.95 (br. s, 1H), 5.58 (d, A of AB, JAB = 16.1 Hz, 1H), 5.53 (d, B of AB, JAB = 15.9 Hz, 1H). | 572.3 | A | |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-1749 | 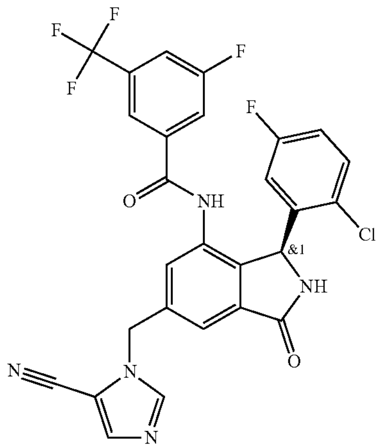 [SMILES: N#Cc1cncn1Cc1cc(NC(=O)c2cc(F)cc(C(F)(F)F)c2)c2c(c1)C(=O)N[C@@H]2c1cc(F)ccc1Cl] | Fc1ccc(C1)c(c1)[C@H]1NC(=O)c2cc(Cn3cncc3C#N)cc(NC(=O)c3cc(F)cc(c3)C(F)(F)F)c12 | 1H-NMR (400 MHz, DMSO-d6) 10.67 (br. s, 1H), 9.20 (s, 1H), 8.32 (s, 1H), 7.94 (s, 1H), 7.91 (br. d, 7.6 Hz, 1H), 7.72 (br. d, 9.1 Hz, 1H), 7.64 (s, 1H), 7.52 (s, 1H), 7.44-7.37 (m, 1H), 7.31 (dd, 8.8, 5.1 Hz, 1H), 7.09 (app. td, 8.5, 3.0 Hz, 1H), 6.64 (br. s, 1H), 5.96 (br. s, 1H), 5.60 (d, A of AB, JAB = 16.1 Hz, 1H), 5.55 (d, B of AB, JAB = 15.7 Hz, 1H). | 572.2 | B | |
| I-1750 | 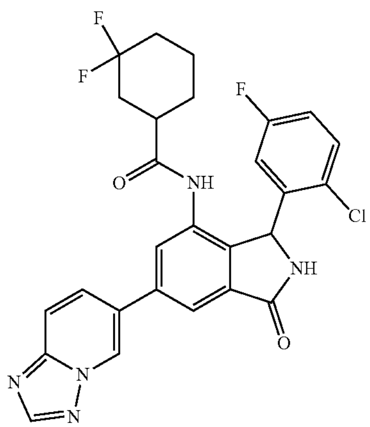 [SMILES: O=C1NC(c2cc(F)ccc2Cl)c2c(NC(=O)C3CCCC(F)(F)C3)cc(-c3ccc4ncnn4c3)cc21] | Fc1ccc(C1)c(c1)C1NC(=O)c2cc(cc(NC(=O)C3CCCC(F)(F)C3)c12)-c1ccc2ncnn2c1 | 1H-NMR (400 MHz, DMSO-d6) 9.98 (s, 2H), 9.45 (s, 2H), 9.23 (br. s, 2H), 8.57 (s, 2H), 8.12-8.08 (m, 2H), 8.03-8.01 (m, 2H), 7.98 (d, 9.2 Hz, 2H), 7.82 (dd, 6.8, 1.4 Hz, 2H), 7.56-7.50 (m, 2H), 7.31-7.23 (m, 2H), 6.58 (br. s, 2H), 6.11 (br. s, 2H), 2.42-2.30 (m, 2H), 2.02-1.91 (m, 2H), 1.90-1.58 (m, 8H), 1.56-1.49 (m, 1H), 1.41-1.28 (m, 3H), 1.24-1.08 (m, 2H). | 540.3 | D | |
| I-1751 | 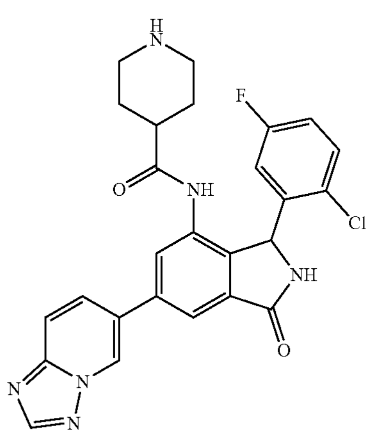 [SMILES: O=C1NC(c2cc(F)ccc2Cl)c2c(NC(=O)C3CCNCC3)cc(-c3ccc4ncnn4c3)cc21] | Fc1ccc(C1)c(c1)C1NC(=O)c2cc(cc(NC(=O)C3CCNCC3)c12)-c1ccc2ncnn2c1 | NMR (400 MHz, DMSO-d6) 10.13 (br s, 1H), 9.44 (s, 1H), 9.24 (br s, 1H), 8.57 (s, 1H), 8.10 (dd, 9.3, 1.7 Hz, 1H), 8.01 (d, 1.2 Hz, 1H), 7.97 (d, 9.2 Hz, 1H), 7.85 (d, 1.4 Hz, 1H), 7.60-7.47 (m, 1H), 7.24 (td, 8.4, 3.0 Hz, 1H), 6.59 (br s, 1H), 6.14 (br s, 1H), 3.14-2.97 (m, 2H), 2.63 (t, 10.8 Hz, 2H), 2.36-2.22 (m, 1H), 1.62-1.27 (m, 4H). | 505 | E | |

TABLE 2-continued

Representative Compounds of the Invention with Bioactivity Data.

| Ex. No. | Structure | SMILES | ¹H NMR | MS | ADP-Glo IC₅₀ | MCF 10A IC₅₀ |
|---|---|---|---|---|---|---|
| I-1752 | 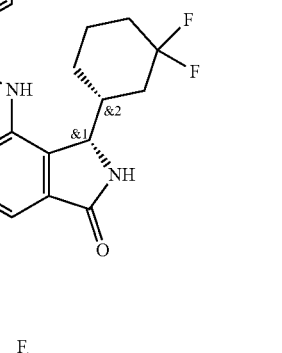 | Fc1cc(cc (c1)C(F) (F)F)C(= O)Nc1cc cc2C(=O) N[C@@ H]([C@ @H]3CC CC(F)(F) C3)c12 | 1H NMR (400 MHz, DMSOd6) 10.89 (s, 1H), 8.81 (s, 1H), 8.08 (s, 1H), 8.05-7.99 (m, 2H), 7.65-7.53 (m, 3H), 4.88 (s, 1H), 2.25-2.13 (m, 1 H), 2.03-1.83 (m, 2H), 1.77 (d, 13.5 Hz, 1H), 1.69-1.51 (m, 2H), 1.43-1.28 (m, 1H), 1.28-1.11 (m, 2H), 1.06-0.92 (m, 1H). | 455.3 | D | |
| I-1753 | 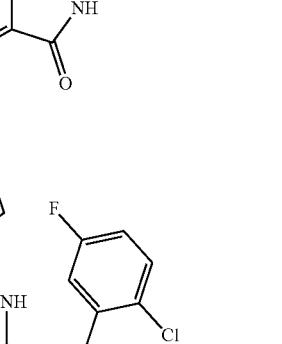 | Fc1ccc(C 1)c(c1)C1 NC(=O)c 2cc(Br)cc (NC(=O) N3CC4C C(F)(C4) C3)c12 | 1H NMR (400 MHz, DMSO):-' 9.27 (br s, 1H), 8.38 (s, 1H), 7.63 (d, 1.5 Hz, 1H), 7.50 (br s, 1H), 7.48 (d, 1.7 Hz, 1H), 7.25 (td, 8.2, 2.7 Hz, 1H), 6.55 (br s, 1H), 5.97 (br s, 1H), 3.60-3.41 (m, 3H), 3.28-3.22 (m, 1H), 2.47-2.36 (m, 1H), 2.22 (dd, 18.0, 8.6 Hz, 2H), 1.62 (br s, 2H). | 496.2 | E | |
| I-1754 | 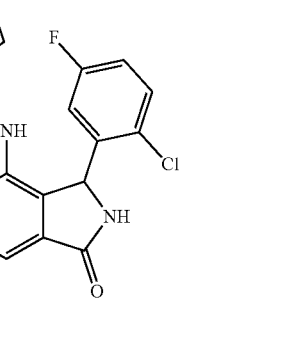 | Fc1ccc(C 1)c(c1)C1 NC(=O)c 2cc(Br)cc (NC(=O) N3CC4C CC4(C3) C(F)(F)F) c12 | 1H NMR (400 MHz, DMSO):-' 9.21 (br s, 1H), 8.62 (s, 1H), 7.63 (s, 1H), 7.57 (d, 1.7 Hz, 0.5H), 7.56 (d, 1.7 Hz, 0.5H), 7.44 (br s, 1H), 7.22 (2 overlapping td, 8.4, 3.1 Hz, 1H), 6.59 (br s, 1H), 6.02 (br s, 1H), 3.65 (d, 11.4 Hz, 0.5H), 3.46 (d, 11.0 Hz, 0.5H), 3.30 (d, 11.7 H2, 1H), 3.24 (d, 11.8 Hz, 0.5H), 3.15 (dd, 11.1, 6.4 Hz, 0.5H), 3.05-2.94 (m, 1H), 2.94-2.86 (m, 0.5H), 2.76-2.65 (m, 0.5H), 2.36-2.24 (m, 1H), 2.19-2.05 (m, 1H), 1.90-1.81 (m, 0.5H), 1.81-1.71 (m, 0.5H), 1.66-1.54 (m, 0.5H), 1.51-1.39 (m, 0.5H). | 546.2 | D | |
| I-1755 | 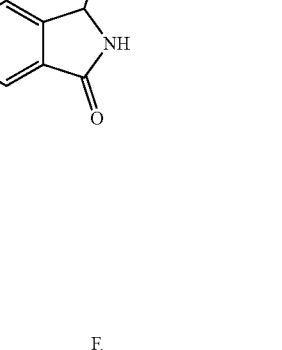 | Fc1ccc(C 1)c(c1)C1 NC(=O)c 2cc(Br)cc (NC(=O) NC3(CC (F)(F)F)C C3)c12 | 1H NMR (400 MHz, DMSO):-' 9.16 (s, 1H), 8.64 (br s, 0.5H), 8.49 (br s, 0.5H), 7.75 (s, 1H), 7.53 (s, 1H), 7.49-7.41 (m, 1H), 7.35 (s, 1H), 7.20 (td, 8.3, 2.8 Hz, 1H), 6.64 (br s, 1H), 6.11 (s, 1H), 2.49-2.34 (m, 2H), 0.76-0.52 (m, 4H). | 520.1 | E | |

TABLE 2-continued

Representative Compounds of the Invention with Bioactivity Data.

| Ex. No. | Structure | SMILES | $^1$H NMR | MS | ADP-Glo IC$_{50}$ | MCF 10A IC$_{50}$ |
|---|---|---|---|---|---|---|
| I-1756 | 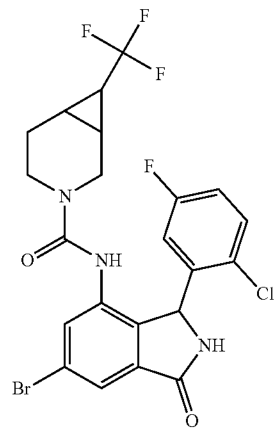 [SMILES: O=C1NC(c2cc(F)ccc2Cl)c2c(NC(=O)N3CCC4C(C3)C4C(F)(F)F)cc(Br)cc21] | Fc1ccc(C 1)c(c1)C1 NC(=O)c 2cc(Br)cc (NC(=O) N3CCC4 C(C3)C4 C(F)(F)F) c12 | 1H NMR (400 MHz, DMSO):-' 9.17 (br s, 1H), 8.40 (s, 0.5H), 8.36 (s, 0.5H), 7.58 (d, 1.7 Hz, 0.5H), 7.57 (d, 1.7 Hz, 0.5H), 7.51 (d, 1.7 Hz, 0.5H), 7.43 (br s and d, 1.7 Hz, 1.5H), 7.27-7.18 (m, 1H), 6.63 (br s, 1H), 5.90 (br s, 1H), 3.61-3.52 (m, 0.5H), 3.48-3.43 (m, 1.5H), 3.19-3.11 (m, 1H), 2.81-2.72 (m, 0.5H), 2.43-2.33 (m, 0.5H), 2.04-1.94 (m, 0.5H), 1.90-1.80 (m, 0.5H), 1.80-1.66 (m, 1H), 1.57-1.33 (m, 3H). | 546.1 | D | |
| I-1757 | 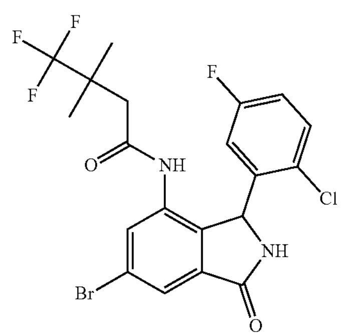 [SMILES: CC(C)(CC(=O)Nc1cc(Br)cc2c1C(c1cc(F)ccc1Cl)NC2=O)C(F)(F)F] | CC(C)(C C(=O)Nc 1cc(Br)cc 2C(=O)N C(c12)c1 cc(F)ccc1 Cl)C(F) (F)F | 1H NMR (400 MHz, DMSO):-' 9.95 (s, 1H), 9.27 (s, 1H), 7.74-7.70 (m, 2H), 7.51 (br s, 1H), 7.24 (td, 8.4, 3.1 Hz, 1H), 6.63 (br s, 1H), 6.04 (br s, 1H), 2.21 (2 overlapping d, 13.9 Hz, 2H), 1.01 (br s, 3H), 0.94 (s, 3H). | 507 | E | |
| I-1758 | 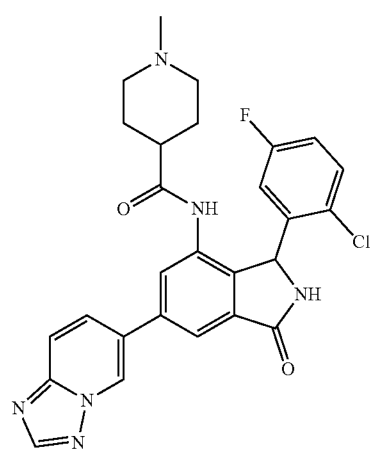 [SMILES: CN1CCC(C(=O)Nc2cc(-c3ccc4ncnn4c3)cc3c2C(c2cc(F)ccc2Cl)NC3=O)CC1] | CN1CCC (CC1)C (=O)Nc1c c(cc2C(= O)NC(c1 2)c1cc(F) ccc1Cl)- c1ccc2nc nn2c1 | NMR (400 MHz, DMSO-d6) 9.88 (br s, 1H), 9.44 (s, 1H), 9.22 (br s, 1H), 8.57 (s, 1H), 8.09 (dd, 9.3, 1.7 Hz, 1H), 8.00 (d, 1.2 Hz, 1H), 7.97 (d, 9.2 Hz, 1H), 7.81 (d, 1.3 Hz, 1H), 7.60-7.40 (m, 1H), 7.25 (td, 8.4, 3.1 Hz, 1H), 6.56 (br s, 1H), 6.13 (br s, 1H), 2.72 (t, 11.2 Hz, 2H), 2.14 (s, 3H), 2.08-1.93 (m, 1H), 1.86-1.72 (m, 2H), 1.49-1.18 (m, 4H). | 519 | E | |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-1759 | 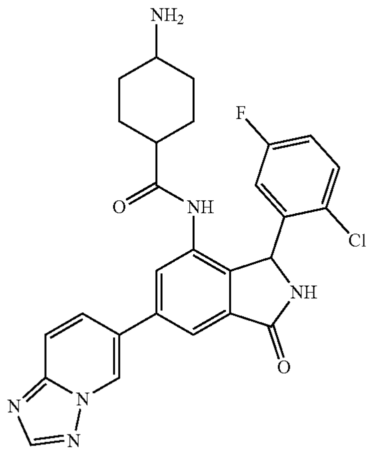 [SMILES: NC1CCC(C(=O)Nc2cc(-c3ccc4ncnn4c3)cc3c2C(c2cc(F)ccc2Cl)NC3=O)CC1] | NC1CCC(CC1)C(=O)Nc1cc(cc2C(=O)NC(c12)c1cc(F)ccc1Cl)-c1ccc2ncnn2c1 | NMR (400 MHz, DMSO-d6) 9.95 (br s, 1H), 9.44 (s, 1H), 9.21 (br s, 1H), 8.57 (s, 1H), 8.39 (br s, 2H), 8.00 (s, 1H), 7.97 (d, 9.0 Hz, 1H), 7.96 (s, 1H), 7.82 (br d, 4.7 Hz, 1H), 7.58-7.47 (m, 1H), 7.29-7.21 (m, 1H), 6.70 (br s, 1H), 6.11 (br s, 1H), 2.89-2.70 (m, 1H), 2.09-1.95 (m, 1H), 1.93-1.78 (m, 2H), 1.60-1.44 (m, 1H), 1.43-1.30 (m, 1H), 1.30-1.09 (m, 4H). | 519 | E | |
| I-1760 | 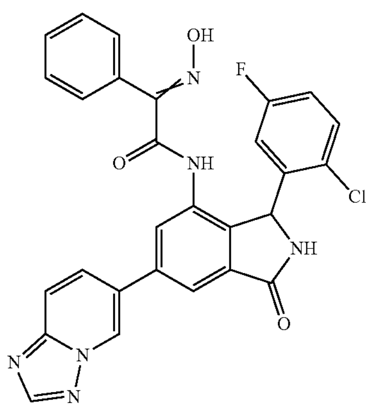 [SMILES: O=C(Nc1cc(-c2ccc3ncnn3c2)cc2c1C(c1cc(F)ccc1Cl)NC2=O)C(=NO)c1ccccc1] | ON=C(C(=O)Nc1cc(cc2C(=O)NC(c12)c1cc(F)ccc1Cl)-c1ccc2ncnn2c1)c1ccccc1 | NMR (400 MHz, DMSO-d6) 10.62 (br s, 1H), 9.45 (br s, 1H), 9.27 (br s, 1H), 8.59 (s, 1H), 8.15-7.95 (m, 5H), 7.63-7.50 (m, 1H), 7.42-7.37 (m, 1H), 7.32-7.24 (m, 3H), 7.14 (s, 1H), 7.12 (s, 1H), 6.60 (br s, 1H), 6.33 (br s, 1H). | 541 | E | |
| I-1761 | 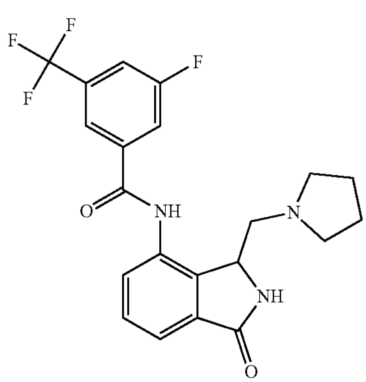 [SMILES: O=C(Nc1cccc2c1C(CN1CCCC1)NC2=O)c1cc(F)cc(C(F)(F)F)c1] | Fc1cc(cc(c1)C(F)(F)F)C(=O)Nc1cccc2C(=O)NC(CN3CCCC3)c12 | NMR (400 MHz, CD3CN) 12.43 (br. s, 1H), 8.45 (dd, 7.3, 1.6 Hz, 1H) 7.93 (s, 1H), 7.77 (br. d, 8.6 Hz, 1H), 7.68 (br. d, 8.6 Hz, 1H), 7.54-7.48 (m, 2H), 6.86 (br. s, 1H), 4.79 (ddd, 8.9, 4.5, 1.0 Hz, 1H), 2.79 (d, 4.9 Hz, 1H), 2.77 (s, 1H) 2.75-2.67 (m, 2H), 2.59-2.51 (m, 2H), 1.35 1.28 (m, 3H), 1.28-1.22 (m, 1H) | 422.2 | E | |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-1762 | 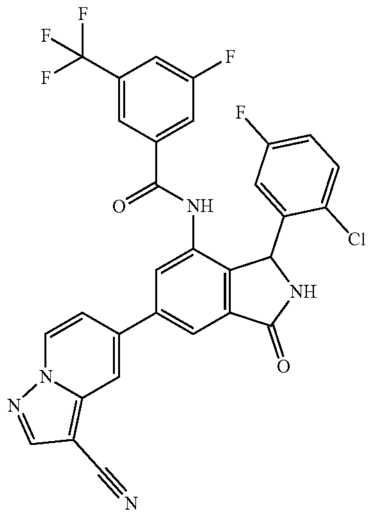 [SMILES: N#Cc1cnn2ccc(-c3cc(NC(=O)c4cc(F)cc(C(F)(F)F)c4)c4c(c3)C(=O)NC4c3cc(F)ccc3Cl)cc12] | Fc1ccc(C1)c(c1)C1NC(=O)c2cc(cc(NC(=O)c3cc(F)cc(c3)C(F)(F)F)c12)-c1ccn2ncc(C#N)c2c1 | 1H NMR (DMSO-d6, 400 MHz) 10.64 (s, 1H), 9.28 (br s, 1H), 9.07 (d, 7.3 Hz, 1H), 8.70 (s, 1H), 8.39 (d, 1.3 Hz, 1H), 8.24 (d, 1.5 Hz, 1H), 8.08-8.11 (m, 1H), 7.95-8.00 (m, 1H), 7.76-7.81 (m, 1H), 7.71-7.74 (m, 2H), 7.70 (d, 2.0 Hz, 1H), 7.32-7.37 (m, 1H), 7.09-7.15 (m, 1H), 6.02-6.14 (m, 1H) | 608.4 | A | |
| I-1763 | 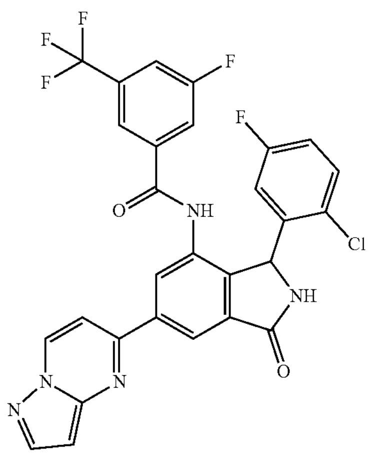 [SMILES: O=C(Nc1cc(-c2ccn3nccc3n2)cc2c1C(c1cc(F)ccc1Cl)NC2=O)c1cc(F)cc(C(F)(F)F)c1] | Fc1ccc(C1)c(c1)C1NC(=O)c2cc(cc(NC(=O)c3cc(F)cc(c3)C(F)(F)F)c12)-c1ccn2nccc2n1 | 1H NMR (DMSO-d6, 400 MHz):-' = 10.70 (s, 1H), 9.27-9.34 (m, 1H), 9.25 (dd, 7.3, 0.8 Hz, 1H), 8.48 (d, 1.0 Hz, 1H), 8.42 (d, 1.0 Hz, 1H), 8.29 (d, 2.3 Hz, 1H), 7.97 (br d, 8.6 Hz, 1H), 7.84 (d, 7.3 Hz, 1H), 7.80 (br d, 8.8 Hz, 1H), 7.74 (s, 1H), 7.34 (dd, 8.8, 5.3 Hz, 1H), 7.11 (td, 8.4, 3.2 Hz, 1H), 6.81 (dd, 2.3, 0.8 Hz, 1H), 6.02-6.20 (m, 1H) | 584.4 | A | |
| I-1764 | 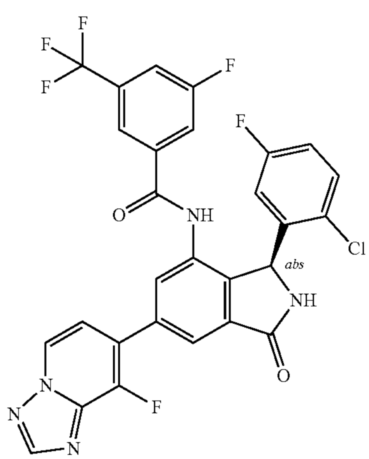 [SMILES: O=C(Nc1cc(-c2ccn3ncnc3c2F)cc2c1[C@@H](c1cc(F)ccc1Cl)NC2=O)c1cc(F)cc(C(F)(F)F)c1] | Fc1ccc(C1)c(c1)[C@H]1NC(=O)c2cc(cc(NC(=O)c3cc(F)cc(c3)C(F)(F)F)c12)-c1ccn2ncnc2c1F | 1H NMR (400 MHz, DMSO) δ 10.69 (s, 1H), 9.31 (s, 1H), 8.99 (d, J = 7.1 Hz, 1H), 8.65 (s, 1H), 8.00 (d, J = 1.4 Hz, 1H), 7.95 (dt, J = 8.6, 1.9 Hz, 1H), 7.85 (s, 1H), 7.76 (dd, J = 9.1, 2.5 Hz, 1H), 7.68 (s, 1H), 7.50 (q, J = 7.1 Hz, 1H), 7.34 (dd, J = 8.9, 5.2 Hz, 1H), 7.15-7.07 (m, 1H), 6.69 (s, 1H), 6.07 (s, 1H). | 602.18 | D | |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-1765 | 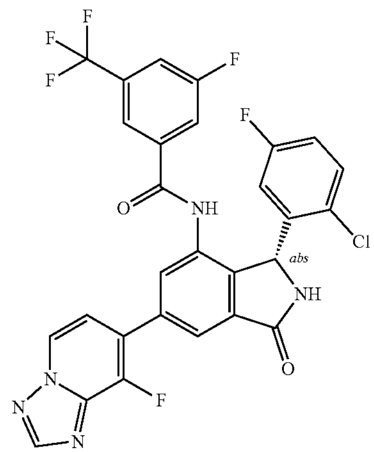 [SMILES: O=C(Nc1cc(-c2ccn3ncnc3c2F)cc2c1[C@H](c1cc(F)ccc1Cl)NC2=O)c1cc(F)cc(C(F)(F)F)c1] | Fc1ccc(C1)c(c1)[C@@H]1NC(=O)c2cc(cc(NC(=O)c3cc(F)cc(c3)C(F)(F)F)c12)-c1ccn2ncnc2c1F | 1H NMR (400 MHz, DMSO) δ 10.69 (s, 1H), 9.31 (s, 1H), 8.99 (d, J = 7.1 Hz, 1H), 8.65 (s, 1H), 8.00 (d, J = 1.4 Hz, 1H), 7.95 (dt, J = 8.6, 1.9 Hz, 1H), 7.85 (s, 1H), 7.76 (dd, J = 9.1, 2.5 Hz, 1H), 7.68 (s, 1H), 7.50 (q, J = 7.1 Hz, 1H), 7.34 (dd, J = 8.9, 5.2 Hz, 1H), 7.15-7.07 (m, 1H), 6.69 (s, 1H), 6.07 (s, 1H). | 602.18 | A | |
| I-1766 | 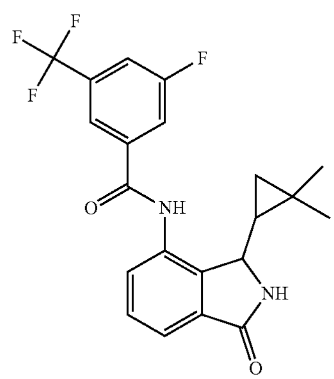 [SMILES: CC1(C)CC1C1NC(=O)c2cccc(NC(=O)c3cc(F)cc(C(F)(F)F)c3)c21] | CC1(C)CC1C1NC(=O)c2ccc(NC(=O)c3cc(F)cc(c3)C(F)(F)F)c12 | NMR (400 MHz, DMSO-d6) 10.56 (s, 1H), 8.77 (s, 1H), 8.20 (s, 1H), 8.14 (br. d, 9.2 Hz, 1H), 8.03 (br. d, 8.4 Hz, 1H), 7.66-7.51 (m, 3H), 4.48-4.41 (m, 1H), 1.14 (s, 3H), 0.93 (s, 3H), 0.34-0.24 (m, 3H). | 407.2 | D | |
| I-1767 | 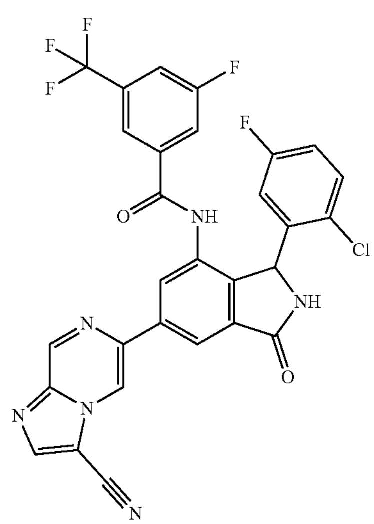 [SMILES: N#Cc1cnc2cnc(-c3cc(NC(=O)c4cc(F)cc(C(F)(F)F)c4)c4c(c3)C(=O)NC4c3cc(F)ccc3Cl)cn12] | Fc1ccc(C1)c(c1)C1NC(=O)c2cc(cc(NC(=O)c3cc(F)cc(c3)C(F)(F)F)c12)-c1cn2c(cnc2cn1)C#N | | 609.03 | A | |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-1768 | 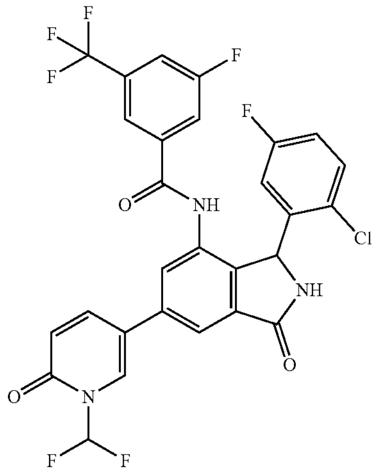 [SMILES: O=C(Nc1cc(-c2ccc(=O)n(C(F)F)c2)cc2c1C(c1cc(F)ccc1Cl)NC2=O)c1cc(F)cc(C(F)(F)F)c1] | FC(F)n1cc(ccc1=O)-c1cc2C(=O)NC(c2c(NC(=O)c2cc(F)cc(c2)C(F)(F)F)c1)c1cc(F)ccc1Cl | | 610.5 | A | |
| I-1769 | 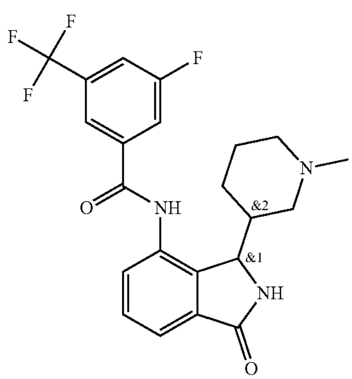 [SMILES: CN1CCCC(C2NC(=O)c3cccc(NC(=O)c4cc(F)cc(C(F)(F)F)c4)c32)C1] | CN1CCCC(C1)C1NC(=O)c2cccc(NC(=O)c3cc(F)cc(c3)C(F)(F)F)c12 | (400 MHz, DMSO-d6) 10.80 (s, 1H), 8.79 (s, 1H), 8.15 (s, 1H), 8.09 (d, 9.1 Hz, 1H), 8.04 (d, 8.4 Hz, 1H), 7.62 (dd, 6.9, 1.9 Hz, 1H), 7.60-7.52 (m, 2H), 4.81 (d, 1.2 Hz, 1H), 2.60 (d, 10.4 Hz, 1H), 2.15-2.04 (m, 1H), 1.89 (s, 3H), 1.83 (d, 10.8 Hz, 1H), 1.64-1.56 (m, 3H), 1.39 (t, 10.9 Hz, 1H), 1.31-1.21 (m, 2H) | 436.3 | E | |
| I-1770 | 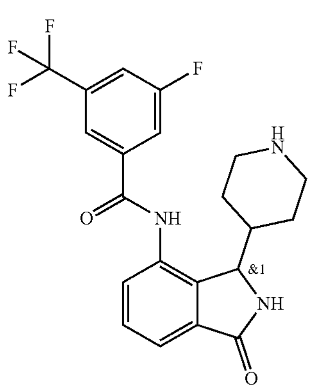 [SMILES: O=C(Nc1cccc2c1C(C1CCNCC1)NC2=O)c1cc(F)cc(C(F)(F)F)c1] | Fc1cc(cc(c1)C(F)(F)F)C(=O)Nc1ccc c2C(=O)NC(C3CCNCC3)c12 | (400 MHz, DMSO-d6) 10.72 (br s, 1H), 8.78 (s, 1H), 8.14 (s, 1H), 8.10 (d, 9.0 Hz, 1H), 8.04 (d, 8.5 Hz, 1H), 7.61 (dd, 7.3, 1.4 Hz, 1H), 7.59-7.50 (m, 2H), 4.77 (d, 1.1 Hz, 1H), 2.98 (d, 11.8 Hz, 1H), 2.82 (d, 11.5 Hz, 1H), 2.35-2.20 (m, 2H), 2.00-1.87 (m, 1H), 1.55-1.43 (m, 2H), 0.93-0.80 (m, 1H), 0.57 (d, 10.8 Hz, 1H) | 422.3 | D | |

TABLE 2-continued

Representative Compounds of the Invention with Bioactivity Data.

| Ex. No. | Structure | SMILES | ¹H NMR | MS | ADP-Glo IC₅₀ | MCF 10A IC₅₀ |
|---|---|---|---|---|---|---|
| I-1771 | 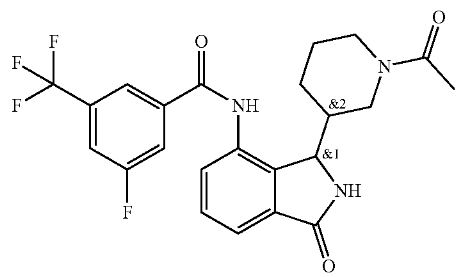 [SMILES: CC(=O)N1CCCC(C2NC(=O)c3cccc(NC(=O)c4cc(F)cc(C(F)(F)F)c4)c32)C1] | CC(=O)N1CCCC(C1)C1NC(=O)c2cccc(NC(=O)c3cc(F)cc(c3)C(F)(F)F)c12 | (400 MHz, DMSO-d6) 10.96 (br s, 0.5H), 10.85 (br s, 0.5H), 8.89 (s, 0.5H), 8.83 (s, 0.5H), 8.13-7.97 (m, 3H), 7.69-7.52 (m, 3H), 4.87 (d, 0.9 Hz, 0.5H), 4.77 (d, 1.4 Hz, 0.5H), 4.27 (d, 12.3 Hz, 0.5H), 3.68 (d, 12.3 Hz, 0.5H), 3.64 (d, 12.3 Hz, 0.5H), 2.77 (app t, 12.3 Hz, 1H), 2.55-2.51 (m, 1H), 2.22 (1, 12.1 Hz, 0.5H), 1.94 (t, 12.1 Hz., 1H), 1.89 (s, 1.5H), 1.86-1.64 (m, 2.5H), 1.62 (s, 1.5H), 1.60-1.51 (m, 0.5H), 1.21-1.00 (m, 1H) | 464.3 | E | |
| I-1772 | 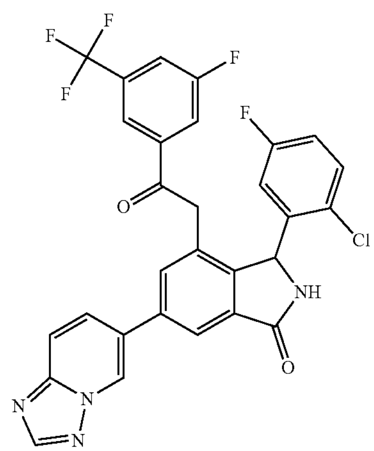 [SMILES: O=C(Cc1cc(-c2ccc3ncnn3c2)cc2c1C(c1cc(F)ccc1Cl)NC2=O)c1cc(F)cc(C(F)(F)F)c1] | Fc1ccc(C1)c(c1)C1NC(=O)c2cc(cc(CC(=O)c3cc(F)cc(c3)C(F)(F)F)c12)-c1ccc2ncnn2c1 | | 583.2 | B | |
| I-1773 | 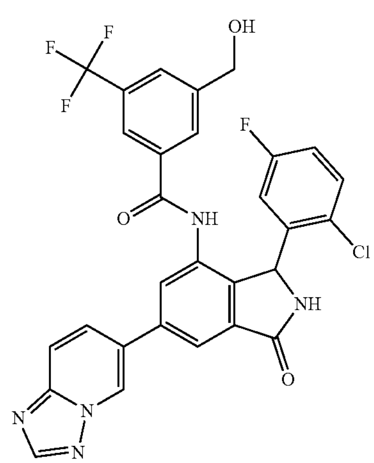 [SMILES: O=C(Nc1cc(-c2ccc3ncnn3c2)cc2c1C(c1cc(F)ccc1Cl)NC2=O)c1cc(CO)cc(C(F)(F)F)c1] | OCc1cc(cc(c1)C(F)(F)F)C(=O)Nc1cc(cc2C(=O)NC(c12)c1cc(F)ccc1Cl)-c1ccc2ncnn2c1 | NMR (400 MHz, DMSO-d6) 9.35 (s, 1H), 9.07 (s, 1H), 8.54 (s, 1H), 8.12 (s, 1H), 8.02 (dd, 9.3, 1.8 Hz, 1H), 7.99 (s, 1H), 7.89 (d, 9.2 Hz, 1H), 7.70 (s, 1H), 7.54 (dd, 8.3, 5.1 Hz, 1H), 7.40 (d, 1.3 Hz, 1H), 7.24 (td, 8.0, 3.0 Hz, 1H), 7.18 (s, 1H), 6.73 (br s, 1H), 5.96 (s, 1H), 5.69 (t, 6.2 Hz, 1H), 4.71 (dd, 16.1, 6.3 Hz, 1H), 4.53 (dd, 16.0, 5.5 Hz, 1H). | 596.3 | E | |

TABLE 2-continued

Representative Compounds of the Invention with Bioactivity Data.

| Ex. No. | Structure | SMILES | $^1$H NMR | MS | ADP-Glo IC$_{50}$ | MCF 10A IC$_{50}$ |
|---|---|---|---|---|---|---|
| I-1774 | 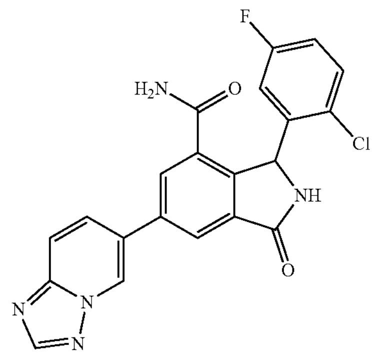 [SMILES: NC(=O)c1cc(-c2ccc3ncnn3c2)cc2c1C(c1cc(F)ccc1Cl)NC2=O] | NC(=O)c1cc(cc2C(=O)NC(c12)c1cc(F)ccc1Cl)-c1ccc2ncnn2c1 | (400 MHz, DMSO-d6) 9.59 (d, 0.8 Hz, 1 H), 9.30 (s, 1 H), 8.59 (s, 1 H), 8.37 (s, 1 H), 8.29 (d, 1.5 Hz, 1 H), 8.26 (dd, 9.3, 1.8 Hz, 1 H), 8.11 (s, 1 H), 8.01 (d, 9.3 Hz, 1 H), 7.49 (br s, 1 H), 7.45 (s, 1 H), 7.18 (td, 8.4, 3.1 Hz, 1 H), 6.43 (br s, 1 H). | 422.1 | D | |
| I-1775 | 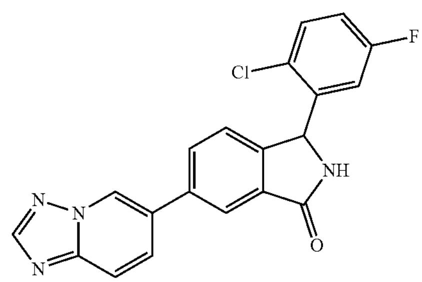 [SMILES: O=C1NC(c2cc(F)ccc2Cl)c2ccc(-c3ccc4ncnn4c3)cc21] | Fc1ccc(C1)c(c1)C1NC(=O)c2cc(ccc12)-c1ccc2ncnn2c1 | (400 MHz, DMSO-d6) 9.42 (app d, 0.8 Hz, 1 H), 9.17 (s, 1 H), 8.56 (s, 1 H), 8.13 (d, 1.4 Hz, 1 H), 8.09 (dd, 9.3, 1.8 Hz, 1 H), 8.01 (dd, 8.0, 1.8 Hz, 1 H), 7.95 (dd, 9.3, 0.5 Hz, 1 H), 7.66 (dd, 8.9, 5.1 Hz, 1 H), 7.53 (d, 8.0 Hz, 1 H), 7.28 (ddd, 8.8, 8.1, 3.1 Hz, 1 H), 7.01 (dd, 9.3, 3.0 Hz, 1 H), 6.18 (s, 1 H). | 379.2 | E | |
| I-1776 | 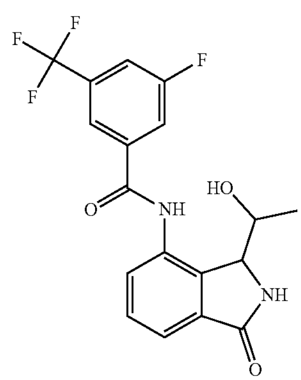 [SMILES: CC(O)C1NC(=O)c2cccc(NC(=O)c3cc(F)cc(C(F)(F)F)c3)c21] | CC(O)C1NC(=O)c2cccc(NC(=O)c3cc(F)cc(c3)C(F)(F)F)c12 | NMR (400 MHz, DMSO-d6) 11.29 (br. s, 1H), 8.72 (s, 1H), 8.44 (d, 7.5 Hz, 1H), 8.10 (s, 1H), 8.07-8.00 (m, 2H), 7.55 (t, 7.7 Hz, 1H), 7.48 (dd, 7.4, 0.8 Hz, 1H), 6.88 (br. s, 1H), 4.87 (d, 2.9 Hz, 1H), 4.29-4.22 (m, 1H), 0.73 (d, 6.3 Hz, 3H). | 383.2 | D | |
| I-1777 | 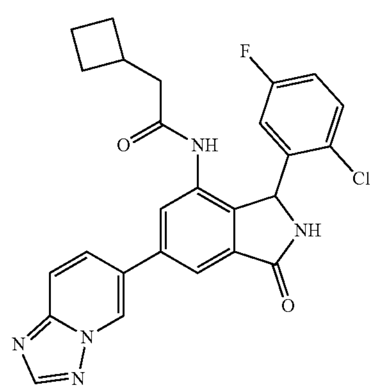 [SMILES: O=C(CC1CCC1)Nc1cc(-c2ccc3ncnn3c2)cc2c1C(c1cc(F)ccc1Cl)NC2=O] | Fc1ccc(C1)c(c1)C1NC(=O)c2cc(cc(NC(=O)CC3CCC3)c12)-c1ccc2ncnn2c1 | 1H NMR (400 MHz, DMSO-d6) 9.69 (s, 1H), 9.42 (d, 1.6 Hz, 1H), 9.16 (s, 1H), 8.57 (s, 1H), 8.08 (dd, 9.3, 1.9 Hz, 1H), 8.01-7.93 (m, 2H), 7.84 (d, 1.7 Hz, 1H), 7.53 (d, 7.7 Hz, 1H), 7.26 (td, 8.4, 3.1 Hz, 1H), 6.66 (s, 1H), 6.12 (s, 1H), 2.43-2.33 (m, 1H), 2.25-2.09 (m, 2H), 1.95-1.82 (m, 2H), 1.81-1.68 (m, 2H), 1.51 (p, 8.7 Hz., 2H). | 490.25 | E | |

TABLE 2-continued

Representative Compounds of the Invention with Bioactivity Data.

| Ex. No. | Structure | SMILES | $^1$H NMR | MS | ADP-Glo IC$_{50}$ | MCF 10A IC$_{50}$ |
|---|---|---|---|---|---|---|
| I-1778 | 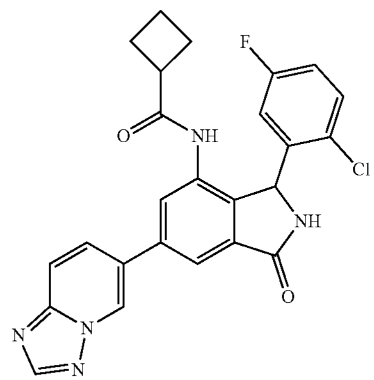 [SMILES: O=C1NC(c2cc(F)ccc2Cl)c2c(NC(=O)C3CCC3)cc(-c3ccc4ncnn4c3)cc21] | Fc1ccc(C1)c(c1)C1NC(=O)c2cc(cc(NC(=O)C3CCC3)c12)-c1ccc2ncnn2c1 | 1H NMR (400 MHz, DMSO-d6) 9.69-9.10 (m, 2H), 8.56 (s, 1H), 8.09 (dd, 9.3, 1.9 Hz, 1H), 8.03-7.91 (m, 2H), 7.80 (t, 1.8 Hz, 1H), 7.51 (dd, 9.0, 5.2 Hz, 1H), 7.24 (td, 8.4, 3.1 Hz, 1H), 6.67 (s, 1H), 6.13 (s, 1H), 2.96 (ddt, 12.4, 9.0, 4.9 Hz, 1H), 2.05-1.58 (m, 6H) | 476.1 | E | |
| I-1779 | 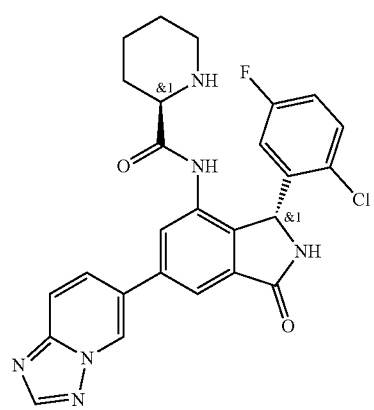 [SMILES: O=C1N[C@@H](c2cc(F)ccc2Cl)c2c(NC(=O)[C@H]3CCCCN3)cc(-c3ccc4ncnn4c3)cc21] | Fc1ccc(C1)c(c1)[C@@H]1NC(=O)c2cc(cc(NC(=O)[C@H]3CCCCN3)c12)-c1ccc2ncnn2c1 | 1H NMR (400 MHz, DMSO-d6) 9.41 (t, 1.3 Hz, 1H), 9.27 (s, 1H), 8.97 (s, 1H), 8.77 (q, 16.4, 13.1 Hz, 1H), 8.59 (s, 1H), 8.18-7.92 (m, 4H), 7.55 (t, 7.2 Hz, 2H), 7.28 (td, 8.4, 3.1 Hz, 1H), 6.11 (s, 1H), 3.93-3.71 (m, 1H), 3.23 (d, 12.7 Hz, 1H), 3.02-2.88 (m, 1H), 1.81-1.34 (m, 7H), 0.97 (q, 11.7 Hz, 1H). | 505.15 | E | |
| I-1780 | 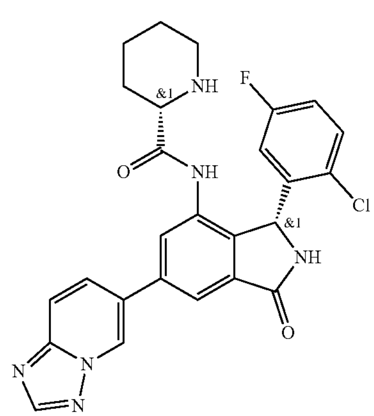 [SMILES: O=C1N[C@@H](c2cc(F)ccc2Cl)c2c(NC(=O)[C@@H]3CCCCN3)cc(-c3ccc4ncnn4c3)cc21] | Fc1ccc(C1)c(c1)[C@@H]1NC(=O)c2cc(cc(NC(=O)[C@@H]3CCCCN3)c12)-c1ccc2ncnn2c1 | 1H NMR (400 MHz, DMSO-d6) 9.41 (t, 1.3 Hz, 1H), 9.27 (s, 1H), 8.97 (s, 1H), 8.77 (q, 16.4, 13.1 Hz, 1H), 8.59 (s, 1H), 8.18-7.92 (m, 4H), 7.55 (t, 7.2 Hz, 2H), 7.28 (td, 8.4, 3.1 Hz, 1H), 6.11 (s, 1H), 3.93-3.71 (m, 1H), 3.23 (d, 12.7 Hz, 1H), 3.02-2.88 (m, 1H), 1.81-1.34 (m, 7H), 0.97 (q, 11.7 Hz, 1H). | 505.15 | E | |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-1781 | 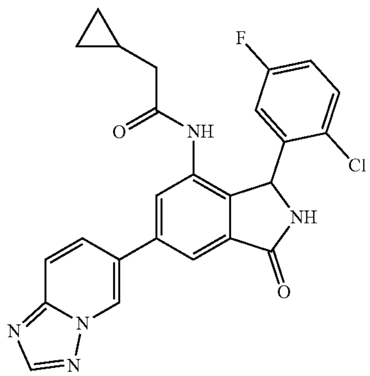 [SMILES: O=C(CC1CC1)Nc1cc(-c2ccc3ncnn3c2)cc2c1C(c1cc(F)ccc1Cl)NC2=O] | Fc1ccc(C1)c(c1)C1NC(=O)c2cc(cc(NC(=O)CC3CC3)c12)-c1ccc2ncnn2c1 | 1H NMR (400 MHz, DMSO-d6) 9.80-9.14 (m, 2H), 8.57 (s, 1H), 8.09 (dd, 9.3, 1.9 Hz, 1H), 8.02-7.92 (m, 2H), 7.85 (t, 1.9 Hz, 1H), 7.52 (dd, 8.9, 5.1 Hz, 1H), 7.24 (td, 8.4, 3.1 Hz, 1H), 6.66 (s, 1H), 6.13 (s, 1H), 2.03-1.87 (m, 2H), 0.77 (ddt, 12.4, 7.8, 3.7 Hz, 1H), 0.45-0.25 (m, 2H), 0.04-0.07 (m, 2H). | 476.1 | E | |
| I-1782 | 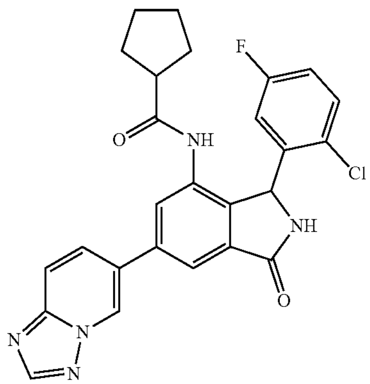 [SMILES: O=C1NC(c2cc(F)ccc2Cl)c2c(NC(=O)C3CCCC3)cc(-c3ccc4ncnn4c3)cc21] | Fc1ccc(C1)c(c1)C1NC(=O)c2cc(cc(NC(=O)C3CCCC3)c12)-c1ccc2ncnn2c1 | 1H NMR (400 MHz, DMSO-d6) 9.84-8.98 (m, 2H), 8.57 (s, 1H), 8.10 (dd, 9.3, 1.9 Hz, 1H), 8.03-7.93 (m, 2H), 7.81 (d, 1.7 Hz, 1H), 7.52 (dd, 9.1, 5.1 Hz, 1H), 7.25 (td, 8.4, 3.1 Hz, 1H), 6.63 (s, 1H), 6.14 (s, 1H), 2.68 (tt, 3.7, 1.8 Hz, 1H), 1.66-1.37 (m, 7H), 1.26 (d, 18.9 Hz, 1H). | 490.1 | E | |
| I-1783 | 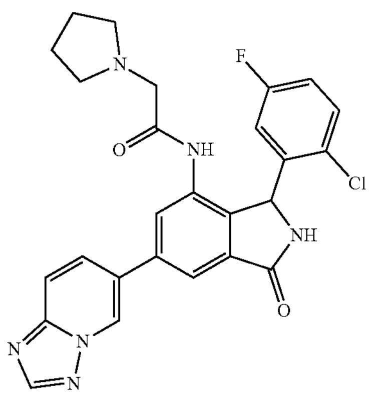 [SMILES: O=C(CN1CCCC1)Nc1cc(-c2ccc3ncnn3c2)cc2c1C(c1cc(F)ccc1Cl)NC2=O] | Fc1ccc(C1)c(c1)C1NC(=O)c2cc(cc(NC(=O)CN3CCCC3)c12)-c1ccc2ncnn2c1 | 1H NMR (400 MHz, DMSO-d6) 9.45-9.40 (m, 1H), 9.30 (d, 59.5 Hz, 1H), 8.57 (s, 1H), 8.21 (dd, 3.5, 1.7 Hz, 1H), 8.09 (dd, 9.3, 1.9 Hz, 1H), 8.02-7.95 (m, 2H), 7.57 (s, 1H), 7.29 (td, 8.4, 3.1 Hz, 1H), 6.67 (s, 1H), 6.18 (s, 1H), 3.11-2.94 (m, 2H), 2.38-2.11 (m, 4H), 1.72-1.59 (m, 4H) | 505.15 | E | |
| I-1784 | 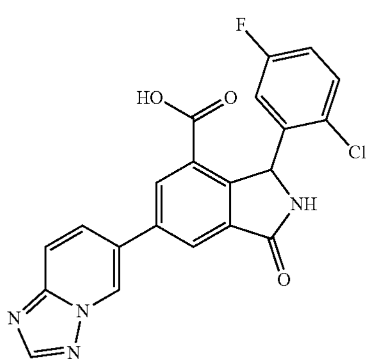 [SMILES: O=C(O)c1cc(-c2ccc3ncnn3c2)cc2c1C(c1cc(F)ccc1Cl)NC2=O] | OC(=O)c1cc(cc2C(=O)NC(c12)c1cc(F)ccc1Cl)-c1ccc2ncnn2c1 | 1H NMR (400 MHz, DMSO-d6) 9.49-9.27 (s, 1H), 8.57 (s, 1H), 8.44 (d, 1.9 Hz, 1H), 8.30 (d, 1.9 Hz, 1H), 8.15 (dd, 9.3, 1.9 Hz, 1H), 7.97 (d, 9.2 Hz, 1H), 7.51 (dd, 9.1, 5.2 Hz, 1H), 7.17 (td, 8.4, 3.1 Hz, 1H), 6.41 (s, 2H). | 422.95 | E | |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-1785 | 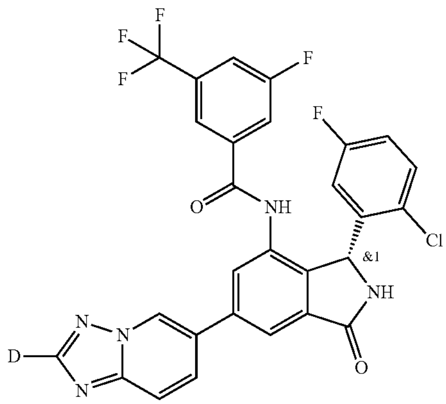 [SMILES: [2H]c1nc2ccc(-c3cc(NC(=O)c4cc(F)cc(C(F)(F)F)c4)c4c(c3)C(=O)N[C@H]4c3cc(F)ccc3Cl)cn2n1] | [2H]c1nc2ccc(cn2n1)-c1cc2C(=O)N[C@H](c2c(NC(=O)c2cc(F)cc(c2)C(F)(F)F)c1)c1cc(F)ccc1Cl | 1H NMR (400 MHz, Methanol-d4) 9.27 (dd, 1.9, 0.9 Hz, 1H), 8.22-8.12 (m, 2H), 7.99-7.89 (m, 2H), 7.75-7.66 (m, 3H), 7.32 (dd, 8.9, 5.1 Hz, 1H), 7.04 (ddd, 8.8, 7.7, 3.0 Hz, 1H), 6.72 (s, 1H), 6.29 (s, 1H). | 585.05 | A | |
| I-1786 | 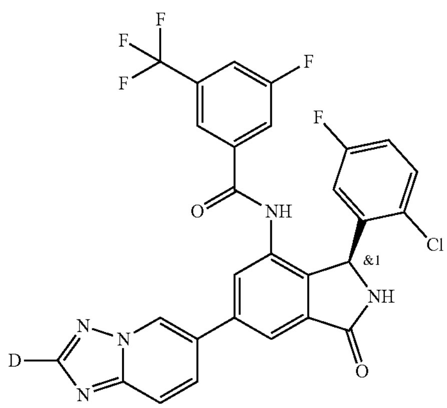 [SMILES: [2H]c1nc2ccc(-c3cc(NC(=O)c4cc(F)cc(C(F)(F)F)c4)c4c(c3)C(=O)N[C@@H]4c3cc(F)ccc3Cl)cn2n1] | [2H]c1nc2ccc(cn2n1)-c1cc2C(=O)N[C@@H](c2c(NC(=O)c2cc(F)cc(c2)C(F)(F)F)c1)c1cc(F)ccc1Cl | 1H NMR (400 MHz, Methanol-d4) 9.27 (dd, 1.9, 0.9 Hz, 1H), 8.22-8.12 (m, 2H), 7.99-7.89 (m, 2H), 7.76-7.66 (m, 3H), 7.32 (dd, 8.9, 5.1 Hz, 1H), 7.04 (ddd, 8.9, 7.7, 3.0 Hz, 1H), 6.72 (s, 1H), 6.29 (s, 1H). | 585.1 | B | |
| I-1787 | 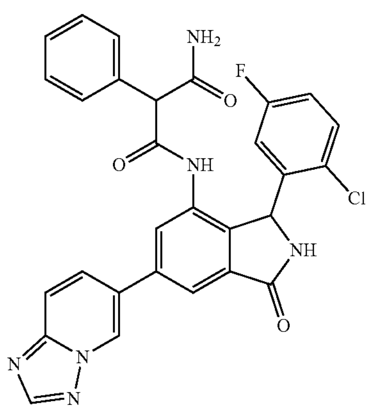 [SMILES: NC(=O)C(C(=O)Nc1cc(-c2ccc3ncnn3c2)cc2c1C(c1cc(F)ccc1Cl)NC2=O)c1ccccc1] | NC(=O)C(C(=O)Nc1cc(cc2C(=O)NC(c12)c1cc(F)ccc1Cl)-c1ccc2ncnn2c1)ccccc1 | NMR (400 MHz, DMSO-d6) 10.47 (br s, 0.6H), 10.13 (br s, 0.4H), 9.44-9.42 (m, 0.5H), 9.42-9.40 (m, 0.5H), 9.25 (br s, 0.6H), 9.21 (br s, 0.4H), 8.57 (s, 1H), 8.34 (d, 1.5 Hz, 0.5H), 8.10-8.04 (m, 1.5H), 8.01-7.94 (m, 2H), 7.75 (br s, 0.6H), 7.61 (br s, 0.4H), 7.54-7.36 (m, 2H), 7.31-7.14 (m, 5H), 7.04 (dd, 7.4, 1.5 Hz, 1H), 6.61 (br s, 1H), 6.14 (br s, 1H), 4.36 (br s, 0.6H), 4.35 (br s, 0.4H). | 555 | D | |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-1788 | 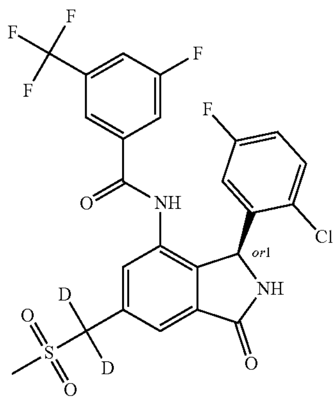 [SMILES: [2H]C([2H])(c1cc(NC(=O)c2cc(F)cc(C(F)(F)F)c2)c2c(c1)C(=O)N[C@@H]2c1cc(F)ccc1Cl)S(C)(=O)=O] | [2H]C([2H])(c1cc2C(=O)N[C@@H](c2c(NC(=O)c2cc(F)cc(c2)C(F)(F)F)c1cc(F)ccc1Cl)S(C)(=O)=O | NMR (400 MHz, CD3CN) 8.72 (br, s, 1H), 7.78 (d, 1.4 Hz, 1H), 7.65 (br, d, 8.5 Hz, 1H), 7.63 (s, 1H), 7.60 (br, d, 9.1 Hz, 1H), 7.56 (s, 1H), 7.30 (br, s, 1H), 7.26 (dd, 8.9, 5.1 Hz, 1H), 6.98 (ddd, 8.8, 8.1, 3.1 Hz, 1H), 6.66 (br, s, 1H | 561 | B | |
| I-1789 | 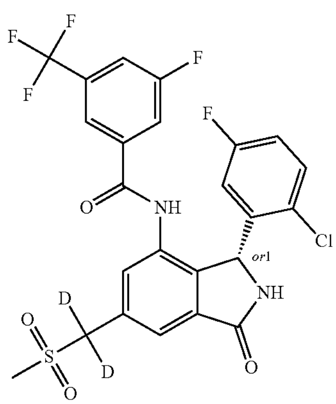 [SMILES: [2H]C([2H])(c1cc(NC(=O)c2cc(F)cc(C(F)(F)F)c2)c2c(c1)C(=O)N[C@H]2c1cc(F)ccc1Cl)S(C)(=O)=O] | [2H]C([2H])(c1cc2C(=O)N[C@H](c2c(NC(=O)c2cc(F)cc(c2)C(F)(F)F)c1cc(F)ccc1Cl)S(C)(=O)=O | NMR (400 MHz, CD3CN) 8.72 (br, s, 1H), 7.78 (d, 1.4 Hz, 1H), 7.65 (br, d, 8.5 Hz, 1H), 7.63 (s, 1H), 7.60 (br, d, 9.1 Hz, 1H), 7.56 (s, 1H), 7.30 (br, s, 1H), 7.26 (dd, 8.9, 5.1 Hz, 1H), 6.98 (ddd, 8.8, 8.1, 3.1 Hz, 1H), 6.66 (br, s, 1H) | 561 | A | |
| I-1790 | 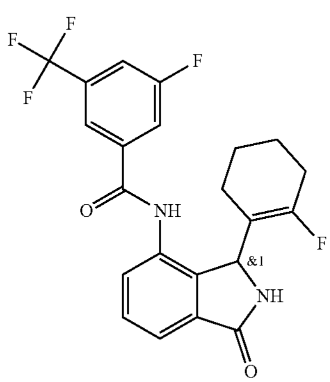 [SMILES: O=C(Nc1cccc2c1C(C1=C(F)CCCC1)NC2=O)c1cc(F)cc(C(F)(F)F)c1] | FC1=C(CCCC1)C1NC(=O)c2cccc(NC(=O)c3cc(F)cc(c3)C(F)(F)F)c12 | NMR (400 MHz, DMSO-d6) 10.62 (s, 1H), 8.66 (s, 1H), 8.14 (s, 1H), 8.07-8.00 (m, 2H), 7.62 (dd, 7.4, 1.4 Hz, 1H), 7.58 (t, 7.4 Hz, 1H), 7.51 (dd, 7.5, 1.3 Hz, 1H), 5.73 (s, 1H), 2.10-1.97 (m, , 1H), 1.64-1.40 (m, , 3H), 1.38-1.18 (m, 3H), 1.09 (m, 1H). | 437 | C | |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-1791 | 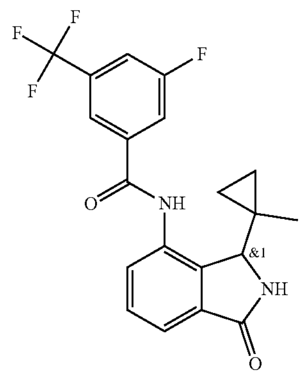 [SMILES: CC1(C2NC(=O)c3cccc(NC(=O)c4cc(F)cc(C(F)(F)F)c4)c32)CC1] | CC1(CC1)C1NC(=O)c2cccc(NC(=O)c3cc(F)cc(c3)C(F)(F)F)c12 | NMR (400 MHz, DMSO-d6) 10.59 (s, 1H), 8.72 (s, 1H), 8.24 (s, 1H), 8.16 (d, 9.2 Hz, 1H), 8.04 (d, 8.5 Hz, 1H), 7.63-7.53 (m, 3H), 4.04 (s, 1H), 0.54 (m, 2H), 0.43 (s, 3H), 0.32-0.23 (m, 1H), 0.19-0.11 (m, 1H). | 393 | E | |
| I-1792 | 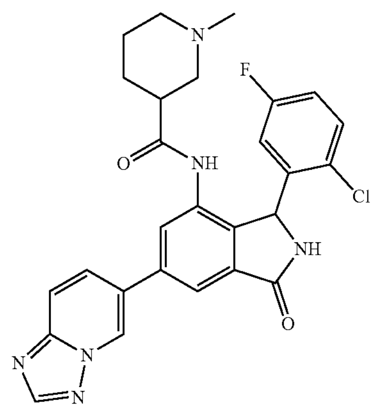 | CN1CCCC(C1)C(=O)Nc1cc(cc2C(=O)NC(c12)c1cc(F)ccc1Cl)-c1ccc2ncnn2c1 | NMR (400 MHz, DMSO-d6) 10.01 (br s, 0.5H), 9.97 (br s, 0.5H), 9.46-9.43 (m, 1H), 9.23 (br s, 1H), 8.57 (s, 1H), 8.10 (dt, 9.3, 1.8 Hz, 1H), 8.02-7.92 (m, 2.5H), 7.79 (d, 1.5 Hz, 0.5H), 7.62-7.46 (m, 1H), 7.32-7.22 (m, 1H), 6.50 (br s, 1H), 6.10 (br s, 1H), 2.67-2.54 (m, 1H), 2.44-2.37 (m, 0.5H), 2.36-2.26 (m, 1H), 2.25-2.13 (m, 0.5H), 2.09 (s, 1.5H), 2.06 (s, 1.5H), 1.83-1.59 (m, 2H), 1.57-1.29 (m, 3H), 1.23-1.06 (m, 1H). | 519 | D | |
| I-1793 | 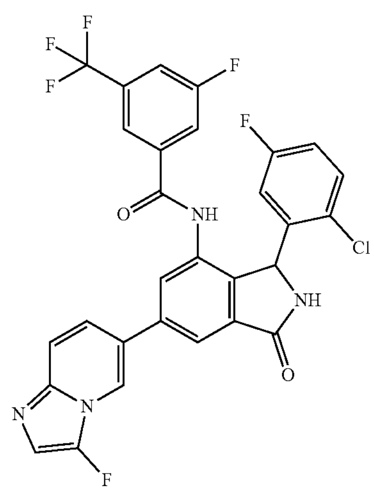 [SMILES: O=C(Nc1cc(-c2ccc3ncc(F)n3c2)cc2c1C(c1cc(F)ccc1Cl)NC2=O)c1cc(F)cc(C(F)(F)F)c1] | Fc1cnc2cc(cn12)-c1cc2C(=O)NC(c2c(NC(=O)c2cc(F)cc(c2)C(F)(F)c1)c1cc(F)ccc1Cl | 1H NMR (500 MHz, DMSO) 10.61 (s, 1H), 9.22 (s, 1H), 8.75 (s, 1H), 8.09 (d, 1.6 Hz, 1H), 7.95 (d, 8.4 Hz, 1H), 7.91 (s, 1H), 7.77 (d, 9.0 Hz, 1H), 7.71 (s, 1H), 7.69 (dd, 9.5, 1.8 Hz, 1H), 7.66 (d, 1.7 Hz, 1H), 7.61 (ddt, 9.7, 6.9, 3.9 Hz, 2H), 7.57-7.52 (m, 1H), 7.42 (d, 7.2 Hz, 1H), 7.33 (dd, 8.9, 5.2 Hz, 1H), 7.10 (td, 8.3, 3.1 Hz, 1H), 6.05 (s, 1H). | 601.23 | A | |

TABLE 2-continued

Representative Compounds of the Invention with Bioactivity Data.

| Ex. No. | Structure | SMILES | $^1$H NMR | MS | ADP-Glo IC$_{50}$ | MCF 10A IC$_{50}$ |
|---|---|---|---|---|---|---|
| I-1794 | 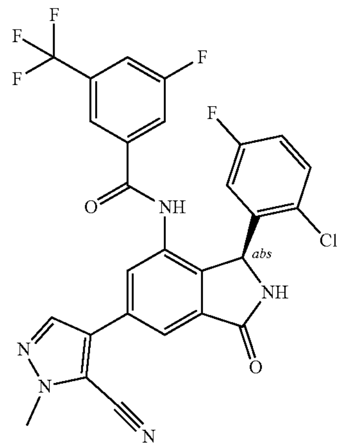 [SMILES: Cn1ncc(-c2cc(NC(=O)c3cc(F)cc(C(F)(F)F)c3)c3c(c2)C(=O)N[C@@H]3c2cc(F)ccc2Cl)c1C#N] | Cn1ncc(c1C#N)-c1cc2C(=O)N[C@@H](c2c(NC(=O)c2cc(F)cc(c2)C(F)(F)F)c1)c1cc(F)ccc1Cl | | 572.4 | D | |
| I-1795 | 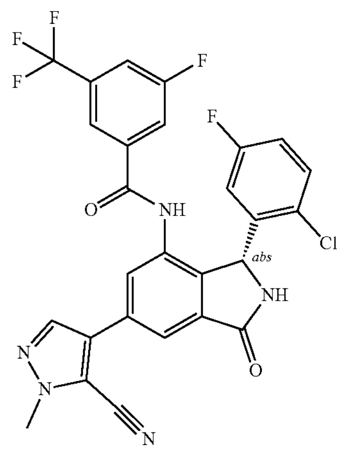 [SMILES: Cn1ncc(-c2cc(NC(=O)c3cc(F)cc(C(F)(F)F)c3)c3c(c2)C(=O)N[C@H]3c2cc(F)ccc2Cl)c1C#N] | Cn1ncc(c1C#N)-c1cc2C(=O)N[C@H](c2c(NC(=O)c2cc(F)cc(c2)C(F)(F)F)c1)c1cc(F)ccc1Cl | | 572.4 | A | |
| I-1796 | 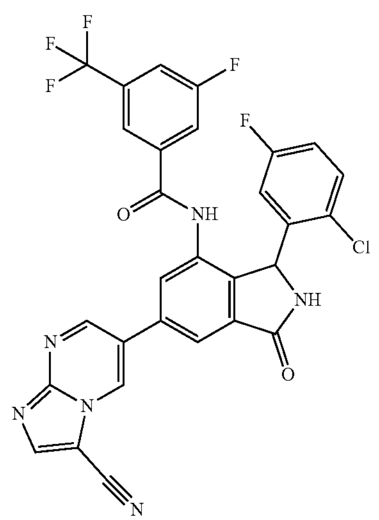 [SMILES: N#Cc1cnc2ncc(-c3cc(NC(=O)c4cc(F)cc(C(F)(F)F)c4)c4c(c3)C(=O)NC4c3cc(F)ccc3Cl)cn12] | Fc1ccc(C1)c(c1)C1NC(=O)c2cc(cc(NC(=O)c3cc(F)cc(c3)C(F)(F)F)c12)-c1cnc2ncc(C#N)n2c1 | | 609.08 | A | |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-1797 | 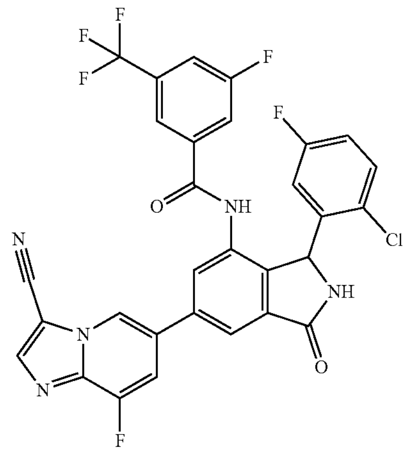 [SMILES: N#Cc1cnc2c(F)cc(-c3cc(NC(=O)c4cc(F)cc(C(F)(F)F)c4)c4c(c3)C(=O)NC4c3cc(F)ccc3Cl)cn12] | Fc1ccc(C1)c(c1)C1NC(=O)c2cc(cc(NC(=O)c3cc(F)cc(c3)C(F)(F)F)c12)-c1cc(F)c2ncc(C#N)n2c1 | | 626.09 | A | |
| I-1798 | 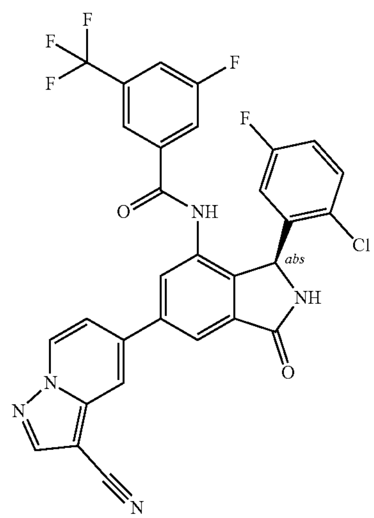 [SMILES: N#Cc1cnn2ccc(-c3cc(NC(=O)c4cc(F)cc(C(F)(F)F)c4)c4c(c3)C(=O)N[C@@H]4c3cc(F)ccc3Cl)cc12] | Fc1ccc(C1)c(c1)[C@H]1NC(=O)c2cc(cc(NC(=O)c3cc(F)cc(c3)C(F)(F)F)c12)-c1ccn2ncc(C#N)c2c1 | | 608.5 | D | |
| I-1799 | 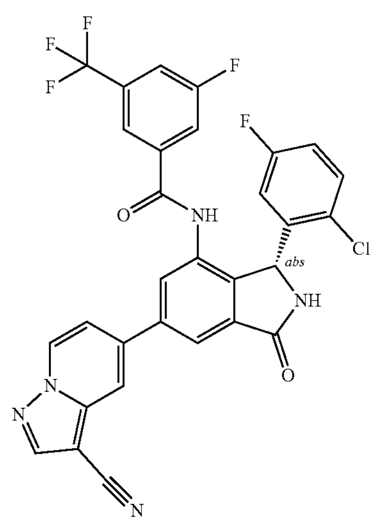 [SMILES: N#Cc1cnn2ccc(-c3cc(NC(=O)c4cc(F)cc(C(F)(F)F)c4)c4c(c3)C(=O)N[C@H]4c3cc(F)ccc3Cl)cc12] | Fc1ccc(C1)c(c1)[C@@H]1NC(=O)c2cc(cc(NC(=O)c3cc(F)cc(c3)C(F)(F)F)c12)-c1ccn2ncc(C#N)c2c1 | | 608.5 | A | |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-1800 | 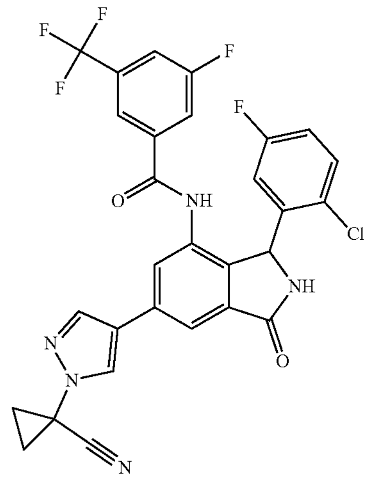 [SMILES: N#CC1(n2cc(-c3cc(NC(=O)c4cc(F)cc(C(F)(F)F)c4)c4c(c3)C(=O)NC4c3cc(F)ccc3Cl)cn2)CC1] | Fc1ccc(C1)c(c1)C1NC(=O)c2cc(cc(NC(=O)c3cc(F)cc(c3)C(F)(F)F)c12)-c1cnn(c1)C1(CC1)C#N | (400 MHz, DMSO-d6) 10.57 (s, 1 H), 9.16 (s, 1 H), 8.74 (s, 1 H), 8.23 (s, 1 H), 8.01-7.93 (m, 2 H), 7.80-7.70 (m, 3 H), 7.32 (dd, 8.9, 5.2 Hz, 1 H), 7.09 (td, 8.5, 2.9 Hz, 1 H), 6.57 (br s, 1 H), 5.98 (s, 1 H), 1.98-1.85 (m, 4 H). | 596.3 | A | |
| I-1801 | 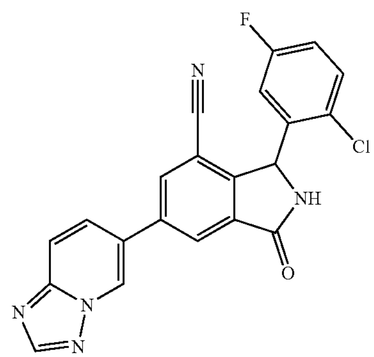 [SMILES: N#Cc1cc(-c2ccc3ncnn3c2)cc2c1C(c1cc(F)ccc1Cl)NC2=O] | Fc1ccc(C1)c(c1)C1NC(=O)c2cc(cc(C#N)c12)-c1ccc2ncnn2c1 | (400 MHz, DMSO-d6) 9.60 (s, 1 H), 9.51 (s, 1 H), 8.63-8.57 (m, 2 H), 8.49 (s, 1 H), 8.22 (dd, 9.3, 1.7 Hz, 1 H), 7.98 (d, 9.3 Hz, 1 H), 7.69-7.49 (m, 1 H), 7.34 (td, 8.4, 2.6 Hz, 1 H), 6.35 (br s, 1 H). | 402.2 | D | |
| I-1802 | 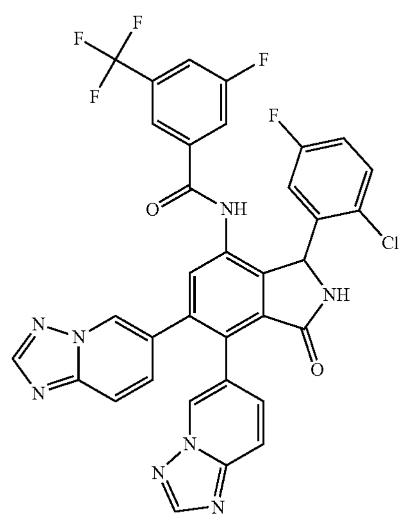 [SMILES: O=C(Nc1cc(-c2ccc3ncnn3c2)c(-c2ccc3ncnn3c2)c2c1C(c1cc(F)ccc1Cl)NC2=O)c1cc(F)cc(C(F)(F)F)c1] | Fc1ccc(C1)c(c1)C1NC(=O)c2c1c(NC(=O)c1cc(F)cc(c1)C(F)(F)F)cc(-c1ccc3ncnn3c1)c2-c1ccc2ncnn2c1 | (400 MHz, CD3CN) 8.83 (br s, 0.5 H), 8.75-8.67 (m, 0.5 H), 8.66 (s, 1 H), 8.27 (d, 2.6 Hz, 2 H), 8.10 (s, 1 H), 7.76 (s, 1 H), 7.66 (dd, 17.2, 8.7 Hz, 2 H), 7.61 (s, 1 H), 7.54 (dd, 18.1, 9.1 Hz, 2 H), 7.46 (br s, 1 H), 7.35 (dd, 9.2, 1.7 Hz, 2 H), 7.30 (dd, 8.9, 5.1 Hz, 1 H), 7.03 (td, 8.4, 3.0 Hz, 1 H), 6.84 (br s, 1 H), 6.21 (br s, 1 H) | 701.2 | B | |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-1803 | 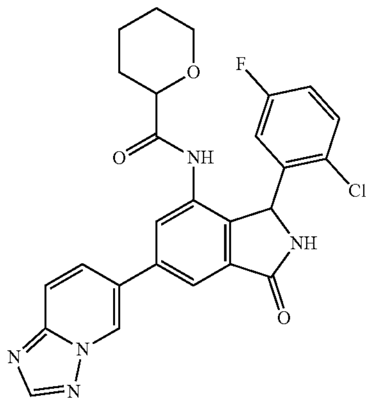 [SMILES: O=C1NC(c2cc(F)ccc2Cl)c2c(NC(=O)C3CCCCO3)cc(-c3ccc4ncnn4c3)cc21] | Fc1ccc(C1)c(c1)C1NC(=O)c2cc(cc(NC(=O)C3CCCCO3)c12)-c1ccc2ncnn2c1 | NMR (400 MHz, DMSO-d6) 9.45-9.39 (m, 1H), 9.22 (s, 1H), 9.18 (s, 0.5H), 9.02 (s, 0.5 H), 8.57 (s, 1H), 8.20 (s, 0.5H), 8.17 (d, 1.3 Hz, 1H), 8.09 (d, 1.6 Hz, 1H), 8.09-8.04 (m, 1H), 8.01-7.93 (m, 2H), 7.51 (br s, 1H), 7.34-7.21 (m, 1H), 7.00-6.35 (br s, 1H), 6.19 (br s, 1H), 3.88 (dd, 16.0, 13.5 Hz, 1H), 3.72 (dd, 12.8, 11.4, 2.4 Hz, 1H), 3.52-3.35 (m, 2H), 1.82-1.57 (m, 2H), 1.57-1.29 (m, 3H), 1.11-0.71 (m, 1H). | 506.3 | E | |
| I-1804 | 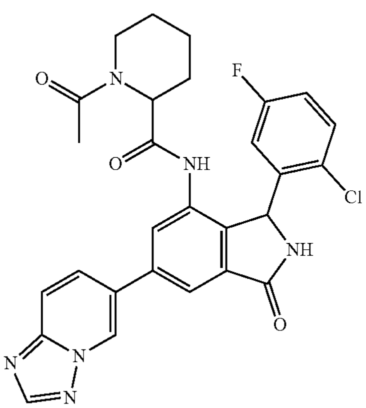 [SMILES: CC(=O)N1CCCCC1C(=O)Nc1cc(-c2ccc3ncnn3c2)cc2c1C(c1cc(F)ccc1Cl)NC2=O] | CC(=O)N1CCCCC1C(=O)Nc1cc(cc2C(=O)NC(c12)c1cc(F)ccc1Cl)-c1ccc2ncnn2c1 | NMR (400 MHz, DMSO-d6) 9.87 (s, 0.1H), 9.85 (s, 0.2H), 9.74 (s, 0.3H), 9.65 (s, 0.3H), 9.44-9.42 (s, 0.6H), 9.41-9.39(s, 0.5H), 9.24-9.14 (m, 1H), 8.56-8.51 (m, 1H), 8.10-8.03 (m, 1H), 8.03-7.99 (m, 1H), 7.98-7.91 (m, 2H), 7.86-7.78 (m, 0.5H), 7.57-7.46 (m, 1H), 7.26-7.17 (m, 1H), 6.50 (br s, 1H), 6.20 (br s, 0.6H), 6.16 (br s, 0.4H), 5.08-4.96 (m, 1H), 4.45-3.98 (m, 0.4H), 3.63-3.46 (m, 0.6H), 2.94-2.67 (m, 0.5H), 1.98 (s, 2H), 1.90 (s, 1H), 1.94-1.76 (submerged m, 1H), 1.58-1.45 (m, 0.5 H), 1.43-1.14 (m, 4H), 1.14-0.48 (m, 1H). mixture of diastereomers and possible rotamers | 547.2 | E | |
| I-1805 | 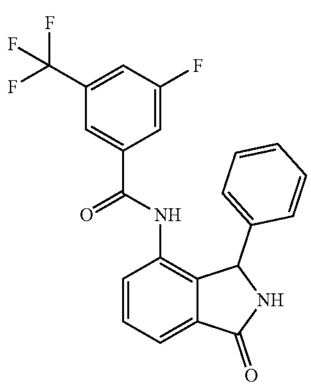 [SMILES: O=C(Nc1cccc2c1C(c1ccccc1)NC2=O)c1cc(F)cc(C(F)(F)F)c1] | Fc1cc(cc(c1)C(F)(F)F)C(=O)Nc1ccccc2C(=O)NC(c12)c1ccccc1 | NMR (400 MHz, DMSO-d6) 10.40 (s, 1H), 9.09 (s, 1H), 7.95 (br. d, 8.5 Hz, 1H), 7.69-7.65 (m, 2H), 7.62-7.57 (m, 2H), 7.52 (dd, 7.1, 0.7 Hz, 1H), 7.22-7.11 (m, 3H), 6.99-6.95 (m, 2H), 5.73 (s, 1H). | 415.3 | D | |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-1806 | 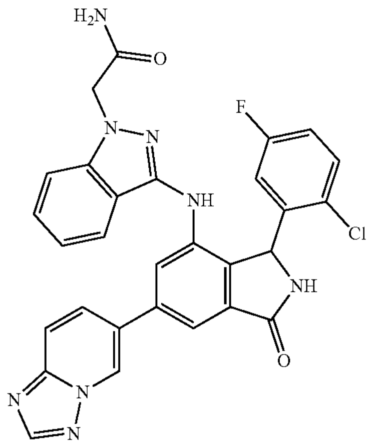 [SMILES: NC(=O)Cn1nc(Nc2cc(-c3ccc4ncnn4c3)cc3c2C(c2cc(F)ccc2Cl)NC3=O)c2ccccc21] | NC(=O)Cn1nc(Nc2cc(cc3C(=O)NC(c23)c2cc(F)ccc2Cl)-c2ccc3ncnn3c2)c2ccccc12 | 1H NMR (400 MHz, DMSO-d6) 9.35 (dd, 1.9, 0.9 Hz, 1H), 9.05 (s, 1H), 8.56 (s, 1H), 8.38 (s, 1H), 8.10-7.95 (m, 3H), 7.74 (d, 1.6 Hz, 1H), 7.59 (s, 1H), 7.47 (d, 8.4 Hz, 1H), 7.39-7.29 (m, 2H), 7.24 (dd, 8.8, 4.9 Hz, 2H), 7.08-6.95 (m, 2H), 6.72 (s, 1H), 6.12 (s, 1H), 5.00-4.82 (m, 2H). | 567.3 | D | |
| I-1807 | 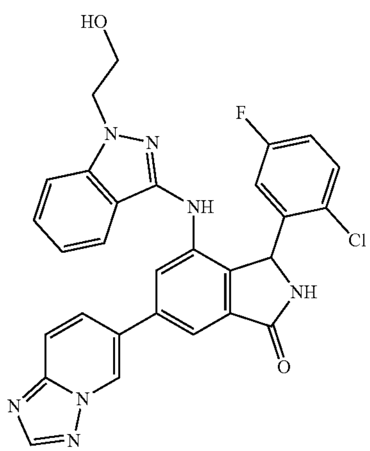 [SMILES: O=C1NC(c2cc(F)ccc2Cl)c2c(Nc3nn(CCO)c4ccccc34)cc(-c3ccc4ncnn4c3)cc21] | OCCn1nc(Nc2cc(cc3C(=O)NC(c23)c2cc(F)ccc2Cl)-c2ccc3ncnn3c2)c2ccccc12 | 1H NMR (400 MHz, DMSO-d6) 9.34 (s, 1H), 9.07 (s, 1H), 8.56 (s, 1H), 8.33 (s, 1H), 8.09-8.02 (m, 2H), 7.97 (d, 9.3 Hz, 1H), 7.72 (d, 1.6 Hz, 1H), 7.50 (d, 8.5 Hz, 1H), 7.33 (dt, 9.3, 2.2 Hz, 2H), 7.26 (dd, 8.8, 5.2 Hz, 1H), 7.03 (td, 8.4, 3.2 Hz, 1H), 6.94 (d, 7.5 Hz, 1H), 6.65 (s, 1H), 6.13 (s, 1H), 4.83 (t, 5.4 Hz, 1H), 4.31 (t, 5.7 Hz, 2H), 3.80 (t, 5.8 Hz, 2H). | 554.35 | D | |
| I-1808 | 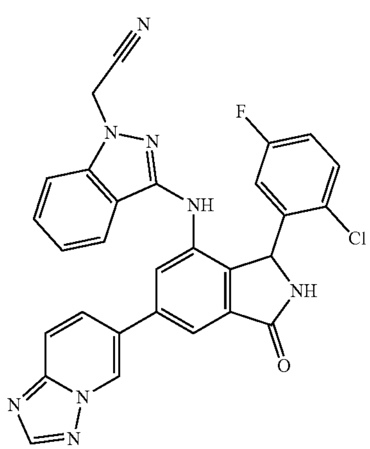 [SMILES: N#CCn1nc(Nc2cc(-c3ccc4ncnn4c3)cc3c2C(c2cc(F)ccc2Cl)NC3=O)c2ccccc21] | Fc1ccc(C1)c(c1)C1NC(=O)c2cc(cc(Nc3nn(CC#N)c4cccc c34)c12)-c1ccc2ncnn2c1 | 1H NMR (400 MHz, DMSO-d6) 9.39 (t, 1.4 Hz, 1H), 9.13 (s, 1H), 8.68 (s, 1H), 8.57 (s, 1H), 8.09 (dd, 9.3, 1.9 Hz, 1H), 8.02 (t, 2.1 Hz, 1H), 7.97 (d, 9.2 Hz, 1H), 7.83 (d, 1.6 Hz, 1H), 7.63 (d, 8.8 Hz, 1H), 7.51-7.41 (m, 2H), 7.21 (dd, 8.8, 5.1 Hz, 1H), 7.09 (dd, 8.2, 6.8 Hz, 1H), 7.00 (td, 8.3, 3.1 Hz, 1H), 6.57 (s, 1H), 6.18 (s, 1H), 5.63 (d, 2.8 Hz, 2H). | 549.1 | D | |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-1809 | 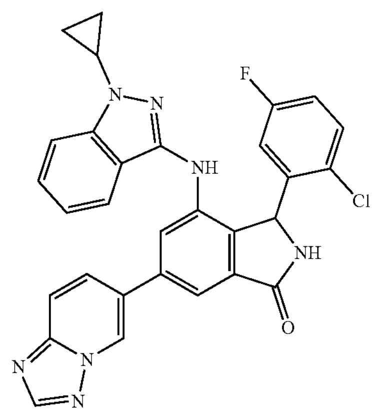 [SMILES: O=C1NC(c2cc(F)ccc2Cl)c2c(Nc3nn(C4CC4)c4ccccc34)cc(-c3ccc4ncnn4c3)cc21] | Fc1ccc(C1)c(c1)C1NC(=O)c2cc(cc(Nc3nn(C4CC4)c4ccccc34)c12)-c1ccc2ncnn2c1 | 1H NMR (400 MHz, DMSO-d6) 9.36 (t, 1.4 Hz, 1H), 9.08 (s, 1H), 8.57 (s, 1H), 8.40 (s, 1H), 8.10-8.02 (m, 2H), 7.98 (d, 9.0 Hz, 1H), 7.74 (d, 1.6 Hz, 1H), 7.53 (d, 8.4 Hz, 1H), 7.36 (dd, 14.1, 7.2 Hz, 2H), 7.25-7.20 (m, 1H), 7.07-6.98 (m, 2H), 6.60 (s, 1H), 6.10 (d, 2.8 Hz., 1H), 3.57 (p, 5.3 Hz, 1H), 1.08 (tq, 5.9, 1.9 Hz, 4H). | 550.25 | D | |
| I-1810 | 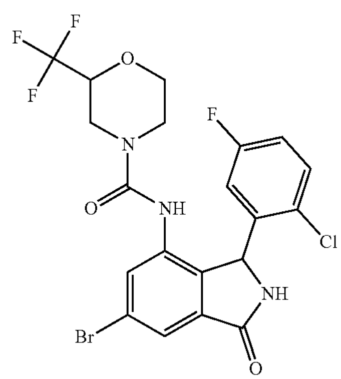 [SMILES: O=C1NC(c2cc(F)ccc2Cl)c2c(NC(=O)N3CCOC(C(F)(F)F)C3)cc(Br)cc21] | Fc1ccc(C1)c(c1)C1NC(=O)c2cc(Br)cc(NC(=O)N3CCOC(C3)C(F)(F)F)c12 | 1H NMR (400 MHz, DMSO-d6) 9.21 (s, 1H), 8.89 (s, 1H), 7.65 (d, 1.7 Hz, 1H), 7.53 (d, 1.7 Hz, 1H), 7.48 (dd, 4.5, 1.7 Hz, 1H), 7.27 (ddt, 11.2, 8.4, 2.7 Hz, 1H), 6.65 (s, 1H), 5.96 (s, 1H), 3.92 (dd, 19.6, 10.6 Hz, 2H), 3.58 (dd, 27.2, 13.5 Hz, 1H), 2.55 (s, 3H). | 535.95 | D | |
| I-1812 | 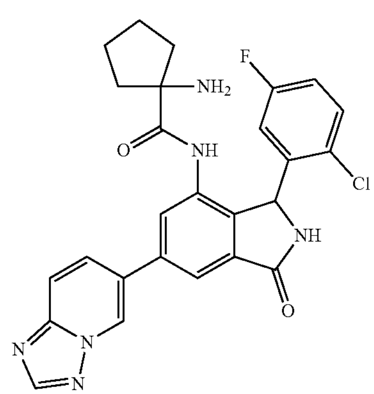 [SMILES: NC1(C(=O)Nc2cc(-c3ccc4ncnn4c3)cc3c2C(c2cc(F)ccc2Cl)NC3=O)CCCC1] | NC1(CCCC1)C(=O)Nc1cc(cc2C(=O)NC(c12)c1cc(F)ccc1Cl)-c1ccc2ncnn2c1 | 1H NMR (400 MHz, DMSO-d6) 9.46 (d, 2.1 Hz, 1H), 9.23 (s, 1H), 8.58 (s, 1H), 8.30-7.87 (m, 5H), 7.53 (s, 1H), 7.28 (td, 8.4, 3.1 Hz, 1H), 6.08 (s, 1H), 1.82 (d, 73.1 Hz, 8H). | 505.15 | E | |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-1813 | 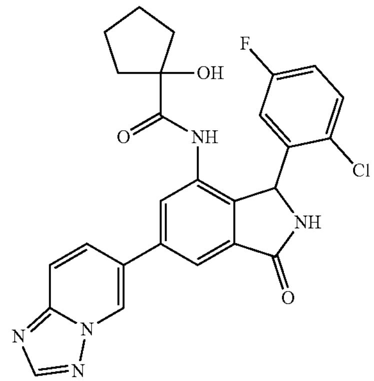 [SMILES: O=C1NC(c2cc(F)ccc2Cl)c2c(NC(=O)C3(O)CCCC3)cc(-c3ccc4ncnn4c3)cc21] | OC1(CCCC1)C(=O)Nc1cc(cc2C(=O)NC(c12)c1cc(F)ccc1Cl)-c1ccc2ncnn2c1 | 1H NMR (400 MHz, DMSO-d6) 9.58-9.35 (m, 2H), 9.20 (s, 1H), 8.57 (s, 1H), 8.20-8.06 (m, 2H), 8.03-7.94 (m, 2H), 7.54 (d, 8.3 Hz, 1H), 7.26 (ddd, 8.8, 7.9, 3.1 Hz, 1H), 6.67 (s, 1H), 6.25 (s, 1H), 5.49 (s, 1H), 1.83-1.55 (m, 6H), 1.54-1.31 (m, 2H). | 506.15 | E | |
| I-1814 | 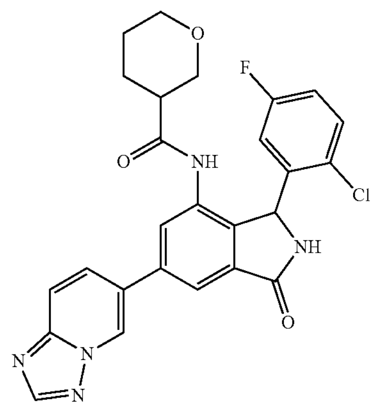 | Fc1ccc(C1)c(c1)C1NC(=O)c2cc(cc(NC(=O)C3CCCOC3)c12)-c1ccc2ncnn2c1 | NMR (400 MHz, DMSO-d6) 9.93 (br s, 0.5H), 9.91 (br s, 0.5H), 9.44 (s, 1H), 9.22 (br s, 1H), 8.57 (s, 1H), 8.09 (dd, 9.3, 1.8 Hz, 1H), 8.01 (s, 1H), 7.97 (d, 9.3 Hz, 1H), 7.81 (dd, 9.4, 1.4 Hz, 1H), 7.62-7.46 (m, 1H), 7.32-7.21 (m, 1H), 6.59 (br s, 1H), 6.09 (br s, 1H), 3.74 (d, 10.6 Hz, 1H), 3.61 (dd, 11.1, 3.7 Hz, 0.5H), 3.25-2.98 (m, 2H), 2.40-2.27 (m, 1H), 1.72-1.59 (m, 0.5H), 1.58-1.32 (m, 4H). | 506 | E | |
| I-1815 | 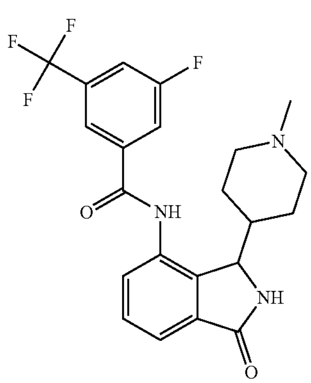 [SMILES: CN1CCC(C2NC(=O)c3cccc(NC(=O)c4cc(F)cc(C(F)(F)F)c4)c32)CC1] | CN1CCC(CC1)C1NC(=O)c2cccc(NC(=O)c3cc(F)cc(c3)C(F)(F)F)c12 | (400 MHz, DMSO-d6) 10.82 (br s, 1H), 8.80 (s, 1H), 8.13 (s, 1H), 8.09 (d, 8.9 Hz, 1H), 8.04 (d, 8.5 Hz, 1H), 7.65-7.48 (m, 3H), 4.79 (d, 1.5 Hz, 1H), 2.79 (d, 7.5 Hz, 1H), 2.65 (d, 11.6 Hz, 2H), 2.06 (s, 3H), 1.86-1.74 (m, 1H), 1.69-1.55 (m, 3H), 1.54-1.44 (m, 1H), 0.98 (qd, 12.4, 3.9 Hz, 1H), 0.59 (d, 12.5 Hz, 1H) | 436.3 | E | |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-1816 | 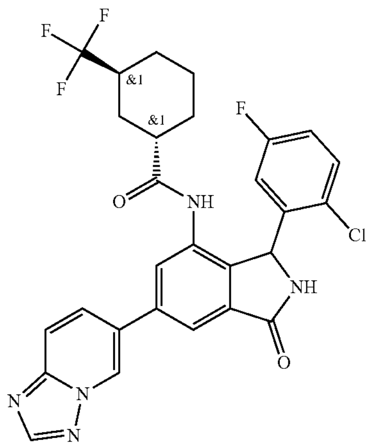 [SMILES: O=C1NC(c2cc(F)ccc2Cl)c2c(NC(=O)[C@H]3CCC[C@H](C(F)(F)F)C3)cc(-c3ccc4ncnn4c3)cc21] | Fc1ccc(C1)c(c1)C1NC(=O)c2cc(cc(NC(=O)[C@H]3CCC[C@@H](C3)C(F)(F)F)c12)-c1ccc2ncnn2c1 | 1H-NMR (400 MHz, DMSO-d6) 9.90 (br. s, 1H), 9.84 (br. s, 1H), 9.45-9.43 (m, 2H), 9.23 (br. s, 2H), 8.58-8.57 (m, 2H), 8.10 (dd, 9.2, 0.9 Hz, 2H), 8.03-7.98 (m, 3H), 7.95 (dd, 12.1, 1.9 Hz, 2H), 7.82-7.80 (m, 1H), 7.56-7.50 (m, 2H), 7.28-7.20 (m, 2H), 6.51 (br. s, 2H), 6.22 (br. s, 1H), 6.20 (br. s, 1H), 2.61-2.55 (m, 2H), 1.93-1.83 (m, 2H), 1.68-1.59 (m, 2H), 1.56-1.48 (m, 2H), 1.44-1.30 (m, 6H), 1.27-1.14 (m, 4H), 1.04-0.77 (m, 2H). | 572.4 | A | |
| I-1817 | 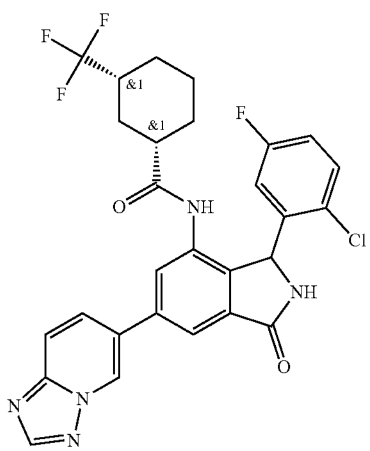 [SMILES: O=C1NC(c2cc(F)ccc2Cl)c2c(NC(=O)[C@H]3CCC[C@@H](C(F)(F)F)C3)cc(-c3ccc4ncnn4c3)cc21] | Fc1ccc(C1)c(c1)C1NC(=O)c2cc(cc(NC(=O)[C@H]3CCC[C@H](C3)C(F)(F)F)c12)c1ccc2ncnn2c1 | 1H-NMR (400 MHz, DMSO-d6) 10.03 (br. s, 1H), 9.95 (br. s, 1H), 9.44 (s, 2H), 9.22 (br. s, 2H), 8.58-8.56 (m, 2H), 8.10 (dd, 9.3, 1.3 Hz, 2H), 8.01 (d, 1.1 Hz, 2H), 7.97 (d, 9.3 Hz, 2H), 7.80 (dd, 10.6, 0.9 Hz, 2H), 7.53-7.43 (m, 2H), 7.25-7.19 (m, 2H), 6.57 (br. s, 2H), 6.12 (br. s, 2H), 2.31-2.14 (m, 4H), 1.83-1.71 (m, 4H), 1.68-1.53 (m, 2H), 1.43-1.34 (m, 2H), 1.30-1.20 (m, 2H), 1.15-0.98 (m, 6H). | 572.3 | B | |
| I-1818 | 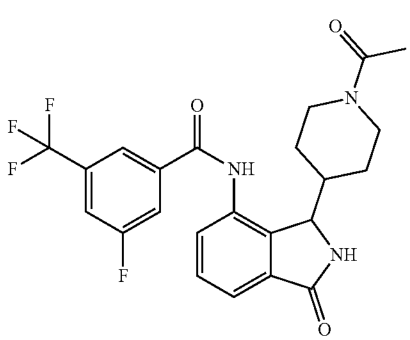 [SMILES: CC(=O)N1CCC(C2NC(=O)c3cccc(NC(=O)c4cc(F)cc(C(F)(F)F)c4)c32)CC1] | CC(=O)N1CCC(CC1)C1NC(=O)c2cccc(NC(=O)c3cc(F)cc(c3)C(F)(F)F)c12 | (400 MHz, DMSO-d6) 10.73 (br s, 1H), 8.76 (s, 0.5H), 8.73 (s, 0.5H), 8.16 (s, 1H), 8.12 (d, 8.9 Hz, 1H), 8.04 (d, 8.5 Hz, 1H), 7.64 (dd, 3.0, 1.6 Hz, 0.5H), 7.62 (dd, 3.2, 1.7 Hz, 0.5H), 7.60-7.51 (m, 2H), 4.83 (s, 1H), 4.41 (d, 12.9 Hz, 0.5H), 4.25 (d, 13.0 Hz, 0.5H), 3.81 (d, 13.4 Hz, 0.5H), 3.67 (d, 13.3 Hz, 0.5H), 2.85-2.68 (m, 1H), 2.29-2.16 (m, 1H), 2.16-2.03 (m, 1H), 1.93 (s, 1.5H), 1.89 (s, 1.5H), 1.64-1.48 (m, 1.5H), 1.48-1.32 (m, 0.5H), 0.94-0.82 (m, 0.5H), 0.81-0.70 (m, 0.5H), 0.69-0.58 (m, 1H) | 464.3 | E | |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-1819 | 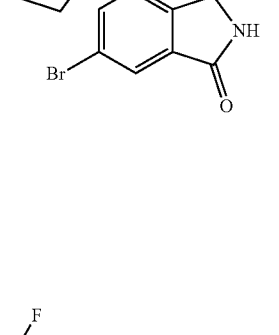 | Fc1ccc(C1)c(c1)C1NC(=O)c2cc(Br)cc(NC(=O)C3(CCCC3)c3cc(F)ccc3F)c12 | 1H NMR(400 MHz, DMSO):-' 9.22 (s, 1H), 8.93 (s, 1H), 7.70 (d, 1.4 Hz, 1H), 7.57 (d, 1.4 Hz, 1H), 7.52 (dd, 8.1, 5.1 Hz, 1H), 7.24 (td, 8.4, 3.0 Hz, 1H), 7.19-7.02 (m, 3H), 6.50 (brs, 1H), 6.10 (s, 1H), 2.07-1.93 (m, 2H), 1.80-1.64 (m, 2H), 1.54-1.30 (m, 4H) | 563.2 | E | |
| I-1820 | 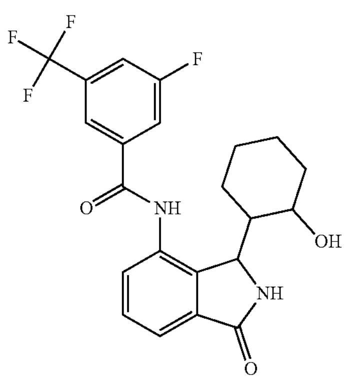 [SMILES: O=C(Nc1cccc2c1C(C1CCCCC1O)NC2=O)c1cc(F)cc(C(F)(F)F)c1] | OC1CCCCC1C1NC(=O)c2cccc(NC(=O)c3cc(F)cc(c3)C(F)(F)F)c12 | NMR (400 MHz, DMSO-d6) 10.66 (br. s, 1H), 8.60 (s, 1H), 8.16 (s, 1H), 8.11 (br. d, 9.1 Hz, 1H), 8.00 (br. d, 8.6 Hz, 1H), 7.73 (dd, 7.3, 1.0 Hz, 1H), 7.50-7.43 (m, 2H), 4.97 (d, 1.2 Hz, 1H), 4.34 (br. s, 1H), 3.27-3.16 (m, 1H), 1.82 (app. t, 11.2 Hz, 1H), 1.72-1.62 (m, 1H), 1.58-1.47 (m, 2H), 1.39 (app. d, 12.2 Hz., 1H), 1.29-1.20 (m, 1H), 1.05-0.96 (m, 2H), 0.84-0.71 (m, 1H). | 437.2 | E | |
| I-1821 | 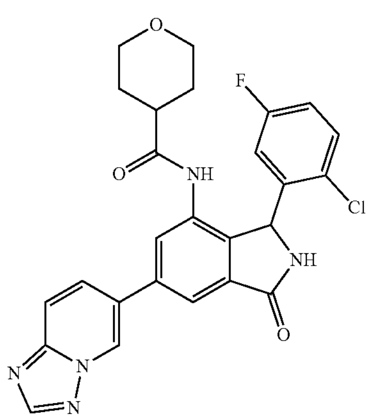 [SMILES: O=C1NC(c2cc(F)ccc2Cl)c2c(NC(=O)C3CCOCC3)cc(-c3ccc4ncnn4c3)cc21] | Fc1ccc(C1)c(c1)C1NC(=O)c2cc(cc(NC(=O)C3CCOCC3)c12)-c1ccc2ncnn2c1 | NMR (400 MHz, DMSO-d6) 9.88 (s, 1H), 9.45-9.43 (m, 1H), 9.22 (br s, 1H), 8.57 (s, 1H), 8.09 (dd, 9.3, 1.8 Hz, 1H), 8.01 (d, 1.5 Hz, 1H), 7.97 (dd, 9.2, 0.6 Hz, 1H), 7.81 (d, 1.5 Hz, 1H), 7.59-7.46 (m, 1H), 7.25 (td, 8.4, 3.1 Hz, 1H), 6.57 (br s, 1H), 6.13 (br s, 1H), 3.87-3.62 (m, 2H), 3.38-3.07 (m, 2H), 2.41-2.23 (m, 1H), 1.45-1.37 (m, 2H), 1.36-1.16 (m, 2H). | 506 | E | |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-1822 | 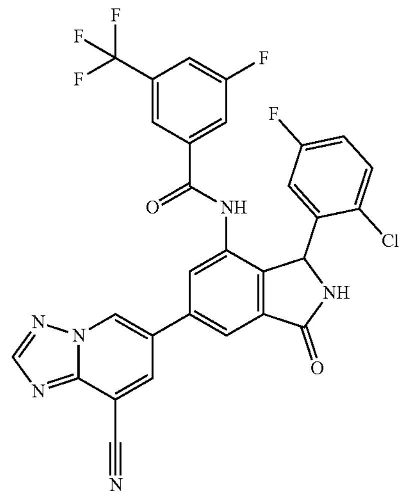 [SMILES: N#Cc1cc(-c2cc(NC(=O)c3cc(F)cc(C(F)(F)F)c3)c3c(c2)C(=O)NC3c2cc(F)ccc2Cl)cn2ncnc12] | Fc1ccc(C1)c(c1)C1NC(=O)c2cc(cc(NC(=O)c3cc(F)cc(c3)C(F)(F)F)c12)-c1cc(C#N)c2ncnn2c1 | | 609.13 | A | |
| I-1823 | 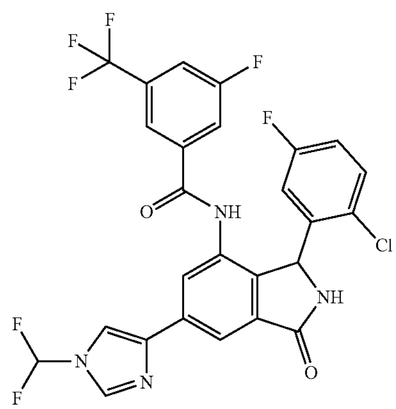 [SMILES: O=C(Nc1cc(-c2cn(C(F)F)cn2)cc2c1C(c1cc(F)ccc1Cl)NC2=O)c1cc(F)cc(C(F)(F)F)c1] | FC(F)n1cnc(c1)-c1cc2C(=O)NC(c2c(NC(=O)c2cc(F)cc(c2)C(F)(F)F)c1)c1cc(F)ccc1Cl | | 583.4 | A | |
| I-1824 | 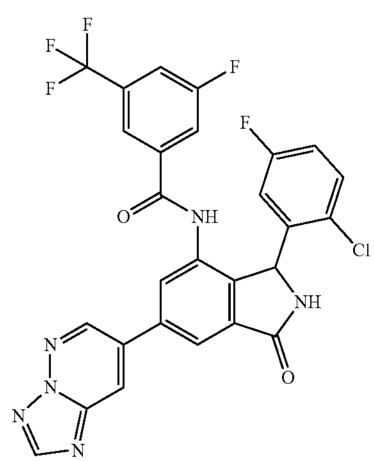 | Fc1ccc(C1)c(c1)C1NC(=O)c2cc(cc(NC(=O)c3cc(F)cc(c3)C(F)(F)F)c12)-c1cnn2ncnc2c1 | 1H NMR (500 MHz, DMSO) δ 10.68 (s, 1H), 9.29 (s, 1H), 9.27 (d, J = 2.4 Hz, 1H), 8.88 (d, J = 2.4 Hz, 1H), 8.73 (s, 1H), 8.30 (d, J = 1.6 Hz, 1H), 8.09 (d, J = 1.7 Hz, 1H), 7.96 (dt, J = 8.5, 2.0 Hz, 1H), 7.77 (d, J = 8.7 Hz, 1H), 7.72 (s, 1H), 7.34 (dd, J = 8.9, 5.1 Hz, 1H), 7.11 (td, J = 8.4, 3.1 Hz, 1H), 6.08 (s, 1H). | 585.12 | A | |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-1825 | 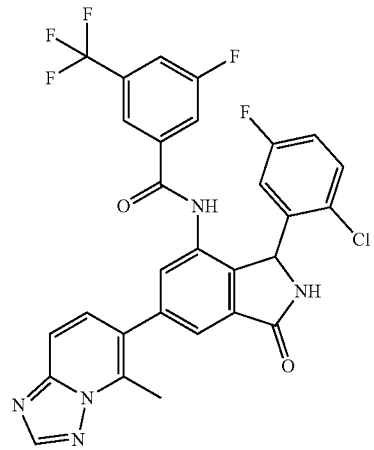 [SMILES: Cc1c(-c2cc(NC(=O)c3cc(F)cc(C(F)(F)F)c3)c3c(c2)C(=O)NC3c2cc(F)ccc2Cl)ccc2ncnn12] | Cc1c(ccc2ncnn12)-c1cc2C(=O)NC(c2c(NC(=O)c2cc(F)cc(c2)C(F)(F)F)c1)c1cc(F)ccc1Cl | | | A | |
| I-1826 | 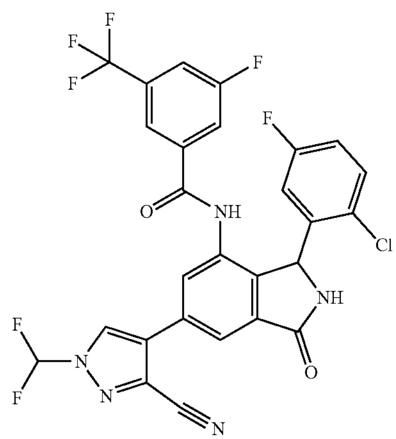 [SMILES: N#Cc1nn(C(F)F)cc1-c1cc(NC(=O)c2cc(F)cc(C(F)(F)F)c2)c2c(c1)C(=O)NC2c1cc(F)ccc1Cl] | FC(F)n1cc(c(n1)C#N)-c1cc2C(=O)NC(c2c(NC(=O)c2cc(F)cc(c2)C(F)(F)F)c1)c1cc(F)ccc1Cl | | 608.5 | A | |
| I-1827 | 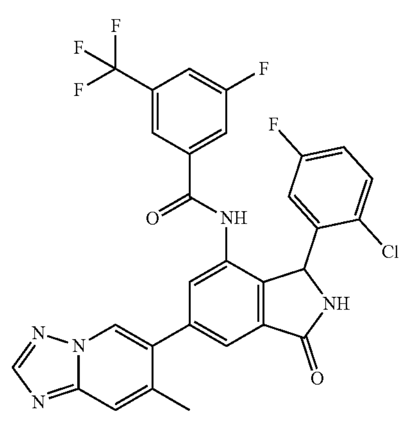 [SMILES: Cc1cc2ncnn2cc1-c1cc(NC(=O)c2cc(F)cc(C(F)(F)F)c2)c2c(c1)C(=O)NC2c1cc(F)ccc1Cl] | Cc1cc2ncnn2cc1-c1cc2C(=O)NC(c2c(NC(=O)c2cc(F)cc(c2)C(F)(F)F)c1)c1cc(F)ccc1Cl | | 598.08 | A | |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-1828 | 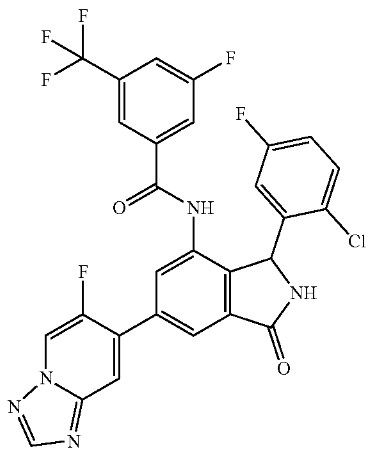 [SMILES: O=C(Nc1cc(-c2cc3ncnn3cc2F)cc2c1C(c1cc(F)ccc1Cl)NC2=O)c1cc(F)cc(C(F)(F)F)c1] | Fc1ccc(C1)c(c1)C1NC(=O)c2cc(cc(NC(=O)c3cc(F)cc(c3)C(F)(F)F)c12)-c1cc2ncnn2cc1F | | 602.08 | A | |
| I-1829 | 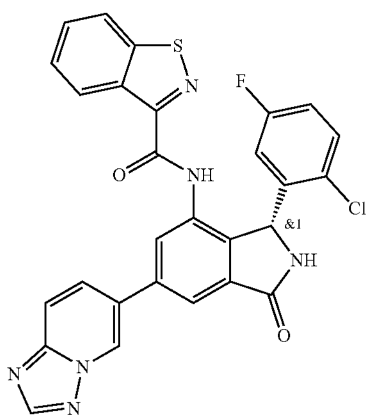 [SMILES: O=C1N[C@@H](c2cc(F)ccc2Cl)c2c(NC(=O)c3nsc4ccccc34)cc(-c3ccc4ncnn4c3)cc21] | Fc1ccc(C1)c(c1)[C@@H]1NC(=O)c2cc(cc(NC(=O)c3nsc4ccccc34)c12)-c1ccc2ncnn2c1 | 1H NMR (400 MHz, DMSO-d6) 10.54 (s, 1H), 9.48 (dd, 1.9, 0.9 Hz, 1H), 9.26 (s, 1H), 8.70 (d, 8.2 Hz, 1H), 8.58 (s, 1H), 8.33 (dt, 8.3, 1.1 Hz, 1H), 8.19-8.12 (m, 2H), 8.11 (d, 1.7 Hz, 1H), 8.00 (dd, 9.3, 0.9 Hz, 1H), 7.70 (ddd, 8.3, 6.9, 1.2 Hz, 1H), 7.62 (ddd, 8.1, 7.0, 1.1 Hz, 1H), 7.33-7.24 (m, 1H), 7.04 (td, 8.4, 3.0 Hz, 1H), 6.82 (s, 1H), 6.29 (s, 1H). | 555.1 | A | |
| I-1830 | 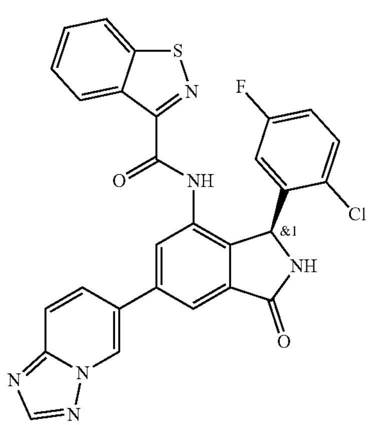 [SMILES: O=C1N[C@H](c2cc(F)ccc2Cl)c2c(NC(=O)c3nsc4ccccc34)cc(-c3ccc4ncnn4c3)cc21] | Fc1ccc(C1)c(c1)[C@H]1NC(=O)c2cc(cc(NC(=O)c3nsc4ccccc34)c12)-c1ccc2ncnn2c1 | 1H NMR (400 MHz, DMSO-d6) 10.54 (s, 1H), 9.48 (dd, 1.9, 0.9 Hz, 1H), 9.26 (s, 1H), 8.70 (d, 8.2 Hz, 1H), 8.58 (s, 1H), 8.33 (dt, 8.3, 1.1 Hz, 1H), 8.19-8.12 (m, 2H), 8.11 (d, 1.7 Hz, 1H), 8.00 (dd, 9.3, 0.9 Hz, 1H), 7.70 (ddd, 8.3, 6.9, 1.2 Hz, 1H), 7.62 (ddd, 8.1, 7.0, 1.1 Hz, 1H), 7.33-7.24 (m, 1H), 7.04 (td, 8.4, 3.0 Hz, 1H), 6.82 (s, 1H), 6.29 (s, 1H). | 555.1 | D | |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-1831 | 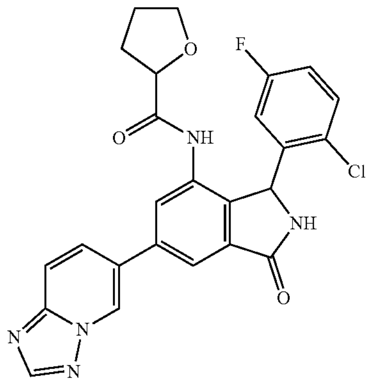 [SMILES: O=C1NC(c2cc(F)ccc2Cl)c2c(NC(=O)C3CCCO3)cc(-c3ccc4ncnn4c3)cc21] | Fc1ccc(C1)c(c1)C1NC(=O)c2cc(cc(NC(=O)C3CCCO3)c12)-c1ccc2ncnn2c1 | NMR (400 MHz, DMSO-d6) 9.57 (s, 1H), 9.445-9.44(m, 1H), 9.44-9.42 (m, 0.7H), 9.44-9.42 (m, 0.3H), 9.24 (s, 1H), 8.57 (s, 1H), 8.14-8.06 (m, 1.5H), 8.03 (s, 1.5 H), 8.02-7.94 (m, 1.5H), 7.63-7.49 (m, 1H), 7.33-7.17 (m, 1H), 6.67 (br s, 1H), 6.24 (s, 0.3H), 6.20 (s, 0.7H), 4.26-4.16 (m, 1H), 3.77-3.52 (m, 2H), 2.12-1.95 (m, 1H), 1.81-1.59 (m, 1H), 1.59-1.20 (m, 2H). | 492.3 | E | |
| I-1832 | 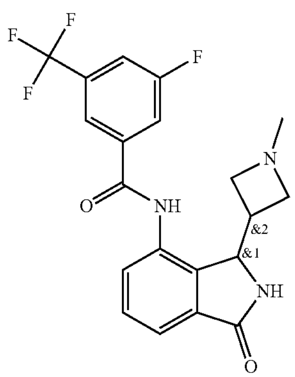 [SMILES: CN1CC(C2NC(=O)c3cccc(NC(=O)c4cc(F)cc(C(F)(F)F)c4)c32)C1] | CN1CC(C1)C1NC(=O)c2cccc(NC(=O)c3cc(F)cc(c3)C(F)(F)F)c12 | NMR (400 MHz, MeCN-d3) 9.46 (br. s, 1H), 8.68 (br. s, 1H), 8.16 (d, 0.4 Hz, 1H), 8.02 (dt, 9.1, 1.7 Hz, 1H), 7.73 (dt, 8.7, 1.5 Hz, 1H), 7.65 (dd, 7.2, 1.3 Hz, 1H), 7.61-7.52 (m, 2H), 5.07 (d, 2.9 Hz, 1H), 4.08 (dd, 10.2, 6.4 Hz, 1H), 3.84 (t, 9.4 Hz, 1H), 3.43 (app. t, 1H), 3.38 (m, 1H), 3.23 (dd, 8.9, 5.8 Hz, 1H), 2.53 (s, 3H) | 408.2 | E | |
| I-1833 | 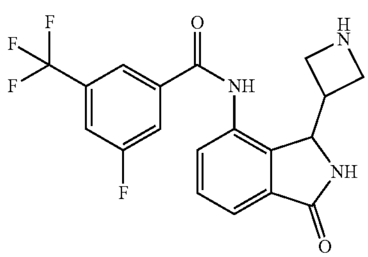 [SMILES: O=C(Nc1cccc2c1C(C1CNC1)NC2=O)c1cc(F)cc(C(F)(F)F)c1] | Fc1cc(cc(c1)C(F)(F)F)C(=O)Nc1cccc2C(=O)NC(C3CNC3)c12 | NMR (400 MHz, MeCN-d3) 9.46 (br. s, 1H), 8.83 (br. s, 1H), 8.15 (s, 1H), 8.02 (d, 9.2 Hz, 1H), 7.73 (d, 8.5 Hz, 1H), 7.66 (dd, 7.1, 1.2 Hz, 1H), 7.61-7.51 (m, 2H), 5.07 (d, 1.3 Hz, 1H), 4.21-4.07 (m, 1H), 4.08-3.90 (m, 1H), 3.69-3.52 (m, 1H), 3.50-3.40 (m, 1H), 3.24 (m, 1H). | 394.1 | E | |
| I-1834 | 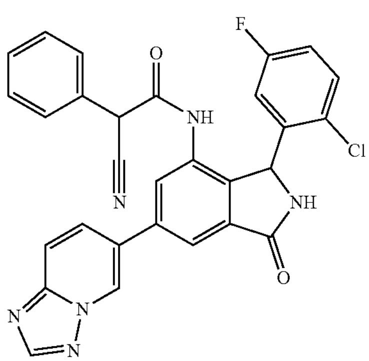 [SMILES: N#CC(C(=O)Nc1cc(-c2ccc3ncnn3c2)cc2c1C(c1cc(F)ccc1Cl)NC2=O)c1ccccc1] | Fc1ccc(C1)c(c1)C1NC(=O)c2cc(cc(NC(=O)C(C#N)c3ccccc3)c12)-c1ccc2ncnn2c1 | NMR (400 MHz, DMSO-d6) 10.59 (br s, 1H), 9.44 (br s, 1H), 9.21 (br s, 1H), 8.57 (s, 1H), 8.14-8.02 (m, 2H), 7.96 (d, 9.2 Hz, 1H), 7.86-6.71 (m, 8H), 6.70-6.22 (m, 1H), 6.10 (s, 1H), 5.20 (s, 0.3H), 5.13 (s, 0.3H). | 537 | D | |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-1835 | 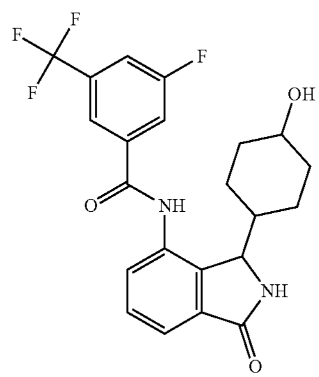 [SMILES: O=C(Nc1cccc2c1C(C1CCC(O)CC1)NC2=O)c1cc(F)cc(C(F)(F)F)c1] | OC1CCC(CC1)C1NC(=O)c2cccc(NC(=O)c3cc(F)cc(c3)C(F)(F)F)c12 | NMR (400 MHz, DMSO-d6) 10.74 (br s, 1H), 8.70 (s, 1H), 8.14 (s, 1H), 8.09 (d, 8.9 Hz, 1H), 8.05 (d, 8.5 Hz, 1H), 7p.61-7.49 (m, 3H), 4.77 (s, 1H), 4.45 (d, 4.2 Hz, 1H), 3.24-3.12 (m, 1H), 1.92-1.68 (m, 2H), 1.64 (d, 11.9 Hz, 1H), 1.57 (d, 13.34 H, 1H), 1.39 (qd, 13.4, 3.2 Hz, 1H), 0.98-0.70 (m, 3H), 0.68-0.60 (m, 1H). | 437.1 | | E |
| I-1836 | 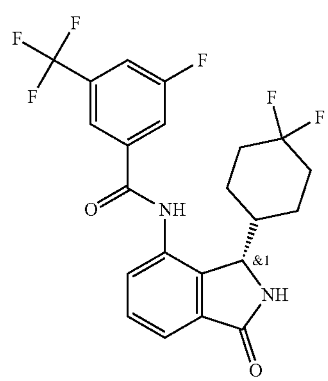 [SMILES: O=C(Nc1cccc2c1[C@H](C1CCC(F)(F)CC1)NC2=O)c1cc(F)cc(C(F)(F)F)c1] | Fc1cc(cc(c1)C(F)(F)F)C(=O)Nc1cccc2C(=O)N[C@@H](C3CCC(F)(F)CC3)c12 | NMR (400 MHz, DMSOD6) 10.83 (br s, 1H), 8.79 (s, 1H), 8.15 (s, 1H), 8.13 (d, 9.2 Hz, 1H), 8.03 (d, 8.5 Hz, 1H), 7.64 (dd, 7.3, 1.5 Hz, 1H), 7.59-7.51 (m, 2H), 4.86 (br s, 1H), 2.09-1.95 (m, 2H), 1.90-1.80 (m, 1H), 1.7-1.51 (m, 4H), 1.05-0.90 (qd, 13.7, 3.6 Hz, 1H), 0.73 (app. Br d, 12.7 Hz, 1H). | 457.3 | | E |
| I-1837 | 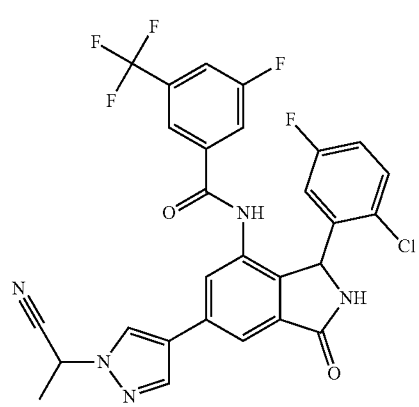 [SMILES: CC(C#N)n1cc(-c2cc(NC(=O)c3cc(F)cc(C(F)(F)F)c3)c3c(c2)C(=O)NC3c2cc(F)ccc2Cl)cn1] | CC(C#N)n1cc(cn1)-c1cc2C(=O)NC(c2c(NC(=O)c2cc(F)cc(c2)C(F)(F)F)c1cc(F)ccc1Cl | (400 MHz, DMSO-d6) 10.55 (br s, 1 H), 9.17 (br s, 1 H), 8.62 (s, 1 H), 8.23 (s, 1 H), 7.98-7.94 (m, 2 H), 7.79-7.68 (m, 3 H), 7.32 (dd, 8.9, 5.2 Hz, 1 H), 7.09 (td, 8.5, 2.9 Hz, 1 H), 6.58 (br s, 1 H), 5.98 (br s, 1 H), 5.88 (q, 7.1 Hz, 1 H), 1.86 (d, 7.1 Hz, 3 H). | 584.3 | | A |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-1838 | 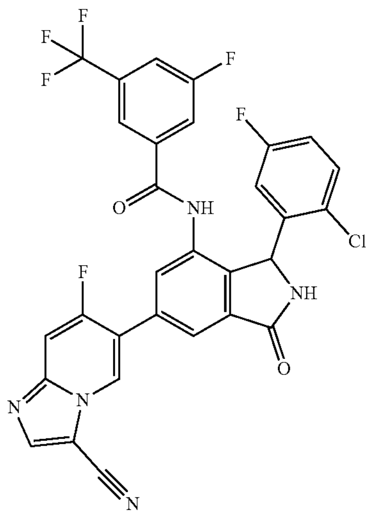 [SMILES: N#Cc1cnc2cc(F)c(-c3cc(NC(=O)c4cc(F)cc(C(F)(F)F)c4)c4c(c3)C(=O)NC4c3cc(F)ccc3Cl)cn12] | Fc1ccc(C 1)c(c1)C1 NC(=O)c 2cc(cc(N C(=O)c3 cc(F)cc(c 3)C(F)(F) F)c12)- c1cn2c(c nc2cc1F) C#N | | 626.14 | A | |
| I-1839 | 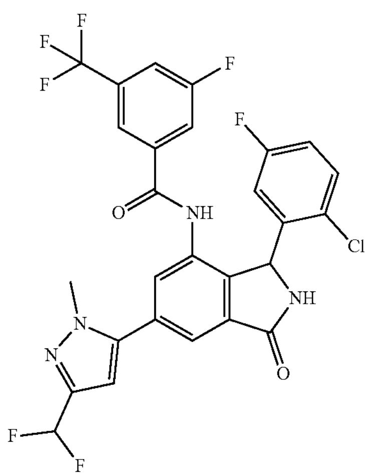 [SMILES: Cn1nc(C(F)F)cc1-c1cc(NC(=O)c2cc(F)cc(C(F)(F)F)c2)c2c(c1)C(=O)NC2c1cc(F)ccc1Cl] | Cn1nc(cc 1- c1cc2C(= O)NC(c2 c(NC(=O) c2cc(F)c c(c2)C(F) (F)F)c1)c 1cc(F)ccc 1Cl)C(F) F | | | A | |
| I-1840 | 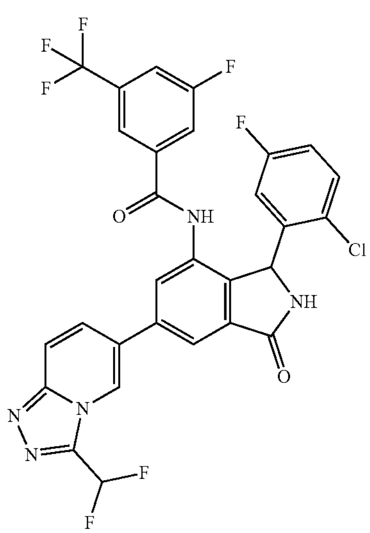 [SMILES: O=C(Nc1cc(-c2ccc3nnc(C(F)F)n3c2)cc2c1C(c1cc(F)ccc1Cl)NC2=O)c1cc(F)cc(C(F)(F)F)c1] | FC(F)c1n nc2ccc(c n12)- c1cc2C(= O)NC(c2 c(NC(=O) c2cc(F)c c(c2)C(F) (F)F)c1)c 1cc(F)ccc 1Cl | | | A | |

TABLE 2-continued

Representative Compounds of the Invention with Bioactivity Data.

| Ex. No. | Structure | SMILES | $^1$H NMR | MS | ADP-Glo IC$_{50}$ | MCF 10A IC$_{50}$ |
|---|---|---|---|---|---|---|
| I-1841 | 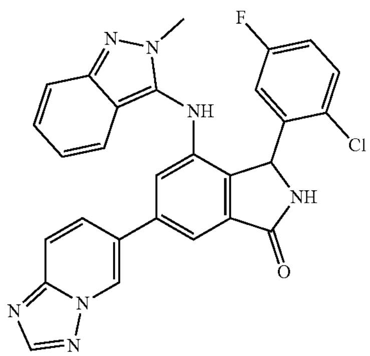 [SMILES: Cn1nc2ccccc2c1Nc1cc(-c2ccc3ncnn3c2)cc2c1C(c1cc(F)ccc1Cl)NC2=O] | Cn1nc2cccc c2c1Nc1cc(cc2 C(=O)NC(c12)c1 cc(F)ccc1Cl)- c1ccc2ncnn2c1 | 1H NMR (400 MHz, DMSO-d6) 9.35-9.29 (m, 1H), 9.08 (s, 1H), 8.54 (s, 1H), 8.24 (s, 1H), 7.97 (dd, 9.3, 1.8 Hz, 1H), 7.92 (d, 9.2 Hz, 1H), 7.71 (d, 1.6 Hz, 1H), 7.50 (dd, 8.8, 5.5 Hz, 2H), 7.29-7.14 (m, 3H), 7.07 (d, 8.4 Hz, 1H), 6.88 (dd, 8.5, 6.5 Hz, 1H), 6.55 (d, 8.9 Hz, 1H), 5.59 (s, 1H), 3.55 (s, 3H). | 524.15 | E | |
| I-1842 | 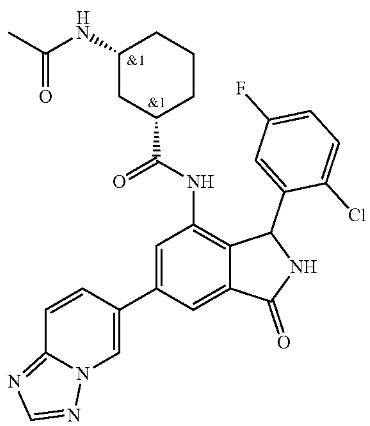 [SMILES: CC(=O)N[C@@H]1CCC[C@H](C(=O)Nc2cc(-c3ccc4ncnn4c3)cc3c2C(c2cc(F)ccc2Cl)NC3=O)C1] | CC(=O) N[C@@H]1CCC [C@@H](C1)C(=O) Nc1cc(cc2C(=O) NC(c12)c1cc(F)ccc 1Cl)- c1ccc2ncnn2c1 | 1H NMR (400 MHz, DMSO-d6) 9.85-9.56 (m, 1H), 9.44 (s, 1H), 9.19 (s, 1H), 8.57 (s, 1H), 8.14-8.06 (m, 1H), 8.03-7.94 (m, 2H), 7.82-7.77 (m, 1H), 7.67 (dd, 33.9, 7.4 Hz, 1H), 7.50 (s, 1H), 7.32-7.15 (m, 1H), 6.56 (s, 1H), 6.14 (s, 1H), 3.93 (s, 1H), 2.37 (s, 1H), 2.16 (t, 12.0 Hz, 1H), 1.86-1.76 (m, 3H), 1.69 (s, 1H), 1.62 (d, 17.6 Hz, 1H), 1.43 (s, 3H), 1.24 (S, 1H), 1.22-1.08 (m, 1H), 1.07-0.97 (m, 2H). | 561.2 | E | |
| I-1843 | 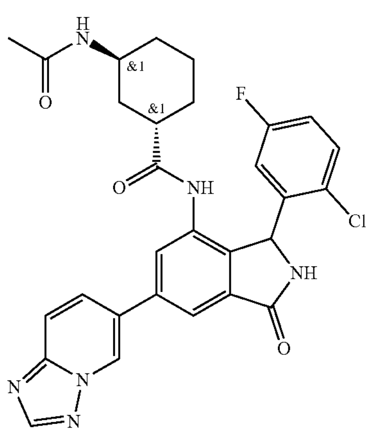 [SMILES: CC(=O)N[C@H]1CCC[C@H](C(=O)Nc2cc(-c3ccc4ncnn4c3)cc3c2C(c2cc(F)ccc2Cl)NC3=O)C1] | CC(=O) N[C@H]1CCC[C@@H](C1)C(=O) Nc1cc(cc2C(=O)N C(c12)c1cc(F)ccc1Cl)- c1ccc2ncnn2c1 | 1H NMR (400 MHz, DMSO-d6) 9.82 (s, 1H), 9.43 (dd, 1.9, 0.9 Hz, 1H), 9.18 (s, 1H), 8.57 (s, 1H), 8.09 (dd, 9.4, 1.9 H7, 1H), 8.02-7.94 (m, 2H), 7.79 (d, 1.7 Hz, 1H), 7.70 (d, 8.0 Hz, 1H), 7.48 (td, 8.3, 3.1 Hz, 1H), 7.19 (td, 8.3, 3.1 Hz, 1H), 6.11 (s, 1H), 3.45 (s, 1H), 3.32 (s, 1H), 2.14 (d, 12.9 Hz, 1H), 1.81 (s, 3H), 1.69 (t, 12.3 Hz, 2H), 1.43 (s, 2H), 1.22 (d, 14.9 Hz, 1H), 1.15 (s, 1H), 1.05 (s, 2H). | 561.2 | E | |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-1844 | 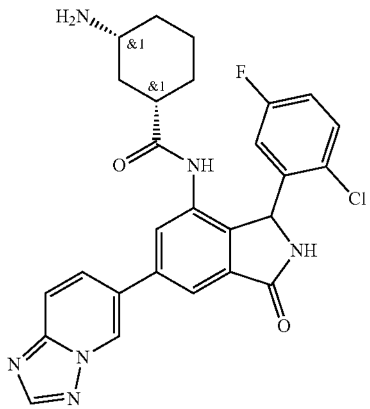 [SMILES: N[C@@H]1CCC[C@H](C(=O)Nc2cc(-c3ccc4ncnn4c3)cc3c2C(c2cc(F)ccc2Cl)NC3=O)C1] | N[C@@H]1CCC[C@@H](C1)C(=O)Nc1cc(c2C(=O)NC(c12)c1cc(F)ccc1Cl)-c1ccc2ncnn2c1 | 1H NMR (400 MHz, DMSO-d6) 9.76 (d, 33.5 Hz, 1H), 9.43 (d, 2.0 Hz, 1H), 9.20 (s, 1H), 8.57 (d, 1.2 Hz, 1H), 8.14-8.05 (m, 1H), 8.03-7.98 (m, 1H), 7.98-7.67 (m, 1H), 7.52 (s, 1H), 7.25 (t, 8.5 Hz, 1H), 6.61 (s, 1H), 6.14 (s, 1H), 2.14 (s, 1H), 2.08-1.74 (m, 1H), 1.67 (s, 2H), 1.51 (s, 1H), 1.42 (d, 12.6 Hz, 1H), 1.21 (s, 5H), 1.02-0.88 (m, 1H). | 519.2 | E | |
| I-1845 | 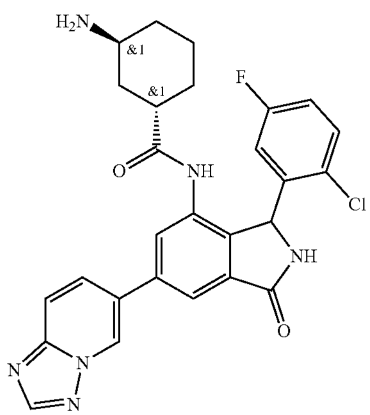 [SMILES: N[C@H]1CCC[C@H](C(=O)Nc2cc(-c3ccc4ncnn4c3)cc3c2C(c2cc(F)ccc2Cl)NC3=O)C1] | N[C@H]1CCC[C@@H](C1)C(=O)Nc1cc(cc2C(=O)NC(c12)c1cc(F)ccc1Cl)-c1ccc2ncnn2c1 | 1H NMR (400 MHz, DMSO-d6) 9.76 (d, 33.5 Hz, 1H), 9.46-9.41 (m, 1H), 9.19 (s, 1H), 8.57 (s, 1H), 8.09 (dd, 9.3, 2.0 Hz, 1H), 8.03-7.94 (m, 2H), 7.86-7.76 (m, 1H), 7.52 (s, 1H), 7.25 (t, 8.6 Hz, 1H), 6.65 (s, 1H), 6.14 (s, 1H), 2.25-1.96 (m, 1H), 1.95-1.74 (m, 2H), 1.65 (s, 2H), 1.20 (d, 34.2 Hz, 4H), 1.09-0.38 (m, 3H) | 519.2 | E | |
| I-1846 | 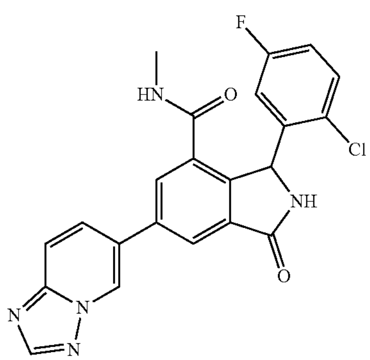 [SMILES: CNC(=O)c1cc(-c2ccc3ncnn3c2)cc2c1C(c1cc(F)ccc1Cl)NC2=O] | CNC(=O)c1cc(cc2C(=O)NC(c12)c1cc(F)ccc1Cl)-c1ccc2ncnn2c1 | 1H NMR (400 MHz, DMSO-d6)9.56 (t, 1.4 Hz, 1H), 9.29 (s, 1H), 8.60 (s, 1H), 8.54 (d, 4.8 Hz, 1H), 8.30-78.10 (m, 3H), 8.10-7.90 (s, 1H), 7.52 (d, 9.1 Hz, 1H), 7.19 (td, 8.4, 3.1 Hz, 1H), 6.41 (s, 2H), 2.61-2.55 (m, 3H). | 436 | E | |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-1847 | 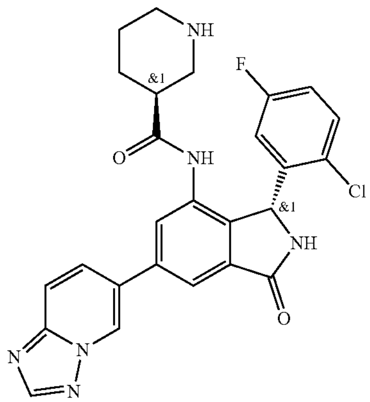 [SMILES: O=C1N[C@@H](c2cc(F)ccc2Cl)c2c(NC(=O)[C@H]3CCCNC3)cc(-c3ccc4ncnn4c3)cc21] | Fc1ccc(C1)c(c1)[C@@H]1NC(=O)c2cc(cc(NC(=O)[C@H]3CCCNC3)c12)-c1ccc2ncnn2c1 | 1H NMR (400 MHz, DMSO-d6) 10.12-9.12 (m, 2H), 8.57 (s, 1H), 8.09 (dd, 9.3, 1.9 Hz, 1H), 8.02-7.84 (m, 3H), 7.53 (d, 10.1 Hz, 1H), 7.35-7.10 (m, 1H), 6.58 (s, 1H), 6.12 (s, 1H), 2.86-2.71 (m, 2H), 2.33 (s, 1H), 2.22 (d, 9.8 Hz, 1H), 1.51-1.15 (m, 6H). | 505.15 | E | |
| I-1848 | 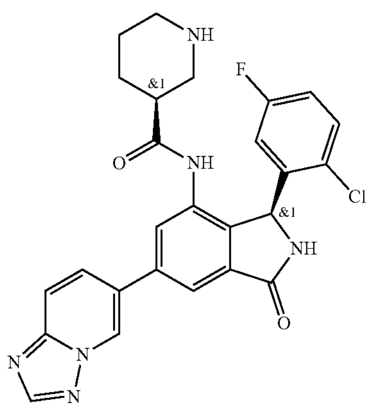 [SMILES: O=C1N[C@H](c2cc(F)ccc2Cl)c2c(NC(=O)[C@H]3CCCNC3)cc(-c3ccc4ncnn4c3)cc21] | Fc1ccc(C1)c(c1)C@H]1NC(=O)c2cc(cc(NC(=O)[C@H]3CCCNC3)c12)-c1ccc2ncnn2c1 | 1H NMR (400 MHz, DMSO-d6) 10.12-9.12 (m, 2H), 8.57 (s, 1H), 8.09 (dd, 9.3, 1.9 Hz, 1H), 8.02-7.84 (m, 3H), 7.53 (d, 10.1 Hz, 1H), 7.35-7.10 (m, 1H), 6.58 (s, 1H), 6.12 (s, 1H), 2.86-2.71 (m, 2H), 2.33 (s, 1H), 2.22 (d, 9.8 Hz, 1H), 1.51-1.15 (m, 6H). | 505.15 | E | |
| I-1849 | 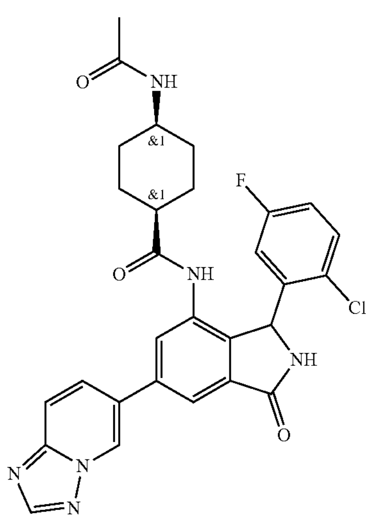 [SMILES: CC(=O)N[C@H]1CC[C@@H](C(=O)Nc2cc(-c3ccc4ncnn4c3)cc3c2C(c2cc(F)ccc2Cl)NC3=O)CC1] | CC(=O)N[C@H]1CC[C@H](CC1)C(=O)Nc1cc(cc2C(=O)NC(c12)c1cc(F)ccc1Cl)-c1ccc2ncnn2c1 | 1H NMR (400 MHz, DMSO-d6) 9.45-9.40 (m, 1H), 9.38 (s, 1H), 9.23 (s, 1H), 8.57 (s, 1H), 8.21 (dd, 3.5, 1.7 Hz, 1H), 8.09-7.95 (m, 2H), 7.93-7.82 (s, 1H), 7.79-7.68 (s, 1H), 7.57 (s, 1H), 7.29 (td, 8.4, 3.1 Hz, 1H), 6.67 (s, 1H), 6.18 (s, 1H), 3.87-3.62 (s, 1H), 2.19-2.05 (m, 1H), 1.87-1.79 (m, 3H), 1.69-1.58 (m, 2H), 1.58-1.53 (m,1H), 1.45-1.37 (m,2H), 1.37-1.29 (m,1H), 1.29-1.17(m, 2H). | 561.05 | E | |

TABLE 2-continued

Representative Compounds of the Invention with Bioactivity Data.

| Ex. No. | Structure | SMILES | $^1$H NMR | MS | ADP-Glo IC$_{50}$ | MCF 10A IC$_{50}$ |
|---|---|---|---|---|---|---|
| I-1850 | 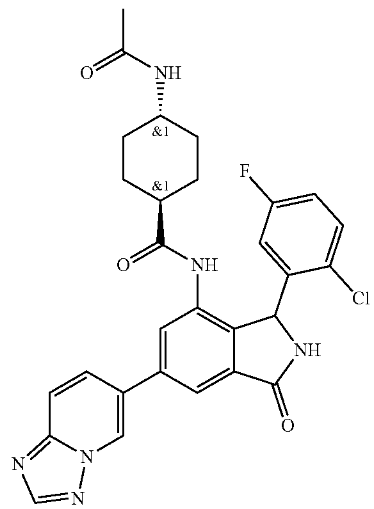 [SMILES: CC(=O)N[C@H]1CC[C@H](C(=O)Nc2cc(-c3ccc4ncnn4c3)cc3c2C(c2cc(F)ccc2Cl)NC3=O)CC1] | CC(=O)N[C@H]1CC[C@@H](CC1)C(=O)Nc1cc(cc2C(=O)NC(c12)c1cc(F)ccc1Cl)-c1ccc2ncnn2c1 | 1H NMR (400 MHz, DMSO-d6) 9.74 (s, 1H), 9.44 (t, 1.3 Hz, 1H), 9.20 (s, 1H), 8.58 (s, 1H), 8.09 (dd, 9.3, 1.9 Hz, 1H), 8.02-7.94 (m, 2H), 7.81 (d, 1.7 Hz, 1H), 7.70 (d, 7.8 Hz, 1H), 7.53 (s, 1H), 7.26 (td, 8.4, 3.1 Hz, 1H), 6.13 (s, 1H), 2.06-1.96 (m, 1H), 1.87-1.65 (m, 5H), 1.53 (dd, 8.8, 4.7 Hz., 1H), 1.36 (s, 1H), 1.32-1.23 (m, 3H), 1.21-0.98 (m, 2H). | 561.1 | E | |
| I-1851 | 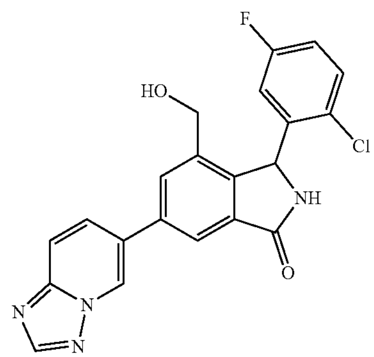 | OCc1cc(cc2C(=O)NC(c12)c1cc(F)ccc1Cl)-c1ccc2ncnn2c1 | 1H NMR (400 MHz, DMSO-d6) 9.43-9.38 (m, 1H), 9.18 (s, 1H), 8.56 (s, 1H), 8.10 (dd, 9.3, 1.9 Hz, 1H), 8.05 (d, 1.8 Hz, 1H), 8.02 (d, 1.8 Hz, 1H), 7.97 (d, 9.3 Hz, 1H), 7.60 (s, 1H), 7.28 (td, 8.4, 3.1 Hz, 1H), 6.85-6.27 (m, 1H), 6.14 (s, 1H), 5.29 (t, 5.3 Hz, 1H), 4.42 (dd, 14.2, 5.6 Hz, 1H), 4.10 (dd, 14.4, 5.1 Hz, 1H). | 409.05 | E | |
| I-1852 | 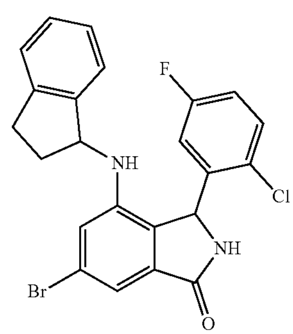 [SMILES: O=C1NC(c2cc(F)ccc2Cl)c2c(NC3CCc4ccccc43)cc(Br)cc21] | Fc1ccc(C1)c(c1)C1NC(=O)c2cc(Br)cc(NC3CCc4ccccc34)c12 | 1H NMR (400 MHz, DMSO-d6) 9.06 (d, 10.4 Hz, 1H), 7.48 (ddd, 24.1, 8.9, 5.2 Hz, 1H), 7.27-6.97 (m, 6H), 6.40 (d, 7.5 Hz, 1H), 5.86 (d, 22.4 Hz, 1H), 5.15-4.81 (m, 2H), 2.97-2.77 (m, 1H), 2.76-2.58 (m, 1H), 2.37-2.18 (m, 1H), 1.80-1.33 (m, 1H). | 471 | E | |
| I-1853 | 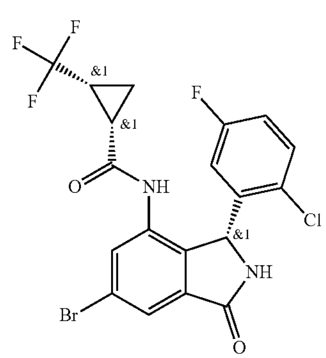 [SMILES: O=C1N[C@@H](c2cc(F)ccc2Cl)c2c(NC(=O)[C@H]3C[C@H]3C(F)(F)F)cc(Br)cc21] | Fc1ccc(C1)c(c1)[C@@H]1NC(=O)c2cc(Br)cc(NC(=O)[C@H]3C[C@H]3C(F)(F)F)c12 | 1H NMR (400 MHz, DMSO-d6) 10.36 (s, 1H), 9.24 (s, 1H), 7.74 (d, 1.7 Hz, 1H), 7.65 (d, 1.8 Hz, 1H), 7.48 (dd, 9.0, 5.0 Hz, 1H), 7.24 (td, 8.4, 3.1 Hz, 1H), 6.92-6.21 (s, 1H), 5.94 (s, 1H), 2.06 (qd, 7.2, 4.2 Hz, 1H), 1.92 (td, 7.1, 4.1 Hz, 1H), 1.16 (t, 7.4 Hz, 2H). | 490.85 | E | |

TABLE 2-continued

Representative Compounds of the Invention with Bioactivity Data.

| Ex. No. | Structure | SMILES | $^1$H NMR | MS | ADP-Glo IC$_{50}$ | MCF 10A IC$_{50}$ |
|---|---|---|---|---|---|---|
| I-1854 | 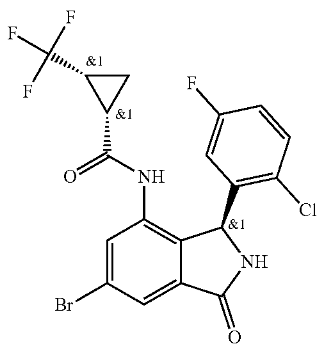 [SMILES: O=C1N[C@H](c2cc(F)ccc2Cl)c2c(NC(=O)[C@H]3C[C@H]3C(F)(F)F)cc(Br)cc21] | Fc1ccc(C1)c(c1)[C@H]1NC(=O)c2cc(Br)cc(NC(=O)[C@H]3C[C@H]3C(F)(F)F)c12 | 1H NMR (400 MHz, DMSO-d6) 10.46 (s, 1H), 9.25 (s, 1H), 7.75 (d, 1.7 Hz, 1H), 7.57 (d, 1.8 Hz, 1H), 7.47 (t, 7.0 Hz, 1H), 7.23 (td, 8.4, 3.1 Hz, 1H), 6.72 (s, 1H), 5.95 (s, 1H), 2.03 (s, 1H), 1.92 (dt, 9.3, 5.0 Hz, 1H), 1.26-1.08 (m, 2H). | 490.8 | E | |
| I-1855 | 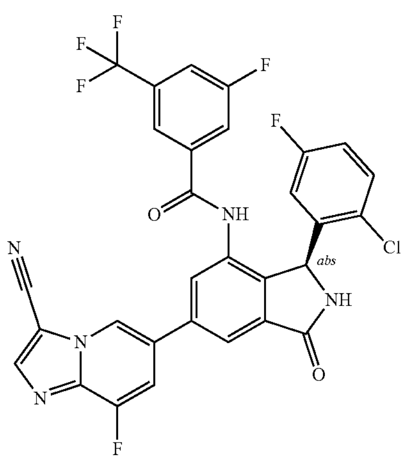 [SMILES: N#Cc1cnc2c(F)cc(-c3cc(NC(=O)c4cc(F)cc(C(F)(F)F)c4)c4c(c3)C(=O)N[C@@H]4c3cc(F)ccc3Cl)cn12] | Fc1ccc(C1)c(c1)[C@H]1NC(=O)c2cc(cc(NC(=O)c3cc(F)cc(c3)C(F)(F)F)c12)-c1cc(F)c2ncc(C#N)n2c1 | | 626.2 | C | |
| I-1856 | 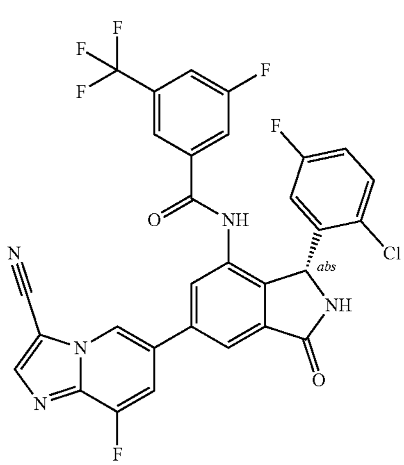 [SMILES: N#Cc1cnc2c(F)cc(-c3cc(NC(=O)c4cc(F)cc(C(F)(F)F)c4)c4c(c3)C(=O)N[C@H]4c3cc(F)ccc3Cl)cn12] | Fc1ccc(C1)c(c1)[C@@H]1NC(=O)c2cc(cc(NC(=O)c3cc(F)cc(c3)C(F)(F)F)c12)-c1cc(F)c2ncc(C#N)n2c1 | | 626.2 | A | |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-1857 | 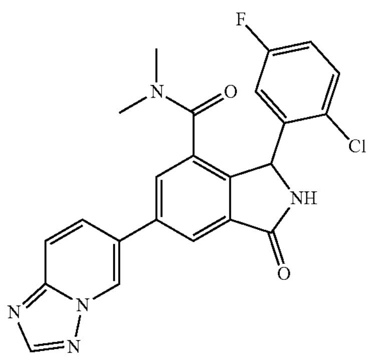 [SMILES: CN(C)C(=O)c1cc(-c2ccc3ncnn3c2)cc2c1C(c1cc(F)ccc1Cl)NC2=O] | CN(C)C(=O)c1cc(cc2C(=O)NC(c12)c1cc(F)ccc1Cl)-c1ccc2ncnn2c1 | | | | E |
| I-1858 | 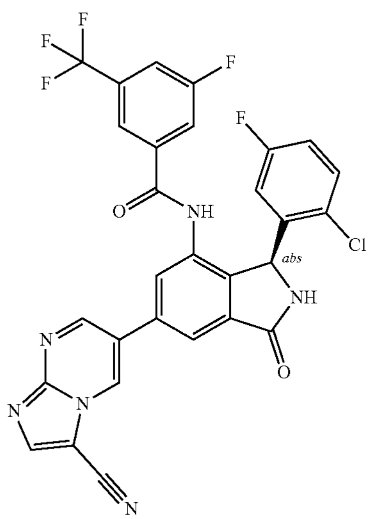 [SMILES: N#Cc1cnc2ncc(-c3cc(NC(=O)c4cc(F)cc(C(F)(F)F)c4)c4c(c3)C(=O)N[C@@H]4c3cc(F)ccc3Cl)cn12] | Fc1ccc(C1)c(c1)[C@H]1NC(=O)c2cc(cc(NC(=O)c3cc(F)cc(c3)C(F)(F)F)c12)-c1cnc2ncc(C#N)n2c1 | | 609.2 | | C |
| I-1859 | 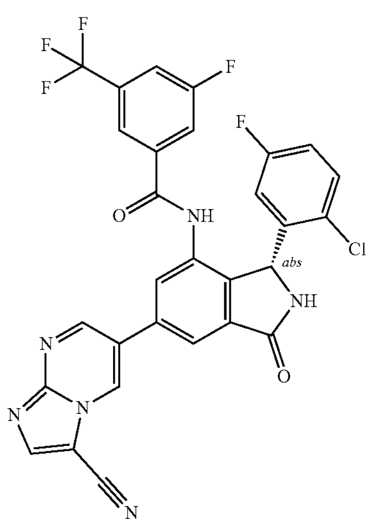 [SMILES: N#Cc1cnc2ncc(-c3cc(NC(=O)c4cc(F)cc(C(F)(F)F)c4)c4c(c3)C(=O)N[C@H]4c3cc(F)ccc3Cl)cn12] | Fc1ccc(C1)c(c1)[C@@H]1NC(=O)c2cc(cc(NC(=O)c3cc(F)cc(c3)C(F)(F)F)c12)-c1cnc2ncc(C#N)n2c1 | | 609.2 | | A |

TABLE 2-continued

Representative Compounds of the Invention with Bioactivity Data.

| Ex. No. | Structure | SMILES | $^1$H NMR | MS | ADP-Glo IC$_{50}$ | MCF 10A IC$_{50}$ |
|---|---|---|---|---|---|---|
| I-1860 | 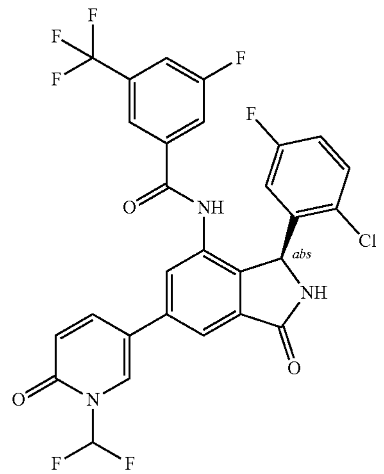 [SMILES: O=C(Nc1cc(-c2ccc(=O)n(C(F)F)c2)cc2c1[C@@H](c1cc(F)ccc1Cl)NC2=O)c1cc(F)cc(C(F)(F)F)c1] | FC(F)n1cc(ccc1=O)-c1cc2C(=O)N[C@@H](c2c(NC(=O)c2cc(F)cc(c2)C(F)(F)F)c1)c1cc(F)ccc1Cl | | 610.5 | D | |
| I-1861 | 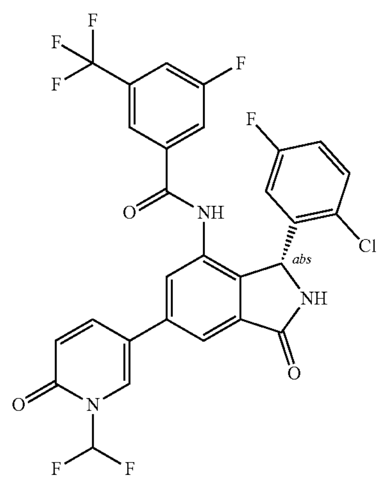 [SMILES: O=C(Nc1cc(-c2ccc(=O)n(C(F)F)c2)cc2c1[C@H](c1cc(F)ccc1Cl)NC2=O)c1cc(F)cc(C(F)(F)F)c1] | FC(F)n1cc(ccc1=O)-c1cc2C(=O)N[C@H](c2c(NC(=O)c2cc(F)cc(c2)C(F)(F)F)c1)c1cc(F)ccc1Cl | | 610.5 | A | |
| I-1862 | 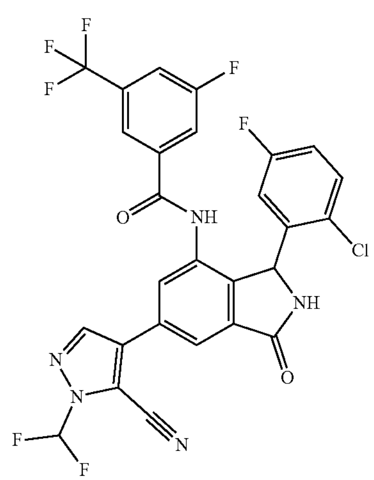 [SMILES: N#Cc1c(-c2cc(NC(=O)c3cc(F)cc(C(F)(F)F)c3)c3c(c2)C(=O)NC3c2cc(F)ccc2Cl)cnn1C(F)F] | FC(F)n1ncc(c1C#N)-c1cc2C(=O)NC(c2c(NC(=O)c2cc(F)cc(c2)C(F)(F)F)c1)c1cc(F)ccc1Cl | | | A | |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-1863 | 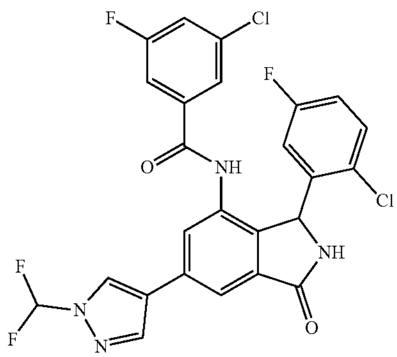 [SMILES: O=C(Nc1cc(-c2cnn(C(F)F)c2)cc2c1C(c1cc(F)ccc1Cl)NC2=O)c1cc(F)cc(Cl)c1] | FC(F)n1c c(cn1)- c1cc2C(= O)NC(c2 c(NC(=O) c2cc(F)c c(Cl)c2)c 1)c1cc(F) ccc1Cl | | | | A |
| I-1864 | 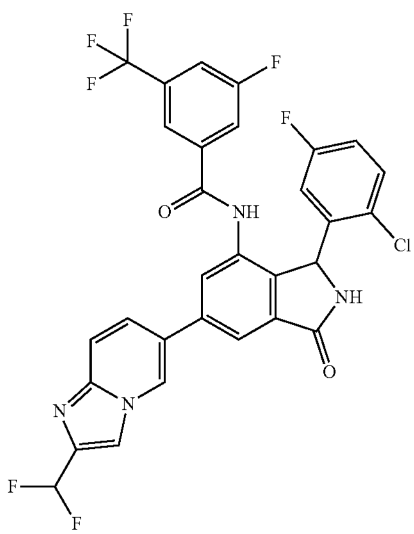 | FC(F)c1c n2cc(ccc 2n1)- c1cc2C(= O)NC(c2 c(NC(=O) c2cc(F)c c(c2)C(F) (F)F)c1)c 1cc(F)ccc 1Cl | | 633.14 | | A |
| I-1865 | 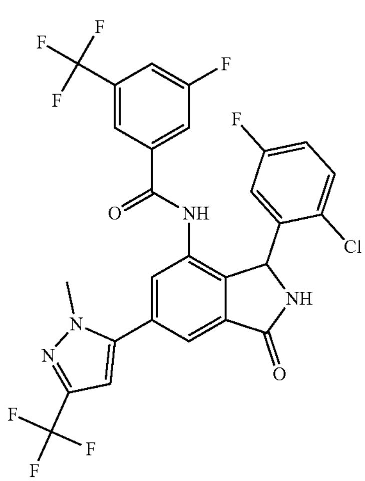 [SMILES: Cn1nc(C(F)(F)F)cc1-c1cc(NC(=O)c2cc(F)cc(C(F)(F)F)c2)c2c(c1)C(=O)NC2c1cc(F)ccc1Cl] | Cn1nc(cc 1- c1cc2C(= O)NC(c2 c(NC(=O) c2cc(F)c c(c2)C(F) (F)F)c1)c 1cc(F)ccc 1Cl)C(F) (F)F | | | | A |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-1866 | 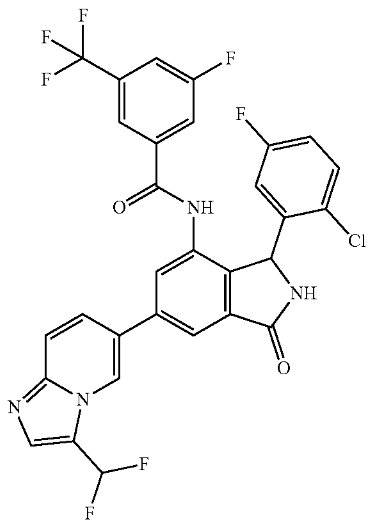 [SMILES: O=C(Nc1cc(-c2ccc3ncc(C(F)F)n3c2)cc2c1C(c1cc(F)ccc1Cl)NC2=O)c1cc(F)cc(C(F)(F)F)c1] | FC(F)c1cnc2ccc(cn12)-c1cc2C(=O)NC(c2c(NC(=O)c2cc(F)cc(c2)C(F)(F)F)c1)c1cc(F)ccc1Cl | | 633.19 | A | |
| I-1867 | 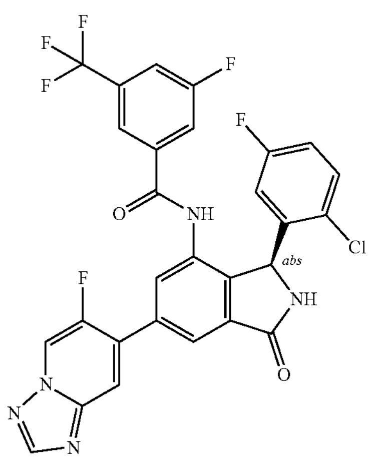 [SMILES: O=C(Nc1cc(-c2cc3ncnn3cc2F)cc2c1[C@@H](c1cc(F)ccc1Cl)NC2=O)c1cc(F)cc(C(F)(F)F)c1] | Fc1ccc(C1)c(c1)[C@H]1NC(=O)c2cc(cc(NC(=O)c3cc(F)cc(c3)C(F)(F)F)c12)-c1cc2ncnn2cc1F | 1H NMR (400 MHz, DMSO) δ 10.67 (s, 1H), 9.53 (d, J = 5.3 Hz, 1H), 9.31 (s, 1H), 8.61 (s, 1H), 8.19 (d, J = 7.3 Hz, 1H), 7.97 (d, J = 11.3 Hz, 2H), 7.82 (s, 1H), 7.76 (d, J = 9.2 Hz, 1H), 7.68 (s, 1H), 7.34 (dd, J = 8.9, 5.2 Hz, 1H), 7.15-7.09 (m, 1H), 6.08 (s, 1H). | 608.08 | D | |
| I-1868 | 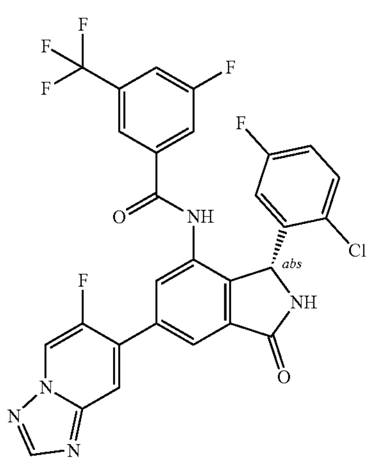 [SMILES: O=C(Nc1cc(-c2cc3ncnn3cc2F)cc2c1[C@H](c1cc(F)ccc1Cl)NC2=O)c1cc(F)cc(C(F)(F)F)c1] | Fc1ccc(C1)c(c1)[C@@H]1NC(=O)c2cc(cc(NC(=O)c3cc(F)cc(c3)C(F)(F)F)c12)-c1cc2ncnn2cc1F | 1H NMR (400 MHz, DMSO) δ 10.67 (s, 1H), 9.53 (d, J = 5.3 Hz, 1H), 9.31 (s, 1H), 8.61 (s, 1H), 8.19 (d, J = 7.3 Hz, 1H), 7.97 (d, J = 11.3 Hz, 2H), 7.82 (s, 1H), 7.76 (d, J = 9.2 Hz, 1H), 7.68 (s, 1H), 7.34 (dd, J = 8.9, 5.2 Hz, 1H), 7.15-7.09 (m, 1H), 6.08 (s, 1H). | 602.08 | A | |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-1869 | 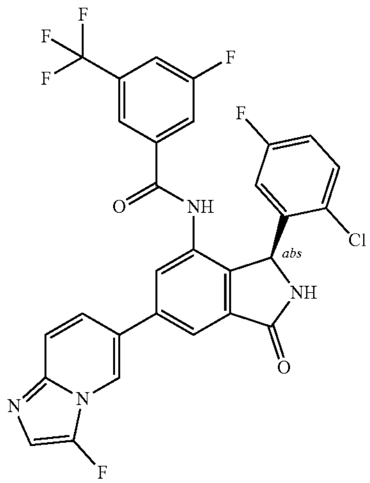 | Fc1cnc2ccc(cn12)-c1cc2C(=O)N[C@@H](c2c(NC(=O)c2cc(F)cc(c2)C(F)(F)F)c1)c1cc(F)ccc1Cl | 1H NMR (500 MHz, DMSO) δ 10.61 (s, 1H), 9.22 (s, 1H), 8.75 (s, 1H), 8.09 (d, J = 1.6 Hz, 1H), 7.95 (d, J = 8.4 Hz, 1H), 7.91 (s, 1H), 7.77 (d, J = 9.0 Hz, 1H), 7.71 (s, 1H), 7.69 (dd, J = 9.5, 1.8 Hz, 1H), 7.66 (d, J = 1.7 Hz, 1H), 7.61 (ddt, J = 9.7, 6.9, 3.9 Hz, 2H), 7.57-7.52 (m, 1H), 7.42 (d, J = 7.2 Hz, 1H), 7.33 (dd, J = 8.9, 5.2 Hz, 1H), 7.10 (td, J = 8.3, 3.1 Hz, 1H), 6.05 (s, 1H). | 601.18 | C | |
| I-1870 | 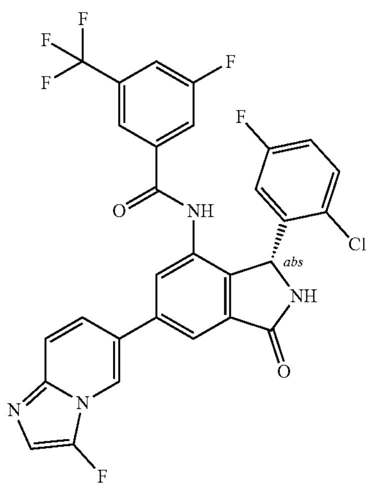 [SMILES: O=C(Nc1cc(-c2ccc3ncc(F)n3c2)cc2c1[C@H](c1cc(F)ccc1Cl)NC2=O)c1cc(F)cc(C(F)(F)F)c1] | Fc1cnc2ccc(cn12)-c1cc2C(=O)N[C@H](c2c(NC(=O)c2cc(F)cc(c2)C(F)(F)F)c1)c1cc(F)ccc1Cl | 1H NMR (500 MHz, DMSO) δ 10.61 (s, 1H), 9.22 (s, 1H), 8.75 (s, 1H), 8.09 (d, J = 1.6 Hz, 1H), 7.95 (d, J = 8.4 Hz, 1H), 7.91 (s, 1H), 7.77 (d, J = 9.0 Hz, 1H), 7.71 (s, 1H), 7.69 (dd, J = 9.5, 1.8 Hz, 1H), 7.66 (d, J= 1.7 Hz, 1H), 7.61 (ddt, J = 9.7, 6.9, 3.9 Hz, 2H), 7.57-7.52 (m, 1H), 7.42 (d, J = 7.2 Hz, 1H), 7.33 (dd, J = 8.9, 5.2 Hz, 1H), 7.10 (td, J = 8.3, 3.1 Hz, 1H), 6.05 (s, 1H). | 601.18 | A | |
| I-1871 | 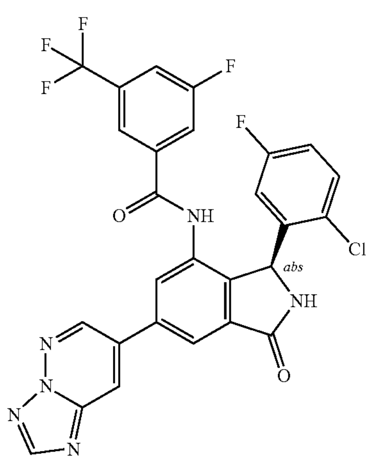 [SMILES: O=C(Nc1cc(-c2cnn3ncnc3c2)cc2c1[C@@H](c1cc(F)ccc1Cl)NC2=O)c1cc(F)cc(C(F)(F)F)c1] | Fc1ccc(C1)c(c1)[C@H]1NC(=O)c2cc(cc(NC(=O)c3cc(F)cc(c3)C(F)(F)F)c12)-c1cnn2ncnc2c1 | 1H NMR (500 MHz, DMSO) δ 10.68 (s, 1H), 9.29 (s, 1H), 9.27 (d, J = 2.4 Hz, 1H), 8.88 (d, J = 2.4 Hz, 1H), 8.73 (s, 1H), 8.30 (d, J = 1.6 Hz, 1H), 8.09 (d, J = 1.7 Hz, 1H), 7.96 (dt, J = 8.5, 2.0 Hz, 1H), 7.77 (d, J = 8.7 Hz, 1H), 7.72 (s, 1H), 7.34 (dd, J = 8.9, 5.1 Hz, 1H), 7.11 (td, J = 8.4, 3.1 Hz, 1H), 6.08 (s, 1H). | 585.12 | B | |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-1872 | 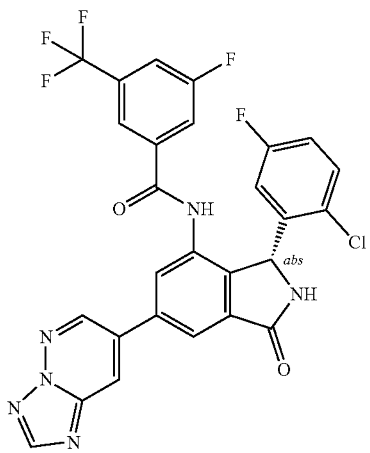 [SMILES: O=C(Nc1cc(-c2cnn3ncnc3c2)cc2c1[C@H](c1cc(F)ccc1Cl)NC2=O)c1cc(F)cc(C(F)(F)F)c1] | Fc1ccc(C1)c(c1)[C@@H]1NC(=O)c2cc(cc(NC(=O)c3cc(F)cc(c3)C(F)(F)F)c12)-c1cnn2ncnc2c1 | 1H NMR (500 MHz, DMSO) δ 10.68 (s, 1H), 9.29 (s, 1H), 9.27 (d, J = 2.4 Hz, 1H), 8.88 (d, J = 2.4 Hz, 1H), 8.73 (s, 1H), 8.30 (d, J = 1.6 Hz, 1H), 8.09 (d, J = 1.7 Hz, 1H), 7.96 (dt, J = 8.5, 2.0 Hz, 1H), 7.77 (d, J = 8.7 H7, 1H), 7.72 (s, 1H), 7.34 (dd, J = 8.9, 5.1 Hz, 1H), 7.11 (td, J = 8.4, 3.1 Hz, 1H), 6.08 (s, 1H). | 585.12 | A | |
| I-1873 | 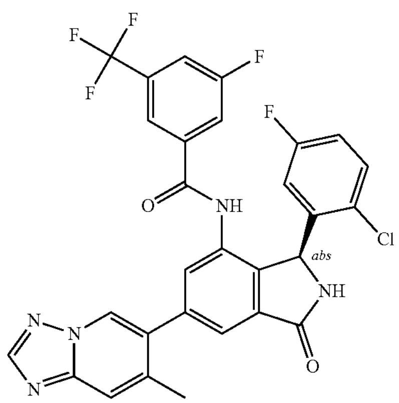 [SMILES: Cc1cc2ncnn2cc1-c1cc(NC(=O)c2cc(F)cc(C(F)(F)F)c2)c2c(c1)C(=O)N[C@@H]2c1cc(F)ccc1Cl] | Cc1cc2ncnn2cc1-c1cc2C(=O)N[C@@H](c2c(NC(=O)c2cc(F)cc(c2)C(F)(F)F)c1)c1cc(F)ccc1Cl | | | D | |
| I-1874 | 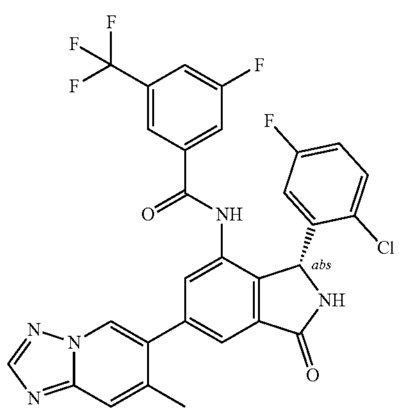 | Cc1cc2ncnn2cc1-c1cc2C(=O)N[C@H](c2c(NC(=O)c2cc(F)cc(c2)C(F)(F)F)c1)c1cc(F)ccc1Cl | | | A | |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-1875 | 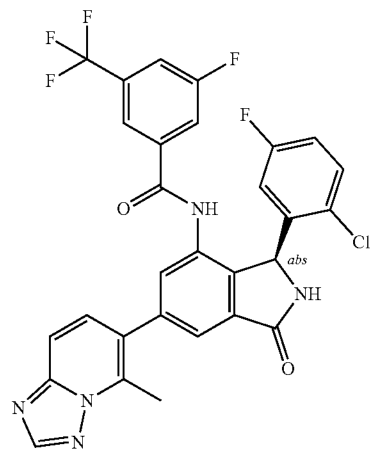 [SMILES: Cc1c(-c2cc(NC(=O)c3cc(F)cc(C(F)(F)F)c3)c3c(c2)C(=O)N[C@@H]3c2cc(F)ccc2Cl)ccc2ncnn12] | Cc1c(ccc2ncnn12)-c1cc2C(=O)N[C@@H](c2c(NC(=O)c2cc(F)cc(c2)C(F)(F)F)c1)c1cc(F)ccc1Cl | | | D | |
| I-1876 | 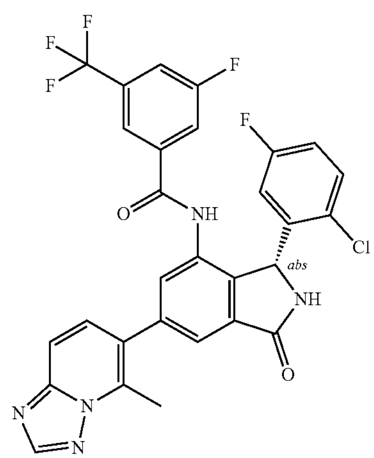 [SMILES: Cc1c(-c2cc(NC(=O)c3cc(F)cc(C(F)(F)F)c3)c3c(c2)C(=O)N[C@H]3c2cc(F)ccc2Cl)ccc2ncnn12] | Cc1c(ccc2ncnn12)-c1cc2C(=O)N[C@H](c2c(NC(=O)c2cc(F)cc(c2)C(F)(F)F)c1)c1cc(F)ccc1Cl | | | A | |
| I-1877 | 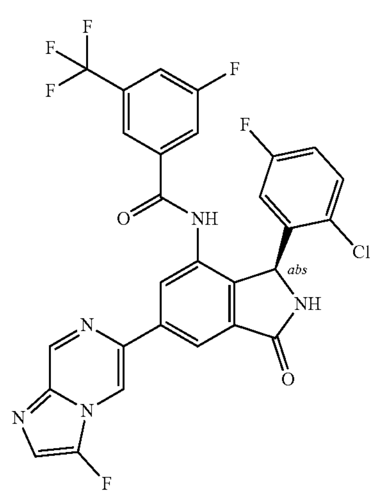 [SMILES: O=C(Nc1cc(-c2cn3c(F)cnc3cn2)cc2c1[C@@H](c1cc(F)ccc1Cl)NC2=O)c1cc(F)cc(C(F)(F)F)c1] | Fc1cnc2cnc(cn12)-c1cc2C(=O)N[C@@H](c2c(NC(=O)c2cc(F)cc(c2)C(F)(F)F)c1)c1cc(F)ccc1Cl | 1H NMR (400 MHz, DMSO) δ 10.65 (s, 1H), 9.27 (d, J = 1.4 Hz, 1H), 9.26-9.21 (m, 1H), 9.17 (t, J = 1.7 Hz, 1H), 8.47 (d, J = 1.6 Hz, 1H), 8.33 (d, J = 1.6 Hz, 1H), 7.96 (d, J = 8.4 Hz, 1H), 7.78 (d, J = 9.1 Hz, 1H), 7.75-7.69 (m, 2H), 7.33 (dd, J = 8.9, 5.2 Hz, 1H), 7.10 (td, J = 8.4, 3.0 Hz, 1H). | 602.18 | D | |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-1878 | 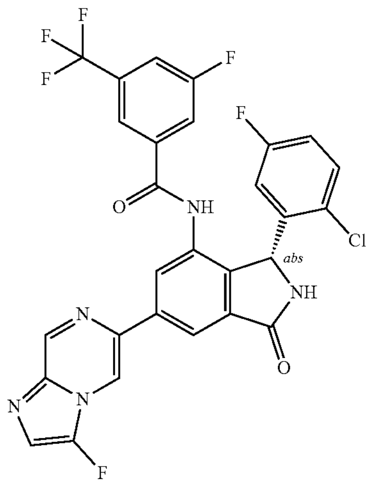 [SMILES: O=C(Nc1cc(-c2cn3c(F)cnc3cn2)cc2c1[C@H](c1cc(F)ccc1Cl)NC2=O)c1cc(F)cc(C(F)(F)F)c1] | Fc1cnc2cnc(cn12)-c1cc2C(=O)N[C@H](c2c(NC(=O)c2cc(F)cc(c2)C(F)(F)F)c1)c1cc(F)ccc1Cl | 1H NMR (400 MHz, DMSO) δ 10.65 (s, 1H), 9.27 (d, J = 1.4 Hz, 1H), 9.26-9.21 (m, 1H), 9.17 (t, J = 1.7 Hz., 1H), 8.47 (d, J = 1.6 Hz, 1H), 8.33 (d, J = 1.6 Hz, 1H), 7.96 (d, J = 8.4 Hz, 1H), 7.78 (d, J = 9.1 Hz, 1H), 7.75-7.69 (m, 2H), 7.33 (dd, J = 8.9, 5.2 Hz, 1H), 7.10 (td, J = 8.4, 3.0 Hz, 1H). | 602.18 | A | |
| I-1879 | 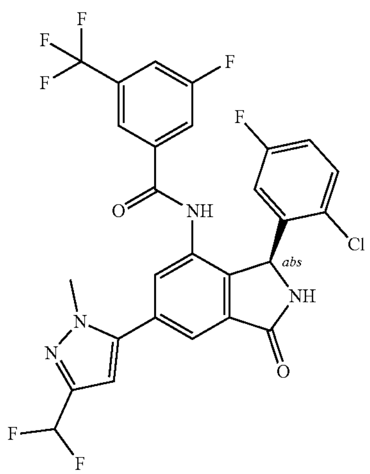 [SMILES: Cn1nc(C(F)F)cc1-c1cc(NC(=O)c2cc(F)cc(C(F)(F)F)c2)c2c(c1)C(=O)N[C@@H]2c1cc(F)ccc1Cl] | Cn1nc(cc1-c1cc2C(=O)N[C@@H](c2c(NC(=O)c2cc(F)cc(c2)C(F)(F)F)c1)c1cc(F)ccc1Cl)C(F)F | | | D | |
| I-1880 | 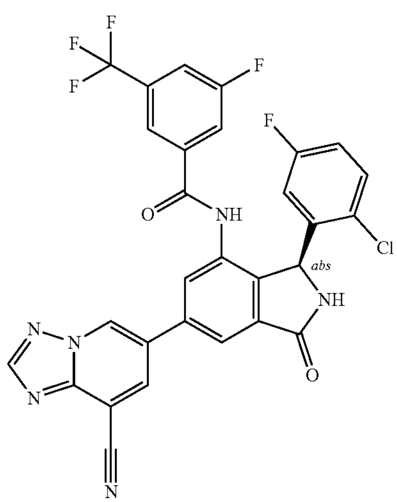 [SMILES: N#Cc1cc(-c2cc(NC(=O)c3cc(F)cc(C(F)(F)F)c3)c3c(c2)C(=O)N[C@@H]3c2cc(F)ccc2Cl)cn2ncnc12] | Fc1ccc(C1)c(c1)[C@H]1NC(=O)c2cc(cc(NC(=O)c3cc(F)cc(c3)C(F)(F)F)c12)-c1cc(C#N)c2ncnn2c1 | | 609.08 | C | |

TABLE 2-continued

Representative Compounds of the Invention with Bioactivity Data.

| Ex. No. | Structure | SMILES | $^1$H NMR | MS | ADP-Glo IC$_{50}$ | MCF 10A IC$_{50}$ |
|---|---|---|---|---|---|---|
| I-1881 | 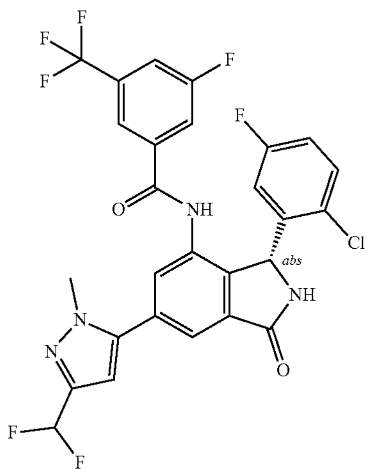 | Cn1nc(cc1-c1cc2C(=O)N[C@H](c2c(NC(=O)c2cc(F)cc(c2)C(F)(F)F)c1c c(F)ccc1Cl)C(F)F | 1H NMR (500 MHz, DMSO) δ 10.59 (s, 1H), 9.27 (s, 1H), 7.95 (d, J = 8.2 Hz, 1H), 7.85 (d, J = 1.5 Hz, 1H), 7.73 (d, J = 9.0 Hz, 1H), 7.71-7.64 (m, 2H), 7.33 (dd, J = 8.9, 5.2 Hz, 1H), 7.15 7.06 (m, 2H), 7.02 (s, 1H), 6.83 (d, J = 1.3 Hz, 1H), 4.07 (q, J = 5.3 Hz, 1H), 3.96 (s, 3H), 3.16 (d, J = 5.2 Hz, 3H). | 597.18 | A | |
| I-1882 | 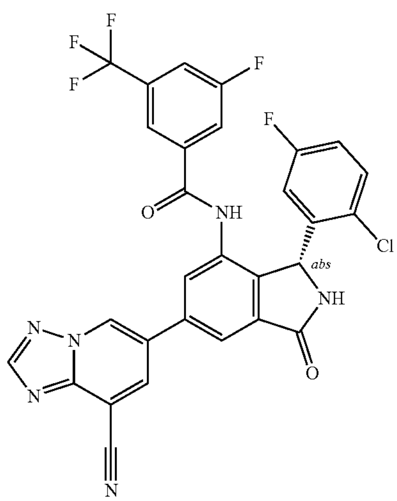 | Fc1ccc(C1)c(c1)[C@@H]1NC(=O)c2cc(cc(NC(=O)c3cc(F)cc(c3)C(F)(F)F)c12)-c1cc(C#N)c2ncnn2c1 | 1H NMR (500 MHz, DMSO) δ 10.65 (s, 1H), 9.83 (d, J = 1.7 Hz, 1H), 9.26 (s, 1H), 8.94 (d, J = 1.7 Hz, 1H), 8.76 (s, 1H), 8.23 (d, J = 1.7 Hz, 1H), 8.03 (d, J = 1.8 Hz, 1H), 7.96 (dt, J = 8.6, 2.0 Hz, 1H), 7.77 (d, J = 8.7 Hz, 1H), 7.73 (s, 1H), 7.34 (dd, J = 8.9, 5.2 Hz, 1H), 7.11 (td, J = 8.4, 3.1 Hz, 1H), 6.07 (s, 1H) | 609.08 | A | |
| I-1883 | 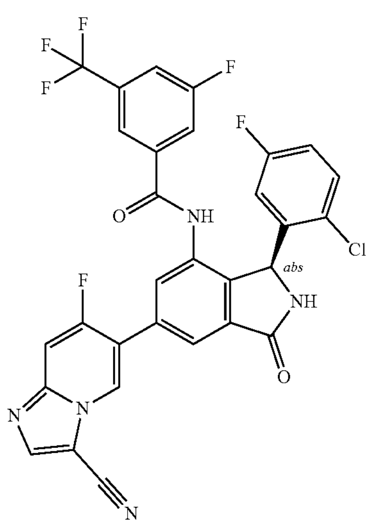 [SMILES: N#Cc1cnc2cc(F)c(-c3cc(NC(=O)c4cc(F)cc(C(F)(F)F)c4)c4c(c3)C(=O)N[C@@H]4c3cc(F)ccc3Cl)cn12] | Fc1ccc(C1)c(c1)[C@H]1NC(=O)c2cc(cc(NC(=O)c3cc(F)cc(c3)C(F)(F)F)c12)-c1cn2c(nc2cc1F)C#N | 1H NMR (400 MHz,DMSO) δ 10.66 (s, 1H), 9.31 (s, 1H), 9.22-9.16 (m, 1H), 8.55 (s, 1H), 8.20 (d, J = 7.1 Hz, 1H), 7.97 (d, J = 9.2 Hz, 2H), 7.82 (s, 1H), 7.76 (d, J = 9.1 Hz, 1H), 7.68 (s, 1H), 7.34 (dd, J = 8.9, 5.2 Hz, 1H), 7.12(td, J = 8.4, 3.0 Hz, 1H) | 626.09 | D | |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-1884 | 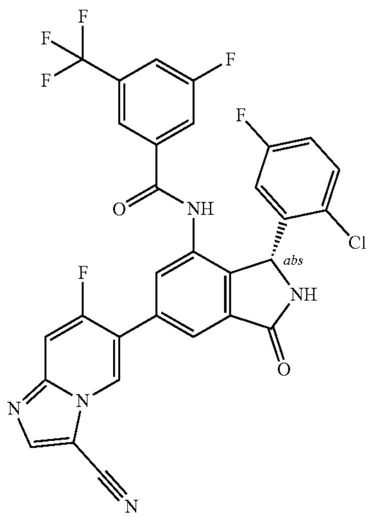 [SMILES: N#Cc1cnc2cc(F)c(-c3cc(NC(=O)c4cc(F)cc(C(F)(F)F)c4)c4c(c3)C(=O)N[C@H]4c3cc(F)ccc3Cl)cn12] | Fc1ccc(C1)c(c1)[C@@H]1NC(=O)c2cc(cc(NC(=O)c3cc(F)cc(c3)C(F)(F)F)c12)-c1cn2c(cnc2cc1F)C#N | 1H NMR (400 MHz, DMSO) δ 10.66 (s, 1H), 9.31 (s, 1H), 9.22-9.16 (m, 1H), 8.55 (s, 1H), 8.20 (d, J = 7.1 Hz, 1H), 7.97 (d, J = 9.2 Hz, 2H), 7.82 (s, 1H), 7.76 (d, J = 9.1 Hz, 1H), 7.68 (s, 1H), 7.34 (dd, J = 8.9, 5.2 Hz, 1H), 7.12 (td, J = 8.4, 3.0 Hz, 1H) | 626.09 | A | |
| I-1885 | 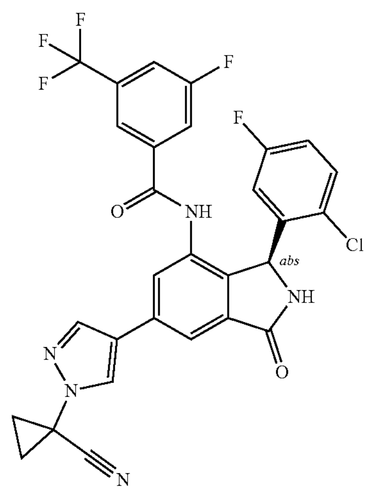 [SMILES: N#CC1(n2cc(-c3cc(NC(=O)c4cc(F)cc(C(F)(F)F)c4)c4c(c3)C(=O)N[C@@H]4c3cc(F)ccc3Cl)cn2)CC1] | Fc1ccc(C1)c(c1)[C@H]1NC(=O)c2cc(cc(NC(=O)c3cc(F)cc(c3)C(F)(F)F)c12)-c1cnn(c1)C1(CC1)C#N | | 598.2 | C | |
| I-1886 | 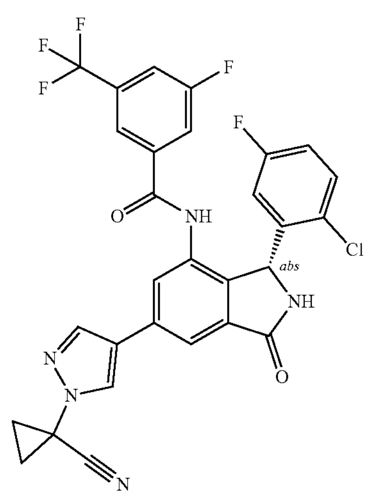 [SMILES: N#CC1(n2cc(-c3cc(NC(=O)c4cc(F)cc(C(F)(F)F)c4)c4c(c3)C(=O)N[C@H]4c3cc(F)ccc3Cl)cn2)CC1] | Fc1ccc(C1)c(c1)[C@@H]1NC(=O)c2cc(cc(NC(=O)c3cc(F)cc(c3)C(F)(F)F)c12)-c1cnn(c1)C1(CC1)C#N | | 598.2 | A | |

TABLE 2-continued

Representative Compounds of the Invention with Bioactivity Data.

| Ex. No. | Structure | SMILES | $^1$H NMR | MS | ADP-Glo IC$_{50}$ | MCF 10A IC$_{50}$ |
|---|---|---|---|---|---|---|
| I-1887 | 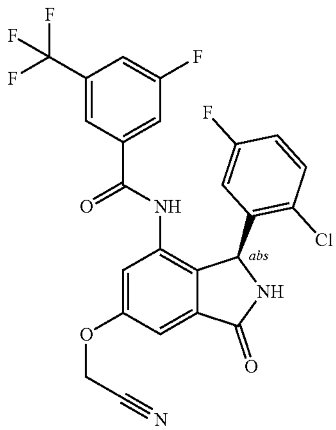 [SMILES: N#CCOc1cc(NC(=O)c2cc(F)cc(C(F)(F)F)c2)c2c(c1)C(=O)N[C@@H]2c1cc(F)ccc1Cl] | Fc1ccc(C1)c(c1)[C@H]1NC(=O)c2cc(OCC#N)cc(NC(=O)c3cc(F)cc(c3)C(F)(F)F)c12 | | 523.07 | C | |
| I-1888 | 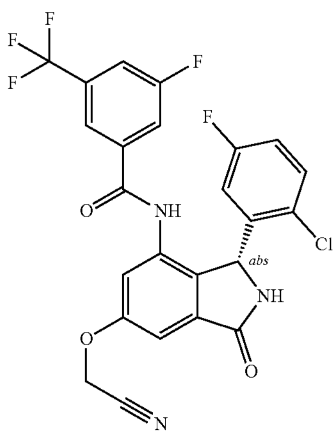 [SMILES: N#CCOc1cc(NC(=O)c2cc(F)cc(C(F)(F)F)c2)c2c(c1)C(=O)N[C@H]2c1cc(F)ccc1Cl] | Fc1ccc(C1)c(c1)[C@@H]1NC(=O)c2cc(OCC#N)cc(NC(=O)c3cc(F)cc(c3)C(F)(F)F)c12 | | 523.07 | A | |
| I-1889 | 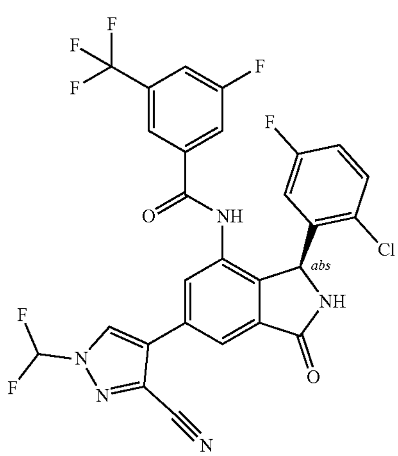 [SMILES: N#Cc1nn(C(F)F)cc1-c1cc(NC(=O)c2cc(F)cc(C(F)(F)F)c2)c2c(c1)C(=O)N[C@@H]2c1cc(F)ccc1Cl] | FC(F)n1cc(c(n1)C#N)-c1cc2C(=O)N[C@@H](c2c(NC(=O)c2cc(F)cc(c2)C(F)(F)F)c1)c1cc(F)ccc1Cl | 1H NMR (DMSO-d6, 400 MHz): δ = 10.69 (s, 1H), 9.32 (br s, 1H), 9.23 (s, 1H), 7.89-8.22 (m, 3H), 7.86 (s, 1H), 7.74 (br d, J = 8.3 Hz, 1H), 7.66 (s, 1H), 7.34 (dd, J = 8.8, 5.1 Hz, 1H), 7.12 (td, J = 8.4, 2.9 Hz, 1H), 6.38-6.88 (m, 1H), 5.82-6.20 ppm (m, 1H). | 608.5 | D | |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-1890 | 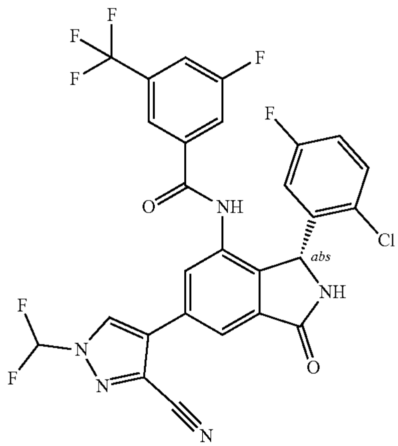 [SMILES: N#Cc1nn(C(F)F)cc1-c1cc(NC(=O)c2cc(F)cc(C(F)(F)F)c2)c2c(c1)C(=O)N[C@H]2c1cc(F)ccc1Cl] | FC(F)n1cc(c(n1)C#N)-c1cc2C(=O)N[C@H](c2c(NC(=O)c2cc(F)cc(c2)C(F)(F)F)c1c c(F)ccc1Cl | 1H NMR (DMSO-d6, 400 MHz): δ = 10.69 (s, 1H), 9.32 (br s, 1H), 9.23 (s, 1H), 7.89-8.22 (m, 3H), 7.86 (s, 1H), 7.74 (br d, J = 8.3 Hz, 1H), 7.66 (s, 1H), 7.34 (dd, J = 8.8, 5.1 Hz, 1H), 7.12 (td, J = 8.4, 2.9 Hz, 1H), 6.38-6.88 (m, 1H), 5.82-6.20 ppm (m, 1H). | 608.4 | A | |
| I-1891 | 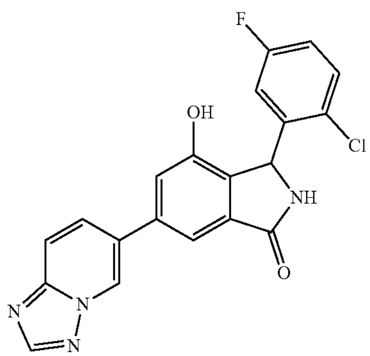 [SMILES: O=C1NC(c2cc(F)ccc2Cl)c2c(O)cc(-c3ccc4ncnn4c3)cc21] | Oc1cc(cc2C(=O)NC(c12)c1cc(F)ccc1Cl)-c1ccc2ncnn2c1 | (400 MHz, CD3CN) 9.01-8.99 (m, 1 H), 8.35 (br s, 1 H), 7.93 (dd, 9.3, 1.8 Hz, 1 H), 7.82 (dd, 9.2, 0.6 Hz, 1 H), 7.64 (d, 1.4 Hz, 1 H), 7.49 (dd, 8.8, 5.1 Hz, 1 H), 7.32 (d, 1.5 Hz, 1 H), 7.22 (br s, 1 H), 7.09 (ddd, 8.8, 8.0, 3.1 Hz, 1 H), 6.76 (dd, 9.4, 3.1 Hz, 1 H), 6.11 (br s, 1 H). | 393.3 | D | |
| I-1892 | 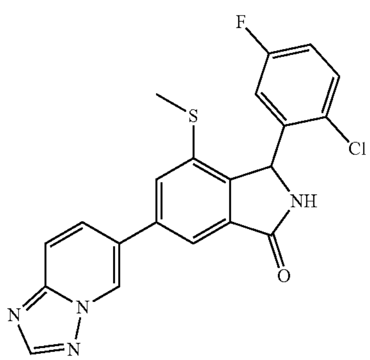 [SMILES: CSc1cc(-c2ccc3ncnn3c2)cc2c1C(c1cc(F)ccc1Cl)NC2=O] | CSc1cc(cc2C(=O)NC(c12)c1cc(F)ccc1Cl)-c1ccc2ncnn2c1 | | 425.05 | E | |
| I-1893 | 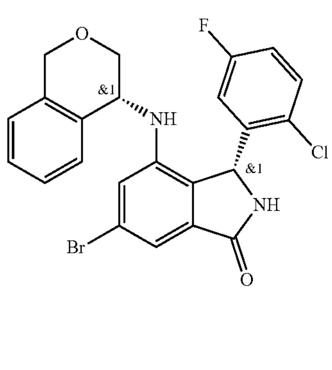 [SMILES: O=C1N[C@@H](c2cc(F)ccc2Cl)c2c(N[C@H]3COCc4ccccc43)cc(Br)cc21] | Fc1ccc(C1)c(c1)[C@@H]1NC(=O)c2cc(Br)cc(N[C@H]3COCc4ccccc34)c12 | 1H NMR (400 MHz, DMSO-d6) 9.05 (s, 1H), 7.40 (dd, 8.9, 5.2 Hz, 1H), 7.30-7.23 (m, 2H), 7.18 (td, 7.5, 1.3 Hz, 1H), 7.13 (d, 1.5 Hz, 1H), 7.05-6.92 (m, 2H), 6.84 (s, 1H), 6.55 (s, 1H), 5.80 (s, 1H), 4.88 (d, 9.3 Hz, 1H), 4.71 (q, 5.0 Hz, 1H), 4.67 (s, 2H), 3.84 (dd, 11.4, 4.2 Hz, 1H), 3.63 (dd, 11.4, 5.8 Hz., 1H). | 487 | E | |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-1894 | 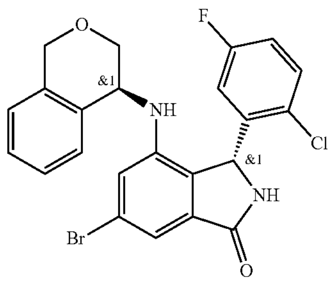 [SMILES: O=C1N[C@@H](c2cc(F)ccc2Cl)c2c(N[C@@H]3COCc4ccccc43)cc(Br)cc21] | Fc1ccc(C1)c(c1)[C@@H]1NC(=O)c2cc(Br)cc(N[C@@H]3COCc4ccccc34)c12 | 1H NMR (400 MHz, DMSO-d6) 9.05 (s, 1H), 7.40 (dd, 8.9, 5.2 Hz, 1H), 7.30-7.23 (m, 2H), 7.18 (td, 7.5, 1.3 Hz, 1H), 7.13 (d, 1.5 Hz, 1H), 7.05-6.92 (m, 2H), 6.84 (s, 1H), 6.55 (s, 1H), 5.80 (s, 1H), 4.88 (d, 9.3 Hz, 1H), 4.71 (q, 5.0 Hz, 1H), 4.67 (s, 2H), 3.99 (dd, 11.4, 4.2 Hz, 1H), 3.70 (dd, 11.4, 5.8 Hz, 1H). | 487 | E | |
| I-1895 | 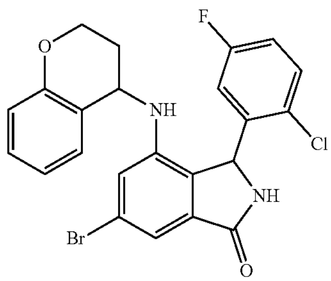 [SMILES: O=C1NC(c2cc(F)ccc2Cl)c2c(NC3CCOc4ccccc43)cc(Br)cc21] | Fc1ccc(C1)c(c1)C1NC(=O)c2cc(Br)cc(NC3CCOc4ccccc34)c12 | 1H NMR (400 MHz, DMSO-d6) 9.06 (d, 17.1 Hz, 1H), 7.48 (td, 9.3, 5.2 Hz, 1H), 7.34-7.20 (m, 2H), 7.20-7.10 (m, 2H), 7.10-7.02 (m, 1H), 6.95-6.80 (m, 1H), 6.80-6.36 (m, 2H), 5.88 (s, 1H), 5.10 (d, 7.5 Hz, 1H), 4.74 (dt, 9.3, 4.9 Hz, 1H), 4.00 (ddd, 9.9, 5.7, 3.2 Hz, 1H), 3.52-3.42 (m, 1H), 1.82 (ddd, 13.5, 8.9, 4.5 Hz, 1H), 1.62 (d, 13.7 Hz, 1H) | 486.95 | B | |
| I-1896 | 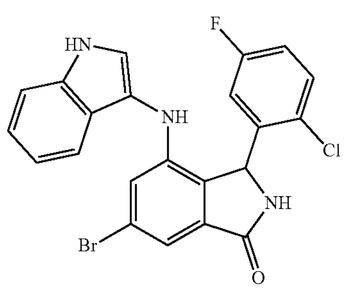 [SMILES: O=C1NC(c2cc(F)ccc2Cl)c2c(Nc3c[nH]c4ccccc34)cc(Br)cc21] | Fc1ccc(C1)c(c1)C1NC(=O)c2cc(Br)cc(Nc3c[nH]c4cccc34)c12 | 1H NMR (400 MHz, DMSO-d6) 11.00 (d, 2.7 Hz, 1H), 9.08 (s, 1H), 7.47 (ddd, 8.8, 5.2, 1.4 Hz, 1H), 7.37 (d, 8.2 Hz, 1H), 7.25-7.15 (m, 2H), 7.15-7.03 (m, 3H), 6.98-6.91 (m, 1H), 6.91 (ddd, 7.8, 6.5, 0.9 Hz, 1H), 6.78 (dd, 3.4, 1.7 Hz, 2H), 5.86 (d, 1.2 Hz, 1H). | 470 | E | |
| I-1897 | 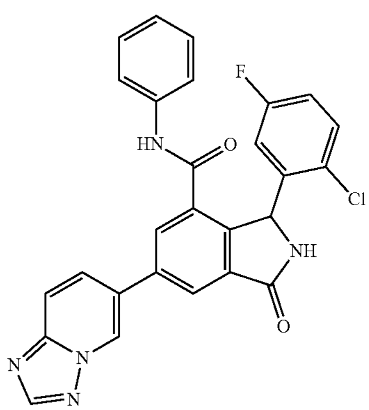 [SMILES: O=C(Nc1ccccc1)c1cc(-c2ccc3ncnn3c2)cc2c1C(c1cc(F)ccc1Cl)NC2=O] | Fc1ccc(C1)c(c1)C1NC(=O)c2cc(cc(C(=O)Nc3ccccc3)c12)-c1ccc2ncnn2c1 | 1H NMR (400 MHz, DMSO-d6) 10.39 (s, 1H), 9.61 (1, 1.3 Hz, 1H), 9.35 (s, 1H), 8.59 (s, 1H), 8.40 (s, 1H), 8.34 (d, 1.7 Hz, 1H), 8.28 (dd, 9.3, 1.9 Hz, 1H), 8.01 (d, 9.3 Hz, 1H), 7.49-7.38 (m, 3H), 7.30 (t, 7.9 Hz, 2H), 7.17-7.03 (m, 2H), 6.46 (s, 2H). | 498.15 | E | |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-1898 | 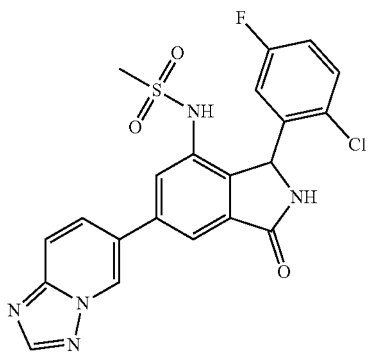 [SMILES: CS(=O)(=O)Nc1cc(-c2ccc3ncnn3c2)cc2c1C(c1cc(F)ccc1Cl)NC2=O] | CS(=O)(=O)Nc1c c(cc2C(=O)NC(c1 2)c1cc(F)ccc1Cl)-c1ccc2ncnn2c1 | 1H NMR (400 MHz, DMSO-d6) 9.33 (d, 98.3 Hz, 2H), 8.58 (s, 1H), 8.09 (dd, 9.3, 1.9 Hz, 1H), 7.98 (d, 9.5 Hz, 2H), 7.86 (d, 1.6 Hz, 1H), 7.53 (t, 7.2 Hz, 1H), 7.26 (td, 8.4, 3.1 Hz, 1H), 7.08-6.30 (s, 1H), 6.17 (s, 1H), 2.86 (m, 3H) | 472.05 | D | |
| I-1899 | 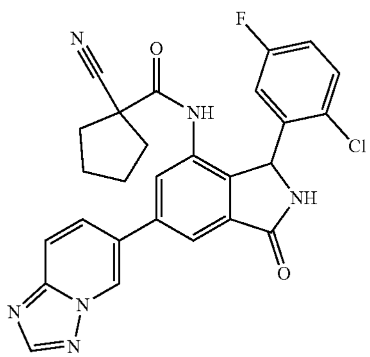 [SMILES: N#CC1(C(=O)Nc2cc(-c3ccc4ncnn4c3)cc3c2C(c2cc(F)ccc2Cl)NC3=O)CCCC1] | Fc1ccc(C1)c(c1)C1 NC(=O)c 2cc(cc(N C(=O)C3 (CCCC3) C#N)c12)-c1ccc2nc nn2c1 | 1H NMR (400 MHz, DMSO-d6) 10.31 (s, 1H), 9.49-9.44 (m, 1H), 9.26 (s, 1H), 8.57 (s, 1H), 8.16-8.06 (m, 2H), 7.98 (d, 9.3 Hz, 1H), 7.86 (d, 1.8 Hz, 1H), 7.53 (s, 1H), 7.25 (td, 8.4, 3.1 Hz, 1H), 6.56 (s, 1H), 6.09 (s, 1H), 2.13-2.02 (m, 1H), 2.04 (s, 1H), 2.02-1.93 (m, 1H), 1.97-1.83 (m, 1H), 1.78-1.55 (m, 4H) | 515.05 | E | |
| I-1900 | 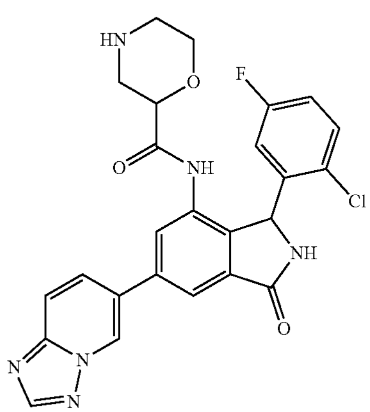 [SMILES: O=C1NC(c2cc(F)ccc2Cl)c2c(NC(=O)C3CNCCO3)cc(-c3ccc4ncnn4c3)cc21] | Fc1ccc(C1)c(c1)C1 NC(=O)c 2cc(cc(N C(=O)C3 CNCCO3) c12)-c1ccc2nc nn2c1 | NMR (400 MHz, DMSO-d6) 9.42 (dd, 3.1, 1.3 Hz, 1H), 9.27 (br s, 0.4H), 9.23 (br s, 0.6H), 9.15 (br s, 0.4H), 8.57 (s, 1H), 8.31 (s, 2H), 8.14 (d, 1.4 Hz, 0.4H), 8.10-8.07 (m, 0.6H), 8.06 (d, 1.6 Hz, 0.6H), 8.01 (d, 1.5 Hz, 0.4H), 7.98 (dd, 3.7, 1.3 Hz, 0.5H), 7.96 (dd, 2.3, 0.8 Hz, 0.5H), 7.66-7.45 (m, 1H), 7.32-7.24 (m, 1H), 6.67 (br s, 1H), 6.27-6.08 (m, 1H), 3.84-3.69 (m, 2H), 3.49-3.39 (m, 1H), 2.88 (d, 12.0 Hz, 0.5H), 2.79 (d, 12.0 Hz, 0.5H), 2.67 (d, 12.0 Hz, 1H), 2.57-2.51 (submerged m, 1H), 2.12 (br s, 0.5H), 2.03 (dd, 12.3, 10.3 Hz, 0.5H). | 507 | E | |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-1901 | 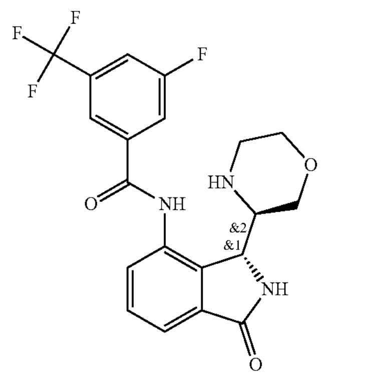 [SMILES: O=C(Nc1cccc2c1[C@H]([C@@H]1COCCN1)NC2=O)c1cc(F)cc(C(F)(F)F)c1] | Fc1cc(cc(c1)C(F)(F)F)C(=O)Nc1ccc c2C(=O)N[C@@H]([C@@H]3COCCN3)c1 2 | (400 MHz, CD3CN) 8.61 (dd, 7.9, 1.1 Hz, 1H), 8.04 (s, 1H), 7.92 (d, 9.1 Hz, 1H), 7.69 (d, 8.5 Hz, 1H), 7.57-7.47 (m, 2H), 6.93 (br s, 1H), 4.66 (s, 1H), 3.65 (dd, 11.6, 3.2 Hz, 1H), 3.49 (dd, 11.4, 3.0 Hz, 1H), 3.35 (dt, 10.5, 2.7 Hz, 1H), 3.28 (td, 11.7, 2.4 Hz, 1H), 3.06 (br s, 1H), 2.90 (td, 12.0, 3.4 Hz, 1H), 2.75 (t, 11.0 Hz, 1H), 2.63 (d, 12.0 Hz, 1H) | 424.2 | E | |
| I-1902 | 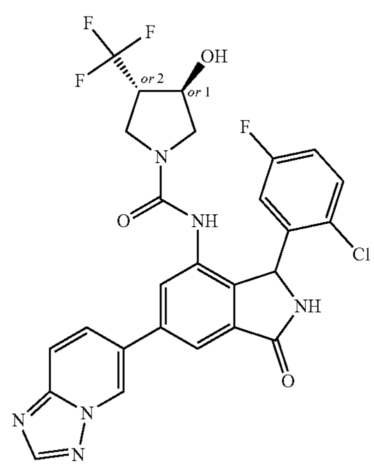 [SMILES: O=C1NC(c2cc(F)ccc2Cl)c2c(NC(=O)N3C[C@H](O)[C@@H](C(F)(F)F)C3)cc(-c3ccc4ncnn4c3)cc21] | O[C@H]1CN(C[C@@H]1C(F)(F)F)C(=O)Nc1cc(cc2C(=O)NC(c12)c1cc(F)ccc1Cl)-c1ccc2ncnn2c1 | 1H-NMR (400 MHz, DMSO-d6) 9.40-9.38 (m, 2H), 9.16 (br. s, 2H), 8.57 (s, 2H), 8.45 (br. s, 1H), 8.39 (br. s, 1H), 8.09-8.04 (m, 2H), 7.99-7.95 (m, 2H), 7.93 (s, 2H), 7.73-7.70 (m, 2H), 7.51-7.44 (m, 2H), 7.28-7.19 (m, 2H), 6.65 (br. s, 2H), 6.09 (br. s. 2H), 5.72 (d, 5.4 Hz, 1H), 5.69 (d, 4.7 Hz 1H), 4.32-4.26 (m, 1H), 4.24-4.18 (m, 1H), 3.72-3.55 (m, 2H), 3.39-3.29 (m, 2H), 3.15-3.09 (m, 2H), 3.02-2.82 (m, 4H). | 575.2 | D | |
| I-1903 | 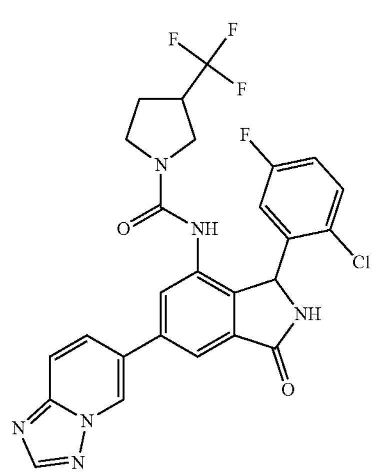 [SMILES: O=C1NC(c2cc(F)ccc2Cl)c2c(NC(=O)N3CCC(C(F)(F)F)C3)cc(-c3ccc4ncnn4c3)cc21] | Fc1ccc(C1)c(c1)C1NC(=O)c2cc(cc(NC(=O)N3CCC(C3)C(F)(F)F)c12)-c1ccc2ncnn2c1 | 1H-NMR (400 MHz, DMSO-d6) 9.40-9.38 (m, 2H), 9.16 (br. s, 2H), 8.56 (s, 2H), 8.44 (br. s, 1H), 8.40 (br. s, 1H), 8.08-8.04 (m, 2H), 7.99-7.95 (m, 2H), 7.93-7.91 (m, 2H), 7.71-7.69 (m, 2H), 7.52-7.46 (m, 2H), 7.29-7.20 (m, 2H), 6.66 (br. s, 2H), 6.07 (br. s, 2H), 3.58 (dd, 10.5, 8.8 Hz, 1H), 3.49-3.40 (m, 1H), 3.36-3.29 (m, 3H), 3.27-3.12 (m, 3H), 3.01-2.88 (m, 2H), 2.14-2.02 (m, 2H), 1.93-1.77 (m, 2H). | 559.3 | D | |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-1904 | 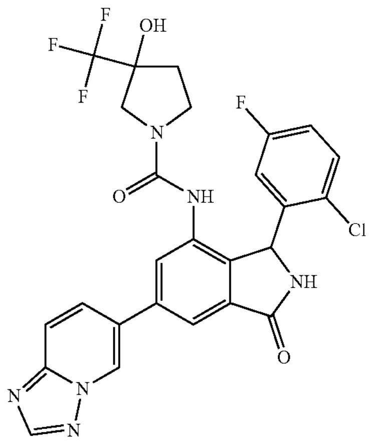 [SMILES: O=C1NC(c2cc(F)ccc2Cl)c2c(NC(=O)N3CCC(O)(C(F)(F)F)C3)cc(-c3ccc4ncnn4c3)cc21] | OC1(CCN(C1)C(=O)Nc1cc(cc2C(=O)NC(c12)c1cc(F)ccc1Cl)-c1ccc2ncnn2c1)C(F)(F)F | 1H-NMR (400 MHz, DMSO-d6) 9.40-9.38 (m, 2H), 9.15 (br. s, 2H), 8.57 (s, 2H), 8.46 (br. s, 1H), 8.36 (br. s, 1H), 8.08-8.04 (m, 2H), 7.99-7.95 (m, 2H), 7.93-7.91 (m, 2H), 7.73-7.71 (m, 1H), 7.70-7.68 (m,1H), 7.50-7.44 (m, 2H), 7.28-7.18 (m, 2H), 6.69 (br. s, 2H), 6.52 (s, 1H), 6.45 (s, 1H), 6.07 (br. s, 2H), 3.70-3.61 (m, 1H), 3.52 (d, 11.4 Hz, 1H), 3.42-3.35 (m, 3H), 3.25-3.15 (m, 2H), 3.03-2.89 (m, 1H), 2.01-1.90 (m, 4H). | 575.3 | E | |
| I-1905 | 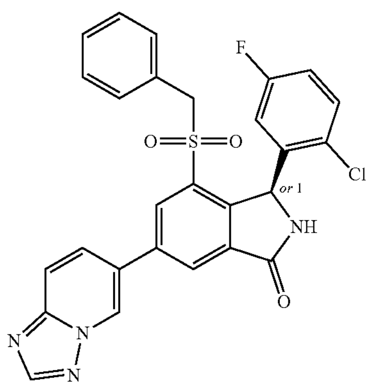 [SMILES: O=C1N[C@H](c2cc(F)ccc2Cl)c2c1cc(-c1ccc3ncnn3c1)cc2S(=O)(=O)Cc1ccccc1] | Fc1ccc(C1)c(c1)[C@H]1NC(=O)c2cc(cc(c12)S(=O)(=O)Cc1ccccc1)-c1ccc2ncnn2c1 | 1H NMR (400 MHz, DMSO-d6) 9.59 (br. s, 1H), 9.49 (br. s, 1H), 8.62 (s, 1H), 8.50 (d, 1.5 Hz, 1H), 8.29 (br. s, 1H), 8.16-8.09 (m, 1H), 8.02 (d, 8.5 Hz, 1H), 7.62 (br. s, 1H), 7.40-7.28 (m, 3H), 7.24 (br. s, 1H), 7.02 (d, 6.4 Hz, 2H), 6.42 (br. s, 1H), 6.08 (s, 1H), 4.58 (d, 12.8 Hz, 1H), 4.25 (d, 12.5 Hz, 1H). | 533.1 | D | |
| I-1906 | 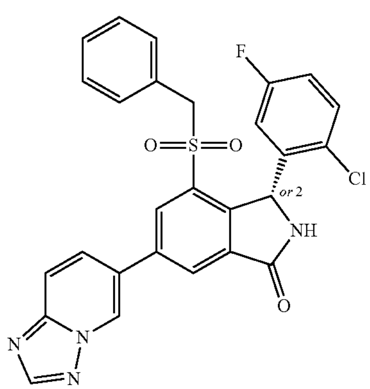 [SMILES: O=C1N[C@@H](c2cc(F)ccc2Cl)c2c1cc(-c1ccc3ncnn3c1)cc2S(=O)(=O)Cc1ccccc1] | Fc1ccc(C1)c(c1)[C@@H]1NC(=O)c2cc(cc(c12)S(=O)(=O)Cc1ccccc1)-c1ccc2ncnn2c1 | | 533.1 | E | |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-1907 | 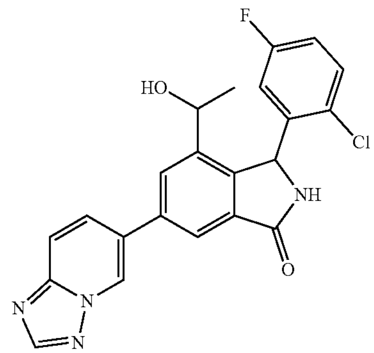 [SMILES: CC(O)c1cc(-c2ccc3ncnn3c2)cc2c1C(c1cc(F)ccc1Cl)NC2=O] | CC(O)c1cc(cc2C(=O)NC(c12)c1cc(F)ccc1Cl)-c1ccc2ncnn2c1 | 1H NMR (400 MHz, DMSO-d6) 9.43 (br. s, 1H), 9.23 (br. s, 1H), 8.57 (s, 1H), 8.14-8.10 (m, 1H), 8.09 (d, 1.8 Hz, 1H), 8.08-8.01 (m, 2H), 7.98 (br. s, 1H), 7.71-7.54 (m, 1H), 7.28 (td, 8.5, 2.9 Hz, 1H), 6.51 (br. s, 1H), 6.22 (br. s, 1H), 5.28 (d, 3.5 Hz, 1H), 4.54-4.41 (m, 1H), 1.25 (d, 5.0 Hz, 3H) | 423.1 | E | |
| I-1908 | 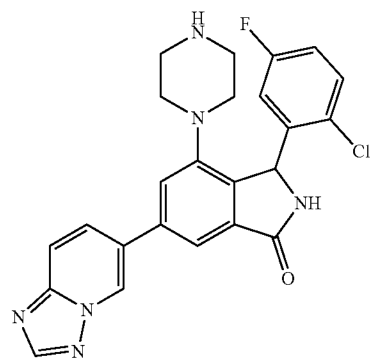 [SMILES: O=C1NC(c2cc(F)ccc2Cl)c2c1cc(-c1ccc3ncnn3c1)cc2N1CCNCC1] | Fc1ccc(C1)c(c1)C1NC(=O)c2cc(cc(N3CCNCC3)c12)-c1ccc2ncnn2c1 | NMR (400 MHz, DMSO-d6) 9.49 (dd-1.7, 0.8 Hz, 1H), 9.22 (s, 1H), 8.56 (s, 1H), 8.14 (dd, 9.3, 1.8 Hz, 1H), 7.94 (dd, 9.3, 0.7 Hz, 1H), 7.73 (d, 1.4 Hz, 1H), 7.57 (dd, 8.6, 5.5 Hz, 1H), 7.50 (d, 1.4 Hz, 1H), 7.28 (ddd, 8.8, 8.0, 3.1 Hz, 1H), 6.67 (br s, 1H), 6.17 (s, 1H), 3.16-3.05 (m, 2H), 2.78 2.66 (m, 2H), 2.48-2.32 (m, 4H). | 463 | E | |
| I-1909 | 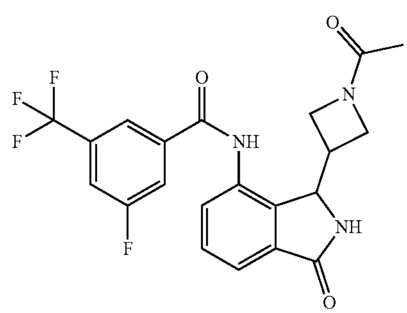 [SMILES: CC(=O)N1CC(C2NC(=O)c3cccc(NC(=O)c4cc(F)cc(C(F)(F)F)c4)c32)C1] | CC(=O)N1CC(C1)NC(=O)c2cccc(NC(=O)c3cc(F)cc(c3)C(F)(F)F)c12 | NMR (400 MHz, DMSO-d6) 10.71 (br. s, 1H), 9.11 (d, 7.2 Hz, 1H), 8.20 (s, 1H), 8.17 (d, 9.0 Hz, 1H), 8.03 (d, 8.3 Hz, 1H), 7.64-7.54 (m, 3H), 5.00 (2 d, 3.6 Hz, 1H), 4.13 (t, 8.6 Hz, 0.5H), 4.07 (dd, 8.5, 5.9 Hz, 0.5H), 3.92-3.81 (m, 1H), 3.67-3.59 (m, 0.5H), 3.38 (m, 0.5H), 3.18-3.05 (m, 1.5H), 2.93-2.87 (m, 0.5H), 1.67 (s, 1.5H), 1.61 (s, 1.5H). | 436.2 | E | |
| I-1910 | 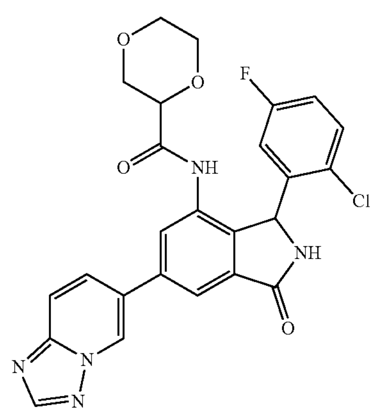 [SMILES: O=C1NC(c2cc(F)ccc2Cl)c2c(NC(=O)C3COCCO3)cc(-c3ccc4ncnn4c3)cc21] | Fc1ccc(C1)c(c1)C1NC(=O)c2cc(cc(NC(=O)C3COCCO3)c12)-c1ccc2ncnn2c1 | NMR (400 MHz, DMSO-d6) 9.54 (br s, 0.5H), 9.43 (s, 1H), 9.43 (br s, 0.5H), 9.23 (br s, 1H), 8.57 (s, 1H), 8.12-7.94 (m, 5H), 7.64-7.46 (m, 1H), 7.29 (ddd, 8.2, 6.4, 4.0 Hz, 1H), 6.61 (br s, 1H), 6.18 (br s, 0.5H), 6.13 (br s, 0.5H), 4.00 (ddd, 19.6, 9.4, 3.1 Hz, 1H), 3.81-3.55 (m, 5H), 3.40-3.30 (m, 0.5H), 2.97-2.88 (m, 0.5H). | 508 | E | |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-1911 | 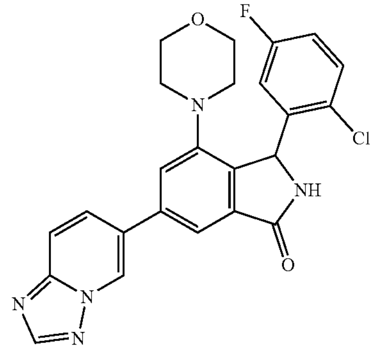 [SMILES: O=C1NC(c2cc(F)ccc2Cl)c2c1cc(-c1ccc3ncnn3c1)cc2N1CCOCC1] | Fc1ccc(C1)c(c1)C1NC(=O)c2cc(cc(N3CCOCC3)c12)-c1ccc2ncnn2c1 | NMR (400 MHz, DMSO-d6) 9.50 (dd, 1.7, 0.8 Hz, 1H), 9.25 (s, 1H), 8.56 (s, 1H), 8.21-8.13 (m, 1H), 7.95 (dd, 9.3, 0.7 Hz, 1H), 7.78 (d, 1.4 Hz, 1H), 7.62-7.54 (m, 2H), 7.28 ddd, 8.8, 8.0, 3.1 Hz, 1H), 6.77 (br s, 1H), 6.18 (s, 1H), 3.33-3.26 (m, 4H), 3.21-3.13 (m, 2H), 2.78-2.69 (m, 2H). | 464.2 | E | |
| I-1912 | 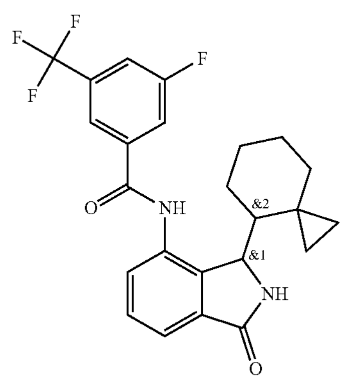 [SMILES: O=C(Nc1cccc2c1C(C1CCCCC13CC3)NC2=O)c1cc(F)cc(C(F)(F)F)c1] | Fc1cc(cc(c1)C(F)(F)F)C(=O)Nc1ccc2C(=O)NC(C3CCCC33CC3)c12 | 1H NMR (400 MHz, DMSO-d6) 10.77 (s, 0.3H), 10.74 (s, 0.7H), 8.70 (s, 0.3H), 8.61 (s, 0.7H), 8.15 (s, 4.0 Hz, 0.3H), 8.14 (s, 0.7H), 8.11 8.06 (br, d, 9.3 Hz, 1H), 8.03 (br, d, 8.5 Hz, 1H), 7.62-7.49 (m, 3H), 4.86 (d, 3.0 Hz, 0.3H), 4.63 (s, 0.7H), 1.87-1.75 (m, 0.7H), 1.75-1.61 (m, 0.3H), 1.61-1.45 (m, 1.4H), 1.45-1.31 (m, 2.1H), 1.27-1.19 (m, 0.7H), 1.18-1.06 (m, 0.7H), 1.05-0.96 (m, 0.7H), 0.95-0.85 (m, 1.4H), 0.76-0.64 (m, 0.3H), 0.59-0.52 (m, 0.7H), 0.34 (dt, 9.0, 4.5 Hz, 0.7H), 0.20 (dt, 9.9, 5.0 Hz, 0.7H), 0.06 (t, 3.8 Hz, 0.3H),−0.01-0.14 (m, 1.2H),−0.14-0.21 (m, 0.3H),−0.34 (t, 6.7 Hz, 0.3H). | 447 | D | |
| I-1913 | 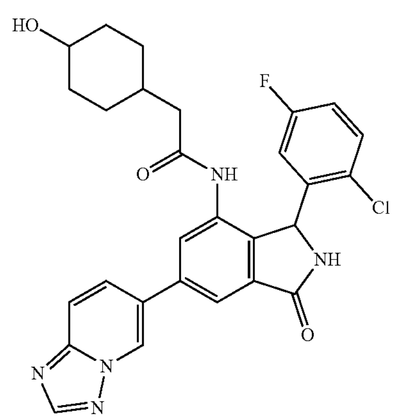 [SMILES: O=C(CC1CCC(O)CC1)Nc1cc(-c2ccc3ncnn3c2)cc2c1C(c1cc(F)ccc1Cl)NC2=O] | OC1CCC(CC(=O)Nc2cc(cc3C(=O)NC(c23)c2cc(F)ccc2Cl)-c2ccc3ncnn3c2)CC1 | 1H NMR (400 MHz, DMSO-d6) 9.75 (br s, 0.2H), 9.74 (br s, 0.8H), 9.42-9.38 (m, 1H), 9.16 (br s, 1H), 8.53 (s, 1H), 8.04 (dt, 10.2, 5.1 Hz, 1H), 7.96 (m, 2H), 7.85-7.81 (m, 1H), 7.57-7.40 (m, 1H), 7.24-7.18 (m, 1H), 6.52 (br s, 1H), 6.16 (br s, 1H), 4.42 (s, 0.8H), 4.21 (s, 0.2H), 3.24-3.14 (m, 1H), 1.94-1.84 (m, 2H), 1.67 (d, 11.2 Hz, 2H), 1.45-1.23 (m, 3H), 1.06-0.90 (m, 2H), 0.82-0.65 (m, 2H). | 534.3 | E | |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-1914 | 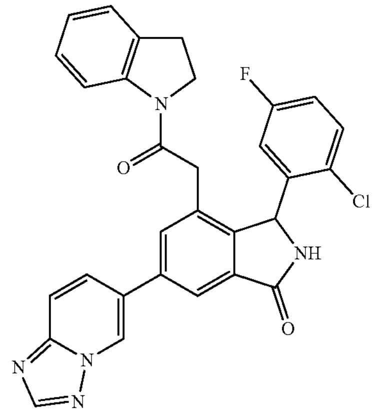 [SMILES: O=C1NC(c2cc(F)ccc2Cl)c2c(CC(=O)N3CCc4ccccc43)cc(-c3ccc4ncnn4c3)cc21] | Fc1ccc(C1)c(c1)C1NC(=O)c2cc(cc(CC(=O)N3CCc4ccccc34)c12)-c1ccc2ncnn2c1 | 1H NMR (400 MHz, DMSO-d6) 9.44 (dd, 1.1, 0.6 Hz, 1H), 9.25 (br s, 1H), 8.56 (s, 1H), 8.12 (dd, 9.3, 1.8 Hz, 2H), 7.97 (d, 9.4 Hz, 1H), 7.96 (br s, 1H), 7.83 (d, 8.0 Hz, 1H), 7.48 (br s, 1H), 7.23 (d, 7.4 Hz, 1H), 7.10 (t, 7.7 Hz, 1H), 7.07-7.02 (m, 1H), 6.98 (t, 7.4 Hz, 1H), 6.50 (br. d, 7.9 Hz, 1H), 6.17 (br. s, 1H), 4.00 (dd, 18.6, 8.5 Hz, 1H), 3.84 (m, 2H), 3.53-3.44 (m, 1H), 3.14 (t, 8.3 Hz, 2H). | 538.2 | E | |
| I-1915 | 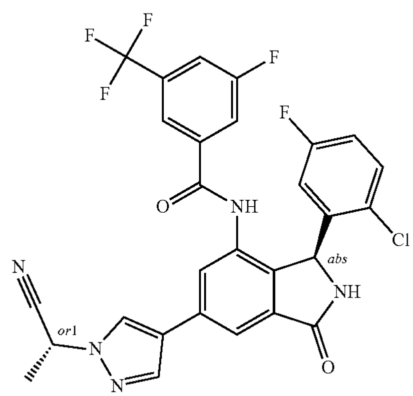 [SMILES: C[C@H](C#N)n1cc(-c2cc(NC(=O)c3cc(F)cc(C(F)(F)F)c3)c3c(c2)C(=O)N[C@@H]3c2cc(F)ccc2Cl)cn1] | C[C@H](C#N)n1cc(cn1)-c1cc2C(=O)N[C@@H](c2c(NC(=O)c2cc(F)cc(c2)C(F)(F)F)c1)c1cc(F)ccc1Cl | | | D | |
| I-1916 | 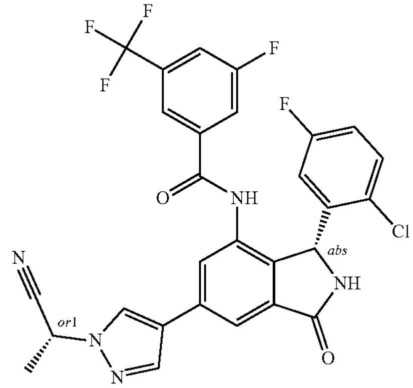 [SMILES: C[C@H](C#N)n1cc(-c2cc(NC(=O)c3cc(F)cc(C(F)(F)F)c3)c3c(c2)C(=O)N[C@H]3c2cc(F)ccc2Cl)cn1] | C[C@H](C#N)n1cc(cn1)-c1cc2C(=O)N[C@@H](c2c(NC(=O)c2cc(F)cc(c2)C(F)(F)F)c1)c1cc(F)ccc1Cl | 1H NMR(400 MHz, DMSO-d6) δ 10.82 (br s, 1 H), 9.16 (s, 1 H), 8.61 (s, 1 H), 8.22 (s, 1 H), 7.96-7.93 (m, 2 H), 7.83-7.70 (m, 3 H), 7.31 (dd, J = 8.9, 5.2 Hz, 1 H), 7.08 (td, J = 8.3, 3.0 Hz, 1 H), 6.62 (brs, 1 H), 5.99 (brs, 1 H), 5.89 (q, J = 7.1 Hz, 1 H), 1.86 (d, J = 7.1 Hz, 3 H). | 586.3 | A | |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-1917 | 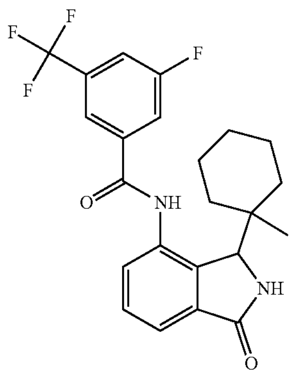 [SMILES: CC1(C2NC(=O)c3cccc(NC(=O)c4cc(F)cc(C(F)(F)F)c4)c32)CCCCC1] | CC1(CCCCC1)C1NC(=O)c2cccc(NC(=O)c3cc(F)cc(c3)C(F)(F)F)c12 | 1H NMR (400 MHz, DMSO-d6) 10.75 (s, 1H), 8.75 (s, 1H), 8.15 (s, 1H), 8.08 (d, 9.0 Hz, 1H), 8.02 (d, 8.5 Hz, 1H), 7.60-7.49 (m, 3H), 4.69 (s, 1H), 1.47-1.10 (m, 9H), 1.06-0.98 (m, 1H), 0.51 (s, 3H). | 435 | E | |
| I-1918 | 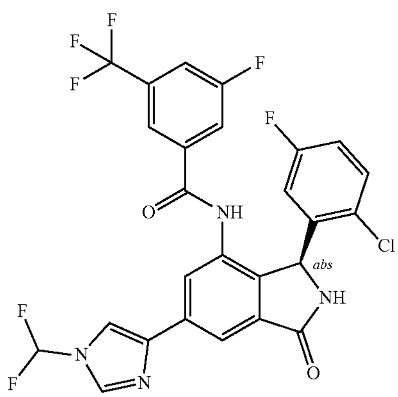 [SMILES: O=C(Nc1cc(-c2cn(C(F)F)cn2)cc2c1[C@@H](c1cc(F)ccc1Cl)NC2=O)c1cc(F)cc(C(F)(F)F)c1] | FC(F)n1cnc(c1)-c1cc2C(=O)N[C@@H](c2c(NC(=O)c2cc(F)cc(c2)C(F)(F)F)c1)c1cc(F)ccc1Cl | 1H NMR (400 MHz, DMSO) δ 10.56 (s, 1H), 9.18 (s, 1H), 8.94 (s, 1H), 8.43 (s, 1H), 8.06 (d, J = 1.6 Hz, 1H), 8.02-7.79 (m, 3H), 7.75 (d, J = 9.1 Hz, 1H), 7.70 (d, J = 2.2 Hz, 1H), 7.31 (dd, J = 8.9, 5.1 Hz, 1H), 7.09 (td, J = 8.3, 3.1 Hz, 1H), 6.86-6.58 (m, 1H), 5.98 (s, 1H). | 583.2 | D | |
| I-1919 | 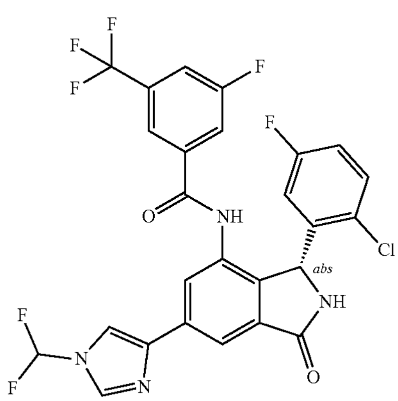 [SMILES: O=C(Nc1cc(-c2cn(C(F)F)cn2)cc2c1[C@H](c1cc(F)ccc1Cl)NC2=O)c1cc(F)cc(C(F)(F)F)c1] | FC(F)n1cnc(c1)-c1cc2C(=O)N[C@H](c2c(NC(=O)c2cc(F)cc(c2)C(F)(F)F)c1)c1cc(F)ccc1Cl | 1H NMR (400 MHz, DMSO) δ 10.56 (s, 1H), 9.18 (s, 1H), 8.94 (s, 1H), 8.43 (s, 1H), 8.06 (d, J = 1.6 Hz, 1H), 8.02 7.79 (m, 3H), 7.75 (d, J = 9.1 Hz, 1H), 7.70 (d, J = 2.2 Hz, 1H), 7.31 (dd, J = 8.9, 5.1 Hz, 1H), 7.09 (td, J = 8.3, 3.1 Hz, 1H), 6.86-6.58 (m, 1H), 5.98 (s, 1H). | 583.2 | A | |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-1920 | 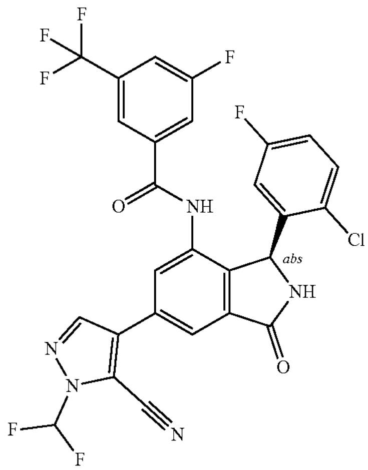 [SMILES: N#Cc1c(-c2cc(NC(=O)c3cc(F)cc(C(F)(F)F)c3)c3c(c2)C(=O)N[C@@H]3c2cc(F)ccc2Cl)cnn1C(F)F] | FC(F)n1ncc(c1C#N)-c1cc2C(=O)N[C@@H](c2c(NC(=O)c2cc(F)cc(c2)C(F)(F)F)c1)c1cc(F)ccc1Cl | 1H NMR (400 MHz, DMSO) δ 10.71 (s, 1H), 9.32 (s, 1H), 8.71 (s, 1H), 8.13 (d, J = 1.6 Hz, 1H), 7.97 (d, J = 8.4 Hz, 1H), 7.90 (d, J = 1.6 Hz, 1H), 7.73 (d, J = 9.0 Hz, 1H), 7.65 (s, 1H), 7.33 (dd, J = 8.9, 5.2 Hz, 1H), 7.11 (td, J = 8.8, 8.4, 3.0 Hz, 1H), 6.01 (s, 1H). | 608.13 | D | |
| I-1921 | 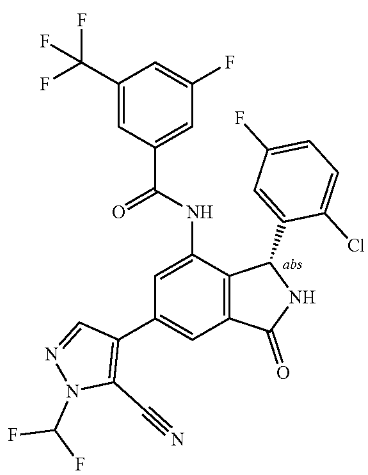 [SMILES: N#Cc1c(-c2cc(NC(=O)c3cc(F)cc(C(F)(F)F)c3)c3c(c2)C(=O)N[C@H]3c2cc(F)ccc2Cl)cnn1C(F)F] | FC(F)n1ncc(c1C#N)-c1cc2C(=O)N[C@H](c2c(NC(=O)c2cc(F)cc(c2)C(F)(F)F)c1)c1cc(F)ccc1Cl | 1H NMR (400 MHz, DMSO) δ 10.71 (s, 1H), 9.32 (s, 1H), 8.71 (s, 1H), 8.13 (d, J = 1.6 Hz, 1H), 7.97 (d, J = 8.4 Hz, 1H), 7.90 (d, J = 1.6 Hz, 1H), 7.73 (d, J = 9.0 Hz, 1H), 7.65 (s, 1H), 7.33 (dd, J = 8.9, 5.2 Hz, 1H), 7.11 (td, J = 8.8, 8.4, 3.0 Hz, 1H), 6.01 (s, 1H). | 608.13 | A | |
| I-1922 | 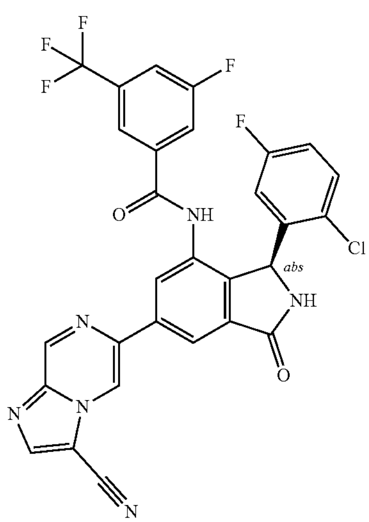 [SMILES: N#Cc1cnc2cnc(-c3cc(NC(=O)c4cc(F)cc(C(F)(F)F)c4)c4c(c3)C(=O)N[C@@H]4c3cc(F)ccc3Cl)cn12] | Fc1ccc(C1)c(c1)[C@H]1NC(=O)c2cc(cc(NC(=O)c3cc(F)cc(c3)C(F)(F)F)c12)-c1cn2c(cnc2cn1)C#N | 1H NMR (400 MHz, DMSO) δ 10.67 (s, 1H), 9.52 (d, J = 1.5 Hz, 1H), 9.46 (d, J = 1.5 Hz, 1H), 9.24 (s, 1H), 8.67 (s, 1H), 8.55 (d, J = 1.6 Hz, 1H), 8.43-8.34 (m, 1H), 7.95 (d, J = 8.6 Hz, 1H), 7.79 (d, J = 9.1 Hz, 1H), 7.72 (s, 1H), 7.33 (dd, J = 8.9, 5.2 Hz, 1H), 7.10 (td, J = 8.4, 3.1 Hz, 1H), 6.62 (s, 1H), 6.06 (s, 1H). | 609.18 | D | |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-1923 | 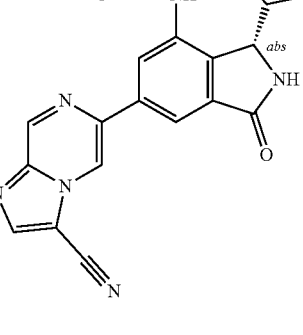 | Fc1ccc(C1)c(c1)[C@@H]1NC(=O)c2cc(cc(NC(=O)c3cc(F)cc(c3)C(F)(F)F)c12)-c1cn2c(cnc2cn1)C#N | 1H NMR (400 MHz, DMSO) δ 10.67 (s, 1H), 9.52 (d, J = 1.5 Hz, 1H), 9.46 (d, J = 1.5 Hz, 1H), 9.24 (s, 1H), 8.67 (s, 1H), 8.55 (d, J = 1.6 Hz, 1H), 8.43-8.34 (m, 1H), 7.95 (d, J = 8.6 Hz, 1H), 7.79 (d, J = 9.1 Hz, 1H), 7.72 (s, 1H), 7.33 (dd, J = 8.9, 5.2 Hz, 1H), 7.10 (td, J = 8.4, 3.1 Hz, 1H), 6.62 (s, 1H), 6.06 (s, 1H). | 609.18 | A | |
| I-1924 | 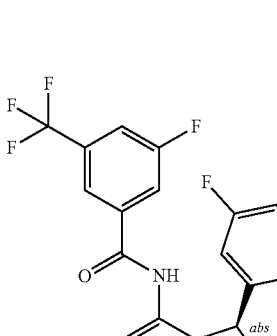 | FC(F)c1nnc2ccc(cn12)-c1cc2C(=O)N[C@@H](c2c(NC(=O)c2cc(F)cc(c2)C(F)(F)F)c1)c1cc(F)ccc1Cl | 1H NMR (500 MHz, DMSO) δ 12.67 (s, 1H), 10.64 (s, 1H), 9.26 (s, 1H), 9.03 (t, J = 1.4 Hz, 1H), 8.12 (d, J = 1.7 Hz, 1H), 8.10-7.99 (m, 2H), 7.98-7.83 (m, 3H), 7.79-7.72 (m, 1H), 7.70 (s, 1H), 7.33 (dd, J = 8.9, 5.1 Hz, 1H), 7.10 (td, J = 8.3, 3.0 Hz, 1H), 6.07 (s, 1H) | 634.19 | D | |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-1925 | 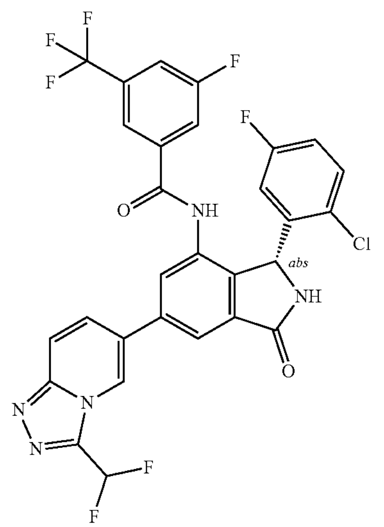 | FC(F)c1nnc2ccc(cn12)-c1cc2C(=O)N[C@H](c2c(NC(=O)c2cc(F)cc(c2)C(F)(F)F)c1c(F)ccc1Cl | 1H NMR (500 MHz, DMSO) δ 12.67 (s, 1H), 10.64 (s, 1H), 9.26 (s, 1H), 9.03 (t, J = 1.4 Hz, 1H), 8.12 (d, J = 1.7 Hz, 1H), 8.10-7.99 (m, 2H), 7.98-7.83 (m, 3H), 7.79-7.72 (m, 1H), 7.70 (s, 1H), 7.33 (dd, J = 8.9, 5.1 Hz, 1H), 7.10 (td, J = 8.3, 3.0 Hz, 1H), 6.07 (s, 1H) | 634.19 | A | |
| I-1926 | 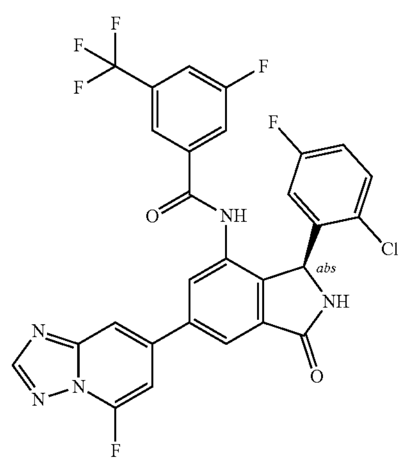 [SMILES: O=C(Nc1cc(-c2cc(F)n3ncnc3c2)cc2c1[C@@H](c1cc(F)ccc1Cl)NC2=O)c1cc(F)cc(C(F)(F)F)c1] | Fc1ccc(C1)c(c1)[C@H]1NC(=O)c2cc(cc(NC(=O)c3cc(F)cc(c3)C(F)(F)F)c12)-c1cc(F)n2ncnc2c1 | | 602.03 | D | |
| I-1927 | 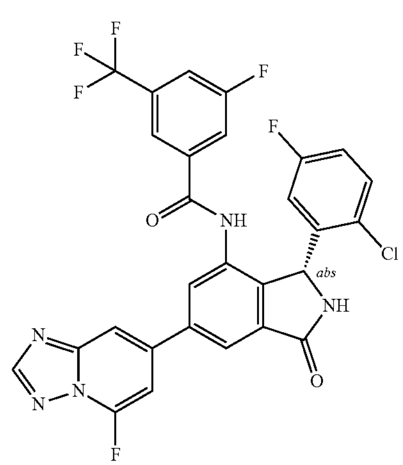 [SMILES: O=C(Nc1cc(-c2cc(F)n3ncnc3c2)cc2c1[C@H](c1cc(F)ccc1Cl)NC2=O)c1cc(F)cc(C(F)(F)F)c1] | Fc1ccc(C1)c(c1)[C@@H]1NC(=O)c2cc(cc(NC(=O)c3cc(F)cc(c3)C(F)(F)F)c12)-c1cc(F)n2ncnc2c1 | | 602.03 | A | |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-1928 | 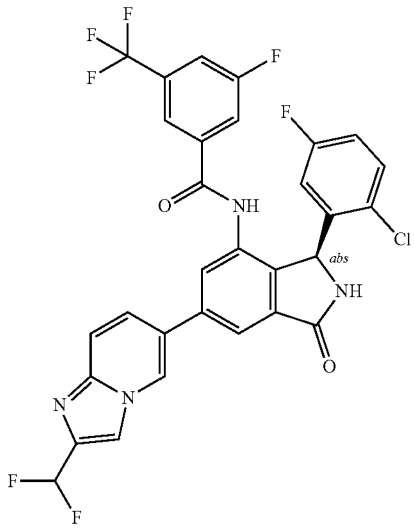 [SMILES: O=C(Nc1cc(-c2ccc3nc(C(F)F)cn3c2)cc2c1[C@@H](c1cc(F)ccc1Cl)NC2=O)c1cc(F)cc(C(F)(F)F)c1] | FC(F)c1cn2cc(ccc2n1)-c1cc2C(=O)N[C@@H](c2c(NC(=O)c2cc(F)cc(c2)C(F)(F)F)c1)c1cc(F)ccc1Cl | 1H NMR (400 MHz, DMSO) δ 10.64 (s, 1H), 9.26 (s, 1H), 9.18 (dd, J = 2.0, 1.1 Hz, 1H), 8.27 (t, J = 1.9 Hz, 1H), 8.04 (d, J = 1.6 Hz, 1H), 7.97 (d, J = 8.5 Hz, 1H), 7.86 (s, 1H), 7.82 (dd, J = 9.5, 1.9 Hz, 1H), 7.79-7.69 (m, 3H), 7.33 (dd, J = 5.6, 3.3 Hz, 1H), 7.19 (s, 1H), 7.11 (td, J = 8.4, 3.0 Hz, 1H), 6.05 (s, 1H). | 633.24 | D | |
| I-1929 | 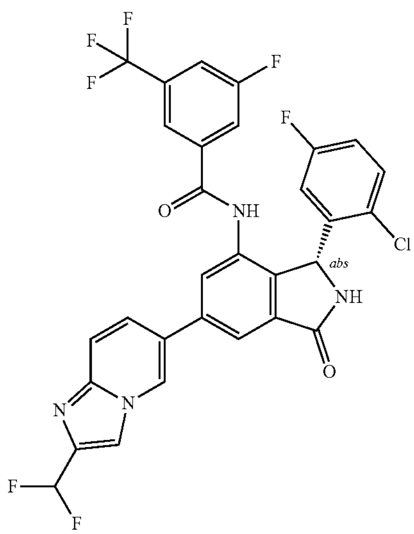 [SMILES: O=C(Nc1cc(-c2ccc3nc(C(F)F)cn3c2)cc2c1[C@H](c1cc(F)ccc1Cl)NC2=O)c1cc(F)cc(C(F)(F)F)c1] | FC(F)c1cn2cc(ccc2n1)-c1cc2C(=O)N[C@H](c2c(NC(=O)c2cc(F)cc(c2)C(F)(F)F)c1)c1cc(F)ccc1Cl | 1H NMR (400 MHz, DMSO) δ 10.64 (s, 1H), 9.26 (s, 1H), 9.18 (dd, J = 2.0, 1.1 Hz, 1H), 8.27 (t, J = 1.9 Hz, 1H), 8.04 (d, J = 1.6 Hz, 1H), 7.97 (d, J = 8.5 Hz, 1H), 7.86 (s, 1H), 7.82 (dd, J = 9.5, 1.9 H2, 1H), 7.79-7.69 (m, 3H), 7.33 (dd, J = 5.6, 3.3 Hz, 1H), 7.19 (s, 1H), 7.11 (td, J = 8.4, 3.0 Hz, 1H), 6.05 (s, 1H). | 633.24 | A | |
| I-1930 | 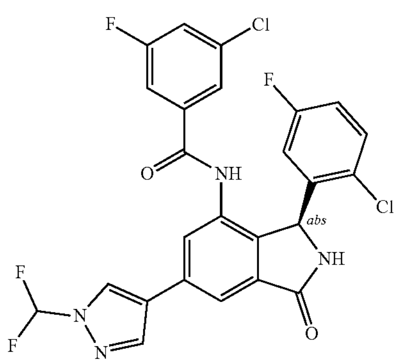 [SMILES: O=C(Nc1cc(-c2cnn(C(F)F)c2)cc2c1[C@@H](c1cc(F)ccc1Cl)NC2=O)c1cc(F)cc(Cl)c1] | FC(F)n1cc(cn1)-c1cc2C(=O)N[C@@H](c2c(NC(=O)c2cc(F)cc(C1)c2)c1)c1cc(F)ccc1Cl | 1H NMR (400 MHz, DMSO) δ 10.56 (s, 1H), 9.18 (s, 1H), 8.94 (s, 1H), 8.43 (s, 1H), 8.06 (d, J = 1.6 Hz, 1H), 8.02-7.79 (m, 3H), 7.75 (d, J = 9.1 Hz, 1H), 7.70 (d, J = 2.2 Hz, 1H), 7.31 (dd, J = 8.9, 5.1 Hz, 1H), 7.09 (td, J = 8.3, 3.1 Hz, 1H), 6.86-6.58 (m, 1H), 5.98 (s, 1H). | 583.2 | D | |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-1931 | 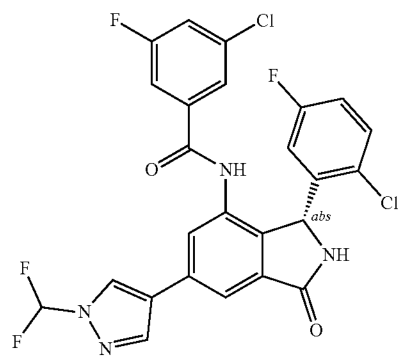 [SMILES: O=C(Nc1cc(-c2cnn(C(F)F)c2)cc2c1[C@H](c1cc(F)ccc1Cl)NC2=O)c1cc(F)cc(Cl)c1] | FC(F)n1cc(cn1)-c1cc2C(=O)N[C@H](c2c(NC(=O)c2cc(F)cc(Cl)c2)c1)c1cc(F)ccc1Cl | 1H NMR (400 MHz, DMSO) δ 10.56 (s, 1H), 9.18 (s, 1H), 8.94 (s, 1H), 8.43 (s, 1H), 8.06 (d, J = 1.6 Hz, 1H), 8.02-7.79 (m, 3H), 7.75 (d, J = 9.1 Hz, 1H), 7.70 (d, J = 2.2 Hz, 1H), 7.31 (dd, J = 8.9, 5.1 Hz, 1H), 7.09 (td, J = 8.3, 3.1 Hz, 1H), 6.86-6.58 (m, 1H), 5.98 (s, 1H). | 583.2 | A | |
| I-1932 | 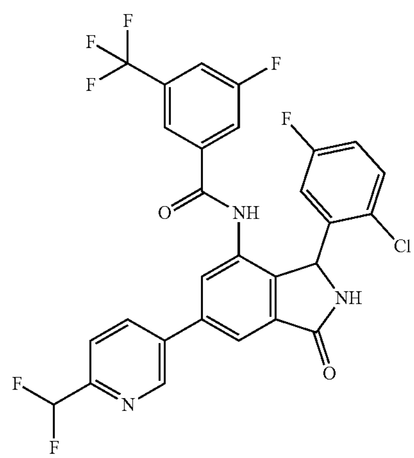 [SMILES: O=C(Nc1cc(-c2ccc(C(F)F)nc2)cc2c1C(c1cc(F)ccc1Cl)NC2=O)c1cc(F)cc(C(F)(F)F)c1] | FC(F)c1cc(cn1)-c1cc2C(=O)NC(c2c(NC(=O)c2cc(F)cc(c2)C(F)(F)F)c1)c1cc(F)ccc1Cl | 1H NMR (DMSO-d6, 400 MHz): δ = 10.66 (s, 1H), 9.28 (br s, 1H), 9.13 (d, J = 2.0 Hz, 1H), 8.43 (dd, J = 8.1, 2.3 Hz, 1H), 8.10 (d, J = 1.3 Hz, 1H), 7.97 (br d, J = 8.6 Hz, 1H), 7.93 (s, 1H), 7.84 (d, J = 8.3 Hz, 1H), 7.77 (br d, J = 9.1 Hz, 1H), 7.70 (s, 1H), 7.34 (dd, J = 8.8, 5.3 Hz, 1H), 6.90-7.22 (m, 2H), 6.46-6.84 (m, 1H), 5.85-6.25 ppm (m, 1H) | 594.4 | B | |
| I-1933 | 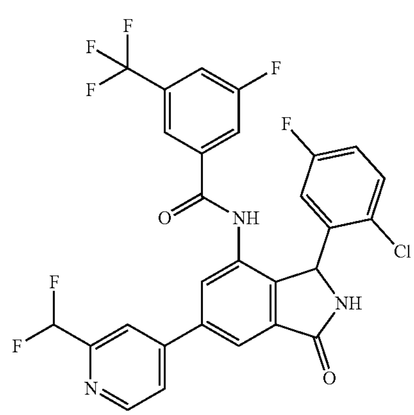 [SMILES: O=C(Nc1cc(-c2ccnc(C(F)F)c2)cc2c1C(c1cc(F)ccc1Cl)NC2=O)c1cc(F)cc(C(F)(F)F)c1] | FC(F)c1cc(ccn1)-c1cc2C(=O)NC(c2c(NC(=O)c2cc(F)cc(c2)C(F)(F)F)c1)c1cc(F)ccc1Cl | 1H NMR (DMSO-d6, 400 MHz): δ = 10.66 (s, 1H), 9.21-9.41 (m, 1H), 8.81 (d, J = 5.1 Hz, 1H), 8.17 (d, J = 1.3 Hz, 1H), 8.12 (s, 1H), 8.07 (br d, J = 5.3 Hz, 1H), 8.02 (s, 1H), 7.98 (br d, J = 8.6 Hz, 1H), 7.78 (br d, J = 9.1 Hz, 1H), 7.71 (s, 1H), 7.34 (dd, J = 9.0, 5.2 Hz, 1H), 6.90-7.20 (m, 2H), 6.39-6.71 (m, 1H), 5.92-6.26 ppm (m, 1H). | 594.4 | A | |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-1934 | 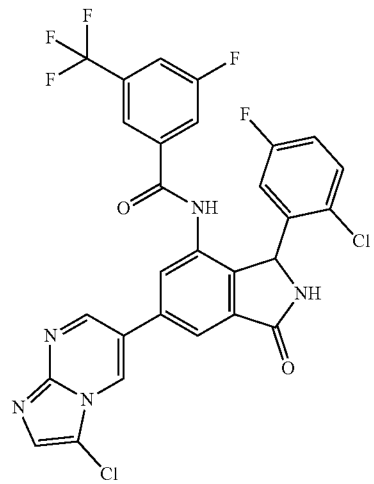 [SMILES: O=C(Nc1cc(-c2cnc3ncc(Cl)n3c2)cc2c1C(c1cc(F)ccc1Cl)NC2=O)c1cc(F)cc(C(F)(F)F)c1] | Fc1ccc(C1)c(c1)CNC(=O)c2cc(cc(NC(=O)c3cc(F)cc(c3)C(F)(F)F)c12)-c1cnc2ncc(Cl)n2c1 | 1H NMR (400 MHz, DMSO) 10.67 (s, 1H), 9.28 (s, 1H), 9.18 (d, 2.5 Hz, 1H), 9.06 (d, 2.5 Hz, 1H), 8.21 (d, 1.6 Hz, 1H), 7.96 (d, 16.9 Hz, 2H), 7.77 (d, 9.4 Hz, 1H), 7.71 (s, 1H), 7.34 (dd, 8.9, 5.2 Hz, 1H), 7.11 (td, 8.3, 3.1 Hz, 1H), 6.06 (s, 1H). | 618.13 | A | |
| I-1935 | 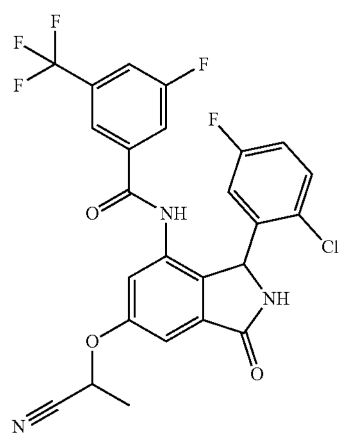 [SMILES: CC(C#N)Oc1cc(NC(=O)c2cc(F)cc(C(F)(F)F)c2)c2c(c1)C(=O)NC2c1cc(F)ccc1Cl] | CC(Oc1cc2C(=O)NC(c2c(NC(=O)c2cc(F)cc(c2)C(F)(F)F)c1)c1cc(F)ccc1Cl)C#N | | 523.07 | A | |
| I-1936 | 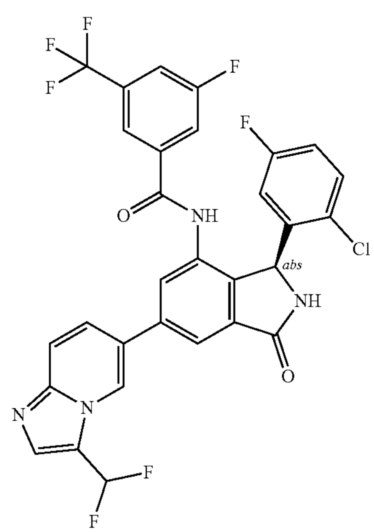 [SMILES: O=C(Nc1cc(-c2ccc3ncc(C(F)F)n3c2)cc2c1[C@@H](c1cc(F)ccc1Cl)NC2=O)c1cc(F)cc(C(F)(F)F)c1] | FC(F)c1cnc2ccc(cn12)-c1cc2C(=O)N[C@@H](c2c(NC(=O)c2cc(F)cc(c2)C(F)(F)F)c1)c1cc(F)ccc1Cl | 1H NMR (400 MHz, DMSO) δ 10.65 (s, 1H), 9.27 (s, 1H), 8.90 (t, J = 1.4 Hz, 1H), 8.07 (d, J = 1.6 Hz, 1H), 8.00 (s, 1H), 8.01-7.85 (m, 3H), 7.89-7.80 (m, 2H), 7.76 (d, J = 9.1 Hz, 1H), 7.69 (s, 2H), 7.33 (dd, J = 8.9, 5.2 Hz, 1H), 7.10 (td, J = 8.4, 3.1 Hz, 1H), 6.06 (s, 1H) | 633.19 | C | |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-1937 | 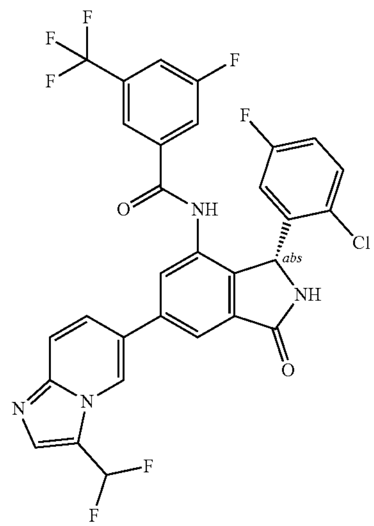 [SMILES: O=C(Nc1cc(-c2ccc3ncc(C(F)F)n3c2)cc2c1[C@H](c1cc(F)ccc1Cl)NC2=O)c1cc(F)cc(C(F)(F)F)c1] | FC(F)c1cnc2ccc(cn12)-c1cc2C(=O)N[C@H](c2c(NC(=O)c2cc(F)cc(c2)C(F)(F)F)c1c(F)ccc1Cl | 1H NMR (400 MHz, DMSO) δ 10.65 (s, 1H), 9.27 (s, 1H), 8.90 (t, J = 1.4 Hz, 1H), 8.07 (d, J = 1.6 Hz, 1H), 8.00 (s, 1H), 8.01-7.85 (m, 3H), 7.89-7.80 (m, 2H), 7.76 (d, J = 9.1 Hz, 1H), 7.69 (s, 2H), 7.33 (dd, J = 8.9, 5.2 Hz, 1H), 7.10 (td, J = 8.4, 3.1 Hz, 1H), 6.06 (s, 1H) | 633.19 | A | |
| I-1938 | 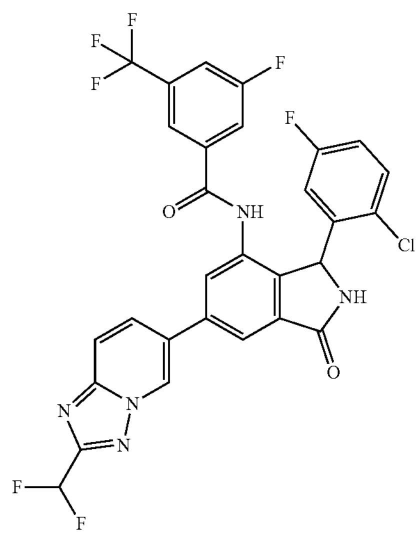 [SMILES: O=C(Nc1cc(-c2ccc3nc(C(F)F)nn3c2)cc2c1C(c1cc(F)ccc1Cl)NC2=O)c1cc(F)cc(C(F)(F)F)c1] | FC(F)c1nc2ccc(cn2n1)-c1cc2C(=O)NC(c2c(NC(=O)c2cc(F)cc(c2)C(F)(F)F)c1c(F)ccc1Cl | 1H NMR (400 MHz, DMSO) δ 10.65 (s, 1H), 9.56 (dd, J = 1.9, 0.9 Hz, 1H), 9.27 (s, 1H), 8.25 (dd, J = 9.4, 1.8 Hz, 1H), 8.15 (d, J = 1.7 Hz, 1H), 8.07 (dd, J = 9.3, 0.9 Hz, 1H), 8.00-7.93 (m, 2H), 7.76 (d, J = 9.1 Hz, 1H), 7.70 (s, 1H), 7.38-7.28 (m, 2H), 7.11 (td, J = 8.4, 3.1 Hz, 1H), 3.16 (d, J = 3.5 Hz, 1H). | 634.19 | A | |
| I-1939 | 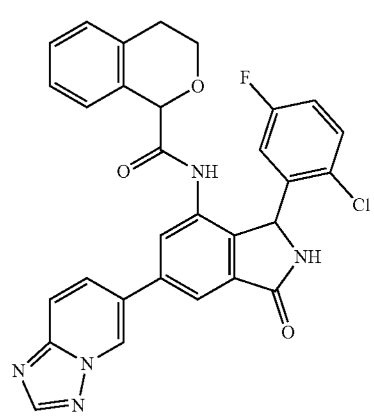 [SMILES: O=C1NC(c2cc(F)ccc2Cl)c2c(NC(=O)C3OCCc4ccccc43)cc(-c3ccc4ncnn4c3)cc21] | Fc1ccc(C1)c(c1)C1NC(=O)c2cc(cc(NC(=O)C3OCCc4ccccc34)c12)-c1ccc2ncnn2c1 | NMR (400 MHz, DMSO-d6) 9.69 (br s, 1H), 9.56 (br s, 1H), 9.44 (dd, 1.7, 0.8 Hz, 1H), 9.42 (dd, 1.6, 0.8 Hz, 1H), 9.22 (br s, 1H), 9.15 (br s, 1H), 8.58 (s, 1H), 8.57 (s, 1H), 8.16-8.05 (m, 4H), 8.02-7.94 (m, 4H), 7.43-7.34 (m, 2H), 7.27-7.15 (m, 11.2, 5.8 Hz, 6H), 7.14-7.02 (m, 6H), 6.54 (br s, 1H), 6.22 (br s, 1H), 6.14 (br s, 1H), 5.13 (s, 1H), 5.10 (s, 1H), 3.98-3.89 (m, 1H), 3.80-3.71 (m, 2H), 3.71-3.63 (m, 1H), 2.82-2.64 (m, 4H). | 554.3 | D | |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-1940 | 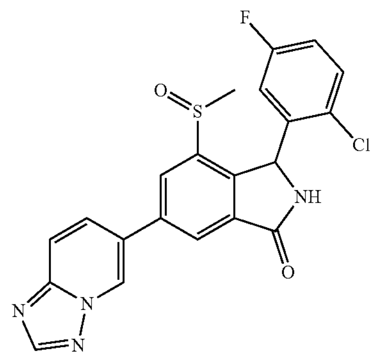 [SMILES: CS(=O)c1cc(-c2ccc3ncnn3c2)cc2c1C(c1cc(F)ccc1Cl)NC2=O] | CS(=O)c1cc(cc2C(=O)NC(c12)cc1cc(F)ccc1Cl)-c1ccc2ncnn2c1 | 1H NMR (400 MHz, DMSO-d6) 9.61 (d, 17.7 Hz, 1H), 9.42 (s, 1H), 8.59 (s, 1H), 8.43 (s, 1H), 8.33 (d, 7.0 Hz., 1H), 8.20 (dd, 16.4, 9.4 Hz, 1H), 8.00 (d, 9.3 Hz, 1H), 7.62 (s, 1H), 7.33 (d, 12.4 Hz, 1H), 6.68 (s, 1H), 6.43-6.26 (s, 1H), 2.20 (s, 3H). | 441.2 | E | |
| I-1941 | 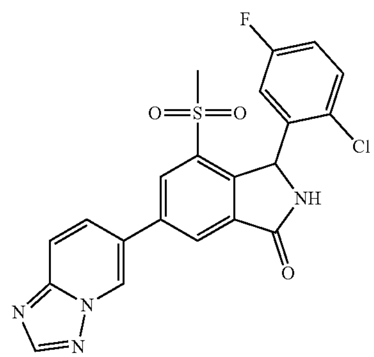 [SMILES: CS(=O)(=O)c1cc(-c2ccc3ncnn3c2)cc2c1C(c1cc(F)ccc1Cl)NC2=O] | CS(=O)(=O)c1cc(cc2C(=O)NC(c12)c1cc(F)ccc1Cl)-c1ccc2ncnn2c1 | 1H NMR (400 MHz, DMSO-d6) 9.67 (s, 1H), 9.58 (s, 1H), 8.61 (s, 1H), 8.51 (s, 2H), 8.26 (d, 9.4 Hz, 1H), 8.02 (d, 9.3 Hz, 1H), 7.62 (s, 1H), 7.26 (s, 1H), 6.53 (s, 1H), 6.47-6.25 (s, 1H), 2.94 (s, 3H) | 456.95 | E | |
| I-1942 | 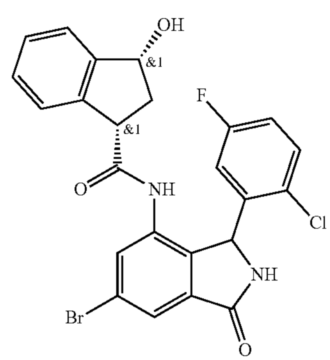 [SMILES: O=C1NC(c2cc(F)ccc2Cl)c2c(NC(=O)[C@H]3C[C@@H](O)c4ccccc43)cc(Br)cc21] | O[C@@H]1C[C@H](C(=O)Nc2cc(Br)cc3C(=O)NC(c23)c2cc(F)ccc2Cl)c2ccccc12 | 1H NMR (400 MHz, DMSO-d6) 10.16 (d, 46.4 Hz, 1H), 9.25 (s, 1H), 7.81 (d, 51.4 Hz, 2H), 7.53 (d, 26.0 Hz, 1H), 7.40-7.20 (m, 3H), 7.11 (q, 6.8 Hz, 1H), 6.66 (d, 7.6 Hz, 1H), 6.09 (s, 1H), 5.40 (dd, 14.7, 6.9 Hz, 1H), 4.97 (dt, 14.0, 7.0 Hz, 1H), 3.63 (dd, 16.2, 8.2 Hz, 1H), 2.30 (dd, 14.3, 7.7 Hz, 1H), 1.98 (s, 1H), 1.80-1.65 (m, 1H). | 517.05 | E | |
| I-1943 | 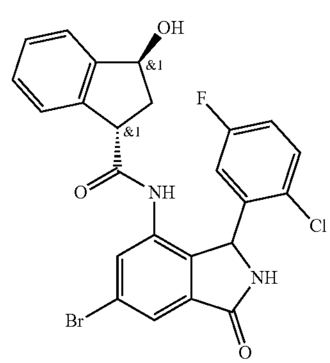 [SMILES: O=C1NC(c2cc(F)ccc2Cl)c2c(NC(=O)[C@H]3C[C@H](O)c4ccccc43)cc(Br)cc21] | O[C@H]1C[C@H](C(=O)Nc2cc(Br)cc3C(=O)NC(c23)c2cc(F)ccc2Cl)c2ccccc12 | 1H NMR (400 MHz, DMSO-d6) 10.11 (d, 35.6 Hz, 1H), 9.22 (d, 22.3 Hz, 1H), 7.85-7.70 (m, 2H), 7.65 (d, 1.8 Hz, 2H), 7.37-7.28 (s, 1H), 7.22 (m, 2H), 7.16-7.07 (s, 1H), 6.72-6.18 (s, 1H), 6.82 (dd, 25.9, 7.5 Hz, 1H), 6.04 (m, 2H), 5.29-5.07 (s, 1H), 2.37-2.00 (s, 1H), 1.82 (ddd, 13.1, 8.2, 5.0 Hz, 1H). | 517.05 | E | |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-1944 | 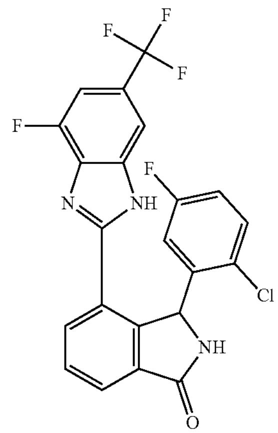 [SMILES: O=C1NC(c2cc(F)ccc2Cl)c2c1cccc2-c1nc2c(F)cc(C(F)(F)F)cc2[nH]1] | Fc1ccc(C1)c(c1)C1NC(=O)c2cccc(-c3nc4c(F)cc(cc4[nH]3)C(F)(F)F)c12 | 1H NMR (400 MHz, DMSO-d6) 9.33 (s, 1H), 8.31 (d, 7.6 Hz, 1H), 7.96 (d, 7.5 Hz, 1H), 7.85 (t, 7.6 Hz, 1H), 7.65 (s, 1H), 7.38 (d, 10.6 Hz, 2H), 6.95 (td, 8.4, 3.1 Hz, 1H), 6.69 (s, 1H), 6.21 (s, 1H) | 464.05 | A | |
| I-1945 | 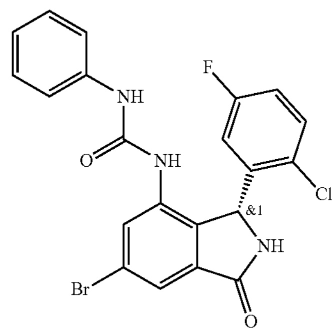 [SMILES: O=C(Nc1ccccc1)Nc1cc(Br)cc2c1[C@H](c1cc(F)ccc1Cl)NC2=O] | Fc1ccc(C1)c(c1)[C@@H]1NC(=O)c2cc(Br)cc(NC(=O)Nc3ccccc3)c12 | 1H NMR (400 MHz, DMSO-d6) 9.26-8.26 (m, 2H), 7.85-7.76 (m, 1H), 7.62 (d, 1.7 Hz, 1H), 7.46 (dd, 8.9, 5.1 Hz, 1H), 7.39-7.31 (m, 2H), 7.31-7.14 (m, 3H), 6.98 (td, 7.3, 1.3 Hz, 1H), 6.88-6.59 (m, 1H), 6.06 (s, 1H). | 476 | E | |
| I-1946 | 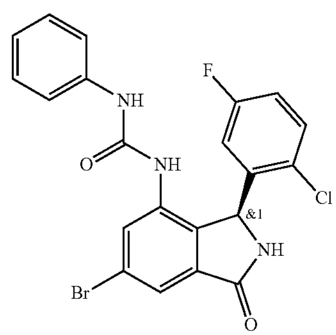 [SMILES: O=C(Nc1ccccc1)Nc1cc(Br)cc2c1[C@@H](c1cc(F)ccc1Cl)NC2=O] | Fc1ccc(C1)c(c1)[C@H]1NC(=O)c2cc(Br)cc(NC(=O)Nc3ccccc3)c12 | 1H NMR (400 MHz, DMSO-d6) 9.26-8.26 (m, 2H), 7.85-7.76 (m, 1H), 7.62 (d, 1.7 Hz, 1H), 7.46 (dd, 8.9, 5.1 Hz, 1H), 7.39-7.31 (m, 2H), 7.31-7.14 (m, 3H), 6.98 (td, 7.3, 1.3 Hz, 1H), 6.88-6.59 (m, 1H), 6.06 (s, 1H). | 476 | D | |
| I-1947 | 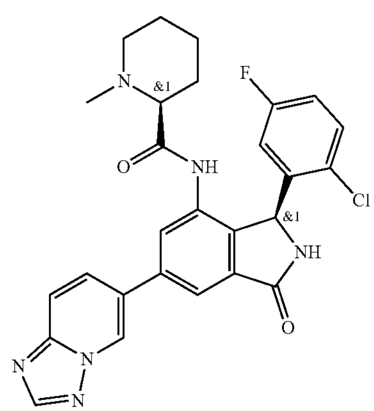 [SMILES: CN1CCCC[C@H]1C(=O)Nc1cc(-c2ccc3ncnn3c2)cc2c1[C@@H](c1cc(F)ccc1Cl)NC2=O] | CN1CCCC[C@H]1C(=O)Nc1cc(cc2C(=O)N[C@H](c12)c1cc(F)ccc1Cl)-c1ccc2ncnn2c1 | 1H NMR (400 MHz, DMSO-d6) 9.43 (d, 1.8 Hz, 2H), 8.57 (s, 1H), 8.18 (d, 1.7 Hz, 1H), 8.09 (dd, 9.3, 1.9 Hz, 1H), 8.03-7.94 (m, 2H), 7.55 (s, 1H), 7.26 (td, 8.4, 3.1 Hz, 1H), 6.16 (d, 69.1 Hz, 2H), 5.93 (d, 2H), 3.00-2.76 (m, 2H), 1.90 (s, 4H), 1.54 (d, 12.0 Hz, 2H), 1.38 (d, 13.2 Hz, 2H), 1.15 (s, 1H). | 519.25 | E | |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-1948 | 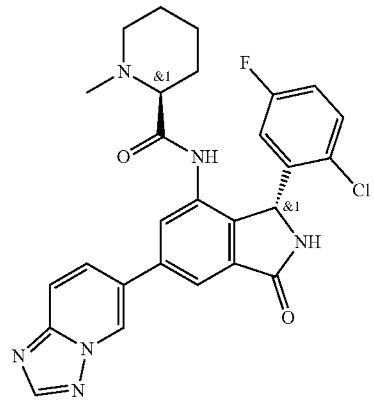 [SMILES: CN1CCCC[C@H]1C(=O)Nc1cc(-c2ccc3ncnn3c2)cc2c1[C@H](c1cc(F)ccc1Cl)NC2=O] | CN1CCCC[C@H]1C(=O)Nc1cc(cc2C(=O)N[C@H](c12)c1cc(F)ccc1Cl)-c1ccc2ncnn2c1 | 1H NMR (400 MHz, DMSO-d6) 9.43 (d, 1.8 Hz, 2H), 8.57 (s, 1H), 8.18 (d, 1.7 Hz, 1H), 8.09 (dd, 9.3, 1.9 Hz, 1H), 8.03-7.94 (m, 2H), 7.55 (s, 1H), 7.26 (td, 8.4, 3.1 Hz, 1H), 6.16 (d, 69.1 Hz, 2H), 5.93 (d, 2H), 3.00-2.76 (m, 2H), 1.90 (s, 4H), 1.54 (d, 12.0 Hz, 2H), 1.38 (d, 13.2 Hz, 2H), 1.15 (s, 1H). | 519.2 | E | |
| I-1949 | 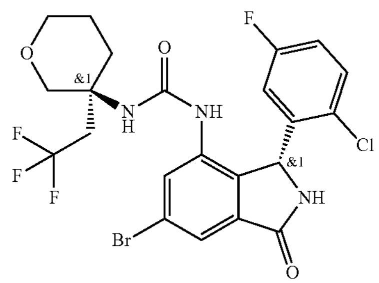 [SMILES: O=C(Nc1cc(Br)cc2c1[C@H](c1cc(F)ccc1Cl)NC2=O)N[C@]1(CC(F)(F)F)CCCOC1] | Fc1ccc(C1)c(c1)[C@H]1NC(=O)c2cc(Br)cc(NC(=O)N[C@@]3(CC(F)(F)F)CCCOC3)c12 | 1H NMR (400 MHz, DMSO):-' 9.17 (s, 1H), 8.52 (s, 1H), 7.83 (d, 1.0 Hz, 1H), 7.52 (d, 1.7 Hz, 1H), 7.48 (dd, 8.3, 5.3 Hz, 1H), 7.22 (td, 8.4, 3.1 Hz, 1H), 6.71 (br s, 1H), 6.58 (s, 1H), 6.01 (s, 1H), 3.67-3.49 (m, 4H), 2.85-2.63 (m, 2H), 2.01-1.90 (m, 1H), 1.61-1.49 (m, 1H), 1.47-1.33 (m, 2H). | 564.2 | E | |
| I-1950 | 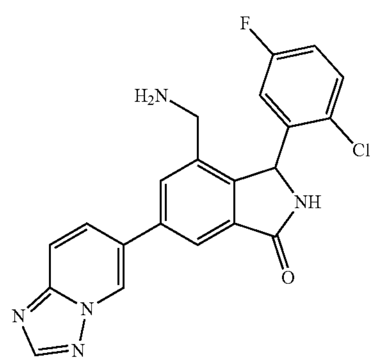 [SMILES: NCc1cc(-c2ccc3ncnn3c2)cc2c1C(c1cc(F)ccc1Cl)NC2=O] | NCc1cc(cc2C(=O)NC(c12)c1cc(F)ccc1Cl)-c1ccc2ncnn2c1 | 1H NMR (400 MHz, DMSO-d6) 9.45 (s, 1H), 9.19 (s, 1H), 8.56 (s, 1H), 8.15 (dd, 9.3, 1.9 Hz, 1H), 8.10 (s, 1H), 8.02 (s, 1H), 7.97 (d, 9.3 Hz, 1H), 7.64 (s, 1H), 7.28 (s, 1H), 6.50 (s, 1H), 6.17 (s, 1H), 3.61 (d, 15.6 Hz, 2H). | 408.08 | E | |
| I-1951 | 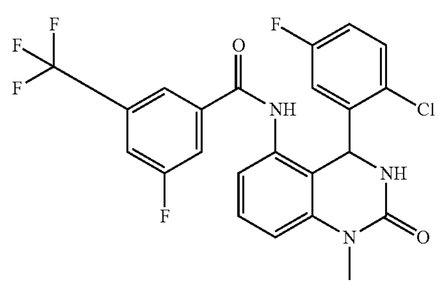 [SMILES: CN1C(=O)NC(c2cc(F)ccc2Cl)c2c(NC(=O)c3cc(F)cc(CC(F)(F)F)c3)cccc21] | CN1C(=O)NC(c2cc(F)ccc2Cl)c2c(NC(=O)c3cc(F)cc(c3)C(F)(F)F)cccc12 | 1H NMR (Chloroform-d, 400 MHz) 7.62 (1H, dt, 8.8, 1.9 Hz), 7.51 (4H, q, 3.5, 2.6 Hz), 7.43 (1H, dd, 8.9, 4.9 Hz), 7.18 (1H, s), 7.03 (2H, ddt, 10.4, 6.0, 3.2 Hz), 6.60 (1H, dd, 8.7, 3.0 Hz), 6.14 (1H, dd, 3.1, 1.3 Hz), 5.55 (1H, d, 3.1 Hz), 3.41 (3H, s) | 494.1 | D | |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-1952 | 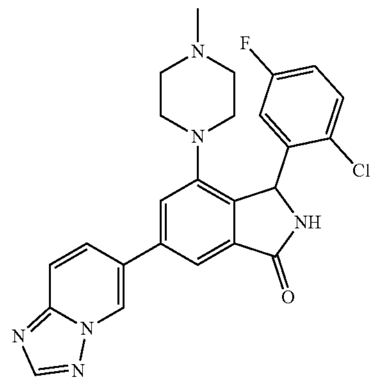 [SMILES: CN1CCN(c2cc(-c3ccc4ncnn4c3)cc3c2C(c2cc(F)ccc2Cl)NC3=O)CC1] | CN1CCN(CC1)c1cc c(cc2C(=O)NC(c1 2)c1cc(F)ccc1Cl)-c1ccc2ncnn2c1 | NMR (400 MHz, CD3CN) 9.09 (br s, 1H), 8.36 (br s, 1H), 8.04 (s, 0.5H), 8.00 (dd, 9.3, 1.9 Hz, 1H), 7.84 (br s, 0.5H), 7.82 (d, 1.5 Hz, 1H), 7.56-7.51 (m, 2H), 7.34-7.29 (m, 1H), 7.14 (ddd, 8.8, 8.0, 3.1 Hz, 1H), 6.62 (br s, 0.5H), 6.60 (br s, 0.5H), 6.20 (s, 1H), 3.41-3.33 (m, 2H), 3.05-2.96 (m, 2H), 2.74-2.54 (m, 4H), 2.44 (s, 3H). | 477 | E | |
| I-1953 | 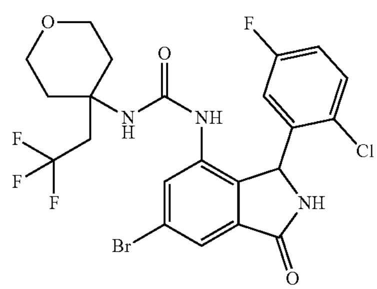 [SMILES: O=C(Nc1cc(Br)cc2c1C(c1cc(F)ccc1Cl)NC2=O)NC1(CC(F)(F)F)CCOCC1] | Fc1ccc(C1)c(c1)C1NC(=O)c2cc(Br)cc(NC(=O)NC3(CC(F)(F)F)CCOCC3)c12 | 1H NMR (400 MHz, DMSO-d6) 9.19 (s, 1H), 8.07 (s, 1H), 7.76 (d, 1.7 Hz, 1H), 7.54 (d. 1.7 Hz, 1H), 7.49 (dd, 8.7, 5.0 Hz, 1H), 7.27-7.19 (m, 1H), 6.71 (br s, 1H), 6.48 (s, 1H), 6.06 (s, 1H), 3.65-3.50 (m, 2H), 3.30-3.14 (m, 2H), 2.80-2.65 (m, 2H), 1.96-1.86 (m, 2H), 1.67-1.50 (m, 2H). | 564.1 | E | |
| I-1954 | 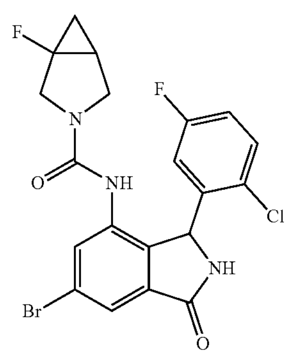 [SMILES: O=C1NC(c2cc(F)ccc2Cl)c2c(NC(=O)N3CC4CC4(F)C3)cc(Br)cc21] | Fc1ccc(C1)c(c1)C1NC(=O)c2cc(Br)cc(NC(=O)N3CC4CC4(F)C3)c12 | 1H NMR (400 MHz, DMSO-d6) 9.19 (s, 1H), 8.38 (s, 1H), 7.62 (d, 1.5 Hz., 1H), 7.56-7.42 (m, 2H), 7.30-7.22 (m, 1H), 7.06-6.18 (m, 1H), 5.95 (br s, 1H), 3.95-3.84 (m, 0.5H), 3.81-3.49 (m, 1.5H), 3.24-3.15 (m, 1H), 3.12-2.70 (m, 1H), 2.05-1.92 (m, 1H), 1.55-1.40 (m, 1H), 0.46 (br s, 1H). | 482 | E | |
| I-1955 | 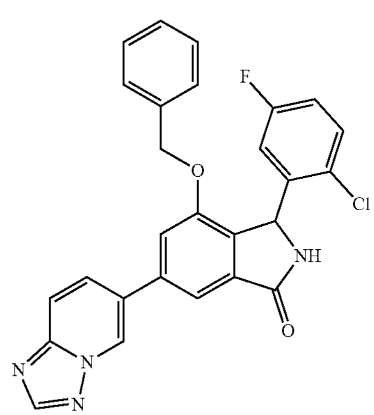 [SMILES: O=C1NC(c2cc(F)ccc2Cl)c2c(OCc3ccccc3)cc(-c3ccc4ncnn4c3)cc21] | Fc1ccc(C1)c(c1)C1NC(=O)c2cc(cc(OCc3ccccc3)c12)-c1ccc2ncnn2c1 | (400 MHz, DMSO-d6) 9.52-9.50 (m, 1 H), 9.19 (s, 1 H), 8.57 (s, 1 H), 8.16 (dd, 9.3, 1.8 Hz, 1H), 7.96 (d, 9.4 Hz, 1 H), 7.75-7.70 (m, 2 H), 7.52 (dd, 8.9, 5.1 Hz, 1 H), 7.31-7.24 (m, 4 H), 7.02-6.96 (m, 2 H), 6.88 (br s, 1 H), 6.07 (s, 1 H), 5.28-5.18 (m, 2 H). | 485.2 | E | |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-1956 | 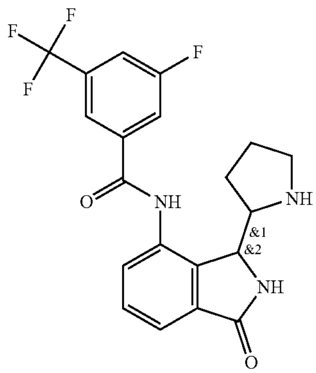 [SMILES: O=C(Nc1cccc2c1C(C1CCCN1)NC2=O)c1cc(F)cc(C(F)(F)F)c1] | Fc1cc(cc(c1)C(F)(F)F)C(=O)Nc1cccc2C(=O)NC(C3CCCN3)c12 | NMR (400 MHz, DMSO-d6) 8.87 (s, 1H), 8.46 (d, 7.9 Hz, 1H), 8.37 (m, 2H), 8.06 (d, 4.8 Hz, 1H), 8.01 (d, 8.0 Hz), 7.61-7.49 (m, 1H), 7.43 (d, 7.3 Hz, 1H), 4.58 (d, 10.2 Hz, 1H), 3.06-23.00 (m, 1H), 2.89-2.81 (m, 1H), 2.78-2.66 (m, 1H), 1.92-1.81 (m, 2H), 1.60-1.48 (m, 2H). | 408.1 | E | |
| I-1957 | 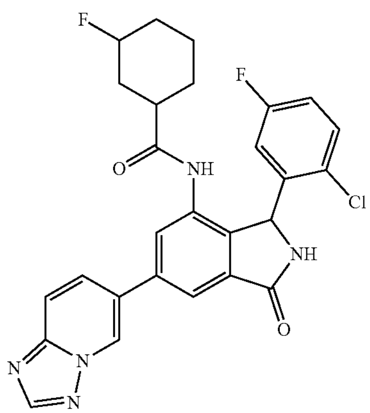 [SMILES: O=C1NC(c2cc(F)ccc2Cl)c2c(NC(=O)C3CCCC(F)C3)cc(-c3ccc4ncnn4c3)cc21] | FC1CCCC(C1)C(=O)Nc1cc(cc2C(=O)NC(c12)c1cc(F)ccc1Cl)-c1ccc2ncnn2c1 | NMR (400 MHz, DMSO-d6) 9.92 (br. s, 1H), 9.90-9.87 (m, 1H), 9.45-9.43 (m, 2H), 9.21 (s, 2H), 8.57 (s, 2H), 8.11-8.07 (m, 2H), 8.01-7.99 (m, 2H), 7.99-7.95 (m, 2H), 7.86-7.80 (m, 2H), 7.55-7.49 (m, 2H), 7.29-7.22 (m, 2H), 6.58 (br. s, 2H), 6.13 (br. s, 2H), 4.96-4.90 (m, 1H), 4.84-4.78 (m, 1H), 2.48-2.39 (m, 2H), 1.85-1.65 (m, 4H), 1.61-1.35 (m, 8H), 1.32-1.12 (m, 4H). | 522.3 | D | |
| I-1958 | 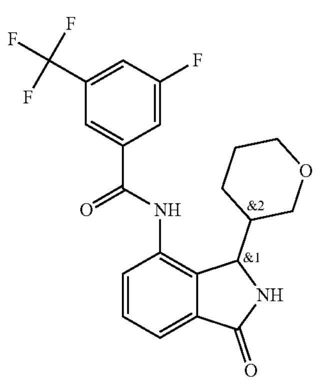 [SMILES: O=C(Nc1cccc2c1C(C1CCCOC1)NC2=O)c1cc(F)cc(C(F)(F)F)c1] | Fc1cc(cc(c1)C(F)(F)F)C(=O)Nc1ccc c2C(=O)NC(C3CCOC3)c12 | (400 MHz, CD3CN) 9.13 (s, 0.6H), 9.06 (s, 0.4H), 8.11 (s, 1H), 7.96 (d, 9.1 Hz,1H), 7.74 (d, 8.4 Hz,1H), 7.67-7.57 (m, 2H), 7.57-7.51 (m, 7.6 Hz, 1H), 6.97 (s, 0.6H), 6.85 (s, 0.4H), 4.83 (s, 1H), 3.85 (dd, 11.1, 2.1 Hz, 0.4H), 3.77-3.63 (m, 1H), 3.32 (t, 10.9 Hz, 0.4H), 3.27-3.11 (m, 1H), 3.11-3.02 (m, 0.6H), 2.95 (t, 10.9 Hz, 0.6H), 2.12 (m, 1H), 1.88-1.78 (m, 0.6H), 1.61-1.32 (m, 3H), 1.12-0.99 (m, 0.6H), 0.96-0.84 (m, 0.4H) | 423.1 | E | |

TABLE 2-continued

Representative Compounds of the Invention with Bioactivity Data.

| Ex. No. | Structure | SMILES | ¹H NMR | MS | ADP-Glo IC₅₀ | MCF 10A IC₅₀ |
|---|---|---|---|---|---|---|
| I-1959 | 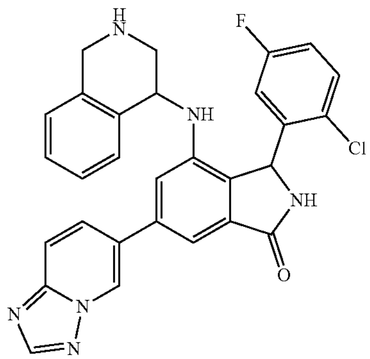 [SMILES: O=C1NC(c2cc(F)ccc2Cl)c2c(NC3CNCc4ccccc43)cc(-c3ccc4ncnn4c3)cc21] | Fc1ccc(C1)c(c1)CNC(=O)c2cc(cc(NC3CNCc4ccccc34)c12)-c1ccc2ncnn2c1 | 1H NMR (400 MHz, DMSO-d6) 9.47-9.42 (m, 1H), 9.01 (s, 1H), 8.55 (s, 1H), 8.14 (dd, 9.3, 1.9 Hz, 1H), 7.94 (d, 9.3 Hz., 1H), 7.48-7.37 (m, 3H), 7.26 (td, 8.4, 3.1 Hz, 1H), 7.13 (td, 7.5, 1.3 Hz, 1H), 7.02 (d, 7.6 Hz, 1H), 6.91 (t, 7.4 Hz, 1H), 6.61 (d, 7.7 Hz, 1H), 5.88 (s, 1H), 4.86-4.77 (m, 2H), 3.86 (s, 2H), 3.24 (dd, 12.0, 4.1 Hz, 1H), 2.87 (dd, 12.5, 5.8 Hz, 1H). | 525.1 | D | |
| I-1960 | 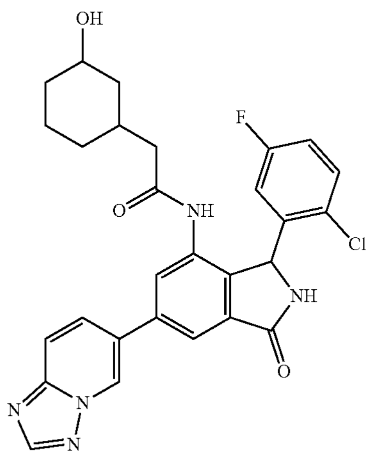 [SMILES: O=C(CC1CCCC(O)C1)Nc1cc(-c2ccc3ncnn3c2)cc2c1C(c1cc(F)ccc1Cl)NC2=O] | OC1CCCC(CC(=O)Nc2cc(cc3C(=O)NC(c23)c2cc(F)ccc2Cl)-c2ccc3ncnn3c2)C1 | NMR (400 MHz, DMSO-d6) 9.79 (br s, 1H), 9.43 (br s, 1H), 9.26-9.13 (m, 1H), 8.57 (d, 2.5 Hz, 1H), 8.13-7.94 (m, 4H), 7.60-7.43 (m, 1H), 7.35-7.17 (m, 1H), 6.59 (br s, 1H), 6.16 (br s, 1H), 4.47 (br s, 1H), 3.81-3.57 (m, 1H), 2.01-1.90 (m, 2H), 1.48-1.08 (m, 9H). | 534.2 | E | |
| I-1961 | 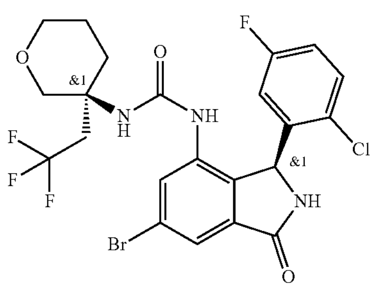 [SMILES: O=C(Nc1cc(Br)cc2c1[C@@H](c1cc(F)ccc1Cl)NC2=O)N[C@]1(CC(F)(F)F)CCCOC1] | Fc1ccc(C1)c(c1)[C@@H]1NC(=O)c2cc(Br)cc(NC(=O)N[C@@]3(CC(F)(F)F)CCCOC3)c12 | 1H NMR (400 MHz, DMSO-d6) 9.18 (s, 1H), 8.49 (s, 1H), 7.77 (d, 1.7 Hz, 1H), 7.53 (d, 1.7 Hz, 1H), 7.48 (dd, 8.6, 5.1 Hz, 1H), 7.21 (td, 8.4, 3.1 Hz, 1H), 6.65 (br s, 1H), 6.58 (s, 1H), 6. (s, 1H), 3.64 (dd, 10.8, 2.5 Hz, 2H), 3.44-3.35 (m, 2H), 2.92-2.75 (m, 1H), 2.69-2.53 (m, 1H), 2.17-2.05 (m, 1H), 1.59-1.47 (m, 1H), 1.47-1.32 (m, 2H). | 564.2 | E | |
| I-1962 | 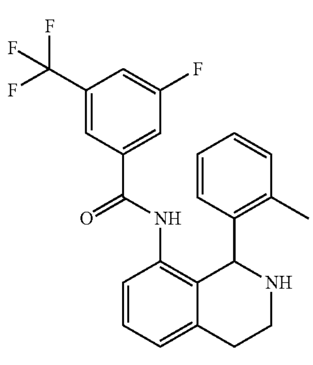 [SMILES: Cc1ccccc1C1NCCc2cccc(NC(=O)c3cc(F)cc(C(F)(F)F)c3)c21] | CC(C=CC=C1)=C1C2NCCC3=CC=CC(NC(C4=CC(F)=CC(C(F)(F)F)=C4)=O)=C32 | | 428.2 | E | |

TABLE 2-continued

Representative Compounds of the Invention with Bioactivity Data.

| Ex. No. | Structure | SMILES | ¹H NMR | MS | ADP-Glo IC$_{50}$ | MCF-10A IC$_{50}$ |
|---|---|---|---|---|---|---|
| I-1963 | 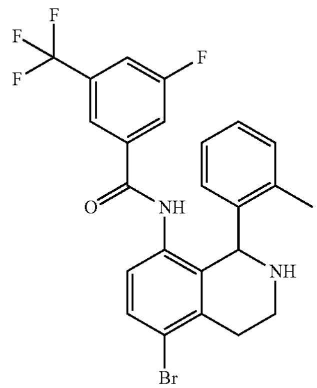 [SMILES: Cc1ccccc1C1NCCc2c(Br)ccc(NC(=O)c3cc(F)cc(C(F)(F)F)c3)c21] | CC(C=CC=C1)=C1C2NCCC3=C(Br)C=CC(NC(C4=CC(F)=CC(C(F)(F)F)=C4)=O)=C32 | | 506.1 | E | |
| I-1964 | 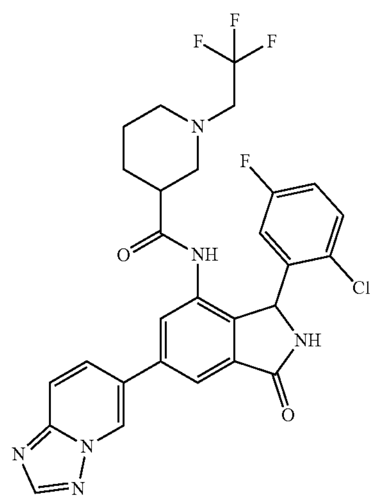 [SMILES: O=C1NC(c2cc(F)ccc2Cl)c2c(NC(=O)C3CCCN(CC(F)(F)F)C3)cc(-c3ccc4ncnn4c3)cc21] | Fc1ccc(Cl)c(c1)C1NC(=O)c2cc(cc(NC(=O)C3CCN(CC(F)(F)F)C3)c12)-c1ccc2ncnn2c1 | 1H-NMR (400 MHz, DMSO-d6) as a ca. 1:1 mixture of diastereomers 9.93 (br. s, 1H), 9.91 (br. s, 1H), 9.45-9.43 (m, 2H), 9.21 (br. s, 2H), 8.57 (s, 2H), 8.11-8.07 (m, 2H), 8.01 (d, J = 1.1 Hz, 2H), 7.97 (d, J = 9.3 Hz, 2H), 7.82-7.77 (m, 2H), 7.56-7.49 (m, 2H), 7.28-7.22 (m, 2H), 6.56 (br. s, 2H), 6.09 (br. s, 2H), 3.20-3.06 (m, 3H), 3.03-2.92 (m, 1H), 2.84-2.78 (m, 2H), 2.70-2.65 (m, 1H), 2.55-2.44 (m, 1H), 2.36-2.27 (m, 2H), 2.22 (m, 3H), 2.14-2.06 (m, 1H), 1.59-1.50 (m, 3H), 1.43-1.32 (m, 3H), 1.24-1.05 (m, 2H). | 587.3 | E | |
| I-1965 | 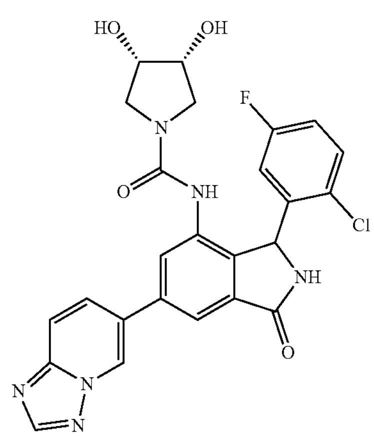 [SMILES: O=C1NC(c2cc(F)ccc2Cl)c2c(NC(=O)N3C[C@@H](O)[C@@H](O)C3)cc(-c3ccc4ncnn4c3)cc21] | O[C@H]1CN(C[C@H]1O)C(=O)Nc1cc(cc2C(=O)NC(c12)c1cc(F)ccc1Cl)-c1ccc2ncnn2c1 | 1H-NMR (400 MHz, DMSO-d6) 9.38-9.37 (m, 1H), 9.13 (br. s, 1H), 8.56 (s, 1H), 8.19 (br. s, 1H), 8.05 (dd, J = 9.3, 1.8 Hz, 1H), 7.96 (dd, J = 9.2, 0.6 Hz, 1H), 7.89 (d, J = 1.5 Hz, 1H), 7.72 (br. s, 1H), 7.52-7.45 (m, 1H), 7.24 (app. td, J = 8.6, 3.2 Hz, 1H), 6.66 (br. s, 1H), 6.08 (br. s, 1H), 4.96-4.89 (m, 2H), 3.95-3.89 (m, 1H), 3.89-3.82 (m, 1H), 3.44-3.32 (m, 2H), 3.08 (dd, J = 10.1, 5.6 Hz, 1H), 3.02-2.94 (m, 1H). Multiplet at 3.44-3.32 is partially obscured by the H2O peak. | 523 | E | |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-1966 | 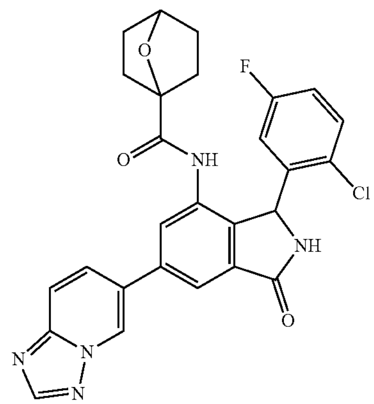 [SMILES: O=C1NC(c2cc(F)ccc2Cl)c2c(NC(=O)C34CCC(CC3)O4)cc(-c3ccc4ncnn4c3)cc21] | Fc1ccc (Cl)c(c1) C1NC(= O)c2cc (cc(NC(= O)C34C CC(CC3) O4)c12)- c1ccc2n cnn2c1 | NMR (400 MHz, DMSO-d6) 9.46-9.40 (m, 2H), 9.21 (br s, 1H), 8.57 (s, 1H), 8.10 (dd, J = 9.3, 1.8 Hz, 1H), 8.03-8.00 (m, 2H), 7.97 (dd, J = 9.3, 0.5 Hz, 1H), 7.59-7.44 (m, 1H), 7.29-7.21 (m, 1H), 6.61 (br s, 1H), 6.22 (br s, 1H), 4.60 (t, J = 4.9 Hz, 1H), 1.79-1.58 (m, 4H), 1.58-1.48 (m, 2H), 1.39-1.13 (m, 2H). av. 10% impurity | 518.3 | E | |
| I-1967 | 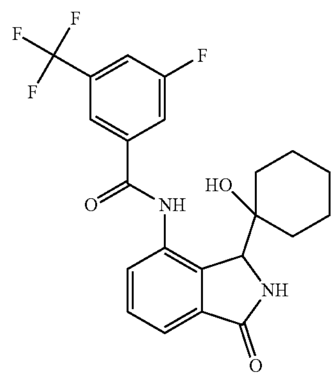 [SMILES: O=C(Nc1cccc2c1C(C1(O)CCCCC1)NC2=O)c1cc(F)cc(C(F)(F)F)c1] | OC1(C CCCC1) C1NC(= O)c2ccc c(NC(= O)c3cc (F)cc(c3) C(F)(F) F)c12 | NMR (400 MHz, DMSO-d6) 10.70 (br. s, 1H), 8.71 (s, 1H), 8.09 (s, 1H), 8.04 (br. d, J = 9.0 Hz, 1H), 7.99 (br. d, J = 8.4 Hz, 1H), 7.58-7.45 (m, 3H), 4.71 (s, 1H), 4.18 (br. s, 1H), 3.69 (s, 1H), 1.85-1.66 (m, 2H), 1.61 (d, J = 13.4 Hz, 1H), 1.44 (d, J = 11.5 Hz, 1H), 1.28-1.17 (m, 1H), 1.16-1.02 (m, 3H), 0.32 (d, J = 10.8 Hz, 1H). | 437.1 | E | |
| I-1968 | 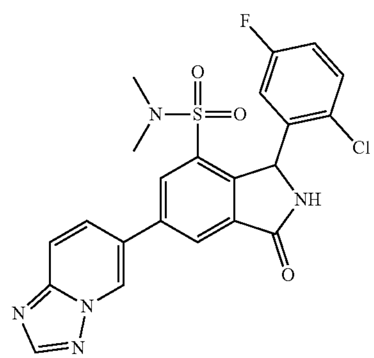 | CN(C)S (=O)(= O)c1cc (cc2C(= O)NC(c 12)c1cc (F)ccc1C 1)-c1ccc2n cnn2c1 | 1H NMR (400 MHz, DMSO-d6) 9.60 (d, J = 2.1 Hz, 1H), 9.57 (s, 1H), 8.61 (s, 1H), 8.47 (s, 1H), 8.24 (s, 1H), 8.19 (dd, J = 9.3, 1.9 Hz, 1H), 8.00 (d, J = 9.3 Hz, 1H), 7.59 (s, 1H), 7.22 (s, 1H), 6.25 (d, J = 103.6 Hz, 1H), 2.62 (s, 6H). | 486 | E | |
| I-1969 | 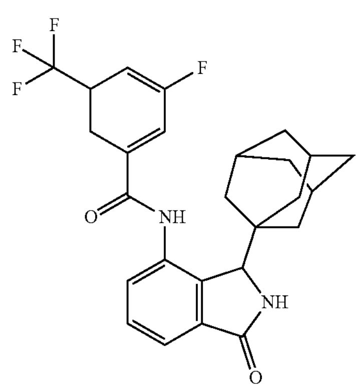 [SMILES: O=C(Nc1cccc2c1C(C13CC4CC(CC(C4)C1)C3)NC2=O)C1=CC(F)=CC(C(F)(F)F)C1] | Fc1cc(cc (c1)C(F) (F)F)C(= O)Nc1cc cc2C(=O) NC(c12) C12CC3 CC(CC (C3)C1)C2 | NMR (400 MHz, DMSOd6) 10.78 (s, 1H), 8.72 (s, 1H), 8.14 (s, 1H), 8.07 (d, J = 9.2 Hz, 1H), 8.02 (d, J = 8.2 Hz, 1H), 7.59-7.50 (m, 3H), 4.50 (s, 1H), 1.81 (br s, 3H), 1.56 (d, J = 13.4 Hz, 3H), 1.52 (m, 3H), 1.44 (d, J = 11.5 Hz, 3H), 1.31 (d, J = 11.8 Hz, 3H). Presence of an impurity at 3.9 10-15% by NMR. | 473.3 | E | |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-1970 | 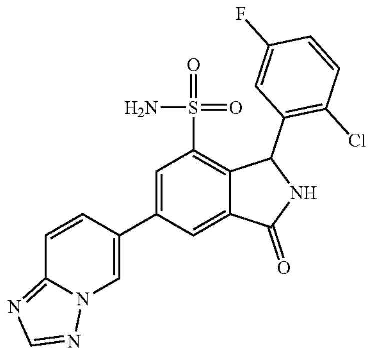 | NS(=O)(=O)c1cc(cc2C(=O)NC(c12)c1cc(F)cc1Cl)-c1ccc2ncnn2c1 | 1H NMR (400 MHz, DMSO-d6) 9.55 (d, J = 1.8 Hz, 1H), 9.45 (s, 1H), 8.61 (s, 1H), 8.55 (s, 1H), 8.42 (d, J = 1.7 Hz, 1H), 8.20 (dd, J = 9.3, 1.9 Hz, 1H), 8.05 (d, J = 9.3 Hz, 1H), 7.53 (s, 1H), 7.20 (td, J = 8.4, 3.1 Hz, 1H), 7.10 (s, 1H), 6.37 (s, 1H). | 458 | E | |
| I-1971 | 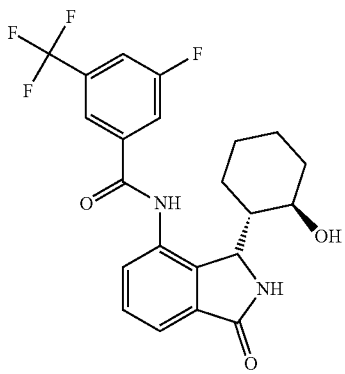 [SMILES: O=C(Nc1cccc2c1C([C@@H]1CCCC[C@H]1O)NC2=O)c1cc(F)cc(C(F)(F)F)c1] | [H][C@]1(CCCC[C@H]1O)C1NC(=O)c2cccc(NC(=O)c3cc(F)cc(c3)C(F)(F)F)c12 | (400 MHz, DMSO-d6) 10.74 (s, 1H), 8.12 (s, 1H), 8.08 (d, J = 9.0 Hz, 1H), 8.04 (d, J = 8.5 Hz, 1H), 7.65 (dd, J = 7.4, 1.2 Hz, 1H), 7.59-7.50 (m, 3H), 4.94-4.88 (m, 2H), 3.94-3.88 (m, 1H), 1.92 (d, J = 12.4 Hz, 1H), 1.66 (d, J = 13.6 Hz, 1H), 1.55-1.39 (m, 2H), 1.30-1.20 (m, 2H), 1.15 (d, J = 13.3 Hz, 1H), 1.03-0.89 (m, 1H), 0.47 (d, J = 10.5 Hz, 1H) [single diastereomer]. | 437.2 | E | |
| I-1972 | 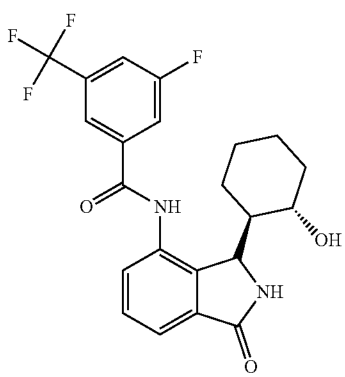 [SMILES: O=C(Nc1cccc2c1C([C@H]1CCCC[C@@H]1O)NC2=O)c1cc(F)cc(C(F)(F)F)c1] | [H][C@]1(CCCC[C@@H]1O)C1NC(=O)c2ccc c(NC(=O)c3cc(F)cc(c3)C(F)(F)F)c12 | (400 MHz, DMSO-d6) 10.64 (s, 1H), 8.59 (s, 1H), 8.14 (s, 1H), 8.07 (d, J = 8.8 Hz, 1H), 8.01 (d, J = 8.5 Hz, 1H), 7.59-7.48 (m, 3H), 5.30 (d, J = 1.1 Hz, 1H), 4.70 (d, J = 4.5 Hz, 1H), 3.44-3.35 (m, 1H), 1.85 (d, J = 8.9 Hz, 1H), 1.73 (t, J = 10.5 Hz, 1H), 1.54 (d, J = 12.7 Hz, 1H), 1.42 (d, J = 12.6 Hz, 1H), 1.14-0.86 (m, 3H), 0.75-0.66 (m, 1H), 0.66-0.55 (m, 1H) [single diastereomer] [~5 wt % TBSOH as impurity]. | 437.2 | E | |
| I-1973 | 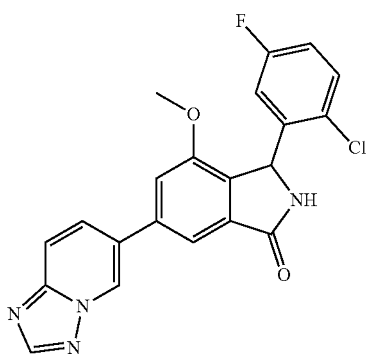 | COc1cc(cc2C(=O)NC(c12)c1cc(F)ccc1Cl)-c1ccc2ncnn2c1 | 1H NMR (400 MHz, DMSO-d6) 9.51 (t, J = 1.4 Hz, 1H), 9.15 (s, 1H), 8.57 (s, 1H), 8.17 (dd, J = 9.3, 1.8 Hz, 1H), 7.96 (dd, J = 9.3, 0.9 Hz, 1H), 7.72 (d, J = 1.3 Hz, 1H), 7.62-7.53 (m, 2H), 7.24 (td, J = 8.4, 3.1 Hz, 1H), 6.81 (s, 1H), 6.04 (s, 1H), 3.82 (s, 3H). | 409.05 | E | |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-1974 | 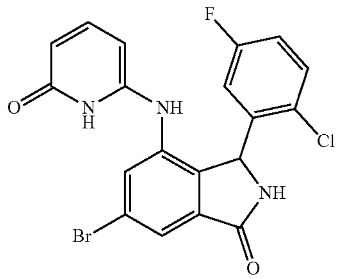 [SMILES: O=C1NC(c2cc(F)ccc2Cl)c2c(Nc3cccc(=O)[nH]3)cc(Br)cc21] | Fc1ccc(Cl)c(c1)C1NC(=O)c2cc(Br)cc(Nc3cccc(=O)[nH]3)c12 | 1H NMR (400 MHz, DMSO-d6) 10.31 (s, 1H), 9.14 (s, 1H), 8.46 (s, 1H), 7.71 (d, J = 4.3 Hz, 1H), 7.53 (s, 1H), 7.41-7.23 (m, 2H), 7.13 (td, J = 8.4, 3.1 Hz, 1H), 6.49 (s, 1H), 6.11 (s, 1H), 6.00 (s, 1H), 5.90 (s, 1H). | 449.95 | D | |
| I-1975 | 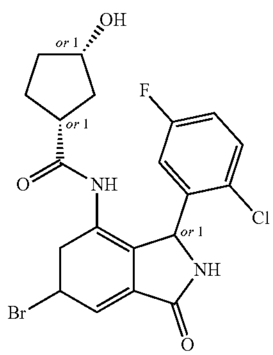 [SMILES: O=C1NC(c2cc(F)ccc2Cl)C2=C(NC(=O)[C@@H]3CC[C@H](O)C3)CC(Br)C=C12] | O[C@H]1CC[C@H](C1)C(=O)Nc1cc(Br)cc2C(=O)NC(c12)c1cc(F)ccc1Cl | 1H NMR (400 MHz, DMSO-d6) 9.68 (d, J = 17.2 Hz, 1H), 9.22 (s, 1H), 7.72-7.61 (m, 2H), 7.47 (d, J = 7.3 Hz, 1H), 7.24 (td, J = 8.4, 3.1 Hz, 1H), 6.67 (s, 1H), 6.01 (s, 1H), 4.62 (dd, J = 4.7, 2.8 Hz, 1H), 4.03-3.96 (m, 1H), 2.54 (s, 1H), 1.87-1.69 (m, 1H), 1.59 (dt, J = 10.3, 6.9 Hz, 1H), 1.56-1.29 (m, 4H). | 466.95 | E | |
| I-1976 | 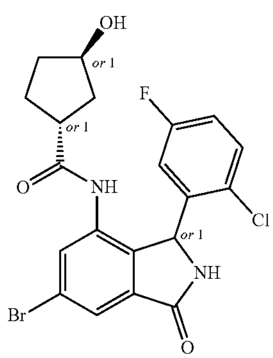 [SMILES: O=C1NC(c2cc(F)ccc2Cl)c2c(NC(=O)[C@@H]3CC[C@@H](O)C3)cc(Br)cc21] | O[C@@H]1CC[C@H](C1)C(=O)Nc1cc(Br)cc2C(=O)NC(c12)c1cc(F)ccc1Cl | 1H NMR (400 MHz, DMSO-d6) 9.75 (s, 1H), 9.23 (s, 1H), 7.69 (d, J = 1.5 Hz, 1H), 7.61 (dt, J = 6.0, 2.0 Hz, 1H), 7.48 (d, J = 6.9 Hz, 1H), 7.29-7.19 (m, 1H), 6.67 (s, 1H), 6.02 (s, 1H), 4.47 (t, J = 3.9 Hz, 1H), 4.09 (s, 1H), 2.54 (s, 1H), 1.73-1.60 (m, 1H), 1.64 (s, 2H), 1.50 (dd, J = 8.5, 3.9 Hz, 1H), 1.40 (s, 2H). | 467.05 | E | |
| I-1977 | 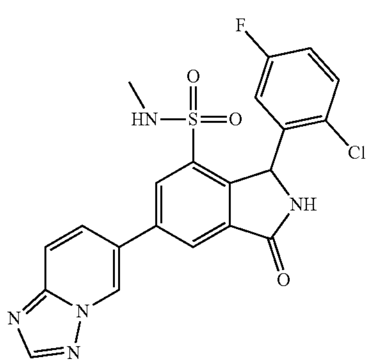 [SMILES: CNS(=O)(=O)c1cc(-c2ccc3ncnn3c2)cc2c1C(c1cc(F)ccc1Cl)NC2=O] | CNS(=O)(=O)c1cc(cc2C(=O)NC(c12)c1cc(F)ccc1Cl)-c1ccc2ncnn2c1 | 1H NMR (400 MHz, DMSO-d6) 9.56 (d, J = 1.9 Hz, 1H), 9.50 (s, 1H), 8.61 (s, 1H), 8.45 (s, 1H), 8.40 (s, 1H), 8.19 (dd, J = 9.3, 1.9 Hz, 1H), 8.04 (d, J = 9.3 Hz, 1H), 7.55 (s, 2H), 7.21 (td, J = 8.4, 3.0 Hz, 1H), 6.38 (s, 2H), 2.33 (s, 3H). | 472 | E | |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-1978 | 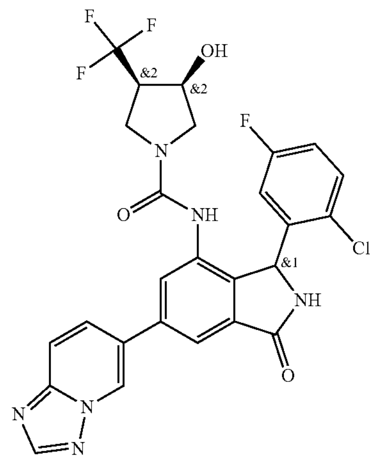 [SMILES: O=C1NC(c2cc(F)ccc2Cl)c2c(NC(=O)N3C[C@@H](C(F)(F)F)[C@@H](O)C3)cc(-c3ccc4ncnn4c3)cc21] | O[C@H]1CN(C[C@H]1C(F)(F)F)C(=O)Nc1cc(c2C(=O)NC(c12)c1cc(F)ccc1Cl)-c1ccc2ncnn2c1 | 1H-NMR (400 MHz, DMSO-d6) as a ca. 1:1 mixture of diastereomers 9.39-9.38 (m, 2H), 9.16 (br. s, 2H), 8.56 (s, 2H), 8.35 (br. s, 1H), 8.27 (br. s, 1H), 8.08-8.04 (m, 2H), 7.99-7.95 (m, 2H), 7.93-7.90 (m, 2H), 7.82-7.78 (m, 1H), 7.74 (d, J = 1.1 Hz, 1H), 7.53-7.46 (m, 2H), 7.23 (app. td, J = 8.4, 3.0 Hz, 2H), 6.68 (br. s, 2H), 6.10 (br. s, 2H), 5.58 (br. d, J = 4.3 Hz, 1H), 5.49 (d, J = 4.5 Hz, 1H), 4.44-4.36 (m, 2H), 3.67-3.51 (m, 1H), 3.47-3.40 (m, 3H), 3.31-3.20 (m, 2H), 3.16-3.03 (m, 1H), 3.02-2.86 (m, 3H). | 575.3 | D | |
| I-1979 | 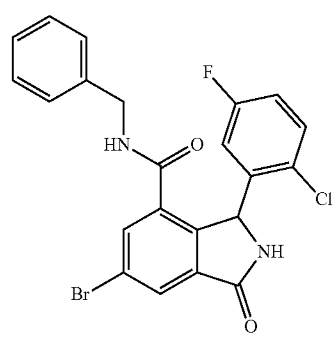 [SMILES: O=C(NCc1ccccc1)c1cc(Br)cc2c1C(c1cc(F)ccc1Cl)NC2=O] | Fc1ccc(Cl)c(c1)C1NC(=O)c2cc(Br)cc(C(=O)NCc3ccccc3)c12 | 1H NMR (400 MHz, DMSO-d6) 9.34 (s, 1H), 9.08 (dd, J = 7.3, 4.7 Hz, 1H), 8.08 (s, 1H), 8.01 (d, J = 1.8 Hz, 1H), 7.49 (s, 1H), 7.30-7.17 (m, 4H), 6.87 (dd, J = 6.7, 2.9 Hz, 2H), 6.36 (s, 1H), 4.61-4.39 (m, 1H), 4.15-3.88 (m, 1H). | 475 | E | |
| I-1980 | 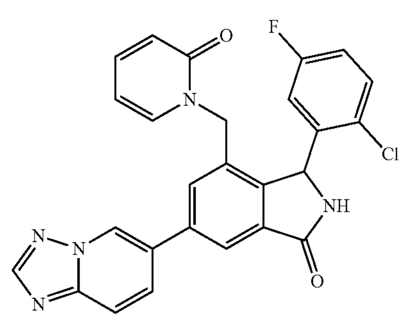 [SMILES: O=C1NC(c2cc(F)ccc2Cl)c2c(Cn3ccccc3=O)cc(-c3ccc4ncnn4c3)cc21] | Fc1ccc(Cl)c(c1)C1NC(=O)c2cc(cc(Cn3ccccc3=O)c12)-c1ccc2ncnn2c1 | NMR (400 MHz, DMSO-d6) 9.38 (br. s, 1H), 8.56 (s, 1H), 8.52 (br. s, 2H), 8.13-8.10 (m, 1H), 7.90-7.92 (m, 2H), 7.68-7.56 (m, 2H), 7.43-7.34 (m, 1H), 7.26 (ddd, J = 8.6, 8.0, 2.9 Hz, 1H), 6.51 (br. s, 1H), 6.37 (br. s, 1H), 6.33 (d, J = 9.3 Hz, 1H), 6.19 (app. t, J = 7.0 Hz, 1H), 4.88 (d, J = 14.5 Hz, 1H), 4.72 (d, J = 14.8 Hz, 1H); contains acetonitrile (2.08); contains some impurities (~10% by LC). | 486.2 | E | |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-1981 | 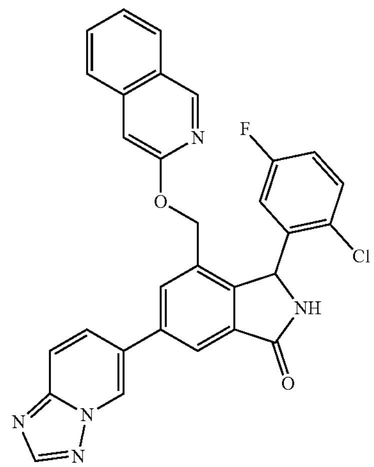 [SMILES: O=C1NC(c2cc(F)ccc2Cl)c2c(COc3cc4ccccc4cn3)cc(-c3ccc4ncnn4c3)cc21] | Fc1ccc(Cl)c(c1)C1NC(=O)c2cc(cc(COc3cc4ccc c4cn3)c12)-c1ccc2nc nn2c1 | NMR (400 MHz, DMSO-d6) 9.49 (dd, J = 1.7, 0.8 Hz, 1H), 9.32 (br. s, 1H), 8.98 (s, 1H), 8.57 (s, 1H), 8.21 (br. s, 1H), 8.17 (submerged br. s, 1H), 8.15 (overlapping dd, J = 4.6, 1.8 Hz, 1H), 8.01 (d, J = 8.3 Hz, 1H), 7.97 (d, J = 9.2 Hz, 1H), 7.78 (d, J = 8.1 Hz, 1H), 7.65 (ddd, J = 8.2, 6.8, 1.0, 1H), 7.44 (ddd, J = 8.0, 6.8, 1.0 Hz, 1H), 7.38 (dd, J = 8.8, 5.2 Hz, 1H), 7.13 (br. s, 1H), 7.03 (br. s, 1H), 6.57 (br. s, 1H), 6.35 (br. s, 1H), 5.27 (d, J = 12.2 Hz, 1H), 5.15 (br. s, 1H). contains 8% ammonium formate salt (8.43); contains residual acetonitrile (2.08). | 536.2 | D | |
| I-1982 | 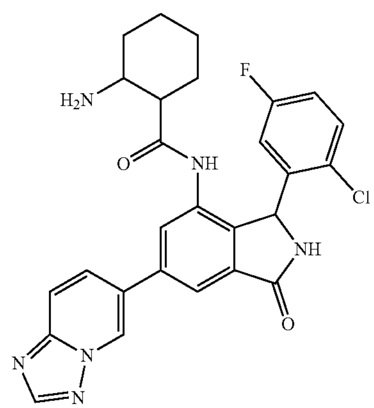 [SMILES: NC1CCCCC1C(=O)Nc1cc(-c2ccc3ncnn3c2)cc2c1C(c1cc(F)ccc1Cl)NC2=O] | NC1CCCCC1C(=O)Nc1cc(cc2C(=O)NC(c12)c1cc(F)ccc1Cl)-c1ccc2ncnn2c1 | 1H NMR (400 MHz, DMSO-d6) 9.43 (s, 1H), 9.22 (d, J = 9.8 Hz, 1H), 8.58 (s, 1H), 8.40-8.05 (m, 2H), 8.05-7.98 (m, 2H), 7.53 (s, 1H), 7.32-7.20 (m, 1H), 6.90-6.35 (m,1H), 6.17 (s, 1H), 3.10-2.90 (m, 1H), 2.25-1.90 (m, 1H), 1.85-1.50 (m,2H), 1.50-1.35(m,2H), 1.35-1.15(m,4H), 1.15-0.80(m,2H) | 519.1 | E | |
| I-1983 | 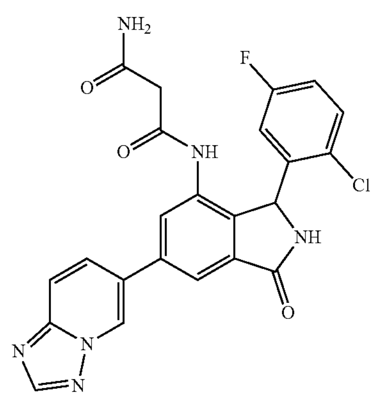 [SMILES: NC(=O)CC(=O)Nc1cc(-c2ccc3ncnn3c2)cc2c1C(c1cc(F)ccc1Cl)NC2=O] | NC(=O)CC(=O)Nc1cc(cc2C(=O)NC(c12)c1cc(F)ccc1Cl)-c1ccc2ncnn2c1 | NMR (400 MHz, DMSO-d6) 10.05 (br s, 1H), 9.43 (d, J = 0.7 Hz, 1H), 9.21 (br s, 1H), 8.57 (s, 1H), 8.08 (dd, J = 9.3, 1.5 Hz, 1H), 8.01 (d, J = 0.9 Hz, 1H), 7.98-7.91 (m, 2H), 7.54-7.44 (m, 2H), 7.23 (td, J = 8.3, 3.0 Hz, 1H), 7.17-7.08 (m, 1H), 6.74 (br s, 1H), 6.07 (br s, 1H), 3.00 (d, J = 15.9 Hz, 1H), 2.96 (d, J = 16.2 Hz, 1H). | 479 | E | |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-1984 | 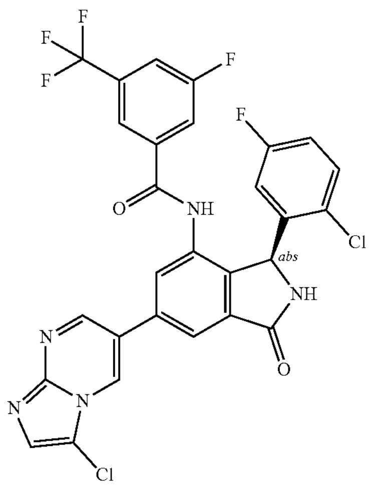 [SMILES: O=C(Nc1cc(-c2cnc3ncc(Cl)n3c2)cc2c1[C@@H](c1cc(F)ccc1Cl)NC2=O)c1cc(F)cc(C(F)(F)F)c1] | Fc1ccc(Cl)c(c1)[C@H]1NC(=O)c2cc(cc(NC(=O)c3cc(F)cc(c3)C(F)(F)F)c12)-c1cnc2ncc(Cl)n2c1 | 1H NMR (400 MHz, DMSO) δ 10.67 (s, 1H), 9.28 (s, 1H), 9.18 (d, J = 2.5 Hz, 1H), 9.06 (d, J = 2.5 Hz, 1H), 8.21 (d, J = 1.6 Hz, 1H), 7.96 (d, J = 16.9 Hz, 2H), 7.77 (d, J = 9.4 Hz, 1H), 7.71 (s, 1H), 7.34 (dd, J = 8.9, 5.2 Hz, 1H), 7.11 (td, J = 8.3, 3.1 Hz, 1H), 6.06 (s, 1H). | 619.18 | C | |
| I-1985 | 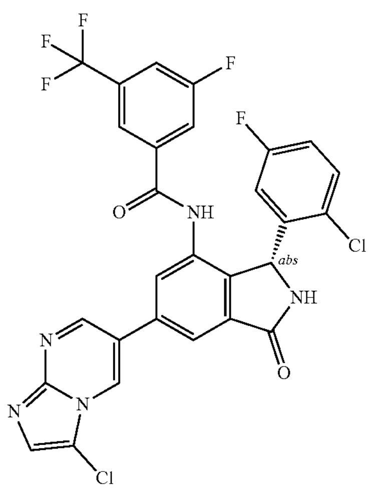 [SMILES: O=C(Nc1cc(-c2cnc3ncc(Cl)n3c2)cc2c1[C@H](c1cc(F)ccc1Cl)NC2=O)c1cc(F)cc(C(F)(F)F)c1] | Fc1ccc(Cl)c(c1)[C@@H]1NC(=O)c2cc(cc(NC(=O)c3cc(F)cc(c3)C(F)(F)F)c12)-c1cnc2ncc(Cl)n2c1 | 1H NMR (400 MHz, DMSO) δ 10.67 (s, 1H), 9.28 (s, 1H), 9.18 (d, J = 2.5 Hz, 1H), 9.06 (d, J = 2.5 Hz, 1H), 8.21 (d, J = 1.6 Hz, 1H), 7.96 (d, J = 16.9 Hz, 2H), 7.77 (d, J = 9.4 Hz, 1H), 7.71 (s, 1H), 7.34 (dd, J = 8.9, 5.2 Hz, 1H), 7.11 (td, J = 8.3, 3.1 Hz, 1H), 6.06 (s, 1H). | 619.18 | A | |
| I-1986 | 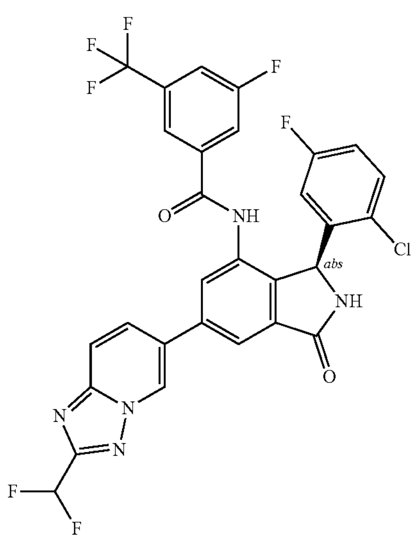 [SMILES: O=C(Nc1cc(-c2ccc3nc(C(F)F)nn3c2)cc2c1[C@@H](c1cc(F)ccc1Cl)NC2=O)c1cc(F)cc(C(F)(F)F)c1] | FC(F)c1nc2ccc(cn2n1)c1cc2C(=O)N[C@@H](c2c(NC(=O)c2cc(F)cc(c2)C(F)(F)F)c1)c1cc(F)ccc1Cl | 1H NMR (400 MHz, DMSO) δ 10.65 (s, 1H), 9.56 (dd, J = 1.9, 0.9 Hz, 1H), 9.27 (s, 1H), 8.25 (dd, J = 9.4, 1.8 Hz, 1H), 8.15 (d, J = 1.7 Hz, 1H), 8.07 (dd, J = 9.3, 0.9 Hz, 1H), 8.00-7.93 (m, 2H), 7.76 (d, J = 9.1 Hz, 1H), 7.70 (s, 1H), 7.38-7.28 (m, 2H), 7.11 (td, J = 8.4, 3.1 Hz, 1H), 3.16 (d, J = 3.5 Hz, 1H). | 634.19 | D | |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-1987 | 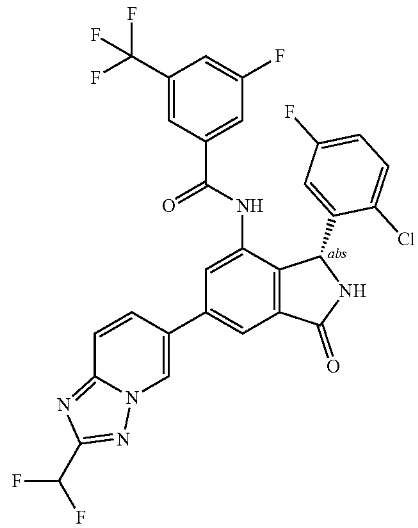 [SMILES: O=C(Nc1cc(-c2ccc3nc(C(F)F)nn3c2)cc2c1[C@H](c1cc(F)ccc1Cl)NC2=O)c1cc(F)cc(C(F)(F)F)c1] | FC(F)c1 nc2ccc (cn2n1)-c1cc2C (=O)N[C @H](c2 c(NC(= O)c2cc (F)cc(c2) C(F)(F) F)c1)c1 cc(F)ccc 1Cl | 1H NMR (400 MHz, DMSO) δ 10.65 (s, 1H), 9.56 (dd, J = 1.9, 0.9 Hz, 1H), 9.27 (s, 1H), 8.25 (dd, J = 9.4, 1.8 Hz, 1H), 8.15 (d, J = 1.7 Hz, 1H), 8.07 (dd, J = 9.3, 0.9 Hz, 1H), 8.00-7.93 (m, 2H), 7.76 (d, J = 9.1 Hz, 1H), 7.70 (s, 1H), 7.38-7.28 (m, 2H), 7.11 (td, J = 8.4, 3.1 Hz, 1H), 3.16 (d, J = 3.5 Hz, 1H). | 634.19 | A | |
| I-1988 | 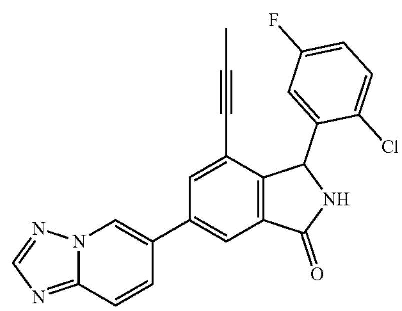 [SMILES: CC#Cc1cc(-c2ccc3ncnn3c2)cc2c1C(c1cc(F)ccc1Cl)NC2=O] | CC#Cc1 cc(cc2C (=O)NC (c12)c1c c(F)ccc1 Cl)-c1ccc2n cnn2c1 | 1H NMR (400 MHz, DMSO-d6) 9.47 (d, J = 2.4 Hz, 1H), 9.29 (s, OH), 8.56 (s, 1H), 8.17-8.08 (m, 2H), 8.00 (d, J = 1.7 Hz, 1H), 7.94 (d, J = 9.3 Hz, 1H), 7.58 (s, 1H), 7.27 (td, J = 8.4, 3.1 Hz, 1H), 6.12 (s, 1H), 2.96 (q, J = 2.1 Hz, 1H), 1.87 (s, 3H). | 417.05 | E | |
| I-1989 | 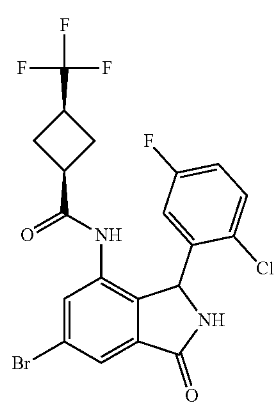 [SMILES: O=C1NC(c2cc(F)ccc2Cl)c2c(NC(=O)[C@H]3C[C@@H](C(F)(F)F)C3)cc(Br)cc21] | Fc1ccc (Cl)c(c1) C1NC(= O)c2cc (Br)cc(N C(=O) [C@H]3 C[C@H] (C3)C (F)(F)F)c 12 | 1H NMR (400 MHz, DMSO-d6) 9.78 (s, 1H), 9.24 (s, 1H), 7.72 (d, J = 1.8 Hz, 1H), 7.62 (d, J = 1.8 Hz, 1H), 7.47 (d, J = 7.6 Hz, 1H), 7.23 (ddd, J = 8.8, 7.9, 3.1 Hz, 1H), 6.64 (s, 1H), 6.02 (s, 1H), 3.09 (dq, J = 18.2, 9.1 Hz, 1H), 2.91 (p, J = 9.0 Hz, 1H), 2.13-1.86 (m, 4H). | 506.9 | D | |

TABLE 2-continued

Representative Compounds of the Invention with Bioactivity Data.

| Ex. No. | Structure | SMILES | $^1$H NMR | MS | ADP-Glo IC$_{50}$ | MCF 10A IC$_{50}$ |
|---|---|---|---|---|---|---|
| I-1990 | 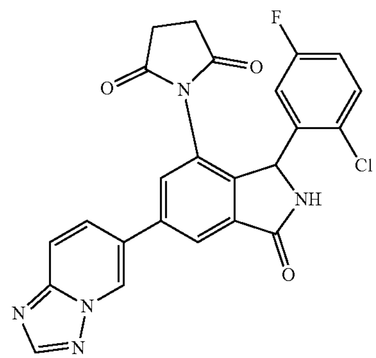 [SMILES: O=C1NC(c2cc(F)ccc2Cl)c2c1cc(-c1ccc3ncnn3c1)cc2N1C(=O)CCC1=O] | Fc1ccc(Cl)c(c1)C1NC(=O)c2cc(cc(N3C(=O)CCC3=O)c12)-c1ccc2ncnn2c1 | NMR (400 MHz, DMSO-d6) 9.45 (d, J = 0.8 Hz, 1H), 9.36 (br s, 1H), 8.58 (s, 1H), 8.32 (br s, 1H), 8.06 (dd, J = 9.3, 1.8 Hz, 1H), 8.01-7.95 (m, 2H), 7.70-7.48 (m, 1H), 7.25 (td, J = 8.6, 2.9 Hz, 1H), 6.56 (br s, 1h), 5.96 (br s, H), 2.92-2.76 (m, 1H), 2.76-2.60 (m, 2H), 2.44-2.11 (m, 1H).. | 476 | E | |
| I-1991 | 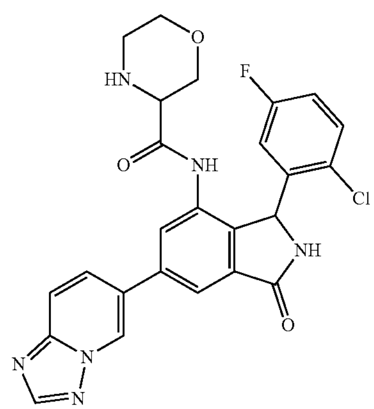 [SMILES: O=C1NC(c2cc(F)ccc2Cl)c2c(NC(=O)C3COCCN3)cc(-c3ccc4ncnn4c3)cc21] | Fc1ccc(Cl)c(c1)C1NC(=O)c2cc(cc(NC(=O)C3COCCN3)c12)-c1ccc2ncnn2c1 | NMR (400 MHz, DMSO-d6) 9.67-9.47 (m, 1H), 9.43-9.38 (m, 1H), 9.31-9.19 (m, 1H), 8.58 (s, 1H), 8.29 (s, 1H), 8.25 (s, 1H), 8.16 (d, J = 1.6 Hz, 1H), 8.11-8.03 (m, 1H), 8.02-7.93 (m, 2H), 7.66-7.48(m, 1H), 7.36-7.22 (m, 1H), 6.14 (br s, 1H), 3.58-3.44 (m, 2H), 3.42-3.19 (m, 4H), 3.18-3.07 (m, 1H). mixture of diastereomers (1:1.6) | 507.3 | E | |
| I-1992 | 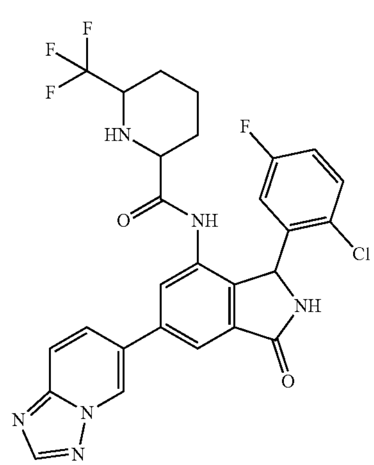 [SMILES: O=C1NC(c2cc(F)ccc2Cl)c2c(NC(=O)C3CCCC(C(F)(F)F)N3)cc(-c3ccc4ncnn4c3)cc21] | Fc1ccc(Cl)c(c1)C1NC(=O)c2cc(cc(NC(=O)C3CCCC(N3)C(F)(F)F)c12)-c1ccc2ncnn2c1 | NMR (400 MHz, ACN-d3) 9.05 (s, 1H), 8.43-8.32 (m, 1H), 8.12 (d, J = 9.2 Hz, 1H), 7.96 (d, J = 11.0 Hz, 1H), 7.50 (s, 1H), 7.31 (, 1Hs), 7.23-7.04 (m, 1H), 6.62 (br s, 1H), 6.27 (br , 1H), 3.33-3.10 (m, 2H), 1.87-1.59 (m, 4H), 1.46-1.33 (m, 1H), 1.33-1.11 (m, 1H), 0.96-0.78 (m, 1H). Mixture of diastereomers (3:1); major reported | 573.1 | D | |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-1993 | 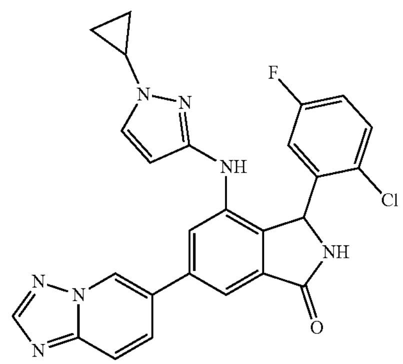 [SMILES: O=C1NC(c2cc(F)ccc2Cl)c2c(Nc3ccn(C4CC4)n3)cc(-c3ccc4ncnn4c3)cc21] | Fc1ccc(Cl)c(c1)C1NC(=O)c2cc(cc(Nc3ccn(n3)C3CC3)c12)-cccc2ncnn2c1 | 1H NMR (400 MHz, DMSO-d6) 9.35-9.30 (m, 1H), 9.06 (s, 1H), 8.56 (s, 1H), 8.03 (dd, J = 9.3, 1.8 Hz, 1H), 8.00-7.92 (m, 2H), 7.83 (s, 1H), 7.59 (dd, J = 11.8, 1.9 Hz, 2H), 7.48 (dd, J = 8.8, 5.2 Hz, 1H), 7.20 (td, J=8.3, 3.1 Hz, 1H), 6.62 (s, 1H), 6.09 (s, 1H), 5.75 (d, J = 2.3 Hz, 1H), 3.57 (tt, J = 7.3, 3.9 Hz, 1H), 1.02-0.85 (m, 4H). | 500.05 | E | |
| I-1994 | 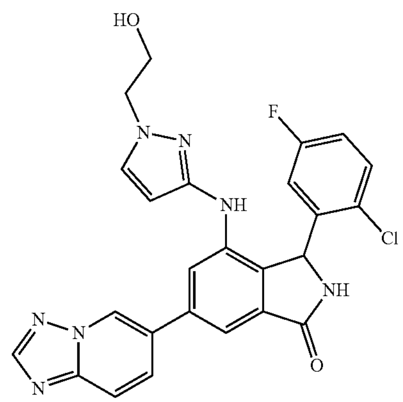 [SMILES: O=C1NC(c2cc(F)ccc2Cl)c2c(Nc3ccn(CCO)n3)cc(-c3ccc4ncnn4c3)cc21] | OCCn1ccc(Nc2cc(cc3C(=O)NC(c23)c2cc(F)ccc2Cl)-c2ccc3ncnn3c2)n1 | 1H NMR (400 MHz, DMSO-d6) 9.32 (dd, J = 1.8, 1.0 Hz, 1H), 9.05 (s, 1H), 8.56 (s, 1H), 8.02 (dd, J = 9.3, 1.8 Hz, 1H), 8.00-7.92 (m, 2H), 7.78 (s, 1H), 7.60 (d, J = 1.6 Hz, 1H), 7.53 (d, J = 2.3 Hz, 1H), 7.49 (dd, J = 8.9, 5.2 Hz, 1H), 7.21 (ddd, J = 8.9, 7.9, 3.1 Hz, 1H), 6.69 (s, 1H), 6.11 (s, 1H), 5.76 (d, J = 2.3 Hz, 1H), 4.86 (t, J = 5.3 Hz, 1H), 4.02 (td, J = 5.5, 1.6 Hz, 2H), 3.72 (q, J = 5.7 Hz, 2H). | 504 | E | |
| I-1995 | 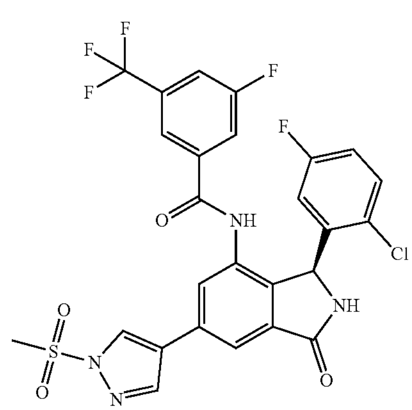 [SMILES: CS(=O)(=O)n1cc(-c2cc(NC(=O)c3cc(F)cc(C(F)(F)F)c3)c3c(c2)C(=O)N[C@@H]3c2cc(F)ccc2Cl)cn1] | CS(=O)(=O)n1cc(cn1)-c1cc2C(=O)N[C@@H](c2c(NC(=O)c2cc(F)cc(c2)C(F)(F)F)c1)c1cc(F)ccc1Cl | (400 MHz, DMSO-d6) 10.58 (br s, 1 H), 9.19 (br s, 1 H), 8.98 (s, 1 H), 8.64 (s, 1 H), 8.13 (s, 1 H), 7.99-7.91 (m, 2 H), 7.76 (d, J = 8.9 Hz, 1 H), 7.72 (s, 1 H), 7.32 (dd, J = 8.9, 5.1 Hz, 1 H), 7.10 (td, J = 8.5, 2.9 Hz, 1 H), 6.58 (br s, 1 H), 5.99 (br s, 1 H), 3.61 (s, 3 H). | 609.1 | C | |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-1996 | 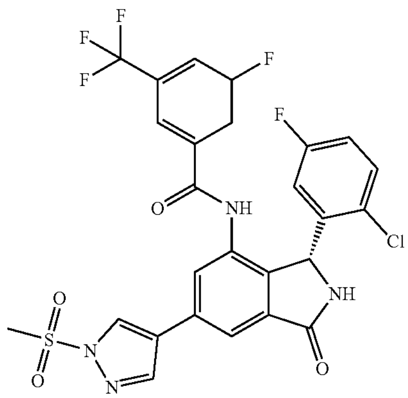 [SMILES: CS(=O)(=O)n1cc(-c2cc(NC(=O)C3=CC(C(F)(F)F)=CC(F)C3)c3c(c2)C(=O)N[C@H]3c2cc(F)ccc2Cl)cn1] | CS(=O)(=O)n1cc(cn1)-c1cc2C(=O)N[C@H](c2c(NC(=O)c2cc(F)cc(c2)C(F)(F)F)c1)c1cc(F)ccc1Cl | (400 MHz, DMSO-d6) 10.58 (br s, 1 H), 9.18 (br s, 1 H), 8.97 (s, 1 H), 8.64 (s, 1 H), 8.13 (s, 1 H), 8.00-7.88 (m, 2 H), 7.76 (d, J = 8.9 Hz, 1 H), 7.73 (s, 1 H), 7.32 (dd, J = 8.9, 5.2 Hz, 1 H), 7.10 (td, J = 8.5, 3.0 Hz, 1 H), 6.61 (br s, 1 H), 5.99 (br s, 1 H), 3.61 (s, 3 H). | 609.1 | A | |
| I-1997 | 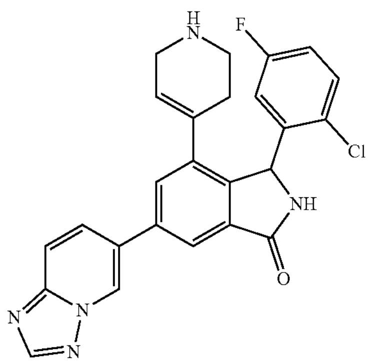 [SMILES: O=C1NC(c2cc(F)ccc2Cl)c2c1cc(-c1ccc3ncnn3c1)cc2C1=CCNCC1] | Fc1ccc(Cl)c(c1)C1NC(=O)c2cc(cc(c12)C1=CCNCC1)-c1ccc2ncnn2c1 | NMR (400 MHz, DMSO-d6) 9.50 (d, J = 0.7 Hz, 1H), 9.27 (br s, 1H), 8.56 (s, 1H), 8.33 (br s, 1H), 8.16 (dd, J = 9.3, 1.8 Hz, 1H), 8.06 (d, J = 1.4 Hz, 1H), 7.95 (d, J = 9.3 Hz, 1H), 7.83 (s, 1H), 7.62-7.47 (m, 1H), 7.25 (td, J = 8.4, 3.1 Hz, 1H), 6.46 (br s, 1H), 6.29 (br s, 1H), 5.84 (br s, 1H), 3.46-3.08 (m, 2H), 2.98-2.71 (m, 1H), 2.58 (br d, J = 12.3 Hz, 1H), 2.39-2.16 (m, 1H), 1.47 (br d, J = 13.5 Hz, 1H). | 460 | E | |
| I-1998 | 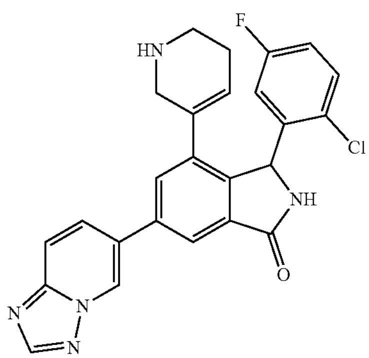 | Fc1ccc(Cl)c(c1)C1NC(=O)c2cc(cc(c12)C1=CCCNC1)-c1ccc2ncnn2c1 | NMR (400 MHz, DMSO-d6) 9.53-9.51 (m, 1H), 9.27 (br s, 1H), 8.56 (s, 1H), 8.18 (dd, J = 9.3, 1.4 Hz, 1H), 8.06 (s, 1H), 7.94 (d, J = 9.3 Hz, 1H), 7.89 (s, 1H), 7.66-7.46 (m, 1H), 7.25 (td, J = 8.4, 3.0 Hz, 1H), 6.41 (br s, 1H), 6.29 (br s, 1H), 5.90 (br s, 1H), 3.69 (br d, J = 18.1 Hz, 1H), 2.92-2.72 (m, 1H), 2.47-2.34 (m, 1H), 2.17-1.87 (m, 3H). One proton missing or submerged. | 460 | E | |
| I-1999 | 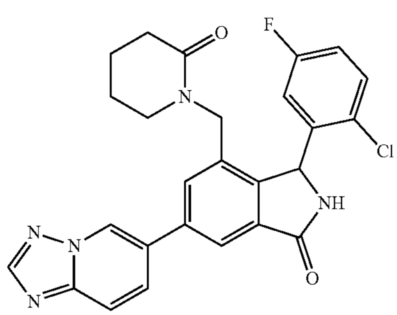 [SMILES: O=C1NC(c2cc(F)ccc2Cl)c2c(CN3CCCCC3=O)cc(-c3ccc4ncnn4c3)cc21] | Fc1ccc(Cl)c(c1)C1NC(=O)c2cc(cc(CN3CCCCC3=O)c12)-c1ccc2ncnn2c1 | NMR (400 MHz, DMSO-d6) 9.42-9.40 (m, 1H), 9.36-9.18 (m, 1H), 8.57 (s, 1H), 8.10-8.03 (m, 2H), 7.97 (d, J = 9.3 Hz, 1H), 7.64 (s, 2H), 7.30 (td, J = 8.3, 3.1 Hz, 1H), 6.51 (br. s, 1H), 6.23 (br. s, 1H), 4.40 (d, J = 15.3 Hz, 1H), 4.07 (d, J = 15.3 Hz, 1H), 3.23-3.05 (m, 1H), 3.05-2.83 (m, 1H), 2.28-2.21 (m, 2H), 1.85-1.55 (m, 4H) | 490.2 | E | |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-2000 | 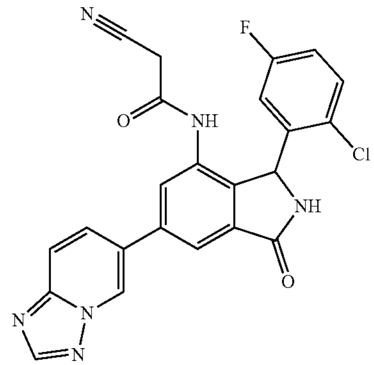 [SMILES: N#CCC(=O)Nc1cc(-c2ccc3ncnn3c2)cc2c1C(c1cc(F)ccc1Cl)NC2=O] | Fc1ccc(Cl)c(c1)C1NC(=O)c2cc(cc(NC(=O)CC#N)c12)-c1ccc2ncnn2c1 | NMR (400 MHz, DMSO-d6) 9.45 (s, 1H), 9.24 (br s, H), 8.57 (s, 1H), 8.15-8.05 (m, 2H), 7.97 (d, J = 9.2 Hz, 1H), 7.81 (s, 1H), 7.66-7.44 (m, 1H), 7.25 (td, J = 8.4, 3.0 Hz, 1H), 6.68 (br s, 1H), 6.03 (br s, 1H), 3.66 (d, J = 18.6 Hz, 1H), 3.52 (d, J = 18.6 Hz, 1H). Amide NH missing/submerged. | 461 | E | |
| I-2001 | 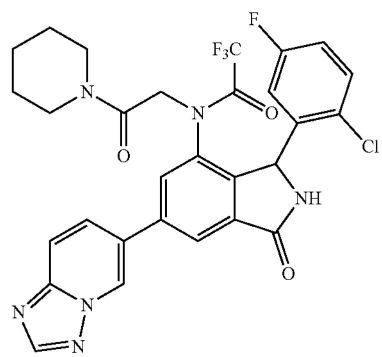 [SMILES: O=C1NC(c2cc(F)ccc2Cl)c2c1cc(-c1ccc3ncnn3c1)cc2N(CC(=O)N1CCCCC1)C(=O)C(F)(F)F] | Fc1ccc(Cl)c(c1)C1NC(=O)c2cc(cc(N(CC(=O)N3CCCC3)C(=O)C(F)(F)F)c12)-c1ccc2ncnn2c1 | NMR (400 MHz, DMSO-d6) 11.47 (s, 1H), 9.98 (s, 1H), 9.58 (s, 1H), 9.40 (br s, 1H), 8.92 (dd, J = 9.4, 1.3 Hz, 1H), 8.56 (d, J = 9.4 Hz, 1H), 8.35 (s, 1H), 8.10 (s, 1H), 7.68-7.39 (m, 1H), 7.27 (td, J = 8.4, 3.1 Hz, 1H), 6.07 (br s, 1H), 5.72 (s, 2H), 3.57-3.40 (m, 4H), 1.75-1.58 (m, 4H), 1.56-1.39 (m, 2H). | 615 | E | |
| I-2002 | 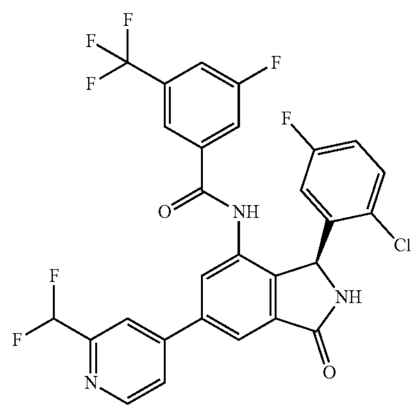 [SMILES: O=C(Nc1cc(-c2ccnc(C(F)F)c2)cc2c1[C@@H](c1cc(F)ccc1Cl)NC2=O)c1cc(F)cc(C(F)(F)F)c1] | FC(F)c1cc(ccn1)c1cc2C(=O)N[C@@H](c2c(NC(=O)c2cc(F)cc(c2)C(F)(F)F)c1)c1cc(F)ccc1Cl | 1H NMR (DMSO-d6, 400 MHz) δ 10.66 (s, 1H), 9.21-9.41 (m, 1H), 8.81 (d, J = 5.1 Hz, 1H), 8.17 (d, J = 1.3 Hz, 1H), 8.12 (s, 1H), 8.07 (br d, J = 5.3 Hz, 1H), 8.02 (s, 1H), 7.98 (br d, J = 8.6 Hz, 1H), 7.78 (br d, J = 9.1 Hz, 1H), 7.71 (s, 1H), 7.34 (dd, J = 9.0, 5.2 Hz, 1H), 6.90-7.20 (m, 2H), 6.39-6.71 (m, 1H), 5.92-6.26 ppm (m, 1H). | 594.2 | D | |
| I-2003 | 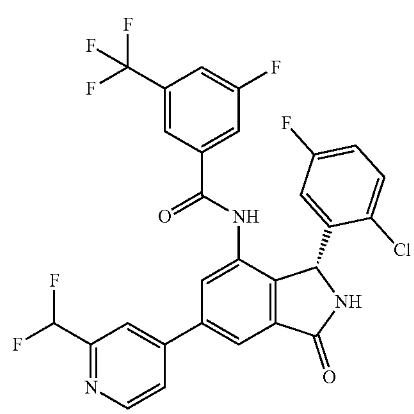 [SMILES: O=C(Nc1cc(-c2ccnc(C(F)F)c2)cc2c1[C@H](c1cc(F)ccc1Cl)NC2=O)c1cc(F)cc(C(F)(F)F)c1] | FC(F)c1cc(ccn1)-c1cc2C(=O)N[C@H](c2c(NC(=O)c2cc(F)cc(c2)C(F)(F)F)c1)c1cc(F)ccc1Cl | 1H NMR (DMSO-d6, 400 MHz) δ 10.66 (s, 1H), 9.21-9.41 (m, 1H), 8.81 (d, J = 5.1 Hz, 1H), 8.17 (d, J = 1.3 Hz, 1H), 8.12 (s, 1H), 8.07 (br d, J = 5.3 Hz, 1H), 8.02 (s, 1H), 7.98 (br d, J = 8.6 Hz, 1H), 7.78 (br d, J = 9.1 Hz, 1H), 7.71 (s, 1H), 7.34 (dd, J = 9.0, 5.2 Hz, 1H), 6.90-7.20 (m, 2H), 6.39-6.71 (m, 1H), 5.92-6.26 ppm (m, 1H). | 594.4 | A | |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-2004 | 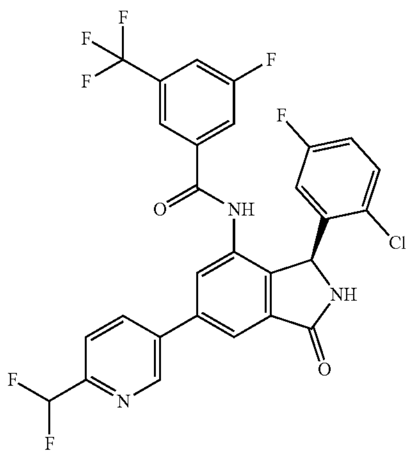 [SMILES: O=C(Nc1cc(-c2ccc(C(F)F)nc2)cc2c1[C@@H](c1cc(F)ccc1Cl)NC2=O)c1cc(F)cc(C(F)(F)F)c1] | FC(F)c1ccc(cn1)-c1cc2C(=O)N[C@@H](c2c(NC(=O)c2cc(F)cc(c2)C(F)(F)F)c1)c1cc(F)ccc1Cl | 1H NMR (DMSO-d6, 400 MHz) δ 10.66 (s, 1H), 9.28 (br s, 1H), 9.13 (d, J = 2.0 Hz, 1H), 8.43 (dd, J = 8.1, 2.3 Hz, 1H), 8.10 (d, J = 1.3 Hz, 1H), 7.97 (br d, J = 8.6 Hz, 1H), 7.93 (s, 1H), 7.84 (d, J = 8.3 Hz, 1H), 7.77 (br d, J = 9.1 Hz, 1H), 7.70 (s, 1H), 7.34 (dd, J = 8.8, 5.3 Hz, 1H), 6.90-7.22 (m, 2H), 6.46-6.84 (m, 1H), 5.85-6.25 ppm (m, 1H). | 594.2 | D | |
| I-2005 | 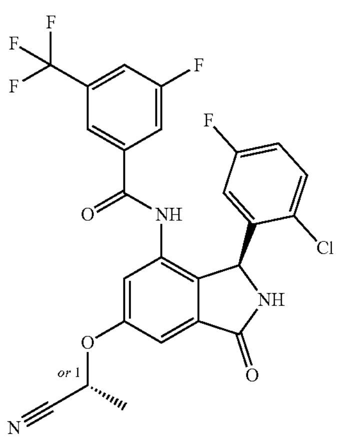 [SMILES: C[C@H](C#N)Oc1cc(NC(=O)c2cc(F)cc(C(F)(F)F)c2)c2c(c1)C(=O)N[C@@H]2c1cc(F)ccc1Cl] | C[C@H](Oc1cc2C(=O)N[C@H](c2c(NC(=O)c2cc(F)cc(c2)C(F)(F)F)c1)c1cc(F)ccc1Cl)C#N | | 536.1 | D | |
| I-2006 | 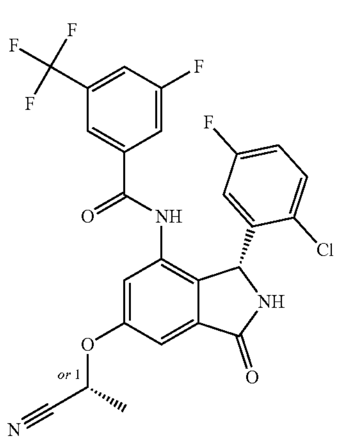 [SMILES: C[C@H](C#N)Oc1cc(NC(=O)c2cc(F)cc(C(F)(F)F)c2)c2c(c1)C(=O)N[C@H]2c1cc(F)ccc1Cl] | C[C@@H](Oc1cc2C(=O)N[C@H](c2c(NC(=O)c2cc(F)cc(c2)C(F)(F)F)c1)c1cc(F)ccc1)C#N | | 536.1 | A | |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-2007 | 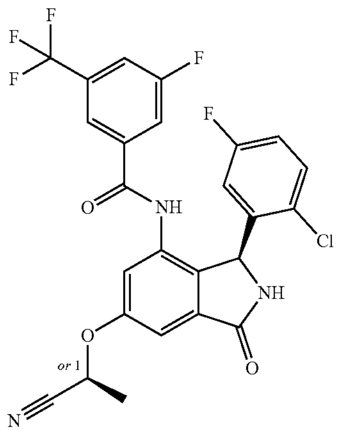 [SMILES: C[C@@H](C#N)Oc1cc(NC(=O)c2cc(F)cc(C(F)(F)F)c2)c2c(c1)C(=O)N[C@@H]2c1cc(F)ccc1Cl] | C[C@H](Oc1cc2C(=O)N[C@@H](c2c(NC(=O)c2cc(F)cc(c2)C(F)(F)F)c1)c1cc(F)ccc1Cl)C#N | | 536.1 | D | |
| I-2008 | 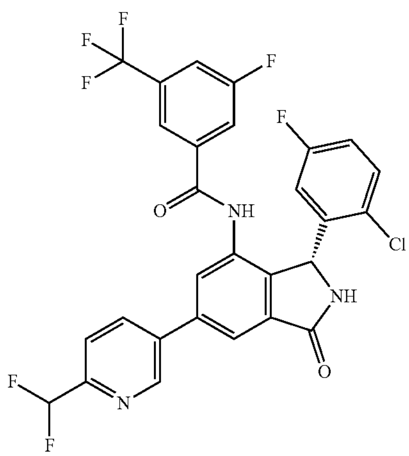 [SMILES: O=C(Nc1cc(-c2ccc(C(F)F)nc2)cc2c1[C@H](c1cc(F)ccc1Cl)NC2=O)c1cc(F)cc(C(F)(F)F)c1] | FC(F)c1ccc(cn1)-c1cc2C(=O)N[C@H](c2c(NC(=O)c2cc(F)cc(c2)C(F)(F)F)c1)c1cc(F)ccc1Cl | 1H NMR (DMSO-d6, 400 MHz): δ = 10.66 (s, 1H), 9.28 (br s, 1H), 9.13 (d, J = 2.0 Hz, 1H), 8.43 (dd, J = 8.1, 2.3 Hz, 1H), 8.10 (d, J = 1.3 Hz, 1H), 7.97 (br d, J = 8.6 Hz, 1H), 7.93 (s, 1H), 7.84 (d, J = 8.3 Hz, 1H), 7.77 (br d, J = 9.1 Hz, 1H), 7.70 (s, 1H), 7.34 (dd, J = 8.8, 5.3 Hz, 1H), 6.90-7.22 (m, 2H), 6.46-6.84 (m, 1H), 5.85-6.25 ppm (m, 1H). | 594.5 | A | |
| I-2009 | 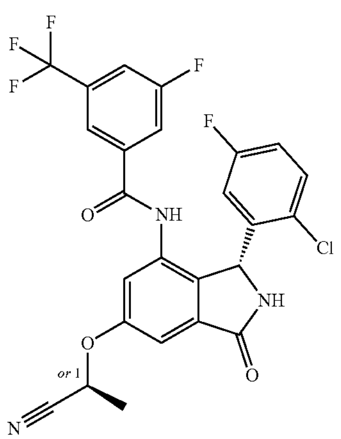 [SMILES: C[C@@H](C#N)Oc1cc(NC(=O)c2cc(F)cc(C(F)(F)F)c2)c2c(c1)C(=O)N[C@H]2c1cc(F)ccc1Cl] | C[C@@H](Oc1cc2C(=O)N[C@@H](c2c(NC(=O)c2cc(F)cc(c2)C(F)(F)F)c1)c1cc(F)ccc1Cl)C#N | | 536.1 | A | |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-2010 | 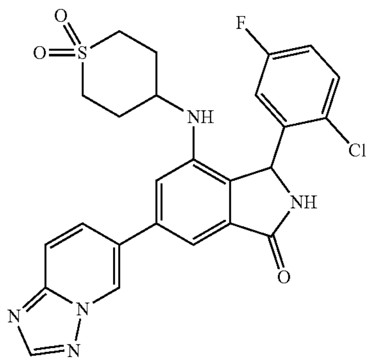 [SMILES: O=C1NC(c2cc(F)ccc2Cl)c2c(NC3CCS(=O)(=O)CC3)cc(-c3ccc4ncnn4c3)cc21] | Fc1ccc(Cl)c(c1)C1NC(=O)c2cc(cc(NC3CCS(=O)(=O)CC3)c12)c1ccc2nccnn2c1 | | 526 | E | |
| I-2012 | 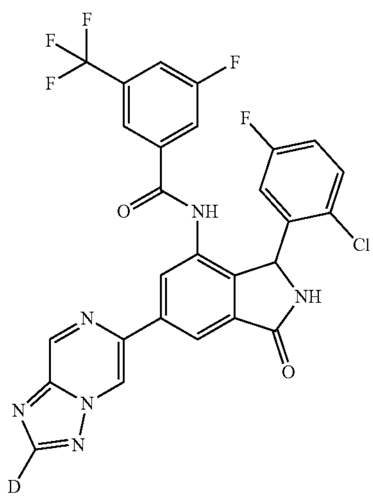 [SMILES: [2H]c1nc2cnc(-c3cc(NC(=O)c4cc(F)cc(C(F)(F)F)c4)c4c(c3)C(=O)NC4c3cc(F)ccc3Cl)cn2n1] | [2H]c1nc2cnc(cn2n1)-c1cc2C(=O)NC(c2c(NC(=O)c2cc(F)cc(c2)C(F)(F)F)c1)c1cc(F)ccc1Cl | 1H NMR (400 MHz, DMSO-d6) 10.69 (s, 1H), 9.92 (s, 1H), 9.54 (s, 1H), 9.26 (s, 1H), 8.48 (s, 1H), 8.35 (s, 1H), 7.94 (d, J = 8.3 Hz, 1H), 7.77 (d, J = 9.0 Hz, 1H), 7.71 (s, 1H), 7.37-7.30 (m, 1H), 7.11 (d, J = 8.7 Hz, 1H), 6.39 (br s, 1H). | 586.15 | A | |
| I-2013 | 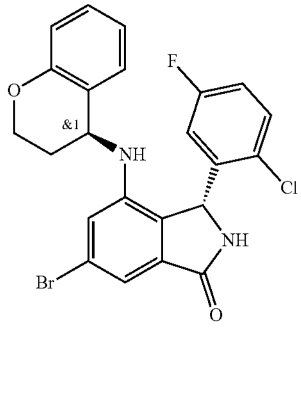 [SMILES: O=C1N[C@@H](c2cc(F)ccc2Cl)c2c(N[C@H]3CCOc4ccccc43)cc(Br)cc21] | Fc1ccc(Cl)c(c1)[C@@H]1NC(=O)c2cc(Br)cc(N[C@@H]3COc4ccccc34)c12 | 1H NMR (400 MHz, DMSO-d6) 9.08 (s, 0H), 7.49 (dd, J = 8.9, 5.1 Hz, 1H), 7.33-7.22 (m, 2H), 7.19-7.12 (m, 2H), 7.06 (ddd, J = 6.7, 4.8, 1.7 Hz, 1H), 6.85 (t, J = 7.5 Hz, 1H), 6.76 (dd, J = 8.3, 1.2 Hz, 2H), 5.89 (s, 1H), 5.10 (d, J = 7.5 Hz, 1H), 4.74 (dt, J = 9.3, 4.7 Hz, 1H), 4.00 (ddd, J = 10.2, 5.9, 3.3 Hz, 1H), 3.53-3.43 (m, 1H), 1.83 (tq, J = 8.0, 3.7 Hz, 1H), 1.63 (d, J = 14.6 Hz, 1H). | 486.9 | E | |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-2014 | 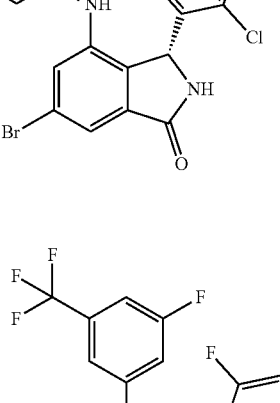 | Fc1ccc(Cl)c(c1)[C@@H]1NC(=O)c2cc(Br)cc(N[C@H]3CCOc4cccc34)c12 | 1H NMR (400 MHz, DMSO-d6) 9.08 (s, 0H), 7.49 (dd, J = 8.9, 5.1 Hz, 1H), 7.33-7.22 (m, 2H), 7.19-7.12 (m, 2H), 7.06 (ddd, J = 6.7, 4.8, 1.7 Hz, 1H), 6.85 (t, J = 7.5 Hz, 1H), 6.76 (dd, J = 8.3, 1.2 Hz, 2H), 5.89 (s, 1H), 5.10 (d, J = 7.5 Hz, 1H), 4.74 (dt, J = 9.3, 4.7 Hz, 1H), 4.00 (ddd, J = 10.2, 5.9, 3.3 Hz, 1H), 3.53-3.43 (m, 1H), 1.83 (tq, J = 8.0, 3.7 Hz, 1H), 1.63 (d, J = 14.6 Hz, (H). | 486.9 | E | |
| I-2015 | 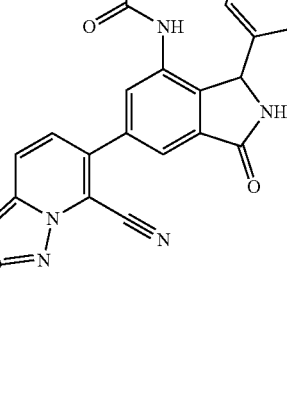 | [2H]c1nc2ccc(-c3cc4C(=O)NC(c4c(NC(=O)c4cc(F)cc(c4C(F)(F)F)c3)c3cc(F)ccc3Cl)c(C#N)n2n1 | 1H NMR (400 MHz, DMSO-d6) 10.72 (d, J = 2.1 Hz, 1H), 9.35 (s, 1H), 8.34 (s, 1H), 8.08 (s, 1H), 7.96 (s, 2H), 7.85 (dd, J = 9.3, 1.9 Hz, 1H) , 7.69 (s, 1H), 7.38 (s, 1H), 7.22 (s, 1H), 7.14 (s, 1H), 6.64-7.08 (d, J = 9.3 Hz , 1H), 6.10 (br s, 1H). | 610 | A | |
| I-2016 | 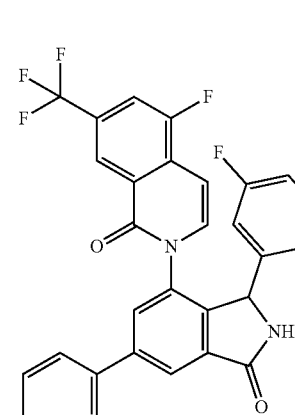 | Fc1ccc(Cl)c(c1)C1NC(=O)c2cc(cc(c12)-n1ccc2c(F)cc(cc2c1=O)C(F)(F)F)-c1ccc2ncnn2c1 | 1H NMR (400 MHz, DMSO-d6) 9.57 (d, J = 25.7 Hz, 1H), 9.37 (s, 1H), 8.58 (d, J = 4.1 Hz, 1H), 8.36 (d, J = 10.4 Hz, 2H), 8.29-8.07 (m, 3H), 7.99 (dd, J = 9.4, 6.2 Hz, 1H), 7.87 (s, 1H), 7.11 (dd, J = 134.1, 73.8 Hz, 3H), 6.52 (d, J = 7.7 Hz, 1H), 6.08-5.69 (m, 1H). | 608.1 | D | |

| Ex. No. | Structure | SMILES | ¹H NMR | MS | ADP-Glo IC$_{50}$ | MCF 10A IC$_{50}$ |
|---|---|---|---|---|---|---|
| I-2017 | 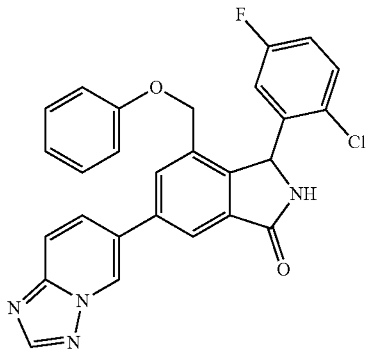 [SMILES: O=C1NC(c2cc(F)ccc2Cl)c2c(COc3ccccc3)cc(-c3ccc4ncnn4c3)cc21] | Fc1ccc(Cl)c(c1)C1NC(=O)c2cc(cc(COc3ccccc3)c12)-c1ccc2ncnn2c1 | 1H NMR (400 MHz, DMSO-d6) 9.49 (s, 1H), 9.29 (s, 1H), 8.57 (s, 1H), 8.22-8.12 (m, 3H), 7.98 (d, J = 9.3 Hz, 1H), 7.46 (s, 1H), 7.24 (t, J = 7.8 Hz, 2H), 7.19 (s, 1H), 6.92 (t, J = 7.3 Hz, 1H), 6.81 (d, J = 8.0 Hz, 2H), 6.57 (s, 1H), 6.27 (s, 1H), 4.91 (d, J = 11.4 Hz, 1H), 4.83 (s, 1H). | 485.15 | E | |
| I-2018 | 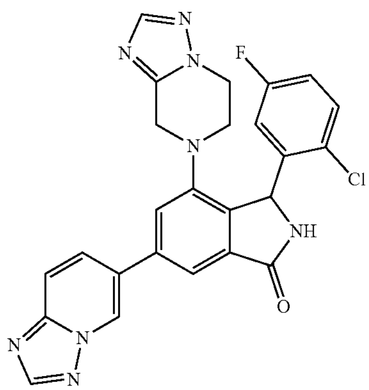 [SMILES: O=C1NC(c2cc(F)ccc2Cl)c2c1cc(-c1ccc3ncnn3c1)cc2N1CCn2ncnc2C1] | Fc1ccc(Cl)c(c1)C1NC(=O)c2cc(cc(N3CCn4ncnc4C3)c12)-c1ccc2ncnn2c1 | NMR (400 MHz, DMSO-d6) 9.57 (dd, J = 1.7, 0.8 Hz, 1H), 9.32-9.22 (m, 1H), 8.57 (s, 1H), 8.20 (dd, J = 9.3, 1.8 Hz, 1H), 7.97 (dd, J = 9.3, 0.6 Hz, 1H), 7.92 (s, 1H), 7.90 (d, J = 1.3 Hz, 1H), 7.81 (d, J = 1.3 Hz, 1H), 7.81 (d, J = 1.3 Hz, 1H), 7.44 (dd, J = 8.8, 5.1 Hz, 1H), 7.21-7.15 (m, 1H), 6.85 (br s, 1H), 6.30 (s, 1H), 4.56 (d, J = 15.9 Hz, 1H), 4.09 (d, J = 15.9 Hz, 1H), 3.93-3.81 (m, 1H), 3.79-3.64 (m, 1H), 3.39-3.27 (m, 1H). | 501 | E | |
| I-2019 | 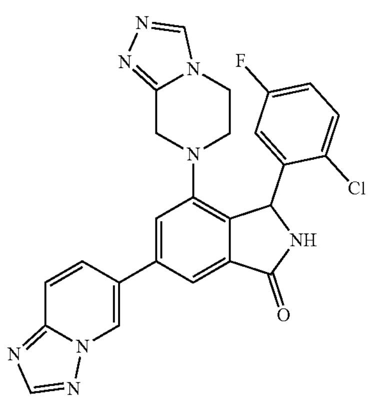 [SMILES: O=C1NC(c2cc(F)ccc2Cl)c2c1cc(-c1ccc3ncnn3c1)cc2N1CCn2cnnc2C1] | Fc1ccc(Cl)c(c1)C1NC(=O)c2cc(cc(N3CCn4cnnc4C3)c12)-c1ccc2ncnn2c1 | NMR (400 MHz, DMSO-d6) 9.59-9.56 (m, 1H), 9.25 (s, 1H), 8.57 (s, 1H), 8.41 (s, 1H), 8.20 (dd, J = 9.3, 1.8 Hz, 1H), 7.99-7.95 (m, 1H), 7.89 (d, J = 1.3 Hz, 1H), 7.79 (d, J = 1.1 Hz, 1H), 7.44 (dd, J = 8.7, 5.4 Hz, 1H), 7.19 (ddd, J = 11.0, 6.8, 2.3 Hz, 1H), 6.75 (br s, 1H), 6.30 (s, 1H), 4.58 (d, J = 15.4 Hz, 1H), 4.15 (d, J = 15.5 Hz, 1H), 3.81-3.74 (m, 1H), 3.72-3.65 (m, 1H), 3.64-3.56 (m, 1H), 3.27-3.20 (submerged m, 1H). | 501 | E | |
| I-2020 | 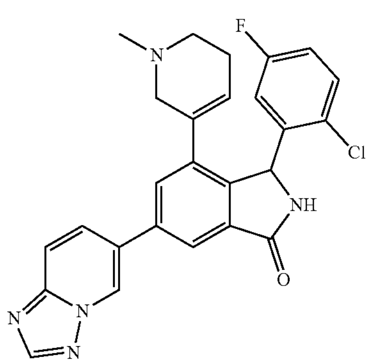 [SMILES: CN1CCC=C(c2cc(-c3ccc4ncnn4c3)cc3c2C(c2cc(F)ccc2Cl)NC3=O)C1] | CN1CCC=C(C1)c1cc(cc2C(=O)NC(c12)c1cc(F)ccc1Cl)-c1ccc2ncnn2c1 | NMR (400 MHz, DMSO-d6) 9.59-9.47 (m, 1H), 9.25 (br s, 1H), 8.56 (s, 1H), 8.19 (d, J = 9.3 Hz, 1H), 8.06 (s, 1H), 8.02-7.84 (m, 1H), 7.70-7.42 (m, 1H), 7.24 (td, J = 8.4, 2.8 Hz, 1H), 6.41 (br s, 1H), 6.29 (br s, 1H), 5.86 (s, 1H), 3.42 (br d, J = 16.1 Hz, 1H), 2.24-2.08 (m, 2H), 2.04 (s, 3H), 2.04-1.93 (m, 1H), 1.90-1.72 (m, 1H), 1.63-1.47 (m, 1H). | 474 | E | |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-2021 | 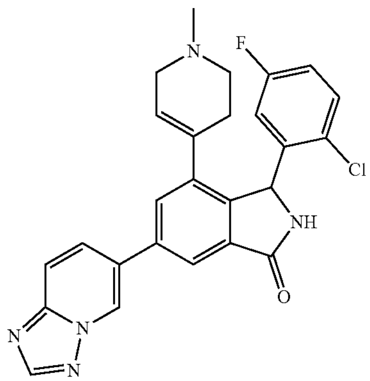 [SMILES: CN1CC=C(c2cc(-c3ccc4ncnn4c3)cc3c2C(c2cc(F)ccc2Cl)NC3=O)CC1] | CN1CCC(=CC1)c1cc(cc2C(=O)NC(c12)c1cc(F)ccc1Cl)-c1ccc2ncnn2c1 | | 474 | E | |
| I-2022 | 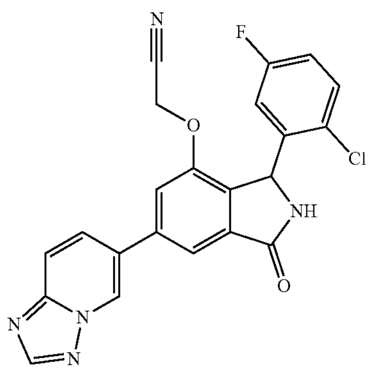 [SMILES: N#CCOc1cc(-c2ccc3ncnn3c2)cc2c1C(c1cc(F)ccc1Cl)NC2=O] | Fc1ccc(Cl)c(c1)C1NC(=O)c2cc(cc(OCC#N)c12)-c1ccc2ncnn2c1 | NMR (400 MHz, DMSO-d6) 9.52 (br, s, 1H), 9.25 (br, s, 1H), 8.59 (s, 1H), 8.19 (dd, J = 9.3, 1.9 Hz, 1H), 8.00 (dd, J = 9.3, 0.8 Hz, 1H), 7.88 (d, J = 1.2 Hz, 1H), 7.79 (d, J = 1.2 Hz, 1H), 7.57 (dd, J = 8.8, 5.2 Hz, 1H), 7.28-7.22 (m, 1H), 6.87 (br, s, 1H), 6.10 (s, 1H), 5.27 (s, 2H). | 434 | E | |
| I-2023 | 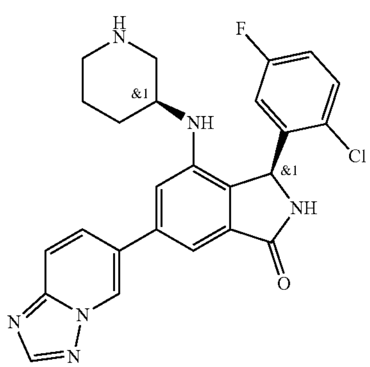 [SMILES: O=C1N[C@H](c2cc(F)ccc2Cl)c2c(N[C@H]3CCCNC3)cc(-c3ccc4ncnn4c3)cc21] | Fc1ccc(Cl)c(c1)[C@@H]1NC(=O)c2cc(cc(N[C@@H]3CCCNC3)c12)-c1ccc2ncnn2c1 | NMR (400 MHz, DMSO-d6) 9.43 (s, 1H), 9.06 (s, 1H), 8.55 (s, 1H), 8.11 (d, J = 9.1 Hz, 1H), 7.92 (d, J = 9.2 Hz, 1H), 7.56 (dd, J = 8.3, 5.0 Hz, 1H), 7.38 (s, 1H), 7.32-7.22 (m, 2H), 6.87 (br s, 1H), 5.96 (s, 1H), 4.54 (d, J = 7.7 Hz, 1H), 3.93-3.70 (m, 1H), 3.28-3.07 (m, 1H), 2.99-2.74 (m, 1H), 2.72-2.53 (m, 1H), 1.61-1.17 (m, 4H). | 477 | E | |
| I-2024 | 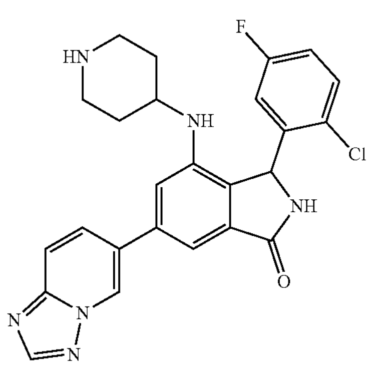 [SMILES: O=C1NC(c2cc(F)ccc2Cl)c2c(NC3CCNCC3)cc(-c3ccc4ncnn4c3)cc21] | Fc1ccc(Cl)c(c1)C1NC(=O)c2cc(cc(NC3CCNCC3)c12)-c1ccc2ncnn2c1 | NMR (400 MHz, DMSO-d6) 9.41 (s, 1H), 9.06 (s, 1H), 8.57 (s, 1H), 8.09 (d, J = 8.9 Hz, 1H), 7.93 (d, J = 8.7 Hz, 1H), 7.67-7.51 (m, 1H), 7.39 (s, 1H), 7.34-7.19 (m, 2H), 6.82 (br s, 1H), 5.97 (s, 1H), 4.55-4.24 (m, 1H), 3.92-3.55 (m, 1H), 3.49-2.54 (m, 3H), 1.77-0.99 (m, 4H). | 477 | E | |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-2025 | 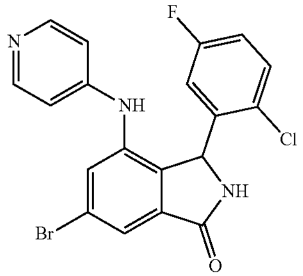 [SMILES: O=C1NC(c2cc(F)ccc2Cl)c2c(Nc3ccncc3)cc(Br)cc21] | Fc1ccc(Cl)c(c1)C1NC(=O)c2cc(Br)cc(Nc3ccncc3)c12 | 1H NMR (400 MHz, DMS)-d6) 9.23 (s, 1H), 8.47 (br. s, 1H), 8.07 (br. s, 2H), 7.68 (d, J = 1.6 Hz, 1H), 7.57 (d, J = 1.6 Hz, 1H), 7.28 (dd, J = 8.8, 5.2 Hz, 1H), 7.05 (td, J = 8.4, 3.1 Hz, 1H), 6.62 (br. s, 1H), 6.45 (d, J = 4.2 Hz, 2H), 5.86 (s, 1H) | 432 | E | |
| I-2026 | 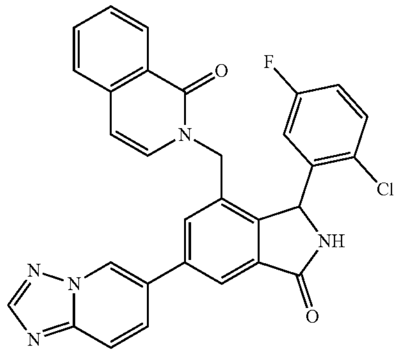 [SMILES: O=C1NC(c2cc(F)ccc2Cl)c2c(Cn3ccc4ccccc4c3=O)cc(-c3ccc4ncnn4c3)cc21] | Fc1ccc(Cl)c(c1)C1NC(=O)c2cc(cc(Cn3cccc4cccc4c3=O)c12)-c1ccc2ncnn2c1 | 1H NMR (400 MHz, DMSO-d6) 9.38 (s, 1H), 8.54 (s, 1H), 8.14 (d, J = 8.2 Hz, 1H), 8.11 (d, J = 1.1 Hz, 1H), 7.99 (dd, J = 9.3, 1.5 Hz, 1H), 7.92 (dd, J = 9.3, 0.6 Hz, 1H), 7.75 (br. s, 1H), 7.72-7.65 (m, 1H), 7.65-7.58 (m, 1H), 7.59-7.51 (m, 1H), 7.52-7.44 (m, 1H), 7.39 (br. s, 1H), 7.12 (br. s, 1H), 6.60 (d, J = 7.4 Hz, 1H), 6.56-6.27 (m, 1H), 5.54 (m, 2H), 4.94 (dd, J = 34.6, 15.0 Hz, 2H) | 536.2 | E | |
| I-2027 | 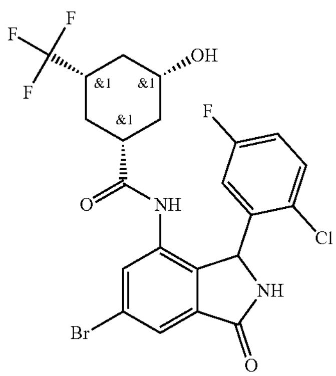 [SMILES: O=C1NC(c2cc(F)ccc2Cl)c2c(NC(=O)[C@H]3C[C@@H](O)C[C@@H](C(F)(F)F)C3)cc(Br)cc21] | O[C@@H]1C[C@@H](C[C@@H](C1)C(F)(F)F)C(=O)Nc1cc(Br)cc2C(=O)NC(c12)c1cc(F)ccc1Cl | 1H-NMR (400 MHz, DMSO-d6) as a ca. 1:1 mixture of diastereomers, 9.94 (br. s, 1H), 9.83 (br. s, 1H), 9.25 (br. s, 2H), 7.71 (s, 2H), 7.61 (d, J = 1.4 Hz, 1H), 7.55 (d, J = 0.9 Hz, 1H), 7.49-7.41 (m, 2H), 7.22-7.16 (m, 2H), 6.51 (br. s, 2H), 6.01 (br. s, 2H), 4.90-4.87 (m, 2H), 3.47-3.38 (m, 2H), 2.40-2.29 (m, 3H), 2.24-2.13 (m, 2H), 1.96-1.89 (m, 1H), 1.77-1.69 (m, 1H), 1.62-1.54 (m, 1H), 1.54-1.46 (m, 1H), 1.10-0.80 (m, 6H). | 549.1 | E | |
| I-2028 | 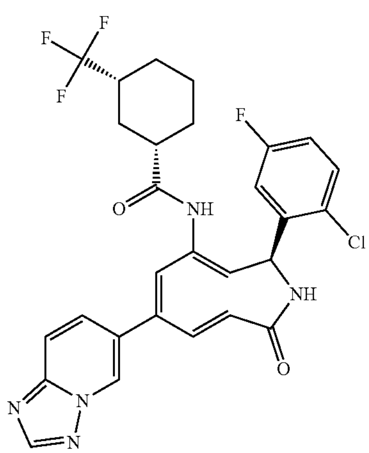 [SMILES: O=C1/C=C/C(c2ccc3ncnn3c2)=C\C(NC(=O)[C@H]2CCC[C@@H](C(F)(F)F)C2)=C\[C@@H](c2cc(F)ccc2Cl)N1] | Fc1ccc(Cl)c(c1)[C@H]1NC(=O)c2cc(cc(NC(=O)[C@H]3CCC[C@H](C3)C(F)(F)F)c12)-c1ccc2ncnn2c1 | | 588.5 | D | |

TABLE 2-continued
Representative Compounds of the Invention with Bioactivity Data.
| Ex. No. | Structure | SMILES | ¹H NMR | MS | ADP-Glo IC$_{50}$ | MCF 10A IC$_{50}$ |
|---|---|---|---|---|---|---|
| I-2033 | 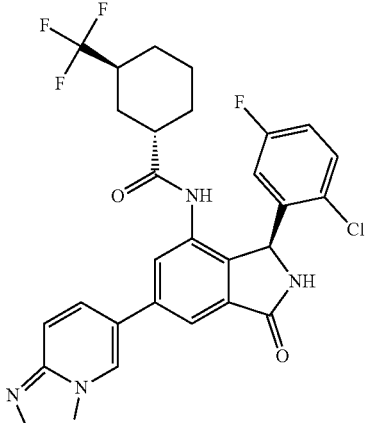 | Fc1ccc(Cl)c(c1)[C@H]1NC(=O)c2cc(cc(NC(=O)[C@H]3CCC[C@@H](C3)C(F)(F)F)c12)-c1ccc2ncnn2c1 | | 588.5 | D | |
| I-2034 | 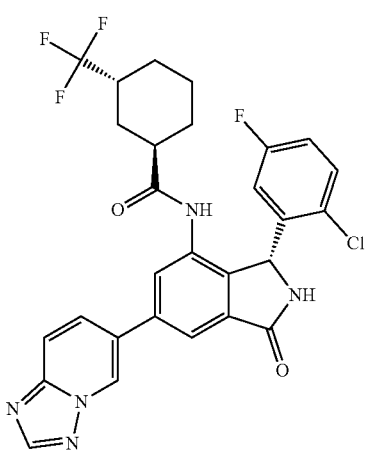 [SMILES: O=C1N[C@@H](c2cc(F)ccc2Cl)c2c(NC(=O)[C@@H]3CCC[C@@H](C(F)(F)F)C3)cc(-c3ccc4ncnn4c3)cc21] | Fc1ccc(Cl)c(c1)[C@@H]1NC(=O)c2cc(cc(NC(=O)[C@@H]3CCC[C@H](C3)C(F)(F)F)c12)-c1ccc2ncnn2c1 | | 588.5 | A | A |
| I-2035 | 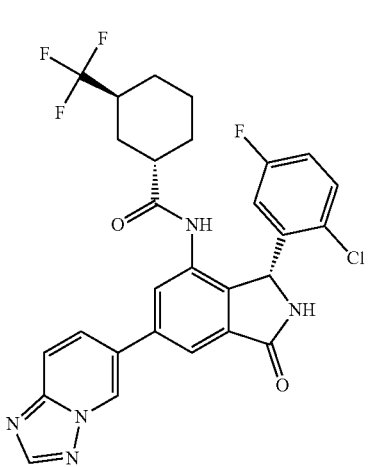 [SMILES: O=C1N[C@@H](c2cc(F)ccc2Cl)c2c(NC(=O)[C@H]3CCC[C@H](C(F)(F)F)C3)cc(-c3ccc4ncnn4c3)cc21] | Fc1ccc(Cl)c(c1)[C@@H]1NC(=O)c2cc(cc(NC(=O)[C@H]3CCC[C@@H](C3)C(F)(F)F)c12)-c1ccc2ncnn2c1 | | 588.5 | A | |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-2036 | 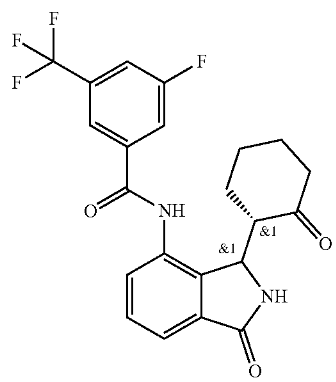 [SMILES: O=C(Nc1cccc2c1C([C@@H]1CCCCC1=O)NC2=O)c1cc(F)cc(C(F)(F)F)c1] | [H][C@]1(CCCCC1=O)[C@@H]1NC(=O)c2cccc(NC(=O)c3cc(F)cc(C(F)(F)F)c12 | (400 MHz, DMSO-d6) 10.60 (s, 1H), 8.24 (s, 1H), 8.13 (s, 1H), 8.09 (d, J = 9.1 Hz, 1H), 8.01 (d, J = 8.4 Hz, 1H), 7.62 (dd, J = 7.4, 1.4 Hz, 1H), 7.60-7.51 (m, 2H), 5.43 (s, 1H), 2.93 (dd, J = 11.8, 5.1 Hz, 1H), 2.35-2.20 (m, 2H), 1.95-1.83 (m, 1H), 1.70-1.60 (m, 1H), 1.53-1.38 (m, 2H), 1.27-1.11 (m, 1H), 1.07-0.97 (m, 1H). | 435.3 | E | |
| I-2037 | 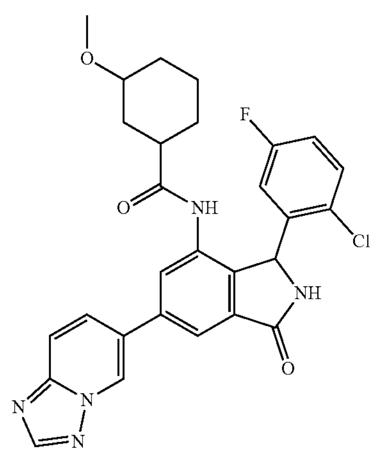 [SMILES: COC1CCCC(C(=O)Nc2cc(-c3ccc4ncnn4c3)cc3c2C(c2cc(F)ccc2Cl)NC3=O)C1] | COC1CCCC(C1)C(=O)Nc1cc(c2C(=O)NC(c12)c1cc(F)ccc1Cl)-c1ccc2ncnn2c1 | NMR (400 MHz, DMSO-d6) 9.82 (s, 1H), 9.45-9.41 (m, , 1H), 9.20 (s, 1H), 8.57 (s, 1H), 8.09 (dd, J = 9.3, 1.8 Hz, 1H), 8.01-7.93 (m, 2H), 7.80 (dd, J = 6.6, 1.6 Hz, 1H), 7.56-7.48 (m, 1H), 7.31-7.16 (m, 1H), 6.73 (br s, 1H), 6.12 (s, 1H), 3.21 (s, 3H), 3.08-2.94 (m, 1H), 2.16-2.03 (m, 1H), 1.99-1.80 (m, 1.5H), 1.76-1.59 (m, 1.5H), 1.49-0.83 (m, 5H). 1:1 mixture of diastereomers (one reported); approx. | 534.2 | E | |
| I-2038 | 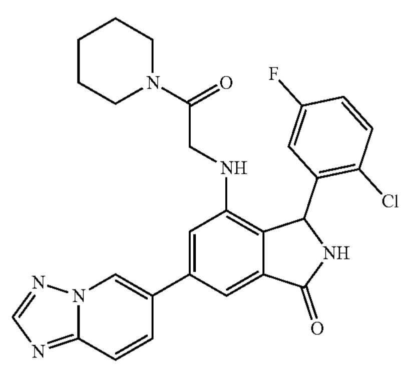 [SMILES: O=C1NC(c2cc(F)ccc2Cl)c2c(NCC(=O)N3CCCCC3)cc(-c3ccc4ncnn4c3)cc21] | Fc1ccc(Cl)c(c1)C1NC(=O)c2cc(cc(NCC(=O)N3CCCCC3)c12)-c1ccc2ncnn2c1 | 1H NMR (400 MHz, DMSO-d6) 9.28 (s, 1H), 8.54 (s, 1H), 8.00 (d, J = 9.2, 1.5 Hz, 1H), 7.94 (d, J = 9.2 Hz, 1H), 7.68 (dd, J = 10.3, 5.1 Hz, 1H), 7.50-7.13 (m, 4H), 6.49 (d, J = 7.6 Hz, 1H), 6.07 (br. s, 1H), 5.05-4.92 (m, 2H), 4.94 (s, 1H), 4.63 (d, J = 17.1 Hz, 1H), 3.62-3.47 (m, 2H), 3.27-3.18 (submerged m, 2H), 1.62-1.38 (m, 6H) | 519.2 | E | |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-2039 | 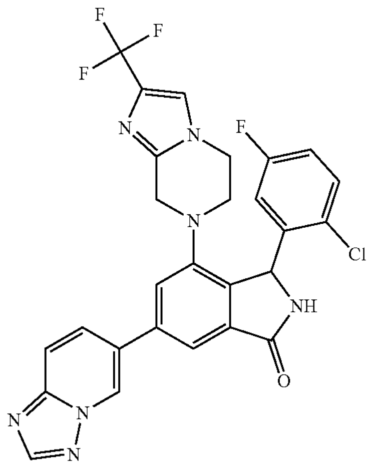 [SMILES: O=C1NC(c2cc(F)ccc2Cl)c2c1cc(-c1ccc3ncnn3c1)cc2N1CCn2cc(C(F)(F)F)nc2C1] | Fc1ccc(Cl)c(c1)C1NC(=O)c2cc(cc(N3CCn4cc(nc4C3)C(F)(F)F)c12)-c1ccc2ncnn2c1 | NMR (400 MHz, DMSO-d6) 9.55 (dd, J = 1.8, 0.9 Hz, 1H), 9.23 (br s, 1H), 8.57 (s, 1H), 8.19 (dd, J = 9.3, 1.8 Hz, 1H), 7.96 (dd, J = 9.3, 0.7 Hz, 1H), 7.88 (d, J = 1.4 Hz, 1H), 7.76 (d, J = 1.3 Hz, 1H), 7.70 (d, J = 1.3 Hz, 1H), 7.43 (dd, J = 8.8, 5.2 Hz, 1H), 7.18 (ddd, J = 8.8, 8.0, 3.1 Hz, 1H), 6.72 (br s, 1H), 6.29 (br s, 1H), 4.48 (d, J = 15.6 Hz, 1H), 4.05 (d, J = 15.5 Hz, 1H), 3.77 (dd, J = 13.9, 6.4 Hz, 1H), 3.69-3.59 (m, 2H), 3.30-3.23 (submerged m, 1H). | 568 | E | |
| I-2040 | 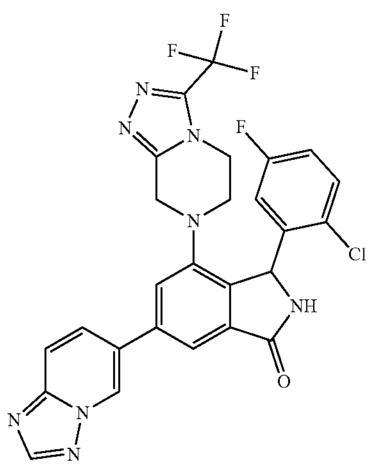 [SMILES: O=C1NC(c2cc(F)ccc2Cl)c2c1cc(-c1ccc3ncnn3c1)cc2N1CCn2c(nnc2C(F)(F)F)C1] | Fc1ccc(Cl)c(c1)C1NC(=O)c2cc(cc(N3CCn4c(C3)nnc4C(F)(F)F)c12)-c1ccc2ncnn2c1 | NMR (400 MHz, DMSO-d6) 9.57 (dd, J = 1.7, 0.8 Hz, 1H), 9.23 (br s, 1H), 8.57 (s, 1H), 8.20 (dd, J = 9.3, 1.8 Hz, 1H), 7.97 (dd, J = 9.3, 0.7 Hz, 1H), 7.93 (d, J = 1.4 Hz, 1H), 7.83 (d, J = 1.4 Hz, 1H), 7.37 (dd, J = 8.9, 5.1 Hz, 1H), 7.19-7.13 (m, 1H), 6.76 (br s, 1H), 6.27 (br s, 1H), 4.68 (d, J = 15.9 Hz, 1H), 4.17 (d, J = 15.9 Hz, 1H), 4.02-3.90 (m, 1H), 3.64 (q, J = 6.5 Hz, 2H), 3.40-3.34 (submerged m, 1H). | 569 | E | |
| I-2041 | 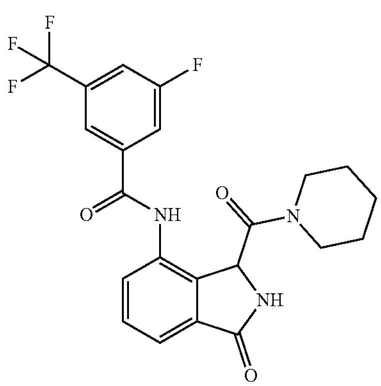 [SMILES: O=C(Nc1cccc2c1C(C(=O)N1CCCCC1)NC2=O)c1cc(F)cc(C(F)(F)F)c1] | Fc1cc(cc(c1)C(F)(F)F)C(=O)Nc1cccc2C(=O)NC(C(=O)N3CCCCC3)c12 | NMR (400 MHz, DMSO-d6) 10.77 (br. s, 1H), 9.08 (s, 1H), 8.14 (s, 1H), 8.08 (br. d, J = 9.2 Hz, 1H), 8.04 (br. d, J = 8.5 Hz, 1H), 7.62-7.52 (m, 3H), 5.74 (s, 1H), 3.52-3.43 (m, 1H), 3.37-3.28 (submerged m, 2H), 3.13-3.04 (m, 1H), 1.50-1.38 (m, 2H), 1.35-1.24 (m, 3H), 0.91-0.80 (m, 1H). | 450.2 | E | |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-2042 | 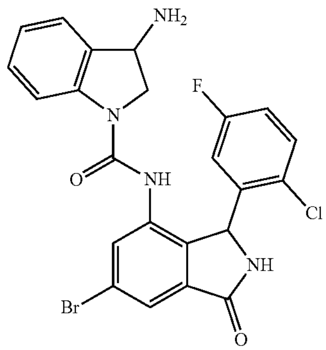 [SMILES: NC1CN(C(=O)Nc2cc(Br)cc3c2C(c2cc(F)ccc2Cl)NC3=O)c2ccccc21] | NC1CN(C(=O)Nc2cc(Br)cc3C(=O)NC(c23)c2cc(F)ccc2Cl)c2ccccc12 | 1H NMR (400 MHz, DMSO-d6) 9.21 (s, 1H), 8.70 (d, J = 51.2 Hz, 1H), 7.78-7.56 (m, 3H), 7.43-7.33 (m, 2H), 7.17 (dddt, J = 16.9, 11.7, 8.6, 5.4 Hz, 2H), 7.05-6.95 (m, 1H), 6.70 (s, 1H), 6.08-5.85 (m, 1H), 4.46 (t, J = 7.3 Hz, 1H), 4.00 (dd, J = 10.8, 9.0 Hz, 1H), 3.76-3.64 (m, 1H), 3.52 (dd, J = 10.9, 5.8 Hz, 1H), 3.07-2.90 (m, 1H). | 515.05 | D | |
| I-2043 | 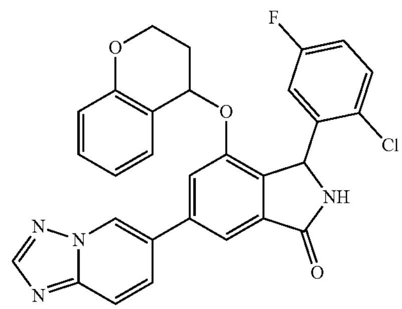 [SMILES: O=C1NC(c2cc(F)ccc2Cl)c2c(OC3CCOc4ccccc43)cc(-c3ccc4ncnn4c3)cc21] | Fc1ccc(Cl)c(c1)C1NC(=O)c2cc(cc(OC3CCOc4ccccc34)c12)-c1ccc2ncnn2c1 | NMR (400 MHz, DMSO-d6) 9.56 (br, s, 1H), 9.13 (s, 1H), 8.58 (s, 1H), 8.23-8.18 (m, 1H), 7.97 (dd, J = 9.3, 0.7 Hz, 1H), 7.91 (d, J = 15.1 Hz, 1H), 7.75 (dd, J = 6.9, 1.2 Hz, 1H), 7.41 (dd, J = 8.9, 5.2 Hz, 0.6H), 7.29 (dd, J = 7.6, 1.6 Hz, 0.6H), 7.27-7.20 (m, 1.2H), 7.15 (ddd, J = 9.8, 3.9, 1.6 Hz, 1H), 7.10-7.04 (m, 0.4H), 6.90 (td, J = 7.5, 1.1 Hz, 0.6H), 6.83-6.79 (m, 1H), 6.77 (submerged s, 1H), 6.73 (dd, J = 8.2, 0.9 Hz, 1H), 6.61 (td, J = 7.4, 1.1 Hz, 0.4H), 6.45 (dd, J = 7.6, 1.5 Hz, 0.4H), 5.96 (s, 0.4H), 5.87 (s, 0.6H), 5.84 (t, J = 2.9 Hz, 0.6H), 5.77 (m, 0.4H), 4.21 (m, 1H), 3.86 (m, 0.6H), 3.03 (m, 0.4H), 2.22 (m, 1H), 1.93 (m, 0.6H), 1.72 (m, 0.4H) | 527 | E | |
| I-2044 | 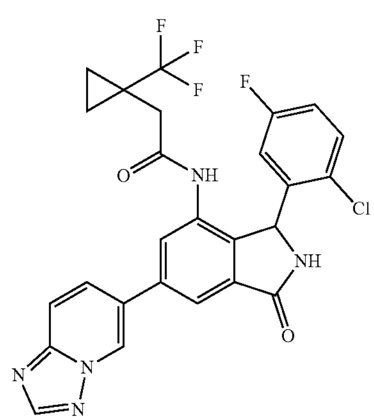 [SMILES: O=C(CC1(C(F)(F)F)CC1)Nc1cc(-c2ccc3ncnn3c2)cc2c1C(c1cc(F)ccc1Cl)NC2=O] | Fc1ccc(Cl)c(c1)C1NC(=O)c2cc(cc(NC(=O)CC3(CC3)C(F)(F)F)c12)-c1ccc2ncnn2c1 | 1H-NMR (400 MHz, DMSO-d6) 9.88 (br. s, 1H), 9.43 (dd, J = 1.7, 0.8 Hz, 1H), 9.20 (br. s, 1H), 8.57 (s, 1H), 8.08 (dd, J = 9.3, 1.8 Hz, 1H), 8.01 (d, J = 1.5 Hz, 1H), 7.97 (dd, J = 9.3, 0.8 Hz, 1H), 7.89 (d, J = 1.5 Hz, 1H), 7.52 (dd, J = 8.0, 4.8 Hz, 1H), 7.24 (ddd, J = 8.7, 8.1, 3.1 Hz, 1H), 6.66 (br. s, 1H), 6.11 (s, 1H), 2.49-2.46 (m, 1H), 2.29 (d, J = 15.3 Hz, 1H), 0.93-0.88 (m, 1H), 0.85-0.78 (m, 3H). Multiplet 2.49-2.46 is a doublet partially obscured by the DMSO peak. | 544.3 | D | |

TABLE 2-continued

Representative Compounds of the Invention with Bioactivity Data.

| Ex. No. | Structure | SMILES | $^1$H NMR | MS | ADP-Glo IC$_{50}$ | MCF 10A IC$_{50}$ |
|---|---|---|---|---|---|---|
| I-2045 | 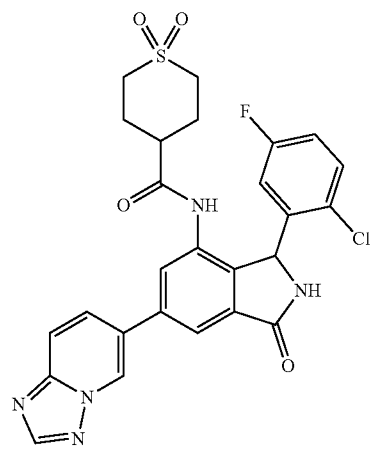 [SMILES: O=C1NC(c2cc(F)ccc2Cl)c2c(NC(=O)C3CCS(=O)(=O)CC3)cc(-c3ccc4ncnn4c3)cc21] | Fc1ccc(Cl)c(c1)C1NC(=O)c2cc(cc(NC(=O)C3CCS(=O)(=O)CC3)c12)-c1ccc2ncnn2c1 | NMR (400 MHz, DMSO-d6) 10.17-10.01 (m, 1H), 9.44 (d, J = 0.7 Hz, 1H), 9.24 (br s, 1H), 8.57 (s, 1H), 8.10 (dd, J = 9.3, 1.8 Hz, 1H), 8.03 (d, J = 1.5 Hz, 1H), 7.98 (d, J = 9.3 Hz, 1H), 7.82 (s, 1H), 7.58-7.46 (m, 1H), 7.25 (td, J = 8.4, 3.1 Hz, 1H), 6.56 (br s, 1H), 6.16 (br s, 1H), 3.20-3.07 (m, 2H), 3.07-2.95 (m, 2H), 2.48-2.38 (m, 1H), 1.96-1.74 (m, 3H), 1.73-1.62 (m, 1H). | 554 | D | |
| I-2046 | 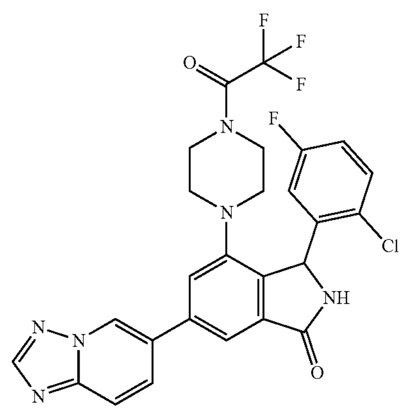 [SMILES: O=C1NC(c2cc(F)ccc2Cl)c2c1cc(-c1ccc3ncnn3c1)cc2N1CCN(C(=O)C(F)(F)F)CC1] | Fc1ccc(Cl)c(c1)C1NC(=O)c2cc(cc(N3CCN(CC3)C(=O)C(F)(F)F)c12)-c1ccc2ncnn2c1 | 1H NMR (400 MHz, DMSO-d6) 9.51 (dd, J = 1.7, 0.8 Hz, 1H), 9.24 (s, 1H), 8.56 (s, 1H), 8.17 (dd, J = 9.3, 1.8 Hz, 1H), 7.95 (dd, J = 9.3, 0.6 Hz, 1H), 7.87 (d, J = 1.4 Hz, 1H), 7.72 (d, J = 1.3 Hz, 1H), 7.58 (dd, J = 8.3, 5.1 Hz, 1H), 7.27 (ddd, J = 8.9, 8.0, 3.1 Hz, 1H), 6.79 (br. s, 1H), 6.19 (s, 1H), 3.51-3.37 (m, 3H), 3.29-3.14 (m, 3H), 2.89-2.77 (m, 1H), 2.79-2.68 (m, 1H) | 559.2 | E | |
| I-2047 | 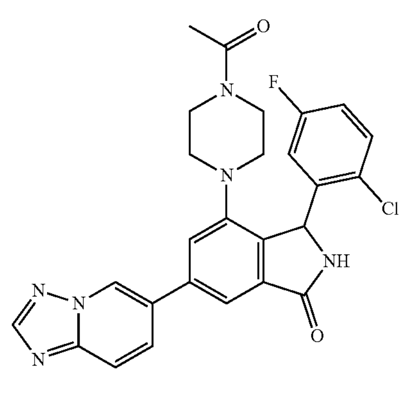 [SMILES: CC(=O)N1CCN(c2cc(-c3ccc4ncnn4c3)cc3c2C(c2cc(F)ccc2Cl)NC3=O)CC1] | CC(=O)N1CCN(CC1)c1cc(cc2C(=O)NC(c12)c1cc(F)ccc1Cl)-c1ccc2ncnn2c1 | 1H NMR (400 MHz, DMSO-d6) 9.50 (d, J = 0.8 Hz, 1H), 9.24 (s, 1H), 8.56 (s, 1H), 8.16 (dd, J = 9.3, 1.8 Hz, 1H), 7.95 (d, J = 9.3 Hz, 1H), 7.82 (d, J = 1.4 Hz, 1H), 7.62 (d, J = 1.4 Hz, 1H), 7.58 (dd, J = 8.5, 5.2 Hz, 1H), 7.27 (ddd, J = 8.71, 7.03, 3.10 Hz, 1H ), 6.74 (br. s, 1H), 6.20 (s, 1H), 3.29-3.04 (m, 6H), 2.85-2.68 (m, 1H), 2.71-2.57 (m, 1H), 1.98 (s, 3H); multiplet at 3.29-3.04 6H overlaps with residual water peak | 505.2 | E | |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-2048 | 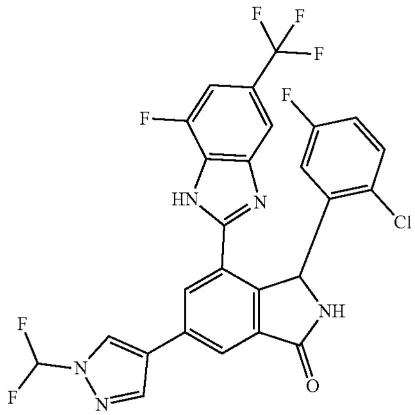 [SMILES: O=C1NC(c2cc(F)ccc2Cl)c2c1cc(-c1cnn(C(F)F)c1)cc2-c1nc2cc(C(F)(F)F)cc(F)c2[nH]1] | FC(F)n1cc(cn1)-c1cc2C(=O)NC(c2c(c1)-c1nc2cc(cc(F)c2[nH]1)C(F)(F)F)c1cc(F)ccc1Cl | 1H NMR (400 MHz, DMSO-d6) 9.31 (s, 1H), 8.98 (s, 1H), 8.71 (s, 1H), 8.52 (s, 1H), 8.23 (s, 1H), 8.07-7.77 (m, 1H), 7.63 (s, 1H), 7.37 (s, 1H), 7.28 (d, J = 10.6 Hz, 1H), 6.95 (td, J = 8.4, 3.1 Hz, 1H), 6.70 (s, 1H), 1.23 (s, 1H). | 580 | D | |
| I-2049 | 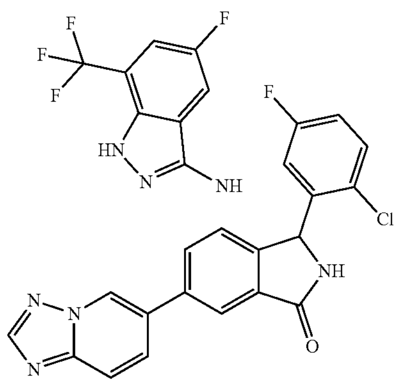 | Fc1ccc(Cl)c(c1)C1NC(=O)c2cc(cc(Nc3n[nH]c4c(cc(F)cc34)C(F)(F)F)c12)-c1ccc2ncnn2c1 | 1H NMR (400 MHz, DMSO-d6) 12.89 (s, 1H), 9.41 (d, J = 1.7 Hz, 1H), 9.11 (s, 1H), 8.59 (d, J = 6.7 Hz, 2H), 8.10 (dd, J = 9.3, 1.8 Hz, 1H), 8.05-7.96 (m, 2H), 7.78 (d, J = 1.6 Hz, 1H), 7.71 (d, J = 8.3 Hz, 1H), 7.40 (d, J = 8.2 Hz, 1H), 7.19 (dd, J = 8.8, 5.2 Hz, 1H), 7.00 (td, J = 8.4, 3.1 Hz, 1H), 6.55 (s, 1H), 6.03 (s, 1H). | 596.15 | A | |
| I-2050 | 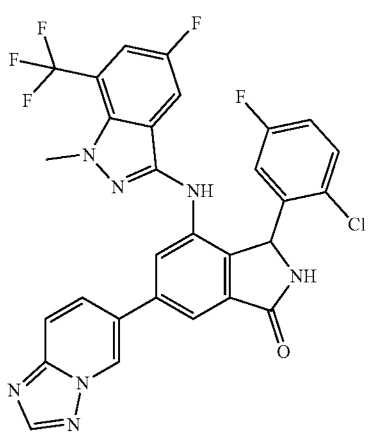 [SMILES: Cn1nc(Nc2cc(-c3ccc4ncnn4c3)cc3c2C(c2cc(F)ccc2Cl)NC3=O)c2cc(F)cc(C(F)(F)F)c21] | Cn1nc(Nc2cc(c3C(=O)NC(c23)c2cc(F)ccc2Cl)-c2ccc3ncnn3c2)c2cc(F)cc(c12)C(F)(F)F | 1H NMR (400 MHz, DMSO-d6) 9.37 (d, J = 1.4 Hz, 1H), 9.13 (s, 1H), 8.55 (s, 1H), 8.36 (s, 1H), 8.06-7.99 (m, 1H), 7.93 (d, J = 9.3 Hz, 1H), 7.76 (d, J = 1.5 Hz, 1H), 7.60 (d, J = 8.9 Hz, 1H), 7.45 (dd, J = 9.0, 5.2 Hz, 1H), 7.31 (s, 1H), 7.21 (td, J = 8.3, 3.1 Hz, 1H), 7.08 (d, J = 8.6 Hz, 1H), 6.64 (s, 1H), 5.61 (s, 1H), 3.65 (s, 3H). | 610.2 | C | |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-2051 | 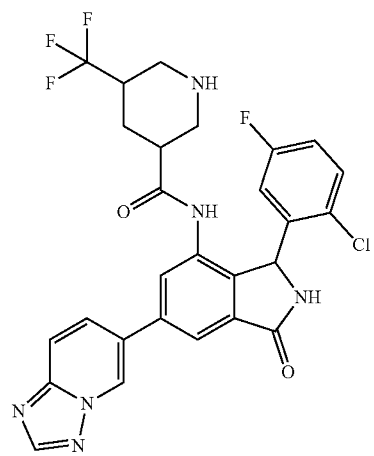 [SMILES: O=C1NC(c2cc(F)ccc2Cl)c2c(NC(=O)C3CNCC(C(F)(F)F)C3)cc(-c3ccc4ncnn4c3)cc21] | Fc1ccc(Cl)c(c1)C1NC(=O)c2cc(cc(NC(=O)C3CNCC(C3)C(F)(F)F)c12)-c1ccc2ncnn2c1 | 1H-NMR (400 MHz, DMSO-d6) as a ca. 3:2:1:1 mixture of diastereomers; for the major diastereomer 10.15 (br. s, 1H), 9.44 (s, 1H), 9.23 (br. s, 1H), 8.58 (s, 1H), 8.12-8.08 (m, 1H), 8.06-7.96 (m, 3H), 7.58-7.49 (m, 1H), 7.27-7.20 (m, 1H), 6.57 (br. s, 1H), 6.19 (br. s, 1H), 6.16 (br. s, 1H), 2.87-2.77 (m, 1H), 2.62-2.47 (m, 2H), 2.44-2.37 (m, 1H), 2.31-2.09 (m, 2H), 1.95-1.82 (m, 1H), 1.63-1.53 (m, 1H). | 573.3 | E | |
| I-2052 | 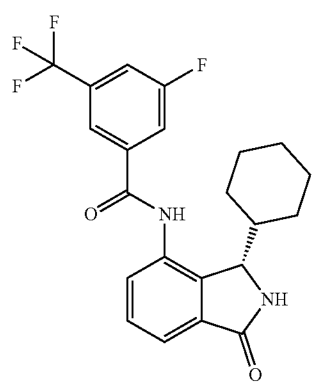 [SMILES: O=C(Nc1cccc2c1[C@H](C1CCCCC1)NC2=O)c1cc(F)cc(C(F)(F)F)c1] | Fc1cc(cc(c1)C(F)(F)F)C(=O)Nc1cccc2C(=O)N[C@@H](C3CCCCC3)c12 | NMR (400 MHz, DMSO-d6) 10.74 (br. s, 1H), 8.74 (s, 1H), 8.13 (s, 1H), 8.08 (br. d, J = 9.0 Hz, 1H), 8.04 (br. d, J = 8.5 Hz, 1H), 7.62-7.49 (m, 3H), 4.73 (d, J = 1.3 Hz, 1H), 1.90-1.80 (m, 1H), 1.73-1.64 (m, 1H), 1.59-1.50 (m, 3H), 1.39-1.27 (m, 1H), 1.06-0.86 (m, 3H), 0.79-0.61 (m, 2H). | 421.2 | D | |
| I-2053 | 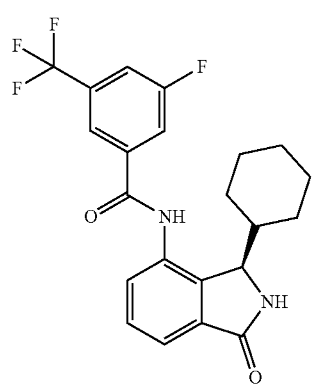 [SMILES: O=C(Nc1cccc2c1[C@@H](C1CCCCC1)NC2=O)c1cc(F)cc(C(F)(F)F)c1] | Fc1cc(cc(c1)C(F)(F)F)C(=O)Nc1cccc2C(=O)N[C@H](C3CCCCC3)c12 | NMR (400 MHz, DMSO-d6) 10.74 (br. s, 1H), 8.74 (s, 1H), 8.13 (s, 1H), 8.08 (br. d, J = 9.0 Hz, 1H), 8.04 (br. d, J = 8.5 Hz, 1H), 7.62-7.49 (m, 3H), 4.73 (d, J = 1.3 Hz, 1H), 1.90-1.80 (m, 1H), 1.73-1.64 (m, 1H), 1.59-1.50 (m, 3H), 1.39-1.27 (m, 1H), 1.06-0.86 (m, 3H), 0.79-0.61 (m, 2H). | 421.2 | E | |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-2054 | 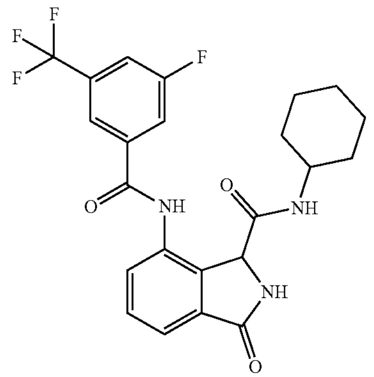 [SMILES: O=C(Nc1cccc2c1C(C(=O)NC1CCCCC1)NC2=O)c1cc(F)cc(C(F)(F)F)c1] | Fc1cc(cc(c1)C(F)(F)F)C(=O)Nc1cccc2C(=O)NC(C(=O)NC3CCCC3)c12 | NMR (400 MHz, DMSO-d6) 11.33 (s, 1H), 8.94 (d, J = 0.6 Hz, 1H), 8.27 (s, 1H), 8.21 (d, J = 8.0 Hz, 1H), 8.17 (br. d, J = 9.3 Hz, 1H), 8.12 (dd, J = 7.6, 1.0 Hz, 1H), 8.04 (br. d, J = 8.7 Hz, 1H), 7.57 (d, J = 7.7 Hz), 7.53 (dd, J = 7.5, 1.2 Hz), 5.43 (d, J = 0.9 Hz, 1H), 3.56-3.41 (m, 1H), 1.62-1.46 (m, 4H), 1.24-1.10 (m, 4H), 1.09-0.93 (m, 2H). 9:1 mixture of 2 rotamers. | 464.1 | E | |
| I-2055 | 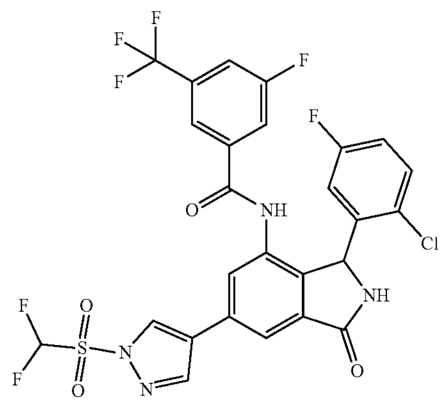 [SMILES: O=C(Nc1cc(-c2cnn(S(=O)(=O)C(F)F)c2)cc2c1C(c1cc(F)ccc1Cl)NC2=O)c1cc(F)cc(C(F)(F)F)c1] | FC(F)S(=O)=O)n1cc(cn1)-c1cc2C(=O)NC(c2c(NC(=O)c2cc(F)cc(c2)C(F)(F)F)c1)c1cc(F)ccc1Cl | (400 MHz, DMSO-d6) 10.59 (s, 1 H), 9.27 (s, 1 H), 9.22 (br s, 1 H), 8.90 (s, 1 H), 8.23 (s, 1 H), 7.97 (overlapped s, 1 H), 7.97 (overlapped d, J = 10.8 Hz, 1 H), 7.76 (d, J = 9.0 Hz, 1 H), 7.73 (s, 1 H), 7.73 (t, J = 51.4 Hz, 1 H), 7.32 (dd, J = 8.9, 5.2 Hz, 1 H), 7.10 (td, J = 8.5, 3.0 Hz, 1 H), 6.60 (br s, 1 H), 6.01 (br s, 1 H). | 645.2 | A | |
| I-2056 | 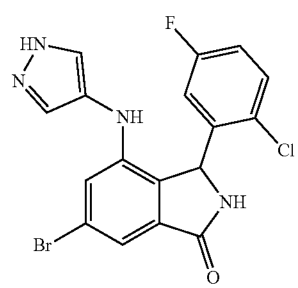 [SMILES: O=C1NC(c2cc(F)ccc2Cl)c2c(Nc3cn[nH]c3)cc(Br)cc21] | Fc1ccc(Cl)c(c1)C1NC(=O)c2cc(Br)cc(Nc3cn[nH]c3)c12 | 1H NMR (400 MHz, DMSO-d6) 12.75 (s, 1H), 9.09 (s, 1H), 7.59 (br. s, 1H), 7.51 (dd, J = 8.8, 5.2 Hz, 1H), 7.23 (ddd, J = 8.8, 8.0, 3.1 Hz, 2H), 7.15 (d, J = 1.6 Hz, 1H), 6.98-6.94 (m, 2H), 6.68 (br. s, 1H), 5.82 (s, 1H) | 421 | E | |
| I-2057 | 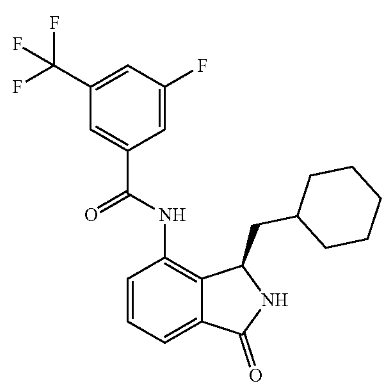 [SMILES: O=C(Nc1cccc2c1[C@@H](CC1CCCCC1)NC2=O)c1cc(F)cc(C(F)(F)F)c1] | Fc1cc(cc(c1)C(F)(F)F)C(=O)Nc1cccc2C(=O)N[C@H](CC3CCCCC3)c12 | NMR (400 MHz, DMSO-d6) 10.78 (s, 1H), 8.91 (s, 1H), 8.17 (s, 1H), 8.12 (d, J = 9.0 Hz, 1H), 8.05 (d, J = 8.4 Hz, 1H), 7.60-7.50 (m, 3H), 4.83 (br, d, J = 8.0 Hz, 1H), 1.83-1.66 (m, 2H), 1.57-1.37 (m, 5H), 1.18-0.90 (m, 4H), 0.81-0.58 (m, 2H). | 435 | D | |

TABLE 2-continued

Representative Compounds of the Invention with Bioactivity Data.

| Ex. No. | Structure | SMILES | $^1$H NMR | MS | ADP-Glo IC$_{50}$ | MCF 10A IC$_{50}$ |
|---|---|---|---|---|---|---|
| I-2058 | 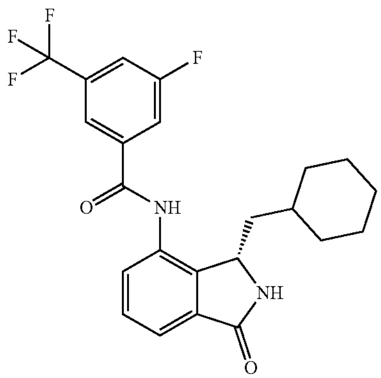 [SMILES: O=C(Nc1cccc2c1[C@H](CC1CCCCC1)NC2=O)c1cc(F)cc(C(F)(F)F)c1] | Fc1cc(cc(c1)C(F)(F)F)C(=O)Nc1cccc2C(=O)N[C@@H](CC3CCCCC3)c12 | NMR (400 MHz, DMSO-d6) 10.78 (s, 1H), 8.91 (s, 1H), 8.17 (s, 1H), 8.12 (d, J = 9.0 Hz, 1H), 8.05 (d, J = 8.4 Hz, 1H), 7.60-7.50 (m, 3H), 4.83 (br, d, J = 8.0 Hz, 1H), 1.83-1.66 (m, 2H), 1.57-1.37 (m, 5H), 1.18-0.90 (m, 4H), 0.81-0.58 (m, 2H). | 435 | C | |
| I-2059 | 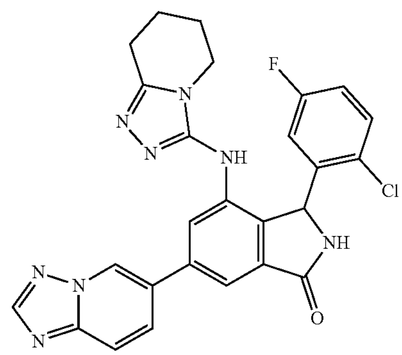 [SMILES: O=C1NC(c2cc(F)ccc2Cl)c2c(Nc3nnc4n3CCCC4)cc(-c3ccc4ncnn4c3)cc21] | Fc1ccc(Cl)c(c1)C1NC(=O)c2cc(cc(Nc3nnc4CCCn34)c12)-c1ccc2nccnn2c1 | 1H NMR (400 MHz, DMSO-d6) 9.32 (s, 1H), 8.92 (s, 1H), 8.52 (s), 8.22 (br. s, 1H), 8.04 (dd, J = 9.4, 1.4 Hz, 1H), 7.95 (d, J = 9.3 Hz, 1H), 7.81-7.70 (m, 2H), 7.44 (dd, J = 8.9, 5.2 Hz, 1H), 7.20 (td, J = 8.7, 2.9 Hz, 1H), 6.46 (d, J = 8.6 Hz, 1H), 5.92 (s, 1H), 3.53-3.40 (m, 1H), 2.92-2.79 (m, 1H), 2.77-2.69 (m, 2H), 1.87-1.63 (m, 4H). | 515.3 | E | |
| I-2060 | 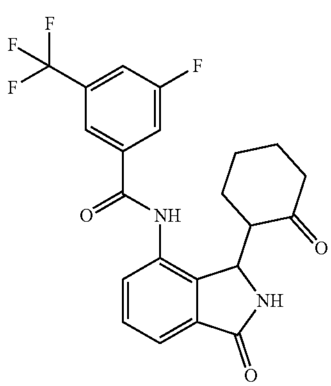 [SMILES: O=C(Nc1cccc2c1C(C1CCCCC1=O)NC2=O)c1cc(F)cc(C(F)(F)F)c1] | Fc1cc(cc(c1)C(F)(F)F)C(=O)Nc1cccc2C(=O)NC(C3CCCCC3-O)c12 | (400 MHz, DMSO-d6) 10.62 (br s, 0.65H), 10.37 (s, 0.35H), 8.55 (s, 0.35H), 8.25 (s, 0.65H), 8.15 (s, 0.35H), 8.13 (s, 0.65H), 8.10 (d, J = 10.4, 1.4 Hz, 1H), 8.02 (d, J = 8.5 Hz, 1H), 7.61 (td, J = 7.3, 1.1 Hz, 1H), 7.57-7.48 (m, 2H), 5.43 (s, 0.65H), 5.11 (d, J = 1.2 Hz, 0.35H), 2.97-2.89 (m, 0.65H), 2.84-2.77 (m, 0.35H), 2.30-2.19 (m, 1.3H), 1.96-1.78 (m, 1H), 1.76-1.56 (m, 2H), 1.53-1.39 (m, 2H), 1.38-1.27 (m, 0.35H), 1.25-1.11 (m, 1H), 1.07-0.97 (m, 0.65H) [~2:1 ratio of diastereomers]. | 435.2 | E | |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-2061 | 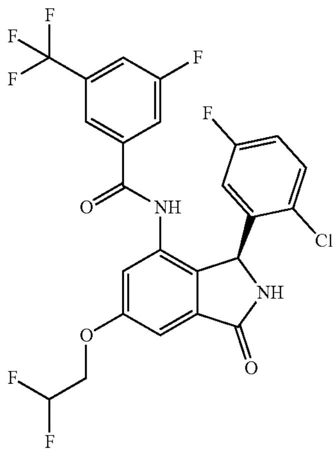 [SMILES: O=C(Nc1cc(OCC(F)F)cc2c1[C@@H](c1cc(F)ccc1Cl)NC2=O)c1cc(F)cc(C(F)(F)F)c1] | FC(F)COc1cc2C(=O)N[C@H](c2c(NC(=O)c2cc(F)cc(c2)C(F)(F)F)c1)c1cc(F)ccc1Cl | | | D | |
| I-2062 | 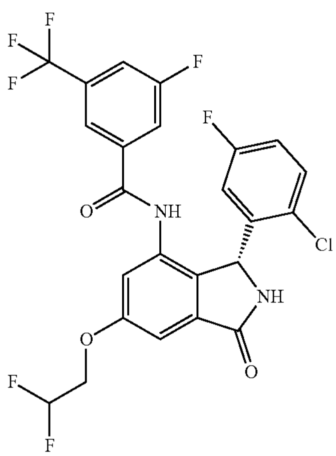 [SMILES: O=C(Nc1cc(OCC(F)F)cc2c1[C@H](c1cc(F)ccc1Cl)NC2=O)c1cc(F)cc(C(F)(F)F)c1] | FC(F)COc1cc2C(=O)N[C@@H](c2c(NC(=O)c2cc(F)cc(c2)C(F)(F)F)c1)c1cc(F)ccc1Cl | | 547.1 | A | |
| I-2063 | 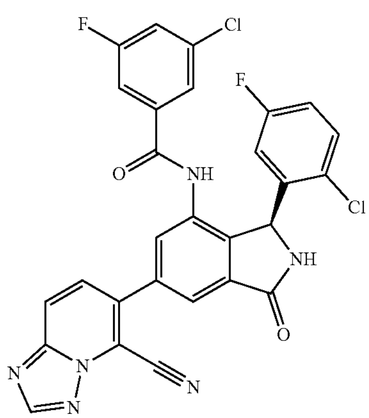 [SMILES: N#Cc1c(-c2cc(NC(=O)c3cc(F)cc(Cl)c3)c3c(c2)C(=O)N[C@@H]3c2cc(F)ccc2Cl)ccc2ncnn12] | Fc1ccc(Cl)c(c1)[C@@H]1NC(=O)c2cc(cc(NC(=O)c3cc(F)cc(Cl)c3)c12)c1ccc2ncnn2c1C#N | | 576.2 | C | |

TABLE 2-continued

Representative Compounds of the Invention with Bioactivity Data.

| Ex. No. | Structure | SMILES | $^1$H NMR | MS | ADP-Glo IC$_{50}$ | MCF 10A IC$_{50}$ |
|---|---|---|---|---|---|---|
| I-2064 | 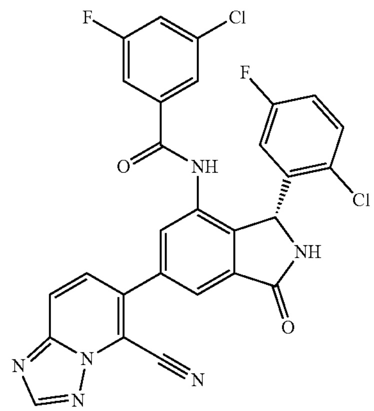 [SMILES: N#Cc1c(-c2cc(NC(=O)c3cc(F)cc(Cl)c3)c3c(c2)C(=O)N[C@H]3c2cc(F)ccc2Cl)ccc2ncnn12] | Fc1ccc(Cl)c(c1)[C@H]1NC(=O)c2cc(cc(NC(=O)c3cc(F)cc(Cl)c3)c12)-c1ccc2ncnn2c1C#N | | 576.2 | A | |
| I-2065 | 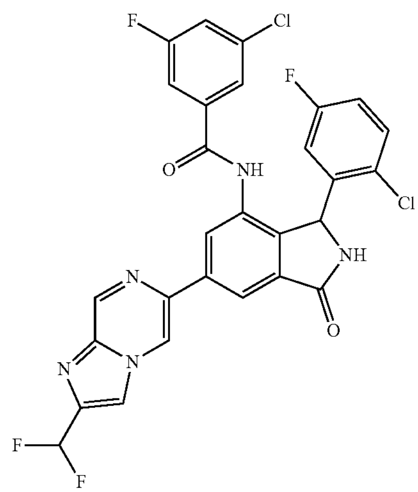 [SMILES: O=C(Nc1cc(-c2cn3cc(C(F)F)nc3cn2)cc2c1C(c1cc(F)ccc1Cl)NC2=O)c1cc(F)cc(Cl)c1] | FC(F)c1cn2cc(ncc2n1)-c1cc2C(=O)NC(c2c(NC(=O)c2cc(F)cc(c2)C(F)(F)F)c1)c1cc(F)ccc1Cl | | | A | |
| I-2066 | 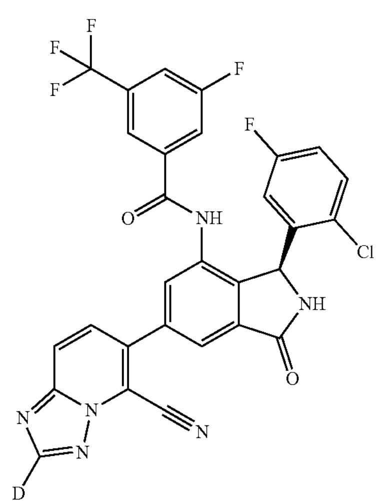 [SMILES: [2H]c1nc2ccc(-c3cc(NC(=O)c4cc(F)cc(C(F)(F)F)c4)c4c(c3)C(=O)N[C@@H]4c3cc(F)ccc3Cl)c(C#N)n2n1] | [2H]c1nc2ccc(-c3cc4C(=O)N[C@H](c4c(NC(=O)c4cc(F)cc(c4)C(F)(F)F)c3)c3cc(F)ccc3Cl)c(C#N)n2n1 | | 610.00 | D | |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---------|-----------|--------|--------|-----|-----|-----|
| I-2067 | 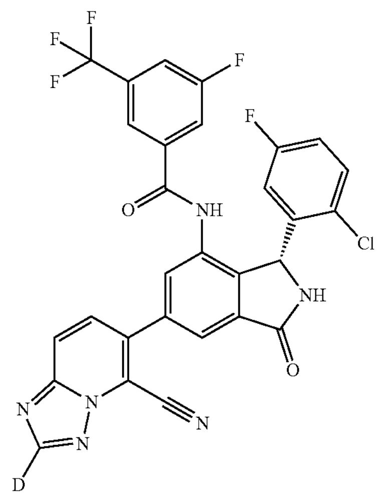 [SMILES: [2H]c1nc2ccc(-c3cc(NC(=O)c4cc(F)cc(C(F)(F)F)c4)c4c(c3)C(=O)N[C@H]4c3cc(F)ccc3Cl)c(C#N)n2n1] | [2H]c1nc2ccc(-c3cc4C(=O)N[C@@H](c4c(NC(=O)c4cc(F)cc(c4)C(F)(F)F)c3)c3cc(F)ccc3Cl)c(C#N)n2n1 | | 610.00 | A | |
| I-2068 | 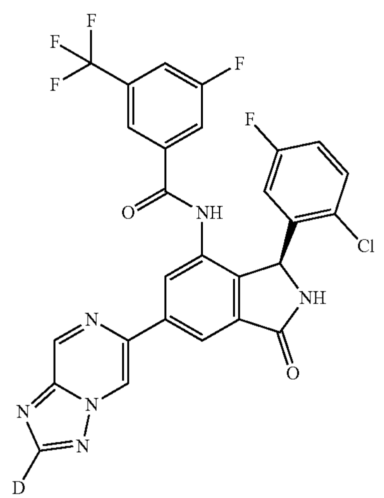 [SMILES: [2H]c1nc2cnc(-c3cc(NC(=O)c4cc(F)cc(C(F)(F)F)c4)c4c(c3)C(=O)N[C@@H]4c3cc(F)ccc3Cl)cn2n1] | [2H]c1nc2cnc(cn2n1)-c1cc2C(=O)N[C@H](c2c(NC(=O)c2cc(F)cc(c2)C(F)(F)F)c1)c1cc(F)ccc1Cl | | 586.15 | D | |
| I-2069 | 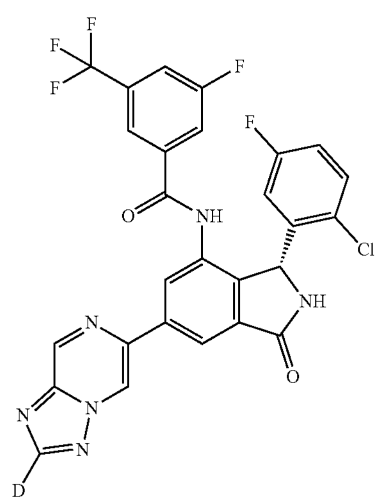 [SMILES: [2H]c1nc2cnc(-c3cc(NC(=O)c4cc(F)cc(C(F)(F)F)c4)c4c(c3)C(=O)N[C@H]4c3cc(F)ccc3Cl)cn2n1] | [2H]c1nc2cnc(cn2n1)-c1cc2C(=O)N[C@@H](c2c(NC(=O)c2cc(F)cc(c2)C(F)(F)F)c1)c1cc(F)ccc1Cl | | 586.15 | A | |

TABLE 2-continued

Representative Compounds of the Invention with Bioactivity Data.

| Ex. No. | Structure | SMILES | $^1$H NMR | MS | ADP-Glo IC$_{50}$ | MCF 10A IC$_{50}$ |
|---|---|---|---|---|---|---|
| I-2070 | 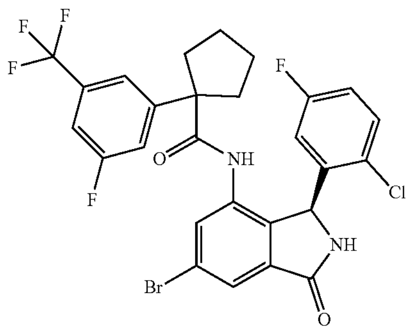 [SMILES: O=C1N[C@H](c2cc(F)ccc2Cl)c2c(NC(=O)C3(c4cc(F)cc(C(F)(F)F)c4)CCCC3)cc(Br)cc21] | Fc1ccc(Cl)c(c1)[C@@H]1NC(=O)c2cc(Br)cc(NC(=O)C3(CCCC3)c3cc(F)cc(c3)C(F)(F)F)c12 | | | | E |
| I-2071 | 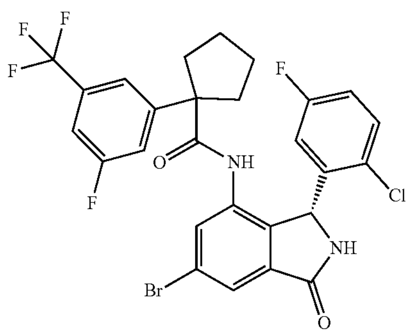 [SMILES: O=C1N[C@@H](c2cc(F)ccc2Cl)c2c(NC(=O)C3(c4cc(F)cc(C(F)(F)F)c4)CCCC3)cc(Br)cc21] | Fc1ccc(Cl)c(c1)[C@H]1NC(=O)c2cc(Br)cc(NC(=O)C3(CCCC3)c3cc(F)cc(c3)C(F)(F)F)c12 | | | | E |
| I-2072 | 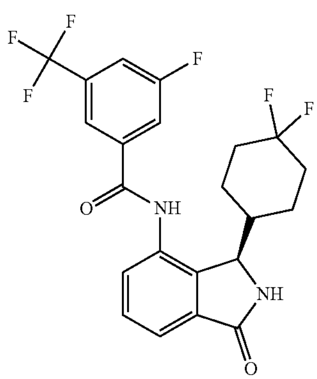 [SMILES: O=C(Nc1cccc2c1[C@@H](C1CCC(F)(F)CC1)NC2=O)c1cc(F)cc(C(F)(F)F)c1] | Fc1cc(cc(c1)C(F)(F)F)C(=O)Nc1cccc2C(=O)N[C@H](C3CCC(F)(F)CC3)c12 | | 457.3 | | E |
| I-2073 | 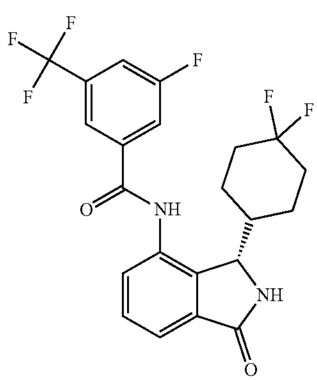 [SMILES: O=C(Nc1cccc2c1[C@H](C1CCC(F)(F)CC1)NC2=O)c1cc(F)cc(C(F)(F)F)c1] | Fc1cc(cc(c1)C(F)(F)F)C(=O)Nc1cccc2C(=O)N[C@@H](C3CCC(F)(F)CC3)c12 | | 457.3 | | E |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-2074 | 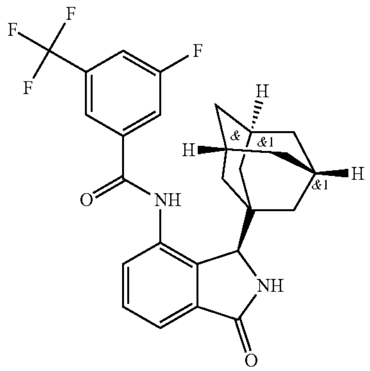 [SMILES: O=C(Nc1cccc2c1[C@@H](C13C[C@H]4C[C@@H](C1)C[C@@H](C3)C4)NC2=O)c1cc(F)cc(C(F)(F)F)c1] | Fc1cc(cc(c1)C(F)(F)F)C(=O)Nc1cccc2C(=O)N[C@H](c12)C12C[C@H]3C[C@H](C[C@H](C3)C1)C2 | | 473.3 | E | |
| I-2075 | 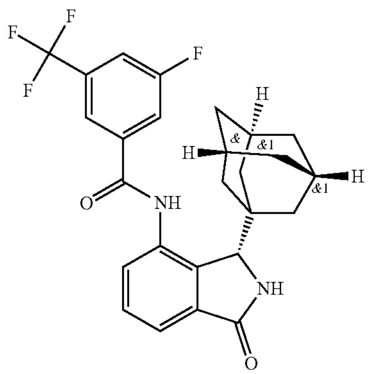 [SMILES: O=C(Nc1cccc2c1[C@H](C13C[C@H]4C[C@@H](C1)C[C@@H](C3)C4)NC2=O)c1cc(F)cc(C(F)(F)F)c1] | Fc1cc(cc(c1)C(F)(F)F)C(=O)Nc1cccc2C(=O)N[C@@H](c12)C12C[C@H]3C[C@H](C[C@H](C3)C1)C2 | | 473.3 | D | |
| I-2076 | 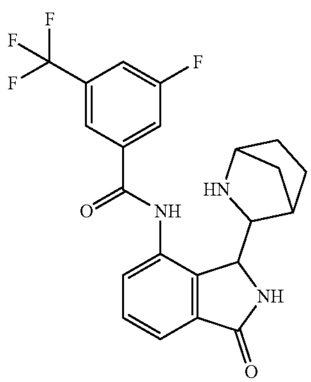 [SMILES: O=C(Nc1cccc2c1C(C1NC3CCC1C3)NC2=O)c1cc(F)cc(C(F)(F)F)c1] | Fc1cc(cc(c1)C(F)(F)F)C(=O)Nc1cccc2C(=O)NC(C3NC4CCC3C4)c12 | NMR (400 MHz, DMSOd6) 8.98 (s, 1H), 8.48 (dd, J = 8.0, 1.0 Hz, 1H), 8.26 (s, 1H), 8.07 (s, 1H), 8.03 (d, J = 8.9 Hz, 1H), 7.52 (t, J = 7.7 Hz, 1H), 7.43 (dd, J = 7.4, 1.0 Hz, 1H), 4.64 (d, J = 10.0 Hz, 1H), 3.21 (s, 1H), 2.79 (d, J = 3.5 Hz, 1H), 2.03 (d, J = 9.4 Hz, 1H), 1.66-1.47 (m, 2H), 1.29 (m, 4H). | 434.3 | E | |
| I-2077 | 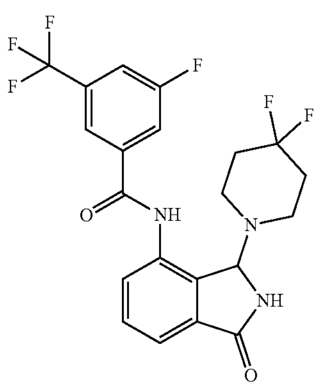 [SMILES: O=C(Nc1cccc2c1C(N1CCC(F)(F)CC1)NC2=O)c1cc(F)cc(C(F)(F)F)c1] | Fc1cc(cc(c1)C(F)(F)F)C(=O)Nc1cccc2C(=O)NC(N3CCC(F)(F)CC3)c12 | NMR (400 MHz, DMSO d6) 10.35 (s, 1H), 8.97 (s, 1H), 8.14-8.12 (m, 1H), 8.11 (dd, J = 7.9, 0.9 Hz, 2H), 8.11-8.07 (submerged broad dt, J = 9.3, 2 Hz, 1H), 8.05 (broad dt, J = 8.5, 1.4 Hz, 1H), 7.60 (t, J = 7.7 Hz, 1H), 7.51 (dd, J = 7.5, 0.9 Hz, 1H), 5.72 (s, 1H), 2.69-2.57 (m, 2H), 2.45-2.34 (m, 2H), 1.93-1.77 (m, 2H), 1.70 (m, 2H). | 458.3 | D | |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-2078 | 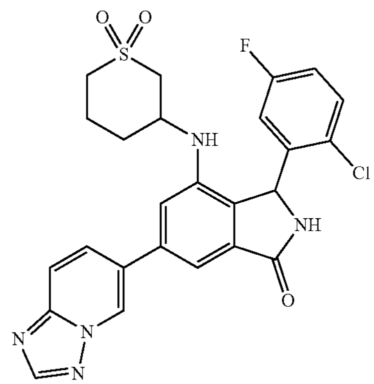 [SMILES: O=C1NC(c2cc(F)ccc2Cl)c2c(NC3CCCS(=O)(=O)C3)cc(-c3ccc4ncnn4c3)cc21] | Fc1ccc(Cl)c(c1)C1NC(=O)c2cc(cc(NC3CCCS(=O)(=O)C3)c12)-c1ccc2ncnn2c1 | NMR (400 MHz, DMSO) 9.49-9.47 (m, 0.6H), 9.47-9.45 (m, 0.4H), 9.09 (s, 0.6H), 9.08 (s. 0.4H), 8.56 (s, 1H), 8.12 (d, J = 1.8 Hz, 0.4H), 8.09 (d, J = 1.8 Hz, 0.6H), 7.95 (s, 0.6H), 7.93 (s, 0.4H), 7.62-7.54 (m, 1H), 7.43 (d, J = 1.2 Hz, 0.4H), 7.42 (d, J = 1.1 Hz, 0.6H), 7.31-7.18 (m, 3H), 7.12 (s, 1H), 6.99 (s, 1H), 6.81 (br s, 1H), 5.93 (s, 0.4H), 5.91 (s, 0.6H), 4.67 (d, J = 8.8 Hz, 0.4H), 4.63 (d, J = 9.5 Hz, 0.6H), 4.27-4.09 (m, 1H), 3.55-3.45 (m, 0.6H), 3.21-2.91 (m, 3H), 2.77-2.68 (m, 0.4H), 2.08-1.60 (m, 3H), 1.56-1.29 (m, 1H). ~3:2 mix of diastereomers. | 526 | E | |
| I-2079 | 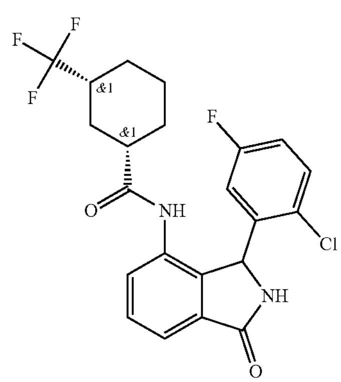 [SMILES: O=C1NC(c2cc(F)ccc2Cl)c2c(NC(=O)[C@H]3CCC[C@@H](C(F)(F)F)C3)cccc21] | Fc1ccc(Cl)c(c1)C1NC(=O)c2cccc(NC(=O)[C@H]3CCC[C@H](C3)C(F)(F)F)c12 | 1H-NMR (400 MHz, DMSO-d6) as a ca. 1:1 mixture of diastereomers, 9.82 (br. s, 1H), 9.73 (br. s, 1H), 9.09 (br. s, 2H), 7.63-7.54 (m, 4H), 7.51-7.42 (m, 2H), 7.41-7.34 (m, 2H), 7.25-7.16 (m, 2H), 6.42 (br. s, 2H), 6.04 (br. s, 2H), 2.30-2.08 (m, 4H), 1.85-1.68 (m, 4H), 1.64-1.50 (m, 2H), 1.40-0.92 (m, 10H). | 455.3 | C | |
| I-2080 | 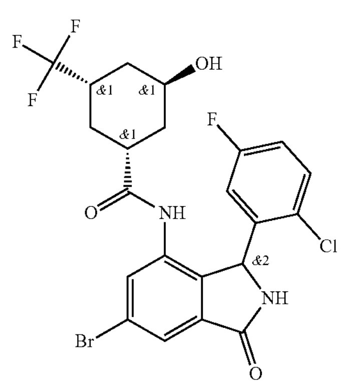 [SMILES: O=C1NC(c2cc(F)ccc2Cl)c2c(NC(=O)[C@H]3C[C@H](O)C[C@@H](C(F)(F)F)C3)cc(Br)cc21] | O[C@H]1C[C@@H](C[C@@H](C1)C(F)(F)F)C(=O)Nc1cc(Br)cc2C(=O)NC(c12)c1cc(F)ccc1Cl | 1H-NMR (400 MHz, DMSO-d6) as a ca. 1:1 mixture of diastereomers, 9.98 (br. s, 1H), 9.87 (br. s, 1H), 9.25 (br. s, 2H), 7.71 (d, J = 1.5 Hz, 1H), 7.70 (d, J = 1.5 Hz, 1H), 7.65 (d, J = 1.6 Hz, 1H), 7.54 (d, J = 1.5 Hz, 1H), 7.50-7.41 (m, 2H), 7.23-7.17 (m, 2H), 6.53 (br. s, 2H), 6.01 (br. s, 2H), 4.84 (d, J = 2.6 Hz, 1H), 4.80 (d, J = 2.8 Hz, 1H), 4.04 (br. s, 1H), 4.02 (br. s, 1H), 2.61-2.53 (m, 2H), 2.47-2.38 (m, 2H), 1.80-1.72 (m, 2H), 1.58-1.51 (m, 1H), 1.50-1.44 (m, 1H), 1.41-1.17 (m, 7H), 1.11-1.00 (m, 1H). | 549.1 | D | |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-2081 | 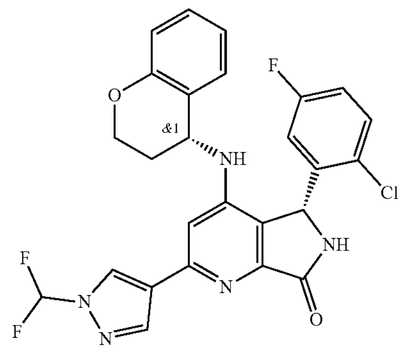 [SMILES: O=C1N[C@@H](c2cc(F)ccc2Cl)c2c(N[C@@H]3CCOc4ccccc43)cc(-c3cnn(C(F)F)c3)nc21] | FC(F)n1cc(cn1)-c1cc(N[C@H]2CCOc3ccccc23)c2[C@H](NC(=O)c2n1)c1cc(F)ccc1Cl | | 526.1 | D | |
| I-2082 | 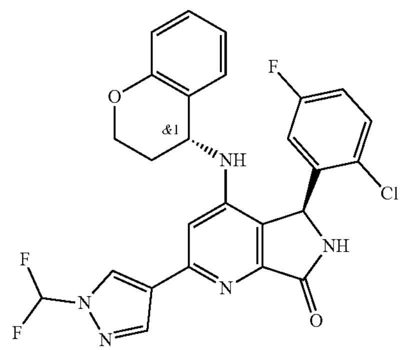 [SMILES: O=C1N[C@H](c2cc(F)ccc2Cl)c2c(N[C@@H]3CCOc4ccccc43)cc(-c3cnn(C(F)F)c3)nc21] | FC(F)n1cc(cn1)-c1cc(N[C@H]2CCOc3ccccc23)c2[C@@H](NC(=O)c2n1)c1cc(F)ccc1Cl | | 526.1 | E | |
| I-2083 | 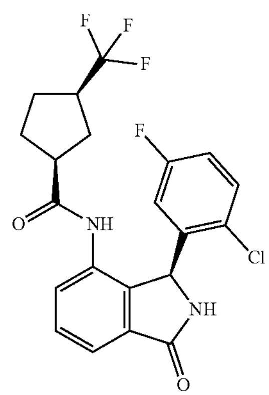 [SMILES: O=C1N[C@H](c2cc(F)ccc2Cl)c2c(NC(=O)[C@H]3CC[C@@H](C(F)(F)F)C3)cccc21] | Fc1ccc(Cl)c(c1)[C@H]1NC(=O)c2cccc(NC(=O)[C@H]3CC[C@H](C3)C(F)(F)F)c12 | 1H NMR (400 MHz, DMSO-d6) Ä¤ 9.80 (s, 1H), 9.08 (s, 1H), 7.61 (dd, J = 7.4, 1.4 Hz, 1H), 7.58 (t, J = 7.5 Hz, 1H), 7.46 (s, 1H), 7.39 (dd, J = 7.5, 1.5 Hz, 1H), 7.22 (ddd, J = 8.9, 8.0, 3.1 Hz, 1H), 6.51 (s, 1H), 6.05 (s, 1H), 2.83 (d, J = 8.3 Hz, 1H), 2.78 (d, J = 8.9 Hz, 1H), 1.84-1.56 (dt, J = 12.9, 7.8 Hz, 4H), 1.55-1.24 (d, J = 12.4 Hz, 2H). | 441.05 | E | |
| I-2084 | 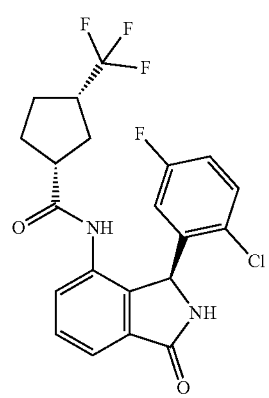 [SMILES: O=C1N[C@H](c2cc(F)ccc2Cl)c2c(NC(=O)[C@@H]3CC[C@H](C(F)(F)F)C3)cccc21] | Fc1ccc(Cl)c(c1)[C@H]1NC(=O)c2cccc(NC(=O)[C@@H]3CC[C@@H](C3)C(F)(F)F)c12 | 1H NMR (400 MHz, DMSO-d6)9.78 (s, 1H), 9.10-9.06 (m, 1H), 7.61 (dd, J = 7.4, 1.5 Hz, 1H), 7.58 (t, J = 7.4 Hz, 1H), 7.49 (s, 1H), 7.39 (dd, J = 7.4, 1.5 Hz, 1H), 7.22 (ddd, J = 8.8, 8.0, 3.1 Hz, 1H), 6.47 (s, 1H), 6.07 (s, 1H), 2.80 (h, J = 8.9 Hz, 1H), 2.63 (p, J = 8.3 Hz, 1H), 1.87-1.57 (dt, J = 12.9, 7.8 Hz, 4H), 1.55-1.24 (d, J = 12.4 Hz, 2H). | 441.05 | E | |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-2085 | 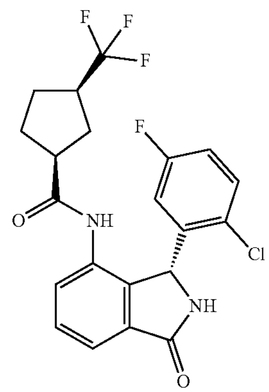 [SMILES: O=C1N[C@@H](c2cc(F)ccc2Cl)c2c(NC(=O)[C@H]3CC[C@@H](C(F)(F)F)C3)cccc21] | Fc1ccc(Cl)c(c1)[C@@H]1NC(=O)c2ccc c(NC(=O)[C@H]3CC[C@H](C3)C(F)(F)F)c12 | 1H NMR (400 MHz, DMSO-d6) Ä¤ 9.81 (s, 1H), 9.08 (s, 1H), 7.65-7.53 (m, 2H), 7.47 (t, J = 7.2 Hz, 1H), 7.39 (dd, J = 7.4, 1.5 Hz, 1H), 7.22 (td, J = 8.4, 3.1 Hz, 1H), 6.43 (s, 1H), 6.05 (s, 1H), 2.81 (dq, J = 18.3, 9.1 Hz, 1H), 2.58 (q, J = 8.8, 8.1 Hz, 1H), 1.86-1.57 (dt, J = 12.9, 7.8 Hz, 4H), 1.56-1.24 (d, J = 12.4 Hz, 2H). | 441.05 | D | |
| I-2086 | 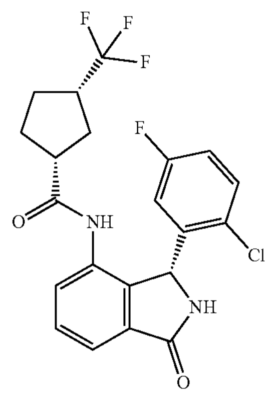 [SMILES: O=C1N[C@@H](c2cc(F)ccc2Cl)c2c(NC(=O)[C@@H]3CC[C@H](C(F)(F)F)C3)cccc21] | Fc1ccc(Cl)c(c1)[C@@H]1NC(=O)c2ccc c(NC(=O)[C@@H]3CC[C@@H](C3)C(F)(F)F)c12 | 1H NMR (400 MHz, DMSO-d6) Ä¤ 9.78 (s, 1H), 9.08 (s, 1H), 7.61 (dd, J = 7.5, 1.5 Hz, 1H), 7.58 (t, J = 7.4 Hz, 1H), 7.53-7.46 (m, 1H), 7.39 (dd, J = 7.4, 1.5 Hz, 1H), 7.22 (td, J = 8.4, 3.1 Hz, 1H), 6.48 (s, 1H), 6.06 (s, 1H), 2.80 (dq, J = 18.0, 9.0 Hz, 1H), 2.62 (dt, J = 10.1, 7.7 Hz, 1H), 1.84-1.57 (dt, J = 12.9, 7.8 Hz, 4H), 1.56-1.24 (d, J = 12.4 Hz, 2H). | 441.05 | D | |
| I-2087 | 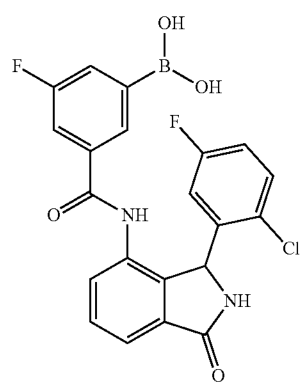 [SMILES: O=C(Nc1cccc2c1C(c1cc(F)ccc1Cl)NC2=O)c1cc(F)cc(B(O)O)c1] | OB(O)c1cc(F)cc(c1)C(=O)Nc1cccc2C(=O)NC(c12)c1cc(F)ccc1Cl | NMR (400 MHz, DMSO-d6) 10.23 (br s, 0.8H), 10.10 (br s, 0.2H), 9.23-9.01 (m, 1H), 8.36 (s, 1H), 7.91 (br s, 0.6H), 7.89-7.83 (m, 0.6H), 7.75-7.39 (m, 5H), 7.33 (dd, J = 8.8, 5.2 Hz, 1H), 7.29-7.22 (m, 1H), 7.10 (td, J = 8.4, 2.4 Hz, 1H), 7.03-6.85 (m, 1H), 6.55 (br s, 1H), 6.10 (br s, 0.5H), 6.03 (br s, 0.5H). | 443 | E | |
| I-2088 | 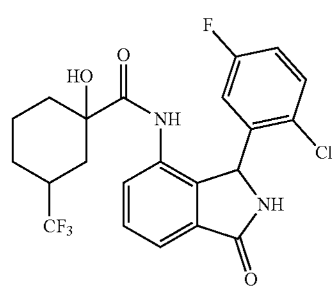 [SMILES: O=C1NC(c2cc(F)ccc2Cl)c2c(NC(=O)C3(O)CCCC(C(F)(F)F)C3)cccc21] | OC1(CCCC(C1)C(F)(F)F)C(=O)Nc1cccc2C(=O)NC(c12)c1cc(F)ccc1Cl | 1H NMR (400 MHz, acetonitrile-d3) 8.61 (br. s, 1H), 7.80 (dd, J = 7.8, 0.6 Hz, 1H), 7.65 (dd, J = 3.0, 1.0 Hz, 1H), 7.58 (ddd, J = 7.6, 1.4 Hz, 1H), 7.47 (dd, J = 8.9, 5.1 Hz, 1H), 7.24 (br. s, 1H), 7.10 (ddd, J = 8.7, 8.1, 3.1 Hz, 1H), 6.57 (br. s, 1H), 6.20 (br. s, 1H), 3.77 (s, 1H), 3.02-2.79 (m, 1H), 1.89-1.79 (m, 1H), 1.68-1.45 (m, 3H), 1.34-1.06 (m, 4H). 1:1 mixture of diastereomers | 471.3 | E | |

TABLE 2-continued

Representative Compounds of the Invention with Bioactivity Data.

| Ex. No. | Structure | SMILES | $^1$H NMR | MS | ADP-Glo IC$_{50}$ | MCF 10A IC$_{50}$ |
|---|---|---|---|---|---|---|
| I-2089 | 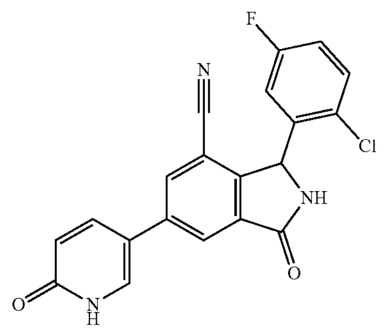 [SMILES: N#Cc1cc(-c2ccc(=O)[nH]c2)cc2c1C(c1cc(F)ccc1Cl)NC2=O] | Fc1ccc(Cl)c(c1)C1NC(=O)c2cc(cc(C#N)c12)-c1ccc(=O)[nH]c1 | | | | E |
| I-2090 | 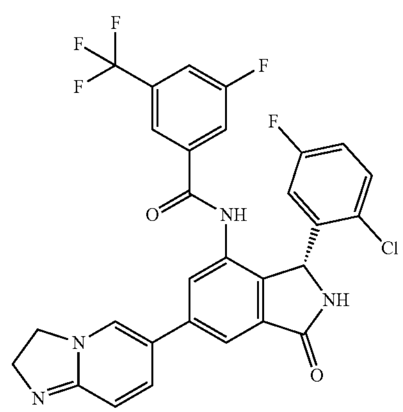 [SMILES: O=C(Nc1cc(C2=CN3CCN=C3C=C2)cc2c1[C@H](c1cc(F)ccc1Cl)NC2=O)c1cc(F)cc(C(F)(F)F)c1] | Fc1ccc(Cl)c(c1)[C@@H]1NC(=O)c2cc(cc(NC(=O)c3cc(F)cc(c3)C(F)(F)F)c12)C1=CN2CCN=C2C=C1 | 1H NMR (400 MHz, DMSO-d6) 10.30 (s, 1H), 9.13 (s, 1H), 8.12 (s, 1H), 7.93 (d, J = 8.4 Hz, 1H), 7.80-7.70 (m, 3H), 7.66 (s, 1H), 7.53 (d, J = 9.5 Hz, 1H), 7.33 (dd, J = 8.9, 5.1 Hz, 1H), 7.10 (td, J = 8.4, 3.1 Hz, 1H), 6.71 (s, 1H), 6.44 (d, J = 9.6 Hz, 1H), 5.99 (s, 1H), 4.16 (t, J = 10.3 Hz, 2H), 3.83 (t, J = 10.3 Hz, 2H). | 585.1 | A | |
| I-2091 | 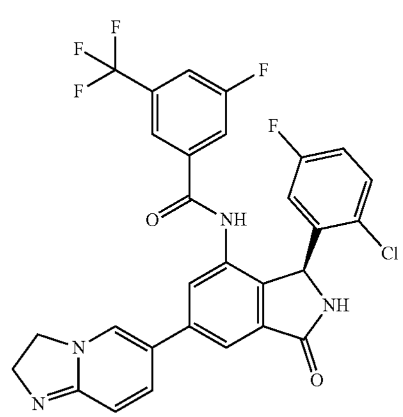 [SMILES: O=C(Nc1cc(C2=CN3CCN=C3C=C2)cc2c1[C@@H](c1cc(F)ccc1Cl)NC2=O)c1cc(F)cc(C(F)(F)F)c1] | Fc1ccc(Cl)c(c1)[C@H]1NC(=O)c2cc(cc(NC(=O)c3cc(F)cc(c3)C(F)(F)F)c12)C1=CN2CCN=C2C=C1 | 1H NMR (400 MHz, DMSO-d6) 10.30 (s, 1H), 9.13 (s, 1H), 8.12 (s, 1H), 7.93 (d, J = 8.4 Hz, 1H), 7.80-7.70 (m, 3H), 7.66 (s, 1H), 7.53 (d, J = 9.5 Hz, 1H), 7.33 (dd, J = 8.9, 5.1 Hz, 1H), 7.10 (td, J = 8.4, 3.1 Hz, 1H), 6.71 (s, 1H), 6.44 (d, J = 9.6 Hz, 1H), 5.99 (s, 1H), 4.16 (t, J = 10.3 Hz, 2H), 3.83 (t, J = 10.3 Hz, 2H). | 585.1 | C | |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-2092 | 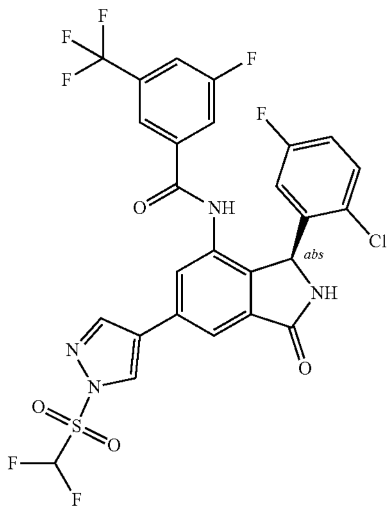 [SMILES: O=C(Nc1cc(-c2cnn(S(=O)(=O)C(F)F)c2)cc2c1[C@@H](c1cc(F)ccc1Cl)NC2=O)c1cc(F)cc(C(F)(F)F)c1] | FC(F)S(=O)(=O)n1cc(cn1)-c1cc2C(=O)N[C@@H](c2c(NC(=O)c2cc(F)cc(c2)C(F)(F)F)c1)c1cc(F)ccc1Cl | (400 MHz, DMSO-d6) 10.60 (s, 1 H), 9.26 (s, 1 H), 9.22 (s, 1 H), 8.89 (s, 1 H), 8.22 (s, 1 H), 7.98 (s, 1 H), 7.97 (overlapped d, J = 11.0 Hz, 1 H), 7.76 (d, J = 8.9 Hz, 1 H), 7.73 (overlapped app t, J = 51.3 Hz, 1 H)7.73 (s, 1 H), 7.32 (dd, J = 8.9, 5.2 Hz, 1 H), 7.10 (td, J = 8.5, 3.0 Hz, 1 H), 6.61 (br s, 1 H), 6.01 (s, 1 H). | 645.2 | B | |
| I-2093 | 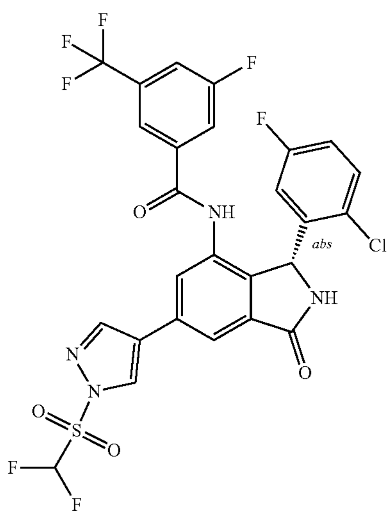 [SMILES: O=C(Nc1cc(-c2cnn(S(=O)(=O)C(F)F)c2)cc2c1[C@H](c1cc(F)ccc1Cl)NC2=O)c1cc(F)cc(C(F)(F)F)c1] | FC(F)S(=O)(=O)n1cc(cn1)-c1cc2C(=O)N[C@H](c2c(NC(=O)c2cc(F)cc(c2)C(F)(F)F)c1)c1cc(F)ccc1Cl | (400 MHz, DMSO-d6) 10.60 (br s, 1 H), 9.27 (s, 1 H), 9.22 (s, 1 H), 8.90 (s, 1 H), 8.22 (s, 1 H), 7.98 (s, 1 H), 7.97 (overlapped d, J = 11.4 Hz, 1 H), 7.76 (d, J = 8.9 Hz, 1 H), 7.73 (overlapped app t, j = 51.6 Hz, 1 H), 7.73 (s, 1 H), 7.32 (dd, J = 8.9, 5.2 Hz, 1 H), 7.10 (td, J = 8.4, 3.0 Hz, 1 H), 6.61 (br s, 1 H), 6.00 (br s, 1 H). | 645.2 | A | |
| I-2094 | 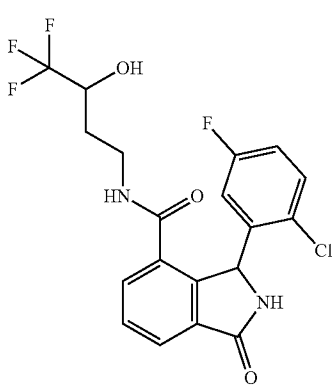 [SMILES: O=C(NCCC(O)C(F)(F)F)c1cccc2c1C(c1cc(F)ccc1Cl)NC2=O] | OC(CCNC(=O)c1cccc2C(=O)NC(c12)c1cc(F)ccc1Cl)C(F)(F)F | 1H NMR (400 MHz, DMSO-d6)9.19 (s, 1H), 8.54-8.47 (m, 1H), 7.87 (d, J = 7.4 Hz, 1H), 7.80 (t, J = 7.8 Hz, 1H), 7.68 (t, J = 7.6 Hz, 1H), 7.45 (d, J = 7.7 Hz, 1H), 7.14 (td, J = 8.4, 3.1 Hz, 1H), 6.37-6.31 (m, 2H), 6.10 (dd, J = 8.8, 6.6 Hz, 1H), 3.86-3.79 (m, 1H), 3.27-3.10 (m, 1H), 3.10-2.96 (m, 1H), 1.51-1.20 (m, 2H). | 431.15 | E | |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-2095 | 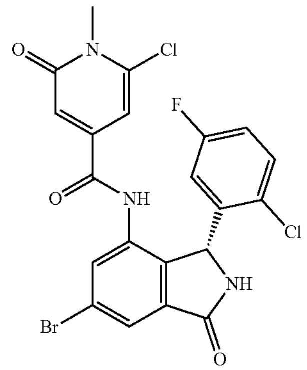 [SMILES: Cn1c(Cl)cc(C(=O)Nc2cc(Br)cc3c2[C@H](c2cc(F)ccc2Cl)NC3=O)cc1=O] | Cn1c(Cl)cc(cc1=O)C(=O)Nc1cc(Br)cc2C(=O)N[C@H](c12)c1cc(F)ccc1Cl | 1H NMR (400 MHz, DMSO-d6)10.43 (s, 1H), 9.30 (s, 1H), 7.82 (d, J = 1.7 Hz, 1H), 7.71 (d, J = 1.8 Hz, 1H), 7.47-7.39 (m, 1H), 7.19 (ddd, J = 8.8, 7.9, 3.1 Hz, 1H), 6.66-6.48 (m, 3H), 5.97 (s, 1H), 3.57 (s, 3H). | 525.9 | E | |
| I-2096 | 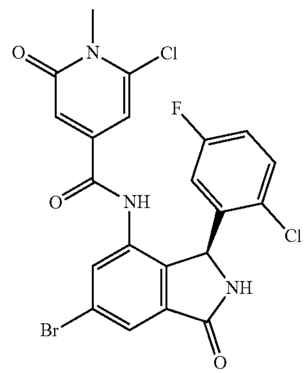 [SMILES: Cn1c(Cl)cc(C(=O)Nc2cc(Br)cc3c2[C@@H](c2cc(F)ccc2Cl)NC3=O)cc1=O] | Cn1c(Cl)cc(cc1=O)C(=O)Nc1cc(Br)cc2C(=O)N[C@@H](c12)c1cc(F)ccc1Cl | 1H NMR (400 MHz, DMSO-d6)10.43 (s, 1H), 9.30 (s, 1H), 7.82 (d, J = 1.7 Hz, 1H), 7.71 (d, J = 1.8 Hz, 1H), 7.43 (t, J = 7.1 Hz, 1H), 7.19 (ddd, J = 8.8, 7.9, 3.1 Hz, 1H), 6.70-6.48 (m, 3H), 5.97 (s, 1H), 3.57 (s, 3H). | 525.9 | E | |
| I-2097 | 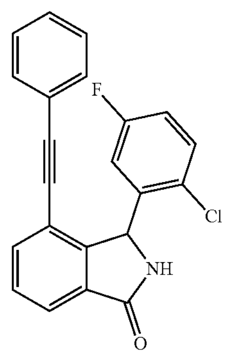 [SMILES: O=C1NC(c2cc(F)ccc2Cl)c2c(C#Cc3ccccc3)cccc21] | Fc1ccc(Cl)c(c1)C1NC(=O)c2ccc(C#Cc3ccccc3)c12 | 1H NMR (400 MHz, DMSO-d6) 9.24 (s, 1H), 7.80 (d, J = 7.5 Hz, 1H), 7.75 (d, J = 7.5 Hz, 1H), 7.63 (t, J = 7.6 Hz, 1H), 7.52 (s, 1H), 7.45-7.37 (m, 3H), 7.28 (dt, J = 9.6, 3.2 Hz, 2H), 7.23 (dd, J = 8.6, 3.0 Hz, 1H), 6.16 (s, 1H). | 362 | E | |
| I-2098 | 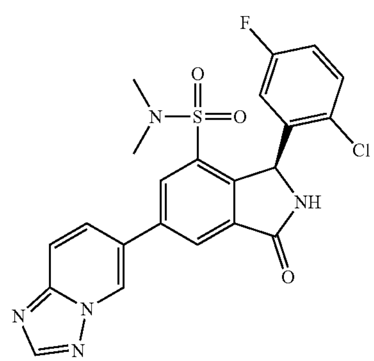 [SMILES: CN(C)S(=O)(=O)c1cc(-c2ccc3ncnn3c2)cc2c1[C@@H](c1cc(F)ccc1Cl)NC2=O] | CN(C)S(=O)(=O)c1cc(cc2C(=O)N[C@H](c12)c1cc(F)ccc1Cl)-c1ccc2ncnn2c1 | 1H NMR (400 MHz, DMSO-d6) 9.61 (dd, J = 1.9, 0.9 Hz, 1H), 9.57 (s, 1H), 8.61 (s, 1H), 8.47 (s, 1H), 8.26-8.16 (m, 2H), 8.00 (d, J = 9.2 Hz, 1H), 7.60 (s, 1H), 7.22 (s, 1H), 6.39 (s, 1H), 2.62 (s, 6H). | 486.05 | E | |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-2099 | 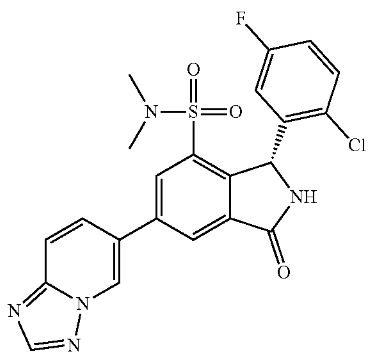 [SMILES: CN(C)S(=O)(=O)c1cc(-c2ccc3ncnn3c2)cc2c1[C@H](c1cc(F)ccc1Cl)NC2=O] | CN(C)S(=O)(=O)c1cc(cc2C(=O)N[C@@H](c12)c1cc(F)ccc1Cl)-c1ccc2ncnn2c1 | 1H NMR (400 MHz, DMSO-d6) 9.61 (dd, J = 1.9, 0.9 Hz, 1H), 9.57 (s, 1H), 8.61 (s, 1H), 8.47 (s, 1H), 8.26-8.16 (m, 2H), 8.00 (d, J = 9.2 Hz, 1H), 7.60 (s, 1H), 7.22 (s, 1H), 6.39 (s, 1H), 2.62 (s, 6H). | 486.05 | E | |
| I-2100 | 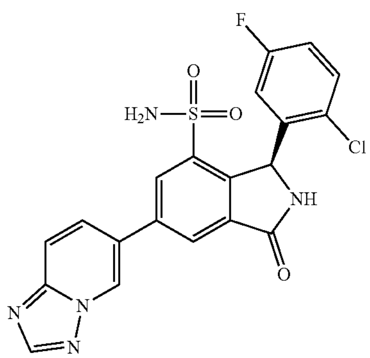 [SMILES: NS(=O)(=O)c1cc(-c2ccc3ncnn3c2)cc2c1[C@@H](c1cc(F)ccc1Cl)NC2=O] | NS(=O)(=O)c1cc(cc2C(=O)N[C@H](c12)c1cc(F)ccc1Cl)-c1ccc2ncnn2c1 | 1H NMR (400 MHz, DMSO-d6) 9.56 (dd, J = 1.8, 0.9 Hz, 1H), 9.48 (s, 1H), 8.62 (s, 1H), 8.55 (s, 1H), 8.42 (d, J = 1.7 Hz, 1H), 8.20 (dd, J = 9.3, 1.9 Hz, 1H), 8.06 (d, J = 9.3 Hz, 1H), 7.56 (s, 2H), 7.21 (td, J = 8.4, 3.0 Hz, 1H), 6.37 (s, 2H). | 458 | E | |
| I-2101 | 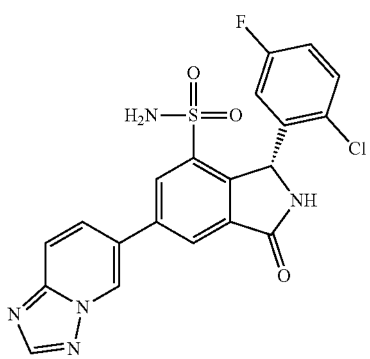 [SMILES: NS(=O)(=O)c1cc(-c2ccc3ncnn3c2)cc2c1[C@H](c1cc(F)ccc1Cl)NC2=O] | NS(=O)(=O)c1cc(cc2C(=O)N[C@@H](c12)c1cc(F)ccc1Cl)-c1ccc2ncnn2c1 | 1H NMR (400 MHz, DMSO-d6) 9.56 (dd, J = 1.8, 0.9 Hz, 1H), 9.48 (s, 1H), 8.62 (s, 1H), 8.55 (s, 1H), 8.42 (d, J = 1.7 Hz, 1H), 8.20 (dd, J = 9.3, 1.9 Hz, 1H), 8.06 (d, J = 9.3 Hz, 1H), 7.56 (s, 2H), 7.21 (td, J = 8.4, 3.0 Hz, 1H), 6.37 (s, 2H). | 458 | E | |
| I-2102 | 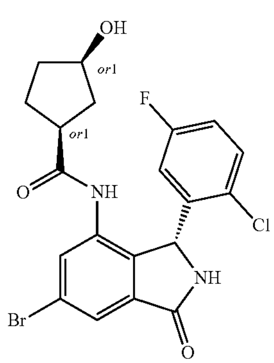 [SMILES: O=C1N[C@@H](c2cc(F)ccc2Cl)c2c(NC(=O)[C@H]3CC[C@@H](O)C3)cc(Br)cc21] | O[C@H]1CC[C@H](C1)C(=O)Nc1cc(Br)cc2C(=O)N[C@H](c12)c1cc(F)ccc1C1 | 1H NMR (400 MHz, DMSO-d6) 9.71 (s, 1H), 9.23 (s, 1H), 7.70 (s, 1H), 7.64 (d, J = 1.7 Hz, 1H), 7.49 (s, 1H), 7.24 (td, J = 8.4, 3.1 Hz, 1H), 6.67 (s, 1H), 6.01 (s, 1H), 4.62 (d, J = 4.7 Hz, 1H), 4.04-3.96 (m, 1H), 2.42 (q, J = 8.2 Hz, 1H), 1.87-1.75 (m, 1H), 1.59 (d, J = 6.6 Hz, 1H), 1.43 (s, 3H), 1.34 (ddd, J = 13.8, 8.7, 6.3 Hz, 1H), 1.24 (s, 1H). | 467.05 | E | |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-2103 | 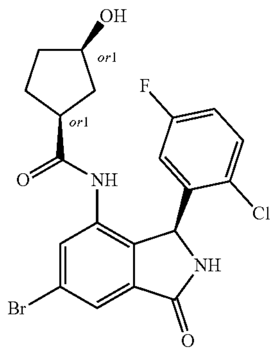 [SMILES: O=C1N[C@H](c2cc(F)ccc2Cl)c2c(NC(=O)[C@H]3CC[C@@H](O)C3)cc(Br)cc21] | O[C@H]1CC[C@H](C1)C(=O)Nc1cc(Br)cc2C(=O)N[C@@H](c12)c1cc(F)ccc1Cl | 1H NMR (400 MHz, DMSO-d6) 9.67 (s, 1H), 9.23 (s, 1H), 7.72-7.61 (m, 2H), 7.48 (s, 1H), 7.24 (td, J = 8.5, 3.1 Hz, 1H), 6.67 (s, 1H), 6.01 (s, 1H), 4.61 (d, J = 4.6 Hz, 1H), 4.00 (q, J = 5.6 Hz, 1H), 2.42 (q, J = 8.3 Hz, 1H), 1.75 (dt, J = 13.9, 7.3 Hz, 1H), 1.64-1.37 (m, 2H), 1.42 (s, 3H), 1.24 (s, 1H). | 467.05 | E | |
| I-2104 | 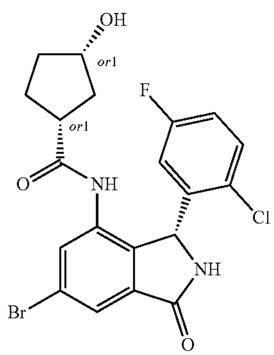 [SMILES: O=C1N[C@@H](c2cc(F)ccc2Cl)c2c(NC(=O)[C@@H]3CC[C@H](O)C3)cc(Br)cc21] | O[C@@H]1CC[C@@H](C1)C(=O)Nc1cc(Br)cc2C(=O)N[C@H](c12)c1cc(F)ccc1Cl | 1H NMR (400 MHz, DMSO-d6) 9.71 (s, 1H), 9.23 (s, 1H), 7.70 (d, J = 1.7 Hz, 1H), 7.64 (d, J = 1.7 Hz, 1H), 7.49 (s, 1H), 7.24 (td, J = 8.4, 3.0 Hz, 1H), 6.67 (s, 1H), 6.01 (s, 1H), 4.62 (d, J = 4.7 Hz, 1H), 3.99 (q, J = 5.6 Hz, 1H), 2.42 (q, J = 8.3 Hz, 1H), 1.81 (ddd, J = 14.0, 8.5, 6.2 Hz, 1H), 1.60 (s, 1H), 1.44 (s, 3H), 1.35 (ddd, J = 12.9, 8.6, 6.1 Hz, 1H). | 467.05 | E | |
| I-2105 | 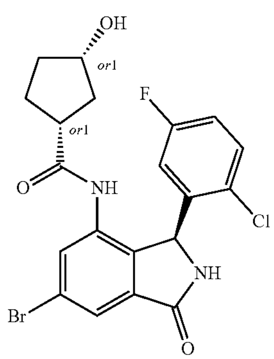 [SMILES: O=C1N[C@H](c2cc(F)ccc2Cl)c2c(NC(=O)[C@@H]3CC[C@H](O)C3)cc(Br)cc21] | O[C@@H]1CC[C@@H](C1)C(=O)Nc1cc(Br)cc2C(=O)N[C@@H](c12)c1cc(F)ccc1Cl | 1H NMR (400 MHz, DMSO-d6) 9.67 (s, 1H), 9.23 (s, 1H), 7.72-7.64 (m, 2H), 7.48 (s, 1H), 7.24 (td, J = 8.4, 3.1 Hz, 1H), 6.68 (s, 1H), 6.01 (s, 1H), 4.62 (d, J = 4.6 Hz, 1H), 4.00 (q, J = 5.6 Hz, 1H), 2.42 (q, J = 8.3 Hz, 1H), 1.75 (dt, J = 13.9, 7.1 Hz, 1H), 1.64-1.49 (m, 1H), 1.53-1.40 (m, 1H), 1.39 (dd, J = 9.4, 4.9 Hz, 3H), 1.17 (t, J = 7.2 Hz, 1H). | 467.05 | E | |
| I-2106 | 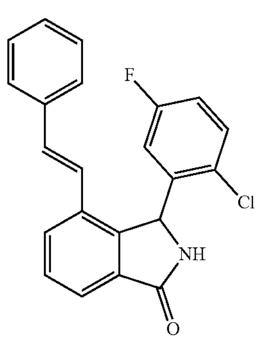 [SMILES: O=C1NC(c2cc(F)ccc2Cl)c2c(/C=C/c3ccccc3)cccc21] | Fc1ccc(Cl)c(c1)C1NC(=O)c2ccc(\C=C\c3ccccc3)c12 | 1H NMR (400 MHz, DMSO-d6) 9.17 (s, 1H), 7.97 (d, J = 7.7 Hz, 1H), 7.69 (d, J = 7.4 Hz, 1H), 7.60 (m, 2H), 7.42-7.32 (m, 4H), 7.28 (td, J = 5.9, 2.6 Hz, 1H), 7.24-7.17 (m, 2H), 6.91 (d, J = 16.3 Hz, 1H), 6.76-6.40 (s, 1H), 6.28 (s, 1H) | 364.1 | E | |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-2107 | 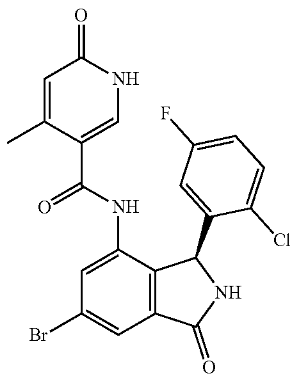 [SMILES: Cc1cc(=O)[nH]cc1C(=O)Nc1cc(Br)cc2c1[C@@H](c1cc(F)ccc1Cl)NC2=O] | Cc1cc(=O)[nH]cc1C(=O)Nc1cc(Br)cc2C(=O)N[C@@H](c12)c1cc(F)ccc1Cl | 1H NMR (400 MHz, DMSO-d6) Ã¤ 11.73 (s, 1H), 10.04 (s, 1H), 9.24 (s, 1H), 7.74 (d, J = 1.7 Hz, 1H), 7.67-7.62 (m, 1H), 7.46 (dd, J = 8.8, 5.1 Hz, 1H), 7.21 (td, J = 8.4, 3.1 Hz, 1H), 6.90 (s, 1H), 6.64 (s, 1H), 6.16 (s, 1H), 5.96 (s, 1H), 2.11 (s, 3H). | 492.15 | E | |
| I-2108 | 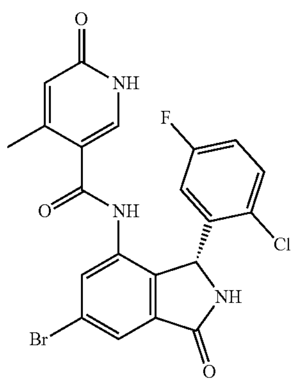 | Cc1cc(=O)[nH]cc1C(=O)Nc1cc(Br)cc2C(=O)N[C@H](c12)c1cc(F)ccc1Cl | 1H NMR (400 MHz, DMSO-d6) Ã¤ 11.72 (s, 1H), 10.05 (s, 1H), 9.24 (s, 1H), 7.74 (d, J = 1.7 Hz, 1H), 7.64 (s, 1H), 7.46 (dd, J = 8.7, 5.1 Hz, 1H), 7.21 (td, J = 8.4, 3.1 Hz, 1H), 6.90 (s, 1H), 6.65 (s, 1H), 6.16 (s, 1H), 5.97 (s, 1H), 2.11 (s, 3H). | 492.15 | E | |
| I-2109 | 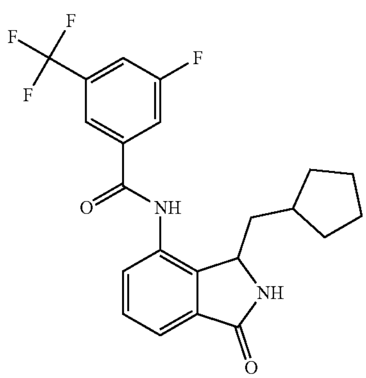 | Fc1cc(cc(c1)C(F)(F)F)C(=O)Nc1cccc2C(=O)NC(CC3CCCC3)c12 | (400 MHz, DMSO-d6) 10.78 (s, 1H), 8.88 (s, 1H), 8.17 (s, 1H), 8.12 (d, J = 8.9 Hz, 1H), 8.04 (d, J = 8.5 Hz, 1H), 7.60-7.50 (m, 3H), 4.77 (d, J = 7.2 Hz, 1H), 1.93-1.81 (m, 1H), 1.81-1.72 (m, 1H), 1.69-1.60 (m, 1H), 1.51-1.41 (m, 1H), 1.39-1.22 (m, 5H), 1.04 (tt, J = 15.2, 7.4 Hz, 1H), 0.94-0.81 (m, 1H). | 421.4 | D | |
| I-2110 | 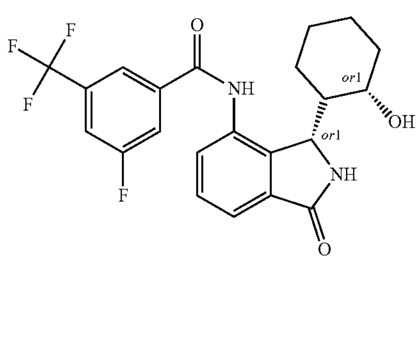 [SMILES: O=C(Nc1cccc2c1[C@H](C1CCCC[C@@H]1O)NC2=O)c1cc(F)cc(C(F)(F)F)c1] | O[C@H]1CCCC1[C@@H]1NC(=O)c2cccc(NC(=O)c3cc(F)cc(c3)C(F)(F)F)c12 | (400 MHz, DMSO-d6) 10.90 (s, 1H), 8.53 (s, 1H), 8.10 (s, 1H), 8.03 (t, J = 8.5 Hz, 2H), 7.71 (dd, J = 6.8, 2.1 Hz, 1H), 7.55-7.48 (m, 2H), 4.75 (d, J = 3.9 Hz, 1H), 4.25 (br s, 1H), 3.57 (s, 1H), 1.73-1.41 (m, 5H), 1.32-1.20 (m, 2H), 1.16-1.08 (m, 1H), 1.06-0.94 (m, 1H) [single diastereomer] | 437.4 | E | |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-2111 | 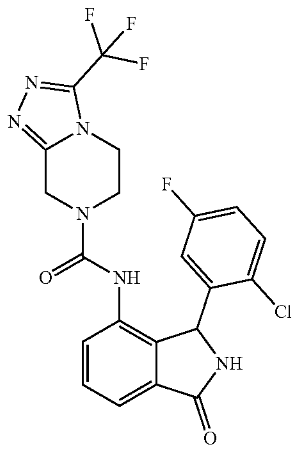 [SMILES: O=C1NC(c2cc(F)ccc2Cl)c2c(NC(=O)N3CCn4c(nnc4C(F)(F)F)C3)cccc21] | Fc1ccc(Cl)c(c1)C1NC(=O)c2cccc(NC(=O)N3CCn4c(C3)nnc4C(F)(F)F)c12 | NMR (400 MHz, DMSO-d6) 9.05 (br s, 1H), 8.98 (br s, 1H), 7.56 (d, J = 2.2 Hz, 2H), 7.34-7.25 (m, 1H), 7.19 (dd, J = 7.6, 5.4 Hz, 1H), 6.98 (td, J = 8.1, 2.4 Hz, 1H), 6.37 (br s, 1H), 5.95 (br s, 1H), 4.74 (d, J = 17.1 Hz, 1H), 4.43 (d, J = 16.9 Hz, 1H), 4.13-3.98 (m, 1H), 3.97-3.87 (m, 1H), 3.86-3.74 (m, 1H), 3.68-3.55 (m, 1H). | 495 | E | |
| I-2112 | 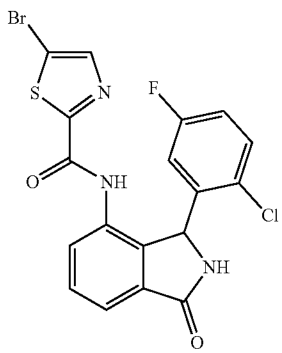 [SMILES: O=C(Nc1cccc2c1C(c1cc(F)ccc1Cl)NC2=O)c1ncc(Br)s1] | Fc1ccc(Cl)c(c1)C1NC(=O)c2cccc(NC(=O)c3ncc(Br)s3)c12 | NMR (400 MHz, DMSO-d6) 10.53 (br s, 1H), 9.13 (br s, 1H), 8.12 (s, 1H), 7.68 (d, J = 7.9 Hz, 1H), 7.64-7.51 (m, 2H), 7.33 (dd, J = 8.7, 4.9 Hz, 1H), 7.09 (td, J = 8.1, 3.1 Hz, 1H), 6.51 (br s, 1H), 6.07 (br s, 1H). | 468 | E | |
| I-2113 | 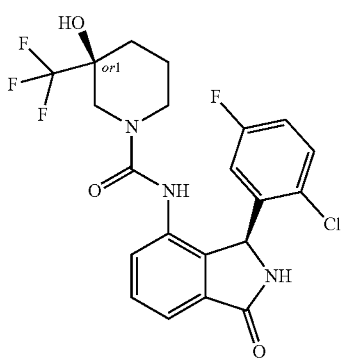 [SMILES: O=C1N[C@H](c2cc(F)ccc2Cl)c2c(NC(=O)N3CCC[C@@](O)(C(F)(F)F)C3)cccc21] | O[C@@]1(CCCN(C1)C(=O)Nc1cccc2C(=O)N[C@@H](c12)c1cc(F)ccc1Cl)C(F)(F)F | | 472 | E | |
| I-2114 | 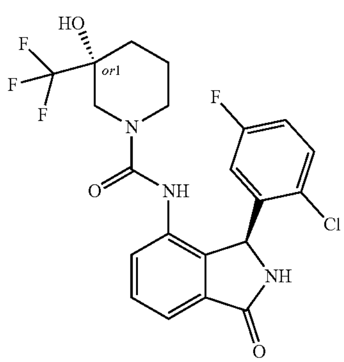 [SMILES: O=C1N[C@H](c2cc(F)ccc2Cl)c2c(NC(=O)N3CCC[C@](O)(C(F)(F)F)C3)cccc21] | O[C@]1(CCCN(C1)C(=O)Nc1cccc2C(=O)N[C@H](c12)c1cc(F)ccc1Cl)C(F)(F)F | | 472.1 | E | |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-2115 | 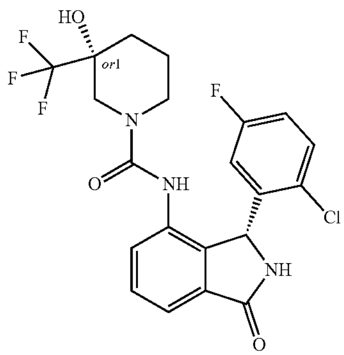 [SMILES: O=C1N[C@@H](c2cc(F)ccc2Cl)c2c(NC(=O)N3CCC[C@](O)(C(F)(F)F)C3)cccc21] | O[C@]1(CCCN(C1)C(=O)Nc1cccc2C(=O)N[C@@H](c12)c1cc c(F)ccc1Cl)C(F)(F)F | | 472.1 | E | |
| I-2116 | 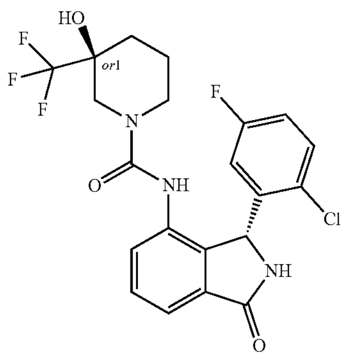 [SMILES: O=C1N[C@@H](c2cc(F)ccc2Cl)c2c(NC(=O)N3CCC[C@@](O)(C(F)(F)F)C3)cccc21] | O[C@@]1(CCCN(C1)C(=O)Nc1cccc2C(=O)N[C@H](c12)c1cc c(F)ccc1Cl)C(F)(F)F | | 472.1 | E | |
| I-2117 | 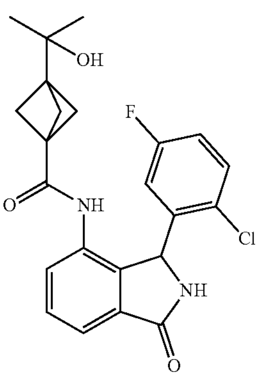 [SMILES: CC(C)(O)C12CC(C(=O)Nc3cccc4c3C(c3cc(F)ccc3Cl)NC4=O)(C1)C2] | CC(C)(O)C12CC(C1)(C2)C(=O)Nc1cccc2C(=O)NC(c12)c1cc(F)ccc1Cl | NMR (400 MHz, DMSO-d6) 9.38 (s, 1H), 9.05 (br s, 1H), 7.60 (dd, J = 7.4, 0.9 Hz, 1H), 7.55 (app. t, J = 7.5 Hz, 1H), 7.54-7.40 (m, 1H), 7.39 (dd, J = 7.6, 1.1 Hz, 1H), 7.24 (td, J = 8.4, 3.1 Hz, 1H), 6.56 (br s, 1H), 5.98 (br s, 1H), 4.17 (br s, 1H), 1.58 (s, 6H), 0.98 (s, 6H). | 429 | E | |
| I-2118 | 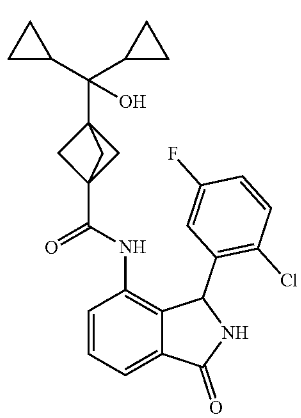 [SMILES: O=C1NC(c2cc(F)ccc2Cl)c2c(NC(=O)C34CC(C(O)(C5CC5)C5CC5)(C3)C4)cccc21] | OC(C1CC1)(C1CC1)C12CC(C1)(C2)C(=O)Nc1cccc2C(=O)NC(c12)c1cc c(F)ccc1Cl | NMR (400 MHz, DMSO-d6) 9.34 (s, 1H), 9.04 (br s, 1H), 7.59 (dd, J = 7.4, 1.0 Hz, 1H), 7.55 (app. t, J = 7.5 Hz, 1H), 7.51-7.42 (m, 1H), 7.40 (dd, J = 7.6, 1.2 Hz, 1H), 7.27-7.20 (m, 1H), 6.60 (br s, 1H), 5.99 (br s, 1H), 3.51 (s, 1H), 1.70 (s, 6H), 0.72-0.60 (m, 2H), 0.32-0.21 (m, 4H), 0.22-0.09 (m, 4H). | 481 | E | |

TABLE 2-continued

Representative Compounds of the Invention with Bioactivity Data.

| Ex. No. | Structure | SMILES | $^1$H NMR | MS | ADP-Glo IC$_{50}$ | MCF 10A IC$_{50}$ |
|---|---|---|---|---|---|---|
| I-2119 | 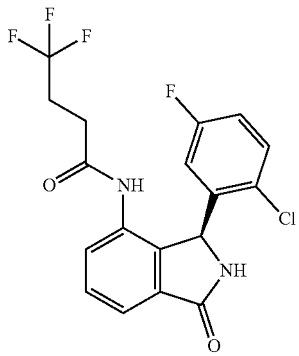 [SMILES: O=C(CCC(F)(F)F)Nc1cccc2c1[C@@H](c1cc(F)ccc1Cl)NC2=O] | Fc1ccc(Cl)c(c1)[C@H]1NC(=O)c2cccc(NC(=O)CCC(F)(F)F)c12 | 1H NMR (400 MHz, DMSO-d6) 9.85 (s, 1H), 9.09 (s, 1H), 7.63 (m, 2H), 7.58 (t, J = 7.5 Hz, 1H), 7.50 (s, 1H), 7.39 (d, J = 7.6 Hz, 1H), 7.24 (td, J = 8.4, 3.1 Hz, 1H), 5.97 (s, 1H), 2.33 (dq, J = 14.9, 10.4, 8.9 Hz, 3H), 2.17 (q, J = 9.3, 8.6 Hz, 1H). | 401.15 | E | |
| I-2120 | 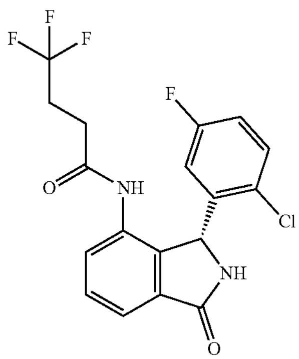 [SMILES: O=C(CCC(F)(F)F)Nc1cccc2c1[C@H](c1cc(F)ccc1Cl)NC2=O] | Fc1ccc(Cl)c(c1)[C@@H]1NC(=O)c2cccc(NC(=O)CCC(F)(F)F)c12 | 1H NMR (400 MHz, DMSO-d6) 9.85 (s, 1H), 9.09 (s, 1H), 7.63 (m, 2H), 7.58 (t, J = 7.5 Hz, 1H), 7.50 (s, 1H), 7.39 (d, J = 7.6 Hz, 1H), 7.24 (td, J = 8.4, 3.1 Hz, 1H), 5.97 (s, 1H), 2.33 (dq, J = 14.9, 10.4, 8.9 Hz, 3H), 2.17 (q, J = 9.3, 8.6 Hz, 1H). | 401.2 | E | |
| I-2121 | 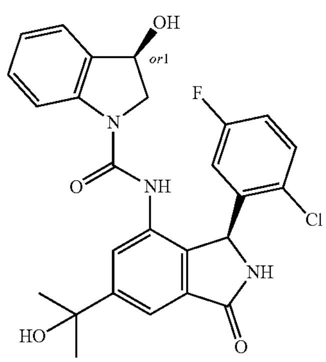 [SMILES: CC(C)(O)c1cc(NC(=O)N2C[C@H](O)c3ccccc32)c2c(c1)C(=O)N[C@@H]2c1cc(F)ccc1Cl] | CC(C)(O)c1cc2C(=O)N[C@@H](c2c(NC(=O)N2C[C@H](O)c3ccccc23)c1)c1cc(F)ccc1Cl | 1H NMR (400 MHz, DMSO-d6) 9.01 (s, 1H), 8.50 (s, 1H), 7.74-7.63 (m, 2H), 7.56 (d, J = 1.7 Hz, 1H), 7.38-7.28 (m, 2H), 7.23-7.14 (m, 1H), 7.09 (td, J = 8.4, 3.1 Hz, 1H), 6.95 (t, J = 7.4 Hz, 1H), 6.53 (s, 1H), 6.07 (s, 1H), 5.60 (d, J = 5.0 Hz, 1H), 5.26 (s, 1H), 5.15 (dd, J = 8.4, 4.3 Hz, 1H), 3.98 (dd, J = 11.1, 8.0 Hz, 1H), 3.20 (dt, J = 10.7, 5.2 Hz, 1H), 1.50 (s, 6H). | 496.2 | D | |
| I-2122 | 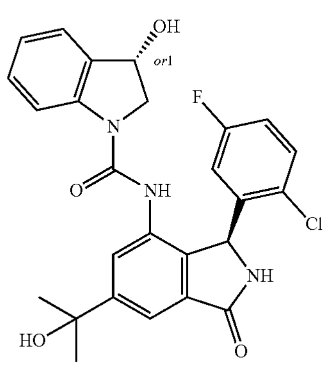 [SMILES: CC(C)(O)c1cc(NC(=O)N2C[C@@H](O)c3ccccc32)c2c(c1)C(=O)N[C@@H]2c1cc(F)ccc1Cl] | CC(C)(O)c1cc2C(=O)N[C@@H](c2c(NC(=O)N2C[C@@H](O)c3ccccc23)c1)c1cc(F)ccc1Cl | 1H NMR (400 MHz, DMSO-d6) 8.99 (s, 1H), 8.63 (s, 1H), 7.84 (d, J = 8.2 Hz, 1H), 7.66 (d, J = 1.5 Hz, 1H), 7.51 (s, 1H), 7.40-7.30 (m, 2H), 7.24 (t, J = 7.7 Hz, 1H), 7.16 (td, J = 8.4, 3.1 Hz, 1H), 6.98 (t, J = 7.5 Hz, 1H), 6.54 (s, 1H), 5.98 (s, 1H), 5.64 (d, J = 6.0 Hz, 1H), 5.27 (s, 1H), 5.09 (s, 1H), 3.72 (dd, J = 11.2, 3.5 Hz, 1H), 3.21 (s, 1H), 1.50 (s, 6H). | 496.2 | E | |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-2123 | 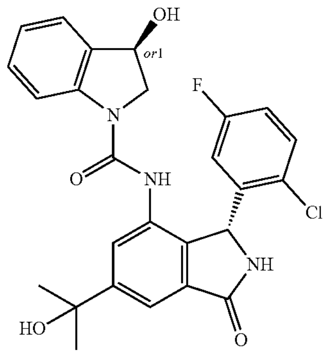 [SMILES: CC(C)(O)c1cc(NC(=O)N2C[C@H](O)c3ccccc32)c2c(c1)C(=O)N[C@H]2c1cc(F)ccc1Cl] | CC(C)(O)c1cc2C(=O)N[C@H](c2c(NC(=O)N2C[C@H](O)c3cccc23)c1)c1cc(F)ccc1Cl | 1H NMR (400 MHz, DMSO-d6) 9.02 (s, 1H), 8.52 (s, 1H), 7.74-7.65 (m, 2H), 7.56 (d, J = 1.6 Hz, 1H), 7.38-7.28 (m, 2H), 7.23-7.14 (m, 1H), 7.10 (td, J = 8.4, 3.1 Hz, 1H), 6.99-6.91 (m, 1H), 6.53 (s, 1H), 6.08 (s, 1H), 5.62 (s, 1H), 5.27 (s, 1H), 5.15 (dd, J = 8.2, 3.9 Hz, 1H), 3.99 (dd, J = 11.1, 8.0 Hz, 1H), 3.21 (s, 1H), 1.50 (s, 6H). | 496.2 | C | |
| I-2124 | 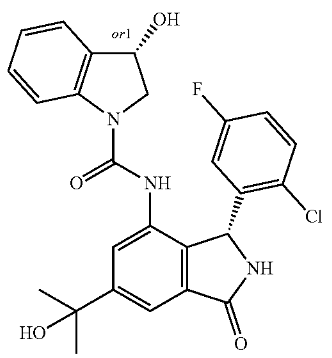 [SMILES: CC(C)(O)c1cc(NC(=O)N2C[C@@H](O)c3ccccc32)c2c(c1)C(=O)N[C@H]2c1cc(F)ccc1Cl] | CC(C)(O)c1cc2C(=O)N[C@H](c2c(NC(=O)N2C[C@@H](O)c3ccccc23)c1)c1cc(F)ccc1Cl | 1H NMR (400 MHz, DMSO-d6) 8.99 (s, 1H), 8.63 (s, 1H), 7.84 (d, J = 8.2 Hz, 1H), 7.66 (d, J = 1.5 Hz, 1H), 7.51 (s, 1H), 7.40-7.30 (m, 2H), 7.24 (t, J = 7.7 Hz, 1H), 7.16 (td, J = 8.3, 3.1 Hz, 1H), 6.98 (t, J = 7.4 Hz, 1H), 6.53 (s, 1H), 5.98 (s, 1H), 5.65 (s, 1H), 5.27 (s, 1H), 5.08 (s, 1H), 3.72 (dd, J = 11.4, 3.5 Hz, 1H), 3.21 (s, 1H), 1.50 (s, 6H). | 496.2 | A | B |
| I-2125 | 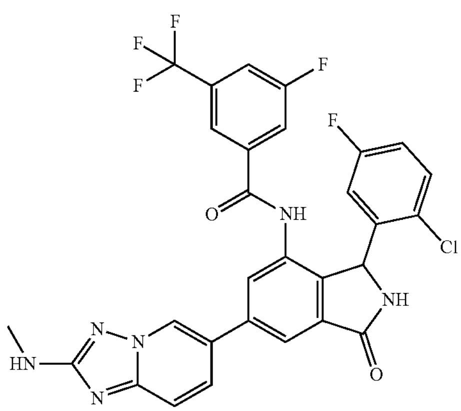 [SMILES: CNc1nc2ccc(-c3cc(NC(=O)c4cc(F)cc(C(F)(F)F)c4)c4c(c3)C(=O)NC4c3cc(F)ccc3Cl)cn2n1] | CNc1nc2ccc(cn2n1)-c1cc2C(=O)NC(c2c(NC(=O)c2cc(F)cc(c2)C(F)(F)F)c1)c1cc(F)ccc1Cl | 1H NMR (400 MHz, DMSO-d6) 10.60 (s, 1H), 9.39-8.97 (m, 2H), 8.04 (d, J = 1.6 Hz, 1H), 7.97 (dt, J = 8.7, 2.1 Hz, 1H), 7.93-7.85 (m, 2H), 7.81-7.69 (m, 2H), 7.54-7.47 (m, 1H), 7.34 (dd, J = 8.9, 5.2 Hz, 1H), 7.11 (td, J = 8.4, 3.1 Hz, 1H), 6.58 (q, J = 4.9 Hz, 2H), 6.05 (s, 1H), 2.86 (d, J = 4.9 Hz, 3H) | 613.15 | A | A |
| I-2126 | 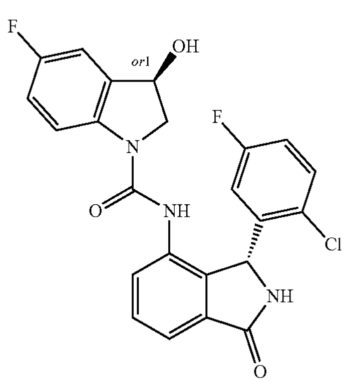 [SMILES: O=C1N[C@@H](c2cc(F)ccc2Cl)c2c(NC(=O)N3C[C@H](O)c4cc(F)ccc43)cccc21] | O[C@H]1CN(C(=O)Nc2cccc3C(=O)N[C@H](c23)c2cc(F)ccc2Cl)c2ccc(F)cc12 | 1H NMR (400 MHz, DMSO-d6) 9.06 (s, 1H), 8.50 (s, 1H), 7.70 (dd, J = 8.8, 4.7 Hz, 1H), 7.60-7.57 (t, J = 7.4 Hz, 2H), 7.44 (dd, J = 7.3, 1.6 Hz, 1H), 7.35 (dd, J = 8.9, 5.2 Hz, 1H), 7.15-7.03 (m, 3H), 6.57 (s, 1H), 6.09 (s, 1H), 5.73 (d, J = 5.1 Hz, 1H), 5.15 (dt, J = 8.4, 4.5 Hz, 1H), 3.97 (dd, J = 11.0, 8.1 Hz, 1H), 3.23 (dd, J = 11.1, 4.1 Hz, 1H). | 456.05 | C | |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-2127 | 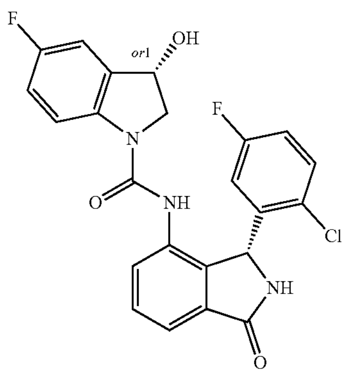 [SMILES: O=C1N[C@@H](c2cc(F)ccc2Cl)c2c(NC(=O)N3C[C@@H](O)c4cc(F)ccc43)cccc21] | O[C@@H]1CN(C(=O)Nc2cccc3C(=O)N[C@H](c23)c2cc(F)ccc2Cl)c2ccc(F)cc12 | 1H NMR (400 MHz, DMSO-d6) 9.04 (s, 1H), 8.62 (s, 1H), 7.83 (dd, J = 8.8, 4.7 Hz, 1H), 7.62-7.52 (m, 2H), 7.37 (dd, J = 8.8, 5.3 Hz, 2H), 7.21-7.10 (m, 2H), 7.08 (td, J = 9.0, 2.8 Hz, 1H), 6.53 (s, 1H), 6.00 (s, 1H), 5.76 (d, J = 6.0 Hz, 1H), 5.08 (s, 1H), 3.71 (dd, J = 11.3, 3.6 Hz, 1H), 3.31 (s, 1H). | 456.05 | A | A |
| I-2128 | 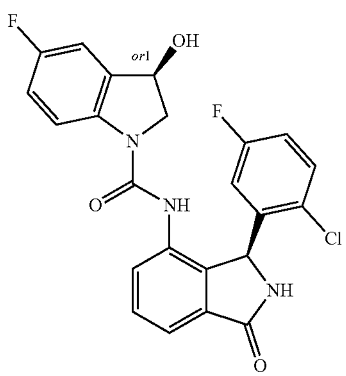 [SMILES: O=C1N[C@H](c2cc(F)ccc2Cl)c2c(NC(=O)N3C[C@H](O)c4cc(F)ccc43)cccc21] | O[C@H]1CN(C(=O)Nc2cccc3C(=O)N[C@@H](c23)c2cc(F)ccc2Cl)c2cc(F)cc12 | 1H NMR (400 MHz, DMSO-d6) 9.04 (s, 1H), 8.63 (s, 1H), 7.83 (dd, J = 8.9, 4.7 Hz, 1H), 7.62-7.52 (m, 2H), 7.37 (dd, J = 8.8, 5.6 Hz, 2H), 7.15-7.08 (m, 3H), 6.54 (s, 1H), 6.00 (s, 1H), 5.76 (d, J = 6.0 Hz, 1H), 5.08 (dt, J = 8.2, 4.4 Hz, 1H), 3.71 (dd, J = 11.3, 3.7 Hz, 1H), 3.25 (s, 1H). | 456.1 | E | |
| I-2129 | 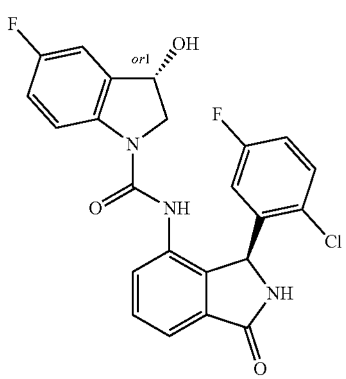 [SMILES: O=C1N[C@H](c2cc(F)ccc2Cl)c2c(NC(=O)N3C[C@@H](O)c4cc(F)ccc43)cccc21] | O[C@@H]1CN(C(=O)Nc2cccc3C(=O)N[C@H](c23)c2cc(F)ccc2Cl)c2ccc(F)cc12 | 1H NMR (400 MHz, DMSO-d6) 9.06 (s, 1H), 8.50 (s, 1H), 7.70 (dd, J = 8.9, 4.7 Hz, 1H), 7.64-7.53 (m, 2H), 7.44 (dd, J = 7.3, 1.6 Hz, 1H), 7.35 (dd, J = 8.9, 5.2 Hz, 1H), 7.12-6.98 (m, 3H), 6.56 (s, 1H), 6.09 (s, 1H), 5.73 (d, J = 5.0 Hz, 1H), 5.15 (dt, J = 8.6, 4.5 Hz, 1H), 3.97 (dd, J = 11.1, 8.1 Hz, 1H), 3.23 (dd, J = 11.0, 4.1 Hz, 1H). | 456.05 | E | |
| I-2130 | 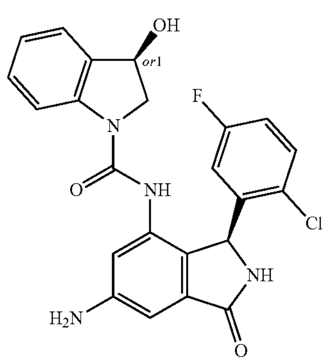 [SMILES: Nc1cc(NC(=O)N2C[C@H](O)c3ccccc32)c2c(c1)C(=O)N[C@@H]2c1cc(F)ccc1Cl] | Nc1cc2C(=O)N[C@@H](c2c(NC(=O)N2C[C@H](O)c3ccccc23)c1)c1cc(F)ccc1Cl | 1H NMR (400 MHz, DMSO-d6) 8.80 (s, 1H), 8.16 (s, 1H), 7.69 (d, J = 8.1 Hz, 1H), 7.36-7.26 (m, 2H), 7.22-7.13 (m, 1H), 7.06 (ddd, J = 8.8, 7.9, 3.1 Hz, 1H), 6.93 (td, J = 7.4, 1.1 Hz, 1H), 6.73 (dd, J = 16.6, 2.0 Hz, 2H), 6.53 (s, 1H), 5.94 (s, 1H), 5.59 (d, J = 5.3 Hz, 1H), 5.50 (s, 2H), 5.12 (dt, J = 8.7, 4.5 Hz, 1H), 3.85 (dd, J = 11.1, 8.0 Hz, 1H), 3.27 (dd, J = 11.0, 3.9 Hz, 1H). | 453.15 | D | |

TABLE 2-continued

Representative Compounds of the Invention with Bioactivity Data.

| Ex. No. | Structure | SMILES | ¹H NMR | MS | ADP-Glo IC₅₀ | MCF 10A IC₅₀ |
|---|---|---|---|---|---|---|
| I-2131 | 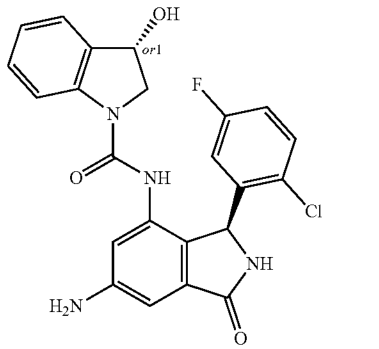 [SMILES: Nc1cc(NC(=O)N2C[C@@H](O)c3ccccc32)c2c(c1)C(=O)N[C@@H]2c1cc(F)ccc1Cl] | Nc1cc2C(=O)N[C@@H](c2c(NC(=O)N2C[C@@H](O)c3cccc23)c1)c1cc(F)ccc1Cl | 1H NMR (400 MHz, DMSO-d6) 8.77 (s, 1H), 8.30 (s, 1H), 7.82 (d, J = 8.1 Hz, 1H), 7.37-7.28 (m, 2H), 7.26-7.17 (m, 1H), 7.12 (td, J = 8.3, 3.1 Hz, 1H), 6.95 (t, J = 7.4 Hz, 1H), 6.74 (d, J = 2.0 Hz, 1H), 6.63 (d, J = 2.0 Hz, 1H), 6.52 (s, 1H), 5.84 (s, 1H), 5.66 (s, 1H), 5.50 (s, 2H), 5.07 (dd, J = 8.1, 3.5 Hz, 1H), 3.63 (dd, J = 11.3, 3.6 Hz, 1H), 3.25 (d, J = 9.9 Hz, 1H). | 453.15 | D | |
| I-2132 | 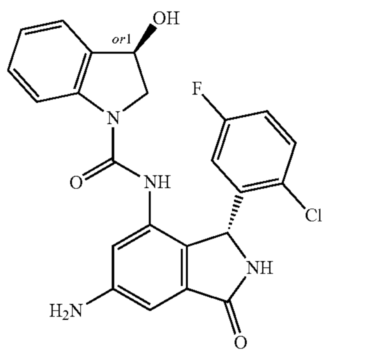 [SMILES: Nc1cc(NC(=O)N2C[C@H](O)c3ccccc32)c2c(c1)C(=O)N[C@H]2c1cc(F)ccc1Cl] | Nc1cc2C(=O)N[C@H](c2c(NC(=O)N2C[C@H](O)c3cccc23)c1)c1cc(F)ccc1Cl | 1H NMR (400 MHz, DMSO-d6) 8.80 (s, 1H), 8.17 (s, 1H), 7.69 (d, J = 8.1 Hz, 1H), 7.36-7.26 (m, 2H), 7.17 (td, J = 7.7, 1.4 Hz, 1H), 7.10-7.01 (m, 1H), 6.93 (td, J = 7.4, 1.0 Hz, 1H), 6.73 (d, J = 16.7, 2.0 Hz, 2H), 6.53 (s, 1H), 5.94 (s, 1H), 5.59 (d, J = 5.3 Hz, 1H), 5.50 (s, 2H), 5.12 (dt, J = 8.4, 4.3 Hz, 1H), 3.85 (dd, J = 11.1, 8.0 Hz, 1H), 3.27 (dd, J = 11.0, 3.9 Hz, 1H). | 453.1 | A | |
| I-2133 | 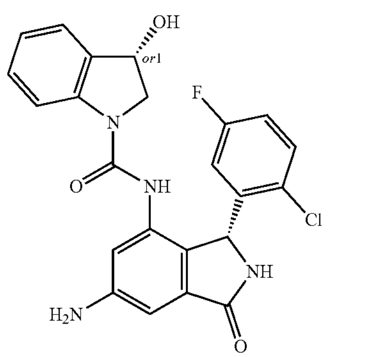 [SMILES: Nc1cc(NC(=O)N2C[C@@H](O)c3ccccc32)c2c(c1)C(=O)N[C@H]2c1cc(F)ccc1Cl] | Nc1cc2C(=O)N[C@H](c2c(NC(=O)N2C[C@@H](O)c3ccccc23)c1)c1cc(F)ccc1Cl | 1H NMR (400 MHz, DMSO-d6) 8.76 (s, 1H), 8.28 (s, 1H), 7.82 (d, J = 8.1 Hz, 1H), 7.37-7.28 (m, 2H), 7.22 (t, J = 7.7 Hz, 1H), 7.12 (td, J = 8.3, 3.1 Hz, 1H), 7.00-6.91 (m, 1H), 6.74 (d, J = 2.0 Hz, 1H), 6.62 (d, J = 2.0 Hz, 1H), 6.52 (s, 1H), 5.84 (s, 1H), 5.60 (d, J = 6.1 Hz, 1H), 5.49 (s, 2H), 5.07 (s, 1H), 3.62 (dd, J = 11.3, 3.6 Hz, 1H), 3.24 (s, 1H). | 453.1 | A | A |
| I-2134 | 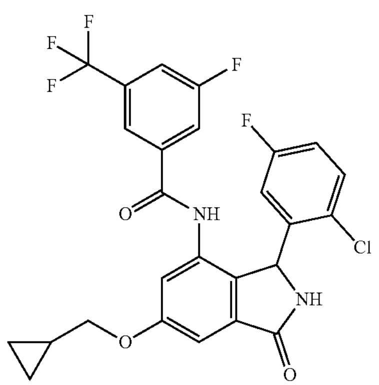 [SMILES: O=C(Nc1cc(OCC2CC2)cc2c1C(c1cc(F)ccc1Cl)NC2=O)c1cc(F)cc(C(F)(F)F)c1] | Fc1ccc(Cl)c(c1)C1NC(=O)c2cc(OCC3CC3)cc(NC(=O)c3cc(F)cc(c3)C(F)(F)F)c12 | 1H NMR (400 MHz, DMSO-d6) 10.43 (s, 1H), 9.11 (s, 1H), 7.95 (d, J = 8.4 Hz, 1H), 7.72 (d, J = 9.1 Hz, 1H), 7.64 (s, 1H), 7.31 (dd, J = 8.9, 5.1 Hz, 1H), 7.18 (d, J = 2.3 Hz, 1H), 7.13-7.05 (m, 2H), 6.56 (s, 1H), 5.93 (s, 0H), 3.96 (d, J = 7.0 Hz, 2H), 1.27 (dd, J = 12.1, 7.1 Hz, 1H), 0.65-0.56 (m, 2H), 0.42-0.33 (m, 2H). | 537.15 | B | |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-2135 | 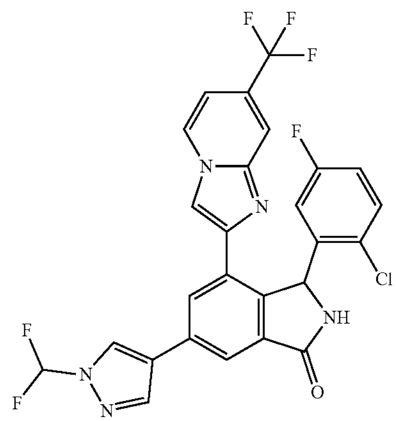 [SMILES: O=C1NC(c2cc(F)ccc2Cl)c2c1cc(-c1cnn(C(F)F)c1)cc2-c1cn2ccc(C(F)(F)F)cc2n1] | FC(F)n1cc(cn1)-c1cc2C(=O)NC(c2c(c1)-c1cn2ccc(cc2n1)C(F)(F)F)c1cc(F)ccc1Cl | 1H NMR (400 MHz, DMSO-d6) Ä¤ 9.28 (s, 1H), 9.04 (s, 1H), 8.72 (d, J = 7.2 Hz, 1H), 8.66 (s, 1H), 8.56 (s, 1H), 8.47 (s, 1H), 8.14 (d, J = 1.7 Hz, 1H), 8.06 (s, 0H), 7.91 (s, OH), 7.79 (d, J = 21.3 Hz, 1H), 7.38 (s, 1H), 7.17 (dd, J = 7.2, 1.9 Hz, 2H), 6.96 (td, J = 8.4, 3.1 Hz, 1H), 6.70 (s, 1H). | 562 | D | |
| I-2136 | 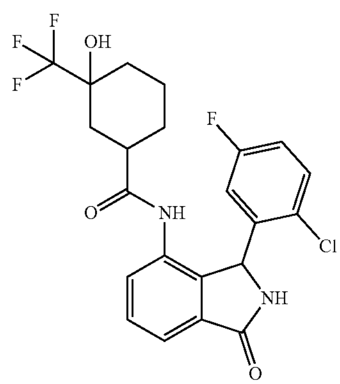 [SMILES: O=C1NC(c2cc(F)ccc2Cl)c2c(NC(=O)C3CCCC(O)(C(F)(F)F)C3)cccc21] | OC1(CCCC(C1)C(=O)Nc1cccc2C(=O)NC(c12)c1cc(F)ccc1Cl)C(F)(F)F | | 471.2 | E | |
| I-2137 | 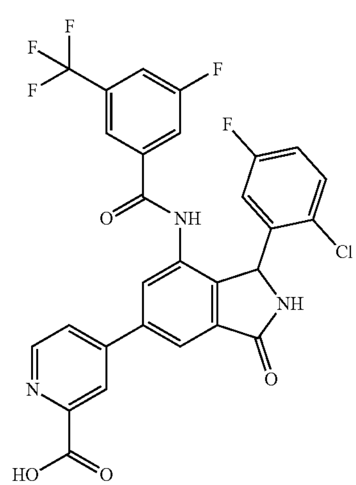 [SMILES: O=C(Nc1cc(-c2ccnc(C(=O)O)c2)cc2c1C(c1cc(F)ccc1Cl)NC2=O)c1cc(F)cc(C(F)(F)F)c1] | OC(=O)c1cc(ccn1)-c1cc2C(=O)NC(c2c(NC(=O)c2cc(F)cc(c2)C(F)(F)F)c1)c1cc(F)ccc1Cl | 1H NMR (400 MHz, DMSO-d6) 10.65 (s, 1H), 9.30 (s, 1H), 8.44 (dd, J = 51.6, 28.1 Hz, 2H), 8.26-7.91 (m, 5H), 7.78 (d, J = 8.8 Hz, 1H), 7.71 (s, 1H), 7.34 (dd, J = 8.9, 5.2 Hz, 1H), 7.12 (d, J = 8.1 Hz, 1H), 6.09 (s, 1H). | 588.25 | A | |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-2138 | 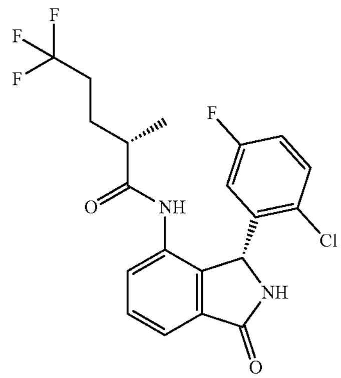 [SMILES: C[C@@H](CCC(F)(F)F)C(=O)Nc1cccc2c1[C@H](c1cc(F)ccc1Cl)NC2=O] | C[C@@H](CCC(F)(F)F)C(=O)Nc1cccc2C(=O)N[C@@H](c12)c1cc(F)ccc1Cl | 1H NMR (400 MHz, DMSO-d6) 9.80 (s, 1H), 9.10 (s, 1H), 7.65-7.55 (m, 2H), 7.47 (td, J = 7.5, 3.0 Hz, 2H), 7.21 (td, J = 8.4, 3.1 Hz, 1H), 6.43 (s, 1H), 6.15 (s, 1H), 2.28 (p, J = 6.9 Hz, 1H), 2.09-1.89 (s, 2H), 1.51-1.38 (m, 1H), 1.32 (tt, J = 12.2, 5.9 Hz, 1H), 0.85 (d, J = 6.8 Hz, 3H). | 429.2 | D | |
| I-2139 | 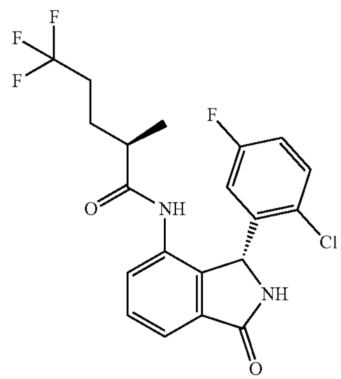 [SMILES: C[C@H](CCC(F)(F)F)C(=O)Nc1cccc2c1[C@H](c1cc(F)ccc1Cl)NC2=O] | C[C@H](CCC(F)(F)F)C(=O)Nc1cccc2C(=O)N[C@H](c12)c1cc(F)ccc1Cl | 1H NMR (400 MHz, DMSO-d6) 9.82 (s, 1H), 9.10 (s, 1H), 7.65-7.54 (m, 2H), 7.50 (dd, J = 8.9, 5.1 Hz, 1H), 7.43 (dd, J = 7.4, 1.5 Hz, 1H), 7.21 (td, J = 8.4, 3.1 Hz, 1H), 6.46 (s, 1H), 6.10 (s, 1H), 2.27 (dq, J = 13.9, 6.6 Hz, 1H), 2.15-1.85 (m, 2H), 1.60 (dddd, J = 13.1, 11.2, 8.3, 4.9 Hz, 1H), 1.39 (ddt, J = 13.3, 11.2, 5.5 Hz, 1H), 0.77 (d, J = 6.9 Hz, 3H). | 429.2 | E | |
| I-2140 | 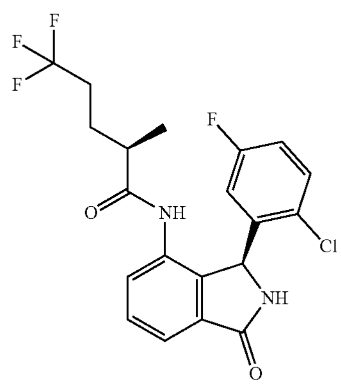 [SMILES: C[C@H](CCC(F)(F)F)C(=O)Nc1cccc2c1[C@@H](c1cc(F)ccc1Cl)NC2=O] | C[C@H](CCC(F)(F)F)C(=O)Nc1cccc2C(=O)N[C@@H](c12)c1cc(F)ccc1Cl | 1H NMR (400 MHz, DMSO-d6) 9.80 (s, 1H), 9.10 (s, 1H), 7.65-7.55 (m, 2H), 7.47 (td, J = 8.3, 7.2, 3.5 Hz, 2H), 7.21 (ddd, J = 8.8, 8.0, 3.1 Hz, 1H), 6.43 (s, 1H), 6.15 (s, 1H), 2.27 (p, J = 6.9 Hz, 1H), 2.09-1.89 (s, 2H), 1.51-1.38 (m, 1H), 1.32 (tq, J = 12.3, 5.8 Hz, 1H), 0.85 (d, J = 6.9 Hz, 3H). | 429.2 | E | |
| I-2141 | 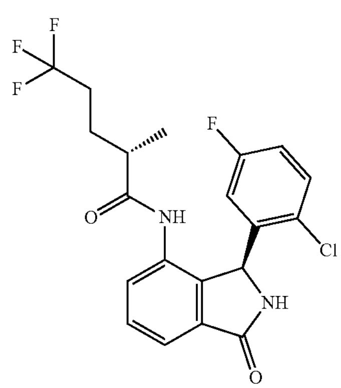 [SMILES: C[C@@H](CCC(F)(F)F)C(=O)Nc1cccc2c1[C@@H](c1cc(F)ccc1Cl)NC2=O] | C[C@@H](CCC(F)(F)F)C(=O)Nc1cccc2C(=O)N[C@H](c12)c1cc(F)ccc1Cl | 1H NMR (400 MHz, DMSO-d6) 9.82 (s, 1H), 9.10 (s, 1H), 7.65-7.54 (m, 2H), 7.50 (dd, J = 8.9, 5.1 Hz, 1H), 7.43 (dd, J = 7.4, 1.5 Hz, 1H), 7.21 (td, J = 8.4, 3.1 Hz, 1H), 6.46 (s, 1H), 6.10 (s, 1H), 2.27 (dq, J = 13.9, 6.6 Hz, 1H), 2.15-1.85 (m, 2H), 1.60 (dddd, J = 13.1, 11.2, 8.3, 4.9 Hz, 1H), 1.39 (ddt, J = 13.3, 11.2, 5.5 Hz, 1H), 0.77 (d, J = 6.9 Hz, 3H). | 429.2 | E | |

TABLE 2-continued

Representative Compounds of the Invention with Bioactivity Data.

| Ex. No. | Structure | SMILES | $^1$H NMR | MS | ADP-Glo IC$_{50}$ | MCF 10A IC$_{50}$ |
|---|---|---|---|---|---|---|
| I-2142 | 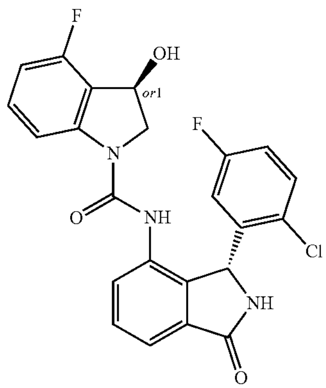 [SMILES: O=C1N[C@@H](c2cc(F)ccc2Cl)c2c(NC(=O)N3C[C@H](O)c4c(F)cccc43)cccc21] | O[C@@H]1CN(C(=O)Nc2ccc3C(=O)N[C@H](c23)c2cc(F)ccc2Cl)c2cccc(F)c12 | 1H NMR (400 MHz, DMSO-d6) 9.05 (s, 1H), 8.71 (s, 1H), 7.74 (d, J = 8.1 Hz, 1H), 7.64-7.53 (m, 2H), 7.43-7.33 (m, 2H), 7.31 (td, J = 8.2, 5.9 Hz, 1H), 7.17 (td, J = 8.4, 3.1 Hz, 1H), 6.78 (t, J = 8.6 Hz, 1H), 6.54 (s, 1H), 6.01 (s, 1H), 5.80 (d, J = 6.8 Hz, 1H), 5.24 (td, J = 7.2, 2.2 Hz, 1H), 3.80 (dd, J = 11.5, 2.3 Hz, 1H), 3.21 (s, 1H). | 456.2 | A | A |
| I-2143 | 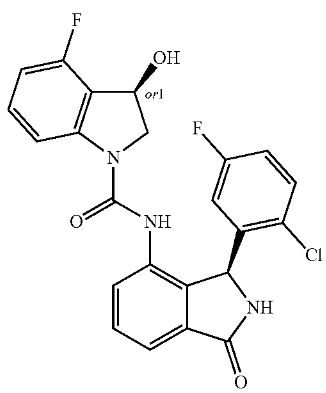 [SMILES: O=C1N[C@H](c2cc(F)ccc2Cl)c2c(NC(=O)N3C[C@H](O)c4c(F)cccc43)cccc21] | O[C@@H]1CN(C(=O)Nc2ccc3C(=O)N[C@@H](c23)c2cc(F)ccc2Cl)c2cccc(F)c12 | 1H NMR (400 MHz, DMSO-d6) 9.09 (s, 1H), 8.59 (s, 1H), 7.65-7.54 (m, 2H), 7.53-7.42 (m, 2H), 7.35 (dd, J = 8.9, 5.1 Hz, 1H), 7.24 (td, J = 8.2, 5.9 Hz, 1H), 7.09 (td, J = 8.4, 3.1 Hz, 1H), 6.74 (t, J = 8.6 Hz, 1H), 6.56 (s, 1H), 6.10 (s, 1H), 5.75 (d, J = 5.6 Hz, 1H), 5.30 (ddd, J = 7.8, 5.7, 2.4 Hz, 1H), 3.92 (dd, J = 11.3, 7.5 Hz, 1H), 3.38 (dd, J = 11.3, 2.5 Hz, 1H). | 456.2 | C | |
| I-2144 | 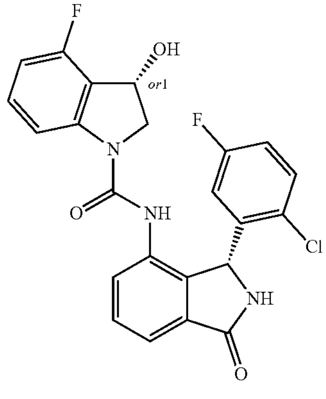 [SMILES: O=C1N[C@@H](c2cc(F)ccc2Cl)c2c(NC(=O)N3C[C@@H](O)c4c(F)cccc43)cccc21] | O[C@H]1CN(C(=O)Nc2cccc3C(=O)N[C@H](c23)c2cc(F)ccc2Cl)c2cccc(F)c12 | 1H NMR (400 MHz, DMSO-d6) 9.08 (s, 1H), 8.59 (s, 1H), 7.61-7.58 (dd, J = 7.5, 1.5 Hz, 2H), 7.50-7.42 (t, J = 7.4 Hz, 2H), 7.35 (dd, J = 8.9, 5.1 Hz, 1H), 7.24 (td, J = 8.2, 5.9 Hz, 1H), 7.09 (td, J = 8.4, 3.1 Hz, 1H), 6.74 (t, J = 8.6 Hz, 1H), 6.56 (s, 1H), 6.10 (s, 1H), 5.75 (d, J = 5.6 Hz, 1H), 5.29 (ddd, J = 7.9, 5.5, 2.4 Hz, 1H), 3.92 (dd, J = 11.3, 7.5 Hz, 1H), 3.37 (dd, J = 11.5, 2.6 Hz, 1H). | 456.2 | D | |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-2145 | 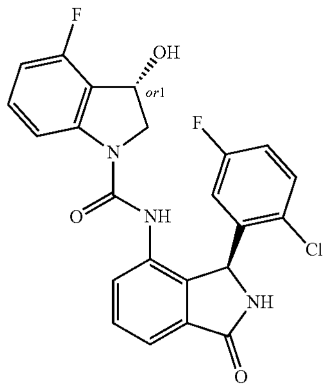 [SMILES: O=C1N[C@H](c2cc(F)ccc2Cl)c2c(NC(=O)N3C[C@@H](O)c4c(F)cccc43)cccc21] | O[C@H]1CN(C(=O)Nc2cccc3C(=O)N[C@@H](c23)c2cc(F)ccc2Cl)c2ccc(F)c12 | 1H NMR (400 MHz, DMSO-d6) 9.05 (s, 1H), 8.71 (s, 1H), 7.74 (d, J = 8.1 Hz, 1H), 7.64-7.53 (m, 2H), 7.43-7.35 (m, 2H), 7.31 (td, J = 8.2, 5.9 Hz, 1H), 7.17 (td, J = 8.4, 3.1 Hz, 1H), 6.78 (t, J = 8.6 Hz, 1H), 6.54 (s, 1H), 6.01 (s, 1H), 5.80 (d, J = 6.7 Hz, 1H), 5.28-5.20 (m, 1H), 3.80 (dd, J = 11.6, 2.3 Hz, 1H), 3.21 (s, 1H). | 456.2 | D | |
| I-2146 | 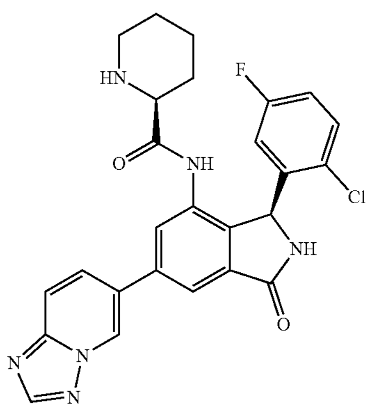 [SMILES: O=C1N[C@H](c2cc(F)ccc2Cl)c2c(NC(=O)[C@@H]3CCCCN3)cc(-c3ccc4ncnn4c3)cc21] | Fc1ccc(Cl)c(c1)[C@@H]1NC(=O)c2cc(cc(NC(=O)[C@H]3CCCN3)c12)-c1ccc2ncnn2c1 | 1H NMR (400 MHz, DMSO-d6) Ä¤ 9.40 (dd, J = 1.8, 0.9 Hz, 1H), 9.24 (s, 1H), 8.58 (s, 1H), 8.25 (d, J = 25.7 Hz, 1H), 8.06 (dd, J = 9.3, 1.8 Hz, 1H), 8.03-7.94 (m, 2H), 7.56 (s, 1H), 7.30 (td, J = 8.3, 3.1 Hz, 1H), 6.17 (s, 1H), 3.06 (d, J = 9.4 Hz, 1H), 2.82-2.64 (m, 1H), 2.43 (d, J = 11.3 Hz, 1H), 1.58-1.00 (m, 6H), 0.99-0.85 (m, 1H). | 505.35 | E | |
| I-2147 | 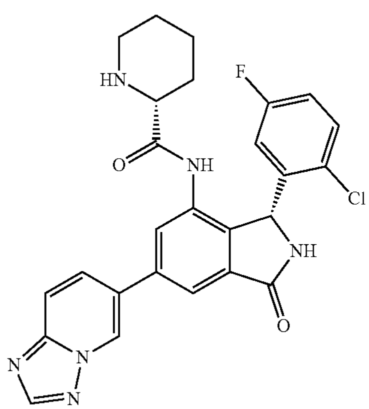 [SMILES: O=C1N[C@@H](c2cc(F)ccc2Cl)c2c(NC(=O)[C@H]3CCCCN3)cc(-c3ccc4ncnn4c3)cc21] | Fc1ccc(Cl)c(c1)[C@H]1NC(=O)c2cc(cc(NC(=O)[C@@H]3CCCN3)c12)-c1ccc2ncnn2c1 | 1H NMR (400 MHz, DMSO-d6) Ä¤ 9.40 (dd, J = 1.8, 0.9 Hz, 1H), 9.24 (s, 1H), 8.58 (s, 1H), 8.25 (d, J = 25.7 Hz, 1H), 8.06 (dd, J = 9.3, 1.8 Hz, 1H), 8.03-7.94 (m, 2H), 7.56 (s, 1H), 7.30 (td, J = 8.3, 3.1 Hz, 1H), 6.17 (s, 1H), 3.06 (d, J = 9.4 Hz, 1H), 2.82-2.64 (m, 1H), 2.43 (d, J = 11.3 Hz, 1H), 1.58-1.00 (m, 6H), 0.99-0.85 (m, 1H). | 505.35 | E | |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-2148 | 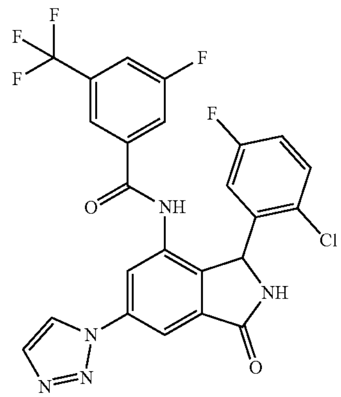 [SMILES: O=C(Nc1cc(-n2ccnn2)cc2c1C(c1cc(F)ccc1Cl)NC2=O)c1cc(F)cc(C(F)(F)F)c1] | Fc1ccc(Cl)c(c1)C1NC(=O)c2cc(cc(NC(=O)c3cc(F)cc(c3)C(F)(F)F)c12)-n1ccnn1 | 1H NMR (400 MHz, DMSO-d6) 10.75 (s, 1H), 9.36 (s, 1H), 9.12-9.07 (m, 1H), 8.26-8.18 (m, 2H), 8.05 (d, J = 1.2 Hz, 1H), 7.96 (d, J = 8.3 Hz, 1H), 7.77 (d, J = 9.1 Hz, 1H), 7.71 (s, 1H), 7.36 (dd, J = 8.9, 5.2 Hz, 1H), 7.12 (td, J = 8.4, 3.1 Hz, 1H), 6.08 (s, 1H). | 534 | A | |
| I-2149 | 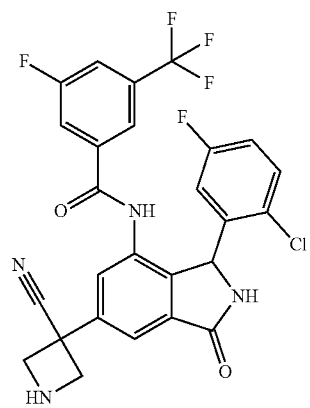 [SMILES: N#CC1(c2cc(NC(=O)c3cc(F)cc(C(F)(F)F)c3)c3c(c2)C(=O)NC3c2cc(F)ccc2Cl)CNC1] | Fc1ccc(Cl)c(cl)C1NC(=O)c2cc(NC(=O)C3(CNC3)C#N)cc(NC(=O)c3cc(F)cc(c3)C(F)(F)F)c12 | (400 MHz, DMSO-d6) 10.84 (br s, 1 H), 10.55 (s, 1 H), 9.20 (br s, 1 H), 8.14 (s, 1 H), 8.00 (d, J = 1.2 Hz, 1 H), 7.95 (d, J = 8.3 Hz, 1 H), 7.82 (d, J = 1.3 Hz, 1 H), 7.72 (d, J = 8.8 Hz, 1 H), 7.63 (s, 1 H), 7.32 (dd, J = 8.9, 5.2 Hz, 1 H), 7.09 (td, J = 8.5, 3.0 Hz, 1 H), 6.60 (br s, 1 H), 5.96 (br s, 1 H), 4.05 (dd, J = 8.2, 3.1 Hz, 2 H), 3.91 (d, J = 8.2 Hz, 2 H). | 590.2 | A | D |
| I-2150 | 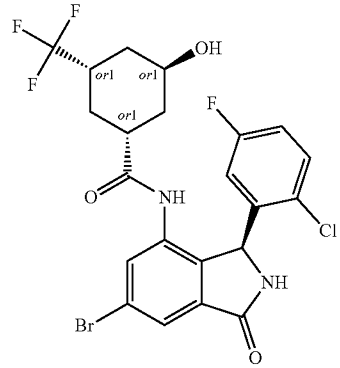 [SMILES: O=C1N[C@H](c2cc(F)ccc2Cl)c2c(NC(=O)[C@H]3C[C@H](O)C[C@@H](C(F)(F)F)C3)cc(Br)cc21] | O[C@@H]1C[C@H](C[C@H](C1)C(F)(F)F)C(=O)Nc1cc(Br)cc2C(=O)N[C@H](c12)c1cc(F)ccc1Cl | 1H-NMR (400 MHz, DMSO-d6) 9.89 (br. s, 1H), 9.25 (br. s, 1H), 7.69 (d, J = 1.4 Hz, 1H), 7.65 (d, J = 1.6 Hz, 1H), 7.51-7.44 (m, 1H), 7.20 (app. td, J = 8.3, 3.0 Hz, 1H), 6.55 (br. s, 1H), 6.02 (br. s, 1H), 4.86 (br. s, 1H), 4.01 (br. s, 1H), 2.57 (tt, J = 12.2, 3.1 Hz, 1H), 2.48-2.39 (m, 1H), 1.80-1.73 (m, 1H), 1.51-1.44 (m, 1H), 1.41-1.34 (m, 1H), 1.34-1.28 (m, 1H), 1.27-1.17 (m, 1H), 1.11-1.00 (m, 1H).. | 549.3 | D | |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-2151 | 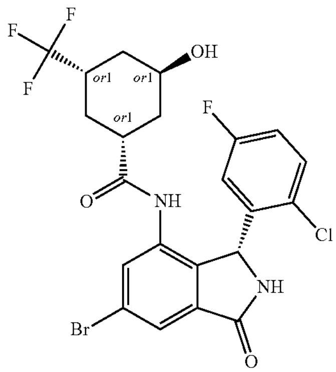 [SMILES: O=C1N[C@@H](c2cc(F)ccc2Cl)c2c(NC(=O)[C@H]3C[C@H](O)C[C@@H](C(F)(F)F)C3)cc(Br)cc21] | O[C@@H]1C[C@H](C[C@H](C1)C(F)(F)F)C(=O)Nc1cc(Br)cc2C(=O)N[C@@H](c12)c1cc(F)ccc1Cl | 1H-NMR (400 MHz, DMSO-d6) 9.99 (br. s, 1H), 9.25 (br. s, 1H), 7.71 (d, J = 1.7 Hz, 1H), 7.54 (d, J = 1.7 Hz, 1H), 7.44 (dd, J = 8.5, 5.1 Hz, 1H), 7.20 (ddd, J = 8.8, 8.2, 3.1 Hz, 1H), 6.51 (br. s, 1H), 6.01 (br. s, 1H), 4.81 (br. d, J = 2.4 Hz, 1H), 4.04 (br. s, 1H), 2.56 (tt, J = 12.5, 3.3 Hz, 1H), 2.47-2.38 (m, 1H), 1.80-1.72 (m, 1H), 1.57-1.50 (m, 1H), 1.34-1.22 (m, 4H). | 549.3 | D | |
| I-2152 | 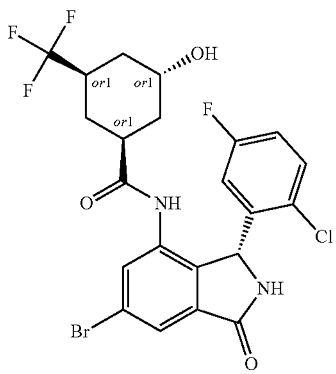 [SMILES: O=C1N[C@@H](c2cc(F)ccc2Cl)c2c(NC(=O)[C@@H]3C[C@@H](O)C[C@H](C(F)(F)F)C3)cc(Br)cc21] | O[C@H]1C[C@@H](C[C@@H](C1)C(F)(F)F)C(=O)Nc1cc(Br)cc2C(=O)N[C@H](c12)c1cc(F)ccc1Cl | 1H-NMR (400 MHz, DMSO-d6) 9.98 (br. s, 1H), 9.25 (br. s, 1H), 7.71 (d, J = 1.7 Hz, 1H), 7.54 (d, J = 1.7 Hz, 1H), 7.44 (dd, J = 8.5, 5.1 Hz, 1H), 7.20 (ddd, J = 8.7, 8.1, 3.1 Hz, 1H), 6.52 (br. s, 1H), 6.01 (br. s, 1H), 4.80 (br. d, J = 2.8 Hz, 1H), 4.04 (br. s, 1H), 2.56 (tt, J = 12.4, 3.3 Hz, 1H), 2.47-2.38 (m, 1H), 1.80-1.72 (m, 1H), 1.58-1.51 (m, 1H), 1.34-1.23 (m, 4H). | 549.3 | D | |
| I-2153 | 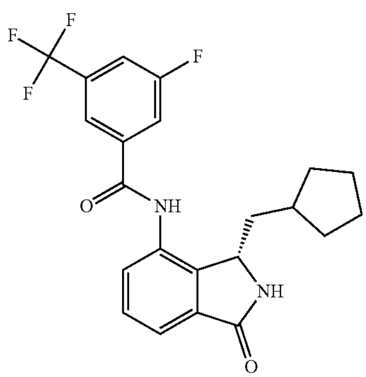 | Fc1cc(cc(c1)C(F)(F)F)C(=O)Nc1cccc2C(=O)N[C@H](CC3CCCC3)c12 | (400 MHz, DMSO-d6) 10.78 (s, 1H), 8.88 (s, 1H), 8.17 (s, 1H), 8.12 (d, J = 8.9 Hz, 1H), 8.04 (d, J = 8.5 Hz, 1H), 7.60-7.50 (m, 3H), 4.77 (d, J = 7.2 Hz, 1H), 1.93-1.81 (m, 1H), 1.81-1.72 (m, 1H), 1.69-1.60 (m, 1H), 1.51-1.41 (m, 1H), 1.39-1.22 (m, 5H), 1.04 (tt, J = 15.2, 7.4 Hz, 1H), 0.94-0.81 (m, 1H). | 421.4 | D | |
| I-2154 | 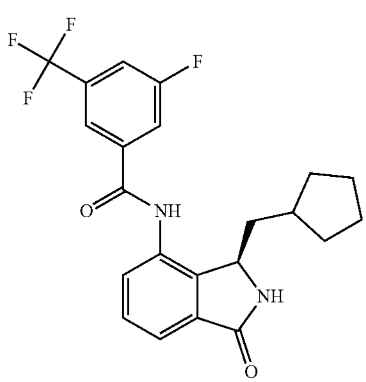 [SMILES: O=C(Nc1cccc2c1[C@@H](CC1CCCC1)NC2=O)c1cc(F)cc(C(F)(F)F)c1] | Fc1cc(cc(c1)C(F)(F)F)C(=O)Nc1cccc2C(=O)N[C@@H](CC3CCCC3)c12 | (400 MHz, DMSO-d6) 10.78 (s, 1H), 8.88 (s, 1H), 8.17 (s, 1H), 8.12 (d, J = 8.9 Hz, 1H), 8.04 (d, J = 8.5 Hz, 1H), 7.60-7.50 (m, 3H), 4.77 (d, J = 7.2 Hz, 1H), 1.93-1.81 (m, 1H), 1.81-1.72 (m, 1H), 1.69-1.60 (m, 1H), 1.51-1.41 (m, 1H), 1.39-1.22 (m, 5H), 1.04 (tt, J = 15.2, 7.4 Hz, 1H), 0.94-0.81 (m, 1H). | 421.4 | D | |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-2155 | 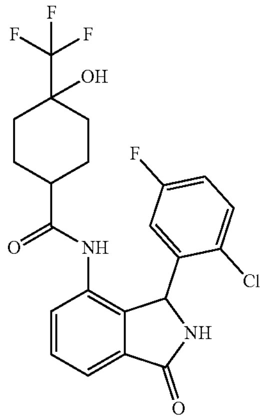 [SMILES: O=C1NC(c2cc(F)ccc2Cl)c2c(NC(=O)C3CCC(O)(C(F)(F)F)CC3)cccc21] | OC1(CCC(CC1)C(=O)Nc1cccc2C(=O)NC(c12)c1cc(F)ccc1Cl)C(F)(F)F | | 471.2 | E | |
| I-2156 | 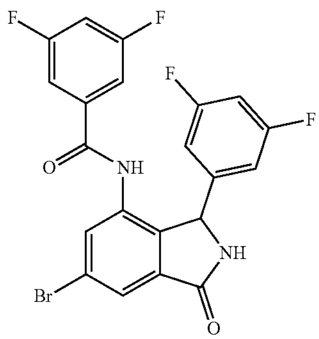 [SMILES: O=C(Nc1cc(Br)cc2c1C(c1cc(F)cc(F)c1)NC2=O)c1cc(F)cc(F)c1] | Fc1cc(F)cc(c1)C1NC(=O)c2cc(Br)cc(NC(=O)c3cc(F)cc(F)c3)c12 | 1H NMR (400 MHz, DMSO) 10.33 (s, 1H), 9.28-9.23 (m, 1H), 7.8-7.75 (m, 2H), 7.54 (tt, J = 9.1, 2.4 Hz, 1H), 7.33 (ddd, J = 6.9, 2.4, 1.3 Hz, 2H), 7.10 (tt, J = 9.3, 2.4 Hz, 1H), 6.79-6.69 (m, 2H), 5.75 (d, J = 1.1 Hz, 1H). | 408 | D | |
| I-2157 | 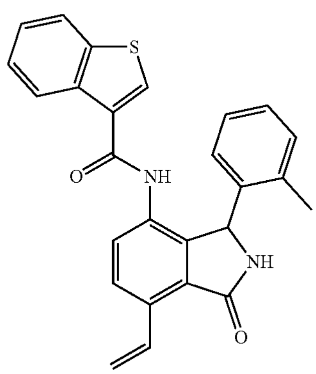 [SMILES: C=Cc1ccc(NC(=O)c2csc3ccccc23)c2c1C(=O)NC2c1ccccc1C] | O=C1C2=C(C=C)C=CC(NC(C3=CSC4=C3C=CC=C4)=O)=C2C(C5=C(C)C=CC=C5)N1 | | 425.3 | | |
| I-2158 | 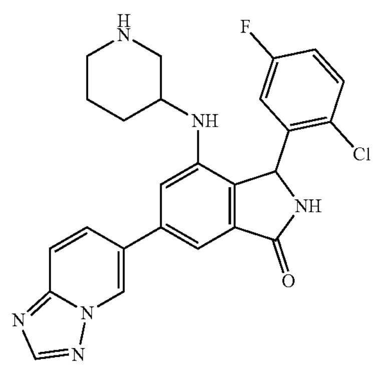 [SMILES: O=C1NC(c2cc(F)ccc2Cl)c2c(NC3CCCNC3)cc(-c3ccc4ncnn4c3)cc21] | Fc1ccc(C1)c(c1)C1NC(=O)c2cc(cc(NC3CCCNC3)c12)-c1ccc2ncnn2c1 | | 477.0 | E | |

TABLE 2-continued

Representative Compounds of the Invention with Bioactivity Data.

| Ex. No. | Structure | SMILES | $^1$H NMR | MS | ADP-Glo IC$_{50}$ | MCF 10A IC$_{50}$ |
|---|---|---|---|---|---|---|
| I-2159 | 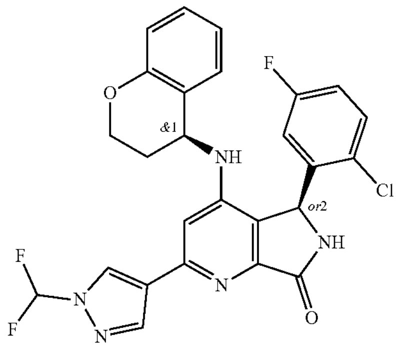 [SMILES: O=C1N[C@H](c2cc(F)ccc2Cl)c2c(N[C@H]3CCOc4ccccc43)cc(-c3cnn(C(F)F)c3)nc21] | FC(F)n1c c(cn1)- c1cc(N[C@ H]2CC Oc3cccc 23)c2[C@ H](NC (=O)c2n1) c1cc(F)c cc1Cl | | 526.1 | D | |
| I-2160 | 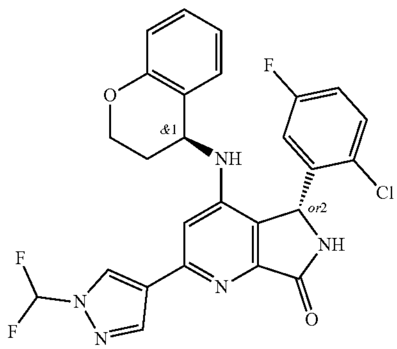 [SMILES: O=C1N[C@@H](c2cc(F)ccc2Cl)c2c(N[C@H]3CCOc4ccccc43)cc(-c3cnn(C(F)F)c3)nc21] | FC(F)n1c c(cn1)- c1cc(N[C @H]2CC Oc3cccc 23)c2[C @@H] (NC(=O)c 2n1)c1cc (F)ccc1C 1 | | 526.1 | E | |
| I-2161 | 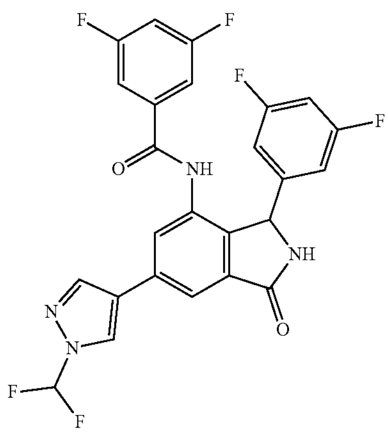 [SMILES: O=C(Nc1cc(-c2cnn(C(F)F)c2)cc2c1C(c1cc(F)cc(F)c1)NC2=O)c1cc(F)cc(F)c1] | FC(F)n1c c(cn1)- c1cc2C(= O)NC(c2 c(NC(=O) c2cc(F)c c(F)c2)c1) c1cc(F)c c(F)c1 | (400 MHz, DMSO) δ 10.33 (s, 1H), 9.15 (d, J = 1.3 Hz, 1H), 8.90 (d, J = 0.7 Hz, 1H), 8.39 (d, J = 0.7 Hz, 1H), 8.02 (d, J = 1.6 Hz, 1H), 7.84 (d, J = 1.6 Hz, 1H), 7.60-7.43 (m, 2H), 7.42-7.34 (m, 2H), 7.10 (tt, J = 9.3, 2.4 Hz, 1H), 6.76-6.68 (m, 2H), 5.75 (s, 1H). | 517.0 | B | |
| I-2162 | 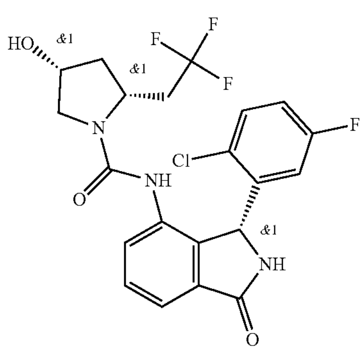 [SMILES: O=C1N[C@@H](c2cc(F)ccc2Cl)c2c(NC(=O)N3C[C@H](O)C[C@@H]3CC(F)(F)F)cccc21] | O[C@@ H]1C[C @H](CC (F)(F)F) N(C1)C (=O)Nc1c ccc2C(= O)N[C@ H](c12)c 1cc(F)cc c1Cl | (400 MHz, CD3CN) δ 7.62-7.58 (m, 1H), 7.57-7.49 (m, 2H), 7.45 (dd, J = 8.9, 5.2 Hz, 1H), 7.16 (br s, 1H), 7.09 (ddd, J = 8.9, 8.0, 3.1 Hz, 1H), 6.62 (br s, 1H), 6.62 (br S [submerged peak], 1H), 6.20 (br s, 1H), 4.37-4.33 (m, 1H), 4.04-3.96 (m, 1H), 3.23 (dd, J = 10.1, 4.7 Hz, 1H), 2.88 (d, J = 10.1 Hz, 1H), 2.85-2.75 (m, 1H), 2.54-2.42 (m, 1H), 2.03-1.97 (m, 2H), 1.91-1.84 (m, 1H) ppm | 472.2 | D | |

TABLE 2-continued

Representative Compounds of the Invention with Bioactivity Data.

| Ex. No. | Structure | SMILES | $^1$H NMR | MS | ADP-Glo IC$_{50}$ | MCF 10A IC$_{50}$ |
|---|---|---|---|---|---|---|
| I-2163 | 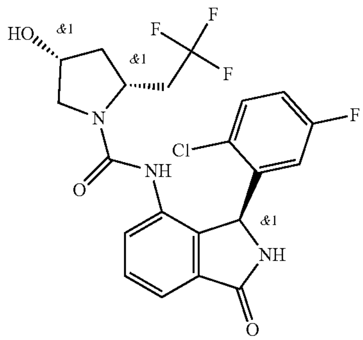 [SMILES: O=C1N[C@H](c2cc(F)ccc2Cl)c2c(NC(=O)N3C[C@H](O)C[C@@H]3CC(F)(F)F)cccc21] | O[C@@H]1C[C@H](CC(F)(F)F)N(C1)C(=O)Nc1cccc2C(=O)N[C@@H](c12)c1cc(F)ccc1Cl | (400 MHz, CD3CN) δ 7.62-7.58 (m, 1H), 7.52 (t, J = 7.6 Hz, 1H), 7.46-7.38 (m, 1H), 7.35 (d, J = 7.7 Hz, 1H), 7.14 (br s, 1H), 7.07 (ddd, J = 8.8, 8.0, 3.1 Hz, 1H), 6.71 (br s, 1H), 6.62 (br s, 1H), 6.13 (br s, 1H), 4.27 (ddd, J = 7.7, 5.1, 2.7 Hz, 1H), 4.21 (d, J = 8.7 Hz, 1H), 3.05 (d, J = 10.5 Hz, 1H), 2.83-2.71 (m, 1H), 2.64-2.52 (m, 1H), 2.51-2.37 (m, 2H), 2.09-1.99 (m, 1H), 1.90-1.82 (m, 1H) ppm [~5:1 diastereomeric ratio- major diastereomer described] | 472.2 | E | |
| I-2164 | 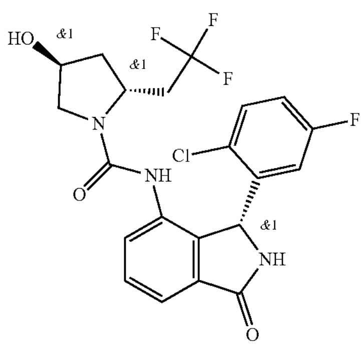 [SMILES: O=C1N[C@@H](c2cc(F)ccc2Cl)c2c(NC(=O)N3C[C@@H](O)C[C@@H]3CC(F)(F)F)cccc21] | O[C@H]1C[C@H](CC(F)(F)F)N(C1)C(=O)Nc1cccc2C(=O)N[C@H](c12)c1cc(F)ccc1Cl | (400 MHz, CD3CN) δ 7.63-7.58 (m, 2H), 7.55 (d, J = 7.5 Hz, 1H), 7.46 (dd, J = 8.9, 5.1 Hz, 1H), 7.17 (br s, 1H), 7.10 (ddd, J = 8.8, 8.0, 3.1 Hz, 1H), 6.61 (br s, 1H), 6.61 (br s [submerged], 1H), 6.21 (br s, 1H), 4.31-4.25 (m, 1H), 4.09-4.00 (m, 1H), 3.14 (dd, J = 9.8, 5.0 Hz, 1H), 3.05-2.92 (m, 1H), 2.88 (dd, J = 9.8, 3.0 Hz, 1H), 2.12-2.08 (m, 1H [submerged under water peak]), 2.03-1.97 (m, 1H), 1.92-1.83 (m, 2H) ppm | 472.2 | D | |
| I-2165 | 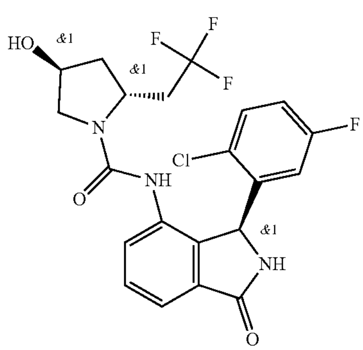 [SMILES: O=C1N[C@H](c2cc(F)ccc2Cl)c2c(NC(=O)N3C[C@@H](O)C[C@@H]3CC(F)(F)F)cccc21] | O[C@H]1C[C@H](CC(F)(F)F)N(C1)C(=O)Nc1cccc2C(=O)N[C@@H](c12)c1cc(F)ccc1Cl | (400 MHz, CD3CN) δ 7.62-7.58 (m, 1H), 7.52 (t, J = 7.6 Hz, 1H), 7.45-7.37 (m, 2H), 7.13 (br s, 1H), 7.10-7.01 (m, 1H), 6.68 (br s, 1H), 6.58 (br s, 1H), 6.18 (br s, 1H), 4.33-4.25 (m, 1H), 4.20-4.12 (m, 1H), 3.30 (dd, J = 10.1, 4.8 Hz, 1H), 2.81-2.67 (m, 2H), 2.12-2.07 (m, 1H [submerged under water peak]), 2.07-1.98 (m, 1H), 1.92-1.83 (m, 2H) ppm [~4:1 diastereomeric ratio- major diastereomer described] | 472.2 | E | |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-2166 | 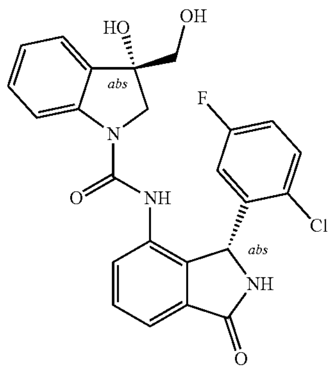 [SMILES: O=C1N[C@@H](c2cc(F)ccc2Cl)c2c(NC(=O)N3C[C@](O)(CO)c4ccccc43)cccc21] | OC[C@@]1(O)CN(C(=O)Nc2cccc3C(=O)N[C@H](c23)c2cc(F)ccc2Cl)c2ccccc12 | (400 MHz, DMSO-d6) 9.03 (s, 1H), 8.55 (s, 2H), 7.80 (d, J = 8.1 Hz, 1H), 7.61-7.51 (m, 2H), 7.41 (dd, J = 7.2, 1.8 Hz, 1H), 7.35 (dd, J = 8.9, 5.1 Hz, 1H), 7.29 (d, J = 7.4 Hz, 1H), 7.21 (t, J = 7.7 Hz, 1H), 7.12 (td, J = 8.4, 3.1 Hz, 1H), 7.00-6.91 (m, 1H), 6.08 (s, 1H), 5.51 (s, 1H), 4.90 (t, J = 5.6 Hz, 1H), 3.68 (d, J = 10.9 Hz, 1H), 3.53 (dd, J = 11.0, 5.0 Hz, 1H), 3.46-3.36 (m, 2H). | 468.1 | D | |
| I-2167 | 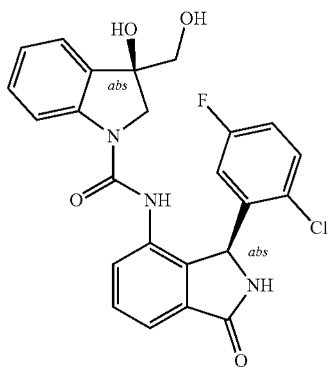 [SMILES: O=C1N[C@H](c2cc(F)ccc2Cl)c2c(NC(=O)N3C[C@@](O)(CO)c4ccccc43)cccc21] | OC[C@]1(O)CN(C(=O)Nc2cccc3C(=O)N[C@@H](c23)c2cc(F)ccc2Cl)c2ccccc12 | (400 MHz, DMSO-d6) 9.05 (s, 1H), 8.44 (s, 1H), 7.75 (d, J = 8.1 Hz, 1H), 7.57 (d, J = 7.2 Hz, 2H), 7.50 (s, 1H), 7.37 (dd, J = 8.8, 5.1 Hz, 1H), 7.28 (d, J = 7.4 Hz, 1H), 7.19 (t, J = 7.8 Hz, 1H), 7.11 (dt, J = 8.4, 4.2 Hz, 1H), 6.95 (t, J = 7.4 Hz, 1H), 6.14 (s, 1H), 5.43 (s, 1H), 4.92 (s, 1H), 3.93 (d, J = 10.9 Hz, 1H), 3.50 (s, 2H), 3.27 (d, J = 10.7 Hz, 2H). | 468.1 | E | |
| I-2168 | 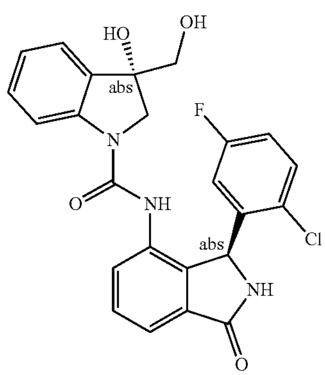 [SMILES: O=C1N[C@H](c2cc(F)ccc2Cl)c2c(NC(=O)N3C[C@](O)(CO)c4ccccc43)cccc21] | OC[C@@]1(O)CN(C(=O)Nc2cccc3C(=O)N[C@@H](c23)c2cc(F)ccc2Cl)c2ccccc12 | (400 MHz, DMSO-d6) 9.03 (s, 1H), 8.56 (s, 1H), 7.80 (d, J = 8.1 Hz, 1H), 7.62-7.51 (m, 2H), 7.41 (dd, J = 7.2, 1.8 Hz, 1H), 7.35 (dd, J = 8.9, 5.2 Hz, 1H), 7.31-7.26 (m, 1H), 7.21 (t, J = 7.7 Hz, 1H), 7.12 (td, J = 8.3, 3.1 Hz, 1H), 6.95 (t, J = 7.4 Hz, 1H), 6.54 (s, 1H), 6.08 (s, 1H), 5.52 (s, 1H), 4.92 (s, 1H), 3.68 (d, J = 10.9 Hz, 1H), 3.53 (d, J = 10.9 Hz, 1H), 3.41 (t, J = 11.7 Hz, 2H). | 468.1 | E | |
| I-2169 | 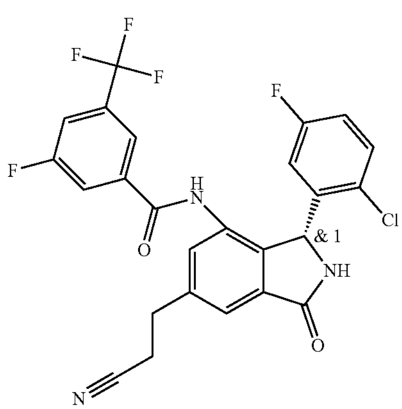 [SMILES: N#CCCc1cc(NC(=O)c2cc(F)cc(C(F)(F)F)c2)c2c(c1)C(=O)N[C@H]2c1cc(F)ccc1Cl] | Fc1ccc(C1)c(c1)[C@@H]1NC(=O)c2cc(CCC#N)cc(NC(=O)c3cc(F)cc(c3)C(F)(F)F)c12 | (400 MHz, DMSO-d6) 10.54 (s, 1H), 9.15 (s, 1H), 7.95 (d, J = 8.4 Hz, 1H), 7.74 (d, J = 9.1 Hz, 1H), 7.67 (d, J = 9.8 Hz, 2H), 7.43 (s, 1H), 7.32 (dd, J = 8.9, 5.2 Hz, 1H), 7.10 (td, J = 8.4, 3.1 Hz, 1H), 5.96 (s, 1H), 3.13-2.99 (m, 2H), 2.94 (t, J = 7.1 Hz, 2H). | 520.2 | A | A |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-2170 | 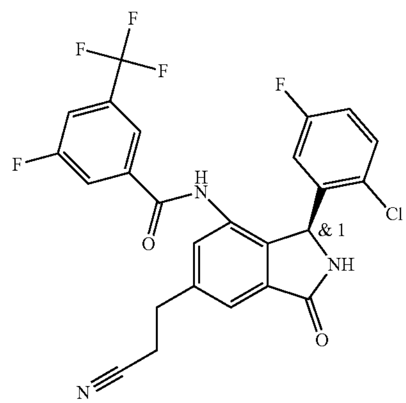 [SMILES: N#CCCc1cc(NC(=O)c2cc(F)cc(C(F)(F)F)c2)c2c(c1)C(=O)N[C@@H]2c1cc(F)ccc1Cl] | Fc1ccc(C 1)c(c1)[C @H]1NC (=O)c2cc (CCC#N) cc(NC(= O)c3cc(F) cc(c3)C (F)(F)F)c 12 | (400 MHz, DMSO-d6) 10.54 (s, 1H), 9.15 (s, 1H), 7.95 (d, J = 8.4 Hz, 1H), 7.74 (d, J = 9.1 Hz, 1H), 7.67 (d, J = 9.8 Hz, 2H), 7.43 (s, 1H), 7.32 (dd, J = 8.9, 5.2 Hz, 1H), 7.10 (td, J = 8.4, 3.1 Hz, 1H), 5.96 (s, 1H), 3.13- 2.99 (m, 2H), 2.94 (t, J = 7.1 Hz, 2H). | 520.2 | E | |
| I-2171 | 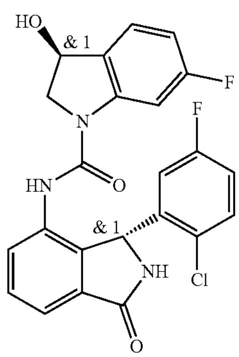 [SMILES: O=C1N[C@@H](c2cc(F)ccc2Cl)c2c(NC(=O)N3C[C@@H](O)c4ccc(F)cc43)cccc21] | O[C@@ H]1CN (C(=O)Nc 2cccc3C (=O)N[C @H](c23) c2cc(F)c cc2Cl)c2 cc(F)ccc 12 | (400 MHz, DMSO-d6) δ9.08 (s, 1H), 8.63 (s, 1H), 7.58 (q, J = 7.9, 7.4 Hz, 2H), 7.49-7.26 (m, 4H), 7.09 (td, J = 8.4, 3.1 Hz, 1H), 6.75 (td, J = 8.7, 2.5 Hz, 1H), 6.55 (s, 1H), 6.08 (s, 1H), 5.79-5.49 (m, 1H), 5.12 (dd, J = 7.7, 3.4 Hz, 1H), 3.97 (dd, J = 11.1, 7.9 Hz, 1H), 3.29 (dd, J = 11.1, 3.5 Hz, 1H). | 456.3 | A | A |
| I-2172 | 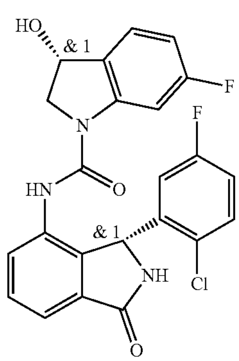 [SMILES: O=C1N[C@@H](c2cc(F)ccc2Cl)c2c(NC(=O)N3C[C@H](O)c4ccc(F)cc43)cccc21] | O[C@H] 1CN(C(= O)Nc2cc cc3C(=O) N[C@H] (c23)c2c c(F)ccc2 Cl)c2cc (F)ccc12 | (400 MHz, DMSO-d6) δ9.08 (s, 1H), 8.63 (s, 1H), 7.58 (q, J = 7.9, 7.4 Hz, 2H), 7.49-7.26 (m, 4H), 7.09 (td, J = 8.4, 3.1 Hz, 1H), 6.75 (td, J = 8.7, 2.5 Hz, 1H), 6.55 (s, 1H), 6.08 (s, 1H), 5.79-5.49 (m, 1H), 5.12 (dd, J = 7.7, 3.4 Hz, 1H), 3.97 (dd, J = 11.1, 7.9 Hz, 1H), 3.29 (dd, J = 11.1, 3.5 Hz, 1H). | 456.3 | C | |
| I-2173 | 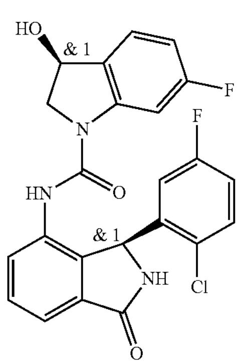 [SMILES: O=C1N[C@H](c2cc(F)ccc2Cl)c2c(NC(=O)N3C[C@@H](O)c4ccc(F)cc43)cccc21] | O[C@@ H]1CN (C(=O)Nc 2cccc3C (=O)N[C @@H](c 23)c2cc (F)ccc2Cl) c2cc(F)c cc12 | (400 MHz, DMSO-d6) δ9.08 (s, 1H), 8.63 (s, 1H), 7.58 (q, J = 7.9, 7.4 Hz, 2H), 7.49-7.26 (m, 4H), 7.09 (td, J = 8.4, 3.1 Hz, 1H), 6.75 (td, J = 8.7, 2.5 Hz, 1H), 6.55 (s, 1H), 6.08 (s, 1H), 5.79-5.49 (m, 1H), 5.12 (dd, J = 7.7, 3.4 Hz, 1H), 3.97 (dd, J = 11.1, 7.9 Hz, 1H), 3.29 (dd, J = 11.1, 3.5 Hz, 1H). | 456.3 | D | |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-2174 | 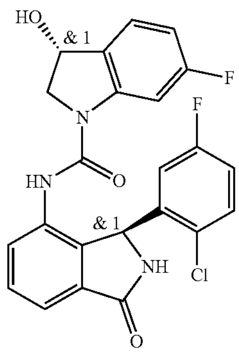 [SMILES: O=C1N[C@H](c2cc(F)ccc2Cl)c2c(NC(=O)N3C[C@H](O)c4ccc(F)cc43)cccc21] | O[C@H]1CN(C(=O)Nc2ccc3C(=O)N[C@@H](c23)c2cc(F)ccc2Cl)c2cc(F)ccc12 | (400 MHz, DMSO-d6) δ9.08 (s, 1H), 8.63 (s, 1H), 7.58 (q, J = 7.9, 7.4 Hz, 2H), 7.49-7.26 (m, 4H), 7.09 (td, J = 8.4, 3.1 Hz, 1H), 6.75 (td, J = 8.7, 2.5 Hz, 1H), 6.55 (s, 1H), 6.08 (s, 1H), 5.79-5.49 (m, 1H), 5.12 (dd, J = 7.7, 3.4 Hz, 1H), 3.97 (dd, J = 11.1, 7.9 Hz, 1H), 3.29 (dd, J = 11.1, 3.5 Hz, 1H). | 456.3 | E | |
| I-2175 | 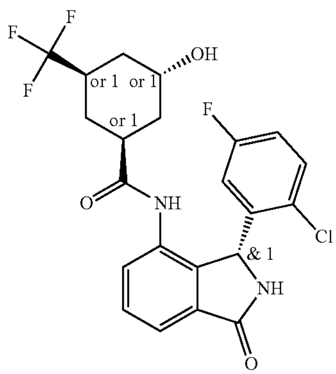 [SMILES: O=C1N[C@@H](c2cc(F)ccc2Cl)c2c(NC(=O)[C@@H]3C[C@@H](O)C[C@H](C(F)(F)F)C3)cccc21] | O[C@@H]1C[C@H](C[C@H](C1)C(F)(F)F)C(=O)Nc1cccc2C(=O)N[C@H](c12)c1cc(F)ccc1Cl | (400 MHz, DMSO-d6) δ 9.93 (br. s, 1H), 9.08 (br. s, 1H), 7.62-7.54 (m, 2H), 7.44 (dd, J = 8.6, 4.8 Hz, 1H), 7.33 (dd, J = 7.4, 1.3 Hz, 1H), 7.18 (ddd, J = 8.8, 8.1, 3.1 Hz, 1H), 6.41 (br. s, 1H), 6.05 (br. s, 1H), 4.81 (br. s, 1H), 4.05 (br. s, 1H), 2.57 (tt, J = 12.1, 3.3 Hz, 1H), 2.46-2.38 (m, 1H), 1.80-1.72 (m, 1H), 1.60-1.54 (m, 1H), 1.37-1.19 (m, 3H), 0.98-0.88 (m, 1H). | 471.4 | E | |
| I-2176 | 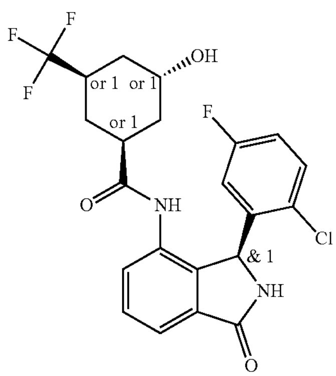 [SMILES: O=C1N[C@H](c2cc(F)ccc2Cl)c2c(NC(=O)[C@@H]3C[C@@H](O)C[C@H](C(F)(F)F)C3)cccc21] | O[C@@@H](C[C@H](C1)C(F)(F)F)C(=O)Nc1cccc2C(=O)N[C@@H](c12)c1cc(F)ccc1Cl | (400 MHz, DMSO-d6) δ 9.79 (br. s, 1H), 9.08 (br. s, 1H), 7.61-7.54 (m, 2H), 7.48 (dd, J = 7.4, 4.8 Hz, 1H), 7.43 (dd, J = 7.2, 0.9 Hz, 1H), 7.19 (app. td, J = 8.3, 3.0 Hz, 1H), 6.44 (br. s, 1H), 6.06 (br. s, 1H), 4.84 (br. s, 1H), 4.01 (br. s, 1H), 2.58 (tt, J = 13.3, 3.8 Hz, 1H), 2.46-2.39 (m, 1H), 1.81-1.74 (m, 1H), 1.53-1.46 (m, 1H), 1.39-1.18 (m, 3H), 1.08 (app. q, J = 12.8 Hz, 1H). | 471.4 | E | |
| I-2177 | 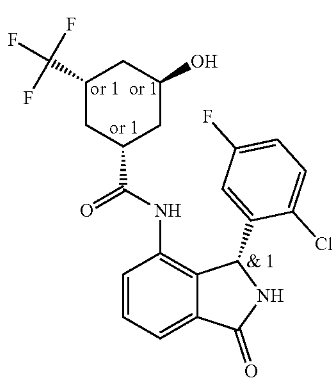 [SMILES: O=C1N[C@@H](c2cc(F)ccc2Cl)c2c(NC(=O)[C@H]3C[C@H](O)C[C@@H](C(F)(F)F)C3)cccc21] | O[C@H]1C[C@@H](C[C@@H](C1)C(F)(F)F)C(=O)Nc1cccc2C(=O)N[C@H](c12)c1cc(F)ccc1Cl | (400 MHz, DMSO-d6) δ 9.77 (br. s, 1H), 9.07 (br. s, 1H), 7.61-7.54 (m, 2H), 7.48 (dd, J = 7.7, 5.0 Hz, 1H), 7.43 (dd, J = 7.1, 1.5 Hz, 1H), 7.19 (td, J = 8.4, 3.1 Hz, 1H), 6.45 (br. s, 1H), 6.06 (br. s, 1H), 4.82 (d, J = 2.8 Hz, 1H), 4.01 (br. s, 1H), 2.59 (tt, J = 12.0, 3.4 Hz, 1H), 2.48-2.40 (m, 1H), 1.81-1.73 (m, 1H), 1.53-1.47 (m, 1H), 1.38-1.18 (m, 3H), 1.08 (app. q, J = 12.7 Hz, 1H). | 471.4 | D | |

TABLE 2-continued

Representative Compounds of the Invention with Bioactivity Data.

| Ex. No. | Structure | SMILES | $^1$H NMR | MS | ADP-Glo IC$_{50}$ | MCF 10A IC$_{50}$ |
|---|---|---|---|---|---|---|
| I-2178 | 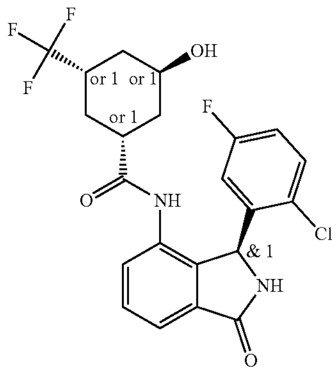 [SMILES: O=C1N[C@H](c2cc(F)ccc2Cl)c2c(NC(=O)[C@H]3C[C@H](O)C[C@@H](C(F)(F)F)C3)cccc21] | O[C@H]1C[C@@H](C[C@@H](C1)C(F)(F)F)C(=O)Nc1cccc2C(=O)N[C@@H](c12)c1cc(F)ccc1Cl | (400 MHz, DMSO-d6) δ 9.91 (br. s, 1H), 9.08 (br. s, 1H), 7.62-7.54 (m, 2H), 7.44 (dd, J = 8.3, 5.1 Hz, 1H), 7.33 (dd, J = 7.4, 1.0 Hz, 1H), 7.19 (ddd, J = 8.8, 8.1, 3.1 Hz, 1H), 6.40 (br. s, 1H), 6.05 (br. s, 1H), 4.78 (br. s, 1H), 4.05 (br. s, 1H), 2.58 (tt, J = 12.4, 3.6 Hz, 1H), 2.47-2.37 (m, 1H), 1.80-1.73 (m, 1H), 1.60-1.53 (m, 1H), 1.38-1.19 (m, 2H), 0.93 (app. q, J = 11.8 Hz, 1H). | 471.4 | E | |
| I-2179 | 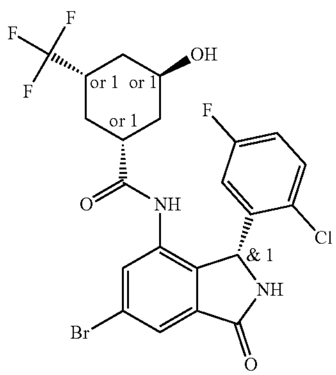 [SMILES: O=C1N[C@@H](c2cc(F)ccc2Cl)c2c(NC(=O)[C@H]3C[C@H](O)C[C@@H](C(F)(F)F)C3)cc(Br)cc21] | O[C@H]1C[C@@H](C[C@@H]C1)C(F)(F)F)C(=O)Nc1cc(Br)cc2C(=O)N[C@H](c12)c1cc(F)ccc1Cl | (400 MHz, DMSO-d6) δ 9.88 (br. s, 1H), 9.25 (br. s, 1H), 7.69 (d, J = 1.7 Hz, 1H), 7.65 (d, J = 1.7 Hz, 1H), 7.48 (dd, J = 7.1, 4.6 Hz, 1H), 7.20 (ddd, J = 8.8, 8.1, 3.1 Hz, 1H), 6.56 (br. s, 1H), 6.02 (br. s, 1H), 4.85 (d, J = 2.4 Hz, 1H), 4.01 (br. s, 1H), 2.58 (tt, J = 12.6, 3.6 Hz, 1H), 2.48-2.39 (m, 1H), 1.80-1.73 (m, 1H), 1.51-1.45 (m, 1H), 1.40-1.34 (m, 1H), 1.34-1.29 (m, 1H), 1.28-1.20 (m, 1H), 1.11-1.00 (m, 1H). | 549.3 | C | |
| I-2180 | 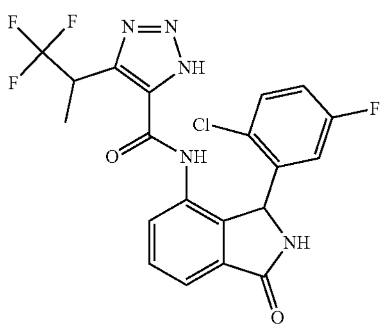 [SMILES: CC(c1nn[nH]c1C(=O)Nc1cccc2c1C(c1cc(F)ccc1Cl)NC2=O)C(F)(F)F] | CC(c1nn[nH]c1C(=O)Nc1cccc2C(=O)NC(c12)c1cc(F)ccc1Cl)C(F)(F)F | (400 MHz, DMSO-d6) δ 11.20 (br s, 1H), 10.26 (br s, 1H), 10.18 (br s, 1H), 9.10 (br s, 1H), 9.08 (br s, 1H), 7.69-7.63 (m, 2H), 7.63-7.54 (m, 4H), 7.35-7.28 (m, 2H), 7.13-7.00 (m, 2H), 6.62 (br s, 2H), 6.12 (br s, 2H), 4.66 (br s, 1H), 4.55 (br s, 1H), 1.48 (d, J = 7.1 Hz, 3H), 1.42 (d, J = 7.3 Hz, 3H). 1:1 Mixture of diastereomers (both reported) | 468.0 | E | |
| I-2181 | 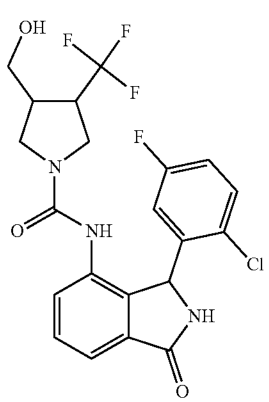 [SMILES: O=C1NC(c2cc(F)ccc2Cl)c2c(NC(=O)N3CC(CO)C(C(F)(F)F)C3)cccc21] | OCC1CN(CC1C(F)(F)F)C(=O)Nc1cccc2C(=O)NC(c12)c1cc(F)ccc1Cl | (400 MHz, CD3CN) δ 7.59 (overlapping dd J = 7.5, 1.3 Hz, 0.5H), 7.59 (overlapping dd J = 7.5, 1.5 Hz, 0.5H), 7.52 (t, J = 7.6 Hz, 1H), 7.47-7.40 (m, 2H), 7.18 (br s, 1H), 7.11-7.04 (m, 1H), 6.68 (br s, 0.5H), 6.65 (br s, 0.5H), 6.59 (submerged br s, 1H), 6.15 (br s, 1H), 3.66-3.59 (m, 0.5H), 3.60-3.33 (m, 5.5H), 3.21-3.11 (m, 1H), 2.96-2.84 (m, 1H), 2.54-2.38 (submerged m, 1H). | 472.0 | E | |

TABLE 2-continued

Representative Compounds of the Invention with Bioactivity Data.

| Ex. No. | Structure | SMILES | $^1$H NMR | MS | ADP-Glo IC$_{50}$ | MCF 10A IC$_{50}$ |
|---|---|---|---|---|---|---|
| I-2182 | 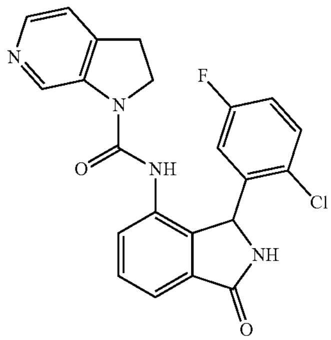 [SMILES: O=C1NC(c2cc(F)ccc2Cl)c2c(NC(=O)N3CCc4ccncc43)cccc21] | Fc1ccc(C1)c(c1)C1NC(=O)c2cccc(NC(=O)N3CCc4ccncc34)c12 | (400 MHz, DMSO-d6) 9.07 (s, 1H), 8.87 (s, 1H), 8.71 (s, 1H), 8.13 (d, J = 4.7 Hz, 1H), 7.65-7.53 (m, 2H), 7.42-7.33 (m, 2H), 7.29-7.23 (m, 1H), 7.15 (ddd, J = 8.9, 7.9, 3.1 Hz, 1H), 6.55 (s, 1H), 6.01 (s, 1H), 3.89 (q, J = 9.8 Hz, 1H), 3.20-2.99 (m, 3H). | 423.2 | E | |
| I-2183 | 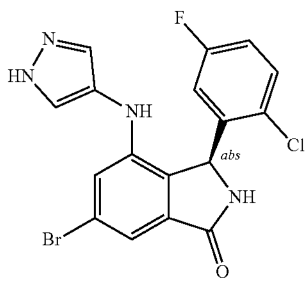 [SMILES: O=C1N[C@H](c2cc(F)ccc2Cl)c2c(Nc3cn[nH]c3)cc(Br)cc21] | Fc1ccc(C1)c(c1)[C@H]1NC(=O)c2cc(Br)cc(Nc3cn[nH]c3)c12 | (400 MHz, DMSO-d6) δ 12.75 (s, 1H), 9.09 (s, 1H), 7.59 (br. s, 1H), 7.51 (dd, J = 8.8, 5.2 Hz, 1H), 7.23 (ddd, J = 8.8, 8.0, 3.1 Hz, 2H), 7.15 (d, J = 1.6 Hz, 1H), 6.98-6.94 (m, 2H), 6.68 (br. s, 1H), 5.82 (s, 1H); racemic mixture. | 421.1 | E | |
| I-2184 | 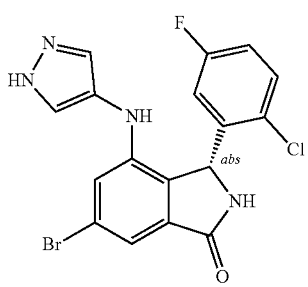 [SMILES: O=C1N[C@@H](c2cc(F)ccc2Cl)c2c(Nc3cn[nH]c3)cc(Br)cc21] | Fc1ccc(C1)c(c1)[C@@H]1NC(=O)c2cc(Br)cc(Nc3cn[nH]c3)c12 | (400 MHz, DMSO-d6) δ 12.75 (s, 1H), 9.09 (s, 1H), 7.59 (br. s, 1H), 7.51 (dd, J = 8.8, 5.2 Hz, 1H), 7.23 (ddd, J = 8.8, 8.0, 3.1 Hz, 2H), 7.15 (d, J = 1.6 Hz, 1H), 6.98-6.94 (m, 2H), 6.68 (br. s, 1H), 5.82 (s, 1H) | 421.1 | E | |
| I-2185 | 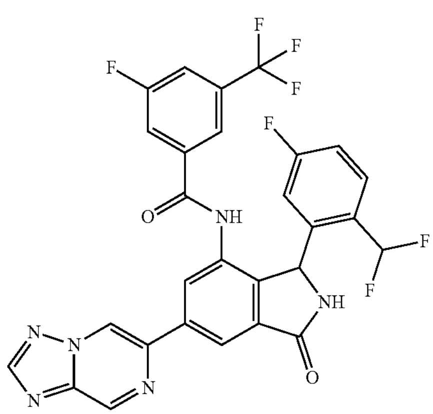 [SMILES: O=C(Nc1cc(-c2cn3ncnc3cn2)cc2c1C(c1cc(F)ccc1C(F)F)NC2=O)c1cc(F)cc(C(F)(F)F)c1] | FC(F)c1ccc(F)cc1C1NC(=O)c2cc(c(NC(=O)c3cc(F)cc(c3)C(F)(F)F)c12)-c1cn2ncnc2cn1 | | | A | A |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-2186 | 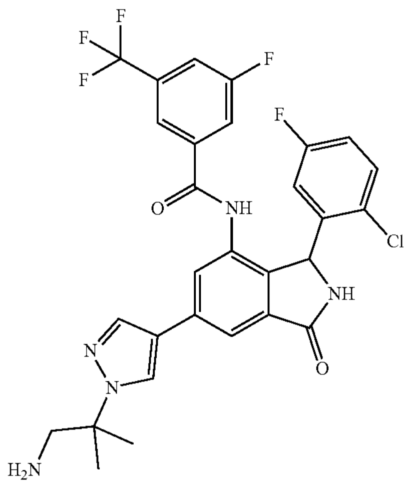 [SMILES: CC(C)(CN)n1cc(-c2cc(NC(=O)c3cc(F)cc(C(F)(F)F)c3)c3c(c2)C(=O)NC3c2cc(F)ccc2Cl)cn1] | CC(C)(CN)n1cc(cn1)-c1cc2C(=O)NC(c2c(NC(=O)c2cc(F)cc(c2)C(F)(F)F)c1)c1cc(F)ccc1Cl | | 604.3 | A | B |
| I-2187 | 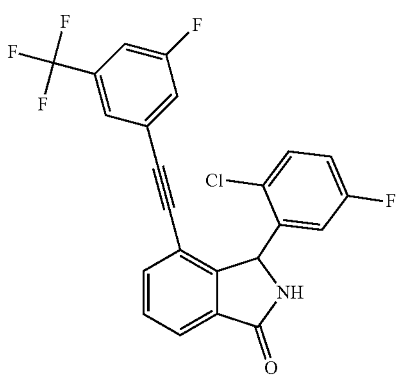 [SMILES: O=C1NC(c2cc(F)ccc2Cl)c2c(C#Cc3cc(F)cc(C(F)(F)F)c3)cccc21] | Fc1ccc(C1)c(c1)C1NC(=O)c2cccc(C#Cc3cc(F)cc(c3)C(F)(F)F)c12 | | 448.2 | E | |
| I-2188 | 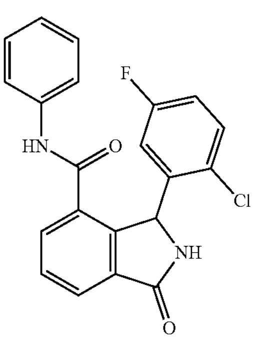 [SMILES: O=C(Nc1ccccc1)c1cccc2c1C(c1cc(F)ccc1Cl)NC2=O] | Fc1ccc(C1)c(c1)C1NC(=O)c2cccc(C(=O)Nc3ccccc3)c12 | (400 MHz, DMSO-d6) 10.32 (s, 1H), 9.25 (s, 1H), 7.93 (dd, J = 7.7, 3.9 Hz, 2H), 7.74 (t, J = 7.5 Hz, 1H), 7.41 (d, J = 8.1 Hz, 3H), 7.27 (t, J = 7.9 Hz, 2H), 7.16-7.01 (m, 2H), 6.41 (s, 1H). | 381.2 | E | |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-2189 | 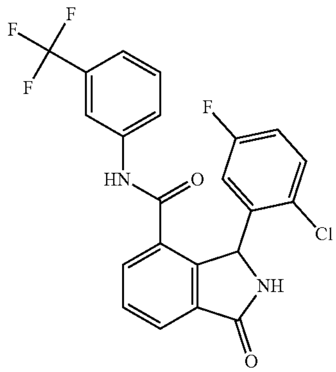 [SMILES: O=C(Nc1cccc(C(F)(F)F)c1)c1cccc2c1C(c1cc(F)ccc1Cl)NC2=O] | Fc1ccc(C1)c(c1)C1NC(=O)c2cccc(C(=O)Nc3cccc(c3)C(F)(F)F)c12 | (400 MHz, DMSO-d6) 10.65 (s, 1H), 9.28 (s, 1H), 7.95 (t, J = 7.3 Hz, 2H), 7.81 (s, 1H), 7.76 (t, J = 7.6 Hz, 1H), 7.65 (d, J = 8.2 Hz, 1H), 7.53 (t, J = 8.0 Hz, 1H), 7.45-7.38 (m, 1H), 7.35 (dd, J = 8.9, 5.2 Hz, 1H), 7.10 (ddd, J = 8.9, 7.9, 3.1 Hz, 1H), 6.40 (s, 1H). | 449.2 | D | |
| I-2190 | 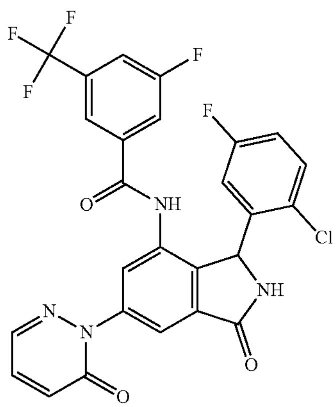 [SMILES: O=C(Nc1cc(-n2ncccc2=O)cc2c1C(c1cc(F)ccc1Cl)NC2=O)c1cc(F)cc(C(F)(F)F)c1] | Fc1ccc(C1)c(c1)C1NC(=O)c2cc(cc(NC(=O)c3cc(F)cc(c3)C(F)(F)F)c12)-n1nccc1=O | (400 MHz, DMSO-d6) 10.67 (s, 1H), 9.29 (s, 1H), 8.13 (dd, J = 3.8, 1.6 Hz, 1H), 7.92 (dd, J = 12.0, 5.2 Hz, 2H), 7.84-7.73 (m, 2H), 7.69 (s, 1H), 7.55 (dd, J = 9.5, 3.8 Hz, 1H), 7.35 (dd, J = 8.9, 5.2 Hz, 1H), 7.13 (ddd, J = 16.8, 9.0, 2.3 Hz, 2H), 6.73 (s, 1H), 6.04 (s, 1H). | 561.1 | B | |
| I-2191 | 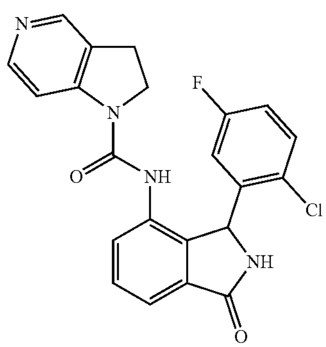 [SMILES: O=C1NC(c2cc(F)ccc2Cl)c2c(NC(=O)N3CCc4cnccc43)cccc21] | Fc1ccc(C1)c(c1)C1NC(=O)c2cccc(NC(=O)N3CCc4cnccc34)c12 | (400 MHz, DMSO-d6) 9.09 (s, 1H), 8.81 (s, 1H), 8.31-8.26 (m, 1H), 8.23 (d, J = 5.4 Hz, 1H), 7.66-7.60 (m, 1H), 7.63-7.54 (m, 2H), 7.43-7.35 (m, 2H), 7.16 (ddd, J = 8.8, 7.9, 3.1 Hz, 1H), 6.59 (s, 1H), 6.00 (s, 1H), 3.92 (td, J = 10.1, 7.0 Hz, 1H), 3.19-3.08 (m, 2H), 3.08 (s, 1H). | 423.1 | D | |
| I-2192 | 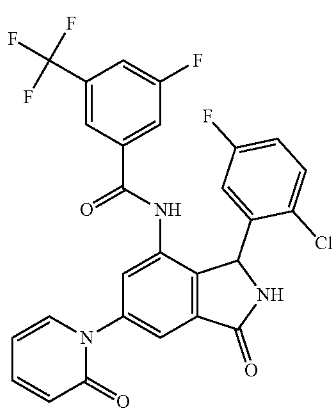 [SMILES: O=C(Nc1cc(-n2ccccc2=O)cc2c1C(c1cc(F)ccc1Cl)NC2=O)c1cc(F)cc(C(F)(F)F)c1] | Fc1ccc(C1)c(c1)C1NC(=O)c2cc(cc(NC(=O)c3cc(F)cc(c3)C(F)(F)F)c12)-n1ccccc1=O | (400 MHz, DMSO-d6) 10.68 (s, 1H), 9.32 (s, 1H), 7.95 (d, J = 8.4 Hz, 1H), 7.82-7.71 (m, 2H), 7.71-7.65 (m, 2H), 7.62-7.53 (m, 2H), 7.36 (dd, J = 8.9, 5.2 Hz, 1H), 7.13 (td, J = 8.4, 3.0 Hz, 1H), 7.00-6.76 (s, 1H), 6.55 (dt, J = 9.2, 1.0 Hz, 1H), 6.38 (td, J = 6.7, 1.4 Hz, 1H), 6.06 (s, 1H). | 560.1 | A | B |

| Ex. No. | Structure | SMILES | ¹H NMR | MS | ADP-Glo IC$_{50}$ | MCF 10A IC$_{50}$ |
|---|---|---|---|---|---|---|
| I-2193 | 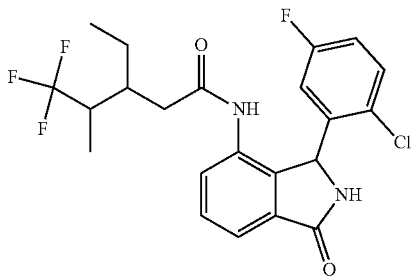 [SMILES: CCC(CC(=O)Nc1cccc2c1C(c1cc(F)ccc1Cl)NC2=O)C(C)C(F)(F)F] | CCC(CC(=O)Nc1cccc2C(=O)NC(c12)c1cc(F)ccc1Cl)C(C)C(F)(F)F | (400 MHz, DMSO-d6) δ, 9.74 (br. s, 1H), 9.08 (br. s, 1H), 7.65-7.52 (m, 2H), 7.53-7.46 (m, 1H), 7.42 (dd, J = 7.4, 1.4 Hz, 1H), 7.26-7.16 (m, 1H), 6.42 (br. s, 1H), 6.07 (br. s, 1H), 2.48-2.28 (m, 1H), 2.21-1.74 (m, 3H), 1.24-0.95 (m, 2H), 0.94 (d, J = 2.0 Hz, 3H), 0.75 (t, J = 7.3 H, 3 Hz) | 457.2 | D | |
| I-2194 | 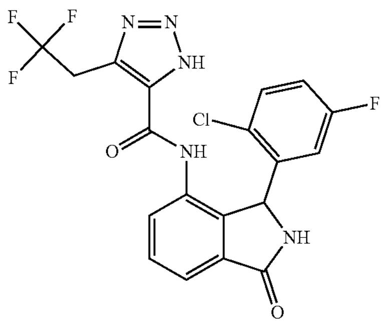 [SMILES: O=C1NC(c2cc(F)ccc2Cl)c2c(NC(=O)c3[nH]nnc3CC(F)(F)F)cccc21] | Fc1ccc(C1)c(c1)C1NC(=O)c2cccc(NC(=O)c3[nH]nnc3CC(F)(F)F)c12 | (400 MHz, DMSO-d6) δ 10.19 (br s, 1H), 9.10 (br s, 1H), 7.68-7.62 (m, 1H), 7.62-7.56 (m, 2H), 7.31 (dd, J = 8.8, 5.2 Hz, 1H), 7.07 (td, J = 8.4, 3.1 Hz, 1H), 6.62 (br s, 1H), 6.12 (br s, 1H), 4.11-3.97 (m, 2H). | 454.0 | E | |
| I-2195 | 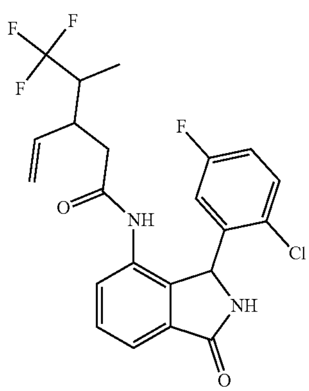 [SMILES: C=CC(CC(=O)Nc1cccc2c1C(c1cc(F)ccc1Cl)NC2=O)C(C)C(F)(F)F] | CC(C(CC(=O)Nc1cccc2C(=O)NC(c12)c1cc(F)ccc1Cl)C=C)C(F)(F)F | (400 MHz, DMSO-d6) δ 9.67 (br. s, 1H), 9.07 (br. s, 1H), 7.68-7.51 (m, 2H), 7.54-7.44 (m, 1H), 7.41 (dd, J = 7.5, 1.4 Hz, 1H), 7.32-7.10 (m, 1H), 6.59 (br. s, 1H), 6.04 (br. s, 1H), 5.58 (dd, J = 17.6, 8.5 Hz, 1H), 5.04-4.87 (m, 2H), 2.87-2.63 (m, 1H), 2.35-1.88 (m, 2H), 0.99 (d, J = 7.1 Hz, 3H); 1:1 mixture of diastereomers. | 455.3 | D | |
| I-2196 | 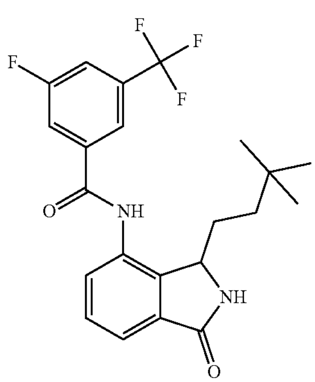 [SMILES: CC(C)(C)CCC1NC(=O)c2cccc(NC(=O)c3cc(F)cc(C(F)(F)F)c3)c21] | CC(C)(C)CCC1NC(=O)c2cccc(NC(=O)c3cc(F)cc(c3)C(F)(F)F)c12 | (400 MHz, DMSOd6) δ 10.79 (s, 1H), 8.72 (s, 1H), 8.16 (s, 1H), 8.09 (d, J = 8.9 Hz, 1H), 8.03 (d, J = 8.4 Hz, 1H), 7.60-7.51 (m, 3H), 4.79 (dd, J = 6.4, 2.4 Hz, 1H), 1.88-1.76 (m, 1H), 1.43-1.28 (m, 1H), 0.99-0.81 (m, 2H), 0.68 (s, 9H). | 423.4 | D | |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-2197 | 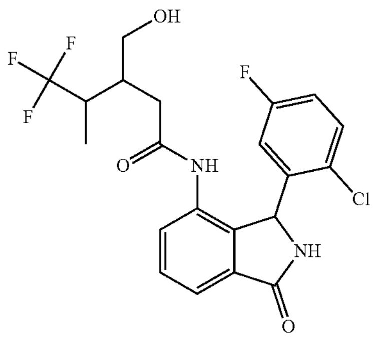 [SMILES: CC(C(CO)CC(=O)Nc1cccc2c1C(c1cc(F)ccc1Cl)NC2=O)C(F)(F)F] | CC(C(C O)CC(= O)Nc1cc cc2C(=O) NC(c12) c1cc(F)c cc1Cl)C (F)(F)F | (400 MHz, DMSO-d6) δ 9.72 (s, 1H), 9.07 (s, 1H), 7.68-7.53 (m, 2H), 7.52-7.44 (m, 1H), 7.39 (dd, J = 7.5, 1.3 Hz, 1H), 7.27-7.15 (m, 1H), 6.59 (br. s, 1H), 6.01 (overlapping br. s, 1H), 4.82 (overlapping d, J = 5.0 Hz, 1H), 3.32-3.13 (m, 1H), 3.15-2.97 (m, 1H), 2.75-2.54 (m, 1H), 2.41-2.15 (m, 1H), 2.10-1.76 (m, 2H), 0.94 (d, J = 3.6 Hz, 3H); 1:1 mixture of diastereomers | 459.2 | E | |
| I-2198 | 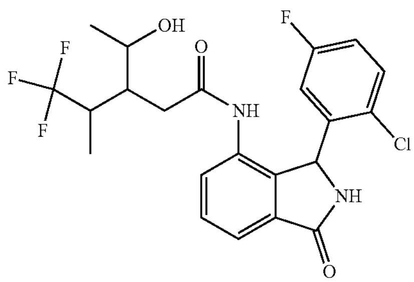 [SMILES: CC(O)C(CC(=O)Nc1cccc2c1C(c1cc(F)ccc1Cl)NC2=O)C(C)C(F)(F)F] | CC(O)C (CC(=O) Nc1ccc c2C(=O)N C(c12)c1 cc(F)ccc 1Cl)C(C) C(F)(F)F | (400 MHz, DMSO-d6) δ 9.64 (br. s, 1H), 9.06 (br. s, 1H), 7.65-7.51 (m, 2H), 7.51-7.32 (m, 2H), 7.26-7.11 (m, 1H), 6.50 (br. s, 1H), 6.06 (br. s, 1H), 4.70 (d, J = 4.2 Hz, 1H), 3.71-3.38 (m, 1H), 3.00-2.57 (m, 1H), 2.39-1.84 (m, 3H), 1.00-0.93 (m, 3H), 0.89 (d, J = 6.2 Hz, 3H); 1:1:0.85:0.75 mixture of diastereomers. | 473.3 | E | |
| I-2199 | 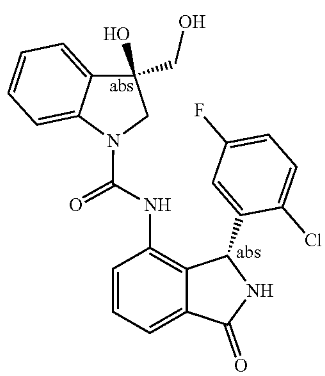 [SMILES: O=C1N[C@@H](c2cc(F)ccc2Cl)c2c(NC(=O)N3C[C@@](O)(CO)c4ccccc43)cccc21] | OC[C@] 1(O)CN (C(=O)Nc 2cccc3C (=O)N[C@ H](c23) c2cc(F)c cc2Cl)c2 ccccc12 | (400 MHz, DMSO-d6) 9.05 (s, 1H), 8.43 (s, 1H), 7.75 (d, J = 8.1 Hz, 1H), 7.62-7.52 (m, 2H), 7.49 (dd, J = 7.0, 2.0 Hz, 1H), 7.36 (dd, J = 8.9, 5.1 Hz, 1H), 7.28 (d, J = 7.4 Hz, 1H), 7.23-7.15 (m, 1H), 7.10 (td, J = 8.4, 3.1 Hz, 1H), 6.95 (t, J = 7.5 Hz, 1H), 6.14 (s, 1H), 5.41 (s, 1H), 4.90 (t, J = 5.4 Hz, 1H), 3.93 (d, J = 10.8 Hz, 1H), 3.50 (d, J = 5.5 Hz, 2H), 3.27 (d, J = 10.7 Hz, 1H). | 468.1 | E | |
| I-2200 | 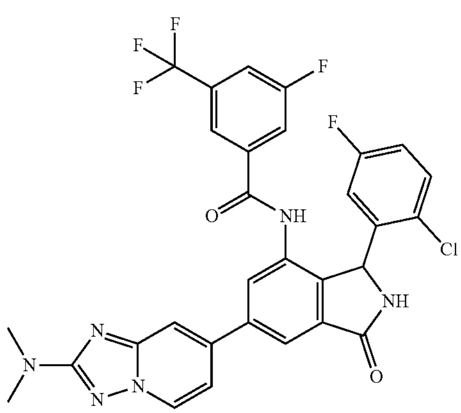 [SMILES: CN(C)c1nc2cc(-c3cc(NC(=O)c4cc(F)cc(C(F)(F)F)c4)c4c(c3)C(=O)NC4c3cc(F)ccc3Cl)ccn2n1] | CN(C)c1 nc2cc(cc n2n1)-c1cc2C(= O)NC(c2 c(NC(=O) c2cc(F)c c(c2)C(F) (F)F)c1) c1cc(F)c cc1Cl | (DMSO-d6, 400 MHz) 10.61 (1H, s), 9.23 (1H, s), 9.16 (1H, s), 8.04 (1H, s), 7.99-7.86 (3H, m), 7.78 (1H, d, J = 9.0 Hz), 7.72 (1H, s), 7.56 (1H, d, J = 9.2 Hz), 7.34 (1H, dd, J = 8.9, 5.1 Hz), 7.16-7.08 (1H, m), 6.03 (1H, s), 3.08 (6H, s) | 627.1 | A | A |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-2201 | 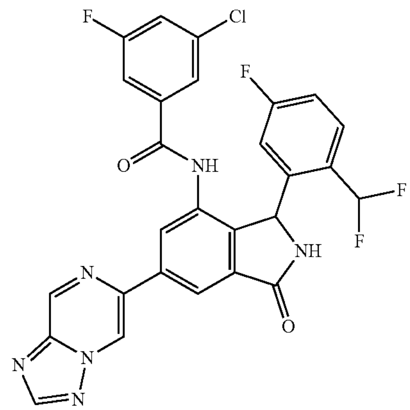 [SMILES: O=C(Nc1cc(-c2cn3ncnc3cn2)cc2c1C(c1cc(F)ccc1C(F)F)NC2=O)c1cc(F)cc(Cl)c1] | FC(F)c1cc(F)cc1C1NC(=O)c2cc(cc(NC(=O)c3cc(F)cc(Cl)c312)-c1cn2ncnc2cn1 | | 567.2 | A | B |
| I-2202 | 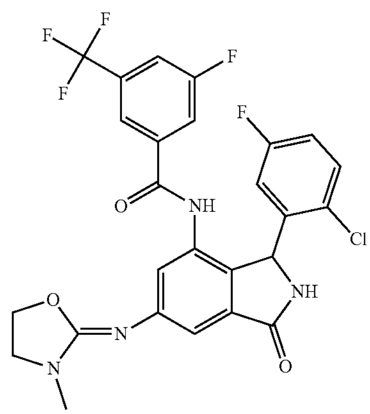 [SMILES: CN1CCO/C1=N\c1cc(NC(=O)c2cc(F)cc(C(F)(F)F)c2)c2c(c1)C(=O)NC2c1cc(F)ccc1Cl] | CN1CCO\C1=N/c1cc2C(=O)NC(c2c(NC(=O)c2cc(F)cc(c2)C(F)(F)F)c1)c1cc(F)ccc1Cl | | 565.0 | | B |
| I-2203 | 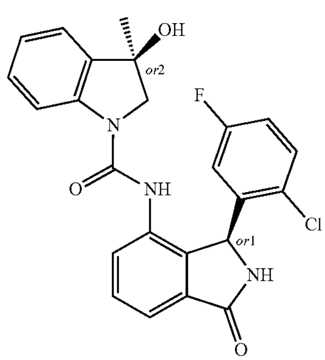 [SMILES: C[C@]1(O)CN(C(=O)Nc2cccc3c2[C@@H](c2cc(F)ccc2Cl)NC3=O)c2ccccc21] | C[C@]1(O)CN(C(=O)Nc2ccc3C(=O)N[C@@H](c23)c2cc(F)ccc2Cl)c2ccccc12 | (400 MHz, DMSO-d6) 9.07 (s, 1H), 8.39 (s, 1H), 7.67 (d, J = 8.1 Hz, 1H), 7.61-7.51 (m, 3H), 7.37 (dd, J = 8.8, 5.2 Hz, 1H), 7.29 (dd, J = 7.5, 1.4 Hz, 1H), 7.21-7.13 (m, 1H), 7.09 (td, J = 8.4, 3.1 Hz, 1H), 7.00-6.92 (m, 1H), 6.53 (s, 1H) 6.14 (s, 1H), 5.46 (s, 1H), 3.59 (d, J = 10.6 Hz, 1H), 3.51 (d, J = 10.5 Hz, 1H), 1.45 (s, 3H). | 452.0 | D | |
| I-2204 | 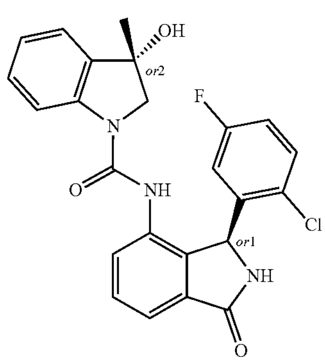 [SMILES: C[C@@]1(O)CN(C(=O)Nc2cccc3c2[C@@H](c2cc(F)ccc2Cl)NC3=O)c2ccccc21] | C[C@@]1(O)CN(C(=O)Nc2ccc3C(=O)N[C@@H](c23)c2cc(F)ccc2Cl)c2ccccc12 | | 450.0 | D | |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-2205 | 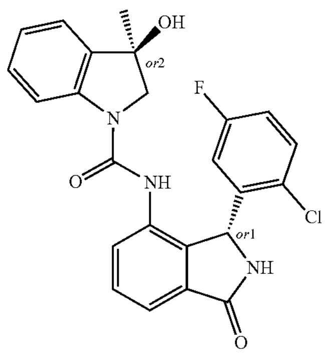 [SMILES: C[C@]1(O)CN(C(=O)Nc2cccc3c2[C@H](c2cc(F)ccc2Cl)NC3=O)c2ccccc21] | C[C@]1(O)CN(C(=O)Nc2cccc3C(=O)N[C@H](c23)c2cc(F)ccc2Cl)c2ccccc12 | (400 MHz, DMSO-d6) 9.04 (s, 1H), 8.58 (s, 1H), 7.84 (d, J = 8.1 Hz, 1H), 7.72-7.51 (m, 2H), 7.42-7.34 (m, 2H), 7.31 (dd, J = 7.4, 1.3 Hz, 1H), 7.26-7.12 (m, 3H), 6.98 (td, J = 7.4, 1.1 Hz, 1H), 6.58 (s, 1H), 6.01 (s, 1H), 5.52 (s, 1H), 3.84 (d, J = 10.8 Hz, 1H), 1.41 (s, 3H). | 450.0 | A | A |
| I-2206 | 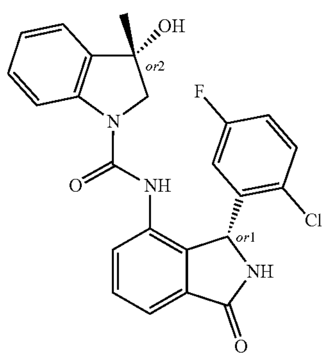 [SMILES: C[C@@]1(O)CN(C(=O)Nc2cccc3c2[C@H](c2cc(F)ccc2Cl)NC3=O)c2ccccc21] | C[C@@]1(O)CN(C(=O)Nc2cccc3C(=O)N[C@H](c23)c2cc(F)ccc2Cl)c2ccccc12 | (400 MHz, DMSO-d6) 9.04 (s, 1H), 8.58 (s, 1H), 7.84 (d, J = 8.0 Hz, 1H), 7.57 (d, J = 7.3 Hz, 2H), 7.37 (dd, J = 9.0, 5.5 Hz, 2H), 7.31 (d, J = 7.4 Hz, 1H), 7.26-7.12 (m, 2H), 6.53-6.98 (t, J = 7.4 Hz, 1H), 6.01 (s, 1H), 5.51 (s, 1H), 3.84 (d, J = 10.8 Hz, 1H), 2.97 (s, 1H), 1.41 (s, 3H). | 452.0 | E | |
| I-2207 | 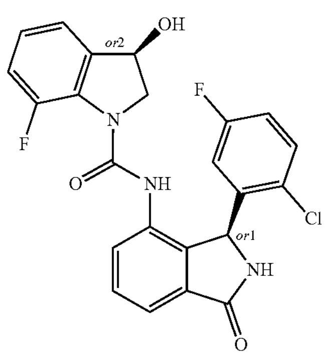 [SMILES: O=C1N[C@H](c2cc(F)ccc2Cl)c2c(NC(=O)N3C[C@H](O)c4cccc(F)c43)cccc21] | O[C@H]1CN(C(=O)Nc2cccc3C(=O)N[C@@H](c23)c2cc(F)ccc2Cl)c2c1cccc2F | (400 MHz, DMSO-d6) 9.09 (s, 1H), 9.04 (s, 1H), 7.57 (d, J = 4.3 Hz, 2H), 7.49 (s, 1H), 7.43-7.37 (m, 1H), 7.26 (td; J = 8.4, 3.1 Hz, 1H), 7.16 (dd, J = 5.2, 3.4 Hz, 1H), 7.13-7.04 (m, 2H), 5.94 (s, 1H), 5.77 (d, J = 6.2 Hz, 1H), 5.15 (q, J = 6.7 Hz, 1H), 3.51 (dd, J = 11.3, 6.0 Hz, 1H), 3.24 (t, J = 9.6 Hz, 1H). | 456.1 | D | |
| I-2208 | 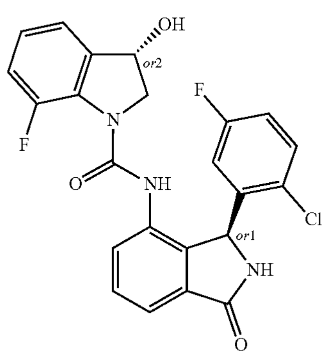 [SMILES: O=C1N[C@H](c2cc(F)ccc2Cl)c2c(NC(=O)N3C[C@@H](O)c4cccc(F)c43)cccc21] | O[C@@H]1CN(C(=O)Nc2cccc3C(=O)N[C@@H](c23)c2cc(F)ccc2Cl)c2c1cccc2F | (400 MHz, DMSO-d6) 9.09 (s, 1H), 9.04 (s, 1H), 7.57 (d, J = 4.3 Hz, 2H), 7.49 (s, 1H), 7.43-7.37 (m, 1H), 7.26 (td, J = 8.4, 3.1 Hz, 1H), 7.16 (dd, J = 5.2, 3.4 Hz, 1H), 7.13-7.04 (m, 2H), 5.94 (s, 1H), 5.77 (d, J = 6.2 Hz, 1H), 5.15 (q, J = 6.7 Hz, 1H), 3.51 (dd, J = 11.3, 6.0 Hz, 1H), 3.24 (t, J = 9.6 Hz, 1H). | 456.1 | E | |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-2209 | 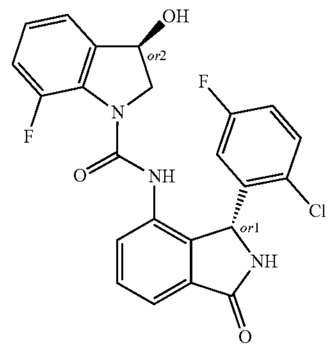 [SMILES: O=C1N[C@@H](c2cc(F)ccc2Cl)c2c(NC(=O)N3C[C@H](O)c4cccc(F)c43)cccc21] | O[C@H]1CN(C(=O)Nc2ccc c3C(=O)N[C@H](c23)c2c c(F)ccc2Cl)c2c1ccc2F | (400 MHz, DMSO-d6) 9.09 (s, 1H), 9.04 (s, 1H), 7.57 (d, J = 4.3 Hz, 2H), 7.49 (s, 1H), 7.43-7.37 (m, 1H), 7.26 (td, J = 8.4, 3.1 Hz, 1H), 7.16 (dd, J = 5.2, 3.4 Hz, 1H), 7.13-7.04 (m, 2H), 5.94 (s, 1H), 5.77 (d, J = 6.2 Hz, 1H), 5.15 (q, J = 6.7 Hz, 1H), 3.51 (dd, J = 11.3, 6.0 Hz, 1H), 3.24 (t, J = 9.6 Hz, 1H). | 456.1 | E | |
| I-2210 | 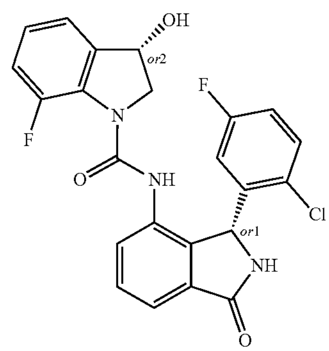 [SMILES: O=C1N[C@@H](c2cc(F)ccc2Cl)c2c(NC(=O)N3C[C@@H](O)c4cccc(F)c43)cccc21] | O[C@@H]1CN(C(=O)Nc2cccc3C(=O)N[C@H](c23)c2cc(F)ccc2Cl)c2c1cccc2F | (400 MHz, DMSO-d6) 9.09 (s, 1H), 9.04 (s, 1H), 7.57 (d, J = 4.3 Hz, 2H), 7.49 (s, 1H), 7.43-7.37 (m, 1H), 7.26 (td, J = 8.4, 3.1 Hz, 1H), 7.16 (dd, J = 5.2, 3.4 Hz, 1H), 7.13-7.04 (m, 2H), 5.94 (s, 1H), 5.77 (d, J = 6.2 Hz, 1H), 5.15 (q, J = 6.7 Hz, 1H), 3.51 (dd, J = 11.3, 6.0 Hz, 1H), 3.24 (t, J = 9.6 Hz, 1H). | 456.1 | E | |
| I-2211 | 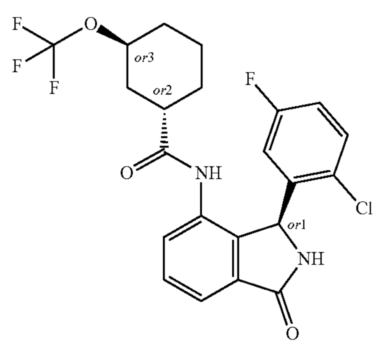 [SMILES: O=C1N[C@H](c2cc(F)ccc2Cl)c2c(NC(=O)[C@H]3CCC[C@H](OC(F)(F)F)C3)cccc21] | Fc1ccc(C1)c(c1)[C@H]1NC(=O)c2ccc c(NC(=O)[C@H]3CCC[C@@H](C3)OC(F)(F)F)c12 | Mixture (400 MHz, DMSO-d6) δ 9.79 (br s, 0.35H), 9.77 (br s, 0.15H), 9.76 (br s, 0.15H), 9.73 (br s, 0.35H), 9.09 (br s, 1H), 7.63-7.54 (m, 2H), 7.52-7.44 (m, 1H), 7.43-7.35 (m, 1H), 7.25-7.16 (m, 1H), 6.46 (br s, 1H), 6.03 (br s, 1H), 4.74-4.70 (m, 0.15H), 4.70-4.67 (m, 0.15H), 4.33-4.27 (m, 0.35H), 4.27-4.21 (m, 0.35H), 2.46-2.40 (m, 0.15H), 2.39-2.30 (m, 0.15H), 2.26-2.20 (m, 0.35H), 2.20-2.14 (m, 0.35H), 1.95 (br s, 1H), 1.84-1.38 (m, 4.3H), 1.37-1.16 (m, 2H), 1.13-1.00 (m, 0.3H), 0.99-0.86 (m, 0.3H). | 471.0 | E | |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-2212 | 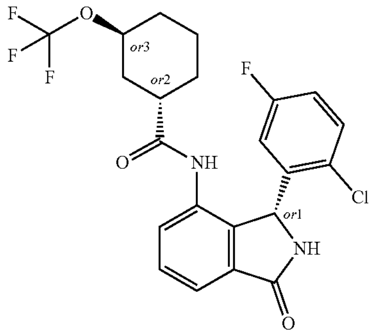 [SMILES: O=C1N[C@@H](c2cc(F)ccc2Cl)c2c(NC(=O)[C@H]3CCC[C@H](OC(F)(F)F)C3)cccc21] | Fc1ccc(C1)c(c1)[C@@H]1NC(=O)c2cccc(NC(=O)[C@H]3CCC[C@@H](C3)OC(F)(F)F)c12 | Mixture (400 MHz, DMSO-d6) δ 9.79 (br s, 0.35H), 9.77 (br s, 0.15H), 9.76 (br s, 0.15H), 9.73 (br S, 0.35H), 9.09 (br s, 1H), 7.63-7.54 (m, 2H), 7.52-7.44 (m, 1H), 7.43-7.35 (m, 1H), 7.25-7.16 (m, 1H), 6.46 (br s, 1H), 6.03 (br s, 1H), 4.74-4.70 (m, 0.15H), 4.70-4.67 (m, 0.15H), 4.33-4.27 (m, 0.35H), 4.27-4.21 (m, 0.35H), 2.46-2.40 (m, 0.15H), 2.39-2.30 (m, 0.15H), 2.26-2.20 (m, 0.35H), 2.20-2.14 (m, 0.35H), 1.95 (br s, 1H), 1.84-1.38 (m, 4.3H), 1.37-1.16 (m, 2H), 1.13-1.00 (m, 0.3H), 0.99-0.86 (m, 0.3H). | 471.0 | E | |
| I-2213 | 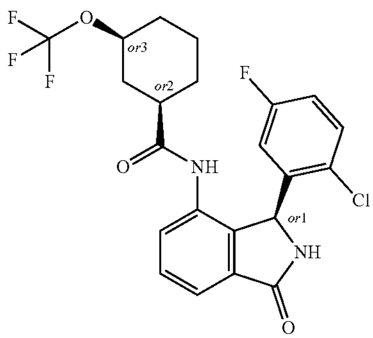 [SMILES: O=C1N[C@H](c2cc(F)ccc2Cl)c2c(NC(=O)[C@@H]3CCC[C@H](OC(F)(F)F)C3)cccc21] | Fc1ccc(C1)c(c1)[C@H]1NC(=O)c2cccc(NC(=O)[C@@H]3CCC[C@@H](C3)OC(F)(F)F)c12 | Mixture (400 MHz, DMSO-d6) δ 9.79 (br s, 0.35H), 9.77 (br s, 0.15H), 9.76 (br s, 0.15H), 9.73 (br S, 0.35H), 9.09 (br s, 1H), 7.63-7.54 (m, 2H), 7.52-7.44 (m, 1H), 7.43-7.35 (m, 1H), 7.25-7.16 (m, 1H), 6.46 (br s, 1H), 6.03 (br s, 1H), 4.74-4.70 (m, 0.15H), 4.70-4.67 (m, 0.15H), 4.33-4.27 (m, 0.35H), 4.27-4.21 (m, 0.35H), 2.46-2.40 (m, 0.15H), 2.39-2.30 (m, 0.15H), 2.26-2.20 (m, 0.35H), 2.20-2.14 (m, 0.35H), 1.95 (br s, 1H), 1.84-1.38 (m, 4.3H), 1.37-1.16 (m, 2H), 1.13-1.00 (m, 0.3H), 0.99-0.86 (m, 0.3H). | 471.0 | E | |
| I-2214 | 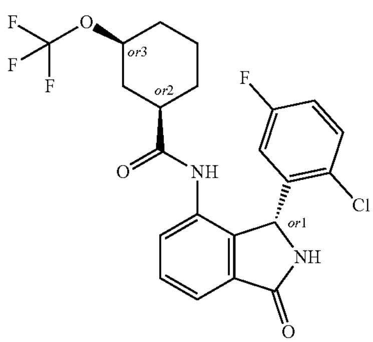 [SMILES: O=C1N[C@@H](c2cc(F)ccc2Cl)c2c(NC(=O)[C@@H]3CCC[C@H](OC(F)(F)F)C3)cccc21] | Fc1ccc(C1)c(c1)[C@@H]1NC(=O)c2cccc(NC(=O)[C@@H]3CCC[C@@H](C3)OC(F)F)c12 | Mixture (400 MHz, DMSO-d6) δ 9.79 (br s, 0.35H), 9.77 (br s, 0.15H), 9.76 (br s, 0.15H), 9.73 (br s, 0.35H), 9.09 (br s, 1H), 7.63-7.54 (m, 2H), 7.52-7.44 (m, 1H), 7.43-7.35 (m, 1H), 7.25-7.16 (m, 1H), 6.46 (br s, 1H), 6.03 (br s, 1H), 4.74-4.70 (m, 0.15H), 4.70-4.67 (m, 0.15H), 4.33-4.27 (m, 0.35H), 4.27-4.21 (m, 0.35H), 2.46-2.40 (m, 0.15H), 2.39-2.30 (m, 0.15H), 2.26-2.20 (m, 0.35H), 2.20-2.14 (m, 0.35H), 1.95 (br s, 1H), 1.84-1.38 (m, 4.3H), 1.37-1.16 (m, 2H), 1.13-1.00 (m, 0.3H), 0.99-0.86 (m, 0.3H). | 471.0 | E | |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-2215 | 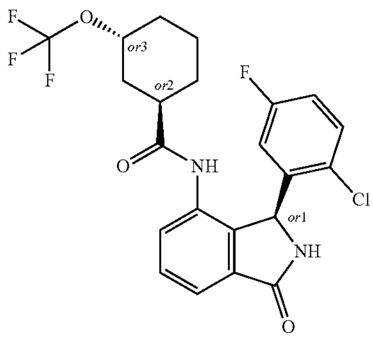 [SMILES: O=C1N[C@H](c2cc(F)ccc2Cl)c2c(NC(=O)[C@@H]3CCC[C@@H](OC(F)(F)F)C3)cccc21] | Fc1ccc(C1)c(c1)[C@H]1NC(=O)c2ccc(NC(=O)[C@@H]3CCC[C@H](C3)OC(F)(F)F)c12 | Mixture (400 MHz, DMSO-d6) δ 9.79 (br s, 0.35H), 9.77 (br s, 0.15H), 9.76 (br s, 0.15H), 9.73 (br S, 0.35H), 9.09 (br s, 1H), 7.63-7.54 (m, 2H), 7.52-7.44 (m, 1H), 7.43-7.35 (m, 1H), 7.25-7.16 (m, 1H), 6.46 (br s, 1H), 6.03 (br s, 1H), 4.74-4.70 (m, 0.15H), 4.70-4.67 (m, 0.15H), 4.33-4.27 (m, 0.35H), 4.27-4.21 (m, 0.35H), 2.46-2.40 (m, 0.15H), 2.39-2.30 (m, 0.15H), 2.26-2.20 (m, 0.35H), 2.20-2.14 (m, 0.35H), 1.95 (br s, 1H), 1.84-1.38 (m, 4.3H), 1.37-1.16 (m, 2H), 1.13-1.00 (m, 0.3H), 0.99-0.86 (m, 0.3H). | 471.0 | | E |
| I-2216 | 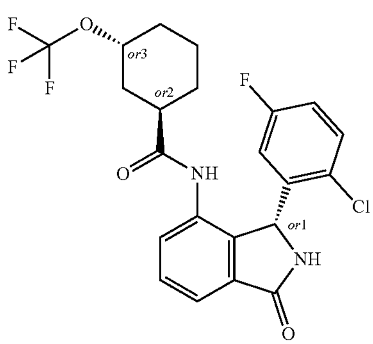 [SMILES: O=C1N[C@@H](c2cc(F)ccc2Cl)c2c(NC(=O)[C@@H]3CCC[C@@H](OC(F)(F)F)C3)cccc21] | Fc1ccc(C1)c(c1)[C@@H]1NC(=O)c2cccc(NC(=O)[C@@H]3CCC[C@H](C3)OC(F)(F)F)c12 | Mixture (400 MHz, DMSO-d6) δ 9.79 (br s, 0.35H), 9.77 (br s, 0.15H), 9.76 (br 0.15H), 9.73 (br s, 0.35H), 9.09 (br s, 1H), 7.63-7.54 (m, 2H), 7.52-7.44 (m, 1H), 7.43-7.35 (m, 1H), 7.25-7.16 (m, 1H), 6.46 (br s, 1H), 6.03 (br s, 1H), 4.74-4.70 (m, 0.15H), 4.70-4.67 (m, 0.15H), 4.33-4.27 (m, 0.35H), 4.27-4.21 (m, 0.35H), 2.46-2.40 (m, 0.15H), 2.39-2.30 (m, 0.15H), 2.26-2.20 (m, 0.35H), 2.20-2.14 (m, 0.35H), 1.95 (br s, 1H), 1.84-1.38 (m, 4.3H), 1.37-1.16 (m, 2H), 1.13-1.00 (m, 0.3H), 0.99-0.86 (m, 0.3H). | 471.0 | | E |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-2217 | 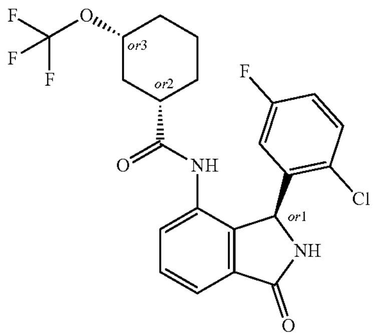 [SMILES: O=C1N[C@H](c2cc(F)ccc2Cl)c2c(NC(=O)[C@H]3CCC[C@@H](OC(F)(F)F)C3)cccc21] | Fc1ccc(C1)c(c1)[C@H]1NC(=O)c2ccc c(NC(=O)[C@H]3CCC[C@H](C3)OC(F)(F)F)c12 | Mixture (400 MHz, DMSO-d6) δ 9.79 (br s, 0.35H), 9.77 (br s, 0.15H), 9.76 (br s, 0.15H), 9.73 (br S, 0.35H), 9.09 (br s, 1H), 7.63-7.54 (m, 2H), 7.52-7.44 (m, 1H), 7.43-7.35 (m, 1H), 7.25-7.16 (m, 1H), 6.46 (br s, 1H), 6.03 (br s, 1H), 4.74-4.70 (m, 0.15H), 4.70-4.67 (m, 0.15H), 4.33-4.27 (m, 0.35H), 4.27-4.21 (m, 0.35H), 2.46-2.40 (m, 0.15H), 2.39-2.30 (m, 0.15H), 2.26-2.20 (m, 0.35H), 2.20-2.14 (m, 0.35H), 1.95 (br s, 1H), 1.84-1.38 (m, 4.3H), 1.37-1.16 (m, 2H), 1.13-1.00 (m, 0.3H), 0.99-0.86 (m, 0.3H). | 471.0 | E | |
| I-2218 | 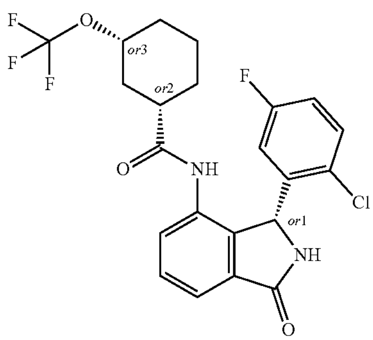 [SMILES: O=C1N[C@@H](c2cc(F)ccc2Cl)c2c(NC(=O)[C@H]3CCC[C@@H](OC(F)(F)F)C3)cccc21] | Fc1ccc(C1)c(c1)[C@@H]1NC(=O)c2cccc(NC(=O)[C@H]3CCC[C@H](C3)OC(F)(F)F)c12 | Mixture (400 MHz, DMSO-d6) δ 9.79 (br s, 0.35H), 9.77 (br s, 0.15H), 9.76 (br s, 0.15H), 9.73 (br s, 0.35H), 9.09 (br s, 1H), 7.63-7.54 (m, 2H), 7.52-7.44 (m, 1H), 7.43-7.35 (m, 1H), 7.25-7.16 (m, 1H), 6.46 (br s, 1H), 6.03 (br s, 1H), 4.74-4.70 (m, 0.15H), 4.70-4.67 (m, 0.15H), 4.33-4.27 (m, 0.35H), 4.27-4.21 (m, 0.35H), 2.46-2.40 (m, 0.15H), 2.39-2.30 (m, 0.15H), 2.26-2.20 (m, 0.35H), 2.20-2.14 (m, 0.35H), 1.95 (br s, 1H), 1.84-1.38 (m, 4.3H), 1.37-1.16 (m, 2H), 1.13-1.00 (m, 0.3H), 0.99-0.86 (m, 0.3H). | 471.0 | E | |
| I-2219 | 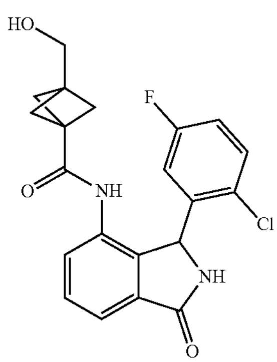 [SMILES: O=C1NC(c2cc(F)ccc2Cl)c2c(NC(=O)C34CC(CO)(C3)C4)cccc21] | OCC12CC(C1)(C2)C(=O)Nc1cccc2C(=O)NC(c12)c1cc(F)ccc1Cl | (400 MHz, DMSO-d6) δ 9.41 (br. s, 1H), 9.05 (br. s, 1H), 7.60 (dd, J = 7.4, 0.9 Hz, 1H), 7.55 (t, J = 7.5 Hz, 1H), 7.51-7.44 (m, 1H), 7.38 (dd, J = 7.6, 1.0 Hz, 1H), 7.24 (ddd, J = 8.8, 8.1, 3.1 Hz, 1H), 6.54 (br. s, 1H), 5.97 (br. s, 1H), 4.53 (t, J = 5.6 Hz, 1H), 3.33-3.31 (m, 2H), 1.65-1.59 (m, 6H). | 401.3 | E | |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-2220 | 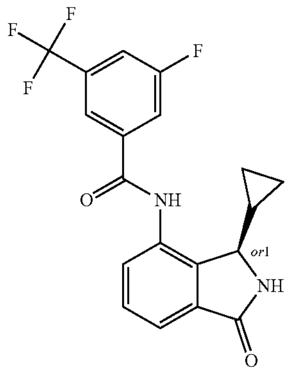 [SMILES: O=C(Nc1cccc2c1[C@@H](C1CC1)NC2=O)c1cc(F)cc(C(F)(F)F)c1] | Fc1cc(cc(c1)C(F)(F)F)C(=O)Nc1cccc2C(=O)N[C@H](C3CC3)c12 | | 379.4 | E | |
| I-2221 | 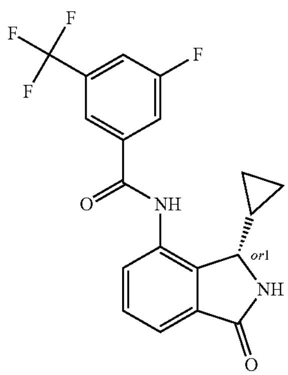 [SMILES: O=C(Nc1cccc2c1[C@H](C1CC1)NC2=O)c1cc(F)cc(C(F)(F)F)c1] | Fc1cc(cc(c1)C(F)(F)F)C(=O)Nc1cccc2C(=O)N[C@@H](C3CC3)c12 | | 379.3 | E | |
| I-2222 | 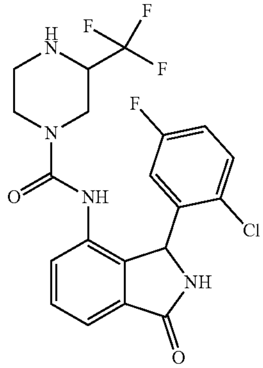 [SMILES: O=C1NC(c2cc(F)ccc2Cl)c2c(NC(=O)N3CCNC(C(F)(F)F)C3)cccc21] | Fc1ccc(C1)c(c1)C1NC(=O)c2cccc(NC(=O)N3CCNC(C3)C(F)(F)F)c12 | (400 MHz, DMSO-d6) δ 9.03 (br s, 1H), 8.65 (s, 0.6H), 8.63 (s, 0.4H), 7.63-7.45 (m, 3H), 7.33-7.13 (m, 2H), 6.48 (br s, 1H), 5.99 (br s, 1H), 3.81 (br d, J = 11.4 Hz, 1H), 3.62 (submerged br d, J = 12.0 Hz, 0.6H), 3.20-3.04 (m, 0.6H), 2.93-2.55 (m, 3.6H), 2.49-2.35 (submerged m, 1H), 2.21-2.05 (m, 0.4H). | 457.0 | E | |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-2223 | 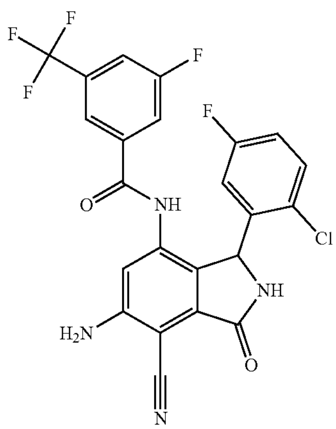 [SMILES: N#Cc1c(N)cc(NC(=O)c2cc(F)cc(C(F)(F)F)c2)c2c1C(=O)NC2c1cc(F)ccc1Cl] | Nc1cc(NC(=O)c2cc(F)cc(c2)C(F)(F)F)c2C(NC(=O)c2c1C#N)c1cc(F)ccc1Cl | (400 MHz, DMSO-d6) δ 10.42 (br s, 1 H), 9.16 (br s, 1 H), 7.94-7.82 (m, 1 H), 7.67 (d, J = 9.0 Hz, 1 H), 7.59 (s, 1 H), 7.31 (dd, J = 8.8, 5.2 Hz, 1 H), 7.07 (td, J = 8.4, 3.0 Hz, 1 H), 7.07 (submerged s, 1 H) 6.66 (br s, 1 H), 6.40 (br s, 1 H), 6.40 (submerged br s, 1 H), 5.82 (br s, 1 H). | 507.2 | A | A |
| I-2224 | 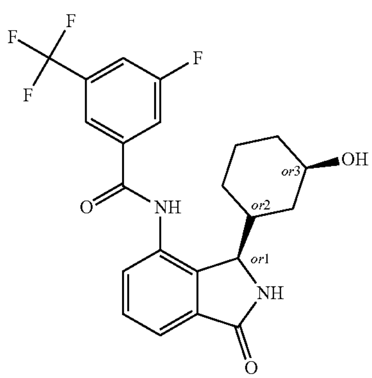 [SMILES: O=C(Nc1cccc2c1[C@@H](C1CCC[C@@H](O)C1)NC2=O)c1cc(F)cc(C(F)(F)F)c1] | O[C@@H]1CCC[C@@H](C1)C1NC(=O)c2cccc(NC(=O)c3cc(F)cc(c3)C(F)(F)F)c12 | (400 MHz, DMSO-d6) δ 10.73 (s, 1H), 8.74 (s, 1H), 8.13 (s, 1H), 8.08 (d, J = 9.4 Hz, 1H), 8.04 (d, J = 8.2 Hz, 1H), 7.66-7.49 (m, 3H), 4.73 (s, 1H), 4.60 (d, J = 3.9 Hz, 1H), 3.25-3.02 (m, 1H), 1.99-1.82 (m, 1H), 1.81-1.58 (m, 2H), 1.59-1.35 (m, 1H), 1.23 (dd, J = 23.9, 12.0 Hz, 1H), 1.09-0.73 (m, 2H), 0.75-0.43 (m, 2H); 2.5:1 mixture of diastereomers; major diastereomer described. | 437.3 | E | |
| I-2225 | 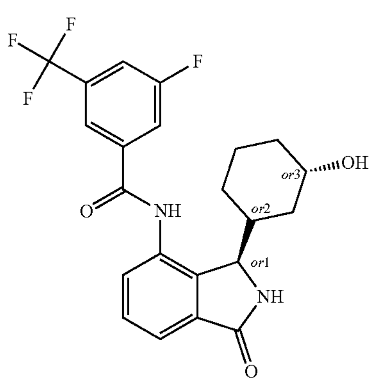 [SMILES: O=C(Nc1cccc2c1[C@@H](C1CCC[C@H](O)C1)NC2=O)c1cc(F)cc(C(F)(F)F)c1] | O[C@H]1CCCC(C1)[C@H]1NC(=O)c2cccc(NC(=O)c3cc(F)cc(c3)C(F)(F)F)c12 | (400 MHz, DMSO-d6) δ 10.73 (s, 1H), 8.74 (s, 1H), 8.13 (s, 1H), 8.08 (d, J = 9.4 Hz, 1H), 8.04 (d, J = 8.2 Hz, 1H), 7.66-7.49 (m, 3H), 4.73 (s, 1H), 4.60 (d, J = 3.9 Hz, 1H), 3.25-3.02 (m, 1H), 1.99-1.82 (m, 1H), 1.81-1.58 (m, 2H), 1.59-1.35 (m, 1H), 1.23 (dd, J = 23.9, 12.0 Hz, 1H), 1.09-0.73 (m, 2H), 0.75-0.43 (m, 2H); 2.5:1 mixture of diastereomers; major diastereomer described. | 437.3 | E | |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-2226 | 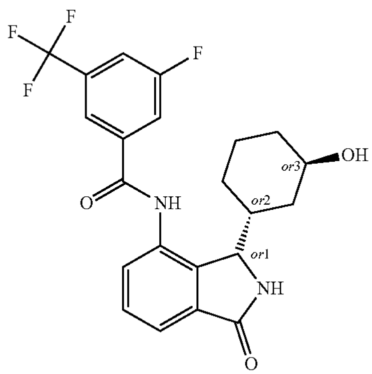 [SMILES: O=C(Nc1cccc2c1C([C@@H]1CCC[C@@H](O)C1)NC2=O)c1cc(F)cc(C(F)(F)F)c1] | O[C@@H]1CCC[C@H](C1)C1NC(=O)c2cccc(NC(=O)c3cc(F)cc(c3)C(F)(F)F)c12 | (400 MHz, DMSO-d6) δ 10.73 (s, 1H), 8.74 (s, 1H), 8.13 (s, 1H), 8.08 (d, J = 9.4 Hz, 1H), 8.04 (d, J = 8.2 Hz, 1H), 7.66-7.49 (m, 3H), 4.73 (s, 1H), 4.60 (d, J = 3.9 Hz, 1H), 3.25-3.02 (m, 1H), 1.99-1.82 (m, 1H), 1.81-1.58 (m, 2H), 1.59-1.35 (m, 1H), 1.23 (dd, J = 23.9, 12.0 Hz, 1H), 1.09-0.73 (m, 2H), 0.75-0.43 (m, 2H); 2.5:1 mixture of diastereomers; major diastereomer described. | 437.3 | E | |
| I-2227 | 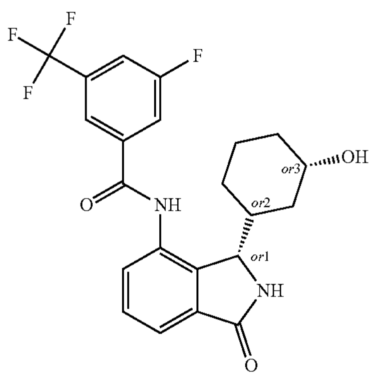 [SMILES: O=C(Nc1cccc2c1[C@H](C1CCC[C@H](O)C1)NC2=O)c1cc(F)cc(C(F)(F)F)c1] | O[C@H]1CCC[C@H](C1)C1NC(=O)c2cccc(NC(=O)c3cc(F)cc(c3)C(F)(F)F)c12 | (400 MHz, DMSO-d6) δ 10.73 (s, 1H), 8.74 (s, 1H), 8.13 (s, 1H), 8.08 (d, J = 9.4 Hz, 1H), 8.04 (d, J = 8.2 Hz, 1H), 7.66-7.49 (m, 3H), 4.73 (s, 1H), 4.60 (d, J = 3.9 Hz, 1H), 3.25-3.02 (m, 1H), 1.99-1.82 (m, 1H), 1.81-1.58 (m, 2H), 1.59-1.35 (m, 1H), 1.23 (dd, J = 23.9, 12.0 Hz, 1H), 1.09-0.73 (m, 2H), 0.75-0.43 (m, 2H); 2.5:1 mixture of diastereomers; major diastereomer described. | 437.3 | E | |
| I-2228 | 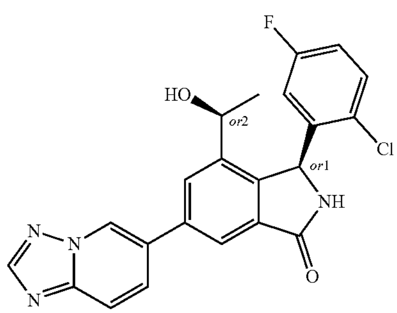 [SMILES: C[C@H](O)c1cc(-c2ccc3ncnn3c2)cc2c1[C@@H](c1cc(F)ccc1Cl)NC2=O] | C[C@H](O)c1cc(cc2C(=O)N[C@@H](c12)c1cc(F)ccc1Cl)-c1ccc2ncnn2c1 | (400 MHz, DMSO-d6) δ 9.43 (br. s, 1H), 9.23 (br. s, 1H), 8.57 (s, 1H), 8.14-8.10 (m, 1H), 8.09 (d, J = 1.8 Hz, 1H), 8.08-8.01 (m, 2H), 7.98 (br. s, 1H), 7.71-7.54 (m, 1H), 7.28 (td, J = 8.5, 2.9 Hz, 1H), 6.51 (br. s, 1H), 6.22 (br. s, 1H), 5.28 (d, J = 3.5 Hz, 1H), 4.54-4.41 (m, 1H), 1.25 (d, J = 5.0 Hz, 3H); 3:1 mixture of diastereomers; major diastereomer described. | 423.1 | E | |
| I-2229 | 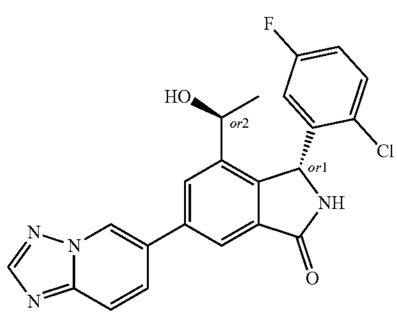 [SMILES: C[C@H](O)c1cc(-c2ccc3ncnn3c2)cc2c1[C@H](c1cc(F)ccc1Cl)NC2=O] | C[C@H](O)c1cc(cc2C(=O)N[C@H](c12)c1cc(F)ccc1Cl)c1ccc2ncnn2c1 | (400 MHz, DMSO-d6) δ 9.43 (br. s, 1H), 9.23 (br. s, 1H), 8.57 (s, 1H), 8.14-8.10 (m, 1H), 8.09 (d, J = 1.8 Hz, 1H), 8.08-8.01 (m, 2H), 7.98 (br. s, 1H), 7.71-7.54 (m, 1H), 7.28 (td, J = 8.5, 2.9 Hz, 1H), 6.51 (br. s, 1H), 6.22 (br. s, 1H), 5.28 (d, J = 3.5 Hz, 1H), 4.54-4.41 (m, 1H), 1.25 (d, J = 5.0 Hz, 3H); 3:1 mixture of diastereomers; major diastereomer described | 423.1 | E | |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-2230 | 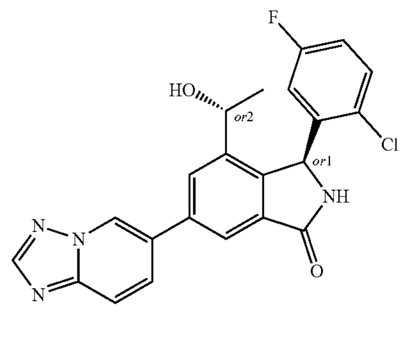 [SMILES: C[C@@H](O)c1cc(-c2ccc3ncnn3c2)cc2c1[C@@H](c1cc(F)ccc1Cl)NC2=O] | C[C@@H](O)c1c c(cc2C(= O)N[C@ @H](c12) c1cc(F)c cc1Cl)- c1ccc2nc nn2c1 | (400 MHz, DMSO-d6) δ 9.43 (br. s, 1H), 9.23 (br. s, 1H), 8.57 (s, 1H), 8.14-8.10 (m, 1H), 8.09 (d, J = 1.8 Hz, 1H), 8.08-8.01 (m, 2H), 7.98 (br. s, 1H), 7.71-7.54 (m, 1H), 7.28 (td, J = 8.5, 2.9 Hz, 1H), 6.51 (br. s, 1H), 6.22 (br. s, 1H), 5.28 (d, J = 3.5 Hz, 1H), 4.54-4.41 (m, 1H), 1.25 (d, J = 5.0 Hz, 3H); 3:1 mixture of diastereomers; major diastereomer described. | 423.1 | E | |
| I-2231 | 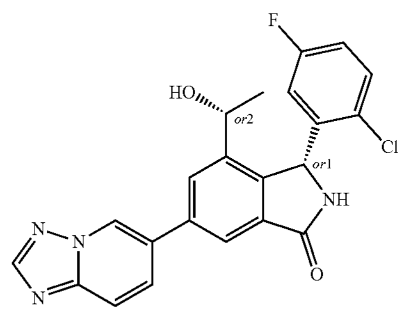 [SMILES: C[C@@H](O)c1cc(-c2ccc3ncnn3c2)cc2c1[C@H](c1cc(F)ccc1Cl)NC2=O] | C[C@@H](O)c1c c(cc2C(= O)N[C@ H](c12)c 1cc(F)cc c1Cl)- c1ccc2nc nn2c1 | (400 MHz, DMSO-d6) δ 9.43 (br. s, 1H), 9.23 (br. s, 1H), 8.57 (s, 1H), 8.14-8.10 (m, 1H), 8.09 (d, J = 1.8 Hz, 1H), 8.08-8.01 (m, 2H), 7.98 (br. s, 1H), 7.71-7.54 (m, 1H), 7.28 (td, J = 8.5, 2.9 Hz, 1H), 6.51 (br. s, 1H), 6.22 (br. s, 1H), 5.28 (d, J = 3.5 Hz, 1H), 4.54-4.41 (m, 1H), 1.25 (d, J = 5.0 Hz, 3H); 3:1 mixture of diastereomers; major diastereomer described. | 423.1 | E | |
| I-2232 | 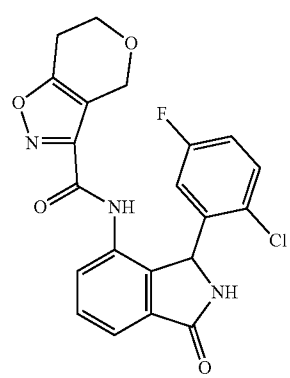 [SMILES: O=C1NC(c2cc(F)ccc2Cl)c2c(NC(=O)c3noc4c3COCC4)cccc21] | Fc1ccc(C 1)c(c1)C1 NC(=O)c 2cccc(N C(=O)c3 noc4CC OCc34)c 12 | | | E | |
| I-2233 | 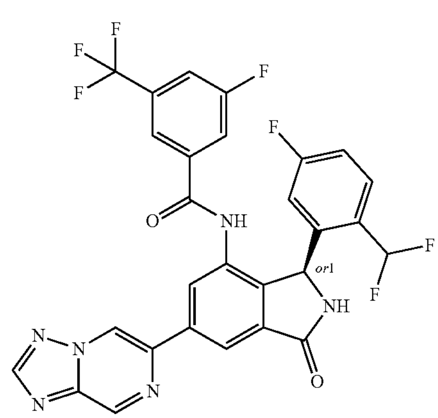 [SMILES: O=C(Nc1cc(-c2cn3ncnc3cn2)cc2c1[C@@H](c1cc(F)ccc1C(F)F)NC2=O)c1cc(F)cc(C(F)(F)F)c1] | FC(F)c1c cc(F)cc1 [C@H]1N C(=O)c2 cc(cc(NC (=O)c3cc (F)cc(c3) C(F)(F)F) c12)- c1cn2ncn c2cn1 | | 601.3 | D | |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-2234 | 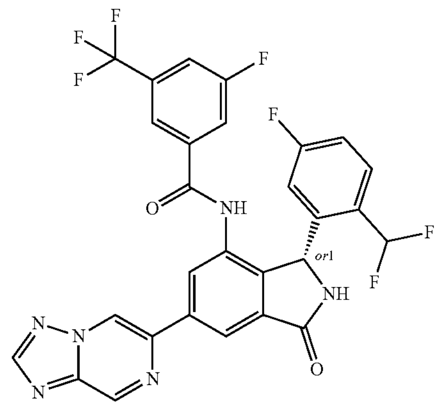 [SMILES: O=C(Nc1cc(-c2cn3ncnc3cn2)cc2c1[C@H](c1cc(F)ccc1C(F)F)NC2=O)c1cc(F)cc(C(F)(F)F)c1] | FC(F)c1cc(F)cc1[C@@H]1NC(=O)c2cc(cc(NC(=O)c3cc(F)cc(c3)C(F)(F)F)c12)-c1cn2cnc2cn1 | | 603.1 | | A |
| I-2235 | 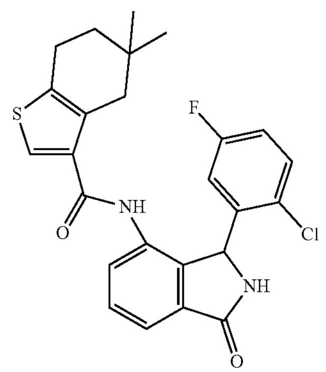 [SMILES: CC1(C)CCc2scc(C(=O)Nc3cccc4c3C(c3cc(F)ccc3Cl)NC4=O)c2C1] | CC1(C)CCc2scc(C(=O)Nc3cccc4C(=O)NC(c34)c3cc(F)ccc3Cl)c2C1 | | | | D |
| I-2236 | 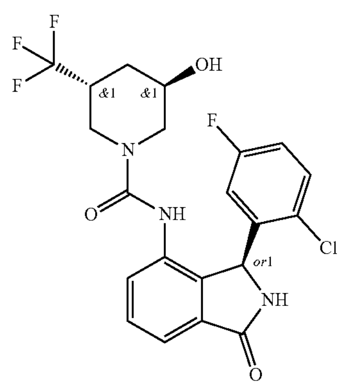 [SMILES: O=C1N[C@H](c2cc(F)ccc2Cl)c2c(NC(=O)N3C[C@H](O)C[C@@H](C(F)(F)F)C3)cccc21] | O[C@@H]1C[C@H](CN(C1)C(=O)Nc1cccc2C(=O)N[C@@H](c12)c1cc(F)ccc1Cl)C(F)(F)F | | 472.0 | | E |
| I-2237 | 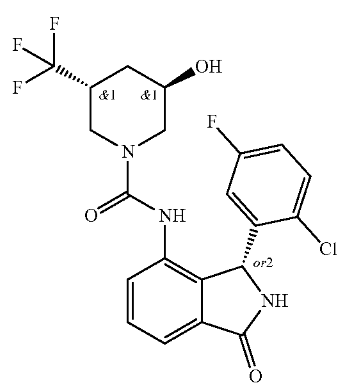 [SMILES: O=C1N[C@@H](c2cc(F)ccc2Cl)c2c(NC(=O)N3C[C@H](O)C[C@@H](C(F)(F)F)C3)cccc21] | O[C@@H]1C[C@H](CN(C1)C(=O)Nc1cccc2C(=O)N[C@H](c12)c1cc(F)ccc1Cl)C(F)(F)F | | 472.0 | | D |

TABLE 2-continued

Representative Compounds of the Invention with Bioactivity Data.

| Ex. No. | Structure | SMILES | $^1$H NMR | MS | ADP-Glo IC$_{50}$ | MCF 10A IC$_{50}$ |
|---|---|---|---|---|---|---|
| I-2238 | 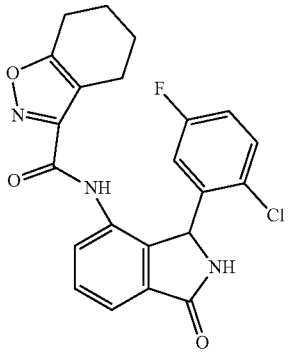 [SMILES: O=C1NC(c2cc(F)ccc2Cl)c2c(NC(=O)c3noc4c3CCCC4)cccc21] | Fc1ccc(C1)c(c1)C1NC(=O)c2cccc(NC(=O)c3noc4CCCCc34)c12 | | | D | |
| I-2239 | 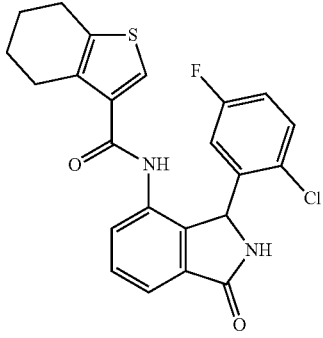 [SMILES: O=C(Nc1cccc2c1C(c1cc(F)ccc1Cl)NC2=O)c1csc2c1CCCC2] | Fc1ccc(C1)c(c1)C1NC(=O)c2cccc(NC(=O)c3csc4CCCCc34)c12 | | | A | B |
| I-2240 | 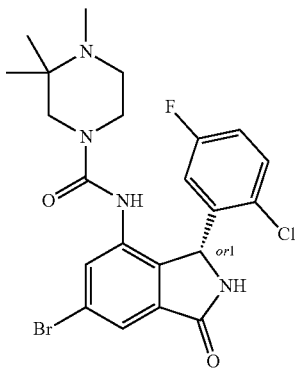 [SMILES: CN1CCN(C(=O)Nc2cc(Br)cc3c2[C@H](c2cc(F)ccc2Cl)NC3=O)CC1(C)C] | CN1CCN(CC1(C)C)C(=O)Nc1cc(Br)cc2C(=O)N[C@H](c12)c1cc(F)ccc1Cl | (400 MHz, DMSO-d6) δ 9.16 (s, 1H), 8.49 (s, 1H), 7.59 (d, J = 1.4 Hz, 1H), 7.53 (d, J = 1.5 Hz, 1H), 7.51-7.44 (m, 1H), 7.23 (td, J = 8.4, 3.0 Hz, 1H), 6.61 (br. s, 1H), 6.01 (br. s, 1H), 3.23-3.16 (m, 1H), 3.02-2.96 (m, 1H), 2.92 (d, J = 13.4 Hz, 1H), 2.76 (d, J = 12.6 Hz, 1H), 2.32-2.20 (m, 2H), 2.06 (s, 3H), 0.84 (s, 3H), 0.69 (s, 3H). | 511.3 | E | |
| I-2241 | 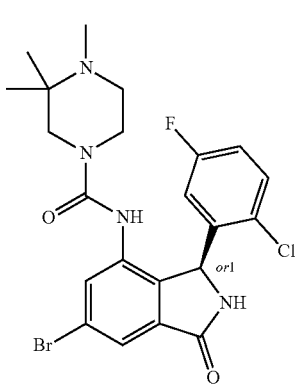 [SMILES: CN1CCN(C(=O)Nc2cc(Br)cc3c2[C@@H](c2cc(F)ccc2Cl)NC3=O)CC1(C)C] | CN1CCN(CC1(C)C)C(=O)Nc1cc(Br)cc2C(=O)N[C@@H](c12)c1cc(F)ccc1Cl | (400 MHz, DMSO-d6) δ 9.16 (s, 1H), 8.49 (s, 1H), 7.59 (d, J = 1.4 Hz, 1H), 7.53 (d, J = 1.5 Hz, 1H), 7.51-7.44 (m, 1H), 7.23 (td, J = 8.4, 3.0 Hz, 1H), 6.61 (br. s, 1H), 6.01 (br. s, 1H), 3.23-3.16 (m, 1H), 3.02-2.96 (m, 1H), 2.92 (d, J = 13.4 Hz, 1H), 2.76 (d, J = 12.6 Hz, 1H), 2.32-2.20 (m, 2H), 2.06 (s, 3H), 0.84 (s, 3H), 0.69 (s, 3H). | 511.3 | E | |

| Ex. No. | Structure | SMILES | ¹H NMR | MS | ADP-Glo IC$_{50}$ | MCF 10A IC$_{50}$ |
|---|---|---|---|---|---|---|
| I-2242 | 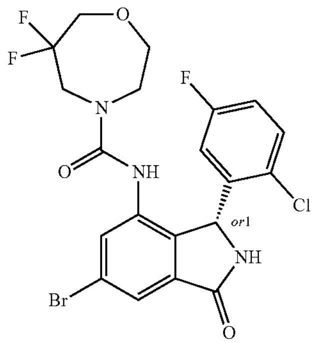 [SMILES: O=C1N[C@@H](c2cc(F)ccc2Cl)c2c(NC(=O)N3CCOCC(F)(F)C3)cc(Br)cc21] | Fc1ccc(C1)c(c1)[C@@H]1NC(=O)c2cc(Br)cc(NC(=O)N3CCOCC(F)(F)C3)c12 | (400 MHz, DMSO-d6) δ 9.22 (s, 1H), 8.66 (s, 1H), 7.66 (d, J = 1.6 Hz, 1H), 7.55 (d, J = 1.7 Hz, 1H), 7.53-7.47 (m, 1H), 7.23 (td, J = 8.4, 3.1 Hz, 1H), 6.57 (br. s, 1H), 6.04 (br. s, 1H), 4.17 (dt, J = 15.4, 11.2 Hz, 1H), 3.77-3.53 (m, 4H), 3.52-3.41 (m, 2H), 3.19 (ddd, J = 14.6, 8.0, 3.6 Hz, 1H). | 520.3 | E | |
| I-2243 | 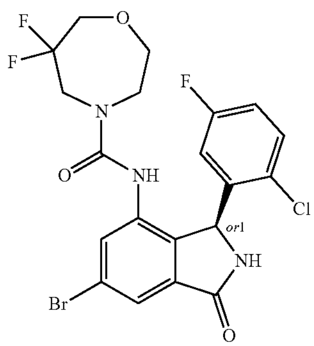 [SMILES: O=C1N[C@H](c2cc(F)ccc2Cl)c2c(NC(=O)N3CCOCC(F)(F)C3)cc(Br)cc21] | Fc1ccc(C1)c(c1)[C@H]1NC(=O)c2cc(Br)cc(NC(=O)N3CCOCC(F)(F)C3)c12 | (400 MHz, DMSO-d6) δ 9.22 (s, 1H), 8.66 (s, 1H), 7.66 (d, J = 1.6 Hz, 1H), 7.55 (d, J = 1.7 Hz, 1H), 7.53-7.47 (m, 1H), 7.23 (td, J = 8.4, 3.1 Hz, 1H), 6.57 (br. s, 1H), 6.04 (br. s, 1H), 4.17 (dt, J = 15.4, 11.2 Hz, 1H), 3.77-3.53 (m, 4H), 3.52-3.41 (m, 2H), 3.19 (ddd, J = 14.6, 8.0, 3.6 Hz, 1H). | 520.3 | E | |
| I-2244 | 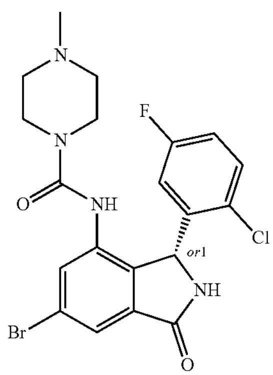 [SMILES: CN1CCN(C(=O)Nc2cc(Br)cc3c2[C@H](c2cc(F)ccc2Cl)NC3=O)CC1] | CN1CCN(CC1)C(=O)Nc1cc(Br)cc2C(=O)N[C@H](c12)c1cc(F)ccc1Cl | (400 MHz, DMSO-d6) δ 9.17 (br. s, 1H), 8.64 (s, 1H), 7.58 (d, J = 1.7 Hz, 1H), 7.54-7.48 (m, 1H), 7.47 (d, J = 1.7 Hz, 1H), 7.25 (ddd, J = 8.7, 8.1, 3.1 Hz, 1H), 6.57 (br. s, 1H), 5.97 (br. s, 1H), 3.22-3.11 (m, 2H), 3.03-2.93 (m, 2H), 2.18-2.09 (m, 2H), 2.12 (s, 3H), 2.05-1.95 (m, 2H). | 483.3 | E | |
| I-2245 | 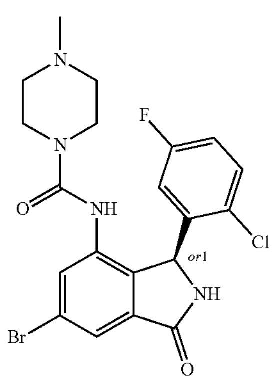 [SMILES: CN1CCN(C(=O)Nc2cc(Br)cc3c2[C@@H](c2cc(F)ccc2Cl)NC3=O)CC1] | CN1CCN(CC1)C(=O)Nc1cc(Br)cc2C(=O)N[C@@H](c12)c1cc(F)ccc1Cl | (400 MHz, DMSO-d6) δ 9.17 (br. s, 1H), 8.64 (s, 1H), 7.58 (d, J = 1.7 Hz, 1H), 7.54-7.48 (m, 1H), 7.47 (d, J = 1.7 Hz, 1H), 7.25 (ddd, J = 8.7, 8.1, 3.1 Hz, 1H), 6.57 (br. s, 1H), 5.97 (br. s, 1H), 3.22-3.11 (m, 2H), 3.03-2.93 (m, 2H), 2.18-2.09 (m, 2H), 2.12 (s, 3H), 2.05-1.95 (m, 2H). | 483.3 | E | |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-2246 | 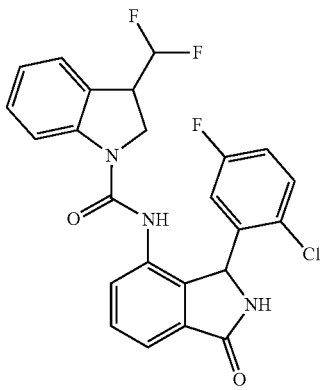 [SMILES: O=C1NC(c2cc(F)ccc2Cl)c2c(NC(=O)N3CC(C(F)F)c4ccccc43)cccc21] | FC(F)C1 CN(C(= O)Nc2cc cc3C(=O) NC(c23) c2cc(F)c cc2Cl)c2 ccccc12 | (400 MHz, DMSO-d6) δ as a ca. 1:1 mixture of diastereomers, δ 9.07 (br. s, 2H), 8.67 (br. s, 1H), 8.66 (br. s, 1H), 7.81 (d, J = 8.0 Hz, 1H), 7.72 (d, J = 8.1 Hz, 1H), 7.61-7.54 (m, 4H), 7.43-7.34 (m, 4H), 7.30 (dd, J = 7.0, 4.5 Hz, 2H), 7.26-7.19 (m, 2H), 7.18-7.09 (m, 2H), 6.99-6.93 (m, 2H), 6.56 (br. s, 2H), 6.30-6.00 (m, 1H), 6.25 (td, J = 55.9, 3.5 Hz, 1H), 6.05 (br. s, 2H), 4.06-3.83 (m, 5H), 3.39 (dd, J = 10.2, 4.2 Hz, 1H). | 472.4 | A | B |
| I-2247 | 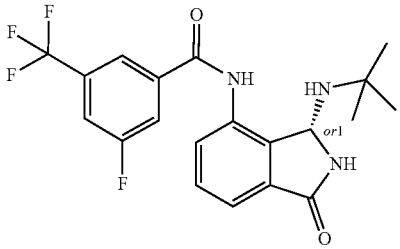 [SMILES: CC(C)(C)N[C@@H]1NC(=O)c2cccc(NC(=O)c3cc(F)cc(C(F)(F)F)c3)c21] | CC(C)(C) N[C@@ H]1NC(= O)c2cccc (NC(=O) c3cc(F)c c(c3)C(F) (F)F)c12 | | 410.2 | E | |
| I-2248 | 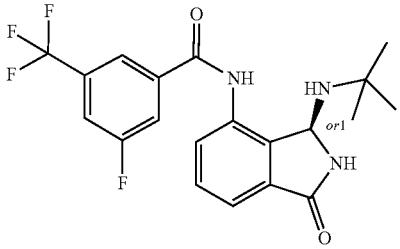 [SMILES: CC(C)(C)N[C@H]1NC(=O)c2cccc(NC(=O)c3cc(F)cc(C(F)(F)F)c3)c21] | CC(C)(C) N[C@H] 1NC(=O) c2cccc (NC(=O)c 3cc(F)cc (c3)C(F) (F)F)c12 | | 410.2 | E | |
| I-2249 | 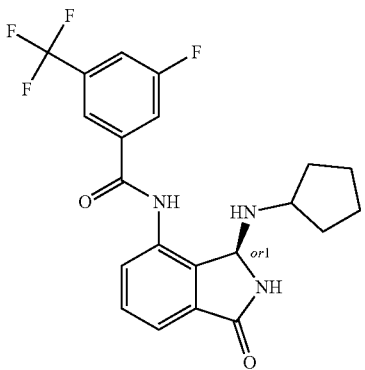 [SMILES: O=C(Nc1cccc2c1[C@@H](NC1CCCC1)NC2=O)c1cc(F)cc(C(F)(F)F)c1] | Fc1cc(cc (c1)C(F) (F)F)C(= O)Nc1cc cc2C(=O) N[C@H] (NC3CC CC3)c12 | | 422.2 | E | |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-2250 | 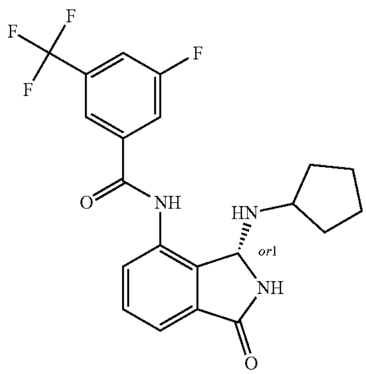 [SMILES: O=C(Nc1cccc2c1[C@H](NC1CCCC1)NC2=O)c1cc(F)cc(C(F)(F)F)c1] | Fc1cc(cc (c1)C(F) (F)F)C(= O)Nc1cc cc2C(=O) N[C@@ H](NC3 CCCC3) c12 | | 422.3 | E | |
| I-2251 | 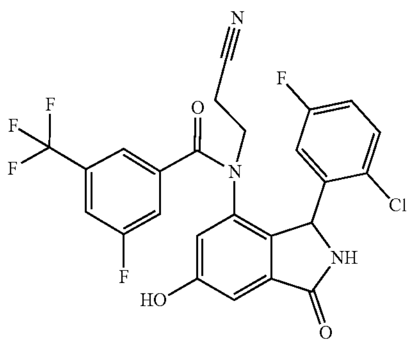 [SMILES: N#CCCN(C(=O)c1cc(F)cc(C(F)(F)F)c1)c1cc(O)cc2c1C(c1cc(F)ccc1Cl)NC2=O] | Oc1cc2C (=O)NC (c2c(c1)N (CCC#N) C(=O)c1 cc(F)cc(c 1)C(F)(F) F)c1cc (F)ccc1Cl | (400 MHz, DMSO-d6) 10.44 (s, 1H), 9.15 (d, J = 53.9 Hz, 1H), 8.00-7.44 (m, 3H), 7.38-6.99 (m, 3H), 6.86 (d, J = 47.8 Hz, 1H), 6.40 (dd, J = 78.9, 38.4 Hz, 1H), 6.02-5.06 (m, 1H), 4.68 (s, 1H), 3.69 (d, J = 151.1 Hz, 1H), 2.95-2.62 (m, 2H). | 536.3 | E | |
| I-2252 | 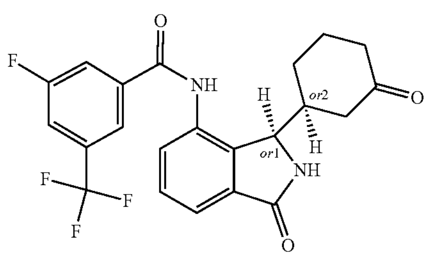 [SMILES: O=C1CCC[C@H]([C@H]2NC(=O)c3cccc(NC(=O)c4cc(F)cc(C(F)(F)F)c4)c32)C1] | [H][C@ @]1(NC (=O)c2ccc c(NC(=O) c3cc(F)c c(c3)C(F) (F)F)c12) [C@@] 1([H])CC CC(=O) C1 | (400 MHz, DMSO-d6) δ 10.76 (s, 1H), 8.89 (s, 1H), 8.15-8.05 (m, 2H), 8.02 (d, J = 8.5 Hz, 1H), 7.66-7.51 (m, 3H), 4.96 (s, 1H), 2.40-2.13 (m, 3H), 2.14-2.01 (m, 1H), 2.02-1.89 (m, 1H), 1.89-1.61 (m, 2H), 1.52-1.19 (m, 1H), 1.20-0.99 (m, 1H); ~1.25:1 mixture of diastereomers, major diastereomer described | 435.2 | E | |
| I-2253 | 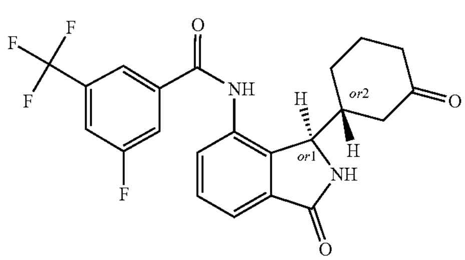 [SMILES: O=C1CCC[C@@H]([C@H]2NC(=O)c3cccc(NC(=O)c4cc(F)cc(C(F)(F)F)c4)c32)C1] | [H][C@ @]1(NC (=O)c2ccc c(NC(=O) c3cc(F)c c(c3)C(F) (F)F)c12) [C@]1 ([H])CCC C(=O)C1 | (400 MHz, DMSO-d6) δ 10.76 (s, 1H), 8.89 (s, 1H), 8.15-8.05 (m, 2H), 8.02 (d, J = 8.5 Hz, 1H), 7.66-7.51 (m, 3H), 4.96 (s, 1H), 2.40-2.13 (m, 3H), 2.14-2.01 (m, 1H), 2.02-1.89 (m, 1H), 1.89-1.61 (m, 2H), 1.52-1.19 (m, 1H), 1.20-0.99 (m, 1H); ~1.25:1 mixture of diastereomers; major diastereomer described. | 435.2 | E | |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-2254 | 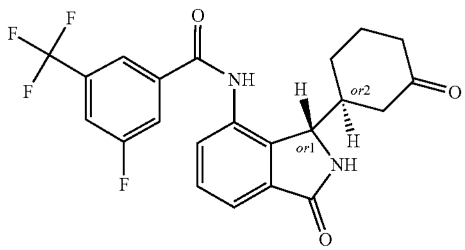 [SMILES: O=C1CCC[C@H]([C@@H]2NC(=O)c3cccc(NC(=O)c4cc(F)cc(C(F)(F)F)c4)c32)C1] | [H][C@]1(NC(=O)c2cccc(NC(=O)c3cc(F)cc(c3)C(F)(F)F)c12)[C@@]1([H])CCCC(=O)C1 | (400 MHz, DMSO-d6) δ 10.76 (s, 1H), 8.89 (s, 1H), 8.15-8.05 (m, 2H), 8.02 (d, J = 8.5 Hz, 1H), 7.66-7.51 (m, 3H), 4.96 (s, 1H), 2.40-2.13 (m, 3H), 2.14-2.01 (m, 1H), 2.02-1.89 (m, 1H), 1.89-1.61 (m, 2H), 1.52-1.19 (m, 1H), 1.20-0.99 (m, 1H); ~1.25:1 mixture of diastereomers; major diastereomer described. | 435.2 | E | |
| I-2255 | 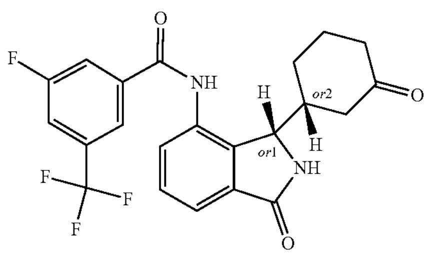 [SMILES: O=C1CCC[C@@H]([C@@H]2NC(=O)c3cccc(NC(=O)c4cc(F)cc(C(F)(F)F)c4)c32)C1] | [H][C@]1(NC(=O)c2cccc(NC(=O)c3cc(F)cc(c3)C(F)(F)F)c12)[C@]1([H])CCCC(=O)C1 | of the mixture of diastereomers: 1H (400 MHz, DMSO-d6) δ 10.76 (s, 1H), 8.89 (s, 1H), 8.15-8.05 (m, 2H), 8.02 (d, J = 8.5 Hz, 1H), 7.66-7.51 (m, 3H), 4.96 (s, 1H), 2.40-2.13 (m, 3H), 2.14-2.01 (m, 1H), 2.02-1.89 (m, 1H), 1.89-1.61 (m, 2H), 1.52-1.19 (m, 1H), 1.20-0.99 (m, 1H); ~1.25:1 mixture of diastereomers; major diastereomer described. | 435.2 | E | |
| I-2256 | 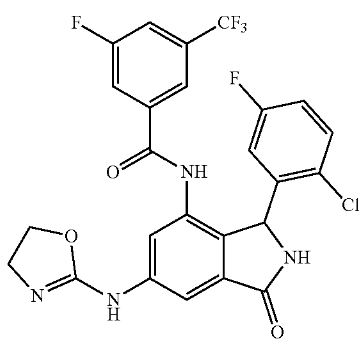 [SMILES: O=C(Nc1cc(NC2=NCCO2)cc2c1C(c1cc(F)ccc1Cl)NC2=O)c1cc(F)cc(C(F)(F)F)c1] | FC(F)(C1=CC(F)=CC(C(NC2=C3C(NC(C3=CC(NC4=NCCO4)=C2)=O)C5=CC(F)=CC=C5Cl)=O)=C1)F | (500 MHz, DMSO) δ 10.44 (s, 1H), 9.01 (s, 1H), 7.93-7.88 (m, 1H), 7.77-7.67 (m, 2H), 7.61 (s, 1H), 7.28 (dt, J = 8.9, 4.6 Hz, 1H), 7.06 (td, J = 8.3, 3.1 Hz, 1H), 5.87 (s, 1H), 4.30 (t, J = 8.5 Hz, 2H), 3.76 (s, 2H). | 551.0 | A | B |
| I-2257 | 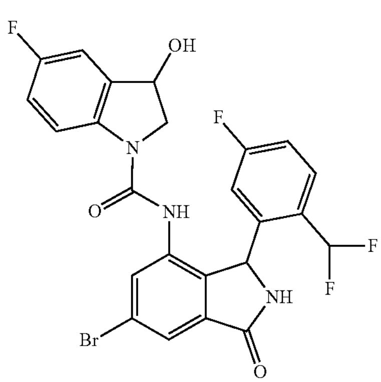 [SMILES: O=C1NC(c2cc(F)ccc2C(F)F)c2c(NC(=O)N3CC(O)c4cc(F)ccc43)cc(Br)cc21] | OC1CN(C(=O)Nc2cc(Br)cc3C(=O)NC(c23)c2cc(F)ccc2C(F)F)c2ccc(F)cc12 | | 550.1 | A | B |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-2258 | 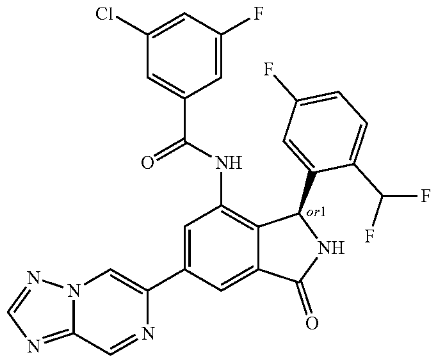 [SMILES: O=C(Nc1cc(-c2cn3ncnc3cn2)cc2c1[C@@H](c1cc(F)ccc1C(F)F)NC2=O)c1cc(F)cc(Cl)c1] | FC(F)c1cc(F)cc1[C@H]1NC(=O)c2cc(cc(NC(=O)c3cc(F)cc(Cl)c3)c12)-c1cn2ncnc2cn1 | | 567.3 | D | |
| I-2259 | 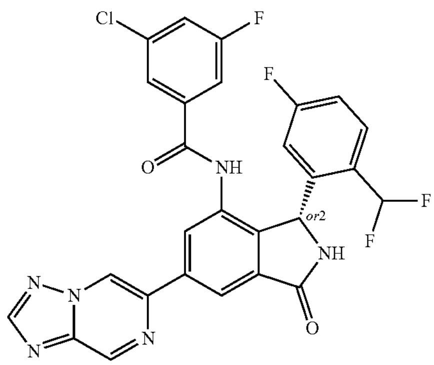 [SMILES: O=C(Nc1cc(-c2cn3ncnc3cn2)cc2c1[C@H](c1cc(F)ccc1C(F)F)NC2=O)c1cc(F)cc(Cl)c1] | FC(F)c1cc(F)cc1[C@@H]1NC(=O)c2cc(cc(NC(=O)c3cc(F)cc(Cl)c3)c12)-c1cn2ncnc2cn1 | | 567.3 | A | A |
| I-2260 | 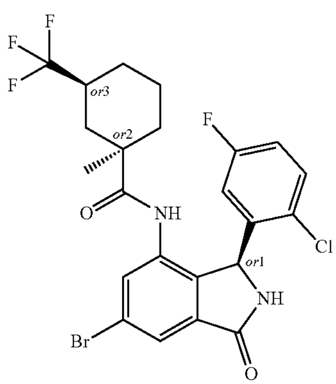 [SMILES: C[C@@]1(C(=O)Nc2cc(Br)cc3c2[C@@H](c2cc(F)ccc2Cl)NC3=O)CCC[C@H](C(F)(F)F)C1] | C[C@]1(CCC[C@@H](C1)C(F)(F)F)C(=O)Nc1cc(Br)cc2C(=O)N[C@@H](c12)c1cc(F)ccc1Cl | | 547.1 | C | |
| I-2261 | 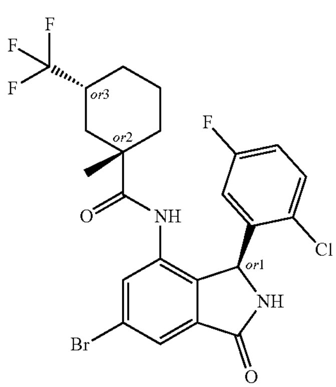 [SMILES: C[C@]1(C(=O)Nc2cc(Br)cc3c2[C@@H](c2cc(F)ccc2Cl)NC3=O)CCC[C@@H](C(F)(F)F)C1] | C[C@@]1(CCC[C@H](C1)C(F)(F)F)C(=O)Nc1cc(Br)cc2C(=O)N[C@@H](c12)c1cc(F)ccc1Cl | | 547.1 | A | A |

TABLE 2-continued

Representative Compounds of the Invention with Bioactivity Data.

| Ex. No. | Structure | SMILES | $^1$H NMR | MS | ADP-Glo IC$_{50}$ | MCF 10A IC$_{50}$ |
|---|---|---|---|---|---|---|
| I-2262 | 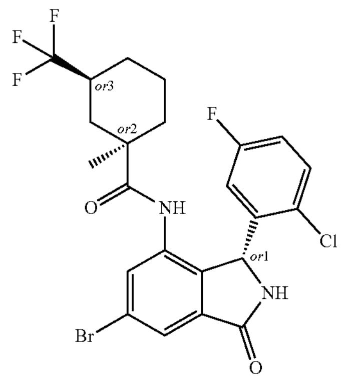 [SMILES: C[C@@]1(C(=O)Nc2cc(Br)cc3c2[C@H](c2cc(F)ccc2Cl)NC3=O)CCC[C@H](C(F)(F)F)C1] | C[C@]1(CCC[C@@H](C1)C(F)(F)F)C(=O)Nc1cc(Br)cc2C(=O)N[C@H](c12)c1cc(F)ccc1Cl | | 547.1 | B | B |
| I-2263 | 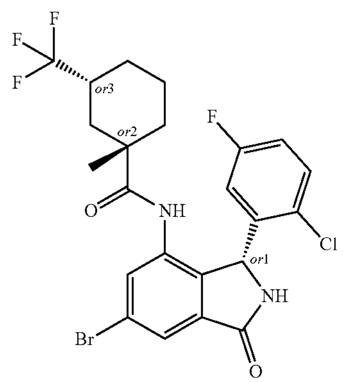 [SMILES: C[C@]1(C(=O)Nc2cc(Br)cc3c2[C@H](c2cc(F)ccc2Cl)NC3=O)CCC[C@@H](C(F)(F)F)C1] | C[C@@]1(CCC[C@H](C1)C(F)(F)F)C(=O)Nc1cc(Br)cc2C(=O)N[C@H](c12)c1cc(F)ccc1Cl | | 547.1 | D | |
| I-2264 | 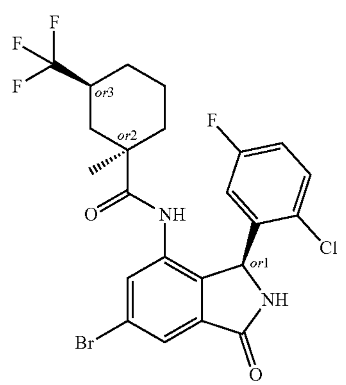 [SMILES: C[C@@]1(C(=O)Nc2cc(Br)cc3c2[C@@H](c2cc(F)ccc2Cl)NC3=O)CCC[C@H](C(F)(F)F)C1] | C[C@]1(CCC[C@@H](C1)C(F)(F)F)C(=O)Nc1cc(Br)cc2C(=O)N[C@@H](c12)c1cc(F)ccc1Cl | | 547.1 | B | |
| I-2265 | 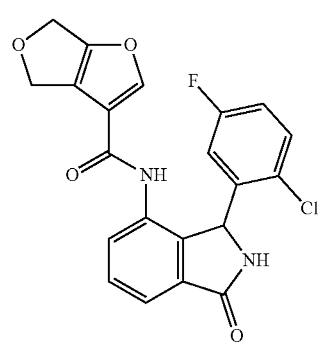 [SMILES: O=C(Nc1cccc2c1C(c1cc(F)ccc1Cl)NC2=O)c1coc2c1COC2] | Fc1ccc(C1)c(c1)C1NC(=O)c2cccc(NC(=O)c3coc4COCc34)c12 | | 98.0 | E | |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-2266 | 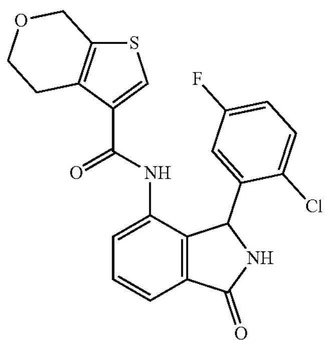 | Fc1ccc(C1)c(c1)C1NC(=O)c2cccc(NC(=O)c3csc4COCCc34)c12 | | 98.0 | B | |
| I-2267 | 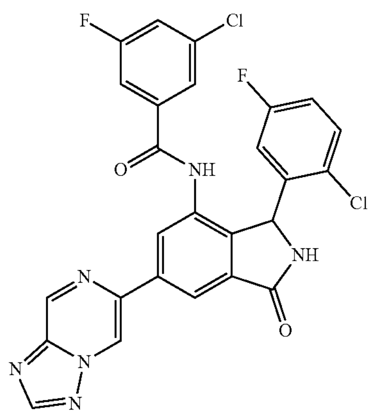 [SMILES: O=C(Nc1cc(-c2cn3ncnc3cn2)cc2c1C(c1cc(F)ccc1Cl)NC2=O)c1cc(F)cc(Cl)c1] | Fc1ccc(C1)c(c1)C1NC(=O)c2cc(cc(NC(=O)c3cc(F)cc(Cl)c3)c12)-c1cn2ncnc2cn1 | | | D | |
| I-2268 | 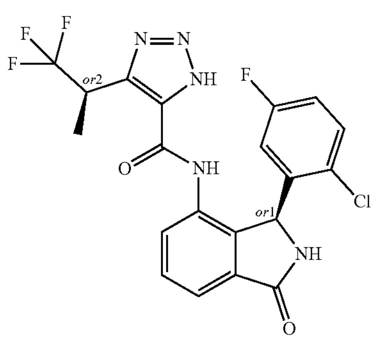 [SMILES: C[C@H](c1nn[nH]c1C(=O)Nc1cccc2c1[C@@H](c1cc(F)ccc1Cl)NC2=O)C(F)(F)F] | C[C@H](c1nn[nH]c1C(=O)Nc1cccc2C(=O)N[C@@H](c12)c1cc(F)ccc1Cl)C(F)(F)F | | 468.0 | E | |
| I-2269 | 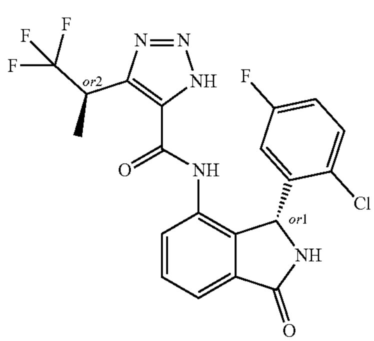 [SMILES: C[C@H](c1nn[nH]c1C(=O)Nc1cccc2c1[C@H](c1cc(F)ccc1Cl)NC2=O)C(F)(F)F] | C[C@H](c1nn[nH]c1C(=O)Nc1cccc2C(=O)N[C@H](c12)c1cc(F)ccc1Cl)C(F)(F)F | | 468.0 | E | |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-2270 | 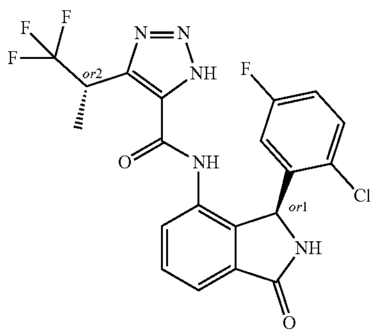 [SMILES: C[C@@H](c1nn[nH]c1C(=O)Nc1cccc2c1[C@@H](c1cc(F)ccc1Cl)NC2=O)C(F)(F)F] | C[C@@H](c1nn[nH]c1C(=O)Nc1cccc2C(=O)N[C@@H](c12)c1cc(F)ccc1Cl)C(F)(F)F | | 468.0 | E | |
| I-2271 | 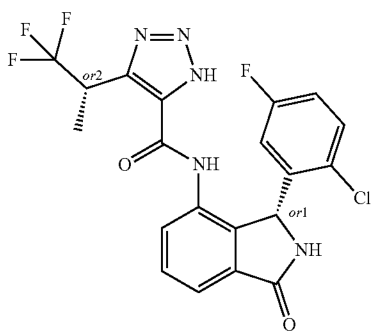 [SMILES: C[C@@H](c1nn[nH]c1C(=O)Nc1cccc2c1[C@H](c1cc(F)ccc1Cl)NC2=O)C(F)(F)F] | C[C@@H](c1nn[nH]c1C(=O)Nc1cccc2C(=O)N[C@H](c12)c1cc(F)ccc1Cl)C(F)(F)F | | 468.0 | D | |
| I-2272 | 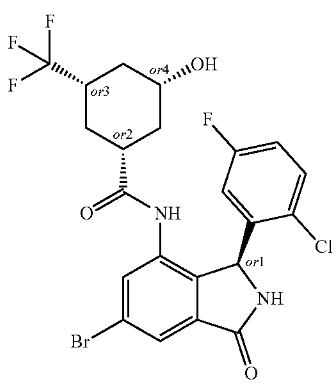 [SMILES: O=C1N[C@H](c2cc(F)ccc2Cl)c2c(NC(=O)[C@H]3C[C@@H](O)C[C@@H](C(F)(F)F)C3)cc(Br)cc21] | O[C@@H]1C[C@@H](C[C@@H](C1)C(F)(F)F)C(=O)Nc1cc(Br)cc2C(=O)N[C@@H](c12)c1cc(F)ccc1Cl | | 549.0 | E | |
| I-2273 | 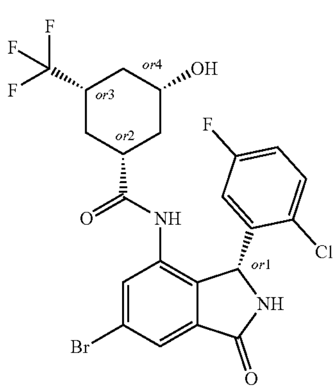 [SMILES: O=C1N[C@@H](c2cc(F)ccc2Cl)c2c(NC(=O)[C@H]3C[C@@H](O)C[C@@H](C(F)(F)F)C3)cc(Br)cc21] | O[C@@H]1C[C@@H](C[C@@H](C1)C(F)(F)F)C(=O)Nc1cc(Br)cc2C(=O)N[C@H](c12)c1cc(F)ccc1Cl | | 550.9 | E | |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-2274 | 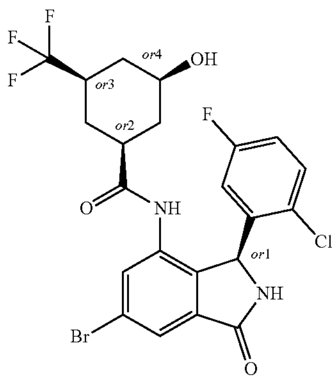 [SMILES: O=C1N[C@H](c2cc(F)ccc2Cl)c2c(NC(=O)[C@@H]3C[C@H](O)C[C@H](C(F)(F)F)C3)cc(Br)cc21] | O[C@H]1C[C@H](C[C@H](C1)C(F)(F)F)C(=O)Nc1cc(Br)cc2C(=O)N[C@@H](c12)c1cc(F)ccc1Cl | | 550.9 | E | |
| I-2275 | 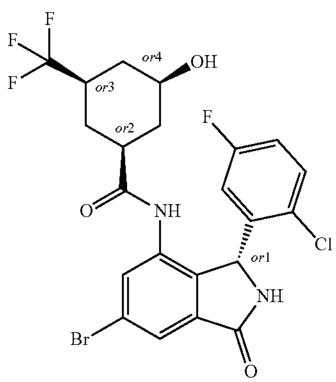 [SMILES: O=C1N[C@@H](c2cc(F)ccc2Cl)c2c(NC(=O)[C@@H]3C[C@H](O)C[C@H](C(F)(F)F)C3)cc(Br)cc21] | O[C@H]1C[C@H](C[C@H](C1)C(F)(F)F)C(=O)Nc1cc(Br)cc2C(=O)N[C@H](c12)c1cc(F)ccc1Cl | | 551.0 | E | |
| I-2276 | 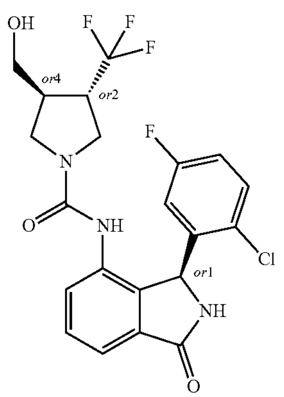 [SMILES: O=C1N[C@H](c2cc(F)ccc2Cl)c2c(NC(=O)N3C[C@@H](CO)[C@H](C(F)(F)F)C3)cccc21] | OC[C@@H]1CN(C[C@H]1C(F)(F)F)C(=O)Nc1cccc2C(=O)N[C@@H](c12)c1cc(F)ccc1Cl | | 470.2 | E | |
| I-2277 | 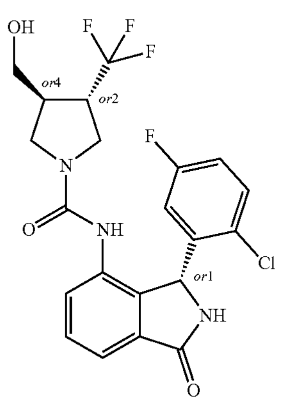 [SMILES: O=C1N[C@@H](c2cc(F)ccc2Cl)c2c(NC(=O)N3C[C@@H](CO)[C@H](C(F)(F)F)C3)cccc21] | OC[C@@H]1CN(C[C@H]1C(F)(F)F)C(=O)Nc1cccc2C(=O)N[C@H](c12)c1cc(F)ccc1Cl | | 470.2 | D | |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-2278 | 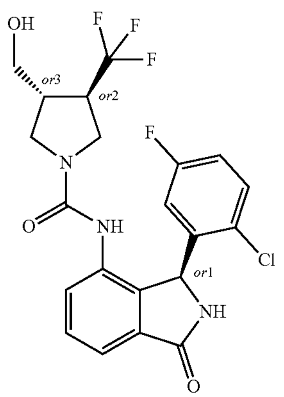 [SMILES: O=C1N[C@H](c2cc(F)ccc2Cl)c2c(NC(=O)N3C[C@H](CO)[C@@H](C(F)(F)F)C3)cccc21] | OC[C@H]1CN(C[C@@H]1C(F)(F)F)C(=O)Nc1cccc2C(=O)N[C@@H](c12)c1cc(F)ccc1Cl | | 470.2 | E | |
| I-2279 | 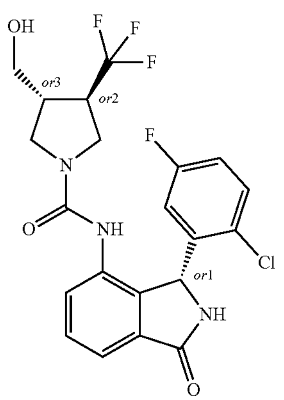 [SMILES: O=C1N[C@@H](c2cc(F)ccc2Cl)c2c(NC(=O)N3C[C@H](CO)[C@@H](C(F)(F)F)C3)cccc21] | OC[C@H]1CN(C[C@@H]1C(F)(F)F)C(=O)Nc1cccc2C(=O)N[C@H](c12)c1cc(F)ccc1Cl | | 470.2 | E | |
| I-2280 | 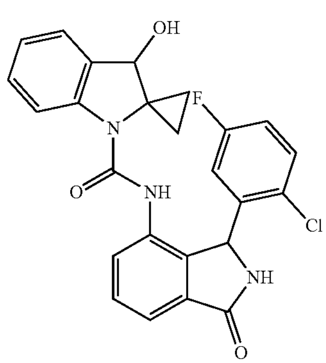 [SMILES: O=C1NC(c2cc(F)ccc2Cl)c2c(NC(=O)N3c4ccccc4C(O)C34CC4)cccc21] | OC1c2ccccc2N(C(=O)Nc2cccc3C(=O)NC(c23)c2cc(F)ccc2Cl)C11CC1 | (400 MHz, DMSO-d6) δ 9.23 (s,, 1H), 9.07 (br. s, 1H), 7.52 (m, 2H), 7.38 (d, J = 5.2 Hz, 1H), 7.35 (d, J = 5.2 Hz, 1H), 7.28-7.21 (m, 1H), 7.16-6.99 (m, 1H), 6.96-6.83 (m, 2H), 6.42 (br. s, , 1H), 6.13 (br. s, 1H), 6.00 (br. s, 1H), 5.62 (d, J = 6.8 Hz, 1H), 5.04 (d, J = 5.3 Hz, 1H), 1.78 (dt, J = 10.3, 5.2 Hz, 1H), 1.33 (ddd, J = 12.0, 8.1, 4.5 Hz, 1H), 1.10 (dt, J = 9.7, 5.0 Hz, 1H), 0.46 (ddd, J = 10.0, 7.2, 4.7 Hz, 1H); mixture of diastereomers. | 464.4 | E | |

TABLE 2-continued

Representative Compounds of the Invention with Bioactivity Data.

| Ex. No. | Structure | SMILES | $^1$H NMR | MS | ADP-Glo IC$_{50}$ | MCF 10A IC$_{50}$ |
|---|---|---|---|---|---|---|
| I-2281 | 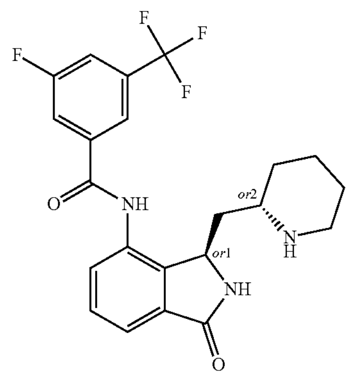 [SMILES: O=C(Nc1cccc2c1[C@@H](C[C@@H]1CCCCN1)NC2=O)c1cc(F)cc(C(F)(F)F)c1] | Fc1cc(cc(c1)C(F)(F)F)C(=O)Nc1cccc2C(=O)N[C@H](C[C@@H]3CCCCN3)c12 | | 436.4 | E | |
| I-2282 | 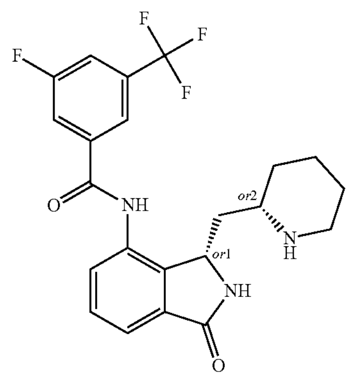 [SMILES: O=C(Nc1cccc2c1[C@H](C[C@@H]1CCCCN1)NC2=O)c1cc(F)cc(C(F)(F)F)c1] | Fc1cc(cc(c1)C(F)(F)F)C(=O)Nc1cccc2C(=O)N[C@@H](C[C@@H]3CCCCN3)c12 | | 426.4 | E | |
| I-2283 | 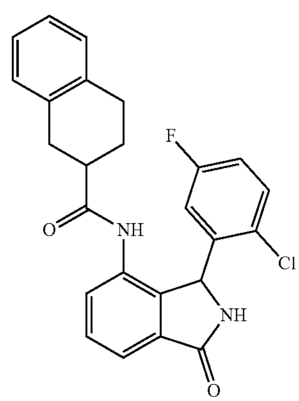 [SMILES: O=C1NC(c2cc(F)ccc2Cl)c2c(NC(=O)C3CCc4ccccc4C3)cccc21] | Fc1ccc(C1)c(c1)C1NC(=O)c2cccc(NC(=O)C3CCc4ccccc4C3)c12 | (400 MHz, DMSO-d6) δ 9.81 (s, 1H), 9.11 (br. s, 1H), 7.65-7.49 (m, 3H), 7.45 (ddd, J = 11.5, 7.2, 1.7 Hz, 1H), 7.34-7.23 (m, 1H), 7.11-7.03 (m, 3H), 7.02-6.88 (m, 1H), 6.48 (br. s, 1H), 6.09 (br. s, 1H), 2.80-2.59 (m, 2H), 2.61-2.52 (m, 1H), 2.48-2.22 (m, 2H), 1.55 (m, 2H); mixture of diastereomers. | 435.4 | E | |
| I-2284 | 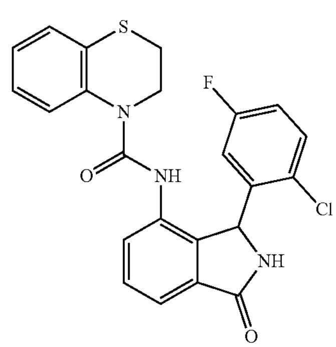 [SMILES: O=C1NC(c2cc(F)ccc2Cl)c2c(NC(=O)N3CCSc4ccccc43)cccc21] | Fc1ccc(C1)c(c1)C1NC(=O)c2cccc(NC(=O)N3CCSc4ccccc34)c12 | (400 MHz, DMSO-d6) δ 9.07 (br s, 1H), 8.64 (s, 1H), 7.58-7.45 (m, 3H), 7.38 (d, J = 7.3 Hz, 1H), 7.26 (td, J = 8.4, 3.1 Hz, 1H), 7.16 (dd, J = 7.9, 1.4 Hz, 1H), 6.99 (td, J = 7.7, 1.3 Hz, 1H), 6.79 (td, J = 7.7, 1.3 Hz, 1H), 6.46 (br s, 1H), 6.20 (br s, 1H), 6.07 (br s, 1H), 4.37 (br d, J = 11.4 Hz, 1H ), 3.20-3.04 (m, 2H), 3.03-2.91 (m, 1H). | 454.0 | E | |

TABLE 2-continued

Representative Compounds of the Invention with Bioactivity Data.

| Ex. No. | Structure | SMILES | $^1$H NMR | MS | ADP-Glo IC$_{50}$ | MCF 10A IC$_{50}$ |
|---|---|---|---|---|---|---|
| I-2285 | 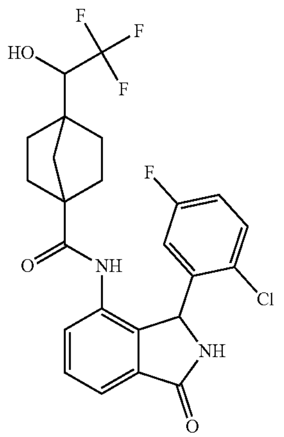 [SMILES: O=C1NC(c2cc(F)ccc2Cl)c2c(NC(=O)C34CCC(C(O)C(F)(F)F)(CC3)C4)cccc21] | OC(C(F)(F)F)C12CCC(CC1)(C2)C(=O)Nc1cccc2C(=O)NC(c12)c1cc(F)ccc1Cl | (400 MHz, DMSO-d6) δ 9.29 (s, 0.5H), 9.28 (s, 0.5H), 9.08 (br s, 1H), 7.60 (dd, J = 7.4, 1.1 Hz, 1H), 7.56 (t, J = 7.5 Hz, 1H), 7.53-7.44 (m, 1H), 7.37 (dd, J = 7.4, 1.0 Hz, 1H), 7.22 (td, J = 8.4, 3.1 Hz, 1H), 6.44 (br s, 1H), 6.25 (d, J = 2.7 Hz, 0.5H), 6.24 (d, J = 2.8 Hz, 0.5H), 6.04 (br s, 1H), 4.02-3.93 (m, 1H), 1.82-1.68 (m, 1H), 1.62-1.15 (m, 9H). 1:1 mix of diastereomers | 473.0 | E | |
| I-2286 | 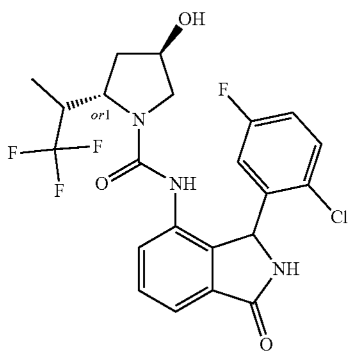 [SMILES: CC([C@@H]1C[C@@H](O)CN1C(=O)Nc1cccc2c1C(c1cc(F)ccc1Cl)NC2=O)C(F)(F)F] | CC([C@@H]1C[C@@H](O)CN1C(=O)Nc1cccc2C(=O)NC(c12)c1cc(F)ccc1Cl)C(F)(F)F | (400 MHz, CD3CN) δ 7.74 (d, J = 7.6 Hz, 0.4H), 7.65-7.44 (m, 3.6H), 7.17 (br s, 1H), 7.14-7.06 (m, 1H), 6.66 (br s, 0.4H), 6.57 (br s, 1H), 6.50 (br s, 0.6H), 6.31-6.24 (m, 1H), 4.34-4.24 (m, 0.6H), 4.16 (p, J = 6.9 Hz, 0.4H), 4.13-4.05 (m, 1H), 3.37-3.30 (m, 0.4H), 3.29-3.02 (m, 1H), 3.02-2.88 (m, 0.6H), 2.83 (dd, J = 10.1, 2.9 Hz, 0.6H), 2.77 (dd, J = 9.7, 6.9 Hz, 0.4H), 2.09-2.00 (m, 2H [submerged under H2O]), 1.04 (d, J = 7.3 Hz, 1.2H), 0.89 (d, J = 6.9 Hz, 1.8H) ppm [~1.5-1 mixture of diastereomers] | 486.3 | C | |
| I-2287 | 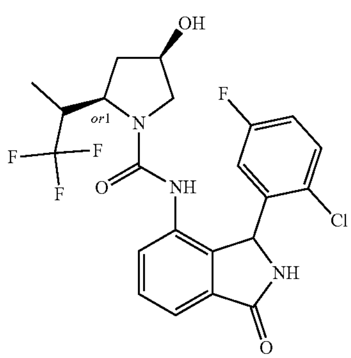 [SMILES: CC([C@H]1C[C@@H](O)CN1C(=O)Nc1cccc2c1C(c1cc(F)ccc1Cl)NC2=O)C(F)(F)F] | CC([C@H]1C[C@@H](O)CN1C(=O)Nc1cccc2C(=O)NC(c12)c1cc(F)ccc1Cl)C(F)(F)F | (400 MHz, CD3CN) δ 7.60 (s, 0.4H), 7.58 (s, 0.6H), 7.52 (t, J = 7.6 Hz, 1H), 7.48-7.38 (m, 1H), 7.32 (d, J = 8.0 Hz, 0.4H), 7.30 (d, J = 7.8 Hz, 0.6H), 7.15 (br s, 1H), 7.13-7.03 (m, 1H), 6.86 (br s, 0.6H), 6.82 (br s, 0.4H), 6.56 (br s, 1H), 6.11 (br s, 1H), 4.36-4.26 (m, 0.4H), 4.26-4.15 (m, 1H), 3.98 (p, J = 7.3 Hz, 0.4H), 3.22-3.08 (m, 0.4H), 3.00 (dd, J = 10.5, 3.0 Hz, 0.4H), 2.96-2.87 (m, 1H), 2.82 (dd, J = 9.8, 7.6 Hz, 1H), 2.75 (dd, J = 10.6, 5.9 Hz, 0.4H), 2.13-2.04 (m, 1H [submerged under H2O peak]), 1.74-1.63 (m, 1H), 1.00 (d, J = 7.2 Hz, 1.2H), 0.97 (d, J = 7.1 Hz, 1.8H) ppm [~1.5:1 mixture of diastereomers] | 486.3 | E | |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-2288 | 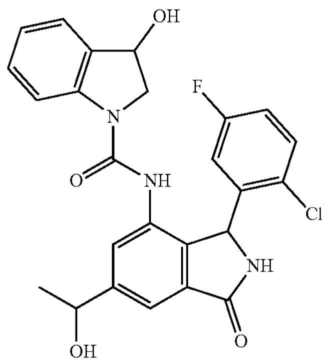 [SMILES: CC(O)c1cc(NC(=O)N2CC(O)c3ccccc32)c2c(c1)C(=O)NC2c1cc(F)ccc1Cl] | CC(O)c1cc2C(=O)NC(c2c(NC(=O)N2CC(O)c3ccccc23)c1)c1cc(F)ccc1Cl | (400 MHz, DMSO-d6) 9.02 (d, J = 10.9 Hz, 1H), 8.62-8.49 (m, 1H), 7.84-7.71 (m, 1H), 7.56 (ddd, J = 11.8, 4.1, 1.4 Hz, 1H), 7.49-7.30 (m, 3H), 7.30-7.05 (m, 2H), 6.96 (dtd, J = 9.8, 7.4, 1.0 Hz, 1H), 6.53 (s, 1H), 6.08-5.99 (m, 1H), 5.62 (ddd, J = 13.7, 5.6, 1.8 Hz, 1H), 5.39 (dd, J = 4.4, 2.6 Hz, 1H), 5.15-5.09 (m, 1H), 4.86 (dp, J = 12.3, 6.3 Hz, 1H), 4.01-3.70 m, 1H), 3.30-3.15 (m, 1H), 1.40 (dd, J = 6.4, 2.0 Hz, 3H). | 482.3 | A | D |
| I-2289 | 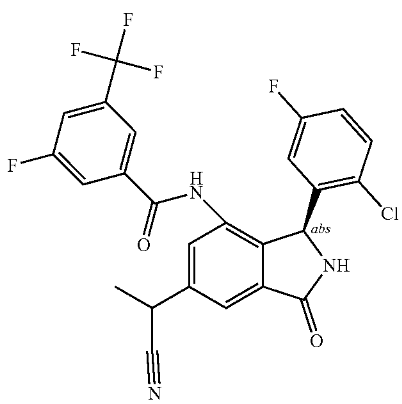 [SMILES: CC(C#N)c1cc(NC(=O)c2cc(F)cc(C(F)(F)F)c2)c2c(c1)C(=O)N[C@@H]2c1cc(F)ccc1Cl] | CC(C#N)c1cc2C(=O)N[C@@H](c2c(NC(=O)c2cc(F)cc(c2)C(F)(F)F)c1)c1cc(F)ccc1Cl | (400 MHz, DMSO-d6) 10.60 (s, 1H), 9.23 (s, 1H), 7.95 (d, J = 8.5 Hz, 1H), 7.74 (d, J = 4.9 Hz, 2H), 7.66 (s, 1H), 7.57 (s, 1H), 7.33 (dd, J = 8.9, 5.1 Hz, 1H), 7.10 (td, J = 8.3, 3.1 Hz, 1H), 7.10-5.99 (s, 1H), 5.99 (s, 1H), 4.57 (dd, J = 7.2, 4.1 Hz, 1H), 1.64 (dd, J = 7.3, 4.5 Hz, 3H). | 520.1 | D | |
| I-2290 | 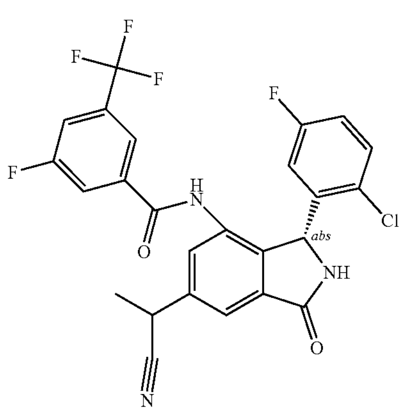 [SMILES: CC(C#N)c1cc(NC(=O)c2cc(F)cc(C(F)(F)F)c2)c2c(c1)C(=O)N[C@H]2c1cc(F)ccc1Cl] | CC(C#N)c1cc2C(=O)N[C@H](c2c(NC(=O)c2cc(F)cc(c2)C(F)(F)F)c1)c1cc(F)ccc1Cl | (400 MHz, DMSO-d6) 10.60 (d, J = 10.8 Hz, 1H), 9.24 (s, 1H), 7.96 (d, J = 8.4 Hz, 1H), 7.78-7.71 (m, 2H), 7.66 (s, 1H), 7.56 (d, J = 7.4 Hz, 1H), 7.33 (dd, J = 8.9, 5.1 Hz, 1H), 7.10 (td, J = 8.4, 3.1 Hz, 1H), 6.68 (s, 1H), 5.99 (s, 1H), 4.57 (q, J = 7.2 Hz, 1H), 1.64 (dd, J = 7.2, 4.6 Hz, 3H). | 520.1 | A | A |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-2291 | 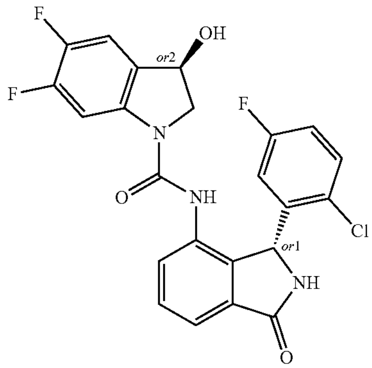 [SMILES: O=C1N[C@@H](c2cc(F)ccc2Cl)c2c(NC(=O)N3C[C@H](O)c4cc(F)c(F)cc43)cccc21] | O[C@H]1CN(C(=O)Nc2ccc c3C(=O)N[C@H](c23)c2c c(F)ccc2Cl)c2cc(F)c(F)cc12 | (400 MHz, DMSO-d6) 9.09 (s, 1H), 8.65 (s, 1H), 7.67-7.53 (m, 3H), 7.42 (dd, J = 7.6, 1.3 Hz, 1H), 7.39-7.30 (m, 2H), 7.14-7.05 (m, 1H), 6.56 (s, 1H), 6.08 (s, 1H), 5.76 (dt, J = 4.4, 1.8 Hz, 1H), 5.14 (dt, J = 8.6, 4.3 Hz, 1H), 3.99 (dd, J = 11.0, 8.1 Hz, 1H), 3.23 (dd, J = 11.2, 3.8 Hz, 1H). | 474.0 | D | |
| I-2292 | 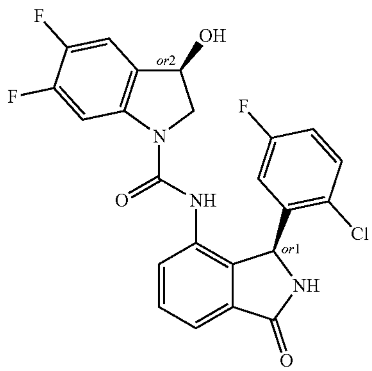 [SMILES: O=C1N[C@H](c2cc(F)ccc2Cl)c2c(NC(=O)N3C[C@H](O)c4cc(F)c(F)cc43)cccc21] | O[C@H]1CN(C(=O)Nc2ccc c3C(=O)N[C@@H](c23)c2cc(F)ccc2Cl)c2cc(F)c(F)cc12 | (400 MHz, DMSO-d6) 9.09 (s, 1H), 8.64 (s, 1H), 7.67-7.54 (m, 3H), 7.42 (dd, J = 7.5, 1.4 Hz, 1H), 7.39-7.30 (m, 2H), 7.10 (ddd, J = 8.9, 7.9, 3.1 Hz, 1H), 6.55 (s, 1H), 6.07 (s, 1H), 5.76 (d, J = 5.0 Hz, 1H), 5.14 (dt, J = 8.4, 4.3 Hz, 1H), 3.99 (dd, J = 11.1, 8.0 Hz, 1H), 3.23 (dd, J = 11.0, 3.8 Hz, 1H). | 474.0 | E | |
| I-2293 | 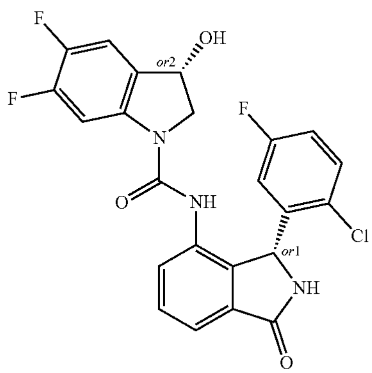 [SMILES: O=C1N[C@@H](c2cc(F)ccc2Cl)c2c(NC(=O)N3C[C@@H](O)c4cc(F)c(F)cc43)cccc21] | O[C@@H]1CN(C(=O)Nc2cccc3C(=O)N[C@H](c23)c2cc(F)ccc2Cl)c2cc(F)c(F)cc12 | (400 MHz, DMSO-d6) 9.07 (s, 1H), 7.79 (s, 1H), 7.64-7.53 (m, 2H), 7.42-7.33 (m, 3H), 7.16 (td, J = 8.3, 3.1 Hz, 1H), 6.05 (s, 2H), 5.09-5.02 (m, 1H), 3.74 (dd, J = 11.3, 3.3 Hz, 1H), 3.34 (s, 2H). | 474.0 | A | A |
| I-2294 | 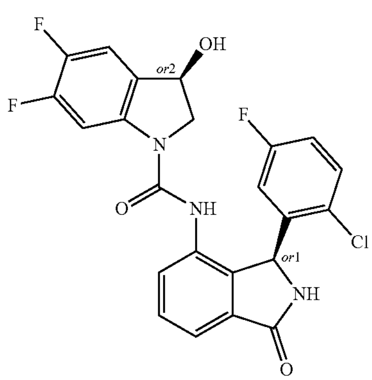 [SMILES: O=C1N[C@H](c2cc(F)ccc2Cl)c2c(NC(=O)N3C[C@H](O)c4cc(F)c(F)cc43)cccc21] | O[C@H]1CN(C(=O)Nc2ccc c3C(=O)N[C@@H](c23)c2cc(F)ccc2Cl)c2cc(F)c(F)cc12 | (400 MHz, DMSO-d6) 9.07 (s, 1H), 8.75 (s, 1H), 7.79 (d, J = 6.1 Hz, 1H), 7.64-7.57 (m, 1H), 7.57 (t, J = 7.4 Hz, 1H), 7.38 (dt, J = 8.8, 4.9 Hz, 3H), 7.16 (ddd, J = 8.9, 7.9, 3.1 Hz, 1H), 6.54 (s, 1H), 5.98 (d, J = 6.9 Hz, 1H), 5.78 (dd, J = 6.0, 1.3 Hz, 1H), 5.05 (d, J = 8.4 Hz, 1H), 3.74 (dd, J = 11.4, 3.3 Hz, 1H), 3.23 (s, 1H). | 474.0 | E | |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-2295 | 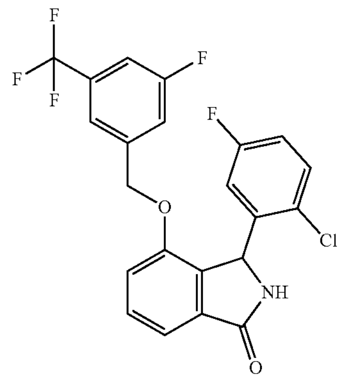 [SMILES: O=C1NC(c2cc(F)ccc2Cl)c2c(OCc3cc(F)cc(C(F)(F)F)c3)cccc21] | Fc1ccc(C1)c(c1)C1NC(=O)c2cccc(OCc3cc(F)cc(c3)C(F)(F)F)c12 | (400 MHz, DMSO-d6) δ9.10 (s, 1H), 7.65-7.59 (m, 1H), 7.55 (t, J = 7.8 Hz, 1H), 7.43 (dd, J = 8.9, 5.1 Hz, 1H), 7.37 (d, J = 7.5 Hz, 1H), 7.33 (s, 1H), 7.27 (d, J = 8.1 Hz, 1H), 7.20 (td, J = 8.4, 3.1 Hz, 1H), 7.08 (d, J = 9.5 Hz, 1H), 6.79 (s, 1H), 6.04 (s, 1H), 5.19 (s, 2H). | 454.0 | E | |
| I-2296 | 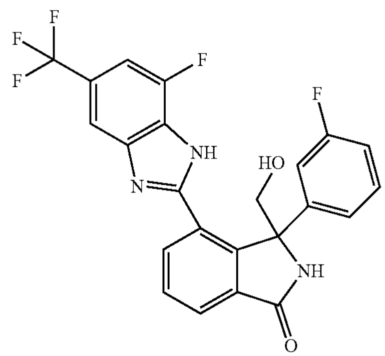 [SMILES: O=C1NC(CO)(c2cccc(F)c2)c2c1cccc2-c1nc2cc(C(F)(F)F)cc(F)c2[nH]1] | OCC1(NC(=O)c2cccc(-c3nc4cc(cc(F)c4[nH]3)C(F)(F)F)c12)c1cccc(F)c1 | (400 MHz, DMSO-d6) δ9.05 (s, 1H), 8.03 (d, J = 7.6 Hz, 1H), 7.89 (d, J = 7.4 Hz, 1H), 7.73 (d, J = 7.6 Hz, 1H), 7.61 (s, 1H), 7.33 (d, J = 10.6 Hz, 1H), 6.99 (q, J = 7.5 Hz, 1H), 6.89-6.75 (m, 3H), 4.75 (d, J = 10.6 Hz, 1H), 4.60 (s, 1H). | 460.3 | D | |
| I-2297 | 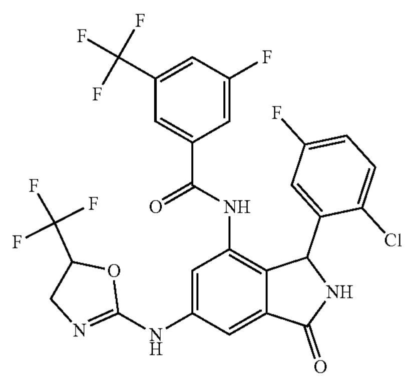 [SMILES: O=C(Nc1cc(NC2=NCC(C(F)(F)F)O2)cc2c1C(c1cc(F)ccc1Cl)NC2=O)c1cc(F)cc(C(F)(F)F)c1] | FC(F)(C1OC(NC(C=C23)=CC(NC(C4=CC(C(F)(F)F)=CC(F)=C4)=O)=C3C(NC2=O)C5=CC(F)=CC=C5Cl)=NC1)F | (400 MHz, DMSO) δ 10.50 (d, J = 3.8 Hz, 1H), 10.16-10.11 (m, 1H), 9.08 (s, 1H), 7.98 (s, 0H), 7.92 (dt, J = 8.5, 1.9 Hz, 2H), 7.78 (s, 1H), 7.73-7.66 (m, 2H), 7.63-7.58 (m, 1H), 7.28 (ddd, J = 8.9, 5.2, 2.8 Hz, 1H), 7.11-7.01 (m, 0H), 7.06 (s, 1H), 6.64 (s, 2H), 5.87 (s, 1H), 5.32 (d, J = 8.4 Hz, 1H), 4.16 (t, J = 11.8 Hz, 1H), 3.98-3.90 (m, 1H). | 619.0 | A | B |
| I-2298 | 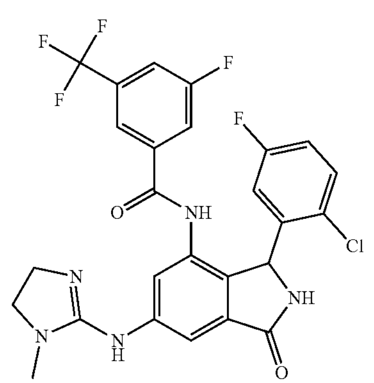 [SMILES: CN1CCN=C1Nc1cc(NC(=O)c2cc(F)cc(C(F)(F)F)c2)c2c(c1)C(=O)NC2c1cc(F)ccc1Cl] | FC(F)(C1=CC(F)=CC(C(NC2=C3C(NC(C3=CC(NC4=NCCN4C)=C2)=O)C5=CC(F)=CC=C5Cl)=O)=C1)F | (400 MHz, DMSO) δ 10.53 (s, 1H), 9.25 (s, 1H), 7.96 (dt, J = 8.4, 2.1 Hz, 1H), 7.78 (s, 5H), 7.74-7.58 (m, 2H), 7.53 (d, J = 1.9 Hz, 1H), 7.39-7.28 (m, 2H), 7.27-7.10 (m, 1H), 7.08 (s, 2H), 6.62 (s, 1H), 6.02 (s, 1H), 3.75-3.65 (m, 2H), 3.65-3.49 (m, 3H), 3.03 (s, 3H), 1.25 (dd, J = 7.0, 2.2 Hz, 3H). | 564.0 | B | |

TABLE 2-continued
Representative Compounds of the Invention with Bioactivity Data.
| Ex. No. | Structure | SMILES | ¹H NMR | MS | ADP-Glo IC$_{50}$ | MCF 10A IC$_{50}$ |
|---|---|---|---|---|---|---|
| I-2299 | 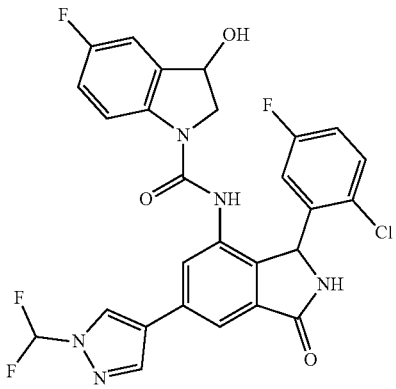 [SMILES: O=C1NC(c2cc(F)ccc2Cl)c2c(NC(=O)N3CC(O)c4cc(F)ccc43)cc(-c3cnn(C(F)F)c3)cc21] | OC1CN(C(=O)Nc2cc(cc3C(=O)NC(c23)c2ccc(F)ccc2C1)-c2cnn(c2)C(F)F)c2ccc(F)cc12 | | 572.2 | A | B |
| I-2300 | 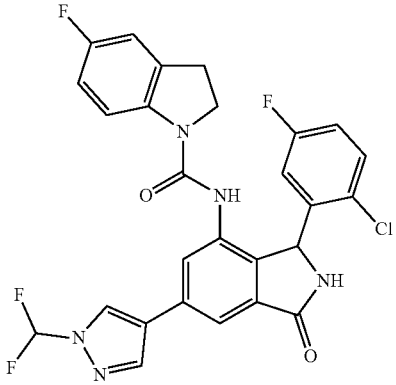 [SMILES: O=C1NC(c2cc(F)ccc2Cl)c2c(NC(=O)N3CCc4cc(F)ccc43)cc(-c3cnn(C(F)F)c3)cc21] | FC(F)n1cc(cn1)-c1cc2C(=O)NC(c2c(NC(=O)N2CCc3cc(F)ccc23)c1)c1cc(F)ccc1Cl | | 556.2 | A | B |
| I-2301 | 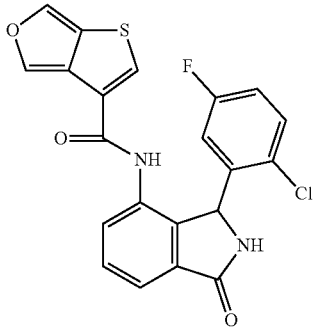 [SMILES: O=C1NC(c2cc(F)ccc2Cl)c2c(NC(=O)c3csc4cocc34)cccc21] | Fc1ccc(C1)c(c1)C1NC(=O)c2cccc(NC(=O)c3csc4cocc34)c12 | | 98.0 | E | |
| I-2302 | 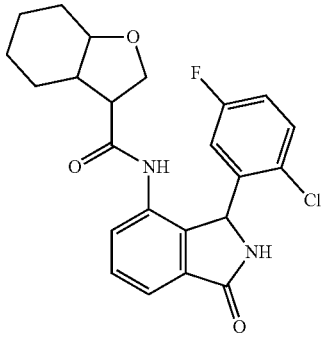 [SMILES: O=C1NC(c2cc(F)ccc2Cl)c2c(NC(=O)C3COC4CCCCC43)cccc21] | Fc1ccc(C1)c(c1)C1NC(=O)c2cccc(NC(=O)C3COC4CCCCC34)c12 | | 98.0 | E | |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-2303 | 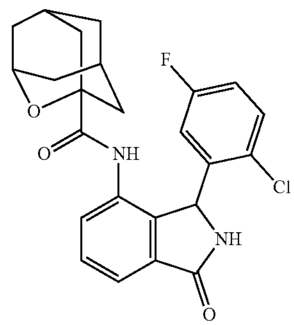 [SMILES: O=C1NC(c2cc(F)ccc2Cl)c2c(NC(=O)C34CC5CC(CC(C5)O3)C4)cccc21] | Fc1ccc(C1)c(c1)C1NC(=O)c2cccc(NC(=O)C34CC5CC(CC(C5)O3)C4)c12 | | 98.0 | | E |
| I-2304 | 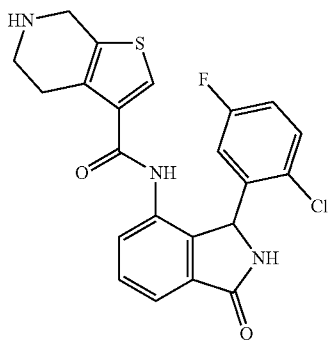 [SMILES: O=C(Nc1cccc2c1C(c1cc(F)ccc1Cl)NC2=O)c1csc2c1CCNC2] | Fc1ccc(C1)c(c1)C1NC(=O)c2cccc(NC(=O)c3csc4CNCCc34)c12 | | 97.0 | | E |
| I-2305 | 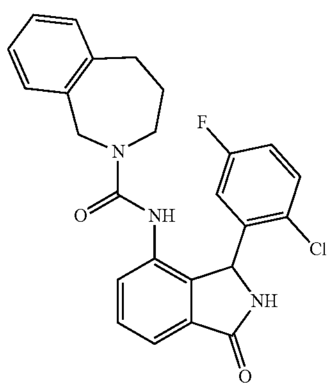 [SMILES: O=C1NC(c2cc(F)ccc2Cl)c2c(NC(=O)N3CCCc4ccccc4C3)cccc21] | Fc1ccc(C1)c(c1)C1NC(=O)c2cccc(NC(=O)N3CCCc4ccccc4C3)c12 | (400 MHz, DMSO-d6) 8.95 (s, 1H), 8.20 (s, 1H), 7.48 (q, J = 3.3, 2.4 Hz, 2H), 7.29 (td, J = 6.2, 5.6, 2.7 Hz, 2H), 7.20-7.10 (m, 3H), 7.07 (ddd, J = 11.5, 7.5, 3.4 Hz, 2H), 6.38 (s, 1H), 6.01 (s, 1H), 4.50 (d, J = 14.9 Hz, 1H), 4.25 (d, J = 14.9 Hz, 1H), 3.50 (d, J = 14.3 Hz, 1H), 2.82 (q, J = 6.1 Hz, 2H), 2.50 (p, J = 1.9 Hz, 1H), 1.55-1.47 (m, 2H). | 450.1 | | E |
| I-2306 | 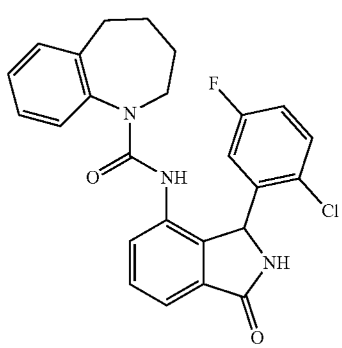 [SMILES: O=C1NC(c2cc(F)ccc2Cl)c2c(NC(=O)N3CCCCc4ccccc43)cccc21] | Fc1ccc(C1)c(c1)C1NC(=O)c2cccc(NC(=O)N3CCCCc4ccccc34)c12 | (400 MHz, DMSO-d6) 9.04-9.00 (m, 1H), 7.55 (s, 5H), 7.49 (d, J = 4.3 Hz, 1H), 7.34-7.21 (m, 1H), 7.15 (td, J = 7.5, 1.4 Hz, 1H), 7.00 (s, 1H), 6.41 (s, 2H), 6.11-6.06 (m, 1H), 2.68 (d, J = 2.1 Hz, 2H), 2.51 (d, J = 1.9 Hz, 1H), 2.52-2.12 (m, 2H), 1.65 (s, 1H), 1.53 (s, 1H), 1.35 (s, 1H). | 450.1 | | E |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-2307 | 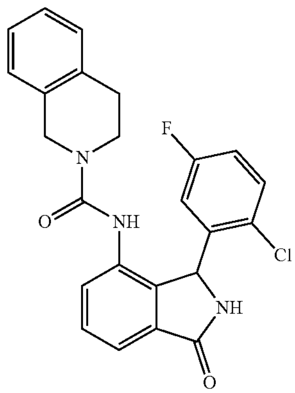 [SMILES: O=C1NC(c2cc(F)ccc2Cl)c2c(NC(=O)N3CCc4ccccc4C3)cccc21] | Fc1ccc(C1)c(c1)C1NC(=O)c2cccc(NC(=O)N3CCc4cccc4C3)c12 | (400 MHz, DMSO-d6) 9.01 (s, 1H), 8.57 (s, 1H), 7.51 (q, J = 4.4, 3.7 Hz, 2H), 7.32 (dd, J = 5.9, 3.0 Hz, 1H), 7.17 (tdd, J = 9.2, 7.1, 4.3 Hz, 4H), 7.08-7.01 (m, 1H), 6.97 (t, J = 9.0 Hz, 1H), 6.40 (s, 1H), 6.01 (s, 1H), 4.41 (d, J = 16.4 Hz, 1H), 4.15 (d, J = 16.4 Hz, 1H), 3.45 (ddd, J = 12.2, 6.7, 4.7 Hz, 1H), 3.22 (ddd, J = 12.6, 7.4, 4.5 Hz, 1H), 2.77-2.67 (m, 1H), 2.55 (d, J = 5.6 Hz, 1H). | 436.1 | E | |
| I-2308 | 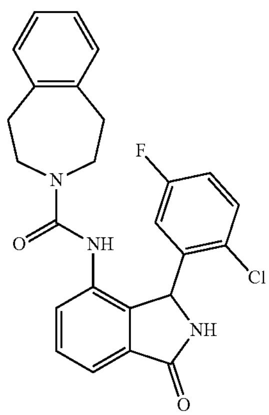 [SMILES: O=C1NC(c2cc(F)ccc2Cl)c2c(NC(=O)N3CCc4ccccc4CC3)cccc21] | Fc1ccc(C1)c(c1)C1NC(=O)c2cccc(NC(=O)N3CCc4cccc4CC3)c12 | (400 MHz, DMSO-d6) 9.04 (s, 1H), 8.56 (s, 1H), 7.53 (q, J = 4.4, 3.5 Hz, 2H), 7.40-7.30 (m, 2H), 7.11 (dd, J = 16.8, 3.0 Hz, 5H), 6.49 (s, 1H), 6.13 (s, 1H), 3.34 (s, 2H), 3.32 (s, 2H), 2.68 (d, J = 18.1 Hz, 2H), 2.47 (s, 2H). | 450.1 | E | |
| I-2309 | 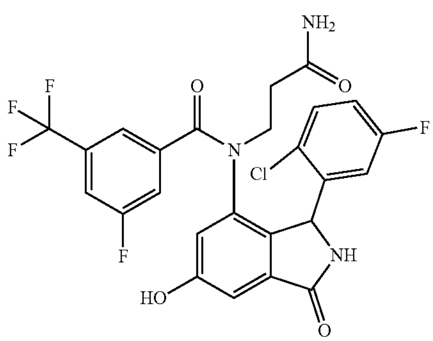 [SMILES: NC(=O)CCN(C(=O)c1cc(F)cc(C(F)(F)F)c1)c1cc(O)cc2c1C(c1cc(F)ccc1Cl)NC2=O] | NC(=O)CCN(C(=O)c1cc(F)cc(c1)C(F)(F)F)c1cc(O)cc2C(=O)NC(c12)c1cc(F)ccc1Cl | (400 MHz, DMSO-d6) 10.26 (s, 1H), 9.13 (d, J = 53.2 Hz, 1H), 7.86-6.66 (m, 7H), 6.63-5.97 (m, 1H), 5.97-4.24 (m, 1H), 3.58 (d, J = 67.6 Hz, 1H), 2.48-2.12 (m, 2H). | 554.2 | E | |
| I-2310 | 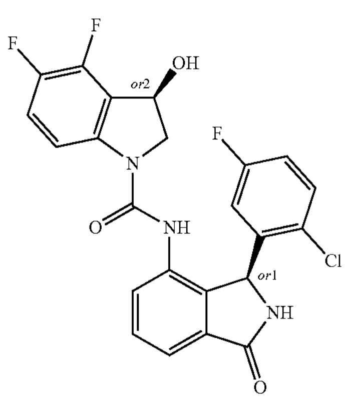 [SMILES: O=C1N[C@H](c2cc(F)ccc2Cl)c2c(NC(=O)N3C[C@H](O)c4c3ccc(F)c4F)cccc21] | O[C@H]1CN(C(=O)Nc2cccc3C(=O)N[C@@H](c23)c2cc(F)ccc2Cl)c2c cc(F)c(F)c12 | (400 MHz, DMSO-d6) 9.05 (s, 1H), 8.73 (s, 1H), 7.68 (s, 1H), 7.58 (d, J = 8.7 Hz, 2H), 7.49-7.27 (m, 3H), 7.17 (td, J = 8.4, 3.1 Hz, 1H), 6.82-6.24 (s, 1H), 5.97 (s, 2H), 5.27 (d, J = 7.2 Hz, 1H), 3.81 (d, J = 11.4 Hz, 1H), 3.23 (s, 1H). | 474.1 | A | A |

TABLE 2-continued

Representative Compounds of the Invention with Bioactivity Data.

| Ex. No. | Structure | SMILES | ¹H NMR | MS | ADP-Glo $IC_{50}$ | MCF 10A $IC_{50}$ |
|---|---|---|---|---|---|---|
| I-2311 | 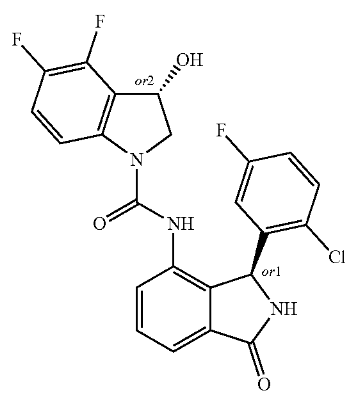 [SMILES: O=C1N[C@H](c2cc(F)ccc2Cl)c2c(NC(=O)N3C[C@@H](O)c4c3ccc(F)c4F)cccc21] | O[C@@H]1CN(C(=O)Nc2cccc3C(=O)N[C@@H](c23)c2cc(F)ccc2Cl)c2ccc(F)c(F)c12 | (400 MHz, DMSO-d6) 9.08 (s, 1H), 8.60 (s, 1H), 7.58 (dd, J = 12.9, 5.6 Hz, 2H), 7.45 (q, J = 6.9, 5.3 Hz, 2H), 7.36 (dd, J = 8.9, 5.1 Hz, 1H), 7.27 (q, J = 9.4 Hz, 1H), 7.10 (td, J = 8.4, 3.1 Hz, 1H), 6.52 (s, 1H), 6.08 (s, 1H), 5.92 (d, J = 4.9 Hz, 1H), 5.34 (s, 1H), 3.96 (dd, J = 11.3, 7.6 Hz, 1H), 3.36 (d, J = 2.9 Hz, 1H). | 474.3 | D | |
| I-2312 | 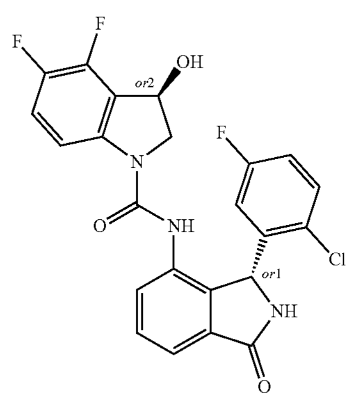 [SMILES: O=C1N[C@@H](c2cc(F)ccc2Cl)c2c(NC(=O)N3C[C@H](O)c4c3ccc(F)c4F)cccc21] | O[C@H]1CN(C(=O)Nc2cccc3C(=O)N[C@H](c23)c2cc(F)ccc2Cl)c2ccc(F)c(F)c12 | (400 MHz, DMSO-d6) 9.09 (s, 1H), 8.59 (s, 1H), 7.64-7.51 (m, 2H), 7.48-7.40 (m, 2H), 7.36 (dd, J = 8.9, 5.1 Hz, 1H), 7.28 (dt, J = 11.0, 8.6 Hz, 1H), 7.10 (ddd, J = 8.9, 7.9, 3.1 Hz, 1H), 6.55 (s, 1H), 6.08 (s, 1H), 5.93 (d, J = 5.8 Hz, 1H), 5.39-5.30 (m, 1H), 3.96 (dd, J = 11.2, 7.7 Hz, 1H), 3.36 (d, J = 2.9 Hz, 1H). | 474.3 | D | |
| I-2313 | 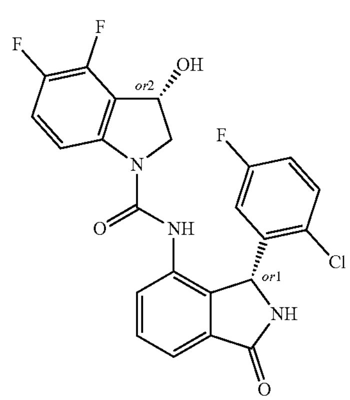 [SMILES: O=C1N[C@@H](c2cc(F)ccc2Cl)c2c(NC(=O)N3C[C@@H](O)c4c3ccc(F)c4F)cccc21] | O[C@@H]1CN(C(=O)Nc2cccc3C(=O)N[C@H](c23)c2cc(F)cc2Cl)c2ccc(F)c(F)c12 | (400 MHz, DMSO-d6) 9.06 (s, 1H), 8.73 (s, 1H), 7.69 (d, J = 8.8 Hz, 1H), 7.62-7.49 (m, 2H), 7.44-7.25 (m, 3H), 7.17 (td, J = 8.3, 3.1 Hz, 1H), 6.50 (s, 1H), 5.98 (m, 2H), 5.28 (t, J = 7.1 Hz, 1H), 3.81 (dd, J = 11.5, 2.4 Hz, 1H), 3.21 (s, 1H). | 474.3 | D | |

TABLE 2-continued

Representative Compounds of the Invention with Bioactivity Data.

| Ex. No. | Structure | SMILES | $^1$H NMR | MS | ADP-Glo IC$_{50}$ | MCF 10A IC$_{50}$ |
|---|---|---|---|---|---|---|
| I-2314 | 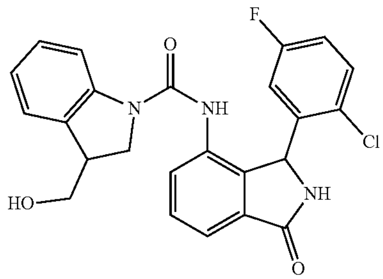 [SMILES: O=C1NC(c2cc(F)ccc2Cl)c2c(NC(=O)N3CC(CO)c4ccccc43)cccc21] | OCC1CN(C(=O)Nc2cccc3C(=O)NC(c23)c2cc(F)ccc2Cl)c2ccccc12 | (400 MHz, DMSO-d6) δ 9.04 (br. s, 1H), 8.58 (br. s, 0.5H), 8.56 (br. s, 0.5H), 7.79-7.67 (m, 1H), 7.60-7.52 (m, 2H), 7.43-7.32 (m, 2H), 7.21 (d, J = 7.3 Hz, 1H), 7.18-7.07 (m, 2H), 6.89 (ddd, J = 7.4, 4.1, 0.9 Hz, 1H), 6.48 (br. s, 1H), 6.03 (br. s, 1H), 4.94 (br. s, 1H), 3.93 (t, J = 9.9 Hz, 0.5H), 3.74 (dd, J = 10.0, 4.6 Hz, 0.5H), 3.69-3.55 (m, 1H), 3.41-3.38 (submerged m, 1H), 3.28-3.09 (m, 2H); 1:1 mixture of diastereomers. | 452.3 | D | |
| I-2315 | 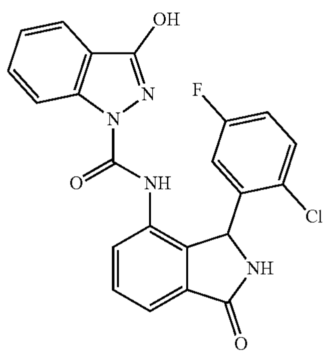 [SMILES: O=C1NC(c2cc(F)ccc2Cl)c2c(NC(=O)n3nc(O)c4ccccc43)cccc21] | Oc1nn(C(=O)Nc2cccc3C(=O)NC(c23)c2cc(F)ccc2Cl)c2ccccc12 | (400 MHz, DMSO-d6) δ 9.38 (s, 1H), 9.10 (s, 1H), 8.11 (d, J = 8.4 Hz, 1H), 7.85 (d, J = 8.0 Hz, 1H), 7.68 (dd, J = 7.5, 1.1 Hz, 1H), 7.65-7.57 (m, 2H), 7.56-7.50 (m, 1H), 7.34-7.21 (m, 2H), 7.01 (td, J = 8.5, 3.0 Hz, 1H), 6.66 (br s, 1H), 6.21 (br s, 1H). | 437.0 | D | |
| I-2316 | 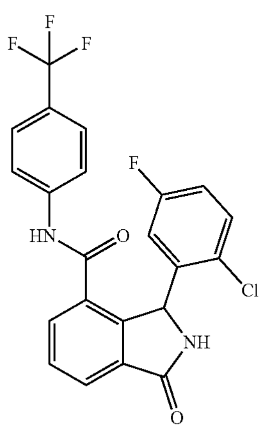 [SMILES: O=C(Nc1ccc(C(F)(F)F)cc1)c1cccc2c1C(c1cc(F)ccc1Cl)NC2=O] | Fc1ccc(C1)c(c1)C1NC(=O)c2cccc(C(=O)Nc3cc(cc3)C(F)(F)F)c12 | (400 MHz, DMSO-d6) δ 10.71 (s, 1 H), 9.28 (s, 1 H), 7.95 (d, J = 7.5 Hz, 1 H), 7.75 (t, J = 7.6 Hz, 1 H), 7.64 (app s, 4 H), 7.37 (dd, J = 8.1, 5.1 Hz, 1 H), 7.14-7.07 (m, 1 H), 6.50 (submerged br s, 1 H), 6.41 (overlapped br s, 1 H). | 449.2 | E | |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-2317 | 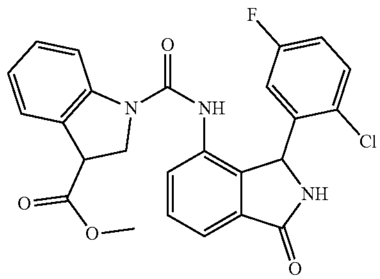 [SMILES: COC(=O)C1CN(C(=O)Nc2cccc3c2C(c2cc(F)ccc2Cl)NC3=O)c2ccccc21] | COC(=O)C1CN(C(=O)Nc2cccc3C(=O)NC(c23)c2cc(F)ccc2Cl)c2ccccc12 | (400 MHz, DMSO-d6) δ 9.05 (br. s, 1H), 8.71 (br. s, 0.5H), 8.68 (br. s, 0.5H), 7.73 (d, J = 8.0 Hz, 1H), 7.66-7.47 (m, 2H), 7.44-7.29 (m, 3H), 7.24-7.06 (m, 2H), 6.95 (ddd, J = 7.5, 3.3, 1.0 Hz, 1H), 6.57 (br. s, 1H), 6.04 (br. s, 1H), 4.41 (dd, J = 10.3, 6.2 Hz, 0.5H), 4.32 (dd, J = 10.3, 6.0 Hz, 0.5H), 4.22 (dd, J = 10.4, 6.1 Hz, 0.5H), 4.06 (t, J = 10.6 Hz, 0.5H), 3.74-3.69 (submerged m, 0.5H), 3.74 (s, 1.5H), 3.72 (s, 0.5H), 3.42-3.32 (submerged m, 0.5H); 1:1 mixture. of diastereomers. | 435.4 | E | |
| I-2318 | 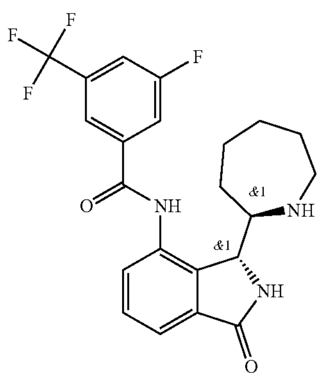 [SMILES: O=C(Nc1cccc2c1[C@H]([C@H]1CCCCCN1)NC2=O)c1cc(F)cc(C(F)(F)F)c1] | Fc1cc(cc(c1)C(F)(F)F)C(=O)Nc1ccc c2C(=O)N[C@@H]([C@H]3CCCCCN3)c12 | (400 MHz, CD3CN) δ 8.75 (dd, J = 7.6, 1.5 Hz, 0.5H), 8.55 (dd, J = 7.6, 1.4 Hz, 0.5H), 8.07 (s, 0.5H (formate salt)), 8.03 (s, 0.5H), 8.01 (s, 0.5H), 7.94-7.86 (m, 1H), 7.68 (d, J = 8.5 Hz, 1H), 7.53-7.45 (m, 2H), 6.95 (br s, 0.5H), 6.87 (br s, 0.5H), 4.72 (d, J = 1.7 Hz, 0.5H), 4.53 (d, J = 9.8 Hz, 0.5H), 3.40 (dt, J = 9.0, 2.5 Hz, 0.5H), 2.77-2.69 (m, 1H), 2.65-2.36 (m, 2H, submerged under H2O peak)), 1.85-1.78 (m, 0.5H), 1.71-1.53 (m, 3H), 1.52-1.35 (m, 3H) ppm [~1:1 dr, NH protons not observed]. | 436.4 | E | |
| I-2319 | 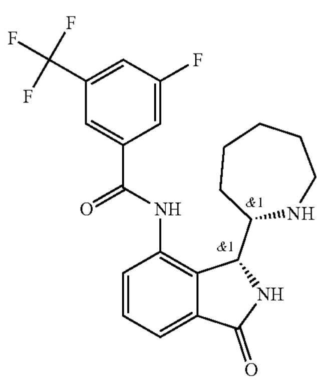 [SMILES: O=C(Nc1cccc2c1[C@H]([C@@H]1CCCCCN1)NC2=O)c1cc(F)cc(C(F)(F)F)c1] | Fc1cc(cc(c1)C(F)(F)F)C(=O)Nc1ccc c2C(=O)~[C@@H]([C@@H]3CCCCCN3)c12 | (400 MHz, CD3CN) δ 8.55 (dd, J = 7.6, 1.5 Hz, 1H), 8.09 (s, 0.5H, formate salt)), 8.01 (s, 1H), 7.90 (d, J = 9.0 Hz, 1H), 7.68 (d, J = 8.6 Hz, 1H), 7.55-7.45 (m, 2H), 6.95 (br s, 1H), 4.53 (dd, J = 9.6, 1.0 Hz, 1H), 2.77-2.68 (m, 1H), 2.60-2.51 (m, 1H), 2.44-2.36 (m, 1H (submerged under H2O peak)), 1.85-1.78 (m, 1H), 1.74-1.55 (m, 3H), 1.53-1.37 (m, 3H) ppm [single diastereomer, NH protons not observed]. | 436.4 | E | |

TABLE 2-continued

Representative Compounds of the Invention with Bioactivity Data.

| Ex. No. | Structure | SMILES | $^1$H NMR | MS | ADP-Glo IC$_{50}$ | MCF 10A IC$_{50}$ |
|---|---|---|---|---|---|---|
| I-2320 | 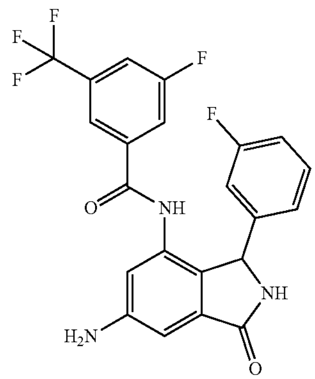 [SMILES: Nc1cc(NC(=O)c2cc(F)cc(C(F)(F)F)c2)c2c(c1)C(=O)NC2c1cccc(F)c1] | Nc1cc2C(=O)NC(c2c(NC(=O)c2cc(F)cc(c2)C(F)(F)F)c1)c1ccc(F)c1 | (400 MHz, DMSO-d6) δ 10.17 (s, 1 H), 8.84 (s, 1 H), 7.93 (d, J = 8.4 Hz, 1 H), 7.70 (d, J = 9.0 Hz, 1 H), 7.62 (s, 1 H), 7.20-7.12 (m, 1 H), 6.98 (td, J = 8.5, 2.4 Hz, 1 H), 6.81 (d, J = 1.8 Hz, 1 H), 6.78 (d, J = 7.7 Hz, 1 H), 6.74-6.68 (m, 2 H), 5.57 (br s, 2 H), 5.52 (s, 1 H). | 448.2 | C | |
| I-2321 | 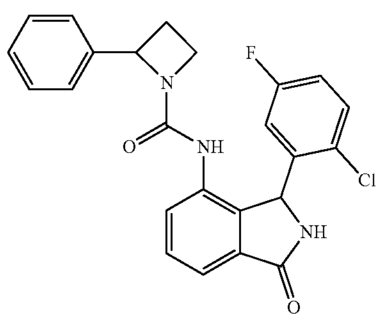 [SMILES: O=C1NC(c2cc(F)ccc2Cl)c2c(NC(=O)N3CCC3c3ccccc3)cccc21] | Fc1ccc(C1)c(c1)C1NC(=O)c2cccc(NC(=O)N3CCC3c3ccccc3)c12 | (400 MHz, DMSO-d6) δ 9.05 (br s, 0.5H), 9.01 (br s, 0.5H), 8.51 (s, 0.5H), 8.04 (s, 0.5H), 7.58-7.53 (m, 1H), 7.53-7.47 (m, 2H), 7.38-7.27 (m, 3H), 7.26-7.20 (m, 4H), 6.61 (br s, 1H), 6.08 (br s, 0.5H), 6.03 (submerged br s, 0.5H), 5.21 (t, J = 8.1 Hz, 0.5H), 4.92 (t, J = 7.7 Hz, 0.5H), 3.86-3.74 (m, 1H), 3.61 (dd, J = 16.0, 7.7 Hz, 0.5H), 3.04 (dd, J = 14.3, 7.6 Hz, 0.5H), 2.47 (submerged m, 1H), 2.04-1.87 (m, 1H). 1:1 Mix of diastereomers | 436.0 | E | |
| I-2322 | 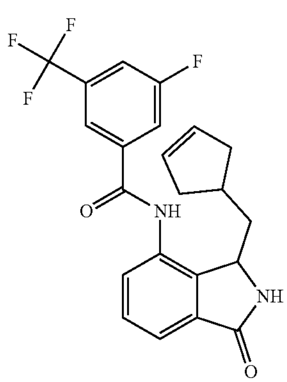 [SMILES: O=C(Nc1cccc2c1C(CC1CC=CC1)NC2=O)c1cc(F)cc(C(F)(F)F)c1] | Fc1cc(cc(c1)C(F)(F)F)C(=O)Nc1ccc2C(=O)NC(CC3CC=CC3)c12 | (400 MHz, DMSO d6) δ 10.79 (s, 1H), 8.94 (s, 1H), 8.14 (s, 1H), 8.09 (d, J = 9.0 Hz, 1H), 8.03 (d, J = 8.4 Hz, 1H), 7.61-7.50 (m, 3H), 5.55-5.49 (m, 1H), 5.42-5.37 (m, 1H), 4.80 (d, J = 7.6 Hz, 1H), 2.40-2.28 (m, 2H), 2.28-2.16 (m, 1H), 2.00-1.86 (m, 2H), 1.78-1.66 (m, 1H), 1.34-1.24 (m, 1H). | 419.4 | E | |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-2323 | 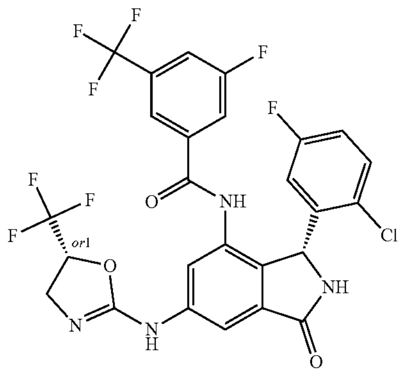 [SMILES: O=C(Nc1cc(NC2=NC[C@H](C(F)(F)F)O2)cc2c1[C@H](c1cc(F)ccc1Cl)NC2=O)c1cc(F)cc(C(F)(F)F)c1] | FC(F)([C@@H]1OC(NC(C=C23)=CC(NC(C4=CC(C(F)(F)F)=CC(F)=C4)=O)=C3[C@@H](NC2=O)C5=CC(F)=CC=C5Cl)=NC1)F | | 619.0 | B | |
| I-2324 | 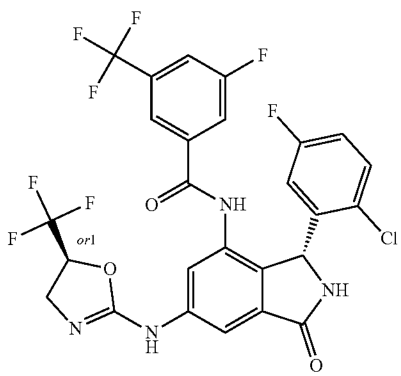 [SMILES: O=C(Nc1cc(NC2=NC[C@@H](C(F)(F)F)O2)cc2c1[C@H](c1cc(F)ccc1Cl)NC2=O)c1cc(F)cc(C(F)(F)F)c1] | FC(F)([C@H]1OC(NC(C=C23)=CC(NC(C4=CC(C(F)(F)F)=CC(F)=C4)=O)=C3[C@@H](NC2=O)C5=CC(F)=CC=C5Cl)=NC1)F | | 619.0 | A | A |
| I-2325 | 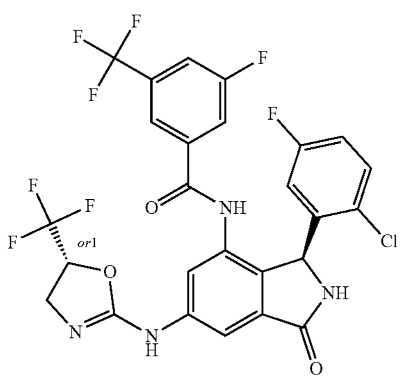 [SMILES: O=C(Nc1cc(NC2=NC[C@H](C(F)(F)F)O2)cc2c1[C@@H](c1cc(F)ccc1Cl)NC2=O)c1cc(F)cc(C(F)(F)F)c1] | FC(F)([C@@H]1OC(NC(C=C23)=CC(NC(C4=CC(C(F)(F)F)=CC(F)=C4)=O)=C3[C@H](NC2=O)C5=CC(F)=CC=C5Cl)=NC1)F | | 619.0 | D | |
| I-2326 | 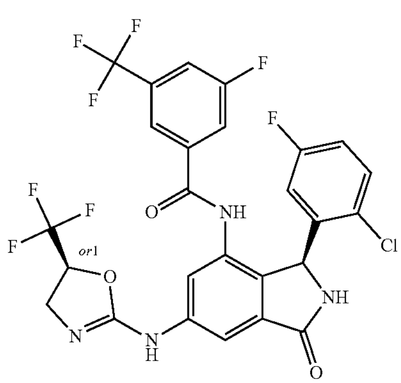 [SMILES: O=C(Nc1cc(NC2=NC[C@@H](C(F)(F)F)O2)cc2c1[C@@H](c1cc(F)ccc1Cl)NC2=O)c1cc(F)cc(C(F)(F)F)c1] | FC(F)([C@H]1OC(NC(C=C23)=CC(NC(C4=CC(C(F)(F)F)=CC(F)=C4)=O)=C3[C@H](NC2=O)C5=CC(F)=CC=C5Cl)=NC1)F | | 619.0 | D | |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-2327 | 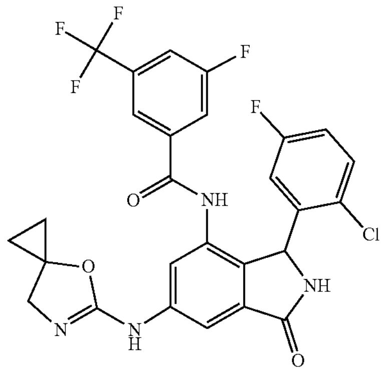 [SMILES: O=C(Nc1cc(NC2=NCC3(CC3)O2)cc2c1C(c1cc(F)ccc1Cl)NC2=O)c1cc(F)cc(C(F)(F)F)c1] | FC(F)(C1=CC(F)=CC(C(NC2=C3C(NC(C3=CC(NC4=NCC5(CC5)O4)=C2)=O)C6=CC(F)=CC=C6Cl)=O)=C1)F | (500 MHz, DMSO) δ 10.45 (s, 1H), 9.02 (s, 1H), 7.90 (d, J = 8.5 Hz, 1H), 7.70 (d, J = 9.3 Hz, 1H), 7.63 (d, J = 15.0 Hz, 1H), 7.33-7.24 (m, 1H), 7.06 (qd, J = 8.1, 4.1 Hz, 1H), 6.67 (s, 2H), 5.87 (s, 1H), 3.87-3.80 (m, 2H), 1.15-1.09 (m, 2H), 0.77 (s, 2H). | 577.0 | B | |
| I-2328 | 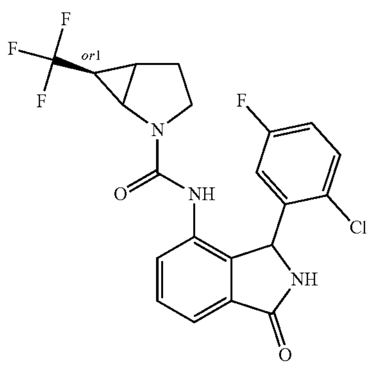 [SMILES: O=C1NC(c2cc(F)ccc2Cl)c2c(NC(=O)N3CCC4C3[C@H]4C(F)(F)F)cccc21] | Fc1ccc(C1)c(c1)C1NC(=O)c2cccc(NC(=O)N3CCC4C3[C@H]4C(F)(F)F)c12 | | 454.3 | E | |
| I-2329 | 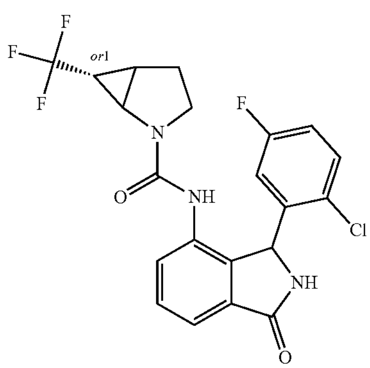 [SMILES: O=C1NC(c2cc(F)ccc2Cl)c2c(NC(=O)N3CCC4C3[C@@H]4C(F)(F)F)cccc21] | Fc1ccc(C1)c(c1)C1NC(=O)c2cccc(NC(=O)N3CCC4C3[C@@H]4C(F)(F)F)c12 | | 454.2 | D | |
| I-2330 | 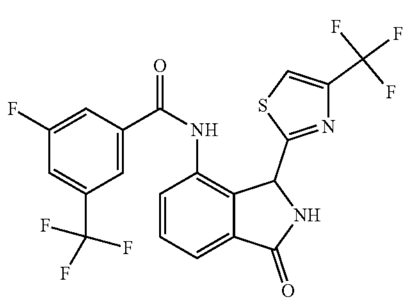 [SMILES: O=C(Nc1cccc2c1C(c1nc(C(F)(F)F)cs1)NC2=O)c1cc(F)cc(C(F)(F)F)c1] | Fc1cc(cc(c1)C(F)(F)F)C(=O)Nc1ccc2C(=O)NC(c3nc(cs3)C(F)(F)F)c12 | (400 MHz, DMSO-d6) δ 10.67 (s, 1H), 9.59 (d, J = 1.3 Hz, 1H), 8.42 (s, 1H), 8.05-7.98 (m, 3H), 7.73-7.63 (m, 3H), 6.34 (d, J = 1.3 Hz, 1H) | 490.2 | E | |

TABLE 2-continued

Representative Compounds of the Invention with Bioactivity Data.

| Ex. No. | Structure | SMILES | $^1$H NMR | MS | ADP-Glo IC$_{50}$ | MCF 10A IC$_{50}$ |
|---|---|---|---|---|---|---|
| I-2331 | 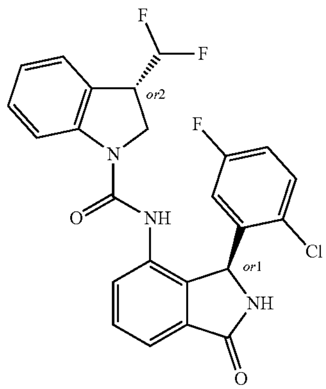 [SMILES: O=C1N[C@H](c2cc(F)ccc2Cl)c2c(NC(=O)N3C[C@@H](C(F)F)c4ccccc43)cccc21] | FC(F)[C@@H]1CN(C(=O)Nc2cccc3C(=O)N[C@@H](c23)c2cc(F)ccc2Cl)c2ccccc12 | | 470.2 | D | |
| I-2332 | 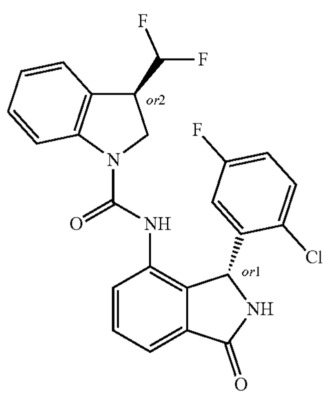 [SMILES: O=C1N[C@@H](c2cc(F)ccc2Cl)c2c(NC(=O)N3C[C@H](C(F)F)c4ccccc43)cccc21] | FC(F)[C@H]1CN(C(=O)Nc2cccc3C(=O)N[C@H](c23)c2cc(F)ccc2Cl)c2ccccc12 | | 470.2 | D | |
| I-2333 | 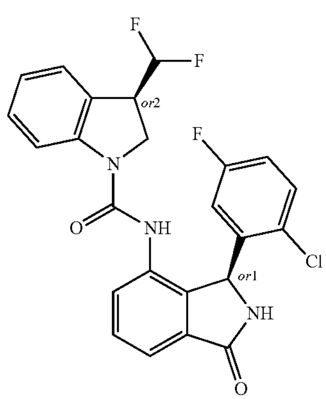 [SMILES: O=C1N[C@H](c2cc(F)ccc2Cl)c2c(NC(=O)N3C[C@H](C(F)F)c4ccccc43)cccc21] | FC(F)[C@H]1CN(C(=O)Nc2cccc3C(=O)N[C@@H](c23)c2cc(F)ccc2Cl)c2ccccc12 | | 470.2 | A | B |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-2334 | 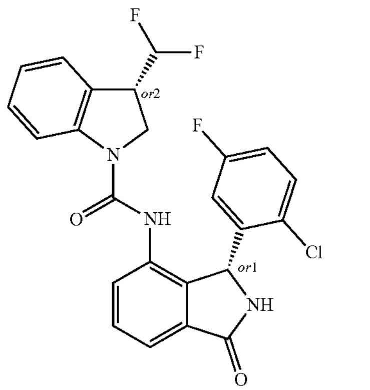 [SMILES: O=C1N[C@@H](c2cc(F)ccc2Cl)c2c(NC(=O)N3C[C@@H](C(F)F)c4ccccc43)cccc21] | FC(F)[C@@H]1CN(C(=O)Nc2cccc3C(=O)N[C@H](c23)c2cc(F)ccc2Cl)c2cccc12 | | 470.2 | A | B |
| I-2335 | 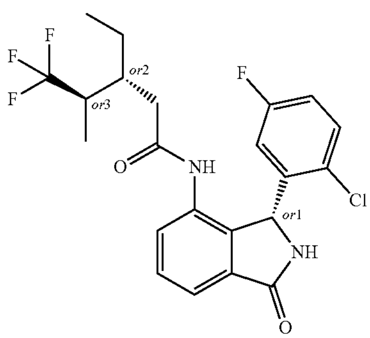 [SMILES: CC[C@H](CC(=O)Nc1cccc2c1[C@H](c1cc(F)ccc1Cl)NC2=O)[C@@H](C)C(F)(F)F] | CC[C@H](CC(=O)Nc1ccccc2C(=O)N[C@H](c12)c1cc(F)ccc1Cl)[C@@H](C)C(F)(F)F | | 455.2 | D | |
| I-2336 | 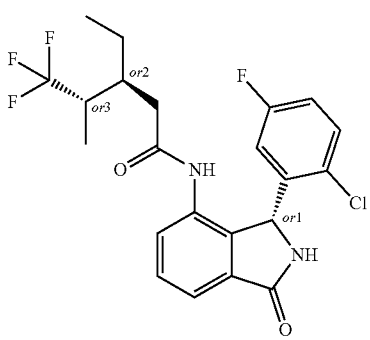 [SMILES: CC[C@@H](CC(=O)Nc1cccc2c1[C@H](c1cc(F)ccc1Cl)NC2=O)[C@H](C)C(F)(F)F] | CC[C@@H](CC(=O)Nc1cccc2C(=O)N[C@@H](c12)c1cc(F)ccc1Cl)[C@H](C)C(F)(F)F | | 455.2 | D | |
| I-2337 | 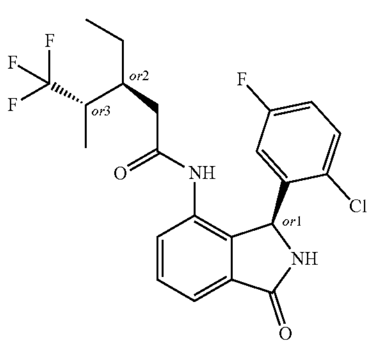 [SMILES: CC[C@@H](CC(=O)Nc1cccc2c1[C@@H](c1cc(F)ccc1Cl)NC2=O)[C@H](C)C(F)(F)F] | CC[C@@H](CC(=O)Nc1cccc2C(=O)N[C@@H](c12)c1cc(F)ccc1Cl)[C@@H](C)C(F)(F)F | | 455.2 | E | |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-2338 | 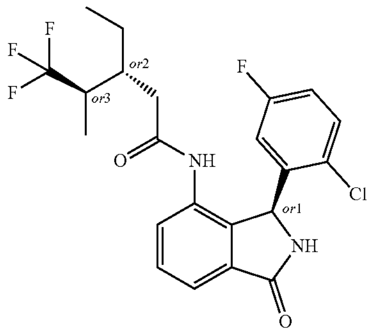 [SMILES: CC[C@H](CC(=O)Nc1cccc2c1[C@@H](c1cc(F)ccc1Cl)NC2=O)[C@@H](C)C(F)(F)F] | CC[C@H](CC(=O)Nc1ccc c2C(=O)N[C@@H](c12)c 1cc(F)cc c1Cl)[C@@H](C)C(F)(F)F | | 455.2 | E | |
| I-2339 | 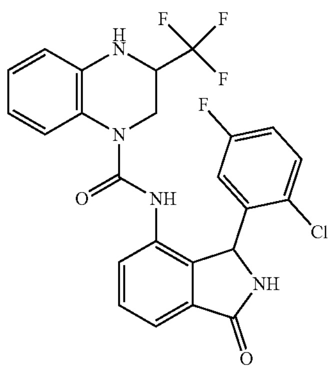 [SMILES: O=C1NC(c2cc(F)ccc2Cl)c2c(NC(=O)N3CC(C(F)(F)F)Nc4ccccc43)cccc21] | Fc1ccc(C1)c(c1)C1NC(=O)c 2cccc(NC(=O)N3 CC(Nc4c cccc34)C(F)(F)F)c 12 | (400 MHz, DMSO-d6) δ 9.06 (br s, 1H), 8.76 (s, 0.5H), 8.24 (s, 0.5H), 7.69-7.58 (m, 0.5H), 7.58-7.41 (m, 3H), 7.32 (d, J = 7.5 Hz, 0.5H), 7.27-7.18 (m, 1H), 6.94-6.80 (m, 2H), 6.78-6.74 (m, 1H), 6.40 (t, J = 7.6 Hz, 1H), 6.27 (dd, J = 15.2, 8.0 Hz, 1H), 6.09 (br s, 1H), 5.73 (br s, 1H), 4.79 (br d, J = 14.3 Hz, 0.5H), 4.39-4.23 (m, 0.5H), 4.21-4.00 (m, 1H), 3.35 (submerged m, 0.5H), 2.75 (br d, J = 12.9 Hz, 0.5H). 1:1 Mix of diastereomers. | 505.0 | E | |
| I-2340 | 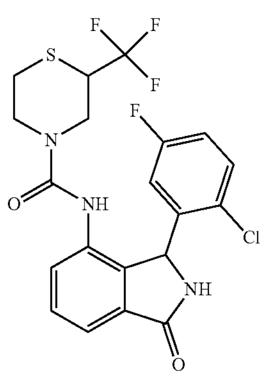 [SMILES: O=C1NC(c2cc(F)ccc2Cl)c2c(NC(=O)N3CCSC(C(F)(F)F)C3)cccc21] | Fc1ccc(C1)c(c1)C1NC(=O)c 2cccc(NC(=O)N3 CCSC(C3)C(F)(F)F)c12 | (400 MHz, DMSO-d6) δ 9.06 (br s, 0.5H), 9.04 (br s, 0.5H), 8.66 (br s, 0.5H), 8.64 (br s, 0.5H) 7.61-7.46 (m, 3H), 7.35-7.19 (m, 2H), 6.51 (br s, 1H), 6.03 (br s, 0.5H), 5.98 (br s, 0.5H), 4.19 (br d, J = 12.1 Hz, 0.5H), 3.93 (dd, J = 14.1, 2.7 Hz, 0.5H), 3.69-3.56 (m, 1H), 3.55-3.44 (m, 1H), 3.42-3.35 (submerged m, 0.5H), 3.19 (dd, J = 11.3, 9.7 Hz, 0.5H), 3.13-2.97 (m, 1H), 2.79-2.66 (m, 1H), 2.60 (dd, J = 12.8, 9.0 Hz, 0.5H), 2.26 (br d, J = 12.4 Hz, 0.5H). 1:1 Mix of diastereomers | 474.0 | E | |

TABLE 2-continued

Representative Compounds of the Invention with Bioactivity Data.

| Ex. No. | Structure | SMILES | ¹H NMR | MS | ADP-Glo IC₅₀ | MCF 10A IC₅₀ |
|---|---|---|---|---|---|---|
| I-2341 | 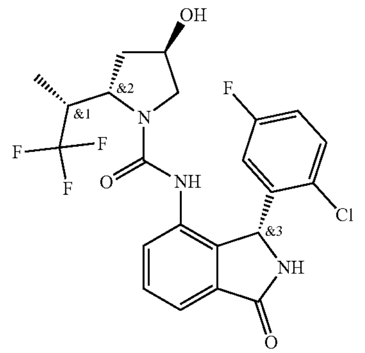 [SMILES: C[C@H]([C@@H]1C[C@@H](O)CN1C(=O)Nc1cccc2c1[C@H](c1cc(F)ccc1Cl)NC2=O)C(F)(F)F] | C[C@H]([C@@H]1C[C@@H](O)CN1C(=O)Nc1ccc2C(=O)N[C@H](c12)c1cc(F)ccc1Cl)C(F)(F)F | (400 MHz, CD3CN) δ 7.63-7.58 (m, 2H), 7.57-7.45 (m, 2H), 7.21 (br s, 1H), 7.10 (ddd, J = 8.8, 8.0, 3.1 Hz, 1H), 6.69 (br s, 1H), 6.56 (br s, 1H), 6.28 (s, 1H), 4.16 (p, J = 7.0 Hz, 1H), 4.09 (td, J = 8.1, 3.9 Hz, 1H), 3.34 (dd, J = 9.5, 7.1 Hz, 1H), 3.29-3.16 (m, 1H), 2.77 (dd, J = 9.7, 6.9 Hz), 2.13-2.04 (m, 1H [submerged under H2O]), 1.73-1.63 (m, 1H), 0.89 (d, J = 7.1 Hz, 3H) ppm [95:5 dr, 85% purity]. | 486.4 | B | |
| I-2342 | 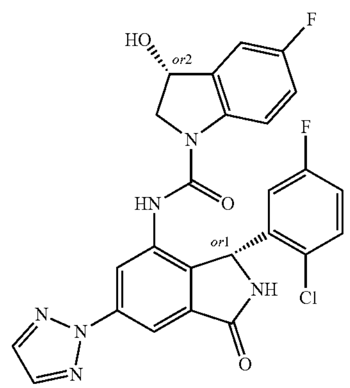 [SMILES: O=C1N[C@@H](c2cc(F)ccc2Cl)c2c(NC(=O)N3C[C@H](O)c4cc(F)ccc43)cc(-n3nccn3)cc21] | O[C@H]1CN(C(=O)Nc2cc(cc3C(=O)N[C@H](c23)c2cc(F)ccc2Cl)-n2nccn2)c2ccc(F)cc12 | (400 MHz, DMSO-d6) 9.27 (s, 1H), 8.93 (s, 1H), 8.22 (s, 2H), 8.16 (d, J = 2.0 Hz, 1H), 8.08 (d, J = 2.0 Hz, 1H), 7.86 (s, 1H), 7.38 (dd, J = 8.9, 5.1 Hz, 1H), 7.17 (ddd, J = 13.5, 8.1, 2.9 Hz, 2H), 7.10 (td, J = 9.0, 2.8 Hz, 1H), 6.07 (s, 1H), 5.78 (d, J = 6.0 Hz, 1H), 5.06 (d, J = 9.2 Hz, 1H), 3.73 (dd, J = 11.4, 3.6 Hz, 1H), 3.24 (s, 1H). | 523.3 | B | |
| I-2343 | 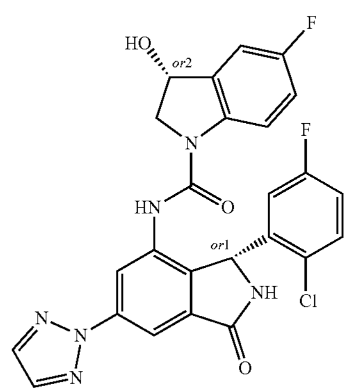 [SMILES: O=C1N[C@@H](c2cc(F)ccc2Cl)c2c(NC(=O)N3C[C@H](O)c4cc(F)ccc43)cc(-n3nccn3)cc21] | O[C@H]1CN(C(=O)Nc2cc(cc3C(=O)N[C@@H](c23)c2cc(F)ccc2Cl)-n2nccn2)c2ccc(F)cc12 | (400 MHz, DMSO-d6) 9.29 (s, 1H), 8.77 (s, 1H), 8.23 (d, J = 8.6 Hz, 3H), 8.09 (d, J = 1.9 Hz, 1H), 7.75 (dd, J = 8.7, 4.7 Hz, 1H), 7.37 (dd, J = 8.9, 5.1 Hz, 1H), 7.17-7.10 (m, 2H), 7.12-7.02 (m, 1H), 6.16 (s, 1H), 5.75 (d, J = 5.0 Hz, 1H), 5.15 (s, 1H), 4.03-3.93 (m, 1H), 3.26-3.19 (m, 1H). | 523.2 | D | |
| I-2344 | 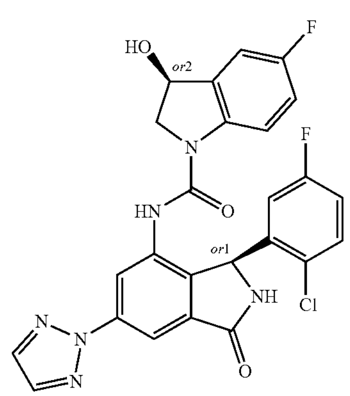 [SMILES: O=C1N[C@H](c2cc(F)ccc2Cl)c2c(NC(=O)N3C[C@@H](O)c4cc(F)ccc43)cc(-n3nccn3)cc21] | O[C@@H]1CN(C(=O)Nc2cc(cc3C(=O)N[C@@H](c23)c2cc(F)ccc2Cl)-n2nccn2)c2ccc(F)cc12 | | 523.1 | D | |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-2345 | 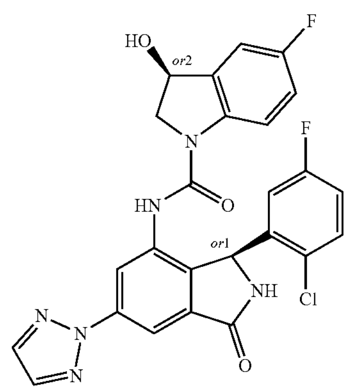 [SMILES: O=C1N[C@H](c2cc(F)ccc2Cl)c2c(NC(=O)N3C[C@@H](O)c4cc(F)ccc43)cc(-n3nccn3)cc21] | O[C@@H]1CN(C(=O)Nc2cc(cc3C(=O)N[C@@H](c23)c2cc(F)ccc2Cl)-n2nccn2)c2ccc(F)cc12 | (400 MHz, DMSO-d6) 9.27 (s, 1H), 8.94 (s, 1H), 8.22 (s, 2H), 8.16 (s, 1H), 8.08 (s, 1H), 7.86 (s, 1H), 7.38 (dd, J = 8.9, 5.1 Hz, 1H), 7.22-7.06 (m, 3H), 6.16-5.95(s, 1H), 5.79 (d, J = 6.0 Hz, 1H), 5.07 (s, 1H), 3.77-3.69 (m, 1H). | 523.2 | D | |
| I-2346 | 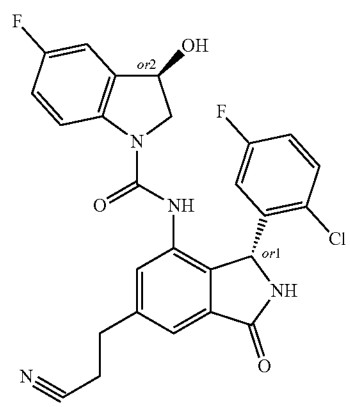 [SMILES: N#CCCc1cc(NC(=O)N2C[C@H](O)c3cc(F)ccc32)c2c(c1)C(=O)N[C@H]2c1cc(F)ccc1Cl] | O[C@H]1CN(C(=O)Nc2cc(CCC#N)cc3C(=O)N[C@H](c23)c2cc(F)ccc2Cl)c2ccc(F)cc12 | (400 MHz, DMSO-d6) 9.05 (s, 1H), 8.66 (s, 1H), 7.83 (dd, J = 9.1, 4.7 Hz, 1H), 7.55 (d, J = 1.5 Hz, 1H), 7.37 (dd, J = 8.9, 5.1 Hz, 1H), 7.29 (s, 1H), 7.15 (ddd, J = 13.3, 8.0, 2.9 Hz, 2H), 7.08 (td, J = 9.0, 2.8 Hz, 1H), 6.53 (s, 1H), 5.97 (s, 1H), 5.76 (d, J = 6.0 Hz, 1H), 5.07 (s, 1H), 3.71 (dd, J = 11.4, 3.6 Hz, 1H), 3.23 (s, 1H), 3.11-2.95 (m, 2H), 2.91 (t, J = 7.6 Hz, 2H). | 509.1 | A | B |
| I-2347 | 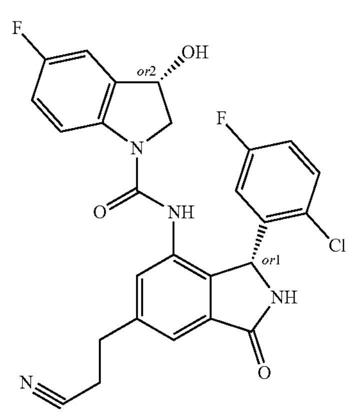 [SMILES: N#CCCc1cc(NC(=O)N2C[C@@H](O)c3cc(F)ccc32)c2c(c1)C(=O)N[C@H]2c1cc(F)ccc1Cl] | O[C@@H]1CN(C(=O)Nc2cc(CCC#N)cc3C(=O)N[C@H](c23)c2cc(F)cc2Cl)c2ccc(F)cc12 | (400 MHz, DMSO-d6) 9.05 (s, 1H), 8.66 (s, 1H), 7.83 (dd, J = 9.1, 4.7 Hz, 1H), 7.55 (d, J = 1.5 Hz, 1H), 7.37 (dd, J = 8.9, 5.1 Hz, 1H), 7.29 (s, 1H), 7.15 (ddd, J = 13.3, 8.0, 2.9 Hz, 2H), 7.08 (td, J = 9.0, 2.8 Hz, 1H), 6.53 (s, 1H), 5.97 (s, 1H), 5.76 (d, J = 6.0 Hz, 1H), 5.07 (s, 1H), 3.71 (dd, J = 11.4, 3.6 Hz, 1H), 3.23 (s, 1H), 3.11-2.95 (m, 2H), 2.91 (t, J = 7.6 Hz, 2H). | 509.1 | B | |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-2348 | 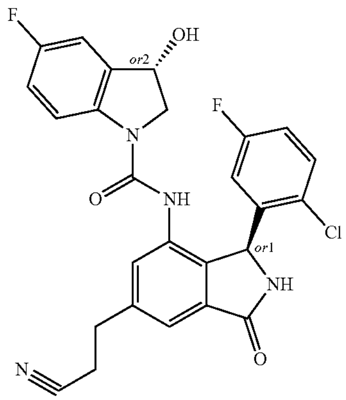 [SMILES: N#CCCc1cc(NC(=O)N2C[C@@H](O)c3cc(F)ccc32)c2c(c1)C(=O)N[C@@H]2c1cc(F)ccc1Cl] | O[C@@H]1CN(C(=O)Nc2cc(CCC#N)cc3C(=O)N[C@@H](c23)c2cc(F)ccc2Cl)c2ccc(F)cc12 | (400 MHz, DMSO-d6) 9.05 (s, 1H), 8.66 (s, 1H), 7.83 (dd, J = 9.1, 4.7 Hz, 1H), 7.55 (d, J = 1.5 Hz, 1H), 7.37 (dd, J = 8.9, 5.1 Hz, 1H), 7.29 (s, 1H), 7.15 (ddd, J = 13.3, 8.0, 2.9 Hz, 2H), 7.08 (td, J = 9.0, 2.8 Hz, 1H), 6.53 (s, 1H), 5.97 (s, 1H), 5.76 (d, J = 6.0 Hz, 1H), 5.07 (s, 1H), 3.71 (dd, J = 11.4, 3.6 Hz, 1H), 3.23 (s, 1H), 3.11-2.95 (m, 2H), 2.91 (t, J = 7.6 Hz, 2H). | 509.1 | D | |
| I-2349 | 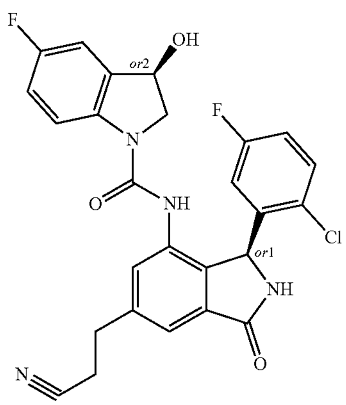 [SMILES: N#CCCc1cc(NC(=O)N2C[C@H](O)c3cc(F)ccc32)c2c(c1)C(=O)N[C@@H]2c1cc(F)ccc1Cl] | O[C@H]1CN(C(=O)Nc2cc(CCC#N)cc3C(=O)N[C@@H](c23)c2cc(F)cc2Cl)c2ccc(F)cc12 | (400 MHz, DMSO-d6) 9.05 (s, 1H), 8.66 (s, 1H), 7.83 (dd, J = 9.1, 4.7 Hz, 1H), 7.55 (d, J = 1.5 Hz, 1H), 7.37 (dd, J = 8.9, 5.1 Hz, 1H), 7.29 (s, 1H), 7.15 (ddd, J = 13.3, 8.0, 2.9 Hz, 2H), 7.08 (td, J = 9.0, 2.8 Hz, 1H), 6.53 (s, 1H), 5.97 (s, 1H), 5.76 (d, J = 6.0 Hz, 1H), 5.07 (s, 1H), 3.71 (dd, J = 11.4, 3.6 Hz, 1H), 3.23 (s, 1H), 3.11-2.95 (m, 2H), 2.91 (t, J = 7.6 Hz, 2H). | 509.1 | D | |
| I-2350 | 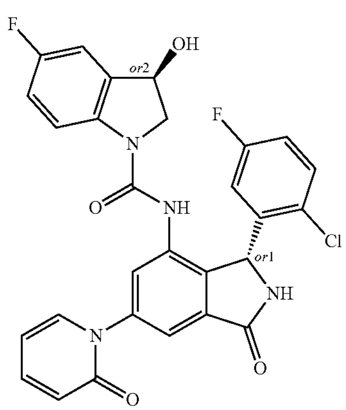 [SMILES: O=C1N[C@@H](c2cc(F)ccc2Cl)c2c(NC(=O)N3C[C@H](O)c4cc(F)ccc43)cc(-n3ccccc3=O)cc21] | O[C@H]1CN(C(=O)Nc2cc(cc3C(=O)N[C@H](c23)c2cc(F)cc2Cl)-n2ccccc2=O)c2ccc(F)cc12 | (400 MHz, DMSO-d6) 9.23 (s, 1H), 8.84 (s, 1H), 7.85-7.77 (m, 2H), 7.60-7.51 (m, 2H), 7.46-7.36 (m, 2H), 7.15 (dddd, J = 34.3, 18.0, 8.6, 3.0 Hz, 3H), 6.80-6.51 (m, 2H), 6.37 (td, J = 6.7, 1.4 Hz, 1H), 6.09 (s, 1H), 5.77 (d, J = 6.0 Hz, 1H), 5.08 (s, 1H), 3.70 (dd, J = 11.3, 3.6 Hz, 1H), 3.30-3.10 (s, 1H). | 531.2 | A | C |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-2351 | 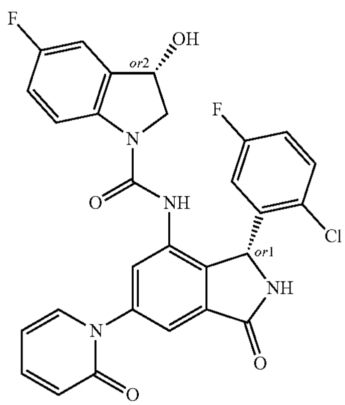 [SMILES: O=C1N[C@@H](c2cc(F)ccc2Cl)c2c(NC(=O)N3C[C@@H](O)c4cc(F)ccc43)cc(-n3ccccc3=O)cc21] | O[C@@H]1CN(C(=O)Nc2cc(cc3C(=O)N[C@H](c23)c2cc(F)ccc2Cl)-n2ccccc2=O)c2ccc(F)cc12 | (400 MHz, DMSO-d6) 9.26 (s, 1H), 8.70 (s, 1H), 7.77-7.73 (m, 2H), 7.61-7.50 (m, 3H), 7.39 (dd, J = 8.9, 5.2 Hz, 1H), 7.14 (ddd, J = 11.2, 8.0, 3.0 Hz, 2H), 7.05 (td, J = 9.1, 2.8 Hz, 1H), 6.80-6.54 (m, 2H), 6.37 (td, J = 6.7, 1.3 Hz, 1H), 6.17 (s, 1H), 5.75 (d, J = 5.0 Hz, 1H), 5.15 (dt, J = 8.7, 4.5 Hz, 1H), 3.97 (dd, J = 11.1, 8.1 Hz, 1H), 3.22 (dd, J = 11.1, 4.0 Hz, 1H). | 531.1 | B | |
| I-2352 | 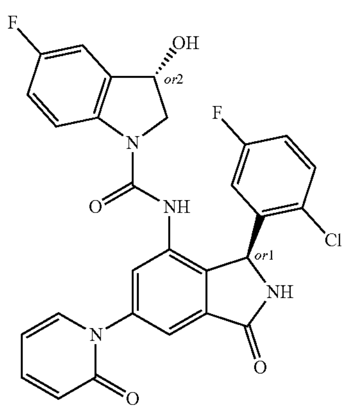 [SMILES: O=C1N[C@H](c2cc(F)ccc2Cl)c2c(NC(=O)N3C[C@@H](O)c4cc(F)ccc43)cc(-n3ccccc3=O)cc21] | O[C@@H]1CN(C(=O)Nc2cc(cc3C(=O)N[C@@H](c23)c2cc(F)ccc2Cl)-n2ccccc2=O)c2ccc(F)cc12 | (400 MHz, DMSO-d6) 9.26 (s, 1H), 8.70 (s, 1H), 7.81-7.69 (m, 2H), 7.60-7.50 (m, 3H), 7.39 (dd, J = 8.9, 5.2 Hz, 1H), 7.14 (ddd, J = 11.5, 8.0, 3.0 Hz, 2H), 7.05 (td, J = 9.0, 2.8 Hz, 1H), 6.80-6.54 (m, 2H), 6.37 (td, J = 6.7, 1.3 Hz, 1H), 6.17 (s, 1H), 5.75 (d, J = 5.0 Hz, 1H), 5.15 (dt, J = 8.7, 4.5 Hz, 1H), 3.97 (dd, J = 11.0, 8.0 Hz, 1H), 3.22 (dd, J = 11.2, 4.0 Hz, 1H). | 531.2 | D | |
| I-2353 | 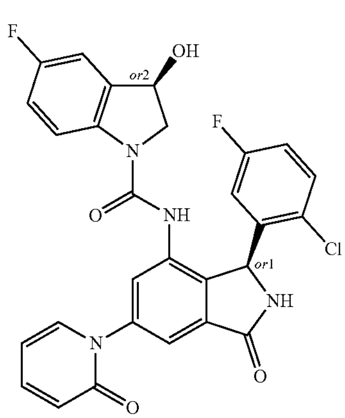 [SMILES: O=C1N[C@H](c2cc(F)ccc2Cl)c2c(NC(=O)N3C[C@H](O)c4cc(F)ccc43)cc(-n3ccccc3=O)cc21] | O[C@H]1CN(C(=O)Nc2cc(cc3C(=O)N[C@@H](c23)c2cc(F)ccc2Cl)-n2ccccc2=O)c2ccc(F)cc12 | (400 MHz, DMSO-d6) 9.23 (s, 1H), 8.83 (s, 1H), 7.84 (dd, J = 8.5, 4.6 Hz, 1H), 7.77 (dd, J = 6.9, 2.1 Hz, 1H), 7.60-7.51 (m, 2H), 7.46-7.36 (m, 2H), 7.15 (dddd, J = 34.5, 18.1, 8.6, 3.0 Hz, 3H), 6.80-6.50 (m, 2H), 6.37 (td, J = 6.7, 1.4 Hz, 1H), 6.08 (s, 1H), 5.77 (d, J = 6.0 Hz, 1H), 5.08 (s, 1H), 3.70 (dd, J = 11.3, 3.6 Hz, 1H), 3.25 (s, 1H). | 531.2 | D | |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-2354 | 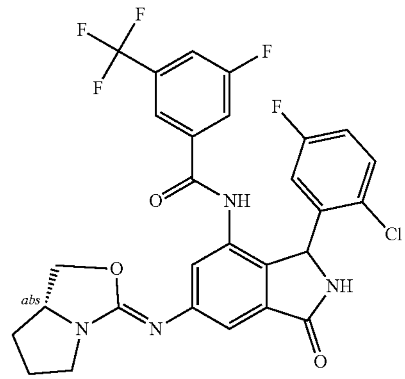 [SMILES: O=C(Nc1cc(/N=C2\OC[C@H]3CCCN23)cc2c1C(c1cc(F)ccc1Cl)NC2=O)c1cc(F)cc(C(F)(F)F)c1] | Fc1ccc(C1)c(c1)C1NC(=O)c2cc(cc(NC(=O)c3cc(F)cc(c3)C(F)(F)F)c12)\N=C1/OC[C@H]2CCCN12 | (500 MHz, DMSO) δ 10.33 (d, J = 3.4 Hz, 1H), 8.98 (s, 1H), 7.90 (dt, J = 8.3, 2.0 Hz, 1H), 7.70 (d, J = 9.1 Hz, 1H), 7.64 (s, 1H), 7.31-7.22 (m, 2H), 7.06 (td, J = 8.2, 3.0 Hz, 1H), 7.03 (s, 1H), 5.89 (s, 1H), 5.74 (s, 1H), 4.63-4.55 (m, 1H), 4.27 (s, 1H), 3.97 (s, 1H), 3.62 (s, 1H), 3.16 (s, 2H), 2.03-1.95 (m, 2H), 1.93-1.86 (m, 1H), 1.53-1.40 (m, 1H). | 591.0 | B | |
| I-2355 | 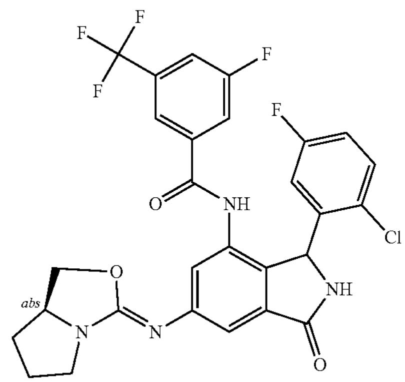 [SMILES: O=C(Nc1cc(/N=C2\OC[C@@H]3CCCN23)cc2c1C(c1cc(F)ccc1Cl)NC2=O)c1cc(F)cc(C(F)(F)F)c1] | Fc1ccc(C1)c(c1)C1NC(=O)c2cc(cc(NC(=O)c3cc(F)cc(c3)C(F)(F)F)c12)\N=C1/OC[C@@H]2CCCN12 | | 591.0 | B | |
| I-2356 | 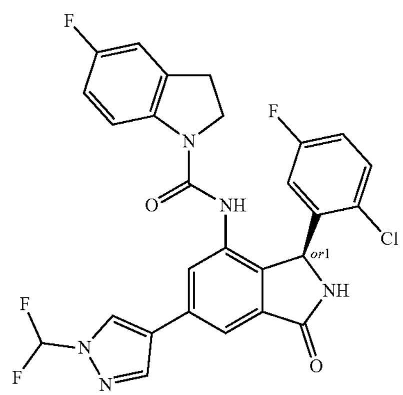 [SMILES: O=C1N[C@H](c2cc(F)ccc2Cl)c2c(NC(=O)N3CCc4cc(F)ccc43)cc(-c3cnn(C(F)F)c3)cc21] | FC(F)n1cc(cn1)-c1cc2C(=O)N[C@@H](c2c(NC(=O)N2CCc3cc(F)ccc23)c1)c1cc(F)ccc1Cl | | 556.3 | D | |
| I-2357 | 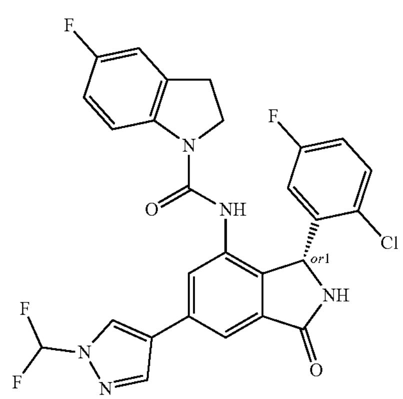 [SMILES: O=C1N[C@@H](c2cc(F)ccc2Cl)c2c(NC(=O)N3CCc4cc(F)ccc43)cc(-c3cnn(C(F)F)c3)cc21] | FC(F)n1cc(cn1)-c1cc2C(=O)N[C@H](c2c(NC(=O)N2CCc3cc(F)ccc23)c1)c1cc(F)ccc1Cl | | 556.3 | A | A |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-2358 | 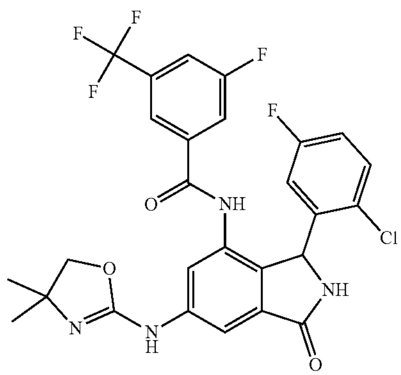 [SMILES: CC1(C)COC(Nc2cc(NC(=O)c3cc(F)cc(C(F)(F)F)c3)c3c(c2)C(=O)NC3c2cc(F)ccc2Cl)=N1] | FC(F)(C1=CC(F)=CC(C(NC2=C3C(NC(C3=CC(NC4=NC(C)(C)CO4)=C2)=O)C5=CC(F)=CC=C5Cl)=O)=C1)F | (500 MHz, DMSO) δ 10.43 (s, 1H), 9.01 (s, 1H), 8.13 (s, 1H), 7.91 (dd, J = 8.2, 2.2 Hz, 1H), 7.68 (d, J = 9.2 Hz, 1H), 7.60 (s, 1H), 7.50 (s, 1H), 7.27 (dd, J = 8.8, 5.2 Hz, 1H), 7.06 (tt, J = 8.6, 4.3 Hz, 1H), 6.59 (s, 1H), 5.85 (s, 1H), 3.98 (s, 2H), 1.26 (d, J = 3.3 Hz, 6H). | 579.0 | B | |
| I-2359 | 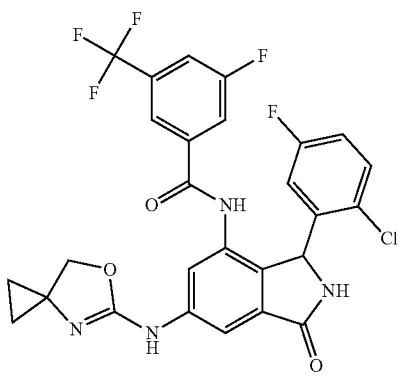 [SMILES: O=C(Nc1cc(NC2=NC3(CC3)CO2)cc2c1C(c1cc(F)ccc1Cl)NC2=O)c1cc(F)cc(C(F)(F)F)c1] | FC(F)(C1=CC(F)=CC(C(NC2=C3C(NC(C3=CC(NC4=NC5(CC5)CO4)=C2)=O)C6=C(F)=CC=C6Cl)=O)=C1)F | (500 MHz, DMSO) δ 10.45 (s, 1H), 9.03 (s, 1H), 8.12 (s, 1H), 7.94-7.87 (m, 2H), 7.68 (d, J = 9.4 Hz, 1H), 7.58 (s, 2H), 7.27 (dd, J = 8.8, 5.1 Hz, 1H), 7.06 (td, J = 8.4, 3.1 Hz, 1H), 6.50 (s, 1H), 5.84 (s, 1H), 4.25 (s, 2H), 1.22 (s, 0H), 0.95-0.90 (m, 2H), 0.75-0.68 (m, 2H). | 577.0 | A | B |
| I-2360 | 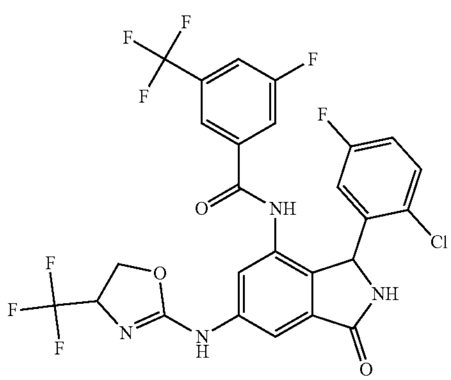 [SMILES: O=C(Nc1cc(NC2=NC(C(F)(F)F)CO2)cc2c1C(c1cc(F)ccc1Cl)NC2=O)c1cc(F)cc(C(F)(F)F)c1] | FC(F)(C1=CC(F)=CC(C(NC2=C3C(NC(C3=CC(NC4=NC(C(F)(F)F)CO4)=C2)=O)C5=CC(F)=CC=C5Cl)=O)=C1)F | (400 MHz, DMSO) δ 10.54 (d, J = 7.4 Hz, 1H), 10.14 (s, 1H), 9.09 (s, 1H), 8.47 (s, 1H), 8.03 (s, 1H), 7.98-7.88 (m, 2H), 7.72-7.63 (m, 2H), 7.58 (s, 1H), 7.28 (dd, J = 8.9, 5.1 Hz, 1H), 7.06 (s, 1H), 6.84 (s, 3H), 5.85 (s, 1H), 5.74 (s, 1H), 4.89 (s, 1H), 4.51 (t, J = 9.4 Hz, 1H), 4.44-4.35 (m, 1H). | 619.0 | A | C |
| I-2361 | 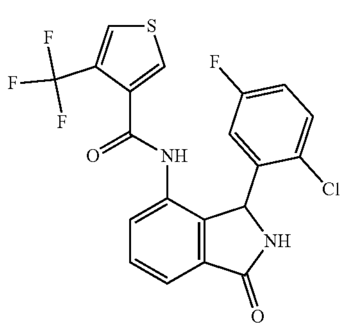 [SMILES: O=C(Nc1cccc2c1C(c1cc(F)ccc1Cl)NC2=O)c1cscc1C(F)(F)F] | Fc1ccc(C1)c(c1)C1NC(=O)c2cccc(NC(=O)c3cscc3C(F)(F)F)c12 | | | | D |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-2362 | 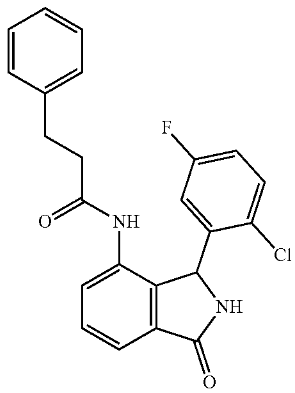 [SMILES: O=C(CCc1ccccc1)Nc1cccc2c1C(c1cc(F)ccc1Cl)NC2=O] | Fc1ccc(C1)c(c1)C1NC(=O)c2cccc(NC(=O)CCc3ccccc3)c12 | (400 MHz, DMSO-d6) 9.70 (s, 1H), 9.09 (s, 1H), 7.61 (dd, J = 7.6, 1.3 Hz, 1H), 7.56 (t, J = 7.5 Hz, 1H), 7.51 (s, 1H), 7.37 (dd, J = 7.5, 1.3 Hz, 1H), 7.32-7.10 (m, 6H), 6.02 (s, 1H), 2.70-2.57 (s, 1H), 2.57-2.52 (s, 1H), 2.34-2.16 (m, 2H). | 409.3 | E | |
| I-2363 | 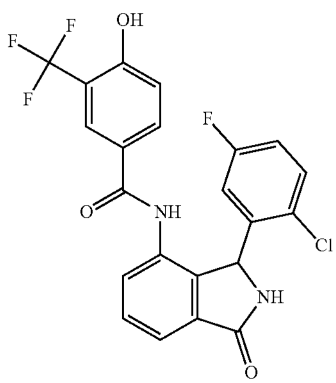 [SMILES: O=C(Nc1cccc2c1C(c1cc(F)ccc1Cl)NC2=O)c1ccc(O)c(C(F)(F)F)c1] | Oc1ccc(c1C(F)(F)F)C(=O)Nc1cccc2C(=O)NC(c12)c1cc(F)ccc1Cl | (400 MHz, DMSO-d6) 9.95 (s, 1H), 9.09 (s, 1H), 7.61 (p, J = 7.9, 7.5 Hz, 5H), 7.49 (d, J = 7.4 Hz, 1H), 7.31 (dd, J = 8.9, 5.2 Hz, 1H), 7.08 (td, J = 8.5, 3.1 Hz, 1H), 6.81 (s, 1H), 6.60 (s, 1H), 6.02 (s, 1H). | 465.1 | E | |
| I-2364 | 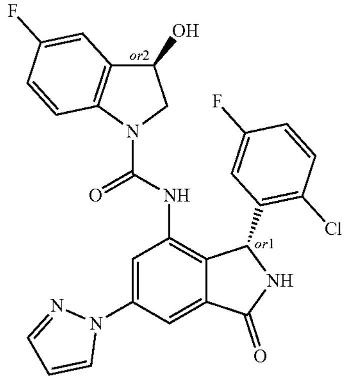 [SMILES: O=C1N[C@@H](c2cc(F)ccc2Cl)c2c(NC(=O)N3C[C@H](O)c4cc(F)ccc43)cc(-n3cccn3)cc21] | O[C@H]1CN(C(=O)Nc2cc(cc3C(=O)N[C@H](c23)c2cc(F)ccc2Cl)-n2cccn2)c2ccc(F)cc12 | (400 MHz; DMSO-d6) 9.18 (s, 1H), 8.85 (s, 1H), 8.71 (d, J = 2.6 Hz, 1H), 8.03-7.95 (m, 2H), 7.88-7.79 (m, 2H), 7.38 (dd, J = 9.0, 5.1 Hz, 1H), 7.22-7.05 (m, 3H), 6.63-6.57 (m, 1H), 6.02 (s, 1H), 5.78 (d, J = 6.0 Hz, 1H), 5.07 (s, 2H), 3.77-3.69 (m, 1H), 3.34 (s, 1H). | 522.3 | A | B |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-2365 | 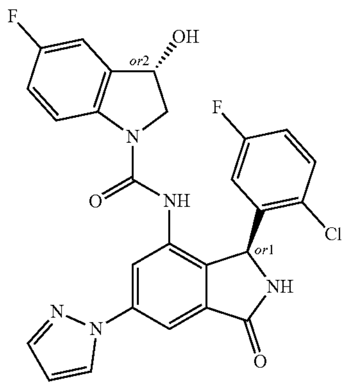 [SMILES: O=C1N[C@H](c2cc(F)ccc2Cl)c2c(NC(=O)N3C[C@@H](O)c4cc(F)ccc43)cc(-n3cccn3)cc21] | O[C@@H]1CN(C(=O)Nc2cc(cc3C(=O)N[C@@H](c23)c2cc(F)ccc2Cl)-n2cccn2)c2ccc(F)cc12 | (400 MHz, DMSO-d6) 9.21 (s, 1H), 8.74-8.68 (m, 2H), 8.07-7.99 (m, 2H), 7.81 (d, J = 1.8 Hz, 1H), 7.74 (dd, J = 9.0, 4.7 Hz, 1H), 7.36 (dd, J = 8.9, 5.1 Hz, 1H), 7.11 (td, J = 8.5, 3.0 Hz, 2H), 7.05 (td, J = 9.0, 2.8 Hz, 1H), 6.73 (s, 1H), 6.60 (t, J = 2.1 Hz, 1H), 6.12 (s, 1H), 5.75 (d, J = 5.0 Hz, 1H), 5.16 (dt, J = 8.3, 4.6 Hz, 1H), 3.99 (dd, J = 11.1, 8.1 Hz, 1H), 3.22 (dd, J = 11.2, 4.1 Hz, 1H). | 522.4 | C | |
| I-2366 | 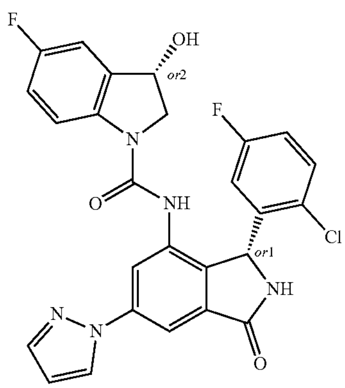 [SMILES: O=C1N[C@@H](c2cc(F)ccc2Cl)c2c(NC(=O)N3C[C@@H](O)c4cc(F)ccc43)cc(-n3cccn3)cc21] | O[C@@H]1CN(C(=O)Nc2cc(cc3C(=O)N[C@@H](c23)c2cc(F)ccc2Cl)-n2cccn2)c2ccc(F)cc12 | (400 MHz, DMSO-d6) 9.21 (s, 1H), 8.74-8.68 (m, 2H), 8.07-7.99 (m, 2H), 7.81 (d, J = 1.7 Hz, 1H), 7.74 (dd, J = 8.9, 4.7 Hz, 1H), 7.36 (dd, J = 8.9, 5.1 Hz, 1H), 7.11 (td, J = 8.4, 3.0 Hz, 3H), 6.60 (t, J = 2.1 Hz, 2H), 6.12 (s, 1H), 5.75 (d, J = 5.0 Hz, 1H), 5.16 (dt, J = 8.6, 4.5 Hz, 1H), 3.99 (dd, J = 11.1, 8.1 Hz, 1H), 3.22 (dd, J = 11.0, 4.1 Hz, 1H). | 522.3 | D | |
| I-2367 | 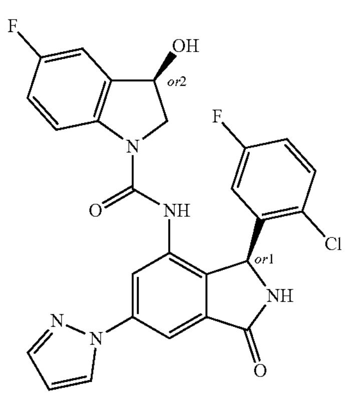 [SMILES: O=C1N[C@H](c2cc(F)ccc2Cl)c2c(NC(=O)N3C[C@H](O)c4cc(F)ccc43)cc(-n3cccn3)cc21] | O[C@H]1CN(C(=O)Nc2cc(cc3C(=O)N[C@@H](c23)c2cc(F)ccc2Cl)-n2cccn2)c2ccc(F)cc12 | (400 MHz, DMSO-d6) 9.19 (s, 1H), 8.85 (s, 1H), 8.72 (d, J = 2.5 Hz, 1H), 7.99 (dd, J = 11.9, 2.0 Hz, 2H), 7.81 (d, J = 1.7 Hz, 1H), 7.38 (dd, J = 8.9, 5.1 Hz, 1H), 7.22-7.11 (m, 2H), 7.11 (dd, J = 8.9, 2.8 Hz, 2H), 6.63-6.57 (m, 1H), 6.02 (s, 1H), 5.78 (d, J = 6.0 Hz, 1H), 5.07 (s, 1H), 3.73 (dd, J = 11.3, 3.6 Hz, 1H), 3.24 (s, 1H), 1.13 (s, 1H). | 522.4 | D | |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-2368 | 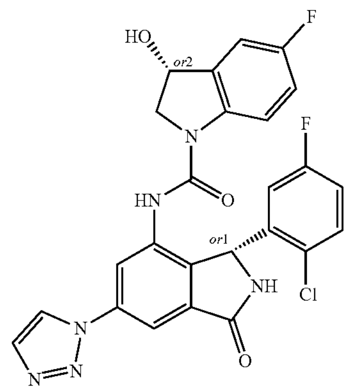 [SMILES: O=C1N[C@@H](c2cc(F)ccc2Cl)c2c(NC(=O)N3C[C@H](O)c4cc(F)ccc43)cc(-n3ccnn3)cc21] | O[C@H]1CN(C(=O)Nc2cc(cc3C(=O)N[C@H](c23)c2cc(F)cc2Cl)-n2ccnn2)c2ccc(F)cc12 | (400 MHz, DMSO-d6)9.30 (s, 1H), 9.07 (d, J = 1.2 Hz, 1H), 8.79 (s, 1H), 8.14 (d, J = 2.0 Hz, 1H), 8.09 (d, J = 2.0 Hz, 1H), 8.03 (d, J = 1.2 Hz, 1H), 7.75 (dd, J = 8.9, 4.7 Hz, 1H), 7.38 (dd, J = 8.9, 5.1 Hz, 1H), 7.20-7.11 (m, 2H), 7.06 (d, J = 2.9 Hz, 1H), 7.00-6.50 (m, 1H), 6.17 (s, 1H), 5.75 (s, 1H), 5.16 (s, 1H), 3.99 (dd, J = 11.1, 8.0 Hz, 1H), 3.24 (dd, J = 11.1, 4.0 Hz, 1H). | 523.1 | D | |
| I-2369 | 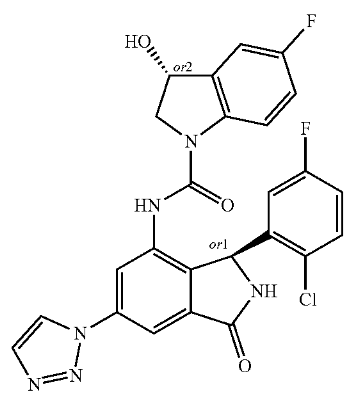 [SMILES: O=C1N[C@H](c2cc(F)ccc2Cl)c2c(NC(=O)N3C[C@H](O)c4cc(F)ccc43)cc(-n3ccnn3)cc21] | O[C@H]1CN(C(=O)Nc2cc(cc3C(=O)N[C@@H](c23)c2cc(F)cc2Cl)-n2ccnn2)c2ccc(F)cc12 | (400 MHz, DMSO-d6) 9.29 (s, 1H), 9.08 (d, J = 1.2 Hz, 1H), 8.96 (s, 1H), 8.17-7.98 (m, 3H), 7.86 (s, 1H), 7.39 (dd, J = 8.9, 5.1 Hz, 1H), 7.27-7.03 (m, 3H), 7.00-6.50 (m, 1H), 6.30-5.90 (m, 1H), 5.79 (d, J = 6.0 Hz, 1H), 5.09 (d, J = 9.0 Hz, 1H), 3.73 (dd, J = 11.4, 3.5 Hz, 1H), 3.17 (d, J = 5.2 Hz, 1H). | 523.1 | A | B |
| I-2370 | 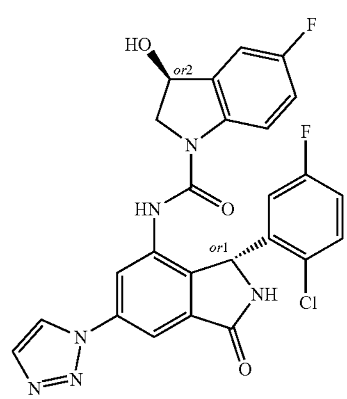 [SMILES: O=C1N[C@@H](c2cc(F)ccc2Cl)c2c(NC(=O)N3C[C@@H](O)c4cc(F)ccc43)cc(-n3ccnn3)cc21] | O[C@@H]1CN(C(=O)Nc2cc(cc3C(=O)N[C@H](c23)c2cc(F)cc2Cl)-n2ccnn2)c2ccc(F)cc12 | (400 MHz, DMSO-d6) 9.32 (s, 1H), 9.08 (s, 1H), 8.81 (s, 1H), 8.14 (d, J = 2.0 Hz, 1H), 8.10 (d, J = 1.9 Hz, 1H), 8.04 (s, 1H), 7.75 (dd, J = 8.9, 4.7 Hz, 1H), 7.38 (dd, J = 8.9, 5.1 Hz, 1H), 7.17-7.10 (m, 2H), 7.07 (dd, J = 9.1, 2.8 Hz, 1H), 6.90-6.50 (m, 1H), 6.17 (s, 1H), 5.76 (d, J = 4.9 Hz, 1H), 5.16 (dt, J = 8.7, 4.4 Hz, 1H), 4.16-3.90 (m, 1H), 3.23 (dd, J = 11.1, 4.0 Hz, 1H). | 523.1 | C | |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-2371 | 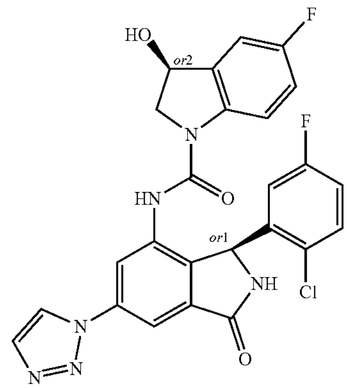 [SMILES: O=C1N[C@H](c2cc(F)ccc2Cl)c2c(NC(=O)N3C[C@@H](O)c4cc(F)ccc43)cc(-n3ccnn3)cc21] | O[C@@H]1CN(C(=O)Nc2cc(cc3C(=O)N[C@@H](c23)c2cc(F)ccc2Cl)-n2ccnn2)c2ccc(F)cc12 | (400 MHz, DMSO-d6) 9.28 (s, 1H), 9.07 (d, J = 1.2 Hz, 1H), 8.95 (s, 1H), 8.23-8.05 (m, 2H), 8.04 (d, J = 1.2 Hz, 1H), 7.86 (s, 1H), 7.39 (dd, J = 8.9, 5.1 Hz, 1H), 7.28-7.04 (m, 3H), 7.00-6.50 (m, 1H), 6.20-6.10 (m,1H), 5.78 (d, J = 6.0 Hz, 1H), 5.08 (s, 1H), 3.73 (dd, J = 11.3, 3.6 Hz, 1H), 3.30-3.20 (m,1H) | 523.1 | D | |
| I-2372 | 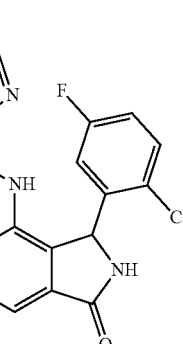 | Fc1ccc(C1)c(c1)C1NC(=O)c2cccc(NC(=O)\C=C\c3cccc3)c12 | (400 MHz, DMSO-d6) 9.95 (s, 1H), 9.08 (s, 1H), 7.67-7.60 (m, 1H), 7.64-7.52 (m, 3H), 7.49-7.39 (m, 5H), 7.39 (s, 1H), 7.14 (td, J = 8.3, 2.9 Hz, 1H), 6.49 (d, J = 15.8 Hz, 1H), 6.06 (s, 1H). | 407.1 | E | |
| I-2373 | 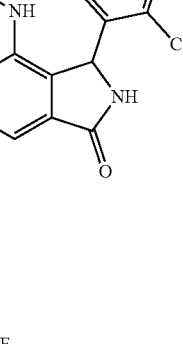 | Fc1ccc(C1)c(c1)C1NC(=O)c2cccc(NC(=O)n3ncc4cccc34)c12 | (400 MHz, DMSO-d6) δ 9.15 (br s, 1H), 8.38 (s, 1H), 8.20 (d, J = 8.4 Hz, 1H), 7.88 (d, J = 7.9 Hz, 1H), 7.78-7.54 (m, 4H), 7.37 (t, J = 7.4 Hz, 1H), 7.23 (dd, J = 8.6, 5.1 Hz, 1H), 6.99 (td, J = 7.3, 1.4 Hz, 1H), 6.61 (br s, 1H), 6.21 (br s, 1H). | 421.0 | B | |
| I-2374 | 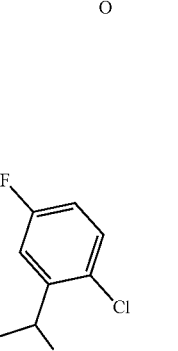 | Fc1ccc(C1)c(c1)C1NC(=O)c2cccc(NC(=O)C3CCc4cccc4CC3)c12 | (400 MHz, DMSO-d6) δ 9.63 (br. s, 1H), 9.04 (br. s, 1H), 7.58-7.49 (m, 2H), 7.49-7.41 (m, 1H), 7.37 (dd, J = 7.2, 1.7 Hz, 1H), 7.22 (ddd, J = 8.8, 8.1, 3.1 Hz, 1H), 7.09-7.00 (m, 4H), 6.51 (br. s, 1H), 6.01 (br. s, 1H), 2.75-2.53 (m, 4H), 2.37 (ddd, J = 11.2, 7.2, 3.0 Hz, 1H), 1.65-1.57 (m, 1H), 1.54-1.34 (m, 1H), 1.26-1.03 (m, 2H). | 449.2 | E | |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-2375 | 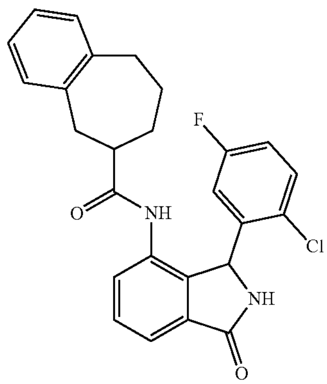 [SMILES: O=C1NC(c2cc(F)ccc2Cl)c2c(NC(=O)C3CCCc4ccccc4C3)cccc21] | Fc1ccc(C1)c(c1)C1NC(=O)c2cccc(NC(=O)C3CCCc4cccc4C3)c12 | (400 MHz, DMSO-d6) δ 9.70 (br. s, 0.5H), 9.68 (br. s, 0.5H), 9.11 (br. s, 1H), 7.67-7.51 (m, 3H), 7.43 (dd, J = 3.2, 1.7 Hz, 0.5H), 7.41 (dd, J = 3.41, 1.6 Hz, 0.5H), 7.28 (two overlapping ddd, J = 7.3, 3.3, 1.7 Hz, 1H), 7.12-6.99 (m, 3H), 7.05-6.94 (m, 0.5H), 6.93-6.80 (m, 0.5H), 6.10 (br. s, 1H), 2.88-2.62 (m, 3H), 2.39 (d, J = 14.0 Hz, 0.5H), 2.28-2.12 (m, 0.5H), 2.10-1.95 (m, 1H), 1.96-1.75 (m, 1H), 1.81-1.39 (m, 2H), 1.21-1.00 (m, 1H); 1:1 mixture of isomers. | 449.3 | E | |
| I-2376 | 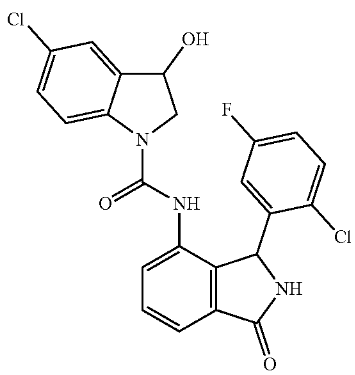 [SMILES: O=C1NC(c2cc(F)ccc2Cl)c2c(NC(=O)N3CC(O)c4cc(Cl)ccc43)cccc21] | OC1CN(C(=O)Nc2cccc3C(=O)NC(c23)c2cc(F)ccc2Cl)c2ccc(Cl)cc12 | (400 MHz, DMSO-d6) δ 9.08 (br s, 0.5 H), 9.06 (br s, 0.5 H), 8.70 (s, 0.5 H), 8.58 (s, 0.5 H), 7.83 (d, J = 8.5 Hz, 0.5 H), 7.70 (d, J = 8.7 Hz, 0.5 H), 7.64-7.52 (m, 2 H), 7.42 (dd, J = 7.4, 1.3 Hz, 0.5 H), 7.39-7.26 (m, 3 H), 7.24 (dd, J = 8.7, 2.3 Hz, 0.5 H), 7.19-7.13 (m, 0.5 H), 7.09 (td, J = 8.4, 3.1 Hz, 0.5 H), 6.51 (br s, 1 H), 6.07 (br s, 1 H), 5.99 (br s, 1 H), 5.76 (app dd, J = 10.6, 5.4 Hz, 1 H), 5.15 (dt, J = 8.1, 4.2 Hz, 0.5 H), 5.10-5.04 (m, 0.5 H), 3.96 (dd, J = 11.0, 8.1 Hz, 0.5 H), 3.71 (dd, J = 11.3, 3.4 Hz, 0.5 H), 3.21 (d, J = 3.8 Hz, 0.5 H), 3.19 (d, J = 3.7 Hz, 0.5 H). Approximately 1:1 mixture of diastereomers. | 472.2 | D | |
| I-2377 | 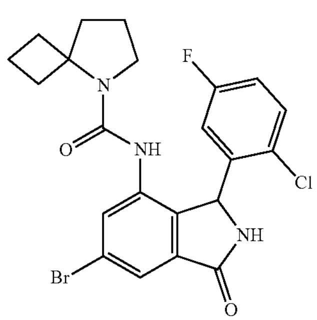 [SMILES: O=C1NC(c2cc(F)ccc2Cl)c2c(NC(=O)N3CCCC34CCC4)cc(Br)cc21] | Fc1ccc(C1)c(c1)C1NC(=O)c2cc(Br)cc(NC(=O)N3CCCC33CCC3)c12 | | 97.0 | C | |

| Ex. No. | Structure | SMILES | ¹H NMR | MS | ADP-Glo IC$_{50}$ | MCF 10A IC$_{50}$ |
|---|---|---|---|---|---|---|
| I-2378 | 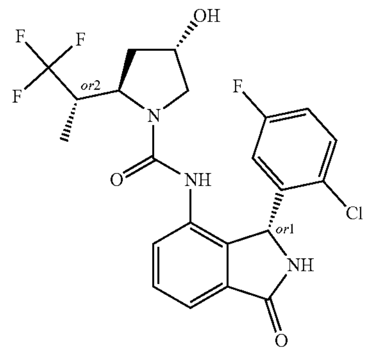 [SMILES: C[C@@H]([C@H]1C[C@H](O)CN1C(=O)Nc1cccc2c1[C@H](c1cc(F)ccc1Cl)NC2=O)C(F)(F)F] | C[C@@H]([C@H]1C[C@H](O)CN1C(=O)Nc1ccc2C(=O)N[C@H](c12)c1cc(F)ccc1Cl)C(F)(F)F | (400 MHz, CD3CN) δ 7.58 (dd, J = 7.4, 1.1 Hz, 1H), 7.52 (t, J = 7.6 Hz, 1H), 7.45-7.39 (m, 2H), 7.12 (br s, 1H), 7.04 (ddd, J = 8.8, 8.0, 3.1 Hz, 1H), 6.67 (br s, 1H), 6.57 (br s, 1H), 6.17 (br s, 1H), 4.36-4.30 (m, 1H), 4.26-4.19 (m, 1H), 3.31 (dd, J = 10.0, 5.3 Hz, 1H), 2.88-2.76 (m, 1H), 2.68 (dd, J = 9.8, 3.6 Hz, 1H), 2.07-2.00 (m, 1H), 1.91-1.82 (m, 1H), 1.01 (d, J = 7.3 Hz, 3H) ppm [single diastereomer] | 486.4 | E | |
| I-2379 | 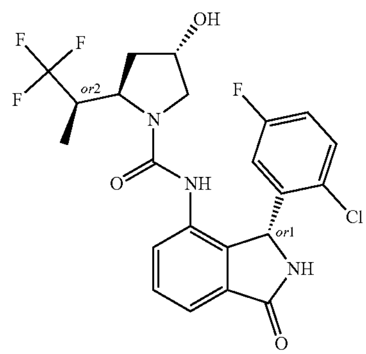 [SMILES: C[C@H]([C@H]1C[C@H](O)CN1C(=O)Nc1cccc2c1[C@H](c1cc(F)ccc1Cl)NC2=O)C(F)(F)F] | C[C@H]([C@H]1C[C@H](O)CN1C(=O)Nc1ccc2C(=O)N[C@H](c12)c1cc(F)ccc1Cl)C(F)(F)F | (400 MHz, CD3CN) δ 7.59 (dd, J = 7.4, 1.0 Hz, 1H), 7.53 (t, J = 7.6 Hz, 1H), 7.45-7.38 (m, 2H), 7.15 (br s, 1H), 7.04 (ddd, J = 8.8, 8.1, 3.1 Hz, 1H), 6.73 (br s, 1H), 6.56 (br s, 1H), 6.19 (br s, 1H), 4.34 (td, J = 8.2, 3.7 Hz, 1H), 4.30-4.23 (m, 1H), 3.26 (dd, J = 10.4, 4.2 Hz, 1H), 3.21-3.00 (m, 1H), 2.88 (d, J = 10.3 Hz, 1H), 2.13-2.07 (m, 1H [submerged under H2O peak]), 1.83-1.74 (m, 1H), 0.82 (d, J = 7.2 Hz, 3H) ppm. | 486.4 | E | |
| I-2380 | 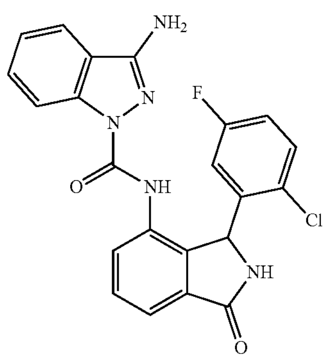 [SMILES: Nc1nn(C(=O)Nc2cccc3c2C(c2cc(F)ccc2Cl)NC3=O)c2ccccc12] | Cc1nn(C(=O)Nc2cccc3C(=O)NC(c23)c2cc(F)ccc2Cl)c2ccccc12 | (400 MHz, DMSO) δ 9.61 (s, 1H), 9.13 (s, 1H), 8.15 (dt, J = 8.4, 0.9 Hz, 1H), 7.84 (dt, J = 8.0, 1.0 Hz, 1H), 7.81 (dd, J = 6.6, 2.3 Hz, 1H), 7.65-7.60 (m, 2H), 7.57 (ddd, J = 8.3, 7.1, 1.1 Hz, 1H), 7.35 (ddd, J = 8.0, 7.1, 0.9 Hz, 1H), 7.30 (dd, J = 8.8, 5.1 Hz, 1H), 7.04 (ddd, J = 8.8, 7.9, 3.1 Hz, 1H), 6.82-6.50 (m, 1H), 6.21 (s, 1H), 2.54 (s, 3H) | 435.0 | C | |
| I-2381 | 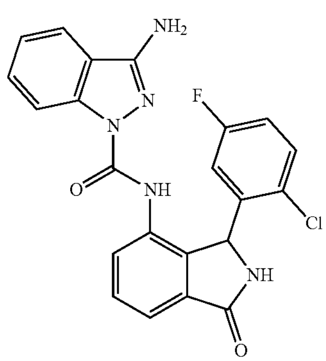 [SMILES: Nc1nn(C(=O)Nc2cccc3c2C(c2cc(F)ccc2Cl)NC3=O)c2ccccc12] | Nc1nn(C(=O)Nc2cccc3C(=O)NC(c23)c2cc(F)ccc2Cl)c2ccccc12 | (400 MHz, DMSO) δ 9.10 (s, 1H), 9.08 (s, 1H), 8.09-8.03 (m, 1H), 7.86 (dt, J = 8.0, 1.0 Hz, 1H), 7.78 (dd, J = 6.0, 3.0 Hz, 1H), 7.58 (q, J = 3.7, 3.0 Hz, 2H), 7.50 (ddd, J = 8.3, 7.1, 1.2 Hz, 1H), 7.37 (t, J = 6.7 Hz, 1H), 7.24 (ddd, J = 8.0, 7.1, 0.9 Hz, 1H), 7.07 (ddd, J = 8.9, 7.9, 3.1 Hz, 1H), 6.86-6.50 (m, 1H), 6.20 (s, 1H), 6.13 (s, 2H) | 436.0 | B | |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-2382 | 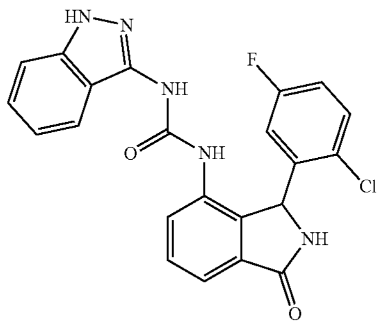 [SMILES: O=C(Nc1cccc2c1C(c1cc(F)ccc1Cl)NC2=O)Nc1n[nH]c2ccccc12] | Fc1ccc(C1)c(c1)C1NC(=O)c2cccc(NC(=O)Nc3n[nH]c4ccccc34)c12 | (500 MHz, DMSO) δ 12.16 (s, 1H), 9.70 (s, 1H), 9.43 (s, 1H), 9.09 (s, 1H), 7.89 (d, J = 8.3 Hz, 1H), 7.85 (d, J = 7.5 Hz, 1H), 7.60-7.52 (m, 2H), 7.43-7.32 (m, 3H), 7.08 (td, J = 8.4, 3.1 Hz, 1H), 7.02 (ddd, J = 7.9, 6.7, 1.0 Hz, 1H), 6.78-6.42 (m, 1H), 6.10 (s, 1H) | 436.0 | D | |
| I-2383 | 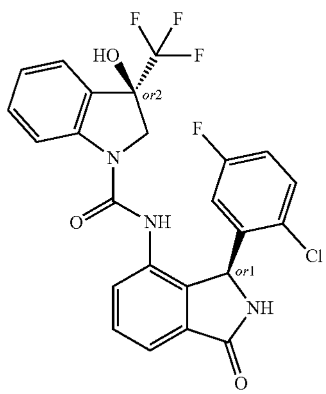 [SMILES: O=C1N[C@H](c2cc(F)ccc2Cl)c2c(NC(=O)N3C[C@@](O)(C(F)(F)F)c4ccccc43)cccc21] | O[C@]1(CN(C(=O)Nc2ccccc3C(=O)N[C@@H](c23)c2cc(F)ccc2Cl)c2cccc12)C(F)(F)F | (400 MHz, DMSOd6) δ 9.08 (s, 1H), 8.80 (s, 1H), 7.89 (d, J = 8.2 Hz, 1H), 7.64-7.55 (m, 2H), 7.39 (m, 3H), 7.31 (dd, J = 8.9, 5.2 Hz, 1H), 7.24 (s, 1H), 7.12 (td, J = 8.5, 3.0 Hz, 1H), 7.06 (t, J = 7.5 Hz, 1H), 6.52 (br s, 1H), 6.03 (s, 1H), 3.97 (d, J = 12.0 Hz, 1H), 3.48 (d, J = 11.5 H, 1Hz). | 506.3 | E | |
| I-2384 | 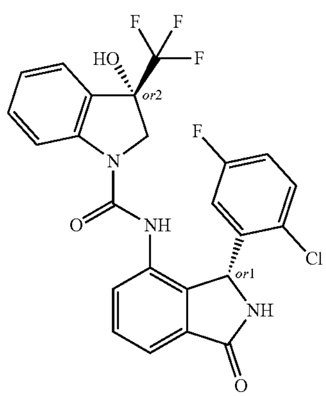 [SMILES: O=C1N[C@@H](c2cc(F)ccc2Cl)c2c(NC(=O)N3C[C@](O)(C(F)(F)F)c4ccccc43)cccc21] | O[C@@]1(CN(C(=O)Nc2cccc3C(=O)N[C@H](c23)c2cc(F)ccc2Cl)c2cccc12)C(F)(F)F | (400 MHz, DMSOd6) δ 9.10 (s, 1H), 8.70 (, 1Hs), 7.81 (d, J = 8.2 H, 1Hz), 7.67-7.55 (m, 2H), 7.48 (dd, J = 7.3, 1.5 Hz, 1H), 7.42 (d, J = 7.6 Hz, 1H), 7.36 (td, J = 7.1, 1.1 Hz, 1H), 7.33 (d, J = 5.3 Hz, 1H), 7.21 (s, 1H), 7.11 (td, J = 8.7, 3.2 Hz, 1H), 7.05 (td, J = 7.9, 0.9 Hz, 1H ), 6.53 (br s, 1H), 6.08 (s, 1H), 4.16 (d, J = 12.0 Hz, 1H), 3.44 (d, J = 12.0 Hz, 1H). | 506.3 | D | |
| I-2385 | 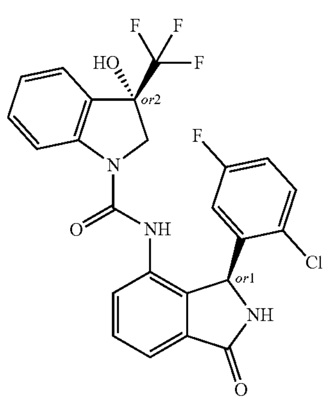 [SMILES: O=C1N[C@H](c2cc(F)ccc2Cl)c2c(NC(=O)N3C[C@](O)(C(F)(F)F)c4ccccc43)cccc21] | O[C@@]1(CN(C(=O)Nc2cccc3C(=O)N[C@@H](c23)c2cc(F)ccc2Cl)c2cccc12)C(F)(F)F | (400 MHz, DMSOd6) δ 9.10 (s, 1H), 8.70 (, 1 Hs), 7.81 (d, J = 8.2 H, 1 Hz), 7.67-7.55 (m, 2H), 7.48 (dd, J = 7.3, 1.5 Hz, 1H), 7.42 (d, J = 7.6 Hz, 1H), 7.36 (td, J = 7.1, 1.1 Hz, 1H), 7.33 (d, J = 5.3 Hz, 1H), 7.21 (s, 1H), 7.11 (td, J = 8.7, 3.2 Hz, 1H), 7.05 (td, J = 7.9, 0.9 Hz, 1H), 6.53 (br s, 1H), 6.08 (s, 1H), 4.16 (d, J = 12.0 Hz, 1H), 3.44 (d, J = 12.0 Hz, 1H). | 506.3 | D | |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-2386 | 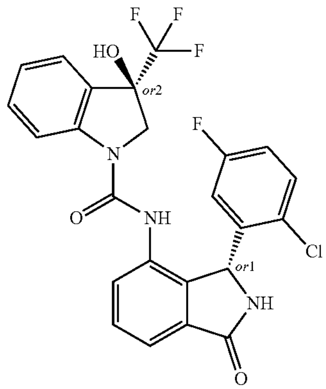 [SMILES: O=C1N[C@@H](c2cc(F)ccc2Cl)c2c(NC(=O)N3C[C@@](O)(C(F)(F)F)c4ccccc43)cccc21] | O[C@]1(CN(C(=O)Nc2ccc3C(=O)N[C@H](c23)c2cc(F)ccc2Cl)c2ccccc12)C(F)(F)F | (400 MHz, DMSOd6) δ 9.08 (s, 1H), 8.80 (s, 1H), 7.89 (d, J = 8.2 Hz, 1H), 7.64-7.55 (m, 2H), 7.39 (m, 3H), 7.31 (dd, J = 8.9, 5.2 Hz, 1H), 7.24 (s, 1H), 7.12 (td, J = 8.5, 3.0 Hz, 1H), 7.06 (t, J = 7.5 Hz, 1H), 6.52 (br s, 1H), 6.03 (s, 1H), 3.97 (d, J = 12.0 Hz, 1H), 3.48 (d, J = 11.5 H, 1Hz). | 506.3 | A | A |
| I-2387 | 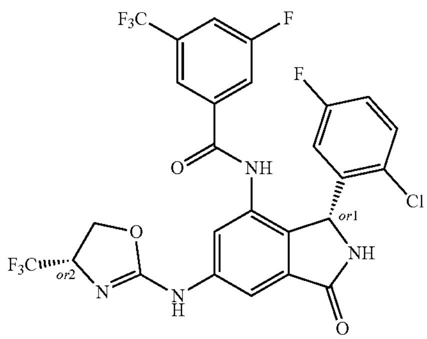 [SMILES: O=C(Nc1cc(NC2=N[C@H](C(F)(F)F)CO2)cc2c1[C@H](c1cc(F)ccc1Cl)NC2=O)c1cc(F)cc(C(F)(F)F)c1] | O=C1C2=CC(NC3=N[C@H](C(F)(F)F)CO3)=CC(NC(C(C4=CC(F)=CC(C(F)(F)F)=C4)=O)=C2[C@H](C5=C(Cl)C=CC(F)=C5)N1 | | 619.0 | A | B |
| I-2388 | 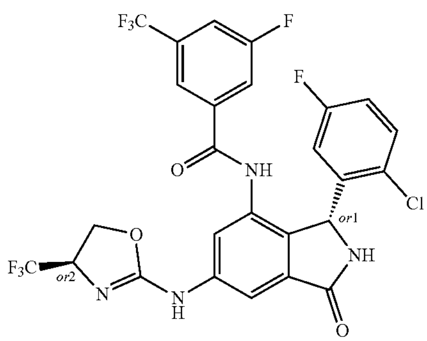 [SMILES: O=C(Nc1cc(NC2=N[C@@H](C(F)(F)F)CO2)cc2c1[C@H](c1cc(F)ccc1Cl)NC2=O)c1cc(F)cc(C(F)(F)F)c1] | O=C1C2=CC(NC3=N[C@@H](C(F)(F)F)CO3)=CC(NC(C(C4=CC(F)=CC(C(F)(F)F)=C4)=O)=C2[C@H](C5=C(Cl)C=CC(F)=C5)N1 | | 619.0 | A | B |
| I-2389 | 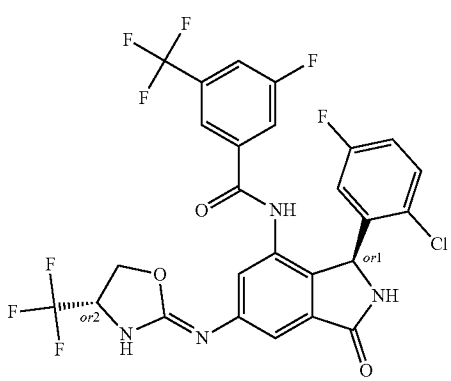 [SMILES: O=C(Nc1cc(/N=C2/N[C@H](C(F)(F)F)CO2)cc2c1[C@@H](c1cc(F)ccc1Cl)NC2=O)c1cc(F)cc(C(F)(F)F)c1] | Fc1ccc(C1)c(c1)[C@H]1NC(=O)c2cc(cc(NC(=O)c3cc(F)cc(c3)C(F)(F)F)c12)\N=C1\N[C@@H](CO1)C(F)(F)F | | 619.0 | D | |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-2390 | 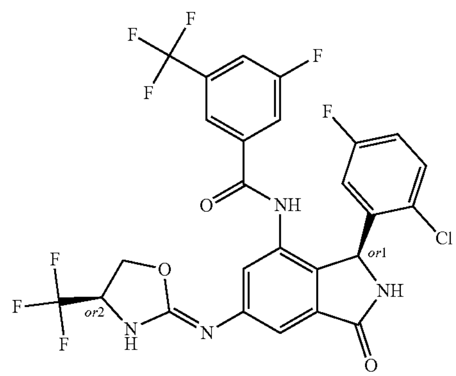 [SMILES: O=C(Nc1cc(/N=C2/N[C@@H](C(F)(F)F)CO2)cc2c1[C@@H](c1cc(F)ccc1Cl)NC2=O)c1cc(F)cc(C(F)(F)F)c1] | Fc1ccc(C1)c(c1)[C@H]1NC(=O)c2cc(cc(NC(=O)c3cc(F)cc(c3)C(F)(F)F)c12)\N=C1\N[C@H](CO1)C(F)(F)F | | 619.0 | D | |
| I-2391 | 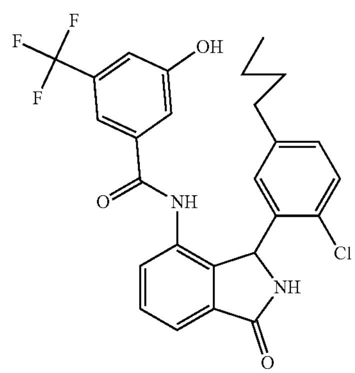 [SMILES: CCCCc1ccc(Cl)c(C2NC(=O)c3cccc(NC(=O)c4cc(O)cc(C(F)(F)F)c4)c32)c1] | CCCCc1ccc(Cl)c(c1)C1NC(=O)c2cc cc(NC(=O)c3cc(O)cc(c3)C(F)(F)F)c12 | (400 MHz, DMSO) δ 10.81 (s, 1H), 10.26 (s, 1H), 8.99 (s, 1H), 8.49 (s, 1H), 7.66-7.61 (m, 1H), 7.57 (t, J = 7.6 Hz, 1H), 7.44 (s, 1H), 7.27 (s, 1H), 7.15 (d, J = 8.2 Hz, 2H), 7.08 (s, 1H), 7.00 (dd, J = 8.2, 2.2 Hz, 1H), 6.78 (s, 1H), 5.96 (s, 1H), 2.18 (s, 2H), 1.12-1.06 (m, 4H), 0.77-0.69 (m, 2H). | 503.0 | D | |
| I-2392 | 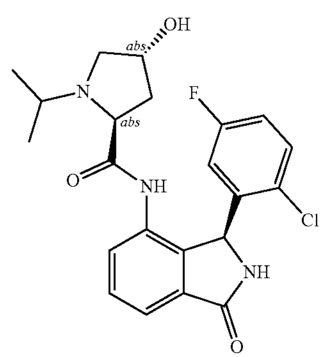 [SMILES: CC(C)N1C[C@H](O)C[C@H]1C(=O)Nc1cccc2c1[C@@H](c1cc(F)ccc1Cl)NC2=O] | CC(C)N1C[C@H](O)C[C@H]1C(=O)Nc1cccc2C(=O)NC(c12)c1cc(F)ccc1Cl | (400 MHz, DMSO-d6) δ 9.23 (br. s, 1H), 9.16 (br. s, 1H), 8.07 (dd, J = 7.5, 1.4 Hz, 0.6H), 7.91 (dd, J = 7.1, 1.8 Hz, 0.3H), 7.69-7.43 (m, 3H), 7.33-7.29 (m, 0.6H), 7.29-7.25 (m, 0.4H), 6.42 (br. s, 1H), 6.14 (br. s, 1H), 4.84 (br. s, 1H), 4.01-3.93 (m, 0.3H), 3.70-3.61 (m, 0.7H), 3.28 (overlapping dd, J = 5.8, 3.7 Hz, 1H), 3.03 (dd, J = 9.3, 5.3 Hz, 0.3H), 2.83 (dd, J = 9.4, 5.2 Hz, 0.7H), 2.43 (td, J = 12.9, 6.4 Hz, 1H), 2.37-2.24 (m, 1H), 1.88-1.79 (m, 0.3H), 1.80-1.68 (m, 0.7H), 1.65-1.48 (m, 0.3H), 1.33 (dt, J = 15.8, 4.8 Hz, 0.7H), 0.89 (overlapping d, J = 5.0 Hz, 4H), 0.71 (d, J = 6.4 Hz, 1H), 0.68 (d, J = 6.3 Hz, 1H); 2:1 mixture of diastereomers | 432.3 | E | |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-2393 | 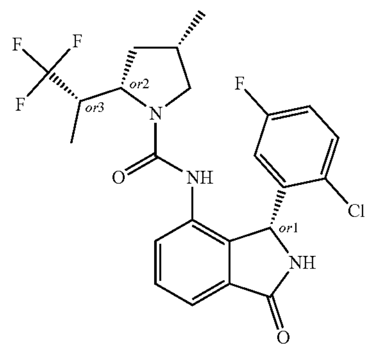 [SMILES: C[C@H]1C[C@@H]([C@H](C)C(F)(F)F)N(C(=O)Nc2cccc3c2[C@H](c2cc(F)ccc2Cl)NC3=O)C1] | C[C@@H]([C@@H]1C[C@H](O)CN1C(=O)Nc1ccc2C(=O)N[C@H](c12)c1cc(F)ccc1Cl)C(F)(F)F | (400 MHz, CD3CN) δ 7.65-7.45 (m, 3H), 7.45-7.38 (m, 1H), 7.18-7.01 (m, 2H), 6.70 (d, J = 5.1 Hz, 1H), 6.57 (br s, 1H), 6.30 (br s, 0.5H), 6.19 (br s, 0.5H), 4.38-4.22 (m, 2H), 3.26 (dd, J = 10.4, 4.2 Hz, 1H), 3.16 (dd, J = 10.3, 4.3 Hz, 1H), 2.99 (d, J = 10.3 Hz, 1H), 2.87 (d, J = 10.1 Hz, 1H), 1.82-1.74 (m, 1H), 0.82 (d, J = 7.2 Hz, 1.25H), 0.78 (d, J = 7.2 Hz, 1.75H) ppm [dr = 60:40]. | 486.3 | C | |
| I-2394 | 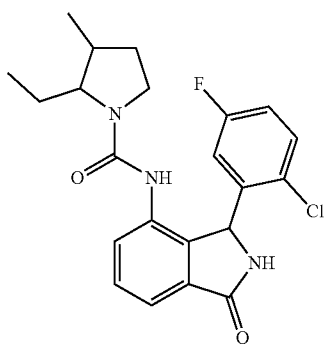 [SMILES: CCC1C(C)CCN1C(=O)Nc1cccc2c1C(c1cc(F)ccc1Cl)NC2=O] | CCC1C(C)CCN1C(=O)Nc1ccc2C(=O)NC(c12)c1cc(F)ccc1Cl | (400 MHz, DMSO-d6) as a ca. 1:1:1:1 mixture of diastereomers δ 9.00 (br. s, 4H), 8.13 (br. s, 1H), 8.08 (br. s, 1H), 7.78 (br. s, 1H), 7.69 (br. s, 1H), 7.55-7.44 (m, 14H), 7.30-7.18 (m, 6H), 6.59 (br. s, 4H), 6.13 (br. s, 2H), 6.06 (br. s, 1H), 6.02 (br. s, 1H), 3.83 (app. q, J = 6.8 Hz, 1H), 3.51 (dd, J = 12.2, 6.3 Hz, 1H), 3.32-3.28 (m, 1H), 3.28-3.01 (m, 6H), 3.00-2.92 (m, 1H), 2.45 2.35 (m, 1H), 2.13 1.68 (m, 8H), 1.65 1.56 (m, 1H), 1.56-1.13 (m, 12H), 0.97-0.91 (m, 9H), 0.82 (d, J = 6.8 Hz, 3H), 0.79-0.67 (m, 12H). | 416.4 | D | |
| I-2395 | 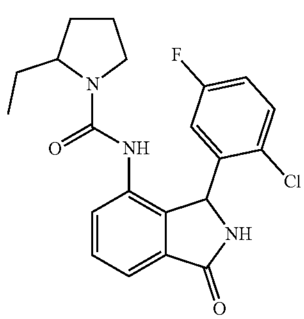 [SMILES: CCC1CCCN1C(=O)Nc1cccc2c1C(c1cc(F)ccc1Cl)NC2=O] | CCC1CCCN1C(=O)Nc1ccc2C(=O)NC(c12)c1cc(F)ccc1Cl | (400 MHz, DMSO-d6) as a ca. 1:1 mixture of diastereomers δ 9.00 (br. s, 2H), 8.13 (s, 1H), 7.79 (s, 1H), 7.51-7.44 (m, 7H), 7.26-7.18 (m, 3H), 6.58 (br. s, 2H), 6.08 (br. s, 1H), 6.01 (br. s, 1H), 3.80-3.73 (m, 1H), 3.48-3.38 (m, 1H), 3.23-3.16 (m, 1H), 3.12 (dd, J = 16.5, 8.0 Hz, 1H), 3.00-2.93 (m, 1H), 2.60-2.52 (m, 1H), 1.79-1.54 (m, 10H), 1.15-1.00 (m, 2H), 0.75 (t, J = 6.8 Hz, 3H), 0.72 (t, J = 6.7 Hz, 3H). | 402.4 | D | |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-2396 | 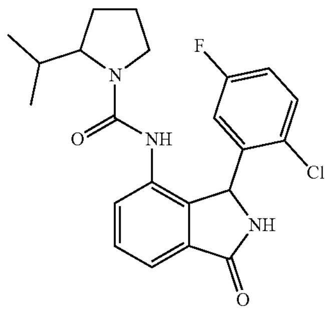 [SMILES: CC(C)C1CCCN1C(=O)Nc1cccc2c1C(c1cc(F)ccc1Cl)NC2=O] | CC(C)C1 CCCN1C (=O)Nc1 cccc2C(= O)NC(c1 2)c1cc(F) ccc1Cl | (400 MHz, DMSO-d6) as a ca. 1:1 mixture of diastereomers, δ 9.01 (br. s, 2H), 8.19 (s, 1H), 7.80 (s, 1H), 7.57-7.46 (m, 7H), 7.27-7.18 (m, 3H), 6.54 (br. s, 2H); 6.16 (br. s, 1H), 6.00 (br. s, 1H), 3.81 (dd, J = 11.5, 5.6 Hz, 1H), 3.54-3.49 (m, 1H), 3.21-3.11 (m, 2H), 3.03 (ddd, J = 10.1, 7.6, 4.6 Hz, 1H), 2.06-1.96 (m, 1H), 1.90-1.79 (m, 1H), 1.77-1.49 (m, 9H), 0.79-0.73 (m, 6H), 0.67 (d, J = 6.8 Hz, 3H), 0.62 (d, J = 6.8 Hz, 3H). | 416.4 | D | |
| I-2397 | 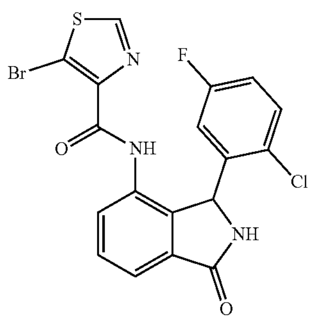 [SMILES: O=C1NC(c2cc(F)ccc2Cl)c2c(NC(=O)c3ncsc3Br)cccc21] | Fc1ccc(C 1)c(c1)C1 NC(=O)c 2cccc(N C(=O)c3 ncsc3Br) c12 | (400 MHz, DMSO-d6) δ 9.97 (br s, 1H), 9.12 (s, 1H), 9.10 (submerged br s, 1H), 7.72 (dd, J = 7.3, 0.6 Hz, 1H), 7.67-7.50 (m, 2H), 7.35 (dd, J = 8.3, 5.1 Hz, 1H), 7.11 (td, J = 8.5, 3.0 Hz, 1H), 6.68 (br s, 1H), 6.10 (br s, 1H). | 466.0 | D | |
| I-2398 | 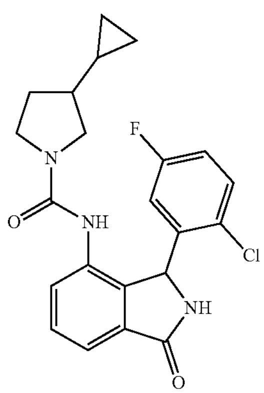 [SMILES: O=C1NC(c2cc(F)ccc2Cl)c2c(NC(=O)N3CCC(C4CC4)C3)cccc21] | Fc1ccc(C 1)c(c1)C1 NC(=O)c 2cccc(N C(=O)N3 CCC(C3) C3CC3)c 12 | (400 MHz, DMSO-d6) δ 9.00 (br s, 1H), 8.10 (s, 0.5H), 8.04 (s, 0.5H), 7.55-7.40 (m, 3H), 7.33-7.26 (m, 1H), 7.26-7.19 (m, 1H), 6.58 (br s, 1H), 5.99 (br s, 1H), 3.22-3.11 (overlapping m, 1H), 3.10-2.65 (submerged m, 2H), 2.94-2.84 (overlapping m, 1H), 1.94-1.73 (m, 1H), 1.58-1.29 (m, 2H), 0.68-0.51 (m, 1H), 0.47-0.33 (m, 2H), 0.22-0.02 (m, 2H). | 414.0 | E | |
| I-2399 | 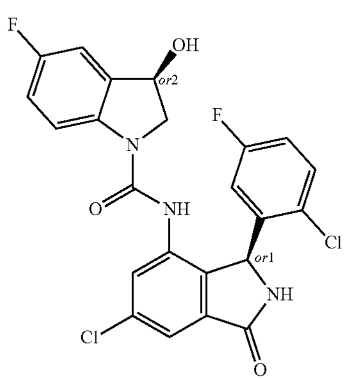 [SMILES: O=C1N[C@H](c2cc(F)ccc2Cl)c2c(NC(=O)N3C[C@H](O)c4cc(F)ccc43)cc(Cl)cc21] | O[C@H] 1CN(C(= O)Nc2cc (Cl)cc3C (=O)N[C @@H](c 23)c2cc (F)ccc2Cl) c2ccc(F) cc12 | (400 MHz, DMSO-d6) δ9.23 (s, 1H), 8.61 (s, 1H), 7.70 (dd, J = 8.9, 4.7 Hz, 1H), 7.56 (d, J = 11.8 Hz, 2H), 7.36 (dd, J = 8.9, 5.1 Hz, 1H), 7.08 (dtd, J = 26.7, 9.0, 8.6, 2.9 Hz, 3H), 6.61 (s, 1H), 6.08 (s, 1H), 5.88-5.64 (m, 1H), 5.34-4.92 (m, 1H), 3.91 (dd, J = 11.0, 8.1 Hz, 1H), 3.24 (dd, J = 11.1, 3.9 Hz, 1H). | 490.0 | D | |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-2400 | 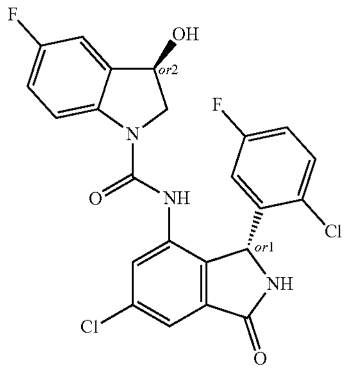 [SMILES: O=C1N[C@@H](c2cc(F)ccc2Cl)c2c(NC(=O)N3C[C@H](O)c4cc(F)ccc43)cc(Cl)cc21] | O[C@H]1CN(C(=O)Nc2cc(Cl)cc3C(=O)N[C@H](c23)c2cc(F)ccc2Cl)c2ccc(F)cc12 | (400 MHz, DMSO-d6) δ9.23 (s, 1H), 8.61 (s, 1H), 7.70 (dd, J = 8.9, 4.7 Hz, 1H), 7.56 (d, J = 11.8 Hz, 2H), 7.36 (dd, J = 8.9, 5.1 Hz, 1H), 7.08 (dtd, J = 26.7, 9.0, 8.6, 2.9 Hz, 3H), 6.61 (s, 1H), 6.08 (s, 1H), 5.88-5.64 (m, 1H), 5.34-4.92 (m, 1H), 3.91 (dd, J = 11.0, 8.1 Hz, 1H), 3.24 (dd, J = 11.1, 3.9 Hz, 1H). | 490.0 | B | |
| I-2401 | 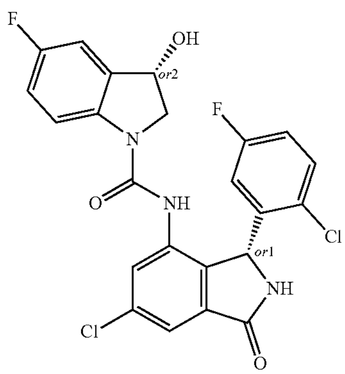 [SMILES: O=C1N[C@@H](c2cc(F)ccc2Cl)c2c(NC(=O)N3C[C@@H](O)c4cc(F)ccc43)cc(Cl)cc21] | O[C@@H]1CN(C(=O)Nc2cc(Cl)cc3C(=O)N[C@H](c23)c2cc(F)ccc2Cl)c2ccc(F)cc12 | (400 MHz, DMSO-d6) δ9.23 (s, 1H), 8.61 (s, 1H), 7.70 (dd, J = 8.9, 4.7 Hz, 1H), 7.56 (d, J = 11.8 Hz, 2H), 7.36 (dd, J = 8.9, 5.1 Hz, 1H), 7.08 (dtd, J = 26.7, 9.0, 8.6, 2.9 Hz, 3H), 6.61 (s, 1H), 6.08 (s, 1H), 5.88-5.64 (m, 1H), 5.34-4.92 (m, 1H), 3.91 (dd, J = 11.0, 8.1 Hz, 1H), 3.24 (dd, J = 11.1, 3.9 Hz, 1H). | 490.0 | E | |
| I-2402 | 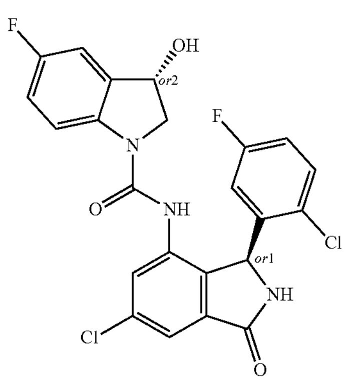 [SMILES: O=C1N[C@H](c2cc(F)ccc2Cl)c2c(NC(=O)N3C[C@@H](O)c4cc(F)ccc43)cc(Cl)cc21] | O[C@@H]1CN(C(=O)Nc2cc(Cl)cc3C(=O)N[C@@H](c23)c2cc(F)ccc2Cl)c2ccc(F)cc12 | (400 MHz, DMSO-d6) δ9.23 (s, 1H), 8.61 (s, 1H), 7.70 (dd, J = 8.9, 4.7 Hz, 1H), 7.56 (d, J = 11.8 Hz, 2H), 7.36 (dd, J = 8.9, 5.1 Hz, 1H), 7.08 (dtd, J = 26.7, 9.0, 8.6, 2.9 Hz, 3H), 6.61 (s, 1H), 6.08 (s, 1H), 5.88-5.64 (m, 1H), 5.34-4.92 (m, 1H), 3.91 (dd, J = 11.0, 8.1 Hz, 1H), 3.24 (dd, J = 11.1, 3.9 Hz, 1H). | 487.9 | A | A |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-2403 | 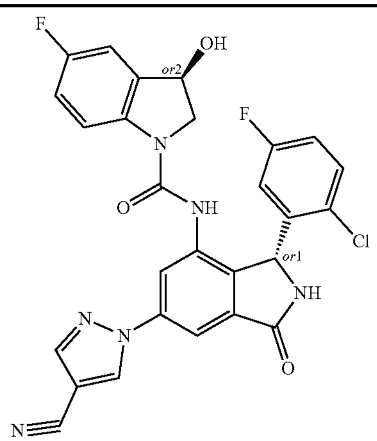 | O[C@H]1CN(C(=O)Nc2cc(cc3C(=O)N[C@H](c23)c2cc(F)ccc2Cl)-n2cc(cn2)C#N)c2ccc(F)cc12 | (400 MHz, DMSO-d6) 9.54 (s, 1H), 9.26 (s, 1H), 8.93 (s, 1H), 8.46 (d, J = 24.6 Hz, 1H), 8.29-7.70 (m, 3H), 7.45 (d, J = 23.9 Hz, 1H), 7.25-7.01 (m, 3H), 6.97-6.45 (s, 1H), 6.08 (s, 1H), 5.79 (s, 1H), 5.07 (s, 1H), 3.72 (d, J = 9.9 Hz, 1H), 3.42 (s, 1H). | 547.1 | A | B |
| I-2404 | 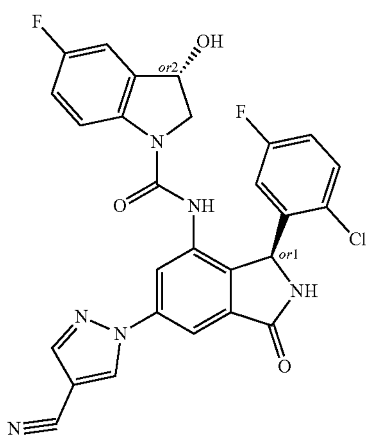 [SMILES: N#Cc1cnn(-c2cc(NC(=O)N3C[C@@H](O)c4cc(F)ccc43)c3c(c2)C(=O)N[C@@H]3c2cc(F)ccc2Cl)c1] | O[C@@H]1CN(C(=O)Nc2cc(cc3C(=O)N[C@@H](c23)c2cc(F)ccc2Cl)-n2cc(cn2)C#N)c2ccc(F)cc12 | (400 MHz, DMSO-d6) 9.54 (s, 1H), 9.29 (s, 1H), 8.86 (d, J = 63.1 Hz, 1H), 8.43 (s, 1H), 8.26-7.79 (m, 2H), 7.74 (dd, J = 8.8, 4.7 Hz, 1H), 7.38 (dt, J = 9.1, 4.7 Hz, 1H), 7.21-7.10 (m, 2H), 7.10-6.95 (s, 1H), 6.93-6.36 (m, 1H), 6.15 (s, 1H), 5.77 (s, 1H), 5.23-5.00 (m, 1H), 3.97 (dd, J = 11.0, 8.1 Hz, 1H), 3.26-3.16 (m, 1H). | 547.2 | B | |
| I-2405 | 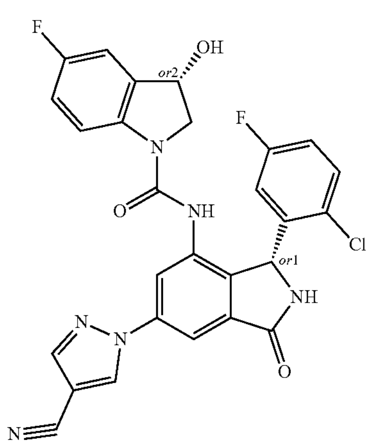 [SMILES: N#Cc1cnn(-c2cc(NC(=O)N3C[C@@H](O)c4cc(F)ccc43)c3c(c2)C(=O)N[C@H]3c2cc(F)ccc2Cl)c1] | O[C@@H]1CN(C(=O)Nc2cc(cc3C(=O)N[C@H](c23)c2cc(F)ccc2Cl)-n2cc(cn2)C#N)c2ccc(F)cc12 | (400 MHz, DMSO-d6) 9.54 (s, 1H), 9.29 (s, 1H), 8.86 (d, J = 63.1 Hz, 1H), 8.43 (s, 1H), 8.11-7.94 (m, 2H), 7.74 (dd, J = 8.8, 4.7 Hz, 1H), 7.38 (dt, J = 9.1, 4.7 Hz, 1H), 7.21-6.93 (m, 3H), 6.93-6.36 (m, 1H), 6.15 (s, 1H), 5.77 (s, 1H), 5.23-5.00 (m, 1H), 3.97 (dd, J = 11.0, 8.1 Hz, 1H), 3.26-3.16 (m, 1H). | 547.2 | A | |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-2406 | 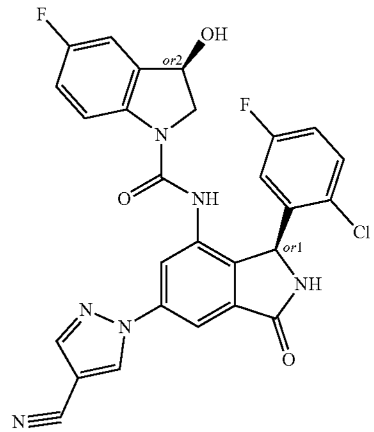 [SMILES: N#Cc1cnn(-c2cc(NC(=O)N3C[C@H](O)c4cc(F)ccc43)c3c(c2)C(=O)N[C@@H]3c2cc(F)ccc2Cl)c1] | O[C@H]1CN(C(=O)Nc2cc(cc3C(=O)N[C@@H](c23)c2cc(F)ccc2Cl)-n2cc(cn2)C#N)c2ccc(F)cc12 | (400 MHz, DMSO-d6) 9.54 (s, 1H), 9.26 (s, 1H), 8.93 (s, 1H), 8.46 (d, J = 24.6 Hz, 1H), 8.02 (d, J = 23.9 Hz, 2H), 7.86 (s, 1H), 7.39 (dd, J = 8.9, 5.1 Hz, 1H), 7.24-7.02 (m, 3H), 6.98-6.37 (m, 1H), 6.08 (s, 1H), 5.79 (s, 1H), 5.07 (s, 1H), 3.72 (d, J = 9.9 Hz, 1H), 3.17 (d, J = 4.5 Hz, 1H) | 547.1 | D | |
| I-2407 | 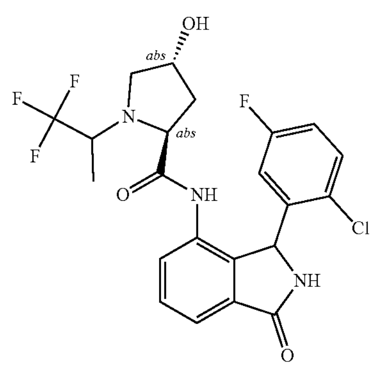 [SMILES: CC(N1C[C@H](O)C[C@H]1C(=O)Nc1cccc2c1C(c1cc(F)ccc1Cl)NC2=O)C(F)(F)F] | CC(N1C[C@H](O)C[C@H]1C(=O)Nc1cccc2C(=O)NC(c12)c1cc(F)ccc1Cl)C(F)(F)F | (400 MHz, DMSO-d6) δ 9.29 (br. s, 1H), 9.16 (br. s, 0.3H), 9.15 (br. s, 0.6H), 9.11 (br. s, 0.3H), 7.95-7.80 (m, 0.2H), 7.83-7.68 (m, 0.8H), 7.67-7.39 (m, 3H), 7.35-7.09 (m, 1H), 6.71 (br. s, 0.3H), 6.38 (br. s, 0.7H), 6.15 (br. s, 0.3H), 6.08 (br. s, 0.7H), 4.88 (br. s, 1H), 4.14-3.78 (m, 1H), 3.79-3.53 (m, 1H), 3.55-3.40 (m, 0.2H), 3.28-3.07 (m, 1H), 3.08-2.91 (m, 0.8H), 2.93-2.82 (m, 0.2H), 2.71-2.59 (m, 0.2H), 2.60-2.52 (m, 0.8H), 1.86-1.64 (m, 1H), 1.50-1.26 (m, 1H), 1.15 (d, J = 7.0 Hz, 0.7H), 1.08 (d, J = 7.0 Hz, 1.6H), 1.07 (d, J = 6.9 Hz, 0.2H), 1.05 (d, J = 6.8 Hz, 0.5H); 1.4:1:0.9:0.2 mixture of diastereomers according to LCMS | 486.3 | E | |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-2408 | 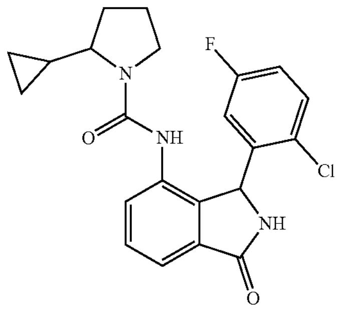 [SMILES: O=C1NC(c2cc(F)ccc2Cl)c2c(NC(=O)N3CCCC3C3CC3)cccc21] | Fc1ccc(C1)c(c1)C1NC(=O)c2cccc(NC(=O)N3CCCC3C3CC3)c12 | (400 MHz, DMSO-d6) δ 9.00 (br s, 1H), 8.18 (br s, 0.6H), 7.74 (br s, 0.4H), 7.56-7.38 (m, 3H), 7.29-7.17 (m, 2H), 6.57 (submerged br s, 1H), 6.04 (br. s, 0.6H), 5.97 (submerged br s, 0.4H), 3.64 (t, J = 7.3 Hz, 0.6H), 3.28 (dt, J = 15.1, 7.6 Hz, 1H), 3.04 (dd, J = 8.5, 5.3 Hz, 1H), 2.41-2.27 (m, 0.6H), 1.96-1.81 (m, 1H), 1.81-1.53 (m, 3.4H), 0.95-0.81 (m, 0.4H), 0.81-0.66 (m, 0.6H), 0.58-0.40 (m, 1H), 0.39-0.29 (m, 1H), 0.28-0.21 (m, 1H), 0.15-0.02 (m, 1H). Mixture 3:2 of diastereomer | 414.0 | E | |
| I-2409 | 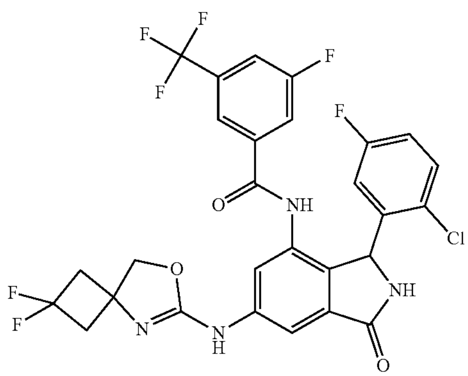 [SMILES: O=C(Nc1cc(NC2=NC3(CO2)CC(F)(F)C3)cc2c1C(c1cc(F)ccc1Cl)NC2=O)c1cc(F)cc(C(F)(F)F)c1] | FC(F)(C1=CC(F)=CC(C(NC2=C3C(NC(C3=CC(NC4=NC5(CC(F)(F)C5)CO4)=C2)=O)C6=CC(F)=CC6Cl)=O)=C1)F | (400 MHz, DMSO) δ 10.49 (s, 1H), 9.84 (s, 1H), 9.08 (s, 1H), 8.02 (s, 2H), 7.92 (d, J = 8.4 Hz, 1H), 7.72-7.61 (m, 3H), 7.58 (s, 1H), 7.28 (dd, J = 8.9, 5.1 Hz, 1H), 7.07 (td, J = 8.3, 3.0 Hz, 1H), 5.85 (s, 1H), 4.40 (s, 2H), 2.89 (dd, J = 14.3, 10.7 Hz, 5H), 2.06 (s, 2H), 1.06 (s, 1H). | 627.0 | A | C |
| I-2410 | 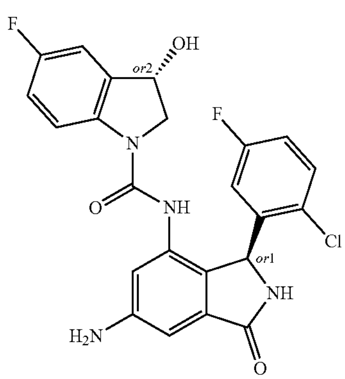 [SMILES: Nc1cc(NC(=O)N2C[C@@H](O)c3cc(F)ccc32)c2c(c1)C(=O)N[C@@H]2c1cc(F)ccc1Cl] | Nc1cc2C(=O)N[C@@H](c2c(NC(=O)N2C[C@@H](O)c3cc(F)ccc23)c1)c1cc(F)ccc1Cl | (400 MHz, DMSO-d6) 8.79 (s, 1H), 8.33 (s, 1H), 7.81 (dd, J = 8.9, 4.7 Hz, 1H), 7.33 (dd, J = 8.8, 5.2 Hz, 1H), 7.12 (ddt, J = 8.5, 5.8, 3.1 Hz, 2H), 7.06 (td, J = 9.0, 2.7 Hz, 1H), 6.74 (d, J = 2.0 Hz, 1H), 6.60 (d, J = 2.0 Hz, 1H), 6.51 (s, 1H), 5.82 (s, 1H), 5.74 (d, J = 6.0 Hz, 1H), 5.51 (s, 2H), 5.05 (s, 1H), 3.66 (dd, J = 11.4, 3.6 Hz, 1H), 3.27-3.19 (m, 1H). | 471.1 | A | A |

TABLE 2-continued

Representative Compounds of the Invention with Bioactivity Data.

| Ex. No. | Structure | SMILES | 1H NMR | MS | ADP-Glo IC50 | MCF 10A IC50 |
|---|---|---|---|---|---|---|
| I-2411 | 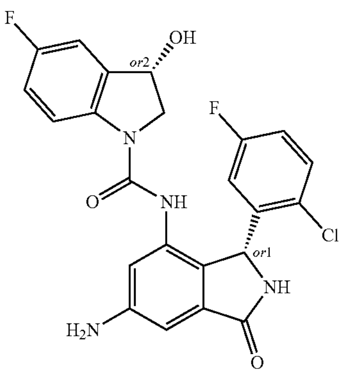 [SMILES: Nc1cc(NC(=O)N2C[C@@H](O)c3cc(F)ccc32)c2c(c1)C(=O)N[C@H]2c1cc(F)ccc1Cl] | Nc1cc2C(=O)N[C@H](c2c(NC(=O)N2C[C@@H](O)c3cc(F)ccc23)c1)c1cc(F)ccc1Cl | (400 MHz, DMSO-d6) 8.81 (s, 1H), 8.20 (s, 1H), 7.70 (dd, J = 9.1, 4.7 Hz, 1H), 7.32 (dd, J = 8.8, 5.2 Hz, 1H), 7.13-6.98 (m, 3H), 6.75 (d, J = 2.0 Hz, 1H), 6.67 (d, J = 2.0 Hz, 1H), 6.52 (s, 1H), 5.92 (s, 1H), 5.71 (d, J = 5.2 Hz, 1H), 5.51 (s, 2H), 5.13 (s, 1H), 3.96-3.87 (m, 1H), 3.23 (d, J = 8.9 Hz, 1H). | 471.1 | A | D |
| I-2412 | 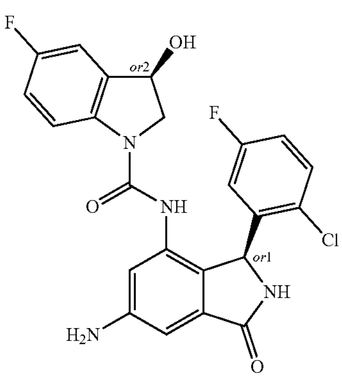 [SMILES: Nc1cc(NC(=O)N2C[C@H](O)c3cc(F)ccc32)c2c(c1)C(=O)N[C@@H]2c1cc(F)ccc1Cl] | Nc1cc2C(=O)N[C@@H](c2c(NC(=O)N2C[C@H](O)c3cc(F)cc23)c1)c1cc(F)cc1Cl | (400 MHz, DMSO-d6) 8.78 (s, 1H), 8.33 (s, 1H), 7.82 (dd, J = 8.8, 4.8 Hz, 1H), 7.34 (dd, J = 8.8, 5.2 Hz, 1H), 7.12 (ddt, J = 8.5, 5.5, 3.0 Hz, 2H), 7.06 (td, J = 9.1, 2.8 Hz, 1H), 6.74 (d, J = 2.0 Hz, 1H), 6.60 (d, J = 2.0 Hz, 1H), 6.51 (s, 1H), 5.82 (s, 1H), 5.73 (d, J = 6.0 Hz, 1H), 5.51 (s, 2H), 5.05 (s, 1H), 3.66 (dd, J = 11.3, 3.6 Hz, 1H), 3.23 (s, 1H). | 471.2 | D | |
| I-2413 | 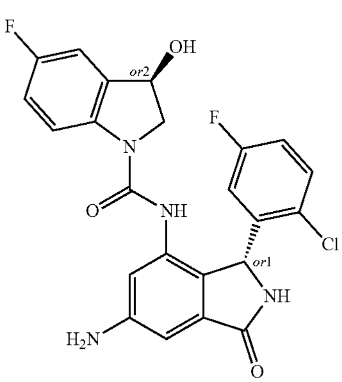 [SMILES: Nc1cc(NC(=O)N2C[C@H](O)c3cc(F)ccc32)c2c(c1)C(=O)N[C@H]2c1cc(F)ccc1Cl] | Nc1cc2C(=O)N[C@H](c2c(NC(=O)N2C[C@H](O)c3c(F)ccc23)c1)c1c(F)ccc1Cl | (400 MHz, DMSO-d6) 8.81 (s, 1H), 8.20 (s, 1H), 7.70 (dd, J = 8.9, 4.8 Hz, 1H), 7.32 (dd, J = 8.8, 5.2 Hz, 1H), 7.13-7.07 (m, 1H), 7.06 (dd, J = 8.7, 5.6 Hz, 1H), 7.06-6.97 (m, 1H), 6.75 (d, J = 2.0 Hz, 1H), 6.67 (d, J = 2.0 Hz, 1H), 6.53 (s, 1H), 5.92 (s, 1H), 5.71 (d, J = 5.1 Hz, 1H), 5.51 (s, 2H), 5.13 (dt, J = 8.7, 4.6 Hz, 1H), 3.91 (dd, J = 11.1, 8.1 Hz, 1H), 3.23 (dd, J = 11.1, 4.1 Hz, 1H). | 471.2 | E | |

TABLE 2-continued

Representative Compounds of the Invention with Bioactivity Data.

| Ex. No. | Structure | SMILES | $^1$H NMR | MS | ADP-Glo IC$_{50}$ | MCF 10A IC$_{50}$ |
|---|---|---|---|---|---|---|
| I-2414 | 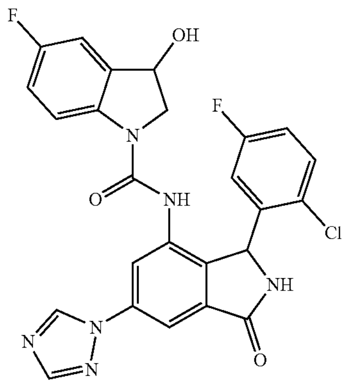 [SMILES: O=C1NC(c2cc(F)ccc2Cl)c2c(NC(=O)N3CC(O)c4cc(F)ccc43)cc(-n3cncn3)cc21] | OC1CN(C(=O)Nc2cc(cc3C(=O)NC(c23)c2cc(F)ccc2C1)-n2cncn2)c2ccc(F)cc12 | (400 MHz, DMSO-d6) δ 9.51 (br s, 1 H), 9.28 (br s, 1 H), 8.94 (br s, 0.5 H), 8.79 (s, 0.5 H), 8.30 (s, 0.5 H), 8.30 (s, 0.5 H), 8.12-8.09 (m, 1 H), 8.03 (d, J = 1.8 Hz, 0.5 H), 7.96 (d, J = 1.6 Hz, 0.5 H), 7.85 (dd, J = 8.0, 4.4 Hz, 0.5 H), 7.73 (dd, J = 8.8, 4.7 Hz, 0.5 H), 7.41-7.33 (m, 1 H), 7.21-7.00 (m, 3 H), 6.67 (br s, 1 H), 6.14 (br s, 0.5 H), 6.06 (br s, 0.5 H), 5.15 (dd, J = 7.9, 3.9 Hz, 0.5 H), 5.07 (dd, J = 7.7, 3.2 Hz, 0.5 H), 3.98 (dd, J = 10.9, 8.2 Hz, 0.5 H), 3.72 (dd, J = 11.3, 3.4 Hz, 0.5 H), 3.21 (dd, J = 11.0, 3.8 Hz, 0.5 H). 0.5 H submerged under water signal. ~1:1 mixture of diastereomers. | 523.3 | B | D |
| I-2415 | 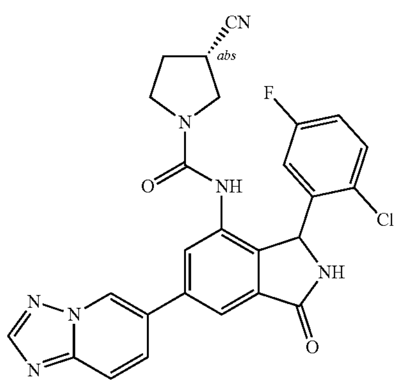 [SMILES: N#C[C@H]1CCN(C(=O)Nc2cc(-c3ccc4ncnn4c3)cc3c2C(c2cc(F)ccc2Cl)NC3=O)C1] | Fc1ccc(C1)c(c1)C1NC(=O)c2cc(cc(NC(=O)N3cc[C@@H](C3)C#N)c12)-c1ccc2ncnn2c1 | (400 MHz, DMSO-d6) δ 9.39 (br s, 1H), 9.17 (br s, 1H), 8.56 (s, 1H), 8.44 (d, J = 7.6 Hz, 1H), 8.06 (dt, J = 9.3, 1.6 Hz, 1H), 7.97 (d, J = 9.2 Hz, 1H), 7.93 (s, 1H), 7.70 (dd, J = 2.4, 1.8 Hz, 1H), 7.51 (br s, 1H), 7.28-7.20 (m, 1H), 6.70 (br s, 1H), 6.07 (br s, 1H), 3.58 (dd, J = 10.6, 7.1 Hz, 1H), 3.47-3.36 (m, 4H[submerged under H2O peak]), 2.24-1.95 (m, 2H) ppm [1:1 mixture of diastereomers]. | 516.4 | E | |
| I-2416 | 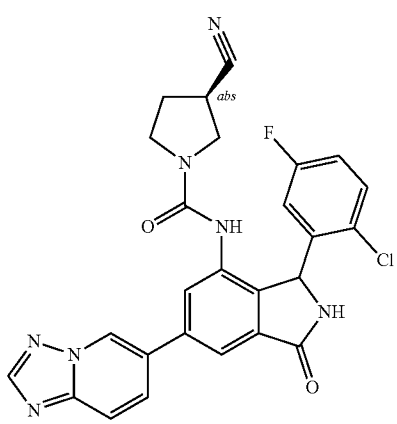 [SMILES: N#C[C@@H]1CCN(C(=O)Nc2cc(-c3ccc4ncnn4c3)cc3c2C(c2cc(F)ccc2Cl)NC3=O)C1] | Fc1ccc(C1)c(c1)C1NC(=O)c2cc(cc(NC(=O)N3CC[C@H](C3)C#N)c12)-c1ccc2ncnn2c1 | (400 MHz, DMSO-d6) δ 9.39 (br s, 1H), 9.17 (br s, 1H), 8.56 (s, 1H), 8.44 (d, J = 7.6 Hz, 1H), 8.06 (dt, J = 9.3, 1.6 Hz, 1H), 7.97 (d, J = 9.2 Hz, 1H), 7.93 (s, 1H), 7.70 (dd, J =2.4, 1.8 Hz, 1H), 7.51 (br s, 1H), 7.28-7.20 (m, 1H), 6.70 (br s, 1H), 6.07 (br s, 1H), 3.58 (dd, J = 10.6, 7.1 Hz, 1H), 3.47-3.36 (m, 4H[submerged under H2O peak]), 2.24-1.95 (m, 2H) ppm [1:1 mixture of diastereomers]. | 516.4 | E | |

TABLE 2-continued

Representative Compounds of the Invention with Bioactivity Data.

| Ex. No. | Structure | SMILES | $^1$H NMR | MS | ADP-Glo IC$_{50}$ | MCF 10A IC$_{50}$ |
|---|---|---|---|---|---|---|
| I-2417 | 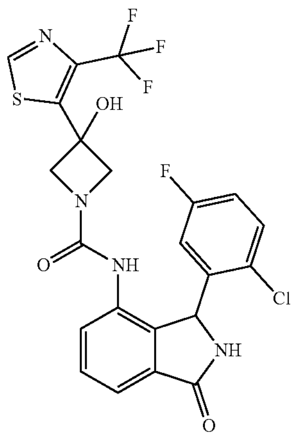 [SMILES: O=C1NC(c2cc(F)ccc2Cl)c2c(NC(=O)N3CC(O)(c4scnc4C(F)(F)F)C3)cccc21] | OC1(CN (C1)C(= O)Nc1cc cc2C(=O) NC(c12) c1cc(F)c cc1Cl)c1 scnc1C(F) (F)F | (400 MHz, DMSO-d6) δ 9.20 (m, 1H), 9.03 (br s, 1H), 8.51 (br s, 1H), 7.60-7.48 (m, 2H), 7.43-7.32 (m, 1H), 7.18 (dd, J = 8.3, 5.5 Hz, 1H), 6.99 (td, J = 8.4, 2.9 Hz, 1H), 6.90 (br s, 1H), 6.47 (br s, 1H), 6.03 (br s, 1H), 4.10 (d, J = 9.0 Hz, 1H), 4.03 (d, J = 9.1 Hz, 1H), 3.87 (d, J = 9.1 Hz, 1H), 3.66 (d, J = 10.5 Hz, 1H). | 527.0 | E | |
| I-2418 | 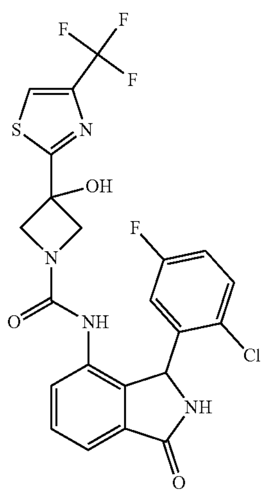 [SMILES: O=C1NC(c2cc(F)ccc2Cl)c2c(NC(=O)N3CC(O)(c4nc(C(F)(F)F)cs4)C3)cccc21] | OC1(CN (C1)C(= O)Nc1cc cc2C(=O) NC(c12) c1cc(F)c cc1Cl)c1 nc(cs1)C (F)(F)F | (400 MHz, DMSO-d6) δ 9.05 (br s, 1H), 8.51 (d, J = 0.9 Hz, 1H), 8.39 (br s, 1H), 7.56-7.50 (m, 2H), 7.50-7.42 (m, 2H), 7.39 (br s, 1H), 7.16 (ddd, J = 8.9, 8.0, 3.1 Hz, 1H), 6.57 (br s, 1H), 6.09 (br s, 1H), 4.11 (d, J = 8.5 Hz, 1H), 3.99 (d, J = 8.5 Hz, 1H), 3.92 (d, J = 8.5 Hz, 1H), 3.70 (d, J = 8.7 Hz, 1H). | 527.0 | | |
| I-2419 | 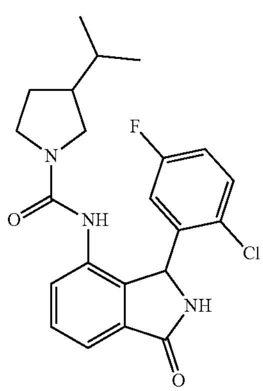 [SMILES: CC(C)C1CCN(C(=O)Nc2cccc3c2C(c2cc(F)ccc2Cl)NC3=O)C1] | CC(C)C1 CCN(C1) C(=O)Nc 1cccc2C (=O)NC(c 12)c1cc (F)ccc1Cl | (400 MHz, DMSO-d6) δ 9.00 (br s, 1H), 8.12 (s, 0.5H), 8.02 (s, 0.5H), 7.65-7.36 (m, 3H), 7.43-7.15 (m, 2H), 6.56 (br s, 1H), 5.97 (br s, 1H), 3.61-3.38 (submerged m, 2H), 3.23-3.02 (m, 1H), 2.84-2.64 (m, 1H), 1.88 (td, J = 12.2, 6.3 Hz, 1H), 1.77-1.51 (m, 1H), 1.47-1.16 (m, 2H), 0.89 (dd, J = 6.6, 1.6 Hz, 3H), 0.84 (d, J = 6.5 Hz, 3H). Partial formate salt @8.22 ppm. 1:1 Mixture of diastereomers | 416.0 | E | |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-2420 | 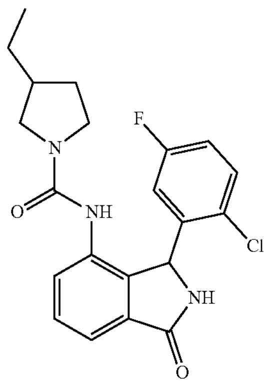 [SMILES: CCC1CCN(C(=O)Nc2cccc3c2C(c2cc(F)ccc2Cl)NC3=O)C1] | CCC1CCN(C1)C(=O)Nc1cccc2C(=O)NC(c2)c1cc(F)ccc1Cl | (400 MHz, DMSO-d6) δ 9.00 (br s, 1H), 8.09 (s, 0.5H), 8.03 (s, 0.5H), 7.55-7.42 (m, 3H), 7.35-7.17 (m, 2H), 6.55 (br s, 1H), 5.98 (br s, 1H), 3.58-3.35 (submerged m, 2H), 3.26-3.08 (m, 1H), 2.82-2.64 (m, 1H), 2.02-1.78 (m, 2H), 1.44-1.10 (m, 3H), 0.95-0.80 (m, 3H). Partial formate salt @8.23 ppm. 1:1 Mix of diastereomers. | 402.0 | E | |
| I-2421 | 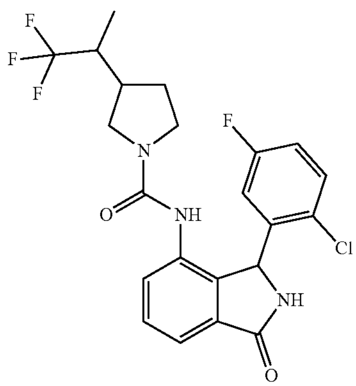 [SMILES: CC(C1CCN(C(=O)Nc2cccc3c2C(c2cc(F)ccc2Cl)NC3=O)C1)C(F)(F)F] | CC(C1CCN(C1)C(=O)Nc1cccc2C(=O)NC(c2)c1cc(F)ccc1Cl)C(F)(F)F | (400 MHz, DMS)-d6) δ 9.01 (br. s, 1H), 8.26 (br. s, 0.2H), 8.24 (br. s, 0.3H), 8.14 (br. s, 0.3H), 8.11 (br. s, 0.2H), 7.54-7.42 (m, 3H), 7.33-7.15 (m, 2H), 6.59 (br. s, 1H), 5.97 (br. s, 1H), 3.69-3.53 (m, 1H), 3.53-3.39 (m, 1H), 3.24-3.04 (m, 1H), 2.99-2.88 (m, 1H), 2.47-2.24 (m, 1H), 2.24-1.99 (m, 1H), 2.02-1.81 (m, 1H), 1.67-1.30 (m, 1H), 1.10 (d, J = 6.9 Hz, 0.8H), 1.09 (d, J = 6.9 Hz, 0.8H), 1.03 (d, J = 6.7 Hz, 0.7H), 1.02 (d, J = 6.7 Hz, 0.7H); ~1.3:1.2:1:1 mixture of diastereomers; contains ~5% formate salt-due to peak at 8.25 ppm | 470.2 | E | |
| I-2422 | 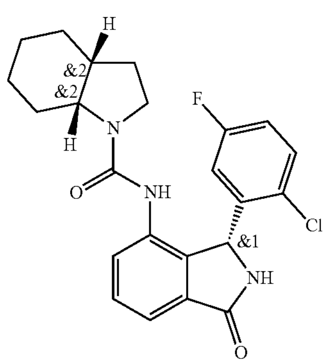 [SMILES: O=C1N[C@@H](c2cc(F)ccc2Cl)c2c(NC(=O)N3CC[C@H]4CCCC[C@H]43)cccc21] | [H][C@@]12CCN(C(=O)Nc3cccc4C(=O)NC(c34)c3cc(F)ccc3Cl)[C@]1([H])CCCC2 | (400 MHz, DMSO-d6) δ as a ca. 1:1 mixture of diastereomers, δ 8.99 (br. s, 2H), 8.04 (br. s, 1H), 7:78 (br. s, 1H), 7.52-7.40 (m, 7H), 7.27-7.17 (m, 3H), 6.60 (br. s, 2H), 6.05 (br. s, 2H), 3.77-3.68 (m, 1H), 3.39-3.28 (m, 1H), 3.21 (dd, J = 17.4, 9.1 Hz, 1H), 3.05-2.95 (m, 1H), 2.15-1.97 (m, 2H), 1.90-1.72 (m, 3H), 1.71-1.47 (m, 8H), 1.44-1.32 (m, 4H), 1.32-1.17 (m, 3H), 1.12-0.87 (m, 4H). Multiplet at 3.39-3.28 ppm is obscured by the peak for residual H2O. | 428.4 | D | |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-2423 | 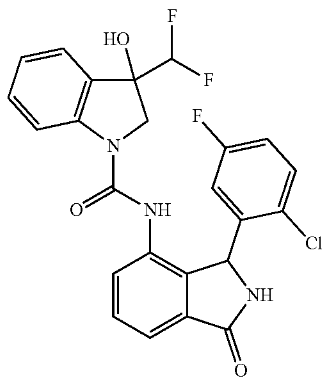 [SMILES: O=C1NC(c2cc(F)ccc2Cl)c2c(NC(=O)N3CC(O)(C(F)F)c4ccccc43)cccc21] | OC1(CN(C(=O)Nc2cccc3Cc(=O)NC(c23)c2cc(F)ccc2Cl)c2ccccc12)C(F)F | (400 MHz, DMSO-d6) δ as a ca. 1:1 mixture of diastereomers δ 9.11-9.04 (m, 2H), 8.72 (br. s, 1H), 8.62 (br. s, 1H), 7.86 (br. d, J = 8.1 Hz, 1H), 7.78 (d, J = 8.3 Hz, 1H), 7.62-7.54 (m, 4H), 7.48 (dd, J = 7.3, 1.7 Hz, 1H), 7.42-7.37 (m, 3H), 7.37-7.26 (m, 4H), 7.14-7.08 (m, 2H), 7.01 (tdd, J = 7.5, 5.0, 0.9 Hz, 2H), 6.55 (s, 1H), 6.63-6.43 (m, 2H), 6.49 (s, 1H), 6.38-6.07 (m, 2H), 6.11 (br. s, 1H), 6.05 (br. s, 1H), 4.06 (d, J = 11.7 Hz, 1H), 3.82 (br. d, J = 12.2 Hz, 1H), 3.45 (br. d, J = 11.3 Hz, 1H), 3.33-3.30 (m, 1H). Multiplet at 3.33-3.30 ppm is partially obscured by the peak for residual H2O. | 488.3 | A | B |
| I-2424 | 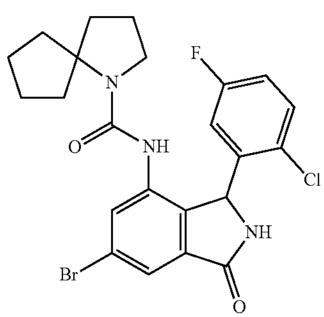 [SMILES: O=C1NC(c2cc(F)ccc2Cl)c2c(NC(=O)N3CCCC34CCCC4)cc(Br)cc21] | Fc1ccc(C1)c(c1)C1NC(=O)c2cc(Br)cc(NC(=O)N3CCCC33CCCC3)c12 | | 98.0 | C | |
| I-2425 | 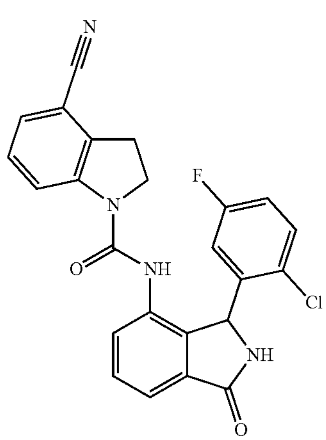 [SMILES: N#Cc1cccc2c1CCN2C(=O)Nc1cccc2c1C(c1cc(F)ccc1Cl)NC2=O] | Fc1ccc(C1)c(c1)C1NC(=O)c2cccc(NC(=O)N3CCc4c3cccc4C#N)c12 | | 447.1 | E | |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-2426 | 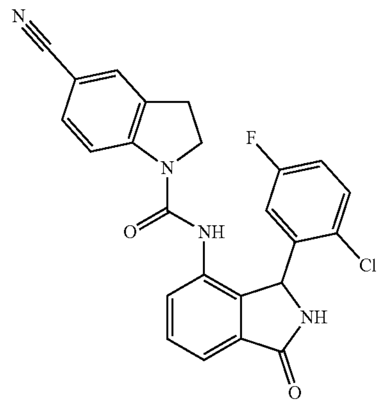 [SMILES: N#Cc1ccc2c(c1)CCN2C(=O)Nc1cccc2c1C(c1cc(F)ccc1Cl)NC2=O] | Fc1ccc(C1)c(c1)C1NC(=O)c2cccc(NC(=O)N3CCc4cc(ccc34)C#N)c12 | | 446.9 | E | |
| I-2427 | 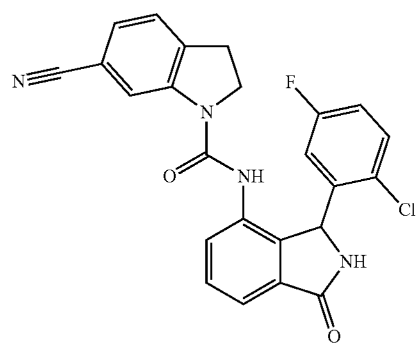 [SMILES: N#Cc1ccc2c(c1)N(C(=O)Nc1cccc3c1C(c1cc(F)ccc1Cl)NC3=O)CC2] | Fc1ccc(C1)c(c1)C1NC(=O)c2cccc(NC(=O)N3CCc4ccc(cc34)C#N)c12 | | 447.0 | D | |
| I-2428 | 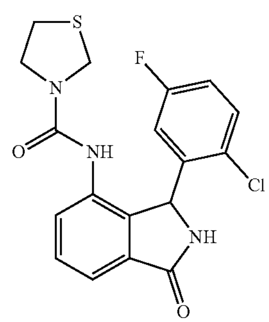 [SMILES: O=C1NC(c2cc(F)ccc2Cl)c2c(NC(=O)N3CCSC3)cccc21] | Fc1ccc(C1)c(c1)C1NC(=O)c2cccc(NC(=O)N3CCSC3)c12 | | 391.8 | E | |
| I-2429 | 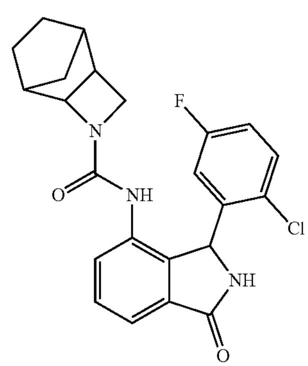 [SMILES: O=C1NC(c2cc(F)ccc2Cl)c2c(NC(=O)N3CC4C5CCC(C5)C43)cccc21] | Fc1ccc(C1)c(c1)C1NC(=O)c2cccc(NC(=O)N3CC4C3CC3CCC4C3)c12 | | 426.0 | E | |

TABLE 2-continued

Representative Compounds of the Invention with Bioactivity Data.

| Ex. No. | Structure | SMILES | $^1$H NMR | MS | ADP-Glo IC$_{50}$ | MCF 10A IC$_{50}$ |
|---|---|---|---|---|---|---|
| I-2430 | 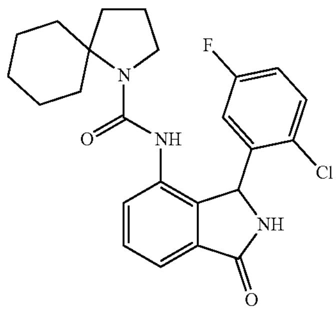 [SMILES: O=C1NC(c2cc(F)ccc2Cl)c2c(NC(=O)N3CCCC34CCCCC4)cccc21] | Fc1ccc(C1)c(c1)C1NC(=O)c2cccc(NC(=O)N3CCCC33CCCCC3)c12 | | 442.0 | C | |
| I-2431 | 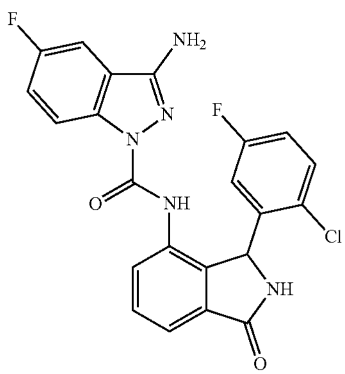 [SMILES: Nc1nn(C(=O)Nc2cccc3c2C(c2cc(F)ccc2Cl)NC3=O)c2ccc(F)cc12] | Nc1nn(C(=O)Nc2cccc3C(=O)NC(c23)c2cc(F)ccc2Cl)c2ccc(F)cc12 | | 453.9 | C | |
| I-2432 | 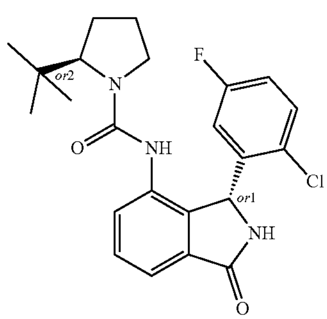 [SMILES: CC(C)(C)[C@H]1CCCN1C(=O)Nc1cccc2c1[C@H](c1cc(F)ccc1Cl)NC2=O] | CC(C)(C)[C@H]1CCCN1C(=O)Nc1cccc2C(=O)N[C@H](c12)c1cc(F)ccc1Cl | (400 MHz, DMSO-d6) as a ~19:1 mixture of diastereomers, δ 9.02 (br. s, 1H), 7.77 (br. s, 1H), 7.74 (br. d, J = 7.1 Hz, 1H), 7.54-7.47 (m, 3H), 7.23 (ddd, J = 8.8, 8.1, 3.1 Hz, 1H), 6.63 (br. s, 1H), 6.16 (br. s, 1H), 3.74-3.70 (m, 1H), 3.15-3.07 (m, 1H), 3.05-2.96 (m, 1H), 1.82-1.65 (m, 2H), 1.58-1.48 (m, 2H), 0.78 (s, 9H). | 430.4 | C | |
| I-2433 | 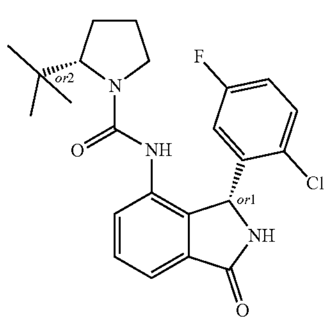 [SMILES: CC(C)(C)[C@@H]1CCCN1C(=O)Nc1cccc2c1[C@H](c1cc(F)ccc1Cl)NC2=O] | CC(C)(C)[C@@H]1CCCN1C(=O)Nc1cccc2C(=O)N[C@H](c12)c1cc(F)ccc1Cl | (400 MHz, DMSO-d6) δ as a ~19:1 mixture of diastereomers, δ 9.00 (br. s, 1H), 8.33 (br. s, 1H), 7.52-7.44 (m, 3H), 7.26-7.19 (m, 2H), 6.36 (br. s, 1H), 5.98 (br. s, 1H), 3.99 (d, J = 7.9 Hz, 1H), 3.21-3.13 (m, 1H), 2.45-2.36 (m, 1H), 1.78-1.61 (m, 3H), 1.53-1.44 (m, 1H), 0.75 (s, 9H). | 430.4 | D | |

TABLE 2-continued

Representative Compounds of the Invention with Bioactivity Data.

| Ex. No. | Structure | SMILES | $^1$H NMR | MS | ADP-Glo IC$_{50}$ | MCF 10A IC$_{50}$ |
|---|---|---|---|---|---|---|
| I-2434 | 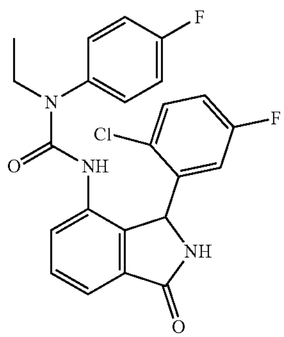 [SMILES: CCN(C(=O)Nc1cccc2c1C(c1cc(F)ccc1Cl)NC2=O)c1ccc(F)cc1] | CCN(C(=O)Nc1cccc2C(=O)NC(c12)c1cc(F)ccc1Cl)c1ccc(F)cc1 | (400 MHz, DMSO-d6) 9.05 (s, 1H), 7.73 (s, 1H), 7.61 (s, 1H), 7.53-7.43 (m, 2H), 7.35 (ddd, J = 10.9, 7.2, 2.7 Hz, 2H), 7.09 (t, J = 8.6 Hz, 2H), 6.64 (dd, J = 8.7, 5.0 Hz, 2H), 6.42 (s, 1H), 6.08 (s, 1H), 3.64 (dt, J = 14.2, 7.1 Hz, 1H), 3.42 (dq, J = 13.9, 6.9 Hz, 1H), 0.90 (t, J = 7.0 Hz, 3H). | 442.3 | E | |
| I-2435 | 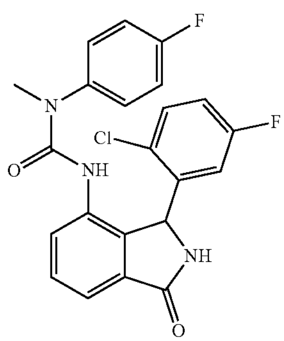 [SMILES: CN(C(=O)Nc1cccc2c1C(c1cc(F)ccc1Cl)NC2=O)c1ccc(F)cc1] | CN(C(=O)Nc1ccc c2C(=O)NC(c12)c1cc(F)cc c1Cl)c1ccc(F)cc1 | (400 MHz, DMSO-d6) 9.04 (s, 1H), 7.91 (s, 1H), 7.58 (s, 1H), 7.54-7.45 (m, 2H), 7.33 (ddd, J = 11.7, 8.6, 4.7 Hz, 2H), 7.10 (t, J = 8.8 Hz, 2H), 6.85-6.75 (m, 2H), 6.43 (s, 1H), 6.04 (s, 1H), 3.05 (s, 3H). | 428.2 | E | |
| I-2436 | 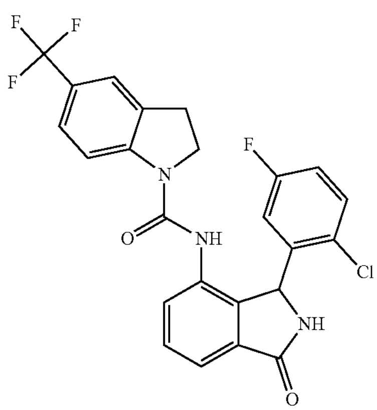 [SMILES: O=C1NC(c2cc(F)ccc2Cl)c2c(NC(=O)N3CCc4cc(C(F)(F)F)ccc43)cccc21] | Fc1ccc(C1)c(c1)C1NC(=O)cN2cccc(NC(=O)N3CCc4cc(ccc34)C(F)(F)F)c12 | (400 MHz, DMSO-d6) 9.07 (s, 1H), 8.72 (s, 1H), 7.87 (d, J = 8.4 Hz, 1H), 7.62 (d, J = 6.6 Hz, 1H), 7.61-7.54 (m, 2H), 7.54-7.45 (m, 2H), 7.43-7.35 (m, 2H), 7.16 (td, J = 8.4, 3.1 Hz, 1H), 6.01 (s, 1H), 3.95 (td, J = 10.1, 7.0 Hz, 1H), 3.12 (pt, J = 16.8, 7.8 Hz, 2H). | 490.3 | E | |
| I-2437 | 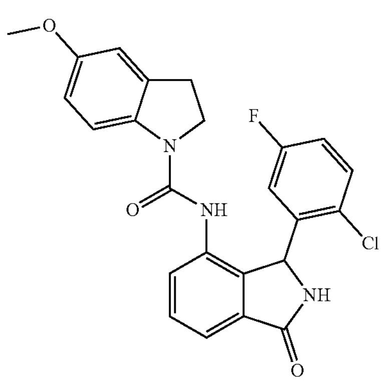 [SMILES: COc1ccc2c(c1)CCN2C(=O)Nc1cccc2c1C(c1cc(F)ccc1Cl)NC2=O] | COc1ccc2N(CCc2c1)C(=O)Nc1cccc2C(=O)NC(c12)c1cc(F)ccc1Cl | | 452.3 | E | |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-2438 | 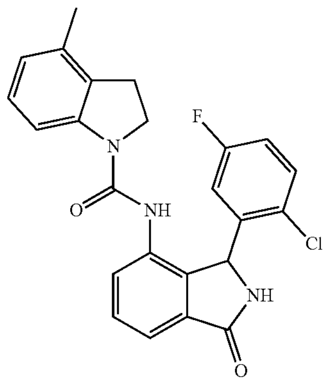 [SMILES: Cc1cccc2c1CCN2C(=O)Nc1cccc2c1C(c1cc(F)ccc1Cl)NC2=O] | Cc1cccc2 N(CCc12) C(=O)N c1cccc2C (=O)NC (c12)c1cc (F)ccc1C 1 | (400 MHz, DMSO-d6) 9.05 (s, 1H), 8.49 (s, 1H), 7.62-7.50 (m, 3H), 7.45-7.36 (m, 2H), 7.16 (td, J = 8.4, 3.1 Hz, 1H), 7.01 (t, J = 7.8 Hz, 1H), 6.73 (d, J = 7.5 Hz, 1H), 6.57 (s, 1H), 6.03 (s, 1H), 3.87 (td, J = 10.1, 7.2 Hz, 1H), 3.27 (s, 1H), 2.96 (tp, J = 14.3, 7.0 Hz, 2H), 2.19 (s, 3H). | 436.2 | D | |
| I-2439 | 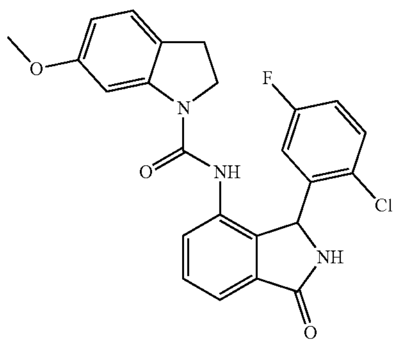 [SMILES: COc1ccc2c(c1)N(C(=O)Nc1cccc3c1C(c1cc(F)ccc1Cl)NC3=O)CC2] | COc1ccc 2CCN(C (=O)Nc3c ccc4C(= O)NC(c3 4)c3cc(F) ccc3Cl)c 2c1 | (400 MHz, DMSO-d6) 9.06 (s, 1H), 8.54 (s, 1H), 7.63-7.52 (m, 2H), 7.43-7.33 (m, 3H), 7.16 (td, J = 8.4, 3.1 Hz, 1H), 7.05 (d, J = 8.2 Hz, 1H), 6.60 (s, 1H), 6.47 (dd, J = 8.2, 2.5 Hz, 1H), 6.02 (s, 1H), 3.87 (td, J = 9.9, 7.4 Hz, 1H), 3.70 (s, 3H), 3.28 (d, J = 17.2 Hz, 1H), 3.04-2.85 (m, 2H). | 452.2 | D | |
| I-2440 | 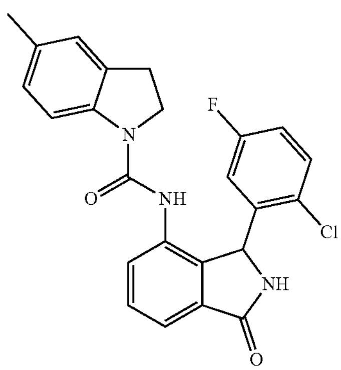 [SMILES: Cc1ccc2c(c1)CCN2C(=O)Nc1cccc2c1C(c1cc(F)ccc1Cl)NC2=O] | Cc1ccc2 N(CCc2c 1)C(=O) Nc1cccc 2C(=O)N C(c12)c1 cc(F)ccc 1Cl | (400 MHz, DMSO-d6) 9.03 (s, 1H), 8.47 (s, 1H), 7.56 (q, J = 7.5 Hz, 3H), 7.43-7.34 (m, 2H), 7.15 (td, J = 8.4, 3.1 Hz, 1H), 6.98 (s, 1H), 6.90 (d, J = 8.2 Hz, 1H), 6.58 (s, 1H), 6.02 (s, 1H), 3.83 (td, J = 9.9, 7.4 Hz, 1H), 3.23-3.15 (m, 1H), 2.98 (dt, J = 13.6, 7.0 Hz, 2H), 2.24 (s, 3H). | 436.2 | E | |
| I-2441 | 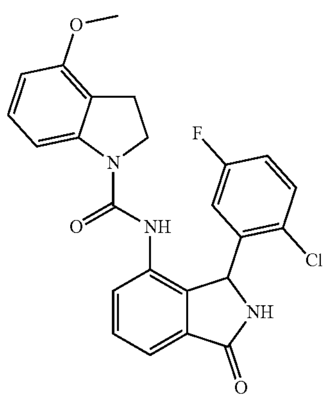 [SMILES: COc1cccc2c1CCN2C(=O)Nc1cccc2c1C(c1cc(F)ccc1Cl)NC2=O] | COc1ccc c2N(CCc 12)C(=O) Nc1cccc 2C(=O)N C(c12)c1 cc(F)ccc 1Cl | (400 MHz, DMSO-d6) 9.06 (s, 1H), 8.65 (s, 1H), 7.68 (d, J = 8.0 Hz, 1H), 7.64-7.53 (m, 2H), 7.39 (td, J = 8.3, 7.4, 2.7 Hz, 2H), 7.22-7.12 (m, 2H), 6.97 (d, J = 7.9 Hz, 1H), 6.56 (s, 1H), 6.00 (s, 1H), 3.94 (td, J = 10.3, 7.0 Hz, 1H), 3.25 (s, 1H), 3.08 (tdd, J = 16.5, 10.3, 6.4 Hz, 2H). | 456.2 | E | |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-2442 | 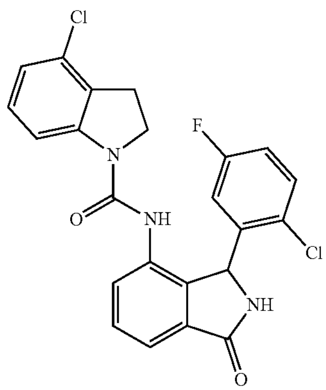 [SMILES: O=C1NC(c2cc(F)ccc2Cl)c2c(NC(=O)N3CCc4c(Cl)cccc43)cccc21] | Fc1ccc(C1)c(c1)C1NC(=O)c2cccc(NC(=O)N3CCc4c3cccc4Cl)c12 | (400 MHz, DMSO-d6) 9.06 (s, 1H), 8.65 (s, 1H), 7.68 (d, J = 8.0 Hz, 1H), 7.64-7.53 (m, 2H), 7.39 (td, J = 8.3, 7.4, 2.7. Hz, 2H), 7.22-7.12 (m, 2H), 6.97 (d, J = 7.9 Hz, 1H), 6.56 (s, 1H), 6.00 (s, 1H), 3.94 (td, J = 10.3, 7.0 Hz, 1H), 3.25 (s, 1H), 3.08 (tdd, J = 16.5, 10.3, 6.4 Hz, 2H). | 456.2 | D | |
| I-2443 | 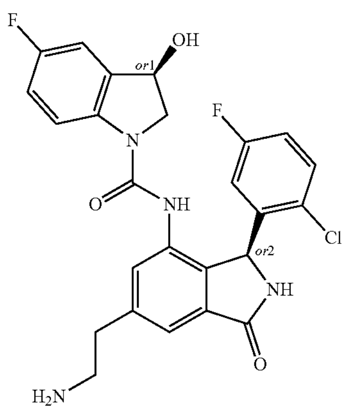 [SMILES: NCCc1cc(NC(=O)N2C[C@H](O)c3cc(F)ccc32)c2c(c1)C(=O)N[C@@H]2c1cc(F)ccc1Cl] | NCCc1cc2C(=O)N[C@@H](c2c(NC(=O)N2C[C@H](O)c3cc(F)ccc23)c1)c1cc(F)ccc1Cl | (400 MHz, DMSO-d6) 9.00 (s, 1H), 8.60 (s, 1H), 7.83 (dd, J = 8.9, 4.7 Hz, 1H), 7.42 (d, J = 1.5 Hz, 1H), 7.36 (dd, J = 8.9, 5.2 Hz, 1H), 7.21 (d, J = 1.5 Hz, 1H), 7.15 (tt, J = 8.2, 2.9 Hz, 2H), 7.08 (td, J = 9.0, 2.8 Hz, 1H), 6.55 (s, 1H), 5.96 (s, 1H), 5.77 (s, 1H), 5.07 (dd, J = 8.4, 3.5 Hz, 1H), 3.71 (dd, J = 11.3, 3.6 Hz, 1H), 3.27 (d, J = 32.4 Hz, 4H), 2.90-2.70 (m, 3H). | 499.2 | A | D |
| I-2444 | 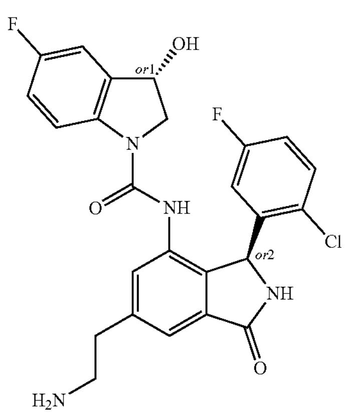 [SMILES: NCCc1cc(NC(=O)N2C[C@@H](O)c3cc(F)ccc32)c2c(c1)C(=O)N[C@@H]2c1cc(F)ccc1Cl] | NCCc1cc2C(=O)N[C@@H](c2c(NC(=O)N2C[C@@H](O)c3cc(F)ccc23)c1)c1cc(F)ccc1Cl | (400 MHz, DMSO-d6) 9.00 (s, 1H), 8.60 (s, 1H), 7.83 (dd, J = 8.9, 4.7 Hz, 1H), 7.42 (d, J = 1.5 Hz, 1H), 7.36 (dd, J = 8.9, 5.2 Hz, 1H), 7.21 (d, J = 1.5 Hz, 1H), 7.15 (tt, J = 8.2, 2.9 Hz, 2H), 7.08 (td, J = 9.0, 2.8 Hz, 1H), 6.55 (s, 1H), 5.96 (s, 1H), 5.77 (s, 1H), 5.07 (dd, J = 8.4, 3.5 Hz, 1H), 3.71 (dd, J = 11.3, 3.6 Hz, 1H), 3.27 (d, J = 32.4 Hz, 4H), 2.90-2.70 (m, 3H). | 499.2 | B | |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-2445 | 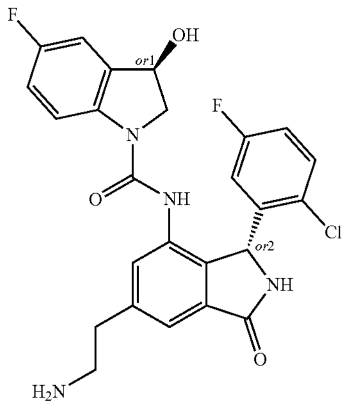 [SMILES: NCCc1cc(NC(=O)N2C[C@H](O)c3cc(F)ccc32)c2c(c1)C(=O)N[C@H]2c1cc(F)ccc1Cl] | NCCc1cc2C(=O)N[C@H](c2c(NC(=O)N2C[C@H](O)c3cc(F)ccc23)c1)c1cc(F)ccc1Cl | (400 MHz, DMSO-d6) 9.00 (s, 1H), 8.60 (s, 1H), 7.83 (dd, J = 8.9, 4.7 Hz, 1H), 7.42 (d, J = 1.5 Hz, 1H), 7.36 (dd, J = 8.9, 5.2 Hz, 1H), 7.21 (d, J = 1.5 Hz, 1H), 7.15 (tt, J = 8.2, 2.9 Hz, 2H), 7.08 (td, J = 9.0, 2.8 Hz, 1H), 6.55 (s, 1H), 5.96 (s, 1H), 5.77 (s, 1H), 5.07 (dd, J = 8.4, 3.5 Hz, 1H), 3.71 (dd, J = 11.3, 3.6 Hz, 1H), 3.27 (d, J = 32.4 Hz, 4H), 2.90-2.70 (m, 3H). | 499.2 | D | |
| I-2446 | 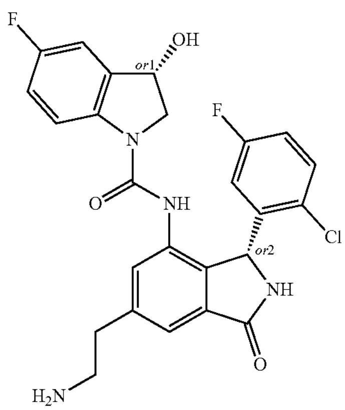 [SMILES: NCCc1cc(NC(=O)N2C[C@@H](O)c3cc(F)ccc32)c2c(c1)C(=O)N[C@H]2c1cc(F)ccc1Cl] | NCCc1cc2C(=O)N[C@H](c2c(NC(=O)N2C[C@@H](O)c3cc(F)ccc23)c1)c1cc(F)ccc1Cl | (400 MHz, DMSO-d6) 9.00 (s, 1H), 8.60 (s, 1H), 7.83 (dd, J = 8.9, 4.7 Hz, 1H), 7.42 (d, J = 1.5 Hz, 1H), 7.36 (dd, J = 8.9, 5.2 Hz, 1H), 7.21 (d, J = 1.5 Hz, 1H), 7.15 (tt, J = 8.2, 2.9 Hz, 2H), 7.08 (td, J = 9.0, 2.8 Hz, 1H), 6.55 (s, 1H), 5.96 (s, 1H), 5.77 (s, 1H), 5.07 (dd, J = 8.4, 3.5 Hz, 1H), 3.71 (dd, J = 11.3, 3.6 Hz, 1H), 3.27 (d, J = 32.4 Hz, 4H), 2.90-2.70 (m, 3H). | 499.2 | D | |
| I-2447 | 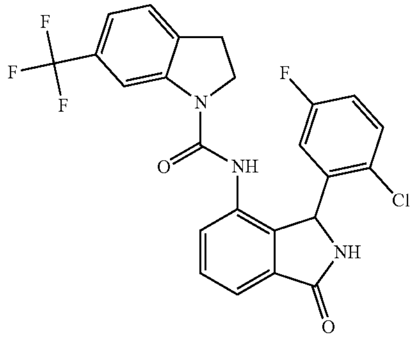 [SMILES: O=C1NC(c2cc(F)ccc2Cl)c2c(NC(=O)N3CCc4ccc(C(F)(F)F)cc43)cccc21] | Fc1ccc(C1)c(c1)C1NC(=O)c2cccc(NC(=O)N3CCc4ccc(cc34)C(F)(F)F)c12 | (400 MHz, DMSO-d6) 9.08 (s, 1H), 8.73 (s, 1H), 8.00 (s, 1H), 7.66-7.59 (m, 1H), 7.58 (t, J = 7.5 Hz, 1H), 7.43-7.32 (m, 3H), 7.25 (d, J = 7.5 Hz, 1H), 7.13 (td, J = 8.4, 3.1 Hz, 1H), 6.56 (s, 1H), 6.03 (s, 1H), 3.95 (td, J = 10.0, 7.0 Hz, 1H), 3.21 (s, 1H), 3.13 (q, J = 10.1 Hz, 2H). | 490.2 | D | |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-2448 | 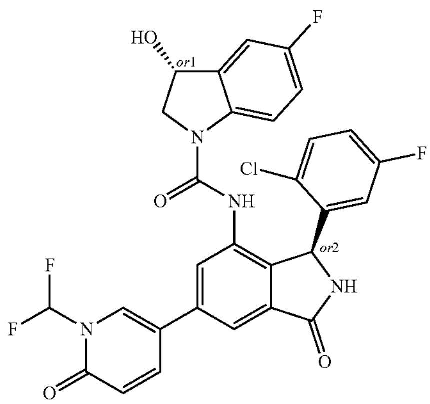 [SMILES: O=C1N[C@H](c2cc(F)ccc2Cl)c2c(NC(=O)N3C[C@H](O)c4cc(F)ccc43)cc(-c3ccc(=O)n(C(F)F)c3)cc21] | O[C@H]1CN(C(=O)Nc2cc(cc3C(=O)N[C@@H](c23)c2cc(F)ccc2Cl)-c2ccc(=O)n(c2)C(F)F)c2ccc(F)cc12 | (400 MHz, DMSO-d6) 9.12 (s, 1H), 8.73 (s, 1H), 8.16 (d, J = 2.6 Hz, 1H), 8.11-8.04 (m, 1H), 7.94-7.72 (m, 3H), 7.63 (d, J = 1.7 Hz, 1H), 7.38 (dd, J = 8.9, 5.2 Hz, 1H), 7.21-7.02 (m, 3H), 6.69 (d, J = 9.7 Hz, 2H), 6.05 (s, 1H), 5.79 (s, 1H), 5.12-5.05 (m, 1H), 3.73 (dd, J = 11.4, 3.6 Hz, 1H), 3.25 (dd, J = 11.0, 4.0 Hz, 1H). | 599.1 | A | B |
| I-2449 | 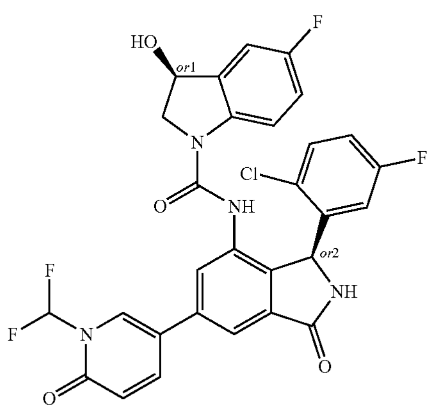 [SMILES: O=C1N[C@H](c2cc(F)ccc2Cl)c2c(NC(=O)N3C[C@@H](O)c4cc(F)ccc43)cc(-c3ccc(=O)n(C(F)F)c3)cc21] | O[C@@H]1CN(C(=O)Nc2cc(cc3C(=O)N[C@@H](c23)c2cc(F)ccc2Cl)-c2ccc(=O)n(c2)C(F)F)c2ccc(F)cc12 | (400 MHz, DMSO-d6) 9.14 (s, 1H), 8.59 (s, 1H), 8.15 (d, J = 2.6 Hz, 1H), 8.12-8.03 (m, 1H), 7.92 (s, 1H), 7.83 (d, J = 1.6 Hz, 1H), 7.78-7.64 (m, 2H), 7.36 (dd, J = 8.9, 5.1 Hz, 1H), 7.18-6.96 (m, 3H), 6.68 (d, J = 9.7 Hz, 2H), 6.13 (s, 1H), 5.74 (d, J = 4.9 Hz, 1H), 5.31-5.07 (m, 1H), 4.00 (dd, J = 11.1, 8.0 Hz, 1H), 3.25 (dd, J = 11.0, 4.0 Hz, 1H). | 599.1 | B | |
| I-2450 | 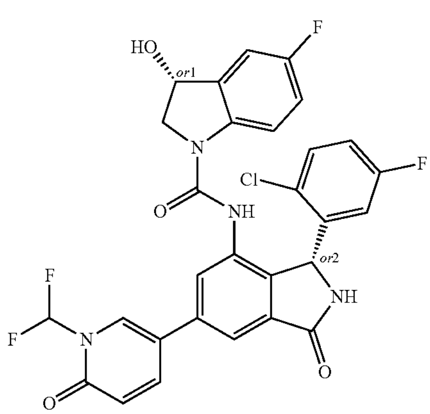 [SMILES: O=C1N[C@@H](c2cc(F)ccc2Cl)c2c(NC(=O)N3C[C@H](O)c4cc(F)ccc43)cc(-c3ccc(=O)n(C(F)F)c3)cc21] | O[C@H]1CN(C(=O)Nc2cc(cc3C(=O)N[C@H](c23)c2cc(F)ccc2Cl)-c2ccc(=O)n(c2)C(F)F)c2ccc(F)cc12 | (400 MHz, DMSO-d6) 9.14 (s, 1H), 8.60 (s, 1H), 8.15 (d, J = 2.6 Hz, 1H), 8.11-8.03 (m, 1H), 7.92 (s, 1H), 7.83 (d, J = 1.6 Hz, 1H), 7.80-7.66 (m, 2H), 7.36 (dd, J = 8.9, 5.1 Hz, 1H), 7.18-6.95 (m, 3H), 6.68 (m, 2H), 6.13 (s, 1H), 5.75 (s, 1H), 5.16 (dd, J = 8.0, 4.0 Hz, 1H), 4.00 (dd, J = 11.1, 8.1 Hz, 1H), 3.25 (dd, J = 11.0, 4.0 Hz, 1H). | 599.0 | D | |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-2451 | 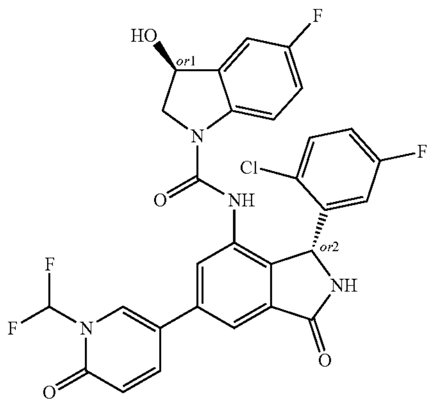 [SMILES: O=C1N[C@@H](c2cc(F)ccc2Cl)c2c(NC(=O)N3C[C@@H](O)c4cc(F)ccc43)cc(-c3ccc(=O)n(C(F)F)c3)cc21] | O[C@@H]1CN(C(=O)Nc2cc(cc3C(=O)N[C@H](c23)c2cc(F)ccc2Cl)-c2ccc(=O)n(c2)C(F)F)c2ccc(F)cc12 | (400 MHz, DMSO-d6) 9.12 (s, 1H), 8.73 (s, 1H), 8.16 (d, J = 2.6 Hz, 1H), 8.11-8.03 (m, 1H), 7.92 (s, 1H), 7.88-7.75 (m, 2H), 7.63 (d, J = 1.7 Hz, 1H), 7.38 (dd, J = 8.9, 5.2 Hz, 1H), 7.21-7.01 (m, 3H), 6.69 (d, J = 9.7 Hz, 2H), 6.13 (s, 1H), 5.86 (s, 1H), 5.09 (d, J = 7.6 Hz, 1H), 3.73 (dd, J = 11.3, 3.6 Hz, 1H), 3.25 (dd, J = 11.0, 4.0 Hz, 1H). | 599.2 | D | |
| I-2452 | 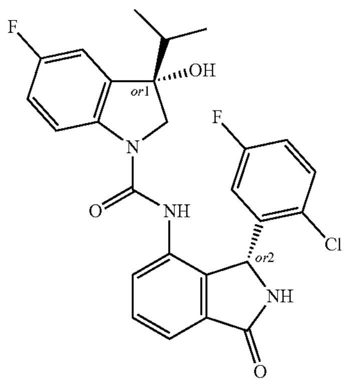 [SMILES: CC(C)[C@@]1(O)CN(C(=O)Nc2cccc3c2[C@H](c2cc(F)ccc2Cl)NC3=O)c2ccc(F)cc21] | CC(C)[C@@]1(O)CN(C(=O)Nc2cccc3C(=O)N[C@H](c23)c2cc(F)ccc2Cl)c2ccc(F)cc12 | (400 MHz, DMSO-d6) 9.05 (s, 1H), 8.60 (s, 1H), 7.89 (s, 1H), 7.63-7.53 (m, 2H), 7.42 (dd, J = 7.1, 1.8 Hz, 1H), 7.34 (dd, J = 8.9, 5.1 Hz, 1H), 7.14 (td, J = 8.4, 3.1 Hz, 1H), 7.09-7.02 (m, 2H), 6.55 (s, 1H), 6.11 (s, 1H), 5.54 (s, 1H), 3.64 (d, J = 11.2 Hz, 1H), 3.30 (s, 1H), 2.15-2.04 (m, 1H), 0.89 (d, J = 6.7 Hz, 3H), 0.55 (d, J = 6.8 Hz, 3H). | 498.3 | D | |
| I-2453 | 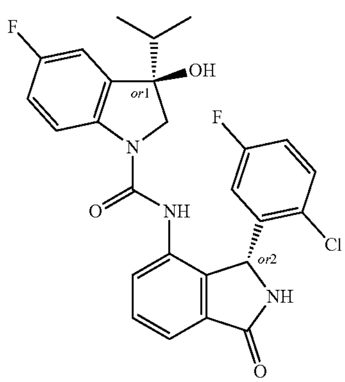 [SMILES: CC(C)[C@]1(O)CN(C(=O)Nc2cccc3c2[C@H](c2cc(F)ccc2Cl)NC3=O)c2ccc(F)cc21] | CC(C)[C@]1(O)CN(C(=O)Nc2cccc3C(=O)N[C@H](c23)c2cc(F)ccc2Cl)c2ccc(F)cc12 | (400 MHz, DMSO-d6) 9.08 (s, 1H), 8.41 (s, 1H), 7.74 (dd, J = 8.8, 4.7 Hz, 1H), 7.58 (d, J = 1.9 Hz, 3H), 7.39 (dd, J = 8.9, 5.1 Hz, 1H), 7.13 (td, J = 8.5, 3.1 Hz, 1H), 7.08-6.97 (m, 2H), 6.55 (s, 1H), 6.17 (s, 1H), 5.48 (s, 1H), 3.78 (d, J = 11.1 Hz, 1H), 3.35 (s, 1H), 2.08 (s, 1H), 0.94 (d, J = 6.7 Hz, 3H), 0.57 (d, J = 6.8 Hz, 3H). | 498.3 | D | |
| I-2454 | 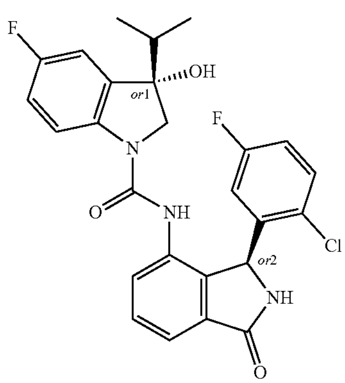 [SMILES: CC(C)[C@@]1(O)CN(C(=O)Nc2cccc3c2[C@@H](c2cc(F)ccc2Cl)NC3=O)c2ccc(F)cc21] | CC(C)[C@@]1(O)CN(C(=O)Nc2cccc3C(=O)N[C@@H](c23)c2cc(F)ccc2Cl)c2ccc(F)cc12 | (400 MHz, DMSO-d6) 9.05 (s, 1H), 8.60 (s, 1H), 7.89 (s, 1H), 7.63-7.53 (m, 2H), 7.42 (dd, J = 7.1, 1.8 Hz, 1H), 7.34 (dd, J = 8.9, 5.2 Hz, 1H), 7.14 (td, J = 8.3, 3.1 Hz, 1H), 7.06 (ddt, J = 6.9, 3.9, 2.1 Hz, 2H), 6.55 (s, 1H), 6.11 (s, 1H), 5.54 (s, 1H), 3.64 (d, J = 11.3 Hz, 1H), 3.35 (s, 1H), 2.15-2.04 (m, 1H), 0.89 (d, J = 6.7 Hz, 3H), 0.55 (d, J = 6.8 Hz, 3H). | 498.3 | B | |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-2455 | 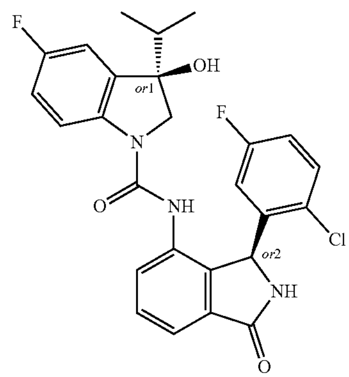 [SMILES: CC(C)[C@]1(O)CN(C(=O)Nc2cccc3c2[C@@H](c2cc(F)ccc2Cl)NC3=O)c2ccc(F)cc21] | CC(C)[C@]1(O)CN(C(=O)Nc2cccc3C(=O)N[C@@H](c23)c2cc(F)ccc2Cl)c2ccc(F)cc12 | (400 MHz, DMSO-d6) 9.08 (s, 1H), 8.41 (s, 1H), 7.74 (dd, J = 8.8, 4.8 Hz, 1H), 7.58 (d, J = 1.9 Hz, 3H), 7.39 (dd, J = 8.9, 5.1 Hz, 1H), 7.13 (td, J = 8.4, 3.1 Hz, 1H), 7.08-7.02 (m, 1H), 7.02 (dd, J = 9.0, 6.3 Hz, 1H), 6.55 (s, 1H), 6.17 (s, 1H), 5.48 (s, 1H), 3.78 (d, J = 11.1 Hz, 1H), 3.29 (s, 1H), 2.07 (q, J = 6.7 Hz, 1H), 0.94 (d, J = 6.7 Hz, 3H), 0.57 (d, J = 6.8 Hz, 3H). | 498.3 | D | |
| I-2456 | 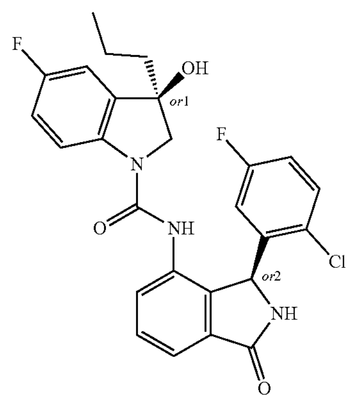 [SMILES: CCC[C@]1(O)CN(C(=O)Nc2cccc3c2[C@@H](c2cc(F)ccc2Cl)NC3=O)c2ccc(F)cc21] | CCC[C@]1(O)CN(C(=O)Nc2cccc3C(=O)N[C@@H](c23)c2cc(F)ccc2Cl)c2ccc(F)cc12 | (400 MHz, DMSO-d6) δ 9.05 (s, 1H), 8.62 (s, 1H), 7.86 (s, 1H), 7.62-7.52 (m, 2H), 7.41-7.32 (m, 2H), 7.14 (td, J = 8.3, 3.1 Hz, 1H), 7.11-7.01 (m, 2H), 6.03 (s, 1H), 5.55 (s, 1H), 3.77 (d, J = 11.0 Hz, 1H), 3.12 (d, J = 11.0 Hz, 1H), 1.77 (td, J = 12.2, 11.2, 4.4 Hz, 1H), 1.52 (td, J = 13.3, 12.6, 4.4 Hz, 1H), 1.26 (d, J = 14.2 Hz, 1H), 1.07-0.88 (m, 4H). | 498.2 | D | |
| I-2457 | 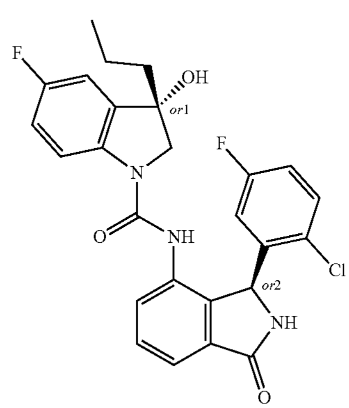 [SMILES: CCC[C@@]1(O)CN(C(=O)Nc2cccc3c2[C@@H](c2cc(F)ccc2Cl)NC3=O)c2ccc(F)cc21] | CCC[C@@]1(O)CN(C(=O)Nc2cccc3C(=O)N[C@@H](c23)c2cc(F)ccc2Cl)c2ccc(F)cc12 | (400 MHz, DMSO-d6) δ 9.05 (s, 1H), 8.62 (s, 1H), 7.86 (s, 1H), 7.62-7.52 (m, 2H), 7.41-7.32 (m, 2H), 7.14 (td, J = 8.3, 3.1 Hz, 1H), 7.11-7.01 (m, 2H), 6.03 (s, 1H), 5.55 (s, 1H), 3.77 (d, J = 11.0 Hz, 1H), 3.12 (d, J = 11.0 Hz, 1H), 1.77 (td, J = 12.2, 11.2, 4.4 Hz, 1H), 1.52 (td, J = 13.3, 12.6, 4.4 Hz, 1H), 1.26 (d, J = 14.2 Hz, 1H), 1.07-0.88 (m, 4H). | 498.2 | C | |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-2458 | 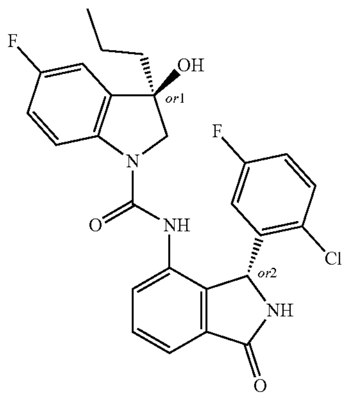 [SMILES: CCC[C@]1(O)CN(C(=O)Nc2cccc3c2[C@H](c2cc(F)ccc2Cl)NC3=O)c2ccc(F)cc21] | CCC[C@]1(O)CN(C(=O)Nc2cccc3C(=O)N[C@H](c23)c2cc(F)ccc2Cl)c2ccc(F)cc12 | (400 MHz, DMSO-d6) δ 9.05 (s, 1H), 8.62 (s, 1H), 7.86 (s, 1H), 7.62-7.52 (m, 2H), 7.41-7.32 (m, 2H), 7.14 (td, J = 8.3, 3.1 Hz, 1H), 7.11-7.01 (m, 2H), 6.03 (s, 1H), 5.55 (s, 1H), 3.77 (d, J = 11.0 Hz, 1H), 3.12 (d, J = 11.0 Hz, 1H), 1.77 (td, J = 12.2, 11.2, 4.4 Hz, 1H), 1.52 (td, J = 13.3, 12.6, 4.4 Hz, 1H), 1.26 (d, J = 14.2 Hz, 1H), 1.07-0.88 (m, 4H). | 498.2 | | D |
| I-2459 | 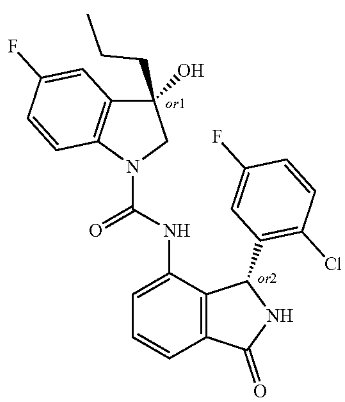 [SMILES: CCC[C@@]1(O)CN(C(=O)Nc2cccc3c2[C@H](c2cc(F)ccc2Cl)NC3=O)c2ccc(F)cc21] | CCC[C@@]1(O)CN(C(=O)Nc2cccc3C(=O)N[C@H](c23)c2cc(F)ccc2Cl)c2ccc(F)cc12 | (400 MHz, DMSO-d6) δ 9.05 (s, 1H), 8.62 (s, 1H), 7.86 (s, 1H), 7.62-7.52 (m, 2H), 7.41-7.32 (m, 2H), 7.14 (td, J = 8.3, 3.1 Hz, 1H), 7.11-7.01 (m, 2H), 6.03 (s, 1H), 5.55 (s, 1H), 3.77 (d, J = 11.0 Hz, 1H), 3.12 (d, J = 11.0 Hz, 1H), 1.77 (td, J = 12.2, 11.2, 4.4 Hz, 1H), 1.52 (td, J = 13.3, 12.6, 4.4 Hz, 1H), 1.26 (d, J = 14:2 Hz, 1H), 1.07-0.88 (m, 4H). | 498.2 | | D |
| I-2460 | 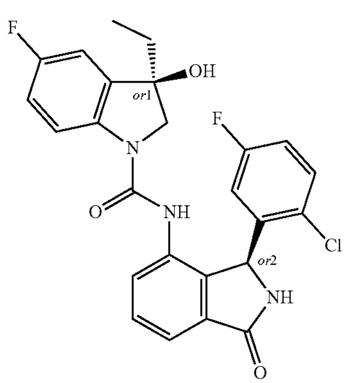 [SMILES: CC[C@]1(O)CN(C(=O)Nc2cccc3c2[C@@H](c2cc(F)ccc2Cl)NC3=O)c2ccc(F)cc21] | CC[C@]1(O)CN(C(=O)Nc2cccc3C(=O)N[C@@H](c23)c2cc(F)ccc2Cl)c2ccc(F)cc12 | (400 MHz, DMSO-d6) δ 9.05 (s, 1H), 8.63 (s, 1H), 7.86 (dd, J = 8.7, 4.5 Hz, 1H), 7.64-7.52 (m, 2H), 7.42-7.33 (m, 2H), 7.15 (td, J = 8.4, 3.1 Hz, 1H), 7.11-7.01 (m, 2H), 6.55 (s, 1H), 6.04 (s, 1H), 5.56 (s, 1H), 3.76 (d, J = 11.0 Hz, 1H), 3.13 (d, J = 11.0 Hz, 1H), 1.80 (dq, J = 14.1, 7.1 Hz, 1H), 1.57 (dq, J = 14.6, 7.4 Hz, 1H), 0.76 (t, J = 7.3 Hz, 3H). | 484.2 | | D |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-2461 | 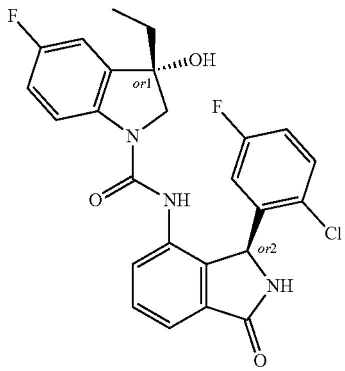 [SMILES: CC[C@@]1(O)CN(C(=O)Nc2cccc3c2[C@@H](c2cc(F)ccc2Cl)NC3=O)c2ccc(F)cc21] | CC[C@@]1(O)CN(C(=O)Nc2cccc3C(=O)N[C@@H](c23)c2cc(F)ccc2Cl)c2ccc(F)cc12 | (400 MHz, DMSO-d6) δ 9.05 (s, 1H), 8.63 (s, 1H), 7.86 (dd, J = 8.7, 4.5 Hz, 1H), 7.64-7.52 (m, 2H), 7.42-7.33 (m, 2H), 7.15 (td, J = 8.4, 3.1 Hz, 1H), 7.11-7.01 (m, 2H), 6.55 (s, 1H), 6.04 (s, 1H), 5.56 (s, 1H), 3.76 (d, J = 11.0 Hz, 1H), 3.13 (d, J = 11.0 Hz, 1H), 1.80 (dq, J = 14.1, 7.1 Hz, 1H), 1.57 (dq, J = 14.6, 7.4 Hz, 1H), 0.76 (t, J = 7.3 Hz, 3H). | 484.2 | A | A |
| I-2462 | 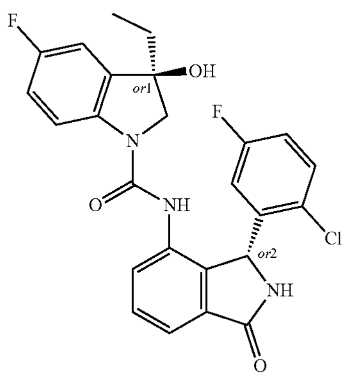 [SMILES: CC[C@]1(O)CN(C(=O)Nc2cccc3c2[C@H](c2cc(F)ccc2Cl)NC3=O)c2ccc(F)cc21] | CC[C@]1(O)CN(C(=O)Nc2cccc3C(=O)N[C@H](c23)c2cc(F)ccc2Cl)c2ccc(F)cc12 | (400 MHz, DMSO-d6) δ 9.05 (s, 1H), 8.63 (s, 1H), 7.86 (dd, J = 8.7, 4.5 Hz, 1H), 7.64-7.52 (m, 2H), 7.42-7.33 (m, 2H), 7.15 (td, J = 8.4, 3.1 Hz, 1H), 7.11-7.01 (m, 2H), 6.55 (s, 1H), 6.04 (s, 1H), 5.56 (s, 1H), 3.76 (d, J = 11.0 Hz, 1H), 3.13 (d, J = 11.0 Hz, 1H), 1.80 (dq, J = 14.1, 7.1 Hz, 1H), 1.57 (dq, J = 14.6, 7.4 Hz, 1H), 0.76 (t, J = 7.3 Hz, 3H). | 484.2 | D | |
| I-2463 | 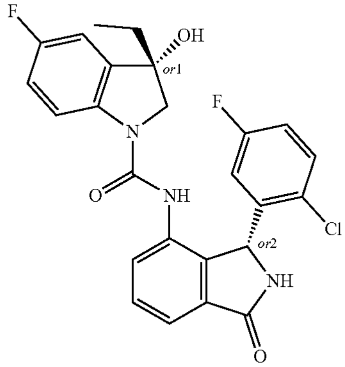 [SMILES: CC[C@@]1(O)CN(C(=O)Nc2cccc3c2[C@H](c2cc(F)ccc2Cl)NC3=O)c2ccc(F)cc21] | CC[C@@]1(O)CN(C(=O)Nc2cccc3C(=O)N[C@H](c23)cc(F)ccc2Cl)c2ccc(F)cc12 | (400 MHz, DMSO-d6) δ 9.05 (s, 1H), 8.63 (s, 1H), 7.86 (dd, J = 8.7, 4.5 Hz, 1H), 7.64-7.52 (m, 2H), 7.42-7.33 (m, 2H), 7.15 (td, J = 8.4, 3.1 Hz, 1H), 7.11-7.01 (m, 2H), 6.55 (s, 1H), 6.04 (s, 1H), 5.56 (s, 1H), 3.76 (d, J = 11.0 Hz, 1H), 3.13 (d, J = 11.0 Hz, 1H), 1.80 (dq, J = 14.1, 7.1 Hz, 1H), 1.57 (dq, J = 14.6, 7.4 Hz, 1H), 0.76 (t, J = 7.3 Hz, 3H). | 484.2 | D | |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-2464 | lp;3p | OC1CN(C(=O)Nc2cccc3C(=O)NC(c23)c2cc(F)ccc2Cl)c2cc(Cl)ccc12 | (400 MHz, DMSO-d6) δ 9.08 (br s, 1 H), 8.74 (s, 0.5 H), 8.67 (s, 0.5 H), 7.83 (s, 0.5 H), 7.67-7.51 (m, 2.5 H), 7.47-7.26 (m, 3 H), 7.15 (td, J = 8.4, 3.0 Hz, 0.5 H), 7.08 (td, J = 8.5, 3.0 Hz, 0.5 H), 7.02 (dd, J = 8.1, 1.8 Hz, 0.5 H), 6.99 (dd, J = 8.0, 1.8 Hz, 0.5 H), 6.55 (br s, 1 H), 6.07 (br s, 0.5 H), 6.00 (br s, 0.5 H), 5.72 (s, 1 H), 5.12 (dd, J = 7.7, 3.1 Hz, 0.5 H), 5.06 (dd, J = 7.2, 2.5 Hz, 0.5 H), 3.96 (dd, J = 10.9, 8.0 Hz, 0.5 H), 3.71 (dd, J = 11.3, 3.2 Hz, 0.5 H), 3.26 (dd, J = 11.1, 3.3 Hz, 0.5 H). ~1:1 mixture of diastereomers | 472.2 | A | C |
| I-2465 | 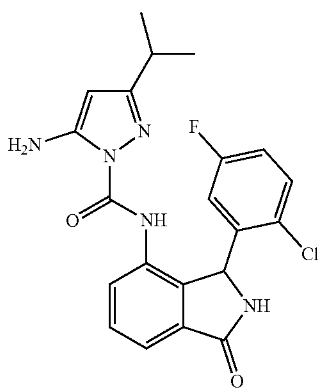 [SMILES: CC(C)c1cc(N)n(C(=O)Nc2cccc3c2C(c2cc(F)ccc2Cl)NC3=O)n1] | CC(C)c1cc(N)n(n1)C(=O)Nc1cccc2C(=O)NC(c12)c1cc(F)ccc1Cl | | 428.1 | | E |
| I-2466 | 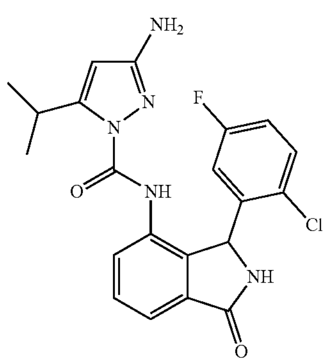 [SMILES: CC(C)c1cc(N)nn1C(=O)Nc1cccc2c1C(c1cc(F)ccc1Cl)NC2=O] | CC(C)c1cc(N)nn1C(=O)Nc1cccc2C(=O)NC(c12)c1cc(F)ccc1Cl | | 428.0 | | E |

TABLE 2-continued

Representative Compounds of the Invention with Bioactivity Data.

| Ex. No. | Structure | SMILES | $^1$H NMR | MS | ADP-Glo IC$_{50}$ | MCF 10A IC$_{50}$ |
|---|---|---|---|---|---|---|
| I-2467 | 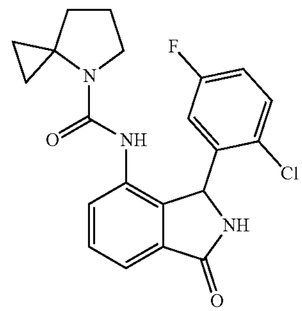 [SMILES: O=C1NC(c2cc(F)ccc2Cl)c2c(NC(=O)N3CCCC34CC4)cccc21] | Fc1ccc(C1)c(c1)C1NC(=O)c2cccc(NC(=O)N3CCCC33CC3)c12 | (400 MHz, DMSO-d6) δ 8.98 (br s, 1H), 7.97 (s, 1H), 7.70-7.37 (m, 3H), 7.37-7.15 (m, 2H), 6.61 (br s, 1H), 5.89 (br s, 1H), 3.29 (submerged m, 1H), 2.78-2.55 (m, 1H), 1.94-1.81 (m, 1H), 1.82-1.71 (m, 2H), 1.70-1.57 (m, 2H), 1.49-1.35 (m, 1H), 0.46-0.25 (m, 2H). | 400.0 | D | |
| I-2468 | 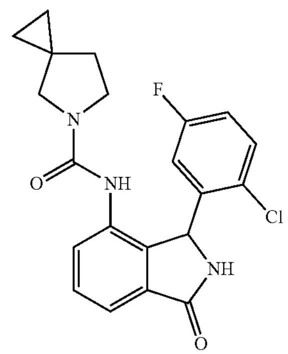 [SMILES: O=C1NC(c2cc(F)ccc2Cl)c2c(NC(=O)N3CCC4(CC4)C3)cccc21] | Fc1ccc(C1)c(c1)C1NC(=O)c2cccc(NC(=O)N3CCC4(CC4)C3)c12 | (400 MHz, DMSO-d6) δ 9.00 (br s, 1H), 8.06 (br s, 1H), 7.59-7.41 (m, 3H), 7.29 (p, J = 3.8 Hz, 1H), 7.24 (td, J = 8.4, 3.1 Hz, 1H), 6.59 (br s, 1H), 6.00 (br s, 1H), 3.39 (submerged m, 1H), 3.17 (d, J = 9.8 Hz, 1H), 2.94 (br s, 1H), 2.70 (br s, 1H), 1.76-1.55 (m, 2H), 0.63-0.39 (m, 4H). | 400.0 | E | |
| I-2469 | 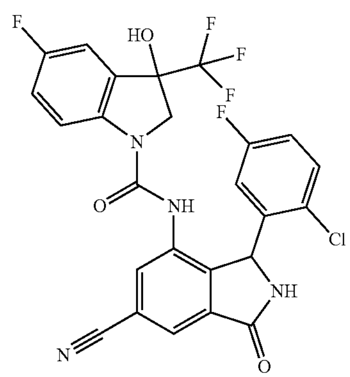 [SMILES: N#Cc1cc(NC(=O)N2CC(O)(C(F)(F)F)c3cc(F)ccc32)c2c(c1)C(=O)NC2c1cc(F)ccc1Cl] | OC1(CN(C(=O)Nc2cc(cc3C(=O)NC(c23)c2cc(F)ccc2Cl)C#N)c2ccc(F)cc12)C(F)(F)F | (400 MHz, DMSO-d6) δ 9.40 (br. s, 1H), 8.99 (br. s, 2H), 8.05 (s, 2H), 7.92 (s, 2H), 7.85 (dd, J = 8.9, 4.6 Hz, 1H), 7.82 (s, 1H), 7.52-7.39 (m, 2H), 7.36 (td, J = 8.3, 5.5 Hz, 2H), 7.31-7.25 (m, 2H), 7.25-7.18 (m, J = 7.8 Hz, 2H), 7.18-7.05 (m, 2H), 6.63 (br. s, 2H), 6.14 (s, 2H), 4.15 (d, J = 11.8 Hz, 1H), 3.97 (d, J = 12.0 Hz, 1H), 3.52 (d, J = 11.8 Hz, 1H), 3.45 (d, J = 11.8 Hz, 1H); 1:1 mixture of diastereomers | 547.3 | A | A |
| I-2470 | 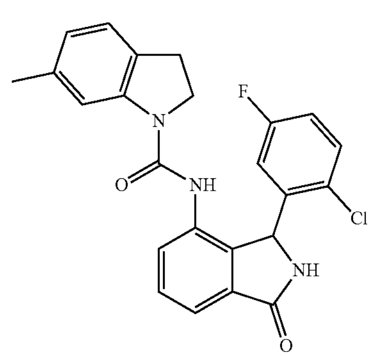 [SMILES: Cc1ccc2c(c1)N(C(=O)Nc1cccc3c1C(c1cc(F)ccc1Cl)NC3=O)CC2] | Cc1ccc2CCN(C(=O)Nc3cccc4C(=O)NC(c34)c3cc(F)ccc3Cl)c2c1 | (400 MHz, DMSO-d6) 9.05 (s, 1H), 8.55 (s, 1H), 7.61-7.52 (m, 2H), 7.46 (s, 1H), 7.42-7.34 (m, 2H), 7.15 (td, J = 8.4, 3.1 Hz, 1H), 7.04 (d, J = 7.5 Hz, 2H), 6.75-6.68 (m, 1H), 6.20 (s, 1H) 3.89-3.77 (m, 1H), 3.34 (s, 2H), 3.28 (s, 1H), 2.24 (s, 3H). | 436.2 | B | |

TABLE 2-continued

Representative Compounds of the Invention with Bioactivity Data.

| Ex. No. | Structure | SMILES | $^1$H NMR | MS | ADP-Glo IC$_{50}$ | MCF 10A IC$_{50}$ |
|---|---|---|---|---|---|---|
| I-2471 | 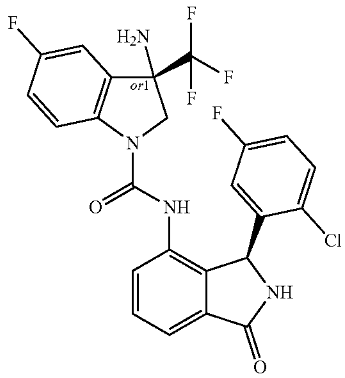 [SMILES: N[C@]1(C(F)(F)F)CN(C(=O)Nc2cccc3c2[C@@H](c2cc(F)ccc2Cl)NC3=O)c2ccc(F)cc21] | N[C@]1(CN(C(=O)Nc2ccc3C(=O)N[C@H](c23)c2cc(F)ccc2Cl)c2ccc(F)cc12)C(F)(F)F | (400 MHz, DMSO-d6) δ 9.08 (br s, 1H), 8.68 (s, 1H), 7.78 (dd, J = 8.9, 4.6 Hz, 1H), 7.63-7.54 (m, 2H), 7.45 (dd, J = 7.3, 1.4 Hz, 1H), 7.37 (dd, J = 8.7, 5.3 Hz, 1H), 7.28 (dd, J = 8.1, 2.5 Hz, 1H), 7.19-7.08 (m, 2H), 6.49 (br s, 1H), 6.06 (br s, 1H), 4.21 (d, J = 11.5 Hz, 1H), 3.30-3.25 (m, 1H [submerged under H2O peak-see COSY]), 2.89-2.83 (br s, 2H) ppm [dr = 95:5, racemic]. | 523.4 | D | |
| I-2472 | 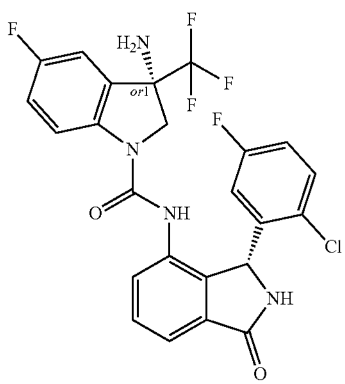 [SMILES: N[C@]1(C(F)(F)F)CN(C(=O)Nc2cccc3c2[C@H](c2cc(F)ccc2Cl)NC3=O)c2ccc(F)cc21] | N[C@@]1(CN(C(=O)Nc2ccc3C(=O)N[C@H](c23)c2cc(F)cc2Cl)c2cc(F)cc12)C(F)(F)F | (400 MHz, DMSO-d6) δ 9.08 (br s, 1H), 8.77 (s, 1H), 7.81 (dd, J = 8.6, 4.4 Hz, 1H), 7.63-7.54 (m, 2H), 7.36 (dd, J = 7.4, 1.3 Hz, 1H), 7.33 (dd, J = 8.9, 5.2 Hz, 1H), 7.26 (dd, J = 8.3, 2.5 Hz, 1H), 7.19-7.09 (m, 2H), 6.53 (br s, 1H), 6.04 (br s, 1H), 3.85 (d, J = 11.6 Hz, 1H), 3.54 (d, J = 11.5 Hz, 1H), 2.96-2.87 (br s, 2H) ppm [single diasteromer]. | 523.4 | C | |
| I-2473 | 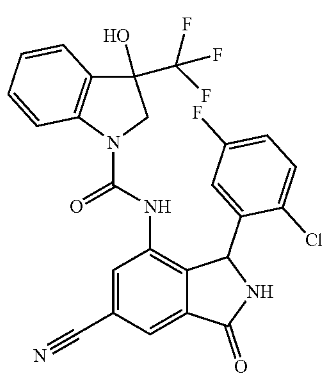 [SMILES: N#Cc1cc(NC(=O)N2CC(O)(C(F)(F)F)c3ccccc32)c2c(c1)C(=O)NC2c1cc(F)ccc1Cl] | OC1(CN(C(=O)Nc2cc(cc3C(=O)NC(c23)c2cc(F)ccc2Cl)C#N)c2ccccc12)C(F)(F)F | (400 MHz, DMSO-d6) δ 9.40 (br. s, 2H), 8.96 (br. s, 2H), 8.04 (s, 2H), 7.95 (d, J = 1.3 Hz, 1H), 7.83 (d, J = 1.3 Hz, 1H), 7.63 (d, J = 1.2 Hz, 1H), 7.60 (d, J = 1.2 Hz, 1H), 7.44 (d, J = 7.7 Hz, 2H), 7.42-7.31 (m, 4H), 7.32-7.22 (m, 2H), 7.23-7.01 (m, 4H), 6.71 (br. s, 2H), 6.16 (br. s, 2H), 4.08 (d, J = 12.0 Hz, 1H), 3.92 (d, J = 11.9 Hz, 1H), 3.50 (d, J = 11.6 Hz, 1H), 3.47 (d, J = 11.6 Hz, 1H) ; 1:1 mixture of diastereomers | 529.3 | A | A |

TABLE 2-continued

Representative Compounds of the Invention with Bioactivity Data.

| Ex. No. | Structure | SMILES | $^1$H NMR | MS | ADP-Glo IC$_{50}$ | MCF 10A IC$_{50}$ |
|---|---|---|---|---|---|---|
| I-2474 | 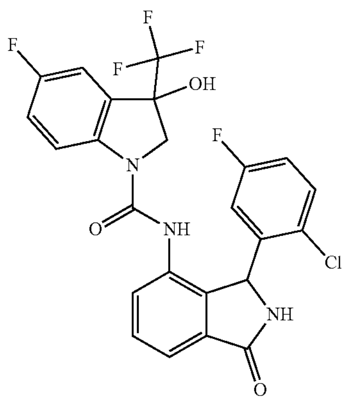 [SMILES: O=C1NC(c2cc(F)ccc2Cl)c2c(NC(=O)N3CC(O)(C(F)(F)F)c4cc(F)ccc43)cccc21] | OC1(CN(C(=O)Nc2cccc3C(=O)NC(c23)c2cc(F)ccc2Cl)c2ccc(F)cc12)C(F)(F)F | | 524.3 | A | B |
| I-2475 | 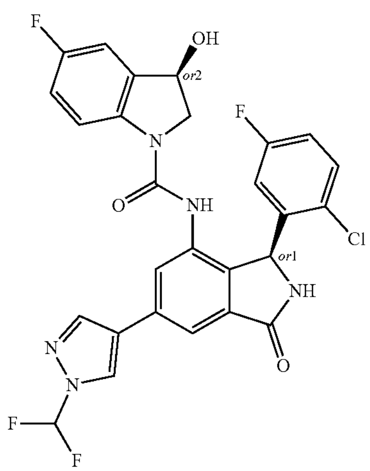 [SMILES: O=C1N[C@H](c2cc(F)ccc2Cl)c2c(NC(=O)N3C[C@H](O)c4cc(F)ccc43)cc(-c3cnn(C(F)F)c3)cc21] | O[C@H]1CN(C(=O)Nc2cc(cc3C(=O)N[C@@H](c23)c2cc(F)ccc2Cl)-c2cnn(c2)C(F)F)c2ccc(F)cc12 | (400 MHz, DMSO) δ9.08 (s, 1H), 8.87 (s, 1H), 8.68 (s, 1H), 8.38 (s, 1H), 8.01-7.65 (m, 4H), 7.37 (dd, J = 8.9, 5.1 Hz, 1H), 7.19-7.04 (m, 3H), 6.73-6.48 (m, 1H), 6.00 (s, 1H), 5.76 (d, J = 5.9 Hz, 1H), 5.12-5.03 (m, 1H), 3.69 (dd, J = 11.4, 3.6 Hz, 1H), 3.29-3.27 (m, 1H) | 571.9 | D | |
| I-2476 | 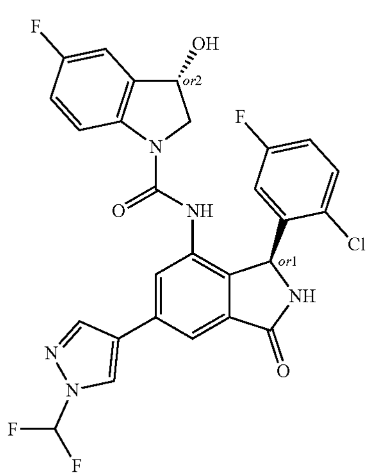 [SMILES: O=C1N[C@H](c2cc(F)ccc2Cl)c2c(NC(=O)N3C[C@@H](O)c4cc(F)ccc43)cc(-c3cnn(C(F)F)c3)cc21] | O[C@@H]1CN(C(=O)Nc2cc(cc3C(=O)N[C@@H](c23)c2cc(F)ccc2Cl)-c2cnn(c2)C(F)F)c2ccc(F)cc12 | (400 MHz, DMSO) δ9.10 (s, 1H), 8.87 (d, J = 0.8 Hz, 1H), 8.55 (s, 1H), 8.38 (d, J = 0.7 Hz, 1H), 8.00-7.68 (m, 4H), 7.34 (dd, J = 8.8, 5.2 Hz, 1H), 7.13-6.99 (m, 3H), 6.79-6.43 (m, 1H), 6.08 (s, 1H), 5.73 (d, J = 5.0 Hz, 1H), 5.15 (dt, J = 8.6, 4.5 Hz, 1H), 3.96 (dd, J = 11.1, 8.1 Hz, 1H), 3.28-3.20 (m, 1H) | 571.9 | E | |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-2477 | 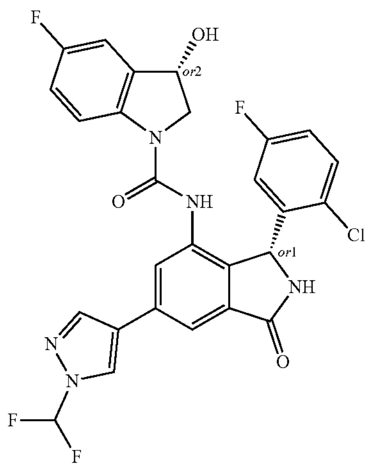 [SMILES: O=C1N[C@@H](c2cc(F)ccc2Cl)c2c(NC(=O)N3C[C@@H](O)c4cc(F)ccc43)cc(-c3cnn(C(F)F)c3)cc21] | O[C@@H]1CN(C(=O)Nc2cc(cc3C(=O)N[C@H](c23)c2cc(F)ccc2Cl)-c2cnn(c2)C(F)F)cc2ccc(F)cc12 | (400 MHz, DMSO) δ9.08 (s, 1H), 8.87 (d, J = 0.8 Hz, 1H), 8.68 (s, 1H), 8.38 (d, J = 0.8 Hz, 1H), 8.01-7.65 (m, 4H), 7.37 (dd, J = 8.9, 5.2 Hz, 1H), 7.18-7.03 (m, 3H), 6.76-6.40 (m, 1H), 6.00 (s, 1H), 5.76 (d, J = 5.9 Hz, 1H), 5.07 (t, J = 8.6 Hz, 1H), 3.69 (dd, J = 11.4, 3.6 Hz, 1H), 3.30-3.20 (m, 1H) | 571.9 | A | A |
| I-2478 | 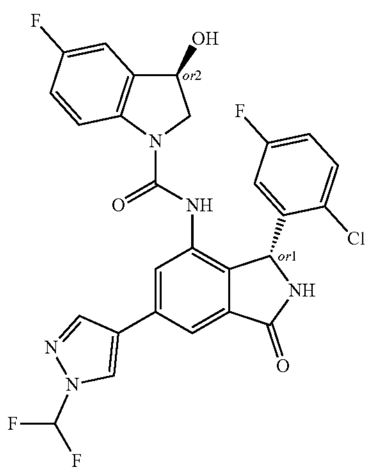 [SMILES: O=C1N[C@@H](c2cc(F)ccc2Cl)c2c(NC(=O)N3C[C@H](O)c4cc(F)ccc43)cc(-c3cnn(C(F)F)c3)cc21] | O[C@H]1CN(C(=O)Nc2cc(cc3C(=O)N[C@H](c23)c2cc(F)ccc2Cl)-c2cnn(c2)C(F)F)cc2ccc(F)cc12 | (400 MHz, DMSO) δ9.10 (s, 1H), 8.87 (d, J = 0.8 Hz, 1H), 8.55 (s, 1H), 8.38 (d, J = 0.7 Hz, 1H), 8.01-7.67 (m, 4H), 7.34 (dd, J = 8.9, 5.1 Hz, 1H), 7.14-6.99 (m, 3H), 6.75-6.48 (m, 1H), 6.08 (s, 1H), 5.73 (d, J = 4.9 Hz, 1H), 5.15 (dt, J = 8.7, 4.5 Hz, 1H), 3.96 (dd, J = 11.1, 8.1 Hz, 1H), 3.27-3.20 (m, 1H) | 571.9 | B | |
| I-2479 | 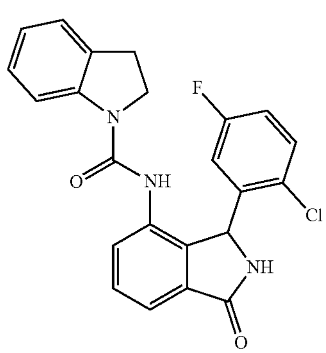 [SMILES: O=C1NC(c2cc(F)ccc2Cl)c2c(NC(=O)N3CCc4ccccc43)cccc21] | Fc1ccc(C1)c(c1)C1NC(=O)c2cccc(NC(=O)N3CCc4cccc34)c12 | (400 MHz, DMSO-d6) 9.05 (s, 1H), 8.54 (s, 1H), 7.70 (d, J = 8.0 Hz, 1H), 7.62-7.52 (m, 2H), 7.38 (dt, J = 8.3, 3.6 Hz, 2H), 7.20-7.11 (m, 2H), 7.14-7.05 (m, 1H), 6.89 (td, J = 7.5, 1.1 Hz, 1H), 6.57 (s, 1H), 6.02 (s, 1H), 3.85 (td, J = 10.0, 7.4 Hz, 1H), 3.34 (s, 1H), 3.12-2.93 (m, 2H). | 422.1 | A | B |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-2480 | 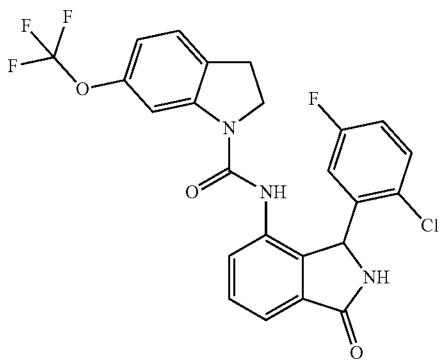 [SMILES: O=C1NC(c2cc(F)ccc2Cl)c2c(NC(=O)N3CCc4ccc(OC(F)(F)F)cc43)cccc21] | Fc1ccc(C1)c(c1)C1NC(=O)c2cccc(NC(=O)N3CCc4ccc(OC(F)(F)F)cc34)c12 | (400 MHz, DMSO-d6) δ9.07 (s, 1H), 8.68 (s, 1H), 7.70 (s, 1H), 7.64-7.53 (m, 2H), 7.43-7.34 (m, 2H), 7.26 (d, J = 8.1 Hz, 1H), 7.14 (ddd, J = 8.9, 7.9, 3.1 Hz, 1H), 6.86 (ddd, J = 8.2, 2.4, 1.1 Hz, 1H), 6.55 (s, 1H), 6.02 (s, 1H), 3.94 (td, J = 10.1, 6.8 Hz, 1H), 3.29 (s, 1H), 3.15-2.96 (m, 2H). | 506.4 | D | |
| I-2481 | 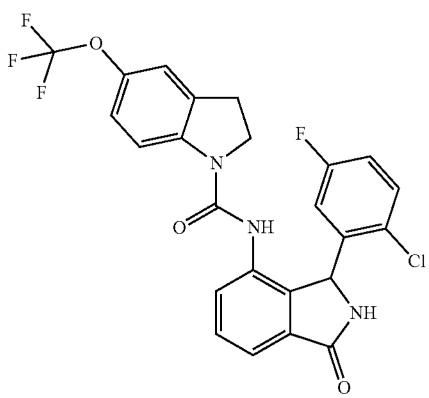 [SMILES: O=C1NC(c2cc(F)ccc2Cl)c2c(NC(=O)N3CCc4cc(OC(F)(F)F)ccc43)cccc21] | Fc1ccc(C1)c(c1)C1NC(=O)c2cccc(NC(=O)N3CCc4cc(OC(F)(F)F)ccc34)c12 | (400 MHz, DMSO-d6) δ9.05 (s, 1H), 8.63 (s, 1H), 7.76 (d, J = 8.8 Hz, 1H), 7.63-7.54 (m, 2H), 7.39 (dd, J = 8.0, 6.2 Hz, 2H), 7.22-7.08 (m, 3H), 6.47 (s, 1H), 6.00 (s, 1H), 3.92 (td, J = 10.1, 7.1 Hz, 1H), 3.25 (s, 1H), 3.09 (td, J = 19.3, 18.0, 8.3 Hz, 2H). | 506.2 | D | |
| I-2482 | 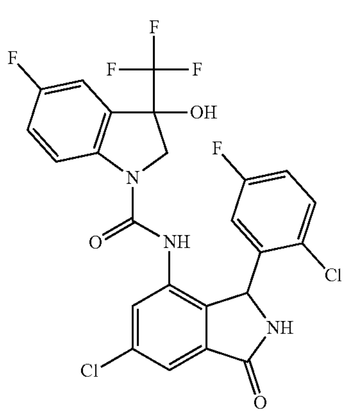 [SMILES: O=C1NC(c2cc(F)ccc2Cl)c2c(NC(=O)N3CC(O)(C(F)(F)F)c4cc(F)ccc43)cc(Cl)cc21] | OC1(CN(C(=O)Nc2cc(Cl)cc3C(=O)NC(c23)c2cc(F)cc2Cl)c2ccc(F)cc12)C(F)(F)F | (400 MHz, DMSO-d6) δ 9.26 (br s, 1H), 8.93 (br s, 0.5H), 8.85 (br s, 0.5H), 7.60 (d, J = 1.5 Hz, 1H), 7.57 (d, J = 1.8 Hz, 0.5H), 7.47 (d, J = 1.8 Hz, 0.5H), 7.38-7.24 (m, 4H), 7.24-7.18 (m, 1H), 7.17-7.08 (m, 1H), 6.65 (br s, 1H), 6.03 (br s, 1H), 4.14 (d, J = 12.3 Hz, 1H), 3.95 (d, J = 12.0 Hz, 0.5H), 3.48 (submerged dd, J = 28.0, 12.6 Hz, 1H). 1:1 mixture of diastereomers. | 558.0 | A | A |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-2483 | 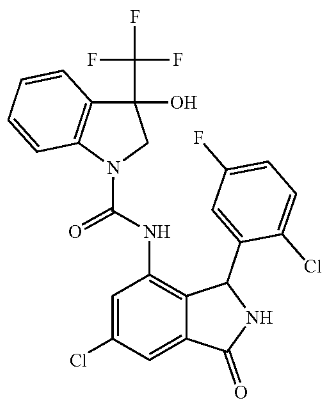 [SMILES: O=C1NC(c2cc(F)ccc2Cl)c2c(NC(=O)N3CC(O)(C(F)(F)F)c4ccccc43)cc(Cl)cc21] | OC1(CN(C(=O)Nc2cc(Cl)cc3C(=O)NC(c23)c2cc(F)ccc2Cl)c2ccccc12)C(F)(F)F | (400 MHz, DMSO-d6) δ 9.27 (br s, 1H), 8.91 (br s, 0.5H), 8.81 (br s, 0.5H), 7.60 (d, J = 1.1 Hz, 1H), 7.49 (d, J = 1.8 Hz, 1H), 7.43 (d, J = 7.6 Hz, 1H), 7.40-7.30 (m, 3H), 7.19-7.02 (m, 3H), 6.68 (br s, 1H), 6.08 (br s, 0.5H), 6.03 (br s, 0.5H), 4.09 (d, J = 12.0 Hz, 0.5H), 3.92 (d, J = 12.0 Hz, 0.5H), 3.49 (submerged overlapped dd, J = 28.0, 12.6 Hz, 1H). 1:1 mixture of diastereomers. | 540.0 | A | A |
| I-2484 | 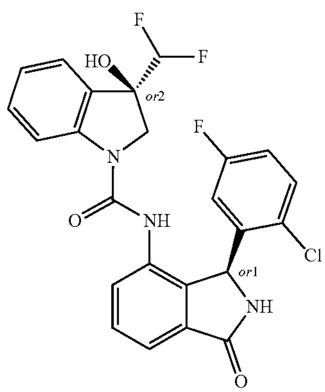 [SMILES: O=C1N[C@H](c2cc(F)ccc2Cl)c2c(NC(=O)N3C[C@@](O)(C(F)F)c4ccccc43)cccc21] | O[C@]1(CN(C(=O)Nc2cccc3C(=O)N[C@@H](c23)c2cc(F)ccc2Cl)c2ccccc12)C(F)F | | 487.9 | | E |
| I-2485 | 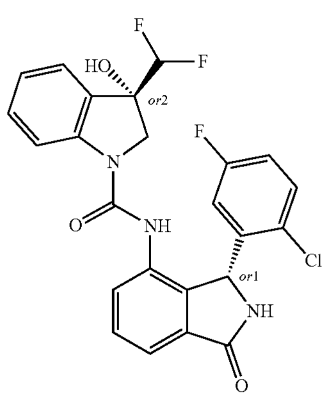 [SMILES: O=C1N[C@@H](c2cc(F)ccc2Cl)c2c(NC(=O)N3C[C@](O)(C(F)F)c4ccccc43)cccc21] | O[C@@]1(CN(C(=O)Nc2ccc3C(=O)N[C@H](c23)c2cc(F)ccc2Cl)c2ccccc12)C(F)F | | 487.9 | | D |

TABLE 2-continued

Representative Compounds of the Invention with Bioactivity Data.

| Ex. No. | Structure | SMILES | $^1$H NMR | MS | ADP-Glo IC$_{50}$ | MCF 10A IC$_{50}$ |
|---|---|---|---|---|---|---|
| I-2486 | 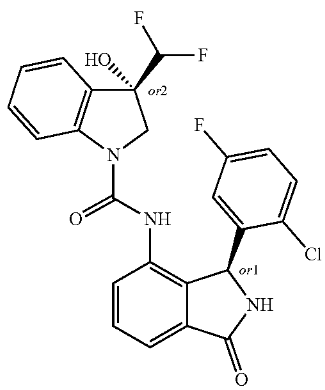 [SMILES: O=C1N[C@H](c2cc(F)ccc2Cl)c2c(NC(=O)N3C[C@](O)(C(F)F)c4ccccc43)cccc21] | O[C@@]1(CN(C(=O)Nc2cccc3C(=O)N[C@@H](c23)c2cc(F)ccc2Cl)c2ccccc12)C(F)F | | 487.9 | E | |
| I-2487 | 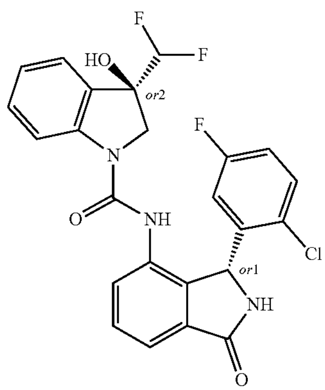 [SMILES: O=C1N[C@@H](c2cc(F)ccc2Cl)c2c(NC(=O)N3C[C@@](O)(C(F)F)c4ccccc43)cccc21] | O[C@]1(CN(C(=O)Nc2cccc3C(=O)N[C@H](c23)c2cc(F)ccc2Cl)c2ccccc12)C(F)F | | 487.9 | A | A |
| I-2488 | 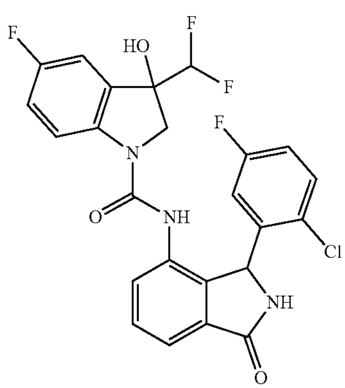 [SMILES: O=C1NC(c2cc(F)ccc2Cl)c2c(NC(=O)N3CC(O)(C(F)F)c4cc(F)ccc43)cccc21] | OC1(CN(C(=O)Nc2cccc3C(=O)NC(c23)c2cc(F)ccc2C1)c2ccc(F)cc12)C(F)F | (400 MHz, DMSO-d6) δ as a ca. 1:1 mixture of diastereomers, δ 9.09 (br. s, 1H), 9.07 (br. s, 1H), 8.75 (br. s, 1H), 8.65 (br. s, 1H), 7.88 (dd, J = 8.1, 4.0 Hz, 1H), 7.79 (dd, J = 8.9, 4.7 Hz, 1H), 7.62-7.54 (m, 4H), 7.46 (dd, J = 7.4, 1.5 Hz, 1H), 7.40-7.28 (m, 3H), 7.28-7.21 (m, 2H), 7.21-7.08 (m, 4H), 6.70 (s, 1H), 6.64 (s, 1H), 6.55 (br. s, 2H), 6.27 (td, J = 55.3, 3.1 Hz, 2H), 6.08 (br. s, 1H), 6.03 (br. s, 1H), 4.10 (d, J = 11.8 Hz, 1H), 3.86 (d, J = 11.8 Hz, 1H), 3.45 (d, J = 11.7 Hz, 1H), 3.32-3.28 (m, 1H). Multiplet at 3.32-3.28 ppm is partially obscured by the peak for residual H2O. | 506.3 | A | B |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-2489 | 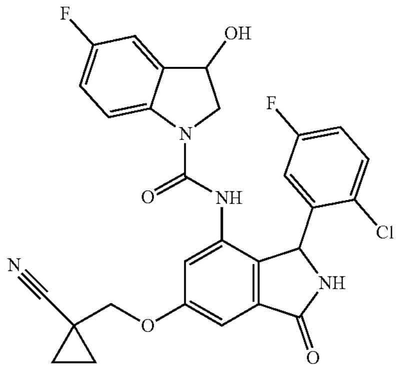 [SMILES: N#CC1(COc2cc(NC(=O)N3CC(O)c4cc(F)ccc43)c3c(c2)C(=O)NC3c2cc(F)ccc2Cl)CC1] | OC1CN(C(=O)Nc2cc(OCC3(CC3)C#N)cc3C(=O)NC(c23)c2cc(F)ccc2C1)c2ccc(F)cc12 | (400 MHz, DMSO-d6) δ 9.05 (br s, 1 H), 8.60 (br s, 1 H), 7.81 (dd, J = 8.5, 4.7 Hz, 0.5 H), 7.69 (dd, J = 8.9, 4.7 Hz, 0.5 H), 7.35 (dt, J = 9.3, 4.8 Hz, 1 H), 7.18-6.98 (m, 5 H), 6.57 (br s, 1 H), 6.03 (br s, 0.5 H), 5.94 (br s, 0.5 H), 5.77 (br s, 1 H), 5.13 (dd, J = 7.9, 3.9 Hz, 0.5 H), 5.06 (dd, J = 7.8, 3.2 Hz, 0.5 H), 4.19 (dd, J = 10.4, 3.6 Hz, 1 H), 4.11 (dd, J = 10.4, 2.8 Hz, 1 H), 3.90 (dd, J = 11.0, 8.1 Hz, 0.5 H), 3.66 (dd, J = 11.2, 3.5 Hz, 0.5 H), 3.27 (d, J = 4.0 Hz, 0.5 H), 3.24 (d, J = 3.9 Hz, 0.5 H), 1.39 (app q, J = 4.5 Hz, 2 H), 1.19 (dd, J = 7.0, 4.7 Hz, 2 H). ~1:1 mixture of diastereomers. | 551.3 | A | C |
| I-2490 | 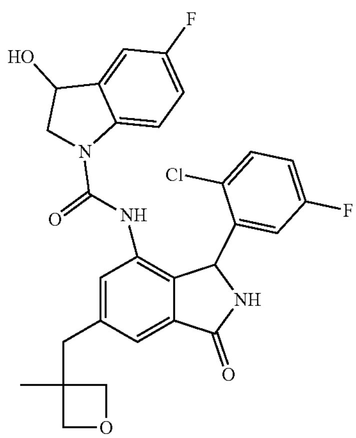 [SMILES: CC1(Cc2cc(NC(=O)N3CC(O)c4cc(F)ccc43)c3c(c2)C(=O)NC3c2cc(F)ccc2Cl)COC1] | CC1(Cc2cc3C(=O)NC(c3c(NC(=O)N3CC(O)c4cc(F)cc34)c2)c2cc(F)cc2Cl)COC1 | | 540.0 | | C |
| I-2491 | 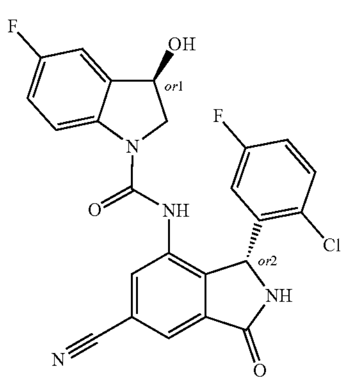 [SMILES: N#Cc1cc(NC(=O)N2C[C@H](O)c3cc(F)ccc32)c2c(c1)C(=O)N[C@H]2c1cc(F)ccc1Cl] | O[C@H]1CN(C(=O)Nc2cc(cc3C(=O)N[C@H](c23)c2cc(F)cc2Cl)C#N)c2ccc(F)cc12 | (400 MHz, DMSO-d6) 9.37 (s, 1H), 8.76 (s, 1H), 8.02 (d, J = 1.4 Hz, 1H), 7.88 (d, J = 1.4 Hz, 1H), 7.70 (dd, J = 8.9, 4.7 Hz, 1H), 7.37 (dd, J = 8.9, 5.2 Hz, 1H), 7.12 (td, J = 8.3, 3.0 Hz, 2H), 7.05 (td, J = 9.1, 2.8 Hz, 1H), 6.17 (s, 1H), 5.76 (d, J = 5.0 Hz, 1H), 5.15 (dt, J = 8.5, 4.4 Hz, 1H), 3.92 (dd, J = 11.0, 8.0 Hz, 1H), 3.22 (d, J = 3.9 Hz, 1H), 3.09 (d, J = 7.0 Hz, 1H). | 481.1 | B | |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-2492 | 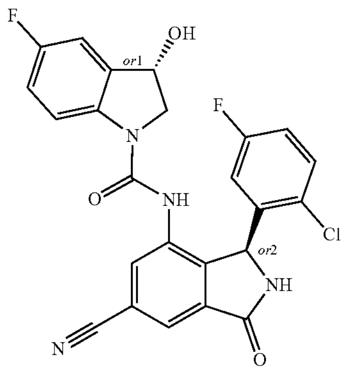 [SMILES: N#Cc1cc(NC(=O)N2C[C@@H](O)c3cc(F)ccc32)c2c(c1)C(=O)N[C@@H]2c1cc(F)ccc1Cl] | O[C@@H]1CN(C(=O)Nc2cc(cc3C(=O)N[C@@H](c23)c2cc(F)ccc2Cl)C#N)c2ccc(F)cc12 | | 482.3 | C | |
| I-2493 | 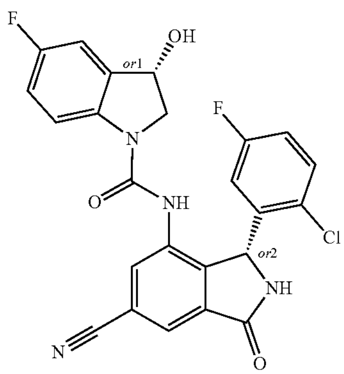 [SMILES: N#Cc1cc(NC(=O)N2C[C@@H](O)c3cc(F)ccc32)c2c(c1)C(=O)N[C@H]2c1cc(F)ccc1Cl] | O[C@@H]1CN(C(=O)Nc2cc(cc3C(=O)N[C@H](c23)c2cc(F)ccc2Cl)C#N)c2ccc(F)cc12 | (400 MHz, DMSO-d6) 9.37 (s, 1H), 8.89 (s, 1H), 8.75 (s, 1H), 8.04-7.99 (m, 2H), 7.87 (d, J = 1.4 Hz, 1H), 7.82-7.77 (m, 1H), 7.70 (dd, J = 8.9, 4.7 Hz, 1H), 7.38 (dt, J = 8.9, 5.5 Hz, 2H), 6.70 (s, 2H), 5.15 (dt, J = 8.6, 4.4 Hz, 1H), 3.92 (dd, J = 11.0, 8.0 Hz, 1H), 3.23 (dd, J = 11.0, 4.0 Hz, 1H). | 481.3 | B | |
| I-2494 | 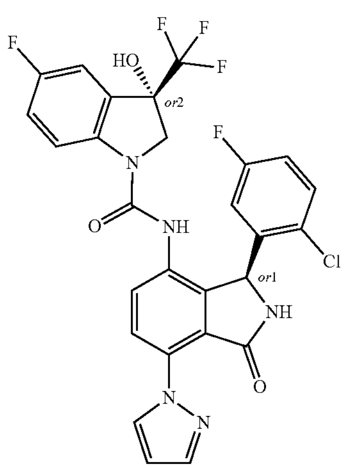 [SMILES: O=C1N[C@H](c2cc(F)ccc2Cl)c2c(NC(=O)N3C[C@](O)(C(F)(F)F)c4cc(F)ccc43)ccc(-n3cccn3)c21] | O[C@@]1(CN(C(=O)Nc2cc(c3C(=O)N[C@@H](c23)c2cc(F)ccc2Cl)-n2cccn2)c2ccc(F)cc12)C(F)(F)F | (400 MHz, DMSO-d6) 9.28 (s, 1H), 8.74 (s, 1H), 8.69-8.64 (m, 1H), 7.89-7.81 (m, 2H), 7.78 (d, J = 1.7 Hz, 1H), 7.58 (d, J = 8.6 Hz, 1H), 7.42 (s, 1H), 7.36 (dd, J = 8.9, 5.1 Hz, 1H), 7.30-7.19 (m, 2H), 7.18-7.09 (m, 1H), 6.76 (s, 1H), 6.51 (t, J = 2.1 Hz, 1H), 6.11 (s, 1H), 4.23 (d, J = 12.0 Hz, 1H), 3.50 (d, J = 11.1 Hz, 1H). | 590.2 | D | |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-2495 | 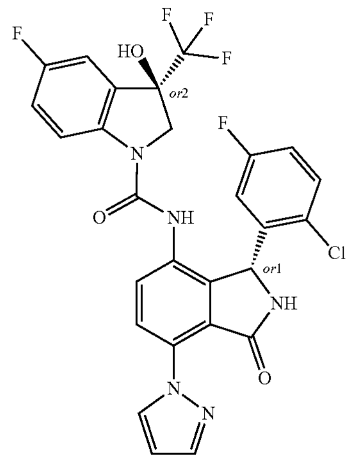 [SMILES: O=C1N[C@@H](c2cc(F)ccc2Cl)c2c(NC(=O)N3C[C@@](O)(C(F)(F)F)c4cc(F)ccc43)ccc(-n3cccn3)c21] | O[C@]1(CN(C(=O)Nc2ccc(c3C(=O)N[C@H](c23)c2cc(F)cc2Cl)-n2cccn2)c2ccc(F)cc12)C(F)(F)F | (400 MHz, DMSO-d6) 9.26 (s, 1H), 8.82 (s, 1H), 8.65 (s, 1H), 7.93 (s, 1H), 7.85 (d, J = 8.5 Hz, 1H), 7.78 (d, J = 1.8 Hz, 1H), 7.50 (d, J = 8.5 Hz, 1H), 7.42 (s, 1H), 7.39-7.18 (m, 3H), 7.16 (td, J = 8.4, 3.1 Hz, 1H), 6.76 (s, 1H), 6.54-6.48 (m, 1H), 6.07 (s, 1H), 4.01 (d, J = 12.1 Hz, 1H), 3.54 (d, J = 12.0 Hz, 1H). | 590.2 | E | |
| I-2496 | 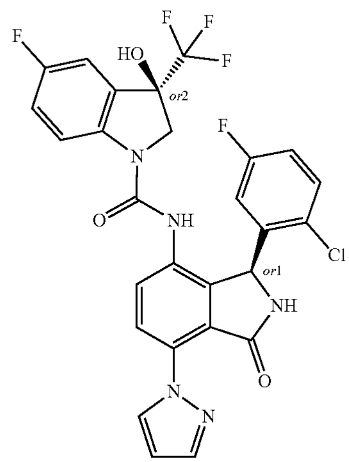 [SMILES: O=C1N[C@H](c2cc(F)ccc2Cl)c2c(NC(=O)N3C[C@@](O)(C(F)(F)F)c4cc(F)ccc43)ccc(-n3cccn3)c21] | O[C@]1(CN(C(=O)Nc2ccc(c3C(=O)N[C@@H](c23)c2cc(F)cc2Cl)-n2cccn2)c2ccc(F)cc12)C(F)(F)F | (400 MHz, DMSO-d6) 9.27 (s, 1H), 8.73 (s, 1H), 8.66 (s, 1H), 7.89-7.81 (m, 2H), 7.78 (d, J = 1.7 Hz, 1H), 7.58 (d, J = 8.6 Hz, 1H), 7.41 (s, 1H), 7.36 (dd, J = 8.9, 5.1 Hz, 1H), 7.30-7.19 (m, 2H), 7.18-7.09 (m, 1H), 6.84 (s, 1H), 6.51 (dd, J = 2.5, 1.8 Hz, 1H), 6.11 (s, 1H), 4.22 (d, J = 12.0 Hz, 1H), 3.51 (s, 1H). | 590.2 | D | |
| I-2497 | 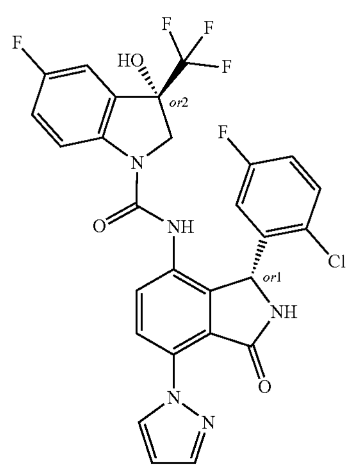 [SMILES: O=C1N[C@@H](c2cc(F)ccc2Cl)c2c(NC(=O)N3C[C@](O)(C(F)(F)F)c4cc(F)ccc43)ccc(-n3cccn3)c21] | O[C@@]1(CN(C(=O)Nc2cc(c3C(=O)N[C@H](c23)c2cc(F)cc2Cl)-n2cccn2)c2ccc(F)cc12)C(F)(F)F | (400 MHz, DMSO-d6) 9.27 (s, 1H), 8.83 (s, 1H), 8.65 (s, 1H), 7.93 (d, J = 6.6 Hz, 1H), 7.86 (d, J = 8.5 Hz, 1H), 7.78 (d, J = 1.7 Hz, 1H), 7.50 (d, J = 8.5 Hz, 1H), 7.43 (s, 1H), 7.35 (dd, J = 8.9, 5.1 Hz, 1H), 7.32-7.12 (m, 3H), 6.76 (s, 1H), 6.54-6.48 (m, 1H), 6.07 (s, 1H), 4.02 (d, J = 12.0 Hz, 1H), 3.55 (d, J = 12.1 Hz, 1H). | 590.2 | A | A |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-2498 | 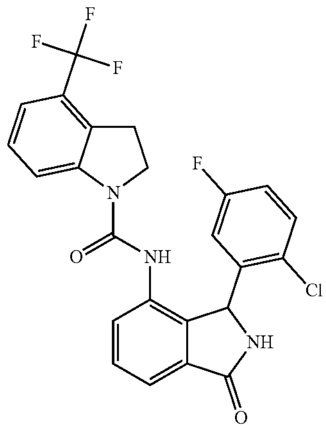 [SMILES: O=C1NC(c2cc(F)ccc2Cl)c2c(NC(=O)N3CCc4c3cccc4C(F)(F)F)cccc21] | Fc1ccc(C1)c(c1)C1NC(=O)c2cccc(NC(=O)N3CCc4c3ccc4C(F)(F)F)c12 | (400 MHz, DMSO-d6) δ 9.06 (s, 1H), 8.72 (s, 1H), 8.01 (d, J = 8.1 Hz, 1H), 7.63-7.55 (m, 2H), 7.43-7.32 (m, 3H), 7.25-7.13 (m, 2H), 6.57 (s, 1H), 6.00 (s, 1H), 3.97 (td, J = 10.0, 6.6 Hz, 1H), 3.34 (s, 3H). | 490.1 | D | |
| I-2499 | 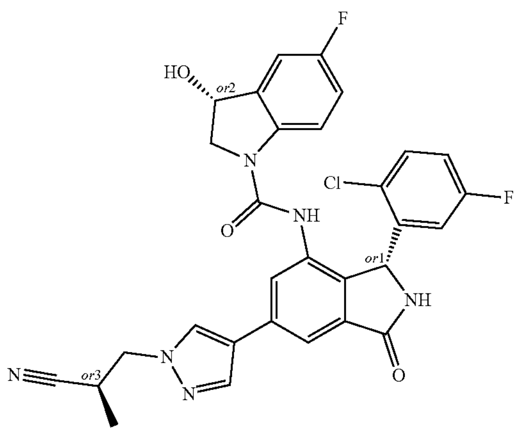 [SMILES: C[C@@H](C#N)Cn1cc(-c2cc(NC(=O)N3C[C@H](O)c4cc(F)ccc43)c3c(c2)C(=O)N[C@H]3c2cc(F)ccc2Cl)cn1] | C[C@H](Cn1cc(cn1)-c1cc2C(=O)N[C@H](c2c(NC(=O)N2C[C@H](O)c3cc(F)ccc23)c1)c1cc(F)ccc1Cl)C#N | (400 MHz, DMSO-d6) 9.08 (s, 1H), 8.55 (s, 1H), 8.40 (d, J = 0.8 Hz, 1H), 8.10 (d, J = 0.7 Hz, 1H), 7.80 (d, J = 1.5 Hz, 1H), 7.73 (dd, J = 8.9, 4.7 Hz, 1H), 7.64 (d, J = 1.5 Hz, 1H), 7.35 (dd, J = 8.9, 5.2 Hz, 1H), 7.17-6.97 (m, 3H), 6.64 (s, 1H), 6.09 (s, 1H), 5.75 (d, J = 5.0 Hz, 1H), 5.16 (dt, J = 8.6, 4.6 Hz, 1H), 4.58-4.29 (m, 2H), 3.98 (dd, J = 11.1, 8.1 Hz, 1H), 3.52-3.40 (m, 1H), 3.24 (dd, J = 11.0, 4.1 Hz, 1H), 1.28 (d, J = 7.1 Hz, 3H). | 589.3 | D | |
| I-2500 | 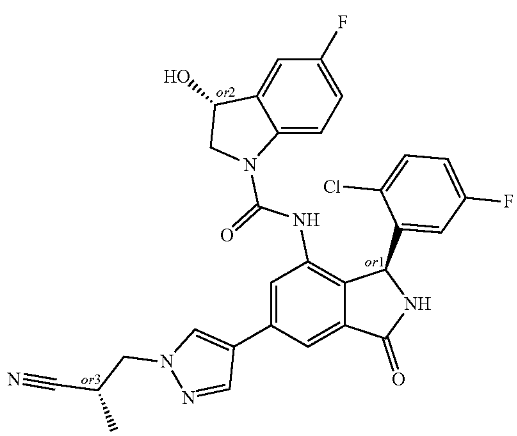 [SMILES: C[C@H](C#N)Cn1cc(-c2cc(NC(=O)N3C[C@H](O)c4cc(F)ccc43)c3c(c2)C(=O)N[C@@H]3c2cc(F)ccc2Cl)cn1] | C[C@@H](Cn1cc(cn1)-c1cc2C(=O)N[C@@H](c2c(NC(=O)N2C[C@H](O)c3cc(F)ccc23)c1)c1cc(F)ccc1Cl)C#N | (400 MHz, DMSO-d6) 9.08 (s, 1H), 8.54 (s, 1H), 8.40 (s, 1H), 8.10 (s, 1H), 7.80 (d, J = 1.5 Hz, 1H), 7.73 (dd, J = 8.9, 4.7 Hz, 1H), 7.63 (d, J = 1.5 Hz, 1H), 7.35 (dd, J = 8.9, 5.1 Hz, 1H), 7.16-6.99 (m, 3H), 6.63 (s, 1H), 6.09 (s, 1H), 5.74 (d, J = 5.0 Hz, 1H), 5.16 (dt, J = 8.6, 4.5 Hz, 1H), 4.53-4.31 (m, 2H), 3.98 (dd, J = 11.1, 8.1 Hz, 1H), 3.53-3.42 (m, 1H), 3.24 (dd, J = 11.2, 4.1 Hz, 1H), 1.28 (d, J = 7.1 Hz, 3H). | 589.3 | B | |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-2501 | 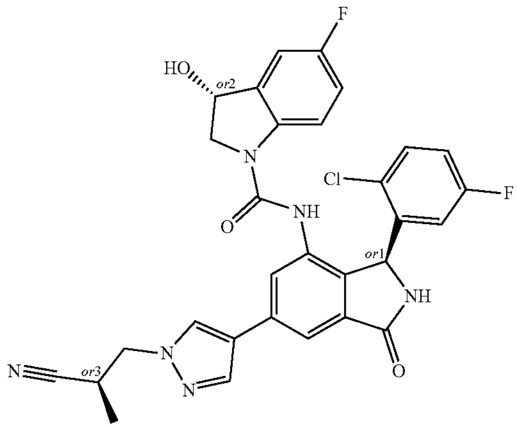 [SMILES: C[C@@H](C#N)Cn1cc(-c2cc(NC(=O)N3C[C@H](O)c4cc(F)ccc43)c3c(c2)C(=O)N[C@@H]3c2cc(F)ccc2Cl)cn1] | C[C@H](Cn1cc(cn1)-c1cc2C(=O)N[C@@H](c2c(NC(=O)N2C[C@H](O)c3cc(F)ccc23)c1)c1cc(F)ccc1Cl)C#N | (400 MHz, DMSO-d6) 9.08 (s, 1H), 8.54 (s, 1H), 8.40 (s, 1H), 8.09 (s, 1H), 7.80 (d, J = 1.5 Hz, 1H), 7.73 (dd, J = 8.9, 4.7 Hz, 1H), 7.63 (d, J = 1.6 Hz, 1H), 7.35 (dd, J = 8.9, 5.1 Hz, 1H), 7.16-6.97 (m, 3H), 6.63 (s, 1H), 6.09 (s, 1H), 5.74 (d, J = 5.0 Hz, 1H), 5.16 (dt, J = 8.6, 4.5 Hz, 1H), 4.53-4.33 (m, 2H), 3.98 (dd, J = 11.1, 8.1 Hz, 1H), 3.48 (h, J = 7.0 Hz, 1H), 3.25 (dd, J = 11.1, 4.1 Hz, 1H), 1.27 (d, J = 7.1 Hz, 3H). | 589.3 | B | |
| I-2502 | 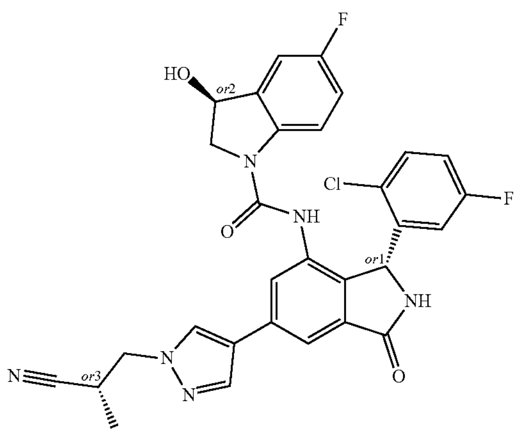 [SMILES: C[C@H](C#N)Cn1cc(-c2cc(NC(=O)N3C[C@@H](O)c4cc(F)ccc43)c3c(c2)C(=O)N[C@H]3c2cc(F)ccc2Cl)cn1] | C[C@@H](Cn1cc(cn1)-c1cc2C(=O)N[C@H](c2c(NC(=O)N2C[C@@H](O)c3cc(F)ccc23)c1)c1cc(F)ccc1Cl)C#N | (400 MHz, DMSO-d6) 9.08 (s, 1H), 8.54 (s, 1H), 8.40 (s, 1H), 8.09 (s, 1H), 7.80 (d, J = 1.5 Hz, 1H), 7.73 (dd, J = 8.9, 4.7 Hz, 1H), 7.63 (d, J = 1.5 Hz, 1H), 7.35 (dd, J = 8.9, 5.1 Hz, 1H), 7.16-6.93 (m, 3H), 6.63 (s, 1H), 6.09 (s, 1H), 5.74 (d, J = 5.0 Hz, 1H), 5.16 (dt, J = 8.7, 4.5 Hz, 1H), 4.51-4.35 (m, 2H), 3.98 (dd, J = 11.1, 8.1 Hz, 1H), 3.48 (p, J = 6.9 Hz, 1H), 3.25 (dd, J = 11.2, 4.1 Hz, 1H), 1.27 (d, J = 7.1 Hz, 3H). | 589.3 | D | |
| I-2503 | 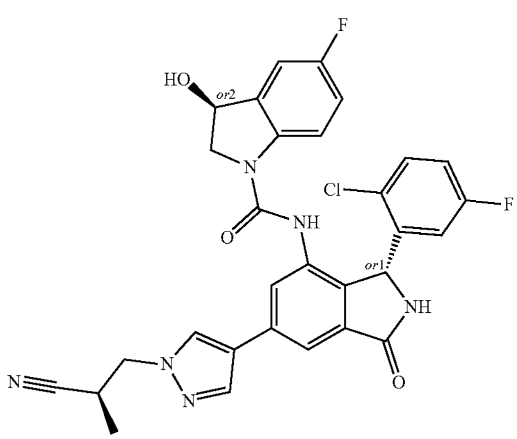 [SMILES: C[C@@H](C#N)Cn1cc(-c2cc(NC(=O)N3C[C@@H](O)c4cc(F)ccc43)c3c(c2)C(=O)N[C@H]3c2cc(F)ccc2Cl)cn1] | C[C@H](Cn1cc(cn1)-c1cc2C(=O)N[C@H](c2c(NC(=O)N2C[C@@H](O)c3cc(F)ccc23)c1)c1cc(F)ccc1Cl)C#N | (400 MHz, DMSO-d6) 9.06 (s, 1H), 8.67 (s, 1H), 8.40 (s, 1H), 8.10 (d, J = 2.4 Hz, 1H), 7.85 (d, J = 3.9 Hz, 1H), 7.79 (s, 1H), 7.60-7.55 (m, 1H), 7.37 (dd, J = 8.9, 5.1 Hz, 1H), 7.20-7.05 (m, 3H), 6.64 (s, 1H), 6.00 (s, 1H), 5.77 (d, J = 6.0 Hz, 1H), 5.09 (s, 1H), 4.51-4.31 (m, 2H), 3.71 (dd, J = 11.4, 3.6 Hz, 1H), 3.47 (p, J = 7.0 Hz, 1H), 3.28 (s, 1H), 1.28 (dd, J = 7.1, 1.7 Hz, 3H). | 589.2 | A | C |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-2504 | 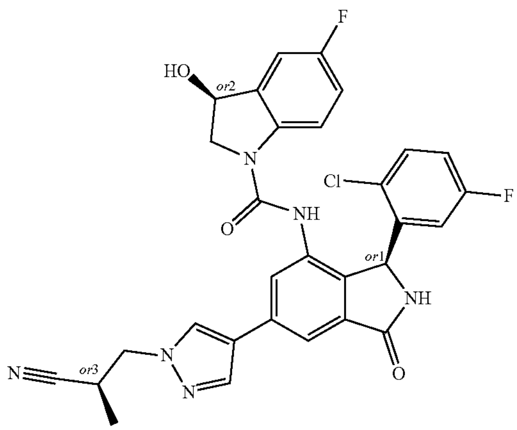 [SMILES: C[C@@H](C#N)Cn1cc(-c2cc(NC(=O)N3C[C@@H](O)c4cc(F)ccc43)c3c(c2)C(=O)N[C@@H]3c2cc(F)ccc2Cl)cn1] | C[C@@H](Cn1c c(cn1)-c1cc2C(=O)N[C@@H](c2c(NC(=O)N2C[C@@H](O)c3cc(F)cc c23)c1)c1cc(F)cc c1Cl)C#N | (400 MHz, DMSO-d6) 9.06 (s, 1H), 8.67 (s, 1H), 8.40 (s, 1H), 8.10 (s, 1H), 7.85 (dd, J = 8.9, 4.7 Hz, 1H), 7.79 (d, J = 1.5 Hz, 1H), 7.58 (d, J = 1.5 Hz, 1H), 7.37 (dd, J = 8.9, 5.1 Hz, 1H), 7.19-7.06 (m, 3H), 6.62 (s, 1H), 6.00 (s, 1H), 5.77 (d, J = 5.9 Hz, 1H), 5.16-4.99 (m, 1H), 4.47-4.34 (m, 2H), 3.71 (dd, J = 11.4, 3.6 Hz, 1H), 3.54-3.41 (m, 1H), 3.27 (s, 1H), 1.28 (d, J = 7.1 Hz, 3H). | 589.2 | D | |
| I-2505 | 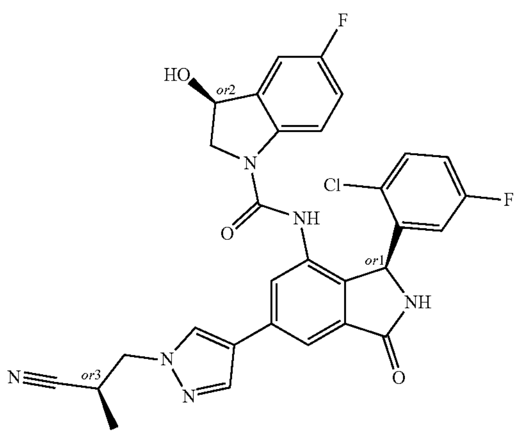 [SMILES: C[C@@H](C#N)Cn1cc(-c2cc(NC(=O)N3C[C@@H](O)c4cc(F)ccc43)c3c(c2)C(=O)N[C@@H]3c2cc(F)ccc2Cl)cn1] | C[C@H](Cn1cc(c n1)-c1cc2C(=O)N[C@@H](c2c(NC(=O)N2C[C@@H](O)c3cc(F)cc c23)c1)c1cc(F)cc c1Cl)C#N | (400 MHz, DMSO-d6) 9.06 (s, 1H), 8.67 (s, 1H), 8.40 (s, 1H), 8.09 (s, 1H), 7.85 (dd, J = 8.8, 4.7 Hz, 1H), 7.79 (d, J = 1.5 Hz, 1H), 7.58 (d, J = 1.5 Hz, 1H), 7.38 (dd, J = 8.9, 5.1 Hz, 1H), 7.21-7.05 (m, 3H), 6.62 (s, 1H), 6.00 (s, 1H), 5.77 (d, J = 5.9 Hz, 1H), 5.08 (q, J = 5.8, 3.6 Hz, 1H), 4.48-4.33 (m, 2H), 3.71 (dd, J = 11.4, 3.6 Hz, 1H), 3.48 (h, J = 7.0 Hz, 1H), 3.28 (s, 1H), 1.28 (d, J = 7.0 Hz, 3H). | 589.3 | D | |
| I-2506 | 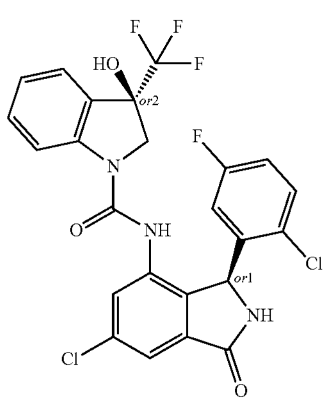 [SMILES: O=C1N[C@H](c2cc(F)ccc2Cl)c2c(NC(=O)N3C[C@@](O)(C(F)(F)F)c4ccccc43)cc(Cl)cc21] | O[C@]1(CN(C(=O)Nc2cc(Cl)cc3C(=O)N[C@@H](c23)c2cc(F)ccc2Cl)c2ccccc12)C(F)(F)F | | | D | |

TABLE 2-continued

Representative Compounds of the Invention with Bioactivity Data.

| Ex. No. | Structure | SMILES | $^1$H NMR | MS | ADP-Glo IC$_{50}$ | MCF 10A IC$_{50}$ |
|---|---|---|---|---|---|---|
| I-2507 | 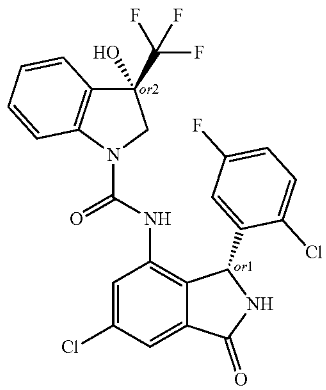 [SMILES: O=C1N[C@@H](c2cc(F)ccc2Cl)c2c(NC(=O)N3C[C@](O)(C(F)(F)F)c4ccccc43)cc(Cl)cc21] | O[C@@]1(CN(C(=O)Nc2cc(Cl)cc3C(=O)N[C@H](c23)c2cc(F)ccc2Cl)c2cccc12)C(F)(F)F | | | D | |
| I-2508 | 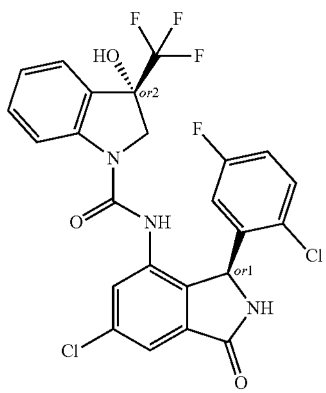 [SMILES: O=C1N[C@H](c2cc(F)ccc2Cl)c2c(NC(=O)N3C[C@](O)(C(F)(F)F)c4ccccc43)cc(Cl)cc21] | O[C@@]1(CN(C(=O)Nc2cc(Cl)cc3C(=O)N[C@@H](c23)c2cc(F)ccc2Cl)c2cccc12)C(F)(F)F | | | D | |
| I-2509 | 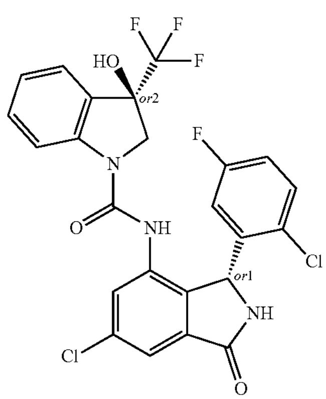 [SMILES: O=C1N[C@@H](c2cc(F)ccc2Cl)c2c(NC(=O)N3C[C@@](O)(C(F)(F)F)c4ccccc43)cc(Cl)cc21] | O[C@]1(CN(C(=O)Nc2cc(Cl)cc3C(=O)N[C@H](c23)c2cc(F)cc2Cl)c2cccc12)C(F)(F)F | | | A | A |

TABLE 2-continued

Representative Compounds of the Invention with Bioactivity Data.

| Ex. No. | Structure | SMILES | $^1$H NMR | MS | ADP-Glo IC$_{50}$ | MCF 10A IC$_{50}$ |
|---|---|---|---|---|---|---|
| I-2510 | 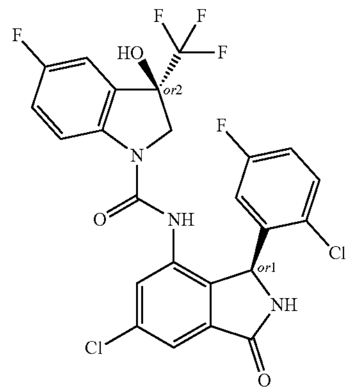 [SMILES: O=C1N[C@H](c2cc(F)ccc2Cl)c2c(NC(=O)N3C[C@@](O)(C(F)(F)F)c4cc(F)ccc43)cc(Cl)cc21] | O[C@]1(CN(C(=O)Nc2cc(Cl)cc3C(=O)N[C@@H](c23)c2cc(F)ccc2Cl)c2ccc(F)cc12)C(F)(F)F | | | D | |
| I-2511 | 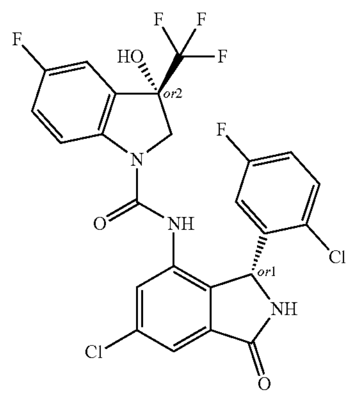 [SMILES: O=C1N[C@@H](c2cc(F)ccc2Cl)c2c(NC(=O)N3C[C@](O)(C(F)(F)F)c4cc(F)ccc43)cc(Cl)cc21] | O[C@@]1(CN(C(=O)Nc2cc(Cl)cc3C(=O)N[C@H](c23)c2cc(F)ccc2Cl)c2ccc(F)cc12)C(F)(F)F | | | B | |
| I-2512 | 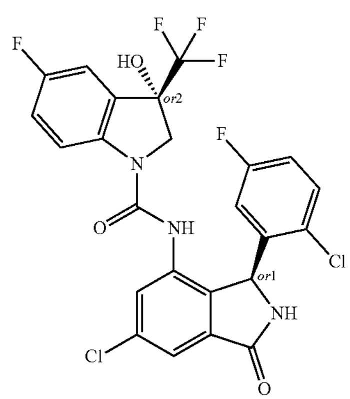 [SMILES: O=C1N[C@H](c2cc(F)ccc2Cl)c2c(NC(=O)N3C[C@](O)(C(F)(F)F)c4cc(F)ccc43)cc(Cl)cc21] | O[C@@]1(CN(C(=O)Nc2cc(Cl)cc3C(=O)N[C@@H](c23)c2cc(F)ccc2C1)c2ccc(F)cc12)C(F)(F)F | | | D | |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-2513 | 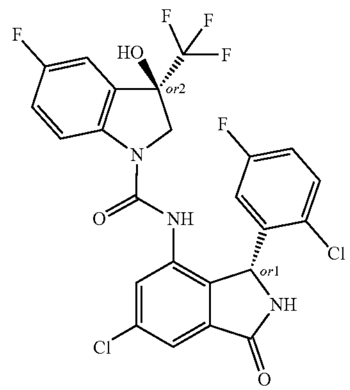 [SMILES: O=C1N[C@@H](c2cc(F)ccc2Cl)c2c(NC(=O)N3C[C@@](O)(C(F)(F)F)c4cc(F)ccc43)cc(Cl)cc21] | O[C@]1(CN(C(=O)Nc2ccc(Cl)cc3C(=O)N[C@H](c23)c2cc(F)ccc2Cl)c2ccc(F)cc12)C(F)(F)F | | | A | A |
| I-2514 | 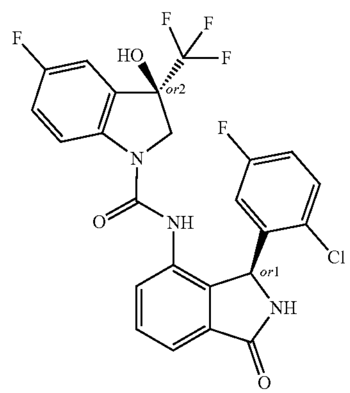 [SMILES: O=C1N[C@H](c2cc(F)ccc2Cl)c2c(NC(=O)N3C[C@@](O)(C(F)(F)F)c4cc(F)ccc43)cccc21] | O[C@]1(CN(C(=O)Nc2cccc3C(=O)N[C@@H](c23)c2cc(F)ccc2Cl)c2cc(F)cc12)C(F)(F)F | | | | E |
| I-2515 | 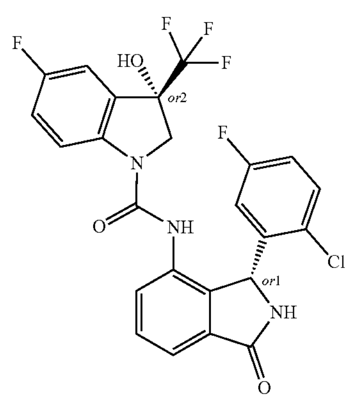 [SMILES: O=C1N[C@@H](c2cc(F)ccc2Cl)c2c(NC(=O)N3C[C@](O)(C(F)(F)F)c4cc(F)ccc43)cccc21] | O[C@@]1(CN(C(=O)Nc2cccc3C(=O)N[C@H](c23)c2cc(F)ccc2Cl)c2cc(F)cc12)C(F)(F)F | | | | D |

TABLE 2-continued

Representative Compounds of the Invention with Bioactivity Data.

| Ex. No. | Structure | SMILES | $^1$H NMR | MS | ADP-Glo IC$_{50}$ | MCF 10A IC$_{50}$ |
|---|---|---|---|---|---|---|
| I-2516 | 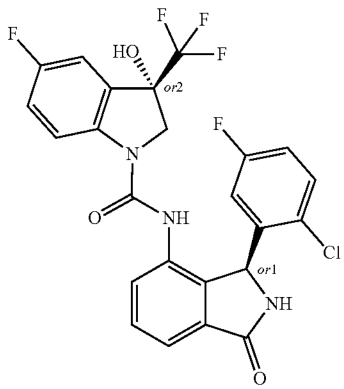 [SMILES: O=C1N[C@H](c2cc(F)ccc2Cl)c2c(NC(=O)N3C[C@](O)(C(F)(F)F)c4cc(F)ccc43)cccc21] | O[C@@]1(CN(C(=O)Nc2ccc3C(=O)N[C@@H](c23)c2cc(F)cc2Cl)c2ccc(F)cc12)C(F)(F)F | (400 MHz, DMSO-d6) 9.00 (d, J = 17.4 Hz, 1H), 8.68 (s, 1H), 7.96-7.81 (m, 1H), 7.46 (s, 1H), 7.40-7.17 (m, 6H), 7.11 (td, J = 8.4, 3.1 Hz, 1H), 6.55 (s, 1H), 6.03 (s, 1H), 4.24 (d, J = 12.0 Hz, 1H), 3.41 (d, J = 12.1 Hz, 1H), 2.97-2.74 (m, 4H). | 524.1 | D | |
| I-2517 | 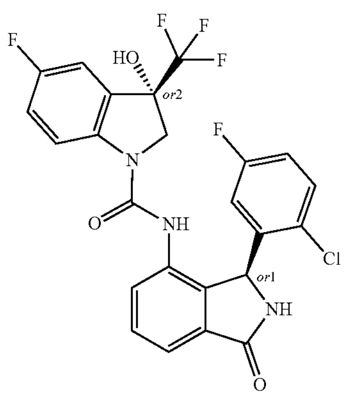 [SMILES: O=C1N[C@H](c2cc(F)ccc2Cl)c2c(NC(=O)N3C[C@](O)(C(F)(F)F)c4cc(F)ccc43)cccc21] | O[C@@]1(CN(C(=O)Nc2ccc3C(=O)N[C@@H](c23)c2cc(F)cc2Cl)c2ccc(F)cc12)C(F)(F)F | (400 MHz, DMSO-d6) 9.00 (d, J = 17.4 Hz, 1H), 8.68 (s, 1H), 7.96-7.81 (m, 1H), 7.46 (s, 1H), 7.40-7.17 (m, 6H), 7.11 (td, J = 8.4, 3.1 Hz, 1H), 6.55 (s, 1H), 6.03 (s, 1H), 4.24 (d, J = 12.0 Hz, 1H), 3.41 (d, J = 12.1 Hz, 1H), 2.97-2.74 (m, 4H). | 524.1 | | |
| I-2518 | 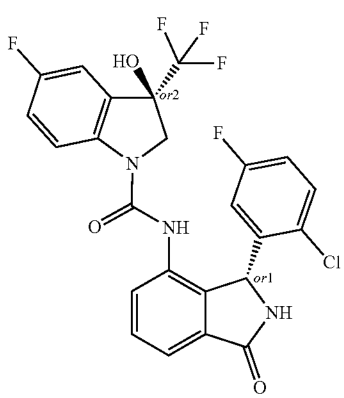 [SMILES: O=C1N[C@@H](c2cc(F)ccc2Cl)c2c(NC(=O)N3C[C@@](O)(C(F)(F)F)c4cc(F)ccc43)cccc21] | O[C@]1(CN(C(=O)Nc2ccc3C(=O)N[C@H](c23)c2cc(F)ccc2Cl)c2ccc(F)cc12)C(F)(F)F | | | A | A |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-2519 | 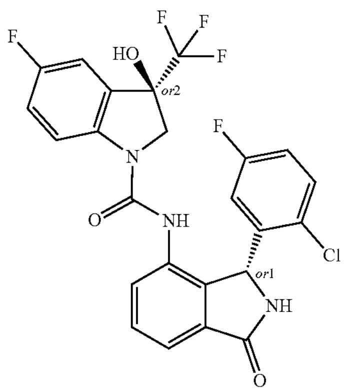 [SMILES: O=C1N[C@@H](c2cc(F)ccc2Cl)c2c(NC(=O)N3C[C@@](O)(C(F)(F)F)c4cc(F)ccc43)cccc21] | O[C@]1(CN(C(=O)Nc2cccc3C(=O)N[C@H](c23)c2cc(F)ccc2Cl)c2ccc(F)cc12)C(F)(F)F | (400 MHz, DMSO-d6) 9.35 (s, 1H), 8.99 (s, 1H), 8.77 (s, 1H), 7.93-7.88 (m, 2H),7.88-7.70 (m,1H), 7.58 (d, J = 8.4 Hz, 1H), 7.44 (s, 1H), 7.35 (dd, J = 8.9, 5.1 Hz, 1H), 7.29 (td, J = 9.0, 2.8 Hz, 1H), 7.23 (dd, J = 8.1, 2.7 Hz, 1H), 7.17 (td, J = 8.4, 3.1 Hz, 1H), 6.77 (s, 1H), 6.11 (s, 1H), 4.03 (d, J = 12.1 Hz, 1H), 3.54 (d, J = 12.2 Hz, 1H). | 591.1 | | |
| I-2520 | 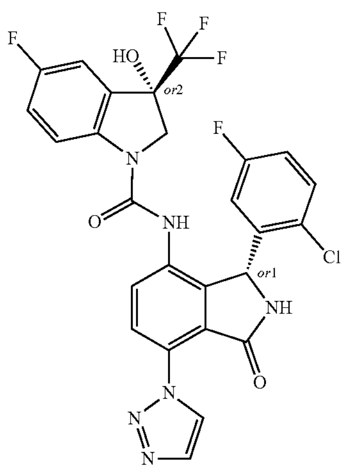 [SMILES: O=C1N[C@@H](c2cc(F)ccc2Cl)c2c(NC(=O)N3C[C@](O)(C(F)(F)F)c4cc(F)ccc43)ccc(-n3ccnn3)c21] | O[C@@]1(CN(C(=O)Nc2ccc(c3C(=O)N[C@H](c23)c2cc(F)ccc2Cl)-n2ccnn2)c2ccc(F)cc12)C(F)(F)F | (400 MHz, DMSO-d6) 9.35 (s, 1H), 8.89 (s, 1H), 8.78 (s, 1H), 7.93-7.81 (m, 3H), 7.66 (d, J = 8.4 Hz, 1H), 7.42-7.37 (m, 2H), 7.26 (qd, J = 8.6, 8.2, 2.8 Hz, 2H), 7.15 (td, J = 8.4, 3.1 Hz, 1H), 6.77 (s, 1H), 4.24 (d, J = 12.0 Hz, 1H), 3.48 (d, J = 12.1 Hz, 1H), 2.87 (s, 1H). | 591.1 | A | A |
| I-2521 | 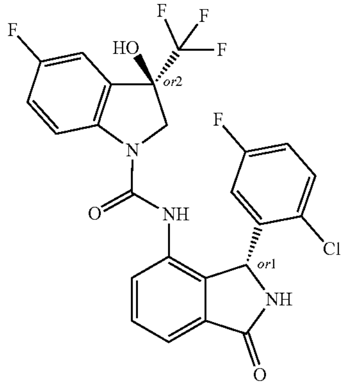 [SMILES: O=C1N[C@@H](c2cc(F)ccc2Cl)c2c(NC(=O)N3C[C@@](O)(C(F)(F)F)c4cc(F)ccc43)cccc21] | O[C@@]1(CN(C(=O)Nc2ccc(c3C(=O)N[C@@H](c23)c2cc(F)ccc2Cl)-n2ccnn2)c2ccc(F)cc12)C(F)(F)F | | | D | |

TABLE 2-continued

Representative Compounds of the Invention with Bioactivity Data.

| Ex. No. | Structure | SMILES | $^1$H NMR | MS | ADP-Glo IC$_{50}$ | MCF 10A IC$_{50}$ |
|---|---|---|---|---|---|---|
| I-2522 | 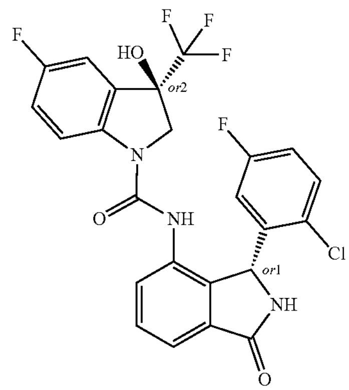 [SMILES: O=C1N[C@@H](c2cc(F)ccc2Cl)c2c(NC(=O)N3C[C@@](O)(C(F)(F)F)c4cc(F)ccc43)cccc21] | O[C@@]1(CN(C(=O)Nc2ccc(c3C(=O)N[C@@H](c23)c2cc(F)ccc2Cl)-n2ccnn2)c2ccc(F)cc12)C(F)(F)F | (400 MHz, DMSO-d6) 9.35 (s, 1H), 8.98 (s, 1H), 8.77 (s, 1H), 7.93-7.84 (m, 2H), 7.80-7.70 (m, 1H), 7.61-7.54 (m, 1H), 7.44 (s, 1H), 7.40-7.30 (m, 1H), 7.30-7.25 (m, 1H), 7.23 (dd, J = 8.0, 2.8 Hz, 1H), 7.17 (td, J = 8.4, 3.0 Hz, 1H), 6.80 (s, 1H), 6.11 (s, 1H), 4.03 (d, J = 12.1 Hz, 1H), 3.54 (d, J = 12.0 Hz, 1H). | 591.1 | | |
| I-2523 | 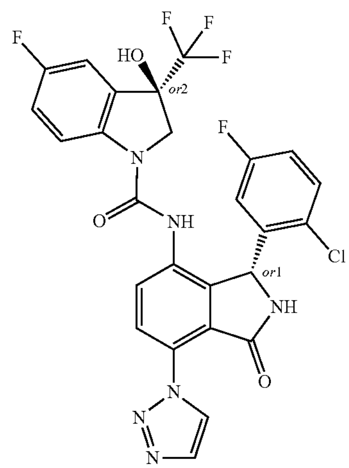 [SMILES: O=C1N[C@@H](c2cc(F)ccc2Cl)c2c(NC(=O)N3C[C@@](O)(C(F)(F)F)c4cc(F)ccc43)ccc(-n3ccnn3)c21] | O[C@]1(CN(C(=O)Nc2ccc(c3C(=O)N[C@@H](c23)c2cc(F)ccc2Cl)-n2ccnn2)c2ccc(F)cc12)C(F)(F)F | (400 MHz, DMSO-d6) 9.35 (s, 1H), 8.89 (s, 1H), 8.78 (s, 1H), 7.93 (d, J = 1.1 Hz, 1H), 7.90-7.81 (m, 2H), 7.66 (d, J = 8.4 Hz, 1H), 7.42-7.37 (m, 2H), 7.26 (qd, J = 8.7, 2.8 Hz, 2H), 7.15 (td, J = 8.3, 3.1 Hz, 1H), 6.79 (s, 1H), 6.15 (s, 1H), 4.24 (d, J = 12.0 Hz, 1H), 3.48 (d, J = 12.2 Hz, 1H). | 591.1 | D | |
| I-2524 | 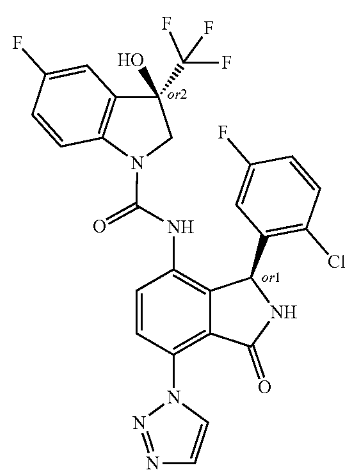 [SMILES: O=C1N[C@H](c2cc(F)ccc2Cl)c2c(NC(=O)N3C[C@@](O)(C(F)(F)F)c4cc(F)ccc43)ccc(-n3ccnn3)c21] | O[C@]1(CN(C(=O)Nc2ccc(c3C(=O)N[C@@H](c23)c2cc(F)ccc2Cl)-n2ccnn2)c2ccc(F)cc12)C(F)(F)F | (400 MHz, DMSO-d6) 9.18 (s, 1H), 9.02 (s, 1H), 8.10 (s, 2H), 8.00-7.85(m,1H), 7.68 (d, J = 8.3 Hz, 1H), 7.55 (d, J = 8.3 Hz, 1H), 7.43 (s, 1H), 7.36 (dd, J = 8.9, 5.1 Hz, 1H), 7.29 (td, J = 9.0, 2.8 Hz, 1H), 7.25-7.12 (m, 1H),7.12-6.90 (m, 1H), 6.70 (s, 1H), 6.07 (s, 1H), 4.02 (d, J = 12.0 Hz, 1H), 3.51 (d, J = 12.0 Hz, 1H). | 591.1 | D | |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-2525 | 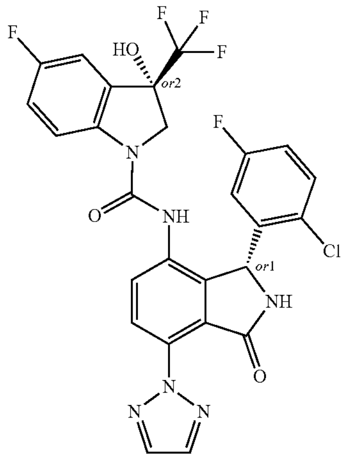 [SMILES: O=C1N[C@@H](c2cc(F)ccc2Cl)c2c(NC(=O)N3C[C@](O)(C(F)(F)F)c4cc(F)ccc43)ccc(-n3nccn3)c21] | O[C@@]1(CN(C(=O)Nc2cc(c3C(=O)N[C@H](c23)c2cc(F)cc2Cl)-n2nccn2)c2ccc(F)cc12)C(F)(F)F | (400 MHz, DMSO-d6) 9.18 (s, 1H), 9.02 (s, 1H), 8.10 (s, 2H), 7.95 (s, 1H), 7.68 (d, J = 8.3 Hz, 1H), 7.55 (d, J = 8.3 Hz, 1H), 7.44 (s, 1H), 7.36 (dd, J = 8.9, 5.1 Hz, 1H), 7.29 (td, J = 9.1, 2.8 Hz, 1H), 7.22 (dd, J = 8.1, 2.7 Hz, 1H), 7.16 (td, J = 8.3, 3.1 Hz, 1H), 6.69 (s, 1H), 6.07 (s, 1H), 4.02 (d, J = 12.1 Hz, 1H), 3.51 (d, J = 12.0 Hz, 1H), 0.99 (t, J = 7.2 Hz, 1H). | 591.1 | A | A |
| I-2526 | 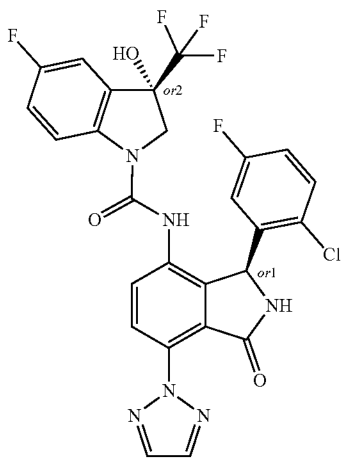 [SMILES: O=C1N[C@H](c2cc(F)ccc2Cl)c2c(NC(=O)N3C[C@](O)(C(F)(F)F)c4cc(F)ccc43)ccc(-n3nccn3)c21] | O[C@@]1(CN(C(=O)Nc2cc(c3C(=O)N[C@@H](c23)c2cc(F)cc2Cl)-n2nccn2)c2ccc(F)cc12)C(F)(F)F | (400 MHz, DMSO-d6) 9.19 (s, 1H), 8.91 (s, 1H), 8.10 (s, 2H), 7.87 (dd, J = 9.0, 4.7 Hz, 1H), 7.66 (q, J = 8.4 Hz, 2H), 7.43-7.34 (m, 2H), 7.32-7.20 (m, 2H), 7.15 (td, J = 8.3, 3.1 Hz, 1H), 6.64 (s, 1H), 6.11 (s, 1H), 4.21 (d, J = 12.0 Hz, 1H), 3.44 (d, J = 12.0 Hz, 1H). | 591.1 | | D |
| I-2527 | 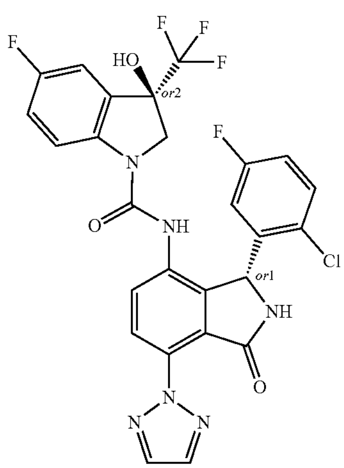 [SMILES: O=C1N[C@@H](c2cc(F)ccc2Cl)c2c(NC(=O)N3C[C@@](O)(C(F)(F)F)c4cc(F)ccc43)ccc(-n3nccn3)c21] | O[C@]1(CN(C(=O)Nc2cc(c3C(=O)N[C@H](c23)c2cc(F)cc2Cl)-n2nccn2)c2ccc(F)cc12)C(F)(F)F | (400 MHz, DMSO-d6) 9.19 (s, 1H), 8.92 (s, 1H), 8.10 (s, 2H), 7.87 (dd, J = 8.9, 4.7 Hz, 1H), 7.66 (q, J = 8.3 Hz, 2H), 7.44-7.34 (m, 2H), 7.32-7.20 (m, 2H), 7.15 (td, J = 8.3, 3.1 Hz, 1H), 6.71 (s, 1H), 6.11 (s, 1H), 4.21 (d, J = 12.1 Hz, 1H), 3.45 (d, J = 12.0 Hz, 1H). | 591.2 | | D |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-2528 | 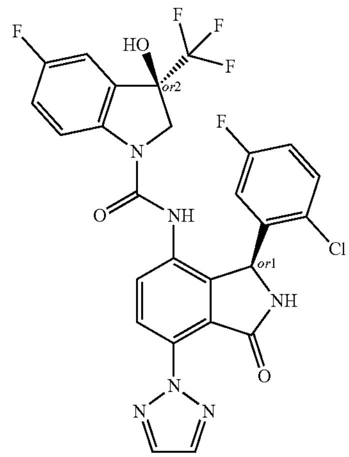 [SMILES: O=C1N[C@H](c2cc(F)ccc2Cl)c2c(NC(=O)N3C[C@@](O)(C(F)(F)F)c4cc(F)ccc43)ccc(-n3nccn3)c21] | O[C@]1(CN(C(=O)Nc2ccc(c3C(=O)N[C@@H](c23)c2cc(F)cc2Cl)-n2nccn2)c2ccc(F)cc12)C(F)(F)F | (400 MHz, DMSO-d6) 9.27 (s, 1H), 9.03 (s, 1H), 7.94 (dd, J = 9.2, 4.6 Hz, 1H), 7.78 (dd, J = 7.0, 2.1 Hz, 1H), 7.61 (d, J = 1.9 Hz, 1H), 7.56 (ddd, J = 9.0, 6.6, 2.1 Hz, 1H), 7.52-7.40 (m, 2H), 7.36 (dd, J = 8.9, 5.2 Hz, 1H), 7.29 (td, J = 9.0, 2.8 Hz, 1H), 7.21 (dd, J = 8.1, 2.7 Hz, 1H), 7.16 (td, J = 8.4, 3.1 Hz, 1H), 6.55 (dt, J = 9.4, 1.0 Hz, 2H), 6.38 (td, J = 6.7, 1.4 Hz, 1H), 6.11 (s, 1H), 4.00 (d, J = 12.1 Hz, 1H), 3.52 (d, J = 12.1 Hz, 1H). | 617.2 | D | |
| I-2529 | 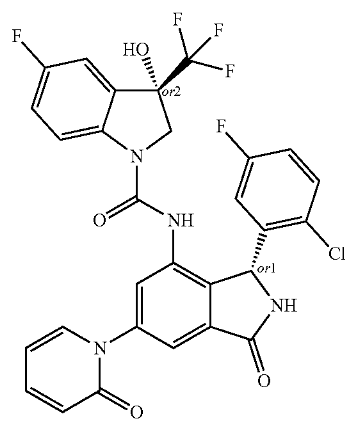 [SMILES: O=C1N[C@@H](c2cc(F)ccc2Cl)c2c(NC(=O)N3C[C@](O)(C(F)(F)F)c4cc(F)ccc43)cc(-n3ccccc3=O)cc21] | O[C@@]1(CN(C(=O)Nc2cc(cc3C(=O)N[C@H](c23)c2cc(F)cc2Cl)-n2ccccc2=O)c2ccc(F)cc12)C(F)(F)F | (400 MHz, DMSO-d6) 9.27 (s, 1H), 8.92 (s, 1H), 7.87 (dd, J = 9.0, 4.7 Hz, 1H), 7.78 (dd, J = 7.0, 2.1 Hz, 1H), 7.61 (d, J = 1.9 Hz, 1H), 7.59-7.51 (m, 2H), 7.45-7.35 (m, 2H), 7.31-7.19 (m, 2H), 7.16 (td, J = 8.4, 3.1 Hz, 1H), 6.58-6.50 (m, 1H), 6.38 (td, J = 6.7, 1.4 Hz, 2H), 6.15 (s, 1H), 4.22 (d, J = 12.0 Hz, 1H), 3.52 (d, J = 12.1 Hz, 1H). | 617.2 | D | |
| I-2530 | 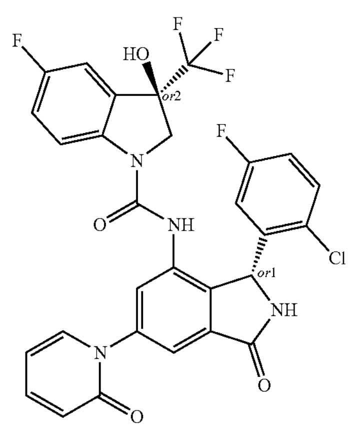 [SMILES: O=C1N[C@@H](c2cc(F)ccc2Cl)c2c(NC(=O)N3C[C@@](O)(C(F)(F)F)c4cc(F)ccc43)cc(-n3ccccc3=O)cc21] | O[C@]1(CN(C(=O)Nc2cc(cc3C(=O)N[C@H](c23)c2cc(F)cc2Cl)-n2ccccc2=O)c2ccc(F)cc12)C(F)(F)F | (400 MHz, DMSO-d6) 9.27 (s, 1H), 8.92 (s, 1H), 7.87 (dd, J = 9.0, 4.7 Hz, 1H), 7.78 (dd, J = 6.9, 2.1 Hz, 1H), 7.61 (d, J = 1.9 Hz, 1H), 7.60-7.51 (m, 2H), 7.43-7.35 (m, 2H), 7.31-7.11 (m, 3H), 6.63 (s, 1H), 6.58-6.51 (m, 1H), 6.38 (td, J = 6.7, 1.4 Hz, 1H), 6.15 (s, 1H), 4.22 (d, J = 12.1 Hz, 1H), 3.43 (d, J = 12.0 Hz, 1H). | 617.2 | D | |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-2531 | 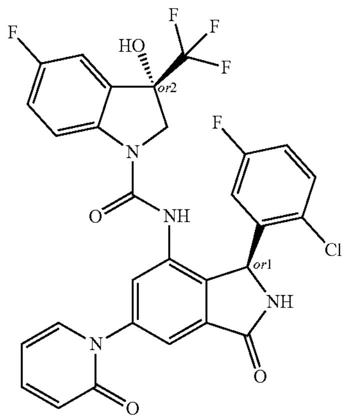 [SMILES: O=C1N[C@H](c2cc(F)ccc2Cl)c2c(NC(=O)N3C[C@](O)(C(F)(F)F)c4cc(F)ccc43)cc(-n3ccccc3=O)cc21] | O[C@@]1(CN(C(=O)Nc2cc(cc3C(=O)N[C@@H](c23)c2cc(F)ccc2Cl)-n2ccccc2=O)c2ccc(F)cc12)C(F)(F)F | (400 MHz, DMSO-d6) 9.26 (s, 1H), 9.03 (s, 1H), 7.94 (dd, J = 9.1, 4.6 Hz, 1H), 7.78 (dd, J = 6.9, 2.1 Hz, 1H), 7.61 (d, J = 1.9 Hz, 1H), 7.56 (ddd, J = 9.0, 6.6, 2.1 Hz, 1H), 7.48-7.40 (m, 2H), 7.36 (dd, J = 8.9, 5.1 Hz, 1H), 7.28 (td, J = 9.1, 2.8 Hz, 1H), 7.24-7.12 (m, 2H), 6.58-6.51 (m, 2H), 6.38 (td, J = 6.7, 1.4 Hz, 1H), 6.11 (s, 1H), 4.00 (d, J = 12.1 Hz, 1H), 3.52 (d, J = 12.1 Hz, 1H). | 617.2 | D | |
| I-2532 | 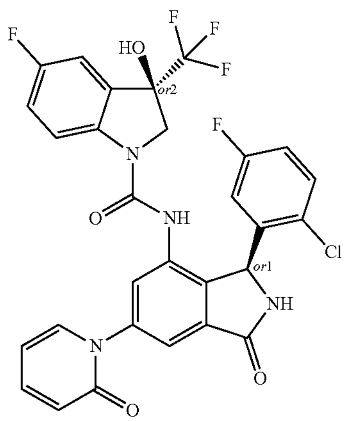 [SMILES: O=C1N[C@H](c2cc(F)ccc2Cl)c2c(NC(=O)N3C[C@@](O)(C(F)(F)F)c4cc(F)ccc43)cc(-n3ccccc3=O)cc21] | O[C@]1(CN(C(=O)Nc2cc(cc3C(=O)N[C@@H](c23)c2cc(F)ccc2Cl)-n2ccccc2=O)c2ccc(F)cc12)C(F)(F)F | (400 MHz, DMSO-d6) 9.24 (s, 1H), 9.02 (s, 1H), 8.13 (dd, J = 3.8, 1.7 Hz, 1H), 7.95 (s, 1H), 7.84 (d, J = 1.9 Hz, 1H), 7.66 (d, J = 1.9 Hz, 1H), 7.55 (dd, J = 9.5, 3.8 Hz, 1H), 7.41 (s, 1H), 7.35 (dd, J = 8.9, 5.2 Hz, 1H), 7.29 (td, J = 9.0, 2.8 Hz, 1H), 7.24-7.11 (m, 3H), 6.67 (s, 1H), 6.08 (s, 1H), 4.01 (d, J = 12.1 Hz, 1H), 3.52 (d, J = 12.1 Hz, 1H). | 618.2 | A | A |
| I-2533 | 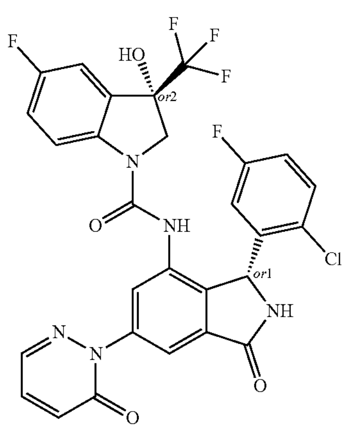 | O[C@@]1(CN(C(=O)Nc2cc(cc3C(=O)N[C@H](c23)c2cc(F)ccc2Cl)-n2nccc2=O)c2ccc(F)cc12)C(F)(F)F | (400 MHz, DMSO-d6) 9.25 (s, 1H), 8.92 (s, 1H), 8.13 (dd, J = 3.8, 1.7 Hz, 1H), 7.92-7.81 (m, 2H), 7.74 (d, J = 1.9 Hz, 1H), 7.54 (dd, J = 9.5, 3.8 Hz, 1H), 7.44-7.34 (m, 2H), 7.31-7.19 (m, 2H), 7.15 (ddd, J = 9.5, 5.3, 2.4 Hz, 2H), 6.63 (s, 1H), 6.12 (s, 1H), 4.24 (d, J = 12.1 Hz, 1H), 3.42 (d, J = 12.2 Hz, 1H). | 618.1 | D | |

TABLE 2-continued

Representative Compounds of the Invention with Bioactivity Data.

| Ex. No. | Structure | SMILES | $^1$H NMR | MS | ADP-Glo IC$_{50}$ | MCF 10A IC$_{50}$ |
|---|---|---|---|---|---|---|
| I-2534 | 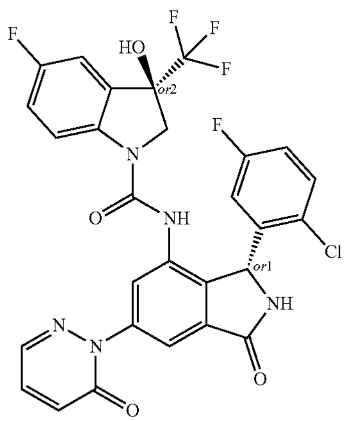 [SMILES: O=C1N[C@@H](c2cc(F)ccc2Cl)c2c(NC(=O)N3C[C@@](O)(C(F)(F)F)c4cc(F)ccc43)cc(-n3ncccc3=O)cc21] | O[C@]1(CN(C(=O)Nc2cc(cc3C(=O)N[C@H](c23)c2cc(F)ccc2Cl)-n2ncccc2=O)c2ccc(F)cc12)C(F)(F)F | (400 MHz, DMSO-d6) 9.25 (s, 1H), 8.92 (s, 1H), 8.13 (dd, J = 3.8, 1.6 Hz, 1H), 7.92-7.81 (m, 2H), 7.74 (d, J = 1.9 Hz, 1H), 7.54 (dd, J = 9.5, 3.8 Hz, 1H), 7.42-7.34 (m, 2H), 7.31-7.10 (m, 4H), 6.66 (s, 1H), 6.12 (s, 1H), 4.24 (d, J = 12.0 Hz, 1H), 3.42 (d, J = 12.1 Hz, 1H). | 618.1 | C | |
| I-2535 | 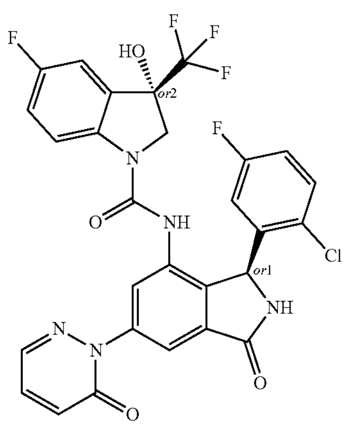 [SMILES: O=C1N[C@H](c2cc(F)ccc2Cl)c2c(NC(=O)N3C[C@](O)(C(F)(F)F)c4cc(F)ccc43)cc(-n3ncccc3=O)cc21] | O[C@@]1(CN(C(=O)Nc2cc(cc3C(=O)N[C@@H](c23)c2cc(F)ccc2Cl)-n2ncccc2=O)c2ccc(F)cc12)C(F)(F)F | (400 MHz, DMSO-d6) 9.24 (s, 1H), 9.02 (s, 1H), 8.13 (dd, J = 3.8, 1.7 Hz, 1H), 7.94 (d, J = 6.8 Hz, 1H), 7.84 (d, J = 1.9 Hz, 1H), 7.66 (d, J = 1.9 Hz, 1H), 7.55 (dd, J = 9.5, 3.8 Hz, 1H), 7.41 (s, 1H), 7.35 (dd, J = 8.9, 5.1 Hz, 1H), 7.29 (td, J = 9.0, 2.8 Hz, 1H), 7.24-7.11 (m, 3H), 6.66 (s, 1H), 6.08 (s, 1H), 4.01 (d, J = 12.1 Hz, 1H), 3.52 (d, J = 12.0 Hz, 1H). | 618.2 | D | |
| I-2536 | 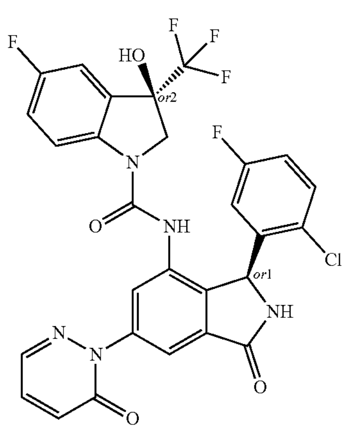 [SMILES: O=C1N[C@H](c2cc(F)ccc2Cl)c2c(NC(=O)N3C[C@@](O)(C(F)(F)F)c4cc(F)ccc43)cc(-n3ncccc3=O)cc21] | O[C@]1(CN(C(=O)Nc2cc(cc3C(=O)N[C@@H](c23)c2cc(F)ccc2Cl)-n2ncccc2=O)c2ccc(F)cc12)C(F)(F)F | (400 MHz, DMSO-d6) δ9.15 (s, 1H), 8.61 (s, 1H), 7.72 (dd, J = 8.9, 4.7 Hz, 1H), 7.57 (s, 1H), 7.46 (s, 1H), 7.36 (dd, J = 8.9, 5.2 Hz, 1H), 7.07 (dtd, J = 28.1, 9.0, 8.6, 2.9 Hz, 3H), 6.60 (s, 1H), 6.08 (s, 1H), 5.74 (d, J = 4.5 Hz, 1H), 5.16 (dd, J = 8.3, 4.2 Hz, 1H), 4.23 (s, 2H), 3.98 (dd, J = 11.1, 8.1 Hz, 1H), 3.21 (dd, J = 10.9, 4.1 Hz, 1H). | 495.2 | A | A |

TABLE 2-continued

Representative Compounds of the Invention with Bioactivity Data.

| Ex. No. | Structure | SMILES | $^1$H NMR | MS | ADP-Glo IC$_{50}$ | MCF 10A IC$_{50}$ |
|---|---|---|---|---|---|---|
| I-2537 | 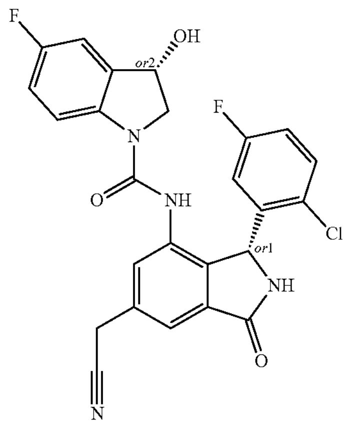 [SMILES: N#CCc1cc(NC(=O)N2C[C@@H](O)c3cc(F)ccc32)c2c(c1)C(=O)N[C@H]2c1cc(F)ccc1Cl] | O[C@@H]1CN(C(=O)Nc2cc(CC#N)cc3C(=O)N[C@H](c23)c2cc(F)ccc2Cl)c2ccc(F)cc12 | (400 MHz, DMSO-d6) δ 9.15 (s, 1H), 8.61 (s, 1H), 7.72 (dd, J = 8.9, 4.7 Hz, 1H), 7.57 (s, 1H), 7.46 (s, 1H), 7.36 (dd, J = 8.9, 5.2 Hz, 1H), 7.07 (dtd, J = 28.1, 9.0, 8.6, 2.9 Hz, 3H), 6.60 (s, 1H), 6.08 (s, 1H), 5.74 (d, J = 4.5 Hz, 1H), 5.16 (dd, J = 8.3, 4.2 Hz, 1H), 4.23 (s, 2H), 3.98 (dd, J = 11.1, 8.1 Hz, 1H), 3.21 (dd, J = 10.9, 4.1 Hz, 1H). | 495.1 | A | A |
| I-2538 | 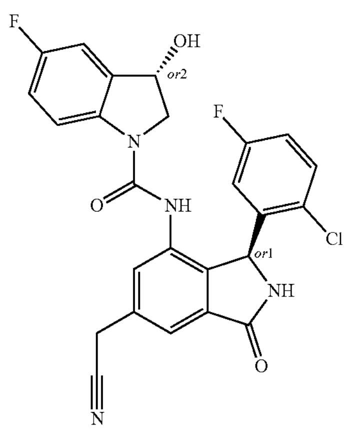 [SMILES: N#CCc1cc(NC(=O)N2C[C@@H](O)c3cc(F)ccc32)c2c(c1)C(=O)N[C@@H]2c1cc(F)ccc1Cl] | O[C@@H]1CN(C(=O)Nc2cc(CC#N)cc3C(=O)N[C@@H](c23)c2cc(F)ccc2Cl)c2ccc(F)cc12 | (400 MHz, DMSO-d6) δ 9.15 (s, 1H), 8.61 (s, 1H), 7.72 (dd, J = 8.9, 4.7 Hz, 1H), 7.57 (s, 1H), 7.46 (s, 1H), 7.36 (dd, J = 8.9, 5.2 Hz, 1H), 7.07 (dtd, J = 28.1, 9.0, 8.6, 2.9 Hz, 3H), 6.60 (s, 1H), 6.08 (s, 1H), 5.74 (d, J = 4.5 Hz, 1H), 5.16 (dd, J = 8.3, 4.2 Hz, 1H), 4.23 (s, 2H), 3.98 (dd, J = 11.1, 8.1 Hz, 1H), 3.21 (dd, J = 10.9, 4.1 Hz, 1H). | 495.1 | A | |
| I-2539 | 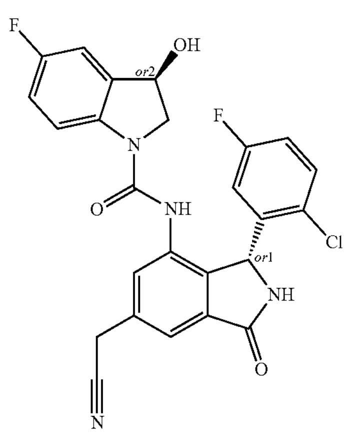 [SMILES: N#CCc1cc(NC(=O)N2C[C@H](O)c3cc(F)ccc32)c2c(c1)C(=O)N[C@H]2c1cc(F)ccc1Cl] | O[C@H]1CN(C(=O)Nc2cc(CC#N)cc3C(=O)N[C@H](c23)c2cc(F)ccc2Cl)c2ccc(F)cc12 | (400 MHz, DMSO-d6) δ 9.15 (s, 1H), 8.61 (s, 1H), 7.72 (dd, J = 8.9, 4.7 Hz, 1H), 7.57 (s, 1H), 7.46 (s, 1H), 7.36 (dd, J = 8.9, 5.2 Hz, 1H), 7.07 (dtd, J = 28.1, 9.0, 8.6, 2.9 Hz, 3H), 6.60 (s, 1H), 6.08 (s, 1H), 5.74 (d, J = 4.5 Hz, 1H), 5.16 (dd, J = 8.3, 4.2 Hz, 1H), 4.23 (s, 2H), 3.98 (dd, J = 11.1, 8.1 Hz, 1H), 3.21 (dd, J = 10.9, 4.1 Hz, 1H). | 495.2 | D | |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-2540 | 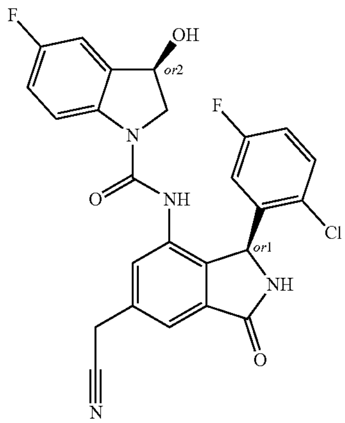 [SMILES: N#CCc1cc(NC(=O)N2C[C@H](O)c3cc(F)ccc32)c2c(c1)C(=O)N[C@@H]2c1cc(F)ccc1Cl] | O[C@H]1CN(C(=O)Nc2cc(CC#N)cc3C(=O)N[C@@H](c23)c2cc(F)cc c2Cl)c2c cc(F)cc1 2 | (400 MHz, DMSO-d6) 9.09 (s, 1H), 8.86 (s, 1H), 7.93 (s, 1H), 7.54 (s, 1H), 7.43 (s, 1H), 7.38-7.23 (m, 3H), 7.20 (dd, J = 8.1, 2.8 Hz, 1H), 7.13 (td, J = 8.4, 3.1 Hz, 1H), 6.53 (s, 1H), 6.01 (s, 1H), 4.56 (s, 2H), 4.01 (d, J = 12.1 Hz, 1H), 3.50 (d, J = 12.0 Hz, 1H), 3.36 (s, 3H). | 568.3 | B | |
| I-2541 | 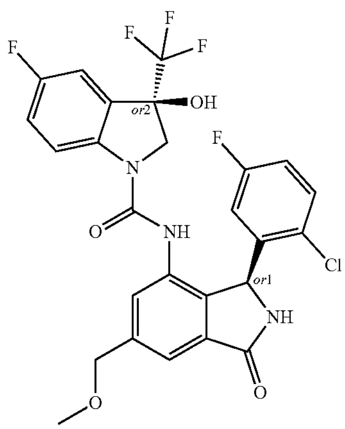 [SMILES: COCc1cc(NC(=O)N2C[C@@](O)(C(F)(F)F)c3cc(F)ccc32)c2c(c1)C(=O)N[C@@H]2c1cc(F)ccc1Cl] | COCc1cc2C(=O)N[C@@H](c2c(NC(=O)N2C[C@](O)(c3cc(F)c cc23)C(F)(F)F)c1)c1cc(F)c cc1Cl | (400 MHz, DMSO-d6) 9.10 (s, 1H), 8.76 (s, 1H), 7.86 (dd, J = 9.0, 4.7 Hz, 1H), 7.54 (s, 1H), 7.44 (d, J = 1.4 Hz, 1H), 7.40 (s, 1H), 7.35 (dd, J = 8.9, 5.1 Hz, 1H), 7.30-7.18 (m, 2H), 7.12 (td, J = 8.3, 3.1 Hz, 1H), 6.53 (s, 1H), 6.06 (s, 1H), 4.56 (s, 2H), 4.24 (d, J = 12.0 Hz, 1H), 3.41 (d, J = 12.0 Hz, 1H), 3.36 (s, 3H). | 568.3 | A | A |
| I-2542 | 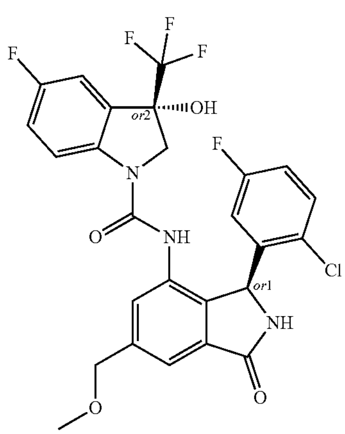 [SMILES: COCc1cc(NC(=O)N2C[C@](O)(C(F)(F)F)c3cc(F)ccc32)c2c(c1)C(=O)N[C@@H]2c1cc(F)ccc1Cl] | COCc1cc2C(=O)N[C@@H](c2c(NC(=O)N2C[C@@](O)(c3cc(F)c ccc23)C(F)(F)F)c1)c1cc(F)c ccc1Cl | (400 MHz, DMSO-d6) 9.10 (s, 1H), 8.75 (s, 1H), 7.86 (dd, J = 9.0, 4.7 Hz, 1H), 7.54 (s, 1H), 7.44 (d, J = 1.4 Hz, 1H), 7.41-7.31 (m, 2H), 7.30-7.18 (m, 2H), 7.12 (td, J = 8.4, 3.1 Hz, 1H), 6.54 (s, 1H), 6.05 (s, 1H), 4.56 (s, 2H), 4.24 (d, J = 12.1 Hz, 1H), 3.41 (d, J = 12.0 Hz, 1H), 3.36 (s, 3H). | 568.3 | D | |

TABLE 2-continued

Representative Compounds of the Invention with Bioactivity Data.

| Ex. No. | Structure | SMILES | $^1$H NMR | MS | ADP-Glo IC$_{50}$ | MCF 10A IC$_{50}$ |
|---|---|---|---|---|---|---|
| I-2543 | 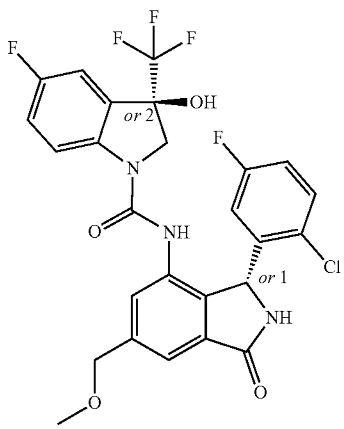 [SMILES: COCc1cc(NC(=O)N2C[C@@](O)(C(F)(F)F)c3cc(F)ccc32)c2c(c1)C(=O)N[C@H]2c1cc(F)ccc1Cl] | COCc1cc2C(=O)N[C@H](c2c(NC(=O)N2C[C@](O)(c3cc(F)ccc23)C(F)(F)F)c1)c1cc(F)ccc1Cl | (400 MHz, DMSO-d6) 9.09 (s, 1H), 8.85 (s, 1H), 7.93 (s, 1H), 7.54 (d, J = 1.4 Hz, 1H), 7.41 (s, 1H), 7.36 (d, J = 1.4 Hz, 1H), 7.32 (dd, J = 8.9, 5.2 Hz, 1H), 7.27 (td, J = 9.0, 2.7 Hz, 1H), 7.20 (dd, J = 8.1, 2.8 Hz, 1H), 7.13 (td, J = 8.3, 3.1 Hz, 1H), 6.54 (s, 1H), 6.01 (s, 1H), 4.56 (s, 2H), 4.01 (d, J = 12.1 Hz, 1H), 3.50 (d, J = 12.1 Hz, 1H), 3.36 (s, 3H). | 568.3 | D | |
| I-2544 | 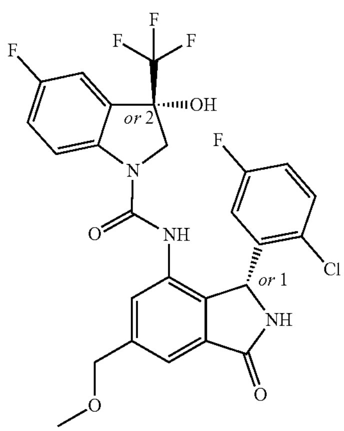 [SMILES: COCc1cc(NC(=O)N2C[C@](O)(C(F)(F)F)c3cc(F)ccc32)c2c(c1)C(=O)N[C@H]2c1cc(F)ccc1Cl] | COCc1cc2C(=O)N[C@H](c2c(NC(=O)N2C[C@@](O)(c3cc(F)ccc23)C(F)(F)F)c1)c1cc(F)ccc1Cl | (400 MHz, DMSO-d6) δ 9.26 (br s, 1H), 8.88 (s, 0.5H), 8.78 (s, 0.5H), 7.88 (dd, J = 8.0, 3.9 Hz, 0.5H), 7.81 (dd, J = 8.9, 4.7 Hz, 0.5H), 7.58 (s, 1H), 7.48 (d, J = 1.8 Hz, 1H), 7.39-7.30 (m, 1H), 7.29-7.23 (m, 1H), 7.18 (dd, J = 8.9, 2.7 Hz, 1H), 7.16-7.08 (m, 1H), 6.66 (br s, 1H), 6.27 (app. t, J = 55.4, 3.6 Hz, 1H), 6.09 (overlapping br s, 0.5H), 6.05 (overlapping br s, 0.5H), 4.04 (d, J = 11.5 Hz, 0.5H), 3.82 (d, J = 11.9 Hz, 0.5H), 3.47 (d, J = 11.6 Hz, 0.5H), 3.33 (d, J = 11.3 Hz, 0.5H). 1:1 Mix of diastereomers. | 540.0 | D | |
| I-2545 | 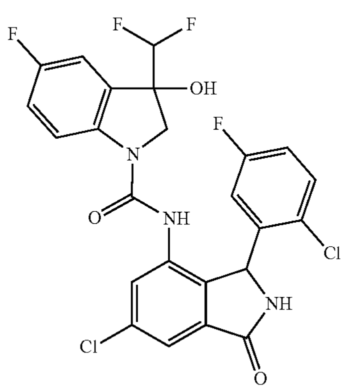 [SMILES: O=C1NC(c2cc(F)ccc2Cl)c2c(NC(=O)N3CC(O)(C(F)F)c4cc(F)ccc43)cc(Cl)cc21] | OC1(CN(C(=O)Nc2cc(Cl)cc3C(=O)NC(c23)c2cc(F)ccc2Cl)c2ccc(F)cc12)C(F)F | (400 MHz, ) δ 9.39 (br. s, 2H), 8.99 (s, 1H), 8.89 (s, 1H), 8.03 (br. s, 2H), 7.91 (2 overlapping s, 2H), 7.81 (2 overlapping s, 2H), 7.45-7.30 (m, 2H), 7.32-7.21 (m, 3H), 7.22-7.17 (m, 2H), 7.17-7.08 (m, 3H), 6.74 (s, 1H), 6.67 (s, 1H), 6.28 (app. td, J = 55.2, 3.1 Hz, 2H (CHF2 signal)), 6.15 (br. s, 2H), 4.03 (br. d, J = 11.2 Hz, 1H), 3.80 (br. d, J = 11.9 Hz, 1H), 3.46 (br. d, J = 11.4 Hz, 1H), 3.30 (submerged br. d, J = 11.9 Hz, 1H); approximately. 1:1 mixture of diastereomers | 529.2 | A | A |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-2546 | 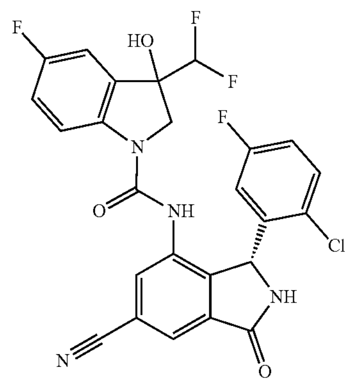 [SMILES: N#Cc1cc(NC(=O)N2CC(O)(C(F)F)c3cc(F)ccc32)c2c(c1)C(=O)N[C@H]2c1cc(F)ccc1Cl] | OC1(CN(C(=O)Nc2cc(cc3C(=O)NC(c23)c2cc(F)ccc2Cl)C#N)c2ccc(F)cc12)C(F)F | (400 MHz, DMSO-d6) 9.30 (s, 1H), 9.07 (s, 1H), 8.47 (s, 1H), 8.12 (s, 2H), 8.04 (s, 1H), 7.95 (s, 1H), 7.36 (dd, J = 8.9, 5.1 Hz, 1H), 7.28 (s, 1H), 7.24-7.13 (m, 2H), 7.17-7.10 (m, 1H), 6.10 (s, 1H), 4.04 (s, 1H), 3.54 (s, 1H). | 591.2 | | B |
| I-2547 | 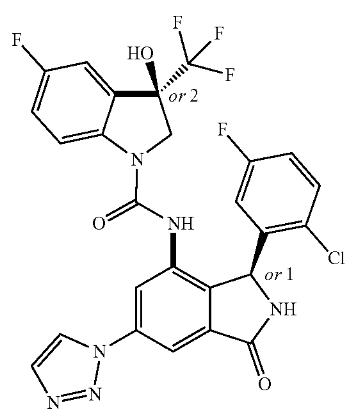 | O[C@]1(CN(C(=O)Nc2cc(cc3C(=O)N[C@@H](c23)c2cc(F)ccc2Cl)-n2ccnn2)c2ccc(F)cc12)C(F)(F)F | (400 MHz, DMSO-d6) 9.32 (s, 1H), 9.07 (s, 2H), 8.20 (s, 1H), 8.10 (s, 1H), 8.04 (d, J = 1.2 Hz, 1H), 7.90 (dd, J = 9.0, 4.6 Hz, 1H), 7.38 (dd, J = 8.9, 5.1 Hz, 2H), 7.31-7.19 (m, 2H), 7.15 (td, J = 8.4, 3.1 Hz, 1H), 6.15 (s, 1H), 4.23 (d, J = 12.1 Hz, 1H), 3.45 (d, J = 11.7 Hz, 1H). | 591.1 | A | A |
| I-2548 | 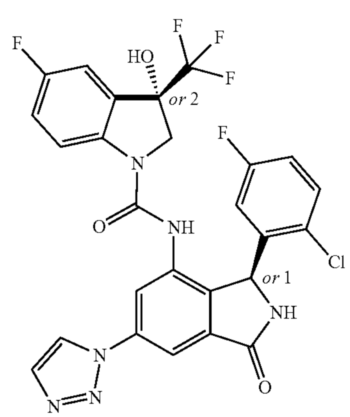 | O[C@@]1(CN(C(=O)Nc2cc(cc3C(=O)N[C@@H](c23)c2cc(F)ccc2Cl)-n2ccnn2)c2ccc(F)cc12)C(F)(F)F | (400 MHz, DMSO-d6) 9.33 (s, 1H), 9.08 (d, J = 1.3 Hz, 1H), 9.03 (s, 1H), 8.19-8.07 (m, 2H), 8.04 (d, J = 1.2 Hz, 1H), 7.90 (dd, J = 9.0, 4.6 Hz, 1H), 7.42 (s, 1H), 7.38 (dd, J = 8.9, 5.1 Hz, 1H), 7.32-7.20 (m, 2H), 7.15 (td, J = 8.3, 3.1 Hz, 1H), 6.15 (s, 1H), 4.24 (d, J = 12.0 Hz, 1H), 3.43 (d, J = 11.8 Hz, 1H). | 591.2 | D | |

TABLE 2-continued

Representative Compounds of the Invention with Bioactivity Data.

| Ex. No. | Structure | SMILES | $^1$H NMR | MS | ADP-Glo IC$_{50}$ | MCF 10A IC$_{50}$ |
|---|---|---|---|---|---|---|
| I-2549 | 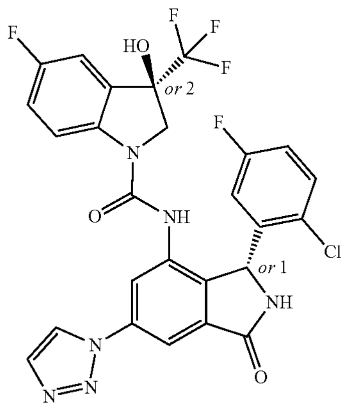 [SMILES: O=C1N[C@@H](c2cc(F)ccc2Cl)c2c(NC(=O)N3C[C@@](O)(C(F)(F)F)c4cc(F)ccc43)cc(-n3ccnn3)cc21] | O[C@]1(CN(C(=O)Nc2cc(cc3C(=O)N[C@H](c23)c2cc(F)ccc2Cl)-n2ccnn2)c2ccc(F)cc12)C(F)(F)F | (400 MHz, DMSO-d6) 9.31 (s, 1H), 9.15 (s, 1H), 9.07 (s, 1H), 8.11 (s, 2H), 8.04 (s, 1H), 7.94 (s, 1H), 7.46 (s, 1H), 7.36 (dd, J = 8.9, 5.1 Hz, 1H), 7.28 (s, 1H), 7.22 (d, J = 7.9 Hz, 1H), 7.15 (td, J = 8.4, 3.1 Hz, 1H), 6.11 (s, 1H), 4.01 (s, 1H), 3.54 (s, 1H). | 591.1 | B | |
| I-2550 | 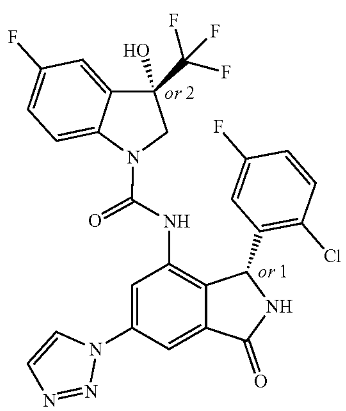 [SMILES: O=C1N[C@@H](c2cc(F)ccc2Cl)c2c(NC(=O)N3C[C@](O)(C(F)(F)F)c4cc(F)ccc43)cc(-n3ccnn3)cc21] | O[C@@]1(CN(C(=O)Nc2cc(cc3C(=O)N[C@H](c23)c2cc(F)ccc2Cl)-n2ccnn2)c2ccc(F)cc12)C(F)(F)F | | | D | |
| I-2551 | 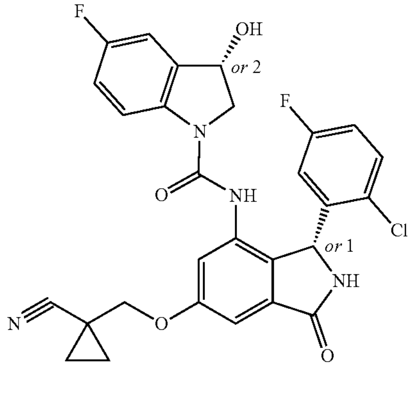 [SMILES: N#CC1(COc2cc(NC(=O)N3C[C@@H](O)c4cc(F)ccc43)c3c(c2)C(=O)N[C@H]3c2cc(F)ccc2Cl)CC1] | O[C@@H]1CN(C(=O)Nc2cc(OCC3(CC3)C#N)cc3C(=O)N[C@H](c23)c2cc(F)ccc2Cl)c2ccc(F)cc12 | | | D | |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-2552 | 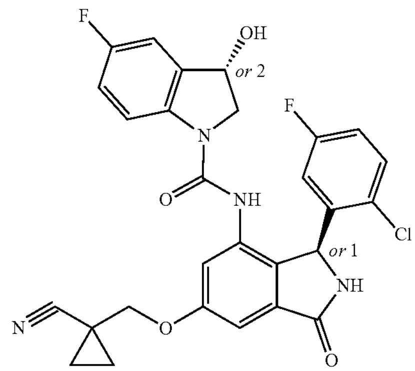 [SMILES: N#CC1(COc2cc(NC(=O)N3C[C@@H](O)c4cc(F)ccc43)c3c(c2)C(=O)N[C@@H]3c2cc(F)ccc2Cl)CC1] | O[C@@H]1CN(C(=O)Nc2cc(OCC3(CC3)C#N)cc3C(=O)N[C@@H](c23)c2cc(F)ccc2Cl)c2ccc(F)cc12 | | | A | B |
| I-2553 | 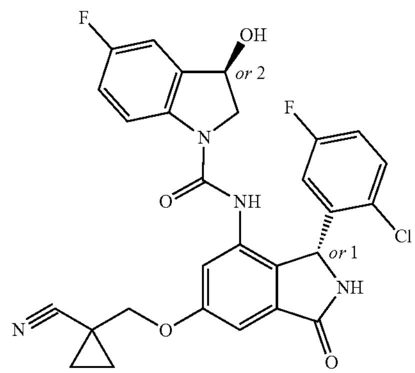 [SMILES: N#CC1(COc2cc(NC(=O)N3C[C@H](O)c4cc(F)ccc43)c3c(c2)C(=O)N[C@H]3c2cc(F)ccc2Cl)CC1] | O[C@H]1CN(C(=O)Nc2cc(OCC3(CC3)C#N)cc3C(=O)N[C@H](c23)c2cc(F)ccc2Cl)c2ccc(F)cc12 | | | | B |
| I-2554 | 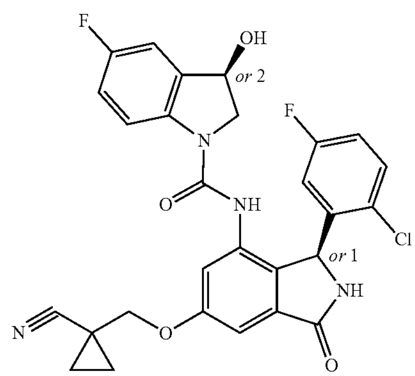 [SMILES: N#CC1(COc2cc(NC(=O)N3C[C@H](O)c4cc(F)ccc43)c3c(c2)C(=O)N[C@@H]3c2cc(F)ccc2Cl)CC1] | O[C@H]1CN(C(=O)Nc2cc(OCC3(CC3)C#N)cc3C(=O)N[C@@H](c23)c2cc(F)ccc2Cl)c2ccc(F)cc12 | | | | B |
| I-2555 | 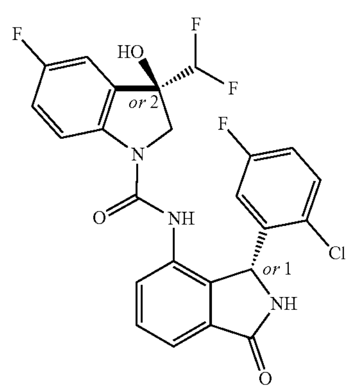 | O[C@]1(CN(C(=O)Nc2cc cc3C(=O)N[C@H](c23)c2cc(F)ccc2Cl)c2ccc(F)cc12)C(F)F | | | | D |

TABLE 2-continued

Representative Compounds of the Invention with Bioactivity Data.

| Ex. No. | Structure | SMILES | $^1$H NMR | MS | ADP-Glo IC$_{50}$ | MCF 10A IC$_{50}$ |
|---|---|---|---|---|---|---|
| I-2556 | 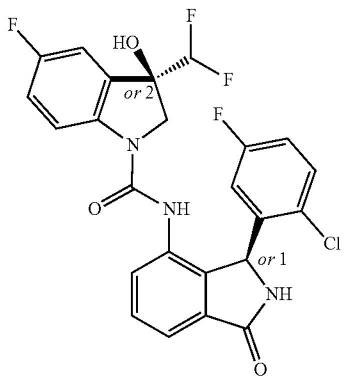 | O[C@]1(CN(C(=O)Nc2ccc3C(=O)N[C@@H](c23)c2cc(F)cc2Cl)c2ccc(F)cc12)C(F)F | | | C | |
| I-2557 | 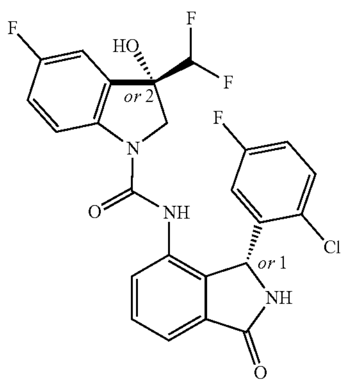 | O[C@@]1(CN(C(=O)Nc2cccc3C(=O)N[C@H](c23)c2cc(F)cc2Cl)c2cc(F)cc12)C(F)F | | | D | |
| I-2558 | 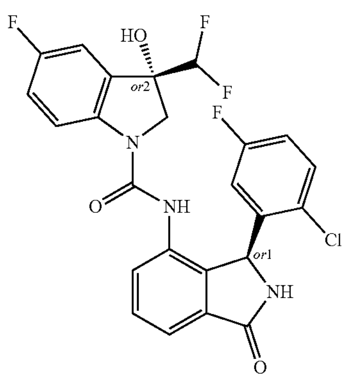 [SMILES: O=C1N[C@H](c2cc(F)ccc2Cl)c2c(NC(=O)N3C[C@](O)(C(F)F)c4cc(F)ccc43)cccc21] | O[C@@]1(CN(C(=O)Nc2cccc3C(=O)N[C@@H](c23)c2cc(F)cc2Cl)c2ccc(F)cc12)C(F)F | | | A | A |
| I-2559 | 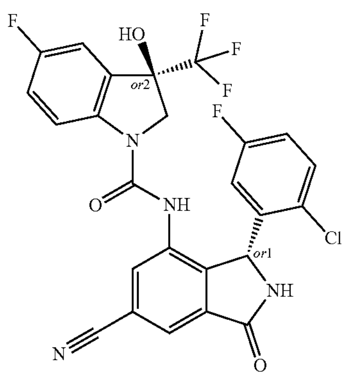 [SMILES: N#Cc1cc(NC(=O)N2C[C@@](O)(C(F)(F)F)c3cc(F)ccc32)c2c(c1)C(=O)N[C@H]2c1cc(F)ccc1Cl] | O[C@]1(CN(C(=O)Nc2cc(cc3C(=O)N[C@H](c23)c2cc(F)cc2Cl)C#N)c2ccc(F)cc12)C(F)(F)F | | | D | |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-2560 | 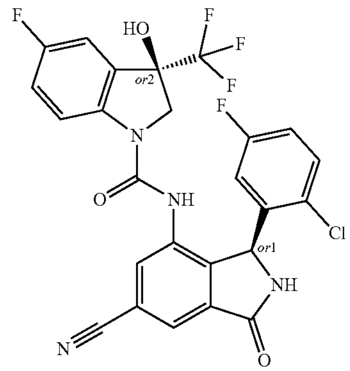 [SMILES: N#Cc1cc(NC(=O)N2C[C@@](O)(C(F)(F)F)c3cc(F)ccc32)c2c(c1)C(=O)N[C@@H]2c1cc(F)ccc1Cl] | O[C@]1(CN(C(=O)Nc2cc(cc3C(=O)N[C@@H](c23)c2cc(F)ccc2Cl)C#N)c2ccc(F)cc12)C(F)(F)F | | | A | A |
| I-2561 | 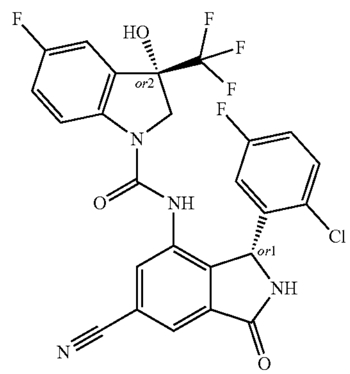 [SMILES: N#Cc1cc(NC(=O)N2C[C@](O)(C(F)(F)F)c3cc(F)ccc32)c2c(c1)C(=O)N[C@H]2c1cc(F)ccc1Cl] | O[C@@]1(CN(C(=O)Nc2cc(cc3C(=O)N[C@H](c23)c2cc(F)ccc2Cl)C#N)c2ccc(F)cc12)C(F)(F)F | | | D | |
| I-2562 | 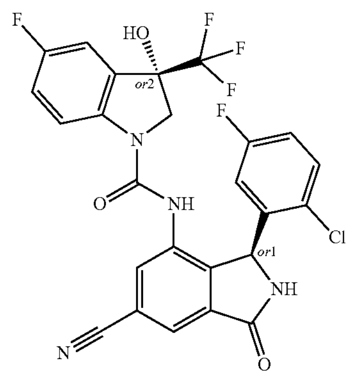 [SMILES: N#Cc1cc(NC(=O)N2C[C@](O)(C(F)(F)F)c3cc(F)ccc32)c2c(c1)C(=O)N[C@@H]2c1cc(F)ccc1Cl] | O[C@@]1(CN(C(=O)Nc2cc(cc3C(=O)N[C@@H](c23)c2cc(F)ccc2Cl)C#N)c2ccc(F)cc12)C(F)(F)F | | | A | A |
| I-2563 | 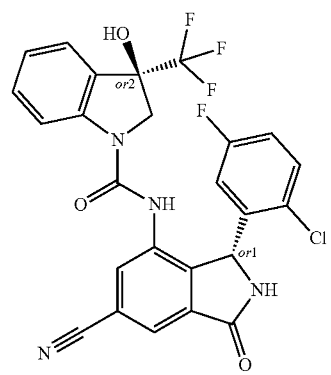 [SMILES: N#Cc1cc(NC(=O)N2C[C@@](O)(C(F)(F)F)c3ccccc32)c2c(c1)C(=O)N[C@H]2c1cc(F)ccc1Cl] | O[C@]1(CN(C(=O)Nc2cc(cc3C(=O)N[C@H](c23)c2cc(F)ccc2Cl)C#N)c2cccc12)C(F)(F)F | | | D | |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-2564 | 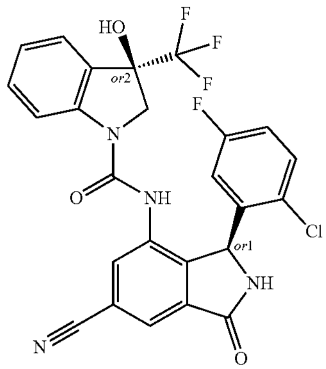 [SMILES: N#Cc1cc(NC(=O)N2C[C@@](O)(C(F)(F)F)c3ccccc32)c2c(c1)C(=O)N[C@@H]2c1cc(F)ccc1Cl] | O[C@]1(CN(C(=O)Nc2cc(cc3C(=O)N[C@@H](c23)c2cc(F)ccc2Cl)C#N)c2ccccc12)C(F)(F)F | | | A | A |
| I-2565 | 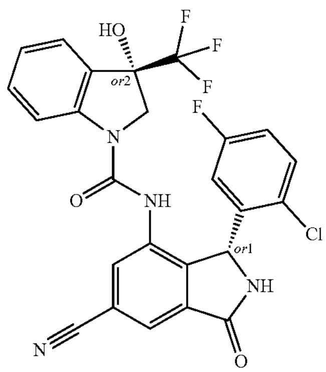 [SMILES: N#Cc1cc(NC(=O)N2C[C@](O)(C(F)(F)F)c3ccccc32)c2c(c1)C(=O)N[C@H]2c1cc(F)ccc1Cl] | O[C@@]1(CN(C(=O)Nc2cc(cc3C(=O)N[C@H](c23)c2cc(F)ccc2Cl)C#N)c2ccccc12)C(F)(F)F | | | D | |
| I-2566 | 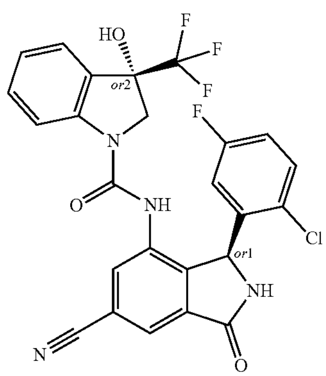 [SMILES: N#Cc1cc(NC(=O)N2C[C@](O)(C(F)(F)F)c3ccccc32)c2c(c1)C(=O)N[C@@H]2c1cc(F)ccc1Cl] | O[C@@]1(CN(C(=O)Nc2cc(cc3C(=O)N[C@@H](c23)c2cc(F)ccc2Cl)C#N)c2ccccc12)C(F)(F)F | (400 MHz, DMSO) δ 9.06 (s, 1H), 8.80 (s, 0.5H), 8.70 (s, 0.5H), 7.90 (dd, J = 8.9, 4.6 Hz, 0.5H), 7.82 (dd, J = 8.9, 4.7 Hz, 0.5H), 7.63-7.53 (m, 2H), 7.47 7.17 (m, 5H), 7.15-7.06 (m, 1H), 6.77-6.30 (m, 1H), 6.03 (s, 1H). | 526.3 | A | A |
| I-2567 | 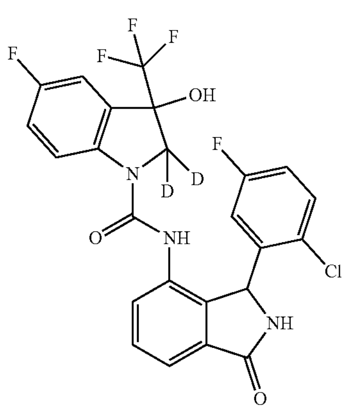 [SMILES: [2H]C1([2H])N(C(=O)Nc2cccc3c2C(c2cc(F)ccc2Cl)NC3=O)c2ccc(F)cc2C1(O)C(F)(F)F] | [2H]C1([2H])N(C(=O)Nc2cccc3C(=O)NC(c23)c2cc(F)ccc2Cl)c2ccc(F)cc2C1(O)C(F)(F)F | (400 MHz, DMSO d6) δ 9.08 (br. s, 1H), 8.89 (s, 1H), 8.31 (s, 1H), 7.97-7.87 (m, 1H), 7.67 (s, 1H), 7.47 (d, J = 3.3 Hz, 1H), 7.39 (d, J = 3.1 Hz, 1H), 7.37-7.29 (m, 1H), 7.28-7.17 (m, 3H), 7.16-7.06 (m, 1H), 6:52 (br. s, 1H), 6.04 (br. s, 1H), 4.23 (d, J = 11.6 Hz, 1H), 3.96 (d, J = 2.8 Hz, 2H), 3.50 (d, J = 10.2 Hz, 1H). 1:1 mixture | 553.4 | A | A |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-2568 | 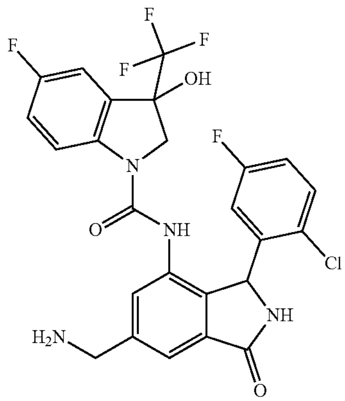 [SMILES: NCc1cc(NC(=O)N2CC(O)(C(F)(F)F)c3cc(F)ccc32)c2c(c1)C(=O)NC2c1cc(F)ccc1Cl] | NCc1cc2C(=O)NC(c2c(NC(=O)N2CC(O)(c3cc(F)cc c23)C(F)(F)F)c1)c1cc(F)ccc1Cl | | 591.1 | A | D |
| I-2569 | 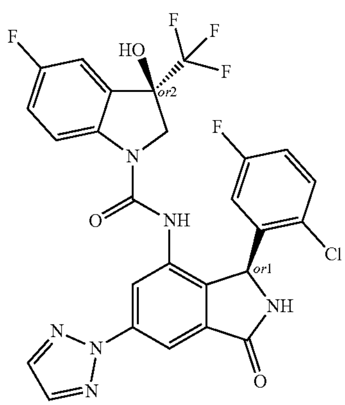 [SMILES: O=C1N[C@H](c2cc(F)ccc2Cl)c2c(NC(=O)N3C[C@@](O)(C(F)(F)F)c4cc(F)ccc43)cc(-n3nccn3)cc21] | O[C@]1(CN(C(=O)Nc2cc(cc3C(=O)N[C@@H](c23)c2cc(F)ccc2Cl)-n2nccn2)c2ccc(F)cc12)C(F)(F)F | (400 MHz, DMSO-d6) 9.30 (s, 1H), 8.99 (s, 1H), 8.28-8.20 (m, 3H), 8.12 (d, J = 1.9 Hz, 1H), 7.90 (dd, J = 8.9, 4.7 Hz, 1H), 7.41-7.33 (m, 2H), 7.32-7.19 (m, 2H), 7.14 (td, J = 8.3, 3.1 Hz, 1H), 6.72 (s, 1H), 6.14 (s, 1H), 4.23 (d, J = 12.0 Hz, 1H), 3.44 (d, J = 12.1 Hz, 1H). | 591.1 | A | A |
| I-2570 | 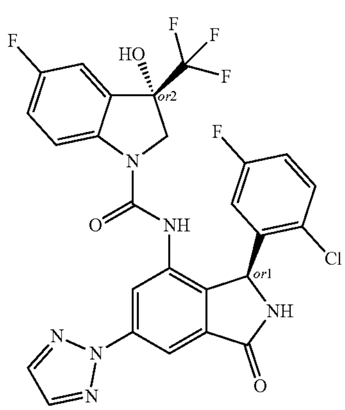 [SMILES: O=C1N[C@H](c2cc(F)ccc2Cl)c2c(NC(=O)N3C[C@](O)(C(F)(F)F)c4cc(F)ccc43)cc(-n3nccn3)cc21] | O[C@@]1(CN(C(=O)Nc2cc(cc3C(=O)N[C@@H](c23)c2cc(F)ccc2Cl)-n2nccn2)c2ccc(F)cc12)C(F)(F)F | (400 MHz, DMSO-d6) 9.30 (s, 1H), 8.99 (s, 1H), 8.28-8.20 (m, 3H), 8.12 (d, J = 1.9 Hz, 1H), 7.90 (dd, J = 9.0, 4.7 Hz, 1H), 7.41-7.33 (m, 2H), 7.26 (ddd, J = 21.4, 8.9, 2.8 Hz, 2H), 7.14 (td, J = 8.3, 3.1 Hz, 1H), 6.71 (s, 1H), 6.14 (s, 1H), 4.23 (d, J = 12.0 Hz, 1H), 3.44 (d, J = 11.9 Hz, 1H). | 591.1 | D | |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-2571 | 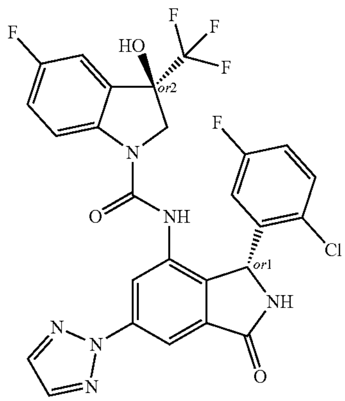 [SMILES: O=C1N[C@@H](c2cc(F)ccc2Cl)c2c(NC(=O)N3C[C@@](O)(C(F)(F)F)c4cc(F)ccc43)cc(-n3nccn3)cc21] | O[C@]1(CN(C(=O)Nc2cc(cc3C(=O)N[C@H](c23)c2cc(F)cc c2Cl)-n2nccn2)c2ccc(F)cc12)C(F)(F)F | (400 MHz, DMSO-d6) 9.29 (s, 1H), 9.09 (s, 1H), 8.22 (s, 2H), 8.18 (d, J = 2.0 Hz, 1H), 8.12 (d, J = 1.9 Hz, 1H), 7.96 (d, J = 9.0 Hz, 1H), 7.42 (s, 1H), 7.39-7.25 (m, 2H), 7.22 (dd, J = 8.0, 2.7 Hz, 1H), 7.14 (td, J = 8.4, 3.1 Hz, 1H), 6.71 (s, 1H), 6.10 (s, 1H), 4.03 (d, J = 12.2 Hz, 1H), 3.54 (d, J = 12.0 Hz, 1H). | 591.4 | D | |
| I-2572 | 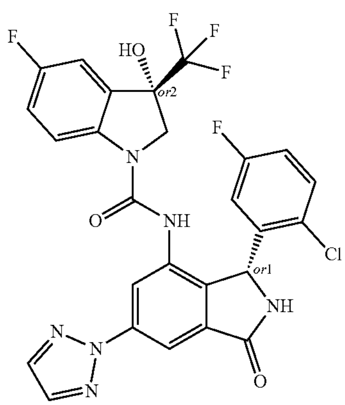 [SMILES: O=C1N[C@@H](c2cc(F)ccc2Cl)c2c(NC(=O)N3C[C@](O)(C(F)(F)F)c4cc(F)ccc43)cc(-n3nccn3)cc21] | O[C@@]1(CN(C(=O)Nc2cc(cc3C(=O)N[C@H](c23)c2cc(F)cc c2Cl)-n2nccn2)c2ccc(F)cc12)C(F)(F)F | (400 MHz, DMSO-d6) 7.86 (s, 1H), 7.79 (s, 1H), 7.67 (dd, J = 6.4, 3.5 Hz, 1H), 7.28 (dt, J = 8.6, 4.2 Hz, 1H), 7.23 (s, 1H), 7.19 (dd, J = 8.1, 2.6 Hz, 1H), 7.07 (s, 1H), 6.58 (s, 1H), 5.91 (s, 1H), 4.00 (s, 1H), 3.42 (d, J = 12.1 Hz, 1H), 2.08 (d, J = 2.6 Hz, 3H). | 581.2 | D | |
| I-2573 | 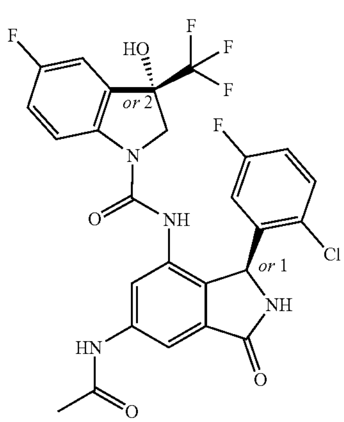 | CC(=O)Nc1cc2C(=O)N[C@@H](c2c(NC(=O)N2C[C@@](O)(c3cc(F)ccc23)C(F)(F)F)c1cc(F)ccc1Cl | (400 MHz, DMSO-d6) 10.26 (s, 1H), 9.05 (s, 1H), 8.73 (s, 1H), 7.89-7.81 (m, 2H), 7.79 (d, J = 1.9 Hz, 1H), 7.37-7.29 (m, 2H), 7.23 (ddd, J = 18.6, 9.4, 2.8 Hz, 2H), 7.11 (td, J = 8.3, 3.1 Hz, 1H), 6.57 (s, 1H), 5.99 (s, 1H), 4.22 (d, J = 12.0 Hz, 1H), 3.40 (d, J = 12.0 Hz, 1H), 2.11 (s, 3H). | 581.2 | A | A |

TABLE 2-continued

Representative Compounds of the Invention with Bioactivity Data.

| Ex. No. | Structure | SMILES | $^1$H NMR | MS | ADP-Glo IC$_{50}$ | MCF 10A IC$_{50}$ |
|---|---|---|---|---|---|---|
| I-2574 | 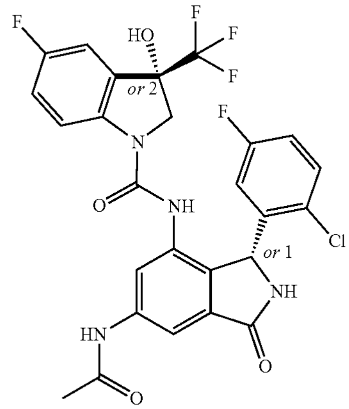 | CC(=O) Nc1cc2C (=O)N[C @H](c2c (NC(=O) N2C[C@ @](O)(c3 cc(F)ccc 23)C(F) (F)F)c1)c 1cc(F)cc c1Cl | (400 MHz, DMSO-d6) 10.26 (s, 1H), 9.05 (s, 1H), 8.73 (s, 1H), 7.89-7.81 (m, 2H), 7.79 (d, J = 1.9 Hz, 1H), 7.37-7.29 (m, 2H), 7.23 (ddd, J = 18.5, 9.3, 2.8 Hz, 2H), 7.11 (td, J = 8.3, 3.1 Hz, 1H), 6.56 (s, 1H), 5.99 (s, 1H), 4.22 (d, J = 12.0 Hz, 1H), 3.40 (d, J = 12.1 Hz, 1H), 2.11 (s, 3H). | 581.2 | B | |
| I-2575 | 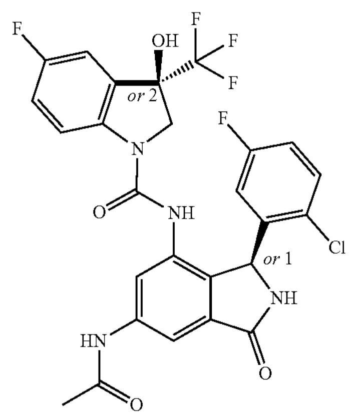 | CC(=O) Nc1cc2C (=O)N[C @@H](c 2c(NC(= O)N2C [C@](O) (c3cc(F)c cc23)C(F) (F)F)c1) c1cc(F)c cc1Cl | (400 MHz, DMSO-d6) 10.26 (s, 1H), 9.04 (s, 1H), 8.84 (s, 1H), 7.93 (dd, J = 9.3, 4.6 Hz, 1H), 7.83 (d, J = 1.8 Hz, 1H), 7.72 (d, J = 1.9 Hz, 1H), 7.36 (s, 1H), 7.35-7.23 (m, 2H), 7.20 (dd, J = 8.1, 2.7 Hz, 1H), 7.12 (td, J = 8.4, 3.1 Hz, 1H), 6.57 (s, 1H), 5.95 (s, 1H), 4.02 (d, J = 12.2 Hz, 1H), 3.48 (d, J = 12.1 Hz, 1H), 2.11 (s, 3H). | 581.2 | D | |
| I-2576 | 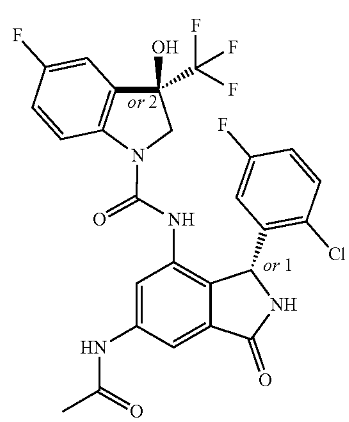 | CC(=O) Nc1cc2C (=O)N[C @H](c2c (NC(=O) N2C[C@] (O)(c3cc (F)ccc23) C(F)(F)F c1)c1cc (F)ccc1Cl | (400 MHz, DMSO-d6) 9.27 (s, 1H), 8.89 (s, 1H), 7.87 (dd, J = 9.0, 4.6 Hz, 1H), 7.78 (s, 1H), 7.70 (s, 1H), 7.42-7.32 (m, 2H), 7.30-7.18 (m, 2H), 7.17-7.07 (m, 1H), 6.90-6.40 (m, 1H), 6.12 (s, 1H), 4.21 (d, J = 12.0 Hz, 1H), 3.43 (d, J = 12.2 Hz, 1H | 574.1 | D | |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-2577 | 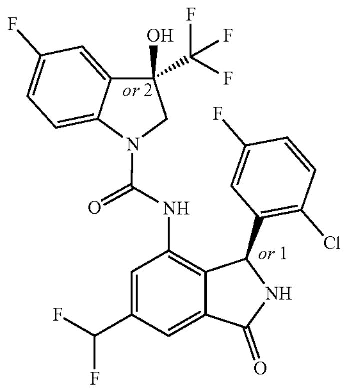 [SMILES: O=C1N[C@H](c2cc(F)ccc2Cl)c2c(NC(=O)N3C[C@@](O)(C(F)(F)F)c4cc(F)ccc43)cc(C(F)F)cc21] | O[C@]1(CN(C(=O)Nc2cc(cc3C(=O)N[C@@H](c23)c2cc(F)ccc2Cl)C(F)F)c2cc c(F)cc12)C(F)(F)F | (400 MHz, DMSO-d6) 9.28 (s, 1H), 8.90 (s, 1H), 7.87 (dd, J = 9.0, 4.6 Hz, 1H), 7.78 (s, 1H), 7.70 (s, 1H), 7.43-7.33 (m, 2H), 7.32-7.19 (m, 2H), 7.18-7.06 (m, 1H), 6.90-6.12 (m, 1H), 4.21 (d, J = 12.0 Hz, 1H), 3.43 (d, J = 12.1 Hz, 1H). | 574.0 | D | |
| I-2578 | 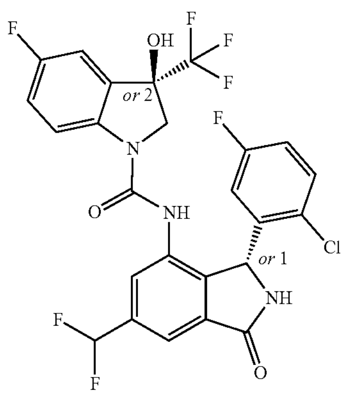 [SMILES: O=C1N[C@@H](c2cc(F)ccc2Cl)c2c(NC(=O)N3C[C@@](O)(C(F)(F)F)c4cc(F)ccc43)cc(C(F)F)cc21] | O[C@]1(CN(C(=O)Nc2cc(cc3C(=O)N[C@H](c23)c2cc(F)cc c2Cl)C(F)F)c2ccc(F)cc12)C(F)(F)F | (400 MHz, DMSO-d6) 9.27 (s, 1H), 9.00 (s, 1H), 7.93 (s, 1H), 7.78 (s, 1H), 7.61 (s, 1H), 7.43 (s, 1H), 7.41-7.18 (m, 4H), 7.15-7.07 (m, 1H), 6.90-6.40 (m, 1H), 6.08 (s, 1H), 4.00 (d, J = 12.1 Hz, 1H), 3.51 (d, J = 12.1 Hz, 1H). | 574.1 | D | |
| I-2579 | 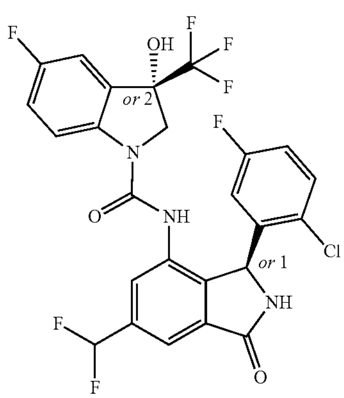 [SMILES: O=C1N[C@H](c2cc(F)ccc2Cl)c2c(NC(=O)N3C[C@](O)(C(F)(F)F)c4cc(F)ccc43)cc(C(F)F)cc21] | O[C@@]1(CN(C(=O)Nc2cc(cc3C(=O)N[C@@H](c23)c2cc(F)ccc2Cl)C(F)F)c2cc c(F)cc12)C(F)(F)F | (400 MHz, DMSO-d6) 9.26 (s, 1H), 8.99 (s, 1H), 7.93 (s, 1H), 7.78 (s, 1H), 7.61 (s, 1H), 7.42 (s, 1H), 7.37-7.32 (m, 1H), 7.28 (td, J = 9.0, 2.7 Hz, 1H), 7.25-7.07 (m, 3H), 6.90-6.40 (m, 1H), 6.08 (s, 1H), 4.00 (d, J = 12.1 Hz, 1H), 3.52 (d, J = 12.1 Hz, 1H). | 574.1 | A | A |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-2580 | 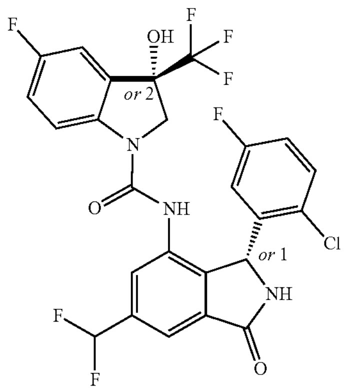 | O[C@@]1(CN(C(=O)Nc2cc(cc3C(=O)N[C@H](c23)c2cc(F)cc c2Cl)C(F)F)c2ccc(F)cc12)C(F)(F)F | (400 MHz, DMSO-d6) 9.00 (d, J = 17.4 Hz, 1H), 8.68 (s, 1H), 7.96-7.81 (m, 1H), 7.46 (s, 1H), 7.40-7.17 (m, 6H), 7.11 (td, J = 8.4, 3.1 Hz, 1H), 6.55 (s, 1H), 6.03 (s, 1H), 4.24 (d, J = 12.0 Hz, 1H), 3.41 (d, J = 12.1 Hz, 1H), 2.97-2.74 (m, 4H). | 567.2 | D | |
| I-2581 | 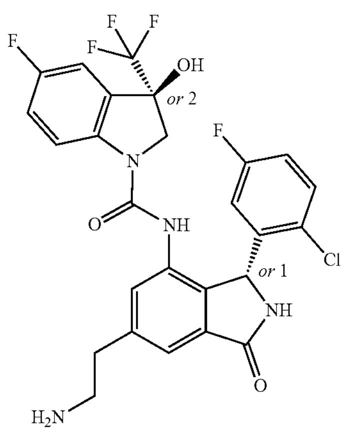 [SMILES: NCCc1cc(NC(=O)N2C[C@@](O)(C(F)(F)F)c3cc(F)ccc32)c2c(c1)C(=O)N[C@H]2c1cc(F)ccc1Cl] | NCCc1cc2C(=O)N[C@H](c2c(NC(=O)N2C[C@](O)(c3cc(F)c cc23)C(F)(F)F)c1)c1cc(F)c cc1Cl | (400 MHz, DMSO-d6) 9.00 (d, J = 17.4 Hz, 1H), 8.68 (s, 1H), 7.96-7.81 (m, 1H), 7.46 (s, 1H), 7.40-7.17 (m, 6H), 7.11 (td, J = 8.4, 3.1 Hz, 1H), 6.55 (s, 1H), 6.03 (s, 1H), 4.24 (d, J = 12.0 Hz, 1H), 3.41 (d, J = 12.1 Hz, 1H), 2.97-2.74 (m, 4H). | 567.2 | A | D |
| I-2582 | 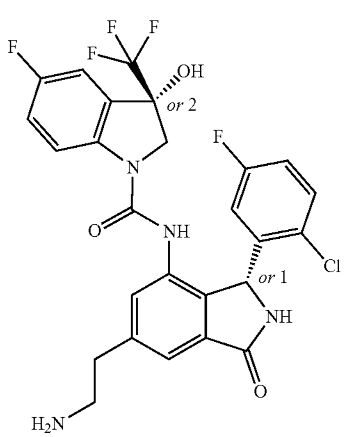 [SMILES: NCCc1cc(NC(=O)N2C[C@](O)(C(F)(F)F)c3cc(F)ccc32)c2c(c1)C(=O)N[C@H]2c1cc(F)ccc1Cl] | NCCc1cc2C(=O)N[C@H](c2c(NC(=O)N2C[c@@](O)(c3cc(F)c cc23)C(F)(F)F)c1)c1cc(F)c cc1Cl | (400 MHz, DMSO-d6) 9.00 (d, J = 17.4 Hz, 1H), 8.68 (s, 1H), 7.96-7.81 (m, 1H), 7.46 (s, 1H), 7.40-7.17 (m, 6H), 7.11 (td, J = 8.4, 3.1 Hz, 1H), 6.55 (s, 1H), 6.03 (s, 1H), 4.24 (d, J = 12.0 Hz, 1H), 3.41 (d, J = 12.1 Hz, 1H), 2.97-2.74 (m, 4H). | 567.2 | B | |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-2583 | 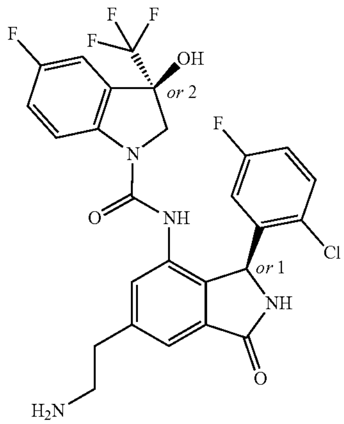 [SMILES: NCCc1cc(NC(=O)N2C[C@@](O)(C(F)(F)F)c3cc(F)ccc32)c2c(c1)C(=O)N[C@@H]2c1cc(F)ccc1Cl] | NCCc1cc2C(=O)N[C@@H](c2c(NC(=O)N2C[C@](O)(c3cc(F)cc23)C(F)(F)F)c1)c1cc(F)ccc1Cl | (400 MHz, DMSO-d6) 9.00 (d, J = 17.4 Hz, 1H), 8.68 (s, 1H), 7.96-7.81 (m, 1H), 7.46 (s, 1H), 7.40-7.17 (m, 6H), 7.11 (td, J = 8.4, 3.1 Hz, 1H), 6.55 (s, 1H), 6.03 (s, 1H), 4.24 (d, J = 12.0 Hz, 1H), 3.41 (d, J = 12.1 Hz, 1H), 2.97-2.74 (m, 4H). | 567.1 | D | |
| I-2584 | 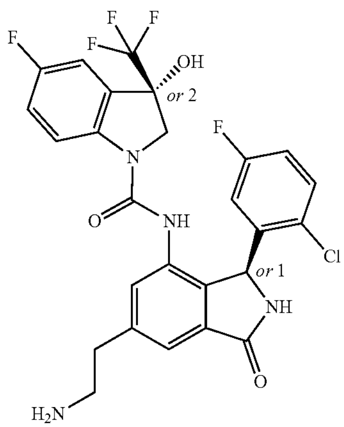 [SMILES: NCCc1cc(NC(=O)N2C[C@](O)(C(F)(F)F)c3cc(F)ccc32)c2c(c1)C(=O)N[C@@H]2c1cc(F)ccc1Cl] | NCCc1cc2C(=O)N[C@@H](c2c(NC(=O)N2C[C@@](O)(c3cc(F)ccc23)C(F)(F)F)c1cc(F)ccc1Cl | (400 MHz, DMSO-d6) as a ca. 1:1 mixture of diastereomers, δ 9.15 (br. s, 1H), 9.13 (br. s, 1H), 8.89 (br. s, 1H), 8.77 (br. s, 1H), 7.90 (br. d, J = 7.8 Hz, 1H), 7.83 (d, J = 8.2 Hz, 1H), 7.59-7.57 (m, 1H), 7.51-7.49 (m, 1H), 7.45-7.29 (m, 7H), 7.22 (s, 1H), 7.20 (s, 1H), 7.14-7.04 (m, 4H), 6.58 (br. s, 2H), 6.08 (br. s, 1H), 6.03 (br. s, 1H), 4.24 (s, 4H), 4.17 (d, A of AB, JAB = 12.1 Hz, 1H), 3.97 (d, A of AB, JAB = 12.4 Hz, 1H), 3.48 (d, B of AB, JAB = 11.8 Hz, 1H), 3.43 (d, B of AB, JAB = 11.9 Hz, 1H). | 545.4 | D | |
| I-2585 | 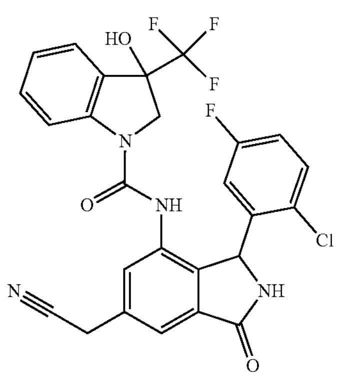 [SMILES: N#CCc1cc(NC(=O)N2CC(O)(C(F)(F)F)c3ccccc32)c2c(c1)C(=O)NC2c1cc(F)ccc1Cl] | OC1(CN(C(=O)Nc2cc(CC#N)cc3C(=O)NC(c23)c2cc(F)ccc2Cl)cccc12)C(F)(F)F | (400 MHz, DMSO-d6) δ as a ca. 3:2 mixture of diastereomers; for both diastereomers, δ 9.16 (br. s, 1H), 9.15 (br. s, 1H), 8.86 (br. s, 1H), 8.75 (br. s, 1H), 7.89 (dd, J = 8.4, 3.9 Hz, 1H), 7.81 (dd, J = 8.9, 4.7 Hz, 1H), 7.57 (br. s, 2H), 7.47 (d, J = 1.2 Hz, 1H), 7.39 (d, J = 1.2 Hz, 1H), 7.37-7.30 (m, 2H), 7.28-7.21 (m, 2H), 7.20-7.16 (m, 2H), 7.15-7.08 (m, 2H), 6.71 (s, 1H), 6.64 (s, 1H), 6.58 (br. s, 1H), 6.42-6.12 (m, 2H), 6.07 (br. s, 1H), 6.03 (br. s, 1H), 4.23 (s, 4H), 4.11 (d, A of AB, JAB = 11.8 Hz, 1H), 3.86 (d, A of AB, JAB = 11.3 Hz, 1H), 3.44 (d, B of AB JAB = 11.4 Hz, 1H), 3.29 (d, B of AB JAB = 12.3 Hz, 1H). | 545.3 | A | A |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-2586 | 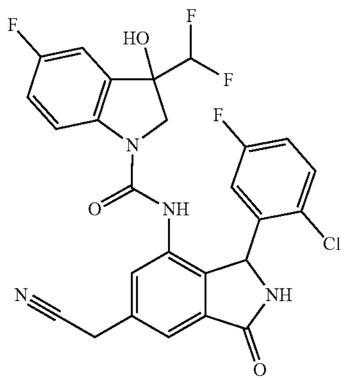 [SMILES: N#CCc1cc(NC(=O)N2CC(O)(C(F)F)c3cc(F)ccc32)c2c(c1)C(=O)NC2c1cc(F)ccc1Cl] | OC1(CN(C(=O)Nc2cc(CC#N)cc3C(=O)NC(c23)c2cc(F)ccc2C1)c2ccc(F)cc12)C(F)F | (400 MHz, DMSO-d6) δ 9.18 (br s, 1 H), 8.85 (br s, 2 H), 7.95-7.80 (m, 1 H), 7.35-7.23 (m, 2 H), 7.23-7.17 (m, 1 H), 7.14-7.05 (m, 1 H), 6.81 (s, 0.5 H), 6.74 (s, 0.5 H), 6.65 (br s, 1 H), 6.52-6.44 (m, 1 H), 5.90 (br s, 1 H), 4.19 (d, J = 12.0 Hz, 0.5 H), 3.97 (d, J = 12.1 Hz, 0.5 H), 3.45 (submerged d, J = 12.0 Hz, 0.5 H), 3.30 (submerged d, J = 12.2 Hz, 0.5 H), 2.90-2.72 (m, 3 H). ~1:1 mixture of diastereomers. | 578.3 | A | B |
| I-2587 | 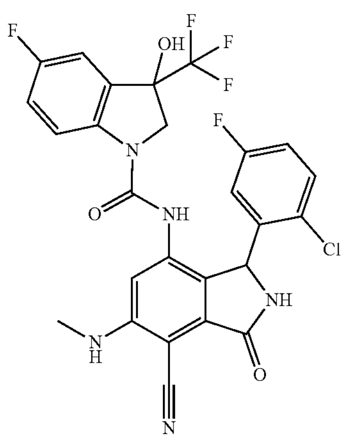 [SMILES: CNc1cc(NC(=O)N2CC(O)(C(F)(F)F)c3cc(F)ccc32)c2c(c1C#N)C(=O)NC2c1cc(F)ccc1Cl] | CNc1cc(NC(=O)N2CC(O)(c3cc(F)ccc23)C(F)(F)F)c2C(NC(=O)c2c1C#N)c1cc(F)ccc1Cl | | | A | B |
| I-2588 | 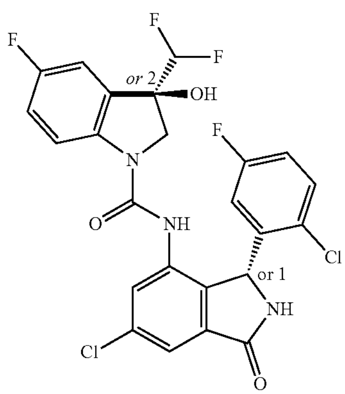 [SMILES: O=C1N[C@@H](c2cc(F)ccc2Cl)c2c(NC(=O)N3C[C@@](O)(C(F)F)c4cc(F)ccc43)cc(Cl)cc21] | O[C@]1(CN(C(=O)Nc2cc(Cl)cc3C(=O)N[C@H](c23)c2cc(F)cc2Cl)c2ccc(F)cc12)C(F)F | | | | D |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-2589 | 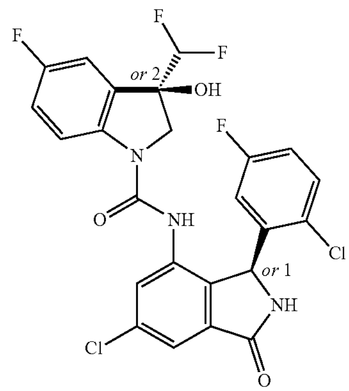 [SMILES: O=C1N[C@H](c2cc(F)ccc2Cl)c2c(NC(=O)N3C[C@@](O)(C(F)F)c4cc(F)ccc43)cc(Cl)cc21] | O[C@]1(CN(C(=O)Nc2cc(Cl)cc3C(=O)N[C@@H](c23)c2cc(F)ccc2Cl)c2ccc(F)cc12)C(F)F | | | D | |
| I-2590 | 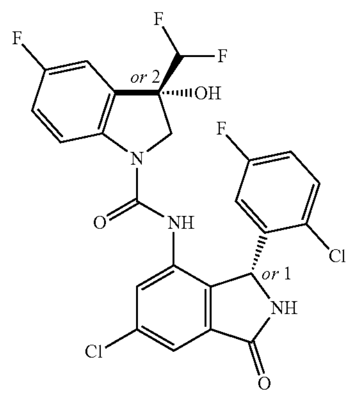 [SMILES: O=C1N[C@@H](c2cc(F)ccc2Cl)c2c(NC(=O)N3C[C@](O)(C(F)F)c4cc(F)ccc43)cc(Cl)cc21] | O[C@@]1(CN(C(=O)Nc2cc(Cl)cc3C(=O)N[C@H](c23)c2cc(F)ccc2Cl)c2ccc(F)cc12)C(F)F | | | D | |
| I-2591 | 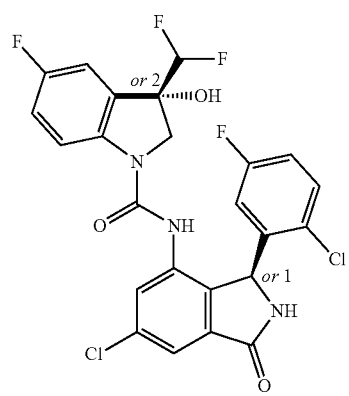 [SMILES: O=C1N[C@H](c2cc(F)ccc2Cl)c2c(NC(=O)N3C[C@](O)(C(F)F)c4cc(F)ccc43)cc(Cl)cc21] | O[C@@]1(CN(C(=O)Nc2cc(Cl)cc3C(=O)N[C@@H](c23)c2cc(F)ccc2C1)c2ccc(F)cc12)C(F)F | | 525.9 | A | A |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-2592 | 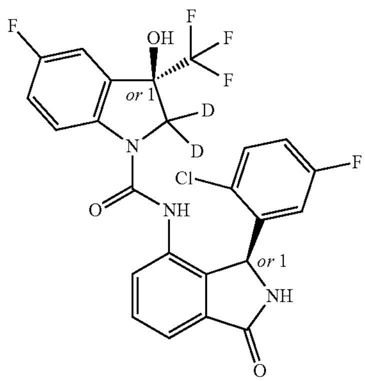 [SMILES: [2H]C1([2H])N(C(=O)Nc2cccc3c2[C@@H](c2cc(F)ccc2Cl)NC3=O)c2ccc(F)cc2[C@]1(O)C(F)(F)F] | [2H]C1([2H])N(C(=O)Nc2cccc3C(=O)N[C@@H](c23)c2cc(F)cc2Cl)c2ccc(F)cc2[C@]1(O)C(F)(F)F | | 525.9 | D | |
| I-2593 | 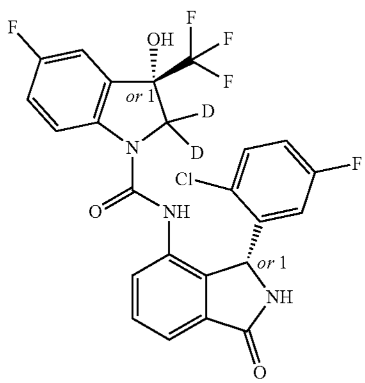 [SMILES: [2H]C1([2H])N(C(=O)Nc2cccc3c2[C@H](c2cc(F)ccc2Cl)NC3=O)c2ccc(F)cc2[C@@]1(O)C(F)(F)F] | [2H]C1([2H])N(C(=O)Nc2cccc3C(=O)N[C@H](c23)c2cc(F)cc2Cl)c2cc(F)cc2[C@@]1(O)C(F)(F)F | | 525.8 | D | |
| I-2594 | 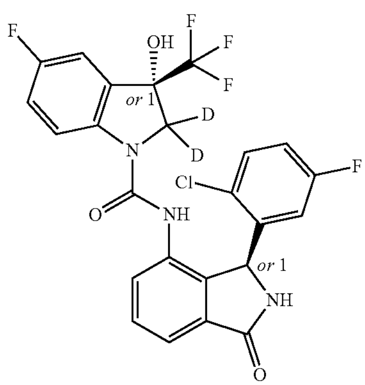 [SMILES: [2H]C1([2H])N(C(=O)Nc2cccc3c2[C@@H](c2cc(F)ccc2Cl)NC3=O)c2ccc(F)cc2[C@@]1(O)C(F)(F)F] | [2H]C1([2H])N(C(=O)Nc2cccc3C(=O)N[C@@H](c23)c2cc(F)cc2Cl)c2ccc(F)cc2[C@@]1(O)C(F)(F)F | (400 MHz, DMSO) δ 9.05 (s, 1H), 8.79 (s, 1H), 7.90 (dd, J = 8.9, 4.7 Hz, 1H), 7.63-7.53 (m, 2H), 7.39-7.35 (m, 2H), 7.31 (dd, J = 8.9, 5.1 Hz, 1H), 7.25 (td, J = 9.0, 2.8 Hz, 1H), 7.19 (dd, J = 8.1, 2.7 Hz, 1H), 7.15-7.08 (m, 1H), 6.65-6.38 (m, 1H), 6.01 (s, 1H). | 525.9 | D | |
| I-2595 | 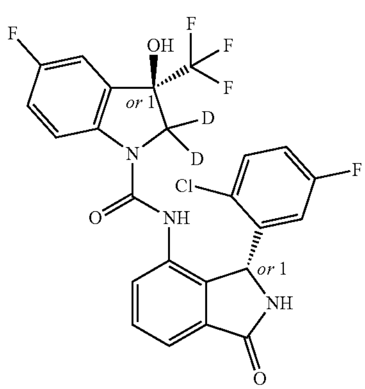 [SMILES: [2H]C1([2H])N(C(=O)Nc2cccc3c2[C@H](c2cc(F)ccc2Cl)NC3=O)c2ccc(F)cc2[C@]1(O)C(F)(F)F] | [2H]C1([2H])N(C(=O)Nc2cccc3C(=O)N[C@H](c23)c2cc(F)cc2Cl)c2cc(F)cc2[C@]1(O)C(F)(F)F | | 525.9 | A | A |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-2596 | 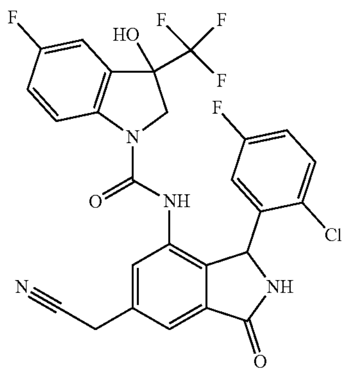 [SMILES: N#CCc1cc(NC(=O)N2CC(O)(C(F)(F)F)c3cc(F)ccc32)c2c(c1)C(=O)NC2c1cc(F)ccc1Cl] | OC1(CN(C(=O)Nc2cc(CC#N)cc3C(=O)NC(c23)c2cc(F)ccc2C1)c2ccc(F)cc12)C(F)(F)F | (400 MHz, DMSO-d6) δ as a ca. 1:1 mixture of diastereomers, δ 9.17 (br. s, 2H), 8.94 (s, 1H), 8.83 (s, 1H), 7.95-7.90 (m, 1H), 7.86 (dd, J = 8.9, 4.7 Hz, 1H), 7.59 (br. s, 2H), 7.47 (d, J = 1.3 Hz, 1H), 7.42-7.38 (m, 3H), 7.37-7.30 (m, 2H), 7.30-7.19 (m, 5H), 7.16-7.09 (m, 2H), 6.56 (br. s, 2H), 6.11-5.97 (m, 2H), 4.24 (s, 4H), 4.23-4.20 (m, 1H), 4.01 (d, J = 12.1 Hz, 1H), 3.48 (d, J = 12.0 Hz, 1H), 3.39 (d, J = 12.1 Hz, 1H). Multiplet at 4.23-4.20 ppm is partially obscured by 4H singlet at 4.24 ppm. | 563.3 | A | A |
| I-2597 | 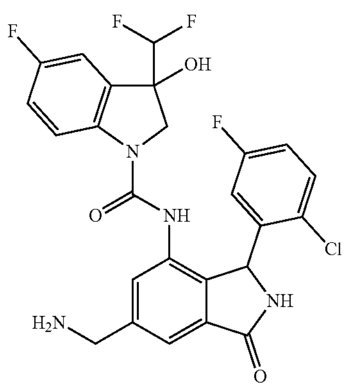 [SMILES: NCc1cc(NC(=O)N2CC(O)(C(F)F)c3cc(F)ccc32)c2c(c1)C(=O)NC2c1cc(F)ccc1Cl] | NCc1cc2C(=O)NC(c2c(NC(=O)N2CC(O)(C(F)F)c3cc(F)ccc23)c1)c1c(F)ccc1Cl | (400 MHz, DMSOD6) δ 9.10 (s, 1H), 8.84 (s, 1H), 8.34 (s, 1H), 7.87 (dd, J = 8.4, 4.4 Hz, 1H), 7.67 (s, 1H), 7.49 (s, 1H), 7.34 (dd, J = 8.9, 5.2 Hz, 1H), 7.26 (dd, J = 6.2, 3.0 Hz, 1 H), 7.07-7.21 (m, 2H), 6.51 (br s, 1H), 6.28 (td, J = 55.4, 1.9 Hz, 1H), 6.08 (br. s, 1H), 4.12 (d, J = 11.8 Hz, 1H), 3.99 (s, 2H), 3.46 (d, J = 12.0 Hz, 1H). | 535.2 | A | D |
| I-2598 | 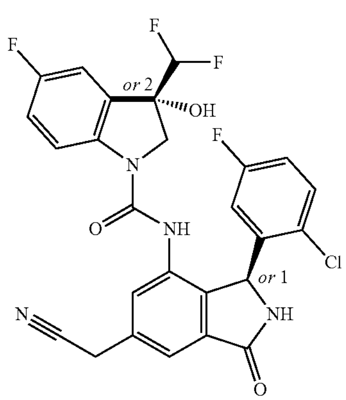 [SMILES: N#CCc1cc(NC(=O)N2C[C@@](O)(C(F)F)c3cc(F)ccc32)c2c(c1)C(=O)N[C@@H]2c1cc(F)ccc1Cl] | O[C@@]1(CN(C(=O)Nc2cc(CC#N)cc3C(=O)N[C@@H](c23)c2cc(F)cc2Cl)c2cc(F)cc12)C(F)F | | | | D |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-2599 | 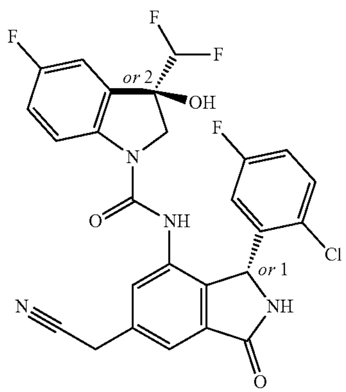 [SMILES: N#CCc1cc(NC(=O)N2C[C@@](O)(C(F)F)c3cc(F)ccc32)c2c(c1)C(=O)N[C@H]2c1cc(F)ccc1Cl] | O[C@]1(CN(C(=O)Nc2cc(CC#N)cc3C(=O)N[C@H](c23)c2cc(F)ccc2Cl)c2ccc(F)cc12)C(F)F | | | B | |
| I-2600 | 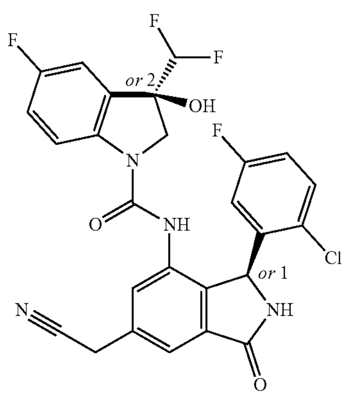 [SMILES: N#CCc1cc(NC(=O)N2C[C@@](O)(C(F)F)c3cc(F)ccc32)c2c(c1)C(=O)N[C@@H]2c1cc(F)ccc1Cl] | O[C@]1(CN(C(=O)Nc2cc(CC#N)cc3C(=O)N[C@@H](c23)c2cc(F)cc2Cl)c2ccc(F)cc12)C(F)F | | | C | |
| I-2601 | 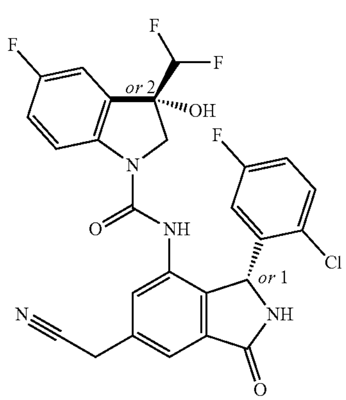 [SMILES: N#CCc1cc(NC(=O)N2C[C@@](O)(C(F)F)c3cc(F)ccc32)c2c(c1)C(=O)N[C@H]2c1cc(F)ccc1Cl] | O[C@@]1(CN(C(=O)Nc2cc(CC#N)cc3C(=O)N[C@H](c23)c2cc(F)ccc2Cl)c2ccc(F)cc12)C(F)F | | | A | A |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-2602 | 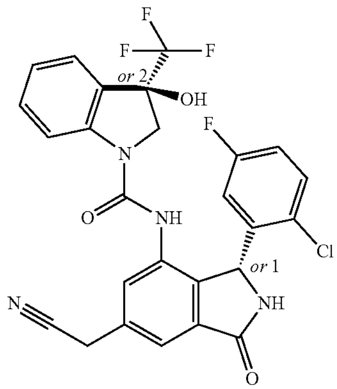 [SMILES: N#CCc1cc(NC(=O)N2C[C@@](O)(C(F)(F)F)c3ccccc32)c2c(c1)C(=O)N[C@H]2c1cc(F)ccc1Cl] | O[C@]1(CN(C(=O)Nc2ccc(CC#N)cc3C(=O)N[C@H](c23)c2cc(F)ccc2Cl)c2cccc12)C(F)(F)F | | | D | |
| I-2603 | 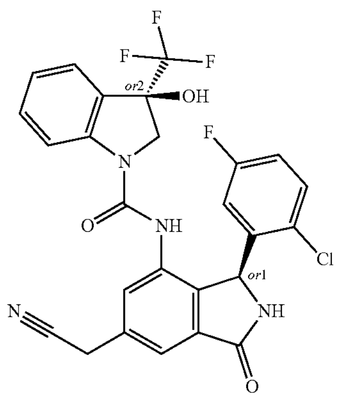 [SMILES: N#CCc1cc(NC(=O)N2C[C@@](O)(C(F)(F)F)c3ccccc32)c2c(c1)C(=O)N[C@@H]2c1cc(F)ccc1Cl] | O[C@]1(CN(C(=O)Nc2ccc(CC#N)cc3C(=O)N[C@@H](c23)c2cc(F)ccc2Cl)c2cccc12)C(F)(F)F | | | D | |
| I-2604 | 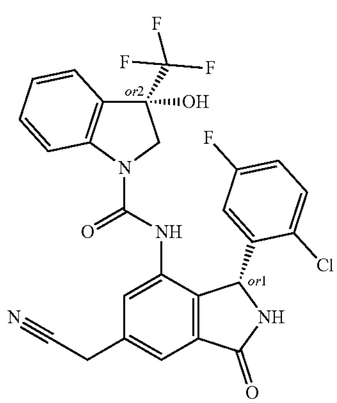 [SMILES: N#CCc1cc(NC(=O)N2C[C@](O)(C(F)(F)F)c3ccccc32)c2c(c1)C(=O)N[C@H]2c1cc(F)ccc1Cl] | O[C@@]1(CN(C(=O)Nc2cc(CC#N)cc3C(=O)N[C@H](c23)c2cc(F)ccc2Cl)c2cccc12)C(F)(F)F | | | C | |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-2605 | 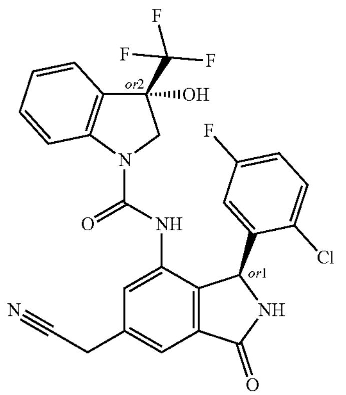 [SMILES: N#CCc1cc(NC(=O)N2C[C@](O)(C(F)(F)F)c3ccccc32)c2c(c1)C(=O)N[C@@H]2c1cc(F)ccc1Cl] | O[C@@]1(CN(C(=O)Nc2cc(CC#N)cc3C(=O)N[C@@H](c23)c2cc(F)ccc2Cl)c2ccccc12)C(F)(F)F | | | A | A |
| I-2606 | 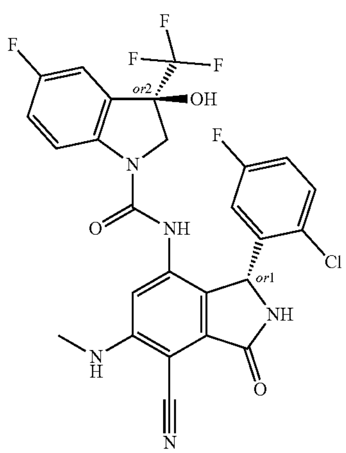 [SMILES: CNc1cc(NC(=O)N2C[C@@](O)(C(F)(F)F)c3cc(F)ccc32)c2c(c1C#N)C(=O)N[C@H]2c1cc(F)ccc1Cl] | CNc1cc(NC(=O)N2C[C@](O)(c3cc(F)ccc23)C(F)(F)F)c2[C@@H](NC(=O)c2c1C#N)c1cc(F)ccc1Cl | | | D | |
| I-2607 | 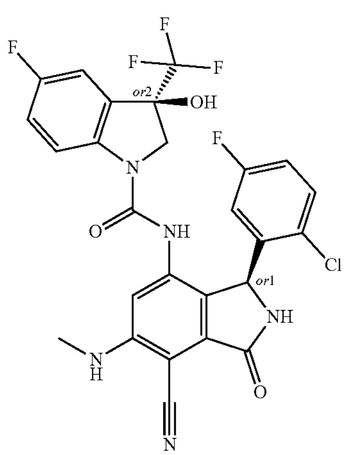 [SMILES: CNc1cc(NC(=O)N2C[C@@](O)(C(F)(F)F)c3cc(F)ccc32)c2c(c1C#N)C(=O)N[C@@H]2c1cc(F)ccc1Cl] | CNc1cc(NC(=O)N2C[C@](O)(c3cc(F)ccc23)C(F)(F)F)c2[C@H](NC(=O)c2c1C#N)c1cc(F)ccc1Cl | | | D | |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-2608 | 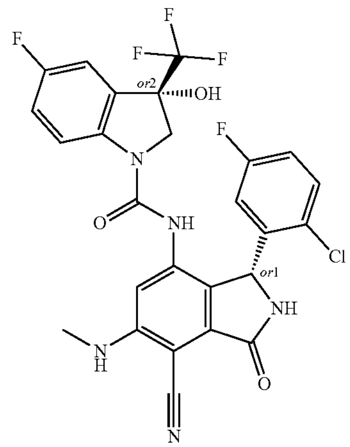 [SMILES: CNc1cc(NC(=O)N2C[C@](O)(C(F)(F)F)c3cc(F)ccc32)c2c(c1C#N)C(=O)N[C@H]2c1cc(F)ccc1Cl] | CNc1cc(NC(=O)N2C[C@@](O)(c3cc(F)ccc23)C(F)(F)F)c2[C@@H](NC(=O)c2c1C#N)c1cc(F)ccc1Cl | | | D | |
| I-2609 | 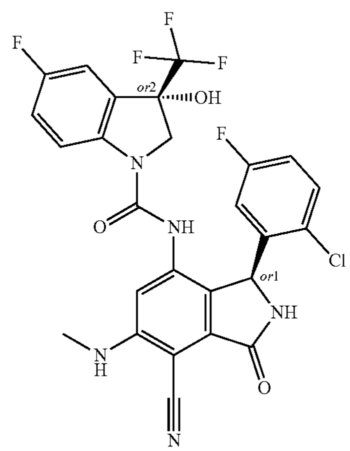 [SMILES: CNc1cc(NC(=O)N2C[C@](O)(C(F)(F)F)c3cc(F)ccc32)c2c(c1C#N)C(=O)N[C@@H]2c1cc(F)ccc1Cl] | CNc1cc(NC(=O)N2C[C@@](O)(c3cc(F)ccc23)C(F)(F)F)c2[C@H](NC(=O)c2c1C#N)c1cc(F)ccc1Cl | | | A | A |
| I-2610 | 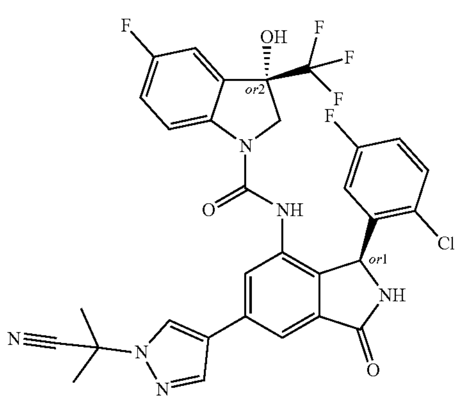 [SMILES: CC(C)(C#N)n1cc(-c2cc(NC(=O)N3C[C@](O)(C(F)(F)F)c4cc(F)ccc43)c3c(c2)C(=O)N[C@@H]3c2cc(F)ccc2Cl)cn1] | CC(C)(C#N)n1cc(cn1)-c1cc2C(=O)N[C@@H](c2c(NC(=O)N2C[C@@](O)(c3cc(F)ccc23)C(F)(F)F)c1)c1cc(F)ccc1Cl | (400 MHz, DMSO-d6) 9.10 (s, 1H), 8.78-8.73 m, 2H), 8.21 (s, 1H), 7.95 (d, J = 1.6 Hz, 1H), 7.88 (dd, J = 9.0, 4.7 Hz, 1H), 7.73 (d, J = 1.5 Hz, 1H), 7.40-7.35 (m, 2H), 7.25 (qd, J = 8.8, 2.8 Hz, 2H), 7.12 (ddd, J = 8.9, 7.8, 3.1 Hz, 1H), 6.59 (s, 1H), 6.06 (s, 1H), 4.27 (d, J = 12.1 Hz, 1H), 3.44 (d, J = 12.0 Hz, 1H), 2.04 (s, 6H). | 671.1 | D | |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-2611 | 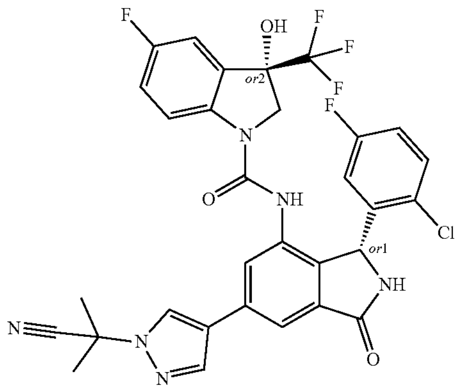 [SMILES: CC(C)(C#N)n1cc(-c2cc(NC(=O)N3C[C@](O)(C(F)(F)F)c4cc(F)ccc43)c3c(c2)C(=O)N[C@H]3c2cc(F)ccc2Cl)cn1] | CC(C)(C#N)n1cc(cn1)-c1cc2C(=O)N[C@H](c2c(NC(=O)N2C[C@@](O)(c3cc(F)ccc23)C(F)(F)F)c1)c1cc(F)ccc1Cl | (400 MHz, DMSO-d6) 9.10 (s, 1H), 8.78-8.73 (m, 2H), 8.21 (s, 1H), 7.95 (d, J = 1.6 Hz, 1H), 7.88 (dd, J = 9.0, 4.7 Hz, 1H), 7.73 (d, J = 1.5 Hz, 1H), 7.40 (s, 1H), 7.35 (dd, J = 8.9, 5.2 Hz, 1H), 7.25 (qd, J = 8.8, 2.8 Hz, 2H), 7.12 (ddd, J = 8.9, 7.8, 3.1 Hz, 1H), 6.59 (s, 1H), 6.06 (s, 1H), 4.27 (d, J = 12.1 Hz, 1H), 3.44 (d, J = 12.0 Hz, 1H), 2.04 (s, 6H). | 671.2 | B | |
| I-2612 | 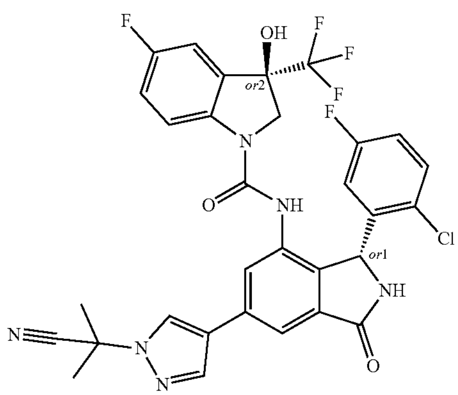 [SMILES: CC(C)(C#N)n1cc(-c2cc(NC(=O)N3C[C@@](O)(C(F)(F)F)c4cc(F)ccc43)c3c(c2)C(=O)N[C@H]3c2cc(F)ccc2Cl)cn1] | CC(C)(C#N)n1cc(cn1)-c1cc2C(=O)N[C@H](c2c(NC(=O)N2C[C@](O)(c3cc(F)ccc23)C(F)(F)F)c1)c1cc(F)ccc1Cl | (400 MHz, DMSO-d6) 9.09 (s, 1H), 8.85 (s, 1H), 8.73 (s, 1H), 8.20 (s, 1H), 7.95 (d, J = 1.5 Hz, 2H), 7.67 (d, J = 1.5 Hz, 1H), 7.42 (s, 1H), 7.37-7.18 (m, 3H), 7.13 (td, J = 8.4, 3.1 Hz, 1H), 6.60 (s, 1H), 6.03 (s, 1H), 4.00 (d, J = 12.1 Hz, 1H), 3.59 (d, J = 12.1 Hz, 1H), 2.04 (s, 6H). | 671.1 | D | |
| I-2613 | 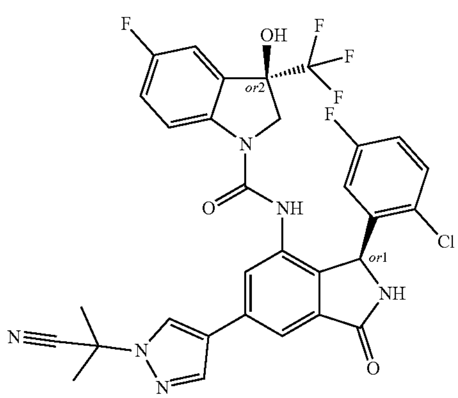 [SMILES: CC(C)(C#N)n1cc(-c2cc(NC(=O)N3C[C@@](O)(C(F)(F)F)c4cc(F)ccc43)c3c(c2)C(=O)N[C@@H]3c2cc(F)ccc2Cl)cn1] | CC(C)(C#N)n1cc(cn1)-c1cc2C(=O)N[C@@H](c2c(NC(=O)N2C[C@@](O)(c3cc(F)ccc23)C(F)(F)F)c1)c1cc(F)ccc1Cl | (400 MHz, DMSO-d6) 9.09 (s, 1H), 8.85 (s, 1H), 8.73 (s, 1H), 8.20 (s, 1H), 7.95 (d, J = 1.5 Hz, 2H), 7.67 (d, J = 1.5 Hz, 1H), 7.42 (s, 1H), 7.37-7.18 (m, 3H), 7.13 (td, J = 8.4, 3.1 Hz, 1H), 6.60 (s, 1H), 6.03 (s, 1H), 4.00 (d, J = 12.1 Hz, 1H), 3.59 (d, J = 12.1 Hz, 1H), 2.04 (s, 6H). | 657.1 | A | A |

TABLE 2-continued

Representative Compounds of the Invention with Bioactivity Data.

| Ex. No. | Structure | SMILES | $^1$H NMR | MS | ADP-Glo IC$_{50}$ | MCF 10A IC$_{50}$ |
|---|---|---|---|---|---|---|
| I-2614 | 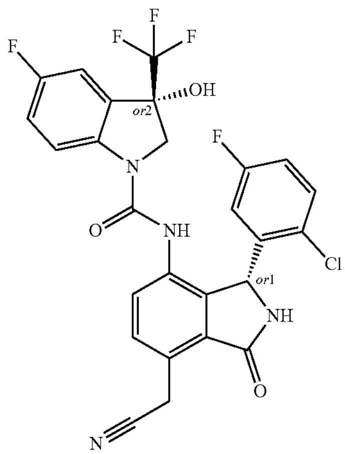 [SMILES: N#CCc1ccc(NC(=O)N2C[C@](O)(C(F)(F)F)c3cc(F)ccc32)c2c1C(=O)N[C@H]2c1cc(F)ccc1Cl] | O[C@@]1(CN(C(=O)Nc2ccc(CC#N)c3C(=O)N[C@H](c23)c2cc(F)ccc2Cl)c2ccc(F)cc12)C(F)(F)F | (400 MHz, DMSO-d6) δ9.23 (s, 1H), 8.75 (d, J = 7.2 Hz, 1H), 7.84 (dd, J = 8.9, 4.7 Hz, 1H), 7.58 (d, J = 8.1 Hz, 1H), 7.49 (dd, J = 8.1, 1.9 Hz, 1H), 7.41-7.33 (m, 2H), 7.30-7.18 (m, 2H), 7.12 (td, J = 8.4, 3.1 Hz, 1H), 6.06 (s, 1H), 4.79-4.39 (m, 2H), 4.21 (d, J = 11.9 Hz, 1H), 3.45 (d, J = 12.1 Hz, 1H). | 563.4 | A | A |
| I-2615 | 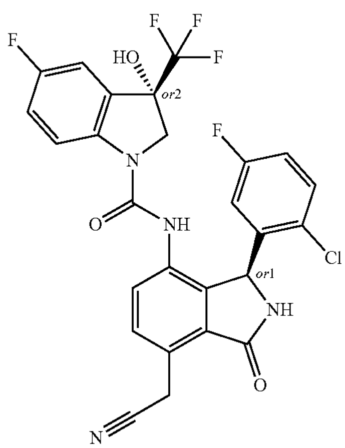 [SMILES: N#CCc1ccc(NC(=O)N2C[C@](O)(C(F)(F)F)c3cc(F)ccc32)c2c1C(=O)N[C@@H]2c1cc(F)ccc1Cl] | O[C@@]1(CN(C(=O)Nc2ccc(CC#N)c3C(=O)N[C@@H](c23)c2cc(F)ccc2Cl)c2ccc(F)cc12)C(F)(F)F | (400 MHz, DMSO-d6) δ9.23 (s, 1H), 8.75 (d, J = 7.2 Hz, 1H), 7.84 (dd, J = 8.9, 4.7 Hz, 1H), 7.58 (d, J = 8.1 Hz, 1H), 7.49 (dd, J = 8.1, 1.9 Hz, 1H), 7.41-7.33 (m, 2H), 7.30-7.18 (m, 2H), 7.12 (td, J = 8.4, 3.1 Hz, 1H), 6.06 (s, 1H), 4.79-4.39 (m, 2H), 4.21 (d, J = 11.9 Hz, 1H), 3.45 (d, J = 12.1 Hz, 1H). | 563.4 | D | |
| I-2616 | 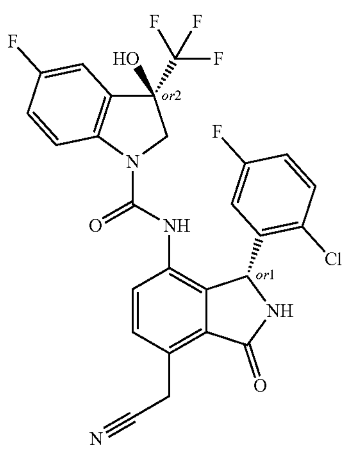 [SMILES: N#CCc1ccc(NC(=O)N2C[C@@](O)(C(F)(F)F)c3cc(F)ccc32)c2c1C(=O)N[C@H]2c1cc(F)ccc1Cl] | O[C@]1(CN(C(=O)Nc2ccc(CC#N)c3C(=O)N[C@H](c23)c2cc(F)ccc2Cl)c2ccc(F)cc12)C(F)(F)F | (400 MHz, DMSO-d6) δ9.23 (s, 1H), 8.75 (d, J = 7.2 Hz, 1H), 7.84 (dd, J = 8.9, 4.7 Hz, 1H), 7.58 (d, J = 8.1 Hz, 1H), 7.49 (dd, J = 8.1, 1.9 Hz, 1H), 7.41-7.33 (m, 2H), 7.30-7.18 (m, 2H), 7.12 (td, J = 8.4, 3.1 Hz, 1H), 6.06 (s, 1H), 4.79-4.39 (m, 2H), 4.21 (d, J = 11.9 Hz, 1H), 3.45 (d, J = 12.1 Hz, 1H). | 563.4 | D | |

TABLE 2-continued

Representative Compounds of the Invention with Bioactivity Data.

| Ex. No. | Structure | SMILES | ¹H NMR | MS | ADP-Glo IC₅₀ | MCF 10A IC₅₀ |
|---|---|---|---|---|---|---|
| I-2617 | 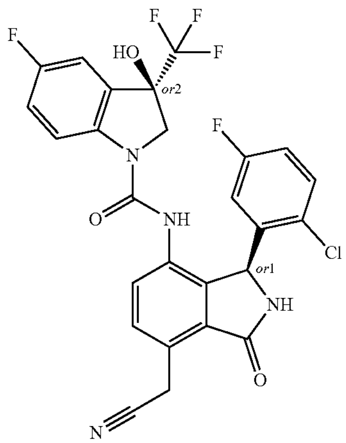 [SMILES: N#CCc1ccc(NC(=O)N2C[C@@](O)(C(F)(F)F)c3cc(F)ccc32)c2c1C(=O)N[C@@H]2c1cc(F)ccc1Cl] | O[C@]1(CN(C(=O)Nc2ccc(CC#N)c3C(=O)N[C@@H](c23)c2cc(F)ccc2Cl)c2ccc(F)cc12)C(F)(F)F | (400 MHz, DMSO-d6) δ9.23 (s, 1H), 8.75 (d, J = 7.2 Hz, 1H), 7.84 (dd, J = 8.9, 4.7 Hz, 1H), 7.58 (d, J = 8.1 Hz, 1H), 7.49 (dd, J = 8.1, 1.9 Hz, 1H), 7.41-7.33 (m, 2H), 7.30-7.18 (m, 2H), 7.12 (td, J = 8.4, 3.1 Hz, 1H), 6.06 (s, 1H), 4.79-4.39 (m, 2H), 4.21 (d, J = 11.9 Hz, 1H), 3.45 (d, J = 12.1 Hz, 1H). | 563.4 | D | |
| I-2618 | 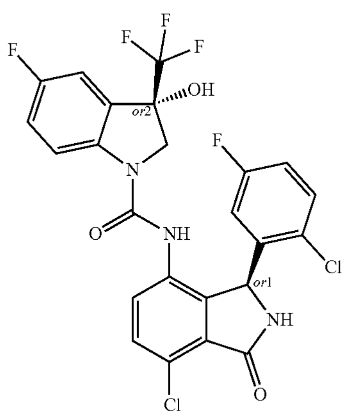 [SMILES: O=C1N[C@H](c2cc(F)ccc2Cl)c2c(NC(=O)N3C[C@](O)(C(F)(F)F)c4cc(F)ccc43)ccc(Cl)c21] | O[C@@]1(CN(C(=O)Nc2cc(Cl)c3C(=O)N[C@@H](c23)c2cc(F)ccc2C1)c2ccc(F)cc12)C(F)(F)F | (400 MHz, DMSO-d6) 9.19 (s, 1H), 8.82 (s, 1H), 7.91 (s, 1H), 7.57 (d, J = 8.4 Hz, 1H), 7.42-7.10 (m, 6H), 6.66 (s, 1H), 5.99 (s, 1H), 3.98 (d, J = 12.1 Hz, 1H), 3.50 (d, J = 12.1 Hz, 1H). | 558.1 | A | A |
| I-2619 | 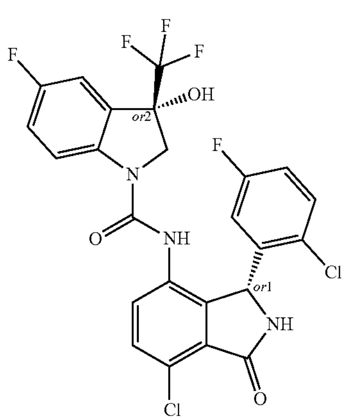 [SMILES: O=C1N[C@@H](c2cc(F)ccc2Cl)c2c(NC(=O)N3C[C@](O)(C(F)(F)F)c4cc(F)ccc43)ccc(Cl)c21] | O[C@@]1(CN(C(=O)Nc2cc(Cl)c3C(=O)N[C@H](c23)c2cc(F)ccc2Cl)c2ccc(F)cc12)C(F)F | (400 MHz, DMSO-d6) 9.20 (s, 1H), 8.72 (s, 1H), 7.83 (dd, J = 8.9, 4.7 Hz, 1H), 7.58 (d, J = 8.4 Hz, 1H), 7.46 (d, J = 8.4 Hz, 1H), 7.41-7.31 (m, 2H), 7.29-7.18 (m, 2H), 7.13 (td, J = 8.4, 3.1 Hz, 1H), 6.64 (s, 1H), 6.03 (s, 1H), 4.17 (d, J = 12.0 Hz, 1H), 3.44 (d, J = 12.1 Hz, 1H). | 558.1 | D | |

TABLE 2-continued

Representative Compounds of the Invention with Bioactivity Data.

| Ex. No. | Structure | SMILES | $^1$H NMR | MS | ADP-Glo IC$_{50}$ | MCF 10A IC$_{50}$ |
|---|---|---|---|---|---|---|
| I-2620 | 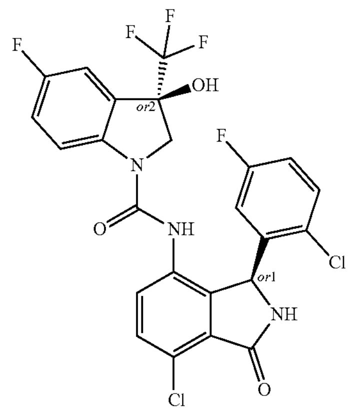 [SMILES: O=C1N[C@H](c2cc(F)ccc2Cl)c2c(NC(=O)N3C[C@@](O)(C(F)(F)F)c4cc(F)ccc43)ccc(Cl)c21] | O[C@]1 (CN(C(= O)Nc2cc c(Cl)c3C (=O)N[C @@H](c 23)c2cc (F)ccc2Cl) c2ccc(F) cc12)C(F) (F)F | (400 MHz, DMSO-d6) 9.19 (s, 1H), 8.81 (s, 1H), 7.90 (d, J = 6.3 Hz, 1H), 7.57 (d, J = 8.4 Hz, 1H), 7.42-7.34 (m, 2H), 7.34 (dd, J = 8.9, 5.2 Hz, 1H), 7.27 (td, J = 9.0, 2.8 Hz, 1H), 7.21 (dd, J = 8.1, 2.8 Hz, 1H), 7.14 (td, J = 8.4, 3.0 Hz, 1H), 6.63 (s, 1H), 5.99 (s, 1H), 3.97 (d, J = 12.1 Hz, 1H), 3.50 (d, J = 12.1 Hz, 1H). | 558.1 | D | |
| I-2621 | 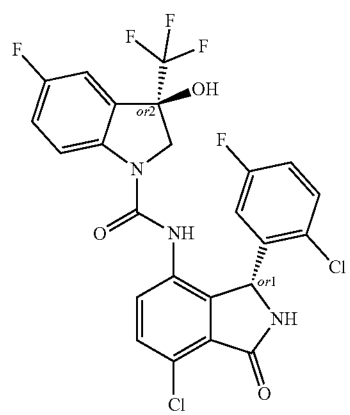 [SMILES: O=C1N[C@@H](c2cc(F)ccc2Cl)c2c(NC(=O)N3C[C@@](O)(C(F)(F)F)c4cc(F)ccc43)ccc(Cl)c21] | O[C@]1 (CN(C(= O)Nc2cc c(Cl)c3C (=O)N[C @H](c23) c2cc(F)c cc2Cl)c2 ccc(F)cc 12)C(F) (F)F | (400 MHz, DMSO-d6) 9.20 (s, 1H), 8.72 (s, 1H), 7.83 (dd, J = 8.9, 4.7 Hz, 1H), 7.58 (d, J = 8.4 Hz, 1H), 7.46 (d, J = 8.4 Hz, 1H), 7.42-7.31 (m, 2H), 7.29-7.18 (m, 2H), 7.13 (ddd, J = 8.8, 7.9, 3.1 Hz, 1H), 6.64 (s, 1H), 6.03 (s, 1H), 4.17 (d, J = 12.0 Hz, 1H), 3.44 (d, J = 12.0 Hz, 1H). | 558.1 | C | |
| I-2622 | 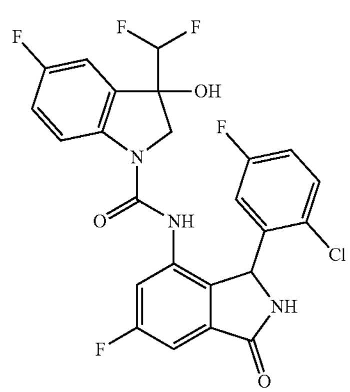 [SMILES: O=C1NC(c2cc(F)ccc2Cl)c2c(NC(=O)N3CC(O)(C(F)F)c4cc(F)ccc43)cc(F)cc21] | OC1(CN (C(=O)N c2cc(F)c c3C(=O) NC(c23) c2cc(F)c cc2Cl)c2 ccc(F)cc 12)C(F)F | (400 MHz, DMSO-d6) δ 9.25 (br s, 1H), 8.85 (br s, 0.5H), 8.74 (br s, 0.5H), 7.87 (br dd, J = 8.1, 4.1 Hz, 0.5H), 7.80 (dd, J = 8.9, 4.5 Hz, 0.5H), 7.42-7.30 (m, 3H), 7.30-7.21 (m, 2H), 7.19 (dd, J = 8.8, 2.4 Hz, 1H), 7.16-7.08 (m, 1H), 6.72 (br s, 0.5H), 6.66 (br s, 0.5H), 6.27 (td, J = 55.3, 4.5 Hz, 1H), 6.04 (br s, 1H), 4.01 (d, J = 11.4 Hz, 0.5H), 3.79 (d, J = 12.0 Hz, 0.5H), 3.48 (d, J = 11.8 Hz, 0.5H). 1:1 mix of diastereomers | 524.0 | A | B |

TABLE 2-continued
Representative Compounds of the Invention with Bioactivity Data.
| Ex. No. | Structure | SMILES | $^1$H NMR | MS | ADP-Glo IC$_{50}$ | MCF 10A IC$_{50}$ |
|---|---|---|---|---|---|---|
| I-2623 | 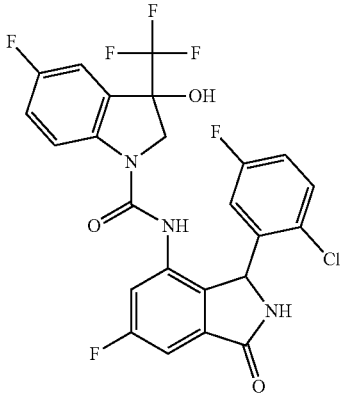 [SMILES: O=C1NC(c2cc(F)ccc2Cl)c2c(NC(=O)N3CC(O)(C(F)(F)F)c4cc(F)ccc43)cc(F)cc21] | OC1(CN(C(=O)Nc2cc(F)cc3C(=O)NC(c23)c2cc(F)cc2Cl)c2ccc(F)cc12)C(F)(F)F | | 542.0 | A | A |
| I-2624 | 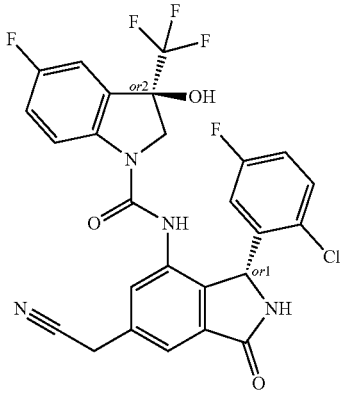 [SMILES: N#CCc1cc(NC(=O)N2C[C@@](O)(C(F)(F)F)c3cc(F)ccc32)c2c(c1)C(=O)N[C@H]2c1cc(F)ccc1Cl] | O[C@]1(CN(C(=O)Nc2cc(CC#N)cc3C(=O)N[C@H](c23)c2cc(F)ccc2Cl)c2ccc(F)cc12)C(F)(F)F | | | D | |
| I-2625 | 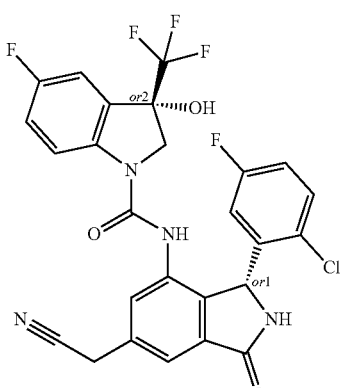 | O[C@@]1(CN(C(=O)Nc2cc(CC#N)cc3C(=O)N[C@H](c23)c2cc(F)ccc2Cl)c2ccc(F)cc12)C(F)(F)F | | | D | |

TABLE 2-continued

Representative Compounds of the Invention with Bioactivity Data.

| Ex. No. | Structure | SMILES | $^1$H NMR | MS | ADP-Glo IC$_{50}$ | MCF 10A IC$_{50}$ |
|---|---|---|---|---|---|---|
| I-2626 | 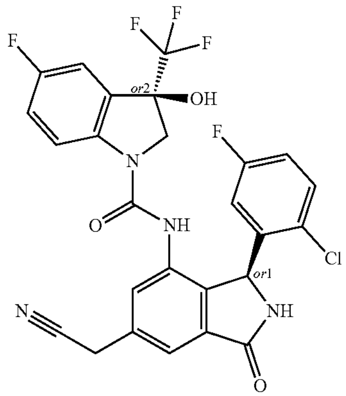 [SMILES: N#CCc1cc(NC(=O)N2C[C@@](O)(C(F)(F)F)c3cc(F)ccc32)c2c(c1)C(=O)N[C@@H]2c1cc(F)ccc1Cl] | O[C@]1(CN(C(=O)Nc2cc(CC#N)cc3C(=O)N[C@@H](c23)c2cc(F)ccc2Cl)c2ccc(F)cc12)C(F)(F)F | | | C | |
| I-2627 | 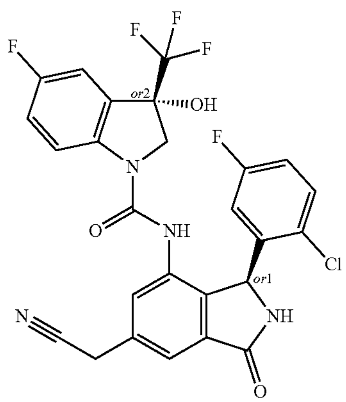 [SMILES: N#CCc1cc(NC(=O)N2C[C@](O)(C(F)(F)F)c3cc(F)ccc32)c2c(c1)C(=O)N[C@@H]2c1cc(F)ccc1Cl] | O[C@@]1(CN(C(=O)Nc2cc(CC#N)cc3C(=O)N[C@@H](c23)c2cc(F)ccc2Cl)c2ccc(F)cc12)C(F)(F)F | | | A | A |
| I-2628 | 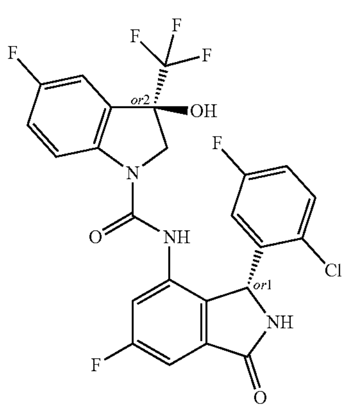 [SMILES: O=C1N[C@@H](c2cc(F)ccc2Cl)c2c(NC(=O)N3C[C@@](O)(C(F)(F)F)c4cc(F)ccc43)cc(F)cc21] | O[C@]1(CN(C(=O)Nc2cc(F)cc3C(=O)N[C@H](c23)c2cc(F)cc2Cl)c2ccc(F)cc12)C(F)(F)F | | | D | |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-2629 | 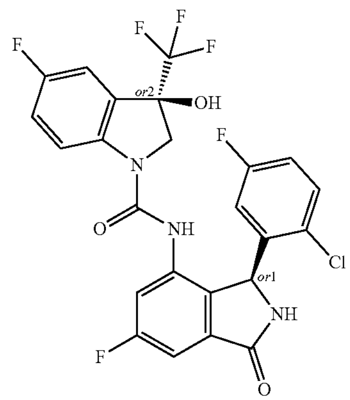 [SMILES: O=C1N[C@H](c2cc(F)ccc2Cl)c2c(NC(=O)N3C[C@@](O)(C(F)(F)F)c4cc(F)ccc43)cc(F)cc21] | O[C@]1(CN(C(=O)Nc2cc(F)cc3C(=O)N[C@@H](c23)c2cc(F)ccc2Cl)c2ccc(F)cc12)C(F)(F)F | | | D | |
| I-2630 | 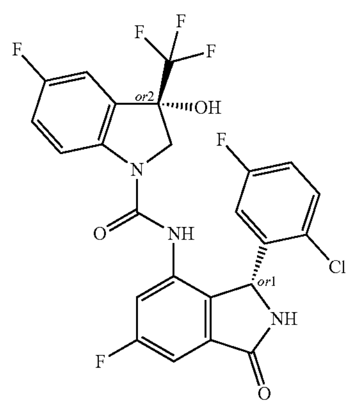 [SMILES: O=C1N[C@@H](c2cc(F)ccc2Cl)c2c(NC(=O)N3C[C@](O)(C(F)(F)F)c4cc(F)ccc43)cc(F)cc21] | O[C@@]1(CN(C(=O)Nc2cc(F)cc3C(=O)N[C@H](c23)c2cc(F)ccc2Cl)c2ccc(F)cc12)C(F)(F)F | | | D | A |
| I-2631 | 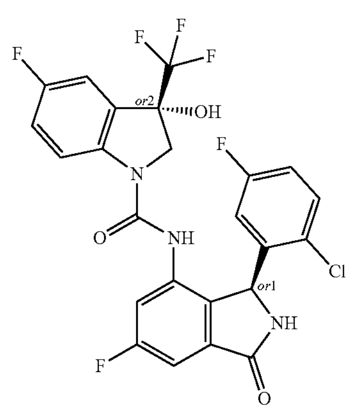 [SMILES: O=C1N[C@H](c2cc(F)ccc2Cl)c2c(NC(=O)N3C[C@](O)(C(F)(F)F)c4cc(F)ccc43)cc(F)cc21] | O[C@@]1(CN(C(=O)Nc2cc(F)cc3C(=O)N[C@@H](c23)c2cc(F)ccc2Cl)c2ccc(F)cc12)C(F)(F)F | | | | A |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-2632 | 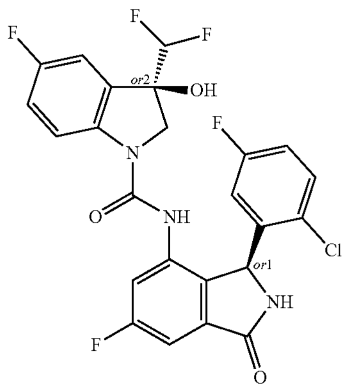 [SMILES: O=C1N[C@H](c2cc(F)ccc2Cl)c2c(NC(=O)N3C[C@@](O)(C(F)F)c4cc(F)ccc43)cc(F)cc21] | O[C@]1(CN(C(=O)Nc2cc(F)cc3C(=O)N[C@@H](c23)c2cc(F)ccc2Cl)c2ccc(F)cc12)C(F)F | | | D | |
| I-2633 | 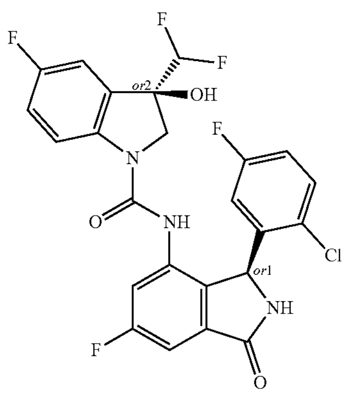 [SMILES: O=C1N[C@H](c2cc(F)ccc2Cl)c2c(NC(=O)N3C[C@@](O)(C(F)F)c4cc(F)ccc43)cc(F)cc21] | O[C@]1(CN(C(=O)Nc2cc(F)cc3C(=O)N[C@H](c23)c2cc(F)ccc2Cl)c2ccc(F)cc12)C(F)F | | | D | |
| I-2634 | 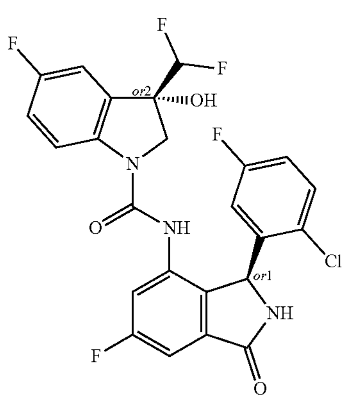 [SMILES: O=C1N[C@H](c2cc(F)ccc2Cl)c2c(NC(=O)N3C[C@](O)(C(F)F)c4cc(F)ccc43)cc(F)cc21] | O[C@@]1(CN(C(=O)Nc2cc(F)cc3C(=O)N[C@@H](c23)c2cc(F)ccc2Cl)c2ccc(F)cc12)C(F)F | | | D | |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-2635 | 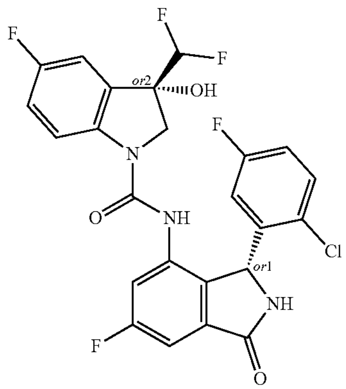 [SMILES: O=C1N[C@@H](c2cc(F)ccc2Cl)c2c(NC(=O)N3C[C@](O)(C(F)F)c4cc(F)ccc43)cc(F)cc21] | O[C@@]1(CN(C(=O)Nc2cc(F)cc3C(=O)N[C@H](c23)c2cc(F)ccc2Cl)c2ccc(F)cc12)C(F)F | | | A | A |
| I-2636 | 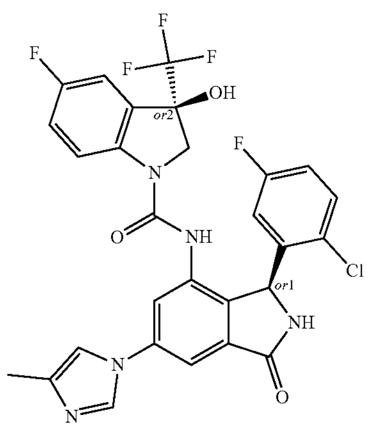 [SMILES: Cc1cn(-c2cc(NC(=O)N3C[C@@](O)(C(F)(F)F)c4cc(F)ccc43)c3c(c2)C(=O)N[C@@H]3c2cc(F)ccc2Cl)cn1] | Cc1cn(cn1)-c1cc2C(=O)N[C@@H](c2c(NC(=O)N2C[C@](O)(c3cc(F)ccc23)C(F)(F)F)c1cc(F)ccc1Cl | (400 MHz, DMSO-d6) 9.23 (s, 1H), 8.96 (s, 1H), 8.26 (d, J = 1.5 Hz, 1H), 7.90 (d, J = 14.8 Hz, 1H), 7.82 (d, J = 2.0 Hz, 1H), 7.62 (d, J = 2.0 Hz, 1H), 7.56 (t, J = 1.3 Hz, 1H), 7.44 (s, 1H), 7.34 (dd, J = 8.9, 5.1 Hz, 1H), 7.28 (td, J = 9.0, 2.8 Hz, 1H), 7.22 (dd, J = 8.0, 2.7 Hz, 1H), 7.14 (td, J = 8.4, 3.1 Hz, 1H), 6.77 (d, J = 81.8 Hz, 1H), 6.06 (s, 1H), 3.98 (d, J = 12.1 Hz, 1H), 3.57 (d, J = 11.9 Hz, 1H), 2.19 (d, J = 1.0 Hz, 3H). | 604.1 | D | |
| I-2637 | 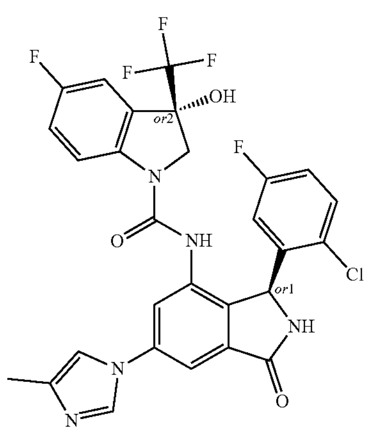 [SMILES: Cc1cn(-c2cc(NC(=O)N3C[C@](O)(C(F)(F)F)c4cc(F)ccc43)c3c(c2)C(=O)N[C@@H]3c2cc(F)ccc2Cl)cn1] | Cc1cn(cn1)-c1cc2C(=O)N[C@@H](c2c(NC(=O)N2C[C@@](O)(c3cc(F)ccc23)C(F)(F)F)c1cc(F)ccc1Cl | (400 MHz, DMSO-d6) 9.23 (s, 1H), 8.96 (s, 1H), 8.26 (d, J = 1.5 Hz, 1H), 7.90 (d, J = 14.8 Hz, 1H), 7.82 (d, J = 2.0 Hz, 1H), 7.62 (d, J = 2.0 Hz, 1H), 7.56 (t, J = 1.3 Hz, 1H), 7.44 (s, 1H), 7.34 (dd, J = 8.9, 5.1 Hz, 1H), 7.28 (td, J = 9.0, 2.8 Hz, 1H), 7.22 (dd, J = 8.0, 2.7 Hz, 1H), 7.14 (td, J = 8.4, 3.1 Hz, 1H), 6.77 (d, J = 81.8 Hz, 1H), 6.06 (s, 1H), 3.98 (d, J = 12.1 Hz, 1H), 3.57 (d, J = 11.9 Hz, 1H), 2.19 (d, J = 1.0 Hz, 3H). | 604.4 | A | A |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-2638 | 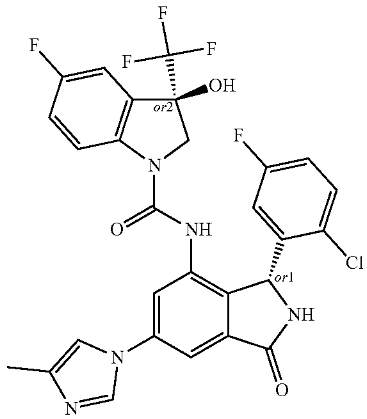 [SMILES: Cc1cn(-c2cc(NC(=O)N3C[C@@](O)(C(F)(F)F)c4cc(F)ccc43)c3c(c2)C(=O)N[C@H]3c2cc(F)ccc2Cl)cn1] | Cc1cn(cn1)-c1cc2C(=O)N[C@H](c2c(NC(=O)N2C[C@](O)(c3cc(F)ccc23)C(F)(F)F)c1cc(F)ccc1Cl | (400 MHz, DMSO-d6) 9.23 (s, 1H), 8.96 (s, 1H), 8.26 (d, J = 1.5 Hz, 1H), 7.90 (d, J = 14.8 Hz, 1H), 7.82 (d, J = 2.0 Hz, 1H), 7.62 (d, J = 2.0 Hz, 1H), 7.56 (t, J = 1.3 Hz, 1H), 7.44 (s, 1H), 7.34 (dd, J = 8.9, 5.1 Hz, 1H), 7.28 (td, J = 9.0, 2.8 Hz, 1H), 7.22 (dd, J = 8.0, 2.7 Hz, 1H), 7.14 (td, J = 8.4, 3.1 Hz, 1H), 6.77 (d, J = 81.8 Hz, 1H), 6.06 (s, 1H), 3.98 (d, J = 12.1 Hz, 1H), 3.57 (d, J = 11.9 Hz, 1H), 2.19 (d, J = 1.0 Hz, 3H). | 604.1 | D | |
| I-2639 | 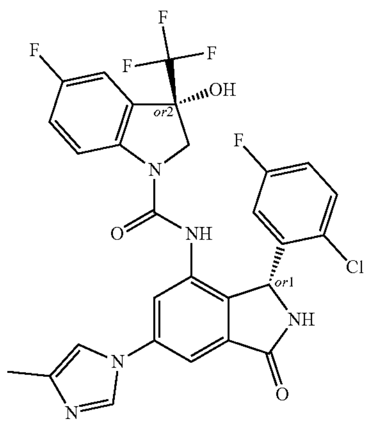 [SMILES: Cc1cn(-c2cc(NC(=O)N3C[C@](O)(C(F)(F)F)c4cc(F)ccc43)c3c(c2)C(=O)N[C@H]3c2cc(F)ccc2Cl)cn1] | Cc1cn(cn1)-c1cc2C(=O)N[C@H](c2c(NC(=O)N2C[C@@](O)(c3cc(F)ccc23)C(F)(F)F)c1cc(F)ccc1Cl | (400 MHz, DMSO-d6) 9.23 (s, 1H), 8.96 (s, 1H), 8.26 (d, J = 1.5 Hz, 1H), 7.90 (d, J = 14.8 Hz, 1H), 7.82 (d, J = 2.0 Hz, 1H), 7.62 (d, J = 2.0 Hz, 1H), 7.56 (t, J = 1.3 Hz, 1H), 7.44 (s, 1H), 7.34 (dd, J = 8.9, 5.1 Hz, 1H), 7.28 (td, J = 9.0, 2.8 Hz, 1H), 7.22 (dd, J = 8.0, 2.7 Hz, 1H), 7.14 (td, J = 8.4, 3.1 Hz, 1H), 6.77 (d, J = 81.8 Hz, 1H), 6.06 (s, 1H), 3.98 (d, J = 12.1 Hz, 1H), 3.57 (d, J = 11.9 Hz, 1H), 2.19 (d, J = 1.0 Hz, 3H). | 604.4 | E | |
| I-2640 | 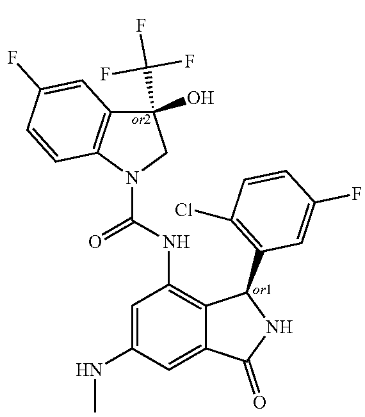 [SMILES: CNc1cc(NC(=O)N2C[C@@](O)(C(F)(F)F)c3cc(F)ccc32)c2c(c1)C(=O)N[C@@H]2c1cc(F)ccc1Cl] | CNc1cc2C(=O)N[C@@H](c2c(NC(=O)N2C[C@](O)(c3cc(F)ccc23)C(F)(F)F)c1cc(F)ccc1Cl | (400 MHz, DMSO-d6) 8.83 (s, 1H), 8.57 (s, 1H), 7.90 (dd, J = 9.1, 4.7 Hz, 1H), 7.35 (s, 1H), 7.31-7.21 (m, 2H), 7.18 (dd, J = 8.1, 2.8 Hz, 1H), 7.09 (td, J = 8.3, 3.1 Hz, 1H), 6.70 (d, J = 2.1 Hz, 1H), 6.58 (d, J = 2.1 Hz, 1H), 6.52 (s, 1H), 6.21-6.05 (m, 1H), 5.87 (s, 1H), 3.98 (d, J = 12.1 Hz, 1H), 3.50 (d, J = 12.0 Hz, 1H), 2.75 (d, J = 4.9 Hz, 3H). | 553.1 | A | A |

TABLE 2-continued

Representative Compounds of the Invention with Bioactivity Data.

| Ex. No. | Structure | SMILES | $^1$H NMR | MS | ADP-Glo IC$_{50}$ | MCF 10A IC$_{50}$ |
|---|---|---|---|---|---|---|
| I-2641 | 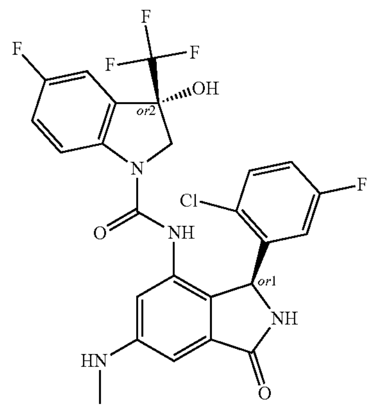 [SMILES: CNc1cc(NC(=O)N2C[C@](O)(C(F)(F)F)c3cc(F)ccc32)c2c(c1)C(=O)N[C@@H]2c1cc(F)ccc1Cl] | CNc1cc2C(=O)N[C@@H](c2c(NC(=O)N2C[C@@](O)(c3cc(F)ccc23)C(F)(F)F)c1)cc(F)ccc1Cl | (400 MHz, DMSO-d6) 8.85 (s, 1H), 8.49 (s, 1H), 7.84 (dd, J = 9.0, 4.7 Hz, 1H), 7.35-7.27 (m, 2H), 7.26-7.17 (m, 2H), 7.08 (ddd, J = 8.8, 7.8, 3.1 Hz, 1H), 6.68 (dd, J = 17.1, 2.1 Hz, 2H), 6.50 (s, 1H), 6.14 (d, J = 5.2 Hz, 1H), 5.91 (s, 1H), 4.20 (d, J = 12.0 Hz, 1H), 3.41 (d, J = 12.1 Hz, 1H), 2.75 (d, J = 4.9 Hz, 3H). | 553.1 | C | |
| I-2642 | 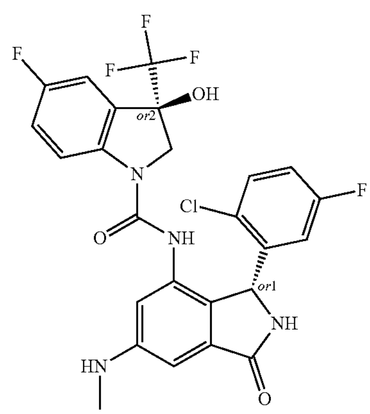 [SMILES: CNc1cc(NC(=O)N2C[C@@](O)(C(F)(F)F)c3cc(F)ccc32)c2c(c1)C(=O)N[C@H]2c1cc(F)ccc1Cl] | CNc1cc2C(=O)N[C@H](c2c(NC(=O)N2C[C@](O)(c3cc(F)ccc23)C(F)(F)c1)cc(F)cc1Cl | (400 MHz, DMSO-d6) 8.85 (s, 1H), 8.49 (s, 1H), 7.84 (dd, J = 9.0, 4.7 Hz, 1H), 7.35-7.28 (m, 2H), 7.27-7.15 (m, 2H), 7.08 (ddd, J = 8.9, 7.9, 3.2 Hz, 1H), 6.68 (dd, J = 17.1, 2.1 Hz, 2H), 6.51 (s, 1H), 6.13 (d, J = 5.1 Hz, 1H), 5.91 (s, 1H), 4.20 (d, J = 12.1 Hz, 1H), 3.41 (d, J = 12.1 Hz, 1H), 2.75 (d, J = 4.9 Hz, 3H). | 553.1 | B | |
| I-2643 | 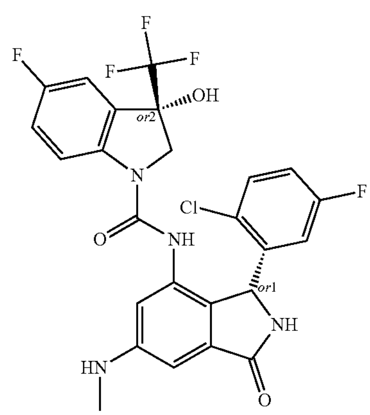 | CNc1cc2C(=O)N[C@H](c2c(NC(=O)N2C[C@@](O)(c3cc(F)cc23)C(F)(F)c1)cc(F)cc1Cl | (400 MHz, DMSO-d6) 8.83 (s, 1H), 8.57 (s, 1H), 7.90 (dd, J = 9.1, 4.6 Hz, 1H), 7.35 (s, 1H), 7.31-7.21 (m, 2H), 7.18 (dd, J = 8.1, 2.8 Hz, 1H), 7.09 (td, J = 8.3, 3.1 Hz, 1H), 6.70 (d, J = 2.0 Hz, 1H), 6.58 (d, J = 2.1 Hz, 1H), 6.51 (s, 1H), 6.14 (d, J = 5.1 Hz, 1H), 5.87 (s, 1H), 3.98 (d, J = 12.1 Hz, 1H), 3.50 (d, J = 12.1 Hz, 1H), 2.75 (d, J = 4.9 Hz, 3H). | 553.1 | D | |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-2644 | 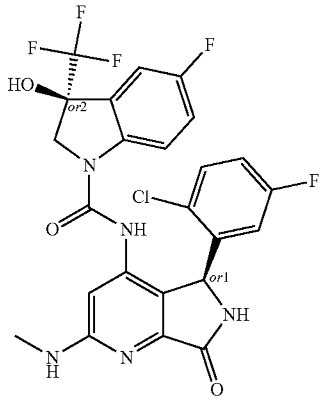 [SMILES: CNc1cc(NC(=O)N2C[C@](O)(C(F)(F)F)c3cc(F)ccc32)c2c(n1)C(=O)N[C@@H]2c1cc(F)ccc1Cl] | CNc1cc(NC(=O)N2C[C@@](O)(c3cc(F)ccc23)C(F)(F)F)c2[C@H](NC(=O)c2n1)c1cc(F)ccc1Cl | (400 MHz, DMSO-d6) 9.07-9.03 (m, 1H), 8.84 (s, 1H), 7.90 (dd, J = 9.0, 4.6 Hz, 1H), 7.38 (s, 1H), 7.34-7.23 (m, 2H), 7.19 (dd, J = 8.1, 2.7 Hz, 1H), 7.08 (td, J = 8.4, 3.1 Hz, 1H), 6.96 (d, J = 5.1 Hz, 1H), 6.66 (s, 1H), 6.49 (s, 1H), 5.87 (s, 1H), 3.93 (d, J = 12.1 Hz, 1H), 3.52 (d, J = 12.0 Hz, 1H), 2.86 (d, J = 4.8 Hz, 3H). | 554.4 | A | A |
| I-2645 | 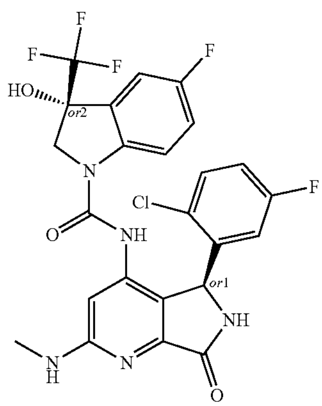 [SMILES: CNc1cc(NC(=O)N2C[C@@](O)(C(F)(F)F)c3cc(F)ccc32)c2c(n1)C(=O)N[C@@H]2c1cc(F)ccc1Cl] | CNc1cc(NC(=O)N2C[C@](O)(c3cc(F)ccc23)C(F)(F)F)c2[C@H](NC(=O)c2n1)c1cc(F)ccc1Cl | (400 MHz, DMSO-d6) 9.06 (s, 1H), 8.74 (s, 1H), 7.85 (dd, J = 9.0, 4.6 Hz, 1H), 7.37-7.30 (m, 2H), 7.30-7.17 (m, 2H), 7.10 (ddd, J = 8.9, 7.9, 3.1 Hz, 1H), 6.96 (d, J = 4.9 Hz, 1H), 6.66 (s, 1H), 6.59 (s, 1H), 5.89 (s, 1H), 4.11 (d, J = 12.0 Hz, 1H), 3.38 (d, J = 12.0 Hz, 1H), 2.86 (d, J = 4.7 Hz, 3H). | 554.4 | D | |
| I-2646 | 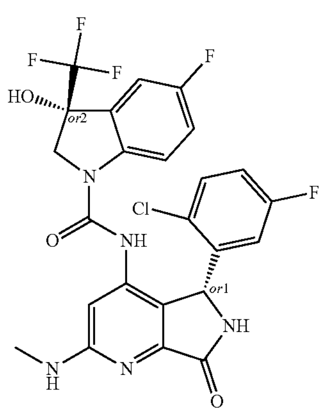 [SMILES: CNc1cc(NC(=O)N2C[C@@](O)(C(F)(F)F)c3cc(F)ccc32)c2c(n1)C(=O)N[C@H]2c1cc(F)ccc1Cl] | CNc1cc(NC(=O)N2C[C@](O)(c3cc(F)ccc23)C(F)(F)F)c2[C@@H](NC(=O)c2n1)c1cc(F)ccc1Cl | (400 MHz, DMSO-d6) 9.07 (s, 1H), 8.74 (s, 1H), 7.86 (dd, J = 9.0, 4.7 Hz, 1H), 7.37-7.30 (m, 2H), 7.26 (td, J = 9.0, 2.8 Hz, 1H), 7.21 (dd, J = 8.0, 2.7 Hz, 1H), 7.10 (td, J = 8.4, 3.1 Hz, 1H), 6.96 (q, J = 4.8 Hz, 1H), 6.66 (s, 1H), 6.59 (s, 1H), 5.89 (s, 1H), 4.11 (d, J = 12.0 Hz, 1H), 3.38 (d, J = 12.0 Hz, 1H), 2.86 (d, J = 4.7 Hz, 3H). | 554.1 | C | |

TABLE 2-continued

Representative Compounds of the Invention with Bioactivity Data.

| Ex. No. | Structure | SMILES | $^1$H NMR | MS | ADP-Glo IC$_{50}$ | MCF 10A IC$_{50}$ |
|---|---|---|---|---|---|---|
| I-2647 | 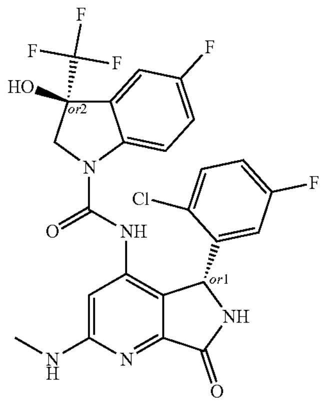 [SMILES: CNc1cc(NC(=O)N2C[C@](O)(C(F)(F)F)c3cc(F)ccc32)c2c(n1)C(=O)N[C@H]2c1cc(F)ccc1Cl] | CNc1cc(NC(=O)N2C[C@@](O)(c3cc(F)ccc23)C(F)(F)F)c2[C@@H](NC(=O)c2n1)c1cc(F)ccc1Cl | (400 MHz, DMSO-d6) 9.05 (s, 1H), 8.84 (s, 1H), 7.90 (dd, J = 9.1, 4.7 Hz, 1H), 7.37 (s, 1H), 7.34-7.28 (m, 1H), 7.31-7.23 (m, 1H), 7.20 (d, J = 8.1 Hz, 1H), 7.08 (td, J = 8.3, 3.1 Hz, 1H), 6.96 (s, 1H), 6.66 (s, 1H), 6.49 (s, 1H), 5.86 (s, 1H), 3.92 (d, J = 12.2 Hz, 1H), 3.52 (d, J = 12.0 Hz, 1H), 2.85 (d, J = 4.7 Hz, 3H). | 554.3 | B | |
| I-2648 | 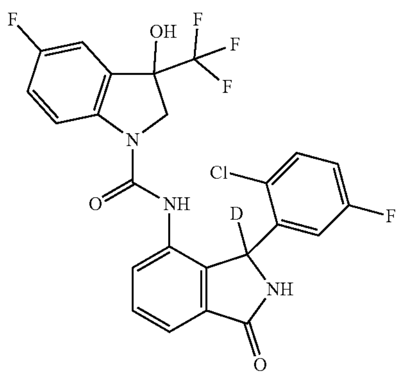 [SMILES: [2H]C1(c2cc(F)ccc2Cl)NC(=O)c2cccc(NC(=O)N3CC(O)(C(F)(F)F)c4cc(F)ccc43)c21] | [2H]C1(NC(=O)c2cccc(NC(=O)N3CC(O)(c4cc(F)ccc34)C(F)(F)F)c12)c1cc(F)ccc1Cl | (400 MHz, DMSO-d6) δ 8.60 (br s, 1H), 8.36 (d, J = 8.1 Hz, 0.5H), 8.19 (d, J = 7.9 Hz, 0.5H), 7.88 (td, J = 10.1, 5.5 Hz, 1H), 7.47-7.36 (m, 1H), 7.17 (t, J = 7.9 Hz, 1H), 7.08 (ddd, J = 16.8, 8.5, 2.9 Hz, 1H), 6.98-6.80 (m, 3H), 6.70 (br s, 1H), 6.36 (br s, 1H), 3.98 (d, J = 14.0 Hz, 0.5H), 3.77 (d, J = 13.9 Hz, 0.5H), 3.56 (d, J = 12.6 Hz, 0.5H), 3.26 (submerged d, J = 13.6 Hz, 0.5H). | 525.0 | A | A |
| I-2649 | 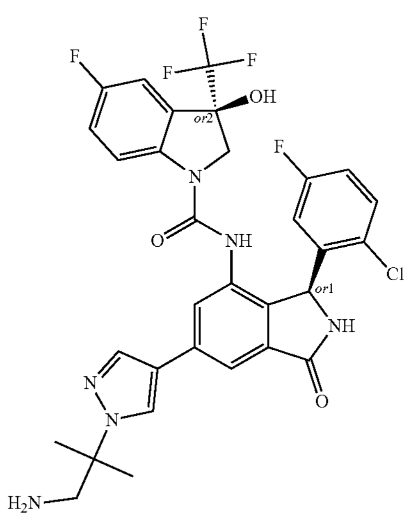 [SMILES: CC(C)(CN)n1cc(-c2cc(NC(=O)N3C[C@@](O)(C(F)(F)F)c4cc(F)ccc43)c3c(c2)C(=O)N[C@@H]3c2cc(F)ccc2Cl)cn1] | CC(C)(CN)n1cc(cn1)-c1cc2C(=O)N[C@@H](c2c(NC(=O)N2C[C@](O)(c3cc(F)ccc23)C(F)(F)F)c1)c1cc(F)ccc1Cl | (400 MHz, DMSO-d6) 9.04 (s, 1H), 8.81 (s, 1H), 8.44 (s, 1H), 8.00 (s, 1H), 7.96-7.86 (m, 2H), 7.64-7.56 (m, 1H), 7.41 (s, 1H), 7.33-7.27 (m, 2H), 7.25-7.17 (m, 1H), 7.12 (td, J = 8.4, 3.1 Hz, 1H), 6.80-6.30 (s, 1H), 6.01 (s, 1H), 4.01 (d, J = 12.1 Hz, 1H), 3.58 (d, J = 12.1 Hz, 1H), 2.89 (s, 2H), 2.00 (s, 1H), 1.52 (s, 6H), 1.25 (m, 1H). | 661.2 | A | B |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-2650 | 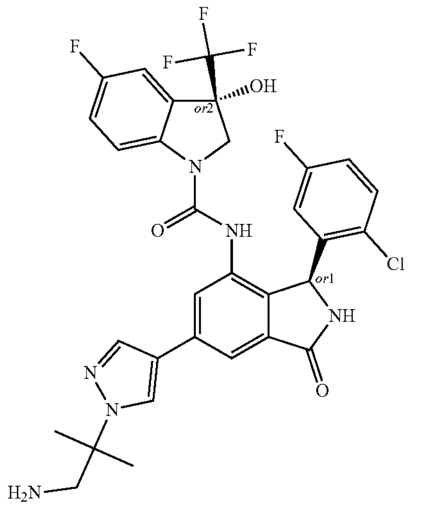 [SMILES: CC(C)(CN)n1cc(-c2cc(NC(=O)N3C[C@](O)(C(F)(F)F)c4cc(F)ccc43)c3c(c2)C(=O)N[C@@H]3c2cc(F)ccc2Cl)cn1] | CC(C)(CN)n1cc(cn1)-c1cc2C(=O)N[C@@H](c2c(NC(=O)N2C[C@](O)(c3cc(F)ccc23)C(F)(F)F)c1)cc(F)ccc1Cl | (400 MHz, DMSO-d6) 9.04 (s, 1H), 8.81 (s, 1H), 8.44 (s, 1H), 8.00 (s, 1H), 7.96-7.86 (m, 2H), 7.64-7.56 (m, 1H), 7.41 (s, 1H), 7.33-7.27 (m, 2H), 7.25-7.17 (m, 1H), 7.12 (td, J = 8.4, 3.1 Hz, 1H), 6.80-6.30 (s,1H), 6.01 (s, 1H), 4.01 (d, J = 12.1 Hz, 1H), 3.58 (d, J = 12.1 Hz, 1H), 2.89 (s, 2H), 2.00 (s, 1H), 1.52 (s, 6H), 1.25(m,1H). | 661.2 | C | |
| I-2651 | 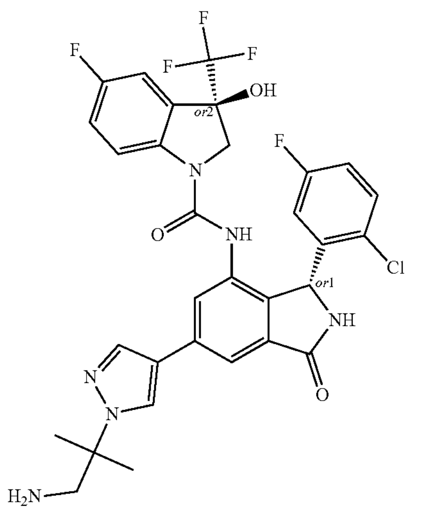 [SMILES: CC(C)(CN)n1cc(-c2cc(NC(=O)N3C[C@@](O)(C(F)(F)F)c4cc(F)ccc43)c3c(c2)C(=O)N[C@H]3c2cc(F)ccc2Cl)cn1] | CC(C)(CN)n1cc(cn1)-c1cc2C(=O)N[C@H](c2c(NC(=O)N2C[C@](O)(c3cc(F)ccc23)C(F)(F)F)c1)cc(F)ccc1Cl | (400 MHz, DMSO-d6) 9.04 (s, 1H), 8.81 (s, 1H), 8.44 (s, 1H), 8.00 (s, 1H), 7.96-7.86 (m, 2H), 7.64-7.56 (m, 1H), 7.41 (s, 1H), 7.33-7.27 (m, 2H), 7.25-7.17 (m, 1H), 7.12 (td, J = 8.4, 3.1 Hz, 1H), 6.80-6.30 (s, 1H), 6.01 (s, 1H), 4.01 (d, J = 12.1 Hz, 1H), 3.58 (d, J = 12.1 Hz, 1H), 2.89 (s, 2H), 2.00 (s, 1H), 1.52 (s, 6H), 1.25 (m, 1H). | 661.1 | D | |
| I-2652 | 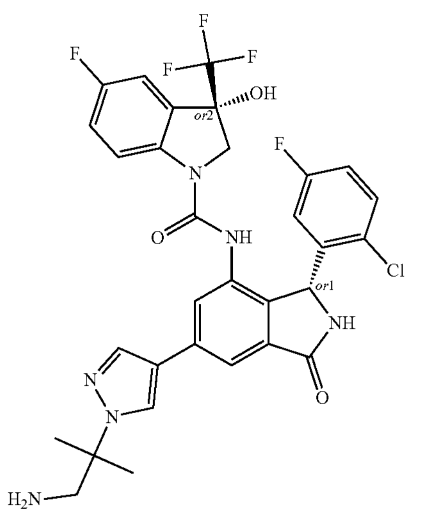 [SMILES: CC(C)(CN)n1cc(-c2cc(NC(=O)N3C[C@](O)(C(F)(F)F)c4cc(F)ccc43)c3c(c2)C(=O)N[C@H]3c2cc(F)ccc2Cl)cn1] | CC(C)(CN)n1cc(cn1)-c1cc2C(=O)N[C@H](c2c(NC(=O)N2C[C@@](O)(c3cc(F)ccc23)C(F)(F)F)c1)cc(F)ccc1Cl | (400 MHz, DMSO-d6) 9.04 (s, 1H), 8.81 (s, 1H), 8.44 (s, 1H), 8.00 (s, 1H), 7.96-7.86 (m, 2H), 7.64-7.56 (m, 1H), 7.41 (s, 1H), 7.33-7.27 (m, 2H), 7.25-7.17 (m, 1H), 7.12 (td, J = 8.4, 3.1 Hz, 1H), 6.80-6.30 (s, 1H), 6.01 (s, 1H), 4.01 (d, J = 12.1 Hz, 1H), 3.58 (d, J = 12.1 Hz, 1H), 2.89 (s, 2H), 2.00 (s, 1H), 1.52 (s, 6H), 1.25 (m, 1H). | 661.1 | D | |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-2653 | 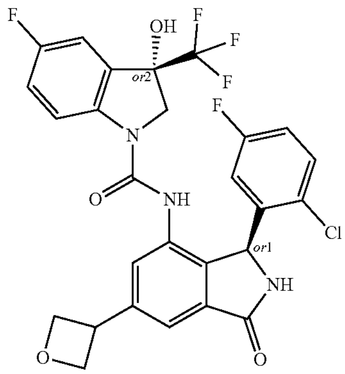 [SMILES: O=C1N[C@H](c2cc(F)ccc2Cl)c2c(NC(=O)N3C[C@](O)(C(F)(F)F)c4cc(F)ccc43)cc(C3COC3)cc21] | O[C@@]1(CN(C(=O)Nc2cc(cc3C(=O)N[C@@H](c23)c2cc(F)cc2Cl)C2COC2)ccc(F)cc12)C(F)(F)F | (400 MHz, DMSO-d6) 9.11 (s, 1H), 8.77 (s, 1H), 7.87 (dd, J = 8.9, 4.7 Hz, 1H), 7.63-7.59 (m, 1H), 7.54 (d, J = 1.6 Hz, 1H), 7.41-7.31 (m, 2H), 7.24 (ddd, J = 18.3, 9.2, 2.7 Hz, 2H), 7.12 (td, J = 8.4, 3.1 Hz, 1H), 6.56 (s, 1H), 6.06 (s, 1H), 5.02 (dd, J = 8.3, 6.0 Hz, 2H), 4.67 (dt, J = 11.3, 6.3 Hz, 2H), 4.41 (p, J = 7.4 Hz, 1H), 4.26 (d, J = 12.1 Hz, 1H), 3.41 (d, J = 12.0 Hz, 1H). | 580.1 | E | |
| I-2654 | 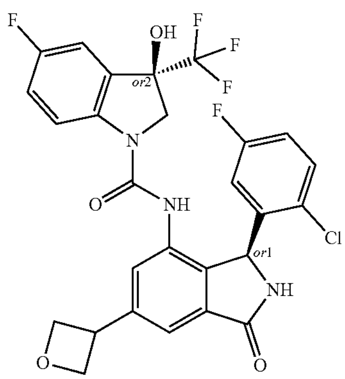 [SMILES: O=C1N[C@H](c2cc(F)ccc2Cl)c2c(NC(=O)N3C[C@@](O)(C(F)(F)F)c4cc(F)ccc43)cc(C3COC3)cc21] | O[C@]1(CN(C(=O)Nc2cc(cc3C(=O)N[C@@H](c23)c2cc(F)cc2Cl)C2COC2)ccc(F)cc12)C(F)(F)F | (400 MHz, DMSO-d6) 9.09 (s, 1H), 8.86 (s, 1H), 7.92 (dd, J = 9.0, 4.6 Hz, 1H), 7.61 (d, J = 1.6 Hz, 1H), 7.47 (d, J = 1.6 Hz, 1H), 7.41 (s, 1H), 7.32 (dd, J = 8.9, 5.2 Hz, 1H), 7.28 (td, J = 9.0, 2.8 Hz, 1H), 7.21 (dd, J = 8.0, 2.7 Hz, 1H), 7.13 (td, J = 8.4, 3.1 Hz, 1H), 6.56 (s, 1H), 6.02 (s, 1H), 5.02 (ddd, J = 8.3, 6.0, 1.1 Hz, 2H), 4.66 (dt, J = 10.8, 6.3 Hz, 2H), 4.46-4.35 (m, 1H), 4.02 (d, J = 12.1 Hz, 1H), 3.52 (d, J = 12.0 Hz, 1H). | 580.1 | D | |
| I-2655 | 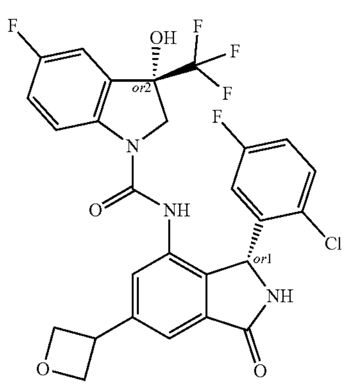 [SMILES: O=C1N[C@@H](c2cc(F)ccc2Cl)c2c(NC(=O)N3C[C@](O)(C(F)(F)F)c4cc(F)ccc43)cc(C3COC3)cc21] | O[C@@]1(CN(C(=O)Nc2cc(cc3C(=O)N[C@H](c23)c2cc(F)cc2Cl)C2COC2)ccc(F)cc12)C(F)(F)F | (400 MHz, DMSO-d6) 9.08 (s, 1H), 8.85 (s, 1H), 7.92 (dd, J = 9.1, 4.6 Hz, 1H), 7.61 (d, J = 1.5 Hz, 1H), 7.47 (d, J = 1.6 Hz, 1H), 7.40 (s, 1H), 7.36-7.18 (m, 3H), 7.12 (td, J = 8.3, 3.1 Hz, 1H), 6.56 (s, 1H), 6.02 (s, 1H), 5.02 (ddd, J = 8.3, 5.9, 1.1 Hz, 2H), 4.66 (dt, J = 10.6, 6.3 Hz, 2H), 4.40 (p, J = 7.2 Hz, 1H), 4.02 (d, J = 12.1 Hz, 1H), 3.53 (d, J = 12.0 Hz, 1H), 1.45-1.20 (m, 1H). | 580.1 | A | A |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-2656 | 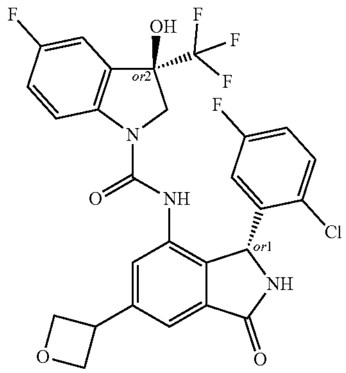 [SMILES: O=C1N[C@@H](c2cc(F)ccc2Cl)c2c(NC(=O)N3C[C@@](O)(C(F)(F)F)c4cc(F)ccc43)cc(C3COC3)cc21] | O[C@]1(CN(C(=O)Nc2cc(cc3C(=O)N[C@H](c23)c2cc(F)ccc2Cl)COC2)c2ccc(F)cc12)C(F)(F)F | (400 MHz, DMSO-d6) 9.09 (s, 1H), 8.76 (s, 1H), 7.87 (dd, J = 9.0, 4.7 Hz, 1H), 7.61 (d, J = 1.6 Hz, 1H), 7.53 (d, J = 1.5 Hz, 1H), 7.40-7.31 (m, 2H), 7.30-7.21 (m, 1H), 7.25-7.18 (m, 1H), 7.12 (ddd, J = 8.9, 7.9, 3.1 Hz, 1H), 6.56 (s, 1H), 6.06 (s, 1H), 5.02 (dd, J = 8.3, 6.0 Hz, 2H), 4.67 (dt, J = 11.2, 6.3 Hz, 2H), 4.40 (ddd, J = 14.8, 8.4, 6.7 Hz, 1H), 4.26 (d, J = 12.0 Hz, 1H), 3.41 (d, J = 12.1 Hz, 1H). | 580.1 | C | |
| I-2657 | 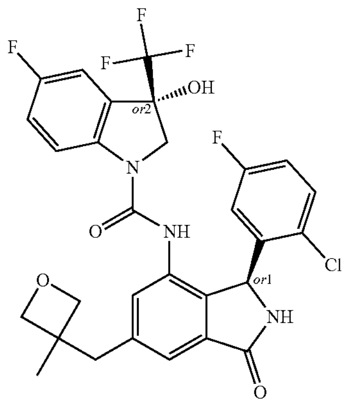 [SMILES: CC1(Cc2cc(NC(=O)N3C[C@](O)(C(F)(F)F)c4cc(F)ccc43)c3c(c2)C(=O)N[C@@H]3c2cc(F)ccc2Cl)COC1] | CC1(Cc2cc3C(=O)N[C@@H](c3c(NC(=O)N3C[C@@](O)(c4cc(F)ccc34)C(F)(F)F)c2c2cc(F)ccc2Cl)COC1 | (400 MHz, DMSO-d6) 9.03 (s, 1H), 8.76 (s, 1H), 7.92 (dd, J = 8.8, 4.6 Hz, 1H), 7.44-7.35 (m, 2H), 7.35-7.23 (m, 2H), 7.20 (dd, J = 8.7, 2.2 Hz, 2H), 7.12 (td, J = 8.4, 3.1 Hz, 1H), 6.56 (s, 1H), 5.99 (s, 1H), 4.58 (t, J = 5.7 Hz, 2H), 4.24 (dd, J = 5.6, 3.3 Hz, 2H), 4.00 (d, J = 12.1 Hz, 1H), 3.51 (d, J = 12.1 Hz, 1H), 3.14-2.92 (m, 2H), 1.24 (s, 3H). | 608.4 | A | A |
| I-2658 | 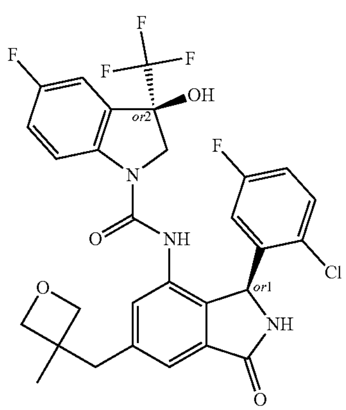 [SMILES: CC1(Cc2cc(NC(=O)N3C[C@@](O)(C(F)(F)F)c4cc(F)ccc43)c3c(c2)C(=O)N[C@@H]3c2cc(F)ccc2Cl)COC1] | CC1(Cc2cc3C(=O)N[C@@H](c3c(NC(=O)N3C[C@](O)(c4cc(F)ccc34)C(F)(F)F)c2c2cc(F)ccc2Cl)COC1 | (400 MHz, DMSO-d6) 9.05 (s, 1H), 8.68 (s, 1H), 7.85 (dd, J = 8.9, 4.7 Hz, 1H), 7.41 (d, J = 1.3 Hz, 1H), 7.37-7.31 (m, 2H), 7.29-7.18 (m, 3H), 7.11 (ddd, J = 8.9, 7.9, 3.1 Hz, 1H), 6.56 (s, 1H), 6.02 (s, 1H), 4.57 (t, J = 5.9 Hz, 2H), 4.33-4.02 (m, 3H), 3.41 (d, J = 12.0 Hz, 1H), 3.10 (d, J = 13.4 Hz, 1H), 3.01 (d, J = 13.4 Hz, 1H), 1.24 (s, 3H). | 608.4 | D | |

TABLE 2-continued

Representative Compounds of the Invention with Bioactivity Data.

| Ex. No. | Structure | SMILES | $^1$H NMR | MS | ADP-Glo IC$_{50}$ | MCF 10A IC$_{50}$ |
|---|---|---|---|---|---|---|
| I-2659 | 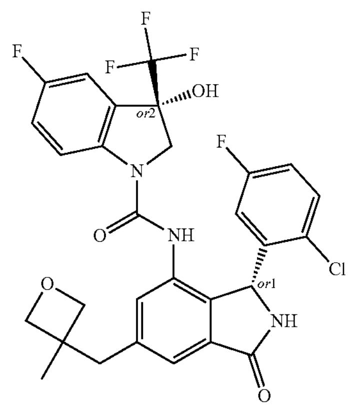 [SMILES: CC1(Cc2cc(NC(=O)N3C[C@](O)(C(F)(F)F)c4cc(F)ccc43)c3c(c2)C(=O)N[C@H]3c2cc(F)ccc2Cl)COC1] | CC1(Cc2cc3C(=O)N[C@H](c3c(NC(=O)N3C[C@@](O)(c4cc(F)ccc34)C(F)(F)F)c2)c2cc(F)ccc2Cl)COC1 | (400 MHz, DMSO-d6) 9.05 (s, 1H), 8.69 (s, 1H), 7.85 (dd, J = 9.0, 4.7 Hz, 1H), 7.41 (d, J = 1.4 Hz, 1H), 7.38-7.30 (m, 2H), 7.30-7.17 (m, 3H), 7.11 (td, J = 8.3, 3.1 Hz, 1H), 6.56 (s, 1H), 6.02 (s, 1H), 4.57 (t, J = 5.9 Hz, 2H), 4.28-4.10 (m, 3H), 3.40 (d, J = 12.0 Hz, 1H), 3.10 (d, J = 13.4 Hz, 1H), 3.01 (d, J = 13.4 Hz, 1H), 1.24 (s, 3H). | 608.4 | D | |
| I-2660 | 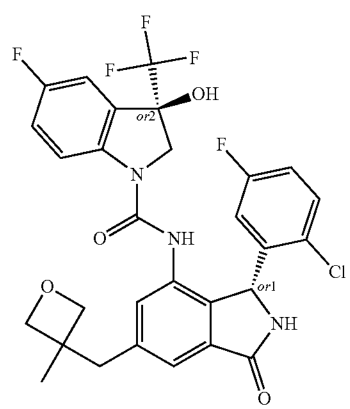 [SMILES: CC1(Cc2cc(NC(=O)N3C[C@@](O)(C(F)(F)F)c4cc(F)ccc43)c3c(c2)C(=O)N[C@H]3c2cc(F)ccc2Cl)COC1] | CC1(Cc2cc3C(=O)N[C@H](c3c(NC(=O)N3C[C@](O)(c4cc(F)ccc34)C(F)(F)c2)c2cc(F)cc2Cl)COC1 | (400 MHz, DMSO-d6) 9.04 (s, 1H), 8.77 (s, 1H), 7.92 (dd, J = 9.0, 4.7 Hz, 1H), 7.40 (d, J = 10.1 Hz, 2H), 7.35-7.23 (m, 2H), 7.22-7.16 (m, 2H), 7.12 (td, J = 8.4, 3.1 Hz, 1H), 6.95-6.14 (m, 1H), 5.98 (s, 1H), 4.58 (t, J = 5.8 Hz, 2H), 4.24 (dd, J = 5.6, 3.4 Hz, 2H), 4.00 (d, J = 12.1 Hz, 1H), 3.51 (d, J = 12.1 Hz, 1H), 3.10 (d, J = 13.5 Hz, 1H), 3.01 (d, J = 13.4 Hz, 1H), 1.24 (s, 3H). | 608.1 | E | |
| I-2661 | 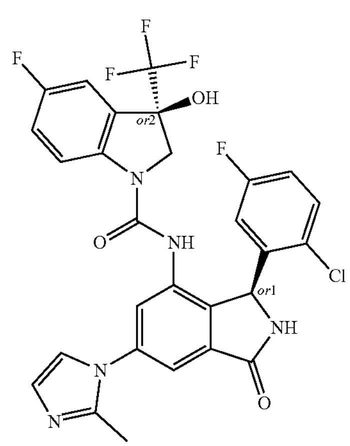 [SMILES: Cc1nccn1-c1cc(NC(=O)N2C[C@@](O)(C(F)(F)F)c3cc(F)ccc32)c2c(c1)C(=O)N[C@@H]2c1cc(F)ccc1Cl] | Cc1nccn1-c1cc2C(=O)N[C@@H](c2c(NC(=O)N2C[C@](O)(c3cc(F)ccc23)C(F)(F)F)c1)c1cc(F)ccc1Cl | (400 MHz, DMSO-d6) 9.28 (s, 1H), 8.99 (s, 1H), 7.92 (t, J = 6.0 Hz, 1H), 7.61 (d, J = 1.9 Hz, 1H), 7.51-7.39 (m, 3H), 7.43-7.32 (m, 1H), 7.29 (td, J = 9.0, 2.7 Hz, 1H), 7.22 (dd, J = 8.1, 2.7 Hz, 1H), 7.15 (td, J = 8.4, 3.1 Hz, 1H), 6.98 (d, J = 1.5 Hz, 1H), 6.74 (s, 2H), 6.11 (s, 1H), 3.99 (d, J = 11.8 Hz, 1H), 3.55 (d, J = 12.0 Hz, 1H), 2.37 (s, 3H). | 604.1 | A | A |

TABLE 2-continued

Representative Compounds of the Invention with Bioactivity Data.

| Ex. No. | Structure | SMILES | $^1$H NMR | MS | ADP-Glo IC$_{50}$ | MCF 10A IC$_{50}$ |
|---|---|---|---|---|---|---|
| I-2662 | 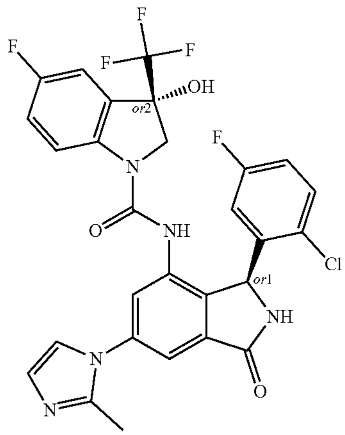 [SMILES: Cc1nccn1-c1cc(NC(=O)N2C[C@](O)(C(F)(F)F)c3cc(F)ccc32)c2c(c1)C(=O)N[C@@H]2c1cc(F)ccc1Cl] | Cc1nccn1-c1cc2C(=O)N[C@@H](c2c(NC(=O)N2C[C@@](O)(c3cc(F)ccc23)C(F)(F)F)c1)c1cc(F)ccc1Cl | (400 MHz, DMSO-d6) 9.29 (s, 1H), 8.89 (s, 1H), 7.86 (dd, J = 9.0, 4.6 Hz, 1H), 7.61 (d, J = 1.9 Hz, 1H), 7.54 (d, J = 1.9 Hz, 1H), 7.43 (d, J = 1.4 Hz, 1H), 7.43-7.34 (m, 2H), 7.31-7.19 (m, 2H), 7.19-7.10 (m, 1H), 6.96 (d, J = 1.4 Hz, 1H), 6.72 (s, 1H), 6.15 (s, 1H), 4.18 (d, J = 12.0 Hz, 1H), 3.46 (d, J = 12.0 Hz, 1H), 2.37 (s, 3H). | 604.1 | D | |
| I-2663 | 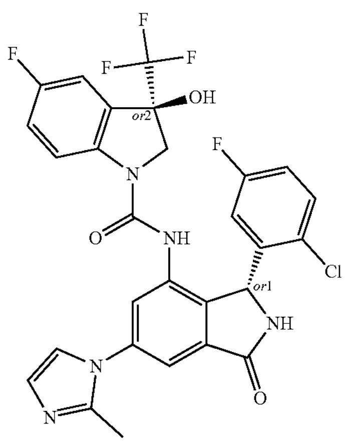 [SMILES: Cc1nccn1-c1cc(NC(=O)N2C[C@@](O)(C(F)(F)F)c3cc(F)ccc32)c2c(c1)C(=O)N[C@H]2c1cc(F)ccc1Cl] | Cc1nccn1-c1cc2C(=O)N[C@H](c2c(NC(=O)N2C[C@](O)(c3cc(F)ccc23)C(F)(F)F)c1)c1cc(F)ccc1Cl | (400 MHz, DMSO-d6) 9.28 (s, 1H), 8.88 (s, 1H), 7.86 (dd, J = 9.0, 4.7 Hz, 1H), 7.61 (d, J = 1.9 Hz, 1H), 7.54 (d, J = 1.9 Hz, 1H), 7.43 (d, J = 1.5 Hz, 1H), 7.41-7.34 (m, 2H), 7.31-7.19 (m, 2H), 7.15 (td, J = 8.4, 3.1 Hz, 1H), 6.96 (d, J = 1.4 Hz, 1H), 6.14 (s, 1H), 4.18 (d, J = 11.9 Hz, 1H), 3.46 (d, J = 12.0 Hz, 1H), 2.37 (s, 3H). | 604.1 | D | |
| I-2664 | 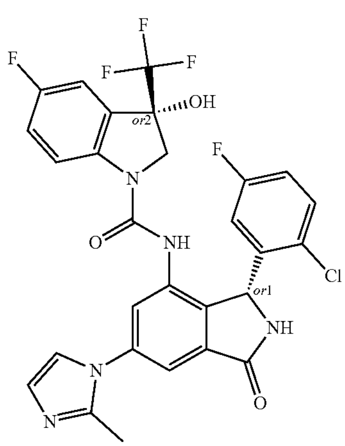 [SMILES: Cc1nccn1-c1cc(NC(=O)N2C[C@](O)(C(F)(F)F)c3cc(F)ccc32)c2c(c1)C(=O)N[C@H]2c1cc(F)ccc1Cl] | Cc1nccn1-c1cc2C(=O)N[C@H](c2c(NC(=O)N2C[C@@](O)(c3cc(F)ccc23)C(F)(F)F)c1)c1cc(F)ccc1Cl | (400 MHz, DMSO-d6) 9.28 (s, 1H), 8.99 (s, 1H), 7.93 (dd, J = 8.9, 4.6 Hz, 1H), 7.61 (d, J = 1.9 Hz, 1H), 7.43 (dd, J = 14.4, 1.9 Hz, 3H), 7.41-7.19 (m, 3H), 7.15 (td, J = 8.4, 3.1 Hz, 1H), 6.96 (d, J = 1.4 Hz, 1H), 6.11 (s, 1H), 4.00 (d, J = 12.0 Hz, 1H), 3.55 (d, J = 12.0 Hz, 1H), 2.37 (s, 3H). | 604.1 | D | |

TABLE 2-continued

Representative Compounds of the Invention with Bioactivity Data.

| Ex. No. | Structure | SMILES | $^1$H NMR | MS | ADP-Glo IC$_{50}$ | MCF 10A IC$_{50}$ |
|---|---|---|---|---|---|---|
| I-2665 | 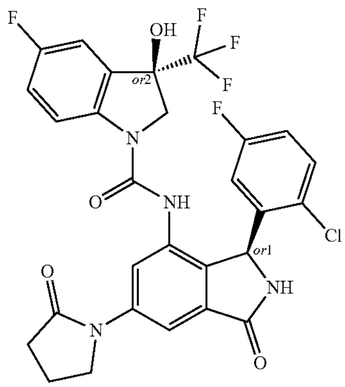 [SMILES: O=C1N[C@H](c2cc(F)ccc2Cl)c2c(NC(=O)N3C[C@@](O)(C(F)(F)F)c4cc(F)ccc43)cc(N3CCCC3=O)cc21] | O[C@]1(CN(C(=O)Nc2cc(cc3C(=O)N[C@@H](c23)c2cc(F)cc2Cl)N2CCCC2=O)c2ccc(F)cc12)C(F)(F)F | (400 MHz, DMSO-d6) 9.11 (s, 1H), 8.95 (s, 1H), 7.93 (s, 1H), 7.85 (d, J = 2.0 Hz, 1H), 7.81 (d, J = 2.0 Hz, 1H), 7.40 (s, 1H), 7.36-7.24 (m, 2H), 7.21 (d, J = 8.2 Hz, 1H), 7.13 (td, J = 8.3, 3.1 Hz, 1H), 6.54 (s, 1H), 5.99 (s, 1H), 4.09-3.85 (m, 3H), 2.56 (d, J = 8.5 Hz, 3H), 2.11 (p, J = 7.5 Hz, 2H). | 607.2 | A | A |
| I-2666 | 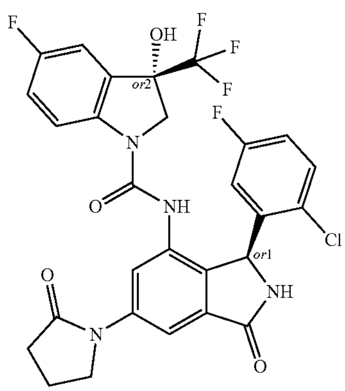 [SMILES: O=C1N[C@H](c2cc(F)ccc2Cl)c2c(NC(=O)N3C[C@](O)(C(F)(F)F)c4cc(F)ccc43)cc(N3CCCC3=O)cc21] | O[C@@]1(CN(C(=O)Nc2cc(cc3C(=O)N[C@@H](c23)c2cc(F)cc2Cl)N2CCCC2=O)c2ccc(F)cc12)C(F)(F)F | (400 MHz, DMSO-d6) 9.10 (s, 1H), 8.83 (s, 1H), 7.91-7.80 (m, 3H), 7.38-7.30 (m, 2H), 7.30-7.19 (m, 2H), 7.11 (td, J = 8.3, 3.1 Hz, 1H), 6.54 (s, 1H), 6.01 (s, 1H), 4.29 (d, J = 12.0 Hz, 1H), 4.01 "C. 3.86 (m, 2H), 3.32 (s, 1H), 2.57 (t, J = 8.0 Hz, 2H), 2.17 "C. 2.05 (m, 2H). | 607.1 | D | |
| I-2667 | 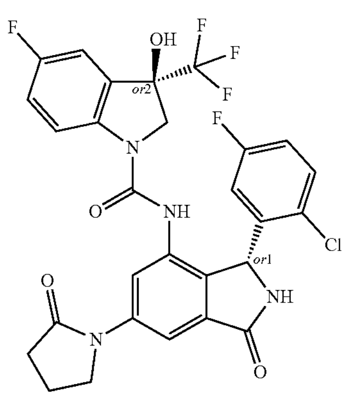 [SMILES: O=C1N[C@@H](c2cc(F)ccc2Cl)c2c(NC(=O)N3C[C@@](O)(C(F)(F)F)c4cc(F)ccc43)cc(N3CCCC3=O)cc21] | O[C@]1(CN(C(=O)Nc2cc(cc3C(=O)N[C@@H](c23)c2cc(F)cc2Cl)N2CCCC2=O)c2ccc(F)cc12)C(F)(F)F | (400 MHz, DMSO-d6) 9.10 (s, 1H), 8.83 (s, 1H), 7.91-7.80 (m, 3H), 7.38-7.30 (m, 2H), 7.30-7.18 (m, 2H), 7.11 (td, J = 8.4, 3.1 Hz, 1H), 6.55 (s, 1H), 6.01 (s, 1H), 4.29 (d, J = 12.1 Hz, 1H), 4.01-3.86 (m, 2H), 3.32 (s, 1H), 2.57 (t, J = 8.0 Hz, 2H), 2.17 "C. 2.05 (m, 2H). | 607.2 | D | |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-2668 | 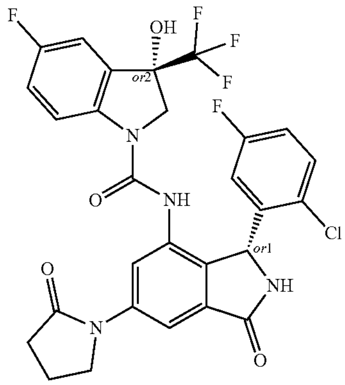 [SMILES: O=C1N[C@@H](c2cc(F)ccc2Cl)c2c(NC(=O)N3C[C@](O)(C(F)(F)F)c4cc(F)ccc43)cc(N3CCCC3=O)cc21] | O[C@@]1(CN(C(=O)Nc2cc(cc3C(=O)N[C@H](c23)c2cc(F)ccc2Cl)N2CCCC2=O)c2ccc(F)cc12)C(F)(F)F | (400 MHz, DMSO-d6) 9.09 (s, 1H), 8.93 (s, 1H), 7.93 (s, 1H), 7.83 (dd, J = 18.0, 2.0 Hz, 2H), 7.38 (s, 1H), 7.33 (d, J = 5.2 Hz, 1H), 7.34-7.23 (m, 1H), 7.23-7.17 (m, 1H), 7.12 (td, J = 8.2, 3.0 Hz, 1H), 6.58 (s, 1H), 5.99 (s, 1H), 4.05 (d, J = 12.3 Hz, 1H), 4.02-3.85 (m, 2H), 3.51-3.41 (m, 1H), 2.58 (d, J = 8.0 Hz, 2H), 2.11 (dd, J = 14.4, 6.9 Hz, 2H). | 607.1 | E | |
| I-2669 | 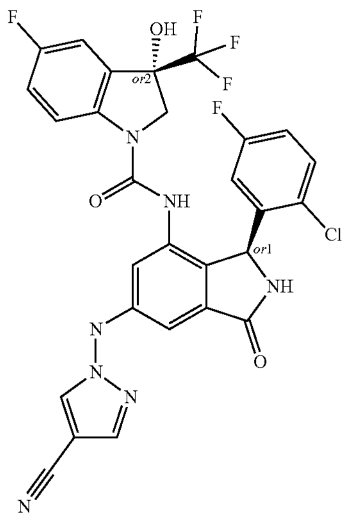 [SMILES: N#Cc1cnn(Nc2cc(NC(=O)N3C[C@](O)(C(F)(F)F)c4cc(F)ccc43)c3c(c2)C(=O)N[C@@H]3c2cc(F)ccc2Cl)c1] | O[C@@]1(CN(C(=O)Nc2cc(Cn3cc(cn3)C#N)cc3C(=O)N[C@@H](c23)c2cc(F)ccc2Cl)c2ccc(F)cc12)C(F)(F)F | (400 MHz, DMSO-d6) 9.14 (s, 1H), 8.87 (s, 1H), 8.79 (s, 1H), 8.15 (s, 1H), 7.91 (s, 1H), 7.53 (s, 1H), 7.41 (s, 1H), 7.36-7.23 (m, 3H), 7.20 (d, J = 8.2 Hz, 1H), 7.13 (td, J = 8.4, 3.0 Hz, 1H), 6.51 (s, 1H), 6.00 (s, 1H), 5.58 (s, 2H), 4.00 (d, J = 12.0 Hz, 1H), 3.46 (d, J = 12.0 Hz, 1H) | 629.2 | A | A |
| I-2670 | 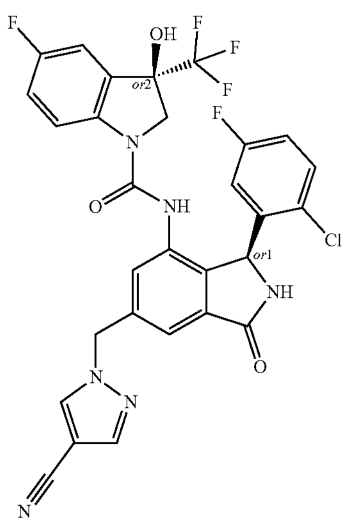 [SMILES: N#Cc1cnn(Cc2cc(NC(=O)N3C[C@@](O)(C(F)(F)F)c4cc(F)ccc43)c3c(c2)C(=O)N[C@@H]3c2cc(F)ccc2Cl)c1] | O[C@]1(CN(C(=O)Nc2cc(Cn3cc(cn3)C#N)cc3C(=O)N[C@@H](c23)c2cc(F)ccc2Cl)c2cc(F)cc12)C(F)(F)F | (400 MHz, DMSO-d6) 9.15 (s, 1H), 8.78 (d, J = 3.6 Hz, 2H), 8.15 (s, 1H), 7.84 (dd, J = 9.0, 4.7 Hz, 1H), 7.52 (s, 1H), 7.39 (s, 1H), 7.37-7.30 (m, 2H), 7.30-7.19 (m, 2H), 7.12 (td, J = 8.3, 3.0 Hz, 1H), 6.51 (s, 1H), 6.04 (s, 1H), 5.57 (s, 2H), 4.22 (d, J = 12.0 Hz, 1H), 3.34 (s, 1H). | 629.2 | C | |

TABLE 2-continued

Representative Compounds of the Invention with Bioactivity Data.

| Ex. No. | Structure | SMILES | ¹H NMR | MS | ADP-Glo IC₅₀ | MCF 10A IC₅₀ |
|---|---|---|---|---|---|---|
| I-2671 | 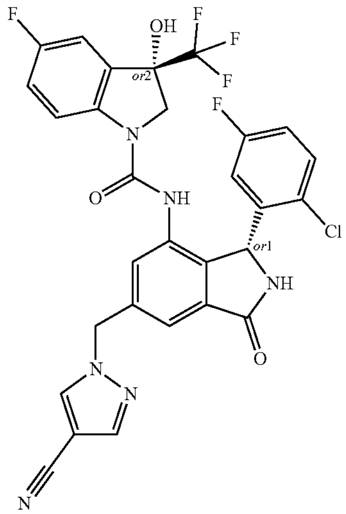 [SMILES: N#Cc1cnn(Cc2cc(NC(=O)N3C[C@](O)(C(F)(F)F)c4cc(F)ccc43)c3c(c2)C(=O)N[C@H]3c2cc(F)ccc2Cl)c1] | O[C@@]1(CN(C(=O)Nc2cc(Cn3cc(cn3)C#N)cc3C(=O)N[C@H](c23)c2cc(F)cc2Cl)c2ccc(F)cc1)C(F)(F)F | (400 MHz, DMSO-d6) 9.15 (s, 1H), 8.78 (d, J = 3.6 Hz, 2H), 8.15 (s, 1H), 7.84 (dd, J = 8.9, 4.7 Hz, 1H), 7.52 (s, 1H), 7.42-7.30 (m, 3H), 7.24 (ddd, J = 18.5, 9.3, 2.8 Hz, 2H), 7.12 (td, J = 8.3, 3.1 Hz, 1H), 6.51 (s, 1H), 6.03 (s, 1H), 5.57 (s, 2H), 4.22 (d, J = 12.1 Hz, 1H), 3.37 (s, 1H). | 629.2 | C | |
| I-2672 | 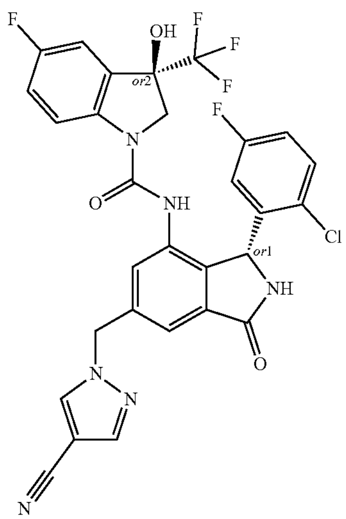 [SMILES: N#Cc1cnn(Cc2cc(NC(=O)N3C[C@@](O)(C(F)(F)F)c4cc(F)ccc43)c3c(c2)C(=O)N[C@H]3c2cc(F)ccc2Cl)c1] | O[C@]1(CN(C(=O)Nc2cc(Cn3cc(cn3)C#N)cc3C(=O)N[C@H](c23)c2c(F)ccc2Cl)c2ccc(F)cc12)C(F)(F)F | (400 MHz, DMSO-d6) 9.14 (s, 1H), 8.87 (s, 1H), 8.79 (s, 1H), 8.15 (s, 1H), 7.91 (s, 1H), 7.53 (s, 1H), 7.40 (s, 1H), 7.36-7.23 (m, 3H), 7.21 (d, J = 8.0 Hz, 1H), 7.13 (td, J = 8.3, 3.0 Hz, 1H), 6.51 (s, 1H), 6.00 (s, 1H), 5.58 (s, 2H), 3.99 (d, J = 12.1 Hz, 1H), 3.46 (d, J = 11.7 Hz, 1H). | 629.2 | E | |
| I-2673 | 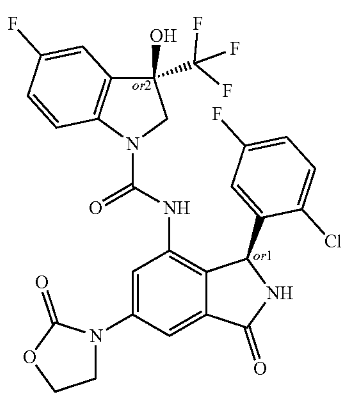 [SMILES: O=C1N[C@H](c2cc(F)ccc2Cl)c2c(NC(=O)N3C[C@@](O)(C(F)(F)F)c4cc(F)ccc43)cc(N3CCOC3=O)cc21] | O[C@]1(CN(C(=O)Nc2cc(cc3C(=O)N[C@@H](c23)c2cc(F)ccc2Cl)N2CCOC2=O)c2ccc(F)cc12)C(F)(F)F | (400 MHz, DMSO-d6) 9.13 (s, 1H), 8.98 (s, 1H), 7.75 (d, J = 2.1 Hz, 1H), 7.69 (d, J = 2.1 Hz, 1H), 7.40 (s, 1H), 7.36-7.24 (m, 2H), 7.21 (dd, J = 8.0, 2.7 Hz, 1H), 7.13 (td, J = 8.3, 3.1 Hz, 1H), 6.56 (s, 1H), 5.99 (s, 1H), 4.50 (t, J = 8.0 Hz, 2H), 4.17 (dq, J = 27.7, 8.3 Hz, 2H), 4.06 (d, J = 12.2 Hz, 1H), 3.46 (d, J = 12.1 Hz, 1H). | 609.4 | A | A |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-2674 | 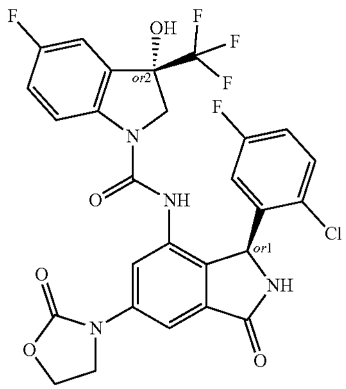 [SMILES: O=C1N[C@H](c2cc(F)ccc2Cl)c2c(NC(=O)N3C[C@](O)(C(F)(F)F)c4cc(F)ccc43)cc(N3CCOC3=O)cc21] | O[C@@]1(CN(C(=O)Nc2cc(cc3C(=O)N[C@@H](c23)c2cc(F)cc c2Cl)N2CCOC2=O)c2ccc(F)cc12)C(F)(F)F | (400 MHz, DMSO-d6) 9.13 (s, 1H), 8.98 (s, 1H), 7.75 (d, J = 2.1 Hz, 1H), 7.69 (d, J = 2.1 Hz, 1H), 7.40 (s, 1H), 7.36-7.24 (m, 2H), 7.21 (dd, J = 8.0, 2.7 Hz, 1H), 7.13 (td, J = 8.3, 3.1 Hz, 1H), 6.56 (s, 1H), 5.99 (s, 1H), 4.50 (t, J = 8.0 Hz, 2H), 4.17 (dq, J = 27.7, 8.3 Hz, 2H), 4.06 (d, J = 12.2 Hz, 1H), 3.46 (d, J = 12.1 Hz, 1H). | 609.4 | D | |
| I-2675 | 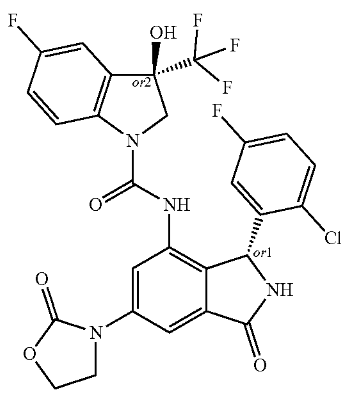 [SMILES: O=C1N[C@@H](c2cc(F)ccc2Cl)c2c(NC(=O)N3C[C@@](O)(C(F)(F)F)c4cc(F)ccc43)cc(N3CCOC3=O)cc21] | O[C@]1(CN(C(=O)Nc2cc(cc3C(=O)N[C@H](c23)c2cc(F)cc c2Cl)N2CCOC2=O)c2ccc(F)cc12)C(F)(F)F | (400 MHz, DMSO-d6) 9.13 (s, 1H), 8.98 (s, 1H), 7.75 (d, J = 2.1 Hz, 1H), 7.69 (d, J = 2.1 Hz, 1H), 7.40 (s, 1H), 7.36-7.24 (m, 2H), 7.21 (dd, J = 8.0, 2.7 Hz, 1H), 7.13 (td, J = 8.3, 3.1 Hz, 1H), 6.56 (s, 1H), 5.99 (s, 1H), 4.50 (t, J = 8.0 Hz, 2H), 4.17 (dq, J = 27.7, 8.3 Hz, 2H), 4.06 (d, J = 12.2 Hz, 1H), 3.46 (d, J = 12.1 .Hz, 1H). | 609.2 | D | |
| I-2676 | 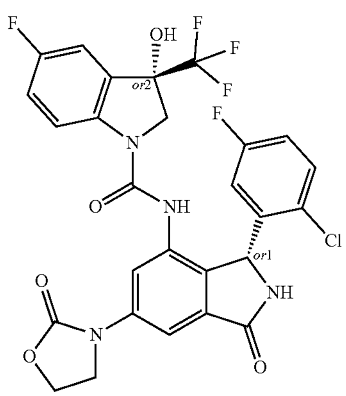 [SMILES: O=C1N[C@@H](c2cc(F)ccc2Cl)c2c(NC(=O)N3C[C@](O)(C(F)(F)F)c4cc(F)ccc43)cc(N3CCOC3=O)cc21] | O[C@@]1(CN(C(=O)Nc2cc(cc3C(=O)N[C@H](c23)c2cc(F)cc c2Cl)N2CCOC2=O)c2ccc(F)cc12)C(F)(F)F | (400 MHz, DMSO-d6) 9.13 (s, 1H), 8.98 (s, 1H), 7.75 (d, J = 2.1 Hz, 1H), 7.69 (d, J = 2.1 Hz, 1H), 7.40 (s, 1H), 7.36-7.24 (m, 2H), 7.21 (dd, J = 8.0, 2.7 Hz, 1H), 7.13 (td, J = 8.3, 3.1 Hz, 1H), 6.56 (s, 1H), 5.99 (s, 1H), 4.50 (t, J = 8.0 Hz, 2H), 4.17 (dq, J = 27.7, 8.3 Hz, 2H), 4.06 (d, J = 12.2 Hz, 1H), 3.46 (d, J = 12.1 Hz, 1H). | 609.2 | E | |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-2677 | 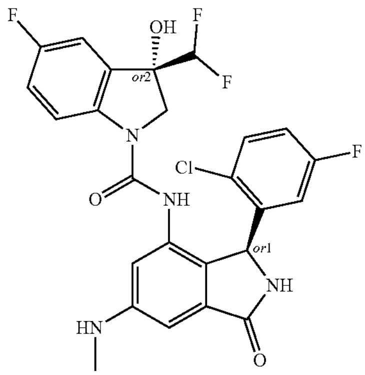 [SMILES: CNc1cc(NC(=O)N2C[C@](O)(C(F)F)c3cc(F)ccc32)c2c(c1)C(=O)N[C@@H]2c1cc(F)ccc1Cl] | CNc1cc2C(=O)N[C@@H](c2c(NC(=O)N2C[C@](O)(C(F)F)c3cc(F)ccc23)c1)c1cc(F)ccc1Cl | (400 MHz, DMSO-d6) 8.82 (s, 1H), 8.49 (s, 1H), 7.87 (dd, J = 8.9, 4.7 Hz, 1H), 7.29 (dd, J = 8.9, 5.2 Hz, 1H), 7.24 (dd, J = 8.3, 2.8 Hz, 1H), 7.17 (td, J = 9.0, 2.8 Hz, 1H), 7.08 (td, J = 8.3, 3.1 Hz, 1H), 6.69 (d, J = 2.1 Hz, 1H), 6.65 (s, 1H), 6.59 (d, J = 2.1 Hz, 1H), 6.45 (d, J = 47.5 Hz, 1H), 6.25 (s, 1H), 6.15-6.07 (m, 1H), 5.89 (s, 1H), 3.87-3.79 (m, 1H), 3.46 (d, J = 11.7 Hz, 1H), 2.75 (d, J = 5.0 Hz, 3H). | 535.1 | A | A |
| I-2678 | 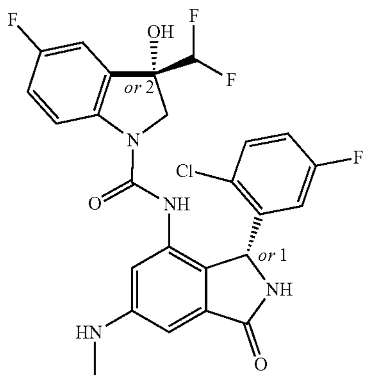 | CNc1cc2C(=O)N[C@H](c2c(NC(=O)N2C[C@](O)(C(F)F)c3cc(F)ccc23)c1)c1cc(F)ccc1Cl | (400 MHz, DMSO-d6) 8.84 (s, 1H), 8.40 (s, 1H), 7.80 (dd, J = 9.0, 4.7 Hz, 1H), 7.32 (dd, J = 8.9, 5.2 Hz, 1H), 7.22 (dd, J = 8.2, 2.8 Hz, 1H), 7.15 (td, J = 9.1, 2.8 Hz, 1H), 7.08 (td, J = 8.3, 3.1 Hz, 1H), 6.70-6.64 (m, 2H), 6.60 (s, 1H), 6.45 (d, J = 47.1 Hz, 1H), 6.25 (s, 1H), 6.16-6.08 (m, 1H), 5.93 (s, 1H), 4.09 (d, J = 11.7 Hz, 1H), 3.30 (d, J = 3.6 Hz, 1H), 2.75 (d, J = 4.9 Hz, 3H). | 535.1 | D | |
| I-2679 | 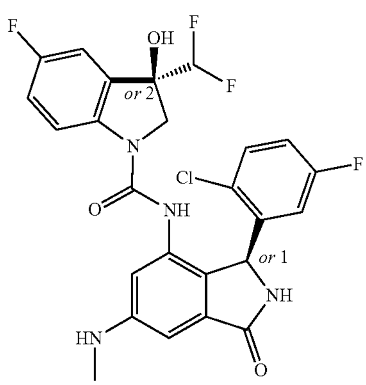 | CNc1cc2C(=O)N[C@@H](c2c(NC(=O)N2C[C@@](O)(C(F)F)c3cc(F)ccc23)c1)c1cc(F)ccc1Cl | (400 MHz, DMSO-d6) 8.84 (s, 1H), 8.40 (s, 1H), 7.80 (dd, J = 9.0, 4.7 Hz, 1H), 7.32 (dd, J = 8.8, 5.1 Hz, 1H), 7.22 (dd, J = 8.3, 2.8 Hz, 1H), 7.15 (td, J = 9.0, 2.8 Hz, 1H), 7.08 (td, J = 8.4, 3.1 Hz, 1H), 6.71-6.64 (m, 2H), 6.60 (s, 1H), 6.39 (s, 1H), 6.25 (s, 1H), 6.15-6.05 (m, 1H), 5.93 (s, 1H), 4.09 (d, J = 11.7 Hz, 1H), 3.29 (s, 1H), 2.75 (d, J = 5.0 Hz, 3H). | 535.1 | E | |
| I-2680 | 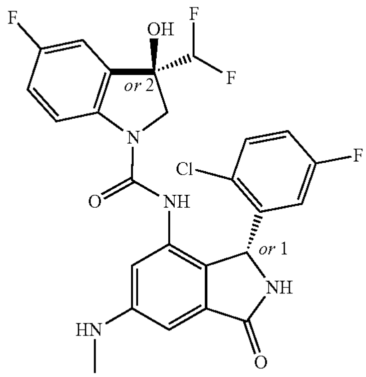 | CNc1cc2C(=O)N[C@H](c2c(NC(=O)N2C[C@@](O)(C(F)F)c3cc(F)ccc23)c1)c1cc(F)ccc1Cl | (400 MHz, DMSO-d6) 8.82 (s, 1H), 8.49 (s, 1H), 7.87 (dd, J = 8.9, 4.7. Hz, 1H), 7.29 (dd, J = 8.9, 5.1 Hz, 1H), 7.23 (dd, J = 8.2, 2.8 Hz, 1H), 7.17 (td, J = 9.1, 2.8 Hz, 1H), 7.08 (td, J = 8.4, 3.1 Hz, 1H), 6.69 (d, J = 2.1 Hz, 1H), 6.65 (s, 1H), 6.59 (d, J = 2.1 Hz, 1H), 6.45 (d, J = 46.0 Hz, 1H), 6.25 (s, 1H), 6.12 (d, J = 5.6 Hz, 1H), 5.89 (s, 1H), 3.83 (d, J = 11.8 Hz, 1H), 3.46 (d, J = 11.8 Hz, 1H), 2.75 (d, J = 4.9 Hz, 3H). | 535.2 | E | |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-2681 | 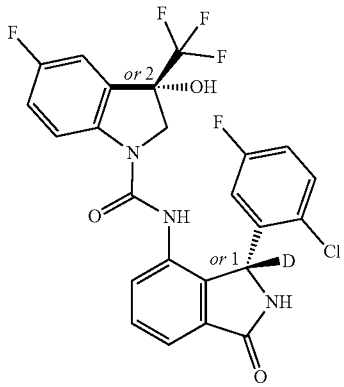 | [2H][C@]1(NC(=O)c2cccc(NC(=O)N3C[C@@](O)(c4cc(F)ccc34)C(F)(F)F)c12)c1cc(F)ccc1Cl | | | D | |
| I-2682 | 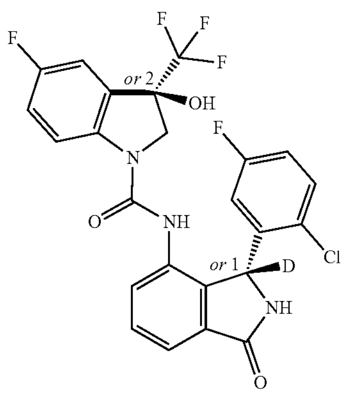 | [2H][C@]1(NC(=O)c2cccc(NC(=O)N3C[C@](O)(c4cc(F)ccc34)C(F)(F)F)c12)c1cc(F)ccc1Cl | | | A | A |
| I-2683 | 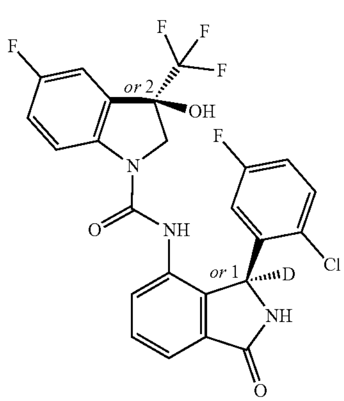 | [2H][C@@]1(NC(=O)c2cccc(NC(=O)N3C[C@](O)(c4cc(F)ccc34)C(F)(F)F)c12)c1cc(F)ccc1Cl | | | D | |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-2684 | 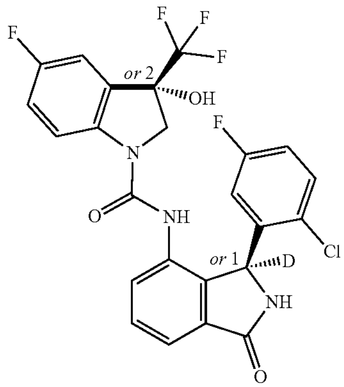 | [2H][C@@]1(NC(=O)c2cccc(NC(=O)N3C[C@@](O)(c4cc(F)ccc34)C(F)(F)F)c12)c1cc(F)ccc1Cl | | | E | |
| I-2685 | 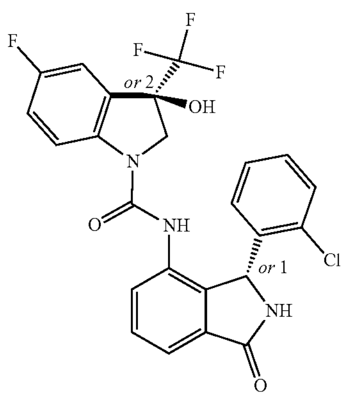 | O[C@]1(CN(C(=O)Nc2cccc3C(=O)N[C@H](c23)c2cccc2Cl)c2ccc(F)cc12)C(F)(F)F | | | E | |
| I-2686 | 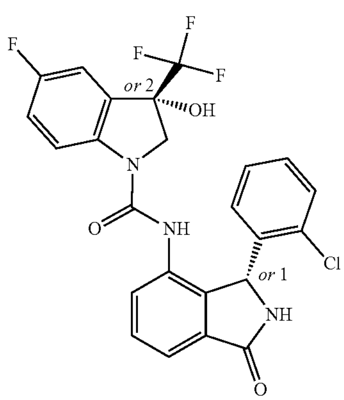 [SMILES: O=C1N[C@@H](c2ccccc2Cl)c2c(NC(=O)N3C[C@](O)(C(F)(F)F)c4cc(F)ccc43)cccc21] | O[C@@]1(CN(C(=O)Nc2cccc3C(=O)N[C@H](c23)c2ccccc2Cl)c2ccc(F)cc12)C(F)(F)F | | | E | |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-2687 | 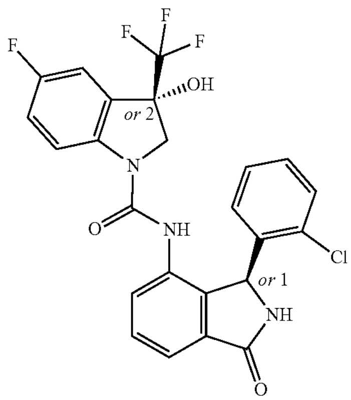 [SMILES: O=C1N[C@H](c2ccccc2Cl)c2c(NC(=O)N3C[C@](O)(C(F)(F)F)c4cc(F)ccc43)cccc21] | O[C@@]1(CN(C(=O)Nc2cccc3C(=O)N[C@@H](c23)c2cccc2Cl)c2ccc(F)cc12)C(F)(F)F | | | D | |
| I-2688 | 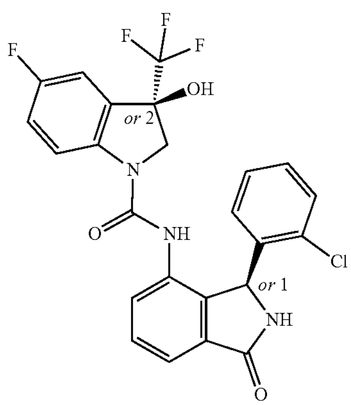 [SMILES: O=C1N[C@H](c2ccccc2Cl)c2c(NC(=O)N3C[C@@](O)(C(F)(F)F)c4cc(F)ccc43)cccc21] | O[C@]1(CN(C(=O)Nc2cccc3C(=O)N[C@@H](c23)c2cccc2C1)c2ccc(F)cc12)C(F)(F)F | | | A | A |
| I-2689 | 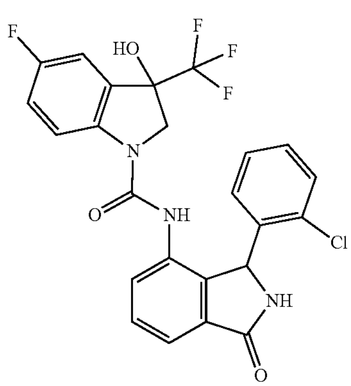 [SMILES: O=C1NC(c2ccccc2Cl)c2c(NC(=O)N3CC(O)(C(F)(F)F)c4cc(F)ccc43)cccc21] | OC1(CN(C(=O)Nc2cccc3C(=O)NC(c23)c2cccc2Cl)c2ccc(F)cc12)C(F)(F)F | (400 MHz, DMSO-d6) δ 9.06 (br s, 1H), 8.75 (s, 0.5H), 8.66 (s, 0.5H), 7.90 (dd, J = 8.7, 4.7 Hz, 0.5H), 7.85 (dd, J = 8.4, 4.5 Hz, 0.5H), 7.59 (t, J = 7.0 Hz, 1H), 7.55 (d, J = 7.4 Hz, 1H), 7.48-7.34 (m, 2H), 7.32-7.17 (m, 5H), 7.17-7.05 (m, 1H), 6.09 (br s, 1H), 4.17 (d, J = 11.9 Hz, 0.5H), 3.97 (d, J = 12.1 Hz, 0.5H), 3.43 (d, J = 11.5 Hz, 0.5H), 3.31 (submerged d, 0.5H). 1:1 mix of diastereomers. | 506.0 | | |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-2690 | 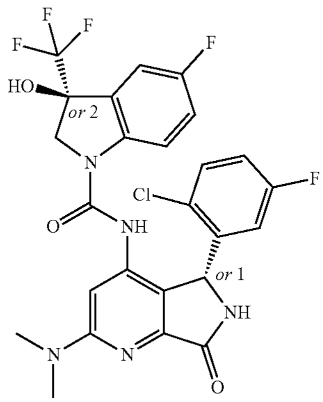 [SMILES: CN(C)c1cc(NC(=O)N2C[C@](O)(C(F)(F)F)c3cc(F)ccc32)c2c(n1)C(=O)N[C@H]2c1cc(F)ccc1Cl] | CN(C)c1cc(NC(=O)N2C[C@@](O)(c3cc(F)ccc23)C(F)(F)Fc2[C@@H](NC(=O)c2n1)cc1cc(F)ccc1Cl | (400 MHz, DMSO-d6) 9.13 (s, 1H), 8.98 (s, 1H), 7.90 (dd, J = 9.1, 4.7 Hz, 1H), 7.41 (s, 1H), 7.34-7.24 (m, 2H), 7.20 (dd, J = 8.1, 2.7 Hz, 1H), 7.08 (td, J = 8.3, 3.1 Hz, 1H), 6.60 (s, 2H), 5.90 (s, 1H), 3.98 (d, J = 12.1 Hz, 1H), 3.52 (d, J = 12.1 Hz, 1H), 3.11 (s, 6H). | 568.4 | A | A |
| I-2691 | 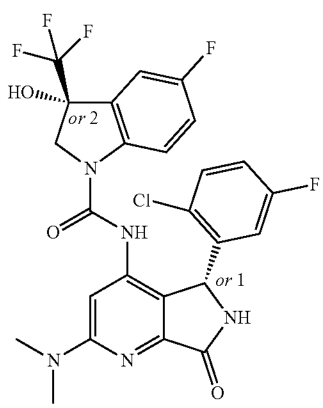 [SMILES: CN(C)c1cc(NC(=O)N2C[C@@](O)(C(F)(F)F)c3cc(F)ccc32)c2c(n1)C(=O)N[C@H]2c1cc(F)ccc1Cl] | CN(C)c1cc(NC(=O)N2C[C@](O)(c3cc(F)cc23)C(F)(F)Fc2[C@@H](NC(=O)c2n1)c1cc(F)ccc1C1 | (400 MHz, DMSO-d6) 9.14 (s, 1H), 8.89 (s, 1H), 7.88 (dd, J = 9.0, 4.6 Hz, 1H), 7.36 (s, 1H), 7.33 (dd, J = 8.8, 5.1 Hz, 1H), 7.32-7.18 (m, 2H), 7.10 (ddd, J = 8.9, 7.8, 3.1 Hz, 1H), 6.68 (s, 1H), 5.91 (s, 1H), 4.21 (d, J = 12.1 Hz, 2H), 3.12 (s, 6H). | 568.4 | D | |
| I-2692 | 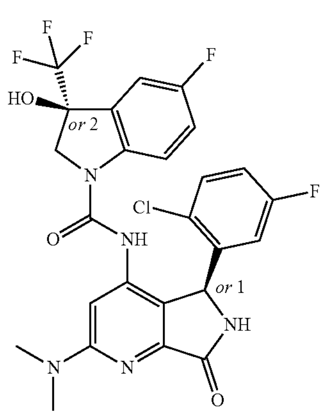 [SMILES: CN(C)c1cc(NC(=O)N2C[C@](O)(C(F)(F)F)c3cc(F)ccc32)c2c(n1)C(=O)N[C@@H]2c1cc(F)ccc1Cl] | CN(C)c1cc(NC(=O)N2C[C@@](O)(c3cc(F)ccc23)C(F)(F)Fc2[C@H](NC(=O)c2n1)c1cc(F)ccc1C1 | (400 MHz, DMSO-d6) 9.14 (s, 1H), 8.90 (s, 1H), 7.88 (dd, J = 9.1, 4.6 Hz, 1H), 7.37 (s, 1H), 7.33 (dd, J = 8.8, 5.2 Hz, 1H), 7.26 (ddd, J = 16.8, 8.4, 2.8 Hz, 2H), 7.21 (d, J = 2.8 Hz, 1H), 7.10 (td, J = 8.3, 3.1 Hz, 1H), 6.74 (s, 1H), 6.68 (s, 1H), 5.92 (s; 1H), 4.21 (d, J = 12.1 Hz, 1H), 3.12 (s, 6H). | 568.4 | E | |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-2693 | 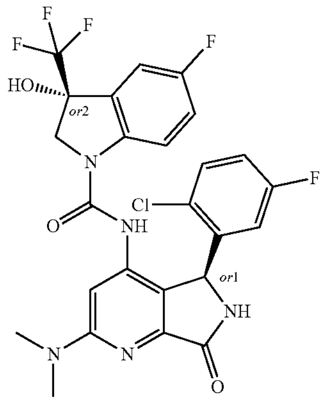 [SMILES: CN(C)c1cc(NC(=O)N2C[C@@](O)(C(F)(F)F)c3cc(F)ccc32)c2c(n1)C(=O)N[C@@H]2c1cc(F)ccc1Cl] | CN(C)c1cc(NC(=O)N2C[C@](O)(c3cc(F)ccc23)C(F)(F)F)c2[C@H](NC(=O)c2n1)cc(F)ccc1Cl | (400 MHz, DMSO-d6) 9.13 (s, 1H), 8.98 (s, 1H), 7.89 (dd, J = 9.1, 4.7 Hz, 1H), 7.40 (s, 1H), 7.34-7.24 (m, 2H), 7.20 (dd, J = 8.1, 2.7 Hz, 1H), 7.07 (ddd, J = 8.8, 7.9, 3.1 Hz, 1H), 6.60 (s, 2H), 5.90 (s, 1H), 3.97 (d, J = 12.0 Hz, 1H), 3.52 (d, J = 12.0 Hz, 1H), 3.11 (s, 6H). | 568.0 | E | |
| I-2694 | 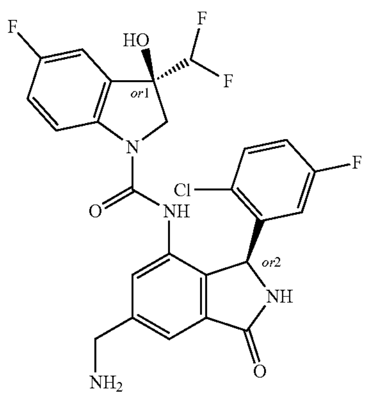 [SMILES: NCc1cc(NC(=O)N2C[C@@](O)(C(F)F)c3cc(F)ccc32)c2c(c1)C(=O)N[C@@H]2c1cc(F)ccc1Cl] | NCc1cc2C(=O)N[C@@H](c2c(NC(=O)N2C[C@@](O)(C(F)F)c3cc(F)ccc23)c1)c1cc(F)ccc1Cl | | 533.3 | A | B |
| I-2695 | 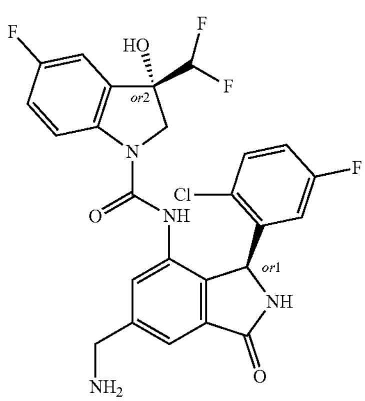 [SMILES: NCc1cc(NC(=O)N2C[C@](O)(C(F)F)c3cc(F)ccc32)c2c(c1)C(=O)N[C@@H]2c1cc(F)ccc1Cl] | NCc1cc2C(=O)N[C@@H](c2c(NC(=O)N2C[C@](O)(C(F)F)c3cc(F)ccc23)c1)c1cc(F)ccc1Cl | | 533.3 | D | |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-2696 | 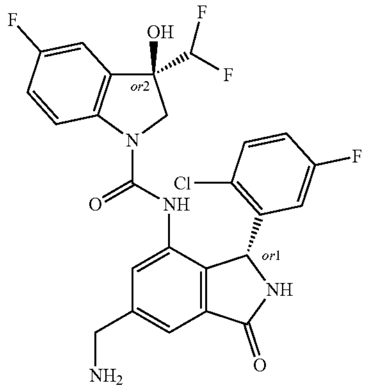 [SMILES: NCc1cc(NC(=O)N2C[C@@](O)(C(F)F)c3cc(F)ccc32)c2c(c1)C(=O)N[C@H]2c1cc(F)ccc1Cl] | NCc1cc2C(=O)N[C@H](c2c(NC(=O)N2C[C@@](O)(C(F)F)c3cc(F)ccc23)c1)c1cc(F)ccc1Cl | | 533.3 | D | |
| I-2697 | 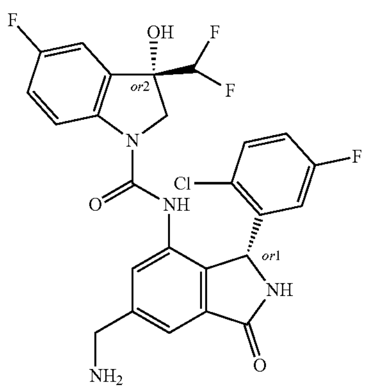 [SMILES: NCc1cc(NC(=O)N2C[C@](O)(C(F)F)c3cc(F)ccc32)c2c(c1)C(=O)N[C@H]2c1cc(F)ccc1Cl] | NCc1cc2C(=O)N[C@H](c2c(NC(=O)N2C[C@](O)(C(F)F)c3cc(F)ccc23)c1)c1cc(F)ccc1Cl | | 533.3 | D | |
| I-2698 | 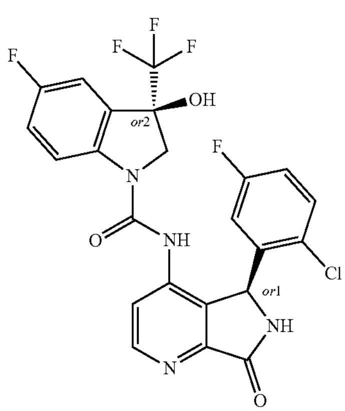 [SMILES: O=C1N[C@H](c2cc(F)ccc2Cl)c2c(NC(=O)N3C[C@@](O)(C(F)(F)F)c4cc(F)ccc43)ccnc21] | O[C@]1(CN(C(=O)Nc2ccnc3C(=O)N[C@@H](c23)c2cc(F)ccc2Cl)c2cc(F)cc12)C(F)(F)F | (400 MHz, DMSO-d6) 9.41 (s, 1H), 9.27 (s, 1H), 8.68 (s, 1H), 7.92 (d, J = 6.8 Hz, 1H), 7.42 (s, 2H), 7.34-7.29 (m, 2H), 7.21 (d, J = 7.5 Hz, 1H), 7.11 (td, J = 8.4, 3.1 Hz, 1H), 6.73 (s, 1H), 6.02 (s, 1H), 3.98 (s, 1H), 3.54 (d, J = 12.2 Hz, 1H). | 525.0 | A | B |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-2699 | 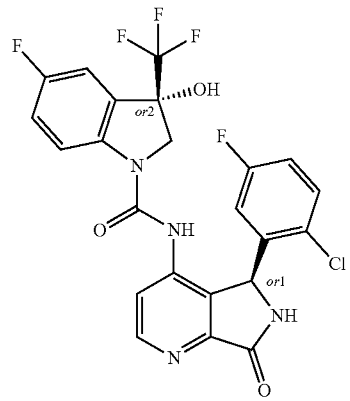 [SMILES: O=C1N[C@H](c2cc(F)ccc2Cl)c2c(NC(=O)N3C[C@](O)(C(F)(F)F)c4cc(F)ccc43)ccnc21] | O[C@@]1(CN(C(=O)Nc2cnc3C(=O)N[C@@H](c23)c2cc(F)cc2Cl)c2ccc(F)cc12)C(F)(F)F | (400 MHz, DMSO-d6) 9.42 (s, 1H), 9.17 (s, 1H), 8.70 (s, 1H), 7.88 (dd, J = 9.2, 4.5 Hz, 1H), 7.49 (d, J = 5.4 Hz, 1H), 7.40-7.32 (m, 2H), 7.28 (t, J = 8.9 Hz, 1H), 7.23 (d, J = 7.8 Hz, 1H), 7.12 (td, J = 8.9, 8.5, 3.1 Hz, 1H), 6.79 (s, 1H), 6.04 (s, 1H), 4.17 (d, J = 12.1 Hz, 1H), 3.37 (d, J = 11.9 Hz, 1H). | 525.0 | D | |
| I-2700 | 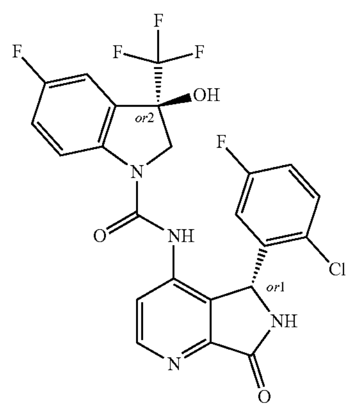 [SMILES: O=C1N[C@@H](c2cc(F)ccc2Cl)c2c(NC(=O)N3C[C@@](O)(C(F)(F)F)c4cc(F)ccc43)ccnc21] | O[C@]1(CN(C(=O)Nc2ccnc3C(=O)N[C@H](c23)c2cc(F)ccc2Cl)c2ccc(F)cc12)C(F)(F)F | (400 MHz, DMSO-d6) 9.42 (s, 1H), 9.18 (s, 1H), 8.70 (d, J = 5.4 Hz, 1H), 7.88 (dd, J = 9.1, 4.6 Hz, 1H), 7.49 (d, J = 5.4 Hz, 1H), 7.40-7.20 (m, 4H), 7.12 (td, J = 8.4, 3.1 Hz, 1H), 6.82 (s, 1H), 6.05 (s, 1H), 4.18 (d, J = 12.1 Hz, 1H), 3.37 (d, J = 12.1 Hz, 1H). | 525.0 | D | |
| I-2701 | 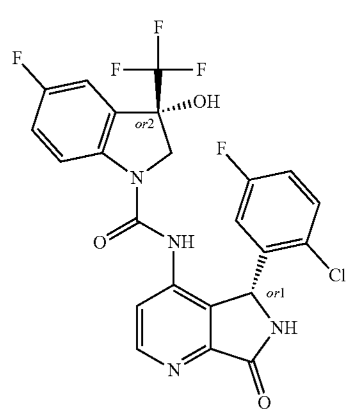 [SMILES: O=C1N[C@@H](c2cc(F)ccc2Cl)c2c(NC(=O)N3C[C@](O)(C(F)(F)F)c4cc(F)ccc43)ccnc21] | O[C@@]1(CN(C(=O)Nc2cnc3C(=O)N[C@H](c23)c2cc(F)cc2Cl)c2cc(F)cc12)C(F)(F)F | (400 MHz, DMSO-d6) 9.42 (s, 1H), 9.27 (s, 1H), 8.70 (d, J = 5.3 Hz, 1H), 7.92 (s, 1H), 7.50-7.40 (m, 1H), 7.40-7.37 (m, 1H), 7.37-7.26 (m, 2H), 7.22 (d, J = 8.4 Hz, 1H), 7.10 (td, J = 8.4, 3.0 Hz, 1H), 6.81 (s, 1H), 6.03 (s, 1H), 4.00 (d, J = 12.1 Hz, 1H), 3.52 (d, J = 12.0 Hz, 1H). | 524.9 | D | |

TABLE 2-continued

Representative Compounds of the Invention with Bioactivity Data.

| Ex. No. | Structure | SMILES | ¹H NMR | MS | ADP-Glo IC$_{50}$ | MCF 10A IC$_{50}$ |
|---|---|---|---|---|---|---|
| I-2702 | 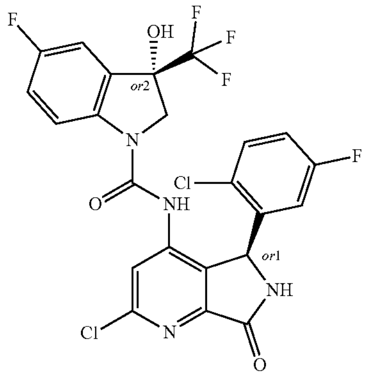 [SMILES: O=C1N[C@H](c2cc(F)ccc2Cl)c2c(NC(=O)N3C[C@](O)(C(F)(F)F)c4cc(F)ccc43)cc(Cl)nc21] | O[C@@]1(CN(C(=O)Nc2cc(Cl)nc3C(=O)N[C@@H](c23)c2cc(F)ccc2Cl)c2ccc(F)cc12)C(F)(F)F | (400 MHz, DMSO-d6) 9.57 (s, 1H), 9.34 (s, 1H), 7.88 (s, 1H), 7.63 (s, 1H), 7.38 (s, 2H), 7.28 (s, 1H), 7.22 (s, 1H), 7.14 (td, J = 8.4, 3.1 Hz, 1H), 7.01-6.03 (s, 1H), 6.04 (s, 1H), 4.06 (s, 1H), 3.45 (s, 1H). | 559.1 | D | |
| I-2703 | 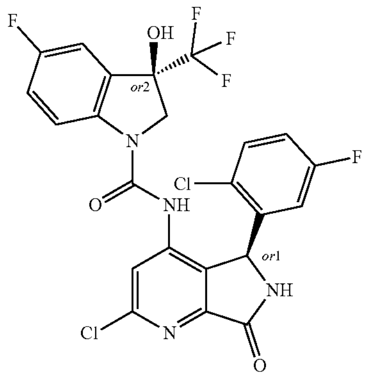 [SMILES: O=C1N[C@H](c2cc(F)ccc2Cl)c2c(NC(=O)N3C[C@@](O)(C(F)(F)F)c4cc(F)ccc43)cc(Cl)nc21] | O[C@]1(CN(C(=O)Nc2cc(Cl)nc3C(=O)N[C@@H](c23)c2cc(F)ccc2Cl)c2ccc(F)cc12)C(F)(F)F | (400 MHz, DMSO-d6) 9.58 (s, 1H), 9.43 (s, 1H), 7.90 (s, 1H), 7.51 (s, 1H), 7.46 (s, 1H), 7.33 (s, 2H), 7.22 (s, 1H), 7.11 (t, J = 7.8 Hz, 1H), 6.27 (s, 2H), 3.90 (s, 1H), 3.58 (s, 1H). | 559.1 | A | A |
| I-2704 | 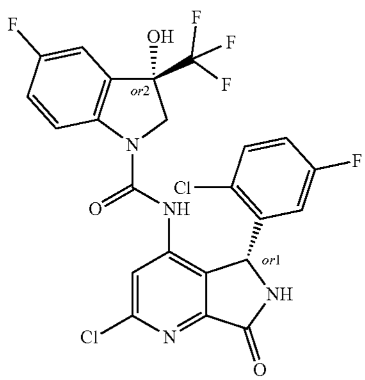 [SMILES: O=C1N[C@@H](c2cc(F)ccc2Cl)c2c(NC(=O)N3C[C@](O)(C(F)(F)F)c4cc(F)ccc43)cc(Cl)nc21] | O[C@@]1(CN(C(=O)Nc2cc(Cl)nc3C(=O)N[C@H](c23)c2cc(F)ccc2Cl)c2ccc(F)cc12)C(F)(F)F | | 559.1 | A | A |
| I-2705 | 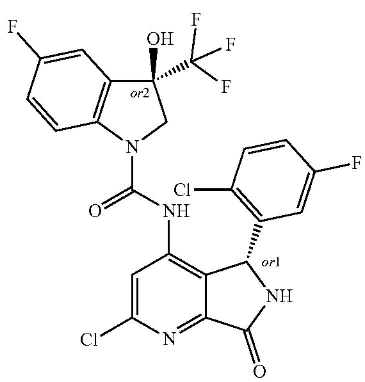 [SMILES: O=C1N[C@@H](c2cc(F)ccc2Cl)c2c(NC(=O)N3C[C@@](O)(C(F)(F)F)c4cc(F)ccc43)cc(Cl)nc21] | O[C@]1(CN(C(=O)Nc2cc(Cl)nc3C(=O)N[C@H](c23)c2cc(F)ccc2Cl)c2ccc(F)cc12)C(F)(F)F | | 559.1 | D | |

TABLE 2-continued

Representative Compounds of the Invention with Bioactivity Data.

| Ex. No. | Structure | SMILES | $^1$H NMR | MS | ADP-Glo IC$_{50}$ | MCF 10A IC$_{50}$ |
|---|---|---|---|---|---|---|
| I-2706 | 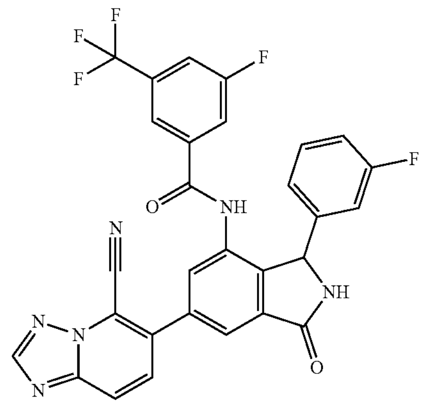 [SMILES: N#Cc1c(-c2cc(NC(=O)c3cc(F)cc(C(F)(F)F)c3)c3c(c2)C(=O)NC3c2cccc(F)c2)ccc2ncnn12] | Fc1ccc(c1)C1NC(=O)c2cc(cc(NC(=O)c3cc(F)cc(c3)C(F)(F)F)c12)-c1ccc2ncnn2c1C#N | | | | |
| I-2707 | 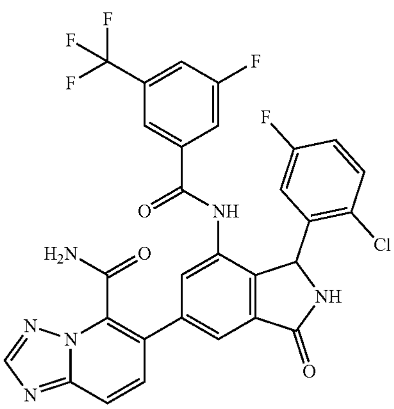 [SMILES: NC(=O)c1c(-c2cc(NC(=O)c3cc(F)cc(C(F)(F)F)c3)c3c(c2)C(=O)NC3c2cc(F)ccc2Cl)ccc2ncnn12] | NC(=O)c1c(ccc2ncnn12)-c1cc2C(=O)NC(c2c(NC(=O)c2cc(F)cc(c2)C(F)(F)F)c1)c1cc(F)ccc1Cl | | | | |

In chemical structures in Table 1 above, and the Examples, below, stereogenic centers are described according to the Enhanced Stereo Representation format (MDL/Biovia, e.g. using labels "on1", "or2", "abs", "and1"). (See, for example, the structures of Compounds I-1, I-2, I-4, I-5, I-292, and I-293.)

In some embodiments, the present invention provides a compound in Table 1, above, wherein the compound is denoted as having an ADP-Glo IC$_{50}$ of "A". In some embodiments, the present invention provides a compound in Table 1, above, wherein the compound is denoted as having an ADP-Glo IC$_{50}$ of "A" or "B". In some embodiments, the present invention provides a compound in Table 1, above, wherein the compound is denoted as having an ADP-Glo IC$_{50}$ of "A" or "B" or "C". In some embodiments, the present invention provides a compound in Table 1, above, wherein the compound is denoted as having an ADP-Glo IC$_{50}$ of "A" or "B" or "C" or "D".

In some embodiments, the present invention provides a compound in Table 1, above, wherein the compound is denoted as having an MCF10A IC$_{50}$ of "A". In some embodiments, the present invention provides a compound in Table 1, above, wherein the compound is denoted as having an MCF10A IC$_{50}$ of "A" or "B". In some embodiments, the present invention provides a compound in Table 1, above, wherein the compound is denoted as having an MCF10A IC$_{50}$ of "A" or "B" or "C". In some embodiments, the present invention provides a compound in Table 1, above, wherein the compound is denoted as having an MCF10A IC$_{50}$ of "A" or "B" or "C" or "D".

In some embodiments, the present invention comprises a compound of formula I selected from those depicted in Table 1, above, or a pharmaceutically acceptable salt, stereoisomer, or mixture of stereoisomers thereof. In some embodiments, the present invention provides a compound of formula I selected from those depicted in Table 1, above, or a pharmaceutically acceptable salt thereof. In some embodiments, the present invention provides a compound of formula I selected from those depicted in Table 1, above.

In some embodiments, the present invention comprises a compound of formula II selected from those depicted in Table 1, above, or a pharmaceutically acceptable salt, stereoisomer, or mixture of stereoisomers thereof. In some embodiments, the present invention provides a compound of formula II selected from those depicted in Table 1, above, or a pharmaceutically acceptable salt thereof. In some embodiments, the present invention provides a compound of formula II selected from those depicted in Table 1, above.

In some embodiments, the present invention comprises a compound of formula III selected from those depicted in Table 1, above, or a pharmaceutically acceptable salt, stereoisomer, or mixture of stereoisomers thereof. In some embodiments, the present invention provides a compound of formula III selected from those depicted in Table 1, above, or a pharmaceutically acceptable salt thereof. In some embodiments, the present invention provides a compound of formula III selected from those depicted in Table 1, above.

In some embodiments, the present invention comprises a compound of formula IV selected from those depicted in Table 1, above, or a pharmaceutically acceptable salt, stereoisomer, or mixture of stereoisomers thereof. In some embodiments, the present invention provides a compound of formula IV selected from those depicted in Table 1, above, or a pharmaceutically acceptable salt thereof. In some embodiments, the present invention provides a compound of formula IV selected from those depicted in Table 1, above.

In some embodiments, the present invention comprises a compound of formula V, VI, VII, VIII, IX, X, XI, XII, XIII, XIV, XV, XVI, XVII, XVIII, XIX, XX, XXI, XXII, XXIII, XXIV, XXV, XXVI, XXVII, XXVIII, XXIX, XXX, XXXI, XXXII, XXXIII, XXXIV, XXXV, XXXVI, XXXVII, XXXVIII, XXXIX, or XXXX, selected from those depicted in Table 1, above, or a pharmaceutically acceptable salt, stereoisomer, or mixture of stereoisomers thereof. In some embodiments, the present invention provides a compound of formula V, VI, VII, VIII, IX, X, XI, XII, XIII, XIV, XV, XVI, XVII, XVIII, XIX, XX, XXI, XXII, XXIII, XXIV, XXV, XXVI, XXVII, XXVIII, XXIX, XXX, XXXI, XXXII, XXXIII, XXXIV, XXXV, XXXVI, XXXVII, XXXVIII, XXXIX, or XXXX, selected from those depicted in Table 1, above, or a pharmaceutically acceptable salt thereof. In some embodiments, the present invention provides a compound of formula V, VI, VII, VIII, IX, X, XI, XII, XIII, XIV, XV, XVI, XVII, XVIII, XIX, XX, XXI, XXII, XXIII, XXIV, XXV, XXVI, XXVII, XXVIII, XXIX, XXX, XXXI, XXXII, XXXIII, XXXIV, XXXV, XXXVI, XXXVII, XXXVIII, XXXIX, or XXXX, selected from those depicted in Table 1, above.

4. General Methods of Providing the Present Compounds

The compounds of this invention may be prepared or isolated, in general, by synthetic and/or semi-synthetic methods known to those skilled in the art, methods illustrated in the following Schemes, and by methods described in detail in the Examples, below. The scope of the disclosure is not to be construed as limited to specific embodiments disclosed in these Schemes, however, which are illustrative only. At least some of the compounds identified herein as "Intermediates", e.g. compounds with numbers preceded by "Int-", are contemplated as compounds of the disclosure.

In the Schemes, it is understood by one skilled in the art of organic synthesis that the functionality present on various portions of the molecule should be compatible with the reagents and reactions proposed. Substituents not compatible with the reaction conditions will be apparent to one skilled in the art, and alternate methods are therefore indicated (for example, use of protecting groups or alternative reactions). Protecting group chemistry and strategy is well known in the art, for example, as described in detail in "Protecting Groups in Organic Synthesis", T. W. Greene and P. G. M. Wuts, 3$^{rd}$ edition, John Wiley & Sons, 1999, the entire contents of which are hereby incorporated by reference. The starting materials for the Schemes are either commercially available or are readily prepared by one skilled in the art of organic synthesis from known materials using standard methods.

General principles of organic chemistry and synthesis, well known in the art, are described in, for example, "Organic Chemistry", Thomas Sorrell, University Science Books, Sausalito: 1999; "March's Advanced Organic Chemistry", 5$^{th}$ Ed., Ed.: Smith, M. B. and March, J., John Wiley & Sons, New York: 2001; and "Comprehensive Organic Synthesis", 2$^{nd}$ Ed., Ed.: Knochel, P. and Molander, G. A., Elsevier, Amsterdam: 2014; the entire contents of each of which are hereby incorporated by reference. For example, certain embodiments below refer to leaving groups. Suitable leaving groups are well known in the art, as described in, for example, the preceding references. Such leaving groups include, but are not limited to, halogen, alkoxy, sulphonyloxy, optionally substituted alkylsulphonyloxy, optionally substituted alkenylsulfonyloxy, optionally substituted arylsulfonyloxy, and diazonium moieties. Examples of suitable leaving groups include chloro, iodo, bromo, fluoro, methanesulfonyl (mesyl), tosyl, triflate, nitro-phenylsulfonyl (nosyl), and bromo-phenylsulfonyl (brosyl).

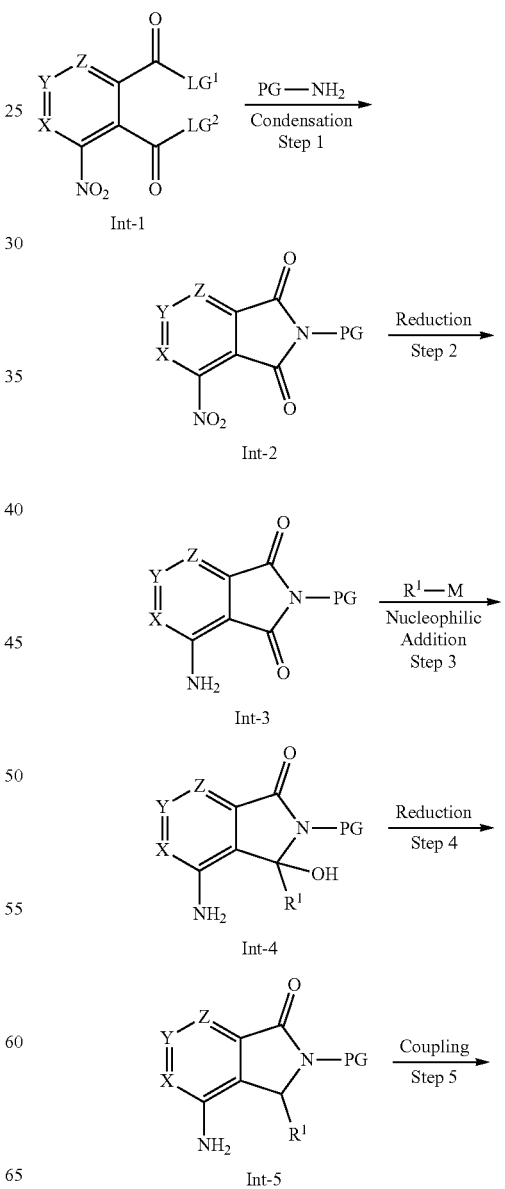

Scheme 1

1751

-continued

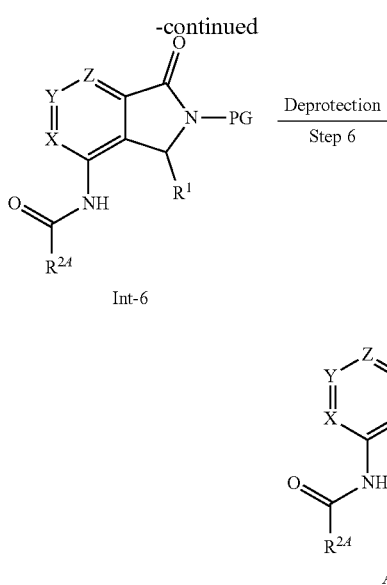

Int-6

| Deprotection |
| Step 6 |

A

In some embodiments, compounds of formula A (i.e. compounds of formula I, wherein Q is CH, and $R^2$ is $—N(H)C(O)—R^{2A}$) are prepared according to the general procedure depicted in Scheme 1, above. In some embodiments, Step 1 comprises the condensation of Int-1 with a primary amine of formula $PG-NH_2$, thereby forming a compound of formula Int-2, wherein X, Y, and Z are as defined in embodiments herein, $LG^1$ and $LG^2$ are leaving groups, and PG is a protecting group. In some embodiments, $LG^1$ and $LG^2$ taken together are —O— (i.e. Int-1 is a bicyclic anhydride). In some embodiments, $LG^1$ and $LG^2$ are Cl. In some embodiments, PG is p-methoxybenzyl (PMB). In some embodiments, PG is 2,4-dimethoxybenzyl (DMB).

In some embodiments, Step 2 comprises the reduction of a compound of formula Int-2, thereby forming a compound of formula Int-3, wherein X, Y, and Z are as defined in embodiments herein and PG is a protecting group. In some embodiments, the reduction is conducted with iron and ammonium chloride.

In some embodiments, Step 3 comprises the nucleophilic addition of an organometallic reagent of formula $R^1$-M with Int-3, thereby forming a compound of formula Int-4, wherein X, Y, Z, and $R^1$ are as defined in embodiments herein and PG is a protecting group. In some embodiments, the organometallic reagent of formula $R^1$-M is a Grignard reagent of formula $R^1$—MgBr or $R^1$—MgCl. In some embodiments, the organometallic reagent of formula $R^1$-M is a Grignard reagent of formula $R^1$—MgBr. In some embodiments, the $R^1$ is phenyl substituted with $r^1$ instances of $R^{1C}$.

In some embodiments, Step 4 comprises the reduction of a compound of formula Int-4, thereby forming a compound of formula Int-5, wherein X, Y, Z, and $R^1$ are as defined in embodiments herein and PG is a protecting group. In some embodiments, the reduction is conducted with a silane and acid. In some embodiments, the reduction is conducted with a trialkylsilane and trifluoroacetic acid.

In some embodiments, Step 5 comprises the coupling of Int-5 with a reagent comprising $R^{2A}$, thereby forming a compound of formula Int-6, wherein X, Y, Z, $R^1$, and $R^{2A}$ are as defined in embodiments herein and PG is a protecting group.

1752

In some embodiments, the reagent comprising $R^{2A}$ is a compound of formula $R^{2A}$—C(O)Cl. In some embodiments, the reagent comprising $R^{2A}$ is a compound of formula $R^{2A}$—C(O)OH, and Step 5 further comprises an amide-coupling reagent. In some embodiments, the amide-coupling reagent is 1-[bis(dimethylamino)methylene]-1H-1,2,3-triazolo[4,5-b]pyridinium 3-oxid hexafluorophosphate (HATU) or tetramethylchloroformamidinium hexafluorophosphate (TCFH) and N-methylimidazole (NMI). In some embodiments, the amide-coupling reagent is tetramethylchloroformamidinium hexafluorophosphate (TCFH) and N-methylimidazole (NMI). In some embodiments, the amide-coupling reagent is 1-[bis(dimethylamino)methylene]-1H-1,2,3-triazolo[4,5-h]pyridinium 3-oxid hexafluorophosphate (HATU).

In some embodiments, the reagent comprising $R^{2A}$ comprises a primary or secondary amine, and Step 5 further comprises a carbonyl-equivalent reagent. In some embodiments, the carbonyl-equivalent reagent is triphosgene.

In some embodiments, Step 6 comprises the deprotection of a compound of formula Int-6, thereby forming a compound of formula A, wherein X, Y, Z, $R^1$, and $R^{2A}$ are as defined in embodiments herein. In some embodiments, the deprotection is conducted with an acid. In some embodiments, the deprotection is conducted with trifluoroacetic acid. In some embodiments, the deprotection is conducted with trifluoroacetic acid and trifluoromethanesulfonic acid. In some embodiments, the deprotection is conducted with an oxidant. In some embodiments, the deprotection is conducted with cerium (IV) ammonium nitrate.

In some embodiments, the order of performing Step 5 and Step 6 is reversed.

Scheme 2

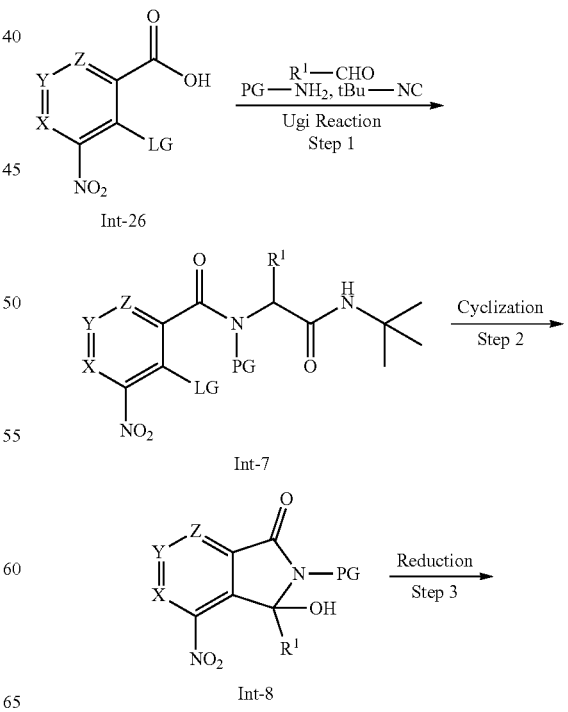

-continued

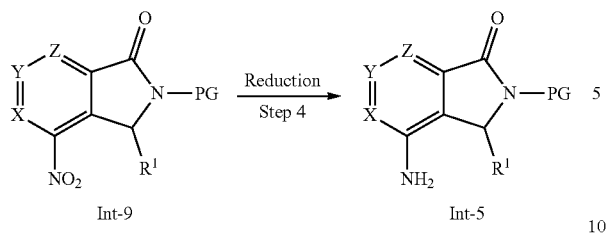

Int-9        Int-5

In some embodiments, compounds of formula Int-5 are prepared according to the general procedure depicted in Scheme 2, above. In some embodiments, Step 1 comprises the Ugi reaction condensation of Int-26 with an aldehyde of formula $R^1$—CHO, a primary amine of formula PG-$NH_2$, and t-butyl isocyanide, thereby forming a compound of formula Int-7, wherein $R^1$, X, Y, and Z are as defined in embodiments herein, LG is a leaving group, and PG is a protecting group. In some embodiments, LG is a halogen. In some embodiments, LG is F. In some embodiments, LG is Cl. In some embodiments, PG is p-methoxybenzyl (PMB). In some embodiments, PG is 2,4-dimethoxybenzyl (DMB).

In some embodiments, Step 2 comprises the cyclization of a compound of formula Int-7, thereby forming a compound of formula Int-8, wherein $R^1$, X, Y, and Z are as defined in embodiments herein and PG is a protecting group. In some embodiments, the cyclization is conducted with a base. In some embodiments, the cyclization is conducted with an organic base. In some embodiments, the cyclization is conducted with 2-(t-butyl)-1,1,3,3-tetramethylguanidine. In some embodiments, the cyclization is conducted with an inorganic base. In some embodiments, the cyclization is conducted with potassium carbonate. In some embodiments, the cyclization is catalyzed by a phase-transfer reagent. In some embodiments, the cyclization is catalyzed by a tetraalkylammonium phase-transfer reagent.

In some embodiments, Step 3 comprises the reduction of a compound of formula Int-8, thereby forming a compound of formula Int-9, wherein $R^1$, X, Y, and Z are as defined in embodiments herein and PG is a protecting group. In some embodiments, the reduction is conducted with a silane and acid. In some embodiments, the reduction is conducted with a trialkylsilane and trifluoroacetic acid.

In some embodiments, Step 4 comprises the reduction of a compound of formula Int-9, thereby forming a compound of formula Int-5, wherein $R^1$, X, Y, and Z are as defined in embodiments herein and PG is a protecting group. In some embodiments, the reduction is conducted with iron and ammonium chloride.

Scheme 3

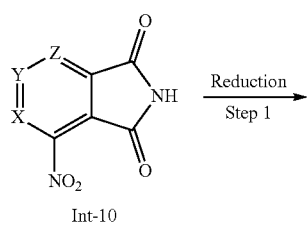

Int-10

-continued

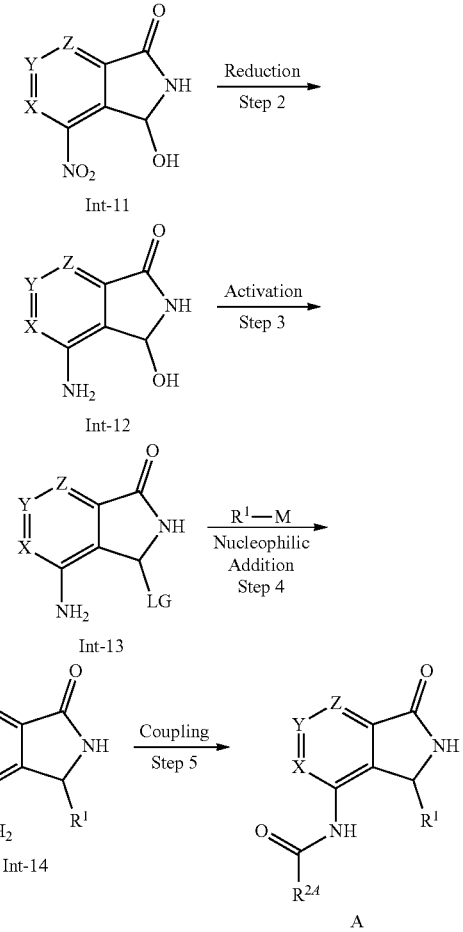

In some embodiments, compounds of formula A (i.e. compounds of formula I, wherein Q is CH, and $R^2$ is —N(H)C(O)—$R^{2A}$) are prepared according to the general procedure depicted in Scheme 4, above. In some embodiments, Step 1 comprises the reduction of a compound of formula Int-10, thereby forming a compound of formula Int-11, wherein X, Y, and Z, are as defined in embodiments herein. In some embodiments, the reduction is conducted with a metal hydride. In some embodiments, the reduction is conducted with sodium borohydride.

In some embodiments, Step 2 comprises the reduction of a compound of formula Int-11, thereby forming a compound of formula Int-12, wherein X, Y, and Z are as defined in embodiments herein. In some embodiments, the reduction is conducted with iron and ammonium chloride.

In some embodiments, Step 3 comprises the activation of a compound of formula Int-12, thereby forming a compound of formula Int-13, wherein X, Y, and Z are as defined in embodiments herein and LG is a leaving group. In some embodiments, the activation is an alcoholysis reaction. In some embodiments, the leaving group is an alkoxy group. In some embodiments, the activation is a methanolysis. In some embodiments, the leaving group is a methoxy group.

In some embodiments, Step 4 comprises the nucleophilic addition of an organometallic reagent of formula $R^1$-M with Int-13, thereby forming a compound of formula Int-14, wherein X, Y, Z, and $R^1$ are as defined in embodiments herein. In some embodiments, the organometallic reagent of formula $R^1$-M is a Grignard reagent of formula $R^1$—MgBr or $R^1$—MgCl.

In some embodiments, Step 5 comprises the coupling of Int-14 with a reagent comprising $R^{2A}$, thereby forming a compound of formula A, wherein X, Y, Z, $R^1$, and $R^{2A}$ are as defined in embodiments herein.

In some embodiments, the reagent comprising $R^2$ is a compound of formula $R^{2A}$—C(O)Cl. In some embodiments, the reagent comprising $R^{2A}$ is a compound of formula $R^{2A}$—C(O)OH, and Step 5 further comprises an amide-coupling reagent. In some embodiments, the amide-coupling reagent is tetramethylchloroformamidinium hexafluorophosphate (TCFH) and N-methylimidazole (NMI) or 1-[bis(dimethylamino)methylene]-1H-1,2,3-triazolo[4,5-b]pyridinium 3-oxid hexafluorophosphate (HATU).

In some embodiments, the reagent comprising $R^{2A}$ comprises a primary or secondary amine, and Step 5 further comprises a carbonyl-equivalent reagent. In some embodiments, the carbonyl-equivalent reagent is triphosgene.

thereby forming a compound of formula Int-17, wherein $R^1$, X, Y, and Z are as defined in embodiments herein, $LG^1$ is a leaving group, and PG is a protecting group. In some embodiments, $LG^2$ is Cl. In some embodiments, the condensation is conducted with a strong base. In some embodiments, the condensation is conducted with butyl lithium. In some embodiments, the condensation is conducted with LHMDS.

In some embodiments, Step 3 comprises the reduction of a compound of formula Int-17, thereby forming a compound of formula Int-18, wherein $R^1$, X, Y, and Z are as defined in embodiments herein, $LG^1$ is a leaving group, and PG is a protecting group. In some embodiments, the reduction is conducted with a silane and acid. In some embodiments, the reduction is conducted with a trialkylsilane and trifluoroacetic acid.

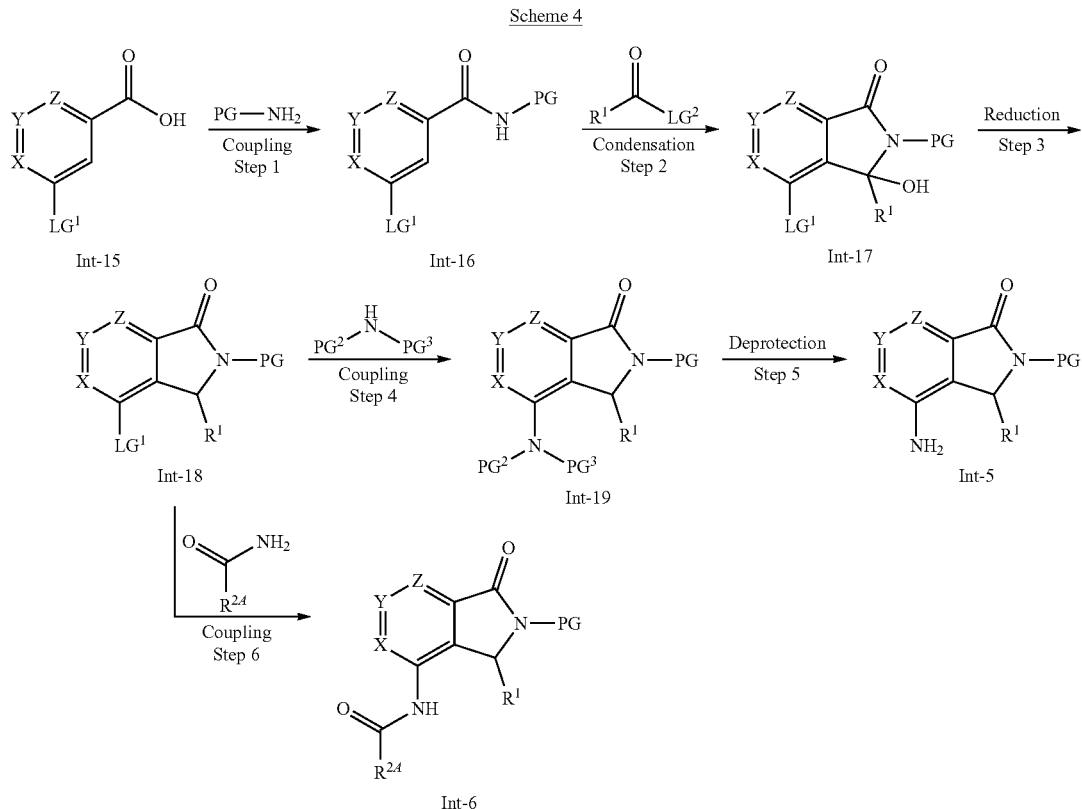

Scheme 4

In some embodiments, compounds of formula Int-5 or Int-6 are prepared according to the general procedure depicted in Scheme 4, above. In some embodiments, Step 1 comprises the coupling of Int-15 with a primary amine of formula PG-NH$_2$, thereby forming a compound of formula Int-16, wherein X, Y, and Z are as defined in embodiments herein, $LG^1$ is a leaving group, and PG is a protecting group. In some embodiments, one or more of X, Y, or Z is nitrogen. In some embodiments, X is nitrogen. In some embodiments, Z is nitrogen.

In some embodiments, $LG^1$ is a halogen. In some embodiments, $LG^1$ is Cl. In some embodiments, PG is 2,4-dimethoxybenzyl (DMB). In some embodiments, PG is p-methoxybenzyl (PMB).

In some embodiments, Step 2 comprises the condensation of Int-16 with a compound of formula $R^1$—C(O)-LG$^2$, In some embodiments, Step 4 comprises the coupling of Int-18 with a compound of formula PG$^2$-N(H)-PG$^3$, thereby forming a compound of formula Int-19, wherein $R^1$, X, Y, and Z are as defined in embodiments herein, and PG, PG$^2$, and PG$^3$ are protecting groups. In some embodiments, PG$^2$ is 2,4-dimethoxybenzyl (DMB). In some embodiments, PG$^2$ is p-methoxybenzyl (PMB). In some embodiments, PG$^3$ is H. In some embodiments, PG$^3$ is 2,4-dimethoxybenzyl (DMB). In some embodiments, PG$^3$ is p-methoxybenzyl (PMB). In some embodiments, PG$^{2A}$-N-PG$^3$ is taken together to represent azide (N$_3$).

In some embodiments, the coupling is conducted with a base. In some embodiments, the coupling is conducted with an organic base. In some embodiments, the coupling is conducted with a trialkylamine base. In some embodiments, the coupling is conducted with an inorganic base. In some embodiments, the coupling is conducted with a transition-metal catalyst. In some embodiments, the coupling is conducted with a palladium catalyst.

In some embodiments, Step 5 comprises the deprotection of a compound of formula Int-19, thereby forming a compound of formula Int-5, wherein $R^1$, X, Y, and Z are as defined in embodiments herein, and PG is a protecting group. In some embodiments, the deprotection is conducted with an acid. In some embodiments, the deprotection is conducted with hydrochloric acid. In some embodiments, the deprotection is conducted with trifluoroacetic acid. In some embodiments, the deprotection is conducted with a reductant (for example, when $PG^2$-N-$PG^3$ is taken together to represent azide). In some embodiments, the deprotection is conducted with a phosphine reductant.

In some embodiments, Step 6 comprises the coupling of Int-18 with a compound of formula $R^{2A}$—C(O)$NH_2$, thereby forming a compound of formula Int-6, wherein $R^1$, $R^{2A}$, X, Y, and Z are as defined in embodiments herein, and PG is a protecting group. In some embodiments, the coupling is a transition-metal-mediated coupling reaction. In some embodiments, the coupling is a Pd-catalyzed coupling reaction.

formula $R^1$—CHO, a primary amine of formula PG-$NH_2$, and t-butyl isocyanide, thereby forming a compound of formula Int-21, wherein $R^1$, X, Y, and Z are as defined in embodiments herein, LG is a leaving group, and PG is a protecting group. In some embodiments, LG is a halogen. In some embodiments, LG is Br. In some embodiments, LG is Cl. In some embodiments, PG is 2,4-dimethoxybenzyl (DMB). In some embodiments, PG is p-methoxybenzyl (PMB).

In some embodiments, Step 2 comprises the cyclization of a compound of formula Int-21, thereby forming a compound of formula Int-22, wherein $R^1$, X, Y, and Z are as defined in embodiments herein, LG is a leaving group, and PG is a protecting group. In some embodiments, the cyclization is conducted with a base. In some embodiments, the cyclization is conducted with an inorganic base. In some embodiments, the cyclization is conducted with sodium hydride. In some embodiments, the cyclization is conducted with potassium carbonate. In some embodiments, the cyclization is catalyzed by a phase-transfer reagent. In some embodiments, the cyclization is catalyzed by a tetraalkylammonium phase-transfer reagent. In some embodiments, the cyclization is conducted with an organic base. In some embodiments, the cyclization is conducted with 2-(t-butyl)-1,1,3,3-tetramethylguanidine.

In some embodiments, Step 3 comprises the reduction of a compound of formula Int-22, thereby forming a compound of formula Int-23, wherein $R^1$, X, Y, and Z are as defined in embodiments herein, LG is a leaving group, and PG is a protecting group. In some embodiments, the reduction is conducted with a silane and a Lewis acid. In some embodiments, the reduction is conducted with a trialkylsilane and trifluoroboron diethyletherate. In some embodiments, the reduction is conducted with a silane and acid. In some embodiments, the reduction is conducted with a trialkylsilane and trifluoroacetic acid.

In some embodiments, Step 4 comprises the coupling of a compound of formula Int-23, thereby forming a compound of formula Int-5, wherein $R^1$, X, Y, and Z are as defined in embodiments herein and PG is a protecting group. In some embodiments, the coupling is a transition-metal-mediated coupling reaction. In some embodiments, the coupling is a Pd-catalyzed coupling reaction. In some embodiments, the coupling is a Pd-catalyzed coupling reaction conducted with benzophenone imine.

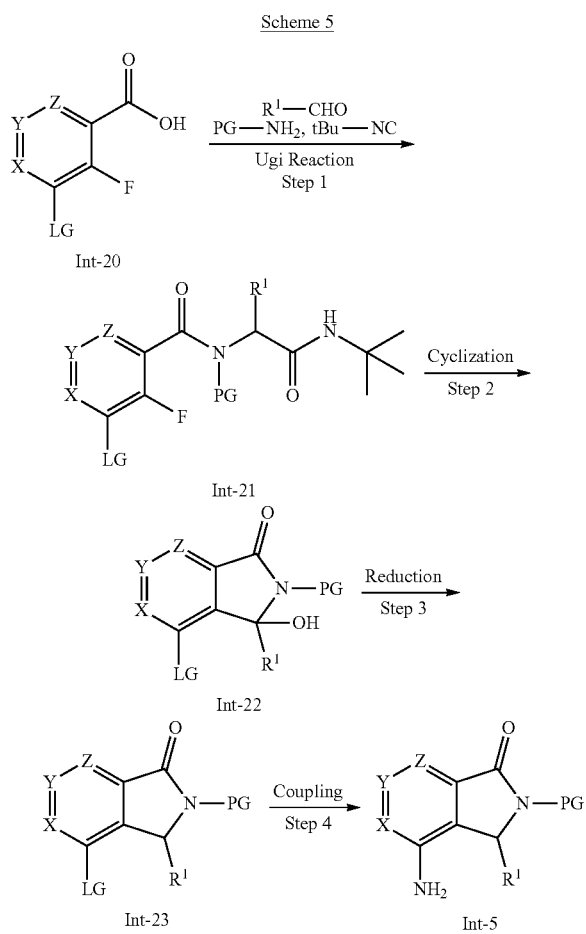

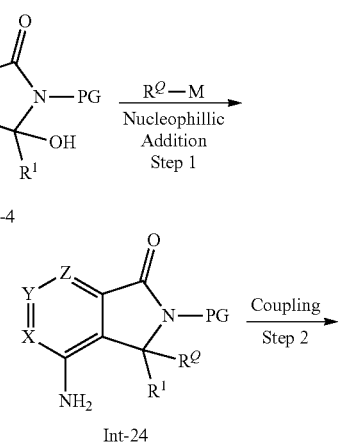

In some embodiments, compounds of formula Int-5 are prepared according to the general procedure depicted in Scheme 5, above. In some embodiments, Step 1 comprises the Ugi reaction condensation of Int-20 with an aldehyde of

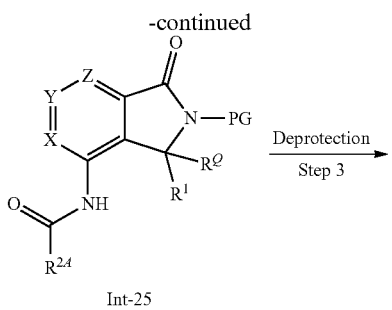

Int-25

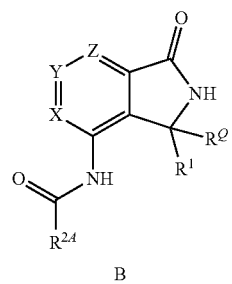

B

In some embodiments, compounds of formula B (i.e. compounds of formula I, wherein Q is $C(R^Q)$, and $R^2$ is $-N(H)C(O)-R^{24}$) are prepared according to the general procedure depicted in Scheme 6, above. In some embodiments, Step 1 comprises the nucleophilic addition of an organometallic reagent of formula $R^Q$-M with Int-4, thereby forming a compound of formula Int-24, wherein X, Y, Z, $R^1$, and $R^Q$ are as defined in embodiments herein and PG is a protecting group. In some embodiments, PG is p-methoxybenzyl (PMB). In some embodiments, PG is 2,4-dimethoxybenzyl (DMB). In some embodiments, the organometallic reagent of formula $R^Q$-M is a Grignard reagent of formula $R^Q$—MgBr or $R^Q$—MgCl. In some embodiments, the nucleophilic addition is conducted with a Lewis acid. In some embodiments, the nucleophilic addition is conducted with trifluoroboron diethyletherate.

In some embodiments, Step 2 comprises the coupling of Int-24 with a reagent comprising $R^{24}$, thereby forming a compound of formula Int-25, wherein X, Y, Z, $R^1$, $R^Q$, and $R^{24}$ are as defined in embodiments herein and PG is a protecting group.

In some embodiments, the reagent comprising $R^A$ is a compound of formula $R^{24}$—C(O)Cl. In some embodiments, the reagent comprising $R^{24}$ is a compound of formula $R^{24}$—C(O)OH, and Step 2 further comprises an amide-coupling reagent. In some embodiments, the amide-coupling reagent is tetramethylchloroformamidinium hexafluorophosphate (TCFH) and N-methylimidazole (NMI). In some embodiments, the amide-coupling reagent is 1-[bis(dimethylamino)methylene]-1H-1,2,3-triazolo[4,5-b]pyridinium 3-oxid hexafluorophosphate (HATU).

In some embodiments, the reagent comprising $R^{24}$ comprises a primary or secondary amine, and Step 2 further comprises a carbonyl-equivalent reagent. In some embodiments, the carbonyl-equivalent reagent is triphosgene.

In some embodiments, Step 3 comprises the deprotection of a compound of formula Int-25, thereby forming a compound of formula B, wherein X, Y, Z, $R^1$, $R^Q$, and $R^{24}$ are as defined in embodiments herein. In some embodiments, the deprotection is conducted with an acid. In some embodiments, the deprotection is conducted with trifluoroacetic acid. In some embodiments, the deprotection is conducted with trifluoroacetic acid and trifluoromethanesulfonic acid.

In some embodiments, the deprotection is conducted with an oxidant. In some embodiments, the deprotection is conducted with cerium (IV) ammonium nitrate.

In some embodiments, the order of performing Step 2 and Step 3 is reversed.

Additional compounds of Formula B may be prepared by conducting nucleophilic addition, as described for Step 1 of Scheme 6 above, instead of the reduction Step 3 in Scheme 2, Scheme 4, and Scheme 5 above. The remainder of the steps are conducted as described in Scheme 2, Scheme 4, and Scheme 5 to prepare compounds of Int-24 (rather than Int-5) or Int-25 (rather than Int-6).

Scheme 7

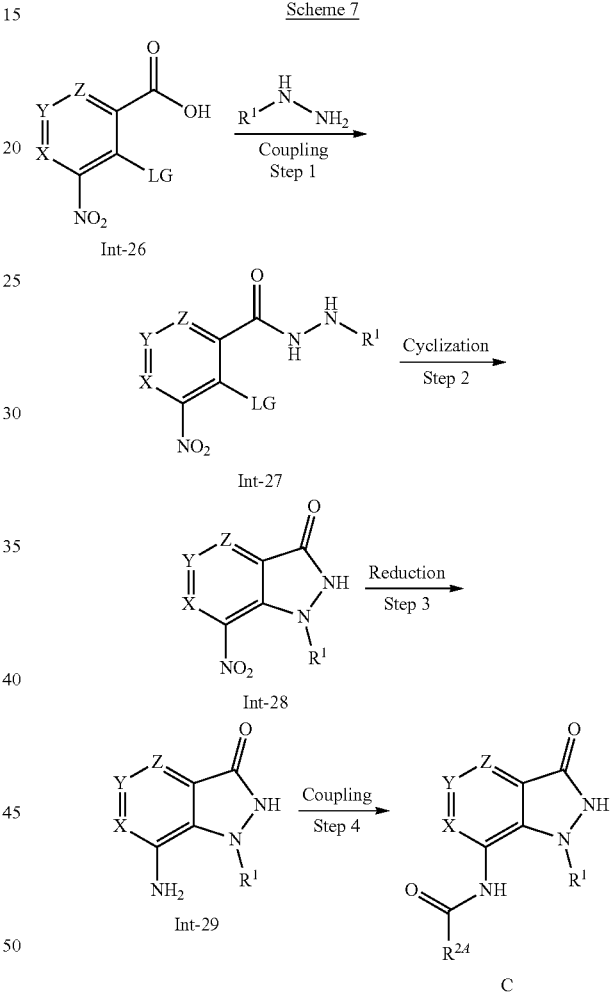

In some embodiments, compounds of formula C (i.e. compounds of formula I, wherein Q is N, and $R^2$ is $-N(H)C(O)-R^{24}$) are prepared according to the general procedure depicted in Scheme 7, above. In some embodiments, Step 1 comprises the coupling of Int-26 with a hydrazine of formula $R^1$—N(H)—NH$_2$, thereby forming a compound of formula Int-27, wherein $R^1$, X, Y, and Z are as defined in embodiments herein and LG is a leaving group. In some embodiments, LG is a halogen. In some embodiments, LG is Cl. In some embodiments, LG is F. In some embodiments, Step 5 further comprises an amide-coupling reagent. In some embodiments, the amide-coupling reagent is 1-[bis(dimethylamino)methylene]-1H-1,2,3-triazolo[4,5-b]pyridinium 3-oxid hexafluorophosphate (HATU).

In some embodiments, Step 2 comprises the cyclization of a compound of formula Int-27, thereby forming a compound of formula Int-28, wherein $R^1$, X, Y, and Z are as defined in embodiments herein. In some embodiments, the cyclization is conducted with a base. In some embodiments, the cyclization is conducted with an inorganic base. In some embodiments, the cyclization is conducted with potassium tert-butoxide. In some embodiments, the cyclization is conducted with potassium carbonate. In some embodiments, the cyclization is catalyzed by a phase-transfer reagent. In some embodiments, the cyclization is catalyzed by a tetraalkylammonium phase-transfer reagent. In some embodiments, the cyclization is conducted with an organic base. In some embodiments, the cyclization is conducted with 2-(t-butyl)-1,1,3,3-tetramethylguanidine.

In some embodiments, Step 3 comprises the reduction of a compound of formula Int-28, thereby forming a compound of formula Int-29, wherein $R^1$, X, Y, and Z are as defined in embodiments herein. In some embodiments, the reduction is conducted with iron and ammonium chloride.

In some embodiments, Step 4 comprises the coupling of Int-29 with a reagent comprising $R^{2A}$, thereby forming a compound of formula C, wherein X, Y, Z, $R^1$, and $R^{2A}$ are as defined in embodiments herein.

In some embodiments, the reagent comprising $R^{2A}$ is a compound of formula $R^{2A}$—C(O)Cl. In some embodiments, the reagent comprising $R^{2A}$ is a compound of formula $R^{2A}$—C(O)OH, and Step 4 further comprises an amide-coupling reagent. In some embodiments, the amide-coupling reagent is tetramethylchloroformamidinium hexafluorophosphate (TCFH) and N-methylimidazole (NMI). In some embodiments, the amide-coupling reagent is 1-[bis(dimethylamino)methylene]-1H-1,2,3-triazolo[4,5-b]pyridinium 3-oxid hexafluorophosphate (HATU).

In some embodiments, the reagent comprising $R^{2A}$ comprises a primary or secondary amine, and Step 4 further comprises a carbonyl-equivalent reagent. In some embodiments, the carbonyl-equivalent reagent is triphosgene.

In some embodiments, the coupling of Step 4 also results in acylation of the indazalonyl nitrogen atom. In said embodiments, the undesired acyl substituent may be selectively removed under basic conditions. Accordingly, in some embodiments, the coupling of Step 4 is followed by treatment of the product with a base, thereby forming a compound of Formula C, wherein X, Y, Z, $R^1$, and $R^{2A}$ are as defined in embodiments herein.

In some embodiments, the coupling of Step 4 is followed by treatment of the product with an inorganic base in an alcohol solvent. In some embodiments, the coupling of Step 4 is followed by treatment with potassium carbonate in methanol.

Functional Group Transformations

In some embodiments, the synthesis of compounds of formula I further comprises a functional group transformation. Functional group transformations are well known in the art, as described in, for example, "Organic Chemistry", Thomas Sorrell, University Science Books, Sausalito: 1999; "March's Advanced Organic Chemistry", $5^{th}$ Ed., Ed.: Smith, M. B. and March, J., John Wiley & Sons, New York: 2001; and "Comprehensive Organic Synthesis", $2^{nd}$ Ed., Ed.: Knochel, P. and Molander, G. A., Elsevier, Amsterdam: 2014.

In some embodiments, the functional group transformation is conducted on Int-5. In some embodiments, the functional group transformation is conducted on Int-6. In some embodiments, the functional group transformation is conducted on a compound of formula A. In some embodiments, the functional group transformation is conducted on Int-14. In some embodiments, the functional group transformation is conducted on Int-24. In some embodiments, the functional group transformation is conducted on Int-25. In some embodiments, the functional group transformation is conducted on a compound of formula B. In some embodiments, the functional group transformation is conducted on Int-28. In some embodiments, the functional group transformation is conducted on Int-29. In some embodiments, the functional group transformation is conducted on a compound of formula C.

In some embodiments, when X, Y, or Z is carbon substituted with a halogen, the synthesis of compounds of formula I further comprises a functional group transformation of the halogen. In some embodiments, the halogen is bromine.

In some embodiments, the functional group transformation is a transition-metal-mediated coupling reaction. In some embodiments, the functional group transformation is a Suzuki coupling. In some embodiments, the functional group transformation is a Ni-mediated photoredox coupling. In some embodiments, the functional group transformation is a Pd-mediated C—N coupling. In some embodiments, the functional group transformation is a Stille coupling. In some embodiments, the functional group transformation is a Pd-mediated cyanation. In some embodiments, the functional group transformation is a Heck coupling. In some embodiments, the functional group transformation is a carbonylation. In some embodiments, the carbonylation is conducted in the presence of an alcohol and forms an ester. In some embodiments, the carbonylation is conducted in the presence of an amine and forms an amide. In some embodiments, the carbonylation is Pd-catalyzed. In some embodiments, the carbonylation is Co-mediated.

In some embodiments, when X, Y, or Z is carbon substituted with a group comprising an alkene, the synthesis of compounds of formula I further comprises a functional group transformation of the alkene. In some embodiments, the functional group transformation is an oxidation of the alkene. In some embodiments, the functional group transformation is a hydroboration of the alkene. In some embodiments, the functional group transformation is a dihydroxylation of the alkene. In some embodiments, the functional group transformation is an oxidative cleavage of the alkene. In some embodiments, the functional group transformation is a reduction of the alkene.

In some embodiments, when X, Y, or Z is carbon substituted with a group comprising an ester, the synthesis of compounds of formula 1 further comprises a functional group transformation of the ester. In some embodiments, the functional group transformation is a reduction of the ester to an alcohol. In some embodiments, the functional group transformation is a saponifcation of the ester to a carboxylic acid. In some embodiments, the resulting carboxylic acid is further converted to an amide. In some embodiments, the functional group transformation is a cyclopropanation of the ester.

In some embodiments, when X, Y, or Z is carbon substituted with a group comprising an aldehyde or ketone, the synthesis of compounds of formula I further comprises a functional group transformation of the aldehyde or ketone. In some embodiments, the functional group transformation is a nucleophilic addition to the aldehyde or ketone. In some embodiments, the functional group transformation is an organometallic addition to the aldehyde or ketone. In some embodiments, the functional group transformation is a Grignard addition to the aldehyde or ketone. In some embodiments, the functional group transformation is a reduction of the aldehyde or ketone to an alcohol. In some embodiments, the functional group transformation is a reductive amination of the aldehyde or ketone.

5. Uses, Formulation, and Administration

Pharmaceutically Acceptable Compositions

According to another embodiment, the invention provides a composition comprising a compound of this invention, or a pharmaceutically acceptable derivative thereof, and a pharmaceutically acceptable carrier, adjuvant, or vehicle. In some embodiments, the invention provides a pharmaceutical composition comprising a compound of this invention, and a pharmaceutically acceptable carrier. The amount of compound in compositions of this invention is such that is effective to measurably inhibit a PI3Kα protein kinase, or a mutant thereof, in a biological sample or in a patient. In certain embodiments, the amount of compound in compositions of this invention is such that it is effective to measurably inhibit a PI3Kα protein kinase, or a mutant thereof, in a biological sample or in a patient. In certain embodiments, a composition of this invention is formulated for administration to a patient in need of such composition. In some embodiments, a composition of this invention is formulated for oral administration to a patient.

The terms "subject" and "patient," as used herein, means an animal (i.e., a member of the kingdom animal), preferably a mammal, and most preferably a human. In some embodiments, the subject is a human, mouse, rat, cat, monkey, dog, horse, or pig. In some embodiments, the subject is a human. In some embodiments, the subject is a mouse, rat, cat, monkey, dog, horse, or pig.

The term "pharmaceutically acceptable carrier, adjuvant, or vehicle" refers to a non-toxic carrier, adjuvant, or vehicle that does not destroy the pharmacological activity of the compound with which it is formulated. Pharmaceutically acceptable carriers, adjuvants or vehicles that may be used in the compositions of this invention include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

A "pharmaceutically acceptable derivative" means any non-toxic salt, ester, salt of an ester or other derivative of a compound of this invention that, upon administration to a recipient, is capable of providing, either directly or indirectly, a compound of this invention or an inhibitorily active metabolite or residue thereof.

As used herein, the term "inhibitorily active metabolite or residue thereof" means that a metabolite or residue thereof is also an inhibitor of a PI3Kα protein kinase, or a mutant thereof.

Compositions of the present invention may be administered orally, parenterally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques. Preferably, the compositions are administered orally, intraperitoneally or intravenously.

Sterile injectable forms of the compositions of this invention may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium.

For this purpose, any bland fixed oil may be employed including synthetic mono- or diglycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents that are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation.

Pharmaceutically acceptable compositions of this invention may be orally administered in any orally acceptable dosage form including, but not limited to, capsules, tablets, aqueous suspensions or solutions. In the case of tablets for oral use, carriers commonly used include lactose and corn starch. Lubricating agents, such as magnesium stearate, are also typically added. For oral administration in a capsule form, useful diluents include lactose and dried cornstarch. When aqueous suspensions are required for oral use, the active ingredient is combined with emulsifying and suspending agents. If desired, certain sweetening, flavoring or coloring agents may also be added.

Alternatively, pharmaceutically acceptable compositions of this invention may be administered in the form of suppositories for rectal or vaginal administration. These can be prepared by mixing the agent with a suitable non-irritating excipient that is solid at room temperature but liquid at rectal or vaginal temperature and therefore will melt in the rectum or vagina to release the drug. Such materials include cocoa butter, beeswax and polyethylene glycols.

Pharmaceutically acceptable compositions of this invention may also be administered topically, especially when the target of treatment includes areas or organs readily accessible by topical application, including diseases of the eye, the skin, or the lower intestinal tract. Suitable topical formulations are readily prepared for each of these areas or organs.

Topical application for the lower intestinal tract can be effected in a rectal suppository formulation (see above) or in a suitable enema formulation. Topically-transdermal patches may also be used.

For topical applications, provided pharmaceutically acceptable compositions may be formulated in a suitable ointment containing the active component suspended or dissolved in one or more carriers. Carriers for topical administration of compounds of this invention include, but are not limited to, mineral oil, liquid petrolatum, white petrolatum, propylene glycol, polyoxyethylene, polyoxypropylene compound, emulsifying wax and water. Alternatively, provided pharmaceutically acceptable compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

For ophthalmic use, provided pharmaceutically acceptable compositions may be formulated as micronized suspensions in isotonic, pH adjusted sterile saline, or, preferably, as solutions in isotonic, pH adjusted sterile saline, either with or without a preservative such as benzylalkonium chloride. Alternatively, for ophthalmic uses, the pharmaceutically acceptable compositions may be formulated in an ointment such as petrolatum.

Pharmaceutically acceptable compositions of this invention may also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

Preferably, pharmaceutically acceptable compositions of this invention are formulated for oral administration. Such formulations may be administered with or without food. In some embodiments, pharmaceutically acceptable compositions of this invention are administered without food. In other embodiments, pharmaceutically acceptable compositions of this invention are administered with food.

The amount of compounds of the present invention that may be combined with the carrier materials to produce a composition in a single dosage form will vary depending upon the patient treated, the particular mode of administration. Preferably, provided compositions should be formulated so that a dosage of between 0.01-100 mg/kg body weight/day of the inhibitor can be administered to a patient receiving these compositions.

It should also be understood that a specific dosage and treatment regimen for any particular patient will depend upon a variety of factors, including the activity of the specific compound employed, the age, body weight, general health, sex, diet, time of administration, rate of excretion, drug combination, and the judgment of the treating physician and the severity of the particular disease being treated. The amount of a compound of the present invention in the composition will also depend upon the particular compound in the composition.

The precise dose to be employed in the compositions will also depend on the route of administration, and should be decided according to the judgment of the practitioner and each subject's circumstances. In specific embodiments of the disclosure, suitable dose ranges for oral administration of the compounds of the disclosure are generally about 1 mg/day to about 1000 mg/day. In some embodiments, the oral dose is about 1 mg/day to about 800 mg/day. In some embodiments, the oral dose is about 1 mg/day to about 500 mg/day. In some embodiments, the oral dose is about 1 mg/day to about 250 mg/day. In some embodiments, the oral dose is about 1 mg/day to about 100 mg/day. In some embodiments, the oral dose is about 5 mg/day to about 50 mg/day. In some embodiments, the oral dose is about 5 mg/day. In some embodiments, the oral dose is about 10 mg/day. In some embodiments, the oral dose is about 20 mg/day. In some embodiments, the oral dose is about 30 mg/day. In some embodiments, the oral dose is about 40 mg/day. In some embodiments, the oral dose is about 50 mg/day. In some embodiments, the oral dose is about 60 mg/day. In some embodiments, the oral dose is about 70 mg/day. In some embodiments, the oral dose is about 100 mg/day. It will be recognized that any of the dosages listed herein may constitute an upper or lower dosage range, and may be combined with any other dosage to constitute a dosage range comprising an upper and lower limit.

In some embodiments, pharmaceutically acceptable compositions contain a provided compound and/or a pharmaceutically acceptable salt thereof at a concentration ranging from about 0.01 to about 90 wt %, about 0.01 to about 80 wt %, about 0.01 to about 70 wt %, about 0.01 to about 60 wt %, about 0.01 to about 50 wt %, about 0.01 to about 40 wt %, about 0.01 to about 30 wt %, about 0.01 to about 20 wt %, about 0.01 to about 2.0 wt %, about 0.01 to about 1 wt %, about 0.05 to about 0.5 wt %, about 1 to about 30 wt %, or about 1 to about 20 wt %.

The composition can be formulated as a solution, suspension, ointment, or a capsule, and the like. The pharmaceutical composition can be prepared as an aqueous solution and can contain additional components, such as preservatives, buffers, tonicity agents, antioxidants, stabilizers, viscosity-modifying ingredients and the like.

Pharmaceutically acceptable carriers are well-known to those skilled in the art, and include, e.g., adjuvants, diluents, excipients, fillers, lubricants and vehicles. In some embodiments, the carrier is a diluent, adjuvant, excipient, or vehicle. In some embodiments, the carrier is a diluent, adjuvant, or excipient. In some embodiments, the carrier is a diluent or adjuvant. In some embodiments, the carrier is an excipient.

Examples of pharmaceutically acceptable carriers may include, e.g., water or saline solution, polymers such as polyethylene glycol, carbohydrates and derivatives thereof, oils, fatty acids, or alcohols. Non-limiting examples of oils as pharmaceutical carriers include oils of petroleum, animal, vegetable or synthetic origin, such as peanut oil, soybean oil, mineral oil, sesame oil and the like. The pharmaceutical carriers may also be saline, gum acacia, gelatin, starch paste, tale, keratin, colloidal silica, urea, and the like. In addition, auxiliary, stabilizing, thickening, lubricating and coloring agents may be used. Other examples of suitable pharmaceutical carriers are described in e.g., Remington's: The Science and Practice of Pharmacy, 22nd Ed. (Allen, Loyd V., Jr ed., Pharmaceutical Press (2012)); Modem Pharmaceutics, $5^{th}$ Ed. (Alexander T. Florence, Juergen Siepmann, CRC Press (2009)); Handbook of Pharmaceutical Excipients, $7^{th}$ Ed. (Rowe, Raymond C.; Sheskey, Paul J.; Cook, Walter G.; Fenton, Marian E. eds., Pharmaceutical Press (2012)) (each of which hereby incorporated by reference in its entirety).

The pharmaceutically acceptable carriers employed herein may be selected from various organic or inorganic materials that are used as materials for pharmaceutical formulations and which are incorporated as analgesic agents, buffers, binders, disintegrants, diluents, emulsifiers, excipients, extenders, glidants, solubilizers, stabilizers, suspending agents, tonicity agents, vehicles and viscosity-increasing agents. Pharmaceutical additives, such as antioxidants, aromatics, colorants, flavor-improving agents, preservatives, and sweeteners, may also be added. Examples of acceptable pharmaceutical carriers include carboxymethyl cellulose, crystalline cellulose, glycerin, gum arabic, lactose, magnesium stearate, methyl cellulose, powders, saline, sodium alginate, sucrose, starch, talc and water, among others. In some embodiments, the term "pharmaceutically acceptable" means approved by a regulatory agency of the Federal or a state government or listed in the U.S. Pharmacopeia or other generally recognized pharmacopeia for use in animals, and more particularly in humans.

Surfactants such as, e.g., detergents, are also suitable for use in the formulations. Specific examples of surfactants include polyvinylpyrrolidone, polyvinyl alcohols, copolymers of vinyl acetate and of vinylpyrrolidone, polyethylene glycols, benzyl alcohol, mannitol, glycerol, sorbitol or polyoxyethylenated esters of sorbitan; lecithin or sodium carboxymethylcellulose; or acrylic derivatives, such as methacrylates and others, anionic surfactants, such as alkaline stearates, in particular sodium, potassium or ammonium stearate; calcium stearate or triethanolamine stearate; alkyl sulfates, in particular sodium lauryl sulfate and sodium cetyl sulfate; sodium dodecylbenzenesulphonate or sodium dioctyl sulphosuccinate; or fatty acids, in particular those derived from coconut oil, cationic surfactants, such as water-soluble quaternary ammonium salts of formula $N^+R'R''R'''R''''Y^-$, in which the R radicals are identical or different optionally hydroxylated hydrocarbon radicals and $Y^-$ is an anion of a strong acid, such as halide, sulfate and sulfonate anions; cetyltrimethylammonium bromide is one of the cationic surfactants which can be used, amine salts of formula $N^+R'R''R'''$, in which the R radicals are identical or different optionally hydroxylated hydrocarbon radicals; octadecylamine hydrochloride is one of the cationic surfactants which can be used, non-ionic surfactants, such as optionally polyoxyethylenated esters of sorbitan, in particular Polysorbate 80, or polyoxyethylenated alkyl ethers; polyethylene glycol stearate, polyoxyethylenated derivatives of castor oil, polyglycerol esters, polyoxyethylenated fatty alcohols, polyoxyethylenated fatty acids or copolymers of ethylene oxide and of propylene oxide, amphoteric surfactants, such as substituted lauryl compounds of betaine.

Suitable pharmaceutical carriers may also include excipients such as starch, glucose, lactose, sucrose, gelatin, malt, rice, flour, chalk, silica gel, sodium stearate, glycerol monostearate, talc, sodium chloride, dried skim milk, glycerol, propylene, glycol, polyethylene glycol 300, water, ethanol, polysorbate 20, and the like. The present compositions, if desired, may also contain wetting or emulsifying agents, or pH buffering agents.

Tablets and capsule formulations may further contain one or more adjuvants, binders, diluents, disintegrants, excipients, fillers, or lubricants, each of which are known in the art. Examples of such include carbohydrates such as lactose or sucrose, dibasic calcium phosphate anhydrous, corn starch, mannitol, xylitol, cellulose or derivatives thereof, microcrystalline cellulose, gelatin, stearates, silicon dioxide, talc, sodium starch glycolate, acacia, flavoring agents, preservatives, buffering agents, disintegrants, and colorants. Orally administered compositions may contain one or more optional agents such as, e.g., sweetening agents such as fructose, aspartame or saccharin; flavoring agents such as peppermint, oil of wintergreen, or cherry; coloring agents; and preservative agents, to provide a pharmaceutically palatable preparation.

Uses of Compounds and Pharmaceutically Acceptable Compositions

Compounds and compositions described herein are generally useful for the inhibition of a kinase or a mutant thereof. In some embodiments, the kinase inhibited by the compounds and compositions described herein is a phosphatidylinositol 3-kinase (PI3K). In some embodiments, the kinase inhibited by the compounds and compositions described herein is one or more of a PI3Kα, PI3Kδ, and PI3Kγ. In some embodiments, the kinase inhibited by the compounds and compositions described herein is a PI3Kα. In some embodiments, the kinase inhibited by the compounds and compositions described herein is a PI3Kα containing at least one of the following mutations: H1047R, E542K, and E545K.

Compounds or compositions of the disclosure can be useful in applications that benefit from inhibition of PI3K enzymes. For example, PI3K inhibitors of the present invention are useful for the treatment of cellular proliferative diseases generally. Compounds or compositions of the disclosure can be useful in applications that benefit from inhibition of PI3Kα enzymes. For example, PI3Kα inhibitors of the present invention are useful for the treatment of cellular proliferative diseases generally.

Aberrant regulation of PI3K, which often increases survival through Aid activation, is one of the most prevalent events in human cancer and has been shown to occur at multiple levels. The tumor suppressor gene PTEN, which dephosphorylates phosphoinositides at the 3' position of the inositol ring, and in so doing antagonizes PI3K activity, is functionally deleted in a variety of tumors. In other tumors, the genes for the p110 alpha isoform, PIK3CA, and for Akt are amplified, and increased protein expression of their gene products has been demonstrated in several human cancers. Furthermore, mutations and translocation of p85 alpha that serve to up-regulate the p85-p110 complex have been described in human cancers. Finally, somatic missense mutations in PIK3CA that activate downstream signaling pathways have been described at significant frequencies in a wide diversity of human cancers (Kang et el., Proc. Natl. Acad. Sci. USA 102:802 (2005); Samuels et al., Science 304:554 (2004); Samuels et al., Cancer Cell 7:561-573 (2005)). These observations show that deregulation of phosphoinositol-3 kinase, and the upstream and downstream components of this signaling pathway, is one of the most common deregulations associated with human cancers and proliferative diseases (Parsons et al., Nature 436:792 (2005); Hennessey at el., Nature Rev. Drug Disc. 4:988-1004 (2005)).

The activity of a compound utilized in this invention as an inhibitor of a PI3K kinase, for example, a PI3Kα, or a mutant thereof, may be assayed in vitro, in vivo or in a cell line. In vitro assays include assays that determine inhibition of either the phosphorylation activity and/or the subsequent functional consequences, or ATPase activity of an activated PI3Kα, or a mutant thereof. Alternative in vitro assays quantitate the ability of the inhibitor to bind to a a PI3Kα. Inhibitor binding may be measured by radiolabeling the inhibitor prior to binding, isolating the inhibitor/PI3Kα complex and determining the amount of radiolabel bound. Alternatively, inhibitor binding may be determined by running a competition experiment where new inhibitors are incubated with a PI3Kα bound to known radioligands. Representative in vitro and in vivo assays useful in assaying a PI3Kα inhibitor include those described and disclosed in the patent and scientific publications described herein. Detailed conditions for assaying a compound utilized in this invention as an inhibitor of a PI3Kα, or a mutant thereof, are set forth in the Examples below.

Treatment of Disorders

Provided compounds are inhibitors of PI3Kα and are therefore useful for treating one or more disorders associated with activity of PI3Kα or mutants thereof. Thus, in certain embodiments, the present invention provides a method of treating a PI3Kα-mediated disorder in a subject, comprising administering a therapeutically effective amount of a compound of the present invention, or a pharmaceutically acceptable salt thereof, or a pharmaceutically acceptable composition of either of the foregoing, to a subject in need thereof. In certain embodiments, the present invention provides a method of treating a PI3Kα-mediated disorder in a subject comprising administering a therapeutically effective amount of a compound of the present invention, or a pharmaceutically acceptable composition thereof, to a subject in need thereof. In some embodiments, the subject has a mutant PI3Kα. In some embodiments, the subject has PI3Kα containing at least one of the following mutations: H1047R, E542K, and E545K.

As used herein, the term "PI3Kα-mediated" disorders, diseases, and/or conditions means any disease or other deleterious condition in which PI3Kα or a mutant thereof is known to play a role. Accordingly, another embodiment of the present invention relates to treating or lessening the severity of one or more diseases in which PI3Kα, or a mutant thereof, is known to play a role. Such PI3Kα-mediated disorders include, but are not limited to, cellular proliferative disorders (e.g. cancer). In some embodiments, the PI3Kα-mediated disorder is a disorder mediated by a mutant PI3Kα. In some embodiments, the PI3Kα-mediated disorder is a disorder mediated by a PI3Kα containing at least one of the following mutations: H1047R, E542K, and E545K.

In some embodiments, the present invention provides a method for treating a cellular proliferative disease, said method comprising administering to a patient in need thereof a therapeutically effective amount of a compound of the present invention, or a pharmaceutically acceptable salt thereof, or a pharmaceutically acceptable composition of either of the foregoing. In some embodiments, the present invention provides a method for treating a cellular proliferative disease, said method comprising administering to a patient in need thereof, a therapeutically effective amount of a compound of the present invention, or a pharmaceutically acceptable composition thereof.

In some embodiments, the method of treatment comprises the steps of: i) identifying a subject in need of such treatment; (ii) providing a disclosed compound, or a pharmaceutically acceptable salt thereof; and (iii) administering said provided compound in a therapeutically effective amount to treat, suppress and/or prevent the disease state or condition in a subject in need of such treatment. In some embodiments, the subject has a mutant PI3Kα. In some embodiments, the subject has PI3Kα containing at least one of the following mutations: H1047R, E542K, and E545K.

In some embodiments, the method of treatment comprises the steps of: i) identifying a subject in need of such treatment; (ii) providing a composition comprising a disclosed compound, or a pharmaceutically acceptable salt thereof, and (iii) administering said composition in a therapeutically effective amount to treat, suppress and/or prevent the disease state or condition in a subject in need of such treatment. In some embodiments, the subject has a mutant PI3Kα. In some embodiments, the subject has PI3Kα containing at least one of the following mutations: H1047R, E542K, and E545K.

Another aspect of the invention provides a compound according to the definitions herein, or a pharmaceutically acceptable salt thereof, or a pharmaceutical composition of either of the foregoing, for use in the treatment of a disorder described herein. Another aspect of the invention provides the use of a compound according to the definitions herein, or a pharmaceutically acceptable salt thereof, or a pharmaceutical composition of either of the foregoing, for the treatment of a disorder described herein. Similarly, the invention provides the use of a compound according to the definitions herein, or a pharmaceutically acceptable salt thereof, for the preparation of a medicament for the treatment of a disorder described herein.

Cellular Proliferative Diseases

In some embodiments, the disorder is a cellular proliferative disease. In some embodiments, the cellular proliferative disease is cancer. In some embodiments, the cancer is a tumor. In some embodiments, the cancer is a solid tumor. In some embodiments, the cellular proliferative disease is a tumor and/or cancerous cell growth. In some embodiments, the cellular proliferative disease is a tumor. In some embodiments, the cellular proliferative disease is a solid tumor. In some embodiments, the cellular proliferative disease is a cancerous cell growth.

In some embodiments, the cancer is selected from sarcoma; lung; bronchus; prostate; breast (including sporadic breast cancers and sufferers of Cowden disease); pancreas; gastrointestinal; colon; rectum; carcinoma; colon carcinoma; adenoma; colorectal adenoma; thyroid; liver; intrahepatic bile duct; hepatocellular; adrenal gland; stomach; gastric; glioma; glioblastoma; endometrial; melanoma; kidney; renal pelvis; urinary bladder; uterine corpus; uterine cervix; vagina; ovary (including clear cell ovarian cancer); multiple myeloma; esophagus; a leukemia; acute myelogenous leukemia; chronic myelogenous leukemia; lymphocytic leukemia; myeloid leukemia; brain; a carcinoma of the brain; oral cavity and pharynx; larynx; small intestine; non-Hodgkin lymphoma; villous colon adenoma; a neoplasia; a neoplasia of epithelial character; lymphoma; a mammary carcinoma; basal cell carcinoma; squamous cell carcinoma; actinic keratosis; neck; head; polycythemia vera; essential thrombocythemia; myelofibrosis with myeloid metaplasia; and Waldenstrom macroglobulinemia.

In some embodiments, the cancer is selected from lung; bronchus; prostate; breast (including sporadic breast cancers and Cowden disease); pancreas; gastrointestinal; colon; rectum; thyroid; liver; intrahepatic bile duct; hepatocellular; adrenal gland; stomach; gastric; endometrial; kidney; renal pelvis; urinary bladder; uterine corpus; uterine cervix; vagina; ovary (including clear cell ovarian cancer); esophagus; a leukemia; acute myelogenous leukemia; chronic myelogenous leukemia; lymphocytic leukemia; myeloid leukemia; brain; oral cavity and pharynx; larynx; small intestine; neck; and head. In some embodiments, the cancer is selected from sarcoma; carcinoma; colon carcinoma; adenoma; colorectal adenoma; glioma; glioblastoma; melanoma; multiple myeloma; a carcinoma of the brain; non-Hodgkin lymphoma; villous colon adenoma; a neoplasia; a neoplasia of epithelial character; lymphoma; a mammary carcinoma; basal cell carcinoma; squamous cell carcinoma; actinic keratosis; polycythemia vera; essential thrombocythemia; myelofibrosis with myeloid metaplasia; and Waldenstrom macroglobulinemia.

In some embodiments, the cancer is selected from lung; bronchus; prostate; breast (including sporadic breast cancers and Cowden disease); pancreas; gastrointestinal; colon; rectum; thyroid; liver; intrahepatic bile duct; hepatocellular; adrenal gland; stomach; gastric; endometrial; kidney; renal pelvis; urinary bladder; uterine corpus; uterine cervix; vagina; ovary (including clear cell ovarian cancer); esophagus; brain; oral cavity and pharynx; larynx; small intestine; neck; and head. In some embodiments, the cancer is a leukemia. In some embodiments, the cancer is acute myclogenous leukemia; chronic myclogenous leukemia; lymphocytic leukemia; or myeloid leukemia.

In some embodiments, the cancer is breast cancer (including sporadic breast cancers and Cowden disease). In some embodiments, the cancer is breast cancer. In some embodiments, the cancer is ER+/HER2– breast cancer. In some embodiments, the cancer is ER+/HER2– breast cancer, and the subject is intolerant to, or ineligible for, treatment with alpelisib. In some embodiments, the cancer is sporadic breast cancer. In some embodiments, the cancer is Cowden disease.

In some embodiments, the cancer is ovarian cancer. In some embodiments, the ovarian cancer is clear cell ovarian cancer.

In some embodiments, the cellular proliferative disease has mutant PI3Kα. In some embodiments, the cancer has mutant PI3Kα. In some embodiments, the breast cancer has mutant PI3Kα. In some embodiments, the ovarian cancer has mutant PI3Kα. In some embodiments, the clear cell ovarian cancer has mutant PI3Kα.

In some embodiments, the cellular proliferative disease has PI3Kα containing at least one of the following mutations: H1047R, E542K, and E545K. In some embodiments, the cancer has PI3Kα containing at least one of the following mutations: H1047R, E542K, and E545K. In some embodiments, the breast cancer has PI3Kα containing at least one of the following mutations: H1047R, E542K, and E545K. In some embodiments, the ovarian cancer has PI3Kα containing at least one of the following mutations: H1047R, E542K, and E545K. In some embodiments, the clear cell ovarian cancer has PI3Kα containing at least one of the following mutations: H1047R, E542K, and E545K.

In some embodiments, the cancer is adenoma; carcinoma; sarcoma; glioma; glioblastoma; melanoma; multiple myeloma; or lymphoma. In some embodiments, the cancer is a colorectal adenoma or avillous colon adenoma. In some embodiments, the cancer is colon carcinoma; a carcinoma of the brain; a mammary carcinoma; basal cell carcinoma; or a squamous cell carcinoma. In some embodiments, the cancer is a neoplasia or a neoplasia of epithelial character. In some embodiments, the cancer is non-Hodgkin lymphoma. In some embodiments, the cancer is actinic keratosis; polycythemia vera; essential thrombocythemia; myelofibrosis with myeloid metaplasia; or Waldenstrom macroglobulinemia.

In some embodiments, the cellular proliferative disease displays overexpression or amplification of PI3Kα, somatic mutation of PIK3CA, germline mutations or somatic mutation of PTEN, or mutations and translocation of p85α that serve to up-regulate the p85-p110 complex. In some embodiments, the cellular proliferative disease displays overexpression or amplification of PI3Kα. In some embodiments, the cellular proliferative disease displays somatic mutation of PIK3CA. In some embodiments, the cellular proliferative disease displays germline mutations or somatic mutation of PTEN. In some embodiments, the cellular proliferative disease displays mutations and translocation of p85α that serve to up-regulate the p85-p110 complex.

Additional Disorders

In some embodiments, the PI3Kα-mediated disorder is selected from the group consisting of: polycythemia vera, essential thrombocythemia, myelofibrosis with myeloid metaplasia, asthma, COPD, ARDS, PROS (PI3K-related overgrowth syndrome), venous malformation, Loffler's syndrome, eosinophilic pneumonia, parasitic (in particular metazoan) infestation (including tropical eosinophilia), bronchopulmonary aspergillosis, polyarteritis nodosa (including Churg-Strauss syndrome), eosinophilic granuloma, eosinophil-related disorders affecting the airways occasioned by drug-reaction, psoriasis, contact dermatitis, atopic dermatitis, alopecia greata, erythema multiforme, dermatitis herpetiformis, scleroderma, vitiligo, hypersensitivity angiitis, urticaria, bullous pemphigoid, lupus erythematosus, pemphisus, epidermolysis bullosa acquisita, autoimmune haematogical disorders (e.g. haemolytic anaemia, aplastic anaemia, pure red cell anaemia and idiopathic thrombocytopenia), systemic lupus erythematosus, polychondritis, Wegener granulomatosis, dermatomyositis, chronic active hepatitis, myasthenia gravis, Steven-Johnson syndrome, idiopathic sprue, autoimmune inflammatory bowel disease (e.g. ulcerative colitis and Crohn's disease), endocrine opthalmopathy, Graves' disease, sarcoidosis, alveolitis, chronic hypersensitivity pneumonitis, multiple sclerosis, primary biliary cirrhosis, uveitis (anterior and posterior), interstitial lung fibrosis, psoriatic arthritis, glomerulonephritis, cardiovascular diseases, atherosclerosis, hypertension, deep venous thrombosis, stroke, myocardial infarction, unstable angina, thromboembolism, pulmonary embolism, thrombolytic diseases, acute arterial ischemia, peripheral thrombotic occlusions, and coronary artery disease, reperfusion injuries, retinopathy, such as diabetic retinopathy or hyperbaric oxygen-induced retinopathy, and conditions characterized by elevated intraocular pressure or secretion of ocular aqueous humor, such as glaucoma.

In some embodiments, the PI3Kα-mediated disorder is polycythemia vera, essential thrombocythemia, or myelofibrosis with myeloid metaplasia. In some embodiments, the PI3Kα-mediated disorder is asthma, COPD, ARDS, PROS (PI3K-related overgrowth syndrome), venous malformation, Loffler's syndrome, eosinophilic pneumonia, parasitic (in particular metazoan) infestation (including tropical cosinophilia), or bronchopulmonary aspergillosis. In some embodiments, the PI3Kα-mediated disorder is polyarteritis nodosa (including Churg-Strauss syndrome), cosinophilic granuloma, cosinophil-related disorders affecting the airways occasioned by drug-reaction, psoriasis, contact dermatitis, atopic dermatitis, alopecia greata, erythema multiforme, dermatitis herpetiformis, or scleroderma. In some embodiments, the PI3Kα-mediated disorder is vitiligo, hypersensitivity angiitis, urticaria, bullous pemphigoid, lupus erythematosus, pemphisus, epidermolysis bullosa acquisita, or autoimmune haematogical disorders (e.g. haemolytic anaemia, aplastic anaemia, pure red cell anaemia and idiopathic thrombocytopenia). In some embodiments, the PI3Kα-mediated disorder is systemic lupus erythematosus, polychondritis, scleroderma, Wegener granulomatosis, dermatomyositis, chronic active hepatitis, myasthenia gravis, Steven-Johnson syndrome, idiopathic sprue, or autoimmune inflammatory bowel disease (e.g. ulcerative colitis and Crohn's disease).

In some embodiments, the PI3Kα-mediated disorder is endocrine opthalmopathy, Graves' disease, sarcoidosis, alveolitis, chronic hypersensitivity pneumonitis, multiple sclerosis, primary biliary cirrhosis, uveitis (anterior and posterior), interstitial lung fibrosis, or psoriatic arthritis. In some embodiments, the PI3Kα-mediated disorder is glomerulonephritis, cardiovascular diseases, atherosclerosis, hypertension, deep venous thrombosis, stroke, myocardial infarction, unstable angina, thromboembolism, pulmonary embolism, thrombolytic diseases, acute arterial ischemia, peripheral thrombotic occlusions, and coronary artery disease, or reperfusion injuries. In some embodiments, the PI3Kα-mediated disorder is retinopathy, such as diabetic retinopathy or hyperbaric oxygen-induced retinopathy, and conditions characterized by elevated intraocular pressure or secretion of ocular aqueous humor, such as glaucoma.

Routes of Administration and Dosage Forms

The compounds and compositions, according to the methods of the present invention, may be administered using any amount and any route of administration effective for treating or lessening the severity of the disorder (e.g. a proliferative disorder). The exact amount required will vary from subject to subject, depending on the species, age, and general condition of the subject, the severity of the infection, the particular agent, its mode of administration, and the like. Compounds of the invention are preferably formulated in unit dosage form for ease of administration and uniformity of dosage. The expression "unit dosage form" as used herein refers to a physically discrete unit of agent appropriate for the patient to be treated. It will be understood, however, that the total daily usage of the compounds and compositions of the present invention will be decided by the attending physician within the scope of sound medical judgment. The specific effective dose level for any particular patient or organism will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed, and like factors well known in the medical arts.

Pharmaceutically acceptable compositions of this invention can be administered to humans and other animals orally, rectally, parenterally, intracisternally, intravaginally, intraperitoneally, topically (as by powders, ointments, or drops), bucally, as an oral or nasal spray, or the like. In certain embodiments, the compounds of the invention may be administered orally or parenterally at dosage levels of about 0.01 mg/kg to about 50 mg/kg and preferably from about 1 mg/kg to about 25 mg/kg, of subject body weight per day, one or more times a day, to obtain the desired therapeutic effect.

Liquid dosage forms for oral administration include, but are not limited to, pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

Injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a compound of the present invention, it is often desirable to slow the absorption of the compound from subcutaneous or intramuscular injection. This may be accomplished by the use of a liquid suspension of crystalline or amorphous material with poor water solubility. The rate of absorption of the compound then depends upon its rate of dissolution that, in turn, may depend upon crystal size and crystalline form. Alternatively, delayed absorption of a parenterally administered compound form is accomplished by dissolving or suspending the compound in an oil vehicle. Injectable depot forms are made by forming microencapsule matrices of the compound in biodegradable polymers such as polylactide-polyglycolide. Depending upon the ratio of compound to polymer and the nature of the particular polymer employed, the rate of compound release can be controlled. Examples of other biodegradable polymers include poly(orthoesters) and poly(anhydrides). Depot injectable formulations are also prepared by entrapping the compound in liposomes or microemulsions that are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes. Solid compositions of a similar type may also be employed as fillers in soft and hard-filled gelatin capsules using such excipients as lactose or milk sugar as well as high molecular weight polyethylene glycols and the like.

The active compounds can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, ear drops, and eye drops are also contemplated as being within the scope of this invention. Additionally, the present invention contemplates the use of transdermal patches, which have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

Dosage Amounts and Regimens

In accordance with the methods of the present disclosure, the compounds of the disclosure are administered to the subject in a therapeutically effective amount, e.g., to reduce or ameliorate symptoms of the disorder in the subject. This amount is readily determined by the skilled artisan, based upon known procedures, including analysis of titration curves established in vivo and methods and assays disclosed herein.

In some embodiments, the methods comprise administration of a therapeutically effective dosage of the compounds of the disclosure. In some embodiments, the therapeutically effective dosage is at least about 0.0001 mg/kg body weight, at least about 0.001 mg/kg body weight, at least about 0.01 mg/kg body weight, at least about 0.05 mg/kg body weight, at least about 0.1 mg/kg body weight, at least about 0.25 mg/kg body weight, at least about 0.3 mg/kg body weight, at least about 0.5 mg/kg body weight, at least about 0.75 mg/kg body weight, at least about 1 mg/kg body weight, at least about 2 mg/kg body weight, at least about 3 mg/kg body weight, at least about 4 mg/kg body weight, at least about 5 mg/kg body weight, at least about 6 mg/kg body weight, at least about 7 mg/kg body weight, at least about 8 mg/kg body weight, at least about 9 mg/kg body weight, at least about 10 mg/kg body weight, at least about 15 mg/kg body weight, at least about 20 mg/kg body weight, at least about 25 mg/kg body weight, at least about 30 mg/kg body weight, at least about 40 mg/kg body weight, at least about 50 mg/kg body weight, at least about 75 mg/kg body weight, at least about 100 mg/kg body weight, at least about 200 mg/kg body weight, at least about 250 mg/kg body weight, at least about 300 mg/kg body weight, at least about 350 mg/kg body weight, at least about 400 mg/kg body weight, at least about 450 mg/kg body weight, at least about 500 mg/kg body weight, at least about 550 mg/kg body weight, at least about 600 mg/kg body weight, at least about 650 mg/kg body weight, at least about 700 mg/kg body weight, at least about 750 mg/kg body weight, at least about 800 mg/kg body weight, at least about 900 mg/kg body weight, or at least about 1000 mg/kg body weight. It will be recognized that any of the dosages listed herein may constitute an upper or lower dosage range, and may be combined with any other dosage to constitute a dosage range comprising an upper and lower limit.

In some embodiments, the therapeutically effective dosage is in the range of about 0.1 mg to about 10 mg/kg body weight, about 0.1 mg to about 6 mg/kg body weight, about 0.1 mg to about 4 mg/kg body weight, or about 0.1 mg to about 2 mg/kg body weight.

In some embodiments the therapeutically effective dosage is in the range of about 1 to 500 mg, about 2 to 150 mg, about 2 to 120 mg, about 2 to 80 mg, about 2 to 40 mg, about 5 to 150 mg, about 5 to 120 mg, about 5 to 80 mg, about 10 to 150 mg, about 10 to 120 mg, about 10 to 80 mg, about 10 to 40 mg, about 20 to 150 mg, about 20 to 120 mg, about 20 to 80 mg, about 20 to 40 mg, about 40 to 150 mg, about 40 to 120 mg or about 40 to 80 mg.

In some embodiments, the methods comprise a single dosage or administration (e.g., as a single injection or deposition). Alternatively, in some embodiments, the methods comprise administration once daily, twice daily, three times daily or four times daily to a subject in need thereof for a period of from about 2 to about 28 days, or from about 7 to about 10 days, or from about 7 to about 15 days, or longer. In some embodiments, the methods comprise chronic administration. In yet other embodiments, the methods comprise administration over the course of several weeks, months, years or decades. In still other embodiments, the methods comprise administration over the course of several weeks. In still other embodiments, the methods comprise administration over the course of several months.

In still other embodiments, the methods comprise administration over the course of several years. In still other embodiments, the methods comprise administration over the course of several decades.

The dosage administered can vary depending upon known factors such as the pharmacodynamic characteristics of the active ingredient and its mode and route of administration; time of administration of active ingredient; age, sex, health and weight of the recipient; nature and extent of symptoms; kind of concurrent treatment, frequency of treatment and the effect desired; and rate of excretion. These are all readily determined and may be used by the skilled artisan to adjust or titrate dosages and/or dosing regimens.

Inhibition of Protein Kinases

According to one embodiment, the invention relates to a method of inhibiting protein kinase activity in a biological sample comprising the step of contacting said biological sample with a compound of this invention, or a composition comprising said compound. According to another embodiment, the invention relates to a method of inhibiting activity of a PI3K, or a mutant thereof, in a biological sample comprising the step of contacting said biological sample with a compound of this invention, or a composition comprising said compound. According to another embodiment, the invention relates to a method of inhibiting activity of PI3Kα, or a mutant thereof, in a biological sample comprising the step of contacting said biological sample with a compound of this invention, or a composition comprising said compound. In some embodiments, the PI3Kα is a mutant PI3Kα. In some embodiments, the PI3Kα contains at least one of the following mutations: H1047R, E542K, and E545K.

In another embodiment, the invention provides a method of selectively inhibiting PI3Kα over one or both of PI3Kδ and PI3Kγ. In some embodiments, a compound of the present invention is more than 5-fold selective over PI3Kδ and PI3Kγ. In some embodiments, a compound of the present invention is more than 10-fold selective over PI3Kδ and PI3Kγ. In some embodiments, a compound of the present invention is more than 50-fold selective over PI3Kδ and PI3Kγ. In some embodiments, a compound of the present invention is more than 100-fold selective over PI3Kδ and PI3Kγ. In some embodiments, a compound of the present invention is more than 200-fold selective over PI3Kδ and PI3Kγ. In some embodiments, the PI3Kα is a mutant PI3Kα. In some embodiments, the PI3Kα contains at least one of the following mutations: H1047R, E542K, and E545K.

In another embodiment, the invention provides a method of selectively inhibiting a mutant PI3Kγ over a wild-type PI3Kα. In some embodiments, a compound of the present invention is more than 5-fold selective for mutant PI3Kα over wild-type PI3Kα. In some embodiments, a compound of the present invention is more than 10-fold selective for mutant PI3Kα over wild-type PI3Kα. In some embodiments, a compound of the present invention is more than 50-fold selective for mutant PI3Kα over wild-type PI3Kα. In some embodiments, a compound of the present invention is more than 100-fold selective for mutant PI3Kα over wild-type PI3Kα. In some embodiments, a compound of the present invention is more than 200-fold selective for mutant PI3Kα over wild-type PI3Kα. In some embodiments, the mutant PI3Kα contains at least one of the following mutations: H1047R, E542K, and E545K.

The term "biological sample", as used herein, includes, without limitation, cell cultures or extracts thereof; biopsied material obtained from a mammal or extracts thereof; and blood, saliva, urine, feces, semen, tears, or other body fluids or extracts thereof.

Inhibition of activity of a PI3K (for example, PI3Kα, or a mutant thereof) in a biological sample is useful for a variety of purposes that are known to one of skill in the art. Examples of such purposes include, but are not limited to, blood transfusion, organ-transplantation, biological specimen storage, and biological assays.

Another embodiment of the present invention relates to a method of inhibiting protein kinase activity in a patient comprising the step of administering to said patient a compound of the present invention, or a composition comprising said compound.

According to another embodiment, the invention relates to a method of inhibiting activity of a PI3K, or a mutant thereof, in a patient comprising the step of administering to said patient a compound of the present invention, or a composition comprising said compound. In some embodiments, the invention relates to a method of inhibiting activity of PI3Kα, or a mutant thereof, in a patient comprising the step of administering to said patient a compound of the present invention, or a composition comprising said compound. In some embodiments, the PI3Kα is a mutant PI3Kα. In some embodiments, the PI3Kα contains at least one of the following mutations: H1047R, E542K, and E545K.

According to another embodiment, the present invention provides a method for treating a disorder mediated by a PI3K, or a mutant thereof, in a patient in need thereof, comprising the step of administering to said patient a compound according to the present invention or pharmaceutically acceptable composition thereof. In some embodiments, the present invention provides a method for treating a disorder mediated by PI3Kα, or a mutant thereof, in a patient in need thereof, comprising the step of administering to said patient a compound according to the present invention or pharmaceutically acceptable composition thereof. In some embodiments, the PI3Kα is a mutant PI3Kα. In some embodiments, the PI3Kα contains at least one of the following mutations: H1047R, E542K, and E545K.

According to another embodiment, the present invention provides a method of inhibiting signaling activity of PI3Kα, or a mutant thereof, in a subject, comprising administering a therapeutically effective amount of a compound according to the present invention, or a pharmaceutically acceptable composition thereof, to a subject in need thereof. In some embodiments, the present invention provides a method of inhibiting PI3Kα signaling activity in a subject, comprising administering a therapeutically effective amount of a compound according to the present invention, or a pharmaceutically acceptable composition thereof, to a subject in need thereof. In some embodiments, the PI3Kα is a mutant PI3Kα. In some embodiments, the PI3Kα contains at least one of the following mutations: H1047R, E542K, and E545K. In some embodiments, the subject has a mutant PI3Kα. In some embodiments, the subject has PI3Kα containing at least one of the following mutations: H1047R, E542K, and E545K.

The compounds described herein can also inhibit PI3Kα function through incorporation into agents that catalyze the destruction of PI3Kα. For example, the compounds can be incorporated into proteolysis targeting chimeras (PROTACs). A PROTAC is a bifunctional molecule, with one portion capable of engaging an E3 ubiquitin ligase, and the other portion having the ability to bind to a target protein meant for degradation by the cellular protein quality control machinery. Recruitment of the target protein to the specific E3 ligase results in its tagging for destruction (i.e., ubiquitination) and subsequent degradation by the proteasome. Any E3 ligase can be used. The portion of the PROTAC that engages the E3 ligase is connected to the portion of the PROTAC that engages the target protein via a linker which consists of a variable chain of atoms. Recruitment of PI3Kα to the E3 ligase will thus result in the destruction of the PI3Kα protein. The variable chain of atoms can include, for example, rings, heteroatoms, and/or repeating polymeric units. It can be rigid or flexible. It can be attached to the two portions described above using standard techniques in the art of organic synthesis.

Combination Therapies

Depending upon the particular disorder, condition, or disease, to be treated, additional therapeutic agents, that are normally administered to treat that condition, may be administered in combination with compounds and compositions of this invention. As used herein, additional therapeutic agents that are normally administered to treat a particular disease, or condition, are known as "appropriate for the disease, or condition, being treated."

Additionally, PI3K serves as a second messenger node that integrates parallel signaling pathways, and evidence is emerging that the combination of a PI3K inhibitor with inhibitors of other pathways will be useful in treating cancer and cellular proliferative diseases.

Accordingly, in certain embodiments, the method of treatment comprises administering the compound or composition of the invention in combination with one or more additional therapeutic agents. In certain other embodiments, the methods of treatment comprise administering the compound or composition of the invention as the only therapeutic agent.

Approximately 20-30% of human breast cancers overexpress Her-2/neu-ErbB2, the target for the drug trastuzumab. Although trastuzumab has demonstrated durable responses in some patients expressing Her2/neu-ErbB2, only a subset of these patients respond. Recent work has indicated that this limited response rate can be substantially improved by the combination of trastuzumab with inhibitors of PI3K or the PI13K/AKT pathway (Chan et al., Breast Can. Res. Treat. 91:187 (2005), Woods Ignatoski et al., Brit. J. Cancer 82:666 (2000), Nagata et al., Cancer Cell 6:117 (2004)). Accordingly, in certain embodiments, the method of treatment comprises administering the compound or composition of the invention in combination with trastuzumab. In certain embodiments, the cancer is a human breast cancer that overexpresses Her-2/neu-ErbB2.

A variety of human malignancies express activating mutations or increased levels of Her1/EGFR and a number of antibody and small molecule inhibitors have been developed against this receptor tyrosine kinase including tarceva, gefitinib and erbitux. However, while EGFR inhibitors demonstrate anti-tumor activity in certain human tumors (e.g., NSCLC), they fail to increase overall patient survival in all patients with EGFR-expressing tumors. This may be rationalized by the fact that many downstream targets of Her1/EGFR are mutated or deregulated at high frequencies in a variety of malignancies, including the PI3K/Akt pathway.

For example, gefitinib inhibits the growth of an adenocarcinoma cell line in in vitro assays. Nonetheless, subclones of these cell lines can be selected that are resistant to gefitinib that demonstrate increased activation of the PI3/Akt pathway. Down-regulation or inhibition of this pathway renders the resistant sub-clones sensitive to gefitinib (Kokubo et al., Brit. J. Cancer 92:1711 (2005)). Furthermore, in an in vitro model of breast cancer with a cell line that harbors a PTEN mutation and over-expresses EGFR inhibition of both the PI3K/Akt pathway and EGFR produced a synergistic effect (She et al., Cancer Cell 8:287-297 (2005)). These results indicate that the combination of gefitinib and PI3K/Akt pathway inhibitors would be an attractive therapeutic strategy in cancer.

Accordingly, in certain embodiments, the method of treatment comprises administering the compound or composition of the invention in combination with an inhibitor of Her1/EGFR. In certain embodiments, the method of treatment comprises administering the compound or composition of the invention in combination with one or more of tarceva, gefitinib, and erbitux. In certain embodiments, the method of treatment comprises administering the compound or composition of the invention in combination with gefitinib.

In certain embodiments, the cancer expresses activating mutations or increased levels of Her1/EGFR.

The combination of AEE778 (an inhibitor of Her-2/neu/ErbB2, VEGFR and EGFR) and RAD001 (an inhibitor of mTOR, a downstream target of Akt) produced greater combined efficacy that either agent alone in a glioblastoma xenograft model (Goudar et al., Mol. Cancer. Ther. 4:101-112 (2005)).

Anti-estrogens, such as tamoxifen, inhibit breast cancer growth through induction of cell cycle arrest that requires the action of the cell cycle inhibitor p27Kip. Recently, it has been shown that activation of the Ras-Raf-MAP Kinase pathway alters the phosphorylation status of p27Kip such that its inhibitory activity in arresting the cell cycle is attenuated, thereby contributing to anti-estrogen resistance (Donovan, et al, J. Biol. Chem. 276:40888, (2001)). As reported by Donovan et al., inhibition of MAPK signaling through treatment with MEK inhibitor reversed the aberrant phosphorylation status of p27 in hormone refractory breast cancer cell lines and in so doing restored hormone sensitivity. Similarly, phosphorylation of p27Kip by Aid also abrogates its role to arrest the cell cycle (Viglietto et al., Nat. Med. 8:1145 (2002)).

Accordingly, in certain embodiments, the method of treatment comprises administering the compound or composition of the invention in combination with a treatment for a hormone-dependent cancer. In certain embodiments, the method of treatment comprises administering the compound or composition of the invention in combination with tamoxifen. In certain embodiments, the cancer is a hormone dependent cancer, such as breast and prostate cancers. By this use, it is aimed to reverse hormone resistance commonly seen in these cancers with conventional anticancer agents.

In hematological cancers, such as chronic myelogenous leukemia (CML), chromosomal translocation is responsible for the constitutively activated BCR-Abl tyrosine kinase. The afflicted patients are responsive to imatinib, a small molecule tyrosine kinase inhibitor, as a result of inhibition of Abl kinase activity. However, many patients with advanced stage disease respond to imatinib initially, but then relapse later due to resistance-conferring mutations in the Abl kinase domain. In vitro studies have demonstrated that BCR-Abl employs the Ras-Raf kinase pathway to elicit its effects. In addition, inhibiting more than one kinase in the same pathway provides additional protection against resistance-conferring mutations.

Accordingly, in another aspect, the compounds and compositions of the invention are used in combination with at least one additional agent selected from the group of kinase inhibitors, such as imatinib, in the treatment of hematological cancers, such as chronic myelogenous leukemia (CML). By this use, it is aimed to reverse or prevent resistance to said at least one additional agent.

Because activation of the PI3K/Akt pathway drives cell survival, inhibition of the pathway in combination with therapies that drive apoptosis in cancer cells, including radiotherapy and chemotherapy, will result in improved responses (Ghobrial et al., CA Cancer J. Clin 55:178-194 (2005)). As an example, combination of PI3 kinase inhibitor with carboplatin demonstrated synergistic effects in both in vitro proliferation and apoptosis assays as well as in in vivo tumor efficacy in a xenograft model of ovarian cancer (Westfall and Skinner, Mol. Cancer Ther. 4:1764-1771 (2005)).

In some embodiments, the one or more additional therapeutic agents is selected from antibodies, antibody-drug conjugates, kinase inhibitors, immunomodulators, and histone deacetylase inhibitors. Synergistic combinations with PIK3CA inhibitors and other therapeutic agents are described in, for example, Castel et al., Mol. Cell Oncol. (2014)1(3) e963447.

In some embodiments, the one or more additional therapeutic agent is selected from the following agents, or a pharmaceutically acceptable salt thereof: BCR-ABL inhibitors (see e.g. Ultimo et al. Oncotarget (2017) 8 (14) 23213-23227.): e.g. imatinib, inilotinib, nilotinib, dasatinib, bosutinib, ponatinib, bafetinib, danusertib, saracatinib, PF03814735; ALK inhibitors (see e.g. Yang et al. Tumour Biol. (2014) 35 (10) 9759-67): e.g. crizotinib, NVP-TAE684, ceritinib, alectinib, brigatinib, entrecinib, lorlatinib; BRAF inhibitors (see e.g. Silva et al. Mol. Cancer Res. (2014) 12, 447-463): e.g. vemurafenib, dabrafenib; FGFR inhibitors (see e.g. Packer et al. Mol. Cancer Ther. (2017) 16(4) 637-648): e.g. infigratinib, dovitinib, erdafitinib, TAS-120, pemigatinib, BLU-554, AZD4547; FLT3 inhibitors: e.g. sunitinib, midostaurin, tanutinib, sorafenib, lestaurtinib, quizartinib, and crenolanib; MEK Inhibitors (see e.g. Jokinen et al. Ther. Adv. Med. Oncol. (2015) 7(3) 170-180): e.g. trametinib, cobimetinib, binimetinib, selumetinib; ERK inhibitors: e.g. ulixertinib, MK 8353, $L^Y$ 3214996; KRAS inhibitors: e.g. AMG-510, MRTX849, ARS-3248; Tyrosine kinase inhibitors (see e.g. Makhov et al. Mol. Cancer. Ther. (2012) 11(7) 1510-1517): e.g. erlotinib, linifanib, sunitinib, pazopanib; Epidermal growth factor receptor (EGFR) inhibitors (see e.g. She et al. BMC Cancer (2016) 16, 587): gefitnib, osimertinib, cetuximab, panitumumab; HER2 receptor inhibitors (see e.g. Lopez et al. Mol. Cancer Ther. (2015) 14(11) 2519-2526): e.g. trastuzumab, pertuzumab, neratinib, lapatinib, lapatinib; MET inhibitors (see e.g. Hervieu et al. Front. Mol. Biosci. (2018) 5, 86): e.g. crizotinib, cabozantinib; CD20 antibodies: e.g. rituximab, tositumomab, ofatumumab; DNA Synthesis inhibitors: e.g. capecitabine, gemcitabine, nelarabine, hydroxycarbamide; Antineoplastic agents (see e.g. Wang et al. Cell Death & Disease (2018) 9, 739): e.g. oxaliplatin, carboplatin, cisplatin; Immunomodulators: e.g. afutuzumab, lenalidomide, thalidomide, pomalidomide; CD40 inhibitors: e.g. dacetuzumab; Pro-apoptotic receptor agonists (PARAs): e.g. dulanermin; Heat Shock Protein (HSP) inhibitors (see e.g. Chen et al. Oncotarget (2014) 5 (9). 2372-2389): e.g. tanespimycin; Hedgehog antagonists (see e.g. Chaturvedi et al. Oncotarget (2018) 9 (24), 16619-16633): e.g. vismodegib; Proteasome inhibitors (see e.g. Lin et al. it. J. Oncol. (2014) 44 (2), 557-562): e.g. bortezomib; PI3K inhibitors: e.g. pictilisib, dactolisib, alpelisib, buparlisib, taselisib, idelalisib, duvelisib, umbralisib; SHP2 inhibitors (see e.g. Sun et al. Am. J. Cancer Res. (2019) 9 (1), 149-159: e.g. SHP099, RMC-4550, RMC-4630); BCL-2 inhibitors (see e.g. Bojarczuk et al. Blood (2018) 133 (1), 70-80): e.g. venetoclax; Aromatase inhibitors (see e.g. Mayer et al. Clin. Cancer Res. (2019) 25 (10), 2975-2987): exemestane, letrozole, anastrozole, fulvestrant, tamoxifen; mTOR inhibitors (see e.g. Woo et al. Oncogenesis (2017) 6, e385): e.g. temsirolimus, ridaforolimus, everolimus, sirolimus; CTLA-4 inhibitors (see e.g. O'Donnell et al. (2018) 48, 91-103): e.g. tremelimumab, ipilimumab; PD1 inhibitors (see O'Donnell, supra): e.g. nivolumab, pembrolizumab; an immunoadhesin; Other immune checkpoint inhibitors (see e.g. Zappasodi et al. Cancer Cell (2018) 33, 581-598, where the term "immune checkpoint" refers to a group of molecules on the cell surface of CD4 and CD8 T cells. Immune checkpoint molecules include, but are not limited to, Programmed Death 1 (PD-1), Cytotoxic T-Lymphocyte Antigen 4 (CTLA-4), B7H1, B7H4, OX-40, CD 137, CD40, and LAG3. Immunotherapeutic agents which can act as immune checkpoint inhibitors useful in the methods of the present disclosure, include, but are not limited to, inhibitors of PD-L1, PD-L2, CTLA4, TIM3, LAG3, VISTA, BTLA, TIGIT, LAIR1, CD 160, 2B4 and/or TGFR beta): e.g. pidilizumab, AMP-224; PDL1 inhibitors (see e.g. O'Donnell supra): e.g. MSB0010718C; YW243.55.S70, MPDL3280A; MEDI-4736, MSB-0010718C, or MDX-1105; Histone deacetylase inhibitors (HDI, see e.g. Rahmani et al. Clin. Cancer Res. (2014) 20(18), 4849-4860): e.g. vorinostat; Androgen Receptor inhibitors (see e.g. Thomas et al. Mol. Cancer Ther. (2013) 12(11), 2342-2355): e.g. enzalutamide, abiraterone acetate, orteronel, galeterone, seviteronel, bicalutamide, flutamide; Androgens: e.g. fluoxymesterone; CDK4/6 inhibitors (see e.g. Gul et al. Am. J. Cancer Res. (2018) 8(12), 2359-2376): e.g. alvocidib, palbociclib, ribociclib, trilaciclib, abemaciclib.

In some embodiments, the one or more additional therapeutic agent is selected from the following agents: anti-FGFR antibodies; FGFR inhibitors, cytotoxic agents; Estrogen Receptor-targeted or other endocrine therapies, immune-checkpoint inhibitors, CDK inhibitors, Receptor Tyrosine Kinase inhibitors, BRAF inhibitors, MEK inhibitors, other PI3K inhibitors, SHP2 inhibitors, and SRC inhibitors. (See Katoh, Nat. Rev. Clin. Oncol. (2019), 16:105-122; Chae, et al. Oncotarget (2017), 8:16052-16074; Formisano et al., Nat. Comm. (2019), 10:1373-1386; and references cited therein.)

The structure of the active compounds identified by code numbers, generic or trade names may be taken from the actual edition of the standard compendium "The Merck Index" or from databases, e.g. Patents International (e.g. IMS World Publications).

A compound of the current invention may also be used in combination with known therapeutic processes, for example, the administration of hormones or radiation. In certain embodiments, a provided compound is used as a radiosensitizer, especially for the treatment of tumors which exhibit poor sensitivity to radiotherapy.

A compound of the current invention can be administered alone or in combination with one or more other therapeutic compounds, possible combination therapy taking the form of fixed combinations or the administration of a compound of the invention and one or more other therapeutic compounds being staggered or given independently of one another, or the combined administration of fixed combinations and one or more other therapeutic compounds. A compound of the current invention can besides or in addition be administered especially for tumor therapy in combination with chemotherapy, radiotherapy, immunotherapy, phototherapy, surgical intervention, or a combination of these. Long-term therapy is equally possible as is adjuvant therapy in the context of other treatment strategies, as described above. Other possible treatments are therapy to maintain the patient's status after tumor regression, or even chemopreventive therapy, for example in patients at risk.

Those additional agents may be administered separately from an inventive compound-containing composition, as part of a multiple dosage regimen. Alternatively, those agents may be part of a single dosage form, mixed together with a compound of this invention in a single composition. If administered as part of a multiple dosage regime, the two active agents may be submitted simultaneously, sequentially or within a period of time from one another normally within five hours from one another.

As used herein, the term "combination," "combined," and related terms refers to the simultaneous or sequential administration of therapeutic agents in accordance with this invention. For example, a compound of the present invention may be administered with another therapeutic agent simultaneously or sequentially in separate unit dosage forms or together in a single unit dosage form. Accordingly, the present invention provides a single unit dosage form comprising a compound of the current invention, an additional therapeutic agent, and a pharmaceutically acceptable carrier, adjuvant, or vehicle.

The amount of both an inventive compound and additional therapeutic agent (in those compositions which comprise an additional therapeutic agent as described above) that may be combined with the carrier materials to produce a single dosage form will vary depending upon the host treated and the particular mode of administration. Preferably, compositions of this invention should be formulated so that a dosage of between 0.01-100 mg/kg body weight/day of an inventive compound can be administered.

In those compositions which comprise an additional therapeutic agent, that additional therapeutic agent and the compound of this invention may act synergistically. Therefore, the amount of additional therapeutic agent in such compositions will be less than that required in a monotherapy utilizing only that therapeutic agent. In such compositions a dosage of between 0.01-1,000 µg/kg body weight/day of the additional therapeutic agent can be administered.

The amount of additional therapeutic agent present in the compositions of this invention will be no more than the amount that would normally be administered in a composition comprising that therapeutic agent as the only active agent. Preferably the amount of additional therapeutic agent in the presently disclosed compositions will range from about 50% to 100% of the amount normally present in a composition comprising that agent as the only therapeutically active agent.

The compounds of this invention, or pharmaceutical compositions thereof, may also be incorporated into compositions for coating an implantable medical device, such as prostheses, artificial valves, vascular grafts, stents and catheters. Vascular stents, for example, have been used to overcome restenosis (re-narrowing of the vessel wall after injury). However, patients using stents or other implantable devices risk clot formation or platelet activation. These unwanted effects may be prevented or mitigated by pre-coating the device with a pharmaceutically acceptable composition comprising a kinase inhibitor. Implantable devices coated with a compound of this invention are another embodiment of the present invention.

Any of the compounds and/or compositions of the disclosure may be provided in a kit comprising the compounds and/or compositions. Thus, in some embodiments, the compound and/or composition of the disclosure is provided in a kit.

The disclosure is further described by the following non-limiting Examples.

EXAMPLES

Examples are provided herein to facilitate a more complete understanding of the disclosure. The following examples serve to illustrate the exemplary modes of making and practicing the subject matter of the disclosure. However, the scope of the disclosure is not to be construed as limited to specific embodiments disclosed in these examples, which are illustrative only.

As depicted in the Examples below, in certain exemplary embodiments, compounds are prepared according to the following general procedures. It will be appreciated that, although the general methods depict the synthesis of certain compounds of the present invention, the following general methods, and other methods known to one of ordinary skill in the art, can be applied to other classes and subclasses and species of each of these compounds, as described herein. Additional compounds of the invention were prepared by methods substantially similar to those described herein in the Examples and methods known to one skilled in the art.

In the description of the synthetic methods described below, unless otherwise stated, it is to be understood that all reaction conditions (for example, reaction solvent, atmosphere, temperature, duration, and workup procedures) are selected from the standard conditions for that reaction, unless otherwise indicated. The starting materials for the Examples are either commercially available or are readily prepared by standard methods from known materials.

LIST OF ABBREVIATIONS aq: aqueous
Ac: acetyl
ACN or MeCN: acetonitrile
AmF: ammonium formate
anhyd.: anhydrous
BINAP: (+)-2,2'-Bis(diphenylphosphino)-1,1'-binaphthalene
Bn: Benzyl
conc.: concentrated
DBU: 1,8-Diazabicyclo[5.4.0]undec-7-ene
DCE: Dichloroethane
DCM: Dichloromethane
DIPEA: Diisopropylamine
DMF: N,N-dimethylformamide
DMP: Dess-Martin periodinane
DMPU: N,N'-Dimethylpropyleneurea
DMSO: dimethylsulfoxide
DIPEA: diisopropylethylamine
EA or EtOAc: ethyl acetate
EDCT, EDC, or EDAC: 1-Ethyl-3-(3-dimethylaminopropyl)carbodiimide
equiv or eq: molar equivalents
Et: ethyl
HATU: 1-[Bis(dimethylamino)methylene]-1H-1,2,3-triazolo[4,5-b]pyridinium 3-oxid Hexafluorophosphate
HPLC: high pressure liquid chromatography
LCMS or LC-MS: liquid chromatography-mass spectrometry
Ms: methanesulfonyl
NBS: N-bromosuccinimide
NMR: nuclear magnetic resonance
PE: petroleum ether
PMB: p-methoxybenzyl
rt or RT: room temperature
sat: saturated
TBS: tert-butyldimethylsilyl
TEA: triethylamine
Tf: trifluoromethanesulfonate
TFA: trifluoroacetic acid
THF: tetrahydrofuran
TLC: thin layer chromatography
Tol: toluene
UV: ultra violet LC-MS Method Summaries
LCMS Method 1
  Instrumentation
  LC: Waters Acquity UPLC
  UV Detection: Waters Acquity PDA (198-360 nm), 20 pts/sec, 220 and 254 nm MS Detection: Waters SQD, EST (ES+/ES−, 120-1200 amu)
Mobile Phase
  Eluent A1: Milli-Q H$_2$O+10 mM Ammonium Formate pH: 3.8 (AmF)
  Eluent B1: ACN
  Column Waters Acquity UPLC CSH C18, 1.8 μm, 2.1×30 mm at 40° C.
  Gradient 5% to 100% B in 2.0 minutes; hold 100% B for 0.7 minute
  Flow 0.9 mL/min
  Run Time 2.7 minutes
LCMS Method 2
Instrumentation
  LC: Waters Acquity UPLC
  UV Detection: Waters Acquity PDA (198-360 nm), 20 pts/sec, 220 and 254 nm
  MS Detection: Waters SQD, ESI (ES+/ES−, 120-1200 amu)
Mobile Phase
  Eluent A1: Milli-Q H$_2$O+10 mM Ammonium Formate pH: 3.8 (AmF)
  Eluent B1: ACN Column Waters Acquity UPLC CSH C18, 1.8 μm, 2.1×30 mm at 40° C.
  Gradient 5% to 100% B in 5.2 minutes; hold 100% B for 1.2 minutes
  Flow 0.9 mL/min
  Run Time 7 minutes Example 1

N-(1-Oxo-3-(o-tolyl)isoindolin-4-yl)benzo[b]thiophene-3-carboxamide (I-1)

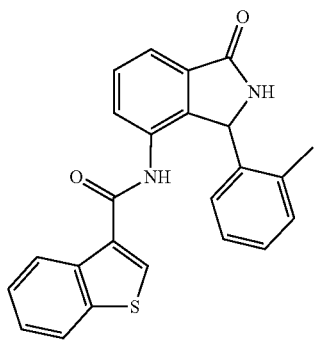 [SMILES: Cc1ccccc1C1NC(=O)c2cccc(NC(=O)c3csc4ccccc34)c21]

2-(4-methoxybenzyl)-4-nitroisoindoline-1,3-dione

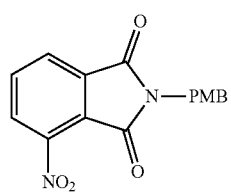

Step 1: To a mixture of 4-nitroisobenzofuran-1,3-dione (40.0 g, 207 mmol, 1.00 eq.) in HOAc (500 mL) was added PMBNH$_2$ (36.9 g, 269 mmol, 34.9 mL, 1.30 eq.) at 25° C., then heated to 85° C. and stirred at 85° C. for 10 hrs. Two batches of the mixture were poured into water (1.00 L), then filtered and the filter cake was washed with petroleum ether (200 mL), dried in vacuum to afford 2-(4-methoxybenzyl)-4-nitroisoindoline-1,3-dione (120 g, 383 mmol, 92.6% yield, 100% purity) as a light yellow solid. MS: m/z=334.9 [M+Na]$^+$; $^1$H NMR (400 MHz, DMSO-d$_6$) δ 8.28 (d, J=8.0 Hz, 1H), 8.17 (d, J=7.2 Hz, 1H), 8.05 (t, J=8.0 Hz, 1H), 7.27 (d, J=8.4 Hz, 2H), 6.88 (d, J=8.4 Hz, 2H), 4.70 (s, 2H), 3.72 (s, 3H).

4-amino-2-(4-methoxybenzyl)isoindoline-1,3-dione

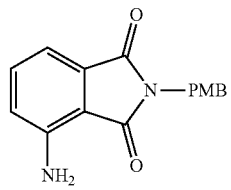

Step 2: To a solution of 2-(4-methoxybenzyl)-4-nitroisoindoline-1,3-dione (48.8 g, 156 mmol, 1.00 equiv.) in EtOH (700 mL)/H$_2$O (200 mL) was added NH$_4$Cl (33.4 g, 625 mmol, 4.00 eq.) at 25° C. The mixture was heated to 40° C. and Fe (26.2 g, 469 mmol, 3.00 eq.) was added into the mixture at 40° C. Then the mixture was heated to 80° C. and stirred at 80° C. for 1 hr. Two batches of the mixture were filtered, and the filter cake was washed with ethyl acetate (5×800 mL). The filtrate was concentrated in vacuum to afford a residue. To the residue was added water (400 mL) and extracted with ethyl acetate (3×800 mL). The combined organic layer was washed with brine (800 mL), dried over Na$_2$SO$_4$, and filtered. The filtrate was concentrated to afford 4-amino-2-(4-methoxybenzyl)isoindoline-1,3-dione (85.5 g, 298 mmol, 95.5% yield, 98.5% purity) as a yellow solid. MS: m/z=283.1 [M+H]$^+$; $^1$H NMR (400 MHz, DMSO-d$_6$) δ 7.43 (t, J=6.0 Hz, 1H), 7.22 (d, J=8.4 Hz, 2H), 6.99-6.96 (m, 2H), 6.87 (d, J=8.4 Hz, 2H), 6.46 (s, 2H), 4.61 (s, 2H), 3.71 (s, 3H).

4-amino-3-hydroxy-2-(4-methoxybenzyl)-3-(o-tolyl)isoindolin-1-one

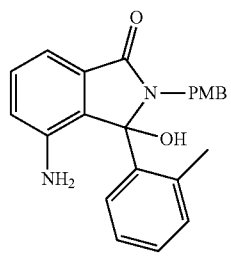

Step 3: To a solution of 4-amino-2-(4-methoxybenzyl)isoindoline-1,3-dione (50.0 g, 174 mmol, 1.00 eq.) in DCM (1.50 L) was added o-tolylmagnesium bromide (1.00 M in Et$_2$O, 436 mL, 2.50 eq.) dropwise at 0° C., then warmed to 20° C. and stirred at 20° C. for 1 hr. The mixture was poured into a saturated aqueous solution of NH$_4$Cl (1.50 L) and extracted with ethyl acetate (3×800 mL). The combined organic layer was washed with brine (800 mL), dried over Na$_2$SO$_4$, and filtered. The filtrate was concentrated to afford 4-amino-3-hydroxy-2-(4-methoxybenzyl)-3-(o-tolyl)isoindolin-1-one (72.4 g, crude) as a yellow solid. MS: m/z=357.4 [M−OH]$^+$.

4-amino-2-(4-methoxybenzyl)-3-(o-tolyl)isoindolin-1-one

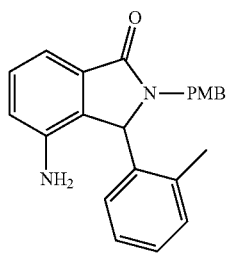

Step 4: To a solution of 4-amino-3-hydroxy-2-(4-methoxybenzyl)-3-(o-tolyl)isoindolin-1-one (67.4 g, 180 mmol, 1.00 eq.) in DCM (680 mL) was added TFA (205 g, 1.80 mol, 133 mL, 10.0 eq.) at 25° C. The mixture was cooled to 0° C., then triethylsilane (41.9 g, 360 mmol, 57.5 mL, 2.00 eq.) was added at 0° C. The mixture was warmed to 25° C. and stirred at 25° C. for 1 hr. The mixture was concentrated in vacuum to afford a residue. To the residue was added water (500 mL), the pH was adjusted to 8 by addition of ammonia, and the mixture was extracted with DCM (3×500 mL). The combined organic layer was washed with brine (500 mL), dried over Na$_2$SO$_4$, and filtered. The filtrate was concentrated to afford a crude product. The crude product was purified by column chromatography (SiO$_2$, petroleum ether/ethyl acetate=1:0 to 0:1) to afford 4-amino-2-(4-methoxybenzyl)-3-(o-tolyl)isoindolin-1-one (30.0 g, 81.7 mmol, 45.4% yield, 97.6% purity) as a yellow solid. MS: m/z=359.1 [M+H]$^+$; $^1$H NMR (400 MHz, DMSO-d$_6$) δ 7.56-7.55 (m, 1H), 7.28-7.24 (m, 6H), 7.10-7.00 (m, 8H), 6.99-6.74 (m, 6H), 6.48 (d, J=7.6 Hz, 1H), 5.52 (s, 1H), 5.39 (s, 1H), 5.00-4.94 (m, 2H), 4.56 (s, 2H), 4.43 (s, 2H), 3.72 (s, 6H), 3.57 (d, J=14.8 Hz, 1H), 3.48 (d, J=15.2 Hz, 1H), 2.26 (s, 3H), 1.50 (s, 2H).

N-{2-[(4-methoxyphenyl)methyl]-3-(2-methylphenyl)-1-oxo-2,3-dihydro-1H-isoindol-4-yl}-1-benzothiophene-3-carboxamide

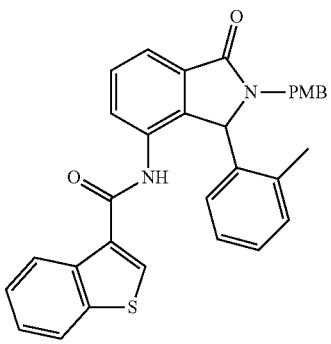

Step 5: To a solution of 4-amino-2-[(4-methoxyphenyl)methyl]-3-(2-methylphenyl)-2,3-dihydro-1H-isoindol-1-one (50 mg, 0.14 mmol) in DCM (2.0 mL) was added pyridine (56 µL, 0.70 mmol, 5 eq.), 1-benzothiophene-3-carbonyl chloride (27 mg, 0.14 mmol, 1 eq.) at RT, and the mixture was stirred at RT for 1.5 hrs. The solution was concentrated by rotary evaporation. The resulting crude mixture was purified by prep-HPLC (40-80% ACN/water) to provide the desired product as a white solid (45 mg, 63% yield). MS: m/z=519.3 [M+H]$^+$.

N-[3-(2-methylphenyl)-1-oxo-2,3-dihydro-1H-isoindol-4-yl]-1-benzothiophene-3-carboxamide (I-1)

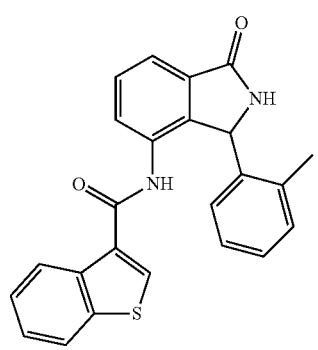 [SMILES: Cc1ccccc1C1NC(=O)c2cccc(NC(=O)c3csc4ccccc34)c21]

Step 6: N-{2-[(4-methoxyphenyl)methyl]-3-(2-methylphenyl)-1-oxo-2,3-dihydro-1H-isoindol-4-yl}-1-benzothiophene-3-carboxamide (40 mg, 0.077 mmol) was dissolved in TFA (2.0 mL). The solution was stirred at 100° C. for 45 min in a microwave reactor. The solution was concentrated by rotary evaporation. The resulting crude mixture was purified by prep-HPLC (30-70% ACN/water) to provide the desired product as a white solid (18 mg, 60% yield). MS: m/z=399.2 [M+H]$^+$; $^1$H NMR (400 MHz, DMSO-d$_6$) δ 10.09 (s, 1H), 9.02 (s, 1H), 7.94-8.07 (m, 2H), 7.52-7.72 (m, 4H), 7.32-7.46 (m, 2H), 7.04-7.15 (m, 1H), 6.91-7.00 (m, 2H), 6.62 (br s, 1H), 6.02 (s, 1H), 2.07-2.30 (m, 3H).

Example 2

N-(1-Oxo-3-(o-tolyl)isoindolin-4-yl)bicyclo[2.2.2]octane-1-carboxamide (I-179)

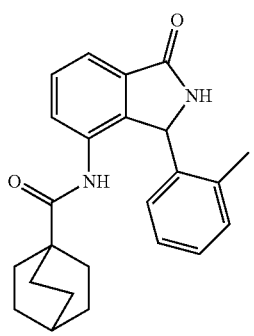 [SMILES: Cc1ccccc1C1NC(=O)c2cccc(NC(=O)C34CCC(CC3)CC4)c21]

N-(2-(4-Methoxybenzyl)-1-oxo-3-(o-tolyl)isoindolin-4-yl)bicyclo[2.2.2]octane-1-carboxamide

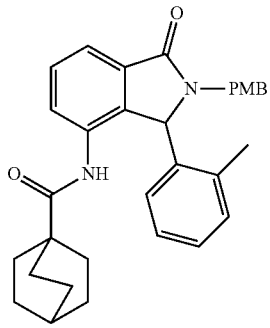

Step 1: A flame-dried, round-bottomed flask equipped with a magnetic stirrer bar was charged with a solution of 4-amino-2-(4-methoxybenzyl)-3-(o-tolyl)isoindolin-1-one (50.0 mg, 139 μmol) in dry pyridine (0.70 mL) under nitrogen, and the solution was cooled to 0° C. with stirring. A solution of bicyclo[2.2.2]octane-1-carbonyl chloride (47.9 mg, 278 μmol) in DCM (1.30 mL) was then added dropwise, and the reaction mixture warmed to ambient temperature and stirred for 16 hours. The reaction mixture was then partitioned between saturated aqueous NaHCO₃ solution (10 mL) and DCM (10 mL), and the mixture passed through a phase separator. The organic phase was then concentrated in vacuo to afford the crude product. Purification by reverse-phase chromatography on C18 (eluting with 55-80% ACN in 10 mmol aqueous AmF) furnished N-(2-(4-methoxybenzyl)-1-oxo-3-(o-tolyl)isoindolin-4-yl)bicyclo[2.2.2]octane-1-carboxamide (43 mg, 86.4 μmol, 62% yield) as an amorphous orange solid. LC-MS (Method 1): 1.60 min, m/z=495.4 [M+H]⁺.

N-(1-oxo-3-(o-tolyl)isoindolin-4-yl)bicyclo[2.2.2]octane-1-carboxamide (I-179)

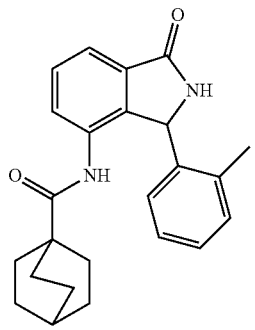 [SMILES: Cc1ccccc1C1NC(=O)c2cccc(NC(=O)C34CCC(CC3)CC4)c21]

Step 2: A solution of N-(2-(4-methoxybenzyl)-1-oxo-3-(o-tolyl)isoindolin-4-yl)bicyclo[2.2.2]octane-1-carboxamide (40.0 mg, 80.8 μmol) in TFA (0.54 mL) was heated at 90° C. with stirring in a sealed tube for 18 hours. The reaction mixture was then cooled to ambient temperature and concentrated in vacuo. The residue was purified directly by reverse-phase flash chromatography on C18 (eluting with 40-65% ACN in 10 mmol aqueous AmF) to afford N-(1-oxo-3-(o-tolyl)isoindolin-4-yl)bicyclo[2.2.2]octane-1-carboxamide (21.0 mg, 56.0 μmol, 70% yield) as an amorphous orange solid. LC-MS (Method 2): 2.45 min, m/z=375.3 [M+H]⁺; ¹H NMR (400 MHz, DMSO-d₆) δ 8.97 (s, 1H), 8.75 (s, 1H), 7.57-7.54 (m, 1H), 7.53-7.49 (m, 1H), 7.45 (dd, J=7.5, 1.4 Hz, 1H), 7.18 (d, J=4.0 Hz, 2H), 7.06-6.98 (m, 1H), 6.47 (br. s, 1H), 5.94 (s, 1H), 2.32 (br. s, 3H), 1.50-1.45 (m, 1H), 1.42-1.33 (m, 6H), 1.32-1.21 (m, 6H).

Example 3

N-(1-Oxo-3-(o-tolyl)isoindolin-4-yl)-[1,2,4]triazolo[4,3-a]pyridine-3-carboxamide (I-328)

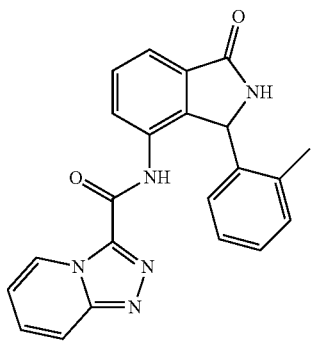 [SMILES: Cc1ccccc1C1NC(=O)c2cccc(NC(=O)c3nnc4ccccn34)c21]

[1,2,4]Triazolo[4,3-a]pyridine-3-carbonyl chloride

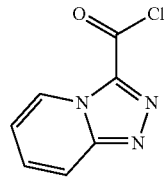 [SMILES: O=C(Cl)c1nnc2ccccn12]

Step 1: Thionyl chloride (20.0 μL, 275 μmol) was added dropwise to a stirring solution of [1,2,4]triazolo[4,3-a]pyridine-3-carboxylic acid (34.0 mg, 208 μmol) and DIPEA (0.15 mL, 858 μmol) in DCM (0.83 mL) at 0° C. The reaction mixture was stirred at this temperature for 15 mins, then warmed to ambient temperature and stirred for a further 1.5 hours. The volatiles were then removed in vacuo, and the crude [1,2,4]triazolo[4,3-a]pyridine-3-carbonyl chloride was used directly in the next step, assuming quantitative yield.

N-(2-(4-Methoxybenzyl)-1-oxo-3-(o-tolyl)isoindolin-4-yl)-[1,2,4]triazolo[4,3-a]pyridine-3-carboxamide

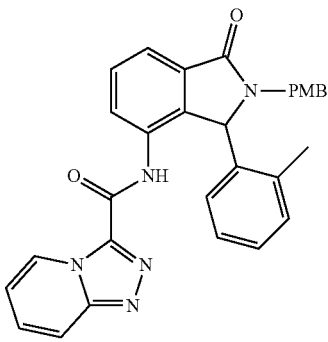

Step 2: A flame-dried, round-bottomed flask equipped with a magnetic stirrer bar was charged with a solution of 4-amino-2-(4-methoxybenzyl)-3-(o-tolyl)isoindolin-1-one (50 mg, 139 μmol) in dry pyridine (0.70 mL) under nitrogen, and the solution cooled to 0° C. with stirring. A solution of [1,2,4]triazolo[4,3-a]pyridine-3-carbonyl chloride (37.7 mg, 208 μmol) in DCM (1.30 mL) was then added dropwise. The reaction mixture was warmed to ambient temperature and stirred for 16 hours. The reaction mixture was then partitioned between saturated aqueous NaHCO₃ solution (10 mL) and DCM (10 mL), and the mixture was passed through a phase separator. The organic phase was then concentrated in vacuo to afford the crude product. Purification by reverse-phase chromatography on C18 (eluting with 37-57% ACN in 10 mmol aqueous AmF) afforded N-(2-(4-methoxybenzyl)-1-oxo-3-(o-tolyl)isoindolin-4-yl)-[1,2,4]triazolo[4,3-a]pyridine-3-carboxamide (39 mg, 58.0 μmol, 56% yield) as an amorphous yellow solid. LC-MS (Method 1): 1.20 min, m/z=504.3 [M+H]⁺.

N-(1-oxo-3-(o-tolyl)isoindolin-4-yl)-[1,2,4]triazolo[4,3-a]pyridine-3-carboxamide (I-328)

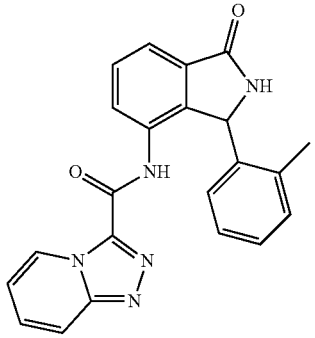 [SMILES: Cc1ccccc1C1NC(=O)c2cccc(NC(=O)c3nnc4ccccn34)c21]

Step 3: A solution of N-(2-(4-methoxybenzyl)-1-oxo-3-(o-tolyl)isoindolin-4-yl)-[1,2,4]triazolo[4,3-a]pyridine-3-carboxamide (39.0 mg, 58.0 μmol) in TFA (0.55 mL) was heated at 90° C. with stirring in a sealed tube for 42 hours. The reaction mixture was then cooled to ambient temperature and concentrated in vacuo. The residue was purified directly by reverse-phase flash chromatography on C18 (eluting with 18-38% ACN in 10 mmol aqueous AmF) to afford N-(1-oxo-3-(o-tolyl)isoindolin-4-yl)-[1,2,4]triazolo[4,3-a]pyridine-3-carboxamide (16.7 mg, 43.5 μmol, 75% yield) as an amorphous white solid.

LC-MS (Method 2): 1.51 min, m/z=384.3 [M+H]⁺; ¹H NMR (400 MHz, DMSO-d₆) δ 10.61 (br. s, 1H), 9.07 (dt, J=7.0, 1.1 Hz, 1H), 9.05 (s, 1H), 7.98 (dt, J=9.3, 1.1 Hz, 1H), 7.69 (dd, J=2.7, 1.2 Hz, 1H), 7.67 (dd, J=3.0, 1.2 Hz, 1H), 7.64-7.58 (m, 2H), 7.24 (td, J=6.9, 1.1 Hz, 1H), 6.93-6.86 (m, 2H), 6.82 (br. s, 1H), 6.66 (br. s, 1H), 6.09 (s, 1H), 2.19 (br. s, 3H). The compound appeared to have been isolated as a partial formate salt, based on the presence of a singlet at 8.42 ppm.

Example 4

7-Chloro-N-[3-(2-methylphenyl)-1-oxo-2,3-dihydro-1H-isoindol-4-yl]imidazo[1,5-a]pyridine-1-carboxamide (I-258)

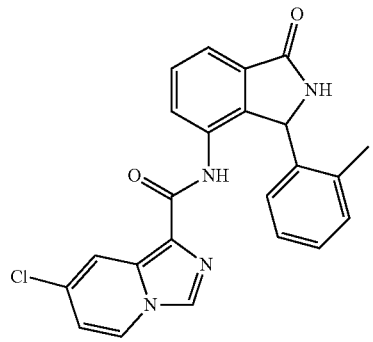 [SMILES: Cc1ccccc1C1NC(=O)c2cccc(NC(=O)c3ncn4ccc(Cl)cc34)c21]

Methyl 2-(4-chloropyridin-2-yl)-2-(hydroxyimino)acetate

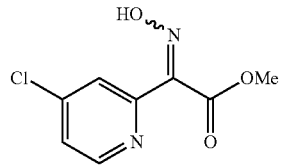 [SMILES: COC(=O)C(=NO)c1cc(Cl)ccn1]

Step 1: A solution of sodium nitrite (242 mg, 3.51 mmol) in water (1.10 mL) was added dropwise to a stirring solution of methyl 2-(4-chloropyridin-2-yl)acetate (652 mg, 3.51 mmol) in acetic acid (4.30 mL) at ambient temperature, and the reaction mixture was stirred at ambient temperature for 4 hours. The volatiles were then removed in vacuo, and the residue was suspended in water (25 mL). The pH was adjusted to 7-8 by addition of solid K₂CO₃, and the resulting suspension was poured into a separatory funnel and extracted into EtOAc (3×10 mL). The combined organic phases were washed with saturated NaCl solution, dried (anhydrous MgSO₄), filtered, and concentrated in vacuo to afford methyl 2-(4-chloropyridin-2-yl)-2-(hydroxyimino)acetate (762 mg, 3.55 mmol) as a yellow-green gum in quantitative yield as a 3:1 mixture of geometric isomers. The crude product was used directly in the next step without further purification. LC-MS (Method 1): 0.68 min (minor isomer), 0.80 min (major isomer), m/z=215.1 [M+H]⁺; Minor Isomer ¹H NMR (400 MHz, CDCl₃) δ 8.53 (d, J=5.5 Hz, 1H), 7.87 (d, J=1.8 Hz, 1H), 7.34 (dd, J=5.4, 2.0 Hz, 1H), 3.99 (s, 3H); Major Isomer ¹H NMR (400 MHz, CDCl₃) δ 8.49-8.46 (m, 1H), 8.24 (dd, J=2.0, 0.5 Hz, 1H), 7.53 (dd, J=5.5, 2.0 Hz, 1H), 3.96 (s, 3H).

Methyl 2-amino-2-(4-chloropyridin-2-yl)acetate

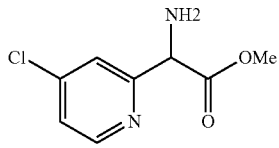 [SMILES: COC(=O)C(N)c1cc(Cl)ccn1]

Step 2: To a vigorously stirring solution of methyl 2-(4-chloropyridin-2-yl)-2-(hydroxyimino)acetate (762 mg, 3.55 mmol) in acetic acid (18.0 mL) at ambient temperature was added zinc dust (1.15 g, 17.7 mmol) in one portion. The reaction mixture was stirred at ambient temperature for 2.5 hours. The volatiles were then removed in vacuo, and the residue was partitioned between EtOAc (20 mL) and saturated aqueous NaHCO₃ solution (25 mL). The biphasic supernatant was decanted into a separatory funnel, and the phases were separated. The aqueous phase was extracted with EtOAc (2×20 mL). The combined organics were washed with saturated NaCl solution, dried (anhydrous MgSO₄), filtered, and concentrated in vacuo to afford crude methyl 2-amino-2-(4-chloropyridin-2-yl)acetate, which was used immediately in the next step without further purification, assuming quantitative yield.

Methyl 7-chloroimidazo[1,5-a]pyridine-1-carboxylate

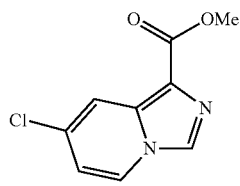 [SMILES: COC(=O)c1ncn2ccc(Cl)cc12]

Step 3: A microwave vial equipped with a magnetic stirring bar was charged with a mixture of methyl 2-amino-2-(4-chloropyridin-2-yl)acetate (712 mg, 3.55 mmol) and triethyl orthoformate (0.88 mL, 5.29 mmol). The vial was sealed, and the reaction mixture irradiated in a microwave reactor at 150° C. for 10 minutes before cooling to ambient temperature. The reaction mixture was concentrated in vacuo, and the residue was purified by reverse-phase flash chromatography on C18 (eluting with 18-38% ACN in 10 mmol aqueous AmF) to furnish methyl 7-chloroimidazo[1,5-a]pyridine-1-carboxylate (17 mg, 80.7 μmol, 2.3% yield) as an amorphous beige solid. LC-MS (Method 1): 0.75 min, m/z=211.0 [M+H]⁺.

7-Chloroimidazo[1,5-a]pyridine-1-carboxylic acid

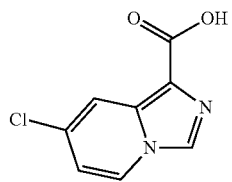 [SMILES: O=C(O)c1ncn2ccc(Cl)cc12]

Step 4: Aqueous 2M NaOH solution (0.05 mL, 0.10 mmol) was added in one portion to a stirring suspension of methyl 7-chloroimidazo[1,5-a]pyridine-1-carboxylate (17.0 mg, 80.7 μmol) in methanol (0.12 mL) and water (0.12 mL), and the mixture stirred at ambient temperature for 20 hours. The reaction mixture was then concentrated in vacuo to remove the volatiles, and the residue was diluted with water (10 mL). The mixture was acidified to pH 2-3 with concentrated HCl, and extracted with a 4:1 mixture of CHCl₃:TPA (3×10 mL). The combined organic phases were washed with saturated aqueous NaCl solution, dried (anhydrous MgSO₄), filtered, and concentrated in vacuo to afford crude 7-chloroimidazo[1,5-a]pyridine-1-carboxylic acid (13.0 mg, 66.1 μmol, 82% yield) as a pale yellow solid. The crude acid was used directly in the next step without further purification. LC-MS (Method 1): 0.55 min, m/z=415.2 [2M+Na]⁺.

7-Chloroimidazo[1,5-a]pyridine-1-carbonyl chloride

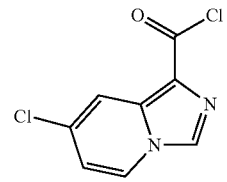 [SMILES: O=C(Cl)c1ncn2ccc(Cl)cc12]

Step 5: Thionyl chloride (10.0 μL, 137 μmol) was added dropwise to a stirring solution of 7-chloroimidazo[1,5-a]pyridine-1-carboxylic acid (13.0 mg, 66.1 μmol) and DIPEA (40.0 μL, 230 μmol) in DCM (0.27 mL) at 0° C. The reaction mixture was stirred at this temperature for 15 mins, then warmed to ambient temperature and stirred for a further 1.5 hours. The volatiles were then removed in vacuo, and the crude 7-chloroimidazo[1,5-a]pyridine-1-carbonyl chloride was used directly in the next step, assuming quantitative yield. 7-Chloro-N-(2-(4-methoxybenzyl)-1-oxo-3-(o-tolyl)isoindolin-4-yl)imidazo[1,5-a]pyridine-1-carboxamide

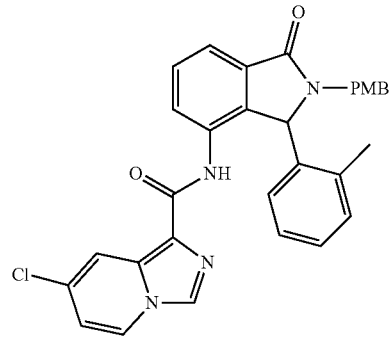

Step 6: A flame-dried round-bottomed flask equipped with a magnetic stirrer bar was charged with a solution of 4-amino-2-(4-methoxybenzyl)-3-(o-tolyl)isoindolin-1-one (28.4 mg, 79.3 µmol) in dry pyridine (0.33 mL) under nitrogen, and the solution was cooled to 0° C. with stirring. A solution of 7-chloroimidazo[1,5-a]pyridine-1-carbonyl chloride (14.2 mg, 66.1 µmol) in DCM (0.80 mL) was then added dropwise, and the reaction mixture was warmed to ambient temperature and stirred for 16 hours. The reaction mixture was then partitioned between saturated aqueous NaHCO$_3$ solution (10 mL) and DCM (10 mL), and the mixture passed through a phase separator. The organic phase was then concentrated in vacuo to afford the crude product. Purification by reverse-phase flash chromatography on C18 (eluting with 50-75% ACN in 10 mmol aqueous AmF) furnished 7-chloro-N-(2-(4-methoxybenzyl)-1-oxo-3-(o-tolyl)isoindolin-4-yl)imidazo[1,5-a]pyridine-1-carboxamide (8.0 mg, 14.8 µmol, 23% yield) as an amorphous orange-brown solid. LC-MS (Method 1): 1.46 min, m/z=537.3 [M+H]$^+$.

7-chloro-N-[3-(2-methylphenyl)-1-oxo-2,3-dihydro-1H-isoindol-4-yl]imidazo[1,5-a]pyridine-1-carboxamide (I-258)

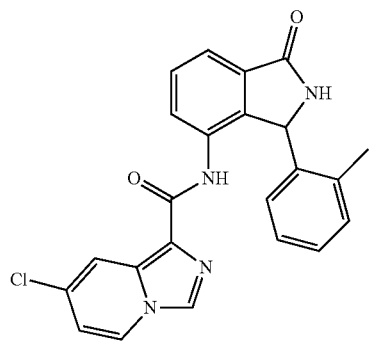 [SMILES: Cc1ccccc1C1NC(=O)c2cccc(NC(=O)c3ncn4ccc(Cl)cc34)c21]

Step 7: A solution of 7-chloro-N-(2-(4-methoxybenzyl)-1-oxo-3-(o-tolyl)isoindolin-4-yl)imidazo[1,5-a]pyridine-1-carboxamide (8.0 mg, 14.8 µmol) in TFA (0.10 mL) was heated at 90° C. with stirring in a sealed tube for 18 hours. The reaction mixture was then cooled to ambient temperature and concentrated in vacuo. The residue was purified directly by reverse-phase flash chromatography on C18 (eluting with 35-55% ACN in 10 mmol aqueous AmF) to afford 7-chloro-N-(1-oxo-3-(o-tolyl)isoindolin-4-yl)imidazo[1,5-a]pyridine-1-carboxamide (5.0 mg, 11.9 µmol, 81% yield) as an amorphous off-white solid. LC-MS (Method 2): 2.17 min, m/z=417.2 [M+H]$^+$; $^1$H NMR (400 MHz, DMSO-d$_6$) δ 9.29 (s, 1H), 9.02 (s, 1H), 8.52 (dd, J=7.4, 0.8 Hz, 1H), 8.42 (s, 1H), 8.03-7.98 (m, 2H), 7.56 (d, J=1.7 Hz, 1H), 7.55 (s, 1H), 7.09-7.02 (m, 2H), 7.01-6.94 (m, 2H), 6.69 (br. s, 1H), 6.15 (s, 1H), 2.35 (br. s, 3H).

Example 5

7-Chloro-N-(1-oxo-3-(o-tolyl)isoindolin-4-yl)-3-methylimidazo[1,5-a]pyridine-1-carboxamide (I-277)

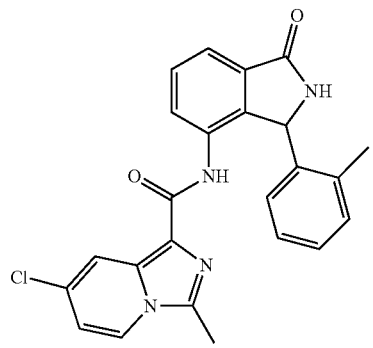 [SMILES: Cc1ccccc1C1NC(=O)c2cccc(NC(=O)c3nc(C)n4ccc(Cl)cc34)c21]

N-((4-Chloropyridin-2-yl)methyl)acetamide

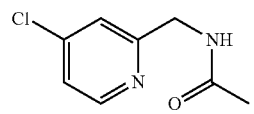

Step 1: Acetyl chloride (0.43 mL, 6.05 mmol) was added dropwise to a stirring solution of (4-chloropyridin-2-yl)methanamine (684 mg, 4.79 mmol) and pyridine (0.78 mL, 9.64 mmol) at 0° C. The reaction mixture was stirred at 0° C. for 15 minutes, then warmed to ambient temperature and stirred for 2 hours. The reaction mixture was then concentrated in vacuo and the crude N-((4-chloropyridin-2-yl)methyl)acetamide was used directly in the next step without further purification, assuming quantitative yield. LC-MS (Method 1): 0.47 min, m/z=185.0 [M+H]$^+$. 1-(7-Chloro-3-methylimidazo[1,5-a]pyridin-1-yl)-2,2,2-trifluoroethanone

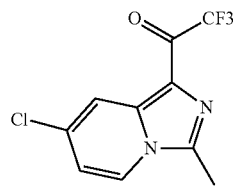 [SMILES: Cc1nc(C(=O)C(F)(F)F)c2cc(Cl)ccn12]

Step 2: Crude N-((4-chloropyridin-2-yl)methyl)acetamide (884 mg, 4.78 mmol) was dissolved in DCM (16.0 mL), pyridine (1.20 mL, 14.7 mmol) was added, and the resulting solution was cooled to −5° C. with stirring. Trifluoroacetic anhydride (1.50 mL, 10.7 mmol) was then added slowly dropwise. The reaction mixture was allowed to slowly warm to ambient temperature with stirring over 3 hours. The reaction was then quenched with saturated aqueous NaHCO$_3$ solution (20 mL), and the mixture was extracted with DCM (3×20 mL). The combined organics were washed with saturated aqueous NaCl solution, dried (anhydrous MgSO$_4$), filtered, and concentrated in vacuo. Purification of the residue by reverse-phase flash chromatography on C18 (eluting with 30-55% ACN in 10 mmol aqueous AmF) furnished 1-(7-chloro-3-methylimidazo[1,5-a]pyridin-1-yl)-2,2,2-trifluoroethanone (1.02 g, 3.89 mmol, 82% yield over two steps) as a yellow solid. $^1$H NMR (400 MHz, CDCl$_3$) δ 8.41 (dd, J=2.0, 0.9 Hz, 1H), 7.91 (dd, J=7.3, 0.8 Hz, 1H), 7.00 (dd, J=7.3, 2.1 Hz, 1H), 2.74 (s, 3H).

7-Chloro-3-methylimidazo[1,5-a]pyridine-1-carboxylic acid

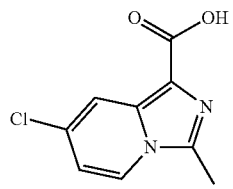

Step 3: A microwave vial equipped with a magnetic stirrer bar was charged with a suspension of 1-(7-chloro-3-methylimidazo[1,5-a]pyridin-1-yl)-2,2,2-trifluoroethanone (400 mg, 1.52 mmol) in 2M aqueous NaOH solution (4.50 mL, 9.00 mmol). The vial was sealed and irradiated in a microwave reactor at 110° C. for 10 minutes. The reaction mixture was cooled to ambient temperature, diluted with water (30 mL), and extracted with EtOAc (2×10 mL). The aqueous phase was then acidified to pH 2-3 with conc. HCl, during which a precipitate was evolved. The precipitate was collected by vacuum filtration, washed with water, and dried by suction to furnish 7-chloro-3-methylimidazo[1,5-a]pyridine-1-carboxylic acid (260 mg, 1.23 mmol, 81% yield) as an amorphous beige solid. LC-MS (Method 1): 0.58 min, m/z=211.1 [M+H].

7-Chloro-3-methylimidazo[1,5-a]pyridine-1-carbonyl chloride

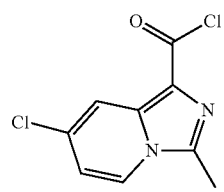

Step 4: Thionyl chloride (20.0 μL, 275 μmol) was added dropwise to a stirring solution of 7-chloro-3-methylimidazo[1,5-a]pyridine-1-carboxylic acid (44.0 mg, 0.21 mmol) and DIPEA (0.15 mL, 0.86 mmol) in DCM (1.10 mL) at 0° C. The reaction mixture was stirred at this temperature for 15 mins, then warmed to ambient temperature and stirred for a further 1.5 hours. The volatiles were then removed in vacuo, and the crude 7-chloro-3-methylimidazo[1,5-a]pyridine-1-carbonyl chloride used directly in the next step, assuming quantitative yield.

7-Chloro-N-(2-(4-methoxybenzyl)-1-oxo-3-(o-tolyl)isoindolin-4-yl)-3-methylimidazo[1,5-a]pyridine-1-carboxamide

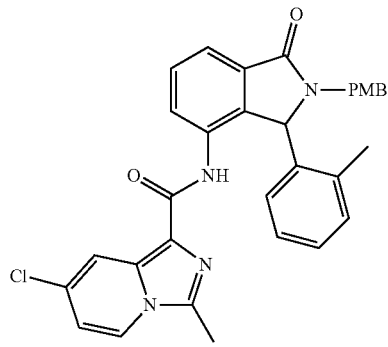

Step 5: A flame-dried round-bottomed flask equipped with a magnetic stirrer bar was charged with a solution of 4-amino-2-(4-methoxybenzyl)-3-(o-tolyl)isoindolin-1-one (50.0 mg, 139 μmol) in dry pyridine (0.70 mL) under nitrogen, and the solution cooled to 0° C. with stirring. A solution of 7-chloro-3-methylimidazo[1,5-a]pyridine-1-carbonyl chloride (47.6 mg, 208 μmol) in DCM (1.40 mL) was then added dropwise, and the reaction mixture was warmed to ambient temperature and stirred for 16 hours. The reaction mixture was then partitioned between saturated aqueous NaHCO$_3$ solution (10 mL) and DCM (10 mL), and the mixture was passed through a phase separator. The organic phase was then concentrated in vacuo to afford the crude product. Purification by reverse-phase flash chromatography on C18 (eluting with 55-75% ACN in 10 mmol aqueous AmF) furnished 7-chloro-N-(2-(4-methoxybenzyl)-1-oxo-3-(o-tolyl)isoindolin-4-yl)-3-methylimidazo[1,5-a]pyridine-1-carboxamide (62 mg, 0.11 mmol, 79% yield) as an amorphous orange-brown solid. LC-MS (Method 1): 1.54 min, m/z=551.3 [M+H][1].

7-Chloro-N-(1-oxo-3-(o-tolyl)isoindolin-4-yl)-3-methylimidazo[1,5-a]pyridine-1-carboxamide (I-277)

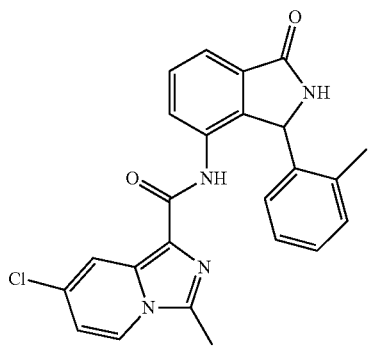 [SMILES: Cc1ccccc1C1NC(=O)c2cccc(NC(=O)c3nc(C)n4ccc(Cl)cc34)c21]

Step 6: A solution of 7-chloro-N-(2-(4-methoxybenzyl)-1-oxo-3-(o-tolyl)isoindolin-4-yl)-3-methylimidazo[1,5-a]pyridine-1-carboxamide (62 mg, 109 μmol) in TFA (0.73 mL) was heated at 90° C. with stirring in a sealed tube for 18 hours. The reaction mixture was then cooled to ambient temperature and concentrated in vacuo. The residue was purified directly by reverse-phase flash chromatography on C18 (eluting with 36-56% ACN in 10 mmol aqueous AmF) to afford 7-chloro-N-(1-oxo-3-(o-tolyl)isoindolin-4-yl)imidazo[1,5-a]pyridine-1-carboxamide (6.0 mg, 13.9 μmol, 13% yield) as an amorphous off-white solid. LC-MS (Method 2): 2.17 min, m/z=417.2 [M+H]F; $^1$H NMR (400 MHz, DMSO-$d_6$) δ 9.05 (s, 1H), 9.04 (s, 1H), 8.33 (dd, J=7.6, 0.5 Hz, 1H), 8.17 (dd, J=7.4, 1.3 Hz, 1H), 7.98 (dd, J=2.1, 0.7 Hz, 1H), 7.59-7.50 (m, 2H), 7.17 (br. d, J=7.4 Hz, 1H), 7.14-7.08 (m, 1H), 7.03 (br. t, J=7.2 Hz, 1H), 6.97 (dd, J=7.5, 2.1 Hz, 1H), 6.72 (br. s, 1H), 6.12 (s, 1H), 2.61 (s, 3H), 2.45 (br. s, 3H). The broad singlet at 2.45 ppm overlaps with the DMSO-$d_5$ peak.

Additional compounds prepared according to the methods of Examples 1-5 are listed in Table 2 below. Corresponding $^1$H NMR and mass spectrometry characterization for these compounds are described in Table 1. Certain compounds in Table 2 below were prepared by replacing 4-amino-2-(4-methoxybenzyl)-3-(o-tolyl)isoindolin-1-one, as described in Examples 1-5, with other compounds whose preparation is described further below in the Examples.

TABLE 2

Additional Exemplary Compounds

| Compound | Compound | Compound |
| --- | --- | --- |
| I-2 | I-61 | I-216 |
| I-4 | I-62 | I-279 |
| I-5 | I-67 | I-292 |
| I-11 | I-69 | I-316 |
| I-16 | I-74 | I-317 |
| I-19 | I-78 | I-318 |
| I-20 | I-79 | I-340 |
| I-21 | I-81 | I-341 |
| I-25 | I-86 | I-369 |
| I-26 | I-97 | I-376 |
| I-30 | I-98 | I-377 |
| I-36 | I-105 | I-378 |
| I-37 | I-107 | I-387 |
| I-38 | I-109 | I-388 |
| I-42 | I-111 | I-612 |
| I-46 | I-112 | I-638 |
| I-47 | I-124 | I-693 |
| I-48 | I-144 | I-752 |
| I-54 | I-198 | I-850 |
| I-58 | I-203 | I-1610 |
| I-59 | I-206 | I-1617 |

Example 6

6,8-Difluoro-N-(1-oxo-3-(o-tolyl)isoindolin-4-yl)imidazo[1,5-a]pyridine-3-carboxamide (I-180)

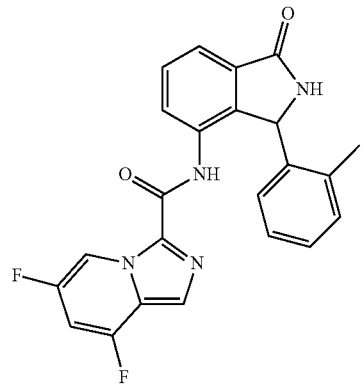 [SMILES: Cc1ccccc1C1NC(=O)c2cccc(NC(=O)c3ncc4c(F)cc(F)cn34)c21]

Ethyl 2-(((3,5-difluoropyridin-2-yl)methyl)amino)-2-oxoacetate

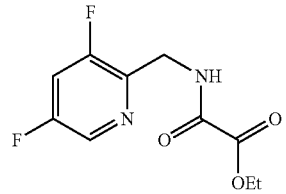

Step 1: A flame-dried, round-bottomed flask equipped with a magnetic stirrer bar was charged with a solution of (3,5-difluoropyridin-2-yl)methanamine (500 mg, 3.46 mmol) and triethylamine (0.97 mL, 6.95 mmol) in DCM (7.00 mL), and the mixture was cooled to 0° C. with stirring. Ethyl chlorooxoacetate (0.39 mL, 3.49 mmol) was added slowly dropwise, and the reaction mixture was allowed to warm to ambient temperature and stirred for 3 days. The reaction was quenched with water (20 mL) and the mixture was extracted with DCM (3×20 mL). The combined organic phases were washed with saturated aqueous NaCl solution, dried (anhyd. MgSO$_4$), filtered, and concentrated in vacuo. Purification by flash chromatography on silica gel (eluting with 5-80% EtOAc in hexanes) furnished ethyl 2-(((3,5-difluoropyridin-2-yl)methyl)amino)-2-oxoacetate (452 mg, 1.85 mmol, 53% yield) as a yellow gum. LC-MS (Method 1): 0.61 min, m/z=245.1 [M+H]$^+$; $^1$H NMR (400 MHz, CDCl$_3$) δ 8.32 (d, 2.3 Hz, 1H), 8.21 (br. s, 1H), 7.27-7.22 (m, 1H), 4.69 (dt, 5.1, 1.6 Hz, 1H), 4.39 (q, 7.1 Hz, 2H), 1.40 (t, 7.2 Hz, 3H).

1801

Ethyl 6,8-difluoroimidazo[1,5-a]pyridine-3-carboxylate

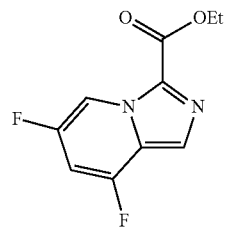 [SMILES: CCOC(=O)c1ncc2c(F)cc(F)cn12]

Step 2: A round-bottomed flask equipped with a magnetic stirrer bar and a reflux condenser was charged with a solution of ethyl 2-(((3,5-difluoropyridin-2-yl)methyl)amino)-2-oxoacetate (412 mg, 1.68 mmol) in DCE (4.10 mL), then POCl$_3$ (1.50 mL, 16.0 mmol) was added dropwise at ambient temperature with stirring. The reaction mixture was then heated to 120° C. with stirring for 18 hours, before cooling to ambient temperature. The volatiles were removed in vacuo, and the residue carefully quenched by addition of saturated aqueous NaHCO$_3$ solution (20 mL). The mixture was extracted with EtOAc (3×25 mL), and the combined organic phases were dried (anhyd. MgSO$_4$), filtered, and concentrated in vacuo. Purification of the residue by flash chromatography on silica gel (eluting with 5-20% EtOAc in hexanes) afforded ethyl 6,8-difluoroimidazo[1,5-a]pyridine-3-carboxylate (306 mg, 1.35 mmol, 80% yield) as a very pale yellow solid. LC-MS (Method 1): 0.94 min, m/z=227.7 [M+H]$^-$.

6,8-Difluoroimidazo[1,5-a]pyridine-3-carboxylic acid

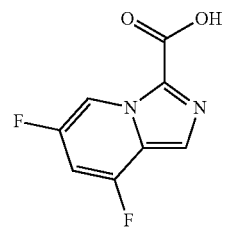 [SMILES: O=C(O)c1ncc2c(F)cc(F)cn12]

Step 3: Aqueous 2M NaOH solution (0.25 mL, 0.50 mmol) was added in one portion to a stirring solution of ethyl 6,8-difluoroimidazo[1,5-a]pyridine-3-carboxylate (100 mg, 0.44 mmol) in ethanol (0.67 mL) and water (0.67 mL), and the mixture was stirred at ambient temperature for 18 hours. The reaction mixture was then concentrated in vacuo to remove the volatiles, and the residue diluted with water (10 mL). The mixture was acidified to pH 2-3 with concentrated HCl. The resulting precipitate was collected by vacuum filtration, washed with water, and dried by suction to afford 6,8-difluoroimidazo[1,5-a]pyridine-3-carboxylic acid (73 mg, 0.37 mmol, 83% yield) as a pale yellow solid. LC-MS (Method 1): 0.48 min, m/z=197.1 [M–H]$^-$.

1802

6,8-Difluoroimidazo[1,5-a]pyridine-3-carbonyl chloride

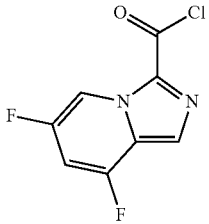

Step 4: Thionyl chloride (30.0 µL, 41.4 µmol) was added dropwise to a stirring solution of 6,8-difluoroimidazo[1,5-a]pyridine-3-carboxylic acid (55.0 mg, 278 µmol) and DIPEA (0.20 mL, 1.14 mmol) in DCM (1.10 mL) at 0° C. The reaction mixture was stirred at this temperature for 15 mins, then warmed to ambient temperature and stirred for a further 1.5 hours. The volatiles were then removed in vacuo, and the crude 6,8-difluoroimidazo[1,5-a]pyridine-3-carbonyl chloride was used directly in the next step, assuming quantitative yield.

6,8-Difluoro-N-(2-(4-methoxybenzyl)-1-oxo-3-(o-tolyl)isoindolin-4-yl)imidazo[1,5-a]pyridine-3-carboxamide

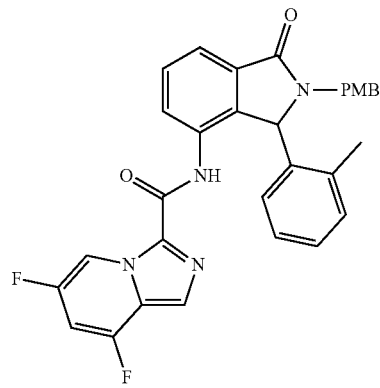

Step 5: A flame-dried, round-bottomed flask equipped with a magnetic stirrer bar was charged with a solution of 4-amino-2-(4-methoxybenzyl)-3-(o-tolyl)isoindolin-1-one (50 mg, 139 µmol) in dry pyridine (0.70 mL) under nitrogen, and the solution was cooled to 0° C. with stirring. A solution of 6,8-difluoroimidazo[1,5-a]pyridine-3-carbonyl chloride (60.2 mg, 278 µmol) in DCM (1.30 mL) was then added dropwise, and the reaction mixture was warmed to ambient temperature and stirred for 16 hours. The reaction mixture was then partitioned between saturated aqueous NaHCO$_3$ solution (10 mL) and DCM (10 mL), and the mixture passed through a phase separator. The organic phase was then concentrated in vacuo to afford the crude product. Purification by flash chromatography on silica gel (eluting with 10% EtOAc in hexanes) furnished 6,8-difluoro-N-(2-(4-methoxybenzyl)-1-oxo-3-(o-tolyl)isoindolin-4-yl)imidazo[1,5-a]pyridine-3-carboxamide (77 mg, 142 µmol, quantitative yield) as an amorphous orange-brown solid. LC-MS (Method 1): 1.60 min, m/z=539.3 [M+H]$^-$.

6,8-Difluoro-N-(1-oxo-3-(o-tolyl)isoindolin-4-yl)imidazo[1,5-a]pyridine-3-carboxamide (I-180)

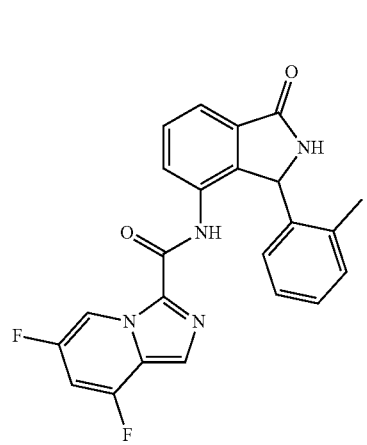 [SMILES: Cc1ccccc1C1NC(=O)c2cccc(NC(=O)c3ncc4c(F)cc(F)cn34)c21]

Step 6: A solution of 6,8-difluoro-N-(2-(4-methoxybenzyl)-1-oxo-3-(o-tolyl)isoindolin-4-yl)imidazo[1,5-a]pyridine-3-carboxamide (57.0 mg, 105 μmol) in TFA (0.70 mL) was heated at 75° C. with stirring in a sealed tube for 40 hours. The reaction mixture was then cooled to ambient temperature and concentrated in vacuo. The residue was purified directly by reverse-phase flash chromatography on C18 (eluting with 40-65% ACN in 10 mmol aqueous AmF) to afford 6,8-difluoro-N-(1-oxo-3-(o-tolyl)isoindolin-4-yl)imidazo[1,5-a]pyridine-3-carboxamide (17.0 mg, 40.6 μmol, 39% yield) as an amorphous orange solid. LC-MS (Method 2): 2.51 min, m/z=419.3 [M+H]$^+$; $^1$H NMR (400 MHz, DMSO-d$_6$) δ 10.02 (br. s, 1H), 9.14 (d, 4.0 Hz, 1H), 9.03 (s, 1H), 7.84 (d, 0.8 Hz, 1H), 7.78 (dd, 7.6, 1.2 Hz, 1H), 7.65-7.62 (m, 1H), 7.62-7.57 (m, 1H), 7.44 (ddd, 10.6, 8.8, 1.8 Hz, 1H), 6.99-6.92 (m, 2H), 6.90-6.85 (m, 1H), 6.68 (br. s, 1H), 6.10 (s, 1H), 2.23 (br. s, 3H).

Additional compounds prepared according to the methods of Example 6 are listed in Table 3 below.

TABLE 3

| Additional Exemplary Compounds |
| --- |
| Compound |
| I-151 |
| I-285 |
| I-342 |

Example 7

N-(1-Oxo-3-(o-tolyl)isoindolin-4-yl)-1,2,3,4-tetrahydro-1,4-methanonaphthalene-1-carboxamide (I-226)

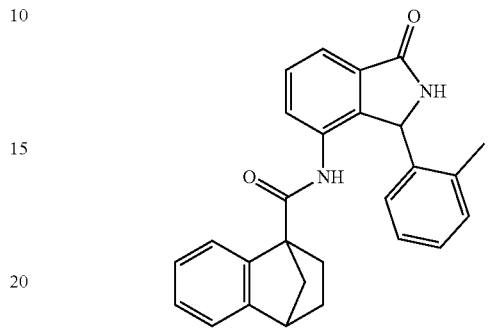

N-(2-(4-Methoxybenzyl)-1-oxo-3-(o-tolyl)isoindolin-4-yl)-1,2,3,4-tetrahydro-1,4-methanonaphthalene-1-carboxamide

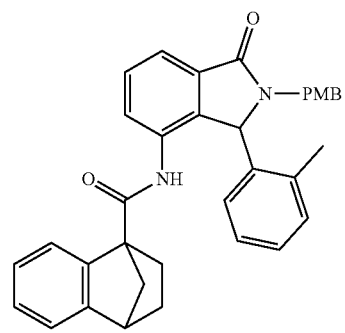

Step 1: A screw-top glass reaction tube equipped with a magnetic stirrer bar was charged with a vigorously stirring mixture of 4-amino-2-(4-methoxybenzyl)-3-(o-tolyl)isoindolin-1-one (50.0 mg, 139 μmol) and 1,2,3,4-tetrahydro-1,4-methanonaphthalene-1-carboxylic acid (31.2 mg, 166 μmol) in DCM (0.50 mL) at ambient temperature. N-methylimidazole (40.0 μL, 500 μmol) was added dropwise, followed by tetramethylchloroformamidinium hexafluorophosphate (TCFH, 46.5 mg, 166 μmol) in one portion, and the reaction mixture stirred at ambient temperature for 24 hours. The reaction mixture was then partitioned between DCM (10 mL) and water (10 mL), and the mixture passed through a phase separator. The organic phase was concentrated in vacuo, and the residue was purified by reverse-phase flash chromatography on C18 (eluting with 55-80% ACN in 10 mmol aqueous AmF) to afford N-(2-(4-methoxybenzyl)-1-oxo-3-(o-tolyl)isoindolin-4-yl)-1,2,3,4-tetrahydro-1,4-methanonaphthalene-1-carboxamide (57.0 mg, 107 μmol, 78% yield) as an amorphous off-white solid. LC-MS (Method 1): 1.58 min, m/z=529.4 [M+H]$^+$.

1805

N-(1-oxo-3-(o-tolyl)isoindolin-4-yl)-1,2,3,4-tetrahydro-1,4-methanonaphthalene-1-carboxamide (I-226)

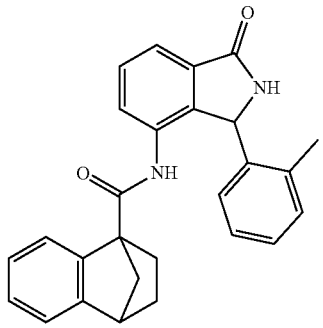 [SMILES: Cc1ccccc1C1NC(=O)c2cccc(NC(=O)C34CCC(C3)c3ccccc34)c21]

Step 2: A solution of N-(2-(4-methoxybenzyl)-1-oxo-3-(o-tolyl)isoindolin-4-yl)-1,2,3,4-tetrahydro-1,4-methanonaphthalene-1-carboxamide (57.0 mg, 107 μmol) in TFA (0.71 mL) was heated at 90° C. with stirring in a sealed tube for 18 hours. The reaction mixture was then cooled to ambient temperature and concentrated in vacuo. The residue was purified directly by reverse-phase flash chromatography on C18 (eluting with 40-60% ACN in 10 mmol aqueous AmF) to afford N-(1-oxo-3-(o-tolyl)isoindolin-4-yl)-1,2,3,4-tetrahydro-1,4-methanonaphthalene-1-carboxamide (37.0 mg, 90.5 μmol, 85% yield) as an amorphous off-white solid. LC-MS (Method 2): 2.49 min, m/z=409.4 [M+H]$^+$; $^1$H NMR (400 MHz, DMSO-$d_6$) as a 1:1 mixture of diastereomers δ 9.02 (br. s, 1H), 8.99 (br. s, 1H), 8.80 (br. s, 2H), 7.67-7.53 (m, 6H), 7.23-7.10 (m, 6H), 7.09-6.91 (m, 6H), 6.85 (d, J=7.2 Hz, 1H), 6.66-6.58 (m, 3H), 6.07 (s, 2H), 3.31 (dd, J=11.4, 3.4 Hz, 2H), 2.29 (br. s, 6H), 1.93-1.84 (m, 2H), 1.81-1.76 (m, 1H), 1.76-1.64 (m, 3H), 1.44 (d, J=8.7 Hz, 1H), 1.36 (d, J=8.7 Hz, 1H), 1.22-1.14 (m, 1H), 1.14-1.08 (m, 1H), 1.08-0.99 (m, 2H). The spectrum was recorded at 70° C. (343K).

Example 8

N-(1-oxo-3-(o-tolyl)isoindolin-4-yl)benzo[d]isothiazole-3-carboxamide (I-13)

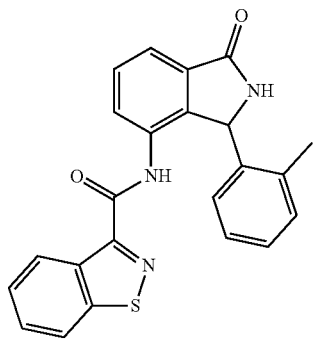 [SMILES: Cc1ccccc1C1NC(=O)c2cccc(NC(=O)c3nsc4ccccc34)c21]

1806

N-(2-(4-methoxybenzyl)-1-oxo-3-(o-tolyl)isoindolin-4-yl)benzo[d]isothiazole-3-carboxamide

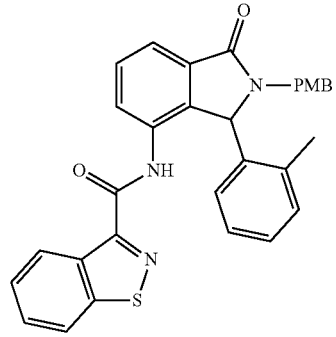

Step 1: To a solution of 4-amino-2-(4-methoxybenzyl)-3-(o-tolyl)isoindolin-1-one (100 mg, 0.278 mmol), 1-[bis(dimethylamino)methylene]-1H-1,2,3-triazolo[4,5-b]pyridinium 3-oxid hexafluorophosphate (HATU, 127 mg, 0.336 mmol), and 1,2-benzothiazole-3-carboxylic acid (50 mg, 0.27 mmol) in anhydrous DMF (1.5 mL), was added NaHCO$_3$ (70 mg, 0.83 mmol). The resulting mixture was stirred under an atmosphere of nitrogen at 22° C. After 18 h, the reaction mixture was treated with a saturated aqueous NaHCO$_3$ solution and extracted with EtOAc (3×10 mL). The combined organic layers were dried over sodium sulfate, filtered, and concentrated by rotary evaporation. The resulting material was purified by C18 column chromatography (eluting with 20% to 100% MeCN/10 mM AmF). The product-containing fractions were combined and lyophilized to obtain the title compound as a white powder (105 mg, 72% yield). m/z=520.4 [M+H]$^+$.

N-(1-Oxo-3-(o-tolyl)isoindolin-4-yl)benzo[d]isothiazole-3-carboxamide (I-13)

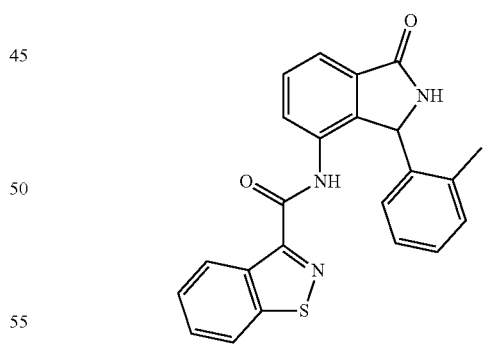

Step 2: N-(2-(4-methoxybenzyl)-1-oxo-3-(o-tolyl)isoindolin-4-yl)benzo[d]isothiazole-3-carboxamide (105 mg, 0.202 mmol) was treated with trifluoroacetic acid (5.0 mL), and the resulting mixture was stirred at 120° C. After 2 h, the reaction mixture was concentrated by rotary evaporation, and the resulting material was purified by C18 column chromatography (eluting with 20% to 100% McCN/10 mM AmF). The product-containing fractions were combined and lyophilized to obtain the title compound as a white powder (45 mg, 58% yield). m/z=400.3 [M+H]$^+$; $^1$H NMR (400

MHz, DMSO-d$_6$) 10.15 (s, 1H), 9.05 (s, 1H), 8.58 (d, J=8.2 Hz, 1H), 8.29 (d, J=8.2 Hz, 1H), 7.80 (dd, J=7.6, 1.2 Hz, 1H), 7.74-7.55 (m, 4H), 7.06-6.93 (m, 2H), 6.89 (t, J=13.3 Hz, 1H), 6.68 (br s, 1H), 6.12 (s, 1H), 2.40-2.10 (br s, 3H).

Additional compounds prepared according to the methods of Examples 7 and 8 are listed in Table 4 below. Certain compounds in Table 4 below were prepared by replacing 4-amino-2-(4-methoxybenzyl)-3-(o-tolyl)isoindolin-1-one, as described in Examples 7 and 8, with other compounds whose preparation is described further below in the Examples.

TABLE 4

Additional Exemplary Compounds

| Compound | Compound | Compound |
|---|---|---|
| I-12 | I-2177 | I-2225 |
| I-17 | I-2178 | I-2226 |
| I-24 | I-2179 | I-2227 |
| I-41 | I-2180 | I-2232 |
| I-63 | I-2193 | I-2235 |
| I-72 | I-2194 | I-2238 |
| I-73 | I-2195 | I-2239 |
| I-129 | I-2196 | I-2247 |
| I-133 | I-2197 | I-2248 |
| I-197 | I-2198 | I-2249 |
| I-200 | I-2211 | I-2250 |
| I-256 | I-2212 | I-2252 |
| I-337 | I-2213 | I-2253 |
| I-612 | I-2214 | I-2254 |
| I-638 | I-2215 | I-2255 |
| I-693 | I-2216 | I-2260 |
| I-752 | I-2217 | I-2261 |
| I-850 | I-2218 | I-2262 |
| I-1610 | I-2219 | I-2263 |
| I-1617 | I-2220 | I-2264 |
| I-2175 | I-2221 | I-2265 |
| I-2176 | I-2224 | I-2266 |
| I-2268 | I-2301 | I-2338 |
| I-2269 | I-2302 | I-2361 |
| I-2270 | I-2303 | I-2362 |
| I-2271 | I-2304 | I-2363 |
| I-2272 | I-2318 | I-2372 |
| I-2273 | I-2319 | I-2374 |
| I-2274 | I-2322 | I-2375 |
| I-2275 | I-2330 | I-2391 |
| I-2281 | I-2335 | I-2392 |
| I-2282 | I-2336 | I-2397 |
| I-2283 | I-2337 | I-2407 |

Example 9

N-[3-(2-methylphenyl)-1-oxo-2,3-dihydro-1H-isoindol-4-yl]-2,3-dihydro-1H-indole-1-carboxamide (I-43)

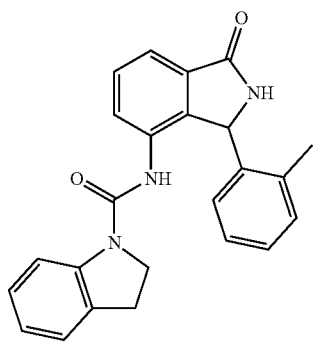 [SMILES: Cc1ccccc1C1NC(=O)c2cccc(NC(=O)N3CCc4ccccc43)c21]

N-{2-[(4-methoxyphenyl)methyl]-3-(2-methylphenyl)-1-oxo-2,3-dihydro-1H-isoindol-4-yl}-2,3-dihydro-1H-indole-1-carboxamide

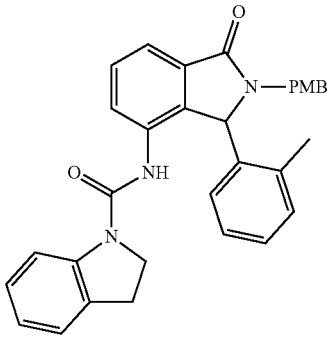

Step 1: To a solution of 4-amino-2-(4-methoxybenzyl)-3-(o-tolyl)isoindolin-1-one (50 mg, 139 µmol, 1.00 eq.) in anhydrous THF (0.7 mL) was added DIPEA (19.2 µL, 139 µmol, 1.00 eq.). The mixture was stirred and cooled to 0° C. A solution of triphosgene (41.8 mg, 141 µmol, 1.01 eq.) in anhydrous THF (0.7 mL) was added dropwise at 0° C. The mixture was stirred overnight at room temperature. The solution was then added to a solution of 2,3-dihydro-1H-indole (116 mg, 973 µmol, 7.00 eq.) in pyridine (1.5 mL) and DMAP (catalytic amount). The resulting mixture was stirred at room temperature overnight. The reaction mixture was diluted with aqueous NH$_4$Cl and extracted with dichloromethane. The organic layer was concentrated to obtain N-{2-[(4-methoxyphenyl)methyl]-3-(2-methylphenyl)-1-oxo-2,3-dihydro-1H-isoindol-4-yl}-2,3-dihydro-1H-indole-1-carboxamide as a brown oil (35 mg), which was used in the next step without further purification. LC-MS (Method 1): 1.42 min, m/z=504.4 [M+H]$^+$.

N-[3-(2-methylphenyl)-1-oxo-2,3-dihydro-1H-isoindol-4-yl]-2,3-dihydro-1H-indole-1-carboxamide (I-43)

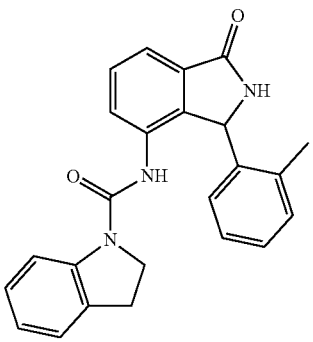 [SMILES: Cc1ccccc1C1NC(=O)c2cccc(NC(=O)N3CCc4ccccc43)c21]

Step 2: A solution of N-{2-[(4-methoxyphenyl)methyl]-3-(2-methylphenyl)-1-oxo-2,3-dihydro-1H-isoindol-4-yl}-2,3-dihydro-1H-indole-1-carboxamide (35 mg, crude) in trifluoroacetic acid (10 ml, 130 mmol) was stirred overnight at 80° C. The reaction mixture was concentrated. The resulting residue was purified by reverse-phase column chromatography (C18: 12 g column; 10 mM AmF in water/acetonitrile)

and lyophilized to give N-[3-(2-methylphenyl)-1-oxo-2,3-dihydro-1H-isoindol-4-yl]-2,3-dihydro-1H-indole-1-carboxamide (18.8 mg, 49.0 μmol, 35% yield) as a white solid. LC-MS (Method 1): 1.51 min, >99% purity, m/z=383.9 [M+H]$^-$; $^1$H NMR (400 MHz, DMSO-d$_6$) δ 8.95 (s, 1H), 8.37 (s, 1H), 7.68 (d, J=8.0 Hz, 1H), 7.60-7.50 (m, 2H), 7.47-7.35 (m, 1H), 7.19-7.06 (m, 3H), 7.02 (d, J=7.3 Hz, 1H), 6.95 (t, J=7.1 Hz, 1H), 6.88 (td, J=7.4, 1.0 Hz, 1H), 6.54 (s, 1H), 5.88 (s, 1H), 3.68-3.50 (m, 1H), 3.01-2.80 (m, 3H), 2.07 (s, 3H).

Additional compounds prepared according to the methods of Example 9 are listed in Table 5 below. Certain compounds in Table 5 below were prepared by replacing 4-amino-2-(4-methoxybenzyl)-3-(o-tolyl)isoindolin-1-one, as described in Example 9, with other compounds whose preparation is described further below in the Examples.

TABLE 5

Additional Exemplary Compounds

| Compound | Compound | Compound |
|---|---|---|
| I-43 | I-597 | I-1051 |
| I-44 | I-598 | I-1176 |
| I-45 | I-612 | I-1256 |
| I-55 | I-638 | I-1257 |
| I-60 | I-642 | I-1269 |
| I-95 | I-661 | I-1270 |
| I-96 | I-685 | I-1294 |
| I-104 | I-686 | I-1318 |
| I-110 | I-693 | I-1382 |
| I-308 | I-698 | I-1383 |
| I-309 | I-713 | I-1429 |
| I-405 | I-714 | I-1459 |
| I-430 | I-716 | I-1462 |
| I-432 | I-720 | I-1507 |
| I-433 | I-722 | I-1508 |
| I-481 | I-752 | I-1509 |
| I-482 | I-766 | I-1510 |
| I-491 | I-769 | I-1511 |
| I-542 | I-772 | I-1512 |
| I-543 | I-988 | I-1513 |
| I-544 | I-989 | I-1514 |
| I-574 | I-990 | I-1576 |
| I-576 | I-992 | I-1577 |
| I-577 | I-1050 | I-1578 |
| I-1579 | I-2121 | I-2204 |
| I-1610 | I-2122 | I-2205 |
| I-1663 | I-2123 | I-2206 |
| I-1715 | I-2124 | I-2207 |
| I-1716 | I-2126 | I-2208 |
| I-1717 | I-2127 | I-2209 |
| I-1718 | I-2128 | I-2210 |
| I-1720 | I-2129 | I-2222 |
| I-1721 | I-2130 | I-2236 |
| I-1722 | I-2131 | I-2237 |
| I-1753 | I-2132 | I-2240 |
| I-1754 | I-2133 | I-2241 |
| I-1755 | I-2142 | I-2242 |
| I-1756 | I-2143 | I-2243 |
| I-1810 | I-2144 | I-2244 |
| I-1902 | I-2145 | I-2245 |
| I-1903 | I-2162 | I-2246 |
| I-1904 | I-2163 | I-2257 |
| I-1945 | I-2164 | I-2276 |
| I-1946 | I-2165 | I-2277 |
| I-1949 | I-2166 | I-2278 |
| I-1953 | I-2167 | I-2279 |
| I-1954 | I-2168 | I-2280 |
| I-1961 | I-2171 | I-2284 |
| I-1965 | I-2172 | I-2286 |
| I-1978 | I-2173 | I-2287 |
| I-2042 | I-2174 | I-2288 |
| I-2111 | I-2181 | I-2291 |
| I-2113 | I-2182 | I-2292 |
| I-2114 | I-2191 | I-2293 |
| I-2115 | I-2199 | I-2294 |

TABLE 5-continued

Additional Exemplary Compounds

| Compound | Compound | Compound |
|---|---|---|
| I-2116 | I-2203 | I-2299 |
| I-2300 | I-2352 | I-2402 |
| I-2305 | I-2353 | I-2403 |
| I-2306 | I-2356 | I-2404 |
| I-2307 | I-2357 | I-2405 |
| I-2308 | I-2364 | I-2406 |
| I-2310 | I-2365 | I-2408 |
| I-2311 | I-2366 | I-2410 |
| I-2312 | I-2367 | I-2411 |
| I-2313 | I-2368 | I-2412 |
| I-2314 | I-2369 | I-2413 |
| I-2315 | I-2370 | I-2414 |
| I-2317 | I-2371 | I-2415 |
| I-2321 | I-2373 | I-2416 |
| I-2328 | I-2376 | I-2417 |
| I-2329 | I-2377 | I-2418 |
| I-2331 | I-2378 | I-2419 |
| I-2332 | I-2379 | I-2420 |
| I-2333 | I-2380 | I-2421 |
| I-2334 | I-2381 | I-2422 |
| I-2339 | I-2382 | I-2423 |
| I-2340 | I-2383 | I-2424 |
| I-2341 | I-2384 | I-2425 |
| I-2342 | I-2385 | I-2426 |
| I-2343 | I-2386 | I-2427 |
| I-2344 | I-2393 | I-2428 |
| I-2345 | I-2394 | I-2429 |
| I-2346 | I-2395 | I-2430 |
| I-2347 | I-2396 | I-2431 |
| I-2348 | I-2398 | I-2432 |
| I-2349 | I-2399 | I-2433 |
| I-2350 | I-2400 | I-2434 |
| I-2351 | I-2401 | I-2435 |
| I-2436 | I-2468 | I-2500 |
| I-2437 | I-2469 | I-2501 |
| I-2438 | I-2470 | I-2502 |
| I-2439 | I-2471 | I-2503 |
| I-2440 | I-2472 | I-2504 |
| I-2441 | I-2473 | I-2505 |
| I-2442 | I-2474 | I-2506 |
| I-2443 | I-2475 | I-2507 |
| I-2444 | I-2476 | I-2508 |
| I-2445 | I-2477 | I-2509 |
| I-2446 | I-2478 | I-2510 |
| I-2447 | I-2479 | I-2511 |
| I-2448 | I-2480 | I-2512 |
| I-2449 | I-2481 | I-2513 |
| I-2450 | I-2482 | I-2514 |
| I-2451 | I-2483 | I-2515 |
| I-2452 | I-2484 | I-2516 |
| I-2453 | I-2485 | I-2517 |
| I-2454 | I-2486 | I-2518 |
| I-2455 | I-2487 | I-2519 |
| I-2456 | I-2488 | I-2520 |
| I-2457 | I-2489 | I-2521 |
| I-2458 | I-2490 | I-2522 |
| I-2459 | I-2491 | I-2523 |
| I-2460 | I-2492 | I-2524 |
| I-2461 | I-2493 | I-2525 |
| I-2462 | I-2494 | I-2526 |
| I-2463 | I-2495 | I-2527 |
| I-2464 | I-2496 | I-2528 |
| I-2465 | I-2497 | I-2529 |
| I-2466 | I-2498 | I-2530 |
| I-2467 | I-2499 | I-2531 |
| I-2532 | I-2564 | I-2596 |
| I-2533 | I-2565 | I-2597 |
| I-2534 | I-2566 | I-2598 |
| I-2535 | I-2567 | I-2599 |
| I-2536 | I-2568 | I-2600 |
| I-2537 | I-2569 | I-2601 |
| I-2538 | I-2570 | I-2602 |
| I-2539 | I-2571 | I-2603 |
| I-2540 | I-2572 | I-2604 |
| I-2541 | I-2573 | I-2605 |
| I-2542 | I-2574 | I-2606 |

TABLE 5-continued

Additional Exemplary Compounds

| Compound | Compound | Compound |
|---|---|---|
| I-2543 | I-2575 | I-2607 |
| I-2544 | I-2576 | I-2608 |
| I-2545 | I-2577 | I-2609 |
| I-2546 | I-2578 | I-2610 |
| I-2547 | I-2579 | I-2611 |
| I-2548 | I-2580 | I-2612 |
| I-2549 | I-2581 | I-2613 |
| I-2550 | I-2582 | I-2614 |
| I-2551 | I-2583 | I-2615 |
| I-2552 | I-2584 | I-2616 |
| I-2553 | I-2585 | I-2617 |
| I-2554 | I-2586 | I-2618 |
| I-2555 | I-2587 | I-2619 |
| I-2556 | I-2588 | I-2620 |
| I-2557 | I-2589 | I-2621 |
| I-2558 | I-2590 | I-2622 |
| I-2559 | I-2591 | I-2623 |
| I-2560 | I-2592 | I-2624 |
| I-2561 | I-2593 | I-2625 |
| I-2562 | I-2594 | I-2626 |
| I-2563 | I-2595 | I-2627 |
| I-2628 | I-2653 | I-2674 |
| I-2629 | I-2654 | I-2675 |
| I-2630 | I-2655 | I-2676 |
| I-2631 | I-2656 | I-2677 |
| I-2632 | I-2657 | I-2678 |
| I-2633 | I-2658 | I-2679 |
| I-2634 | I-2659 | I-2680 |
| I-2635 | I-2660 | I-2681 |
| I-2636 | I-2661 | I-2682 |
| I-2637 | I-2662 | I-2683 |
| I-2638 | I-2663 | I-2684 |
| I-2639 | I-2664 | I-2685 |
| I-2640 | I-2665 | I-2686 |
| I-2641 | I-2666 | I-2687 |
| I-2642 | I-2667 | I-2688 |
| I-2643 | I-2668 | I-2689 |
| I-2648 | I-2669 | I-2694 |
| I-2649 | I-2670 | I-2695 |
| I-2650 | I-2671 | I-2696 |
| I-2651 | I-2672 | I-2697 |
| I-2652 | I-2673 | |

Example 10

N-[6-bromo-3-(2-methylphenyl)-1-oxo-2,3-dihydro-1H-isoindol-4-yl]-1-benzothiophene-3-carboxamide (I-29) and N-[6-(1-methyl-1H-pyrazol-4-yl)-3-(2-methylphenyl)-1-oxo-2,3-dihydro-1H-isoindol-4-yl]-1-benzothiophene-3-carboxamide (I-115)

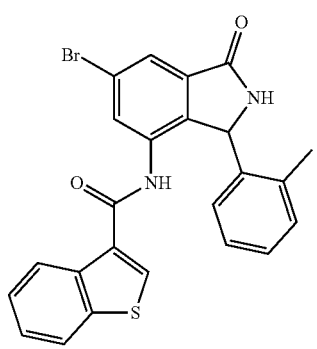

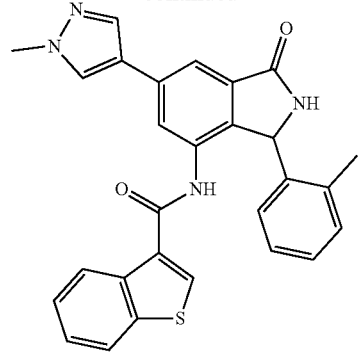

5-Bromo-3-nitrophthalic acid

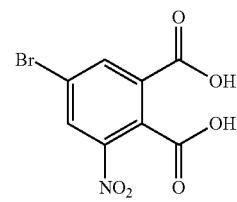 [SMILES: O=C(O)c1cc(Br)cc([N+](=O)[O-])c1C(=O)O]

Step 1: To a solution of 5-bromo-2-methyl-3-nitrobenzoic acid (290 g, 1.12 mol, 1.00 eq) in $H_2O$ (2.90 L) was added KOH (313 g, 5.58 mol, 5.00 eq) at 25° C. To the mixture was added $KMnO_4$ (881 g, 5.58 mol, 5.00 eq) at 70° C., and then the reaction mixture was stirred at 70° C. for 16 hrs. To the reaction mixture was added $Na_2SO_3$ (10%, 3.00 L), then the mixture was filtered. To the filtrate was added 6 M HCl to adjust the pH to 1, and the aqueous phase was extracted three times with ethyl acetate. The combined organic phases were dried over $Na_2SO_4$, filtered, and concentrated under reduced pressure to give 5-bromo-3-nitrophthalic acid (173 g) as a yellow solid. LC-MS (Method 1, 220 nm): 1.73 min, 73.4% purity; $^1$H NMR (400 MHz, DMSO-$d_6$) δ 8.53 (s, 1H), 8.34 (s, 1H).

5-Bromo-3-nitrophthaloyl dichloride

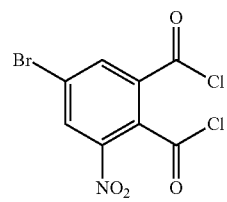 [SMILES: O=C(Cl)c1cc(Br)cc([N+](=O)[O-])c1C(=O)Cl]

Step 2: To a solution of 5-bromo-3-nitrophthalic acid (75.0 g, 259 mmol, 1.00 eq) in toluene (130 mL) was added $SOCl_2$ (245 g, 2.06 mol, 149 mL, 7.97 eq) at 25° C., then the mixture was heated to 100° C. and stirred at 100° C. for 3.5 hrs. Two batches of the mixture were concentrated and then dissolved in, and concentrated from, toluene (3×100 mL) to give 5-bromo-3-nitrophthaloyl dichloride (165 g) as a brown oil. The product was used in the next step without further purification. For LC-MS analysis, the product was quenched with MeOH: LC-MS (Method 1, 220 nm): 0.21 min, m/z=318.0 [M+H]$^+$.

6-Bromo-2-(4-methoxybenzyl)-4-nitroisoindoline-1,3-dione

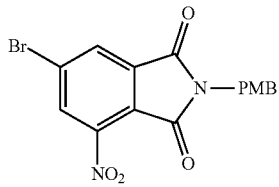

Step 3: To a solution of 5-bromo-3-nitrophthaloyl dichloride (82.3 g, 252 mmol, 1.00 eq) in THF (140 mL) was added a mixture of PMBNH$_2$ (41.4 g, 302 mmol, 39.1 mL, 1.20 eq) and Et$_3$N (83.7 g, 827 mmol, 115 mL, 3.28 eq) in THF (50 mL) dropwise at 0° C., then the mixture was heated to 70° C., and stirred at 70° C. for 15 hrs. The mixture was concentrated and then dissolved in AcOH (189 g, 3.15 mol, 180 mL, 12.5 eq). The mixture was heated to 90° C. and stirred at 90° C. for 4.5 hrs. Two batches of the mixture were diluted with DCM (200 mL) and concentrated. The residue was dissolved in, then concentrated from, toluene (2×200 mL) to give a residue. The residue was dissolved in ethyl acetate (500 mL) and poured into water (500 mL). The aqueous phase was extracted with ethyl acetate (3×500 mL). The combined organic layer was washed with brine (500 mL), dried over Na$_2$SO$_4$, and filtered. The filtrate was concentrated to afford 6-bromo-2-(4-methoxybenzyl)-4-nitroisoindoline-1,3-dione (204 g) as a yellow solid. LC-MS (Method 1, 220 nm): 0.99 min, m/z=415.2 [M+Na]$^+$; $^1$H NMR (400 MHz, DMSO-d$_6$) δ 8.58 (d, J=1.6 Hz, 1H), 8.41 (d, J=1.6 Hz, 1H), 7.27 (d, J=8.8 Hz, 2H), 6.88 (d, J=8.8 Hz, 2H), 4.69 (s, 2H), 3.72 (s, 3H).

4-amino-6-bromo-2-(4-methoxybenzyl)isoindoline-1,3-dione

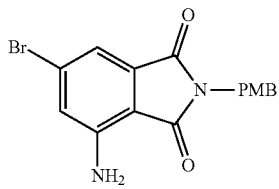

Step 4: To a solution of 6-bromo-2-(4-methoxybenzyl)-4-nitroisoindoline-1,3-dione (100 g, 256 mmol, 1.00 eq) in EtOH (1.00 L)/H$_2$O (200 mL) was added NH$_4$Cl (54.7 g, 1.02 mol, 4.00 eq) at 25° C. The mixture was heated to 40° C., and then Fe (42.8 g, 767 mmol, 3.00 eq) was added into the mixture at 40° C. The resulting mixture was heated to 80° C. and stirred at 80° C. for 1.5 hrs. Two batches of the mixture were poured into water (200 mL), filtered, and the filtrate was concentrated in vacuum. The resulting residue was extracted with ethyl acetate (3×200 mL). The combined organic layer was washed with brine (200 mL), dried over Na$_2$SO$_4$, filtered, and the filtrate was concentrated. The residue was purified by column chromatography (SiO$_2$, petroleum ether/ethyl acetate=1/0 to 0/1, Product R$_f$=0.5 in 3/1 petroleum ether/ethyl acetate) to afford 4-amino-6-bromo-2-(4-methoxybenzyl)isoindoline-1,3-dione (63.3 g, 145.5 mmol, 83.0% purity) as a yellow solid. LC-MS (Method 1, 220 nm): 0.99 min, m/z=361.1 [M+H]$^+$; $^1$H NMR (400 MHz, DMSO-d$_6$) δ 7.22-7.18 (m, 3H), 7.06 (d, J=2.0 Hz, 1H), 6.87 (d, J=8.8 Hz, 2H), 6.65 (s, 2H), 4.61 (s, 2H), 3.71 (s, 3H).

4-Amino-6-bromo-3-hydroxy-2-(4-methoxybenzyl)-3-(o-tolyl)isoindolin-1-one

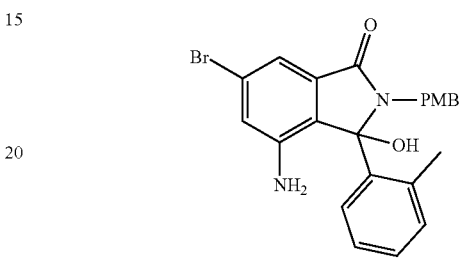

Step 5: To a solution of 4-amino-6-bromo-2-(4-methoxybenzyl)isoindoline-1,3-dione (77.3 g, 178 mmol, 1.00 eq) in DCM (1.00 L) was added o-tolylmagnesium bromide (0.9 M in diethyl ether, 493 mL, 2.50 eq) dropwise at 0° C., then the mixture was warmed to 25° C. and stirred at 25° C. for 1.5 hrs. The mixture was poured into a saturated aqueous solution of NH$_4$Cl (800 mL) and extracted with ethyl acetate (3×800 mL). The combined organic layer was washed with brine (800 mL), dried over Na$_2$SO$_4$, and filtered. The filtrate was concentrated to afford 4-amino-6-bromo-3-hydroxy-2-(4-methoxybenzyl)-3-(o-tolyl)isoindolin-1-one (145.4 g, crude) as a black-brown oil. The product was used in the next step without further purification. LC-MS (Method 1, 220 nm): 0.99 min, m/z=437.2 [M−OH]$^+$.

4-Amino-6-bromo-2-(4-methoxybenzyl)-3-(o-tolyl)isoindolin-1-one

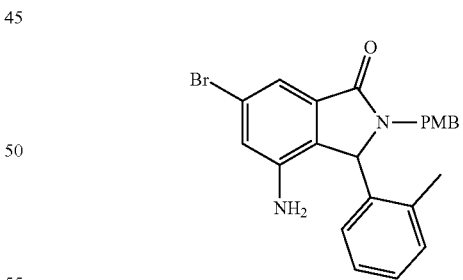

Step 6: To a solution of 4-amino-6-bromo-3-hydroxy-2-(4-methoxybenzyl)-3-(o-tolyl)isoindolin-1-one (131 g, 289 mmol, 1.00 eq) in DCM (1.00 L) was added TFA (330 g, 2.89 mol, 214 mL, 10.0 eq) at 25° C., then to the mixture was added triethylsilane (67.2 g, 578 mmol, 92.3 mL, 2.00 eq) at 0° C. The mixture was warmed to 25° C. and stirred at 25° C. for 1 hr. Two batches of the mixture were concentrated in vacuum to afford a residue. To the residue was added water (500 mL), and the pH was adjusted to 8 with the addition of ammonia. The mixture was extracted with DCM (3×500 mL). The combined organic layer was washed with brine (500 mL), dried over Na$_2$SO$_4$, filtered, and the filtrate was concentrated. The residue was purified by column chromatography (SiO$_2$, petroleum ether/ethyl acetate=1/0 to 0/1) and prep-HPLC to afford 4-amino-6-bromo-2-(4-methoxybenzyl)-3-(o-tolyl)isoindolin-1-one (41.0 g, 86.3 mmol, 94.4% purity) as a red-brown solid and 7-amino-5-bromo-2-(4-methoxybenzyl)-3-(o-tolyl)isoindolin-1-one (29.0 g, 61.7 mmol, 93.1% purity) as a yellow solid.

Characterization data for 4-amino-6-bromo-2-(4-methoxybenzyl)-3-(o-tolyl)isoindolin-1-one: LC-MS (Method 1, 220 nm): 1.00 min, m/z=437.2 [M+H]$^+$; $^1$H NMR (400 MHz, DMSO-d$_6$) δ 7.54-7.53 (m, 1H), 7.28-7.23 (m, 4H), 7.15 (d, J=1.2 Hz, 1H), 6.99-6.97 (m, 8H), 6.93-6.83 (m, 5H), 6.48 (d, J=7.6 Hz, 1H), 5.52 (s, 1H), 5.39 (s, 1H), 4.95-4.87 (m, 3H), 4.74 (s, 1H), 3.71 (s, 6H), 3.58 (d, J=14.8 Hz 1H), 3.49 (d, J=15.6 Hz, 1H), 2.25 (s, 3H), 1.51 (s, 2H).

N-[6-bromo-3-(2-methylphenyl)-1-oxo-2,3-dihydro-1H-isoindol-4-yl]-1-benzothiophene-3-carboxamide (I-29)

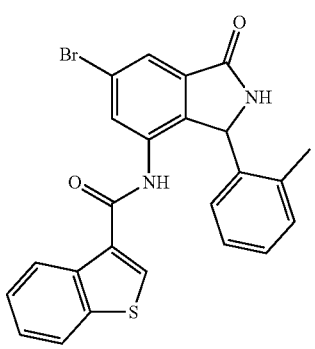 [SMILES: Cc1ccccc1C1NC(=O)c2cc(Br)cc(NC(=O)c3csc4ccccc34)c21]

Steps 7 and 8: According to the procedures of Example 1, Steps 5 and 6, 4-amino-6-bromo-2-(4-methoxybenzyl)-3-(o-tolyl)isoindolin-1-one was converted to N-[6-bromo-3-(2-methylphenyl)-1-oxo-2,3-dihydro-1H-isoindol-4-yl]-1-benzothiophene-3-carboxamide. MS: m/z=477.0 [M+H]$^+$; $^1$H NMR (400 MHz, DMSO-d$_6$) δ 10.12-10.35 (m, 1H), 9.13-9.35 (m, 1H), 7.96-8.08 (m, 2H), 7.80-7.87 (m, 1H), 7.71-7.78 (m, 1H), 7.56-7.68 (m, 1H), 7.32-7.49 (m, 2H), 7.05-7.14 (m, 1H), 6.88-7.05 (m, 2H), 6.44-6.82 (m, 1H), 5.91-6.11 (m, 1H), 1.82-2.38 (m, 3H).

N-[6-(1-methyl-1H-pyrazol-4-yl)-3-(2-methylphenyl)-1-oxo-2,3-dihydro-1H-isoindol-4-yl]-1-benzothiophene-3-carboxamide (I-115)

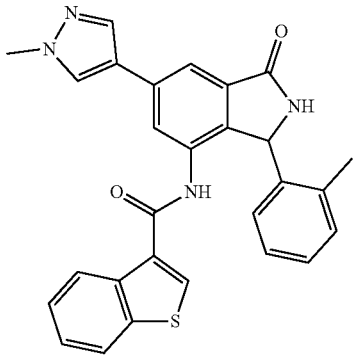

Step 9: N-[6-bromo-3-(2-methylphenyl)-1-oxo-2,3-dihydro-1H-isoindol-4-yl]-1-benzothiophene-3-carboxamide (40 mg, 83.7 μmol), 1-methyl-4-(4,4,5,5-tetramethyl-1,3,2-dioxaborolan-2-yl)-1H-pyrazole (19.1 mg), and Na$_2$CO$_3$ (26 mg) were suspended in dioxane (0.5 mL) in a screw-top glass reaction tube equipped with stir bar. The suspension was subjected to freeze-pump-thaw cycle (3 cycles), and then nitrogen was bubbled through the suspension for 10 mins. Palladium (11) bis(triphenylphosphine) dichloride (1.8 mg, 2.56 μmol) was then added to the suspension. The glass reaction tube was sealed and placed in a pre-heated oil bath (110° C., external) for 5 h with stirring. The reaction mixture was filtered through Celite and washed with ethyl acetate. The combined filtrate was concentrated under reduced pressure, and the residue was purified by reverse-phase flash column chromatography (eluting with 0-100% acetonitrile in water with 10 mM AmF) to furnish after lyophilization N-[6-(1-methyl-1H-pyrazol-4-yl)-3-(2-methylphenyl)-1-oxo-2,3-dihydro-1H-isoindol-4-yl]-1-benzothiophene-3-carboxamide (3.3 mg, 7.8% yield) as a white solid. MS: m/z=479.3 [M+H]$^+$; $^1$H NMR (400 MHz, CDCl$_3$) δ 8.46 (br s, 1H), 8.26 (br s, 1H), 7.88 (s, 1H), 7.86 (d, J=1.4 Hz, 1H), 7.76 (s, 1H), 7.49-7.40 (m, 3H), 7.36 (d, J=7.3 Hz, 1H), 7.24-7.21 (m, 1H), 6.85 (s, 1H), 6.35 (s, 1H), 5.87 (s, 1H), 3.97 (s, 3H), 1.55 (s, 3H).

Additional compounds prepared according to the methods of Example 10 are listed in Table 6 below. Certain compounds in Table 6 below were prepared by replacing N-[6-bromo-3-(2-methylphenyl)-1-oxo-2,3-dihydro-1H-isoindol-4-yl]-1-benzothiophene-3-carboxamide, as described in Example 10, with other compounds whose preparation is described further below in the Examples.

TABLE 6

| Additional Exemplary Compounds |
| --- |
| Compound |
| I-220 |
| I-141 |

Example 11

3-Fluoro-N-[3-(2-methylphenyl)-6-(isopropyl)-1-oxo-2,3-dihydro-1H-isoindol-4-yl]-5-(trifluoromethyl)benzamide (I-266)

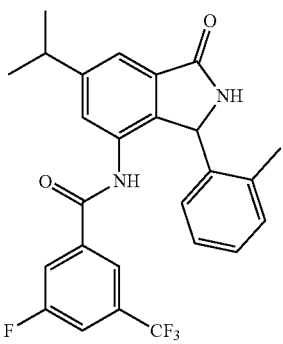 [SMILES: Cc1ccccc1C1NC(=O)c2cc(C(C)C)cc(NC(=O)c3cc(F)cc(C(F)(F)F)c3)c21]

4-Amino-2-[(4-methoxyphenyl)methyl]-3-(2-methylphenyl)-6-(propan-2-yl)-2,3-dihydro-1H-isoindol-1-one

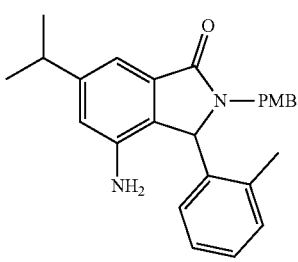

Step 1: A stock solution of nickel(II) dichloride 1,2-dimethoxyethane (6.25 mg) and 4,4'-di-tert-butyl-2,2'-dipyridyl (8.75 mg) in dioxane (0.5 mL) in a 4-mL vial was sparged with nitrogen for 15 mins (until the solution turned light blue). In a separate 4-mL vial with a stir bar, a solution of 4-amino-6-bromo-2-[(4-methoxyphenyl)methyl]-3-(2-methylphenyl)-2,3-dihydro-1H-isoindol-1-one (50 mg, 114 µmol) and [Ir{dFCF$_3$ppy}$_2$(bpy)]PF$_6$ (28.3 mg, 1.0 eq) in dioxane (0.6 mL) was purged with nitrogen with stirring. To this solution were added, in order, 1,1,1,3,3,3-hexamethyl-2-(trimethylsilyl)trisilane (35.1 µL, 1.0 eq), lithium hydroxide (5.46 mg, 2 eq), 100 µL of the nickel/ligand stock solution, and 2-bromopropane (12.7 µL, 1.2 eq). The reaction mixture was sparged for 10 minutes, then sealed. The reaction mixture was placed 6 cm in front of a Blue LED light with stirring for 72 hours. The reaction mixture was concentrated, and the residue was purified by silica gel column chromatography (eluting with 0-100% EtOAc in heptane) to yield 4-amino-2-[(4-methoxyphenyl)methyl]-3-(2-methylphenyl)-6-(propan-2-yl)-2,3-dihydro-1H-isoindol-1-one (30 mg, 74.9 µmol, 65.7%).

3-Fluoro-N-[3-(2-methylphenyl)-6-(isopropyl)-1-oxo-2,3-dihydro-1H-isoindol-4-yl]-5-(trifluoromethyl)benzamide (I-266)

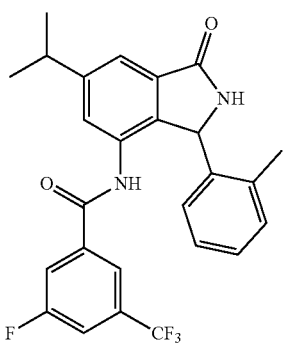 [SMILES: Cc1ccccc1C1NC(=O)c2cc(C(C)C)cc(NC(=O)c3cc(F)cc(C(F)(F)F)c3)c21]

Step 2: To a suspension of 3-fluoro-5-(trifluoromethyl)benzoic acid (39.9 mg, 192 µmol) in DCE (0.2 mL) was added 1-chloro-N,N,2-trimethyl-1-propenylamine (25.3 µL, 2 eq). The mixture was stirred at RT for 5 mins, until the solution became clear, then added to a solution of 4-amino-2-[(4-methoxyphenyl)methyl]-3-(isopropyl)-6-(2-methylpropyl)-2,3-dihydro-1H-isoindol-1-one (40 mg, 96.4 µmol), DMAP (3.70 mg, 9.64 µmol), and pyridine (38.9 µL, 5 eq) in 1,1-dichloroethane (1 mL). The reaction mixture was stirred for approximately 20 minutes, then concentrated.

The residue was treated with 1 mL of TFA and stirred at 100° C. for 2 hours. The reaction was diluted with toluene, then concentrated, three times. The residue was purified prep-HPLC to yield 3-fluoro-N-[3-(2-methylphenyl)-6-(isopropyl)-1-oxo-2,3-dihydro-1H-isoindol-4-yl]-5-(trifluoromethyl)benzamide (9.7 mg, 20.0 µmol, 20.7%). MS: m/z=471.4 [M+H]$^+$; $^1$H NMR (400 MHz, DMSO-d$_6$) δ 1.29 (d, J=6.82 Hz, 6H), 2.17 (br d, J=1.26 Hz, 3H), 3.02-3.14 (m, 1H), 5.85 (s, 1H), 6.60 (s, 1H), 6.87-6.99 (m, 2H), 7.01-7.09 (m, 1H), 7.33-7.41 (m, 2H), 7.49 (br d, 8.84 Hz, 1H), 7.55 (d, J=1.26 Hz, 1H), 7.87 (br d, J=8.59 Hz, 1H), 8.99 (s, 1H), 10.33 (s, 1H).

Additional compounds prepared according to the methods of Example 11 are listed in Table 7 below. Certain compounds in Table 7 below were prepared with other compounds whose preparation is described elsewhere in the Examples.

TABLE 7

| Additional Exemplary Compounds |
| --- |
| Compound |
| I-268 |
| I-293 |

Example 12

N-(6-Bromo-3-(2-chloro-5-fluorophenyl)-1-oxoisoindolin-4-yl)-3-fluoro-5-(trifluoromethyl)benzamide

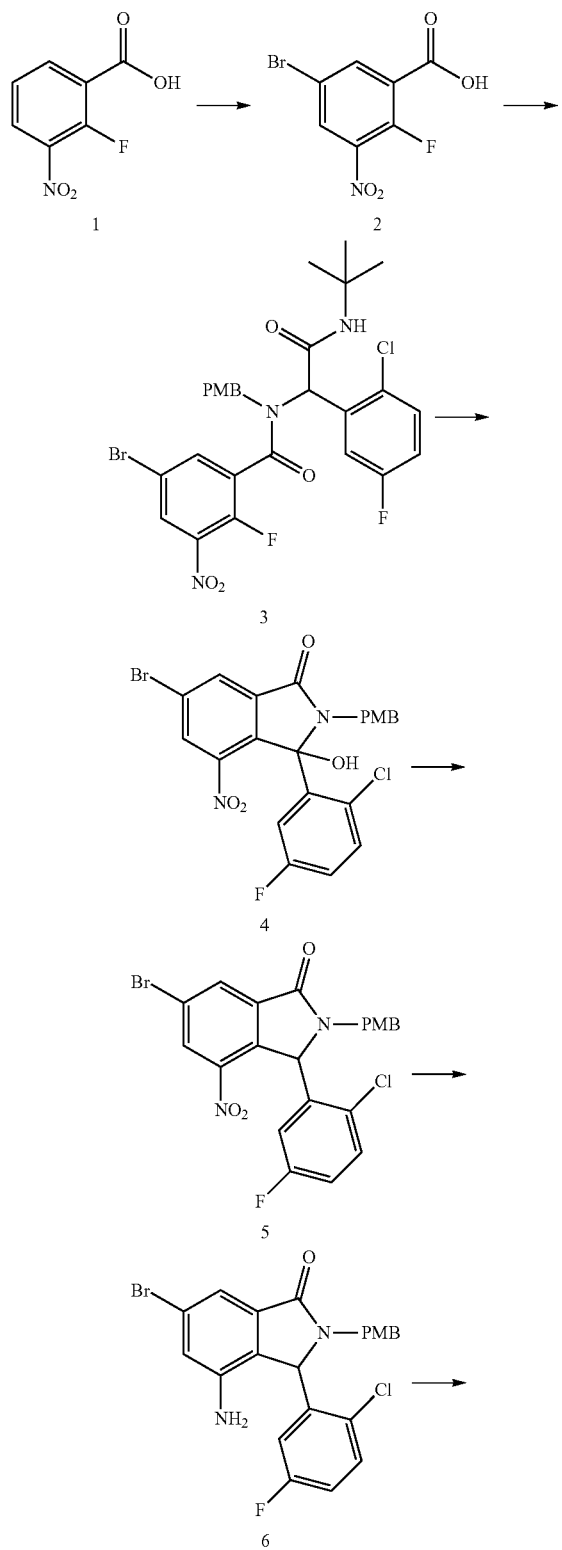

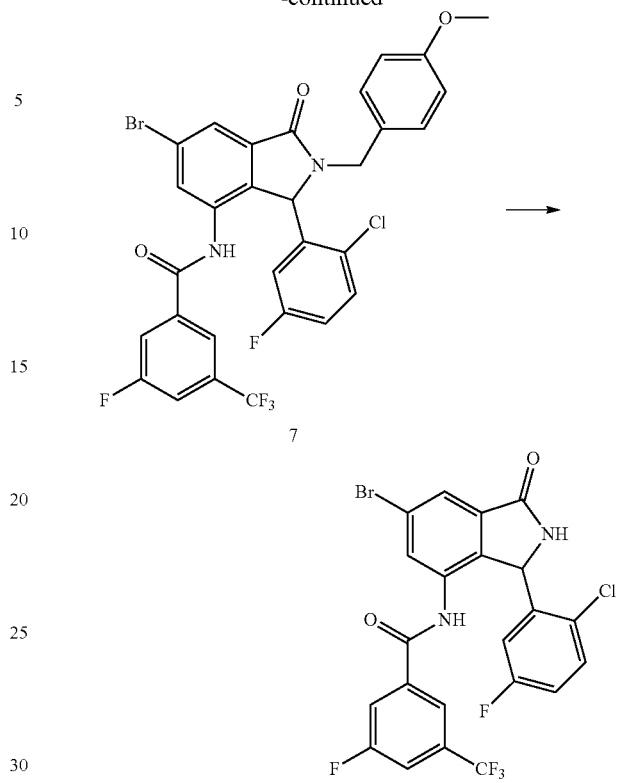

Step 1: To a solution of Compound 1 (185 g, 999 mmol) in $H_2SO_4$ (1.20 L) was added 1,3-dibromo-5,5-dimethylhydantoin (143 g, 500 mmol) at 20° C., the mixture was stirred at 85° C. for 2 h. The mixture was cooled to 20° C., which was then poured to ice water (5.00 L) and filtered. The filtered cake was concentrated under vacuum to afford Compound 2 (240 g, 84.5% yield) as a yellow solid. $^1$H NMR (400 MHz, DMSO-$d_6$) δ 14.15 (br, 1H), 8.55 (d, J=3.2 Hz, 1H), 8.32-8.29 (m, 1H).

Step 2: To a solution of 2-chloro-5-fluorobenzaldehyde (67.0 g, 423 mmol) in MeOH (1.20 L) was sequentially added the following reagents, (4-methoxyphenyl)methanamine (58.0 g, 423 mmol), Compound 2 (120 g, 423 mmol), and tert-butyl isocyanide (35.1 g, 423 mmol) at 20° C. under $N_2$. The mixture was stirred at 20° C. for 2 h. The mixture was directly concentrated. The residue was purified by column chromatography ($SiO_2$, Petroleum ether/Ethyl acetate=50:1 to 5:1, $R_f$=0.40) to afford Compound 3 (248 g, 88.6% yield) as a yellow solid. MS: m/z=648.1 [M+Na]$^-$; $^1$H NMR (400 MHz, DMSO-$d_6$) δ 8.52 (br, 1H), 8.26-8.20 (m, 1H), 7.90 (s, 1H), 7.61-7.51 (m, 1H), 7.28-7.08 (m, 3H), 6.89-6.77 (m, 2H), 6.62-6.60 (m, 2H), 5.39-5.13 (m, 1H), 4.55-4.27 (m, 1H), 3.65 (s, 3H), 1.30-1.25 (m, 9H).

Step 3: To a solution of Compound 3 (243 g, 367 mmol) in ACN (1.50 L) was added 2-tert-butyl-1,1,3,3-tetramethylguanidine (94.3 g, 550 mmol) at 20° C. The mixture was stirred at 50° C. for 2 h. The mixture was concentrated to give Compound 4 (191 g, crude) as a black oil. MS: m/z=522.9 [M+H]$^+$.

Step 4: To a solution of Compound 4 (191 g, 367 mmol) in TFA (1.50 L) was added triethylsilane (213 g, 1.83 mol) at 20° C. The mixture was stirred at 90° C. for 5 h. The mixture was directly concentrated to give Compound 5 (186 g, crude) as a green oil. MS: m/z=505.9 [M+H]$^+$.

Step 5: To a solution of Compound 5 (186 g, 367 mmol) in EtOH (1.20 L) and AcOH (150 mL) was added NH$_4$Cl (137 g, 2.57 mol) at 20° C. The mixture was heated to 50° C. and added Fe (143 g, 2.57 mol) in portions. The mixture was stirred at 80° C. for 1 h. The mixture was diluted with MeOH (2.00 L) and ethyl acetate (2.00 L). Then the mixture was poured into water (4.00 L). The mixture was extracted with ethyl acetate (2.00 L×3). The combined organic layers were washed with brine (2.50 L), dried over Na$_2$SO$_4$, filtered, and concentrated. The crude product was purified by silica gel column chromatography (Petroleum ether/Ethyl acetate=50/1 to 5/1, R$_f$=0.40). Then the crude product was purified by prep-HPLC (column: Phenomenex luna C18 250, 50 mm, 10 um; mobile phase: [water (0.225% FA)-ACN]; B %: 40%-70%, 30 min) to afford Compound 6 (30.5 g, 14.2% yield) as an off-white solid. MS: m/z=476.8 [M+H]$^+$; $^1$H NMR (400 MHz, CDCl$_3$) δ 7.49 (d, J=1.6 Hz, 1H), 7.45-7.41 (m, 1H), 7.12-7.08 (m, 2H), 7.05-7.00 (m, 1H), 6.88 (d, J=1.6 Hz, 1H), 6.83-6.79 (m, 2H), 6.52 (dd, J=3.2, 3.2 Hz, 1H), 5.70 (d, J=1.6 Hz, 1H), 5.17 (d, J=14.8 Hz, 1H), 3.79 (s, 3H), 3.68 (d, J=14.8 Hz, 1H).

Step 6: 4-Amino-6-bromo-3-(2-chloro-5-fluorophenyl)-2-[(4-methoxyphenyl)methyl]-2,3-dihydro-1H-isoindol-1-one (7.0 g, 14.7 mmol) was dissolved in 500 mL of ACN and treated with pyridine (2.32 g, 29.4 mmol) and 3-fluoro-5-(trifluoromethyl)benzoyl chloride (3.33 g, 14.7 mmol). After an hour, a second aliquot of 3-fluoro-5-(trifluoromethyl)benzoyl chloride (0.833 g, 3.67 mmol) was added and the reaction was allowed to stir for 72 h. The mixture was diluted with EtOAc and water. The organic layer was washed with brine, dried over sodium sulfate, filtered, then concentrated to yield N-[6-bromo-3-(2-chloro-5-fluorophenyl)-2-[(4-methoxyphenyl)methyl]-1-oxo-2,3-dihydro-1H-isoindol-4-yl]-3-fluoro-5-(trifluoromethyl)benzamide (11 g, 16.5 mmol)

Step 7: Compound 7 (8.5 g, 12.7 mmol) was added to a flask and dissolved in methane sulfonic acid (35 mL) and heated to 60° C. for 16 h. Aqueous sodium carbonate (10%) was added to the mixture. The aqueous layer was extracted with EtOAc, the organics were then washed with brine, dried over sodium sulfate, filtered, and concentrated to afford N-[6-bromo-3-(2-chloro-5-fluorophenyl)-1-oxo-2,3-dihydro-1H-isoindol-4-yl]-3-fluoro-5-(trifluoromethyl)benzamide (6 g, 86.5% yield).

Additional compounds prepared according to the methods of Example 12 are listed in Table 8 below. Certain compounds in Table 8 were prepared with other compounds whose preparation is described elsewhere in the Examples.

TABLE 8

| Additional Exemplary Compounds Compound |
| --- |
| I-49 |
| I-57 |
| I-83 |
| I-84 |
| I-85 |
| I-99 |
| I-101 |
| I-102 |
| I-122 |
| I-137 |
| I-138 |
| I-157 |
| I-158 |
| I-159 |
| I-160 |
| I-167 |

TABLE 8-continued

| Additional Exemplary Compounds Compound |
| --- |
| I-168 |
| I-169 |
| I-170 |
| I-221 |
| I-241 |
| I-281 |
| I-325 |
| I-330 |
| I-331 |
| I-332 |
| I-371 |
| I-372 |

Example 13

N-[4-Chloro-1-(2-methylphenyl)-3-oxo-1H,2H,3H-pyrrolo[3,4-e]pyridin-7-yl]-3-fluoro-5-(trifluoromethyl)benzamide (I-232)

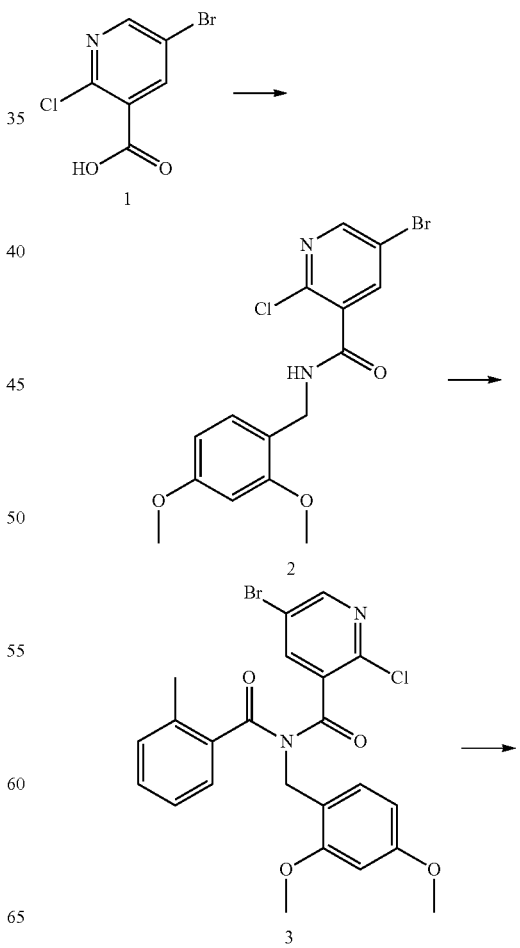

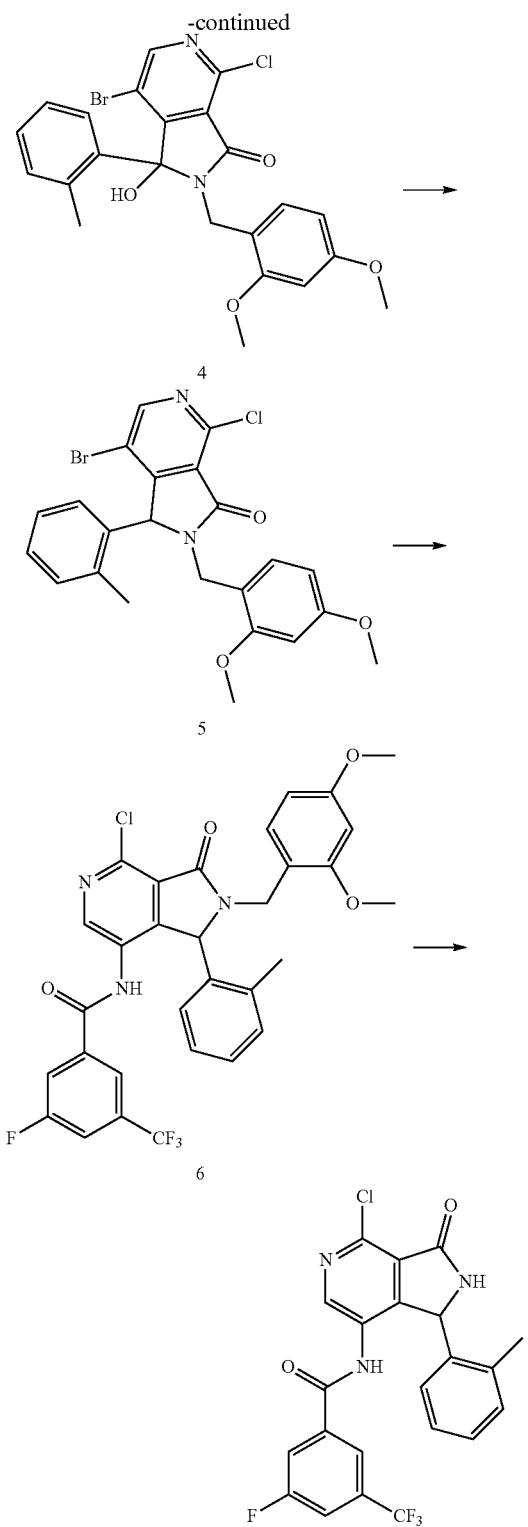

Step 1: To a solution of Compound 1 (30.0 g, 127 mmol) and 2,4-dimethoxybenzylamine (22.3 g, 133 mmol) in DMF (180 mL) was added HOBt (25.7 g, 190 mmol), EDCI (36.5 g, 190 mmol) and DIPEA (41.0 g, 317 mmol) at 0° C. The mixture was stirred at 10-20° C. for 4 h. The mixture was poured into 900 mL water with stirring and extracted with ethyl acetate (1.00 L×3). The organic layer was adjusted pH to 6-7 with 0.5 N HCl, washed with saturated NaHCO$_3$ solution (200 mL) and brine (200 mL×2), dried and concentrated. The residue was triturated with petroleum ether/ethyl acetate=20/1 (300 mL) for 2 h. The mixture was filtered, and the filter cake was dried to give Compound 2 (32.0 g, crude) as a light yellow solid. $^1$H NMR (400 MHz, CDCl$_3$) δ 8.47 (d, J=2.4 Hz, 1H), 8.23 (d, J=2.8 Hz, 1H), 7.25 (d, J=8.0 Hz, 1H), 7.07 (br, s, 1H), 6.48-6.45 (m, 2H), 4.57 (d, J=5.6 Hz, 2H), 3.85 (s, 3H), 3.81 (s, 3H).

Step 2: To a solution of Compound 2 (32.0 g, 83.0 mmol) in THF (320 mL) was added NaH (4.98 g, 124 mmol, 60% purity, 1.50 eq) at 0° C. The mixture was stirred for 0.5 hours at 0° C. and followed by dropwise addition of p-toluoyl chloride (17.5 g, 113 mmol, 14.7 mL, 1.36 eq). The mixture was stirred for additional 2 h at 0-25° C. The mixture was quenched by addition of 150 mL of NH$_4$Cl aqueous solution and extracted with ethyl acetate (150 mL×3). The organic layer was dried and concentrated. The residue was purified by column chromatography (SiO2, petroleum ether/ethyl acetate=1/0 to 5/1, R$_f$=0.50) to give compound 3 (12.8 g) as a yellow solid. $^1$H NMR (400 MHz, CDCl$_3$) δ 8.24 (d, J=2.4 Hz, 1H), 7.43 (d, J=2.4 Hz, 1H), 7.31 (d, J=8.4 Hz, 1H), 7.25-7.19 (m, 2H), 7.13 (d, J=7.2 Hz, 1H), 7.00 (d, J=7.6 Hz, 1H), 6.50-6.47 (m, 1H), 6.43 (d, J=2.4 Hz, 1H), 5.12 (s, 2H), 3.81 (s, 3H), 3.69 (s, 3H), 2.20 (s, 3H).

Step 3: To a solution of compound 3 (12.8 g, 25.4 mmol, 1.00 eq) in THF (128 mL) at −50° C. was added LiHMDS (1 M, 38.1 mL, 1.50 eq). The mixture was stirred at −50° C. for additional 4 hours. The mixture was quenched by 650 mL of saturated NH$_4$Cl solution and extracted with 650 mL×2 of ethyl acetate. The organic layers were combined, washed with brine (650 mL), dried and concentrated to give compound 4 (12.0 g, crude) as a yellow solid. $^1$H NMR (400 MHz, CDCl$_3$) δ 8.48 (s, 1H), 8.21 (d, J=7.6 Hz, 1H), 7.43 (d, J=8.4 Hz, 1H), 7.39 (t, J=7.2 Hz, 1H), 7.30 (t, J=7.0 Hz, 1H), 7.02 (d, J=7.6 Hz, 1H), 6.43-6.41 (m, 1H), 6.34 (d, J=2.0 Hz, 1H), 5.34 (br, s, 1H), 4.54 (d, J=14.4 Hz, 1H), 4.05 (d, J=14.8 Hz, 1H), 3.79 (s, 3H), 3.75 (s, 3H), 1.63 (s, 3H).

Step 4: To a solution of compound 4 (12.0 g, 23.8 mmol) and TFA (67.9 g, 596 mmol) in DCM (120 mL) was added Et$_3$SiH (27.7 g, 238 mmol, 38.1 mL, 10.0 eq). The mixture was stirred at 10-20° C. for 16 h. The mixture was adjusted pH to 7-8 with saturated Na$_2$CO$_3$ solution and extracted with DCM (200 mL×3). The organic layer was washed with brine (100 mL), dried over Na$_2$SO$_4$, filtered, and concentrated. The residue was triturated with a solution of petroleum ether/ethyl acetate=20/1 (50.0 mL) for 12 h, and then filtered to give a filter cake. The cake was dried under vacuum to give compound 5 (8.58 g, 66.2% yield) as a yellow solid. MS: m/z=488.9 [M+H]$^+$; $^1$H NMR (400 MHz, CDCl$_3$) δ 8.48-8.47 (m, 1H), 7.24-7.19 (m, 2H), 7.12-7.08 (m, 1H), 7.04 (d, J=8.0 Hz, 1H), 6.54 (d, J=7.6 Hz, 1H), 6.44-6.41 (m, 2H), 5.59 (s, 1H), 5.03-4.96 (m, 1H), 3.84-3.80 (m, 4H), 3.74-3.72 (m, 3H), 2.33 (s, 3H).

Step 5: A reaction vial was charged with 7-bromo-4-chloro-2-[(2,4-dimethoxyphenyl)methyl]-1-(2-methylphenyl)-1H,2H,3H-pyrrolo[3,4-c]pyridin-3-one (250 mg, 0.512 mmol), 3-fluoro-5-(trifluoromethyl)benzamide (81.6 mg, 0.394 mmol), sodium tert-butoxide (56.8 mg, 0.591 mmol), Pd$_2$(dba)$_3$ (21.6 mg, 23.6 umol), and Xanthphos (4.56 mg, 7.88 umol). The reaction vessel was evacuated and back-filled with nitrogen 3×followed by the addition of dry toluene (5 mL). Heated to 100° C. for 16 h. Quenched with 1N HCl. Diluted with water (5 mL) and extracted with EtOAc (2×10 mL), dried over sodium sulfate and dried onto SiO2. Purified on a CombiFlash® EZ Prep flash column using 0-60% EtOAc in heptanes (40 mm column). Combined fractions were concentrated to give N-{4-chloro-2-

[(2,4-dimethoxyphenyl)methyl]-1-(2-methylphenyl)-3-oxo-1H,2H,3H-pyrrolo[3,4-c]pyridin-7-yl}-3-fluoro-5-(trifluoromethyl)benzamide (321 mg, 25.6%) as an orange solid. MS: m/z=614.28 [M+H]⁺.

Step 6: A solution of N-{4-chloro-2-[(2,4-dimethoxyphenyl)methyl]-1-(2-methylphenyl)-3-oxo-1H,2H,3H-pyrrolo[3,4-c]pyridin-7-yl}-3-fluoro-5-(trifluoromethyl)benzamide (15 mg, 0.02443 mmol) in TFA (500 uL) was heated at 100° C. for 16 h. The mixture was concentrated and purified by reverse-phase HPLC purification (20-40% acetonitrile/water w/0.1% formic acid) to afford N-[4-chloro-1-(2-methylphenyl)-3-oxo-1H,2H,3H-pyrrolo[3,4-c]pyridin-7-yl]-3-fluoro-5-(trifluoromethyl)benzamide (5 mg, 0.01078 mmol).

Example 14

N-(4-Amino-3-oxo-1-(o-tolyl)-2,3-dihydro-1H-pyrrolo[3,4-c]pyridin-7-yl)-3-fluoro-5-(trifluoromethyl)benzamide (I-262)

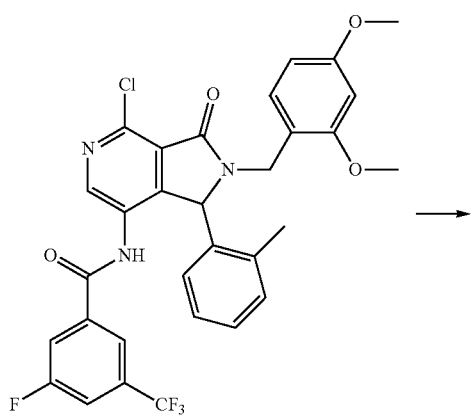

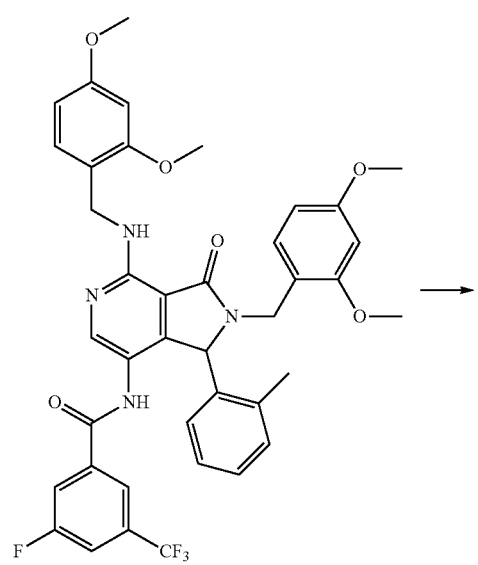

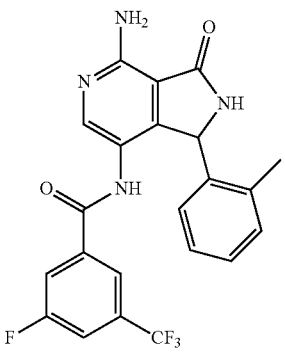

Step 1: Dissolved N-{4-chloro-2-[(2,4-dimethoxyphenyl)methyl]-1-(2-methylphenyl)-3-oxo-1H,2H,3H-pyrrolo[3,4-c]pyridin-7-yl}-3-fluoro-5-(trifluoromethyl)benzamide (75 mg, 0.1221 mmol) in DMF. Bubbled with N₂ for 5 min. Added 1-(2,4-dimethoxyphenyl)methanamine (20.1 μL, 0.1343 mmol) followed by ethylbis(propan-2-yl)amine (31.8 μL, 0.1831 mmol). Stirred at 100° C. for 16 h. The mixture was diluted with EtOAc, extracted with water (2×), washed with brine, dried over Na₂SO₄, and concentrated. The concentrate was purified on prep-HPLC using 0-50% EtOAc in heptanes to give N-{2-[(2,4-dimethoxyphenyl)methyl]-4-{[(2,4-dimethoxyphenyl)methyl]amino}-1-(2-methylphenyl)-3-oxo-1H,2H,3H-pyrrolo[3,4-c]pyridin-7-yl}-3-fluoro-5-(trifluoromethyl)benzamide (59.0 mg, 65%). MS: m/z=745.53 [M+H].

Step 2: N-{2-[(2,4-dimethoxyphenyl)methyl]-4-{[(2,4-dimethoxyphenyl)methyl]amino}-1-(2-methylphenyl)-3-oxo-1H,2H,3H-pyrrolo[3,4-c]pyridin-7-yl}-3-fluoro-5-(trifluoromethyl)benzamide (59.0 mg, 0.07922 mmol) was dissolved in TFA (1 mL) and stirred at RT for 1 h. The mixture was heated to 100° C. for 16 h, and concentrated. The concentrate was dissolved in DCM (1 mL) and to the solution was added Et₃SiH (3 eq) and TFA (10 eq), which was stirred at 80° C. for 1 h. Purified by reverse-phase HPLC to give N-(4-amino-3-oxo-1-(o-tolyl)-2,3-dihydro-1H-pyrrolo[3,4-c]pyridin-7-yl)-3-fluoro-5-(trifluoromethyl)benzamide (5 mg, 0.011 mmol).

Example 15

N-[3-(2-Methylphenyl)-1-oxo-1H,2H,3H-pyrrolo[3,4-c]pyridin-4-yl]-1,2-benzothiazole-3-carboxamide (I-176)

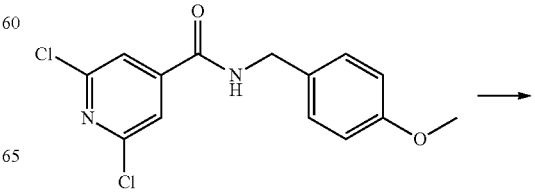

-continued

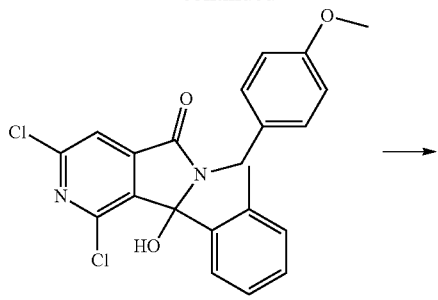

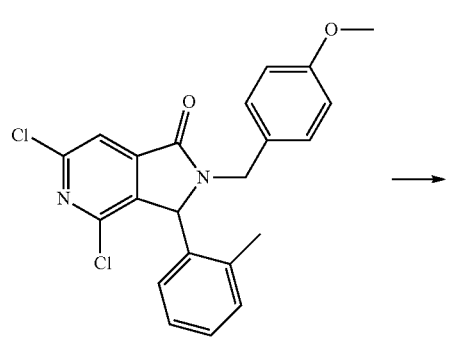

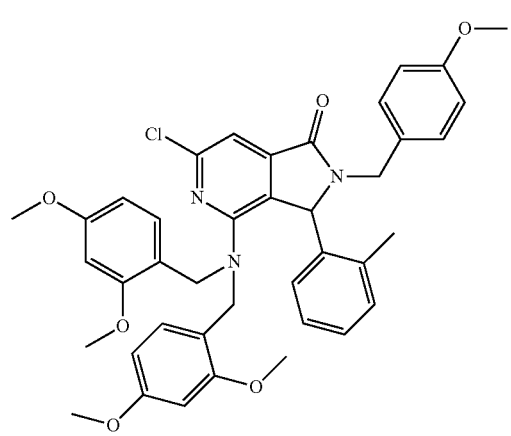

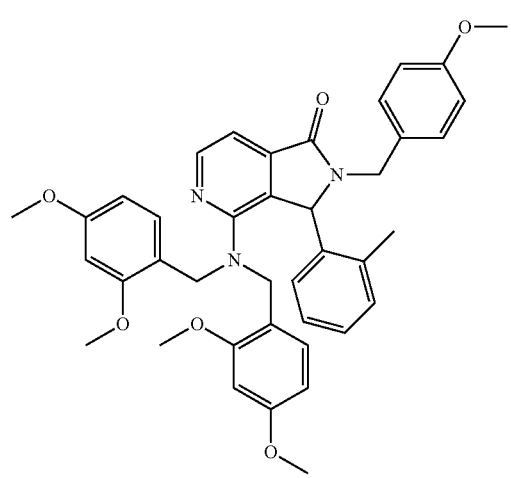

-continued

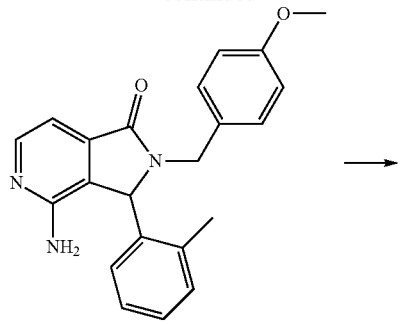

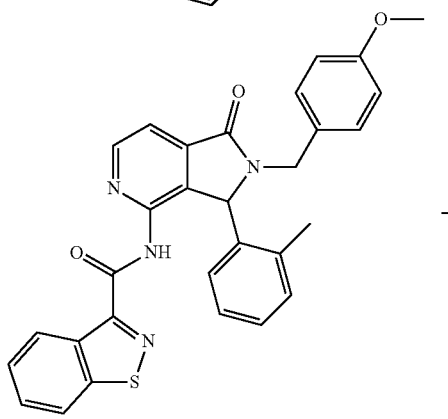

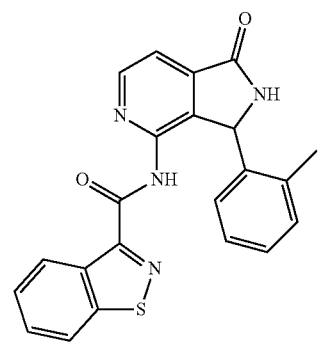

Step 1: To a stirred −50° C. solution under N₂ atmosphere of 2,6-dichloro-N-[(4-methoxyphenyl)methyl]pyridine-4-carboxamide (2.0 g, 6.42 mmol) in THF (32.0 mL) was slowly added LiHMDS (7.05 mL of a 1.0 M solution in THF). The orange solution was stirred at −78° C. for 1 h. To the reaction was added dropwise over 2 min a solution of 2-methylbenzoyl chloride (919 µL, 7.06 mmol). The reaction was stirred 0.5 h at −78° C. and then 16 h at ambient temperature. The mixture was cooled back between −50 to −78° C. and 1.1 equiv. of 1M LiHMDS in THF (7.05 mL) was slowly added. The reaction was stirred at −50 to −78° C. for 1 hour. The mixture was slowly quenched with water and concentrated to remove THF. The suspension was diluted with EtOAc. The layers were separated, and the aqueous layer was extracted twice with EtOAc. The organic layers were combined, washed with brine, dried over Na₂SO₄ and filtered. The crude product was purified by flash chromatography (50 g, solid loading, 0-50% EtOAc/hexanes) to afford 4,6-dichloro-3-hydroxy-2-[(4-methoxyphenyl)methyl]-3-(2-methylphenyl)-1H,2H,3H-pyrrolo[3,4-c]pyridin-1-one (812 mg, 29.5% yield).

Step 2: To a stirred 0° C. solution of 4,6-dichloro-3-hydroxy-2-[(4-methoxyphenyl)methyl]-3-(2-methylphenyl)-1H,2H,3H-pyrrolo[3,4-c]pyridin-1-one (812.8 mg, 1.89 mmol) in DCM (8.45 mL) under nitrogen was added TFA (2.89 mL) followed by triethylsilane (3.00 mL, 18.9 mmol). The reaction was then allowed to warm to ambient temperature and stirred for 16 h. The mixture was diluted with DCM (20 mL) and quenched with saturated aq. NaHCO$_3$ until pH 6-7. The organic layer was extracted once more, washed with brine, dried over Na$_2$SO$_4$, filtered, and concentrated. The crude product was purified by normal phase chromatography (50 g, 30-70% EtOAc/hexanes). Fractions were concentrated to yield 4,6-dichloro-2-[(4-methoxyphenyl)methyl]-3-(2-methylphenyl)-1H,2H,3H-pyrrolo[3,4-c]pyridin-1-one (502 mg, 64.2% yield).

Step 3: A tube containing 4,6-dichloro-2-[(4-methoxyphenyl)methyl]-3-(2-methylphenyl)-1H,2H,3H-pyrrolo[3,4-c]pyridin-1-one (243 mg, 0.5879 mmol), bis[(2,4-dimethoxyphenyl)methyl]amine (205 mg, 0.6466 mmol), ethylbis(propan-2-yl)amine (1.52 mL, 8.81 mmol) and 2-propanol (2.35 mL) was sealed and stirred at 150° C. for 30 h and then cooled to ambient temperature. The mixture was diluted in water/EtOAc. The pH of aqueous layer was adjusted with NH$_4$Cl to pH 7-8. The aqueous layer was extracted twice with EtOAc. The organic layers were combined, washed with brine, and concentrated. The crude product was purified by reverse phase chromatography (30 g, 30%-100% ACN/Ammonium formate (aq)). Fractions containing product were concentrated to yield 4-{bis[(2,4-dimethoxyphenyl)methyl]amino}-6-chloro-2-[(4-methoxyphenyl)methyl]-3-(2-methylphenyl)-1H,2H,3H-pyrrolo[3,4-c]pyridin-1-one (24 mg, 6.1% yield).

Step 4: 4-{Bis[(2,4-dimethoxyphenyl)methyl]amino}-6-chloro-2-[(4-methoxyphenyl)methyl]-3-(2-methylphenyl)-1H,2H,3H-pyrrolo[3,4-c]pyridin-1-one (25 mg, 0.03601 mmol) and NaOAc anhydrous (12.3 mg) were dissolved in methanol (1.2 mL). The solution was purged with N$_2$ and 9.6 mg of Pd/C 10% wt was added. The mixture was purged again with N$_2$ and then with H2. The mixture was stirred at RT under a H2 atmosphere for 16 h. The mixture was purged with N$_2$ and 5 mg of Pd/C 10% wt was added. The mixture was purged again with N$_2$ and then with H$_2$. The mixture was stirred at RT under a H$_2$ atmosphere for 16 h. The mixture was filtered through Celite®, washed with EtOAc/MeOH, concentrated and dried on vacuum to yield 4-{bis[(2,4-dimethoxyphenyl)methyl]amino}-2-[(4-methoxyphenyl)methyl]-3-(2-methylphenyl)-1H,2H,3H-pyrrolo[3,4-c]pyridin-1-one (3 mg).

Step 5: Solid 4-{bis[(2,4-dimethoxyphenyl)methyl]amino}-2-[(4-methoxyphenyl)methyl]-3-(2-methylphenyl)-1H,2H,3H-pyrrolo[3,4-c]pyridin-1-one (24 mg, 0.03637 mmol) was treated with trifluoroacetic acid (0.70 mL, 0.08289 mmol) and stirred at ambient temperature. After 20 min, the mixture was concentrated. The crude mixture containing 4-amino-2-[(4-methoxyphenyl)methyl]-3-(2-methylphenyl)-1H,2H,3H-pyrrolo[3,4-c]pyridin-1-one (13 mg) was used directly for the next step.

Step 6: 4-Amino-2-[(4-methoxyphenyl)methyl]-3-(2-methylphenyl)-1H,2H,3H-pyrrolo[3,4-c]pyridin-1-one (13.0 mg, 0.03616 mmol) was dissolved in pyridine (0.36 mL) and 1,2-benzothiazole-3-carbonyl chloride (10.7 mg, 0.05424 mmol) was added. The mixture was stirred at ambient temperature for 2 h. Approximately 10.7 mg of 1,2-benzothiazole-3-carbonyl chloride was added to the mixture, and it was stirred one more hour. Water (0.4 mL) and 5 mg of K$_2$CO$_3$ were added to the reaction. The mixture was stirred 0.5 h at ambient temperature. The mixture was concentrated, diluted in DCM and water. The pH was adjusted to 7-8 and the layers were separated. The aqueous layer was extracted twice with DCM. The organic layers were combined, washed with brine, dried over Na$_2$SO$_4$, filtered and concentrated. Crude product containing N-(2-(4-methoxybenzyl)-1-oxo-3-(o-tolyl)-2,3-dihydro-1H-pyrrolo[3,4-c]pyridin-4-yl)benzo[d]isothiazole-3-carboxamide (18.8 mg) was used directly in the next step.

Step 7: To a stirred 0° C. solution of N-(2-(4-methoxybenzyl)-1-oxo-3-(o-tolyl)-2,3-dihydro-1H-pyrrolo[3,4-c]pyridin-4-yl)benzo[d]isothiazole-3-carboxamide (19.4 mg, 0.03615 mmol) in DCM (0.18 mL) under nitrogen was added TFA with 0.2% triflic acid (55.3 uL) followed by triethylsilane (57.6 µL, 0.3615 mmol). The reaction was allowed to warm to ambient temperature and stirred for 16 h. The mixture was concentrated, diluted with DCM/water and slowly quenched with saturated aq. NaHCO$_3$ until pH 6-7. The organic layer was extracted once more, washed with brine, and concentrated. The crude product was purified by reverse-phase chromatography (10 g, 10-75% ACN/Ammonium formate 10 mM). The pure fractions were combined, concentrated, and lyophilized to yield N-[3-(2-methylphenyl)-1-oxo-1H,2H,3H-pyrrolo[3,4-c]pyridin-4-yl]-1,2-benzothiazole-3-carboxamide (1 mg, 6.6% yield).

Example 16

N-[5-(2-Chlorophenyl)-2-(methylsulfanyl)-7-oxo-5H,6H,7H-pyrrolo[3,4-d]pyrimidin-4-yl]-3-fluoro-5-(trifluoromethyl)benzamide

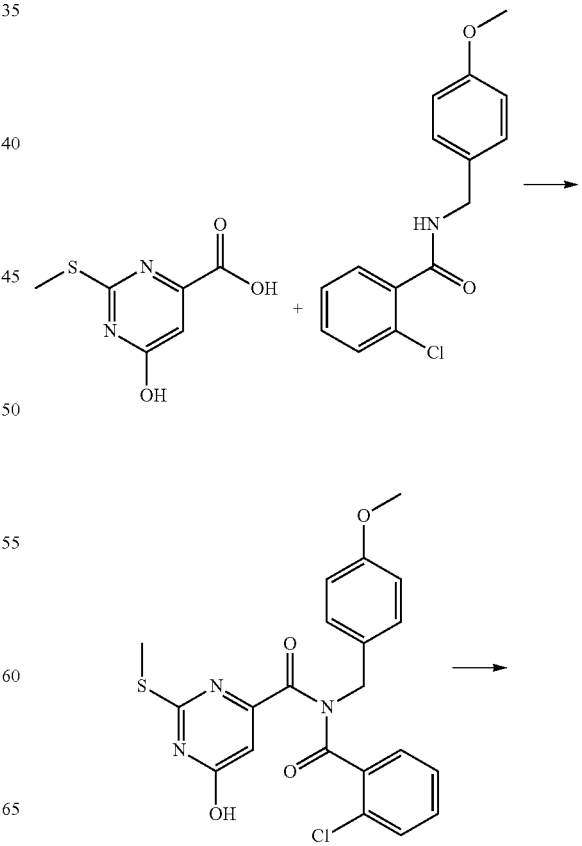

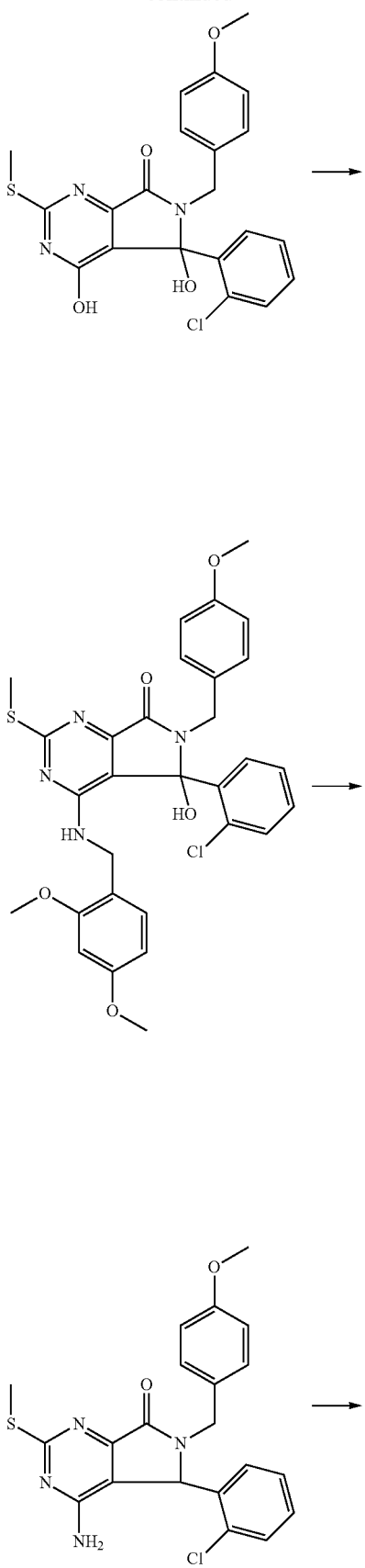

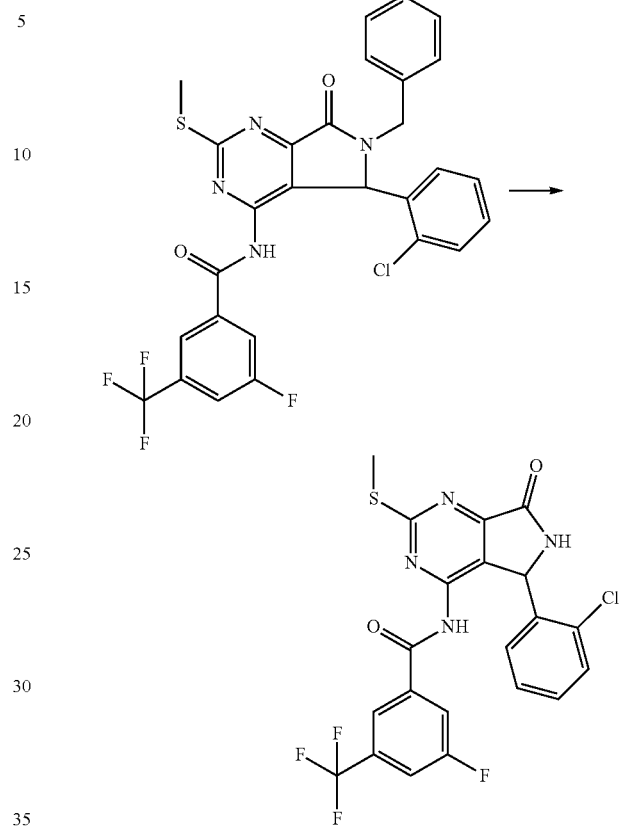

Step 1: To a round bottom flask was added 6-hydroxy-2-(methylsulfanyl)pyrimidine-4-carboxylic acid (1.29 g, 6.95 mmol), which was suspended in POCl₃ (15 mL) and heated to 95° C. After 2 h the reaction was cooled, concentrated, and redissolved in THF (10 mL). In a separate flask, 2-chloro-N-[(4-methoxyphenyl)methyl]benzamide (1.6 g, 5.80 mmol) in THF (15 mL) was cooled to −78° C. and charged with lithiobis(trimethylsilyl)amine (5.80 mL, 5.80 mmol). The solution from flask one was added to the second flask dropwise. After 30 min, the reaction was quenched with water and extracted with ethyl acetate. The organic layers were concentrated to yield 6-chloro-N-(2-chlorobenzoyl)-N-[(4-methoxyphenyl)methyl]-2-(methylsulfanyl)pyrimidine-4-carboxamide (550 mg, 20.5% yield).

Step 2: A mixture of 6-chloro-N-(2-chlorobenzoyl)-N-[(4-methoxyphenyl)methyl]-2-(methylsulfanyl)pyrimidine-4-carboxamide (547 mg, 1.18 mmol) in THF was cooled to −78° C. and charged with lithiobis(trimethylsilyl)amine (1.18 mL, 1.18 mmol). The reaction was stirred at −78° C. for 1 h, and the solution was allowed to warm to −20° C. The reaction was then quenched with saturated with NH₄Cl, and the aqueous layer was extracted with ethyl acetate. The organic layer was concentrated to yield 4-chloro-5-(2-chlorophenyl)-5-hydroxy-6-[(4-methoxyphenyl)methyl]-2-(methylsulfanyl)-5H,6H,7H-pyrrolo[3,4-d]pyrimidin-7-one (418 mg, 0.90 mmol, 76%).

Step 3: To a vial was added 4-chloro-5-(2-chlorophenyl)-5-hydroxy-6-[(4-methoxyphenyl)methyl]-2-(methylsulfa-nyl)-5H,6H,7H-pyrrolo[3,4-d]pyrimidin-7-one (350 mg, 0.7570 mmol) in THF (5 mL), which was then charged with triethylamine (315 μL, 2.27 mmol) and 1-(2,4-dimethoxyphenyl)methanamine (151 mg, 0.9084 mmol) and stirred at ambient temperature. After 6 h, the reaction was poured into a brine solution and extracted with ethyl acetate. The organic layer was concentrated to yield 5-(2-chlorophenyl)-4-{[(2,4-dimethoxyphenyl)methyl]amino}-5-hydroxy-6-[(4-methoxyphenyl)methyl]-2-(methylsulfanyl)-5H,6H,7H-pyrrolo[3,4-d]pyrimidin-7-one (484 mg, crude).

Step 4: To a vial was added 5-(2-chlorophenyl)-4-{[(2,4-dimethoxyphenyl)methyl]amino}-5-hydroxy-6-[(4-methoxyphenyl)methyl]-2-(methylsulfanyl)-5H,6H,7H-pyrrolo[3,4-d]pyrimidin-7-one (450 mg, 0.7587 mmol), then TFA (4 mL), then triethylsilane (1.21 mL, 7.58 mmol) and the mixture was heated to 80° C. After 4 h the reaction was concentrated. The crude material was dissolved in DCM, washed with saturated sodium bicarbonate, then dried over sodium sulfate. The organic layer was filtered and concentrated to yield 4-amino-5-(2-chlorophenyl)-6-[(4-methoxyphenyl)methyl]-2-(methylsulfanyl)-5H,6H,7H-pyrrolo[3,4-d]pyrimidin-7-one (265 mg, 82% yield).

Step 5: To a vial containing 3-fluoro-5-(trifluoromethyl)benzoic acid (36.5 mg, 0.1756 mmol) in toluene (1 mL) was added (1-chloro-2-methylprop-1-en-1-yl)dimethylamine (23.1 μL, 0.1756 mmol), and the mixture was stirred at ambient temperature for 30 min to create a stock solution. In a separate vial, 4-amino-5-(2-chlorophenyl)-6-[(4-methoxyphenyl)methyl]-2-(methylsulfanyl)-5H,6H,7H-pyrrolo[3,4-d]pyrimidin-7-one (50 mg, 0.1171 mmol) in THF (3 mL) was cooled to 0° C., and was charged with lithiobis(trimethylsilyl)amine (175 μL, 0.1756 mmol). After 15 min, the stock solution of acid chloride was added and stirred for 30 min. The solvent was removed, and the residue was purified by prep-HPLC to yield N-[5-(2-chlorophenyl)-6-[(4-methoxyphenyl)methyl]-2-(methylsulfanyl)-7-oxo-5H,6H,7H-pyrrolo[3,4-d]pyrimidin-4-yl]-3-fluoro-5-(trifluoromethyl)benzamide (15 mg, 20% yield).

Step 6: To a microwave vial was added N-[5-(2-chlorophenyl)-6-[(4-methoxyphenyl)methyl]-2-(methylsulfanyl)-7-oxo-5H,6H,7H-pyrrolo[3,4-d]pyrimidin-4-yl]-3-fluoro-5-(trifluoromethyl)benzamide (15 mg, 0.02431 mmol) in TFA+1% TfOH (1.5 mL), which was heated in a microwave at 75° C. for 50 min. The solvent was removed, and the residue was purified by prep-HPLC to yield N-[5-(2-chlorophenyl)-2-(methylsulfanyl)-7-oxo-5H,6H,7H-pyrrolo[3,4-d]pyrimidin-4-yl]-3-fluoro-5-(trifluoromethyl)benzamide (6.5 mg, 54% yield).

Example 17

3-Fluoro-N-[1-(1-methylcyclohexyl)-3-oxo-2,3-dihydro-1H-indazol-7-yl]-5-(trifluoromethyl)benzamide

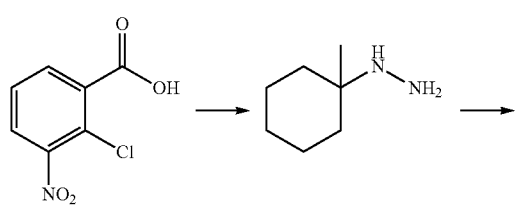

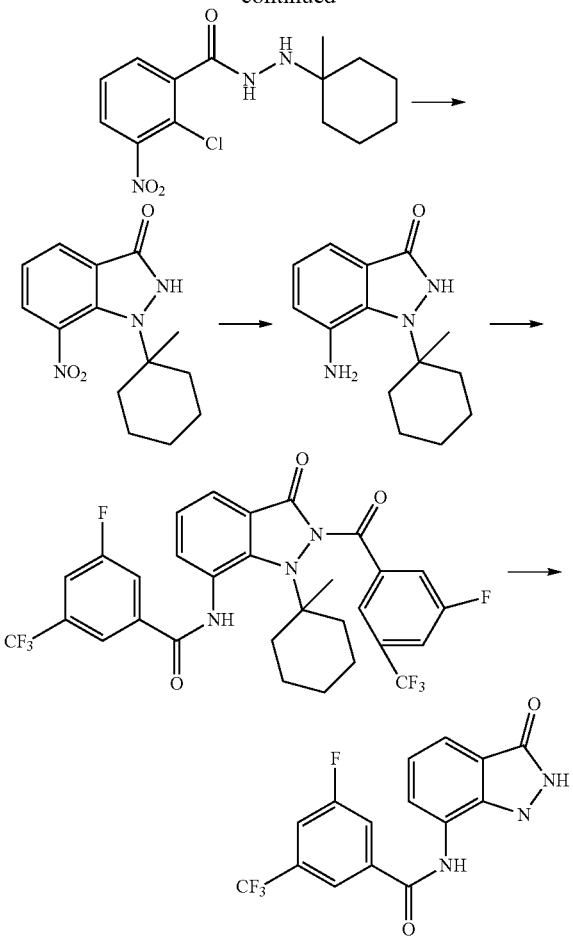

Step 1: To a solution of 2-chloro-3-nitrobenzoic acid (1 g, 4.96 mmol), (1-methylcyclohexyl)hydrazine (635 mg, 4.96 mmol) and HATU (2.82 g, 7.44 mmol) in DMF (50 mL) was added sodium bicarbonate (1.24 g, 14.8 mmol). The mixture was stirred at ambient temperature overnight, and then the mixture was washed with sat. NaHCO₃ and brine. The reaction mixture was concentrated and purified by reverse-phase chromatography (30 g column, 10 mM ammonium formate in water/acetonitrile system (5-100%)) and lyophilized to give 2-chloro-N'-(1-methylcyclohexyl)-3-nitrobenzohydrazide (500 mg, 26.9% yield).

Step 2: To a round bottomed flask was added 2-chloro-N'-(1-methylcyclohexyl)-3-nitrobenzohydrazide (500 mg, 1.60 mmol), sodium tert-butoxide (230 mg, 2.40 mmol), and DMF (20 mL). The mixture was stirred at 90° C. for 2 h under inert atmosphere. The reaction mixture was concentrated and purified by reverse-phase chromatography (30 g column, 10 mM ammonium formate in water/acetonitrile system (5-100%)) and fractions were lyophilized to give 1-(1-methylcyclohexyl)-7-nitro-2,3-dihydro-1H-indazol-3-one (180 mg, 39.9% yield).

Step 3: A 30-mL vial was charged with 1-(1-methylcyclohexyl)-7-nitro-2,3-dihydro-1H-indazol-3-one (180 mg, 653 μmol), iron (364 mg, 6.52 mmol) and acetic acid (668 μL, 11.7 mmol). The mixture was suspended in 4:1 MeOH/water (15 mL) and vigorously stirred at 90° C. for 30 min. The mixture was filtered through a pad of Celite®. The filtrate was concentrated under reduced pressure to give 7-amino-1-(1-methylcyclohexyl)-2,3-dihydro-1H-indazol-3-one (70 mg, 43.7% yield).

1835

Step 4: To a solution of 7-amino-1-(1-methylcyclohexyl)-2,3-dihydro-1H-indazol-3-one (70 mg, 285 μmol) in DCM (5 mL) were added pyridine (112 mg, 1.42 mmol) and 3-fluoro-5-(trifluoromethyl)benzoyl chloride (129 mg, 570 μmol), and the resulting mixture was stirred at ambient temperature for 1 hour. Reaction mixture was concentrated, washed with aq. NH$_4$Cl, extracted with DCM. The organic layer was concentrated to obtain the crude sticky residue (150 mg) which was used in the next step without further purification. Yield was assumed quantitative.

Step 5: 3-Fluoro-N-{2-[3-fluoro-5-(trifluoromethyl)benzoyl]-1-(1-methylcyclohexyl)-3-oxo-2,3-dihydro-1H-indazol-7-yl}-5-(trifluoromethyl)benzamide (180 mg, 287 μmol) was dissolved in methanol (10 mL), then potassium carbonate (395 mg, 2.86 mmol) was added, and the reaction mixture was stirred at 60° C. for 1 hour. The reaction mixture was concentrated and purified by reverse-phase chromatography (30 g column, 10 mM ammonium formate in water/acetonitrile system (5-100%)) to give 3-fluoro-N-[1-(1-methylcyclohexyl)-3-oxo-2,3-dihydro-1H-indazol-7-yl]-5-(trifluoromethyl)benzamide (80 mg, 181 μmol, 63.8%).

Additional compounds prepared according to the methods of Example 17 are listed in Table 9 below. Certain compounds in Table 9 were prepared with other compounds whose preparation is described elsewhere in the Examples.

TABLE 9

Additional Exemplary Compounds
Compound

I-68
I-117
I-152
I-178
I-252
I-323

Example 18

N-(1,1-Dioxido-3-(o-tolyl)-2,3-dihydrobenzo[d]isothiazol-4-yl)-3-fluoro-5-(trifluoromethyl)benzamide

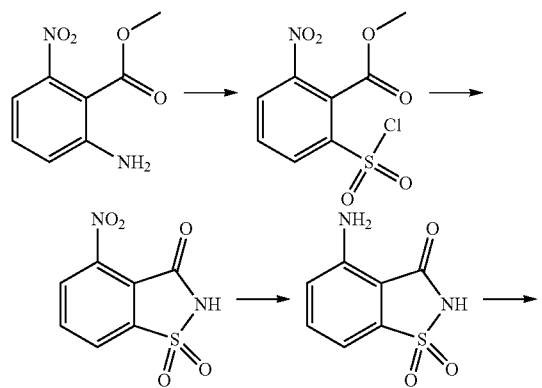

1836

-continued

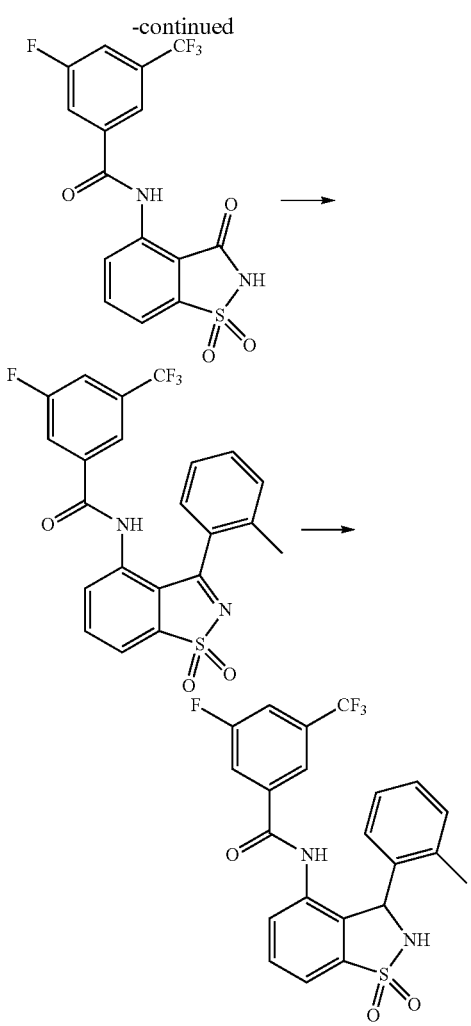

Step 1: (A) To water (36 mL) cooled to 0° C. was added thionyl chloride (6.08 mL, 4.3 eq, 14.2 mmol) keeping the temperature at 0-7° C. (very exothermic, slow careful addition with dropping funnel). The mixture allowed to warm to room temperature for 1 hour after which CuCl (191 mg, 0.1 eq) was added and the solution cooled to −3° C. using a brine/ice bath. (B) Concentrated hydrogen chloride (30 mL, 1.0 eq, 36% w/w) was added to methyl 2-amino-6-nitrobenzoate (3.8 g, 19.3 mmol) keeping the temperature below 30° C. with ice/brine mixture cooling, and the mixture was cooled to −5° C. Sodium nitrite (1.52 g, 1.15 eq) was dissolved in water (5 mL) (exothermic, slow careful addition with dropping funnel required) was added dropwise keeping the temperature between −5 and 0° C. and stirred for an additional 15 min. The slurry from (B) was added dropwise to solution (A) while keeping the temperature of both solutions between 0 and −5° C. and this mixture stirred for 30 min, filtered, rinsed with water, and air dried, which resulted in a wet cake. Material was dried under vacuum to give methyl 2-(chlorosulfonyl)-6-nitrobenzoate (5.34 g, 99% yield).

Step 2: A round bottom flask was charged with methyl 2-(chlorosulfonyl)-6-nitrobenzoate (1 g, 3.57 mmol) and dioxane (5 mL), and the mixture was cooled to 0° C. using an ice bath. Ammonium hydroxide (5 mL, conc. 35 wt %) was added dropwise, and the mixture was allowed to warm to RT over 90 min. The mixture was cooled to 0° C., and conc. HCl (ca. 4 mL) was added to reach pH 1. Water (30 mL) was added and the reaction mixture was filtered on a fritted funnel, which was rinsed with water and air dried to afford 4-nitrobenzo[d]isothiazol-3(2H)-one 1,1-dioxide (560 mg, 68.7% yield) as an off-white solid.

Step 3: A reaction vial was loaded with 4-nitrobenzo[d]isothiazol-3(2H)-one 1,1-dioxide (500 mg, 2.19 mmol), palladium hydroxide, 20 wt. % Pd on carbon, wet (100 mg, 0.429 eq) and purged with nitrogen. Anhydrous methanol (8 mL) was added and nitrogen purging was continued for 2 minutes, followed by purging with hydrogen (from a balloon) for 5 minutes. The mixture was stirred at ambient temperature for 16 hours. The mixture was purged with nitrogen and filtered through a small celite pad on a fritted funnel. The filtrate was concentrated to dryness to afford 4-aminobenzo[d]isothiazol-3(2H)-one 1,1-dioxide (368 mg, 1.81 mmol, 82.9%) as a tan powder.

Step 4: A round bottom flask was charged with 4-aminobenzo[d]isothiazol-3(2H)-one 1,1-dioxide (236 mg, 1.19 mmol), 4-dimethylaminopyridine (14.5 mg, 0.1 eq) and anhydrous pyridine (3 mL), followed by dropwise addition of 3-fluoro-5-(trifluoromethyl)benzoyl chloride (403 mg, 1.78 mmol). The reaction mixture was stirred at ambient temperature for 1 hour. The reaction mixture was diluted with DCM (50 mL) and water (10 mL) and acidified to pH 1 with 1 M HCl (ca. 30 mL). The DCM phase was separated out, and the aqueous phase was extracted with EtOAc (30 mL). The organic phases were combined, dried over sodium sulfate, and concentrated to dryness. The crude mixture was triturated with DCM (ca. 8 mL) and filtered to afford N-(1,1-dioxido-3-oxo-2,3-dihydrobenzo[d]isothiazol-4-yl)-3-fluoro-5-(trifluoromethyl)benzamide (355 mg, 0.9142 mmol, 76.8%) as a tan solid.

Step 5: A dry round bottom flask under nitrogen was charged with N-(1,1-dioxido-3-oxo-2,3-dihydrobenzo[d]isothiazol-4-yl)-3-fluoro-5-(trifluoromethyl)benzamide (100 mg, 0.2575 mmol) and anhydrous tetrahydrofuran (1.03 mL), and the mixture was cooled to 0° C. Bromo(2-methylphenyl)magnesium (772 µL, 0.7725 mmol, 1 M in THF) was added dropwise and warmed to ambient temperature over 1 hour. After 1 hour, a second portion of bromo(2-methylphenyl)magnesium (257 ul, 257 uM, 1 M in THF) was added, and stirred at ambient temperature for 3 hours, followed by a third portion of bromo(2-methylphenyl)magnesium (257 ul, 257 uM, 1 M in THF) and the mixture was stirred at ambient temperature overnight. The reaction mixture was quenched with saturated NH$_4$Cl (5 mL), diluted with water (5 mL), and extracted with EtOAc (3×12 mL), dried over sodium sulfate and concentrated to dryness to afford N-(1,1-dioxido-3-(o-tolyl)benzo[d]isothiazol-4-yl)-3-fluoro-5-(trifluoromethyl)benzamide (120 mg, 0.1038 mmol, 40.3%). The crude product was used directly for the next step.

Step 6: A round bottom flask was charged with crude N-(1,1-dioxido-3-(o-tolyl)benzo[d]isothiazol-4-yl)-3-fluoro-5-(trifluoromethyl)benzamide (60 mg, 0.1297 mmol) and anhydrous methanol (1.29 mL), then sodium borohydride (14.7 mg, 3 eq) was added (instant gas evolution). The reaction mixture was stirred for 3 hours. The reaction mixture was concentrated to dryness and purified by reverse-phase flash chromatography (12 g C18 cartridge, 10 to 80% ACN in ammonium formate (aq)). An impurity (Rt=1.80 min) co-eluted with the desired product. All fractions containing desired product were concentrated together and re-purified by normal-phase flash chromatography (12 g cartridge, 0 to 25% EtOAc in DCM) to afford N-(1,1-dioxido-3-(o-tolyl)-2,3-dihydrobenzo[d]isothiazol-4-yl)-3-fluoro-5-(trifluoromethyl)benzamide (17 mg, 28.2%) as a white solid after lyophilization.

Example 19

(Z)—N-[3-(2-Chloro-5-fluorophenyl)-1-sulfanylidene-2,3-dihydro-1H-isoindol-4-yl]-3-fluoro-N'-hydroxy-5-(trifluoromethyl)benzimidamide

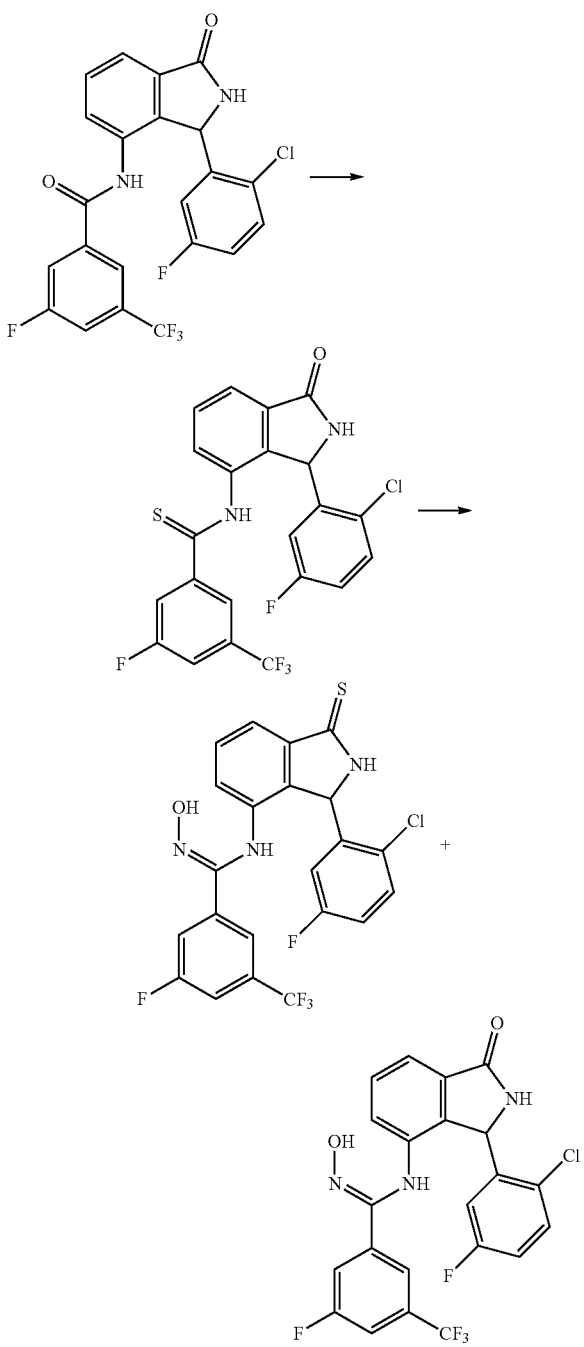

Step 1: A suspension of N-[3-(2-chloro-5-fluorophenyl)-1-oxo-2,3-dihydro-1H-isoindol-4-yl]-3-fluoro-5-(trifluoromethyl)benzamide (0.065 g, 139 µmol) in toluene (2 mL) was treated with bis(4-methoxyphenyl)-1,3,2,4-dithiadiphosphetane-2,4-dithione (60.2 mg). The mixture was stirred at 100° C. for 3 h and then purified by silica-gel chromatography (0-100% EtOAc/hexanes) to provide N-[3-(2-chloro-5-fluorophenyl)-1-oxo-2,3-dihydro-1H-isoindol-4-yl]-3-fluoro-5-(trifluoromethyl)benzene-1-carbothioamide (0.038 g, 78.6 µmol, 56%).

Step 2: A solution of N-[3-(2-chloro-5-fluorophenyl)-1-oxo-2,3-dihydro-1H-isoindol-4-yl]-3-fluoro-5-(trifluoromethyl)benzene-1-carbothioamide (0.038 g, 78.6 µmol) in ethanol (3 mL) was treated with NaHCO₃ (2 eq) and hydroxylamine hydrochloride (2 eq). The mixture was stirred at 70° C. for 48 h and then purified by reverse-phase HPLC (20-70% ACN/water) to provide (Z)—N-[3-(2-chloro-5-fluorophenyl)-1-sulfanylidene-2,3-dihydro-1H-isoindol-4-yl]-3-fluoro-N'-hydroxy-5-(trifluoromethyl)benzimidamide (0.005 g, 7.02 µmol, 9% yield) as light-yellow powder.

Example 20

5-Bromo-4-(2-methylphenyl)-3,4-dihydro-2H-1,3-benzoxazin-2-one

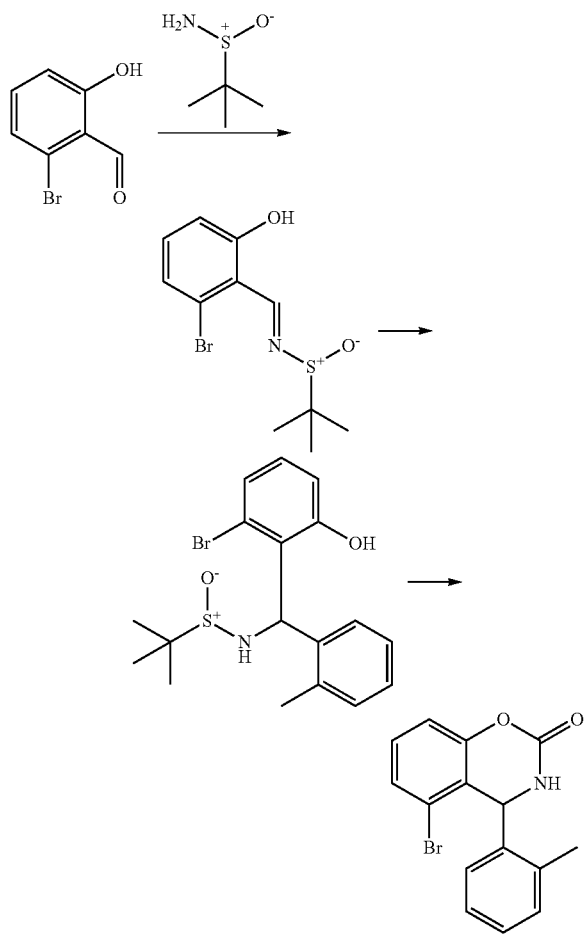

Step 1: To 2-bromo-6-hydroxybenzaldehyde (1.72 g, 8.55 mmol) and 2-methylpropane-2-sulfinamide (1.23 g, 10.2 mmol) in THF (25 mL) was added tetraethoxytitanium (5.35 mL, 25.6 mmol). The mixture was stirred at ambient temperature for 2 hours. The solution was then quenched with aqueous sodium bicarbonate. The aqueous layer was extracted with DCM. The organic layer was concentrated to afford N-[(E)-(2-bromo-6-hydroxyphenyl)methylidene]-2-methylpropane-2-sulfinamide (2.6 g, 8.55 mmol, 99%).

Step 2: To a solution of N-[(E)-(2-bromo-6-hydroxyphenyl)methylidene]-2-methylpropane-2-sulfinamide (200 mg, 0.6574 mmol) in THF (3 mL) at 0° C. was added bromo(2-methylphenyl)magnesium (985 µL, 1.97 mmol, 2 M in THF). Reaction was allowed to warm to ambient temperature after 5 minutes of stirring at 0° C. Mixture was stirred for 15 minutes before quenching with saturated NH₄Cl. The aqueous layer was extracted with ethyl acetate, and the organic layer was concentrated to yield N-[(2-bromo-6-hydroxyphenyl)(2-methylphenyl)methyl]-2-methylpropane-2-sulfinamide (260 mg, 0.650 mmol, 99%).

Step 3: To N-[(2-bromo-6-hydroxyphenyl)(2-methylphenyl)methyl]-2-methylpropane-2-sulfinamide (210 mg, 0.5298 mmol) in 2-MeTHF (3 mL) was added 1-(1H-imidazole-1-carbonyl)-1H-imidazole (170 mg, 1.05 mmol) and heated to 90° C. for 16 h. The solution was cooled, then MTBE was added dropwise until solid started to precipitate. The solid was then filtered and dried to afford 5-bromo-4-(2-methylphenyl)-3,4-dihydro-2H-1,3-benzoxazin-2-one (95 mg, 0.538 mmol, 56.5%).

Example 21

N-(4-(2-Chlorophenyl)-2-oxo-1,2,3,4-tetrahydroquinazolin-5-yl)-3-fluoro-5-(trifluoromethyl)benzamide

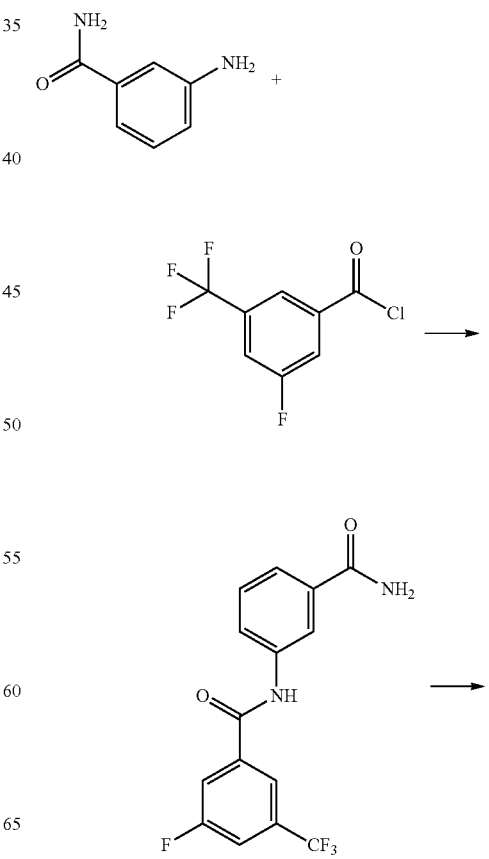

1841

-continued

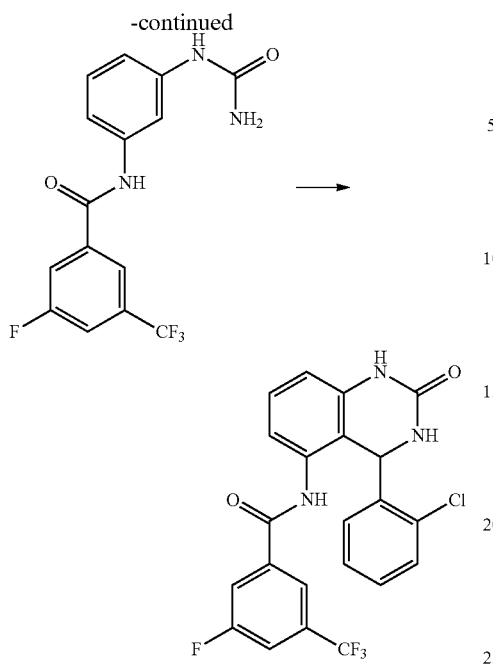

Step 1: A round bottom flask was charged with 3-aminobenzamide (500 mg, 3.67 mmol) and 4-dimethylaminopyridine (22.4 mg, 0.05 eq) and flushed with nitrogen. Anhydrous pyridine (7.34 mL) was added followed by 3-fluoro-5-(trifluoromethyl)benzoyl chloride (837 µL, 5.50 mmol), and the reaction mixture was stirred at ambient temperature for 1.5 hours. Water (20 mL) was added, and the reaction mixture was stirred for 10 minutes. The mixture was filtered through a fritted funnel, and the precipitate was rinsed with water and a small amount of acetonitrile, then air dried to afford N-(3-carbamoylphenyl)-3-fluoro-5-(trifluoromethyl) benzamide (726 mg, 2.22 mmol, 61.0%) as a white powder.

Step 2: A solution of N-(3-carbamoylphenyl)-3-fluoro-5-(trifluoromethyl)benzamide (175 mg, 0.5867 mmol) and N,N-diisopropylethylamine (107 µL, 1.05 eq) in anhydrous THF (2.93 mL) under nitrogen was cooled to 0° C. using an ice bath, and a solution of triphosgene (174 mg, 0.5867 mmol) in THF (3 mL) was added dropwise. The reaction mixture was stirred at 0° C. for 1 hour followed by the dropwise addition of ammonium hydroxide (390 µL, 5.86 mmol, 25 wt % in water) and stirred for 10 minutes. The reaction mixture was diluted with water (15 mL), extracted with EtOAc (2×15 mL), washed with saturated NH$_4$Cl, dried over sodium sulfate, filtered, and concentrated to afford N-[3-(carbamoylamino)phenyl]-3-fluoro-5-(trifluoromethyl)benzamide (210 mg, 0.5845 mmol, 99.5%) as a tan solid.

Step 3: A reaction vial was charged with N-[3-(carbamoylamino)phenyl]-3-fluoro-5-(trifluoromethyl)benzamide (100 mg, 0.2930 mmol) and 2-chlorobenzaldehyde (49.4 mg, 0.3515 mmol), and phosphorus pentoxide in MeOH (7.7% weight, 0.5 mL, 1.0 eq) was added. The reaction mixture was heated to 80° C. for 45 min, then poured into sat. NaHCO$_3$. The mixture was extracted with EtOAc (2×15 mL), washed with saturated NaHCO$_3$ (10 mL), dried over sodium sulfate and concentrated to dryness. Purification via reverse-phase chromatography (12 g C18 cartridge, 5 to 70% ACN in AmF) afforded N-(4-(2-chlorophenyl)-2-oxo-1,2,3,4-tetrahydroquinazolin-5-yl)-3-fluoro-5-(trifluoromethyl)benzamide (8 mg, 5.65%) as a white solid.

1842

Example 22

N-[1-(2-Chlorophenyl)-3-oxo-1,2,3,4-tetrahydroisoquinolin-8-yl]-3-fluoro-5-(trifluoromethyl)benzamide

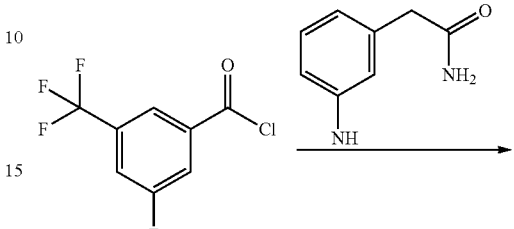

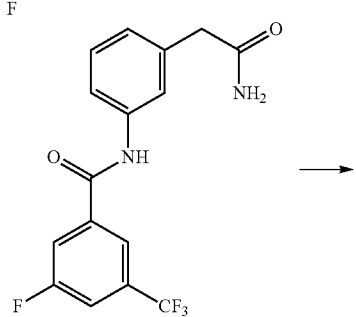

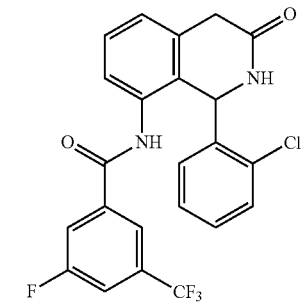

Step 1: A round bottom flask was charged with 2-(3-aminophenyl)acetamide (250 mg, 1.66 mmol) and 4-dimethylaminopyridine (10.1 mg, 0.05 eq) and flushed with nitrogen. Anh. pyridine (5.53 mL) was added followed by 3-fluoro-5-(trifluoromethyl)benzoyl chloride (379 µL, 2.48 mmol), and the reaction mixture was stirred at ambient temperature for 16 hours. Water (20 mL) was added to the reaction mixture, stirred for 10 min, and the precipitate was filtered and air dried. The residue was dried under high vacuum to afford N-[3-(carbamoylmethyl)phenyl]-3-fluoro-5-(trifluoromethyl)benzamide (570 mg, 1.40 mmol, 84.7%) as a tan powder.

Step 2: A reaction vial was charged with N-[3-(carbamoylmethyl)phenyl]-3-fluoro-5-(trifluoromethyl)benzamide (100 mg, 0.2938 mmol) and 2-chlorobenzaldehyde (45.4 mg, 0.3231 mmol), then P$_2$O$_5$ in MeOH (7.7% weight, 0.5 mL, 1.0 eq) was added, and the reaction mixture was heated to 80° C. for 2 h. Once cooled, the reaction mixture was slowly poured into sat. NaHCO$_3$ (20 mL). The precipitate was filtered-off, dissolved in EtOAc and concentrated to dryness. Purification by reverse-phase chromatography (12 g C18 cartridge, 10 to 70% ACN in AmF) afforded N-[1-(2-chlorophenyl)-3-oxo-1,2,3,4-tetrahydroisoquinolin-8-yl]-3-fluoro-5-(trifluoromethyl)benzamide (24 mg, 0.05185 mmol, 17.7%) as white powder after lyophilisation.

Example 23
N-[5-(2-Chloro-5-fluorophenyl)-1-methyl-2,7-dioxo-1H,2H,5H,6H,7H-pyrrolo[3,4-b]pyridin-4-yl]-3-fluoro-5-(trifluoromethyl)benzamide
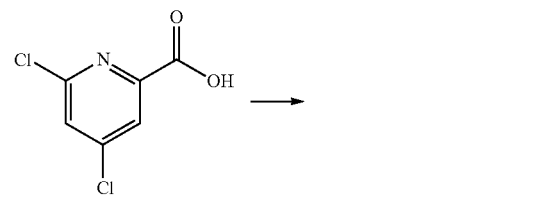
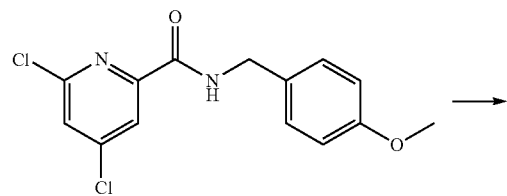
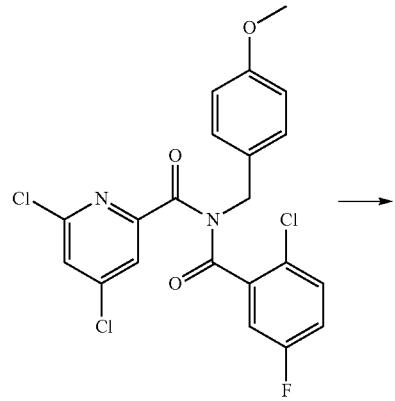
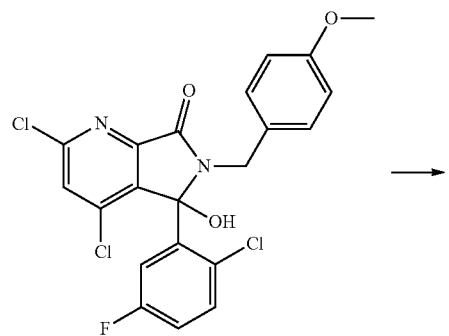
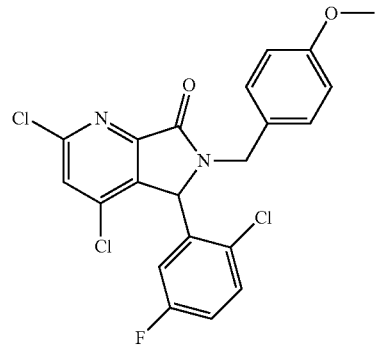
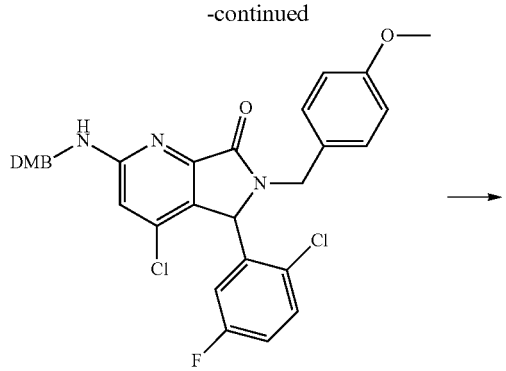
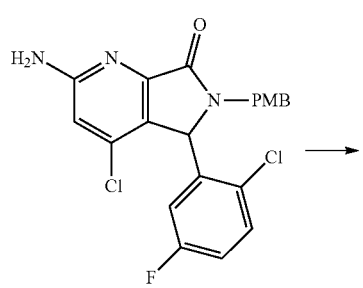
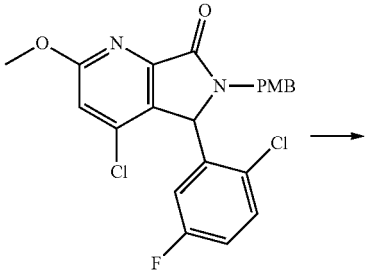
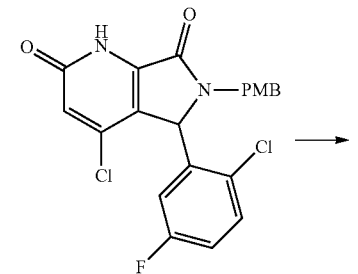
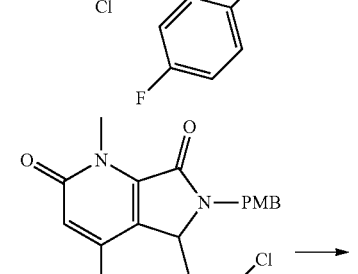

-continued

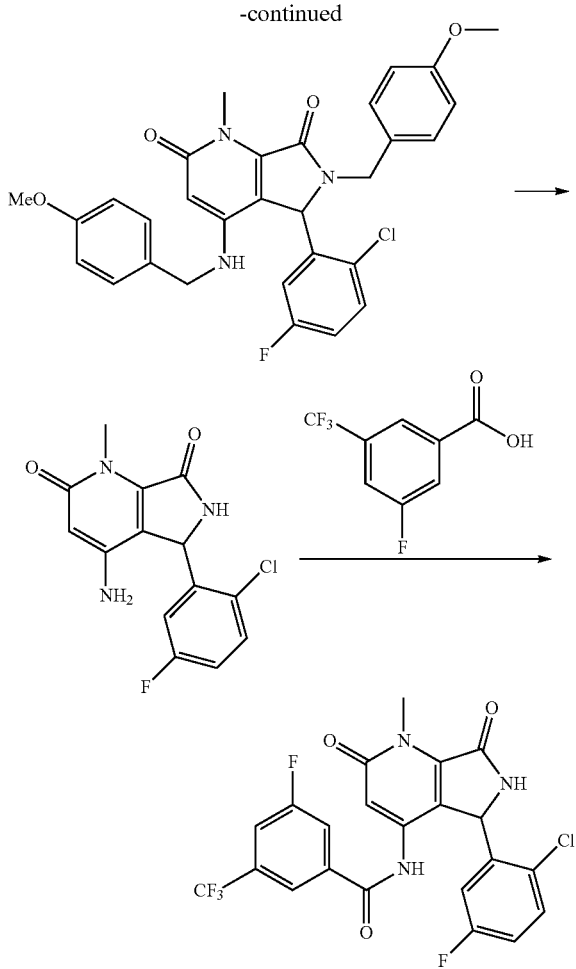

Step 1: To a solution of 4,6-dichloropicolinic acid (58.0 g, 302 mmol) in dichloromethane (1.80 L) was added CDI (73.4 g, 453 mmol, 1.50 eq) and DMAP (1.11 g, 9.06 mmol, 0.03 eq) at 15° C., and the mixture was stirred for 12 h. Then to the reaction mixture was added (4-methoxyphenyl)methanamine (41.4 g, 302 mmol, 39.1 mL) at 25° C., and the mixture was stirred for 1.5 h. The mixture was poured into water (2.00 L). The organic layers were washed with water (500 mL×2) and brine (500 mL), dried over $Na_2SO_4$, filtered, and concentrated. The residue from two batches of the preceding procedure was purified by column chromatography on silica gel eluted with petroleum ether:ethyl acetate=1:0 to 10:1 (Product: P1: $R_f$=0.50) to afford 4,6-dichloro-N-(4-methoxybenzyl)picolinamide (165 g, 453 mmol, 75.1% yield) as a brown solid.

Step 2: To a mixture of 4,6-dichloro-N-(4-methoxybenzyl)picolinamide (88.0 g, 282 mmol, 1.00 eq) in THF (800 mL) was added NaH (22.6 g, 565 mmol) at 25° C., and the mixture was stirred for 2 h. Then to the mixture was added a solution of 2-chloro-5-fluorobenzoyl chloride (81.8 g, 424 mmol) in THF (80.0 mL) at 25° C., and the mixture was stirred for 2 h. Two batches of the preceding reaction mixture were combined and quenched with water (2.00 L). The resulting solution was extracted with ethyl acetate (1.00 L×2). The combined organic layers were washed with brine (500 mL), dried over $Na_2SO_4$, filtered and concentrated. The residue was purified by column chromatography on silica gel eluted with petroleum ether:ethyl acetate=1:0 to 80:1 (product: P1: $R_f$=0.60) to afford 4,6-dichloro-N-(2-chloro-5-fluorobenzoyl)-N-(4-methoxybenzyl)picolinamide (160 g, 57.4% yield) as a yellow solid.

Step 3: To a solution of 4,6-dichloro-N-(2-chloro-5-fluorobenzoyl)-N-(4-methoxybenzyl)picolinamide (72.0 g, 153 mmol, 1.00 eq) in THF (720 mL) was added LiHMDS (1.00 M, 230 mL, 1.50 eq) at −50° C. The mixture was stirred at −50° C. for 3 h. Two batches of the preceding mixture were combined and quenched with water (3.00 L). The resulting solution was extracted with ethyl acetate (1.50 L×2). The combined organic layers were washed with brine (1.00 L), dried over $Na_2SO_4$, filtered and concentrated. The residue was purified by column chromatography on silica gel eluted with petroleum ether:ethyl acetate=1:0 to 1:1 (Product: P1: $R_f$=0.30) to afford 2,4-dichloro-5-(2-chloro-5-fluorophenyl)-5-hydroxy-6-(4-methoxybenzyl)-5,6-dihydro-7H-pyrrolo[3,4-b]pyridin-7-one (34.0 g, 68.3 mmol, 14.8% yield) as a white solid.

Step 4: To a solution of 2,4-dichloro-5-(2-chloro-5-fluorophenyl)-5-hydroxy-6-(4-methoxybenzyl)-5,6-dihydro-7H-pyrrolo[3,4-b]pyridin-7-one (34.0 g, 68.3 mmol) in dichloromethane (340 mL) was added $Et_3SiH$ (79.4 g, 683 mmol, 109 mL) and $BF_3·Et_2O$ (31.0 g, 218 mmol) at 25° C. Then the mixture was stirred at 40° C. for 15 h. The mixture was adjusted pH 6~7 with saturated $NaHCO_3$ solution. The resulting mixture was extracted with dichloromethane (400 mL×2). The combined organic layers were washed with brine (300 mL), dried over $Na_2SO_4$, filtered and concentrated. The residue was purified by column chromatography on silica gel eluted with petroleum ether:ethyl acetate=1:0 to 10:1 (Product: P1: $R_f$=0.50) to afford 2,4-dichloro-5-(2-chloro-5-fluorophenyl)-6-(4-methoxybenzyl)-5,6-dihydro-7H-pyrrolo[3,4-b]pyridin-7-one (32.0 g, 64.4 mmol, 95.8% yield) as a white solid.

Step 5: To a solution of 2,4-dichloro-5-(2-chloro-5-fluorophenyl)-6-(4-methoxybenzyl)-5,6-dihydro-7H-pyrrolo[3,4-b]pyridin-7-one (6.40 g, 13.5 mmol) in i-PrOH (40.3 mL) was added (2,4-dimethoxyphenyl)methanamine (3.40 g, 20.3 mmol) and DIEA (5.26 g, 40.7 mmol) in a sealed tube. The mixture was stirred at 190° C. for 5 h. The reaction mixture was combined and concentrated to afford the crude product. Then the crude product was dissolved in 100 mL DCM, washed with hydrochloric acid (0.50 M, 50.0 mL) and brine (100 mL), dried over $Na_2SO_4$, filtered and concentrated. The residue was purified by prep-HPLC (column: Phenomenex luna c18 250 mm*100 mm*10.0 um; mobile phase: [water (0.225% FA)-ACN]; B %: 45.0%-75.0%, 20 min) to afford 4-chloro-5-(2-chloro-5-fluorophenyl)-2-((2,4-dimethoxybenzyl)amino)-6-(4-methoxybenzyl)-5,6-dihydro-7H-pyrrolo[3,4-b]pyridin-7-one (2.6 g, 4.4 mmol, 32.9% yield).

Step 6: A suspension of 4-chloro-5-(2-chloro-5-fluorophenyl)-2-((2,4-dimethoxybenzyl)amino)-6-(4-methoxybenzyl)-5,6-dihydro-7H-pyrrolo[3,4-b]pyridin-7-one (13.0 g, 22.3 mmol, 1.00 eq) in TFA (120 g, 1.05 mol, 78.0 mL, 47.2 eq) was stirred at 25° C. for 7 hours. The reaction mixture was adjusted pH 9.00 with saturated $NaHCO_3$ solution. The resulting mixture was extracted with ethyl acetate (1.00 L×3). The combined organic layers were washed with brine (500 mL), dried over $Na_2SO_4$, filtered and concentrated to afford 2-amino-4-chloro-5-(2-chloro-5-fluorophenyl)-6-[(4-methoxyphenyl)methyl]-5H,6H,7H-pyrrolo[3,4-b]pyridin-7-one (9.97 g, 17.3 mmol, 77.9% yield) as an off-white solid.

Step 7: To a solution of 2-amino-4-chloro-5-(2-chloro-5-fluorophenyl)-6-[(4-methoxyphenyl)methyl]-5H,6H,7H-pyrrolo[3,4-b]pyridin-7-one (1 g, 2.31 mmol) in MeOH (10 mL) at 0° C. was added TFA (880 uL) followed by tert-butyl nitrite (1.35 mL, 11.5 mmol). The mixture was stirred at ambient temperature for 5 hours, and then a saturated aqueous solution of NaHCO$_3$ was added. The mixture was extracted with AcOEt (3×), and the combined organic layers were washed with brine, dried over Na$_2$SO$_4$, filtered, and concentrated under reduced pressure. Purification by silica gel chromatography (0 to 30% acetone/heptanes) afforded 4-chloro-5-(2-chloro-5-fluorophenyl)-2-methoxy-6-[(4-methoxyphenyl)methyl]-5H,6H,7H-pyrrolo[3,4-b]pyridin-7-one (725 mg, 70%) as a white foam/solid.

Step 8: 4-Chloro-5-(2-chloro-5-fluorophenyl)-2-methoxy-6-[(4-methoxyphenyl)methyl]-5H,6H,7H-pyrrolo[3,4-b]pyridin-7-one (525 mg, 1.17 mmol) was dissolved in a solution of HCl in dioxane (4M, 15 mL). The mixture was stirred at ambient temperature for 24 hours, and a saturated aqueous solution of NaHCO$_3$ was added with caution. The mixture was extracted with DCM (3×), and the combined organic layers were washed with brine, dried over Na$_2$SO$_4$, filtered and concentrated under reduced pressure, affording 4-chloro-5-(2-chloro-5-fluorophenyl)-6-(4-methoxybenzyl)-4a,5,6,7a-tetrahydro-1H-pyrrolo[3,4-b]pyridine-2,7-dione (506 mg, 1.17 mmol, 100%) as a clear oil.

Step 9: To a solution of 4-chloro-5-(2-chloro-5-fluorophenyl)-6-(4-methoxybenzyl)-4a,5,6,7a-tetrahydro-1H-pyrrolo[3,4-b]pyridine-2,7-dione (506 mg, 1.17 mmol) in dry and degassed DMF (5.8 mL) at ambient temperature was added iodomethane (88.5 μL, 1.75 mmol), followed by dipotassium carbonate (485 mg, 3.51 mmol). The mixture was stirred at ambient temperature for 12 hours, and a degassed saturated aqueous solution of NH$_4$Cl was then added. The mixture was extracted with DCM (3×), and the combined organic layers were washed with brine, dried over MgSO$_4$, filtered and concentrated under reduced pressure. Purification by silica gel chromatography (0 to 20% acetone/heptanes) afforded 4-chloro-5-(2-chloro-5-fluorophenyl)-6-(4-methoxybenzyl)-1-methyl-5,6-dihydro-1H-pyrrolo[3,4-b]pyridine-2,7-dione (432 mg, 83%) as an oil.

Step 10: 4-Chloro-5-(2-chloro-5-fluorophenyl)-6-(4-methoxybenzyl)-1-methyl-5,6-dihydro-1H-pyrrolo[3,4-b]pyridine-2,7-dione (432 mg, 0.9658 mmol) was diluted in 1-(4-methoxyphenyl)methanamine (6.5 mL, 49.7 mmol) and the mixture was stirred at 120° C. for 12 hours (sealed tube). The mixture was then diluted with AcOEt and washed with a 1N solution of HCl. The layers were separated, and the aqueous layer was extracted with AcOEt (3×). The combined organic layers were washed with 1N HCl, then with brine, dried over MgSO$_4$, filtered, and concentrated under reduced pressure. Purification by silica gel chromatography (0 to 40% acetone/hexanes) afforded 5-(2-chloro-5-fluorophenyl)-6-(4-methoxybenzyl)-4-((4-methoxybenzyl)amino)-1-methyl-5,6-dihydro-1H-pyrrolo[3,4-b]pyridine-2,7-dione (489 mg, 92%) as a white solid foam.

Step 11: 5-(2-Chloro-5-fluorophenyl)-6-(4-methoxybenzyl)-4-((4-methoxybenzyl)amino)-1-methyl-5,6-dihydro-1H-pyrrolo[3,4-b]pyridine-2,7-dione (425 mg, 0.7755 mmol) was dissolved in TFA (0.6 mL) and stirred at 120° C. for 4 h. Four drops of TfOH were added and stirring was continued at 80° C. for 12 h. The mixture was carefully poured into a saturated aqueous solution of NaHCO$_3$ and extracted with DCM (3×) and 2MeTHF (3×). The combined organic layers were washed with brine, dried over Na$_2$SO$_4$, filtered and concentrated under reduced pressure. The resulting solid was precipitated in MeOH and recovered by filtration, affording 4-amino-5-(2-chloro-5-fluorophenyl)-1-methyl-1H,2H,5H,6H,7H-pyrrolo[3,4-b]pyridine-2,7-dione (260 mg, crude) as an orange solid.

Step 12: To a solution of 4-amino-5-(2-chloro-5-fluorophenyl)-1-methyl-1H,2H,5H,6H,7H-pyrrolo[3,4-b]pyridine-2,7-dione (50 mg, 0.1624 mmol) in dry DCM (2 mL) at ambient temperature were added 3-fluoro-5-(trifluoromethyl)benzoic acid (40.5 mg, 0.1948 mmol), 1-methyl-1H-imidazole (40.0 mg, 0.4872 mmol) and [chloro(dimethylamino)methylidene]dimethylazanium hexafluorophosphate (68.3 mg, 0.2436 mmol). The mixture was stirred at ambient temperature for 12 h. The reaction mixture was then diluted with DCM (10 mL) and H$_2$O (10 mL) and passed through a phase separator cartridge. The organic portion was then concentrated in vacuo. Product was purified by reverse-phase chromatography (12 g column, water/ACN; water solvent is 10 mM ammonium formate) to yield N-[5-(2-chloro-5-fluorophenyl)-1-methyl-2,7-dioxo-1H,2H,5H,6H,7H-pyrrolo[3,4-b]pyridin-4-yl]-3-fluoro-5-(trifluoromethyl)benzamide (8.79 mg, 10.8%).

Example 24

4-Amino-3-methoxyisoindolin-1-one

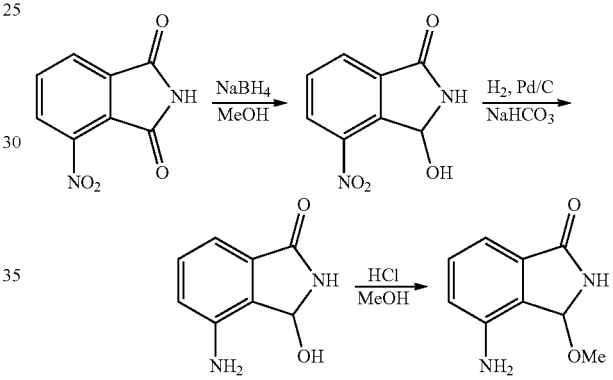

Step 1: To a solution of 4-nitro-2,3-dihydro-1H-isoindole-1,3-dione (15 g, 78.0 mmol) in a mixture of DCM (150 mL) and methanol (150 mL) at 0° C. was added NaBH$_4$ (2.95 g, 78.0 mmol) by portions. The mixture was allowed to warm to RT and stirred for 1h. The mixture was concentrate to approximately 100 mL and filtered on a Büchner funnel, affording 8.6 g of 3-hydroxy-4-nitroisoindolin-1-one as a white powder. The filtrate was recovered and re-concentrated, then filtered again. Repetition of this procedure afforded an additional 4.7 g of 3-hydroxy-4-nitroisoindolin-1-one (13.3 g, 88%) as a white solid. LC-MS (Method 1): 0.4 min, m/z=193.1 [M−H]⁻.

Step 2: To a suspension of 3-hydroxy-4-nitroisoindolin-1-one (7 g, 36 mmol) in methanol (150 mL) was added Pd/C (10% on carbon, 2.5 g) followed by NaHCO$_3$ (5 g). The mixture was degassed with hydrogen (vacuum and fill) and stirred at room temperature under a pressure of hydrogen for 12 h. The mixture was then filtered on a plug of Celite® (washed with MeOH) and concentrated under reduced pressure. The crude 4-amino-3-hydroxyisoindolin-1-one was carried to next step without further purification.

Step 3: The crude 4-amino-3-hydroxyisoindolin-1-one was diluted in MeOH (150 mL) and a 4N solution of HCL (10 mL) was then added. The mixture was stirred at 60° C. for 15 min and then allowed to cool to room temperature. Volatiles were removed under reduced pressure and the mixture was treated with a sat. aq. solution of NaHCO$_3$. The mixture was extracted with DCM (3×) and MeTHF (3×). The combined organic layers were washed with brine, dried over Na$_2$SO$_4$, filtered and concentrated under reduced pressure. Purification by silica gel chromatography (0 to 80% acetone/hexanes) afforded 4-amino-3-methoxyisoindolin-1-one (1 g, 22%) as an orange solid. LC-MS (Method 1): 0.38 min, m/z=179.2 [M+H]$^+$.

Example 25

6-([1,2,4]Triazolo[1,5-a]pyridin-6-yl)-4-bromo-3-(2-chloro-5-fluorophenyl)-2-(4-methoxybenzyl)isoindolin-1-one

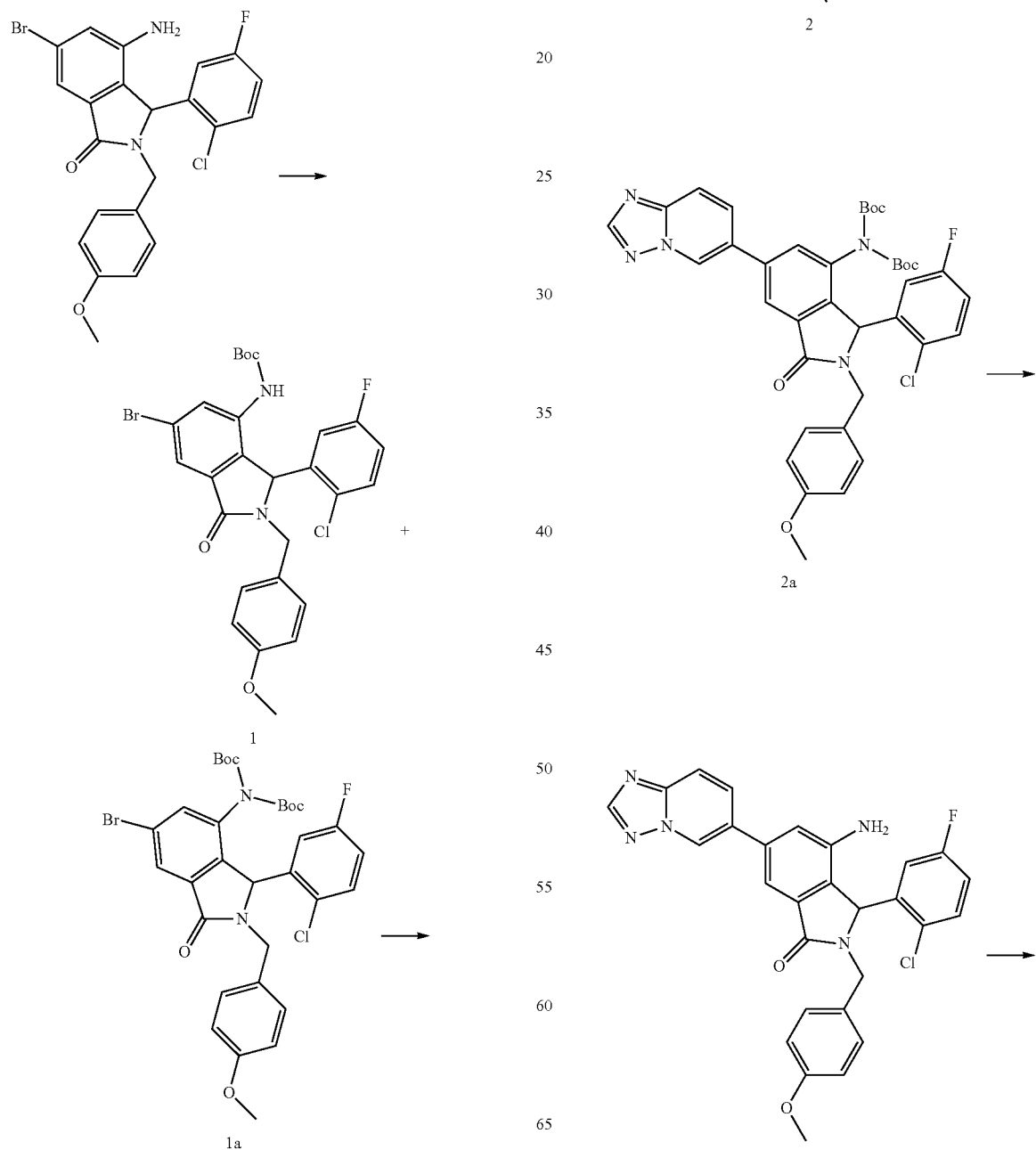

-continued

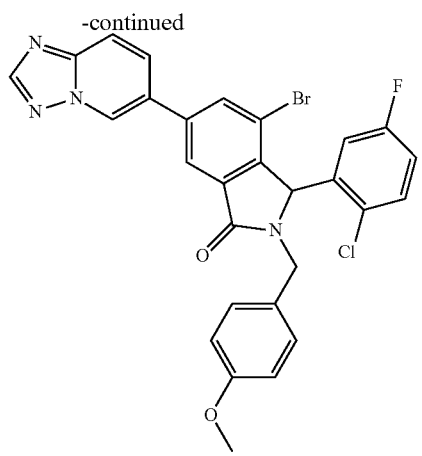

Step 1: To a solution of 4-amino-6-bromo-3-(2-chloro-5-fluorophenyl)-2-(4-methoxybenzyl)isoindolin-1-one (125 g, 263 mmol) in DCM (1.25 L) was added DMAP (38.5 g, 315 mmol) and BOc$_2$O (86.0 g, 394 mmol) at 20° C., and the mixture was stirred at 20° C. for 12 h. The reaction was poured into H$_2$O (2.00 L) and divided. The combined organic layers were washed with saturated NH$_4$Cl solution (1.50 mL*3), washed with brine (1.50 L), dried over Na$_2$SO$_4$, filtered, and concentrated under reduced pressure to give a residue. The residue was purified by column chromatography (SiO$_2$, petroleum ether/ethyl acetate=100/1 to 10/1, R$_f$=0.55) to give Compound 1 & 1a (196 g, crude) as a yellow solid.

Step 2: To a solution of Compound 1 & 1 a (98.0 g, crude) in DMF (980 mL) was added 6-(4,4,5,5-tetramethyl-1,3,2-dioxaborolan-2-yl)-[1,2,4]triazolo[1,5-a]pyridine (50.1 g, 204 mmol) and K$_2$CO$_3$ (2 M, 255 mL). The mixture was purged with N$_2$ for three times. Then Pd(dppf)Cl$_2$ (6.23 g, 8.51 mmol, 0.05 eq) was added to the mixture at 20° C. The mixture was purged with N$_2$ for three times again. Then the mixture was heated to 90° C. and stirred at 90° C. for 1 h. The reaction was poured into H$_2$O (5.00 L), stirred and filtered. The filter cake was diluted with ethyl acetate (3.00 L) and filtered. The combined organic layers were washed with saturated NH$_4$Cl solution (1.50 L), washed with brine (1.50 L), dried over Na$_2$SO$_4$, filtered and concentrated under reduced pressure to give compound 2 & 2a (85.0 g, crude) as a black brown solid.

Step 3: To a solution of compound 2 & 2a (85.0 g, crude) in DCM (850 mL) was added TFA (655 g, 5.74 mol) at 20° C., then the mixture was stirred at 20° C. for 3 h. The reaction was concentrated under reduced pressure to give oil. The oil was diluted with DCM (1.00 L), poured into 2 N NaOH (2.00 L) and ice, and extracted with DCM (1.00 L*3). The combined organic layers were washed with brine (2.00 L), dried over Na$_2$SO$_4$, filtered, and concentrated under reduced pressure to give a residue. The residue was purified by column chromatography (SiO$_2$, petroleum ether/ethyl acetate=10/1 to ethyl acetate/dichloromethane=4/1, R$_f$=0.40) to give 6-([1,2,4]triazolo[1,5-a]pyridin-6-yl)-4-amino-3-(2-chloro-5-fluorophenyl)-2-(4-methoxybenzyl)isoindolin-1-one (57.5 g) as a yellow amorphous solid.

Step 4: To a solution of 6-([1,2,4]triazolo[1,5-a]pyridin-6-yl)-4-amino-3-(2-chloro-5-fluorophenyl)-2-(4-methoxybenzyl)isoindolin-1-one (11.6 g, 22.6 mmol) in ACN (110 mL) and HBr (173 g, 705 mmol) was added NaNO$_2$ (1.71 g, 24.8 mmol, 1.10 eq) at 0° C. The diazonium solution was stirred for a further 30 min at 0° C., and then CuBr (3.89 g, 27.1 mmol) was added to the mixture and stirred at 0° C. for 1 h. The mixture was poured into ice-water (2.00 L) and extracted with DCM (1.00 L*3). The combined organic layers were dried over Na$_2$SO$_4$, filtered, and concentrated under reduced pressure to give a residue. The residue was purified by column chromatography (SiO$_2$, petroleum ether/ethyl acetate=1/1 to 0/1, R$_f$=0.50). The resulting product was triturated with ethyl acetate (200 mL) at 25° C. for 16 h to give 6-([1,2,4]triazolo[1,5-a]pyridin-6-yl)-4-bromo-3-(2-chloro-5-fluorophenyl)-2-(4-methoxybenzyl)isoindolin-1-one (8.3 g, 12.8 mmol, 56.7% yield) as a green solid.

Example 26

N-(3-(2-Chloro-5-fluorophenyl)-1-oxo-6-(4,4,5,5-tetramethyl-1,3,2-dioxaborolan-2-yl)isoindolin-4-yl)-3-fluoro-5-(trifluoromethyl)benzamide

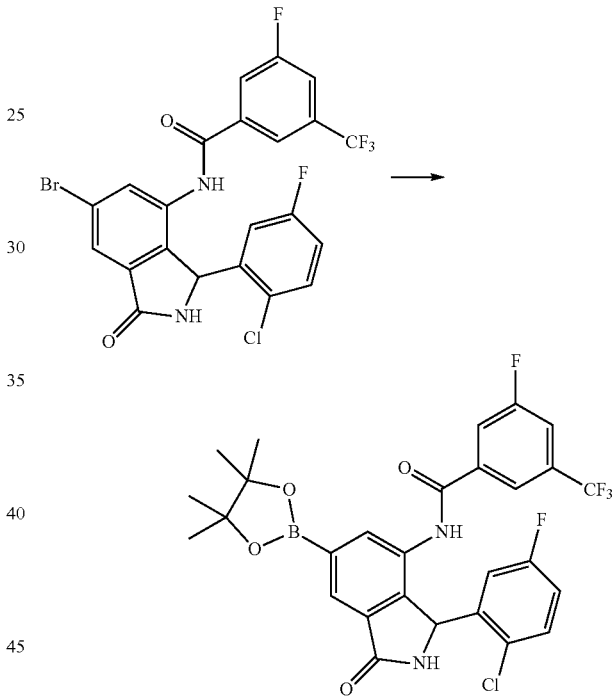

To a solution of N-(6-bromo-3-(2-chloro-5-fluorophenyl)-1-oxoisoindolin-4-yl)-3-fluoro-5-(trifluoromethyl)benzamide (160 g, 261 mmol) and B$_2$Pin$_2$ (79.5 g, 313 mmol, 1.20 eq) in dioxane (1.60 L) was added KOAc (76.8 g, 783 mmol) and Pd(dppf)Cl$_2$ (9.55 g, 13.1 mmol, 0.05 eq) at 25° C. The mixture was purged with N$_2$ three times, heated to 90° C., and stirred at 90° C. for 14 hrs. To the reaction mixture was added half saturated brine (0.50 L) followed by saturated Na$_2$S$_2$O$_3$ aqueous solution (0.80 L). The aqueous layer was extracted with EtOAc (1.0 L), then the mixture was filtered. After separating the organic layer, the aqueous layer was extracted EtOAc (1.00 L) again. The combined organic layer was washed with brine (0.50 L), dried over Na$_2$SO$_4$, filtered, and concentrated. The crude product was dissolved in MTBE (3.00 V of crude, 600 mL), which was slowly dropped into heptanes (10.0 V of crude, 2.00 L), then the mixture was stirred at 25° C. for 2 h. The mixture was filtered, and the filter cake was dried under vacuum. The resulting product was triturated with petroleum ether: ethyl acetate=5:1 (600 mL) at 25° C. for 10 hrs. The mixture was filtered, and the filter cake was dried under vacuum. N-(3-(2-chloro-5-fluorophenyl)-1-oxo-6-(4,4,5,5-tetramethyl-1,3,2-dioxaborolan-2-yl)isoindolin-4-yl)-3-fluoro-5-(trifluoromethyl)benzamide (157 g, 96.3% yield) was obtained as a tan amorphous solid.

Example 27

N-(3-(2-Chloro-5-fluorophenyl)-6-hydroxy-1-oxoisoindolin-4-yl)-3-fluoro-5-(trifluoromethyl)benzamide

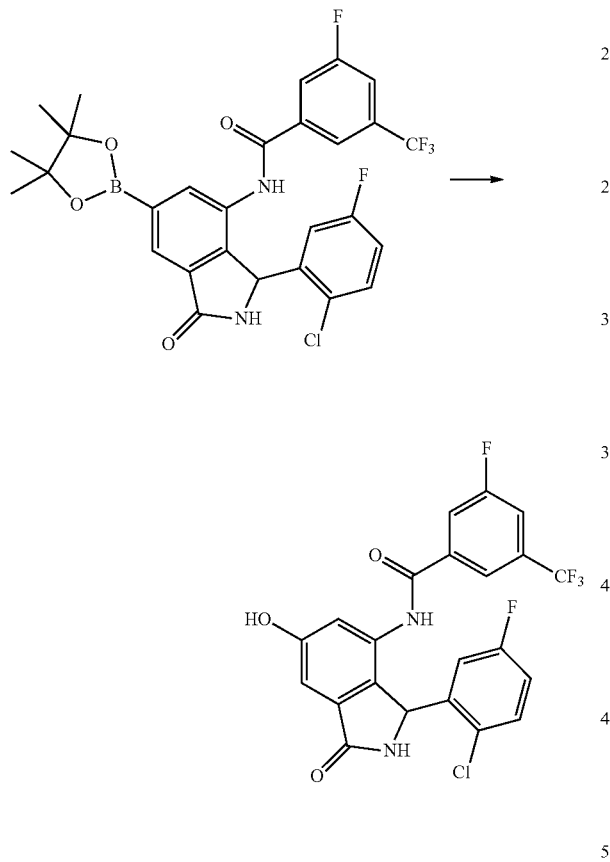

To a solution of N-(3-(2-chloro-5-fluorophenyl)-1-oxo-6-(4,4,5,5-tetramethyl-1,3,2-dioxaborolan-2-yl)isoindolin-4-yl)-3-fluoro-5-(trifluoromethyl)benzamide (97.0 g, 0.164 mol, 1.00 eq) in ACN (1.00 L) was added $H_2O_2$-urea (28.9 g, 0.307 mol, 1.88 eq) at 25° C. under $N_2$ atmosphere, then the mixture was stirred at 25° C. for 12 hrs. To the mixture was added half saturated brine (0.50 L) followed by saturated $Na_2S_2O_3$ aqueous solution (0.80 L). The aqueous layer was extracted with ethyl acetate (1.00 L), and then the mixture was filtered. After separating the organic layer, the aqueous layer was extracted again with ethyl acetate (1.00 L). The combined organic layer was washed with brine (0.50 L), dried over $Na_2SO_4$, filtered and concentrated. The crude product was purified by column chromatography ($SiO_2$, ethyl acetate: dichloromethane=1:10-1:4-1:1, $R_f$=0.30). The crude product was dissolved in MTBE (150 mL, 3.00 V of crude), which was slowly dropped into heptanes (520 mL, 10.0 V of crude), then the mixture was heated to 50° C., and stirred at 50° C. for 1 hr. The mixture was cooled to 25° C. and filtered, and the filter cake was dried under vacuum to afford N-(3-(2-chloro-5-fluorophenyl)-6-hydroxy-1-oxoisoindolin-4-yl)-3-fluoro-5-(trifluoromethyl)benzamide (51.0 g, 61.7% yield) as a yellow solid.

Example 28

Methyl 1-(2-chloro-5-fluorophenyl)-7-(3-fluoro-5-(trifluoromethyl)benzamido)-3-oxoisoindoline-5-carboxylate

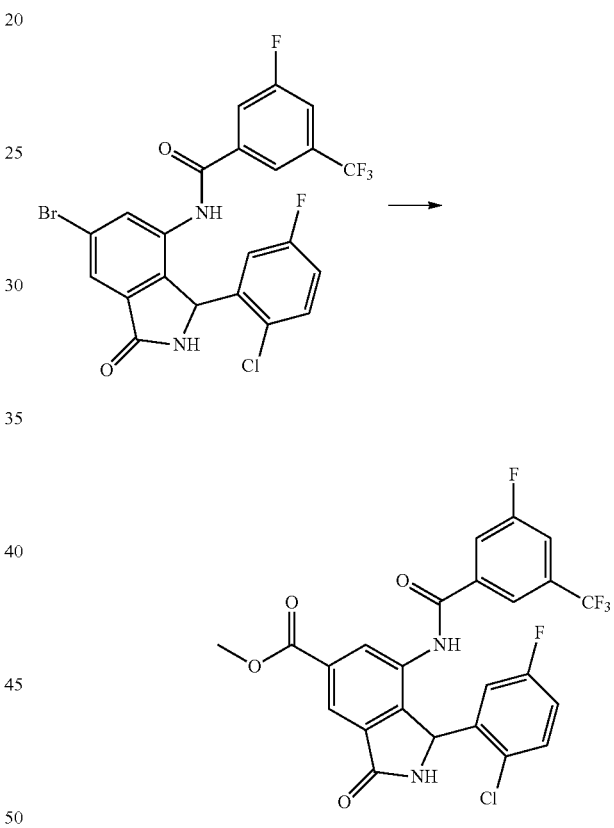

To a solution of N-(6-bromo-3-(2-chloro-5-fluorophenyl)-1-oxoisoindolin-4-yl)-3-fluoro-5-(trifluoromethyl)benzamide (120 g, 220 mmol) in MeOH (1.00 L) was added $Et_3N$ (44.5 g, 440 mmol, 61.2 mL) and Pd(dppf)$Cl_2$ (16.1 g, 22.0 mmol) at 25° C. The mixture was degassed and purged with CO three times. The mixture was heated to 80° C. and stirred at 80° C. for 16 hrs under CO (50 psi). The mixture was concentrated, and the residue was purified by column chromatography ($SiO_2$, petroleum ether: ethyl acetate=50:1-0: 1, $R_f$=0.1) to give methyl 1-(2-chloro-5-fluorophenyl)-7-(3-fluoro-5-(trifluoromethyl)benzamido)-3-oxoisoindoline-5-carboxylate (58.0 g, 103 mmol, 47.0% yield, 93.6% purity) as a pink solid.

Example 29

N-(6-(Bromomethyl)-3-(2-chloro-5-fluorophenyl)-1-oxoisoindolin-4-yl)-3-fluoro-5-(trifluoromethyl)benzamide

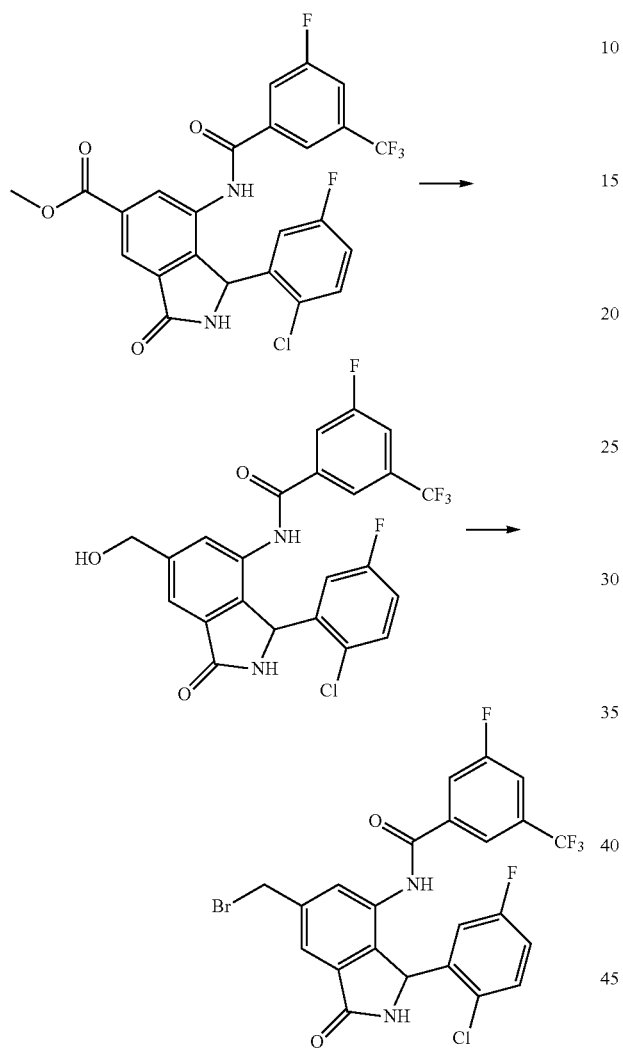

Step 1: To a solution of lithium aluminum hydride (7.16 g, 188 mmol, 2.20 eq) in THF (100 mL) was added methyl 1-(2-chloro-5-fluorophenyl)-7-(3-fluoro-5-(trifluoromethyl) benzamido)-3-oxoisoindoline-5-carboxylate (45.0 g, 85.7 mmol, 1.00 eq) dissolved in THF (300 mL) at 0° C. The mixture was warmed to 25° C. and stirred at 25° C. for 2 hours. The mixture was cooled to −10° C. and poured into Na$_2$SO$_4$*10H$_2$O (110 g) under stirring, then filtered under reduced pressure and the filtrate was concentrated under pressure. The residue was triturated with mixture solution (petroleum ether: ethyl acetate=5:1, 300 mL) at 25° C. for 30 mins and filtered under pressure to obtain N-(3-(2-chloro-5-fluorophenyl)-6-(hydroxymethyl)-1-oxoisoindolin-4-yl)-3-fluoro-5-(trifluoromethyl)benzamide (50.0 g, crude) as a brown solid.

Step 2: To a solution of N-(3-(2-chloro-5-fluorophenyl)-6-(hydroxymethyl)-1-oxoisoindolin-4-yl)-3-fluoro-5-(trifluoromethyl)benzamide (36.0 g, 72.5 mmol) in THF (1200 mL) was added PBr$_3$ (23.5 g, 86.96 mmol) at −20° C., then the mixture was warmed to 0° C. and stirred at 0° C. for 2 h. The mixture was slowly warmed to 10° C. and stirred at 10° C. for 10 h. The mixture was dropped into saturated NH$_4$Cl (200 mL) at −20° C., then extracted with ethyl acetate (500 mL*3). The combined organic layers were washed with brine (200 mL*3), dried over Na$_2$SO$_4$, filtered and concentrated under reduced pressure. The residue was triturated with mixture solvent (petroleum ether: ethyl acetate=3:1, 100 mL) at 10° C. for 30 mins to obtain N-(6-(bromomethyl)-3-(2-chloro-5-fluorophenyl)-1-oxoisoindolin-4-yl)-3-fluoro-5-(trifluoromethyl)benzamide (27.6 g, 46.9 mmol, 64.7% yield) as a white solid.

Example 30

(1-(2-Chloro-5-fluorophenyl)-7-(3-fluoro-5-(trifluoromethyl)benzamido)-3-oxoisoindolin-5-yl)methanesulfonyl chloride

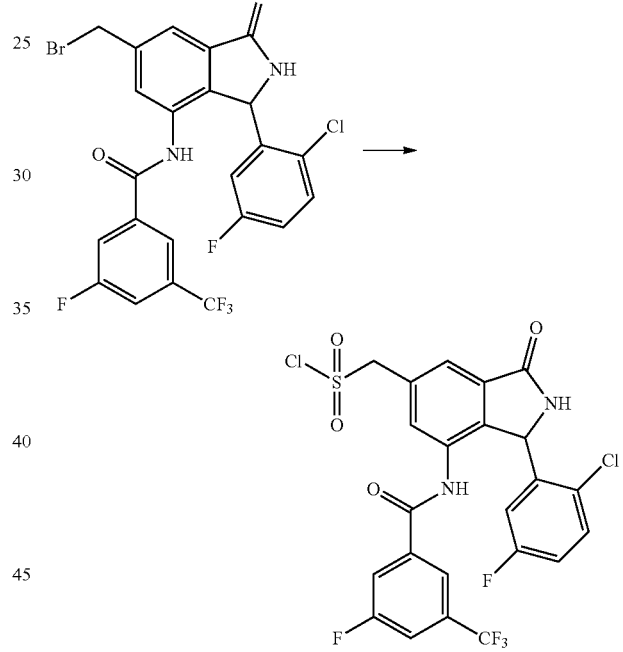

A 100 mL round bottom flask was charged with N-(6-(bromomethyl)-3-(2-chloro-5-fluorophenyl)-1-oxoisoindolin-4-yl)-3-fluoro-5-(trifluoromethyl)benzamide (1.05 g, 1.0 eq.) and thiourea (149 mg, 1.05 eq.). Ethanol (30 mL) was added, and the reaction media was heated to 80° C. and kept under stirring for 3 h. The reaction media was cooled to ambient temperature, and ethanol was removed under reduced pressure to afford a white powder. The mixture was dissolved in MeCN (6 mL) and cooled to 0 C. Hydrochloric acid (1N, 1.3 mL) was added dropwise to the reaction mixture, which was kept under stirring at 0° C. for 20 min, at which point N-chlorosuccinimide (998 mg, 4 eq.) was added portionwise. The reaction media was allowed to warm to ambient temperature. After 30 min of stirring, the reaction mixture was concentrated to yield (1-(2-chloro-5-fluorophenyl)-7-(3-fluoro-5-(trifluoromethyl)benzamido)-3-oxoisoindolin-5-yl)methanesulfonyl chloride as an orange solid (1.01 g, 92% yield)

Example 31

N-(3-(2-Chloro-5-fluorophenyl)-6-formyl-1-oxoisoindolin-4-yl)-3-fluoro-5-(trifluoromethyl)benzamide (I-333)

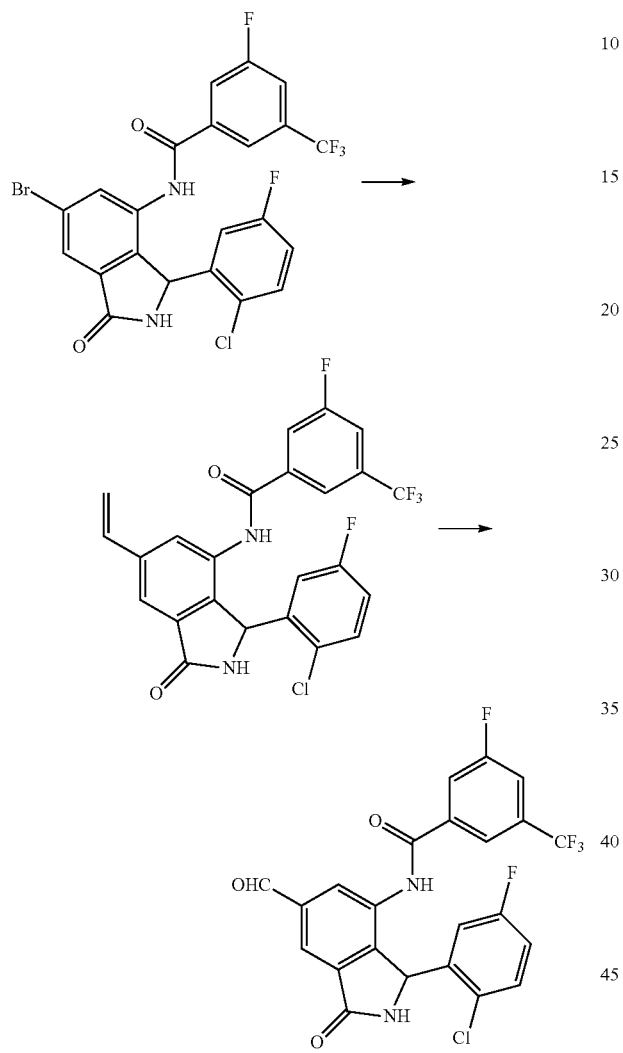

Step 1: To a solution of N-(6-bromo-3-(2-chloro-5-fluorophenyl)-1-oxoisoindolin-4-yl)-3-fluoro-5-(trifluoromethyl)benzamide (200 g, 367 mmol) in dioxane (2.00 L) and H₂O (400 mL) was added vinylboronic acid pinacol ester (113 g, 733 mmol), Pd(dppf)Cl₂ (26.8 g, 36.7 mmol) and NaHCO₃ (154 g, 1.83 mol) at 25° C., then the mixture was heated to 80° C. and stirred at 80° C. for 12 h. The mixture was poured into water (2.50 L) and extracted with ethyl acetate (1.00 L*2). The combined organic phase was washed with brine (1.00 L*2), dried with anhydrous Na₂SO₄, filtered, and concentrated in vacuum. The resulting residue was purified by column chromatography (SiO₂, petroleum ether: ethyl acetate=50: 1-0: 1, R$_f$=0.25) to give N-(3-(2-chloro-5-fluorophenyl)-1-oxo-6-vinylisoindolin-4-yl)-3-fluoro-5-(trifluoromethyl)benzamide (135 g, 70.1% yield) as a brown solid.

Step 2: Ozone was bubbled into a solution of N-(3-(2-chloro-5-fluorophenyl)-1-oxo-6-vinylisoindolin-4-yl)-3-fluoro-5-(trifluoromethyl)benzamide (52.0 g, 106 mmol) in DCM (2.00 L) at −78° C. for 0.5 h. After excess O3 was purged with N₂, Me₂S (7.21 g, 116 mmol) was added at −78° C., and the mixture was stirred at −78° C. for 0.5 hr. Two batches of the reaction mixture were quenched with saturated NaHCO₃ solution (2.00 L), and the mixture was extracted with DCM (1.20 L*3). The combined organic layers were washed with brine (1.00 L), dried over Na₂SO₄, filtered, and concentrated. The resulting residue was purified by prep-HPLC (column: Phenomenex luna C18 (250*70 mm, 15 um); mobile phase: [water (0.225% FA)-ACN]; B %: 43ACN %-63ACN %, 20 min) to give N-(3-(2-chloro-5-fluorophenyl)-6-formyl-1-oxoisoindolin-4-yl)-3-fluoro-5-(trifluoromethyl)benzamide (42.0 g, 40.1% yield) as an off-white solid.

Example 32

N-(2-([1,2,4]Triazolo[1,5-a]pyridin-6-yl)-5-(2-chloro-5-fluorophenyl)-7-oxo-6,7-dihydro-5H-pyrrolo[3,4-b]pyridin-4-yl)-3-fluoro-5-(trifluoromethyl)benzamide

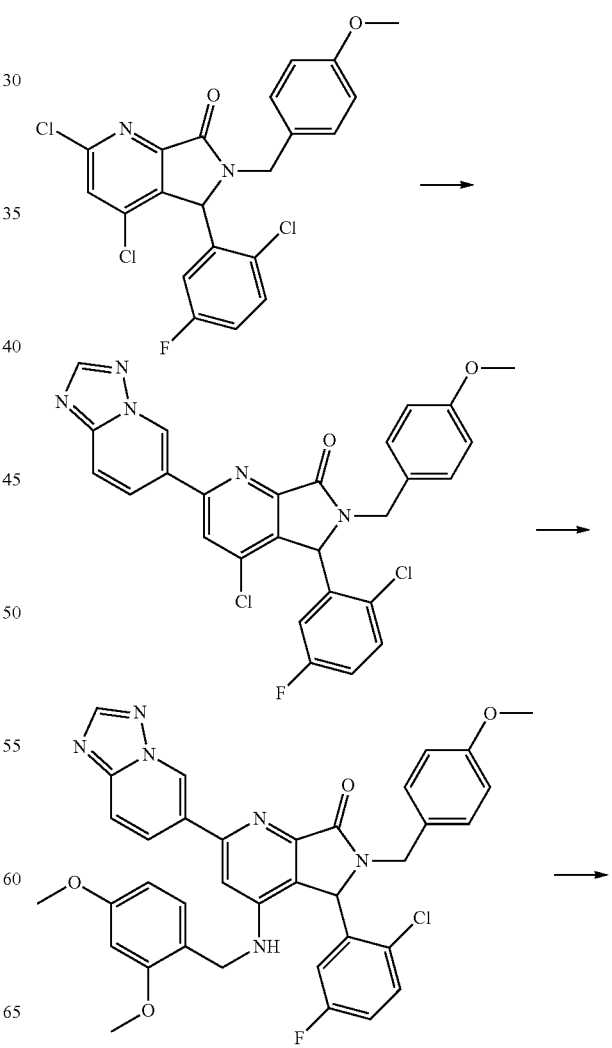

-continued

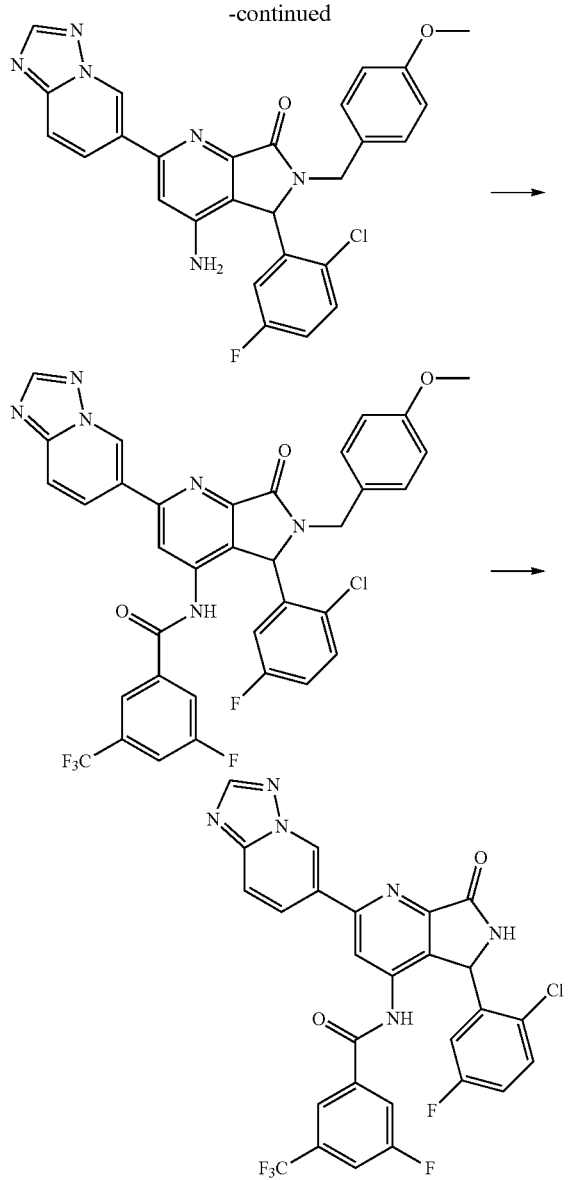

Step 1: 2,4-Dichloro-5-(2-chloro-5-fluorophenyl)-6-(4-methoxybenzyl)-5,6-dihydro-7H-pyrrolo[3,4-b]pyridin-7-one (6.000 g, 13.2 mmol) was slurried in a mixture of dimethoxyethane (60 mL) and ethanol (30 mL). To this was added 6-(4,4,5,5-tetramethyl-1,3,2-dioxaborolan-2-yl)-[1,2,4]triazolo[1,5-a]pyridine (3.23 g, 13.2 mmol), followed by 25 mL of 1.5 M aqueous sodium carbonate. The mixture was degassed for 10 min by bubbling $N_2$ directly into the slurry. Palladium(2+) bis(triphenylphosphine) dichloride (370 mg, 528 μmol) was added, and the mixture was heated to 80° C. for 3 h. The reaction mixture was cooled to RT and diluted with ethyl acetate (150 mL) and water (50 mL). The mixture was extracted with ethyl acetate (100 mL). The combined organic layers were washed with brine (100 mL), dried over $Na_2SO_4$, filtered, and concentrated. The residue was purified by column chromatography on silica gel eluted with heptanes:ethyl acetate=1:1 to 0:100 (Product: P1: $R_f$=0.50) to afford 2-([1,2,4]triazolo[1,5-a]pyridin-6-yl)-4-chloro-5-(2-chloro-5-fluorophenyl)-6-(4-methoxybenzyl)-5,6-dihydro-7H-pyrrolo[3,4-b]pyridin-7-one (3.1 g, 42.9% yield) as an off-white solid.

Step 2: 2-([1,2,4]Triazolo[1,5-a]pyridin-6-yl)-4-chloro-5-(2-chloro-5-fluorophenyl)-6-(4-methoxybenzyl)-5,6-dihydro-7H-pyrrolo[3,4-b]pyridin-7-one (2.0 g, 3.74 mmol) was dissolved in 3 mL of NMP and treated with 1-(2,4-dimethoxyphenyl)methanamine (2.8 mL, 18.7 mmol). The mixture was heated to 150° C. for 30 min. The reaction was cooled to room temperature, diluted with ethyl acetate (50 mL) and aqueous LiCl (25 mL). The organic layer was washed with 4×25 mL aqueous LiCl, dried over $Na_2SO_4$, filtered, and concentrated to afford 2-([1,2,4]triazolo[1,5-a]pyridin-6-yl)-5-(2-chloro-5-fluorophenyl)-4-((2,4-dimethoxybenzyl)amino)-6-(4-methoxybenzyl)-5,6-dihydro-7H-pyrrolo[3,4-b]pyridin-7-one (2.5 g, 3.60 mmol, 96.7% yield) as an off-white solid.

Step 3: 2-([1,2,4]Triazolo[1,5-a]pyridin-6-yl)-5-(2-chloro-5-fluorophenyl)-4-((2,4-dimethoxybenzyl)amino)-6-(4-methoxybenzyl)-5,6-dihydro-7H-pyrrolo[3,4-b]pyridin-7-one (2.5 g, 3.75 mmol) was dissolved in DCM (2 mL) and dropped into trifluoroacetic acid (5.7 mL, 75 mmol, 20 eq). The mixture was stirred at room temperature for 16 h. The mixture was concentrated in vacuo then diluted with dichloromethane (50 mL). This was slowly added to an ice cold, stirring mixture of saturated aqueous sodium bicarbonate (50 mL). The pH was then adjusted to pH 10 via addition of 2N sodium hydroxide. The mixture was stirred for 5 h. The organic layer was washed with water (50 mL), brine (50 mL), dried over $Na_2SO_4$, filtered and concentrated. The resulting residue was triturated with MTBE (25 mL) for 60 mins and then filtered to afford 2-([1,2,4]triazolo[1,5-a]pyridin-6-yl)-4-amino-5-(2-chloro-5-fluorophenyl)-6-(4-methoxybenzyl)-5,6-dihydro-7H-pyrrolo[3,4-b]pyridin-7-one (1.6 g, 82.9% yield) as an off-white solid.

Step 4: 2-([1,2,4]Triazolo[1,5-a]pyridin-6-yl)-4-amino-5-(2-chloro-5-fluorophenyl)-6-(4-methoxybenzyl)-5,6-dihydro-7H-pyrrolo[3,4-b]pyridin-7-one (2.50 g, 4.85 mmol) was dissolved in acetonitrile (30 mL). Pyridine (3.9 mL, 48.5 mmol) was added, followed by 3-fluoro-5-(trifluoromethyl)benzoyl chloride (1.31 g, 5.81 mmol, 1.2 eq). The reaction was heated to 80° C. for 16 h. The reaction was cooled to room temperature and diluted with ethyl acetate (100 mL). This was carefully washed with 10% aqueous sodium carbonate (3×50 mL), followed by brine (50 mL). The solution was dried over $Na_2SO_4$, filtered and concentrated. The residue was triturated in MTBE (25 mL) for 2 h and filtered to afford N-(2-([1,2,4]triazolo[1,5-a]pyridin-6-yl)-5-(2-chloro-5-fluorophenyl)-6-(4-methoxybenzyl)-7-oxo-6,7-dihydro-5H-pyrrolo[3,4-b]pyridin-4-yl)-3-fluoro-5-(trifluoromethyl)benzamide (2.5 g, 73.3% yield).

Step 5: N-(2-([1,2,4]Triazolo[1,5-a]pyridin-6-yl)-5-(2-chloro-5-fluorophenyl)-6-(4-methoxybenzyl)-7-oxo-6,7-dihydro-5H-pyrrolo[3,4-b]pyridin-4-yl)-3-fluoro-5-(trifluoromethyl)benzamide (1.00 g, 1.41 mmol) was dissolved in acetonitrile (18 mL). Ceric ammonium nitrate (1.54 g, 2.82 mmol) was added as a solution in water (2 mL). The reaction was warmed to 40° C. for 30 min. The reaction was cooled to RT and carefully quenched with a solution of sodium bisulfite in water. The mixture was extracted with MeTHF (3×20 mL). The combined organics were then washed with water (20 mL), brine (30 mL), dried over $Na_2SO_4$, filtered and concentrated. The residue was purified by column chromatography on silica gel eluted with dichloromethane:methanol=100:0 to 85:15 to afford N-(2-([1,2,4]triazolo[1,5-a]pyridin-6-yl)-5-(2-chloro-5-fluorophenyl)-7-oxo-6,7-dihydro-5H-pyrrolo[3,4-b]pyridin-4-yl)-3-fluoro-5-(trifluoromethyl)benzamide (514 mg, 62.3% yield) as a white solid.

Example 33

N-[3-(2-Chloro-5-fluorophenyl)-6-(1H-indol-2-yl)-1-oxo-2,3-dihydro-1H-isoindol-4-yl]-3-fluoro-5-(trifluoromethyl)benzamide

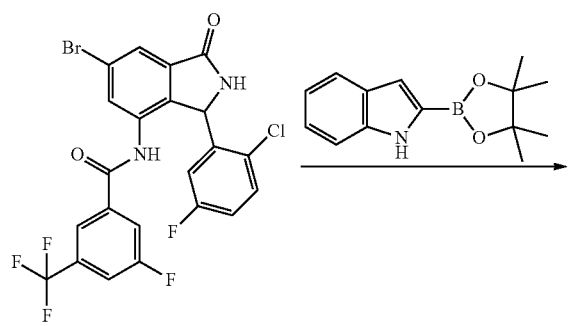

To an 8-mL vial was added N-[6-bromo-3-(2-chloro-5-fluorophenyl)-1-oxo-2,3-dihydro-1H-isoindol-4-yl]-3-fluoro-5-(trifluoromethyl)benzamide (100 mg, 183 µmol), 2-(4,4,5,5-tetramethyl-1,3,2-dioxaborolan-2-yl)-1H-indole (44.4 mg, 1 eq), sodium carbonate (48.4 mg, 2.5 eq), and palladium bis(triphenylphosphine) dichloride (10.5 mg, 0.15 eq). The vial was purged with nitrogen and sealed. The solids were then dissolved in dioxane (1.6 mL) and water (0.4 mL). The reaction was then stirred and heated to 90° C. for 1 hour before checking the reaction progress via LCMS. The reaction mixture was cooled and filtered through a pad of silica. The filtrate was concentrated, and the resulting material was purified on the AccQ Prep system eluting with 30-60% water with 0.1% formic acid. Product-containing fractions were concentrated to yield N-[3-(2-chloro-5-fluorophenyl)-6-(1H-indol-2-yl)-1-oxo-2,3-dihydro-1H-isoindol-4-yl]-3-fluoro-5-(trifluoromethyl)benzamide (87.6 mg, 82.6%).

Example 34

N-[3-(2-Chloro-5-fluorophenyl)-6-[3-(difluoromethyl)imidazo[1,2-a]pyridin-6-yl]-1-oxo-2,3-dihydro-1H-isoindol-4-yl]-3-fluoro-5-(trifluoromethyl)benzamide

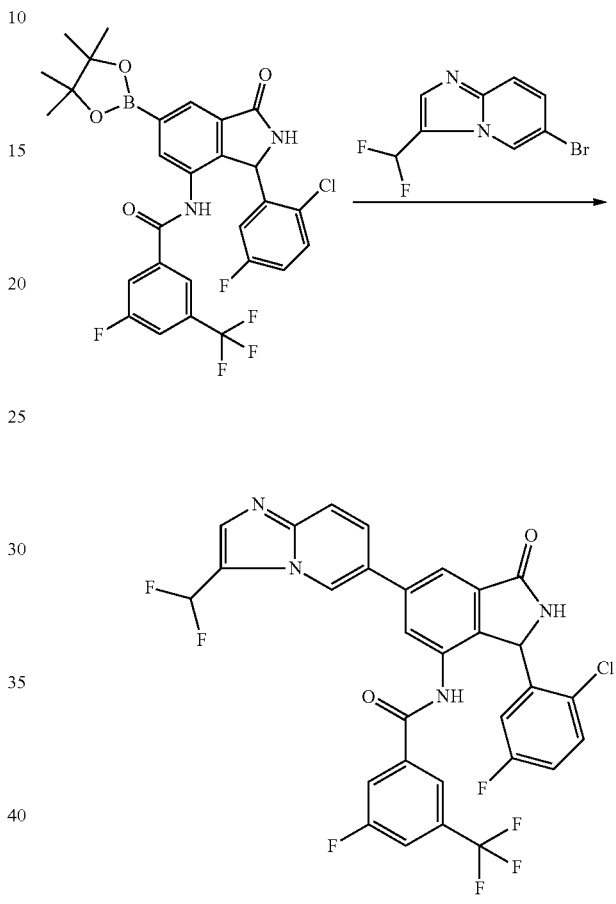

To a vial was added N-[3-(2-chloro-5-fluorophenyl)-1-oxo-6-(4,4,5,5-tetramethyl-1,3,2-dioxaborolan-2-yl)-2,3-dihydro-1H-isoindol-4-yl]-3-fluoro-5-(trifluoromethyl)benzamide (381 mg, 644 µmol), 6-bromo-3-(difluoromethyl)imidazo[1,2-a]pyridine (145 mg, 586 µmol), palladium(2+) bis(triphenylphosphane) dichloride (61.6 mg, 87.8 µmol), and disodium carbonate (185 mg, 1.75 mmol). The vial was purged and back filled with nitrogen, and then water (250 µL) and dioxane (1 mL) were added. The reaction mixture was then heated to 90° C. for 20 mins. The reaction progress was then checked via LCMS, which showed complete conversion to product. The mixture was then cooled, filtered, and placed on the AccQ prep system. Fractions containing product were concentrated to yield N-[3-(2-chloro-5-fluorophenyl)-6-[3-(difluoromethyl)imidazo[1,2-a]pyridin-6-yl]-1-oxo-2,3-dihydro-1H-isoindol-4-yl]-3-fluoro-5-(trifluoromethyl)benzamide (145 mg, 39.1%).

Additional compounds prepared according to the methods of Example 33 and Example 34 are listed in Table 10 below. Certain compounds in Table 10 were prepared with other compounds whose preparation is described elsewhere in the Examples.

TABLE 10

Additional Exemplary Compounds
Compound

| Compound |
|---|
| I-705 |
| I-712 |
| I-732 |
| I-736 |
| I-737 |
| I-738 |
| I-741 |
| I-782 |
| I-783 |
| I-784 |
| I-815 |
| I-821 |
| I-822 |
| I-823 |
| I-824 |
| I-825 |
| I-826 |
| I-827 |
| I-838 |
| I-849 |
| I-851 |
| I-852 |
| I-853 |
| I-854 |
| I-855 |
| I-865 |
| I-866 |
| I-881 |
| I-882 |
| I-883 |
| I-884 |
| I-885 |
| I-886 |
| I-887 |
| I-888 |
| I-890 |
| I-891 |
| I-892 |
| I-893 |
| I-894 |
| I-895 |
| I-896 |
| I-902 |
| I-905 |
| I-906 |
| I-915 |
| I-918 |
| I-919 |
| I-921 |
| I-927 |
| I-928 |
| I-929 |
| I-930 |
| I-931 |
| I-932 |
| I-933 |
| I-934 |
| I-940 |
| I-941 |
| I-943 |
| I-945 |
| I-946 |
| I-948 |
| I-949 |
| I-967 |
| I-969 |
| I-970 |
| I-971 |
| I-972 |
| I-975 |
| I-979 |
| I-980 |
| I-981 |
| I-982 |
| I-984 |
| I-985 |
| I-986 |

TABLE 10-continued

Additional Exemplary Compounds
Compound

| Compound |
|---|
| I-987 |
| I-996 |
| I-1000 |
| I-1003 |
| I-1004 |
| I-1006 |
| I-1007 |
| I-1008 |
| I-1009 |
| I-1010 |
| I-1011 |
| I-1012 |
| I-1023 |
| I-1024 |
| I-1025 |
| I-1026 |
| I-1027 |
| I-1028 |
| I-1030 |
| I-1032 |
| I-1033 |
| I-1034 |
| I-1035 |
| I-1036 |
| I-1037 |
| I-1038 |
| I-1039 |
| I-1041 |
| I-1042 |
| I-1043 |
| I-1044 |
| I-1045 |
| I-1047 |
| I-1048 |
| I-1049 |
| I-1053 |
| I-1054 |
| I-1055 |
| I-1056 |
| I-1057 |
| I-1059 |
| I-1061 |
| I-1062 |
| I-1063 |
| I-1065 |
| I-1089 |
| I-1090 |
| I-1091 |
| I-1092 |
| I-1093 |
| I-1094 |
| I-1095 |
| I-1098 |
| I-1101 |
| I-1102 |
| I-1103 |
| I-1105 |
| I-1106 |
| I-1107 |
| I-1108 |
| I-1111 |
| I-1116 |
| I-1117 |
| I-1121 |
| I-1122 |
| I-1123 |
| I-1124 |
| I-1136 |
| I-1137 |
| I-1150 |
| I-1151 |
| I-1152 |
| I-1156 |
| I-1163 |
| I-1165 |
| I-1166 |
| I-1167 |

TABLE 10-continued

Additional Exemplary Compounds
Compound

| Compound |
|---|
| I-1168 |
| I-1169 |
| I-1170 |
| I-1171 |
| I-1172 |
| I-1173 |
| I-1174 |
| I-1190 |
| I-1193 |
| I-1195 |
| I-1197 |
| I-1207 |
| I-1208 |
| I-1214 |
| I-1215 |
| I-1216 |
| I-1217 |
| I-1219 |
| I-1220 |
| I-1222 |
| I-1231 |
| I-1232 |
| I-1264 |
| I-1265 |
| I-1272 |
| I-1303 |
| I-1329 |
| I-1330 |
| I-1331 |
| I-1332 |
| I-1335 |
| I-1340 |
| I-1342 |
| I-1343 |
| I-1368 |
| I-1369 |
| I-1373 |
| I-1374 |
| I-1390 |
| I-1405 |
| I-1406 |
| I-1407 |
| I-1408 |
| I-1409 |
| I-1410 |
| I-1411 |
| I-1413 |
| I-1415 |
| I-1416 |
| I-1419 |
| I-1437 |
| I-1438 |
| I-1439 |
| I-1440 |
| I-1441 |
| I-1442 |
| I-1443 |
| I-1444 |
| I-1445 |
| I-1448 |
| I-1449 |
| I-1452 |
| I-1453 |
| I-1454 |
| I-1455 |
| I-1456 |
| I-1458 |
| I-1464 |
| I-1474 |
| I-1482 |
| I-1483 |
| I-1492 |
| I-1499 |
| I-1500 |
| I-1506 |
| I-1529 |
| I-1530 |

TABLE 10-continued

Additional Exemplary Compounds
Compound

| Compound |
|---|
| I-1531 |
| I-1537 |
| I-1538 |
| I-1539 |
| I-1540 |
| I-1542 |
| I-1544 |
| I-1547 |
| I-1549 |
| I-1550 |
| I-1552 |
| I-1553 |
| I-1573 |
| I-1574 |
| I-1583 |
| I-1584 |
| I-1585 |
| I-1586 |
| I-1589 |
| I-1598 |
| I-1599 |
| I-1600 |
| I-1601 |
| I-1602 |
| I-1603 |
| I-1604 |
| I-1605 |
| I-1609 |
| I-1624 |
| I-1627 |
| I-1628 |
| I-1630 |
| I-1631 |
| I-1645 |
| I-1646 |
| I-1647 |
| I-1648 |
| I-1649 |
| I-1650 |
| I-1652 |
| I-1653 |
| I-1662 |
| I-1664 |
| I-1665 |
| I-1667 |
| I-1676 |
| I-1684 |
| I-1685 |
| I-1688 |
| I-1690 |
| I-1692 |
| I-1693 |
| I-1694 |
| I-1696 |
| I-1700 |
| I-1701 |
| I-1702 |
| I-1703 |
| I-1704 |
| I-1707 |
| I-1708 |
| I-1723 |
| I-1724 |
| I-1730 |
| I-1734 |
| I-1743 |
| I-1744 |
| I-1750 |
| I-1751 |
| I-1758 |
| I-1759 |
| I-1760 |
| I-1767 |
| I-1773 |
| I-1777 |
| I-1778 |
| I-1779 |

TABLE 10-continued

Additional Exemplary Compounds

| Compound |
|---|
| I-1780 |
| I-1781 |
| I-1782 |
| I-1783 |
| I-1785 |
| I-1786 |
| I-1787 |
| I-1792 |
| I-1793 |
| I-1796 |
| I-1797 |
| I-1802 |
| I-1803 |
| I-1804 |
| I-1812 |
| I-1813 |
| I-1814 |
| I-1816 |
| I-1817 |
| I-1821 |
| I-1822 |
| I-1825 |
| I-1827 |
| I-1829 |
| I-1830 |
| I-1831 |
| I-1834 |
| I-1838 |
| I-1839 |
| I-1840 |
| I-1842 |
| I-1843 |
| I-1844 |
| I-1845 |
| I-1847 |
| I-1848 |
| I-1849 |
| I-1850 |
| I-1855 |
| I-1856 |
| I-1858 |
| I-1859 |
| I-1864 |
| I-1865 |
| I-1866 |
| I-1869 |
| I-1870 |
| I-1873 |
| I-1874 |
| I-1875 |
| I-1876 |
| I-1877 |
| I-1878 |
| I-1879 |
| I-1880 |
| I-1881 |
| I-1882 |
| I-1883 |
| I-1884 |
| I-1899 |
| I-1900 |
| I-1910 |
| I-1913 |
| I-1922 |
| I-1923 |
| I-1924 |
| I-1925 |
| I-1928 |
| I-1929 |
| I-1932 |
| I-1933 |
| I-1934 |
| I-1936 |
| I-1937 |
| I-1938 |
| I-1939 |
| I-1947 |

TABLE 10-continued

Additional Exemplary Compounds

| Compound |
|---|
| I-1948 |
| I-1957 |
| I-1960 |
| I-1964 |
| I-1966 |
| I-1982 |
| I-1983 |
| I-1984 |
| I-1985 |
| I-1986 |
| I-1987 |
| I-1990 |
| I-1991 |
| I-1992 |
| I-2000 |
| I-2001 |
| I-2002 |
| I-2003 |
| I-2004 |
| I-2008 |
| I-2012 |
| I-2015 |
| I-2028 |
| I-2029 |
| I-2030 |
| I-2031 |
| I-2032 |
| I-2033 |
| I-2034 |
| I-2035 |
| I-2037 |
| I-2044 |
| I-2045 |
| I-2051 |
| I-2063 |
| I-2064 |
| I-2065 |
| I-2066 |
| I-2067 |
| I-2068 |
| I-2069 |
| I-2125 |
| I-2137 |
| I-2146 |
| I-2147 |
| I-2161 |
| I-2169 |
| I-2170 |
| I-2185 |
| I-2185 |
| I-2186 |
| I-2200 |
| I-2201 |
| I-2233 |
| I-2234 |
| I-2258 |
| I-2259 |
| I-2267 |
| I-2289 |
| I-2290 |
| I-2706 |
| I-2707 |

Example 35

N-[3-(2-Chloro-5-fluorophenyl)-6-[(oxetan-2-yl)methyl]-1-oxo-2,3-dihydro-1H-isoindol-4-yl]-3-fluoro-5-(trifluoromethyl)benzamide

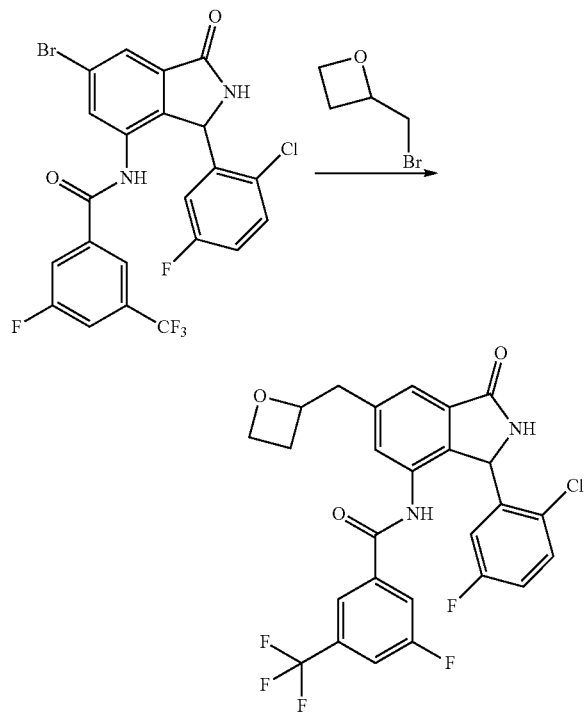

To a 4-mL vial were added 4,4'-di-tert-butyl-2,2'-dipyridyl (3.67 mg, 0.05 eq) and NiCl$_2$ (3.07 mg, 0.01 eq), and dioxane (1.0 mL). The solution was stirred and sparged with nitrogen for 15 mins, until it turned light blue. While the nickel ligand stock solution was stirring, to an 8-mL vial with a stir bar was added N-[6-bromo-3-(2-chloro-5-fluorophenyl)-1-oxo-2,3-dihydro-1H-isoindol-4-yl]-3-fluoro-5-(trifluoromethyl)benzamide (150 mg, 274 μmol) and [Ir{dF(CF$_3$)ppy}$_2$(dtbpy)]PF6 (3.07 mg, 0.01 eq) dissolved in dioxane (2.73 mL). The mixture was purged with nitrogen and stirred. To the Ir-containing mixture were added, in order, lutidine (95.1 μL, 3 eq), 1,1,1,3,3,3-hexamethyldisilazane (68.1 mg, 1.0 eq), the nickel ligand stock solution, then 2-(bromomethyl)oxetane (39.5 μL, 1.5 eq). The reaction was sparged for 10 minutes before sealing with parafilm and vacuum grease. The reaction was placed in the Merck photoreactor to run at 100% intensity (wavelengths: 365 nm to 450 nm) for 3 hours before checking reaction progress via LCMS. The reaction was concentrated and purified on the AccQ system eluting with 30-60% water with 0.1% formic acid. Product-containing fractions were lyophilized to yield N-[3-(2-chloro-5-fluorophenyl)-6-[(oxetan-2-yl)methyl]-1-oxo-2,3-dihydro-1H-isoindol-4-yl]-3-fluoro-5-(trifluoromethyl)benzamide (94 mg, 63.9%).

Additional compounds prepared according to the methods of Example 35 are listed in Table 11 below. Certain compounds in Table 11 were prepared with other compounds whose preparation is described elsewhere in the Examples.

TABLE 11

| Additional Exemplary Compounds Compound |
|---|
| I-529 |
| I-1376 |

Example 36

N-[3-(2-Chloro-5-fluorophenyl)-1-oxo-6-(5-oxo-5,6-dihydro-1,6-naphthyridin-6-yl)-2,3-dihydro-1H-isoindol-4-yl]-3-fluoro-5-(trifluoromethyl)benzamide

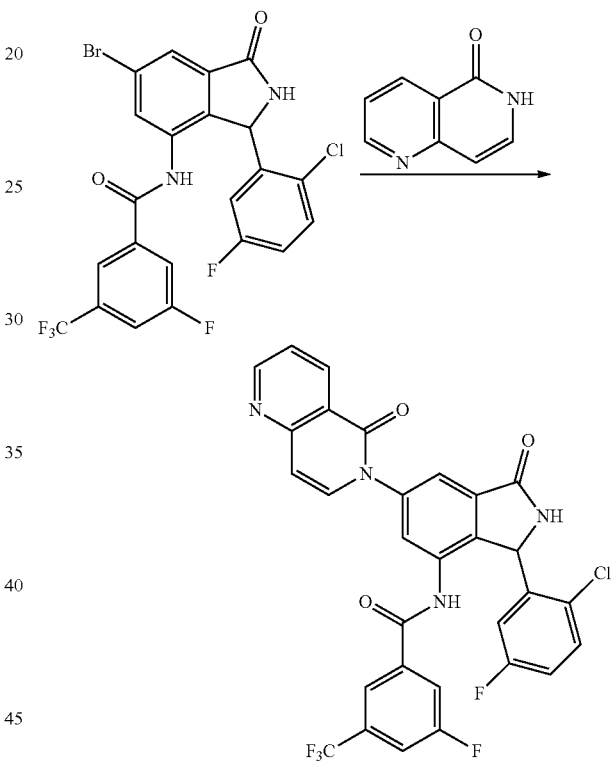

A resealable reaction vial was charged with 5,6-dihydro-1,6-naphthyridin-5-one (20 mg, 0.1368 mmol), N-[6-bromo-3-(2-chloro-5-fluorophenyl)-1-oxo-2,3-dihydro-1H-isoindol-4-yl]-3-fluoro-5-(trifluoromethyl)benzamide (74.6 mg, 0.1368 mmol), copper (I) iodide (3.90 mg, 0.15 eq), dipotassium carbonate (8.50 mg, 0.45 eq), and a stirbar before being evacuated and purged with nitrogen three times. Dimethylformamide (0.5 mL) was added, and the mixture was stirred at 130° C. overnight. Reaction mixture was then cooled and diluted with water. The aqueous layer was extracted with ethyl acetate 3 times. The organic layer was washed with brine, dried over sodium sulfate, filtered, and concentrated. The resulting material was purified by prep-HPLC (acetonitrile/water/0.1% formic acid). Product-containing fractions were lyophilized to yield product N-[3-(2-chloro-5-fluorophenyl)-1-oxo-6-(5-oxo-5,6-dihydro-1,6-naphthyridin-6-yl)-2,3-dihydro-1H-isoindol-4-yl]-3-fluoro-5-(trifluoromethyl)benzamide (3.91 mg, 4.4%).

Example 37

N-[3-(2-Chloro-5-fluorophenyl)-1-oxo-6-[(pyrimidin-5-yl)methoxy]-2,3-dihydro-1H-isoindol-4-yl]-3-fluoro-5-(trifluoromethyl)benzamide

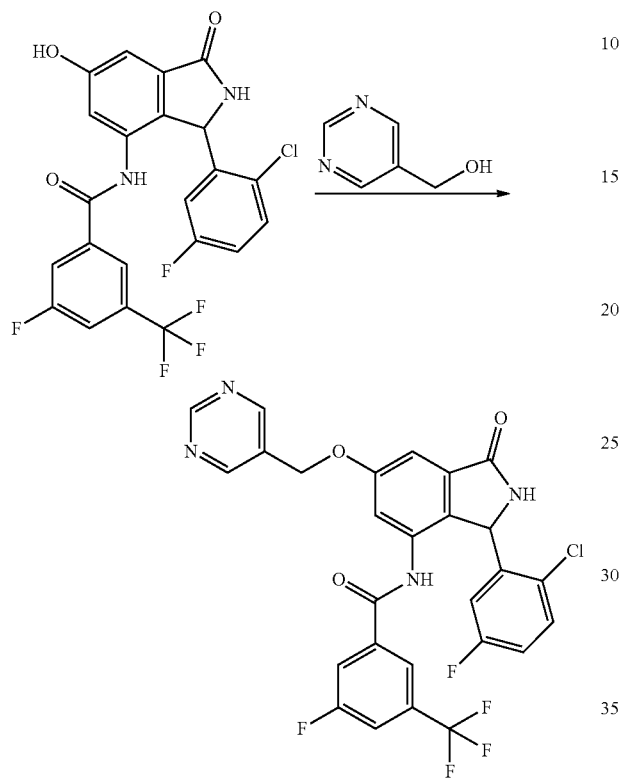

To a 20-mL vial was added N-[3-(2-chloro-5-fluorophenyl)-6-hydroxy-1-oxo-2,3-dihydro-1H-isoindol-4-yl]-3-fluoro-5-(trifluoromethyl)benzamide (100 mg, 207 µmol), (pyrimidin-5-yl)methanol (22.7 mg, 207 µmol), triphenylphosphine (70.5 mg, 1.3 eq), and diisopropyl azodicarboxylate (52.8 µL, 1.3 eq) dissolved in tetrahydrofuran (5 mL). The reaction was stirred and heated at reflux for 20 mins. Reaction progress was checked via LCMS and showed complete conversion to product. The reaction mixture was purified with AccQ prep system to yield N-[3-(2-chloro-5-fluorophenyl)-1-oxo-6-[(pyrimidin-5-yl)methoxy]-2,3-dihydro-1H-isoindol-4-yl]-3-fluoro-5-(trifluoromethyl)benzamide (46.4 mg, 38.9%).

Additional compounds prepared according to the methods of Example 37 are listed in Table 12 below. Certain compounds in Table 12 were prepared with other compounds whose preparation is described elsewhere in the Examples.

TABLE 12

| Additional Exemplary Compounds Compound |
| --- |
| I-708 |
| I-709 |
| I-735 |
| I-739 |
| I-740 |
| I-748 |
| I-773 |
| I-812 |
| I-819 |
| I-873 |
| I-977 |
| I-1064 |
| I-1113 |
| I-1129 |
| I-1131 |
| I-1132 |
| I-1135 |
| I-1149 |
| I-1160 |
| I-1184 |
| I-1192 |
| I-1198 |
| I-1205 |
| I-1210 |
| I-873 |
| I-977 |
| I-1064 |
| I-1113 |
| I-1129 |
| I-1131 |
| I-1132 |
| I-1135 |
| I-1149 |
| I-1160 |
| I-1184 |
| I-1192 |
| I-1198 |
| I-1205 |
| I-1210 |
| I-1221 |
| I-1234 |
| I-1239 |
| I-1251 |
| I-1252 |
| I-1253 |
| I-1289 |
| I-1295 |
| I-1298 |
| I-1304 |
| I-1305 |
| I-1320 |
| I-1322 |
| I-1333 |
| I-1334 |
| I-1338 |
| I-1341 |
| I-1346 |
| I-1347 |
| I-1348 |
| I-1357 |
| I-1366 |
| I-1375 |
| I-1378 |
| I-1412 |
| I-1414 |
| I-1421 |
| I-1431 |
| I-1432 |
| I-1457 |
| I-1466 |
| I-1467 |
| I-1468 |
| I-1517 |
| I-1518 |
| I-1519 |
| I-1520 |
| I-1521 |
| I-1522 |
| I-1523 |
| I-1524 |
| I-1525 |
| I-1526 |
| I-1527 |

TABLE 12-continued

Additional Exemplary Compounds
Compound

I-1541
I-1566
I-1567
I-1568
I-1569
I-1735
I-1736
I-1887
I-1888
I-1935
I-2005
I-2006
I-2007
I-2009
I-2061
I-2062
I-2134

Example 38

N-[3-(2-Chloro-5-fluorophenyl)-1-oxo-6-{[(1r*,3r**)-3-hydroxycyclobutyl]amino}-2,3-dihydro-1H-isoindol-4-yl]-3-fluoro-5-(trifluoromethyl)benzamide

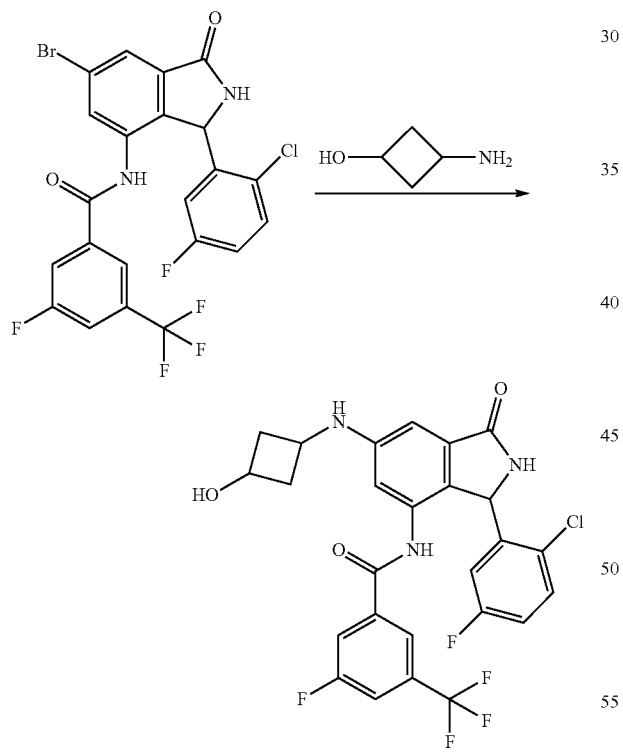

In a microwave vial, a solution of N-[6-bromo-3-(2-chloro-5-fluorophenyl)-1-oxo-2,3-dihydro-1H-isoindol-4-yl]-3-fluoro-5-(trifluoromethyl)benzamide (70 mg, 128 µmol), (1r*,3r**)-3-aminocyclobutan-1-ol hydrochloride (31.6 mg) and BrettPhos Pd G4 (35.3 mg) in toluene (1.5 mL) was degassed by passing nitrogen through the solution. To the reaction mixture, lithium bis(trimethylsilyl)azanide (512 µL, 512 µmol) was added. The tube was sealed and heated at 110° C. for 1 hour. The reaction was quenched with water (2 mL) and the mixture was passed through Celite®. The crude mixture was purified on C18 reverse-phase column (12 g cartridge) using water with ACN 5-60% as an eluent. The fractions containing the desired product were collected and lyophilized to yield N-[3-(2-chloro-5-fluorophenyl)-1-oxo-6-{[(1r*,3r**)-3-hydroxycyclobutyl]amino}-2,3-dihydro-1H-isoindol-4-yl]-3-fluoro-5-(trifluoromethyl)benzamide (2 mg, 2.8%).

Additional compounds prepared according to the methods of Example 38 are listed in Table 13 below. Certain compounds in Table 13 were prepared with other compounds whose preparation is described elsewhere in the Examples.

TABLE 13

Additional Exemplary Compounds
Compound

I-39
I-51
I-53
I-275
I-284
I-288
I-304
I-311
I-312
I-310
I-321
I-329
I-338
I-343
I-359
I-370
I-375
I-478
I-530
I-532
I-540
I-541
I-609
I-613
I-695
I-707
I-721
I-723
I-728
I-729
I-730
I-780
I-781
I-814
I-830
I-848
I-868
I-869
I-899
I-900
I-960
I-1015
I-1040
I-1069
I-1070
I-1082
I-1086
I-1125
I-1126
I-1127
I-1128
I-1140
I-1146
I-1164
I-1181
I-1189
I-1227
I-1233
I-1236
I-1237
I-1248

TABLE 13-continued

Additional Exemplary Compounds
Compound

I-1249
I-1250
I-1260
I-1261
I-1262
I-1263
I-1267
I-1273
I-1291
I-1299
I-1301
I-1309
I-1310
I-1354
I-1387
I-1388
I-2148
I-2192

Example 39

N-(6-(Aminomethyl)-1-oxo-3-(o-tolyl)isoindolin-4-yl)benzo[b]thiophene-3-carboxamide (I-88)

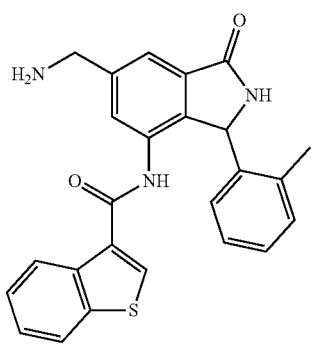 [SMILES: Cc1ccccc1C1NC(=O)c2cc(CN)cc(NC(=O)c3csc4ccccc34)c21]

A reaction vessel was charged with N-[6-bromo-3-(2-methylphenyl)-1-oxo-2,3-dihydro-1H-isoindol-4-yl]-1-benzothiophene-3-carboxamide (20 mg, 0.04189 mmol), 2-{[(tert-butoxy)carbonyl]amino}acetic acid (22.0 mg, 0.1256 mmol), $Cs_2CO_3$ (40.8 mg, 0.1256 mmol), $NiCl_2 \cdot DME$ (1.37 mg, 0.006283 mmol), 4,4'-di-tert-butyl-2,2'-dipyridyl (1.68 mg, 0.006283 mmol), and $[Ir\{dF(CF_3)ppy\}_2(dtbpy)]PF_6$ (0.02 mol %). The reaction vessel was sealed, evacuated, and purged with $N_2$. Then 0.3 mL of DMAC was added, and the mixture was stirred for 16 hrs at ambient temperature while irradiating with a Kessel lamp. The reaction mixture was diluted with EtOAc and filtered through a plug of silica.

The filtrate was concentrated, then diluted with 1:1 TFA and DCM and stirred for 4 hrs. The reaction was concentrated, and the product was purified by reverse phase HPLC using a gradient of water (0.1% FA) and acetonitrile (0.1% FA) 80/20 to 30/70 in 13 minutes then 5/95. Product-containing fractions were combined and lyophilized to provide N-(6-(aminomethyl)-1-oxo-3-(o-tolyl)isoindolin-4-yl)benzo[b]thiophene-3-carboxamide (2 mg, 10%).

Additional compounds prepared according to the methods of Example 39 are listed in Table 14 below. Certain compounds in Table 14 below were prepared with other compounds whose preparation is described elsewhere in the Examples.

TABLE 14

Additional Exemplary Compounds
Compound

I-87
I-89
I-90
I-126
I-140
I-155
I-207
I-223
I-260

Example 40

N-[6-Amino-3-(2-methylphenyl)-1-oxo-2,3-dihydro-1H-isoindol-4-yl]-1,2-benzothiazole-3-carboxamide (I-50)

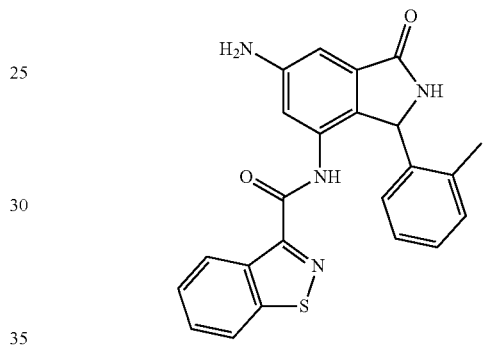

A reaction vessel was charged with N-[6-bromo-3-(2-methylphenyl)-1-oxo-2,3-dihydro-1H-isoindol-4-yl]-1,2-benzothiazole-3-carboxamide (50 mg, 0.1 mmol) and $Pd(tBu)_3P$-G4 (13.7 mg, 0.017 mmol). The reaction vessel was evacuated and purged with $N_2$. Then 0.6 mL of toluene was added, and the mixture was stirred for 5 min at ambient temperature. Then LiHMDS (0.5 mL, 0.5 mmol) was added, and the mixture was stirred for 16 hours at 50° C. The mixture was diluted with 2 mL of MeOH (0.1% FA), stirred, and then concentrated. The resulting residue was diluted with 2 mL of DMSO and purified by reverse phase HPLC using a gradient of water (0.1% FA) and acetonitrile (0.1% FA) 70/30 to 35/65 in 13 minutes, then 5/95. Product-containing fractions were combined and lyophilized to provide N-[6-amino-3-(2-methylphenyl)-1-oxo-2,3-dihydro-1H-isoindol-4-yl]-1,2-benzothiazole-3-carboxamide (10 mg, 20%).

Additional compounds prepared according to the methods of Example 40 are listed in Table 15 below. Certain compounds in Table 15 below were prepared with other compounds whose preparation is described elsewhere in the Examples.

TABLE 15

Additional Exemplary Compounds
Compound

I-34
I-40
I-65

TABLE 15-continued

Additional Exemplary Compounds
Compound

I-66
I-91
I-92
I-125
I-213
I-217
I-218
I-289

Example 41

N-[6-Ethenyl-3-(2-methylphenyl)-1-oxo-2,3-dihydro-1H-isoindol-4-yl]-1-benzothiophene-3-carboxamide (I-100)

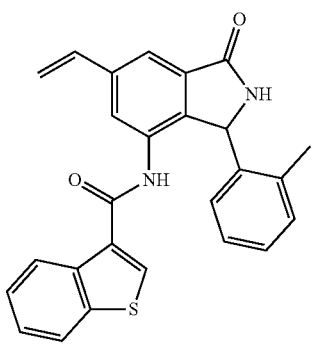 [SMILES: C=Cc1cc(NC(=O)c2csc3ccccc23)c2c(c1)C(=O)NC2c1ccccc1C]

To a screw-top glass reaction vial equipped with a stir bar was added N-[6-bromo-3-(2-methylphenyl)-1-oxo-2,3-dihydro-1H-isoindol-4-yl]-1-benzothiophene-3-carboxamide (80 mg, 167.0 µmol), 1,4-dioxane (1.5 mL), tributyl(vinyl)tin (80 µL, 273 umol), DABCO (2.00 mg, 17.8 µmol), and TBAF (500 µL). The suspension was degassed by freeze-pump-thaw cycle (3 cycles), followed by bubbling with nitrogen gas for 10 min. Palladium acetate (2.00 mg, 8.90 µmol) was then introduced into the suspension. The suspension was sealed, and the vial was placed in a pre-heated oil bath (110° C., external) until the reaction was deemed complete (ca. 16 h). The reaction mixture was filtered through Celite and washed with ethyl acetate. The combined organic fraction was evaporated under reduced pressure to afford the crude residue. This crude residue was filtered through a small pad of silica, and eluted first with hexanes, and then with ethyl acetate. The combined organic fraction was evaporated under reduced pressure to afford a crude product. Approximately half of this crude product was purified by normal-phase flash column chromatography (eluting with 20% EtOAc in Hexanes to 100% ethyl acetate in gradient) to afford N-[6-ethenyl-3-(2-methylphenyl)-1-oxo-2,3-dihydro-1H-isoindol-4-yl]-1-benzothiophene-3-carboxamide (9 mg) as an off-white solid.

Example 42

N-[6-(2-Hydroxyethyl)-3-(2-methylphenyl)-1-oxo-2,3-dihydro-1H-isoindol-4-yl]-1-benzothiophene-3-carboxamide (I-181)

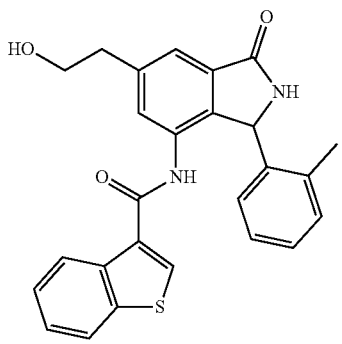 [SMILES: Cc1ccccc1C1NC(=O)c2cc(CCO)cc(NC(=O)c3csc4ccccc34)c21]

Step 1: A round bottom flask equipped with a stir bar was charged with a solution of crude N-[6-ethenyl-3-(2-methylphenyl)-1-oxo-2,3-dihydro-1H-isoindol-4-yl]-1-benzothiophene-3-carboxamide (~25 mg, ~59 µmol) in THF (1.0 mL). To this solution was added an excess of $BH_3 \cdot THF$ (1.0 M THF solution, 0.2 mL, 200 µmol) at room temperature. The solution was then stirred for 4 hours at room temperature. To this solution was added sodium perborate tetrahydrate (30.7 mg, 200 µmol), and the mixture was stirred for 5 minutes. To the solution was then added water (1.0 mL), and the mixture was stirred overnight. The solution was evaporated under reduced pressure to afford a crude residue. The crude residue was purified by reverse-phase flash column chromatography (12 g, C18, eluting with increasing amount of acetonitrile (0-100%) from initial 10 mM ammonium bicarbonate in water) to afford a mixture of the desired alcohol and a minor impurity as white powder after lyophilization. This white powder was purified further using prep-HPLC (gradient 20% to 100% acetonitrile in 0.1% FA in water) to afford, after lyophilization of pure fractions, 3.2 mg of N-[6-(2-hydroxyethyl)-3-(2-methylphenyl)-1-oxo-2,3-dihydro-1H-isoindol-4-yl]-1-benzothiophene-3-carboxamide as a white solid.

Additional compounds prepared according to the methods of Example 42 are listed in Table 16 below. Certain compounds in Table 16 below were prepared with other compounds whose preparation is described elsewhere in the Examples.

Example 43

N-[6-(1,2-Dihydroxyethyl)-3-(2-methylphenyl)-1-oxo-2,3-dihydro-1H-isoindol-4-yl]-1-benzothiophene-3-carboxamide (I-139)

TABLE 16

Additional Exemplary Compounds
Compound

I-119
I-434
I-579

Example 43

N-[6-(1,2-Dihydroxyethyl)-3-(2-methylphenyl)-1-oxo-2,3-dihydro-1H-isoindol-4-yl]-1-benzothiophene-3-carboxamide (I-139)

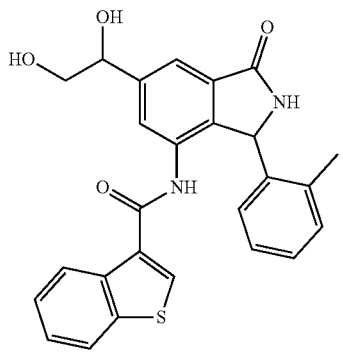 [SMILES: Cc1ccccc1C1NC(=O)c2cc(C(O)CO)cc(NC(=O)c3csc4ccccc34)c21]

Step 1: A round bottom flask equipped with a stir bar was charged with a solution of crude N-[6-ethenyl-3-(2-methylphenyl)-1-oxo-2,3-dihydro-1H-isoindol-4-yl]-1-benzothiophene-3-carboxamide (~25 mg, ~59 µmol) in THF (1.5 mL) and water (0.4 mL). To this reaction mixture was added NMO (6.6 mg, 56 µmol) and potassium osmate(VI) dihydrate (1.9 mg, 5 µmol). The solution was stirred for two hours. The volatiles were evaporated under reduced pressure to afford a residue, which was purified by normal-phase flash column chromatography (eluting with 20% EtOAc/Hexanes to 100% EtOAc in gradient, then 10% MeOH in EtOAc), to afford the 1:1 mixture of desired diol diastereomers from the MeOH/EtOAc fractions. The solvent was evaporated under reduced pressure to afford a concentrated diol mixture. The diol mixture was purified further by reverse-phase flash column chromatography (eluting with 10 mM ammonium bicarbonate in water to 100% acetonitrile in gradient). Lyophilization of the pure fractions afforded 4.8 mg of the desired diol N-[6-(1,2-dihydroxyethyl)-3-(2-methylphenyl)-1-oxo-2,3-dihydro-1H-isoindol-4-yl]-1-benzothiophene-3-carboxamide as a 1:1 mixture of diastereomers as a white solid.

Additional compounds prepared according to the methods of Example 43 are listed in Table 17 below. Certain compounds in Table 17 below were prepared with other compounds whose preparation is described elsewhere in the Examples.

TABLE 17

| Additional Exemplary Compounds Compound |
| --- |
| I-120 |
| I-382 |

Example 44

N-[6-(Hydroxymethyl)-3-(2-methylphenyl)-1-oxo-2,3-dihydro-1H-isoindol-4-yl]-1,2-benzothiazole-3-carboxamide (I-131)

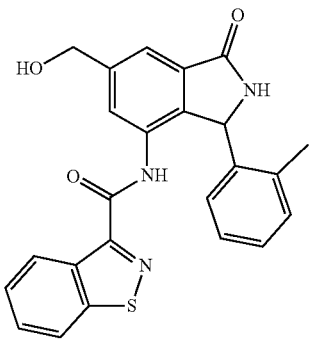 [SMILES: Cc1ccccc1C1NC(=O)c2cc(CO)cc(NC(=O)c3nsc4ccccc34)c21]

Methyl 7-amino-2-(4-methoxybenzyl)-3-oxo-1-(o-tolyl)isoindoline-5-carboxylate and Methyl 2-(4-methoxybenzyl)-7-((methoxycarbonyl)amino)-3-oxo-1-(o-tolyl)isoindoline-5-carboxylate

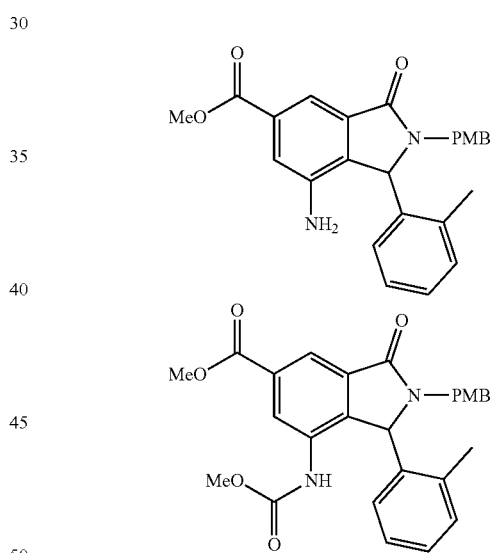

Step 1: To a solution of 4-amino-6-bromo-2-(4-methoxybenzyl)-3-(o-tolyl)isoindolin-1-one (17.1 g, 39.1 mmol, 1.00 equiv.) in MeOH (500 mL) was added DPPF (2.17 g, 3.91 mmol, 0.10 equiv.), Pd(OAc)$_2$ (1.76 g, 7.82 mmol, 0.20 equiv.), and KOAc (11.5 g, 117 mmol, 3.00 equiv.). The mixture was degassed and purged with CO three times. The mixture was heated to 80° C. and stirred at 80° C. for 10 hrs under CO (50 psi). LCMS showed significant unconsumed 4-amino-6-bromo-2-(4-methoxybenzyl)-3-(o-tolyl)isoindolin-1-one. The mixture was stirred at 80° C. for 120 hrs. The mixture was filtered, and the filtrate was concentrated in vacuum to give the crude product. The crude product was purified by column chromatography (SiO$_2$, petroleum ether/ethyl acetate=1/0 to 0/1) to afford methyl 7-amino-2-(4-methoxybenzyl)-3-oxo-1-(o-tolyl)isoindoline-5-carboxylate (MS: m/z=417.2 [M+H]$^1$) and methyl 2-(4-methoxybenzyl)-

7-((methoxycarbonyl)amino)-3-oxo-1-(o-tolyl)isoindoline-5-carboxylate (11.5 g, 22.9 mmol, 58.6% yield, 94.5% purity) as a light yellow solid.

Characterization data for methyl 2-(4-methoxybenzyl)-7-((methoxycarbonyl)amino)-3-oxo-1-(o-tolyl)isoindoline-5-carboxylat: MS: m/z=475.3 [M+H]$^+$; $^1$H NMR (400 MHz, DMSO-d$_6$) δ 9.17 (d, J=16.4 Hz, 1H), 8.13 (dd, J=23.6, 1.2 Hz, 1H), 7.94 (d, J=1.2 Hz, 1H), 7.60 (d, J=19.4 Hz, 1H), 6.93-6.83 (d, J=19.4 Hz, 1H), 7.45 (d, J=24 Hz, 1H), 7.28-7.22 (m, 5H), 7.07-7.00 (m, 6H), 6.91-6.87 (m, 4H), 6.46 (d, J=7.6 Hz, 1H), 6.29 (d, J=7.6 Hz, 1H), 5.97 (s, 1H), 5.73 (s, 1H), 5.63 (s, 1H), 5.50 (s, 1H), 5.01-4.91 (m, 2H), 4.77 (s, 1H), 3.92 (d, J=4.8 Hz, 4H), 3.87 (d, J=4.8 Hz, 2H), 3.74 (d, J=8.0 Hz, 6H), 3.62 (d, J=14.8 Hz, 1H), 3.49 (d, J=9.6 Hz, 5H), 2.25 (d, J=18.4 Hz, 3H), 1.48 (s, 1H), 1.34 (s, 2H).

4-Amino-6-(hydroxymethyl)-2-[(4-methoxyphenyl)methyl]-3-(2-methylphenyl)-2,3-dihydro-1H-isoindol-1-one

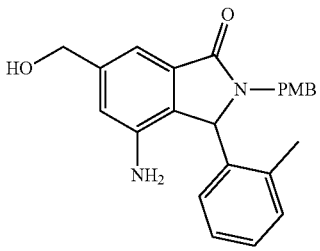

Step 2: A solution of methyl 7-amino-2-(4-methoxybenzyl)-3-oxo-1-(o-tolyl)isoindoline-5-carboxylate (516 mg, 1.24 mmol) in THF (6.19 mL) was stirred under nitrogen atmosphere and cooled to 0° C. using an ice bath. Then a solution of borane lithium hydride (930 µL, 1.86 mmol, 2 M in THF) was added, and the mixture was warmed to room temperature overnight. The reaction mixture was quenched with water (20 mL), extracted with DCM (3×20 mL), and the combined organic phases were concentrated under reduced pressure. The resulting residue was purified by reverse-phase chromatography (60 g column C18, 10 to 100% ACN/AmF 10 mM) to afford after lyophilisation 4-amino-6-(hydroxymethyl)-2-[(4-methoxyphenyl)methyl]-3-(2-methylphenyl)-2,3-dihydro-1H-isoindol-1-one (188 mg, 0.484 mmol, 39% yield) as a white powder. MS: m/z=389.3 [M+H]$^−$.

N-[6-(Hydroxymethyl)-2-[(4-methoxyphenyl)methyl]-3-(2-methylphenyl)-1-oxo-2,3-dihydro-1H-isoindol-4-yl]-1,2-benzothiazole-3-carboxamide

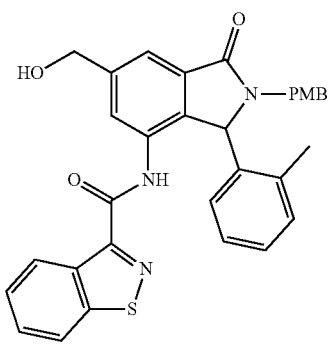

Step 3: To a solution of 4-amino-6-(hydroxymethyl)-2-[(4-methoxyphenyl)methyl]-3-(2-methylphenyl)-2,3-dihydro-1H-isoindol-1-one (150 mg, 0.3861 mmol) in DCM (1.93 mL) was added 1H-imidazole (65.7 mg, 0.9652 mmol), and the reaction mixture was cooled to 0° C. using an ice bath. Then tert-butyl(chloro)dimethylsilane (69.8 mg, 0.4633 mmol) was added, and the reaction mixture was stirred for 2h at room temperature.

To the reaction mixture was added 1,2-benzothiazole-3-carbonyl chloride (76.3 mg, 0.3861 mmol), and the reaction mixture was stirred for 3 days at room temperature. The reaction mixture was concentrated to dryness and purified by reverse phase chromatography (60 g C18 column, 10 to 100% ACN/AmF 10 mM) to afford after lyophilisation N-[6-(hydroxymethyl)-2-[(4-methoxyphenyl)methyl]-3-(2-methylphenyl)-1-oxo-2,3-dihydro-1H-isoindol-4-yl]-1,2-benzothiazole-3-carboxamide (80.5 mg, 0.1466 mmol, 38% yield) as an orange powder. MS: m/z=550.3 [M+H]$^+$; $^1$H NMR (400 MHz, DMSO-d$_6$) δ 10.18 (s, 0.31H), 10.06 (s, 0.48H), 8.58 (d, J=8.2 Hz, 0.32H), 8.52 (d, J=8.2 Hz, 0.53H), 8.29 (d, J=8.3 Hz, 1H), 7.72 (d, J=4.5 Hz, 1H), 7.71-7.67 (m, 1H), 7.67-7.63 (m, 1H), 7.60-7.52 (m, 1H), 7.27 (d, J=7.0 Hz, 0.38H), 7.11-6.81 (m, 7H), 6.74 (t, J=6.7 Hz, 0.36H), 6.42-6.35 (m, 0.57H), 5.96 (s, 0.51H), 5.76 (s, 0.33H), 5.45 (td, J=5.8, 2.9 Hz, 1H), 5.00 (dd, J=15.0, 11.1 Hz, 1H), 4.65 (t, J=5.2 Hz, 2H), 3.73 (s, 3H), 3.61 (d, J=14.9 Hz, 0.40H), 3.47 (d, J=15.5 Hz, 0.71H), 2.10 (s, 2H), 1.44 (s, 1H). The compound appears to exist as non-interconverting rotamers in DMSO solution at ambient temperature.

1883

N-[6-(Hydroxymethyl)-3-(2-methylphenyl)-1-oxo-2,3-dihydro-1H-isoindol-4-yl]-1,2-benzothiazole-3-carboxamide

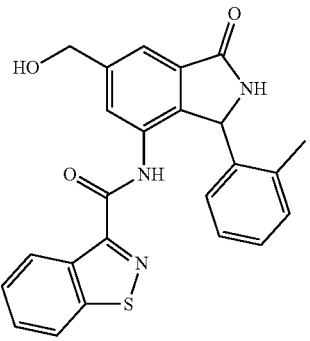 [SMILES: Cc1ccccc1C1NC(=O)c2cc(CO)cc(NC(=O)c3nsc4ccccc34)c21]

Step 4: In a sealed tube N-[6-(hydroxymethyl)-2-[(4-methoxyphenyl)methyl]-3-(2-methylphenyl)-1-oxo-2,3-dihydro-1H-isoindol-4-yl]-1,2-benzothiazole-3-carboxamide (231 mg, 0.420 mmol) was dissolved in trifluoroacetic acid (6.42 mL, 84.0 mmol). The resulting mixture was heated at 90° C. for 24 h. The reaction was diluted with DCM (50 mL), the organic layer was washed with water (2×5 mL), and the organic phase was concentrated under reduced pressure. The residue was purified by reverse phase chromatography (60 g $C_{18}$ cartridge, 10 to 100% ACN/AmF 10 mM) to afford N-[6-(hydroxymethyl)-3-(2-methylphenyl)-1-oxo-2,3-dihydro-1H-isoindol-4-yl]-1,2-benzothiazole-3-carboxamide (123 mg, 0.288 mmol, 68% yield) as a brown powder after lyophilisation.

Additional compounds prepared according to the methods of Example 44 are listed in Table 18 below. Certain compounds in Table 18 below were prepared with other compounds whose preparation is described elsewhere in the Examples.

TABLE 18

| Additional Exemplary Compounds |
| --- |
| Compound |
| I-154 |
| I-185 |
| I-224 |
| I-306 |
| I-307 |
| I-314 |
| I-373 |

1884

Example 45

N-(6-((Methylsulfonyl)methyl)-1-oxo-3-(o-tolyl)isoindolin-4-yl)benzo[d]isothiazole-3-carboxamide (I-202)

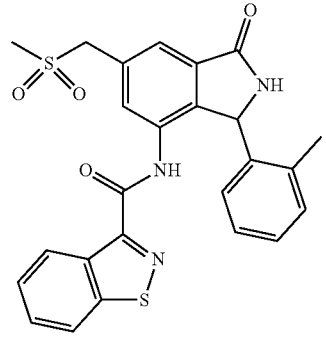

N-(6-(Bromomethyl)-1-oxo-3-(o-tolyl)isoindolin-4-yl)benzo[d]isothiazole-3-carboxamide

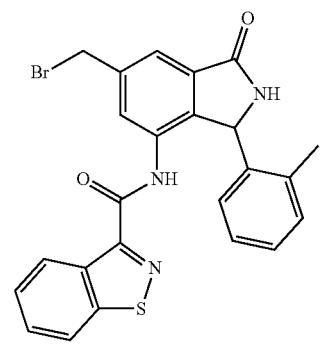 [SMILES: Cc1ccccc1C1NC(=O)c2cc(CBr)cc(NC(=O)c3nsc4ccccc34)c21]

Step 1: A flask was charged with N-(6-(hydroxymethyl)-1-oxo-3-(o-tolyl)isoindolin-4-yl)benzo[d]isothiazole-3-carboxamide (7 mg, 0.0163 mmol), dichloromethane (0.13 mL) triphenylphosphine (4.69 mg, 0.0179 mmol), and tetrabromomethane (5.93 mg, 0.0179 mmol). The reaction mixture was stirred for 1.5 h at room temperature. The reaction mixture was concentrated under reduced pressure and purified by reverse phase chromatography (30 g C18 cartridge, 10 to 100% ACN/AmF 10 mM) to afford N-(6-(bromomethyl)-1-oxo-3-(o-tolyl)isoindolin-4-yl)benzo[d]isothiazole-3-carboxamide (9.00 mg, 0.0183 mmol) as a beige powder. MS: m/z=492.2 $[M+H]^+$.

1885

N-(6-((Methylsulfonyl)methyl)-1-oxo-3-(o-tolyl)isoindolin-4-yl)benzo[d]isothiazole-3-carboxamide

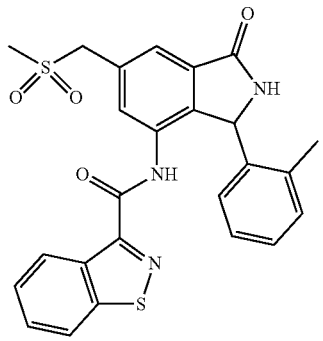

Step 2: A sealed tube was charged with N-(6-(bromomethyl)-1-oxo-3-(o-tolyl)isoindolin-4-yl)benzo[d]isothiazole-3-carboxamide (9.00 mg, 0.01827 mmol), DMF (0.09 mL), and sodium methanesulfinate (4.66 mg, 0.04567 mmol). The reaction mixture was heated to 70° C. for 6 h. The reaction mixture was cooled to room temperature then directly purified on reverse phase chromatography (30 g C18 cartridge, 10 to 100% ACN/AmF 10 mM) to afford after lyophilisation N-(6-((methylsulfonyl)methyl)-1-oxo-3-(o-tolyl)isoindolin-4-yl)benzo[d]isothiazole-3-carboxamide (5.44 mg, 0.0111 mmol, 60% yield) as a white powder. MS: m/z=492.3 [M+H]$^+$; $^1$H NMR (400 MHz, CDCl$_3$) δ 8.90 (d, J=7.7 Hz, 1H), 8.87 (s, 1H), 8.59 (s, 1H), 7.94 (d, J=7.8 Hz, 1H), 7.79 (d, J=1.2 Hz, 1H), 7.72-7.62 (m, 1H), 7.60-7.50 (m, 3H), 7.46 (td, J=7.4, 3.0 Hz, 1H), 7.17 (br s, 1H), 6.65 (s, 1H), 6.00 (br s, 1H), 4.41 (s, 2H), 2.89 (s, 3H), 2.16 (s, 1H), 1.24 (br s, 3H).

Additional compounds prepared according to the methods of Example 45 are listed in Table 19 below. Certain compounds in Table 19 below were prepared with other compounds whose preparation is described elsewhere in the Examples.

TABLE 19

| Additional Exemplary Compounds |
| --- |
| Compound |
| I-231 |
| I-310 |

1886

Example 46

N-(6-(Methoxymethyl)-1-oxo-3-(o-tolyl)isoindolin-4-yl)-N-methylbenzo[d]isothiazole-3-carboxamide
(I-134)

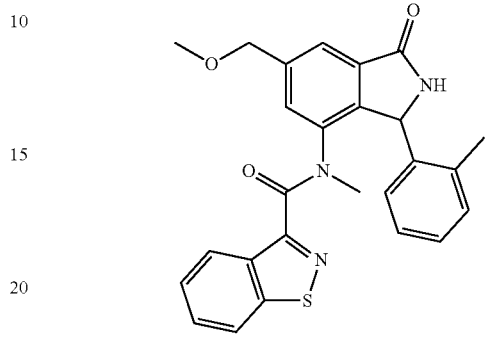

N-(2-(4-Methoxybenzyl)-6-(methoxymethyl)-1-oxo-3-(o-tolyl)isoindolin-4-yl)-N-methylbenzo[d]isothiazole-3-carboxamide

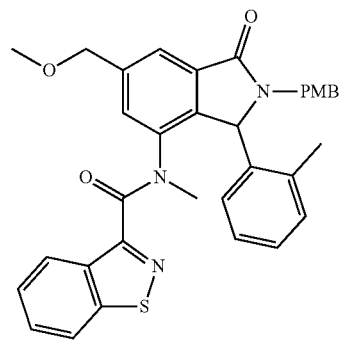

Step 1: To a solution of N-(6-(hydroxymethyl)-2-(4-methoxybenzyl)-1-oxo-3-(o-tolyl)isoindolin-4-yl)benzo[d]isothiazole-3-carboxamide (20 mg, 0.036 mmol) in DMF (0.18 mL) cooled to 0° C. using an ice bath, was added sodium hydride (3.05 mg, 0.0764 mmol) and the mixture was stirred for 30 minutes. Iodomethane (2.71 µL, 0.0437 mmol) was added, and the reaction mixture was warmed to room temperature for 2 h. The reaction was quenched with water (10 mL), the aqueous layer was extracted with DCM (3×10 mL), and the combined organic layers were concentrated under reduced pressure. The residue was purified by reverse phase chromatography (30 g C18 Biotage, 10 to 100% ACN/AmF 10 mM) to afford after lyophilisation N-(2-(4-methoxybenzyl)-6-(methoxymethyl)-1-oxo-3-(o-tolyl)isoindolin-4-yl)-N-methylbenzo[d]isothiazole-3-carboxamide (10.5 mg, 0.0183 mmol, 50% yield) as a beige powder. MS: m/z=578.4 [M+H]$^+$.

N-(6-(Methoxymethyl)-1-oxo-3-(o-tolyl)isoindolin-4-yl)-N-methylbenzo[d]isothiazole-3-carboxamide

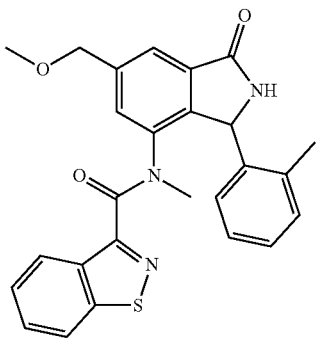

Step 2: A sealed tube was charged with N-(2-(4-methoxybenzyl)-6-(methoxymethyl)-1-oxo-3-(o-tolyl)isoindolin-4-yl)-N-methylbenzo[d]isothiazole-3-carboxamide (10.5 mg, 0.0183 mmol) and trifluoroacetic acid (317 µL, 4.15 mmol), and the reaction mixture was heated to 90° C. for 24 h. The resulting mixture was diluted with DCM (20 mL), washed with water (2×50 mL), and concentrated under reduced pressure. The residue was purified by reverse-phase chromatography (30 g C18 cartridge, 10 to 100% ACN/AmF 10 mM) affording after lyophilisation N-(6-(methoxymethyl)-1-oxo-3-(o-tolyl)isoindolin-4-yl)-N-methylbenzo[d]isothiazole-3-carboxamide (3.84 mg, 0.00839 mmol, 40% yield) as a beige powder.

Example 47

N-(6-(Methoxymethyl)-1-oxo-3-(o-tolyl)isoindolin-4-yl)benzo[d]isothiazole-3-carboxamide (I-146)

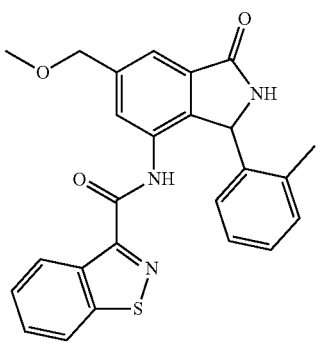

(7-(Benzo[d]isothiazole-3-carboxamido)-2-(4-methoxybenzyl)-3-oxo-1-(o-tolyl)isoindolin-5-yl)methyl methanesulfonate

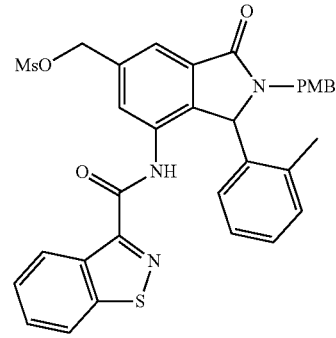

Step 1: To a solution of N-(6-(hydroxymethyl)-2-(4-methoxybenzyl)-1-oxo-3-(o-tolyl)isoindolin-4-yl)benzo[d]isothiazole-3-carboxamide (25 mg, 0.036 mmol) in anhydrous DCM (0.23 mL) was added triethylamine (19.0 µL, 0.14 mmol), and the mixture was cooled to 0° C. using an ice bath. Methanesulfonyl methanesulfonate (11.8 mg, 0.0682 mmol) was added, and the reaction mixture was stirred for 30 minutes at room temperature. The mixture was quenched with water (20 mL). The layers were separated, and the aqueous layer was further extracted with DCM (3×20 mL). The combined organics were washed with brine, dried over sodium sulfate, and concentrated to provide (7-(benzo[d]isothiazole-3-carboxamido)-2-(4-methoxybenzyl)-3-oxo-1-(o-tolyl)isoindolin-5-yl)methyl methanesulfonate which was used directly in the next step. MS: m/z=628.2 [M+H]⁺.

N-(2-(4-Methoxybenzyl)-6-(methoxymethyl)-1-oxo-3-(o-tolyl)isoindolin-4-yl)benzo[d]isothiazole-3-carboxamide

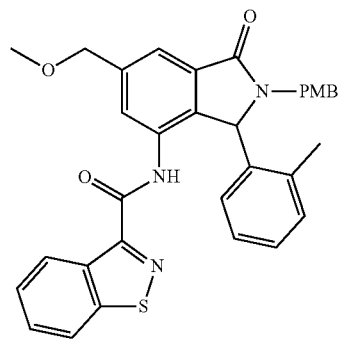

Step 2: To a solution of (7-(benzo[d]isothiazole-3-carboxamido)-2-(4-methoxybenzyl)-3-oxo-1-(o-tolyl)isoindolin-5-yl)methyl methanesulfonate in methanol (1 mL) was added sodium methanolate (1.0 mL, 4.36 mmol, 25% w/w in MeOH), and the mixture was stirred for 18 h at room temperature. The mixture was concentrated under reduced pressure, and the crude was purified by reverse-phase chromatography (30 g C$_{18}$ cartridge, 10 to 100% ACN/AmF 10 mM) to afford after lyophilisation N-(2-(4-methoxybenzyl)-6-(methoxymethyl)-1-oxo-3-(o-tolyl)isoindolin-4-yl)benzo

[d]isothiazole-3-carboxamide (13.0 mg, 0.0231 mmol, 50% yield over two steps) as a beige powder. MS: m/z=564.3 [M+H]+.

N-(6-(Methoxymethyl)-1-oxo-3-(o-tolyl)isoindolin-4-yl)benzo[d]isothiazole-3-carboxamide

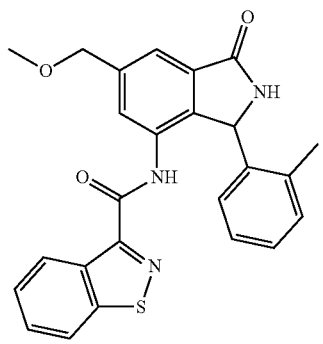

Step 3: A sealed tube was charged with N-(2-(4-methoxybenzyl)-6-(methoxymethyl)-1-oxo-3-(o-tolyl)isoindolin-4-yl)benzo[d]isothiazole-3-carboxamide (13.0 mg, 0.0231 mmol) and trifluoroacetic acid (352 μL, 4.61 mmol), and the reaction mixture was heated to 90° C. for 24 h. The resulting mixture was diluted with DCM (20 mL), washed with water (2×50 mL), and concentrated under reduced pressure. The residue was purified by reverse-phase chromatography (30 g C18 cartridge, 10 to 100% ACN/AmF 10 mM) affording after lyophilisation N-(6-(methoxymethyl)-1-oxo-3-(o-tolyl)isoindolin-4-yl)benzo[d]isothiazole-3-carboxamide (6 mg, 0.013 mmol, 55% yield) as a beige powder.

Example 48

7-(Benzo[b]thiophene-3-carboxamido)-N-methyl-3-oxo-1-(o-tolyl)isoindoline-5-carboxamide (I-6), (R)-7-(Benzo[b]thiophene-3-carboxamido)-N-methyl-3-oxo-1-(o-tolyl)isoindoline-5-carboxamide (I-75), and (S)-7-(Benzo[b]thiophene-3-carboxamido)-N-methyl-3-oxo-1-(o-tolyl)isoindoline-5-carboxamide (I-76)

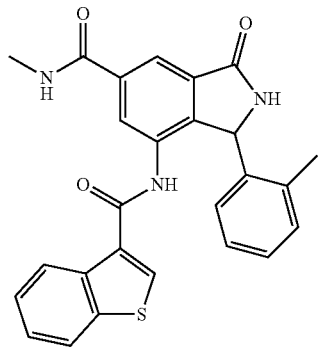

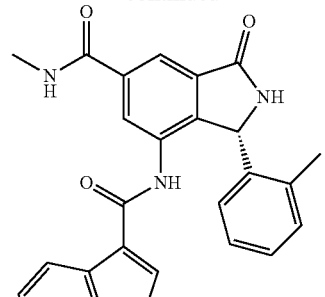

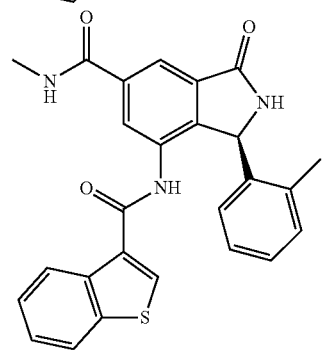

7-Amino-2-(4-methoxybenzyl)-3-oxo-1-(o-tolyl)isoindoline-5-carboxylic acid

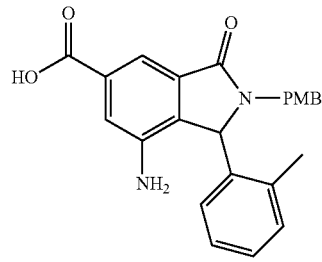

Step 1: To a mixture of methyl 2-(4-methoxybenzyl)-7-((methoxycarbonyl)amino)-3-oxo-1-(o-tolyl)isoindoline-5-carboxylate (10.0 g, 19.9 mmol, 1.00 equiv.) in MeOH (200 mL) was added NaOH (2 M, 99.6 mL, 10.0 equiv.) at 25° C. Then the mixture was heated to 60° C. and stirred at 60° C. for 4 h. The mixture was concentrated in vacuum to afford a residue. The residue was diluted with water (200 mL), and washed with ethyl acetate (3×200 mL). The aqueous layer was adjusted to pH=3, then extracted with ethyl acetate (3×20.0 mL). The combined organic layers were washed with brine (20.0 mL), dried over Na$_2$SO$_4$, filtered, and the filtrate was concentrated. The crude product was purified by column chromatography (SiO$_2$, 0 to 5% MeOH in DCM) to afford 7-amino-2-(4-methoxybenzyl)-3-oxo-1-(o-tolyl)isoindoline-5-carboxylic acid (3.50 g, 7.89 mmol, 39.6% yield, 90.7% purity) as a yellow solid. MS: m/z=401.1 [M−H]−; $^1$H NMR (400 MHz, DMSO-d$_6$) δ 12.93 (s, 1H), 7.60-7.54 (m, 3H), 7.44-7.39 (m, 2H), 7.31-7.21 (m, 4H), 7.03-6.99 (m, 6H), 6.88-6.86 (m, 4H), 6.46 (d, J=8.0 Hz, 1H), 5.60 (s, 1H), 5.48 (s, 1H), 4.99-4.93 (m, 1H), 4.85 (s, 1H), 4.71 (s, 2H), 3.73 (s, 6H), 3.65 (d, J=8.0 Hz, 1H), 3.60 (d, J=14.8 Hz, 1H), 3.51 (d, J=15.6 Hz, 1H), 2.26 (s, 3H), 1.48 (s, 2H).

7-Amino-2-(4-methoxybenzyl)-N-methyl-3-oxo-1-(o-tolyl)isoindoline-5-carboxamide

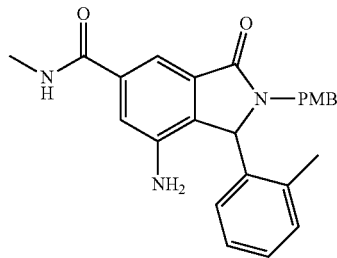

Step 2: To a solution of 7-amino-2-(4-methoxybenzyl)-3-oxo-1-(o-tolyl)isoindoline-5-carboxylic acid (844 mg, 2.10 mmol, 1.00 equiv.) in DMF (10 mL) was added DIPEA (2.17 g, 16.8 mmol, 2.92 mL, 8.00 equiv.) at 25° C. The mixture was cooled to 0° C., then HOBt (567 mg, 4.19 mmol, 2.00 equiv.) and EDCI (804 mg, 4.19 mmol, 2.00 equiv.) were added at 0° C. The mixture was warmed to 25° C. and stirred at 25° C. for 0.5 hr. Then MeNH$_2$—HCl (708 mg, 10.5 mmol, 5.00 equiv.) was added to the reaction mixture, and the mixture was stirred at 25° C. for 4 hrs. The mixture was poured into water (40.0 mL) and extracted with ethyl acetate (3×40.0 mL). The combined organic layer was washed with brine (40.0 mL), dried over Na$_2$SO$_4$, filtered, and concentrated. The residue was purified by column chromatography (SiO$_2$, Petroleum ether/Ethyl acetate=1:0 to 0:1) to afford compound 7-amino-2-(4-methoxybenzyl)-N-methyl-3-oxo-1-(o-tolyl)isoindoline-5-carboxamide (340 mg) as a light yellow solid. MS: m/z=414.3 [M+H]$^+$; $^1$H NMR (400 MHz, DMSO-d$_6$) δ 8.50-8.47 (m, 2H), 7.57-7.52 (m, 2H), 7.44 (d, J=1.2 Hz, 1H), 7.37-7.20 (m, 7H), 7.10-7.00 (m, 4H), 6.90-6.85 (m, 7H), 6.62 (d, J=8.4 Hz, 2H), 6.46 (d, J=8.0 Hz, 1H), 5.58 (s, 1H), 5.45 (s, 1H), 5.00-4.94 (m, 1H), 4.68 (t, J=19.2 Hz, 4H), 3.72 (s, 3H), 3.65 (s, 3H), 3.59 (d, J=14.8 Hz, 1H), 3.51 (d, J=15.2 Hz, 1H), 2.78-2.75 (m, 6H), 2.26 (s, 2H), 1.30 (s, 2H).

7-(Benzo[h]thiophene-3-carboxamido)-2-(4-methoxybenzyl)-N-methyl-3-oxo-1-(o-tolyl)isoindoline-5-carboxamide

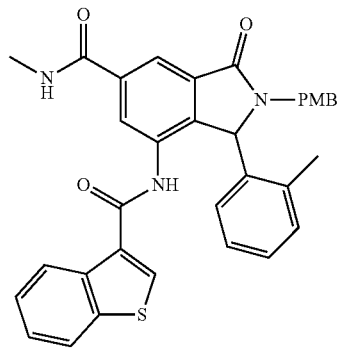

Step 3: To a mixture of 7-amino-2-(4-methoxybenzyl)-N-methyl-3-oxo-1-(o-tolyl)isoindoline-5-carboxamide (340 mg, 818 μmol, 1.00 equiv.) and benzo[b]thiophene-3-carbonyl chloride (241 mg, 1.23 mmol, 1.50 equiv.) in THF (8.00 mL) was added Et$_3$N (248.42 mg, 2.45 mmol, 342 μL, 3.00 equiv.). The mixture was stirred at 50° C. for 8 hrs. The mixture was concentrated in vacuum to afford the crude product. The crude product was purified by prep-HPLC (Column: Waters X bridge BEH C18 250*50 mm*10 μm; Mobile phase: 42%-72% ACN in water (10 mM NH$_4$HCO$_3$)) to afford 7-(benzo[b]thiophene-3-carboxamido)-2-(4-methoxybenzyl)-N-methyl-3-oxo-1-(o-tolyl)isoindoline-5-carboxamide (130 mg, 224 μmol, 99.2% purity) as a white solid. MS: m/z=576.4 [M+H]$^+$; $^1$H NMR (400 MHz, DMSO-d$_6$) δ 10.18 (d, J=43.2 Hz, 1H), 8.80-8.77 (m, 1H), 8.24 (d, J=21.2 Hz, 1H), 8.16-8.13 (m, 1H), 8.07-7.96 (m, 3H), 7.79 (d, J=20.0 Hz, 7H), 6.62 (d, J=8.4 Hz, 2H), 6.46 (d, J=8.0 Hz, 1H), 5.58 (s, 1H), 5.45 (s, 1H), 5.00-4.94 (m, 1H), 7.42-7.36 (m, 2H), 7.18-7.00 (m, 5H), 6.92-6.86 (m, 3H), 6.34 (d, J=7.2 Hz, 1H), 5.94 (s, 1H), 5.71 (s, 1H), 5.00 (dd, J=14.8, 3.6 Hz, 1H), 3.73 (s, 3H), 3.63 (d, J=15.2 Hz, 1H), 3.53 (d, J=15.6 Hz, 1H), 2.83 (t, J=4.8 Hz, 3H), 1.94 (s, 2H), 1.39 (s, 1H).

7-(Benzo[b]thiophene-3-carboxamido)-N-methyl-3-oxo-1-(o-tolyl)isoindoline-5-carboxamide

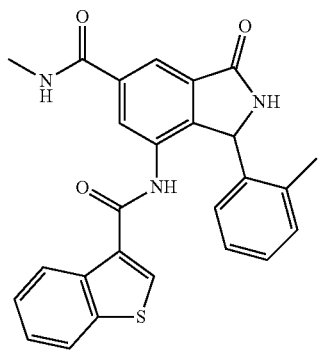

Step 4: A solution of 7-(benzo[h]thiophene-3-carboxamido)-2-(4-methoxybenzyl)-N-methyl-3-oxo-1-(o-tolyl)isoindoline-5-carboxamide (130 mg, 226 μmol, 1.00 equiv.) in TFA (4.00 g, 35.1 mmol, 2.60 mL, 156 equiv.) was stirred at 100° C. for 75 hrs. The mixture was concentrated in vacuum to afford the residue. The residue was dissolved in ethyl acetate (20.0 mL), poured into saturated aqueous solution of NaHCO$_3$ (20.0 mL), extracted with ethyl acetate (3×20.0 mL). The combined organic layer was washed with brine (20.0 mL), dried over Na$_2$SO$_4$, filtered, and concentrated. The crude product was purified by prep-HPLC (Column: Waters Xbridge 150*25 mm*5 μm; Mobile phase: 28%-58% ACN in water (10 mM NH$_4$HCO$_3$)) to afford 7-(benzo[b]thiophene-3-carboxamido)-N-methyl-3-oxo-1-(o-tolyl)isoindoline-5-carboxamide (76.0 mg, 167 μmol, 73.8% yield, 100% purity) as a white solid. MS: m/z=456.2 [M+H]$^+$; $^1$H NMR (400 MHz, CD$_3$OD) δ 8.18 (d, J=1.2 Hz, 1H), 8.13 (t, J=5.6 Hz, 1H), 8.02 (d, J=1.6 Hz, 1H), 7.92-7.89 (m, 1H), 7.42-7.39 (m, 3H), 7.16-7.12 (m, 1H), 7.03-7.00 (m, 2H), 6.15 (s, 1H), 2.98 (s, 3H), 2.21-2.18 (m, 3H).

1893

(R)-7-(Benzo[b]thiophene-3-carboxamido)-N-methyl-3-oxo-1-(o-tolyl)isoindoline-5-carboxamide and (S)-7-(Benzo[b]thiophene-3-carboxamido)-N-methyl-3-oxo-1-(o-tolyl)isoindoline-5-carboxamide

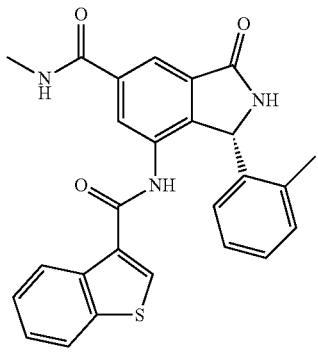

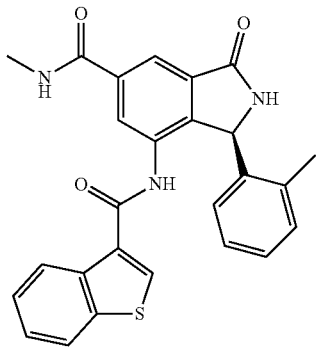

Step 5: The enantiomers of 7-(benzo[b]thiophene-3-carboxamido)-N-methyl-3-oxo-1-(o-tolyl)isoindoline-5-carboxamide were resolved by SFC (Column: REGIS (S,S)-WHELK-01 (250 mm*50 mm, 10 μm); Mobile phase: 50% [0.1% NH$_3$H$_2$O in MeOH]) to afford (S)-7-(benzo[b]thiophene-3-carboxamido)-N-methyl-3-oxo-1-(o-tolyl)isoindoline-5-carboxamide (27.7 mg, 60.2 μmol, 36.0% yield, 99.0% purity, 99.6% ee) as a white solid and (R)—7-(benzo[b]thiophene-3-carboxamido)-N-methyl-3-oxo-1-(o-tolyl) isoindoline-5-carboxamide (25.8 mg, 55.9 μmol, 33.4% yield, 98.5% purity, 99.8% ee) as an off-white solid.

Additional compounds prepared according to the methods of Example 48 are listed in Table 20 below. Certain compounds in Table 20 below were prepared with other compounds whose preparation is described elsewhere in the Examples.

TABLE 20

| Additional Exemplary Compounds Compound |
| --- |
| I-121 |
| I-123 |
| I-156 |
| I-163 |
| I-164 |
| I-165 |
| I-166 |
| I-211 |
| I-212 |

1894

Example 49

N-[6-(1-hydroxycyclopropyl)-3-(2-methylphenyl)-1-oxo-2,3-dihydro-1H-isoindol-4-yl]-1,2-benzothiazole-3-carboxamide (I-315)

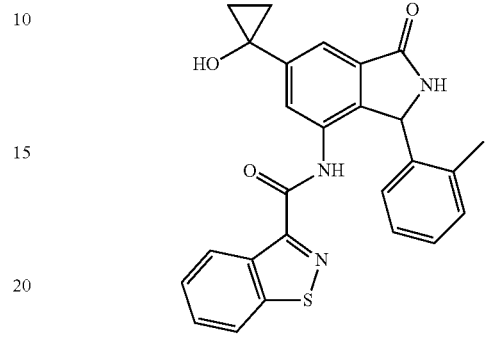

Methyl 7-(1,2-benzothiazole-3-amido)-2-[(4-methoxyphenyl)methyl]-1-(2-methylphenyl)-3-oxo-2,3-dihydro-1H-isoindole-5-carboxylate

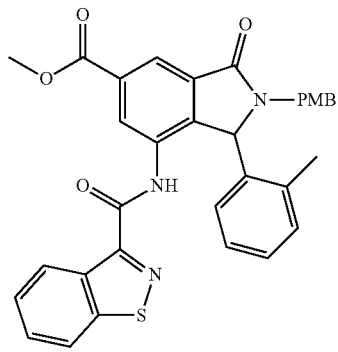

Step 1: A solution of 1,2-benzothiazole-3-carbonyl chloride (110 mg, 0.56 mmol) in DCM (2.0 mL) was added to a solution of methyl 7-amino-2-(4-methoxybenzyl)-3-oxo-1-(o-tolyl)isoindoline-5-carboxylate (154 mg, 0.372 mmol) in DCM (2.0 mL) at 0° C. The reaction mixture was stirred at 0° C. for 10-15 min, then allowed to reach room temperature overnight. The reaction mixture was quenched with saturated sodium bicarbonate (1.0 mL), and stirred for 30 minutes. The reaction mixture was diluted with DCM (10 mL), and washed with saturated sodium bicarbonate (15 mL×3), water (15 mL), and then brine (15 mL). The organic layer was dried with Na$_2$SO$_4$, and filtered. The filtrate was evaporated under reduced pressure to afford methyl 7-(1,2-benzothiazole-3-amido)-2-[(4-methoxyphenyl)methyl]-1-(2-methylphenyl)-3-oxo-2,3-dihydro-1H-isoindole-5-carboxylate, which was used in the next step without further purification. MS: m/z=578.2 [M+H]$^+$.

Methyl 7-(benzo[d]isothiazole-3-carboxamido)-3-oxo-1-(o-tolyl)isoindoline-5-carboxylate

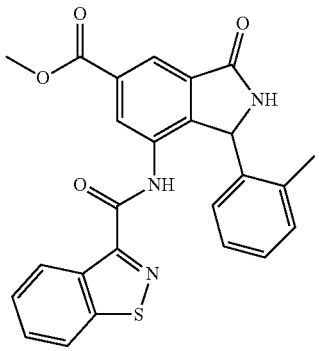

Step 2: Methyl 7-(1,2-benzothiazole-3-amido)-2-[(4-methoxyphenyl)methyl]-1-(2-methylphenyl)-3-oxo-2,3-dihydro-1H-isoindole-5-carboxylate was dissolved in trifluoroacetic acid (2.0 mL, 17.5 μmol) at room temperature in a screw-top glass reaction vial equipped with a stir bar and septum under nitrogen atmosphere. Excess triethylsilane (100 μL, 625 μmol) was added, and the solution was stirred at room temperature for 30 min. The septa was quickly replaced with a plastic cap, and the reaction mixture was sealed from the oxygen atmosphere. The reaction mixture was placed in a pre-heated oil bath (105° C., external) and stirred overnight. The reaction mixture was diluted with DCM (10 mL), and then all volatiles were evaporated to furnish a crude residue. To the crude residue was added diethyl ether (3 mL) and MeOH (10 mL). The resulting suspension was shaken, and the insoluble fraction was allowed to settle. The supernatant was slowly filtered followed by the solid, and the remaining solid was washed with MeOH (3 mL×3). The washing and filtration steps were repeated two more times to afford 93 mg of methyl 7-(benzo[d]isothiazole-3-carboxamido)-3-oxo-1-(o-tolyl)isoindoline-5-carboxylate as a light brown solid, which was used in the next step without further purification. MS: m/z=458.1 [M+H]$^1$.

N-[6-(1-hydroxycyclopropyl)-3-(2-methylphenyl)-1-oxo-2,3-dihydro-1H-isoindol-4-yl]-1,2-benzothiazole-3-carboxamide

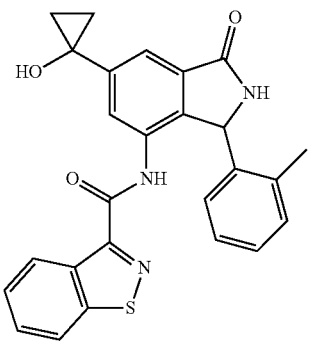 [SMILES: Cc1ccccc1C1NC(=O)c2cc(C3(O)CC3)cc(NC(=O)c3nsc4ccccc34)c21]

Step 3: A flame-dried, round-bottom flask equipped with a stir bar was charged with methyl 7-(benzo[d]isothiazole-3-carboxamido)-3-oxo-1-(o-tolyl)isoindoline-5-carboxylate (30 mg, 65.5 μmol). The solid was suspended in THF (5.0 mL), and stirred vigorously at room temperature for 10 minutes. Titanium tetraisopropoxide (50 μL, 168 μmol) was added, and the mixture was stirred for 10 minutes at room temperature. To the resulting solution was added dropwise over 3 hours ethylmagnesium bromide (0.8 mL, 3.0 M, 2.40 mmol). The solution was quenched with dropwise addition of 1M HCl (1 mL), then diluted with DCM (20 mL). The mixture was washed with water (20 mL×3), then with brine (20 mL×3). The solvent was evaporated. The resulting residue was purified by reverse-phase flash column chromatography (eluting with 0 to 100% acetonitrile in 10 mM AmF in water) to afford after lyophilization N-[6-(1-hydroxycyclopropyl)-3-(2-methylphenyl)-1-oxo-2,3-dihydro-1H-isoindol-4-yl]-1,2-benzothiazole-3-carboxamide (13 mg) as a white powder.

Example 50

N-(7-Cyano-1-oxo-3-(o-tolyl)isoindolin-4-yl)benzo[b]thiophene-3-carboxamide (I-132)

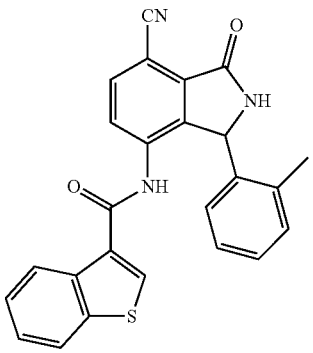 [SMILES: Cc1ccccc1C1NC(=O)c2c(C#N)ccc(NC(=O)c3csc4ccccc34)c21]

6-Bromo-2-methyl-3-nitrobenzoic acid

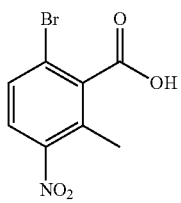

Step 1: To a solution of 2-bromo-6-methylbenzoic acid (240 g, 1.12 mol, 1.00 equiv.) in H$_2$SO$_4$ (1.20 L) at 0° C. was added dropwise a mixture of HNO$_3$ (76.5 g, 1.21 mol, 54.7 mL, 1.09 equiv.) in H$_2$SO$_4$ (100 mL). The mixture was stirred at 0° C. for 45 min. The mixture was poured into ice water (5.00 L), and solids precipitated. The suspension was filtered. The filter cake was dried under reduced pressure to afford an approximately equimolar mixture of 6-bromo-2-methyl-3-nitrobenzoic acid and a regioisomer (339 g, crude) as a light yellow solid. MS: m/z=261.9 [M+H]$^+$; $^1$H NMR (400 MHz, CDCl$_3$) δ 7.84 (d, J=8.8 Hz, 1H), 7.81 (d, J=8.0 Hz, 0.5H), 7.65 (d, J=8.8 Hz, 1H), 7.37 (d, J=8.4 Hz, 0.9H), 2.61 (s, 3H), 2.52 (s, 1.5H).

1897
4-Amino-7-bromo-2-(4-methoxybenzyl)-3-(o-tolyl)isoindolin-1-one

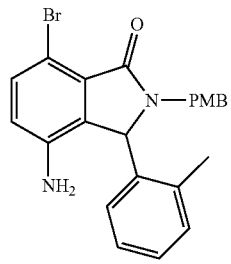

Steps 2 through 7: Using the procedures described in Example 10, Steps 1 through 6,6-bromo-2-methyl-3-nitrobenzoic acid was converted to 4-amino-7-bromo-2-(4-methoxybenzyl)-3-(o-tolyl)isoindolin-1-one in 2% yield over the six steps. (The undesired regioisomer generated in Step 1 was removed by reverse-phase chromatography after the iron-mediated nitro-group reduction of Step 5.) The 4-amino-7-bromo-2-(4-methoxybenzyl)-3-(o-tolyl)isoindolin-1-one product was isolated as a white solid following purification by reverse-phase HPLC. MS: m/z=439.2 [M+H]$^+$; $^1$H NMR (400 MHz, DMSO-$d_6$) δ 7.57-7.55 (m, 0.5H), 7.39-7.34 (m, 1H), 7.30-7.20 (m, 2H), 7.11-6.99 (m, 3H), 6.88-6.85 (m, 2H) 6.76-6.68 (m, 1H), 6.49 (d, J=7.6 Hz, 0.5H), 5.50 (s, 0.5H), 5.38 (s, 0.5H), 4.96-4.90 (m, 1H), 4.72 (s, 1H), 4.57 (s, 1H), 3.72 (s, 3H), 3.58 (d, J=14.8 Hz, 0.5H), 3.48 (d, J=15.2 Hz, 0.5H), 2.25 (s, 1.7H), 1.52 (s, 1.3H).

N-(7-Bromo-1-oxo-3-(o-tolyl)isoindolin-4-yl)benzo[h]thiophene-3-carboxamide

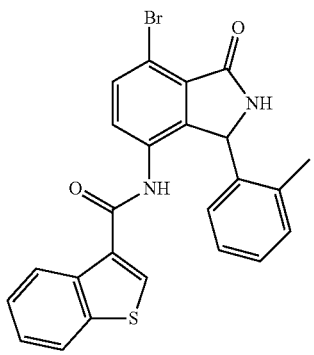 [SMILES: Cc1ccccc1C1NC(=O)c2c(Br)ccc(NC(=O)c3csc4ccccc34)c21]

Steps 8 and 9: According to the procedures of Example 1, Steps 5 and 6,4-amino-7-bromo-2-(4-methoxybenzyl)-3-(o-tolyl)isoindolin-1-one was converted to N-(7-bromo-1-oxo-3-(o-tolyl)isoindolin-4-yl)benzo[b]thiophene-3-carboxamide.

1898
N-(7-Cyano-1-oxo-3-(o-tolyl)isoindolin-4-yl)benzo[b]thiophene-3-carboxamide

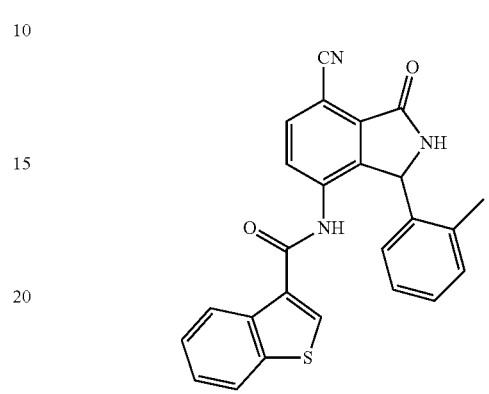

Step 10: A microwave vial equipped with a Teflon-coated stir bar and rubber septum was charged with N-(7-bromo-1-oxo-3-(o-tolyl)isoindolin-4-yl)benzo[b]thiophene-3-carboxamide (30 mg, 0.0628 mmol), followed by Pd$_2$(dba)$_3$ (11.5 mg, 0.0126 mmol), dppf (6.96 mg, 0.0126 mmol), Zn(CN)$_2$ (14.7 mg, 0.126 mmol), zinc (821 pg, 0.0126 mmol), DMF (1.9 mL), and water (0.1 mL). The dark turbid solution, under moderate stirring, at room temperature, was degassed by bubbling with nitrogen gas for about 5 minutes. The vial was then placed in a pre-heated oil bath (105° C., external), and vigorously stirred for 3 hours. The mixture was cooled to room temperature and directly loaded onto a C18 column (24 g), which was eluted with 10-60% acetonitrile in 10 mM aq. AmF. Fractions containing pure product were combined, acetonitrile was removed under reduced pressure, and the remaining aqueous solution was lyophilized to afford N-(7-cyano-1-oxo-3-(o-tolyl)isoindolin-4-yl)benzo[b]thiophene-3-carboxamide as a tan, amorphous solid (18 mg).

Additional compounds prepared according to the methods of Example 50 are listed in Table 21 below. Certain compounds in Table 21 below were prepared with other compounds whose preparation is described elsewhere in the Examples.

TABLE 21

| Additional Exemplary Compounds |
|---|
| Compound |
| I-116 |
| I-237 |
| I-313 |

Example 51

N-[7-Ethenyl-3-(2-methylphenyl)-1-oxo-2,3-di-hydro-1H-isoindol-4-yl]-1-benzothiophene-3-carboxamide (I-2157)

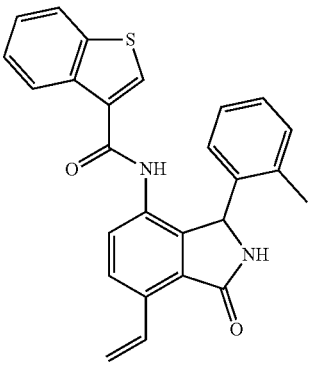 [SMILES: C=Cc1ccc(NC(=O)c2csc3ccccc23)c2c1C(=O)NC2c1ccccc1C]

A 50 mL round-bottomed flask equipped with a Teflon-coated stir bar and rubber septum was charged with N-(7-bromo-1-oxo-3-(o-tolyl)isoindolin-4-yl)benzo[b]thiophene-3-carboxamide (100 mg, 0.209 mmol), followed by potassium vinyltrifluoroborate (139 mg, 1.04 mmol), $K_2CO_3$ (201 mg, 1.46 mmol), and THF:water (10 mL, 9:1). The brown color turbid solution, under slow stirring, was degassed by bubbling with nitrogen gas for about five minutes. Then Pd(dppf)Cl$_2$ (29 mg, 0.042 mmol) was added, and the rubber septum was quickly exchanged for a reflux condenser. The system was evacuated under house vacuum, and back-filled with nitrogen gas. The flask was then placed in a pre-heated oil bath (63° C., external), and the mixture stirred for 40 hours. The mixture was diluted with ethyl acetate (20 mL), and washed with water (2×20 mL). The combined aqueous layers were extracted with ethyl acetate (20 mL). The combined organics were washed with brine (20 mL), dried over sodium sulfate, filtered, and solvents removed under reduced pressure to afford a tan paste. The residue was purified by silica gel flash chromatography (ethyl acetate/hexanes) to afford N-[7-ethenyl-3-(2-methylphenyl)-1-oxo-2,3-dihydro-1H-isoindol-4-yl]-1-benzothiophene-3-carboxamide (65 mg) as a tan powder. MS: m/z=425.3 [M+H]$^+$.

Additional compounds prepared according to the methods of Example 51 are listed in Table 22 below. Certain compounds in Table 22 below were prepared with other compounds whose preparation is described elsewhere in the Examples.

TABLE 22

| Additional Exemplary Compounds Compound |
| --- |
| I-205 |

Example 52

7-(Benzo[b]thiophene-3-carboxamido)-3-oxo-1-(o-tolyl)isoindoline-4-carboxamide (I-149)

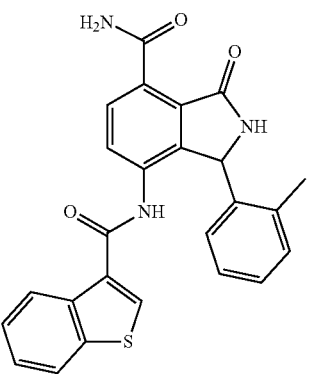 [SMILES: Cc1ccccc1C1NC(=O)c2c(C(N)=O)ccc(NC(=O)c3csc4ccccc34)c21]

A microwave vial equipped with a Teflon-coated stir bar and rubber septum was charged with N-(7-bromo-1-oxo-3-(o-tolyl)isoindolin-4-yl)benzo[b]thiophene-3-carboxamide (20 mg, 0.0419 mmol), followed by Pd(OAc)$_2$ (1.88 mg, 0.00838 mmol), Xantphos (4.84 mg, 0.00838 mmol), 4-dimethylaminopyridine (10.2 mg, 0.0838 mmol), Co$_2$(CO)$_8$ (3.6 mg, 0.010 mmol), and dioxane (2 mL). This dark color turbid solution, under moderate stirring, was degassed by bubbling with nitrogen gas for five minutes, and then a 2M solution of ammonia in isopropanol (0.1 mL, 0.20 mmol) was added. The rubber septum was quickly exchanged for a microwave vial cap and sealed. The vial was then placed in a Biotage microwave reactor and irradiated at 90° C. for one hour. The mixture was directly loaded onto a C18 column (24 g, 1 mL of DMF was used to rinse the vial), and the column was eluted with 10-60% acetonitrile in 10 mM aq. AmF. The fractions containing pure product were lyophilized to afford 7-(benzo[b]thiophene-3-carboxamido)-3-oxo-1-(o-tolyl)isoindoline-4-carboxamide as an off-white amorphous solid (9 mg).

Additional compounds prepared according to the methods of Example 52 are listed in Table 23 below. Certain compounds in Table 23 below were prepared with other compounds whose preparation is described elsewhere in the Examples.

TABLE 23

| Additional Exemplary Compounds Compound |
| --- |
| I-150 |
| I-219 |
| I-225 |
| I-261 |
| I-276 |
| I-278 |
| I-339 |

Example 53

N-(7-Methyl-1-oxo-3-(o-tolyl)isoindolin-4-yl)benzo[b]thiophene-3-carboxamide (I-153)

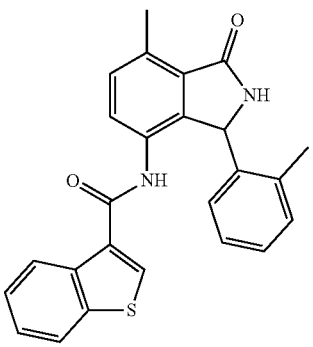 [SMILES: Cc1ccccc1C1NC(=O)c2c(C)ccc(NC(=O)c3csc4ccccc34)c21]

A microwave vial equipped with a Teflon-coated stir bar and rubber septum was charged with N-(7-bromo-1-oxo-3-(o-tolyl)isoindolin-4-yl)benzo[b]thiophene-3-carboxamide (20 mg, 0.0419 mmol), followed by Pd$_2$(dba)$_3$ (3.83 mg, 0.00419 mmol), DABAL-Me3 (10.7 mg, 0.0419 mmol), Xphos (3.99 mg, 0.00838 mmol), and THF (2 mL). The dark color reaction mixture was then heated to reflux and vigorously stirred for 9 hours. The mixture was cooled to RT, and additional DABAL-Me3 (5 mg) was added. The mixture was again heated to reflux and vigorously stirred for 18 hours. The mixture was cooled to RT, diluted with ethyl acetate (20 mL), and washed with water (2×20 mL). The combined aqueous layers were extracted with ethyl acetate (10 mL). The combined organics were dried over sodium sulfate, filtered, and solvents removed under reduced pressure. The resulting residue was purified by reverse phase chromatography (load in DMF, C18 column, 24 g, 10-50% Acetonitrile in 10 mM aq. AmF). The fractions containing pure product were lyophilized to afford N-(7-methyl-1-oxo-3-(o-tolyl)isoindolin-4-yl)benzo[b]thiophene-3-carboxamide (2.6 mg) as a white amorphous solid.

Example 54

N-(6-Acetyl-3-(2-chloro-5-fluorophenyl)-1-oxoisoindolin-4-yl)-3-fluoro-5-(trifluoromethyl)benzamide (I-127)

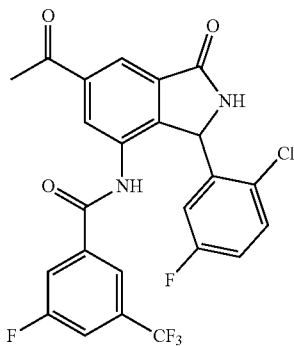 [SMILES: CC(=O)c1cc(NC(=O)c2cc(F)cc(C(F)(F)F)c2)c2c(c1)C(=O)NC2c1cc(F)ccc1Cl]

N-[6-Bromo-3-(2-chloro-5-fluorophenyl)-1-oxo-2,3-dihydro-1H-isoindol-4-yl]-3-fluoro-5-(trifluoromethyl)benzamide (600 mg, 1.09 mmol), tributyl(1-ethoxyethenyl)stannane (787 mg, 2.18 mmol) and bis(triphenylphosphine)palladium(II) dichloride (153 mg, 0.218 mmol) were combined and evacuated/purged with nitrogen. Dioxane (4 mL) was added, and the mixture was heated to 90° C. for 4 hrs. The mixture was diluted with EtOAc, filtered through a plug of silica, and the filtrate was concentrated to provide N-(3-(2-chloro-5-fluorophenyl)-6-(1-ethoxyvinyl)-1-oxoisoindolin-4-yl)-3-fluoro-5-(trifluoromethyl)benzamide.

The resulting residue was stirred in TFA (2.5 mL) and water (0.5 mL) for 2 hr, then concentrated and purified by reverse phase HPLC to provide N-(6-acetyl-3-(2-chloro-5-fluorophenyl)-1-oxoisoindolin-4-yl)-3-fluoro-5-(trifluoromethyl)benzamide (0.42 g, 72%).

Example 55

N-(3-(2-chloro-5-fluorophenyl)-6-(2-hydroxypropan-2-yl)-1-oxoisoindolin-4-yl)-3-fluoro-5-(trifluoromethyl)benzamide (I-128)

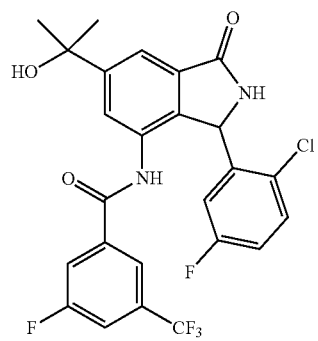 [SMILES: CC(C)(O)c1cc(NC(=O)c2cc(F)cc(C(F)(F)F)c2)c2c(c1)C(=O)NC2c1cc(F)ccc1Cl]

To a solution of N-(6-acetyl-3-(2-chloro-5-fluorophenyl)-1-oxoisoindolin-4-yl)-3-fluoro-5-(trifluoromethyl)benzamide (400 mg, 0.7 mmol) in THF (5 mL) at 0° C. was dropwise added MeMgBr, 3.0 M in Et$_2$O (3.5 mmol, 1.16 mL). After completion of the reaction, the reaction was quenched with aq NH$_4$Cl, and the mixture was extracted with EtOAc. The organics were washed with brine, dried, and concentrated. The residue was purified by reverse phase HPLC using a gradient of water (0.1% FA) and acetonitrile (0.1% FA) 70/30 to 35/65 in 13 minutes then 5/95. Product-containing fractions were combined and lyophilized to provide N-(3-(2-chloro-5-fluorophenyl)-6-(2-hydroxypropan-2-yl)-1-oxoisoindolin-4-yl)-3-fluoro-5-(trifluoromethyl)benzamide (0.25 g, 67%).

Additional compounds prepared according to the methods of Examples 54 and 55 are listed in Table 24 below.

TABLE 24

| Additional Exemplary Compounds Compound |
|---|
| I-135 |
| I-136 |
| I-189 |
| I-190 |
| I-191 |
| I-192 |
| I-214 |

1903

TABLE 24-continued

Additional Exemplary Compounds
Compound

I-215
I-238
I-239
I-242
I-250
I-263
I-264
I-267
I-271
I-272
I-280
I-290
I-298
I-299
I-308
I-355
I-356

Example 56

N-(3-(2-chloro-5-fluorophenyl)-1-oxo-6-(2,2,2-trifluoro-1-hydroxyethyl)isoindolin-4-yl)-3-fluoro-5-(trifluoromethyl)benzamide (I-270)

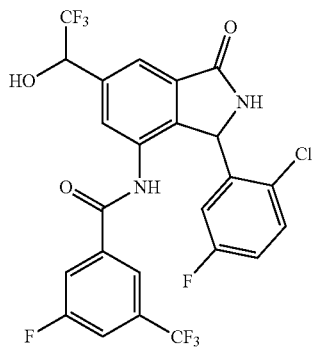 [SMILES: O=C(Nc1cc(C(O)C(F)(F)F)cc2c1C(c1cc(F)ccc1Cl)NC2=O)c1cc(F)cc(C(F)(F)F)c1]

To N-[3-(2-chloro-5-fluorophenyl)-6-formyl-1-oxo-2,3-dihydro-1H-isoindol-4-yl]-3-fluoro-5-(trifluoromethyl)benzamide (110 mg, 0.2223 mmol) in 0.5 mL of DMF was added $K_2CO_3$ (28 mg, 0.2 mmol) and trimethyl(trifluoromethyl)silane (80 mg, 0.5626 mmol). The mixture was stirred at RT for 16 hrs. The mixture was then taken in 1 mL of MeOH and added 50 µL of conc. HCl and stirred for 1 hr. The mixture was taken in 2 mL of DMSO and purified by reverse-phase HPLC using a gradient of water (0.1% FA) and acetonitrile (0.1% FA) 70/30 to 35/65 in 13 minutes, then 5/95. Product-containing fractions were combined and lyophilized to provide N-(3-(2-chloro-5-fluorophenyl)-1-oxo-6-(2,2,2-trifluoro-1-hydroxyethyl)isoindolin-4-yl)-3-fluoro-5-(trifluoromethyl)benzamide (35 mg, 27%).

1904

Additional compounds prepared according to the method of Example 56 are listed in Table 25 below.

TABLE 25

Additional Exemplary Compounds
Compound

I-297
I-334

Example 57

N-(3-(2-Chloro-5-fluorophenyl)-6-((3,3-difluoroazetidin-1-yl)methyl)-1-oxoisoindolin-4-yl)-3-fluoro-5-(trifluoromethyl)benzamide (I-348)

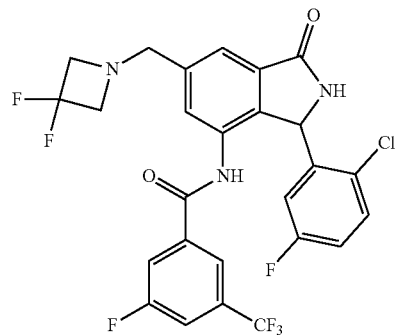 [SMILES: O=C(Nc1cc(CN2CC(F)(F)C2)cc2c1C(c1cc(F)ccc1Cl)NC2=O)c1cc(F)cc(C(F)(F)F)c1]

A solution of N-[3-(2-chloro-5-fluorophenyl)-6-formyl-1-oxo-2,3-dihydro-1H-isoindol-4-yl]-3-fluoro-5-(trifluoromethyl)benzamide (15 mg, 0.030 mmol) in THF (1 mL) was treated with 3,3-difluoroazetidine hydrochloride (8 mg, 0.061 mmol) and polymer-bound Biotage® MP-Triacetoxyborohydride (2 mmol/g, 40 mg). The mixture was stirred at 45° C. for 12 h and then diluted with EtOAc. It was filtered and then concentrated by rotary evaporation. The residue was subjected to reverse-phase HPLC purification (15-60% acetonitrile/water) to afford N-(3-(2-chloro-5-fluorophenyl)-6-((3,3-difluoroazetidin-1-yl)methyl)-1-oxoisoindolin-4-yl)-3-fluoro-5-(trifluoromethyl)benzamide (5 mg, 29% yield) as an off-white powder.

Additional compounds prepared according to the method of Example 57 are listed in Table 26 below.

TABLE 26

Additional Exemplary Compounds
Compound

I-349
I-350
I-352
I-353

Example 58

N-[3-(2-chloro-5-fluorophenyl)-6-(1-hydroxycyclopropyl)-1-oxo-2,3-dihydro-1H-isoindol-4-yl]-3-fluoro-5-(trifluoromethyl)benzamide (I-374)

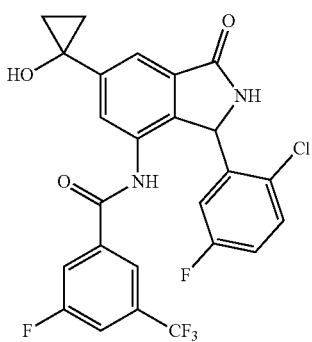 [SMILES: O=C(Nc1cc(C2(O)CC2)cc2c1C(c1cc(F)ccc1Cl)NC2=O)c1cc(F)cc(C(F)(F)F)c1]

Methyl 1-(2-chloro-5-fluorophenyl)-7-[3-fluoro-5-(trifluoromethyl)benzamido]-3-oxo-2,3-dihydro-1H-isoindole-5-carboxylate

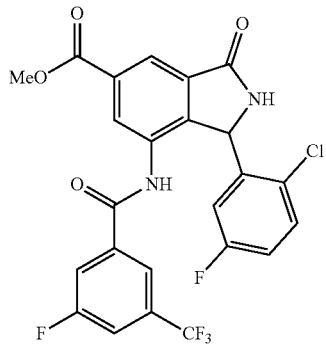 [SMILES: COC(=O)c1cc(NC(=O)c2cc(F)cc(C(F)(F)F)c2)c2c(c1)C(=O)NC2c1cc(F)ccc1Cl]

Step 1: A screw-top glass reaction vial equipped with a stir bar and a rubber septa was charged with N-[6-bromo-3-(2-chloro-5-fluorophenyl)-1-oxo-2,3-dihydro-1H-isoindol-4-yl]-3-fluoro-5-(trifluoromethyl)benzamide (90 mg, 164 µmol), palladium(II) acetate (7.36 mg, 32.8 µmol), methanol (1.58 g, 49.3 mmol), Co$_2$(CO)$_8$ (16.6 mg, 48.8 µmol), Xantphos (18.8 mg, 32.6 µmol), and 4-dimethylaminopyridine (20 mg, 164 µmol). The reaction mixture was degassed by bubbling with nitrogen gas (balloon) under vigorous stirring for two minutes, the rubber septa was quickly replaced with a plastic cap, and the reaction mixture was sealed from the atmosphere. The vial was then placed in a pre-heated oil bath (85° C., external), and the mixture was vigorously stirred for 7 h. The volatiles were evaporated under reduced pressure to afford a residue, which was purified by normal-phase flash column chromatography (eluted with 0-100% EtOAc/heptanes in gradient) to furnish methyl 1-(2-chloro-5-fluorophenyl)-7-[3-fluoro-5-(trifluoromethyl)benzamido]-3-oxo-2,3-dihydro-1H-isoindole-5-carboxylate (73 mg) as an off-white solid. MS: m/z=525.3 [M+H]$^1$; $^1$H NMR (400 MHz, DMSO-d$_6$) δ 10.66 (s, 1H), 9.35 (br s, 1H), 8.13 (dd, J=16.4, 1.2 Hz, 2H), 7.96 (d, J=8.3 Hz, 1H), 7.76 (d, J=8.8 Hz, 1H), 7.68 (s, 1H), 7.33 (dd, J=8.9, 5.2 Hz, 1H), 7.10 (td, J=8.5, 3.1 Hz, 1H), 6.04 (br s, 1H), 3.93 (s, 3H). One proton expected at ca. 6.8 ppm was not observed.

N-[3-(2-chloro-5-fluorophenyl)-6-(1-hydroxycyclopropyl)-1-oxo-2,3-dihydro-1H-isoindol-4-yl]-3-fluoro-5-(trifluoromethyl)benzamide

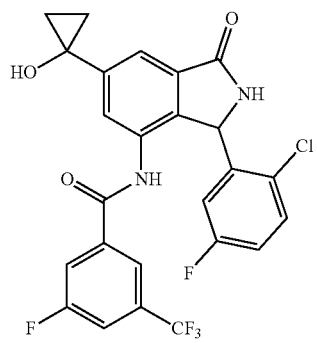

Step 2: According to the procedure of Example 49, Step 3, methyl 1-(2-chloro-5-fluorophenyl)-7-[3-fluoro-5-(trifluoromethyl)benzamido]-3-oxo-2,3-dihydro-1H-isoindole-5-carboxylate was converted to N-[3-(2-chloro-5-fluorophenyl)-6-(1-hydroxycyclopropyl)-1-oxo-2,3-dihydro-1H-isoindol-4-yl]-3-fluoro-5-(trifluoromethyl)benzamide, which was isolated as an off-white solid following reverse-phase chromatography (10 mM AmF in a gradient of 0-100% CH$_3$CN in water).

Example 59

N-(3-Cyclohexyl-1-oxoisoindolin-4-yl)benzo[d]isothiazole-3-carboxamide (I-204)

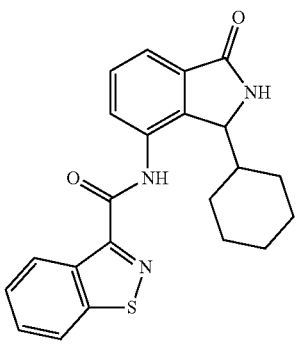 [SMILES: O=C1NC(C2CCCCC2)c2c(NC(=O)c3nsc4ccccc34)cccc21]

4-Amino-3-cyclohexylisoindolin-1-one

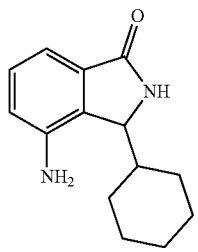 [SMILES: Nc1cccc2c1C(C1CCCCC1)NC2=O]

Step 1: To a solution of 4-amino-3-methoxyisoindolin-1-one (50 mg, 0.28 mmol) in dry THF (0.35 mL) at 0° C. under a nitrogen atmosphere was added a 1 M solution of bromo (cyclohexyl)magnesium (841 μL, 0.841 mmol) in THF. The mixture was stirred at R.T. for 15 min. Another portion of 1M solution of bromo(cyclohexyl)magnesium (560 uL, 0.56 mmol) was added and stirring was continued at R.T. for 15 min. A sat. aq solution of NH₄Cl was then added, and the mixture was extracted with EtOAct (3×). The combined organic layers were washed with brine, dried over Na₂SO₄, filtered, and concentrated under reduced pressure. The resulting 4-amino-3-cyclohexylisoindolin-1-one, as a brown oil, was used in the next step without further purification.

N-(3-Cyclohexyl-1-oxoisoindolin-4-yl)benzo[d]iso-thiazole-3-carboxamide

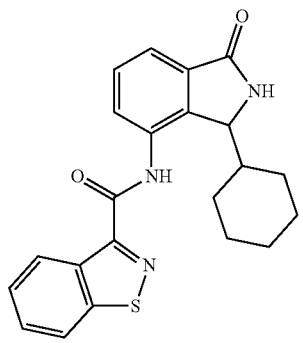 [SMILES: O=C1NC(C2CCCCC2)c2c(NC(=O)c3nsc4ccccc34)cccc21]

Step 2: The 4-amino-3-cyclohexylisoindolin-1-one from the previous step was dissolved in dry DMF (0.94 mL) at room temperature under a nitrogen atmosphere, and 1,2-benzothiazole-3-carboxylic acid (60.3 mg, 0.337 mmol) was added, followed by HATU (159 mg, 0.421 mmol) and finally DIPEA (197 μL, 1.12 mmol). The mixture was stirred at room temperature for 12h. The mixture was then diluted with water and extracted with AcOEt (3×).

The combined organic layers were washed with brine, dried over Na₂SO₄, filtered and concentrated under reduced pressure. Purification by reverse phase chromatography (5 to 70% ACN/aqueous AmF 10 mM) followed by purification by normal phase chromatography (0 to 60% acetone/hexanes) afforded N-(3-cyclohexyl-1-oxoisoindolin-4-yl) benzo[d]isothiazole-3-carboxamide (10 mg, 10%) as a yellow powder after lyophilisation.

Additional compounds prepared according to the methods of Example 59 are listed in Table 27 below.

TABLE 27

| Additional Exemplary Compounds |
| Compound |
| --- |
| I-8 |
| I-18 |
| I-106 |
| I-259 |
| I-327 |

Example 60

N-(7-oxo-5-(o-tolyl)-6,7-dihydro-5H-pyrrolo[3,4-b]pyridin-4-yl)indoline-1-carboxamide (I-147)

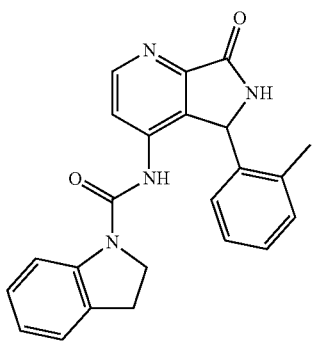 [SMILES: Cc1ccccc1C1NC(=O)c2nccc(NC(=O)N3CCc4ccccc43)c21]

4-Chloro-N-(2,4-dimethoxybenzyl)picolinamide

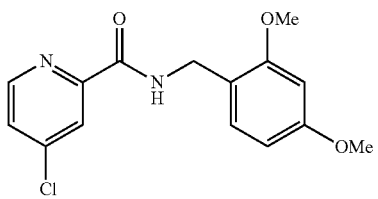 [SMILES: COc1ccc(CNC(=O)c2cc(Cl)ccn2)c(OC)c1]

Step 1: To a solution of 4-chloropicolinic acid (200 g, 1.27 mol, 1.00 eq) in DCM (2.00 L) was added CDI (216 g, 1.33 mol, 1.05 eq) and DMAP (4.65 g, 38.1 mmol, 0.03 eq) at 15° C. for 0.5 h. Then a solution of (2,4-dimethoxyphenyl) methanamine (212 g, 1.27 mol, 191 mL, 1.00 eq) in DCM (400 mL) was added, and the mixture was stirred at 25° C. for 1 h. The reaction mixture was concentrated. The residue was purified by fast flash column chromatography (SiO₂, petroleum ether/ethyl acetate=3/1), to obtain 4-chloro-N-(2, 4-dimethoxybenzyl)picolinamide (316 g, 1.03 mol, 81.1% yield) as a white solid.

4-Chloro-6-(2,4-dimethoxybenzyl)-5-hydroxy-5-(o-tolyl)-5,6-dihydro-7H-pyrrolo[3,4-b]pyridin-7-one

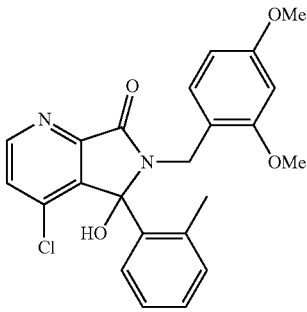 [SMILES: COc1ccc(CN2C(=O)c3nccc(Cl)c3C2(O)c2ccccc2C)c(OC)c1]

Step 2: To a solution of n-BuLi (2.50 M, 391 mL, 3.00 eq) in THF (1.20 L) at −78° C. was added a solution of 4-chloro-N-(2,4-dimethoxybenzyl)picolinamide (100 g, 326 mmol, 1.00 eq) in THF (200 mL). The mixture was stirred at −40 to −50° C. for nearly 3 h. The reaction was then cooled back to −78° C. To the reaction was added dropwise over 15 minutes a solution of 2-methylbenzoyl chloride (101 g, 652 mmol, 84.7 mL, 2.00 eq) in THF (200 mL). The reaction was stirred for 1 h at −78° C., before removal of the dry ice/ethyl acetate bath. The reaction was then stirred at 25° C. for 2 h. The mixture was poured into water (2.00 L) and extracted with ethyl acetate (3×500 mL). The combined organic layer was washed with brine (500 mL), dried over Na$_2$SO$_4$, and concentrated. The resulting yellow oil was purified once by column chromatography (SiO2, petroleum ether/ethyl acetate=50/1 to 1/1) and twice by column chromatography (SiO$_2$, DCM/MeOH=1/0 to 50/1), to obtain 4-chloro-6-(2,4-dimethoxybenzyl)-5-hydroxy-5-(o-tolyl)-5,6-dihydro-7H-pyrrolo[3,4-b]pyridin-7-one (125 g) as a white solid. MS: m/z=425.0 [M+H]$^+$; $^1$H NMR (400 MHz, DMSO-d$_6$) δ 9.02 (t, J=6.4 Hz, 1H), 8.73 (d, J=5.2 Hz, 1H), 7.94 (d, J=5.2 Hz, 1H), 7.44-7.47 (m, 1H), 7.36 (d, J=7.2 Hz, 1H), 7.21 (d, J=4.0 Hz, 1H), 6.91 (d, J=8.4 Hz, 1H), 6.52 (d, J=2.4 Hz, 1H), 6.39 (dd, J=2.4, 8.4 Hz, 1H), 4.25 (d, J=6.0 Hz, 2H), 3.76 (s, 3H), 3.72 (s, 3H), 2.65 (s, 3H).

4-Chloro-6-(2,4-dimethoxybenzyl)-5-(o-tolyl)-5,6-dihydro-7H-pyrrolo[3,4-b]pyridin-7-one

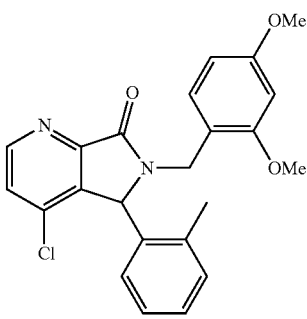 [SMILES: COc1ccc(CN2C(=O)c3nccc(Cl)c3C2c2ccccc2C)c(OC)c1]

Step 3: To a stirred solution of 4-chloro-6-(2,4-dimethoxybenzyl)-5-hydroxy-5-(o-tolyl)-5,6-dihydro-7H-pyrrolo[3,4-b]pyridin-7-one (75.0 g, 177 mmol, 1.00 eq) in DCM (1.10 L) was added TFA (503 g, 4.41 mol, 327 mL, 25.0 eq) at 25° C. The mixture was cooled to 0° C., then triethylsilane (205 g, 1.77 mol, 282 mL, 10.0 eq) was added. The mixture was warmed to 25° C., stirred at 25° C. for 12 h, and then concentrated. The residue was purified by reverse-phase HPLC (0.1% FA condition) to afford 4-chloro-6-(2,4-dimethoxybenzyl)-5-(o-tolyl)-5,6-dihydro-7H-pyrrolo[3,4-b]pyridin-7-one (62.0 g, 152 mmol, 85.9% yield) as a white solid. MS: m/z=409.1 [M+H]$^+$; $^1$H NMR (400 MHz, DMSO-d$_6$) δ 8.73 (d, J=5.2 Hz, 1H), 7.66 (d, J=5.6 Hz, 1H), 7.20-7.28 (m, 2H), 7.04-7.08 (m, 1H), 6.95 (d, J=8.4 Hz, 1H), 6.45-6.50 (m, 4H), 5.78 (s, 1H), 4.82 (dd, J=3.6, 14.8 Hz, 1H), 3.73 (s, 3H), 3.64 (s, 3H), 2.24 (s, 3H).

6-(2,4-Dimethoxybenzyl)-4-((2,4-dimethoxybenzyl)amino)-5-(o-tolyl)-5,6-dihydro-7H-pyrrolo[3,4-b]pyridin-7-one

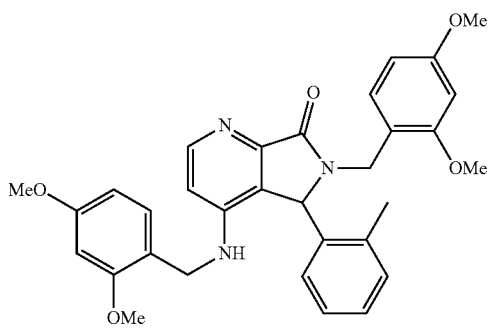 [SMILES: COc1ccc(CNc2ccnc3c2C(c2ccccc2C)N(Cc2ccc(OC)cc2OC)C3=O)c(OC)c1]

Step 4: A mixture of 4-chloro-6-(2,4-dimethoxybenzyl)-5-(o-tolyl)-5,6-dihydro-7H-pyrrolo[3,4-b]pyridin-7-one (70.0 g, 171 mmol, 1.00 eq), (2,4-dimethoxyphenyl) methanamine (42.9 g, 256 mmol, 38.6 mL, 1.50 eq), Cs$_2$CO$_3$ (55.7 g, 171 mmol, 1.00 eq), Pd$_2$(dba)$_3$ (15.6 g, 17.1 mmol, 0.10 eq), and BRETTPHOS (18.3 g, 34.2 mmol, 0.20 eq) in dioxane (700 mL) was degassed and purged with N$_2$ three times, and then the mixture was stirred at 90° C. for 12 h under N$_2$ atmosphere. Additional (2,4-dimethoxyphenyl) methanamine (14.3 g, 85.6 mmol, 12.8 mL, 0.50 eq) was added, the mixture was purged with N$_2$ three times, and then the mixture was stirred at 90° C. for 18 h under N$_2$ atmosphere. The reaction mixture was diluted with H$_2$O (600 mL) and extracted with ethyl acetate (3×400 mL). The combined organic layers were washed with satd. aq. NaCl (800 mL), dried over Na$_2$SO$_4$, filtered, and concentrated under reduced pressure. The resulting residue was purified by column chromatography (SiO$_2$, petroleum ether/ethyl acetate=1/0 to 0/1, ethyl acetate/methanol=20/1) to afford 6-(2,4-dimethoxybenzyl)-4-((2,4-dimethoxybenzyl)amino)-5-(o-tolyl)-5,6-dihydro-7H-pyrrolo[3,4-b]pyridin-7-one (60.0 g, 94.1 mmol, 55.0% yield, 84.7% purity) as a brown oil. MS: m/z=540.0 [M+H]$^+$; $^1$H NMR (400 MHz, CDCl$_3$) δ 8.39-8.42 (m, 1H), 7.29-7.30 (m, 1H), 7.21-7.23 (m, 1H), 7.17-7.18 (m, 1H), 7.14 (s, 1H), 7.12 (s, 1H), 7.07-7.09 (m, 1H), 6.91-6.94 (m, 1H), 6.78-6.80 (m, 1H), 6.70 (d, J=8.4 Hz, 1H), 6.54 (d, J=6.0 Hz, 1H), 6.29-6.32 (m, 2H), 5.36 (s, 1H), 3.76-3.80 (m, 12H), 3.66 (s, 2H), 3.63 (s, 2H), 2.08 (s, 3H).

4-Amino-6-(2,4-dimethoxybenzyl)-5-(o-tolyl)-5,6-dihydro-7H-pyrrolo[3,4-b]pyridin-7-one

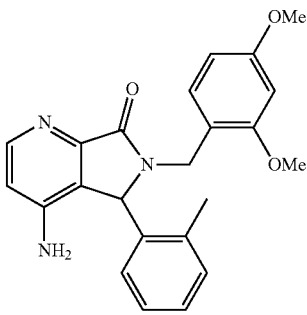 [SMILES: COc1ccc(CN2C(=O)c3nccc(N)c3C2c2ccccc2C)c(OC)c1]

Step 5: A solution of 6-(2,4-dimethoxybenzyl)-4-((2,4-dimethoxybenzyl)amino)-5-(o-tolyl)-5,6-dihydro-7H-pyrrolo[3,4-b]pyridin-7-one (60.0 g, 111 mmol, 1.00 eq) in HCl/MeOH (4.00 M, 600 mL, 21.6 eq) was stirred at 35° C. for 7 h. Additional HCl/MeOH (4.00 M, 600 mL, 21.6 eq) was added to the mixture, then the mixture was stirred at 35° C. for 16 h. Additional HCl/MeOH (4.00 M, 600 mL, 21.6 eq) was added to the mixture, then the mixture was stirred at 35° C. for 22 h. The reaction mixture was concentrated under vacuum, and the residue was dissolved in DCM (2.00 L). The mixture was adjusted to pH=8 with saturated NaHCO$_3$ (1.00 L) and stirred at 25° C. for 0.5 h. The mixture was extracted with DCM (2×2.00 L). The combined organic layers were washed with brine (2×200 mL), dried over Na$_2$SO$_4$, filtered, and concentrated. The resulting brown gum was purified by reversed-phase HPLC (0.1% FA condition) to afford 4-amino-6-(2,4-dimethoxybenzyl)-5-(o-tolyl)-5,6-dihydro-7H-pyrrolo[3,4-b]pyridin-7-one (20.4 g, 50.4 mmol, 45.3% yield, 96.0% purity) as a white solid. MS: m/z=390.2 [M+H]$^+$; $^1$H NMR (400 MHz, DMSO-d$_6$) δ 8.17-8.23 (m, 1H), 7.52-7.54 (m, 1H), 7.18-7.27 (m, 2H), 7.06-7.09 (m, 1H), 6.97 (d, J=8.4 Hz, 1H), 6.84 (d, J=8.4 Hz, 1H), 6.59-6.65 (m, 1H), 6.44-6.53 (m, 3H), 5.39-5.48 (m, 2H), 4.69-4.82 (m, 1H), 3.69-3.78 (m, 6H), 2.25 (s, 2H), 1.15 (s, 1H).

N-(6-(2,4-Dimethoxybenzyl)-7-oxo-5-(o-tolyl)-6,7-dihydro-5H-pyrrolo[3,4-b]pyridin-4-yl)indoline-1-carboxamide

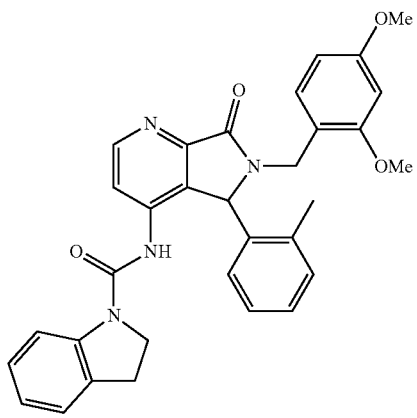 [SMILES: COc1ccc(CN2C(=O)c3nccc(NC(=O)N4CCc5ccccc54)c3C2c2ccccc2C)c(OC)c1]

Step 6: 4-Amino-6-(2,4-dimethoxybenzyl)-5-(o-tolyl)-5H-pyrrolo[3,4-b]pyridine-7(6H)-one (1.00 g, 1.87 mmol) and carbonyldiimidazole (457 mg, 2.82 mmol) were dissolved in DCM (25 mL). To the resulting mixture were added N,N-diisopropylethylamine (0.54 mL, 3.08 mmol) and 4-dimethylaminopyridine (2.5 mg, 0.020 mmol). The resulting mixture was stirred at 40° C. After 24 h, the reaction mixture was cooled to 22° C., and indoline (457 mg, 3.84 mmol) was added to the solution. The resulting mixture was stirred at 22° C. for 1 h and then diluted with a saturated aqueous NH$_4$Cl solution and extracted with DCM. The organic layer was dried over sodium sulfate, filtered, and concentrated by rotary evaporation. The resulting N-(6-(2,4-dimethoxybenzyl)-7-oxo-5-(o-tolyl)-6,7-dihydro-5H-pyrrolo[3,4-b]pyridin-4-yl)indoline-1-carboxamide was directly subjected to the subsequent reaction without further purification.

N-(7-Oxo-5-(o-tolyl)-6,7-dihydro-5H-pyrrolo[3,4-b]pyridin-4-yl)indoline-1-carboxamide

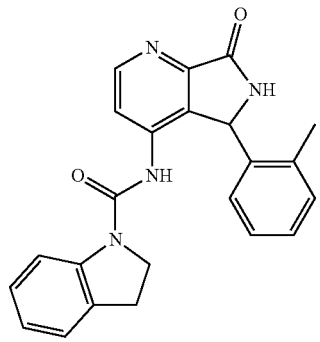 [SMILES: Cc1ccccc1C1NC(=O)c2nccc(NC(=O)N3CCc4ccccc43)c21]

Step 7: The N-(6-(2,4-dimethoxybenzyl)-7-oxo-5-(o-tolyl)-6,7-dihydro-5H-pyrrolo[3,4-b]pyridin-4-yl)indoline-1-carboxamide (ca. 1.00 mmol) from the preceding step was treated with trifluoroacetic acid (14.2 mL) and trifluoromethanesulfonic acid (0.41 mL, 4.67 mmol). The resulting mixture was stirred at 40° C. After 1 h, the reaction mixture was concentrated, diluted with saturated aqueous NaHCO$_3$, and extracted with DCM. The organic layer was dried over sodium sulfate, filtered, and concentrated by rotary evaporation. The resulting mixture was purified by C18 silica gel column chromatography (20% to 100% MeCN/10 mM AmF (aq)). The product-containing fractions were combined and lyophilized to obtain N-(7-oxo-5-(o-tolyl)-6,7-dihydro-5H-pyrrolo[3,4-b]pyridin-4-yl)indoline-1-carboxamide (38 mg, 5.3% over two steps) as a white powder.

Additional compounds prepared according to the methods of Example 60 are listed in Table 28 below.

TABLE 28

| Additional Exemplary Compounds Compound |
| --- |
| I-148 |
| I-177 |
| I-199 |
| I-227 |
| I-228 |
| I-229 |
| I-230 |
| I-245 |

TABLE 28-continued

Additional Exemplary Compounds
Compound

I-246
I-247
I-248
I-249
I-251
I-257
I-282
I-296
I-300
I-301
I-302
I-303
I-324

Example 61

N-(5-(2,3-Difluorophenyl)-7-oxo-6,7-dihydro-5H-pyrrolo[3,4-b]pyridin-4-yl)benzo[b]thiophene-3-carboxamide (I-15)

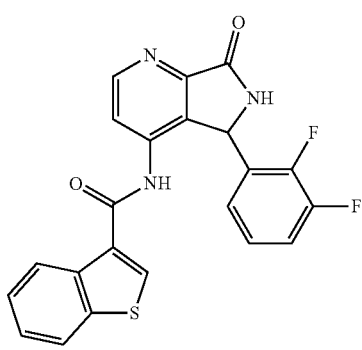 [SMILES: O=C1NC(c2cccc(F)c2F)c2c(NC(=O)c3csc4ccccc34)ccnc21]

4-Amino-5-(2,3-difluorophenyl)-6-(2,4-dimethoxy-benzyl)-5,6-dihydro-7H-pyrrolo[3,4-b]pyridin-7-one

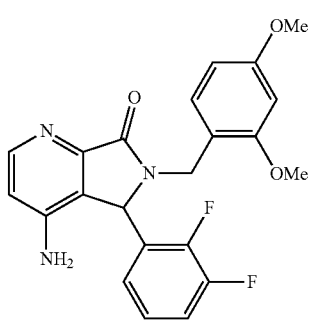 [SMILES: COc1ccc(CN2C(=O)c3nccc(N)c3C2c2cccc(F)c2F)c(OC)c1]

Steps 1 to 5: According to the procedures of Example 60, Steps 1 to 5, 4-amino-5-(2,3-difluorophenyl)-6-(2,4-dimethoxybenzyl)-5,6-dihydro-7H-pyrrolo[3,4-b]pyridin-7-one was synthesized.

N-(5-(2,3-Difluorophenyl)-6-(2,4-dimethoxybenzyl)-7-oxo-6,7-dihydro-5H-pyrrolo[3,4-b]pyridin-4-yl)benzo[b]thiophene-3-carboxamide

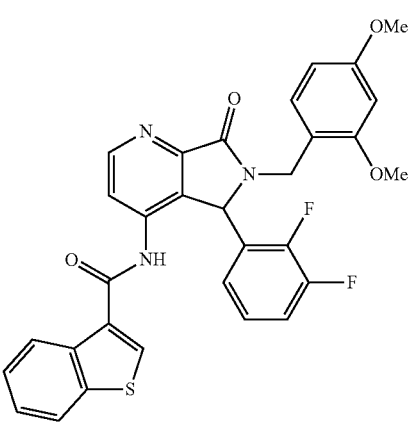 [SMILES: COc1ccc(CN2C(=O)c3nccc(NC(=O)c4csc5ccccc45)c3C2c2cccc(F)c2F)c(OC)c1]

Step 6: To a stirred solution of (1-chloro-2-methylprop-1-en-1-yl)dimethylamine (257 mg, 1.93 mmol, 4 eq) in toluene (1.6 mL) was added 1-benzothiophene-3-carboxylic acid (343 mg, 1.93 mmol, 4 eq). The suspension quickly turned into a clear, light pink solution, which was stirred for 30 minutes. About 0.4 mL of this solution was added to a stirred solution of 4-amino-5-(2,3-difluorophenyl)-6-(2,4-dimethoxybenzyl)-5,6-dihydro-7H-pyrrolo[3,4-b]pyridin-7-one (200 mg, 0.483 mmol) in pyridine (1 mL). To this solution was added catalytic DMAP (24 mg, 0.19 mmol, 0.4 eq). The mixture was stirred at room temperature for 5 minutes and then at 75-80° C. for 5 hours. Every hour an additional 0.4 mL of the preformed acid chloride solution in toluene was added to the mixture until the reaction was nearly completed. The mixture was cooled to room temperature and quenched with methanol (2 mL). The mixture was stirred 10 minutes after quenching and was then concentrated. The residue was eluted on 12 g column eluted with a gradient of 10:90:1 MeOH/DCM/NH$_4$OH in DCM, to afford N-(5-(2,3-difluorophenyl)-6-(2,4-dimethoxybenzyl)-7-oxo-6,7-dihydro-5H-pyrrolo[3,4-b]pyridin-4-yl)benzo[b]thiophene-3-carboxamide (214 mg, ~95% purity, 73.5% yield) as a light yellow, foamy solid. A small amount of residual pyridine was still present after purification. MS: m/z=572.5 [M+H]$^+$.

1915

N-(5-(2,3-Difluorophenyl)-7-oxo-6,7-dihydro-5H-pyrrolo[3,4-b]pyridin-4-yl)benzo[b]thiophene-3-carboxamide

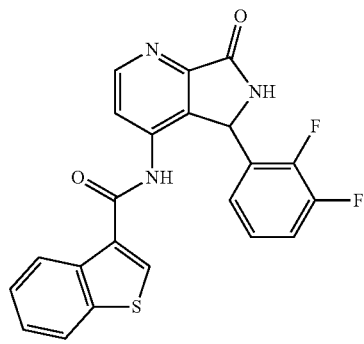 [SMILES: O=C1NC(c2cccc(F)c2F)c2c(NC(=O)c3csc4ccccc34)ccnc21]

Step 7: To a solution of N-(5-(2,3-difluorophenyl)-6-(2,4-dimethoxybenzyl)-7-oxo-6,7-dihydro-5H-pyrrolo[3,4-b]pyridin-4-yl)benzo[b]thiophene-3-carboxamide (197 mg, 0.342 mmol) in acetonitrile (6.8 mL) was added a solution of ammonium cerium (IV) nitrate (559 mg, 1.02 mmol, 3.0 eq). The mixture was stirred for 15 minutes at RT. The mixture was carefully treated with saturated aqueous NaHCO$_3$ (25 mL). The resulting solid was isolated by filtration, dried, and loaded as a silica gel slurry onto a 24 gram silica gel column, which was eluted with a gradient of 10:90:1 MeOH/DCM/NH$_4$OH in DCM. Product-containing fractions (eluting between 6.7% and 7.5% MeOH/DCM) were combined, concentrated, and dried. The resulting yellow solid (93 mg) was then treated with dichloromethane (2 mL). A light yellow solid was isolated by filtration and dried to yield N-(5-(2,3-difluorophenyl)-7-oxo-6,7-dihydro-5H-pyrrolo[3,4-b]pyridin-4-yl)benzo[b]thiophene-3-carboxamide (84.5 mg, 58% yield).

Additional compounds prepared according to the methods of Example 60 and 61 are listed in Table 29 below.

TABLE 29

| Additional Exemplary Compounds Compound |
| --- |
| I-7 |
| I-9 |
| I-22 |
| I-23 |
| I-32 |
| I-33 |
| I-70 |
| I-71 |
| I-142 |
| I-171 |
| I-172 |
| I-173 |
| I-174 |
| I-175 |
| I-208 |
| I-209 |
| I-210 |
| I-234 |
| I-235 |
| I-240 |
| I-305 |

1916

Example 62

3-Fluoro-N-(4-methyl-3-oxo-1-(o-tolyl)-2,3-dihydro-1H-pyrrolo[3,4-c]pyridin-7-yl)-5-(trifluoromethyl)benzamide (I-244)

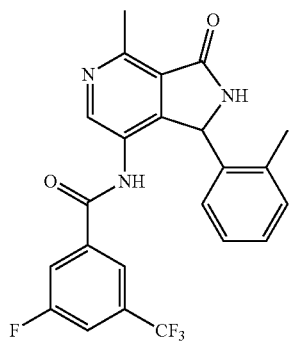 [SMILES: Cc1ccccc1C1NC(=O)c2c(C)ncc(NC(=O)c3cc(F)cc(C(F)(F)F)c3)c21]

N-(2-(2,4-Dimethoxybenzyl)-4-methyl-3-oxo-1-(o-tolyl)-2,3-dihydro-1H-pyrrolo[3,4-c]pyridin-7-yl)-3-fluoro-5-(trifluoromethyl)benzamide

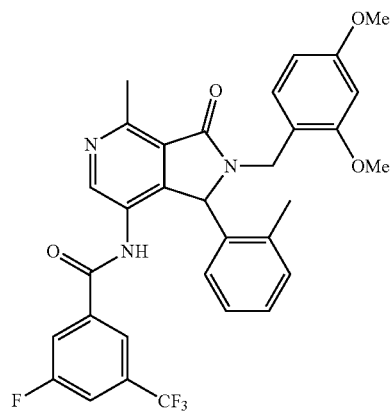 [SMILES: COc1ccc(CN2C(=O)c3c(C)ncc(NC(=O)c4cc(F)cc(C(F)(F)F)c4)c3C2c2ccccc2C)c(OC)c1]

Step 1: To a solution of N-(4-chloro-2-(2,4-dimethoxybenzyl)-3-oxo-1-(o-tolyl)-2,3-dihydro-1H-pyrrolo[3,4-c]pyridin-7-yl)-3-fluoro-5-(trifluoromethyl)benzamide (50 mg, 0.0814 mmol) in dioxane (500 µL) and water (50 µL) was added potassium carbonate (33.7 mg, 0.2442 mmol), trimethyl-1,3,5,2,4,6-trioxatriborinane (12.4 µL, 0.0896 mmol), and tetrakis(triphenylphosphine) palladium (4.70 mg, 0.00407 mmol). The mixture was stirred at 100° C. for 16 h, then quenched with 1N HCl (100 µL), then diluted with water. The resulting mixture was extracted with EtOAc three times. The combined organics were dried over Na$_2$SO$_4$, filtered, and concentrated. The resulting residue was used directly in the next step without further purification.

1917

3-Fluoro-N-(4-methyl-3-oxo-1-(o-tolyl)-2,3-di-hydro-1H-pyrrolo[3,4-c]pyridin-7-yl)-5-(trifluoromethyl)benzamide

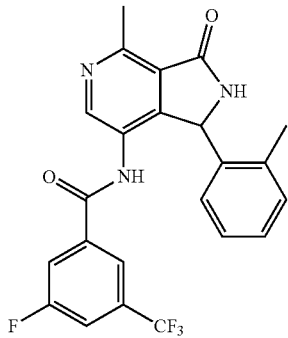 [SMILES: Cc1ccccc1C1NC(=O)c2c(C)ncc(NC(=O)c3cc(F)cc(C(F)(F)F)c3)c21]

Step 2: According to the procedures of Example 13, Step 6, N-(2-(2,4-dimethoxybenzyl)-4-methyl-3-oxo-1-(o-tolyl)-2,3-dihydro-1H-pyrrolo[3,4-c]pyridin-7-yl)-3-fluoro-5-(trifluoromethyl)benzamide was converted to 3-fluoro-N-(4-methyl-3-oxo-1-(o-tolyl)-2,3-dihydro-1H-pyrrolo[3,4-c]pyridin-7-yl)-5-(trifluoromethyl)benzamide.

Example 63

N-(1-Chloro-1-(2-chloro-5-fluorophenyl)-4-(3,3-difluoroazetidin-1-yl)-3-oxo-2,3-dihydro-1H-pyrrolo[3,4-c]pyridin-7-yl)-3-fluoro-5-(trifluoromethyl)benzamide (I-274)

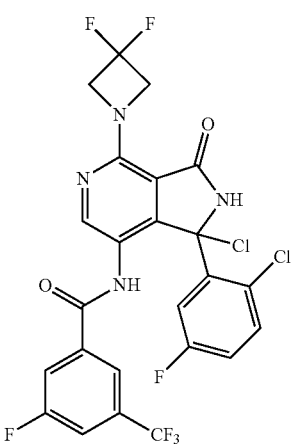 [SMILES: O=C(Nc1cnc(N2CC(F)(F)C2)c2c1C(Cl)(c1cc(F)ccc1Cl)NC2=O)c1cc(F)cc(C(F)(F)F)c1]

1918

N-[4-Chloro-1-(2-chloro-5-fluorophenyl)-3-oxo-1H,2H,3H-pyrrolo[3,4-c]pyridin-7-yl]-3-fluoro-5-(trifluoromethyl)benzamide

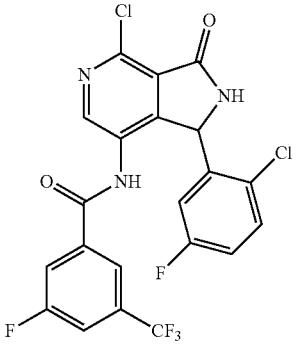 [SMILES: O=C(Nc1cnc(Cl)c2c1C(c1cc(F)ccc1Cl)NC2=O)c1cc(F)cc(C(F)(F)F)c1]

Steps 1-6: By analogy to the procedures of Example 13, Steps 1-6, N-[4-chloro-1-(2-chloro-5-fluorophenyl)-3-oxo-1H,2H,3H-pyrrolo[3,4-c]pyridin-7-yl]-3-fluoro-5-(trifluoromethyl)benzamide was prepared.

N-(1-Chloro-1-(2-chloro-5-fluorophenyl)-4-(3,3-difluoroazetidin-1-yl)-3-oxo-2,3-dihydro-1H-pyrrolo[3,4-c]pyridin-7-yl)-3-fluoro-5-(trifluoromethyl)benzamide

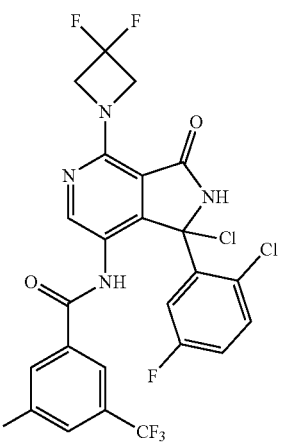

Step 7: A conical microwave reaction tube was charged with N-[4-chloro-1-(2-chloro-5-fluorophenyl)-3-oxo-1H,2H,3H-pyrrolo[3,4-c]pyridin-7-yl]-3-fluoro-5-(trifluoromethyl)benzamide (11 mg, 21.9 μmol, 1.0 eq.), 3,3-difluoroazetidine hydrochloride (3.65 mg, 28.4 μmol, 1.3 eq.), and cesium carbonate (17.8 mg, 54.7 μmol, 2.5 eq.) and purged with nitrogen for 5 minutes. Dry DMF (0.5 mL) was then added to the reaction media, which was sealed and stirred at 85° C. for 2 h. The reaction media was allowed to cool to room temperature, diluted with EtOAc (4 mL), and the organic phase was washed 4 times with half-saturated NaHCO$_3$ (aq). The organic layer was then dried over anhydrous MgSO$_4$ and concentrated under vacuum. The crude mixture was purified over C18 column, eluting with water (10 mM formate): acetonitrile 95:5 to 0:100. The pure fractions were lyophilized to afford N-(1-chloro-1-(2-chloro-5-fluorophenyl)-4-(3,3-difluoroazetidin-1-yl)-3-oxo- 2,3-dihydro-1H-pyrrolo[3,4-c]pyridin-7-yl)-3-fluoro-5-(trifluoromethyl)benzamide (3.2 mg). MS: m/z=593.1 [M+H]f; ¹H NMR (400 MHz, CD₃OD) δ 8.71 (s, 1H), 7.87 (s, 1H), 7.77 (d, J=8.6 Hz, 1H), 7.68-7.58 (m, 2H), 7.49-7.32 (m, 1H), 7.14-6.97 (m, 1H), 3.82-3.56 (m, 4H).

Additional compounds prepared by analogy to the methods of Examples 13, 14, 62, 63, and other Examples herein, are listed in Table 30 below.

TABLE 30

| Additional Exemplary Compounds Compound |
| --- |
| I-143 |
| I-233 |
| I-236 |
| I-243 |
| I-253 |
| I-254 |
| I-255 |
| I-265 |
| I-287 |
| I-320 |

Example 64

N-(3-(2-(Difluoromethyl)-5-fluorophenyl)-5-fluoro-1-oxoisoindolin-4-yl)-3-fluoro-5-(trifluoromethyl)benzamide (I-283)

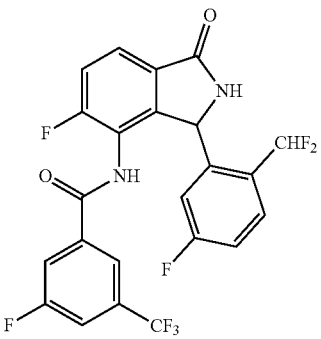 [SMILES: O=C(Nc1c(F)ccc2c1C(c1cc(F)ccc1C(F)F)NC2=O)c1cc(F)cc(C(F)(F)F)c1]

2-[1-(3-Bromo-2,4-difluorophenyl)-N-[(2,4-dimethoxyphenyl)methyl]formamido]-N-tert-butyl-2-[2-(difluoromethyl)-5-fluorophenyl]acetamide

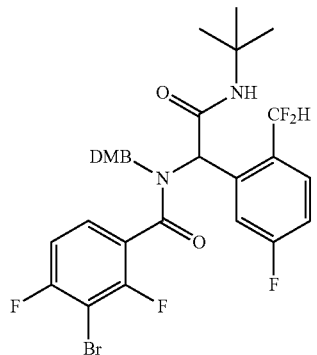

Step 1: To a solution of 2-(difluoromethyl)-5-fluorobenzaldehyde (405 mg, 2.33 mmol) in methanol (5 mL) was added 1-(2,4-dimethoxyphenyl)methanamine (350 µL, 2.33 mmol), followed by 3-bromo-2,4-difluorobenzoic acid (500 mg, 2.10 mmol), and 2-isocyano-2-methylpropane (193 mg, 2.33 mmol). The mixture was stirred at room temperature overnight. The reaction mixture was concentrated in vacuo to obtain a yellow solid. The resulting 2-[1-(3-bromo-2,4-difluorophenyl)-N-[(2,4-dimethoxyphenyl)methyl]formamido]-N-tert-butyl-2-[2-(difluoromethyl)-5-fluorophenyl]acetamide was used in the next step without further purification. LC-MS (Method 1): 1.62 min, m/z=644.2 [M+H]¹. 4-Bromo-3-[2-(difluoromethyl)-5-fluorophenyl]-2-[(2,4-dimethoxyphenyl)methyl]-5-fluoro-2,3-dihydro-1H-isoindol-1-one

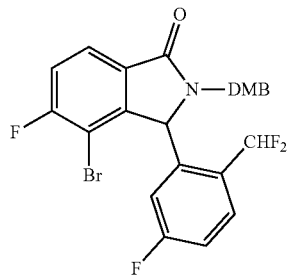

Step 2: A solution of 2-[1-(3-bromo-2,4-difluorophenyl)-N-[(2,4-dimethoxyphenyl)methyl]formamido]-N-tert-butyl-2-[2-(difluoromethyl)-5-fluorophenyl]acetamide (1.0 g, 1.55 mmol) in DMF (6.2 mL) was evacuated and purged with nitrogen three times, and the reaction mixture was stirred at −78° C. for 5 minutes. Then NaH (92.8 mg, 3.87 mmol) was added under nitrogen atmosphere, and the reaction was stirred overnight from −78° C. to 22° C. The reaction mixture was neutralized with sat. NH₄Cl and then extracted with EtOAc (10 mL). The aqueous phase was extracted with EtOAc (3×5 mL). The combined organic layers were washed with brine solution, dried over sodium sulfate, filtered, and concentrated in vacuo. The resulting residue contained both 4-bromo-3-[2-(difluoromethyl)-5-fluorophenyl]-2-[(2,4-dimethoxyphenyl)methyl]-5-fluoro-2,3-dihydro-1H-isoindol-1-one and oxidized product 4-bromo-3-[2-(difluoromethyl)-5-fluorophenyl]-2-[(2,4-dimethoxyphenyl)methyl]-5-fluoro-3-hydroxy-2,3-dihydro-1H-isoindol-1-one. The mixture was purified by normal phase chromatography (50 g column, hexane/acetone). The purified desired 4-bromo-3-[2-(difluoromethyl)-5-fluorophenyl]-2-[(2,4-dimethoxyphenyl)methyl]-5-fluoro-2,3-dihydro-1H-isoindol-1-one was used in Step 3.

The purified oxidized product was subjected to a reduction reaction: A solution of 4-bromo-3-[2-(difluoromethyl)-5-fluorophenyl]-2-[(2,4-dimethoxyphenyl)methyl]-5-fluoro-3-hydroxy-2,3-dihydro-1H-isoindol-1-one (500 mg, 0.9253 mmol) in DCM (2 mL) was cooled to −78° C. and BF₃OEt₂ (182 µL, 1.48 mmol) was added. After 15 min, triethylsilane (1.46 mL, 9.25 mmol) was added. The mixture was stirred at −78° C. for additional 15 minutes and then warmed to 22° C. and stirred for 3 h. The mixture was diluted with aq. NaHCO₃ and extracted with DCM. The organics were dried over sodium sulfate, filtered, and concentrated in vacuo. The resulting 4-bromo-3-[2-(difluoromethyl)-5-fluorophenyl]-2-[(2,4-dimethoxyphenyl)methyl]-

5-fluoro-2,3-dihydro-1H-isoindol-1-one was combined with the previous portion and used in the next step without further purification.

4-Amino-3-[2-(difluoromethyl)-5-fluorophenyl]-2-[(2,4-dimethoxyphenyl)methyl]-5-fluoro-2,3-dihydro-1H-isoindol-1-one

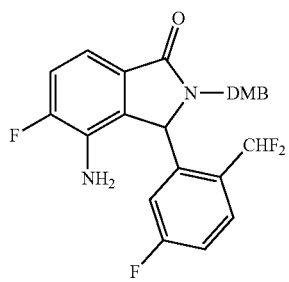

Step 3: To a solution of 4-bromo-3-[2-(difluoromethyl)-5-fluorophenyl]-2-[(2,4-dimethoxyphenyl)methyl]-5-fluoro-2,3-dihydro-1H-isoindol-1-one (20 mg, 0.03814 mmol) in toluene (0.4 mL) was added diphenylmethanimine (8.29 mg, 0.04576 mmol), followed by (S)-BINAP (7.12 mg, 0.01144 mmol), Pd$_2$(dba)$_3$ (3.49 mg, 0.003814 mmol), and NaOtBu (5.49 mg, 0.05721 mmol). The mixture was stirred at 80° C. for 16 h. The reaction mixture was quenched with 1 M HCl and stirred at 22° C. overnight. Then, the reaction mixture was diluted with DCM (10 mL) and NaHCO$_3$ (15 mL), and the aqueous phase was extracted with DCM (3×5 mL). The combined organic layers were washed with brine solution, dried over sodium sulfate, filtered, and concentrated in vacuo. The residue was purified by reverse phase chromatography (30 g column, water/ACN; water solvent is 10 mM ammonium formate) to afford 4-amino-3-[2-(difluoromethyl)-5-fluorophenyl]-2-[(2,4-dimethoxyphenyl)methyl]-5-fluoro-2,3-dihydro-1H-isoindol-1-one. LC-MS (Method 1): 1.30 min, m/z=461.3 [M+H]$^+$.

N-{3-[2-(difluoromethyl)-5-fluorophenyl]-2-[(2,4-dimethoxyphenyl)methyl]-5-fluoro-1-oxo-2,3-dihydro-1H-isoindol-4-yl}-3-fluoro-5-(trifluoromethyl)benzamide

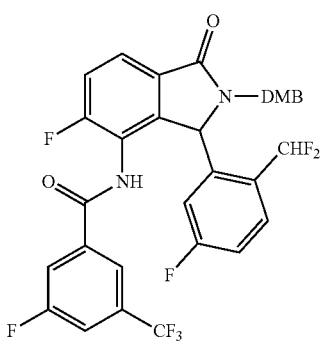

Step 4: To a solution of 4-amino-3-[2-(difluoromethyl)-5-fluorophenyl]-2-[(2,4-dimethoxyphenyl)methyl]-5-fluoro-2,3-dihydro-1H-isoindol-1-one (10 mg, 0.0217 mmol) in DCM (1 mL) was added 3-fluoro-5-(trifluoromethyl)benzoyl chloride (7.37 mg, 0.0326 mmol) and K$_2$CO$_3$ (15 mg, 0.108 mmol). The reaction mixture was stirred for 3 hrs at 50° C. The reaction mixture was diluted with EtOAc (10 mL) and NaHCO$_3$ (15 mL), and the aqueous phase was extracted with EtOAc (3×5 mL). The combined organic layers were washed with brine solution, dried over sodium sulfate, filtered, and concentrated in vacuo. The resulting residue was purified by reverse-phase chromatography (30 g column, water/ACN; water solvent is 10 mM ammonium formate). LC-MS (Method 1): 1.52 min, m/z=651.7 [M+H]$^+$.

N-(3-(2-(Difluoromethyl)-5-fluorophenyl)-5-fluoro-1-oxoisoindolin-4-yl)-3-fluoro-5-(trifluoromethyl)benzamide

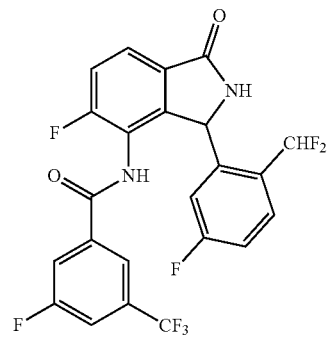

Step 5: A mixture of N-{3-[2-(difluoromethyl)-5-fluorophenyl]-2-[(2,4-dimethoxyphenyl)methyl]-5-fluoro-1-oxo-2,3-dihydro-1H-isoindol-4-yl}-3-fluoro-5-(trifluoromethyl)benzamide (10 mg, 0.01537 mmol) in TFA (2 mL) was heated to 40° C. in a sealed tube for 1 hour. The reaction mixture was then cooled to ambient temperature and concentrated in vacuo. The resulting residue was purified by reverse-phase chromatography (30 g column, water/ACN; water solvent is 10 mM ammonium formate) to afford N-(3-(2-(difluoromethyl)-5-fluorophenyl)-5-fluoro-1-oxoisoindolin-4-yl)-3-fluoro-5-(trifluoromethyl)benzamide (0.79 mg, 5% yield over 2 steps).

Example 65

N-(3-Methyl-1-oxo-3-(o-tolyl)isoindolin-4-yl)benzo[b]thiophene-3-carboxamide (I-80)

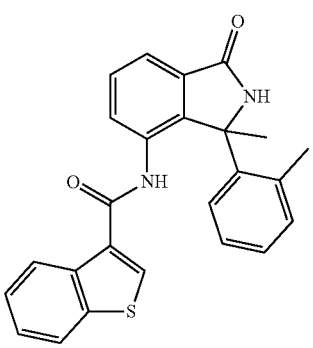 [SMILES: Cc1ccccc1C1(C)NC(=O)c2cccc(NC(=O)c3csc4ccccc34)c21]

1923
4-Amino-2-(4-methoxybenzyl)-3-methyl-3-(o-tolyl)
isoindolin-1-one

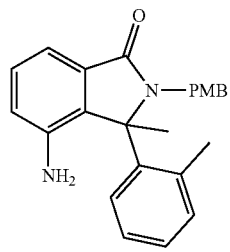

Step 1: To a solution of 4-amino-3-hydroxy-2-(4-methoxybenzyl)-3-(o-tolyl)isoindolin-1-one (300 mg, 0.801 mmol) in dry THF (3 mL) at room temperature under a nitrogen atmosphere was added BF$_3$·OEt$_2$ (295 μL, 2.40 mmol). The purple solution was then stirred at room temperature for 12h, then a solution of chloro(methyl)magnesium (4.8 mL, 3M in THF, 14.3 mmol) was added. The mixture was stirred for another 1 h, and then a saturated (aq) solution of NH$_4$Cl (20 mL) was added slowly. The mixture was diluted with EtOAc and extracted with EtOAc (3×). The combined organic layers were washed with brine, dried over Na$_2$SO$_4$, filtered, and concentrated under reduced pressure to yield an orange foam. The resulting 4-amino-2-(4-methoxybenzyl)-3-methyl-3-(o-tolyl)isoindolin-1-one was used without further purification. LC-MS (Method 1): 1.24 min, m/z=373.3 [M+H][1].

4-Amino-3-methyl-3-(o-tolyl)isoindolin-1-one

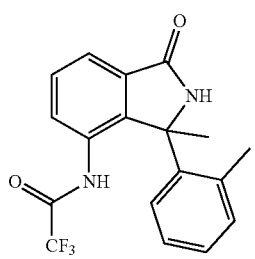 [SMILES: Cc1ccccc1C1(C)NC(=O)c2cccc(NC(=O)C(F)(F)F)c21]

Step 2: A solution of 4-amino-2-(4-methoxybenzyl)-3-methyl-3-(o-tolyl)isoindolin-1-one (150 mg, 0.282 mmol) in TFA (15 mL) was heated at 170° C. for 80 min under microwave irradiation. Analysis indicated the major product was 2,2,2-trifluoro-N-(3-methyl-1-oxo-3-(o-tolyl)isoindolin-4-yl)acetamide. The mixture was then concentrated under reduced pressure and dissolved in MeOH (10 mL). Potassium carbonate (500 mg, 3.56 mmol) was added, and the mixture was heated at 60° C. for 12 h. The mixture was then diluted with a satd. (aq) solution of NH$_4$Cl and extracted with DCM (4×). The combined organic layers were washed with brine, dried over Na$_2$SO$_4$, filtered, and concentrated under reduced pressure to afford 4-amino-3-methyl-3-(o-tolyl)isoindolin-1-one, which was used in the next step without further purification.

1924
N-(3-Methyl-1-oxo-3-(o-tolyl)isoindolin-4-yl)benzo
[h]thiophene-3-carboxamide

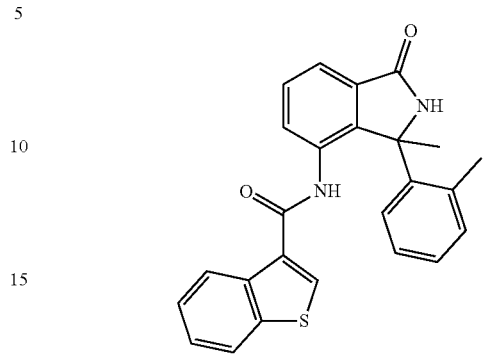

Step 3: The 4-amino-3-methyl-3-(o-tolyl)isoindolin-1-one from the previous step was dissolved in pyridine (6 mL) and 1-benzothiophene-3-carbonyl chloride (110 mg, 0.563 mmol) was added. The mixture was stirred at room temperature for 12 h. The mixture was then diluted with a satd. (aq) solution of CuSO$_4$ and extracted with EtOAc (3×). The combined organic layers were washed with water, then satd. NaHCO$_3$ (aq), and finally with brine, then dried over Na$_2$SO$_4$, filtered, and concentrated under reduced pressure. Purification by reverse phase chromatography (5 to 70% ACN/Water [AmF 10 mM]) followed by purification by normal phase chromatography (0 to 60% acetone/heptanes) afforded N-(3-methyl-1-oxo-3-(o-tolyl)isoindolin-4-yl)benzo[b]thiophene-3-carboxamide (43 mg, 37% over two steps) as a white powder after lyophilisation.

Additional compounds prepared by analogy to the methods of Example 65, and other Examples herein, are listed in Table 31 below.

TABLE 31

| Additional Exemplary Compounds |
| --- |
| Compound |
| I-130 |

Example 66

N-(1-(2-chlorophenyl)-6-methoxy-3-oxo-2,3-di-hydro-1H-pyrrolo[3,4-c]pyridin-7-yl)-3-fluoro-5-(trifluoromethyl)benzamide (I-335)

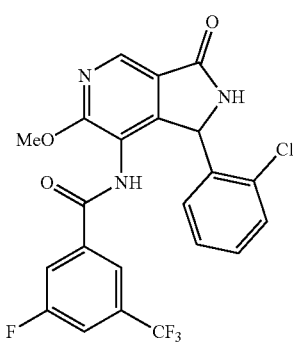 [SMILES: COc1ncc2c(c1NC(=O)c1cc(F)cc(C(F)(F)F)c1)C(c1ccccc1Cl)NC2=O]

1925

2-Chloro-N-(2,4-dimethoxybenzyl)benzamide

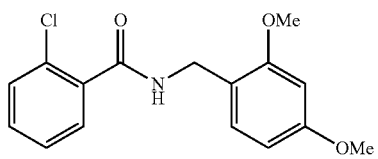 [SMILES: COc1ccc(CNC(=O)c2ccccc2Cl)c(OC)c1]

Step 1: To a solution of 1-(2,4-dimethoxyphenyl)methanamine (4.76 g, 28.5 mmol) in DCM (30 mL) was added DIPEA (9.91 mL, 57.0 mmol). The solution was cooled to 0-5° C., then 2-chlorobenzoyl chloride (3.61 mL, 28.5 mmol) was added dropwise. The mixture was warmed to RT and stirred for 2 h. The mixture was diluted with DCM and washed with water. The organic layer was dried and concentrated. Heptane was added, and the mixture was sonicated until solid separated. The mixture was filtered and air dried to afford 2-chloro-N-(2,4-dimethoxybenzyl)benzamide (7.89 g, 25.8 mmol, 90.5% yield) as a white solid. MS: m/z=306.3 [M+H]$^+$.

1-(2-Chlorophenyl)-2-(2,4-dimethoxybenzyl)-6-methoxy-7-nitro-1,2-dihydro-3H-pyrrolo[3,4-c]pyridin-3-one

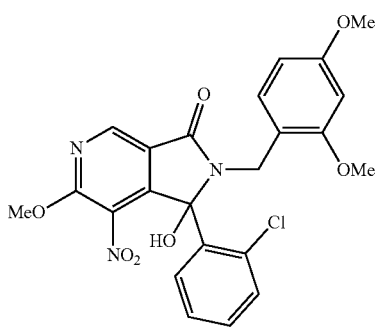

Step 2: To a solution of 2-chloro-N-(2,4-dimethoxybenzyl)benzamide (1.51 g, 4.97 mmol) in THF (25 mL) at −50° C. was added LHMDS (4.97 mL, 4.97 mmol) dropwise over 15 min, keeping temperature at −50° C. The mixture was stirred at −50° C. for 15 min, then 6-chloro-5-nitropyridine-3-carbonyl chloride (1.1 g, 4.97 mmol) was added dropwise over 15 min. Upon completion of addition, the mixture was warmed to −20° C. over 30 min. After 30 min, the mixture was cooled to −50° C. and a second equivalent of LHMDS (4.97 mL, 4.97 mmol) was added dropwise over 15 min. The mixture was warmed to room temperature over 45 min. The reaction mixture was quenched at room temperature with MeOH (25 mL). The solution was concentrated onto SiO2 and purified by normal phase chromatography (0-100% ethyl acetate in heptanes) to afford 1-(2-chlorophenyl)-2-(2,4-dimethoxybenzyl)-6-methoxy-7-nitro-1,2-dihydro-3H-pyrrolo[3,4-c]pyridin-3-one (1.24 g, 0.638 mmol, 12.8%, 30% pure by HPLC). MS: m/z=486.12 [M+H]$^+$.

1926

7-Amino-1-(2-chlorophenyl)-2-(2,4-dimethoxybenzyl)-1-hydroxy-6-methoxy-1,2-dihydro-3H-pyrrolo[3,4-c]pyridin-3-one

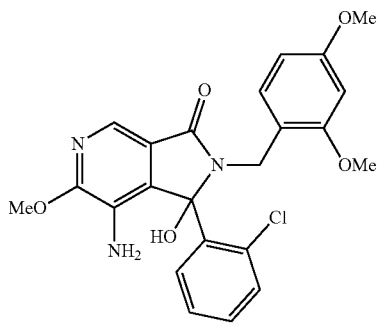 [SMILES: COc1ccc(CN2C(=O)c3cnc(OC)c([N+](=O)[O-])c3C2(O)c2ccccc2Cl)c(OC)c1]

Step 3: A solution of 1-(2-chlorophenyl)-2-(2,4-dimethoxybenzyl)-6-methoxy-7-nitro-1,2-dihydro-3H-pyrrolo[3,4-c]pyridin-3-one as prepared in the previous step (300 mg, 0.6174 mmol) in MeOH (4 mL) and AcOH (2 mL) was cooled to 0° C., and iron (172 mg, 3.08 mmol) was added. The mixture was warmed to RT, then heated at 80° C. for 1 h. The mixture was partitioned between EtOAc and water, then filtered through a pad of celite to remove any solids. The layers were separated layers, and the organic layer was washed with brine, dried over Na$_2$SO$_4$, filtered, and concentrated. The resulting 7-amino-1-(2-chlorophenyl)-2-(2,4-dimethoxybenzyl)-1-hydroxy-6-methoxy-1,2-dihydro-3H-pyrrolo[3,4-c]pyridin-3-one (35% pure by LCMS) was used directly in the next step without further purification.

N-(1-(2-Chlorophenyl)-2-(2,4-dimethoxybenzyl)-1-hydroxy-6-methoxy-3-oxo-2,3-dihydro-1H-pyrrolo[3,4-c]pyridin-7-yl)-3-fluoro-5-(trifluoromethyl)benzamide

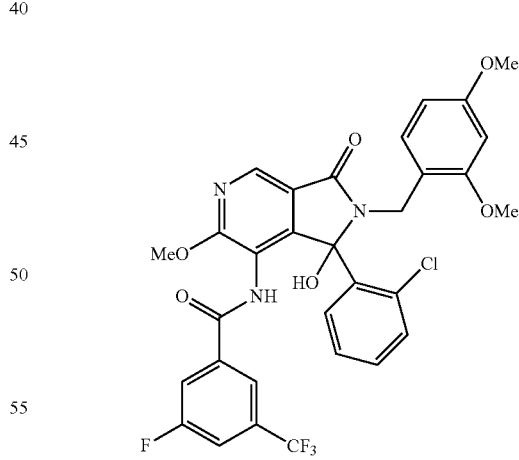

Step 4: A suspension of 3-fluoro-5-(trifluoromethyl)benzoic acid (94.6 mg, 0.4546 mmol) in DCE (5 mL) was treated with (1-chloro-2-methylprop-1-en-1-yl)dimethylamine (60.7 mg, 0.4546 mmol). The mixture was stirred at RT for 15 min, before it was transferred to a solution of 7-amino-1-(2-chlorophenyl)-2-(2,4-dimethoxybenzyl)-1-hydroxy-6-methoxy-1,2-dihydro-3H-pyrrolo[3,4-c]pyridin-3-one as prepared in the previous step (100 mg, 0.2273 mmol), DMAP (8.74 mg, 0.0227 mmol), and pyridine (90.9

µL, 1.13 mmol) in DCE (5 mL). The mixture was stirred at 60° C. for 16 h. The mixture was concentrated and the resulting N-(1-(2-chlorophenyl)-2-(2,4-dimethoxybenzyl)-1-hydroxy-6-methoxy-3-oxo-2,3-dihydro-1H-pyrrolo[3,4-c]pyridin-7-yl)-3-fluoro-5-(trifluoromethyl)benzamide was used in the next step without further purification.

N-(1-(2-chlorophenyl)-6-methoxy-3-oxo-2,3-dihydro-1H-pyrrolo[3,4-c]pyridin-7-yl)-3-fluoro-5-(trifluoromethyl)benzamide

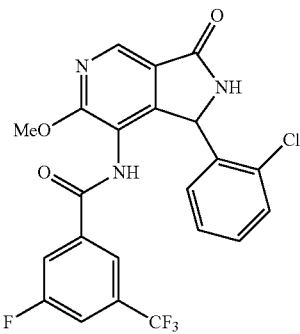 [SMILES: COc1ncc2c(c1NC(=O)c1cc(F)cc(C(F)(F)F)c1)C(c1ccccc1Cl)NC2=O]

Step 5: N-(1-(2-chlorophenyl)-2-(2,4-dimethoxybenzyl)-1-hydroxy-6-methoxy-3-oxo-2,3-dihydro-1H-pyrrolo[3,4-c]pyridin-7-yl)-3-fluoro-5-(trifluoromethyl)benzamide as prepared in the previous step was dissolved in TFA (1 mL) and stirred at 80° C. for 30 min. The mixture was cooled to room temperature, triethylsilane (108 µL, 0.682 mmol) was added, and the mixture was heated at 80° C. for 30 min. The mixture was concentrated, and the residue was purified by reverse phase purification to give N-(1-(2-chlorophenyl)-6-methoxy-3-oxo-2,3-dihydro-1H-pyrrolo[3,4-c]pyridin-7-yl)-3-fluoro-5-(trifluoromethyl)benzamide (6 mg, 0.01250 mmol, 5.50% from step 2) as a white solid.

Example 67

6-([1,2,4]triazolo[1,5-a]pyridin-6-yl)-3-(2-chloro-5-fluorophenyl)-4-(piperidin-3-ylamino)isoindolin-1-one (I-2158)

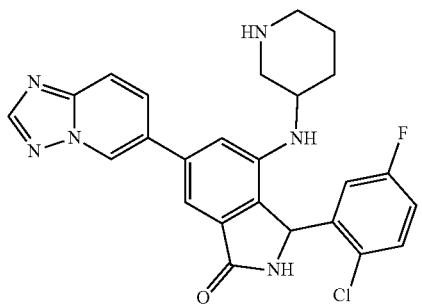 [SMILES: O=C1NC(c2cc(F)ccc2Cl)c2c(NC3CCCNC3)cc(-c3ccc4ncnn4c3)cc21]

tert-butyl 3-((6-([1,2,4]triazolo[1,5-a]pyridin-6-yl)-3-(2-chloro-5-fluorophenyl)-2-(4-methoxybenzyl)-1-oxoisoindolin-4-yl)amino)piperidine-1-carboxylate

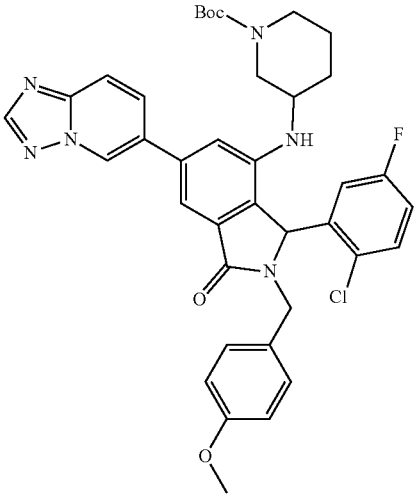 [SMILES: COc1ccc(CN2C(=O)c3cc(-c4ccc5ncnn5c4)cc(NC4CCCN(C(=O)OC(C)(C)C)C4)c3C2c2cc(F)ccc2Cl)cc1]

Step 1: A 25 mL microwave vial equipped with a stir bar was charged with 4-bromo-3-(2-chloro-5-fluorophenyl)-2-[(4-methoxyphenyl)methyl]-6-{[1,2,4]triazolo[1,5-a]pyridin-6-yl}-2,3-dihydro-1H-isoindol-1-one (300 mg, 0.5191 mmol), Pd₂dba₃ (47.5 mg, 0.05191 mmol), DavePhos (40.8 mg, 0.1038 mmol), sodium tert-butoxide (148 mg, 1.55 mmol) and tert-butyl 3-aminopiperidine-1-carboxylate (187 µL, 2 eq) before diluting with toluene (4 mL). The mixture was sparged with nitrogen before sealing and heating at 110° C. for 1 h. After concentration in vacuo, the mixture was subjected to reverse phase C18 chromatography and lyophilized to afford tert-butyl 3-((6-([1,2,4]triazolo[1,5-a]pyridin-6-yl)-3-(2-chloro-5-fluorophenyl)-2-(4-methoxybenzyl)-1-oxoisoindolin-4-yl)amino)piperidine-1-carboxylate (150 mg, 0.22 mmol, 41.5% yield).

6-([1,2,4]triazolo[1,5-a]pyridin-6-yl)-3-(2-chloro-5-fluorophenyl)-4-(piperidin-3-ylamino)isoindolin-1-one

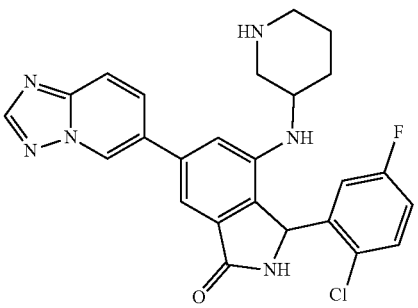 [SMILES: O=C1NC(c2cc(F)ccc2Cl)c2c(NC3CCCNC3)cc(-c3ccc4ncnn4c3)cc21]

Step 2: A 20 mL sealed tube equipped with a stir bar was charged with tert-butyl 3-{[3-(2-chloro-5-fluorophenyl)-2-[(4-methoxyphenyl)methyl]-1-oxo-6-{[1,2,4]triazolo[1,5-a]pyridin-6-yl}-2,3-dihydro-1H-isoindol-4-yl]amino}piperidine-1-carboxylate (150 mg, 0.2151 mmol) followed by dilution in trifluoroacetic acid (20 mL) and addition of trifluoromethanesulfonic acid (28.4 μL, 1.5 eq). The vial was sealed and heated at 90° C. for 1 h. The mixture was diluted with DCM and concentrated, subjected to reverse-phase chromotography (C18-30 g), and lyophilized to afford 6-([1,2,4]triazolo[1,5-a]pyridin-6-yl)-3-(2-chloro-5-fluorophenyl)-4-(piperidin-3-ylamino)isoindolin-1-one (20 mg, 0.042 mmol, 19.6% yield). MS: m/z=477.0 [M+H]$^+$.

Example 68

(S)—N-[3-(2-chloro-5-fluorophenyl)-1-oxo-6-{[1,2,4]triazolo[1,5-a]pyridin-6-yl}-2,3-dihydro-1H-isoindol-4-yl]-3-fluoro-5-(trifluoromethyl)benzamide (I-943) and (R)—N-[3-(2-chloro-5-fluorophenyl)-1-oxo-6-{[1,2,4]triazolo[1,5-a]pyridin-6-yl}-2,3-dihydro-1H-isoindol-4-yl]-3-fluoro-5-(trifluoromethyl)benzamide (I-945)

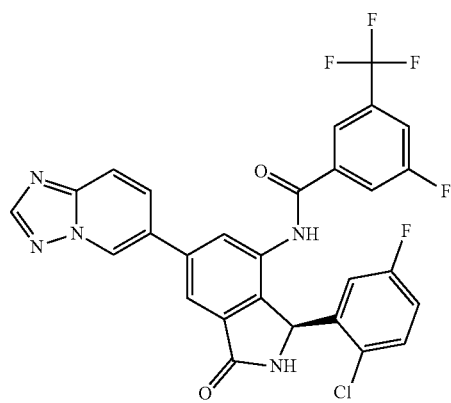

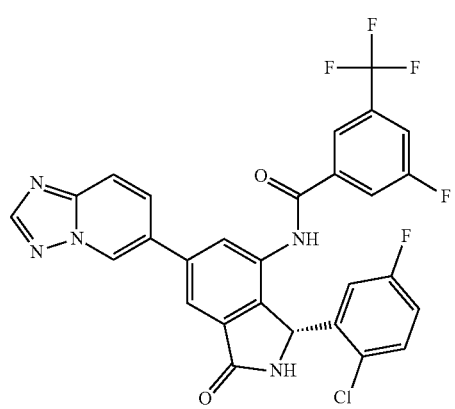 [SMILES: O=C(Nc1cc(-c2ccc3ncnn3c2)cc2c1C(c1cc(F)ccc1Cl)NC2=O)c1cc(F)cc(C(F)(F)F)c1]

N-[3-(2-chloro-5-fluorophenyl)-1-oxo-6-{[1,2,4]triazolo[1,5-a]pyridin-6-yl}-2,3-dihydro-1H-isoindol-4-yl]-3-fluoro-5-(trifluoromethyl)benzamide

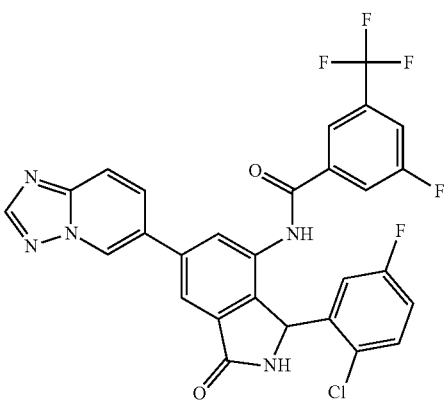

Step 1: A N$_2$-degassed mixture of N-[6-bromo-3-(2-chloro-5-fluorophenyl)-1-oxo-2,3-dihydro-1H-isoindol-4-yl]-3-fluoro-5-(trifluoromethyl)benzamide (32.1 mg), 6-(4,4,5,5-tetramethyl-1,3,2-dioxaborolan-2-yl)-[1,2,4]triazolo[1,5-a]pyridine (23.0 mg), palladium(II) bis(triphenylphosphane) dichloride (6.18 mg), disodium carbonate (18.6 mg) in acetonitrile (1.17 mL)/water (0.4 mL) was stirred in a sealed tube for 40 minutes at 110° C. The mixture was cooled, diluted with THF (10 mL) and brine (8 mL), and the layers were separated. The organic layer was concentrated. The crude was loaded as a silica gel slurry onto a 12 g silica gel column, which was eluted with DCM to 10:90:1 MeOH/DCM/NH$_4$OH gradient over 25 minutes. The product eluted between 5.5% and 6.2% MeOH/DCM. The fractions containing product were combined, concentrated in vacuo, and dried to yield a foamy, white solid (25.0 mg). MS: m/z=584.0 [M+H]$^+$. $^1$H NMR (400 MHz, DMSO-d$_6$) δ 10.65 (s, 1H), 9.48 (s, 1H), 9.34-9.26 (br s, 1H), 8.58 (s, 2H), 8.34 (s, 2H), 8.00 (m, 3H), 7.97 (m, 1H), 7.76 (d, J=7.6 Hz, 1H), 7.59 (s, 1H), 7.42 (t, J=7.7 Hz, 1H), 6.04 (br s, 1H).

(S)—N-[3-(2-chloro-5-fluorophenyl)-1-oxo-6-{[1,2,4]triazolo[1,5-a]pyridin-6-yl}-2,3-dihydro-1H-isoindol-4-yl]-3-fluoro-5-(trifluoromethyl)benzamide (I-943) and (R)—N-[3-(2-chloro-5-fluorophenyl)-1-oxo-6-{[1,2,4]triazolo[1,5-a]pyridin-6-yl}-2,3-dihydro-1H-isoindol-4-yl]-3-fluoro-5-(trifluoromethyl)benzamide (I-945)

Step 2: 90.3 mg of the racemate from step 1 (combined over multiple reaction runs) was subjected to chiral separation by SFC (method: Column: ChiralPak AS-H 30×250 mm Mobile Phase: 55% methanol in CO$_2$; Flow Rate: 80 mL/min; Sample: 90.3 mg of sample was dissolved in 10 mL methanol+10 mL dichloromethane; Injection: 2.5 mL; Detection: 220 nm). Separation yielded two peaks.

Peak1 (retention time: 0.66 min): (S)—N-[3-(2-chloro-5-fluorophenyl)-1-oxo-6-{[1,2,4]triazolo[1,5-a]pyridin-6-yl}-2,3-dihydro-1H-isoindol-4-yl]-3-fluoro-5-(trifluoromethyl)benzamide was isolated as a white solid in 100% LC purity and 100% in chiral purity (38.8 mg). MS: m/z=584.3 [M+H]$^+$. $^1$H NMR (DMSO-d$_6$, 400 MHz): δ=10.64 (s, 1H), 9.48 (s, 1H), 9.26 (br s, 1H), 8.58 (s, 1H), 8.10-8.19 (m, 2H), 7.99 (br d, J=9.9 Hz, 3H), 7.75-7.83 (m, 1H), 7.73 (s, 1H), 7.35 (dd, J=8.8, 5.3 Hz, 1H), 7.12 (td, J=8.3, 3.0 Hz, 1H), 6.51-6.97 (m, 1H), 6.07 (br s, 1H).

Peak 2 (retention time: 2.48 min): (R)—N-[3-(2-chloro-5-fluorophenyl)-1-oxo-6-{[1,2,4]triazolo[1,5-a]pyridin-6-yl}-2,3-dihydro-1H-isoindol-4-yl]-3-fluoro-5-(trifluoromethyl)benzamide was isolated as a white solid in 100% LC purity and 99.89% in chiral purity (37.6 mg). MS: m/z=584.3 [M+H]⁺. ¹H NMR (DMSO-d₆, 400 MHz): δ=10.64 (s, 1H), 9.48 (s, 1H), 9.26 (br s, 1H), 8.58 (s, 1H), 8.10-8.19 (m, 2H), 7.99 (br d, J=9.9 Hz, 3H), 7.75-7.83 (m, 1H), 7.73 (s, 1H), 7.35 (dd, J=8.8, 5.3 Hz, 1H), 7.12 (td, J=8.3, 3.0 Hz, 1H), 6.51-6.97 (m, 1H), 6.07 ppm (br s, 1H).

Example 69

(S)—N-(3-(2-chloro-5-fluorophenyl)-6-(5-cyano-[1,2,4]triazolo[1,5-a]pyridin-6-yl)-1-oxoisoindolin-4-yl)-3-fluoro-5-(trifluoromethyl)benzamide (I-1647) and (R)—N-(3-(2-chloro-5-fluorophenyl)-6-(5-cyano-[1,2,4]triazolo[1,5-a]pyridin-6-yl)-1-oxoisoindolin-4-yl)-3-fluoro-5-(trifluoromethyl)benzamide (I-1648)

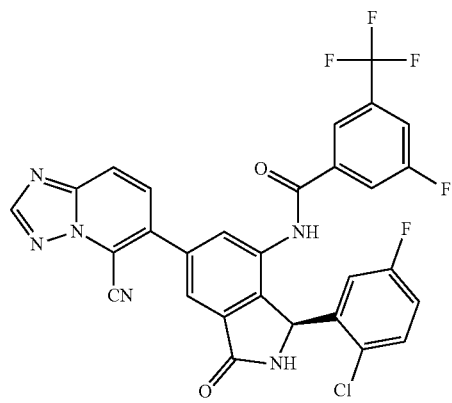

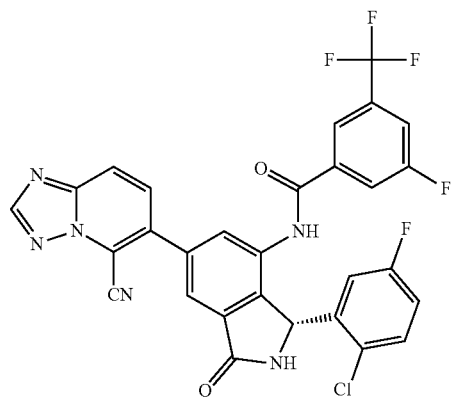 [SMILES: N#Cc1c(-c2cc(NC(=O)c3cc(F)cc(C(F)(F)F)c3)c3c(c2)C(=O)NC3c2cc(F)ccc2Cl)ccc2ncnn12]

N-(3-(2-chloro-5-fluorophenyl)-6-(5-cyano-[1,2,4]triazolo[1,5-a]pyridin-6-yl)-1-oxoisoindolin-4-yl)-3-fluoro-5-(trifluoromethyl)benzamide

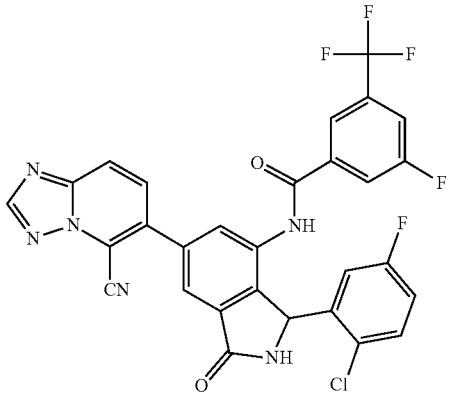

Step 1: To a sealed tube fitted with stir bar were added [1-(2-chloro-5-fluorophenyl)-7-[3-fluoro-5-(trifluoromethyl)benzamido]-3-oxo-2,3-dihydro-1H-isoindol5-yl]boronic acid (50 mg, 0.09792 mmol), 6-bromo-[1,2,4]triazolo[1,5-a]pyridine-5-carbonitrile (21.8 mg, 0.09792 mmol), palladium(II) bis(triphenylphosphane) dichloride (10.3 mg, 0.01468 mmol), acetonitrile (2 mL, 0.05M), and a solution of disodium carbonate (31.1 mg, 0.2937 mmol) in water (0.65 mL). The mixture was degassed with nitrogen for 30 seconds, and the tube was sealed. The reaction was heated at 90° C. for 45 min. The reaction was cooled to RT, filtered through a pad of Celite®, and concentrated. The residue was purified on prep-HPLC (AccQ Prep; eluting with 30-60% acetonitrile in water w/0.1% formic acid). Combined fractions containing product were concentrated in vacuo to yield a solid (10 mg, 15.9% yield). MS: m/z=609.08 [M+H]⁺. ¹H NMR (500 MHz, DMSO-d₆) δ 10.71 (s, 1H), 9.33 (s, 1H), 8.79 (s, 1H), 8.33 (d, J=9.2 Hz, 1H), 8.06 (s, 1H), 7.98 (d, J=9.3 Hz, 1H), 7.95 (d, J=7.7 Hz, 1H), 7.83 (s, 1H), 7.75 (d, J=9.1 Hz, 1H), 7.68 (s, 1H), 7.35 (dd, J=8.9, 5.1 Hz, 1H), 7.12 (td, J=8.4, 3.1 Hz, 1H), 6.54 (s, 1H), 6.08 (s, 1H).

(S)—N-(3-(2-chloro-5-fluorophenyl)-6-(5-cyano-[1,2,4]triazolo[1,5-a]pyridin-6-yl)-1-oxoisoindolin-4-yl)-3-fluoro-5-(trifluoromethyl)benzamide (I-1647) and (R)—N-(3-(2-chloro-5-fluorophenyl)-6-(5-cyano-[1,2,4]triazolo[1,5-a]pyridin-6-yl)-1-oxoisoindolin-4-yl)-3-fluoro-5-(trifluoromethyl)benzamide (I-1648)

Step 2: 100.0 mg of the racemate from step 1 (combined over multiple reaction runs) was subjected to chiral separation by SFC (method: UniChiral AS-5H 21×250 mm; Mobile Phase: 60% ethanol in CO₂; Flow Rate: 70 mL/min; Sample: 100.0 mg of sample was dissolved in 5 mL methanol+5 mL dichloromethane; Injection: 2.5 mL; Detection: 254 nm). Separation yielded two peaks.

Peak 1 (retention time: 0.83 min): (S)—N-(3-(2-chloro-5-fluorophenyl)-6-(5-cyano-[1,2,4]triazolo[1,5-a]pyridin-6-yl)-1-oxoisoindolin-4-yl)-3-fluoro-5-(trifluoromethyl)benzamide was isolated as a solid (40 mg). MS: m/z=609.1 [M+H]⁺. ¹H NMR (500 MHz, DMSO-d₆) δ 10.71 (s, 1H), 9.33 (s, 1H), 8.80 (s, 1H), 8.34 (d, J=9.2 Hz, 1H), 8.07 (s, 1H), 7.97 (t, J=9.9 Hz, 2H), 7.83 (s, 1H), 7.75 (d, J=9.2 Hz, 1H), 7.68 (s, 1H), 7.35 (dd, J=8.8, 5.1 Hz, 1H), 7.13 (d, J=8.0 Hz, 1H).

Peak 2 (retention time: 3.11 min): (R)—N-(3-(2-chloro-5-fluorophenyl)-6-(5-cyano-[1,2,4]triazolo[1,5-a]pyridin-6-yl)-1-oxoisoindolin-4-yl)-3-fluoro-5-(trifluoromethyl)benzamide was isolated as a solid (43 mg). MS: m/z=609.1 [M+H]$^+$. $^1$H NMR (500 MHz, DMSO-d$_6$) δ 10.71 (s, 1H), 9.33 (s, 1H), 8.80 (s, 1H), 8.34 (d, J=9.2 Hz, 1H), 8.07 (s, 1H), 7.97 (t, J=9.9 Hz, 2H), 7.83 (s, 1H), 7.75 (d, J=9.2 Hz, 1H), 7.68 (s, 1H), 7.35 (dd, J=8.8, 5.1 Hz, 1H), 7.13 (d, J=8.0 Hz, 1H).

Example 70

(S)—N-(3-(2-chloro-5-fluorophenyl)-6-(1-(difluoromethyl)-1H-pyrazol-4-yl)-1-oxoisoindolin-4-yl)-3-fluoro-5-(trifluoromethyl)benzamide (I-1739) and (R)—N-(3-(2-chloro-5-fluorophenyl)-6-(1-(difluoromethyl)-1H-pyrazol-4-yl)-1-oxoisoindolin-4-yl)-3-fluoro-5-(trifluoromethyl)benzamide (I-1740)

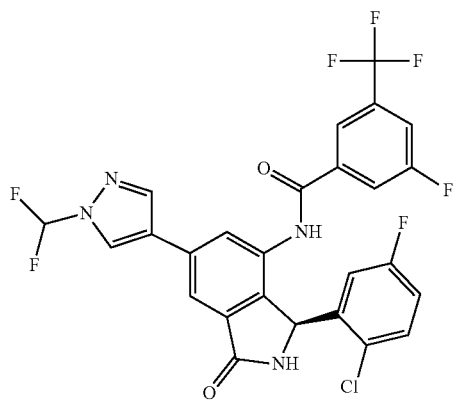

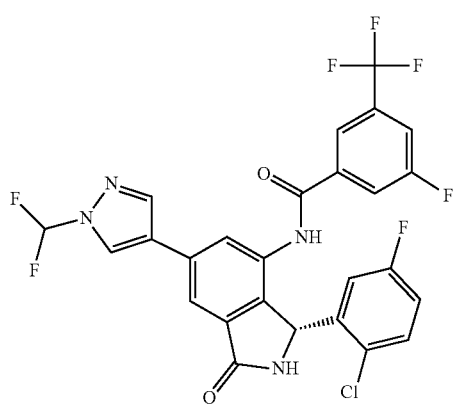

N-(3-(2-chloro-5-fluorophenyl)-6-(5-cyano-[1,2,4]triazolo[1,5-a]pyridin-6-yl)-1-oxoisoindolin-4-yl)-3-fluoro-5-(trifluoromethyl)benzamide

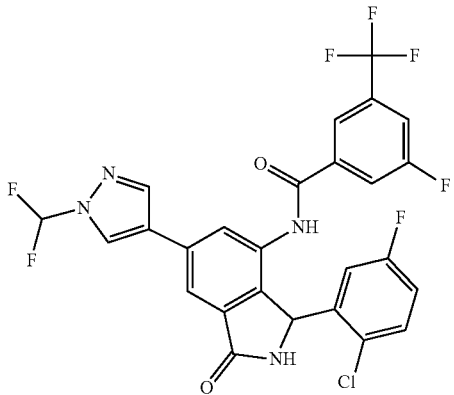 [SMILES: O=C(Nc1cc(-c2cnn(C(F)F)c2)cc2c1C(c1cc(F)ccc1Cl)NC2=O)c1cc(F)cc(C(F)(F)F)c1]

Step 1: To a sealed tube fitted with stir bar were added N-[6-bromo-3-(2-chloro-5-fluorophenyl)-1-oxo-2,3-dihydro-1H-isoindol-4-yl]-3-fluoro-5-(trifluoromethyl)benzamide (350 mg, 0.641 mmol, 1 eq), 1-(difluoromethyl)-4-(4,4,5,5-tetramethyl-1,3,2-dioxaborolan-2-yl)-1H-pyrazole (211 mg, 0.865 mmol, 1.35 eq), bis(triphenylphosphine)palladium (II) dichloride (67.4 mg, 0.096 mmol, 0.15 eq), dioxane (4.3 mL, 0.15M), and a solution of sodium carbonate (203 mg, 1.92 mmol, 3.0 eq) in water (1.4 mL). The mixture was degassed with nitrogen for 30 seconds, and the tube was sealed. The reaction was stirred at 100° C. for a total of 55 minutes. The reaction was cooled to R.T. and treated with water (30 mL). A dark brown solid was isolated by filtration. The crude (>400 mg) was loaded as a silica gel slurry on a 24 g silica gel column, which was eluted with DCM to 10:90:1 MeOH/DCM/NH$_4$OH gradient over 25 minutes. The product eluted at ~3.8% MeOH/DCM. The fractions containing desired product were combined, concentrated, and dried to yield a tan solid (94.0 mg). MS: m/z=583.4 [M+H]$^+$. $^1$H NMR (400 MHz, DMSO-d$_6$) δ 10.56 (s, 1H), 9.18 (s, 1H), 8.94 (s, 1H), 8.43 (s, 1H), 8.06 (d, J=1.6 Hz, 1H), 8.02-7.79 (m, 3H), 7.75 (d, J=9.1 Hz, 1H), 7.70 (d, J=2.2 Hz, 1H), 7.31 (dd, J=8.9, 5.1 Hz, 1H), 7.09 (td, J=8.3, 3.1 Hz, 1H), 6.86-6.58 (m, 1H), 5.98 (s, 1H).

(S)—N-(3-(2-chloro-5-fluorophenyl)-6-(1-(difluoromethyl)-1H-pyrazol-4-yl)-1-oxoisoindolin-4-yl)-3-fluoro-5-(trifluoromethyl)benzamide (I-1739) and (R)—N-(3-(2-chloro-5-fluorophenyl)-6-(1-(difluoromethyl)-1H-pyrazol-4-yl)-1-oxoisoindolin-4-yl)-3-fluoro-5-(trifluoromethyl)benzamide (I-1740)

Step 2: 85.1 mg of the racemate from step 1 was subjected to chiral separation by SFC (Column: UniChiral AS-5H 21×250 mm; Mobile Phase: 45% methanol in CO$_2$; Flow Rate: 70 mL/min; Sample: 85.1 mg of sample was dissolved in 10 mL methanol+5 mL dichloromethane; Injection: 2.5 mL; Detection: 254 nm). Separation yielded two peaks.

Peak 1 (retention time: 0.45 min): (S)—N-(3-(2-chloro-5-fluorophenyl)-6-(1-(difluoromethyl)-1H-pyrazol-4-yl)-1-oxoisoindolin-4-yl)-3-fluoro-5-(trifluoromethyl)benzamide was isolated as a solid (42.8 mg). MS: m/z=583.4 [M+H]$^+$. $^1$H NMR (500 MHz, DMSO-d$_6$) δ 10.55 (s, 1H), 9.17 (s, 1H), 8.94 (s, 1H), 8.44 (s, 1H), 8.06 (d, J=1.5 Hz, 1H), 7.99-7.69 (m, 5H), 7.32 (dd, J=8.9, 5.1 Hz, 1H), 7.09 (td, J=8.4, 3.1 Hz, 1H), 6.92-6.41 (m, 1H), 5.99 (s, 1H).

Peak 2 (retention time: 0.74 min): (R)—N-(3-(2-chloro-5-fluorophenyl)-6-(1-(difluoromethyl)-1H-pyrazol-4-yl)-1-oxoisoindolin-4-yl)-3-fluoro-5-(trifluoromethyl)benzamide as a solid (23.4 mg). MS: m/z=583.4 [M+H]$^+$. $^1$H NMR (500 MHz, DMSO-d$_6$) δ 10.55 (s, 1H), 9.17 (s, 1H), 8.94 (s, 1H), 8.44 (s, 1H), 8.06 (d, J=1.5 Hz, 1H), 7.99-7.69 (m, 5H), 7.32 (dd, J=8.9, 5.1 Hz, 1H), 7.09 (td, J=8.4, 3.1 Hz, 1H), 6.92-6.41 (m, 1H), 5.99 (s, 1H).

Example 71

(S)—N-(3-(2-chloro-5-fluorophenyl)-6-(1-methyl-6-oxo-1,6-dihydropyridin-3-yl)-1-oxoisoindolin-4-yl)-3-fluoro-5-(trifluoromethyl)benzamide (I-701) and (R)—N-(3-(2-chloro-5-fluorophenyl)-6-(1-methyl-6-oxo-1,6-dihydropyridin-3-yl)-1-oxoisoindolin-4-yl)-3-fluoro-5-(trifluoromethyl)benzamide (I-702)

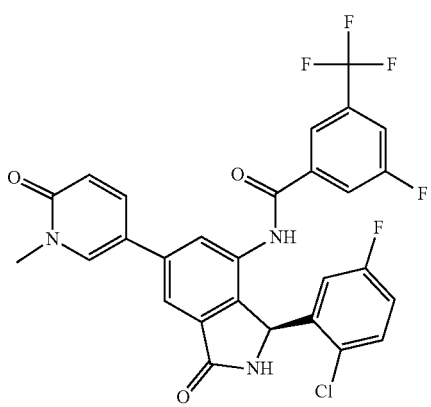

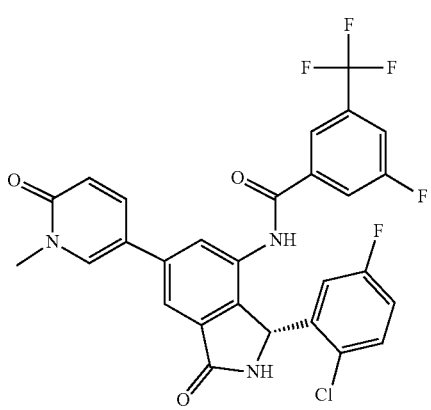

N-[3-(2-chloro-5-fluorophenyl)-2-[(4-methoxyphenyl)methyl]-6-(1-methyl-6-oxo-1,6-dihydropyridin-3-yl)-1-oxo-2,3-dihydro-1H-isoindol-4-yl]-3-fluoro-5-(trifluoromethyl)benzamide

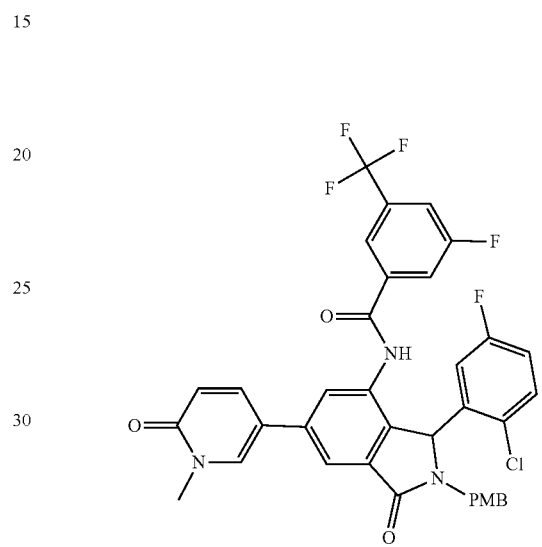

Step 1: A N$_2$-degassed mixture of N-[6-bromo-3-(2-chloro-5-fluorophenyl)-2-[(4-methoxyphenyl)methyl]-1-oxo-2,3-dihydro-1H-isoindol-4-yl]-3-fluoro-5-(trifluoromethyl)benzamide (140 mg), 1-methyl-5-(4,4,5,5-tetramethyl-1,3,2-dioxaborolan-2-yl)-1,2-dihydropyridin-2-one (83.6 mg), palladium(II) bis(triphenylphosphane) dichloride (22.0 mg), disodium carbonate (66.7 mg) in acetonitrile (4.19 mL)/water (1.40 mL) was stirred in a sealed tube for 40 minutes at 105° C. The mixture was cooled, diluted with THF (7-8 mL) and brine (10 mL), and the layers were separated. The organic layer was concentrated. The crude was loaded as a silica gel slurry onto a 24 g silica gel column, which was eluted with DCM to 10:90:1 MeOH/DCM/NH$_4$OH gradient over 20 minutes. The product eluted between 47% and 5.2% MeOH/DCM. The combined fractions were concentrated in vacuo and dried to yield an off-white/light gray-green, foamy solid weighing 114.1 mg. MS: m/z=694.7 [M+H]$^+$.

N-[3-(2-chloro-5-fluorophenyl)-6-(1-methyl-6-oxo-1,6-dihydropyridin-3-yl)-1-oxo-2,3-dihydro-1H-isoindol-4-yl]-3-fluoro-5-(trifluoromethyl)benzamide

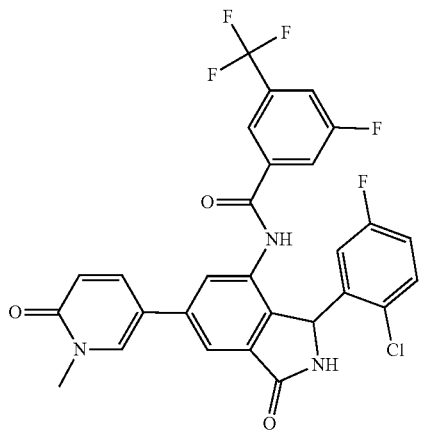 [SMILES: Cn1cc(-c2cc(NC(=O)c3cc(F)cc(C(F)(F)F)c3)c3c(c2)C(=O)NC3c2cc(F)ccc2Cl)ccc1=O]

Step 2: A mixture of N-[3-(2-chloro-5-fluorophenyl)-2-[(4-methoxyphenyl)methyl]-6-(1-methyl-6-oxo-1,6-dihydropyridin-3-yl)-1-oxo-2,3-dihydro-1H-isoindol-4-yl]-3-fluoro-5-(trifluor methyl)benzamide (114.1 mg) and 10% TFA in DCM (5.5 mL) was heated for 14 hours at 100° C. in microwave. After cooling, the mixture was concentrated and eluted on 12 gram silica gel column with DCM to 10:90:1 MeOH/DCM/NH$_4$OH. The product eluted between 6.1% and 6.7% MeOH/DCM, which was concentrated in vacuo and dried to yield 61.6 mg. MS: m/z=574.5 [M+H]$^+$; $^1$H NMR (400 MHz, DMSO-d$_6$) δ 10.90 (s, 1H), 9.52 (s, 1H), 8.62 (d, J=1.5 Hz, 1H), 8.18 (dd, J=8.6, 1.6 Hz, 1H), 7.98 (d, J=8.7, 1H), 7.87 (s, 1H), 7.75 (d, J=8.5, 1H), 7.67 (s, 1H), 7.35 (m, 1H), 7.10 (td, 8.6, 1.6 Hz, 1H), 6.57 (d, J=8.8 Hz, 1H), 6.02 (s, 1H), 3.59 (s, 3H).

(S)—N-(3-(2-chloro-5-fluorophenyl)-6-(1-methyl-6-oxo-1,6-dihydropyridin-3-yl)-1-oxoisoindolin-4-yl)-3-fluoro-5-(trifluoromethyl)benzamide (I-701) and
(R)—N-(3-(2-chloro-5-fluorophenyl)-6-(1-methyl-6-oxo-1,6-dihydropyridin-3-yl)-1-oxoisoindolin-4-yl)-3-fluoro-5-(trifluoromethyl)benzamide (I-702)

Step 3: 55 mg of the racemate from step 2 was subjected to chiral separation by SFC (method: Column: ChiralPak IC-H 21×250 mm; Mobile Phase: 40% methanol in CO$_2$; Flow Rate: 70 mL/min; Sample: 54.8 mg of sample was dissolved in 4 mL methanol+4 mL dichloromethane; Injection: 1 mL; Detection: 220 nm). Separation yielded two peaks.

Peak1 (retention time: 2.4 min): (S)—N-(3-(2-chloro-5-fluorophenyl)-6-(1-methyl-6-oxo-1,6-dihydropyridin-3-yl)-1-oxoisoindolin-4-yl)-3-fluoro-5-(trifluoromethyl)benzamide was isolated as a white solid in 100% LC purity and 100% in chiral purity (20.2 mg). MS: m/z=574.3 [M+H]$^+$; $^1$H NMR (400 MHz, DMSO-d$_6$) δ 10.90 (s, 1H), 9.52 (s, 1H), 8.62 (d, J=1.5 Hz, 1H), 8.18 (dd, J=8.6, 1.6 Hz, 1H), 7.98 (d, J=8.7, 1H), 7.87 (s, 1H), 7.75 (d, J=8.5, 1H), 7.67 (s, 1H), 7.35 (m, 1H), 7.10 (td, 8.6, 1.6 Hz, 1H), 6.57 (d, J=8.8 Hz, 1H), 6.02 (s, 1H), 3.59 (s, 3H).

Peak2 (retention time: 3.72 min): (R)—N-(3-(2-chloro-5-fluorophenyl)-6-(1-methyl-6-oxo-1,6-dihydropyridin-3-yl)-1-oxoisoindolin-4-yl)-3-fluoro-5-(trifluoromethyl)benzamide was isolated as a white solid in 100% LC purity and 100% in chiral purity (20.1 mg). MS: m/z=574.2 [M+H]$^+$; $^1$H NMR (400 MHz, DMSO-d$_6$) δ 10.90 (s, 1H), 9.52 (s, 1H), 8.62 (d, J=1.5 Hz, 1H), 8.18 (dd, J=8.6, 1.6 Hz, 1H), 7.98 (d, J=8.7, 1H), 7.87 (s, 1H), 7.75 (d, J=8.5, 1H), 7.67 (s, 1H), 7.35 (m, 1H), 7.10 (td, 8.6, 1.6 Hz, 1H), 6.57 (d, J=8.8 Hz, 1H), 6.02 (s, 1H), 3.59 (s, 3H).

Example 72

4-Amino-2-chloro-6-(2,4-dimethoxybenzyl)-5-(o-tolyl)-5,6-dihydro-7H-pyrrolo[3,4-b]pyridin-7-one

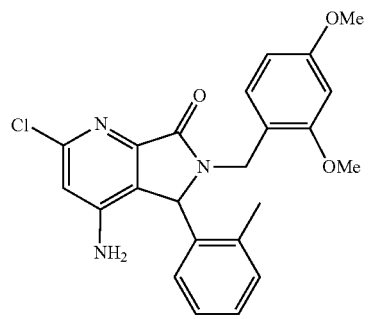 [SMILES: COc1ccc(CN2C(=O)c3nc(Cl)cc(N)c3C2c2ccccc2C)c(OC)c1]

4,6-Dichloro-N-(2,4-dimethoxybenzyl)picolinamide

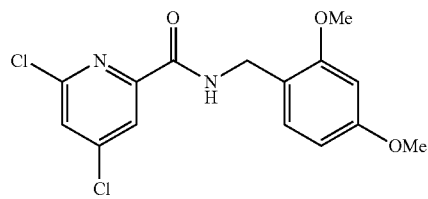 [SMILES: COc1ccc(CNC(=O)c2cc(Cl)cc(Cl)n2)c(OC)c1]

Step 1: To a solution of 4,6-dichloropicolinic acid (50.0 g, 260 mmol, 1.00 eq) in DCM (250 mL) was added CDT (44.3 g, 273 mmol, 1.05 eq) and DMAP (1.59 g, 13.02 mmol, 0.05 eq), and the mixture was stirred at 45° C. for 2 h. Then the mixture was cooled to 15° C., and a solution of 2,4-dimethoxybenzylamine (43.5 g, 260 mmol, 39.2 mL, 1.00 eq) in DCM (50 mL) was added. The mixture was stirred at 15° C. for 5 h. Water (700 mL) was added, and the mixture was extracted with DCM (3×300 mL). The organic phase was adjusted to pH=4 with 1M HCl, and extracted with DCM (300 mL). The combined organic layers were washed with satd. NaCl (50 mL), dried over Na$_2$SO$_4$, filtered, and concentrated under reduced pressure to afford 4,6-dichloro-N-(2,4-dimethoxybenzyl)picolinamide (68.0 g, 165 mmol, 63.5% yield, 83.0% purity) as a white solid. MS: m/z=341.0 [M+H]$^1$; $^1$H NMR (400 MHz, CDCl$_3$) δ 8.15 (s, 1H), 8.14 (s, 1H), 7.45 (d, J=0.8 Hz, 1H), 7.26 (t, J=7.2 Hz, 1H), 6.50-6.42 (m, 2H), 3.88 (s, 3H), 3.80 (s, 3H).

4,6-Dichloro-N-(2,4-dimethoxybenzyl)-N-(2-methylbenzoyl)picolinamide

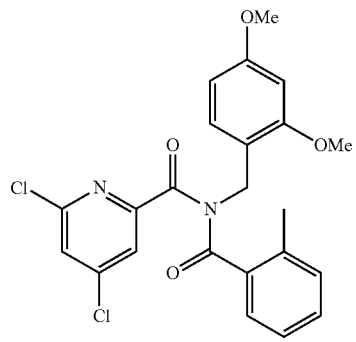 [SMILES: COc1ccc(CN(C(=O)c2cc(Cl)cc(Cl)n2)C(=O)c2ccccc2C)c(OC)c1]

Step 2: To a suspension of NaH (10.6 g, 264 mmol, 60% purity, 1.50 eq) in THF (300 mL) at 0° C. under N₂ was added 4,6-dichloro-N-(2,4-dimethoxybenzyl)picolinamide (60.0 g, 176 mmol, 1.00 eq) in THF (100 mL). The mixture was stirred at 0° C. for 0.5 h. Then, 2-methylbenzoyl chloride (28.8 g, 186 mmol, 24.2 mL, 1.06 eq) was added dropwise at 0° C., and the mixture was stirred at 0° C. for 2 h. The mixture was quenched with 1.0 L of NH₄Cl and extracted with ethyl acetate (3×500 mL). The combined organic layers were washed with brine, dried over Na₂SO₄, and concentrated. The residue was purified by silica gel column chromatography (petroleum ether:ethyl acetate=100:0 to 100:6) to afford 4,6-dichloro-N-(2,4-dimethoxybenzyl)-N-(2-methylbenzoyl)picolinamide (35.0 g, 64.7 mmol, 36.8 yield, 84.9% purity) as a brown oil. MS: m/z=483.1 [M+Na]; ¹H NMR (400 MHz, CDCl₃) δ 7.40 (d, J=4.2 Hz, 1H), 7.37 (d, J=0.8 Hz, 1H), 7.18-7.16 (m, 3H), 7.02-7.00 (m, 2H), 6.48 (d, J=4.2 Hz, 1H), 6.41 (d, J=1.2 Hz, 1H), 5.12 (s, 2H), 3.80 (s, 3H), 3.66 (s, 3H), 2.44 (s, 3H).

2,4-Dichloro-6-(2,4-dimethoxybenzyl)-5-hydroxy-5-(o-tolyl)-5,6-dihydro-7H-pyrrolo[3,4-b]pyridin-7-one

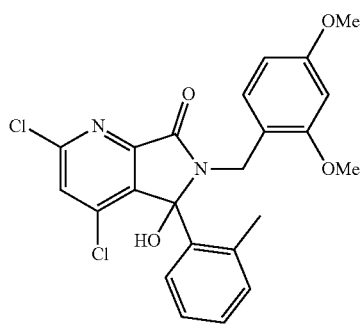 [SMILES: COc1ccc(CN2C(=O)c3nc(Cl)cc(Cl)c3C2(O)c2ccccc2C)c(OC)c1]

Step 3: To a solution of 4,6-dichloro-N-(2,4-dimethoxybenzyl)-N-(2-methylbenzoyl)picolinamide (44.8 g, 97.4 mmol, 1.00 eq) in THF (450 mL) at −50° C. was added LiHMDS (1 M, 146 mL, 1.50 eq). The solution was stirred at −50° C. for 3 h. The mixture was quenched with saturated NH₄Cl solution (1.0 L) and extracted with ethyl acetate (2×500 mL). The organic layers were combined, washed with brine (500 mL), dried, and concentrated. The residue was purified by silica gel column chromatography (petroleum ether:ethyl acetate=100:1 to 100:11) to afford 2,4-dichloro-6-(2,4-dimethoxybenzyl)-5-hydroxy-5-(o-tolyl)-5,6-dihydro-7H-pyrrolo[3,4-b]pyridin-7-one (29.0 g, 33.5 mmol, 34.3% yield, 53.0% purity) as a yellow oil. MS: m/z=459.0 [M+H]⁺; ¹H NMR (400 MHz, DMSO-d₆) δ 8.99 (t, J=6.2 Hz, 1H), 8.21 (s, 1H), 7.35 (s, 1H), 7.23 (d, J=3.6 Hz, 1H), 7.16 (d, J=4.0 Hz, 1H) 6.88 (d, J=4.0 Hz, 1H), 6.55 (d, J=1.2 Hz, 1H), 6.53-6.50 (m, 3H), 4.24 (d, J=3.2 Hz, 2H), 3.80 (s, 3H), 3.70 (s, 3H), 2.64 (s, 3H).

2,4-Dichloro-6-(2,4-dimethoxybenzyl)-5-(o-tolyl)-5,6-dihydro-7H-pyrrolo[3,4-b]pyridin-7-one

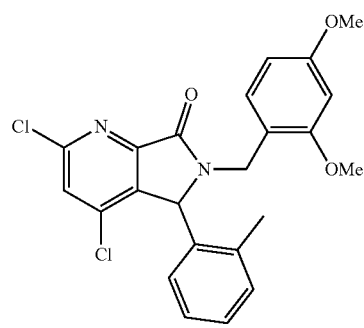 [SMILES: COc1ccc(CN2C(=O)c3nc(Cl)cc(Cl)c3C2c2ccccc2C)c(OC)c1]

Step 4: To a solution of 2,4-dichloro-6-(2,4-dimethoxybenzyl)-5-hydroxy-5-(o-tolyl)-5,6-dihydro-7H-pyrrolo[3,4-b]pyridin-7-one (28.0 g, 32.3 mmol, 1.00 eq) and TFA (92.1 g, 808 mmol, 59.8 mL, 25.0 eq) in DCM (280 mL) was added Et₃SiH (37.6 g, 323 mmol, 51.6 mL, 10.0 eq) at 20° C. The solution was stirred at 25° C. for 12 h. The mixture was concentrated. The crude product was purified by prep-HPLC (TFA condition) to give 2,4-dichloro-6-(2,4-dimethoxybenzyl)-5-(o-tolyl)-5,6-dihydro-7H-pyrrolo[3,4-b]pyridin-7-one (7.85 g, 17.5 mmol, 54.3% yield, 99.0% purity) as a brown solid. MS: m/z=443.0 [M+H]⁺; ¹H NMR (400 MHz, DMSO-d₆) δ 7.95 (s, 1H), 7.23, (s, 1H), 7.09-7.08 (m, 1H), 6.95 (d, J=4.2 Hz, 1H), 6.57 (d, J=5.8 Hz, 1H) 6.51 (s, 1H), 6.50-6.44 (m, 1H), 5.78 (s, 1H), 4.80 (d, J=7.6 Hz, 1H), 3.77 (s, 1H), 3.74 (s, 3H), 3.65 (s, 3H), 2.22 (s, 3H).

2-Chloro-6-(2,4-dimethoxybenzyl)-4-((2,4-dimethoxybenzyl)amino)-5-(o-tolyl)-5,6-dihydro-7H-pyrrolo[3,4-b]pyridin-7-one and 4-Chloro-6-(2,4-dimethoxybenzyl)-2-((2,4-dimethoxybenzyl)amino)-5-(o-tolyl)-5,6-dihydro-7H-pyrrolo[3,4-b]pyridin-7-one

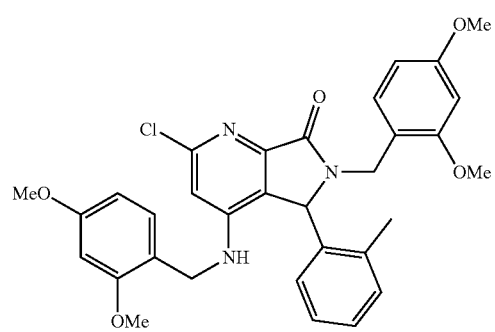

-continued

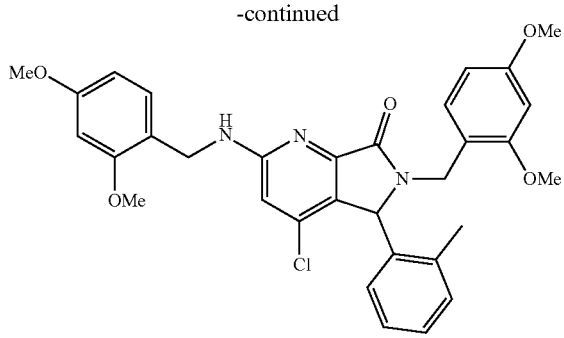

Step 5: To a solution of 2,4-dichloro-6-(2,4-dimethoxybenzyl)-5-(o-tolyl)-5,6-dihydro-7H-pyrrolo[3,4-b]pyridin-7-one (3.92 g, 8.84 mmol, 1.00 eq) in i-PrOH (25.0 mL) was added compound 2,4-dimethoxybenzylamine (2.22 g, 13.3 mmol, 2.00 mL, 1.50 eq) and DIPEA (3.43 g, 26.5 mmol, 4.62 mL, 3.00 eq) in a sealed tube. The mixture was stirred at 160° C. for 5 h. The mixture was concentrated. The residue was purified by prep-HPLC (Column: Phenomenex Luna C18 (250*80 mm*15 µm); Mobile phase: 56%-86% CH₃CN in water (0.1% TFA) over 20 min) to afford 2-chloro-6-(2,4-dimethoxybenzyl)-4-((2,4-dimethoxybenzyl)amino)-5-(o-tolyl)-5,6-dihydro-7H-pyrrolo[3,4-b]pyridin-7-one (4.79 g, 8.20 mmol, 46.4% yield, 98.24% purity) as a light yellow solid and 4-chloro-6-(2,4-dimethoxybenzyl)-2-((2,4-dimethoxybenzyl)amino)-5-(o-tolyl)-5,6-dihydro-7H-pyrrolo[3,4-b]pyridin-7-one (1.35 g, 2.28 mmol, 12.9% yield, 97.0% purity) as a yellow solid.

2-Chloro-6-(2,4-dimethoxybenzyl)-4-((2,4-dimethoxybenzyl)amino)-5-(o-tolyl)-5,6-dihydro-7H-pyrrolo[3,4-b]pyridin-7-one: MS: m/z=574.2 [M+H]⁺; ¹H NMR (400 MHz, DMSO-d₆) δ 7.50 (d, J=3.4 Hz, 1H), 7.29-7.25 (m, 2H), 7.14-7.10 (m, 1H), 7.00-6.84 (m, 1H), 6.70-6.63 (m, 2H) 6.52-6.43 (m, 4H), 5.76-5.38 (m, 2H), 4.79-4.67 (m, 1H), 4.16-4.14 (m, 2H), 3.74 (s, 3H), 3.70 (s, 3H), 3.69 (s, 3H), 3.66 (s, 3H), 2.21 (s, 2H), 1.55 (s, 1H).

4-Chloro-6-(2,4-dimethoxybenzyl)-2-((2,4-dimethoxybenzyl)amino)-5-(o-tolyl)-5,6-dihydro-7H-pyrrolo[3,4-b]pyridin-7-one: MS: m/z=574.4 [M+H]⁺; ¹H NMR (400 MHz, DMSO-d₆) δ 7.41 (s, 1H), 8.21 (s, 1H), 7.20-7.18 (m, 3H), 7.11-7.07 (m, 1H), 6.78 (d, J=3.2 Hz, 1H), 6.58 (s, 1H), 6.54 (s, 1H), 6.52-6.50 (m, 4H), 5.52 (s, 1H), 4.75 (d, J=7.6 Hz, 3H), 4.43 (s, 2H), 3.81 (s, 3H), 3.77 (s, 3H), 3.73 (s, 3H), 3.65 (s, 3H), 2.19 (s, 2H), 1.61 (s, 1H).

4-Amino-2-chloro-6-(2,4-dimethoxybenzyl)-5-(o-tolyl)-5,6-dihydro-7H-pyrrolo[3,4-b]pyridin-7-one

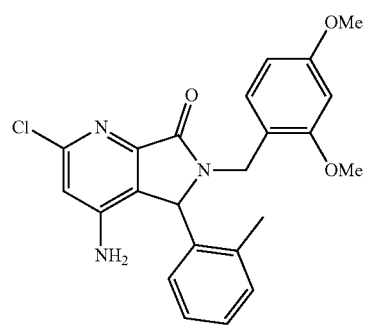 [SMILES: COc1ccc(CN2C(=O)c3nc(Cl)cc(N)c3C2c2ccccc2C)c(OC)c1]

Step 6: A solution of 2-chloro-6-(2,4-dimethoxybenzyl)-4-((2,4-dimethoxybenzyl)amino)-5-(o-tolyl)-5,6-dihydro-7H-pyrrolo[3,4-b]pyridin-7-one (3.60 g, 6.27 mmol, 1.00 eq) and TFA (17.9 g, 157 mmol, 11.6 mL, 25.0 eq) was stirred at 25° C. for 2 h. The mixture was poured into satd. Na₂CO₃ (200 mL) and filtered. The filtrate was extracted with ethyl acetate (2×150 mL). The combined organics were dried over Na₂SO₄ and concentrated. The residue was purified by reversed-phase HPLC (0.1% NH₃H₂O) to afford 4-amino-2-chloro-6-(2,4-dimethoxybenzyl)-5-(o-tolyl)-5,6-dihydro-7H-pyrrolo[3,4-b]pyridin-7-one (1.18 g, 2.76 mmol, 43.9% yield, 99.1% purity) as a white solid. MS: m/z=424.3 [M+H]⁺; ¹H NMR (400 MHz, DMSO-d₆) δ 7.51 (t, J=2.6 Hz, 1H), 7.28-7.20 (m, 2H), 7.11-7.08 (s, 1H), 6.98-6.84 (m, 1H), 6.86 (d, J=9.0 Hz, 1H) 6.53-6.51 (m, 1H), 6.46-6.44 (m, 1H), 5.87-5.80 (m, 2H), 5.48 (d, J=10.8 Hz, 1H), 4.80-4.66 (m, 1H), 3.74 (s, 3H), 3.70 (s, 3H), 2.24 (s, 2H), 1.59 (s, 1H).

Example 73

N-(5-(2-Chlorophenyl)-7-oxo-2-(1H-pyrazol-4-yl)-6,7-dihydro-5H-pyrrolo[3,4-b]pyridin-4-yl)benzo[d]isothiazole-3-carboxamide (I-94)

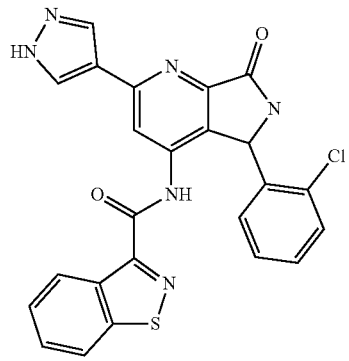 [SMILES: O=C1NC(c2ccccc2Cl)c2c(NC(=O)c3nsc4ccccc34)cc(-c3cn[nH]c3)nc21]

4-Amino-2-chloro-5-(2-chlorophenyl)-6-(4-methoxybenzyl)-5,6-dihydro-7H-pyrrolo[3,4-b]pyridin-7-one

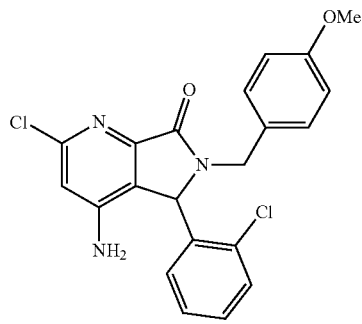 [SMILES: COc1ccc(CN2C(=O)c3nc(Cl)cc(N)c3C2c2ccccc2Cl)cc1]

Step 1 to 6: According to the procedures of Example 68, Steps 1 to 6, 4,6-dichloropicolinic acid, 4-methoxybenzylamine, and 2-chlorobenzoyl chloride were converted to 4-amino-2-chloro-5-(2-chlorophenyl)-6-(4-methoxybenzyl)-5,6-dihydro-7H-pyrrolo[3,4-b]pyridin-7-one. MS: m/z=414.3 [M+H]⁺.

N-[2-Chloro-5-(2-chlorophenyl)-6-[(4-methoxyphenyl)methyl]-7-oxo-5H,6H,7H-pyrrolo[3,4-b]pyridin-4-yl]-1,2-benzothiazole-3-carboxamide

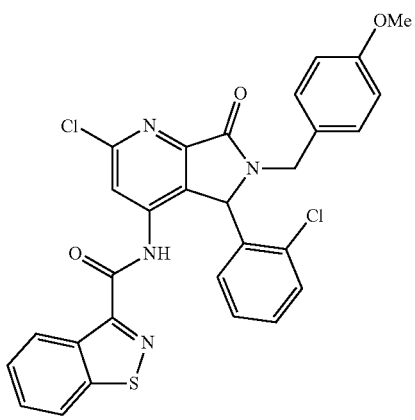 [SMILES: COc1ccc(CN2C(=O)c3nc(Cl)cc(NC(=O)c4nsc5ccccc45)c3C2c2ccccc2Cl)cc1]

Step 7: To a stirred solution of (1-chloro-2-methylprop-1-en-1-yl)dimethylamine (624 mg, 4.67 mmol) in toluene (3.89 mL) was added 1,2-benzothiazole-3-carboxylic acid (836 mg, 4.67 mmol). The suspension very quickly turned into a clear, light pink solution, which was stirred for 30 minutes before addition of 1.3 mL to a solution of 4-amino-2-chloro-5-(2-chlorophenyl)-6-[(4-methoxyphenyl)methyl]-5H,6H,7H-pyrrolo[3,4-b]pyridin-7-one (323 mg, 0.779 mmol) in pyridine (2.6 mL). To this reaction solution was added catalytic DMAP. The solution was stirred at room temperature for 5 minutes and then at 65° C. for 30 minutes. A total of 6 equivalents of acid chloride was added in several portions. The reaction was eventually cooled to R.T. and quenched with MeOH (3 mL), then concentrated and loaded onto a 12 g silica gel column eluted with DCM to 10:90:1 MeOH/DCM/NH₄OH gradient over 25 minutes. The product eluted between 3% and 3.5% MeOH/DCM to yield a light yellow, foamy solid (316 mg, 70.5% yield). MS: m/z=575.5 [M+H]⁺.

N-[2-Chloro-5-(2-chlorophenyl)-7-oxo-5H,6H,7H-pyrrolo[3,4-b]pyridin-4-yl]-1,2-benzothiazole-3-carboxamide (I-93)

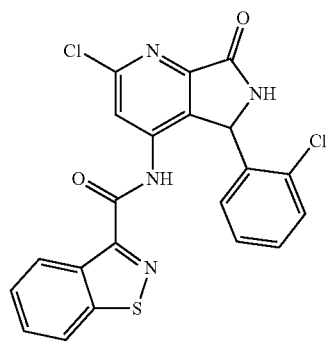 [SMILES: O=C1NC(c2ccccc2Cl)c2c(NC(=O)c3nsc4ccccc34)cc(Cl)nc21]

Step 8: To a solution of N-[2-chloro-5-(2-chlorophenyl)-6-[(4-methoxyphenyl)methyl]-7-oxo-5H,6H,7H-pyrrolo[3,4-b]pyridin-4-yl]-1,2-benzothiazole-3-carboxamide (251 mg, 0.436 mmol) in acetonitrile (8.7 mL) was added a solution of cerium ammonium nitrate (712 mg, 1.30 mmol) in water (0.87 mL). The mixture was stirred 1 hour at RT. The reaction was treated with saturated aqueous NaHCO₃ (25 mL). A yellow precipitate was isolated by filtration, dried, and eluted on a 12 g silica gel column with a DCM to 10:90:1 MeOH/DCM/NH₄OH gradient over 25 minutes. The major product peak eluted between 5.5% and 6.7% MeOH/DCM. The fractions containing pure product were combined, concentrated, and dried to yield N-[2-chloro-5-(2-chlorophenyl)-7-oxo-5H,6H,7H-pyrrolo[3,4-b]pyridin-4-yl]-1,2-benzothiazole-3-carboxamide (44 mg, 21.8% yield). MS: m/z=455.3 [M+H]¹; ¹H NMR (400 MHz, DMSO-d₆) δ 10.53 (s, 1H), 9.65 (s, 1H), 8.67 (d, 1H), 8.32 (d, 1H), 7.98 (s, 1H), 7.69 (t, 1H), 7.62 (t, 1H), 7.33 (d, 1H), 7.22 (t, 1H), 7.14 (t, 1H).

N-(5-(2-Chlorophenyl)-7-oxo-2-(1H-pyrazol-4-yl)-6,7-dihydro-5H-pyrrolo[3,4-h]pyridin-4-yl)benzo[d]isothiazole-3-carboxamide (I-94)

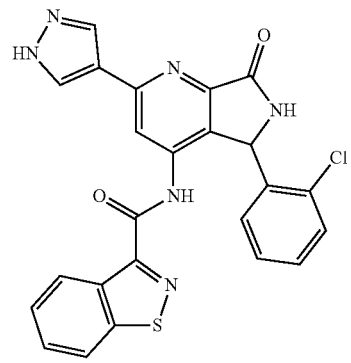 [SMILES: O=C1NC(c2ccccc2Cl)c2c(NC(=O)c3nsc4ccccc34)cc(-c3cn[nH]c3)nc21]

Step 9: To a mixture of N-[2-chloro-5-(2-chlorophenyl)-7-oxo-5H,6H,7H-pyrrolo[3,4-b]pyridin-4-yl]-1,2-benzothiazole-3-carboxamide (18.3 mg, 0.04 mmol), tert-butyl 4-(4,4,5,5-tetramethyl-1,3,2-dioxaborolan-2-yl)-1H-pyrazole-1-carboxylate (17.6 mg, 0.06 mmol, 1.5 eq), bis(triphenylphosphine) palladium (II) dichloride (4.2 mg, 0.006 mmol, 0.15 eq) in a sealed tube were added acetonitrile (0.8 mL) and a solution of sodium carbonate (12.7 mg, 0.12 mmol, 3 eq) in water (0.27 mL). The reaction mixture was briefly degassed with nitrogen before sealing the tube. The reaction mixture was then stirred at 115° C. for 20 minutes before cooling back to RT. The reaction mixture was diluted with THF (5 mL) and brine (3 mL), and the layers were separated. The organic layer was dried over sodium sulfate, filtered, and concentrated. The crude was loaded as a silica gel slurry onto a 12 gram silica gel column and eluted with a gradient of DCM to 10:90:1 MeOH/DCM/NH₄OH over 20 minutes. The fractions eluting between 7% and 9%

MeOH/DCM were combined, concentrated, and dried to yield racemic N-[5-(2-chlorophenyl)-7-oxo-2-(1H-pyrazol-4-yl)-5H,6H,7Hpyrrolo[3,4-b]pyridin-4-yl]-1,2-benzothiazole-3-carboxamide as a light yellow solid (6.8 mg, 35% yield). MS: m/z=487.3 [M+H]$^+$; $^1$H NMR (400 MHz, DMSO-d$_6$) δ 13.20 (br s, 1H), 10.48 (s, 1H), 9.46 (s, 1H), 8.69 (d, J=8.1 Hz, 1H), 8.41 (br s, 1H), 8.33 (d, J=8.1 Hz, 1H), 8.10 (br s, 1H), 8.07 (s, 1H), 7.60-7.73 (m, 3H), 7.30 (d, J=7.8 Hz, 1H), 7.15-7.21 (m, 1H), 7.09-7.14 (m, 1H), 6.29 ppm (br s, 1H).

Additional compounds prepared according to the method of Examples 68 and 69 are listed in Table 32 below.

TABLE 32

Additional Exemplary Compounds
Compound

| |
|---|
| I-108 |
| I-113 |
| I-114 |
| I-161 |
| I-162 |
| I-182 |
| I-186 |
| I-187 |
| I-193 |
| I-194 |
| I-195 |
| I-196 |
| I-379 |
| I-380 |
| I-381 |
| I-384 |
| I-386 |

Example 74

N-[5-(2-Chloro-5-fluorophenyl)-2-(3,3-difluoroazetidin-1-yl)-7-oxo-5H,6H,7H-pyrrolo[3,4-b]pyridin-4-yl]-3-fluoro-5-(trifluoromethyl)benzamide (I-286)

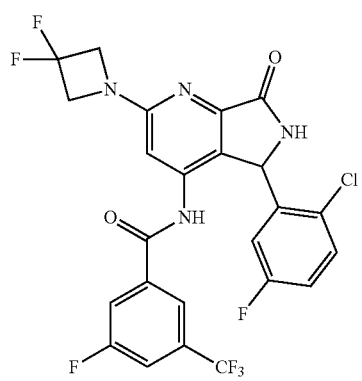 [SMILES: O=C(Nc1cc(N2CC(F)(F)C2)nc2c1C(c1cc(F)ccc1Cl)NC2=O)c1cc(F)cc(C(F)(F)F)c1]

4-Amino-2-chloro-5-(2-chloro-5-fluorophenyl)-6-(2,4-dimethoxybenzyl)-5,6-dihydro-7H-pyrrolo[3,4-b]pyridin-7-one

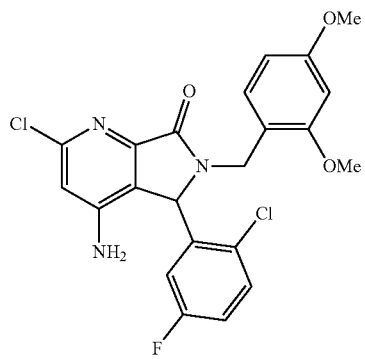 [SMILES: COc1ccc(CN2C(=O)c3nc(Cl)cc(N)c3C2c2cc(F)ccc2Cl)c(OC)c1]

Step 1 to 6: According to the procedures of Example 68, Steps 1 to 6, 4,6-dichloropicolinic acid, 2,4-dimethoxybenzylamine, and 2-chloro-5-fluorobenzoyl chloride were converted to 4-amino-2-chloro-5-(2-chloro-5-fluorophenyl)-6-(2,4-dimethoxybenzyl)-5,6-dihydro-7H-pyrrolo[3,4-b]pyridin-7-one.

N-(2-Chloro-5-(2-chloro-5-fluorophenyl)-6-(2,4-dimethoxybenzyl)-7-oxo-6,7-dihydro-5H-pyrrolo[3,4-b]pyridin-4-yl)-3-fluoro-5-(trifluoromethyl)benzamide

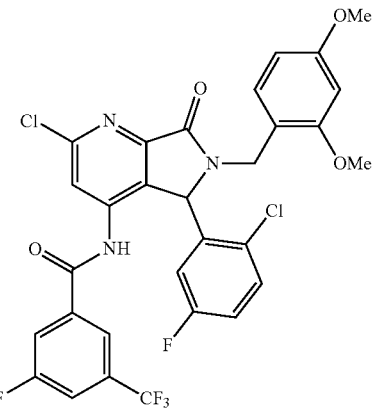

Step 7: To a mixture of 4-amino-2-chloro-5-(2-chloro-5-fluorophenyl)-6-(2,4-dimethoxybenzyl)-5,6-dihydro-7H-pyrrolo[3,4-b]pyridin-7-one (1.00 g, 2.31 mmol) in dry pyridine (14.7 mL) under nitrogen was added dropwise 3-fluoro-5-(trifluoromethyl)benzoyl chloride (530.4 μL, 3.47 mmol). Then 4-dimethylaminopyridine (14 mg, 0.115 mmol) was added, and the mixture was stirred at ambient temperature for 6 h. The mixture was quenched with water, and the pH was adjusted with a saturated aqueous NaHCO$_3$ solution. The product was extracted with DCM. The organic phase was then dried over sodium sulfate, filtered, and concentrated by rotary evaporation. Purification by normal-phase silica chromatography (0% to 70% EtOAc/hexanes) furnished N-(2-chloro-5-(2-chloro-5-fluorophenyl)-6-(2,4- dimethoxybenzyl)-7-oxo-6,7-dihydro-5H-pyrrolo[3,4-b]pyridin-4-yl)-3-fluoro-5-(trifluoromethyl)benzamide as a white solid (67% yield).

N-(5-(2-Chloro-5-fluorophenyl)-2-(3,3-difluoroazetidin-1-yl)-6-(2,4-dimethoxybenzyl)-7-oxo-6,7-dihydro-5H-pyrrolo[3,4-b]pyridin-4-yl)-3-fluoro-5-(trifluoromethyl)benzamide

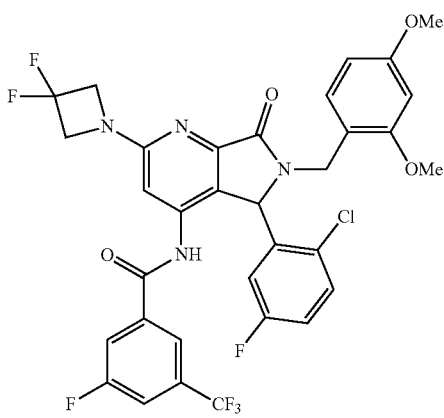 [SMILES: COc1ccc(CN2C(=O)c3nc(N4CC(F)(F)C4)cc(NC(=O)c4cc(F)cc(C(F)(F)F)c4)c3C2c2cc(F)ccc2Cl)c(OC)c1]

Step 8: A vial containing N-(2-chloro-5-(2-chloro-5-fluorophenyl)-6-(2,4-dimethoxybenzyl)-7-oxo-6,7-dihydro-5H-pyrrolo[3,4-b]pyridin-4-yl)-3-fluoro-5-(trifluoromethyl)benzamide (1.00 g, 1.61 mmol), 3,3-difluoroazetidine hydrochloride (416.24 mg, 3.21 mmol), and BrettPhos Pd Gen.4 (728.3 mg, 0.803 mmol) was evacuated under vacuum and purged with nitrogen. Toluene (10.7 mL, 0.15 M) was added, and the mixture was purged once more with nitrogen. Then LiHMDS (1M in THF, 8.03 mL, 8.03 mmol) was added to the mixture, and the mixture was stirred at 105° C. for 2 h. The mixture was cooled to 22° C. and quenched with DCM and water under inert atmosphere. The bi-phasic solution was then diluted with a saturated aqueous $NH_4Cl$ solution and extracted with DCM. The organic layer was dried over sodium sulfate, filtered, and concentrated by rotary evaporation. The resulting product mixture was directly subjected to the subsequent reaction without further purification.

N-[5-(2-Chloro-5-fluorophenyl)-2-(3,3-difluoroazetidin-1-yl)-7-oxo-5H,6H,7H-pyrrolo[3,4-b]pyridin-4-yl]-3-fluoro-5-(trifluoromethyl)benzamide (I-286)

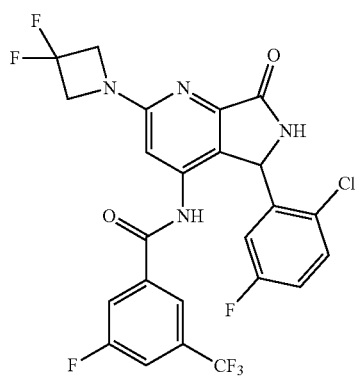 [SMILES: O=C(Nc1cc(N2CC(F)(F)C2)nc2c1C(c1cc(F)ccc1Cl)NC2=O)c1cc(F)cc(C(F)(F)F)c1]

Step 9: The product mixture from the previous step containing N-(5-(2-Chloro-5-fluorophenyl)-2-(3,3-difluoroazetidin-1-yl)-6-(2,4-dimethoxybenzyl)-7-oxo-6,7-dihydro-5H-pyrrolo[3,4-b]pyridin-4-yl)-3-fluoro-5-(trifluoromethyl)benzamide (ca. 1.00 mmol) was treated with trifluoroacetic acid (22 mL) and trifluoromethanesulfonic acid (0.1 mL, 1 mmol). The resulting mixture was stirred at 90° C. for 1 h. The mixture was cooled to room temperature and concentrated. The residue was purified by C18 silica gel column chromatography (30% to 80% MeCN/10 mM Ammonium Bicarbonate aq.). The product-containing fractions were combined and lyophilized to obtain N-[5-(2-chloro-5-fluorophenyl)-2-(3,3-difluoroazetidin-1-yl)-7-oxo-5H,6H,7H-pyrrolo[3,4-b]pyridin-4-yl]-3-fluoro-5-(trifluoromethyl)benzamide as a white powder (64.8 mg, 11.5% over two steps). MS: m/z=559.3 [M+H]$^+$; $^1$H NMR (400 MHz, DMSO-$d_6$) δ 10.72 (br s, 1H), 9.30 (br s, 1H), 7.94 (d, J=6.5 Hz, 1H), 7.71 (d, J=9.0 Hz, 1H), 7.62 (s, 1H), 7.34 (dd, J=8.9, 5.2 Hz, 1H), 7.17-6.97 (m, 1H), 6.94-6.56 (m, 2H), 5.91 (br s, 1H), 4.65-4.33 (m, 4H).

Additional compounds prepared according to the method of Examples 68-70 are listed in Table 33 below.

TABLE 33

| Additional Exemplary Compounds Compound |
| --- |
| I-273 |
| I-284 |
| I-288 |
| I-291 |
| I-319 |
| I-321 |
| I-322 |
| I-329 |
| I-338 |
| I-354 |
| I-357 |
| I-356 |
| I-366 |
| I-367 |
| I-368 |

Example 75

Methyl 4-(1,2-benzothiazole-3-amido)-5-(2-chlorophenyl)-7-oxo-5H,6H,7H-pyrrolo[3,4-b]pyridine-2-carboxylate (I-222)

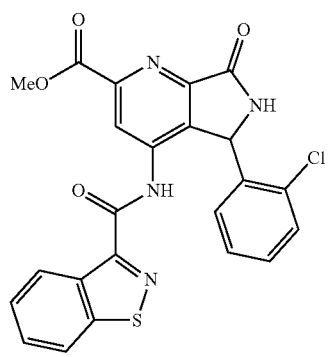 [SMILES: COC(=O)c1cc(NC(=O)c2nsc3ccccc23)c2c(n1)C(=O)NC2c1ccccc1Cl]

1949

4-Chloro-6-(methoxycarbonyl)pyridine-2-carboxylic acid

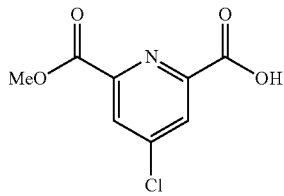 [SMILES: COC(=O)c1cc(Cl)cc(C(=O)O)n1]

Step 1: 4-Chloropyridine-2,6-dicarboxylic acid (8.15 g, 40.4 mmol) was mixed with thionyl chloride (58.8 mL, 807 mmol) and warmed to reflux. After 5 hours of stirring, the mixture was cooled to room temperature and stirred for 16 hours. The excess thionyl chloride was removed by rotary evaporation. The residue was dissolved with anhydrous dichloroethane (161 mL) and then cooled to 0-5° C. Methanol (1.87 mL, 46.4 mmol) and DIPEA (8.07 mL, 46.4 mmol) were added dropwise to the mixture (exothermic). The mixture was stirred for 2.5 hours at room temperature. The volatiles were removed by rotary evaporation. The residue containing a mixture of monomethyl ester, dimethyl ester, and starting material was purified by normal phase chromatography (0-50% acetonitrile/DCM). The pure fractions were combined, concentrated, and dried under vacuum to afford 4-chloro-6-(methoxycarbonyl)pyridine-2-carboxylic acid as an off-white solid (2.28 g, 26% yield, 90% purity by LC/MS).

Methyl 4-chloro-6-{[(4-methoxyphenyl)methyl]carbamoyl}pyridine-2-carboxylate

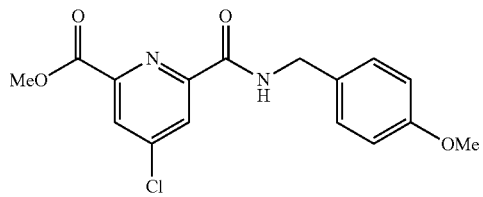 [SMILES: COC(=O)c1cc(Cl)cc(C(=O)NCc2ccc(OC)cc2)n1]

Step 2: Thionyl chloride (15.2 mL, 10 mmol) was added dropwise to a stirred suspension of 4-chloro-6-(methoxycarbonyl)pyridine-2-carboxylic acid (2.28 g, 10.5 mmol) in DMF (10 mL) at room temperature. After 25 mins and following gas evolution, the mixture was warmed to 40° C. for 20 mins. The excess of thionyl chloride was removed by rotary evaporation, and the residue was dissolved in dry dichloroethane (42.0 mL) and cooled to 0° C. Triethylamine (3.12 mL, 22.5 mmol) and 1-(4-methoxyphenyl)methanamine (2.04 mL, 15.7 mmol) were added to the solution. The mixture was stirred at room temperature for 1 hour. The mixture was slowly quenched with water. The layers were separated, and the aqueous layer was extracted with EtOAc. The organic layers were combined, dried over Na$_2$SO$_4$, and the solvents were evaporated. The residue was purified through normal phase silica gel chromatography (20-75% EtOAc/hexanes) to afford methyl 4-chloro-6-{[(4-methoxyphenyl)methyl]carbamoyl}pyridine-2-carboxylate as a yellow solid (2.56 g, 73% yield).

1950

Methyl 4-chloro-5-(2-chlorophenyl)-5-hydroxy-6-[(4-methoxyphenyl)methyl]-7-oxo-5H,6H,7H-pyrrolo[3,4-b]pyridine-2-carboxylate

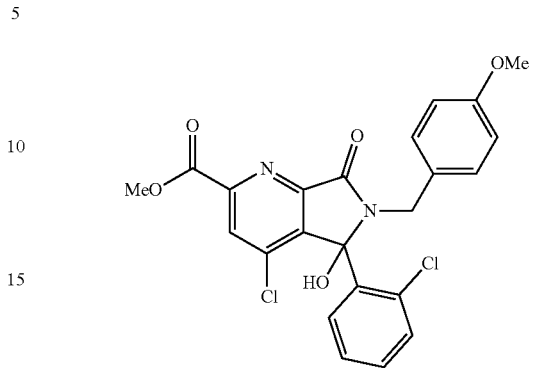

Step 3: To a stirred −50° C. solution of methyl 4-chloro-6-{[(4-methoxyphenyl) methyl]carbamoyl}pyridine-2-carboxylate (1.53 g, 4.57 mmol) in THF (22.8 mL) under nitrogen atmosphere was slowly added LiHMDS (1.0 M solution in THF, 5.0 mL, 5.0 mmol). The solution was stirred at −78° C. for 1 hour. To the mixture was added dropwise 2-chlorobenzoyl chloride (635 µL, 5.02 mmol) over 2 minutes. The mixture was stirred 0.5 hour at −78° C. and then 2.5 hours at room temperature. The mixture was cooled back between −50° C. and −78° C., and then LiHMDS (1M in THF, 5.0 mL, 5.0 mmol) was slowly added. The mixture was stirred between −50° C. and −78° C. for 1 hour. The mixture was slowly quenched with a solution of AcOH (0.6 mL) in MeOH (25 mL). The solution was then diluted in water and EtOAc. The layers were separated, and the aqueous layer was extracted three times with EtOAc. The organic layers were combined, washed with brine, dried over Na$_2$SO$_4$, filtered, and concentrated. The residue was purified by normal phase silica chromatography (0-60% acetone/heptanes) to afford methyl 4-chloro-5-(2-chlorophenyl)-5-hydroxy-6-[(4-methoxyphenyl)methyl]-7-oxo-5H,6H,7H-pyrrolo[3,4-b]pyridine-2-carboxylate as an off-white solid (1.03 g, 38% yield).

Methyl 4-chloro-5-(2-chlorophenyl)-6-[(4-methoxyphenyl)methyl]-7-oxo-5H,6H,7H-pyrrolo[3,4-b]pyridine-2-carboxylate

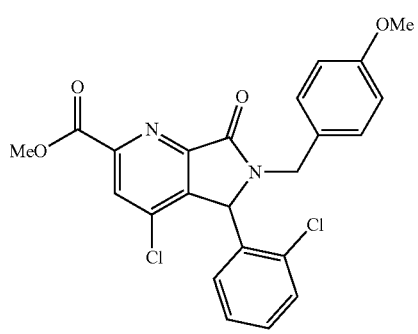 [SMILES: COC(=O)c1cc(Cl)c2c(n1)C(=O)N(Cc1ccc(OC)cc1)C2c1ccccc1Cl]

Step 4: To a stirred 0° C. solution of methyl 4-chloro-5-(2-chlorophenyl)-5-hydroxy-6-[(4-methoxyphenyl)methyl]-7-oxo-5H,6H,7H-pyrrolo[3,4-b]pyridine-2-carboxylate (1.03 g, 2.17 mmol) in DCM (10.8 mL) under nitrogen was added TFA (3.31 mL, 43.4 mmol) followed by triethylsilane (3.46 mL, 21.7 mmol). The mixture was then allowed to warm to room temperature and stirred for 16 hours. The mixture was cooled to 0° C. and a second portion of TFA (1.65 mL, 21.7 mmol) and triethylsilane (1.73 mL, 10.9 mmol) were added. The mixture was warmed to room temperature and stirred for 16 hours. The mixture was diluted with DCM and quenched with saturated aqueous solution of NaHCO₃ until pH 6-7 was obtained. The layers were separated, and the aqueous layer was extracted once with DCM. The organic layers were combined, washed with brine, dried over Na₂SO₄, filtered, and concentrated. The residue was purified by normal phase silica gel column (30-100% acetone/hexanes) to afford methyl 4-chloro-5-(2-chlorophenyl)-6-[(4-methoxyphenyl) methyl]-7-oxo-5H, 6H,7H-pyrrolo[3,4-b]pyridine-2-carboxylate as a yellow solid (684.8 mg, 69% yield).

Methyl 4-azido-5-(2-chlorophenyl)-5-hydroxy-6-[(4-methoxyphenyl)methyl]-7-oxo-5H,6H,7H-pyrrolo[3,4-b]pyridine-2-carboxylate

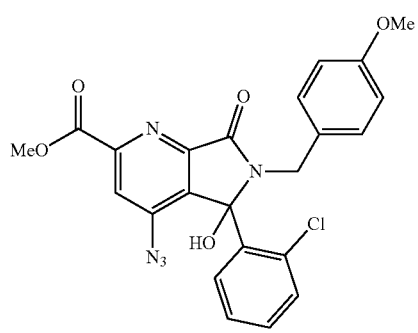 [SMILES: COC(=O)c1cc(N=[N+]=[N-])c2c(n1)C(=O)N(Cc1ccc(OC)cc1)C2(O)c1ccccc1Cl]

Step 5: To a round bottom flask was added methyl 4-chloro-5-(2-chlorophenyl)-6-[(4-methoxyphenyl)methyl]-7-oxo-5H,6H,7H-pyrrolo[3,4-b]pyridine-2-carboxylate (500 mg, 1.09 mmol) in DMF (5.7 mL). Sodium azide (105 mg, 1.63 mmol) was added, and the mixture was stirred at 70° C. for 1.5 hours. The mixture was cooled to room temperature, then diluted with water and extracted with DCM. The aqueous layer was extracted once more with DCM. The organic layers were combined, washed with brine, dried over Na₂SO₄, filtered, and concentrated. The resulting methyl 4-azido-5-(2-chlorophenyl)-5-hydroxy-6-[(4-methoxyphenyl)methyl]-7-oxo-5H,6H,7H-pyrrolo[3,4-b]pyridine-2-carboxylate was directly subjected to the subsequent reaction without further purification.

Methyl 4-amino-5-(2-chlorophenyl)-5-hydroxy-6-[(4-methoxyphenyl)methyl]-7-oxo-5H,6H,7H-pyrrolo[3,4-b]pyridine-2-carboxylate

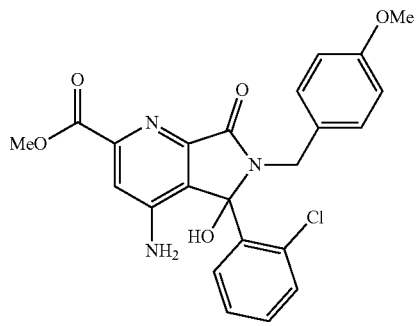 [SMILES: COC(=O)c1cc(N)c2c(n1)C(=O)N(Cc1ccc(OC)cc1)C2(O)c1ccccc1Cl]

Step 6: To a solution of methyl 4-azido-5-(2-chlorophenyl)-5-hydroxy-6-[(4-methoxyphenyl)methyl]-7-oxo-5H, 6H,7H-pyrrolo[3,4-b]pyridine-2-carboxylate (505 mg, 1.05 mmol) in THF (10.5 mL) and water (2.10 mL) was added triphenylphosphine (826 mg, 3.15 mmol). The mixture was heated at 60° C. for 2 hours. The mixture was cooled to room temperature and concentrated hydrochloric acid (2.62 mL, 31.5 mmol) was added dropwise (exothermic addition). The mixture was heated at 60° C. for 2 hours and then cooled to room temperature. The volatiles were concentrated by rotary evaporation, and the residue was diluted in DCM and water. The aqueous layer was basified with a saturated aqueous solution of NaHCO₃. The layers were separated, and the aqueous layer was extracted twice with DCM. The organic layers were combined, washed with brine, dried over Na₂SO₄, filtered, and concentrated. The residue was purified by normal-phase silica chromatography (0-15% MeOH/DCM) follow by a second purification by normal phase silica chromatography (0-80% acetone/heptanes) to afford methyl 4-amino-5-(2-chlorophenyl)-5-hydroxy-6-[(4-methoxyphenyl)methyl]-7-oxo-5H,6H,7H-pyrrolo[3,4-b]pyridine-2-carboxylate as a yellow solid (100.7 mg, 21% yield over 2 steps).

Methyl 4-amino-5-(2-chlorophenyl)-6-[(4-methoxyphenyl)methyl]-7-oxo-5H,6H,7H-pyrrolo[3,4-b]pyridine-2-carboxylate

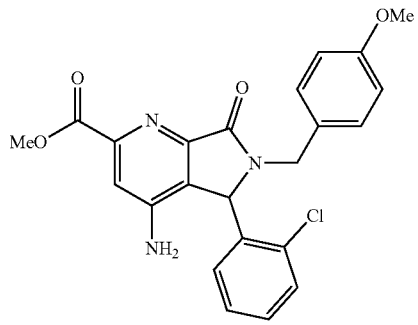 [SMILES: COC(=O)c1cc(N)c2c(n1)C(=O)N(Cc1ccc(OC)cc1)C2c1ccccc1Cl]

Step 7: To a stirred solution of methyl 4-amino-5-(2-chlorophenyl)-5-hydroxy-6-[(4-methoxyphenyl)methyl]-7-oxo-5H,6H,7H-pyrrolo[3,4-b]pyridine-2-carboxylate (87.6 mg, 0.193 mmol) in DCE (2.57 mL) under nitrogen was added trifluoroborane diethyl etherate (76.1 μL, 0.618 mmol) followed by triethylsilane (307 μL, 1.93 mmol). The mixture was heated to 80° C., stirred for 15 hours, and then cooled to room temperature. A second portion of trifluoroborane diethyl etherate (76.1 μL, 0.618 mmol) and triethylsilane (307 μL, 1.93 mmol) was added, and the mixture was heated to 80° C. and stirred 15 hours. The mixture was cooled to room temperature and diluted with DCM and water. The pH was adjusted to 8-9 with a saturated aqueous solution of NaHCO$_3$. The layers were separated, and the aqueous layer was extracted with DCM twice. The organic layers were combined, washed with brine, dried over Na$_2$SO$_4$, filtered, and concentrated. The residue was directly used for the next step without any further purification.

Methyl 4-(1,2-benzothiazole-3-amido)-5-(2-chlorophenyl)-6-[(4-methoxyphenyl)methyl]-7-oxo-5H,6H,7H-pyrrolo[3,4-b]pyridine-2-carboxylate

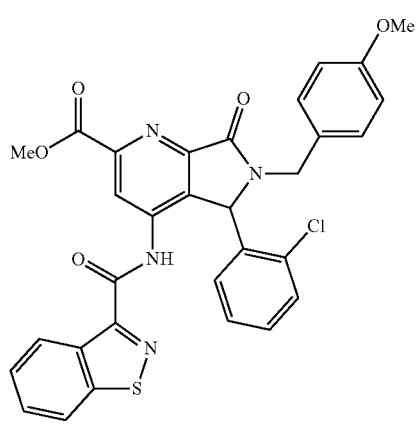 [SMILES: COC(=O)c1cc(NC(=O)c2nsc3ccccc23)c2c(n1)C(=O)N(Cc1ccc(OC)cc1)C2c1ccccc1Cl]

Step 8: The residue from the previous step containing methyl 4-amino-5-(2-chlorophenyl)-6-[(4-methoxyphenyl)methyl]-7-oxo-5H,6H,7H-pyrrolo[3,4-b]pyridine-2-carboxylate (84.5 mg, 0.193 mmol) and 1,2-benzothiazole-3-carboxylic acid (44.9 mg, 0.251 mmol) were dissolved in DCM (0.96 mL). N-Methylimidazole (53.7 uL, 0.675 mmol) was added, followed by tetramethylchloroformamidinium hexafluorophosphate (64.9 mg, 0.231 mmol). The mixture was stirred at room temperature for 16 hours and then diluted with DCM and water. The pH was adjusted to 7-8 with a saturated aqueous solution of NaHCO$_3$. The layers were separated, and the aqueous layer was extracted with DCM. The combined organics were washed with brine, dried with Na$_2$SO$_4$, filtered, and concentrated. The resulting residue was directly subjected to the subsequent reaction without further purification.

Methyl 4-(1,2-benzothiazole-3-amido)-5-(2-chlorophenyl)-7-oxo-5H,6H,7H-pyrrolo[3,4-b]pyridine-2-carboxylate (I-222)

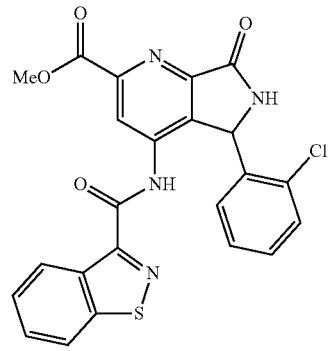 [SMILES: COC(=O)c1cc(NC(=O)c2nsc3ccccc23)c2c(n1)C(=O)NC2c1ccccc1Cl]

Step 9: According to the procedures of Example 37, Step 7, methyl 4-(1,2-benzothiazole-3-amido)-5-(2-chlorophenyl)-6-[(4-methoxyphenyl)methyl]-7-oxo-5H,6H,7H-pyrrolo[3,4-b]pyridine-2-carboxylate was converted to methyl 4-(1,2-benzothiazole-3-amido)-5-(2-chlorophenyl)-7-oxo-5H,6H,7H-pyrrolo[3,4-b]pyridine-2-carboxylate. The residue was purified by normal-phase silica chromatography (0% to 10% MeOH/DCM). The residue was suspended in water and the precipitate filtered. The solid was then dissolved with a mixture of acetonitrile/water and lyophilized to obtain methyl 4-(1,2-benzothiazole-3-amido)-5-(2-chlorophenyl)-7-oxo-5H,6H,7H-pyrrolo[3,4-b]pyridine-2-carboxylate as an off-white powder (4.62 mg, 13% yield over 3 steps). MS: m/z=479.2 [M+H]f; $^1$H NMR (400 MHz, DMSO-d$_6$) δ 10.61 (br s, 1H), 9.70 (br s, 1H), 8.70 (d, J=7.9 Hz, 1H), 8.60 (s, 1H), 8.33 (d, J=8.2 Hz, 1H), 7.70 (ddd, J=8.3, 7.0, 1.2 Hz, 1H), 7.67-7.52 (m, 1H), 7.33 (d, J=7.7 Hz, 1H), 7.23 (td, J=7.9, 1.6 Hz, 1H), 7.15 (td, J=7.4, 1.1 Hz, 1H), 6.40 (br s, 1H), 3.97 (s, 3H).

Example 76

Selected compounds of the present invention were tested in an ADP-Glo Biochemical PIK3CA Kinase Assay. Compounds to be assayed were plated in 16 doses of 1:2 serial dilutions (20 nL volume each well) on a 1536-well plate, and the plate warmed to room temperature. PIK3CA enzyme (e.g. H1047R, E542K, E545K, or wild-type) (1 μL of 2 nM solution in Enzyme Assay Buffer (comprising 50 mM HEPES pH 7.4, 50 mM NaCl, 6 mM MgCl$_2$, 5 mM DTT and 0.03% CHAPS)) was added and shaken for 10 seconds and preincubated for 30 minutes. To the well was added 1 μL of 200 μM ATP and 20 μM of diC8-PIP2 in Substrate Assay Buffer (50 mM HEPES pH 7.4, 50 mM NaCl, 5 mM DTI and 0.03% CHAPS) to start the reaction, and the plate was shaken for 10 seconds, then spun briefly at 1500 rpm, and then incubated for 60 minutes at room temperature. The reaction was stopped by adding 2 μL of ADP-Glo reagent (Promega), and spinning briefly at 1500 rpm, and then incubating for 40 minutes. ADP-Glo Detection reagent (Promega) was added and the plate spun briefly at 1500 rpm, then incubated for 30 minutes. The plate was read on an Envision 2105 (Perkin Elmer), and the IC$_{50}$ values were calculated using Genedata software.

Results of the ADP-Glo Biochemical PIK3CA Kinase Assay using H1047R PIK3CA enzyme are presented in Table 1. Compounds having an $IC_{50}$ less than or equal to 100 nM are represented as "A"; compounds having an $IC_{50}$ greater than 100 nM but less than or equal to 500 nM are represented as "B"; compounds having an $IC_{50}$ greater than 500 nM but less than or equal to 1 µM are represented as "C"; compounds having an $IC_{50}$ greater than 1 µM but less than or equal to 10 µM are represented as "D"; and compounds having an $IC_{50}$ greater than 10 µM but less than or equal to 100 µM are represented as "E".

Example 77

Selected compounds of the present invention were tested in a MCF10A Cell-Based PIK3CA Kinase Assay, namely the CisBio Phospho-AKT (Ser473) HTRF assay, to measure the degree of PIK3CA-mediated AKT phosphorylation. MCF10A cells (immortalized non-transformed breast cell line) overexpressing hotspot PIK3CA mutations (including H1047R, E542K, and E545K mutations) were used. Cells were seeded at 5,000 cells per well in DMEM/F12 (Thermo Fisher Scientific) supplemented with 0.5 mg/mL hydrocortisone, 100 ng/mL Cholera Toxin, 10 µg/mL insulin, and 0.5% horse serum. Once plated, cells were placed in a 5% $CO_2$, 37° C. incubator to adhere overnight.

The following day, compounds were added to the cell plates in 12 doses of 1:3 serial dilutions. The dose response curves were run in duplicate. Compound addition was carried out utilizing an Echo 55 Liquid Handler acoustic dispenser (Labcyte). The cell plates were incubated for 2 hours in a 5% $CO_2$, 37° C. incubator. Following compound incubation, the cells were lysed for 60 min at room temperature. Finally, a 4-hour incubation with the HTRF antibodies was performed at room temperature. All reagents, both lysis buffer and antibodies, were used from the CisBio pAKT S473 HTRF assay kit, as per the manufacturers protocol. Plates were read on an Envision 2105 (Perkin Elmer), and the $IC_{50}$ values were calculated using Genedata software.

Results of the MCF10A Cell-Based PIK3CA Kinase Assay are presented in Table 1. Compounds having an $IC_{50}$ less than or equal to 1 µM are represented as "A"; compounds having an $IC_{50}$ greater than 1 µM but less than or equal to 5 uM are represented as "B"; compounds having an $IC_{50}$ greater than 5 µM but less than or equal to 10 µM are represented as "C"; compounds having an $IC_{50}$ greater than 10 µM but less than or equal to 36 µM are represented as "D"; and compounds having an $IC_{50}$ greater than 36 µM but less than or equal to 100 µM are represented as "E".

INCORPORATION BY REFERENCE

All publications and patents mentioned herein are hereby incorporated by reference in their entirety for all purposes as if each individual publication or patent was specifically and individually incorporated by reference. In case of conflict, the present application, including any definitions herein, will control.

EQUIVALENTS

While specific embodiments of the subject disclosure have been discussed, the above specification is illustrative and not restrictive. Many variations of the present disclosure will become apparent to those skilled in the art upon review of this specification. The full scope of the disclosure should be determined by reference to the claims, along with their full scope of equivalents, and the specification, along with such variations.

Unless otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in this specification and attached claims are approximations that may vary depending upon the desired properties sought to be obtained by the present disclosure.

What is claimed is:

1. A compound, which is:

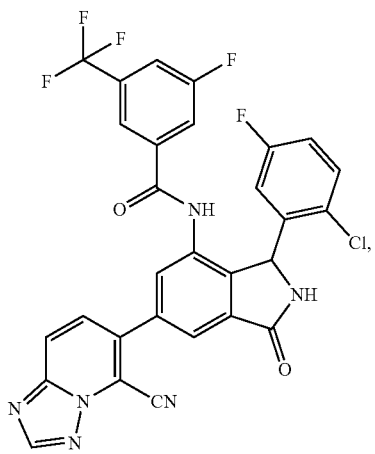 [SMILES: N#Cc1c(-c2cc(NC(=O)c3cc(F)cc(C(F)(F)F)c3)c3c(c2)C(=O)NC3c2cc(F)ccc2Cl)ccc2ncnn12]

or a pharmaceutically acceptable salt thereof.

2. A pharmaceutical composition comprising a pharmaceutically acceptable carrier, adjuvant, or vehicle and the compound of claim 1, or a pharmaceutically acceptable salt thereof.

3. A compound, which is:

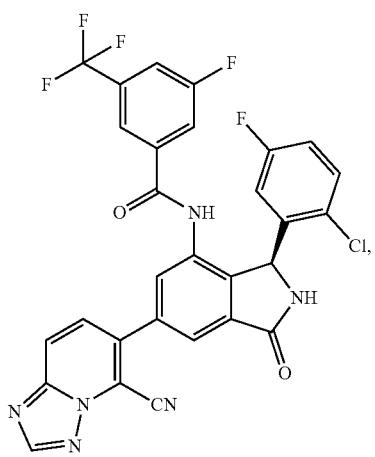 [SMILES: N#Cc1c(-c2cc(NC(=O)c3cc(F)cc(C(F)(F)F)c3)c3c(c2)C(=O)N[C@@H]3c2cc(F)ccc2Cl)ccc2ncnn12]

or a pharmaceutically acceptable salt thereof.

4. A pharmaceutical composition comprising a pharmaceutically acceptable carrier, adjuvant, or vehicle and the compound of claim 3, or a pharmaceutically acceptable salt thereof.

5. A compound, which is:
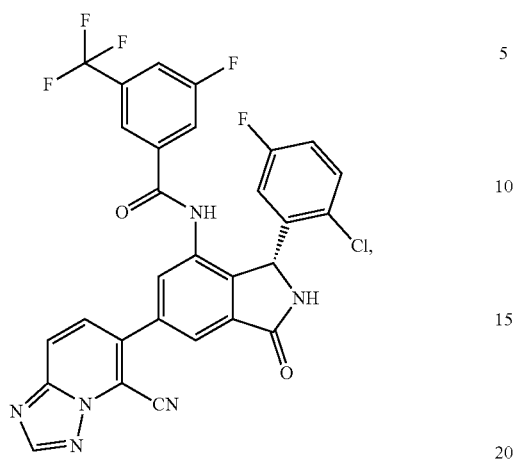
or a pharmaceutically acceptable salt thereof.
6. A pharmaceutical composition comprising a pharmaceutically acceptable carrier, adjuvant, or vehicle and the compound of claim 5, or a pharmaceutically acceptable salt thereof.
* * * * *

UNITED STATES PATENT AND TRADEMARK OFFICE
CERTIFICATE OF CORRECTION

Page 1 of 1

PATENT NO. : 12,219,327 B2
APPLICATION NO. : 18/208023
DATED : February 4, 2025
INVENTOR(S) : Dipietro et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 88 days.

Signed and Sealed this
Second Day of September, 2025

Coke Morgan Stewart
*Acting Director of the United States Patent and Trademark Office*